US007572882B2

(12) United States Patent
Sette et al.

(10) Patent No.: US 7,572,882 B2
(45) Date of Patent: Aug. 11, 2009

(54) INDUCING CELLULAR IMMUNE RESPONSES TO HUMAN PAPILLOMAVIRUS USING PEPTIDE AND NUCLEIC ACID COMPOSITIONS

(75) Inventors: Alessandro Sette, La Jolla, CA (US); John Sidney, San Diego, CA (US); Scott Southwood, Santee, CA (US); Robert Chesnut, Cardiff-by-the-Sea, CA (US); Esteban Celis, Rochester, MN (US); Howard M. Grey, La Jolla, CA (US)

(73) Assignee: Pharmexa Inc., San Diego, CA (US)

( * ) Notice: Subject to any disclaimer, the term of this patent is extended or adjusted under 35 U.S.C. 154(b) by 1056 days.

(21) Appl. No.: 10/149,136

(22) PCT Filed: Dec. 11, 2000

(86) PCT No.: PCT/US00/33549

§ 371 (c)(1),
(2), (4) Date: Oct. 29, 2002

(87) PCT Pub. No.: WO01/41799

PCT Pub. Date: Jun. 14, 2001

(65) Prior Publication Data

US 2007/0053922 A1    Mar. 8, 2007

(51) Int. Cl.
*A61K 38/03* (2006.01)
(52) U.S. Cl. ...................................... 530/300; 530/350
(58) Field of Classification Search ................. 530/300, 530/350
See application file for complete search history.

(56) References Cited

U.S. PATENT DOCUMENTS

| | | | |
|---|---|---|---|
| 4,235,877 A | 11/1980 | Fullerton | |
| 4,487,715 A | 12/1984 | Nitecki et al. | |
| 4,599,230 A | 7/1986 | Milich et al. | |
| 4,837,028 A | 6/1989 | Allen | |
| 5,013,548 A | 5/1991 | Haynes et al. | |
| 5,128,319 A | 7/1992 | Arlinghaus | |
| 5,180,806 A | 1/1993 | Dillner et al. | |
| 5,200,320 A | 4/1993 | Sette et al. | |
| 5,503,829 A | 4/1996 | Ladant et al. | |
| 5,618,536 A | 4/1997 | Lowy et al. | |
| 5,662,907 A | 9/1997 | Kubo et al. | |
| 5,716,620 A | 2/1998 | Lowy et al. | |
| 5,736,142 A | 4/1998 | Sette et al. | |
| 5,753,233 A | 5/1998 | Bleul et al. | |
| 5,783,567 A | 7/1998 | Hedley et al. | |
| 5,821,048 A | 10/1998 | Howley et al. | |
| 5,853,755 A | 12/1998 | Foldvari et al. | |
| 5,855,891 A | 1/1999 | Lowy et al. | |
| 5,871,998 A | 2/1999 | Lowy et al. | |
| 5,955,087 A * | 9/1999 | Whittle et al. ........... 424/204.1 |
| 5,985,610 A | 11/1999 | Lowy et al. | |
| 6,034,214 A | 3/2000 | Boon et al. | |
| 6,037,135 A | 3/2000 | Kubo et al. | |
| 6,365,160 B1 | 4/2002 | Webb et al. | |
| 6,413,935 B1 | 7/2002 | Sette et al. | |
| 6,419,931 B1 | 7/2002 | Vitiello et al. | |
| 6,602,510 B1 | 8/2003 | Fikes et al. | |
| 2002/0098197 A1 | 7/2002 | Sette et al. | |
| 2002/0160960 A1 | 10/2002 | Sette et al. | |
| 2002/0168374 A1 | 11/2002 | Kubo et al. | |
| 2002/0177694 A1 | 11/2002 | Sette et al. | |
| 2003/0143672 A1 | 7/2003 | Tangri et al. | |
| 2003/0216342 A1 | 11/2003 | Fikes et al. | |
| 2003/0216343 A1 | 11/2003 | Fikes et al. | |
| 2004/0096445 A1 | 5/2004 | Sidney et al. | |
| 2004/0157273 A1 | 8/2004 | Sidney et al. | |
| 2005/0049197 A1 | 3/2005 | Sette et al. | |

FOREIGN PATENT DOCUMENTS

| | | |
|---|---|---|
| EP | 0 044 710 A1 | 1/1982 |
| EP | 0 226 513 A1 | 6/1987 |
| EP | 0 433 242 | 6/1991 |
| EP | 0 378 881 | 6/1993 |
| EP | 0 429 816 | 6/1999 |
| WO | WO 91/18294 | 11/1991 |
| WO | WO 92/02543 A1 | 2/1992 |
| WO | WO 92/12996 A2 | 8/1992 |
| WO | WO 92/21033 A1 | 11/1992 |
| WO | WO 93/03764 | 3/1993 |
| WO | WO 93/03764 A1 | 3/1993 |
| WO | WO 93/22338 | 11/1993 |
| WO | WO 93/22338 A1 | 11/1993 |
| WO | WO 94/03205 A1 | 2/1994 |
| WO | WO 94/11738 A1 | 5/1994 |
| WO | WO 94/20127 | 9/1994 |
| WO | WO 94/20127 A1 | 9/1994 |
| WO | WO 95/07707 | 3/1995 |
| WO | WO 95/31476 A1 | 11/1995 |
| WO | WO 96/03140 A1 | 2/1996 |
| WO | WO 96/19496 A1 | 6/1996 |
| WO | WO 96/22067 | 7/1996 |
| WO | WO 97/34617 | 9/1997 |
| WO | WO 97/41440 | 11/1997 |

(Continued)

OTHER PUBLICATIONS

Konya et al. J Gen Virology 1997 78:2615-2620.*

(Continued)

*Primary Examiner*—Bruce Campell
*Assistant Examiner*—Myron G. Hill
(74) *Attorney, Agent, or Firm*—Sterne, Kessler, Goldstein & Fox P.L.L.C.

(57) ABSTRACT

This invention uses our knowledge of the mechanisms by which antigen is recognized by T cells to identify and prepare human papillomavirus (HPV) epitopes, and to develop epitope-based vaccines directed towards HPV. More specifically, this application communicates our discovery of pharmaceutical compositions and methods of use in the prevention and treatment of HPV infection.

13 Claims, No Drawings

FOREIGN PATENT DOCUMENTS

| WO | WO 99/45954 | 9/1999 |
|---|---|---|
| WO | WO 01/00225 | 1/2001 |

OTHER PUBLICATIONS

Ngelangel, N et al., Causes of cervical cancer in the Philippines: a case-control study J Natl Cancer Inst 1998; 90: 43-49.*
NCBL #S36564.*
Rotzschke, O., et al., "Peptide motifs of closely related HLA class I molecules encompass substantial differences," *Eur. J. Immunol.* 22:2453-2456, VCH Verlagsgesellschaft mbH (Sep. 1992).
Rötzschke, O., and Falk, K., "Origin, structure and motifs of naturally processed MHC class II ligands," *Curr. Opin. Immunol.* 6:45-51, Current Biology, Ltd. (Feb. 1994).
Rudinger, J., "Characteristics of the amino acids as components of a peptide hormone sequence," in *Peptide Hormones*, Parson, J.A., ed., University Park Press, Baltimore, MD, pp. 1-7 (1976).
Castellanos, M.R., et al., "Synthetic Peptides Induce a Cytotoxic Response against Human Paillomavirus Type-18," *Gynecol. Oncol.* 83:77-83, Academic Press (Jul. 2001).
Castellanos, M.R., et al., A rapid method to identify cytotoxic T-lymphocyte peptide epitopes from HLA-A2 (+) donors, *Crit. Rev. Oncol. Hematol.* 39:133-138, Elsevier Science Ireland, Ltd. (Jul.-Aug. 2001).
"HPV and Animal PV Nucleic Acid Sequences," *Human Papillomaviruses 1997 Compendium, Part I. HPV and Animal PV Nucleotide Sequences in GenBank style*, pp. I-1-I17, The Human Papillomavirus Database (Sep. 1997).
Kast, W.M., et al., "Role of HLA-A Motifs in Identification of Potential CTL Epitopes in Human Papillomavirus Type 16 E6 and E7 Proteins," *J. Immunol.* 152:3904-3912, The American Association of Immunologist (Apr. 1994).
Ressing, M.E., et al., "Human CTL Epitopes Encoded by Human Papillomavirus Type 16 E6 and E7 Identified Through In Vivo and In Vitro Immunogenecity Studies of HLA-A*0201-Binding Peptides," *J. Immunol.* 154:5934-5942, The American Association of Immunologists (Jun. 1995).
Rowen, D., and Lacey, C., "Toward a human papillomavirus vaccine," *Dermatologic Clinics* 16:835-838, W.B. Saunders (Oct. 1998).
Yoon, H., et al., "Synthetic peptides of human papillomavirus type 185 E6 harboring HLA-A2.1 motif can induce peptide-specific cytotoxic T-cells from peripheral blood mononuclear cells of healthy donors," *Virus Res.* 54:23-29, Elsevier Science B.V. (Mar. 1998).
Co-pending U.S. Appl. No. 08/205,713, inventor Grey, filed Mar. 4, 1994 (Not Published).
Co-pending U.S. Appl. No. 08/344,824, inventors Sette et al., filed Nov. 23, 1994 (Not Published).
Co-pending U.S. Appl. No. 08/347,610, inventors Kubo et al., filed Dec. 1, 1994 (Not Published).
Co-pending U.S. Appl. No. 09/017,524, inventors Kubo et al., filed Feb. 3, 1998 (Not Published).
Co-pending U.S. Appl. No. 09/641,528, inventors Sette et al., filed Aug. 15, 2000 (Not Published).
Alexander, M., et al., "Generation of tumor-specific cytolytic T lymphocytes from peripheral blood of cervical cancer patients by in vitro stimulation with a synthetic human papillomavirus type 16 E7 epitope," *Am. J. Obstet. Gynecol.* 175:1586-1593, Mosby-Year Book (1996).
Bremers, A.J.A., et al., "The Use of Epstein-Barr Virus-Transformed B Lymphocyte Cell Lines in a Peptide-Reconstitution Assay: Identification of CEA-Related HLA-A*0301-Restricted Potential Cytotoxic T-Lymphocyte Epitopes," *J. Immunother.* 18:77-85, Lippincott-Raven (1995).
Busch, R., et al., "Degenerate binding of immunogenic peptides to HLA-DR proteins on B cell surfaces," *Int. Immunol.* 2:443-451, Oxford University Press (1990).
Feltkamp, M.C.W., et al., "Vaccination with cytotoxic T lymphocyte epitope-containing peptide protects against a tumor induced by human papillomavirus type 16-transformed cells," *Eur. J. Immunol.* 23:2242-2249, VCH Verlagsgesellschaft (1993).

Kast, W.M., et al., "Role of HLA-A Motifs in Identification of Potential CTL Epitopes in Human Papillomavirus Type 16 E6 and E7 Proteins," *J. Immunol.* 152:3904-3912, American Association of Immunologists (1994).
Melief, C.J.M., and Kast, W.M., "Lessons from T Cell Responses to Virus Induced Tumours for Cancer Eradication in General," *Cancer Surv.* 13:81-99, Cold Spring Harbor Press (1992).
Rammensee, H-G., et al., "MHC ligands and peptide motifs: first listing," *Immunogen.* 41:178-228, Springer-Verlag (1995).
Ressing, M.E., et al., "Human CTL Epitopes Encoded by Human Papillomavirus Type 16 E6 and E7 Identified Through In Vivo and In Vitro Immunogenicity Studies of HLA-A*0201-Binding Peptides," *J. Immunol.* 154:5934-5943, American Association of Immunologists (1995).
Schultz, M., et al., "Peptide-induced antiviral protection by cytotoxic T cells," *Proc. Natl. Acad. Sci. USA* 88:991-993, National Academy of Sciences (1991).
Sidney, J., et al., "Specificity and Degeneracy in Peptide Binding to HLA-B7-Like Class I Molecules," *J. Immunol.* 157:3480-3490, American Association of Immunologists (1996).
Toes, R.E.M., et al., "Protective anti-tumor immunity induced by vaccination with recombinant adenoviruses encoding multiple tumor-associated cytotoxic T lymphocyte epitopes in a string-of-beads fashion," *Proc. Natl. Acad. Sci. USA* 94:14660-14665, National Academy of Sciences (1997).
Altuvia, Y., et al., "A Structure-Based Algorithm to Predict Potential Binding Peptides ot MHC Molecules with Hydrophobic Binding Pockets," *Hum. Immunol.* 58:1-11, Elsevier Science Inc. (1997).
Geisbill, J., et al., "Detection and characterization of human papilloma virus type 45 DNA in the cervical carcinoma cell line MS751," *J. Gen. Virol.* 78:655-658, Society for General Microbiology (1997).
European Search Report for European Application No. 00 98 6316, European Patent Office, Netherlands, mailed Mar. 9, 2005.
Alexander, J., et al., "Development of High Potency Universal DR-Restricted Helper Epitopes by Modification of High Affinity DR-Blocking Peptides," *Immunity* 1:751-761, Cell Press (1994).
Arndt, S.O., et al., "Selection of the MHC Class II-Associated Peptide Repertoire by HLA-DM," *Immunol. Res.* 16:261-272, Humana Press (Dec. 1997).
Barouch, D., et al., "HLA-A2 Subtypes Are Functionally Distinct in Peptide Binding and Presentation," *J. Exp. Med.* 182:1847-1856, Rockefeller University Press (1995).
Bender, A., et al., "Improved methods for the generation of dendritic cells from nonproliferating progenitors in human blood," *J. Immunol. Methods* 196:121-135, Elsevier Science (1996).
Ben-Yedidia, T., and Arnon, R., "Design of peptide and polypeptide vaccines," *Curr. Opin. Biotechnol.* 8:442-448, Current Biology, Ltd. (1997).
Carbone, F.R., and Bevan, M.J., "Induction of Ovalbumin-Specific Cytotoxic T Cells by In Vivo Peptide Immunization," *J. Exp. Med.* 169:603-612, Rockefeller University Press (1989).
Carbone, F.R., et al., "Induction of Cytotoxic T Lymphocytes by Primary In Vitro Stimulation with Peptides," *J. Exp. Med.* 167:1767-1779, Rockefeller University Press (1988).
Cassell, D., and Forman, J., "Linked Recognition of Helper and Cytotoxic Antigenic Determinants for the Generation of Cytotoxic T Lymphocytes," *Ann. N.Y. Acad. Sci.* 532:51-60, New York Academy Of Sciences (1991).
Deres, K., et al., "In vivo priming of virus-specific cytotoxic T lymphocytes with synthetic lipopeptide vaccine," *Nature* 342:561-564, Nature Publishing Group (1989).
del Guercio, M-F., et al., "Potent immunogenic short linear peptide constructs composed of B cell epitopes and Pan DR T Helper Epitopes (PADRE) for antibody responses in vivo," *Vaccine* 15:441-448, Elsevier Science (Mar. 1997).
DiBrino, M., et al., "Endogenous Peptides with Distinct Amino Acid Anchor Residue Motifs Bind to HLA-A1 and HLA-B8," *J. Immunol.* 152:620-631, American Association of Immunologists (1994).
DiBrino, M., et al., "The HLA-B14 Peptide Binding Site Can Accommodate Peptides with Different Combinations of Anchor Residues," *J. Biol. Chem.* 269:32426-32434, American Society for Biochemistry and Molecular Biology (1994).

Donnelly, J.J., et al., "DNA Vaccines," *Annu. Rev. Immunol. 15*:617-648, Annual Reviews Inc. (Apr.1997).

Francis, M.J., et al., "Non-responsiveness to a foot-and-mouth disease virus peptide overcome by addition of foreign helper T-cell determinants," *Nature 330*:168-170, Nature Publication Group (1987).

Fynan, E.F., et al., "DNA vaccines: Protective immunizations by parental, mucosal, and gene-gun inoculations," *Proc. Natl. Acad. Sci. USA 90*:11478-11482, National Academy of Sciences (1993).

Gileadi, U., et al., "Effect of epitope flanking residues on the presentation of N-terminal cytotoxic T lymphocyte epitopes," *Eur. J. Immunol. 29*:2213-2222, Wiley-VCH Verlag GmbH (Jul. 1999).

Golvano, J., et al., "Polarity of immunogens: implications for vaccine design," *Eur. J. Immunol. 20*:2363-2366, VCH Verlagsgesellschaft mbH (1990).

Gulukota, K., et al., "Two Complementary Methods for Predicting Peptides Binding Major Histocompatibility Complex Molecules," *J. Mol. Biol. 267*:1258-1267, Academic Press Limited (Apr. 1997).

Hahn, Y.S., et al., "CD8$^+$ T Cell Recognition of an Endogenously Processed Epitope is Regulated Primarily by Residues within the Epitope," *J. Exp. Med. 176*:1335-1341, Rockefeller University Press (1992).

Hahn, Y.S., et al., "Presentation of Viral Antigen to Class I Major Histocompatibility Complex-Restricted Cytotoxic T Lymphocyte. Recognition of an Immunodominant Influenza Hemagglutinin Site by Cytotoxic T Lymphocyte is Independent of the Position of the Site in the Hemagglutinin Translation Product," *J. Exp. Med. 174*:733-736, Rockefeller University Press (1991).

Hammer, J., et al., "Precise Prediction of Major Histocompatibility Complex Class II-Peptide Interaction Based on Peptide Side Chain Scanning," *J. Exp. Med. 180*:2353-2358, Rockefeller University Press (1994).

Hill, C.M., et al., "Exploration of Requirements for Peptide Binding to HLA DRB1*0101 and DRB1*0401," *J. Immunol. 152*:2890-2898, American Association of Immunologists (1994).

Huczko, E.L., et al., "Characteristics of Endogenous Peptides Eluted from the Class I MHC Molecule HLA-B7 Determined by Mass Spectrometry and Computer Modeling," *J. Immunol. 151*:2572-2587, American Association of Immunologists (1993).

Ishioka, G.Y., et al., "Class I MHC-restricted, peptide specific cytotoxic T lymphocytes generated by peptide priming in vivo," in *Vaccinies90: Modern Approaches to New Vaccines Including Prevention of AIDS*, Brown, F., et al., eds., Cold Spring harbor Laboratory Press, Cold Spring Harbor, NY, pp. 7-11 (1990).

Ishioka, G.Y., et al., "Induction of Class I MHC-Restricted, Peptide-Specific Cytolytic T Lymphocytes by Peptide Priming In Vivo," *J. Immunol. 143*:1094-1100, American Association of Immunologists (1989).

Jardetzky, T.S., et al., "Peptide binding to HLA-DR1: a peptide with most residues substituted to alanine retains MHC binding," *EMBO J. 9*:1797-1803, Oxford University Press (1990).

Kast, W.M., et al., "Protection against lethal Sendai virus infection by in vivo priming of virus-specific cytotoxic T lymphocytes with a free synthetic peptide," *Proc. Natl. Acad. Sci. USA 88*:2283-2287, National Academy of Sciences (1991).

Kondo, A., et al., "Two disticnt HLA-A*0101-specific submotifs illustrate alternative peptide binding modes," *Immunogenetics 45*:249-258, Springer-Verlag (Jan. 1997).

Kubitscheck, U., et al., "Peptide Binding to Class I Molecules of the Major Histocompatibility Complex on the Surface of Living Target Cells," *Scand. J. Immunol. 36*:341-348, Blackwell Scientific Publications (1992).

Kubo, R.T., et al., "Definition of Specific Peptide Motifs for Four Major HLA-A Alleles," *J. Immunol. 152*:3913-3924, American Association of Immunologists (1994).

Kumar, A., et al., "Universal T Helper Cell Determinants Enhance Immunogenicity of a *Plasmodium falciparum* Merozoite Surface Antigen Peptide," *J. Immunol. 148*:1499-1505, American Association of Immunologists (1992).

Lasarte, J-J., et al., "Induction fo Cytotoxic T Lymphocytes in Mice against the Principal Neutralizing Domain of HIV-1 by Immunization with an Engineered T-Cytotoxic-T-Helper Synthetic Helper Peptide Construct," *Cell. Immunol. 141*:211-218, Academic Press Inc. (1992).

Madden, D.R., et al., "The structure of HLA-B27 reveals nonamer self-peptides bound in an extended conformation," *Nature 353*:321-325, Nature Publishing Group (1991).

Maier, R., et al., "Peptide motifs of HLA-A3, -A24, and -B7 molecules as determined by pool sequencing," *Immunogenetics 40*:306-308, Springer-Verlag (1994).

Martinon, F., et al., "Immunization of Mice with Lipopeptides Bypasses the Prerequisite for Adjuvant," *J. Immunol. 149*:3416-3422, American Association of Immunologists (1992).

Niedermann, G., et al., "Contribution of Proteasome-Mediated Proteolysis to the Hierarchy of Epitopes Presented by Major Histocompatibility Complex Class I Molecules," *Immunity 2*:289-299, Cell Press (1995).

Niedermann, G., et al., "The specificity of proteasomes: impact on MHC class I processing and presentation of antigens," *Immunol. Rev. 172*:29-48, Munksgaard (Dec. 1999).

Nikolić-Žugić, J., and Carbone, F.R., "Peptide Presentation by Class-I Major Histocompatibility Complex Molecules," *Immunol. Res. 10*:54-65, S. Karger AG (1991).

O'Sullivan, D., et al., "Characterization of the Specificity of Peptide Binding to Four DR Haplotypes," *J. Immunol. 145*:1799-1808, American Association of Immunologists (1990).

O'Sullivan, D., et al., "On the Interaction of Promiscuous Antigenic Peptides with Different DR Alleles," *J. Immunol. 147*:2663-2669, American Association of Immunologists (1991).

Panina-Bordignon, P., et al., "Universally immunogenic T cell eptiopes: promiscuous binding to human MHC class II and promiscuous recognition by T cells," *Eur. J. Immunol. 19*:2237-2242, VCH Verlagsgesellschaft mbH (1989).

Paz, P., et al., "Discrete Proteolytic Intermediates in the MHC Class I Antigen Processing Pathway and MHC I-Dependent Peptide Trimming in the ER," *Immunity 11*:241-251, Cell Press (Aug. 1999).

Penna, A., et al., "Cytotoxic T Lymphocytes Recognize an HLA-A2-Restricted Epitope Within the Hepatitis B Virus Nucleocapsid Antigen," *J. Exp. Med. 174*:1565-1570, Rockefeller University Press (1991).

Pryjma, J.,et al., "Induction and Suppression of Immunoglobulin Synthesis in Cultures of Human Lymphocytes: Effects of Pokeweed Mitogen and *Staphylococcus aureus* Cowan I," *J. Immunol. 124*:656-661, Williams & Wilkins Co. (1980).

Rahemtulla, A., et al., "Normal development and function of CD8$^+$ cells but markedly decreased helper cell activity in mice lacking CD4," *Nature 353*:180-183, Nature Publishing Group (1991).

Rammensee, H-G., et al., "SYFPEITHI: database for MHC ligands and peptide motifs," *Immunogenetics 50*:213-219, Springer-Verlag (Nov. 1999).

Reitermann, A., et al., "Lipopeptide Derivatives of Bacterial Lipoprotein Constitute Potent Immune Adjuvants Combined with or Covalently Coupled to Antigen or Hapten," *Biol. Chem. Hoppe Seyler 370*:343-352, Walter De Gruyter (1989).

Restifo, N.P., et al., "Antigen Processing In Vivo and the Elicitation of Primary CTL Responses," *J. Immunol. 154*:4414-4422, American Association of Immunologists (1995).

Saper, M.A., et al., "Refined Structure of the Human Histocompatibility Antigen HLA-A2 at 2.5 Å Resolution," *J. Mol. Biol. 219*:277-319, Academic Press Ltd. (1991).

Schaeffer, E.B., et al., "Relative contribution of 'determinant selection' and 'holes in the T-cell repertoire' to T-cell responses," *Proc. Natl. Acad. Sci. USA 86*:4649-4653, National Academy of Sciences (1989).

Schumacher, T.N.M., et al., "Peptide selection by MHC class I molecules," *Nature 350*:703-706, Nature Publishing Group (1991).

Sette, A., and Sidney, J., "HLA supertypes and supermotifs: a functional perspective on HLA polymorphism," *Curr. Opin. Immunol. 10*:478-482, Current Biology Publications (Aug. 1998).

Sette, A., et al., "A Novel Approach to the Generation of High Affinity Class II-Binding Peptides," *J. Immunol. 145*:1809-1813, American Association of Immunologists (1990).

Sette, A., et al., "Effect of Conformational Propensity of Peptide Antigens in Their Interaction with MHC Class II Molecules," *J. Immunol.* 143:1268-1273, American Association of Immunologists (1989).

Sette, A., et al., "Peptide Binding to the Most Frequent HLA-A Class I Alleles Measured by Quantitative Molecular Binding Assays," *Mol. Immunol.* 31:813-822, Pergamon Press (1994).

Sidney, J., et al., "Definition of an HLA-A3-Like Supermotif Demonstrates the Overlapping Peptide-Binding Repertoires of Common HLA Molecules," *Hum. Immunol.* 45:79-93, Elsevier Science Inc. (1996).

Sidney, J., et al., "Practical, biochemical and evolutionary implications of the discovery of HLA class I supermotifs," *Immunol. Today* 17:261-266, Elsevier Science (1996).

Sidney, J., et al., "The HLA-A*0207 Peptide Binding Repertoire is Limited to a Subset of the A*0201 Repertoire," *Hum. Immunol.* 58:12-20, Elsevier Science Inc. (Nov. 1997).

Sinigaglia, F., and Hammer, J., "Defining rules for the peptide-MHC class II interaction," *Curr. Opin. Immunol.* 6:52-56, Current Biology Ltd. (1994).

Southwood, S., et al., "Several Common HLA-DR types Share Largely Overlapping Peptide Binding Repertoires," *J. Immunol.* 160:3363-3373, American Association of Immunologists (Apr. 1998).

Sprent, J., and Schaefer, M., "Properties of Purified T Cell Subsets. I. In Vitro Responses to Class I vs. Class II H-2 Alloantigens," *J. Exp. Med.* 162:2068-2088, Rockefeller University Press (1985).

Stark, J.M., et al., "Immunogenicity of liqid-conjugated antigens. I. The Influence of Chain Length and Degree of Conjugation on Induction of Antibody in Mice," *Immunology* 39:345-352, Blackwell Scientific Publications (1980).

Steinman, R.M., "Dendritic cells and immune-based therapies," *Exp. Hematol.* 24:859-862, Elsevier Science Inc. (1996).

Sudo, T., et al., "Differences in MHC Class I Self Peptide Repertoires Among HLA-A2 Subtypes," *J. Immunol.* 155:4749-4756, American Association of Immunologists (1995).

Sugawara, S., et al., "A simple method to eliminte the antigenicity of surface class I MHC molecules from the membrane of viable cells by acid treatment at pH 3," *J. Immunol. Methods* 100:83-90, Elsevier Science (1987).

Tam, J.P., and Lu, Y.-A., "Vaccine engineering: Enhancement of immunogenicity of synthetic peptide vaccines related to hepatitis in chemically defined models consisting of T- and B-cell epitopes," *Proc. Natl. Acad. Sci. USA* 86:9084-9088, National Academy of Sciences (1989).

Townsend, A., and Bodmer, H., "Antigen Recognition by Class I-Restricted T Lymphocytes," *Ann. Rev. Immunol.* 7:601-624, Annual Reviews, Inc. (1989).

von Boehmer, H., and Haas, W., "Distinct Ir Genes for Helper and Killer Cells in the Cytotoxic Response to H-Y Antigen," *J. Exp. Med.* 150:1134-1142, Rockefeller University Press (1979).

Watari, E., et al.,"A Synthetic Peptide Induces Long-Term Protection from Lethal Infection with Herpes Simplex Virus 2," *J. Exp. Med.* 165:459-470, Rockefeller University Press (1987).

Wentworth, P.A., et al., "In Vitro Induction of Primary, Antigen-Specific CTL from Human Peripheral Blood Mononuclear Cells Stimulated with Synthetic Peptides," *Mol. Immunol.* 32:603-612, Elsevier Science Ltd. (1995).

Wherry, E.J., et al., "The Induction of Virus-Specific CTL as a Function of Increasing Epitope Expression: Responses Rise Steadily Until Excessively High Levels of Epitope Are Attained," *J. Immunol.* 163:3735-3745, American Association of Immunologists (Oct. 1999).

Widmann, C., et al., "T helper epitopes enhance the cytotoxic response of mice immunized with MHC class I-restriced malaria peptides," *J. Immunol. Meth.* 155:95-99, Elsevier Science Publishers B.V. (1992)

Wiesmüller, K-H., et al., "Lipopeptide-Helper-T-Cell Epitope-CTL Epitope Conjugate Induces Antibodies Against the CTL Epitope," *Innovation Perspective Solid Phase Synthesis Collect. Papers, Int. Symp. 2nd*, pp. 499-502 (1991).

Wiesmüller, K-H., et al., "Novel low-molecular-weight synthetic vaccine against foot-and mouth disease containing a potent B cell and macrophage activator," *Vaccine* 7:29-33, Butterworth & Co. (1989).

Yewdell, J.W., and Bennink, J.R., "Immunodominance in Major Histocompatibility Complex Class I-Restricted T Lymphocyte Responses," *Annu. Rev. Immunol.* 17:51-88, Annual Reviews Inc. (Apr. 1999).

Zhou, X., et al., "In vivo primary induction of virus-specific CTL by immunization with 9-mer synthetic peptides," *J. Immunol. Methods* 153:193-200, Elsevier Science Publishers B.V. (1992).

Zinkernagel, R.M., et al., "The Lymphoreticular System in Triggering Virus Plus Self-Specific Cytotoxic T Cells: Evidence for T Help," *J. Exp. Med.* 147:897-911, Rockefeller University Press (1978).

Altuvia, Y. et al., "A Structure-Based Algorithm to Predict Potential Binding Peptides to MHC Molecules with Hydrophobic Binding Pockets," *Human Immunol.* 58:1-11, Elsevier Science Inc. (1997).

Aichele, P., et al., "Antiviral cytotoxic T cell response induced by in vivo priming with a free synthetic peptide," *J. Exp. Med.* 171:1815-1820, Rockefeller University Press (1990).

Alexander, J., et al., "Derivation of HLA-A11/$K^b$ Transgenic Mice. Functional CTL Repertoire and Recognition of Human All-Restricted CTL Epitopes," *J. Immunol.* 159:4753-4761, The American Association of Immunologists (Nov. 1997).

Bergmann, C.C., et al., "Differential Effects of Flanking Residues on Presentation of Epitopes from Chimeric Peptides," *J. Virol.* 68:5306-5310, American Society for Microbiology (Aug. 1994).

Bertoni, R., et al., "Human Histocompatibility Leukocyte Antigen-binding Supermotifs Predict Broadly Cross-reactive Cytotoxic T Lymphocyte Responses in Patients with Acute Hepatitis," *J. Clin. Invest.* 100:503-513, The American Society for Clinical Investigation, Inc. (Aug. 1997).

Bertoni, R., et al., "Human Class I Supertypes and CTL Repertoires Extend to Chimpanzees," *J. Immunol.* 161:4447-4455, American Association of Immunologists (Oct. 1998).

Bjorkman, P.J., et al., "Structure of the human class I histocompatibility antigen, HLA-A2," *Nature* 329:506-512, Macmillan Publishers, Ltd. (1987).

Bjorkman, P.J., et al., "The foreign antigen binding site and T cell recognition regions of class I histocompatibility antigens," *Nature* 329:512-518, Macmillan Publishers, Ltd. (1987).

Buus, S., et al., "Autologous Peptides Constitutively Occupy the Antigen Binding Site on Ia," *Science* 242:1045-1047, American Association for the Advancement of Science (1988).

Carreno, B.M., et al., "HLA-B37 and HLA-A2.1 molecules bind largely nonoverlapping sets of peptides," *Proc. Natl. Acad. Sci. USA* 87:3420-3424, National Academy Press (1990).

Corr, M., et al., "Endogenous Peptides on a Soluble Major Histocompatibility Complex Class I Molecule, H-$2L^d_s$: Sequence Motif, Quantitative Binding, and Molecular Modeling of the Complex," *J. Exp. Med.* 176:1681-1692, Rockefeller University Press (Dec. 1992).

De Bruijn, M.L.H., et al., "Peptide loading of empty major histocompatibility complex molecules on RMA-S cells allows the induction of primary cytotoxic T lymphocyte responses," *Eur. J. Immunol.* 21:2963-2970, VCH Verlagsgesellschaft mbH (1991).

Del Val, M., et al., "Efficient Processing of an Antigenic Sequence for Presentaton by MHC Class I Molecules Depends on Its Neighboring Residues in the Protein," *Cell* 66:1145-1153, Cell Press (1991).

Deres, K., et al. "In vivo priming of virus-specific cytotoxic T lymphocytes with synthetic lipopeptide vaccine," *Nature* 342:561-564, Macmillan Publishers, Ltd. (1989).

DiBrino, M., et al., "HLA-A1 and HLA-A3 T Cell Epitopes Derived from Influenza Virus Proteins Predicted from Peptide Binding Motifs," *J. Immunol.* 151:5930-5935, The Association of Immunologists (Dec. 1993).

DiBrino, M., et al., "Endogenous peptides bound to HLA-A3 possess a specific combination of anchor residues that permit identification of potential antigenic peptides," *Proc. Natl. Acad. Sci. USA* 90:1508-1512, National Academy Press (Feb. 1993).

Ding, Y.-H., et al., "Two Human T Cell Receptors Bind in a Similar Diagonal Mode to the HLA-A2/Tax Peptide Complex Using Different TCR Amino Acids," *Immunity* 8:403-11, Cell Press (Apr. 1998).

Eisenlohr, L.C., et al., "Flanking Sequences Influence the Presentation of an Endogenously Synthesized Peptide to Cytotoxic T Lymphocytes," *J. Exp. Med. 175*:481-487, The Rockfeller University Press (Feb. 1992).

Engelhard, V.H., "Structure of peptides associated with MHC Class I molecules," *Curr. Opin. Immunol. 6*:13-23, Current Biology, Ltd. (Feb. 1994).

Falk, K., et al., "Allele-specific motifs revealed by sequencing of self-peptides eluted from MHC molecules," *Nature 351*:290-296, Macmillan Publishers, Ltd. (1991).

Falk, K., et al., "*MHC peptide motif register*. Peptide motifs of HLA-B35 and -B37 molecules," *Immunogenetics 38*:161-162, Springer-Verlag (Apr. 1993).

Falk, K., et al., "Allele-specific peptide ligand motifs of HLA-C molecules," *Proc. Natl. Acad. Sci. USA 90*:12005-12009, National Academy Press (Dec. 1993).

Falk, K., et al., "Pool sequencing of natural HLA-DR, DQ, and DP ligands reveals detailed peptide motifs, constraints of processing, and general rules," *Immunogenetics 39*:230-242, Springer-Verlag (Feb. 1994).

Falk, K., et al., "Peptide motifs of HLA-A1, -A11, -A31, and -A33 molecules," *Immunogenetics 40*:238-241, Springer-Verlag (Jul. 1994).

Foon, K.A., "Biological Response Modifiers: The New Immunotherapy," *Cancer Res. 49*:1621-1639, American Association for Cancer Research (1989).

Geysen, H.M., et al., "Cognitive Features of Continuous Antigenic Determinants," *J. Mol. Recognit. 1*:32-41, Heyden & Sons, Ltd. (1988).

Guo, H.-C., et al., "Different length peptides bind to HLA-Aw68 similarly at their ends but bulge out in the middle," *Nature 360*:364-366, Macmillan Publishers, Ltd. (Nov. 1992).

Henderson, R.A., et al., "HLA-A2.1-Associated Peptides from a Mutant Cell Line: A Second Pathway of Antigen Presentation," *Science 255*:1264-1266, American Association for the Advancement of Science (Mar. 1992).

Hill, A., et al., "Characterization of two Epstein-Barr virus epitopes restricted by HLA-B7," *Eur. J. Immunol. 25*:18-24, VCH Verlagsgesellschaft mbH (Jan. 1995).

Hunt, D.F., et al., "Characterization of Peptides Bound to the Class I MHC Molecule HLA-A2.1 by Mass Spectrometry," *Science 255*:1261-1263, American Association for the Advancement of Science (Mar. 1992).

Ishioka, G.Y., et al., "Utilization of MHC Class I Transgenic Mice for Development of Minigene DNA Vaccines Encoding Multiple HLA-Restricted CTL Epitopes," *J. Immunol. 162*:3915-3925, The American Association of Immunologists (Apr. 1999).

Jameson, S.C., and Bevan, M.J., "Dissection of major histocompatibility complex (MHC) and T cell receptor contact residues in a $K^b$-restricted ovalbumin peptide and an assessment of the predictive power of MHC-binding motifs," *Eur. J. Immunol. 22*:2663-2667, VCH Verlagsgesellschaft mbH (Oct. 1992).

Jardetzky, T.S., et al., "Identification of self peptides bound to purified HLA-B27," *Nature 353*:326-329, Macmillan Publishers, Ltd. (1991).

Kannagi, M., et al., "Target Epitope in the Tax Protein of Human T-Cell Leukemia Virus Type I Recognized by Class I Major Histocompatibility Complex-Restricted Cells," *J. Virol. 66*:2928-2933, American Society for Microbiology (May 1992).

Kast, W.M., et al., "Strict peptide length is not required for the induction of cytotoxic T lymphocyte-mediated antiviral protection by peptide vaccination," *Eur. J. Immunol. 23*:1189-1192, VCH Verlagsgesellschaft mbH (May 1993).

Krieger, J.I., et al., "Single amino acid changes in DR and antigen define residues critical for peptide-MHC binding and T cell recognition," *J. Immunol. 146*:2331-2340, American Association of Immunologists (1991).

Lipford, G.B., et al., "Primary in vivo Responses to Ovalbumin. Probing the Predictive Value of the $K^b$ Binding Motif," *J. Immunol. 150*:1212-1222, The American Association of Immunologists (Feb. 1993).

Maryanski, J.L., et al., "Synthetic peptides as antigens and competitors in recognition by H-2-restricted cytolytic T cells specific for HLA," *J. Exp. Med. 167*:1391-1405, Rockefeller University Press (1988).

Maryanski, J.L., t al., "Competitor Analogs for Defined T Cell Antigens: Peptides Incorporating a Putative Binding Motif and Polyproline or Polyglycine Spacers," *Cell 60*:63-72, Cell Press (1990).

Morrison, J., et al., "Identification of the nonamer peptide from influenza A matrix protein and the role of pockets of HLA-A2 in its recognition by cytotoxic T lymphocytes," *Eur. J. Immunol. 22*:903-907, VCH Verlagsgesellschaft mbH (Apr. 1992).

Niedermann, G., et al., "The proteolytic fragments generated by vertebrate proteosomes: Structural relationships to major histocompatibility complex class I binding peptides," *Proc. Natl. Acad. Sci. USA 93*:8572-8577, National Academy Press (Aug. 1996).

Ochoa-Garay, J., et al., "The ability of peptides to induce cytotoxic T cells in vitro does not strongly correlate with their affinity for the $H-2L^d$ molecule: implications for vaccine design and immunotherapy," *Mol. Immunol. 34*:273-281, Elsevier Science, Ltd. (Feb. 1997).

Pamer, E.G., et al., "Precise prediction of a dominant class I MHC-restricted epitome of *Listeria monocytogenes*," *Nature 353*:852-855, Macmillan Publishers, Ltd. (1991).

Parham, P., et al., "The Origins of HLA-A,B,C Polymorphism," *Immunol. Rev. 143*:141-180, Munksgaard (Feb. 1995).

Parker, K.C., et al., "Peptide Binding to HLA-A2 and HLA-B27 Isolated from *Escherichia coli*," *J. Biol. Chem. 267*:5451-5459, American Society for Biochemistry and Molecular Biology, Inc. (Mar. 1992).

Parker, K.C., et al., "Sequence motifs important for peptide binding to the human MHC class I molecule, HLA-A2," *J. Immunol. 149*:3580-3587, American Association of Immunologists (Dec. 1992).

Rammensee, H.-G., et al., "Peptides Naturally Presented by MHC Class I Molecules," *Annu. Rev. Immunol. 11*:213-224, Annual Reviews, Inc. (Jan. 1993).

Rammensee, H.-G., et al., "MHC ligands and peptide motifs: first listing," *Immunogenetics 41*:178-228, Springer-Verlag (Feb. 1995).

Reddehase, M.J., et al., "A pentapeptide as minimal antigenic determinant for MHC class I-restricted T lymphocytes," *Nature 337*:651-653, Macmillan Publishers, Ltd. (1989).

Romero, P., et al., "$H-2K^d$-restricted Antigenic Peptides Share a Simple Binding Motif," *J. Exp. Med. 174*:603-612, Rockefeller University Press (1991).

Rothbard, J.B., "Major histocompatibility complex-peptide interactions," *Curr. Opin. Immunol. 2*:99-105, Current Biology, Ltd. (1989).

Rötzschke, O., et al., "Isolation and analysis of naturally processed viral peptides as recognized by cytotoxic T cells," *Nature 348*:252-254, Macmillan Publishers, Ltd. (1990).

Rötzschke, O., et al., "Characterization of Naturally Occurring Minor Histocompatibility Peptides Including H-4 and H-Y," *Science 249*:283-287, American Association for the Advancement of Science (1990).

Rötzschke, O., and Falk, K., "Naturally-occurring peptide antigens derived from the MHC class-I-restricted processing pathway," *Immunol. Today 12*:447-455, Elsevier Science Publishers, Ltd. (1991).

Ruppert, J., et al., "Prominent Role of Secondary Anchor Residues in Peptide Binding to HLA-A2.1 Molecules," *Cell 74*:929-937, Cell Press (Sep. 1993).

Schulz, M., et al., "Major histocompatibility complex binding and T cell recognition of a viral nonapeptide containing a minimal tetrapeptide," *Eur. J. Immunol. 21*:1181-1185, VCH Verlagsgesellschaft mbH (1991).

Sette, A., et al., "Prediction of major histocompatibility complex binding regions of protein antigens by sequence pattern analysis," *Proc. Natl. Acad. Sci. USA 86*:3296-3300, National Academy Press (1989).

Sette, A., et al., "Random association between the peptide repertoire of A2.1 class I and several different DR class II molecules," *J. Immunol. 147*:3893-3900, The American Association of Immunologists (1991).

Sette, A., et al., "The Relationship Between Class I Binding Affinity and Immunogenicity of Potential Cytotoxic T Cell Epitopes," *J. Immunol. 153*:5586-5592, The American Association of Immunologists (Dec. 1994).

Shastri, N., et al., "Presentation of Endogenous Peptide/MHC Class I Complexes Is Profoundly Influenced by Specific C-Terminal Flanking Residues," *J. Immunol. 155*:4339-4346, The American Association of Immunologists (Nov. 1995).

Sherman, L.A., et al., "Extracellular Processing of Peptide Antigens That Bind Class I Major Histocompatibility Molecules," *J. Exp. Med. 175*:1221-1226, The Rockefeller University Press (May 1992).

Shimojo, N., et al., "Specificity of peptide binding by the HLA-A2.1 molecule," *J. Immunol. 143*:2939-2947, The American Association of Immunologists (1989).

Sidney, J., et al., "Several HLA Alleles Share Overlapping Peptide Specificities," *J. Immunol. 154*:247-259, The American Association of Immunologists (Jan. 1995).

Threlkeld, S.C., et al., "Degenerate and Promiscuous Recognition by CTL of Peptides Presented by the MHC Class I A3-like Superfamily, Implications for Vaccine Development," *J. Immunol. 159*:1648-1657, The American Association of Immunologists (Aug. 1997).

Wentworth, P.A., et al., "Differences and similarities in the A2.1-restricted cytotoxic T cell repertoire in humans and human leukocyte antigen-transgenic mice," *Eur. J. Immunol. 26*:97-101, VCH Verlagsgesellschaft mbH (Jan. 1996).

Whitton, J.L., et al., "Molecular Analyses of a Five-Amino-Acid Cytotoxic T-Lymphocyte (CTL) Epitope: an Immunodominant Region Which Induces Nonreciprocal CTL Cross-Reactivity," *J. Virol. 63*:4303-4310, American Society for Microbiology (1989).

Yewdell, J.W., and Bennink, J.R., "Cell Biology of Antigen Processing and Presentation to Major Histocompatibility Complex Class I Molecule-Restricted T Lymphocytes," *Adv. Immunol. 52*:1-123, Academic Press (Jul. 1992).

York, I.A., and Rock, K.L., "Antigen processing and presentation by the class I major histocompatibility complex," *Annu. Rev. Immunol. 14*:369-396, Annual Reviews, Inc. (Apr. 1996).

Zhang, Q-J., et al., "An HLA-A11-specific motif in nonamer peptides derived from viral and cellular proteins," *Proc. Natl. Acad. Sci. USA 90*:2217-2221, National Academy Press (Mar. 1993).

Parker, K.C., et al., "Scheme for Ranking Potential HLA-A2 Binding Peptides Based on Independent Binding of Individual Peptide Side-Chains," *J. Immunol. 152*:163-175, The American Association of Immunologists (Jan. 1994).

Dialog File 351, Accession No. 7180926, Derwent WPI English language abstract for EP 0 226 513, 1987.

Dialog File 351, Accession No. 9263567, Derwent WPI English language abstract for WO 92/21033, 1992.

Dialog File 351, Accession No. 9888606, Derwent WPI English language abstract for WO 94/11738, 1994.

Co-pending U.S. Appl. No. 11/027,670 to Sette et al.

\* cited by examiner

```
                       SEQUENCE LISTING

<160> NUMBER OF SEQ ID NOS: 88

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:peptide
      epitope HPV 16 protein E1 starting at position 206

<400> SEQUENCE: 1

Ala Met Leu Ala Lys Phe Lys Glu Leu Tyr
  1               5                  10

<210> SEQ ID NO 2
<211> LENGTH: 649
<212> TYPE: PRT
<213> ORGANISM: Human papillomavirus type 6a
```

```
<400> SEQUENCE: 2

Met Ala Asp Asp Ser Gly Thr Glu Asn Glu Gly Ser Gly Cys Thr Gly
  1               5                  10                  15

Trp Phe Met Val Glu Ala Ile Val Gln His Pro Thr Gly Thr Gln Ile
             20                  25                  30

Ser Asp Asp Glu Asp Glu Glu Val Glu Asp Ser Gly Tyr Asp Met Val
         35                  40                  45

Asp Phe Ile Asp Asp Ser Asn Ile Thr His Asn Ser Leu Glu Ala Gln
     50                  55                  60

Ala Leu Phe Asn Arg Gln Glu Ala Asp Thr His Tyr Ala Thr Val Gln
 65                  70                  75                  80

Asp Leu Lys Arg Lys Tyr Leu Gly Ser Pro Tyr Val Ser Pro Ile Asn
                 85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
        115                 120                 125

Thr Arg Glu Leu Thr Asp Ser Gly Tyr Gly Tyr Ser Glu Val Glu Ala
130                 135                 140

Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
        195                 200                 205

Leu Gly Lys Phe Lys Glu Cys Phe Gly Leu Ser Phe Ile Asp Leu Ile
    210                 215                 220

Arg Pro Phe Lys Ser Asp Lys Thr Thr Cys Ala Asp Trp Val Val Ala
225                 230                 235                 240

Gly Phe Gly Ile His His Ser Ile Ser Glu Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Val Arg Phe Lys Val Asn Lys Ser Arg
        275                 280                 285

Ser Thr Val Ala Arg Thr Leu Ala Thr Leu Leu Asn Ile Pro Asp Asn
    290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
    370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
```

```
                    405                 410                 415
Glu Met Arg Lys Met Ser Ile Lys Gln Trp Ile Lys His Arg Gly Ser
                420                 425                 430
Lys Ile Glu Gly Thr Gly Asn Trp Lys Pro Ile Val Gln Phe Leu Arg
            435                 440                 445
His Gln Asn Ile Glu Phe Ile Pro Phe Leu Ser Lys Phe Lys Leu Trp
        450                 455                 460
Leu His Gly Thr Pro Lys Lys Asn Cys Ile Ala Ile Val Gly Pro Pro
465                 470                 475                 480
Asp Thr Gly Lys Ser Tyr Phe Cys Met Ser Leu Ile Ser Phe Leu Gly
                485                 490                 495
Gly Thr Val Ile Ser His Val Asn Ser Ser Ser His Phe Trp Leu Gln
            500                 505                 510
Pro Leu Val Asp Ala Lys Val Ala Leu Leu Asp Asp Ala Thr Gln Pro
        515                 520                 525
Cys Trp Ile Tyr Met Asp Thr Tyr Met Arg Asn Leu Leu Asp Gly Asn
        530                 535                 540
Pro Met Ser Ile Asp Arg Lys His Lys Ala Leu Thr Leu Ile Lys Cys
545                 550                 555                 560
Pro Pro Leu Leu Val Thr Ser Asn Ile Asp Ile Thr Lys Glu Glu Lys
                565                 570                 575
Tyr Lys Tyr Leu His Thr Arg Val Thr Thr Phe Thr Phe Pro Asn Pro
            580                 585                 590
Phe Pro Phe Asp Arg Asn Gly Asn Ala Val Tyr Glu Leu Ser Asn Ala
        595                 600                 605
Asn Trp Lys Cys Phe Phe Glu Arg Leu Ser Ser Ser Leu Asp Ile Gln
        610                 615                 620
Asp Ser Glu Asp Glu Glu Asp Gly Ser Asn Ser Gln Ala Phe Arg Cys
625                 630                 635                 640
Val Pro Gly Thr Val Val Arg Thr Leu
                645

<210> SEQ ID NO 3
<211> LENGTH: 368
<212> TYPE: PRT
<213> ORGANISM: Human papillomavirus type 6a

<400> SEQUENCE: 3

Met Glu Ala Ile Ala Lys Arg Leu Asp Ala Cys Gln Glu Gln Leu Leu
1               5                   10                  15
Glu Leu Tyr Glu Glu Asn Ser Thr Asp Leu Asn Lys His Val Leu His
                20                  25                  30
Trp Lys Cys Met Arg His Glu Ser Val Leu Leu Tyr Lys Ala Lys Gln
            35                  40                  45
Met Gly Leu Ser His Ile Gly Met Gln Val Val Pro Pro Leu Lys Val
        50                  55                  60
Ser Glu Ala Lys Gly His Asn Ala Ile Glu Met Gln Met His Leu Glu
65                  70                  75                  80
Ser Leu Leu Lys Thr Glu Tyr Ser Met Glu Pro Trp Thr Leu Gln Glu
                85                  90                  95
Thr Ser Tyr Glu Met Trp Gln Thr Pro Pro Lys Arg Cys Phe Lys Lys
            100                 105                 110
Arg Gly Lys Thr Val Glu Val Lys Phe Asp Gly Cys Ala Asn Asn Thr
        115                 120                 125
```

-continued

```
Met Asp Tyr Val Val Trp Thr Asp Val Tyr Val Gln Asp Thr Asp Ser
        130                 135                 140

Trp Val Lys Val His Ser Met Val Asp Ala Lys Gly Ile Tyr Tyr Thr
145                 150                 155                 160

Cys Gly Gln Phe Lys Thr Tyr Tyr Val Asn Phe Val Lys Glu Ala Glu
                165                 170                 175

Lys Tyr Gly Ser Thr Lys Gln Trp Glu Val Cys Tyr Gly Ser Thr Val
            180                 185                 190

Ile Cys Ser Pro Ala Ser Val Ser Thr Thr Gln Glu Val Ser Ile
        195                 200                 205

Pro Glu Ser Thr Thr Tyr Thr Pro Ala Gln Thr Ser Thr Pro Val Ser
    210                 215                 220

Ser Ser Thr Gln Glu Asp Ala Val Gln Thr Pro Pro Arg Lys Arg Ala
225                 230                 235                 240

Arg Gly Val Gln Gln Ser Pro Cys Asn Ala Leu Cys Val Ala His Ile
                245                 250                 255

Gly Pro Val Asp Ser Gly Asn His Asn Leu Ile Thr Asn Asn His Asp
            260                 265                 270

Gln His Gln Arg Arg Asn Asn Ser Asn Ser Ser Ala Thr Pro Ile Val
        275                 280                 285

Gln Phe Gln Gly Glu Ser Asn Cys Leu Lys Cys Phe Arg Tyr Arg Leu
    290                 295                 300

Asn Asp Lys His Arg His Leu Phe Asp Leu Ile Ser Ser Thr Trp His
305                 310                 315                 320

Trp Ala Ser Pro Lys Ala Pro His Lys His Ala Ile Val Thr Val Thr
                325                 330                 335

Tyr His Ser Glu Glu Gln Arg Gln Gln Phe Leu Asn Val Val Lys Ile
            340                 345                 350

Pro Pro Thr Ile Arg His Lys Leu Gly Phe Met Ser Leu His Leu Leu
        355                 360                 365

<210> SEQ ID NO 4
<211> LENGTH: 99
<212> TYPE: PRT
<213> ORGANISM: Human papillomavirus type 6a

<400> SEQUENCE: 4

Met Ala Ala Gln Leu Tyr Val Leu Leu His Leu Tyr Leu Ala Leu His
  1               5                  10                  15

Lys Lys Tyr Pro Phe Leu Asn Leu Leu His Thr Pro His Arg Pro
                20                  25                  30

Pro Pro Leu Cys Pro Gln Ala Pro Arg Lys Thr Gln Cys Lys Arg Arg
            35                  40                  45

Leu Glu Asn Glu His Glu Glu Ser Asn Ser His Leu Ala Thr Pro Cys
    50                  55                  60

Val Trp Pro Thr Leu Asp Pro Trp Thr Val Glu Thr Thr Thr Ser Ser
65                  70                  75                  80

Leu Thr Ile Thr Thr Ser Thr Lys Glu Gly Thr Thr Val Thr Val Gln
                85                  90                  95

Leu Arg Leu

<210> SEQ ID NO 5
<211> LENGTH: 91
<212> TYPE: PRT
<213> ORGANISM: Human papillomavirus type 6a
```

-continued

```
<400> SEQUENCE: 5

Met Glu Val Val Pro Val Gln Ile Ala Ala Gly Thr Thr Ser Thr Leu
1               5                   10                  15

Ile Leu Pro Val Ile Ile Ala Phe Val Val Cys Phe Val Ser Ile Ile
                20                  25                  30

Leu Ile Val Trp Ile Ser Asp Phe Ile Val Tyr Thr Ser Val Leu Val
            35                  40                  45

Leu Thr Leu Leu Leu Tyr Leu Leu Trp Leu Leu Leu Thr Thr Pro
        50                  55                  60

Leu Gln Phe Phe Leu Leu Thr Leu Leu Val Cys Tyr Cys Pro Ala Leu
65                  70                  75                  80

Tyr Ile His His Tyr Ile Val Asn Thr Gln Gln
                85                  90

<210> SEQ ID NO 6
<211> LENGTH: 150
<212> TYPE: PRT
<213> ORGANISM: Human papillomavirus type 6a

<400> SEQUENCE: 6

Met Glu Ser Ala Asn Ala Ser Thr Ser Ala Thr Thr Ile Asp Gln Leu
1               5                   10                  15

Cys Lys Thr Phe Asn Leu Ser Met His Thr Leu Gln Ile Asn Cys Val
                20                  25                  30

Phe Cys Lys Asn Ala Leu Thr Thr Ala Glu Ile Tyr Ser Tyr Ala Tyr
            35                  40                  45

Lys Gln Leu Lys Val Leu Phe Arg Gly Gly Tyr Pro Tyr Ala Ala Cys
        50                  55                  60

Ala Cys Cys Leu Glu Phe His Gly Lys Ile Asn Gln Tyr Arg His Phe
65                  70                  75                  80

Asp Tyr Ala Gly Tyr Ala Thr Thr Val Glu Glu Glu Thr Lys Gln Asp
                85                  90                  95

Ile Leu Asp Val Leu Ile Arg Cys Tyr Leu Cys His Lys Pro Leu Cys
            100                 105                 110

Glu Val Glu Lys Val Lys His Ile Leu Thr Lys Ala Arg Phe Ile Lys
        115                 120                 125

Leu Asn Cys Thr Trp Lys Gly Arg Cys Leu His Cys Trp Thr Thr Cys
130                 135                 140

Met Glu Asp Met Leu Pro
145                 150

<210> SEQ ID NO 7
<211> LENGTH: 98
<212> TYPE: PRT
<213> ORGANISM: Human papillomavirus type 6a

<400> SEQUENCE: 7

Met His Gly Arg His Val Thr Leu Lys Asp Ile Val Leu Asp Leu Gln
1               5                   10                  15

Pro Pro Asp Pro Val Gly Leu His Cys Tyr Glu Gln Leu Val Asp Ser
                20                  25                  30

Ser Glu Asp Glu Val Asp Glu Val Asp Gly Gln Asp Ser Gln Pro Leu
            35                  40                  45

Lys Gln His Phe Gln Ile Val Thr Cys Cys Cys Gly Cys Asp Ser Asn
        50                  55                  60

Val Arg Leu Val Val Gln Cys Thr Glu Thr Asp Ile Arg Glu Val Gln
```

```
            65                  70                  75                  80
Gln Leu Leu Leu Gly Thr Leu Asp Ile Val Cys Pro Ile Cys Ala Pro
                    85                  90                  95

Lys Thr

<210> SEQ ID NO 8
<211> LENGTH: 500
<212> TYPE: PRT
<213> ORGANISM: Human papillomavirus type 6a

<400> SEQUENCE: 8

Met Trp Arg Pro Ser Asp Ser Thr Val Tyr Val Pro Pro Pro Asn Pro
  1               5                  10                  15

Val Ser Lys Val Val Ala Thr Asp Ala Tyr Val Thr Arg Thr Asn Ile
                 20                  25                  30

Phe Tyr His Ala Ser Ser Arg Leu Leu Ala Val Gly His Pro Tyr
             35                  40                  45

Phe Ser Ile Lys Arg Ala Asn Lys Thr Val Val Pro Lys Val Ser Gly
         50                  55                  60

Tyr Gln Tyr Arg Val Phe Lys Val Val Leu Pro Asp Pro Asn Lys Phe
 65                  70                  75                  80

Ala Leu Pro Asp Ser Ser Leu Phe Asp Pro Thr Thr Gln Arg Leu Val
                 85                  90                  95

Trp Ala Cys Thr Gly Leu Glu Val Gly Arg Gly Gln Pro Leu Gly Val
                100                 105                 110

Gly Val Ser Gly His Pro Phe Leu Asn Lys Tyr Asp Asp Val Glu Asn
            115                 120                 125

Ser Gly Ser Gly Gly Asn Pro Gly Gln Asp Asn Arg Val Asn Val Gly
        130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
```

-continued

```
                340                 345                 350
Ser Asp Tyr Lys Glu Tyr Met Arg His Val Glu Glu Tyr Asp Leu Gln
            355                 360                 365

Phe Ile Phe Gln Leu Cys Ser Ile Thr Leu Ser Ala Glu Val Met Ala
        370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
            435                 440                 445

Lys Phe Ser Ser Glu Leu Asp Gln Tyr Pro Leu Gly Arg Lys Phe Leu
        450                 455                 460

Leu Gln Ser Gly Tyr Arg Gly Arg Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
            500

<210> SEQ ID NO 9
<211> LENGTH: 459
<212> TYPE: PRT
<213> ORGANISM: Human papillomavirus type 6a

<400> SEQUENCE: 9

Met Ala His Ser Arg Ala Arg Arg Lys Arg Ala Ser Ala Thr Gln
1               5                  10                  15

Leu Tyr Gln Thr Cys Lys Leu Thr Gly Thr Cys Pro Pro Asp Val Ile
            20                  25                  30

Pro Lys Val Glu His Asn Thr Ile Ala Asp Gln Ile Leu Lys Trp Gly
        35                  40                  45

Ser Leu Gly Val Phe Phe Gly Gly Leu Gly Ile Gly Thr Gly Ser Gly
    50                  55                  60

Thr Gly Gly Arg Thr Gly Tyr Val Pro Leu Gly Thr Ser Ala Lys Pro
65                  70                  75                  80

Ser Ile Thr Ser Gly Pro Met Ala Arg Pro Pro Val Val Val Glu Pro
                85                  90                  95

Val Ala Pro Ser Asp Pro Ser Ile Val Ser Leu Ile Glu Glu Ser Ala
            100                 105                 110

Ile Ile Asn Ala Gly Ala Pro Glu Ile Val Pro Pro Ala His Gly Gly
        115                 120                 125

Phe Thr Ile Thr Ser Ser Glu Thr Thr Pro Ala Ile Leu Asp Val
    130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Ile Thr Ser His Pro Ile Glu Glu
            180                 185                 190

Ile Pro Leu Asp Thr Phe Val Ile Ser Ser Ser Asp Ser Gly Pro Thr
        195                 200                 205
```

-continued

```
Ser Ser Thr Pro Val Pro Gly Thr Ala Pro Arg Pro Arg Val Gly Leu
    210                 215                 220

Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
                245                 250                 255

Glu Asp Val Ser Val Gln Phe Ser His Asp Ser Ile His Asn Ala Pro
                260                 265                 270

Asp Glu Ala Phe Met Asp Ile Ile Arg Leu His Arg Pro Ala Ile Ala
            275                 280                 285

Ser Arg Arg Gly Leu Val Arg Tyr Ser Arg Ile Gly Gln Arg Gly Ser
    290                 295                 300

Met His Thr Arg Ser Gly Lys His Ile Gly Ala Arg Ile His Tyr Phe
305                 310                 315                 320

Tyr Asp Ile Ser Pro Ile Ala Gln Ala Ala Glu Glu Ile Glu Met His
                325                 330                 335

Pro Leu Val Ala Ala Gln Asp Thr Phe Asp Ile Tyr Ala Glu Ser
                340                 345                 350

Phe Glu Pro Asp Ile Asn Pro Thr Gln His Pro Val Thr Asn Ile Ser
            355                 360                 365

Asp Thr Tyr Leu Thr Ser Thr Pro Asn Thr Val Thr Gln Pro Trp Gly
    370                 375                 380

Asn Thr Thr Val Pro Leu Ser Ser Ile Pro Asn Asp Leu Phe Leu Gln
385                 390                 395                 400

Ser Gly Pro Asp Ile Thr Phe Pro Thr Ala Pro Met Gly Thr Pro Phe
                405                 410                 415

Ser Pro Val Thr Ala Leu Pro Thr Gly Pro Val Phe Ile Thr Gly Ser
            420                 425                 430

Gly Phe Tyr Leu His Pro Ala Trp Tyr Phe Ala Arg Lys Arg Arg Lys
    435                 440                 445

Arg Ile Pro Leu Phe Phe Ser Asp Val Ala Ala
    450                 455

<210> SEQ ID NO 10
<211> LENGTH: 649
<212> TYPE: PRT
<213> ORGANISM: Human papillomavirus type 6b

<400> SEQUENCE: 10

Met Ala Asp Asp Ser Gly Thr Glu Asn Glu Gly Ser Gly Cys Thr Gly
1               5                   10                  15

Trp Phe Met Val Glu Ala Ile Val Gln His Pro Thr Gly Thr Gln Ile
                20                  25                  30

Ser Asp Asp Glu Asp Glu Val Glu Asp Ser Gly Tyr Asp Met Val
            35                  40                  45

Asp Phe Ile Asp Asp Ser Asn Ile Thr His Asn Ser Leu Glu Ala Gln
    50                  55                  60

Ala Leu Phe Asn Arg Gln Glu Ala Asp Thr His Tyr Ala Thr Val Gln
65                  70                  75                  80

Asp Leu Lys Arg Lys Tyr Leu Gly Ser Pro Tyr Val Ser Pro Ile Asn
                85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
    115                 120                 125
```

```
Thr Arg Glu Leu Thr Asp Ser Gly Tyr Gly Tyr Ser Glu Val Glu Ala
        130                 135                 140

Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
        195                 200                 205

Leu Gly Lys Phe Lys Glu Cys Phe Gly Leu Ser Phe Ile Asp Leu Ile
    210                 215                 220

Arg Pro Phe Lys Ser Asp Lys Thr Thr Cys Leu Asp Trp Val Val Ala
225                 230                 235                 240

Gly Phe Gly Ile His His Ser Ile Ser Glu Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Leu Arg Phe Lys Val Asn Lys Ser Arg
        275                 280                 285

Ser Thr Val Ala Arg Thr Leu Ala Thr Leu Leu Asn Ile Pro Glu Asn
    290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
    370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
                405                 410                 415

Glu Met Arg Lys Met Ser Ile Lys Gln Trp Ile Lys His Arg Gly Ser
            420                 425                 430

Lys Ile Glu Gly Thr Gly Asn Trp Lys Pro Ile Val Gln Phe Leu Arg
        435                 440                 445

His Gln Asn Ile Glu Phe Ile Pro Phe Leu Thr Lys Phe Lys Leu Trp
    450                 455                 460

Leu His Gly Thr Pro Lys Lys Asn Cys Ile Ala Ile Val Gly Pro Pro
465                 470                 475                 480

Asp Thr Gly Lys Ser Tyr Phe Cys Met Ser Leu Ile Ser Phe Leu Gly
                485                 490                 495

Gly Thr Val Ile Ser His Val Asn Ser Ser Ser His Phe Trp Leu Gln
            500                 505                 510

Pro Leu Val Asp Ala Lys Val Ala Leu Leu Asp Asp Ala Thr Gln Pro
        515                 520                 525

Cys Trp Ile Tyr Met Asp Thr Tyr Met Arg Asn Leu Leu Asp Gly Asn
530                 535                 540
```

```
Pro Met Ser Ile Asp Arg Lys His Lys Ala Leu Thr Leu Ile Lys Cys
545                 550                 555                 560

Pro Pro Leu Leu Val Thr Ser Asn Ile Asp Ile Thr Lys Glu Asp Lys
                565                 570                 575

Tyr Lys Tyr Leu His Thr Arg Val Thr Thr Phe Thr Phe Pro Asn Pro
            580                 585                 590

Phe Pro Phe Asp Arg Asn Gly Asn Ala Val Tyr Glu Leu Ser Asn Thr
        595                 600                 605

Asn Trp Lys Cys Phe Phe Glu Arg Leu Ser Ser Leu Asp Ile Gln
    610                 615                 620

Asp Ser Glu Asp Glu Glu Asp Gly Ser Asn Ser Gln Ala Phe Arg Cys
625                 630                 635                 640

Val Pro Gly Thr Val Val Arg Thr Leu
                645
```

<210> SEQ ID NO 11
<211> LENGTH: 368
<212> TYPE: PRT
<213> ORGANISM: Human papillomavirus type 6b

<400> SEQUENCE: 11

```
Met Glu Ala Ile Ala Lys Arg Leu Asp Ala Cys Gln Glu Gln Leu Leu
1               5                   10                  15

Glu Leu Tyr Glu Glu Asn Ser Thr Asp Leu His Lys His Val Leu His
            20                  25                  30

Trp Lys Cys Met Arg His Glu Ser Val Leu Leu Tyr Lys Ala Lys Gln
        35                  40                  45

Met Gly Leu Ser His Ile Gly Met Gln Val Val Pro Pro Leu Lys Val
    50                  55                  60

Ser Glu Ala Lys Gly His Asn Ala Ile Glu Met Gln Met His Leu Glu
65                  70                  75                  80

Ser Leu Leu Arg Thr Glu Tyr Ser Met Glu Pro Trp Thr Leu Gln Glu
                85                  90                  95

Thr Ser Tyr Glu Met Trp Gln Thr Pro Pro Lys Arg Cys Phe Lys Lys
            100                 105                 110

Arg Gly Lys Thr Val Glu Val Lys Phe Asp Gly Cys Ala Asn Asn Thr
        115                 120                 125

Met Asp Tyr Val Val Trp Thr Asp Val Tyr Val Gln Asp Asn Asp Thr
    130                 135                 140

Trp Val Lys Val His Ser Met Val Asp Ala Lys Gly Ile Tyr Tyr Thr
145                 150                 155                 160

Cys Gly Gln Phe Lys Thr Tyr Tyr Val Asn Phe Val Lys Glu Ala Glu
                165                 170                 175

Lys Tyr Gly Ser Thr Lys His Trp Glu Val Cys Tyr Gly Ser Thr Val
            180                 185                 190

Ile Cys Ser Pro Ala Ser Val Ser Ser Thr Thr Gln Glu Val Ser Ile
        195                 200                 205

Pro Glu Ser Thr Thr Tyr Thr Pro Ala Gln Thr Thr Thr Leu Val Ser
    210                 215                 220

Ser Ser Thr Lys Glu Asp Ala Val Gln Thr Pro Pro Arg Lys Arg Ala
225                 230                 235                 240

Arg Gly Val Gln Gln Ser Pro Cys Asn Ala Leu Cys Val Ala His Ile
                245                 250                 255

Gly Pro Val Asp Ser Gly Asn His Asn Leu Ile Thr Asn Asn His Asp
            260                 265                 270
```

-continued

Gln His Gln Arg Arg Asn Asn Ser Asn Ser Ser Ala Thr Pro Ile Val
            275                 280                 285

Gln Phe Gln Gly Glu Ser Asn Cys Leu Lys Cys Phe Arg Tyr Arg Leu
        290                 295                 300

Asn Asp Arg His Arg His Leu Phe Asp Leu Ile Ser Ser Thr Trp His
305                 310                 315                 320

Trp Ala Ser Ser Lys Ala Pro His Lys His Ala Ile Val Thr Val Thr
                325                 330                 335

Tyr Asp Ser Glu Glu Gln Arg Gln Gln Phe Leu Asp Val Val Lys Ile
            340                 345                 350

Pro Pro Thr Ile Ser His Lys Leu Gly Phe Met Ser Leu His Leu Leu
        355                 360                 365

<210> SEQ ID NO 12
<211> LENGTH: 109
<212> TYPE: PRT
<213> ORGANISM: Human papillomavirus type 6b

<400> SEQUENCE: 12

Met Gly Ala Pro Asn Ile Gly Lys Tyr Val Met Ala Ala Gln Leu Tyr
 1               5                  10                  15

Val Leu Leu His Leu Tyr Leu Ala Leu His Lys Lys Tyr Pro Phe Leu
            20                  25                  30

Asn Leu Leu His Thr Pro Pro His Arg Pro Pro Leu Cys Pro Gln
        35                  40                  45

Ala Pro Arg Lys Thr Gln Cys Lys Arg Arg Leu Gly Asn Glu His Glu
    50                  55                  60

Glu Ser Asn Ser Pro Leu Ala Thr Pro Cys Val Trp Pro Thr Leu Asp
65                  70                  75                  80

Pro Trp Thr Val Glu Thr Thr Thr Ser Ser Leu Thr Ile Thr Thr Ser
                85                  90                  95

Thr Lys Asp Gly Thr Thr Val Thr Val Gln Leu Arg Leu
            100                 105

<210> SEQ ID NO 13
<211> LENGTH: 91
<212> TYPE: PRT
<213> ORGANISM: Human papillomavirus type 6b

<400> SEQUENCE: 13

Met Glu Val Val Pro Val Gln Ile Ala Ala Gly Thr Thr Ser Thr Phe
 1               5                  10                  15

Ile Leu Pro Val Ile Ile Ala Phe Val Val Cys Phe Val Ser Ile Ile
            20                  25                  30

Leu Ile Val Trp Ile Ser Glu Phe Ile Val Tyr Thr Ser Val Leu Val
        35                  40                  45

Leu Thr Leu Leu Leu Tyr Leu Leu Trp Leu Leu Leu Thr Thr Pro
    50                  55                  60

Leu Gln Phe Phe Leu Leu Thr Leu Leu Val Cys Tyr Cys Pro Ala Leu
65                  70                  75                  80

Tyr Ile His Tyr Tyr Ile Val Thr Thr Gln Gln
                85                  90

<210> SEQ ID NO 14
<211> LENGTH: 72
<212> TYPE: PRT
<213> ORGANISM: Human papillomavirus type 6b

```
<400> SEQUENCE: 14

Met Met Leu Thr Cys Gln Phe Asn Asp Gly Asp Thr Trp Leu Gly Leu
 1               5                  10                  15

Trp Leu Leu Cys Ala Phe Ile Val Gly Met Leu Gly Leu Leu Met
             20                  25                  30

His Tyr Arg Ala Val Gln Gly Asp Lys His Thr Lys Cys Lys Lys Cys
             35                  40                  45

Asn Lys His Asn Cys Asn Asp Asp Tyr Val Thr Met His Tyr Thr Thr
             50                  55                  60

Asp Gly Asp Tyr Ile Tyr Met Asn
 65                  70

<210> SEQ ID NO 15
<211> LENGTH: 150
<212> TYPE: PRT
<213> ORGANISM: Human papillomavirus type 6b

<400> SEQUENCE: 15

Met Glu Ser Ala Asn Ala Ser Thr Ser Ala Thr Thr Ile Asp Gln Leu
 1               5                  10                  15

Cys Lys Thr Phe Asn Leu Ser Met His Thr Leu Gln Ile Asn Cys Val
             20                  25                  30

Phe Cys Lys Asn Ala Leu Thr Thr Ala Glu Ile Tyr Ser Tyr Ala Tyr
             35                  40                  45

Lys His Leu Lys Val Leu Phe Arg Gly Gly Tyr Pro Tyr Ala Ala Cys
             50                  55                  60

Ala Cys Cys Leu Glu Phe His Gly Lys Ile Asn Gln Tyr Arg His Phe
 65                  70                  75                  80

Asp Tyr Ala Gly Tyr Ala Thr Thr Val Glu Glu Thr Lys Gln Asp
             85                  90                  95

Ile Leu Asp Val Leu Ile Arg Cys Tyr Leu Cys His Lys Pro Leu Cys
                100                 105                 110

Glu Val Glu Lys Val Lys His Ile Leu Thr Lys Ala Arg Phe Ile Lys
            115                 120                 125

Leu Asn Cys Thr Trp Lys Gly Arg Cys Leu His Cys Trp Thr Thr Cys
        130                 135                 140

Met Glu Asp Met Leu Pro
145                 150

<210> SEQ ID NO 16
<211> LENGTH: 98
<212> TYPE: PRT
<213> ORGANISM: Human papillomavirus type 6b

<400> SEQUENCE: 16

Met His Gly Arg His Val Thr Leu Lys Asp Ile Val Leu Asp Leu Gln
 1               5                  10                  15

Pro Pro Asp Pro Val Gly Leu His Cys Tyr Glu Gln Leu Val Asp Ser
             20                  25                  30

Ser Glu Asp Glu Val Asp Glu Val Asp Gly Gln Asp Ser Gln Pro Leu
             35                  40                  45

Lys Gln His Phe Gln Ile Val Thr Cys Cys Cys Gly Cys Asp Ser Asn
             50                  55                  60

Val Arg Leu Val Val Gln Cys Thr Glu Thr Asp Ile Arg Glu Val Gln
 65                  70                  75                  80
```

```
Gln Leu Leu Leu Gly Thr Leu Asn Ile Val Cys Pro Ile Cys Ala Pro
                85                  90                  95

Lys Thr

<210> SEQ ID NO 17
<211> LENGTH: 500
<212> TYPE: PRT
<213> ORGANISM: Human papillomavirus type 6a

<400> SEQUENCE: 17

Met Trp Arg Pro Ser Asp Ser Thr Val Tyr Val Pro Pro Asn Pro
  1               5                  10                  15

Val Ser Lys Val Val Ala Thr Asp Ala Tyr Val Thr Arg Thr Asn Ile
                 20                  25                  30

Phe Tyr His Ala Ser Ser Arg Leu Leu Ala Val Gly His Pro Tyr
             35                  40                  45

Phe Ser Ile Lys Arg Ala Asn Lys Thr Val Val Pro Lys Val Ser Gly
             50                  55                  60

Tyr Gln Tyr Arg Val Phe Lys Val Val Leu Pro Asp Pro Asn Lys Phe
 65                  70                  75                  80

Ala Leu Pro Asp Ser Ser Leu Phe Asp Pro Thr Thr Gln Arg Leu Val
                 85                  90                  95

Trp Ala Cys Thr Gly Leu Glu Val Gly Arg Gly Gln Pro Leu Gly Val
                100                 105                 110

Gly Val Ser Gly His Pro Phe Leu Asn Lys Tyr Asp Asp Val Glu Asn
                115                 120                 125

Ser Gly Ser Gly Gly Asn Pro Gly Gln Asp Asn Arg Val Asn Val Gly
            130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
                180                 185                 190

Asp Gly Asp Met Val Asp Thr Gly Phe Gly Ala Met Asn Phe Ala Asp
                195                 200                 205

Leu Gln Thr Asn Lys Ser Asp Val Pro Ile Asp Ile Cys Gly Thr Thr
            210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
                260                 265                 270

Ile Lys Gly Ser Gly Asn Arg Thr Ser Val Gly Ser Ser Ile Tyr Val
            275                 280                 285

Asn Thr Pro Ser Gly Ser Leu Val Ser Ser Glu Ala Gln Leu Phe Asn
            290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
                340                 345                 350
```

```
Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
        370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
                420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
450                 455                 460

Leu Gln Ser Gly Tyr Arg Gly Arg Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
        500

<210> SEQ ID NO 18
<211> LENGTH: 459
<212> TYPE: PRT
<213> ORGANISM: Human papillomavirus type 6b

<400> SEQUENCE: 18

Met Ala His Ser Arg Ala Arg Arg Lys Arg Ala Ser Ala Thr Gln
1               5                   10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
        50                  55                  60

Thr Gly Gly Arg Thr Gly Tyr Val Pro Leu Gln Thr Ser Ala Lys Pro
65                  70                  75                  80

Ser Ile Thr Ser Gly Pro Met Ala Arg Pro Pro Val Val Glu Pro
                85                  90                  95

Val Ala Pro Ser Asp Pro Ser Ile Val Ser Leu Ile Glu Glu Ser Ala
                100                 105                 110

Ile Ile Asn Ala Gly Ala Pro Glu Ile Val Pro Pro Ala His Gly Gly
            115                 120                 125

Phe Thr Ile Thr Ser Ser Glu Thr Thr Thr Pro Ala Ile Leu Asp Val
        130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Val Thr Ser His Pro Ile Glu Glu
            180                 185                 190

Ile Pro Leu Asp Thr Phe Val Val Ser Ser Ser Asp Ser Gly Pro Thr
        195                 200                 205

Ser Ser Thr Pro Val Pro Gly Thr Ala Pro Arg Pro Arg Val Gly Leu
    210                 215                 220
```

```
Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
            245                 250                 255

Glu Asp Val Ser Val Gln Phe Ser His Asp Ser Ile His Asn Ala Pro
        260                 265                 270

Asp Glu Ala Phe Met Asp Ile Ile Arg Leu His Arg Pro Ala Ile Ala
    275                 280                 285

Ser Arg Arg Gly Leu Val Arg Tyr Ser Arg Ile Gly Gln Arg Gly Ser
290                 295                 300

Met His Thr Arg Ser Gly Lys His Ile Gly Ala Arg Ile His Tyr Phe
305                 310                 315                 320

Tyr Asp Ile Ser Pro Ile Ala Gln Ala Ala Glu Glu Ile Glu Met His
                325                 330                 335

Pro Leu Val Ala Ala Gln Asp Asp Thr Phe Asp Ile Tyr Ala Glu Ser
            340                 345                 350

Phe Glu Pro Gly Ile Asn Pro Thr Gln His Pro Val Thr Asn Ile Ser
        355                 360                 365

Asp Thr Tyr Leu Thr Ser Thr Pro Asn Thr Val Thr Gln Pro Trp Gly
    370                 375                 380

Asn Thr Thr Val Pro Leu Ser Leu Pro Asn Asp Leu Phe Leu Gln Ser
385                 390                 395                 400

Gly Pro Asp Ile Thr Phe Pro Thr Ala Pro Met Gly Thr Pro Phe Ser
                405                 410                 415

Pro Val Thr Pro Ala Leu Pro Thr Gly Pro Val Phe Ile Thr Gly Ser
            420                 425                 430

Gly Phe Tyr Leu His Pro Ala Trp Tyr Phe Ala Arg Lys Arg Arg Lys
        435                 440                 445

Arg Ile Pro Leu Phe Phe Ser Asp Val Ala Ala
    450                 455

<210> SEQ ID NO 19
<211> LENGTH: 649
<212> TYPE: PRT
<213> ORGANISM: Human papillomavirus type 11

<400> SEQUENCE: 19

Met Ala Asp Asp Ser Gly Thr Glu Asn Glu Gly Ser Gly Cys Thr Gly
1               5                   10                  15

Trp Phe Met Val Glu Ala Ile Val Glu His Thr Thr Gly Thr Gln Ile
                20                  25                  30

Ser Glu Asp Glu Glu Glu Val Glu Asp Ser Gly Tyr Asp Met Val
            35                  40                  45

Asp Phe Ile Asp Asp Arg His Ile Thr Gln Asn Ser Val Glu Ala Gln
    50                  55                  60

Ala Leu Phe Asn Arg Gln Glu Ala Asp Ala His Tyr Ala Thr Val Gln
65                  70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Arg Leu Phe Glu
        115                 120                 125

Thr Arg Glu Leu Thr Asp Ser Gly Tyr Gly Tyr Ser Glu Val Glu Ala
```

-continued

```
            130                 135                 140
Ala Thr Gln Val Glu Lys His Gly Asp Pro Glu Asn Gly Gly Asp Gly
145                 150                 155                 160
Gln Glu Arg Asp Thr Gly Arg Asp Ile Glu Gly Glu Gly Val Glu His
                165                 170                 175
Arg Glu Ala Glu Ala Val Asp Asp Ser Thr Arg Glu His Ala Asp Thr
                180                 185                 190
Ser Gly Ile Leu Glu Leu Leu Lys Cys Lys Asp Ile Arg Ser Thr Leu
                195                 200                 205
His Gly Lys Phe Lys Asp Cys Phe Gly Leu Ser Phe Val Asp Leu Ile
            210                 215                 220
Arg Pro Phe Lys Ser Asp Arg Thr Thr Cys Ala Asp Trp Val Val Ala
225                 230                 235                 240
Gly Phe Gly Ile His His Ser Ile Ala Asp Ala Phe Gln Lys Leu Ile
                245                 250                 255
Glu Pro Leu Ser Leu Tyr Ala His Ile Gln Trp Leu Thr Asn Ala Trp
                260                 265                 270
Gly Met Val Leu Leu Val Leu Ile Arg Phe Lys Val Asn Lys Ser Arg
            275                 280                 285
Cys Thr Val Ala Arg Thr Leu Gly Thr Leu Leu Asn Ile Pro Glu Asn
            290                 295                 300
His Met Leu Ile Glu Pro Pro Lys Ile Gln Ser Gly Val Arg Ala Leu
305                 310                 315                 320
Tyr Trp Phe Arg Thr Gly Ile Ser Asn Ala Ser Thr Val Ile Gly Glu
                325                 330                 335
Ala Pro Glu Trp Ile Thr Arg Gln Thr Val Ile Glu His Ser Leu Ala
                340                 345                 350
Asp Ser Gln Phe Lys Leu Thr Glu Met Val Gln Trp Ala Tyr Asp Asn
                355                 360                 365
Asp Ile Cys Glu Glu Ser Glu Ile Ala Phe Glu Tyr Ala Gln Arg Gly
            370                 375                 380
Asp Phe Asp Ser Asn Ala Arg Ala Phe Leu Asn Ser Asn Met Gln Ala
385                 390                 395                 400
Lys Tyr Val Lys Asp Cys Ala Ile Met Cys Arg His Tyr Lys His Ala
                405                 410                 415
Glu Met Lys Lys Met Ser Ile Lys Gln Trp Ile Lys Tyr Arg Gly Thr
                420                 425                 430
Lys Val Asp Ser Val Gly Asn Trp Lys Pro Ile Val Gln Phe Leu Arg
            435                 440                 445
His Gln Asn Ile Glu Phe Ile Pro Phe Leu Ser Lys Leu Lys Leu Trp
            450                 455                 460
Leu His Gly Thr Pro Lys Lys Asn Cys Ile Ala Ile Val Gly Pro Pro
465                 470                 475                 480
Asp Thr Gly Lys Ser Cys Phe Cys Met Ser Leu Ile Lys Phe Leu Gly
                485                 490                 495
Gly Thr Val Ile Ser Tyr Val Asn Ser Cys Ser His Phe Trp Leu Gln
                500                 505                 510
Pro Leu Thr Asp Ala Lys Val Ala Leu Leu Asp Asp Ala Thr Gln Pro
            515                 520                 525
Cys Trp Thr Tyr Met Asp Thr Tyr Met Arg Asn Leu Leu Asp Gly Asn
            530                 535                 540
Pro Met Ser Ile Asp Arg Lys His Arg Ala Leu Thr Leu Ile Lys Cys
545                 550                 555                 560
```

```
Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
                580                 585                 590

Phe Pro Phe Asp Arg Asn Gly Asn Ala Val Tyr Glu Leu Ser Asp Ala
                595                 600                 605

Asn Trp Lys Cys Phe Phe Glu Arg Leu Ser Ser Leu Asp Ile Glu
                610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

<210> SEQ ID NO 20
<211> LENGTH: 367
<212> TYPE: PRT
<213> ORGANISM: Human papillomavirus type 11

<400> SEQUENCE: 20

Met Glu Ala Ile Ala Lys Arg Leu Asp Ala Cys Gln Asp Gln Leu Leu
 1               5                  10                  15

Glu Leu Tyr Glu Glu Asn Ser Ile Asp Ile His Lys His Ile Met His
                20                  25                  30

Trp Lys Cys Ile Arg Leu Glu Ser Val Leu Leu His Lys Ala Lys Gln
            35                  40                  45

Met Gly Leu Ser His Ile Gly Leu Gln Val Val Pro Pro Leu Thr Val
        50                  55                  60

Ser Glu Thr Lys Gly His Asn Ala Ile Glu Met Gln Met His Leu Glu
65                  70                  75                  80

Ser Leu Ala Lys Thr Gln Tyr Gly Val Glu Pro Trp Thr Leu Gln Asp
                85                  90                  95

Thr Ser Tyr Glu Met Trp Leu Thr Pro Pro Lys Arg Cys Phe Lys Lys
                100                 105                 110

Gln Gly Asn Thr Val Glu Val Lys Phe Asp Gly Cys Glu Asp Asn Val
            115                 120                 125

Met Glu Tyr Val Val Trp Thr His Ile Tyr Leu Gln Asp Asn Asp Ser
        130                 135                 140

Trp Val Lys Val Thr Ser Ser Val Asp Ala Lys Gly Ile Tyr Tyr Thr
145                 150                 155                 160

Cys Gly Gln Phe Lys Thr Tyr Tyr Val Asn Phe Asn Lys Glu Ala Gln
                165                 170                 175

Lys Tyr Gly Ser Thr Asn His Trp Glu Val Cys Tyr Gly Ser Thr Val
                180                 185                 190

Ile Cys Ser Pro Ala Ser Val Ser Ser Thr Val Arg Glu Val Ser Ile
            195                 200                 205

Ala Glu Pro Thr Thr Tyr Thr Pro Ala Gln Thr Thr Ala Pro Thr Val
        210                 215                 220

Ser Ala Cys Thr Thr Glu Asp Gly Val Ser Ala Pro Pro Arg Lys Arg
225                 230                 235                 240

Ala Arg Gly Pro Ser Thr Asn Asn Thr Leu Cys Val Ala Asn Ile Arg
                245                 250                 255

Ser Val Asp Ser Thr Ile Asn Asn Ile Val Thr Asp Asn Tyr Asn Lys
                260                 265                 270

His Gln Arg Arg Asn Asn Cys His Ser Ala Ala Thr Pro Ile Val Gln
```

```
                275                 280                 285
Leu Gln Gly Asp Ser Asn Cys Leu Lys Cys Phe Arg Tyr Arg Leu Asn
            290                 295                 300

Asp Lys Tyr Lys His Leu Phe Glu Leu Ala Ser Ser Thr Trp His Trp
305                 310                 315                 320

Ala Ser Pro Glu Ala Pro His Lys Asn Ala Ile Val Thr Leu Thr Tyr
                325                 330                 335

Ser Ser Glu Glu Gln Arg Gln Gln Phe Leu Asn Ser Val Lys Ile Pro
            340                 345                 350

Pro Thr Ile Arg His Lys Val Gly Phe Met Ser Leu His Leu Leu
            355                 360                 365

<210> SEQ ID NO 21
<211> LENGTH: 108
<212> TYPE: PRT
<213> ORGANISM: Human papillomavirus type 11

<400> SEQUENCE: 21

Met Val Val Pro Ile Ile Gly Lys Tyr Val Met Ala Ala Gln Leu Tyr
1               5                   10                  15

Val Leu Leu His Leu Tyr Leu Ala Leu Tyr Glu Lys Tyr Pro Leu Leu
            20                  25                  30

Asn Leu Leu His Thr Pro His Arg Pro Pro Leu Gln Cys Pro
        35                  40                  45

Pro Ala Pro Arg Lys Thr Ala Cys Arg Arg Arg Leu Gly Ser Glu His
    50                  55                  60

Val Asp Arg Pro Leu Thr Thr Pro Cys Val Trp Pro Thr Ser Asp Pro
65                  70                  75                  80

Trp Thr Val Gln Ser Thr Thr Ser Ser Leu Thr Ile Thr Thr Ser Thr
                85                  90                  95

Lys Glu Gly Thr Thr Val Thr Val Gln Leu Arg Leu
            100                 105

<210> SEQ ID NO 22
<211> LENGTH: 91
<212> TYPE: PRT
<213> ORGANISM: Human papillomavirus type 11

<400> SEQUENCE: 22

Met Glu Val Val Pro Val Gln Ile Ala Ala Ala Thr Thr Thr Thr Leu
1               5                   10                  15

Ile Leu Pro Val Val Ile Ala Phe Ala Val Cys Ile Leu Ser Ile Val
            20                  25                  30

Leu Ile Ile Leu Ile Ser Asp Phe Val Val Tyr Thr Ser Val Leu Val
        35                  40                  45

Leu Thr Leu Leu Leu Tyr Leu Leu Leu Trp Leu Leu Leu Thr Thr Pro
    50                  55                  60

Leu Gln Phe Phe Leu Leu Thr Leu Cys Val Cys Tyr Phe Pro Ala Phe
65                  70                  75                  80

Tyr Ile His Ile Tyr Ile Val Gln Thr Gln Gln
                85                  90

<210> SEQ ID NO 23
<211> LENGTH: 74
<212> TYPE: PRT
<213> ORGANISM: Human papillomavirus type 11

<400> SEQUENCE: 23
```

-continued

```
Met Val Met Leu Thr Cys His Leu Asn Asp Gly Asp Thr Trp Leu Phe
 1               5                   10                  15

Leu Trp Leu Phe Thr Ala Phe Val Val Ala Val Leu Gly Leu Leu Leu
                20                  25                  30

Leu His Tyr Arg Ala Val His Gly Thr Glu Lys Thr Lys Cys Ala Lys
            35                  40                  45

Cys Lys Ser Asn Arg Asn Thr Thr Val Asp Tyr Val Tyr Met Ser His
        50                  55                  60

Gly Asp Asn Gly Asp Tyr Val Tyr Met Asn
65                  70
```

<210> SEQ ID NO 24
<211> LENGTH: 150
<212> TYPE: PRT
<213> ORGANISM: Human papillomavirus type 11

<400> SEQUENCE: 24

```
Met Glu Ser Lys Asp Ala Ser Thr Ser Ala Thr Ser Ile Asp Gln Leu
 1               5                   10                  15

Cys Lys Thr Phe Asn Leu Ser Leu His Thr Leu Gln Ile Gln Cys Val
                20                  25                  30

Phe Cys Arg Asn Ala Leu Thr Thr Ala Glu Ile Tyr Ala Tyr Ala Tyr
            35                  40                  45

Lys Asn Leu Lys Val Val Trp Arg Asp Asn Phe Pro Phe Ala Ala Cys
        50                  55                  60

Ala Cys Cys Leu Glu Leu Gln Gly Lys Ile Asn Gln Tyr Arg His Phe
65                  70                  75                  80

Asn Tyr Ala Ala Tyr Ala Pro Thr Val Glu Glu Glu Thr Asn Glu Asp
                85                  90                  95

Ile Leu Lys Val Leu Ile Arg Cys Tyr Leu Cys His Lys Pro Leu Cys
            100                 105                 110

Glu Ile Glu Lys Leu Lys His Ile Leu Gly Lys Ala Arg Phe Ile Lys
        115                 120                 125

Leu Asn Asn Gln Trp Lys Gly Arg Cys Leu His Cys Trp Thr Thr Cys
130                 135                 140

Met Glu Asp Leu Leu Pro
145                 150
```

<210> SEQ ID NO 25
<211> LENGTH: 98
<212> TYPE: PRT
<213> ORGANISM: Human papillomavirus type 11

<400> SEQUENCE: 25

```
Met His Gly Arg Leu Val Thr Leu Lys Asp Ile Val Leu Asp Leu Gln
 1               5                   10                  15

Pro Pro Asp Pro Val Gly Leu His Cys Tyr Glu Gln Leu Glu Asp Ser
                20                  25                  30

Ser Glu Asp Glu Val Asp Lys Val Asp Lys Gln Asp Ala Gln Pro Leu
            35                  40                  45

Thr Gln His Tyr Gln Ile Leu Thr Cys Cys Cys Gly Cys Asp Ser Asn
        50                  55                  60

Val Arg Leu Val Val Glu Cys Thr Asp Gly Asp Ile Arg Gln Leu Gln
65                  70                  75                  80

Asp Leu Leu Leu Gly Thr Leu Asn Ile Val Cys Pro Ile Cys Ala Pro
                85                  90                  95
```

Lys Pro

<210> SEQ ID NO 26
<211> LENGTH: 501
<212> TYPE: PRT
<213> ORGANISM: Human papillomavirus type 11

<400> SEQUENCE: 26

```
Met Trp Arg Pro Ser Asp Ser Thr Val Tyr Val Pro Pro Asn Pro
  1               5                  10                  15

Val Ser Lys Val Val Ala Thr Asp Ala Tyr Val Lys Arg Thr Asn Ile
             20                  25                  30

Phe Tyr His Ala Ser Ser Ser Arg Leu Leu Ala Val Gly His Pro Tyr
             35                  40                  45

Tyr Ser Ile Lys Lys Val Asn Lys Thr Val Val Pro Lys Val Ser Gly
 50                  55                  60

Tyr Gln Tyr Arg Val Phe Lys Val Val Leu Pro Asp Pro Asn Lys Phe
 65                  70                  75                  80

Ala Leu Pro Asp Ser Ser Leu Phe Asp Pro Thr Thr Gln Arg Leu Val
             85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
            115                 120                 125

Ser Gly Gly Tyr Gly Gly Asn Pro Gly Gln Asp Asn Arg Val Asn Val
            130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
                180                 185                 190

Gln Asp Gly Asp Met Val Asp Thr Gly Phe Gly Ala Met Asn Phe Ala
                195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
                260                 265                 270

Leu Val Lys Gly Gly Asn Asn Arg Ser Ser Val Ala Ser Ser Ile Tyr
            275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
                340                 345                 350

Asn Ser Asp Tyr Lys Glu Tyr Met Arg His Val Glu Glu Phe Asp Leu
            355                 360                 365
```

```
Gln Phe Ile Phe Gln Leu Cys Ser Ile Thr Leu Ser Ala Glu Val Met
        370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
                420                 425                 430

Lys Gln Asp Pro Tyr Lys Asp Met Ser Phe Trp Glu Val Asn Leu Lys
                435                 440                 445

Glu Lys Phe Ser Ser Glu Leu Asp Gln Phe Pro Leu Gly Arg Lys Phe
        450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
                485                 490                 495

Thr Lys Thr Lys Lys
                500

<210> SEQ ID NO 27
<211> LENGTH: 455
<212> TYPE: PRT
<213> ORGANISM: Human papillomavirus type 11

<400> SEQUENCE: 27

Met Lys Pro Arg Ala Arg Arg Lys Arg Ala Ser Ala Thr Gln Leu
  1               5                  10                  15

Tyr Gln Thr Cys Lys Ala Thr Gly Thr Cys Pro Pro Asp Val Ile Pro
                20                  25                  30

Lys Val Glu His Thr Thr Ile Ala Asp Gln Ile Leu Lys Trp Gly Ser
            35                  40                  45

Leu Gly Val Phe Phe Gly Gly Leu Gly Ile Gly Thr Gly Ala Gly Ser
        50                  55                  60

Gly Gly Arg Ala Gly Tyr Ile Pro Leu Gly Ser Ser Pro Lys Pro Ala
65                  70                  75                  80

Ile Thr Gly Gly Pro Ala Ala Arg Pro Pro Val Leu Val Glu Pro Val
                85                  90                  95

Ala Pro Ser Asp Pro Ser Ile Val Ser Leu Ile Glu Glu Ser Ala Ile
                100                 105                 110

Ile Asn Ala Gly Ala Pro Glu Val Val Pro Pro Thr Gln Gly Gly Phe
            115                 120                 125

Thr Ile Thr Ser Ser Glu Ser Thr Thr Pro Ala Ile Leu Asp Val Ser
        130                 135                 140

Val Thr Asn His Thr Thr Thr Ser Val Phe Gln Asn Pro Leu Phe Thr
145                 150                 155                 160

Glu Pro Ser Val Ile Gln Pro Gln Pro Pro Val Glu Ala Ser Gly His
                165                 170                 175

Ile Leu Ile Ser Ala Pro Thr Ile Thr Ser Gln His Val Glu Asp Ile
            180                 185                 190

Pro Leu Asp Thr Phe Val Val Ser Ser Asp Ser Gly Pro Thr Ser
        195                 200                 205

Ser Thr Pro Leu Pro Arg Ala Phe Pro Arg Pro Arg Val Gly Leu Tyr
        210                 215                 220

Ser Arg Ala Leu Gln Gln Val Gln Val Thr Asp Pro Ala Phe Leu Ser
```

-continued

```
                225                 230                 235                 240

Thr Pro Gln Arg Leu Val Thr Tyr Asp Asn Pro Val Tyr Glu Gly Glu
                    245                 250                 255

Asp Val Ser Leu Gln Phe Thr His Glu Ser Ile His Asn Ala Pro Asp
                260                 265                 270

Glu Ala Phe Met Asp Ile Ile Arg Leu His Arg Pro Ala Ile Thr Ser
            275                 280                 285

Arg Arg Gly Leu Val Arg Phe Ser Arg Ile Gly Gln Arg Gly Ser Met
        290                 295                 300

Tyr Thr Arg Ser Gly Gln His Ile Gly Ala Arg Ile His Tyr Phe Gln
305                 310                 315                 320

Asp Ile Ser Pro Val Thr Gln Ala Ala Glu Glu Ile Glu Leu His Pro
                325                 330                 335

Leu Val Ala Ala Glu Asn Asp Thr Phe Asp Ile Tyr Ala Glu Pro Phe
                340                 345                 350

Asp Pro Ile Pro Asp Pro Val Gln His Ser Val Thr Gln Ser Tyr Leu
            355                 360                 365

Thr Ser Thr Pro Asn Thr Leu Ser Gln Ser Trp Gly Asn Thr Thr Val
        370                 375                 380

Pro Leu Ser Ile Pro Ser Asp Trp Phe Val Gln Ser Gly Pro Asp Ile
385                 390                 395                 400

Thr Phe Pro Thr Ala Ser Met Gly Thr Pro Phe Ser Pro Val Thr Pro
                405                 410                 415

Ala Leu Pro Thr Gly Pro Val Phe Ile Thr Gly Ser Asp Phe Tyr Leu
                420                 425                 430

His Pro Thr Trp Tyr Phe Ala Arg Arg Arg Arg Lys Arg Ile Pro Leu
            435                 440                 445

Phe Phe Thr Asp Val Ala Ala
    450                 455

<210> SEQ ID NO 28
<211> LENGTH: 649
<212> TYPE: PRT
<213> ORGANISM: Human papillomavirus type 16

<400> SEQUENCE: 28

Met Ala Asp Pro Ala Gly Thr Asn Gly Glu Glu Gly Thr Gly Cys Asn
  1               5                  10                  15

Gly Trp Phe Tyr Val Glu Ala Val Val Glu Lys Lys Thr Gly Asp Ala
                 20                  25                  30

Ile Ser Asp Asp Glu Asn Glu Asn Asp Ser Asp Thr Gly Glu Asp Leu
             35                  40                  45

Val Asp Phe Ile Val Asn Asp Asn Asp Tyr Leu Thr Gln Ala Glu Thr
         50                  55                  60

Glu Thr Ala His Ala Leu Phe Thr Ala Gln Glu Ala Lys Gln His Arg
 65                  70                  75                  80

Asp Ala Val Gln Val Leu Lys Arg Lys Tyr Leu Val Ser Pro Leu Ser
                 85                  90                  95

Asp Ile Ser Gly Cys Val Asp Asn Asn Ile Ser Pro Arg Leu Lys Ala
            100                 105                 110

Ile Cys Ile Glu Lys Gln Ser Arg Ala Ala Lys Arg Arg Leu Phe Glu
        115                 120                 125

Ser Glu Asp Ser Gly Tyr Gly Asn Thr Glu Val Glu Thr Gln Gln Met
    130                 135                 140
```

-continued

```
Leu Gln Val Glu Gly Arg His Glu Thr Glu Thr Pro Cys Ser Gln Tyr
145                 150                 155                 160

Ser Gly Gly Ser Gly Gly Cys Ser Gln Tyr Ser Gly Ser Gly
            165                 170                 175

Gly Glu Gly Val Ser Glu Arg His Thr Ile Cys Gln Thr Pro Leu Thr
                180                 185                 190

Asn Ile Leu Asn Val Leu Lys Thr Ser Asn Ala Lys Ala Ala Met Leu
            195                 200                 205

Ala Lys Phe Lys Glu Leu Tyr Gly Val Ser Phe Ser Glu Leu Val Arg
    210                 215                 220

Pro Phe Lys Ser Asn Lys Ser Thr Cys Cys Asp Trp Cys Ile Ala Ala
225                 230                 235                 240

Phe Gly Leu Thr Pro Ser Ile Ala Asp Ser Ile Lys Thr Leu Leu Gln
                245                 250                 255

Gln Tyr Cys Leu Tyr Leu His Ile Gln Ser Leu Ala Cys Ser Trp Gly
            260                 265                 270

Met Val Val Leu Leu Leu Val Arg Tyr Lys Cys Gly Lys Asn Arg Glu
            275                 280                 285

Thr Ile Glu Lys Leu Leu Ser Lys Leu Leu Cys Val Ser Pro Met Cys
290                 295                 300

Met Met Ile Glu Pro Pro Lys Leu Arg Ser Thr Ala Ala Ala Leu Tyr
305                 310                 315                 320

Trp Tyr Lys Thr Gly Ile Ser Asn Ile Ser Glu Val Tyr Gly Asp Thr
                325                 330                 335

Pro Glu Trp Ile Gln Arg Gln Thr Val Leu Gln His Ser Phe Asn Asp
                340                 345                 350

Cys Thr Phe Glu Leu Ser Gln Met Val Gln Trp Ala Tyr Asp Asn Asp
            355                 360                 365

Ile Val Asp Asp Ser Glu Ile Ala Tyr Lys Tyr Ala Gln Leu Ala Asp
            370                 375                 380

Thr Asn Ser Asn Ala Ser Ala Phe Leu Lys Ser Asn Ser Gln Ala Lys
385                 390                 395                 400

Ile Val Lys Asp Cys Ala Thr Met Cys Arg His Tyr Lys Arg Ala Glu
                405                 410                 415

Lys Lys Gln Met Ser Met Ser Gln Trp Ile Lys Tyr Arg Cys Asp Arg
            420                 425                 430

Val Asp Asp Gly Gly Asp Trp Lys Gln Ile Val Met Phe Leu Arg Tyr
            435                 440                 445

Gln Gly Val Glu Phe Met Ser Phe Leu Thr Ala Leu Lys Arg Phe Leu
    450                 455                 460

Gln Gly Ile Pro Lys Lys Asn Cys Ile Leu Leu Tyr Gly Ala Ala Asn
465                 470                 475                 480

Thr Gly Lys Ser Leu Phe Gly Met Ser Leu Met Lys Phe Leu Gln Gly
                485                 490                 495

Ser Val Ile Cys Phe Val Asn Ser Lys Ser His Phe Trp Leu Gln Pro
            500                 505                 510

Leu Ala Asp Ala Lys Ile Gly Met Leu Asp Asp Ala Thr Val Pro Cys
    515                 520                 525

Trp Asn Tyr Ile Asp Asp Asn Leu Arg Asn Ala Leu Asp Gly Asn Leu
            530                 535                 540

Val Ser Met Asp Val Lys His Arg Pro Leu Val Gln Leu Lys Cys Pro
545                 550                 555                 560

Pro Leu Leu Ile Thr Ser Asn Ile Asn Ala Gly Thr Asp Ser Arg Trp
```

-continued

```
                 565                 570                 575

Pro Tyr Leu His Asn Arg Leu Val Val Phe Thr Phe Pro Asn Glu Phe
            580                 585                 590

Pro Phe Asp Glu Asn Gly Asn Pro Val Tyr Glu Leu Asn Asp Lys Asn
        595                 600                 605

Trp Lys Ser Phe Phe Ser Arg Thr Trp Ser Arg Leu Ser Leu His Glu
    610                 615                 620

Asp Glu Asp Lys Glu Asn Asp Gly Asp Ser Leu Pro Thr Phe Lys Cys
625                 630                 635                 640

Val Ser Gly Gln Asn Thr Asn Thr Leu
                645

<210> SEQ ID NO 29
<211> LENGTH: 365
<212> TYPE: PRT
<213> ORGANISM: Human papillomavirus type 16

<400> SEQUENCE: 29

Met Glu Thr Leu Cys Gln Arg Leu Asn Val Cys Gln Asp Lys Ile Leu
 1               5                  10                  15

Thr His Tyr Glu Asn Asp Ser Thr Asp Leu Arg Asp His Ile Asp Tyr
             20                  25                  30

Trp Lys His Met Arg Leu Glu Cys Ala Ile Tyr Tyr Lys Ala Arg Glu
         35                  40                  45

Met Gly Phe Lys His Ile Asn His Gln Val Val Pro Thr Leu Ala Val
     50                  55                  60

Ser Lys Asn Lys Ala Leu Gln Ala Ile Glu Leu Gln Leu Thr Leu Glu
 65                  70                  75                  80

Thr Ile Tyr Asn Ser Gln Tyr Ser Asn Glu Lys Trp Thr Leu Gln Asp
                 85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285
```

```
Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
            355                 360                 365
```

<210> SEQ ID NO 30
<211> LENGTH: 83
<212> TYPE: PRT
<213> ORGANISM: Human papillomavirus type 16

<400> SEQUENCE: 30

```
Met Thr Asn Leu Asp Thr Ala Ser Thr Thr Leu Leu Ala Cys Phe Leu
  1               5                  10                  15

Leu Cys Phe Cys Val Leu Leu Cys Val Cys Leu Leu Ile Arg Pro Leu
             20                  25                  30

Leu Leu Ser Val Ser Thr Tyr Thr Ser Leu Ile Ile Leu Val Leu Leu
         35                  40                  45

Leu Trp Ile Thr Ala Ala Ser Ala Phe Arg Cys Phe Ile Val Tyr Ile
     50                  55                  60

Ile Phe Val Tyr Ile Pro Leu Phe Leu Ile His Thr His Ala Arg Phe
 65                  70                  75                  80

Leu Ile Thr
```

<210> SEQ ID NO 31
<211> LENGTH: 158
<212> TYPE: PRT
<213> ORGANISM: Human papillomavirus type 16

<400> SEQUENCE: 31

```
Met His Gln Lys Arg Thr Ala Met Phe Gln Asp Pro Gln Glu Arg Pro
  1               5                  10                  15

Arg Lys Leu Pro Gln Leu Cys Thr Glu Leu Gln Thr Thr Ile His Asp
             20                  25                  30

Ile Ile Leu Glu Cys Val Tyr Cys Lys Gln Gln Leu Leu Arg Arg Glu
         35                  40                  45

Val Tyr Asp Phe Ala Phe Arg Asp Leu Cys Ile Val Tyr Arg Asp Gly
     50                  55                  60

Asn Pro Tyr Ala Val Cys Asp Lys Cys Leu Lys Phe Tyr Ser Lys Ile
 65                  70                  75                  80

Ser Glu Tyr Arg His Tyr Cys Tyr Ser Leu Tyr Gly Thr Thr Leu Glu
             85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

-continued

```
<210> SEQ ID NO 32
<211> LENGTH: 98
<212> TYPE: PRT
<213> ORGANISM: Human papillomavirus type 16

<400> SEQUENCE: 32

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 33
<211> LENGTH: 531
<212> TYPE: PRT
<213> ORGANISM: Human papillomavirus type 16

<400> SEQUENCE: 33

Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
                20                  25                  30

Ser Glu Ala Thr Val Tyr Leu Pro Pro Val Pro Val Ser Lys Val Val
            35                  40                  45

Ser Thr Asp Glu Tyr Val Ala Arg Thr Asn Ile Tyr Tyr His Ala Gly
50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
            115                 120                 125

Val Gly Val Glu Val Gly Arg Gly Gln Pro Leu Gly Val Gly Ile Ser
130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
            195                 200                 205

Gly Asp Cys Pro Pro Leu Glu Leu Ile Asn Thr Val Ile Gln Asp Gly
210                 215                 220

Asp Met Val Asp Thr Gly Phe Gly Ala Met Asp Phe Thr Thr Leu Gln
225                 230                 235                 240
```

```
Ala Asn Lys Ser Glu Val Pro Leu Asp Ile Cys Thr Ser Ile Cys Lys
            245                 250                 255

Tyr Pro Asp Tyr Ile Lys Met Val Ser Glu Pro Tyr Gly Asp Ser Leu
        260                 265                 270

Phe Phe Tyr Leu Arg Arg Glu Gln Met Phe Val Arg His Leu Phe Asn
    275                 280                 285

Arg Ala Gly Ala Val Gly Glu Asn Val Pro Asp Leu Tyr Ile Lys
290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
            325                 330                 335

Tyr Trp Leu Gln Arg Ala Gln Gly His Asn Asn Gly Ile Cys Trp Gly
        340                 345                 350

Asn Gln Leu Phe Val Thr Val Val Asp Thr Thr Arg Ser Thr Asn Met
    355                 360                 365

Ser Leu Cys Ala Ala Ile Ser Thr Ser Glu Thr Thr Tyr Lys Asn Thr
370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
            405                 410                 415

Ile His Ser Met Asn Ser Thr Ile Leu Glu Asp Trp Asn Phe Gly Leu
        420                 425                 430

Gln Pro Pro Pro Gly Gly Thr Leu Glu Asp Thr Tyr Arg Phe Val Thr
    435                 440                 445

Ser Gln Ala Ile Ala Cys Gln Lys His Thr Pro Pro Ala Pro Lys Glu
450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
            485                 490                 495

Gln Ala Gly Leu Lys Ala Lys Pro Lys Phe Thr Leu Gly Lys Arg Lys
        500                 505                 510

Ala Thr Pro Thr Thr Ser Ser Ser Thr Thr Ala Lys Arg Lys Lys
    515                 520                 525

Arg Lys Leu
530

<210> SEQ ID NO 34
<211> LENGTH: 473
<212> TYPE: PRT
<213> ORGANISM: Human papillomavirus type 16

<400> SEQUENCE: 34

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
```

-continued

```
             65                  70                  75                  80
    Thr Ala Thr Asp Thr Leu Ala Pro Val Arg Pro Leu Thr Val Asp
                         85                  90                  95
    Pro Val Gly Pro Ser Asp Pro Ser Ile Val Ser Leu Val Glu Glu Thr
                        100                 105                 110
    Ser Phe Ile Asp Ala Gly Ala Pro Thr Ser Val Pro Ser Ile Pro Pro
                115                 120                 125
    Asp Val Ser Gly Phe Ser Ile Thr Thr Ser Thr Asp Thr Thr Pro Ala
        130                 135                 140
    Ile Leu Asp Ile Asn Asn Thr Val Thr Val Thr Thr His Asn Asn
    145                 150                 155                 160
    Pro Thr Phe Thr Asp Pro Ser Val Leu Gln Pro Pro Thr Pro Ala Glu
                    165                 170                 175
    Thr Gly Gly His Phe Thr Leu Ser Ser Ser Thr Ile Ser Thr His Asn
                    180                 185                 190
    Tyr Glu Glu Ile Pro Met Asp Thr Phe Ile Val Ser Thr Asn Pro Asn
                195                 200                 205
    Thr Val Thr Ser Ser Thr Pro Ile Pro Gly Ser Arg Pro Val Ala Arg
    210                 215                 220
    Leu Gly Leu Tyr Ser Arg Thr Gln Gln Val Lys Val Val Asp Pro
    225                 230                 235                 240
    Ala Phe Ile Thr Thr Pro Thr Lys Leu Ile Thr Tyr Asp Asn Pro Ala
                        245                 250                 255
    Tyr Glu Gly Ile Asp Val Asp Asn Thr Leu Tyr Phe Ser Ser Asn Asp
                260                 265                 270
    Asn Ser Ile Asn Ile Ala Pro Asp Pro Asp Phe Leu Asp Ile Val Ala
            275                 280                 285
    Leu His Arg Pro Ala Leu Thr Ser Arg Arg Thr Gly Ile Arg Tyr Ser
        290                 295                 300
    Arg Ile Gly Asn Lys Gln Thr Leu Arg Thr Arg Ser Gly Lys Ser Ile
    305                 310                 315                 320
    Gly Ala Lys Val His Tyr Tyr Tyr Asp Phe Ser Thr Ile Asp Ser Ala
                        325                 330                 335
    Glu Glu Ile Glu Leu Gln Thr Ile Thr Pro Ser Thr Tyr Thr Thr Thr
                    340                 345                 350
    Ser His Ala Ala Leu Pro Thr Ser Ile Asn Asn Gly Leu Tyr Asp Ile
            355                 360                 365
    Tyr Ala Asp Asp Phe Ile Thr Asp Thr Ser Thr Thr Pro Val Pro Ser
            370                 375                 380
    Val Pro Ser Thr Ser Leu Ser Gly Tyr Ile Pro Ala Asn Thr Thr Ile
    385                 390                 395                 400
    Pro Phe Gly Gly Ala Tyr Asn Ile Pro Leu Val Ser Gly Pro Asp Ile
                    405                 410                 415
    Pro Ile Asn Ile Thr Asp Gln Ala Pro Ser Leu Ile Pro Ile Val Pro
                    420                 425                 430
    Gly Ser Pro Gln Tyr Thr Ile Ile Ala Asp Ala Gly Asp Phe Tyr Leu
                    435                 440                 445
    His Pro Ser Tyr Tyr Met Leu Arg Lys Arg Lys Arg Leu Pro Tyr
        450                 455                 460
    Phe Phe Ser Asp Val Ser Leu Ala Ala
    465                 470

<210> SEQ ID NO 35
```

```
<211> LENGTH: 657
<212> TYPE: PRT
<213> ORGANISM: Human papillomavirus type 18

<400> SEQUENCE: 35
```

| | | | | | | | | | | | | | | |
|---|---|---|---|---|---|---|---|---|---|---|---|---|---|---|
|Met|Ala|Asp|Pro|Glu|Gly|Thr|Asp|Gly|Glu|Gly|Thr|Gly|Cys|Asn|Gly|
|1| | | |5| | | | |10| | | | |15|

| | | | | | | | | | | | | | | |
|---|---|---|---|---|---|---|---|---|---|---|---|---|---|---|
|Trp|Phe|Tyr|Val|Gln|Ala|Ile|Val|Asp|Lys|Lys|Thr|Gly|Asp|Val|Ile|
| | | |20| | | | |25| | | | |30| | |

Ser Asp Asp Glu Asp Glu Asn Ala Thr Asp Thr Gly Ser Asp Met Val
          35                  40                  45

Asp Phe Ile Asp Thr Gln Gly Thr Phe Cys Glu Gln Ala Glu Leu Glu
    50                  55                  60

Thr Ala Gln Ala Leu Phe His Ala Gln Glu Val His Asn Asp Ala Gln
65                  70                  75                  80

Val Leu His Val Leu Lys Arg Lys Phe Ala Gly Gly Ser Thr Glu Asn
                85                  90                  95

Ser Pro Leu Gly Glu Arg Leu Glu Val Asp Thr Glu Leu Ser Pro Arg
            100                 105                 110

Leu Gln Glu Ile Ser Leu Asn Ser Gly Gln Lys Ala Lys Arg Arg
        115                 120                 125

Leu Phe Thr Ile Ser Asp Ser Gly Tyr Gly Cys Ser Glu Val Glu Ala
    130                 135                 140

Thr Gln Ile Gln Val Thr Thr Asn Gly Glu His Gly Gly Asn Val Cys
145                 150                 155                 160

Ser Gly Gly Ser Thr Glu Ala Ile Asp Asn Gly Gly Thr Glu Gly Asn
                165                 170                 175

Asn Ser Ser Val Asp Gly Thr Ser Asp Asn Ser Asn Ile Glu Asn Val
            180                 185                 190

Asn Pro Gln Cys Thr Ile Ala Gln Leu Lys Asp Leu Leu Lys Val Asn
        195                 200                 205

Asn Lys Gln Gly Ala Met Leu Ala Val Phe Lys Asp Thr Tyr Gly Leu
    210                 215                 220

Ser Phe Thr Asp Leu Val Arg Asn Phe Lys Ser Asp Lys Thr Thr Cys
225                 230                 235                 240

Thr Asp Trp Val Thr Ala Ile Phe Gly Val Asn Pro Thr Ile Ala Glu
                245                 250                 255

Gly Phe Lys Thr Leu Ile Gln Pro Phe Ile Leu Tyr Ala His Ile Gln
            260                 265                 270

Cys Leu Asp Cys Lys Trp Gly Val Leu Ile Leu Ala Leu Leu Arg Tyr
        275                 280                 285

Lys Cys Gly Lys Ser Arg Leu Thr Val Ala Lys Gly Leu Ser Thr Leu
    290                 295                 300

Leu His Val Pro Glu Thr Cys Met Leu Ile Gln Pro Pro Lys Leu Arg
305                 310                 315                 320

Ser Ser Val Ala Ala Leu Tyr Trp Tyr Arg Thr Gly Ile Ser Asn Ile
                325                 330                 335

Ser Glu Val Met Gly Asp Thr Pro Glu Trp Ile Gln Arg Leu Thr Ile
            340                 345                 350

Ile Gln His Gly Ile Asp Asp Ser Asn Phe Asp Leu Ser Glu Met Val
        355                 360                 365

Gln Trp Ala Phe Asp Asn Glu Leu Thr Asp Glu Ser Asp Met Ala Phe
    370                 375                 380

Glu Tyr Ala Leu Leu Ala Asp Ser Asn Ser Asn Ala Ala Ala Phe Leu

```
385                 390                 395                 400
Lys Ser Asn Cys Gln Ala Lys Tyr Leu Lys Asp Cys Ala Thr Met Cys
                405                 410                 415
Lys His Tyr Arg Arg Ala Gln Lys Arg Gln Met Asn Met Ser Gln Trp
                420                 425                 430
Ile Arg Phe Arg Cys Ser Lys Ile Asp Glu Gly Gly Asp Trp Arg Pro
                435                 440                 445
Ile Val Gln Phe Leu Arg Tyr Gln Gln Ile Glu Phe Ile Thr Phe Leu
    450                 455                 460
Gly Ala Leu Lys Ser Phe Leu Lys Gly Thr Pro Lys Lys Asn Cys Leu
465                 470                 475                 480
Val Phe Cys Gly Pro Ala Asn Thr Gly Lys Ser Tyr Phe Gly Met Ser
                485                 490                 495
Phe Ile His Phe Ile Gln Gly Ala Val Ile Ser Phe Val Asn Ser Thr
                500                 505                 510
Ser His Phe Trp Leu Glu Pro Leu Thr Asp Thr Lys Val Ala Met Leu
                515                 520                 525
Asp Asp Ala Thr Thr Thr Cys Trp Thr Tyr Phe Asp Thr Tyr Met Arg
530                 535                 540
Asn Ala Leu Asp Gly Asn Pro Ile Ser Ile Asp Arg Lys His Lys Pro
545                 550                 555                 560
Leu Ile Gln Leu Lys Cys Pro Pro Ile Leu Leu Thr Thr Asn Ile His
                565                 570                 575
Pro Ala Lys Asp Asn Arg Trp Pro Tyr Leu Glu Ser Arg Ile Thr Val
                580                 585                 590
Phe Glu Phe Pro Asn Ala Phe Pro Phe Asp Lys Asn Gly Asn Pro Val
                595                 600                 605
Tyr Glu Ile Asn Asp Lys Asn Trp Lys Cys Phe Phe Glu Arg Thr Trp
                610                 615                 620
Ser Arg Leu Asp Leu His Glu Glu Glu Asp Ala Asp Thr Glu Gly
625                 630                 635                 640
Asn Pro Phe Gly Thr Phe Lys Leu Arg Ala Gly Gln Asn His Arg Pro
                645                 650                 655
Leu

<210> SEQ ID NO 36
<211> LENGTH: 365
<212> TYPE: PRT
<213> ORGANISM: Human papillomavirus type 18

<400> SEQUENCE: 36

Met Gln Thr Pro Lys Glu Thr Leu Ser Glu Arg Leu Ser Cys Val Gln
1               5                   10                  15
Asp Lys Ile Ile Asp His Tyr Glu Asn Asp Ser Lys Asp Ile Asp Ser
                20                  25                  30
Gln Ile Gln Tyr Trp Gln Leu Ile Arg Trp Glu Asn Ala Ile Phe Phe
        35                  40                  45
Ala Ala Arg Glu His Gly Ile Gln Thr Leu Asn His Gln Val Val Pro
    50                  55                  60
Ala Tyr Asn Ile Ser Lys Ser Lys Ala His Lys Ala Ile Glu Leu Gln
65                  70                  75                  80
Met Ala Leu Gln Gly Leu Ala Gln Ser Arg Tyr Lys Thr Glu Asp Trp
                85                  90                  95
Thr Leu Gln Asp Thr Cys Glu Glu Leu Trp Asn Thr Glu Pro Thr His
```

```
                100                 105                 110
Cys Phe Lys Lys Gly Gly Gln Thr Val Gln Val Tyr Phe Asp Gly Asn
            115                 120                 125

Lys Asp Asn Cys Met Thr Tyr Val Ala Trp Asp Ser Val Tyr Tyr Met
        130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
        195                 200                 205

Asp Asp Thr Val Ser Ala Thr Gln Leu Val Lys Gln Leu Gln His Thr
210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
            260                 265                 270

Thr Gly Asn Asn Lys Arg Arg Lys Leu Cys Ser Gly Asn Thr Thr Pro
        275                 280                 285

Ile Ile His Leu Lys Gly Asp Arg Asn Ser Leu Lys Cys Leu Arg Tyr
290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
            340                 345                 350

Pro Asp Ser Val Gln Ile Leu Val Gly Tyr Met Thr Met
        355                 360                 365

<210> SEQ ID NO 37
<211> LENGTH: 73
<212> TYPE: PRT
<213> ORGANISM: Human papillomavirus type 18

<400> SEQUENCE: 37

Met Leu Ser Leu Ile Phe Leu Phe Cys Phe Cys Val Cys Met Tyr Val
 1               5                  10                  15

Cys Cys His Val Pro Leu Leu Pro Ser Val Cys Met Cys Ala Tyr Ala
            20                  25                  30

Trp Val Leu Val Phe Val Tyr Ile Val Val Ile Thr Ser Pro Ala Thr
        35                  40                  45

Ala Phe Thr Val Tyr Val Phe Cys Phe Leu Leu Pro Met Leu Leu Leu
    50                  55                  60

His Ile His Ala Ile Leu Ser Leu Gln
65                  70

<210> SEQ ID NO 38
<211> LENGTH: 158
<212> TYPE: PRT
<213> ORGANISM: Human papillomavirus type 18
```

```
<400> SEQUENCE: 38

Met Ala Arg Phe Glu Asp Pro Thr Arg Arg Pro Tyr Lys Leu Pro Asp
 1               5                  10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
130                 135                 140

Ala Arg Gln Glu Arg Leu Gln Arg Arg Glu Thr Gln Val
145                 150                 155

<210> SEQ ID NO 39
<211> LENGTH: 105
<212> TYPE: PRT
<213> ORGANISM: Human papillomavirus type 18

<400> SEQUENCE: 39

Met His Gly Pro Lys Ala Thr Leu Gln Asp Ile Val Leu His Leu Glu
 1               5                  10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Lys Leu Val Val Glu Ser Ser Ala
 65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 40
<211> LENGTH: 568
<212> TYPE: PRT
<213> ORGANISM: Human papillomavirus type 18

<400> SEQUENCE: 40

Met Cys Leu Tyr Thr Arg Val Leu Ile Leu His Tyr His Leu Leu Pro
 1               5                  10                  15

Leu Tyr Gly Pro Leu Tyr His Pro Arg Pro Leu Pro Leu His Ser Ile
                20                  25                  30

Leu Val Tyr Met Val His Ile Ile Ile Cys Gly His Tyr Ile Ile Leu
            35                  40                  45

Phe Leu Arg Asn Val Asn Val Phe Pro Ile Phe Leu Gln Met Ala Leu
```

-continued

```
                 50                  55                  60
Trp Arg Pro Ser Asp Asn Thr Val Tyr Leu Pro Pro Ser Val Ala
 65                  70                  75                  80

Arg Val Val Asn Thr Asp Asp Tyr Val Thr Pro Thr Ser Ile Phe Tyr
                     85                  90                  95

His Ala Gly Ser Ser Arg Leu Leu Thr Val Gly Asn Pro Tyr Phe Arg
                    100                 105                 110

Val Pro Ala Gly Gly Asn Lys Gln Asp Ile Pro Lys Val Ser Ala
                115                 120                 125

Tyr Gln Tyr Arg Val Phe Arg Val Gln Leu Pro Asp Pro Asn Lys Phe
                130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
                180                 185                 190

Ser His Ala Ala Thr Ser Asn Val Ser Glu Asp Val Arg Asp Asn Val
                195                 200                 205

Ser Val Asp Tyr Lys Gln Thr Gln Leu Cys Ile Leu Gly Cys Ala Pro
                210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
                260                 265                 270

Thr Leu Gln Asp Thr Lys Cys Glu Val Pro Leu Asp Ile Cys Gln Ser
                275                 280                 285

Ile Cys Lys Tyr Pro Asp Tyr Leu Gln Met Ser Ala Asp Pro Tyr Gly
                290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Pro Ala Ser Pro Gly Ser Cys Val Tyr
                340                 345                 350

Ser Pro Ser Pro Ser Gly Ser Ile Val Thr Ser Asp Ser Gln Leu Phe
                355                 360                 365

Asn Lys Pro Tyr Trp Leu His Lys Ala Gln Gly His Asn Asn Gly Val
                370                 375                 380

Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                    405                 410                 415

Tyr Asp Ala Thr Lys Phe Lys Gln Tyr Ser Arg His Val Glu Glu Tyr
                420                 425                 430

Asp Leu Gln Phe Ile Phe Gln Leu Cys Thr Ile Thr Leu Thr Ala Asp
                435                 440                 445

Val Met Ser Tyr Ile His Ser Met Asn Ser Ser Ile Leu Glu Asp Trp
                450                 455                 460

Asn Phe Gly Val Pro Pro Pro Thr Thr Ser Leu Val Asp Thr Tyr
465                 470                 475                 480
```

-continued

```
Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
            500                 505                 510

Leu Lys Glu Lys Phe Ser Leu Asp Leu Asp Gln Tyr Pro Leu Gly Arg
        515                 520                 525

Lys Phe Leu Val Gln Ala Gly Leu Arg Arg Lys Pro Thr Ile Gly Pro
    530                 535                 540

Arg Lys Arg Ser Ala Pro Ser Ala Thr Thr Ser Ser Lys Pro Ala Lys
545                 550                 555                 560

Arg Val Arg Val Arg Ala Arg Lys
                565

<210> SEQ ID NO 41
<211> LENGTH: 462
<212> TYPE: PRT
<213> ORGANISM: Human papillomavirus type 18

<400> SEQUENCE: 41

Met Val Ser His Arg Ala Ala Arg Arg Lys Arg Ala Ser Val Thr Asp
  1               5                  10                  15

Leu Tyr Lys Thr Cys Lys Gln Ser Gly Thr Cys Pro Pro Asp Val Val
                 20                  25                  30

Pro Lys Val Glu Gly Thr Thr Leu Ala Asp Lys Ile Leu Gln Trp Ser
             35                  40                  45

Ser Leu Gly Ile Phe Leu Gly Gly Leu Gly Ile Gly Thr Gly Ser Gly
         50                  55                  60

Thr Gly Gly Arg Thr Gly Tyr Ile Pro Leu Gly Gly Arg Ser Asn Thr
 65                  70                  75                  80

Val Val Asp Val Gly Pro Thr Arg Pro Pro Val Val Ile Glu Pro Val
                 85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
    130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Ala Gly Pro
    210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
```

-continued

```
                275                 280                 285
Ser Arg Arg Gly Thr Val Arg Phe Ser Arg Leu Gly Gln Arg Ala Thr
    290                 295                 300

Met Phe Thr Arg Ser Gly Thr Gln Ile Gly Ala Arg Val His Phe Tyr
305                 310                 315                 320

His Asp Ile Ser Pro Ile Ala Pro Ser Pro Glu Tyr Ile Glu Leu Gln
                325                 330                 335

Pro Leu Val Ser Ala Thr Glu Asp Asn Asp Leu Phe Asp Ile Tyr Ala
                340                 345                 350

Asp Asp Met Asp Pro Ala Val Pro Val Pro Ser Arg Ser Thr Thr Ser
            355                 360                 365

Phe Ala Phe Phe Lys Tyr Ser Pro Thr Ile Ser Ser Ala Ser Ser Tyr
    370                 375                 380

Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
                405                 410                 415

Val Ser Pro Thr Ala Pro Ala Ser Thr Gln Tyr Ile Gly Ile His Gly
            420                 425                 430

Thr His Tyr Tyr Leu Trp Pro Leu Tyr Tyr Phe Ile Pro Lys Lys Arg
    435                 440                 445

Lys Arg Val Pro Tyr Phe Phe Ala Asp Gly Phe Val Ala Ala
    450                 455                 460

<210> SEQ ID NO 42
<211> LENGTH: 629
<212> TYPE: PRT
<213> ORGANISM: Human papillomavirus type 31

<400> SEQUENCE: 42

Met Ala Asp Pro Ala Gly Thr Asp Gly Glu Gly Thr Gly Cys Asn Gly
1               5                   10                  15

Trp Phe Tyr Val Glu Ala Val Ile Asp Arg Gln Thr Gly Asp Asn Ile
                20                  25                  30

Ser Glu Asp Glu Asn Glu Asp Ser Ser Asp Thr Gly Glu Asp Met Val
            35                  40                  45

Asp Phe Ile Asp Asn Cys Asn Val Tyr Asn Asn Gln Ala Glu Ala Glu
        50                  55                  60

Thr Ala Gln Ala Leu Phe His Ala Gln Glu Ala Glu His Ala Glu
65                  70                  75                  80

Ala Val Gln Val Leu Lys Arg Lys Tyr Val Gly Ser Pro Leu Ser Asp
                85                  90                  95

Ile Ser Ser Cys Val Asp Tyr Asn Ile Ser Pro Arg Leu Lys Ala Ile
            100                 105                 110

Cys Ile Glu Asn Asn Ser Lys Thr Ala Lys Arg Arg Leu Phe Glu Leu
        115                 120                 125

Pro Asp Ser Gly Tyr Gly Asn Thr Glu Val Glu Thr Gln Gln Met Val
    130                 135                 140

Gln Val Glu Glu Gln Gln Thr Thr Leu Ser Cys Asn Gly Ser Asp Gly
145                 150                 155                 160

Thr His Ser Glu Arg Glu Asn Glu Thr Pro Thr Arg Asn Ile Leu Gln
                165                 170                 175

Val Leu Lys Thr Ser Asn Gly Lys Ala Ala Met Leu Gly Lys Phe Lys
            180                 185                 190
```

-continued

```
Glu Leu Tyr Gly Val Ser Phe Met Glu Leu Ile Arg Pro Phe Gln Ser
            195                 200                 205

Asn Lys Ser Thr Cys Thr Asp Trp Cys Val Ala Ala Phe Gly Val Thr
        210                 215                 220

Gly Thr Val Ala Glu Gly Phe Lys Thr Leu Leu Gln Pro Tyr Cys Leu
225                 230                 235                 240

Tyr Cys His Leu Gln Ser Leu Ala Cys Ser Trp Gly Met Val Met Leu
                245                 250                 255

Met Leu Val Arg Phe Lys Cys Ala Lys Asn Arg Ile Thr Ile Glu Lys
            260                 265                 270

Leu Leu Glu Lys Leu Leu Cys Ile Ser Thr Asn Cys Met Leu Ile Gln
        275                 280                 285

Pro Pro Lys Leu Arg Ser Thr Ala Ala Ala Leu Tyr Trp Tyr Arg Thr
    290                 295                 300

Gly Met Ser Asn Ile Ser Asp Val Tyr Gly Glu Thr Pro Glu Trp Ile
305                 310                 315                 320

Glu Arg Gln Thr Val Leu Gln His Ser Phe Asn Asp Thr Thr Phe Asp
                325                 330                 335

Leu Ser Gln Met Val Gln Trp Ala Tyr Asp Asn Asp Val Met Asp Asp
            340                 345                 350

Ser Glu Ile Ala Tyr Lys Tyr Ala Gln Leu Ala Asp Ser Asp Ser Asn
        355                 360                 365

Ala Cys Ala Phe Leu Lys Ser Asn Ser Gln Ala Lys Ile Val Lys Asp
    370                 375                 380

Cys Gly Thr Met Cys Arg His Tyr Lys Arg Ala Glu Lys Arg Gln Met
385                 390                 395                 400

Ser Met Gly Gln Trp Ile Lys Ser Arg Cys Asp Lys Val Ser Asp Glu
                405                 410                 415

Gly Asp Trp Arg Asp Ile Val Lys Phe Leu Arg Tyr Gln Gln Ile Glu
            420                 425                 430

Phe Val Ser Phe Leu Ser Ala Leu Lys Leu Phe Leu Lys Gly Val Pro
        435                 440                 445

Lys Lys Asn Cys Ile Leu Ile His Gly Ala Pro Asn Thr Gly Lys Ser
    450                 455                 460

Tyr Phe Gly Met Ser Leu Ile Ser Phe Leu Gln Gly Cys Ile Ile Ser
465                 470                 475                 480

Tyr Ala Asn Ser Lys Ser His Phe Trp Leu Gln Pro Leu Ala Asp Ala
                485                 490                 495

Lys Ile Gly Met Leu Asp Asp Ala Thr Thr Pro Cys Trp His Tyr Ile
            500                 505                 510

Asp Asn Tyr Leu Arg Asn Ala Leu Asp Gly Asn Pro Val Ser Ile Asp
        515                 520                 525

Val Lys His Lys Ala Leu Met Gln Leu Lys Cys Pro Pro Leu Leu Ile
    530                 535                 540

Thr Ser Asn Ile Asn Ala Gly Lys Asp Asp Arg Trp Pro Tyr Leu His
545                 550                 555                 560

Ser Arg Leu Val Val Phe Thr Phe Pro Asn Pro Phe Pro Phe Asp Lys
                565                 570                 575

Asn Gly Asn Pro Val Tyr Glu Leu Ser Asp Lys Asn Trp Lys Ser Phe
            580                 585                 590

Phe Ser Arg Thr Trp Cys Arg Leu Asn Leu His Glu Glu Asp Lys
        595                 600                 605

Glu Asn Asp Gly Asp Ser Phe Ser Thr Phe Lys Cys Val Ser Gly Gln
```

Asn Ile Arg Thr Leu
625

<210> SEQ ID NO 43
<211> LENGTH: 372
<212> TYPE: PRT
<213> ORGANISM: Human papillomavirus type 31

<400> SEQUENCE: 43

Met Glu Thr Leu Ser Gln Arg Leu Asn Val Cys Gln Asp Lys Ile Leu
 1               5                  10                  15

Glu His Tyr Glu Asn Asp Ser Lys Arg Leu Cys Asp His Ile Asp Tyr
            20                  25                  30

Trp Lys His Ile Arg Leu Glu Cys Val Leu Met Tyr Lys Ala Arg Glu
        35                  40                  45

Met Gly Ile His Ser Ile Asn His Gln Val Val Pro Ala Leu Ser Val
    50                  55                  60

Ser Lys Ala Lys Ala Leu Gln Ala Ile Glu Leu Gln Met Met Leu Glu
65                  70                  75                  80

Thr Leu Asn Asn Thr Glu Tyr Lys Asn Glu Asp Trp Thr Met Gln Gln
                85                  90                  95

Thr Ser Leu Glu Leu Tyr Leu Thr Ala Pro Thr Gly Cys Leu Lys Lys
            100                 105                 110

His Gly Tyr Thr Val Glu Val Gln Phe Asp Gly Asp Val His Asn Thr
        115                 120                 125

Met His Tyr Thr Asn Trp Lys Phe Ile Tyr Leu Cys Ile Asp Gly Gln
    130                 135                 140

Cys Thr Val Val Glu Gly Gln Val Asn Cys Lys Gly Ile Tyr Tyr Val
145                 150                 155                 160

His Glu Gly His Ile Thr Tyr Phe Val Asn Phe Thr Glu Glu Ala Lys
                165                 170                 175

Lys Tyr Gly Thr Gly Lys Lys Trp Glu Val His Ala Gly Gly Gln Val
            180                 185                 190

Ile Val Phe Pro Glu Ser Val Phe Ser Ser Asp Glu Ile Ser Phe Ala
        195                 200                 205

Gly Ile Val Thr Lys Leu Pro Thr Ala Asn Asn Thr Thr Thr Ser Asn
    210                 215                 220

Ser Lys Thr Cys Ala Leu Gly Thr Ser Glu Gly Val Arg Arg Ala Thr
225                 230                 235                 240

Thr Ser Thr Lys Arg Pro Arg Thr Glu Pro Glu His Arg Asn Thr His
                245                 250                 255

His Pro Asn Lys Leu Leu Arg Gly Asp Ser Val Asp Ser Val Asn Cys
            260                 265                 270

Gly Val Ile Ser Ala Ala Ala Cys Thr Asn Gln Thr Arg Ala Val Ser
        275                 280                 285

Cys Pro Ala Thr Thr Pro Ile Ile His Leu Lys Gly Asp Ala Asn Ile
    290                 295                 300

Leu Lys Cys Leu Arg Tyr Arg Leu Ser Lys Tyr Lys Gln Leu Tyr Glu
305                 310                 315                 320

Gln Val Ser Ser Thr Trp His Trp Thr Cys Thr Asp Gly Lys His Lys
                325                 330                 335

Asn Ala Ile Val Thr Leu Thr Tyr Ile Ser Thr Ser Gln Arg Asp Asp
            340                 345                 350

```
Phe Leu Asn Thr Val Lys Ile Pro Asn Thr Val Ser Val Ser Thr Gly
            355                 360                 365
Tyr Met Thr Ile
    370

<210> SEQ ID NO 44
<211> LENGTH: 84
<212> TYPE: PRT
<213> ORGANISM: Human papillomavirus type 31

<400> SEQUENCE: 44

Met Ile Glu Leu Asn Ile Ser Thr Val Ser Ile Val Leu Cys Phe Leu
  1               5                  10                  15

Leu Cys Phe Cys Val Leu Leu Phe Val Cys Leu Val Ile Arg Pro Leu
                 20                  25                  30

Val Leu Ser Val Ser Val Tyr Ala Thr Leu Leu Leu Ile Val Ile
             35                  40                  45

Leu Trp Val Ile Ala Thr Ser Pro Leu Arg Cys Phe Cys Ile Tyr Val
     50                  55                  60

Val Phe Ile Tyr Ile Pro Leu Phe Val Ile His Thr His Ala Ser Phe
 65                  70                  75                  80

Leu Ser Gln Gln

<210> SEQ ID NO 45
<211> LENGTH: 149
<212> TYPE: PRT
<213> ORGANISM: Human papillomavirus type 31

<400> SEQUENCE: 45

Met Phe Lys Asn Pro Ala Glu Arg Pro Arg Lys Leu His Glu Leu Ser
  1               5                  10                  15

Ser Ala Leu Glu Ile Pro Tyr Asp Glu Leu Arg Leu Asn Cys Val Tyr
                 20                  25                  30

Cys Lys Gly Gln Leu Thr Glu Thr Glu Val Leu Asp Phe Ala Phe Thr
             35                  40                  45

Asp Leu Thr Ile Val Tyr Arg Asp Asp Thr Pro His Gly Val Cys Thr
     50                  55                  60

Lys Cys Leu Arg Phe Tyr Ser Lys Val Ser Glu Phe Arg Trp Tyr Arg
 65                  70                  75                  80

Tyr Ser Val Tyr Gly Thr Thr Leu Glu Lys Leu Thr Asn Lys Gly Ile
                 85                  90                  95

Cys Asp Leu Leu Ile Arg Cys Ile Thr Cys Gln Arg Pro Leu Cys Pro
            100                 105                 110

Glu Glu Lys Gln Arg His Leu Asp Lys Lys Lys Arg Phe His Asn Ile
            115                 120                 125

Gly Gly Arg Trp Thr Gly Arg Cys Ile Ala Cys Trp Arg Arg Pro Arg
        130                 135                 140

Thr Glu Thr Gln Val
145

<210> SEQ ID NO 46
<211> LENGTH: 98
<212> TYPE: PRT
<213> ORGANISM: Human papillomavirus type 31

<400> SEQUENCE: 46

Met Arg Gly Glu Thr Pro Thr Leu Gln Asp Tyr Val Leu Asp Leu Gln
  1               5                  10                  15
```

```
Pro Glu Ala Thr Asp Leu His Cys Tyr Glu Gln Leu Pro Asp Ser Ser
                20                  25                  30

Asp Glu Glu Asp Val Ile Asp Ser Pro Ala Gly Gln Ala Glu Pro Asp
         35                  40                  45

Thr Ser Asn Tyr Asn Ile Val Thr Phe Cys Cys Gln Cys Lys Ser Thr
 50                  55                  60

Leu Arg Leu Cys Val Gln Ser Thr Gln Val Asp Ile Arg Ile Leu Gln
 65                  70                  75                  80

Glu Leu Leu Met Gly Ser Phe Gly Ile Val Cys Pro Asn Cys Ser Thr
                 85                  90                  95

Arg Leu

<210> SEQ ID NO 47
<211> LENGTH: 504
<212> TYPE: PRT
<213> ORGANISM: Human papillomavirus type 31

<400> SEQUENCE: 47

Met Ser Leu Trp Arg Pro Ser Glu Ala Thr Val Tyr Leu Pro Pro Val
 1               5                  10                  15

Pro Val Ser Lys Val Val Ser Thr Asp Glu Tyr Val Thr Arg Thr Asn
                20                  25                  30

Ile Tyr Tyr His Ala Gly Ser Ala Arg Leu Leu Thr Val Gly His Pro
             35                  40                  45

Tyr Tyr Ser Ile Pro Lys Ser Asp Asn Pro Lys Lys Ile Val Val Pro
 50                  55                  60

Lys Val Ser Gly Leu Gln Tyr Arg Val Phe Arg Val Arg Leu Pro Asp
 65                  70                  75                  80

Pro Asn Lys Phe Gly Phe Pro Asp Thr Ser Phe Tyr Asn Pro Glu Thr
                 85                  90                  95

Gln Arg Leu Val Trp Ala Cys Val Gly Leu Glu Val Gly Arg Gly Gln
                100                 105                 110

Pro Leu Gly Val Gly Ile Ser Gly His Pro Leu Leu Asn Lys Phe Asp
            115                 120                 125

Asp Thr Glu Asn Ser Asn Arg Tyr Ala Gly Gly Pro Gly Thr Asp Asn
130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
    210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285
```

```
Asn Ser Thr Tyr Phe Pro Thr Pro Ser Gly Ser Met Val Thr Ser Asp
    290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
        340                 345                 350

Asp Thr Thr Phe Lys Ser Ser Asn Phe Lys Glu Tyr Leu Arg His Gly
            355                 360                 365

Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Thr
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
    450                 455                 460

Leu Gly Arg Lys Phe Leu Leu Gln Ala Gly Tyr Arg Ala Arg Pro Lys
465                 470                 475                 480

Phe Lys Ala Gly Lys Arg Ser Ala Pro Ser Ala Ser Thr Thr Thr Pro
                485                 490                 495

Ala Lys Arg Lys Lys Thr Lys Lys
            500

<210> SEQ ID NO 48
<211> LENGTH: 466
<212> TYPE: PRT
<213> ORGANISM: Human papillomavirus type 31

<400> SEQUENCE: 48

Met Arg Ser Lys Arg Ser Thr Lys Arg Thr Lys Arg Ala Ser Ala Thr
1               5                   10                  15

Gln Leu Tyr Gln Thr Cys Lys Ala Ala Gly Thr Cys Pro Ser Asp Val
            20                  25                  30

Ile Pro Lys Ile Glu His Thr Thr Ile Ala Asp Gln Ile Leu Arg Tyr
        35                  40                  45

Gly Ser Met Gly Val Phe Phe Gly Gly Leu Gly Ile Gly Ser Gly Ser
    50                  55                  60

Gly Thr Gly Gly Arg Thr Gly Tyr Val Pro Leu Ser Thr Arg Pro Ser
65                  70                  75                  80

Thr Val Ser Glu Ala Ser Ile Pro Ile Arg Pro Pro Val Ser Ile Asp
                85                  90                  95

Pro Val Gly Pro Leu Asp Pro Ser Ile Val Ser Leu Val Glu Glu Ser
            100                 105                 110

Gly Ile Val Asp Val Gly Ala Pro Ala Pro Ile Pro His Pro Pro Thr
        115                 120                 125

Thr Ser Gly Phe Asp Ile Ala Thr Thr Ala Asp Thr Thr Pro Ala Ile
    130                 135                 140

Leu Asp Val Thr Ser Val Ser Thr His Glu Asn Pro Thr Phe Thr Asp
```

-continued

```
            145                 150                 155                 160
Pro Ser Val Leu Gln Pro Thr Pro Ala Glu Thr Ser Gly His Leu
                    165                 170                 175

Leu Leu Ser Ser Ser Ile Ser Thr His Asn Tyr Glu Glu Ile Pro
                180                 185                 190

Met Asp Thr Phe Ile Val Ser Thr Asn Asn Glu Asn Ile Thr Ser Ser
                195                 200                 205

Thr Pro Ile Pro Gly Val Arg Arg Pro Ala Arg Leu Gly Leu Tyr Ser
        210                 215                 220

Lys Ala Thr Gln Gln Val Lys Val Ile Asp Pro Thr Phe Leu Ser Ala
225                 230                 235                 240

Pro Lys Gln Leu Ile Thr Tyr Glu Asn Pro Ala Tyr Glu Thr Val Asn
                    245                 250                 255

Ala Glu Glu Ser Leu Tyr Phe Ser Asn Thr Ser His Asn Ile Ala Pro
                260                 265                 270

Asp Pro Asp Phe Leu Asp Ile Ile Ala Leu His Arg Pro Ala Leu Thr
                275                 280                 285

Ser Arg Arg Asn Thr Val Arg Tyr Ser Arg Leu Gly Asn Lys Gln Thr
        290                 295                 300

Leu Arg Thr Arg Ser Gly Ala Thr Ile Gly Ala Arg Val His Tyr Tyr
305                 310                 315                 320

Tyr Asp Ile Ser Ser Ile Asn Pro Ala Gly Glu Ser Ile Glu Met Gln
                    325                 330                 335

Pro Leu Gly Ala Ser Ala Thr Thr Thr Ser Thr Leu Asn Asp Gly Leu
                340                 345                 350

Tyr Asp Ile Tyr Ala Asp Thr Asp Phe Thr Val Asp Thr Pro Ala Thr
                355                 360                 365

His Asn Val Ser Pro Ser Thr Ala Val Gln Ser Thr Ser Ala Val Ser
        370                 375                 380

Ala Tyr Val Pro Thr Asn Thr Thr Val Pro Leu Ser Thr Gly Phe Asp
385                 390                 395                 400

Ile Pro Ile Phe Ser Gly Pro Asp Val Pro Ile Glu His Ala Pro Thr
                    405                 410                 415

Gln Val Phe Pro Phe Pro Leu Ala Pro Thr Thr Pro Gln Val Ser Ile
                420                 425                 430

Phe Val Asp Gly Gly Asp Phe Tyr Leu His Pro Ser Tyr Tyr Met Leu
        435                 440                 445

Lys Arg Arg Arg Lys Arg Val Ser Tyr Phe Phe Thr Asp Val Ser Val
    450                 455                 460

Ala Ala
465

<210> SEQ ID NO 49
<211> LENGTH: 643
<212> TYPE: PRT
<213> ORGANISM: Human papillomavirus type 45

<400> SEQUENCE: 49

Met Ala Asp Pro Glu Gly Thr Asp Gly Glu Gly Thr Gly Cys Asn Gly
  1               5                  10                  15

Trp Phe Phe Val Glu Thr Ile Val Glu Lys Lys Thr Gly Asp Val Ile
                 20                  25                  30

Ser Asp Asp Glu Asp Glu Thr Ala Thr Asp Thr Gly Ser Asp Met Val
         35                  40                  45
```

-continued

```
Asp Phe Ile Asp Thr Gln Leu Ser Ile Cys Glu Gln Ala Glu Gln Glu
 50                  55                  60

Thr Ala Gln Ala Leu Phe His Ala Gln Glu Val Gln Asn Asp Ala Gln
 65                  70                  75                  80

Val Leu His Leu Leu Lys Arg Lys Phe Ala Gly Gly Ser Lys Glu Asn
                 85                  90                  95

Ser Pro Leu Gly Glu Gln Leu Ser Val Asp Thr Asp Leu Ser Pro Arg
            100                 105                 110

Leu Gln Glu Ile Ser Leu Asn Ser Gly His Lys Lys Ala Lys Arg Arg
        115                 120                 125

Leu Phe Thr Ile Ser Asp Ser Gly Tyr Gly Cys Ser Glu Val Glu Ala
    130                 135                 140

Ala Glu Thr Gln Val Thr Val Asn Thr Asn Ala Glu Asn Gly Gly Ser
145                 150                 155                 160

Val His Ser Thr Gln Ser Ser Gly Gly Asp Ser Ser Asp Asn Ala Glu
                165                 170                 175

Asn Val Asp Pro His Cys Ser Ile Thr Glu Leu Lys Glu Leu Leu Gln
            180                 185                 190

Ala Ser Asn Lys Lys Ala Ala Met Leu Ala Val Phe Lys Asp Ile Tyr
        195                 200                 205

Gly Leu Ser Phe Thr Asp Leu Val Arg Asn Phe Lys Ser Asp Lys Thr
    210                 215                 220

Thr Cys Thr Asp Trp Val Met Ala Ile Phe Gly Val Asn Pro Thr Val
225                 230                 235                 240

Ala Glu Gly Phe Lys Thr Leu Ile Lys Pro Ala Thr Leu Tyr Ala His
                245                 250                 255

Ile Gln Cys Leu Asp Cys Lys Trp Gly Val Leu Ile Leu Ala Leu Leu
            260                 265                 270

Arg Tyr Lys Cys Gly Lys Asn Arg Leu Thr Val Ala Lys Gly Leu Ser
        275                 280                 285

Thr Leu Leu His Val Pro Glu Thr Cys Met Leu Ile Glu Pro Pro Lys
    290                 295                 300

Leu Arg Ser Ser Val Ala Ala Leu Tyr Trp Tyr Arg Thr Gly Ile Ser
305                 310                 315                 320

Asn Ile Ser Glu Val Ser Gly Asp Thr Pro Glu Trp Ile Gln Arg Leu
                325                 330                 335

Thr Ile Ile Gln His Gly Ile Asp Asp Ser Asn Phe Asp Leu Ser Asp
            340                 345                 350

Met Val Gln Trp Ala Phe Asp Asn Asp Leu Thr Asp Glu Ser Asp Met
        355                 360                 365

Ala Phe Gln Tyr Ala Gln Leu Ala Asp Cys Asn Ser Asn Ala Ala Ala
    370                 375                 380

Phe Leu Lys Ser Asn Cys Gln Ala Lys Tyr Leu Lys Asp Cys Ala Val
385                 390                 395                 400

Met Cys Arg His Tyr Lys Arg Ala Gln Lys Arg Gln Met Asn Met Ser
                405                 410                 415

Gln Trp Ile Lys Tyr Arg Cys Ser Lys Ile Asp Glu Gly Gly Asp Trp
            420                 425                 430

Arg Pro Ile Val Gln Phe Leu Arg Tyr Gln Gly Val Glu Phe Ile Ser
        435                 440                 445

Phe Leu Arg Ala Leu Lys Glu Phe Leu Lys Gly Thr Pro Lys Lys Asn
    450                 455                 460

Cys Ile Leu Leu Tyr Gly Pro Ala Asn Thr Gly Lys Ser Tyr Phe Gly
```

-continued

```
                465                 470                 475                 480
Met Ser Phe Ile His Phe Leu Gln Gly Ala Ile Ile Ser Phe Val Asn
                    485                 490                 495
Ser Asn Ser His Phe Trp Leu Glu Pro Leu Ala Asp Thr Lys Val Ala
                500                 505                 510
Met Leu Asp Asp Ala Thr His Thr Cys Trp Thr Tyr Phe Asp Asn Tyr
                515                 520                 525
Met Arg Asn Ala Leu Asp Gly Asn Pro Ile Ser Ile Asp Arg Lys His
            530                 535                 540
Lys Pro Leu Leu Gln Leu Lys Cys Pro Ile Leu Leu Thr Ser Asn Ile
545                 550                 555                 560
Ile Asp Pro Ala Lys Asp Asn Lys Trp Pro Tyr Leu Glu Ser Arg Val
                565                 570                 575
Thr Val Phe Thr Phe Pro His Ala Phe Pro Phe Asp Lys Asn Gly Asn
                580                 585                 590
Pro Val Tyr Glu Ile Asn Asp Lys Asn Trp Lys Cys Phe Phe Glu Arg
                595                 600                 605
Thr Trp Ser Arg Leu Asp Leu His Glu Asp Asp Glu Asp Ala Asp Thr
            610                 615                 620
Glu Gly Ile Pro Phe Gly Thr Phe Lys Cys Val Thr Gly Gln Asn Thr
625                 630                 635                 640
Arg Pro Leu

<210> SEQ ID NO 50
<211> LENGTH: 368
<212> TYPE: PRT
<213> ORGANISM: Human papillomavirus type 45

<400> SEQUENCE: 50

Met Lys Met Gln Thr Pro Lys Glu Ser Leu Ser Glu Arg Leu Ser Ala
1               5                   10                  15
Leu Gln Asp Lys Ile Leu Asp His Tyr Glu Asn Asp Ser Lys Asp Ile
                20                  25                  30
Asn Ser Gln Ile Ser Tyr Trp Gln Leu Ile Arg Leu Glu Asn Ala Ile
            35                  40                  45
Leu Phe Thr Ala Arg Glu His Gly Ile Thr Lys Leu Asn His Gln Val
        50                  55                  60
Val Pro Pro Ile Asn Ile Ser Lys Ser Lys Ala His Lys Ala Ile Glu
65                  70                  75                  80
Leu Gln Met Ala Leu Lys Gly Leu Ala Gln Ser Lys Tyr Asn Asn Glu
                85                  90                  95
Glu Trp Thr Leu Gln Asp Thr Cys Glu Glu Leu Trp Asn Thr Glu Pro
            100                 105                 110
Ser Gln Cys Phe Lys Lys Gly Gly Lys Thr Val His Val Tyr Phe Asp
        115                 120                 125
Gly Asn Lys Asp Asn Cys Met Asn Tyr Val Val Trp Asp Ser Ile Tyr
    130                 135                 140
Tyr Ile Thr Glu Thr Gly Ile Trp Asp Lys Thr Ala Ala Cys Val Ser
145                 150                 155                 160
Tyr Trp Gly Val Tyr Tyr Ile Lys Asp Gly Asp Thr Thr Tyr Tyr Val
                165                 170                 175
Gln Phe Lys Ser Glu Cys Glu Lys Tyr Gly Asn Ser Asn Thr Trp Glu
            180                 185                 190
Val Gln Tyr Gly Gly Asn Val Ile Asp Cys Asn Asp Ser Met Cys Ser
```

```
                195                 200                 205
Thr Ser Asp Asp Thr Val Ser Ala Thr Gln Ile Val Arg Gln Leu Gln
        210                 215                 220

His Ala Ser Thr Ser Thr Pro Lys Thr Ala Ser Val Gly Thr Pro Lys
225                 230                 235                 240

Pro His Ile Gln Thr Pro Ala Thr Lys Arg Pro Arg Gln Cys Gly Leu
                245                 250                 255

Thr Glu Gln His His Gly Arg Val Asn Thr His Val His Asn Pro Leu
        260                 265                 270

Leu Cys Ser Ser Thr Ser Asn Asn Lys Arg Arg Lys Val Cys Ser Gly
        275                 280                 285

Asn Thr Thr Pro Ile Ile His Leu Lys Gly Asp Lys Asn Ser Leu Lys
        290                 295                 300

Cys Leu Arg Tyr Arg Leu Arg Lys Tyr Ala Asp His Tyr Ser Glu Ile
305                 310                 315                 320

Ser Ser Thr Trp His Trp Thr Gly Cys Asn Lys Asn Thr Gly Ile Leu
                325                 330                 335

Thr Val Thr Tyr Asn Ser Glu Val Gln Arg Asn Thr Phe Leu Asp Val
        340                 345                 350

Val Thr Ile Pro Asn Ser Val Gln Ile Ser Val Gly Tyr Met Thr Ile
        355                 360                 365

<210> SEQ ID NO 51
<211> LENGTH: 158
<212> TYPE: PRT
<213> ORGANISM: Human papillomavirus type 45

<400> SEQUENCE: 51

Met Ala Arg Phe Asp Asp Pro Thr Gln Arg Pro Tyr Lys Leu Pro Asp
1               5                   10                  15

Leu Cys Thr Glu Leu Asn Thr Ser Leu Gln Asp Val Ser Ile Ala Cys
                20                  25                  30

Val Tyr Cys Lys Ala Thr Leu Glu Arg Thr Glu Val Tyr Gln Phe Ala
            35                  40                  45

Phe Lys Asp Leu Phe Ile Val Tyr Arg Asp Cys Ile Ala Tyr Ala Ala
        50                  55                  60

Cys His Lys Cys Ile Asp Phe Tyr Ser Arg Ile Arg Glu Leu Arg Tyr
65                  70                  75                  80

Tyr Ser Asn Ser Val Tyr Gly Glu Thr Leu Glu Lys Ile Thr Asn Thr
                85                  90                  95

Glu Leu Tyr Asn Leu Leu Ile Arg Cys Leu Arg Cys Gln Lys Pro Leu
            100                 105                 110

Asn Pro Ala Glu Lys Arg Arg His Leu Lys Asp Lys Arg Arg Phe His
        115                 120                 125

Ser Ile Ala Gly Gln Tyr Arg Gly Gln Cys Asn Thr Cys Cys Asp Gln
        130                 135                 140

Ala Arg Gln Glu Arg Leu Arg Arg Arg Glu Thr Gln Val
145                 150                 155

<210> SEQ ID NO 52
<211> LENGTH: 106
<212> TYPE: PRT
<213> ORGANISM: Human papillomavirus type 45

<400> SEQUENCE: 52

Met His Gly Pro Arg Ala Thr Leu Gln Glu Ile Val Leu His Leu Glu
1               5                   10                  15
```

```
                1               5                  10                  15
Pro Gln Asn Glu Leu Asp Pro Val Asp Leu Leu Cys Tyr Glu Gln Leu
                    20                  25                  30

Ser Glu Ser Glu Glu Asn Asp Glu Ala Asp Gly Val Ser His Ala
                35                  40                  45

Gln Leu Pro Ala Arg Arg Ala Glu Pro Gln Arg His Lys Ile Leu Cys
            50                  55                  60

Val Cys Cys Lys Cys Asp Gly Arg Ile Glu Leu Thr Val Glu Ser Ser
65                  70                  75                  80

Ala Asp Asp Leu Arg Thr Leu Gln Gln Leu Phe Leu Ser Thr Leu Ser
                    85                  90                  95

Phe Val Cys Pro Trp Cys Ala Thr Asn Gln
                100                 105

<210> SEQ ID NO 53
<211> LENGTH: 536
<212> TYPE: PRT
<213> ORGANISM: Human papillomavirus type 45

<400> SEQUENCE: 53

Met Ala His Asn Ile Ile Tyr Gly His Gly Ile Ile Phe Leu Lys
1               5                   10                  15

Asn Val Asn Val Phe Pro Ile Phe Leu Gln Met Ala Leu Trp Arg Pro
                    20                  25                  30

Ser Asp Ser Thr Val Tyr Leu Pro Pro Ser Val Ala Arg Val Val
                35                  40                  45

Asn Thr Asp Asp Tyr Val Ser Arg Thr Ser Ile Phe Tyr His Ala Gly
            50                  55                  60

Ser Ser Arg Leu Leu Thr Val Gly Asn Pro Tyr Phe Arg Val Val Pro
65                  70                  75                  80

Ser Gly Ala Gly Asn Lys Gln Ala Val Pro Lys Val Ser Ala Tyr Gln
                    85                  90                  95

Tyr Arg Val Phe Arg Val Ala Leu Pro Asp Pro Asn Lys Phe Gly Leu
                100                 105                 110

Pro Asp Ser Thr Ile Tyr Asn Pro Glu Thr Gln Arg Leu Val Trp Ala
            115                 120                 125

Cys Val Gly Met Glu Ile Gly Arg Gly Gln Pro Leu Gly Ile Gly Leu
130                 135                 140

Ser Gly His Pro Phe Tyr Asn Lys Leu Asp Asp Thr Glu Ser Ala His
145                 150                 155                 160

Ala Ala Thr Ala Val Ile Thr Gln Asp Val Arg Asp Asn Val Ser Val
                165                 170                 175

Asp Tyr Lys Gln Thr Gln Leu Cys Ile Leu Gly Cys Val Pro Ala Ile
            180                 185                 190

Gly Glu His Trp Ala Lys Gly Thr Leu Cys Lys Pro Ala Gln Leu Gln
        195                 200                 205

Pro Gly Asp Cys Pro Pro Leu Glu Leu Lys Asn Thr Ile Ile Glu Asp
    210                 215                 220

Gly Asp Met Val Asp Thr Gly Tyr Gly Ala Met Asp Phe Ser Thr Leu
225                 230                 235                 240

Gln Asp Thr Lys Cys Glu Val Pro Leu Asp Ile Cys Gln Ser Ile Cys
                245                 250                 255

Lys Tyr Pro Asp Tyr Leu Gln Met Ser Ala Asp Pro Tyr Gly Asp Ser
            260                 265                 270
```

```
Met Phe Phe Cys Leu Arg Arg Glu Gln Leu Phe Ala Arg His Phe Trp
            275                 280                 285
Asn Arg Ala Gly Val Met Gly Asp Thr Val Pro Thr Asp Leu Tyr Ile
        290                 295                 300
Lys Gly Thr Ser Ala Asn Met Arg Glu Thr Pro Gly Ser Cys Val Tyr
305                 310                 315                 320
Ser Pro Ser Pro Ser Gly Ser Ile Thr Thr Ser Asp Ser Gln Leu Phe
                325                 330                 335
Asn Lys Pro Tyr Trp Leu His Lys Ala Gln Gly His Asn Asn Gly Ile
            340                 345                 350
Cys Trp His Asn Gln Leu Phe Val Thr Val Val Asp Thr Thr Arg Ser
        355                 360                 365
Thr Asn Leu Thr Leu Cys Ala Ser Thr Gln Asn Pro Val Pro Asn Thr
370                 375                 380
Tyr Asp Pro Thr Lys Phe Lys His Tyr Ser Arg His Val Glu Glu Tyr
385                 390                 395                 400
Asp Leu Gln Phe Ile Phe Gln Leu Cys Thr Ile Thr Leu Thr Ala Glu
                405                 410                 415
Val Met Ser Tyr Ile His Ser Met Asn Ser Ser Ile Leu Glu Asn Trp
            420                 425                 430
Asn Phe Gly Val Pro Pro Pro Thr Thr Ser Leu Val Asp Thr Tyr
        435                 440                 445
Arg Phe Val Gln Ser Val Ala Val Thr Cys Gln Lys Asp Thr Thr Pro
    450                 455                 460
Pro Glu Lys Gln Asp Pro Tyr Asp Lys Leu Lys Phe Trp Thr Val Asp
465                 470                 475                 480
Leu Lys Glu Lys Phe Ser Ser Asp Leu Asp Gln Tyr Pro Leu Gly Arg
                485                 490                 495
Lys Phe Leu Val Gln Ala Gly Leu Arg Arg Arg Pro Thr Ile Gly Pro
            500                 505                 510
Arg Lys Arg Pro Ala Ala Ser Thr Ser Thr Ala Ser Arg Pro Ala Lys
        515                 520                 525
Arg Val Arg Ile Arg Ser Lys Lys
    530                 535

<210> SEQ ID NO 54
<211> LENGTH: 463
<212> TYPE: PRT
<213> ORGANISM: Human papillomavirus type 45

<400> SEQUENCE: 54

Met Val Ser His Arg Ala Ala Arg Arg Lys Arg Ala Ser Ala Thr Asp
 1               5                  10                  15
Leu Tyr Arg Thr Cys Lys Gln Ser Gly Thr Cys Pro Pro Asp Val Ile
                20                  25                  30
Asn Lys Val Glu Gly Thr Thr Leu Ala Asp Lys Ile Leu Gln Trp Ser
            35                  40                  45
Ser Leu Gly Ile Phe Leu Gly Gly Leu Gly Ile Gly Thr Gly Ser Gly
        50                  55                  60
Ser Gly Gly Arg Thr Gly Tyr Val Pro Leu Gly Gly Arg Ser Asn Thr
65                  70                  75                  80
Val Val Asp Val Gly Pro Thr Arg Pro Pro Val Val Ile Glu Pro Val
                85                  90                  95
Gly Pro Thr Asp Pro Ser Ile Val Thr Leu Val Glu Asp Ser Ser Val
            100                 105                 110
```

```
Val Ala Ser Gly Ala Pro Val Pro Thr Phe Thr Gly Thr Ser Gly Phe
            115                 120                 125

Glu Ile Thr Ser Ser Gly Thr Thr Pro Ala Val Leu Asp Ile Thr
        130                 135                 140

Pro Thr Val Asp Ser Val Ser Ile Ser Ser Thr Ser Phe Thr Asn Pro
145                 150                 155                 160

Ala Phe Ser Asp Pro Ser Ile Ile Glu Val Pro Gln Thr Gly Glu Val
                165                 170                 175

Ser Gly Asn Ile Phe Val Gly Thr Pro Thr Ser Gly Ser His Gly Tyr
            180                 185                 190

Glu Glu Ile Pro Leu Gln Thr Phe Ala Ser Ser Gly Ser Gly Thr Glu
        195                 200                 205

Pro Ile Ser Ser Thr Pro Leu Pro Thr Val Arg Arg Val Arg Gly Pro
210                 215                 220

Arg Leu Tyr Ser Arg Ala Asn Gln Gln Val Arg Val Ser Thr Ser Gln
225                 230                 235                 240

Phe Leu Thr His Pro Ser Ser Leu Val Thr Phe Asp Asn Pro Ala Tyr
                245                 250                 255

Glu Pro Leu Asp Thr Thr Leu Ser Phe Glu Pro Thr Ser Asn Val Pro
            260                 265                 270

Asp Ser Asp Phe Met Asp Ile Ile Arg Leu His Arg Pro Ala Leu Ser
        275                 280                 285

Ser Arg Arg Gly Thr Val Arg Phe Ser Arg Leu Gly Gln Arg Ala Thr
290                 295                 300

Met Phe Thr Arg Ser Gly Lys Gln Ile Gly Gly Arg Val His Phe Tyr
305                 310                 315                 320

His Asp Ile Ser Pro Ile Ala Ala Thr Glu Glu Ile Glu Leu Gln Pro
                325                 330                 335

Leu Ile Ser Ala Thr Asn Asp Ser Asp Leu Phe Asp Val Tyr Ala Asp
            340                 345                 350

Phe Pro Pro Pro Ala Ser Thr Thr Pro Ser Thr Ile His Lys Ser Phe
        355                 360                 365

Thr Tyr Pro Lys Tyr Ser Leu Thr Met Pro Ser Thr Ala Ala Ser Ser
370                 375                 380

Tyr Ser Asn Val Thr Val Pro Leu Thr Ser Ala Trp Asp Val Pro Ile
385                 390                 395                 400

Tyr Thr Gly Pro Asp Ile Ile Leu Pro Ser His Thr Pro Met Trp Pro
                405                 410                 415

Ser Thr Ser Pro Thr Asn Ala Ser Thr Thr Thr Tyr Ile Gly Ile His
            420                 425                 430

Gly Thr Gln Tyr Tyr Leu Trp Pro Trp Tyr Tyr Phe Pro Lys Lys
        435                 440                 445

Arg Lys Arg Ile Pro Tyr Phe Phe Ala Asp Gly Phe Val Ala Ala
    450                 455                 460

<210> SEQ ID NO 55
<211> LENGTH: 644
<212> TYPE: PRT
<213> ORGANISM: Human papillomavirus type 33

<400> SEQUENCE: 55

Met Ala Asp Pro Glu Gly Thr Asn Gly Ala Gly Met Gly Cys Thr Gly
1               5                   10                  15

Trp Phe Glu Val Glu Ala Val Ile Glu Arg Arg Thr Gly Asp Asn Ile
```

-continued

```
                20                  25                  30
Ser Glu Asp Glu Asp Glu Thr Ala Asp Ser Gly Thr Asp Leu Leu
        35                  40                  45
Glu Phe Ile Asp Asp Ser Met Glu Asn Ser Ile Gln Ala Asp Thr Glu
    50                  55                  60
Ala Ala Arg Ala Leu Phe Asn Ile Gln Glu Gly Glu Asp Asp Leu Asn
65                  70                  75                  80
Ala Val Cys Ala Leu Lys Arg Lys Phe Ala Ala Cys Ser Gln Ser Ala
                85                  90                  95
Ala Glu Asp Val Val Asp Arg Ala Ala Asn Pro Cys Arg Thr Ser Ile
            100                 105                 110
Asn Lys Asn Lys Glu Cys Thr Tyr Arg Lys Arg Lys Ile Asp Glu Leu
        115                 120                 125
Glu Asp Ser Gly Tyr Gly Asn Thr Glu Val Glu Thr Gln Gln Met Val
    130                 135                 140
Gln Gln Val Glu Ser Gln Asn Gly Asp Thr Asn Leu Asn Asp Leu Glu
145                 150                 155                 160
Ser Ser Gly Val Gly Asp Asp Ser Glu Val Ser Cys Glu Thr Asn Val
                165                 170                 175
Asp Ser Cys Glu Asn Val Thr Leu Gln Glu Ile Ser Asn Val Leu His
            180                 185                 190
Ser Ser Asn Thr Lys Ala Asn Ile Leu Tyr Lys Phe Lys Glu Ala Tyr
        195                 200                 205
Gly Ile Ser Phe Met Glu Leu Val Arg Pro Phe Lys Ser Asp Lys Thr
    210                 215                 220
Ser Cys Thr Asp Trp Cys Ile Thr Gly Tyr Gly Ile Ser Pro Ser Val
225                 230                 235                 240
Ala Glu Ser Leu Lys Val Leu Ile Lys Gln His Ser Leu Tyr Thr His
                245                 250                 255
Leu Gln Cys Leu Thr Cys Asp Arg Gly Ile Ile Ile Leu Leu Leu Ile
            260                 265                 270
Arg Phe Arg Cys Ser Lys Asn Arg Leu Thr Val Ala Lys Leu Met Ser
        275                 280                 285
Asn Leu Leu Ser Ile Pro Glu Thr Cys Met Val Ile Glu Pro Pro Lys
    290                 295                 300
Leu Arg Ser Gln Thr Cys Ala Leu Tyr Trp Phe Arg Thr Ala Met Ser
305                 310                 315                 320
Asn Ile Ser Asp Val Gln Gly Thr Thr Pro Glu Trp Ile Asp Arg Leu
                325                 330                 335
Thr Val Leu Gln His Ser Phe Asn Asp Asn Ile Phe Asp Leu Ser Glu
            340                 345                 350
Met Val Gln Trp Ala Tyr Asp Asn Glu Leu Thr Asp Ser Asp Ile
        355                 360                 365
Ala Tyr Tyr Tyr Ala Gln Leu Ala Asp Ser Asn Ser Asn Ala Ala Ala
    370                 375                 380
Phe Leu Lys Ser Asn Ser Gln Ala Lys Ile Val Lys Asp Cys Gly Ile
385                 390                 395                 400
Met Cys Arg His Tyr Lys Lys Ala Glu Lys Arg Lys Met Ser Ile Gly
                405                 410                 415
Gln Trp Ile Gln Ser Arg Cys Glu Lys Thr Asn Asp Gly Gly Asn Trp
            420                 425                 430
Arg Pro Ile Val Gln Leu Leu Arg Tyr Gln Asn Ile Glu Phe Thr Ala
        435                 440                 445
```

```
Phe Leu Gly Ala Phe Lys Lys Phe Leu Lys Gly Ile Pro Lys Lys Ser
    450                 455                 460

Cys Met Leu Ile Cys Gly Pro Ala Asn Thr Gly Lys Ser Tyr Phe Gly
465                 470                 475                 480

Met Ser Leu Ile Gln Phe Leu Lys Gly Cys Val Ile Ser Cys Val Asn
                485                 490                 495

Ser Lys Ser His Phe Trp Leu Gln Pro Leu Ser Asp Ala Lys Ile Gly
            500                 505                 510

Met Ile Asp Asp Val Thr Pro Ile Ser Trp Thr Tyr Ile Asp Asp Tyr
        515                 520                 525

Met Arg Asn Ala Leu Asp Gly Asn Glu Ile Ser Ile Asp Val Lys His
    530                 535                 540

Arg Ala Leu Val Gln Leu Lys Cys Pro Pro Leu Leu Leu Thr Ser Asn
545                 550                 555                 560

Thr Asn Ala Gly Thr Asp Ser Arg Trp Pro Tyr Leu His Ser Arg Leu
                565                 570                 575

Thr Val Phe Glu Phe Lys Asn Pro Phe Pro Phe Asp Glu Asn Gly Asn
            580                 585                 590

Pro Val Tyr Ala Ile Asn Asp Glu Asn Trp Lys Ser Phe Phe Ser Arg
        595                 600                 605

Thr Trp Cys Lys Leu Asp Leu Ile Glu Glu Asp Lys Glu Asn His
    610                 615                 620

Gly Gly Asn Ile Ser Thr Phe Lys Cys Ser Ala Gly Glu Asn Thr Arg
625                 630                 635                 640

Ser Leu Arg Ser

<210> SEQ ID NO 56
<211> LENGTH: 353
<212> TYPE: PRT
<213> ORGANISM: Human papillomavirus type 33

<400> SEQUENCE: 56

Met Glu Glu Ile Ser Ala Arg Leu Asn Ala Val Gln Glu Lys Ile Leu
  1               5                  10                  15

Asp Leu Tyr Glu Ala Asp Lys Thr Asp Leu Pro Ser Gln Ile Glu His
            20                  25                  30

Trp Lys Leu Ile Arg Met Glu Cys Ala Leu Leu Tyr Thr Ala Lys Gln
        35                  40                  45

Met Gly Phe Ser His Leu Cys His Gln Val Val Pro Ser Leu Leu Ala
    50                  55                  60

Ser Lys Thr Lys Ala Phe Gln Val Ile Glu Leu Gln Met Ala Leu Glu
65                  70                  75                  80

Thr Leu Ser Lys Ser Gln Tyr Ser Thr Ser Gln Trp Thr Leu Gln Gln
                85                  90                  95

Thr Ser Leu Glu Val Trp Leu Cys Glu Pro Pro Lys Cys Phe Lys Lys
            100                 105                 110

Gln Gly Glu Thr Val Thr Val Gln Tyr Asp Asn Asp Lys Lys Asn Thr
        115                 120                 125

Met Asp Tyr Thr Asn Trp Gly Glu Ile Tyr Ile Glu Glu Asp Thr
    130                 135                 140

Cys Thr Met Val Thr Gly Lys Val Asp Tyr Ile Gly Met Tyr Tyr Ile
145                 150                 155                 160

His Asn Cys Glu Lys Val Tyr Phe Lys Tyr Phe Lys Glu Asp Ala Ala
                165                 170                 175
```

```
Lys Tyr Ser Lys Thr Gln Met Trp Glu Val His Val Gly Gly Gln Val
                180                 185                 190

Ile Val Cys Pro Thr Ser Ile Ser Ser Asn Gln Ile Ser Thr Thr Glu
            195                 200                 205

Thr Ala Asp Ile Gln Thr Asp Asn Asp Asn Arg Pro Pro Gln Ala Ala
        210                 215                 220

Ala Lys Arg Arg Arg Pro Ala Asp Thr Thr Asp Thr Ala Gln Pro Leu
225                 230                 235                 240

Thr Lys Leu Phe Cys Ala Asp Pro Ala Leu Asp Asn Arg Thr Ala Arg
                245                 250                 255

Thr Ala Thr Asn Cys Thr Asn Lys Gln Arg Thr Val Cys Ser Ser Asn
            260                 265                 270

Val Ala Pro Ile Val His Leu Lys Gly Glu Ser Asn Ser Leu Lys Cys
        275                 280                 285

Leu Arg Tyr Arg Leu Lys Pro Tyr Lys Glu Leu Tyr Ser Ser Met Ser
290                 295                 300

Ser Thr Trp His Trp Thr Ser Asp Asn Lys Asn Ser Lys Asn Gly Ile
305                 310                 315                 320

Val Thr Val Thr Phe Val Thr Glu Gln Gln Gln Met Phe Leu Gly
                325                 330                 335

Thr Val Lys Ile Pro Pro Thr Val Gln Ile Ser Thr Gly Phe Met Thr
                340                 345                 350

Leu

<210> SEQ ID NO 57
<211> LENGTH: 75
<212> TYPE: PRT
<213> ORGANISM: Human papillomavirus type 33

<400> SEQUENCE: 57

Met Ile Phe Val Phe Val Leu Cys Phe Ile Leu Phe Leu Cys Leu Ser
1               5                   10                  15

Leu Leu Leu Arg Pro Leu Ile Leu Ser Ile Ser Thr Tyr Ala Trp Leu
                20                  25                  30

Leu Val Leu Val Leu Leu Leu Trp Val Phe Val Gly Ser Pro Leu Lys
            35                  40                  45

Ile Phe Phe Cys Tyr Leu Leu Phe Leu Tyr Leu Pro Met Met Cys Ile
        50                  55                  60

Asn Phe His Ala Gln His Met Thr Gln Gln Glu
65                  70                  75

<210> SEQ ID NO 58
<211> LENGTH: 149
<212> TYPE: PRT
<213> ORGANISM: Human papillomavirus type 33

<400> SEQUENCE: 58

Met Phe Gln Asp Thr Glu Glu Lys Pro Arg Thr Leu His Asp Leu Cys
1               5                   10                  15

Gln Ala Leu Glu Thr Thr Ile His Asn Ile Glu Leu Gln Cys Val Glu
                20                  25                  30

Cys Lys Lys Pro Leu Gln Arg Ser Glu Val Tyr Asp Phe Ala Phe Ala
            35                  40                  45

Asp Leu Thr Val Val Tyr Arg Glu Gly Asn Pro Phe Gly Ile Cys Lys
        50                  55                  60
```

```
Leu Cys Leu Arg Phe Leu Ser Lys Ile Ser Glu Tyr Arg His Tyr Asn
 65                  70                  75                  80

Tyr Ser Val Tyr Gly Asn Thr Leu Glu Gln Thr Val Lys Lys Pro Leu
                 85                  90                  95

Asn Glu Ile Leu Ile Arg Cys Ile Cys Gln Arg Pro Leu Cys Pro
            100                 105                 110

Gln Glu Lys Lys Arg His Val Asp Leu Asn Lys Arg Phe His Asn Ile
        115                 120                 125

Ser Gly Arg Trp Ala Gly Arg Cys Ala Ala Cys Trp Arg Ser Arg Arg
    130                 135                 140

Arg Glu Thr Ala Leu
145

<210> SEQ ID NO 59
<211> LENGTH: 97
<212> TYPE: PRT
<213> ORGANISM: Human papillomavirus type 33

<400> SEQUENCE: 59

Met Arg Gly His Lys Pro Thr Leu Lys Glu Tyr Val Leu Asp Leu Tyr
  1               5                  10                  15

Pro Glu Pro Thr Asp Leu Tyr Cys Tyr Glu Gln Leu Ser Asp Ser Ser
                 20                  25                  30

Asp Glu Asp Glu Gly Leu Asp Arg Pro Asp Gly Gln Ala Gln Pro Ala
             35                  40                  45

Thr Ala Asp Tyr Tyr Ile Val Thr Cys Cys His Thr Cys Asn Thr Thr
     50                  55                  60

Val Arg Leu Cys Val Asn Ser Thr Ala Ser Asp Leu Arg Thr Ile Gln
 65                  70                  75                  80

Gln Leu Leu Met Gly Thr Val Asn Ile Val Cys Pro Thr Cys Ala Gln
                 85                  90                  95

Gln

<210> SEQ ID NO 60
<211> LENGTH: 499
<212> TYPE: PRT
<213> ORGANISM: Human papillomavirus type 33

<400> SEQUENCE: 60

Met Ser Val Trp Arg Pro Ser Glu Ala Thr Val Tyr Leu Pro Pro Val
  1               5                  10                  15

Pro Val Ser Lys Val Val Ser Thr Asp Glu Tyr Val Ser Arg Thr Ser
                 20                  25                  30

Ile Tyr Tyr Tyr Ala Gly Ser Ser Arg Leu Leu Ala Val Gly His Pro
             35                  40                  45

Tyr Phe Ser Ile Lys Asn Pro Thr Asn Ala Lys Lys Leu Leu Val Pro
     50                  55                  60

Lys Val Ser Gly Leu Gln Tyr Arg Val Phe Arg Val Arg Leu Pro Asp
 65                  70                  75                  80

Pro Asn Lys Phe Gly Phe Pro Asp Thr Ser Phe Tyr Asn Pro Asp Thr
                 85                  90                  95

Gln Arg Leu Val Trp Ala Cys Val Gly Leu Glu Ile Gly Arg Gly Gln
            100                 105                 110

Pro Leu Gly Val Gly Ile Ser Gly His Pro Leu Leu Asn Lys Phe Asp
        115                 120                 125

Asp Thr Glu Thr Gly Asn Lys Tyr Pro Gly Gln Pro Gly Ala Asp Asn
```

-continued

```
            130                 135                 140
Arg Glu Cys Leu Ser Met Asp Tyr Lys Gln Thr Gln Leu Cys Leu Leu
145                 150                 155                 160

Gly Cys Lys Pro Pro Thr Gly Glu His Trp Gly Lys Gly Val Ala Cys
                165                 170                 175

Thr Asn Ala Ala Pro Ala Asn Asp Cys Pro Leu Glu Leu Ile Asn
            180                 185                 190

Thr Ile Ile Glu Asp Gly Asp Met Val Asp Thr Gly Phe Gly Cys Met
                195                 200                 205

Asp Phe Lys Thr Leu Gln Ala Asn Lys Ser Asp Val Pro Ile Asp Ile
210                 215                 220

Cys Gly Ser Thr Cys Lys Tyr Pro Asp Tyr Leu Lys Met Thr Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Thr Leu Gly Glu Ala Val Pro
                260                 265                 270

Asp Asp Leu Tyr Ile Lys Gly Ser Gly Thr Thr Ala Ser Ile Gln Ser
            275                 280                 285

Ser Ala Phe Phe Pro Thr Pro Ser Gly Ser Met Val Thr Ser Glu Ser
290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Val Phe Val Thr Val Val Asp Thr
                325                 330                 335

Thr Arg Ser Thr Asn Met Thr Leu Cys Thr Gln Val Thr Ser Asp Ser
                340                 345                 350

Thr Tyr Lys Asn Glu Asn Phe Lys Glu Tyr Ile Arg His Val Glu Glu
            355                 360                 365

Tyr Asp Leu Gln Phe Val Phe Gln Leu Cys Lys Val Thr Leu Thr Ala
370                 375                 380

Glu Val Met Thr Tyr Ile His Ala Met Asn Pro Asp Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Val Pro
                420                 425                 430

Pro Lys Glu Lys Glu Asp Pro Leu Gly Lys Tyr Thr Phe Trp Glu Val
            435                 440                 445

Asp Leu Lys Glu Lys Phe Ser Ala Asp Leu Asp Gln Phe Pro Leu Gly
450                 455                 460

Arg Lys Phe Leu Leu Gln Ala Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys

<210> SEQ ID NO 61
<211> LENGTH: 467
<212> TYPE: PRT
<213> ORGANISM: Human papillomavirus type 33

<400> SEQUENCE: 61

Met Arg His Lys Arg Ser Thr Arg Arg Lys Arg Ala Ser Ala Thr Gln
```

-continued

```
  1               5              10              15
Leu Tyr Gln Thr Cys Lys Ala Thr Gly Thr Cys Pro Pro Asp Val Ile
                 20                  25                  30

Pro Lys Val Glu Gly Ser Thr Ile Ala Asp Gln Ile Leu Lys Tyr Gly
                 35                  40                  45

Ser Leu Gly Val Phe Phe Gly Leu Gly Ile Gly Thr Gly Ser Gly
                 50                  55                  60

Ser Gly Gly Arg Thr Gly Tyr Val Pro Ile Gly Thr Asp Pro Pro Thr
 65                  70                  75                  80

Ala Ala Ile Pro Leu Gln Pro Ile Arg Pro Pro Val Thr Val Asp Thr
                 85                  90                  95

Val Gly Pro Leu Asp Ser Ser Ile Val Ser Leu Ile Glu Glu Thr Ser
                100                 105                 110

Phe Ile Glu Ala Gly Ala Pro Ala Pro Ser Ile Pro Thr Pro Ser Gly
                115                 120                 125

Phe Asp Val Thr Thr Ser Ala Asp Thr Thr Pro Ala Ile Ile Asn Val
                130                 135                 140

Ser Ser Val Gly Glu Ser Ser Ile Gln Thr Ile Ser Thr His Leu Asn
145                 150                 155                 160

Pro Thr Phe Thr Glu Pro Ser Val Leu His Pro Pro Ala Pro Ala Glu
                165                 170                 175

Ala Ser Gly His Phe Ile Phe Ser Ser Pro Thr Val Ser Thr Gln Ser
                180                 185                 190

Tyr Glu Asn Ile Pro Met Asp Thr Phe Val Val Ser Thr Asp Ser Ser
                195                 200                 205

Asn Val Thr Ser Ser Thr Pro Ile Pro Gly Ser Arg Pro Val Ala Arg
                210                 215                 220

Leu Gly Leu Tyr Ser Arg Asn Thr Gln Gln Val Lys Val Val Asp Pro
225                 230                 235                 240

Ala Phe Leu Thr Ser Pro His Lys Leu Ile Thr Tyr Asp Asn Pro Ala
                245                 250                 255

Phe Glu Ser Phe Asp Pro Glu Asp Thr Leu Gln Phe Gln His Ser Asp
                260                 265                 270

Ile Ser Pro Ala Pro Asp Pro Asp Phe Leu Asp Ile Ile Ala Leu His
                275                 280                 285

Arg Pro Ala Ile Thr Ser Arg Arg His Thr Val Arg Phe Ser Arg Val
                290                 295                 300

Gly Gln Lys Ala Thr Leu Lys Thr Arg Ser Gly Lys Gln Ile Gly Ala
305                 310                 315                 320

Arg Ile His Tyr Tyr Gln Asp Leu Ser Pro Ile Val Pro Leu Asp His
                325                 330                 335

Thr Val Pro Asn Glu Gln Tyr Glu Leu Gln Pro Leu His Asp Thr Ser
                340                 345                 350

Thr Ser Ser Tyr Ser Ile Asn Asp Gly Leu Tyr Asp Val Tyr Ala Asp
                355                 360                 365

Asp Val Asp Asn Val His Thr Pro Met Gln His Ser Tyr Ser Thr Phe
                370                 375                 380

Ala Thr Thr Arg Thr Ser Asn Val Ser Ile Pro Leu Asn Thr Gly Phe
385                 390                 395                 400

Asp Thr Pro Val Met Ser Gly Pro Asp Ile Pro Ser Pro Leu Phe Pro
                405                 410                 415

Thr Ser Ser Pro Phe Val Pro Ile Ser Pro Phe Pro Phe Asp Thr
                420                 425                 430
```

```
Ile Val Val Asp Gly Ala Asp Phe Val Leu His Pro Ser Tyr Phe Ile
            435                 440                 445

Leu Arg Arg Arg Arg Lys Arg Phe Pro Tyr Phe Phe Thr Asp Val Arg
        450                 455                 460

Val Ala Ala
465

<210> SEQ ID NO 62
<211> LENGTH: 310
<212> TYPE: PRT
<213> ORGANISM: Human papillomavirus type 56

<400> SEQUENCE: 62

Met Val Pro Cys Leu Gln Val Cys Lys Ala Lys Ala Cys Ser Ala Ile
  1               5                  10                  15

Glu Val Gln Ile Ala Leu Glu Ser Leu Ser Thr Thr Ile Tyr Asn Asn
             20                  25                  30

Glu Glu Trp Thr Leu Arg Asp Thr Cys Glu Glu Leu Trp Leu Thr Glu
         35                  40                  45

Pro Lys Lys Cys Phe Lys Lys Glu Gly Gln His Ile Glu Val Trp Phe
     50                  55                  60

Asp Gly Ser Lys Asn Asn Cys Met Gln Tyr Val Ala Trp Lys Tyr Ile
 65                  70                  75                  80

Tyr Tyr Asn Gly Asp Cys Gly Trp Gln Lys Val Cys Ser Gly Val Asp
                 85                  90                  95

Tyr Arg Gly Ile Tyr Tyr Val His Asp Gly His Lys Thr Tyr Tyr Thr
            100                 105                 110

Asp Phe Glu Gln Glu Ala Lys Lys Phe Gly Cys Lys Asn Ile Trp Glu
        115                 120                 125

Val His Met Glu Asn Glu Ser Ile Tyr Cys Pro Asp Ser Val Ser Ser
    130                 135                 140

Thr Cys Arg Tyr Asn Val Ser Pro Val Glu Thr Val Asn Glu Tyr Asn
145                 150                 155                 160

Thr His Lys Thr Thr Thr Thr Thr Ser Thr Ser Val Gly Asn Gln Asp
                165                 170                 175

Ala Ala Val Ser His Arg Pro Gly Lys Arg Pro Arg Leu Arg Glu Ser
            180                 185                 190

Glu Phe Asp Ser Ser Arg Glu Ser His Ala Lys Cys Val Thr Thr His
        195                 200                 205

Thr His Ile Ser Asp Thr Asp Asn Thr Asp Ser Arg Ser Arg Ser Ile
    210                 215                 220

Asn Asn Asn Asn His Pro Gly Asp Lys Thr Thr Pro Val Val His Leu
225                 230                 235                 240

Lys Gly Glu Pro Asn Arg Leu Lys Cys Cys Arg Tyr Arg Phe Gln Lys
                245                 250                 255

Tyr Lys Thr Leu Phe Val Asp Val Thr Ser Thr Tyr His Trp Thr Ser
            260                 265                 270

Thr Asp Asn Lys Asn Tyr Ser Ile Ile Thr Ile Tyr Lys Asp Glu
        275                 280                 285

Thr Gln Arg Asn Ser Phe Leu Ser His Val Lys Ile Pro Val Val Tyr
    290                 295                 300

Arg Leu Val Trp Asp Lys
305                 310
```

```
<210> SEQ ID NO 63
<211> LENGTH: 155
<212> TYPE: PRT
<213> ORGANISM: Human papillomavirus type 56

<400> SEQUENCE: 63

Met Glu Pro Gln Phe Asn Asn Pro Gln Glu Arg Pro Arg Ser Leu His
1               5                   10                  15

His Leu Ser Glu Val Leu Glu Ile Pro Leu Ile Asp Leu Arg Leu Ser
            20                  25                  30

Cys Val Tyr Cys Lys Lys Glu Leu Thr Arg Ala Glu Val Tyr Asn Phe
        35                  40                  45

Ala Cys Thr Glu Leu Lys Leu Val Tyr Arg Asp Asp Phe Pro Tyr Ala
    50                  55                  60

Val Cys Arg Val Cys Leu Leu Phe Tyr Ser Lys Val Arg Lys Tyr Arg
65                  70                  75                  80

Tyr Tyr Asp Tyr Ser Val Tyr Gly Ala Thr Leu Glu Ser Ile Thr Lys
                85                  90                  95

Lys Gln Leu Cys Asp Leu Leu Ile Arg Cys Tyr Arg Cys Gln Ser Pro
            100                 105                 110

Leu Thr Pro Glu Glu Lys Gln Leu His Cys Asp Arg Lys Arg Arg Phe
        115                 120                 125

His Leu Ile Ala His Gly Trp Thr Gly Ser Cys Leu Gly Cys Trp Arg
    130                 135                 140

Gln Thr Ser Arg Glu Pro Arg Glu Ser Thr Val
145                 150                 155

<210> SEQ ID NO 64
<211> LENGTH: 105
<212> TYPE: PRT
<213> ORGANISM: Human papillomavirus type 56

<400> SEQUENCE: 64

Met His Gly Lys Val Pro Thr Leu Gln Asp Val Val Leu Glu Leu Thr
1               5                   10                  15

Pro Gln Thr Glu Ile Asp Leu Gln Cys Asn Glu Gln Leu Asp Ser Ser
            20                  25                  30

Glu Asp Glu Asp Glu Asp Val Asp His Leu Gln Glu Arg Pro Gln
        35                  40                  45

Gln Ala Arg Gln Ala Lys Gln His Thr Cys Tyr Leu Ile His Val Pro
    50                  55                  60

Cys Cys Glu Cys Lys Phe Val Val Gln Leu Asp Ile Gln Ser Thr Lys
65                  70                  75                  80

Glu Asp Leu Arg Val Val Gln Gln Leu Leu Met Gly Ala Leu Thr Val
                85                  90                  95

Thr Cys Pro Leu Cys Ala Ser Ser Asn
            100                 105

<210> SEQ ID NO 65
<211> LENGTH: 534
<212> TYPE: PRT
<213> ORGANISM: Human papillomavirus type 56

<400> SEQUENCE: 65

Met Met Leu Pro Met Met Tyr Ile Tyr Arg Asp Pro Pro Leu His Tyr
1               5                   10                  15

Gly Leu Cys Ile Phe Leu Asp Val Gly Ala Val Asn Val Phe Pro Ile
            20                  25                  30
```

-continued

```
Phe Leu Gln Met Ala Thr Trp Arg Pro Ser Glu Asn Lys Val Tyr Leu
        35                  40                  45

Pro Pro Thr Pro Val Ser Lys Val Ala Thr Asp Ser Tyr Val Lys
    50                  55                  60

Arg Thr Ser Ile Phe Tyr His Ala Gly Ser Ser Arg Leu Leu Ala Val
65                  70                  75                  80

Gly His Pro Tyr Tyr Ser Val Thr Lys Asp Asn Thr Lys Thr Asn Ile
                    85                  90                  95

Pro Lys Val Ser Ala Tyr Gln Tyr Arg Val Phe Arg Val Arg Leu Pro
            100                 105                 110

Asp Pro Asn Lys Phe Gly Leu Pro Asp Thr Asn Ile Tyr Asn Pro Asp
            115                 120                 125

Gln Glu Arg Leu Val Trp Ala Cys Val Gly Leu Glu Val Gly Arg Gly
            130                 135                 140

Gln Pro Leu Gly Ala Gly Leu Ser Gly His Pro Leu Phe Asn Arg Leu
145                 150                 155                 160

Asp Asp Thr Glu Ser Ser Asn Leu Ala Asn Asn Asn Val Ile Glu Asp
                    165                 170                 175

Ser Arg Asp Asn Ile Ser Val Asp Gly Lys Gln Thr Gln Leu Cys Ile
                    180                 185                 190

Val Gly Cys Thr Pro Ala Met Gly Glu His Trp Thr Lys Gly Ala Val
            195                 200                 205

Cys Lys Ser Thr Gln Val Thr Thr Gly Asp Cys Pro Pro Leu Ala Leu
            210                 215                 220

Ile Asn Thr Pro Ile Glu Asp Gly Asp Met Ile Asp Thr Gly Phe Gly
225                 230                 235                 240

Ala Met Asp Phe Lys Val Leu Gln Glu Ser Lys Ala Glu Val Pro Leu
                    245                 250                 255

Asp Ile Val Gln Ser Thr Cys Lys Tyr Pro Asp Tyr Leu Lys Met Ser
            260                 265                 270

Ala Asp Ala Tyr Gly Asp Ser Met Trp Phe Tyr Leu Arg Arg Glu Gln
            275                 280                 285

Leu Phe Ala Arg His Tyr Phe Asn Arg Ala Gly Lys Val Gly Glu Thr
            290                 295                 300

Ile Pro Ala Glu Leu Tyr Leu Lys Gly Ser Asn Gly Arg Glu Pro Pro
305                 310                 315                 320

Pro Ser Ser Val Tyr Val Ala Thr Pro Ser Gly Ser Met Ile Thr Ser
                    325                 330                 335

Glu Ala Gln Leu Phe Asn Lys Pro Tyr Trp Leu Gln Arg Ala Gln Gly
            340                 345                 350

His Asn Asn Gly Ile Cys Trp Gly Asn Gln Leu Phe Val Thr Val Val
            355                 360                 365

Asp Thr Thr Arg Ser Thr Asn Met Thr Ile Ser Thr Ala Thr Glu Gln
            370                 375                 380

Leu Ser Lys Tyr Asp Ala Arg Lys Ile Asn Gln Tyr Leu Arg His Val
385                 390                 395                 400

Glu Glu Tyr Glu Leu Gln Phe Val Phe Gln Leu Cys Lys Ile Thr Leu
                    405                 410                 415

Ser Ala Glu Val Met Ala Tyr Leu His Asn Met Asn Ala Asn Leu Leu
            420                 425                 430

Glu Asp Trp Asn Ile Gly Leu Ser Pro Pro Val Ala Thr Ser Leu Glu
            435                 440                 445
```

-continued

Asp Lys Tyr Arg Tyr Val Arg Ser Thr Ala Ile Thr Cys Gln Arg Glu
    450                 455                 460

Gln Pro Pro Thr Glu Lys Gln Asp Pro Leu Ala Lys Tyr Lys Phe Trp
465                 470                 475                 480

Asp Val Asn Leu Gln Asp Ser Phe Ser Thr Asp Leu Asp Gln Phe Pro
                485                 490                 495

Leu Gly Arg Lys Phe Leu Met Gln Leu Gly Thr Arg Ser Lys Pro Ala
            500                 505                 510

Val Ala Thr Ser Lys Lys Arg Ser Ala Pro Thr Ser Thr Ser Thr Pro
            515                 520                 525

Ala Lys Arg Lys Arg Arg
            530

<210> SEQ ID NO 66
<211> LENGTH: 464
<212> TYPE: PRT
<213> ORGANISM: Human papillomavirus type 56

<400> SEQUENCE: 66

Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Val
                20                  25                  30

Asn Lys Ile Glu Gln Lys Thr Trp Ala Asp Lys Ile Leu Gln Trp Gly
            35                  40                  45

Ser Leu Phe Thr Tyr Phe Gly Gly Leu Gly Ile Gly Thr Gly Thr Gly
    50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg Pro Pro Ile Val Val Glu Ser Val
                85                  90                  95

Gly Pro Thr Asp Pro Ser Ile Val Thr Leu Val Glu Glu Ser Ser Val
                100                 105                 110

Ile Glu Ser Gly Ala Gly Ile Pro Asn Phe Thr Gly Ser Gly Gly Phe
            115                 120                 125

Glu Ile Thr Ser Ser Ser Thr Thr Thr Pro Ala Val Leu Asp Ile Thr
    130                 135                 140

Pro Thr Ser Ser Thr Val His Val Ser Ser Thr His Ile Thr Asn Pro
145                 150                 155                 160

Leu Phe Ile Asp Pro Pro Val Ile Glu Ala Pro Gln Thr Gly Glu Val
                165                 170                 175

Ser Gly Asn Ile Leu Ile Ser Thr Pro Thr Ser Gly Ile His Ser Tyr
                180                 185                 190

Glu Glu Ile Pro Met Gln Thr Phe Ala Val His Gly Ser Gly Thr Glu
            195                 200                 205

Pro Ile Ser Ser Thr Pro Ile Pro Gly Phe Arg Arg Ile Ala Ala Pro
    210                 215                 220

Arg Leu Tyr Arg Lys Ala Phe Gln Gln Val Lys Val Thr Asp Pro Ala
225                 230                 235                 240

Phe Leu Asp Arg Pro Ala Thr Leu Val Ser Ala Asp Asn Pro Leu Phe
                245                 250                 255

Glu Gly Thr Asp Thr Ser Leu Ala Phe Ser Pro Ser Gly Val Ala Pro
            260                 265                 270

Asp Pro Asp Phe Met Asn Ile Val Ala Leu His Arg Pro Ala Phe Thr
        275                 280                 285

-continued

```
Thr Arg Arg Gly Gly Val Arg Phe Ser Arg Leu Gly Arg Lys Ala Thr
    290                 295                 300
Ile Gln Thr Arg Arg Gly Thr Gln Ile Gly Ala Arg Val His Tyr Tyr
305                 310                 315                 320
Tyr Asp Ile Ser Pro Ile Ala Gln Ala Glu Glu Ile Glu Met Gln Pro
                325                 330                 335
Leu Leu Ser Ala Asn Asn Ser Phe Asp Gly Leu Tyr Asp Ile Tyr Ala
            340                 345                 350
Asn Ile Asp Asp Glu Ala Pro Gly Leu Ser Ser Gln Ser Val Ala Thr
        355                 360                 365
Pro Ser Ala His Leu Pro Ile Lys Pro Ser Thr Leu Ser Phe Ala Ser
    370                 375                 380
Asn Thr Thr Asn Val Thr Ala Pro Leu Gly Asn Val Trp Glu Thr Pro
385                 390                 395                 400
Phe Tyr Ser Gly Pro Asp Ile Val Leu Pro Thr Gly Pro Ser Thr Trp
                405                 410                 415
Pro Phe Val Pro Gln Ser Pro Tyr Asp Val Thr His Asp Val Tyr Ile
            420                 425                 430
Gln Gly Ser Ser Phe Ala Leu Trp Pro Val Tyr Phe Phe Arg Arg Arg
        435                 440                 445
Arg Arg Lys Arg Ile Pro Tyr Phe Phe Ala Asp Gly Asp Val Ala Ala
    450                 455                 460

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence:tetanus
      toxoid positions 830-843

<400> SEQUENCE: 67

Gln Tyr Ile Lys Ala Asn Ser Lys Phe Ile Gly Ile Thr Glu
  1               5                  10

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence:Plasmodium
      falciparum circumsporozoite (CS) protein positions
      378-398

<400> SEQUENCE: 68

Asp Ile Glu Lys Lys Ile Ala Lys Met Glu Lys Ala Ser Ser Val Phe
  1               5                  10                  15
Asn Val Val Asn Ser
            20

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence:Streptococcus
      18kD protein position 116

<400> SEQUENCE: 69

Gly Ala Val Asp Ser Ile Leu Gly Gly Val Ala Thr Tyr Gly Ala Ala
  1               5                  10                  15
```

```
<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence:pan-DR
      binding epitope peptide
<220> FEATURE:
<221> NAME/KEY: MISC_FEATURE
<222> LOCATION: (1)..(1)
<223> OTHER INFORMATION: May be either D- or L-Alanine
<220> FEATURE:
<221> NAME/KEY: MISC_FEATURE
<222> LOCATION: (3)..(3)
<223> OTHER INFORMATION: Xaa = Cyclohexylalanine, Phenylalanine or
      Tyrosine
<220> FEATURE:
<221> NAME/KEY: MISC_FEATURE
<222> LOCATION: (13)..(13)
<223> OTHER INFORMATION: May be either D- or L-Alanine

<400> SEQUENCE: 70

Ala Lys Xaa Val Ala Ala Trp Thr Leu Lys Ala Ala Ala
 1               5                  10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:standard
      peptide 944.02

<400> SEQUENCE: 71

Tyr Leu Glu Pro Ala Ile Ala Lys Tyr
 1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence:standard
      peptide 941.01

<400> SEQUENCE: 72

Phe Leu Pro Ser Asp Tyr Phe Pro Ser Val
 1               5                  10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence:standard
      peptide 1072.34

<400> SEQUENCE: 73

Tyr Val Ile Lys Val Ser Ala Arg Val
 1               5

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence:standard
      peptide 941.12
```

```
<400> SEQUENCE: 74

Lys Val Phe Pro Tyr Ala Leu Ile Asn Lys
 1               5                  10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence:standard
      peptide 940.06

<400> SEQUENCE: 75

Ala Val Asp Leu Tyr His Phe Leu Lys
 1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence:standard
      peptide 1083.02

<400> SEQUENCE: 76

Ser Thr Leu Pro Glu Thr Tyr Val Val Arg Arg
 1               5                  10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence:standard
      peptide 979.02

<400> SEQUENCE: 77

Ala Tyr Ile Asp Asn Tyr Asn Lys Phe
       1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence:standard
      peptide 1075.23

<400> SEQUENCE: 78

Ala Pro Arg Thr Leu Val Tyr Leu Leu
 1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence:standard
      peptide 1021.05

<400> SEQUENCE: 79

Phe Pro Phe Lys Tyr Ala Ala Ala Phe
 1               5

<210> SEQ ID NO 80
<211> LENGTH: 13
<212> TYPE: PRT
```

```
<213> ORGANISM: Artificial Sequence
<220> FEATURE:
<223> OTHER INFORMATION: Description of Artificial Sequence:standard
      peptide 515.01

<400> SEQUENCE: 80

Pro Lys Tyr Val Lys Gln Asn Thr Leu Lys Leu Ala Thr
  1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence:standard
      peptide 829.02

<400> SEQUENCE: 81

Tyr Lys Thr Ile Ala Phe Asp Glu Glu Ala Arg Arg
  1               5                  10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence:standard
      peptide 717.01

<400> SEQUENCE: 82

Tyr Ala Arg Phe Gln Ser Gln Thr Thr Leu Lys Gln Lys Thr
  1               5                  10

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence:standard
      peptide 1200.05

<400> SEQUENCE: 83

Glu Ala Leu Ile His Gln Leu Lys Ile Asn Pro Tyr Val Leu Ser
  1               5                  10                  15

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence:standard
      peptide 650.22

<400> SEQUENCE: 84

Gln Tyr Ile Lys Ala Asn Ala Lys Phe Ile Gly Ile Thr Glu
  1               5                  10

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence:standard
      peptide 507.02

<400> SEQUENCE: 85

Gly Arg Thr Gln Asp Glu Asn Pro Val Val His Phe Phe Lys Asn Ile
  1               5                  10                  15
```

```
Val Thr Pro Arg Thr Pro Pro Pro
            20

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence:standard
      peptide 511

<400> SEQUENCE: 86

Asn Gly Gln Ile Gly Asn Asp Pro Asn Arg Asp Ile Leu
  1               5                  10

<210> SEQ ID NO 87
<211> LENGTH: 9
<212> TYPE: PRT
<213> ORGANISM: Artificial Sequence
<220> FEATURE:
<223> OTHER INFORMATION: DR7 preferred motif
<220> FEATURE:
<221> NAME/KEY: MISC_FEATURE
<222> LOCATION: (1)..(1)
<223> OTHER INFORMATION: May be  Met, Phe, Leu, Ile, Val, Trp or Tyr
<220> FEATURE:
<221> NAME/KEY: MISC_FEATURE
<222> LOCATION: (5)..(5)
<223> OTHER INFORMATION: May be any amino acid
<220> FEATURE:
<221> NAME/KEY: MISC_FEATURE
<222> LOCATION: (6)..(6)
<223> OTHER INFORMATION: May be Ile, Val, Met, Ser, Ala, Cys, Thr, Pro
      or Leu
<220> FEATURE:
<221> NAME/KEY: MISC_FEATURE
<222> LOCATION: (8)..(8)
<223> OTHER INFORMATION: May be any amino acid
<220> FEATURE:
<221> NAME/KEY: MISC_FEATURE
<222> LOCATION: (9)..(9)
<223> OTHER INFORMATION: May be either Ile or Val

<400> SEQUENCE: 87

Xaa Met Trp Ala Xaa Xaa Met Xaa Xaa
  1               5

<210> SEQ ID NO 88
<211> LENGTH: 9
<212> TYPE: PRT
<213> ORGANISM: Artificial Sequence
<220> FEATURE:
<223> OTHER INFORMATION: DR7 deleterious motif
<220> FEATURE:
<221> NAME/KEY: MISC_FEATURE
<222> LOCATION: (1)..(1)
<223> OTHER INFORMATION: May be any amino acid
<220> FEATURE:
<221> NAME/KEY: MISC_FEATURE
<222> LOCATION: (3)..(3)
<223> OTHER INFORMATION: May be any amino acid
<220> FEATURE:
<221> NAME/KEY: MISC_FEATURE
<222> LOCATION: (5)..(6)
<223> OTHER INFORMATION: May be any amino acid
<220> FEATURE:
<221> NAME/KEY: MISC_FEATURE
```

```
-continued

<222> LOCATION: (7)..(7)
<223> OTHER INFORMATION: May be Gly, Arg or Asp

<400> SEQUENCE: 88

Xaa Cys Xaa Gly Xaa Xaa Xaa Asn Gly
1               5
```

INDUCING CELLULAR IMMUNE RESPONSES TO HUMAN PAPILLOMAVIRUS USING PEPTIDE AND NUCLEIC ACID COMPOSITIONS

CROSS-REFERENCE TO RELATED APPLICATIONS

The present application is a national phase of International Appl. No. PCT/US00/33549, filed Dec. 11, 2000, which published under PCT Article 21(2) in English and which is herein incorporated by reference, said PCT/US00/33549 claims the benefit of U.S. application Ser. No. 09/641,528, filed Aug. 15, 2000, now U.S. Pat. No. 7,026,443, which is herein incorporated by reference, said application Ser. No. 09/641,528 claims the benefit of U.S. Provisional Application No. 60/172,705, filed Dec. 10, 1999, which is herein incorporated by reference.

I. BACKGROUND OF THE INVENTION

Human papillomavirus (HPV) is a member of the papillomaviridae, a group of small DNA viruses that infect a variety of higher vertebrates. More than 80 types of HPVs have been identified. Of these, more than 30 can infect the genital tract. Some types, generally types 6 and 11, may cause genital warts, which are typically benign and rarely develop into cancer. Other strains of HPV, "cancer-associated", or "high-risk" types, can more frequently lead to the development of cancer. The primary mode of transmission of these strains of HPV is through sexual contact.

The main manifestations of the genital warts are cauliflower-like condylomata acuminata that usually involve moist surfaces; keratotic and smooth papular warts, usually on dry surfaces; and subclinical "flat" warts, which are found on any mucosal or cutaneous surface (Handsfield, H., *Am. J. Med.* 102(5A): 16-20, 1997). These warts are typically benign but are a source of inter-individual spread of the virus (Ponten, J. & Guo, Z., *Cancer Surv.* 32:201-29, 1998). At least three HPV strains associated with genital warts have been identified: type 6a (see, e.g., Hofmann, K. J., et al., *Virology* 209(2):506-518, 1995), type 6b (see, e.g., Hofmann et al., supra) and type 11 (see, e.g., Dartmann, K. et al., *Virology* 151(1):124-130, 1986).

Cancer-associated HPVs have been linked with cancer in both men and women; they include, but are not limited to, HPV-16, HPV-18, HPV-31, HPV-45, HPV-33 and HPV-56. Other HPV strains, including types 6 and 11 as well as others, e.g., HPV-5 and HPV-8, are less frequently associated with cancer. The high risk types are typically associated with the development of cervical carcinoma and premalignant lesions of the cervix in women, but are also associated with similar malignant and premalignant lesions at other anatomic sites within the lower genital or anogenital tract. These lesions include neoplasia of the vagina, vulva, perineum, the penis, and the anus. HPV infection has also been associated with respiratory tract papillomas, and rarely, cancer, as well as abnormal growth or neoplasia in other epithelial tissues. See, e.g. VIROLOGY, $2^{ND}$ ED, Fields et al., Eds. Raven Press, New York, 1990, Chapters 58 and 59, for a review of HPV association with cancer.

The HPV genome consists of three functional regions, the early region, the late region, and the "long control region". The early region gene products control viral replication, transcription and cellular transformation They include the HPV E1 and E2 proteins, which play a role in HPV DNA replication, and the E6 and E7 oncoproteins, which are involved in the control of cellular proliferation. The late region include the genes that encode the structural proteins L1 and L2, which are the major and minor capsid proteins, respectively. The "long control region" contains such sequences as enhancer and promoter regulatory regions.

HPV expresses different proteins at different stages of the infection, for example early, as well as late, proteins. Even in latent infections, however, early proteins are often expressed and are therefore useful targets for vaccine-based therapies. For example, high-grade dysplasia and cervical squamous cell carcinoma continue to express E6 and E7, which therefore can be targeted to treat disease at both early and late stages of infection.

Treatment for HPV infection is often unsatisfactory because of persistence of virus after treatment and recurrence of clinically apparent disease is common. The treatment may require frequent visits to clinics and is not directed at elimination of the virus but at clearing warts. Because of persistence of virus after treatment, recurrence of clinically apparent disease is common.

Thus, a need exists for an efficacious vaccine to both prevent and treat HPV infection and to treat cancer that is associated with HPV infection. Effective HPV vaccines would be a significant advance in the control of sexually transmissable infections and could also protect against clinical disease, particularly cancers such as cervical cancer. (see, e.g., Rowen, P. & Lacey, C., *Dermatologic Clinics* 16(4):835-838, 1998).

Virus-specific, human leukocyte antigen (HLA) class I-restricted cytotoxic T lymphocytes (CTL) are known to play a major role in the prevention and clearance of virus infections in vivo (Oldstone et al., *Nature* 321:239, 1989; Jamieson et al., *J. Virol.* 61:3930, 1987; Yap et al, *Nature* 273:238, 1978; Lukacher et al., *J. Exp. Med.* 160:814, 1994; McMichael et al., *N. Engl. J. Med.* 309:13, 1983; Sethi et al., *J. Gen. Virol.* 64:443, 1983; Watari et al., *J. Exp. Med.* 165:459, 1987; Yasukawa et al., *J. Immunol.* 143:2051, 1989; Tigges et al., *J. Virol.* 66:1622, 1993; Reddenhase et al., *J. Virol.* 55:263, 1985; Quinnan et al., *N. Engl. J. Med.* 307:6, 1982). HLA class I molecules are expressed on the surface of almost all nucleated cells. Following intracellular processing of antigens, epitopes from the antigens are presented as a complex with the HLA class I molecules on the surface of such cells. CTL recognize the peptide-HLA class I complex, which then results in the destruction of the cell bearing the HLA-peptide complex directly by the CTL and/or via the activation of non-destructive mechanisms e.g., the production of interferon, that inhibit viral replication.

Virus-specific T helper lymphocytes are also known to be critical for maintaining effective immunity in chronic viral infections. Historically, HTL responses were viewed as primarily supporting the expansion of specific CTL and B cell populations; however, more recent data indicate that HTL may directly contribute to the control of virus replication. For example, a decline in $CD4^+$ T cells and a corresponding loss in HTL function characterize infection with HIV (Lane et al., *New Engl. J. Med.* 313:79, 1985). Furthermore, studies in HIV infected patients have also shown that there is an inverse relationship between virus-specific HTL responses and viral load, suggesting that HTL plays a role in viremia (see, e.g., Rosenberg et al., *Science* 278:1447, 1997).

The development of vaccines with prophylactic and therapeutic efficacy against HPV is ongoing. Early vaccine development was hampered by the inability to culture HPV. With the introduction of cloning techniques and protein expression, however, some attempts have been made to stimulate humoral and CTL response to HPV (See, e.g., Rowen, P. &

Lacey, C., *Dermatologic Clinics* 16(4):835-838 (1998)). Studies to date, however, have been inconclusive.

Activation of T helper cells and cytotoxic lymphocytes (CTLs) in the development of vaccines has also been analyzed. Lehtinen, M., et al. for instance, has shown that some peptides from the E2 protein of HPV type 16 activate T helper cells and CTLs (*Biochem. Biophys. Res. Commun.* 209(2): 541-6 (1995). Similarly, Tarpey et al, has shown that some peptides from HPV type 11 E7 protein can stimulate human HPV-specific CTLs in vitro (*Immunology* 81:222-227 (1994)) and Borysiewicz et al. have reported a recombinant vaccinia virus expressing HPV 16 and HPV 17 E6 and E7 that stimulated CTL responses in at least one patient (*Lancet* 347:1347-1357, 1996).

The epitope approach, as we have described, allows the incorporation of various antibody, CTL and HTL epitopes, from various proteins, in a single vaccine composition. Such a composition may simultaneously target multiple dominant and subdominant epitopes and thereby be used to achieve effective immunization in a diverse population.

The information provided in this section is intended to disclose the presently understood state of the art as of the filing date of the present application. Information is included in this section which was generated subsequent to the priority date of this application. Accordingly, information in this section is not intended, in any way, to delineate the priority date for the invention.

II. SUMMARY OF THE INVENTION

This invention applies our knowledge of the mechanisms by which antigen is recognized by T cells, for example, to develop epitope-based vaccines directed towards HPV. More specifically, this application communicates our discovery of specific epitope pharmaceutical compositions and methods of use in the prevention and treatment of HPV infection.

Upon development of appropriate technology, the use of epitope-based vaccines has several advantages over current vaccines, particularly when compared to the use of whole antigens in vaccine compositions. There is evidence that the immune response to whole antigens is directed largely toward variable regions of the antigen, allowing for immune escape due to mutations. The epitopes for inclusion in an epitope-based vaccine may be selected from conserved regions of viral or tumor-associated antigens, which thereby reduces the likelihood of escape mutants. Furthermore, immunosuppressive epitopes that may be present in whole antigens can be avoided with the use of epitope-based vaccines.

An additional advantage of an epitope-based vaccine approach is the ability to combine selected epitopes (CTL and HTL), and further, to modify the composition of the epitopes, achieving, for example, enhanced immunogenicity. Accordingly, the immune response can be modulated, as appropriate, for the target disease. Similar engineering of the response is not possible with traditional approaches.

Another major benefit of epitope-based immune-stimulating vaccines is their safety. The possible pathological side effects caused by infectious agents or whole protein antigens, which might have their own intrinsic biological activity, is eliminated.

An epitope-based vaccine also provides the ability to direct and focus an immune response to multiple selected antigens from the same pathogen. Thus, patient-by-patient variability in the immune response to a particular pathogen may be alleviated by inclusion of epitopes from multiple antigens from the pathogen in a vaccine composition. In the case of HPV, epitopes derived from multiple strains may also be included. A "pathogen" may be an infectious agent or a tumor associated molecule.

One of the most formidable obstacles to the development of broadly efficacious epitope-based immunotherapeutics, however, has been the extreme polymorphism of HLA molecules. To date, effective non-genetically biased coverage of a population has been a task of considerable complexity; such coverage has required that epitopes be used that are specific for HLA molecules corresponding to each individual HLA allele. Impractically large numbers of epitopes would therefore have to be used in order to cover ethnically diverse populations. Thus, there has existed a need for peptide epitopes that are bound by multiple HLA antigen molecules for use in epitope-based vaccines. The greater the number of HLA antigen molecules bound, the greater the breadth of population coverage by the vaccine.

Furthermore, as described herein in greater detail, a need has existed to modulate peptide binding properties, e.g., so that peptides that are able to bind to multiple HLA antigens do so with an affinity that will stimulate an immune response. Identification of epitopes restricted by more than one HLA allele at an affinity that correlates with immunogenicity is important to provide thorough population coverage, and to allow the elicitation of responses of sufficient vigor to prevent or clear an infection in a diverse segment of the population. Such a response can also target a broad array of epitopes. The technology disclosed herein provides for such favored immune responses.

In a preferred embodiment, epitopes for inclusion in vaccine compositions of the invention are selected by a process whereby protein sequences of known antigens are evaluated for the presence of motif or supermotif-bearing epitopes. Peptides corresponding to a motif- or supermotif-bearing epitope are then synthesized and tested for the ability to bind to the HLA molecule that recognizes the selected motif. Those peptides that bind at an intermediate or high affinity i.e., an $IC_{50}$ (or a $K_D$ value) of 500 nM or less for HLA class I molecules or an $IC_{50}$ of 1000 nM or less for HLA class II molecules, are further evaluated for their ability to induce a CTL or HTL response. Immunogenic peptide epitopes are selected for inclusion in vaccine compositions.

Supermotif-bearing peptides may additionally be tested for the ability to bind to multiple alleles within the HLA supertype family. Moreover, peptide epitopes may be analogued to modify binding affinity and/or the ability to bind to multiple alleles within an HLA supertype.

The invention also includes embodiments comprising methods for monitoring or evaluating an immune response to HPV in a patient having a known HLA-type. Such methods comprise incubating a T lymphocyte sample from the patient with a peptide composition comprising an HPV epitope that has an amino acid sequence described in Tables VII to Table XX which binds the product of at least one HLA allele present in the patient, and detecting for the presence of a T lymphocyte that binds to the peptide. A CTL peptide epitope may, for example, be used as a component of a tetrameric complex for this type of analysis.

An alternative modality for defining the peptide epitopes in accordance with the invention is to recite the physical properties, such as length; primary structure; or charge, which are correlated with binding to a particular allele-specific HLA molecule or group of allele-specific HLA molecules. A further modality for defining peptide epitopes is to recite the physical properties of an HLA binding pocket, or properties shared by several allele-specific HLA binding pockets (e.g.

pocket configuration and charge distribution) and reciting that the peptide epitope fits and binds to the pocket or pockets.

As will be apparent from the discussion below, other methods and embodiments are also contemplated. Further, novel synthetic peptides produced by any of the methods described herein are also part of the invention.

III. DETAILED DESCRIPTION OF THE INVENTION

The peptides and corresponding nucleic acid compositions of the present invention are useful for stimulating an immune response to HPV by stimulating the production of CTL or HTL responses. The peptide epitopes, which are derived directly or indirectly from native HPV protein amino acid sequences, are able to bind to HLA molecules and stimulate an immune response to HPV. The complete sequence of the HPV proteins to be analyzed can be obtained from Genbank. Epitopes and analogs thereof can also be readily determined from sequence information that may subsequently be discovered for heretofore unknown variants of HPV, as will be clear from the disclosure provided below.

The epitopes of the invention have been identified in a number of ways, as will be discussed below. Also discussed in greater detail is that analog peptides have been derived and the binding activity for HLA molecules modulated by modifying specific amino acid residues to create peptide analogs exhibiting altered immunogenicity. Further, the present invention provides compositions and combinations of compositions that enable epitope-based vaccines that are capable of interacting with HLA molecules encoded by various genetic alleles to provide broader population coverage than prior vaccines.

III.A. Definitions

The invention can be better understood with reference to the following definitions, which are listed alphabetically:

A "computer" or "computer system" generally includes: a processor; at least one information storage/retrieval apparatus such as, for example, a hard drive, a disk drive or a tape drive; at least one input apparatus such as, for example, a keyboard, a mouse, a touch screen, or a microphone; and display structure. Additionally, the computer may include a communication channel in communication with a network. Such a computer may include more or less than what is listed above.

A "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form.

"Cross-reactive binding" indicates that a peptide is bound by more than one HLA molecule; a synonym is degenerate binding.

A "cryptic epitope" elicits a response by immunization with an isolated peptide, but the response is not cross-reactive in vitro when intact whole protein which comprises the epitope is used as an antigen.

A "dominant epitope" is an epitope that induces an immune response upon immunization with a whole native antigen (see, e.g., Sercarz, et al., *Annu. Rev. Immunol.* 11:729-766, 1993). Such a response is cross-reactive in vitro with an isolated peptide epitope.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

An "HLA supertype or family", as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms.

Throughout this disclosure, results are expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide.

Binding may also be determined using other assay systems including those using: live cells (e.g., Ceppellini et al., *Nature* 339:392, 1989; Christnick et al., *Nature* 352:67, 1991; Busch et al., *Int. Immunol.* 2:443, 19990; Hill et al., *J. Immunol.* 147:189, 1991; del Guercio et al., *J. Immunol.* 154:685, 1995), cell free systems using detergent lysates (e.g., Cerundolo et al., *J. Immunol.* 21:2069, 1991), immobilized purified MHC (e.g., Hill et al., *J. Immunol.* 152, 2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al., *Cell* 62:285, 1990; Parker et al., *J. Immunol.* 149:1896, 1992).

As used herein, "high affinity" with respect to HLA class I molecules is defined as binding with an $IC_{50}$, or $K_D$ value, of 50 nM or less; "intermediate affinity" is binding with an $IC_{50}$ or $K_D$ value of between about 50 and about 500 nM. "High affinity" with respect to binding to HLA class II molecules is defined as binding with an $IC_{50}$ or $K_D$ value of 100 nM or less; "intermediate affinity" is binding with an $IC_{50}$ or $K_D$ value of between about 100 and about 1000 nM.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, and electrostatic bonding.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, New York, 1993.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" or "deleterious residue" is an amino acid which, if present at certain positions (typically not primary anchor positions) in a peptide epitope, results in decreased binding affinity of the peptide for the peptide's corresponding HLA molecule.

A "non-native" sequence or "construct" refers to a sequence that is not found in nature, i.e., is "non-naturally occurring". Such sequences include, e.g., peptides that are lipidated or otherwise modified, and polyepitopic compositions that contain epitopes that are not contiguous in a native protein sequence.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing peptides of the invention are 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

It is to be appreciated that protein or peptide molecules that comprise an epitope of the invention as well as additional amino acid(s) are within the bounds of the invention. In certain embodiments, there is a limitation on the length of a peptide of the invention which is not otherwise a construct as defined herein. An embodiment that is length-limited occurs when the protein/peptide comprising an epitope of the invention comprises a region (i.e., a contiguous series of amino acids) having 100% identity with a native sequence. In order to avoid a recited definition of epitope from reading, e.g., on whole natural molecules, the length of any region that has 100% identity with a native peptide sequence is limited. Thus, for a peptide comprising an epitope of the invention and a region with 100% identity with a native peptide sequence (and which is not otherwise a construct), the region with 100% identity to a native sequence generally has a length of: less than or equal to 600 amino acids, often less than or equal to 500 amino acids, often less than or equal to 400 amino acids, often less than or equal to 250 amino acids, often less than or equal to 100 amino acids, often less than or equal to 85 amino acids, often less than or equal to 75 amino acids, often less than or equal to 65 amino acids, and often less than or equal to 50 amino acids. In certain embodiments, an "epitope" of the invention which is not a construct is comprised by a peptide having a region with less than 51 amino acids that has 100% identity to a native peptide sequence, in any increment of (50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5) down to 5 amino acids.

Certain peptide or protein sequences longer than 600 amino acids are within the scope of the invention. Such longer sequences are within the scope of the invention so long as they do not comprise any contiguous sequence of more than 600 amino acids that have 100% identity with a native peptide sequence, or if longer than 600 amino acids, they are a construct. For any peptide that has five contiguous residues or less that correspond to a native sequence, there is no limitation on the maximal length of that peptide in order to fall within the scope of the invention. It is presently preferred that a CTL epitope of the invention be less than 600 residues long in any increment down to eight amino acid residues.

"Pharmaceutically acceptable" refers to a non-toxic, inert, and/or physiologically compatible composition.

A "pharmaceutical excipient" comprises a material such as an adjuvant, a carrier, pH-adjusting and buffering agents, tonicity adjusting agents, wetting agents, preservative, and the like.

A "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, for example, the primary anchor residues are located at position 2 (from the amino terminal position) and at the carboxyl terminal position of a 9-residue peptide epitope in accordance with the invention. The primary anchor positions for each motif and supermotif are set forth in Table 1. For example, analog peptides can be created by altering the presence or absence of particular residues in these primary anchor positions. Such analogs are used to modulate the binding affinity of a peptide comprising a particular motif or supermotif.

"Promiscuous recognition" is where a distinct peptide is recognized by the same T cell clone in the context of various HLA molecules. Promiscuous recognition or binding is synonymous with cross-reactive binding.

A "protective immune response" or "therapeutic immune response" refers to a CTL and/or an HTL response to an antigen derived from an infectious agent or a tumor antigen, which prevents or at least partially arrests disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

A "secondary anchor residue" is an amino acid at a position other than a primary anchor position in a peptide which may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high or intermediate affinity binding peptides, or a residue otherwise associated with high or intermediate affinity binding. For example, analog peptides can be created by altering the presence or absence of particular residues in these secondary anchor positions. Such analogs are used to finely modulate the binding affinity of a peptide comprising a particular motif or supermotif.

A "subdominant epitope" is an epitope which evokes little or no response upon immunization with whole antigens which comprise the epitope, but for which a response can be obtained by immunization with an isolated peptide, and this response (unlike the case of cryptic epitopes) is detected when whole protein is used to recall the response in vitro or in vivo.

A "supermotif" is a peptide binding specificity shared by HLA molecules encoded by two or more HLA alleles. Preferably, a supermotif-bearing peptide is recognized with high or intermediate affinity (as defined herein) by two or more HLA antigens.

"Synthetic peptide" refers to a peptide that is man-made using such methods as chemical synthesis or recombinant DNA technology.

As used herein, a "vaccine" is a composition that contains one or more peptides of the invention. There are numerous embodiments of vaccines in accordance with the invention, such as by a cocktail of one or more peptides; one or more epitopes of the invention comprised by a polyepitopic peptide; or nucleic acids that encode such peptides or polypeptides, e.g., a minigene that encodes a polyepitopic peptide. The "one or more peptides" can include any whole unit integer from 1-150, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I-binding peptides of the invention can be admixed with, or linked to, HLA class II-binding peptides, to facilitate activation of both cytotoxic T lymphocytes and helper T lymphocytes. Vaccines can also comprise peptide-pulsed antigen presenting cells, e.g., dendritic cells.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.) In addition to these symbols, "B" in the single letter abbreviations used herein designates α-amino butyric acid.

III.B. Stimulation of CTL and HTL Responses

The mechanism by which T cells recognize antigens has been delineated during the past ten years. Based on our understanding of the immune system we have developed efficacious peptide epitope vaccine compositions that can induce a therapeutic or prophylactic immune response to HPV in a broad population. For an understanding of the value and efficacy of the claimed compositions, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are described herein and are set forth in Tables I, II, and III (see also, e.g., Southwood, et al., *J. Immunol.* 160:3363, 1998; Rammiensee, et al., *Immunogenetics* 41:178, 1995; Rammensee et al., SYFPEITHI, access via web at: http://134.2.96.221/scripts.hla-server.dll/home.htm; Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al, *J. Immunol.* 155:4307-4312, 1995; Sidney et al., *J. Immunol.* 157:3480-3490, 1996; Sidney et al., *Human Immunol.* 45:79-93, 1996; Sette, A. and Sidney, *J. Immunogenetics* 1999 November;50(3-4):201-12, Review).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that have the potential of binding particular HLA antigen(s).

The present inventors have found that the correlation of binding affinity with immunogenicity, which is disclosed herein, is an important factor to be considered when evaluating candidate peptides. Thus, by a combination of motif searches and HLA-peptide binding assays, candidates for epitope-based vaccines have been identified. After determining their binding affinity, additional confirmatory work can be performed to select, amongst these vaccine candidates, epitopes with preferred characteristics in terms of population coverage, antigenicity, and immuogenicity.

Various strategies can be utilized to evaluate immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998); This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997); In this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have effectively been vaccinated, recovered from infection, and/or from chronically infected patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997); In applying this strategy, recall responses are detected by culturing PBL from subjects that have been naturally exposed to the antigen, for instance through infection, and thus have generated an immune response "naturally", or from patients who were vaccinated against the infection. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays for T cell activity including $^{51}$Cr release involving peptide-sensitized targets, T cell proliferation, or lymphokine release.

The following describes the peptide epitopes and corresponding nucleic acids of the invention.

III.C. Binding Affinity of Peptide Epitopes for HLA Molecules

As indicated herein, the large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele-specific HLA molecules.

CTL-inducing peptides of interest for vaccine compositions preferably include those that have an $IC_{50}$ or binding affinity value for class I HLA molecules of 500 nM or better (ie., the value is <500 nM). HTL-inducing peptides preferably include those that have an $IC_{50}$ or binding affinity value for class II HLA molecules of 1000 nM or better, (i.e., the value is <1,000 nM). For example, peptide binding is assessed by testing the capacity of a candidate peptide to bind to a purified HLA molecule in vitro. Peptides exhibiting high or intermediate affinity are then considered for further analysis. Selected peptides are tested on other members of the supertype family. In preferred embodiments, peptides that exhibit cross-reactive binding are then used in cellular screening analyses or vaccines.

As disclosed herein, higher HLA binding affinity is correlated with greater immunogenicity. Greater immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high binding peptides have been found to be immunogenic, as contrasted with about 50% of the peptides which bind with intermediate affinity. Moreover, higher binding affinity peptides lead to more vigorous immunogenic responses. As a result, less peptide is required to elicit a similar biological effect if a high affinity binding peptide is used. Thus, in preferred embodiments of the invention, high affinity binding epitopes are particularly useful.

The relationship between binding affinity for HLA class I molecules and immunogenicity of discrete peptide epitopes on bound antigens has been determined for the first time in the art by the present inventors. The correlation between binding affinity and immunogenicity was analyzed in two different experimental approaches (see, e.g., Sette, et al., *J. Immunol.* 153:5586-5592, 1994). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL from acute hepatitis patients. Pursuant to these approaches, it was determined that an affinity threshold value of approximately 500 nM (preferably 50 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses (see, e.g., Schaeffer et al. *Proc. Natl. Acad. Sci. USA* 86:4649-4653, 1989).

An affinity threshold associated with immunogenicity in the context of HLA class II DR molecules has also been delineated (see, e.g., Southwood et al *J. Immunology* 160: 3363-3373,1998, and co-pending U.S. Ser. No. 09/009,953 filed Jan. 21, 1998). In order to define a biologically significant threshold of DR binding affinity, a database of the binding affinities of 32 DR-restricted epitopes for their restricting element (i.e., the HLA molecule that binds the motif) was compiled. In approximately half of the cases (15 of 32 epitopes), DR restriction was associated with high binding affinities, i.e. binding affinity values of 100 nM or less. In the other half of the cases (16 of 32), DR restriction was associated with intermediate affinity (binding affinity values in the 100-1000 nM range). In only one of 32 cases was DR restriction associated with an $IC_{50}$ of 1000 nM or greater. Thus, 1000 nM can be defined as an affinity threshold associated with immunogenicity in the context of DR molecules.

In the case of tumor-associated antigens (TAAs), many CTL peptide epitopes that have been shown to induce CTL that lyse peptide-pulsed target cells and tumor cell targets endogenously expressing the epitope exhibit binding affinity or $IC_{50}$ values of 200 nM or less. In a study that evaluated the association of binding affinity and immunogenicity of a small set of such TAA epitopes, 100% (10/10) of the high binders, i.e., peptide epitopes binding at an affinity of 50 nM or less, were immunogenic and 80% (8/10) of them elicited CTLs that specifically recognized tumor cells. In the 51 to 200 nM range, very similar figures were obtained. With respect to analog peptides, CTL inductions positive for wildtype peptide and tumor cells were noted for 86% (6/7) and 71% (5/7) of the peptides, respectively. In the 201-500 nM range, most peptides (4/5 wildtype) were positive for induction of CTL recognizing wildtype peptide, but tumor recognition was not detected.

The binding affinity of peptides for HLA molecules can be determined as described in Example 1, below.

III.D. Peptide Epitope Binding Motifs and Supermotifs

Through the study of single amino acid substituted antigen analogs and the sequencing of endogenously bound, naturally processed peptides, critical residues required for allele-specific binding to HLA molecules have been identified. The presence of these residues correlates with binding affinity for HLA molecules. The identification of motifs and/or supermotifs that correlate with high and intermediate affinity binding is an important issue with respect to the identification of immunogenic peptide epitopes for the inclusion in a vaccine. Kast et al. (*J. Immunol.* 152:3904-3912, 1994) have shown that motif-bearing peptides account for 90% of the epitopes that bind to allele-specific HLA class I molecules. In this study all possible peptides of 9 amino acids in length and overlapping by eight amino acids (240 peptides), which cover the entire sequence of the E6 and E7 proteins of human papillomavirus type 16, were evaluated for binding to five allele-specific HLA molecules that are expressed at high frequency among different ethnic groups. This unbiased set of peptides allowed an evaluation of the predictive value of HLA class I motifs. From the set of 240 peptides, 22 peptides were identified that bound to an allele-specific HLA molecule with high or intermediate affinity. Of these 22 peptides, 20 (i.e. 91%) were motif-bearing. Thus, this study demonstrates the value of motifs for the identification of peptide epitopes for inclusion in a vaccine: application of motif-based identification techniques will identify about 90% of the potential epitopes in a target antigen protein sequence.

Such peptide epitopes are identified in the Tables described below.

Peptides of the present invention may also comprise epitopes that bind to MHC class II DR molecules. A greater degree of heterogeneity in both size and binding frame position of the motif, relative to the N and C termini of the peptide, exists for class II peptide ligands. This increased heterogeneity of HLA class II peptide ligands is due to the structure of the binding groove of the HLA class II molecule which, unlike its class I counterpart, is open at both ends. Crystallographic analysis of HLA class II DRB*0101-peptide complexes showed that the major energy of binding is contributed by peptide residues complexed with complementary pockets on the DRB*0101 molecules. An important anchor residue engages the deepest hydrophobic pocket (see, e.g., Madden, D. R. *Ann. Rev. Immunol.* 13:587, 1995) and is referred to as position 1 (P1). P1 may represent the N-terminal residue of a class II binding peptide epitope, but more typically is flanked towards the N-terminus by one or more residues. Other studies have also pointed to an important role for the peptide residue in the $6^{th}$ position towards the C-terminus, relative to P1, for binding to various DR molecules.

In the past few years evidence has accumulated to demonstrate that a large fraction of HLA class I and class II molecules can be classified into a relatively few supertypes, each characterized by largely overlapping peptide binding repertoires, and consensus structures of the main peptide binding pockets. Thus, peptides of the present invention are identified by any one of several HLA-specific amino acid motifs (see, e.g., Tables I-III), or if the presence of the motif corresponds to the ability to bind several allele-specific HLA antigens, a supermotif. The HLA molecules that bind to peptides that possess a particular amino acid supermotif are collectively referred to as an HLA "supertype."

The peptide motifs and supermotifs described below, and summarized in Tables I-III, provide guidance for the identification and use of peptide epitopes in accordance with the invention.

Examples of peptide epitopes bearing a respective supermotif or motif are included in Tables as designated in the description of each motif or supermotif below. The Tables include a binding affinity ratio listing for some of the peptide epitopes. The ratio may be converted to $IC_{50}$ by using the following formula: $IC_{50}$ of the standard peptide/ratio=$IC_{50}$ of the test peptide (i.e., the peptide epitope). The $IC_{50}$ values of standard peptides used to determine binding affinities for Class I peptides are shown in Table IV. The $IC_{50}$ values of standard peptides used to determine binding affinities for Class II peptides are shown in Table V. For example, where an HLA-A2.1 motif-bearing peptide shows a relative binding ratio of 0.01 for HLA-A*0201, the $IC_{50}$ value is 500 nM, and where an HLA-A2.1 motif-bearing peptide shows a relative binding ratio of 0.1 for HLA-A*0201, the $IC_{50}$ value is 50 mM.

The peptides used as standards for the binding assays described herein are examples of standards; alternative standard peptides can also be used when performing binding studies.

To obtain the peptide epitope sequences listed in Tables VII-XX, protein sequence data for HPV types 6a, 6b, 11a, 16, 18, 31, 33, 45, and 56 were evaluated for the presence of the designated supermotif or motif. Seven HPV structural and regulatory proteins, E1, E2, E5, E6, E7, L1 and L2 were included in the analysis. E4 was also included in the evaluation of some of the strains. Peptide epitopes can additionally be evaluated on the basis of their conservancy (i.e., the amount of variance) among the available protein sequences for each HPV antigen.

In the Tables, motif- and/or supermotif-bearing amino acids sequences identified in the indicated HPV strains are designated by position number and length of the epitope with reference to the HPV sequences and numbering provided below. For each sequence, the four columns provide the following information: column 1 indicates the HPV strain; column 2 indicates the HPV protein in which the motif-bearing sequence is found, e.g., E1, E2, E4, E5, E6, E7, L1, or L2; column 3 indicates the length of the epitope, or in the case of HLA Class II epitopes, the length of the core sequence; and column 4 designates the amino acid position in the HPV protein sequence that corresponds to the first amino acid residue of the epitope. For those sections of the Tables that include only three columns, corresponding to columns 2, 3, and 4, the HPV strain is indicated in the heading at the top of the page. For example, the first peptide epitope listed in Table VII, i.e., the HLA-A1 supermotif, for HPV 16, protein E1 is a sequence of 10 residues in length starting at position 206. Accordingly, the amino acid sequence of the epitope is AMLAKFKELY (SEQ ID NO:1).

For HPV strain 11, the number and position listed for protein E5 refers to either the HPV11 E5a or HPV11 E5b sequence set out below. Because the epitope must include the designated motif or supermotif, e.g., HLA-A2, it can readily be determined whether the sequence refers to HPV11 E5a or E5b by checking the amino acid sequences of both E5a and E5b and selecting the sequence that conforms to the motif listed in Table I (SEQ ID NO:2).

HPV STRAINS AND AMINO ACID SEQUENCES OF HPV PROTEINS

HPV6A E1

```
1   MADDSGTENEGSGCTGWFMVEAIVQHPTGTQISDDEDEEVEDSGYDMVDEIDDSNITHNS     60  (SEQ ID NO:2)
    LEAQALFNRQEADTHYATVQDLKRKYLGSPYVSPINTIAEAVESEISPRLDAIKLTRQPK    120
    KVKRRLFQTRELTDSGYGYSEVEAGTGTQVEKHGVPENGGDGQEKDTGRDIEGEEHTEAE    180
    APTNSVREHAGTAGILELLKCKDLRAALLGKFKECFGLSFIDLIRPFKSDKTTCADWVVA    240
    GFGIHHSISEAFQKLIEPLSLYAHIQWLTNAWGMVLLVLVRFKVNKSRSTVARTLATLLN    300
    IPDNQMLIEPPKIQSGVAALYWFRTGISNASTVIGEAPEWITRQTVIEHGLADSQFKLTE    360
    MVQWAYDNDICEESEIAFEYAQRGDFDSNARAPLNSNMQAKYVKDCATMCRHYKHAEMRK    420
    MSIKQWIKHRGSKIEGTGNWKPIVQFLRHQNIEFIPFLSKFKLWLHGTPKKNCIAIVGPP    480
    DTGKSYFCMSLISFLGGTVISHVNSSSHFWLQPLVDAKVALLDDATQPCWIYMDTYMRNL    540
    LDGNPMSIDRKHKALTLIKCPPLLVTSNIDITKEEKYKYLHTRVTTFTFPNPFPFDRNGN    600
    AVYELSNANWKCFFERLSSSLDIQDSEDEEDGSNSQAFRCVPGTVVRTL              649
```

HPV6A E2

```
1   MEAIAKRLDACQEQLLELYEENSTDLNKHVLHWKCMRHESVLLYKAKQMGLSHIGMQVVP     60  (SEQ ID NO:3)
    PLKVSEAKGHNAIEMQMHLESLLKTEYSMEPWTLQETSYEMWQTPPKRCFKKRGKTVEVK    120
    FDGCANNTMDYVVWTDVYVQDTDSWVKVHSMVDAKGIYYTCGQPKTYYVNFVKEAEKYGS    180
    TKQWEVCYGSTVICSPASVSSTTQEVSIPESTTYTPAQTSTPVSSSTQEDAVQTPPRKRA    240
    RGVQQSPCNALCVAHIGPVDSGNHNLITNNHDQHQRRNNSNSSATPIVQFQGESNCLKCF    300
    RYRLNDKHRHLFDLISSTWHWASPKAPHKHAIVTVTYHSEEQRQQFLNVVKIPPTIRHKL    360
    GFMSLHLL                                                       368
```

HPV6A E4

```
1   MAAQLYVLLHLYLALHKKYPFLNLLHTPPHRPPPLCPQAPRKTQCKRRLENEHEESNSHL     60  (SEQ ID NO:4)
    ATPCVWPTLDPWTVETTTSSLTITTSTKEGTTVTVQLRL                         99
```

HPV6A E5

```
1   MEVVPVQIAAGTTSTLILPVIIAFVVCFVSIILIVWISDFIVYTSVLVLTLLLYLLLWLL     60  (SEQ ID NO:5)
    LTTPLQFFLLTLLVCYCPALYIHHYIVNTQQ                                 91
```

HPV6A E6

```
1   MESANASTSATTIDQLCKTFNLSMHTLQINCVFCKNALTTAEIYSYAYKQLKVLFRGGYP     60  (SEQ ID NO:6)
    YAACACCLEFHGKINQYRHFDYAGYATTVEEETKQDILDVLIRCYLCHKPLCEVEKVKHI    120
    LTKARFIKLNCTWKGRCLHCWTTCMEDMLP                                  150
```

HPV6A E7

```
1   MHGRHVTLKDIVLDLQPPDPVGLHCYEQLVDSSEDEVDEVDGQDSQPLKQHFQIVTCCCG     60  (SEQ ID NO:7)
    CDSNVRLVVQCTETDIREVQQLLLGTLDIVCPICAPKT                          98
```

HPV6A L1

```
1   MWRPSDSTVYVPPPNPVSKVVATDAYVTRTNIFYHASSSRLLAVGHPYFSIKRANKTVVP     60  (SEQ ID NO:8)
    KVSGYQYRVFKVVLPDPNKFALPDSSLFDPTTQRLVWACTGLEVGRGQPLGVGVSGHPFL    120
    NKYDDVENSGSGGNPGQDNRVNVGMDYKQTQLCMVGCAPPLGEHWGKGKQCTNTPVQAGD    180
    CPPLELITSVIQDGDMVDTGFGAMNFADLQTNKSDVPIDICGTTCKYPDYLQMAADPYGD    240
    RLFFFLRKEQMFARHFFNRAGEVGEPVPDTLIIKGSGNRTSVGSSIYVNTPSGSLVSSEA    300
    QLFNKPYWLQKAQGHNNGICWGNQLFVTVVDTTRSTNMTLCASVTTSSTYTNSDYKEYMR    360
    HVEEYDLQFIFQLCSITLSAEVMAYIHTMNPSVLEDWNFGLSPPPNGTLEDTYRYVQSQA    420
    ITCQKPTPEKEKPDPYKNLSFWEVNLKEKFSSELDQYPLGRKFLLQSGYRGRSSIRTGVK    480
    RPAVSKASAAPKRKRAKTKR                                            500
```

HPV STRAINS AND AMINO ACID SEQUENCES OF HPV PROTEINS

HPV6A L2

```
1   MAHSRARRRKRASATQLYQTCKLTGTCPPDVIPKVEHNTIADQILKWGSLGVFFGGLGIG    60 (SEQ ID NO:9)
    TGSGTGGRTGYVPLGTSAKPSITSGPMARPPVVVEPVAPSDPSIVSLIEESAIINAGAPE   120
    IVPPAHGGFTITSSETTTPAILDVSVTSHTTTSIFRNPVFTEPSVTQPQPPVEANGHILI   180
    SAPTITSHPIEEIPLDTFVISSSDSGPTSSTPVPGTAPRPRVGLYSRALHQVQVTDPAFL   240
    STPQRLITYDNPVYEGEDVSVQFSHDSIHNAPDEAFMDIIRLHRPAIASRRGLVRYSRIG   300
    QRGSMHTRSGKHIGARIHYFYDISPIAQAAEEIEMHPLVAAQDDTFDIYAESFEPDINPT   360
    QHPVTNISDTYLTSTPNTVTQPWGNTTVPLSSIPNDLFLQSGPDITFPTAPMGTPFSPVT   420
    ALPTGPVFITGSGFYLHPAWYFARKRRKRIPLFFSDVAA                        459
```

HPV6B E1

```
1   MADDSGTENEGSGCTGWFMVEAIVQHPTGTQISDDEDEEVEDSGYDMVDFIDDSNITHNS    60 (SEQ ID NO:10)
    LEAQALFNRQEADTHYATVQDLKRKYLGSPYVSPINTIAEAVESEISPRLDAIKLTRQPK   120
    KVKRRLFQTRELTDSGYGYSEVEAGTGTQVEKHGVPENGGDGQEKDTGRDIEGEEHTEAE   180
    APTNSVREHAGTAGILELLKCKDLRAALLGKFKECFGLSFIDLIRPFKSDKTTCLDWVVA   240
    GFGIHHSISEAFQKLIEPLSLYAHIQWLTNAWGMVLLVLLRFKVNKSRSTVARTLATLLN   300
    IPENQMLIEPPKIQSGVAALYWFRTGISNASTVIGEAPEWITRQTVIEHGLADSQFKLTE   360
    MVQWAYDNDICEESEIAFEYAQRGDFDSNARAFLNSNMQAKYVKDCATMCRHYKHAEMRK   420
    MSIKQWIKHRGSKIEGTGNWKPIVQFLRHQNIEFIPFLTKFKLWLHGTPKKNCIAIVGPP   480
    DTGKSYFCMSLISFLGGTVISHVNSSSHFWLQPLVDAKVALLDDATQPCWIYMDTYMRNL   540
    LDGNPMSIDRKHKALTLIKCPPLLVTSNIDITKEDKYKYLHTRVTTFTFPNPFPFDRNGN   600
    AVYELSNTNWKCFFERLSSSLDIQDSEDEEDGSNSQAFRCVPGTVVRTL              649
```

HPV6B E2

```
1   MEAIAKRLDACQEQLLELYEENSTDLHKHVLHWKCMRHESVLLYKAKQMGLSHIGMQVVP    60 (SEQ ID NO:11)
    PLKVSEAKGHNAIEMQMHLESLLRTEYSMEPWTLQETSYEMWQTPPKRCFKKRGKTVEVK   120
    FDGCANNTMDYVVWTDVYVQDNDTWVKVHSMVDAKGIYYTCGQFKTYYVNFVKEAEKYGS   180
    TKHWEVCYGSTVICSPASVSSTTQEVSIPESTTYTPAQTSTLVSSSTKEDAVQTPPRKRA   240
    RGVQQSPCNALCVAHIGPVDSGNHNLITNNHDQHQRRNNSNSSATPIVQFQGESNCLKCF   300
    RYRLNDRHRHLFDLISSTWHWASSKAPHKHAIVTVTYDSEEQRQQFLDVVKIPPTISHKL   360
    GFMSLHLL                                                       368
```

HPV6B E4

```
1   MGAPNIGKYVMAAQLYVLLHLYLALHKKYPFLNLLHTPPHRPPPLCPQAPRKTQCKRRLG    60 (SEQ ID NO:12)
    NEHEESNSPLATPCVWPTLDPWFVETTTSSLTITTSTKDGTTVTVQLRL              109
```

HPV6B E5A

```
1   MEVVPVQIAAGTTSTFILPVIIAFVVCFVSIILIVWISEFIVYTSVLVLTLLLYLLLWLL    60 (SEQ ID NO:13)
    LTTPLQFFLLTLLVCYCPALYIHYYIVTTQQ                                91
```

HPV6B E5B

```
1   MMLTCQFNDGDTWLGLWLLCAFIVGMLGLLLMHYRAVQGDKHTKCKKCNKHNCNDDYVTM    60 (SEQ ID NO:14)
    HYTTDGDYIYMN                                                   72
```

HPV6B E6

```
1   MESANASTSATTIDQLCKTFNLSMHTLQINCVFCKNALTTAEIYSYAYKHLKVLFRGGYP    60 (SEQ ID NO:15)
    YAACACCLEFHGKINQYRHFDYAGYATTVEEETKQDTLDVLIRCYLCHKPLCEVEKVKHI   120
    LTKARFIKLNCTWKGRCLHCWTTCMEDMLP                                 150
```

HPV6B E7

```
1   MHGRHVTLKDIVLDLQPPDPVGLHCYEQLVDSSEDEVDEVDGQDSQPLKQHFQIVTCCCG    60 (SEQ ID NO:16)
    CDSNVRLVVQCTETDIREVQQLLLGTLNIVCPICAPKT                         98
```

HPVGA L1

```
1   MWRPSDSTVYVPPPNPVSKVVATDAYVTRTNIFYHASSSRLLAVGHPYFSIKRANKTVVP    60 (SEQ ID NO:17)
    KVSGYQYRVEKVVLPDPNKFALPDSSLFDPTTQRLVWACTGLEVGRGQPLGVGVSGHPFL   120
    NKYDDVENSGSGGNPGQDNRVNVGMDYKQTQLCMVGCAPPLGEHWGKGKQCTNTPVQAGD   180
    CPPLELITSVIQDGDMVDTGFGAMNFADLQTNKSDVPIDICGTTCKYPDYLQMAADPYGD   240
    RLFFFLRKEQMFARHFFNRAGEVGEPVPDTLIIKGSGNRTSVGSSIYVNTPSGSLVSSEA   300
    QLFNKPYWLQKAQGHNNGICWGNQLFVTVVDTTRSTNMTLCASVTTSSTYTNSDYKEYMR   360
    HVEEYDLQFIFQLCSITLSAEVMAYIHTMNPSVLEDWNFGLSPPPNGTLEDTYRYVQSQA   420
    ITCQKPTPEKEKPDPYKNLSFWEVNLKEKESSELDQYPLGRKFLLQSGYRGRSSIRTGVK   480
    RPAVSKASAAPKRKRAKTKR                                           500
```

HPV STRAINS AND AMINO ACID SEQUENCES OF HPV PROTEINS

HPV6B L2

```
1   MAHSRARRRKRASATQLYQTCKLTGTCPPDVIPKVEHNTIADQILKWGSLGVFFGGLGIG    60 (SEQ ID NO:18)
    TCSGTGGRTGYVPLQTSAKPSITSGPMARPPVVVEPVAPSDPSIVSLIEESAIINAGAPE   120
    IVPPAHGGFTITSSETTTPAILDVSVTSHTTTSIFRNPVFTEPSVTQPQPPVEANGHILI   180
    SAPTVTSHPIEEIPLDTFVVSSSDSGPTSSTPVPGTAPRPRVGLYSRALHQVQVTDPAFL   240
    STPQRLITYDNPVYEGEDVSVQFSHDSIHNAPDEAFMDIIRLHRPAIASRRGLVRYSRIG   300
    QRGSMHTRSGKHIGARIHYFYDISPIAQAAEEIEMHPLVAAQDDTFDIYAESFEPGINPT   360
    QHPVTNISDTYLTSTPNTVTQPWGNTTVPLSLPNDLFLQSGPDITFPTAPMGTPFSPVTP   420
    ALPTGPVFITGSGFYLHPAWYFARKRRKRIPLFFSDVAA                         453
```

HPV11 E1

```
1   MADDSGTENEGSGCTGWFMVEAIVEHTTGTQISEDEEEEVEDSGYDMVDFIDDRHITQNS    60 (SEQ ID NO:19)
    VEAQALFNRQEADAHYATVQDLKRKYLGSPYVSPISNVANAVESEISPRLDAIKLTTQPK   120
    KVKRRLFETRELTDSGYGYSEVEAATQVEKHGDPENGGDGQERDTGRDIEGEGVEHREAE   180
    AVDDSTREHADTSGILELLKCKDIRSTLHGKFKDCFGLSFVDLIRPEKSDRTTCADWVVA   240
    GFGIHHSIADAFQKLIEPLSLYAHIQWLTNAWGMVLLVLIRFKVNKSRCTVARTLGTLLN   300
    IPENHMLIEPPKIQSGVRALYWFRTGISNASTVIGEAPEWITRQTVIEHSLADSQFKLTE   360
    MVQWAYDNDICEESEIAFEYAQRGDFDSNARAFLNSNMQAKYVKDCAIMCRHYKHAEMKK   420
    MSIKQWIKYRGTKVDSVGNWKPIVQFLRHQNIEFIPFLSKLKLWLHGTPKKNCIAIVGPP   480
    DTGKSCFCMSLIKFLGGTVISYVNSCSHFWLQPLTDAKVALLDDATQPCWTYMDTYMRNL   540
    LDGNPMSIDRKHRALTLIKCPPLLVTSNIDISKEEKYKYLHSRVTTFTFPNPFPFDRNGN   600
    AVYELSDANWKCFFERLSSSLDIEDSEDEEDGSNSQAFRCVPGSVVRTL              649
```

HPV11 E2

```
1   MEAIAKRLDACQDQLLELYEENSIDIHKHIMHWKCIRLESVLLHKAKQMGLSHIGLQVVP    60 (SEQ ID NO:20)
    PLTVSETKGHNAIEMQMHLESLAKTQYGVEPWTLQDTSYEMWLTPPKRCFKKQGNTVEVK   120
    FDGCEDNVMEYVVWTHIYLQDNDSWVKVTSSVDAKGIYYTCGQEKTYYVNFNKEAQKYGS   180
    TNHWEVCYGSTVICSPASVSSTVREVSIAEPTTYTPAQTTAPTVSACTTEDGVSAPPRKR   240
    ARGPSTNNTLCVANIRSVDSTINNIVTDNYNKHQRRNNCHSAATPIVQLQGDSNCLKCFR   300
    YRLNDKYKHLFELASSTWHWASPEAPHKNAIVTLTYSSEEQRQQFLNSVKIPPTIRHKVG   360
    FMSLHLL                                                         367
```

HPV11 E4

```
1   MVVPIIGKYVMAAQLYVLLHLYLALYEKYPLLNLLHTPPHRPPPLQCPPAPRKTACRRRL    60 (SEQ ID NO:21)
    GSEHVDRPLTTPCVWPTSDPWTVQSTTSSLTITTSTKECTTVTVQLRL              108
```

HPV11 E5A

```
1   MEVVPVQIAAATTTTLILPVVIAEAVCILSIVLIILISDFVVYTSVLVLTLLLYLLLWLL    60 (SEQ ID NO:22)
    LTTPLQFFLTLCVCYFPAFIHIYIVQTQQ                                   91
```

HPV11 E5B

```
1   MVMLTCHLNDGDTWLFLWLFTAFVVAVLGLLLLHYRAVHGTEKTKCAKCKSNRNTTVDYV    60 (SEQ ID NO:23)
    YMSHGDNGDYVYMN                                                  74
```

HPV11 E6

```
1   MESKDASTSATSIDQLCKTFNLSLHTLQIQCVFCRNALTTAEIYAYAYKNLKVVWRDNFP    60 (SEQ ID NO:24)
    FAACACCLELQGKINQYRHFNYAAYAPTVEEETNEDILKVLIRCYLCHKPLCEIEKLKHI   120
    LGKARFIKLNNQWKGRCLHCWTTCMEDLLP                                  150
```

HPV11 E7

```
1   MHGRLVTLKDIVLDLQPPDPVGLHCYEQLEDSSEDEVDKVDKQDAQPLTQHYQILTCCCG    60 (SEQ ID NO:25)
    CDSNVRLVVECTDGDIRQLQDLLLGTLNIVCPICAPKP                          98
```

HPV11 L1

```
1   MWRPSDSTVYVPPPNPVSKVVATDAYVKRTNIFYHASSSRLLAVGHPYYSIKKVNKTVVP    60 (SEQ ID NO:26)
    KVSGYQYRVFKVVLPDPNKFALPDSSLFDPTTQRLVWACTGLEVGRGQPLGVGVSGHPLL   120
    NKYDDVENSGGYGGNPGQDNRVNVGMDYKQTQLCMVGCAPPLGEHWGKGTQCSNTSVQNG   180
    DCPPLELITSVIQDGDMVDTGFGAMNFADLQTNKSDVPLDICGTVCKYPDYLQMAADPYG   240
    DRLFFYLRKEQMFARHFFNRAGTVGEPVPDDLLVKGGNNRSSVASSIYVHTPSGSLVSSE   300
    AQLFNKPYWLQKAQGHNNGICWGNHLFVTVVDTTRSTNMTLCASVSKSATYTNSDYKEYM   360
    RHVEEFDLQFIFQLCSITLSAEVMAYIHTMNPSVLEDWNFGLSPPPNGTLEDTYRYVQSQ   420
    AITCQKPTPEKEKQDPYKDMSFWEVNLKEKFSSELDQFPLGRKFLLQSGYRGRTSARTGI   480
    KRPAVSKPSTAPKRKRTKTKK                                           501
```

HPV STRAINS AND AMINO ACID SEQUENCES OF HPV PROTEINS

HPV11 L2

```
1   MKPRARRRKRASATQLYQTCKATGTCPPDVIPKVEHTTIADQILKWGSLGVFFGGLGIGT   60  (SEQ ID NO:27)
    GAGSGGRAGYIPLGSSPKPAITGGPAARPPVLVEPVAPSDPSIVSLIEESAIINAGAPEV  120
    VPPTQGGFTITSSESTTPAILDVSVTNHTTTSVFQNPLFTEPSVIQPQPPVEASGHILIS  180
    APTITSQHVEDIPLDTFVVSSSDSGPTSSTPLPRAFPRPRVGLYSRALQQVQVTDPAFLS  240
    TPQRLVTYDNPVYEGEDVSLQFTHESIHNAPDEAFMDIIRLHRPAITSRRGLVRFSRIGQ  300
    RGSMYTRSGQHIGARIHYFQDISPVTQAAEETELHPLVAAENDTFDIYAEPFDPIPDPVQ  360
    HSVTQSYLTSTPNTLSQSWGNTTVPLSIPSDWFVQSGPDITFPTASMGTPFSPVTPALPT  420
    GPVFITGSDFYLHPTWYFARRRRKRIPLFFTDVAA                            455
```

HPV16 E1

```
1   MADPAGTNGEEGTGCNGWFYVEAVVEKKTGDAISDDENENDSDTGEDLVDFIVNDNDYLT   60  (SEQ ID NO:28)
    QAETETAHALFTAQEAKQHRDAVQVLKRKYLVSPLSDISGCVDNNISPRLKAICIEKQSR  120
    AAKRRLFESEDSGYGNTEVETQQMLQVEGRHETETPCSQYSGGSGGGCSQYSSGSGGEV   180
    SERHTICQTPLTNILNVLKTSNAKAAMLAKFKELYGVSFSELVRPEKSNKSTCCDWCIAA  240
    FGLTPSIADSIKTLLQQYCLYLHIQSLACSWGMVVLLLVRYKCGKNRETIEKLLSKLLCV  300
    SPMCMMIEPPKLRSTAAALYWYKTGISNISEVYGDTPEWIQRQTVLQHSFNDCTFELSQM  360
    VQWAYDNDIVDDSEIAYKYAQLADTNSNASAFLKSNSQAKIVKDCATMCRHYKRAEKKQM  420
    SMSQWIKYRCDRVDDGGDWKQIVMFLRYQGVEFMSFLTALKRFLQGIPKKNCILLYGAAN  480
    TGKSLFGMSLMKFLQGSVICFVNSKSHFWLQPLADAKIGMLDDATVPCWNYIDDNLRNAL  540
    DGNLVSMDVKHRPLVQLKCPPLLITSNINAGTDSRWPYLHNRLVVFTFPNEFPFDENGNP  600
    VYELNDKNWKSFFSRTWSRLSLHEDEDKENDGDSLPTFKCVSGQNTNTL             649
```

HPV16 E2 Accession number W2WLHS

```
1   METLCQRLNVCQDKILTHYENDSTDLRDHIDYWKHMRLECAIYYKAREMGFKHINHQVVP   60  (SEQ ID NO:29)
    TLAVSKNKALQAIELQLTLETIYNSQYSNEKWTLQDVSLEVYLTAPTGCIKKHGYTVEVQ  120
    FDGDICNTMHYTNWTHIYICEEASVTVVEGQVDYYGLYYVHEGIRTYFVQFKDDAEKYSK  180
    NKVWEVHAGGQVILCPTSVFSSNEVSSPEIIRQHLANHPAATHTKAVALGTEETQTTIQR  240
    PRSEPDTGNPCHTTKLLHRDSVDSAPILTAFNSSHKGRINCNSNTTPIVHLKGDANTLKC  300
    LRYRFKKHCTLYTAVSSTWHWTGHNVKHKSAIVTLTYDSEWQRDQFLSQVKIPKTITVST  360
    GFMSI                                                          365
```

HPV16 E5 Accession number W5WLHS

```
1   MTNLDTASTTLLACFLLCFCVLLCVLLIRPLLLSVSTYTSLIILVLLLWITAASAFRCF   60  (SEQ ID NO:30)
    IVYIIFVYIPLFLIHTHARFLIT                                        83
```

HPV16 E6

```
1   MHQKRTAMPQDPQERPRKLPQLCTELQTTIHDIILECVYCKQQLLRREVYDFAFRDLCIV   60  (SEQ ID NO:31)
    YRDGNPYAVCDKCLKFYSKISEYRHYCYSLYGTTLEQQYNKPLCDLLIRCINCQKPLCPE  120
    EKQRHLDKKQRFHNIRGRWTGRCMSCCRSSRTRRETQL                         158
```

HPV16 E7

```
1   MHGDTPTLHEYMLDLQPETTDLYCYEQLNDSSEEEDEIDGPAGQAEPDRAHYNIVTFCCK   60  (SEQ ID NO:32)
    CDSTLRLCVQSTHVDIRTLEDLLMGTLGIVCPICSQKP                         98
```

HPV16 L1 Accession number AAD33259

```
1   MQVTFIYILVITCYENDVNVYHIFFQMSLWLPSEATVYLPPVPVSKVVSTDEYVARTNIY   60  (SEQ ID NO:33)
    YHAGTSRLLAVGHPYFPIKKPNNNKILVPKVSGLQYRVFRIHLPDPNKFGFPDTSEYNPD  120
    TQRLVWACVGVEVGRGQPLGVGISGHPLLNKLDDTENASAYAANAGVDNRECISMDYKQT  180
    QLCLIGCKPPIGEHWGKGSPCTNVAVNPGDCPPLELINTVIQDGDMVDTGFGAMDFTTLQ  240
    ANKSEVPLDICTSICKYPDYIKMVSEPYGDSLFFYLRREQMFVRHLFNRAGAVGENVPDD  300
    LYIKGSGSTANLASSNYFPTPSGSMVTSDAQIFNKPYWLQRAQGHNNGICWGNQLFVTVV  360
    DTTRSTNMSLCAAISTSETTYKNTNFKEYLRHGEEYDLQFIFQLCKITLTADVMTYIHSM  420
    NSTILEDWNFGLQPPPGGTLEDTYRFVTSQAIACQKHTPPAPKEDPLKKYTFWEVNLKEK  480
    FSADLDQFPLGRKFLLQAGLKAKPKETLGKRKATPTTSSTSTTAKRKKRKL            531
```

HPV16 L2 Accession number AAD33258

```
1   MRHKRSAKRTKRASATQLYKTCKQAGTCPPDIIPKVEGKTIADQILQYGSMGVFFGGLGI   60  (SEQ ID NO:34)
    GTGSGTGGRTGYIPLGTRPPTATDTLAPVRPPLTVDPVGPSDPSIVSLVEETSFIDAGAP  120
    TSVPSIPPDVSGFSITTSTDTTPAILDINNTVTTVTTHNNPTFTDPSVLQPPTPAETGHH  180
    FTLSSSTISTHNYEEIPMDTFIVSTNPNTVTSSTPIPGSRPVARLGLYSRTTQQVKVVDP  240
    AFITTPTKLITYDNPAYEGIDVDNTLYFSSNDNSINIAPDPDFLDIVALHRPALTSRRTG  300
    IRYSRIGNKQTLRTRSGKSIGAKVHYYYDESTIDSAEEIELQTITPSTYTTSHAALPTS   360
    INNGLYDIYADDFITDTSTTPVPSVPSTSLSGYIPANTTIPFGGAYNIPLVSGPDIPINI  420
    TDQAPSLIPIVPGSPQYTIIADAGDFYLHPSYYMLRKRRKRLPYFFSDVSLAA          473
```

HPV STRAINS AND AMINO ACID SEQUENCES OF HPV PROTEINS

HPV18 E1

```
1   MADPEGTDGEGTGCNGWFYVQAIVDKKTGDVISDDEDENATDTGSDMVDFIDTQGTFCEQ    60   (SEQ ID NO:35)
    AELETAQALFHAQEVHNDAQVLHVLKRKFAGGSTENSPLGERLEVDTELSPRLQEISLNS   120
    GQKKAKRRLFTISDSGYGCSEVEATQIQVTTNGEHGGNVCSGGSTEAIDNGGTEGNNSSV   180
    DGTSDNSNIENVNPQCTIAQLKDLLKVNNKQGAMLAVFKDTYGLSFTDLVRNFKSDKTTC   240
    TDWVTAIFGVNPTIAEGFKTLIQPPFILYAHIQCLDCKWGVLILALLRYKCGKSRLTVAKG   300
    LSTLLHVPETCMLIQPPKLRSSVAALYWYRTGISNISEVMGDTPEWIQRLTIIQHGIDDS   360
    NFDLSEMVQWAFDNELTDESDMAFEYALLADSNSNAAAFLKSNCQAKYLKDCATMCKHYR   420
    RAQKRQMNMSQWIRFRCSKIDEGGDWRPIVQFLRYQQIEFITFLGALKSFLKGTPKKNCL   480
    VFCGPANTGKSYFGMSFIHFIQCAVISFVNSTSHFWLEPLTDTKVAMLDDATTTCWTYFD   540
    TYMRNALDGNPISIDRKHKPLIQLKCPPILLTTNIHPAKDNRWPYLESRITVFEFPNAFP   600
    FDKNGNPVYEINDKNWKCFFERTWSRLDLHEEEEDADTEGNPFGTEKLRAGQNHRPL    657
```

HPV18 E2 Accession number W2WL18

```
1   MQTPKETLSERLSCVQDKIIDHYENDSKDIDSQIQYWQLIRWENAIFFAAREHGIQTLNH    60   (SEQ ID NO:36)
    QVVPAYNISKSKAHKAIELQMALQGLAQSRYKTEDWTLQDTCEELWNTEPTHCFKKGGQT   120
    VQVYFDGNKDNCMTYVAWDSVYYMTDAGTWDKTATCVSHRGLYYVKEGYNTFYIEFKSEC   180
    EKYGNTGTWEVHFGNNVIDCNDSMCSTSDDTVSATQLVKQLQHTPSPYSSTVSVGTAKTY   240
    GQTSAATRPGHCGLAEKQHCGPVNPLLGAATPTGNNKRRKLCSGNTTPIIHLKGDRNSLK   300
    CLRYRLRKHSDHYRDISSTWHWTGAGNEKTGILTVTYHSETQRTKFLNTVAIPDSVQILV   360
    GYMTM   365
```

HPV18 E5 Accession number W5WL18

```
1   MLSLIFLFCFCVCMYVCCHVPLLPSVCMCAYAWVLVFVYIVVITSPATAFTVYVFCFLLP    60   (SEQ ID NO:37)
    MLLLHIHAILSLQ    73
```

HPV18 E6

```
1   MARFEDPTRRPYKLPDLCTELNTSLQDIEITCVYCKTVLELTEVFEEAFKDLFVVYRDSI    60   (SEQ ID NO:38)
    PHAACHKCIDFYSRIRELRHYSDSVYGDTLEKLTNTGLYNLLIRCLRCQKPLNPAEKLRH   120
    LNEKRRFHNIAGHYRGQCHSCCNRARQERLQRRRETQV    158
```

HPV18 E7

```
1   MHGPKATLQDIVLHLEPQNEIPVDLLCHEQLSDSEEENDEIDGVNHQHLPARRAEPQRHT    60   (SEQ ID NO:39)
    MLCMCCKCEARIKLVVESSADDLRAFQQLFLNTLSEVCPWCASQQ   105
```

HPV18 L1 Accession number CAA28671

```
1   MCLYTRVLILHYHLLPLYGPLYHPRPLPLHSILVYMVHIIICGHYIILFLRNVNVFPIFL    60   (SEQ ID NO:40)
    QMALWRPSDNTVYLPPPSVARVVNTDDYVTPTSIFYHAGSSRLLTVGNPYFRVPAGGGNK   120
    QDIPKVSAYQYRVFRVQLPDPNKFGLPDTSIYNPETQRLVWACAGVEIGRGQPLGVGLSG   180
    HPFYNKLDDTESSHAATSNVSEDVRDNVSVDYKQTQLCILGCAPAIGEHWAKGTACKSRP   240
    LSQGDCPPLELKNTVLEDGDMVDTGYGAMDFSTLQDTKCEVPLDICQSICKYPDYLQMSA   300
    DPYGDSMFFCLRREQLFARHEWNRAGTMGDTVPQSLYIKGTGMPASPGSCVYSPSPSGSI   360
    VTSDSQLFNKPYWLHKAQGHNNGVCWHNQLFVTVVDTTPSTNLTICASTQSPVPGQYDAT   420
    KFKQYSRHVEEYDLQFIFQLCTITLTADVMSYIHSMNSSILEDWNFGVPPPPTTSLVDTY   480
    RFVQSVAITCQKDAAPAENKDPYDKLKFWNVDLKEKFSLDLDQYPLGRKFLVQAGLRRKP   540
    TIGPRKRSAPSATTSSKPAKRVRVRARK    568
```

HPV18 L2 Accession number P2WL18

```
1   MVSHRAARRKRASVTDLYKTCKQSGTCPPDVVPKVEGTTLADKILQWSSLGIFLGGLGIG    60   (SEQ ID NO:41)
    TGSGTGGRTGYIPLGGRSNTVVDVGPTRPPVVIEPVGPTDPSIVTLIEDSSVVTSGAPRP   120
    TFTGTSGFDITSAGTTTPAVLDITPSSTSVSISTTNFTNPAFSDPSIIEVPGTGEVAGNV   180
    FVGTPTSGTHGYEEIPLQTFASSGTGEEPISSTPLPTVRRVAGPRLYSRAYQQVSVANPE   240
    FLTRPSSLITYDNPAFEPVDTTLTFDPRSDVPDSDFMDIIRLHRPALTSRRGTVRFSRLG   300
    QRATMFTRSGTQIGARVHFYHDISPIAPSPEYIELQPLVSATEDNDLFDIYADDMDPAVP   360
    VPSRSTTSFAFEKYSPTISSASSYSNVTVPLTSSWDVPVYTGPDITLPSTTSVWPIVSPT   420
    APASTQYIGIHGTHYYLWPLYYFIPKKRKRVPYFFADGFVAA    462
```

HPV31 E1 Accession number W1WL31

```
1   MADPAGTDGEGTGCNGWFYVEAVIDRQTGDNISEDENEDSSDTGEDMVDFIDNCNVYNNQ    60   (SEQ ID NO:42)
    AEAETAQALFHAQEAEEHAEAVQVLKRKYVGSPLSDISSCVDYNISPRLKAICIENNSKT   120
    AKRRLFELPDSGYGNTEVETQQMVQVEEQQTTLSCNGSDGTHSERENETPTRNILQVLKT   180
    SNGKAAMLGKFKELYGVSFMELIRPFQSNKSTCTDWCVAAFGVTGTVAEGFKTLLQPYCL   240
    YCHLQSLACSWGMVMLMLVRFKCAKNRITIEKLLEKLLCISTNCMLIQPPKLRSTAAALY   300
    WYRTGMSNISDVYGETPEWIERQTVLQHSFNDTTFDLSQMVQWAYDNDVMDDSEIAYKYA   360
    QLADSDSNACAFLKSNSQAKIVKDCGTMCRHYKRAEKRQMSMGQWIKSRCDKVSDEGDWR   420
    DIVKFLRYQQIEFVSFLSALKLFLKGVPKKNCILIHGAPNTGKSYFGMSLISFLQGCIIS   480
```

HPV STRAINS AND AMINO ACID SEQUENCES OF HPV PROTEINS

```
     YANSKSHFWLQPLADAKIGMLDDATTPCWHYIDNYLRNALDGNPVSIDVKHKALMQLKCP   540
     PLLITSNINAGKDDRWPYLHSRLVVFTFPNPFPFDKNGNPVYELSDKNWKSFFSRTWCRL   600
     NLHEEEDKENDGDSFSTFKCVSGQNIRTL                                  629
```

HPV31 E2 Accession number W2WL31

```
1    METLSQRLNVCQDKILEHYENDSKRLCDHIDYWKHIRLECVLMYKAREMGIHSINHQVVP   60 (SEQ ID NO:43)
     ALSVSKAKALQAIELQMMLETLNNTEYKNEDWTMQQTSLELYLTAPTGCLKKHGYTVEVQ   120
     FDGDVHNTMHYTNWKFIYLCIDGQCTVVEGQVNCKGIYYVHEGHITYFVNFTEEAKKYGT   180
     GKKWEVHAGGQVIVFPESVFSSDEISFAGIVTKLPTANNTTTSNSKTCALGTSEGVRRAT   240
     TSTKRPRTEPEHRNTHHPNKLLRGDSVDSVNCGVISAAACTNQTRAVSCPATTPIIHLKG   300
     DANILKCLRYRLSKYKQLYEQVSSTWHWTCTDGKHKNAIVTLTYISTSQRDDFLNTVKIP   360
     NTVSVSTGYMTI                                                   372
```

HPV31 E5 Accession number W5WL31

```
1    MIELNISTVSIVLCFLLCECVLLFVCLVIRPLVLSVSVYATLLLLIVILWVIATSPLRCF   60 (SEQ ID NO:44)
     CIYVVFIYIPLFVIHTHASFLSQQ                                       84
```

HPV31 E6 Accession number W6WL31

```
1    MFKNPAERPRKLHELSSALEIPYDELRLNCVYCKGQLTETEVLDFAFTDLTIVYRDDTPH   60 (SEQ ID NO:45)
     GVCTKCLRFYSKVSEFRWYRYSVYGTTLEKLTNKGICDLLIRCITCQRPLCPEEKQRHLD   120
     KKKRFHNIGGRWTGRCIACWRRPPTETQV                                  149
```

HPV31 E7 Accession number W7WL31

```
1    MRGETPTLQDYVLDLQPEATDLHCYEQLPDSSDEEDVIDSPAGQAEPDTSNYNIVTFCCQ   60 (SEQ ID NO:46)
     CKSTLRLCVQSTQVDIRILQELLMGSFGIVCPNCSTRL                         98
```

HPV31 L1 Accession number P1WL31

```
1    MSLWRPSEATVYLPPVPVSKVVSTDEYVTRTNIYYHAGSARLLTVGHPYYSIPKSDNPKK   60 (SEQ ID NO:47)
     IVVPKVSGLQYRVFRVRLPDPNKFGFPDTSFYNPETQRLVWACVGLEVGRGQPLGVGISG   120
     HPLLNKFDDTENSNRYAGGPGTDNRECISMDYKQTQLCLLGCKPPIGEHWGKGSPCSNNA   180
     ITPGDCPPLELKNSVTQDGDMVDTGFGAMDFTALQDTKSNVPLDICNSICKYPDYLKMVA   240
     EPYGDTLFFYLRREQMFVRHFFNRSGTVGESVPTDLYIKGSGSTATLANSTYEPTPSGSM   300
     VTSDAQIFNKPYWMQRAQGHNNGICWGNQLFVTVVDTTRSTNMSVCAAIANSDTTFKSSN   360
     FKEYLRHGEEFDLQFIFQLCKITLSADIMTYIHSMNPAILEDWNFGLTTPPSGSLEDTYR   420
     FVTSQAITCQKTAPQKPKEDPFKDYVFWEVNLKEKFSADLDQFPLGRKFLLQAGYRARPK   480
     FKAGKRSAPSASTTTPAKRKKTKK                                       504
```

HPV31 L2 Accession number P2WL31

```
1    MRSKRSTKRTKRASATQLYQTCKAAGTCPSDVIPKIEHTTIADQILRYGSMGVFFGGLGI   60 (SEQ ID NO:48)
     GSGSGTGGRTGYVPLSTRPSTVSEASIPIRPPVSIDPVGPLDPSIVSLVEESGIVDVGAP   120
     APIPHPPTTSGFDIATTADTTPAILDVTSVSTHENPTFTDPSVLQPPTPAETSGHLLLSS   180
     SSISTHNYEEIPMDTFIVSTNNENITSSTPIPGVRRPARLGLYSKATQQVKVIDPTFLSA   240
     PKQLITYENPAYETVNAEESLYFSNTSHNIAPDPDFLDIIALHRPALTSRRNTVRYSRLG   300
     NKQTLRTRSGATIGARVHYYYDISSINPAGESIEMQPLGASATTTSTLNDGLYDIYADTD   360
     FTVDTPATHNVSPSTAVQSTSAVSAYVPTNTTVPLSTGFDIPIFSGPDVPIEHAPTQVFP   420
     FPLAPTTPQVSIFVDGGDFYLHPSYYMLKRRRKRVSYFFTDVSVAA                 466
```

HPV45 E1 Accession number S36563

```
1    MADPEGTDGEGTGCNGWFFVETIVEKKTGDVISDDEDETATDTGSDMVDFIDTQLSICEQ   60 (SEQ ID NO:49)
     AEQETAQALFHAQEVQNDAQVLHLLKRKFAGGSKENSPLGEQLSVDTDLSPRLQEISLNS   120
     GHKKAKRRLFTISDSGYGCSEVEAAETQVTVNTNAENGGSVHSTQSSGGDSSDNAENVDP   180
     HCSITELKELLQASNKKAAMLAVFKDIYGLSFTDLVRNFKSDKTTCTDWVMAIFGVNPTV   240
     AEGFKTLIKPATLYAHIQCLDCKWGVLILALLRYKCGKNRLTVAKGLSTLLHVPETCMLI   300
     EPPKLRSSVAALYWYRTGISNISEVSGDTPEWIQRLTIIQHGIDDSNFDLSDMVQWAFDN   360
     DLTDESDMAFQYAQLADCNSNAAAFLKSNCQAKYLKDCAVMCRHYKRAQKRQMNMSQWIK   420
     YRCSKIDEGGDWRPIVQELRYQGVEFISFLRALKEFLKGTPKKNCILLYGPANTGKSYFG   480
     MSFIHFLQGAIISFVNSNSHFWLEPLADTKVAMLDDATHTCWTYFDNYMRNALDGNPISI   540
     DRKHKPLLQLKCPPILLTSNIDPAKDNKWPYLESRVTVFTFPHAFPFDKNGNPVYEINDK   600
     NWKCFFERTWSRLDLHEDDEDADTEGIPFGTFKCVTGQNTRPL                    643
```

HPV45 E2 Accession number S36564

```
     MKMQTPKESLSERLSALQDKILDHYENDSKDINSQISYWQLIRLENAILFTAREHGITKL   60 (SEQ ID NO:50)
     NHQVVPPINISKSKAHKAIELQMALKGLAQSKYNNEEWTLQDTCEELWNTEPSQCFKKGG   120
     KTVHVYFDGNKDNCMNYVVWDSIYYITETGIWDKTAACVSYWGVYYIKDGDTTYYVQFKS   180
     ECEKYGNSNTWEVQYGGNVIDCNDSMCSTSDDTVSATQIVRQLQHASTSTPKTASVGTPK   240
     PHIQTPATKRPRQCGLTEQEHGRVNTHVHNPLLCSSTSNNKRRKVCSGNTTPIIHLKGDK   300
     NSLKCLRYRLRKYADHYSEISSTWHWTGCNKNTGILTVTYNSEVQRNTFLDVVTIPNSVQ   360
     ISVGYMTI                                                       368
```

HPV STRAINS AND AMINO ACID SEQUENCES OF HPV PROTEINS

HPV45 E6 Accession number CAB44706

```
1   MARFDDPTQRPYKLPDLCTELNTSLQDVSIACVYCKATLERTEVYQFAKKDLFIVYRDCI   60  (SEQ ID NO:51)
    AYAACHKCIDFYSRIRELRYYSNSVYGETLEKITNTELYNLLIRCLRCQKPLNPAEKRRH   120
    LKDKRRFHSIAGQYRGQCNTCCDQARQERLRRRRETQV                       158
```

HPV45 E7 Accession number CAB44707

```
1   MHGPRATLQEIVLHLEPQNELDPVDLLCYEQLSESEEENDEADGVSHAQLPARRAEPQRH   60  (SEQ ID NO:52)
    KILCVCCKCDGRIELTVESSADDLRTLQQLFLSTLSFVCPWCATNQ               106
```

HPV45 L1 Accession number CAB44705

```
1   MAHNIIYGHGIIIFLKNVNVFPIFLQMALWRPSDSTVYLPPPSVARVVNTDDYVSRTSIF   60  (SEQ ID NO:53)
    YHAGSSRLLTVGNPYFRVVPSGAGNKQAVPKVSAYQYRVFRVALPDPNKFGLPDSTIYNP   120
    ETQRLVWACVGMEIGRGQPLGIGLSGHPFYNKLDDTESAHAATAVITQDVRDNVSVDYKQ   180
    TQLCILGCVPAIGEHWAKGTLCKPAQLQPGDCPPLELKNTIIEDGDMVDTGYGAMDFSTL   240
    QDTKCEVPLDICQSICKYPDYLQMSADPYGDSMFFCLRREQLFARHFWNRAGVMGDTVPT   300
    DLYIKGTSANMRETPGSCVYSPSPSGSITTSDSQLPNKPYWLHKAQGHNNGICWHNQLFV   360
    TVVDTTRSTNLTLCASTQNPVPNTYDPTKFKHYSRHVEEYDLQFIFQLCTITLTAEVMSY   420
    IHSMNSSILENWNEGVPPPPTTSLVDTYRFVQSVAVTCQKDTTPPEKQDPYDKLKFWTVD   480
    LKEKFSSDLDQYPLGRKFLVQAGLRRRPTIGPRKRPAASTSTASRPAKRVRIRSKK     536
```

HPV45 L2 Accession number S36565

```
1   MVSHRAARRKRASATDLYRTCKQSGTCPPDVINKVEGTTLADKILQWSSLGIFLGGLGIG   60  (SEQ ID NO:54)
    TGSGSGGRTGYVPLGGRSNTVVDVGPTRPPVVIEPVGPTDPSIVTLVEDSSVVASGAPVP   120
    TFTGTSGFEITSSGTTTPAVLDITPTVDSVSISSTSPTNPAFSDPSIIEVPQTGEVSGNI   180
    FVGTPTSGSHGYEEIPLQTFASSGSGTEPISSTPLPTVRRVRGPRLYSRANQQVRVSTSQ   240
    FLTHPSSLVTFDNPAYEPLDTTLSFEPTSNVPDSDFMDIIRLHRPALSSRRGTVRFSRLG   300
    QRATMFTRSGKQIGGRVHFYHDISPIAATEEIELQPLISATNDSDLFDVYADFPPPASTT   360
    PSTIHKSFTYPKYSLTMPSTAASSYSNVTVPLTSAWDVPIYTGPDIILPSHTPMWPSTSP   420
    TNASTTTYIGIHGTQYYLWPWYYFPKKRKRIPYFFADGFVAA                   463
```

HPV33 E1 Accession number W1WL33

```
1   MADPEGTNGAGMGCTGWFEVEAVIERRTGDNISEDEDETADDSGTDLLEFIDDSMENSIQ   60  (SEQ ID NO:55)
    ADTEAARALPNIQEGEDDLNAVCALKRKFAACSQSAAEDVVDRAANPCRTSINKNKECTY   120
    RKRKIDELEDSGYGNTEVETQQMVQQVESQNGDTNLNDLESSGVGDDSEVSCETNVDSCE   180
    NVTLQEISNVLHSSNTKANILYKFKEAYGISFMELVRPFKSDKTSCTDWCITGYGISPSV   240
    AESLKVLIKQHSLYTHLQCLTCDRGIIILLLIRFRCSKNRLTVAKLMSNLLSIPETCMVI   300
    EPPKLRSQTCALYWFRTAMSNISDVQGTTPEWIDRLTVLQHSFNDNIFDLSEMVQWAYDN   360
    ELTDDSDIAYYYAQLADSNSNAAAFLKSNSQAKIVKDCGIMCRHYKKAEKRKMSIGQWIQ   420
    SRCEKTNDGGNWRPIVQLLRYQNIEFTAFLGAFKKFLKGIPKKSCMLICGPANTGKSYFG   480
    MSLIQFPLKGCVISCVNSKSHFWLQPLSDAKIGMIDDVTPISWTYIDDYMRNALDGNEISI   540
    DVKHRALVQLKCPPLLLTSNTNAGTDSRWPYLHSRLTVFEFKNPFPFDENGNPVYAINDE   600
    NWKSFFSRTWCKLDLIEEEDKENHGGNISTFKCSAGENTRSLRS                 644
```

HPV33 E2 Accession number W2WL33

```
1   MEEISARLNAVQEKILDLYEADKTDLPSQIEHWKLIRMECALLYTAKQMGFSHLCHQVVP   60  (SEQ ID NO:56)
    SLLASKTKAFQVIELQMALETLSKSQYSTSQWTLQQTSLEVWLCEPPKCFKKQGETVTVQ   120
    YDNDKKNTMDYTNWGEIYIIEEDTCTMVTGKVDYIGMYYIHNCEKVYFKYEKEDAAKYSK   180
    TQMWEVHVGGQVIVCPTSISSNQISTTETADIQTDNDNRPPQAAAKRRRPADTTDTAQPL   240
    TKLFCADPALDNRTARTATNCTNKQRTVCSSNVAPIVHLKGESNSLKCLRYRLKPYKELY   300
    SSMSSTWHWTSDNKNSKNGIVTVTFVTEQQQQMFLGTVKIPPTVQISTGFMTL        353
```

HPV33 E5 Accession number W5WL33

```
1   MIFVFVLCFILFLCLSLLLRPLILSISTYAWLLVLVLLLWVFVGSPLKIKFCYLLFLYLP   60  (SEQ ID NO:57)
    MMCINFHAQHMTQQE                                              75
```

HPV33 E6 Accession number W6WL33

```
1   MFQDTEEKPRTLHDLCQALETTIHNIELQCVECKKPLQRSEVYDFAFADLTVVYREGNPF   60  (SEQ ID NO:58)
    GICKLCLRFLSKISEYRHYNYSVYGNTLEQTVKKPLNEILIRCIICQRPLCPQEKKRHVD   120
    LNKRFHNISGRWAGRCAACWRSRRRETAL                                149
```

HPV33 E7 Accession number W7WL33

```
1   MRGHKPTLKEYVLDLYPEPTDLYCYEQLSDSSDEDEGLDRPDGQAQPATADYYIVTCCHT   60  (SEQ ID NO:59)
    CNTTVRLCVNSTASDLRTIQQLLMGTVNIVCPTCAQQ                        97
```

HPV33 L1 Accession number P1WL33

```
1   MSVWRPSEATVYLPPVPVSKVVSTDEYVSRTSIYYYAGSSRLLAVGHPYFSIKNPTNAKK   60  (SEQ ID NO:60)
    LLVPKVSGLQYRVFRVRLPDPNKFGFPDTSFYNPDTQRLVWACVGLEIGRGQPLGVGISG   120
```

-continued

| HPV STRAINS AND AMINO ACID SEQUENCES OF HPV PROTEINS | |
|---|---|
| HPLLNKFDDTETGNKYPGQPGADNRECLSMDYKQTQLCLLGCKPPTGEHWGKGVACTNAA | 180 |
| PANDCPPLELINTIIEDGDMVDTGFGCMDFKTLQANKSDVPIDICGSTSKYPDYLKMTSE | 240 |
| PYGDSLFFFLRREQMFVRHEFNRAGTLGEAVPDDLYIKGSGTTASIQSSAFFPTPSGSMV | 300 |
| TSESQLFNKPYWLQRAQGHNNGICWGNQVFVTVVDTTRSTNMTLCTQVTSDSTYKNENFK | 360 |
| EYIRHVEEYDLQFVFQLCKVTLTAEVMTYIHAMNPDILEDWQFGLTPPPSASLQDTYRFV | 420 |
| TSQAITCQKTVPPKEKEDPLGKYTFWEVDLKEKFSADLDQFPLGRKFLLQAGLKAKPKLK | 480 |
| RAAPTSTRTSSAKRKKVKK | 499 |

HPV33 L2 Accession number P2WL33

| 1 | MRHKRSTRRKRASATQLYQTCKATGTCPPDVIPKVEGSTIADQILKYGSLGVFFGGLGIG | 60 (SEQ ID NO:61) |
|---|---|---|
| | TGSGSGGRTGYVPIGTDPPTAAIPLQPIRPPVTVDTVGPLDSSIVSLIEETSEIEAGAPA | 120 |
| | PSIPTPSGFDVTTSADTTPAIYNVSSVGESSIQTISTHLNPTFTEPSVLHPPAPAEASGH | 180 |
| | FIFSSPTVSTQSYENIPMDTFVVSTDSSNVTSSTPIPGSRPVARLGLYSRNTQQVKVVDP | 240 |
| | AFLTSPHKLITYDNPAFESFDPEDTLQFQHSDISPAPDPDFLDIIALHRPAITSRRHTVR | 300 |
| | FSRVGQKATLKTRSGKQIGARIHYYQDLSPIVPLDHTVPNEQYELQPLHDTSTSSYSIND | 360 |
| | GLYDVYADDVDNVHTPMQHSYSTFATTRTSNVSIPLNTGFDTPVMSGPDIPSPLFPTSSP | 420 |
| | FVPISPFFPFDTIVVDGADFVLHPSYFILRRRRKRFPYFFTDVRVAA | 467 |

HPV56 E2 Accession number S36581

| 1 | MVPCLQVCKAKACSAIEVQIALESLSTTIYNNEEWTLRDTCEELWLTEPKKCEKKEGQHI | 60 (SEQ ID NO:62) |
|---|---|---|
| | EVWFDGSKNNCMQYVAWKYIYYNGDCGWQKVCSGVDYRGIYYVHDGHKTYYTDFEQEAKK | 120 |
| | FGCKNIWEVHMENESIYCPDSVSSTCRYNVSPVETVNEYNTHKTTTTTSTSVGNQDAAVS | 180 |
| | HRPGKRPRLRESEFDSSRESHAKCVTTHTHISDTDNTDSRSRSINNNNHPGDKTTPVVHL | 240 |
| | KGEPNRLKCCRYRFQKYKTLFVDVTSTYHWTSTDNKNYSIITIIYKDETQRNSFLSHVKI | 300 |
| | PVVYRLVWDK | 310 |

HPV56 E6 Accession number W6WL56

| 1 | MEPQFNNPQERPRSLHHLSEVLEIPLIDLRLSCVYCKKELTRAEVYNFACTELKLVYRDD | 60 (SEQ ID NO:63) |
|---|---|---|
| | FPYAVCRVCLLFYSKVRKYRYYDYSVYGATLESITKKQLCDLLIRCYRCQSPLTPEEKQL | 120 |
| | HCDRKRRFHLIAHGWTGSCLCCWRQTSREPRESTV | 155 |

HPV56 E7 Accession number S36580

| 1 | MHGKVPTLQDVVLELTPQTEIDLQCNEQLDSSEDEDEDEVDHLQERPQQARQAKQHTCYL | 60 (SEQ ID NO:64) |
|---|---|---|
| | IHVPCCECKFVVQLDIQSTKEDLRVVQQLLMGALTVTCPLCASSN | 105 |

HPV56 L1 Accession number S38563

| 1 | MMLPMMYIYRDPPLHYGLCIFLDVGAVNVFPIFLQMATWRPSENKVYLPPTPVSKVVATD | 60 (SEQ ID NO:65) |
|---|---|---|
| | SYVKRTSIFYHAGSSRLLAVGHPYYSVTKDNTKTNIPKVSAYQYRVFRVRLPDPNKFGLP | 120 |
| | DTNIYNPDQERLVWACVGLEVGRGQPLGAGLSGHPLFNRLDDTESSNLANNNVIEDSRDN | 180 |
| | ISVDGKQTQLCIVGCTPAMGEHWTKGAVCKSTQVTTGDCPPLALINTPIEDGDMIDTGFG | 240 |
| | AMDFKVLQESKAEVPLDIVQSTCKYPDYLKMSADAYGDSMWFYLRREQLFARHYFNRAGK | 300 |
| | VGETIPAELYLKGSNGREFPPSSVYVATPSGSMITSEAQLENKPYWLQRAQGHNNGICWG | 360 |
| | NQLFVTVVDTTRSTNMTISTATEQLSKYDARKINQYLRHVEEYELQFVFQLCKITLSAEV | 420 |
| | MAYLHNMNANLLEDWNIGLSPPVATSLEDKYRYVRSTAITCQREQPPTEKQDPLAKYKFW | 480 |
| | DVNLQDSFSTDLDQFPLGRKFLMQLGTRSKPAVATSKKRSAPTSTSTPAKRKRR | 534 |

HPV56 L2 Accession number S36582

| 1 | MVAHRATRRKRASATQLYKTCKLSGTCPEDVVNKIEQKTWADKILQWGSLFTYFGGLGIG | 60 (SEQ ID NO:66) |
|---|---|---|
| | TGTGSGGRAGYVPLGSRPSPIVDVTPARPPIVVESVGPTDPSIVTLVEESSVIESGAGIP | 120 |
| | NFTGSGGFEITSSSTTTPAVLDITPTSSTVHVSSTHITNPLFIDPPVIEAPQTGEVSGNI | 180 |
| | LISTPTSGIHSYEEIPMQTFAVHGSGTEPISSTPIPGFRRIAAPRLYRKAFQQVKVTDPA | 240 |
| | FLDRPATLVSADNPLFEGTDTSLAFSPSGVAPDPDFMNIVALHRPAFTTRRGGVRFSRLG | 300 |
| | RKATIQTRRGTQIGARVHYYYDISPIAQAEEIEMQPLLSANNSFDGLYDIYANIDDEAPG | 360 |
| | LSSQSVATPSAHLPIKPSTLSFASNTTNVTAPLGNVWETPFYSGPDIVLPTGPSTWPFVP | 420 |
| | QSPYDVTHDVYIQGSSFALWPVYFFRRRRRKRIPYFFADGDVAA | 464 |

HLA Class I Motifs Indicative of CTL Inducing Peptide Epitopes:

The primary anchor residues of the HLA class I peptide epitope supermotifs and motifs delineated below are summarized in Table I. The HLA class I motifs set out in Table I(a) are those most particularly relevant to the invention claimed here. Primary and secondary anchor positions are summarized in Table II. Allele-specific HLA molecules that comprise HLA class I supertype families are listed in Table VI. In some cases, peptide epitopes may be listed in both a motif and a supermotif Table. The relationship of a particular motif and respective supermotif is indicated in the description of the individual motifs.

III.D.1. HLA-A1 Supermotif

The HLA-A1 supermotif is characterized by the presence in peptide ligands of a small (T or S) or hydrophobic (L, I, V, or M) primary anchor residue in position 2, and an aromatic (Y, F, or W) primary anchor residue at the C-terminal position of the epitope. The corresponding family of HLA molecules that bind to the A1 supermotif (i.e., the HLA-A1 supertype) is comprised of at least A*0101, A*2601, A*2602, A*2501, and A*3201 (see, e.g., DiBrino, M. et al., *J. Immunol.* 151:5930, 1993; DiBrino, M. et al., *J. Immunol.* 152:620, 1994; Kondo, A. et al., *Immunogenetics* 45:249, 1997). Other allele-specific HLA molecules predicted to be members of the A1 superfamily are shown in Table VI. Peptides binding to each of the individual HLA proteins can be modulated by substitutions at primary and/or secondary anchor positions, preferably choosing respective residues specified for the supermotif.

Representative peptide epitopes that comprise the A1 supermotif are set forth in Table VII.

III.D.2. HLA-A2 Supermotif

Primary anchor specificities for allele-specific HLA-A2.1 molecules (see, e.g., Falk et al., *Nature* 351:290-296, 1991; Hunt et al., *Science* 255:1261-1263, 1992; Parker et al., *J. Immunol.* 149:3580-3587, 1992; Ruppert et al., *Cell* 74:929-937, 1993) and cross-reactive binding among HLA-A2 and -A28 molecules have been described. (See, e.g., Fruci et al., *Human Immunol.* 38:187-192, 1993; Tanigaki et al., *Human Immunol.* 39:155-162, 1994; Del Guercio et al., *J. Immunol.* 154:685-693, 1995; Kast et al., *J. Immunol.* 152:3904-3912, 1994 for reviews of relevant data.) These primary anchor residues define the HLA-A2 supermotif; which presence in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901. Other allele-specific HLA molecules predicted to be members of the A2 superfamily are shown in Table VI. As explained in detail below, binding to each of the individual allele-specific HLA molecules can be modulated by substitutions at the primary anchor and/or secondary anchor positions, preferably choosing respective residues specified for the supermotif.

Representative peptide epitopes that comprise an A2 supermotif are set forth in Table VIII. The motifs comprising the primary anchor residues V, A, T, or Q at position 2 and L, I, V, A, or T at the C-terminal position are those most particularly relevant to the invention claimed herein.

III.D.3. HLA-A3 Supermotif

The HLA-A3 supermotif is characterized by the presence in peptide ligands of A, L, I, V, M, S, or, T as a primary anchor at position 2, and a positively charged residue, R or K, at the C-terminal position of the epitope, e.g., in position 9 of 9-mers (see, e.g., Sidney et al., *Hum. Immunol.* 45:79, 1996). Exemplary members of the corresponding family of HLA molecules (the HLA-A3 supertype) that bind the A3 supermotif include at least A*0301, A*1101, A*3101, A*3301, and A*6801. Other allele-specific HLA molecules predicted to be members of the A3 supertype are shown in Table VI. As explained in detail below, peptide binding to each of the individual allele-specific HLA proteins can be modulated by substitutions of amino acids at the primary and/or secondary anchor positions of the peptide, preferably choosing respective residues specified for the supermotif.

Representative peptide epitopes that comprise the A3 supermotif are set forth in Table IX.

III.D.4. HLA-A24 Supermotif

The HLA-A24 supermotif is characterized by the presence in peptide ligands of an aromatic (F, W, or Y) or hydrophobic aliphatic (L, I, V, M, or T) residue as a primary anchor in position 2, and Y, F, W, L, I, or M as primary anchor at the C-terminal position of the epitope (see, e.g., Sette and Sidney, *Immunogenetics* 1999 November;50(3-4):201-12 Review). The corresponding family of HLA molecules that bind to the A24 supermotif (i.e., the A24 supertype) includes at least A*2402, A*3001, and A*2301. Other allele-specific HLA molecules predicted to be members of the A24 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the A24 supermotif are set forth in Table X.

III.D.5. HLA-B7 Supermotif

The HLA-B7 supermotif is characterized by peptides bearing proline in position 2 as a primary anchor, and a hydrophobic or aliphatic amino acid (L, I, V, M, A, F, W, or Y) as the primary anchor at the C-terminal position of the epitope. The corresponding family of HLA molecules that bind the B7 supermotif (i.e., the HLA-B7 supertype) is comprised of at least twenty six HLA-B proteins including: B*0702, B*0703, B*0704, B*0705, B* 1508, B*3501, B*3502, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, and B*7801 (see, e.g., Sidney, et al., *J. Immunol.* 154:247, 1995; Barber, et al., *Curr. Biol.* 5:179, 1995; Hill, et al., *Nature* 360:434, 1992; Rammensee, et al., *Immunogenetics* 41:178, 1995 for reviews of relevant data). Other allele-specific HLA molecules predicted to be members of the B7 supertype are shown in Table VI. As explained in detail below, peptide binding to each of the individual allele-specific HLA proteins can be modulated by substitutions at the primary and/or secondary anchor positions of the peptide, preferably choosing respective residues specified for the supermotif.

Representative peptide epitopes that comprise the B7 supermotif are set forth in Table XI.

III.D.6. HLA-B27 Supermotif

The HLA-B27 supermotif is characterized by the presence in peptide ligands of a positively charged (R, H, or K) residue as a primary anchor at position 2, and a hydrophobic (F, Y, L, W, M, I, A, or V) residue as a primary anchor at the C-terminal position of the epitope (see, e.g., Sidney and Sette, *Immunogenetics* 1999 November;50(3-4):20-12, Review). Exemplary members of the corresponding family of HLA molecules that bind to the B27 supermotif (i.e., the B27 supertype) include at least B*1401, B*1402, B*1509, B*2702, B*2703, B*2704, B*2705, B*2706, 13*3801, B*3901, B*3902, and B*7301. Other allele-specific HLA molecules predicted to be members of the B27 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B27 supermotif are set forth in Table XII.

III.D.7. HLA-B44 Supermotif

The HLA-B44 supermotif is characterized by the presence in peptide ligands of negatively-charged (D or E) residues as a primary anchor in position 2, and hydrophobic residues (F, W, Y, L, I, M, V, or A) as a primary anchor at the C-terminal position of the epitope (see, e.g., Sidney et al., *Immunol. Today* 17:261, 1996). Exemplary members of the corresponding family of HLA molecules that bind to the B44 supermotif (i.e., the B44 supertype) include at least: B*1801, B*1802, B*3701, B*4001, B*4002, B*4006, B*4402, B*4403, and B*4006. Peptide binding to each of the allele-specific HLA molecules can be modulated by substitutions at primary and/or secondary anchor positions; preferably choosing respective residues specified for the supermotif.

III.D.8. HILA-B58 Supermotif

The HLA-B58 supermotif is characterized by the presence in peptide ligands of a small aliphatic residue (A, S, or T) as a primary anchor residue at position 2, and an aromatic or hydrophobic residue (F, W, Y, L, I, V, M, or A) as a primary anchor residue at the C-terminal position of the epitope (see, e.g., Sidney and Sette, Immunogenetics 1999 November;50 (3-4):201-12, Review). Exemplary members of the corresponding family of HLA molecules that bind to the B58 supermotif (i.e., the B58 supertype) include at least: B*1516, B*1517, B*5701, B*5702, and B*5801. Other allele-specific HLA molecules predicted to be members of the B58 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B58 supermotif are set forth in Table XIII.

III.D.9. HLA-B62 Supermotif

The HLA-B62 supermotif is characterized by the presence in peptide ligands of the polar aliphatic residue Q or a hydrophobic aliphatic residue (L, V, M, I, or P) as a primary anchor in position 2, and a hydrophobic residue (F, W, Y, M, I, V, L, or A) as a primary anchor at the C-terminal position of the epitope (see, e.g., Sidney and Sette, *Immunogenetics* 1999 November;50(3-4):201-12, Review). Exemplary members of the corresponding family of HLA molecules that bind to the B62 supermotif (i.e., the B62 supertype) include at least: B1*1501, B*1502, B*1513, and B5201. Other allele-specific HLA molecules predicted to be members of the B62 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B62 supermotif are set forth in Table XIV.

III.D.10. HLA-A1 Motif

The HLA-A 1 motif is characterized by the presence in peptide ligands of T, S, or M as a primary anchor residue at position 2 and the presence of Y as a primary anchor residue at the C-terminal position of the epitope. An alternative allele-specific A1 motif is characterized by a primary anchor residue at position 3 rather than position 2. This motif is characterized by the presence of D, E, A, or S as a primary anchor residue in position 3, and a Y as a primary anchor residue at the C-terminal position of the epitope (see, e.g., DiBrino et al., *J. Immunol.;* 152:620, 1994; Kondo et al, *Immunogenetics* 45:249, 1997; and Kubo et al., *J. Immunol.* 152:3913, 1994 for reviews of relevant data). Peptide binding to HLA A1 can be modulated by substitutions at primary and/or secondary anchor positions, preferably choosing respective residues specified for the motif.

Representative peptide epitopes that comprise either A1 motif are set forth in Table XV. Those epitopes comprising T, S, or M at position 2 and Y at the C-terminal position are also included in the listing of HLA-A1 supermotif-bearing peptides listed in Table VII, as these residues are a subset of the A1 supermotif primary anchors.

III.D.11. HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., *Nature* 351:290-296, 1991) and was further found to comprise an I at position 2 and I or A at the C-terminal position of a nine amino acid peptide (see, e.g., Hunt et al., *Science* 255:1261-1263, Mar. 6, 1992; Parker et al, *J. Immunol.* 149:3580-3587, 1992). The A*0201 allele-specific motif has also been defined by the present inventors to additionally comprise V, A, T, or Q as a primary anchor residue at position 2, and M or T as a primary anchor residue at the C-terminal position of the epitope (see, e.g., Kast et al., *J. Immunol.* 152:3904-3912, 1994). Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. The preferred and tolerated residues that characterize the primary anchor positions of the HLA-A*0201 motif are identical to the residues describing the A2 supermotif. (For reviews of relevant data, see, e.g., Del Guercio et al., *J. Immunol.* 154:685-693, 1995; Ruppert et al., *Cell* 74:929-937, 1993; Sidney et al., *Immunol. Today* 17:261-266, 1996; Sette and Sidney, *Curr. Opin. in Immunol.* 10:478-482, 1998). Secondary anchor residues that characterize the A*0201 motif have additionally been defined (see, e.g., Ruppert et al., *Cell* 74:929-937, 1993). These are shown in Table II. Peptide binding to HLA-A*0201 molecules can be modulated by substitutions at primary and/or secondary anchor positions, preferably choosing respective residues specified for the motif.

Representative peptide epitopes that comprise an A*0201 motif are set forth in Table VIII. The A*0201 motifs comprising the primary anchor residues V, A, T, or Q at position 2 and L, I, V, A, or T at the C-terminal position are those most particularly relevant to the invention claimed herein.

III.D.12. HLA-A3 Motif

The HLA-A3 motif is characterized by the presence in peptide ligands of L, M, V, I, S, A, T, F, C, G, or D as a primary anchor residue at position 2, and the presence of K, Y, R, H, F, or A as a primary anchor residue at the C-terminal position of the epitope (see, e.g., DiBrino et al., *Proc. Natl. Acad. Sci USA* 90:1508, 1993; and Kubo et al, *J. Immunol.* 152:3913-3924, 1994). Peptide binding to HLA-A3 can be modulated by substitutions at primary and/or secondary anchor positions, preferably choosing respective residues specified for the motif.

Representative peptide epitopes that comprise the A3 motif are set forth in Table XVI. Those epitopes that also comprise the A3 supermotif are also listed in Table IX. The A3 supermotif primary anchor residues comprise a subset of the A3- and A11-allele specific motif primary anchor residues.

III.D.13. HLA-A11 Motif

The HLA-A11 motif is characterized by the presence in peptide ligands of V, T, M, L, I, S, A, G, N, C, D, or F as a primary anchor residue in position 2, and K, R, Y, or H as a primary anchor residue at the C-terminal position of the epitope (see, e.g., Zhang et al., *Proc. Natl. Acad Sci USA* 90:2217-2221, 1993; and Kubo et al, *J. Immunol.* 152:3913-3924, 1994). Peptide binding to HLA-A11 can be modulated by substitutions at primary and/or secondary anchor positions, preferably choosing respective residues specified for the motif.

Representative peptide epitopes that comprise the A11 motif are set forth in Table XVII; peptide epitopes comprising the A3 allele-specific motif are also present in this Table because of the extensive overlap between the A3 and A11 motif primary anchor specificities. Further, those peptide epitopes that comprise the A3 supermotif are also listed in Table IX.

III.D.14. HLA-A24 Motif

The HLA-A24 motif is characterized by the presence in peptide ligands of Y, F, W, or M as a primary anchor residue in position 2, and F, L, I, or W as a primary anchor residue at the C-terminal position of the epitope (see, e.g., Kondo et al., *J. Immunol.* 155:4307-4312, 1995; and Kubo et al., *J. Immunol.* 152:3913-3924, 1994). Peptide binding to HLA-A24 molecules can be modulated by substitutions at primary and/or secondary anchor positions; preferably choosing respective residues specified for the motif.

Representative peptide epitopes that comprise the A24 motif are set forth in Table XVIII. These epitopes are also listed in Table X, which sets forth HLA-A24-supermotif-bearing peptides, as the primary anchor residues characterizing the A24 allele-specific motif comprise a subset of the A24 supermotif primary anchor residues.

Motifs Indicative of Class II HTL Inducing Peptide Epitopes

The primary and secondary anchor residues of the HLA class II peptide epitope supermotifs and motifs delineated below are summarized in Table III.

III.D.15. HLA DR-14-7 Supermotif

Motifs have also been identified for peptides that bind to three common HLA class II allele-specific HLA molecules: HLA DRB1*0401, DRB1*0101, and DRB1*0701 (see, e.g., the review by Southwood et al *J. Immunology* 160:3363-3373,1998). Collectively, the common residues from these motifs delineate the HLA DR-1-4-7 supermotif Peptides that bind to these DR molecules carry a supermotif characterized by a large aromatic or hydrophobic residue (Y, F, W, L, I, V, or M) as a primary anchor residue in position 1, and a small, non-charged residue (S, T, C, A, P, V, I, L, or M) as a primary anchor residue in position 6 of a 9-mer core region. Allele-specific secondary effects and secondary anchors for each of these HLA types have also been identified (Southwood et al., supra). These are set forth in Table III. Peptide binding to HLA-DRB1*0401, DRB1*0101, and/or DRB1*0701 can be modulated by substitutions at primary and/or secondary anchor positions, preferably choosing respective residues specified for the supermotif.

Representative 9-mer epitopes comprising the DR-1-4-7 supermotif, wherein position 1 of the supermotif is at position 1 of the nine-residue core, are set forth in Table XIX. Exemplary epitopes of 15 amino acids in length that comprises the nine residue core include the three residues on either side that flank the nine residue core. HTL epitopes that comprise the core sequences can also be of lengths other than 15 amino acids, supra. Accordingly, epitopes of the invention include sequnces that typically comprise the nine residue core plus 1, 2, 3 (as in the exemplary 15-mer), 4, or 5 flanking residues on either side of the nine residue core.

III.D.16. HLA DR3 Motifs

Two alternative motifs (i.e., submotifs) characterize peptide epitopes that bind to HLA-DR3 molecules (see, e.g., Geluk et al., *J. Immunol.* 152:5742, 1994). In the first motif (submotif DR3A) a large, hydrophobic residue (L, 1, V, M, F, or Y) is present in anchor position 1 of a 9-mer core, and D is present as an anchor at position 4, towards the carboxyl terminus of the epitope. As in other class II motifs, core position 1 may or may not occupy the peptide N-terminal position.

The alternative DR3 submotif provides for lack of the large, hydrophobic residue at anchor position 1, and/or lack of the negatively charged or amide-like anchor residue at position 4, by the presence of a positive charge at position 6 towards the carboxyl terminus of the epitope. Thus, for the alternative allele-specific DR3 motif (submotif DR3B): L, I, V, M, F, Y, A, or Y is present at anchor position 1; D, N, Q, E, S, or T is present at anchor position 4; and K, R, or H is present at anchor position 6. Peptide binding to HLA-DR3 can be modulated by substitutions at primary and/or secondary anchor positions, preferably choosing respective residues specified for the motif.

Representative 9-mer epitopes corresponding to a nine residue sequence comprising the DR3a and DR3b submotifs (wherein position 1 of the motif is at position 1 of the nine residue core) are set forth in Table XXa and b. Exemplary epitopes of 15 amino acids in length that comprises the nine residue core include the three residues on either side that flank the nine residue core. HTL epitopes that comprises the cores sequences can also be of lengths other than 15 amino acids, supra. Accordingly, epitopes of the invention include sequnces that typically comprise the nine residue core plus 1, 2, 3 (as in the exemplary 15-mer), 4, or 5 flanking residues on either side of the nine residue core.

Each of the HLA class I or class II epitopes set out in the Tables herein are deemed singly to be an inventive aspect of this application. Further, it is also an inventive aspect of this application that each epitope may be used in combination with any other epitope.

III.E. Enhancing Population Coverage of the Vaccine

Vaccines that have broad population coverage are preferred because they are more commercially viable and generally applicable to the most people. Broad population coverage can be obtained using the peptides of the invention (and nucleic acid compositions that encode such peptides) through selecting peptide epitopes that bind to HLA alleles which, when considered in total, are present in most of the population. The Table below lists the overall frequencies of the HLA class I supertypes in various ethnicities (section a) and the combined population coverage achieved by the A2-, A3-, and B7-supertypes (section b). The A2-, A3-, and B7 supertypes are each present on the average of over 40% in each of these five major ethnic groups. Coverage in excess of 80% is achieved with a combination of these supermotifs. These results suggest that effective and non-ethnically biased population coverage is achieved upon use of a limited number of cross-reactive peptides. Although the population coverage reached with these three main peptide specificities is high, coverage can be expanded to reach 95% population coverage and above, and more easily achieve truly multispecific responses upon use of additional supermotif or allele-specific motif bearing peptides.

The B44-, A1-, and A24-supertypes are each present, on average, in a range from 25% to 40% in these major ethnic populations (section a). While less prevalent overall, the B27-, B58-, and B62 supertypes are each present with a frequency >25% in at least one major ethnic group (section a). In section b, the Table summarizes the estimated prevalence of combinations of HLA supertypes that have been identified in five major ethnic groups. The incremental coverage obtained by the inclusion of A 1,- A24-, and B44-supertypes to the A2, A3, and B7 coverage and coverage obtained with all of the supertypes described herein, is shown.

The data presented herein, together with the previous definition of the A2-, A3-, and B7-supertypes, indicates that all antigens, with the possible exception of A29, B8, and B46, can be classified into a total of nine HLA supertypes. By including epitopes from the six most frequent supertypes, an average population coverage of 99% is obtained for five major ethnic groups.

In particular, it has been noted that a significant number of epitopes derived from known non-viral tumor associated antigens (TAA) bind HLA class I with intermediate affinity ($IC_{50}$ in the 50-500 nM range). For example, it has been found that 8 of 15 known TAA peptides recognized by tumor infiltrating lymphocytes (TIL) or CTL bound in the 50-500 nM range. (These data are in contrast with estimates that 90% of known Population coverage with combined HLA Supertypes

| HLA-SUPERTYPES | PHENOTYPIC FREQUENCY | | | | | |
| --- | --- | --- | --- | --- | --- | --- |
| | Caucasian | North American Black | Japanese | Chinese | Hispanic | Average |
| a. Individual Supertypes | | | | | | |
| A2 | 45.8 | 39.0 | 42.4 | 45.9 | 43.0 | 43.2 |
| A3 | 37.5 | 42.1 | 45.8 | 52.7 | 43.1 | 44.2 |
| B7 | 43.2 | 55.1 | 57.1 | 43.0 | 49.3 | 49.5 |
| A1 | 47.1 | 16.1 | 21.8 | 14.7 | 26.3 | 25.2 |
| A24 | 23.9 | 38.9 | 58.6 | 40.1 | 38.3 | 40.0 |
| B44 | 43.0 | 21.2 | 42.9 | 39.1 | 39.0 | 37.0 |
| B27 | 28.4 | 26.1 | 13.3 | 13.9 | 35.3 | 23.4 |
| B62 | 12.6 | 4.8 | 36.5 | 25.4 | 11.1 | 18.1 |
| B58 | 10.0 | 25.1 | 1.6 | 9.0 | 5.9 | 10.3 |
| b. Combined Supertypes | | | | | | |
| A2, A3, B7 | 84.3 | 86.8 | 89.5 | 89.8 | 86.8 | 87.4 |
| A2, A3, B7, A24, B44, A1 | 99.5 | 98.1 | 100.0 | 99.5 | 99.4 | 99.3 |
| A2, A3, B7, A24, B44, A1, B27, B62, B58 | 99.9 | 99.6 | 100.0 | 99.8 | 99.9 | 99.8 |

III.F. Immune Response-Stimulating Peptide Analogs

In general, CTL and HTL responses to whole antigens are not directed against all possible epitopes. Rather, they are restricted to a few "immunodominant" determinants (Zinkernagel, et al., *Adv. Immunol.* 27:5159, 1979; Bennink, et al., *J. Exp. Med.* 168:19351939, 1988; Rawle, et al., *J. Immunol.* 146:3977-3984, 1991). It has been recognized that immunodominance (Benacerraf, et al., *Science* 175:273-279, 1972) could be explained by either the ability of a given epitope to selectively bind a particular HLA protein (determinant selection theory) (Vitiello, et al., *J. Immunol.* 131: 1635, 1983); Rosenthal, et al., *Nature* 267:156-158, 1977), or to be selectively recognized by the existing TCR (T cell receptor) specificities (repertoire theory) (Klein, J., IMMUNOLOGY, THE SCIENCE OF SELFNONSELF DISCRIMINATION, John Wiley & Sons, New York, pp. 270-310, 1982). It has been demonstrated that additional factors, mostly linked to processing events, can also play a key role in dictating, beyond strict immunogenicity, which of the many potential determinants will be presented as immunodominant (Sercarz, et al., *Annu. Rev. Immunol.* 11:729-766, 1993).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524-531, 1995). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

viral antigens were bound by HLA class I molecules with $IC_{50}$ of 50 nM or less, while only approximately 10% bound in the 50-500 nM range (Sette, et al., *J. Immunol.,* 153:558-5592, 1994). In the cancer setting this phenomenon is probably due to elimination or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow existing T cells to be recruited, which will then lead to a therapeutic or prophylactic response. However, the binding of HLA molecules to subdominant epitopes is often less vigorous than to dominant ones. Accordingly, there is a need to be able to modulate the binding affinity of particular immunogenic epitopes for one or more HLA molecules, and thereby to modulate the immune response elicited by the peptide, for example to prepare analog peptides which elicit a more vigorous response. This ability would greatly enhance the usefulness of peptide epitope-based vaccines and therapeutic agents.

Although peptides with suitable cross-reactivity among all alleles of a superfamily are identified by the screening procedures described above, cross-reactivity is not always as complete as possible, and in certain cases procedures to increase cross-reactivity of peptides can be useful; moreover, such procedures can also be used to modify other properties of the peptides such as binding affinity or peptide stability. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides which exhibit the broadest cross-reactivity patterns, can be produced in accordance with the teachings herein. The present concepts related to analog generation are set forth in greater detail in co-pending U.S. Ser. No. 09/226,775 filed Jan. 6, 1999.

In brief, the strategy employed utilizes the motifs or supermotifs which correlate with binding to certain HLA molecules. The motifs or supermotifs are defined by having primary anchors, and in many cases secondary anchors. Analog peptides can be created by substituting amino acid residues at primary anchor, secondary anchor, or at primary and secondary anchor positions. Generally, analogs are made for peptides that already bear a motif or supermotif. Preferred secondary anchor residues of supermotifs and motifs that have been defined for HLA class I and class II binding peptides are shown in Tables II and III, respectively.

For a number of the motifs or supermotifs in accordance with the invention, residues are defined which are deleterious to binding to allele-specific HLA molecules or members of HLA supertypes that bind the respective motif or supermotif (Tables II and III). Accordingly, removal of such residues that are detrimental to binding can be performed in accordance with the present invention. For example, in the case of the A3 supertype, when all peptides that have such deleterious residues are removed from the population of peptides used in the analysis, the incidence of cross-reactivity increased from 22% to 37% (see, e.g., Sidney, J. et al., *Hu. Immunol.* 45:79, 1996). Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

To ensure that an analog peptide, when used as a vaccine, actually elicits a CTL response to the native epitope in vivo (or, in the case of class II epitopes, elicits helper T cells that cross-react with the wild type peptides), the analog peptide may be used to immunize T cells in vitro from individuals of the appropriate HLA allele. Thereafter, the immunized cells' capacity to induce lysis of wild type peptide sensitized target cells is evaluated. It will be desirable to use as antigen presenting cells, cells that have been either infected, or transfected with the appropriate genes, or, in the case of class II epitopes only, cells that have been pulsed with whole protein antigens, to establish whether endogenously produced antigen is also recognized by the relevant T cells.

Another embodiment of the invention is to create analogs of weak binding peptides, to thereby ensure adequate numbers of cross-reactive cellular binders. Class I binding peptides exhibiting binding affinities of 500-5000 nM, and carrying an acceptable but suboptimal primary anchor residue at one or both positions can be "fixed" by substituting preferred anchor residues in accordance with the respective supertype. The analog peptides can then be tested for crossbinding activity.

Another embodiment for generating effective peptide analogs involves the substitution of residues that have an adverse impact on peptide stability or solubility in, e.g., a liquid environment. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g., the review by Sette et al., In: *Persistent Viral Infections*, Eds. R. Ahmed and I. Chen, John Wiley & Sons, England, 1999). Substitution of cysteine with α-amino butyric acid may occur at any residue of a peptide epitope, i.e. at either anchor or non-anchor positions.

III.G. Computer Screening of Protein Sequences from Disease-Related Antigens for Supermotif- or Motif-Bearing Peptides In order to identify supermotif- or motif-bearing epitopes in a target antigen, a native protein sequence, e.g., a tumor-associated antigen, or sequences from an infectious organism, or a donor tissue for transplantation, is screened using a means for computing, such as an intellectual calculation or a computer, to determine the presence of a supermotif or motif within the sequence. The information obtained from the analysis of native peptide can be used directly to evaluate the status of the native peptide or may be utilized subsequently to generate the peptide epitope.

Computer programs that allow the rapid screening of protein sequences for the occurrence of the subject supermotifs or motifs are encompassed by the present invention; as are programs that permit the generation of analog peptides. These programs are implemented to analyze any identified amino acid sequence or operate on an unknown sequence and simultaneously determine the sequence and identify motif-bearing epitopes thereof; analogs can be simultaneously determined as well. Generally, the identified sequences will be from a pathogenic organism or a tumor-associated peptide. For example, the target molecules considered herein include, without limitation, the E1, E2, E4, E5a, E5b, E6, E7, L1 and L2 proteins of HPV.

In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide, be conserved in a designated percentage, of the sequences evaluated for a specific protein antigen.

To target a broad population that may be infected with a number of different strains, it is preferable to include in vaccine compositions epitopes that are representative of HPV antigen sequences from different HPV strains. As appreciated by those in the art, regions with greater or lessor degrees of conservancy among HPv strains can be employed as appropriate for a given antigenic target.

It is important that the selection criteria utilized for prediction of peptide binding are as accurate as possible, to correlate most efficiently with actual binding. Prediction of peptides that bind, for example, to HLA-A*0201, on the basis of the presence of the appropriate primary anchors, is positive at about a 30% rate (see, e.g., Ruppert, J. et al. *Cell* 74:929, 1993). However, by extensively analyzing peptide-HLA binding data disclosed herein, data in related patent applications, and data in the art, the present inventors have developed a number of allele-specific polynomial algorithms that dramatically increase the predictive value over identification on the basis of the presence of primary anchor residues alone. These algorithms take into account not only the presence or absence of primary anchors, but also consider the positive or deleterious presence of secondary anchor residues (to account for the impact of different amino acids at different positions). The algorithms are essentially based on the premise that the overall affinity (or ΔG) of peptide-HLA interactions can be approximated as a linear polynomial function of the type:

$$\Delta G = a_{1i} \times a_{2i} \times a_{3i} \ldots \times a_{ni}$$

where $a_{ji}$ is a coefficient that represents the effect of the presence of a given amino acid (j) at a given position (i) along the sequence of a peptide of n amino acids. An important assumption of this method is that the effects at each position are essentially independent of each other. This assumption is justified by studies that demonstrated that peptides are bound to HLA molecules and recognized by T cells in essentially an extended conformation. Derivation of specific algorithm coefficients has been described, for example, in Gulukota, K. et al., *J. Mol. Biol.* 267:1258, 1997.

Additional methods to identify preferred peptide sequences, which also make use of specific motifs, include the use of neural networks and molecular modeling programs (see, e.g., Milik et al., *Nature Biotechnology* 16:753, 1998; Altuvia et al., *Hum. Immunol.* 58:1, 1997; Altuvia et al, *J. Mol. Biol.* 249:244, 1995; Buus, S. *Curr. Opin. Immunol.* 11:209-213, 1999; Brusic, V. et al., *Bioinformatics* 14:121-130, 1998; Parker et al., *J. Immunol.* 152:163, 1993; Meister et al., *Vaccine* 13:581, 1995; Hammer et al., *J. Exp. Med.* 180:2353, 1994; Sturniolo et al., *Nature Biotechnol.* 17:555 1999).

For example, it has been shown that in sets of A*0201 motif-bearing peptides containing at least one preferred secondary anchor residue while avoiding the presence of any deleterious secondary anchor residues, 69% of the peptides will bind A*0201 with an $IC_{50}$ less than 500 nM (Ruppert, J. et al. *Cell* 74:929, 1993). These algorithms are also flexible in that cut-off scores may be adjusted to select sets of peptides with greater or lower predicted binding properties, as desired.

In utilizing computer screening to identify peptide epitopes, a protein sequence or translated sequence may be analyzed using software developed to search for motifs, for example the "FINDPATTERNS" program (Devereux, et al. *Nucl. Acids Res.* 12:387-395,1984) or MotifSearch 1.4 software program (D. Brown, San Diego, Calif.) to identify potential peptide sequences containing appropriate HLA binding motifs. The identified peptides can be scored using customized polynomial algorithms to predict their capacity to bind specific HLA class I or class II alleles. As appreciated by one of ordinary skill in the art, a large array of computer programming software and hardware options are available in the relevant art which can be employed to implement the motifs of the invention in order to evaluate (e.g., without limitation, to identify epitopes, identify epitope concentration per peptide length, or to generate analogs) known or unknown peptide sequences.

In accordance with the procedures described above, HPV peptide epitopes that are able to bind HLA supertype groups or allele-specific HLA molecules have been identified (Tables VII-XX).

III.H. Preparation of Peptide Epitopes

Peptides in accordance with the invention can be prepared synthetically, by recombinant DNA technology or chemical synthesis, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention can be a variety of lengths, and either in their neutral (uncharged) forms or in forms which are salts. The peptides in accordance with the invention are either free of modifications such as glycosylation, side chain oxidation, or phosphorylation; or they contain these modifications, subject to the condition that modifications do not destroy the biological activity of the peptides as described herein.

When possible, it may be desirable to optimize HLA class I binding epitopes of the invention, such as can be used in a polyepitopic construct, to a length of about 8 to about 13 amino acid residues, often 8 to 11, preferably 9 to 10. HLA class II binding peptide epitopes of the invention may be optimized to a length of about 6 to about 30 amino acids in length, preferably to between about 13 and about 20 residues. Preferably, the peptide epitopes are commensurate in size with endogenously processed pathogen-derived peptides or tumor cell peptides that are bound to the relevant HLA molecules, however, the identification and preparation of peptides that comprise epitopes of the invention can also be carried out using the techniques described herein.

In alternative embodiments, epitopes of the invention can be linked as a polyepitopic peptide, or as a minigene that encodes a polyepitopic peptide.

In another embodiment, it is preferred to identify native peptide regions that contain a high concentration of class I and/or class II epitopes. Such a sequence is generally selected on the basis that it contains the greatest number of epitopes per amino acid length. It is to be appreciated that epitopes can be present in a nested or overlapping manner, e.g. a 10 amino acid long peptide could contain two 9 amino acid long epitopes and one 10 amino acid long epitope; upon intracellular processing, each epitope can be exposed and bound by an HLA molecule upon administration of such a peptide. This larger, preferably multi-epitopic, peptide can be generated synthetically, recombinantly, or via cleavage from the native source.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. (See, for example, Stewart & Young, SOLID PHASE PEPTIDE SYNTHESIS, 2D. ED., Pierce Chemical Co., 1984). Further, individual peptide epitopes can be joined using chemical ligation to produce larger peptides that are still within the bounds of the invention.

Alternatively, recombinant DNA technology can be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant polypeptides which comprise one or more peptide sequences of the invention can be used to present the appropriate T cell epitope.

The nucleotide coding sequence for peptide epitopes of the preferred lengths contemplated herein can be synthesized by chemical techniques, for example, the phosphotriester method of Matteucci, et al., *J. Am. Chem. Soc.* 103:3185 (1981). Peptide analogs can be made simply by substituting the appropriate and desired nucleic acid base(s) for those that encode the native peptide sequence; exemplary nucleic acid substitutions are those that encode an amino acid defined by the motifs/supermotifs herein. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

III.I. Assays to Detect T-Cell Responses

Once HLA binding peptides are identified, they can be tested for the ability to elicit a T-cell response. The preparation and evaluation of motif-bearing peptides are described in PCT publications WO 94/20127 and WO 94/03205. Briefly, peptides comprising epitopes from a particular antigen are synthesized and tested for their ability to bind to the appropriate HLA proteins. These assays may involve evaluating the binding of a peptide of the invention to purified HLA class I molecules in relation to the binding of a radioiodinated reference peptide. Alternatively, cells expressing empty class I molecules (i.e. lacking peptide therein) may be evaluated for peptide binding by immunofluorescent staining and flow microfluorimetry. Other assays that may be used to evaluate peptide binding include peptide-dependent class I assembly assays and/or the inhibition of CTL recognition by peptide competition. Those peptides that bind to the class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease.

Analogous assays are used for evaluation of HLA class II binding peptides. HLA class II motif-bearing peptides that are shown to bind, typically at an affinity of 1000 nM or less, are further evaluated for the ability to stimulate HTL responses.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant non-human mammalian cell lines that are deficient in their ability to load class I molecules with internally processed peptides and that have been transfected with the appropriate human class I gene, may be used to test for the capacity of the peptide to induce in vitro primary CTL responses.

Peripheral blood mononuclear cells (PBMCs) may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Additionally, a method has been devised which allows direct quantification of antigen-specific T cells by staining with Fluorescein-labelled HLA tetrameric complexes (Altman, J. D. et al., $Proc. Natl. Acad. Sci. USA$ 90:10330, 1993; Altman, J. D. et al., $Science$ 274:94, 1996). Other relatively recent technical developments include staining for intracellular lymphokines, and interferon release assays or ELISPOT assays. Tetramer staining, intracellular lymphokine staining and ELISPOT assays all appear to be at least 10-fold more sensitive than more conventional assays (Lalvani, A. et al., $J. Exp. Med.$ 186:859, 1997; Dunbar, P. R. et al., $Curr. Biol.$ 8:413, 1998; Murali-Krishna, K. et al., $Immunity$ 8:177, 1998).

HTL activation may also be assessed using such techniques known to those in the art such as T cell proliferation and secretion of lymphokines, e.g. IL-2 (see, e.g. Alexander et al., Immunity 1:751-761, 1994).

Alternatively, immunization of HLA transgenic mice can be used to determine immunogenicity of peptide epitopes. Several transgenic mouse models including mice with human A2.1, A11 (which can additionally be used to analyze HLA-A3 epitopes), and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. Mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

III.J. Use of Peptide Epitopes as Diagnostic Agents and for Evaluating Immune Responses In one aspect of the invention, HLA class I and class II binding peptides as described herein can be used as reagents to evaluate an immune response. The immune response to be evaluated is induced by using as an immunogen any agent that may result in the production of antigen-specific CTLs or HTLs that recognize and bind to the peptide epitope(s) to be employed as the reagent. The peptide reagent need not be used as the immunogen. Assay systems that are used for such an analysis include relatively recent technical developments such as tetramers, staining for intracellular lymphokines and interferon release assays, or ELISPOT assays.

For example, a peptide of the invention is used in a tetramer staining assay to assess peripheral blood mononuclear cells for the presence of antigen-specific CTLs following exposure to a pathogen or immunogen. The HLA-tetrameric complex is used to directly visualize antigen-specific CTLs (see, e.g., Ogg et al., $Science$ 279:2103-2106, 1998; and Altman et al., $Science$ 174:94-96, 1996) and determine the frequency of the antigen-specific CTL population in a sample of peripheral blood mononuclear cells.

A tetramer reagent using a peptide of the invention is generated as follows: A peptide that binds to an HLA molecule is refolded in the presence of the corresponding HLA heavy chain and 2-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells can then be readily identified, for example, by flow cytometry. Such procedures are used for diagnostic or prognostic purposes. Cells identified by the procedure can also be used for therapeutic purposes.

Peptides of the invention are also used as reagents to evaluate immune recall responses. (see, e.g., Bertoni et al., *J. Clin. Invest.* 100:503-513, 1997 and Penna et al., *J. Exp. Med.* 174:1565-1570, 1991.) For example, patient PBMC samples from individuals infected with HPV are analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for CTL or for HTL activity.

The peptides are also used as reagents to evaluate the efficacy of a vaccine. PBMCs obtained from a patient vaccinated with an immunogen are analyzed using, for example, either of the methods described above. The patient is HLA typed, and peptide epitope reagents that recognize the allele-specific molecules present in that patient are selected for the analysis. The immunogenicity of the vaccine is indicated by the presence of HPV epitope-specific CTLs and/or HTLs in the PBMC sample.

The peptides of the invention are also be used to make antibodies, using techniques well known in the art (see, e.g. *Current Protocols in Immunology*, Wiley/Greene, NY; and *Antibodies A Laboratory Manual Harlow*, Harlow and Lane, Cold Spring Harbor Laboratory Press, 1989), which may be useful as reagents to diagnose HPV infection. Such antibodies include those that recognize a peptide in the context of an HLA molecule, i.e., antibodies that bind to a peptide-MHC complex.

III.K. Vaccine Compositions

Vaccines and methods of preparing vaccines that contain an immunogenically effective amount of one or more peptides as described herein are further embodiments of the invention. Once appropriately immunogenic epitopes have been defined, they can be sorted and delivered by various means, herein referred to as "vaccine" compositions. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

Vaccine compositions of the invention include nucleic acid-mediated modalities. DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, for example, as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (*Bacille Calmette Guerin*). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine (P₃CSS).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later infection, or at least partially resistant to developing an ongoing chronic infection, or derives at least some therapeutic benefit when the antigen was tumor-associated.

In some embodiments, it may be desirable to combine the class I peptide components with components that induce or facilitate neutralizing antibody and or helper T cell responses to the target antigen of interest. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo.

Vaccine compositions, either DNA- or peptide-based, can also be administered in vivo in combination with dendritic cell mobilization whereby loading of dendritic cells occurs in vivo.

Antigenic peptides are used to elicit a CTL and/or HTL response ex vivo, as well. The resulting CTL or HTL cells, can be used to treat chronic infections, or tumors in patients that do not respond to other conventional forms of therapy, or will not respond to a therapeutic vaccine peptide or nucleic acid in accordance with the invention. Ex vivo CTL or HTL responses to a particular antigen (infectious or tumor-associated antigen) are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (an infected cell or a tumor cell). Transfected dendritic cells may also be used as antigen presenting cells.

The vaccine compositions of the invention may also be used in combination with other procedures to remove warts or treat HPV infections. Such procedures include cryosurgery, application of caustic agents, electrodessication, surgical excision and laser ablation (Fauci et al. *HARRISON'S PRINCIPLES OF INTERNAL MEDICINE*, 14th ED., McGraw-Hill Co., Inc, 1998), as well as treatment with antiviral drugs such as interferon-α (see, e.g., Stellato, G., et al., *Clin. Diagn. Virol.* 7(3):167-72 (1997)) or interferon-inducing drugs such as imiquimod. Topical antimetabolites such a 5-fluorouracil may also be applied.

In patients with HPV-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles are balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with clearance of HPV infection or tumor clearance. For HLA Class I this includes 3-4 epitopes that come from at least one TAA. For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs as described, e.g., in Example 15.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope. When selecting epitopes for infectious disease-related antigens it is preferable to select either native or analoged epitopes.

5.) Of particular relevance are epitopes referred to as "nested epitopes." Nested epitopes occur where at least two epitopes overlap in a given peptide sequence. A nested peptide sequence can comprise both HLA class I and HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

8.) When selecting an array of epitopes of an infectious agent, it is preferred that at least some of the epitopes are derived from early and late proteins. The early proteins of HPV are expressed when the virus is replicating, either following acute or dormant infection. Therefore, it is particularly preferred to use epitopes from early stage proteins to alleviate disease manifestations at the earliest stage possible.

III.K.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, e.g., co-pending application U.S. Ser. No. 09/311,784; Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived from multiple regions of one or more HPV antigens, the PADRE universal helper T cell epitope (or multiple HTL epitopes from HPV antigens), and an endoplasmic reticulum-translocating signal sequence can be engineered. A vaccine may also comprise epitopes that are derived from other TAAs.

The immunogenicity of a multi-epitopic minigene can be tested in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in E. coli, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

III.K.2. Combinations of CTL Peptides With Helper Peptides

Vaccine compositions comprising CTL peptides of the invention can be modified to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. The use of T helper epitopes in conjunction with CTL epitopes to enhance immunogenicity is illustrated, for example, in the co-pending applications U.S. Ser. No. 08/820,360, U.S. Ser. No. 08/197,484, and U.S. Ser. No. 08/464,234.

Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in the majority of the population. This can be accomplished by selecting peptides that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830-843 (QYIKANSKFIGITE; SEQ ID NO:67), Plasmodium falciparum circumsporozoite (CS) protein at positions 378-398 (DIEKKIAKMEKASS-VFNVVNS; SEQ ID NO:68), and Streptococcus 18 kD protein at positions 116 (GAVDSILGGVATYGAA; SEQ ID NO:69). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO:70), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

III.K.3. Combinations of CTL Peptides With T Cell Priming Agents

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, $E.$ $coli$ lipoproteins, such as tripalmitoyl-S-glycerylcysteinly-seryl-serine ($P_3CSS$) can be used to prime virus specific CTL when covalently attached to an appropriate peptide (see, e.g., Deres, et al., $Nature$ 342:561, 1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses.

CTL and/or HTL peptides can also be modified by the addition of amino acids to the termini of a peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly class I peptides. However, it is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxyl amidation, e.g., ammonia, methylamine, etc. In some instances these modifications may provide sites for linking to a support or other molecule.

IV.J.4. Vaccine Compositions Comprising DC Pulsed With CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin (Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to one or more HPV antigens of interest. Optionally, a helper T cell (HTL) peptide such as a PADRE family molecule, can be included to facilitate the CTL response. Thus, a vaccine in accordance with the invention, preferably comprising epitopes from multiple HPV antigens, is used to treat HPV infection or cancer resulting from HPV infection.

III.L. Administration of Vaccines for Therapeutic or Prophylactic Purposes

The peptides of the present invention and pharmaceutical and vaccine compositions of the invention are typically used to treat and/or prevent cancer associated with HPV infection. Vaccine compositions containing the peptides of the invention are administered to a patient infected with HPV or to an individual susceptible to, or otherwise at risk for, HPV infection to elicit an immune response against HPV antigens and thus enhance the patient's own immune response capabilities.

As noted above, peptides comprising CTL and/or HTL epitopes of the invention induce immune responses when presented by HLA molecules and contacted with a CTL or HTL specific for an epitope comprised by the peptide. The peptides (or DNA encoding them) can be administered individually or as fusions of one or more peptide sequences. The manner in which the peptide is contacted with the CTL or HTL is not critical to the invention. For instance, the peptide can be contacted with the CTL or HTL either in vivo or in vitro. If the contacting occurs in vivo, the peptide itself can be administered to the patient, or other vehicles, e.g., DNA vectors encoding one or more peptides, viral vectors encoding the peptide(s), liposomes and the like, can be used, as described herein.

When the peptide is contacted in vitro, the vaccinating agent can comprise a population of cells, e.g., peptide-pulsed dendritic cells, or HPV-specific CTLs, which have been induced by pulsing antigen-presenting cells in vitro with the peptide or by transfecting antigen-presenting cells with a minigene of the invention. Such a cell population is subsequently administered to a patient in a therapeutically effective dose.

In therapeutic applications, peptide and/or nucleic acid compositions are administered to a patient in an amount sufficient to elicit an effective CTL and/or HTL response to the virus antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already infected with HPV. The peptides or DNA encoding them can be administered individually or as fusions of one or more peptide sequences. HPV-infected patients, with or without neoplasia, can be treated with the immunogenic peptides separately or in conjunction with other treatments, such as surgery, as appropriate.

For therapeutic use, administration should generally begin at the first diagnosis of HPV infection or HPV-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses HPV antigens, a vaccine comprising HPV-specific CTL may be more efficacious in killing tumor cells in patient with advanced disease than alternative embodiments.

Where susceptible individuals are identified prior to or during infection, the composition can be targeted to them, thus minimizing the need for administration to a larger population. Susceptible populations include those individuals who are sexually active.

The peptide or other compositions used for the treatment or prophylaxis of HPV infection can be used, e.g., in persons who have not manifested symptoms, e.g., genital warts or neoplastic growth. In this context, it is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the viral infection, or neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., Remington's Pharmaceutical Sciences, $17^{th}$ Edition, A. Gennaro, Editor, Mack Publising Co., Easton, Pa., 1985).

The peptides of the invention, and/or nucleic acids encoding the peptides, can also be administered via liposomes, which may also serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

III.M. HLA Expression: Implications for T Cell-Based Immunotherapy

Disease Progression in Cancer and Infectious Disease

It is well recognized that a dynamic interaction between exists between host and disease, both in the cancer and infectious disease settings. In the infectious disease setting, it is well established that pathogens evolve during disease. The strains that predominate early in HIV infection are different from the ones that are associated with AIDS and later disease stages (NS versus S strains). It has long been hypothesized that pathogen forms that are effective in establishing infection may differ from the ones most effective in terms of replication and chronicity.

Similarly, it is widely recognized that the pathological process by which an individual succumbs to a neoplastic disease is complex. During the course of disease, many changes occur in cancer cells. The tumor accumulates alterations which are in part related to dysfunctional regulation of growth and differentiation, but also related to maximizing its growth potential, escape from drug treatment and/or the body's immunosurveillance. Neoplastic disease results in the accumulation of several different biochemical alterations of cancer cells, as a function of disease progression. It also results in significant levels of intra- and inter-cancer heterogeneity, particularly in the late, metastatic stage.

Familiar examples of cellular alterations affecting treatment outcomes include the outgrowth of radiation or chemotherapy resistant tumors during the course of therapy. These examples parallel the emergence of drug resistant viral strains as a result of aggressive chemotherapy, e.g., of chronic HBV and HIV infection, and the current resurgence of drug resistant organisms that cause Tuberculosis and Malaria. It appears that significant heterogeneity of responses is also associated with other approaches to cancer therapy, including anti-angiogenesis drugs, passive antibody immunotherapy, and active T cell-based immunotherapy. Thus, in view of such phenomena, epitopes from multiple disease-related antigens can be used in vaccines and therapeutics thereby counteracting the ability of diseased cells to mutate and escape treatment.

The Interplay Between Disease and the Immune System

One of the main factors contributing to the dynamic interplay between host and disease is the immune response mounted against the pathogen, infected cell, or malignant cell. In many conditions such immune responses control the disease. Several animal model systems and prospective studies of natural infection in humans suggest that immune responses against a pathogen can control the pathogen, prevent progression to severe disease and/or eliminate the pathogen. A common theme is the requirement for a multispecific T cell response, and that narrowly focused responses appear to be less effective. These observations guide skilled artisan as to embodiments of methods and compositions of the present invention that provide for a broad immune response.

In the cancer setting there are several findings that indicate that immune responses can impact neoplastic growth:

First, the demonstration in many different animal models, that anti-tumor T cells, restricted by MHC class I, can prevent or treat tumors.

Second, encouraging results have come from immunotherapy trials.

Third, observations made in the course of natural disease correlated the type and composition of T cell infiltrate within tumors with positive clinical outcomes (Coulie P G, et al. Antitumor immunity at work in a melanoma patient In *Advances in Cancer Research,* 213-242, 1999).

Finally, tumors commonly have the ability to mutate, thereby changing their immunological recognition. For example, the presence of monospecific CTL was also correlated with control of tumor growth, until antigen loss emerged (Riker A, et al., Immune selection after antigen-specific immunotherapy of melanoma *Surgery*, August: 126(2): 112-20, 1999; Marchand M, et al., Tumor regressions observed in patients with metastatic melanoma treated with an antigenic peptide encoded by gene MAGE-3 and presented by HLA-A1 *Int. J. Cancer* 80(2):219-30, Jan. 18, 1999). Similarly, loss of beta 2 microglobulin was detected in 5/13 lines established from melanoma patients after receiving immunotherapy at the NCI (Restifo N P, et al., Loss of functional Beta2-microglobulin in metastatic melanomas from five patients receiving immunotherapy *Journal of the National Cancer Institute*, Vol. 88 (2), 100-108, January 1996). It has long been recognized that HLA class I is frequently altered in various tumor types. This has led to a hypothesis that this phenomenon might reflect immune pressure exerted on the tumor by means of class I restricted CTL. The extent and degree of alteration in HLA class I expression appears to be reflective of past immune pressures, and may also have prognostic value (van Duinen S G, et al., Level of HLA antigens in locoregional metastases and clinical course of the disease in patients with melanoma *Cancer Research* 48, 1019-1025, February 1988; Möller P, et al., Influence of major histocompatibility complex class I and II antigens on survival in colorectal carcinoma *Cancer Research* 51, 729-736, January 1991). Taken together, these observations provide a rationale for immunotherapy of cancer and infectious disease, and suggest that effective strategies need to account for the complex series of pathological changes associated with disease.

The Three Main Types of Alterations in HLA Expression in Tumors and Their Functional Significance The level and pattern of expression of HLA class I antigens in tumors has been studied in many different tumor types and alterations have been reported in all types of tumors studied. The molecular mechanisms underlining HLA class I alterations have been demonstrated to be quite heterogeneous. They include alterations in the TAP/processing pathways, mutations of β2-microglobulin and specific HLA heavy chains, alterations in the regulatory elements controlling over class I expression and loss of entire chromosome sections. There are several reviews on this topic, see, e.g.,: Garrido F, et al., Natural history of HLA expression during turnout development *Immunol Today* 14(10):491-499, 1993; Kaklamanis L, et al., Loss of HLA class-I alleles, heavy chains and β2-microglobulin in colorectal cancer *Int. J. Cancer*, 51(3):379-85, May 28, 1992. There are three main types of HLA Class I alteration (complete loss, allele-specific loss and decreased expression). The functional significance of each alteration is discussed separately:

Complete Loss of HLA Expression

Complete loss of HLA expression can result from a variety of different molecular mechanisms, reviewed in (Algarra I, et al., The HLA crossroad in tumor immunology *Human Immunology* 61, 65-73, 2000; Browning M, et al., Mechanisms of loss of HLA class I expression on colorectal tumor cells *Tissue Antigens* 47:364-371, 1996; Ferrone S, et al., Loss of HLA class I antigens by melanoma cells: molecular mechanisms, functional significance and clinical relevance *Immunology Today*, 16(10): 487494, 1995; Garrido F, et al., Natural history of HLA expression during tumour development *Immunology Today* 14(10):491499, 1993; Tait, B D, HLA Class I expression on human cancer cells: Implications for effective immunotherapy *Hum Immunol* 61, 158-165, 2000). In functional terms, this type of alteration has several important implications.

While the complete absence of class I expression will eliminate CTL recognition of those tumor cells, the loss of HLA class I will also render the tumor cells extraordinary sensitive to lysis from NK cells (Ohnmacht, GA, et al., Heterogeneity in expression of human leukocyte antigens and melanoma-associated antigens in advanced melanoma *J Cellular Phys* 182:332-338, 2000; Liunggren H G, et al., Host resistance directed selectively against H-2 deficient lymphoma variants: Analysis of the mechanism *J. Exp. Med., Dec* 1;162(6):1745-59, 1985; Maio M, et al., Reduction in susceptibility to natural killer cell-mediated lysis of human FO-1 melanoma cells after induction of HLA class I antigen expression by transfection with B2m gene *J. Clin. Invest*. 88(1):282-9, July 1991; Schrier P I, et al., Relationship between myc oncogene activation and MHC class I expression *Adv. Cancer Res.*, 60:181-246, 1993).

The complementary interplay between loss of HLA expression and gain in NK sensitivity is exemplified by the classic studies of Coulie and coworkers (Coulie, P G, et al., Antitumor immunity at work in a melanoma patient. In *Advances in Cancer Research*, 213-242, 1999) which described the evolution of a patient's immune response over the course of several years. Because of increased sensitivity to NK lysis, it is predicted that approaches leading to stimulation of innate immunity in general and NK activity in particular would be of special significance. An example of such approach is the induction of large amounts of dendritic cells (DC) by various hematopoietic growth factors, such as Flt3 ligand or ProGP. The rationale for this approach resides in the well known fact that dendritic cells produce large amounts of IL-12, one of the most potent stimulators for innate immunity and NK activity in particular. Alternatively, IL-12 is administered directly, or as nucleic acids that encode it. In this light, it is interesting to note that Flt3 ligand treatment results in transient tumor regression of a class I negative prostate murine cancer model (Ciavarra R P, et al., Flt3-Ligand induces transient tumor regression in an ectopic treatment model of major histocompatibility complex-negative prostate cancer *Cancer Res* 60:2081-84, 2000). In this context, specific anti-tumor vaccines in accordance with the invention synergize with these types of hematopoietic growth factors to facilitate both CTL and NK cell responses, thereby appreciably impairing a cell's ability to mutate and thereby escape efficacious treatment. Thus, an embodiment of the present invention comprises a composition of the invention together with a method or composition that augments functional activity or numbers of NK cells. Such an embodiment can comprise a protocol that provides a composition of the invention sequentially with an NK-inducing modality, or contemporaneous with an NK-inducing modality.

Secondly, complete loss of HLA frequently occurs only in a fraction of the tumor cells, while the remainder of tumor cells continue to exhibit normal expression. In functional terms, the tumor would still be subject, in part, to direct attack from a CTL response; the portion of cells lacking HLA subject to an NK response. Even if only a CTL response were used, destruction of the HLA expressing fraction of the tumor has dramatic effects on survival times and quality of life.

It should also be noted that in the case of heterogeneous HLA expression, both normal HLA-expressing as well as defective cells are predicted to be susceptible to immune destruction based on "bystander effects." Such effects were demonstrated, e.g., in the studies of Rosendahl and colleagues that investigated in vivo mechanisms of action of antibody targeted superantigens (Rosendahl A, et al., Perforin and IFN-gamma are involved in the antitumor effects of antibody-targeted superantigens *J. Immunol.* 160(11):5309-13, Jun. 1, 1998). The bystander effect is understood to be mediated by cytokines elicited from, e.g., CTLs acting on an HLA-bearing target cell, whereby the cytokines are in the environment of other diseased cells that are concomitantly killed.

Allele-specific Loss

One of the most common types of alterations in class I molecules is the selective loss of certain alleles in individuals heterozygous for HLA. Allele-specific alterations might reflect the tumor adaptation to immune pressure, exerted by an immunodominant response restricted by a single HLA restriction element. This type of alteration allows the tumor to retain class I expression and thus escape NK cell recognition, yet still be susceptible to a CTL-based vaccine in accordance with the invention which comprises epitopes corresponding to the remaining HLA type. Thus, a practical solution to overcome the potential hurdle of allele-specific loss relies on the induction of multispecific responses. Just as the inclusion of multiple disease-associated antigens in a vaccine of the invention guards against mutations that yield loss of a specific disease antigens, simultaneously targeting multiple HLA specificities and multiple disease-related antigens prevents disease escape by allele-specific losses.

Decrease in Expression (Allele-specific or Not)

The sensitivity of effector CTL has long been demonstrated (Brower, R C, et al., Minimal requirements for peptide mediated activation of CD8+CTL *Mol. Immunol.*, 31;1285-93, 1994; Chriustnick, ET, et al. Low numbers of MHC class I-peptide complexes required to trigger a T cell response *Nature* 352:67-70, 1991; Sykulev, Y, et al., Evidence that a single peptide-MHC complex on a target cell can elicit a cytolytic T cell response *Immunity*, 4(6):565-71, June 1996). Even a single peptide/MHC complex can result in tumor cells lysis and release of anti-tumor lymphokines. The biological significance of decreased HLA expression and possible tumor escape from immune recognition is not fully known.

Nevertheless, it has been demonstrated that CTL recognition of as few as one MHC/peptide complex is sufficient to lead to tumor cell lysis.

Further, it is commonly observed that expression of HLA can be upregulated by gamma IFN, commonly secreted by effector CTL. Additionally, HLA class I expression can be induced in vivo by both alpha and beta IFN (Halloran, et al. Local T cell responses induce widespread MHC expression. *J Immunol* 148:3837, 1992; Pestka, S, et al., Interferons and their actions *Annu. Rev. Biochem.* 56:727-77, 1987). Conversely, decreased levels of HLA class I expression also render cells more susceptible to NK lysis.

With regard to gamma IFN, Torres et al (Torres, M J, et al., Loss of an HLA haplotype in pancreas cancer tissue and its corresponding tumor derived cell line. *Tissue Antigens* 47:372-81, 1996) note that HLA expression is upregulated by gamma IFN in pancreatic cancer, unless a total loss of haplotype has occurred. Similarly, Rees and Mian note that allelic deletion and loss can be restored, at least partially, by cytokines such as IFN-gamma (Rees, R., et al. Selective MHC expression in tumours modulates adaptive and innate antitumour responses *Cancer Immunol Immunother* 48:374-81, 1999). It has also been noted that IFN-gamma treatment results in upregulation of class I molecules in the majority of the cases studied (Browning M, et al., Mechanisms of loss of HLA class I expression on colorectal tumor cells. *Tissue Antigens* 47:364-71, 1996). Kaklamakis, et al. also suggested that adjuvant immunotherapy with IFN-gamma may be beneficial in the case of HLA class I negative tumors (Kaklamanis L, Loss of transporter in antigen processing 1 transport protein and major histocompatibility complex class I molecules in metastatic versus primary breast cancer. *Cancer Research* 55:5191-94, November 1995). It is important to underline that IFN-gamma production is induced and self-amplified by local inflammation/immunization (Halloran, et al. Local T cell responses induce widespread MHC expression *J. Immunol* 148:3837, 1992), resulting in large increases in MHC expressions even in sites distant from the inflammatory site.

Finally, studies have demonstrated that decreased HLA expression can render tumor cells more susceptible to NK lysis (Ohnmacht, G A, et al., Heterogeneity in expression of human leukocyte antigens and melanoma-associated antigens in advanced melanoma *J Cellular Phys* 182:332-38, 2000; Liunggren H G, et al., Host resistance directed selectively against H-2 deficient lymphoma variants: Analysis of the mechanism *J. Exp. Med.*, 162(6):1745-59, Dec. 1, 1985; Maio M, et al., Reduction in susceptibility to natural killer cell-mediated lysis of human FO-1 melanoma cells after induction of HLA class I antigen expression by transfection with β2m gene *J. Clin. Invest.* 88(1):282-9, July 1991; Schrier P I, et al., Relationship between myc oncogene activation and MHC class I expression *Adv. Cancer Res.*, 60:181-246, 1993). If decreases in HLA expression benefit a tumor because it facilitates CTL escape, but render the tumor susceptible to NK lysis, then a minimal level of HLA expression that allows for resistance to NK activity would be selected for (Garrido F, et al., Implications for immunosurveillance of altered HLA class I phenotypes in human tumours *Immunol Today* 18(2):89-96, February 1997). Therefore, a therapeutic compositions or methods in accordance with the invention together with a treatment to upregulate HLA expression and/or treatment with high affinity T-cells renders the tumor sensitive to CTL destruction.

Frequency of Alterations in HLA Expression

The frequency of alterations in class I expression is the subject of numerous studies (Algarra I, et al., The HLA crossroad in tumor immunology *Human Immunology* 61, 65-73, 2000). Rees and Mian estimate allelic loss to occur overall in 3-20% of tumors, and allelic deletion to occur in 15-50% of tumors. It should be noted that each cell carries two separate sets of class I genes, each gene carrying one HLA-A and one HLA-B locus. Thus, fully heterozygous individuals carry two different HLA-A molecules and two different HLA-B molecules. Accordingly, the actual frequency of losses for any specific allele could be as little as one quarter of the overall frequency. They also note that, in general, a gradient of expression exists between normal cells, primary tumors and tumor metastasis. In a study from Natali and coworkers (Natali P G, et al., Selective changes in expression of HLA class I polymorphic determinants in human solid tumors *PNAS USA* 86:6719-6723, September 1989), solid tumors were investigated for total HLA expression, using W6/32 antibody, and for allele-specific expression of the A2 antigen, as evaluated by use of the BB7.2 antibody. Tumor samples were derived from primary cancers or metastasis, for 13 different tumor types, and scored as negative if less than 20%, reduced if in the 30-80% range, and normal above 80%. All tumors, both primary and metastatic, were HLA positive with W6/32. In terms of A2 expression, a reduction was noted in 16.1% of the cases, and A2 was scored as undetectable in 39.4% of the cases. Garrido and coworkers (Garrido F, et al., Natural history of HLA expression during tumour development *Immunol Today* 14(10):491-99, 1993) emphasize that HLA changes appear to occur at a particular step in the progression from benign to most aggressive. Jiminez et al (Jiminez P, et al., Microsatellite instability analysis in tumors with different mechanisms for total loss of HLA expression. *Cancer Immunol Immunother* 48:684-90, 2000) have analyzed 118 different tumors (68 colorectal, 34 laryngeal and 16 melanomas). The frequencies reported for total loss of HLA expression were 11% for colon, 18% for melanoma and 13% for larynx. Thus, HLA class I expression is altered in a significant fraction of the tumor types, possibly as a reflection of immune pressure, or simply a reflection of the accumulation of pathological changes and alterations in diseased cells.

Immunotherapy in the Context of HLA Loss

A majority of the tumors express HLA class I, with a general tendency for the more severe alterations to be found in later stage and less differentiated tumors. This pattern is encouraging in the context of immunotherapy, especially considering that: 1) the relatively low sensitivity of immunohistochemical techniques might underestimate HLA expression in tumors; 2) class I expression can be induced in tumor cells as a result of local inflammation and lymphokine release; and, 3) class I negative cells are sensitive to lysis by NK cells.

Accordingly, various embodiments of the present invention can be selected in view of the fact that there can be a degree of loss of HLA molecules, particularly in the context of neoplastic disease. For example, the treating physician can assay a patient's tumor to ascertain whether HLA is being expressed. If a percentage of tumor cells express no class I HLA, then embodiments of the present invention that comprise methods or compositions that elicit NK cell responses can be employed. As noted herein, such NK-inducing methods or composition can comprise a Flt3 ligand or ProGP which facilitate mobilization of dendritic cells, the rationale being that dendritic cells produce large amounts of IL-12. IL-12 can also be administered directly in either amino acid or nucleic acid form. It should be noted that compositions in accordance with the invention can be administered concurrently with NK cell-inducing compositions, or these compositions can be administered sequentially.

In the context of allele-specific HLA loss, a tumor retains class I expression and may thus escape NK cell recognition, yet still be susceptible to a CTL-based vaccine in accordance with the invention which comprises epitopes corresponding to the remaining HLA type. The concept here is analogous to embodiments of the invention that include multiple disease antigens to guard against mutations that yield loss of a specific antigen. Thus, one can simultaneously target multiple HLA specificities and epitopes from multiple disease-related antigens to prevent tumor escape by allele-specific loss as well as disease-related antigen loss. In addition, embodiments of the present invention can be combined with alternative therapeutic compositions and methods. Such alternative compositions and methods comprise, without limitation, radiation, cytotoxic pharmaceuticals, and/or compositions/methods that induce humoral antibody responses.

Moreover, it has been observed that expression of HLA can be upregulated by gamma IFN, which is commonly secreted by effector CTL, and that HLA class I expression can be induced in vivo by both alpha and beta IFN. Thus, embodiments of the invention can also comprise alpha, beta and/or gamma IFN to facilitate upregualtion of HLA.

III.N. Reprieve Periods from Therapies that Induce Side Effects: "Scheduled Treatment Interruptions or Drug Holidays"

Recent evidence has shown that certain patients infected with a pathogen, whom are initially treated with a therapeutic regimen to reduce pathogen load, have been able to maintain decreased pathogen load when removed from the therapeutic regimen, i.e., during a "drug holiday" (Rosenberg, E., et al., Immune control of HIV-1 after early treatment of acute infection Nature 407:523-26, Sep. 28, 2000) As appreciated by those skilled in the art, many therapeutic regimens for both pathogens and cancer have numerous, often severe, side effects. During the drug holiday, the patient's immune system is keeping the disease in check. Methods for using compositions of the invention are used in the context of drug holidays for cancer and pathogenic infection.

For treatment of an infection, where therapies are not particularly immunosuppressive, compositions of the invention are administered concurrently with the standard therapy. During this period, the patient's immune system is directed to induce responses against the epitopes comprised by the present inventive compositions. Upon removal from the treatment having side effects, the patient is primed to respond to the infectious pathogen should the pathogen load begin to increase. Composition of the invention can be provided during the drug holiday as well.

For patients with cancer, many therapies are immunosuppressive. Thus, upon achievement of a remission or identification that the patient is refractory to standard treatment, then upon removal from the immunosuppressive therapy, a composition in accordance with the invention is administered. Accordingly, as the patient's immune system reconstitutes, precious immune resources are simultaneously directed against the cancer. Composition of the invention can also be administered concurrently with an immunosuppressive regimen if desired.

III.O. Kits

The peptide and nucleic acid compositions of this invention can be provided in kit form together with instructions for vaccine administration. Typically the kit would include desired peptide compositions in a container, preferably in unit dosage form and instructions for administration. An alternative kit would include a minigene construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

III.P. Overview

Epitopes in accordance with the present invention were successfully used to induce an immune response. Immune responses with these epitopes have been induced by administering the epitopes in various forms. The epitopes have been administered as peptides, as nucleic acids, and as viral vectors comprising nucleic acids that encode the epitope(s) of the invention. Upon administration of peptide-based epitope forms, immune responses have been induced by direct loading of an epitope onto an empty HLA molecule that is expressed on a cell, and via internalization of the epitope and processing via the HLA class I pathway; in either event, the HLA molecule expressing the epitope was then able to interact with and induce a CTL response. Peptides can be delivered directly or using such agents as liposomes. They can additionally be delivered using ballistic delivery, in which the peptides are typically in a crystalline form. When DNA is used to induce an immune response, it is administered either as naked DNA, generally in a dose range of approximately 1-5 mg, or via the ballistic "gene gun" delivery, typically in a dose range of approximately 10-100 µg. The DNA can be delivered in a variety of conformations, e.g. linear, circular etc. Various viral vectors have also successfully been used that comprise nucleic acids which encode epitopes in accordance with the invention.

Accordingly compositions in accordance with the invention exist in several forms. Embodiments of each of these composition forms in accordance with the invention have been successfully used to induce an immune response.

One composition in accordance with the invention comprises a plurality of peptides. This plurality or cocktail of peptides is generally admixed with one or more pharmaceutically acceptable excipients. The peptide cocktail can comprise multiple copies of the same peptide or can comprise a mixture of peptides. The peptides can be analogs of naturally occurring epitopes. The peptides can comprise artificial amino acids and/or chemical modifications such as addition of a surface active molecule, e.g., lipidation; acetylation, glycosylation, biotinylation, phosphorylation etc. The peptides can be CTL or HTL epitopes. In a preferred embodiment the peptide cocktail comprises a plurality of different CTL epitopes and at least one HTL epitope. The HTL epitope can be naturally or non-naturally (e.g., PADRE®, Epimmune Inc., San Diego, Calif.). The number of distinct epitopes in an embodiment of the invention is generally a whole unit integer from one through one hundred fifty (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 150).

An additional embodiment of a composition in accordance with the invention comprises a polypeptide multi-epitope construct, i.e., a polyepitopic peptide. Polyepitopic peptides in accordance with the invention are prepared by use of technologies well-known in the art. By use of these known technologies, epitopes in accordance with the invention are connected one to another. The polyepitopic peptides can be linear or non-linear, e.g., multivalent. These polyepitopic constructs can comprise artificial amino acids, spacing or spacer amino acids, flanking amino acids, or chemical modifications between adjacent epitope units. The polyepitopic construct can be a heteropolymer or a homopolymer. The polyepitopic constructs generally comprise epitopes in a quantity of any whole unit integer between 2-150 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 150). The polyepitopic construct can comprise CTL and/or HTL epitopes. One or more of the epitopes in the construct can be modified, e.g., by addition of a surface active material, e.g. a lipid, or chemically modified, e.g., acetylation, etc. Moreover, bonds in the multiepitopic construct can be other than peptide bonds, e.g., covalent bonds, ester or ether bonds, disulfide bonds, hydrogen bonds, ionic bonds etc.

Alternatively, a composition in accordance with the invention comprises construct which comprises a series, sequence, stretch, etc., of amino acids that have homology to (i.e., corresponds to or is contiguous with) to a native sequence. This stretch of amino acids comprises at least one subsequence of amino acids that, if cleaved or isolated from the longer series of amino acids, functions as an HLA class I or HLA class 11 epitope in accordance with the invention. In this embodiment, the peptide sequence is modified, so as to become a construct as defined herein, by use of any number of techniques known or to be provided in the art. The polyepitopic constructs can contain homology to a native sequence in any whole unit integer increment from 70-100%, e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent.

A further embodiment of a composition in accordance with the invention is an antigen presenting cell that comprises one or more epitopes in accordance with the invention. The antigen presenting cell can be a "professional" antigen presenting cell, such as a dendritic cell. The antigen presenting cell can comprise the epitope of the invention by any means known or to be determined in the art. Such means include pulsing of dendritic cells with one or more individual epitopes or with one or more peptides that comprise multiple epitopes, by nucleic acid administration such as ballistic nucleic acid delivery or by other techniques in the art for administration of nucleic acids, including vector-based, e.g. viral vector, delivery of nucleic acids.

Further embodiments of compositions in accordance with the invention comprise nucleic acids that encode one or more peptides of the invention, or nucleic acids which encode a polyepitopic peptide in accordance with the invention. As appreciated by one of ordinary skill in the art, various nucleic acids compositions will encode the same peptide due to the redundancy of the genetic code. Each of these nucleic acid compositions falls within the scope of the present invention. This embodiment of the invention comprises DNA or RNA, and in certain embodiments a combination of DNA and RNA. It is to be appreciated that any composition comprising nucleic acids that will encode a peptide in accordance with the invention or any other peptide based composition in accordance with the invention, falls within the scope of this invention.

It is to be appreciated that peptide-based forms of the invention (as well as the nucleic acids that encode them) can comprise analogs of epitopes of the invention generated using priniciples already known, or to be known, in the art. Principles related to analoging are now known in the art, and are disclosed herein; moreover, analoging principles (heteroclitic analoging) are disclosed in co-pending application serial number U.S. Ser. No. 09/226,775 filed 6 Jan. 1999. Generally the compositions of the invention are isolated or purified.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

IV. EXAMPLES

The following example of peptide binding to HLA molecules demonstrates quantification of binding affinities of HLA class I and class II peptides. Binding assays can be performed with peptides that are either motif-bearing or not motif-bearing.

Example 1

HLA Class I and Class II Binding Assays

The following example of peptide binding to HLA molecules demonstrates quantification of binding affinities of HLA class I and class II peptides. Binding assays can be performed with peptides that are either motif-bearing or not motif-bearing.

HLA class I and class II binding assays using purified HLA molecules were performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) were incubated with various unlabeled peptide inhibitors and 1-10 nM $^{125}$I-radiolabeled probe peptides as described. Following incubation, MHC-peptide complexes were separated from free peptide by gel filtration and the fraction of peptide bound was determined. Typically, in preliminary experiments, each MHC preparation was titered in the presence of fixed amounts of radiolabeled peptides to determine the concentration of HLA molecules necessary to bind 10-20% of the total radioactivity. All subsequent inhibition and direct binding assays were performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation has proven to be the most accurate and consistent for comparing peptides that have been tested on different days, or with different lots of purified MHC.

Binding assays as outlined above may be used to analyze supermotif and/or motif-bearing epitopes as, for example, described in Example 2.

Example 2

Identification of HLA Supermotif- and Motif-Bearing CTL Candidate Epitopes

Vaccine compositions of the invention can include multiple epitopes that comprise multiple HLA supermotifs or motifs to achieve broad population coverage. This example illustrates the identification of supermotif- and motif-bearing epitopes for the inclusion in such a vaccine composition. Calculation of population coverage was performed using the strategy described below.

Computer Searches and Algorthims for Identification of Supermotif and/or Motif-bearing Epitopes The searches performed to identify the motif-bearing peptide sequences in Examples 2 and 5 employed the protein sequence data from seven proteins (E1, E2, E5, E6, E7, L1 and L2) from HPV types 16, 18, 31, 33, 45, and 56.

| Accession numbers for HPV types | | | |
|---|---|---|---|
| Protein | 6a | 6b | 11 |
| E1 | Q84293 | P03113 | W1WL11 |
|  | AAA74213 | CAA25020 | P04014 |
|  |  | W1WL6 | AAA46929 |
| E2 | Q84294 | P03119 | AAA46930 |
|  | AAA74214 | CAA25021 | W2WLI1 |
|  |  | W2WL6 | P04015 |
| E4 | Q84295 | CAA25022 | P04016 |
|  | AAA74215 | W4WL6 | W4WL11 |
|  |  |  | AAA46931 |
| E5a | Q84296 | P06460 | W5WL11 |
|  | AAA74216 | CAA25023 | P04017 |
|  |  | W5WL6A | AAA46932 |
| E5b | N.A. | P06461 | W5WL1B |
|  |  | CAA25024 | P04018 |
|  |  | W5WLB | AAA46933 |
| E6 | Q84291 | P06462 | W6WL11 |
|  | AAA74211 | CAA250I8 | P04019 |
|  |  | W6WL6 | AAA21703 |
|  |  |  | AAA46927 |
| E7 | Q84929 | P06464 | AAA46928 |
|  | AAA74212 | CAA25019 | AAA21704 |
|  |  | W7WL6 | W7WL11 |
|  |  |  | P04020 |
| L1 | P03100 | P03100 | P04012 |
|  | AAA74218 | CAA25026 | P1WL11 |
|  |  | P1WL6 | AAA4635 |
| L2 | Q84297 | P03106 | P2WL11 |
|  |  | CAA25025 | AAA46934 |
|  |  | P2WL6 | P04013 |

| Strain | Protein Antigen | Accession number |
|---|---|---|
| HPV16 | E1 | W1SLHS |
| HPV16 | E2 | W2WLHS |
| HPV16 | E5 | W5WLHS |
| HPV16 | E6 | W6WLHS |
| HPV16 | E7 | W7WLHS |
| HPV16 | L1 | AAD33259 |
| HPV16 | L2 | AAD33258 |
| HPV18 | E1 | W1WL18 |
| HPV18 | E2 | WL18 |
| HPV18 | E5 | W5WL18 |
| HPV18 | E6 | W6WL18 |
| HPV18 | E7 | PO6788 |
| HPV18 | L1 | CAA28671 |
| HPV18 | L2 | P2WL18 |
| HPV31 | E1 | W1WL31 |
| HPV31 | E2 | W2WL3 |
| HPV31 | E5 | W5WL31 |
| HPV31 | E6 | W6WL31 |
| HPV31 | E7 | W7WL31 |
| HPV31 | L1 | P1WL31 |
| HPV31 | L2 | P2WL31 |
| HPV45 | E1 | S36563 |
| HPV45 | E2 | S36564 |
| HPV45 | E6 | CAB44706 |
| HPV45 | E7 | CAB44707 |
| HPV45 | L1 | CAB44705 |
| HPV45 | L2 | S36565 |
| HPV33 | E1 | W1WL33 |
| HPV33 | E2 | W2WL33 |
| HPV33 | E5 | W5WL33 |
| HPV33 | E6 | W6WL33 |
| HPV33 | E7 | W7WL33 |
| HPV33 | L1 | P1WL33 |
| HPV33 | L2 | P2WL33 |
| HPV56 | E2 | S36581 |
| HPV56 | E6 | W6WL56 |
| HPV56 | E7 | S36580 |
| HPV56 | L1 | S38563 |
| HPV56 | L2 | S36582 |

Computer searches for epitopes bearing HLA Class I or Class II supermotifs or motifs were performed as follows. All translated HPV protein sequences were analyzed using a text string search software program, e.g., MotifSearch 1.4 (D. Brown, San Diego) to identify potential peptide sequences containing appropriate HLA binding motifs; alternative programs are readily produced in accordance with information in the art in view of the motif/supermotif disclosure herein. Furthermore, such calculations can be made mentally.

Identified A2-, A3-, and DR-supermotif sequences were scored using polynomial algorithms to predict their capacity to bind to specific HLA-Class I or Class II molecules. These polynomial algorithms take into account both extended and refined motifs (that is, to account for the impact of different amino acids at different positions), and are essentially based on the premise that the overall affinity (or $\Delta G$) of peptide-HLA molecule interactions can be approximated as a linear polynomial function of the type:

$$\text{``}\Delta G\text{''} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide. This assumption is justified by studies from our laboratories that demonstrated that peptides are bound to MHC and recognized by T cells in essentially an extended conformation (data omitted herein).

The method of derivation of specific algorithm coefficients has been described in Gulukota et al, *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Complete protein sequences from the seven HPV structural and regulatory proteins of the HPV strains listed above were aligned, then scanned, utilizing motif identification software, to identify 9- and 10-mer sequences containing the HLA-A2-supermotif main anchor specificity.

HLA-A2 supermotif-bearing sequences are shown in Table VIII. Typically, these sequences are then scored using the A2 algorithm and the peptides corresponding to the positive-scoring sequences are synthesized and tested for their capacity to bind purified HLA-A*0201 molecules in vitro (HLA-A*0201 is considered a prototype A2 supertype molecule).

Examples of peptides that bind to HLA-A*0201 with $IC_{50}$ values $\leq$500 nM are shown in Table VIII. These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The HPV protein sequences scanned above were also examined for the presence of peptides with the HLA-A3-supermotif primary anchors (Table IX).

Peptides corresponding to the supermotif-bearing sequences are then synthesized and tested for binding to HLA-A*0301 and HLA-A* 1101 molecules, the two most prevalent A3-supertype alleles. The peptides that are found to bind one of the two alleles with binding affinities of $\leq$500 nM, often $\leq$200 nM, are then tested for binding cross-reactivity to the other common A3-supertype alleles (A*3101, A*3301, and A*6801) to identify those that can bind at least three of the five HLA-A3-supertype molecules tested.

Selection of HLA-B7 Supermotif Bearing Epitopes

The same HPV target antigen protein sequences were also analyzed for the presence of 9- or 10-mer peptides with the HLA-B7-supermotif (Table XI).

Corresponding peptides are synthesized and tested for binding to HLA-B*0702, the most common B7-supertype allele (i.e., the prototype B7 supertype allele). Peptides binding B*0702 with $IC_{50}$ of <500 nM are identified using standard methods. These peptides are then tested for binding to other common B7-supertype molecules (B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can, for example, also be incorporated into potential vaccine constructs. An analysis of the protein sequence data from the HPV target antigens utilized above can also be performed to identify HLA-A 1- and A24-motif-containing sequences.

High affinity and/or cross-reactive binding epitopes that bear other motif and/or supermotifs are identified using analogous methodology.

Example 3

Confirmation of Immunogenicity

Cross-reactive candidate CTL A2-supermotif-bearing peptides that are identified as described in Example 2 were selected for in vitro immunogenicity testing. Testing was performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to test the ability of peptide-specific CTLs to recognize endogenous antigen.

Primary CTL Induction Cultures:

Generation of Dendritic Cells (DC): PBMCs are thawed in RPMI with 30 g/ml DNAse, washed twice and resuspended in complete medium (RPMI-1640 plus 5% AB human serum, non-essential amino acids, sodium pyruvate, L-glutamine and penicillin/strpetomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three tines with 3 ml RPMI to remove most of the non-adherent and loosely adherent cells. Three ml of complete medium containing 50 ng/ml of GM-CSF and 1,000 U/ml of IL-4 are then added to each well. TNF is added to the DCs on day 6 at 75 ng/nl and the cells are used for CTL induction cultures on day 7.

Induction of CTL with DC and Peptide: CD8+ T-cells are isolated by positive selection with Dynal immunomagnetic beads (Dynabeads® M-450) and the detacha-bead® reagent. Typically about $200\text{-}250 \times 10^6$ PBMC are processed to obtain $24 \times 10^6$ CD8+ T-cells (enough for a 48-well plate culture). Briefly, the PBMCs are thawed in RPMI with 30 g/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 μl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 1001/ml detacha-bead® reagent and 30 μg/ml DNAse. The mixture is incubated for 1 hour at room temperature with continuous mixing. The beads are washed again with PBS/AB/DNAse to collect the CD8+T-cells. The DC are collected and centrifuged at 1300 rpm for 5-7 minutes, washed once with PBS with 1% BSA, counted and pulsed with 40 μg/ml of peptide at a cell concentration of $1\text{-}2 \times 10^6$/ml in the presence of 3 μg/ml $\beta_2$-microglobulin for 4 hours at 20° C. The DC are then irradiated (4,200 rads), washed 1 time with medium and counted again.

Setting up induction cultures: 0.25 ml cytokine-generated DC (@$1 \times 10^5$ cells/ml) are co-cultured with 0.25 ml of CD8+ T-cells (@$2 \times 10^6$ cell/ml) in each well of a 48-well plate in the presence of 10 ng/ml of IL-7. Recombinant human IL10 is added the next day at a final concentration of 10 ng/ml and rhuman IL2 is added 48 hours later at 10 IU/ml.

Restimulation of the induction cultures with peptide-pulsed adherent cells: Seven and fourteen days after the primary induction the cells are restimulated with peptide-pulsed adherent cells. The PBMCS are thawed and washed twice with RPMI and DNAse. The cells are resuspended at $5 \times 10^6$ cells/ml and irradiated at –4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml B2 microglobulin in 0.25 ml RPMI/5% AB per well for 2 hours at 37° C. Peptide solution from each well is aspirated and the wells are washed once with RPMI. Most of the media is aspirated from the induction cultures (CD8+cells) and brought to 0.5 ml with fresh media. The cells are then transferred to the wells containing the peptide-pulsed adherent cells. Twenty four hours later rhuman IL10 is added at a final concentration of 10 ng/ml and rhuman IL2 is added the next day and again 2-3 days later at 50 IU/ml (Tsai et al., *Critical Reviews in Immunology* 18(1-2):65-75, 1998). Seven days later the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side by side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labelled with 200 μCi of $^{51}$Cr sodium chromate (Dupont, Wilmington, Del.) for 1 hour at 37° C. Labelled target cells are resuspended at $10^6$ per ml and diluted 1:10 with K562 cells at a concentration of $3.3 \times 10^6$/ml (an NK-sensitive erythroblastoma cell line used to reduce non-specific lysis). Target cells (100 μl) and 100 μl of effectors are plated in 96 well round-bottom plates and incubated for 5 hours at 37° C. At that time, 100 μl of supernatant are collected from each well and percent lysis is determined according to the formula: [(cpm of the test sample-cpm of the spontaneous $^{51}$Cr release sample)/(cpm of the maximal $^{51}$Cr release sample-cpm of the spontaneous $^{51}$Cr release sample)]×100. Maximum and spontaneous release are determined by incubating the labelled targets with 1% Trition X-100 and media alone, respectively. A positive culture is defined as one in which the specific lysis (sample-background) is 10% or higher in the case of individual wells and is 15% or more at the 2 highest E:T ratios when expanded cultures are assayed.

In situ Measurement of Human γIFN Production as an Indicator of Peptide-specific and Endogenous Recognition Immulon 2 plates are coated with mouse anti-human IFNγ monoclonal antibody (4 μg/ml 0.1M NaHCO$_3$, pH 8.2) overnight at 4° C. The plates are washed with Ca$^{2+}$, Mg$^{2+}$-free PBS/0.05% Tween 20 and blocked with PBS/10% FCS for 2 hours, after which the CILs (100 μl/well) and targets (100 μl/well) are added to each well, leaving empty wells for the standards and blanks (which received media only). The target cells, either peptide-pulsed or endogenous targets, are used at a concentration of $1 \times 10^6$ cells/ml. The plates are incubated for 48 hours at 37° C. with 5% CO$_2$.

Recombinant human IFNγ is added to the standard wells starting at 400 μg or 1200 μg/100 μl/well and the plate incubated for 2 hours at 37° C. The plates are washed and 100 l of biotinylated mouse anti-human IFNγ monoclonal antibody (2 μg/ml in PBS/3% FCS/0.05% Tween 20) are added and incubated for 2 hours at room temperature. After washing again, 100 μl HRP-streptavidin (1:4000) are added and the plates incubated for 1 hour at room temperature. The plates are then washed 6× with wash buffer, 100 μl/well developing solution (TMB 1:1) are added, and the plates allowed to develop for 5-15 minutes. The reaction is stopped with 50 μl/well 1M H$_3$PO$_4$ and read at OD450. A culture is considered positive if it measured at least 50 μg of IFNγ/well above background and is twice the background level of expression.

CTL Expansion. Those cultures that demonstrate specific lytic activity against peptide-pulsed targets and/or tumor targets are expanded over a two week period with anti-CD3. Briefly, $5 \times 10^4$ CD8+cells are added to a T25 flask containing the following: $1 \times 10^6$ irradiated (4,200 rad) PBMC (autologous or allogeneic) per ml, $2 \times 10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 251 μM 2-mercaptoethanol, L-glutamine and penicillin/streptomycin. Rhuman IL2 is added 24 hours later at a final concentration of 200 IU/ml and every 3 days thereafter with fresh media at 50 IU/ml. The cells are split if the cell concentration exceeded $1 \times 10^6$/ml and the cultures are assayed between days 13 and 15 at E:T ratios of 30, 10, 3 and 1:1 in the $^{51}$Cr release assay or at $1 \times 10^6$/ml in the in situ IFN assay using the same targets as before the expansion.

Cultures are expanded in the absence of anti-CD3$^+$ as follows. Those cultures that demonstrate specific lytic activity against peptide and endogenous targets are selected and $5 \times 10^4$ CD8$^+$ cells are added to a T25 flask containing the following: $1 \times 10^6$ autologous PBMC per ml which have been peptide-pulsed with 10 g/ml peptide for 2 hours at 37° C. and irradiated (4,200 rad); $2 \times 10^5$ irradiated (8,000 rad) EBV-transformed cells per ml RPMI-1640 containing 10%(v/v) human AB serum, non-essential AA, sodium pyruvate, 25 mM 2-ME, L-glutamine and gentamicin.

Immunogenicity of A2 Supermotif-bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least 2 donors (unless otherwise noted) and preferably, also recognizes the endogenously expressed peptide.

Immunogenicity is additionally confirmed using PBMCs isolated from HPV-infected patients. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified in Example 2 are evaluated in a manner analogous to the evaluation of A2- and A3-supermotif-bearing peptides.

Peptides bearing other supermotifs/motifs, e.g., HLA-A1, HLA-A24 etc. are also evaluated using similar methodology Example 4

Implementation of the Extended Supermotif to Improve the Binding Capacity of Native Epitopes by Creating Analog HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged, or "fixed" to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, on the basis of the data disclosed, e.g., in related and co-pending U.S. Ser. No. 09/226,775, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is tested for binding to one or all supertype members and then analogued to modulate binding affinity to any one (or more) of the supertype members to add population coverage.

The selection of analogs for immunogenicity in a cellular screening analysis is typically further restricted by the capacity of the parent peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to demonstrate that analog-specific CTLs are also able to recognize the wild-type peptide and, when possible, target cells that endogenously express the epitope.

Analoging of HLA-A3 and B7-Supermotif-bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A* 11 (prototype A3 supertype alleles). Those peptides that demonstrate ≦500 nM binding capacity are then tested for A3-supertype cross-reactivity.

Similarly to the A2- and A3-motif bearing peptides, peptides binding 3 or more B7-supertype alleles can be improved, where possible, to achieve increased cross-reactive binding. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoguing at primary anchor residues of other motif and/or supermotif-bearing epitopes is performed in a like manner.

The analog peptides are then be tested for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at postion 1 is analyzed. The peptide is then analoged to, for example, substitute L for F at position 1. The analoged peptide is evaluated for increased binding affinity/and or increased cross-reactivity. Such a procedure identifies analoged peptides with modulated binding affinity.

Engineered analogs with sufficiently improved binding capacity or cross-reactivity can also be tested for immunogenicity in HLA-B7-transgenic mice, following for example, IFA immunization or lipopeptide immunization. Analogued peptides are additionally tested for the ability to stimulate a recall response using PBMC from HPV-infected patients.

Other Analoguing Strategies

Another form of peptide analoguing, unrelated to the anchor positions, involves the substitution of a cysteine with α-amino butyric acid. Due to its chemical nature, cysteine has the propensity to form disulfide bridges and sufficiently alter the peptide structurally so as to reduce binding capacity. Subtitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of even single amino acid substitutions, the binding affinity and/or cross-reactivity of peptide ligands for HLA supertype molecules can be modulated.

Example 5

Identification of HPV-derived Sequences With HLA-DR Binding Motifs

Peptide epitopes bearing an HLA class II supermotif or motif are identified as outlined below using methodology similar to that described in Examples 1-3.

Selection of HLA-DR-supermotif-bearing Epitopes.

To identify HPV-derived, HLA class II HTL epitopes, the protein sequences from the same HPV antigens used for the identification of HLA Class I supermotif/motif sequences were analyzed for the presence of sequences bearing an HLA-DR-motif or supermotif. Specifically, 15-mer sequences were selected comprising a DR-supermotif, further comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The HPV-derived peptides identified above are tested for their binding capacity for various common HLA-DR molecules. All peptides are initially tested for binding to the DR molecules in the primary panel: DR1, DR4w4, and DR7. Peptides binding at least 2 of these 3 DR molecules are then tested for binding to DR2w2 β1, DR2w2 β2, DR6w19, and DR9 molecules in secondary assays. Finally, peptides binding at least 2 of the 4 secondary panel DR molecules, and thus cumulatively at least 4 of 7 different DR molecules, are screened for binding to DR4w15, DR5w11, and DR8w2 molecules in tertiary assays. Peptides binding at least 7 of the 10 DR molecules comprising the primary, secondary, and tertiary screening assays are considered cross-reactive DR binders. HPV-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is an important criterion in the selection of HTL epitopes. However, data generated previously indicated that DR3 only rarely cross-reacts with other DR alleles (Sidney et al., *J. Immunol.* 149:2634-2640, 1992; Geluk et al., *J. Immunol.* 152:5742-5748, 1994; Southwood et al., *J. Immunol.* 160: 3363-3373, 1998). This is not entirely surprising in that the DR3 peptide-binding motif appears to be distinct from the specificity of most other DR alleles. For maximum efficiency in developing vaccine candidates it would be desirable for DR3 motifs to be clustered in proximity with DR supermotif regions. Thus, peptides shown to be candidates may also be assayed for their DR3 binding capacity. However, in view of the distinct binding specificity of the DR3 motif, peptides binding only to DR3 can also be considered as candidates for inclusion in a vaccine formulation.

To efficiently identify peptides that bind DR3, target HPV antigens are analyzed for sequences carrying one of the two DR3 specific binding motifs reported by Geluk et al. (*J. Immunol.* 152:5742-5748, 1994). The corresponding peptides are then synthesized and tested for the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class U motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 6

Immunogenicity of HPV-derived HTL Epitopes

This example determines immunogenic DR supermotif- and DR3 motif-bearing epitopes among those identified using the methodology in Example 5.

Immunogenicity of HTL epitopes are evaluated in a manner analogous to the determination of immunogenicity of CTL epitopes by assessing the ability to stimulate HTL responses and/or by using appropriate transgenic mouse models. Immunogenicity is determined by screening for: 1.) in vitro primary induction using normal PBMC or 2.) recall responses from cancer patient PBMCs.

Example 7

Calculation of Phenotypic Frequencies of HLA-supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles were determined. Gene frequencies for each HLA allele were calculated from antigen or allele frequencies utilizing the binomial distribution formulae gf=1−(SQRT(1−af)) (see, e.g., Sidney et al., *Human Immunol.* 45:79-93, 1996). To obtain overall phenotypic frequencies, cumulative gene frequencies were calculated, and the cumulative antigen frequencies derived by the use of the inverse formula [af=1−(1−Cgf)$^2$].

Where frequency data was not available at the level of DNA typing, correspondence to the serologically defined antigen frequencies was assumed. To obtain total potential supertype population coverage no linkage disequilibrium was assumed, and only alleles confirmed to belong to each of the supertypes were included (minimal estimates). Estimates of total potential coverage achieved by inter-loci combinations were made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations.

Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups, supra. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 8

CTL Recognition of Endogenous Processed Antigens After Priming

This example determines that CTL induced by native or analogued peptide epitopes identified and selected as described in Examples 1-6 recognize endogenously synthesized, i.e., native antigens.

Effector cells isolated from transgenic mice that are immunized with peptide epitopes as in Example 3, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with HPV expression vectors.

The result will demonstrate that CTL lines obtained from animals primed with peptide epitope recognize endogenously synthesized HPV antigen. The choice of transgenic mouse model to be used for such an analysis depends upon the epitope(s) that is being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A 1 and A24) are being developed. HLA-DR1 and HLA-DR3 mouse models have also been developed, which may be used to evaluate HTL epitopes.

Example 9

Activity of CTL-HTL Conjugated Epitopes in Transgenic Mice

This example illustrates the induction of CTLs and HTLs in transgenic mice by use of a tumor associated antigen CTL/HTL peptide conjugate whereby the vaccine composition comprises peptides to be administered to an HPV-infected patient. The peptide composition can comprise multiple CTL and/or HTL epitopes and further, can comprise epitopes selected from multiple HPV target antigens. The epitopes are identified using methodology as described in Examples 1-6 This analysis demonstrates the enhanced immunogenicity that can be achieved by inclusion of one or more HTL epitopes in a vaccine composition. Such a peptide composition can comprise an HTL epitope conjugated to a preferred CTL epitope containing, for example, at least one CTL epitope that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753-4761, 1997). For example, A2/K$^b$ mice, which are transgenic for the human HLA A2.1 allele and are useful for the assessment of the immunogenicity of HLA-A*0201 motif- or HLA-A2 supermotif-bearing epitopes, are primed subcutaneously (base of the tail) with a 0.1 ml of peptide in Incomplete Freund's Adjuvant, or if the peptide composition is a lipidated CTL/HTL conjugate, in DMSO/saline or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 10.5×10$^6$) are incubated at 37° C. in the presence of 200 μl of $^{51}$Cr. After 60 minutes, cells are washed three times and resuspended in R10 medium. Peptide is added where required at a concentration of 1 μg/ml. For the assay, 10$^4$ $^{51}$Cr-labeled target cells are added to different concentrations of effector cells (final volume of 200 μl) in U-bottom 96-well plates. After a 6 hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a 6 hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector (E): target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)−(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using the CTL epitope as outlined in Example 3. Analyses similar to this may be performed to evaluate the immunogenicity of peptide conjugates containing multiple CTL epitopes and/or multiple HTL epitopes. In accordance with these procedures it is found that a CTL response is induced, and concomitantly that an HTL response is induced upon administration of such compositions.

Example 10

Selection of CTL and HTL Epitopes for Inclusion in an HPV-specific Vaccine

This example illustrates the procedure for the selection of peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting an array of epitopes for inclusion in a vaccine composition. Each of the following principles is balanced in order to make the selection.

Epitopes are selected which, upon administration, mimic immune responses that have been observed to be correlated with HPV clearance. The number of epitopes used depends on observations of patients who spontaneously clear HPV. For example, if it has been observed that patients who spontaneously clear HPV generate an immune response to at least 3 epitopes on at least one HPV antigen, then 3-4 epitopes should be included for HLA class I. A similar rationale is used to determine HLA class H epitopes.

When selecting an array of HPV epitopes, it is preferred that at least some of the epitopes are derived from early and late proteins. The early proteins of HPV are expressed when the virus is replicating, either following acute or dormant infection. Therefore, it is particularly preferred to use epitopes from early stage proteins to alleviate disease manifestations at the earliest stage possible.

Epitopes are often selected that have a binding affinity of an $IC_{50}$ of 500 nM or less for an HLA class I molecule, or for class II, an $IC_{50}$ of 1000 nM or less.

Sufficient supermotif bearing peptides, or a sufficient array of allele-specific motif bearing peptides, are selected to give broad population coverage. For example, epitopes are selected to provide at least 80% population coverage. A Monte Carlo analysis, a statistical evaluation known in the art, can be employed to assess breadth, or redundancy, of population coverage.

When creating a polyepitopic compositions, e.g. a minigene, it is typically desirable to generate the smallest peptide possible that encompasses the epitopes of interest. The principles employed are similar, if not the same, as those employed when selecting a peptide comprising nested epitopes.

In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

A vaccine composition comprised of selected peptides, when administered, is safe, efficacious, and elicits an immune response similar in magnitude to an immune response that controls or clears an acute HPV infection.

Example 11

Construction of Minigene Multi-Epitope DNA Plasmids

This example provides general guidance for the construction of a minigene expression plasmid. Minigene plasmids may, of course, contain various configurations of CTL and/or HTL epitopes or epitope analogs as described herein. Examples of the construction and evaluation of expression plasmids are described, for example, in co-pending U.S. Ser. No. 09/311,784 filed May 13, 1999.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived from multiple HPV antigens, preferably including both early and late phase antigens, are selected such that multiple supermotifs/motifs are represented to ensure broad population coverage. Similarly, HLA class II epitopes are selected from multiple HPV antigens to provide broad population coverage, i.e. both HLA DR-1-4-7 supermotif-bearing epitopes and HLA DR-3 motif-bearing epitopes are selected for inclusion in the minigene construct. The selected CIL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in co-pending application U.S. Ser. No. 09/311,784 filed May 13, 1999, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Ellmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene can be prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH_4)_2SO_4$, 20 mM Tris-chloride, pH 8.75, 2 mM $MgSO_4$, 0.1% Triton X-100, 100 µg/ml BSA), 0.25 mM each diNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 12

The Plasmid Construct and the Degree to Which it Induces Immunogenicity

The degree to which a plasmid construct, for example a plasmid constructed in accordance with Example 11, is able to induce immunogenicity can be evaluated in vitro by testing for epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by infected or transfected target cells, and then determining the concentration of peptide necessary to obtained equivalent levels of lysis or lymphokine release (see, e.g., Kageyama et al., *J. Immunol.* 154:567-576, 1995).

Alternatively, immunogenicity can be evaluated through in vivo injections into mice and subsequent in vitro assessment of CTL and HTL activity, which are analysed using cytotoxicity and proliferation assays, respectively, as detailed e.g., in copending U.S. Ser. No. 09/311,784 filed May 13, 1999 and Alexander et al., *Immunity* 1:751-761, 1994.

For example, to assess the capacity of a DNA minigene construct (e.g., a pMin minigene construct generated as decribed in U.S. Ser. No. 09/311,784) containing at least one HLA-A2 supermotif peptide to induce CTLs in vivo, HLA-A2.1/$K^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine. It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes.

To assess the capacity of a class II epitope encoding minigene to induce HTLs in vivo, DR transgenic mice, or for those epitope that cross react with the appropriate mouse MHC molecule, I-$A^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4$^+$ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. *Immunity* 1:751-761, 1994). The results indicate the magnitude of the HTL response, thus demonstrating the in vivo immunogenicity of the minigene.

DNA minigenes, constructed as described in Example 11, may also be evaluated as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/$K^b$ transgenic mice are immunized IM with 100 g of a DNA minigene encoding the immunogenic peptides including at least one HLA-A2 supermotif-bearing peptide. After an incubation period (ranging from 3-9 weeks), the mice are boosted IP with 1 pfu/mouse of a recombinant vaccinia virus expressing the same sequence encoded by the DNA minigene. Control mice are immunized with 100 g of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an IFN-ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes.

The use of prime boost protocols in humans is described in Example 20.

Example 13

Peptide Composition for Prophylactic Uses

Vaccine compositions of the present invention can be used to prevent HPV infection in persons who are at risk for such infection. For example, a polyepitopic peptide epitope composition (or a nucleic acid comprising the same) containing multiple CTL and HTL epitopes such as those selected in Examples 9 and/or 10, which are also selected to target greater than 80% of the population, is administered to individuals at risk for HPV infection.

For example, a peptide-based composition can be provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against HPV infection.

Alternatively, a composition typically comprising transfecting agents can be used for the administration of a nucleic acid-based vaccine in accordance with methodologies known in the art and disclosed herein.

Example 14

Polyepitopic Vaccine Compositions Derived from Native HPV Sequences

A native HPV polyprotein sequence is screened, preferably using computer algorithms defined for each class I and/or class II supermotif or motif, to identify "relatively short" regions of the polyprotein that comprise multiple epitopes and is preferably less in length than an entire native antigen. This relatively short sequence that contains multiple distinct, even overlapping, epitopes is selected and used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e. frame shifted relative to one another). For example, with f overlapping epitopes, two 9-mer epitopes and one 10-mer epitope can be present in a 10 amino acid peptide. Such a vaccine composition is administered for therapeutic or prophylactic purposes.

The vaccine composition will include, for example, three CTL epitopes from at least one HPV target antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent analogs) directs the immune response to multiple peptide sequences that are actually present in native HPV antigens thus avoiding the need to evaluate any junctional epitopes. Lastly, the embodiment provides an economy of scale when producing nucleic acid vaccine compositions.

Related to this embodiment, computer programs can be derived in accordance with principles in the art, which identify in a target sequence, the greatest number of epitopes per sequence length.

Example 15

Polyepitopic Vaccine Compositions from Multiple Antigens

The HPV peptide epitopes of the present invention are used in conjunction with peptide epitopes from other target tumor-associated antigens to create a vaccine composition that is useful for the prevention or treatment of cancer resulting from HPV infection in multiple patients.

For example, a vaccine composition can be provided as a single polypeptide that incorporates multiple epitopes from HPV antigens as well as tumor-associated antigens that are often expressed with a target cancer, e.g., cervical cancer, associated with HPV infection, or can be administered as a composition comprising one or more discrete epitopes. Alternatively, the vaccine can be administered as a minigene construct or as dendritic cells which have been loaded with the peptide epitopes in vitro.

Example 16

Use of Peptides to Evaluate an Immune Response

Peptides of the invention may be used to analyze an immune response for the presence of specific CTL or HTL populations directed to HPV. Such an analysis may be performed in a manner as that described by Ogg et al., Science 279:2103-2106, 1998. In the following example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, HPV HLA-A*0201-specific CTL frequencies from HLA A*0201-positive individuals at different stages of infection or following immunization using an HPV peptide containing an A*0201 motif. Tetrameric complexes are synthesized as described (Musey et al., N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5'triphosphate and magnesium Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive uninfected donors. The percentage of cells stained with the tetramer is then determined by flow cytometry. The results indicate the number of cells in the PBMC sample that contain epitope-restricted CTLs, thereby readily indicating the extent of immune response to the HPV epitope, and thus the stage of infection with HPV, the status of exposure to HPV, or exposure to a vaccine that elicits a protective or therapeutic response.

Example 17

Use of Peptide Epitopes to Evaluate Recall Responses

The peptide epitopes of the invention are used as reagents to evaluate T cell responses, such as acute or recall responses, in patients. Such an analysis may be performed on patients who have recovered from infection, who are chronically infected with HPV, or who have been vaccinated with an HPV vaccine.

For example, the class I restricted CTL response of persons who have been vaccinated may be analyzed. The vaccine may be any HPV vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128-140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 ul of complete RPMI and 20 U/ml final concentration of rIL-2 are added to each well. On day 7 the cultures are transferred into a 96-well flat-bottom plate and restimulated with peptide, rIL-2 and 105 irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with uninfected control subjects as previously described (Rehermann, et al., Nature Med. 2:1104,1108, 1996; Rehermann et al., J. Clin. Invest. 97:1655-1665, 1996; and Rehermann et al. J. Clin. Invest. 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. J. Virol. 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to HPV or an HPV vaccine.

The class II restricted HTL responses may also be analyzed. Purified PBMC are cultured in a 96-well flat bottom plate at a density of $1.5 \times 10^5$ cells/well and are stimulated with 10 µg/ml synthetic peptide, whole antigen, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 18

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 19

Phase II Trials in Patients Infected With HPV

Phase II trials are performed to study the effect of administering the CTL-HTL peptide compositions to patients having cancer associated with HPV infection. The main objectives of the trials are to determine an effective dose and regimen for inducing CTLs in HPV-infected patients with cancer, to establish the safety of inducing a CTL and HTL response in these patients, and to see to what extent activation of CTLs improves the clinical picture of chronically infected HPV patients, as manifested by a reduction in viral load, e.g., the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them are infected with HPV and are HIV, HCV, HBV and delta hepatitis virus (HDV) negative, but are positive for HPV DNA as monitered by PCR.

Clinical manifestations or antigen-specific T-cell responses are monitored to assess the effects of administering the peptide compositions. The vaccine composition is found to be both safe and efficacious in the treatment of HPV infection.

Example 20

Induction of CTL Responses Using a Prime Boost Protocol

A prime boost protocol similar in its underlying principle to that used to evaluate the efficacy of a DNA vaccine in transgenic mice, such as described in Example 12, can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in Example 11, in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5-10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples will be obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve protective immunity against HPV is generated.

Example 21

Administration of Vaccine Compositions Using Dendritic Cells (DC)

Vaccines comprising peptide epitopes of the invention can be administered using APCs, or "professional" APCs such as DC. In this example, the peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction of the specific target cells that bear the proteins from which the epitopes in the vaccine are derived.

For example, a cocktail of epitope-bearing peptides is administered ex vivo to PBMC, or isolated DC therefrom. A pharmaceutical to facilitate harvesting of DC can be used, such as Progenipoietin (Monsanto, St. Louis, Mo.) or GM-CSF/IL-4. After pulsing the DC with peptides and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although $2-50 \times 10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC containing DC generated after treatment with an agent such as Progenipoietin are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5 \times 10^6$ DC, then the patient will be injected with a total of $2.5 \times 10^8$ peptide-loaded PBMC. The percent DC mobilized by an agent such as Progenipoietin™ is typically estimated to be between 2-10%, but can vary as appreciated by one of skill in the art.

Ex vivo Activation of CTL/HTL Responses

Alternatively, ex vivo CTL or HTL responses to HPV antigens can be induced by incubating in tissue culture the patient's, or genetically compatible, CTL or HTL precursor cells together with a source of APC, such as DC, and the appropriate immunogenic peptides. After an appropriate incubation time (typically about 7-28 days), in which the precursor cells are activated and expanded into effector cells, the cells are infused back into the patient, where they will destroy (CTL) or facilitate destruction (HTL) of their specific target cells, i.e., tumor cells.

Example 22

Alternative Method of Identifying Motif-Bearing Peptides

Another method of identifying motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be infected with a pathogenic organism or transfected with nucleic acids that express the antigen of interest, e.g. HPV regulatory or structural proteins. Peptides produced by endogenous antigen processing of peptides produced consequent to infection (or as a result of transfection) will then bind to HLA molecules within the cell and be transported and displayed on the cell surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can be infected with a pathogen or transfected with nucleic acid encoding an antigen of interest to isolate peptides corresponding to the pathogen or antigen of interest that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than infection or transfection, such as loading with a protein antigen, can be used to provide a source of antigen to the cell.

The above examples are provided to illustrate the invention but not to limit its scope. For example, the human terminology for the Major Histocompatibility Complex, namely HLA, is used throughout this document. It is to be appreciated that these principles can be extended to other species as well. Thus, other variants of the invention will be readily apparent to one of ordinary skill in the art and are encompassed by the appended claims. All publications, patents, and patent application cited herein are hereby incorporated by reference for all purposes.

TABLE I

|  | POSITION 2 (Primary Anchor) | POSITION 3 (Primary Anchor) | POSITION C Terminus (Primary Anchor) |
|---|---|---|---|
| SUPERMOTIFS |  |  |  |
| A1 | T, I, *L, V, M, S* |  | F, W, Y |
| A2 | L, I, V, M, *A, T, Q* |  | I, V, *M, A, T, L* |
| A3 | V, S, M, A, *T, L, I* |  | R, K |
| A24 | Y, F, *W, I, V, L, M, T* |  | F, I, *Y, W, L, M* |
| B7 | P |  | V, I, L, F, *M, W, Y, A* |
| B27 | R, H, K |  | F, Y, L, *W, M, I, V, A* |
| B44 | E, *D* |  | F, W, L, I, M, V, A |
| B58 | A, T, S |  | F, W, Y, *L, I, V, M, A* |
| B62 | Q, L, *I, V, M, P* |  | F, W, Y, *M, I, V, L, A* |
| MOTIFS |  |  |  |
| A1 | T, S, M |  | Y |
| A1 |  | D, E, *A, S* | Y |
| A2.1 | L, M, *V, Q, I, A, T* |  | V, *L, I, M, A, T* |
| A3 | L, M, V, I, S, A, T, F, *C, G, D* |  | K, Y, R, *H, F, A* |
| A11 | V, T, M, L, I, S, A, *G, N, C, D, F* |  | K, *R, Y, H* |
| A24 | V, F, W, *M* |  | F, L, I, W |
| A*3101 | M, V, T, *A, L, I, S* |  | R, *K* |
| A*3301 | M, V, A, L, F, *I, S, T* |  | R, K |
| A*6801 | A, V, T, *M, S, L, I* |  | R, K |
| B*0702 | P |  | L, M, F, *W, Y, A, I, V* |
| B*3501 | P |  | L, M, F, W, Y, *I, V, A* |
| B51 | P |  | L, I, V, F, *W, Y, A, M* |
| B*5301 | P |  | I, M, F, W, Y, *A, L, V* |
| B*5401 | P |  | A, T, I, V, *L, M, F, W, Y* |

Bolded residues are preferred, italicized residues are less preferred: A peptide is considered motif-bearing if it has primary anchors at each primary anchor position for a motif or supermotif as specified in the above table.

TABLE Ia

| | POSITION 2 (Primary Anchor) | POSITION 3 (Primary Anchor) | POSITION C Terminus (Primary Anchor) |
|---|---|---|---|
| SUPERMOTIFS | | | |
| A1 | T, I, *L, V, M, S* | | F, W, Y |
| A1 | V, *Q, A, T* | | I, V, *L, M, A, T* |
| A3 | V, S, M, A, *T, L, I* | | R, K |
| A24 | Y, F, *W, I, V, L, M, T* | | F, I, *Y, W, L, M* |
| B7 | P | | V, I, L, F, *M, W, Y, A* |
| B27 | R, H, K | | F, Y, L, *W, M, I, V, A* |
| B58 | A, T, S | | F, W, Y, *L, I, V, M, A* |
| B62 | Q, L, *I, V, M, P* | | F, W, Y, *M, I, V, L, A* |
| MOTIFS | | | |
| A1 | T, S, M | | Y |
| A1 | | D, E, *A, S* | Y |
| A2.1 | *V, Q, A, T\ | | V**, *L, I, M, A, T* |
| A3.2 | L, M, V, I, S, A, T, F, *C, G, D* | | K, Y, R, *H, F, A* |
| A11 | V, T, M, L, I, S, A, *G, N, C, D, F* | | K, *R, H, Y* |
| A24 | Y, F, W | | F, L, I, W |

*If 2 is V, or Q, the C-term is not L
Bolded residues are preferred, italicized residues are less preferred: A peptide is considered motif-bearing if it has primary anchors at each primary anchor position for a motif or supermotif as specified in the above table.

TABLE II

| | | POSITION | | | | | | | | | |
|---|---|---|---|---|---|---|---|---|---|---|---|
| | | 1 | 2 | 3 | 4 | 5 | 6 | 7 | 8 | 9 or C-terminus | C-terminus |
| SUPERMOTIFS | | | | | | | | | | | |
| A1 | | | 1° Anchor T, I, *L, V, M, S* | | | | | | | | 1° Anchor F, W, Y |
| A2 | | | 1° Anchor L, I, V, M, A, T, *Q* | | | | | | | | 1° Anchor L, I, V, M, A, T |
| A3 | preferred | | 1° Anchor V, S, M, A, T, L, *I* | Y, F, W, (4/5) | | | Y, F, W, (3/5) | Y, F, W, (4/5) | P, (4/5) | | 1° Anchor R, K |
| | deleterious | D, E (3/5); P, (5/5) | | D, E, (4/5) | | | | | | | |
| A24 | | | 1° Anchor Y, F, *W, I, V, L, M, T* | | | | | | | | 1° Anchor F, I, *Y, W, L, M* |
| B7 | preferred | F, W, Y (5/5) L, I, V, M, (3/5) | 1° Anchor P | F, W, Y (4/5) | | | | | F, W, Y, (3/5) | | 1° Anchor V, I, L, F, *M, W, Y, A* |
| | deleterious | D, E (3/5); P (5/5); G (4/5); A (3/5); Q, N, (3/5) | | | | D, E, (3/5) | G, (4/5) | Q, N, (4/5) | D, E, (4/5) | | |
| B27 | | | 1° Anchor R, H, K | | | | | | | | 1° Anchor F, Y, L, *W, M, V, A* |
| B44 | | | 1° Anchor E, *D* | | | | | | | | 1° Anchor F, W, Y, L, I, M, V, A |
| B58 | | | 1° Anchor A, T, S | | | | | | | | 1° Anchor F, W, Y, *L, I, V, M, A* |
| B62 | | | 1° Anchor Q, L, *I, V, M, P* | | | | | | | | 1° Anchor F, W, Y, *M, I, V, L, A* |

TABLE II-continued

| | | \multicolumn{9}{c}{POSITION} | |
|---|---|---|---|---|---|---|---|---|---|---|
| | | 1 | 2 | 3 | 4 | 5 | 6 | 7 | 8 | 9 or C-terminus | C-terminus |
| MOTIFS | | | | | | | | | | | |
| A1 9-mer | preferred | G, F, Y, W, | 1° Anchor S, T, M, | D, E, A, | Y, F, W, | | P, | D, E, Q, N, | Y, F, W, | | 1° Anchor Y |
| | deleterious | D, E, | | R, H, K, L, I, V, M, P, | A, | G, | A, | | | | |
| A1 9-mer | preferred | G, R, H, K | A, S, T, C, L, I, V, M, | 1° Anchor D, E, *A, S* | G, S, T, C, | | A, S, T, C, | L, I, V, M, | D, E, | | 1° Anchor Y |
| | deleterious | A | R, H, K, D, E, P, Y, F, W, | | D, E, | P, Q, N, | R, H, K, | P, G, | G, P, | | |
| A1 10-mer | preferred | Y, F, W, | 1° Anchor S, T, M | D, E, A, Q, N, | A, | Y, F, W, Q, N, | | P, A, S, T, C, | G, D, E, | P, | 1° Anchor Y |
| | deleterious | G, P, | | R, H, K, G, L, I V, M, | D, E, | R, H, K, | Q, N, A | R, H, K, Y, F, W, | R, H, K, | A | |
| A1 10-mer | preferred | Y, F, W, | S, T, C, L, I, V, M, | 1° Anchor D, E, *A, S* | A, | Y, F, W, | | P, G, | G, | Y, F, W, | 1° Anchor Y |
| | deleterious | R, H, K, | R, H, K, D, E, P, Y, F, W, | | | P, | G, | P, R, H, K, | Q, N, | | |
| A2.1 9-mer | preferred | Y, F, W, | 1° Anchor L, M, *I, V, Q, A, T* | Y, F, W, | S, T, C, | Y, F, W, | | A, | P | 1° Anchor V, *L, I, M, A, T* | |
| | deleterious | D, E, P, | | D, E, R, K, H | | | R, K, H | D, E, R, K, H | | | |
| A2.1 10-mer | preferred | A, Y, F, W, | 1° Anchor L, M, *I, V, Q, A, T* | L, V, I, M, | G, | | G, | | F, Y, W, L, V, I, M, | | 1° Anchor V, *L, I, M, A, T* |
| | deleterious | D, E, P, | | D, E, | R, K, H, A, | P, | | R, K, H, | D, E, R, K, H, | R, K, H, | |
| A3 | preferred | R, H, K, | 1° Anchor L, M, V, I, S, A, T, F, *C, G, D* | Y, F, W, | P, R, H, K, Y, F, W, | A, | Y, F, W, | | P, | 1° Anchor K, Y, R, *H, F, A* | |
| | deleterious | D, E, P, | | D, E | | | | | | | |
| A11 | preferred | A, | 1° Anchor V, T, L, M, I, S, A, G, N, *C, D, F* | Y, F, W, | Y, FW, | A, | Y, F, W, | Y, FW, | P, | 1° Anchor K,, *RY, H* | |
| | deleterious | D, E, P, | | | | | | A | G, | | |
| A24 9-mer | preferred | Y, F, W, R, H, K, | 1° Anchor Y, F, W, *M* | | | S, T, C | | | Y, F, W, | Y, F, W, | 1° Anchor F, L, I, W |
| | deleterious | D, E, G, | | D, E, | G, | Q, N, P, | D, E, R, H, K, | G, | A, Q, N, | | |
| A24 10-mer | preferred | | 1° Anchor Y, F, W, *M* | | P, | Y, F, W, P, | | P, | | | 1° Anchor F, L, I, W |
| | deleterious | | | G, D, E | Q, N | R, H, K | D, E | A | Q, N, | D, E, A, | |
| A3101 | preferred | R, H, K, | 1° Anchor M, V, T, *A, L, I, S* | Y, F, W, | P, | | Y, F, W, | Y, F, W, | A, P, | 1° Anchor R, *K* | |
| | deleterious | D, E, P, | | D, E, | | A, D, E, | D, E, | D, E, | D, E, | | |
| A3301 | preferred | | 1° Anchor M, V, A, L, F, *I, S, T* | Y, F, W | | | | A, Y, F, W | | 1° Anchor R, K | |
| | deleterious | G, P | | D, E | | | | | | | |
| A6801 | preferred | Y, F, W, S, T, C, | 1° Anchor A, V, T, *M, S, L, I* | | | Y, F, W, | L, I, V, M | | Y, F, W, | P, | 1° Anchor R, K |
| | deleterious | G, P, | | D, E, G, | | R, H, K, | | | A, | | |
| B0702 | preferred | R, H, K, F, W, Y, | 1° Anchor P | R, H, K, | | R, H, K, | R, H, K, | R, H, K, | P, A, | 1° Anchor L, M, F, *W, Y, A, I, V* | |
| | deleterious | D, E, Q, N, P, | | D, E, P, | D, E, | D, E, | G, D, E, | Q, N, | D, E | | |

TABLE II-continued

| | | POSITION | | | | | | | | |
|---|---|---|---|---|---|---|---|---|---|---|
| | | 1 | 2 | 3 | 4 | 5 | 6 | 7 | 8 | 9 or C-terminus | C-terminus |
| B3501 | preferred | F, W, Y, L, I, V, M, | 1° Anchor P | F, W, Y, | | | | F, W, Y, | | 1° Anchor L, M, F, W, Y, *I, V, A* |
| | deleterious | A, G, P, | | | | G, | G, | | | |
| B51 | preferred | L, I, V, M, F, W, Y, | 1° Anchor P | F, W, Y, | S, T, C, | F, W, Y, | | G, | F, W, Y, | 1° Anchor L, I, V, F, *W, Y, A, M* |
| | deleterious | A, G, P, D, E, R, H, K, S, T, C, | | | | D, E, | G, | D, E, Q, N, | G, D, E, | |
| B5301 | preferred | L, I, V, M, F, W, Y, | 1° Anchor P | F, W, Y, | S, T, C, | F, W, Y, | | L, I, V, M, F, W, Y, | F, W, Y, | 1° Anchor I, M, F, W, Y, *A, L, V* |
| | deleterious | A, G, P, Q, N, | | | | | G, | R, H, K, Q, N, | D, E, | |
| B5401 | preferred | F, W, Y, | 1° Anchor P | F, W, Y, L, I, V, M, | | L, I, V, M, | | A, L, I, V, M, | F, W, Y, A, P, | 1° Anchor A, T, I, V, *L, M, F, W, Y* |
| | deleterious | G, P, Q, N, D, E, | | G, D, E, S, T, C, | | R, H, K, D, E, | D, E, | Q, N, D, G, E, | D, E, | |

Italicized residues indicate less preferred or "tolerated" residues.
The information in Table II is specific for 9-mers unless otherwise specified.
Secondary anchor specificities are designated for each position independently.

TABLE III

| SEQ ID NO: | MOTIFS | | POSITION | | | | | | | |
|---|---|---|---|---|---|---|---|---|---|---|
| | | | 1° anchor 1 | 2 | 3 | 4 | 5 | 1° anchor 6 | 7 | 8 | 9 |
| | DR4 | preferred | F, M, Y, *L, I, V, W,* | M, T, | | | I, | V, S, T, C, P, A, *L, I, M,* | M, H, | | M, H |
| | | deleterious | | | | W, | | | R, | | W, D, E |
| | DR1 | preferred | M, F, *L, I, V, W, Y,* | | | P, A, M, Q, | | V, M, A, T, *S, P, L, I, C,* | M, | | A, V, M |
| | | deleterious | | C, | C, H | F, D | C, W, D | | G, D, E, | D | |
| 87 | DR7 | preferred | M, F, *L, I, V, W, Y,* | M, W, | | A, | | I, V, M, S, A, *C, T, P, L,* | M, | | I, V |
| 88 | | deleterious | | C, | G, | | | | G, R, D, | N | G |
| | DR Supermotif | | M, F, *L, I, V, W, Y,* | | | | | V, M, S, T, A, *C, P, L, I,* | | | |

| DR3 MOTIFS | | POSITION | | | | |
|---|---|---|---|---|---|---|
| | 1° anchor 1 | 2 | 3 | 1° anchor 4 | 5 | 1° anchor 6 |
| motif a preferred | L, I, V, M, F, Y, | | | D | | |
| motif b preferred | L, I, V, M, F, A, Y, | | | D, N, Q, E, S, T | | K, R, H |

Italicized residues indicate less preferred or "tolerated" residues. Secondary anchor specificities are designated for each position independently.

| TABLE IV | | | | | TABLE IV-continued | | | | |
|---|---|---|---|---|---|---|---|---|---|
| HLA Class I Standard Peptide Binding Affinity. | | | | | HLA Class I Standard Peptide Binding Affinity. | | | | |
| ALLELE | STANDARD PEPTIDE | SEQUENCE | SEQ ID NO: | STANDARD BINDING AFFINITY (nM) | ALLELE | STANDARD PEPTIDE | SEQUENCE | SEQ ID NO: | STANDARD BINDING AFFINITY (nM) |
| A*0101 | 944.02 | YLEPAIAKY | 71 | 25 | A*0206 | 941.01 | FLPSDYFPSV | 72 | 3.7 |
| A*0201 | 941.01 | FLPSDYFPSV | 72 | 5.0 | A*0207 | 941.01 | FLPSDYFPSV | 72 | 23 |
| A*0202 | 941.01 | FLPSDYFPSV | 72 | 4.3 | A*6802 | 1072.34 | YVIKVSARV | 73 | 8.0 |
| A*0203 | 941.01 | FLPSDYFPSV | 72 | 10 | A*0301 | 941.12 | KVFPYALINK | 74 | 11 |
| A*0205 | 941.01 | FLPSDYFPSV | 72 | 4.3 | A*1101 | 940.06 | AVDLYHFLK | 75 | 6.0 |

TABLE IV-continued

HLA Class I Standard Peptide Binding Affinity.

| ALLELE | STANDARD PEPTIDE | SEQUENCE | SEQ ID NO: | STANDARD BINDING AFFINITY (nM) |
|---|---|---|---|---|
| A*3101 | 941.12 | KVFPYALINK | 74 | 18 |
| A*3301 | 1083.02 | STLPETYVVRR | 76 | 29 |
| A*6801 | 941.12 | KVFPYALINK | 74 | 8.0 |
| A*2402 | 979.02 | AYIDNYNKF | 77 | 12 |
| B*0702 | 1075.23 | APRTLVYLL | 78 | 5.5 |
| B*3501 | 1021.05 | FPFKYAAAF | 79 | 7.2 |
| B51 | 1021.05 | FPFKYAAAF | 79 | 5.5 |
| B*5301 | 1021.05 | FPFKYAAAF | 79 | 9.3 |
| B*5401 | 1021.05 | FPFKYAAAF | 79 | 10 |

TABLE V

HLA Class II Standard Peptide Binding Affinity.

| Allele | Nomenclature | Standard Peptide | Sequence | SEQ ID NO: | Binding Affinity (nM) |
|---|---|---|---|---|---|
| DRB1*0101 | DR1 | 515.01 | PKYVKQNTLKLAT | 80 | 5.0 |
| DRB1*0301 | DR3 | 829.02 | YKTIAFDEEARR | 81 | 300 |
| DRB1*0401 | DR4w4 | 515.01 | PKYVKQNTLKLAT | 80 | 45 |
| DRB1*0404 | DR4w14 | 717.01 | YARFQSQTTLKQKT | 82 | 50 |
| DRB1*0405 | DR4w15 | 717.01 | YARFQSQTTLKQKT | 82 | 38 |
| DRB1*0701 | DR7 | 553.01 | QYIKANSKFIGITE | 67 | 25 |
| DRB1*0802 | DR8w2 | 553.01 | QYIKANSKFIGITE | 67 | 49 |
| DRB1*0803 | DR8w3 | 553.01 | QYIKANSKFIGITE | 67 | 1600 |
| DRB1*0901 | DR9 | 553.01 | QYIKANSKFIGITE | 67 | 75 |
| DRB1*1101 | DR5w11 | 553.01 | QYIKANSKFIGITE | 67 | 20 |
| DRB1*1201 | DR5w12 | 1200.05 | EALIHQLKINPYVLS | 83 | 298 |
| DRB1*1302 | DR6w19 | 650.22 | QYIKANAKFIGITE | 84 | 3.5 |
| DRB1*1501 | DR2w2β1 | 507.02 | GRTQDENPVVHFFKNIVTPRTPPP | 85 | 9.1 |
| DRB3*0101 | DR52a | 511 | NGQIGNDPNRDIL | 86 | 470 |
| DRB4*0101 | DRw53 | 717.01 | YARFQSQTTLKQKT | 82 | 58 |
| DRB5*0101 | DR2w2β2 | 553.01 | QYIKANSKFIGITE | 67 | 20 |

TABLE VII

HLA-A1 Supermotif Peptides

| 1 | 2 | 3 | 4 |
|---|---|---|---|
| HPV16 | E1 | 10 | 206 |
| HPV16 | E1 | 8 | 524 |
| HPV16 | E1 | 9 | 82 |
| HPV16 | E1 | 11 | 353 |
| HPV16 | E1 | 10 | 368 |
| HPV16 | E1 | 11 | 41 |
| HPV16 | E1 | 8 | 372 |
| HPV16 | E1 | 10 | 249 |
| HPV16 | E1 | 9 | 43 |
| HPV16 | E1 | 9 | 384 |
| HPV16 | E1 | 10 | 603 |
| HPV16 | E1 | 11 | 603 |

TABLE VI

Allelle-specific HLA-supertype members

| HLA-supertype | Verified[a] | Predicted[b] |
|---|---|---|
| A1 | A*0101, A*2501, A*2601, A*2602, A*3201 | A*0102, A*2604, A*3601, A*4301, A*8001 |
| A2 | A*0201, A*0202, A*0203, A*0204, A*0205, A*0206, A*0207, A*0209, A*0214, A*6802, A*6901 | A*0208, A*0210, A*0211, A*0212, A*0213 |
| A3 | A*0301, A*1101, A*3101, A*3301, A*6801 | A*0302, A*1102, A*2603, A*3302, A*3303, A*3401, A*3402, A*6601, A*6602, A*7401 |
| A24 | A*2301, A*2402, A*3001 | A*2403, A*2404, A*3002, A*3003 |
| B7 | B*0702, B*0703, B*0704, B*0705, B*1508, B*3501, B*3502, B*3503, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, B*7801 | B*1511, B*4201, B*5901 |
| B27 | B*1401, B*1402, B*1509, B*2702, B*2703, B*2704, B*2705, B*2706, B*3801, B*3901, B*3902, B*7301 | B*2701, B*2707, B*2708, B*3802, B*3903, B*3904, B*3905, B*4801, B*4802, B*1510, B*1518, B*1503 |
| B44 | B*1801, B*1802, B*3701, B*4402, B*4403, B*4404, B*4001, B*4002, B*4006 | B*4101, B*4501, B*4701, B*4901, B*5001 |
| B58 | B*5701, B*5702, B*5801, B*5802. B*1516, B*1517 | |
| B62 | B*1501, B*1502, B*1513, B*5201 | B*1301, B*1302, B*1504, B*1505, B*1506, B*1507, B*1515, B*1520, B*1521, B*1512, B*1514, B*1510 |

[a]Verified alleles include alleles whose specificity has been determined by pool sequencing analysis, peptide binding assays, or by analysis of the sequences of CTL epitopes.
[b]Predicted alleles are alleles whose specificity is predicted on the basis of B and F pocket structure to overlap with the supertype specificity.

TABLE VII-continued

HLA-A1 Supermotif Peptides

| 1 | 2 | 3 | 4 |
|---|---|---|---|
| HPV16 | E1 | 8 | 356 |
| HPV16 | E1 | 10 | 356 |
| HPV16 | E1 | 9 | 63 |
| HPV16 | E1 | 9 | 152 |
| HPV16 | E1 | 9 | 331 |
| HPV16 | E1 | 8 | 51 |
| HPV16 | E1 | 9 | 493 |
| HPV16 | E1 | 9 | 445 |
| HPV16 | E1 | 8 | 456 |
| HPV16 | E1 | 11 | 453 |
| HPV16 | E1 | 8 | 219 |
| HPV16 | E1 | 9 | 586 |
| HPV16 | E1 | 8 | 501 |
| HPV16 | E1 | 9 | 501 |
| HPV16 | E1 | 11 | 466 |
| HPV16 | E1 | 9 | 325 |
| HPV16 | E1 | 11 | 519 |
| HPV16 | E1 | 10 | 272 |
| HPV16 | E1 | 9 | 163 |
| HPV16 | E1 | 8 | 571 |
| HPV16 | E1 | 8 | 12 |
| HPV16 | E1 | 9 | 12 |
| HPV16 | E1 | 11 | 216 |
| HPV16 | E1 | 9 | 263 |
| HPV16 | E1 | 8 | 348 |
| HPV16 | E1 | 11 | 329 |
| HPV16 | E1 | 8 | 326 |
| HPV16 | E1 | 9 | 369 |
| HPV16 | E1 | 11 | 369 |
| HPV16 | E1 | 10 | 311 |
| HPV16 | E1 | 11 | 311 |
| HPV16 | E1 | 8 | 610 |
| HPV16 | E1 | 11 | 483 |
| HPV16 | E1 | 10 | 227 |
| HPV16 | E1 | 11 | 323 |
| HPV16 | E1 | 10 | 252 |
| HPV16 | E1 | 8 | 254 |
| HPV16 | E1 | 9 | 357 |
| HPV16 | E1 | 11 | 48 |
| HPV16 | E1 | 10 | 583 |
| HPV16 | E1 | 9 | 207 |
| HPV16 | E1 | 10 | 520 |
| HPV16 | E1 | 10 | 454 |
| HPV16 | E1 | 9 | 420 |
| HPV16 | E1 | 9 | 273 |
| HPV16 | E1 | 10 | 567 |
| HPV16 | E1 | 10 | 600 |
| HPV16 | E1 | 8 | 441 |
| HPV16 | E1 | 10 | 419 |
| HPV16 | E1 | 10 | 118 |
| HPV16 | E1 | 8 | 343 |
| HPV16 | E1 | 10 | 125 |
| HPV16 | E1 | 11 | 582 |
| HPV16 | E1 | 8 | 313 |
| HPV16 | E1 | 9 | 313 |
| HPV16 | E1 | 10 | 313 |
| HPV16 | E1 | 8 | 432 |
| HPV16 | E1 | 9 | 250 |
| HPV16 | E1 | 10 | 484 |
| HPV16 | E1 | 8 | 421 |
| HPV16 | E1 | 8 | 314 |
| HPV16 | E1 | 9 | 314 |
| HPV16 | E1 | 11 | 231 |
| HPV16 | E1 | 9 | 253 |
| HPV16 | E1 | 11 | 498 |
| HPV16 | E1 | 11 | 345 |
| HPV16 | E1 | 11 | 443 |
| HPV16 | E1 | 10 | 217 |
| HPV16 | E1 | 9 | 584 |
| HPV16 | E1 | 11 | 584 |
| HPV16 | E1 | 8 | 274 |
| HPV16 | E1 | 11 | 261 |
| HPV16 | E1 | 9 | 578 |
| HPV16 | E1 | 11 | 578 |
| HPV16 | E2 | 11 | 331 |
| HPV16 | E2 | 11 | 41 |
| HPV16 | E2 | 8 | 314 |
| HPV16 | E2 | 11 | 309 |
| HPV16 | E2 | 8 | 124 |
| HPV16 | E2 | 11 | 124 |
| HPV16 | E2 | 8 | 25 |
| HPV16 | E2 | 9 | 25 |
| HPV16 | E2 | 9 | 263 |
| HPV16 | E2 | 9 | 338 |
| HPV16 | E2 | 11 | 22 |
| HPV16 | E2 | 10 | 74 |
| HPV16 | E2 | 8 | 80 |
| HPV16 | E2 | 11 | 168 |
| HPV16 | E2 | 9 | 163 |
| HPV16 | E2 | 9 | 35 |
| HPV16 | E2 | 10 | 35 |
| HPV16 | E2 | 8 | 193 |
| HPV16 | E2 | 10 | 332 |
| HPV16 | E2 | 9 | 329 |
| HPV16 | E2 | 9 | 354 |
| HPV16 | E2 | 11 | 77 |
| HPV16 | E2 | 9 | 84 |
| HPV16 | E2 | 8 | 296 |
| HPV16 | E2 | 10 | 296 |
| HPV16 | E2 | 8 | 127 |
| HPV16 | E2 | 11 | 9 |
| HPV16 | E2 | 10 | 106 |
| HPV16 | E2 | 8 | 76 |
| HPV16 | E2 | 8 | 151 |
| HPV16 | E2 | 9 | 151 |
| HPV16 | E2 | 10 | 191 |
| HPV16 | E2 | 8 | 37 |
| HPV16 | E2 | 10 | 23 |
| HPV16 | E2 | 11 | 23 |
| HPV16 | E2 | 11 | 261 |
| HPV16 | E2 | 11 | 144 |
| HPV16 | E2 | 8 | 355 |
| HPV16 | E2 | 10 | 78 |
| HPV16 | E2 | 9 | 297 |
| HPV16 | E2 | 10 | 93 |
| HPV16 | E2 | 8 | 334 |
| HPV16 | E2 | 10 | 310 |
| HPV16 | E2 | 11 | 128 |
| HPV16 | E2 | 9 | 146 |
| HPV16 | E2 | 10 | 146 |
| HPV16 | E2 | 9 | 192 |
| HPV16 | E2 | 9 | 333 |
| HPV16 | E2 | 10 | 145 |
| HPV16 | E2 | 11 | 145 |
| HPV16 | E2 | 8 | 147 |
| HPV16 | E2 | 9 | 147 |
| HPV16 | E2 | 11 | 92 |
| HPV16 | E2 | 8 | 312 |
| HPV16 | E2 | 10 | 312 |
| HPV16 | E2 | 8 | 131 |
| HPV16 | E2 | 9 | 159 |
| HPV16 | E2 | 10 | 159 |
| HPV16 | E5 | 10 | 54 |
| HPV16 | E5 | 9 | 7 |
| HPV16 | E5 | 11 | 5 |
| HPV16 | E5 | 9 | 60 |
| HPV16 | E5 | 9 | 72 |
| HPV16 | E5 | 9 | 64 |
| HPV16 | E5 | 8 | 43 |
| HPV16 | E5 | 10 | 51 |
| HPV16 | E5 | 8 | 51 |
| HPV16 | E5 | 8 | 73 |
| HPV16 | E5 | 9 | 42 |
| HPV16 | E5 | 9 | 11 |
| HPV16 | E5 | 8 | 32 |
| HPV16 | E5 | 11 | 47 |
| HPV16 | E5 | 10 | 48 |
| HPV16 | E5 | 11 | 70 |
| HPV16 | E5 | 9 | 31 |
| HPV16 | E5 | 10 | 41 |

TABLE VII-continued

HLA-A1 Supermotif Peptides

| 1 | 2 | 3 | 4 |
|---|---|---|---|
| HPV16 | E5 | 8 | 8 |
| HPV16 | E5 | 10 | 10 |
| HPV16 | E5 | 11 | 40 |
| HPV16 | E5 | 11 | 9 |
| HPV16 | E5 | 8 | 50 |
| HPV16 | E5 | 11 | 50 |
| HPV16 | E5 | 10 | 53 |
| HPV16 | E6 | 9 | 68 |
| HPV16 | E6 | 10 | 68 |
| HPV16 | E6 | 10 | 58 |
| HPV16 | E6 | 11 | 73 |
| HPV16 | E6 | 8 | 32 |
| HPV16 | E6 | 8 | 92 |
| HPV16 | E6 | 8 | 125 |
| HPV16 | E6 | 9 | 80 |
| HPV16 | E6 | 9 | 59 |
| HPV16 | E6 | 8 | 79 |
| HPV16 | E6 | 10 | 79 |
| HPV16 | E6 | 9 | 44 |
| HPV16 | E6 | 11 | 44 |
| HPV16 | E6 | 8 | 43 |
| HPV16 | E6 | 10 | 43 |
| HPV16 | E6 | 11 | 89 |
| HPV16 | E6 | 11 | 29 |
| HPV16 | E6 | 10 | 77 |
| HPV16 | E7 | 10 | 14 |
| HPV16 | E7 | 8 | 4 |
| HPV16 | E7 | 8 | 18 |
| HPV16 | L1 | 9 | 373 |
| HPV16 | L1 | 11 | 292 |
| HPV16 | L1 | 10 | 251 |
| HPV16 | L1 | 9 | 249 |
| HPV16 | L1 | 11 | 484 |
| HPV16 | L1 | 8 | 154 |
| HPV16 | L1 | 9 | 228 |
| HPV16 | L1 | 8 | 17 |
| HPV16 | L1 | 9 | 17 |
| HPV16 | L1 | 9 | 378 |
| HPV16 | L1 | 8 | 474 |
| HPV16 | L1 | 10 | 5 |
| HPV16 | L1 | 8 | 481 |
| HPV16 | L1 | 9 | 348 |
| HPV16 | L1 | 8 | 499 |
| HPV16 | L1 | 11 | 323 |
| HPV16 | L1 | 11 | 307 |
| HPV16 | L1 | 9 | 438 |
| HPV16 | L1 | 9 | 22 |
| HPV16 | L1 | 8 | 102 |
| HPV16 | L1 | 10 | 102 |
| HPV16 | L1 | 11 | 418 |
| HPV16 | L1 | 11 | 86 |
| HPV16 | L1 | 8 | 374 |
| HPV16 | L1 | 11 | 11 |
| HPV16 | L1 | 10 | 407 |
| HPV16 | L1 | 11 | 406 |
| HPV16 | L1 | 11 | 151 |
| HPV16 | L1 | 10 | 90 |
| HPV16 | L1 | 8 | 46 |
| HPV16 | L1 | 8 | 68 |
| HPV16 | L1 | 9 | 68 |
| HPV16 | L1 | 8 | 409 |
| HPV16 | L1 | 10 | 87 |
| HPV16 | L1 | 11 | 226 |
| HPV16 | L1 | 11 | 263 |
| HPV16 | L1 | 9 | 325 |
| HPV16 | L1 | 8 | 311 |
| HPV16 | L1 | 8 | 421 |
| HPV16 | L1 | 10 | 421 |
| HPV16 | L1 | 11 | 247 |
| HPV16 | L1 | 8 | 466 |
| HPV16 | L1 | 11 | 43 |
| HPV16 | L1 | 8 | 331 |
| HPV16 | L1 | 8 | 280 |
| HPV16 | L1 | 10 | 100 |
| HPV16 | L1 | 9 | 67 |
| HPV16 | L1 | 10 | 67 |
| HPV16 | L1 | 8 | 253 |
| HPV16 | L1 | 11 | 28 |
| HPV16 | L1 | 10 | 419 |
| HPV16 | L1 | 10 | 324 |
| HPV16 | L1 | 10 | 308 |
| HPV16 | L1 | 11 | 308 |
| HPV16 | L1 | 9 | 422 |
| HPV16 | L1 | 8 | 423 |
| HPV16 | L1 | 8 | 439 |
| HPV16 | L1 | 9 | 408 |
| HPV16 | L1 | 11 | 327 |
| HPV16 | L1 | 11 | 376 |
| HPV16 | L1 | 9 | 252 |
| HPV16 | L1 | 11 | 65 |
| HPV16 | L1 | 8 | 379 |
| HPV16 | L1 | 11 | 379 |
| HPV16 | L1 | 10 | 264 |
| HPV16 | L1 | 11 | 264 |
| HPV16 | L1 | 9 | 91 |
| HPV16 | L1 | 10 | 44 |
| HPV16 | L1 | 8 | 326 |
| HPV16 | L1 | 9 | 30 |
| HPV16 | L1 | 9 | 260 |
| HPV16 | L1 | 8 | 7 |
| HPV16 | L1 | 8 | 389 |
| HPV16 | L1 | 8 | 275 |
| HPV16 | L1 | 8 | 53 |
| HPV16 | L1 | 9 | 53 |
| HPV16 | L2 | 11 | 356 |
| HPV16 | L2 | 11 | 293 |
| HPV16 | L2 | 8 | 261 |
| HPV16 | L2 | 10 | 340 |
| HPV16 | L2 | 11 | 242 |
| HPV16 | L2 | 9 | 259 |
| HPV16 | L2 | 10 | 259 |
| HPV16 | L2 | 10 | 364 |
| HPV16 | L2 | 10 | 63 |
| HPV16 | L2 | 11 | 218 |
| HPV16 | L2 | 8 | 65 |
| HPV16 | L2 | 8 | 439 |
| HPV16 | L2 | 9 | 439 |
| HPV16 | L2 | 10 | 45 |
| HPV16 | L2 | 11 | 45 |
| HPV16 | L2 | 10 | 243 |
| HPV16 | L2 | 8 | 250 |
| HPV16 | L2 | 8 | 430 |
| HPV16 | L2 | 10 | 105 |
| HPV16 | L2 | 10 | 248 |
| HPV16 | L2 | 9 | 318 |
| HPV16 | L2 | 10 | 318 |
| HPV16 | L2 | 11 | 318 |
| HPV16 | L2 | 10 | 39 |
| HPV16 | L2 | 8 | 323 |
| HPV16 | L2 | 11 | 427 |
| HPV16 | L2 | 9 | 249 |
| HPV16 | L2 | 11 | 183 |
| HPV16 | L2 | 10 | 294 |
| HPV16 | L2 | 11 | 454 |
| HPV16 | L2 | 8 | 276 |
| HPV16 | L2 | 11 | 273 |
| HPV16 | L2 | 10 | 397 |
| HPV16 | L2 | 9 | 429 |
| HPV16 | L2 | 10 | 124 |
| HPV16 | L2 | 8 | 386 |
| HPV16 | L2 | 11 | 383 |
| HPV16 | L2 | 10 | 172 |
| HPV16 | L2 | 9 | 358 |
| HPV16 | L2 | 8 | 221 |
| HPV16 | L2 | 11 | 44 |
| HPV16 | L2 | 8 | 342 |
| HPV16 | L2 | 9 | 234 |
| HPV16 | L2 | 11 | 9 |
| HPV16 | L2 | 8 | 319 |
| HPV16 | L2 | 9 | 319 |

TABLE VII-continued

HLA-A1 Supermotif Peptides

| 1 | 2 | 3 | 4 |
|---|---|---|---|
| HPV16 | L2 | 10 | 319 |
| HPV16 | L2 | 10 | 274 |
| HPV16 | L2 | 10 | 360 |
| HPV16 | L2 | 9 | 125 |
| HPV16 | L2 | 11 | 104 |
| HPV16 | L2 | 8 | 107 |
| HPV16 | L2 | 10 | 184 |
| HPV16 | L2 | 9 | 185 |
| HPV16 | L2 | 8 | 186 |
| HPV16 | L2 | 10 | 384 |
| HPV16 | L2 | 9 | 40 |
| HPV16 | L2 | 9 | 438 |
| HPV16 | L2 | 10 | 438 |
| HPV16 | L2 | 8 | 399 |
| HPV16 | L2 | 8 | 359 |
| HPV16 | L2 | 11 | 359 |
| HPV16 | L2 | 9 | 295 |
| HPV16 | L2 | 8 | 156 |
| HPV16 | L2 | 9 | 398 |
| HPV16 | L2 | 9 | 244 |
| HPV16 | L2 | 11 | 153 |
| HPV16 | L2 | 10 | 154 |
| HPV16 | L2 | 9 | 106 |
| HPV16 | L2 | 9 | 155 |
| HPV16 | L2 | 10 | 393 |
| HPV16 | L2 | 10 | 437 |
| HPV16 | L2 | 11 | 437 |
| HPV18 | E1 | 10 | 213 |
| HPV18 | E1 | 11 | 526 |
| HPV18 | E1 | 11 | 40 |
| HPV18 | E1 | 8 | 531 |
| HPV18 | E1 | 9 | 531 |
| HPV18 | E1 | 11 | 216 |
| HPV18 | E1 | 10 | 437 |
| HPV18 | E1 | 9 | 240 |
| HPV18 | E1 | 8 | 363 |
| HPV18 | E1 | 10 | 363 |
| HPV18 | E1 | 9 | 391 |
| HPV18 | E1 | 10 | 637 |
| HPV18 | E1 | 9 | 42 |
| HPV18 | E1 | 10 | 610 |
| HPV18 | E1 | 11 | 610 |
| HPV18 | E1 | 9 | 62 |
| HPV18 | E1 | 10 | 375 |
| HPV18 | E1 | 8 | 379 |
| HPV18 | E1 | 9 | 587 |
| HPV18 | E1 | 9 | 338 |
| HPV18 | E1 | 8 | 50 |
| HPV18 | E1 | 9 | 500 |
| HPV18 | E1 | 11 | 460 |
| HPV18 | E1 | 8 | 463 |
| HPV18 | E1 | 10 | 399 |
| HPV18 | E1 | 9 | 452 |
| HPV18 | E1 | 8 | 226 |
| HPV18 | E1 | 8 | 130 |
| HPV18 | E1 | 8 | 508 |
| HPV18 | E1 | 9 | 508 |
| HPV18 | E1 | 11 | 223 |
| HPV18 | E1 | 8 | 11 |
| HPV18 | E1 | 9 | 11 |
| HPV18 | E1 | 10 | 473 |
| HPV18 | E1 | 10 | 279 |
| HPV18 | E1 | 10 | 249 |
| HPV18 | E1 | 9 | 270 |
| HPV18 | E1 | 11 | 352 |
| HPV18 | E1 | 11 | 336 |
| HPV18 | E1 | 10 | 506 |
| HPV18 | E1 | 11 | 506 |
| HPV18 | E1 | 10 | 461 |
| HPV18 | E1 | 10 | 590 |
| HPV18 | E1 | 8 | 439 |
| HPV18 | E1 | 10 | 318 |
| HPV18 | E1 | 11 | 318 |
| HPV18 | E1 | 10 | 234 |
| HPV18 | E1 | 8 | 401 |
| HPV18 | E1 | 8 | 490 |
| HPV18 | E1 | 11 | 490 |
| HPV18 | E1 | 10 | 259 |
| HPV18 | E1 | 8 | 281 |
| HPV18 | E1 | 8 | 261 |
| HPV18 | E1 | 9 | 364 |
| HPV18 | E1 | 10 | 224 |
| HPV18 | E1 | 9 | 376 |
| HPV18 | E1 | 11 | 376 |
| HPV18 | E1 | 9 | 214 |
| HPV18 | E1 | 10 | 527 |
| HPV18 | E1 | 11 | 47 |
| HPV18 | E1 | 10 | 574 |
| HPV18 | E1 | 8 | 428 |
| HPV18 | E1 | 11 | 487 |
| HPV18 | E1 | 8 | 448 |
| HPV18 | E1 | 10 | 607 |
| HPV18 | E1 | 10 | 426 |
| HPV18 | E1 | 10 | 80 |
| HPV18 | E1 | 11 | 589 |
| HPV18 | E1 | 10 | 128 |
| HPV18 | E1 | 8 | 320 |
| HPV18 | E1 | 9 | 320 |
| HPV18 | E1 | 10 | 320 |
| HPV18 | E1 | 8 | 321 |
| HPV18 | E1 | 9 | 321 |
| HPV18 | E1 | 8 | 322 |
| HPV18 | E1 | 9 | 260 |
| HPV18 | E1 | 11 | 238 |
| HPV18 | E1 | 10 | 533 |
| HPV18 | E1 | 8 | 532 |
| HPV18 | E1 | 11 | 532 |
| HPV18 | E1 | 9 | 591 |
| HPV18 | E1 | 11 | 591 |
| HPV18 | E1 | 11 | 505 |
| HPV18 | E1 | 9 | 81 |
| HPV18 | E1 | 9 | 280 |
| HPV18 | E1 | 8 | 339 |
| HPV18 | E1 | 9 | 585 |
| HPV18 | E1 | 11 | 585 |
| HPV18 | E2 | 10 | 82 |
| HPV18 | E2 | 10 | 154 |
| HPV18 | E2 | 11 | 154 |
| HPV18 | E2 | 11 | 132 |
| HPV18 | E2 | 10 | 14 |
| HPV18 | E2 | 8 | 156 |
| HPV18 | E2 | 9 | 156 |
| HPV18 | E2 | 8 | 29 |
| HPV18 | E2 | 9 | 29 |
| HPV18 | E2 | 8 | 315 |
| HPV18 | E2 | 11 | 26 |
| HPV18 | E2 | 9 | 354 |
| HPV18 | E2 | 11 | 104 |
| HPV18 | E2 | 9 | 161 |
| HPV18 | E2 | 9 | 338 |
| HPV18 | E2 | 9 | 329 |
| HPV18 | E2 | 9 | 39 |
| HPV18 | E2 | 10 | 39 |
| HPV18 | E2 | 10 | 133 |
| HPV18 | E2 | 11 | 133 |
| HPV18 | E2 | 8 | 297 |
| HPV18 | E2 | 8 | 107 |
| HPV18 | E2 | 9 | 185 |
| HPV18 | E2 | 10 | 33 |
| HPV18 | E2 | 10 | 38 |
| HPV18 | E2 | 11 | 38 |
| HPV18 | E2 | 9 | 220 |
| HPV18 | E2 | 9 | 88 |
| HPV18 | E2 | 11 | 56 |
| HPV18 | E2 | 9 | 305 |
| HPV18 | E2 | 11 | 230 |
| HPV18 | E2 | 8 | 233 |
| HPV18 | E2 | 8 | 355 |
| HPV18 | E2 | 11 | 140 |
| HPV18 | E2 | 10 | 57 |

TABLE VII-continued

HLA-A1 Supermotif Peptides

| 1 | 2 | 3 | 4 |
|---|---|---|---|
| HPV18 | E2 | 10 | 97 |
| HPV18 | E2 | 10 | 231 |
| HPV18 | E2 | 8 | 157 |
| HPV18 | E2 | 9 | 232 |
| HPV18 | E2 | 11 | 96 |
| HPV18 | E2 | 11 | 173 |
| HPV18 | E2 | 8 | 143 |
| HPV18 | E2 | 8 | 135 |
| HPV18 | E2 | 9 | 135 |
| HPV18 | E2 | 9 | 164 |
| HPV18 | E2 | 10 | 164 |
| HPV18 | E5 | 9 | 47 |
| HPV18 | E5 | 11 | 47 |
| HPV18 | E5 | 11 | 27 |
| HPV18 | E5 | 10 | 6 |
| HPV18 | E5 | 8 | 50 |
| HPV18 | E5 | 8 | 43 |
| HPV18 | E5 | 11 | 43 |
| HPV18 | E5 | 11 | 40 |
| HPV18 | E5 | 10 | 22 |
| HPV18 | E5 | 9 | 2 |
| HPV18 | E5 | 8 | 1 |
| HPV18 | E5 | 10 | 1 |
| HPV18 | E5 | 11 | 21 |
| HPV18 | E5 | 8 | 24 |
| HPV18 | E5 | 10 | 24 |
| HPV18 | E5 | 8 | 3 |
| HPV18 | E5 | 9 | 25 |
| HPV18 | E5 | 10 | 44 |
| HPV18 | E5 | 9 | 42 |
| HPV18 | E5 | 10 | 41 |
| HPV18 | E6 | 8 | 27 |
| HPV18 | E6 | 10 | 77 |
| HPV18 | E6 | 8 | 40 |
| HPV18 | E6 | 10 | 40 |
| HPV18 | E6 | 11 | 43 |
| HPV18 | E6 | 8 | 120 |
| HPV18 | E6 | 11 | 117 |
| HPV18 | E6 | 8 | 92 |
| HPV18 | E6 | 10 | 36 |
| HPV18 | E6 | 9 | 41 |
| HPV18 | E6 | 8 | 74 |
| HPV18 | E6 | 11 | 24 |
| HPV18 | E6 | 11 | 89 |
| HPV18 | E6 | 9 | 37 |
| HPV18 | E6 | 11 | 37 |
| HPV18 | E6 | 8 | 38 |
| HPV18 | E6 | 10 | 38 |
| HPV18 | E6 | 10 | 72 |
| HPV18 | E7 | 9 | 82 |
| HPV18 | E7 | 10 | 77 |
| HPV18 | E7 | 11 | 90 |
| HPV18 | E7 | 9 | 92 |
| HPV18 | E7 | 9 | 88 |
| HPV18 | E7 | 9 | 78 |
| HPV18 | E7 | 8 | 93 |
| HPV18 | L1 | 11 | 63 |
| HPV18 | L1 | 8 | 345 |
| HPV18 | L1 | 11 | 407 |
| HPV18 | L1 | 8 | 310 |
| HPV18 | L1 | 11 | 2 |
| HPV18 | L1 | 9 | 284 |
| HPV18 | L1 | 8 | 122 |
| HPV18 | L1 | 10 | 122 |
| HPV18 | L1 | 11 | 520 |
| HPV18 | L1 | 9 | 364 |
| HPV18 | L1 | 10 | 364 |
| HPV18 | L1 | 9 | 263 |
| HPV18 | L1 | 8 | 330 |
| HPV18 | L1 | 10 | 203 |
| HPV18 | L1 | 8 | 49 |
| HPV18 | L1 | 11 | 49 |
| HPV18 | L1 | 8 | 517 |
| HPV18 | L1 | 8 | 145 |
| HPV18 | L1 | 8 | 177 |
| HPV18 | L1 | 11 | 342 |
| HPV18 | L1 | 11 | 358 |
| HPV18 | L1 | 9 | 383 |
| HPV18 | L1 | 9 | 175 |
| HPV18 | L1 | 10 | 175 |
| HPV18 | L1 | 8 | 38 |
| HPV18 | L1 | 10 | 13 |
| HPV18 | L1 | 11 | 454 |
| HPV18 | L1 | 9 | 428 |
| HPV18 | L1 | 11 | 428 |
| HPV18 | L1 | 10 | 40 |
| HPV18 | L1 | 11 | 39 |
| HPV18 | L1 | 11 | 46 |
| HPV18 | L1 | 10 | 47 |
| HPV18 | L1 | 10 | 9 |
| HPV18 | L1 | 10 | 443 |
| HPV18 | L1 | 9 | 360 |
| HPV18 | L1 | 10 | 125 |
| HPV18 | L1 | 11 | 8 |
| HPV18 | L1 | 9 | 14 |
| HPV18 | L1 | 8 | 103 |
| HPV18 | L1 | 9 | 103 |
| HPV18 | L1 | 8 | 445 |
| HPV18 | L1 | 8 | 104 |
| HPV18 | L1 | 11 | 298 |
| HPV18 | L1 | 11 | 261 |
| HPV18 | L1 | 10 | 36 |
| HPV18 | L1 | 8 | 457 |
| HPV18 | L1 | 10 | 457 |
| HPV18 | L1 | 8 | 510 |
| HPV18 | L1 | 8 | 52 |
| HPV18 | L1 | 9 | 57 |
| HPV18 | L1 | 11 | 282 |
| HPV18 | L1 | 11 | 173 |
| HPV18 | L1 | 8 | 28 |
| HPV18 | L1 | 10 | 26 |
| HPV18 | L1 | 9 | 472 |
| HPV18 | L1 | 11 | 472 |
| HPV18 | L1 | 11 | 412 |
| HPV18 | L1 | 8 | 315 |
| HPV18 | L1 | 8 | 366 |
| HPV18 | L1 | 8 | 137 |
| HPV18 | L1 | 9 | 287 |
| HPV18 | L1 | 8 | 410 |
| HPV18 | L1 | 9 | 102 |
| HPV18 | L1 | 10 | 102 |
| HPV18 | L1 | 10 | 135 |
| HPV18 | L1 | 8 | 81 |
| HPV18 | L1 | 8 | 288 |
| HPV18 | L1 | 8 | 459 |
| HPV18 | L1 | 10 | 359 |
| HPV18 | L1 | 8 | 475 |
| HPV18 | L1 | 10 | 455 |
| HPV18 | L1 | 9 | 458 |
| HPV18 | L1 | 11 | 100 |
| HPV18 | L1 | 10 | 408 |
| HPV18 | L1 | 11 | 78 |
| HPV18 | L1 | 11 | 442 |
| HPV18 | L1 | 9 | 444 |
| HPV18 | L1 | 11 | 327 |
| HPV18 | L1 | 11 | 362 |
| HPV18 | L1 | 9 | 474 |
| HPV18 | L1 | 8 | 473 |
| HPV18 | L1 | 10 | 473 |
| HPV18 | L1 | 9 | 126 |
| HPV18 | L1 | 8 | 89 |
| HPV18 | L1 | 8 | 361 |
| HPV18 | L1 | 9 | 295 |
| HPV18 | L1 | 11 | 35 |
| HPV18 | L1 | 8 | 425 |
| HPV18 | L1 | 9 | 4 |
| HPV18 | L1 | 8 | 88 |
| HPV18 | L1 | 9 | 88 |
| HPV18 | L2 | 11 | 286 |
| HPV18 | L2 | 8 | 341 |

TABLE VII-continued

HLA-A1 Supermotif Peptides

| 1 | 2 | 3 | 4 |
|---|---|---|---|
| HPV18 | L2 | 11 | 341 |
| HPV18 | L2 | 11 | 322 |
| HPV18 | L2 | 11 | 404 |
| HPV18 | L2 | 11 | 443 |
| HPV18 | L2 | 11 | 241 |
| HPV18 | L2 | 11 | 296 |
| HPV18 | L2 | 8 | 429 |
| HPV18 | L2 | 10 | 429 |
| HPV18 | L2 | 10 | 62 |
| HPV18 | L2 | 8 | 64 |
| HPV18 | L2 | 10 | 432 |
| HPV18 | L2 | 11 | 432 |
| HPV18 | L2 | 10 | 183 |
| HPV18 | L2 | 10 | 310 |
| HPV18 | L2 | 11 | 310 |
| HPV18 | L2 | 11 | 37 |
| HPV18 | L2 | 10 | 44 |
| HPV18 | L2 | 10 | 323 |
| HPV18 | L2 | 11 | 152 |
| HPV18 | L2 | 10 | 405 |
| HPV18 | L2 | 8 | 249 |
| HPV18 | L2 | 11 | 43 |
| HPV18 | L2 | 9 | 248 |
| HPV18 | L2 | 10 | 242 |
| HPV18 | L2 | 10 | 287 |
| HPV18 | L2 | 10 | 391 |
| HPV18 | L2 | 11 | 338 |
| HPV18 | L2 | 10 | 386 |
| HPV18 | L2 | 8 | 325 |
| HPV18 | L2 | 11 | 390 |
| HPV18 | L2 | 8 | 362 |
| HPV18 | L2 | 10 | 362 |
| HPV18 | L2 | 11 | 362 |
| HPV18 | L2 | 9 | 419 |
| HPV18 | L2 | 9 | 120 |
| HPV18 | L2 | 9 | 376 |
| HPV18 | L2 | 8 | 185 |
| HPV18 | L2 | 8 | 258 |
| HPV18 | L2 | 10 | 360 |
| HPV18 | L2 | 8 | 312 |
| HPV18 | L2 | 9 | 312 |
| HPV18 | L2 | 10 | 172 |
| HPV18 | L2 | 9 | 233 |
| HPV18 | L2 | 9 | 298 |
| HPV18 | L2 | 9 | 268 |
| HPV18 | L2 | 8 | 364 |
| HPV18 | L2 | 9 | 364 |
| HPV18 | L2 | 11 | 364 |
| HPV18 | L2 | 8 | 220 |
| HPV18 | L2 | 10 | 450 |
| HPV18 | L2 | 10 | 247 |
| HPV18 | L2 | 11 | 246 |
| HPV18 | L2 | B | 393 |
| HPV18 | L2 | 11 | 147 |
| HPV18 | L2 | 10 | 153 |
| HPV18 | L2 | 8 | 365 |
| HPV18 | L2 | 10 | 365 |
| HPV18 | L2 | 9 | 149 |
| HPV18 | L2 | 8 | 377 |
| HPV18 | L2 | 9 | 39 |
| HPV18 | L2 | 9 | 406 |
| HPV18 | L2 | 8 | 367 |
| HPV18 | L2 | 9 | 114 |
| HPV18 | L2 | 9 | 288 |
| HPV18 | L2 | 9 | 392 |
| HPV18 | L2 | 10 | 148 |
| HPV18 | L2 | 10 | 38 |
| HPV18 | L2 | 9 | 154 |
| HPV18 | L2 | 9 | 366 |
| HPV18 | L2 | 8 | 388 |
| HPV18 | L2 | 11 | 217 |
| HPV18 | L2 | 10 | 339 |
| HPV18 | L2 | 8 | 150 |
| HPV18 | L2 | 11 | 417 |
| HPV18 | L2 | 8 | 234 |
| HPV18 | L2 | 10 | 113 |
| HPV18 | L2 | 9 | 387 |
| HPV18 | L2 | 11 | 112 |
| HPV18 | L2 | 9 | 427 |
| HPV18 | L2 | 10 | 427 |
| HPV18 | L2 | 8 | 436 |
| HPV18 | L2 | 11 | 374 |
| HPV31 | E1 | 10 | 186 |
| HPV31 | E1 | 8 | 504 |
| HPV31 | E1 | 9 | 81 |
| HPV31 | E1 | 9 | 213 |
| HPV31 | E1 | 8 | 96 |
| HPV31 | E1 | 8 | 421 |
| HPV31 | E1 | 8 | 336 |
| HPV31 | E1 | 10 | 336 |
| HPV31 | E1 | 9 | 364 |
| HPV31 | E1 | 8 | 352 |
| HPV31 | E1 | 9 | 42 |
| HPV31 | E1 | 10 | 348 |
| HPV31 | E1 | 9 | 311 |
| HPV31 | E1 | 10 | 583 |
| HPV31 | E1 | 11 | 583 |
| HPV31 | E1 | 8 | 50 |
| HPV31 | E1 | 9 | 473 |
| HPV31 | E1 | 9 | 425 |
| HPV31 | E1 | 8 | 436 |
| HPV31 | E1 | 8 | 199 |
| HPV31 | E1 | 9 | 566 |
| HPV31 | E1 | 11 | 433 |
| HPV31 | E1 | 11 | 499 |
| HPV31 | E1 | 9 | 305 |
| HPV31 | E1 | 10 | 252 |
| HPV31 | E1 | 8 | 11 |
| HPV31 | E1 | 9 | 11 |
| HPV31 | E1 | 11 | 196 |
| HPV31 | E1 | 10 | 222 |
| HPV31 | E1 | 9 | 243 |
| HPV31 | E1 | 8 | 328 |
| HPV31 | E1 | 9 | 560 |
| HPV31 | E1 | 11 | 478 |
| HPV31 | E1 | 11 | 309 |
| HPV31 | E1 | 11 | 471 |
| HPV31 | E1 | 10 | 479 |
| HPV31 | E1 | 11 | 479 |
| HPV31 | E1 | 10 | 291 |
| HPV31 | E1 | 11 | 291 |
| HPV31 | E1 | 8 | 590 |
| HPV31 | E1 | 11 | 463 |
| HPV31 | E1 | 8 | 119 |
| HPV31 | E1 | 10 | 232 |
| HPV31 | E1 | 8 | 412 |
| HPV31 | E1 | 8 | 234 |
| HPV31 | E1 | 10 | 94 |
| HPV31 | E1 | 9 | 584 |
| HPV31 | E1 | 10 | 584 |
| HPV31 | E1 | 9 | 337 |
| HPV31 | E1 | 10 | 563 |
| HPV31 | E1 | 10 | 500 |
| HPV31 | E1 | 9 | 187 |
| HPV31 | E1 | 8 | 306 |
| HPV31 | E1 | 11 | 47 |
| HPV31 | E1 | 9 | 253 |
| HPV31 | E1 | 10 | 547 |
| HPV31 | E1 | 10 | 117 |
| HPV31 | E1 | 11 | 93 |
| HPV31 | E1 | 10 | 580 |
| HPV31 | E1 | 10 | 207 |
| HPV31 | E1 | 8 | 323 |
| HPV31 | E1 | 10 | 124 |
| HPV31 | E1 | 11 | 562 |
| HPV31 | E1 | 8 | 293 |
| HPV31 | E1 | 9 | 293 |
| HPV31 | E1 | 10 | 293 |
| HPV31 | E1 | 11 | 303 |
| HPV31 | E1 | 11 | 40 |

TABLE VII-continued

HLA-A1 Supermotif Peptides

| 1 | 2 | 3 | 4 |
|---|---|---|---|
| HPV31 | E1 | 8 | 294 |
| HPV31 | E1 | 9 | 294 |
| HPV31 | E1 | 11 | 211 |
| HPV31 | E1 | 9 | 233 |
| HPV31 | E1 | 11 | 333 |
| HPV31 | E1 | 11 | 505 |
| HPV31 | E1 | 11 | 325 |
| HPV31 | E1 | 9 | 349 |
| HPV31 | E1 | 11 | 349 |
| HPV31 | E1 | 8 | 254 |
| HPV31 | E1 | 10 | 434 |
| HPV31 | E1 | 10 | 197 |
| HPV31 | E1 | 9 | 223 |
| HPV31 | E1 | 9 | 564 |
| HPV31 | E1 | 11 | 564 |
| HPV31 | E1 | 9 | 558 |
| HPV31 | E1 | 11 | 558 |
| HPV31 | E2 | 9 | 307 |
| HPV31 | E2 | 11 | 22 |
| HPV31 | E2 | 8 | 124 |
| HPV31 | E2 | 11 | 124 |
| HPV31 | E2 | 11 | 197 |
| HPV31 | E2 | 8 | 80 |
| HPV31 | E2 | 11 | 185 |
| HPV31 | E2 | 8 | 200 |
| HPV31 | E2 | 8 | 171 |
| HPV31 | E2 | 11 | 168 |
| HPV31 | E2 | 10 | 35 |
| HPV31 | E2 | 8 | 164 |
| HPV31 | E2 | 9 | 345 |
| HPV31 | E2 | 8 | 193 |
| HPV31 | E2 | 8 | 312 |
| HPV31 | E2 | 10 | 78 |
| HPV31 | E2 | 11 | 77 |
| HPV31 | E2 | 8 | 303 |
| HPV31 | E2 | 9 | 84 |
| HPV31 | E2 | 8 | 127 |
| HPV31 | E2 | 10 | 127 |
| HPV31 | E2 | 9 | 361 |
| HPV31 | E2 | 11 | 9 |
| HPV31 | E2 | 10 | 106 |
| HPV31 | E2 | 10 | 317 |
| HPV31 | E2 | 10 | 191 |
| HPV31 | E2 | 8 | 151 |
| HPV31 | E2 | 9 | 151 |
| HPV31 | E2 | 8 | 321 |
| HPV31 | E2 | 8 | 25 |
| HPV31 | E2 | 9 | 25 |
| HPV31 | E2 | 8 | 37 |
| HPV31 | E2 | 9 | 311 |
| HPV31 | E2 | 8 | 346 |
| HPV31 | E2 | 10 | 198 |
| HPV31 | E2 | 9 | 128 |
| HPV31 | E2 | 11 | 128 |
| HPV31 | E2 | 10 | 93 |
| HPV31 | E2 | 8 | 362 |
| HPV31 | E2 | 9 | 192 |
| HPV31 | E2 | 11 | 92 |
| HPV31 | E2 | 10 | 344 |
| HPV31 | E2 | 8 | 131 |
| HPV31 | E2 | 9 | 159 |
| HPV31 | E2 | 10 | 159 |
| HPV31 | E5 | 11 | 40 |
| HPV31 | E5 | 8 | 53 |
| HPV31 | E5 | 11 | 53 |
| HPV31 | E5 | 8 | 61 |
| HPV31 | E5 | 10 | 15 |
| HPV31 | E5 | 9 | 72 |
| HPV31 | E5 | 10 | 6 |
| HPV31 | E5 | 9 | 11 |
| HPV31 | E5 | 9 | 16 |
| HPV31 | E5 | 8 | 43 |
| HPV31 | E5 | 9 | 42 |
| HPV31 | E5 | 8 | 32 |
| HPV31 | E5 | 11 | 5 |
| HPV31 | E5 | 11 | 70 |
| HPV31 | E5 | 8 | 56 |
| HPV31 | E5 | 11 | 56 |
| HPV31 | E5 | 9 | 31 |
| HPV31 | E5 | 10 | 10 |
| HPV31 | E5 | 9 | 7 |
| HPV31 | E5 | 10 | 41 |
| HPV31 | E5 | 10 | 54 |
| HPV31 | E5 | 8 | 8 |
| HPV31 | E5 | 10 | 51 |
| HPV31 | E5 | 8 | 73 |
| HPV31 | E5 | 8 | 12 |
| HPV31 | E5 | 11 | 9 |
| HPV31 | E5 | 9 | 64 |
| HPV31 | E5 | 11 | 50 |
| HPV31 | E5 | 10 | 63 |
| HPV31 | E6 | 11 | 66 |
| HPV31 | E6 | 8 | 63 |
| HPV31 | E6 | 8 | 25 |
| HPV31 | E6 | 10 | 14 |
| HPV31 | E6 | 9 | 39 |
| HPV31 | E6 | 8 | 47 |
| HPV31 | E6 | 9 | 61 |
| HPV31 | E6 | 10 | 61 |
| HPV31 | E6 | 8 | 118 |
| HPV31 | E6 | 8 | 72 |
| HPV31 | E6 | 10 | 72 |
| HPV31 | E6 | 9 | 15 |
| HPV31 | E6 | 9 | 37 |
| HPV31 | E6 | 11 | 37 |
| HPV31 | E6 | 10 | 36 |
| HPV31 | E6 | 8 | 16 |
| HPV31 | E6 | 9 | 73 |
| HPV31 | E6 | 9 | 132 |
| HPV31 | E6 | 9 | 70 |
| HPV31 | E6 | 10 | 70 |
| HPV31 | E7 | 10 | 48 |
| HPV31 | E7 | 8 | 4 |
| HPV31 | E7 | 10 | 78 |
| HPV31 | E7 | 11 | 77 |
| HPV31 | E7 | 9 | 49 |
| HPV31 | L1 | 9 | 348 |
| HPV31 | L1 | 8 | 398 |
| HPV31 | L1 | 8 | 285 |
| HPV31 | L1 | 9 | 285 |
| HPV31 | L1 | 9 | 224 |
| HPV31 | L1 | 11 | 459 |
| HPV31 | L1 | 8 | 129 |
| HPV31 | L1 | 9 | 203 |
| HPV31 | L1 | 9 | 353 |
| HPV31 | L1 | 8 | 270 |
| HPV31 | L1 | 8 | 449 |
| HPV31 | L1 | 8 | 456 |
| HPV31 | L1 | 9 | 323 |
| HPV31 | L1 | 11 | 117 |
| HPV31 | L1 | 9 | 413 |
| HPV31 | L1 | 11 | 298 |
| HPV31 | L1 | 11 | 282 |
| HPV31 | L1 | 11 | 393 |
| HPV31 | L1 | 10 | 118 |
| HPV31 | L1 | 10 | 382 |
| HPV31 | L1 | 11 | 61 |
| HPV31 | L1 | 11 | 381 |
| HPV31 | L1 | 8 | 357 |
| HPV31 | L1 | 10 | 65 |
| HPV31 | L1 | 8 | 20 |
| HPV31 | L1 | 8 | 42 |
| HPV31 | L1 | 9 | 42 |
| HPV31 | L1 | 8 | 384 |
| HPV31 | L1 | 8 | 43 |
| HPV31 | L1 | 11 | 238 |
| HPV31 | L1 | 11 | 201 |
| HPV31 | L1 | 9 | 300 |
| HPV31 | L1 | 11 | 351 |
| HPV31 | L1 | 9 | 227 |

TABLE VII-continued

HLA-A1 Supermotif Peptides

| 1 | 2 | 3 | 4 |
|---|---|---|---|
| HPV31 | L1 | 11 | 222 |
| HPV31 | L1 | 9 | 411 |
| HPV31 | L1 | 11 | 411 |
| HPV31 | L1 | 11 | 17 |
| HPV31 | L1 | 8 | 306 |
| HPV31 | L1 | 8 | 255 |
| HPV31 | L1 | 9 | 41 |
| HPV31 | L1 | 10 | 41 |
| HPV31 | L1 | 8 | 77 |
| HPV31 | L1 | 10 | 77 |
| HPV31 | L1 | 10 | 75 |
| HPV31 | L1 | 8 | 228 |
| HPV31 | L1 | 8 | 414 |
| HPV31 | L1 | 11 | 2 |
| HPV31 | L1 | 10 | 394 |
| HPV31 | L1 | 10 | 299 |
| HPV31 | L1 | 10 | 283 |
| HPV31 | L1 | 11 | 283 |
| HPV31 | L1 | 8 | 286 |
| HPV31 | L1 | 9 | 383 |
| HPV31 | L1 | 11 | 302 |
| HPV31 | L1 | 8 | 354 |
| HPV31 | L1 | 11 | 354 |
| HPV31 | L1 | 11 | 267 |
| HPV31 | L1 | 9 | 66 |
| HPV31 | L1 | 10 | 18 |
| HPV31 | L1 | 8 | 28 |
| HPV31 | L1 | 8 | 301 |
| HPV31 | L1 | 10 | 62 |
| HPV31 | L1 | 9 | 235 |
| HPV31 | L1 | 8 | 364 |
| HPV31 | L1 | 8 | 250 |
| HPV31 | L1 | 8 | 27 |
| HPV31 | L1 | 9 | 27 |
| HPV31 | L2 | 11 | 286 |
| HPV31 | L2 | 9 | 311 |
| HPV31 | L2 | 10 | 311 |
| HPV31 | L2 | 11 | 311 |
| HPV31 | L2 | 11 | 376 |
| HPV31 | L2 | 8 | 354 |
| HPV31 | L2 | 10 | 253 |
| HPV31 | L2 | 11 | 253 |
| HPV31 | L2 | 11 | 237 |
| HPV31 | L2 | 8 | 433 |
| HPV31 | L2 | 11 | 351 |
| HPV31 | L2 | 10 | 63 |
| HPV31 | L2 | 8 | 65 |
| HPV31 | L2 | 11 | 213 |
| HPV31 | L2 | 11 | 38 |
| HPV31 | L2 | 10 | 45 |
| HPV31 | L2 | 11 | 45 |
| HPV31 | L2 | 8 | 245 |
| HPV31 | L2 | 9 | 244 |
| HPV31 | L2 | 10 | 238 |
| HPV31 | L2 | 11 | 178 |
| HPV31 | L2 | 10 | 395 |
| HPV31 | L2 | 10 | 287 |
| HPV31 | L2 | 11 | 447 |
| HPV31 | L2 | 8 | 269 |
| HPV31 | L2 | 10 | 390 |
| HPV31 | L2 | 10 | 410 |
| HPV31 | L2 | 11 | 122 |
| HPV31 | L2 | 11 | 394 |
| HPV31 | L2 | 9 | 425 |
| HPV31 | L2 | 11 | 44 |
| HPV31 | L2 | 10 | 243 |
| HPV31 | L2 | 9 | 378 |
| HPV31 | L2 | 9 | 229 |
| HPV31 | L2 | 11 | 429 |
| HPV31 | L2 | 11 | 9 |
| HPV31 | L2 | 9 | 431 |
| HPV31 | L2 | 10 | 431 |
| HPV31 | L2 | 8 | 181 |
| HPV31 | L2 | 9 | 180 |
| HPV31 | L2 | 10 | 179 |
| HPV31 | L2 | 9 | 396 |
| HPV31 | L2 | 8 | 151 |
| HPV31 | L2 | 8 | 346 |
| HPV31 | L2 | 11 | 346 |
| HPV31 | L2 | 8 | 379 |
| HPV31 | L2 | 10 | 149 |
| HPV31 | L2 | 9 | 40 |
| HPV31 | L2 | 8 | 312 |
| HPV31 | L2 | 9 | 312 |
| HPV31 | L2 | 10 | 312 |
| HPV31 | L2 | 10 | 347 |
| HPV31 | L2 | 11 | 266 |
| HPV31 | L2 | 9 | 288 |
| HPV31 | L2 | 9 | 345 |
| HPV31 | L2 | 11 | 148 |
| HPV31 | L2 | 10 | 39 |
| HPV31 | L2 | 8 | 426 |
| HPV31 | L2 | 10 | 344 |
| HPV31 | L2 | 11 | 343 |
| HPV31 | L2 | 9 | 391 |
| HPV31 | L2 | 9 | 254 |
| HPV31 | L2 | 10 | 254 |
| HPV31 | L2 | 8 | 392 |
| HPV31 | L2 | 10 | 430 |
| HPV31 | L2 | 11 | 430 |
| HPV31 | L2 | 9 | 150 |
| HPV33 | E1 | 10 | 596 |
| HPV33 | E1 | 11 | 596 |
| HPV33 | E1 | 9 | 81 |
| HPV33 | E1 | 9 | 226 |
| HPV33 | E1 | 8 | 494 |
| HPV33 | E1 | 9 | 494 |
| HPV33 | E1 | 8 | 349 |
| HPV33 | E1 | 10 | 349 |
| HPV33 | E1 | 8 | 365 |
| HPV33 | E1 | 9 | 42 |
| HPV33 | E1 | 9 | 377 |
| HPV33 | E1 | 9 | 62 |
| HPV33 | E1 | 9 | 324 |
| HPV33 | E1 | 9 | 516 |
| HPV33 | E1 | 10 | 361 |
| HPV33 | E1 | 11 | 361 |
| HPV33 | E1 | 8 | 449 |
| HPV33 | E1 | 8 | 212 |
| HPV33 | E1 | 8 | 446 |
| HPV33 | E1 | 11 | 446 |
| HPV33 | E1 | 10 | 265 |
| HPV33 | E1 | 11 | 209 |
| HPV33 | E1 | 8 | 11 |
| HPV33 | E1 | 11 | 512 |
| HPV33 | E1 | 8 | 564 |
| HPV33 | E1 | 8 | 341 |
| HPV33 | E1 | 9 | 573 |
| HPV33 | E1 | 11 | 192 |
| HPV33 | E1 | 9 | 266 |
| HPV33 | E1 | 8 | 267 |
| HPV33 | E1 | 9 | 200 |
| HPV33 | E1 | 10 | 492 |
| HPV33 | E1 | 11 | 492 |
| HPV33 | E1 | 11 | 322 |
| HPV33 | E1 | 10 | 210 |
| HPV33 | E1 | 9 | 520 |
| HPV33 | E1 | 10 | 124 |
| HPV33 | E1 | 10 | 304 |
| HPV33 | E1 | 11 | 304 |
| HPV33 | E1 | 10 | 220 |
| HPV33 | E1 | 8 | 603 |
| HPV33 | E1 | 11 | 476 |
| HPV33 | E1 | 8 | 425 |
| HPV33 | E1 | 10 | 245 |
| HPV33 | E1 | 8 | 247 |
| HPV33 | E1 | 9 | 438 |
| HPV33 | E1 | 9 | 350 |
| HPV33 | E1 | 9 | 362 |
| HPV33 | E1 | 10 | 362 |

TABLE VII-continued

HLA-A1 Supermotif Peptides

| 1 | 2 | 3 | 4 |
|---|---|---|---|
| HPV33 | E1 | 11 | 362 |
| HPV33 | E1 | 10 | 576 |
| HPV33 | E1 | 8 | 336 |
| HPV33 | E1 | 10 | 513 |
| HPV33 | E1 | 11 | 443 |
| HPV33 | E1 | 11 | 346 |
| HPV33 | E1 | 10 | 199 |
| HPV33 | E1 | 8 | 195 |
| HPV33 | E1 | 10 | 195 |
| HPV33 | E1 | 10 | 560 |
| HPV33 | E1 | 10 | 519 |
| HPV33 | E1 | 8 | 434 |
| HPV33 | E1 | 10 | 593 |
| HPV33 | E1 | 10 | 437 |
| HPV33 | E1 | 8 | 308 |
| HPV33 | E1 | 11 | 575 |
| HPV33 | E1 | 9 | 335 |
| HPV33 | E1 | 8 | 306 |
| HPV33 | E1 | 9 | 306 |
| HPV33 | E1 | 10 | 306 |
| HPV33 | E1 | 10 | 111 |
| HPV33 | E1 | 10 | 193 |
| HPV33 | E1 | 11 | 224 |
| HPV33 | E1 | 11 | 110 |
| HPV33 | E1 | 9 | 577 |
| HPV33 | E1 | 11 | 577 |
| HPV33 | E1 | 11 | 491 |
| HPV33 | E1 | 9 | 246 |
| HPV33 | E1 | 11 | 338 |
| HPV33 | E1 | 8 | 517 |
| HPV33 | E1 | 9 | 571 |
| HPV33 | E1 | 11 | 571 |
| HPV33 | E2 | 10 | 78 |
| HPV33 | E2 | 11 | 41 |
| HPV33 | E2 | 10 | 10 |
| HPV33 | E2 | 9 | 288 |
| HPV33 | E2 | 10 | 145 |
| HPV33 | E2 | 9 | 25 |
| HPV33 | E2 | 10 | 235 |
| HPV33 | E2 | 10 | 298 |
| HPV33 | E2 | 10 | 282 |
| HPV33 | E2 | 8 | 80 |
| HPV33 | E2 | 11 | 100 |
| HPV33 | E2 | 10 | 325 |
| HPV33 | E2 | 11 | 34 |
| HPV33 | E2 | 9 | 84 |
| HPV33 | E2 | 11 | 23 |
| HPV33 | E2 | 8 | 151 |
| HPV33 | E2 | 9 | 151 |
| HPV33 | E2 | 10 | 35 |
| HPV33 | E2 | 9 | 62 |
| HPV33 | E2 | 10 | 42 |
| HPV33 | E2 | 11 | 82 |
| HPV33 | E2 | 8 | 147 |
| HPV33 | E2 | 11 | 315 |
| HPV33 | E2 | 8 | 284 |
| HPV33 | E2 | 8 | 127 |
| HPV33 | E2 | 11 | 60 |
| HPV33 | E2 | 9 | 342 |
| HPV33 | E2 | 9 | 292 |
| HPV33 | E2 | 8 | 37 |
| HPV33 | E2 | 10 | 61 |
| HPV33 | E2 | 8 | 302 |
| HPV33 | E2 | 9 | 301 |
| HPV33 | E2 | 10 | 93 |
| HPV33 | E2 | 11 | 128 |
| HPV33 | E2 | 9 | 146 |
| HPV33 | E2 | 8 | 343 |
| HPV33 | E2 | 9 | 326 |
| HPV33 | E2 | 11 | 148 |
| HPV33 | E2 | 9 | 102 |
| HPV33 | E2 | 11 | 92 |
| HPV33 | E2 | 9 | 159 |
| HPV33 | E2 | 10 | 159 |
| HPV33 | E2 | 8 | 300 |
| HPV33 | E2 | 10 | 300 |
| HPV33 | E2 | 8 | 44 |
| HPV33 | E2 | 8 | 131 |
| HPV33 | E5 | 11 | 56 |
| HPV33 | E5 | 10 | 3 |
| HPV33 | E5 | 9 | 42 |
| HPV33 | E5 | 10 | 42 |
| HPV33 | E5 | 8 | 5 |
| HPV33 | E5 | 8 | 44 |
| HPV33 | E5 | 10 | 44 |
| HPV33 | E5 | 9 | 23 |
| HPV33 | E5 | 9 | 48 |
| HPV33 | E5 | 11 | 48 |
| HPV33 | E5 | 8 | 22 |
| HPV33 | E5 | 10 | 22 |
| HPV33 | E5 | 9 | 32 |
| HPV33 | E5 | 11 | 32 |
| HPV33 | E5 | 8 | 24 |
| HPV33 | E5 | 8 | 35 |
| HPV33 | E5 | 8 | 33 |
| HPV33 | E5 | 10 | 33 |
| HPV33 | E5 | 9 | 1 |
| HPV33 | E5 | 9 | 21 |
| HPV33 | E5 | 11 | 21 |
| HPV33 | E5 | 8 | 46 |
| HPV33 | E5 | 11 | 46 |
| HPV33 | E5 | 9 | 34 |
| HPV33 | E5 | 10 | 31 |
| HPV33 | E5 | 11 | 40 |
| HPV33 | E5 | 9 | 58 |
| HPV33 | E6 | 11 | 66 |
| HPV33 | E6 | 8 | 69 |
| HPV33 | E6 | 11 | 69 |
| HPV33 | E6 | 9 | 61 |
| HPV33 | E6 | 8 | 118 |
| HPV33 | E6 | 9 | 73 |
| HPV33 | E6 | 8 | 72 |
| HPV33 | E6 | 10 | 72 |
| HPV33 | E6 | 10 | 70 |
| HPV33 | E6 | 11 | 50 |
| HPV33 | E6 | 8 | 36 |
| HPV33 | E6 | 10 | 36 |
| HPV33 | E6 | 9 | 39 |
| HPV33 | E6 | 10 | 51 |
| HPV33 | E6 | 9 | 52 |
| HPV33 | E7 | 10 | 14 |
| HPV33 | E7 | 11 | 6 |
| HPV33 | E7 | 10 | 7 |
| HPV33 | L1 | 10 | 392 |
| HPV33 | L1 | 8 | 284 |
| HPV33 | L1 | 9 | 284 |
| HPV33 | L1 | 9 | 411 |
| HPV33 | L1 | 10 | 345 |
| HPV33 | L1 | 9 | 223 |
| HPV33 | L1 | 8 | 396 |
| HPV33 | L1 | 11 | 457 |
| HPV33 | L1 | 9 | 351 |
| HPV33 | L1 | 8 | 129 |
| HPV33 | L1 | 9 | 202 |
| HPV33 | L1 | 9 | 303 |
| HPV33 | L1 | 10 | 303 |
| HPV33 | L1 | 8 | 447 |
| HPV33 | L1 | 8 | 249 |
| HPV33 | L1 | 8 | 454 |
| HPV33 | L1 | 9 | 322 |
| HPV33 | L1 | 11 | 117 |
| HPV33 | L1 | 11 | 297 |
| HPV33 | L1 | 9 | 226 |
| HPV33 | L1 | 11 | 281 |
| HPV33 | L1 | 9 | 365 |
| HPV33 | L1 | 11 | 365 |
| HPV33 | L1 | 10 | 118 |
| HPV33 | L1 | 10 | 65 |
| HPV33 | L1 | 11 | 379 |
| HPV33 | L1 | 8 | 20 |

TABLE VII-continued

HLA-A1 Supermotif Peptides

| 1 | 2 | 3 | 4 |
|---|---|---|---|
| HPV33 | L1 | 8 | 42 |
| HPV33 | L1 | 9 | 42 |
| HPV33 | L1 | 11 | 61 |
| HPV33 | L1 | 8 | 382 |
| HPV33 | L1 | 10 | 62 |
| HPV33 | L1 | 11 | 237 |
| HPV33 | L1 | 11 | 200 |
| HPV33 | L1 | 9 | 299 |
| HPV33 | L1 | 11 | 221 |
| HPV33 | L1 | 8 | 439 |
| HPV33 | L1 | 9 | 409 |
| HPV33 | L1 | 11 | 409 |
| HPV33 | L1 | 11 | 17 |
| HPV33 | L1 | 8 | 305 |
| HPV33 | L1 | 8 | 254 |
| HPV33 | L1 | 8 | 347 |
| HPV33 | L1 | 9 | 41 |
| HPV33 | L1 | 10 | 41 |
| HPV33 | L1 | 8 | 77 |
| HPV33 | L1 | 10 | 77 |
| HPV33 | L1 | 10 | 75 |
| HPV33 | L1 | 8 | 285 |
| HPV33 | L1 | 8 | 412 |
| HPV33 | L1 | 10 | 298 |
| HPV33 | L1 | 11 | 39 |
| HPV33 | L1 | 8 | 227 |
| HPV33 | L1 | 8 | 352 |
| HPV33 | L1 | 11 | 352 |
| HPV33 | L1 | 11 | 2 |
| HPV33 | L1 | 11 | 266 |
| HPV33 | L1 | 9 | 381 |
| HPV33 | L1 | 11 | 349 |
| HPV33 | L1 | 10 | 238 |
| HPV33 | L1 | 11 | 238 |
| HPV33 | L1 | 11 | 301 |
| HPV33 | L1 | 10 | 282 |
| HPV33 | L1 | 11 | 282 |
| HPV33 | L1 | 9 | 66 |
| HPV33 | L1 | 10 | 18 |
| HPV33 | L1 | 8 | 28 |
| HPV33 | L1 | 9 | 28 |
| HPV33 | L1 | 10 | 380 |
| HPV33 | L1 | 8 | 300 |
| HPV33 | L1 | 8 | 362 |
| HPV33 | L1 | 9 | 234 |
| HPV33 | L1 | 8 | 27 |
| HPV33 | L1 | 9 | 27 |
| HPV33 | L1 | 10 | 27 |
| HPV33 | L2 | 11 | 291 |
| HPV33 | L2 | 10 | 272 |
| HPV33 | L2 | 10 | 431 |
| HPV33 | L2 | 11 | 258 |
| HPV33 | L2 | 10 | 447 |
| HPV33 | L2 | 11 | 242 |
| HPV33 | L2 | 11 | 183 |
| HPV33 | L2 | 8 | 440 |
| HPV33 | L2 | 8 | 421 |
| HPV33 | L2 | 10 | 421 |
| HPV33 | L2 | 8 | 64 |
| HPV33 | L2 | 10 | 62 |
| HPV33 | L2 | 11 | 218 |
| HPV33 | L2 | 11 | 37 |
| HPV33 | L2 | 8 | 374 |
| HPV33 | L2 | 11 | 374 |
| HPV33 | L2 | 8 | 336 |
| HPV33 | L2 | 10 | 44 |
| HPV33 | L2 | 11 | 44 |
| HPV33 | L2 | 9 | 448 |
| HPV33 | L2 | 11 | 448 |
| HPV33 | L2 | 9 | 273 |
| HPV33 | L2 | 9 | 155 |
| HPV33 | L2 | 10 | 292 |
| HPV33 | L2 | 8 | 250 |
| HPV33 | L2 | 11 | 250 |
| HPV33 | L2 | 10 | 104 |
| HPV33 | L2 | 8 | 433 |
| HPV33 | L2 | 10 | 248 |
| HPV33 | L2 | 9 | 249 |
| HPV33 | L2 | 10 | 243 |
| HPV33 | L2 | 11 | 405 |
| HPV33 | L2 | 10 | 372 |
| HPV33 | L2 | 10 | 391 |
| HPV33 | L2 | 8 | 423 |
| HPV33 | L2 | 11 | 333 |
| HPV33 | L2 | 9 | 413 |
| HPV33 | L2 | 10 | 347 |
| HPV33 | L2 | 9 | 376 |
| HPV33 | L2 | 9 | 121 |
| HPV33 | L2 | 11 | 411 |
| HPV33 | L2 | 8 | 186 |
| HPV33 | L2 | 8 | 221 |
| HPV33 | L2 | 8 | 317 |
| HPV33 | L2 | 9 | 317 |
| HPV33 | L2 | 11 | 43 |
| HPV33 | L2 | 11 | 191 |
| HPV33 | L2 | 11 | 153 |
| HPV33 | L2 | 9 | 234 |
| HPV33 | L2 | 10 | 357 |
| HPV33 | L2 | 8 | 393 |
| HPV33 | L2 | 8 | 122 |
| HPV33 | L2 | 11 | 103 |
| HPV33 | L2 | 8 | 106 |
| HPV33 | L2 | 10 | 418 |
| HPV33 | L2 | 11 | 418 |
| HPV33 | L2 | 10 | 184 |
| HPV33 | L2 | 10 | 354 |
| HPV33 | L2 | 8 | 156 |
| HPV33 | L2 | 10 | 38 |
| HPV33 | L2 | 9 | 39 |
| HPV33 | L2 | 10 | 154 |
| HPV33 | L2 | 9 | 432 |
| HPV33 | L2 | 9 | 244 |
| HPV33 | L2 | 9 | 293 |
| HPV33 | L2 | 11 | 417 |
| HPV33 | L2 | 11 | 353 |
| HPV33 | L2 | 9 | 392 |
| HPV33 | L2 | 9 | 105 |
| HPV33 | L2 | 8 | 356 |
| HPV33 | L2 | 11 | 356 |
| HPV45 | E1 | 10 | 199 |
| HPV45 | E1 | 11 | 512 |
| HPV45 | E1 | 11 | 40 |
| HPV45 | E1 | 8 | 517 |
| HPV45 | E1 | 9 | 517 |
| HPV45 | E1 | 11 | 202 |
| HPV45 | E1 | 10 | 423 |
| HPV45 | E1 | 9 | 226 |
| HPV45 | E1 | 8 | 349 |
| HPV45 | E1 | 10 | 349 |
| HPV45 | E1 | 10 | 361 |
| HPV45 | E1 | 10 | 623 |
| HPV45 | E1 | 9 | 42 |
| HPV45 | E1 | 10 | 596 |
| HPV45 | E1 | 11 | 596 |
| HPV45 | E1 | 8 | 365 |
| HPV45 | E1 | 9 | 573 |
| HPV45 | E1 | 9 | 324 |
| HPV45 | E1 | 11 | 446 |
| HPV45 | E1 | 10 | 385 |
| HPV45 | E1 | 9 | 486 |
| HPV45 | E1 | 8 | 449 |
| HPV45 | E1 | 9 | 438 |
| HPV45 | E1 | 8 | 212 |
| HPV45 | E1 | 9 | 579 |
| HPV45 | E1 | 8 | 130 |
| HPV45 | E1 | 8 | 494 |
| HPV45 | E1 | 9 | 494 |
| HPV45 | E1 | 11 | 209 |
| HPV45 | E1 | 8 | 11 |
| HPV45 | E1 | 9 | 11 |

TABLE VII-continued

HLA-A1 Supermotif Peptides

| 1 | 2 | 3 | 4 |
|---|---|---|---|
| HPV45 | E1 | 11 | 459 |
| HPV45 | E1 | 10 | 265 |
| HPV45 | E1 | 10 | 235 |
| HPV45 | E1 | 9 | 256 |
| HPV45 | E1 | 10 | 519 |
| HPV45 | E1 | 11 | 338 |
| HPV45 | E1 | 11 | 491 |
| HPV45 | E1 | 11 | 322 |
| HPV45 | E1 | 10 | 447 |
| HPV45 | E1 | 10 | 492 |
| HPV45 | E1 | 11 | 492 |
| HPV45 | E1 | 8 | 425 |
| HPV45 | E1 | 10 | 304 |
| HPV45 | E1 | 11 | 304 |
| HPV45 | E1 | 10 | 220 |
| HPV45 | E1 | 8 | 387 |
| HPV45 | E1 | 8 | 476 |
| HPV45 | E1 | 11 | 476 |
| HPV45 | E1 | 10 | 245 |
| HPV45 | E1 | 8 | 247 |
| HPV45 | E1 | 8 | 267 |
| HPV45 | E1 | 9 | 350 |
| HPV45 | E1 | 10 | 210 |
| HPV45 | E1 | 9 | 362 |
| HPV45 | E1 | 11 | 362 |
| HPV45 | E1 | 9 | 200 |
| HPV45 | E1 | 10 | 513 |
| HPV45 | E1 | 10 | 560 |
| HPV45 | E1 | 8 | 414 |
| HPV45 | E1 | 11 | 473 |
| HPV45 | E1 | 8 | 434 |
| HPV45 | E1 | 10 | 593 |
| HPV45 | E1 | 10 | 412 |
| HPV45 | E1 | 10 | 80 |
| HPV45 | E1 | 10 | 128 |
| HPV45 | E1 | 8 | 306 |
| HPV45 | E1 | 9 | 306 |
| HPV45 | E1 | 10 | 306 |
| HPV45 | E1 | 11 | 575 |
| HPV45 | E1 | 8 | 307 |
| HPV45 | E1 | 9 | 307 |
| HPV45 | E1 | 8 | 308 |
| HPV45 | E1 | 9 | 246 |
| HPV45 | E1 | 11 | 224 |
| HPV45 | E1 | 9 | 577 |
| HPV45 | E1 | 11 | 577 |
| HPV45 | E1 | 9 | 81 |
| HPV45 | E1 | 9 | 266 |
| HPV45 | E1 | 8 | 325 |
| HPV45 | E1 | 10 | 576 |
| HPV45 | E1 | 9 | 571 |
| HPV45 | E1 | 11 | 571 |
| HPV45 | E2 | 10 | 84 |
| HPV45 | E2 | 10 | 16 |
| HPV45 | E2 | 9 | 305 |
| HPV45 | E2 | 11 | 134 |
| HPV45 | E2 | 8 | 158 |
| HPV45 | E2 | 9 | 158 |
| HPV45 | E2 | 8 | 31 |
| HPV45 | E2 | 9 | 31 |
| HPV45 | E2 | 11 | 28 |
| HPV45 | E2 | 8 | 171 |
| HPV45 | E2 | 8 | 319 |
| HPV45 | E2 | 11 | 106 |
| HPV45 | E2 | 8 | 154 |
| HPV45 | E2 | 9 | 154 |
| HPV45 | E2 | 10 | 41 |
| HPV45 | E2 | 9 | 341 |
| HPV45 | E2 | 8 | 301 |
| HPV45 | E2 | 9 | 187 |
| HPV45 | E2 | 9 | 357 |
| HPV45 | E2 | 8 | 109 |
| HPV45 | E2 | 9 | 332 |
| HPV45 | E2 | 11 | 40 |
| HPV45 | E2 | 9 | 90 |
| HPV45 | E2 | 8 | 43 |
| HPV45 | E2 | 9 | 309 |
| HPV45 | E2 | 11 | 142 |
| HPV45 | E2 | 8 | 358 |
| HPV45 | E2 | 10 | 99 |
| HPV45 | E2 | 8 | 159 |
| HPV45 | E2 | 8 | 138 |
| HPV45 | E2 | 11 | 98 |
| HPV45 | E2 | 9 | 166 |
| HPV45 | E2 | 10 | 166 |
| HPV45 | E2 | 8 | 145 |
| HPV45 | E2 | 8 | 317 |
| HPV45 | E2 | 10 | 317 |
| HPV45 | E2 | 11 | 175 |
| HPV45 | E2 | 8 | 137 |
| HPV45 | E2 | 9 | 137 |
| HPV45 | E6 | 9 | 37 |
| HPV45 | E6 | 11 | 37 |
| HPV45 | E6 | 8 | 27 |
| HPV45 | E6 | 10 | 77 |
| HPV45 | E6 | 11 | 43 |
| HPV45 | E6 | 10 | 53 |
| HPV45 | E6 | 8 | 120 |
| HPV45 | E6 | 9 | 54 |
| HPV45 | E6 | 8 | 92 |
| HPV45 | E6 | 8 | 74 |
| HPV45 | E6 | 9 | 41 |
| HPV45 | E6 | 11 | 24 |
| HPV45 | E6 | 11 | 89 |
| HPV45 | E6 | 8 | 38 |
| HPV45 | E6 | 10 | 38 |
| HPV45 | E6 | 9 | 72 |
| HPV45 | E6 | 10 | 72 |
| HPV45 | E7 | 9 | 83 |
| HPV45 | E7 | 10 | 20 |
| HPV45 | E7 | 11 | 91 |
| HPV45 | E7 | 10 | 92 |
| HPV45 | E7 | 9 | 89 |
| HPV45 | E7 | 9 | 93 |
| HPV45 | E7 | 8 | 94 |
| HPV45 | L1 | 8 | 103 |
| HPV45 | L1 | 11 | 28 |
| HPV45 | L1 | 11 | 375 |
| HPV45 | L1 | 8 | 88 |
| HPV45 | L1 | 10 | 88 |
| HPV45 | L1 | 8 | 276 |
| HPV45 | L1 | 9 | 188 |
| HPV45 | L1 | 9 | 250 |
| HPV45 | L1 | 11 | 488 |
| HPV45 | L1 | 9 | 332 |
| HPV45 | L1 | 10 | 332 |
| HPV45 | L1 | 9 | 229 |
| HPV45 | L1 | 11 | 461 |
| HPV45 | L1 | 8 | 296 |
| HPV45 | L1 | 10 | 169 |
| HPV45 | L1 | 8 | 313 |
| HPV45 | L1 | 8 | 14 |
| HPV45 | L1 | 11 | 14 |
| HPV45 | L1 | 8 | 485 |
| HPV45 | L1 | 9 | 351 |
| HPV45 | L1 | 9 | 141 |
| HPV45 | L1 | 10 | 141 |
| HPV45 | L1 | 8 | 111 |
| HPV45 | L1 | 8 | 143 |
| HPV45 | L1 | 11 | 326 |
| HPV45 | L1 | 11 | 422 |
| HPV45 | L1 | 9 | 396 |
| HPV45 | L1 | 11 | 396 |
| HPV45 | L1 | 10 | 12 |
| HPV45 | L1 | 11 | 11 |
| HPV45 | L1 | 10 | 5 |
| HPV45 | L1 | 10 | 411 |
| HPV45 | L1 | 9 | 328 |
| HPV45 | L1 | 10 | 91 |
| HPV45 | L1 | 8 | 68 |

TABLE VII-continued

HLA-A1 Supermotif Peptides

| 1 | 2 | 3 | 4 |
|---|---|---|---|
| HPV45 | L1 | 9 | 68 |
| HPV45 | L1 | 8 | 413 |
| HPV45 | L1 | 8 | 69 |
| HPV45 | L1 | 11 | 264 |
| HPV45 | L1 | 11 | 227 |
| HPV45 | L1 | 11 | 4 |
| HPV45 | L1 | 11 | 310 |
| HPV45 | L1 | 8 | 425 |
| HPV45 | L1 | 10 | 425 |
| HPV45 | L1 | 8 | 383 |
| HPV45 | L1 | 11 | 383 |
| HPV45 | L1 | 8 | 17 |
| HPV45 | L1 | 9 | 22 |
| HPV45 | L1 | 11 | 248 |
| HPV45 | L1 | 11 | 139 |
| HPV45 | L1 | 9 | 440 |
| HPV45 | L1 | 11 | 440 |
| HPV45 | L1 | 11 | 380 |
| HPV45 | L1 | 8 | 281 |
| HPV45 | L1 | 8 | 334 |
| HPV45 | L1 | 9 | 253 |
| HPV45 | L1 | 9 | 67 |
| HPV45 | L1 | 10 | 67 |
| HPV45 | L1 | 10 | 101 |
| HPV45 | L1 | 8 | 46 |
| HPV45 | L1 | 8 | 254 |
| HPV45 | L1 | 8 | 427 |
| HPV45 | L1 | 10 | 327 |
| HPV45 | L1 | 8 | 443 |
| HPV45 | L1 | 10 | 423 |
| HPV45 | L1 | 9 | 426 |
| HPV45 | L1 | 11 | 65 |
| HPV45 | L1 | 10 | 376 |
| HPV45 | L1 | 11 | 43 |
| HPV45 | L1 | 11 | 410 |
| HPV45 | L1 | 9 | 412 |
| HPV45 | L1 | 11 | 330 |
| HPV45 | L1 | 9 | 442 |
| HPV45 | L1 | 10 | 462 |
| HPV45 | L1 | 8 | 329 |
| HPV45 | L1 | 8 | 441 |
| HPV45 | L1 | 10 | 441 |
| HPV45 | L1 | 8 | 478 |
| HPV45 | L1 | 11 | 293 |
| HPV45 | L1 | 9 | 92 |
| HPV45 | L1 | 8 | 54 |
| HPV45 | L1 | 9 | 477 |
| HPV45 | L1 | 9 | 261 |
| HPV45 | L1 | 8 | 393 |
| HPV45 | L1 | 8 | 53 |
| HPV45 | L1 | 9 | 53 |
| HPV45 | L2 | 11 | 286 |
| HPV45 | L2 | 9 | 114 |
| HPV45 | L2 | 8 | 340 |
| HPV45 | L2 | 11 | 340 |
| HPV45 | L2 | 11 | 405 |
| HPV45 | L2 | 9 | 345 |
| HPV45 | L2 | 8 | 343 |
| HPV45 | L2 | 11 | 343 |
| HPV45 | L2 | 10 | 148 |
| HPV45 | L2 | 11 | 241 |
| HPV45 | L2 | 11 | 296 |
| HPV45 | L2 | 8 | 430 |
| HPV45 | L2 | 10 | 430 |
| HPV45 | L2 | 8 | 64 |
| HPV45 | L2 | 10 | 62 |
| HPV45 | L2 | 10 | 183 |
| HPV45 | L2 | 9 | 433 |
| HPV45 | L2 | 10 | 433 |
| HPV45 | L2 | 11 | 433 |
| HPV45 | L2 | 11 | 37 |
| HPV45 | L2 | 10 | 406 |
| HPV45 | L2 | 9 | 407 |
| HPV45 | L2 | 10 | 44 |
| HPV45 | L2 | 10 | 338 |
| HPV45 | L2 | 11 | 152 |
| HPV45 | L2 | 11 | 43 |
| HPV45 | L2 | 8 | 366 |
| HPV45 | L2 | 11 | 337 |
| HPV45 | L2 | 10 | 287 |
| HPV45 | L2 | 10 | 242 |
| HPV45 | L2 | 11 | 375 |
| HPV45 | L2 | 10 | 392 |
| HPV45 | L2 | 9 | 248 |
| HPV45 | L2 | 10 | 387 |
| HPV45 | L2 | 8 | 258 |
| HPV45 | L2 | 11 | 391 |
| HPV45 | L2 | 8 | 378 |
| HPV45 | L2 | 8 | 361 |
| HPV45 | L2 | 10 | 361 |
| HPV45 | L2 | 9 | 120 |
| HPV45 | L2 | 9 | 420 |
| HPV45 | L2 | 8 | 185 |
| HPV45 | L2 | 10 | 267 |
| HPV45 | L2 | 11 | 118 |
| HPV45 | L2 | 8 | 312 |
| HPV45 | L2 | 9 | 312 |
| HPV45 | L2 | 10 | 172 |
| HPV45 | L2 | 9 | 233 |
| HPV45 | L2 | 10 | 451 |
| HPV45 | L2 | 9 | 298 |
| HPV45 | L2 | 8 | 220 |
| HPV45 | L2 | 10 | 247 |
| HPV45 | L2 | 11 | 246 |
| HPV45 | L2 | 9 | 288 |
| HPV45 | L2 | 10 | 153 |
| HPV45 | L2 | 9 | 362 |
| HPV45 | L2 | 9 | 154 |
| HPV45 | L2 | 11 | 358 |
| HPV45 | L2 | 9 | 149 |
| HPV45 | L2 | 8 | 363 |
| HPV45 | L2 | 11 | 363 |
| HPV45 | L2 | 9 | 39 |
| HPV45 | L2 | 10 | 376 |
| HPV45 | L2 | 9 | 393 |
| HPV45 | L2 | 8 | 155 |
| HPV45 | L2 | 9 | 268 |
| HPV45 | L2 | 11 | 418 |
| HPV45 | L2 | 10 | 38 |
| HPV45 | L2 | 10 | 359 |
| HPV45 | L2 | 11 | 426 |
| HPV45 | L2 | 8 | 389 |
| HPV45 | L2 | 11 | 217 |
| HPV45 | L2 | 8 | 150 |
| HPV45 | L2 | 8 | 249 |
| HPV45 | L2 | 9 | 388 |
| HPV45 | L2 | 11 | 112 |
| HPV45 | L2 | 9 | 428 |
| HPV45 | L2 | 10 | 428 |
| HPV45 | L2 | 8 | 437 |
| HPV45 | L2 | 9 | 437 |
| HPV56 | E2 | 10 | 21 |
| HPV56 | E2 | 9 | 71 |
| HPV56 | E2 | 11 | 71 |
| HPV56 | E2 | 10 | 92 |
| HPV56 | E2 | 11 | 92 |
| HPV56 | E2 | 9 | 140 |
| HPV56 | E2 | 8 | 263 |
| HPV56 | E2 | 11 | 43 |
| HPV56 | E2 | 8 | 23 |
| HPV56 | E2 | 10 | 128 |
| HPV56 | E2 | 11 | 294 |
| HPV56 | E2 | 8 | 261 |
| HPV56 | E2 | 10 | 261 |
| HPV56 | E2 | 9 | 66 |
| HPV56 | E2 | 8 | 94 |
| HPV56 | E2 | 9 | 94 |
| HPV56 | E2 | 8 | 130 |
| HPV56 | E2 | 8 | 297 |
| HPV56 | E2 | 10 | 299 |

TABLE VII-continued

HLA-A1 Supermotif Peptides

| 1 | 2 | 3 | 4 |
|---|---|---|---|
| HPV56 | E2 | 11 | 258 |
| HPV56 | E2 | 8 | 90 |
| HPV56 | E2 | 10 | 295 |
| HPV56 | E2 | 11 | 25 |
| HPV56 | E2 | 8 | 46 |
| HPV56 | E2 | 11 | 149 |
| HPV56 | E2 | 8 | 152 |
| HPV56 | E2 | 8 | 301 |
| HPV56 | E2 | 9 | 246 |
| HPV56 | E2 | 10 | 26 |
| HPV56 | E2 | 8 | 141 |
| HPV56 | E2 | 8 | 28 |
| HPV56 | E2 | 10 | 259 |
| HPV56 | E2 | 10 | 36 |
| HPV56 | E2 | 8 | 271 |
| HPV56 | E2 | 9 | 27 |
| HPV56 | E2 | 10 | 150 |
| HPV56 | E2 | 9 | 45 |
| HPV56 | E2 | 11 | 35 |
| HPV56 | E2 | 9 | 270 |
| HPV56 | E2 | 10 | 79 |
| HPV56 | E2 | 8 | 278 |
| HPV56 | E2 | 11 | 111 |
| HPV56 | E2 | 8 | 74 |
| HPV56 | E2 | 9 | 74 |
| HPV56 | E2 | 9 | 102 |
| HPV56 | E2 | 10 | 102 |
| HPV56 | E6 | 9 | 64 |
| HPV56 | E6 | 10 | 64 |
| HPV56 | E6 | 11 | 69 |
| HPV56 | E6 | 8 | 50 |
| HPV56 | E6 | 8 | 28 |
| HPV56 | E6 | 10 | 52 |
| HPV56 | E6 | 8 | 39 |
| HPV56 | E6 | 10 | 39 |
| HPV56 | E6 | 8 | 54 |
| HPV56 | E6 | 10 | 54 |
| HPV56 | E6 | 8 | 75 |
| HPV56 | E6 | 10 | 75 |
| HPV56 | E6 | 10 | 26 |
| HPV56 | E6 | 10 | 70 |
| HPV56 | E6 | 9 | 40 |
| HPV56 | E6 | 9 | 55 |
| HPV56 | E6 | 11 | 25 |
| HPV56 | E6 | 10 | 98 |
| HPV56 | E6 | 10 | 119 |
| HPV56 | E6 | 9 | 135 |
| HPV56 | E6 | 9 | 73 |
| HPV56 | E6 | 10 | 73 |
| HPV56 | E7 | 9 | 62 |
| HPV56 | E7 | 11 | 60 |
| HPV56 | L1 | 8 | 381 |
| HPV56 | L1 | 8 | 444 |
| HPV56 | L1 | 10 | 444 |
| HPV56 | L1 | 11 | 37 |
| HPV56 | L1 | 8 | 26 |
| HPV56 | L1 | 9 | 195 |
| HPV56 | L1 | 9 | 257 |
| HPV56 | L1 | 11 | 491 |
| HPV56 | L1 | 10 | 486 |
| HPV56 | L1 | 10 | 60 |
| HPV56 | L1 | 11 | 60 |
| HPV56 | L1 | 9 | 236 |
| HPV56 | L1 | 8 | 23 |
| HPV56 | L1 | 11 | 23 |
| HPV56 | L1 | 8 | 481 |
| HPV56 | L1 | 8 | 303 |
| HPV56 | L1 | 10 | 21 |
| HPV56 | L1 | 8 | 488 |
| HPV56 | L1 | 9 | 356 |
| HPV56 | L1 | 8 | 118 |
| HPV56 | L1 | 8 | 150 |
| HPV56 | L1 | 11 | 331 |
| HPV56 | L1 | 9 | 399 |
| HPV56 | L1 | 11 | 399 |
| HPV56 | L1 | 11 | 378 |
| HPV56 | L1 | 10 | 414 |
| HPV56 | L1 | 8 | 334 |
| HPV56 | L1 | 8 | 258 |
| HPV56 | L1 | 11 | 258 |
| HPV56 | L1 | 11 | 413 |
| HPV56 | L1 | 10 | 93 |
| HPV56 | L1 | 11 | 300 |
| HPV56 | L1 | 10 | 98 |
| HPV56 | L1 | 8 | 55 |
| HPV56 | L1 | 8 | 77 |
| HPV56 | L1 | 9 | 77 |
| HPV56 | L1 | 8 | 416 |
| HPV56 | L1 | 11 | 234 |
| HPV56 | L1 | 9 | 333 |
| HPV56 | L1 | 8 | 2 |
| HPV56 | L1 | 9 | 1 |
| HPV56 | L1 | 11 | 271 |
| HPV56 | L1 | 8 | 95 |
| HPV56 | L1 | 10 | 95 |
| HPV56 | L1 | 10 | 426 |
| HPV56 | L1 | 9 | 31 |
| HPV56 | L1 | 8 | 473 |
| HPV56 | L1 | 11 | 255 |
| HPV56 | L1 | 9 | 13 |
| HPV56 | L1 | 11 | 467 |
| HPV56 | L1 | 10 | 442 |
| HPV56 | L1 | 11 | 52 |
| HPV56 | L1 | 8 | 288 |
| HPV56 | L1 | 8 | 339 |
| HPV56 | L1 | 9 | 260 |
| HPV56 | L1 | 9 | 76 |
| HPV56 | L1 | 10 | 76 |
| HPV56 | L1 | 8 | 110 |
| HPV56 | L1 | 10 | 108 |
| HPV56 | L1 | 8 | 446 |
| HPV56 | L1 | 10 | 332 |
| HPV56 | L1 | 11 | 74 |
| HPV56 | L1 | 10 | 379 |
| HPV56 | L1 | 8 | 261 |
| HPV56 | L1 | 9 | 415 |
| HPV56 | L1 | 11 | 335 |
| HPV56 | L1 | 9 | 445 |
| HPV56 | L1 | 9 | 99 |
| HPV56 | L1 | 10 | 53 |
| HPV56 | L1 | 10 | 7 |
| HPV56 | L1 | 9 | 268 |
| HPV56 | L1 | 8 | 396 |
| HPV56 | L1 | 8 | 283 |
| HPV56 | L1 | 8 | 62 |
| HPV56 | L1 | 9 | 62 |
| HPV56 | L2 | 8 | 438 |
| HPV56 | L2 | 11 | 246 |
| HPV56 | L2 | 11 | 406 |
| HPV56 | L2 | 11 | 30 |
| HPV56 | L2 | 9 | 429 |
| HPV56 | L2 | 9 | 114 |
| HPV56 | L2 | 10 | 287 |
| HPV56 | L2 | 11 | 118 |
| HPV56 | L2 | 8 | 64 |
| HPV56 | L2 | 10 | 434 |
| HPV56 | L2 | 11 | 434 |
| HPV56 | L2 | 8 | 258 |
| HPV56 | L2 | 10 | 62 |
| HPV56 | L2 | 10 | 310 |
| HPV56 | L2 | 11 | 310 |
| HPV56 | L2 | 8 | 269 |
| HPV56 | L2 | 11 | 372 |
| HPV56 | L2 | 11 | 190 |
| HPV56 | L2 | 8 | 44 |
| HPV56 | L2 | 10 | 44 |
| HPV56 | L2 | 11 | 44 |
| HPV56 | L2 | 9 | 210 |
| HPV56 | L2 | 11 | 182 |
| HPV56 | L2 | 9 | 279 |

TABLE VII-continued

HLA-A1 Supermotif Peptides

| 1 | 2 | 3 | 4 |
|---|---|---|---|
| HPV56 | L2 | 10 | 407 |
| HPV56 | L2 | 9 | 43 |
| HPV56 | L2 | 11 | 43 |
| HPV56 | L2 | 10 | 38 |
| HPV56 | L2 | 8 | 337 |
| HPV56 | L2 | 11 | 338 |
| HPV56 | L2 | 9 | 248 |
| HPV56 | L2 | 10 | 278 |
| HPV56 | L2 | 10 | 342 |
| HPV56 | L2 | 10 | 388 |
| HPV56 | L2 | 8 | 395 |
| HPV56 | L2 | 9 | 374 |
| HPV56 | L2 | 10 | 209 |
| HPV56 | L2 | 10 | 392 |
| HPV56 | L2 | 11 | 392 |
| HPV56 | L2 | 9 | 336 |
| HPV56 | L2 | 10 | 267 |
| HPV56 | L2 | 9 | 410 |
| HPV56 | L2 | 8 | 185 |
| HPV56 | L2 | 8 | 312 |
| HPV56 | L2 | 9 | 312 |
| HPV56 | L2 | 10 | 312 |
| HPV56 | L2 | 11 | 421 |
| HPV56 | L2 | 9 | 233 |
| HPV56 | L2 | 8 | 220 |
| HPV56 | L2 | 9 | 435 |
| HPV56 | L2 | 10 | 435 |
| HPV56 | L2 | 11 | 435 |
| HPV56 | L2 | 10 | 153 |
| HPV56 | L2 | 8 | 211 |
| HPV56 | L2 | 9 | 154 |
| HPV56 | L2 | 10 | 183 |
| HPV56 | L2 | 11 | 414 |
| HPV56 | L2 | 10 | 247 |
| HPV56 | L2 | 9 | 288 |
| HPV56 | L2 | 11 | 112 |
| HPV56 | L2 | 9 | 408 |
| HPV56 | L2 | 11 | 408 |
| HPV56 | L2 | 8 | 249 |
| HPV56 | L2 | 11 | 152 |
| HPV56 | L2 | 9 | 389 |
| HPV56 | L2 | 10 | 31 |
| HPV56 | L2 | 10 | 431 |

SF 1168080 v1

TABLE VIIA

HPV6A
HLA-A1 Supermotif Peptides

| 2 | 3 | 4 |
|---|---|---|
| L2 | 11 | 286 |
| E4 | 8 | 14 |
| E1 | 11 | 520 |
| E1 | 10 | 207 |
| L1 | 8 | 81 |
| L2 | 8 | 421 |
| E6 | 8 | 37 |
| E6 | 10 | 37 |
| L2 | 9 | 288 |
| E1 | 11 | 330 |
| L1 | 9 | 342 |
| E1 | 8 | 525 |
| E6 | 11 | 10 |
| E1 | 10 | 77 |
| E1 | 10 | 601 |
| E6 | 11 | 67 |
| E2 | 10 | 35 |
| E6 | 11 | 131 |
| E4 | 9 | 64 |
| E1 | 10 | 369 |

TABLE VIIA-continued

HPV6A
HLA-A1 Supermotif Peptides

| 2 | 3 | 4 |
|---|---|---|
| L1 | 9 | 219 |
| E6 | 10 | 96 |
| E1 | 8 | 570 |
| E1 | 10 | 570 |
| E2 | 9 | 313 |
| E1 | 11 | 81 |
| E2 | 9 | 25 |
| E1 | 10 | 203 |
| E1 | 9 | 42 |
| L2 | 11 | 266 |
| E7 | 9 | 44 |
| L2 | 10 | 344 |
| L1 | 9 | 198 |
| E2 | 10 | 136 |
| L2 | 10 | 120 |
| L1 | 11 | 453 |
| E1 | 10 | 604 |
| E1 | 11 | 604 |
| E1 | 9 | 131 |
| E1 | 10 | 417 |
| E2 | 11 | 100 |
| E1 | 8 | 373 |
| E2 | 8 | 80 |
| E2 | 8 | 293 |
| E2 | 10 | 293 |
| L1 | 8 | 443 |
| E2 | 10 | 205 |
| E1 | 8 | 220 |
| E6 | 8 | 126 |
| E1 | 8 | 454 |
| E1 | 11 | 454 |
| L2 | 8 | 428 |
| E5 | 9 | 68 |
| E1 | 10 | 393 |
| L2 | 10 | 398 |
| E1 | 9 | 446 |
| L1 | 8 | 245 |
| E1 | 8 | 457 |
| L2 | 11 | 239 |
| L1 | 8 | 450 |
| E1 | 9 | 587 |
| E2 | 8 | 171 |
| E5 | 9 | 28 |
| L1 | 9 | 318 |
| E1 | 10 | 243 |
| E2 | 9 | 156 |
| E1 | 11 | 217 |
| E1 | 10 | 273 |
| E1 | 8 | 11 |
| L2 | 10 | 431 |
| L2 | 11 | 431 |
| L2 | 10 | 62 |
| E1 | 10 | 431 |
| L1 | 11 | 293 |
| E2 | 10 | 179 |
| L2 | 11 | 215 |
| L2 | 8 | 64 |
| E1 | 11 | 436 |
| L1 | 9 | 407 |
| L1 | 9 | 222 |
| E1 | 8 | 316 |
| L1 | 9 | 111 |
| L1 | 11 | 113 |
| L2 | 8 | 312 |
| L2 | 9 | 312 |
| L2 | 10 | 312 |
| E6 | 8 | 119 |
| E1 | 9 | 264 |
| E4 | 8 | 59 |
| E2 | 10 | 78 |
| E2 | 10 | 110 |
| E4 | 10 | 10 |
| E4 | 9 | 338 |
| E2 | 10 | 149 |

TABLE VIIA-continued

HPV6A
HLA-A1 Supermotif Peptides

| 2 | 3 | 4 |
|---|---|---|
| E2 | 11 | 149 |
| E6 | 9 | 25 |
| L1 | 11 | 387 |
| E1 | 9 | 581 |
| L1 | 9 | 361 |
| L1 | 11 | 361 |
| E1 | 8 | 502 |
| E1 | 9 | 502 |
| E5 | 8 | 21 |
| E5 | 10 | 31 |
| E6 | 9 | 97 |
| E5 | 9 | 32 |
| L2 | 10 | 44 |
| L2 | 11 | 44 |
| E5 | 8 | 17 |
| E1 | 10 | 500 |
| E1 | 11 | 500 |
| E1 | 9 | 571 |
| L1 | 10 | 376 |
| L2 | 8 | 247 |
| E1 | 11 | 476 |
| L2 | 9 | 121 |
| E2 | 10 | 34 |
| E1 | 8 | 433 |
| E6 | 8 | 73 |
| E6 | 10 | 73 |
| E1 | 10 | 312 |
| E1 | 11 | 312 |
| E1 | 9 | 254 |
| E1 | 8 | 357 |
| E1 | 10 | 357 |
| E1 | 10 | 228 |
| E1 | 11 | 484 |
| E2 | 9 | 84 |
| L1 | 10 | 56 |
| E6 | 11 | 116 |
| E6 | 8 | 52 |
| E6 | 10 | 52 |
| L1 | 10 | 61 |
| L1 | 8 | 19 |
| L1 | 10 | 71 |
| E1 | 8 | 255 |
| E5 | 9 | 16 |
| E2 | 8 | 314 |
| L2 | 9 | 246 |
| E5 | 8 | 33 |
| E5 | 11 | 33 |
| L1 | 8 | 41 |
| L1 | 9 | 41 |
| E1 | 10 | 521 |
| E1 | 9 | 208 |
| E2 | 11 | 82 |
| E5 | 9 | 59 |
| E5 | 10 | 59 |
| E5 | 8 | 51 |
| E5 | 8 | 69 |
| E5 | 8 | 60 |
| E5 | 9 | 60 |
| E5 | 10 | 72 |
| L1 | 8 | 378 |
| E1 | 10 | 218 |
| E1 | 9 | 259 |
| E1 | 9 | 605 |
| E1 | 10 | 605 |
| L2 | 9 | 390 |
| L2 | 10 | 240 |
| E1 | 8 | 132 |
| E1 | 9 | 358 |
| E5 | 10 | 49 |
| E6 | 9 | 38 |
| E6 | 11 | 38 |
| E5 | 8 | 61 |
| L2 | 9 | 338 |
| E5 | 9 | 73 |
| E5 | 8 | 47 |
| L1 | 9 | 295 |
| E2 | 8 | 151 |
| E2 | 9 | 151 |
| L1 | 11 | 196 |
| E1 | 9 | 274 |
| E1 | 10 | 568 |
| E1 | 11 | 451 |
| E4 | 10 | 57 |
| E1 | 9 | 59 |
| E1 | 8 | 395 |
| E2 | 10 | 281 |
| L2 | 10 | 38 |
| E2 | 8 | 127 |
| L1 | 11 | 217 |
| L2 | 10 | 189 |
| L1 | 11 | 109 |
| E1 | 10 | 258 |
| L2 | 10 | 389 |
| L2 | 10 | 337 |
| L1 | 9 | 391 |
| L2 | 9 | 408 |
| E2 | 9 | 354 |
| L1 | 11 | 426 |
| L1 | 8 | 90 |
| L2 | 9 | 426 |
| L2 | 10 | 426 |
| E5 | 10 | 19 |
| L1 | 11 | 16 |
| L2 | 11 | 418 |
| L2 | 9 | 363 |
| L2 | 11 | 43 |
| L1 | 8 | 301 |
| E6 | 10 | 50 |
| E4 | 9 | 4 |
| L1 | 8 | 250 |
| L2 | 8 | 400 |
| E1 | 8 | 314 |
| E1 | 9 | 314 |
| E1 | 10 | 314 |
| E2 | 8 | 103 |
| E1 | 10 | 128 |
| L2 | 9 | 231 |
| L2 | 10 | 245 |
| L1 | 9 | 40 |
| L1 | 10 | 40 |
| E2 | 10 | 303 |
| L1 | 9 | 279 |
| L1 | 8 | 140 |
| E1 | 11 | 583 |
| L2 | 8 | 153 |
| L2 | 10 | 267 |
| E5 | 11 | 30 |
| E2 | 8 | 207 |
| L1 | 11 | 375 |
| E1 | 8 | 60 |
| L1 | 10 | 294 |
| E1 | 8 | 260 |
| E6 | 11 | 23 |
| E2 | 9 | 150 |
| E2 | 10 | 150 |
| E2 | 9 | 282 |
| L1 | 11 | 297 |
| L2 | 8 | 391 |
| L1 | 11 | 38 |
| L1 | 9 | 347 |
| E2 | 11 | 23 |
| E2 | 9 | 180 |
| E5 | 11 | 14 |
| L2 | 10 | 374 |
| L2 | 9 | 241 |
| E1 | 10 | 331 |
| L1 | 8 | 348 |
| L1 | 11 | 348 |

TABLE VIIA-continued

HPV6A
HLA-A1 Supermotif Peptides

| 2 | 3 | 4 |
|---|---|---|
| L1 | 8 | 392 |
| E5 | 10 | 45 |
| L2 | 11 | 145 |
| L1 | 8 | 343 |
| L2 | 9 | 39 |
| E6 | 9 | 12 |
| E2 | 8 | 355 |
| L1 | 8 | 408 |
| E5 | 10 | 15 |
| E5 | 9 | 50 |
| E5 | 11 | 71 |
| E2 | 10 | 93 |
| E6 | 8 | 26 |
| L1 | 9 | 377 |
| E2 | 11 | 128 |
| L1 | 10 | 388 |
| L2 | 9 | 147 |
| L2 | 9 | 152 |
| L1 | 10 | 346 |
| L2 | 11 | 373 |
| L1 | 8 | 280 |
| E5 | 11 | 44 |
| E6 | 8 | 39 |
| E6 | 10 | 39 |
| E1 | 11 | 232 |
| L1 | 8 | 223 |
| E1 | 9 | 585 |
| E1 | 11 | 585 |
| E6 | 10 | 11 |
| L2 | 10 | 151 |
| L1 | 11 | 345 |
| L2 | 11 | 150 |
| E1 | 9 | 332 |
| E1 | 9 | 78 |
| L1 | 9 | 57 |
| L1 | 11 | 57 |
| E1 | 11 | 346 |
| E1 | 8 | 333 |
| E5 | 9 | 20 |
| E1 | 11 | 499 |
| E6 | 9 | 53 |
| E1 | 8 | 275 |
| L1 | 8 | 73 |
| E5 | 11 | 48 |
| E5 | 9 | 46 |
| L1 | 10 | 114 |
| L1 | 9 | 62 |
| E5 | 8 | 29 |
| E2 | 9 | 206 |
| L1 | 10 | 17 |
| L1 | 8 | 296 |
| L2 | 10 | 419 |
| L2 | 8 | 364 |
| L1 | 8 | 27 |
| L2 | 10 | 146 |
| E1 | 10 | 584 |
| L1 | 9 | 72 |
| L1 | 8 | 58 |
| L1 | 10 | 58 |
| E5 | 8 | 36 |
| E5 | 10 | 58 |
| E5 | 11 | 58 |
| E2 | 8 | 92 |
| E2 | 11 | 92 |
| E4 | 8 | 12 |
| E4 | 10 | 12 |
| L2 | 8 | 435 |
| E1 | 9 | 579 |
| E1 | 11 | 579 |
| L1 | 9 | 230 |
| L1 | 8 | 358 |
| E2 | 9 | 159 |
| E2 | 10 | 159 |
| L1 | 9 | 350 |

TABLE VIIA-continued

HPV6A
HLA-A1 Supermotif Peptides

| 2 | 3 | 4 |
|---|---|---|
| E2 | 11 | 168 |
| E2 | 8 | 138 |
| L1 | 8 | 26 |
| L1 | 9 | 26 |
| E2 | 8 | 131 |

TABLE VIIB

HPV6B
HLA-A1 Supermotif Peptides

| 2 | 3 | 4 |
|---|---|---|
| L2 | 11 | 286 |
| E4 | 8 | 24 |
| E1 | 11 | 520 |
| E1 | 10 | 207 |
| L1 | 8 | 81 |
| L2 | 8 | 421 |
| E6 | 8 | 37 |
| E6 | 10 | 37 |
| L2 | 9 | 288 |
| E1 | 11 | 330 |
| L1 | 9 | 342 |
| E1 | 8 | 525 |
| E6 | 11 | 10 |
| E1 | 10 | 77 |
| E1 | 10 | 601 |
| E1 | 9 | 234 |
| E6 | 11 | 67 |
| E2 | 10 | 35 |
| E6 | 11 | 131 |
| E4 | 9 | 74 |
| E1 | 10 | 369 |
| L1 | 9 | 219 |
| E6 | 10 | 96 |
| E1 | 8 | 570 |
| E1 | 10 | 570 |
| E2 | 9 | 25 |
| E2 | 9 | 313 |
| E1 | 11 | 81 |
| E1 | 10 | 203 |
| E2 | 9 | 338 |
| E1 | 9 | 42 |
| L2 | 11 | 266 |
| E7 | 9 | 44 |
| L2 | 10 | 344 |
| L1 | 9 | 198 |
| E2 | 10 | 136 |
| L2 | 10 | 120 |
| L1 | 11 | 453 |
| E1 | 10 | 604 |
| E1 | 11 | 604 |
| E1 | 9 | 131 |
| E1 | 10 | 417 |
| E2 | 11 | 100 |
| E1 | 8 | 373 |
| E2 | 8 | 80 |
| E2 | 8 | 293 |
| E2 | 10 | 293 |
| L1 | 8 | 443 |
| E2 | 10 | 205 |
| E1 | 8 | 220 |
| E6 | 8 | 126 |
| E5A | 9 | 16 |
| E1 | 8 | 454 |
| E1 | 11 | 454 |
| L2 | 8 | 428 |
| E5A | 9 | 68 |
| E1 | 10 | 393 |
| L2 | 10 | 397 |

TABLE VIIB-continued

HPV6B
HLA-A1 Supermotif Peptides

| 2 | 3 | 4 |
|---|---|---|
| E1 | 9 | 446 |
| L1 | 8 | 245 |
| L2 | 11 | 239 |
| E1 | 8 | 457 |
| L1 | 8 | 450 |
| E1 | 9 | 587 |
| E2 | 8 | 171 |
| E5A | 9 | 28 |
| L1 | 9 | 318 |
| E1 | 10 | 243 |
| E2 | 9 | 156 |
| E1 | 11 | 217 |
| E5B | 8 | 15 |
| E5B | 10 | 25 |
| E1 | 10 | 273 |
| E1 | 8 | 11 |
| L2 | 10 | 431 |
| L2 | 11 | 431 |
| L2 | 10 | 62 |
| E1 | 10 | 431 |
| L1 | 11 | 293 |
| E2 | 10 | 179 |
| L2 | 11 | 215 |
| L2 | 8 | 64 |
| E1 | 11 | 436 |
| L1 | 9 | 407 |
| L1 | 9 | 222 |
| E1 | 8 | 316 |
| L1 | 9 | 111 |
| L1 | 11 | 113 |
| L2 | 8 | 312 |
| L2 | 9 | 312 |
| L2 | 10 | 312 |
| E6 | 8 | 119 |
| E1 | 9 | 264 |
| E2 | 10 | 78 |
| E2 | 10 | 310 |
| E6 | 10 | 50 |
| E4 | 10 | 20 |
| E2 | 10 | 149 |
| E2 | 11 | 149 |
| E6 | 9 | 25 |
| L1 | 11 | 387 |
| E1 | 9 | 581 |
| L1 | 9 | 361 |
| L1 | 11 | 361 |
| E1 | 8 | 502 |
| E1 | 9 | 502 |
| E5A | 8 | 21 |
| E5A | 10 | 31 |
| E6 | 9 | 97 |
| E5A | 9 | 32 |
| L2 | 10 | 44 |
| L2 | 11 | 44 |
| E5A | 8 | 17 |
| E1 | 10 | 500 |
| E1 | 11 | 500 |
| E1 | 9 | 571 |
| L1 | 10 | 376 |
| L2 | 8 | 247 |
| E1 | 11 | 476 |
| L2 | 9 | 121 |
| E5A | 10 | 34 |
| E1 | 8 | 433 |
| E6 | 8 | 73 |
| E6 | 10 | 73 |
| E1 | 10 | 312 |
| E1 | 11 | 312 |
| E1 | 9 | 254 |
| E1 | 8 | 357 |
| E1 | 10 | 357 |
| E1 | 10 | 228 |
| E1 | 11 | 484 |
| L1 | 10 | 56 |
| E6 | 11 | 116 |
| E6 | 8 | 52 |
| E6 | 10 | 52 |
| L1 | 10 | 61 |
| L1 | 8 | 19 |
| L1 | 10 | 71 |
| E1 | 8 | 255 |
| E2 | 8 | 314 |
| L2 | 9 | 246 |
| E5A | 8 | 33 |
| E5A | 11 | 33 |
| L1 | 8 | 41 |
| L1 | 9 | 41 |
| E1 | 10 | 521 |
| E1 | 9 | 208 |
| E5A | 9 | 59 |
| E5A | 10 | 59 |
| E5A | 8 | 51 |
| E2 | 11 | 82 |
| E5A | 8 | 69 |
| E5A | 8 | 60 |
| E5A | 9 | 60 |
| E5A | 10 | 72 |
| L1 | 8 | 378 |
| E1 | 10 | 218 |
| L2 | 8 | 390 |
| E1 | 9 | 259 |
| E1 | 9 | 605 |
| E1 | 10 | 605 |
| L2 | 10 | 240 |
| E5B | 11 | 3 |
| E1 | 8 | 132 |
| E1 | 9 | 358 |
| E5A | 10 | 49 |
| E6 | 9 | 38 |
| E6 | 11 | 38 |
| E5A | 8 | 61 |
| L2 | 9 | 338 |
| E5A | 9 | 73 |
| E5A | 8 | 47 |
| L1 | 9 | 295 |
| E5B | 9 | 26 |
| E2 | 8 | 151 |
| E2 | 9 | 151 |
| L1 | 11 | 196 |
| E1 | 9 | 274 |
| E1 | 10 | 568 |
| E1 | 11 | 451 |
| E1 | 9 | 59 |
| E1 | 8 | 395 |
| E4 | 10 | 67 |
| E2 | 10 | 201 |
| L2 | 10 | 38 |
| E2 | 8 | 127 |
| E1 | 8 | 607 |
| L1 | 11 | 217 |
| L2 | 10 | 189 |
| E4 | 8 | 69 |
| L1 | 11 | 109 |
| L2 | 9 | 389 |
| E1 | 10 | 258 |
| L2 | 10 | 337 |
| L1 | 9 | 391 |
| L2 | 9 | 407 |
| E2 | 9 | 354 |
| L1 | 11 | 426 |
| L1 | 8 | 90 |
| L2 | 9 | 426 |
| L2 | 10 | 426 |
| E5A | 10 | 19 |
| L1 | 11 | 16 |
| L2 | 9 | 363 |
| E5A | 10 | 7 |
| L2 | 11 | 43 |

TABLE VIIB-continued

HPV6B
HLA-A1 Supermotif Peptides

| 2 | 3 | 4 |
|---|---|---|
| L1 | 8 | 301 |
| E4 | 9 | 14 |
| L1 | 8 | 250 |
| L2 | 8 | 399 |
| E1 | 8 | 314 |
| E1 | 9 | 314 |
| E1 | 10 | 314 |
| E2 | 8 | 103 |
| E1 | 10 | 128 |
| L2 | 9 | 231 |
| L2 | 10 | 245 |
| L1 | 9 | 40 |
| L1 | 10 | 40 |
| E2 | 10 | 303 |
| E2 | 9 | 84 |
| L1 | 9 | 279 |
| L1 | 8 | 140 |
| E1 | 11 | 583 |
| L2 | 8 | 153 |
| L2 | 10 | 267 |
| E5A | 11 | 30 |
| E2 | 8 | 207 |
| L1 | 11 | 375 |
| E1 | 8 | 60 |
| L1 | 10 | 294 |
| E1 | 8 | 260 |
| E6 | 11 | 23 |
| E2 | 9 | 150 |
| E2 | 10 | 150 |
| E2 | 9 | 262 |
| L1 | 11 | 297 |
| L1 | 11 | 38 |
| L1 | 9 | 347 |
| E2 | 11 | 23 |
| E5A | 11 | 14 |
| E2 | 9 | 180 |
| L2 | 10 | 374 |
| L2 | 9 | 241 |
| E1 | 10 | 331 |
| L1 | 8 | 348 |
| L1 | 11 | 348 |
| L1 | 8 | 392 |
| E5A | 10 | 45 |
| L2 | 11 | 145 |
| L1 | 8 | 343 |
| L2 | 9 | 39 |
| E6 | 9 | 12 |
| E2 | 8 | 355 |
| L1 | 8 | 408 |
| E5A | 9 | 50 |
| E5A | 11 | 71 |
| E2 | 10 | 93 |
| E6 | 8 | 26 |
| L1 | 9 | 377 |
| E2 | 11 | 128 |
| E5B | 10 | 59 |
| L1 | 10 | 388 |
| L2 | 9 | 147 |
| L2 | 9 | 152 |
| L1 | 10 | 346 |
| L2 | 11 | 373 |
| L1 | 8 | 280 |
| E5A | 11 | 44 |
| E6 | 8 | 39 |
| E6 | 10 | 39 |
| L1 | 8 | 223 |
| E1 | 11 | 232 |
| E5B | 8 | 63 |
| E1 | 9 | 585 |
| E1 | 11 | 585 |
| E6 | 10 | 11 |
| L2 | 10 | 151 |
| L1 | 11 | 345 |
| L2 | 11 | 150 |

TABLE VIIB-continued

HPV6B
HLA-A1 Supermotif Peptides

| 2 | 3 | 4 |
|---|---|---|
| E1 | 9 | 332 |
| L2 | 11 | 387 |
| E1 | 9 | 78 |
| L1 | 9 | 57 |
| L1 | 11 | 57 |
| E1 | 11 | 346 |
| E1 | 8 | 333 |
| E5A | 9 | 20 |
| E1 | 11 | 499 |
| E6 | 9 | 53 |
| E1 | 8 | 275 |
| L1 | 8 | 73 |
| E5A | 11 | 48 |
| E5A | 9 | 46 |
| L1 | 10 | 114 |
| L1 | 9 | 62 |
| E5A | 8 | 29 |
| E2 | 9 | 206 |
| L1 | 10 | 17 |
| L1 | 8 | 296 |
| E5B | 11 | 58 |
| L2 | 8 | 364 |
| L2 | 11 | 418 |
| L1 | 8 | 27 |
| L2 | 10 | 146 |
| E1 | 10 | 584 |
| L1 | 9 | 72 |
| L1 | 8 | 58 |
| L1 | 10 | 58 |
| E5A | 8 | 36 |
| E5B | 10 | 13 |
| E5A | 10 | 58 |
| E5A | 11 | 58 |
| E2 | 8 | 92 |
| E2 | 11 | 92 |
| E4 | 8 | 22 |
| E4 | 10 | 22 |
| L2 | 8 | 435 |
| E1 | 9 | 579 |
| E1 | 11 | 579 |
| L1 | 9 | 230 |
| L1 | 8 | 358 |
| E2 | 9 | 159 |
| E2 | 10 | 159 |
| L1 | 9 | 350 |
| E5B | 9 | 62 |
| E4 | 8 | 9 |
| E2 | 11 | 168 |
| E2 | 8 | 138 |
| L1 | 8 | 26 |
| L1 | 9 | 26 |
| E2 | 8 | 131 |

TABLE VIIC

HPV11
HLA-A1 Supermotif Peptides

| 2 | 3 | 4 |
|---|---|---|
| L2 | 11 | 285 |
| E1 | 11 | 520 |
| L1 | 8 | 81 |
| L2 | 8 | 417 |
| E6 | 8 | 37 |
| E6 | 10 | 37 |
| E1 | 11 | 330 |
| L1 | 9 | 343 |
| E1 | 8 | 525 |
| E6 | 11 | 10 |
| E1 | 10 | 77 |

TABLE VIIC-continued

HPV11
HLA-A1 Supermotif Peptides

| 2 | 3 | 4 |
|---|---|---|
| L1 | 8 | 349 |
| L1 | 11 | 349 |
| E5 | 10 | 26 |
| E1 | 10 | 601 |
| E6 | 11 | 67 |
| E5 | 8 | 73 |
| E5 | 9 | 73 |
| E4 | 9 | 73 |
| E1 | 10 | 369 |
| L1 | 9 | 220 |
| E2 | 9 | 25 |
| E6 | 10 | 96 |
| E1 | 10 | 203 |
| E1 | 8 | 570 |
| E1 | 10 | 570 |
| E1 | 11 | 81 |
| E1 | 9 | 42 |
| E2 | 8 | 292 |
| E2 | 10 | 292 |
| L2 | 10 | 343 |
| L1 | 9 | 199 |
| E5 | 9 | 12 |
| L1 | 8 | 125 |
| E2 | 9 | 312 |
| L1 | 11 | 454 |
| E6 | 9 | 69 |
| E1 | 10 | 604 |
| E1 | 11 | 604 |
| E1 | 9 | 131 |
| E1 | 10 | 417 |
| E2 | 11 | 100 |
| E1 | 8 | 373 |
| L2 | 11 | 265 |
| E2 | 8 | 80 |
| E1 | 10 | 128 |
| L1 | 8 | 444 |
| E2 | 10 | 205 |
| L2 | 10 | 119 |
| E6 | 8 | 126 |
| E1 | 11 | 454 |
| L2 | 8 | 424 |
| E1 | 9 | 494 |
| E5 | 9 | 68 |
| E5 | 10 | 68 |
| E1 | 10 | 393 |
| E1 | 9 | 446 |
| E1 | 8 | 457 |
| L2 | 11 | 238 |
| E5 | 8 | 16 |
| L2 | 11 | 295 |
| L1 | 8 | 451 |
| E1 | 9 | 587 |
| E1 | 8 | 220 |
| L2 | 10 | 393 |
| L1 | 9 | 319 |
| E1 | 10 | 243 |
| E2 | 9 | 156 |
| E1 | 11 | 217 |
| E1 | 10 | 273 |
| L2 | 10 | 427 |
| L2 | 11 | 427 |
| E1 | 8 | 11 |
| L2 | 8 | 63 |
| L1 | 11 | 294 |
| E2 | 10 | 179 |
| E1 | 10 | 431 |
| L1 | 9 | 408 |
| L1 | 9 | 223 |
| E1 | 8 | 316 |
| L1 | 11 | 113 |
| L2 | 8 | 311 |
| L2 | 9 | 311 |
| E6 | 8 | 119 |
| E1 | 9 | 264 |

TABLE VIIC-continued

HPV11
HLA-A1 Supermotif Peptides

| 2 | 3 | 4 |
|---|---|---|
| E2 | 10 | 136 |
| E2 | 10 | 78 |
| E2 | 10 | 309 |
| E5 | 8 | 7 |
| E5 | 10 | 7 |
| E4 | 10 | 20 |
| E1 | 8 | 349 |
| E1 | 9 | 581 |
| E6 | 9 | 25 |
| L1 | 11 | 388 |
| L2 | 11 | 36 |
| L2 | 10 | 188 |
| L1 | 9 | 362 |
| L1 | 11 | 362 |
| E5 | 10 | 34 |
| E5 | 9 | 35 |
| E6 | 9 | 97 |
| L2 | 10 | 43 |
| L2 | 11 | 43 |
| E5 | 8 | 17 |
| E1 | 9 | 571 |
| E1 | 10 | 500 |
| E1 | 11 | 500 |
| L1 | 10 | 377 |
| L2 | 10 | 286 |
| E5 | 10 | 31 |
| E6 | 8 | 73 |
| E6 | 10 | 73 |
| E1 | 10 | 312 |
| E1 | 11 | 312 |
| E1 | 9 | 254 |
| E6 | 11 | 116 |
| E1 | 8 | 357 |
| E1 | 10 | 357 |
| E1 | 10 | 420 |
| L1 | 10 | 347 |
| E1 | 11 | 484 |
| E1 | 10 | 228 |
| E5 | 10 | 50 |
| E2 | 9 | 84 |
| L1 | 10 | 56 |
| E1 | 8 | 433 |
| L1 | 10 | 61 |
| L1 | 8 | 19 |
| L1 | 10 | 71 |
| E6 | 8 | 52 |
| E6 | 10 | 52 |
| E1 | 8 | 255 |
| E5 | 8 | 33 |
| E5 | 11 | 33 |
| E5 | 9 | 16 |
| E5 | 8 | 36 |
| L1 | 8 | 41 |
| L1 | 9 | 41 |
| E1 | 10 | 521 |
| E4 | 9 | 18 |
| E5 | 9 | 59 |
| E5 | 10 | 59 |
| E5 | 8 | 51 |
| E5 | 8 | 69 |
| E5 | 9 | 69 |
| E5 | 8 | 60 |
| E5 | 9 | 60 |
| L1 | 8 | 379 |
| E1 | 9 | 605 |
| E1 | 10 | 605 |
| E1 | 10 | 218 |
| L2 | 8 | 386 |
| E1 | 9 | 259 |
| L2 | 10 | 239 |
| E5 | 11 | 4 |
| E1 | 8 | 132 |
| E1 | 9 | 358 |
| E5 | 8 | 70 |

TABLE VIIC-continued

HPV11
HLA-A1 Supermotif Peptides

| 2 | 3 | 4 |
|---|---|---|
| E5 | 11 | 70 |
| E5 | 10 | 49 |
| E2 | 8 | 103 |
| E6 | 9 | 38 |
| E6 | 11 | 38 |
| E5 | 8 | 61 |
| L2 | 9 | 337 |
| E5 | 8 | 47 |
| L1 | 9 | 296 |
| L2 | 9 | 245 |
| E5 | 9 | 62 |
| E5 | 11 | 62 |
| E1 | 9 | 421 |
| L1 | 11 | 197 |
| E1 | 9 | 274 |
| E4 | 9 | 1 |
| E1 | 10 | 568 |
| E6 | 10 | 50 |
| E1 | 8 | 395 |
| E1 | 9 | 59 |
| E5 | 8 | 54 |
| E2 | 8 | 127 |
| L1 | 11 | 218 |
| L2 | 8 | 385 |
| L2 | 9 | 385 |
| E1 | 10 | 258 |
| E4 | 8 | 68 |
| L2 | 10 | 336 |
| L1 | 9 | 392 |
| L2 | 9 | 403 |
| E2 | 9 | 353 |
| L1 | 11 | 427 |
| L2 | 11 | 206 |
| L1 | 8 | 90 |
| L2 | 9 | 422 |
| L2 | 10 | 422 |
| L2 | 10 | 358 |
| L1 | 11 | 16 |
| L2 | 11 | 42 |
| L1 | 8 | 302 |
| E4 | 9 | 14 |
| L1 | 8 | 251 |
| L2 | 8 | 395 |
| E1 | 8 | 314 |
| E1 | 9 | 314 |
| E1 | 10 | 314 |
| L2 | 9 | 10 |
| L2 | 9 | 297 |
| L1 | 9 | 40 |
| L1 | 10 | 40 |
| E2 | 10 | 302 |
| L2 | 10 | 244 |
| L1 | 9 | 280 |
| E1 | 8 | 205 |
| L1 | 8 | 141 |
| E1 | 11 | 583 |
| E2 | 8 | 207 |
| E2 | 11 | 23 |
| E6 | 9 | 12 |
| L2 | 10 | 266 |
| E1 | 8 | 422 |
| L1 | 11 | 376 |
| E5 | 11 | 30 |
| E6 | 11 | 23 |
| L1 | 10 | 295 |
| E1 | 8 | 260 |
| L1 | 11 | 298 |
| E2 | 9 | 337 |
| L1 | 11 | 38 |
| L2 | 9 | 208 |
| L1 | 8 | 281 |
| E2 | 9 | 150 |
| E2 | 10 | 150 |
| E2 | 11 | 260 |
| E1 | 11 | 206 |
| E2 | 9 | 180 |
| L2 | 8 | 209 |
| L2 | 10 | 370 |
| L2 | 9 | 240 |
| E1 | 10 | 331 |
| E2 | 8 | 151 |
| E2 | 9 | 151 |
| E1 | 8 | 60 |
| L2 | 8 | 152 |
| E1 | 11 | 436 |
| L1 | 8 | 393 |
| E5 | 10 | 45 |
| L1 | 8 | 344 |
| L2 | 11 | 144 |
| L2 | 9 | 38 |
| E2 | 10 | 261 |
| E2 | 8 | 354 |
| E5 | 10 | 71 |
| E5 | 11 | 71 |
| L1 | 8 | 409 |
| E1 | 10 | 207 |
| E5 | 10 | 15 |
| E5 | 9 | 50 |
| E2 | 10 | 93 |
| E6 | 8 | 26 |
| L1 | 9 | 378 |
| L1 | 10 | 389 |
| E6 | 10 | 11 |
| L2 | 9 | 287 |
| L2 | 10 | 207 |
| E2 | 10 | 149 |
| E2 | 11 | 149 |
| L2 | 11 | 369 |
| L2 | 9 | 151 |
| E5 | 11 | 44 |
| E6 | 8 | 39 |
| E6 | 10 | 39 |
| E1 | 11 | 232 |
| E1 | 9 | 585 |
| E1 | 11 | 585 |
| L2 | 10 | 37 |
| E5 | 11 | 14 |
| L2 | 10 | 150 |
| L2 | 11 | 149 |
| L2 | 11 | 382 |
| L1 | 8 | 224 |
| E1 | 9 | 332 |
| L2 | 10 | 383 |
| L2 | 11 | 383 |
| E1 | 9 | 78 |
| L1 | 9 | 57 |
| L1 | 11 | 57 |
| E1 | 11 | 346 |
| E1 | 8 | 333 |
| E1 | 11 | 499 |
| E5 | 9 | 27 |
| E5 | 9 | 32 |
| E4 | 10 | 17 |
| E1 | 8 | 275 |
| L1 | 8 | 73 |
| E5 | 11 | 48 |
| E5 | 9 | 46 |
| E2 | 11 | 128 |
| L1 | 10 | 114 |
| L1 | 9 | 62 |
| E2 | 9 | 206 |
| L1 | 10 | 17 |
| L1 | 8 | 297 |
| 2 | 10 | 145 |
| L2 | 11 | 414 |
| E2 | 11 | 148 |
| E1 | 10 | 584 |
| L2 | 8 | 246 |

TABLE VIIC-continued

HPV11
HLA-A1 Supermotif Peptides

| 2 | 3 | 4 |
|---|---|---|
| L1 | 9 | 72 |
| E4 | 8 | 2 |
| L1 | 8 | 58 |
| L1 | 10 | 58 |
| L2 | 9 | 120 |
| E6 | 9 | 53 |
| E5 | 10 | 14 |
| E5 | 10 | 58 |
| E5 | 11 | 58 |
| E2 | 9 | 102 |
| E2 | 8 | 92 |
| E2 | 11 | 92 |
| E4 | 8 | 22 |
| L2 | 8 | 431 |
| E1 | 9 | 579 |
| E1 | 11 | 579 |
| E2 | 8 | 138 |
| L1 | 9 | 231 |
| L1 | 8 | 246 |
| L1 | 8 | 359 |
| E5 | 10 | 61 |
| E2 | 10 | 336 |
| E2 | 9 | 159 |
| E2 | 10 | 159 |
| L1 | 9 | 351 |
| L1 | 8 | 26 |
| L1 | 9 | 26 |
| E4 | 11 | 16 |
| E4 | 8 | 9 |
| E2 | 11 | 168 |
| E1 | 8 | 502 |
| E1 | 9 | 502 |
| E2 | 8 | 131 |

SP 1168091 v1

TABLE VIII

HLA-A2 Supermotif-Bearing Peptides

| 1 | 2 | 3 | 4 |
|---|---|---|---|
| HPV16 | E1 | 9 | 316 |
| HPV16 | E1 | 11 | 316 |
| HPV16 | E1 | 9 | 239 |
| HPV16 | E1 | 10 | 239 |
| HPV16 | E1 | 8 | 317 |
| HPV16 | E1 | 10 | 317 |
| HPV16 | E1 | 10 | 205 |
| HPV16 | E1 | 8 | 478 |
| HPV16 | E1 | 11 | 478 |
| HPV16 | E1 | 10 | 112 |
| HPV16 | E1 | 11 | 112 |
| HPV16 | E1 | 9 | 539 |
| HPV16 | E1 | 11 | 539 |
| HPV16 | E1 | 8 | 69 |
| HPV16 | E1 | 9 | 459 |
| HPV16 | E1 | 9 | 318 |
| HPV16 | E1 | 9 | 206 |
| HPV16 | E1 | 10 | 73 |
| HPV16 | E1 | 11 | 73 |
| HPV16 | E1 | 10 | 380 |
| HPV16 | E1 | 10 | 406 |
| HPV16 | E1 | 9 | 524 |
| HPV16 | E1 | 10 | 82 |
| HPV16 | E1 | 11 | 82 |
| HPV16 | E1 | 10 | 23 |
| HPV16 | E1 | 11 | 23 |
| HPV16 | E1 | 11 | 405 |
| HPV16 | E1 | 8 | 237 |
| HPV16 | E1 | 11 | 237 |
| HPV16 | E1 | 8 | 114 |
| HPV16 | E1 | 9 | 114 |
| HPV16 | E1 | 8 | 472 |
| HPV16 | E1 | 10 | 472 |
| HPV16 | E1 | 9 | 259 |
| HPV16 | E1 | 10 | 259 |
| HPV16 | E1 | 9 | 304 |
| HPV16 | E1 | 8 | 187 |
| HPV16 | E1 | 9 | 187 |
| HPV16 | E1 | 11 | 187 |
| HPV16 | E1 | 8 | 353 |
| HPV16 | E1 | 9 | 353 |
| HPV16 | E1 | 10 | 101 |
| HPV16 | E1 | 9 | 640 |
| HPV16 | E1 | 10 | 640 |
| HPV16 | E1 | 8 | 299 |
| HPV16 | E1 | 9 | 299 |
| HPV16 | E1 | 10 | 515 |
| HPV16 | E1 | 11 | 515 |
| HPV16 | E1 | 10 | 523 |
| HPV16 | E1 | 11 | 81 |
| HPV16 | E1 | 10 | 97 |
| HPV16 | E1 | 8 | 368 |
| HPV16 | E1 | 9 | 368 |
| HPV16 | E1 | 10 | 43 |
| HPV16 | E1 | 11 | 43 |
| HPV16 | E1 | 8 | 384 |
| HPV16 | E1 | 10 | 384 |
| HPV16 | E1 | 10 | 335 |
| HPV16 | E1 | 11 | 335 |
| HPV16 | E1 | 8 | 548 |
| HPV16 | E1 | 10 | 548 |
| HPV16 | E1 | 8 | 75 |
| HPV16 | E1 | 9 | 75 |
| HPV16 | E1 | 11 | 75 |
| HPV16 | E1 | 8 | 22 |
| HPV16 | E1 | 11 | 22 |
| HPV16 | E1 | 9 | 374 |
| HPV16 | E1 | 10 | 374 |
| HPV16 | E1 | 9 | 356 |
| HPV16 | E1 | 10 | 213 |
| HPV16 | E1 | 11 | 213 |
| HPV16 | E1 | 8 | 65 |
| HPV16 | E1 | 9 | 65 |
| HPV16 | E1 | 8 | 63 |
| HPV16 | E1 | 10 | 63 |
| HPV16 | E1 | 11 | 63 |
| HPV16 | E1 | 10 | 288 |
| HPV16 | E1 | 11 | 288 |
| HPV16 | E1 | 8 | 140 |
| HPV16 | E1 | 8 | 138 |
| HPV16 | E1 | 10 | 138 |
| HPV16 | E1 | 10 | 331 |
| HPV16 | E1 | 9 | 51 |
| HPV16 | E1 | 10 | 51 |
| HPV16 | E1 | 8 | 392 |
| HPV16 | E1 | 10 | 392 |
| HPV16 | E1 | 11 | 392 |
| HPV16 | E1 | 11 | 463 |
| HPV16 | E1 | 10 | 493 |
| HPV16 | E1 | 10 | 445 |
| HPV16 | E1 | 9 | 456 |
| HPV16 | E1 | 8 | 453 |
| HPV16 | E1 | 10 | 501 |
| HPV16 | E1 | 9 | 477 |
| HPV16 | E1 | 8 | 466 |
| HPV16 | E1 | 9 | 466 |
| HPV16 | E1 | 10 | 466 |
| HPV16 | E1 | 8 | 325 |
| HPV16 | E1 | 10 | 242 |
| HPV16 | E1 | 8 | 519 |
| HPV16 | E1 | 8 | 487 |
| HPV16 | E1 | 8 | 272 |
| HPV16 | E1 | 9 | 571 |
| HPV16 | E1 | 10 | 12 |
| HPV16 | E1 | 8 | 6 |

TABLE VIII-continued

HLA-A2 Supermotif-Bearing Peptides

| 1 | 2 | 3 | 4 |
|---|---|---|---|
| HPV16 | E1 | 8 | 450 |
| HPV16 | E1 | 9 | 450 |
| HPV16 | E1 | 10 | 450 |
| HPV16 | E1 | 11 | 450 |
| HPV16 | E1 | 8 | 179 |
| HPV16 | E1 | 11 | 179 |
| HPV16 | E1 | 8 | 216 |
| HPV16 | E1 | 9 | 68 |
| HPV16 | E1 | 11 | 263 |
| HPV16 | E1 | 8 | 184 |
| HPV16 | E1 | 9 | 184 |
| HPV16 | E1 | 11 | 184 |
| HPV16 | E1 | 10 | 238 |
| HPV16 | E1 | 11 | 238 |
| HPV16 | E1 | 8 | 247 |
| HPV16 | E1 | 9 | 247 |
| HPV16 | E1 | 8 | 375 |
| HPV16 | E1 | 9 | 375 |
| HPV16 | E1 | 11 | 375 |
| HPV16 | E1 | 9 | 473 |
| HPV16 | E1 | 10 | 194 |
| HPV16 | E1 | 10 | 264 |
| HPV16 | E1 | 11 | 264 |
| HPV16 | E1 | 9 | 564 |
| HPV16 | E1 | 8 | 369 |
| HPV16 | E1 | 8 | 401 |
| HPV16 | E1 | 10 | 442 |
| HPV16 | E1 | 8 | 52 |
| HPV16 | E1 | 9 | 52 |
| HPV16 | E1 | 11 | 52 |
| HPV16 | E1 | 11 | 204 |
| HPV16 | E1 | 11 | 111 |
| HPV16 | E1 | 8 | 517 |
| HPV16 | E1 | 9 | 517 |
| HPV16 | E1 | 10 | 517 |
| HPV16 | E1 | 8 | 400 |
| HPV16 | E1 | 9 | 400 |
| HPV16 | E1 | 8 | 296 |
| HPV16 | E1 | 10 | 296 |
| HPV16 | E1 | 11 | 296 |
| HPV16 | E1 | 9 | 292 |
| HPV16 | E1 | 8 | 311 |
| HPV16 | E1 | 9 | 311 |
| HPV16 | E1 | 9 | 77 |
| HPV16 | E1 | 10 | 77 |
| HPV16 | E1 | 9 | 418 |
| HPV16 | E1 | 10 | 117 |
| HPV16 | E1 | 10 | 323 |
| HPV16 | E1 | 9 | 252 |
| HPV16 | E1 | 11 | 252 |
| HPV16 | E1 | 8 | 199 |
| HPV16 | E1 | 9 | 199 |
| HPV16 | E1 | 10 | 199 |
| HPV16 | E1 | 11 | 199 |
| HPV16 | E1 | 8 | 267 |
| HPV16 | E1 | 9 | 267 |
| HPV16 | E1 | 10 | 267 |
| HPV16 | E1 | 11 | 267 |
| HPV16 | E1 | 8 | 513 |
| HPV16 | E1 | 9 | 513 |
| HPV16 | E1 | 8 | 382 |
| HPV16 | E1 | 10 | 382 |
| HPV16 | E1 | 10 | 208 |
| HPV16 | E1 | 8 | 563 |
| HPV16 | E1 | 10 | 563 |
| HPV16 | E1 | 9 | 297 |
| HPV16 | E1 | 10 | 297 |
| HPV16 | E1 | 11 | 297 |
| HPV16 | E1 | 9 | 562 |
| HPV16 | E1 | 11 | 562 |
| HPV16 | E1 | 9 | 254 |
| HPV16 | E1 | 11 | 254 |
| HPV16 | E1 | 8 | 293 |
| HPV16 | E1 | 11 | 293 |
| HPV16 | E1 | 8 | 474 |
| HPV16 | E1 | 9 | 490 |
| HPV16 | E1 | 10 | 490 |
| HPV16 | E1 | 10 | 464 |
| HPV16 | E1 | 11 | 464 |
| HPV16 | E1 | 9 | 494 |
| HPV16 | E1 | 9 | 346 |
| HPV16 | E1 | 9 | 510 |
| HPV16 | E1 | 11 | 510 |
| HPV16 | E1 | 8 | 255 |
| HPV16 | E1 | 10 | 255 |
| HPV16 | E1 | 9 | 145 |
| HPV16 | E1 | 11 | 145 |
| HPV16 | E1 | 8 | 457 |
| HPV16 | E1 | 11 | 457 |
| HPV16 | E1 | 8 | 191 |
| HPV16 | E1 | 10 | 191 |
| HPV16 | E1 | 9 | 243 |
| HPV16 | E1 | 11 | 243 |
| HPV16 | E1 | 8 | 59 |
| HPV16 | E1 | 9 | 59 |
| HPV16 | E1 | 11 | 59 |
| HPV16 | E1 | 9 | 554 |
| HPV16 | E1 | 10 | 554 |
| HPV16 | E1 | 11 | 554 |
| HPV16 | E1 | 11 | 222 |
| HPV16 | E1 | 11 | 544 |
| HPV16 | E1 | 8 | 91 |
| HPV16 | E1 | 10 | 306 |
| HPV16 | E1 | 11 | 306 |
| HPV16 | E1 | 8 | 207 |
| HPV16 | E1 | 11 | 207 |
| HPV16 | E1 | 10 | 144 |
| HPV16 | E1 | 8 | 305 |
| HPV16 | E1 | 11 | 305 |
| HPV16 | E1 | 10 | 360 |
| HPV16 | E1 | 11 | 360 |
| HPV16 | E1 | 11 | 569 |
| HPV16 | E1 | 8 | 202 |
| HPV16 | E1 | 8 | 538 |
| HPV16 | E1 | 10 | 538 |
| HPV16 | E1 | 8 | 193 |
| HPV16 | E1 | 11 | 193 |
| HPV16 | E1 | 9 | 328 |
| HPV16 | E1 | 8 | 105 |
| HPV16 | E1 | 9 | 105 |
| HPV16 | E1 | 11 | 105 |
| HPV16 | E1 | 10 | 535 |
| HPV16 | E1 | 11 | 535 |
| HPV16 | E1 | 9 | 136 |
| HPV16 | E1 | 10 | 136 |
| HPV16 | E1 | 9 | 480 |
| HPV16 | E1 | 11 | 480 |
| HPV16 | E1 | 8 | 196 |
| HPV16 | E1 | 10 | 196 |
| HPV16 | E1 | 11 | 196 |
| HPV16 | E1 | 10 | 4 |
| HPV16 | E1 | 9 | 512 |
| HPV16 | E1 | 10 | 512 |
| HPV16 | E1 | 8 | 561 |
| HPV16 | E1 | 10 | 561 |
| HPV16 | E1 | 9 | 94 |
| HPV16 | E1 | 8 | 190 |
| HPV16 | E1 | 9 | 190 |
| HPV16 | E1 | 11 | 190 |
| HPV16 | E1 | 10 | 553 |
| HPV16 | E1 | 11 | 553 |
| HPV16 | E1 | 11 | 302 |
| HPV16 | E1 | 11 | 636 |
| HPV16 | E1 | 9 | 61 |
| HPV16 | E1 | 10 | 61 |
| HPV16 | E1 | 9 | 398 |
| HPV16 | E1 | 10 | 398 |
| HPV16 | E1 | 11 | 398 |
| HPV16 | E1 | 11 | 441 |
| HPV16 | E1 | 9 | 381 |

TABLE VIII-continued

HLA-A2 Supermotif-Bearing Peptides

| 1 | 2 | 3 | 4 |
|---|---|---|---|
| HPV16 | E1 | 11 | 381 |
| HPV16 | E1 | 8 | 556 |
| HPV16 | E1 | 9 | 556 |
| HPV16 | E1 | 10 | 556 |
| HPV16 | E1 | 11 | 143 |
| HPV16 | E1 | 8 | 419 |
| HPV16 | E1 | 11 | 359 |
| HPV16 | E1 | 9 | 256 |
| HPV16 | E1 | 8 | 188 |
| HPV16 | E1 | 10 | 188 |
| HPV16 | E1 | 11 | 188 |
| HPV16 | E1 | 8 | 146 |
| HPV16 | E1 | 10 | 146 |
| HPV16 | E1 | 8 | 84 |
| HPV16 | E1 | 9 | 84 |
| HPV16 | E1 | 9 | 414 |
| HPV16 | E1 | 8 | 615 |
| HPV16 | E1 | 11 | 432 |
| HPV16 | E1 | 10 | 390 |
| HPV16 | E1 | 8 | 246 |
| HPV16 | E1 | 9 | 246 |
| HPV16 | E1 | 10 | 246 |
| HPV16 | E1 | 11 | 250 |
| HPV16 | E1 | 8 | 266 |
| HPV16 | E1 | 9 | 266 |
| HPV16 | E1 | 10 | 266 |
| HPV16 | E1 | 11 | 266 |
| HPV16 | E1 | 8 | 484 |
| HPV16 | E1 | 11 | 484 |
| HPV16 | E1 | 10 | 489 |
| HPV16 | E1 | 11 | 489 |
| HPV16 | E1 | 8 | 634 |
| HPV16 | E1 | 9 | 546 |
| HPV16 | E1 | 10 | 546 |
| HPV16 | E1 | 10 | 397 |
| HPV16 | E1 | 11 | 397 |
| HPV16 | E1 | 11 | 423 |
| HPV16 | E1 | 11 | 314 |
| HPV16 | E1 | 8 | 231 |
| HPV16 | E1 | 9 | 231 |
| HPV16 | E1 | 0 | 231 |
| HPV16 | E1 | 10 | 315 |
| HPV16 | E1 | 8 | 66 |
| HPV16 | E1 | 11 | 66 |
| HPV16 | E1 | 10 | 458 |
| HPV16 | E1 | 11 | 72 |
| HPV16 | E1 | 8 | 185 |
| HPV16 | E1 | 10 | 185 |
| HPV16 | E1 | 11 | 185 |
| HPV16 | E1 | 9 | 289 |
| HPV16 | E1 | 10 | 289 |
| HPV16 | E1 | 8 | 253 |
| HPV16 | E1 | 10 | 253 |
| HPV16 | E1 | 9 | 407 |
| HPV16 | E1 | 8 | 60 |
| HPV16 | E1 | 10 | 60 |
| HPV16 | E1 | 11 | 60 |
| HPV16 | E1 | 11 | 344 |
| HPV16 | E1 | 8 | 525 |
| HPV16 | E1 | 8 | 85 |
| HPV16 | E1 | 11 | 85 |
| HPV16 | E1 | 9 | 197 |
| HPV16 | E1 | 10 | 197 |
| HPV16 | E1 | 11 | 197 |
| HPV16 | E1 | 10 | 345 |
| HPV16 | E1 | 9 | 443 |
| HPV16 | E1 | 8 | 555 |
| HPV16 | E1 | 9 | 555 |
| HPV16 | E1 | 10 | 555 |
| HPV16 | E1 | 11 | 555 |
| HPV16 | E1 | 9 | 83 |
| HPV16 | E1 | 10 | 83 |
| HPV16 | E1 | 9 | 361 |
| HPV16 | E1 | 10 | 361 |
| HPV16 | E1 | 9 | 24 |
| HPV16 | E1 | 10 | 24 |
| HPV16 | E1 | 8 | 363 |
| HPV16 | E1 | 9 | 425 |
| HPV16 | E1 | 8 | 339 |
| HPV16 | E1 | 8 | 509 |
| HPV16 | E1 | 10 | 509 |
| HPV16 | E1 | 11 | 379 |
| HPV16 | E1 | 9 | 531 |
| HPV16 | E1 | 10 | 531 |
| HPV16 | E1 | 8 | 261 |
| HPV16 | E1 | 8 | 578 |
| HPV16 | E1 | 10 | 578 |
| HPV16 | E1 | 9 | 58 |
| HPV16 | E1 | 10 | 58 |
| HPV16 | E1 | 9 | 90 |
| HPV16 | E1 | 10 | 448 |
| HPV16 | E1 | 11 | 448 |
| HPV16 | E1 | 10 | 20 |
| HPV16 | E1 | 8 | 220 |
| HPV16 | E1 | 9 | 220 |
| HPV16 | E1 | 10 | 220 |
| HPV16 | E1 | 8 | 72 |
| HPV16 | E1 | 10 | 72 |
| HPV16 | E1 | 11 | 72 |
| HPV16 | E1 | 9 | 41 |
| HPV16 | E1 | 9 | 228 |
| HPV16 | E1 | 10 | 228 |
| HPV16 | E1 | 11 | 228 |
| HPV16 | E1 | 9 | 69 |
| HPV16 | E2 | 10 | 69 |
| HPV16 | E2 | 11 | 69 |
| HPV16 | E2 | 8 | 221 |
| HPV16 | E2 | 9 | 221 |
| HPV16 | E2 | 11 | 221 |
| HPV16 | E2 | 9 | 226 |
| HPV16 | E2 | 11 | 226 |
| HPV16 | E2 | 8 | 63 |
| HPV16 | E2 | 10 | 63 |
| HPV16 | E2 | 11 | 63 |
| HPV16 | E2 | 9 | 314 |
| HPV16 | E2 | 10 | 40 |
| HPV16 | E2 | 8 | 109 |
| HPV16 | E2 | 9 | 109 |
| HPV16 | E2 | 11 | 109 |
| HPV16 | E2 | 11 | 300 |
| HPV16 | E2 | 11 | 5 |
| HPV16 | E2 | 10 | 309 |
| HPV16 | E2 | 10 | 174 |
| HPV16 | E2 | 8 | 294 |
| HPV16 | E2 | 9 | 124 |
| HPV16 | E2 | 9 | 344 |
| HPV16 | E2 | 8 | 246 |
| HPV16 | E2 | 9 | 246 |
| HPV16 | E2 | 11 | 246 |
| HPV16 | E2 | 8 | 96 |
| HPV16 | E2 | 9 | 96 |
| HPV16 | E2 | 10 | 96 |
| HPV16 | E2 | 11 | 142 |
| HPV16 | E2 | 8 | 209 |
| HPV16 | E2 | 8 | 74 |
| HPV16 | E2 | 9 | 74 |
| HPV16 | E2 | 11 | 48 |
| HPV16 | E2 | 9 | 2 |
| HPV16 | E2 | 8 | 185 |
| HPV16 | E2 | 9 | 185 |
| HPV16 | E2 | 10 | 185 |
| HPV16 | E2 | 8 | 118 |
| HPV16 | E2 | 11 | 118 |
| HPV16 | E2 | 8 | 204 |
| HPV16 | E2 | 8 | 100 |
| HPV16 | E2 | 11 | 100 |
| HPV16 | E2 | 10 | 346 |
| HPV16 | E2 | 11 | 346 |
| HPV16 | E2 | 8 | 168 |
| HPV16 | E2 | 9 | 156 |

TABLE VIII-continued

HLA-A2 Supermotif-Bearing Peptides

| 1 | 2 | 3 | 4 |
|---|---|---|---|
| HPV16 | E2 | 11 | 156 |
| HPV16 | E2 | 8 | 150 |
| HPV16 | E2 | 11 | 150 |
| HPV16 | E2 | 8 | 190 |
| HPV16 | E2 | 10 | 190 |
| HPV16 | E2 | 8 | 230 |
| HPV16 | E2 | 9 | 230 |
| HPV16 | E2 | 8 | 187 |
| HPV16 | E2 | 11 | 187 |
| HPV16 | E2 | 8 | 29 |
| HPV16 | E2 | 10 | 29 |
| HPV16 | E2 | 9 | 53 |
| HPV16 | E2 | 10 | 53 |
| HPV16 | E2 | 11 | 53 |
| HPV16 | E2 | 8 | 136 |
| HPV16 | E2 | 10 | 136 |
| HPV16 | E2 | 11 | 136 |
| HPV16 | E2 | 8 | 214 |
| HPV16 | E2 | 9 | 214 |
| HPV16 | E2 | 11 | 214 |
| HPV16 | E2 | 8 | 290 |
| HPV16 | E2 | 9 | 290 |
| HPV16 | E2 | 8 | 35 |
| HPV16 | E2 | 8 | 56 |
| HPV16 | E2 | 9 | 56 |
| HPV16 | E2 | 9 | 223 |
| HPV16 | E2 | 11 | 252 |
| HPV16 | E2 | 11 | 210 |
| HPV16 | E2 | 10 | 15 |
| HPV16 | E2 | 10 | 238 |
| HPV16 | E2 | 8 | 356 |
| HPV16 | E2 | 10 | 356 |
| HPV16 | E2 | 8 | 288 |
| HPV16 | E2 | 10 | 288 |
| HPV16 | E2 | 11 | 288 |
| HPV16 | E2 | 8 | 68 |
| HPV16 | E2 | 10 | 68 |
| HPV16 | E2 | 11 | 68 |
| HPV16 | E2 | 10 | 45 |
| HPV16 | E2 | 10 | 225 |
| HPV16 | E2 | 11 | 14 |
| HPV16 | E2 | 8 | 351 |
| HPV16 | E2 | 10 | 351 |
| HPV16 | E2 | 8 | 255 |
| HPV16 | E2 | 11 | 255 |
| HPV16 | E2 | 10 | 354 |
| HPV16 | E2 | 11 | 182 |
| HPV16 | E2 | 8 | 215 |
| HPV16 | E2 | 10 | 215 |
| HPV16 | E2 | 8 | 62 |
| HPV16 | E2 | 9 | 62 |
| HPV16 | E2 | 11 | 62 |
| HPV16 | E2 | 10 | 256 |
| HPV16 | E2 | 8 | 70 |
| HPV16 | E2 | 9 | 70 |
| HPV16 | E2 | 10 | 70 |
| HPV16 | E2 | 8 | 94 |
| HPV16 | E2 | 10 | 94 |
| HPV16 | E2 | 11 | 94 |
| HPV16 | E2 | 8 | 75 |
| HPV16 | E2 | 8 | 103 |
| HPV16 | E2 | 9 | 16 |
| HPV16 | E2 | 11 | 16 |
| HPV16 | E2 | 9 | 127 |
| HPV16 | E2 | 11 | 127 |
| HPV16 | E2 | 8 | 284 |
| HPV16 | E2 | 8 | 9 |
| HPV16 | E2 | 9 | 9 |
| HPV16 | E2 | 8 | 325 |
| HPV16 | E2 | 9 | 325 |
| HPV16 | E2 | 10 | 325 |
| HPV16 | E2 | 11 | 325 |
| HPV16 | E2 | 8 | 219 |
| HPV16 | E2 | 9 | 219 |
| HPV16 | E2 | 10 | 219 |
| HPV16 | E2 | 11 | 219 |
| HPV16 | E2 | 9 | 287 |
| HPV16 | E2 | 11 | 287 |
| HPV16 | E2 | 11 | 106 |
| HPV16 | E2 | 10 | 60 |
| HPV16 | E2 | 11 | 60 |
| HPV16 | E2 | 10 | 196 |
| HPV16 | E2 | 8 | 71 |
| HPV16 | E2 | 9 | 71 |
| HPV16 | E2 | 11 | 71 |
| HPV16 | E2 | 10 | 151 |
| HPV16 | E2 | 9 | 191 |
| HPV16 | E2 | 8 | 349 |
| HPV16 | E2 | 9 | 349 |
| HPV16 | E2 | 10 | 349 |
| HPV16 | E2 | 8 | 57 |
| HPV16 | E2 | 8 | 278 |
| HPV16 | E2 | 9 | 278 |
| HPV16 | E2 | 11 | 278 |
| HPV16 | E2 | 10 | 37 |
| HPV16 | E2 | 9 | 7 |
| HPV16 | E2 | 10 | 7 |
| HPV16 | E2 | 11 | 7 |
| HPV16 | E2 | 9 | 212 |
| HPV16 | E2 | 10 | 212 |
| HPV16 | E2 | 11 | 212 |
| HPV16 | E2 | 11 | 165 |
| HPV16 | E2 | 8 | 98 |
| HPV16 | E2 | 10 | 98 |
| HPV16 | E2 | 8 | 348 |
| HPV16 | E2 | 9 | 348 |
| HPV16 | E2 | 10 | 348 |
| HPV16 | E2 | 11 | 348 |
| HPV16 | E2 | 9 | 85 |
| HPV16 | E2 | 10 | 85 |
| HPV16 | E2 | 8 | 23 |
| HPV16 | E2 | 10 | 317 |
| HPV16 | E2 | 8 | 261 |
| HPV16 | E2 | 9 | 261 |
| HPV16 | E2 | 10 | 261 |
| HPV16 | E2 | 8 | 198 |
| HPV16 | E2 | 9 | 144 |
| HPV16 | E2 | 11 | 269 |
| HPV16 | E2 | 10 | 313 |
| HPV16 | E2 | 11 | 237 |
| HPV16 | E2 | 9 | 355 |
| HPV16 | E2 | 11 | 355 |
| HPV16 | E2 | 9 | 61 |
| HPV16 | E2 | 10 | 61 |
| HPV16 | E2 | 8 | 3 |
| HPV16 | E2 | 9 | 93 |
| HPV16 | E2 | 11 | 93 |
| HPV16 | E2 | 9 | 310 |
| HPV16 | E2 | 8 | 128 |
| HPV16 | E2 | 10 | 128 |
| HPV16 | E2 | 10 | 253 |
| HPV16 | E2 | 11 | 285 |
| HPV16 | E2 | 10 | 116 |
| HPV16 | E2 | 9 | 357 |
| HPV16 | E2 | 8 | 227 |
| HPV16 | E2 | 10 | 227 |
| HPV16 | E2 | 11 | 227 |
| HPV16 | E2 | 8 | 192 |
| HPV16 | E2 | 10 | 119 |
| HPV16 | E2 | 11 | 119 |
| HPV16 | E2 | 8 | 145 |
| HPV16 | E2 | 11 | 147 |
| HPV16 | E2 | 10 | 341 |
| HPV16 | E2 | 11 | 321 |
| HPV16 | E2 | 10 | 134 |
| HPV16 | E2 | 8 | 92 |
| HPV16 | E2 | 10 | 92 |
| HPV16 | E2 | 8 | 138 |
| HPV16 | E2 | 9 | 138 |
| HPV16 | E2 | 10 | 138 |

TABLE VIII-continued

HLA-A2 Supermotif-Bearing Peptides

| 1 | 2 | 3 | 4 |
|---|---|---|---|
| HPV16 | E2 | 11 | 138 |
| HPV16 | E2 | 9 | 102 |
| HPV16 | E2 | 11 | 312 |
| HPV16 | E2 | 9 | 131 |
| HPV16 | E2 | 11 | 115 |
| HPV16 | E2 | 8 | 159 |
| HPV16 | E2 | 11 | 159 |
| HPV16 | E5 | 9 | 53 |
| HPV16 | E5 | 10 | 53 |
| HPV16 | E5 | 8 | 26 |
| HPV16 | E5 | 9 | 26 |
| HPV16 | E5 | 11 | 26 |
| HPV16 | E5 | 9 | 24 |
| HPV16 | E5 | 10 | 24 |
| HPV16 | E5 | 11 | 24 |
| HPV16 | E5 | 8 | 20 |
| HPV16 | E5 | 9 | 20 |
| HPV16 | E5 | 10 | 20 |
| HPV16 | E5 | 8 | 5 |
| HPV16 | E5 | 9 | 5 |
| HPV16 | E5 | 8 | 60 |
| HPV16 | E5 | 10 | 60 |
| HPV16 | E5 | 10 | 72 |
| HPV16 | E5 | 11 | 72 |
| HPV16 | E5 | 8 | 15 |
| HPV16 | E5 | 9 | 15 |
| HPV16 | E5 | 11 | 15 |
| HPV16 | E5 | 8 | 66 |
| HPV16 | E5 | 9 | 66 |
| HPV16 | E5 | 11 | 66 |
| HPV16 | E5 | 8 | 75 |
| HPV16 | E5 | 9 | 75 |
| HPV16 | E5 | 8 | 64 |
| HPV16 | E5 | 10 | 64 |
| HPV16 | E5 | 11 | 64 |
| HPV16 | E5 | 9 | 43 |
| HPV16 | E5 | 10 | 43 |
| HPV16 | E5 | 11 | 43 |
| HPV16 | E5 | 8 | 44 |
| HPV16 | E5 | 9 | 44 |
| HPV16 | E5 | 10 | 44 |
| HPV16 | E5 | 11 | 44 |
| HPV16 | E5 | 11 | 51 |
| HPV16 | E5 | 9 | 61 |
| HPV16 | E5 | 11 | 61 |
| HPV16 | E5 | 10 | 12 |
| HPV16 | E5 | 11 | 12 |
| HPV16 | E5 | 9 | 73 |
| HPV16 | E5 | 10 | 73 |
| HPV16 | E5 | 11 | 73 |
| HPV16 | E5 | 8 | 42 |
| HPV16 | E5 | 10 | 42 |
| HPV16 | E5 | 11 | 42 |
| HPV16 | E5 | 9 | 28 |
| HPV16 | E5 | 11 | 28 |
| HPV16 | E5 | 11 | 11 |
| HPV16 | E5 | 8 | 16 |
| HPV16 | E5 | 10 | 16 |
| HPV16 | E5 | 8 | 22 |
| HPV16 | E5 | 11 | 22 |
| HPV16 | E5 | 8 | 27 |
| HPV16 | E5 | 10 | 27 |
| HPV16 | E5 | 9 | 32 |
| HPV16 | E5 | 11 | 32 |
| HPV16 | E5 | 8 | 47 |
| HPV16 | E5 | 10 | 47 |
| HPV16 | E5 | 8 | 33 |
| HPV16 | E5 | 10 | 33 |
| HPV16 | E5 | 11 | 33 |
| HPV16 | E5 | 9 | 48 |
| HPV16 | E5 | 8 | 45 |
| HPV16 | E5 | 9 | 45 |
| HPV16 | E5 | 10 | 45 |
| HPV16 | E5 | 9 | 1 |
| HPV16 | E5 | 10 | 1 |
| HPV16 | E5 | 11 | 1 |
| HPV16 | E5 | 8 | 3 |
| HPV16 | E5 | 9 | 3 |
| HPV16 | E5 | 10 | 3 |
| HPV16 | E5 | 11 | 3 |
| HPV16 | E5 | 9 | 70 |
| HPV16 | E5 | 8 | 71 |
| HPV16 | E5 | 10 | 31 |
| HPV16 | E5 | 8 | 55 |
| HPV16 | E5 | 10 | 55 |
| HPV16 | E5 | 11 | 55 |
| HPV16 | E5 | 8 | 41 |
| HPV16 | E5 | 9 | 41 |
| HPV16 | E5 | 11 | 41 |
| HPV16 | E5 | 9 | 8 |
| HPV16 | E5 | 10 | 8 |
| HPV16 | E5 | 8 | 37 |
| HPV16 | E5 | 9 | 37 |
| HPV16 | E5 | 10 | 37 |
| HPV16 | E5 | 11 | 37 |
| HPV16 | E5 | 8 | 35 |
| HPV16 | E5 | 9 | 35 |
| HPV16 | E5 | 10 | 35 |
| HPV16 | E5 | 11 | 35 |
| HPV16 | E5 | 10 | 52 |
| HPV16 | E5 | 11 | 52 |
| HPV16 | E5 | 8 | 6 |
| HPV16 | E5 | 11 | 6 |
| HPV16 | E5 | 8 | 10 |
| HPV16 | E5 | 8 | 9 |
| HPV16 | E5 | 9 | 9 |
| HPV16 | E5 | 8 | 21 |
| HPV16 | E5 | 9 | 21 |
| HPV16 | E5 | 8 | 46 |
| HPV16 | E5 | 9 | 46 |
| HPV16 | E5 | 11 | 46 |
| HPV16 | E5 | 9 | 63 |
| HPV16 | E5 | 11 | 63 |
| HPV16 | E5 | 9 | 68 |
| HPV16 | E5 | 11 | 68 |
| HPV16 | E5 | 8 | 39 |
| HPV16 | E5 | 9 | 39 |
| HPV16 | E5 | 10 | 39 |
| HPV16 | E5 | 11 | 39 |
| HPV16 | E6 | 8 | 110 |
| HPV16 | E6 | 11 | 58 |
| HPV16 | E6 | 8 | 73 |
| HPV16 | E6 | 10 | 143 |
| HPV16 | E6 | 8 | 23 |
| HPV16 | E6 | 11 | 23 |
| HPV16 | E6 | 8 | 37 |
| HPV16 | E6 | 9 | 37 |
| HPV16 | E6 | 9 | 25 |
| HPV16 | E6 | 10 | 25 |
| HPV16 | E6 | 11 | 25 |
| HPV16 | E6 | 8 | 96 |
| HPV16 | E6 | 11 | 96 |
| HPV16 | E6 | 10 | 48 |
| HPV16 | E6 | 8 | 52 |
| HPV16 | E6 | 9 | 52 |
| HPV16 | E6 | 11 | 9 |
| HPV16 | E6 | 11 | 125 |
| HPV16 | E6 | 11 | 34 |
| HPV16 | E6 | 10 | 59 |
| HPV16 | E6 | 11 | 59 |
| HPV16 | E6 | 9 | 18 |
| HPV16 | E6 | 11 | 18 |
| HPV16 | E6 | 9 | 41 |
| HPV16 | E6 | 11 | 107 |
| HPV16 | E6 | 10 | 44 |
| HPV16 | E6 | 8 | 26 |
| HPV16 | E6 | 9 | 26 |
| HPV16 | E6 | 10 | 26 |
| HPV16 | E6 | 11 | 134 |
| HPV16 | E6 | 10 | 102 |

TABLE VIII-continued

HLA-A2 Supermotif-Bearing Peptides

| 1 | 2 | 3 | 4 |
|---|---|---|---|
| HPV16 | E6 | 11 | 116 |
| HPV16 | E6 | 8 | 12 |
| HPV16 | E6 | 11 | 12 |
| HPV16 | E6 | 9 | 20 |
| HPV16 | E6 | 10 | 20 |
| HPV16 | E6 | 11 | 20 |
| HPV16 | E6 | 8 | 21 |
| HPV16 | E6 | 9 | 21 |
| HPV16 | E6 | 10 | 21 |
| HPV16 | E6 | 11 | 43 |
| HPV16 | E6 | 8 | 42 |
| HPV16 | E6 | 10 | 97 |
| HPV16 | E6 | 11 | 97 |
| HPV16 | E6 | 8 | 27 |
| HPV16 | E6 | 9 | 27 |
| HPV16 | E6 | 8 | 151 |
| HPV16 | E6 | 10 | 29 |
| HPV16 | E6 | 10 | 94 |
| HPV16 | E6 | 8 | 28 |
| HPV16 | E6 | 11 | 28 |
| HPV16 | E6 | 11 | 93 |
| HPV16 | E6 | 8 | 67 |
| HPV16 | E7 | 9 | 68 |
| HPV16 | E7 | 11 | 68 |
| HPV16 | E7 | 8 | 75 |
| HPV16 | E7 | 9 | 75 |
| HPV16 | E7 | 10 | 75 |
| HPV16 | E7 | 9 | 81 |
| HPV16 | E7 | 10 | 81 |
| HPV16 | E7 | 9 | 14 |
| HPV16 | E7 | 8 | 21 |
| HPV16 | E7 | 9 | 4 |
| HPV16 | E7 | 10 | 4 |
| HPV16 | E7 | 9 | 37 |
| HPV16 | E7 | 11 | 18 |
| HPV16 | E7 | 8 | 43 |
| HPV16 | E7 | 9 | 85 |
| HPV16 | E7 | 10 | 73 |
| HPV16 | E7 | 11 | 73 |
| HPV16 | E7 | 11 | 54 |
| HPV16 | E7 | 8 | 82 |
| HPV16 | E7 | 9 | 82 |
| HPV16 | E7 | 8 | 83 |
| HPV16 | E7 | 11 | 83 |
| HPV16 | E7 | 8 | 15 |
| HPV16 | E7 | 8 | 12 |
| HPV16 | E7 | 9 | 12 |
| HPV16 | E7 | 11 | 12 |
| HPV16 | E7 | 10 | 41 |
| HPV16 | E7 | 8 | 6 |
| HPV16 | E7 | 10 | 6 |
| HPV16 | E7 | 11 | 44 |
| HPV16 | E7 | 8 | 49 |
| HPV16 | E7 | 9 | 66 |
| HPV16 | E7 | 11 | 66 |
| HPV16 | E7 | 8 | 77 |
| HPV16 | E7 | 10 | 77 |
| HPV16 | E7 | 11 | 77 |
| HPV16 | E7 | 8 | 71 |
| HPV16 | E7 | 9 | 71 |
| HPV16 | E7 | 10 | 63 |
| HPV16 | E7 | 9 | 78 |
| HPV16 | E7 | 10 | 78 |
| HPV16 | E7 | 8 | 86 |
| HPV16 | E7 | 9 | 7 |
| HPV16 | E7 | 9 | 64 |
| HPV16 | E7 | 11 | 64 |
| HPV16 | E7 | 10 | 19 |
| HPV16 | E7 | 8 | 69 |
| HPV16 | E7 | 10 | 69 |
| HPV16 | E7 | 11 | 69 |
| HPV16 | E7 | 10 | 55 |
| HPV16 | E7 | 11 | 55 |
| HPV16 | E7 | 9 | 11 |
| HPV16 | E7 | 10 | 11 |
| HPV16 | L1 | 8 | 372 |
| HPV16 | L1 | 9 | 372 |
| HPV16 | L1 | 8 | 451 |
| HPV16 | L1 | 11 | 451 |
| HPV16 | L1 | 8 | 373 |
| HPV16 | L1 | 9 | 233 |
| HPV16 | L1 | 8 | 342 |
| HPV16 | L1 | 10 | 330 |
| HPV16 | L1 | 8 | 513 |
| HPV16 | L1 | 10 | 513 |
| HPV16 | L1 | 11 | 513 |
| HPV16 | L1 | 8 | 35 |
| HPV16 | L1 | 10 | 35 |
| HPV16 | L1 | 10 | 292 |
| HPV16 | L1 | 9 | 70 |
| HPV16 | L1 | 10 | 205 |
| HPV16 | L1 | 9 | 371 |
| HPV16 | L1 | 10 | 371 |
| HPV16 | L1 | 9 | 172 |
| HPV16 | L1 | 11 | 172 |
| HPV16 | L1 | 9 | 183 |
| HPV16 | L1 | 8 | 454 |
| HPV16 | L1 | 11 | 251 |
| HPV16 | L1 | 11 | 329 |
| HPV16 | L1 | 8 | 397 |
| HPV16 | L1 | 11 | 397 |
| HPV16 | L1 | 10 | 300 |
| HPV16 | L1 | 11 | 300 |
| HPV16 | L1 | 9 | 225 |
| HPV16 | L1 | 10 | 225 |
| HPV16 | L1 | 10 | 486 |
| HPV16 | L1 | 11 | 486 |
| HPV16 | L1 | 9 | 154 |
| HPV16 | L1 | 10 | 154 |
| HPV16 | L1 | 10 | 228 |
| HPV16 | L1 | 11 | 228 |
| HPV16 | L1 | 8 | 120 |
| HPV16 | L1 | 10 | 120 |
| HPV16 | L1 | 9 | 113 |
| HPV16 | L1 | 8 | 361 |
| HPV16 | L1 | 10 | 361 |
| HPV16 | L1 | 10 | 442 |
| HPV16 | L1 | 11 | 442 |
| HPV16 | L1 | 9 | 412 |
| HPV16 | L1 | 11 | 17 |
| HPV16 | L1 | 9 | 34 |
| HPV16 | L1 | 11 | 34 |
| HPV16 | L1 | 8 | 279 |
| HPV16 | L1 | 8 | 132 |
| HPV16 | L1 | 10 | 132 |
| HPV16 | L1 | 10 | 474 |
| HPV16 | L1 | 8 | 245 |
| HPV16 | L1 | 10 | 245 |
| HPV16 | L1 | 8 | 400 |
| HPV16 | L1 | 9 | 400 |
| HPV16 | L1 | 10 | 400 |
| HPV16 | L1 | 11 | 400 |
| HPV16 | L1 | 8 | 5 |
| HPV16 | L1 | 9 | 494 |
| HPV16 | L1 | 8 | 402 |
| HPV16 | L1 | 9 | 402 |
| HPV16 | L1 | 10 | 402 |
| HPV16 | L1 | 11 | 25 |
| HPV16 | L1 | 8 | 506 |
| HPV16 | L1 | 9 | 506 |
| HPV16 | L1 | 11 | 506 |
| HPV16 | L1 | 11 | 236 |
| HPV16 | L1 | 9 | 282 |
| HPV16 | L1 | 11 | 282 |
| HPV16 | L1 | 8 | 446 |
| HPV16 | L1 | 8 | 356 |
| HPV16 | L1 | 11 | 356 |
| HPV16 | L1 | 8 | 232 |
| HPV16 | L1 | 10 | 232 |
| HPV16 | L1 | 11 | 291 |

TABLE VIII-continued

HLA-A2 Supermotif-Bearing Peptides

| 1 | 2 | 3 | 4 |
|---|---|---|---|
| HPV16 | L1 | 8 | 348 |
| HPV16 | L1 | 10 | 348 |
| HPV16 | L1 | 11 | 348 |
| HPV16 | L1 | 8 | 142 |
| HPV16 | L1 | 11 | 142 |
| HPV16 | L1 | 9 | 499 |
| HPV16 | L1 | 10 | 499 |
| HPV16 | L1 | 9 | 431 |
| HPV16 | L1 | 10 | 431 |
| HPV16 | L1 | 9 | 93 |
| HPV16 | L1 | 11 | 93 |
| HPV16 | L1 | 8 | 136 |
| HPV16 | L1 | 10 | 438 |
| HPV16 | L1 | 11 | 438 |
| HPV16 | L1 | 8 | 64 |
| HPV16 | L1 | 8 | 166 |
| HPV16 | L1 | 10 | 166 |
| HPV16 | L1 | 10 | 130 |
| HPV16 | L1 | 9 | 140 |
| HPV16 | L1 | 10 | 140 |
| HPV16 | L1 | 8 | 62 |
| HPV16 | L1 | 9 | 62 |
| HPV16 | L1 | 10 | 62 |
| HPV16 | L1 | 8 | 22 |
| HPV16 | L1 | 10 | 22 |
| HPV16 | L1 | 8 | 285 |
| HPV16 | L1 | 9 | 285 |
| HPV16 | L1 | 11 | 457 |
| HPV16 | L1 | 10 | 452 |
| HPV16 | L1 | 9 | 424 |
| HPV16 | L1 | 11 | 8 |
| HPV16 | L1 | 9 | 86 |
| HPV16 | L1 | 9 | 221 |
| HPV16 | L1 | 8 | 11 |
| HPV16 | L1 | 10 | 11 |
| HPV16 | L1 | 8 | 407 |
| HPV16 | L1 | 9 | 407 |
| HPV16 | L1 | 11 | 407 |
| HPV16 | L1 | 8 | 501 |
| HPV16 | L1 | 9 | 512 |
| HPV16 | L1 | 11 | 512 |
| HPV16 | L1 | 10 | 85 |
| HPV16 | L1 | 8 | 406 |
| HPV16 | L1 | 9 | 406 |
| HPV16 | L1 | 10 | 406 |
| HPV16 | L1 | 8 | 151 |
| HPV16 | L1 | 10 | 151 |
| HPV16 | L1 | 11 | 262 |
| HPV16 | L1 | 8 | 178 |
| HPV16 | L1 | 9 | 90 |
| HPV16 | L1 | 9 | 46 |
| HPV16 | L1 | 10 | 46 |
| HPV16 | L1 | 9 | 312 |
| HPV16 | L1 | 10 | 69 |
| HPV16 | L1 | 8 | 184 |
| HPV16 | L1 | 11 | 216 |
| HPV16 | L1 | 11 | 68 |
| HPV16 | L1 | 8 | 148 |
| HPV16 | L1 | 11 | 148 |
| HPV16 | L1 | 8 | 495 |
| HPV16 | L1 | 8 | 239 |
| HPV16 | L1 | 10 | 239 |
| HPV16 | L1 | 10 | 398 |
| HPV16 | L1 | 11 | 398 |
| HPV16 | L1 | 8 | 432 |
| HPV16 | L1 | 9 | 432 |
| HPV16 | L1 | 11 | 339 |
| HPV16 | L1 | 8 | 94 |
| HPV16 | L1 | 10 | 94 |
| HPV16 | L1 | 9 | 409 |
| HPV16 | L1 | 10 | 9 |
| HPV16 | L1 | 8 | 87 |
| HPV16 | L1 | 8 | 124 |
| HPV16 | L1 | 10 | 124 |
| HPV16 | L1 | 8 | 1 |
| HPV16 | L1 | 9 | 1 |
| HPV16 | L1 | 10 | 1 |
| HPV16 | L1 | 11 | 1 |
| HPV16 | L1 | 10 | 414 |
| HPV16 | L1 | 11 | 414 |
| HPV16 | L1 | 8 | 226 |
| HPV16 | L1 | 9 | 226 |
| HPV16 | L1 | 10 | 263 |
| HPV16 | L1 | 8 | 325 |
| HPV16 | L1 | 10 | 164 |
| HPV16 | L1 | 9 | 157 |
| HPV16 | L1 | 11 | 157 |
| HPV16 | L1 | 8 | 58 |
| HPV16 | L1 | 11 | 58 |
| HPV16 | L1 | 10 | 311 |
| HPV16 | L1 | 8 | 476 |
| HPV16 | L1 | 10 | 476 |
| HPV16 | L1 | 8 | 367 |
| HPV16 | L1 | 10 | 367 |
| HPV16 | L1 | 8 | 353 |
| HPV16 | L1 | 10 | 353 |
| HPV16 | L1 | 11 | 353 |
| HPV16 | L1 | 8 | 383 |
| HPV16 | L1 | 9 | 218 |
| HPV16 | L1 | 10 | 218 |
| HPV16 | L1 | 8 | 296 |
| HPV16 | L1 | 9 | 19 |
| HPV16 | L1 | 11 | 19 |
| HPV16 | L1 | 8 | 460 |
| HPV16 | L1 | 10 | 77 |
| HPV16 | L1 | 11 | 77 |
| HPV16 | L1 | 8 | 247 |
| HPV16 | L1 | 8 | 213 |
| HPV16 | L1 | 9 | 213 |
| HPV16 | L1 | 8 | 489 |
| HPV16 | L1 | 10 | 489 |
| HPV16 | L1 | 11 | 138 |
| HPV16 | L1 | 10 | 466 |
| HPV16 | L1 | 9 | 147 |
| HPV16 | L1 | 8 | 319 |
| HPV16 | L1 | 9 | 319 |
| HPV16 | L1 | 8 | 515 |
| HPV16 | L1 | 9 | 515 |
| HPV16 | L1 | 10 | 515 |
| HPV16 | L1 | 8 | 41 |
| HPV16 | L1 | 10 | 41 |
| HPV16 | L1 | 8 | 43 |
| HPV16 | L1 | 11 | 497 |
| HPV16 | L1 | 9 | 450 |
| HPV16 | L1 | 9 | 240 |
| HPV16 | L1 | 11 | 240 |
| HPV16 | L1 | 9 | 331 |
| HPV16 | L1 | 8 | 403 |
| HPV16 | L1 | 9 | 403 |
| HPV16 | L1 | 11 | 403 |
| HPV16 | L1 | 11 | 181 |
| HPV16 | L1 | 9 | 354 |
| HPV16 | L1 | 10 | 354 |
| HPV16 | L1 | 11 | 280 |
| HPV16 | L1 | 10 | 26 |
| HPV16 | L1 | 11 | 26 |
| HPV16 | L1 | 8 | 2 |
| HPV16 | L1 | 9 | 2 |
| HPV16 | L1 | 10 | 2 |
| HPV16 | L1 | 11 | 2 |
| HPV16 | L1 | 9 | 289 |
| HPV16 | L1 | 9 | 341 |
| HPV16 | L1 | 9 | 123 |
| HPV16 | L1 | 11 | 123 |
| HPV16 | L1 | 8 | 56 |
| HPV16 | L1 | 10 | 56 |
| HPV16 | L1 | 9 | 482 |
| HPV16 | L1 | 9 | 159 |
| HPV16 | L1 | 9 | 253 |
| HPV16 | L1 | 11 | 253 |

TABLE VIII-continued

HLA-A2 Supermotif-Bearing Peptides

| 1 | 2 | 3 | 4 |
|---|---|---|---|
| HPV16 | L1 | 8 | 369 |
| HPV16 | L1 | 11 | 369 |
| HPV16 | L1 | 11 | 271 |
| HPV16 | L1 | 8 | 28 |
| HPV16 | L1 | 9 | 28 |
| HPV16 | L1 | 10 | 28 |
| HPV16 | L1 | 9 | 174 |
| HPV16 | L1 | 11 | 174 |
| HPV16 | L1 | 9 | 324 |
| HPV16 | L1 | 10 | 449 |
| HPV16 | L1 | 9 | 49 |
| HPV16 | L1 | 11 | 49 |
| HPV16 | L1 | 11 | 422 |
| HPV16 | L1 | 8 | 365 |
| HPV16 | L1 | 9 | 365 |
| HPV16 | L1 | 10 | 365 |
| HPV16 | L1 | 10 | 375 |
| HPV16 | L1 | 11 | 521 |
| HPV16 | L1 | 8 | 410 |
| HPV16 | L1 | 11 | 410 |
| HPV16 | L1 | 9 | 523 |
| HPV16 | L1 | 10 | 423 |
| HPV16 | L1 | 9 | 439 |
| HPV16 | L1 | 10 | 439 |
| HPV16 | L1 | 8 | 507 |
| HPV16 | L1 | 10 | 507 |
| HPV16 | L1 | 11 | 507 |
| HPV16 | L1 | 9 | 238 |
| HPV16 | L1 | 11 | 238 |
| HPV16 | L1 | 8 | 408 |
| HPV16 | L1 | 10 | 408 |
| HPV16 | L1 | 9 | 121 |
| HPV16 | L1 | 11 | 121 |
| HPV16 | L1 | 10 | 522 |
| HPV16 | L1 | 10 | 237 |
| HPV16 | L1 | 9 | 362 |
| HPV16 | L1 | 11 | 362 |
| HPV16 | L1 | 8 | 516 |
| HPV16 | L1 | 9 | 516 |
| HPV16 | L1 | 8 | 219 |
| HPV16 | L1 | 9 | 219 |
| HPV16 | L1 | 11 | 219 |
| HPV16 | L1 | 9 | 358 |
| HPV16 | L1 | 11 | 358 |
| HPV16 | L1 | 9 | 36 |
| HPV16 | L1 | 10 | 54 |
| HPV16 | L1 | 11 | 204 |
| HPV16 | L1 | 8 | 220 |
| HPV16 | L1 | 10 | 220 |
| HPV16 | L1 | 10 | 220 |
| HPV16 | L1 | 9 | 10 |
| HPV16 | L1 | 11 | 10 |
| HPV16 | L1 | 8 | 413 |
| HPV16 | L1 | 11 | 413 |
| HPV16 | L1 | 8 | 3 |
| HPV16 | L1 | 9 | 3 |
| HPV16 | L1 | 10 | 3 |
| HPV16 | L1 | 10 | 357 |
| HPV16 | L1 | 8 | 359 |
| HPV16 | L1 | 10 | 359 |
| HPV16 | L1 | 8 | 47 |
| HPV16 | L1 | 9 | 47 |
| HPV16 | L1 | 11 | 47 |
| HPV16 | L1 | 8 | 126 |
| HPV16 | L1 | 8 | 30 |
| HPV16 | L1 | 10 | 30 |
| HPV16 | L1 | 8 | 416 |
| HPV16 | L1 | 9 | 416 |
| HPV16 | L1 | 10 | 416 |
| HPV16 | L1 | 8 | 302 |
| HPV16 | L1 | 9 | 302 |
| HPV16 | L1 | 11 | 302 |
| HPV16 | L1 | 10 | 38 |
| HPV16 | L1 | 11 | 38 |
| HPV16 | L1 | 10 | 389 |
| HPV16 | L1 | 9 | 275 |
| HPV16 | L1 | 8 | 470 |
| HPV16 | L1 | 11 | 53 |
| HPV16 | L2 | 11 | 355 |
| HPV16 | L2 | 8 | 144 |
| HPV16 | L2 | 9 | 144 |
| HPV16 | L2 | 10 | 144 |
| HPV16 | L2 | 11 | 144 |
| HPV16 | L2 | 8 | 288 |
| HPV16 | L2 | 10 | 356 |
| HPV16 | L2 | 9 | 293 |
| HPV16 | L2 | 8 | 82 |
| HPV16 | L2 | 11 | 15 |
| HPV16 | L2 | 8 | 116 |
| HPV16 | L2 | 11 | 116 |
| HPV16 | L2 | 10 | 31 |
| HPV16 | L2 | 11 | 31 |
| HPV16 | L2 | 8 | 147 |
| HPV16 | L2 | 9 | 147 |
| HPV16 | L2 | 10 | 147 |
| HPV16 | L2 | 11 | 147 |
| HPV16 | L2 | 10 | 415 |
| HPV16 | L2 | 9 | 285 |
| HPV16 | L2 | 10 | 285 |
| HPV16 | L2 | 11 | 285 |
| HPV16 | L2 | 8 | 367 |
| HPV16 | L2 | 9 | 367 |
| HPV16 | L2 | 11 | 367 |
| HPV16 | L2 | 9 | 422 |
| HPV16 | L2 | 10 | 422 |
| HPV16 | L2 | 9 | 43 |
| HPV16 | L2 | 11 | 43 |
| HPV16 | L2 | 11 | 199 |
| HPV16 | L2 | 10 | 84 |
| HPV16 | L2 | 11 | 84 |
| HPV16 | L2 | 10 | 376 |
| HPV16 | L2 | 9 | 140 |
| HPV16 | L2 | 8 | 129 |
| HPV16 | L2 | 9 | 129 |
| HPV16 | L2 | 11 | 129 |
| HPV16 | L2 | 8 | 338 |
| HPV16 | L2 | 11 | 338 |
| HPV16 | L2 | 8 | 195 |
| HPV16 | L2 | 9 | 195 |
| HPV16 | L2 | 11 | 195 |
| HPV16 | L2 | 9 | 340 |
| HPV16 | L2 | 11 | 340 |
| HPV16 | L2 | 8 | 176 |
| HPV16 | L2 | 9 | 111 |
| HPV16 | L2 | 11 | 111 |
| HPV16 | L2 | 8 | 114 |
| HPV16 | L2 | 10 | 114 |
| HPV16 | L2 | 8 | 373 |
| HPV16 | L2 | 10 | 373 |
| HPV16 | L2 | 8 | 242 |
| HPV16 | L2 | 9 | 242 |
| HPV16 | L2 | 10 | 242 |
| HPV16 | L2 | 9 | 201 |
| HPV16 | L2 | 10 | 201 |
| HPV16 | L2 | 11 | 201 |
| HPV16 | L2 | 11 | 283 |
| HPV16 | L2 | 11 | 163 |
| HPV16 | L2 | 8 | 181 |
| HPV16 | L2 | 10 | 181 |
| HPV16 | L2 | 9 | 118 |
| HPV16 | L2 | 8 | 404 |
| HPV16 | L2 | 8 | 259 |
| HPV16 | L2 | 8 | 59 |
| HPV16 | L2 | 10 | 57 |
| HPV16 | L2 | 11 | 364 |
| HPV16 | L2 | 10 | 226 |
| HPV16 | L2 | 8 | 26 |
| HPV16 | L2 | 11 | 26 |
| HPV16 | L2 | 9 | 65 |
| HPV16 | L2 | 11 | 65 |

TABLE VIII-continued

HLA-A2 Supermotif-Bearing Peptides

| 1 | 2 | 3 | 4 |
|---|---|---|---|
| HPV16 | L2 | 10 | 61 |
| HPV16 | L2 | 8 | 76 |
| HPV16 | L2 | 10 | 76 |
| HPV16 | L2 | 11 | 76 |
| HPV16 | L2 | 9 | 52 |
| HPV16 | L2 | 11 | 52 |
| HPV16 | L2 | 8 | 354 |
| HPV16 | L2 | 9 | 440 |
| HPV16 | L2 | 11 | 41 |
| HPV16 | L2 | 8 | 277 |
| HPV16 | L2 | 10 | 277 |
| HPV16 | L2 | 11 | 277 |
| HPV16 | L2 | 10 | 439 |
| HPV16 | L2 | 9 | 32 |
| HPV16 | L2 | 10 | 32 |
| HPV16 | L2 | 11 | 32 |
| HPV16 | L2 | 8 | 145 |
| HPV16 | L2 | 9 | 145 |
| HPV16 | L2 | 10 | 145 |
| HPV16 | L2 | 11 | 145 |
| HPV16 | L2 | 9 | 45 |
| HPV16 | L2 | 8 | 420 |
| HPV16 | L2 | 9 | 420 |
| HPV16 | L2 | 11 | 420 |
| HPV16 | L2 | 9 | 374 |
| HPV16 | L2 | 8 | 344 |
| HPV16 | L2 | 9 | 344 |
| HPV16 | L2 | 8 | 243 |
| HPV16 | L2 | 9 | 243 |
| HPV16 | L2 | 8 | 135 |
| HPV16 | L2 | 10 | 135 |
| HPV16 | L2 | 11 | 135 |
| HPV16 | L2 | 11 | 250 |
| HPV16 | L2 | 8 | 286 |
| HPV16 | L2 | 9 | 286 |
| HPV16 | L2 | 10 | 286 |
| HPV16 | L2 | 9 | 430 |
| HPV16 | L2 | 10 | 430 |
| HPV16 | L2 | 11 | 430 |
| HPV16 | L2 | 8 | 105 |
| HPV16 | L2 | 11 | 105 |
| HPV16 | L2 | 8 | 202 |
| HPV16 | L2 | 9 | 202 |
| HPV16 | L2 | 10 | 202 |
| HPV16 | L2 | 9 | 248 |
| HPV16 | L2 | 10 | 23 |
| HPV16 | L2 | 11 | 23 |
| HPV16 | L2 | 8 | 20 |
| HPV16 | L2 | 8 | 39 |
| HPV16 | L2 | 8 | 35 |
| HPV16 | L2 | 11 | 35 |
| HPV16 | L2 | 10 | 323 |
| HPV16 | L2 | 11 | 323 |
| HPV16 | L2 | 8 | 236 |
| HPV16 | L2 | 9 | 236 |
| HPV16 | L2 | 10 | 236 |
| HPV16 | L2 | 8 | 86 |
| HPV16 | L2 | 9 | 86 |
| HPV16 | L2 | 10 | 86 |
| HPV16 | L2 | 8 | 249 |
| HPV16 | L2 | 9 | 169 |
| HPV16 | L2 | 8 | 341 |
| HPV16 | L2 | 10 | 341 |
| HPV16 | L2 | 11 | 341 |
| HPV16 | L2 | 8 | 46 |
| HPV16 | L2 | 8 | 294 |
| HPV16 | L2 | 8 | 108 |
| HPV16 | L2 | 10 | 108 |
| HPV16 | L2 | 9 | 410 |
| HPV16 | L2 | 11 | 410 |
| HPV16 | L2 | 9 | 454 |
| HPV16 | L2 | 9 | 276 |
| HPV16 | L2 | 11 | 276 |
| HPV16 | L2 | 10 | 407 |
| HPV16 | L2 | 9 | 419 |
| HPV16 | L2 | 10 | 419 |
| HPV16 | L2 | 9 | 397 |
| HPV16 | L2 | 9 | 208 |
| HPV16 | L2 | 8 | 150 |
| HPV16 | L2 | 9 | 174 |
| HPV16 | L2 | 10 | 174 |
| HPV16 | L2 | 8 | 240 |
| HPV16 | L2 | 10 | 240 |
| HPV16 | L2 | 11 | 240 |
| HPV16 | L2 | 9 | 143 |
| HPV16 | L2 | 10 | 143 |
| HPV16 | L2 | 11 | 143 |
| HPV16 | L2 | 8 | 292 |
| HPV16 | L2 | 10 | 292 |
| HPV16 | L2 | 11 | 395 |
| HPV16 | L2 | 8 | 255 |
| HPV16 | L2 | 11 | 255 |
| HPV16 | L2 | 8 | 417 |
| HPV16 | L2 | 11 | 417 |
| HPV16 | L2 | 8 | 215 |
| HPV16 | L2 | 9 | 215 |
| HPV16 | L2 | 11 | 215 |
| HPV16 | L2 | 10 | 429 |
| HPV16 | L2 | 11 | 429 |
| HPV16 | L2 | 8 | 74 |
| HPV16 | L2 | 9 | 74 |
| HPV16 | L2 | 10 | 74 |
| HPV16 | L2 | 8 | 409 |
| HPV16 | L2 | 10 | 409 |
| HPV16 | L2 | 9 | 197 |
| HPV16 | L2 | 9 | 435 |
| HPV16 | L2 | 8 | 80 |
| HPV16 | L2 | 10 | 80 |
| HPV16 | L2 | 8 | 161 |
| HPV16 | L2 | 9 | 161 |
| HPV16 | L2 | 11 | 246 |
| HPV16 | L2 | 11 | 172 |
| HPV16 | L2 | 8 | 358 |
| HPV16 | L2 | 11 | 358 |
| HPV16 | L2 | 11 | 120 |
| HPV16 | L2 | 11 | 221 |
| HPV16 | L2 | 9 | 97 |
| HPV16 | L2 | 10 | 97 |
| HPV16 | L2 | 8 | 381 |
| HPV16 | L2 | 10 | 381 |
| HPV16 | L2 | 8 | 88 |
| HPV16 | L2 | 11 | 88 |
| HPV16 | L2 | 9 | 24 |
| HPV16 | L2 | 10 | 24 |
| HPV16 | L2 | 8 | 423 |
| HPV16 | L2 | 9 | 423 |
| HPV16 | L2 | 8 | 44 |
| HPV16 | L2 | 10 | 44 |
| HPV16 | L2 | 9 | 17 |
| HPV16 | L2 | 11 | 17 |
| HPV16 | L2 | 9 | 233 |
| HPV16 | L2 | 11 | 233 |
| HPV16 | L2 | 9 | 342 |
| HPV16 | L2 | 10 | 342 |
| HPV16 | L2 | 11 | 342 |
| HPV16 | L2 | 11 | 310 |
| HPV16 | L2 | 8 | 234 |
| HPV16 | L2 | 10 | 234 |
| HPV16 | L2 | 11 | 234 |
| HPV16 | L2 | 10 | 12 |
| HPV16 | L2 | 8 | 305 |
| HPV16 | L2 | 10 | 305 |
| HPV16 | L2 | 8 | 224 |
| HPV16 | L2 | 9 | 224 |
| HPV16 | L2 | 9 | 461 |
| HPV16 | L2 | 11 | 461 |
| HPV16 | L2 | 9 | 298 |
| HPV16 | L2 | 9 | 69 |
| HPV16 | L2 | 8 | 9 |
| HPV16 | L2 | 10 | 9 |

TABLE VIII-continued

HLA-A2 Supermotif-Bearing Peptides

| 1 | 2 | 3 | 4 |
|---|---|---|---|
| HPV16 | L2 | 8 | 313 |
| HPV16 | L2 | 10 | 313 |
| HPV16 | L2 | 8 | 230 |
| HPV16 | L2 | 9 | 230 |
| HPV16 | L2 | 9 | 335 |
| HPV16 | L2 | 10 | 335 |
| HPV16 | L2 | 11 | 335 |
| HPV16 | L2 | 8 | 6 |
| HPV16 | L2 | 10 | 6 |
| HPV16 | L2 | 11 | 6 |
| HPV16 | L2 | 8 | 14 |
| HPV16 | L2 | 11 | 274 |
| HPV16 | L2 | 9 | 360 |
| HPV16 | L2 | 11 | 360 |
| HPV16 | L2 | 11 | 125 |
| HPV16 | L2 | 8 | 134 |
| HPV16 | L2 | 9 | 134 |
| HPV16 | L2 | 11 | 134 |
| HPV16 | L2 | 9 | 104 |
| HPV16 | L2 | 8 | 389 |
| HPV16 | L2 | 10 | 389 |
| HPV16 | L2 | 11 | 389 |
| HPV16 | L2 | 9 | 107 |
| HPV16 | L2 | 11 | 107 |
| HPV16 | L2 | 9 | 50 |
| HPV16 | L2 | 11 | 50 |
| HPV16 | L2 | 8 | 138 |
| HPV16 | L2 | 9 | 138 |
| HPV16 | L2 | 11 | 138 |
| HPV16 | L2 | 8 | 189 |
| HPV16 | L2 | 10 | 189 |
| HPV16 | L2 | 9 | 331 |
| HPV16 | L2 | 11 | 331 |
| HPV16 | L2 | 11 | 186 |
| HPV16 | L2 | 8 | 204 |
| HPV16 | L2 | 11 | 204 |
| HPV16 | L2 | 10 | 213 |
| HPV16 | L2 | 11 | 213 |
| HPV16 | L2 | 8 | 387 |
| HPV16 | L2 | 10 | 387 |
| HPV16 | L2 | 8 | 378 |
| HPV16 | L2 | 11 | 378 |
| HPV16 | L2 | 9 | 347 |
| HPV16 | L2 | 10 | 347 |
| HPV16 | L2 | 11 | 347 |
| HPV16 | L2 | 9 | 167 |
| HPV16 | L2 | 11 | 167 |
| HPV16 | L2 | 9 | 122 |
| HPV16 | L2 | 11 | 384 |
| HPV16 | L2 | 9 | 81 |
| HPV16 | L2 | 8 | 332 |
| HPV16 | L2 | 10 | 332 |
| HPV16 | L2 | 11 | 438 |
| HPV16 | L2 | 10 | 399 |
| HPV16 | L2 | 10 | 187 |
| HPV16 | L2 | 8 | 343 |
| HPV16 | L2 | 9 | 343 |
| HPV16 | L2 | 10 | 343 |
| HPV16 | L2 | 9 | 85 |
| HPV16 | L2 | 10 | 85 |
| HPV16 | L2 | 11 | 85 |
| HPV16 | L2 | 10 | 311 |
| HPV16 | L2 | 9 | 182 |
| HPV16 | L2 | 11 | 265 |
| HPV16 | L2 | 10 | 16 |
| HPV16 | L2 | 10 | 232 |
| HPV16 | L2 | 9 | 156 |
| HPV16 | L2 | 8 | 398 |
| HPV16 | L2 | 11 | 398 |
| HPV16 | L2 | 8 | 141 |
| HPV16 | L2 | 11 | 141 |
| HPV16 | L2 | 8 | 244 |
| HPV16 | L2 | 10 | 379 |
| HPV16 | L2 | 8 | 231 |
| HPV16 | L2 | 11 | 231 |
| HPV16 | L2 | 9 | 351 |
| HPV16 | L2 | 11 | 351 |
| HPV16 | L2 | 9 | 136 |
| HPV16 | L2 | 10 | 136 |
| HPV16 | L2 | 11 | 136 |
| HPV16 | L2 | 8 | 350 |
| HPV16 | L2 | 10 | 350 |
| HPV16 | L2 | 10 | 153 |
| HPV16 | L2 | 8 | 209 |
| HPV16 | L2 | 9 | 154 |
| HPV16 | L2 | 11 | 154 |
| HPV16 | L2 | 8 | 287 |
| HPV16 | L2 | 9 | 287 |
| HPV16 | L2 | 10 | 222 |
| HPV16 | L2 | 11 | 222 |
| HPV16 | L2 | 8 | 168 |
| HPV16 | L2 | 10 | 168 |
| HPV16 | L2 | 8 | 155 |
| HPV16 | L2 | 10 | 155 |
| HPV16 | L2 | 11 | 152 |
| HPV16 | L2 | 8 | 237 |
| HPV16 | L2 | 9 | 237 |
| HPV16 | L2 | 11 | 237 |
| HPV16 | L2 | 9 | 369 |
| HPV16 | L2 | 11 | 369 |
| HPV16 | L2 | 8 | 393 |
| HPV16 | L2 | 10 | 72 |
| HPV16 | L2 | 11 | 72 |
| HPV16 | L2 | 8 | 447 |
| HPV16 | L2 | 9 | 447 |
| HPV16 | L2 | 10 | 453 |
| HPV16 | L2 | 8 | 349 |
| HPV16 | L2 | 9 | 349 |
| HPV18 | L2 | 11 | 349 |
| HPV18 | E1 | 11 | 396 |
| HPV18 | E1 | 10 | 397 |
| HPV18 | E1 | 8 | 324 |
| HPV18 | E1 | 10 | 324 |
| HPV18 | E1 | 8 | 246 |
| HPV18 | E1 | 9 | 246 |
| HPV18 | E1 | 10 | 246 |
| HPV18 | E1 | 10 | 22 |
| HPV18 | E1 | 11 | 22 |
| HPV18 | E1 | 9 | 546 |
| HPV18 | E1 | 8 | 68 |
| HPV18 | E1 | 9 | 466 |
| HPV18 | E1 | 10 | 387 |
| HPV18 | E1 | 11 | 387 |
| HPV18 | E1 | 9 | 325 |
| HPV18 | E1 | 9 | 213 |
| HPV18 | E1 | 8 | 526 |
| HPV18 | E1 | 9 | 526 |
| HPV18 | E1 | 10 | 66 |
| HPV18 | E1 | 8 | 72 |
| HPV18 | E1 | 10 | 72 |
| HPV18 | E1 | 11 | 72 |
| HPV18 | E1 | 8 | 422 |
| HPV18 | E1 | 9 | 199 |
| HPV18 | E1 | 8 | 40 |
| HPV18 | E1 | 9 | 40 |
| HPV18 | E1 | 10 | 413 |
| HPV18 | E1 | 8 | 144 |
| HPV18 | E1 | 11 | 531 |
| HPV18 | E1 | 9 | 216 |
| HPV18 | E1 | 9 | 504 |
| HPV18 | E1 | 11 | 412 |
| HPV18 | E1 | 8 | 273 |
| HPV18 | E1 | 9 | 273 |
| HPV18 | E1 | 10 | 273 |
| HPV18 | E1 | 11 | 273 |
| HPV18 | E1 | 8 | 479 |
| HPV18 | E1 | 10 | 479 |
| HPV18 | E1 | 9 | 311 |
| HPV18 | E1 | 10 | 404 |
| HPV18 | E1 | 11 | 404 |

TABLE VIII-continued

HLA-A2 Supermotif-Bearing Peptides

| 1 | 2 | 3 | 4 |
|---|---|---|---|
| HPV18 | E1 | 8 | 240 |
| HPV18 | E1 | 11 | 240 |
| HPV18 | E1 | 9 | 196 |
| HPV18 | E1 | 10 | 196 |
| HPV18 | E1 | 11 | 635 |
| HPV18 | E1 | 8 | 78 |
| HPV18 | E1 | 8 | 530 |
| HPV18 | E1 | 9 | 628 |
| HPV18 | E1 | 11 | 628 |
| HPV18 | E1 | 11 | 203 |
| HPV18 | E1 | 9 | 363 |
| HPV18 | E1 | 11 | 228 |
| HPV18 | E1 | 8 | 381 |
| HPV18 | E1 | 9 | 381 |
| HPV18 | E1 | 10 | 381 |
| HPV18 | E1 | 8 | 46 |
| HPV18 | E1 | 11 | 46 |
| HPV18 | E1 | 9 | 637 |
| HPV18 | E1 | 8 | 106 |
| HPV18 | E1 | 11 | 106 |
| HPV18 | E1 | 10 | 42 |
| HPV18 | E1 | 10 | 522 |
| HPV18 | E1 | 11 | 522 |
| HPV18 | E1 | 9 | 342 |
| HPV18 | E1 | 10 | 342 |
| HPV18 | E1 | 11 | 342 |
| HPV18 | E1 | 10 | 52 |
| HPV18 | E1 | 8 | 220 |
| HPV18 | E1 | 10 | 220 |
| HPV18 | E1 | 11 | 220 |
| HPV18 | E1 | 8 | 540 |
| HPV18 | E1 | 11 | 30 |
| HPV18 | E1 | 8 | 166 |
| HPV18 | E1 | 8 | 143 |
| HPV18 | E1 | 9 | 143 |
| HPV18 | E1 | 11 | 115 |
| HPV18 | E1 | 8 | 62 |
| HPV18 | E1 | 11 | 62 |
| HPV18 | E1 | 9 | 108 |
| HPV18 | E1 | 11 | 108 |
| HPV18 | E1 | 8 | 375 |
| HPV18 | E1 | 9 | 375 |
| HPV18 | E1 | 11 | 366 |
| HPV18 | E1 | 8 | 59 |
| HPV18 | E1 | 10 | 59 |
| HPV18 | E1 | 11 | 59 |
| HPV18 | E1 | 9 | 64 |
| HPV18 | E1 | 11 | 309 |
| HPV18 | E1 | 10 | 104 |
| HPV18 | E1 | 9 | 141 |
| HPV18 | E1 | 10 | 141 |
| HPV18 | E1 | 11 | 141 |
| HPV18 | E1 | 8 | 74 |
| HPV18 | E1 | 9 | 74 |
| HPV18 | E1 | 11 | 74 |
| HPV18 | E1 | 10 | 338 |
| HPV18 | E1 | 11 | 89 |
| HPV18 | E1 | 8 | 497 |
| HPV18 | E1 | 9 | 497 |
| HPV18 | E1 | 10 | 497 |
| HPV18 | E1 | 10 | 265 |
| HPV18 | E1 | 10 | 500 |
| HPV18 | E1 | 8 | 460 |
| HPV18 | E1 | 9 | 463 |
| HPV18 | E1 | 11 | 470 |
| HPV18 | E1 | 8 | 399 |
| HPV18 | E1 | 11 | 399 |
| HPV18 | E1 | 10 | 452 |
| HPV18 | E1 | 11 | 452 |
| HPV18 | E1 | 10 | 508 |
| HPV18 | E1 | 10 | 465 |
| HPV18 | E1 | 10 | 212 |
| HPV18 | E1 | 10 | 503 |
| HPV18 | E1 | 9 | 356 |
| HPV18 | E1 | 8 | 332 |
| HPV18 | E1 | 9 | 332 |
| HPV18 | E1 | 8 | 223 |
| HPV18 | E1 | 8 | 300 |
| HPV18 | E1 | 11 | 300 |
| HPV18 | E1 | 8 | 494 |
| HPV18 | E1 | 11 | 494 |
| HPV18 | E1 | 9 | 121 |
| HPV18 | E1 | 11 | 121 |
| HPV18 | E1 | 9 | 172 |
| HPV18 | E1 | 9 | 55 |
| HPV18 | E1 | 11 | 55 |
| HPV18 | E1 | 10 | 11 |
| HPV18 | E1 | 8 | 473 |
| HPV18 | E1 | 9 | 473 |
| HPV18 | E1 | 8 | 182 |
| HPV18 | E1 | 11 | 182 |
| HPV18 | E1 | 8 | 279 |
| HPV18 | E1 | 9 | 71 |
| HPV18 | E1 | 11 | 71 |
| HPV18 | E1 | 11 | 270 |
| HPV18 | E1 | 8 | 83 |
| HPV18 | E1 | 8 | 306 |
| HPV18 | E1 | 9 | 306 |
| HPV18 | E1 | 8 | 254 |
| HPV18 | E1 | 9 | 254 |
| HPV18 | E1 | 8 | 198 |
| HPV18 | E1 | 10 | 198 |
| HPV18 | E1 | 10 | 569 |
| HPV18 | E1 | 9 | 266 |
| HPV18 | E1 | 10 | 271 |
| HPV18 | E1 | 11 | 271 |
| HPV18 | E1 | 9 | 501 |
| HPV18 | E1 | 8 | 562 |
| HPV18 | E1 | 9 | 562 |
| HPV18 | E1 | 10 | 562 |
| HPV18 | E1 | 11 | 562 |
| HPV18 | E1 | 8 | 262 |
| HPV18 | E1 | 10 | 262 |
| HPV18 | E1 | 10 | 314 |
| HPV18 | E1 | 11 | 314 |
| HPV18 | E1 | 11 | 347 |
| HPV18 | E1 | 11 | 461 |
| HPV18 | E1 | 9 | 590 |
| HPV18 | E1 | 9 | 23 |
| HPV18 | E1 | 10 | 23 |
| HPV18 | E1 | 10 | 449 |
| HPV18 | E1 | 8 | 124 |
| HPV18 | E1 | 9 | 124 |
| HPV18 | E1 | 11 | 439 |
| HPV18 | E1 | 11 | 647 |
| HPV18 | E1 | 8 | 318 |
| HPV18 | E1 | 9 | 318 |
| HPV18 | E1 | 8 | 210 |
| HPV18 | E1 | 8 | 259 |
| HPV18 | E1 | 9 | 259 |
| HPV18 | E1 | 11 | 259 |
| HPV18 | E1 | 8 | 237 |
| HPV18 | E1 | 9 | 237 |
| HPV18 | E1 | 10 | 237 |
| HPV18 | E1 | 11 | 237 |
| HPV18 | E1 | 8 | 524 |
| HPV18 | E1 | 9 | 524 |
| HPV18 | E1 | 10 | 524 |
| HPV18 | E1 | 11 | 524 |
| HPV18 | E1 | 8 | 206 |
| HPV18 | E1 | 9 | 206 |
| HPV18 | E1 | 10 | 206 |
| HPV18 | E1 | 11 | 206 |
| HPV18 | E1 | 8 | 389 |
| HPV18 | E1 | 9 | 389 |
| HPV18 | E1 | 10 | 389 |
| HPV18 | E1 | 10 | 215 |
| HPV18 | E1 | 9 | 561 |
| HPV18 | E1 | 10 | 561 |
| HPV18 | E1 | 11 | 561 |

TABLE VIII-continued

HLA-A2 Supermotif-Bearing Peptides

| 1 | 2 | 3 | 4 |
|---|---|---|---|
| HPV18 | E1 | 9 | 261 |
| HPV18 | E1 | 11 | 261 |
| HPV18 | E1 | 11 | 313 |
| HPV18 | E1 | 9 | 388 |
| HPV18 | E1 | 10 | 388 |
| HPV18 | E1 | 11 | 388 |
| HPV18 | E1 | 9 | 304 |
| HPV18 | E1 | 10 | 304 |
| HPV18 | E1 | 11 | 304 |
| HPV18 | E1 | 10 | 204 |
| HPV18 | E1 | 11 | 204 |
| HPV18 | E1 | 11 | 285 |
| HPV18 | E1 | 9 | 570 |
| HPV18 | E1 | 8 | 376 |
| HPV18 | E1 | 8 | 520 |
| HPV18 | E1 | 9 | 520 |
| HPV18 | E1 | 8 | 350 |
| HPV18 | E1 | 8 | 571 |
| HPV18 | E1 | 9 | 295 |
| HPV18 | E1 | 10 | 295 |
| HPV18 | E1 | 11 | 295 |
| HPV18 | E1 | 9 | 480 |
| HPV18 | E1 | 10 | 229 |
| HPV18 | E1 | 11 | 229 |
| HPV18 | E1 | 8 | 382 |
| HPV18 | E1 | 9 | 382 |
| HPV18 | E1 | 8 | 214 |
| HPV18 | E1 | 11 | 214 |
| HPV18 | E1 | 8 | 527 |
| HPV18 | E1 | 11 | 527 |
| HPV18 | E1 | 8 | 312 |
| HPV18 | E1 | 10 | 47 |
| HPV18 | E1 | 10 | 367 |
| HPV18 | E1 | 11 | 367 |
| HPV18 | E1 | 8 | 545 |
| HPV18 | E1 | 10 | 545 |
| HPV18 | E1 | 9 | 39 |
| HPV18 | E1 | 10 | 39 |
| HPV18 | E1 | 10 | 188 |
| HPV18 | E1 | 11 | 188 |
| HPV18 | E1 | 0 | 335 |
| HPV18 | E1 | 9 | 487 |
| HPV18 | E1 | 8 | 158 |
| HPV18 | E1 | 10 | 158 |
| HPV18 | E1 | 11 | 158 |
| HPV18 | E1 | 8 | 191 |
| HPV18 | E1 | 9 | 191 |
| HPV18 | E1 | 11 | 191 |
| HPV18 | E1 | 10 | 577 |
| HPV18 | E1 | 11 | 485 |
| HPV18 | E1 | 8 | 568 |
| HPV18 | E1 | 11 | 568 |
| HPV18 | E1 | 11 | 551 |
| HPV18 | E1 | 11 | 448 |
| HPV18 | E1 | 8 | 98 |
| HPV18 | E1 | 10 | 98 |
| HPV18 | E1 | 10 | 560 |
| HPV18 | E1 | 11 | 560 |
| HPV18 | E1 | 8 | 519 |
| HPV18 | E1 | 9 | 519 |
| HPV18 | E1 | 10 | 519 |
| HPV18 | E1 | 8 | 194 |
| HPV18 | E1 | 11 | 194 |
| HPV18 | E1 | 9 | 252 |
| HPV18 | E1 | 10 | 252 |
| HPV18 | E1 | 11 | 252 |
| HPV18 | E1 | 9 | 60 |
| HPV18 | E1 | 10 | 60 |
| HPV18 | E1 | 8 | 21 |
| HPV18 | E1 | 11 | 21 |
| HPV18 | E1 | 9 | 405 |
| HPV18 | E1 | 10 | 405 |
| HPV18 | E1 | 11 | 405 |
| HPV18 | E1 | 9 | 67 |
| HPV18 | E1 | 8 | 457 |
| HPV18 | E1 | 10 | 457 |
| HPV18 | E1 | 11 | 457 |
| HPV18 | E1 | 8 | 563 |
| HPV18 | E1 | 9 | 563 |
| HPV18 | E1 | 10 | 563 |
| HPV18 | E1 | 11 | 563 |
| HPV18 | E1 | 8 | 200 |
| HPV18 | E1 | 8 | 426 |
| HPV18 | E1 | 9 | 456 |
| HPV18 | E1 | 11 | 456 |
| HPV18 | E1 | 11 | 80 |
| HPV18 | E1 | 9 | 649 |
| HPV18 | E1 | 9 | 421 |
| HPV18 | E1 | 10 | 589 |
| HPV18 | E1 | 11 | 626 |
| HPV18 | E1 | 8 | 102 |
| HPV18 | E1 | 9 | 349 |
| HPV18 | E1 | 8 | 294 |
| HPV18 | E1 | 10 | 294 |
| HPV18 | E1 | 11 | 294 |
| HPV18 | E1 | 9 | 425 |
| HPV18 | E1 | 10 | 330 |
| HPV18 | E1 | 11 | 330 |
| HPV18 | E1 | 8 | 622 |
| HPV18 | E1 | 9 | 553 |
| HPV18 | E1 | 10 | 553 |
| HPV18 | E1 | 9 | 117 |
| HPV18 | E1 | 11 | 430 |
| HPV18 | E1 | 10 | 164 |
| HPV18 | E1 | 11 | 93 |
| HPV18 | E1 | 9 | 302 |
| HPV18 | E1 | 11 | 302 |
| HPV18 | E1 | 10 | 511 |
| HPV18 | E1 | 11 | 511 |
| HPV18 | E1 | 10 | 322 |
| HPV18 | E1 | 11 | 179 |
| HPV18 | E1 | 9 | 245 |
| HPV18 | E1 | 10 | 245 |
| HPV18 | E1 | 11 | 245 |
| HPV18 | E1 | 8 | 65 |
| HPV18 | E1 | 11 | 65 |
| HPV18 | E1 | 8 | 253 |
| HPV18 | E1 | 9 | 253 |
| HPV18 | E1 | 10 | 253 |
| HPV18 | E1 | 8 | 197 |
| HPV18 | E1 | 9 | 197 |
| HPV18 | E1 | 11 | 197 |
| HPV18 | E1 | 8 | 260 |
| HPV18 | E1 | 10 | 260 |
| HPV18 | E1 | 8 | 303 |
| HPV18 | E1 | 10 | 303 |
| HPV18 | E1 | 11 | 303 |
| HPV18 | E1 | 9 | 414 |
| HPV18 | E1 | 9 | 53 |
| HPV18 | E1 | 11 | 53 |
| HPV18 | E1 | 8 | 238 |
| HPV18 | E1 | 9 | 238 |
| HPV18 | E1 | 10 | 238 |
| HPV18 | E1 | 9 | 533 |
| HPV18 | E1 | 11 | 533 |
| HPV18 | E1 | 10 | 150 |
| HPV18 | E1 | 10 | 532 |
| HPV18 | E1 | 8 | 296 |
| HPV18 | E1 | 9 | 296 |
| HPV18 | E1 | 10 | 296 |
| HPV18 | E1 | 8 | 591 |
| HPV18 | E1 | 9 | 323 |
| HPV18 | E1 | 11 | 323 |
| HPV18 | E1 | 8 | 297 |
| HPV18 | E1 | 9 | 297 |
| HPV18 | E1 | 11 | 297 |
| HPV18 | E1 | 8 | 525 |
| HPV18 | E1 | 9 | 525 |
| HPV18 | E1 | 10 | 525 |
| HPV18 | E1 | 10 | 31 |

TABLE VIII-continued

HLA-A2 Supermotif-Bearing Peptides

| 1 | 2 | 3 | 4 |
|---|---|---|---|
| HPV18 | E1 | 11 | 31 |
| HPV18 | E1 | 8 | 505 |
| HPV18 | E1 | 10 | 81 |
| HPV18 | E1 | 11 | 84 |
| HPV18 | E1 | 9 | 339 |
| HPV18 | E1 | 9 | 20 |
| HPV18 | E1 | 9 | 450 |
| HPV18 | E1 | 9 | 368 |
| HPV18 | E1 | 10 | 368 |
| HPV18 | E1 | 10 | 244 |
| HPV18 | E1 | 11 | 244 |
| HPV18 | E1 | 11 | 149 |
| HPV18 | E1 | 8 | 370 |
| HPV18 | E1 | 8 | 346 |
| HPV18 | E1 | 9 | 432 |
| HPV18 | E1 | 8 | 516 |
| HPV18 | E1 | 10 | 516 |
| HPV18 | E1 | 11 | 516 |
| HPV18 | E1 | 8 | 536 |
| HPV18 | E1 | 11 | 536 |
| HPV18 | E1 | 8 | 243 |
| HPV18 | E1 | 11 | 243 |
| HPV18 | E1 | 11 | 386 |
| HPV18 | E1 | 8 | 585 |
| HPV18 | E1 | 8 | 408 |
| HPV18 | E1 | 11 | 542 |
| HPV18 | E1 | 8 | 455 |
| HPV18 | E1 | 10 | 455 |
| HPV18 | E1 | 10 | 19 |
| HPV18 | E2 | 9 | 49 |
| HPV18 | E2 | 10 | 49 |
| HPV18 | E2 | 10 | 245 |
| HPV18 | E2 | 11 | 245 |
| HPV18 | E2 | 8 | 76 |
| HPV18 | E2 | 11 | 76 |
| HPV18 | E2 | 11 | 45 |
| HPV18 | E2 | 8 | 351 |
| HPV18 | E2 | 9 | 351 |
| HPV18 | E2 | 10 | 351 |
| HPV18 | E2 | 11 | 87 |
| HPV18 | E2 | 9 | 154 |
| HPV18 | E2 | 8 | 214 |
| HPV18 | E2 | 11 | 214 |
| HPV18 | E2 | 9 | 246 |
| HPV18 | E2 | 10 | 246 |
| HPV18 | E2 | 10 | 132 |
| HPV18 | E2 | 10 | 156 |
| HPV18 | E2 | 8 | 146 |
| HPV18 | E2 | 9 | 146 |
| HPV18 | E2 | 10 | 146 |
| HPV18 | E2 | 11 | 29 |
| HPV18 | E2 | 9 | 315 |
| HPV18 | E2 | 11 | 315 |
| HPV18 | E2 | 9 | 100 |
| HPV18 | E2 | 8 | 210 |
| HPV18 | E2 | 9 | 210 |
| HPV18 | E2 | 9 | 78 |
| HPV18 | E2 | 10 | 78 |
| HPV18 | E2 | 8 | 104 |
| HPV18 | E2 | 10 | 6 |
| HPV18 | E2 | 8 | 340 |
| HPV18 | E2 | 10 | 340 |
| HPV18 | E2 | 11 | 340 |
| HPV18 | E2 | 8 | 190 |
| HPV18 | E2 | 9 | 190 |
| HPV18 | E2 | 8 | 48 |
| HPV18 | E2 | 10 | 48 |
| HPV18 | E2 | 11 | 48 |
| HPV18 | E2 | 11 | 346 |
| HPV18 | E2 | 9 | 324 |
| HPV18 | E2 | 10 | 324 |
| HPV18 | E2 | 11 | 324 |
| HPV18 | E2 | 11 | 331 |
| HPV18 | E2 | 9 | 54 |
| HPV18 | E2 | 10 | 54 |
| HPV18 | E2 | 11 | 253 |
| HPV18 | E2 | 9 | 85 |
| HPV18 | E2 | 11 | 161 |
| HPV18 | E2 | 9 | 235 |
| HPV18 | E2 | 11 | 235 |
| HPV18 | E2 | 8 | 148 |
| HPV18 | E2 | 10 | 148 |
| HPV18 | E2 | 11 | 187 |
| HPV18 | E2 | 9 | 291 |
| HPV18 | E2 | 9 | 60 |
| HPV18 | E2 | 9 | 223 |
| HPV18 | E2 | 10 | 223 |
| HPV18 | E2 | 11 | 289 |
| HPV18 | E2 | 10 | 332 |
| HPV18 | E2 | 8 | 358 |
| HPV18 | E2 | 8 | 55 |
| HPV18 | E2 | 9 | 55 |
| HPV18 | E2 | 11 | 55 |
| HPV18 | E2 | 8 | 72 |
| HPV18 | E2 | 10 | 72 |
| HPV18 | E2 | 11 | 72 |
| HPV18 | E2 | 8 | 75 |
| HPV18 | E2 | 9 | 75 |
| HPV18 | E2 | 8 | 280 |
| HPV18 | E2 | 10 | 280 |
| HPV18 | E2 | 11 | 280 |
| HPV18 | E2 | 10 | 257 |
| HPV18 | E2 | 11 | 257 |
| HPV18 | E2 | 11 | 152 |
| HPV18 | E2 | 10 | 92 |
| HPV18 | E2 | 8 | 329 |
| HPV18 | E2 | 8 | 238 |
| HPV18 | E2 | 9 | 238 |
| HPV18 | E2 | 10 | 238 |
| HPV18 | E2 | 10 | 254 |
| HPV18 | E2 | 8 | 86 |
| HPV18 | E2 | 8 | 39 |
| HPV18 | E2 | 11 | 39 |
| HPV18 | E2 | 8 | 266 |
| HPV18 | E2 | 8 | 98 |
| HPV18 | E2 | 11 | 98 |
| HPV18 | E2 | 11 | 83 |
| HPV18 | E2 | 11 | 221 |
| HPV18 | E2 | 8 | 79 |
| HPV18 | E2 | 9 | 79 |
| HPV18 | E2 | 9 | 333 |
| HPV18 | E2 | 8 | 217 |
| HPV18 | E2 | 8 | 1 |
| HPV18 | E2 | 10 | 144 |
| HPV18 | E2 | 11 | 144 |
| HPV18 | E2 | 9 | 133 |
| HPV18 | E2 | 10 | 67 |
| HPV18 | E2 | 11 | 67 |
| HPV18 | E2 | 8 | 285 |
| HPV18 | E2 | 9 | 348 |
| HPV18 | E2 | 11 | 348 |
| HPV18 | E2 | 9 | 196 |
| HPV18 | E2 | 10 | 64 |
| HPV18 | E2 | 9 | 265 |
| HPV18 | E2 | 10 | 272 |
| HPV18 | E2 | 11 | 110 |
| HPV18 | E2 | 8 | 262 |
| HPV18 | E2 | 9 | 262 |
| HPV18 | E2 | 10 | 262 |
| HPV18 | E2 | 8 | 357 |
| HPV18 | E2 | 9 | 357 |
| HPV18 | E2 | 8 | 33 |
| HPV18 | E2 | 8 | 38 |
| HPV18 | E2 | 9 | 38 |
| HPV18 | E2 | 9 | 216 |
| HPV18 | E2 | 8 | 80 |
| HPV18 | E2 | 8 | 56 |
| HPV18 | E2 | 10 | 56 |
| HPV18 | E2 | 11 | 2 |
| HPV18 | E2 | 8 | 61 |

TABLE VIII-continued

HLA-A2 Supermotif-Bearing Peptides

| 1 | 2 | 3 | 4 |
|---|---|---|---|
| HPV18 | E2 | 9 | 11 |
| HPV18 | E2 | 10 | 11 |
| HPV18 | E2 | 8 | 343 |
| HPV18 | E2 | 9 | 343 |
| HPV18 | E2 | 10 | 343 |
| HPV18 | E2 | 11 | 244 |
| HPV18 | E2 | 9 | 213 |
| HPV18 | E2 | 9 | 298 |
| HPV18 | E2 | 9 | 203 |
| HPV18 | E2 | 10 | 203 |
| HPV18 | E2 | 8 | 32 |
| HPV18 | E2 | 9 | 32 |
| HPV18 | E2 | 9 | 206 |
| HPV18 | E2 | 10 | 206 |
| HPV18 | E2 | 8 | 230 |
| HPV18 | E2 | 10 | 230 |
| HPV18 | E2 | 8 | 318 |
| HPV18 | E2 | 11 | 233 |
| HPV18 | E2 | 9 | 355 |
| HPV18 | E2 | 10 | 355 |
| HPV18 | E2 | 11 | 355 |
| HPV18 | E2 | 8 | 140 |
| HPV18 | E2 | 10 | 140 |
| HPV18 | E2 | 8 | 235 |
| HPV18 | E2 | 10 | 236 |
| HPV18 | E2 | 11 | 236 |
| HPV18 | E2 | 10 | 153 |
| HPV18 | E2 | 9 | 57 |
| HPV18 | E2 | 9 | 97 |
| HPV18 | E2 | 9 | 7 |
| HPV18 | E2 | 10 | 215 |
| HPV18 | E2 | 9 | 341 |
| HPV18 | E2 | 10 | 341 |
| HPV18 | E2 | 11 | 341 |
| HPV18 | E2 | 8 | 349 |
| HPV18 | E2 | 10 | 349 |
| HPV18 | E2 | 11 | 349 |
| HPV18 | E2 | 8 | 211 |
| HPV18 | E2 | 11 | 211 |
| HPV18 | E2 | 9 | 231 |
| HPV18 | E2 | 8 | 334 |
| HPV18 | E2 | 11 | 334 |
| HPV18 | E2 | 9 | 350 |
| HPV18 | E2 | 10 | 350 |
| HPV18 | E2 | 11 | 350 |
| HPV18 | E2 | 9 | 136 |
| HPV18 | E2 | 10 | 136 |
| HPV18 | E2 | 8 | 197 |
| HPV18 | E2 | 11 | 197 |
| HPV18 | E2 | 8 | 356 |
| HPV18 | E2 | 9 | 356 |
| HPV18 | E2 | 10 | 356 |
| HPV18 | E2 | 10 | 335 |
| HPV18 | E2 | 9 | 37 |
| HPV18 | E2 | 10 | 37 |
| HPV18 | E2 | 9 | 322 |
| HPV18 | E2 | 11 | 322 |
| HPV18 | E2 | 10 | 96 |
| HPV18 | E2 | 11 | 143 |
| HPV18 | E2 | 10 | 135 |
| HPV18 | E2 | 11 | 135 |
| HPV18 | E2 | 8 | 164 |
| HPV18 | E2 | 11 | 164 |
| HPV18 | E5 | 8 | 47 |
| HPV18 | E5 | 8 | 29 |
| HPV18 | E5 | 10 | 29 |
| HPV18 | E5 | 8 | 27 |
| HPV18 | E5 | 9 | 27 |
| HPV18 | E5 | 10 | 27 |
| HPV18 | E5 | 8 | 13 |
| HPV18 | E5 | 10 | 13 |
| HPV18 | E5 | 11 | 13 |
| HPV18 | E5 | 10 | 11 |
| HPV18 | E5 | 9 | 6 |
| HPV18 | E5 | 11 | 6 |
| HPV18 | E5 | 8 | 57 |
| HPV18 | E5 | 10 | 57 |
| HPV18 | E5 | 9 | 50 |
| HPV18 | E5 | 10 | 50 |
| HPV18 | E5 | 8 | 37 |
| HPV18 | E5 | 11 | 37 |
| HPV18 | E5 | 8 | 65 |
| HPV18 | E5 | 8 | 19 |
| HPV18 | E5 | 10 | 19 |
| HPV18 | E5 | 9 | 43 |
| HPV18 | E5 | 10 | 43 |
| HPV18 | E5 | 8 | 40 |
| HPV18 | E5 | 9 | 40 |
| HPV18 | E5 | 10 | 40 |
| HPV18 | E5 | 9 | 4 |
| HPV18 | E5 | 11 | 4 |
| HPV18 | E5 | 8 | 63 |
| HPV18 | E5 | 10 | 63 |
| HPV18 | E5 | 8 | 62 |
| HPV18 | E5 | 9 | 62 |
| HPV18 | E5 | 11 | 62 |
| HPV18 | E5 | 9 | 58 |
| HPV18 | E5 | 11 | 58 |
| HPV18 | E5 | 9 | 22 |
| HPV18 | E5 | 11 | 22 |
| HPV18 | E5 | 8 | 35 |
| HPV18 | E5 | 9 | 35 |
| HPV18 | E5 | 10 | 35 |
| HPV18 | E5 | 8 | 61 |
| HPV18 | E5 | 9 | 61 |
| HPV18 | E5 | 10 | 61 |
| HPV18 | E5 | 9 | 46 |
| HPV18 | E5 | 8 | 21 |
| HPV18 | E5 | 10 | 21 |
| HPV18 | E5 | 9 | 60 |
| HPV18 | E5 | 10 | 60 |
| HPV18 | E5 | 11 | 60 |
| HPV18 | E5 | 10 | 3 |
| HPV18 | E5 | 8 | 25 |
| HPV18 | E5 | 10 | 25 |
| HPV18 | E5 | 11 | 25 |
| HPV18 | E5 | 11 | 48 |
| HPV18 | E5 | 8 | 51 |
| HPV18 | E5 | 9 | 51 |
| HPV18 | E5 | 11 | 51 |
| HPV18 | E5 | 8 | 42 |
| HPV18 | E5 | 10 | 42 |
| HPV18 | E5 | 11 | 42 |
| HPV18 | E5 | 8 | 34 |
| HPV18 | E5 | 9 | 34 |
| HPV18 | E5 | 10 | 34 |
| HPV18 | E5 | 11 | 34 |
| HPV18 | E5 | 8 | 41 |
| HPV18 | E5 | 9 | 41 |
| HPV18 | E5 | 11 | 41 |
| HPV18 | E5 | 8 | 33 |
| HPV18 | E5 | 9 | 33 |
| HPV18 | E5 | 10 | 33 |
| HPV18 | E5 | 11 | 33 |
| HPV18 | E5 | 8 | 31 |
| HPV18 | E5 | 10 | 31 |
| HPV18 | E5 | 11 | 31 |
| HPV18 | E5 | 9 | 39 |
| HPV18 | E5 | 10 | 39 |
| HPV18 | E5 | 11 | 39 |
| HPV18 | E5 | 8 | 15 |
| HPV18 | E5 | 9 | 15 |
| HPV18 | E5 | 9 | 53 |
| HPV18 | E5 | 10 | 53 |
| HPV18 | E5 | 11 | 53 |
| HPV18 | E6 | 8 | 68 |
| HPV18 | E6 | 11 | 68 |
| HPV18 | E6 | 8 | 105 |
| HPV18 | E6 | 11 | 105 |
| HPV18 | E6 | 8 | 108 |

TABLE VIII-continued

HLA-A2 Supermotif-Bearing Peptides

| 1 | 2 | 3 | 4 |
|---|---|---|---|
| HPV18 | E6 | 11 | 108 |
| HPV18 | E6 | 8 | 18 |
| HPV18 | E6 | 11 | 18 |
| HPV18 | E6 | 8 | 32 |
| HPV18 | E6 | 10 | 32 |
| HPV18 | E6 | 11 | 32 |
| HPV18 | E6 | 11 | 27 |
| HPV18 | E6 | 8 | 16 |
| HPV18 | E6 | 10 | 16 |
| HPV18 | E6 | 10 | 51 |
| HPV18 | E6 | 9 | 88 |
| HPV18 | E6 | 11 | 88 |
| HPV18 | E6 | 9 | 29 |
| HPV18 | E6 | 10 | 29 |
| HPV18 | E6 | 11 | 29 |
| HPV18 | E6 | 9 | 20 |
| HPV18 | E6 | 11 | 20 |
| HPV18 | E6 | 9 | 77 |
| HPV18 | E6 | 9 | 40 |
| HPV18 | E6 | 10 | 43 |
| HPV18 | E6 | 8 | 47 |
| HPV18 | E6 | 9 | 47 |
| HPV18 | E6 | 8 | 53 |
| HPV18 | E6 | 11 | 53 |
| HPV18 | E6 | 10 | 97 |
| HPV18 | E6 | 10 | 136 |
| HPV18 | E6 | 8 | 62 |
| HPV18 | E6 | 11 | 120 |
| HPV18 | E6 | 8 | 30 |
| HPV18 | E6 | 9 | 30 |
| HPV18 | E6 | 10 | 30 |
| HPV18 | E6 | 9 | 13 |
| HPV18 | E6 | 11 | 13 |
| HPV18 | E6 | 10 | 92 |
| HPV18 | E6 | 11 | 92 |
| HPV18 | E6 | 9 | 36 |
| HPV18 | E6 | 11 | 102 |
| HPV18 | E6 | 9 | 25 |
| HPV18 | E6 | 9 | 150 |
| HPV18 | E6 | 8 | 41 |
| HPV18 | E6 | 9 | 93 |
| HPV18 | E6 | 10 | 93 |
| HPV18 | E6 | 11 | 93 |
| HPV18 | E6 | 8 | 1 |
| HPV18 | E6 | 8 | 95 |
| HPV18 | E6 | 9 | 95 |
| HPV18 | E6 | 9 | 22 |
| HPV18 | E6 | 10 | 22 |
| HPV18 | E6 | 8 | 114 |
| HPV18 | E6 | 8 | 111 |
| HPV18 | E6 | 11 | 111 |
| HPV18 | E6 | 8 | 7 |
| HPV18 | E6 | 11 | 7 |
| HPV18 | E6 | 8 | 149 |
| HPV18 | E6 | 10 | 149 |
| HPV18 | E6 | 11 | 146 |
| HPV18 | E6 | 11 | 59 |
| HPV18 | E6 | 8 | 24 |
| HPV18 | E6 | 10 | 24 |
| HPV18 | E6 | 10 | 84 |
| HPV18 | E6 | 11 | 84 |
| HPV18 | E6 | 8 | 89 |
| HPV18 | E6 | 10 | 89 |
| HPV18 | E6 | 8 | 37 |
| HPV18 | E6 | 11 | 38 |
| HPV18 | E6 | 10 | 54 |
| HPV18 | E6 | 11 | 54 |
| HPV18 | E7 | 8 | 6 |
| HPV18 | E7 | 10 | 6 |
| HPV18 | E7 | 8 | 63 |
| HPV18 | E7 | 10 | 63 |
| HPV18 | E7 | 8 | 24 |
| HPV18 | E7 | 8 | 82 |
| HPV18 | E7 | 10 | 82 |
| HPV18 | E7 | 8 | 69 |
| HPV18 | E7 | 10 | 40 |
| HPV18 | E7 | 8 | 90 |
| HPV18 | E7 | 8 | 86 |
| HPV18 | E7 | 9 | 86 |
| HPV18 | E7 | 9 | 43 |
| HPV18 | E7 | 8 | 14 |
| HPV18 | E7 | 10 | 14 |
| HPV18 | E7 | 9 | 46 |
| HPV18 | E7 | 11 | 11 |
| HPV18 | E7 | 8 | 5 |
| HPV18 | E7 | 9 | 5 |
| HPV18 | E7 | 11 | 5 |
| HPV18 | E7 | 8 | 73 |
| HPV18 | E7 | 11 | 73 |
| HPV18 | E7 | 8 | 8 |
| HPV18 | E7 | 10 | 74 |
| HPV18 | E7 | 10 | 61 |
| HPV18 | E7 | 11 | 92 |
| HPV18 | E7 | 11 | 50 |
| HPV18 | E7 | 9 | 17 |
| HPV18 | E7 | 10 | 17 |
| HPV18 | E7 | 9 | 56 |
| HPV18 | E7 | 10 | 22 |
| HPV18 | E7 | 10 | 88 |
| HPV18 | E7 | 8 | 87 |
| HPV18 | E7 | 11 | 87 |
| HPV18 | E7 | 8 | 53 |
| HPV18 | E7 | 9 | 53 |
| HPV18 | E7 | 10 | 53 |
| HPV18 | E7 | 8 | 84 |
| HPV18 | E7 | 10 | 84 |
| HPV18 | E7 | 11 | 84 |
| HPV18 | E7 | 10 | 71 |
| HPV18 | E7 | 11 | 79 |
| HPV18 | E7 | 9 | 7 |
| HPV18 | E7 | 10 | 93 |
| HPV18 | E7 | 11 | 60 |
| HPV18 | E7 | 10 | 12 |
| HPV18 | E7 | 9 | 75 |
| HPV18 | E7 | 11 | 75 |
| HPV18 | L1 | 10 | 195 |
| HPV18 | L1 | 10 | 225 |
| HPV18 | L1 | 11 | 225 |
| HPV18 | L1 | 8 | 487 |
| HPV18 | L1 | 9 | 487 |
| HPV18 | L1 | 11 | 487 |
| HPV18 | L1 | 9 | 63 |
| HPV18 | L1 | 10 | 63 |
| HPV18 | L1 | 10 | 268 |
| HPV18 | L1 | 8 | 377 |
| HPV18 | L1 | 11 | 419 |
| HPV18 | L1 | 9 | 196 |
| HPV18 | L1 | 8 | 552 |
| HPV18 | L1 | 11 | 552 |
| HPV18 | L1 | 10 | 222 |
| HPV18 | L1 | 8 | 406 |
| HPV18 | L1 | 8 | 218 |
| HPV18 | L1 | 9 | 218 |
| HPV18 | L1 | 9 | 310 |
| HPV18 | L1 | 8 | 2 |
| HPV18 | L1 | 9 | 2 |
| HPV18 | L1 | 8 | 490 |
| HPV18 | L1 | 11 | 286 |
| HPV18 | L1 | 9 | 441 |
| HPV18 | L1 | 10 | 441 |
| HPV18 | L1 | 11 | 350 |
| HPV18 | L1 | 8 | 512 |
| HPV18 | L1 | 10 | 512 |
| HPV18 | L1 | 8 | 433 |
| HPV18 | L1 | 10 | 433 |
| HPV18 | L1 | 11 | 433 |
| HPV18 | L1 | 9 | 260 |
| HPV18 | L1 | 10 | 260 |
| HPV18 | L1 | 10 | 522 |
| HPV18 | L1 | 11 | 522 |

TABLE VIII-continued

HLA-A2 Supermotif-Bearing Peptides

| 1 | 2 | 3 | 4 |
|---|---|---|---|
| HPV18 | L1 | 8 | 189 |
| HPV18 | L1 | 9 | 189 |
| HPV18 | L1 | 11 | 263 |
| HPV18 | L1 | 8 | 276 |
| HPV18 | L1 | 10 | 276 |
| HPV18 | L1 | 9 | 148 |
| HPV18 | L1 | 8 | 396 |
| HPV18 | L1 | 9 | 396 |
| HPV18 | L1 | 10 | 396 |
| HPV18 | L1 | 9 | 330 |
| HPV18 | L1 | 9 | 478 |
| HPV18 | L1 | 10 | 478 |
| HPV18 | L1 | 11 | 478 |
| HPV18 | L1 | 9 | 448 |
| HPV18 | L1 | 8 | 203 |
| HPV18 | L1 | 8 | 167 |
| HPV18 | L1 | 10 | 167 |
| HPV18 | L1 | 8 | 155 |
| HPV18 | L1 | 10 | 155 |
| HPV18 | L1 | 10 | 280 |
| HPV18 | L1 | 9 | 317 |
| HPV18 | L1 | 11 | 317 |
| HPV18 | L1 | 8 | 436 |
| HPV18 | L1 | 9 | 436 |
| HPV18 | L1 | 10 | 436 |
| HPV18 | L1 | 11 | 436 |
| HPV18 | L1 | 10 | 49 |
| HPV18 | L1 | 8 | 438 |
| HPV18 | L1 | 9 | 438 |
| HPV18 | L1 | 10 | 438 |
| HPV18 | L1 | 8 | 482 |
| HPV18 | L1 | 8 | 391 |
| HPV18 | L1 | 11 | 391 |
| HPV18 | L1 | 8 | 267 |
| HPV18 | L1 | 11 | 267 |
| HPV18 | L1 | 8 | 535 |
| HPV18 | L1 | 11 | 177 |
| HPV18 | L1 | 10 | 342 |
| HPV18 | L1 | 8 | 171 |
| HPV18 | L1 | 9 | 233 |
| HPV18 | L1 | 11 | 326 |
| HPV18 | L1 | 8 | 383 |
| HPV18 | L1 | 10 | 383 |
| HPV18 | L1 | 11 | 383 |
| HPV18 | L1 | 10 | 165 |
| HPV18 | L1 | 8 | 467 |
| HPV18 | L1 | 10 | 467 |
| HPV18 | L1 | 11 | 467 |
| HPV18 | L1 | 11 | 194 |
| HPV18 | L1 | 8 | 97 |
| HPV18 | L1 | 9 | 97 |
| HPV18 | L1 | 10 | 97 |
| HPV18 | L1 | 9 | 38 |
| HPV18 | L1 | 10 | 38 |
| HPV18 | L1 | 11 | 38 |
| HPV18 | L1 | 9 | 13 |
| HPV18 | L1 | 10 | 428 |
| HPV18 | L1 | 8 | 40 |
| HPV18 | L1 | 9 | 40 |
| HPV18 | L1 | 11 | 40 |
| HPV18 | L1 | 8 | 39 |
| HPV18 | L1 | 9 | 39 |
| HPV18 | L1 | 10 | 39 |
| HPV18 | L1 | 8 | 46 |
| HPV18 | L1 | 10 | 46 |
| HPV18 | L1 | 9 | 460 |
| HPV18 | L1 | 9 | 47 |
| HPV18 | L1 | 8 | 219 |
| HPV18 | L1 | 9 | 9 |
| HPV18 | L1 | 8 | 32 |
| HPV18 | L1 | 9 | 32 |
| HPV18 | L1 | 10 | 32 |
| HPV18 | L1 | 8 | 488 |
| HPV18 | L1 | 10 | 488 |
| HPV18 | L1 | 8 | 443 |
| HPV18 | L1 | 11 | 443 |
| HPV18 | L1 | 8 | 360 |
| HPV18 | L1 | 9 | 376 |
| HPV18 | L1 | 10 | 186 |
| HPV18 | L1 | 11 | 186 |
| HPV18 | L1 | 9 | 505 |
| HPV18 | L1 | 9 | 120 |
| HPV18 | L1 | 8 | 213 |
| HPV18 | L1 | 11 | 213 |
| HPV18 | L1 | 9 | 125 |
| HPV18 | L1 | 8 | 8 |
| HPV18 | L1 | 10 | 8 |
| HPV18 | L1 | 8 | 14 |
| HPV18 | L1 | 11 | 103 |
| HPV18 | L1 | 8 | 274 |
| HPV18 | L1 | 10 | 274 |
| HPV18 | L1 | 9 | 434 |
| HPV18 | L1 | 10 | 434 |
| HPV18 | L1 | 11 | 434 |
| HPV18 | L1 | 9 | 445 |
| HPV18 | L1 | 11 | 403 |
| HPV18 | L1 | 10 | 104 |
| HPV18 | L1 | 8 | 476 |
| HPV18 | L1 | 11 | 476 |
| HPV18 | L1 | 11 | 531 |
| HPV18 | L1 | 8 | 159 |
| HPV18 | L1 | 10 | 159 |
| HPV18 | L1 | 8 | 33 |
| HPV18 | L1 | 9 | 33 |
| HPV18 | L1 | 10 | 62 |
| HPV18 | L1 | 11 | 62 |
| HPV18 | L1 | 8 | 261 |
| HPV18 | L1 | 9 | 261 |
| HPV18 | L1 | 11 | 36 |
| HPV18 | L1 | 8 | 402 |
| HPV18 | L1 | 8 | 388 |
| HPV18 | L1 | 10 | 388 |
| HPV18 | L1 | 11 | 388 |
| HPV18 | L1 | 9 | 84 |
| HPV18 | L1 | 11 | 84 |
| HPV18 | L1 | 9 | 253 |
| HPV18 | L1 | 10 | 253 |
| HPV18 | L1 | 10 | 70 |
| HPV18 | L1 | 11 | 70 |
| HPV18 | L1 | 10 | 510 |
| HPV18 | L1 | 9 | 54 |
| HPV18 | L1 | 10 | 54 |
| HPV18 | L1 | 11 | 54 |
| HPV18 | L1 | 9 | 52 |
| HPV18 | L1 | 11 | 52 |
| HPV18 | L1 | 10 | 199 |
| HPV18 | L1 | 9 | 207 |
| HPV18 | L1 | 11 | 207 |
| HPV18 | L1 | 11 | 496 |
| HPV18 | L1 | 10 | 114 |
| HPV18 | L1 | 8 | 224 |
| HPV18 | L1 | 11 | 224 |
| HPV18 | L1 | 9 | 558 |
| HPV18 | L1 | 8 | 344 |
| HPV18 | L1 | 8 | 57 |
| HPV18 | L1 | 8 | 282 |
| HPV18 | L1 | 8 | 248 |
| HPV18 | L1 | 9 | 248 |
| HPV18 | L1 | 8 | 525 |
| HPV18 | L1 | 10 | 525 |
| HPV18 | L1 | 9 | 28 |
| HPV18 | L1 | 10 | 28 |
| HPV18 | L1 | 8 | 26 |
| HPV18 | L1 | 9 | 26 |
| HPV18 | L1 | 11 | 26 |
| HPV18 | L1 | 10 | 240 |
| HPV18 | L1 | 8 | 20 |
| HPV18 | L1 | 10 | 20 |
| HPV18 | L1 | 9 | 333 |
| HPV18 | L1 | 11 | 333 |

TABLE VIII-continued

HLA-A2 Supermotif-Bearing Peptides

| 1 | 2 | 3 | 4 |
|---|---|---|---|
| HPV18 | L1 | 10 | 540 |
| HPV18 | L1 | 8 | 91 |
| HPV18 | L1 | 8 | 472 |
| HPV18 | L1 | 8 | 412 |
| HPV18 | L1 | 9 | 412 |
| HPV18 | L1 | 9 | 533 |
| HPV18 | L1 | 10 | 533 |
| HPV18 | L1 | 8 | 216 |
| HPV18 | L1 | 10 | 216 |
| HPV18 | L1 | 11 | 216 |
| HPV18 | L1 | 8 | 439 |
| HPV18 | L1 | 9 | 439 |
| HPV18 | L1 | 11 | 439 |
| HPV18 | L1 | 11 | 315 |
| HPV18 | L1 | 9 | 366 |
| HPV18 | L1 | 9 | 389 |
| HPV18 | L1 | 10 | 389 |
| HPV18 | L1 | 10 | 137 |
| HPV18 | L1 | 11 | 61 |
| HPV18 | L1 | 11 | 297 |
| HPV18 | L1 | 10 | 214 |
| HPV18 | L1 | 8 | 324 |
| HPV18 | L1 | 9 | 324 |
| HPV18 | L1 | 9 | 158 |
| HPV18 | L1 | 11 | 158 |
| HPV18 | L1 | 9 | 6 |
| HPV18 | L1 | 10 | 6 |
| HPV18 | L1 | 9 | 81 |
| HPV18 | L1 | 10 | 81 |
| HPV18 | L1 | 9 | 299 |
| HPV18 | L1 | 9 | 551 |
| HPV18 | L1 | 10 | 127 |
| HPV18 | L1 | 9 | 288 |
| HPV18 | L1 | 11 | 288 |
| HPV18 | L1 | 11 | 93 |
| HPV18 | L1 | 10 | 459 |
| HPV18 | L1 | 9 | 31 |
| HPV18 | L1 | 10 | 31 |
| HPV18 | L1 | 11 | 31 |
| HPV18 | L1 | 9 | 359 |
| HPV18 | L1 | 10 | 150 |
| HPV18 | L1 | 11 | 150 |
| HPV18 | L1 | 9 | 518 |
| HPV18 | L1 | 9 | 475 |
| HPV18 | L1 | 9 | 335 |
| HPV18 | L1 | 11 | 335 |
| HPV18 | L1 | 11 | 306 |
| HPV18 | L1 | 8 | 242 |
| HPV18 | L1 | 10 | 242 |
| HPV18 | L1 | 10 | 365 |
| HPV18 | L1 | 10 | 242 |
| HPV18 | L1 | 8 | 400 |
| HPV18 | L1 | 10 | 400 |
| HPV18 | L1 | 10 | 485 |
| HPV18 | L1 | 11 | 485 |
| HPV18 | L1 | 8 | 78 |
| HPV18 | L1 | 9 | 209 |
| HPV18 | L1 | 11 | 209 |
| HPV18 | L1 | 8 | 234 |
| HPV18 | L1 | 8 | 446 |
| HPV18 | L1 | 11 | 446 |
| HPV18 | L1 | 10 | 404 |
| HPV18 | L1 | 9 | 541 |
| HPV18 | L1 | 8 | 442 |
| HPV18 | L1 | 9 | 442 |
| HPV18 | L1 | 9 | 273 |
| HPV18 | L1 | 11 | 273 |
| HPV18 | L1 | 10 | 444 |
| HPV18 | L1 | 10 | 327 |
| HPV18 | L1 | 9 | 215 |
| HPV18 | L1 | 11 | 215 |
| HPV18 | L1 | 9 | 156 |
| HPV18 | L1 | 11 | 156 |
| HPV18 | L1 | 11 | 409 |
| HPV18 | L1 | 8 | 397 |
| HPV18 | L1 | 9 | 397 |
| HPV18 | L1 | 11 | 397 |
| HPV18 | L1 | 11 | 473 |
| HPV18 | L1 | 10 | 553 |
| HPV18 | L1 | 9 | 105 |
| HPV18 | L1 | 11 | 105 |
| HPV18 | L1 | 8 | 254 |
| HPV18 | L1 | 9 | 254 |
| HPV18 | L1 | 11 | 254 |
| HPV18 | L1 | 8 | 331 |
| HPV18 | L1 | 11 | 331 |
| HPV18 | L1 | 9 | 393 |
| HPV18 | L1 | 11 | 393 |
| HPV18 | L1 | 9 | 71 |
| HPV18 | L1 | 10 | 71 |
| HPV18 | L1 | 9 | 486 |
| HPV18 | L1 | 10 | 486 |
| HPV18 | L1 | 11 | 79 |
| HPV18 | L1 | 8 | 255 |
| HPV18 | L1 | 10 | 255 |
| HPV18 | L1 | 8 | 7 |
| HPV18 | L1 | 9 | 7 |
| HPV18 | L1 | 11 | 7 |
| HPV18 | L1 | 8 | 449 |
| HPV18 | L1 | 10 | 532 |
| HPV18 | L1 | 11 | 532 |
| HPV18 | L1 | 11 | 136 |
| HPV18 | L1 | 10 | 89 |
| HPV18 | L1 | 10 | 392 |
| HPV18 | L1 | 8 | 394 |
| HPV18 | L1 | 8 | 82 |
| HPV18 | L1 | 9 | 82 |
| HPV18 | L1 | 11 | 82 |
| HPV18 | L1 | 8 | 161 |
| HPV18 | L1 | 9 | 452 |
| HPV18 | L1 | 10 | 452 |
| HPV18 | L1 | 9 | 45 |
| HPV18 | L1 | 11 | 45 |
| HPV18 | L1 | 9 | 337 |
| HPV18 | L1 | 8 | 73 |
| HPV18 | L1 | 10 | 73 |
| HPV18 | L1 | 11 | 73 |
| HPV18 | L1 | 8 | 129 |
| HPV18 | L1 | 10 | 129 |
| HPV18 | L1 | 11 | 4 |
| HPV18 | L1 | 11 | 88 |
| HPV18 | L2 | 9 | 6 |
| HPV18 | L2 | 10 | 6 |
| HPV18 | L2 | 8 | 286 |
| HPV18 | L2 | 9 | 286 |
| HPV18 | L2 | 10 | 341 |
| HPV18 | L2 | 9 | 303 |
| HPV18 | L2 | 11 | 303 |
| HPV18 | L2 | 10 | 139 |
| HPV18 | L2 | 9 | 358 |
| HPV18 | L2 | 10 | 358 |
| HPV18 | L2 | 9 | 278 |
| HPV18 | L2 | 10 | 278 |
| HPV18 | L2 | 11 | 278 |
| HPV18 | L2 | 8 | 404 |
| HPV18 | L2 | 10 | 404 |
| HPV18 | L2 | 9 | 142 |
| HPV18 | L2 | 11 | 142 |
| HPV18 | L2 | 8 | 129 |
| HPV18 | L2 | 9 | 129 |
| HPV18 | L2 | 11 | 129 |
| HPV18 | L2 | 10 | 349 |
| HPV18 | L2 | 11 | 349 |
| HPV18 | L2 | 10 | 346 |
| HPV18 | L2 | 11 | 16 |
| HPV18 | L2 | 8 | 354 |
| HPV18 | L2 | 9 | 83 |
| HPV18 | L2 | 10 | 83 |
| HPV18 | L2 | 11 | 83 |
| HPV18 | L2 | 8 | 270 |

TABLE VIII-continued

HLA-A2 Supermotif-Bearing Peptides

| 1 | 2 | 3 | 4 |
|---|---|---|---|
| HPV18 | L2 | 10 | 270 |
| HPV18 | L2 | 11 | 270 |
| HPV18 | L2 | 10 | 396 |
| HPV18 | L2 | 11 | 396 |
| HPV18 | L2 | 9 | 30 |
| HPV18 | L2 | 10 | 30 |
| HPV18 | L2 | 11 | 30 |
| HPV18 | L2 | 8 | 194 |
| HPV18 | L2 | 8 | 334 |
| HPV18 | L2 | 9 | 334 |
| HPV18 | L2 | 8 | 175 |
| HPV18 | L2 | 10 | 175 |
| HPV18 | L2 | 8 | 169 |
| HPV18 | L2 | 9 | 169 |
| HPV18 | L2 | 8 | 455 |
| HPV18 | L2 | 9 | 369 |
| HPV18 | L2 | 10 | 369 |
| HPV18 | L2 | 11 | 200 |
| HPV18 | L2 | 9 | 443 |
| HPV18 | L2 | 9 | 53 |
| HPV18 | L2 | 8 | 241 |
| HPV18 | L2 | 9 | 241 |
| HPV18 | L2 | 10 | 241 |
| HPV18 | L2 | 11 | 276 |
| HPV18 | L2 | 9 | 122 |
| HPV18 | L2 | 10 | 122 |
| HPV18 | L2 | 11 | 157 |
| HPV18 | L2 | 8 | 306 |
| HPV18 | L2 | 10 | 306 |
| HPV18 | L2 | 9 | 181 |
| HPV18 | L2 | 8 | 116 |
| HPV18 | L2 | 10 | 116 |
| HPV18 | L2 | 10 | 314 |
| HPV18 | L2 | 9 | 51 |
| HPV18 | L2 | 11 | 51 |
| HPV18 | L2 | 8 | 58 |
| HPV18 | L2 | 9 | 429 |
| HPV18 | L2 | 10 | 56 |
| HPV18 | L2 | 8 | 300 |
| HPV18 | L2 | 8 | 25 |
| HPV18 | L2 | 11 | 25 |
| HPV18 | L2 | 10 | 204 |
| HPV18 | L2 | 9 | 64 |
| HPV18 | L2 | 11 | 64 |
| HPV18 | L2 | 10 | 60 |
| HPV18 | L2 | 8 | 188 |
| HPV18 | L2 | 10 | 188 |
| HPV18 | L2 | 9 | 432 |
| HPV18 | L2 | 8 | 310 |
| HPV18 | L2 | 8 | 124 |
| HPV18 | L2 | 10 | 124 |
| HPV18 | L2 | 8 | 37 |
| HPV18 | L2 | 9 | 37 |
| HPV18 | L2 | 8 | 134 |
| HPV18 | L2 | 10 | 134 |
| HPV18 | L2 | 11 | 134 |
| HPV18 | L2 | 8 | 292 |
| HPV18 | L2 | 8 | 326 |
| HPV18 | L2 | 10 | 326 |
| HPV18 | L2 | 10 | 167 |
| HPV18 | L2 | 11 | 167 |
| HPV18 | L2 | 8 | 279 |
| HPV18 | L2 | 9 | 279 |
| HPV18 | L2 | 10 | 279 |
| HPV18 | L2 | 9 | 44 |
| HPV18 | L2 | 11 | 44 |
| HPV18 | L2 | 9 | 405 |
| HPV18 | L2 | 8 | 143 |
| HPV18 | L2 | 10 | 143 |
| HPV18 | L2 | 8 | 130 |
| HPV18 | L2 | 10 | 130 |
| HPV18 | L2 | 11 | 130 |
| HPV18 | L2 | 11 | 249 |
| HPV18 | L2 | 8 | 416 |
| HPV18 | L2 | 10 | 416 |
| HPV18 | L2 | 10 | 103 |
| HPV18 | L2 | 11 | 103 |
| HPV18 | L2 | 8 | 43 |
| HPV18 | L2 | 10 | 43 |
| HPV18 | L2 | 10 | 22 |
| HPV18 | L2 | 11 | 22 |
| HPV18 | L2 | 8 | 19 |
| HPV18 | L2 | 8 | 34 |
| HPV18 | L2 | 11 | 34 |
| HPV18 | L2 | 11 | 40 |
| HPV18 | L2 | 8 | 106 |
| HPV18 | L2 | 9 | 106 |
| HPV18 | L2 | 8 | 248 |
| HPV18 | L2 | 8 | 335 |
| HPV18 | L2 | 9 | 197 |
| HPV18 | L2 | 8 | 45 |
| HPV18 | L2 | 10 | 45 |
| HPV18 | L2 | 9 | 263 |
| HPV18 | L2 | 8 | 242 |
| HPV18 | L2 | 9 | 242 |
| HPV18 | L2 | 8 | 287 |
| HPV18 | L2 | 9 | 391 |
| HPV18 | L2 | 11 | 391 |
| HPV18 | L2 | 10 | 338 |
| HPV18 | L2 | 9 | 79 |
| HPV18 | L2 | 8 | 179 |
| HPV18 | L2 | 11 | 179 |
| HPV18 | L2 | 8 | 254 |
| HPV18 | L2 | 9 | 254 |
| HPV18 | L2 | 10 | 254 |
| HPV18 | L2 | 11 | 254 |
| HPV18 | L2 | 8 | 160 |
| HPV18 | L2 | 9 | 160 |
| HPV18 | L2 | 11 | 160 |
| HPV18 | L2 | 9 | 285 |
| HPV18 | L2 | 10 | 285 |
| HPV18 | L2 | 9 | 422 |
| HPV18 | L2 | 11 | 138 |
| HPV18 | L2 | 10 | 357 |
| HPV18 | L2 | 11 | 357 |
| HPV18 | L2 | 9 | 325 |
| HPV18 | L2 | 11 | 325 |
| HPV18 | L2 | 9 | 209 |
| HPV18 | L2 | 10 | 209 |
| HPV18 | L2 | 9 | 415 |
| HPV18 | L2 | 11 | 415 |
| HPV18 | L2 | 8 | 73 |
| HPV18 | L2 | 9 | 73 |
| HPV18 | L2 | 10 | 73 |
| HPV18 | L2 | 8 | 214 |
| HPV18 | L2 | 9 | 214 |
| HPV18 | L2 | 10 | 196 |
| HPV18 | L2 | 8 | 390 |
| HPV18 | L2 | 10 | 390 |
| HPV18 | L2 | 11 | 337 |
| HPV18 | L2 | 10 | 171 |
| HPV18 | L2 | 10 | 419 |
| HPV18 | L2 | 8 | 98 |
| HPV18 | L2 | 9 | 98 |
| HPV18 | L2 | 10 | 98 |
| HPV18 | L2 | 11 | 120 |
| HPV18 | L2 | 8 | 86 |
| HPV18 | L2 | 11 | 86 |
| HPV18 | L2 | 11 | 185 |
| HPV18 | L2 | 11 | 216 |
| HPV18 | L2 | 9 | 95 |
| HPV18 | L2 | 10 | 95 |
| HPV18 | L2 | 11 | 95 |
| HPV18 | L2 | 8 | 360 |
| HPV18 | L2 | 11 | 360 |
| HPV18 | L2 | 10 | 90 |
| HPV18 | L2 | 8 | 398 |
| HPV18 | L2 | 9 | 398 |
| HPV18 | L2 | 10 | 398 |
| HPV18 | L2 | 11 | 232 |

TABLE VIII-continued

HLA-A2 Supermotif-Bearing Peptides

| 1 | 2 | 3 | 4 |
|---|---|---|---|
| HPV18 | L2 | 8 | 198 |
| HPV18 | L2 | 9 | 172 |
| HPV18 | L2 | 11 | 172 |
| HPV18 | L2 | 10 | 233 |
| HPV18 | L2 | 11 | 233 |
| HPV18 | L2 | 8 | 5 |
| HPV18 | L2 | 10 | 5 |
| HPV18 | L2 | 11 | 5 |
| HPV18 | L2 | 10 | 11 |
| HPV18 | L2 | 10 | 302 |
| HPV18 | L2 | 8 | 229 |
| HPV18 | L2 | 9 | 229 |
| HPV18 | L2 | 8 | 298 |
| HPV18 | L2 | 10 | 298 |
| HPV18 | L2 | 8 | 281 |
| HPV18 | L2 | 10 | 225 |
| HPV18 | L2 | 11 | 220 |
| HPV18 | L2 | 8 | 316 |
| HPV18 | L2 | 11 | 316 |
| HPV18 | L2 | 11 | 450 |
| HPV18 | L2 | 8 | 132 |
| HPV18 | L2 | 9 | 132 |
| HPV18 | L2 | 10 | 132 |
| HPV18 | L2 | 8 | 380 |
| HPV18 | L2 | 9 | 380 |
| HPV18 | L2 | 10 | 380 |
| HPV18 | L2 | 8 | 340 |
| HPV18 | L2 | 11 | 340 |
| HPV18 | L2 | 8 | 166 |
| HPV18 | L2 | 11 | 166 |
| HPV18 | L2 | 8 | 151 |
| HPV18 | L2 | 11 | 151 |
| HPV18 | L2 | 11 | 102 |
| HPV18 | L2 | 9 | 49 |
| HPV18 | L2 | 11 | 49 |
| HPV18 | L2 | 9 | 247 |
| HPV18 | L2 | 10 | 212 |
| HPV18 | L2 | 11 | 212 |
| HPV18 | L2 | 10 | 424 |
| HPV18 | L2 | 8 | 147 |
| HPV18 | L2 | 9 | 147 |
| HPV18 | L2 | 9 | 153 |
| HPV18 | L2 | 8 | 409 |
| HPV18 | L2 | 9 | 409 |
| HPV18 | L2 | 8 | 235 |
| HPV18 | L2 | 9 | 235 |
| HPV18 | L2 | 10 | 149 |
| HPV18 | L2 | 8 | 13 |
| HPV18 | L2 | 11 | 111 |
| HPV18 | L2 | 9 | 412 |
| HPV18 | L2 | 10 | 412 |
| HPV18 | L2 | 9 | 420 |
| HPV18 | L2 | 11 | 420 |
| HPV18 | L2 | 11 | 377 |
| HPV18 | L2 | 8 | 105 |
| HPV18 | L2 | 9 | 105 |
| HPV18 | L2 | 10 | 105 |
| HPV18 | L2 | 8 | 406 |
| HPV18 | L2 | 11 | 406 |
| HPV18 | L2 | 10 | 262 |
| HPV18 | L2 | 8 | 304 |
| HPV18 | L2 | 10 | 304 |
| HPV18 | L2 | 9 | 425 |
| HPV18 | L2 | 8 | 38 |
| HPV18 | L2 | 11 | 261 |
| HPV18 | L2 | 8 | 154 |
| HPV18 | L2 | 8 | 136 |
| HPV18 | L2 | 9 | 136 |
| HPV18 | L2 | 8 | 410 |
| HPV18 | L2 | 11 | 410 |
| HPV18 | L2 | 9 | 135 |
| HPV18 | L2 | 10 | 135 |
| HPV18 | L2 | 10 | 388 |
| HPV18 | L2 | 11 | 293 |
| HPV18 | L2 | 10 | 217 |
| HPV18 | L2 | 8 | 80 |
| HPV18 | L2 | 9 | 176 |
| HPV18 | L2 | 11 | 176 |
| HPV18 | L2 | 10 | 221 |
| HPV18 | L2 | 8 | 236 |
| HPV18 | L2 | 8 | 92 |
| HPV18 | L2 | 9 | 140 |
| HPV18 | L2 | 11 | 140 |
| HPV18 | L2 | 9 | 104 |
| HPV18 | L2 | 10 | 104 |
| HPV18 | L2 | 11 | 104 |
| HPV18 | L2 | 9 | 113 |
| HPV18 | L2 | 11 | 113 |
| HPV18 | L2 | 11 | 387 |
| HPV18 | L2 | 11 | 81 |
| HPV18 | L2 | 9 | 91 |
| HPV18 | L2 | 8 | 31 |
| HPV18 | L2 | 9 | 31 |
| HPV18 | L2 | 10 | 31 |
| HPV18 | L2 | 11 | 31 |
| HPV18 | L2 | 10 | 112 |
| HPV18 | L2 | 8 | 351 |
| HPV18 | L2 | 9 | 351 |
| HPV18 | L2 | 11 | 351 |
| HPV18 | L2 | 8 | 332 |
| HPV18 | L2 | 10 | 332 |
| HPV18 | L2 | 11 | 332 |
| HPV18 | L2 | 11 | 427 |
| HPV18 | L2 | 10 | 71 |
| HPV18 | L2 | 11 | 71 |
| HPV18 | L2 | 9 | 436 |
| HPV18 | L2 | 8 | 400 |
| HPV18 | L2 | 11 | 400 |
| HPV31 | E1 | 9 | 296 |
| HPV31 | E1 | 11 | 296 |
| HPV31 | E1 | 8 | 219 |
| HPV31 | E1 | 9 | 219 |
| HPV31 | E1 | 10 | 219 |
| HPV31 | E1 | 8 | 297 |
| HPV31 | E1 | 10 | 297 |
| HPV31 | E1 | 10 | 185 |
| HPV31 | E1 | 10 | 111 |
| HPV31 | E1 | 11 | 111 |
| HPV31 | E1 | 9 | 519 |
| HPV31 | E1 | 8 | 68 |
| HPV31 | E1 | 9 | 439 |
| HPV31 | E1 | 10 | 533 |
| HPV31 | E1 | 11 | 533 |
| HPV31 | E1 | 9 | 298 |
| HPV31 | E1 | 9 | 186 |
| HPV31 | E1 | 10 | 66 |
| HPV31 | E1 | 8 | 72 |
| HPV31 | E1 | 10 | 72 |
| HPV31 | E1 | 11 | 72 |
| HPV31 | E1 | 10 | 360 |
| HPV31 | E1 | 9 | 504 |
| HPV31 | E1 | 11 | 22 |
| HPV31 | E1 | 10 | 81 |
| HPV31 | E1 | 10 | 370 |
| HPV31 | E1 | 8 | 263 |
| HPV31 | E1 | 11 | 263 |
| HPV31 | E1 | 8 | 113 |
| HPV31 | E1 | 9 | 113 |
| HPV31 | E1 | 10 | 452 |
| HPV31 | E1 | 8 | 279 |
| HPV31 | E1 | 9 | 279 |
| HPV31 | E1 | 9 | 239 |
| HPV31 | E1 | 10 | 239 |
| HPV31 | E1 | 9 | 284 |
| HPV31 | E1 | 8 | 213 |
| HPV31 | E1 | 11 | 213 |
| HPV31 | E1 | 8 | 217 |
| HPV31 | E1 | 10 | 217 |
| HPV31 | E1 | 11 | 217 |
| HPV31 | E1 | 10 | 100 |

TABLE VIII-continued

HLA-A2 Supermotif-Bearing Peptides

| 1 | 2 | 3 | 4 |
|---|---|---|---|
| HPV31 | E1 | 9 | 620 |
| HPV31 | E1 | 10 | 620 |
| HPV31 | E1 | 10 | 495 |
| HPV31 | E1 | 11 | 495 |
| HPV31 | E1 | 10 | 503 |
| HPV31 | E1 | 10 | 96 |
| HPV31 | E1 | 11 | 421 |
| HPV31 | E1 | 9 | 336 |
| HPV31 | E1 | 11 | 46 |
| HPV31 | E1 | 10 | 42 |
| HPV31 | E1 | 9 | 332 |
| HPV31 | E1 | 10 | 332 |
| HPV31 | E1 | 8 | 528 |
| HPV31 | E1 | 10 | 528 |
| HPV31 | E1 | 8 | 348 |
| HPV31 | E1 | 9 | 348 |
| HPV31 | E1 | 10 | 311 |
| HPV31 | E1 | 8 | 74 |
| HPV31 | E1 | 9 | 74 |
| HPV31 | E1 | 11 | 74 |
| HPV31 | E1 | 8 | 62 |
| HPV31 | E1 | 11 | 62 |
| HPV31 | E1 | 8 | 21 |
| HPV31 | E1 | 11 | 80 |
| HPV31 | E1 | 9 | 354 |
| HPV31 | E1 | 10 | 354 |
| HPV31 | E1 | 10 | 127 |
| HPV31 | E1 | 8 | 193 |
| HPV31 | E1 | 10 | 193 |
| HPV31 | E1 | 11 | 193 |
| HPV31 | E1 | 9 | 64 |
| HPV31 | E1 | 10 | 315 |
| HPV31 | E1 | 11 | 315 |
| HPV31 | E1 | 8 | 168 |
| HPV31 | E1 | 10 | 168 |
| HPV31 | E1 | 11 | 168 |
| HPV31 | E1 | 8 | 139 |
| HPV31 | E1 | 8 | 137 |
| HPV31 | E1 | 10 | 137 |
| HPV31 | E1 | 11 | 443 |
| HPV31 | E1 | 8 | 372 |
| HPV31 | E1 | 10 | 372 |
| HPV31 | E1 | 11 | 372 |
| HPV31 | E1 | 10 | 473 |
| HPV31 | E1 | 10 | 425 |
| HPV31 | E1 | 9 | 436 |
| HPV31 | E1 | 9 | 206 |
| HPV31 | E1 | 8 | 433 |
| HPV31 | E1 | 10 | 433 |
| HPV31 | E1 | 8 | 499 |
| HPV31 | E1 | 8 | 467 |
| HPV31 | E1 | 8 | 305 |
| HPV31 | E1 | 8 | 252 |
| HPV31 | E1 | 11 | 403 |
| HPV31 | E1 | 10 | 11 |
| HPV31 | E1 | 10 | 160 |
| HPV31 | E1 | 10 | 386 |
| HPV31 | E1 | 9 | 225 |
| HPV31 | E1 | 10 | 225 |
| HPV31 | E1 | 11 | 225 |
| HPV31 | E1 | 8 | 446 |
| HPV31 | E1 | 9 | 446 |
| HPV31 | E1 | 10 | 446 |
| HPV31 | E1 | 8 | 196 |
| HPV31 | E1 | 8 | 78 |
| HPV31 | E1 | 9 | 71 |
| HPV31 | E1 | 11 | 71 |
| HPV31 | E1 | 11 | 243 |
| HPV31 | E1 | 8 | 355 |
| HPV31 | E1 | 9 | 355 |
| HPV31 | E1 | 9 | 453 |
| HPV31 | E1 | 9 | 287 |
| HPV31 | E1 | 10 | 287 |
| HPV31 | E1 | 11 | 287 |
| HPV31 | E1 | 10 | 268 |
| HPV31 | E1 | 11 | 268 |
| HPV31 | E1 | 8 | 381 |
| HPV31 | E1 | 10 | 422 |
| HPV31 | E1 | 11 | 184 |
| HPV31 | E1 | 11 | 110 |
| HPV31 | E1 | 11 | 532 |
| HPV31 | E1 | 8 | 497 |
| HPV31 | E1 | 9 | 497 |
| HPV31 | E1 | 10 | 497 |
| HPV31 | E1 | 8 | 380 |
| HPV31 | E1 | 9 | 380 |
| HPV31 | E1 | 10 | 276 |
| HPV31 | E1 | 11 | 276 |
| HPV31 | E1 | 9 | 272 |
| HPV31 | E1 | 11 | 272 |
| HPV31 | E1 | 8 | 291 |
| HPV31 | E1 | 9 | 291 |
| HPV31 | E1 | 10 | 119 |
| HPV31 | E1 | 9 | 232 |
| HPV31 | E1 | 8 | 179 |
| HPV31 | E1 | 9 | 179 |
| HPV31 | E1 | 10 | 179 |
| HPV31 | E1 | 11 | 412 |
| HPV31 | E1 | 8 | 247 |
| HPV31 | E1 | 9 | 247 |
| HPV31 | E1 | 10 | 247 |
| HPV31 | E1 | 11 | 247 |
| HPV31 | E1 | 8 | 493 |
| HPV31 | E1 | 9 | 493 |
| HPV31 | E1 | 8 | 362 |
| HPV31 | E1 | 10 | 362 |
| HPV31 | E1 | 8 | 454 |
| HPV31 | E1 | 10 | 286 |
| HPV31 | E1 | 11 | 286 |
| HPV31 | E1 | 11 | 202 |
| HPV31 | E1 | 9 | 470 |
| HPV31 | E1 | 10 | 470 |
| HPV31 | E1 | 8 | 543 |
| HPV31 | E1 | 9 | 277 |
| HPV31 | E1 | 10 | 277 |
| HPV31 | E1 | 11 | 277 |
| HPV31 | E1 | 8 | 273 |
| HPV31 | E1 | 10 | 273 |
| HPV31 | E1 | 9 | 542 |
| HPV31 | E1 | 11 | 234 |
| HPV31 | E1 | 9 | 256 |
| HPV31 | E1 | 9 | 534 |
| HPV31 | E1 | 10 | 534 |
| HPV31 | E1 | 11 | 534 |
| HPV31 | E1 | 9 | 474 |
| HPV31 | E1 | 8 | 326 |
| HPV31 | E1 | 9 | 326 |
| HPV31 | E1 | 9 | 490 |
| HPV31 | E1 | 11 | 490 |
| HPV31 | E1 | 10 | 235 |
| HPV31 | E1 | 10 | 244 |
| HPV31 | E1 | 11 | 244 |
| HPV31 | E1 | 11 | 175 |
| HPV31 | E1 | 11 | 258 |
| HPV31 | E1 | 8 | 187 |
| HPV31 | E1 | 11 | 187 |
| HPV31 | E1 | 8 | 285 |
| HPV31 | E1 | 11 | 285 |
| HPV31 | E1 | 10 | 255 |
| HPV31 | E1 | 8 | 257 |
| HPV31 | E1 | 8 | 535 |
| HPV31 | E1 | 9 | 535 |
| HPV31 | E1 | 10 | 535 |
| HPV31 | E1 | 11 | 535 |
| HPV31 | E1 | 10 | 47 |
| HPV31 | E1 | 9 | 143 |
| HPV31 | E1 | 10 | 143 |
| HPV31 | E1 | 11 | 143 |
| HPV31 | E1 | 10 | 340 |
| HPV31 | E1 | 11 | 340 |

TABLE VIII-continued

HLA-A2 Supermotif-Bearing Peptides

| 1 | 2 | 3 | 4 |
|---|---|---|---|
| HPV31 | E1 | 11 | 549 |
| HPV31 | E1 | 8 | 518 |
| HPV31 | E1 | 10 | 518 |
| HPV31 | E1 | 8 | 173 |
| HPV31 | E1 | 9 | 308 |
| HPV31 | E1 | 8 | 104 |
| HPV31 | E1 | 9 | 104 |
| HPV31 | E1 | 11 | 104 |
| HPV31 | E1 | 8 | 59 |
| HPV31 | E1 | 10 | 59 |
| HPV31 | E1 | 11 | 59 |
| HPV31 | E1 | 9 | 135 |
| HPV31 | E1 | 10 | 135 |
| HPV31 | E1 | 9 | 460 |
| HPV31 | E1 | 11 | 460 |
| HPV31 | E1 | 9 | 55 |
| HPV31 | E1 | 11 | 55 |
| HPV31 | E1 | 9 | 4 |
| HPV31 | E1 | 9 | 492 |
| HPV31 | E1 | 10 | 492 |
| HPV31 | E1 | 8 | 541 |
| HPV31 | E1 | 10 | 541 |
| HPV31 | E1 | 9 | 93 |
| HPV31 | E1 | 8 | 170 |
| HPV31 | E1 | 9 | 170 |
| HPV31 | E1 | 11 | 170 |
| HPV31 | E1 | 10 | 524 |
| HPV31 | E1 | 11 | 524 |
| HPV31 | E1 | 9 | 60 |
| HPV31 | E1 | 10 | 60 |
| HPV31 | E1 | 10 | 378 |
| HPV31 | E1 | 11 | 378 |
| HPV31 | E1 | 9 | 67 |
| HPV31 | E1 | 8 | 430 |
| HPV31 | E1 | 10 | 430 |
| HPV31 | E1 | 11 | 430 |
| HPV31 | E1 | 9 | 361 |
| HPV31 | E1 | 11 | 361 |
| HPV31 | E1 | 8 | 536 |
| HPV31 | E1 | 9 | 536 |
| HPV31 | E1 | 10 | 536 |
| HPV31 | E1 | 8 | 399 |
| HPV31 | E1 | 10 | 142 |
| HPV31 | E1 | 11 | 142 |
| HPV31 | E1 | 11 | 339 |
| HPV31 | E1 | 9 | 429 |
| HPV31 | E1 | 11 | 429 |
| HPV31 | E1 | 11 | 141 |
| HPV31 | E1 | 11 | 323 |
| HPV31 | E1 | 8 | 145 |
| HPV31 | E1 | 9 | 145 |
| HPV31 | E1 | 8 | 83 |
| HPV31 | E1 | 10 | 176 |
| HPV31 | E1 | 11 | 176 |
| HPV31 | E1 | 9 | 394 |
| HPV31 | E1 | 8 | 267 |
| HPV31 | E1 | 11 | 267 |
| HPV31 | E1 | 9 | 398 |
| HPV31 | E1 | 10 | 303 |
| HPV31 | E1 | 8 | 595 |
| HPV31 | E1 | 10 | 438 |
| HPV31 | E1 | 8 | 526 |
| HPV31 | E1 | 9 | 526 |
| HPV31 | E1 | 10 | 526 |
| HPV31 | E1 | 8 | 246 |
| HPV31 | E1 | 9 | 246 |
| HPV31 | E1 | 10 | 246 |
| HPV31 | E1 | 11 | 246 |
| HPV31 | E1 | 10 | 469 |
| HPV31 | E1 | 11 | 469 |
| HPV31 | E1 | 11 | 377 |
| HPV31 | E1 | 11 | 294 |
| HPV31 | E1 | 8 | 211 |
| HPV31 | E1 | 9 | 211 |
| HPV31 | E1 | 10 | 211 |
| HPV31 | E1 | 11 | 616 |
| HPV31 | E1 | 10 | 295 |
| HPV31 | E1 | 9 | 120 |
| HPV31 | E1 | 8 | 65 |
| HPV31 | E1 | 11 | 65 |
| HPV31 | E1 | 9 | 269 |
| HPV31 | E1 | 10 | 269 |
| HPV31 | E1 | 8 | 233 |
| HPV31 | E1 | 10 | 152 |
| HPV31 | E1 | 9 | 387 |
| HPV31 | E1 | 8 | 333 |
| HPV31 | E1 | 9 | 333 |
| HPV31 | E1 | 11 | 151 |
| HPV31 | E1 | 8 | 505 |
| HPV31 | E1 | 8 | 226 |
| HPV31 | E1 | 9 | 226 |
| HPV31 | E1 | 10 | 226 |
| HPV31 | E1 | 10 | 324 |
| HPV31 | E1 | 11 | 324 |
| HPV31 | E1 | 9 | 218 |
| HPV31 | E1 | 10 | 218 |
| HPV31 | E1 | 11 | 218 |
| HPV31 | E1 | 8 | 227 |
| HPV31 | E1 | 9 | 227 |
| HPV31 | E1 | 10 | 23 |
| HPV31 | E1 | 11 | 84 |
| HPV31 | E1 | 9 | 177 |
| HPV31 | E1 | 10 | 177 |
| HPV31 | E1 | 11 | 177 |
| HPV31 | E1 | 9 | 325 |
| HPV31 | E1 | 10 | 325 |
| HPV31 | E1 | 8 | 349 |
| HPV31 | E1 | 11 | 254 |
| HPV31 | E1 | 8 | 144 |
| HPV31 | E1 | 9 | 144 |
| HPV31 | E1 | 10 | 144 |
| HPV31 | E1 | 9 | 82 |
| HPV31 | E1 | 9 | 341 |
| HPV31 | E1 | 10 | 341 |
| HPV31 | E1 | 11 | 223 |
| HPV31 | E1 | 8 | 343 |
| HPV31 | E1 | 8 | 319 |
| HPV31 | E1 | 9 | 405 |
| HPV31 | E1 | 8 | 489 |
| HPV31 | E1 | 10 | 489 |
| HPV31 | E1 | 10 | 481 |
| HPV31 | E1 | 11 | 359 |
| HPV31 | E1 | 9 | 511 |
| HPV31 | E1 | 10 | 511 |
| HPV31 | E1 | 8 | 558 |
| HPV31 | E1 | 10 | 558 |
| HPV31 | E1 | 11 | 515 |
| HPV31 | E1 | 10 | 428 |
| HPV31 | E1 | 10 | 19 |
| HPV31 | E1 | 9 | 89 |
| HPV31 | E2 | 8 | 277 |
| HPV31 | E2 | 10 | 277 |
| HPV31 | E2 | 11 | 277 |
| HPV31 | E2 | 9 | 278 |
| HPV31 | E2 | 10 | 278 |
| HPV31 | E2 | 8 | 72 |
| HPV31 | E2 | 10 | 72 |
| HPV31 | E2 | 11 | 72 |
| HPV31 | E2 | 8 | 338 |
| HPV31 | E2 | 10 | 338 |
| HPV31 | E2 | 8 | 229 |
| HPV31 | E2 | 11 | 229 |
| HPV31 | E2 | 9 | 69 |
| HPV31 | E2 | 10 | 69 |
| HPV31 | E2 | 11 | 69 |
| HPV31 | E2 | 9 | 61 |
| HPV31 | E2 | 10 | 61 |
| HPV31 | E2 | 8 | 291 |
| HPV31 | E2 | 10 | 239 |
| HPV31 | E2 | 8 | 286 |

TABLE VIII-continued

HLA-A2 Supermotif-Bearing Peptides

| 1 | 2 | 3 | 4 |
|---|---|---|---|
| HPV31 | E2 | 10 | 286 |
| HPV31 | E2 | 11 | 286 |
| HPV31 | E2 | 9 | 228 |
| HPV31 | E2 | 8 | 140 |
| HPV31 | E2 | 9 | 140 |
| HPV31 | E2 | 8 | 109 |
| HPV31 | E2 | 9 | 109 |
| HPV31 | E2 | 11 | 109 |
| HPV31 | E2 | 9 | 330 |
| HPV31 | E2 | 10 | 330 |
| HPV31 | E2 | 11 | 330 |
| HPV31 | E2 | 8 | 280 |
| HPV31 | E2 | 8 | 145 |
| HPV31 | E2 | 10 | 40 |
| HPV31 | E2 | 8 | 301 |
| HPV31 | E2 | 9 | 124 |
| HPV31 | E2 | 8 | 204 |
| HPV31 | E2 | 9 | 204 |
| HPV31 | E2 | 11 | 204 |
| HPV31 | E2 | 8 | 74 |
| HPV31 | E2 | 9 | 74 |
| HPV31 | E2 | 8 | 100 |
| HPV31 | E2 | 11 | 100 |
| HPV31 | E2 | 11 | 48 |
| HPV31 | E2 | 10 | 320 |
| HPV31 | E2 | 9 | 2 |
| HPV31 | E2 | 8 | 185 |
| HPV31 | E2 | 9 | 185 |
| HPV31 | E2 | 10 | 185 |
| HPV31 | E2 | 8 | 118 |
| HPV31 | E2 | 11 | 118 |
| HPV31 | E2 | 8 | 207 |
| HPV31 | E2 | 10 | 207 |
| HPV31 | E2 | 11 | 207 |
| HPV31 | E2 | 11 | 136 |
| HPV31 | E2 | 10 | 353 |
| HPV31 | E2 | 11 | 353 |
| HPV31 | E2 | 10 | 171 |
| HPV31 | E2 | 8 | 168 |
| HPV31 | E2 | 9 | 50 |
| HPV31 | E2 | 10 | 50 |
| HPV31 | E2 | 8 | 209 |
| HPV31 | E2 | 9 | 209 |
| HPV31 | E2 | 10 | 156 |
| HPV31 | E2 | 11 | 156 |
| HPV31 | E2 | 10 | 143 |
| HPV31 | E2 | 10 | 190 |
| HPV31 | E2 | 8 | 150 |
| HPV31 | E2 | 11 | 150 |
| HPV31 | E2 | 8 | 179 |
| HPV31 | E2 | 10 | 179 |
| HPV31 | E2 | 9 | 231 |
| HPV31 | E2 | 10 | 231 |
| HPV31 | E2 | 11 | 231 |
| HPV31 | E2 | 9 | 273 |
| HPV31 | E2 | 9 | 235 |
| HPV31 | E2 | 8 | 187 |
| HPV31 | E2 | 8 | 29 |
| HPV31 | E2 | 10 | 29 |
| HPV31 | E2 | 8 | 35 |
| HPV31 | E2 | 9 | 35 |
| HPV31 | E2 | 9 | 164 |
| HPV31 | E2 | 8 | 297 |
| HPV31 | E2 | 9 | 297 |
| HPV31 | E2 | 9 | 56 |
| HPV31 | E2 | 8 | 295 |
| HPV31 | E2 | 10 | 295 |
| HPV31 | E2 | 11 | 295 |
| HPV31 | E2 | 9 | 304 |
| HPV31 | E2 | 8 | 165 |
| HPV31 | E2 | 11 | 165 |
| HPV31 | E2 | 8 | 210 |
| HPV31 | E2 | 11 | 210 |
| HPV31 | E2 | 9 | 339 |
| HPV31 | E2 | 8 | 66 |
| HPV31 | E2 | 10 | 66 |
| HPV31 | E2 | 8 | 68 |
| HPV31 | E2 | 10 | 68 |
| HPV31 | E2 | 11 | 68 |
| HPV31 | E2 | 10 | 45 |
| HPV31 | E2 | 8 | 358 |
| HPV31 | E2 | 10 | 358 |
| HPV31 | E2 | 8 | 260 |
| HPV31 | E2 | 11 | 260 |
| HPV31 | E2 | 8 | 213 |
| HPV31 | E2 | 9 | 213 |
| HPV31 | E2 | 10 | 213 |
| HPV31 | E2 | 10 | 316 |
| HPV31 | E2 | 11 | 226 |
| HPV31 | E2 | 10 | 261 |
| HPV31 | E2 | 8 | 42 |
| HPV31 | E2 | 10 | 42 |
| HPV31 | E2 | 8 | 70 |
| HPV31 | E2 | 9 | 70 |
| HPV31 | E2 | 10 | 70 |
| HPV31 | E2 | 8 | 75 |
| HPV31 | E2 | 11 | 75 |
| HPV31 | E2 | 8 | 103 |
| HPV31 | E2 | 8 | 78 |
| HPV31 | E2 | 9 | 77 |
| HPV31 | E2 | 8 | 94 |
| HPV31 | E2 | 10 | 94 |
| HPV31 | E2 | 11 | 94 |
| HPV31 | E2 | 9 | 337 |
| HPV31 | E2 | 11 | 337 |
| HPV31 | E2 | 10 | 303 |
| HPV31 | E2 | 10 | 282 |
| HPV31 | E2 | 11 | 282 |
| HPV31 | E2 | 10 | 84 |
| HPV31 | E2 | 11 | 84 |
| HPV31 | E2 | 8 | 254 |
| HPV31 | E2 | 9 | 254 |
| HPV31 | E2 | 11 | 127 |
| HPV31 | E2 | 19 | 219 |
| HPV31 | E2 | 11 | 219 |
| HPV31 | E2 | 8 | 355 |
| HPV31 | E2 | 9 | 355 |
| HPV31 | E2 | 11 | 355 |
| HPV31 | E2 | 10 | 361 |
| HPV31 | E2 | 11 | 361 |
| HPV31 | E2 | 8 | 9 |
| HPV31 | E2 | 8 | 60 |
| HPV31 | E2 | 10 | 60 |
| HPV31 | E2 | 11 | 60 |
| HPV31 | E2 | 9 | 290 |
| HPV31 | E2 | 9 | 294 |
| HPV31 | E2 | 11 | 294 |
| HPV31 | E2 | 8 | 215 |
| HPV31 | E2 | 11 | 106 |
| HPV31 | E2 | 8 | 71 |
| HPV31 | E2 | 9 | 71 |
| HPV31 | E2 | 11 | 71 |
| HPV31 | E2 | 9 | 317 |
| HPV31 | E2 | 10 | 76 |
| HPV31 | E2 | 9 | 95 |
| HPV31 | E2 | 10 | 95 |
| HPV31 | E2 | 11 | 95 |
| HPV31 | E2 | 9 | 283 |
| HPV31 | E2 | 10 | 283 |
| HPV31 | E2 | 11 | 283 |
| HPV31 | E2 | 8 | 96 |
| HPV31 | E2 | 9 | 96 |
| HPV31 | E2 | 10 | 96 |
| HPV31 | E2 | 9 | 191 |
| HPV31 | E2 | 10 | 151 |
| HPV31 | E2 | 9 | 321 |
| HPV31 | E2 | 11 | 321 |
| HPV31 | E2 | 8 | 57 |
| HPV31 | E2 | 11 | 57 |
| HPV31 | E2 | 11 | 238 |

TABLE VIII-continued

HLA-A2 Supermotif-Bearing Peptides

| 1 | 2 | 3 | 4 |
|---|---|---|---|
| HPV31 | E2 | 8 | 285 |
| HPV31 | E2 | 9 | 285 |
| HPV31 | E2 | 11 | 285 |
| HPV31 | E2 | 10 | 37 |
| HPV31 | E2 | 9 | 7 |
| HPV31 | E2 | 10 | 7 |
| HPV31 | E2 | 8 | 311 |
| HPV31 | E2 | 9 | 247 |
| HPV31 | E2 | 9 | 276 |
| HPV31 | E2 | 11 | 276 |
| HPV31 | E2 | 9 | 53 |
| HPV31 | E2 | 10 | 53 |
| HPV31 | E2 | 8 | 98 |
| HPV31 | E2 | 10 | 98 |
| HPV31 | E2 | 9 | 348 |
| HPV31 | E2 | 10 | 348 |
| HPV31 | E2 | 11 | 5 |
| HPV31 | E2 | 9 | 346 |
| HPV31 | E2 | 11 | 346 |
| HPV31 | E2 | 8 | 324 |
| HPV31 | E2 | 9 | 266 |
| HPV31 | E2 | 10 | 266 |
| HPV31 | E2 | 8 | 198 |
| HPV31 | E2 | 11 | 198 |
| HPV31 | E2 | 9 | 269 |
| HPV31 | E2 | 10 | 269 |
| HPV31 | E2 | 11 | 269 |
| HPV31 | E2 | 8 | 63 |
| HPV31 | E2 | 10 | 63 |
| HPV31 | E2 | 11 | 63 |
| HPV31 | E2 | 8 | 364 |
| HPV31 | E2 | 9 | 364 |
| HPV31 | E2 | 8 | 3 |
| HPV31 | E2 | 10 | 128 |
| HPV31 | E2 | 9 | 93 |
| HPV31 | E2 | 11 | 93 |
| HPV31 | E2 | 11 | 292 |
| HPV31 | E2 | 9 | 221 |
| HPV31 | E2 | 10 | 221 |
| HPV31 | E2 | 9 | 240 |
| HPV31 | E2 | 8 | 220 |
| HPV31 | E2 | 10 | 220 |
| HPV31 | E2 | 11 | 220 |
| HPV31 | E2 | 10 | 116 |
| HPV31 | E2 | 8 | 356 |
| HPV31 | E2 | 10 | 356 |
| HPV31 | E2 | 9 | 362 |
| HPV31 | E2 | 10 | 362 |
| HPV31 | E2 | 11 | 362 |
| HPV31 | E2 | 8 | 274 |
| HPV31 | E2 | 11 | 274 |
| HPV31 | E2 | 8 | 192 |
| HPV31 | E2 | 9 | 41 |
| HPV31 | E2 | 11 | 41 |
| HPV31 | E2 | 10 | 119 |
| HPV31 | E2 | 11 | 119 |
| HPV31 | E2 | 10 | 211 |
| HPV31 | E2 | 11 | 211 |
| HPV31 | E2 | 8 | 340 |
| HPV31 | E2 | 11 | 147 |
| HPV31 | E2 | 10 | 58 |
| HPV31 | E2 | 11 | 328 |
| HPV31 | E2 | 8 | 92 |
| HPV31 | E2 | 10 | 92 |
| HPV31 | E2 | 11 | 344 |
| HPV31 | E2 | 9 | 138 |
| HPV31 | E2 | 10 | 138 |
| HPV31 | E2 | 11 | 138 |
| HPV31 | E2 | 9 | 102 |
| HPV31 | E2 | 9 | 131 |
| HPV31 | E2 | 11 | 131 |
| HPV31 | E2 | 11 | 115 |
| HPV31 | E2 | 8 | 159 |
| HPV31 | E2 | 11 | 159 |
| HPV31 | E5 | 8 | 40 |
| HPV31 | E5 | 9 | 40 |
| HPV31 | E5 | 10 | 40 |
| HPV31 | E5 | 10 | 53 |
| HPV31 | E5 | 9 | 61 |
| HPV31 | E5 | 11 | 61 |
| HPV31 | E5 | 8 | 26 |
| HPV31 | E5 | 9 | 26 |
| HPV31 | E5 | 11 | 26 |
| HPV31 | E5 | 8 | 20 |
| HPV31 | E5 | 9 | 20 |
| HPV31 | E5 | 10 | 20 |
| HPV31 | E5 | 9 | 3 |
| HPV31 | E5 | 10 | 3 |
| HPV31 | E5 | 11 | 3 |
| HPV31 | E5 | 8 | 66 |
| HPV31 | E5 | 9 | 66 |
| HPV31 | E5 | 11 | 66 |
| HPV31 | E5 | 8 | 15 |
| HPV31 | E5 | 9 | 15 |
| HPV31 | E5 | 11 | 15 |
| HPV31 | E5 | 9 | 24 |
| HPV31 | E5 | 10 | 24 |
| HPV31 | E5 | 11 | 24 |
| HPV31 | E5 | 10 | 72 |
| HPV31 | E5 | 11 | 52 |
| HPV31 | E5 | 10 | 48 |
| HPV31 | E5 | 8 | 46 |
| HPV31 | E5 | 9 | 46 |
| HPV31 | E5 | 11 | 11 |
| HPV31 | E5 | 8 | 45 |
| HPV31 | E5 | 9 | 45 |
| HPV31 | E5 | 10 | 45 |
| HPV31 | E5 | 8 | 16 |
| HPV31 | E5 | 10 | 16 |
| HPV31 | E5 | 8 | 22 |
| HPV31 | E5 | 11 | 22 |
| HPV31 | E5 | 8 | 44 |
| HPV31 | E5 | 9 | 44 |
| HPV31 | E5 | 10 | 44 |
| HPV31 | E5 | 11 | 44 |
| HPV31 | E5 | 9 | 43 |
| HPV31 | E5 | 10 | 43 |
| HPV31 | E5 | 11 | 43 |
| HPV31 | E5 | 8 | 42 |
| HPV31 | E5 | 10 | 42 |
| HPV31 | E5 | 11 | 42 |
| HPV31 | E5 | 8 | 27 |
| HPV31 | E5 | 10 | 27 |
| HPV31 | E5 | 9 | 32 |
| HPV31 | E5 | 10 | 32 |
| HPV31 | E5 | 11 | 32 |
| HPV31 | E5 | 8 | 1 |
| HPV31 | E5 | 9 | 1 |
| HPV31 | E5 | 11 | 1 |
| HPV31 | E5 | 8 | 5 |
| HPV31 | E5 | 9 | 5 |
| HPV31 | E5 | 9 | 70 |
| HPV31 | E5 | 9 | 56 |
| HPV31 | E5 | 10 | 56 |
| HPV31 | E5 | 8 | 31 |
| HPV31 | E5 | 10 | 31 |
| HPV31 | E5 | 11 | 31 |
| HPV31 | E5 | 8 | 10 |
| HPV31 | E5 | 10 | 7 |
| HPV31 | E5 | 11 | 7 |
| HPV31 | E5 | 8 | 35 |
| HPV31 | E5 | 9 | 35 |
| HPV31 | E5 | 10 | 35 |
| HPV31 | E5 | 11 | 35 |
| HPV31 | E5 | 8 | 37 |
| HPV31 | E5 | 9 | 37 |
| HPV31 | E5 | 10 | 37 |
| HPV31 | E5 | 11 | 37 |
| HPV31 | E5 | 8 | 41 |
| HPV31 | E5 | 9 | 41 |

TABLE VIII-continued

HLA-A2 Supermotif-Bearing Peptides

| 1 | 2 | 3 | 4 |
|---|---|---|---|
| HPV31 | E5 | 11 | 41 |
| HPV31 | E5 | 9 | 8 |
| HPV31 | E5 | 10 | 8 |
| HPV31 | E5 | 9 | 73 |
| HPV31 | E5 | 8 | 47 |
| HPV31 | E5 | 11 | 47 |
| HPV31 | E5 | 9 | 28 |
| HPV31 | E5 | 11 | 28 |
| HPV31 | E5 | 10 | 12 |
| HPV31 | E5 | 11 | 12 |
| HPV31 | E5 | 8 | 21 |
| HPV31 | E5 | 9 | 21 |
| HPV31 | E5 | 8 | 33 |
| HPV31 | E5 | 9 | 33 |
| HPV31 | E5 | 10 | 33 |
| HPV31 | E5 | 11 | 33 |
| HPV31 | E5 | 8 | 64 |
| HPV31 | E5 | 10 | 64 |
| HPV31 | E5 | 11 | 64 |
| HPV31 | E5 | 8 | 50 |
| HPV31 | E5 | 8 | 39 |
| HPV31 | E5 | 9 | 39 |
| HPV31 | E5 | 10 | 39 |
| HPV31 | E5 | 11 | 39 |
| HPV31 | E5 | 9 | 68 |
| HPV31 | E5 | 11 | 68 |
| HPV31 | E5 | 9 | 63 |
| HPV31 | E5 | 11 | 63 |
| HPV31 | E6 | 9 | 18 |
| HPV31 | E6 | 11 | 18 |
| HPV31 | E6 | 10 | 136 |
| HPV31 | E6 | 8 | 103 |
| HPV31 | E6 | 8 | 66 |
| HPV31 | E6 | 11 | 63 |
| HPV31 | E6 | 8 | 30 |
| HPV31 | E6 | 9 | 30 |
| HPV31 | E6 | 11 | 30 |
| HPV31 | E6 | 8 | 98 |
| HPV31 | E6 | 10 | 49 |
| HPV31 | E6 | 8 | 57 |
| HPV31 | E6 | 11 | 57 |
| HPV31 | E6 | 9 | 20 |
| HPV31 | E6 | 8 | 14 |
| HPV31 | E6 | 8 | 39 |
| HPV31 | E6 | 10 | 39 |
| HPV31 | E6 | 8 | 41 |
| HPV31 | E6 | 10 | 41 |
| HPV31 | E6 | 11 | 41 |
| HPV31 | E6 | 8 | 45 |
| HPV31 | E6 | 9 | 45 |
| HPV31 | E6 | 10 | 95 |
| HPV31 | E6 | 11 | 95 |
| HPV31 | E6 | 8 | 35 |
| HPV31 | E6 | 9 | 35 |
| HPV31 | E6 | 8 | 85 |
| HPV31 | E6 | 11 | 118 |
| HPV31 | E6 | 9 | 137 |
| HPV31 | E6 | 11 | 137 |
| HPV31 | E6 | 11 | 52 |
| HPV31 | E6 | 8 | 11 |
| HPV31 | E6 | 9 | 11 |
| HPV31 | E6 | 11 | 11 |
| HPV31 | E6 | 10 | 90 |
| HPV31 | E6 | 11 | 90 |
| HPV31 | E6 | 11 | 100 |
| HPV31 | E6 | 10 | 37 |
| HPV31 | E6 | 9 | 50 |
| HPV31 | E6 | 9 | 91 |
| HPV31 | E6 | 10 | 91 |
| HPV31 | E6 | 11 | 91 |
| HPV31 | E6 | 11 | 127 |
| HPV31 | E6 | 8 | 5 |
| HPV31 | E6 | 11 | 5 |
| HPV31 | E6 | 11 | 109 |
| HPV31 | E6 | 8 | 36 |
| HPV31 | E6 | 11 | 36 |
| HPV31 | E6 | 11 | 27 |
| HPV31 | E6 | 10 | 17 |
| HPV31 | E6 | 10 | 82 |
| HPV31 | E6 | 11 | 82 |
| HPV31 | E6 | 8 | 51 |
| HPV31 | E6 | 10 | 87 |
| HPV31 | E6 | 11 | 86 |
| HPV31 | E6 | 9 | 42 |
| HPV31 | E6 | 10 | 42 |
| HPV31 | E6 | 11 | 42 |
| HPV31 | E7 | 10 | 19 |
| HPV31 | E7 | 9 | 59 |
| HPV31 | E7 | 11 | 59 |
| HPV31 | E7 | 9 | 68 |
| HPV31 | E7 | 11 | 68 |
| HPV31 | E7 | 8 | 75 |
| HPV31 | E7 | 9 | 75 |
| HPV31 | E7 | 10 | 75 |
| HPV31 | E7 | 8 | 21 |
| HPV31 | E7 | 9 | 14 |
| HPV31 | E7 | 8 | 48 |
| HPV31 | E7 | 9 | 48 |
| HPV31 | E7 | 10 | 36 |
| HPV31 | E7 | 11 | 18 |
| HPV31 | E7 | 9 | 81 |
| HPV31 | E7 | 10 | 81 |
| HPV31 | E7 | 9 | 4 |
| HPV31 | E7 | 10 | 4 |
| HPV31 | E7 | 9 | 88 |
| HPV31 | E7 | 11 | 88 |
| HPV31 | E7 | 8 | 89 |
| HPV31 | E7 | 10 | 89 |
| HPV31 | E7 | 11 | 54 |
| HPV31 | E7 | 8 | 82 |
| HPV31 | E7 | 9 | 82 |
| HPV31 | E7 | 8 | 83 |
| HPV31 | E7 | 8 | 8 |
| HPV31 | E7 | 11 | 79 |
| HPV31 | E7 | 8 | 15 |
| HPV31 | E7 | 9 | 41 |
| HPV31 | E7 | 8 | 6 |
| HPV31 | E7 | 10 | 6 |
| HPV31 | E7 | 11 | 44 |
| HPV31 | E7 | 11 | 27 |
| HPV31 | E7 | 10 | 73 |
| HPV31 | E7 | 11 | 73 |
| HPV31 | E7 | 8 | 77 |
| HPV31 | E7 | 9 | 66 |
| HPV31 | E7 | 11 | 66 |
| HPV31 | E7 | 10 | 63 |
| HPV31 | E7 | 8 | 71 |
| HPV31 | E7 | 9 | 71 |
| HPV31 | E7 | 9 | 7 |
| HPV31 | E7 | 9 | 64 |
| HPV31 | E7 | 11 | 64 |
| HPV31 | E7 | 8 | 72 |
| HPV31 | E7 | 11 | 72 |
| HPV31 | E7 | 9 | 37 |
| HPV31 | E7 | 8 | 12 |
| HPV31 | E7 | 9 | 12 |
| HPV31 | E7 | 11 | 12 |
| HPV31 | E7 | 8 | 69 |
| HPV31 | E7 | 10 | 69 |
| HPV31 | E7 | 11 | 69 |
| HPV31 | E7 | 10 | 55 |
| HPV31 | E7 | 11 | 55 |
| HPV31 | E7 | 9 | 11 |
| HPV31 | E7 | 10 | 11 |
| HPV31 | L1 | 8 | 347 |
| HPV31 | L1 | 9 | 347 |
| HPV31 | L1 | 8 | 348 |
| HPV31 | L1 | 10 | 398 |
| HPV31 | L1 | 11 | 398 |
| HPV31 | L1 | 8 | 426 |

TABLE VIII-continued

HLA-A2 Supermotif-Bearing Peptides

| 1 | 2 | 3 | 4 |
|---|---|---|---|
| HPV31 | L1 | 10 | 180 |
| HPV31 | L1 | 9 | 213 |
| HPV31 | L1 | 11 | 213 |
| HPV31 | L1 | 10 | 208 |
| HPV31 | L1 | 8 | 317 |
| HPV31 | L1 | 10 | 305 |
| HPV31 | L1 | 11 | 285 |
| HPV31 | L1 | 8 | 9 |
| HPV31 | L1 | 10 | 9 |
| HPV31 | L1 | 9 | 346 |
| HPV31 | L1 | 10 | 346 |
| HPV31 | L1 | 9 | 147 |
| HPV31 | L1 | 11 | 147 |
| HPV31 | L1 | 9 | 158 |
| HPV31 | L1 | 11 | 304 |
| HPV31 | L1 | 9 | 387 |
| HPV31 | L1 | 8 | 372 |
| HPV31 | L1 | 11 | 372 |
| HPV31 | L1 | 10 | 275 |
| HPV31 | L1 | 11 | 275 |
| HPV31 | L1 | 9 | 200 |
| HPV31 | L1 | 10 | 200 |
| HPV31 | L1 | 10 | 461 |
| HPV31 | L1 | 11 | 461 |
| HPV31 | L1 | 9 | 129 |
| HPV31 | L1 | 10 | 203 |
| HPV31 | L1 | 11 | 203 |
| HPV31 | L1 | 8 | 216 |
| HPV31 | L1 | 10 | 216 |
| HPV31 | L1 | 9 | 88 |
| HPV31 | L1 | 8 | 336 |
| HPV31 | L1 | 10 | 336 |
| HPV31 | L1 | 10 | 417 |
| HPV31 | L1 | 11 | 417 |
| HPV31 | L1 | 9 | 8 |
| HPV31 | L1 | 11 | 8 |
| HPV31 | L1 | 8 | 95 |
| HPV31 | L1 | 10 | 95 |
| HPV31 | L1 | 8 | 107 |
| HPV31 | L1 | 10 | 107 |
| HPV31 | L1 | 10 | 449 |
| HPV31 | L1 | 8 | 375 |
| HPV31 | L1 | 9 | 375 |
| HPV31 | L1 | 10 | 375 |
| HPV31 | L1 | 9 | 469 |
| HPV31 | L1 | 8 | 377 |
| HPV31 | L1 | 10 | 377 |
| HPV31 | L1 | 11 | 211 |
| HPV31 | L1 | 11 | 257 |
| HPV31 | L1 | 8 | 421 |
| HPV31 | L1 | 8 | 331 |
| HPV31 | L1 | 11 | 331 |
| HPV31 | L1 | 8 | 207 |
| HPV31 | L1 | 11 | 207 |
| HPV31 | L1 | 8 | 323 |
| HPV31 | L1 | 10 | 323 |
| HPV31 | L1 | 11 | 323 |
| HPV31 | L1 | 8 | 117 |
| HPV31 | L1 | 10 | 105 |
| HPV31 | L1 | 9 | 68 |
| HPV31 | L1 | 11 | 68 |
| HPV31 | L1 | 10 | 406 |
| HPV31 | L1 | 8 | 111 |
| HPV31 | L1 | 1 | 141 |
| HPV31 | L1 | 10 | 141 |
| HPV31 | L1 | 9 | 266 |
| HPV31 | L1 | 11 | 266 |
| HPV31 | L1 | 9 | 115 |
| HPV31 | L1 | 10 | 115 |
| HPV31 | L1 | 8 | 36 |
| HPV31 | L1 | 9 | 36 |
| HPV31 | L1 | 10 | 36 |
| HPV31 | L1 | 9 | 399 |
| HPV31 | L1 | 10 | 399 |
| HPV31 | L1 | 11 | 399 |
| HPV31 | L1 | 8 | 388 |
| HPV31 | L1 | 11 | 388 |
| HPV31 | L1 | 9 | 196 |
| HPV31 | L1 | 8 | 382 |
| HPV31 | L1 | 9 | 382 |
| HPV31 | L1 | 11 | 382 |
| HPV31 | L1 | 9 | 181 |
| HPV31 | L1 | 11 | 181 |
| HPV31 | L1 | 9 | 61 |
| HPV31 | L1 | 10 | 482 |
| HPV31 | L1 | 8 | 381 |
| HPV31 | L1 | 9 | 381 |
| HPV31 | L1 | 10 | 381 |
| HPV31 | L1 | 10 | 60 |
| HPV31 | L1 | 10 | 237 |
| HPV31 | L1 | 11 | 237 |
| HPV31 | L1 | 8 | 153 |
| HPV31 | L1 | 9 | 65 |
| HPV31 | L1 | 9 | 20 |
| HPV31 | L1 | 10 | 20 |
| HPV31 | L1 | 9 | 287 |
| HPV31 | L1 | 8 | 159 |
| HPV31 | L1 | 8 | 123 |
| HPV31 | L1 | 8 | 470 |
| HPV31 | L1 | 11 | 42 |
| HPV31 | L1 | 8 | 214 |
| HPV31 | L1 | 10 | 214 |
| HPV31 | L1 | 10 | 373 |
| HPV31 | L1 | 11 | 373 |
| HPV31 | L1 | 8 | 69 |
| HPV31 | L1 | 10 | 69 |
| HPV31 | L1 | 9 | 407 |
| HPV31 | L1 | 10 | 43 |
| HPV31 | L1 | 8 | 99 |
| HPV31 | L1 | 10 | 99 |
| HPV31 | L1 | 11 | 314 |
| HPV31 | L1 | 10 | 389 |
| HPV31 | L1 | 11 | 389 |
| HPV31 | L1 | 9 | 238 |
| HPV31 | L1 | 10 | 238 |
| HPV31 | L1 | 8 | 201 |
| HPV31 | L1 | 9 | 201 |
| HPV31 | L1 | 8 | 300 |
| HPV31 | L1 | 11 | 179 |
| HPV31 | L1 | 9 | 32 |
| HPV31 | L1 | 11 | 32 |
| HPV31 | L1 | 8 | 451 |
| HPV31 | L1 | 10 | 451 |
| HPV31 | L1 | 8 | 342 |
| HPV31 | L1 | 9 | 342 |
| HPV31 | L1 | 8 | 328 |
| HPV31 | L1 | 10 | 328 |
| HPV31 | L1 | 11 | 328 |
| HPV31 | L1 | 10 | 220 |
| HPV31 | L1 | 11 | 397 |
| HPV31 | L1 | 8 | 222 |
| HPV31 | L1 | 8 | 188 |
| HPV31 | L1 | 9 | 188 |
| HPV31 | L1 | 8 | 464 |
| HPV31 | L1 | 10 | 464 |
| HPV31 | L1 | 11 | 113 |
| HPV31 | L1 | 9 | 122 |
| HPV31 | L1 | 8 | 294 |
| HPV31 | L1 | 9 | 294 |
| HPV31 | L1 | 8 | 15 |
| HPV31 | L1 | 10 | 15 |
| HPV31 | L1 | 8 | 17 |
| HPV31 | L1 | 8 | 425 |
| HPV31 | L1 | 9 | 425 |
| HPV31 | L1 | 9 | 306 |
| HPV31 | L1 | 9 | 378 |
| HPV31 | L1 | 11 | 378 |
| HPV31 | L1 | 11 | 156 |
| HPV31 | L1 | 9 | 329 |
| HPV31 | L1 | 10 | 329 |

TABLE VIII-continued

HLA-A2 Supermotif-Bearing Peptides

| 1 | 2 | 3 | 4 |
|---|---|---|---|
| HPV31 | L1 | 9 | 316 |
| HPV31 | L1 | 8 | 476 |
| HPV31 | L1 | 9 | 98 |
| HPV31 | L1 | 11 | 98 |
| HPV31 | L1 | 8 | 30 |
| HPV31 | L1 | 11 | 30 |
| HPV31 | L1 | 8 | 385 |
| HPV31 | L1 | 11 | 385 |
| HPV31 | L1 | 9 | 457 |
| HPV31 | L1 | 8 | 487 |
| HPV31 | L1 | 9 | 487 |
| HPV31 | L1 | 11 | 487 |
| HPV31 | L1 | 8 | 490 |
| HPV31 | L1 | 9 | 228 |
| HPV31 | L1 | 11 | 228 |
| HPV31 | L1 | 11 | 51 |
| HPV31 | L1 | 9 | 414 |
| HPV31 | L1 | 10 | 414 |
| HPV31 | L1 | 8 | 2 |
| HPV31 | L1 | 9 | 2 |
| HPV31 | L1 | 10 | 2 |
| HPV31 | L1 | 9 | 149 |
| HPV31 | L1 | 11 | 149 |
| HPV31 | L1 | 9 | 299 |
| HPV31 | L1 | 9 | 424 |
| HPV31 | L1 | 10 | 424 |
| HPV31 | L1 | 9 | 283 |
| HPV31 | L1 | 9 | 23 |
| HPV31 | L1 | 11 | 23 |
| HPV31 | L1 | 8 | 340 |
| HPV31 | L1 | 9 | 340 |
| HPV31 | L1 | 10 | 340 |
| HPV31 | L1 | 11 | 340 |
| HPV31 | L1 | 11 | 492 |
| HPV31 | L1 | 11 | 290 |
| HPV31 | L1 | 11 | 344 |
| HPV31 | L1 | 8 | 194 |
| HPV31 | L1 | 9 | 194 |
| HPV31 | L1 | 11 | 194 |
| HPV31 | L1 | 8 | 271 |
| HPV31 | L1 | 10 | 212 |
| HPV31 | L1 | 8 | 284 |
| HPV31 | L1 | 10 | 286 |
| HPV31 | L1 | 11 | 246 |
| HPV31 | L1 | 8 | 383 |
| HPV31 | L1 | 10 | 383 |
| HPV31 | L1 | 9 | 96 |
| HPV31 | L1 | 11 | 96 |
| HPV31 | L1 | 9 | 494 |
| HPV31 | L1 | 8 | 408 |
| HPV31 | L1 | 11 | 408 |
| HPV31 | L1 | 9 | 337 |
| HPV31 | L1 | 11 | 337 |
| HPV31 | L1 | 10 | 493 |
| HPV31 | L1 | 8 | 267 |
| HPV31 | L1 | 10 | 267 |
| HPV31 | L1 | 9 | 44 |
| HPV31 | L1 | 9 | 333 |
| HPV31 | L1 | 11 | 333 |
| HPV31 | L1 | 9 | 10 |
| HPV31 | L1 | 8 | 239 |
| HPV31 | L1 | 9 | 239 |
| HPV31 | L1 | 8 | 195 |
| HPV31 | L1 | 10 | 195 |
| HPV31 | L1 | 10 | 28 |
| HPV31 | L1 | 11 | 422 |
| HPV31 | L1 | 10 | 332 |
| HPV31 | L1 | 8 | 334 |
| HPV31 | L1 | 10 | 334 |
| HPV31 | L1 | 8 | 62 |
| HPV31 | L1 | 8 | 21 |
| HPV31 | L1 | 9 | 21 |
| HPV31 | L1 | 11 | 21 |
| HPV31 | L1 | 8 | 101 |
| HPV31 | L1 | 8 | 391 |
| HPV31 | L1 | 9 | 391 |
| HPV31 | L1 | 10 | 391 |
| HPV31 | L1 | 8 | 277 |
| HPV31 | L1 | 9 | 277 |
| HPV31 | L1 | 10 | 277 |
| HPV31 | L1 | 11 | 277 |
| HPV31 | L1 | 10 | 12 |
| HPV31 | L1 | 11 | 12 |
| HPV31 | L1 | 10 | 364 |
| HPV31 | L1 | 9 | 250 |
| HPV31 | L1 | 8 | 445 |
| HPV31 | L1 | 11 | 27 |
| HPV31 | L2 | 9 | 24 |
| HPV31 | L2 | 10 | 24 |
| HPV31 | L2 | 8 | 143 |
| HPV31 | L2 | 10 | 143 |
| HPV31 | L2 | 8 | 281 |
| HPV31 | L2 | 8 | 286 |
| HPV31 | L2 | 9 | 286 |
| HPV31 | L2 | 9 | 367 |
| HPV31 | L2 | 10 | 367 |
| HPV31 | L2 | 11 | 367 |
| HPV31 | L2 | 10 | 15 |
| HPV31 | L2 | 11 | 15 |
| HPV31 | L2 | 8 | 226 |
| HPV31 | L2 | 11 | 226 |
| HPV31 | L2 | 9 | 135 |
| HPV31 | L2 | 10 | 135 |
| HPV31 | L2 | 11 | 135 |
| HPV31 | L2 | 11 | 342 |
| HPV31 | L2 | 8 | 376 |
| HPV31 | L2 | 10 | 376 |
| HPV31 | L2 | 8 | 382 |
| HPV31 | L2 | 10 | 382 |
| HPV31 | L2 | 11 | 382 |
| HPV31 | L2 | 8 | 133 |
| HPV31 | L2 | 9 | 133 |
| HPV31 | L2 | 11 | 133 |
| HPV31 | L2 | 9 | 278 |
| HPV31 | L2 | 10 | 278 |
| HPV31 | L2 | 11 | 278 |
| HPV31 | L2 | 10 | 400 |
| HPV31 | L2 | 8 | 322 |
| HPV31 | L2 | 9 | 354 |
| HPV31 | L2 | 10 | 354 |
| HPV31 | L2 | 9 | 43 |
| HPV31 | L2 | 11 | 43 |
| HPV31 | L2 | 8 | 358 |
| HPV31 | L2 | 10 | 358 |
| HPV31 | L2 | 11 | 358 |
| HPV31 | L2 | 8 | 364 |
| HPV31 | L2 | 9 | 139 |
| HPV31 | L2 | 10 | 139 |
| HPV31 | L2 | 8 | 116 |
| HPV31 | L2 | 9 | 31 |
| HPV31 | L2 | 10 | 31 |
| HPV31 | L2 | 11 | 31 |
| HPV31 | L2 | 10 | 84 |
| HPV31 | L2 | 8 | 190 |
| HPV31 | L2 | 9 | 190 |
| HPV31 | L2 | 11 | 190 |
| HPV31 | L2 | 9 | 334 |
| HPV31 | L2 | 10 | 334 |
| HPV31 | L2 | 11 | 334 |
| HPV31 | L2 | 8 | 171 |
| HPV31 | L2 | 9 | 253 |
| HPV31 | L2 | 10 | 196 |
| HPV31 | L2 | 11 | 196 |
| HPV31 | L2 | 11 | 276 |
| HPV31 | L2 | 8 | 237 |
| HPV31 | L2 | 9 | 237 |
| HPV31 | L2 | 10 | 237 |
| HPV31 | L2 | 11 | 158 |
| HPV31 | L2 | 8 | 459 |
| HPV31 | L2 | 8 | 361 |

TABLE VIII-continued

HLA-A2 Supermotif-Bearing Peptides

| 1 | 2 | 3 | 4 |
|---|---|---|---|
| HPV31 | L2 | 11 | 361 |
| HPV31 | L2 | 9 | 433 |
| HPV31 | L2 | 11 | 118 |
| HPV31 | L2 | 10 | 314 |
| HPV31 | L2 | 9 | 339 |
| HPV31 | L2 | 10 | 339 |
| HPV31 | L2 | 8 | 310 |
| HPV31 | L2 | 8 | 59 |
| HPV31 | L2 | 9 | 113 |
| HPV31 | L2 | 11 | 113 |
| HPV31 | L2 | 10 | 57 |
| HPV31 | L2 | 9 | 351 |
| HPV31 | L2 | 10 | 221 |
| HPV31 | L2 | 8 | 26 |
| HPV31 | L2 | 11 | 26 |
| HPV31 | L2 | 9 | 65 |
| HPV31 | L2 | 11 | 65 |
| HPV31 | L2 | 9 | 52 |
| HPV31 | L2 | 8 | 213 |
| HPV31 | L2 | 10 | 213 |
| HPV31 | L2 | 11 | 413 |
| HPV31 | L2 | 9 | 175 |
| HPV31 | L2 | 11 | 175 |
| HPV31 | L2 | 8 | 38 |
| HPV31 | L2 | 9 | 38 |
| HPV31 | L2 | 11 | 41 |
| HPV31 | L2 | 8 | 280 |
| HPV31 | L2 | 9 | 280 |
| HPV31 | L2 | 8 | 270 |
| HPV31 | L2 | 10 | 270 |
| HPV31 | L2 | 11 | 270 |
| HPV31 | L2 | 8 | 134 |
| HPV31 | L2 | 10 | 134 |
| HPV31 | L2 | 11 | 134 |
| HPV31 | L2 | 8 | 279 |
| HPV31 | L2 | 9 | 279 |
| HPV31 | L2 | 10 | 279 |
| HPV31 | L2 | 9 | 144 |
| HPV31 | L2 | 9 | 45 |
| HPV31 | L2 | 10 | 205 |
| HPV31 | L2 | 10 | 245 |
| HPV31 | L2 | 11 | 245 |
| HPV31 | L2 | 8 | 114 |
| HPV31 | L2 | 10 | 114 |
| HPV31 | L2 | 10 | 105 |
| HPV31 | L2 | 11 | 105 |
| HPV31 | L2 | 9 | 197 |
| HPV31 | L2 | 10 | 197 |
| HPV31 | L2 | 10 | 23 |
| HPV31 | L2 | 11 | 23 |
| HPV31 | L2 | 8 | 225 |
| HPV31 | L2 | 9 | 225 |
| HPV31 | L2 | 8 | 35 |
| HPV31 | L2 | 11 | 35 |
| HPV31 | L2 | 10 | 242 |
| HPV31 | L2 | 10 | 302 |
| HPV31 | L2 | 11 | 302 |
| HPV31 | L2 | 8 | 231 |
| HPV31 | L2 | 10 | 231 |
| HPV31 | L2 | 8 | 423 |
| HPV31 | L2 | 10 | 423 |
| HPV31 | L2 | 8 | 244 |
| HPV31 | L2 | 11 | 244 |
| HPV31 | L2 | 8 | 176 |
| HPV31 | L2 | 10 | 176 |
| HPV31 | L2 | 9 | 177 |
| HPV31 | L2 | 9 | 164 |
| HPV31 | L2 | 8 | 287 |
| HPV31 | L2 | 8 | 108 |
| HPV31 | L2 | 10 | 108 |
| HPV31 | L2 | 9 | 447 |
| HPV31 | L2 | 8 | 335 |
| HPV31 | L2 | 9 | 335 |
| HPV31 | L2 | 10 | 335 |
| HPV31 | L2 | 11 | 335 |
| HPV31 | L2 | 11 | 256 |
| HPV31 | L2 | 9 | 269 |
| HPV31 | L2 | 11 | 269 |
| HPV31 | L2 | 8 | 204 |
| HPV31 | L2 | 11 | 204 |
| HPV31 | L2 | 8 | 390 |
| HPV31 | L2 | 8 | 292 |
| HPV31 | L2 | 8 | 370 |
| HPV31 | L2 | 11 | 370 |
| HPV31 | L2 | 8 | 169 |
| HPV31 | L2 | 9 | 169 |
| HPV31 | L2 | 10 | 169 |
| HPV31 | L2 | 8 | 328 |
| HPV31 | L2 | 11 | 328 |
| HPV31 | L2 | 9 | 142 |
| HPV31 | L2 | 11 | 142 |
| HPV31 | L2 | 9 | 285 |
| HPV31 | L2 | 10 | 285 |
| HPV31 | L2 | 9 | 120 |
| HPV31 | L2 | 10 | 120 |
| HPV31 | L2 | 10 | 217 |
| HPV31 | L2 | 11 | 217 |
| HPV31 | L2 | 10 | 366 |
| HPV31 | L2 | 11 | 366 |
| HPV31 | L2 | 8 | 250 |
| HPV31 | L2 | 9 | 410 |
| HPV31 | L2 | 8 | 402 |
| HPV31 | L2 | 10 | 402 |
| HPV31 | L2 | 9 | 210 |
| HPV31 | L2 | 11 | 210 |
| HPV31 | L2 | 8 | 122 |
| HPV31 | L2 | 8 | 88 |
| HPV31 | L2 | 11 | 88 |
| HPV31 | L2 | 9 | 422 |
| HPV31 | L2 | 11 | 422 |
| HPV31 | L2 | 9 | 100 |
| HPV31 | L2 | 10 | 100 |
| HPV31 | L2 | 8 | 337 |
| HPV31 | L2 | 9 | 337 |
| HPV31 | L2 | 11 | 337 |
| HPV31 | L2 | 8 | 394 |
| HPV31 | L2 | 10 | 394 |
| HPV31 | L2 | 8 | 74 |
| HPV31 | L2 | 9 | 74 |
| HPV31 | L2 | 9 | 192 |
| HPV31 | L2 | 10 | 235 |
| HPV31 | L2 | 11 | 235 |
| HPV31 | L2 | 8 | 156 |
| HPV31 | L2 | 9 | 156 |
| HPV31 | L2 | 8 | 388 |
| HPV31 | L2 | 10 | 388 |
| HPV31 | L2 | 10 | 167 |
| HPV31 | L2 | 11 | 167 |
| HPV31 | L2 | 9 | 415 |
| HPV31 | L2 | 10 | 415 |
| HPV31 | L2 | 8 | 425 |
| HPV31 | L2 | 10 | 425 |
| HPV31 | L2 | 8 | 127 |
| HPV31 | L2 | 9 | 127 |
| HPV31 | L2 | 10 | 127 |
| HPV31 | L2 | 11 | 127 |
| HPV31 | L2 | 9 | 97 |
| HPV31 | L2 | 10 | 97 |
| HPV31 | L2 | 10 | 92 |
| HPV31 | L2 | 8 | 44 |
| HPV31 | L2 | 10 | 44 |
| HPV31 | L2 | 9 | 243 |
| HPV31 | L2 | 8 | 17 |
| HPV31 | L2 | 9 | 17 |
| HPV31 | L2 | 11 | 17 |
| HPV31 | L2 | 9 | 228 |
| HPV31 | L2 | 11 | 228 |
| HPV31 | L2 | 8 | 20 |
| HPV31 | L2 | 9 | 303 |
| HPV31 | L2 | 10 | 303 |

TABLE VIII-continued

HLA-A2 Supermotif-Bearing Peptides

| 1 | 2 | 3 | 4 |
|---|---|---|---|
| HPV31 | L2 | 11 | 303 |
| HPV31 | L2 | 8 | 417 |
| HPV31 | L2 | 10 | 417 |
| HPV31 | L2 | 11 | 417 |
| HPV31 | L2 | 8 | 229 |
| HPV31 | L2 | 10 | 229 |
| HPV31 | L2 | 10 | 12 |
| HPV31 | L2 | 8 | 219 |
| HPV31 | L2 | 9 | 219 |
| HPV31 | L2 | 8 | 298 |
| HPV31 | L2 | 10 | 298 |
| HPV31 | L2 | 9 | 69 |
| HPV31 | L2 | 8 | 9 |
| HPV31 | L2 | 10 | 9 |
| HPV31 | L2 | 8 | 306 |
| HPV31 | L2 | 10 | 306 |
| HPV31 | L2 | 8 | 316 |
| HPV31 | L2 | 11 | 316 |
| HPV31 | L2 | 9 | 454 |
| HPV31 | L2 | 11 | 454 |
| HPV31 | L2 | 8 | 239 |
| HPV31 | L2 | 8 | 14 |
| HPV31 | L2 | 11 | 14 |
| HPV31 | L2 | 8 | 341 |
| HPV31 | L2 | 9 | 381 |
| HPV31 | L2 | 11 | 381 |
| HPV31 | L2 | 8 | 384 |
| HPV31 | L2 | 9 | 384 |
| HPV31 | L2 | 10 | 384 |
| HPV31 | L2 | 8 | 94 |
| HPV31 | L2 | 9 | 332 |
| HPV31 | L2 | 11 | 332 |
| HPV31 | L2 | 11 | 431 |
| HPV31 | L2 | 9 | 325 |
| HPV31 | L2 | 11 | 325 |
| HPV31 | L2 | 8 | 86 |
| HPV31 | L2 | 10 | 86 |
| HPV31 | L2 | 10 | 182 |
| HPV31 | L2 | 11 | 104 |
| HPV31 | L2 | 8 | 107 |
| HPV31 | L2 | 9 | 107 |
| HPV31 | L2 | 11 | 107 |
| HPV31 | L2 | 11 | 260 |
| HPV31 | L2 | 9 | 50 |
| HPV31 | L2 | 11 | 50 |
| HPV31 | L2 | 9 | 374 |
| HPV31 | L2 | 10 | 374 |
| HPV31 | L2 | 8 | 396 |
| HPV31 | L2 | 9 | 151 |
| HPV31 | L2 | 8 | 184 |
| HPV31 | L2 | 10 | 184 |
| HPV31 | L2 | 8 | 6 |
| HPV31 | L2 | 10 | 6 |
| HPV31 | L2 | 11 | 6 |
| HPV31 | L2 | 10 | 346 |
| HPV31 | L2 | 8 | 199 |
| HPV31 | L2 | 11 | 199 |
| HPV31 | L2 | 11 | 208 |
| HPV31 | L2 | 11 | 76 |
| HPV31 | L2 | 99 | 379 |
| HPV31 | L2 | 11 | 379 |
| HPV31 | L2 | 8 | 80 |
| HPV31 | L2 | 10 | 80 |
| HPV31 | L2 | 9 | 162 |
| HPV31 | L2 | 11 | 162 |
| HPV31 | L2 | 9 | 149 |
| HPV31 | L2 | 11 | 149 |
| HPV31 | L2 | 8 | 137 |
| HPV31 | L2 | 9 | 137 |
| HPV31 | L2 | 11 | 137 |
| HPV31 | L2 | 8 | 375 |
| HPV31 | L2 | 9 | 375 |
| HPV31 | L2 | 11 | 375 |
| HPV31 | L2 | 9 | 347 |
| HPV31 | L2 | 11 | 347 |
| HPV31 | L2 | 8 | 304 |
| HPV31 | L2 | 9 | 304 |
| HPV31 | L2 | 10 | 304 |
| HPV31 | L2 | 9 | 16 |
| HPV31 | L2 | 10 | 16 |
| HPV31 | L2 | 10 | 227 |
| HPV31 | L2 | 8 | 416 |
| HPV31 | L2 | 9 | 416 |
| HPV31 | L2 | 11 | 416 |
| HPV31 | L2 | 8 | 136 |
| HPV31 | L2 | 9 | 136 |
| HPV31 | L2 | 10 | 136 |
| HPV31 | L2 | 8 | 39 |
| HPV31 | L2 | 8 | 140 |
| HPV31 | L2 | 9 | 140 |
| HPV31 | L2 | 11 | 140 |
| HPV31 | L2 | 9 | 426 |
| HPV31 | L2 | 8 | 128 |
| HPV31 | L2 | 9 | 128 |
| HPV31 | L2 | 10 | 128 |
| HPV31 | L2 | 11 | 128 |
| HPV31 | L2 | 9 | 344 |
| HPV31 | L2 | 10 | 343 |
| HPV31 | L2 | 11 | 391 |
| HPV31 | L2 | 10 | 362 |
| HPV31 | L2 | 8 | 254 |
| HPV31 | L2 | 10 | 392 |
| HPV31 | L2 | 9 | 81 |
| HPV31 | L2 | 9 | 232 |
| HPV31 | L2 | 8 | 32 |
| HPV31 | L2 | 9 | 32 |
| HPV31 | L2 | 10 | 32 |
| HPV31 | L2 | 11 | 32 |
| HPV31 | L2 | 8 | 163 |
| HPV31 | L2 | 10 | 163 |
| HPV31 | L2 | 9 | 377 |
| HPV31 | L2 | 11 | 377 |
| HPV31 | L2 | 11 | 147 |
| HPV31 | L2 | 8 | 356 |
| HPV31 | L2 | 10 | 356 |
| HPV31 | L2 | 8 | 440 |
| HPV31 | L2 | 9 | 440 |
| HPV31 | L2 | 10 | 440 |
| HPV31 | L2 | 10 | 446 |
| HPV31 | L2 | 9 | 19 |
| HPV31 | L2 | 10 | 72 |
| HPV31 | L2 | 11 | 72 |
| HPV31 | L2 | 8 | 386 |
| HPV31 | L2 | 10 | 386 |
| HPV33 | E1 | 11 | 382 |
| HPV33 | E1 | 8 | 90 |
| HPV33 | E1 | 11 | 90 |
| HPV33 | E1 | 9 | 96 |
| HPV33 | E1 | 10 | 96 |
| HPV33 | E1 | 10 | 383 |
| HPV33 | E1 | 9 | 104 |
| HPV33 | E1 | 8 | 65 |
| HPV33 | E1 | 9 | 532 |
| HPV33 | E1 | 11 | 532 |
| HPV33 | E1 | 8 | 84 |
| HPV33 | E1 | 10 | 546 |
| HPV33 | E1 | 11 | 546 |
| HPV33 | E1 | 8 | 311 |
| HPV33 | E1 | 9 | 311 |
| HPV33 | E1 | 8 | 318 |
| HPV33 | E1 | 11 | 318 |
| HPV33 | E1 | 10 | 373 |
| HPV33 | E1 | 11 | 373 |
| HPV33 | E1 | 10 | 81 |
| HPV33 | E1 | 11 | 81 |
| HPV33 | E1 | 11 | 22 |
| HPV33 | E1 | 8 | 83 |
| HPV33 | E1 | 9 | 83 |
| HPV33 | E1 | 8 | 310 |
| HPV33 | E1 | 9 | 310 |
| HPV33 | E1 | 10 | 310 |

TABLE VIII-continued

HLA-A2 Supermotif-Bearing Peptides

| 1 | 2 | 3 | 4 |
|---|---|---|---|
| HPV33 | E1 | 11 | 230 |
| HPV33 | E1 | 8 | 259 |
| HPV33 | E1 | 9 | 259 |
| HPV33 | E1 | 10 | 259 |
| HPV33 | E1 | 11 | 259 |
| HPV33 | E1 | 8 | 465 |
| HPV33 | E1 | 10 | 465 |
| HPV33 | E1 | 9 | 297 |
| HPV33 | E1 | 11 | 226 |
| HPV33 | E1 | 9 | 14 |
| HPV33 | E1 | 10 | 14 |
| HPV33 | E1 | 11 | 14 |
| HPV33 | E1 | 8 | 118 |
| HPV33 | E1 | 11 | 118 |
| HPV33 | E1 | 10 | 494 |
| HPV33 | E1 | 10 | 508 |
| HPV33 | E1 | 11 | 508 |
| HPV33 | E1 | 9 | 367 |
| HPV33 | E1 | 10 | 367 |
| HPV33 | E1 | 10 | 46 |
| HPV33 | E1 | 8 | 78 |
| HPV33 | E1 | 9 | 349 |
| HPV33 | E1 | 8 | 62 |
| HPV33 | E1 | 11 | 62 |
| HPV33 | E1 | 8 | 541 |
| HPV33 | E1 | 10 | 541 |
| HPV33 | E1 | 10 | 324 |
| HPV33 | E1 | 8 | 516 |
| HPV33 | E1 | 10 | 516 |
| HPV33 | E1 | 9 | 64 |
| HPV33 | E1 | 8 | 21 |
| HPV33 | E1 | 8 | 206 |
| HPV33 | E1 | 10 | 206 |
| HPV33 | E1 | 11 | 206 |
| HPV33 | E1 | 10 | 537 |
| HPV33 | E1 | 11 | 537 |
| HPV33 | E1 | 11 | 186 |
| HPV33 | E1 | 10 | 127 |
| HPV33 | E1 | 8 | 361 |
| HPV33 | E1 | 9 | 361 |
| HPV33 | E1 | 11 | 214 |
| HPV33 | E1 | 11 | 152 |
| HPV33 | E1 | 8 | 38 |
| HPV33 | E1 | 10 | 38 |
| HPV33 | E1 | 11 | 38 |
| HPV33 | E1 | 11 | 295 |
| HPV33 | E1 | 10 | 173 |
| HPV33 | E1 | 11 | 173 |
| HPV33 | E1 | 9 | 139 |
| HPV33 | E1 | 10 | 19 |
| HPV33 | E1 | 8 | 137 |
| HPV33 | E1 | 11 | 137 |
| HPV33 | E1 | 8 | 169 |
| HPV33 | E1 | 8 | 89 |
| HPV33 | E1 | 9 | 89 |
| HPV33 | E1 | 10 | 50 |
| HPV33 | E1 | 9 | 449 |
| HPV33 | E1 | 10 | 486 |
| HPV33 | E1 | 11 | 456 |
| HPV33 | E1 | 8 | 385 |
| HPV33 | E1 | 10 | 385 |
| HPV33 | E1 | 11 | 385 |
| HPV33 | E1 | 10 | 451 |
| HPV33 | E1 | 8 | 265 |
| HPV33 | E1 | 10 | 399 |
| HPV33 | E1 | 8 | 459 |
| HPV33 | E1 | 9 | 459 |
| HPV33 | E1 | 10 | 459 |
| HPV33 | E1 | 8 | 209 |
| HPV33 | E1 | 10 | 235 |
| HPV33 | E1 | 10 | 11 |
| HPV33 | E1 | 9 | 512 |
| HPV33 | E1 | 8 | 480 |
| HPV33 | E1 | 11 | 416 |
| HPV33 | E1 | 8 | 44 |
| HPV33 | E1 | 9 | 564 |
| HPV33 | E1 | 10 | 6 |
| HPV33 | E1 | 10 | 327 |
| HPV33 | E1 | 11 | 327 |
| HPV33 | E1 | 8 | 163 |
| HPV33 | E1 | 11 | 256 |
| HPV33 | E1 | 8 | 368 |
| HPV33 | E1 | 9 | 368 |
| HPV33 | E1 | 8 | 200 |
| HPV33 | E1 | 11 | 200 |
| HPV33 | E1 | 9 | 400 |
| HPV33 | E1 | 8 | 59 |
| HPV33 | E1 | 10 | 59 |
| HPV33 | E1 | 11 | 59 |
| HPV33 | E1 | 8 | 72 |
| HPV33 | E1 | 10 | 72 |
| HPV33 | E1 | 11 | 72 |
| HPV33 | E1 | 8 | 484 |
| HPV33 | E1 | 9 | 484 |
| HPV33 | E1 | 8 | 419 |
| HPV33 | E1 | 10 | 231 |
| HPV33 | E1 | 11 | 231 |
| HPV33 | E1 | 8 | 394 |
| HPV33 | E1 | 10 | 435 |
| HPV33 | E1 | 9 | 407 |
| HPV33 | E1 | 11 | 197 |
| HPV33 | E1 | 8 | 510 |
| HPV33 | E1 | 9 | 510 |
| HPV33 | E1 | 11 | 510 |
| HPV33 | E1 | 8 | 393 |
| HPV33 | E1 | 9 | 393 |
| HPV33 | E1 | 9 | 285 |
| HPV33 | E1 | 8 | 304 |
| HPV33 | E1 | 9 | 304 |
| HPV33 | E1 | 8 | 412 |
| HPV33 | E1 | 9 | 249 |
| HPV33 | E1 | 11 | 425 |
| HPV33 | E1 | 9 | 223 |
| HPV33 | E1 | 10 | 223 |
| HPV33 | E1 | 9 | 245 |
| HPV33 | E1 | 11 | 245 |
| HPV33 | E1 | 8 | 375 |
| HPV33 | E1 | 9 | 375 |
| HPV33 | E1 | 10 | 375 |
| HPV33 | E1 | 8 | 467 |
| HPV33 | E1 | 9 | 247 |
| HPV33 | E1 | 11 | 247 |
| HPV33 | E1 | 9 | 483 |
| HPV33 | E1 | 10 | 483 |
| HPV33 | E1 | 11 | 271 |
| HPV33 | E1 | 9 | 47 |
| HPV33 | E1 | 9 | 555 |
| HPV33 | E1 | 11 | 555 |
| HPV33 | E1 | 10 | 438 |
| HPV33 | E1 | 11 | 438 |
| HPV33 | E1 | 9 | 290 |
| HPV33 | E1 | 10 | 290 |
| HPV33 | E1 | 11 | 290 |
| HPV33 | E1 | 8 | 556 |
| HPV33 | E1 | 10 | 556 |
| HPV33 | E1 | 8 | 286 |
| HPV33 | E1 | 11 | 286 |
| HPV33 | E1 | 10 | 257 |
| HPV33 | E1 | 11 | 257 |
| HPV33 | E1 | 8 | 184 |
| HPV33 | E1 | 9 | 339 |
| HPV33 | E1 | 9 | 503 |
| HPV33 | E1 | 11 | 503 |
| HPV33 | E1 | 8 | 260 |
| HPV33 | E1 | 9 | 260 |
| HPV33 | E1 | 10 | 260 |
| HPV33 | E1 | 11 | 260 |
| HPV33 | E1 | 8 | 362 |
| HPV33 | E1 | 9 | 557 |
| HPV33 | E1 | 10 | 281 |

TABLE VIII-continued

HLA-A2 Supermotif-Bearing Peptides

| 1 | 2 | 3 | 4 |
|---|---|---|---|
| HPV33 | E1 | 11 | 281 |
| HPV33 | E1 | 9 | 547 |
| HPV33 | E1 | 10 | 547 |
| HPV33 | E1 | 11 | 547 |
| HPV33 | E1 | 10 | 215 |
| HPV33 | E1 | 10 | 1 |
| HPV33 | E1 | 8 | 513 |
| HPV33 | E1 | 11 | 513 |
| HPV33 | E1 | 9 | 466 |
| HPV33 | E1 | 8 | 298 |
| HPV33 | E1 | 10 | 353 |
| HPV33 | E1 | 11 | 353 |
| HPV33 | E1 | 11 | 562 |
| HPV33 | E1 | 8 | 531 |
| HPV33 | E1 | 10 | 531 |
| HPV33 | E1 | 11 | 80 |
| HPV33 | E1 | 8 | 443 |
| HPV33 | E1 | 10 | 443 |
| HPV33 | E1 | 8 | 346 |
| HPV33 | E1 | 9 | 346 |
| HPV33 | E1 | 9 | 199 |
| HPV33 | E1 | 9 | 71 |
| HPV33 | E1 | 11 | 71 |
| HPV33 | E1 | 8 | 321 |
| HPV33 | E1 | 9 | 321 |
| HPV33 | E1 | 9 | 31 |
| HPV33 | E1 | 10 | 31 |
| HPV33 | E1 | 9 | 627 |
| HPV33 | E1 | 8 | 287 |
| HPV33 | E1 | 10 | 289 |
| HPV33 | E1 | 11 | 289 |
| HPV33 | E1 | 10 | 155 |
| HPV33 | E1 | 9 | 135 |
| HPV33 | E1 | 10 | 135 |
| HPV33 | E1 | 9 | 473 |
| HPV33 | E1 | 11 | 473 |
| HPV33 | E1 | 8 | 175 |
| HPV33 | E1 | 9 | 175 |
| HPV33 | E1 | 10 | 175 |
| HPV33 | E1 | 8 | 189 |
| HPV33 | E1 | 10 | 189 |
| HPV33 | E1 | 10 | 181 |
| HPV33 | E1 | 11 | 181 |
| HPV33 | E1 | 11 | 471 |
| HPV33 | E1 | 11 | 519 |
| HPV33 | E1 | 11 | 434 |
| HPV33 | E1 | 8 | 554 |
| HPV33 | E1 | 10 | 554 |
| HPV33 | E1 | 9 | 505 |
| HPV33 | E1 | 10 | 505 |
| HPV33 | E1 | 9 | 60 |
| HPV33 | E1 | 10 | 60 |
| HPV33 | E1 | 10 | 391 |
| HPV33 | E1 | 11 | 391 |
| HPV33 | E1 | 9 | 374 |
| HPV33 | E1 | 10 | 374 |
| HPV33 | E1 | 11 | 374 |
| HPV33 | E1 | 8 | 549 |
| HPV33 | E1 | 9 | 549 |
| HPV33 | E1 | 10 | 549 |
| HPV33 | E1 | 8 | 437 |
| HPV33 | E1 | 11 | 437 |
| HPV33 | E1 | 10 | 145 |
| HPV33 | E1 | 10 | 308 |
| HPV33 | E1 | 11 | 308 |
| HPV33 | E1 | 9 | 146 |
| HPV33 | E1 | 11 | 146 |
| HPV33 | E1 | 8 | 103 |
| HPV33 | E1 | 10 | 103 |
| HPV33 | E1 | 11 | 545 |
| HPV33 | E1 | 8 | 280 |
| HPV33 | E1 | 11 | 280 |
| HPV33 | E1 | 10 | 316 |
| HPV33 | E1 | 11 | 109 |
| HPV33 | E1 | 8 | 608 |
| HPV33 | E1 | 9 | 608 |
| HPV33 | E1 | 10 | 95 |
| HPV33 | E1 | 11 | 95 |
| HPV33 | E1 | 9 | 634 |
| HPV33 | E1 | 8 | 539 |
| HPV33 | E1 | 9 | 539 |
| HPV33 | E1 | 10 | 539 |
| HPV33 | E1 | 9 | 111 |
| HPV33 | E1 | 8 | 292 |
| HPV33 | E1 | 9 | 292 |
| HPV33 | E1 | 8 | 58 |
| HPV33 | E1 | 9 | 58 |
| HPV33 | E1 | 11 | 58 |
| HPV33 | E1 | 10 | 482 |
| HPV33 | E1 | 11 | 482 |
| HPV33 | E1 | 11 | 243 |
| HPV33 | E1 | 9 | 252 |
| HPV33 | E1 | 10 | 252 |
| HPV33 | E1 | 8 | 54 |
| HPV33 | E1 | 10 | 54 |
| HPV33 | E1 | 11 | 390 |
| HPV33 | E1 | 8 | 149 |
| HPV33 | E1 | 11 | 149 |
| HPV33 | E1 | 8 | 93 |
| HPV33 | E1 | 9 | 93 |
| HPV33 | E1 | 11 | 307 |
| HPV33 | E1 | 11 | 629 |
| HPV33 | E1 | 8 | 239 |
| HPV33 | E1 | 9 | 239 |
| HPV33 | E1 | 10 | 239 |
| HPV33 | E1 | 9 | 39 |
| HPV33 | E1 | 10 | 39 |
| HPV33 | E1 | 11 | 447 |
| HPV33 | E1 | 9 | 317 |
| HPV33 | E1 | 8 | 183 |
| HPV33 | E1 | 9 | 183 |
| HPV33 | E1 | 8 | 140 |
| HPV33 | E1 | 9 | 328 |
| HPV33 | E1 | 10 | 328 |
| HPV33 | E1 | 11 | 328 |
| HPV33 | E1 | 9 | 282 |
| HPV33 | E1 | 10 | 282 |
| HPV33 | E1 | 11 | 337 |
| HPV33 | E1 | 8 | 240 |
| HPV33 | E1 | 9 | 240 |
| HPV33 | E1 | 8 | 283 |
| HPV33 | E1 | 9 | 283 |
| HPV33 | E1 | 11 | 283 |
| HPV33 | E1 | 11 | 299 |
| HPV33 | E1 | 10 | 23 |
| HPV33 | E1 | 9 | 190 |
| HPV33 | E1 | 11 | 190 |
| HPV33 | E1 | 8 | 246 |
| HPV33 | E1 | 10 | 246 |
| HPV33 | E1 | 10 | 338 |
| HPV33 | E1 | 9 | 325 |
| HPV33 | E1 | 8 | 548 |
| HPV33 | E1 | 9 | 548 |
| HPV33 | E1 | 10 | 548 |
| HPV33 | E1 | 11 | 548 |
| HPV33 | E1 | 9 | 436 |
| HPV33 | E1 | 11 | 144 |
| HPV33 | E1 | 9 | 354 |
| HPV33 | E1 | 10 | 354 |
| HPV33 | E1 | 9 | 182 |
| HPV33 | E1 | 10 | 182 |
| HPV33 | E1 | 9 | 517 |
| HPV33 | E1 | 11 | 100 |
| HPV33 | E1 | 8 | 356 |
| HPV33 | E1 | 8 | 332 |
| HPV33 | E1 | 9 | 418 |
| HPV33 | E1 | 8 | 502 |
| HPV33 | E1 | 10 | 502 |
| HPV33 | E1 | 8 | 522 |
| HPV33 | E1 | 11 | 522 |

TABLE VIII-continued

HLA-A2 Supermotif-Bearing Peptides

| 1 | 2 | 3 | 4 |
|---|---|---|---|
| HPV33 | E1 | 11 | 372 |
| HPV33 | E1 | 9 | 524 |
| HPV33 | E1 | 10 | 524 |
| HPV33 | E1 | 8 | 571 |
| HPV33 | E1 | 11 | 528 |
| HPV33 | E1 | 8 | 441 |
| HPV33 | E1 | 10 | 441 |
| HPV33 | E1 | 8 | 254 |
| HPV33 | E2 | 9 | 223 |
| HPV33 | E2 | 11 | 223 |
| HPV33 | E2 | 8 | 224 |
| HPV33 | E2 | 10 | 224 |
| HPV33 | E2 | 11 | 224 |
| HPV33 | E2 | 9 | 175 |
| HPV33 | E2 | 9 | 249 |
| HPV33 | E2 | 10 | 249 |
| HPV33 | E2 | 11 | 249 |
| HPV33 | E2 | 9 | 41 |
| HPV33 | E2 | 10 | 237 |
| HPV33 | E2 | 10 | 258 |
| HPV33 | E2 | 11 | 258 |
| HPV33 | E2 | 9 | 10 |
| HPV33 | E2 | 10 | 245 |
| HPV33 | E2 | 11 | 245 |
| HPV33 | E2 | 10 | 40 |
| HPV33 | E2 | 8 | 145 |
| HPV33 | E2 | 11 | 145 |
| HPV33 | E2 | 8 | 261 |
| HPV33 | E2 | 8 | 174 |
| HPV33 | E2 | 10 | 174 |
| HPV33 | E2 | 11 | 25 |
| HPV33 | E2 | 8 | 17 |
| HPV33 | E2 | 10 | 17 |
| HPV33 | E2 | 9 | 235 |
| HPV33 | E2 | 10 | 143 |
| HPV33 | E2 | 9 | 232 |
| HPV33 | E2 | 10 | 232 |
| HPV33 | E2 | 11 | 20 |
| HPV33 | E2 | 8 | 3 |
| HPV33 | E2 | 9 | 3 |
| HPV33 | E2 | 9 | 136 |
| HPV33 | E2 | 11 | 136 |
| HPV33 | E2 | 8 | 74 |
| HPV33 | E2 | 9 | 74 |
| HPV33 | E2 | 9 | 298 |
| HPV33 | E2 | 8 | 328 |
| HPV33 | E2 | 10 | 328 |
| HPV33 | E2 | 11 | 328 |
| HPV33 | E2 | 10 | 80 |
| HPV33 | E2 | 8 | 185 |
| HPV33 | E2 | 9 | 185 |
| HPV33 | E2 | 10 | 185 |
| HPV33 | E2 | 10 | 334 |
| HPV33 | E2 | 11 | 334 |
| HPV33 | E2 | 8 | 70 |
| HPV33 | E2 | 9 | 70 |
| HPV33 | E2 | 10 | 70 |
| HPV33 | E2 | 9 | 325 |
| HPV33 | E2 | 11 | 325 |
| HPV33 | E2 | 8 | 319 |
| HPV33 | E2 | 9 | 319 |
| HPV33 | E2 | 11 | 156 |
| HPV33 | E2 | 8 | 190 |
| HPV33 | E2 | 10 | 190 |
| HPV33 | E2 | 8 | 336 |
| HPV33 | E2 | 9 | 336 |
| HPV33 | E2 | 11 | 336 |
| HPV33 | E2 | 10 | 53 |
| HPV33 | E2 | 11 | 53 |
| HPV33 | E2 | 9 | 278 |
| HPV33 | E2 | 8 | 56 |
| HPV33 | E2 | 9 | 56 |
| HPV33 | E2 | 8 | 187 |
| HPV33 | E2 | 11 | 187 |
| HPV33 | E2 | 8 | 139 |
| HPV33 | E2 | 9 | 139 |
| HPV33 | E2 | 10 | 139 |
| HPV33 | E2 | 11 | 139 |
| HPV33 | E2 | 10 | 15 |
| HPV33 | E2 | 11 | 276 |
| HPV33 | E2 | 8 | 320 |
| HPV33 | E2 | 8 | 68 |
| HPV33 | E2 | 10 | 68 |
| HPV33 | E2 | 11 | 68 |
| HPV33 | E2 | 8 | 14 |
| HPV33 | E2 | 11 | 14 |
| HPV33 | E2 | 8 | 339 |
| HPV33 | E2 | 10 | 339 |
| HPV33 | E2 | 8 | 242 |
| HPV33 | E2 | 9 | 242 |
| HPV33 | E2 | 8 | 34 |
| HPV33 | E2 | 9 | 34 |
| HPV33 | E2 | 10 | 34 |
| HPV33 | E2 | 8 | 112 |
| HPV33 | E2 | 8 | 47 |
| HPV33 | E2 | 10 | 264 |
| HPV33 | E2 | 11 | 264 |
| HPV33 | E2 | 8 | 23 |
| HPV33 | E2 | 8 | 66 |
| HPV33 | E2 | 10 | 66 |
| HPV33 | E2 | 9 | 180 |
| HPV33 | E2 | 10 | 151 |
| HPV33 | E2 | 11 | 165 |
| HPV33 | E2 | 10 | 63 |
| HPV33 | E2 | 11 | 63 |
| HPV33 | E2 | 8 | 35 |
| HPV33 | E2 | 9 | 35 |
| HPV33 | E2 | 11 | 35 |
| HPV33 | E2 | 8 | 62 |
| HPV33 | E2 | 11 | 62 |
| HPV33 | E2 | 8 | 42 |
| HPV33 | E2 | 8 | 75 |
| HPV33 | E2 | 8 | 94 |
| HPV33 | E2 | 10 | 94 |
| HPV33 | E2 | 10 | 240 |
| HPV33 | E2 | 11 | 240 |
| HPV33 | E2 | 9 | 147 |
| HPV33 | E2 | 11 | 147 |
| HPV33 | E2 | 8 | 9 |
| HPV33 | E2 | 10 | 9 |
| HPV33 | E2 | 8 | 202 |
| HPV33 | E2 | 9 | 202 |
| HPV33 | E2 | 11 | 202 |
| HPV33 | E2 | 11 | 127 |
| HPV33 | E2 | 8 | 272 |
| HPV33 | E2 | 8 | 230 |
| HPV33 | E2 | 11 | 230 |
| HPV33 | E2 | 8 | 248 |
| HPV33 | E2 | 10 | 248 |
| HPV33 | E2 | 11 | 248 |
| HPV33 | E2 | 8 | 239 |
| HPV33 | E2 | 11 | 239 |
| HPV33 | E2 | 11 | 221 |
| HPV33 | E2 | 9 | 196 |
| HPV33 | E2 | 11 | 196 |
| HPV33 | E2 | 10 | 342 |
| HPV33 | E2 | 11 | 342 |
| HPV33 | E2 | 10 | 222 |
| HPV33 | E2 | 8 | 29 |
| HPV33 | E2 | 10 | 29 |
| HPV33 | E2 | 8 | 345 |
| HPV33 | E2 | 9 | 345 |
| HPV33 | E2 | 8 | 203 |
| HPV33 | E2 | 10 | 203 |
| HPV33 | E2 | 9 | 332 |
| HPV33 | E2 | 11 | 48 |
| HPV33 | E2 | 11 | 182 |
| HPV33 | E2 | 8 | 331 |
| HPV33 | E2 | 10 | 331 |
| HPV33 | E2 | 8 | 330 |

TABLE VIII-continued

HLA-A2 Supermotif-Bearing Peptides

| 1 | 2 | 3 | 4 |
|---|---|---|---|
| HPV33 | E2 | 9 | 330 |
| HPV33 | E2 | 11 | 330 |
| HPV33 | E2 | 9 | 329 |
| HPV33 | E2 | 10 | 329 |
| HPV33 | E2 | 9 | 95 |
| HPV33 | E2 | 11 | 213 |
| HPV33 | E2 | 8 | 96 |
| HPV33 | E2 | 8 | 71 |
| HPV33 | E2 | 9 | 71 |
| HPV33 | E2 | 11 | 71 |
| HPV33 | E2 | 9 | 191 |
| HPV33 | E2 | 8 | 57 |
| HPV33 | E2 | 11 | 57 |
| HPV33 | E2 | 8 | 292 |
| HPV33 | E2 | 9 | 7 |
| HPV33 | E2 | 10 | 7 |
| HPV33 | E2 | 9 | 37 |
| HPV33 | E2 | 10 | 37 |
| HPV33 | E2 | 10 | 253 |
| HPV33 | E2 | 8 | 266 |
| HPV33 | E2 | 9 | 266 |
| HPV33 | E2 | 11 | 266 |
| HPV33 | E2 | 11 | 5 |
| HPV33 | E2 | 9 | 198 |
| HPV33 | E2 | 10 | 198 |
| HPV33 | E2 | 9 | 285 |
| HPV33 | E2 | 9 | 61 |
| HPV33 | E2 | 9 | 302 |
| HPV33 | E2 | 8 | 28 |
| HPV33 | E2 | 9 | 28 |
| HPV33 | E2 | 11 | 28 |
| HPV33 | E2 | 8 | 90 |
| HPV33 | E2 | 10 | 90 |
| HPV33 | E2 | 9 | 85 |
| HPV33 | E2 | 10 | 85 |
| HPV33 | E2 | 10 | 88 |
| HPV33 | E2 | 8 | 205 |
| HPV33 | E2 | 10 | 205 |
| HPV33 | E2 | 10 | 45 |
| HPV33 | E2 | 8 | 236 |
| HPV33 | E2 | 11 | 236 |
| HPV33 | E2 | 9 | 254 |
| HPV33 | E2 | 11 | 257 |
| HPV33 | E2 | 9 | 93 |
| HPV33 | E2 | 11 | 93 |
| HPV33 | E2 | 9 | 81 |
| HPV33 | E2 | 10 | 128 |
| HPV33 | E2 | 10 | 146 |
| HPV33 | E2 | 8 | 181 |
| HPV33 | E2 | 8 | 233 |
| HPV33 | E2 | 9 | 233 |
| HPV33 | E2 | 11 | 233 |
| HPV33 | E2 | 9 | 206 |
| HPV33 | E2 | 8 | 267 |
| HPV33 | E2 | 10 | 267 |
| HPV33 | E2 | 11 | 267 |
| HPV33 | E2 | 8 | 337 |
| HPV33 | E2 | 10 | 337 |
| HPV33 | E2 | 9 | 343 |
| HPV33 | E2 | 10 | 343 |
| HPV33 | E2 | 11 | 343 |
| HPV33 | E2 | 11 | 118 |
| HPV33 | E2 | 8 | 72 |
| HPV33 | E2 | 10 | 72 |
| HPV33 | E2 | 11 | 72 |
| HPV33 | E2 | 8 | 192 |
| HPV33 | E2 | 8 | 11 |
| HPV33 | E2 | 11 | 11 |
| HPV33 | E2 | 8 | 344 |
| HPV33 | E2 | 9 | 344 |
| HPV33 | E2 | 10 | 344 |
| HPV33 | E2 | 10 | 119 |
| HPV33 | E2 | 11 | 119 |
| HPV33 | E2 | 8 | 326 |
| HPV33 | E2 | 10 | 326 |
| HPV33 | E2 | 11 | 323 |
| HPV33 | E2 | 8 | 148 |
| HPV33 | E2 | 10 | 148 |
| HPV33 | E2 | 10 | 58 |
| HPV33 | E2 | 8 | 92 |
| HPV33 | E2 | 10 | 92 |
| HPV33 | E2 | 8 | 159 |
| HPV33 | E2 | 9 | 138 |
| HPV33 | E2 | 10 | 138 |
| HPV33 | E2 | 11 | 138 |
| HPV33 | E2 | 11 | 44 |
| HPV33 | E2 | 9 | 131 |
| HPV33 | E2 | 10 | 131 |
| HPV33 | E5 | 9 | 63 |
| HPV33 | E5 | 10 | 63 |
| HPV33 | E5 | 9 | 14 |
| HPV33 | E5 | 10 | 14 |
| HPV33 | E5 | 11 | 14 |
| HPV33 | E5 | 9 | 9 |
| HPV33 | E5 | 10 | 9 |
| HPV33 | E5 | 11 | 9 |
| HPV33 | E5 | 8 | 12 |
| HPV33 | E5 | 11 | 12 |
| HPV33 | E5 | 9 | 56 |
| HPV33 | E5 | 8 | 3 |
| HPV33 | E5 | 9 | 3 |
| HPV33 | E5 | 11 | 3 |
| HPV33 | E5 | 8 | 42 |
| HPV33 | E5 | 9 | 5 |
| HPV33 | E5 | 11 | 5 |
| HPV33 | E5 | 8 | 10 |
| HPV33 | E5 | 9 | 10 |
| HPV33 | E5 | 10 | 10 |
| HPV33 | E5 | 8 | 23 |
| HPV33 | E5 | 10 | 23 |
| HPV33 | E5 | 11 | 23 |
| HPV33 | E5 | 8 | 48 |
| HPV33 | E5 | 10 | 48 |
| HPV33 | E5 | 9 | 22 |
| HPV33 | E5 | 11 | 22 |
| HPV33 | E5 | 8 | 54 |
| HPV33 | E5 | 9 | 54 |
| HPV33 | E5 | 11 | 54 |
| HPV33 | E5 | 8 | 17 |
| HPV33 | E5 | 10 | 17 |
| HPV33 | E5 | 11 | 37 |
| HPV33 | E5 | 9 | 18 |
| HPV33 | E5 | 11 | 18 |
| HPV33 | E5 | 8 | 32 |
| HPV33 | E5 | 10 | 32 |
| HPV33 | E5 | 10 | 38 |
| HPV33 | E5 | 9 | 35 |
| HPV33 | E5 | 9 | 33 |
| HPV33 | E5 | 11 | 33 |
| HPV33 | E5 | 10 | 1 |
| HPV33 | E5 | 11 | 1 |
| HPV33 | E5 | 8 | 61 |
| HPV33 | E5 | 11 | 61 |
| HPV33 | E5 | 8 | 21 |
| HPV33 | E5 | 10 | 21 |
| HPV33 | E5 | 9 | 46 |
| HPV33 | E5 | 10 | 46 |
| HPV33 | E5 | 9 | 60 |
| HPV33 | E5 | 8 | 25 |
| HPV33 | E5 | 9 | 25 |
| HPV33 | E5 | 10 | 25 |
| HPV33 | E5 | 11 | 25 |
| HPV33 | E5 | 8 | 16 |
| HPV33 | E5 | 9 | 16 |
| HPV33 | E5 | 11 | 16 |
| HPV33 | E5 | 8 | 27 |
| HPV33 | E5 | 9 | 27 |
| HPV33 | E5 | 10 | 27 |
| HPV33 | E5 | 11 | 27 |
| HPV33 | E5 | 8 | 6 |

TABLE VIII-continued

HLA-A2 Supermotif-Bearing Peptides

| 1 | 2 | 3 | 4 |
|---|---|---|---|
| HPV33 | E5 | 10 | 6 |
| HPV33 | E5 | 8 | 36 |
| HPV33 | E5 | 8 | 34 |
| HPV33 | E5 | 10 | 34 |
| HPV33 | E5 | 8 | 31 |
| HPV33 | E5 | 9 | 31 |
| HPV33 | E5 | 11 | 31 |
| HPV33 | E5 | 8 | 40 |
| HPV33 | E5 | 10 | 40 |
| HPV33 | E5 | 8 | 29 |
| HPV33 | E5 | 9 | 29 |
| HPV33 | E5 | 10 | 29 |
| HPV33 | E5 | 11 | 29 |
| HPV33 | E5 | 9 | 53 |
| HPV33 | E5 | 10 | 53 |
| HPV33 | E5 | 11 | 58 |
| HPV33 | E5 | 11 | 137 |
| HPV33 | E6 | 9 | 18 |
| HPV33 | E6 | 11 | 18 |
| HPV33 | E6 | 8 | 103 |
| HPV33 | E6 | 8 | 66 |
| HPV33 | E6 | 8 | 16 |
| HPV33 | E6 | 11 | 16 |
| HPV33 | E6 | 8 | 30 |
| HPV33 | E6 | 8 | 14 |
| HPV33 | E6 | 9 | 14 |
| HPV33 | E6 | 10 | 14 |
| HPV33 | E6 | 9 | 120 |
| HPV33 | E6 | 8 | 4 |
| HPV33 | E6 | 9 | 4 |
| HPV33 | E6 | 8 | 98 |
| HPV33 | E6 | 11 | 27 |
| HPV33 | E6 | 8 | 89 |
| HPV33 | E6 | 11 | 89 |
| HPV33 | E6 | 9 | 20 |
| HPV33 | E6 | 8 | 41 |
| HPV33 | E6 | 10 | 41 |
| HPV33 | E6 | 11 | 41 |
| HPV33 | E6 | 8 | 45 |
| HPV33 | E6 | 9 | 45 |
| HPV33 | E6 | 10 | 2 |
| HPV33 | E6 | 11 | 2 |
| HPV33 | E6 | 10 | 61 |
| HPV33 | E6 | 11 | 118 |
| HPV33 | E6 | 10 | 64 |
| HPV33 | E6 | 11 | 100 |
| HPV33 | E6 | 10 | 28 |
| HPV33 | E6 | 10 | 37 |
| HPV33 | E6 | 11 | 127 |
| HPV33 | E6 | 11 | 86 |
| HPV33 | E6 | 11 | 109 |
| HPV33 | E6 | 10 | 95 |
| HPV33 | E6 | 11 | 95 |
| HPV33 | E6 | 11 | 36 |
| HPV33 | E6 | 8 | 112 |
| HPV33 | E6 | 10 | 112 |
| HPV33 | E6 | 10 | 17 |
| HPV33 | E6 | 10 | 90 |
| HPV33 | E6 | 11 | 90 |
| HPV33 | E6 | 9 | 10 |
| HPV33 | E6 | 10 | 10 |
| HPV33 | E6 | 10 | 82 |
| HPV33 | E6 | 11 | 82 |
| HPV33 | E6 | 10 | 22 |
| HPV33 | E6 | 10 | 87 |
| HPV33 | E6 | 8 | 11 |
| HPV33 | E6 | 9 | 11 |
| HPV33 | E6 | 11 | 11 |
| HPV33 | E6 | 8 | 21 |
| HPV33 | E6 | 11 | 21 |
| HPV33 | E6 | 9 | 91 |
| HPV33 | E6 | 10 | 91 |
| HPV33 | E6 | 11 | 91 |
| HPV33 | E6 | 11 | 52 |
| HPV33 | E7 | 10 | 45 |
| HPV33 | E7 | 11 | 45 |
| HPV33 | E7 | 8 | 48 |
| HPV33 | E7 | 9 | 48 |
| HPV33 | E7 | 9 | 68 |
| HPV33 | E7 | 11 | 68 |
| HPV33 | E7 | 8 | 75 |
| HPV33 | E7 | 9 | 75 |
| HPV33 | E7 | 10 | 75 |
| HPV33 | E7 | 8 | 21 |
| HPV33 | E7 | 9 | 14 |
| HPV33 | E7 | 9 | 37 |
| HPV33 | E7 | 8 | 43 |
| HPV33 | E7 | 9 | 85 |
| HPV33 | E7 | 11 | 85 |
| HPV33 | E7 | 9 | 59 |
| HPV33 | E7 | 11 | 59 |
| HPV33 | E7 | 8 | 79 |
| HPV33 | E7 | 9 | 79 |
| HPV33 | E7 | 11 | 79 |
| HPV33 | E7 | 10 | 54 |
| HPV33 | E7 | 11 | 54 |
| HPV33 | E7 | 8 | 82 |
| HPV33 | E7 | 9 | 82 |
| HPV33 | E7 | 8 | 83 |
| HPV33 | E7 | 11 | 83 |
| HPV33 | E7 | 8 | 88 |
| HPV33 | E7 | 8 | 62 |
| HPV33 | E7 | 11 | 62 |
| HPV33 | E7 | 8 | 47 |
| HPV33 | E7 | 9 | 47 |
| HPV33 | E7 | 10 | 47 |
| HPV33 | E7 | 10 | 19 |
| HPV33 | E7 | 8 | 6 |
| HPV33 | E7 | 10 | 6 |
| HPV33 | E7 | 11 | 44 |
| HPV33 | E7 | 9 | 81 |
| HPV33 | E7 | 10 | 81 |
| HPV33 | E7 | 8 | 80 |
| HPV33 | E7 | 10 | 80 |
| HPV33 | E7 | 11 | 80 |
| HPV33 | E7 | 8 | 66 |
| HPV33 | E7 | 11 | 66 |
| HPV33 | E7 | 8 | 77 |
| HPV33 | E7 | 10 | 77 |
| HPV33 | E7 | 11 | 77 |
| HPV33 | E7 | 8 | 71 |
| HPV33 | E7 | 9 | 71 |
| HPV33 | E7 | 8 | 49 |
| HPV33 | E7 | 8 | 72 |
| HPV33 | E7 | 11 | 72 |
| HPV33 | E7 | 9 | 78 |
| HPV33 | E7 | 10 | 78 |
| HPV33 | E7 | 9 | 7 |
| HPV33 | E7 | 10 | 63 |
| HPV33 | E7 | 11 | 63 |
| HPV33 | E7 | 8 | 86 |
| HPV33 | E7 | 10 | 86 |
| HPV33 | E7 | 9 | 64 |
| HPV33 | E7 | 10 | 64 |
| HPV33 | E7 | 9 | 12 |
| HPV33 | E7 | 11 | 12 |
| HPV33 | E7 | 9 | 55 |
| HPV33 | E7 | 10 | 55 |
| HPV33 | E7 | 11 | 55 |
| HPV33 | E7 | 8 | 53 |
| HPV33 | E7 | 11 | 53 |
| HPV33 | E7 | 10 | 11 |
| HPV33 | L1 | 10 | 179 |
| HPV33 | L1 | 8 | 482 |
| HPV33 | L1 | 11 | 482 |
| HPV33 | L1 | 8 | 424 |
| HPV33 | L1 | 8 | 316 |
| HPV33 | L1 | 8 | 9 |
| HPV33 | L1 | 10 | 9 |
| HPV33 | L1 | 9 | 44 |

TABLE VIII-continued

HLA-A2 Supermotif-Bearing Peptides

| 1 | 2 | 3 | 4 |
|---|---|---|---|
| HPV33 | L1 | 8 | 270 |
| HPV33 | L1 | 9 | 158 |
| HPV33 | L1 | 9 | 147 |
| HPV33 | L1 | 11 | 147 |
| HPV33 | L1 | 9 | 207 |
| HPV33 | L1 | 9 | 345 |
| HPV33 | L1 | 10 | 396 |
| HPV33 | L1 | 11 | 396 |
| HPV33 | L1 | 8 | 449 |
| HPV33 | L1 | 10 | 449 |
| HPV33 | L1 | 8 | 370 |
| HPV33 | L1 | 11 | 370 |
| HPV33 | L1 | 9 | 274 |
| HPV33 | L1 | 10 | 274 |
| HPV33 | L1 | 11 | 274 |
| HPV33 | L1 | 10 | 199 |
| HPV33 | L1 | 10 | 459 |
| HPV33 | L1 | 11 | 459 |
| HPV33 | L1 | 11 | 202 |
| HPV33 | L1 | 8 | 95 |
| HPV33 | L1 | 10 | 95 |
| HPV33 | L1 | 9 | 88 |
| HPV33 | L1 | 8 | 335 |
| HPV33 | L1 | 9 | 335 |
| HPV33 | L1 | 10 | 335 |
| HPV33 | L1 | 10 | 415 |
| HPV33 | L1 | 11 | 415 |
| HPV33 | L1 | 10 | 219 |
| HPV33 | L1 | 9 | 8 |
| HPV33 | L1 | 11 | 8 |
| HPV33 | L1 | 9 | 269 |
| HPV33 | L1 | 8 | 107 |
| HPV33 | L1 | 10 | 107 |
| HPV33 | L1 | 10 | 447 |
| HPV33 | L1 | 8 | 385 |
| HPV33 | L1 | 9 | 385 |
| HPV33 | L1 | 9 | 467 |
| HPV33 | L1 | 9 | 249 |
| HPV33 | L1 | 8 | 375 |
| HPV33 | L1 | 9 | 375 |
| HPV33 | L1 | 10 | 375 |
| HPV33 | L1 | 8 | 373 |
| HPV33 | L1 | 9 | 373 |
| HPV33 | L1 | 10 | 373 |
| HPV33 | L1 | 11 | 373 |
| HPV33 | L1 | 9 | 256 |
| HPV33 | L1 | 11 | 256 |
| HPV33 | L1 | 8 | 419 |
| HPV33 | L1 | 8 | 330 |
| HPV33 | L1 | 11 | 330 |
| HPV33 | L1 | 8 | 141 |
| HPV33 | L1 | 10 | 141 |
| HPV33 | L1 | 8 | 322 |
| HPV33 | L1 | 10 | 322 |
| HPV33 | L1 | 11 | 322 |
| HPV33 | L1 | 8 | 117 |
| HPV33 | L1 | 10 | 105 |
| HPV33 | L1 | 8 | 472 |
| HPV33 | L1 | 11 | 472 |
| HPV33 | L1 | 9 | 68 |
| HPV33 | L1 | 11 | 68 |
| HPV33 | L1 | 8 | 404 |
| HPV33 | L1 | 10 | 404 |
| HPV33 | L1 | 11 | 138 |
| HPV33 | L1 | 8 | 111 |
| HPV33 | L1 | 11 | 265 |
| HPV33 | L1 | 10 | 281 |
| HPV33 | L1 | 8 | 173 |
| HPV33 | L1 | 10 | 173 |
| HPV33 | L1 | 9 | 115 |
| HPV33 | L1 | 10 | 115 |
| HPV33 | L1 | 8 | 391 |
| HPV33 | L1 | 10 | 365 |
| HPV33 | L1 | 8 | 194 |
| HPV33 | L1 | 10 | 194 |
| HPV33 | L1 | 9 | 397 |
| HPV33 | L1 | 10 | 397 |
| HPV33 | L1 | 9 | 286 |
| HPV33 | L1 | 9 | 474 |
| HPV33 | L1 | 10 | 474 |
| HPV33 | L1 | 8 | 478 |
| HPV33 | L1 | 10 | 478 |
| HPV33 | L1 | 10 | 60 |
| HPV33 | L1 | 11 | 236 |
| HPV33 | L1 | 8 | 153 |
| HPV33 | L1 | 10 | 211 |
| HPV33 | L1 | 9 | 65 |
| HPV33 | L1 | 8 | 379 |
| HPV33 | L1 | 9 | 379 |
| HPV33 | L1 | 10 | 379 |
| HPV33 | L1 | 9 | 20 |
| HPV33 | L1 | 10 | 43 |
| HPV33 | L1 | 11 | 190 |
| HPV33 | L1 | 11 | 42 |
| HPV33 | L1 | 8 | 159 |
| HPV33 | L1 | 8 | 123 |
| HPV33 | L1 | 10 | 123 |
| HPV33 | L1 | 8 | 468 |
| HPV33 | L1 | 9 | 61 |
| HPV33 | L1 | 11 | 469 |
| HPV33 | L1 | 8 | 213 |
| HPV33 | L1 | 10 | 213 |
| HPV33 | L1 | 8 | 413 |
| HPV33 | L1 | 9 | 413 |
| HPV33 | L1 | 10 | 371 |
| HPV33 | L1 | 11 | 371 |
| HPV33 | L1 | 11 | 313 |
| HPV33 | L1 | 8 | 69 |
| HPV33 | L1 | 10 | 69 |
| HPV33 | L1 | 9 | 382 |
| HPV33 | L1 | 11 | 382 |
| HPV33 | L1 | 9 | 405 |
| HPV33 | L1 | 8 | 62 |
| HPV33 | L1 | 8 | 99 |
| HPV33 | L1 | 10 | 99 |
| HPV33 | L1 | 8 | 342 |
| HPV33 | L1 | 10 | 237 |
| HPV33 | L1 | 11 | 387 |
| HPV33 | L1 | 9 | 200 |
| HPV33 | L1 | 8 | 299 |
| HPV33 | L1 | 11 | 178 |
| HPV33 | L1 | 10 | 57 |
| HPV33 | L1 | 8 | 341 |
| HPV33 | L1 | 9 | 341 |
| HPV33 | L1 | 8 | 327 |
| HPV33 | L1 | 10 | 327 |
| HPV33 | L1 | 11 | 327 |
| HPV33 | L1 | 9 | 192 |
| HPV33 | L1 | 10 | 192 |
| HPV33 | L1 | 8 | 181 |
| HPV33 | L1 | 10 | 181 |
| HPV33 | L1 | 11 | 181 |
| HPV33 | L1 | 8 | 221 |
| HPV33 | L1 | 8 | 187 |
| HPV33 | L1 | 9 | 187 |
| HPV33 | L1 | 10 | 439 |
| HPV33 | L1 | 8 | 462 |
| HPV33 | L1 | 10 | 462 |
| HPV33 | L1 | 11 | 113 |
| HPV33 | L1 | 9 | 122 |
| HPV33 | L1 | 11 | 122 |
| HPV33 | L1 | 10 | 165 |
| HPV33 | L1 | 11 | 165 |
| HPV33 | L1 | 8 | 55 |
| HPV33 | L1 | 9 | 55 |
| HPV33 | L1 | 8 | 293 |
| HPV33 | L1 | 9 | 293 |
| HPV33 | L1 | 9 | 484 |
| HPV33 | L1 | 8 | 15 |
| HPV33 | L1 | 10 | 15 |

TABLE VIII-continued

HLA-A2 Supermotif-Bearing Peptides

| 1 | 2 | 3 | 4 |
|---|---|---|---|
| HPV33 | L1 | 8 | 17 |
| HPV33 | L1 | 10 | 470 |
| HPV33 | L1 | 8 | 423 |
| HPV33 | L1 | 9 | 423 |
| HPV33 | L1 | 9 | 214 |
| HPV33 | L1 | 11 | 214 |
| HPV33 | L1 | 8 | 376 |
| HPV33 | L1 | 9 | 376 |
| HPV33 | L1 | 11 | 254 |
| HPV33 | L1 | 9 | 328 |
| HPV33 | L1 | 10 | 328 |
| HPV33 | L1 | 9 | 481 |
| HPV33 | L1 | 8 | 263 |
| HPV33 | L1 | 9 | 263 |
| HPV33 | L1 | 9 | 315 |
| HPV33 | L1 | 9 | 98 |
| HPV33 | L1 | 11 | 98 |
| HPV33 | L1 | 8 | 30 |
| HPV33 | L1 | 10 | 488 |
| HPV33 | L1 | 9 | 455 |
| HPV33 | L1 | 11 | 289 |
| HPV33 | L1 | 11 | 410 |
| HPV33 | L1 | 8 | 51 |
| HPV33 | L1 | 11 | 51 |
| HPV33 | L1 | 10 | 285 |
| HPV33 | L1 | 11 | 32 |
| HPV33 | L1 | 11 | 245 |
| HPV33 | L1 | 9 | 412 |
| HPV33 | L1 | 10 | 412 |
| HPV33 | L1 | 9 | 149 |
| HPV33 | L1 | 11 | 149 |
| HPV33 | L1 | 9 | 298 |
| HPV33 | L1 | 9 | 422 |
| HPV33 | L1 | 10 | 422 |
| HPV33 | L1 | 10 | 304 |
| HPV33 | L1 | 9 | 227 |
| HPV33 | L1 | 11 | 227 |
| HPV33 | L1 | 9 | 23 |
| HPV33 | L1 | 11 | 23 |
| HPV33 | L1 | 8 | 339 |
| HPV33 | L1 | 10 | 339 |
| HPV33 | L1 | 11 | 339 |
| HPV33 | L1 | 8 | 2 |
| HPV33 | L1 | 9 | 2 |
| HPV33 | L1 | 10 | 2 |
| HPV33 | L1 | 8 | 383 |
| HPV33 | L1 | 10 | 383 |
| HPV33 | L1 | 11 | 383 |
| HPV33 | L1 | 8 | 283 |
| HPV33 | L1 | 8 | 193 |
| HPV33 | L1 | 9 | 193 |
| HPV33 | L1 | 11 | 193 |
| HPV33 | L1 | 11 | 343 |
| HPV33 | L1 | 10 | 266 |
| HPV33 | L1 | 9 | 212 |
| HPV33 | L1 | 11 | 212 |
| HPV33 | L1 | 8 | 381 |
| HPV33 | L1 | 10 | 381 |
| HPV33 | L1 | 9 | 96 |
| HPV33 | L1 | 11 | 96 |
| HPV33 | L1 | 8 | 346 |
| HPV33 | L1 | 9 | 282 |
| HPV33 | L1 | 8 | 336 |
| HPV33 | L1 | 9 | 336 |
| HPV33 | L1 | 11 | 336 |
| HPV33 | L1 | 11 | 430 |
| HPV33 | L1 | 9 | 332 |
| HPV33 | L1 | 11 | 332 |
| HPV33 | L1 | 9 | 10 |
| HPV33 | L1 | 9 | 174 |
| HPV33 | L1 | 8 | 386 |
| HPV33 | L1 | 8 | 380 |
| HPV33 | L1 | 9 | 380 |
| HPV33 | L1 | 11 | 380 |
| HPV33 | L1 | 11 | 420 |
| HPV33 | L1 | 10 | 331 |
| HPV33 | L1 | 8 | 333 |
| HPV33 | L1 | 10 | 333 |
| HPV33 | L1 | 11 | 333 |
| HPV33 | L1 | 8 | 21 |
| HPV33 | L1 | 11 | 21 |
| HPV33 | L1 | 8 | 101 |
| HPV33 | L1 | 11 | 401 |
| HPV33 | L1 | 8 | 36 |
| HPV33 | L1 | 9 | 36 |
| HPV33 | L1 | 10 | 36 |
| HPV33 | L1 | 9 | 389 |
| HPV33 | L1 | 10 | 389 |
| HPV33 | L1 | 8 | 276 |
| HPV33 | L1 | 9 | 276 |
| HPV33 | L1 | 11 | 276 |
| HPV33 | L1 | 10 | 362 |
| HPV33 | L1 | 10 | 12 |
| HPV33 | L1 | 11 | 12 |
| HPV33 | L1 | 8 | 443 |
| HPV33 | L1 | 11 | 27 |
| HPV33 | L2 | 8 | 81 |
| HPV33 | L2 | 8 | 140 |
| HPV33 | L2 | 11 | 82 |
| HPV33 | L2 | 8 | 291 |
| HPV33 | L2 | 9 | 291 |
| HPV33 | L2 | 8 | 286 |
| HPV33 | L2 | 9 | 23 |
| HPV33 | L2 | 10 | 23 |
| HPV33 | L2 | 11 | 308 |
| HPV33 | L2 | 10 | 14 |
| HPV33 | L2 | 11 | 14 |
| HPV33 | L2 | 8 | 385 |
| HPV33 | L2 | 10 | 385 |
| HPV33 | L2 | 9 | 283 |
| HPV33 | L2 | 10 | 283 |
| HPV33 | L2 | 11 | 283 |
| HPV33 | L2 | 9 | 409 |
| HPV33 | L2 | 11 | 272 |
| HPV33 | L2 | 8 | 327 |
| HPV33 | L2 | 11 | 327 |
| HPV33 | L2 | 9 | 42 |
| HPV33 | L2 | 11 | 42 |
| HPV33 | L2 | 8 | 431 |
| HPV33 | L2 | 11 | 431 |
| HPV33 | L2 | 10 | 264 |
| HPV33 | L2 | 10 | 401 |
| HPV33 | L2 | 9 | 350 |
| HPV33 | L2 | 9 | 136 |
| HPV33 | L2 | 10 | 95 |
| HPV33 | L2 | 11 | 95 |
| HPV33 | L2 | 9 | 369 |
| HPV33 | L2 | 10 | 30 |
| HPV33 | L2 | 11 | 30 |
| HPV33 | L2 | 8 | 130 |
| HPV33 | L2 | 9 | 130 |
| HPV33 | L2 | 11 | 130 |
| HPV33 | L2 | 10 | 364 |
| HPV33 | L2 | 9 | 115 |
| HPV33 | L2 | 11 | 115 |
| HPV33 | L2 | 8 | 344 |
| HPV33 | L2 | 10 | 344 |
| HPV33 | L2 | 8 | 341 |
| HPV33 | L2 | 11 | 341 |
| HPV33 | L2 | 9 | 110 |
| HPV33 | L2 | 11 | 110 |
| HPV33 | L2 | 9 | 384 |
| HPV33 | L2 | 11 | 384 |
| HPV33 | L2 | 8 | 113 |
| HPV33 | L2 | 11 | 113 |
| HPV33 | L2 | 8 | 181 |
| HPV33 | L2 | 10 | 181 |
| HPV33 | L2 | 11 | 281 |
| HPV33 | L2 | 8 | 242 |
| HPV33 | L2 | 9 | 242 |

TABLE VIII-continued

HLA-A2 Supermotif-Bearing Peptides

| 1 | 2 | 3 | 4 |
|---|---|---|---|
| HPV33 | L2 | 10 | 242 |
| HPV33 | L2 | 9 | 268 |
| HPV33 | L2 | 8 | 460 |
| HPV33 | L2 | 11 | 163 |
| HPV33 | L2 | 9 | 440 |
| HPV33 | L2 | 10 | 440 |
| HPV33 | L2 | 10 | 201 |
| HPV33 | L2 | 11 | 201 |
| HPV33 | L2 | 9 | 117 |
| HPV33 | L2 | 10 | 319 |
| HPV33 | L2 | 10 | 361 |
| HPV33 | L2 | 10 | 226 |
| HPV33 | L2 | 8 | 305 |
| HPV33 | L2 | 8 | 25 |
| HPV33 | L2 | 11 | 25 |
| HPV33 | L2 | 8 | 75 |
| HPV33 | L2 | 9 | 75 |
| HPV33 | L2 | 11 | 75 |
| HPV33 | L2 | 10 | 60 |
| HPV33 | L2 | 9 | 51 |
| HPV33 | L2 | 11 | 51 |
| HPV33 | L2 | 11 | 158 |
| HPV33 | L2 | 10 | 374 |
| HPV33 | L2 | 10 | 336 |
| HPV33 | L2 | 8 | 297 |
| HPV33 | L2 | 11 | 40 |
| HPV33 | L2 | 8 | 285 |
| HPV33 | L2 | 9 | 285 |
| HPV33 | L2 | 8 | 284 |
| HPV33 | L2 | 9 | 284 |
| HPV33 | L2 | 10 | 284 |
| HPV33 | L2 | 9 | 44 |
| HPV33 | L2 | 8 | 152 |
| HPV33 | L2 | 11 | 152 |
| HPV33 | L2 | 8 | 292 |
| HPV33 | L2 | 8 | 331 |
| HPV33 | L2 | 8 | 104 |
| HPV33 | L2 | 11 | 104 |
| HPV33 | L2 | 9 | 433 |
| HPV33 | L2 | 10 | 433 |
| HPV33 | L2 | 10 | 22 |
| HPV33 | L2 | 11 | 22 |
| HPV33 | L2 | 9 | 248 |
| HPV33 | L2 | 8 | 311 |
| HPV33 | L2 | 10 | 311 |
| HPV33 | L2 | 8 | 34 |
| HPV33 | L2 | 11 | 34 |
| HPV33 | L2 | 8 | 236 |
| HPV33 | L2 | 9 | 236 |
| HPV33 | L2 | 8 | 107 |
| HPV33 | L2 | 10 | 107 |
| HPV33 | L2 | 8 | 249 |
| HPV33 | L2 | 8 | 266 |
| HPV33 | L2 | 11 | 266 |
| HPV33 | L2 | 8 | 85 |
| HPV33 | L2 | 9 | 85 |
| HPV33 | L2 | 10 | 85 |
| HPV33 | L2 | 9 | 345 |
| HPV33 | L2 | 8 | 243 |
| HPV33 | L2 | 9 | 243 |
| HPV33 | L2 | 9 | 377 |
| HPV33 | L2 | 10 | 377 |
| HPV33 | L2 | 11 | 377 |
| HPV33 | L2 | 8 | 195 |
| HPV33 | L2 | 9 | 195 |
| HPV33 | L2 | 11 | 195 |
| HPV33 | L2 | 8 | 397 |
| HPV33 | L2 | 9 | 397 |
| HPV33 | L2 | 8 | 231 |
| HPV33 | L2 | 11 | 231 |
| HPV33 | L2 | 8 | 391 |
| HPV33 | L2 | 10 | 143 |
| HPV33 | L2 | 8 | 209 |
| HPV33 | L2 | 9 | 174 |
| HPV33 | L2 | 11 | 255 |
| HPV33 | L2 | 10 | 240 |
| HPV33 | L2 | 11 | 240 |
| HPV33 | L2 | 9 | 139 |
| HPV33 | L2 | 9 | 290 |
| HPV33 | L2 | 10 | 290 |
| HPV33 | L2 | 11 | 172 |
| HPV33 | L2 | 8 | 275 |
| HPV33 | L2 | 10 | 275 |
| HPV33 | L2 | 11 | 275 |
| HPV33 | L2 | 8 | 73 |
| HPV33 | L2 | 9 | 73 |
| HPV33 | L2 | 10 | 73 |
| HPV33 | L2 | 11 | 73 |
| HPV33 | L2 | 8 | 215 |
| HPV33 | L2 | 9 | 215 |
| HPV33 | L2 | 11 | 215 |
| HPV33 | L2 | 8 | 87 |
| HPV33 | L2 | 10 | 87 |
| HPV33 | L2 | 11 | 87 |
| HPV33 | L2 | 10 | 423 |
| HPV33 | L2 | 11 | 423 |
| HPV33 | L2 | 8 | 330 |
| HPV33 | L2 | 9 | 330 |
| HPV33 | L2 | 9 | 99 |
| HPV33 | L2 | 10 | 99 |
| HPV33 | L2 | 8 | 395 |
| HPV33 | L2 | 10 | 395 |
| HPV33 | L2 | 11 | 395 |
| HPV33 | L2 | 9 | 84 |
| HPV33 | L2 | 10 | 84 |
| HPV33 | L2 | 11 | 84 |
| HPV33 | L2 | 9 | 197 |
| HPV33 | L2 | 8 | 376 |
| HPV33 | L2 | 10 | 376 |
| HPV33 | L2 | 11 | 376 |
| HPV33 | L2 | 10 | 79 |
| HPV33 | L2 | 8 | 161 |
| HPV33 | L2 | 9 | 161 |
| HPV33 | L2 | 8 | 124 |
| HPV33 | L2 | 9 | 124 |
| HPV33 | L2 | 10 | 124 |
| HPV33 | L2 | 9 | 416 |
| HPV33 | L2 | 11 | 186 |
| HPV33 | L2 | 8 | 403 |
| HPV33 | L2 | 10 | 91 |
| HPV33 | L2 | 8 | 43 |
| HPV33 | L2 | 10 | 43 |
| HPV33 | L2 | 8 | 16 |
| HPV33 | L2 | 9 | 16 |
| HPV33 | L2 | 11 | 16 |
| HPV33 | L2 | 9 | 233 |
| HPV33 | L2 | 11 | 233 |
| HPV33 | L2 | 8 | 19 |
| HPV33 | L2 | 10 | 153 |
| HPV33 | L2 | 8 | 234 |
| HPV33 | L2 | 10 | 234 |
| HPV33 | L2 | 11 | 234 |
| HPV33 | L2 | 10 | 11 |
| HPV33 | L2 | 8 | 321 |
| HPV33 | L2 | 11 | 321 |
| HPV33 | L2 | 9 | 224 |
| HPV33 | L2 | 9 | 68 |
| HPV33 | L2 | 9 | 388 |
| HPV33 | L2 | 11 | 388 |
| HPV33 | L2 | 8 | 303 |
| HPV33 | L2 | 10 | 303 |
| HPV33 | L2 | 8 | 134 |
| HPV33 | L2 | 9 | 134 |
| HPV33 | L2 | 11 | 134 |
| HPV33 | L2 | 8 | 13 |
| HPV33 | L2 | 11 | 13 |
| HPV33 | L2 | 9 | 357 |
| HPV33 | L2 | 11 | 357 |
| HPV33 | L2 | 10 | 393 |
| HPV33 | L2 | 10 | 122 |

TABLE VIII-continued

HLA-A2 Supermotif-Bearing Peptides

| 1 | 2 | 3 | 4 |
|---|---|---|---|
| HPV33 | L2 | 11 | 122 |
| HPV33 | L2 | 9 | 151 |
| HPV33 | L2 | 9 | 103 |
| HPV33 | L2 | 9 | 49 |
| HPV33 | L2 | 11 | 49 |
| HPV33 | L2 | 9 | 106 |
| HPV33 | L2 | 11 | 106 |
| HPV33 | L2 | 8 | 204 |
| HPV33 | L2 | 11 | 204 |
| HPV33 | L2 | 8 | 382 |
| HPV33 | L2 | 11 | 382 |
| HPV33 | L2 | 9 | 156 |
| HPV33 | L2 | 8 | 38 |
| HPV33 | L2 | 10 | 213 |
| HPV33 | L2 | 11 | 213 |
| HPV33 | L2 | 8 | 189 |
| HPV33 | L2 | 10 | 189 |
| HPV33 | L2 | 9 | 6 |
| HPV33 | L2 | 10 | 6 |
| HPV33 | L2 | 11 | 352 |
| HPV33 | L2 | 9 | 146 |
| HPV33 | L2 | 10 | 146 |
| HPV33 | L2 | 9 | 167 |
| HPV33 | L2 | 11 | 167 |
| HPV33 | L2 | 9 | 80 |
| HPV33 | L2 | 9 | 154 |
| HPV33 | L2 | 11 | 154 |
| HPV33 | L2 | 10 | 432 |
| HPV33 | L2 | 11 | 432 |
| HPV33 | L2 | 10 | 309 |
| HPV33 | L2 | 9 | 265 |
| HPV33 | L2 | 9 | 15 |
| HPV33 | L2 | 10 | 15 |
| HPV33 | L2 | 10 | 232 |
| HPV33 | L2 | 9 | 190 |
| HPV33 | L2 | 11 | 190 |
| HPV33 | L2 | 8 | 137 |
| HPV33 | L2 | 11 | 137 |
| HPV33 | L2 | 9 | 386 |
| HPV33 | L2 | 11 | 386 |
| HPV33 | L2 | 9 | 132 |
| HPV33 | L2 | 10 | 132 |
| HPV33 | L2 | 11 | 132 |
| HPV33 | L2 | 8 | 93 |
| HPV33 | L2 | 9 | 96 |
| HPV33 | L2 | 10 | 96 |
| HPV33 | L2 | 10 | 96 |
| HPV33 | L2 | 9 | 337 |
| HPV33 | L2 | 11 | 298 |
| HPV33 | L2 | 10 | 187 |
| HPV33 | L2 | 11 | 222 |
| HPV33 | L2 | 9 | 31 |
| HPV33 | L2 | 10 | 31 |
| HPV33 | L2 | 11 | 31 |
| HPV33 | L2 | 8 | 168 |
| HPV33 | L2 | 10 | 168 |
| HPV33 | L2 | 8 | 441 |
| HPV33 | L2 | 9 | 441 |
| HPV33 | L2 | 11 | 404 |
| HPV33 | L2 | 8 | 131 |
| HPV33 | L2 | 10 | 131 |
| HPV33 | L2 | 11 | 131 |
| HPV33 | L2 | 9 | 92 |
| HPV33 | L2 | 8 | 434 |
| HPV33 | L2 | 9 | 434 |
| HPV33 | L2 | 8 | 237 |
| HPV33 | L2 | 9 | 202 |
| HPV33 | L2 | 10 | 202 |
| HPV33 | L2 | 8 | 366 |
| HPV33 | L2 | 10 | 366 |
| HPV33 | L2 | 8 | 325 |
| HPV33 | L2 | 10 | 325 |
| HPV33 | L2 | 9 | 18 |
| HPV33 | L2 | 10 | 71 |
| HPV33 | L2 | 11 | 71 |
| HPV45 | E1 | 11 | 382 |
| HPV45 | E1 | 8 | 144 |
| HPV45 | E1 | 10 | 144 |
| HPV45 | E1 | 10 | 383 |
| HPV45 | E1 | 8 | 310 |
| HPV45 | E1 | 10 | 310 |
| HPV45 | E1 | 10 | 198 |
| HPV45 | E1 | 8 | 232 |
| HPV45 | E1 | 9 | 232 |
| HPV45 | E1 | 10 | 232 |
| HPV45 | E1 | 9 | 532 |
| HPV45 | E1 | 8 | 68 |
| HPV45 | E1 | 9 | 452 |
| HPV45 | E1 | 9 | 311 |
| HPV45 | E1 | 9 | 199 |
| HPV45 | E1 | 9 | 512 |
| HPV45 | E1 | 10 | 66 |
| HPV45 | E1 | 8 | 72 |
| HPV45 | E1 | 10 | 72 |
| HPV45 | E1 | 11 | 72 |
| HPV45 | E1 | 8 | 408 |
| HPV45 | E1 | 10 | 373 |
| HPV45 | E1 | 11 | 373 |
| HPV45 | E1 | 8 | 40 |
| HPV45 | E1 | 9 | 40 |
| HPV45 | E1 | 10 | 251 |
| HPV45 | E1 | 9 | 202 |
| HPV45 | E1 | 10 | 399 |
| HPV45 | E1 | 11 | 398 |
| HPV45 | E1 | 8 | 465 |
| HPV45 | E1 | 10 | 465 |
| HPV45 | E1 | 8 | 259 |
| HPV45 | E1 | 9 | 259 |
| HPV45 | E1 | 10 | 259 |
| HPV45 | E1 | 11 | 259 |
| HPV45 | E1 | 9 | 297 |
| HPV45 | E1 | 10 | 390 |
| HPV45 | E1 | 11 | 390 |
| HPV45 | E1 | 8 | 226 |
| HPV45 | E1 | 11 | 226 |
| HPV45 | E1 | 10 | 634 |
| HPV45 | E1 | 11 | 621 |
| HPV45 | E1 | 8 | 78 |
| HPV45 | E1 | 8 | 516 |
| HPV45 | E1 | 8 | 206 |
| HPV45 | E1 | 10 | 206 |
| HPV45 | E1 | 11 | 206 |
| HPV45 | E1 | 9 | 614 |
| HPV45 | E1 | 11 | 614 |
| HPV45 | E1 | 9 | 349 |
| HPV45 | E1 | 9 | 108 |
| HPV45 | E1 | 11 | 108 |
| HPV45 | E1 | 8 | 361 |
| HPV45 | E1 | 9 | 361 |
| HPV45 | E1 | 11 | 214 |
| HPV45 | E1 | 9 | 367 |
| HPV45 | E1 | 10 | 367 |
| HPV45 | E1 | 8 | 46 |
| HPV45 | E1 | 10 | 46 |
| HPV45 | E1 | 11 | 352 |
| HPV45 | E1 | 8 | 106 |
| HPV45 | E1 | 11 | 106 |
| HPV45 | E1 | 9 | 623 |
| HPV45 | E1 | 10 | 42 |
| HPV45 | E1 | 10 | 508 |
| HPV45 | E1 | 11 | 508 |
| HPV45 | E1 | 9 | 328 |
| HPV45 | E1 | 10 | 328 |
| HPV45 | E1 | 11 | 328 |
| HPV45 | E1 | 10 | 52 |
| HPV45 | E1 | 10 | 30 |
| HPV45 | E1 | 11 | 30 |
| HPV45 | E1 | 8 | 143 |
| HPV45 | E1 | 9 | 143 |
| HPV45 | E1 | 11 | 143 |

TABLE VIII-continued

HLA-A2 Supermotif-Bearing Peptides

| 1 | 2 | 3 | 4 |
|---|---|---|---|
| HPV45 | E1 | 11 | 115 |
| HPV45 | E1 | 8 | 186 |
| HPV45 | E1 | 10 | 189 |
| HPV45 | E1 | 11 | 189 |
| HPV45 | E1 | 8 | 59 |
| HPV45 | E1 | 10 | 59 |
| HPV45 | E1 | 11 | 59 |
| HPV45 | E1 | 8 | 62 |
| HPV45 | E1 | 11 | 62 |
| HPV45 | E1 | 9 | 101 |
| HPV45 | E1 | 9 | 64 |
| HPV45 | E1 | 10 | 38 |
| HPV45 | E1 | 11 | 38 |
| HPV45 | E1 | 11 | 295 |
| HPV45 | E1 | 8 | 21 |
| HPV45 | E1 | 11 | 21 |
| HPV45 | E1 | 8 | 146 |
| HPV45 | E1 | 10 | 146 |
| HPV45 | E1 | 9 | 141 |
| HPV45 | E1 | 10 | 141 |
| HPV45 | E1 | 11 | 141 |
| HPV45 | E1 | 8 | 74 |
| HPV45 | E1 | 9 | 74 |
| HPV45 | E1 | 11 | 74 |
| HPV45 | E1 | 10 | 324 |
| HPV45 | E1 | 11 | 89 |
| HPV45 | E1 | 8 | 50 |
| HPV45 | E1 | 8 | 483 |
| HPV45 | E1 | 9 | 483 |
| HPV45 | E1 | 10 | 483 |
| HPV45 | E1 | 8 | 446 |
| HPV45 | E1 | 11 | 456 |
| HPV45 | E1 | 8 | 385 |
| HPV45 | E1 | 11 | 385 |
| HPV45 | E1 | 10 | 486 |
| HPV45 | E1 | 9 | 449 |
| HPV45 | E1 | 10 | 438 |
| HPV45 | E1 | 10 | 19 |
| HPV45 | E1 | 10 | 494 |
| HPV45 | E1 | 9 | 342 |
| HPV45 | E1 | 10 | 626 |
| HPV45 | E1 | 11 | 626 |
| HPV45 | E1 | 8 | 318 |
| HPV45 | E1 | 8 | 209 |
| HPV45 | E1 | 8 | 286 |
| HPV45 | E1 | 11 | 286 |
| HPV45 | E1 | 8 | 480 |
| HPV45 | E1 | 11 | 480 |
| HPV45 | E1 | 11 | 630 |
| HPV45 | E1 | 10 | 11 |
| HPV45 | E1 | 8 | 459 |
| HPV45 | E1 | 9 | 459 |
| HPV45 | E1 | 10 | 459 |
| HPV45 | E1 | 8 | 443 |
| HPV45 | E1 | 10 | 443 |
| HPV45 | E1 | 11 | 443 |
| HPV45 | E1 | 8 | 265 |
| HPV45 | E1 | 9 | 71 |
| HPV45 | E1 | 11 | 71 |
| HPV45 | E1 | 11 | 256 |
| HPV45 | E1 | 8 | 83 |
| HPV45 | E1 | 11 | 519 |
| HPV45 | E1 | 8 | 292 |
| HPV45 | E1 | 9 | 292 |
| HPV45 | E1 | 10 | 555 |
| HPV45 | E1 | 9 | 466 |
| HPV45 | E1 | 10 | 257 |
| HPV45 | E1 | 11 | 257 |
| HPV45 | E1 | 11 | 333 |
| HPV45 | E1 | 8 | 184 |
| HPV45 | E1 | 10 | 184 |
| HPV45 | E1 | 9 | 23 |
| HPV45 | E1 | 10 | 23 |
| HPV45 | E1 | 10 | 435 |
| HPV45 | E1 | 11 | 197 |
| HPV45 | E1 | 8 | 124 |
| HPV45 | E1 | 9 | 124 |
| HPV45 | E1 | 11 | 425 |
| HPV45 | E1 | 8 | 304 |
| HPV45 | E1 | 9 | 304 |
| HPV45 | E1 | 8 | 245 |
| HPV45 | E1 | 9 | 245 |
| HPV45 | E1 | 11 | 245 |
| HPV45 | E1 | 8 | 223 |
| HPV45 | E1 | 9 | 223 |
| HPV45 | E1 | 10 | 223 |
| HPV45 | E1 | 11 | 223 |
| HPV45 | E1 | 8 | 510 |
| HPV45 | E1 | 9 | 510 |
| HPV45 | E1 | 11 | 510 |
| HPV45 | E1 | 8 | 375 |
| HPV45 | E1 | 9 | 375 |
| HPV45 | E1 | 10 | 375 |
| HPV45 | E1 | 8 | 506 |
| HPV45 | E1 | 9 | 506 |
| HPV45 | E1 | 10 | 201 |
| HPV45 | E1 | 11 | 299 |
| HPV45 | E1 | 9 | 247 |
| HPV45 | E1 | 11 | 247 |
| HPV45 | E1 | 9 | 290 |
| HPV45 | E1 | 10 | 290 |
| HPV45 | E1 | 11 | 290 |
| HPV45 | E1 | 9 | 190 |
| HPV45 | E1 | 10 | 190 |
| HPV45 | E1 | 11 | 190 |
| HPV45 | E1 | 9 | 547 |
| HPV45 | E1 | 10 | 547 |
| HPV45 | E1 | 11 | 547 |
| HPV45 | E1 | 11 | 271 |
| HPV45 | E1 | 9 | 556 |
| HPV45 | E1 | 8 | 467 |
| HPV45 | E1 | 8 | 191 |
| HPV45 | E1 | 9 | 191 |
| HPV45 | E1 | 10 | 191 |
| HPV45 | E1 | 11 | 191 |
| HPV45 | E1 | 9 | 487 |
| HPV45 | E1 | 8 | 548 |
| HPV45 | E1 | 9 | 548 |
| HPV45 | E1 | 10 | 548 |
| HPV45 | E1 | 11 | 548 |
| HPV45 | E1 | 8 | 362 |
| HPV45 | E1 | 8 | 336 |
| HPV45 | E1 | 8 | 557 |
| HPV45 | E1 | 9 | 281 |
| HPV45 | E1 | 10 | 281 |
| HPV45 | E1 | 11 | 281 |
| HPV45 | E1 | 10 | 215 |
| HPV45 | E1 | 11 | 215 |
| HPV45 | E1 | 8 | 368 |
| HPV45 | E1 | 9 | 368 |
| HPV45 | E1 | 9 | 231 |
| HPV45 | E1 | 10 | 231 |
| HPV45 | E1 | 11 | 231 |
| HPV45 | E1 | 8 | 200 |
| HPV45 | E1 | 11 | 200 |
| HPV45 | E1 | 8 | 513 |
| HPV45 | E1 | 11 | 513 |
| HPV45 | E1 | 8 | 298 |
| HPV45 | E1 | 9 | 47 |
| HPV45 | E1 | 11 | 47 |
| HPV45 | E1 | 10 | 353 |
| HPV45 | E1 | 11 | 353 |
| HPV45 | E1 | 8 | 154 |
| HPV45 | E1 | 11 | 154 |
| HPV45 | E1 | 11 | 174 |
| HPV45 | E1 | 8 | 531 |
| HPV45 | E1 | 10 | 531 |
| HPV45 | E1 | 9 | 321 |
| HPV45 | E1 | 9 | 473 |
| HPV45 | E1 | 10 | 152 |

TABLE VIII-continued

HLA-A2 Supermotif-Bearing Peptides

| 1 | 2 | 3 | 4 |
|---|---|---|---|
| HPV45 | E1 | 8 | 177 |
| HPV45 | E1 | 9 | 177 |
| HPV45 | E1 | 11 | 177 |
| HPV45 | E1 | 10 | 563 |
| HPV45 | E1 | 11 | 471 |
| HPV45 | E1 | 8 | 250 |
| HPV45 | E1 | 11 | 250 |
| HPV45 | E1 | 8 | 554 |
| HPV45 | E1 | 11 | 554 |
| HPV45 | E1 | 11 | 537 |
| HPV45 | E1 | 11 | 434 |
| HPV45 | E1 | 8 | 505 |
| HPV45 | E1 | 9 | 505 |
| HPV45 | E1 | 10 | 505 |
| HPV45 | E1 | 8 | 98 |
| HPV45 | E1 | 10 | 98 |
| HPV45 | E1 | 10 | 546 |
| HPV45 | E1 | 11 | 546 |
| HPV45 | E1 | 9 | 238 |
| HPV45 | E1 | 10 | 238 |
| HPV45 | E1 | 11 | 238 |
| HPV45 | E1 | 9 | 60 |
| HPV45 | E1 | 10 | 60 |
| HPV45 | E1 | 9 | 391 |
| HPV45 | E1 | 10 | 391 |
| HPV45 | E1 | 11 | 391 |
| HPV45 | E1 | 9 | 67 |
| HPV45 | E1 | 8 | 192 |
| HPV45 | E1 | 9 | 192 |
| HPV45 | E1 | 10 | 192 |
| HPV45 | E1 | 11 | 192 |
| HPV45 | E1 | 9 | 374 |
| HPV45 | E1 | 10 | 374 |
| HPV45 | E1 | 11 | 374 |
| HPV45 | E1 | 8 | 549 |
| HPV45 | E1 | 9 | 549 |
| HPV45 | E1 | 10 | 549 |
| HPV45 | E1 | 8 | 54 |
| HPV45 | E1 | 8 | 102 |
| HPV45 | E1 | 8 | 412 |
| HPV45 | E1 | 11 | 80 |
| HPV45 | E1 | 8 | 148 |
| HPV45 | E1 | 10 | 451 |
| HPV45 | E1 | 9 | 407 |
| HPV45 | E1 | 11 | 612 |
| HPV45 | E1 | 9 | 335 |
| HPV45 | E1 | 8 | 280 |
| HPV45 | E1 | 10 | 280 |
| HPV45 | E1 | 11 | 280 |
| HPV45 | E1 | 9 | 411 |
| HPV45 | E1 | 10 | 316 |
| HPV45 | E1 | 8 | 608 |
| HPV45 | E1 | 10 | 575 |
| HPV45 | E1 | 10 | 56 |
| HPV45 | E1 | 11 | 56 |
| HPV45 | E1 | 9 | 539 |
| HPV45 | E1 | 10 | 539 |
| HPV45 | E1 | 8 | 183 |
| HPV45 | E1 | 9 | 183 |
| HPV45 | E1 | 11 | 183 |
| HPV45 | E1 | 9 | 117 |
| HPV45 | E1 | 11 | 416 |
| HPV45 | E1 | 9 | 288 |
| HPV45 | E1 | 11 | 288 |
| HPV45 | E1 | 10 | 308 |
| HPV45 | E1 | 10 | 104 |
| HPV45 | E1 | 8 | 65 |
| HPV45 | E1 | 11 | 65 |
| HPV45 | E1 | 9 | 39 |
| HPV45 | E1 | 10 | 39 |
| HPV45 | E1 | 10 | 22 |
| HPV45 | E1 | 11 | 22 |
| HPV45 | E1 | 8 | 246 |
| HPV45 | E1 | 10 | 246 |
| HPV45 | E1 | 8 | 289 |
| HPV45 | E1 | 10 | 289 |
| HPV45 | E1 | 11 | 289 |
| HPV45 | E1 | 9 | 252 |
| HPV45 | E1 | 9 | 53 |
| HPV45 | E1 | 9 | 147 |
| HPV45 | E1 | 8 | 224 |
| HPV45 | E1 | 9 | 224 |
| HPV45 | E1 | 10 | 224 |
| HPV45 | E1 | 8 | 239 |
| HPV45 | E1 | 9 | 239 |
| HPV45 | E1 | 10 | 239 |
| HPV45 | E1 | 8 | 282 |
| HPV45 | E1 | 9 | 282 |
| HPV45 | E1 | 10 | 282 |
| HPV45 | E1 | 8 | 577 |
| HPV45 | E1 | 9 | 309 |
| HPV45 | E1 | 11 | 309 |
| HPV45 | E1 | 8 | 240 |
| HPV45 | E1 | 9 | 240 |
| HPV45 | E1 | 8 | 283 |
| HPV45 | E1 | 9 | 283 |
| HPV45 | E1 | 11 | 283 |
| HPV45 | E1 | 8 | 511 |
| HPV45 | E1 | 10 | 511 |
| HPV45 | E1 | 9 | 31 |
| HPV45 | E1 | 10 | 31 |
| HPV45 | E1 | 11 | 31 |
| HPV45 | E1 | 10 | 81 |
| HPV45 | E1 | 10 | 230 |
| HPV45 | E1 | 11 | 230 |
| HPV45 | E1 | 9 | 400 |
| HPV45 | E1 | 9 | 436 |
| HPV45 | E1 | 8 | 75 |
| HPV45 | E1 | 10 | 75 |
| HPV45 | E1 | 11 | 75 |
| HPV45 | E1 | 9 | 354 |
| HPV45 | E1 | 10 | 354 |
| HPV45 | E1 | 9 | 635 |
| HPV45 | E1 | 9 | 576 |
| HPV45 | E1 | 9 | 356 |
| HPV45 | E1 | 9 | 418 |
| HPV45 | E1 | 8 | 332 |
| HPV45 | E1 | 8 | 502 |
| HPV45 | E1 | 10 | 502 |
| HPV45 | E1 | 11 | 502 |
| HPV45 | E1 | 8 | 522 |
| HPV45 | E1 | 11 | 522 |
| HPV45 | E1 | 8 | 229 |
| HPV45 | E1 | 11 | 229 |
| HPV45 | E1 | 11 | 372 |
| HPV45 | E1 | 8 | 571 |
| HPV45 | E1 | 10 | 571 |
| HPV45 | E1 | 8 | 394 |
| HPV45 | E1 | 11 | 528 |
| HPV45 | E1 | 10 | 441 |
| HPV45 | E2 | 9 | 156 |
| HPV45 | E2 | 8 | 78 |
| HPV45 | E2 | 11 | 78 |
| HPV45 | E2 | 11 | 47 |
| HPV45 | E2 | 11 | 89 |
| HPV45 | E2 | 10 | 247 |
| HPV45 | E2 | 11 | 247 |
| HPV45 | E2 | 8 | 216 |
| HPV45 | E2 | 11 | 216 |
| HPV45 | E2 | 10 | 305 |
| HPV45 | E2 | 10 | 134 |
| HPV45 | E2 | 10 | 158 |
| HPV45 | E2 | 11 | 31 |
| HPV45 | E2 | 9 | 102 |
| HPV45 | E2 | 8 | 212 |
| HPV45 | E2 | 9 | 212 |
| HPV45 | E2 | 9 | 351 |
| HPV45 | E2 | 11 | 351 |
| HPV45 | E2 | 9 | 319 |
| HPV45 | E2 | 9 | 80 |

TABLE VIII-continued

HLA-A2 Supermotif-Bearing Peptides

| 1 | 2 | 3 | 4 |
|---|---|---|---|
| HPV45 | E2 | 10 | 80 |
| HPV45 | E2 | 9 | 258 |
| HPV45 | E2 | 11 | 258 |
| HPV45 | E2 | 8 | 148 |
| HPV45 | E2 | 9 | 148 |
| HPV45 | E2 | 10 | 148 |
| HPV45 | E2 | 8 | 343 |
| HPV45 | E2 | 10 | 343 |
| HPV45 | E2 | 11 | 343 |
| HPV45 | E2 | 8 | 192 |
| HPV45 | E2 | 9 | 192 |
| HPV45 | E2 | 11 | 349 |
| HPV45 | E2 | 8 | 50 |
| HPV45 | E2 | 9 | 50 |
| HPV45 | E2 | 11 | 50 |
| HPV45 | E2 | 11 | 334 |
| HPV45 | E2 | 9 | 56 |
| HPV45 | E2 | 10 | 56 |
| HPV45 | E2 | 8 | 150 |
| HPV45 | E2 | 10 | 150 |
| HPV45 | E2 | 10 | 255 |
| HPV45 | E2 | 9 | 237 |
| HPV45 | E2 | 11 | 237 |
| HPV45 | E2 | 10 | 163 |
| HPV45 | E2 | 11 | 163 |
| HPV45 | E2 | 9 | 225 |
| HPV45 | E2 | 10 | 225 |
| HPV45 | E2 | 9 | 295 |
| HPV45 | E2 | 9 | 62 |
| HPV45 | E2 | 11 | 267 |
| HPV45 | E2 | 11 | 293 |
| HPV45 | E2 | 10 | 478 |
| HPV45 | E2 | 11 | 48 |
| HPV45 | E2 | 10 | 335 |
| HPV45 | E2 | 10 | 146 |
| HPV45 | E2 | 11 | 146 |
| HPV45 | E2 | 8 | 57 |
| HPV45 | E2 | 9 | 57 |
| HPV45 | E2 | 8 | 57 |
| HPV45 | E2 | 9 | 57 |
| HPV45 | E2 | 8 | 219 |
| HPV45 | E2 | 10 | 219 |
| HPV45 | E2 | 8 | 74 |
| HPV45 | E2 | 10 | 74 |
| HPV45 | E2 | 11 | 74 |
| HPV45 | E2 | 8 | 77 |
| HPV45 | E2 | 9 | 77 |
| HPV45 | E2 | 10 | 59 |
| HPV45 | E2 | 9 | 2 |
| HPV45 | E2 | 11 | 154 |
| HPV45 | E2 | 8 | 284 |
| HPV45 | E2 | 10 | 284 |
| HPV45 | E2 | 11 | 284 |
| HPV45 | E2 | 8 | 41 |
| HPV45 | E2 | 9 | 41 |
| HPV45 | E2 | 11 | 41 |
| HPV45 | E2 | 8 | 100 |
| HPV45 | E2 | 11 | 100 |
| HPV45 | E2 | 8 | 223 |
| HPV45 | E2 | 11 | 223 |
| HPV45 | E2 | 8 | 81 |
| HPV45 | E2 | 9 | 81 |
| HPV45 | E2 | 9 | 256 |
| HPV45 | E2 | 11 | 256 |
| HPV45 | E2 | 9 | 336 |
| HPV45 | E2 | 8 | 3 |
| HPV45 | E2 | 10 | 69 |
| HPV45 | E2 | 11 | 69 |
| HPV45 | E2 | 8 | 347 |
| HPV45 | E2 | 9 | 347 |
| HPV45 | E2 | 8 | 332 |
| HPV45 | E2 | 8 | 265 |
| HPV45 | E2 | 9 | 265 |
| HPV45 | E2 | 8 | 289 |
| HPV45 | E2 | 11 | 189 |
| HPV45 | E2 | 9 | 198 |
| HPV45 | E2 | 11 | 246 |
| HPV45 | E2 | 9 | 67 |
| HPV45 | E2 | 8 | 360 |
| HPV45 | E2 | 9 | 360 |
| HPV45 | E2 | 8 | 35 |
| HPV45 | E2 | 10 | 35 |
| HPV45 | E2 | 9 | 218 |
| HPV45 | E2 | 11 | 218 |
| HPV45 | E2 | 8 | 40 |
| HPV45 | E2 | 9 | 40 |
| HPV45 | E2 | 10 | 40 |
| HPV45 | E2 | 9 | 222 |
| HPV45 | E2 | 8 | 82 |
| HPV45 | E2 | 11 | 4 |
| HPV45 | E2 | 8 | 63 |
| HPV45 | E2 | 9 | 43 |
| HPV45 | E2 | 10 | 43 |
| HPV45 | E2 | 9 | 13 |
| HPV45 | E2 | 10 | 13 |
| HPV45 | E2 | 8 | 221 |
| HPV45 | E2 | 10 | 221 |
| HPV45 | E2 | 10 | 263 |
| HPV45 | E2 | 11 | 263 |
| HPV45 | E2 | 8 | 15 |
| HPV45 | E2 | 9 | 215 |
| HPV45 | E2 | 8 | 142 |
| HPV45 | E2 | 10 | 142 |
| HPV45 | E2 | 9 | 302 |
| HPV45 | E2 | 8 | 9 |
| HPV45 | E2 | 9 | 9 |
| HPV45 | E2 | 9 | 205 |
| HPV45 | E2 | 10 | 205 |
| HPV45 | E2 | 10 | 113 |
| HPV45 | E2 | 11 | 113 |
| HPV45 | E2 | 8 | 34 |
| HPV45 | E2 | 9 | 34 |
| HPV45 | E2 | 11 | 34 |
| HPV45 | E2 | 8 | 229 |
| HPV45 | E2 | 10 | 229 |
| HPV45 | E2 | 9 | 208 |
| HPV45 | E2 | 10 | 208 |
| HPV45 | E2 | 10 | 276 |
| HPV45 | E2 | 8 | 227 |
| HPV45 | E2 | 10 | 227 |
| HPV45 | E2 | 9 | 235 |
| HPV45 | E2 | 11 | 235 |
| HPV45 | E2 | 9 | 358 |
| HPV45 | E2 | 10 | 358 |
| HPV45 | E2 | 11 | 358 |
| HPV45 | E2 | 10 | 155 |
| HPV45 | E2 | 8 | 51 |
| HPV45 | E2 | 10 | 51 |
| HPV45 | E2 | 11 | 233 |
| HPV45 | E2 | 8 | 354 |
| HPV45 | E2 | 10 | 354 |
| HPV45 | E2 | 9 | 99 |
| HPV45 | E2 | 10 | 217 |
| HPV45 | E2 | 8 | 213 |
| HPV45 | E2 | 11 | 213 |
| HPV45 | E2 | 8 | 337 |
| HPV45 | E2 | 8 | 199 |
| HPV45 | E2 | 11 | 199 |
| HPV45 | E2 | 8 | 359 |
| HPV45 | E2 | 9 | 359 |
| HPV45 | E2 | 10 | 359 |
| HPV45 | E2 | 9 | 344 |
| HPV45 | E2 | 10 | 344 |
| HPV45 | E2 | 11 | 344 |
| HPV45 | E2 | 8 | 193 |
| HPV45 | E2 | 9 | 153 |
| HPV45 | E2 | 11 | 353 |
| HPV45 | E2 | 11 | 338 |
| HPV45 | E2 | 8 | 352 |
| HPV45 | E2 | 10 | 352 |

TABLE VIII-continued

HLA-A2 Supermotif-Bearing Peptides

| 1 | 2 | 3 | 4 |
|---|---|---|---|
| HPV45 | E2 | 9 | 138 |
| HPV45 | E2 | 10 | 138 |
| HPV45 | E2 | 9 | 39 |
| HPV45 | E2 | 10 | 39 |
| HPV45 | E2 | 11 | 39 |
| HPV45 | E2 | 8 | 326 |
| HPV45 | E2 | 10 | 326 |
| HPV45 | E2 | 11 | 326 |
| HPV45 | E2 | 10 | 98 |
| HPV45 | E2 | 8 | 313 |
| HPV45 | E2 | 11 | 313 |
| HPV45 | E2 | 8 | 166 |
| HPV45 | E2 | 11 | 166 |
| HPV45 | E2 | 11 | 145 |
| HPV45 | E2 | 10 | 137 |
| HPV45 | E2 | 11 | 137 |
| HPV45 | E6 | 8 | 37 |
| HPV45 | E6 | 11 | 59 |
| HPV45 | E6 | 8 | 68 |
| HPV45 | E6 | 11 | 68 |
| HPV45 | E6 | 8 | 105 |
| HPV45 | E6 | 11 | 105 |
| HPV45 | E6 | 8 | 108 |
| HPV45 | E6 | 8 | 18 |
| HPV45 | E6 | 11 | 18 |
| HPV45 | E6 | 8 | 32 |
| HPV45 | E6 | 11 | 32 |
| HPV45 | E6 | 8 | 16 |
| HPV45 | E6 | 10 | 16 |
| HPV45 | E6 | 10 | 51 |
| HPV45 | E6 | 11 | 51 |
| HPV45 | E6 | 8 | 143 |
| HPV45 | E6 | 11 | 51 |
| HPV45 | E6 | 8 | 143 |
| HPV45 | E6 | 11 | 27 |
| HPV45 | E6 | 9 | 20 |
| HPV45 | E6 | 11 | 20 |
| HPV45 | E6 | 9 | 77 |
| HPV45 | E6 | 10 | 97 |
| HPV45 | E6 | 9 | 88 |
| HPV45 | E6 | 11 | 88 |
| HPV45 | E6 | 10 | 43 |
| HPV45 | E6 | 8 | 47 |
| HPV45 | E6 | 9 | 47 |
| HPV45 | E6 | 8 | 53 |
| HPV45 | E6 | 9 | 53 |
| HPV45 | E6 | 11 | 53 |
| HPV45 | E6 | 10 | 136 |
| HPV45 | E6 | 9 | 132 |
| HPV45 | E6 | 11 | 120 |
| HPV45 | E6 | 8 | 30 |
| HPV45 | E6 | 9 | 30 |
| HPV45 | E6 | 10 | 30 |
| HPV45 | E6 | 11 | 130 |
| HPV45 | E6 | 10 | 60 |
| HPV45 | E6 | 9 | 93 |
| HPV45 | E6 | 10 | 93 |
| HPV45 | E6 | 11 | 93 |
| HPV45 | E6 | 8 | 54 |
| HPV45 | E6 | 10 | 54 |
| HPV45 | E6 | 11 | 54 |
| HPV45 | E6 | 9 | 36 |
| HPV45 | E6 | 10 | 92 |
| HPV45 | E6 | 11 | 92 |
| HPV45 | E6 | 9 | 13 |
| HPV45 | E6 | 11 | 13 |
| HPV45 | E6 | 11 | 102 |
| HPV45 | E6 | 9 | 25 |
| HPV45 | E6 | 8 | 1 |
| HPV45 | E6 | 8 | 95 |
| HPV45 | E6 | 8 | 95 |
| HPV45 | E6 | 9 | 22 |
| HPV45 | E6 | 10 | 22 |
| HPV45 | E6 | 8 | 114 |
| HPV45 | E6 | 11 | 111 |
| HPV45 | E6 | 8 | 7 |
| HPV45 | E6 | 11 | 7 |
| HPV45 | E6 | 8 | 149 |
| HPV45 | E6 | 10 | 149 |
| HPV45 | E6 | 11 | 146 |
| HPV45 | E6 | 8 | 41 |
| HPV45 | E6 | 9 | 29 |
| HPV45 | E6 | 10 | 29 |
| HPV45 | E6 | 11 | 29 |
| HPV45 | E6 | 8 | 24 |
| HPV45 | E6 | 10 | 24 |
| HPV45 | E6 | 10 | 84 |
| HPV45 | E6 | 11 | 84 |
| HPV45 | E6 | 8 | 89 |
| HPV45 | E6 | 10 | 89 |
| HPV45 | E6 | 11 | 38 |
| HPV45 | E6 | 10 | 8 |
| HPV45 | E6 | 8 | 62 |
| HPV45 | E6 | 8 | 45 |
| HPV45 | E6 | 10 | 45 |
| HPV45 | E6 | 11 | 45 |
| HPV45 | E7 | 8 | 48 |
| HPV45 | E7 | 8 | 6 |
| HPV45 | E7 | 10 | 6 |
| HPV45 | E7 | 10 | 64 |
| HPV45 | E7 | 8 | 25 |
| HPV45 | E7 | 8 | 83 |
| HPV45 | E7 | 10 | 83 |
| HPV45 | E7 | 8 | 41 |
| HPV45 | E7 | 10 | 41 |
| HPV45 | E7 | 8 | 20 |
| HPV45 | E7 | 8 | 74 |
| HPV45 | E7 | 11 | 74 |
| HPV45 | E7 | 8 | 91 |
| HPV45 | E7 | 8 | 97 |
| HPV45 | E7 | 8 | 44 |
| HPV45 | E7 | 9 | 47 |
| HPV45 | E7 | 8 | 14 |
| HPV45 | E7 | 11 | 14 |
| HPV45 | E7 | 11 | 11 |
| HPV45 | E7 | 8 | 8 |
| HPV45 | E7 | 8 | 87 |
| HPV45 | E7 | 9 | 87 |
| HPV45 | E7 | 10 | 75 |
| HPV45 | E7 | 8 | 17 |
| HPV45 | E7 | 10 | 17 |
| HPV45 | E7 | 11 | 17 |
| HPV45 | E7 | 9 | 57 |
| HPV45 | E7 | 10 | 23 |
| HPV45 | E7 | 10 | 89 |
| HPV45 | E7 | 8 | 88 |
| HPV45 | E7 | 11 | 88 |
| HPV45 | E7 | 9 | 54 |
| HPV45 | E7 | 10 | 54 |
| HPV45 | E7 | 8 | 5 |
| HPV45 | E7 | 9 | 5 |
| HPV45 | E7 | 11 | 5 |
| HPV45 | E7 | 10 | 72 |
| HPV45 | E7 | 8 | 85 |
| HPV45 | E7 | 10 | 85 |
| HPV45 | E7 | 11 | 85 |
| HPV45 | E7 | 8 | 80 |
| HPV45 | E7 | 11 | 80 |
| HPV45 | E7 | 11 | 93 |
| HPV45 | E7 | 9 | 7 |
| HPV45 | E7 | 9 | 86 |
| HPV45 | E7 | 10 | 86 |
| HPV45 | E7 | 10 | 94 |
| HPV45 | E7 | 11 | 94 |
| HPV45 | E7 | 9 | 76 |
| HPV45 | E7 | 11 | 76 |
| HPV45 | E7 | 10 | 12 |
| HPV45 | L1 | 11 | 517 |
| HPV45 | L1 | 10 | 161 |
| HPV45 | L1 | 10 | 191 |

TABLE VIII-continued

HLA-A2 Supermotif-Bearing Peptides

| 1 | 2 | 3 | 4 |
|---|---|---|---|
| HPV45 | L1 | 11 | 191 |
| HPV45 | L1 | 10 | 103 |
| HPV45 | L1 | 9 | 28 |
| HPV45 | L1 | 10 | 28 |
| HPV45 | L1 | 10 | 234 |
| HPV45 | L1 | 8 | 345 |
| HPV45 | L1 | 11 | 205 |
| HPV45 | L1 | 9 | 162 |
| HPV45 | L1 | 11 | 164 |
| HPV45 | L1 | 8 | 455 |
| HPV45 | L1 | 9 | 455 |
| HPV45 | L1 | 8 | 374 |
| HPV45 | L1 | 11 | 374 |
| HPV45 | L1 | 8 | 184 |
| HPV45 | L1 | 9 | 184 |
| HPV45 | L1 | 9 | 276 |
| HPV45 | L1 | 11 | 252 |
| HPV45 | L1 | 9 | 409 |
| HPV45 | L1 | 10 | 409 |
| HPV45 | L1 | 10 | 188 |
| HPV45 | L1 | 11 | 318 |
| HPV45 | L1 | 10 | 480 |
| HPV45 | L1 | 8 | 401 |
| HPV45 | L1 | 10 | 401 |
| HPV45 | L1 | 11 | 401 |
| HPV45 | L1 | 9 | 301 |
| HPV45 | L1 | 11 | 301 |
| HPV45 | L1 | 9 | 226 |
| HPV45 | L1 | 10 | 226 |
| HPV45 | L1 | 10 | 490 |
| HPV45 | L1 | 11 | 490 |
| HPV45 | L1 | 8 | 155 |
| HPV45 | L1 | 9 | 155 |
| HPV45 | L1 | 10 | 155 |
| HPV45 | L1 | 11 | 155 |
| HPV45 | L1 | 11 | 229 |
| HPV45 | L1 | 8 | 242 |
| HPV45 | L1 | 10 | 242 |
| HPV45 | L1 | 8 | 364 |
| HPV45 | L1 | 9 | 364 |
| HPV45 | L1 | 10 | 364 |
| HPV45 | L1 | 9 | 296 |
| HPV45 | L1 | 9 | 446 |
| HPV45 | L1 | 10 | 446 |
| HPV45 | L1 | 11 | 446 |
| HPV45 | L1 | 8 | 169 |
| HPV45 | L1 | 8 | 133 |
| HPV45 | L1 | 10 | 133 |
| HPV45 | L1 | 8 | 121 |
| HPV45 | L1 | 10 | 121 |
| HPV45 | L1 | 9 | 416 |
| HPV45 | L1 | 10 | 246 |
| HPV45 | L1 | 9 | 283 |
| HPV45 | L1 | 11 | 283 |
| HPV45 | L1 | 8 | 404 |
| HPV45 | L1 | 9 | 404 |
| HPV45 | L1 | 10 | 404 |
| HPV45 | L1 | 11 | 404 |
| HPV45 | L1 | 10 | 14 |
| HPV45 | L1 | 8 | 406 |
| HPV45 | L1 | 9 | 406 |
| HPV45 | L1 | 10 | 406 |
| HPV45 | L1 | 8 | 450 |
| HPV45 | L1 | 8 | 359 |
| HPV45 | L1 | 11 | 359 |
| HPV45 | L1 | 8 | 82 |
| HPV45 | L1 | 11 | 82 |
| HPV45 | L1 | 8 | 233 |
| HPV45 | L1 | 11 | 233 |
| HPV45 | L1 | 8 | 351 |
| HPV45 | L1 | 10 | 351 |
| HPV45 | L1 | 11 | 351 |
| HPV45 | L1 | 9 | 10 |
| HPV45 | L1 | 11 | 10 |
| HPV45 | L1 | 8 | 503 |
| HPV45 | L1 | 11 | 143 |
| HPV45 | L1 | 10 | 131 |
| HPV45 | L1 | 8 | 137 |
| HPV45 | L1 | 9 | 199 |
| HPV45 | L1 | 9 | 306 |
| HPV45 | L1 | 9 | 292 |
| HPV45 | L1 | 11 | 292 |
| HPV45 | L1 | 8 | 435 |
| HPV45 | L1 | 10 | 435 |
| HPV45 | L1 | 11 | 435 |
| HPV45 | L1 | 8 | 160 |
| HPV45 | L1 | 11 | 160 |
| HPV45 | L1 | 8 | 62 |
| HPV45 | L1 | 9 | 62 |
| HPV45 | L1 | 10 | 62 |
| HPV45 | L1 | 10 | 396 |
| HPV45 | L1 | 8 | 221 |
| HPV45 | L1 | 10 | 221 |
| HPV45 | L1 | 9 | 12 |
| HPV45 | L1 | 8 | 11 |
| HPV45 | L1 | 10 | 11 |
| HPV45 | L1 | 8 | 5 |
| HPV45 | L1 | 9 | 5 |
| HPV45 | L1 | 11 | 5 |
| HPV45 | L1 | 9 | 428 |
| HPV45 | L1 | 8 | 185 |
| HPV45 | L1 | 8 | 411 |
| HPV45 | L1 | 11 | 411 |
| HPV45 | L1 | 9 | 166 |
| HPV45 | L1 | 11 | 166 |
| HPV45 | L1 | 8 | 328 |
| HPV45 | L1 | 9 | 344 |
| HPV45 | L1 | 8 | 152 |
| HPV45 | L1 | 10 | 152 |
| HPV45 | L1 | 11 | 152 |
| HPV45 | L1 | 9 | 473 |
| HPV45 | L1 | 9 | 86 |
| HPV45 | L1 | 8 | 467 |
| HPV45 | L1 | 8 | 179 |
| HPV45 | L1 | 11 | 179 |
| HPV45 | L1 | 9 | 91 |
| HPV45 | L1 | 11 | 68 |
| HPV45 | L1 | 8 | 240 |
| HPV45 | L1 | 10 | 240 |
| HPV45 | L1 | 9 | 402 |
| HPV45 | L1 | 10 | 402 |
| HPV45 | L1 | 11 | 402 |
| HPV45 | L1 | 9 | 207 |
| HPV45 | L1 | 11 | 207 |
| HPV45 | L1 | 9 | 413 |
| HPV45 | L1 | 11 | 371 |
| HPV45 | L1 | 10 | 69 |
| HPV45 | L1 | 11 | 69 |
| HPV45 | L1 | 8 | 444 |
| HPV45 | L1 | 11 | 444 |
| HPV45 | L1 | 11 | 499 |
| HPV45 | L1 | 8 | 125 |
| HPV45 | L1 | 10 | 125 |
| HPV45 | L1 | 11 | 1 |
| HPV45 | L1 | 10 | 27 |
| HPV45 | L1 | 11 | 27 |
| HPV45 | L1 | 8 | 227 |
| HPV45 | L1 | 9 | 227 |
| HPV45 | L1 | 8 | 4 |
| HPV45 | L1 | 9 | 4 |
| HPV45 | L1 | 10 | 4 |
| HPV45 | L1 | 8 | 370 |
| HPV45 | L1 | 10 | 310 |
| HPV45 | L1 | 8 | 356 |
| HPV45 | L1 | 10 | 356 |
| HPV45 | L1 | 11 | 356 |
| HPV45 | L1 | 9 | 49 |
| HPV45 | L1 | 11 | 49 |
| HPV45 | L1 | 9 | 219 |
| HPV45 | L1 | 10 | 219 |

TABLE VIII-continued

HLA-A2 Supermotif-Bearing Peptides

| 1 | 2 | 3 | 4 |
|---|---|---|---|
| HPV45 | L1 | 9 | 19 |
| HPV45 | L1 | 10 | 19 |
| HPV45 | L1 | 11 | 19 |
| HPV45 | L1 | 9 | 17 |
| HPV45 | L1 | 11 | 17 |
| HPV45 | L1 | 9 | 173 |
| HPV45 | L1 | 11 | 173 |
| HPV45 | L1 | 8 | 516 |
| HPV45 | L1 | 8 | 190 |
| HPV45 | L1 | 11 | 190 |
| HPV45 | L1 | 8 | 22 |
| HPV45 | L1 | 8 | 248 |
| HPV45 | L1 | 8 | 214 |
| HPV45 | L1 | 9 | 214 |
| HPV45 | L1 | 8 | 493 |
| HPV45 | L1 | 10 | 493 |
| HPV45 | L1 | 9 | 299 |
| HPV45 | L1 | 11 | 299 |
| HPV45 | L1 | 10 | 508 |
| HPV45 | L1 | 11 | 508 |
| HPV45 | L1 | 11 | 387 |
| HPV45 | L1 | 8 | 440 |
| HPV45 | L1 | 9 | 380 |
| HPV45 | L1 | 9 | 501 |
| HPV45 | L1 | 10 | 501 |
| HPV45 | L1 | 8 | 87 |
| HPV45 | L1 | 8 | 182 |
| HPV45 | L1 | 10 | 182 |
| HPV45 | L1 | 11 | 182 |
| HPV45 | L1 | 8 | 407 |
| HPV45 | L1 | 9 | 407 |
| HPV45 | L1 | 11 | 407 |
| HPV45 | L1 | 11 | 281 |
| HPV45 | L1 | 9 | 334 |
| HPV45 | L1 | 9 | 357 |
| HPV45 | L1 | 10 | 357 |
| HPV45 | L1 | 10 | 206 |
| HPV45 | L1 | 11 | 26 |
| HPV45 | L1 | 11 | 263 |
| HPV45 | L1 | 10 | 180 |
| HPV45 | L1 | 8 | 290 |
| HPV45 | L1 | 9 | 290 |
| HPV45 | L1 | 11 | 290 |
| HPV45 | L1 | 9 | 124 |
| HPV45 | L1 | 11 | 124 |
| HPV45 | L1 | 8 | 56 |
| HPV45 | L1 | 9 | 46 |
| HPV45 | L1 | 9 | 265 |
| HPV45 | L1 | 8 | 158 |
| HPV45 | L1 | 9 | 158 |
| HPV45 | L1 | 10 | 158 |
| HPV45 | L1 | 10 | 93 |
| HPV45 | L1 | 11 | 93 |
| HPV45 | L1 | 9 | 254 |
| HPV45 | L1 | 11 | 254 |
| HPV45 | L1 | 11 | 58 |
| HPV45 | L1 | 10 | 427 |
| HPV45 | L1 | 9 | 327 |
| HPV45 | L1 | 9 | 443 |
| HPV45 | L1 | 11 | 272 |
| HPV45 | L1 | 10 | 333 |
| HPV45 | L1 | 10 | 521 |
| HPV45 | L1 | 8 | 115 |
| HPV45 | L1 | 11 | 115 |
| HPV45 | L1 | 10 | 238 |
| HPV45 | L1 | 8 | 368 |
| HPV45 | L1 | 10 | 368 |
| HPV45 | L1 | 9 | 376 |
| HPV45 | L1 | 9 | 519 |
| HPV45 | L1 | 10 | 35 |
| HPV45 | L1 | 11 | 35 |
| HPV45 | L1 | 8 | 43 |
| HPV45 | L1 | 10 | 453 |
| HPV45 | L1 | 11 | 453 |
| HPV45 | L1 | 9 | 175 |
| HPV45 | L1 | 11 | 175 |
| HPV45 | L1 | 8 | 414 |
| HPV45 | L1 | 11 | 414 |
| HPV45 | L1 | 9 | 522 |
| HPV45 | L1 | 11 | 522 |
| HPV45 | L1 | 8 | 163 |
| HPV45 | L1 | 9 | 509 |
| HPV45 | L1 | 10 | 509 |
| HPV45 | L1 | 8 | 220 |
| HPV45 | L1 | 9 | 220 |
| HPV45 | L1 | 11 | 220 |
| HPV45 | L1 | 8 | 410 |
| HPV45 | L1 | 9 | 410 |
| HPV45 | L1 | 10 | 116 |
| HPV45 | L1 | 11 | 116 |
| HPV45 | L1 | 10 | 372 |
| HPV45 | L1 | 8 | 200 |
| HPV45 | L1 | 9 | 239 |
| HPV45 | L1 | 11 | 239 |
| HPV45 | L1 | 10 | 412 |
| HPV45 | L1 | 8 | 167 |
| HPV45 | L1 | 10 | 167 |
| HPV45 | L1 | 9 | 181 |
| HPV45 | L1 | 11 | 181 |
| HPV45 | L1 | 8 | 377 |
| HPV45 | L1 | 9 | 122 |
| HPV45 | L1 | 11 | 122 |
| HPV45 | L1 | 8 | 365 |
| HPV45 | L1 | 9 | 365 |
| HPV45 | L1 | 11 | 365 |
| HPV45 | L1 | 11 | 441 |
| HPV45 | L1 | 9 | 70 |
| HPV45 | L1 | 10 | 70 |
| HPV45 | L1 | 8 | 297 |
| HPV45 | L1 | 11 | 297 |
| HPV45 | L1 | 9 | 361 |
| HPV45 | L1 | 11 | 361 |
| HPV45 | L1 | 9 | 36 |
| HPV45 | L1 | 10 | 36 |
| HPV45 | L1 | 11 | 102 |
| HPV45 | L1 | 11 | 44 |
| HPV45 | L1 | 9 | 454 |
| HPV45 | L1 | 10 | 454 |
| HPV45 | L1 | 10 | 165 |
| HPV45 | L1 | 8 | 293 |
| HPV45 | L1 | 10 | 293 |
| HPV45 | L1 | 8 | 417 |
| HPV45 | L1 | 10 | 500 |
| HPV45 | L1 | 11 | 500 |
| HPV45 | L1 | 8 | 456 |
| HPV45 | L1 | 10 | 360 |
| HPV45 | L1 | 8 | 362 |
| HPV45 | L1 | 10 | 362 |
| HPV45 | L1 | 11 | 362 |
| HPV45 | L1 | 8 | 47 |
| HPV45 | L1 | 11 | 47 |
| HPV45 | L1 | 11 | 78 |
| HPV45 | L1 | 8 | 127 |
| HPV45 | L1 | 10 | 196 |
| HPV45 | L1 | 9 | 420 |
| HPV45 | L1 | 10 | 420 |
| HPV45 | L1 | 9 | 303 |
| HPV45 | L1 | 8 | 38 |
| HPV45 | L1 | 10 | 38 |
| HPV45 | L1 | 11 | 38 |
| HPV45 | L1 | 8 | 95 |
| HPV45 | L1 | 9 | 95 |
| HPV45 | L1 | 10 | 95 |
| HPV45 | L1 | 11 | 53 |
| HPV45 | L2 | 9 | 6 |
| HPV45 | L2 | 10 | 6 |
| HPV45 | L2 | 8 | 381 |
| HPV45 | L2 | 9 | 381 |
| HPV45 | L2 | 10 | 381 |
| HPV45 | L2 | 8 | 327 |

TABLE VIII-continued

HLA-A2 Supermotif-Bearing Peptides

| 1 | 2 | 3 | 4 |
|---|---|---|---|
| HPV45 | L2 | 11 | 327 |
| HPV45 | L2 | 8 | 286 |
| HPV45 | L2 | 9 | 286 |
| HPV45 | L2 | 10 | 328 |
| HPV45 | L2 | 11 | 328 |
| HPV45 | L2 | 11 | 303 |
| HPV45 | L2 | 10 | 340 |
| HPV45 | L2 | 8 | 139 |
| HPV45 | L2 | 9 | 139 |
| HPV45 | L2 | 8 | 405 |
| HPV45 | L2 | 10 | 405 |
| HPV45 | L2 | 9 | 278 |
| HPV45 | L2 | 10 | 278 |
| HPV45 | L2 | 8 | 322 |
| HPV45 | L2 | 11 | 322 |
| HPV45 | L2 | 9 | 142 |
| HPV45 | L2 | 11 | 142 |
| HPV45 | L2 | 11 | 16 |
| HPV45 | L2 | 9 | 260 |
| HPV45 | L2 | 9 | 83 |
| HPV45 | L2 | 10 | 83 |
| HPV45 | L2 | 11 | 83 |
| HPV45 | L2 | 9 | 30 |
| HPV45 | L2 | 10 | 30 |
| HPV45 | L2 | 11 | 30 |
| HPV45 | L2 | 10 | 397 |
| HPV45 | L2 | 11 | 397 |
| HPV45 | L2 | 10 | 348 |
| HPV45 | L2 | 8 | 331 |
| HPV45 | L2 | 10 | 331 |
| HPV45 | L2 | 11 | 331 |
| HPV45 | L2 | 8 | 194 |
| HPV45 | L2 | 8 | 129 |
| HPV45 | L2 | 9 | 129 |
| HPV45 | L2 | 11 | 129 |
| HPV45 | L2 | 8 | 333 |
| HPV45 | L2 | 9 | 333 |
| HPV45 | L2 | 8 | 169 |
| HPV45 | L2 | 8 | 175 |
| HPV45 | L2 | 10 | 175 |
| HPV45 | L2 | 8 | 456 |
| HPV45 | L2 | 8 | 200 |
| HPV45 | L2 | 11 | 200 |
| HPV45 | L2 | 9 | 53 |
| HPV45 | L2 | 8 | 241 |
| HPV45 | L2 | 9 | 241 |
| HPV45 | L2 | 10 | 241 |
| HPV45 | L2 | 11 | 276 |
| HPV45 | L2 | 9 | 122 |
| HPV45 | L2 | 10 | 122 |
| HPV45 | L2 | 11 | 157 |
| HPV45 | L2 | 8 | 306 |
| HPV45 | L2 | 8 | 368 |
| HPV45 | L2 | 9 | 368 |
| HPV45 | L2 | 10 | 368 |
| HPV45 | L2 | 8 | 116 |
| HPV45 | L2 | 10 | 116 |
| HPV45 | L2 | 9 | 51 |
| HPV45 | L2 | 11 | 51 |
| HPV45 | L2 | 9 | 430 |
| HPV45 | L2 | 8 | 300 |
| HPV45 | L2 | 8 | 25 |
| HPV45 | L2 | 11 | 25 |
| HPV45 | L2 | 8 | 206 |
| HPV45 | L2 | 10 | 206 |
| HPV45 | L2 | 10 | 60 |
| HPV45 | L2 | 8 | 124 |
| HPV45 | L2 | 8 | 37 |
| HPV45 | L2 | 9 | 37 |
| HPV45 | L2 | 8 | 134 |
| HPV45 | L2 | 10 | 134 |
| HPV45 | L2 | 11 | 134 |
| HPV45 | L2 | 8 | 292 |
| HPV45 | L2 | 8 | 411 |
| HPV45 | L2 | 11 | 411 |
| HPV45 | L2 | 9 | 326 |
| HPV45 | L2 | 10 | 167 |
| HPV45 | L2 | 9 | 406 |
| HPV45 | L2 | 8 | 279 |
| HPV45 | L2 | 9 | 279 |
| HPV45 | L2 | 8 | 407 |
| HPV45 | L2 | 9 | 44 |
| HPV45 | L2 | 11 | 44 |
| HPV45 | L2 | 8 | 143 |
| HPV45 | L2 | 10 | 143 |
| HPV45 | L2 | 8 | 130 |
| HPV45 | L2 | 10 | 130 |
| HPV45 | L2 | 11 | 130 |
| HPV45 | L2 | 10 | 103 |
| HPV45 | L2 | 11 | 103 |
| HPV45 | L2 | 8 | 43 |
| HPV45 | L2 | 10 | 43 |
| HPV45 | L2 | 10 | 22 |
| HPV45 | L2 | 11 | 22 |
| HPV45 | L2 | 8 | 34 |
| HPV45 | L2 | 11 | 34 |
| HPV45 | L2 | 11 | 40 |
| HPV45 | L2 | 10 | 337 |
| HPV45 | L2 | 8 | 334 |
| HPV45 | L2 | 11 | 197 |
| HPV45 | L2 | 8 | 45 |
| HPV45 | L2 | 10 | 45 |
| HPV45 | L2 | 8 | 242 |
| HPV45 | L2 | 9 | 242 |
| HPV45 | L2 | 8 | 375 |
| HPV45 | L2 | 9 | 392 |
| HPV45 | L2 | 11 | 392 |
| HPV45 | L2 | 8 | 106 |
| HPV45 | L2 | 9 | 106 |
| HPV45 | L2 | 8 | 248 |
| HPV45 | L2 | 8 | 422 |
| HPV45 | L2 | 10 | 422 |
| HPV45 | L2 | 8 | 179 |
| HPV45 | L2 | 8 | 231 |
| HPV45 | L2 | 9 | 79 |
| HPV45 | L2 | 8 | 270 |
| HPV45 | L2 | 10 | 270 |
| HPV45 | L2 | 11 | 270 |
| HPV45 | L2 | 9 | 387 |
| HPV45 | L2 | 8 | 160 |
| HPV45 | L2 | 9 | 160 |
| HPV45 | L2 | 11 | 160 |
| HPV45 | L2 | 9 | 285 |
| HPV45 | L2 | 10 | 285 |
| HPV45 | L2 | 8 | 356 |
| HPV45 | L2 | 9 | 356 |
| HPV45 | L2 | 9 | 138 |
| HPV45 | L2 | 10 | 138 |
| HPV45 | L2 | 8 | 254 |
| HPV45 | L2 | 9 | 254 |
| HPV45 | L2 | 10 | 254 |
| HPV45 | L2 | 8 | 325 |
| HPV45 | L2 | 10 | 325 |
| HPV45 | L2 | 9 | 209 |
| HPV45 | L2 | 10 | 209 |
| HPV45 | L2 | 8 | 399 |
| HPV45 | L2 | 9 | 399 |
| HPV45 | L2 | 10 | 399 |
| HPV45 | L2 | 11 | 258 |
| HPV45 | L2 | 8 | 73 |
| HPV45 | L2 | 9 | 73 |
| HPV45 | L2 | 10 | 73 |
| HPV45 | L2 | 11 | 336 |
| HPV45 | L2 | 8 | 214 |
| HPV45 | L2 | 8 | 391 |
| HPV45 | L2 | 10 | 391 |
| HPV45 | L2 | 9 | 413 |
| HPV45 | L2 | 11 | 413 |
| HPV45 | L2 | 10 | 171 |
| HPV45 | L2 | 8 | 98 |

TABLE VIII-continued

HLA-A2 Supermotif-Bearing Peptides

| 1 | 2 | 3 | 4 |
|---|---|---|---|
| HPV45 | L2 | 9 | 98 |
| HPV45 | L2 | 10 | 98 |
| HPV45 | L2 | 11 | 120 |
| HPV45 | L2 | 8 | 420 |
| HPV45 | L2 | 10 | 420 |
| HPV45 | L2 | 8 | 86 |
| HPV45 | L2 | 11 | 86 |
| HPV45 | L2 | 11 | 185 |
| HPV45 | L2 | 11 | 267 |
| HPV45 | L2 | 8 | 145 |
| HPV45 | L2 | 11 | 145 |
| HPV45 | L2 | 11 | 216 |
| HPV45 | L2 | 9 | 95 |
| HPV45 | L2 | 10 | 95 |
| HPV45 | L2 | 11 | 95 |
| HPV45 | L2 | 8 | 118 |
| HPV45 | L2 | 10 | 90 |
| HPV45 | L2 | 11 | 232 |
| HPV45 | L2 | 10 | 198 |
| HPV45 | L2 | 9 | 172 |
| HPV45 | L2 | 11 | 172 |
| HPV45 | L2 | 10 | 233 |
| HPV45 | L2 | 11 | 233 |
| HPV45 | L2 | 8 | 5 |
| HPV45 | L2 | 10 | 5 |
| HPV45 | L2 | 11 | 5 |
| HPV45 | L2 | 8 | 229 |
| HPV45 | L2 | 10 | 229 |
| HPV45 | L2 | 10 | 11 |
| HPV45 | L2 | 11 | 451 |
| HPV45 | L2 | 8 | 298 |
| HPV45 | L2 | 10 | 298 |
| HPV45 | L2 | 10 | 225 |
| HPV45 | L2 | 8 | 19 |
| HPV45 | L2 | 8 | 316 |
| HPV45 | L2 | 11 | 316 |
| HPV45 | L2 | 11 | 220 |
| HPV45 | L2 | 8 | 235 |
| HPV45 | L2 | 9 | 235 |
| HPV45 | L2 | 8 | 13 |
| HPV45 | L2 | 8 | 339 |
| HPV45 | L2 | 11 | 339 |
| HPV45 | L2 | 9 | 394 |
| HPV45 | L2 | 8 | 166 |
| HPV45 | L2 | 11 | 166 |
| HPV45 | L2 | 8 | 151 |
| HPV45 | L2 | 11 | 151 |
| HPV45 | L2 | 11 | 102 |
| HPV45 | L2 | 9 | 49 |
| HPV45 | L2 | 11 | 49 |
| HPV45 | L2 | 8 | 374 |
| HPV45 | L2 | 9 | 374 |
| HPV45 | L2 | 9 | 247 |
| HPV45 | L2 | 10 | 239 |
| HPV45 | L2 | 11 | 239 |
| HPV45 | L2 | 10 | 379 |
| HPV45 | L2 | 11 | 379 |
| HPV45 | L2 | 8 | 362 |
| HPV45 | L2 | 10 | 212 |
| HPV45 | L2 | 8 | 154 |
| HPV45 | L2 | 9 | 417 |
| HPV45 | L2 | 10 | 417 |
| HPV45 | L2 | 11 | 417 |
| HPV45 | L2 | 8 | 424 |
| HPV45 | L2 | 11 | 424 |
| HPV45 | L2 | 10 | 149 |
| HPV45 | L2 | 9 | 111 |
| HPV45 | L2 | 11 | 111 |
| HPV45 | L2 | 9 | 380 |
| HPV45 | L2 | 10 | 380 |
| HPV45 | L2 | 11 | 380 |
| HPV45 | L2 | 10 | 380 |
| HPV45 | L2 | 11 | 380 |
| HPV45 | L2 | 10 | 262 |
| HPV45 | L2 | 8 | 105 |
| HPV45 | L2 | 9 | 105 |
| HPV45 | L2 | 10 | 105 |
| HPV45 | L2 | 10 | 304 |
| HPV45 | L2 | 8 | 38 |
| HPV45 | L2 | 8 | 261 |
| HPV45 | L2 | 11 | 261 |
| HPV45 | L2 | 8 | 136 |
| HPV45 | L2 | 9 | 136 |
| HPV45 | L2 | 11 | 136 |
| HPV45 | L2 | 11 | 359 |
| HPV45 | L2 | 9 | 135 |
| HPV45 | L2 | 10 | 135 |
| HPV45 | L2 | 10 | 425 |
| HPV45 | L2 | 9 | 426 |
| HPV45 | L2 | 10 | 146 |
| HPV45 | L2 | 10 | 389 |
| HPV45 | L2 | 11 | 293 |
| HPV45 | L2 | 10 | 217 |
| HPV45 | L2 | 8 | 80 |
| HPV45 | L2 | 9 | 113 |
| HPV45 | L2 | 11 | 113 |
| HPV45 | L2 | 8 | 92 |
| HPV45 | L2 | 8 | 31 |
| HPV45 | L2 | 9 | 31 |
| HPV45 | L2 | 10 | 31 |
| HPV45 | L2 | 11 | 31 |
| HPV45 | L2 | 8 | 140 |
| HPV45 | L2 | 11 | 140 |
| HPV45 | L2 | 11 | 249 |
| HPV45 | L2 | 9 | 104 |
| HPV45 | L2 | 10 | 104 |
| HPV45 | L2 | 11 | 104 |
| HPV45 | L2 | 8 | 388 |
| HPV45 | L2 | 11 | 388 |
| HPV45 | L2 | 8 | 112 |
| HPV45 | L2 | 10 | 112 |
| HPV45 | L2 | 11 | 81 |
| HPV45 | L2 | 9 | 91 |
| HPV45 | L2 | 8 | 350 |
| HPV45 | L2 | 10 | 350 |
| HPV45 | L2 | 11 | 350 |
| HPV45 | L2 | 11 | 428 |
| HPV45 | L2 | 8 | 401 |
| HPV45 | L2 | 10 | 71 |
| HPV45 | L2 | 11 | 71 |
| HPV56 | E2 | 8 | 15 |
| HPV56 | E2 | 11 | 15 |
| HPV56 | E2 | 8 | 21 |
| HPV56 | E2 | 9 | 21 |
| HPV56 | E2 | 9 | 4 |
| HPV56 | E2 | 10 | 71 |
| HPV56 | E2 | 8 | 204 |
| HPV56 | E2 | 11 | 204 |
| HPV56 | E2 | 8 | 39 |
| HPV56 | E2 | 9 | 39 |
| HPV56 | E2 | 9 | 263 |
| HPV56 | E2 | 11 | 263 |
| HPV56 | E2 | 10 | 117 |
| HPV56 | E2 | 8 | 288 |
| HPV56 | E2 | 11 | 288 |
| HPV56 | E2 | 8 | 154 |
| HPV56 | E2 | 11 | 154 |
| HPV56 | E2 | 11 | 154 |
| HPV56 | E2 | 9 | 128 |
| HPV56 | E2 | 9 | 17 |
| HPV56 | E2 | 11 | 17 |
| HPV56 | E2 | 9 | 294 |
| HPV56 | E2 | 10 | 294 |
| HPV56 | E2 | 9 | 254 |
| HPV56 | E2 | 11 | 254 |
| HPV56 | E2 | 11 | 261 |
| HPV56 | E2 | 11 | 99 |
| HPV56 | E2 | 10 | 94 |
| HPV56 | E2 | 9 | 201 |
| HPV56 | E2 | 11 | 201 |

TABLE VIII-continued

HLA-A2 Supermotif-Bearing Peptides

| 1 | 2 | 3 | 4 |
|---|---|---|---|
| HPV56 | E2 | 8 | 210 |
| HPV56 | E2 | 9 | 239 |
| HPV56 | E2 | 10 | 208 |
| HPV56 | E2 | 10 | 297 |
| HPV56 | E2 | 11 | 297 |
| HPV56 | E2 | 8 | 20 |
| HPV56 | E2 | 9 | 20 |
| HPV56 | E2 | 10 | 20 |
| HPV56 | E2 | 10 | 280 |
| HPV56 | E2 | 9 | 281 |
| HPV56 | E2 | 8 | 11 |
| HPV56 | E2 | 10 | 11 |
| HPV56 | E2 | 11 | 11 |
| HPV56 | E2 | 8 | 9 |
| HPV56 | E2 | 10 | 9 |
| HPV56 | E2 | 8 | 299 |
| HPV56 | E2 | 9 | 299 |
| HPV56 | E2 | 8 | 258 |
| HPV56 | E2 | 10 | 258 |
| HPV56 | E2 | 8 | 233 |
| HPV56 | E2 | 8 | 163 |
| HPV56 | E2 | 10 | 163 |
| HPV56 | E2 | 11 | 108 |
| HPV56 | E2 | 11 | 90 |
| HPV56 | E2 | 8 | 50 |
| HPV56 | E2 | 11 | 5 |
| HPV56 | E2 | 9 | 72 |
| HPV56 | E2 | 10 | 1 |
| HPV56 | E2 | 9 | 216 |
| HPV56 | E2 | 8 | 160 |
| HPV56 | E2 | 9 | 160 |
| HPV56 | E2 | 11 | 160 |
| HPV56 | E2 | 8 | 149 |
| HPV56 | E2 | 10 | 152 |
| HPV56 | E2 | 9 | 19 |
| HPV56 | E2 | 10 | 19 |
| HPV56 | E2 | 11 | 19 |
| HPV56 | E2 | 10 | 6 |
| HPV56 | E2 | 11 | 6 |
| HPV56 | E2 | 8 | 14 |
| HPV56 | E2 | 9 | 14 |
| HPV56 | E2 | 11 | 279 |
| HPV56 | E2 | 8 | 135 |
| HPV56 | E2 | 11 | 135 |
| HPV56 | E2 | 10 | 144 |
| HPV56 | E2 | 9 | 272 |
| HPV56 | E2 | 10 | 272 |
| HPV56 | E2 | 11 | 272 |
| HPV56 | E2 | 9 | 169 |
| HPV56 | E2 | 10 | 169 |
| HPV56 | E2 | 11 | 169 |
| HPV56 | E2 | 11 | 26 |
| HPV56 | E2 | 8 | 266 |
| HPV56 | E2 | 8 | 171 |
| HPV56 | E2 | 9 | 171 |
| HPV56 | E2 | 10 | 141 |
| HPV56 | E2 | 8 | 282 |
| HPV56 | E2 | 9 | 28 |
| HPV56 | E2 | 10 | 28 |
| HPV56 | E2 | 9 | 259 |
| HPV56 | E2 | 9 | 36 |
| HPV56 | E2 | 11 | 36 |
| HPV56 | E2 | 10 | 289 |
| HPV56 | E2 | 9 | 206 |
| HPV56 | E2 | 10 | 27 |
| HPV56 | E2 | 11 | 27 |
| HPV56 | E2 | 11 | 167 |
| HPV56 | E2 | 8 | 165 |
| HPV56 | E2 | 9 | 164 |
| HPV56 | E2 | 10 | 155 |
| HPV56 | E2 | 11 | 155 |
| HPV56 | E2 | 8 | 18 |
| HPV56 | E2 | 10 | 18 |
| HPV56 | E2 | 11 | 18 |
| HPV56 | E2 | 8 | 264 |
| HPV56 | E2 | 10 | 264 |
| HPV56 | E2 | 10 | 205 |
| HPV56 | E2 | 11 | 237 |
| HPV56 | E2 | 8 | 88 |
| HPV56 | E2 | 10 | 35 |
| HPV56 | E2 | 11 | 270 |
| HPV56 | E2 | 8 | 111 |
| HPV56 | E2 | 8 | 102 |
| HPV56 | E2 | 11 | 102 |
| HPV56 | E6 | 11 | 89 |
| HPV56 | E6 | 8 | 64 |
| HPV56 | E6 | 8 | 139 |
| HPV56 | E6 | 8 | 69 |
| HPV56 | E6 | 8 | 33 |
| HPV56 | E6 | 9 | 33 |
| HPV56 | E6 | 11 | 33 |
| HPV56 | E6 | 9 | 23 |
| HPV56 | E6 | 11 | 39 |
| HPV56 | E6 | 8 | 20 |
| HPV56 | E6 | 10 | 20 |
| HPV56 | E6 | 8 | 44 |
| HPV56 | E6 | 10 | 44 |
| HPV56 | E6 | 8 | 48 |
| HPV56 | E6 | 9 | 48 |
| HPV56 | E6 | 8 | 88 |
| HPV56 | E6 | 8 | 129 |
| HPV56 | E6 | 8 | 17 |
| HPV56 | E6 | 10 | 17 |
| HPV56 | E6 | 11 | 17 |
| HPV56 | E6 | 10 | 131 |
| HPV56 | E6 | 9 | 94 |
| HPV56 | E6 | 10 | 94 |
| HPV56 | E6 | 11 | 94 |
| HPV56 | E6 | 11 | 54 |
| HPV56 | E6 | 8 | 97 |
| HPV56 | E6 | 11 | 130 |
| HPV56 | E6 | 9 | 26 |
| HPV56 | E6 | 11 | 103 |
| HPV56 | E6 | 8 | 113 |
| HPV56 | E6 | 10 | 40 |
| HPV56 | E6 | 10 | 55 |
| HPV56 | E6 | 11 | 55 |
| HPV56 | E6 | 10 | 25 |
| HPV56 | E6 | 9 | 112 |
| HPV56 | E6 | 8 | 8 |
| HPV56 | E6 | 11 | 8 |
| HPV56 | E6 | 10 | 145 |
| HPV56 | E6 | 11 | 145 |
| HPV56 | E6 | 8 | 42 |
| HPV56 | E6 | 10 | 42 |
| HPV56 | E6 | 11 | 30 |
| HPV56 | E6 | 11 | 144 |
| HPV56 | E6 | 10 | 67 |
| HPV56 | E6 | 10 | 93 |
| HPV56 | E6 | 11 | 93 |
| HPV56 | E6 | 8 | 14 |
| HPV56 | E6 | 9 | 14 |
| HPV56 | E6 | 11 | 14 |
| HPV56 | E6 | 10 | 85 |
| HPV56 | E6 | 11 | 85 |
| HPV56 | E6 | 10 | 90 |
| HPV56 | E6 | 9 | 21 |
| HPV56 | E6 | 11 | 21 |
| HPV56 | E6 | 8 | 63 |
| HPV56 | E6 | 9 | 63 |
| HPV56 | E7 | 8 | 93 |
| HPV56 | E7 | 10 | 93 |
| HPV56 | E7 | 9 | 75 |
| HPV56 | E7 | 11 | 75 |
| HPV56 | E7 | 8 | 22 |
| HPV56 | E7 | 8 | 82 |
| HPV56 | E7 | 9 | 82 |
| HPV56 | E7 | 10 | 82 |
| HPV56 | E7 | 10 | 10 |
| HPV56 | E7 | 10 | 20 |

TABLE VIII-continued

HLA-A2 Supermotif-Bearing Peptides

| 1 | 2 | 3 | 4 |
|---|---|---|---|
| HPV56 | E7 | 8 | 14 |
| HPV56 | E7 | 10 | 14 |
| HPV56 | E7 | 10 | 70 |
| HPV56 | E7 | 9 | 92 |
| HPV56 | E7 | 11 | 92 |
| HPV56 | E7 | 9 | 42 |
| HPV56 | E7 | 8 | 56 |
| HPV56 | E7 | 10 | 62 |
| HPV56 | E7 | 11 | 62 |
| HPV56 | E7 | 8 | 76 |
| HPV56 | E7 | 10 | 76 |
| HPV56 | E7 | 11 | 76 |
| HPV56 | E7 | 8 | 54 |
| HPV56 | E7 | 10 | 54 |
| HPV56 | E7 | 8 | 4 |
| HPV56 | E7 | 9 | 4 |
| HPV56 | E7 | 10 | 4 |
| HPV56 | E7 | 8 | 89 |
| HPV56 | E7 | 9 | 89 |
| HPV56 | E7 | 8 | 90 |
| HPV56 | E7 | 11 | 90 |
| HPV56 | E7 | 8 | 8 |
| HPV56 | E7 | 9 | 8 |
| HPV56 | E7 | 8 | 43 |
| HPV56 | E7 | 11 | 43 |
| HPV56 | E7 | 9 | 15 |
| HPV56 | E7 | 9 | 94 |
| HPV56 | E7 | 11 | 47 |
| HPV56 | E7 | 8 | 6 |
| HPV56 | E7 | 10 | 6 |
| HPV56 | E7 | 11 | 6 |
| HPV56 | E7 | 9 | 52 |
| HPV56 | E7 | 10 | 52 |
| HPV56 | E7 | 9 | 49 |
| HPV56 | E7 | 11 | 73 |
| HPV56 | E7 | 8 | 88 |
| HPV56 | E7 | 9 | 88 |
| HPV56 | E7 | 10 | 88 |
| HPV56 | E7 | 10 | 48 |
| HPV56 | E7 | 8 | 87 |
| HPV56 | E7 | 9 | 87 |
| HPV56 | E7 | 10 | 87 |
| HPV56 | E7 | 11 | 87 |
| HPV56 | E7 | 10 | 51 |
| HPV56 | E7 | 11 | 51 |
| HPV56 | E7 | 8 | 84 |
| HPV56 | E7 | 10 | 84 |
| HPV56 | E7 | 11 | 84 |
| HPV56 | E7 | 8 | 78 |
| HPV56 | E7 | 9 | 78 |
| HPV56 | E7 | 9 | 7 |
| HPV56 | E7 | 10 | 7 |
| HPV56 | E7 | 8 | 95 |
| HPV56 | E7 | 8 | 12 |
| HPV56 | E7 | 10 | 12 |
| HPV56 | E7 | 8 | 72 |
| HPV56 | E7 | 8 | 86 |
| HPV56 | E7 | 9 | 86 |
| HPV56 | E7 | 10 | 86 |
| HPV56 | E7 | 11 | 86 |
| HPV56 | E7 | 9 | 11 |
| HPV56 | E7 | 11 | 11 |
| HPV56 | E7 | 9 | 71 |
| HPV56 | E7 | 9 | 85 |
| HPV56 | E7 | 10 | 85 |
| HPV56 | E7 | 11 | 85 |
| HPV56 | L1 | 11 | 458 |
| HPV56 | L1 | 10 | 198 |
| HPV56 | L1 | 11 | 198 |
| HPV56 | L1 | 8 | 350 |
| HPV56 | L1 | 10 | 338 |
| HPV56 | L1 | 9 | 58 |
| HPV56 | L1 | 11 | 58 |
| HPV56 | L1 | 10 | 381 |
| HPV56 | L1 | 8 | 327 |
| HPV56 | L1 | 9 | 327 |
| HPV56 | L1 | 8 | 514 |
| HPV56 | L1 | 10 | 514 |
| HPV56 | L1 | 11 | 444 |
| HPV56 | L1 | 10 | 37 |
| HPV56 | L1 | 10 | 512 |
| HPV56 | L1 | 8 | 207 |
| HPV56 | L1 | 9 | 207 |
| HPV56 | L1 | 10 | 207 |
| HPV56 | L1 | 9 | 79 |
| HPV56 | L1 | 10 | 79 |
| HPV56 | L1 | 9 | 26 |
| HPV56 | L1 | 11 | 26 |
| HPV56 | L1 | 8 | 19 |
| HPV56 | L1 | 9 | 19 |
| HPV56 | L1 | 11 | 19 |
| HPV56 | L1 | 8 | 191 |
| HPV56 | L1 | 9 | 191 |
| HPV56 | L1 | 8 | 461 |
| HPV56 | L1 | 10 | 195 |
| HPV56 | L1 | 9 | 389 |
| HPV56 | L1 | 11 | 274 |
| HPV56 | L1 | 9 | 233 |
| HPV56 | L1 | 10 | 233 |
| HPV56 | L1 | 8 | 128 |
| HPV56 | L1 | 10 | 493 |
| HPV56 | L1 | 11 | 493 |
| HPV56 | L1 | 8 | 162 |
| HPV56 | L1 | 11 | 236 |
| HPV56 | L1 | 8 | 369 |
| HPV56 | L1 | 9 | 369 |
| HPV56 | L1 | 10 | 369 |
| HPV56 | L1 | 10 | 23 |
| HPV56 | L1 | 10 | 481 |
| HPV56 | L1 | 11 | 337 |
| HPV56 | L1 | 8 | 404 |
| HPV56 | L1 | 11 | 404 |
| HPV56 | L1 | 8 | 383 |
| HPV56 | L1 | 11 | 383 |
| HPV56 | L1 | 11 | 464 |
| HPV56 | L1 | 9 | 303 |
| HPV56 | L1 | 8 | 140 |
| HPV56 | L1 | 10 | 140 |
| HPV56 | L1 | 9 | 419 |
| HPV56 | L1 | 11 | 419 |
| HPV56 | L1 | 10 | 253 |
| HPV56 | L1 | 9 | 290 |
| HPV56 | L1 | 9 | 21 |
| HPV56 | L1 | 8 | 409 |
| HPV56 | L1 | 10 | 409 |
| HPV56 | L1 | 8 | 407 |
| HPV56 | L1 | 9 | 407 |
| HPV56 | L1 | 10 | 407 |
| HPV56 | L1 | 8 | 364 |
| HPV56 | L1 | 11 | 364 |
| HPV56 | L1 | 9 | 148 |
| HPV56 | L1 | 8 | 240 |
| HPV56 | L1 | 9 | 206 |
| HPV56 | L1 | 10 | 206 |
| HPV56 | L1 | 11 | 206 |
| HPV56 | L1 | 8 | 25 |
| HPV56 | L1 | 10 | 25 |
| HPV56 | L1 | 8 | 356 |
| HPV56 | L1 | 10 | 356 |
| HPV56 | L1 | 11 | 356 |
| HPV56 | L1 | 8 | 17 |
| HPV56 | L1 | 10 | 17 |
| HPV56 | L1 | 11 | 17 |
| HPV56 | L1 | 10 | 138 |
| HPV56 | L1 | 11 | 150 |
| HPV56 | L1 | 8 | 438 |
| HPV56 | L1 | 10 | 438 |
| HPV56 | L1 | 8 | 144 |
| HPV56 | L1 | 8 | 506 |
| HPV56 | L1 | 9 | 506 |

TABLE VIII-continued

HLA-A2 Supermotif-Bearing Peptides

| 1 | 2 | 3 | 4 |
|---|---|---|---|
| HPV56 | L1 | 10 | 506 |
| HPV56 | L1 | 8 | 71 |
| HPV56 | L1 | 9 | 71 |
| HPV56 | L1 | 10 | 71 |
| HPV56 | L1 | 10 | 399 |
| HPV56 | L1 | 10 | 459 |
| HPV56 | L1 | 8 | 414 |
| HPV56 | L1 | 9 | 414 |
| HPV56 | L1 | 11 | 414 |
| HPV56 | L1 | 8 | 192 |
| HPV56 | L1 | 8 | 251 |
| HPV56 | L1 | 9 | 251 |
| HPV56 | L1 | 9 | 392 |
| HPV56 | L1 | 8 | 413 |
| HPV56 | L1 | 9 | 413 |
| HPV56 | L1 | 10 | 413 |
| HPV56 | L1 | 11 | 270 |
| HPV56 | L1 | 8 | 186 |
| HPV56 | L1 | 11 | 186 |
| HPV56 | L1 | 9 | 93 |
| HPV56 | L1 | 8 | 300 |
| HPV56 | L1 | 10 | 300 |
| HPV56 | L1 | 8 | 245 |
| HPV56 | L1 | 10 | 245 |
| HPV56 | L1 | 9 | 98 |
| HPV56 | L1 | 9 | 55 |
| HPV56 | L1 | 9 | 45 |
| HPV56 | L1 | 9 | 474 |
| HPV56 | L1 | 11 | 474 |
| HPV56 | L1 | 8 | 222 |
| HPV56 | L1 | 10 | 78 |
| HPV56 | L1 | 11 | 78 |
| HPV56 | L1 | 11 | 224 |
| HPV56 | L1 | 11 | 77 |
| HPV56 | L1 | 9 | 431 |
| HPV56 | L1 | 11 | 502 |
| HPV56 | L1 | 9 | 484 |
| HPV56 | L1 | 8 | 247 |
| HPV56 | L1 | 10 | 247 |
| HPV56 | L1 | 10 | 405 |
| HPV56 | L1 | 11 | 405 |
| HPV56 | L1 | 11 | 347 |
| HPV56 | L1 | 8 | 132 |
| HPV56 | L1 | 10 | 132 |
| HPV56 | L1 | 11 | 36 |
| HPV56 | L1 | 9 | 421 |
| HPV56 | L1 | 11 | 421 |
| HPV56 | L1 | 8 | 234 |
| HPV56 | L1 | 9 | 234 |
| HPV56 | L1 | 8 | 333 |
| HPV56 | L1 | 8 | 1 |
| HPV56 | L1 | 10 | 5 |
| HPV56 | L1 | 10 | 503 |
| HPV56 | L1 | 11 | 503 |
| HPV56 | L1 | 10 | 376 |
| HPV56 | L1 | 10 | 428 |
| HPV56 | L1 | 8 | 436 |
| HPV56 | L1 | 9 | 436 |
| HPV56 | L1 | 10 | 436 |
| HPV56 | L1 | 9 | 180 |
| HPV56 | L1 | 11 | 180 |
| HPV56 | L1 | 10 | 123 |
| HPV56 | L1 | 11 | 123 |
| HPV56 | L1 | 8 | 167 |
| HPV56 | L1 | 8 | 430 |
| HPV56 | L1 | 10 | 430 |
| HPV56 | L1 | 8 | 483 |
| HPV56 | L1 | 10 | 483 |
| HPV56 | L1 | 8 | 375 |
| HPV56 | L1 | 11 | 375 |
| HPV56 | L1 | 8 | 361 |
| HPV56 | L1 | 10 | 361 |
| HPV56 | L1 | 11 | 361 |
| HPV56 | L1 | 9 | 91 |
| HPV56 | L1 | 11 | 91 |
| HPV56 | L1 | 9 | 226 |
| HPV56 | L1 | 10 | 226 |
| HPV56 | L1 | 9 | 28 |
| HPV56 | L1 | 10 | 28 |
| HPV56 | L1 | 11 | 28 |
| HPV56 | L1 | 10 | 172 |
| HPV56 | L1 | 8 | 197 |
| HPV56 | L1 | 11 | 197 |
| HPV56 | L1 | 11 | 511 |
| HPV56 | L1 | 8 | 228 |
| HPV56 | L1 | 10 | 228 |
| HPV56 | L1 | 8 | 31 |
| HPV56 | L1 | 10 | 473 |
| HPV56 | L1 | 9 | 221 |
| HPV56 | L1 | 8 | 255 |
| HPV56 | L1 | 9 | 155 |
| HPV56 | L1 | 11 | 146 |
| HPV56 | L1 | 8 | 496 |
| HPV56 | L1 | 10 | 496 |
| HPV56 | L1 | 8 | 13 |
| HPV56 | L1 | 10 | 13 |
| HPV56 | L1 | 11 | 4 |
| HPV56 | L1 | 8 | 467 |
| HPV56 | L1 | 9 | 467 |
| HPV56 | L1 | 8 | 50 |
| HPV56 | L1 | 9 | 50 |
| HPV56 | L1 | 10 | 50 |
| HPV56 | L1 | 8 | 522 |
| HPV56 | L1 | 8 | 52 |
| HPV56 | L1 | 8 | 189 |
| HPV56 | L1 | 10 | 189 |
| HPV56 | L1 | 11 | 189 |
| HPV56 | L1 | 9 | 410 |
| HPV56 | L1 | 11 | 410 |
| HPV56 | L1 | 11 | 288 |
| HPV56 | L1 | 9 | 339 |
| HPV56 | L1 | 9 | 362 |
| HPV56 | L1 | 10 | 362 |
| HPV56 | L1 | 9 | 504 |
| HPV56 | L1 | 10 | 504 |
| HPV56 | L1 | 11 | 504 |
| HPV56 | L1 | 10 | 384 |
| HPV56 | L1 | 10 | 187 |
| HPV56 | L1 | 10 | 213 |
| HPV56 | L1 | 11 | 213 |
| HPV56 | L1 | 8 | 297 |
| HPV56 | L1 | 9 | 297 |
| HPV56 | L1 | 11 | 297 |
| HPV56 | L1 | 9 | 349 |
| HPV56 | L1 | 10 | 159 |
| HPV56 | L1 | 11 | 159 |
| HPV56 | L1 | 10 | 110 |
| HPV56 | L1 | 9 | 131 |
| HPV56 | L1 | 11 | 131 |
| HPV56 | L1 | 8 | 65 |
| HPV56 | L1 | 9 | 272 |
| HPV56 | L1 | 8 | 417 |
| HPV56 | L1 | 11 | 417 |
| HPV56 | L1 | 8 | 520 |
| HPV56 | L1 | 10 | 520 |
| HPV56 | L1 | 10 | 100 |
| HPV56 | L1 | 11 | 67 |
| HPV56 | L1 | 9 | 446 |
| HPV56 | L1 | 9 | 332 |
| HPV56 | L1 | 11 | 279 |
| HPV56 | L1 | 9 | 261 |
| HPV56 | L1 | 11 | 261 |
| HPV56 | L1 | 9 | 489 |
| HPV56 | L1 | 8 | 373 |
| HPV56 | L1 | 9 | 373 |
| HPV56 | L1 | 10 | 373 |
| HPV56 | L1 | 9 | 182 |
| HPV56 | L1 | 11 | 182 |
| HPV56 | L1 | 9 | 86 |
| HPV56 | L1 | 11 | 86 |

TABLE VIII-continued

HLA-A2 Supermotif-Bearing Peptides

| 1 | 2 | 3 | 4 |
|---|---|---|---|
| HPV56 | L1 | 11 | 323 |
| HPV56 | L1 | 11 | 380 |
| HPV56 | L1 | 8 | 304 |
| HPV56 | L1 | 9 | 377 |
| HPV56 | L1 | 8 | 415 |
| HPV56 | L1 | 10 | 415 |
| HPV56 | L1 | 9 | 188 |
| HPV56 | L1 | 11 | 188 |
| HPV56 | L1 | 11 | 212 |
| HPV56 | L1 | 8 | 215 |
| HPV56 | L1 | 9 | 215 |
| HPV56 | L1 | 10 | 215 |
| HPV56 | L1 | 11 | 215 |
| HPV56 | L1 | 8 | 370 |
| HPV56 | L1 | 9 | 370 |
| HPV56 | L1 | 11 | 370 |
| HPV56 | L1 | 9 | 366 |
| HPV56 | L1 | 11 | 366 |
| HPV56 | L1 | 10 | 57 |
| HPV56 | L1 | 8 | 326 |
| HPV56 | L1 | 9 | 326 |
| HPV56 | L1 | 10 | 326 |
| HPV56 | L1 | 9 | 513 |
| HPV56 | L1 | 11 | 513 |
| HPV56 | L1 | 9 | 173 |
| HPV56 | L1 | 11 | 173 |
| HPV56 | L1 | 9 | 246 |
| HPV56 | L1 | 11 | 246 |
| HPV56 | L1 | 8 | 420 |
| HPV56 | L1 | 10 | 420 |
| HPV56 | L1 | 11 | 420 |
| HPV56 | L1 | 11 | 259 |
| HPV56 | L1 | 8 | 87 |
| HPV56 | L1 | 10 | 87 |
| HPV56 | L1 | 9 | 214 |
| HPV56 | L1 | 10 | 214 |
| HPV56 | L1 | 11 | 214 |
| HPV56 | L1 | 10 | 365 |
| HPV56 | L1 | 8 | 56 |
| HPV56 | L1 | 11 | 56 |
| HPV56 | L1 | 8 | 367 |
| HPV56 | L1 | 10 | 367 |
| HPV56 | L1 | 11 | 367 |
| HPV56 | L1 | 8 | 134 |
| HPV56 | L1 | 10 | 203 |
| HPV56 | L1 | 8 | 7 |
| HPV56 | L1 | 9 | 423 |
| HPV56 | L1 | 10 | 423 |
| HPV56 | L1 | 8 | 268 |
| HPV56 | L1 | 10 | 47 |
| HPV56 | L1 | 11 | 47 |
| HPV56 | L1 | 10 | 396 |
| HPV56 | L1 | 9 | 283 |
| HPV56 | L1 | 8 | 102 |
| HPV56 | L1 | 10 | 102 |
| HPV56 | L1 | 9 | 325 |
| HPV56 | L1 | 10 | 325 |
| HPV56 | L1 | 11 | 325 |
| HPV56 | L1 | 11 | 62 |
| HPV56 | L1 | 8 | 453 |
| HPV56 | L2 | 9 | 222 |
| HPV56 | L2 | 8 | 281 |
| HPV56 | L2 | 9 | 281 |
| HPV56 | L2 | 8 | 327 |
| HPV56 | L2 | 11 | 327 |
| HPV56 | L2 | 9 | 303 |
| HPV56 | L2 | 11 | 303 |
| HPV56 | L2 | 10 | 246 |
| HPV56 | L2 | 9 | 367 |
| HPV56 | L2 | 10 | 14 |
| HPV56 | L2 | 9 | 6 |
| HPV56 | L2 | 10 | 6 |
| HPV56 | L2 | 10 | 201 |
| HPV56 | L2 | 8 | 139 |
| HPV56 | L2 | 11 | 139 |
| HPV56 | L2 | 8 | 322 |
| HPV56 | L2 | 11 | 322 |
| HPV56 | L2 | 8 | 142 |
| HPV56 | L2 | 9 | 142 |
| HPV56 | L2 | 11 | 142 |
| HPV56 | L2 | 10 | 406 |
| HPV56 | L2 | 10 | 349 |
| HPV56 | L2 | 11 | 260 |
| HPV56 | L2 | 8 | 425 |
| HPV56 | L2 | 9 | 83 |
| HPV56 | L2 | 10 | 83 |
| HPV56 | L2 | 11 | 83 |
| HPV56 | L2 | 10 | 30 |
| HPV56 | L2 | 10 | 429 |
| HPV56 | L2 | 11 | 429 |
| HPV56 | L2 | 10 | 357 |
| HPV56 | L2 | 11 | 357 |
| HPV56 | L2 | 8 | 169 |
| HPV56 | L2 | 8 | 331 |
| HPV56 | L2 | 10 | 331 |
| HPV56 | L2 | 8 | 194 |
| HPV56 | L2 | 9 | 194 |
| HPV56 | L2 | 8 | 129 |
| HPV56 | L2 | 9 | 129 |
| HPV56 | L2 | 11 | 129 |
| HPV56 | L2 | 8 | 333 |
| HPV56 | L2 | 9 | 36 |
| HPV56 | L2 | 10 | 36 |
| HPV56 | L2 | 10 | 398 |
| HPV56 | L2 | 11 | 398 |
| HPV56 | L2 | 8 | 175 |
| HPV56 | L2 | 10 | 175 |
| HPV56 | L2 | 8 | 457 |
| HPV56 | L2 | 8 | 457 |
| HPV56 | L2 | 8 | 382 |
| HPV56 | L2 | 9 | 382 |
| HPV56 | L2 | 10 | 382 |
| HPV56 | L2 | 8 | 200 |
| HPV56 | L2 | 11 | 200 |
| HPV56 | L2 | 9 | 162 |
| HPV56 | L2 | 8 | 241 |
| HPV56 | L2 | 9 | 241 |
| HPV56 | L2 | 11 | 241 |
| HPV56 | L2 | 11 | 276 |
| HPV56 | L2 | 10 | 231 |
| HPV56 | L2 | 9 | 122 |
| HPV56 | L2 | 10 | 122 |
| HPV56 | L2 | 8 | 287 |
| HPV56 | L2 | 9 | 51 |
| HPV56 | L2 | 11 | 51 |
| HPV56 | L2 | 9 | 418 |
| HPV56 | L2 | 10 | 418 |
| HPV56 | L2 | 8 | 116 |
| HPV56 | L2 | 10 | 314 |
| HPV56 | L2 | 8 | 188 |
| HPV56 | L2 | 10 | 188 |
| HPV56 | L2 | 8 | 56 |
| HPV56 | L2 | 8 | 360 |
| HPV56 | L2 | 9 | 360 |
| HPV56 | L2 | 9 | 346 |
| HPV56 | L2 | 8 | 25 |
| HPV56 | L2 | 11 | 25 |
| HPV56 | L2 | 8 | 206 |
| HPV56 | L2 | 10 | 206 |
| HPV56 | L2 | 8 | 62 |
| HPV56 | L2 | 11 | 62 |
| HPV56 | L2 | 10 | 60 |
| HPV56 | L2 | 8 | 310 |
| HPV56 | L2 | 9 | 269 |
| HPV56 | L2 | 11 | 269 |
| HPV56 | L2 | 11 | 293 |
| HPV56 | L2 | 8 | 156 |
| HPV56 | L2 | 8 | 372 |
| HPV56 | L2 | 9 | 372 |
| HPV56 | L2 | 8 | 151 |

TABLE VIII-continued

HLA-A2 Supermotif-Bearing Peptides

| 1 | 2 | 3 | 4 |
|---|---|---|---|
| HPV56 | L2 | 11 | 151 |
| HPV56 | L2 | 10 | 221 |
| HPV56 | L2 | 9 | 326 |
| HPV56 | L2 | 10 | 380 |
| HPV56 | L2 | 9 | 44 |
| HPV56 | L2 | 8 | 432 |
| HPV56 | L2 | 11 | 432 |
| HPV56 | L2 | 9 | 305 |
| HPV56 | L2 | 11 | 305 |
| HPV56 | L2 | 11 | 157 |
| HPV56 | L2 | 8 | 143 |
| HPV56 | L2 | 10 | 143 |
| HPV56 | L2 | 8 | 130 |
| HPV56 | L2 | 10 | 130 |
| HPV56 | L2 | 8 | 279 |
| HPV56 | L2 | 10 | 279 |
| HPV56 | L2 | 11 | 279 |
| HPV56 | L2 | 11 | 81 |
| HPV56 | L2 | 9 | 407 |
| HPV56 | L2 | 10 | 103 |
| HPV56 | L2 | 11 | 103 |
| HPV56 | L2 | 9 | 91 |
| HPV56 | L2 | 8 | 229 |
| HPV56 | L2 | 9 | 229 |
| HPV56 | L2 | 10 | 302 |
| HPV56 | L2 | 8 | 34 |
| HPV56 | L2 | 11 | 34 |
| HPV56 | L2 | 8 | 43 |
| HPV56 | L2 | 10 | 43 |
| HPV56 | L2 | 10 | 22 |
| HPV56 | L2 | 11 | 22 |
| HPV56 | L2 | 8 | 19 |
| HPV56 | L2 | 8 | 38 |
| HPV56 | L2 | 8 | 235 |
| HPV56 | L2 | 8 | 253 |
| HPV56 | L2 | 9 | 263 |
| HPV56 | L2 | 9 | 181 |
| HPV56 | L2 | 11 | 337 |
| HPV56 | L2 | 8 | 45 |
| HPV56 | L2 | 8 | 106 |
| HPV56 | L2 | 8 | 248 |
| HPV56 | L2 | 11 | 197 |
| HPV56 | L2 | 9 | 353 |
| HPV56 | L2 | 8 | 179 |
| HPV56 | L2 | 11 | 179 |
| HPV56 | L2 | 9 | 278 |
| HPV56 | L2 | 11 | 278 |
| HPV56 | L2 | 9 | 385 |
| HPV56 | L2 | 9 | 388 |
| HPV56 | L2 | 8 | 239 |
| HPV56 | L2 | 9 | 239 |
| HPV56 | L2 | 10 | 239 |
| HPV56 | L2 | 11 | 239 |
| HPV56 | L2 | 10 | 285 |
| HPV56 | L2 | 8 | 86 |
| HPV56 | L2 | 11 | 86 |
| HPV56 | L2 | 11 | 245 |
| HPV56 | L2 | 9 | 138 |
| HPV56 | L2 | 8 | 325 |
| HPV56 | L2 | 10 | 325 |
| HPV56 | L2 | 10 | 374 |
| HPV56 | L2 | 8 | 214 |
| HPV56 | L2 | 9 | 214 |
| HPV56 | L2 | 10 | 214 |
| HPV56 | L2 | 10 | 90 |
| HPV56 | L2 | 8 | 254 |
| HPV56 | L2 | 10 | 254 |
| HPV56 | L2 | 11 | 254 |
| HPV56 | L2 | 8 | 160 |
| HPV56 | L2 | 9 | 160 |
| HPV56 | L2 | 11 | 160 |
| HPV56 | L2 | 8 | 392 |
| HPV56 | L2 | 8 | 73 |
| HPV56 | L2 | 9 | 73 |
| HPV56 | L2 | 10 | 73 |
| HPV56 | L2 | 8 | 420 |
| HPV56 | L2 | 11 | 420 |
| HPV56 | L2 | 10 | 171 |
| HPV56 | L2 | 11 | 171 |
| HPV56 | L2 | 8 | 98 |
| HPV56 | L2 | 9 | 98 |
| HPV56 | L2 | 10 | 98 |
| HPV56 | L2 | 10 | 410 |
| HPV56 | L2 | 11 | 185 |
| HPV56 | L2 | 8 | 145 |
| HPV56 | L2 | 11 | 145 |
| HPV56 | L2 | 8 | 166 |
| HPV56 | L2 | 11 | 166 |
| HPV56 | L2 | 10 | 328 |
| HPV56 | L2 | 11 | 328 |
| HPV56 | L2 | 8 | 16 |
| HPV56 | L2 | 11 | 16 |
| HPV56 | L2 | 9 | 232 |
| HPV56 | L2 | 11 | 232 |
| HPV56 | L2 | 10 | 198 |
| HPV56 | L2 | 9 | 172 |
| HPV56 | L2 | 10 | 172 |
| HPV56 | L2 | 11 | 172 |
| HPV56 | L2 | 8 | 306 |
| HPV56 | L2 | 10 | 306 |
| HPV56 | L2 | 8 | 233 |
| HPV56 | L2 | 10 | 233 |
| HPV56 | L2 | 10 | 11 |
| HPV56 | L2 | 8 | 5 |
| HPV56 | L2 | 10 | 5 |
| HPV56 | L2 | 11 | 5 |
| HPV56 | L2 | 11 | 220 |
| HPV56 | L2 | 11 | 452 |
| HPV56 | L2 | 8 | 298 |
| HPV56 | L2 | 10 | 298 |
| HPV56 | L2 | 10 | 225 |
| HPV56 | L2 | 8 | 316 |
| HPV56 | L2 | 11 | 316 |
| HPV56 | L2 | 10 | 250 |
| HPV56 | L2 | 10 | 370 |
| HPV56 | L2 | 11 | 370 |
| HPV56 | L2 | 9 | 339 |
| HPV56 | L2 | 8 | 13 |
| HPV56 | L2 | 11 | 13 |
| HPV56 | L2 | 11 | 102 |
| HPV56 | L2 | 9 | 262 |
| HPV56 | L2 | 10 | 262 |
| HPV56 | L2 | 9 | 49 |
| HPV56 | L2 | 11 | 49 |
| HPV56 | L2 | 9 | 363 |
| HPV56 | L2 | 11 | 363 |
| HPV56 | L2 | 8 | 154 |
| HPV56 | L2 | 10 | 154 |
| HPV56 | L2 | 9 | 79 |
| HPV56 | L2 | 9 | 378 |
| HPV56 | L2 | 10 | 378 |
| HPV56 | L2 | 10 | 212 |
| HPV56 | L2 | 11 | 212 |
| HPV56 | L2 | 8 | 134 |
| HPV56 | L2 | 10 | 134 |
| HPV56 | L2 | 11 | 134 |
| HPV56 | L2 | 8 | 148 |
| HPV56 | L2 | 10 | 148 |
| HPV56 | L2 | 11 | 148 |
| HPV56 | L2 | 9 | 365 |
| HPV56 | L2 | 11 | 365 |
| HPV56 | L2 | 9 | 95 |
| HPV56 | L2 | 10 | 95 |
| HPV56 | L2 | 11 | 95 |
| HPV56 | L2 | 9 | 111 |
| HPV56 | L2 | 10 | 390 |
| HPV56 | L2 | 8 | 304 |
| HPV56 | L2 | 10 | 304 |
| HPV56 | L2 | 8 | 80 |
| HPV56 | L2 | 8 | 379 |

TABLE VIII-continued

HLA-A2 Supermotif-Bearing Peptides

| 1 | 2 | 3 | 4 |
|---|---|---|---|
| HPV56 | L2 | 9 | 379 |
| HPV56 | L2 | 11 | 379 |
| HPV56 | L2 | 8 | 105 |
| HPV56 | L2 | 9 | 105 |
| HPV56 | L2 | 9 | 247 |
| HPV56 | L2 | 9 | 15 |
| HPV56 | L2 | 8 | 386 |
| HPV56 | L2 | 11 | 386 |
| HPV56 | L2 | 8 | 136 |
| HPV56 | L2 | 9 | 136 |
| HPV56 | L2 | 11 | 136 |
| HPV56 | L2 | 9 | 135 |
| HPV56 | L2 | 10 | 135 |
| HPV56 | L2 | 9 | 149 |
| HPV56 | L2 | 10 | 149 |
| HPV56 | L2 | 11 | 2 |
| HPV56 | L2 | 9 | 280 |
| HPV56 | L2 | 10 | 280 |
| HPV56 | L2 | 8 | 270 |
| HPV56 | L2 | 8 | 366 |
| HPV56 | L2 | 10 | 366 |
| HPV56 | L2 | 10 | 167 |
| HPV56 | L2 | 8 | 112 |
| HPV56 | L2 | 10 | 140 |
| HPV56 | L2 | 11 | 140 |
| HPV56 | L2 | 8 | 408 |
| HPV56 | L2 | 8 | 389 |
| HPV56 | L2 | 11 | 389 |
| HPV56 | L2 | 11 | 236 |
| HPV56 | L2 | 9 | 104 |
| HPV56 | L2 | 10 | 104 |
| HPV56 | L2 | 8 | 84 |
| HPV56 | L2 | 9 | 84 |
| HPV56 | L2 | 10 | 84 |
| HPV56 | L2 | 8 | 92 |
| HPV56 | L2 | 9 | 31 |
| HPV56 | L2 | 11 | 31 |
| HPV56 | L2 | 11 | 40 |
| HPV56 | L2 | 8 | 351 |
| HPV56 | L2 | 11 | 351 |
| HPV56 | L2 | 8 | 431 |
| HPV56 | L2 | 9 | 431 |
| HPV56 | L2 | 10 | 71 |
| HPV56 | L2 | 11 | 71 |

TABLE VIIIA

HPV 6A
HLA-A2 Supermotif Peptides

| 2 | 3 | 4 |
|---|---|---|
| L1 | 9 | 234 |
| L2 | 10 | 329 |
| L2 | 11 | 329 |
| E5 | 8 | 9 |
| E5 | 9 | 9 |
| E5 | 10 | 9 |
| E1 | 8 | 318 |
| E1 | 10 | 318 |
| L1 | 8 | 489 |
| L1 | 10 | 489 |
| L2 | 9 | 340 |
| L2 | 11 | 340 |
| E4 | 8 | 2 |
| E4 | 10 | 2 |
| E2 | 8 | 3 |
| L2 | 8 | 286 |
| L2 | 9 | 286 |
| E2 | 8 | 72 |
| E2 | 11 | 72 |
| L2 | 10 | 112 |
| L2 | 11 | 112 |
| E1 | 11 | 112 |
| L2 | 8 | 140 |
| L2 | 11 | 140 |
| L1 | 8 | 420 |
| E1 | 8 | 475 |
| E1 | 9 | 22 |
| E1 | 11 | 22 |
| E2 | 10 | 250 |
| E1 | 8 | 65 |
| E1 | 10 | 65 |
| E4 | 9 | 14 |
| E4 | 11 | 14 |
| L2 | 8 | 228 |
| L2 | 11 | 228 |
| L1 | 11 | 81 |
| L2 | 9 | 421 |
| L2 | 10 | 421 |
| E1 | 10 | 554 |
| E1 | 11 | 554 |
| E6 | 11 | 37 |
| E5 | 8 | 79 |
| E5 | 9 | 79 |
| E5 | 11 | 79 |
| E1 | 9 | 319 |
| L1 | 9 | 203 |
| L2 | 9 | 327 |
| E1 | 10 | 63 |
| L2 | 8 | 341 |
| L2 | 10 | 341 |
| L1 | 8 | 312 |
| L1 | 10 | 300 |
| E4 | 9 | 3 |
| E4 | 11 | 3 |
| E1 | 10 | 381 |
| E2 | 11 | 217 |
| L1 | 9 | 22 |
| L1 | 11 | 22 |
| E1 | 11 | 296 |
| E1 | 10 | 407 |
| E4 | 8 | 61 |
| E4 | 9 | 61 |
| L2 | 10 | 14 |
| L2 | 11 | 14 |
| E1 | 9 | 525 |
| E1 | 11 | 525 |
| E6 | 10 | 10 |
| E6 | 8 | 86 |
| E1 | 11 | 77 |
| E1 | 10 | 101 |
| L1 | 9 | 43 |
| E2 | 10 | 231 |
| L1 | 8 | 483 |
| E1 | 8 | 601 |
| E6 | 11 | 64 |
| E1 | 11 | 234 |
| E2 | 9 | 124 |
| E2 | 10 | 124 |
| L1 | 9 | 341 |
| L1 | 11 | 341 |
| E1 | 11 | 406 |
| E1 | 10 | 473 |
| E6 | 8 | 67 |
| E6 | 9 | 137 |
| E2 | 9 | 296 |
| E2 | 8 | 35 |
| E2 | 9 | 35 |
| E1 | 8 | 488 |
| E1 | 11 | 488 |
| L1 | 9 | 153 |
| E2 | 8 | 11 |
| E7 | 9 | 71 |
| E1 | 9 | 14 |
| E1 | 10 | 14 |

TABLE VIIIA-continued

HPV 6A
HLA-A2 Supermotif Peptides

| 2 | 3 | 4 |
|---|---|---|
| E1 | 11 | 14 |
| L1 | 8 | 171 |
| E6 | 8 | 131 |
| E2 | 8 | 252 |
| E6 | 8 | 31 |
| E6 | 9 | 31 |
| E6 | 10 | 31 |
| E6 | 11 | 31 |
| E1 | 9 | 640 |
| E1 | 10 | 640 |
| E4 | 10 | 64 |
| E4 | 11 | 64 |
| E2 | 8 | 9 |
| E2 | 10 | 9 |
| E2 | 8 | 153 |
| E1 | 10 | 516 |
| E1 | 11 | 516 |
| E1 | 8 | 524 |
| E1 | 10 | 524 |
| E2 | 11 | 230 |
| L1 | 9 | 24 |
| E1 | 8 | 369 |
| E1 | 9 | 369 |
| E1 | 8 | 170 |
| E1 | 10 | 170 |
| L2 | 9 | 278 |
| L2 | 10 | 278 |
| L2 | 11 | 278 |
| E6 | 11 | 96 |
| L2 | 9 | 356 |
| L2 | 10 | 356 |
| E7 | 8 | 75 |
| E7 | 9 | 75 |
| E7 | 10 | 75 |
| L2 | 8 | 322 |
| L2 | 9 | 322 |
| L2 | 9 | 404 |
| L2 | 11 | 404 |
| E1 | 11 | 570 |
| E7 | 8 | 88 |
| E7 | 11 | 88 |
| L2 | 11 | 347 |
| L2 | 10 | 396 |
| L2 | 11 | 396 |
| E1 | 11 | 222 |
| E2 | 10 | 313 |
| L1 | 8 | 366 |
| L1 | 11 | 366 |
| E7 | 8 | 14 |
| E7 | 10 | 14 |
| L1 | 9 | 208 |
| L1 | 11 | 208 |
| E1 | 11 | 46 |
| L1 | 9 | 195 |
| L1 | 10 | 195 |
| L2 | 9 | 42 |
| L2 | 11 | 42 |
| E6 | 9 | 14 |
| E6 | 11 | 14 |
| L1 | 10 | 455 |
| L1 | 11 | 455 |
| E2 | 8 | 141 |
| E2 | 11 | 141 |
| L1 | 10 | 198 |
| E1 | 9 | 481 |
| E1 | 11 | 481 |
| E1 | 10 | 73 |
| L1 | 8 | 331 |
| L1 | 9 | 331 |
| L1 | 10 | 331 |
| L2 | 10 | 369 |
| L2 | 11 | 369 |
| E1 | 8 | 534 |
| L1 | 10 | 411 |
| L1 | 11 | 411 |
| L2 | 10 | 30 |
| L2 | 11 | 30 |
| E6 | 8 | 99 |
| L1 | 9 | 215 |
| L1 | 10 | 215 |
| L2 | 11 | 258 |
| L2 | 8 | 143 |
| L2 | 9 | 143 |
| L2 | 10 | 143 |
| E2 | 11 | 136 |
| E1 | 8 | 71 |
| E1 | 9 | 71 |
| E1 | 9 | 178 |
| E2 | 8 | 174 |
| L2 | 9 | 274 |
| E1 | 10 | 250 |
| E1 | 8 | 143 |
| E2 | 9 | 2 |
| E1 | 8 | 21 |
| E1 | 10 | 21 |
| E2 | 8 | 66 |
| E2 | 10 | 66 |
| L2 | 8 | 173 |
| L2 | 10 | 173 |
| E1 | 10 | 336 |
| E1 | 11 | 336 |
| E1 | 11 | 180 |
| E1 | 11 | 62 |
| L1 | 11 | 299 |
| E1 | 11 | 100 |
| L2 | 8 | 332 |
| L2 | 9 | 332 |
| L2 | 10 | 332 |
| L2 | 8 | 192 |
| L2 | 9 | 192 |
| E1 | 8 | 105 |
| E1 | 9 | 105 |
| E1 | 11 | 105 |
| L2 | 11 | 120 |
| E6 | 10 | 42 |
| E1 | 8 | 197 |
| E1 | 10 | 197 |
| E1 | 11 | 197 |
| E2 | 8 | 17 |
| E2 | 10 | 17 |
| L2 | 8 | 334 |
| E2 | 9 | 74 |
| E2 | 10 | 74 |
| E1 | 11 | 417 |
| E1 | 11 | 360 |
| E7 | 11 | 27 |
| E2 | 9 | 341 |
| E2 | 10 | 341 |
| E7 | 10 | 73 |
| E7 | 11 | 73 |
| E6 | 9 | 92 |
| E6 | 10 | 92 |
| E6 | 11 | 92 |
| E2 | 9 | 96 |
| L2 | 8 | 135 |
| L2 | 10 | 135 |
| E4 | 8 | 75 |
| E4 | 9 | 75 |
| E4 | 10 | 75 |
| E4 | 11 | 75 |
| E2 | 8 | 185 |
| E2 | 9 | 185 |
| E7 | 10 | 39 |
| E1 | 8 | 141 |
| E1 | 10 | 141 |
| E1 | 9 | 39 |
| E1 | 10 | 39 |
| E6 | 8 | 113 |

TABLE VIIIA-continued

HPV 6A
HLA-A2 Supermotif Peptides

| 2 | 3 | 4 |
|---|---|---|
| E6 | 9 | 113 |
| E6 | 10 | 113 |
| L1 | 9 | 262 |
| L1 | 10 | 262 |
| L1 | 11 | 262 |
| L1 | 8 | 103 |
| L1 | 10 | 103 |
| E2 | 8 | 118 |
| E2 | 11 | 118 |
| L1 | 8 | 381 |
| L1 | 9 | 381 |
| E7 | 9 | 78 |
| E7 | 10 | 78 |
| E2 | 8 | 205 |
| E2 | 9 | 205 |
| E2 | 11 | 205 |
| E5 | 8 | 2 |
| E5 | 9 | 2 |
| E5 | 11 | 2 |
| L1 | 11 | 206 |
| L1 | 8 | 80 |
| L1 | 9 | 252 |
| L2 | 9 | 442 |
| L2 | 11 | 442 |
| E1 | 8 | 50 |
| L1 | 8 | 369 |
| L1 | 9 | 369 |
| L1 | 10 | 369 |
| E1 | 10 | 454 |
| L2 | 9 | 428 |
| E5 | 8 | 40 |
| E5 | 9 | 40 |
| E5 | 10 | 40 |
| E5 | 11 | 40 |
| E1 | 10 | 494 |
| L1 | 8 | 119 |
| E1 | 8 | 393 |
| E1 | 11 | 393 |
| E2 | 10 | 346 |
| E2 | 11 | 346 |
| L2 | 8 | 398 |
| L2 | 9 | 398 |
| E1 | 10 | 446 |
| L1 | 9 | 245 |
| E1 | 9 | 457 |
| L2 | 8 | 239 |
| L2 | 9 | 239 |
| L2 | 10 | 239 |
| L2 | 11 | 276 |
| E1 | 11 | 18 |
| E2 | 8 | 290 |
| E1 | 8 | 252 |
| E1 | 10 | 252 |
| L1 | 8 | 371 |
| L1 | 10 | 371 |
| L2 | 8 | 129 |
| L2 | 9 | 129 |
| L2 | 10 | 129 |
| L2 | 11 | 198 |
| E2 | 11 | 171 |
| E5 | 8 | 28 |
| E5 | 10 | 28 |
| L1 | 8 | 326 |
| L1 | 11 | 326 |
| E5 | 8 | 24 |
| E5 | 9 | 24 |
| E5 | 10 | 24 |
| E5 | 11 | 24 |
| L1 | 8 | 202 |
| L1 | 10 | 202 |
| L2 | 9 | 117 |
| L2 | 10 | 314 |
| L1 | 8 | 318 |
| L1 | 10 | 318 |
| L1 | 11 | 318 |
| L2 | 8 | 58 |
| E1 | 9 | 243 |
| E1 | 11 | 194 |
| E1 | 8 | 326 |
| E1 | 9 | 326 |
| E2 | 11 | 156 |
| E1 | 9 | 350 |
| E1 | 10 | 350 |
| L1 | 10 | 101 |
| L2 | 10 | 56 |
| E7 | 8 | 22 |
| E7 | 9 | 22 |
| E1 | 8 | 217 |
| E2 | 9 | 50 |
| E2 | 10 | 50 |
| L1 | 9 | 400 |
| L1 | 10 | 400 |
| L2 | 8 | 292 |
| L2 | 10 | 223 |
| L1 | 9 | 144 |
| L1 | 11 | 144 |
| E2 | 8 | 55 |
| E2 | 10 | 55 |
| E1 | 8 | 273 |
| L1 | 8 | 136 |
| L1 | 10 | 136 |
| E1 | 10 | 162 |
| E2 | 8 | 162 |
| E2 | 11 | 162 |
| L1 | 8 | 107 |
| L2 | 8 | 300 |
| E1 | 8 | 191 |
| E1 | 9 | 191 |
| L2 | 8 | 215 |
| L2 | 10 | 215 |
| L2 | 8 | 25 |
| L2 | 11 | 25 |
| E1 | 10 | 6 |
| L2 | 9 | 64 |
| L2 | 11 | 64 |
| E1 | 8 | 436 |
| E1 | 9 | 436 |
| L2 | 10 | 60 |
| E1 | 11 | 145 |
| E7 | 9 | 85 |
| E7 | 11 | 85 |
| L1 | 10 | 407 |
| L2 | 8 | 413 |
| L2 | 9 | 413 |
| L2 | 10 | 413 |
| E1 | 8 | 467 |
| E1 | 9 | 467 |
| E1 | 10 | 467 |
| E1 | 11 | 467 |
| E1 | 9 | 147 |
| L2 | 8 | 75 |
| L2 | 9 | 75 |
| L1 | 10 | 222 |
| E5 | 8 | 11 |
| E5 | 10 | 11 |
| E5 | 11 | 11 |
| E4 | 8 | 90 |
| E4 | 10 | 90 |
| E1 | 10 | 316 |
| L2 | 9 | 51 |
| L2 | 11 | 51 |
| L1 | 10 | 111 |
| L1 | 10 | 478 |
| E2 | 9 | 242 |
| E2 | 10 | 242 |
| L1 | 8 | 113 |
| E1 | 9 | 415 |
| E1 | 8 | 189 |

TABLE VIIIA-continued

HPV 6A
HLA-A2 Supermotif Peptides

| 2 | 3 | 4 |
|---|---|---|
| E1 | 10 | 189 |
| E1 | 11 | 189 |
| L1 | 8 | 35 |
| L1 | 9 | 35 |
| L1 | 10 | 35 |
| E2 | 10 | 53 |
| L2 | 8 | 177 |
| L2 | 9 | 177 |
| L2 | 10 | 177 |
| E6 | 9 | 119 |
| E6 | 11 | 119 |
| E1 | 8 | 264 |
| E1 | 11 | 264 |
| E4 | 10 | 59 |
| E4 | 11 | 59 |
| E2 | 8 | 78 |
| E2 | 9 | 310 |
| E1 | 10 | 449 |
| E2 | 11 | 274 |
| L2 | 9 | 230 |
| L2 | 11 | 230 |
| E1 | 8 | 176 |
| E1 | 11 | 176 |
| E6 | 8 | 25 |
| L1 | 8 | 387 |
| E4 | 10 | 26 |
| L2 | 8 | 306 |
| L2 | 10 | 306 |
| E1 | 8 | 581 |
| L2 | 11 | 149 |
| L1 | 10 | 361 |
| E2 | 8 | 29 |
| E1 | 10 | 502 |
| E7 | 8 | 5 |
| E7 | 9 | 5 |
| E7 | 11 | 5 |
| E5 | 8 | 8 |
| E5 | 9 | 8 |
| E5 | 10 | 8 |
| E5 | 11 | 8 |
| L2 | 11 | 40 |
| E1 | 9 | 98 |
| E5 | 8 | 22 |
| E5 | 10 | 22 |
| E5 | 11 | 22 |
| E1 | 9 | 474 |
| L2 | 8 | 326 |
| L2 | 10 | 326 |
| L2 | 8 | 287 |
| E5 | 9 | 21 |
| E5 | 11 | 21 |
| L1 | 9 | 272 |
| L1 | 11 | 272 |
| E5 | 11 | 31 |
| L2 | 9 | 113 |
| L2 | 10 | 113 |
| L2 | 8 | 279 |
| L2 | 9 | 279 |
| L2 | 10 | 279 |
| E6 | 10 | 97 |
| L2 | 10 | 141 |
| L2 | 11 | 141 |
| E1 | 10 | 195 |
| L2 | 8 | 178 |
| L2 | 9 | 178 |
| E5 | 10 | 32 |
| E5 | 11 | 32 |
| L2 | 9 | 44 |
| E5 | 9 | 17 |
| E5 | 10 | 17 |
| E6 | 8 | 120 |
| E6 | 10 | 120 |
| L1 | 9 | 191 |
| E1 | 8 | 313 |

TABLE VIIIA-continued

HPV 6A
HLA-A2 Supermotif Peptides

| 2 | 3 | 4 |
|---|---|---|
| E1 | 10 | 265 |
| E1 | 11 | 265 |
| L2 | 8 | 405 |
| L2 | 10 | 405 |
| L2 | 8 | 429 |
| L2 | 11 | 429 |
| E1 | 8 | 56 |
| E1 | 10 | 56 |
| E1 | 11 | 56 |
| E1 | 10 | 571 |
| L1 | 8 | 376 |
| L1 | 9 | 376 |
| L1 | 11 | 376 |
| E1 | 11 | 341 |
| L2 | 11 | 82 |
| L2 | 9 | 185 |
| L2 | 11 | 185 |
| L2 | 8 | 131 |
| L2 | 10 | 131 |
| L2 | 11 | 131 |
| L1 | 10 | 187 |
| L1 | 11 | 187 |
| E4 | 9 | 83 |
| E4 | 10 | 83 |
| E4 | 11 | 83 |
| E7 | 10 | 89 |
| E7 | 11 | 11 |
| L2 | 10 | 121 |
| L2 | 11 | 121 |
| E1 | 10 | 443 |
| E2 | 11 | 287 |
| E1 | 8 | 23 |
| E1 | 10 | 23 |
| L2 | 9 | 104 |
| L2 | 10 | 104 |
| L2 | 11 | 104 |
| E5 | 8 | 34 |
| E5 | 9 | 34 |
| E5 | 11 | 34 |
| E5 | 8 | 41 |
| E5 | 9 | 41 |
| E5 | 10 | 41 |
| E5 | 11 | 41 |
| E2 | 10 | 45 |
| E1 | 11 | 553 |
| E2 | 8 | 325 |
| E2 | 9 | 325 |
| E2 | 10 | 325 |
| E2 | 11 | 325 |
| L1 | 9 | 311 |
| E6 | 10 | 123 |
| L1 | 11 | 486 |
| E1 | 11 | 433 |
| E6 | 11 | 73 |
| E2 | 10 | 351 |
| E1 | 8 | 312 |
| E1 | 9 | 312 |
| E2 | 9 | 359 |
| E2 | 10 | 359 |
| E1 | 8 | 254 |
| E1 | 10 | 254 |
| E6 | 11 | 128 |
| E1 | 9 | 357 |
| L2 | 10 | 22 |
| L2 | 11 | 22 |
| E1 | 9 | 114 |
| E1 | 8 | 420 |
| L1 | 8 | 169 |
| L1 | 10 | 169 |
| E6 | 8 | 94 |
| E6 | 9 | 94 |
| E7 | 8 | 49 |
| E2 | 8 | 47 |
| E2 | 10 | 47 |

TABLE VIIIA-continued

HPV 6A
HLA-A2 Supermotif Peptides

| 2 | 3 | 4 |
|---|---|---|
| L1 | 8 | 148 |
| L1 | 11 | 148 |
| E2 | 10 | 182 |
| E2 | 11 | 182 |
| E1 | 11 | 424 |
| E2 | 10 | 84 |
| E2 | 11 | 84 |
| E6 | 9 | 18 |
| E6 | 10 | 18 |
| E4 | 8 | 42 |
| E1 | 8 | 231 |
| E1 | 9 | 231 |
| E1 | 10 | 231 |
| E2 | 11 | 115 |
| E2 | 8 | 165 |
| E2 | 11 | 165 |
| E1 | 8 | 518 |
| E1 | 9 | 518 |
| L2 | 8 | 34 |
| L2 | 11 | 34 |
| E2 | 8 | 147 |
| E2 | 11 | 147 |
| E6 | 9 | 116 |
| E1 | 9 | 121 |
| E6 | 11 | 52 |
| E1 | 8 | 283 |
| E1 | 9 | 283 |
| E1 | 10 | 283 |
| E2 | 10 | 63 |
| E2 | 11 | 63 |
| L1 | 9 | 61 |
| L1 | 9 | 19 |
| L1 | 10 | 19 |
| L1 | 11 | 71 |
| E1 | 8 | 351 |
| E1 | 9 | 351 |
| E1 | 11 | 351 |
| E4 | 10 | 13 |
| E4 | 9 | 60 |
| E4 | 10 | 60 |
| L1 | 10 | 42 |
| L2 | 8 | 107 |
| L2 | 10 | 107 |
| E1 | 9 | 255 |
| E1 | 11 | 255 |
| E1 | 11 | 307 |
| L1 | 10 | 271 |
| E1 | 8 | 557 |
| E1 | 9 | 557 |
| E1 | 10 | 557 |
| E5 | 8 | 16 |
| E5 | 10 | 16 |
| E5 | 11 | 16 |
| E6 | 11 | 101 |
| E1 | 10 | 223 |
| E1 | 11 | 223 |
| L2 | 8 | 179 |
| E1 | 8 | 491 |
| E1 | 9 | 491 |
| E1 | 10 | 491 |
| E2 | 9 | 314 |
| L1 | 11 | 186 |
| L2 | 8 | 246 |
| E5 | 9 | 33 |
| E5 | 10 | 33 |
| L1 | 11 | 41 |
| E1 | 11 | 521 |
| E1 | 9 | 540 |
| E2 | 10 | 15 |
| E1 | 11 | 208 |
| E7 | 8 | 83 |
| E7 | 11 | 83 |
| E4 | 8 | 8 |
| E1 | 9 | 198 |

TABLE VIIIA-continued

HPV 6A
HLA-A2 Supermotif Peptides

| 2 | 3 | 4 |
|---|---|---|
| E1 | 10 | 198 |
| E1 | 11 | 198 |
| E2 | 8 | 82 |
| E7 | 8 | 82 |
| E7 | 9 | 82 |
| E5 | 11 | 59 |
| E5 | 8 | 55 |
| E5 | 9 | 55 |
| E5 | 11 | 55 |
| E5 | 9 | 51 |
| E5 | 10 | 51 |
| E5 | 11 | 51 |
| E1 | 9 | 298 |
| E1 | 10 | 298 |
| E1 | 11 | 298 |
| E5 | 11 | 69 |
| E5 | 10 | 60 |
| E5 | 11 | 60 |
| E5 | 8 | 72 |
| E5 | 9 | 72 |
| E5 | 11 | 72 |
| E1 | 9 | 276 |
| E1 | 9 | 563 |
| E1 | 10 | 563 |
| E5 | 8 | 56 |
| E5 | 10 | 56 |
| E2 | 8 | 42 |
| E2 | 10 | 42 |
| E5 | 8 | 52 |
| E5 | 9 | 52 |
| E5 | 10 | 52 |
| E5 | 11 | 52 |
| E2 | 8 | 94 |
| E2 | 11 | 94 |
| E5 | 8 | 65 |
| E5 | 9 | 65 |
| E5 | 10 | 65 |
| L1 | 10 | 367 |
| L1 | 11 | 367 |
| E6 | 11 | 27 |
| L1 | 11 | 309 |
| E1 | 9 | 511 |
| E1 | 10 | 511 |
| E1 | 11 | 511 |
| E7 | 9 | 15 |
| L2 | 8 | 399 |
| L2 | 11 | 399 |
| L1 | 11 | 465 |
| L1 | 8 | 209 |
| L1 | 10 | 209 |
| E1 | 11 | 132 |
| E1 | 8 | 358 |
| L2 | 9 | 23 |
| L2 | 10 | 23 |
| E4 | 11 | 81 |
| E6 | 9 | 121 |
| E1 | 9 | 555 |
| E1 | 10 | 555 |
| E1 | 11 | 555 |
| E5 | 8 | 49 |
| E5 | 9 | 49 |
| E5 | 11 | 49 |
| E5 | 10 | 70 |
| E5 | 11 | 70 |
| E1 | 8 | 268 |
| E1 | 9 | 268 |
| E1 | 10 | 268 |
| E1 | 11 | 268 |
| E1 | 8 | 115 |
| L2 | 8 | 372 |
| L2 | 9 | 372 |
| E6 | 10 | 38 |
| E5 | 9 | 61 |
| E5 | 10 | 61 |

TABLE VIIIA-continued

HPV 6A
HLA-A2 Supermotif Peptides

| 2 | 3 | 4 |
|---|---|---|
| E5 | 11 | 61 |
| L2 | 8 | 338 |
| L2 | 11 | 338 |
| E5 | 8 | 73 |
| E5 | 10 | 73 |
| E1 | 8 | 514 |
| E1 | 9 | 514 |
| E7 | 9 | 29 |
| E5 | 9 | 47 |
| E5 | 10 | 47 |
| E5 | 11 | 47 |
| E1 | 8 | 277 |
| L1 | 8 | 295 |
| E1 | 8 | 564 |
| E1 | 9 | 564 |
| E7 | 8 | 67 |
| E7 | 10 | 67 |
| L1 | 8 | 95 |
| L1 | 10 | 95 |
| L1 | 10 | 233 |
| E4 | 8 | 1 |
| E4 | 9 | 1 |
| E4 | 11 | 1 |
| L2 | 8 | 87 |
| L2 | 11 | 87 |
| L1 | 11 | 383 |
| E1 | 8 | 306 |
| E1 | 10 | 398 |
| E1 | 11 | 398 |
| E2 | 8 | 75 |
| E2 | 9 | 75 |
| E2 | 11 | 75 |
| E2 | 9 | 56 |
| L1 | 8 | 338 |
| L1 | 9 | 338 |
| E2 | 10 | 151 |
| E1 | 10 | 47 |
| E1 | 11 | 47 |
| L1 | 8 | 196 |
| L1 | 9 | 196 |
| E1 | 10 | 19 |
| L1 | 8 | 154 |
| E1 | 11 | 274 |
| E1 | 10 | 361 |
| L2 | 8 | 115 |
| L2 | 11 | 115 |
| E2 | 9 | 71 |
| E2 | 8 | 249 |
| E2 | 11 | 249 |
| E6 | 8 | 36 |
| E1 | 11 | 607 |
| L2 | 8 | 270 |
| L2 | 10 | 270 |
| L2 | 11 | 270 |
| E1 | 10 | 389 |
| E6 | 8 | 5 |
| E6 | 9 | 5 |
| E1 | 9 | 329 |
| E1 | 9 | 600 |
| E1 | 8 | 270 |
| E1 | 9 | 270 |
| E1 | 10 | 270 |
| E1 | 11 | 270 |
| E1 | 8 | 451 |
| L1 | 11 | 31 |
| E1 | 8 | 300 |
| E1 | 9 | 300 |
| L2 | 8 | 366 |
| L2 | 10 | 366 |
| E1 | 9 | 55 |
| E1 | 11 | 55 |
| L1 | 10 | 445 |
| E1 | 8 | 539 |
| E1 | 10 | 539 |

TABLE VIIIA-continued

HPV 6A
HLA-A2 Supermotif Peptides

| 2 | 3 | 4 |
|---|---|---|
| L1 | 9 | 438 |
| E6 | 9 | 21 |
| E1 | 11 | 397 |
| L1 | 8 | 337 |
| L1 | 9 | 337 |
| L1 | 10 | 337 |
| L1 | 8 | 323 |
| L1 | 10 | 323 |
| L1 | 11 | 323 |
| E1 | 10 | 304 |
| E6 | 9 | 75 |
| L2 | 8 | 38 |
| E1 | 11 | 96 |
| E2 | 9 | 127 |
| E2 | 11 | 127 |
| L1 | 8 | 289 |
| L2 | 9 | 385 |
| L2 | 10 | 377 |
| L2 | 11 | 377 |
| L1 | 9 | 142 |
| L1 | 11 | 142 |
| E7 | 9 | 64 |
| E7 | 11 | 64 |
| E2 | 8 | 348 |
| E2 | 9 | 348 |
| L2 | 10 | 237 |
| L2 | 11 | 237 |
| L2 | 8 | 124 |
| L2 | 9 | 124 |
| L2 | 9 | 285 |
| L2 | 10 | 285 |
| L2 | 8 | 139 |
| L2 | 9 | 139 |
| E5 | 9 | 78 |
| E5 | 10 | 78 |
| E2 | 8 | 216 |
| E2 | 8 | 196 |
| E2 | 11 | 196 |
| L1 | 8 | 482 |
| L1 | 9 | 482 |
| L2 | 9 | 325 |
| L2 | 11 | 325 |
| L1 | 8 | 217 |
| L2 | 9 | 189 |
| L2 | 11 | 189 |
| E1 | 8 | 94 |
| E1 | 9 | 94 |
| E1 | 11 | 442 |
| E6 | 8 | 110 |
| E6 | 11 | 110 |
| E4 | 10 | 34 |
| L1 | 8 | 183 |
| L1 | 9 | 183 |
| L2 | 8 | 451 |
| L2 | 9 | 451 |
| L1 | 8 | 458 |
| L2 | 10 | 73 |
| L2 | 11 | 73 |
| E7 | 8 | 47 |
| E7 | 9 | 47 |
| E7 | 10 | 47 |
| E1 | 8 | 562 |
| E1 | 10 | 562 |
| E1 | 11 | 562 |
| E5 | 8 | 64 |
| E5 | 9 | 64 |
| E5 | 10 | 64 |
| E5 | 11 | 64 |
| E1 | 8 | 258 |
| E1 | 11 | 258 |
| L2 | 9 | 389 |
| L2 | 11 | 389 |
| L2 | 9 | 337 |
| E1 | 8 | 513 |

TABLE VIIIA-continued

HPV 6A
HLA-A2 Supermotif Peptides

| 2 | 3 | 4 |
|---|---|---|
| E1 | 9 | 513 |
| E1 | 10 | 513 |
| L2 | 8 | 86 |
| L2 | 9 | 86 |
| L2 | 9 | 411 |
| L2 | 10 | 411 |
| L2 | 11 | 411 |
| E1 | 10 | 545 |
| E1 | 11 | 545 |
| L2 | 11 | 168 |
| L2 | 11 | 243 |
| L2 | 8 | 423 |
| E2 | 10 | 354 |
| L2 | 8 | 183 |
| L2 | 11 | 183 |
| E4 | 8 | 67 |
| E4 | 10 | 67 |
| E4 | 11 | 67 |
| E1 | 9 | 182 |
| E1 | 11 | 182 |
| L2 | 9 | 359 |
| L2 | 10 | 207 |
| L2 | 11 | 207 |
| L1 | 9 | 90 |
| L1 | 11 | 90 |
| L2 | 9 | 96 |
| L2 | 10 | 96 |
| E2 | 9 | 258 |
| E2 | 10 | 258 |
| E2 | 11 | 258 |
| L2 | 8 | 171 |
| L2 | 9 | 171 |
| L2 | 10 | 171 |
| L2 | 11 | 426 |
| L2 | 8 | 158 |
| L2 | 9 | 158 |
| E7 | 10 | 20 |
| E7 | 11 | 20 |
| E5 | 8 | 19 |
| E5 | 11 | 19 |
| L1 | 8 | 266 |
| L2 | 11 | 212 |
| L1 | 10 | 175 |
| E5 | 8 | 5 |
| E5 | 9 | 5 |
| E5 | 11 | 5 |
| L1 | 8 | 16 |
| L1 | 10 | 16 |
| E2 | 10 | 222 |
| E2 | 11 | 222 |
| L2 | 10 | 418 |
| L2 | 8 | 363 |
| L2 | 10 | 363 |
| L2 | 11 | 363 |
| L2 | 8 | 91 |
| L2 | 8 | 252 |
| L2 | 10 | 252 |
| L2 | 8 | 328 |
| L2 | 11 | 328 |
| E1 | 9 | 636 |
| E1 | 10 | 636 |
| E1 | 11 | 636 |
| L1 | 8 | 177 |
| L1 | 10 | 177 |
| L1 | 11 | 177 |
| L1 | 9 | 419 |
| E1 | 9 | 399 |
| E1 | 10 | 399 |
| E1 | 11 | 399 |
| E1 | 9 | 64 |
| E1 | 11 | 64 |
| E5 | 9 | 7 |
| E5 | 10 | 7 |
| E5 | 11 | 7 |

TABLE VIIIA-continued

HPV 6A
HLA-A2 Supermotif Peptides

| 2 | 3 | 4 |
|---|---|---|
| L2 | 8 | 43 |
| L2 | 10 | 43 |
| E6 | 10 | 28 |
| E6 | 11 | 28 |
| E1 | 10 | 31 |
| E6 | 8 | 15 |
| E6 | 10 | 15 |
| L1 | 8 | 151 |
| L1 | 11 | 151 |
| L1 | 9 | 372 |
| L1 | 11 | 372 |
| L1 | 9 | 301 |
| L1 | 9 | 324 |
| L1 | 10 | 324 |
| E2 | 11 | 14 |
| E7 | 9 | 81 |
| E7 | 10 | 81 |
| E7 | 10 | 28 |
| L2 | 8 | 16 |
| L2 | 9 | 16 |
| L2 | 11 | 16 |
| E4 | 8 | 4 |
| E4 | 10 | 4 |
| E4 | 11 | 4 |
| L1 | 11 | 232 |
| L1 | 11 | 250 |
| E2 | 9 | 48 |
| E2 | 11 | 48 |
| E2 | 8 | 76 |
| E2 | 10 | 76 |
| E1 | 9 | 305 |
| E2 | 9 | 344 |
| E7 | 8 | 80 |
| E7 | 10 | 80 |
| E7 | 11 | 80 |
| E2 | 8 | 244 |
| E2 | 10 | 244 |
| E2 | 11 | 244 |
| L2 | 8 | 19 |
| L1 | 9 | 210 |
| L1 | 11 | 210 |
| E2 | 8 | 233 |
| E2 | 11 | 233 |
| L1 | 10 | 149 |
| E2 | 10 | 218 |
| E1 | 8 | 344 |
| E1 | 9 | 344 |
| L2 | 8 | 231 |
| L2 | 10 | 231 |
| L2 | 8 | 233 |
| L2 | 10 | 233 |
| E2 | 8 | 57 |
| E2 | 11 | 57 |
| E1 | 8 | 391 |
| E1 | 10 | 391 |
| L1 | 9 | 259 |
| L2 | 8 | 227 |
| L2 | 9 | 227 |
| L1 | 10 | 53 |
| L2 | 8 | 5 |
| L2 | 10 | 5 |
| L2 | 11 | 5 |
| L2 | 10 | 11 |
| L2 | 8 | 298 |
| L2 | 10 | 298 |
| L2 | 8 | 316 |
| L2 | 11 | 316 |
| L2 | 9 | 449 |
| L2 | 10 | 449 |
| L2 | 11 | 449 |
| E2 | 9 | 7 |
| E2 | 10 | 7 |
| E1 | 8 | 109 |
| L1 | 11 | 241 |

TABLE VIIIA-continued

HPV 6A
HLA-A2 Supermotif Peptides

| 2 | 3 | 4 |
|---|---|---|
| E1 | 8 | 125 |
| E1 | 9 | 125 |
| L2 | 8 | 281 |
| L2 | 9 | 245 |
| E2 | 9 | 303 |
| E1 | 8 | 616 |
| E7 | 9 | 66 |
| E7 | 11 | 66 |
| L1 | 9 | 94 |
| L1 | 11 | 94 |
| E1 | 9 | 69 |
| E1 | 10 | 69 |
| E1 | 11 | 69 |
| E1 | 10 | 117 |
| E2 | 8 | 343 |
| E2 | 10 | 343 |
| E1 | 9 | 343 |
| E1 | 10 | 343 |
| E1 | 9 | 324 |
| E1 | 10 | 324 |
| E1 | 11 | 324 |
| L1 | 8 | 476 |
| L1 | 9 | 476 |
| L2 | 9 | 68 |
| L2 | 11 | 68 |
| E1 | 9 | 293 |
| L1 | 8 | 29 |
| L1 | 8 | 279 |
| L1 | 10 | 279 |
| L2 | 8 | 221 |
| L2 | 9 | 221 |
| L1 | 11 | 140 |
| L1 | 9 | 488 |
| L1 | 11 | 488 |
| L1 | 8 | 379 |
| L1 | 10 | 379 |
| L1 | 11 | 379 |
| L2 | 8 | 111 |
| L2 | 11 | 111 |
| L2 | 11 | 77 |
| E6 | 8 | 3 |
| E6 | 9 | 3 |
| E6 | 10 | 3 |
| E6 | 11 | 3 |
| L2 | 10 | 181 |
| L2 | 8 | 13 |
| L2 | 11 | 13 |
| E6 | 8 | 9 |
| E6 | 11 | 9 |
| E1 | 8 | 547 |
| E1 | 9 | 547 |
| E1 | 10 | 547 |
| E1 | 11 | 547 |
| L2 | 9 | 153 |
| L2 | 9 | 267 |
| L2 | 11 | 267 |
| E5 | 8 | 30 |
| L1 | 8 | 50 |
| L1 | 9 | 50 |
| L1 | 10 | 50 |
| E2 | 9 | 207 |
| E2 | 11 | 207 |
| L2 | 8 | 392 |
| L1 | 10 | 474 |
| L1 | 11 | 474 |
| E1 | 9 | 247 |
| E1 | 10 | 247 |
| L1 | 8 | 375 |
| L1 | 9 | 375 |
| L1 | 10 | 375 |
| L2 | 8 | 81 |
| L2 | 10 | 103 |
| L2 | 11 | 103 |
| L1 | 11 | 285 |
| L1 | 10 | 86 |
| L1 | 11 | 86 |
| L2 | 9 | 49 |
| L2 | 11 | 49 |
| L2 | 8 | 106 |
| L2 | 9 | 106 |
| L2 | 11 | 106 |
| E1 | 9 | 490 |
| E1 | 10 | 490 |
| E1 | 11 | 490 |
| E2 | 9 | 81 |
| E4 | 8 | 80 |
| L1 | 9 | 294 |
| E1 | 9 | 260 |
| E1 | 10 | 260 |
| E2 | 10 | 88 |
| E6 | 10 | 23 |
| L2 | 10 | 304 |
| E2 | 8 | 150 |
| E2 | 11 | 150 |
| E1 | 10 | 635 |
| E1 | 11 | 635 |
| L1 | 10 | 418 |
| E1 | 8 | 354 |
| E1 | 9 | 354 |
| E7 | 10 | 45 |
| E7 | 11 | 45 |
| E2 | 8 | 23 |
| E2 | 9 | 23 |
| E4 | 8 | 86 |
| E4 | 9 | 86 |
| E4 | 10 | 86 |
| E5 | 8 | 14 |
| E5 | 9 | 14 |
| E5 | 10 | 14 |
| L1 | 8 | 335 |
| L1 | 10 | 335 |
| L1 | 11 | 335 |
| L2 | 8 | 241 |
| L2 | 8 | 210 |
| E2 | 8 | 220 |
| E2 | 9 | 226 |
| E6 | 10 | 7 |
| E2 | 8 | 201 |
| E2 | 9 | 211 |
| E2 | 11 | 211 |
| E1 | 8 | 289 |
| E1 | 9 | 289 |
| E1 | 10 | 289 |
| E1 | 11 | 289 |
| E2 | 8 | 190 |
| E2 | 10 | 190 |
| E1 | 11 | 331 |
| L1 | 11 | 7 |
| E2 | 10 | 317 |
| L1 | 8 | 281 |
| L1 | 10 | 281 |
| L1 | 8 | 189 |
| L1 | 9 | 189 |
| L1 | 11 | 189 |
| L1 | 10 | 392 |
| E2 | 10 | 40 |
| E5 | 8 | 45 |
| E5 | 9 | 45 |
| E5 | 11 | 45 |
| L2 | 9 | 260 |
| E1 | 8 | 185 |
| E1 | 9 | 185 |
| E1 | 11 | 185 |
| E2 | 9 | 198 |
| E2 | 11 | 198 |
| L2 | 9 | 164 |
| L2 | 11 | 164 |
| L2 | 8 | 145 |

TABLE VIIIA-continued

HPV 6A
HLA-A2 Supermotif Peptides

| 2 | 3 | 4 |
|---|---|---|
| L2 | 10 | 145 |
| L1 | 9 | 343 |
| E6 | 8 | 40 |
| E1 | 8 | 192 |
| L2 | 8 | 420 |
| L2 | 10 | 420 |
| L2 | 11 | 420 |
| L2 | 11 | 409 |
| L2 | 9 | 216 |
| E1 | 10 | 97 |
| E6 | 8 | 12 |
| E6 | 11 | 12 |
| E2 | 9 | 355 |
| E2 | 11 | 355 |
| L2 | 10 | 184 |
| L2 | 8 | 130 |
| L2 | 9 | 130 |
| L2 | 11 | 130 |
| E4 | 10 | 82 |
| E4 | 11 | 82 |
| E1 | 8 | 294 |
| L1 | 8 | 339 |
| L1 | 11 | 339 |
| E7 | 8 | 86 |
| E7 | 10 | 86 |
| E4 | 9 | 68 |
| E4 | 10 | 68 |
| E4 | 11 | 68 |
| L1 | 9 | 408 |
| L1 | 11 | 270 |
| E1 | 8 | 556 |
| E1 | 9 | 556 |
| E1 | 10 | 556 |
| E1 | 11 | 556 |
| E5 | 8 | 15 |
| E5 | 9 | 15 |
| E5 | 11 | 15 |
| E7 | 9 | 7 |
| E5 | 8 | 50 |
| E5 | 10 | 50 |
| E5 | 11 | 50 |
| E1 | 10 | 297 |
| E1 | 11 | 297 |
| E5 | 9 | 71 |
| E5 | 10 | 71 |
| E2 | 9 | 93 |
| L1 | 8 | 377 |
| L1 | 10 | 377 |
| E1 | 9 | 408 |
| E1 | 11 | 408 |
| E2 | 8 | 128 |
| E2 | 10 | 128 |
| E2 | 8 | 227 |
| E2 | 10 | 203 |
| E2 | 11 | 203 |
| L2 | 8 | 360 |
| L2 | 11 | 360 |
| E1 | 11 | 30 |
| L1 | 9 | 150 |
| L2 | 9 | 15 |
| L2 | 10 | 15 |
| E1 | 8 | 526 |
| E1 | 10 | 526 |
| L2 | 9 | 166 |
| L2 | 8 | 380 |
| L2 | 9 | 380 |
| L2 | 11 | 380 |
| L1 | 9 | 92 |
| L1 | 11 | 92 |
| E1 | 8 | 148 |
| E6 | 9 | 39 |
| E1 | 8 | 232 |
| E1 | 9 | 232 |
| L1 | 9 | 223 |
| L1 | 11 | 223 |
| E6 | 8 | 142 |
| E6 | 9 | 11 |
| L2 | 8 | 137 |
| L2 | 10 | 137 |
| L2 | 11 | 137 |
| E5 | 8 | 62 |
| E5 | 9 | 62 |
| E5 | 10 | 62 |
| E5 | 11 | 62 |
| E2 | 11 | 202 |
| L1 | 8 | 91 |
| L1 | 10 | 91 |
| L1 | 8 | 332 |
| L1 | 9 | 332 |
| L1 | 11 | 332 |
| L2 | 9 | 151 |
| L2 | 11 | 151 |
| E4 | 8 | 77 |
| E4 | 9 | 77 |
| E4 | 11 | 77 |
| E4 | 8 | 84 |
| E4 | 9 | 84 |
| E4 | 10 | 84 |
| E4 | 11 | 84 |
| E5 | 9 | 12 |
| E5 | 10 | 12 |
| E5 | 11 | 12 |
| L2 | 9 | 136 |
| L2 | 11 | 136 |
| L2 | 10 | 150 |
| E4 | 8 | 76 |
| E4 | 9 | 76 |
| E4 | 10 | 76 |
| E6 | 11 | 87 |
| L2 | 8 | 386 |
| E4 | 9 | 91 |
| E2 | 8 | 212 |
| E2 | 10 | 212 |
| E1 | 8 | 290 |
| E1 | 9 | 290 |
| E1 | 10 | 290 |
| E6 | 10 | 88 |
| E6 | 11 | 88 |
| E4 | 9 | 73 |
| E4 | 10 | 73 |
| E4 | 11 | 73 |
| E2 | 10 | 116 |
| 82 | 9 | 191 |
| E1 | 8 | 345 |
| E1 | 10 | 332 |
| E1 | 11 | 332 |
| L2 | 11 | 387 |
| E1 | 10 | 78 |
| L2 | 9 | 378 |
| L2 | 10 | 378 |
| L2 | 11 | 378 |
| E4 | 8 | 92 |
| L1 | 9 | 328 |
| L1 | 11 | 328 |
| L1 | 10 | 8 |
| E1 | 9 | 317 |
| E1 | 11 | 317 |
| L2 | 10 | 339 |
| E1 | 10 | 239 |
| E1 | 8 | 519 |
| L2 | 8 | 97 |
| L2 | 9 | 97 |
| L2 | 11 | 97 |
| E1 | 8 | 291 |
| E1 | 9 | 291 |
| E1 | 11 | 291 |
| L1 | 8 | 21 |
| L1 | 10 | 21 |

TABLE VIIIA-continued

HPV 6A
HLA-A2 Supermotif Peptides

| 2 | 3 | 4 |
|---|---|---|
| E2 | 8 | 192 |
| E2 | 11 | 192 |
| E1 | 9 | 333 |
| E1 | 10 | 333 |
| E5 | 10 | 20 |
| L2 | 9 | 31 |
| L2 | 10 | 31 |
| L2 | 11 | 31 |
| L1 | 8 | 190 |
| L1 | 10 | 190 |
| L2 | 10 | 199 |
| E7 | 10 | 12 |
| L1 | 9 | 393 |
| E6 | 10 | 53 |
| E6 | 11 | 53 |
| E4 | 8 | 7 |
| E4 | 9 | 7 |
| E1 | 10 | 275 |
| E2 | 9 | 41 |
| E2 | 11 | 41 |
| L1 | 9 | 73 |
| L1 | 10 | 73 |
| E5 | 8 | 48 |
| E5 | 9 | 48 |
| E5 | 10 | 48 |
| E5 | 8 | 46 |
| E5 | 10 | 46 |
| E5 | 11 | 46 |
| L1 | 8 | 382 |
| L1 | 9 | 176 |
| L1 | 11 | 176 |
| E7 | 8 | 69 |
| E7 | 11 | 69 |
| E1 | 9 | 79 |
| E2 | 8 | 139 |
| E2 | 10 | 139 |
| E1 | 9 | 444 |
| E2 | 10 | 288 |
| L2 | 8 | 261 |
| L2 | 11 | 261 |
| E1 | 9 | 24 |
| E5 | 8 | 6 |
| E5 | 10 | 6 |
| E5 | 11 | 6 |
| E7 | 8 | 79 |
| E7 | 9 | 79 |
| E7 | 11 | 79 |
| E2 | 8 | 243 |
| E2 | 9 | 243 |
| E2 | 11 | 243 |
| E2 | 9 | 232 |
| L2 | 9 | 232 |
| L2 | 11 | 232 |
| E1 | 9 | 362 |
| L2 | 9 | 419 |
| L2 | 11 | 419 |
| E7 | 11 | 55 |
| L2 | 9 | 234 |
| E7 | 8 | 6 |
| E7 | 10 | 6 |
| L2 | 9 | 364 |
| L2 | 10 | 364 |
| L2 | 8 | 165 |
| L2 | 10 | 165 |
| L2 | 8 | 379 |
| L2 | 9 | 379 |
| L2 | 10 | 379 |
| L1 | 10 | 27 |
| L2 | 9 | 146 |
| E1 | 8 | 565 |
| L1 | 8 | 344 |
| L1 | 10 | 327 |
| E1 | 11 | 238 |
| L1 | 8 | 20 |
| L1 | 9 | 20 |
| L1 | 11 | 20 |
| E5 | 8 | 25 |
| E5 | 9 | 25 |
| E5 | 10 | 25 |
| E5 | 11 | 25 |
| L1 | 8 | 329 |
| L1 | 10 | 329 |
| L1 | 11 | 329 |
| E2 | 8 | 349 |
| L1 | 10 | 72 |
| L1 | 11 | 72 |
| E2 | 10 | 58 |
| E5 | 8 | 3 |
| E5 | 10 | 3 |
| E5 | 11 | 3 |
| E7 | 9 | 68 |
| E2 | 8 | 132 |
| E2 | 11 | 132 |
| L1 | 8 | 97 |
| E2 | 11 | 321 |
| E1 | 9 | 426 |
| E5 | 9 | 36 |
| E5 | 11 | 36 |
| E1 | 8 | 340 |
| E1 | 8 | 530 |
| E1 | 11 | 530 |
| E1 | 11 | 464 |
| E5 | 8 | 58 |
| E1 | 8 | 510 |
| E1 | 10 | 510 |
| E1 | 11 | 510 |
| E1 | 8 | 267 |
| E1 | 9 | 267 |
| E1 | 10 | 267 |
| E1 | 11 | 267 |
| E2 | 9 | 134 |
| E2 | 10 | 92 |
| E6 | 8 | 141 |
| E6 | 9 | 141 |
| E4 | 10 | 72 |
| E4 | 11 | 72 |
| E2 | 8 | 145 |
| E2 | 10 | 145 |
| E1 | 8 | 237 |
| E6 | 8 | 61 |
| L2 | 9 | 349 |
| E6 | 8 | 82 |
| E1 | 8 | 262 |
| E1 | 10 | 262 |
| E1 | 11 | 380 |
| E6 | 9 | 85 |
| E6 | 8 | 46 |
| E6 | 9 | 46 |
| E5 | 9 | 81 |
| L1 | 9 | 385 |
| L1 | 10 | 385 |
| E4 | 11 | 12 |
| E6 | 10 | 105 |
| E1 | 10 | 86 |
| L2 | 9 | 435 |
| E1 | 8 | 579 |
| E1 | 10 | 579 |
| E5 | 8 | 54 |
| E5 | 9 | 54 |
| E5 | 10 | 54 |
| L2 | 8 | 371 |
| L2 | 9 | 371 |
| L2 | 10 | 371 |
| E1 | 9 | 532 |
| E1 | 10 | 532 |
| L1 | 10 | 358 |
| E1 | 11 | 536 |
| L2 | 9 | 18 |

TABLE VIIIA-continued

HPV 6A
HLA-A2 Supermotif Peptides

| 2 | 3 | 4 |
|---|---|---|
| L1 | 8 | 65 |
| L1 | 9 | 65 |
| L1 | 10 | 65 |
| E2 | 8 | 159 |
| E2 | 11 | 159 |
| L1 | 10 | 350 |
| E2 | 8 | 214 |
| E2 | 10 | 214 |
| E5 | 8 | 43 |
| E5 | 9 | 43 |
| E5 | 10 | 43 |
| E5 | 11 | 43 |
| E1 | 8 | 402 |
| E4 | 8 | 6 |
| E4 | 9 | 6 |
| E4 | 10 | 6 |
| E2 | 8 | 168 |
| L1 | 9 | 287 |
| L1 | 10 | 287 |
| L2 | 8 | 71 |
| L1 | 8 | 10 |
| L1 | 11 | 10 |
| E2 | 9 | 138 |
| E2 | 11 | 138 |
| L1 | 8 | 415 |
| E1 | 8 | 91 |
| E1 | 9 | 91 |
| E1 | 11 | 91 |
| L1 | 11 | 26 |
| E2 | 9 | 131 |

TABLE VIIIB

HPV 6B
HLA-A2 Supermotif Peptides

| 2 | 3 | 4 |
|---|---|---|
| L1 | 9 | 234 |
| L2 | 10 | 329 |
| L2 | 11 | 329 |
| E5A | 9 | 9 |
| E5A | 10 | 9 |
| E1 | 8 | 318 |
| E1 | 10 | 318 |
| L1 | 8 | 489 |
| L1 | 10 | 489 |
| L2 | 9 | 340 |
| L2 | 11 | 340 |
| E4 | 8 | 12 |
| E4 | 10 | 12 |
| E2 | 8 | 3 |
| L2 | 8 | 286 |
| L2 | 9 | 286 |
| E2 | 8 | 72 |
| E2 | 11 | 72 |
| L2 | 10 | 112 |
| L2 | 11 | 112 |
| E1 | 11 | 112 |
| L2 | 8 | 140 |
| L2 | 11 | 140 |
| L1 | 8 | 420 |
| E1 | 8 | 475 |
| E1 | 9 | 22 |
| E1 | 11 | 22 |
| E2 | 10 | 250 |
| E1 | 8 | 65 |
| E1 | 10 | 65 |
| E4 | 9 | 24 |
| E4 | 11 | 24 |
| L2 | 8 | 228 |

TABLE VIIIB-continued

HPV 6B
HLA-A2 Supermotif Peptides

| 2 | 3 | 4 |
|---|---|---|
| L2 | 11 | 228 |
| L1 | 11 | 81 |
| L2 | 9 | 421 |
| L2 | 10 | 421 |
| E1 | 10 | 554 |
| E1 | 11 | 554 |
| E6 | 11 | 37 |
| E5A | 8 | 79 |
| E5A | 9 | 79 |
| E5A | 10 | 79 |
| E5A | 11 | 79 |
| E1 | 9 | 319 |
| L1 | 9 | 203 |
| L2 | 9 | 327 |
| E1 | 10 | 63 |
| L2 | 8 | 341 |
| L2 | 10 | 341 |
| L1 | 8 | 312 |
| L1 | 10 | 300 |
| E4 | 9 | 13 |
| E4 | 11 | 13 |
| E1 | 10 | 381 |
| E2 | 11 | 217 |
| L1 | 9 | 22 |
| L1 | 11 | 22 |
| E1 | 11 | 296 |
| E1 | 10 | 407 |
| E4 | 8 | 71 |
| E4 | 9 | 71 |
| L2 | 10 | 14 |
| L2 | 11 | 14 |
| E1 | 9 | 525 |
| E1 | 11 | 525 |
| E6 | 10 | 10 |
| E6 | 8 | 86 |
| E1 | 11 | 77 |
| E1 | 10 | 101 |
| L1 | 9 | 43 |
| E5B | 8 | 36 |
| E2 | 10 | 231 |
| L1 | 8 | 483 |
| E1 | 8 | 601 |
| E6 | 11 | 64 |
| E5B | 8 | 20 |
| E5B | 10 | 20 |
| E5B | 11 | 20 |
| E2 | 9 | 124 |
| E2 | 10 | 124 |
| L1 | 9 | 341 |
| L1 | 11 | 341 |
| E1 | 11 | 406 |
| E1 | 10 | 473 |
| E1 | 11 | 234 |
| E6 | 8 | 67 |
| E6 | 9 | 137 |
| E2 | 9 | 296 |
| E2 | 8 | 35 |
| E2 | 9 | 35 |
| E1 | 8 | 488 |
| E1 | 11 | 488 |
| L1 | 9 | 153 |
| E2 | 8 | 11 |
| E5B | 8 | 5 |
| E5B | 10 | 5 |
| E7 | 9 | 71 |
| E1 | 9 | 14 |
| E1 | 10 | 14 |
| L1 | 11 | 14 |
| L1 | 8 | 171 |
| E6 | 8 | 131 |
| E2 | 8 | 252 |
| E6 | 8 | 31 |
| E6 | 9 | 31 |
| E6 | 10 | 31 |

TABLE VIIIB-continued

HPV 6B
HLA-A2 Supermotif Peptides

| 2 | 3 | 4 |
|---|---|---|
| E6 | 11 | 31 |
| E1 | 9 | 640 |
| E1 | 10 | 640 |
| E4 | 10 | 74 |
| E4 | 11 | 74 |
| E2 | 8 | 9 |
| E2 | 10 | 9 |
| E2 | 8 | 153 |
| E1 | 10 | 516 |
| E1 | 11 | 516 |
| E1 | 8 | 524 |
| E1 | 10 | 524 |
| E2 | 11 | 230 |
| L1 | 9 | 24 |
| E1 | 8 | 369 |
| E1 | 9 | 369 |
| E1 | 8 | 170 |
| E1 | 10 | 170 |
| L2 | 9 | 278 |
| L2 | 10 | 278 |
| L2 | 11 | 278 |
| E6 | 11 | 96 |
| E7 | 8 | 75 |
| E7 | 9 | 75 |
| E7 | 10 | 75 |
| L2 | 8 | 322 |
| L2 | 9 | 322 |
| L2 | 9 | 403 |
| L2 | 11 | 403 |
| E1 | 11 | 570 |
| L2 | 11 | 347 |
| L2 | 10 | 395 |
| L2 | 11 | 395 |
| E1 | 11 | 222 |
| E2 | 10 | 313 |
| L1 | 8 | 366 |
| L1 | 11 | 366 |
| E7 | 8 | 14 |
| E7 | 10 | 14 |
| L1 | 9 | 208 |
| L1 | 11 | 208 |
| E1 | 11 | 46 |
| L1 | 9 | 195 |
| L1 | 10 | 195 |
| L2 | 9 | 42 |
| L2 | 11 | 42 |
| E6 | 9 | 14 |
| E6 | 11 | 14 |
| L1 | 10 | 455 |
| L1 | 11 | 455 |
| L1 | 10 | 198 |
| E1 | 9 | 481 |
| E1 | 11 | 481 |
| E1 | 10 | 73 |
| L1 | 8 | 331 |
| L1 | 9 | 331 |
| L1 | 10 | 331 |
| E5B | 8 | 11 |
| E5B | 9 | 11 |
| E5B | 11 | 11 |
| E2 | 9 | 143 |
| E2 | 10 | 143 |
| L2 | 10 | 369 |
| L2 | 11 | 369 |
| E1 | 8 | 534 |
| L1 | 10 | 411 |
| L1 | 11 | 411 |
| L2 | 10 | 30 |
| L2 | 11 | 30 |
| E6 | 8 | 99 |
| L1 | 9 | 215 |
| L1 | 10 | 215 |
| L2 | 11 | 258 |
| L2 | 8 | 143 |
| L2 | 9 | 143 |
| L2 | 10 | 143 |
| E2 | 8 | 348 |
| E2 | 9 | 348 |
| E2 | 9 | 136 |
| E2 | 11 | 136 |
| E1 | 8 | 71 |
| E1 | 9 | 71 |
| E1 | 9 | 178 |
| E2 | 8 | 174 |
| L2 | 9 | 274 |
| E1 | 10 | 250 |
| E1 | 8 | 143 |
| E2 | 9 | 2 |
| E1 | 8 | 21 |
| E1 | 10 | 21 |
| E2 | 8 | 66 |
| E2 | 10 | 66 |
| L2 | 8 | 173 |
| L2 | 10 | 173 |
| E1 | 10 | 336 |
| E1 | 11 | 336 |
| E1 | 11 | 180 |
| E1 | 11 | 62 |
| L1 | 11 | 299 |
| E1 | 11 | 100 |
| L2 | 8 | 332 |
| L2 | 9 | 332 |
| L2 | 10 | 332 |
| L2 | 8 | 192 |
| L2 | 9 | 192 |
| E1 | 8 | 105 |
| E1 | 9 | 105 |
| E1 | 11 | 105 |
| L2 | 11 | 120 |
| E6 | 10 | 42 |
| E1 | 8 | 197 |
| E1 | 10 | 197 |
| E1 | 11 | 197 |
| E2 | 8 | 17 |
| E2 | 10 | 17 |
| L2 | 8 | 334 |
| E2 | 9 | 74 |
| E2 | 10 | 74 |
| E1 | 11 | 417 |
| E1 | 11 | 360 |
| E7 | 11 | 27 |
| E2 | 9 | 341 |
| E2 | 10 | 341 |
| E7 | 10 | 73 |
| E7 | 11 | 73 |
| E6 | 9 | 92 |
| E6 | 10 | 92 |
| E6 | 11 | 92 |
| E2 | 9 | 96 |
| L2 | 8 | 135 |
| L2 | 10 | 135 |
| E4 | 8 | 85 |
| E4 | 9 | 85 |
| E4 | 10 | 85 |
| E4 | 11 | 85 |
| E2 | 8 | 185 |
| E2 | 9 | 185 |
| E7 | 10 | 39 |
| E1 | 8 | 141 |
| E1 | 10 | 141 |
| E1 | 9 | 39 |
| E1 | 10 | 39 |
| E6 | 8 | 113 |
| E6 | 9 | 113 |
| E6 | 10 | 113 |
| L1 | 9 | 262 |
| L1 | 10 | 262 |
| L1 | 11 | 262 |

TABLE VIIIB-continued

HPV 6B
HLA-A2 Supermotif Peptides

| 2 | 3 | 4 |
|---|---|---|
| L1 | 8 | 103 |
| L1 | 10 | 103 |
| E2 | 8 | 118 |
| E2 | 11 | 118 |
| L1 | 8 | 381 |
| L1 | 9 | 381 |
| E7 | 9 | 78 |
| E7 | 10 | 78 |
| E2 | 8 | 205 |
| E2 | 9 | 205 |
| E2 | 11 | 205 |
| E5A | 8 | 2 |
| E5A | 9 | 2 |
| E5A | 11 | 2 |
| L1 | 11 | 206 |
| L1 | 8 | 80 |
| L1 | 9 | 252 |
| L2 | 9 | 442 |
| L2 | 11 | 442 |
| E1 | 8 | 50 |
| L1 | 8 | 369 |
| L1 | 9 | 369 |
| L1 | 10 | 369 |
| E5A | 8 | 16 |
| E5A | 10 | 16 |
| E5A | 11 | 16 |
| E1 | 10 | 454 |
| L2 | 9 | 428 |
| E5B | 8 | 22 |
| E5B | 9 | 22 |
| E5B | 10 | 22 |
| E5B | 11 | 22 |
| E5A | 8 | 40 |
| E5A | 9 | 40 |
| E5A | 10 | 40 |
| E5A | 11 | 40 |
| E2 | 10 | 346 |
| E2 | 11 | 346 |
| E1 | 10 | 494 |
| L1 | 8 | 119 |
| E1 | 8 | 393 |
| E1 | 11 | 393 |
| L2 | 8 | 397 |
| L2 | 9 | 397 |
| E1 | 10 | 446 |
| L1 | 9 | 245 |
| L2 | 8 | 239 |
| L2 | 9 | 239 |
| L2 | 10 | 239 |
| E1 | 9 | 457 |
| L2 | 11 | 276 |
| E1 | 11 | 18 |
| E2 | 8 | 290 |
| E1 | 8 | 252 |
| E1 | 10 | 252 |
| L1 | 8 | 371 |
| L1 | 10 | 371 |
| L2 | 8 | 129 |
| L2 | 9 | 129 |
| L2 | 10 | 129 |
| E2 | 11 | 171 |
| E5A | 8 | 28 |
| E5A | 10 | 28 |
| L1 | 8 | 326 |
| L1 | 11 | 326 |
| E5A | 8 | 24 |
| E5A | 9 | 24 |
| E5A | 10 | 24 |
| E5A | 11 | 24 |
| L2 | 11 | 198 |
| L1 | 8 | 202 |
| L1 | 10 | 202 |
| L2 | 9 | 117 |
| E4 | 9 | 2 |

TABLE VIIIB-continued

HPV 6B
HLA-A2 Supermotif Peptides

| 2 | 3 | 4 |
|---|---|---|
| E4 | 10 | 2 |
| E4 | 11 | 2 |
| L2 | 10 | 314 |
| L1 | 8 | 318 |
| L1 | 10 | 318 |
| L1 | 11 | 318 |
| L2 | 8 | 58 |
| E1 | 9 | 243 |
| E1 | 11 | 194 |
| L2 | 9 | 356 |
| L2 | 10 | 356 |
| E1 | 8 | 326 |
| E1 | 9 | 326 |
| E2 | 11 | 156 |
| E1 | 9 | 350 |
| E1 | 10 | 350 |
| L1 | 10 | 101 |
| L2 | 10 | 56 |
| E7 | 8 | 22 |
| E7 | 9 | 22 |
| E5B | 9 | 28 |
| E5B | 10 | 28 |
| E1 | 8 | 217 |
| E2 | 9 | 50 |
| E2 | 10 | 50 |
| L1 | 9 | 400 |
| L1 | 10 | 400 |
| L2 | 8 | 292 |
| E5B | 9 | 15 |
| E5B | 10 | 15 |
| L2 | 10 | 223 |
| L1 | 9 | 144 |
| L1 | 11 | 144 |
| E5B | 8 | 25 |
| E2 | 8 | 55 |
| E2 | 10 | 55 |
| E1 | 8 | 273 |
| L1 | 8 | 136 |
| L1 | 10 | 136 |
| E1 | 10 | 162 |
| E2 | 8 | 162 |
| E2 | 11 | 162 |
| L1 | 8 | 107 |
| L2 | 8 | 300 |
| E1 | 8 | 191 |
| E1 | 9 | 191 |
| L2 | 8 | 215 |
| L2 | 10 | 215 |
| L2 | 8 | 25 |
| L2 | 11 | 25 |
| E1 | 10 | 6 |
| L2 | 9 | 64 |
| L2 | 11 | 64 |
| E1 | 8 | 436 |
| E1 | 9 | 436 |
| L2 | 10 | 60 |
| E1 | 11 | 145 |
| L1 | 10 | 407 |
| E7 | 9 | 85 |
| E7 | 11 | 85 |
| L2 | 8 | 412 |
| L2 | 10 | 412 |
| L2 | 11 | 412 |
| E1 | 8 | 467 |
| E1 | 9 | 467 |
| E1 | 10 | 467 |
| E1 | 11 | 467 |
| E1 | 9 | 147 |
| L1 | 10 | 222 |
| E5A | 8 | 11 |
| E5A | 10 | 11 |
| E5A | 11 | 11 |
| E4 | 8 | 100 |
| E4 | 10 | 100 |

TABLE VIIIB-continued

HPV 6B
HLA-A2 Supermotif Peptides

| 2 | 3 | 4 |
|---|---|---|
| E1 | 10 | 316 |
| L2 | 9 | 51 |
| L2 | 11 | 51 |
| L1 | 10 | 111 |
| L1 | 10 | 478 |
| E2 | 9 | 242 |
| E2 | 10 | 242 |
| L1 | 8 | 113 |
| E1 | 9 | 415 |
| E1 | 8 | 189 |
| E1 | 10 | 189 |
| E1 | 11 | 189 |
| L1 | 8 | 35 |
| L1 | 9 | 35 |
| L1 | 10 | 35 |
| E2 | 10 | 53 |
| L2 | 8 | 177 |
| L2 | 9 | 177 |
| L2 | 10 | 177 |
| E6 | 9 | 119 |
| E6 | 11 | 119 |
| E1 | 8 | 264 |
| E1 | 11 | 264 |
| E2 | 8 | 78 |
| E2 | 9 | 310 |
| E1 | 10 | 449 |
| E1 | 11 | 449 |
| E2 | 11 | 274 |
| L2 | 9 | 230 |
| L2 | 11 | 230 |
| E1 | 8 | 176 |
| E1 | 11 | 176 |
| E6 | 8 | 25 |
| L1 | 8 | 387 |
| E4 | 10 | 36 |
| L2 | 8 | 306 |
| L2 | 10 | 306 |
| E1 | 8 | 581 |
| L2 | 11 | 149 |
| L1 | 10 | 361 |
| E2 | 8 | 29 |
| E1 | 10 | 502 |
| E7 | 8 | 5 |
| E7 | 9 | 5 |
| E7 | 11 | 5 |
| E5A | 8 | 8 |
| E5A | 10 | 8 |
| E5A | 11 | 8 |
| L2 | 11 | 40 |
| E1 | 9 | 98 |
| E5A | 8 | 22 |
| E5A | 10 | 22 |
| E5A | 11 | 22 |
| E1 | 9 | 474 |
| L2 | 8 | 326 |
| L2 | 10 | 326 |
| L2 | 8 | 287 |
| E5A | 9 | 21 |
| E5A | 11 | 21 |
| L1 | 9 | 272 |
| L1 | 11 | 272 |
| E5A | 11 | 31 |
| L2 | 9 | 113 |
| L2 | 10 | 113 |
| L2 | 8 | 279 |
| L2 | 9 | 279 |
| L2 | 10 | 279 |
| E6 | 10 | 97 |
| L2 | 10 | 141 |
| L2 | 11 | 141 |
| E1 | 10 | 195 |
| L2 | 8 | 178 |
| L2 | 9 | 178 |
| E5A | 10 | 32 |

TABLE VIIIB-continued

HPV 6B
HLA-A2 Supermotif Peptides

| 2 | 3 | 4 |
|---|---|---|
| E5A | 11 | 32 |
| L2 | 9 | 44 |
| E5A | 9 | 17 |
| E5A | 10 | 17 |
| E6 | 8 | 120 |
| E6 | 10 | 120 |
| L1 | 9 | 191 |
| E1 | 8 | 313 |
| E1 | 10 | 265 |
| E1 | 11 | 265 |
| L2 | 8 | 404 |
| L2 | 10 | 404 |
| L2 | 8 | 429 |
| L2 | 11 | 429 |
| E1 | 8 | 56 |
| E1 | 10 | 56 |
| E1 | 11 | 56 |
| E1 | 10 | 571 |
| L1 | 8 | 376 |
| L1 | 9 | 376 |
| L1 | 11 | 376 |
| E1 | 11 | 341 |
| L2 | 11 | 82 |
| L2 | 8 | 131 |
| L2 | 10 | 131 |
| L2 | 11 | 131 |
| L1 | 10 | 187 |
| L1 | 11 | 187 |
| E4 | 9 | 93 |
| E4 | 10 | 93 |
| E4 | 11 | 93 |
| E7 | 10 | 89 |
| E5B | 8 | 23 |
| E5B | 9 | 23 |
| E5B | 10 | 23 |
| E7 | 11 | 11 |
| L2 | 10 | 121 |
| L2 | 11 | 121 |
| E1 | 10 | 443 |
| E2 | 11 | 287 |
| E1 | 8 | 23 |
| E1 | 10 | 23 |
| L2 | 9 | 104 |
| L2 | 10 | 104 |
| L2 | 11 | 104 |
| E5A | 8 | 34 |
| E5A | 9 | 34 |
| E5A | 11 | 34 |
| E5A | 8 | 41 |
| E5A | 9 | 41 |
| E5A | 10 | 41 |
| E5A | 11 | 41 |
| E2 | 10 | 45 |
| E1 | 11 | 553 |
| E2 | 8 | 325 |
| E2 | 9 | 325 |
| E2 | 10 | 325 |
| E2 | 11 | 325 |
| L1 | 9 | 311 |
| E6 | 10 | 123 |
| L1 | 11 | 486 |
| E1 | 11 | 433 |
| E6 | 11 | 73 |
| E2 | 10 | 351 |
| E1 | 8 | 312 |
| E1 | 9 | 312 |
| E2 | 9 | 359 |
| E2 | 10 | 359 |
| E1 | 8 | 254 |
| E1 | 10 | 254 |
| E6 | 11 | 128 |
| E1 | 9 | 357 |
| L2 | 10 | 22 |
| L2 | 11 | 22 |

TABLE VIIIB-continued

HPV 6B
HLA-A2 Supermotif Peptides

| 2 | 3 | 4 |
|---|---|---|
| E1 | 9 | 114 |
| E1 | 8 | 420 |
| L1 | 8 | 169 |
| L1 | 10 | 169 |
| E6 | 8 | 94 |
| E6 | 9 | 94 |
| E7 | 8 | 49 |
| E2 | 8 | 47 |
| E2 | 10 | 47 |
| L1 | 8 | 148 |
| L1 | 11 | 148 |
| E1 | 11 | 424 |
| E6 | 9 | 18 |
| E6 | 10 | 18 |
| E4 | 8 | 52 |
| E1 | 8 | 231 |
| E1 | 9 | 231 |
| E1 | 10 | 231 |
| E2 | 11 | 115 |
| E2 | 8 | 165 |
| E2 | 11 | 165 |
| E1 | 8 | 518 |
| E1 | 9 | 518 |
| L2 | 8 | 34 |
| L2 | 11 | 34 |
| E2 | 8 | 147 |
| E2 | 11 | 147 |
| E6 | 9 | 116 |
| E1 | 9 | 121 |
| E6 | 11 | 52 |
| E1 | 8 | 283 |
| E1 | 9 | 283 |
| E1 | 10 | 283 |
| E2 | 10 | 63 |
| E2 | 11 | 63 |
| L1 | 9 | 61 |
| L1 | 9 | 19 |
| L1 | 10 | 19 |
| L1 | 11 | 71 |
| E1 | 8 | 351 |
| E1 | 9 | 351 |
| E1 | 11 | 351 |
| E4 | 10 | 23 |
| E4 | 9 | 70 |
| E4 | 10 | 70 |
| L1 | 10 | 42 |
| L2 | 8 | 107 |
| L2 | 10 | 107 |
| E1 | 9 | 255 |
| E1 | 11 | 255 |
| E1 | 11 | 307 |
| L1 | 10 | 271 |
| E1 | 8 | 557 |
| E1 | 9 | 557 |
| E1 | 10 | 557 |
| E6 | 11 | 101 |
| E1 | 10 | 223 |
| E1 | 11 | 223 |
| L2 | 8 | 179 |
| E1 | 8 | 491 |
| E1 | 9 | 491 |
| E1 | 10 | 491 |
| E2 | 9 | 314 |
| L1 | 11 | 186 |
| L2 | 8 | 246 |
| E5A | 9 | 33 |
| E5A | 10 | 33 |
| L1 | 11 | 41 |
| E5B | 9 | 18 |
| E5B | 10 | 18 |
| E1 | 11 | 521 |
| E1 | 9 | 540 |
| E2 | 10 | 15 |
| E1 | 11 | 208 |
| E7 | 8 | 83 |
| E7 | 11 | 83 |
| E4 | 8 | 18 |
| E1 | 9 | 198 |
| E1 | 10 | 198 |
| E1 | 11 | 198 |
| E7 | 8 | 82 |
| E7 | 9 | 82 |
| E5B | 8 | 29 |
| E5B | 9 | 29 |
| E5A | 11 | 59 |
| E5A | 8 | 55 |
| E5A | 9 | 55 |
| E5A | 11 | 55 |
| E5A | 9 | 51 |
| E5A | 10 | 51 |
| E5A | 11 | 51 |
| E5B | 8 | 30 |
| E1 | 9 | 298 |
| E1 | 10 | 298 |
| E1 | 11 | 298 |
| E2 | 8 | 82 |
| E5A | 11 | 69 |
| E5A | 10 | 60 |
| E5A | 11 | 60 |
| E5A | 8 | 72 |
| E5A | 9 | 72 |
| E5A | 11 | 72 |
| E1 | 9 | 276 |
| E1 | 9 | 563 |
| E1 | 10 | 563 |
| E5A | 8 | 56 |
| E5A | 10 | 56 |
| E2 | 8 | 42 |
| E2 | 10 | 42 |
| E5A | 8 | 52 |
| E5A | 9 | 52 |
| E5A | 10 | 52 |
| E5A | 11 | 52 |
| E2 | 8 | 94 |
| E2 | 11 | 94 |
| E5A | 8 | 65 |
| E5A | 9 | 65 |
| E5A | 10 | 65 |
| L1 | 10 | 367 |
| L1 | 11 | 367 |
| E6 | 11 | 27 |
| L1 | 11 | 309 |
| E1 | 9 | 511 |
| E1 | 10 | 511 |
| E1 | 11 | 511 |
| E7 | 9 | 15 |
| L2 | 8 | 398 |
| L2 | 11 | 398 |
| L1 | 11 | 465 |
| L1 | 8 | 209 |
| L1 | 10 | 209 |
| L2 | 9 | 74 |
| L2 | 10 | 74 |
| E5B | 10 | 3 |
| E1 | 11 | 132 |
| E1 | 8 | 358 |
| L2 | 9 | 23 |
| L2 | 10 | 23 |
| E4 | 11 | 91 |
| E6 | 9 | 121 |
| E1 | 8 | 458 |
| E1 | 11 | 458 |
| E1 | 9 | 555 |
| E1 | 10 | 555 |
| E1 | 11 | 555 |
| E5A | 8 | 49 |
| E5A | 9 | 49 |
| E5A | 11 | 49 |

TABLE VIIIB-continued

HPV 6B
HLA-A2 Supermotif Peptides

| 2 | 3 | 4 |
|---|---|---|
| E5A | 10 | 70 |
| E5A | 11 | 70 |
| E1 | 8 | 268 |
| E1 | 9 | 268 |
| E1 | 10 | 268 |
| E1 | 11 | 268 |
| E1 | 8 | 115 |
| L2 | 8 | 372 |
| L2 | 9 | 372 |
| E6 | 10 | 38 |
| E5A | 9 | 61 |
| E5A | 10 | 61 |
| E5A | 11 | 61 |
| L2 | 8 | 338 |
| L2 | 11 | 338 |
| E5A | 8 | 73 |
| E5A | 10 | 73 |
| E1 | 8 | 514 |
| E1 | 9 | 514 |
| E7 | 9 | 29 |
| E1 | 8 | 277 |
| E5A | 9 | 47 |
| E5A | 10 | 47 |
| E5A | 11 | 47 |
| L1 | 8 | 295 |
| E2 | 10 | 222 |
| E2 | 11 | 222 |
| E1 | 8 | 564 |
| E1 | 9 | 564 |
| E7 | 8 | 67 |
| E7 | 10 | 67 |
| L1 | 8 | 95 |
| L1 | 10 | 95 |
| L1 | 10 | 233 |
| E4 | 8 | 11 |
| E4 | 9 | 11 |
| E4 | 11 | 11 |
| L2 | 8 | 87 |
| L2 | 11 | 87 |
| L1 | 11 | 383 |
| E5B | 11 | 26 |
| E1 | 8 | 306 |
| E5B | 11 | 2 |
| E1 | 10 | 398 |
| E1 | 11 | 398 |
| E2 | 8 | 75 |
| E2 | 9 | 75 |
| E2 | 11 | 75 |
| E2 | 9 | 56 |
| L1 | 8 | 338 |
| L1 | 9 | 338 |
| E2 | 10 | 151 |
| E1 | 10 | 47 |
| E1 | 11 | 47 |
| L1 | 8 | 196 |
| L1 | 9 | 196 |
| E1 | 10 | 19 |
| L1 | 8 | 154 |
| E1 | 11 | 274 |
| E1 | 10 | 361 |
| L2 | 8 | 115 |
| L2 | 11 | 115 |
| E2 | 9 | 71 |
| E2 | 8 | 249 |
| E2 | 11 | 249 |
| E6 | 8 | 36 |
| L2 | 8 | 270 |
| L2 | 10 | 270 |
| L2 | 11 | 270 |
| E1 | 10 | 389 |
| E6 | 8 | 5 |
| E6 | 9 | 5 |
| E1 | 9 | 329 |
| E1 | 9 | 600 |

TABLE VIIIB-continued

HPV 6B
HLA-A2 Supermotif Peptides

| 2 | 3 | 4 |
|---|---|---|
| E1 | 8 | 270 |
| E1 | 9 | 270 |
| E1 | 10 | 270 |
| E1 | 11 | 270 |
| E1 | 8 | 451 |
| E1 | 9 | 451 |
| L1 | 11 | 31 |
| E4 | 8 | 5 |
| E4 | 9 | 5 |
| E4 | 11 | 5 |
| E1 | 8 | 300 |
| E1 | 9 | 300 |
| L2 | 8 | 366 |
| L2 | 10 | 366 |
| E1 | 9 | 55 |
| E1 | 11 | 55 |
| E7 | 8 | 88 |
| E7 | 11 | 88 |
| L1 | 10 | 445 |
| E1 | 8 | 539 |
| E1 | 10 | 539 |
| L1 | 9 | 438 |
| E6 | 9 | 21 |
| E1 | 11 | 397 |
| L1 | 8 | 337 |
| L1 | 9 | 337 |
| L1 | 10 | 337 |
| L1 | 8 | 323 |
| L1 | 10 | 323 |
| L1 | 11 | 323 |
| E1 | 10 | 304 |
| E6 | 9 | 75 |
| L2 | 8 | 38 |
| E1 | 11 | 96 |
| E2 | 9 | 127 |
| E2 | 11 | 127 |
| E1 | 11 | 607 |
| L1 | 8 | 289 |
| L2 | 8 | 385 |
| L2 | 10 | 377 |
| L2 | 11 | 377 |
| L1 | 9 | 142 |
| L1 | 11 | 142 |
| E7 | 9 | 64 |
| E7 | 11 | 64 |
| L2 | 10 | 237 |
| L2 | 11 | 237 |
| L2 | 8 | 124 |
| L2 | 9 | 124 |
| L2 | 8 | 285 |
| L2 | 10 | 285 |
| L2 | 8 | 139 |
| L2 | 9 | 139 |
| L2 | 8 | 420 |
| L2 | 10 | 420 |
| L2 | 11 | 420 |
| E5A | 9 | 78 |
| E5A | 10 | 78 |
| E5A | 11 | 78 |
| E2 | 8 | 216 |
| E2 | 8 | 196 |
| E2 | 11 | 196 |
| L1 | 8 | 482 |
| L1 | 9 | 482 |
| L2 | 9 | 325 |
| L2 | 11 | 325 |
| L1 | 8 | 217 |
| L2 | 9 | 189 |
| L2 | 11 | 189 |
| E1 | 8 | 94 |
| E1 | 9 | 94 |
| E1 | 11 | 442 |
| E4 | 10 | 69 |
| E4 | 11 | 69 |

TABLE VIIIB-continued

HPV 6B
HLA-A2 Supermotif Peptides

| 2 | 3 | 4 |
|---|---|---|
| E6 | 8 | 110 |
| E6 | 11 | 110 |
| E4 | 10 | 44 |
| L1 | 8 | 183 |
| L1 | 9 | 183 |
| L2 | 8 | 451 |
| L2 | 9 | 451 |
| L1 | 8 | 458 |
| E7 | 8 | 47 |
| E7 | 9 | 47 |
| E7 | 10 | 47 |
| E1 | 8 | 562 |
| E1 | 10 | 562 |
| E1 | 11 | 562 |
| E5A | 8 | 64 |
| E5A | 9 | 64 |
| E5A | 10 | 64 |
| E5A | 11 | 64 |
| L2 | 10 | 73 |
| L2 | 11 | 73 |
| L2 | 8 | 389 |
| L2 | 10 | 389 |
| E1 | 8 | 258 |
| E1 | 11 | 258 |
| L2 | 9 | 337 |
| E1 | 8 | 513 |
| E1 | 9 | 513 |
| E1 | 10 | 513 |
| L2 | 8 | 86 |
| L2 | 9 | 86 |
| L2 | 9 | 410 |
| L2 | 10 | 410 |
| E1 | 10 | 545 |
| E1 | 11 | 545 |
| L2 | 11 | 168 |
| L2 | 11 | 243 |
| L2 | 8 | 423 |
| E2 | 10 | 354 |
| E4 | 8 | 77 |
| E4 | 10 | 77 |
| E4 | 11 | 77 |
| E1 | 9 | 182 |
| E1 | 11 | 182 |
| L2 | 9 | 359 |
| L2 | 10 | 207 |
| L2 | 11 | 207 |
| L1 | 9 | 90 |
| L1 | 11 | 90 |
| L2 | 8 | 183 |
| L2 | 11 | 183 |
| L2 | 9 | 96 |
| L2 | 10 | 96 |
| E2 | 9 | 258 |
| E2 | 10 | 258 |
| E2 | 11 | 258 |
| L2 | 8 | 171 |
| L2 | 9 | 171 |
| L2 | 10 | 171 |
| L2 | 11 | 426 |
| L2 | 8 | 158 |
| L2 | 9 | 158 |
| E7 | 10 | 20 |
| E7 | 11 | 20 |
| E5A | 8 | 19 |
| E5A | 11 | 19 |
| L1 | 8 | 266 |
| L2 | 11 | 212 |
| L1 | 10 | 175 |
| E5A | 8 | 5 |
| E5A | 9 | 5 |
| E5A | 11 | 5 |
| L1 | 8 | 16 |
| L1 | 10 | 16 |
| L2 | 8 | 363 |

TABLE VIIIB-continued

HPV 6B
HLA-A2 Supermotif Peptides

| 2 | 3 | 4 |
|---|---|---|
| L2 | 10 | 363 |
| L2 | 11 | 363 |
| L2 | 8 | 417 |
| L2 | 11 | 417 |
| L2 | 8 | 91 |
| L2 | 8 | 252 |
| L2 | 10 | 252 |
| L2 | 8 | 328 |
| L2 | 11 | 328 |
| E1 | 9 | 636 |
| E1 | 10 | 636 |
| E1 | 11 | 636 |
| L1 | 8 | 177 |
| L1 | 10 | 177 |
| L1 | 11 | 177 |
| L1 | 9 | 419 |
| E1 | 9 | 399 |
| E1 | 10 | 399 |
| E1 | 11 | 399 |
| E1 | 9 | 64 |
| E1 | 11 | 64 |
| E5A | 9 | 7 |
| E5A | 11 | 7 |
| L2 | 8 | 43 |
| L2 | 10 | 43 |
| E6 | 10 | 28 |
| E6 | 11 | 28 |
| E1 | 10 | 31 |
| E6 | 8 | 15 |
| E6 | 10 | 15 |
| L1 | 8 | 151 |
| L1 | 11 | 151 |
| L1 | 9 | 372 |
| L1 | 11 | 372 |
| L1 | 9 | 301 |
| L1 | 9 | 324 |
| L1 | 10 | 324 |
| E2 | 11 | 14 |
| E7 | 9 | 81 |
| E7 | 10 | 81 |
| E7 | 10 | 28 |
| L2 | 8 | 16 |
| L2 | 9 | 16 |
| L2 | 11 | 16 |
| E4 | 8 | 14 |
| E4 | 10 | 14 |
| E4 | 11 | 14 |
| L1 | 11 | 232 |
| L1 | 11 | 250 |
| E2 | 9 | 48 |
| E2 | 11 | 48 |
| E2 | 8 | 76 |
| E2 | 10 | 76 |
| E1 | 9 | 305 |
| E2 | 9 | 344 |
| E7 | 8 | 80 |
| E7 | 10 | 80 |
| E7 | 11 | 80 |
| E2 | 8 | 244 |
| E2 | 10 | 244 |
| E2 | 11 | 244 |
| L2 | 8 | 19 |
| L1 | 9 | 210 |
| L1 | 11 | 210 |
| E2 | 8 | 233 |
| E2 | 11 | 233 |
| L1 | 10 | 149 |
| L2 | 8 | 75 |
| L2 | 9 | 75 |
| E2 | 10 | 218 |
| E1 | 8 | 344 |
| E1 | 9 | 344 |
| L2 | 8 | 231 |
| L2 | 10 | 231 |

TABLE VIIIB-continued

HPV 6B
HLA-A2 Supermotif Peptides

| 2 | 3 | 4 |
|---|---|---|
| L2 | 8 | 233 |
| L2 | 10 | 233 |
| E2 | 8 | 57 |
| E2 | 11 | 57 |
| E1 | 8 | 391 |
| E1 | 10 | 391 |
| L1 | 9 | 259 |
| L2 | 8 | 227 |
| L2 | 9 | 227 |
| L1 | 10 | 53 |
| L2 | 8 | 5 |
| L2 | 10 | 5 |
| L2 | 11 | 5 |
| L2 | 10 | 11 |
| E5B | 9 | 35 |
| L2 | 8 | 298 |
| L2 | 10 | 298 |
| L2 | 8 | 316 |
| L2 | 11 | 316 |
| L2 | 9 | 449 |
| L2 | 10 | 449 |
| L2 | 11 | 449 |
| E2 | 9 | 7 |
| E2 | 10 | 7 |
| E1 | 8 | 109 |
| L1 | 11 | 241 |
| E1 | 8 | 125 |
| E1 | 9 | 125 |
| L2 | 8 | 281 |
| L2 | 9 | 245 |
| E2 | 9 | 303 |
| E1 | 8 | 616 |
| E7 | 9 | 66 |
| E7 | 11 | 66 |
| L1 | 9 | 94 |
| L1 | 11 | 94 |
| E1 | 9 | 69 |
| E1 | 10 | 69 |
| E1 | 11 | 69 |
| E1 | 10 | 117 |
| E2 | 8 | 343 |
| E2 | 10 | 343 |
| E1 | 9 | 343 |
| E1 | 10 | 343 |
| E2 | 10 | 84 |
| E2 | 11 | 84 |
| E1 | 9 | 324 |
| E1 | 10 | 324 |
| E1 | 11 | 324 |
| L1 | 8 | 476 |
| L1 | 9 | 476 |
| L2 | 9 | 68 |
| L2 | 11 | 68 |
| E1 | 9 | 293 |
| L1 | 8 | 29 |
| L1 | 8 | 279 |
| L1 | 10 | 279 |
| L2 | 8 | 221 |
| L2 | 9 | 221 |
| L1 | 11 | 140 |
| L1 | 9 | 488 |
| L1 | 11 | 488 |
| L1 | 8 | 379 |
| L1 | 10 | 379 |
| L1 | 11 | 379 |
| L2 | 8 | 111 |
| L2 | 11 | 111 |
| L2 | 11 | 77 |
| E6 | 8 | 3 |
| E6 | 9 | 3 |
| E6 | 10 | 3 |
| E6 | 11 | 3 |
| L2 | 10 | 181 |
| L2 | 8 | 13 |
| L2 | 11 | 13 |
| E6 | 8 | 9 |
| E6 | 11 | 9 |
| E1 | 8 | 547 |
| E1 | 9 | 547 |
| E1 | 10 | 547 |
| E1 | 11 | 547 |
| L2 | 9 | 153 |
| L2 | 9 | 267 |
| L2 | 11 | 267 |
| E5A | 8 | 30 |
| L1 | 8 | 50 |
| L1 | 9 | 50 |
| L1 | 10 | 50 |
| E2 | 9 | 207 |
| E2 | 11 | 207 |
| L1 | 10 | 474 |
| L1 | 11 | 474 |
| E1 | 9 | 247 |
| E1 | 10 | 247 |
| L1 | 8 | 375 |
| L1 | 9 | 375 |
| L1 | 10 | 375 |
| L2 | 8 | 81 |
| L2 | 10 | 103 |
| L2 | 11 | 103 |
| L1 | 11 | 285 |
| L1 | 10 | 86 |
| L1 | 11 | 86 |
| L2 | 9 | 49 |
| L2 | 11 | 49 |
| L2 | 8 | 106 |
| L2 | 9 | 106 |
| L2 | 11 | 106 |
| E1 | 9 | 490 |
| E1 | 10 | 490 |
| E1 | 11 | 490 |
| E2 | 9 | 81 |
| L2 | 8 | 391 |
| E4 | 8 | 90 |
| L1 | 9 | 294 |
| E1 | 9 | 260 |
| E1 | 10 | 260 |
| E2 | 10 | 88 |
| E6 | 10 | 23 |
| L2 | 10 | 304 |
| E2 | 8 | 150 |
| E2 | 11 | 150 |
| E1 | 10 | 635 |
| E1 | 11 | 635 |
| L1 | 10 | 418 |
| E1 | 8 | 354 |
| E1 | 9 | 354 |
| E7 | 10 | 45 |
| E7 | 11 | 45 |
| E2 | 8 | 23 |
| E2 | 9 | 23 |
| E5A | 8 | 14 |
| E5A | 9 | 14 |
| E5A | 10 | 14 |
| E4 | 8 | 96 |
| E4 | 9 | 96 |
| E4 | 10 | 96 |
| E2 | 9 | 226 |
| E2 | 8 | 220 |
| L1 | 8 | 335 |
| L1 | 10 | 335 |
| L1 | 11 | 335 |
| L2 | 8 | 241 |
| L2 | 8 | 210 |
| E6 | 10 | 7 |
| E2 | 8 | 201 |
| E2 | 9 | 211 |
| E2 | 11 | 211 |

TABLE VIIIB-continued

HPV 6B
HLA-A2 Supermotif Peptides

| 2 | 3 | 4 |
|---|---|---|
| E1 | 8 | 289 |
| E1 | 9 | 289 |
| E1 | 10 | 289 |
| E1 | 11 | 289 |
| E2 | 8 | 190 |
| E2 | 10 | 190 |
| E1 | 11 | 331 |
| L1 | 11 | 7 |
| E2 | 10 | 317 |
| L1 | 8 | 281 |
| L1 | 10 | 281 |
| L1 | 8 | 189 |
| L1 | 9 | 189 |
| L1 | 11 | 189 |
| L1 | 10 | 392 |
| E2 | 10 | 40 |
| E5A | 8 | 45 |
| E5A | 9 | 45 |
| E5A | 11 | 45 |
| L2 | 9 | 260 |
| E1 | 8 | 185 |
| E1 | 9 | 185 |
| E1 | 11 | 185 |
| E2 | 9 | 198 |
| E2 | 11 | 198 |
| L2 | 9 | 164 |
| L2 | 11 | 164 |
| L2 | 8 | 145 |
| L2 | 10 | 145 |
| L1 | 9 | 343 |
| E6 | 8 | 40 |
| E1 | 8 | 192 |
| L2 | 11 | 408 |
| L2 | 9 | 216 |
| E1 | 10 | 97 |
| E6 | 8 | 12 |
| E6 | 11 | 12 |
| E2 | 9 | 355 |
| E2 | 11 | 355 |
| L2 | 8 | 130 |
| L2 | 9 | 130 |
| L2 | 11 | 130 |
| E4 | 10 | 92 |
| E4 | 11 | 92 |
| E1 | 8 | 294 |
| L1 | 8 | 339 |
| L1 | 11 | 339 |
| E4 | 9 | 78 |
| E4 | 10 | 78 |
| E4 | 11 | 78 |
| L1 | 9 | 408 |
| L1 | 11 | 270 |
| E1 | 8 | 556 |
| E1 | 9 | 556 |
| E1 | 10 | 556 |
| E1 | 11 | 556 |
| E7 | 9 | 7 |
| E5A | 8 | 50 |
| E5A | 10 | 50 |
| E5A | 11 | 50 |
| E1 | 10 | 297 |
| E1 | 11 | 297 |
| E5A | 9 | 71 |
| E5A | 10 | 71 |
| E7 | 8 | 86 |
| E7 | 10 | 86 |
| E2 | 9 | 93 |
| L1 | 8 | 377 |
| L1 | 10 | 377 |
| E2 | 11 | 221 |
| E1 | 9 | 408 |
| E1 | 11 | 408 |
| E2 | 8 | 128 |
| E2 | 10 | 128 |
| E5B | 11 | 59 |
| E2 | 10 | 203 |
| E2 | 11 | 203 |
| L2 | 8 | 360 |
| L2 | 11 | 360 |
| E1 | 11 | 30 |
| L1 | 9 | 150 |
| L2 | 9 | 15 |
| L2 | 10 | 15 |
| E1 | 8 | 526 |
| E1 | 10 | 526 |
| L2 | 9 | 166 |
| L2 | 8 | 380 |
| L2 | 9 | 380 |
| L2 | 11 | 380 |
| L1 | 9 | 92 |
| L1 | 11 | 92 |
| E1 | 8 | 148 |
| E6 | 9 | 39 |
| L1 | 9 | 223 |
| L1 | 11 | 223 |
| E1 | 8 | 232 |
| E1 | 9 | 232 |
| E6 | 8 | 142 |
| E5B | 9 | 63 |
| E6 | 9 | 11 |
| L2 | 8 | 137 |
| L2 | 10 | 137 |
| L2 | 11 | 137 |
| E5A | 8 | 62 |
| E5A | 9 | 62 |
| E5A | 10 | 62 |
| E5A | 11 | 62 |
| E2 | 11 | 202 |
| L1 | 8 | 91 |
| L1 | 10 | 91 |
| L1 | 8 | 332 |
| L1 | 9 | 332 |
| L1 | 11 | 332 |
| L2 | 9 | 151 |
| L2 | 11 | 151 |
| E4 | 8 | 87 |
| E4 | 9 | 87 |
| E4 | 11 | 87 |
| E5A | 9 | 12 |
| E5A | 10 | 12 |
| E5A | 11 | 12 |
| E4 | 8 | 94 |
| E4 | 9 | 94 |
| E4 | 10 | 94 |
| E4 | 11 | 94 |
| L2 | 9 | 136 |
| L2 | 11 | 136 |
| L2 | 10 | 150 |
| E4 | 8 | 86 |
| E4 | 9 | 86 |
| E4 | 10 | 86 |
| E6 | 11 | 87 |
| L2 | 11 | 386 |
| E4 | 9 | 101 |
| E2 | 8 | 212 |
| E2 | 10 | 212 |
| E2 | 11 | 212 |
| E1 | 8 | 290 |
| E1 | 9 | 290 |
| E1 | 10 | 290 |
| E6 | 10 | 88 |
| E6 | 11 | 88 |
| E4 | 9 | 83 |
| E4 | 10 | 83 |
| E4 | 11 | 83 |
| E2 | 10 | 116 |
| E2 | 9 | 191 |
| E1 | 8 | 345 |

TABLE VIIIB-continued

HPV 6B
HLA-A2 Supermotif Peptides

| 2 | 3 | 4 |
|---|---|---|
| E1 | 10 | 332 |
| E1 | 11 | 332 |
| L2 | 10 | 387 |
| E1 | 10 | 78 |
| L2 | 9 | 378 |
| L2 | 10 | 378 |
| L2 | 11 | 378 |
| L2 | 10 | 184 |
| E4 | 8 | 102 |
| L1 | 9 | 328 |
| L1 | 11 | 328 |
| L1 | 10 | 8 |
| E1 | 9 | 317 |
| E1 | 11 | 317 |
| L2 | 10 | 339 |
| E1 | 10 | 239 |
| E1 | 8 | 519 |
| L2 | 8 | 97 |
| L2 | 9 | 97 |
| L2 | 11 | 97 |
| E1 | 8 | 291 |
| E1 | 9 | 291 |
| E1 | 11 | 291 |
| L1 | 8 | 21 |
| L1 | 10 | 21 |
| E2 | 8 | 192 |
| E2 | 11 | 192 |
| E1 | 9 | 333 |
| E1 | 10 | 333 |
| E5A | 10 | 20 |
| L2 | 9 | 31 |
| L2 | 10 | 31 |
| L2 | 11 | 31 |
| L1 | 8 | 190 |
| L1 | 10 | 190 |
| E7 | 10 | 12 |
| L1 | 9 | 393 |
| E6 | 10 | 53 |
| E6 | 11 | 53 |
| E4 | 8 | 17 |
| E4 | 9 | 17 |
| E1 | 10 | 275 |
| E2 | 9 | 41 |
| E2 | 11 | 41 |
| L1 | 9 | 73 |
| L1 | 10 | 73 |
| E5A | 8 | 48 |
| E5A | 9 | 48 |
| E5A | 10 | 48 |
| E5A | 8 | 46 |
| E5A | 10 | 46 |
| E5A | 11 | 46 |
| E4 | 8 | 10 |
| E4 | 9 | 10 |
| E4 | 10 | 10 |
| L1 | 8 | 382 |
| L1 | 9 | 176 |
| L1 | 11 | 176 |
| E7 | 8 | 69 |
| E7 | 11 | 69 |
| E1 | 9 | 79 |
| E2 | 8 | 139 |
| E2 | 10 | 139 |
| E1 | 9 | 444 |
| E2 | 10 | 288 |
| L2 | 8 | 261 |
| L2 | 11 | 261 |
| E1 | 9 | 24 |
| E5A | 8 | 6 |
| E5A | 10 | 6 |
| E7 | 8 | 79 |
| E7 | 9 | 79 |
| E7 | 11 | 79 |
| E2 | 8 | 243 |
| E2 | 9 | 243 |
| E2 | 11 | 243 |
| E2 | 9 | 232 |
| L2 | 9 | 232 |
| L2 | 11 | 232 |
| E1 | 9 | 362 |
| E7 | 11 | 55 |
| L2 | 9 | 234 |
| E7 | 8 | 6 |
| E7 | 10 | 6 |
| L2 | 9 | 364 |
| L2 | 10 | 364 |
| L2 | 10 | 418 |
| L2 | 8 | 165 |
| L2 | 10 | 165 |
| L2 | 8 | 379 |
| L2 | 9 | 379 |
| L2 | 10 | 379 |
| L1 | 10 | 27 |
| L2 | 9 | 185 |
| L2 | 11 | 185 |
| L2 | 9 | 146 |
| E1 | 8 | 565 |
| L1 | 8 | 344 |
| L1 | 10 | 327 |
| E1 | 11 | 238 |
| L1 | 8 | 20 |
| L1 | 9 | 20 |
| L1 | 11 | 20 |
| E5A | 8 | 25 |
| E5A | 9 | 25 |
| E5A | 10 | 25 |
| E5A | 11 | 25 |
| L1 | 8 | 329 |
| L1 | 10 | 329 |
| L1 | 11 | 329 |
| E2 | 8 | 349 |
| L1 | 10 | 72 |
| L1 | 11 | 72 |
| E2 | 10 | 58 |
| E5A | 8 | 3 |
| E5A | 10 | 3 |
| E5A | 11 | 3 |
| E7 | 9 | 68 |
| L2 | 10 | 199 |
| E2 | 8 | 132 |
| L1 | 8 | 97 |
| E2 | 11 | 321 |
| E1 | 9 | 426 |
| E5A | 9 | 36 |
| E5A | 11 | 36 |
| E1 | 8 | 340 |
| E1 | 8 | 530 |
| E1 | 11 | 530 |
| E5B | 9 | 13 |
| E5B | 11 | 13 |
| E1 | 11 | 464 |
| E5B | 8 | 17 |
| E5B | 10 | 17 |
| E5B | 11 | 17 |
| E5A | 8 | 58 |
| E1 | 8 | 510 |
| E1 | 10 | 510 |
| E1 | 11 | 510 |
| E1 | 8 | 267 |
| E1 | 9 | 267 |
| E1 | 10 | 267 |
| E1 | 11 | 267 |
| E2 | 11 | 134 |
| E2 | 10 | 92 |
| E6 | 8 | 141 |
| E6 | 9 | 141 |
| E4 | 10 | 82 |
| E4 | 11 | 82 |

TABLE VIIIB-continued

HPV 6B
HLA-A2 Supermotif Peptides

| 2 | 3 | 4 |
|---|---|---|
| E2 | 8 | 145 |
| E2 | 10 | 145 |
| E1 | 8 | 237 |
| E6 | 8 | 61 |
| L2 | 9 | 349 |
| E6 | 8 | 82 |
| E1 | 8 | 262 |
| E1 | 10 | 262 |
| E1 | 11 | 380 |
| E6 | 9 | 85 |
| E6 | 8 | 46 |
| E6 | 9 | 46 |
| L1 | 9 | 385 |
| L1 | 10 | 385 |
| E5A | 8 | 81 |
| E5A | 9 | 81 |
| E4 | 11 | 22 |
| E6 | 10 | 105 |
| E1 | 10 | 86 |
| L2 | 9 | 435 |
| E1 | 8 | 579 |
| E1 | 10 | 579 |
| E5A | 8 | 54 |
| E5A | 9 | 54 |
| E5A | 10 | 54 |
| L2 | 8 | 371 |
| L2 | 9 | 371 |
| L2 | 10 | 371 |
| E1 | 9 | 532 |
| E1 | 10 | 532 |
| L1 | 10 | 358 |
| E1 | 11 | 536 |
| L2 | 9 | 18 |
| L1 | 8 | 65 |
| L1 | 9 | 65 |
| L1 | 10 | 65 |
| E2 | 8 | 159 |
| E2 | 11 | 159 |
| L1 | 10 | 350 |
| E2 | 8 | 214 |
| E2 | 9 | 214 |
| E2 | 10 | 214 |
| E5A | 8 | 43 |
| E5A | 9 | 43 |
| E5A | 10 | 43 |
| E5A | 11 | 43 |
| E5B | 8 | 62 |
| E5B | 10 | 62 |
| E1 | 8 | 402 |
| E4 | 8 | 16 |
| E4 | 9 | 16 |
| E4 | 10 | 16 |
| E4 | 9 | 9 |
| E4 | 10 | 9 |
| E4 | 11 | 9 |
| E2 | 8 | 168 |
| L1 | 9 | 287 |
| L1 | 10 | 287 |
| L2 | 8 | 71 |
| L1 | 8 | 10 |
| L1 | 11 | 10 |
| E2 | 9 | 138 |
| E2 | 11 | 138 |
| L1 | 8 | 415 |
| E1 | 8 | 91 |
| E1 | 9 | 91 |
| E1 | 11 | 91 |
| E5B | 8 | 57 |
| L1 | 11 | 26 |
| E2 | 9 | 131 |

TABLE VIIIC

HPV11
HLA-A2 Supermotif Peptides

| 2 | 3 | 4 |
|---|---|---|
| E5 | 8 | 9 |
| E5 | 9 | 9 |
| E5 | 10 | 9 |
| E6 | 9 | 62 |
| L1 | 9 | 235 |
| L2 | 10 | 328 |
| L2 | 11 | 328 |
| L2 | 9 | 339 |
| L2 | 11 | 339 |
| E4 | 8 | 12 |
| E4 | 10 | 12 |
| L2 | 8 | 86 |
| L2 | 11 | 86 |
| E2 | 8 | 282 |
| E5 | 8 | 10 |
| E5 | 9 | 10 |
| E5 | 11 | 10 |
| E6 | 11 | 83 |
| E2 | 8 | 3 |
| E2 | 8 | 72 |
| E2 | 11 | 72 |
| L2 | 10 | 111 |
| L2 | 11 | 111 |
| E1 | 11 | 112 |
| L2 | 8 | 139 |
| L2 | 11 | 139 |
| E1 | 10 | 407 |
| L1 | 8 | 421 |
| L2 | 8 | 80 |
| L2 | 8 | 285 |
| L2 | 9 | 285 |
| E1 | 9 | 22 |
| E1 | 11 | 22 |
| E1 | 8 | 475 |
| E1 | 8 | 65 |
| E1 | 10 | 65 |
| L1 | 11 | 81 |
| L2 | 9 | 417 |
| L2 | 10 | 417 |
| L2 | 8 | 227 |
| L2 | 11 | 227 |
| E1 | 10 | 554 |
| E1 | 11 | 554 |
| E6 | 9 | 37 |
| E6 | 11 | 37 |
| E4 | 8 | 24 |
| E4 | 9 | 24 |
| E4 | 11 | 24 |
| E1 | 9 | 319 |
| L1 | 9 | 204 |
| E1 | 10 | 63 |
| L1 | 8 | 313 |
| L1 | 10 | 301 |
| E4 | 9 | 13 |
| E4 | 11 | 13 |
| E7 | 10 | 45 |
| E7 | 11 | 45 |
| E1 | 10 | 381 |
| E2 | 8 | 217 |
| E2 | 10 | 217 |
| L1 | 9 | 22 |
| L1 | 11 | 22 |
| L2 | 9 | 22 |
| L2 | 10 | 22 |
| L2 | 10 | 13 |
| L2 | 11 | 13 |
| E1 | 9 | 525 |
| E1 | 11 | 525 |
| E6 | 10 | 10 |
| E5 | 8 | 11 |
| E5 | 10 | 11 |
| E5 | 11 | 11 |
| E1 | 11 | 77 |
| E5 | 8 | 25 |

TABLE VIIIC-continued

HPV11
HLA-A2 Supermotif Peptides

| 2 | 3 | 4 |
|---|---|---|
| E5 | 9 | 25 |
| E5 | 10 | 25 |
| E5 | 11 | 25 |
| E1 | 10 | 181 |
| E1 | 10 | 101 |
| L1 | 9 | 43 |
| E5 | 8 | 37 |
| E5 | 11 | 37 |
| E5 | 8 | 26 |
| L1 | 8 | 484 |
| E1 | 8 | 601 |
| E6 | 11 | 64 |
| E1 | 11 | 234 |
| E1 | 11 | 406 |
| E5 | 10 | 46 |
| E5 | 11 | 46 |
| L1 | 8 | 342 |
| L1 | 9 | 342 |
| L1 | 11 | 342 |
| E1 | 10 | 473 |
| E5 | 8 | 27 |
| E5 | 9 | 27 |
| E5 | 10 | 27 |
| E5 | 11 | 27 |
| E2 | 8 | 35 |
| E2 | 9 | 35 |
| E6 | 8 | 67 |
| E6 | 9 | 137 |
| E2 | 9 | 295 |
| E1 | 8 | 488 |
| E1 | 11 | 488 |
| L1 | 9 | 154 |
| E2 | 8 | 11 |
| E7 | 9 | 71 |
| E1 | 9 | 14 |
| E1 | 10 | 14 |
| E1 | 11 | 14 |
| E2 | 9 | 227 |
| E1 | 9 | 289 |
| E1 | 10 | 289 |
| E1 | 11 | 289 |
| E2 | 8 | 251 |
| E2 | 11 | 251 |
| E5 | 10 | 73 |
| E6 | 8 | 31 |
| E6 | 9 | 31 |
| E6 | 10 | 31 |
| 65 | 11 | 31 |
| E1 | 9 | 640 |
| E1 | 10 | 640 |
| E4 | 10 | 73 |
| E4 | 11 | 73 |
| E2 | 8 | 9 |
| E2 | 10 | 9 |
| E1 | 10 | 250 |
| E1 | 10 | 73 |
| E2 | 8 | 153 |
| E1 | 10 | 516 |
| E1 | 11 | 516 |
| E1 | 11 | 607 |
| E7 | 11 | 44 |
| E6 | 9 | 5 |
| E1 | 8 | 524 |
| E1 | 10 | 524 |
| L1 | 9 | 24 |
| E1 | 8 | 369 |
| E1 | 9 | 369 |
| L2 | 9 | 277 |
| L2 | 10 | 277 |
| L2 | 11 | 277 |
| E6 | 11 | 96 |
| L2 | 8 | 191 |
| L2 | 9 | 191 |
| E7 | 8 | 75 |
| E7 | 9 | 75 |
| E7 | 10 | 75 |
| E1 | 11 | 570 |
| L2 | 8 | 321 |
| L2 | 9 | 321 |
| L2 | 9 | 399 |
| L2 | 11 | 399 |
| L2 | 10 | 346 |
| E1 | 11 | 222 |
| E7 | 9 | 81 |
| E7 | 10 | 81 |
| L1 | 8 | 367 |
| L1 | 11 | 367 |
| E7 | 8 | 14 |
| E7 | 10 | 14 |
| L1 | 9 | 209 |
| L1 | 11 | 209 |
| L1 | 9 | 439 |
| E1 | 11 | 46 |
| L1 | 9 | 196 |
| L1 | 10 | 196 |
| L1 | 10 | 456 |
| L1 | 11 | 456 |
| L2 | 9 | 41 |
| L2 | 11 | 41 |
| E6 | 9 | 14 |
| E6 | 11 | 14 |
| L1 | 10 | 199 |
| E1 | 9 | 481 |
| E1 | 11 | 481 |
| E1 | 11 | 164 |
| E1 | 8 | 191 |
| E1 | 9 | 191 |
| E2 | 8 | 96 |
| E2 | 9 | 96 |
| L1 | 8 | 332 |
| L1 | 9 | 332 |
| L1 | 10 | 332 |
| E5 | 8 | 12 |
| E5 | 10 | 12 |
| E5 | 11 | 12 |
| E1 | 8 | 534 |
| L1 | 10 | 412 |
| L1 | 11 | 412 |
| L2 | 9 | 29 |
| L2 | 10 | 29 |
| L2 | 11 | 29 |
| L1 | 9 | 216 |
| L1 | 10 | 216 |
| L2 | 11 | 257 |
| L2 | 8 | 142 |
| L2 | 9 | 142 |
| L2 | 10 | 142 |
| E1 | 8 | 71 |
| E1 | 9 | 71 |
| E1 | 9 | 178 |
| L2 | 9 | 273 |
| E2 | 9 | 2 |
| E1 | 8 | 21 |
| E1 | 10 | 21 |
| E1 | 10 | 336 |
| E1 | 11 | 336 |
| E2 | 8 | 324 |
| E2 | 9 | 324 |
| E2 | 10 | 324 |
| E2 | 11 | 324 |
| E1 | 11 | 62 |
| E2 | 8 | 174 |
| L1 | 11 | 300 |
| L2 | 8 | 172 |
| L2 | 10 | 172 |
| E1 | 11 | 180 |
| E6 | 8 | 113 |
| E6 | 9 | 113 |

TABLE VIIIC-continued

HPV11
HLA-A2 Supermotif Peptides

| 2 | 3 | 4 |
|---|---|---|
| L2 | 8 | 331 |
| L2 | 9 | 331 |
| L2 | 10 | 331 |
| E1 | 8 | 105 |
| E1 | 9 | 105 |
| E1 | 11 | 105 |
| E6 | 10 | 42 |
| E2 | 10 | 312 |
| L2 | 8 | 333 |
| E1 | 8 | 197 |
| E1 | 11 | 197 |
| E2 | 8 | 17 |
| E2 | 10 | 17 |
| E1 | 11 | 417 |
| E2 | 9 | 74 |
| E2 | 10 | 74 |
| E1 | 11 | 360 |
| E7 | 11 | 27 |
| E2 | 10 | 340 |
| E2 | 8 | 66 |
| E2 | 10 | 66 |
| E6 | 9 | 92 |
| E6 | 10 | 92 |
| E6 | 11 | 92 |
| E2 | 8 | 185 |
| E2 | 9 | 185 |
| E7 | 10 | 36 |
| E1 | 8 | 141 |
| E1 | 9 | 39 |
| E1 | 10 | 39 |
| L1 | 8 | 103 |
| L1 | 10 | 103 |
| E2 | 11 | 118 |
| L1 | 8 | 382 |
| L1 | 9 | 382 |
| E2 | 8 | 205 |
| E2 | 9 | 205 |
| E2 | 11 | 205 |
| L2 | 11 | 119 |
| E5 | 8 | 2 |
| E5 | 9 | 2 |
| E5 | 10 | 2 |
| E5 | 11 | 2 |
| E6 | 8 | 61 |
| E6 | 10 | 61 |
| L1 | 11 | 207 |
| L1 | 8 | 80 |
| L1 | 9 | 253 |
| L1 | 11 | 253 |
| L2 | 9 | 438 |
| L2 | 11 | 438 |
| E5 | 8 | 24 |
| E5 | 9 | 24 |
| E5 | 10 | 24 |
| E5 | 11 | 24 |
| E1 | 8 | 50 |
| L1 | 8 | 370 |
| L1 | 9 | 370 |
| L1 | 10 | 370 |
| E1 | 8 | 454 |
| E1 | 10 | 454 |
| L2 | 9 | 424 |
| E1 | 10 | 494 |
| L1 | 11 | 464 |
| E1 | 8 | 393 |
| E1 | 11 | 393 |
| E2 | 10 | 345 |
| E2 | 11 | 345 |
| E1 | 10 | 446 |
| E1 | 9 | 457 |
| L2 | 8 | 238 |
| L2 | 9 | 238 |
| L2 | 10 | 238 |
| E5 | 9 | 16 |
| E5 | 10 | 16 |
| E5 | 11 | 16 |
| L2 | 11 | 275 |
| E1 | 10 | 18 |
| E1 | 11 | 18 |
| L2 | 8 | 319 |
| L2 | 10 | 319 |
| L2 | 11 | 319 |
| E1 | 8 | 252 |
| E1 | 10 | 252 |
| L1 | 8 | 372 |
| L1 | 10 | 372 |
| L2 | 11 | 154 |
| E5 | 8 | 20 |
| E5 | 9 | 20 |
| E5 | 11 | 20 |
| L2 | 9 | 262 |
| L2 | 9 | 128 |
| L2 | 10 | 128 |
| L2 | 8 | 393 |
| L2 | 9 | 393 |
| L1 | 8 | 327 |
| L1 | 11 | 327 |
| E5 | 8 | 23 |
| E5 | 9 | 23 |
| E5 | 10 | 23 |
| E5 | 11 | 23 |
| L2 | 11 | 197 |
| E5 | 8 | 40 |
| E5 | 9 | 40 |
| E5 | 10 | 40 |
| E5 | 11 | 40 |
| L2 | 8 | 61 |
| L2 | 11 | 61 |
| L1 | 8 | 203 |
| L1 | 10 | 203 |
| L2 | 9 | 116 |
| L2 | 10 | 313 |
| L1 | 8 | 319 |
| L1 | 10 | 319 |
| L1 | 11 | 319 |
| E1 | 9 | 243 |
| E1 | 11 | 194 |
| E1 | 8 | 326 |
| E1 | 9 | 326 |
| E2 | 11 | 156 |
| L1 | 10 | 101 |
| L2 | 8 | 55 |
| E7 | 8 | 22 |
| E5 | 9 | 29 |
| E5 | 10 | 29 |
| E2 | 8 | 55 |
| E2 | 9 | 55 |
| E2 | 10 | 55 |
| E1 | 8 | 217 |
| E2 | 9 | 50 |
| E2 | 10 | 50 |
| L1 | 9 | 401 |
| L1 | 10 | 401 |
| L2 | 8 | 291 |
| L2 | 10 | 222 |
| L1 | 9 | 145 |
| L1 | 11 | 145 |
| E1 | 8 | 273 |
| L1 | 8 | 137 |
| L1 | 10 | 137 |
| E1 | 10 | 160 |
| E2 | 8 | 162 |
| L2 | 8 | 309 |
| L1 | 8 | 107 |
| L2 | 8 | 299 |
| L2 | 8 | 24 |
| L2 | 11 | 24 |
| E5 | 8 | 40 |

TABLE VIIIC-continued

HPV11
HLA-A2 Supermotif Peptides

| 2 | 3 | 4 |
|---|---|---|
| E1 | 10 | 6 |
| L2 | 10 | 59 |
| L1 | 10 | 408 |
| E1 | 11 | 296 |
| E7 | 9 | 85 |
| E7 | 11 | 85 |
| L2 | 8 | 408 |
| L2 | 10 | 408 |
| L2 | 11 | 408 |
| E1 | 8 | 467 |
| E1 | 9 | 467 |
| E1 | 10 | 467 |
| E1 | 11 | 467 |
| L1 | 9 | 169 |
| E4 | 8 | 99 |
| E4 | 10 | 99 |
| L1 | 10 | 223 |
| L1 | 11 | 262 |
| E1 | 9 | 173 |
| E1 | 10 | 173 |
| E2 | 10 | 88 |
| L2 | 9 | 50 |
| L2 | 11 | 50 |
| L1 | 9 | 111 |
| L1 | 10 | 111 |
| E1 | 10 | 316 |
| E2 | 10 | 232 |
| L1 | 8 | 113 |
| E1 | 8 | 189 |
| E1 | 10 | 189 |
| E1 | 11 | 189 |
| E1 | 9 | 415 |
| L1 | 8 | 35 |
| L1 | 9 | 35 |
| L1 | 10 | 35 |
| E2 | 10 | 53 |
| E2 | 11 | 53 |
| E6 | 9 | 119 |
| E6 | 11 | 119 |
| L2 | 8 | 176 |
| L2 | 9 | 176 |
| L2 | 10 | 176 |
| E2 | 8 | 29 |
| E2 | 10 | 29 |
| E1 | 8 | 264 |
| E1 | 11 | 264 |
| E1 | 9 | 55 |
| E1 | 11 | 55 |
| E2 | 11 | 136 |
| E2 | 8 | 78 |
| E2 | 9 | 309 |
| L1 | 9 | 325 |
| L1 | 10 | 325 |
| E5 | 9 | 7 |
| E5 | 11 | 7 |
| E1 | 9 | 305 |
| E1 | 10 | 449 |
| E2 | 10 | 273 |
| E2 | 11 | 273 |
| E6 | 8 | 25 |
| L1 | 8 | 388 |
| E4 | 10 | 36 |
| L1 | 8 | 290 |
| L2 | 8 | 36 |
| L2 | 9 | 36 |
| L2 | 11 | 148 |
| E4 | 8 | 64 |
| E4 | 11 | 64 |
| L2 | 9 | 188 |
| L2 | 11 | 188 |
| L1 | 10 | 362 |
| E5 | 8 | 8 |
| E5 | 9 | 8 |
| E5 | 10 | 8 |
| E5 | 11 | 8 |
| E1 | 8 | 248 |
| E1 | 9 | 248 |
| L2 | 11 | 39 |
| E2 | 8 | 208 |
| E2 | 10 | 208 |
| E5 | 8 | 22 |
| E5 | 10 | 22 |
| E5 | 11 | 22 |
| E1 | 9 | 474 |
| E4 | 8 | 5 |
| E4 | 9 | 5 |
| E4 | 11 | 5 |
| E5 | 8 | 34 |
| E5 | 9 | 34 |
| E5 | 11 | 34 |
| L2 | 9 | 112 |
| L2 | 10 | 112 |
| L2 | 8 | 278 |
| L2 | 9 | 278 |
| L2 | 10 | 278 |
| L2 | 10 | 140 |
| L2 | 11 | 140 |
| E1 | 10 | 195 |
| E6 | 8 | 120 |
| E6 | 10 | 120 |
| L2 | 8 | 177 |
| L2 | 9 | 177 |
| E5 | 8 | 35 |
| E5 | 10 | 35 |
| E6 | 10 | 97 |
| L2 | 9 | 43 |
| E5 | 9 | 17 |
| E5 | 10 | 17 |
| E5 | 8 | 28 |
| E5 | 9 | 28 |
| E5 | 10 | 28 |
| E1 | 9 | 408 |
| E1 | 11 | 408 |
| E2 | 9 | 30 |
| E6 | 9 | 29 |
| E6 | 10 | 29 |
| E6 | 11 | 29 |
| L1 | 9 | 192 |
| L2 | 9 | 165 |
| E1 | 8 | 313 |
| E1 | 10 | 265 |
| E1 | 11 | 265 |
| L2 | 8 | 400 |
| L2 | 10 | 400 |
| L2 | 11 | 81 |
| L2 | 8 | 425 |
| L2 | 11 | 425 |
| L1 | 8 | 377 |
| L1 | 9 | 377 |
| L1 | 11 | 377 |
| E1 | 8 | 56 |
| E1 | 10 | 56 |
| E1 | 11 | 56 |
| E1 | 11 | 341 |
| L2 | 9 | 184 |
| L2 | 11 | 184 |
| L2 | 8 | 286 |
| L2 | 8 | 130 |
| L2 | 10 | 130 |
| L2 | 11 | 130 |
| L1 | 10 | 188 |
| L1 | 11 | 188 |
| E4 | 9 | 92 |
| E4 | 10 | 92 |
| E4 | 11 | 92 |
| E1 | 8 | 23 |
| E1 | 10 | 23 |
| E7 | 11 | 11 |

TABLE VIIIC-continued

HPV11
HLA-A2 Supermotif Peptides

| 2 | 3 | 4 |
|---|---|---|
| E5 | 11 | 31 |
| E1 | 10 | 443 |
| E2 | 11 | 286 |
| L2 | 9 | 103 |
| L2 | 10 | 103 |
| L2 | 11 | 103 |
| E2 | 10 | 45 |
| L1 | 9 | 312 |
| L2 | 10 | 21 |
| L2 | 11 | 21 |
| E6 | 11 | 73 |
| E2 | 10 | 350 |
| E1 | 8 | 312 |
| E1 | 9 | 312 |
| E1 | 8 | 254 |
| E1 | 10 | 254 |
| E6 | 9 | 116 |
| E1 | 9 | 460 |
| E6 | 11 | 128 |
| E1 | 9 | 357 |
| E1 | 9 | 114 |
| E1 | 8 | 420 |
| E7 | 8 | 42 |
| L1 | 8 | 433 |
| E2 | 8 | 112 |
| E2 | 8 | 47 |
| E2 | 10 | 47 |
| L1 | 8 | 149 |
| L1 | 11 | 149 |
| E1 | 9 | 424 |
| E1 | 11 | 424 |
| E4 | 8 | 53 |
| E6 | 9 | 18 |
| E6 | 10 | 18 |
| E2 | 10 | 84 |
| E2 | 11 | 84 |
| E2 | 11 | 165 |
| E1 | 8 | 518 |
| E1 | 9 | 518 |
| E7 | 10 | 39 |
| E7 | 11 | 39 |
| E1 | 11 | 433 |
| L2 | 8 | 33 |
| L2 | 11 | 33 |
| E2 | 9 | 358 |
| E2 | 10 | 358 |
| E1 | 9 | 121 |
| E6 | 8 | 99 |
| E1 | 8 | 283 |
| E1 | 9 | 283 |
| E1 | 10 | 283 |
| L1 | 10 | 53 |
| L1 | 9 | 61 |
| E2 | 8 | 147 |
| E2 | 11 | 147 |
| L1 | 9 | 19 |
| L1 | 11 | 71 |
| E6 | 11 | 52 |
| E1 | 8 | 351 |
| E1 | 9 | 351 |
| E1 | 11 | 351 |
| E2 | 8 | 82 |
| E4 | 9 | 23 |
| E4 | 10 | 23 |
| E2 | 9 | 313 |
| L1 | 10 | 42 |
| L2 | 8 | 106 |
| L2 | 10 | 106 |
| E1 | 9 | 255 |
| E1 | 11 | 255 |
| E1 | 11 | 307 |
| E5 | 9 | 33 |
| E5 | 10 | 33 |
| E1 | 8 | 557 |

TABLE VIIIC-continued

HPV11
HLA-A2 Supermotif Peptides

| 2 | 3 | 4 |
|---|---|---|
| E1 | 9 | 557 |
| E1 | 10 | 557 |
| E1 | 8 | 491 |
| E1 | 9 | 491 |
| E1 | 10 | 491 |
| E5 | 8 | 16 |
| E5 | 10 | 16 |
| E5 | 11 | 16 |
| E6 | 11 | 101 |
| E1 | 10 | 223 |
| E1 | 11 | 223 |
| L2 | 8 | 178 |
| E5 | 9 | 36 |
| E5 | 11 | 36 |
| L1 | 11 | 187 |
| L1 | 11 | 41 |
| E1 | 11 | 521 |
| E1 | 9 | 540 |
| E2 | 10 | 15 |
| E7 | 8 | 83 |
| E7 | 11 | 83 |
| E2 | 8 | 42 |
| E2 | 10 | 42 |
| E4 | 8 | 18 |
| E5 | 10 | 32 |
| E1 | 10 | 198 |
| E1 | 11 | 198 |
| E7 | 8 | 82 |
| E7 | 9 | 82 |
| E5 | 8 | 31 |
| E5 | 11 | 31 |
| E5 | 8 | 30 |
| E5 | 9 | 30 |
| E5 | 11 | 59 |
| E5 | 8 | 55 |
| E5 | 9 | 55 |
| E5 | 11 | 55 |
| E5 | 9 | 51 |
| E5 | 10 | 51 |
| E5 | 11 | 51 |
| E1 | 9 | 298 |
| E1 | 10 | 298 |
| E1 | 11 | 298 |
| L1 | 8 | 119 |
| L1 | 10 | 465 |
| E5 | 11 | 69 |
| E5 | 10 | 60 |
| E5 | 11 | 60 |
| E1 | 9 | 276 |
| E1 | 9 | 563 |
| E5 | 8 | 56 |
| E5 | 10 | 56 |
| E5 | 8 | 52 |
| E5 | 9 | 52 |
| E5 | 10 | 52 |
| E5 | 11 | 52 |
| E4 | 10 | 45 |
| E4 | 11 | 45 |
| E7 | 8 | 79 |
| E7 | 9 | 79 |
| E7 | 11 | 79 |
| E2 | 8 | 139 |
| E2 | 10 | 139 |
| E2 | 11 | 139 |
| E2 | 8 | 94 |
| E2 | 10 | 94 |
| E2 | 11 | 94 |
| E5 | 8 | 65 |
| E5 | 10 | 65 |
| L1 | 10 | 368 |
| L1 | 11 | 368 |
| L2 | 8 | 260 |
| L2 | 11 | 260 |
| E2 | 8 | 289 |

TABLE VIIIC-continued

HPV11
HLA-A2 Supermotif Peptides

| 2 | 3 | 4 |
|---|---|---|
| E6 | 11 | 27 |
| L1 | 11 | 310 |
| E1 | 9 | 511 |
| E1 | 10 | 511 |
| E1 | 11 | 511 |
| E7 | 9 | 15 |
| L2 | 10 | 228 |
| L1 | 9 | 466 |
| L1 | 11 | 466 |
| L1 | 8 | 210 |
| L1 | 10 | 210 |
| E2 | 8 | 56 |
| E2 | 9 | 56 |
| E7 | 11 | 55 |
| E5 | 10 | 4 |
| E1 | 8 | 514 |
| E1 | 9 | 514 |
| E1 | 11 | 132 |
| E1 | 8 | 358 |
| E4 | 11 | 90 |
| E5 | 10 | 70 |
| E1 | 9 | 555 |
| E1 | 10 | 555 |
| E1 | 11 | 555 |
| E5 | 8 | 49 |
| E5 | 9 | 49 |
| E5 | 11 | 49 |
| E1 | 8 | 268 |
| E1 | 9 | 268 |
| E1 | 10 | 268 |
| E1 | 11 | 268 |
| E7 | 8 | 48 |
| E7 | 9 | 48 |
| L2 | 8 | 368 |
| E6 | 8 | 38 |
| E6 | 10 | 38 |
| E4 | 9 | 69 |
| E5 | 9 | 61 |
| E5 | 10 | 61 |
| E5 | 11 | 61 |
| E1 | 8 | 115 |
| E2 | 11 | 62 |
| L2 | 8 | 337 |
| L2 | 11 | 337 |
| L1 | 11 | 273 |
| E1 | 8 | 277 |
| E5 | 9 | 47 |
| E5 | 10 | 47 |
| E5 | 11 | 47 |
| L1 | 8 | 296 |
| E7 | 8 | 5 |
| E7 | 9 | 5 |
| E7 | 11 | 5 |
| E1 | 8 | 564 |
| L2 | 8 | 245 |
| E7 | 10 | 67 |
| L1 | 8 | 95 |
| L1 | 10 | 95 |
| L1 | 10 | 234 |
| E4 | 8 | 11 |
| E4 | 9 | 11 |
| E4 | 11 | 11 |
| L1 | 11 | 384 |
| E1 | 8 | 306 |
| E5 | 11 | 3 |
| E1 | 10 | 398 |
| E1 | 11 | 398 |
| E2 | 8 | 75 |
| E2 | 9 | 75 |
| E2 | 11 | 75 |
| L1 | 11 | 339 |
| E1 | 10 | 47 |
| E1 | 11 | 47 |
| L1 | 8 | 197 |
| L1 | 9 | 197 |
| E1 | 9 | 19 |
| E1 | 10 | 19 |
| L1 | 8 | 155 |
| E1 | 11 | 274 |
| E5 | 8 | 1 |
| E1 | 10 | 361 |
| E4 | 10 | 1 |
| E4 | 11 | 1 |
| L2 | 8 | 114 |
| L2 | 11 | 114 |
| E2 | 9 | 71 |
| E6 | 8 | 36 |
| E6 | 10 | 36 |
| L2 | 8 | 269 |
| L2 | 10 | 269 |
| L2 | 11 | 269 |
| E1 | 10 | 389 |
| E1 | 9 | 329 |
| E1 | 11 | 100 |
| E1 | 9 | 600 |
| E1 | 8 | 270 |
| E1 | 9 | 270 |
| E1 | 10 | 270 |
| E1 | 11 | 270 |
| E1 | 8 | 451 |
| E1 | 11 | 451 |
| L1 | 11 | 31 |
| E1 | 8 | 300 |
| E1 | 9 | 300 |
| E2 | 8 | 254 |
| E2 | 9 | 254 |
| E7 | 8 | 88 |
| L1 | 10 | 446 |
| E1 | 8 | 539 |
| E1 | 10 | 539 |
| E6 | 9 | 21 |
| E1 | 11 | 397 |
| L1 | 8 | 338 |
| E6 | 8 | 131 |
| E6 | 9 | 75 |
| E6 | 10 | 75 |
| E2 | 8 | 248 |
| E2 | 11 | 248 |
| L2 | 10 | 373 |
| L2 | 11 | 373 |
| E5 | 9 | 54 |
| L2 | 8 | 381 |
| E1 | 10 | 97 |
| L1 | 9 | 143 |
| L1 | 11 | 143 |
| E2 | 9 | 127 |
| E2 | 11 | 127 |
| E7 | 9 | 64 |
| L2 | 8 | 85 |
| L2 | 9 | 85 |
| L2 | 10 | 236 |
| L2 | 11 | 236 |
| E5 | 9 | 78 |
| E5 | 10 | 78 |
| L2 | 8 | 138 |
| L2 | 9 | 138 |
| L2 | 8 | 79 |
| L2 | 9 | 79 |
| L2 | 9 | 284 |
| L2 | 10 | 284 |
| L2 | 8 | 416 |
| L2 | 10 | 416 |
| L2 | 11 | 416 |
| E2 | 8 | 216 |
| E2 | 9 | 216 |
| E2 | 11 | 216 |
| E2 | 8 | 196 |
| E2 | 11 | 196 |

TABLE VIIIC-continued

HPV11
HLA-A2 Supermotif Peptides

| 2 | 3 | 4 |
|---|---|---|
| L1 | 8 | 483 |
| L1 | 9 | 483 |
| E4 | 8 | 4 |
| E4 | 9 | 4 |
| E4 | 10 | 4 |
| L2 | 10 | 354 |
| L2 | 11 | 354 |
| E1 | 8 | 94 |
| E1 | 9 | 94 |
| E1 | 11 | 442 |
| E6 | 8 | 110 |
| E6 | 11 | 110 |
| L1 | 8 | 218 |
| L1 | 8 | 184 |
| L1 | 9 | 184 |
| L2 | 8 | 447 |
| L2 | 9 | 447 |
| L2 | 8 | 157 |
| L2 | 9 | 157 |
| L1 | 10 | 161 |
| L1 | 8 | 459 |
| L2 | 9 | 72 |
| L2 | 10 | 72 |
| L2 | 11 | 72 |
| L1 | 11 | 109 |
| L1 | 9 | 118 |
| E4 | 8 | 30 |
| E1 | 8 | 562 |
| E1 | 10 | 562 |
| L2 | 11 | 211 |
| E4 | 11 | 44 |
| E5 | 8 | 64 |
| E5 | 9 | 64 |
| E5 | 11 | 64 |
| L2 | 10 | 385 |
| E1 | 8 | 258 |
| E1 | 11 | 258 |
| E1 | 8 | 513 |
| E1 | 9 | 513 |
| E1 | 10 | 513 |
| E7 | 8 | 47 |
| E7 | 9 | 47 |
| E7 | 10 | 47 |
| E4 | 10 | 68 |
| L2 | 9 | 336 |
| E1 | 10 | 545 |
| E1 | 11 | 545 |
| L2 | 11 | 167 |
| L2 | 11 | 242 |
| L2 | 8 | 419 |
| E2 | 10 | 353 |
| L2 | 8 | 182 |
| L2 | 11 | 182 |
| L2 | 8 | 123 |
| L2 | 9 | 123 |
| E4 | 8 | 76 |
| E4 | 11 | 76 |
| L2 | 10 | 206 |
| L1 | 9 | 90 |
| L1 | 11 | 90 |
| E2 | 9 | 211 |
| E2 | 10 | 211 |
| E2 | 11 | 211 |
| E6 | 11 | 87 |
| E2 | 8 | 222 |
| L2 | 9 | 95 |
| L2 | 10 | 95 |
| L2 | 8 | 170 |
| L2 | 9 | 170 |
| L2 | 10 | 170 |
| L2 | 11 | 422 |
| E7 | 10 | 20 |
| L2 | 8 | 90 |
| L1 | 8 | 267 |

TABLE VIIIC-continued

HPV11
HLA-A2 Supermotif Peptides

| 2 | 3 | 4 |
|---|---|---|
| L2 | 11 | 358 |
| E5 | 8 | 5 |
| E5 | 9 | 5 |
| E5 | 10 | 5 |
| E5 | 11 | 5 |
| L1 | 8 | 16 |
| L1 | 10 | 16 |
| L2 | 8 | 413 |
| L2 | 11 | 413 |
| L2 | 9 | 324 |
| L2 | 11 | 324 |
| E5 | 8 | 19 |
| E5 | 10 | 19 |
| E5 | 11 | 19 |
| L2 | 8 | 251 |
| L2 | 10 | 251 |
| L2 | 8 | 327 |
| L2 | 11 | 327 |
| E1 | 10 | 636 |
| E1 | 11 | 636 |
| L1 | 9 | 420 |
| E1 | 9 | 399 |
| E1 | 10 | 399 |
| E1 | 11 | 399 |
| E1 | 9 | 64 |
| E1 | 11 | 64 |
| E5 | 8 | 7 |
| E5 | 9 | 7 |
| E5 | 10 | 7 |
| E5 | 11 | 7 |
| L2 | 8 | 42 |
| L2 | 10 | 42 |
| E6 | 10 | 28 |
| E6 | 11 | 28 |
| E1 | 10 | 31 |
| E6 | 8 | 15 |
| E6 | 10 | 15 |
| L1 | 8 | 152 |
| L1 | 11 | 152 |
| L1 | 9 | 373 |
| L1 | 11 | 373 |
| E7 | 10 | 28 |
| L1 | 9 | 302 |
| E2 | 11 | 14 |
| E7 | 9 | 78 |
| E7 | 10 | 78 |
| E2 | 9 | 288 |
| L2 | 8 | 15 |
| L2 | 9 | 15 |
| L2 | 11 | 15 |
| E4 | 8 | 14 |
| E4 | 10 | 14 |
| E4 | 11 | 14 |
| L1 | 11 | 233 |
| L1 | 11 | 251 |
| E2 | 9 | 48 |
| E2 | 11 | 48 |
| E2 | 8 | 76 |
| E2 | 10 | 76 |
| E2 | 9 | 343 |
| L2 | 9 | 229 |
| L2 | 11 | 229 |
| L2 | 8 | 18 |
| L1 | 9 | 211 |
| L1 | 11 | 211 |
| L1 | 10 | 150 |
| E2 | 9 | 218 |
| E2 | 11 | 218 |
| E1 | 8 | 344 |
| E1 | 9 | 344 |
| L2 | 8 | 230 |
| L2 | 10 | 230 |
| L2 | 8 | 232 |
| L2 | 10 | 232 |

TABLE VIIIC-continued

HPV11
HLA-A2 Supermotif Peptides

| 2 | 3 | 4 |
|---|---|---|
| E2 | 8 | 57 |
| E2 | 11 | 57 |
| E1 | 8 | 391 |
| E1 | 10 | 391 |
| L2 | 8 | 214 |
| L2 | 10 | 214 |
| L1 | 9 | 260 |
| L2 | 8 | 226 |
| L2 | 9 | 226 |
| E1 | 11 | 553 |
| E1 | 8 | 318 |
| E1 | 10 | 318 |
| E2 | 10 | 240 |
| E2 | 11 | 240 |
| L2 | 8 | 4 |
| L2 | 10 | 4 |
| L2 | 11 | 4 |
| L2 | 10 | 10 |
| E5 | 9 | 36 |
| L2 | 8 | 297 |
| L2 | 10 | 297 |
| L2 | 8 | 315 |
| L2 | 11 | 315 |
| L2 | 9 | 445 |
| L2 | 10 | 445 |
| L2 | 11 | 445 |
| E2 | 9 | 7 |
| E2 | 10 | 7 |
| E1 | 8 | 109 |
| E1 | 9 | 109 |
| E2 | 10 | 37 |
| E1 | 8 | 125 |
| E1 | 9 | 125 |
| L1 | 11 | 242 |
| E4 | 11 | 59 |
| L2 | 8 | 280 |
| E2 | 9 | 302 |
| E1 | 8 | 616 |
| E7 | 8 | 4 |
| E7 | 9 | 4 |
| E7 | 10 | 4 |
| L2 | 9 | 244 |
| E7 | 11 | 66 |
| L1 | 9 | 94 |
| L1 | 11 | 94 |
| E1 | 9 | 69 |
| E1 | 10 | 69 |
| E1 | 11 | 69 |
| E7 | 8 | 77 |
| E7 | 10 | 77 |
| E7 | 11 | 77 |
| E2 | 8 | 342 |
| E2 | 10 | 342 |
| E1 | 9 | 343 |
| E1 | 10 | 343 |
| L1 | 8 | 477 |
| L1 | 9 | 477 |
| E1 | 9 | 324 |
| E1 | 10 | 324 |
| E1 | 11 | 324 |
| E1 | 9 | 293 |
| L1 | 8 | 29 |
| L1 | 8 | 473 |
| E1 | 8 | 231 |
| E1 | 9 | 231 |
| E1 | 10 | 231 |
| L2 | 8 | 220 |
| L2 | 9 | 220 |
| L1 | 11 | 141 |
| E2 | 9 | 281 |
| E2 | 9 | 225 |
| E2 | 11 | 225 |
| L1 | 8 | 380 |
| L1 | 10 | 380 |
| L1 | 11 | 380 |
| L2 | 8 | 110 |
| L2 | 11 | 110 |
| E2 | 8 | 234 |
| L2 | 10 | 180 |
| L1 | 10 | 475 |
| L1 | 11 | 475 |
| L2 | 8 | 12 |
| L2 | 11 | 12 |
| E6 | 8 | 9 |
| E6 | 11 | 9 |
| E1 | 9 | 247 |
| E1 | 10 | 247 |
| E2 | 9 | 207 |
| E2 | 11 | 207 |
| E2 | 8 | 23 |
| E2 | 9 | 23 |
| E6 | 8 | 12 |
| E6 | 11 | 12 |
| E1 | 8 | 547 |
| E1 | 9 | 547 |
| E1 | 10 | 547 |
| E1 | 11 | 547 |
| L2 | 9 | 266 |
| L2 | 11 | 266 |
| L1 | 8 | 50 |
| L1 | 9 | 50 |
| L1 | 10 | 50 |
| E1 | 11 | 422 |
| L2 | 8 | 387 |
| L1 | 8 | 376 |
| L1 | 9 | 376 |
| L1 | 10 | 376 |
| E5 | 8 | 30 |
| L2 | 10 | 102 |
| L2 | 11 | 102 |
| L1 | 11 | 286 |
| E1 | 9 | 350 |
| E1 | 10 | 350 |
| E2 | 9 | 81 |
| L1 | 10 | 86 |
| L1 | 11 | 86 |
| L2 | 9 | 48 |
| L2 | 11 | 48 |
| E6 | 10 | 23 |
| L2 | 8 | 105 |
| L2 | 9 | 105 |
| L2 | 11 | 105 |
| E1 | 9 | 490 |
| E1 | 10 | 490 |
| E1 | 11 | 490 |
| L2 | 9 | 259 |
| E4 | 8 | 89 |
| L1 | 9 | 295 |
| E1 | 9 | 260 |
| E1 | 10 | 260 |
| L2 | 9 | 406 |
| L2 | 10 | 406 |
| L2 | 10 | 303 |
| E1 | 11 | 635 |
| L1 | 10 | 419 |
| E1 | 8 | 354 |
| E1 | 9 | 354 |
| L2 | 9 | 186 |
| L2 | 11 | 186 |
| L2 | 8 | 376 |
| L2 | 9 | 376 |
| L2 | 11 | 376 |
| L1 | 9 | 489 |
| L1 | 11 | 489 |
| E2 | 8 | 260 |
| E4 | 8 | 95 |
| E4 | 9 | 95 |
| E4 | 10 | 95 |

TABLE VIIIC-continued

HPV11
HLA-A2 Supermotif Peptides

| 2 | 3 | 4 |
|---|---|---|
| L1 | 8 | 336 |
| L1 | 10 | 336 |
| E2 | 8 | 245 |
| E2 | 9 | 245 |
| E2 | 11 | 245 |
| L2 | 8 | 240 |
| E1 | 8 | 185 |
| E1 | 11 | 185 |
| E6 | 10 | 7 |
| L2 | 9 | 135 |
| L2 | 11 | 135 |
| E4 | 8 | 85 |
| E4 | 9 | 85 |
| E4 | 10 | 85 |
| E2 | 8 | 190 |
| E2 | 10 | 190 |
| E1 | 11 | 331 |
| E2 | 8 | 201 |
| E2 | 9 | 201 |
| L1 | 11 | 7 |
| E2 | 10 | 316 |
| L1 | 8 | 282 |
| L1 | 10 | 282 |
| E2 | 10 | 151 |
| E2 | 9 | 257 |
| E2 | 10 | 257 |
| E2 | 11 | 257 |
| L2 | 9 | 152 |
| E1 | 8 | 436 |
| E1 | 9 | 436 |
| L1 | 8 | 190 |
| L1 | 9 | 190 |
| L1 | 11 | 190 |
| L2 | 9 | 163 |
| L2 | 11 | 163 |
| E2 | 8 | 348 |
| L1 | 10 | 393 |
| E2 | 10 | 40 |
| E5 | 8 | 45 |
| E5 | 9 | 45 |
| E5 | 11 | 45 |
| L1 | 10 | 176 |
| L1 | 9 | 344 |
| E2 | 9 | 198 |
| E2 | 11 | 198 |
| L2 | 8 | 144 |
| L2 | 10 | 144 |
| L2 | 8 | 362 |
| L2 | 10 | 362 |
| E6 | 8 | 40 |
| E5 | 8 | 21 |
| E5 | 10 | 21 |
| E5 | 11 | 21 |
| L1 | 8 | 490 |
| L1 | 10 | 490 |
| E2 | 9 | 220 |
| E2 | 10 | 220 |
| L2 | 11 | 404 |
| E2 | 9 | 354 |
| E2 | 11 | 354 |
| L2 | 10 | 183 |
| L2 | 8 | 129 |
| L2 | 9 | 129 |
| L2 | 11 | 129 |
| E4 | 10 | 91 |
| E4 | 11 | 91 |
| L1 | 10 | 340 |
| L1 | 11 | 340 |
| E2 | 10 | 249 |
| E5 | 9 | 71 |
| L1 | 9 | 409 |
| E1 | 8 | 294 |
| E1 | 8 | 556 |
| E1 | 9 | 556 |
| E1 | 10 | 556 |
| E1 | 11 | 556 |
| E5 | 8 | 15 |
| E5 | 9 | 15 |
| E5 | 11 | 15 |
| E7 | 9 | 7 |
| E5 | 8 | 50 |
| E5 | 10 | 50 |
| E5 | 11 | 50 |
| E1 | 10 | 297 |
| E1 | 11 | 297 |
| E7 | 8 | 86 |
| E7 | 10 | 86 |
| E2 | 9 | 93 |
| E2 | 11 | 93 |
| L1 | 8 | 378 |
| L1 | 10 | 378 |
| L2 | 9 | 374 |
| L2 | 10 | 374 |
| L2 | 11 | 374 |
| L2 | 9 | 326 |
| L1 | 8 | 170 |
| L2 | 8 | 124 |
| E7 | 8 | 49 |
| E1 | 11 | 30 |
| L1 | 9 | 151 |
| L2 | 9 | 14 |
| L2 | 10 | 14 |
| E1 | 9 | 57 |
| E1 | 10 | 57 |
| E1 | 8 | 526 |
| E1 | 10 | 526 |
| E1 | 10 | 117 |
| L1 | 9 | 92 |
| L1 | 11 | 92 |
| L2 | 8 | 364 |
| L2 | 11 | 364 |
| E2 | 9 | 85 |
| E2 | 10 | 85 |
| E6 | 9 | 39 |
| E2 | 8 | 219 |
| E2 | 10 | 219 |
| E2 | 11 | 219 |
| E1 | 8 | 232 |
| E1 | 9 | 232 |
| E6 | 8 | 142 |
| E2 | 8 | 228 |
| L2 | 8 | 37 |
| E5 | 8 | 14 |
| E5 | 9 | 14 |
| E5 | 10 | 14 |
| L2 | 8 | 136 |
| L2 | 10 | 136 |
| L2 | 11 | 136 |
| E4 | 8 | 70 |
| E5 | 8 | 62 |
| E5 | 9 | 62 |
| E5 | 10 | 62 |
| E5 | 11 | 62 |
| E1 | 11 | 116 |
| L1 | 8 | 91 |
| L1 | 10 | 91 |
| L1 | 8 | 333 |
| L1 | 9 | 333 |
| L1 | 11 | 333 |
| E4 | 8 | 86 |
| E4 | 9 | 86 |
| E4 | 11 | 86 |
| E4 | 8 | 93 |
| E4 | 9 | 93 |
| E4 | 10 | 93 |
| E4 | 11 | 93 |
| L2 | 9 | 150 |
| L2 | 11 | 150 |

TABLE VIIIC-continued

HPV11
HLA-A2 Supermotif Peptides

| 2 | 3 | 4 |
|---|---|---|
| E5 | 8 | 13 |
| E5 | 9 | 13 |
| E5 | 10 | 13 |
| E5 | 11 | 13 |
| L2 | 10 | 149 |
| E5 | 9 | 12 |
| E5 | 10 | 12 |
| E5 | 11 | 12 |
| E5 | 8 | 55 |
| E4 | 9 | 100 |
| E2 | 8 | 212 |
| E2 | 9 | 212 |
| E2 | 10 | 212 |
| E1 | 8 | 290 |
| E1 | 9 | 290 |
| E1 | 10 | 290 |
| L1 | 9 | 224 |
| L1 | 11 | 224 |
| E6 | 10 | 88 |
| E6 | 11 | 88 |
| L1 | 10 | 263 |
| L1 | 11 | 263 |
| E2 | 9 | 191 |
| E1 | 8 | 345 |
| E1 | 10 | 332 |
| E1 | 11 | 332 |
| E1 | 10 | 78 |
| E4 | 9 | 82 |
| E4 | 10 | 82 |
| E4 | 11 | 82 |
| E2 | 8 | 202 |
| E2 | 11 | 202 |
| E2 | 11 | 223 |
| E2 | 10 | 63 |
| E2 | 11 | 63 |
| E4 | 8 | 101 |
| L1 | 9 | 329 |
| L1 | 11 | 329 |
| L1 | 10 | 8 |
| L2 | 10 | 338 |
| E1 | 10 | 239 |
| E1 | 11 | 239 |
| E1 | 8 | 519 |
| E1 | 9 | 98 |
| E2 | 10 | 252 |
| E2 | 11 | 252 |
| L2 | 8 | 96 |
| L2 | 9 | 96 |
| L2 | 11 | 96 |
| E1 | 8 | 291 |
| E1 | 9 | 291 |
| E1 | 11 | 291 |
| L1 | 9 | 283 |
| L1 | 10 | 21 |
| E5 | 8 | 25 |
| E5 | 9 | 25 |
| E5 | 8 | 21 |
| E5 | 9 | 21 |
| E5 | 11 | 21 |
| E2 | 8 | 192 |
| E2 | 11 | 192 |
| E1 | 9 | 333 |
| E1 | 10 | 333 |
| L2 | 8 | 30 |
| L2 | 9 | 30 |
| L2 | 10 | 30 |
| L2 | 11 | 30 |
| L1 | 8 | 191 |
| L1 | 10 | 191 |
| L2 | 8 | 164 |
| L2 | 10 | 164 |
| E7 | 10 | 12 |
| L1 | 9 | 394 |
| E5 | 11 | 27 |

TABLE VIIIC-continued

HPV11
HLA-A2 Supermotif Peptides

| 2 | 3 | 4 |
|---|---|---|
| E5 | 10 | 32 |
| E5 | 11 | 32 |
| E2 | 9 | 41 |
| E2 | 11 | 41 |
| E4 | 8 | 17 |
| E4 | 9 | 17 |
| E1 | 10 | 275 |
| L1 | 9 | 73 |
| L1 | 10 | 73 |
| E5 | 8 | 48 |
| E5 | 9 | 48 |
| E5 | 10 | 48 |
| E5 | 8 | 46 |
| E5 | 10 | 46 |
| E5 | 11 | 46 |
| E4 | 8 | 10 |
| E4 | 9 | 10 |
| E4 | 10 | 10 |
| L1 | 8 | 383 |
| E2 | 8 | 128 |
| E2 | 10 | 128 |
| E1 | 9 | 79 |
| E1 | 9 | 444 |
| L2 | 10 | 359 |
| L2 | 11 | 359 |
| E5 | 8 | 6 |
| E5 | 9 | 6 |
| E5 | 10 | 6 |
| E5 | 11 | 6 |
| E2 | 10 | 287 |
| L1 | 9 | 177 |
| L1 | 11 | 177 |
| L2 | 8 | 394 |
| L2 | 11 | 394 |
| E4 | 8 | 83 |
| E4 | 9 | 83 |
| E4 | 10 | 83 |
| E4 | 11 | 83 |
| L2 | 9 | 231 |
| L2 | 11 | 231 |
| E1 | 9 | 362 |
| L2 | 9 | 233 |
| E7 | 8 | 6 |
| E7 | 10 | 6 |
| L2 | 9 | 145 |
| L2 | 10 | 414 |
| L2 | 8 | 325 |
| L2 | 10 | 325 |
| L2 | 9 | 363 |
| E2 | 10 | 148 |
| L1 | 10 | 328 |
| E1 | 11 | 238 |
| L1 | 8 | 20 |
| L1 | 11 | 20 |
| E5 | 8 | 24 |
| E5 | 9 | 24 |
| E5 | 10 | 24 |
| L1 | 8 | 330 |
| L1 | 10 | 330 |
| L1 | 11 | 330 |
| E7 | 9 | 68 |
| E5 | 9 | 20 |
| E5 | 10 | 20 |
| L1 | 10 | 72 |
| L1 | 11 | 72 |
| E4 | 9 | 2 |
| E4 | 10 | 2 |
| E4 | 11 | 2 |
| E2 | 10 | 58 |
| L2 | 10 | 120 |
| L2 | 11 | 120 |
| E5 | 8 | 3 |
| E5 | 9 | 3 |
| E5 | 10 | 3 |

TABLE VIIIC-continued

HPV11
HLA-A2 Supermotif Peptides

| 2 | 3 | 4 |
|---|---|---|
| E5 | 11 | 3 |
| L2 | 10 | 198 |
| E6 | 10 | 53 |
| E6 | 11 | 53 |
| E2 | 8 | 132 |
| E5 | 8 | 41 |
| E5 | 9 | 41 |
| E5 | 10 | 41 |
| E5 | 11 | 41 |
| L1 | 8 | 97 |
| E2 | 11 | 320 |
| E1 | 9 | 426 |
| E1 | 8 | 340 |
| E5 | 8 | 14 |
| E5 | 9 | 14 |
| E5 | 11 | 14 |
| E5 | 8 | 18 |
| E5 | 9 | 18 |
| E5 | 10 | 18 |
| E5 | 11 | 18 |
| E1 | 11 | 464 |
| E5 | 8 | 58 |
| E1 | 8 | 510 |
| E1 | 10 | 510 |
| E1 | 11 | 510 |
| E1 | 8 | 267 |
| E1 | 9 | 267 |
| E1 | 10 | 267 |
| E1 | 11 | 267 |
| E2 | 10 | 92 |
| E6 | 8 | 141 |
| E6 | 9 | 141 |
| E4 | 10 | 81 |
| E4 | 11 | 81 |
| E1 | 8 | 530 |
| E1 | 11 | 530 |
| E2 | 8 | 145 |
| E2 | 10 | 145 |
| E1 | 8 | 237 |
| E6 | 8 | 82 |
| L2 | 8 | 348 |
| E1 | 8 | 262 |
| E1 | 10 | 262 |
| E6 | 9 | 85 |
| E1 | 11 | 380 |
| E6 | 8 | 44 |
| E6 | 10 | 44 |
| E6 | 11 | 44 |
| E6 | 8 | 46 |
| E6 | 9 | 46 |
| E5 | 9 | 81 |
| L1 | 9 | 386 |
| L1 | 10 | 386 |
| L2 | 11 | 70 |
| E4 | 10 | 22 |
| E4 | 11 | 22 |
| E6 | 10 | 105 |
| E1 | 10 | 86 |
| L2 | 9 | 431 |
| E1 | 8 | 579 |
| E1 | 10 | 579 |
| E5 | 8 | 54 |
| E5 | 9 | 54 |
| E5 | 10 | 54 |
| E2 | 9 | 138 |
| E2 | 11 | 138 |
| L1 | 9 | 246 |
| L2 | 8 | 367 |
| L2 | 9 | 367 |
| E1 | 9 | 532 |
| E1 | 10 | 532 |
| L1 | 10 | 359 |
| E1 | 11 | 536 |
| E5 | 11 | 61 |

TABLE VIIIC-continued

HPV11
HLA-A2 Supermotif Peptides

| 2 | 3 | 4 |
|---|---|---|
| L2 | 9 | 17 |
| L1 | 8 | 65 |
| L1 | 9 | 65 |
| L1 | 10 | 65 |
| E2 | 8 | 159 |
| E2 | 11 | 159 |
| L1 | 10 | 351 |
| E2 | 8 | 214 |
| E2 | 10 | 214 |
| E2 | 11 | 214 |
| L2 | 8 | 305 |
| L2 | 10 | 305 |
| E5 | 8 | 43 |
| E5 | 9 | 43 |
| E5 | 10 | 43 |
| E5 | 11 | 43 |
| L1 | 9 | 288 |
| L1 | 10 | 288 |
| E1 | 8 | 402 |
| L1 | 11 | 26 |
| E4 | 8 | 16 |
| E4 | 9 | 16 |
| E4 | 10 | 16 |
| E4 | 9 | 9 |
| E4 | 10 | 9 |
| E4 | 11 | 9 |
| E2 | 8 | 168 |
| E1 | 10 | 502 |
| L1 | 8 | 10 |
| L1 | 11 | 10 |
| L1 | 8 | 416 |
| E1 | 8 | 91 |
| E1 | 9 | 91 |
| E1 | 11 | 91 |
| E2 | 9 | 131 |

TABLE IX

HLA-A3 Supermotif Peptides

| 1 | 2 | 3 | 4 |
|---|---|---|---|
| HPV16 | E1 | 8 | 316 |
| HPV16 | E1 | 8 | 205 |
| HPV16 | E1 | 9 | 112 |
| HPV16 | E1 | 9 | 69 |
| HPV16 | E1 | 11 | 459 |
| HPV16 | E1 | 8 | 406 |
| HPV16 | E1 | 9 | 406 |
| HPV16 | E1 | 8 | 82 |
| HPV16 | E1 | 9 | 405 |
| HPV16 | E1 | 10 | 405 |
| HPV16 | E1 | 10 | 114 |
| HPV16 | E1 | 11 | 114 |
| HPV16 | E1 | 8 | 304 |
| HPV16 | E1 | 10 | 304 |
| HPV16 | E1 | 9 | 101 |
| HPV16 | E1 | 11 | 101 |
| HPV16 | E1 | 8 | 81 |
| HPV16 | E1 | 9 | 81 |
| HPV16 | E1 | 11 | 368 |
| HPV16 | E1 | 10 | 573 |
| HPV16 | E1 | 11 | 384 |
| HPV16 | E1 | 8 | 335 |
| HPV16 | E1 | 11 | 548 |
| HPV16 | E1 | 8 | 603 |
| HPV16 | E1 | 10 | 221 |
| HPV16 | E1 | 9 | 288 |
| HPV16 | E1 | 11 | 140 |
| HPV16 | E1 | 9 | 392 |
| HPV16 | E1 | 8 | 463 |

TABLE IX-continued

HLA-A3 Supermotif Peptides

| 1 | 2 | 3 | 4 |
|---|---|---|---|
| HPV16 | E1 | 9 | 453 |
| HPV16 | E1 | 10 | 453 |
| HPV16 | E1 | 9 | 219 |
| HPV16 | E1 | 10 | 71 |
| HPV16 | E1 | 11 | 242 |
| HPV16 | E1 | 9 | 272 |
| HPV16 | E1 | 11 | 272 |
| HPV16 | E1 | 10 | 174 |
| HPV16 | E1 | 10 | 496 |
| HPV16 | E1 | 9 | 216 |
| HPV16 | E1 | 10 | 68 |
| HPV16 | E1 | 11 | 473 |
| HPV16 | E1 | 11 | 194 |
| HPV16 | E1 | 10 | 369 |
| HPV16 | E1 | 10 | 401 |
| HPV16 | E1 | 9 | 204 |
| HPV16 | E1 | 10 | 111 |
| HPV16 | E1 | 11 | 400 |
| HPV16 | E1 | 10 | 610 |
| HPV16 | E1 | 10 | 483 |
| HPV16 | E1 | 10 | 394 |
| HPV16 | E1 | 10 | 276 |
| HPV16 | E1 | 9 | 277 |
| HPV16 | E1 | 11 | 277 |
| HPV16 | E1 | 10 | 474 |
| HPV16 | E1 | 9 | 620 |
| HPV16 | E1 | 9 | 191 |
| HPV16 | E1 | 10 | 243 |
| HPV16 | E1 | 9 | 222 |
| HPV16 | E1 | 8 | 278 |
| HPV16 | E1 | 10 | 278 |
| HPV16 | E1 | 9 | 544 |
| HPV16 | E1 | 8 | 306 |
| HPV16 | E1 | 9 | 305 |
| HPV16 | E1 | 8 | 454 |
| HPV16 | E1 | 9 | 454 |
| HPV16 | E1 | 8 | 420 |
| HPV16 | E1 | 10 | 420 |
| HPV16 | E1 | 8 | 422 |
| HPV16 | E1 | 11 | 422 |
| HPV16 | E1 | 8 | 273 |
| HPV16 | E1 | 10 | 273 |
| HPV16 | E1 | 9 | 202 |
| HPV16 | E1 | 11 | 202 |
| HPV16 | E1 | 9 | 567 |
| HPV16 | E1 | 8 | 543 |
| HPV16 | E1 | 10 | 543 |
| HPV16 | E1 | 9 | 386 |
| HPV16 | E1 | 8 | 396 |
| RPV16 | E1 | 9 | 196 |
| HPV16 | E1 | 10 | 190 |
| HPV16 | E1 | 10 | 302 |
| HPV16 | E1 | 8 | 245 |
| HPV16 | E1 | 8 | 600 |
| HPV16 | E1 | 11 | 600 |
| HPV16 | E1 | 8 | 143 |
| RPV16 | E1 | 9 | 419 |
| HPV16 | E1 | 11 | 419 |
| HPV16 | E1 | 8 | 118 |
| HPV16 | E1 | 9 | 109 |
| HPV16 | E1 | 10 | 619 |
| HPV16 | E1 | 11 | 313 |
| HPV16 | E1 | 9 | 432 |
| HPV16 | E1 | 11 | 390 |
| HPV16 | E1 | 9 | 484 |
| HPV16 | E1 | 8 | 621 |
| HPV16 | E1 | 9 | 421 |
| HPV16 | E1 | 10 | 314 |
| HPV16 | E1 | 9 | 497 |
| HPV16 | E1 | 9 | 315 |
| HPV16 | E1 | 9 | 72 |
| HPV16 | E1 | 8 | 289 |
| HPV16 | E1 | 8 | 407 |
| HPV16 | E1 | 11 | 407 |
| HPV16 | E1 | 11 | 200 |
| HPV16 | E1 | 11 | 565 |
| HPV16 | E1 | 8 | 498 |
| HPV16 | E1 | 8 | 197 |
| HPV16 | E1 | 8 | 275 |
| HPV16 | E1 | 11 | 275 |
| HPV16 | E1 | 8 | 217 |
| HPV16 | E1 | 11 | 217 |
| HPV16 | E1 | 8 | 545 |
| HPV16 | E1 | 9 | 274 |
| HPV16 | E1 | 8 | 425 |
| HPV16 | E1 | 9 | 509 |
| HPV16 | E1 | 8 | 20 |
| HPV16 | E1 | 9 | 20 |
| HPV16 | E2 | 8 | 40 |
| HPV16 | E2 | 8 | 300 |
| HPV16 | E2 | 9 | 174 |
| HPV16 | E2 | 9 | 294 |
| HPV16 | E2 | 11 | 294 |
| HPV16 | E2 | 10 | 25 |
| HPV16 | E2 | 10 | 246 |
| HPV16 | E2 | 8 | 233 |
| HPV16 | E2 | 10 | 233 |
| HPV16 | E2 | 9 | 204 |
| HPV16 | E2 | 9 | 346 |
| HPV16 | E2 | 10 | 168 |
| HPV16 | E2 | 10 | 163 |
| HPV16 | E2 | 10 | 156 |
| HPV16 | E2 | 11 | 230 |
| HPV16 | E2 | 9 | 29 |
| HPV16 | E2 | 10 | 290 |
| HPV16 | E2 | 11 | 35 |
| HPV16 | E2 | 8 | 252 |
| HPV16 | E2 | 10 | 267 |
| HPV16 | E2 | 8 | 45 |
| HPV16 | E2 | 11 | 215 |
| HPV16 | E2 | 8 | 347 |
| HPV16 | E2 | 9 | 268 |
| HPV16 | E2 | 11 | 268 |
| HPV16 | E2 | 9 | 103 |
| HPV16 | E2 | 10 | 103 |
| HPV16 | E2 | 9 | 335 |
| HPV16 | E2 | 11 | 282 |
| HPV16 | E2 | 8 | 84 |
| HPV16 | E2 | 9 | 296 |
| HPV16 | E2 | 11 | 296 |
| HPV16 | E2 | 9 | 284 |
| HPV16 | E2 | 11 | 266 |
| HPV16 | E2 | 9 | 60 |
| HPV16 | E2 | 8 | 235 |
| HPV16 | E2 | 10 | 57 |
| HPV16 | E2 | 9 | 37 |
| HPV16 | E2 | 11 | 37 |
| HPV16 | E2 | 8 | 7 |
| HPV16 | E2 | 8 | 165 |
| HPV16 | E2 | 11 | 317 |
| HPV16 | E2 | 8 | 269 |
| HPV16 | E2 | 10 | 269 |
| HPV16 | E2 | 8 | 104 |
| HPV16 | E2 | 9 | 104 |
| HPV16 | E2 | 11 | 81 |
| HPV16 | E2 | 8 | 61 |
| HPV16 | E2 | 8 | 297 |
| HPV16 | E2 | 10 | 297 |
| HPV16 | E2 | 11 | 297 |
| HPV16 | E2 | 10 | 334 |
| HPV16 | E2 | 8 | 285 |
| HPV16 | E2 | 8 | 205 |
| HPV16 | E2 | 11 | 333 |
| HPV16 | E2 | 9 | 58 |
| HPV16 | E2 | 11 | 58 |
| HPV16 | E2 | 9 | 321 |
| HPV16 | E2 | 10 | 102 |
| HPV16 | E2 | 11 | 102 |
| HPV16 | E5 | 11 | 20 |
| HPV16 | E5 | 8 | 72 |

TABLE IX-continued

HLA-A3 Supermotif Peptides

| 1 | 2 | 3 | 4 |
|---|---|---|---|
| HPV16 | E5 | 8 | 51 |
| HPV16 | E5 | 9 | 22 |
| HPV16 | E5 | 11 | 48 |
| HPV16 | E5 | 10 | 70 |
| HPV16 | E5 | 10 | 21 |
| HPV16 | E5 | 9 | 50 |
| HPV16 | E6 | 9 | 7 |
| HPV16 | E6 | 11 | 7 |
| HPV16 | E6 | 8 | 68 |
| HPV16 | E6 | 9 | 143 |
| HPV16 | E6 | 11 | 143 |
| HPV16 | E6 | 10 | 37 |
| EPV16 | E6 | 11 | 37 |
| HPV16 | E6 | 10 | 32 |
| HPV16 | E6 | 11 | 105 |
| HPV16 | E6 | 8 | 48 |
| HPV16 | E6 | 11 | 52 |
| HPV16 | E6 | 10 | 92 |
| HPV16 | E6 | 9 | 33 |
| HPV16 | E6 | 8 | 34 |
| HPV16 | E6 | 9 | 107 |
| HPV16 | E6 | 10 | 106 |
| HPV16 | E6 | 8 | 144 |
| HPV16 | E6 | 10 | 144 |
| HPV16 | E6 | 11 | 144 |
| HPV16 | E6 | 9 | 134 |
| HPV16 | E6 | 8 | 102 |
| HPV16 | E6 | 9 | 116 |
| HPV16 | E6 | 11 | 5 |
| HPV16 | E6 | 10 | 6 |
| HPV16 | E6 | 8 | 94 |
| HPV16 | E6 | 9 | 93 |
| HPV16 | E6 | 10 | 139 |
| HPV16 | E6 | 9 | 67 |
| HPV16 | E6 | 8 | 77 |
| HPV16 | E7 | 10 | 68 |
| HPV16 | E7 | 10 | 88 |
| HPV16 | E7 | 9 | 89 |
| HPV16 | E7 | 8 | 53 |
| HPV16 | E7 | 9 | 41 |
| HPV16 | E7 | 8 | 70 |
| HPV16 | L1 | 11 | 372 |
| HPV16 | L1 | 9 | 162 |
| HPV16 | L1 | 10 | 373 |
| HPV16 | L1 | 11 | 233 |
| HPV16 | L1 | 10 | 70 |
| HPV16 | L1 | 11 | 70 |
| HPV16 | L1 | 8 | 128 |
| HPV16 | L1 | 8 | 249 |
| HPV16 | L1 | 9 | 484 |
| HPV16 | L1 | 10 | 484 |
| HPV16 | L1 | 10 | 397 |
| HPV16 | L1 | 8 | 270 |
| HPV16 | L1 | 9 | 270 |
| HPV16 | L1 | 11 | 113 |
| HPV16 | L1 | 10 | 378 |
| HPV16 | L1 | 8 | 494 |
| HPV16 | L1 | 10 | 494 |
| HPV16 | L1 | 8 | 236 |
| HPV16 | L1 | 8 | 282 |
| HPV16 | L1 | 11 | 446 |
| HPV16 | L1 | 9 | 356 |
| HPV16 | L1 | 10 | 142 |
| HPV16 | L1 | 8 | 93 |
| HPV16 | L1 | 8 | 438 |
| HPV16 | L1 | 9 | 143 |
| HPV16 | L1 | 9 | 374 |
| HPV16 | L1 | 10 | 501 |
| HPV16 | L1 | 11 | 501 |
| HPV16 | L1 | 8 | 90 |
| HPV16 | L1 | 11 | 90 |
| HPV16 | L1 | 11 | 46 |
| HPV16 | L1 | 11 | 69 |
| HPV16 | L1 | 9 | 495 |
| HPV16 | L1 | 11 | 495 |
| HPV16 | L1 | 11 | 87 |
| HPV16 | L1 | 11 | 325 |
| HPV16 | L1 | 10 | 58 |
| HPV16 | L1 | 9 | 383 |
| HPV16 | L1 | 9 | 296 |
| HPV16 | L1 | 9 | 460 |
| HPV16 | L1 | 10 | 460 |
| HPV16 | L1 | 8 | 190 |
| HPV16 | L1 | 9 | 77 |
| HPV16 | L1 | 10 | 247 |
| HPV16 | L1 | 11 | 515 |
| HPV16 | L1 | 9 | 497 |
| HPV16 | L1 | 11 | 331 |
| HPV16 | L1 | 8 | 181 |
| HPV16 | L1 | 11 | 354 |
| HPV16 | L1 | 10 | 280 |
| HPV16 | L1 | 10 | 179 |
| HPV16 | L1 | 9 | 100 |
| HPV16 | L1 | 11 | 482 |
| HPV16 | L1 | 10 | 253 |
| HPV16 | L1 | 8 | 271 |
| HPV16 | L1 | 8 | 518 |
| HPV16 | L1 | 9 | 518 |
| HPV16 | L1 | 10 | 518 |
| HPV16 | L1 | 11 | 518 |
| HPV16 | L1 | 8 | 49 |
| HPV16 | L1 | 8 | 375 |
| HPV16 | L1 | 8 | 519 |
| HPV16 | L1 | 9 | 519 |
| HPV16 | L1 | 10 | 519 |
| HPV16 | L1 | 11 | 519 |
| HPV16 | L1 | 8 | 521 |
| HPV16 | L1 | 9 | 521 |
| HPV16 | L1 | 10 | 521 |
| HPV16 | L1 | 8 | 523 |
| HPV16 | L1 | 9 | 327 |
| HPV16 | L1 | 10 | 114 |
| HPV16 | L1 | 11 | 252 |
| HPV16 | L1 | 9 | 448 |
| HPV16 | L1 | 9 | 517 |
| HPV16 | L1 | 10 | 517 |
| HPV16 | L1 | 11 | 517 |
| HPV16 | L1 | 8 | 520 |
| HPV16 | L1 | 9 | 520 |
| HPV16 | L1 | 10 | 520 |
| HPV16 | L1 | 11 | 520 |
| HPV16 | L1 | 8 | 522 |
| HPV16 | L1 | 9 | 522 |
| HPV16 | L1 | 10 | 516 |
| HPV16 | L1 | 11 | 516 |
| HPV16 | L1 | 9 | 379 |
| HPV16 | L1 | 11 | 36 |
| HPV16 | L1 | 10 | 91 |
| HPV16 | L1 | 9 | 48 |
| HPV16 | L1 | 10 | 326 |
| HPV16 | L1 | 10 | 447 |
| HPV16 | L1 | 8 | 357 |
| HPV16 | L1 | 10 | 47 |
| HPV16 | L1 | 10 | 126 |
| HPV16 | L1 | 10 | 161 |
| HPV16 | L1 | 9 | 38 |
| HPV16 | L1 | 10 | 275 |
| HPV16 | L1 | 9 | 470 |
| HPV16 | L1 | 11 | 470 |
| HPV16 | L2 | 10 | 288 |
| HPV16 | L2 | 11 | 288 |
| HPV16 | L2 | 10 | 293 |
| HPV16 | L2 | 8 | 13 |
| HPV16 | L2 | 11 | 13 |
| HPV16 | L2 | 9 | 82 |
| HPV16 | L2 | 9 | 15 |
| HPV16 | L2 | 9 | 31 |
| HPV16 | L2 | 9 | 283 |
| HPV16 | L2 | 11 | 59 |
| HPV16 | L2 | 10 | 300 |

TABLE IX-continued

HLA-A3 Supermotif Peptides

| 1 | 2 | 3 | 4 |
|---|---|---|---|
| HPV16 | L2 | 11 | 226 |
| HPV16 | L2 | 10 | 26 |
| HPV16 | L2 | 9 | 61 |
| HPV16 | L2 | 8 | 32 |
| HPV16 | L2 | 9 | 294 |
| HPV16 | L2 | 8 | 454 |
| HPV16 | L2 | 9 | 240 |
| HPV16 | L2 | 11 | 292 |
| HPV16 | L2 | 10 | 215 |
| HPV16 | L2 | 8 | 450 |
| HPV16 | L2 | 9 | 450 |
| HPV16 | L2 | 10 | 450 |
| HPV16 | L2 | 11 | 450 |
| HPV16 | L2 | 11 | 80 |
| HPV16 | L2 | 10 | 221 |
| HPV16 | L2 | 9 | 310 |
| HPV16 | L2 | 9 | 12 |
| HPV16 | L2 | 9 | 305 |
| HPV16 | L2 | 11 | 305 |
| HPV16 | L2 | 8 | 5 |
| HPV16 | L2 | 9 | 315 |
| HPV16 | L2 | 8 | 298 |
| HPV16 | L2 | 10 | 69 |
| HPV16 | L2 | 11 | 313 |
| HPV16 | L2 | 10 | 14 |
| HPV16 | L2 | 9 | 212 |
| HPV16 | L2 | 8 | 213 |
| HPV16 | L2 | 10 | 81 |
| HPV16 | L2 | 8 | 311 |
| HPV16 | L2 | 8 | 295 |
| HPV16 | L2 | 11 | 295 |
| HPV16 | L2 | 10 | 211 |
| HPV16 | L2 | 11 | 287 |
| HPV16 | L2 | 9 | 222 |
| HPV16 | L2 | 11 | 210 |
| HPV16 | L2 | 10 | 447 |
| HPV16 | L2 | 11 | 447 |
| HPV16 | L2 | 8 | 453 |
| HPV16 | L2 | 9 | 453 |
| HPV16 | L2 | 11 | 303 |
| HPV16 | L2 | 9 | 228 |
| HPV18 | E1 | 11 | 397 |
| HPV18 | E1 | 11 | 546 |
| HPV18 | E1 | 11 | 466 |
| HPV18 | E1 | 9 | 284 |
| HPV18 | E1 | 11 | 284 |
| HPV18 | E1 | 8 | 413 |
| NPV18 | E1 | 9 | 413 |
| HPV18 | E1 | 9 | 412 |
| HPV18 | E1 | 10 | 412 |
| HPV18 | E1 | 8 | 311 |
| HPV18 | E1 | 10 | 311 |
| HPV18 | E1 | 11 | 437 |
| HPV18 | E1 | 11 | 196 |
| HPV18 | E1 | 9 | 78 |
| HPV18 | E1 | 10 | 78 |
| HPV18 | E1 | 11 | 78 |
| HPV18 | E1 | 8 | 203 |
| HPV18 | E1 | 10 | 228 |
| HPV18 | E1 | 11 | 391 |
| HPV18 | E1 | 11 | 637 |
| HPV18 | E1 | 8 | 342 |
| HPV18 | E1 | 8 | 610 |
| HPV18 | E1 | 9 | 115 |
| HPV18 | E1 | 10 | 115 |
| HPV18 | E1 | 10 | 309 |
| HPV18 | E1 | 9 | 104 |
| HPV18 | E1 | 9 | 460 |
| HPV18 | E1 | 10 | 463 |
| HPV18 | E1 | 8 | 470 |
| HPV18 | E1 | 9 | 399 |
| HPV18 | E1 | 9 | 226 |
| HPV18 | E1 | 8 | 465 |
| HPV18 | E1 | 8 | 212 |
| HPV18 | E1 | 9 | 223 |
| HPV18 | E1 | 11 | 92 |
| HPV18 | E1 | 9 | 279 |
| HPV18 | E1 | 11 | 279 |
| HPV18 | E1 | 11 | 249 |
| HPV18 | E1 | 8 | 270 |
| HPV18 | E1 | 9 | 198 |
| HPV18 | E1 | 8 | 282 |
| HPV18 | E1 | 11 | 282 |
| HPV18 | E1 | 11 | 569 |
| HPV18 | E1 | 8 | 552 |
| HPV18 | E1 | 8 | 116 |
| HPV18 | E1 | 9 | 116 |
| HPV18 | E1 | 11 | 116 |
| HPV18 | E1 | 8 | 461 |
| HPV18 | E1 | 9 | 439 |
| HPV18 | E1 | 9 | 647 |
| HPV18 | E1 | 9 | 468 |
| HPV18 | E1 | 10 | 468 |
| HPV18 | E1 | 10 | 401 |
| HPV18 | E1 | 8 | 292 |
| HPV18 | E1 | 10 | 283 |
| HPV18 | E1 | 9 | 281 |
| HPV18 | E1 | 8 | 313 |
| HPV18 | E1 | 8 | 285 |
| HPV18 | E1 | 10 | 285 |
| HPV18 | E1 | 10 | 570 |
| HPV18 | E1 | 8 | 224 |
| HPV18 | E1 | 11 | 224 |
| HPV18 | E1 | 9 | 571 |
| HPV18 | E1 | 11 | 480 |
| HPV18 | E1 | 9 | 229 |
| HPV18 | E1 | 9 | 312 |
| HPV18 | E1 | 8 | 429 |
| HPV18 | E1 | 11 | 429 |
| HPV18 | E1 | 9 | 574 |
| HPV18 | E1 | 9 | 428 |
| HPV18 | E1 | 8 | 119 |
| HPV18 | E1 | 9 | 119 |
| HPV18 | E1 | 10 | 119 |
| HPV18 | E1 | 9 | 393 |
| HPV18 | E1 | 9 | 551 |
| HPV18 | E1 | 8 | 252 |
| HPV18 | E1 | 8 | 607 |
| HPV18 | E1 | 11 | 607 |
| HPV18 | E1 | 11 | 200 |
| HPV18 | E1 | 9 | 426 |
| HPV18 | E1 | 11 | 426 |
| HPV18 | E1 | 8 | 80 |
| HPV18 | E1 | 9 | 80 |
| HPV18 | E1 | 11 | 102 |
| HPV18 | E1 | 11 | 320 |
| HPV18 | E1 | 8 | 117 |
| HPV18 | E1 | 10 | 117 |
| HPV18 | E1 | 11 | 117 |
| HPV18 | E1 | 10 | 321 |
| HPV18 | E1 | 10 | 93 |
| HPV18 | E1 | 9 | 322 |
| HPV18 | E1 | 10 | 197 |
| HPV18 | E1 | 8 | 414 |
| HPV18 | E1 | 11 | 414 |
| HPV18 | E1 | 8 | 572 |
| HPV18 | E1 | 11 | 572 |
| HPV18 | E1 | 8 | 323 |
| HPV18 | E1 | 8 | 81 |
| HPV18 | E1 | 8 | 280 |
| HPV18 | E1 | 10 | 280 |
| HPV18 | E1 | 11 | 339 |
| HPV18 | E1 | 8 | 432 |
| HPV18 | E1 | 9 | 516 |
| HPV18 | E1 | 9 | 536 |
| HPV18 | E1 | 10 | 268 |
| HPV18 | E1 | 10 | 408 |
| HPV18 | E1 | 8 | 19 |
| HPV18 | E1 | 9 | 19 |
| HPV18 | E2 | 9 | 269 |

TABLE IX-continued

HLA-A3 Supermotif Peptides

| 1 | 2 | 3 | 4 |
|---|---|---|---|
| HPV18 | E2 | 10 | 269 |
| HPV18 | E2 | 11 | 269 |
| HPV18 | E2 | 9 | 82 |
| HPV18 | E2 | 11 | 82 |
| HPV18 | E2 | 8 | 270 |
| HPV18 | E2 | 9 | 270 |
| HPV18 | E2 | 10 | 270 |
| HPV18 | E2 | 11 | 270 |
| HPV18 | E2 | 8 | 301 |
| HPV18 | E2 | 11 | 156 |
| HPV18 | E2 | 11 | 31 |
| HPV18 | E2 | 10 | 210 |
| HPV18 | E2 | 10 | 268 |
| HPV18 | E2 | 11 | 268 |
| HPV18 | E2 | 8 | 85 |
| HPV18 | E2 | 10 | 291 |
| HPV18 | E2 | 8 | 338 |
| HPV18 | E2 | 10 | 19 |
| HPV18 | E2 | 8 | 289 |
| HPV18 | E2 | 8 | 68 |
| HPV18 | E2 | 11 | 18 |
| HPV18 | E2 | 9 | 152 |
| HPV18 | E2 | 11 | 238 |
| HPV18 | E2 | 11 | 8 |
| HPV18 | E2 | 11 | 333 |
| HPV18 | E2 | 10 | 81 |
| HPV18 | E2 | 9 | 144 |
| HPV18 | E2 | 8 | 44 |
| HPV18 | E2 | 9 | 67 |
| HPV18 | E2 | 9 | 297 |
| HPV18 | E2 | 11 | 297 |
| HPV18 | E2 | 9 | 107 |
| HPV18 | E2 | 10 | 107 |
| HPV18 | E2 | 8 | 170 |
| HPV18 | E2 | 9 | 285 |
| HPV18 | E2 | 9 | 64 |
| HPV18 | E2 | 9 | 288 |
| HPV18 | E2 | 8 | 272 |
| HPV18 | E2 | 9 | 272 |
| HPV18 | E2 | 9 | 33 |
| HPV18 | E2 | 11 | 80 |
| HPV18 | E2 | 10 | 2 |
| HPV18 | E2 | 11 | 119 |
| HPV18 | E2 | 10 | 61 |
| HPV18 | E2 | 8 | 122 |
| HPV18 | E2 | 10 | 305 |
| HPV18 | E2 | 8 | 11 |
| HPV18 | E2 | 8 | 298 |
| HPV18 | E2 | 10 | 298 |
| HPV18 | E2 | 11 | 298 |
| HPV18 | E2 | 10 | 229 |
| HPV18 | E2 | 9 | 230 |
| HPV18 | E2 | 8 | 153 |
| HPV18 | E2 | 8 | 286 |
| HPV18 | E2 | 11 | 286 |
| HPV18 | E2 | 10 | 120 |
| HPV18 | E2 | 9 | 211 |
| HPV18 | E2 | 8 | 231 |
| HPV18 | E2 | 10 | 334 |
| HPV18 | E2 | 8 | 212 |
| HPV18 | E2 | 10 | 157 |
| HPV18 | E2 | 9 | 335 |
| HPV18 | E2 | 11 | 335 |
| HPV18 | E2 | 9 | 62 |
| HPV18 | E2 | 11 | 62 |
| HPV18 | E2 | 8 | 322 |
| HPV18 | E2 | 10 | 173 |
| HPV18 | E2 | 10 | 143 |
| HPV18 | E2 | 11 | 228 |
| HPV18 | E6 | 9 | 68 |
| HPV18 | E6 | 10 | 27 |
| HPV18 | E6 | 10 | 58 |
| HPV15 | E6 | 10 | 83 |
| HPV18 | E6 | 8 | 29 |
| HPV18 | E6 | 11 | 40 |
| HPV18 | E6 | 8 | 43 |
| HPV18 | E6 | 11 | 47 |
| HPV18 | E6 | 8 | 97 |
| HPV18 | E6 | 11 | 97 |
| HPV18 | E6 | 8 | 139 |
| HPV18 | E6 | 11 | 139 |
| HPV18 | E6 | 8 | 117 |
| HPV18 | E6 | 9 | 117 |
| HPV18 | E6 | 10 | 117 |
| HPV18 | E6 | 9 | 102 |
| HPV18 | E6 | 10 | 101 |
| HPV18 | E6 | 10 | 41 |
| HPV18 | E6 | 9 | 1 |
| HPV18 | E6 | 10 | 1 |
| HPV18 | E6 | 8 | 100 |
| HPV18 | E6 | 11 | 100 |
| HPV18 | E6 | 10 | 95 |
| HPV18 | E6 | 11 | 114 |
| HPV18 | E6 | 9 | 111 |
| HPV18 | E6 | 9 | 144 |
| HPV18 | E6 | 10 | 144 |
| HPV18 | E6 | 11 | 144 |
| HPV18 | E6 | 9 | 59 |
| HPV18 | E6 | 9 | 84 |
| HPV18 | E6 | 8 | 72 |
| HPV18 | E7 | 9 | 63 |
| HPV18 | E7 | 11 | 63 |
| HPV18 | E7 | 8 | 77 |
| HPV18 | E7 | 10 | 43 |
| HPV18 | E7 | 11 | 43 |
| HPV18 | E7 | 11 | 48 |
| HPV18 | E7 | 9 | 59 |
| HPV18 | E7 | 11 | 74 |
| HPV18 | E7 | 11 | 61 |
| HPV18 | E7 | 9 | 50 |
| HPV18 | E7 | 8 | 60 |
| HPV18 | E7 | 10 | 75 |
| HPV18 | L1 | 11 | 195 |
| HPV18 | L1 | 8 | 225 |
| HPV18 | L1 | 11 | 268 |
| HPV18 | L1 | 9 | 419 |
| HPV18 | L1 | 10 | 196 |
| HPV18 | L1 | 9 | 552 |
| HPV18 | L1 | 10 | 552 |
| HPV18 | L1 | 8 | 163 |
| HPV18 | L1 | 11 | 222 |
| HPV18 | L1 | 10 | 310 |
| HPV18 | L1 | 8 | 493 |
| HPV18 | L1 | 10 | 418 |
| HPV18 | L1 | 8 | 284 |
| HPV18 | L1 | 11 | 122 |
| HPV18 | L1 | 9 | 520 |
| HPV18 | L1 | 10 | 520 |
| HPV18 | L1 | 8 | 305 |
| HPV18 | L1 | 9 | 305 |
| HPV18 | L1 | 11 | 148 |
| HPV18 | L1 | 10 | 330 |
| HPV18 | L1 | 11 | 203 |
| HPV18 | L1 | 8 | 317 |
| HPV18 | L1 | 8 | 59 |
| HPV18 | L1 | 8 | 530 |
| HPV18 | L1 | 9 | 530 |
| HPV18 | L1 | 10 | 530 |
| HPV18 | L1 | 8 | 271 |
| HPV18 | L1 | 11 | 482 |
| HPV18 | L1 | 11 | 535 |
| HPV18 | L1 | 10 | 177 |
| HPV18 | L1 | 11 | 360 |
| HPV18 | L1 | 10 | 505 |
| HPV18 | L1 | 8 | 125 |
| HPV18 | L1 | 11 | 125 |
| HPV18 | L1 | 10 | 103 |
| HPV18 | L1 | 9 | 178 |
| HPV18 | L1 | 9 | 104 |
| HPV18 | L1 | 8 | 531 |

TABLE IX-continued

HLA-A3 Supermotif Peptides

| 1 | 2 | 3 | 4 |
|---|---|---|---|
| HPV18 | L1 | 9 | 531 |
| HPV18 | L1 | 10 | 496 |
| HPV18 | L1 | 9 | 224 |
| HPV18 | L1 | 8 | 558 |
| HPV18 | L1 | 10 | 558 |
| HPV18 | L1 | 11 | 558 |
| HPV18 | L1 | 10 | 57 |
| HPV18 | L1 | 10 | 282 |
| HPV18 | L1 | 10 | 16 |
| HPV18 | L1 | 8 | 550 |
| HPV18 | L1 | 11 | 550 |
| HPV18 | L1 | 8 | 540 |
| HPV18 | L1 | 10 | 472 |
| HPV18 | L1 | 10 | 412 |
| HPV18 | L1 | 10 | 315 |
| HPV18 | L1 | 11 | 366 |
| HPV18 | L1 | 9 | 484 |
| HPV18 | L1 | 11 | 102 |
| HPV18 | L1 | 11 | 547 |
| HPV18 | L1 | 9 | 112 |
| HPV18 | L1 | 9 | 135 |
| HPV18 | L1 | 8 | 561 |
| HPV18 | L1 | 10 | 548 |
| HPV18 | L1 | 10 | 551 |
| HPV18 | L1 | 11 | 551 |
| HPV18 | L1 | 9 | 127 |
| HPV18 | L1 | 10 | 93 |
| HPV18 | L1 | 9 | 150 |
| HPV18 | L1 | 11 | 518 |
| HPV18 | L1 | 8 | 306 |
| HPV18 | L1 | 9 | 555 |
| HPV18 | L1 | 11 | 555 |
| HPV18 | L1 | 8 | 485 |
| HPV18 | L1 | 9 | 362 |
| HPV18 | L1 | 11 | 92 |
| HPV18 | L1 | 10 | 149 |
| HPV18 | L1 | 8 | 474 |
| HPV18 | L1 | 9 | 197 |
| HPV18 | L1 | 8 | 554 |
| HPV18 | L1 | 10 | 554 |
| HPV18 | L1 | 9 | 473 |
| HPV18 | L1 | 8 | 553 |
| HPV18 | L1 | 9 | 553 |
| HPV18 | L1 | 11 | 553 |
| HPV18 | L1 | 8 | 105 |
| HPV18 | L1 | 9 | 331 |
| HPV18 | L1 | 11 | 71 |
| HPV18 | L1 | 10 | 126 |
| HPV18 | L1 | 10 | 361 |
| HPV18 | L1 | 10 | 161 |
| HPV18 | L1 | 8 | 230 |
| HPV18 | L1 | 10 | 230 |
| HPV18 | L1 | 9 | 73 |
| HPV18 | L2 | 10 | 286 |
| HPV18 | L2 | 8 | 12 |
| HPV18 | L2 | 11 | 12 |
| HPV18 | L2 | 11 | 354 |
| HPV18 | L2 | 9 | 273 |
| HPV18 | L2 | 11 | 109 |
| HPV18 | L2 | 9 | 260 |
| HPV18 | L2 | 8 | 443 |
| HPV18 | L2 | 9 | 276 |
| HPV18 | L2 | 11 | 306 |
| HPV18 | L2 | 11 | 58 |
| HPV18 | L2 | 10 | 25 |
| HPV18 | L2 | 9 | 60 |
| HPV18 | L2 | 11 | 292 |
| HPV18 | L2 | 10 | 210 |
| HPV18 | L2 | 11 | 210 |
| HPV18 | L2 | 10 | 34 |
| HPV18 | L2 | 9 | 287 |
| HPV18 | L2 | 8 | 1 |
| HPV18 | L2 | 9 | 1 |
| HPV18 | L2 | 10 | 1 |
| HPV18 | L2 | 11 | 1 |
| HPV18 | L2 | 10 | 79 |
| HPV18 | L2 | 11 | 285 |
| HPV18 | L2 | 8 | 357 |
| HPV18 | L2 | 11 | 209 |
| HPV18 | L2 | 8 | 439 |
| HPV18 | L2 | 9 | 439 |
| HPV18 | L2 | 10 | 439 |
| HPV18 | L2 | 11 | 439 |
| HPV18 | L2 | 10 | 216 |
| HPV18 | L2 | 11 | 258 |
| HPV18 | L2 | 9 | 11 |
| HPV18 | L2 | 11 | 298 |
| HPV18 | L2 | 10 | 281 |
| HPV18 | L2 | 11 | 281 |
| HPV18 | L2 | 9 | 308 |
| HPV18 | L2 | 10 | 364 |
| HPV18 | L2 | 10 | 68 |
| HPV18 | L2 | 10 | 220 |
| HPV18 | L2 | 9 | 211 |
| HPV18 | L2 | 10 | 211 |
| HPV18 | L2 | 10 | 110 |
| HPV18 | L2 | 8 | 212 |
| HPV18 | L2 | 9 | 212 |
| HPV18 | L2 | 9 | 365 |
| HPV18 | L2 | 10 | 235 |
| HPV18 | L2 | 10 | 13 |
| HPV18 | L2 | 9 | 111 |
| HPV18 | L2 | 8 | 288 |
| HPV18 | L2 | 11 | 288 |
| HPV18 | L2 | 8 | 261 |
| HPV18 | L2 | 8 | 366 |
| HPV18 | L2 | 10 | 293 |
| HPV18 | L2 | 9 | 217 |
| HPV18 | L2 | 9 | 80 |
| HPV18 | L2 | 9 | 221 |
| HPV18 | L2 | 9 | 236 |
| HPV18 | L2 | 8 | 2 |
| HPV18 | L2 | 9 | 2 |
| HPV18 | L2 | 10 | 2 |
| HPV18 | L2 | 11 | 234 |
| HPV18 | L2 | 9 | 14 |
| HPV18 | L2 | 8 | 81 |
| HPV18 | L2 | 8 | 112 |
| HPV18 | L2 | 11 | 436 |
| HPV31 | E1 | 8 | 296 |
| HPV31 | E1 | 8 | 185 |
| HPV31 | E1 | 9 | 111 |
| HPV31 | E1 | 11 | 439 |
| HPV31 | E1 | 8 | 81 |
| HPV31 | E1 | 11 | 370 |
| HPV31 | E1 | 10 | 263 |
| HPV31 | E1 | 10 | 113 |
| HPV31 | E1 | 11 | 113 |
| HPV31 | E1 | 9 | 477 |
| HPV31 | E1 | 8 | 284 |
| HPV31 | E1 | 10 | 284 |
| HPV31 | E1 | 9 | 100 |
| HPV31 | E1 | 11 | 100 |
| HPV31 | E1 | 8 | 620 |
| HPV31 | E1 | 11 | 364 |
| HPV31 | E1 | 9 | 366 |
| HPV31 | E1 | 11 | 528 |
| HPV31 | E1 | 11 | 348 |
| HPV31 | E1 | 8 | 80 |
| HPV31 | E1 | 9 | 80 |
| HPV31 | E1 | 10 | 201 |
| HPV31 | E1 | 8 | 583 |
| HPV31 | E1 | 8 | 315 |
| HPV31 | E1 | 8 | 443 |
| HPV31 | E1 | 9 | 372 |
| HPV31 | E1 | 10 | 436 |
| HPV31 | E1 | 11 | 566 |
| HPV31 | E1 | 9 | 433 |
| HPV31 | E1 | 9 | 252 |
| HPV31 | E1 | 11 | 252 |

TABLE IX-continued

HLA-A3 Supermotif Peptides

| 1 | 2 | 3 | 4 |
|---|---|---|---|
| HPV31 | E1 | 9 | 157 |
| HPV31 | E1 | 8 | 386 |
| HPV31 | E1 | 9 | 386 |
| HPV31 | E1 | 8 | 225 |
| HPV31 | E1 | 9 | 196 |
| HPV31 | E1 | 11 | 222 |
| HPV31 | E1 | 9 | 78 |
| HPV31 | E1 | 10 | 78 |
| HPV31 | E1 | 11 | 78 |
| HPV31 | E1 | 11 | 162 |
| HPV31 | E1 | 8 | 478 |
| HPV31 | E1 | 11 | 453 |
| HPV31 | E1 | 11 | 174 |
| HPV31 | E1 | 9 | 268 |
| HPV31 | E1 | 9 | 544 |
| HPV31 | E1 | 10 | 381 |
| HPV31 | E1 | 9 | 184 |
| HPV31 | E1 | 10 | 110 |
| HPV31 | E1 | 11 | 380 |
| HPV31 | E1 | 9 | 441 |
| HPV31 | E1 | 10 | 441 |
| HPV31 | E1 | 10 | 590 |
| HPV31 | E1 | 10 | 374 |
| HPV31 | E1 | 9 | 412 |
| HPV31 | E1 | 10 | 454 |
| HPV31 | E1 | 8 | 286 |
| HPV31 | E1 | 9 | 202 |
| HPV31 | E1 | 10 | 543 |
| HPV31 | E1 | 11 | 542 |
| HPV31 | E1 | 10 | 256 |
| HPV31 | E1 | 9 | 437 |
| HPV31 | E1 | 8 | 258 |
| HPV31 | E1 | 10 | 258 |
| HPV31 | E1 | 9 | 285 |
| HPV31 | E1 | 8 | 255 |
| HPV31 | E1 | 11 | 255 |
| HPV31 | E1 | 9 | 257 |
| HPV31 | E1 | 11 | 257 |
| HPV31 | E1 | 8 | 400 |
| HPV31 | E1 | 10 | 400 |
| HPV31 | E1 | 8 | 253 |
| HPV31 | E1 | 10 | 253 |
| HPV31 | E1 | 9 | 547 |
| HPV31 | E1 | 8 | 601 |
| HPV31 | E1 | 8 | 117 |
| HPV31 | E1 | 8 | 376 |
| HPV31 | E1 | 10 | 170 |
| HPV31 | E1 | 9 | 524 |
| HPV31 | E1 | 8 | 580 |
| HPV31 | E1 | 11 | 580 |
| HPV31 | E1 | 9 | 399 |
| HPV31 | E1 | 11 | 399 |
| HPV31 | E1 | 9 | 176 |
| HPV31 | E1 | 10 | 267 |
| HPV31 | E1 | 10 | 599 |
| HPV31 | E1 | 11 | 293 |
| HPV31 | E1 | 8 | 438 |
| HPV31 | E1 | 9 | 401 |
| HPV31 | E1 | 11 | 98 |
| HPV31 | E1 | 10 | 294 |
| HPV31 | E1 | 11 | 281 |
| HPV31 | E1 | 9 | 295 |
| HPV31 | E1 | 8 | 269 |
| HPV31 | E1 | 8 | 387 |
| HPV31 | E1 | 11 | 387 |
| HPV31 | E1 | 11 | 180 |
| HPV31 | E1 | 8 | 545 |
| HPV31 | E1 | 11 | 545 |
| HPV31 | E1 | 8 | 177 |
| HPV31 | E1 | 10 | 349 |
| HPV31 | E1 | 9 | 254 |
| HPV31 | E1 | 8 | 413 |
| HPV31 | E1 | 8 | 434 |
| HPV31 | E1 | 8 | 197 |
| HPV31 | E1 | 8 | 525 |
| HPV31 | E1 | 10 | 223 |
| HPV31 | E1 | 8 | 405 |
| HPV31 | E1 | 9 | 489 |
| HPV31 | E1 | 8 | 19 |
| HPV31 | E2 | 9 | 277 |
| HPV31 | E2 | 8 | 278 |
| HPV31 | E2 | 9 | 229 |
| HPV31 | E2 | 10 | 229 |
| HPV31 | E2 | 8 | 61 |
| HPV31 | E2 | 9 | 291 |
| HPV31 | E2 | 9 | 239 |
| HPV31 | E2 | 10 | 228 |
| HPV31 | E2 | 11 | 228 |
| HPV31 | E2 | 8 | 307 |
| HPV31 | E2 | 10 | 307 |
| HPV31 | E2 | 11 | 145 |
| HPV31 | E2 | 8 | 40 |
| HPV31 | E2 | 9 | 301 |
| HPV31 | E2 | 11 | 301 |
| HPV31 | E2 | 9 | 174 |
| HPV31 | E2 | 10 | 174 |
| HPV31 | E2 | 10 | 204 |
| HPV31 | E2 | 9 | 80 |
| HPV31 | E2 | 9 | 168 |
| HPV31 | E2 | 10 | 168 |
| HPV31 | E2 | 8 | 231 |
| HPV31 | E2 | 10 | 235 |
| HPV31 | E2 | 11 | 235 |
| HPV31 | E2 | 9 | 29 |
| HPV31 | E2 | 11 | 35 |
| HPV31 | E2 | 10 | 297 |
| HPV31 | E2 | 10 | 15 |
| HPV31 | E2 | 11 | 15 |
| HPV31 | E2 | 8 | 304 |
| HPV31 | E2 | 11 | 304 |
| HPV31 | E2 | 11 | 275 |
| HPV31 | E2 | 9 | 205 |
| HPV31 | E2 | 11 | 14 |
| HPV31 | E2 | 11 | 4 |
| HPV31 | E2 | 9 | 103 |
| HPV31 | E2 | 10 | 103 |
| HPV31 | E2 | 9 | 342 |
| HPV31 | E2 | 11 | 78 |
| HPV31 | E2 | 9 | 303 |
| HPV31 | E2 | 10 | 254 |
| HPV31 | E2 | 9 | 127 |
| HPV31 | E2 | 8 | 219 |
| HPV31 | E2 | 9 | 60 |
| HPV31 | E2 | 10 | 290 |
| HPV31 | E2 | 10 | 57 |
| HPV31 | E2 | 8 | 238 |
| HPV31 | E2 | 10 | 238 |
| HPV31 | E2 | 10 | 25 |
| HPV31 | E2 | 9 | 37 |
| HPV31 | E2 | 11 | 37 |
| HPV31 | E2 | 8 | 7 |
| HPV31 | E2 | 10 | 276 |
| HPV31 | E2 | 11 | 324 |
| HPV31 | E2 | 11 | 216 |
| HPV31 | E2 | 8 | 104 |
| HPV31 | E2 | 9 | 104 |
| HPV31 | E2 | 8 | 81 |
| HPV31 | E2 | 10 | 341 |
| HPV31 | E2 | 8 | 128 |
| HPV31 | E2 | 8 | 292 |
| HPV31 | E2 | 8 | 240 |
| HPV31 | E2 | 10 | 146 |
| HPV31 | E2 | 11 | 340 |
| HPV31 | E2 | 9 | 147 |
| HPV31 | E2 | 9 | 58 |
| HPV31 | E2 | 11 | 58 |
| HPV31 | E2 | 9 | 328 |
| HPV31 | E2 | 10 | 102 |
| HPV31 | E2 | 11 | 102 |
| HPV31 | E5 | 11 | 20 |

TABLE IX-continued

HLA-A3 Supermotif Peptides

| 1 | 2 | 3 | 4 |
|---|---|---|---|
| HPV31 | E5 | 11 | 48 |
| HPV31 | E5 | 9 | 22 |
| HPV31 | E5 | 8 | 51 |
| HPV31 | E5 | 10 | 21 |
| HPV31 | E5 | 9 | 50 |
| HPV31 | E6 | 10 | 18 |
| HPV31 | E6 | 9 | 136 |
| HPV31 | E6 | 10 | 63 |
| HPV31 | E6 | 11 | 98 |
| HPV31 | E6 | 9 | 57 |
| HPV31 | E6 | 8 | 20 |
| HPV31 | E6 | 10 | 25 |
| HPV31 | E6 | 11 | 45 |
| HPV31 | E6 | 9 | 47 |
| HPV31 | E6 | 8 | 95 |
| HPV31 | E6 | 10 | 85 |
| HPV31 | E6 | 8 | 61 |
| HPV31 | E6 | 8 | 137 |
| HPV31 | E6 | 9 | 72 |
| HPV31 | E6 | 9 | 100 |
| HPV31 | E6 | 10 | 99 |
| HPV31 | E6 | 9 | 127 |
| HPV31 | E6 | 9 | 109 |
| HPV31 | E6 | 8 | 27 |
| HPV31 | E6 | 11 | 17 |
| HPV31 | E6 | 9 | 82 |
| HPV31 | E6 | 8 | 87 |
| HPV31 | E6 | 9 | 86 |
| HPV31 | E6 | 8 | 73 |
| HPV31 | E6 | 10 | 132 |
| HPV31 | E6 | 11 | 132 |
| HPV31 | E6 | 8 | 70 |
| HPV31 | E6 | 11 | 70 |
| HPV31 | E6 | 10 | 81 |
| HPV31 | E7 | 10 | 68 |
| HPV31 | E7 | 10 | 88 |
| HPV31 | E7 | 9 | 89 |
| HPV31 | E7 | 9 | 54 |
| HPV31 | E7 | 10 | 53 |
| HPV31 | E7 | 8 | 70 |
| HPV31 | E7 | 8 | 55 |
| HPV31 | L1 | 11 | 347 |
| HPV31 | L1 | 10 | 348 |
| HPV31 | L1 | 11 | 426 |
| HPV31 | L1 | 11 | 208 |
| HPV31 | L1 | 8 | 491 |
| HPV31 | L1 | 9 | 491 |
| HPV31 | L1 | 10 | 491 |
| HPV31 | L1 | 11 | 491 |
| HPV31 | L1 | 8 | 103 |
| HPV31 | L1 | 8 | 224 |
| HPV31 | L1 | 9 | 459 |
| HPV31 | L1 | 10 | 459 |
| HPV31 | L1 | 10 | 372 |
| HPV31 | L1 | 8 | 245 |
| HPV31 | L1 | 9 | 245 |
| HPV31 | L1 | 11 | 88 |
| HPV31 | L1 | 10 | 353 |
| HPV31 | L1 | 10 | 270 |
| HPV31 | L1 | 8 | 469 |
| HPV31 | L1 | 10 | 469 |
| HPV31 | L1 | 8 | 211 |
| HPV31 | L1 | 8 | 257 |
| HPV31 | L1 | 11 | 421 |
| HPV31 | L1 | 9 | 331 |
| HPV31 | L1 | 10 | 117 |
| HPV31 | L1 | 8 | 68 |
| HPV31 | L1 | 10 | 68 |
| HPV31 | L1 | 8 | 413 |
| HPV31 | L1 | 9 | 349 |
| HPV31 | L1 | 9 | 118 |
| HPV31 | L1 | 10 | 427 |
| HPV31 | L1 | 10 | 357 |
| HPV31 | L1 | 8 | 431 |
| HPV31 | L1 | 8 | 65 |
| HPV31 | L1 | 11 | 65 |
| HPV31 | L1 | 11 | 20 |
| HPV31 | L1 | 9 | 470 |
| HPV31 | L1 | 11 | 470 |
| HPV31 | L1 | 11 | 300 |
| HPV31 | L1 | 10 | 32 |
| HPV31 | L1 | 11 | 227 |
| HPV31 | L1 | 8 | 496 |
| HPV31 | L1 | 9 | 496 |
| HPV31 | L1 | 8 | 165 |
| HPV31 | L1 | 10 | 222 |
| HPV31 | L1 | 10 | 489 |
| HPV31 | L1 | 11 | 489 |
| HPV31 | L1 | 10 | 411 |
| HPV31 | L1 | 9 | 472 |
| HPV31 | L1 | 11 | 472 |
| HPV31 | L1 | 11 | 306 |
| HPV31 | L1 | 8 | 156 |
| HPV31 | L1 | 11 | 329 |
| HPV31 | L1 | 10 | 255 |
| HPV31 | L1 | 10 | 154 |
| HPV31 | L1 | 10 | 476 |
| HPV31 | L1 | 11 | 476 |
| HPV31 | L1 | 9 | 75 |
| HPV31 | L1 | 11 | 457 |
| HPV31 | L1 | 9 | 490 |
| HPV31 | L1 | 10 | 490 |
| HPV31 | L1 | 11 | 490 |
| HPV31 | L1 | 10 | 228 |
| HPV31 | L1 | 9 | 51 |
| HPV31 | L1 | 10 | 51 |
| HPV31 | L1 | 9 | 358 |
| HPV31 | L1 | 8 | 23 |
| HPV31 | L1 | 8 | 492 |
| HPV31 | L1 | 9 | 492 |
| HPV31 | L1 | 10 | 492 |
| HPV31 | L1 | 9 | 271 |
| HPV31 | L1 | 8 | 246 |
| HPV31 | L1 | 9 | 302 |
| HPV31 | L1 | 10 | 89 |
| HPV31 | L1 | 9 | 423 |
| HPV31 | L1 | 9 | 354 |
| HPV31 | L1 | 8 | 494 |
| HPV31 | L1 | 10 | 494 |
| HPV31 | L1 | 11 | 494 |
| HPV31 | L1 | 8 | 493 |
| HPV31 | L1 | 9 | 493 |
| HPV31 | L1 | 11 | 493 |
| HPV31 | L1 | 11 | 44 |
| HPV31 | L1 | 11 | 10 |
| HPV31 | L1 | 10 | 66 |
| HPV31 | L1 | 9 | 22 |
| HPV31 | L1 | 10 | 301 |
| HPV31 | L1 | 10 | 422 |
| HPV31 | L1 | 8 | 332 |
| HPV31 | L1 | 11 | 62 |
| HPV31 | L1 | 10 | 21 |
| HPV31 | L1 | 10 | 101 |
| HPV31 | L1 | 10 | 136 |
| HPV31 | L1 | 9 | 12 |
| HPV31 | L1 | 10 | 250 |
| HPV31 | L1 | 10 | 50 |
| HPV31 | L1 | 11 | 50 |
| HPV31 | L1 | 9 | 445 |
| HPV31 | L1 | 11 | 445 |
| HPV31 | L2 | 10 | 281 |
| HPV31 | L2 | 11 | 281 |
| HPV31 | L2 | 10 | 286 |
| HPV31 | L2 | 11 | 13 |
| HPV31 | L2 | 9 | 15 |
| HPV31 | L2 | 9 | 276 |
| HPV31 | L2 | 11 | 59 |
| HPV31 | L2 | 11 | 221 |
| HPV31 | L2 | 9 | 61 |
| HPV31 | L2 | 10 | 26 |

TABLE IX-continued

HLA-A3 Supermotif Peptides

| 1 | 2 | 3 | 4 |
|---|---|---|---|
| HPV31 | L2 | 10 | 38 |
| HPV31 | L2 | 11 | 280 |
| HPV31 | L2 | 11 | 205 |
| HPV31 | L2 | 9 | 287 |
| HPV31 | L2 | 8 | 447 |
| HPV31 | L2 | 11 | 292 |
| HPV31 | L2 | 11 | 285 |
| HPV31 | L2 | 9 | 217 |
| HPV31 | L2 | 10 | 210 |
| HPV31 | L2 | 8 | 443 |
| HPV31 | L2 | 9 | 443 |
| HPV31 | L2 | 10 | 443 |
| HPV31 | L2 | 11 | 443 |
| HPV31 | L2 | 8 | 235 |
| HPV31 | L2 | 9 | 298 |
| HPV31 | L2 | 11 | 298 |
| HPV31 | L2 | 9 | 308 |
| HPV31 | L2 | 8 | 2 |
| HPV31 | L2 | 10 | 2 |
| HPV31 | L2 | 11 | 2 |
| HPV31 | L2 | 8 | 5 |
| HPV31 | L2 | 10 | 69 |
| HPV31 | L2 | 11 | 306 |
| HPV31 | L2 | 10 | 14 |
| HPV31 | L2 | 9 | 207 |
| HPV31 | L2 | 10 | 207 |
| HPV31 | L2 | 8 | 208 |
| HPV31 | L2 | 9 | 208 |
| HPV31 | L2 | 11 | 80 |
| HPV31 | L2 | 8 | 40 |
| HPV31 | L2 | 8 | 288 |
| HPV31 | L2 | 11 | 288 |
| HPV31 | L2 | 10 | 206 |
| HPV31 | L2 | 11 | 206 |
| HPV31 | L2 | 9 | 39 |
| HPV31 | L2 | 10 | 293 |
| HPV31 | L2 | 10 | 81 |
| HPV31 | L2 | 11 | 232 |
| HPV31 | L2 | 9 | 82 |
| HPV31 | L2 | 10 | 440 |
| HPV31 | L2 | 11 | 440 |
| HPV31 | L2 | 8 | 446 |
| HPV31 | L2 | 9 | 446 |
| HPV31 | L2 | 9 | 223 |
| HPV31 | L2 | 11 | 296 |
| HPV33 | E1 | 8 | 96 |
| HPV33 | E1 | 11 | 383 |
| HPV33 | E1 | 11 | 104 |
| HPV33 | E1 | 8 | 596 |
| HPV33 | E1 | 8 | 81 |
| HPV33 | E1 | 8 | 297 |
| HPV33 | E1 | 10 | 297 |
| HPV33 | E1 | 8 | 633 |
| HPV33 | E1 | 11 | 633 |
| HPV33 | E1 | 10 | 276 |
| HPV33 | E1 | 9 | 490 |
| HPV33 | E1 | 8 | 614 |
| HPV33 | E1 | 9 | 78 |
| HPV33 | E1 | 10 | 78 |
| HPV33 | E1 | 11 | 78 |
| HPV33 | E1 | 11 | 377 |
| HPV33 | E1 | 10 | 566 |
| HPV33 | E1 | 11 | 541 |
| HPV33 | E1 | 11 | 99 |
| HPV33 | E1 | 9 | 537 |
| HPV33 | E1 | 10 | 214 |
| HPV33 | E1 | 8 | 242 |
| HPV33 | E1 | 10 | 295 |
| HPV33 | E1 | 8 | 19 |
| HPV33 | E1 | 9 | 19 |
| HPV33 | E1 | 10 | 449 |
| HPV33 | E1 | 8 | 456 |
| HPV33 | E1 | 9 | 385 |
| HPV33 | E1 | 9 | 212 |
| HPV33 | E1 | 9 | 446 |
| HPV33 | E1 | 10 | 446 |
| HPV33 | E1 | 8 | 451 |
| HPV33 | E1 | 9 | 265 |
| HPV33 | E1 | 11 | 265 |
| HPV33 | E1 | 8 | 399 |
| HPV33 | E1 | 9 | 399 |
| HPV33 | E1 | 9 | 209 |
| HPV33 | E1 | 11 | 235 |
| HPV33 | E1 | 9 | 480 |
| HPV33 | E1 | 9 | 327 |
| HPV33 | E1 | 9 | 256 |
| HPV33 | E1 | 10 | 573 |
| HPV33 | E1 | 8 | 266 |
| HPV33 | E1 | 10 | 266 |
| HPV33 | E1 | 9 | 267 |
| HPV33 | E1 | 8 | 268 |
| HPV33 | E1 | 11 | 268 |
| HPV33 | E1 | 8 | 400 |
| HPV33 | E1 | 11 | 400 |
| HPV33 | E1 | 8 | 210 |
| HPV33 | E1 | 11 | 210 |
| HPV33 | E1 | 8 | 538 |
| HPV33 | E1 | 11 | 187 |
| HPV33 | E1 | 10 | 236 |
| HPV33 | E1 | 11 | 520 |
| HPV33 | E1 | 10 | 394 |
| HPV33 | E1 | 9 | 197 |
| HPV33 | E1 | 11 | 393 |
| HPV33 | E1 | 10 | 612 |
| HPV33 | E1 | 11 | 412 |
| HPV33 | E1 | 10 | 603 |
| HPV33 | E1 | 10 | 387 |
| HPV33 | E1 | 9 | 425 |
| HPV33 | E1 | 10 | 467 |
| HPV33 | E1 | 8 | 271 |
| HPV33 | E1 | 10 | 271 |
| HPV33 | E1 | 9 | 270 |
| HPV33 | E1 | 11 | 270 |
| HPV33 | E1 | 10 | 269 |
| HPV33 | E1 | 9 | 215 |
| HPV33 | E1 | 11 | 466 |
| HPV33 | E1 | 10 | 413 |
| HPV33 | E1 | 8 | 481 |
| HPV33 | E1 | 9 | 298 |
| HPV33 | E1 | 8 | 80 |
| HPV33 | E1 | 9 | 80 |
| HPV33 | E1 | 11 | 57 |
| HPV33 | E1 | 9 | 379 |
| HPV33 | E1 | 8 | 389 |
| HPV33 | E1 | 9 | 195 |
| HPV33 | E1 | 11 | 195 |
| HPV33 | E1 | 9 | 560 |
| HPV33 | E1 | 9 | 189 |
| HPV33 | E1 | 8 | 238 |
| HPV33 | E1 | 11 | 593 |
| HPV33 | E1 | 8 | 60 |
| HPV33 | E1 | 10 | 94 |
| HPV33 | E1 | 9 | 308 |
| HPV33 | E1 | 8 | 575 |
| HPV33 | E1 | 11 | 306 |
| HPV33 | E1 | 8 | 109 |
| HPV33 | E1 | 9 | 95 |
| HPV33 | E1 | 10 | 634 |
| HPV33 | E1 | 9 | 414 |
| HPV33 | E1 | 11 | 111 |
| HPV33 | E1 | 10 | 58 |
| HPV33 | E1 | 11 | 193 |
| HPV33 | E1 | 11 | 239 |
| HPV33 | E1 | 8 | 447 |
| HPV33 | E1 | 9 | 447 |
| HPV33 | E1 | 11 | 558 |
| HPV33 | E1 | 8 | 328 |
| HPV33 | E1 | 10 | 240 |
| HPV33 | E1 | 8 | 299 |
| HPV33 | E1 | 8 | 491 |

TABLE IX-continued

HLA-A3 Supermotif Peptides

| 1 | 2 | 3 | 4 |
|---|---|---|---|
| HPV33 | E1 | 8 | 190 |
| HPV33 | E1 | 10 | 100 |
| HPV33 | E1 | 8 | 418 |
| HPV33 | E1 | 9 | 502 |
| HPV33 | E1 | 9 | 522 |
| HPV33 | E1 | 9 | 595 |
| HPV33 | E1 | 11 | 254 |
| HPV33 | E2 | 8 | 249 |
| HPV33 | E2 | 9 | 258 |
| HPV33 | E2 | 9 | 245 |
| HPV33 | E2 | 8 | 40 |
| HPV33 | E2 | 10 | 288 |
| HPV33 | E2 | 9 | 211 |
| HPV33 | E2 | 10 | 25 |
| HPV33 | E2 | 8 | 235 |
| HPV33 | E2 | 9 | 143 |
| HPV33 | E2 | 11 | 232 |
| HPV33 | E2 | 11 | 74 |
| HPV33 | E2 | 9 | 282 |
| HPV33 | E2 | 11 | 282 |
| HPV33 | E2 | 11 | 115 |
| HPV33 | E2 | 9 | 100 |
| HPV33 | E2 | 10 | 156 |
| HPV33 | E2 | 10 | 278 |
| HPV33 | E2 | 9 | 15 |
| HPV33 | E2 | 11 | 4 |
| HPV33 | E2 | 10 | 14 |
| HPV33 | E2 | 8 | 165 |
| HPV33 | E2 | 8 | 77 |
| HPV33 | E2 | 9 | 284 |
| HPV33 | E2 | 11 | 284 |
| HPV33 | E2 | 9 | 272 |
| HPV33 | E2 | 9 | 248 |
| HPV33 | E2 | 9 | 60 |
| HPV33 | E2 | 8 | 27 |
| HPV33 | E2 | 11 | 27 |
| HPV33 | E2 | 8 | 222 |
| HPV33 | E2 | 9 | 29 |
| HPV33 | E2 | 9 | 76 |
| HPV33 | E2 | 8 | 332 |
| HPV33 | E2 | 10 | 57 |
| HPV33 | E2 | 8 | 7 |
| HPV33 | E2 | 11 | 37 |
| HPV33 | E2 | 9 | 256 |
| HPV33 | E2 | 11 | 256 |
| HPV33 | E2 | 10 | 5 |
| HPV33 | E2 | 11 | 98 |
| HPV33 | E2 | 8 | 285 |
| HPV33 | E2 | 10 | 285 |
| HPV33 | E2 | 8 | 61 |
| HPV33 | E2 | 11 | 270 |
| HPV33 | E2 | 11 | 304 |
| HPV33 | E2 | 10 | 305 |
| HPV33 | E2 | 11 | 209 |
| HPV33 | E2 | 11 | 254 |
| HPV33 | E2 | 8 | 257 |
| HPV33 | E2 | 10 | 257 |
| HPV33 | E2 | 8 | 310 |
| HPV33 | E2 | 10 | 233 |
| HPV33 | E2 | 8 | 118 |
| HPV33 | E2 | 9 | 118 |
| HPV33 | E2 | 10 | 116 |
| HPV33 | E2 | 11 | 116 |
| HPV33 | E2 | 8 | 273 |
| HPV33 | E2 | 9 | 117 |
| HPV33 | E2 | 10 | 117 |
| HPV33 | E2 | 9 | 58 |
| HPV33 | E2 | 11 | 58 |
| HPV33 | E2 | 10 | 102 |
| HPV33 | E2 | 11 | 102 |
| HPV33 | E2 | 9 | 309 |
| HPV33 | E2 | 11 | 159 |
| HPV33 | E5 | 9 | 12 |
| HPV33 | E5 | 11 | 10 |
| HV33 | E5 | 11 | 38 |
| HPV33 | E5 | 9 | 40 |
| HPV33 | E6 | 8 | 137 |
| HPV33 | E6 | 9 | 137 |
| HPV33 | E6 | 8 | 136 |
| HPV33 | E6 | 9 | 136 |
| HPV33 | E6 | 10 | 136 |
| HPV33 | E6 | 10 | 30 |
| HPV33 | E6 | 11 | 98 |
| HPV33 | E6 | 8 | 27 |
| HPV33 | E6 | 9 | 27 |
| HPV33 | E6 | 9 | 47 |
| HPV33 | E6 | 11 | 45 |
| HPV33 | E6 | 9 | 69 |
| HPV33 | E6 | 8 | 61 |
| HPV33 | E6 | 10 | 99 |
| HPV33 | E6 | 8 | 128 |
| HPV33 | E6 | 9 | 64 |
| HPV33 | E6 | 9 | 100 |
| HPV33 | E6 | 8 | 70 |
| HPV33 | E6 | 10 | 25 |
| HPV33 | E6 | 11 | 25 |
| HPV33 | E6 | 9 | 127 |
| HPV33 | E6 | 8 | 86 |
| HPV33 | E6 | 9 | 86 |
| HPV33 | E6 | 8 | 109 |
| HPV33 | E6 | 9 | 109 |
| HPV33 | E6 | 8 | 95 |
| HPV33 | E6 | 8 | 87 |
| HPV33 | E6 | 10 | 132 |
| HPV33 | E7 | 10 | 68 |
| HPV33 | E7 | 11 | 30 |
| HPV33 | E7 | 8 | 59 |
| HPV33 | E7 | 8 | 70 |
| HPV33 | E7 | 10 | 31 |
| HPV33 | L1 | 11 | 424 |
| HPV33 | L1 | 8 | 411 |
| HPV33 | L1 | 10 | 44 |
| HPV33 | L1 | 9 | 270 |
| HPV33 | L1 | 11 | 207 |
| HPV33 | L1 | 11 | 345 |
| HPV33 | L1 | 8 | 103 |
| HPV33 | L1 | 8 | 223 |
| HPV33 | L1 | 9 | 457 |
| HPV33 | L1 | 10 | 457 |
| HPV33 | L1 | 10 | 370 |
| HPV33 | L1 | 8 | 244 |
| HPV33 | L1 | 9 | 244 |
| HPV33 | L1 | 10 | 351 |
| HPV33 | L1 | 10 | 202 |
| HPV33 | L1 | 11 | 88 |
| HPV33 | L1 | 10 | 269 |
| HPV33 | L1 | 8 | 467 |
| HPV33 | L1 | 10 | 467 |
| HPV33 | L1 | 10 | 249 |
| HPV33 | L1 | 10 | 50 |
| HPV33 | L1 | 11 | 50 |
| HPV33 | L1 | 8 | 256 |
| HPV33 | L1 | 11 | 419 |
| HPV33 | L1 | 9 | 330 |
| HPV33 | L1 | 10 | 117 |
| HPV33 | L1 | 9 | 472 |
| HPV33 | L1 | 10 | 472 |
| HPV33 | L1 | 8 | 68 |
| HPV33 | L1 | 10 | 68 |
| HPV33 | L1 | 11 | 226 |
| HPV33 | L1 | 9 | 118 |
| HPV33 | L1 | 10 | 425 |
| HPV33 | L1 | 8 | 474 |
| HPV33 | L1 | 11 | 478 |
| HPV33 | L1 | 8 | 429 |
| HPV33 | L1 | 8 | 65 |
| HPV33 | L1 | 11 | 65 |
| HPV33 | L1 | 11 | 20 |
| HPV33 | L1 | 11 | 43 |
| HPV33 | L1 | 9 | 468 |

TABLE IX-continued

HLA-A3 Supermotif Peptides

| 1 | 2 | 3 | 4 |
|---|---|---|---|
| HPV33 | L1 | 11 | 468 |
| HPV33 | L1 | 11 | 62 |
| HPV33 | L1 | 11 | 299 |
| HPV33 | L1 | 9 | 57 |
| HPV33 | L1 | 10 | 221 |
| HPV33 | L1 | 10 | 409 |
| HPV33 | L1 | 8 | 165 |
| HPV33 | L1 | 11 | 55 |
| HPV33 | L1 | 10 | 484 |
| HPV33 | L1 | 11 | 484 |
| HPV33 | L1 | 9 | 470 |
| HPV33 | L1 | 11 | 470 |
| HPV33 | L1 | 8 | 156 |
| HPV33 | L1 | 11 | 305 |
| HPV33 | L1 | 10 | 254 |
| HPV33 | L1 | 10 | 154 |
| HPV33 | L1 | 11 | 328 |
| HPV33 | L1 | 9 | 347 |
| HPV33 | L1 | 8 | 481 |
| HPV33 | L1 | 8 | 488 |
| HPV33 | L1 | 9 | 488 |
| HPV33 | L1 | 11 | 488 |
| HPV33 | L1 | 9 | 75 |
| HPV33 | L1 | 11 | 455 |
| HPV33 | L1 | 8 | 491 |
| HPV33 | L1 | 9 | 491 |
| HPV33 | L1 | 9 | 410 |
| HPV33 | L1 | 9 | 51 |
| HPV33 | L1 | 10 | 51 |
| HPV33 | L1 | 10 | 32 |
| HPV33 | L1 | 8 | 245 |
| HPV33 | L1 | 9 | 490 |
| HPV33 | L1 | 10 | 490 |
| HPV33 | L1 | 10 | 227 |
| HPV33 | L1 | 8 | 23 |
| HPV33 | L1 | 8 | 486 |
| HPV33 | L1 | 9 | 486 |
| HPV33 | L1 | 10 | 486 |
| HPV33 | L1 | 11 | 486 |
| HPV33 | L1 | 9 | 352 |
| HPV33 | L1 | 9 | 301 |
| HPV33 | L1 | 10 | 89 |
| HPV33 | L1 | 11 | 31 |
| HPV33 | L1 | 9 | 421 |
| HPV33 | L1 | 8 | 489 |
| HPV33 | L1 | 10 | 489 |
| HPV33 | L1 | 11 | 489 |
| HPV33 | L1 | 9 | 485 |
| HPV33 | L1 | 10 | 485 |
| HPV33 | L1 | 11 | 485 |
| HPV33 | L1 | 11 | 10 |
| HPV33 | L1 | 10 | 66 |
| HPV33 | L1 | 9 | 22 |
| HPV33 | L1 | 8 | 348 |
| HPV33 | L1 | 10 | 300 |
| HPV33 | L1 | 10 | 420 |
| HPV33 | L1 | 8 | 331 |
| HPV33 | L1 | 10 | 21 |
| HPV33 | L1 | 10 | 101 |
| HPV33 | L1 | 9 | 12 |
| HPV33 | L1 | 9 | 443 |
| HPV33 | L1 | 11 | 443 |
| HPV33 | L2 | 9 | 81 |
| HPV33 | L2 | 8 | 82 |
| HPV33 | L2 | 10 | 291 |
| HPV33 | L2 | 10 | 286 |
| HPV33 | L2 | 11 | 286 |
| HPV33 | L2 | 11 | 12 |
| HPV33 | L2 | 9 | 308 |
| HPV33 | L2 | 9 | 14 |
| HPV33 | L2 | 8 | 447 |
| HPV33 | L2 | 9 | 447 |
| HPV33 | L2 | 9 | 281 |
| HPV33 | L2 | 11 | 301 |
| HPV33 | L2 | 11 | 440 |
| HPV33 | L2 | 11 | 58 |
| HPV33 | L2 | 11 | 226 |
| HPV33 | L2 | 10 | 37 |
| HPV33 | L2 | 10 | 25 |
| HPV33 | L2 | 9 | 60 |
| HPV33 | L2 | 10 | 379 |
| HPV33 | L2 | 11 | 297 |
| HPV33 | L2 | 11 | 285 |
| HPV33 | L2 | 8 | 448 |
| HPV33 | L2 | 9 | 292 |
| HPV33 | L2 | 10 | 307 |
| HPV33 | L2 | 11 | 311 |
| HPV33 | L2 | 9 | 240 |
| HPV33 | L2 | 11 | 290 |
| HPV33 | L2 | 10 | 215 |
| HPV33 | L2 | 8 | 444 |
| HPV33 | L2 | 9 | 444 |
| HPV33 | L2 | 10 | 444 |
| HPV33 | L2 | 11 | 444 |
| HPV33 | L2 | 11 | 79 |
| HPV33 | L2 | 10 | 221 |
| HPV33 | L2 | 9 | 313 |
| HPV33 | L2 | 9 | 303 |
| HPV33 | L2 | 11 | 303 |
| HPV33 | L2 | 10 | 13 |
| HPV33 | L2 | 9 | 212 |
| HPV33 | L2 | 9 | 38 |
| HPV33 | L2 | 8 | 213 |
| HPV33 | L2 | 10 | 80 |
| HPV33 | L2 | 8 | 39 |
| HPV33 | L2 | 8 | 309 |
| HPV33 | L2 | 8 | 293 |
| HPV33 | L2 | 11 | 293 |
| HPV33 | L2 | 10 | 211 |
| HPV33 | L2 | 10 | 298 |
| HPV33 | L2 | 9 | 222 |
| HPV33 | L2 | 10 | 441 |
| HPV33 | L2 | 11 | 441 |
| HPV33 | L2 | 11 | 210 |
| HPV33 | L2 | 9 | 228 |
| HPV33 | L2 | 8 | 381 |
| HPV45 | E1 | 11 | 383 |
| HPV45 | E1 | 8 | 198 |
| HPV45 | E1 | 11 | 532 |
| HPV45 | E1 | 11 | 452 |
| HPV45 | E1 | 9 | 270 |
| HPV45 | E1 | 11 | 270 |
| HPV45 | E1 | 8 | 399 |
| HPV45 | E1 | 9 | 399 |
| HPV45 | E1 | 9 | 398 |
| HPV45 | E1 | 10 | 398 |
| HPV45 | E1 | 8 | 297 |
| HPV45 | E1 | 10 | 297 |
| HPV45 | E1 | 11 | 423 |
| HPV45 | E1 | 8 | 634 |
| HPV45 | E1 | 9 | 78 |
| HPV45 | E1 | 10 | 78 |
| HPV45 | E1 | 11 | 78 |
| HPV45 | E1 | 10 | 214 |
| HPV45 | E1 | 11 | 623 |
| HPV45 | E1 | 8 | 328 |
| HPV45 | E1 | 8 | 596 |
| HPV45 | E1 | 9 | 115 |
| HPV45 | E1 | 10 | 115 |
| HPV45 | E1 | 11 | 186 |
| HPV45 | E1 | 8 | 189 |
| HPV45 | E1 | 9 | 189 |
| HPV45 | E1 | 10 | 295 |
| HPV45 | E1 | 9 | 446 |
| HPV45 | E1 | 8 | 456 |
| HPV45 | E1 | 9 | 385 |
| HPV45 | E1 | 10 | 449 |
| HPV45 | E1 | 9 | 212 |
| HPV45 | E1 | 11 | 579 |
| HPV45 | E1 | 8 | 19 |

TABLE IX-continued

HLA-A3 Supermotif Peptides

| 1 | 2 | 3 | 4 |
|---|---|---|---|
| HPV45 | E1 | 9 | 19 |
| HPV45 | E1 | 8 | 626 |
| HPV45 | E1 | 9 | 209 |
| HPV45 | E1 | 9 | 443 |
| HPV45 | E1 | 9 | 265 |
| HPV45 | E1 | 11 | 265 |
| HPV45 | E1 | 11 | 235 |
| HPV45 | E1 | 8 | 256 |
| HPV45 | E1 | 8 | 268 |
| HPV45 | E1 | 11 | 268 |
| HPV45 | E1 | 11 | 555 |
| HPV45 | E1 | 11 | 466 |
| HPV45 | E1 | 8 | 447 |
| HPV45 | E1 | 8 | 538 |
| HPV45 | E1 | 8 | 116 |
| HPV45 | E1 | 9 | 116 |
| HPV45 | E1 | 11 | 116 |
| HPV45 | E1 | 9 | 197 |
| HPV45 | E1 | 9 | 425 |
| HPV45 | E1 | 10 | 387 |
| HPV45 | E1 | 10 | 269 |
| HPV45 | E1 | 8 | 299 |
| HPV45 | E1 | 9 | 267 |
| HPV45 | E1 | 11 | 84 |
| HPV45 | E1 | 8 | 190 |
| HPV45 | E1 | 8 | 271 |
| HPV45 | E1 | 10 | 271 |
| HPV45 | E1 | 10 | 556 |
| HPV45 | E1 | 10 | 467 |
| HPV45 | E1 | 8 | 210 |
| HPV45 | E1 | 11 | 210 |
| HPV45 | E1 | 10 | 103 |
| HPV45 | E1 | 9 | 557 |
| HPV45 | E1 | 9 | 215 |
| HPV45 | E1 | 9 | 298 |
| HPV45 | E1 | 8 | 415 |
| HPV45 | E1 | 11 | 415 |
| HPV45 | E1 | 9 | 560 |
| HPV45 | E1 | 9 | 414 |
| HPV45 | E1 | 8 | 119 |
| HPV45 | E1 | 9 | 119 |
| HPV45 | E1 | 10 | 119 |
| HPV45 | E1 | 9 | 379 |
| HPV45 | E1 | 9 | 537 |
| HPV45 | E1 | 8 | 238 |
| HPV45 | E1 | 8 | 593 |
| HPV45 | E1 | 11 | 593 |
| HPV45 | E1 | 11 | 102 |
| HPV45 | E1 | 9 | 412 |
| HPV45 | E1 | 11 | 412 |
| HPV45 | E1 | 8 | 80 |
| HPV45 | E1 | 9 | 80 |
| HPV45 | E1 | 8 | 451 |
| HPV45 | E1 | 11 | 306 |
| HPV45 | E1 | 8 | 117 |
| HPV45 | E1 | 10 | 117 |
| HPV45 | E1 | 11 | 117 |
| HPV45 | E1 | 10 | 307 |
| HPV45 | E1 | 9 | 308 |
| HPV45 | E1 | 9 | 104 |
| HPV45 | E1 | 8 | 558 |
| HPV45 | E1 | 11 | 558 |
| HPV45 | E1 | 11 | 239 |
| HPV45 | E1 | 8 | 309 |
| HPV45 | E1 | 10 | 240 |
| HPV45 | E1 | 8 | 81 |
| HPV45 | E1 | 8 | 266 |
| HPV45 | E1 | 10 | 266 |
| HPV45 | E1 | 8 | 400 |
| NPV45 | E1 | 11 | 400 |
| HPV45 | E1 | 11 | 325 |
| HPV45 | E1 | 8 | 418 |
| HPV45 | E1 | 9 | 502 |
| HPV45 | E1 | 9 | 522 |
| HPV45 | E1 | 10 | 254 |
| HPV45 | E1 | 10 | 394 |
| HPV45 | E2 | 9 | 78 |
| HPV45 | E2 | 9 | 84 |
| HPV45 | E2 | 8 | 305 |
| HPV45 | E2 | 8 | 274 |
| HPV45 | E2 | 9 | 274 |
| HPV45 | E2 | 10 | 274 |
| HPV45 | E2 | 11 | 274 |
| HPV45 | E2 | 11 | 158 |
| HPV45 | E2 | 9 | 171 |
| HPV45 | E2 | 10 | 212 |
| HPV45 | E2 | 10 | 50 |
| HPV45 | E2 | 9 | 255 |
| HPV45 | E2 | 8 | 225 |
| HPV45 | E2 | 8 | 242 |
| HPV45 | E2 | 9 | 242 |
| HPV45 | E2 | 11 | 242 |
| HPV45 | E2 | 10 | 295 |
| HPV45 | E2 | 8 | 124 |
| HPV45 | E2 | 8 | 293 |
| HPV45 | E2 | 10 | 21 |
| HPV45 | E2 | 8 | 70 |
| HPV45 | E2 | 8 | 36 |
| HPV45 | E2 | 9 | 146 |
| HPV45 | E2 | 10 | 77 |
| HPV45 | E2 | 11 | 20 |
| HPV45 | E2 | 9 | 232 |
| HPV45 | E2 | 11 | 121 |
| HPV45 | E2 | 10 | 272 |
| HPV45 | E2 | 11 | 272 |
| HPV45 | E2 | 11 | 10 |
| HPV45 | E2 | 8 | 256 |
| HPV45 | E2 | 11 | 336 |
| HPV45 | E2 | 10 | 83 |
| HPV45 | E2 | 8 | 46 |
| HPV45 | E2 | 9 | 69 |
| HPV45 | E2 | 9 | 301 |
| HPV45 | E2 | 11 | 301 |
| HPV45 | E2 | 11 | 33 |
| HPV45 | E2 | 9 | 109 |
| HPV45 | E2 | 10 | 109 |
| HPV45 | E2 | 9 | 289 |
| HPV45 | E2 | 9 | 292 |
| HPV45 | E2 | 8 | 67 |
| HPV45 | E2 | 11 | 67 |
| HPV45 | E2 | 11 | 271 |
| HPV45 | E2 | 10 | 112 |
| HPV45 | E2 | 9 | 35 |
| HPV45 | E2 | 11 | 222 |
| HPV45 | E2 | 11 | 82 |
| HPV45 | E2 | 9 | 244 |
| HPV45 | E2 | 10 | 4 |
| HPV45 | E2 | 10 | 63 |
| HPV45 | E2 | 11 | 43 |
| HPV45 | E2 | 8 | 13 |
| HPV45 | E2 | 8 | 302 |
| HPV45 | E2 | 10 | 302 |
| HPV45 | E2 | 11 | 302 |
| HPV45 | E2 | 8 | 275 |
| HPV45 | E2 | 9 | 275 |
| HPV45 | E2 | 10 | 275 |
| HPV45 | E2 | 11 | 321 |
| HPV45 | E2 | 8 | 276 |
| HPV45 | E2 | 9 | 276 |
| HPV45 | E2 | 10 | 322 |
| HPV45 | E2 | 9 | 51 |
| HPV45 | E2 | 8 | 233 |
| HPV45 | E2 | 8 | 277 |
| HPV45 | E2 | 8 | 290 |
| HPV45 | E2 | 11 | 290 |
| HPV45 | E2 | 8 | 172 |
| HPV45 | E2 | 10 | 122 |
| HPV45 | E2 | 9 | 213 |
| HPV45 | E2 | 10 | 337 |
| HPV45 | E2 | 8 | 214 |

TABLE IX-continued

HLA-A3 Supermotif Peptides

| 1 | 2 | 3 | 4 |
|---|---|---|---|
| HPV45 | E2 | 10 | 159 |
| HPV45 | E2 | 9 | 338 |
| HPV45 | E2 | 9 | 64 |
| HPV45 | E2 | 11 | 64 |
| HPV45 | E2 | 10 | 145 |
| HPV45 | E2 | 10 | 175 |
| HPV45 | E6 | 9 | 59 |
| HPV45 | E6 | 9 | 68 |
| HPV45 | E6 | 10 | 32 |
| HPV45 | E6 | 10 | 27 |
| HPV45 | E6 | 8 | 97 |
| HPV45 | E6 | 11 | 97 |
| HPV45 | E6 | 8 | 43 |
| HPV45 | E6 | 11 | 47 |
| HPV45 | E6 | 8 | 128 |
| HPV45 | E6 | 8 | 50 |
| HPV45 | E6 | 9 | 102 |
| HPV45 | E6 | 10 | 101 |
| HPV45 | E6 | 10 | 1 |
| HPV45 | E6 | 8 | 100 |
| HPV45 | E6 | 11 | 100 |
| HPV45 | E6 | 10 | 83 |
| HPV45 | E6 | 8 | 139 |
| HPV45 | E6 | 11 | 139 |
| HPV45 | E6 | 10 | 95 |
| HPV45 | E6 | 9 | 114 |
| HPV45 | E6 | 11 | 114 |
| HPV45 | E6 | 8 | 111 |
| HPV45 | E6 | 9 | 111 |
| HPV45 | E6 | 8 | 144 |
| HPV45 | E6 | 9 | 144 |
| HPV45 | E6 | 10 | 144 |
| HPV45 | E6 | 11 | 144 |
| HPV45 | E6 | 10 | 41 |
| HPV45 | E6 | 8 | 29 |
| HPV45 | E6 | 9 | 84 |
| HPV45 | E6 | 9 | 28 |
| HPV45 | E6 | 8 | 72 |
| HPV45 | E7 | 9 | 64 |
| HPV45 | E7 | 8 | 78 |
| HPV45 | E7 | 10 | 44 |
| HPV45 | E7 | 11 | 44 |
| HPV45 | E7 | 8 | 47 |
| HPV45 | E7 | 11 | 62 |
| HPV45 | E7 | 8 | 61 |
| HPV45 | E7 | 11 | 75 |
| HPV45 | E7 | 9 | 51 |
| HPV45 | E7 | 11 | 51 |
| HPV45 | E7 | 11 | 49 |
| HPV45 | E7 | 8 | 54 |
| HPV45 | E7 | 10 | 76 |
| HPV45 | E7 | 9 | 45 |
| HPV45 | E7 | 10 | 45 |
| HPV45 | L1 | 9 | 517 |
| HPV45 | L1 | 11 | 161 |
| HPV45 | L1 | 8 | 191 |
| HPV45 | L1 | 11 | 234 |
| HPV45 | L1 | 9 | 523 |
| HPV45 | L1 | 11 | 523 |
| HPV45 | L1 | 8 | 518 |
| HPV45 | L1 | 11 | 518 |
| HPV45 | L1 | 10 | 162 |
| HPV45 | L1 | 8 | 164 |
| HPV45 | L1 | 11 | 88 |
| HPV45 | L1 | 10 | 276 |
| HPV45 | L1 | 8 | 129 |
| HPV45 | L1 | 11 | 188 |
| HPV45 | L1 | 8 | 250 |
| HPV45 | L1 | 9 | 488 |
| HPV45 | L1 | 10 | 488 |
| HPV45 | L1 | 8 | 271 |
| HPV45 | L1 | 9 | 271 |
| HPV45 | L1 | 11 | 114 |
| HPV45 | L1 | 10 | 296 |
| HPV45 | L1 | 11 | 169 |
| HPV45 | L1 | 8 | 283 |
| HPV45 | L1 | 8 | 24 |
| HPV45 | L1 | 8 | 498 |
| HPV45 | L1 | 9 | 498 |
| HPV45 | L1 | 10 | 498 |
| HPV45 | L1 | 8 | 237 |
| HPV45 | L1 | 11 | 450 |
| HPV45 | L1 | 9 | 359 |
| HPV45 | L1 | 10 | 82 |
| HPV45 | L1 | 11 | 503 |
| HPV45 | L1 | 10 | 143 |
| HPV45 | L1 | 11 | 328 |
| HPV45 | L1 | 10 | 473 |
| HPV45 | L1 | 8 | 91 |
| HPV45 | L1 | 11 | 91 |
| HPV45 | L1 | 10 | 68 |
| HPV45 | L1 | 9 | 144 |
| HPV45 | L1 | 9 | 69 |
| HPV45 | L1 | 8 | 499 |
| HPV45 | L1 | 9 | 499 |
| HPV45 | L1 | 8 | 49 |
| HPV45 | L1 | 9 | 383 |
| HPV45 | L1 | 10 | 516 |
| HPV45 | L1 | 9 | 190 |
| HPV45 | L1 | 8 | 526 |
| HPV45 | L1 | 10 | 526 |
| HPV45 | L1 | 11 | 526 |
| HPV45 | L1 | 10 | 22 |
| HPV45 | L1 | 10 | 248 |
| HPV45 | L1 | 8 | 508 |
| HPV45 | L1 | 9 | 387 |
| HPV45 | L1 | 10 | 440 |
| HPV45 | L1 | 10 | 380 |
| HPV45 | L1 | 10 | 281 |
| HPV45 | L1 | 11 | 334 |
| HPV45 | L1 | 11 | 357 |
| HPV45 | L1 | 9 | 452 |
| HPV45 | L1 | 11 | 67 |
| HPV45 | L1 | 9 | 101 |
| HPV45 | L1 | 8 | 529 |
| HPV45 | L1 | 11 | 46 |
| HPV45 | L1 | 10 | 77 |
| HPV45 | L1 | 9 | 93 |
| HPV45 | L1 | 10 | 58 |
| HPV45 | L1 | 8 | 272 |
| HPV45 | L1 | 11 | 486 |
| HPV45 | L1 | 8 | 521 |
| HPV45 | L1 | 9 | 521 |
| HPV45 | L1 | 11 | 521 |
| HPV45 | L1 | 10 | 115 |
| HPV45 | L1 | 10 | 519 |
| HPV45 | L1 | 11 | 519 |
| HPV45 | L1 | 8 | 453 |
| HPV45 | L1 | 8 | 522 |
| HPV45 | L1 | 10 | 522 |
| HPV45 | L1 | 9 | 163 |
| HPV45 | L1 | 9 | 116 |
| HPV45 | L1 | 9 | 330 |
| HPV45 | L1 | 11 | 57 |
| HPV45 | L1 | 8 | 442 |
| HPV45 | L1 | 9 | 520 |
| HPV45 | L1 | 10 | 520 |
| HPV45 | L1 | 10 | 329 |
| HPV45 | L1 | 9 | 441 |
| HPV45 | L1 | 8 | 70 |
| HPV45 | L1 | 9 | 297 |
| HPV45 | L1 | 11 | 36 |
| HPV45 | L1 | 8 | 102 |
| HPV45 | L1 | 10 | 92 |
| HPV45 | L1 | 8 | 360 |
| HPV45 | L1 | 10 | 47 |
| HPV45 | L1 | 9 | 78 |
| HPV45 | L1 | 10 | 127 |
| HPV45 | L1 | 8 | 196 |
| HPV45 | L1 | 8 | 477 |

TABLE IX-continued

HLA-A3 Supermotif Peptides

| 1 | 2 | 3 | 4 |
|---|---|---|---|
| HPV45 | L1 | 10 | 303 |
| HPV45 | L1 | 9 | 38 |
| HPV45 | L2 | 10 | 286 |
| HPV45 | L2 | 8 | 12 |
| HPV45 | L2 | 11 | 12 |
| HPV45 | L2 | 10 | 357 |
| HPV45 | L2 | 9 | 14 |
| HPV45 | L2 | 9 | 303 |
| HPV45 | L2 | 9 | 273 |
| HPV45 | L2 | 9 | 276 |
| HPV45 | L2 | 11 | 306 |
| HPV45 | L2 | 11 | 58 |
| HPV45 | L2 | 10 | 25 |
| HPV45 | L2 | 9 | 60 |
| HPV45 | L2 | 11 | 292 |
| HPV45 | L2 | 10 | 210 |
| HPV45 | L2 | 11 | 210 |
| HPV45 | L2 | 10 | 34 |
| HPV45 | L2 | 9 | 287 |
| HPV45 | L2 | 8 | 1 |
| HPV45 | L2 | 9 | 1 |
| HPV45 | L2 | 10 | 1 |
| HPV45 | L2 | 11 | 1 |
| HPV45 | L2 | 10 | 79 |
| HPV45 | L2 | 11 | 285 |
| HPV45 | L2 | 11 | 356 |
| HPV45 | L2 | 11 | 209 |
| HPV45 | L2 | 9 | 214 |
| HPV45 | L2 | 10 | 216 |
| HPV45 | L2 | 9 | 11 |
| HPV45 | L2 | 10 | 302 |
| HPV45 | L2 | 11 | 298 |
| HPV45 | L2 | 10 | 281 |
| HFV45 | L2 | 11 | 281 |
| HPV45 | L2 | 11 | 225 |
| HPV45 | L2 | 9 | 308 |
| HPV45 | L2 | 10 | 68 |
| HPV45 | L2 | 10 | 220 |
| HPV45 | L2 | 10 | 13 |
| HPV45 | L2 | 8 | 288 |
| HPV45 | L2 | 11 | 288 |
| HPV45 | L2 | 9 | 211 |
| HPV45 | L2 | 10 | 211 |
| HPV45 | L2 | 11 | 362 |
| HPV45 | L2 | 8 | 212 |
| HPV45 | L2 | 9 | 212 |
| HPV45 | L2 | 11 | 212 |
| HPV45 | L2 | 9 | 358 |
| HPV45 | L2 | 10 | 363 |
| HPV45 | L2 | 8 | 304 |
| HPV45 | L2 | 8 | 359 |
| HPV45 | L2 | 10 | 293 |
| HPV45 | L2 | 9 | 217 |
| HPV45 | L2 | 9 | 80 |
| HPV45 | L2 | 8 | 2 |
| HPV45 | L2 | 9 | 2 |
| HPV45 | L2 | 10 | 2 |
| HPV45 | L2 | 8 | 81 |
| HPV45 | L2 | 11 | 437 |
| HPV45 | L2 | 9 | 227 |
| HPV56 | E2 | 9 | 177 |
| HPV56 | E2 | 10 | 177 |
| HPV56 | E2 | 8 | 178 |
| HPV56 | E2 | 9 | 178 |
| HPV56 | E2 | 11 | 178 |
| HPV56 | E2 | 8 | 4 |
| HPV56 | E2 | 8 | 71 |
| HPV56 | E2 | 10 | 176 |
| HPV56 | E2 | 11 | 176 |
| HPV56 | E2 | 9 | 195 |
| HPV56 | E2 | 8 | 140 |
| HPV56 | E2 | 8 | 213 |
| HPV56 | E2 | 10 | 213 |
| HPV56 | E2 | 8 | 117 |
| HPV56 | E2 | 8 | 43 |
| HPV56 | E2 | 9 | 43 |
| HPV56 | E2 | 8 | 191 |
| HPV56 | E2 | 10 | 154 |
| HPV56 | E2 | 8 | 61 |
| HPV56 | E2 | 10 | 99 |
| HPV56 | E2 | 10 | 59 |
| HPV56 | E2 | 11 | 210 |
| HPV56 | E2 | 8 | 239 |
| HPV56 | E2 | 10 | 239 |
| HPV56 | E2 | 9 | 297 |
| HPV56 | E2 | 9 | 283 |
| HPV56 | E2 | 10 | 211 |
| HPV56 | E2 | 11 | 281 |
| HPV56 | E2 | 9 | 233 |
| HPV56 | E2 | 9 | 90 |
| HPV56 | E2 | 11 | 295 |
| HPV56 | E2 | 9 | 46 |
| HPV56 | E2 | 10 | 46 |
| HPV56 | E2 | 9 | 1 |
| HPV56 | E2 | 11 | 1 |
| HPV56 | E2 | 8 | 292 |
| HPV56 | E2 | 11 | 236 |
| HPV56 | E2 | 10 | 301 |
| HPV56 | E2 | 8 | 246 |
| HPV56 | E2 | 11 | 246 |
| HPV56 | E2 | 11 | 188 |
| HPV56 | E2 | 8 | 279 |
| HPV56 | E2 | 11 | 223 |
| HPV56 | E2 | 8 | 196 |
| HPV56 | E2 | 11 | 266 |
| HPV56 | E2 | 10 | 282 |
| HPV56 | E2 | 11 | 28 |
| HPV56 | E2 | 8 | 234 |
| HPV56 | E2 | 9 | 155 |
| HPV56 | E2 | 8 | 179 |
| HPV56 | E2 | 10 | 179 |
| HPV56 | E2 | 10 | 237 |
| HPV56 | E2 | 9 | 302 |
| HPV56 | E2 | 10 | 45 |
| HPV56 | E2 | 11 | 45 |
| HPV56 | E2 | 9 | 278 |
| HPV56 | E2 | 9 | 111 |
| HPV56 | E2 | 10 | 111 |
| HPV56 | E6 | 8 | 89 |
| HPV56 | E6 | 9 | 89 |
| HPV56 | E6 | 10 | 139 |
| HPV56 | E6 | 9 | 69 |
| HPV56 | E6 | 10 | 69 |
| HPV56 | E6 | 9 | 50 |
| HPV56 | E6 | 10 | 33 |
| HPV56 | E6 | 8 | 101 |
| HPV56 | E6 | 10 | 28 |
| HPV56 | E6 | 11 | 28 |
| HPV56 | E6 | 8 | 23 |
| HPV56 | E6 | 11 | 20 |
| HPV56 | E6 | 11 | 44 |
| HPV56 | E6 | 11 | 48 |
| HPV56 | E6 | 9 | 88 |
| HPV56 | E6 | 10 | 88 |
| HPV56 | E6 | 8 | 137 |
| HPV56 | E6 | 8 | 70 |
| HPV56 | E6 | 9 | 70 |
| HPV56 | E6 | 11 | 70 |
| HPV56 | E6 | 8 | 31 |
| HPV56 | E6 | 8 | 98 |
| HPV56 | E6 | 11 | 98 |
| HPV56 | E6 | 8 | 119 |
| HPV56 | E6 | 9 | 119 |
| HPV56 | E6 | 9 | 110 |
| HPV56 | E6 | 8 | 30 |
| HPV56 | E6 | 9 | 30 |
| HPV56 | E6 | 9 | 67 |
| HPV56 | E6 | 11 | 67 |
| HPV56 | E6 | 8 | 90 |
| HPV56 | E6 | 10 | 21 |

TABLE IX-continued

HLA-A3 Supermotif Peptides

| 1 | 2 | 3 | 4 |
|---|---|---|---|
| HPV56 | E6 | 10 | 135 |
| HPV56 | E6 | 8 | 73 |
| HPV56 | E7 | 10 | 75 |
| HPV56 | E7 | 8 | 39 |
| HPV56 | E7 | 11 | 70 |
| HPV56 | E7 | 10 | 42 |
| HPV56 | E7 | 8 | 62 |
| HPV56 | E7 | 10 | 60 |
| HPV56 | E7 | 8 | 73 |
| HPV56 | E7 | 8 | 77 |
| HPV56 | E7 | 10 | 71 |
| HPV56 | E7 | 11 | 59 |
| HPV56 | L1 | 11 | 241 |
| HPV56 | L1 | 8 | 198 |
| HPV56 | L1 | 8 | 58 |
| HPV56 | L1 | 11 | 381 |
| HPV56 | L1 | 9 | 444 |
| HPV56 | L1 | 9 | 37 |
| HPV56 | L1 | 8 | 512 |
| HPV56 | L1 | 11 | 79 |
| HPV56 | L1 | 11 | 195 |
| HPV56 | L1 | 8 | 136 |
| HPV56 | L1 | 10 | 389 |
| HPV56 | L1 | 8 | 257 |
| HPV56 | L1 | 9 | 491 |
| HPV56 | L1 | 10 | 491 |
| HPV56 | L1 | 8 | 278 |
| HPV56 | L1 | 9 | 278 |
| HPV56 | L1 | 11 | 176 |
| HPV56 | L1 | 10 | 236 |
| HPV56 | L1 | 11 | 121 |
| HPV56 | L1 | 10 | 404 |
| HPV56 | L1 | 10 | 308 |
| HPV56 | L1 | 10 | 303 |
| HPV56 | L1 | 8 | 290 |
| HPV56 | L1 | 11 | 290 |
| HPV56 | L1 | 8 | 501 |
| HPV56 | L1 | 10 | 501 |
| HPV56 | L1 | 8 | 33 |
| HPV56 | L1 | 9 | 364 |
| HPV56 | L1 | 10 | 150 |
| HPV56 | L1 | 10 | 378 |
| HPV56 | L1 | 10 | 334 |
| HPV56 | L1 | 8 | 98 |
| HPV56 | L1 | 11 | 98 |
| HPV56 | L1 | 10 | 55 |
| HPV56 | L1 | 11 | 55 |
| HPV56 | L1 | 11 | 45 |
| HPV56 | L1 | 11 | 168 |
| HPV56 | L1 | 9 | 502 |
| HPV56 | L1 | 9 | 151 |
| HPV56 | L1 | 8 | 385 |
| HPV56 | L1 | 10 | 36 |
| HPV56 | L1 | 11 | 333 |
| HPV56 | L1 | 9 | 2 |
| HPV56 | L1 | 10 | 1 |
| HPV56 | L1 | 11 | 95 |
| HPV56 | L1 | 9 | 123 |
| HPV56 | L1 | 8 | 91 |
| HPV56 | L1 | 9 | 197 |
| HPV56 | L1 | 8 | 511 |
| HPV56 | L1 | 9 | 511 |
| HPV56 | L1 | 10 | 31 |
| HPV56 | L1 | 10 | 255 |
| HPV56 | L1 | 10 | 467 |
| HPV56 | L1 | 9 | 522 |
| HPV56 | L1 | 10 | 522 |
| HPV56 | L1 | 11 | 522 |
| HPV56 | L1 | 9 | 442 |
| HPV56 | L1 | 11 | 442 |
| HPV56 | L1 | 10 | 288 |
| HPV56 | L1 | 11 | 339 |
| HPV56 | L1 | 11 | 362 |
| HPV56 | L1 | 8 | 384 |
| HPV56 | L1 | 9 | 384 |
| HPV56 | L1 | 11 | 35 |
| HPV56 | L1 | 11 | 260 |
| HPV56 | L1 | 10 | 508 |
| HPV56 | L1 | 11 | 508 |
| HPV56 | L1 | 9 | 455 |
| HPV56 | L1 | 9 | 108 |
| HPV56 | L1 | 11 | 520 |
| HPV56 | L1 | 9 | 100 |
| HPV56 | L1 | 11 | 100 |
| HPV56 | L1 | 10 | 67 |
| HPV56 | L1 | 10 | 446 |
| HPV56 | L1 | 8 | 279 |
| HPV56 | L1 | 8 | 456 |
| HPV56 | L1 | 9 | 379 |
| HPV56 | L1 | 10 | 261 |
| HPV56 | L1 | 11 | 489 |
| HPV56 | L1 | 8 | 526 |
| HPV56 | L1 | 9 | 526 |
| HPV56 | L1 | 8 | 524 |
| HPV56 | L1 | 9 | 524 |
| HPV56 | L1 | 10 | 524 |
| HPV56 | L1 | 11 | 524 |
| HPV56 | L1 | 8 | 86 |
| HPV56 | L1 | 8 | 380 |
| HPV56 | L1 | 9 | 304 |
| HPV56 | L1 | 11 | 377 |
| HPV56 | L1 | 9 | 335 |
| HPV56 | L1 | 11 | 66 |
| HPV56 | L1 | 8 | 445 |
| HPV56 | L1 | 11 | 445 |
| HPV56 | L1 | 8 | 525 |
| HPV56 | L1 | 9 | 525 |
| HPV56 | L1 | 10 | 525 |
| HPV56 | L1 | 8 | 523 |
| HPV56 | L1 | 9 | 523 |
| HPV56 | L1 | 10 | 523 |
| HPV56 | L1 | 11 | 523 |
| HPV56 | L1 | 8 | 57 |
| HPV56 | L1 | 9 | 57 |
| HPV56 | L1 | 8 | 443 |
| HPV56 | L1 | 10 | 443 |
| HPV56 | L1 | 10 | 99 |
| HPV56 | L1 | 8 | 365 |
| HPV56 | L1 | 9 | 56 |
| HPV56 | L1 | 10 | 56 |
| HPV56 | L1 | 10 | 134 |
| HPV56 | L1 | 8 | 203 |
| HPV56 | L1 | 8 | 310 |
| HPV56 | L1 | 9 | 47 |
| HPV56 | L1 | 10 | 283 |
| HPV56 | L1 | 9 | 85 |
| HPV56 | L1 | 11 | 453 |
| HPV56 | L2 | 8 | 222 |
| HPV56 | L2 | 10 | 281 |
| HPV56 | L2 | 11 | 281 |
| HPV56 | L2 | 9 | 438 |
| HPV56 | L2 | 10 | 438 |
| HPV56 | L2 | 11 | 438 |
| HPV56 | L2 | 8 | 12 |
| HPV56 | L2 | 11 | 12 |
| HPV56 | L2 | 10 | 367 |
| HPV56 | L2 | 9 | 14 |
| HPV56 | L2 | 9 | 30 |
| HPV56 | L2 | 10 | 437 |
| HPV56 | L2 | 11 | 437 |
| HPV56 | L2 | 9 | 276 |
| HPV56 | L2 | 9 | 287 |
| HPV56 | L2 | 11 | 58 |
| HPV56 | L2 | 10 | 25 |
| HPV56 | L2 | 9 | 60 |
| HPV56 | L2 | 9 | 293 |
| HPV56 | L2 | 10 | 293 |
| HPV56 | L2 | 8 | 221 |
| HPV56 | L2 | 9 | 221 |
| HPV56 | L2 | 10 | 210 |

TABLE IX-continued

HLA-A3 Supermotif Peptides

| 1 | 2 | 3 | 4 |
|---|---|---|---|
| HPV56 | L2 | 11 | 210 |
| HPV56 | L2 | 8 | 81 |
| HPV56 | L2 | 8 | 302 |
| HPV56 | L2 | 10 | 34 |
| HPV56 | L2 | 10 | 235 |
| HPV56 | L2 | 8 | 1 |
| HPV56 | L2 | 9 | 1 |
| HPV56 | L2 | 10 | 1 |
| HPV56 | L2 | 11 | 1 |
| HPV56 | L2 | 11 | 285 |
| HPV56 | L2 | 11 | 209 |
| HPV56 | L2 | 8 | 369 |
| HPV56 | L2 | 11 | 78 |
| HPV56 | L2 | 8 | 441 |
| HPV56 | L2 | 9 | 441 |
| HPV56 | L2 | 10 | 441 |
| HPV56 | L2 | 11 | 441 |
| HPV56 | L2 | 11 | 306 |
| HPV56 | L2 | 10 | 68 |
| HPV56 | L2 | 9 | 11 |
| HPV56 | L2 | 9 | 220 |
| HPV56 | L2 | 10 | 220 |
| HPV56 | L2 | 11 | 298 |
| HPV56 | L2 | 11 | 225 |
| HPV56 | L2 | 10 | 13 |
| HPV56 | L2 | 9 | 211 |
| HPV56 | L2 | 10 | 211 |
| HPV56 | L2 | 10 | 79 |
| HPV56 | L2 | 8 | 212 |
| HPV56 | L2 | 9 | 212 |
| HPV56 | L2 | 9 | 80 |
| HPV56 | L2 | 8 | 288 |
| HPV56 | L2 | 11 | 288 |
| HPV56 | L2 | 8 | 2 |
| HPV56 | L2 | 9 | 2 |
| HPV56 | L2 | 10 | 2 |
| HPV56 | L2 | 11 | 280 |
| HPV56 | L2 | 11 | 366 |
| HPV56 | L2 | 9 | 236 |
| HPV56 | L2 | 8 | 31 |

TABLE IXA

HPV 6A
HLA-A3 Supermotif Peptides

| 2 | 3 | 4 |
|---|---|---|
| L1 | 8 | 234 |
| E1 | 8 | 206 |
| L1 | 9 | 489 |
| L1 | 11 | 489 |
| L2 | 10 | 286 |
| E1 | 9 | 112 |
| E1 | 10 | 112 |
| L1 | 11 | 420 |
| E1 | 10 | 475 |
| L1 | 11 | 203 |
| L1 | 8 | 487 |
| L1 | 9 | 487 |
| L1 | 11 | 487 |
| L2 | 11 | 12 |
| E2 | 8 | 322 |
| L2 | 8 | 288 |
| L2 | 11 | 288 |
| L1 | 8 | 22 |
| E1 | 8 | 407 |
| L2 | 9 | 14 |
| E6 | 9 | 10 |
| E6 | 9 | 86 |
| E1 | 8 | 77 |
| E1 | 9 | 77 |

TABLE IXA-continued

HPV 6A
HLA-A3 Supermotif Peptides

| 2 | 3 | 4 |
|---|---|---|
| E1 | 9 | 101 |
| L1 | 10 | 43 |
| L1 | 11 | 43 |
| E2 | 8 | 231 |
| E2 | 9 | 231 |
| E2 | 11 | 231 |
| L1 | 10 | 483 |
| L1 | 11 | 483 |
| E1 | 11 | 601 |
| E6 | 10 | 64 |
| L1 | 11 | 157 |
| E1 | 9 | 406 |
| E2 | 8 | 296 |
| E2 | 11 | 35 |
| L1 | 8 | 99 |
| E1 | 8 | 640 |
| E1 | 10 | 111 |
| E1 | 11 | 111 |
| E2 | 8 | 230 |
| E2 | 9 | 230 |
| E2 | 10 | 230 |
| L1 | 8 | 219 |
| E6 | 8 | 96 |
| E1 | 9 | 570 |
| E7 | 10 | 88 |
| E1 | 10 | 222 |
| E2 | 10 | 25 |
| E1 | 9 | 203 |
| E1 | 11 | 203 |
| L1 | 11 | 84 |
| E1 | 11 | 73 |
| L1 | 11 | 269 |
| E6 | 11 | 99 |
| E1 | 10 | 178 |
| E2 | 9 | 174 |
| L2 | 8 | 274 |
| L2 | 11 | 274 |
| E1 | 10 | 143 |
| E1 | 8 | 336 |
| E1 | 8 | 180 |
| E1 | 8 | 62 |
| E1 | 10 | 100 |
| E1 | 9 | 375 |
| E1 | 10 | 105 |
| E6 | 8 | 42 |
| E6 | 11 | 42 |
| L1 | 9 | 453 |
| L1 | 10 | 453 |
| E1 | 9 | 197 |
| E1 | 8 | 604 |
| E2 | 11 | 74 |
| E1 | 8 | 417 |
| E2 | 8 | 100 |
| E2 | 9 | 100 |
| E1 | 11 | 373 |
| E2 | 9 | 293 |
| E2 | 11 | 293 |
| E2 | 9 | 39 |
| E7 | 11 | 39 |
| E6 | 11 | 113 |
| L1 | 8 | 206 |
| L1 | 8 | 252 |
| L2 | 8 | 442 |
| E1 | 9 | 220 |
| E6 | 9 | 126 |
| E6 | 11 | 126 |
| E1 | 9 | 454 |
| L1 | 8 | 463 |
| L1 | 10 | 463 |
| E4 | 11 | 21 |
| E1 | 9 | 393 |
| L1 | 10 | 245 |
| L2 | 9 | 276 |
| L1 | 8 | 49 |

TABLE IXA-continued

HPV 6A
HLA-A3 Supermotif Peptides

| 2 | 3 | 4 |
|---|---|---|
| E1 | 11 | 587 |
| L1 | 9 | 326 |
| L2 | 11 | 58 |
| E1 | 9 | 194 |
| E2 | 10 | 156 |
| E1 | 8 | 350 |
| E1 | 9 | 217 |
| L2 | 11 | 292 |
| E2 | 9 | 55 |
| E1 | 9 | 273 |
| E1 | 11 | 273 |
| L1 | 11 | 130 |
| E1 | 11 | 431 |
| L2 | 9 | 303 |
| E1 | 8 | 632 |
| E1 | 10 | 191 |
| L2 | 10 | 25 |
| L2 | 9 | 60 |
| E1 | 8 | 145 |
| L1 | 8 | 407 |
| E4 | 9 | 90 |
| E1 | 9 | 316 |
| L1 | 9 | 478 |
| L1 | 10 | 113 |
| E1 | 10 | 415 |
| E2 | 11 | 53 |
| E6 | 10 | 119 |
| E4 | 8 | 10 |
| E4 | 9 | 10 |
| E1 | 9 | 246 |
| L2 | 8 | 3 |
| L2 | 9 | 3 |
| E6 | 11 | 25 |
| L2 | 11 | 306 |
| L2 | 8 | 149 |
| E2 | 9 | 29 |
| E1 | 8 | 376 |
| E1 | 11 | 474 |
| L2 | 9 | 287 |
| L1 | 8 | 272 |
| E1 | 8 | 195 |
| E1 | 11 | 195 |
| E6 | 9 | 120 |
| E1 | 9 | 106 |
| E2 | 11 | 315 |
| L1 | 10 | 421 |
| E1 | 8 | 571 |
| E2 | 10 | 267 |
| E2 | 11 | 267 |
| L2 | 8 | 82 |
| E7 | 9 | 89 |
| E1 | 9 | 476 |
| L1 | 8 | 486 |
| L1 | 9 | 486 |
| L1 | 10 | 486 |
| E1 | 9 | 433 |
| E2 | 9 | 351 |
| E6 | 9 | 128 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 11 | 420 |
| E1 | 8 | 286 |
| E2 | 9 | 165 |
| E2 | 9 | 147 |
| E6 | 8 | 116 |
| E6 | 10 | 116 |
| E1 | 10 | 121 |
| E1 | 11 | 283 |
| L1 | 8 | 61 |
| L1 | 11 | 61 |
| L1 | 11 | 19 |
| L1 | 9 | 71 |
| L1 | 11 | 42 |
| L1 | 9 | 271 |
| E6 | 9 | 101 |
| E1 | 9 | 223 |
| E2 | 11 | 266 |
| E1 | 11 | 540 |
| E4 | 10 | 8 |
| E4 | 11 | 8 |
| E4 | 8 | 24 |
| E1 | 8 | 198 |
| L1 | 9 | 464 |
| E1 | 8 | 276 |
| E1 | 11 | 276 |
| E1 | 11 | 563 |
| E1 | 8 | 218 |
| E1 | 11 | 218 |
| L1 | 9 | 439 |
| L1 | 11 | 439 |
| E4 | 8 | 81 |
| E6 | 8 | 121 |
| E1 | 9 | 115 |
| E1 | 10 | 115 |
| E1 | 11 | 115 |
| E1 | 10 | 277 |
| E1 | 8 | 279 |
| E1 | 10 | 279 |
| L2 | 10 | 293 |
| L1 | 11 | 295 |
| E1 | 10 | 564 |
| E7 | 11 | 67 |
| L1 | 9 | 233 |
| L2 | 8 | 1 |
| L2 | 9 | 1 |
| L2 | 10 | 1 |
| L2 | 11 | 1 |
| E1 | 8 | 546 |
| E1 | 8 | 421 |
| E1 | 10 | 421 |
| E1 | 8 | 274 |
| E1 | 10 | 274 |
| E1 | 10 | 607 |
| E1 | 9 | 568 |
| E1 | 11 | 568 |
| E1 | 10 | 451 |
| L1 | 10 | 31 |
| E4 | 9 | 23 |
| L1 | 10 | 438 |
| E1 | 8 | 397 |
| L1 | 9 | 352 |
| E1 | 11 | 59 |
| E1 | 10 | 395 |
| L2 | 9 | 38 |
| E2 | 10 | 348 |
| L2 | 9 | 237 |
| L2 | 11 | 285 |
| L1 | 11 | 482 |
| L2 | 8 | 438 |
| L2 | 9 | 438 |
| L2 | 10 | 438 |
| L2 | 11 | 438 |
| L1 | 10 | 217 |
| E6 | 9 | 110 |
| E4 | 8 | 34 |
| E4 | 9 | 34 |
| L1 | 8 | 160 |
| L1 | 10 | 160 |
| E2 | 8 | 61 |
| E1 | 9 | 545 |
| L2 | 10 | 80 |
| L1 | 9 | 266 |
| L2 | 8 | 212 |
| L2 | 10 | 212 |

TABLE IXA-continued

HPV 6A
HLA-A3 Supermotif Peptides

| 2 | 3 | 4 |
|---|---|---|
| E4 | 9 | 38 |
| E4 | 10 | 38 |
| E4 | 11 | 38 |
| E6 | 8 | 28 |
| L1 | 11 | 301 |
| L1 | 11 | 324 |
| L1 | 10 | 232 |
| L1 | 10 | 250 |
| E2 | 9 | 76 |
| E1 | 8 | 305 |
| E1 | 11 | 314 |
| L1 | 11 | 466 |
| L1 | 9 | 417 |
| E2 | 9 | 103 |
| E2 | 10 | 103 |
| E2 | 11 | 103 |
| E2 | 9 | 233 |
| E1 | 9 | 205 |
| E1 | 11 | 391 |
| L1 | 9 | 53 |
| L2 | 11 | 298 |
| E1 | 9 | 109 |
| L1 | 8 | 241 |
| L2 | 10 | 281 |
| L2 | 11 | 281 |
| L2 | 9 | 308 |
| L1 | 9 | 472 |
| L1 | 10 | 472 |
| L1 | 11 | 476 |
| L1 | 9 | 140 |
| L1 | 8 | 488 |
| L1 | 10 | 488 |
| L2 | 10 | 13 |
| E6 | 10 | 9 |
| E1 | 9 | 422 |
| L1 | 8 | 474 |
| E1 | 8 | 247 |
| L2 | 9 | 81 |
| E1 | 10 | 60 |
| L1 | 9 | 86 |
| E4 | 9 | 80 |
| L2 | 8 | 304 |
| L1 | 9 | 297 |
| L1 | 11 | 451 |
| L1 | 8 | 473 |
| L1 | 9 | 473 |
| L1 | 10 | 85 |
| E4 | 10 | 79 |
| L2 | 11 | 209 |
| E2 | 10 | 316 |
| L1 | 10 | 347 |
| L2 | 10 | 210 |
| E2 | 9 | 317 |
| L1 | 9 | 348 |
| E2 | 8 | 40 |
| E6 | 10 | 40 |
| E1 | 9 | 192 |
| E1 | 11 | 192 |
| L2 | 8 | 39 |
| L1 | 10 | 270 |
| E6 | 10 | 26 |
| E6 | 11 | 8 |
| L2 | 10 | 147 |
| E1 | 8 | 566 |
| E1 | 11 | 566 |
| E4 | 11 | 78 |
| L1 | 11 | 346 |
| E2 | 11 | 97 |
| E6 | 11 | 39 |
| E6 | 8 | 11 |
| E6 | 8 | 87 |
| E4 | 8 | 91 |
| E1 | 8 | 78 |
| E2 | 10 | 334 |

TABLE IXA-continued

HPV 6A
HLA-A3 Supermotif Peptides

| 2 | 3 | 4 |
|---|---|---|
| E1 | 8 | 317 |
| L1 | 9 | 21 |
| E1 | 11 | 333 |
| E2 | 8 | 30 |
| E6 | 10 | 100 |
| E4 | 11 | 7 |
| E1 | 9 | 275 |
| E1 | 9 | 278 |
| E1 | 11 | 278 |
| L1 | 9 | 114 |
| L1 | 10 | 62 |
| L1 | 9 | 484 |
| L1 | 10 | 484 |
| L1 | 11 | 484 |
| L1 | 10 | 296 |
| L2 | 11 | 146 |
| E1 | 9 | 565 |
| E2 | 11 | 333 |
| L1 | 8 | 327 |
| E2 | 9 | 335 |
| L1 | 10 | 20 |
| E2 | 9 | 349 |
| E2 | 11 | 349 |
| L1 | 8 | 72 |
| L1 | 11 | 58 |
| E2 | 11 | 58 |
| E7 | 10 | 68 |
| L1 | 10 | 97 |
| E2 | 9 | 321 |
| E1 | 8 | 426 |
| E1 | 9 | 530 |
| E1 | 8 | 464 |
| E1 | 9 | 510 |
| E2 | 11 | 145 |
| E6 | 10 | 85 |
| E1 | 8 | 76 |
| E1 | 9 | 76 |
| E1 | 10 | 76 |
| E6 | 11 | 46 |
| L2 | 10 | 435 |
| L2 | 11 | 435 |
| E6 | 9 | 44 |
| L1 | 11 | 350 |
| E1 | 10 | 402 |
| E2 | 10 | 168 |
| L2 | 9 | 71 |
| L1 | 10 | 10 |
| E2 | 10 | 138 |
| L1 | 11 | 415 |

TABLE IXB

HPV6B
HLA-A3 Supermotif Peptides

| 2 | 3 | 4 |
|---|---|---|
| L1 | 8 | 234 |
| E1 | 8 | 206 |
| L1 | 9 | 489 |
| L1 | 11 | 489 |
| L2 | 10 | 286 |
| E1 | 9 | 112 |
| E1 | 10 | 112 |
| L1 | 11 | 420 |
| E1 | 10 | 475 |
| L1 | 11 | 203 |
| L1 | 8 | 487 |
| L1 | 9 | 487 |
| L1 | 11 | 487 |
| L2 | 11 | 12 |

TABLE IXB-continued

HPV6B
HLA-A3 Supermotif Peptides

| 2 | 3 | 4 |
|---|---|---|
| L2 | 8 | 288 |
| L2 | 11 | 288 |
| E2 | 8 | 322 |
| L1 | 8 | 22 |
| E1 | 8 | 407 |
| L2 | 9 | 14 |
| E6 | 9 | 10 |
| E6 | 9 | 86 |
| E1 | 8 | 77 |
| E1 | 9 | 77 |
| E1 | 9 | 101 |
| L1 | 10 | 43 |
| L1 | 11 | 43 |
| E5B | 9 | 36 |
| E5B | 11 | 36 |
| E2 | 8 | 231 |
| E2 | 9 | 231 |
| E2 | 11 | 231 |
| L1 | 10 | 483 |
| L1 | 11 | 483 |
| E1 | 11 | 601 |
| E6 | 10 | 64 |
| L1 | 11 | 157 |
| E1 | 9 | 406 |
| E2 | 8 | 296 |
| E2 | 11 | 35 |
| L1 | 8 | 99 |
| E1 | 8 | 640 |
| E1 | 10 | 111 |
| E1 | 11 | 111 |
| E2 | 8 | 230 |
| E2 | 9 | 230 |
| E2 | 10 | 230 |
| L1 | 8 | 219 |
| E6 | 8 | 96 |
| E1 | 9 | 570 |
| E2 | 10 | 25 |
| E1 | 10 | 222 |
| E1 | 9 | 203 |
| E1 | 11 | 203 |
| L1 | 11 | 84 |
| E1 | 11 | 73 |
| L1 | 11 | 269 |
| E6 | 11 | 99 |
| E1 | 10 | 178 |
| E2 | 9 | 174 |
| L2 | 8 | 274 |
| L2 | 11 | 274 |
| E1 | 10 | 143 |
| E1 | 8 | 336 |
| E1 | 8 | 180 |
| E1 | 8 | 62 |
| E1 | 10 | 100 |
| E1 | 9 | 375 |
| E1 | 10 | 105 |
| E6 | 8 | 42 |
| E6 | 11 | 42 |
| L1 | 9 | 453 |
| L1 | 10 | 453 |
| E1 | 9 | 197 |
| E1 | 8 | 604 |
| E2 | 11 | 74 |
| E1 | 8 | 417 |
| E2 | 8 | 100 |
| E2 | 9 | 100 |
| E1 | 11 | 373 |
| E2 | 9 | 293 |
| E2 | 11 | 293 |
| E2 | 9 | 39 |
| E7 | 11 | 39 |
| E6 | 11 | 113 |
| L1 | 8 | 206 |
| L1 | 8 | 252 |
| L2 | 8 | 442 |
| E1 | 9 | 220 |
| E6 | 9 | 126 |
| E6 | 11 | 126 |
| E1 | 9 | 454 |
| L1 | 8 | 463 |
| L1 | 10 | 463 |
| E4 | 11 | 31 |
| E1 | 9 | 393 |
| L1 | 10 | 245 |
| L2 | 9 | 276 |
| L1 | 8 | 49 |
| E1 | 11 | 587 |
| L1 | 9 | 326 |
| L2 | 11 | 58 |
| E1 | 9 | 194 |
| E2 | 10 | 156 |
| E1 | 8 | 350 |
| E5B | 8 | 28 |
| E1 | 9 | 217 |
| L2 | 11 | 292 |
| E5B | 11 | 25 |
| E2 | 9 | 55 |
| E1 | 9 | 273 |
| E1 | 11 | 273 |
| L1 | 11 | 130 |
| E1 | 11 | 431 |
| L2 | 9 | 303 |
| E1 | 8 | 632 |
| E1 | 10 | 191 |
| L2 | 10 | 25 |
| L2 | 9 | 60 |
| E1 | 8 | 145 |
| L1 | 8 | 407 |
| E4 | 9 | 100 |
| E1 | 9 | 316 |
| L1 | 9 | 478 |
| L1 | 10 | 113 |
| E1 | 10 | 415 |
| E2 | 11 | 53 |
| E6 | 10 | 119 |
| E4 | 8 | 20 |
| E4 | 9 | 20 |
| E1 | 9 | 246 |
| L2 | 8 | 3 |
| L2 | 9 | 3 |
| E5B | 9 | 42 |
| E6 | 11 | 25 |
| L2 | 11 | 306 |
| L2 | 8 | 149 |
| E2 | 9 | 29 |
| E1 | 8 | 376 |
| E1 | 11 | 474 |
| L2 | 9 | 287 |
| L1 | 8 | 272 |
| E1 | 8 | 195 |
| E1 | 11 | 195 |
| E6 | 9 | 120 |
| E1 | 9 | 106 |
| E2 | 11 | 315 |
| L1 | 10 | 421 |
| E1 | 8 | 571 |
| E2 | 10 | 267 |
| E2 | 11 | 267 |
| L2 | 8 | 82 |
| E7 | 9 | 89 |
| E1 | 9 | 476 |
| L1 | 8 | 486 |
| L1 | 9 | 486 |
| L1 | 10 | 486 |
| E1 | 9 | 433 |
| E2 | 9 | 351 |
| E6 | 9 | 128 |
| E1 | 8 | 114 |
| E1 | 10 | 114 |

TABLE IXB-continued

HPV6B
HLA-A3 Supermotif Peptides

| 2 | 3 | 4 |
|---|---|---|
| E1 | 11 | 114 |
| E1 | 9 | 462 |
| E1 | 10 | 462 |
| E1 | 9 | 420 |
| E1 | 11 | 420 |
| E1 | 8 | 286 |
| E2 | 9 | 165 |
| E2 | 9 | 147 |
| E6 | 8 | 116 |
| E6 | 10 | 116 |
| E1 | 10 | 121 |
| E1 | 11 | 283 |
| L1 | 8 | 61 |
| L1 | 11 | 61 |
| L1 | 11 | 19 |
| L1 | 9 | 71 |
| L1 | 11 | 42 |
| L1 | 9 | 271 |
| E6 | 9 | 101 |
| E1 | 9 | 223 |
| E2 | 11 | 266 |
| E1 | 11 | 540 |
| E4 | 10 | 18 |
| E4 | 11 | 18 |
| E4 | 8 | 34 |
| E1 | 8 | 198 |
| L1 | 9 | 464 |
| E1 | 8 | 279 |
| E1 | 10 | 279 |
| E1 | 8 | 276 |
| E1 | 11 | 276 |
| E1 | 11 | 563 |
| E5B | 11 | 31 |
| E1 | 8 | 218 |
| E1 | 11 | 218 |
| L1 | 9 | 439 |
| L1 | 11 | 439 |
| E4 | 8 | 91 |
| E6 | 8 | 121 |
| E1 | 9 | 115 |
| E1 | 10 | 115 |
| E1 | 11 | 115 |
| E1 | 10 | 277 |
| L2 | 10 | 293 |
| L1 | 11 | 295 |
| E1 | 10 | 564 |
| E7 | 11 | 67 |
| L1 | 9 | 233 |
| L2 | 8 | 1 |
| L2 | 9 | 1 |
| L2 | 10 | 1 |
| L2 | 11 | 1 |
| E5B | 10 | 26 |
| E1 | 8 | 546 |
| E1 | 8 | 421 |
| E1 | 10 | 421 |
| E1 | 8 | 274 |
| E1 | 10 | 274 |
| E1 | 9 | 568 |
| E1 | 11 | 568 |
| E1 | 10 | 451 |
| L1 | 10 | 31 |
| E7 | 10 | 88 |
| E4 | 9 | 33 |
| L1 | 10 | 438 |
| E1 | 8 | 397 |
| L1 | 9 | 352 |
| E1 | 11 | 59 |
| E1 | 10 | 395 |
| L2 | 9 | 38 |
| E1 | 10 | 607 |
| L2 | 9 | 237 |
| L2 | 11 | 285 |
| L1 | 11 | 482 |

TABLE IXB-continued

HPV6B
HLA-A3 Supermotif Peptides

| 2 | 3 | 4 |
|---|---|---|
| L2 | 8 | 438 |
| L2 | 9 | 438 |
| L2 | 10 | 438 |
| L2 | 11 | 438 |
| L1 | 10 | 217 |
| E6 | 9 | 110 |
| E4 | 8 | 44 |
| E4 | 9 | 44 |
| L1 | 8 | 160 |
| L1 | 10 | 160 |
| E2 | 8 | 61 |
| E1 | 9 | 545 |
| L2 | 10 | 80 |
| L1 | 9 | 266 |
| L2 | 8 | 212 |
| L2 | 10 | 212 |
| E4 | 9 | 48 |
| E4 | 10 | 48 |
| E4 | 11 | 48 |
| E6 | 8 | 28 |
| L1 | 11 | 301 |
| L1 | 11 | 324 |
| L1 | 10 | 232 |
| L1 | 10 | 250 |
| E2 | 9 | 76 |
| E1 | 8 | 305 |
| E1 | 11 | 314 |
| L1 | 11 | 466 |
| L1 | 9 | 417 |
| E2 | 9 | 103 |
| E2 | 10 | 103 |
| E2 | 11 | 103 |
| E2 | 9 | 233 |
| E2 | 11 | 218 |
| E1 | 9 | 205 |
| E1 | 11 | 391 |
| L1 | 9 | 53 |
| E5B | 10 | 35 |
| L2 | 11 | 298 |
| E1 | 9 | 109 |
| L1 | 8 | 241 |
| L2 | 10 | 281 |
| L2 | 11 | 281 |
| L2 | 9 | 308 |
| L1 | 9 | 472 |
| L1 | 10 | 472 |
| L1 | 11 | 475 |
| L1 | 9 | 140 |
| L1 | 8 | 488 |
| L1 | 10 | 488 |
| L2 | 10 | 13 |
| E6 | 10 | 9 |
| E1 | 9 | 422 |
| L1 | 8 | 474 |
| E1 | 8 | 247 |
| L2 | 9 | 81 |
| E1 | 10 | 60 |
| L1 | 9 | 86 |
| E4 | 9 | 90 |
| L2 | 8 | 304 |
| L1 | 9 | 297 |
| L1 | 11 | 451 |
| L1 | 8 | 473 |
| L1 | 9 | 473 |
| L1 | 10 | 85 |
| E4 | 10 | 89 |
| L2 | 11 | 209 |
| E2 | 10 | 316 |
| L1 | 10 | 347 |
| E2 | 9 | 220 |
| L2 | 10 | 210 |
| E2 | 9 | 317 |
| L1 | 9 | 348 |
| E2 | 8 | 40 |

TABLE IXB-continued

HPV6B
HLA-A3 Supermotif Peptides

| 2 | 3 | 4 |
|---|---|---|
| E6 | 10 | 40 |
| E1 | 9 | 192 |
| E1 | 11 | 192 |
| L2 | 8 | 39 |
| L1 | 10 | 270 |
| E6 | 10 | 26 |
| E2 | 8 | 221 |
| E6 | 11 | 8 |
| L2 | 10 | 147 |
| E1 | 8 | 566 |
| E1 | 11 | 566 |
| E4 | 11 | 88 |
| L1 | 11 | 346 |
| E2 | 10 | 219 |
| E2 | 11 | 97 |
| E6 | 11 | 39 |
| E6 | 8 | 11 |
| E6 | 8 | 87 |
| E4 | 8 | 101 |
| E1 | 8 | 78 |
| E2 | 10 | 334 |
| E1 | 8 | 317 |
| L1 | 9 | 21 |
| E1 | 11 | 333 |
| E2 | 8 | 30 |
| E6 | 10 | 100 |
| E4 | 11 | 17 |
| E1 | 9 | 278 |
| E1 | 11 | 278 |
| E1 | 9 | 275 |
| L1 | 9 | 114 |
| L1 | 10 | 62 |
| L1 | 9 | 484 |
| L1 | 10 | 484 |
| L1 | 11 | 484 |
| L1 | 19 | 296 |
| L2 | 11 | 146 |
| E1 | 9 | 565 |
| E2 | 11 | 333 |
| L1 | 8 | 327 |
| E2 | 9 | 335 |
| L1 | 10 | 20 |
| E2 | 11 | 349 |
| L1 | 8 | 72 |
| L1 | 11 | 58 |
| E2 | 11 | 58 |
| E7 | 10 | 68 |
| L1 | 10 | 97 |
| E2 | 9 | 321 |
| E1 | 8 | 426 |
| E1 | 9 | 530 |
| E1 | 8 | 464 |
| E1 | 9 | 510 |
| E2 | 11 | 145 |
| E6 | 10 | 85 |
| E1 | 8 | 76 |
| E1 | 9 | 76 |
| E1 | 10 | 76 |
| E6 | 11 | 46 |
| L2 | 10 | 435 |
| L2 | 11 | 435 |
| E6 | 9 | 44 |
| L1 | 11 | 350 |
| E1 | 10 | 402 |
| E2 | 10 | 168 |
| L2 | 9 | 71 |
| L1 | 10 | 10 |
| E2 | 10 | 138 |
| L1 | 11 | 415 |

TABLE IXC

HPV11
HLA-A3 Supermotif Peptides

| 2 | 3 | 4 |
|---|---|---|
| L1 | 8 | 235 |
| E1 | 9 | 112 |
| E1 | 10 | 112 |
| E1 | 8 | 407 |
| L1 | 11 | 421 |
| L2 | 9 | 80 |
| L2 | 10 | 285 |
| E1 | 10 | 475 |
| L1 | 11 | 204 |
| L2 | 11 | 11 |
| E2 | 8 | 321 |
| E2 | 8 | 197 |
| L1 | 8 | 22 |
| L2 | 9 | 13 |
| E6 | 9 | 10 |
| E1 | 8 | 77 |
| E1 | 9 | 77 |
| L1 | 9 | 349 |
| E1 | 9 | 101 |
| L1 | 10 | 43 |
| L1 | 11 | 43 |
| E5 | 9 | 37 |
| E5 | 11 | 26 |
| L1 | 10 | 484 |
| L1 | 11 | 484 |
| E1 | 11 | 601 |
| E6 | 10 | 64 |
| E1 | 9 | 406 |
| E5 | 8 | 46 |
| L1 | 11 | 158 |
| E2 | 11 | 35 |
| E2 | 8 | 295 |
| E2 | 11 | 194 |
| L1 | 8 | 99 |
| E1 | 8 | 640 |
| E1 | 11 | 73 |
| E1 | 10 | 111 |
| E1 | 11 | 111 |
| E1 | 10 | 607 |
| L1 | 8 | 220 |
| E1 | 10 | 168 |
| E2 | 10 | 25 |
| E6 | 8 | 96 |
| E1 | 9 | 203 |
| E1 | 11 | 203 |
| E1 | 9 | 570 |
| E1 | 10 | 222 |
| L1 | 10 | 271 |
| L1 | 10 | 439 |
| E1 | 9 | 46 |
| E2 | 9 | 292 |
| E2 | 11 | 292 |
| E7 | 9 | 31 |
| L1 | 11 | 84 |
| E1 | 10 | 191 |
| E1 | 8 | 143 |
| E1 | 10 | 178 |
| L2 | 8 | 273 |
| L2 | 11 | 273 |
| E1 | 8 | 336 |
| E1 | 8 | 62 |
| E1 | 8 | 180 |
| E1 | 9 | 375 |
| E6 | 11 | 113 |
| E1 | 10 | 105 |
| E6 | 8 | 42 |
| E6 | 11 | 42 |
| L1 | 9 | 454 |
| L1 | 10 | 454 |
| E1 | 9 | 197 |
| E6 | 10 | 69 |
| E1 | 8 | 604 |
| E1 | 8 | 417 |
| E2 | 11 | 74 |

TABLE IXC-continued

HPV11
HLA-A3 Supermotif Peptides

| 2 | 3 | 4 |
|---|---|---|
| E2 | 8 | 100 |
| E2 | 9 | 100 |
| E1 | 11 | 373 |
| E2 | 9 | 39 |
| E6 | 8 | 92 |
| E1 | 10 | 141 |
| L1 | 8 | 207 |
| L1 | 8 | 253 |
| L2 | 8 | 438 |
| E6 | 9 | 126 |
| E6 | 11 | 126 |
| E1 | 9 | 454 |
| L1 | 8 | 464 |
| L1 | 10 | 464 |
| E1 | 9 | 393 |
| L2 | 9 | 275 |
| E1 | 11 | 587 |
| E1 | 9 | 220 |
| L1 | 9 | 327 |
| L2 | 11 | 57 |
| L1 | 9 | 479 |
| E1 | 9 | 194 |
| E2 | 10 | 156 |
| E5 | 8 | 29 |
| E1 | 9 | 217 |
| L2 | 11 | 291 |
| E1 | 9 | 273 |
| E1 | 11 | 273 |
| E1 | 8 | 632 |
| L2 | 10 | 24 |
| E5 | 9 | 40 |
| E5 | 11 | 40 |
| L2 | 9 | 59 |
| E1 | 11 | 431 |
| L1 | 8 | 408 |
| E4 | 9 | 99 |
| E1 | 9 | 316 |
| E2 | 8 | 232 |
| E2 | 9 | 232 |
| E2 | 11 | 232 |
| L1 | 10 | 113 |
| E1 | 10 | 415 |
| E6 | 10 | 119 |
| E2 | 9 | 29 |
| L1 | 11 | 325 |
| E4 | 9 | 20 |
| E1 | 8 | 305 |
| E1 | 9 | 246 |
| E1 | 9 | 349 |
| E6 | 11 | 25 |
| L2 | 10 | 36 |
| E1 | 8 | 376 |
| E1 | 11 | 474 |
| E1 | 8 | 195 |
| E1 | 11 | 195 |
| E6 | 9 | 120 |
| E2 | 8 | 30 |
| E1 | 8 | 571 |
| E1 | 9 | 106 |
| L1 | 10 | 422 |
| L2 | 8 | 81 |
| L2 | 9 | 286 |
| E7 | 9 | 89 |
| E1 | 9 | 476 |
| E2 | 8 | 265 |
| E2 | 11 | 265 |
| E2 | 9 | 350 |
| E6 | 8 | 116 |
| E6 | 10 | 116 |
| E1 | 11 | 460 |
| E6 | 9 | 128 |
| E1 | 8 | 114 |
| E1 | 10 | 114 |
| E1 | 11 | 114 |

TABLE IXC-continued

HPV11
HLA-A3 Supermotif Peptides

| 2 | 3 | 4 |
|---|---|---|
| E1 | 9 | 462 |
| E1 | 10 | 462 |
| E1 | 9 | 420 |
| E1 | 11 | 420 |
| L1 | 11 | 347 |
| E1 | 10 | 484 |
| E1 | 8 | 286 |
| E5 | 8 | 43 |
| E5 | 11 | 43 |
| E2 | 9 | 165 |
| E1 | 9 | 433 |
| E1 | 10 | 121 |
| E6 | 11 | 99 |
| E1 | 11 | 283 |
| L1 | 9 | 53 |
| L1 | 8 | 61 |
| L1 | 11 | 61 |
| E2 | 9 | 147 |
| L1 | 10 | 19 |
| L1 | 11 | 19 |
| L1 | 9 | 71 |
| L1 | 11 | 42 |
| E6 | 9 | 101 |
| E1 | 8 | 279 |
| E1 | 10 | 279 |
| E1 | 9 | 223 |
| E1 | 11 | 540 |
| E4 | 11 | 18 |
| E4 | 8 | 34 |
| E1 | 8 | 198 |
| E4 | 11 | 31 |
| L1 | 9 | 465 |
| L1 | 9 | 272 |
| E1 | 8 | 276 |
| E1 | 11 | 276 |
| E1 | 11 | 563 |
| E1 | 8 | 218 |
| E1 | 11 | 218 |
| E4 | 8 | 90 |
| E2 | 9 | 103 |
| E2 | 10 | 103 |
| E1 | 9 | 115 |
| E1 | 10 | 115 |
| E1 | 11 | 115 |
| E2 | 9 | 334 |
| L1 | 8 | 273 |
| E1 | 10 | 277 |
| L2 | 10 | 292 |
| L1 | 11 | 296 |
| E1 | 10 | 564 |
| E7 | 11 | 67 |
| L1 | 9 | 234 |
| L1 | 9 | 440 |
| L1 | 11 | 440 |
| E1 | 8 | 546 |
| E1 | 8 | 421 |
| E1 | 10 | 421 |
| L1 | 9 | 339 |
| E1 | 8 | 47 |
| E1 | 8 | 274 |
| E1 | 10 | 274 |
| E4 | 8 | 1 |
| E1 | 10 | 100 |
| E1 | 9 | 568 |
| E1 | 11 | 568 |
| E1 | 10 | 451 |
| L1 | 10 | 31 |
| E7 | 10 | 88 |
| E2 | 9 | 264 |
| E4 | 9 | 33 |
| E1 | 8 | 397 |
| L1 | 10 | 338 |
| L1 | 9 | 353 |
| E1 | 10 | 395 |

TABLE IXC-continued

HPV11
HLA-A3 Supermotif Peptides

| 2 | 3 | 4 |
|---|---|---|
| E1 | 11 | 59 |
| E2 | 10 | 347 |
| E2 | 9 | 248 |
| L2 | 9 | 236 |
| L2 | 10 | 79 |
| L2 | 11 | 284 |
| E4 | 9 | 49 |
| E4 | 10 | 49 |
| E4 | 11 | 49 |
| E2 | 9 | 196 |
| L1 | 11 | 483 |
| E6 | 9 | 110 |
| L1 | 10 | 218 |
| L1 | 8 | 161 |
| L2 | 8 | 211 |
| L2 | 10 | 211 |
| E4 | 9 | 44 |
| E4 | 10 | 44 |
| E2 | 8 | 61 |
| E1 | 9 | 545 |
| L1 | 8 | 488 |
| L1 | 9 | 488 |
| L1 | 11 | 488 |
| L2 | 9 | 206 |
| L2 | 8 | 434 |
| L2 | 9 | 434 |
| L2 | 10 | 434 |
| L2 | 11 | 434 |
| L1 | 9 | 267 |
| E6 | 8 | 28 |
| L1 | 11 | 302 |
| E2 | 10 | 288 |
| L1 | 10 | 233 |
| L1 | 10 | 251 |
| E2 | 9 | 76 |
| E1 | 11 | 314 |
| L1 | 11 | 467 |
| L1 | 9 | 418 |
| E1 | 11 | 391 |
| E5 | 8 | 36 |
| E5 | 10 | 36 |
| L2 | 11 | 297 |
| E2 | 9 | 37 |
| E2 | 11 | 37 |
| L1 | 8 | 242 |
| E4 | 9 | 59 |
| L2 | 10 | 280 |
| L2 | 11 | 280 |
| L2 | 9 | 307 |
| E1 | 9 | 205 |
| L1 | 11 | 477 |
| L1 | 9 | 473 |
| L1 | 10 | 473 |
| L1 | 9 | 141 |
| E2 | 9 | 234 |
| L1 | 8 | 475 |
| L2 | 10 | 12 |
| E6 | 10 | 9 |
| L1 | 10 | 348 |
| E1 | 8 | 247 |
| E1 | 9 | 422 |
| E1 | 8 | 350 |
| L1 | 9 | 86 |
| E4 | 9 | 89 |
| L1 | 9 | 298 |
| E7 | 8 | 32 |
| E7 | 11 | 32 |
| L1 | 11 | 452 |
| L1 | 10 | 85 |
| E4 | 10 | 88 |
| L2 | 11 | 208 |
| L1 | 8 | 489 |
| L1 | 10 | 489 |
| E1 | 8 | 206 |
| L2 | 10 | 209 |
| E1 | 10 | 60 |
| E2 | 9 | 348 |
| E2 | 11 | 348 |
| E2 | 8 | 40 |
| E6 | 10 | 40 |
| L1 | 9 | 490 |
| L1 | 11 | 490 |
| L2 | 8 | 38 |
| L1 | 8 | 340 |
| E2 | 8 | 249 |
| E6 | 10 | 26 |
| E2 | 10 | 333 |
| L1 | 8 | 474 |
| L1 | 9 | 474 |
| E6 | 11 | 8 |
| E1 | 9 | 192 |
| E1 | 11 | 192 |
| E6 | 8 | 11 |
| E1 | 8 | 566 |
| E1 | 11 | 566 |
| L2 | 8 | 287 |
| L2 | 11 | 287 |
| E4 | 11 | 87 |
| L2 | 8 | 207 |
| E2 | 11 | 97 |
| E6 | 11 | 39 |
| E2 | 11 | 228 |
| L2 | 9 | 37 |
| E1 | 8 | 116 |
| E1 | 9 | 116 |
| E1 | 10 | 116 |
| E4 | 8 | 100 |
| E1 | 8 | 78 |
| L1 | 8 | 21 |
| L1 | 9 | 21 |
| E1 | 11 | 333 |
| E5 | 10 | 27 |
| E6 | 10 | 100 |
| E1 | 9 | 278 |
| E1 | 11 | 278 |
| E1 | 9 | 275 |
| E2 | 8 | 233 |
| E2 | 10 | 233 |
| L1 | 9 | 114 |
| L1 | 10 | 62 |
| L1 | 9 | 485 |
| L1 | 10 | 485 |
| L1 | 11 | 485 |
| L1 | 10 | 297 |
| E2 | 10 | 266 |
| E2 | 11 | 266 |
| E2 | 11 | 332 |
| E1 | 9 | 565 |
| E2 | 8 | 148 |
| L1 | 8 | 328 |
| L1 | 9 | 20 |
| L1 | 10 | 20 |
| E7 | 10 | 68 |
| L1 | 8 | 72 |
| L1 | 11 | 58 |
| E2 | 11 | 58 |
| L1 | 10 | 97 |
| E2 | 9 | 320 |
| E1 | 8 | 426 |
| E1 | 8 | 464 |
| E1 | 9 | 510 |
| E2 | 10 | 102 |
| E2 | 11 | 102 |
| E1 | 9 | 530 |
| E2 | 11 | 145 |
| E1 | 8 | 76 |
| E1 | 9 | 76 |
| E1 | 10 | 76 |

TABLE IXC-continued

HPV11
HLA-A3 Supermotif Peptides

| 2 | 3 | 4 |
|---|---|---|
| E6 | 9 | 44 |
| E6 | 11 | 46 |
| L2 | 9 | 70 |
| L2 | 10 | 431 |
| L2 | 11 | 431 |
| E2 | 10 | 138 |
| L1 | 10 | 246 |
| L1 | 8 | 49 |
| L1 | 11 | 351 |
| L2 | 11 | 305 |
| E1 | 10 | 402 |
| E2 | 10 | 168 |
| L1 | 10 | 10 |
| L1 | 11 | 416 |

TABLE X

HLA A24 Supermotif Peptides

| 1 | 2 | 3 | 4 |
|---|---|---|---|
| HPV16 | E1 | 8 | 240 |
| HPV16 | E1 | 11 | 391 |
| HPV16 | E1 | 9 | 539 |
| HPV16 | E1 | 9 | 459 |
| HPV16 | E1 | 9 | 318 |
| HPV16 | E1 | 9 | 206 |
| HPV16 | E1 | 10 | 206 |
| HPV16 | E1 | 8 | 524 |
| HPV16 | E1 | 9 | 524 |
| HPV16 | E1 | 9 | 82 |
| HPV16 | E1 | 10 | 82 |
| HPV16 | E1 | 11 | 23 |
| HPV16 | E1 | 9 | 500 |
| HPV16 | E1 | 10 | 500 |
| HPV16 | E1 | 11 | 500 |
| HPV16 | E1 | 11 | 237 |
| HPV16 | E1 | 9 | 259 |
| HPV16 | E1 | 9 | 304 |
| HPV16 | E1 | 8 | 353 |
| HPV16 | E1 | 11 | 353 |
| HPV16 | E1 | 10 | 101 |
| HPV16 | E1 | 10 | 640 |
| HPV16 | E1 | 8 | 299 |
| HPV16 | E1 | 9 | 299 |
| HPV16 | E1 | 9 | 528 |
| HPV16 | E1 | 9 | 50 |
| HPV16 | E1 | 10 | 50 |
| HPV16 | E1 | 10 | 97 |
| HPV16 | E1 | 8 | 368 |
| HPV16 | E1 | 10 | 368 |
| HPV16 | E1 | 9 | 43 |
| HPV16 | E1 | 10 | 43 |
| HPV16 | E1 | 9 | 384 |
| HPV16 | E1 | 10 | 384 |
| HPV16 | E1 | 10 | 548 |
| HPV16 | E1 | 9 | 235 |
| HPV16 | E1 | 8 | 438 |
| HPV16 | E1 | 9 | 438 |
| HPV16 | E1 | 11 | 438 |
| HPV16 | E1 | 9 | 452 |
| HPV16 | E1 | 9 | 374 |
| HPV16 | E1 | 10 | 603 |
| HPV16 | E1 | 11 | 603 |
| HPV16 | E1 | 8 | 356 |
| HPV16 | E1 | 10 | 356 |
| HPV16 | E1 | 10 | 213 |
| HPV16 | E1 | 8 | 63 |
| HPV16 | E1 | 9 | 63 |
| HPV16 | E1 | 9 | 152 |
| HPV16 | E1 | 10 | 288 |

TABLE X-continued

HLA A24 Supermotif Peptides

| 1 | 2 | 3 | 4 |
|---|---|---|---|
| HPV16 | E1 | 11 | 288 |
| HPV16 | E1 | 8 | 138 |
| HPV16 | E1 | 9 | 331 |
| HPV16 | E1 | 10 | 331 |
| HPV16 | E1 | 9 | 338 |
| HPV16 | E1 | 9 | 612 |
| HPV16 | E1 | 11 | 612 |
| HPV16 | E1 | 8 | 51 |
| HPV16 | E1 | 9 | 51 |
| HPV16 | E1 | 10 | 392 |
| HPV16 | E1 | 11 | 463 |
| HPV16 | E1 | 9 | 493 |
| HPV16 | E1 | 9 | 445 |
| HPV16 | E1 | 10 | 445 |
| HPV16 | E1 | 8 | 456 |
| HPV16 | E1 | 9 | 456 |
| HPV16 | E1 | 8 | 453 |
| HPV16 | E1 | 11 | 453 |
| HPV16 | E1 | 9 | 586 |
| HPV16 | E1 | 8 | 501 |
| HPV16 | E1 | 9 | 501 |
| HPV16 | E1 | 10 | 501 |
| HPV16 | E1 | 11 | 508 |
| HPV16 | E1 | 8 | 466 |
| HPV16 | E1 | 9 | 466 |
| HPV16 | E1 | 10 | 466 |
| HPV16 | E1 | 11 | 466 |
| HPV16 | E1 | 9 | 325 |
| HPV16 | E1 | 10 | 242 |
| HPV16 | E1 | 11 | 519 |
| HPV16 | E1 | 8 | 487 |
| HPV16 | E1 | 10 | 272 |
| HPV16 | E1 | 8 | 571 |
| HPV16 | E1 | 9 | 571 |
| HPV16 | E1 | 8 | 12 |
| HPV16 | E1 | 9 | 12 |
| HPV16 | E1 | 8 | 450 |
| HPV16 | E1 | 11 | 450 |
| HPV16 | E1 | 8 | 179 |
| HPV16 | E1 | 11 | 216 |
| HPV16 | E1 | 9 | 263 |
| HPV16 | E1 | 11 | 263 |
| HPV16 | E1 | 8 | 184 |
| HPV16 | E1 | 11 | 184 |
| HPV16 | E1 | 10 | 411 |
| HPV16 | E1 | 9 | 369 |
| HPV16 | E1 | 11 | 369 |
| HPV16 | E1 | 8 | 401 |
| HPV16 | E1 | 8 | 52 |
| HPV16 | E1 | 10 | 210 |
| HPV16 | E1 | 8 | 492 |
| HPV16 | E1 | 10 | 492 |
| HPV16 | E1 | 9 | 400 |
| HPV16 | E1 | 8 | 296 |
| HPV16 | E1 | 10 | 296 |
| HPV16 | E1 | 11 | 296 |
| HPV16 | E1 | 9 | 311 |
| HPV16 | E1 | 10 | 311 |
| HPV16 | E1 | 11 | 311 |
| HPV16 | E1 | 11 | 323 |
| HPV16 | E1 | 9 | 252 |
| HPV16 | E1 | 10 | 252 |
| HPV16 | E1 | 11 | 252 |
| HPV16 | E1 | 9 | 199 |
| HPV16 | E1 | 10 | 199 |
| HPV16 | E1 | 10 | 89 |
| HPV16 | E1 | 9 | 126 |
| HPV16 | E1 | 9 | 485 |
| HPV16 | E1 | 10 | 485 |
| HPV16 | E1 | 9 | 297 |
| HPV16 | E1 | 10 | 297 |
| HPV16 | E1 | 11 | 297 |
| HPV16 | E1 | 8 | 254 |
| HPV16 | E1 | 9 | 254 |
| HPV16 | E1 | 11 | 254 |

TABLE X-continued

HLA A24 Supermotif Peptides

| 1 | 2 | 3 | 4 |
|---|---|---|---|
| HPV16 | E1 | 11 | 293 |
| HPV16 | E1 | 10 | 490 |
| HPV16 | E1 | 8 | 457 |
| HPV16 | E1 | 11 | 457 |
| HPV16 | E1 | 8 | 191 |
| HPV16 | E1 | 9 | 243 |
| HPV16 | E1 | 11 | 48 |
| HPV16 | E1 | 9 | 554 |
| HPV16 | E1 | 10 | 554 |
| HPV16 | E1 | 11 | 554 |
| HPV16 | E1 | 11 | 544 |
| HPV16 | E1 | 8 | 91 |
| HPV16 | E1 | 10 | 583 |
| HPV16 | E1 | 11 | 475 |
| HPV16 | E1 | 9 | 214 |
| HPV16 | E1 | 8 | 260 |
| HPV16 | E1 | 8 | 319 |
| HPV16 | E1 | 11 | 319 |
| HPV16 | E1 | 10 | 444 |
| HPV16 | E1 | 11 | 444 |
| HPV16 | E1 | 8 | 207 |
| HPV16 | E1 | 9 | 207 |
| HPV16 | E1 | 10 | 520 |
| HPV16 | E1 | 8 | 305 |
| HPV16 | E1 | 10 | 360 |
| HPV16 | E1 | 9 | 273 |
| HPV16 | E1 | 10 | 567 |
| HPV16 | E1 | 9 | 105 |
| HPV16 | E1 | 11 | 105 |
| HPV16 | E1 | 10 | 535 |
| HPV16 | E1 | 9 | 136 |
| HPV16 | E1 | 10 | 136 |
| HPV16 | E1 | 9 | 480 |
| HPV16 | E1 | 11 | 480 |
| HPV16 | E1 | 10 | 608 |
| HPV16 | E1 | 11 | 530 |
| HPV16 | E1 | 10 | 593 |
| HPV16 | E1 | 9 | 512 |
| HPV16 | E1 | 10 | 512 |
| HPV16 | E1 | 8 | 561 |
| HPV16 | E1 | 9 | 190 |
| HPV16 | E1 | 10 | 553 |
| HPV16 | E1 | 11 | 553 |
| HPV16 | E1 | 11 | 302 |
| HPV16 | E1 | 10 | 600 |
| HPV16 | E1 | 10 | 577 |
| HPV16 | E1 | 8 | 441 |
| HPV16 | E1 | 8 | 556 |
| HPV16 | E1 | 9 | 556 |
| HPV16 | E1 | 8 | 419 |
| HPV16 | E1 | 10 | 419 |
| HPV16 | E1 | 11 | 359 |
| HPV16 | E1 | 8 | 188 |
| HPV16 | E1 | 11 | 188 |
| HPV16 | E1 | 8 | 343 |
| HPV16 | E1 | 8 | 84 |
| HPV16 | E1 | 8 | 362 |
| HPV16 | E1 | 8 | 257 |
| HPV16 | E1 | 11 | 257 |
| HPV16 | E1 | 10 | 125 |
| HPV16 | E1 | 11 | 582 |
| HPV16 | E1 | 8 | 615 |
| HPV16 | E1 | 8 | 432 |
| HPV16 | E1 | 11 | 432 |
| HPV16 | E1 | 9 | 575 |
| HPV16 | E1 | 11 | 280 |
| HPV16 | E1 | 8 | 447 |
| HPV16 | E1 | 10 | 447 |
| HPV16 | E1 | 11 | 447 |
| HPV16 | E1 | 10 | 611 |
| HPV16 | E1 | 9 | 455 |
| HPV16 | E1 | 10 | 455 |
| HPV16 | E1 | 9 | 349 |
| HPV16 | E1 | 9 | 218 |
| HPV16 | E1 | 9 | 246 |
| HPV16 | E1 | 10 | 246 |
| HPV16 | E1 | 9 | 250 |
| HPV16 | E1 | 11 | 250 |
| HPV16 | E1 | 8 | 266 |
| HPV16 | E1 | 11 | 266 |
| HPV16 | E1 | 8 | 484 |
| HPV16 | E1 | 10 | 484 |
| HPV16 | E1 | 11 | 484 |
| HPV16 | E1 | 11 | 489 |
| HPV16 | E1 | 9 | 546 |
| HPV16 | E1 | 8 | 421 |
| HPV16 | E1 | 8 | 314 |
| HPV16 | E1 | 9 | 314 |
| HPV16 | E1 | 8 | 231 |
| HPV16 | E1 | 11 | 231 |
| HPV16 | E1 | 8 | 270 |
| HPV16 | E1 | 9 | 270 |
| HPV16 | E1 | 10 | 354 |
| HPV16 | E1 | 8 | 587 |
| HPV16 | E1 | 10 | 185 |
| HPV16 | E1 | 11 | 185 |
| HPV16 | E1 | 9 | 289 |
| HPV16 | E1 | 10 | 289 |
| HPV16 | E1 | 8 | 253 |
| HPV16 | E1 | 9 | 253 |
| HPV16 | E1 | 10 | 253 |
| HPV16 | E1 | 8 | 525 |
| HPV16 | E1 | 8 | 585 |
| HPV16 | E1 | 10 | 585 |
| HPV16 | E1 | 11 | 498 |
| HPV16 | E1 | 11 | 85 |
| HPV16 | E1 | 11 | 197 |
| HPV16 | E1 | 11 | 345 |
| HPV16 | E1 | 11 | 443 |
| HPV16 | E1 | 10 | 24 |
| HPV16 | E1 | 9 | 584 |
| HPV16 | E1 | 11 | 584 |
| HPV16 | E1 | 8 | 274 |
| HPV16 | E1 | 9 | 601 |
| HPV16 | E1 | 8 | 332 |
| HPV16 | E1 | 9 | 332 |
| HPV16 | E1 | 8 | 339 |
| HPV16 | E1 | 10 | 509 |
| HPV16 | E1 | 9 | 321 |
| HPV16 | E1 | 10 | 531 |
| HPV16 | E1 | 11 | 261 |
| HPV16 | E1 | 9 | 578 |
| HPV16 | E1 | 11 | 578 |
| HPV16 | E1 | 9 | 90 |
| HPV16 | E1 | 10 | 320 |
| HPV16 | E2 | 10 | 270 |
| HPV16 | E2 | 8 | 72 |
| HPV16 | E2 | 11 | 72 |
| HPV16 | E2 | 11 | 331 |
| HPV16 | E2 | 9 | 41 |
| HPV16 | E2 | 11 | 41 |
| HPV16 | E2 | 11 | 228 |
| HPV16 | E2 | 9 | 69 |
| HPV16 | E2 | 11 | 69 |
| HPV16 | E2 | 9 | 221 |
| HPV16 | E2 | 8 | 63 |
| HPV16 | E2 | 11 | 63 |
| HPV16 | E2 | 8 | 314 |
| HPV16 | E2 | 11 | 309 |
| HPV16 | E2 | 8 | 124 |
| HPV16 | E2 | 11 | 124 |
| HPV16 | E2 | 8 | 25 |
| HPV16 | E2 | 9 | 25 |
| HPV16 | E2 | 11 | 246 |
| HPV16 | E2 | 8 | 96 |
| HPV16 | E2 | 8 | 31 |
| HPV16 | E2 | 9 | 74 |
| HPV16 | E2 | 10 | 74 |
| HPV16 | E2 | 8 | 80 |
| HPV16 | E2 | 9 | 185 |

TABLE X-continued

HLA A24 Supermotif Peptides

| 1 | 2 | 3 | 4 |
|---|---|---|---|
| HPV16 | E2 | 10 | 185 |
| HPV16 | E2 | 8 | 118 |
| HPV16 | E2 | 8 | 204 |
| HPV16 | E2 | 11 | 100 |
| HPV16 | E2 | 8 | 340 |
| HPV16 | E2 | 11 | 346 |
| HPV16 | E2 | 11 | 168 |
| HPV16 | E2 | 9 | 163 |
| HPV16 | E2 | 9 | 156 |
| HPV16 | E2 | 9 | 230 |
| HPV16 | E2 | 8 | 114 |
| HPV16 | E2 | 8 | 29 |
| HPV16 | E2 | 10 | 29 |
| HPV16 | E2 | 10 | 53 |
| HPV16 | E2 | 9 | 290 |
| HPV16 | E2 | 8 | 35 |
| HPV16 | E2 | 9 | 35 |
| HPV16 | E2 | 10 | 35 |
| HPV16 | E2 | 9 | 18 |
| HPV16 | E2 | 8 | 130 |
| HPV16 | E2 | 9 | 130 |
| HPV16 | E2 | 10 | 130 |
| HPV16 | E2 | 8 | 193 |
| HPV16 | E2 | 8 | 356 |
| HPV16 | E2 | 10 | 356 |
| HPV16 | E2 | 11 | 288 |
| HPV16 | E2 | 10 | 332 |
| HPV16 | E2 | 11 | 82 |
| HPV16 | E2 | 8 | 42 |
| HPV16 | E2 | 10 | 42 |
| HPV16 | E2 | 9 | 354 |
| HPV16 | E2 | 10 | 354 |
| HPV16 | E2 | 9 | 91 |
| HPV16 | E2 | 8 | 177 |
| HPV16 | E2 | 8 | 103 |
| HPV16 | E2 | 11 | 16 |
| HPV16 | E2 | 11 | 77 |
| HPV16 | E2 | 9 | 311 |
| HPV16 | E2 | 11 | 311 |
| HPV16 | E2 | 8 | 157 |
| HPV16 | E2 | 11 | 157 |
| HPV16 | E2 | 8 | 296 |
| HPV16 | E2 | 10 | 296 |
| HPV16 | E2 | 8 | 127 |
| HPV16 | E2 | 11 | 127 |
| HPV16 | E2 | 8 | 284 |
| HPV16 | E2 | 8 | 9 |
| HPV16 | E2 | 11 | 9 |
| HPV16 | E2 | 8 | 325 |
| HPV16 | E2 | 11 | 325 |
| HPV16 | E2 | 10 | 106 |
| HPV16 | E2 | 11 | 60 |
| HPV16 | E2 | 10 | 120 |
| HPV16 | E2 | 9 | 170 |
| HPV16 | E2 | 8 | 345 |
| HPV16 | E2 | 8 | 76 |
| HPV16 | E2 | 8 | 151 |
| HPV16 | E2 | 9 | 151 |
| HPV16 | E2 | 10 | 191 |
| HPV16 | E2 | 8 | 349 |
| HPV16 | E2 | 9 | 86 |
| HPV16 | E2 | 8 | 304 |
| HPV16 | E2 | 9 | 304 |
| HPV16 | E2 | 11 | 278 |
| HPV16 | E2 | 8 | 37 |
| HPV16 | E2 | 9 | 7 |
| HPV16 | E2 | 10 | 7 |
| HPV16 | E2 | 10 | 302 |
| HPV16 | E2 | 11 | 302 |
| HPV16 | E2 | 8 | 23 |
| HPV16 | E2 | 10 | 23 |
| HPV16 | E2 | 11 | 23 |
| HPV16 | E2 | 8 | 261 |
| HPV16 | E2 | 11 | 261 |
| HPV16 | E2 | 11 | 144 |
| HPV16 | E2 | 8 | 355 |
| HPV16 | E2 | 9 | 355 |
| HPV16 | E2 | 11 | 355 |
| HPV16 | E2 | 10 | 61 |
| HPV16 | E2 | 10 | 78 |
| HPV16 | E2 | 9 | 297 |
| HPV16 | E2 | 10 | 93 |
| HPV16 | E2 | 11 | 93 |
| HPV16 | E2 | 8 | 334 |
| HPV16 | E2 | 10 | 310 |
| HPV16 | E2 | 10 | 128 |
| HPV16 | E2 | 11 | 128 |
| HPV16 | E2 | 10 | 116 |
| HPV16 | E2 | 9 | 357 |
| HPV16 | E2 | 9 | 146 |
| HPV16 | E2 | 10 | 146 |
| HPV16 | E2 | 11 | 336 |
| HPV16 | E2 | 9 | 192 |
| HPV16 | E2 | 9 | 333 |
| HPV16 | E2 | 10 | 145 |
| HPV16 | E2 | 11 | 145 |
| HPV16 | E2 | 8 | 147 |
| HPV16 | E2 | 9 | 147 |
| HPV16 | E2 | 11 | 147 |
| HPV16 | E2 | 11 | 183 |
| HPV16 | E2 | 10 | 101 |
| HPV16 | E2 | 8 | 92 |
| HPV16 | E2 | 11 | 92 |
| HPV16 | E2 | 9 | 102 |
| HPV16 | E2 | 8 | 312 |
| HPV16 | E2 | 10 | 312 |
| HPV16 | E2 | 8 | 131 |
| HPV16 | E2 | 9 | 131 |
| HPV16 | E2 | 11 | 115 |
| HPV16 | E2 | 9 | 159 |
| HPV16 | E2 | 10 | 159 |
| HPV16 | E2 | 11 | 32 |
| HPV16 | E2 | 11 | 154 |
| HPV16 | E2 | 9 | 43 |
| HPV16 | E2 | 10 | 158 |
| HPV16 | E2 | 11 | 158 |
| HPV16 | E5 | 8 | 56 |
| HPV16 | E5 | 9 | 56 |
| HPV16 | E5 | 10 | 56 |
| HPV16 | E5 | 11 | 56 |
| HPV16 | E5 | 10 | 18 |
| HPV16 | E5 | 11 | 18 |
| HPV16 | E5 | 8 | 59 |
| HPV16 | E5 | 10 | 59 |
| HPV16 | E5 | 11 | 59 |
| HPV16 | E5 | 9 | 14 |
| HPV16 | E5 | 10 | 14 |
| HPV16 | E5 | 8 | 26 |
| HPV16 | E5 | 9 | 26 |
| HPV16 | E5 | 9 | 24 |
| HPV16 | E5 | 10 | 24 |
| HPV16 | E5 | 11 | 24 |
| HPV16 | E5 | 8 | 20 |
| HPV16 | E5 | 9 | 20 |
| HPV16 | E5 | 10 | 20 |
| HPV16 | E5 | 8 | 5 |
| HPV16 | E5 | 11 | 5 |
| HPV16 | E5 | 9 | 60 |
| HPV16 | E5 | 10 | 60 |
| HPV16 | E5 | 9 | 72 |
| HPV16 | E5 | 10 | 72 |
| HPV16 | E5 | 11 | 72 |
| HPV16 | E5 | 8 | 15 |
| HPV16 | E5 | 9 | 15 |
| HPV16 | E5 | 8 | 66 |
| HPV16 | E5 | 9 | 66 |
| HPV16 | E5 | 8 | 75 |
| HPV16 | E5 | 8 | 65 |
| HPV16 | E5 | 9 | 65 |
| HPV16 | E5 | 20 | 65 |

TABLE X-continued

HLA A24 Supermotif Peptides

| 1 | 2 | 3 | 4 |
|---|---|---|---|
| HPV16 | E5 | 8 | 64 |
| HPV16 | E5 | 9 | 64 |
| HPV16 | E5 | 10 | 64 |
| HPV16 | E5 | 11 | 64 |
| HPV16 | E5 | 8 | 43 |
| HPV16 | E5 | 9 | 43 |
| HPV16 | E5 | 8 | 44 |
| HPV16 | E5 | 10 | 51 |
| HPV16 | E5 | 11 | 51 |
| HPV16 | E5 | 8 | 61 |
| HPV16 | E5 | 9 | 61 |
| HPV16 | E5 | 11 | 61 |
| HPV16 | E5 | 10 | 71 |
| HPV16 | E5 | 11 | 71 |
| HPV16 | E5 | 8 | 73 |
| HPV16 | E5 | 9 | 73 |
| HPV16 | E5 | 10 | 73 |
| HPV16 | E5 | 8 | 42 |
| HPV16 | E5 | 9 | 42 |
| HPV16 | E5 | 10 | 42 |
| HPV16 | E5 | 9 | 11 |
| HPV16 | E5 | 8 | 16 |
| HPV16 | E5 | 8 | 22 |
| HPV16 | E5 | 11 | 22 |
| HPV16 | E5 | 8 | 27 |
| HPV16 | E5 | 8 | 32 |
| HPV16 | E5 | 11 | 32 |
| HPV16 | E5 | 11 | 47 |
| HPV16 | E5 | 10 | 33 |
| HPV16 | E5 | 11 | 33 |
| HPV16 | E5 | 10 | 48 |
| HPV16 | E5 | 9 | 49 |
| HPV16 | E5 | 11 | 1 |
| HPV16 | E5 | 9 | 3 |
| HPV16 | E5 | 10 | 3 |
| HPV16 | E5 | 11 | 70 |
| HPV16 | E5 | 9 | 31 |
| HPV16 | E5 | 8 | 41 |
| HPV16 | E5 | 9 | 41 |
| HPV16 | E5 | 10 | 41 |
| HPV16 | E5 | 11 | 41 |
| HPV16 | E5 | 8 | 8 |
| HPV16 | E5 | 9 | 8 |
| HPV16 | E5 | 10 | 8 |
| HPV16 | E5 | 8 | 37 |
| HPV16 | E5 | 9 | 37 |
| HPV16 | E5 | 11 | 37 |
| HPV16 | E5 | 8 | 35 |
| HPV16 | E5 | 9 | 35 |
| HPV16 | E5 | 10 | 35 |
| HPV16 | E5 | 11 | 35 |
| HPV16 | E5 | 8 | 10 |
| HPV16 | E5 | 10 | 10 |
| HPV16 | E5 | 8 | 9 |
| HPV16 | E5 | 9 | 9 |
| HPV16 | E5 | 11 | 9 |
| HPV16 | E5 | 8 | 38 |
| HPV16 | E5 | 10 | 38 |
| HPV16 | E5 | 11 | 38 |
| HPV16 | E5 | 8 | 21 |
| HPV16 | E5 | 9 | 21 |
| HPV16 | E5 | 8 | 62 |
| HPV16 | E5 | 10 | 62 |
| HPV16 | E5 | 11 | 62 |
| HPV16 | E5 | 8 | 67 |
| HPV16 | E5 | 8 | 50 |
| HPV16 | E5 | 11 | 50 |
| HPV16 | E5 | 9 | 63 |
| HPV16 | E5 | 10 | 63 |
| HPV16 | E5 | 11 | 63 |
| HPV16 | E5 | 9 | 39 |
| HPV16 | E5 | 10 | 39 |
| HPV16 | E5 | 11 | 39 |
| HPV16 | E6 | 9 | 53 |
| HPV16 | E6 | 9 | 68 |
| HPV16 | E6 | 10 | 68 |
| HPV16 | E6 | 8 | 110 |
| HPV16 | E6 | 10 | 58 |
| HPV16 | E6 | 8 | 73 |
| HPV16 | E6 | 11 | 73 |
| HPV16 | E6 | 8 | 23 |
| HPV16 | E6 | 11 | 23 |
| HPV16 | E6 | 8 | 37 |
| HPV16 | E6 | 9 | 37 |
| HPV16 | E6 | 9 | 87 |
| HPV16 | E6 | 9 | 51 |
| HPV16 | E6 | 11 | 51 |
| HPV16 | E6 | 8 | 32 |
| HPV16 | E6 | 9 | 25 |
| HPV16 | E6 | 10 | 25 |
| HPV16 | E6 | 11 | 25 |
| HPV16 | E6 | 10 | 48 |
| HPV16 | E6 | 9 | 82 |
| HPV16 | E6 | 10 | 82 |
| HPV16 | E6 | 8 | 76 |
| HPV16 | E6 | 11 | 76 |
| HPV16 | E6 | 8 | 92 |
| HPV16 | E6 | 8 | 125 |
| HPV16 | E6 | 11 | 125 |
| HPV16 | E6 | 11 | 85 |
| HPV16 | E6 | 11 | 34 |
| HPV16 | E6 | 9 | 59 |
| HPV16 | E6 | 9 | 75 |
| HPV16 | E6 | 8 | 79 |
| HPV16 | E6 | 10 | 79 |
| HPV16 | E6 | 9 | 18 |
| HPV16 | E6 | 11 | 107 |
| HPV16 | E6 | 9 | 44 |
| HPV16 | E6 | 11 | 44 |
| HPV16 | E6 | 10 | 90 |
| HPV16 | E6 | 11 | 134 |
| HPV16 | E6 | 10 | 102 |
| HPV16 | E6 | 11 | 116 |
| HPV16 | E6 | 9 | 66 |
| HPV16 | E6 | 11 | 66 |
| HPV16 | E6 | 10 | 21 |
| HPV16 | E6 | 8 | 43 |
| HPV16 | E6 | 10 | 43 |
| HPV16 | E6 | 8 | 27 |
| HPV16 | E6 | 9 | 27 |
| HPV16 | E6 | 9 | 98 |
| HPV16 | E6 | 10 | 98 |
| HPV16 | E6 | 11 | 98 |
| HPV16 | E6 | 9 | 131 |
| HPV16 | E6 | 8 | 151 |
| HPV16 | E6 | 11 | 89 |
| HPV16 | E6 | 11 | 29 |
| HPV16 | E6 | 10 | 94 |
| HPV16 | E6 | 8 | 28 |
| HPV16 | E6 | 11 | 93 |
| HPV16 | E6 | 8 | 38 |
| HPV16 | E6 | 9 | 49 |
| HPV16 | E6 | 11 | 49 |
| HPV16 | E6 | 8 | 60 |
| HPV16 | E7 | 9 | 68 |
| HPV16 | E7 | 8 | 75 |
| HPV16 | E7 | 9 | 75 |
| HPV16 | E7 | 10 | 75 |
| HPV16 | E7 | 9 | 81 |
| HPV16 | E7 | 9 | 14 |
| HPV16 | E7 | 10 | 14 |
| HPV16 | E7 | 8 | 21 |
| HPV16 | E7 | 8 | 4 |
| HPV16 | E7 | 9 | 4 |
| HPV16 | E7 | 10 | 4 |
| HPV16 | E7 | 8 | 18 |
| HPV16 | E7 | 11 | 18 |
| HPV16 | E7 | 9 | 85 |
| HPV16 | E7 | 10 | 73 |
| HPV16 | E7 | 11 | 73 |

TABLE X-continued

HLA A24 Supermotif Peptides

| 1 | 2 | 3 | 4 |
|---|---|---|---|
| HPV16 | E7 | 8 | 82 |
| HPV16 | E7 | 11 | 83 |
| HPV16 | E7 | 11 | 12 |
| HPV16 | E7 | 8 | 6 |
| HPV16 | E7 | 10 | 6 |
| HPV16 | E7 | 11 | 66 |
| HPV16 | E7 | 8 | 77 |
| HPV16 | E7 | 11 | 77 |
| HPV16 | E7 | 9 | 71 |
| HPV16 | E7 | 10 | 56 |
| HPV16 | E7 | 10 | 78 |
| HPV16 | E7 | 8 | 86 |
| HPV16 | E7 | 9 | 7 |
| HPV16 | E7 | 10 | 19 |
| HPV16 | E7 | 11 | 55 |
| HPV16 | L1 | 9 | 373 |
| HPV16 | L1 | 10 | 292 |
| HPV16 | L1 | 11 | 292 |
| HPV16 | L1 | 9 | 70 |
| HPV16 | L1 | 10 | 205 |
| HPV16 | L1 | 11 | 172 |
| HPV16 | L1 | 9 | 183 |
| HPV16 | L1 | 10 | 251 |
| HPV16 | L1 | 11 | 251 |
| HPV16 | L1 | 9 | 13 |
| HPV16 | L1 | 11 | 13 |
| HPV16 | L1 | 9 | 249 |
| HPV16 | L1 | 11 | 484 |
| HPV16 | L1 | 8 | 397 |
| HPV16 | L1 | 11 | 397 |
| HPV16 | L1 | 10 | 225 |
| HPV16 | L1 | 8 | 154 |
| HPV16 | L1 | 9 | 228 |
| HPV16 | L1 | 8 | 361 |
| HPV16 | L1 | 10 | 361 |
| HPV16 | L1 | 11 | 442 |
| HPV16 | L1 | 9 | 412 |
| HPV16 | L1 | 8 | 17 |
| HPV16 | L1 | 9 | 17 |
| HPV16 | L1 | 11 | 17 |
| HPV16 | L1 | 10 | 259 |
| HPV16 | L1 | 9 | 176 |
| HPV16 | L1 | 10 | 176 |
| HPV16 | L1 | 9 | 378 |
| HPV16 | L1 | 8 | 132 |
| HPV16 | L1 | 8 | 474 |
| HPV16 | L1 | 10 | 245 |
| HPV16 | L1 | 8 | 395 |
| HPV16 | L1 | 10 | 395 |
| HPV16 | L1 | 9 | 388 |
| HPV16 | L1 | 11 | 388 |
| HPV16 | L1 | 8 | 52 |
| HPV16 | L1 | 9 | 52 |
| HPV16 | L1 | 10 | 52 |
| HPV16 | L1 | 8 | 24 |
| HPV16 | L1 | 9 | 273 |
| HPV16 | L1 | 10 | 273 |
| HPV16 | L1 | 8 | 400 |
| HPV16 | L1 | 10 | 400 |
| HPV16 | L1 | 10 | 5 |
| HPV16 | L1 | 10 | 472 |
| HPV16 | L1 | 8 | 274 |
| HPV16 | L1 | 9 | 274 |
| HPV16 | L1 | 9 | 116 |
| HPV16 | L1 | 11 | 116 |
| HPV16 | L1 | 10 | 230 |
| HPV16 | L1 | 8 | 110 |
| HPV16 | L1 | 8 | 348 |
| HPV16 | L1 | 9 | 348 |
| HPV16 | L1 | 8 | 142 |
| HPV16 | L1 | 11 | 142 |
| HPV16 | L1 | 8 | 499 |
| HPV16 | L1 | 10 | 499 |
| HPV16 | L1 | 10 | 431 |
| HPV16 | L1 | 9 | 93 |
| HPV16 | L1 | 11 | 93 |
| HPV16 | L1 | 9 | 438 |
| HPV16 | L1 | 8 | 166 |
| HPV16 | L1 | 10 | 166 |
| HPV16 | L1 | 10 | 130 |
| HPV16 | L1 | 9 | 140 |
| HPV16 | L1 | 10 | 140 |
| HPV16 | L1 | 8 | 22 |
| HPV16 | L1 | 9 | 22 |
| HPV16 | L1 | 10 | 22 |
| HPV16 | L1 | 8 | 102 |
| HPV16 | L1 | 10 | 102 |
| HPV16 | L1 | 11 | 457 |
| HPV16 | L1 | 8 | 23 |
| HPV16 | L1 | 9 | 23 |
| HPV16 | L1 | 8 | 332 |
| HPV16 | L1 | 9 | 401 |
| HPV16 | L1 | 9 | 424 |
| HPV16 | L1 | 9 | 86 |
| HPV16 | L1 | 11 | 86 |
| HPV16 | L1 | 11 | 11 |
| HPV16 | L1 | 8 | 407 |
| HPV16 | L1 | 10 | 407 |
| HPV16 | L1 | 11 | 407 |
| HPV16 | L1 | 9 | 6 |
| HPV16 | L1 | 10 | 59 |
| HPV16 | L1 | 11 | 59 |
| HPV16 | L1 | 9 | 108 |
| HPV16 | L1 | 10 | 108 |
| HPV16 | L1 | 8 | 493 |
| HPV16 | L1 | 9 | 480 |
| HPV16 | L1 | 11 | 480 |
| HPV16 | L1 | 10 | 85 |
| HPV16 | L1 | 9 | 406 |
| HPV16 | L1 | 11 | 406 |
| HPV16 | L1 | 11 | 151 |
| HPV16 | L1 | 11 | 262 |
| HPV16 | L1 | 10 | 90 |
| HPV16 | L1 | 8 | 46 |
| HPV16 | L1 | 8 | 256 |
| HPV16 | L1 | 9 | 469 |
| HPV16 | L1 | 10 | 272 |
| HPV16 | L1 | 11 | 272 |
| HPV16 | L1 | 8 | 184 |
| HPV16 | L1 | 11 | 216 |
| HPV16 | L1 | 8 | 68 |
| HPV16 | L1 | 9 | 68 |
| HPV16 | L1 | 11 | 68 |
| HPV16 | L1 | 8 | 409 |
| HPV16 | L1 | 9 | 409 |
| HPV16 | L1 | 8 | 87 |
| HPV16 | L1 | 10 | 87 |
| HPV16 | L1 | 10 | 29 |
| HPV16 | L1 | 11 | 29 |
| HPV16 | L1 | 11 | 414 |
| HPV16 | L1 | 9 | 226 |
| HPV16 | L1 | 11 | 226 |
| HPV16 | L1 | 10 | 263 |
| HPV16 | L1 | 11 | 263 |
| HPV16 | L1 | 8 | 325 |
| HPV16 | L1 | 9 | 325 |
| HPV16 | L1 | 11 | 58 |
| HPV16 | L1 | 8 | 311 |
| HPV16 | L1 | 10 | 476 |
| HPV16 | L1 | 8 | 367 |
| HPV16 | L1 | 8 | 383 |
| HPV16 | L1 | 9 | 218 |
| HPV16 | L1 | 8 | 296 |
| HPV16 | L1 | 9 | 19 |
| HPV16 | L1 | 11 | 19 |
| HPV16 | L1 | 10 | 316 |
| HPV16 | L1 | 10 | 77 |
| HPV16 | L1 | 11 | 77 |
| HPV16 | L1 | 8 | 247 |
| HPV16 | L1 | 11 | 247 |

TABLE X-continued

HLA A24 Supermotif Peptides

| 1 | 2 | 3 | 4 |
|---|---|---|---|
| HPV16 | L1 | 9 | 213 |
| HPV16 | L1 | 8 | 489 |
| HPV16 | L1 | 11 | 138 |
| HPV16 | L1 | 8 | 466 |
| HPV16 | L1 | 11 | 43 |
| HPV16 | L1 | 8 | 267 |
| HPV16 | L1 | 9 | 267 |
| HPV16 | L1 | 10 | 267 |
| HPV16 | L1 | 9 | 399 |
| HPV16 | L1 | 11 | 399 |
| HPV16 | L1 | 8 | 487 |
| HPV16 | L1 | 9 | 487 |
| HPV16 | L1 | 10 | 487 |
| HPV16 | L1 | 8 | 331 |
| HPV16 | L1 | 9 | 331 |
| HPV16 | L1 | 11 | 181 |
| HPV16 | L1 | 8 | 280 |
| HPV16 | L1 | 8 | 2 |
| HPV16 | L1 | 10 | 2 |
| HPV16 | L1 | 9 | 95 |
| HPV16 | L1 | 8 | 445 |
| HPV16 | L1 | 10 | 100 |
| HPV16 | L1 | 9 | 67 |
| HPV16 | L1 | 10 | 67 |
| HPV16 | L1 | 10 | 115 |
| HPV16 | L1 | 8 | 253 |
| HPV16 | L1 | 9 | 253 |
| HPV16 | L1 | 11 | 253 |
| HPV16 | L1 | 11 | 271 |
| HPV16 | L1 | 11 | 28 |
| HPV16 | L1 | 9 | 174 |
| HPV16 | L1 | 11 | 174 |
| HPV16 | L1 | 10 | 419 |
| HPV16 | L1 | 9 | 324 |
| HPV16 | L1 | 10 | 324 |
| HPV16 | L1 | 10 | 308 |
| HPV16 | L1 | 11 | 308 |
| HPV16 | L1 | 11 | 49 |
| HPV16 | L1 | 9 | 422 |
| HPV16 | L1 | 11 | 422 |
| HPV16 | L1 | 10 | 365 |
| HPV16 | L1 | 11 | 521 |
| HPV16 | L1 | 8 | 4 |
| HPV16 | L1 | 11 | 4 |
| HPV16 | L1 | 11 | 471 |
| HPV16 | L1 | 8 | 423 |
| HPV16 | L1 | 10 | 423 |
| HPV16 | L1 | 8 | 439 |
| HPV16 | L1 | 11 | 238 |
| HPV16 | L1 | 9 | 408 |
| HPV16 | L1 | 10 | 408 |
| HPV16 | L1 | 10 | 522 |
| HPV16 | L1 | 9 | 362 |
| HPV16 | L1 | 8 | 379 |
| HPV16 | L1 | 11 | 379 |
| HPV16 | L1 | 8 | 219 |
| HPV16 | L1 | 11 | 358 |
| HPV16 | L1 | 10 | 415 |
| HPV16 | L1 | 11 | 415 |
| HPV16 | L1 | 10 | 380 |
| HPV16 | L1 | 11 | 380 |
| HPV16 | L1 | 10 | 443 |
| HPV16 | L1 | 8 | 413 |
| HPV16 | L1 | 9 | 3 |
| HPV16 | L1 | 8 | 326 |
| HPV16 | L1 | 10 | 359 |
| HPV16 | L1 | 8 | 20 |
| HPV16 | L1 | 10 | 20 |
| HPV16 | L1 | 11 | 20 |
| HPV16 | L1 | 9 | 30 |
| HPV16 | L1 | 10 | 30 |
| HPV16 | L1 | 9 | 317 |
| HPV16 | L1 | 9 | 416 |
| HPV16 | L1 | 10 | 416 |
| HPV16 | L1 | 11 | 302 |
| HPV16 | L1 | 9 | 260 |
| HPV16 | L1 | 8 | 7 |
| HPV16 | L1 | 8 | 389 |
| HPV16 | L1 | 10 | 389 |
| HPV16 | L1 | 8 | 275 |
| HPV16 | L1 | 8 | 470 |
| HPV16 | L1 | 8 | 53 |
| HPV16 | L1 | 9 | 53 |
| HPV16 | L1 | 9 | 60 |
| HPV16 | L1 | 10 | 60 |
| HPV16 | L2 | 9 | 241 |
| HPV16 | L2 | 10 | 241 |
| HPV16 | L2 | 10 | 356 |
| HPV16 | L2 | 11 | 356 |
| HPV16 | L2 | 9 | 293 |
| HPV16 | L2 | 11 | 293 |
| HPV16 | L2 | 11 | 256 |
| HPV16 | L2 | 8 | 282 |
| HPV16 | L2 | 11 | 329 |
| HPV16 | L2 | 8 | 445 |
| HPV16 | L2 | 9 | 445 |
| HPV16 | L2 | 10 | 445 |
| HPV16 | L2 | 11 | 445 |
| HPV16 | L2 | 11 | 31 |
| HPV16 | L2 | 10 | 285 |
| HPV16 | L2 | 8 | 367 |
| HPV16 | L2 | 10 | 84 |
| HPV16 | L2 | 9 | 140 |
| HPV16 | L2 | 8 | 261 |
| HPV16 | L2 | 8 | 195 |
| HPV16 | L2 | 10 | 340 |
| HPV16 | L2 | 8 | 176 |
| HPV16 | L2 | 8 | 242 |
| HPV16 | L2 | 9 | 242 |
| HPV16 | L2 | 11 | 242 |
| HPV16 | L2 | 8 | 181 |
| HPV16 | L2 | 8 | 446 |
| HPV16 | L2 | 9 | 446 |
| HPV16 | L2 | 10 | 446 |
| HPV16 | L2 | 8 | 259 |
| HPV16 | L2 | 9 | 259 |
| HPV16 | L2 | 10 | 259 |
| HPV16 | L2 | 10 | 364 |
| HPV16 | L2 | 11 | 364 |
| HPV16 | L2 | 8 | 26 |
| HPV16 | L2 | 8 | 65 |
| HPV16 | L2 | 9 | 65 |
| HPV16 | L2 | 11 | 65 |
| HPV16 | L2 | 11 | 76 |
| HPV16 | L2 | 9 | 52 |
| HPV16 | L2 | 9 | 392 |
| HPV16 | L2 | 11 | 392 |
| HPV16 | L2 | 9 | 180 |
| HPV16 | L2 | 9 | 325 |
| HPV16 | L2 | 8 | 439 |
| HPV16 | L2 | 9 | 439 |
| HPV16 | L2 | 10 | 439 |
| HPV16 | L2 | 10 | 32 |
| HPV16 | L2 | 10 | 45 |
| HPV16 | L2 | 11 | 45 |
| HPV16 | L2 | 8 | 420 |
| HPV16 | L2 | 9 | 420 |
| HPV16 | L2 | 11 | 420 |
| HPV16 | L2 | 8 | 243 |
| HPV16 | L2 | 10 | 243 |
| HPV16 | L2 | 11 | 135 |
| HPV16 | L2 | 8 | 250 |
| HPV16 | L2 | 11 | 250 |
| HPV16 | L2 | 9 | 286 |
| HPV16 | L2 | 8 | 430 |
| HPV16 | L2 | 10 | 430 |
| HPV16 | L2 | 11 | 430 |
| HPV16 | L2 | 10 | 105 |
| HPV16 | L2 | 11 | 105 |
| HPV16 | L2 | 10 | 248 |

TABLE X-continued

HLA A24 Supermotif Peptides

| 1 | 2 | 3 | 4 |
|---|---|---|---|
| HPV16 | L2 | 8 | 39 |
| HPV16 | L2 | 10 | 39 |
| HPV16 | L2 | 11 | 35 |
| HPV16 | L2 | 8 | 323 |
| HPV16 | L2 | 11 | 323 |
| HPV16 | L2 | 8 | 236 |
| HPV16 | L2 | 11 | 427 |
| HPV16 | L2 | 9 | 249 |
| HPV16 | L2 | 8 | 294 |
| HPV16 | L2 | 10 | 294 |
| HPV16 | L2 | 8 | 108 |
| HPV16 | L2 | 9 | 410 |
| HPV16 | L2 | 11 | 410 |
| HPV16 | L2 | 9 | 365 |
| HPV16 | L2 | 10 | 365 |
| HPV16 | L2 | 10 | 266 |
| HPV16 | L2 | 9 | 454 |
| HPV16 | L2 | 11 | 454 |
| HPV16 | L2 | 8 | 276 |
| HPV16 | L2 | 9 | 276 |
| HPV16 | L2 | 11 | 276 |
| HPV16 | L2 | 10 | 407 |
| HPV16 | L2 | 9 | 419 |
| HPV16 | L2 | 10 | 419 |
| HPV16 | L2 | 10 | 397 |
| HPV16 | L2 | 9 | 208 |
| HPV16 | L2 | 10 | 192 |
| HPV16 | L2 | 11 | 192 |
| HPV16 | L2 | 8 | 401 |
| HPV16 | L2 | 10 | 401 |
| HPV16 | L2 | 11 | 417 |
| HPV16 | L2 | 11 | 215 |
| HPV16 | L2 | 9 | 429 |
| HPV16 | L2 | 11 | 429 |
| HPV16 | L2 | 8 | 409 |
| HPV16 | L2 | 10 | 409 |
| HPV16 | L2 | 9 | 161 |
| HPV16 | L2 | 10 | 172 |
| HPV16 | L2 | 8 | 358 |
| HPV16 | L2 | 9 | 358 |
| HPV16 | L2 | 11 | 358 |
| HPV16 | L2 | 8 | 221 |
| HPV16 | L2 | 9 | 97 |
| HPV16 | L2 | 10 | 381 |
| HPV16 | L2 | 9 | 463 |
| HPV16 | L2 | 8 | 44 |
| HPV16 | L2 | 11 | 44 |
| HPV16 | L2 | 8 | 342 |
| HPV16 | L2 | 11 | 310 |
| HPV16 | L2 | 9 | 234 |
| HPV16 | L2 | 10 | 234 |
| HPV16 | L2 | 8 | 47 |
| HPV16 | L2 | 9 | 47 |
| HPV16 | L2 | 11 | 436 |
| HPV16 | L2 | 8 | 305 |
| HPV16 | L2 | 11 | 461 |
| HPV16 | L2 | 9 | 298 |
| HPV16 | L2 | 10 | 9 |
| HPV16 | L2 | 11 | 9 |
| HPV16 | L2 | 8 | 313 |
| HPV16 | L2 | 11 | 302 |
| HPV16 | L2 | 8 | 319 |
| HPV16 | L2 | 9 | 319 |
| HPV16 | L2 | 10 | 319 |
| HPV16 | L2 | 10 | 274 |
| HPV16 | L2 | 11 | 274 |
| HPV16 | L2 | 9 | 360 |
| HPV16 | L2 | 10 | 360 |
| HPV16 | L2 | 9 | 125 |
| HPV16 | L2 | 11 | 125 |
| HPV16 | L2 | 11 | 104 |
| HPV16 | L2 | 8 | 107 |
| HPV16 | L2 | 9 | 107 |
| HPV16 | L2 | 9 | 50 |
| HPV16 | L2 | 11 | 50 |
| HPV16 | L2 | 8 | 138 |
| HPV16 | L2 | 9 | 138 |
| HPV16 | L2 | 11 | 138 |
| HPV16 | L2 | 8 | 189 |
| HPV16 | L2 | 10 | 189 |
| HPV16 | L2 | 9 | 331 |
| HPV16 | L2 | 11 | 331 |
| HPV16 | L2 | 8 | 186 |
| HPV16 | L2 | 11 | 186 |
| HPV16 | L2 | 8 | 387 |
| HPV16 | L2 | 11 | 347 |
| HPV16 | L2 | 10 | 384 |
| HPV16 | L2 | 11 | 384 |
| HPV16 | L2 | 8 | 162 |
| HPV16 | L2 | 9 | 40 |
| HPV16 | L2 | 8 | 332 |
| HPV16 | L2 | 10 | 332 |
| HPV16 | L2 | 9 | 438 |
| HPV16 | L2 | 10 | 438 |
| HPV16 | L2 | 11 | 438 |
| HPV16 | L2 | 8 | 399 |
| HPV16 | L2 | 10 | 399 |
| HPV16 | L2 | 10 | 187 |
| HPV16 | L2 | 9 | 85 |
| HPV16 | L2 | 10 | 311 |
| HPV16 | L2 | 11 | 265 |
| HPV16 | L2 | 8 | 156 |
| HPV16 | L2 | 9 | 398 |
| HPV16 | L2 | 11 | 398 |
| HPV16 | L2 | 8 | 141 |
| HPV16 | L2 | 9 | 244 |
| HPV16 | L2 | 11 | 351 |
| HPV16 | L2 | 10 | 136 |
| HPV16 | L2 | 11 | 136 |
| HPV16 | L2 | 8 | 350 |
| HPV16 | L2 | 11 | 153 |
| HPV16 | L2 | 8 | 209 |
| HPV16 | L2 | 10 | 154 |
| HPV16 | L2 | 10 | 251 |
| HPV16 | L2 | 10 | 348 |
| HPV16 | L2 | 8 | 53 |
| HPV16 | L2 | 9 | 155 |
| HPV16 | L2 | 8 | 464 |
| HPV16 | L2 | 9 | 267 |
| HPV16 | L2 | 11 | 267 |
| HPV16 | L2 | 8 | 393 |
| HPV16 | L2 | 10 | 393 |
| HPV16 | L2 | 8 | 447 |
| HPV16 | L2 | 9 | 447 |
| HPV16 | L2 | 10 | 453 |
| HPV16 | L2 | 10 | 437 |
| HPV16 | L2 | 11 | 437 |
| HPV16 | L2 | 9 | 349 |
| HPV16 | L2 | 11 | 452 |
| HPV16 | L2 | 8 | 326 |
| HPV18 | E1 | 11 | 398 |
| HPV18 | E1 | 9 | 246 |
| HPV18 | E1 | 11 | 22 |
| HPV18 | E1 | 9 | 546 |
| HPV18 | E1 | 9 | 325 |
| HPV18 | E1 | 10 | 213 |
| HPV18 | E1 | 11 | 526 |
| HPV18 | E1 | 8 | 40 |
| HPV18 | E1 | 11 | 40 |
| HPV18 | E1 | 8 | 531 |
| HPV18 | E1 | 9 | 531 |
| HPV18 | E1 | 9 | 216 |
| HPV18 | E1 | 11 | 216 |
| HPV18 | E1 | 10 | 618 |
| HPV18 | E1 | 9 | 273 |
| HPV18 | E1 | 10 | 273 |
| HPV18 | E1 | 11 | 273 |
| HPV18 | E1 | 9 | 311 |
| HPV18 | E1 | 8 | 240 |
| HPV18 | E1 | 9 | 240 |

TABLE X-continued

HLA A24 Supermotif Peptides

| 1 | 2 | 3 | 4 |
|---|---|---|---|
| HPV18 | E1 | 9 | 196 |
| HPV18 | E1 | 10 | 196 |
| HPV18 | E1 | 8 | 535 |
| HPV18 | E1 | 9 | 535 |
| HPV18 | E1 | 9 | 49 |
| HPV18 | E1 | 8 | 363 |
| HPV18 | E1 | 10 | 363 |
| HPV18 | E1 | 8 | 381 |
| HPV18 | E1 | 9 | 381 |
| HPV18 | E1 | 10 | 637 |
| HPV18 | E1 | 8 | 106 |
| HPV18 | E1 | 11 | 106 |
| HPV18 | E1 | 9 | 42 |
| HPV18 | E1 | 10 | 42 |
| HPV18 | E1 | 9 | 342 |
| HPV18 | E1 | 11 | 342 |
| HPV18 | E1 | 10 | 220 |
| HPV18 | E1 | 8 | 540 |
| HPV18 | E1 | 8 | 445 |
| HPV18 | E1 | 9 | 445 |
| HPV18 | E1 | 11 | 445 |
| HPV18 | E1 | 9 | 459 |
| HPV18 | E1 | 8 | 594 |
| HPV18 | E1 | 10 | 610 |
| HPV18 | E1 | 11 | 610 |
| HPV18 | E1 | 8 | 62 |
| HPV18 | E1 | 9 | 62 |
| HPV18 | E1 | 9 | 108 |
| HPV18 | E1 | 11 | 108 |
| HPV18 | E1 | 8 | 375 |
| HPV18 | E1 | 10 | 375 |
| HPV18 | E1 | 11 | 366 |
| HPV18 | E1 | 11 | 309 |
| HPV18 | E1 | 10 | 104 |
| HPV18 | E1 | 9 | 74 |
| HPV18 | E1 | 9 | 338 |
| HPV18 | E1 | 10 | 338 |
| HPV18 | E1 | 8 | 345 |
| HPV18 | E1 | 9 | 345 |
| HPV18 | E1 | 9 | 619 |
| HPV18 | E1 | 11 | 619 |
| HPV18 | E1 | 8 | 50 |
| HPV18 | E1 | 10 | 497 |
| HPV18 | E1 | 10 | 265 |
| HPV18 | E1 | 9 | 500 |
| HPV18 | E1 | 8 | 460 |
| HPV18 | E1 | 11 | 460 |
| HPV18 | E1 | 8 | 463 |
| HPV18 | E1 | 9 | 463 |
| HPV18 | E1 | 11 | 470 |
| HPV18 | E1 | 10 | 399 |
| HPV18 | E1 | 11 | 399 |
| HPV18 | E1 | 9 | 452 |
| HPV18 | E1 | 10 | 452 |
| HPV18 | E1 | 8 | 226 |
| HPV18 | E1 | 8 | 130 |
| HPV18 | E1 | 8 | 508 |
| HPV18 | E1 | 9 | 508 |
| HPV18 | E1 | 10 | 508 |
| HPV18 | E1 | 9 | 257 |
| HPV18 | E1 | 10 | 257 |
| HPV18 | E1 | 11 | 257 |
| HPV18 | E1 | 9 | 356 |
| HPV18 | E1 | 9 | 332 |
| HPV18 | E1 | 11 | 223 |
| HPV18 | E1 | 8 | 494 |
| HPV18 | E1 | 9 | 55 |
| HPV18 | E1 | 8 | 11 |
| HPV18 | E1 | 9 | 11 |
| HPV18 | E1 | 8 | 473 |
| HPV18 | E1 | 10 | 473 |
| HPV18 | E1 | 8 | 182 |
| HPV18 | E1 | 8 | 279 |
| HPV18 | E1 | 10 | 279 |
| HPV18 | E1 | 10 | 249 |
| HPV18 | E1 | 8 | 16 |
| HPV18 | E1 | 8 | 499 |
| HPV18 | E1 | 10 | 499 |
| HPV18 | E1 | 9 | 270 |
| HPV18 | E1 | 8 | 306 |
| HPV18 | E1 | 9 | 306 |
| HPV18 | E1 | 10 | 418 |
| HPV18 | E1 | 8 | 247 |
| HPV18 | E1 | 11 | 352 |
| HPV18 | E1 | 9 | 266 |
| HPV18 | E1 | 10 | 461 |
| HPV18 | E1 | 11 | 461 |
| HPV18 | E1 | 10 | 590 |
| HPV18 | E1 | 10 | 23 |
| HPV18 | E1 | 10 | 449 |
| HPV18 | E1 | 8 | 439 |
| HPV18 | E1 | 11 | 439 |
| HPV18 | E1 | 11 | 647 |
| HPV18 | E1 | 9 | 318 |
| HPV18 | E1 | 10 | 318 |
| HPV18 | E1 | 11 | 318 |
| HPV18 | E1 | 8 | 259 |
| HPV18 | E1 | 9 | 259 |
| HPV18 | E1 | 10 | 259 |
| HPV18 | E1 | 11 | 237 |
| HPV18 | E1 | 9 | 206 |
| HPV18 | E1 | 10 | 206 |
| HPV18 | E1 | 9 | 277 |
| HPV18 | E1 | 10 | 277 |
| HPV18 | E1 | 9 | 407 |
| HPV18 | E1 | 9 | 129 |
| HPV18 | E1 | 8 | 281 |
| HPV18 | E1 | 9 | 561 |
| HPV18 | E1 | 10 | 561 |
| HPV18 | E1 | 11 | 561 |
| HPV18 | E1 | 8 | 261 |
| HPV18 | E1 | 11 | 261 |
| HPV18 | E1 | 9 | 304 |
| HPV18 | E1 | 10 | 304 |
| HPV18 | E1 | 11 | 304 |
| HPV18 | E1 | 11 | 204 |
| HPV18 | E1 | 11 | 285 |
| HPV18 | E1 | 9 | 376 |
| HPV18 | E1 | 11 | 376 |
| HPV18 | E1 | 8 | 520 |
| HPV18 | E1 | 9 | 520 |
| HPV18 | E1 | 8 | 350 |
| HPV18 | E1 | 10 | 295 |
| HPV18 | E1 | 11 | 295 |
| HPV18 | E1 | 8 | 267 |
| HPV18 | E1 | 8 | 326 |
| HPV18 | E1 | 11 | 326 |
| HPV18 | E1 | 9 | 214 |
| HPV18 | E1 | 11 | 214 |
| HPV18 | E1 | 10 | 527 |
| HPV18 | E1 | 8 | 312 |
| HPV18 | E1 | 11 | 47 |
| HPV18 | E1 | 10 | 367 |
| HPV18 | E1 | 10 | 361 |
| HPV18 | E1 | 11 | 188 |
| HPV18 | E1 | 10 | 574 |
| HPV18 | E1 | 8 | 428 |
| HPV18 | E1 | 9 | 487 |
| HPV18 | E1 | 11 | 487 |
| HPV18 | E1 | 11 | 158 |
| HPV18 | E1 | 8 | 191 |
| HPV18 | E1 | 11 | 191 |
| HPV18 | E1 | 10 | 615 |
| HPV18 | E1 | 10 | 600 |
| HPV18 | E1 | 8 | 264 |
| HPV18 | E1 | 11 | 264 |
| HPV18 | E1 | 8 | 568 |
| HPV18 | E1 | 11 | 551 |
| HPV18 | E1 | 8 | 448 |
| HPV18 | E1 | 11 | 448 |

TABLE X-continued

HLA A24 Supermotif Peptides

| 1 | 2 | 3 | 4 |
|---|---|---|---|
| HPV18 | E1 | 10 | 560 |
| HPV18 | E1 | 11 | 560 |
| HPV18 | E1 | 9 | 519 |
| HPV18 | E1 | 10 | 519 |
| HPV18 | E1 | 10 | 252 |
| HPV18 | E1 | 11 | 252 |
| HPV18 | E1 | 10 | 607 |
| HPV18 | E1 | 10 | 584 |
| HPV18 | E1 | 8 | 451 |
| HPV18 | E1 | 10 | 451 |
| HPV18 | E1 | 11 | 451 |
| HPV18 | E1 | 8 | 457 |
| HPV18 | E1 | 11 | 457 |
| HPV18 | E1 | 8 | 563 |
| HPV18 | E1 | 9 | 563 |
| HPV18 | E1 | 8 | 426 |
| HPV18 | E1 | 10 | 426 |
| HPV18 | E1 | 10 | 80 |
| HPV18 | E1 | 8 | 369 |
| HPV18 | E1 | 10 | 431 |
| HPV18 | E1 | 11 | 589 |
| HPV18 | E1 | 8 | 102 |
| HPV18 | E1 | 10 | 128 |
| HPV18 | E1 | 9 | 349 |
| HPV18 | E1 | 8 | 294 |
| HPV18 | E1 | 11 | 294 |
| HPV18 | E1 | 11 | 330 |
| HPV18 | E1 | 8 | 622 |
| HPV18 | E1 | 9 | 582 |
| HPV18 | E1 | 9 | 287 |
| HPV18 | E1 | 8 | 454 |
| HPV18 | E1 | 10 | 454 |
| HPV18 | E1 | 11 | 454 |
| HPV18 | E1 | 11 | 496 |
| HPV18 | E1 | 9 | 225 |
| HPV18 | E1 | 9 | 507 |
| HPV18 | E1 | 10 | 507 |
| HPV18 | E1 | 11 | 507 |
| HPV18 | E1 | 9 | 553 |
| HPV18 | E1 | 10 | 553 |
| HPV18 | E1 | 11 | 93 |
| HPV18 | E1 | 11 | 302 |
| HPV18 | E1 | 10 | 511 |
| HPV18 | E1 | 8 | 322 |
| HPV18 | E1 | 11 | 179 |
| HPV18 | E1 | 8 | 491 |
| HPV18 | E1 | 10 | 491 |
| HPV18 | E1 | 11 | 491 |
| HPV18 | E1 | 8 | 56 |
| HPV18 | E1 | 9 | 462 |
| HPV18 | E1 | 10 | 462 |
| HPV18 | E1 | 9 | 253 |
| HPV18 | E1 | 10 | 253 |
| HPV18 | E1 | 8 | 197 |
| HPV18 | E1 | 9 | 197 |
| HPV18 | E1 | 8 | 260 |
| HPV18 | E1 | 9 | 260 |
| HPV18 | E1 | 10 | 303 |
| HPV18 | E1 | 11 | 303 |
| HPV18 | E1 | 10 | 238 |
| HPV18 | E1 | 11 | 238 |
| HPV18 | E1 | 10 | 533 |
| HPV18 | E1 | 11 | 533 |
| HPV18 | E1 | 8 | 532 |
| HPV18 | E1 | 11 | 532 |
| HPV18 | E1 | 9 | 296 |
| HPV18 | E1 | 10 | 296 |
| HPV18 | E1 | 9 | 591 |
| HPV18 | E1 | 11 | 591 |
| HPV18 | E1 | 11 | 537 |
| HPV18 | E1 | 9 | 221 |
| HPV18 | E1 | 8 | 592 |
| HPV18 | E1 | 10 | 592 |
| HPV18 | E1 | 8 | 217 |
| HPV18 | E1 | 10 | 217 |
| HPV18 | E1 | 11 | 505 |
| HPV18 | E1 | 9 | 81 |
| HPV18 | E1 | 9 | 280 |
| HPV18 | E1 | 8 | 339 |
| HPV18 | E1 | 9 | 339 |
| HPV18 | E1 | 11 | 244 |
| HPV18 | E1 | 9 | 608 |
| HPV18 | E1 | 8 | 346 |
| HPV18 | E1 | 9 | 432 |
| HPV18 | E1 | 8 | 536 |
| HPV18 | E1 | 9 | 328 |
| HPV18 | E1 | 10 | 538 |
| HPV18 | E1 | 9 | 492 |
| HPV18 | E1 | 10 | 492 |
| HPV18 | E1 | 9 | 585 |
| HPV18 | E1 | 11 | 585 |
| HPV18 | E1 | 8 | 408 |
| HPV18 | E1 | 11 | 542 |
| HPV18 | E1 | 10 | 327 |
| HPV18 | E2 | 8 | 76 |
| HPV18 | E2 | 11 | 76 |
| HPV18 | E2 | 11 | 45 |
| HPV18 | E2 | 8 | 351 |
| HPV18 | E2 | 9 | 351 |
| HPV18 | E2 | 10 | 82 |
| HPV18 | E2 | 9 | 154 |
| HPV18 | E2 | 10 | 154 |
| HPV18 | E2 | 11 | 154 |
| HPV18 | E2 | 8 | 214 |
| HPV18 | E2 | 9 | 246 |
| HPV18 | E2 | 8 | 137 |
| HPV18 | E2 | 11 | 132 |
| HPV18 | E2 | 10 | 14 |
| HPV18 | E2 | 8 | 156 |
| HPV18 | E2 | 9 | 156 |
| HPV18 | E2 | 8 | 29 |
| HPV18 | E2 | 9 | 29 |
| HPV18 | E2 | 11 | 29 |
| HPV18 | E2 | 8 | 315 |
| HPV18 | E2 | 8 | 210 |
| HPV18 | E2 | 11 | 95 |
| HPV18 | E2 | 9 | 175 |
| HPV18 | E2 | 9 | 78 |
| HPV18 | E2 | 11 | 104 |
| HPV18 | E2 | 8 | 340 |
| HPV18 | E2 | 9 | 190 |
| HPV18 | E2 | 9 | 47 |
| HPV18 | E2 | 9 | 161 |
| HPV18 | E2 | 9 | 168 |
| HPV18 | E2 | 9 | 291 |
| HPV18 | E2 | 9 | 22 |
| HPV18 | E2 | 9 | 312 |
| HPV18 | E2 | 11 | 312 |
| HPV18 | E2 | 10 | 46 |
| HPV18 | E2 | 11 | 289 |
| HPV18 | E2 | 8 | 358 |
| HPV18 | E2 | 8 | 345 |
| HPV18 | E2 | 10 | 280 |
| HPV18 | E2 | 11 | 280 |
| HPV18 | E2 | 11 | 152 |
| HPV18 | E2 | 9 | 329 |
| HPV18 | E2 | 8 | 182 |
| HPV18 | E2 | 8 | 39 |
| HPV18 | E2 | 9 | 39 |
| HPV18 | E2 | 10 | 39 |
| HPV18 | E2 | 10 | 105 |
| HPV18 | E2 | 8 | 162 |
| HPV18 | E2 | 11 | 162 |
| HPV18 | E2 | 10 | 133 |
| HPV18 | E2 | 11 | 133 |
| HPV18 | E2 | 11 | 67 |
| HPV18 | E2 | 8 | 107 |
| HPV18 | E2 | 9 | 185 |
| HPV18 | E2 | 8 | 285 |
| HPV18 | E2 | 11 | 348 |

TABLE X-continued

HLA A24 Supermotif Peptides

| 1 | 2 | 3 | 4 |
|---|---|---|---|
| HPV18 | E2 | 9 | 196 |
| HPV18 | E2 | 10 | 272 |
| HPV18 | E2 | 9 | 357 |
| HPV18 | E2 | 8 | 33 |
| HPV18 | E2 | 10 | 33 |
| HPV18 | E2 | 9 | 38 |
| HPV18 | E2 | 10 | 38 |
| HPV18 | E2 | 11 | 38 |
| HPV18 | E2 | 9 | 220 |
| HPV18 | E2 | 11 | 56 |
| HPV18 | E2 | 11 | 2 |
| HPV18 | E2 | 8 | 61 |
| HPV18 | E2 | 8 | 35 |
| HPV18 | E2 | 9 | 305 |
| HPV18 | E2 | 9 | 11 |
| HPV18 | E2 | 10 | 11 |
| HPV18 | E2 | 10 | 343 |
| HPV18 | E2 | 8 | 41 |
| HPV18 | E2 | 9 | 90 |
| HPV18 | E2 | 11 | 303 |
| HPV18 | E2 | 9 | 298 |
| HPV18 | E2 | 11 | 230 |
| HPV18 | E2 | 8 | 233 |
| HPV18 | E2 | 8 | 355 |
| HPV18 | E2 | 9 | 355 |
| HPV18 | E2 | 11 | 355 |
| HPV18 | E2 | 11 | 140 |
| HPV18 | E2 | 10 | 57 |
| HPV18 | E2 | 9 | 97 |
| HPV18 | E2 | 10 | 97 |
| HPV18 | E2 | 10 | 349 |
| HPV18 | E2 | 11 | 349 |
| HPV18 | E2 | 11 | 211 |
| HPV18 | E2 | 10 | 231 |
| HPV18 | E2 | 11 | 188 |
| HPV18 | E2 | 11 | 336 |
| HPV18 | E2 | 9 | 134 |
| HPV18 | E2 | 10 | 134 |
| HPV18 | E2 | 11 | 134 |
| HPV18 | E2 | 8 | 197 |
| HPV18 | E2 | 11 | 123 |
| HPV18 | E2 | 10 | 141 |
| HPV18 | E2 | 11 | 322 |
| HPV18 | E2 | 10 | 96 |
| HPV18 | E2 | 11 | 96 |
| HPV18 | E2 | 10 | 124 |
| HPV18 | E2 | 11 | 173 |
| HPV18 | E2 | 8 | 143 |
| HPV18 | E2 | 8 | 135 |
| HPV18 | E2 | 9 | 135 |
| HPV18 | E2 | 10 | 135 |
| HPV18 | E2 | 9 | 164 |
| HPV18 | E2 | 10 | 164 |
| HPV18 | E2 | 11 | 164 |
| HPV18 | E2 | 11 | 36 |
| HPV18 | E2 | 9 | 142 |
| HPV18 | E2 | 10 | 163 |
| HPV18 | E2 | 11 | 163 |
| HPV18 | E5 | 9 | 49 |
| HPV18 | E5 | 10 | 49 |
| HPV18 | E5 | 11 | 49 |
| HPV18 | E5 | 9 | 47 |
| HPV18 | E5 | 11 | 47 |
| HPV18 | E5 | 8 | 32 |
| HPV18 | E5 | 9 | 32 |
| HPV18 | E5 | 8 | 30 |
| HPV18 | E5 | 10 | 30 |
| HPV18 | E5 | 11 | 30 |
| HPV18 | E5 | 8 | 56 |
| HPV18 | E5 | 9 | 56 |
| HPV18 | E5 | 11 | 56 |
| HPV18 | E5 | 9 | 27 |
| HPV18 | E5 | 11 | 27 |
| HPV18 | E5 | 10 | 13 |
| HPV18 | E5 | 11 | 13 |
| HPV18 | E5 | 9 | 6 |
| HPV18 | E5 | 10 | 6 |
| HPV18 | E5 | 8 | 57 |
| HPV18 | E5 | 10 | 57 |
| HPV18 | E5 | 8 | 50 |
| HPV18 | E5 | 9 | 50 |
| HPV18 | E5 | 10 | 50 |
| HPV18 | E5 | 8 | 65 |
| HPV18 | E5 | 10 | 19 |
| HPV18 | E5 | 10 | 5 |
| HPV18 | E5 | 11 | 5 |
| HPV18 | E5 | 8 | 43 |
| HPV18 | E5 | 11 | 43 |
| HPV18 | E5 | 11 | 40 |
| HPV18 | E5 | 8 | 7 |
| HPV18 | E5 | 9 | 7 |
| HPV18 | E5 | 11 | 4 |
| HPV18 | E5 | 8 | 63 |
| HPV18 | E5 | 10 | 63 |
| HPV18 | E5 | 8 | 62 |
| HPV18 | E5 | 9 | 62 |
| HPV18 | E5 | 11 | 62 |
| HPV18 | E5 | 9 | 58 |
| HPV18 | E5 | 10 | 22 |
| HPV18 | E5 | 9 | 35 |
| HPV18 | E5 | 9 | 61 |
| HPV18 | E5 | 10 | 61 |
| HPV18 | E5 | 8 | 1 |
| HPV18 | E5 | 10 | 1 |
| HPV18 | E5 | 9 | 14 |
| HPV18 | E5 | 10 | 14 |
| HPV18 | E5 | 8 | 21 |
| HPV18 | E5 | 11 | 21 |
| HPV18 | E5 | 10 | 60 |
| HPV18 | E5 | 11 | 60 |
| HPV18 | E5 | 8 | 3 |
| HPV18 | E5 | 9 | 25 |
| HPV18 | E5 | 11 | 25 |
| HPV18 | E5 | 8 | 51 |
| HPV18 | E5 | 9 | 51 |
| HPV18 | E5 | 11 | 51 |
| HPV18 | E5 | 8 | 54 |
| HPV18 | E5 | 9 | 54 |
| HPV18 | E5 | 10 | 54 |
| HPV18 | E5 | 11 | 54 |
| HPV18 | E5 | 8 | 36 |
| HPV18 | E5 | 9 | 42 |
| HPV18 | E5 | 10 | 34 |
| HPV18 | E5 | 10 | 41 |
| HPV18 | E5 | 8 | 52 |
| HPV18 | E5 | 10 | 52 |
| HPV18 | E5 | 11 | 52 |
| HPV18 | E5 | 8 | 33 |
| HPV18 | E5 | 11 | 33 |
| HPV18 | E5 | 8 | 15 |
| HPV18 | E5 | 9 | 15 |
| HPV18 | E5 | 9 | 53 |
| HPV18 | E5 | 10 | 53 |
| HPV18 | E5 | 11 | 53 |
| HPV18 | E6 | 9 | 48 |
| HPV18 | E6 | 8 | 68 |
| HPV18 | E6 | 11 | 68 |
| HPV18 | E6 | 8 | 105 |
| HPV18 | E6 | 8 | 18 |
| HPV18 | E6 | 11 | 18 |
| HPV18 | E6 | 8 | 32 |
| HPV18 | E6 | 10 | 32 |
| HPV18 | E6 | 9 | 70 |
| HPV18 | E6 | 8 | 27 |
| HPV18 | E6 | 10 | 16 |
| HPV18 | E6 | 10 | 51 |
| HPV18 | E6 | 11 | 88 |
| HPV18 | E6 | 8 | 46 |
| HPV18 | E6 | 11 | 46 |
| HPV18 | E6 | 11 | 29 |

TABLE X-continued

HLA A24 Supermotif Peptides

| 1 | 2 | 3 | 4 |
|---|---|---|---|
| HPV18 | E6 | 9 | 20 |
| HPV18 | E6 | 11 | 20 |
| HPV18 | E6 | 10 | 77 |
| HPV18 | E6 | 8 | 40 |
| HPV18 | E6 | 10 | 40 |
| HPV18 | E6 | 10 | 43 |
| HPV18 | E6 | 11 | 43 |
| HPV18 | E6 | 8 | 53 |
| HPV18 | E6 | 8 | 71 |
| HPV18 | E6 | 11 | 71 |
| HPV18 | E6 | 10 | 97 |
| HPV18 | E6 | 8 | 120 |
| HPV18 | E6 | 11 | 120 |
| HPV18 | E6 | 11 | 80 |
| HPV18 | E6 | 10 | 30 |
| HPV18 | E6 | 9 | 13 |
| HPV18 | E6 | 11 | 117 |
| HPV18 | E6 | 8 | 92 |
| HPV18 | E6 | 10 | 92 |
| HPV18 | E6 | 11 | 92 |
| HPV18 | E6 | 10 | 36 |
| HPV18 | E6 | 9 | 52 |
| HPV18 | E6 | 11 | 102 |
| HPV18 | E6 | 9 | 41 |
| HPV18 | E6 | 9 | 93 |
| HPV18 | E6 | 10 | 93 |
| HPV18 | E6 | 11 | 93 |
| HPV18 | E6 | 9 | 98 |
| HPV18 | E6 | 8 | 95 |
| HPV18 | E6 | 9 | 95 |
| HPV18 | E6 | 9 | 22 |
| HPV18 | E6 | 8 | 111 |
| HPV18 | E6 | 11 | 111 |
| HPV18 | E6 | 8 | 7 |
| HPV18 | E6 | 11 | 7 |
| HPV18 | E6 | 11 | 11 |
| HPV18 | E6 | 10 | 3 |
| HPV18 | E6 | 9 | 126 |
| HPV18 | E6 | 8 | 74 |
| HPV18 | E6 | 11 | 59 |
| HPV18 | E6 | 11 | 24 |
| HPV18 | E6 | 10 | 84 |
| HPV18 | E6 | 10 | 89 |
| HPV18 | E6 | 11 | 89 |
| HPV18 | E6 | 9 | 37 |
| HPV18 | E6 | 11 | 37 |
| HPV18 | E6 | 9 | 44 |
| HPV18 | E6 | 10 | 44 |
| HPV18 | E6 | 8 | 38 |
| HPV18 | E6 | 10 | 38 |
| HPV18 | E6 | 9 | 33 |
| HPV18 | E6 | 9 | 85 |
| HPV18 | E7 | 10 | 85 |
| HPV18 | E7 | 8 | 6 |
| HPV18 | E7 | 10 | 6 |
| HPV18 | E7 | 10 | 63 |
| HPV18 | E7 | 8 | 24 |
| HPV18 | E7 | 8 | 82 |
| HPV18 | E7 | 9 | 82 |
| HPV18 | E7 | 10 | 82 |
| HPV18 | E7 | 10 | 40 |
| HPV18 | E7 | 11 | 90 |
| HPV18 | E7 | 8 | 14 |
| HPV18 | E7 | 11 | 11 |
| HPV18 | E7 | 11 | 73 |
| HPV18 | E7 | 8 | 89 |
| HPV18 | E7 | 10 | 74 |
| HPV18 | E7 | 9 | 92 |
| HPV18 | E7 | 10 | 22 |
| HPV18 | E7 | 9 | 88 |
| HPV18 | E7 | 9 | 7 |
| HPV18 | E7 | 8 | 93 |
| HPV18 | E7 | 10 | 12 |
| HPV18 | E7 | 9 | 75 |
| HPV18 | L1 | 11 | 63 |
| HPV18 | L1 | 11 | 128 |
| HPV18 | L1 | 9 | 218 |
| HPV18 | L1 | 8 | 310 |
| HPV18 | L1 | 8 | 2 |
| HPV18 | L1 | 9 | 2 |
| HPV18 | L1 | 11 | 2 |
| HPV18 | L1 | 10 | 441 |
| HPV18 | L1 | 11 | 350 |
| HPV18 | L1 | 9 | 284 |
| HPV18 | L1 | 8 | 122 |
| HPV18 | L1 | 10 | 122 |
| HPV18 | L1 | 11 | 520 |
| HPV18 | L1 | 8 | 512 |
| HPV18 | L1 | 10 | 512 |
| HPV18 | L1 | 8 | 433 |
| HPV18 | L1 | 11 | 433 |
| HPV18 | L1 | 10 | 260 |
| HPV18 | L1 | 9 | 263 |
| HPV18 | L1 | 8 | 276 |
| HPV18 | L1 | 10 | 276 |
| HPV18 | L1 | 8 | 396 |
| HPV18 | L1 | 10 | 396 |
| HPV18 | L1 | 8 | 330 |
| HPV18 | L1 | 9 | 330 |
| HPV18 | L1 | 11 | 478 |
| HPV18 | L1 | 9 | 448 |
| HPV18 | L1 | 10 | 203 |
| HPV18 | L1 | 9 | 211 |
| HPV18 | L1 | 10 | 211 |
| HPV18 | L1 | 10 | 294 |
| HPV18 | L1 | 8 | 87 |
| HPV18 | L1 | 9 | 87 |
| HPV18 | L1 | 10 | 87 |
| HPV18 | L1 | 8 | 167 |
| HPV18 | L1 | 10 | 280 |
| HPV18 | L1 | 8 | 431 |
| HPV18 | L1 | 10 | 431 |
| HPV18 | L1 | 9 | 308 |
| HPV18 | L1 | 10 | 308 |
| HPV18 | L1 | 8 | 436 |
| HPV18 | L1 | 10 | 436 |
| HPV18 | L1 | 8 | 49 |
| HPV18 | L1 | 10 | 49 |
| HPV18 | L1 | 11 | 49 |
| HPV18 | L1 | 8 | 321 |
| HPV18 | L1 | 10 | 508 |
| HPV18 | L1 | 9 | 95 |
| HPV18 | L1 | 10 | 95 |
| HPV18 | L1 | 8 | 145 |
| HPV18 | L1 | 8 | 535 |
| HPV18 | L1 | 8 | 177 |
| HPV18 | L1 | 11 | 177 |
| HPV18 | L1 | 11 | 342 |
| HPV18 | L1 | 9 | 233 |
| HPV18 | L1 | 11 | 326 |
| HPV18 | L1 | 8 | 383 |
| HPV18 | L1 | 9 | 383 |
| HPV18 | L1 | 10 | 165 |
| HPV18 | L1 | 9 | 175 |
| HPV18 | L1 | 10 | 175 |
| HPV18 | L1 | 10 | 467 |
| HPV18 | L1 | 10 | 265 |
| HPV18 | L1 | 9 | 320 |
| HPV18 | L1 | 8 | 38 |
| HPV18 | L1 | 9 | 38 |
| HPV18 | L1 | 10 | 38 |
| HPV18 | L1 | 11 | 38 |
| HPV18 | L1 | 9 | 13 |
| HPV18 | L1 | 10 | 13 |
| HPV18 | L1 | 9 | 428 |
| HPV18 | L1 | 10 | 428 |
| HPV18 | L1 | 11 | 428 |
| HPV18 | L1 | 8 | 11 |
| HPV18 | L1 | 11 | 11 |
| HPV18 | L1 | 8 | 58 |

TABLE X-continued

HLA A24 Supermotif Peptides

| 1 | 2 | 3 | 4 |
|---|---|---|---|
| HPV18 | L1 | 9 | 437 |
| HPV18 | L1 | 10 | 94 |
| HPV18 | L1 | 11 | 94 |
| HPV18 | L1 | 8 | 40 |
| HPV18 | L1 | 9 | 40 |
| HPV18 | L1 | 10 | 40 |
| HPV18 | L1 | 11 | 40 |
| HPV18 | L1 | 8 | 39 |
| HPV18 | L1 | 9 | 39 |
| HPV18 | L1 | 10 | 39 |
| HPV18 | L1 | 11 | 39 |
| HPV18 | L1 | 11 | 46 |
| HPV18 | L1 | 10 | 47 |
| HPV18 | L1 | 8 | 219 |
| HPV18 | L1 | 9 | 9 |
| HPV18 | L1 | 10 | 9 |
| HPV18 | L1 | 8 | 32 |
| HPV18 | L1 | 9 | 32 |
| HPV18 | L1 | 10 | 32 |
| HPV18 | L1 | 8 | 443 |
| HPV18 | L1 | 10 | 443 |
| HPV18 | L1 | 11 | 443 |
| HPV18 | L1 | 8 | 360 |
| HPV18 | L1 | 9 | 360 |
| HPV18 | L1 | 9 | 151 |
| HPV18 | L1 | 11 | 151 |
| HPV18 | L1 | 9 | 143 |
| HPV18 | L1 | 10 | 143 |
| HPV18 | L1 | 8 | 529 |
| HPV18 | L1 | 9 | 516 |
| HPV18 | L1 | 11 | 516 |
| HPV18 | L1 | 11 | 507 |
| HPV18 | L1 | 9 | 505 |
| HPV18 | L1 | 10 | 125 |
| HPV18 | L1 | 8 | 291 |
| HPV18 | L1 | 9 | 48 |
| HPV18 | L1 | 11 | 48 |
| HPV18 | L1 | 8 | 367 |
| HPV18 | L1 | 8 | 8 |
| HPV18 | L1 | 10 | 8 |
| HPV18 | L1 | 11 | 8 |
| HPV18 | L1 | 8 | 14 |
| HPV18 | L1 | 9 | 14 |
| HPV18 | L1 | 8 | 103 |
| HPV18 | L1 | 9 | 103 |
| HPV18 | L1 | 8 | 445 |
| HPV18 | L1 | 9 | 445 |
| HPV18 | L1 | 8 | 104 |
| HPV18 | L1 | 10 | 159 |
| HPV18 | L1 | 8 | 33 |
| HPV18 | L1 | 9 | 33 |
| HPV18 | L1 | 10 | 64 |
| HPV18 | L1 | 11 | 64 |
| HPV18 | L1 | 11 | 17 |
| HPV18 | L1 | 9 | 21 |
| HPV18 | L1 | 8 | 336 |
| HPV18 | L1 | 8 | 3 |
| HPV18 | L1 | 10 | 3 |
| HPV18 | L1 | 10 | 307 |
| HPV18 | L1 | 11 | 307 |
| HPV18 | L1 | 9 | 261 |
| HPV18 | L1 | 11 | 261 |
| HPV18 | L1 | 10 | 36 |
| HPV18 | L1 | 11 | 36 |
| HPV18 | L1 | 11 | 84 |
| HPV18 | L1 | 9 | 253 |
| HPV18 | L1 | 8 | 510 |
| HPV18 | L1 | 10 | 510 |
| HPV18 | L1 | 9 | 54 |
| HPV18 | L1 | 11 | 54 |
| HPV18 | L1 | 8 | 52 |
| HPV18 | L1 | 9 | 52 |
| HPV18 | L1 | 11 | 52 |
| HPV18 | L1 | 11 | 207 |
| HPV18 | L1 | 8 | 57 |
| HPV18 | L1 | 9 | 57 |
| HPV18 | L1 | 8 | 282 |
| HPV18 | L1 | 11 | 282 |
| HPV18 | L1 | 9 | 248 |
| HPV18 | L1 | 11 | 173 |
| HPV18 | L1 | 8 | 28 |
| HPV18 | L1 | 9 | 28 |
| HPV18 | L1 | 8 | 26 |
| HPV18 | L1 | 10 | 26 |
| HPV18 | L1 | 11 | 26 |
| HPV18 | L1 | 10 | 240 |
| HPV18 | L1 | 8 | 20 |
| HPV18 | L1 | 10 | 20 |
| HPV18 | L1 | 9 | 472 |
| HPV18 | L1 | 11 | 472 |
| HPV18 | L1 | 11 | 412 |
| HPV18 | L1 | 8 | 502 |
| HPV18 | L1 | 8 | 302 |
| HPV18 | L1 | 10 | 302 |
| HPV18 | L1 | 9 | 435 |
| HPV18 | L1 | 11 | 435 |
| HPV18 | L1 | 11 | 216 |
| HPV18 | L1 | 8 | 315 |
| HPV18 | L1 | 8 | 366 |
| HPV18 | L1 | 9 | 366 |
| HPV18 | L1 | 8 | 137 |
| HPV18 | L1 | 10 | 137 |
| HPV18 | L1 | 11 | 297 |
| HPV18 | L1 | 10 | 416 |
| HPV18 | L1 | 8 | 523 |
| HPV18 | L1 | 9 | 523 |
| HPV18 | L1 | 9 | 130 |
| HPV18 | L1 | 9 | 424 |
| HPV18 | L1 | 11 | 424 |
| HPV18 | L1 | 8 | 481 |
| HPV18 | L1 | 9 | 102 |
| HPV18 | L1 | 10 | 102 |
| HPV18 | L1 | 11 | 158 |
| HPV18 | L1 | 9 | 6 |
| HPV18 | L1 | 10 | 6 |
| HPV18 | L1 | 10 | 135 |
| HPV18 | L1 | 8 | 81 |
| HPV18 | L1 | 8 | 288 |
| HPV18 | L1 | 9 | 288 |
| HPV18 | L1 | 11 | 288 |
| HPV18 | L1 | 11 | 93 |
| HPV18 | L1 | 8 | 459 |
| HPV18 | L1 | 9 | 31 |
| HPV18 | L1 | 10 | 31 |
| HPV18 | L1 | 11 | 31 |
| HPV18 | L1 | 9 | 359 |
| HPV18 | L1 | 10 | 359 |
| HPV18 | L1 | 10 | 150 |
| HPV18 | L1 | 9 | 518 |
| HPV18 | L1 | 8 | 475 |
| HPV18 | L1 | 9 | 335 |
| HPV18 | L1 | 11 | 306 |
| HPV18 | L1 | 10 | 455 |
| HPV18 | L1 | 10 | 408 |
| HPV18 | L1 | 11 | 78 |
| HPV18 | L1 | 9 | 209 |
| HPV18 | L1 | 11 | 209 |
| HPV18 | L1 | 10 | 451 |
| HPV18 | L1 | 11 | 451 |
| HPV18 | L1 | 9 | 442 |
| HPV18 | L1 | 11 | 442 |
| HPV18 | L1 | 11 | 273 |
| HPV18 | L1 | 9 | 444 |
| HPV18 | L1 | 10 | 444 |
| HPV18 | L1 | 10 | 327 |
| HPV18 | L1 | 11 | 327 |
| HPV18 | L1 | 9 | 397 |
| HPV18 | L1 | 8 | 473 |
| HPV18 | L1 | 10 | 473 |
| HPV18 | L1 | 8 | 254 |

TABLE X-continued

HLA A24 Supermotif Peptides

| 1 | 2 | 3 | 4 |
|---|---|---|---|
| HPV18 | L1 | 8 | 331 |
| HPV18 | L1 | 11 | 393 |
| HPV18 | L1 | 10 | 479 |
| HPV18 | L1 | 8 | 55 |
| HPV18 | L1 | 10 | 55 |
| HPV18 | L1 | 11 | 55 |
| HPV18 | L1 | 8 | 7 |
| HPV18 | L1 | 9 | 7 |
| HPV18 | L1 | 11 | 7 |
| HPV18 | L1 | 8 | 449 |
| HPV18 | L1 | 8 | 89 |
| HPV18 | L1 | 8 | 361 |
| HPV18 | L1 | 10 | 394 |
| HPV18 | L1 | 9 | 160 |
| HPV18 | L1 | 8 | 34 |
| HPV18 | L1 | 10 | 351 |
| HPV18 | L1 | 9 | 452 |
| HPV18 | L1 | 10 | 452 |
| HPV18 | L1 | 9 | 295 |
| HPV18 | L1 | 11 | 35 |
| HPV18 | L1 | 9 | 4 |
| HPV18 | L1 | 11 | 4 |
| HPV18 | L1 | 8 | 88 |
| HPV18 | L1 | 9 | 88 |
| HPV18 | L2 | 9 | 255 |
| HPV18 | L2 | 11 | 255 |
| HPV18 | L2 | 9 | 370 |
| HPV18 | L2 | 8 | 161 |
| HPV18 | L2 | 11 | 286 |
| HPV18 | L2 | 8 | 341 |
| HPV18 | L2 | 10 | 341 |
| HPV18 | L2 | 11 | 341 |
| HPV18 | L2 | 11 | 303 |
| HPV18 | L2 | 8 | 275 |
| HPV18 | L2 | 10 | 278 |
| HPV18 | L2 | 11 | 322 |
| HPV18 | L2 | 11 | 404 |
| HPV18 | L2 | 11 | 142 |
| HPV18 | L2 | 10 | 346 |
| HPV18 | L2 | 11 | 83 |
| HPV18 | L2 | 8 | 270 |
| HPV18 | L2 | 10 | 270 |
| HPV18 | L2 | 11 | 270 |
| HPV18 | L2 | 10 | 396 |
| HPV18 | L2 | 11 | 30 |
| HPV18 | L2 | 9 | 240 |
| HPV18 | L2 | 10 | 240 |
| HPV18 | L2 | 8 | 331 |
| HPV18 | L2 | 8 | 371 |
| HPV18 | L2 | 11 | 443 |
| HPV18 | L2 | 8 | 241 |
| HPV18 | L2 | 9 | 241 |
| HPV18 | L2 | 11 | 241 |
| HPV18 | L2 | 9 | 122 |
| HPV18 | L2 | 11 | 157 |
| HPV18 | L2 | 8 | 306 |
| HPV18 | L2 | 8 | 319 |
| HPV18 | L2 | 9 | 51 |
| HPV18 | L2 | 8 | 429 |
| HPV18 | L2 | 9 | 429 |
| HPV18 | L2 | 10 | 429 |
| HPV18 | L2 | 8 | 64 |
| HPV18 | L2 | 9 | 64 |
| HPV18 | L2 | 11 | 64 |
| HPV18 | L2 | 8 | 188 |
| HPV18 | L2 | 10 | 188 |
| HPV18 | L2 | 9 | 432 |
| HPV18 | L2 | 10 | 432 |
| HPV18 | L2 | 11 | 432 |
| HPV18 | L2 | 10 | 183 |
| HPV18 | L2 | 10 | 310 |
| HPV18 | L2 | 11 | 310 |
| HPV18 | L2 | 8 | 37 |
| HPV18 | L2 | 9 | 37 |
| HPV18 | L2 | 11 | 37 |
| HPV18 | L2 | 8 | 134 |
| HPV18 | L2 | 10 | 134 |
| HPV18 | L2 | 8 | 292 |
| HPV18 | L2 | 10 | 191 |
| HPV18 | L2 | 9 | 318 |
| HPV18 | L2 | 8 | 434 |
| HPV18 | L2 | 9 | 434 |
| HPV18 | L2 | 10 | 434 |
| HPV18 | L2 | 11 | 434 |
| HPV18 | L2 | 8 | 52 |
| HPV18 | L2 | 9 | 279 |
| HPV18 | L2 | 9 | 44 |
| HPV18 | L2 | 10 | 44 |
| HPV18 | L2 | 11 | 44 |
| HPV18 | L2 | 10 | 405 |
| HPV18 | L2 | 10 | 143 |
| HPV18 | L2 | 8 | 249 |
| HPV18 | L2 | 8 | 43 |
| HPV18 | L2 | 10 | 43 |
| HPV18 | L2 | 11 | 43 |
| HPV18 | L2 | 11 | 34 |
| HPV18 | L2 | 9 | 347 |
| HPV18 | L2 | 9 | 248 |
| HPV18 | L2 | 8 | 242 |
| HPV18 | L2 | 10 | 242 |
| HPV18 | L2 | 10 | 287 |
| HPV18 | L2 | 10 | 391 |
| HPV18 | L2 | 10 | 338 |
| HPV18 | L2 | 11 | 338 |
| HPV18 | L2 | 8 | 437 |
| HPV18 | L2 | 9 | 305 |
| HPV18 | L2 | 10 | 386 |
| HPV18 | L2 | 8 | 325 |
| HPV18 | L2 | 9 | 325 |
| HPV18 | L2 | 11 | 325 |
| HPV18 | L2 | 11 | 390 |
| HPV18 | L2 | 11 | 337 |
| HPV18 | L2 | 9 | 419 |
| HPV18 | L2 | 10 | 419 |
| HPV18 | L2 | 9 | 98 |
| HPV18 | L2 | 10 | 98 |
| HPV18 | L2 | 9 | 120 |
| HPV18 | L2 | 11 | 120 |
| HPV18 | L2 | 9 | 376 |
| HPV18 | L2 | 8 | 86 |
| HPV18 | L2 | 8 | 185 |
| HPV18 | L2 | 11 | 185 |
| HPV18 | L2 | 11 | 216 |
| HPV18 | L2 | 8 | 258 |
| HPV18 | L2 | 9 | 95 |
| HPV18 | L2 | 10 | 360 |
| HPV18 | L2 | 8 | 398 |
| HPV18 | L2 | 10 | 398 |
| HPV18 | L2 | 8 | 452 |
| HPV18 | L2 | 8 | 312 |
| HPV18 | L2 | 9 | 312 |
| HPV18 | L2 | 10 | 172 |
| HPV18 | L2 | 9 | 233 |
| HPV18 | L2 | 10 | 233 |
| HPV18 | L2 | 8 | 46 |
| HPV18 | L2 | 9 | 46 |
| HPV18 | L2 | 10 | 426 |
| HPV18 | L2 | 11 | 426 |
| HPV18 | L2 | 11 | 295 |
| HPV18 | L2 | 8 | 298 |
| HPV18 | L2 | 9 | 298 |
| HPV18 | L2 | 8 | 220 |
| HPV18 | L2 | 8 | 316 |
| HPV18 | L2 | 11 | 316 |
| HPV18 | L2 | 10 | 450 |
| HPV18 | L2 | 11 | 368 |
| HPV18 | L2 | 9 | 49 |
| HPV18 | L2 | 11 | 49 |
| HPV18 | L2 | 10 | 247 |
| HPV18 | L2 | 11 | 147 |

TABLE X-continued

HLA A24 Supermotif Peptides

| 1 | 2 | 3 | 4 |
|---|---|---|---|
| HPV18 | L2 | 10 | 153 |
| HPV18 | L2 | 8 | 365 |
| HPV18 | L2 | 10 | 365 |
| HPV18 | L2 | 8 | 409 |
| HPV18 | L2 | 8 | 235 |
| HPV18 | L2 | 9 | 149 |
| HPV18 | L2 | 9 | 383 |
| HPV18 | L2 | 8 | 121 |
| HPV18 | L2 | 10 | 121 |
| HPV18 | L2 | 8 | 377 |
| HPV18 | L2 | 9 | 39 |
| HPV18 | L2 | 9 | 406 |
| HPV18 | L2 | 11 | 406 |
| HPV18 | L2 | 10 | 304 |
| HPV18 | L2 | 8 | 38 |
| HPV18 | L2 | 10 | 38 |
| HPV18 | L2 | 9 | 154 |
| HPV18 | L2 | 8 | 136 |
| HPV18 | L2 | 9 | 366 |
| HPV18 | L2 | 9 | 135 |
| HPV18 | L2 | 8 | 388 |
| HPV18 | L2 | 10 | 217 |
| HPV18 | L2 | 11 | 217 |
| HPV18 | L2 | 10 | 113 |
| HPV18 | L2 | 9 | 387 |
| HPV18 | L2 | 10 | 31 |
| HPV18 | L2 | 11 | 112 |
| HPV18 | L2 | 9 | 399 |
| HPV18 | L2 | 9 | 427 |
| HPV18 | L2 | 10 | 427 |
| HPV18 | L2 | 11 | 427 |
| HPV18 | L2 | 8 | 436 |
| HPV18 | L2 | 9 | 436 |
| HPV18 | L2 | 8 | 400 |
| HPV18 | L2 | 8 | 435 |
| HPV18 | L2 | 9 | 435 |
| HPV18 | L2 | 10 | 435 |
| HPV31 | E1 | 11 | 371 |
| HPV31 | E1 | 9 | 519 |
| HPV31 | E1 | 10 | 533 |
| HPV31 | E1 | 11 | 533 |
| HPV31 | E1 | 9 | 298 |
| HPV31 | E1 | 9 | 186 |
| HPV31 | E1 | 10 | 186 |
| HPV31 | E1 | 8 | 504 |
| HPV31 | E1 | 9 | 504 |
| HPV31 | E1 | 11 | 22 |
| HPV31 | E1 | 9 | 81 |
| HPV31 | E1 | 8 | 279 |
| HPV31 | E1 | 9 | 279 |
| HPV31 | E1 | 9 | 239 |
| HPV31 | E1 | 9 | 284 |
| HPV31 | E1 | 9 | 213 |
| HPV31 | E1 | 10 | 100 |
| HPV31 | E1 | 10 | 620 |
| HPV31 | E1 | 8 | 508 |
| HPV31 | E1 | 9 | 508 |
| HPV31 | E1 | 9 | 49 |
| HPV31 | E1 | 8 | 96 |
| HPV31 | E1 | 10 | 96 |
| HPV31 | E1 | 8 | 421 |
| HPV31 | E1 | 11 | 421 |
| HPV31 | E1 | 8 | 336 |
| HPV31 | E1 | 10 | 336 |
| HPV31 | E1 | 9 | 42 |
| HPV31 | E1 | 10 | 42 |
| HPV31 | E1 | 9 | 332 |
| HPV31 | E1 | 8 | 528 |
| HPV31 | E1 | 10 | 528 |
| HPV31 | E1 | 8 | 348 |
| HPV31 | E1 | 10 | 348 |
| HPV31 | E1 | 9 | 311 |
| HPV31 | E1 | 10 | 311 |
| HPV31 | E1 | 8 | 418 |
| HPV31 | E1 | 9 | 418 |
| HPV31 | E1 | 11 | 418 |
| HPV31 | E1 | 8 | 102 |
| HPV31 | E1 | 11 | 102 |
| HPV31 | E1 | 9 | 432 |
| HPV31 | E1 | 11 | 432 |
| HPV31 | E1 | 9 | 354 |
| HPV31 | E1 | 10 | 583 |
| HPV31 | E1 | 11 | 583 |
| HPV31 | E1 | 8 | 193 |
| HPV31 | E1 | 10 | 193 |
| HPV31 | E1 | 11 | 193 |
| HPV31 | E1 | 8 | 168 |
| HPV31 | E1 | 11 | 168 |
| HPV31 | E1 | 9 | 318 |
| HPV31 | E1 | 9 | 592 |
| HPV31 | E1 | 11 | 592 |
| HPV31 | E1 | 8 | 50 |
| HPV31 | E1 | 11 | 443 |
| HPV31 | E1 | 10 | 372 |
| HPV31 | E1 | 9 | 473 |
| HPV31 | E1 | 9 | 425 |
| HPV31 | E1 | 8 | 436 |
| HPV31 | E1 | 9 | 436 |
| HPV31 | E1 | 8 | 199 |
| HPV31 | E1 | 9 | 566 |
| HPV31 | E1 | 8 | 433 |
| HPV31 | E1 | 10 | 433 |
| HPV31 | E1 | 11 | 433 |
| HPV31 | E1 | 11 | 488 |
| HPV31 | E1 | 9 | 230 |
| HPV31 | E1 | 11 | 230 |
| HPV31 | E1 | 11 | 499 |
| HPV31 | E1 | 8 | 467 |
| HPV31 | E1 | 9 | 305 |
| HPV31 | E1 | 10 | 252 |
| HPV31 | E1 | 8 | 11 |
| HPV31 | E1 | 9 | 11 |
| HPV31 | E1 | 10 | 225 |
| HPV31 | E1 | 11 | 225 |
| HPV31 | E1 | 8 | 446 |
| HPV31 | E1 | 9 | 446 |
| HPV31 | E1 | 10 | 446 |
| HPV31 | E1 | 8 | 196 |
| HPV31 | E1 | 11 | 196 |
| HPV31 | E1 | 10 | 222 |
| HPV31 | E1 | 9 | 16 |
| HPV31 | E1 | 9 | 243 |
| HPV31 | E1 | 11 | 243 |
| HPV31 | E1 | 11 | 510 |
| HPV31 | E1 | 10 | 391 |
| HPV31 | E1 | 11 | 478 |
| HPV31 | E1 | 10 | 268 |
| HPV31 | E1 | 11 | 268 |
| HPV31 | E1 | 8 | 381 |
| HPV31 | E1 | 10 | 422 |
| HPV31 | E1 | 10 | 190 |
| HPV31 | E1 | 11 | 190 |
| HPV31 | E1 | 8 | 424 |
| HPV31 | E1 | 10 | 424 |
| HPV31 | E1 | 9 | 380 |
| HPV31 | E1 | 10 | 276 |
| HPV31 | E1 | 11 | 276 |
| HPV31 | E1 | 9 | 272 |
| HPV31 | E1 | 9 | 291 |
| HPV31 | E1 | 10 | 291 |
| HPV31 | E1 | 11 | 291 |
| HPV31 | E1 | 8 | 119 |
| HPV31 | E1 | 10 | 119 |
| HPV31 | E1 | 9 | 232 |
| HPV31 | E1 | 10 | 232 |
| HPV31 | E1 | 9 | 179 |
| HPV31 | E1 | 10 | 179 |
| HPV31 | E1 | 8 | 412 |
| HPV31 | E1 | 11 | 412 |
| HPV31 | E1 | 10 | 88 |

TABLE X-continued

HLA A24 Supermotif Peptides

| 1 | 2 | 3 | 4 |
|---|---|---|---|
| HPV31 | E1 | 9 | 125 |
| HPV31 | E1 | 9 | 470 |
| HPV31 | E1 | 10 | 470 |
| HPV31 | E1 | 9 | 277 |
| HPV31 | E1 | 10 | 277 |
| HPV31 | E1 | 11 | 277 |
| HPV31 | E1 | 8 | 273 |
| HPV31 | E1 | 8 | 234 |
| HPV31 | E1 | 11 | 234 |
| HPV31 | E1 | 9 | 534 |
| HPV31 | E1 | 10 | 534 |
| HPV31 | E1 | 11 | 534 |
| HPV31 | E1 | 11 | 258 |
| HPV31 | E1 | 10 | 563 |
| HPV31 | E1 | 8 | 240 |
| HPV31 | E1 | 9 | 194 |
| HPV31 | E1 | 10 | 194 |
| HPV31 | E1 | 8 | 299 |
| HPV31 | E1 | 11 | 299 |
| HPV31 | E1 | 10 | 500 |
| HPV31 | E1 | 8 | 187 |
| HPV31 | E1 | 9 | 187 |
| HPV31 | E1 | 8 | 285 |
| HPV31 | E1 | 11 | 47 |
| HPV31 | E1 | 9 | 253 |
| HPV31 | E1 | 11 | 143 |
| HPV31 | E1 | 11 | 340 |
| HPV31 | E1 | 10 | 547 |
| HPV31 | E1 | 9 | 104 |
| HPV31 | E1 | 11 | 104 |
| HPV31 | E1 | 9 | 135 |
| HPV31 | E1 | 9 | 460 |
| HPV31 | E1 | 11 | 460 |
| HPV31 | E1 | 10 | 588 |
| HPV31 | E1 | 10 | 573 |
| HPV31 | E1 | 9 | 492 |
| HPV31 | E1 | 10 | 492 |
| HPV31 | E1 | 8 | 541 |
| HPV31 | E1 | 11 | 93 |
| HPV31 | E1 | 9 | 170 |
| HPV31 | E1 | 11 | 524 |
| HPV31 | E1 | 10 | 580 |
| HPV31 | E1 | 8 | 237 |
| HPV31 | E1 | 11 | 237 |
| HPV31 | E1 | 10 | 557 |
| HPV31 | E1 | 8 | 430 |
| HPV31 | E1 | 11 | 430 |
| HPV31 | E1 | 8 | 536 |
| HPV31 | E1 | 9 | 536 |
| HPV31 | E1 | 8 | 399 |
| HPV31 | E1 | 8 | 323 |
| HPV31 | E1 | 9 | 145 |
| HPV31 | E1 | 9 | 342 |
| HPV31 | E1 | 9 | 260 |
| HPV31 | E1 | 11 | 260 |
| HPV31 | E1 | 8 | 267 |
| HPV31 | E1 | 11 | 267 |
| HPV31 | E1 | 10 | 124 |
| HPV31 | E1 | 11 | 562 |
| HPV31 | E1 | 11 | 303 |
| HPV31 | E1 | 8 | 595 |
| HPV31 | E1 | 9 | 555 |
| HPV31 | E1 | 10 | 427 |
| HPV31 | E1 | 11 | 427 |
| HPV31 | E1 | 10 | 591 |
| HPV31 | E1 | 8 | 472 |
| HPV31 | E1 | 10 | 472 |
| HPV31 | E1 | 8 | 435 |
| HPV31 | E1 | 9 | 435 |
| HPV31 | E1 | 10 | 435 |
| HPV31 | E1 | 9 | 198 |
| HPV31 | E1 | 9 | 329 |
| HPV31 | E1 | 9 | 526 |
| HPV31 | E1 | 10 | 526 |
| HPV31 | E1 | 8 | 246 |
| HPV31 | E1 | 10 | 246 |
| HPV31 | E1 | 11 | 246 |
| HPV31 | E1 | 10 | 469 |
| HPV31 | E1 | 11 | 469 |
| HPV31 | E1 | 8 | 294 |
| HPV31 | E1 | 9 | 294 |
| HPV31 | E1 | 11 | 211 |
| HPV31 | E1 | 11 | 616 |
| HPV31 | E1 | 8 | 250 |
| HPV31 | E1 | 9 | 250 |
| HPV31 | E1 | 9 | 480 |
| HPV31 | E1 | 10 | 480 |
| HPV31 | E1 | 11 | 480 |
| HPV31 | E1 | 8 | 464 |
| HPV31 | E1 | 10 | 464 |
| HPV31 | E1 | 11 | 464 |
| HPV31 | E1 | 10 | 334 |
| HPV31 | E1 | 10 | 617 |
| HPV31 | E1 | 8 | 567 |
| HPV31 | E1 | 9 | 269 |
| HPV31 | E1 | 10 | 269 |
| HPV31 | E1 | 8 | 233 |
| HPV31 | E1 | 9 | 233 |
| HPV31 | E1 | 8 | 333 |
| HPV31 | E1 | 11 | 333 |
| HPV31 | E1 | 8 | 505 |
| HPV31 | E1 | 11 | 505 |
| GPV31 | E1 | 9 | 226 |
| HPV31 | E1 | 10 | 226 |
| HPV31 | E1 | 8 | 565 |
| HPV31 | E1 | 10 | 565 |
| HPV31 | E1 | 10 | 23 |
| HPV31 | E1 | 11 | 84 |
| HPV31 | E1 | 11 | 177 |
| HPV31 | E1 | 11 | 325 |
| HPV31 | E1 | 9 | 349 |
| HPV31 | E1 | 11 | 349 |
| HPV31 | E1 | 8 | 254 |
| HPV31 | E1 | 9 | 223 |
| HPV31 | E1 | 9 | 564 |
| HPV31 | E1 | 11 | 564 |
| HPV31 | E1 | 9 | 581 |
| HPV31 | E1 | 8 | 312 |
| HPV31 | E1 | 9 | 312 |
| HPV31 | E1 | 8 | 17 |
| HPV31 | E1 | 8 | 319 |
| HPV31 | E1 | 10 | 489 |
| HPV31 | E1 | 9 | 301 |
| HPV31 | E1 | 9 | 465 |
| HPV31 | E1 | 10 | 465 |
| HPV31 | E1 | 10 | 511 |
| HPV31 | E1 | 9 | 558 |
| HPV31 | E1 | 11 | 558 |
| HPV31 | E1 | 9 | 89 |
| HPV31 | E1 | 10 | 300 |
| HPV31 | E2 | 8 | 72 |
| HPV31 | E2 | 11 | 72 |
| HPV31 | E2 | 8 | 338 |
| HPV31 | E2 | 9 | 69 |
| HPV31 | E2 | 10 | 69 |
| HPV31 | E2 | 11 | 69 |
| HPV31 | E2 | 10 | 61 |
| HPV31 | E2 | 8 | 291 |
| HPV31 | E2 | 10 | 286 |
| HPV31 | E2 | 11 | 286 |
| HPV31 | E2 | 9 | 307 |
| HPV31 | E2 | 10 | 330 |
| HPV31 | E2 | 10 | 40 |
| HPV31 | E2 | 8 | 352 |
| HPV31 | E2 | 8 | 124 |
| HPV31 | E2 | 11 | 124 |
| HPV31 | E2 | 9 | 91 |
| HPV31 | E2 | 11 | 91 |
| HPV31 | E2 | 8 | 31 |
| HPV31 | E2 | 11 | 204 |

TABLE X-continued

HLA A24 Supermotif Peptides

| 1 | 2 | 3 | 4 |
|---|---|---|---|
| HPV31 | E2 | 9 | 74 |
| HPV31 | E2 | 11 | 100 |
| HPV31 | E2 | 8 | 80 |
| HPV31 | E2 | 9 | 185 |
| HPV31 | E2 | 11 | 185 |
| HPV31 | E2 | 9 | 86 |
| HPV31 | E2 | 8 | 171 |
| HPV31 | E2 | 10 | 168 |
| HPV31 | E2 | 10 | 156 |
| HPV31 | E2 | 8 | 114 |
| HPV31 | E2 | 8 | 29 |
| HPV31 | E2 | 10 | 29 |
| HPV31 | E2 | 8 | 35 |
| HPV31 | E2 | 9 | 35 |
| HPV31 | E2 | 10 | 35 |
| HPV31 | E2 | 8 | 164 |
| HPV31 | E2 | 8 | 297 |
| HPV31 | E2 | 9 | 297 |
| HPV31 | E2 | 9 | 18 |
| HPV31 | E2 | 8 | 130 |
| HPV31 | E2 | 9 | 130 |
| HPV31 | E2 | 10 | 130 |
| HPV31 | E2 | 10 | 295 |
| HPV31 | E2 | 11 | 295 |
| HPV31 | E2 | 9 | 304 |
| HPV31 | E2 | 8 | 193 |
| HPV31 | E2 | 9 | 157 |
| HPV31 | E2 | 11 | 157 |
| HPV31 | E2 | 11 | 183 |
| HPV31 | E2 | 8 | 177 |
| HPV31 | E2 | 8 | 42 |
| HPV31 | E2 | 10 | 42 |
| HPV31 | E2 | 8 | 103 |
| HPV31 | E2 | 9 | 318 |
| HPV31 | E2 | 11 | 318 |
| HPV31 | E2 | 10 | 101 |
| HPV31 | E2 | 10 | 78 |
| HPV31 | E2 | 11 | 77 |
| HPV31 | E2 | 9 | 43 |
| HPV31 | E2 | 9 | 170 |
| HPV31 | E2 | 8 | 303 |
| HPV31 | E2 | 10 | 303 |
| HPV31 | E2 | 9 | 84 |
| HPV31 | E2 | 11 | 84 |
| HPV31 | E2 | 8 | 254 |
| HPV31 | E2 | 9 | 254 |
| HPV31 | E2 | 8 | 127 |
| HPV31 | E2 | 10 | 127 |
| HPV31 | E2 | 11 | 127 |
| HPV31 | E2 | 9 | 361 |
| HPV31 | E2 | 10 | 361 |
| HPV31 | E2 | 8 | 9 |
| HPV31 | E2 | 11 | 9 |
| HPV31 | E2 | 9 | 133 |
| HPV31 | E2 | 11 | 294 |
| HPV31 | E2 | 10 | 106 |
| HPV31 | E2 | 10 | 120 |
| HPV31 | E2 | 10 | 317 |
| HPV31 | E2 | 8 | 96 |
| HPV31 | E2 | 10 | 191 |
| HPV31 | E2 | 8 | 151 |
| HPV31 | E2 | 9 | 151 |
| HPV31 | E2 | 8 | 321 |
| HPV31 | E2 | 8 | 25 |
| HPV31 | E2 | 9 | 25 |
| HPV31 | E2 | 8 | 37 |
| HPV31 | E2 | 9 | 7 |
| HPV31 | E2 | 10 | 7 |
| HPV31 | E2 | 8 | 311 |
| HPV31 | E2 | 9 | 311 |
| HPV31 | E2 | 10 | 309 |
| HPV31 | E2 | 11 | 309 |
| HPV31 | E2 | 9 | 206 |
| HPV31 | E2 | 10 | 53 |
| HPV31 | E2 | 8 | 346 |
| HPV31 | E2 | 9 | 346 |
| HPV31 | E2 | 10 | 266 |
| HPV31 | E2 | 8 | 198 |
| HPV31 | E2 | 10 | 198 |
| HPV31 | E2 | 8 | 63 |
| HPV31 | E2 | 11 | 63 |
| HPV31 | E2 | 9 | 364 |
| HPV31 | E2 | 9 | 128 |
| HPV31 | E2 | 10 | 128 |
| HPV31 | E2 | 11 | 128 |
| HPV31 | E2 | 9 | 93 |
| HPV31 | E2 | 10 | 93 |
| HPV31 | E2 | 11 | 93 |
| HPV31 | E2 | 10 | 221 |
| HPV31 | E2 | 11 | 220 |
| HPV31 | E2 | 8 | 362 |
| HPV31 | E2 | 9 | 362 |
| HPV31 | E2 | 11 | 362 |
| HPV31 | E2 | 11 | 343 |
| HPV31 | E2 | 9 | 199 |
| HPV31 | E2 | 9 | 192 |
| HPV31 | E2 | 9 | 41 |
| HPV31 | E2 | 11 | 41 |
| HPV31 | E2 | 11 | 147 |
| HPV31 | E2 | 8 | 92 |
| HPV31 | E2 | 10 | 92 |
| HPV31 | E2 | 11 | 92 |
| HPV31 | E2 | 10 | 344 |
| HPV31 | E2 | 11 | 344 |
| HPV31 | E2 | 9 | 102 |
| HPV31 | E2 | 8 | 131 |
| HPV31 | E2 | 9 | 131 |
| HPV31 | E2 | 11 | 131 |
| HPV31 | E2 | 9 | 159 |
| HPV31 | E2 | 10 | 159 |
| HPV31 | E2 | 11 | 32 |
| HPV31 | E2 | 8 | 158 |
| HPV31 | E2 | 10 | 158 |
| HPV31 | E2 | 11 | 158 |
| HPV31 | E5 | 9 | 40 |
| HPV31 | E5 | 10 | 40 |
| HPV31 | E5 | 11 | 40 |
| HPV31 | E5 | 8 | 53 |
| HPV31 | E5 | 10 | 53 |
| HPV31 | E5 | 11 | 53 |
| HPV31 | E5 | 8 | 59 |
| HPV31 | E5 | 9 | 59 |
| HPV31 | E5 | 10 | 59 |
| HPV31 | E5 | 11 | 59 |
| HPV31 | E5 | 10 | 18 |
| HPV31 | E5 | 9 | 14 |
| HPV31 | E5 | 10 | 14 |
| HPV31 | E5 | 11 | 14 |
| HPV31 | E5 | 8 | 61 |
| HPV31 | E5 | 9 | 61 |
| HPV31 | E5 | 11 | 61 |
| HPV31 | E5 | 9 | 26 |
| HPV31 | E5 | 8 | 20 |
| HPV31 | E5 | 10 | 20 |
| HPV31 | E5 | 9 | 3 |
| HPV31 | E5 | 11 | 3 |
| HPV31 | E5 | 9 | 66 |
| HPV31 | E5 | 8 | 15 |
| HPV31 | E5 | 9 | 15 |
| HPV31 | E5 | 10 | 15 |
| HPV31 | E5 | 9 | 24 |
| HPV31 | E5 | 11 | 24 |
| HPV31 | E5 | 9 | 72 |
| HPV31 | E5 | 10 | 72 |
| HPV31 | E5 | 10 | 48 |
| HPV31 | E5 | 9 | 11 |
| HPV31 | E5 | 8 | 67 |
| HPV31 | E5 | 8 | 62 |
| HPV31 | E5 | 10 | 62 |
| HPV31 | E5 | 11 | 62 |

TABLE X-continued

HLA A24 Supermotif Peptides

| 1 | 2 | 3 | 4 |
|---|---|---|---|
| HPV31 | E5 | 10 | 23 |
| HPV31 | E5 | 10 | 71 |
| HPV31 | E5 | 11 | 71 |
| HPV31 | E5 | 8 | 45 |
| HPV31 | E5 | 8 | 16 |
| HPV31 | E5 | 9 | 16 |
| HPV31 | E5 | 8 | 22 |
| HPV31 | E5 | 11 | 22 |
| HPV31 | E5 | 9 | 44 |
| HPV31 | E5 | 8 | 43 |
| HPV31 | E5 | 10 | 43 |
| HPV31 | E5 | 8 | 42 |
| HPV31 | E5 | 9 | 42 |
| HPV31 | E5 | 11 | 42 |
| HPV31 | E5 | 8 | 27 |
| HPV31 | E5 | 8 | 32 |
| HPV31 | E5 | 11 | 32 |
| HPV31 | E5 | 9 | 49 |
| HPV31 | E5 | 11 | 1 |
| HPV31 | E5 | 9 | 5 |
| HPV31 | E5 | 11 | 5 |
| HPV31 | E5 | 11 | 70 |
| HPV31 | E5 | 8 | 56 |
| HPV31 | E5 | 11 | 56 |
| HPV31 | E5 | 9 | 31 |
| HPV31 | E5 | 8 | 10 |
| HPV31 | E5 | 10 | 10 |
| HPV31 | E5 | 9 | 7 |
| HPV31 | E5 | 10 | 7 |
| HPV31 | E5 | 11 | 7 |
| HPV31 | E5 | 8 | 35 |
| HPV31 | E5 | 9 | 35 |
| HPV31 | E5 | 10 | 35 |
| HPV31 | E5 | 11 | 35 |
| HPV31 | E5 | 8 | 37 |
| HPV31 | E5 | 9 | 37 |
| HPV31 | E5 | 10 | 37 |
| HPV31 | E5 | 8 | 41 |
| HPV31 | E5 | 9 | 41 |
| HPV31 | E5 | 10 | 41 |
| HPV31 | E5 | 8 | 8 |
| HPV31 | E5 | 9 | 8 |
| HPV31 | E5 | 10 | 8 |
| HPV31 | E5 | 8 | 65 |
| HPV31 | E5 | 10 | 65 |
| HPV31 | E5 | 10 | 51 |
| HPV31 | E5 | 8 | 73 |
| HPV31 | E5 | 9 | 73 |
| HPV31 | E5 | 11 | 47 |
| HPV31 | E5 | 8 | 12 |
| HPV31 | E5 | 11 | 12 |
| HPV31 | E5 | 9 | 21 |
| HPV31 | E5 | 10 | 33 |
| HPV31 | E5 | 11 | 33 |
| HPV31 | E5 | 8 | 64 |
| HPV31 | E5 | 9 | 64 |
| HPV31 | E5 | 11 | 64 |
| HPV31 | E5 | 8 | 38 |
| HPV31 | E5 | 9 | 38 |
| HPV31 | E5 | 11 | 38 |
| HPV31 | E5 | 8 | 50 |
| HPV31 | E5 | 11 | 50 |
| HPV31 | E5 | 9 | 63 |
| HPV31 | E5 | 10 | 63 |
| HPV31 | E6 | 9 | 46 |
| HPV31 | E6 | 9 | 18 |
| HPV31 | E6 | 11 | 18 |
| HPV31 | E6 | 8 | 103 |
| HPV31 | E6 | 11 | 66 |
| HPV31 | E6 | 8 | 63 |
| HPV31 | E6 | 8 | 30 |
| HPV31 | E6 | 9 | 44 |
| HPV31 | E6 | 11 | 44 |
| HPV31 | E6 | 11 | 57 |
| HPV31 | E6 | 10 | 75 |
| HPV31 | E6 | 9 | 20 |
| HPV31 | E6 | 8 | 25 |
| HPV31 | E6 | 8 | 14 |
| HPV31 | E6 | 10 | 14 |
| HPV31 | E6 | 9 | 39 |
| HPV31 | E6 | 10 | 41 |
| HPV31 | E6 | 8 | 47 |
| HPV31 | E6 | 8 | 69 |
| HPV31 | E6 | 10 | 69 |
| HPV31 | E6 | 11 | 69 |
| HPV31 | E6 | 10 | 95 |
| HPV31 | E6 | 9 | 61 |
| HPV31 | E6 | 10 | 61 |
| HPV31 | E6 | 8 | 118 |
| HPV31 | E6 | 11 | 118 |
| HPV31 | E6 | 9 | 11 |
| HPV31 | E6 | 11 | 11 |
| HPV31 | E6 | 10 | 90 |
| HPV31 | E6 | 11 | 90 |
| HPV31 | E6 | 8 | 72 |
| HPV31 | E6 | 10 | 72 |
| HPV31 | E6 | 11 | 100 |
| HPV31 | E6 | 9 | 37 |
| HPV31 | E6 | 11 | 37 |
| HPV31 | E6 | 9 | 91 |
| HPV31 | E6 | 10 | 91 |
| HPV31 | E6 | 11 | 91 |
| HPV31 | E6 | 11 | 127 |
| HPV31 | E6 | 11 | 109 |
| HPV31 | E6 | 11 | 22 |
| HPV31 | E6 | 8 | 36 |
| HPV31 | E6 | 10 | 36 |
| HPV31 | E6 | 9 | 124 |
| HPV31 | E6 | 9 | 68 |
| HPV31 | E6 | 11 | 68 |
| HPV31 | E6 | 11 | 27 |
| HPV31 | E6 | 10 | 131 |
| HPV31 | E6 | 8 | 77 |
| HPV31 | E6 | 9 | 80 |
| HPV31 | E6 | 10 | 82 |
| HPV31 | E6 | 10 | 87 |
| HPV31 | E6 | 11 | 86 |
| HPV31 | E6 | 9 | 42 |
| HPV31 | E6 | 11 | 42 |
| HPV31 | E6 | 9 | 83 |
| HPV31 | E6 | 9 | 132 |
| HPV31 | E6 | 11 | 78 |
| HPV31 | E7 | 10 | 19 |
| HPV31 | E7 | 9 | 68 |
| HPV31 | E7 | 11 | 68 |
| HPV31 | E7 | 8 | 75 |
| HPV31 | E7 | 9 | 75 |
| HPV31 | E7 | 10 | 75 |
| HPV31 | E7 | 8 | 21 |
| HPV31 | E7 | 9 | 14 |
| HPV31 | E7 | 10 | 48 |
| HPV31 | E7 | 9 | 81 |
| HPV31 | E7 | 8 | 4 |
| HPV31 | E7 | 10 | 4 |
| HPV31 | E7 | 11 | 88 |
| HPV31 | E7 | 10 | 78 |
| HPV31 | E7 | 10 | 89 |
| HPV31 | E7 | 8 | 82 |
| HPV31 | E7 | 8 | 6 |
| HPV31 | E7 | 10 | 6 |
| HPV31 | E7 | 10 | 73 |
| HPV31 | E7 | 11 | 73 |
| HPV31 | E7 | 8 | 77 |
| HPV31 | E7 | 11 | 77 |
| HPV31 | E7 | 11 | 66 |
| HPV31 | E7 | 8 | 71 |
| HPV31 | E7 | 9 | 71 |
| HPV31 | E7 | 10 | 56 |
| HPV31 | E7 | 9 | 7 |
| HPV31 | E7 | 11 | 12 |

TABLE X-continued

HLA A24 Supermotif Peptides

| 1 | 2 | 3 | 4 |
|---|---|---|---|
| HPV31 | E7 | 11 | 55 |
| HPV31 | L1 | 9 | 348 |
| HPV31 | L1 | 8 | 398 |
| HPV31 | L1 | 10 | 398 |
| HPV31 | L1 | 10 | 180 |
| HPV31 | L1 | 11 | 213 |
| HPV31 | L1 | 8 | 285 |
| HPV31 | L1 | 9 | 285 |
| HPV31 | L1 | 11 | 147 |
| HPV31 | L1 | 9 | 158 |
| HPV31 | L1 | 9 | 224 |
| HPV31 | L1 | 9 | 387 |
| HPV31 | L1 | 11 | 459 |
| HPV31 | L1 | 8 | 372 |
| HPV31 | L1 | 11 | 372 |
| HPV31 | L1 | 10 | 200 |
| HPV31 | L1 | 8 | 129 |
| HPV31 | L1 | 9 | 203 |
| HPV31 | L1 | 8 | 216 |
| HPV31 | L1 | 10 | 216 |
| HPV31 | L1 | 9 | 353 |
| HPV31 | L1 | 8 | 336 |
| HPV31 | L1 | 11 | 417 |
| HPV31 | L1 | 9 | 151 |
| HPV31 | L1 | 10 | 151 |
| HPV31 | L1 | 10 | 234 |
| HPV31 | L1 | 9 | 444 |
| HPV31 | L1 | 8 | 370 |
| HPV31 | L1 | 10 | 370 |
| HPV31 | L1 | 8 | 107 |
| HPV31 | L1 | 8 | 449 |
| HPV31 | L1 | 9 | 363 |
| HPV31 | L1 | 11 | 363 |
| HPV31 | L1 | 8 | 26 |
| HPV31 | L1 | 9 | 26 |
| HPV31 | L1 | 10 | 26 |
| HPV31 | L1 | 9 | 248 |
| HPV31 | L1 | 10 | 248 |
| HPV31 | L1 | 8 | 375 |
| HPV31 | L1 | 10 | 375 |
| HPV31 | L1 | 10 | 447 |
| HPV31 | L1 | 8 | 249 |
| HPV31 | L1 | 9 | 249 |
| HPV31 | L1 | 9 | 91 |
| HPV31 | L1 | 11 | 91 |
| HPV31 | L1 | 10 | 205 |
| HPV31 | L1 | 8 | 85 |
| HPV31 | L1 | 8 | 323 |
| HPV31 | L1 | 9 | 323 |
| HPV31 | L1 | 8 | 117 |
| HPV31 | L1 | 11 | 117 |
| HPV31 | L1 | 10 | 105 |
| HPV31 | L1 | 11 | 68 |
| HPV31 | L1 | 10 | 406 |
| HPV31 | L1 | 8 | 141 |
| HPV31 | L1 | 10 | 141 |
| HPV31 | L1 | 11 | 266 |
| HPV31 | L1 | 9 | 115 |
| HPV31 | L1 | 10 | 115 |
| HPV31 | L1 | 8 | 474 |
| HPV31 | L1 | 8 | 307 |
| HPV31 | L1 | 9 | 376 |
| HPV31 | L1 | 9 | 399 |
| HPV31 | L1 | 8 | 388 |
| HPV31 | L1 | 8 | 382 |
| HPV31 | L1 | 10 | 382 |
| HPV31 | L1 | 11 | 382 |
| HPV31 | L1 | 9 | 181 |
| HPV31 | L1 | 11 | 181 |
| HPV31 | L1 | 9 | 61 |
| HPV31 | L1 | 11 | 61 |
| HPV31 | L1 | 10 | 33 |
| HPV31 | L1 | 11 | 33 |
| HPV31 | L1 | 11 | 126 |
| HPV31 | L1 | 9 | 83 |
| HPV31 | L1 | 10 | 83 |
| HPV31 | L1 | 8 | 468 |
| HPV31 | L1 | 9 | 455 |
| HPV31 | L1 | 11 | 455 |
| HPV31 | L1 | 8 | 381 |
| HPV31 | L1 | 9 | 381 |
| HPV31 | L1 | 11 | 381 |
| HPV31 | L1 | 10 | 60 |
| HPV31 | L1 | 11 | 237 |
| HPV31 | L1 | 10 | 65 |
| HPV31 | L1 | 8 | 20 |
| HPV31 | L1 | 8 | 231 |
| HPV31 | L1 | 10 | 247 |
| HPV31 | L1 | 11 | 247 |
| HPV31 | L1 | 8 | 159 |
| HPV31 | L1 | 8 | 42 |
| HPV31 | L1 | 9 | 42 |
| HPV31 | L1 | 11 | 42 |
| HPV31 | L1 | 9 | 407 |
| HPV31 | L1 | 8 | 43 |
| HPV31 | L1 | 10 | 43 |
| HPV31 | L1 | 8 | 99 |
| HPV31 | L1 | 10 | 3 |
| HPV31 | L1 | 11 | 3 |
| HPV31 | L1 | 11 | 389 |
| HPV31 | L1 | 10 | 238 |
| HPV31 | L1 | 11 | 238 |
| HPV31 | L1 | 9 | 201 |
| HPV31 | L1 | 11 | 201 |
| HPV31 | L1 | 8 | 300 |
| HPV31 | L1 | 9 | 300 |
| HPV31 | L1 | 11 | 32 |
| HPV31 | L1 | 10 | 451 |
| HPV31 | L1 | 8 | 342 |
| HPV31 | L1 | 10 | 220 |
| HPV31 | L1 | 8 | 441 |
| HPV31 | L1 | 8 | 222 |
| HPV31 | L1 | 11 | 222 |
| HPV31 | L1 | 9 | 188 |
| HPV31 | L1 | 8 | 464 |
| HPV31 | L1 | 11 | 113 |
| HPV31 | L1 | 11 | 17 |
| HPV31 | L1 | 8 | 242 |
| HPV31 | L1 | 9 | 242 |
| HPV31 | L1 | 10 | 242 |
| HPV31 | L1 | 9 | 374 |
| HPV31 | L1 | 11 | 374 |
| HPV31 | L1 | 8 | 462 |
| HPV31 | L1 | 9 | 462 |
| HPV31 | L1 | 10 | 462 |
| HPV31 | L1 | 8 | 306 |
| HPV31 | L1 | 9 | 306 |
| HPV31 | L1 | 11 | 378 |
| HPV31 | L1 | 11 | 156 |
| HPV31 | L1 | 8 | 255 |
| HPV31 | L1 | 9 | 70 |
| HPV31 | L1 | 8 | 420 |
| HPV31 | L1 | 9 | 41 |
| HPV31 | L1 | 10 | 41 |
| HPV31 | L1 | 8 | 77 |
| HPV31 | L1 | 10 | 77 |
| HPV31 | L1 | 9 | 98 |
| HPV31 | L1 | 10 | 75 |
| HPV31 | L1 | 10 | 90 |
| HPV31 | L1 | 8 | 228 |
| HPV31 | L1 | 9 | 228 |
| HPV31 | L1 | 11 | 228 |
| HPV31 | L1 | 11 | 51 |
| HPV31 | L1 | 8 | 414 |
| HPV31 | L1 | 11 | 2 |
| HPV31 | L1 | 9 | 149 |
| HPV31 | L1 | 11 | 149 |
| HPV31 | L1 | 10 | 394 |
| HPV31 | L1 | 9 | 299 |
| HPV31 | L1 | 10 | 299 |

TABLE X-continued

HLA A24 Supermotif Peptides

| 1 | 2 | 3 | 4 |
|---|---|---|---|
| HPV31 | L1 | 10 | 283 |
| HPV31 | L1 | 11 | 283 |
| HPV31 | L1 | 11 | 23 |
| HPV31 | L1 | 10 | 340 |
| HPV31 | L1 | 11 | 290 |
| HPV31 | L1 | 8 | 194 |
| HPV31 | L1 | 8 | 271 |
| HPV31 | L1 | 10 | 355 |
| HPV31 | L1 | 11 | 355 |
| HPV31 | L1 | 8 | 286 |
| HPV31 | L1 | 11 | 246 |
| HPV31 | L1 | 9 | 383 |
| HPV31 | L1 | 10 | 383 |
| HPV31 | L1 | 8 | 354 |
| HPV31 | L1 | 11 | 354 |
| HPV31 | L1 | 8 | 408 |
| HPV31 | L1 | 10 | 267 |
| HPV31 | L1 | 11 | 267 |
| HPV31 | L1 | 9 | 44 |
| HPV31 | L1 | 11 | 333 |
| HPV31 | L1 | 10 | 291 |
| HPV31 | L1 | 10 | 390 |
| HPV31 | L1 | 11 | 390 |
| HPV31 | L1 | 10 | 418 |
| HPV31 | L1 | 11 | 446 |
| HPV31 | L1 | 8 | 28 |
| HPV31 | L1 | 8 | 301 |
| HPV31 | L1 | 10 | 334 |
| HPV31 | L1 | 8 | 62 |
| HPV31 | L1 | 10 | 62 |
| HPV31 | L1 | 9 | 292 |
| HPV31 | L1 | 9 | 391 |
| HPV31 | L1 | 10 | 391 |
| HPV31 | L1 | 11 | 277 |
| HPV31 | L1 | 9 | 235 |
| HPV31 | L1 | 8 | 364 |
| HPV31 | L1 | 10 | 364 |
| HPV31 | L1 | 8 | 250 |
| HPV31 | L1 | 8 | 445 |
| HPV31 | L1 | 8 | 27 |
| HPV31 | L1 | 9 | 27 |
| HPV31 | L1 | 9 | 34 |
| HPV31 | L1 | 10 | 34 |
| HPV31 | L2 | 11 | 286 |
| HPV31 | L2 | 9 | 311 |
| HPV31 | L2 | 10 | 311 |
| HPV31 | L2 | 11 | 311 |
| HPV31 | L2 | 8 | 226 |
| HPV31 | L2 | 10 | 135 |
| HPV31 | L2 | 11 | 135 |
| HPV31 | L2 | 11 | 342 |
| HPV31 | L2 | 11 | 376 |
| HPV31 | L2 | 11 | 251 |
| HPV31 | L2 | 11 | 385 |
| HPV31 | L2 | 8 | 275 |
| HPV31 | L2 | 8 | 438 |
| HPV31 | L2 | 9 | 438 |
| HPV31 | L2 | 10 | 438 |
| HPV31 | L2 | 11 | 438 |
| HPV31 | L2 | 10 | 278 |
| HPV31 | L2 | 8 | 354 |
| HPV31 | L2 | 8 | 116 |
| HPV31 | L2 | 11 | 31 |
| HPV31 | L2 | 8 | 190 |
| HPV31 | L2 | 8 | 171 |
| HPV31 | L2 | 9 | 253 |
| HPV31 | L2 | 10 | 253 |
| HPV31 | L2 | 11 | 253 |
| HPV31 | L2 | 10 | 196 |
| HPV31 | L2 | 8 | 237 |
| HPV31 | L2 | 9 | 237 |
| HPV31 | L2 | 11 | 237 |
| HPV31 | L2 | 8 | 433 |
| HPV31 | L2 | 9 | 433 |
| HPV31 | L2 | 8 | 439 |
| HPV31 | L2 | 9 | 439 |
| HPV31 | L2 | 10 | 439 |
| HPV31 | L2 | 11 | 113 |
| HPV31 | L2 | 11 | 351 |
| HPV31 | L2 | 8 | 26 |
| HPV31 | L2 | 11 | 26 |
| HPV31 | L2 | 8 | 65 |
| HPV31 | L2 | 11 | 65 |
| HPV31 | L2 | 9 | 52 |
| HPV31 | L2 | 8 | 213 |
| HPV31 | L2 | 10 | 213 |
| HPV31 | L2 | 11 | 213 |
| HPV31 | L2 | 9 | 175 |
| HPV31 | L2 | 8 | 38 |
| HPV31 | L2 | 9 | 38 |
| HPV31 | L2 | 11 | 38 |
| HPV31 | L2 | 9 | 318 |
| HPV31 | L2 | 9 | 403 |
| HPV31 | L2 | 8 | 432 |
| HPV31 | L2 | 9 | 432 |
| HPV31 | L2 | 10 | 432 |
| HPV31 | L2 | 9 | 279 |
| HPV31 | L2 | 10 | 45 |
| HPV31 | L2 | 11 | 45 |
| HPV31 | L2 | 8 | 245 |
| HPV31 | L2 | 10 | 114 |
| HPV31 | L2 | 10 | 105 |
| HPV31 | L2 | 9 | 197 |
| HPV31 | L2 | 11 | 35 |
| HPV31 | 12 | 8 | 231 |
| HPV31 | L2 | 9 | 244 |
| HPV31 | L2 | 8 | 176 |
| HPV31 | L2 | 10 | 287 |
| HPV31 | L2 | 10 | 352 |
| HPV31 | L2 | 10 | 261 |
| HPV31 | L2 | 11 | 447 |
| HPV31 | L2 | 8 | 269 |
| HPV31 | L2 | 9 | 269 |
| HPV31 | L2 | 11 | 269 |
| HPV31 | L2 | 8 | 204 |
| HPV31 | L2 | 10 | 390 |
| HPV31 | L2 | 8 | 292 |
| HPV31 | L2 | 10 | 187 |
| HPV31 | L2 | 11 | 187 |
| HPV31 | L2 | 10 | 410 |
| HPV31 | L2 | 10 | 402 |
| HPV31 | L2 | 11 | 210 |
| HPV31 | L2 | 11 | 122 |
| HPV31 | L2 | 8 | 88 |
| HPV31 | L2 | 11 | 422 |
| HPV31 | L2 | 9 | 100 |
| HPV31 | L2 | 8 | 394 |
| HPV31 | L2 | 10 | 394 |
| HPV31 | L2 | 11 | 394 |
| HPV31 | L2 | 10 | 235 |
| HPV31 | L2 | 11 | 235 |
| HPV31 | L2 | 9 | 156 |
| HPV31 | L2 | 8 | 388 |
| HPV31 | L2 | 10 | 167 |
| HPV31 | L2 | 11 | 167 |
| HPV31 | L2 | 9 | 415 |
| HPV31 | L2 | 8 | 425 |
| HPV31 | L2 | 9 | 425 |
| HPV31 | L2 | 8 | 127 |
| HPV31 | L2 | 9 | 97 |
| HPV31 | L2 | 10 | 92 |
| HPV31 | L2 | 8 | 44 |
| HPV31 | L2 | 11 | 44 |
| HPV31 | L2 | 10 | 243 |
| HPV31 | L2 | 11 | 303 |
| HPV31 | L2 | 9 | 229 |
| HPV31 | L2 | 10 | 229 |
| HPV31 | L2 | 11 | 429 |
| HPV31 | L2 | 8 | 298 |
| HPV31 | L2 | 10 | 9 |

TABLE X-continued

HLA A24 Supermotif Peptides

| 1 | 2 | 3 | 4 |
|---|---|---|---|
| HPV31 | L2 | 11 | 9 |
| HPV31 | L2 | 8 | 306 |
| HPV31 | L2 | 8 | 316 |
| HPV31 | L2 | 11 | 316 |
| HPV31 | L2 | 8 | 47 |
| HPV31 | L2 | 9 | 47 |
| HPV31 | L2 | 11 | 295 |
| HPV31 | L2 | 8 | 94 |
| HPV31 | L2 | 9 | 431 |
| HPV31 | L2 | 10 | 431 |
| HPV31 | L2 | 11 | 431 |
| HPV31 | L2 | 9 | 325 |
| HPV31 | L2 | 11 | 325 |
| HPV31 | L2 | 10 | 86 |
| HPV31 | L2 | 10 | 182 |
| HPV31 | L2 | 11 | 104 |
| HPV31 | L2 | 8 | 107 |
| HPV31 | L2 | 11 | 260 |
| HPV31 | L2 | 9 | 50 |
| HPV31 | L2 | 11 | 50 |
| HPV31 | L2 | 8 | 396 |
| HPV31 | L2 | 9 | 396 |
| HPV31 | L2 | 8 | 151 |
| HPV31 | L2 | 8 | 184 |
| HPV31 | L2 | 10 | 184 |
| HPV31 | L2 | 8 | 346 |
| HPV31 | L2 | 10 | 346 |
| HPV31 | L2 | 11 | 346 |
| HPV31 | L2 | 8 | 379 |
| HPV31 | L2 | 8 | 80 |
| HPV31 | L2 | 10 | 80 |
| HPV31 | L2 | 10 | 149 |
| HPV31 | L2 | 11 | 195 |
| HPV31 | L2 | 9 | 236 |
| HPV31 | L2 | 10 | 236 |
| HPV31 | L2 | 8 | 157 |
| HPV31 | L2 | 9 | 40 |
| HPV31 | L2 | 8 | 312 |
| HPV31 | L2 | 9 | 312 |
| HPV31 | L2 | 10 | 312 |
| HPV31 | L2 | 9 | 347 |
| HPV31 | L2 | 10 | 347 |
| HPV31 | L2 | 10 | 304 |
| HPV31 | L2 | 9 | 136 |
| HPV31 | L2 | 10 | 136 |
| HPV31 | L2 | 8 | 39 |
| HPV31 | L2 | 10 | 39 |
| HPV31 | L2 | 8 | 426 |
| HPV31 | L2 | 9 | 344 |
| HPV31 | L2 | 10 | 344 |
| HPV31 | L2 | 10 | 343 |
| HPV31 | L2 | 11 | 343 |
| HPV31 | L2 | 9 | 391 |
| HPV31 | L2 | 11 | 391 |
| HPV31 | L2 | 8 | 254 |
| HPV31 | L2 | 9 | 254 |
| HPV31 | L2 | 10 | 254 |
| HPV31 | L2 | 8 | 392 |
| HPV31 | L2 | 10 | 392 |
| HPV31 | L2 | 9 | 81 |
| HPV31 | L2 | 8 | 53 |
| HPV31 | L2 | 10 | 32 |
| HPV31 | L2 | 9 | 262 |
| HPV31 | L2 | 8 | 440 |
| HPV31 | L2 | 9 | 440 |
| HPV31 | L2 | 10 | 386 |
| HPV31 | L2 | 8 | 319 |
| HPV33 | E1 | 9 | 452 |
| HPV33 | E1 | 9 | 448 |
| HPV33 | E1 | 10 | 448 |
| HPV33 | E1 | 11 | 384 |
| HPV33 | E1 | 10 | 596 |
| HPV33 | E1 | 11 | 596 |
| HPV33 | E1 | 9 | 532 |
| HPV33 | E1 | 10 | 546 |
| HPV33 | E1 | 11 | 546 |
| HPV33 | E1 | 9 | 311 |
| HPV33 | E1 | 9 | 81 |
| HPV33 | E1 | 11 | 22 |
| HPV33 | E1 | 9 | 207 |
| HPV33 | E1 | 8 | 259 |
| HPV33 | E1 | 9 | 259 |
| HPV33 | E1 | 10 | 259 |
| HPV33 | E1 | 11 | 259 |
| HPV33 | E1 | 9 | 297 |
| HPV33 | E1 | 9 | 226 |
| HPV33 | E1 | 11 | 226 |
| HPV33 | E1 | 11 | 14 |
| HPV33 | E1 | 8 | 118 |
| HPV33 | E1 | 11 | 118 |
| HPV33 | E1 | 8 | 494 |
| HPV33 | E1 | 9 | 494 |
| HPV33 | E1 | 10 | 494 |
| HPV33 | E1 | 9 | 367 |
| HPV33 | E1 | 10 | 46 |
| HPV33 | E1 | 8 | 78 |
| HPV33 | E1 | 8 | 349 |
| HPV33 | E1 | 10 | 349 |
| HPV33 | E1 | 8 | 62 |
| HPV33 | E1 | 9 | 62 |
| HPV33 | E1 | 11 | 62 |
| HPV33 | E1 | 10 | 541 |
| HPV33 | E1 | 9 | 324 |
| HPV33 | E1 | 10 | 324 |
| HPV33 | E1 | 9 | 516 |
| HPV33 | E1 | 10 | 516 |
| HPV33 | E1 | 9 | 228 |
| HPV33 | E1 | 11 | 49 |
| HPV33 | E1 | 8 | 580 |
| HPV33 | E1 | 9 | 445 |
| HPV33 | E1 | 11 | 537 |
| HPV33 | E1 | 8 | 361 |
| HPV33 | E1 | 10 | 361 |
| HPV33 | E1 | 11 | 361 |
| HPV33 | E1 | 11 | 352 |
| HPV33 | E1 | 10 | 38 |
| HPV33 | E1 | 11 | 38 |
| HPV33 | E1 | 11 | 295 |
| HPV33 | E1 | 9 | 331 |
| HPV33 | E1 | 9 | 605 |
| HPV33 | E1 | 11 | 605 |
| HPV33 | E1 | 10 | 50 |
| HPV33 | E1 | 8 | 449 |
| HPV33 | E1 | 9 | 449 |
| HPV33 | E1 | 11 | 456 |
| HPV33 | E1 | 10 | 385 |
| HPV33 | E1 | 8 | 212 |
| HPV33 | E1 | 8 | 446 |
| HPV33 | E1 | 11 | 446 |
| HPV33 | E1 | 11 | 501 |
| HPV33 | E1 | 8 | 265 |
| HPV33 | E1 | 10 | 265 |
| HPV33 | E1 | 8 | 459 |
| HPV33 | E1 | 9 | 459 |
| HPV33 | E1 | 10 | 459 |
| HPV33 | E1 | 11 | 209 |
| HPV33 | E1 | 10 | 235 |
| HPV33 | E1 | 8 | 11 |
| HPV33 | E1 | 9 | 512 |
| HPV33 | E1 | 11 | 512 |
| HPV33 | E1 | 8 | 480 |
| HPV33 | E1 | 8 | 44 |
| HPV33 | E1 | 8 | 564 |
| HPV33 | E1 | 9 | 564 |
| HPV33 | E1 | 10 | 327 |
| HPV33 | E1 | 9 | 16 |
| HPV33 | E1 | 11 | 256 |
| HPV33 | E1 | 10 | 404 |
| HPV33 | E1 | 10 | 347 |
| HPV33 | E1 | 9 | 266 |

TABLE X-continued

HLA A24 Supermotif Peptides

| 1 | 2 | 3 | 4 |
|---|---|---|---|
| HPV33 | E1 | 8 | 267 |
| HPV33 | E1 | 9 | 200 |
| HPV33 | E1 | 11 | 200 |
| HPV33 | E1 | 8 | 394 |
| HPV33 | E1 | 10 | 435 |
| HPV33 | E1 | 8 | 203 |
| HPV33 | E1 | 10 | 203 |
| HPV33 | E1 | 11 | 203 |
| HPV33 | E1 | 10 | 124 |
| HPV33 | E1 | 11 | 510 |
| HPV33 | E1 | 8 | 393 |
| HPV33 | E1 | 9 | 393 |
| HPV33 | E1 | 9 | 285 |
| HPV33 | E1 | 9 | 304 |
| HPV33 | E1 | 10 | 304 |
| HPV33 | E1 | 11 | 304 |
| HPV33 | E1 | 8 | 412 |
| HPV33 | E1 | 8 | 425 |
| HPV33 | E1 | 11 | 425 |
| HPV33 | E1 | 9 | 223 |
| HPV33 | E1 | 9 | 245 |
| HPV33 | E1 | 10 | 245 |
| HPV33 | E1 | 11 | 69 |
| HPV33 | E1 | 8 | 247 |
| HPV33 | E1 | 11 | 247 |
| HPV33 | E1 | 10 | 483 |
| HPV33 | E1 | 11 | 271 |
| HPV33 | E1 | 9 | 47 |
| HPV33 | E1 | 9 | 438 |
| HPV33 | E1 | 9 | 290 |
| HPV33 | E1 | 11 | 290 |
| HPV33 | E1 | 8 | 286 |
| HPV33 | E1 | 8 | 260 |
| HPV33 | E1 | 9 | 260 |
| HPV33 | E1 | 10 | 260 |
| HPV33 | E1 | 11 | 260 |
| HPV33 | E1 | 9 | 362 |
| HPV33 | E1 | 10 | 362 |
| HPV33 | E1 | 11 | 362 |
| HPV33 | E1 | 10 | 281 |
| HPV33 | E1 | 11 | 281 |
| HPV33 | E1 | 10 | 576 |
| HPV33 | E1 | 8 | 336 |
| HPV33 | E1 | 9 | 547 |
| HPV33 | E1 | 10 | 547 |
| HPV33 | E1 | 11 | 547 |
| HPV33 | E1 | 8 | 201 |
| HPV33 | E1 | 10 | 201 |
| HPV33 | E1 | 8 | 253 |
| HPV33 | E1 | 8 | 312 |
| HPV33 | E1 | 11 | 312 |
| HPV33 | E1 | 8 | 513 |
| HPV33 | E1 | 10 | 513 |
| HPV33 | E1 | 8 | 298 |
| HPV33 | E1 | 10 | 353 |
| HPV33 | E1 | 8 | 443 |
| HPV33 | E1 | 11 | 443 |
| HPV33 | E1 | 8 | 346 |
| HPV33 | E1 | 11 | 346 |
| HPV33 | E1 | 10 | 199 |
| HPV33 | E1 | 9 | 71 |
| HPV33 | E1 | 10 | 289 |
| HPV33 | E1 | 9 | 135 |
| HPV33 | E1 | 9 | 473 |
| HPV33 | E1 | 11 | 473 |
| HPV33 | E1 | 8 | 195 |
| HPV33 | E1 | 10 | 195 |
| HPV33 | E1 | 10 | 560 |
| HPV33 | E1 | 10 | 175 |
| HPV33 | E1 | 11 | 181 |
| HPV33 | E1 | 10 | 601 |
| HPV33 | E1 | 8 | 431 |
| HPV33 | E1 | 9 | 431 |
| HPV33 | E1 | 11 | 431 |
| HPV33 | E1 | 10 | 586 |
| HPV33 | E1 | 10 | 519 |
| HPV33 | E1 | 11 | 519 |
| HPV33 | E1 | 8 | 434 |
| HPV33 | E1 | 11 | 434 |
| HPV33 | E1 | 9 | 505 |
| HPV33 | E1 | 10 | 505 |
| HPV33 | E1 | 10 | 593 |
| HPV33 | E1 | 10 | 570 |
| HPV33 | E1 | 8 | 485 |
| HPV33 | E1 | 8 | 549 |
| HPV33 | E1 | 9 | 549 |
| HPV33 | E1 | 8 | 437 |
| HPV33 | E1 | 10 | 437 |
| HPV33 | E1 | 8 | 308 |
| HPV33 | E1 | 11 | 146 |
| HPV33 | E1 | 8 | 355 |
| HPV33 | E1 | 9 | 273 |
| HPV33 | E1 | 8 | 280 |
| HPV33 | E1 | 11 | 280 |
| HPV33 | E1 | 11 | 575 |
| HPV33 | E1 | 9 | 335 |
| HPV33 | E1 | 8 | 608 |
| HPV33 | E1 | 9 | 608 |
| HPV33 | E1 | 9 | 568 |
| HPV33 | E1 | 10 | 440 |
| HPV33 | E1 | 11 | 440 |
| HPV33 | E1 | 10 | 604 |
| HPV33 | E1 | 9 | 211 |
| HPV33 | E1 | 9 | 342 |
| HPV33 | E1 | 9 | 539 |
| HPV33 | E1 | 10 | 111 |
| HPV33 | E1 | 9 | 292 |
| HPV33 | E1 | 11 | 482 |
| HPV33 | E1 | 11 | 243 |
| HPV33 | E1 | 9 | 252 |
| HPV33 | E1 | 9 | 239 |
| HPV33 | E1 | 10 | 239 |
| HPV33 | E1 | 8 | 521 |
| HPV33 | E1 | 9 | 521 |
| HPV33 | E1 | 8 | 477 |
| HPV33 | E1 | 10 | 477 |
| HPV33 | E1 | 11 | 477 |
| HPV33 | E1 | 9 | 183 |
| HPV33 | E1 | 9 | 328 |
| HPV33 | E1 | 9 | 282 |
| HPV33 | E1 | 10 | 282 |
| HPV33 | E1 | 9 | 577 |
| HPV33 | E1 | 11 | 577 |
| HPV33 | E1 | 11 | 337 |
| HPV33 | E1 | 8 | 609 |
| HPV33 | E1 | 11 | 523 |
| HPV33 | E1 | 10 | 119 |
| HPV33 | E1 | 8 | 578 |
| HPV33 | E1 | 10 | 578 |
| HPV33 | E1 | 10 | 23 |
| HPV33 | E1 | 11 | 491 |
| HPV33 | E1 | 11 | 190 |
| HPV33 | E1 | 8 | 246 |
| HPV33 | E1 | 9 | 246 |
| HPV33 | E1 | 10 | 338 |
| HPV33 | E1 | 11 | 338 |
| HPV33 | E1 | 10 | 182 |
| HPV33 | E1 | 8 | 517 |
| HPV33 | E1 | 9 | 517 |
| HPV33 | E1 | 9 | 594 |
| HPV33 | E1 | 8 | 17 |
| HPV33 | E1 | 9 | 314 |
| HPV33 | E1 | 8 | 332 |
| HPV33 | E1 | 10 | 502 |
| HPV33 | E1 | 8 | 522 |
| HPV33 | E1 | 9 | 478 |
| HPV33 | E1 | 10 | 478 |
| HPV33 | E1 | 10 | 524 |
| HPV33 | E1 | 9 | 571 |
| HPV33 | E1 | 11 | 571 |

TABLE X-continued

HLA A24 Supermotif Peptides

| 1 | 2 | 3 | 4 |
|---|---|---|---|
| HPV33 | E1 | 11 | 528 |
| HPV33 | E1 | 10 | 313 |
| HPV33 | E2 | 9 | 69 |
| HPV33 | E2 | 11 | 69 |
| HPV33 | E2 | 10 | 78 |
| HPV33 | E2 | 9 | 41 |
| HPV33 | E2 | 11 | 41 |
| HPV33 | E2 | 9 | 10 |
| HPV33 | E2 | 10 | 10 |
| HPV33 | E2 | 9 | 288 |
| HPV33 | E2 | 10 | 145 |
| HPV33 | E2 | 11 | 145 |
| HPV33 | E2 | 9 | 25 |
| HPV33 | E2 | 11 | 25 |
| HPV33 | E2 | 10 | 17 |
| HPV33 | E2 | 9 | 235 |
| HPV33 | E2 | 10 | 235 |
| HPV33 | E2 | 9 | 232 |
| HPV33 | E2 | 8 | 153 |
| HPV33 | E2 | 8 | 130 |
| HPV33 | E2 | 9 | 130 |
| HPV33 | E2 | 10 | 130 |
| HPV33 | E2 | 11 | 130 |
| HPV33 | E2 | 9 | 74 |
| HPV33 | E2 | 10 | 298 |
| HPV33 | E2 | 8 | 80 |
| HPV33 | E2 | 9 | 185 |
| HPV33 | E2 | 11 | 100 |
| HPV33 | E2 | 9 | 325 |
| HPV33 | E2 | 10 | 325 |
| HPV33 | E2 | 11 | 325 |
| HPV33 | E2 | 11 | 336 |
| HPV33 | E2 | 10 | 53 |
| HPV33 | E2 | 11 | 53 |
| HPV33 | E2 | 9 | 278 |
| HPV33 | E2 | 11 | 32 |
| HPV33 | E2 | 9 | 139 |
| HPV33 | E2 | 11 | 276 |
| HPV33 | E2 | 11 | 137 |
| HPV33 | E2 | 8 | 339 |
| HPV33 | E2 | 9 | 242 |
| HPV33 | E2 | 9 | 34 |
| HPV33 | E2 | 10 | 34 |
| HPV33 | E2 | 11 | 34 |
| HPV33 | E2 | 8 | 23 |
| HPV33 | E2 | 11 | 23 |
| HPV33 | E2 | 8 | 66 |
| HPV33 | E2 | 10 | 66 |
| HPV33 | E2 | 8 | 151 |
| HPV33 | E2 | 9 | 151 |
| HPV33 | E2 | 10 | 151 |
| HPV33 | E2 | 10 | 169 |
| HPV33 | E2 | 8 | 177 |
| HPV33 | E2 | 8 | 243 |
| HPV33 | E2 | 8 | 35 |
| HPV33 | E2 | 9 | 35 |
| HPV33 | E2 | 10 | 35 |
| HPV33 | E2 | 9 | 62 |
| HPV33 | E2 | 8 | 42 |
| HPV33 | E2 | 10 | 42 |
| HPV33 | E2 | 11 | 240 |
| HPV33 | E2 | 9 | 18 |
| HPV33 | E2 | 9 | 299 |
| HPV33 | E2 | 11 | 299 |
| HPV33 | E2 | 9 | 43 |
| HPV33 | E2 | 8 | 333 |
| HPV33 | E2 | 8 | 147 |
| HPV33 | E2 | 9 | 147 |
| HPV33 | E2 | 11 | 147 |
| HPV33 | E2 | 11 | 183 |
| HPV33 | E2 | 11 | 157 |
| HPV33 | E2 | 8 | 127 |
| HPV33 | E2 | 11 | 127 |
| HPV33 | E2 | 8 | 272 |
| HPV33 | E2 | 8 | 133 |
| HPV33 | E2 | 9 | 196 |
| HPV33 | E2 | 9 | 342 |
| HPV33 | E2 | 10 | 342 |
| HPV33 | E2 | 9 | 295 |
| HPV33 | E2 | 8 | 29 |
| HPV33 | E2 | 10 | 29 |
| HPV33 | E2 | 9 | 345 |
| HPV33 | E2 | 10 | 203 |
| HPV33 | E2 | 9 | 332 |
| HPV33 | E2 | 8 | 96 |
| HPV33 | E2 | 9 | 71 |
| HPV33 | E2 | 9 | 191 |
| HPV33 | E2 | 9 | 91 |
| HPV33 | E2 | 10 | 120 |
| HPV33 | E2 | 9 | 86 |
| HPV33 | E2 | 8 | 292 |
| HPV33 | E2 | 9 | 292 |
| HPV33 | E2 | 9 | 7 |
| HPV33 | E2 | 10 | 7 |
| HPV33 | E2 | 8 | 37 |
| HPV33 | E2 | 11 | 266 |
| HPV33 | E2 | 10 | 290 |
| HPV33 | E2 | 11 | 290 |
| HPV33 | E2 | 9 | 285 |
| HPV33 | E2 | 10 | 61 |
| HPV33 | E2 | 8 | 302 |
| HPV33 | E2 | 8 | 205 |
| HPV33 | E2 | 10 | 324 |
| HPV33 | E2 | 11 | 324 |
| HPV33 | E2 | 10 | 93 |
| HPV33 | E2 | 11 | 93 |
| HPV33 | E2 | 10 | 128 |
| HPV33 | E2 | 11 | 128 |
| HPV33 | E2 | 9 | 146 |
| HPV33 | E2 | 10 | 146 |
| HPV33 | E2 | 8 | 233 |
| HPV33 | E2 | 11 | 233 |
| HPV33 | E2 | 10 | 267 |
| HPV33 | E2 | 10 | 337 |
| HPV33 | E2 | 8 | 343 |
| HPV33 | E2 | 9 | 343 |
| HPV33 | E2 | 11 | 343 |
| HPV33 | E2 | 8 | 72 |
| HPV33 | E2 | 11 | 72 |
| HPV33 | E2 | 8 | 192 |
| HPV33 | E2 | 8 | 326 |
| HPV33 | E2 | 9 | 326 |
| HPV33 | E2 | 10 | 326 |
| HPV33 | E2 | 11 | 323 |
| HPV33 | E2 | 8 | 148 |
| HPV33 | E2 | 10 | 148 |
| HPV33 | E2 | 11 | 148 |
| HPV33 | E2 | 10 | 101 |
| HPV33 | E2 | 9 | 102 |
| HPV33 | E2 | 8 | 92 |
| HPV33 | E2 | 11 | 92 |
| HPV33 | E2 | 9 | 170 |
| HPV33 | E2 | 9 | 159 |
| HPV33 | E2 | 10 | 159 |
| HPV33 | E2 | 10 | 138 |
| HPV33 | E2 | 8 | 44 |
| HPV33 | E2 | 11 | 44 |
| HPV33 | E2 | 8 | 131 |
| HPV33 | E2 | 9 | 131 |
| HPV33 | E2 | 10 | 131 |
| HPV33 | E2 | 10 | 158 |
| HPV33 | E2 | 11 | 158 |
| HPV33 | E5 | 8 | 30 |
| HPV33 | E5 | 9 | 30 |
| HPV33 | E5 | 10 | 30 |
| HPV33 | E5 | 11 | 30 |
| HPV33 | E5 | 8 | 8 |
| HPV33 | E5 | 10 | 8 |
| HPV33 | E5 | 11 | 8 |
| HPV33 | E5 | 9 | 63 |

TABLE X-continued

HLA A24 Supermotif Peptides

| 1 | 2 | 3 | 4 |
|---|---|---|---|
| HPV33 | E5 | 9 | 14 |
| HPV33 | E5 | 10 | 14 |
| HPV33 | E5 | 11 | 14 |
| HPV33 | E5 | 8 | 52 |
| HPV33 | E5 | 10 | 52 |
| HPV33 | E5 | 11 | 52 |
| HPV33 | E5 | 8 | 50 |
| HPV33 | E5 | 9 | 50 |
| HPV33 | E5 | 10 | 50 |
| HPV33 | E5 | 9 | 9 |
| HPV33 | E5 | 10 | 9 |
| HPV33 | E5 | 11 | 9 |
| HPV33 | E5 | 8 | 12 |
| HPV33 | E5 | 11 | 12 |
| HPV33 | E5 | 9 | 56 |
| HPV33 | E5 | 11 | 56 |
| HPV33 | E5 | 8 | 3 |
| HPV33 | E5 | 9 | 3 |
| HPV33 | E5 | 10 | 3 |
| HPV33 | E5 | 11 | 3 |
| HPV33 | E5 | 8 | 42 |
| HPV33 | E5 | 9 | 42 |
| HPV33 | E5 | 10 | 42 |
| HPV33 | E5 | 8 | 5 |
| HPV33 | E5 | 9 | 5 |
| HPV33 | E5 | 11 | 5 |
| HPV33 | E5 | 8 | 49 |
| HPV33 | E5 | 9 | 49 |
| HPV33 | E5 | 10 | 49 |
| HPV33 | E5 | 11 | 49 |
| HPV33 | E5 | 8 | 2 |
| HPV33 | E5 | 9 | 2 |
| HPV33 | E5 | 10 | 2 |
| HPV33 | E5 | 11 | 2 |
| HPV33 | E5 | 8 | 10 |
| HPV33 | E5 | 9 | 10 |
| HPV33 | E5 | 10 | 10 |
| HPV33 | E5 | 9 | 23 |
| HPV33 | E5 | 10 | 23 |
| HPV33 | E5 | 11 | 23 |
| HPV33 | E5 | 8 | 48 |
| HPV33 | E5 | 9 | 48 |
| HPV33 | E5 | 10 | 48 |
| HPV33 | E5 | 11 | 48 |
| HPV33 | E5 | 8 | 11 |
| HPV33 | E5 | 9 | 11 |
| HPV33 | E5 | 8 | 55 |
| HPV33 | E5 | 10 | 55 |
| HPV33 | E5 | 8 | 22 |
| HPV33 | E5 | 10 | 22 |
| HPV33 | E5 | 11 | 22 |
| HPV33 | E5 | 8 | 54 |
| HPV33 | E5 | 9 | 54 |
| HPV33 | E5 | 11 | 54 |
| HPV33 | E5 | 8 | 17 |
| HPV33 | E5 | 10 | 17 |
| HPV33 | E5 | 11 | 37 |
| HPV33 | E5 | 9 | 18 |
| HPV33 | E5 | 8 | 32 |
| HPV33 | E5 | 9 | 32 |
| HPV33 | E5 | 11 | 32 |
| HPV33 | E5 | 10 | 38 |
| HPV33 | E5 | 8 | 35 |
| HPV33 | E5 | 8 | 33 |
| HPV33 | E5 | 10 | 33 |
| HPV33 | E5 | 9 | 39 |
| HPV33 | E5 | 11 | 39 |
| 8PV33 | E5 | 8 | 57 |
| HPV33 | E5 | 10 | 57 |
| HPV33 | E5 | 9 | 1 |
| HPV33 | E5 | 10 | 1 |
| HPV33 | E5 | 11 | 1 |
| HPV33 | E5 | 11 | 61 |
| HPV33 | E5 | 9 | 21 |
| HPV33 | E5 | 11 | 21 |
| HPV33 | E5 | 8 | 46 |
| HPV33 | E5 | 9 | 46 |
| HPV33 | E5 | 10 | 46 |
| HPV33 | E5 | 11 | 46 |
| HPV33 | E5 | 8 | 25 |
| HPV33 | E5 | 9 | 25 |
| HPV33 | E5 | 11 | 25 |
| HPV33 | E5 | 8 | 16 |
| HPV33 | E5 | 9 | 16 |
| HPV33 | E5 | 11 | 16 |
| HPV33 | E5 | 9 | 27 |
| HPV33 | E5 | 11 | 27 |
| HPV33 | E5 | 8 | 28 |
| HPV33 | E5 | 10 | 28 |
| HPV33 | E5 | 11 | 28 |
| HPV33 | E5 | 9 | 41 |
| HPV33 | E5 | 10 | 41 |
| HPV33 | E5 | 11 | 41 |
| HPV33 | E5 | 8 | 4 |
| HPV33 | E5 | 9 | 4 |
| HPV33 | E5 | 10 | 4 |
| HPV33 | E5 | 8 | 6 |
| HPV33 | E5 | 10 | 6 |
| HPV33 | E5 | 9 | 34 |
| HPV33 | E5 | 8 | 31 |
| HPV33 | E5 | 9 | 31 |
| HPV33 | E5 | 10 | 31 |
| HPV33 | E5 | 8 | 40 |
| HPV33 | E5 | 10 | 40 |
| HPV33 | E5 | 11 | 40 |
| HPV33 | E5 | 9 | 53 |
| HPV33 | E5 | 10 | 53 |
| HPV33 | E5 | 9 | 58 |
| HPV33 | E6 | 9 | 46 |
| HPV33 | E6 | 9 | 18 |
| HPV33 | E6 | 11 | 18 |
| HPV33 | E6 | 8 | 103 |
| HPV33 | E6 | 8 | 66 |
| HPV33 | E6 | 11 | 66 |
| HPV33 | E6 | 8 | 30 |
| HPV33 | E6 | 11 | 139 |
| HPV33 | E6 | 11 | 44 |
| HPV33 | E6 | 10 | 14 |
| HPV33 | E6 | 9 | 120 |
| HPV33 | E6 | 9 | 4 |
| HPV33 | E6 | 8 | 98 |
| HPV33 | E6 | 11 | 27 |
| HPV33 | E6 | 9 | 20 |
| HPV33 | E6 | 10 | 41 |
| HPV33 | E6 | 10 | 75 |
| HPV33 | E6 | 8 | 69 |
| HPV33 | E6 | 11 | 69 |
| HPV33 | E6 | 9 | 61 |
| HPV33 | E6 | 10 | 61 |
| HPV33 | E6 | 8 | 118 |
| HPV33 | E6 | 11 | 118 |
| HPV33 | E6 | 11 | 78 |
| HPV33 | E6 | 8 | 72 |
| HPV33 | E6 | 10 | 72 |
| HPV33 | E6 | 10 | 64 |
| HPV33 | E6 | 11 | 100 |
| HPV33 | E6 | 11 | 50 |
| HPV33 | E6 | 11 | 86 |
| HPV33 | E6 | 9 | 80 |
| HPV33 | E6 | 9 | 59 |
| HPV33 | E6 | 11 | 59 |
| HPV33 | E6 | 10 | 95 |
| HPV33 | E6 | 11 | 95 |
| HPV33 | E6 | 8 | 36 |
| HPV33 | E6 | 10 | 36 |
| HPV33 | E6 | 10 | 90 |
| HPV33 | E6 | 11 | 90 |
| HPV33 | E6 | 9 | 124 |
| HPV33 | E6 | 9 | 68 |
| HPV33 | E6 | 10 | 10 |

TABLE X-continued

HLA A24 Supermotif Peptides

| 1 | 2 | 3 | 4 |
|---|---|---|---|
| HPV33 | E6 | 10 | 131 |
| HPV33 | E6 | 10 | 87 |
| HPV33 | E6 | 9 | 11 |
| HPV33 | E6 | 8 | 21 |
| HPV33 | E6 | 9 | 91 |
| HPV33 | E6 | 10 | 91 |
| HPV33 | E6 | 11 | 91 |
| HPV33 | E6 | 10 | 51 |
| HPV33 | E6 | 9 | 52 |
| HPV33 | E6 | 11 | 52 |
| HPV33 | E6 | 9 | 42 |
| HPV33 | E6 | 8 | 53 |
| HPV33 | E6 | 10 | 53 |
| HPV33 | E7 | 9 | 68 |
| HPV33 | E7 | 8 | 75 |
| HPV33 | E7 | 9 | 75 |
| HPV33 | E7 | 10 | 75 |
| HPV33 | E7 | 8 | 21 |
| HPV33 | E7 | 9 | 14 |
| HPV33 | E7 | 10 | 14 |
| HPV33 | E7 | 9 | 59 |
| HPV33 | E7 | 8 | 82 |
| HPV33 | E7 | 8 | 15 |
| HPV33 | E7 | 9 | 15 |
| HPV33 | E7 | 11 | 15 |
| HPV33 | E7 | 10 | 19 |
| HPV33 | E7 | 8 | 6 |
| HPV33 | E7 | 10 | 6 |
| HPV33 | E7 | 11 | 6 |
| HPV33 | E7 | 9 | 81 |
| HPV33 | E7 | 11 | 66 |
| HPV33 | E7 | 8 | 77 |
| HPV33 | E7 | 9 | 71 |
| HPV33 | E7 | 9 | 7 |
| HPV33 | E7 | 10 | 7 |
| HPV33 | E7 | 11 | 12 |
| HPV33 | L1 | 10 | 290 |
| HPV33 | L1 | 10 | 392 |
| HPV33 | L1 | 9 | 44 |
| HPV33 | L1 | 8 | 270 |
| HPV33 | L1 | 11 | 147 |
| HPV33 | L1 | 10 | 345 |
| HPV33 | L1 | 9 | 223 |
| HPV33 | L1 | 8 | 396 |
| HPV33 | L1 | 10 | 396 |
| HPV33 | L1 | 11 | 457 |
| HPV33 | L1 | 10 | 449 |
| HPV33 | L1 | 8 | 370 |
| HPV33 | L1 | 10 | 199 |
| HPV33 | L1 | 8 | 129 |
| HPV33 | L1 | 9 | 202 |
| HPV33 | L1 | 8 | 335 |
| HPV33 | L1 | 10 | 335 |
| HPV33 | L1 | 11 | 415 |
| HPV33 | L1 | 9 | 151 |
| HPV33 | L1 | 10 | 151 |
| HPV33 | L1 | 10 | 233 |
| HPV33 | L1 | 8 | 107 |
| HPV33 | L1 | 8 | 447 |
| HPV33 | L1 | 9 | 385 |
| HPV33 | L1 | 8 | 368 |
| HPV33 | L1 | 10 | 368 |
| HPV33 | L1 | 9 | 361 |
| HPV33 | L1 | 11 | 361 |
| HPV33 | L1 | 8 | 26 |
| HPV33 | L1 | 9 | 26 |
| HPV33 | L1 | 10 | 26 |
| HPV33 | L1 | 11 | 26 |
| HPV33 | L1 | 9 | 247 |
| HPV33 | L1 | 10 | 247 |
| HPV33 | L1 | 8 | 248 |
| HPV33 | L1 | 9 | 248 |
| HPV33 | L1 | 8 | 260 |
| HPV33 | L1 | 9 | 291 |
| HPV33 | L1 | 8 | 249 |
| HPV33 | L1 | 10 | 373 |
| HPV33 | L1 | 10 | 445 |
| HPV33 | L1 | 9 | 91 |
| HPV33 | L1 | 11 | 91 |
| HPV33 | L1 | 10 | 204 |
| HPV33 | L1 | 8 | 85 |
| HPV33 | L1 | 9 | 322 |
| HPV33 | L1 | 8 | 117 |
| HPV33 | L1 | 11 | 117 |
| HPV33 | L1 | 10 | 105 |
| HPV33 | L1 | 8 | 472 |
| HPV33 | L1 | 11 | 68 |
| HPV33 | L1 | 10 | 404 |
| HPV33 | L1 | 11 | 265 |
| HPV33 | L1 | 11 | 281 |
| HPV33 | L1 | 9 | 115 |
| HPV33 | L1 | 10 | 115 |
| HPV33 | L1 | 9 | 259 |
| HPV33 | L1 | 9 | 365 |
| HPV33 | L1 | 11 | 365 |
| HPV33 | L1 | 9 | 397 |
| HPV33 | L1 | 10 | 33 |
| HPV33 | L1 | 11 | 33 |
| HPV33 | L1 | 11 | 126 |
| HPV33 | L1 | 9 | 83 |
| HPV33 | L1 | 10 | 83 |
| HPV33 | L1 | 8 | 466 |
| HPV33 | L1 | 9 | 453 |
| HPV33 | L1 | 11 | 453 |
| HPV33 | L1 | 10 | 60 |
| HPV33 | L1 | 11 | 236 |
| HPV33 | L1 | 10 | 65 |
| HPV33 | L1 | 9 | 379 |
| HPV33 | L1 | 11 | 379 |
| HPV33 | L1 | 8 | 20 |
| HPV33 | L1 | 8 | 230 |
| HPV33 | L1 | 9 | 442 |
| HPV33 | L1 | 10 | 246 |
| HPV33 | L1 | 11 | 246 |
| HPV33 | L1 | 8 | 306 |
| HPV33 | L1 | 11 | 190 |
| HPV33 | L1 | 8 | 42 |
| HPV33 | L1 | 9 | 42 |
| HPV33 | L1 | 11 | 42 |
| HPV33 | L1 | 9 | 61 |
| HPV33 | L1 | 11 | 61 |
| HPV33 | L1 | 8 | 382 |
| HPV33 | L1 | 9 | 382 |
| HPV33 | L1 | 9 | 405 |
| HPV33 | L1 | 8 | 62 |
| HPV33 | L1 | 10 | 62 |
| HPV33 | L1 | 8 | 99 |
| HPV33 | L1 | 10 | 99 |
| HPV33 | L1 | 10 | 237 |
| HPV33 | L1 | 11 | 237 |
| HPV33 | L1 | 11 | 387 |
| HPV33 | L1 | 9 | 200 |
| HPV33 | L1 | 11 | 200 |
| HPV33 | L1 | 8 | 299 |
| HPV33 | L1 | 9 | 299 |
| HPV33 | L1 | 9 | 192 |
| HPV33 | L1 | 11 | 221 |
| HPV33 | L1 | 8 | 187 |
| HPV33 | L1 | 9 | 187 |
| HPV33 | L1 | 8 | 439 |
| HPV33 | L1 | 8 | 462 |
| HPV33 | L1 | 11 | 113 |
| HPV33 | L1 | 8 | 55 |
| HPV33 | L1 | 11 | 17 |
| HPV33 | L1 | 8 | 241 |
| HPV33 | L1 | 9 | 241 |
| HPV33 | L1 | 10 | 241 |
| HPV33 | L1 | 8 | 460 |
| HPV33 | L1 | 9 | 460 |
| HPV33 | L1 | 10 | 460 |

TABLE X-continued

HLA A24 Supermotif Peptides

| 1 | 2 | 3 | 4 |
|---|---|---|---|
| HPV33 | L1 | 11 | 372 |
| HPV33 | L1 | 8 | 305 |
| HPV33 | L1 | 9 | 305 |
| HPV33 | L1 | 8 | 254 |
| HPV33 | L1 | 8 | 347 |
| HPV33 | L1 | 9 | 70 |
| HPV33 | L1 | 8 | 418 |
| HPV33 | L1 | 9 | 41 |
| HPV33 | L1 | 10 | 41 |
| HPV33 | L1 | 8 | 77 |
| HPV33 | L1 | 10 | 77 |
| HPV33 | L1 | 9 | 98 |
| HPV33 | L1 | 11 | 98 |
| HPV33 | L1 | 10 | 75 |
| HPV33 | L1 | 10 | 90 |
| HPV33 | L1 | 11 | 51 |
| HPV33 | L1 | 8 | 285 |
| HPV33 | L1 | 11 | 32 |
| HPV33 | L1 | 11 | 245 |
| HPV33 | L1 | 8 | 412 |
| HPV33 | L1 | 9 | 149 |
| HPV33 | L1 | 11 | 149 |
| HPV33 | L1 | 9 | 298 |
| HPV33 | L1 | 10 | 298 |
| HPV33 | L1 | 8 | 227 |
| HPV33 | L1 | 9 | 227 |
| HPV33 | L1 | 11 | 227 |
| HPV33 | L1 | 11 | 23 |
| HPV33 | L1 | 8 | 352 |
| HPV33 | L1 | 11 | 352 |
| HPV33 | L1 | 11 | 2 |
| HPV33 | L1 | 11 | 444 |
| HPV33 | L1 | 8 | 193 |
| HPV33 | L1 | 10 | 266 |
| HPV33 | L1 | 11 | 266 |
| HPV33 | L1 | 11 | 212 |
| HPV33 | L1 | 9 | 381 |
| HPV33 | L1 | 10 | 381 |
| HPV33 | L1 | 10 | 282 |
| HPV33 | L1 | 11 | 282 |
| HPV33 | L1 | 9 | 336 |
| HPV33 | L1 | 11 | 430 |
| HPV33 | L1 | 11 | 332 |
| HPV33 | L1 | 10 | 388 |
| HPV33 | L1 | 11 | 388 |
| HPV33 | L1 | 10 | 353 |
| HPV33 | L1 | 11 | 353 |
| HPV33 | L1 | 10 | 416 |
| HPV33 | L1 | 9 | 374 |
| HPV33 | L1 | 8 | 386 |
| HPV33 | L1 | 8 | 380 |
| HPV33 | L1 | 10 | 380 |
| HPV33 | L1 | 11 | 380 |
| HPV33 | L1 | 8 | 300 |
| HPV33 | L1 | 10 | 333 |
| HPV33 | L1 | 9 | 100 |
| HPV33 | L1 | 10 | 3 |
| HPV33 | L1 | 11 | 3 |
| HPV33 | L1 | 9 | 389 |
| HPV33 | L1 | 10 | 389 |
| HPV33 | L1 | 11 | 276 |
| HPV33 | L1 | 8 | 362 |
| HPV33 | L1 | 10 | 362 |
| HPV33 | L1 | 9 | 234 |
| HPV33 | L1 | 8 | 443 |
| HPV33 | L1 | 8 | 27 |
| HPV33 | L1 | 9 | 27 |
| HPV33 | L1 | 10 | 27 |
| HPV33 | L1 | 8 | 35 |
| HPV33 | L1 | 9 | 35 |
| HPV33 | L1 | 9 | 34 |
| HPV33 | L1 | 10 | 34 |
| HPV33 | L2 | 11 | 256 |
| HPV33 | L2 | 9 | 241 |
| HPV33 | L2 | 10 | 241 |
| HPV33 | L2 | 11 | 291 |
| HPV33 | L2 | 10 | 23 |
| HPV33 | L2 | 11 | 308 |
| HPV33 | L2 | 10 | 385 |
| HPV33 | L2 | 8 | 280 |
| HPV33 | L2 | 8 | 439 |
| HPV33 | L2 | 9 | 439 |
| HPV33 | L2 | 10 | 439 |
| HPV33 | L2 | 11 | 439 |
| HPV33 | L2 | 10 | 283 |
| HPV33 | L2 | 10 | 272 |
| HPV33 | L2 | 11 | 272 |
| HPV33 | L2 | 8 | 327 |
| HPV33 | L2 | 10 | 431 |
| HPV33 | L2 | 10 | 264 |
| HPV33 | L2 | 10 | 401 |
| HPV33 | L2 | 9 | 350 |
| HPV33 | L2 | 10 | 95 |
| HPV33 | L2 | 9 | 369 |
| HPV33 | L2 | 11 | 30 |
| HPV33 | L2 | 11 | 113 |
| HPV33 | L2 | 10 | 447 |
| HPV33 | L2 | 8 | 242 |
| HPV33 | L2 | 9 | 242 |
| HPV33 | L2 | 11 | 242 |
| HPV33 | L2 | 8 | 440 |
| HPV33 | L2 | 9 | 440 |
| HPV33 | L2 | 10 | 440 |
| HPV33 | L2 | 8 | 421 |
| HPV33 | L2 | 10 | 421 |
| HPV33 | L2 | 8 | 25 |
| HPV33 | L2 | 9 | 75 |
| HPV33 | L2 | 11 | 75 |
| HPV33 | L2 | 9 | 51 |
| HPV33 | L2 | 8 | 374 |
| HPV33 | L2 | 11 | 374 |
| HPV33 | L2 | 8 | 336 |
| HPV33 | L2 | 10 | 336 |
| HPV33 | L2 | 9 | 323 |
| HPV33 | L2 | 9 | 284 |
| HPV33 | L2 | 10 | 44 |
| HPV33 | L2 | 11 | 44 |
| HPV33 | L2 | 9 | 448 |
| HPV33 | L2 | 11 | 448 |
| HPV33 | L2 | 10 | 292 |
| HPV33 | L2 | 8 | 250 |
| HPV33 | L2 | 11 | 250 |
| HPV33 | L2 | 10 | 104 |
| HPV33 | L2 | 11 | 104 |
| HPV33 | L2 | 8 | 433 |
| HPV33 | L2 | 10 | 433 |
| HPV33 | L2 | 10 | 248 |
| HPV33 | L2 | 8 | 311 |
| HPV33 | L2 | 11 | 34 |
| HPV33 | L2 | 8 | 236 |
| HPV33 | L2 | 8 | 46 |
| HPV33 | L2 | 9 | 46 |
| HPV33 | L2 | 8 | 414 |
| HPV33 | L2 | 11 | 414 |
| HPV33 | L2 | 8 | 107 |
| HPV33 | L2 | 9 | 249 |
| HPV33 | L2 | 8 | 243 |
| HPV33 | L2 | 10 | 243 |
| HPV33 | L2 | 9 | 397 |
| HPV33 | L2 | 10 | 372 |
| HPV33 | L2 | 10 | 391 |
| HPV33 | L2 | 10 | 143 |
| HPV33 | L2 | 8 | 209 |
| HPV33 | L2 | 8 | 426 |
| HPV33 | L2 | 8 | 420 |
| HPV33 | L2 | 9 | 420 |
| HPV33 | L2 | 11 | 420 |
| HPV33 | L2 | 11 | 73 |
| HPV33 | L2 | 11 | 215 |
| HPV33 | L2 | 8 | 423 |

TABLE X-continued

HLA A24 Supermotif Peptides

| 1 | 2 | 3 | 4 |
|---|---|---|---|
| HPV33 | L2 | 11 | 423 |
| HPV33 | L2 | 11 | 333 |
| HPV33 | L2 | 9 | 99 |
| HPV33 | L2 | 10 | 99 |
| HPV33 | L2 | 9 | 413 |
| HPV33 | L2 | 10 | 347 |
| HPV33 | L2 | 11 | 395 |
| HPV33 | L2 | 9 | 376 |
| HPV33 | L2 | 10 | 79 |
| HPV33 | L2 | 9 | 161 |
| HPV33 | L2 | 9 | 416 |
| HPV33 | L2 | 8 | 186 |
| HPV33 | L2 | 11 | 186 |
| HPV33 | L2 | 8 | 221 |
| HPV33 | L2 | 8 | 403 |
| HPV33 | L2 | 10 | 91 |
| HPV33 | L2 | 8 | 317 |
| HPV33 | L2 | 9 | 317 |
| HPV33 | L2 | 8 | 43 |
| HPV33 | L2 | 11 | 43 |
| HPV33 | L2 | 11 | 153 |
| HPV33 | L2 | 9 | 234 |
| HPV33 | L2 | 10 | 234 |
| HPV33 | L2 | 11 | 300 |
| HPV33 | L2 | 8 | 321 |
| HPV33 | L2 | 11 | 321 |
| HPV33 | L2 | 9 | 388 |
| HPV33 | L2 | 8 | 303 |
| HPV33 | L2 | 8 | 259 |
| HPV33 | L2 | 10 | 259 |
| HPV33 | L2 | 10 | 357 |
| HPV33 | L2 | 8 | 393 |
| HPV33 | L2 | 8 | 122 |
| HPV33 | L2 | 9 | 151 |
| HPV33 | L2 | 11 | 103 |
| HPV33 | L2 | 9 | 49 |
| HPV33 | L2 | 11 | 49 |
| HPV33 | L2 | 8 | 106 |
| HPV33 | L2 | 9 | 106 |
| HPV33 | L2 | 8 | 156 |
| HPV33 | L2 | 8 | 38 |
| HPV33 | L2 | 10 | 38 |
| HPV33 | L2 | 8 | 189 |
| HPV33 | L2 | 10 | 189 |
| HPV33 | L2 | 11 | 352 |
| HPV33 | L2 | 10 | 146 |
| HPV33 | L2 | 10 | 192 |
| HPV33 | L2 | 8 | 355 |
| HPV33 | L2 | 9 | 355 |
| HPV33 | L2 | 8 | 162 |
| HPV33 | L2 | 9 | 39 |
| HPV33 | L2 | 10 | 154 |
| HPV33 | L2 | 9 | 432 |
| HPV33 | L2 | 11 | 432 |
| HPV33 | L2 | 10 | 309 |
| HPV33 | L2 | 9 | 265 |
| HPV33 | L2 | 9 | 386 |
| HPV33 | L2 | 11 | 386 |
| HPV33 | L2 | 10 | 132 |
| HPV33 | L2 | 11 | 132 |
| HPV33 | L2 | 8 | 93 |
| HPV33 | L2 | 9 | 96 |
| HPV33 | L2 | 9 | 337 |
| HPV33 | L2 | 10 | 187 |
| HPV33 | L2 | 10 | 251 |
| HPV33 | L2 | 8 | 52 |
| HPV33 | L2 | 10 | 31 |
| HPV33 | L2 | 8 | 441 |
| HPV33 | L2 | 9 | 441 |
| HPV33 | L2 | 11 | 404 |
| HPV33 | L2 | 11 | 131 |
| HPV33 | L2 | 9 | 92 |
| HPV33 | L2 | 9 | 434 |
| HPV33 | L2 | 11 | 446 |
| HPV33 | L2 | 8 | 324 |
| HPV33 | L2 | 11 | 324 |
| HPV45 | E1 | 11 | 384 |
| HPV45 | E1 | 9 | 532 |
| HPV45 | E1 | 9 | 311 |
| HPV45 | E1 | 9 | 199 |
| HPV45 | E1 | 10 | 199 |
| HPV45 | E1 | 11 | 512 |
| HPV45 | E1 | 8 | 40 |
| HPV45 | E1 | 11 | 40 |
| HPV45 | E1 | 8 | 517 |
| HPV45 | E1 | 9 | 517 |
| HPV45 | E1 | 10 | 251 |
| HPV45 | E1 | 9 | 202 |
| HPV45 | E1 | 11 | 202 |
| HPV45 | E1 | 10 | 604 |
| HPV45 | E1 | 9 | 259 |
| HPV45 | E1 | 10 | 259 |
| HPV45 | E1 | 11 | 259 |
| HPV45 | E1 | 9 | 297 |
| HPV45 | E1 | 8 | 226 |
| HPV45 | E1 | 9 | 226 |
| HPV45 | E1 | 10 | 634 |
| HPV45 | E1 | 8 | 521 |
| HPV45 | E1 | 9 | 521 |
| HPV45 | E1 | 9 | 49 |
| HPV45 | E1 | 10 | 206 |
| HPV45 | E1 | 8 | 349 |
| HPV45 | E1 | 10 | 349 |
| HPV45 | E1 | 9 | 108 |
| HPV45 | E1 | 11 | 108 |
| HPV45 | E1 | 8 | 361 |
| HPV45 | E1 | 10 | 361 |
| HPV45 | E1 | 9 | 367 |
| HPV45 | E1 | 10 | 46 |
| HPV45 | E1 | 11 | 352 |
| HPV45 | E1 | 8 | 106 |
| HPV45 | E1 | 11 | 106 |
| HPV45 | E1 | 10 | 623 |
| HPV45 | E1 | 9 | 42 |
| HPV45 | E1 | 10 | 42 |
| HPV45 | E1 | 9 | 328 |
| HPV45 | E1 | 11 | 328 |
| HPV45 | E1 | 8 | 431 |
| HPV45 | E1 | 9 | 431 |
| HPV45 | E1 | 11 | 431 |
| HPV45 | E1 | 9 | 445 |
| HPV45 | E1 | 10 | 596 |
| HPV45 | E1 | 11 | 596 |
| HPV45 | E1 | 10 | 38 |
| HPV45 | E1 | 11 | 295 |
| HPV45 | E1 | 9 | 74 |
| HPV45 | E1 | 11 | 74 |
| HPV45 | E1 | 9 | 324 |
| HPV45 | E1 | 10 | 324 |
| HPV45 | E1 | 8 | 331 |
| HPV45 | E1 | 9 | 331 |
| HPV45 | E1 | 9 | 605 |
| HPV45 | E1 | 11 | 605 |
| HPV45 | E1 | 8 | 50 |
| HPV45 | E1 | 9 | 483 |
| HPV45 | E1 | 10 | 483 |
| HPV45 | E1 | 8 | 446 |
| HPV45 | E1 | 11 | 446 |
| HPV45 | E1 | 11 | 456 |
| HPV45 | E1 | 10 | 385 |
| HPV45 | E1 | 11 | 385 |
| HPV45 | E1 | 9 | 486 |
| HPV45 | E1 | 8 | 449 |
| HPV45 | E1 | 9 | 449 |
| HPV45 | E1 | 9 | 438 |
| HPV45 | E1 | 10 | 438 |
| HPV45 | E1 | 8 | 212 |
| HPV45 | E1 | 9 | 579 |
| HPV45 | E1 | 8 | 130 |
| HPV45 | E1 | 8 | 494 |

TABLE X-continued

HLA A24 Supermotif Peptides

| 1 | 2 | 3 | 4 |
|---|---|---|---|
| HPV45 | E1 | 9 | 494 |
| HPV45 | E1 | 10 | 494 |
| HPV45 | E1 | 11 | 243 |
| HPV45 | E1 | 9 | 342 |
| HPV45 | E1 | 11 | 209 |
| HPV45 | E1 | 8 | 480 |
| HPV45 | E1 | 8 | 11 |
| HPV45 | E1 | 9 | 11 |
| HPV45 | E1 | 8 | 459 |
| HPV45 | E1 | 9 | 459 |
| HPV45 | E1 | 10 | 459 |
| HPV45 | E1 | 11 | 459 |
| HPV45 | E1 | 8 | 443 |
| HPV45 | E1 | 11 | 443 |
| HPV45 | E1 | 8 | 265 |
| HPV45 | E1 | 10 | 265 |
| HPV45 | E1 | 10 | 235 |
| HPV45 | E1 | 8 | 16 |
| HPV45 | E1 | 8 | 485 |
| HPV45 | E1 | 10 | 485 |
| HPV45 | E1 | 9 | 256 |
| HPV45 | E1 | 10 | 519 |
| HPV45 | E1 | 11 | 519 |
| HPV45 | E1 | 8 | 292 |
| HPV45 | E1 | 9 | 292 |
| HPV45 | E1 | 10 | 404 |
| HPV45 | E1 | 11 | 338 |
| HPV45 | E1 | 11 | 491 |
| HPV45 | E1 | 8 | 184 |
| HPV45 | E1 | 10 | 23 |
| HPV45 | E1 | 9 | 207 |
| HPV45 | E1 | 8 | 425 |
| HPV45 | E1 | 11 | 425 |
| HPV45 | E1 | 9 | 304 |
| HPV45 | E1 | 10 | 304 |
| HPV45 | E1 | 11 | 304 |
| HPV45 | E1 | 9 | 245 |
| HPV45 | E1 | 10 | 245 |
| HPV45 | E1 | 9 | 223 |
| HPV45 | E1 | 11 | 223 |
| HPV45 | E1 | 9 | 263 |
| HPV45 | E1 | 10 | 263 |
| HPV45 | E1 | 9 | 393 |
| HPV45 | E1 | 9 | 129 |
| HPV45 | E1 | 8 | 247 |
| HPV45 | E1 | 11 | 247 |
| HPV45 | E1 | 8 | 267 |
| HPV45 | E1 | 9 | 290 |
| HPV45 | E1 | 10 | 290 |
| HPV45 | E1 | 11 | 290 |
| HPV45 | E1 | 11 | 190 |
| HPV45 | E1 | 9 | 547 |
| HPV45 | E1 | 10 | 547 |
| HPV45 | E1 | 11 | 547 |
| HPV45 | E1 | 11 | 271 |
| HPV45 | E1 | 9 | 362 |
| HPV45 | E1 | 11 | 362 |
| HPV45 | E1 | 8 | 336 |
| HPV45 | E1 | 10 | 281 |
| HPV45 | E1 | 11 | 281 |
| HPV45 | E1 | 8 | 253 |
| HPV45 | E1 | 11 | 468 |
| HPV45 | E1 | 8 | 312 |
| HPV45 | E1 | 11 | 312 |
| HPV45 | E1 | 8 | 200 |
| HPV45 | E1 | 9 | 200 |
| HPV45 | E1 | 11 | 200 |
| HPV45 | E1 | 10 | 513 |
| HPV45 | E1 | 8 | 298 |
| HPV45 | E1 | 9 | 47 |
| HPV45 | E1 | 11 | 47 |
| HPV45 | E1 | 10 | 353 |
| HPV45 | E1 | 10 | 347 |
| HPV45 | E1 | 10 | 560 |
| HPV45 | E1 | 8 | 414 |
| HPV45 | E1 | 9 | 473 |
| HPV45 | E1 | 11 | 473 |
| HPV45 | E1 | 8 | 177 |
| HPV45 | E1 | 11 | 177 |
| HPV45 | E1 | 10 | 601 |
| HPV45 | E1 | 10 | 586 |
| HPV45 | E1 | 8 | 554 |
| HPV45 | E1 | 11 | 537 |
| HPV45 | E1 | 8 | 434 |
| HPV45 | E1 | 9 | 505 |
| HPV45 | E1 | 10 | 505 |
| HPV45 | E1 | 10 | 546 |
| HPV45 | E1 | 11 | 546 |
| HPV45 | E1 | 10 | 238 |
| HPV45 | E1 | 11 | 238 |
| HPV45 | E1 | 10 | 593 |
| HPV45 | E1 | 10 | 570 |
| HPV45 | E1 | 10 | 437 |
| HPV45 | E1 | 11 | 437 |
| HPV45 | E1 | 8 | 549 |
| HPV45 | E1 | 9 | 549 |
| HPV45 | E1 | 8 | 102 |
| HPV45 | E1 | 8 | 412 |
| HPV45 | E1 | 10 | 412 |
| HPV45 | E1 | 10 | 80 |
| HPV45 | E1 | 8 | 355 |
| HPV45 | E1 | 10 | 417 |
| HPV45 | E1 | 10 | 128 |
| HPV45 | E1 | 9 | 335 |
| HPV45 | E1 | 8 | 280 |
| HPV45 | E1 | 11 | 280 |
| HPV45 | E1 | 8 | 608 |
| HPV45 | E1 | 11 | 575 |
| HPV45 | E1 | 9 | 273 |
| HPV45 | E1 | 8 | 440 |
| HPV45 | E1 | 10 | 440 |
| HPV45 | E1 | 11 | 440 |
| HPV45 | E1 | 10 | 482 |
| HPV45 | E1 | 11 | 482 |
| HPV45 | E1 | 9 | 448 |
| HPV45 | E1 | 10 | 448 |
| HPV45 | E1 | 9 | 211 |
| HPV45 | E1 | 9 | 493 |
| HPV45 | E1 | 10 | 493 |
| HPV45 | E1 | 11 | 493 |
| HPV45 | E1 | 9 | 539 |
| HPV45 | E1 | 10 | 539 |
| HPV45 | E1 | 8 | 183 |
| HPV45 | E1 | 9 | 183 |
| HPV45 | E1 | 11 | 288 |
| HPV45 | E1 | 8 | 308 |
| HPV45 | E1 | 10 | 104 |
| HPV45 | E1 | 8 | 477 |
| HPV45 | E1 | 10 | 477 |
| HPV45 | E1 | 11 | 477 |
| HPV45 | E1 | 8 | 580 |
| HPV45 | E1 | 11 | 22 |
| HPV45 | E1 | 8 | 246 |
| HPV45 | E1 | 9 | 246 |
| HPV45 | E1 | 10 | 289 |
| HPV45 | E1 | 11 | 289 |
| HPV45 | E1 | 9 | 252 |
| HPV45 | E1 | 8 | 224 |
| HPV45 | E1 | 10 | 224 |
| HPV45 | E1 | 11 | 224 |
| HPV45 | E1 | 9 | 239 |
| HPV45 | E1 | 10 | 239 |
| HPV45 | E1 | 9 | 282 |
| HPV45 | E1 | 10 | 282 |
| HPV45 | E1 | 9 | 577 |
| HPV45 | E1 | 11 | 577 |
| HPV45 | E1 | 11 | 523 |
| HPV45 | E1 | 8 | 203 |
| HPV45 | E1 | 10 | 203 |
| HPV45 | E1 | 8 | 578 |

TABLE X-continued

HLA A24 Supermotif Peptides

| 1 | 2 | 3 | 4 |
|---|---|---|---|
| HPV45 | E1 | 10 | 578 |
| HPV45 | E1 | 9 | 81 |
| HPV45 | E1 | 9 | 266 |
| HPV45 | E1 | 9 | 635 |
| HPV45 | E1 | 10 | 576 |
| HPV45 | E1 | 9 | 594 |
| HPV45 | E1 | 9 | 418 |
| HPV45 | E1 | 8 | 332 |
| HPV45 | E1 | 8 | 522 |
| HPV45 | E1 | 9 | 314 |
| HPV45 | E1 | 10 | 524 |
| HPV45 | E1 | 9 | 478 |
| HPV45 | E1 | 10 | 478 |
| HPV45 | E1 | 9 | 571 |
| HPV45 | E1 | 11 | 571 |
| HPV45 | E1 | 8 | 394 |
| HPV45 | E1 | 11 | 528 |
| HPV45 | E1 | 10 | 313 |
| HPV45 | E2 | 8 | 78 |
| HPV45 | E2 | 11 | 78 |
| HPV45 | E2 | 11 | 47 |
| HPV45 | E2 | 10 | 84 |
| HPV45 | E2 | 10 | 16 |
| HPV45 | E2 | 10 | 247 |
| HPV45 | E2 | 8 | 216 |
| HPV45 | E2 | 9 | 305 |
| HPV45 | E2 | 10 | 134 |
| HPV45 | E2 | 11 | 134 |
| HPV45 | E2 | 8 | 158 |
| HPV45 | E2 | 9 | 158 |
| HPV45 | E2 | 10 | 158 |
| HPV45 | E2 | 8 | 31 |
| HPV45 | E2 | 9 | 31 |
| HPV45 | E2 | 11 | 31 |
| HPV45 | E2 | 8 | 171 |
| HPV45 | E2 | 8 | 212 |
| HPV45 | E2 | 11 | 351 |
| HPV45 | E2 | 8 | 319 |
| HPV45 | E2 | 9 | 80 |
| HPV45 | E2 | 11 | 106 |
| HPV45 | E2 | 8 | 343 |
| HPV45 | E2 | 9 | 192 |
| HPV45 | E2 | 11 | 97 |
| HPV45 | E2 | 8 | 50 |
| HPV45 | E2 | 11 | 50 |
| HPV45 | E2 | 9 | 295 |
| HPV45 | E2 | 11 | 325 |
| HPV45 | E2 | 9 | 24 |
| HPV45 | E2 | 9 | 316 |
| HPV45 | E2 | 11 | 316 |
| HPV45 | E2 | 11 | 293 |
| HPV45 | E2 | 10 | 48 |
| HPV45 | E2 | 11 | 151 |
| HPV45 | E2 | 9 | 143 |
| HPV45 | E2 | 10 | 143 |
| HPV45 | E2 | 10 | 59 |
| HPV45 | E2 | 9 | 2 |
| HPV45 | E2 | 8 | 154 |
| HPV45 | E2 | 9 | 154 |
| HPV45 | E2 | 10 | 284 |
| HPV45 | E2 | 11 | 284 |
| HPV45 | E2 | 9 | 312 |
| HPV45 | E2 | 8 | 184 |
| HPV45 | E2 | 9 | 92 |
| HPV45 | E2 | 9 | 49 |
| HPV45 | E2 | 8 | 41 |
| HPV45 | E2 | 9 | 41 |
| HPV45 | E2 | 10 | 41 |
| HPV45 | E2 | 10 | 107 |
| HPV45 | E2 | 11 | 69 |
| HPV45 | E2 | 8 | 109 |
| HPV45 | E2 | 9 | 347 |
| HPV45 | E2 | 9 | 332 |
| HPV45 | E2 | 8 | 265 |
| HPV45 | E2 | 9 | 265 |
| HPV45 | E2 | 8 | 289 |
| HPV45 | E2 | 9 | 198 |
| HPV45 | E2 | 8 | 136 |
| HPV45 | E2 | 9 | 136 |
| HPV45 | E2 | 10 | 136 |
| HPV45 | E2 | 11 | 136 |
| HPV45 | E2 | 9 | 177 |
| HPV45 | E2 | 9 | 360 |
| HPV45 | E2 | 8 | 35 |
| HPV45 | E2 | 10 | 35 |
| HPV45 | E2 | 9 | 40 |
| HPV45 | E2 | 10 | 40 |
| HPV45 | E2 | 11 | 40 |
| HPV45 | E2 | 11 | 4 |
| HPV45 | E2 | 8 | 63 |
| HPV45 | E2 | 8 | 43 |
| HPV45 | E2 | 9 | 309 |
| HPV45 | E2 | 9 | 13 |
| HPV45 | E2 | 10 | 13 |
| HPV45 | E2 | 10 | 263 |
| HPV45 | E2 | 11 | 263 |
| HPV45 | E2 | 11 | 307 |
| HPV45 | E2 | 10 | 142 |
| HPV45 | E2 | 11 | 142 |
| HPV45 | E2 | 9 | 302 |
| HPV45 | E2 | 9 | 9 |
| HPV45 | E2 | 9 | 235 |
| HPV45 | E2 | 8 | 358 |
| HPV45 | E2 | 9 | 358 |
| HPV45 | E2 | 11 | 358 |
| HPV45 | E2 | 8 | 160 |
| HPV45 | E2 | 8 | 37 |
| HPV45 | E2 | 8 | 348 |
| HPV45 | E2 | 8 | 354 |
| HPV45 | E2 | 9 | 99 |
| HPV45 | E2 | 10 | 99 |
| HPV45 | E2 | 11 | 213 |
| HPV45 | E2 | 11 | 190 |
| HPV45 | E2 | 11 | 339 |
| HPV45 | E2 | 8 | 199 |
| HPV45 | E2 | 9 | 353 |
| HPV45 | E2 | 10 | 352 |
| HPV45 | E2 | 8 | 138 |
| HPV45 | E2 | 9 | 138 |
| HPV45 | E2 | 8 | 139 |
| HPV45 | E2 | 11 | 125 |
| HPV45 | E2 | 11 | 164 |
| HPV45 | E2 | 10 | 326 |
| HPV45 | E2 | 11 | 326 |
| HPV45 | E2 | 10 | 98 |
| HPV45 | E2 | 11 | 98 |
| HPV45 | E2 | 10 | 126 |
| HPV45 | E2 | 9 | 166 |
| HPV45 | E2 | 10 | 166 |
| HPV45 | E2 | 8 | 145 |
| HPV45 | E2 | 11 | 175 |
| HPV45 | E2 | 8 | 137 |
| HPV45 | E2 | 9 | 137 |
| HPV45 | E2 | 10 | 137 |
| HPV45 | E2 | 11 | 38 |
| HPV45 | E2 | 10 | 165 |
| HPV45 | E2 | 11 | 165 |
| HPV45 | E2 | 8 | 144 |
| HPV45 | E2 | 9 | 144 |
| HPV45 | E6 | 9 | 48 |
| HPV45 | E6 | 9 | 37 |
| HPV45 | E6 | 11 | 37 |
| HPV45 | E6 | 9 | 61 |
| HPV45 | E6 | 11 | 61 |
| HPV45 | E6 | 11 | 59 |
| HPV45 | E6 | 8 | 68 |
| HPV45 | E6 | 11 | 68 |
| HPV45 | E6 | 8 | 105 |
| HPV45 | E6 | 8 | 18 |
| HPV45 | E6 | 8 | 32 |

TABLE X-continued

HLA A24 Supermotif Peptides

| 1 | 2 | 3 | 4 |
|---|---|---|---|
| HPV45 | E6 | 9 | 70 |
| HPV45 | E6 | 11 | 70 |
| HPV45 | E6 | 10 | 16 |
| HPV45 | E6 | 10 | 51 |
| HPV45 | E6 | 8 | 27 |
| HPV45 | E6 | 11 | 20 |
| HPV45 | E6 | 10 | 77 |
| HPV45 | E6 | 10 | 97 |
| HPV45 | E6 | 11 | 88 |
| HPV45 | E6 | 10 | 43 |
| HPV45 | E6 | 11 | 43 |
| HPV45 | E6 | 8 | 53 |
| HPV45 | E6 | 10 | 53 |
| HPV45 | E6 | 8 | 71 |
| HPV45 | E6 | 10 | 71 |
| HPV45 | E6 | 11 | 71 |
| HPV45 | E6 | 8 | 120 |
| HPV45 | E6 | 11 | 120 |
| HPV45 | E6 | 9 | 93 |
| HPV45 | E6 | 10 | 93 |
| HPV45 | E6 | 11 | 93 |
| HPV45 | E6 | 9 | 54 |
| HPV45 | E6 | 8 | 92 |
| HPV45 | E6 | 10 | 92 |
| HPV45 | E6 | 11 | 92 |
| HPV45 | E6 | 9 | 13 |
| HPV45 | E6 | 9 | 52 |
| HPV45 | E6 | 11 | 52 |
| HPV45 | E6 | 11 | 102 |
| HPV45 | E6 | 9 | 98 |
| HPV45 | E6 | 8 | 95 |
| HPV45 | E6 | 9 | 95 |
| HPV45 | E6 | 9 | 22 |
| HPV45 | E6 | 11 | 111 |
| HPV45 | E6 | 8 | 7 |
| HPV45 | E6 | 11 | 7 |
| HPV45 | E6 | 11 | 11 |
| HPV45 | E6 | 8 | 46 |
| HPV45 | E6 | 9 | 46 |
| HPV45 | E6 | 11 | 46 |
| HPV45 | E6 | 10 | 3 |
| HPV45 | E6 | 9 | 126 |
| HPV45 | E6 | 8 | 74 |
| HPV45 | E6 | 9 | 41 |
| HPV45 | E6 | 8 | 79 |
| HPV45 | E6 | 11 | 29 |
| HPV45 | E6 | 11 | 24 |
| HPV45 | E6 | 10 | 84 |
| HPV45 | E6 | 10 | 89 |
| HPV45 | E6 | 11 | 89 |
| HPV45 | E6 | 8 | 38 |
| HPV45 | E6 | 10 | 38 |
| HPV45 | E6 | 9 | 85 |
| HPV45 | E6 | 9 | 44 |
| HPV45 | E6 | 10 | 44 |
| HPV45 | E6 | 11 | 44 |
| HPV45 | E6 | 8 | 55 |
| HPV45 | E6 | 11 | 80 |
| HPV45 | E7 | 8 | 6 |
| HPV45 | E7 | 10 | 6 |
| HPV45 | E7 | 10 | 64 |
| HPV45 | E7 | 8 | 25 |
| HPV45 | E7 | 8 | 83 |
| HPV45 | E7 | 9 | 83 |
| HPV45 | E7 | 10 | 83 |
| HPV45 | E7 | 8 | 20 |
| HPV45 | E7 | 10 | 20 |
| HPV45 | E7 | 11 | 74 |
| HPV45 | E7 | 11 | 91 |
| HPV45 | E7 | 8 | 14 |
| HPV45 | E7 | 11 | 11 |
| HPV45 | E7 | 8 | 90 |
| HPV45 | E7 | 10 | 75 |
| HPV45 | E7 | 10 | 23 |
| HPV45 | E7 | 9 | 89 |
| HPV45 | E7 | 8 | 85 |
| HPV45 | E7 | 11 | 85 |
| HPV45 | E7 | 9 | 93 |
| HPV45 | E7 | 9 | 7 |
| HPV45 | E7 | 10 | 86 |
| HPV45 | E7 | 8 | 94 |
| HPV45 | E7 | 9 | 76 |
| HPV45 | E7 | 10 | 12 |
| HPV45 | L1 | 11 | 191 |
| HPV45 | L1 | 8 | 103 |
| HPV45 | L1 | 10 | 103 |
| HPV45 | L1 | 11 | 28 |
| HPV45 | L1 | 8 | 88 |
| HPV45 | L1 | 10 | 88 |
| HPV45 | L1 | 11 | 94 |
| HPV45 | L1 | 9 | 184 |
| HPV45 | L1 | 8 | 276 |
| HPV45 | L1 | 10 | 409 |
| HPV45 | L1 | 9 | 188 |
| HPV45 | L1 | 11 | 318 |
| HPV45 | L1 | 9 | 250 |
| HPV45 | L1 | 11 | 488 |
| HPV45 | L1 | 10 | 480 |
| HPV45 | L1 | 8 | 401 |
| HPV45 | L1 | 11 | 401 |
| HPV45 | L1 | 11 | 301 |
| HPV45 | L1 | 10 | 226 |
| HPV45 | L1 | 9 | 229 |
| HPV45 | L1 | 8 | 242 |
| HPV45 | L1 | 10 | 242 |
| HPV45 | L1 | 11 | 461 |
| HPV45 | L1 | 8 | 364 |
| HPV45 | L1 | 10 | 364 |
| HPV45 | L1 | 8 | 296 |
| HPV45 | L1 | 9 | 296 |
| HPV45 | L1 | 10 | 169 |
| HPV45 | L1 | 9 | 177 |
| HPV45 | L1 | 10 | 177 |
| HPV45 | L1 | 10 | 260 |
| HPV45 | L1 | 8 | 52 |
| HPV45 | L1 | 9 | 52 |
| HPV45 | L1 | 10 | 52 |
| HPV45 | L1 | 8 | 133 |
| HPV45 | L1 | 10 | 133 |
| HPV45 | L1 | 8 | 313 |
| HPV45 | L1 | 9 | 416 |
| HPV45 | L1 | 10 | 246 |
| HPV45 | L1 | 8 | 399 |
| HPV45 | L1 | 10 | 399 |
| HPV45 | L1 | 9 | 274 |
| HPV45 | L1 | 10 | 274 |
| HPV45 | L1 | 8 | 404 |
| HPV45 | L1 | 10 | 404 |
| HPV45 | L1 | 8 | 14 |
| HPV45 | L1 | 10 | 14 |
| HPV45 | L1 | 11 | 14 |
| HPV45 | L1 | 8 | 287 |
| HPV45 | L1 | 10 | 476 |
| HPV45 | L1 | 9 | 60 |
| HPV45 | L1 | 10 | 60 |
| HPV45 | L1 | 8 | 351 |
| HPV45 | L1 | 9 | 351 |
| HPV45 | L1 | 9 | 141 |
| HPV45 | L1 | 10 | 141 |
| HPV45 | L1 | 8 | 111 |
| HPV45 | L1 | 8 | 503 |
| HPV45 | L1 | 8 | 143 |
| HPV45 | L1 | 11 | 143 |
| HPV45 | L1 | 10 | 131 |
| HPV45 | L1 | 9 | 199 |
| HPV45 | L1 | 11 | 292 |
| HPV45 | L1 | 10 | 435 |
| HPV45 | L1 | 10 | 231 |
| HPV45 | L1 | 9 | 286 |
| HPV45 | L1 | 9 | 396 |

TABLE X-continued

HLA A24 Supermotif Peptides

| 1 | 2 | 3 | 4 |
|---|---|---|---|
| HPV45 | L1 | 10 | 396 |
| HPV45 | L1 | 11 | 396 |
| HPV45 | L1 | 9 | 392 |
| HPV45 | L1 | 11 | 392 |
| HPV45 | L1 | 9 | 13 |
| HPV45 | L1 | 11 | 13 |
| HPV45 | L1 | 8 | 23 |
| HPV45 | L1 | 9 | 405 |
| HPV45 | L1 | 10 | 59 |
| HPV45 | L1 | 11 | 59 |
| HPV45 | L1 | 10 | 12 |
| HPV45 | L1 | 11 | 11 |
| HPV45 | L1 | 8 | 5 |
| HPV45 | L1 | 9 | 5 |
| HPV45 | L1 | 10 | 5 |
| HPV45 | L1 | 11 | 5 |
| HPV45 | L1 | 8 | 185 |
| HPV45 | L1 | 8 | 411 |
| HPV45 | L1 | 10 | 411 |
| HPV45 | L1 | 11 | 411 |
| HPV45 | L1 | 8 | 328 |
| HPV45 | L1 | 9 | 328 |
| HPV45 | L1 | 8 | 6 |
| HPV45 | L1 | 9 | 6 |
| HPV45 | L1 | 10 | 6 |
| HPV45 | L1 | 9 | 117 |
| HPV45 | L1 | 11 | 117 |
| HPV45 | L1 | 9 | 109 |
| HPV45 | L1 | 10 | 109 |
| HPV45 | L1 | 8 | 497 |
| HPV45 | L1 | 9 | 484 |
| HPV45 | L1 | 11 | 484 |
| HPV45 | L1 | 11 | 475 |
| HPV45 | L1 | 9 | 473 |
| HPV45 | L1 | 10 | 91 |
| HPV45 | L1 | 8 | 257 |
| HPV45 | L1 | 8 | 335 |
| HPV45 | L1 | 8 | 68 |
| HPV45 | L1 | 9 | 68 |
| HPV45 | L1 | 8 | 413 |
| HPV45 | L1 | 9 | 413 |
| HPV45 | L1 | 8 | 69 |
| HPV45 | L1 | 8 | 125 |
| HPV45 | L1 | 10 | 125 |
| HPV45 | L1 | 10 | 29 |
| HPV45 | L1 | 11 | 29 |
| HPV45 | L1 | 10 | 302 |
| HPV45 | L1 | 10 | 273 |
| HPV45 | L1 | 11 | 273 |
| HPV45 | L1 | 9 | 227 |
| HPV45 | L1 | 11 | 227 |
| HPV45 | L1 | 8 | 4 |
| HPV45 | L1 | 9 | 4 |
| HPV45 | L1 | 10 | 4 |
| HPV45 | L1 | 11 | 4 |
| HPV45 | L1 | 11 | 310 |
| HPV45 | L1 | 11 | 49 |
| HPV45 | L1 | 9 | 219 |
| HPV45 | L1 | 8 | 383 |
| HPV45 | L1 | 11 | 383 |
| HPV45 | L1 | 9 | 19 |
| HPV45 | L1 | 11 | 19 |
| HPV45 | L1 | 8 | 17 |
| HPV45 | L1 | 9 | 17 |
| HPV45 | L1 | 11 | 17 |
| HPV45 | L1 | 11 | 173 |
| HPV45 | L1 | 8 | 22 |
| HPV45 | L1 | 9 | 22 |
| HPV45 | L1 | 8 | 248 |
| HPV45 | L1 | 11 | 248 |
| HPV45 | L1 | 8 | 214 |
| HPV45 | L1 | 9 | 214 |
| HPV45 | L1 | 11 | 139 |
| HPV45 | L1 | 9 | 440 |
| HPV45 | L1 | 11 | 440 |
| HPV45 | L1 | 11 | 380 |
| HPV45 | L1 | 8 | 470 |
| HPV45 | L1 | 8 | 268 |
| HPV45 | L1 | 10 | 268 |
| HPV45 | L1 | 9 | 403 |
| HPV45 | L1 | 11 | 403 |
| HPV45 | L1 | 11 | 182 |
| HPV45 | L1 | 8 | 281 |
| HPV45 | L1 | 8 | 334 |
| HPV45 | L1 | 9 | 334 |
| HPV45 | L1 | 10 | 206 |
| HPV45 | L1 | 11 | 263 |
| HPV45 | L1 | 8 | 491 |
| HPV45 | L1 | 9 | 491 |
| HPV45 | L1 | 9 | 96 |
| HPV45 | L1 | 9 | 67 |
| HPV45 | L1 | 10 | 67 |
| HPV45 | L1 | 9 | 124 |
| HPV45 | L1 | 11 | 124 |
| HPV45 | L1 | 10 | 101 |
| HPV45 | L1 | 8 | 46 |
| HPV45 | L1 | 8 | 254 |
| HPV45 | L1 | 9 | 254 |
| HPV45 | L1 | 11 | 254 |
| HPV45 | L1 | 11 | 58 |
| HPV45 | L1 | 8 | 427 |
| HPV45 | L1 | 9 | 327 |
| HPV45 | L1 | 10 | 327 |
| HPV45 | L1 | 8 | 443 |
| HPV45 | L1 | 11 | 272 |
| HPV45 | L1 | 10 | 423 |
| HPV45 | L1 | 11 | 115 |
| HPV45 | L1 | 10 | 376 |
| HPV45 | L1 | 11 | 43 |
| HPV45 | L1 | 9 | 175 |
| HPV45 | L1 | 11 | 175 |
| HPV45 | L1 | 10 | 419 |
| HPV45 | L1 | 11 | 419 |
| HPV45 | L1 | 8 | 220 |
| HPV45 | L1 | 9 | 410 |
| HPV45 | L1 | 11 | 410 |
| HPV45 | L1 | 10 | 116 |
| HPV45 | L1 | 8 | 200 |
| HPV45 | L1 | 11 | 239 |
| HPV45 | L1 | 9 | 412 |
| HPV45 | L1 | 10 | 412 |
| HPV45 | L1 | 10 | 462 |
| HPV45 | L1 | 9 | 365 |
| HPV45 | L1 | 8 | 329 |
| HPV45 | L1 | 8 | 441 |
| HPV45 | L1 | 10 | 441 |
| HPV45 | L1 | 8 | 478 |
| HPV45 | L1 | 8 | 297 |
| HPV45 | L1 | 11 | 361 |
| HPV45 | L1 | 10 | 384 |
| HPV45 | L1 | 8 | 20 |
| HPV45 | L1 | 10 | 20 |
| HPV45 | L1 | 11 | 20 |
| HPV45 | L1 | 10 | 293 |
| HPV45 | L1 | 11 | 293 |
| HPV45 | L1 | 8 | 417 |
| HPV45 | L1 | 10 | 362 |
| HPV45 | L1 | 9 | 126 |
| HPV45 | L1 | 10 | 319 |
| HPV45 | L1 | 9 | 477 |
| HPV45 | L1 | 9 | 420 |
| HPV45 | L1 | 10 | 420 |
| HPV45 | L1 | 9 | 303 |
| HPV45 | L1 | 9 | 261 |
| HPV45 | L1 | 8 | 53 |
| HPV45 | L1 | 9 | 53 |
| HPV45 | L2 | 8 | 161 |
| HPV45 | L2 | 11 | 286 |
| HPV45 | L2 | 10 | 328 |
| HPV45 | L2 | 11 | 328 |

TABLE X-continued

HLA A24 Supermotif Peptides

| 1 | 2 | 3 | 4 |
|---|---|---|---|
| HPV45 | L2 | 11 | 303 |
| HPV45 | L2 | 8 | 340 |
| HPV45 | L2 | 11 | 340 |
| HPV45 | L2 | 9 | 255 |
| HPV45 | L2 | 11 | 255 |
| HPV45 | L2 | 8 | 275 |
| HPV45 | L2 | 10 | 405 |
| HPV45 | L2 | 11 | 405 |
| HPV45 | L2 | 10 | 278 |
| HPV45 | L2 | 11 | 322 |
| HPV45 | L2 | 11 | 142 |
| HPV45 | L2 | 9 | 345 |
| HPV45 | L2 | 11 | 83 |
| HPV45 | L2 | 11 | 30 |
| HPV45 | L2 | 10 | 397 |
| HPV45 | L2 | 11 | 397 |
| HPV45 | L2 | 8 | 331 |
| HPV45 | L2 | 8 | 241 |
| HPV45 | L2 | 11 | 241 |
| HPV45 | L2 | 9 | 122 |
| HPV45 | L2 | 11 | 157 |
| HPV45 | L2 | 8 | 306 |
| HPV45 | L2 | 8 | 368 |
| HPV45 | L2 | 10 | 368 |
| HPV45 | L2 | 8 | 319 |
| HPV45 | L2 | 9 | 51 |
| HPV45 | L2 | 8 | 430 |
| HPV45 | L2 | 9 | 430 |
| HPV45 | L2 | 10 | 430 |
| HPV45 | L2 | 8 | 25 |
| HPV45 | L2 | 10 | 206 |
| HPV45 | L2 | 10 | 183 |
| HPV45 | L2 | 9 | 433 |
| HPV45 | L2 | 10 | 433 |
| HPV45 | L2 | 11 | 433 |
| HPV45 | L2 | 8 | 37 |
| HPV45 | L2 | 9 | 37 |
| HPV45 | L2 | 11 | 37 |
| HPV45 | L2 | 8 | 134 |
| HPV45 | L2 | 10 | 134 |
| HPV45 | L2 | 8 | 292 |
| HPV45 | L2 | 10 | 191 |
| HPV45 | L2 | 9 | 318 |
| HPV45 | L2 | 8 | 52 |
| HPV45 | L2 | 9 | 406 |
| HPV45 | L2 | 10 | 406 |
| HPV45 | L2 | 9 | 279 |
| HPV45 | L2 | 8 | 407 |
| HPV45 | L2 | 9 | 407 |
| HPV45 | L2 | 9 | 44 |
| HPV45 | L2 | 10 | 44 |
| HPV45 | L2 | 11 | 44 |
| HPV45 | L2 | 10 | 143 |
| HPV45 | L2 | 8 | 400 |
| HPV45 | L2 | 9 | 400 |
| HPV45 | L2 | 8 | 43 |
| HPV45 | L2 | 10 | 43 |
| HPV45 | L2 | 11 | 43 |
| HPV45 | L2 | 11 | 34 |
| HPV45 | L2 | 8 | 346 |
| HPV45 | L2 | 10 | 337 |
| HPV45 | L2 | 11 | 337 |
| HPV45 | L2 | 10 | 242 |
| HPV45 | L2 | 11 | 375 |
| HPV45 | L2 | 9 | 392 |
| HPV45 | L2 | 10 | 392 |
| HPV45 | L2 | 9 | 248 |
| HPV45 | L2 | 8 | 438 |
| HPV45 | L2 | 9 | 305 |
| HPV45 | L2 | 8 | 270 |
| HPV45 | L2 | 10 | 270 |
| HPV45 | L2 | 11 | 270 |
| HPV45 | L2 | 10 | 387 |
| HPV45 | L2 | 8 | 325 |
| HPV45 | L2 | 10 | 325 |
| HPV45 | L2 | 8 | 399 |
| HPV45 | L2 | 9 | 399 |
| HPV45 | L2 | 10 | 399 |
| HPV45 | L2 | 8 | 258 |
| HPV45 | L2 | 11 | 336 |
| HPV45 | L2 | 10 | 391 |
| HPV45 | L2 | 11 | 391 |
| HPV45 | L2 | 9 | 98 |
| HPV45 | L2 | 9 | 120 |
| HPV45 | L2 | 11 | 120 |
| HPV45 | L2 | 9 | 420 |
| HPV45 | L2 | 10 | 420 |
| HPV45 | L2 | 8 | 86 |
| HPV45 | L2 | 8 | 185 |
| HPV45 | L2 | 11 | 185 |
| HPV45 | L2 | 10 | 267 |
| HPV45 | L2 | 11 | 267 |
| HPV45 | L2 | 8 | 145 |
| HPV45 | L2 | 11 | 216 |
| HPV45 | L2 | 9 | 95 |
| HPV45 | L2 | 11 | 118 |
| HPV45 | L2 | 8 | 453 |
| HPV45 | L2 | 9 | 240 |
| HPV45 | L2 | 8 | 312 |
| HPV45 | L2 | 9 | 312 |
| HPV45 | L2 | 9 | 172 |
| HPV45 | L2 | 10 | 172 |
| HPV45 | L2 | 9 | 233 |
| HPV45 | L2 | 10 | 233 |
| HPV45 | L2 | 8 | 46 |
| HPV45 | L2 | 9 | 46 |
| HPV45 | L2 | 8 | 435 |
| HPV45 | L2 | 9 | 435 |
| HPV45 | L2 | 10 | 435 |
| HPV45 | L2 | 11 | 435 |
| HPV45 | L2 | 11 | 295 |
| HPV45 | L2 | 10 | 451 |
| HPV45 | L2 | 8 | 298 |
| HPV45 | L2 | 9 | 298 |
| HPV45 | L2 | 8 | 316 |
| HPV45 | L2 | 11 | 316 |
| HPV45 | L2 | 8 | 220 |
| HPV45 | L2 | 8 | 235 |
| HPV45 | L2 | 9 | 367 |
| HPV45 | L2 | 11 | 367 |
| HPV45 | L2 | 9 | 49 |
| HPV45 | L2 | 11 | 49 |
| HPV45 | L2 | 10 | 247 |
| HPV45 | L2 | 9 | 362 |
| HPV45 | L2 | 9 | 154 |
| HPV45 | L2 | 11 | 358 |
| HPV45 | L2 | 8 | 424 |
| HPV45 | L2 | 9 | 149 |
| HPV45 | L2 | 9 | 384 |
| HPV45 | L2 | 10 | 250 |
| HPV45 | L2 | 8 | 121 |
| HPV45 | L2 | 10 | 121 |
| HPV45 | L2 | 8 | 363 |
| HPV45 | L2 | 11 | 363 |
| HPV45 | L2 | 9 | 39 |
| HPV45 | L2 | 10 | 304 |
| HPV45 | L2 | 10 | 376 |
| HPV45 | L2 | 8 | 38 |
| HPV45 | L2 | 10 | 38 |
| HPV45 | L2 | 8 | 136 |
| HPV45 | L2 | 10 | 359 |
| HPV45 | L2 | 9 | 135 |
| HPV45 | L2 | 11 | 426 |
| HPV45 | L2 | 8 | 389 |
| HPV45 | L2 | 10 | 217 |
| HPV45 | L2 | 11 | 217 |
| HPV45 | L2 | 10 | 427 |
| HPV45 | L2 | 11 | 427 |
| HPV45 | L2 | 9 | 369 |
| HPV45 | L2 | 10 | 31 |

TABLE X-continued

HLA A24 Supermotif Peptides

| 1 | 2 | 3 | 4 |
|---|---|---|---|
| HPV45 | L2 | 8 | 249 |
| HPV45 | L2 | 11 | 249 |
| HPV45 | L2 | 9 | 388 |
| HPV45 | L2 | 11 | 112 |
| HPV45 | L2 | 9 | 444 |
| HPV45 | L2 | 11 | 444 |
| HPV45 | L2 | 9 | 428 |
| HPV45 | L2 | 10 | 428 |
| HPV45 | L2 | 11 | 428 |
| HPV45 | L2 | 8 | 437 |
| HPV45 | L2 | 9 | 437 |
| HPV45 | L2 | 8 | 401 |
| HPV45 | L2 | 10 | 443 |
| HPV45 | L2 | 8 | 436 |
| HPV45 | L2 | 9 | 436 |
| HPV45 | L2 | 10 | 436 |
| HPV45 | L2 | 11 | 442 |
| HPV56 | E2 | 8 | 15 |
| HPV56 | E2 | 11 | 15 |
| HPV56 | E2 | 9 | 21 |
| HPV56 | E2 | 10 | 21 |
| HPV56 | E2 | 9 | 52 |
| HPV56 | E2 | 9 | 71 |
| HPV56 | E2 | 10 | 71 |
| HPV56 | E2 | 11 | 71 |
| HPV56 | E2 | 8 | 204 |
| HPV56 | E2 | 9 | 113 |
| HPV56 | E2 | 8 | 39 |
| HPV56 | E2 | 8 | 263 |
| HPV56 | E2 | 11 | 43 |
| HPV56 | E2 | 8 | 288 |
| HPV56 | E2 | 9 | 128 |
| HPV56 | E2 | 10 | 128 |
| HPV56 | E2 | 9 | 17 |
| HPV56 | E2 | 11 | 34 |
| HPV56 | E2 | 11 | 294 |
| HPV56 | E2 | 8 | 261 |
| HPV56 | E2 | 10 | 261 |
| HPV56 | E2 | 8 | 94 |
| HPV56 | E2 | 9 | 94 |
| HPV56 | E2 | 11 | 87 |
| HPV56 | E2 | 9 | 239 |
| HPV56 | E2 | 8 | 130 |
| HPV56 | E2 | 8 | 297 |
| HPV56 | E2 | 10 | 297 |
| HPV56 | E2 | 10 | 269 |
| HPV56 | E2 | 11 | 126 |
| HPV56 | E2 | 11 | 284 |
| HPV56 | E2 | 9 | 29 |
| HPV56 | E2 | 9 | 80 |
| HPV56 | E2 | 11 | 100 |
| HPV56 | E2 | 8 | 120 |
| HPV56 | E2 | 8 | 299 |
| HPV56 | E2 | 10 | 299 |
| HPV56 | E2 | 11 | 258 |
| HPV56 | E2 | 8 | 233 |
| HPV56 | E2 | 8 | 90 |
| HPV56 | E2 | 11 | 90 |
| HPV56 | E2 | 11 | 78 |
| HPV56 | E2 | 9 | 260 |
| HPV56 | E2 | 11 | 260 |
| HPV56 | E2 | 8 | 46 |
| HPV56 | E2 | 10 | 44 |
| HPV56 | E2 | 9 | 216 |
| HPV56 | E2 | 11 | 149 |
| HPV56 | E2 | 8 | 277 |
| HPV56 | E2 | 9 | 277 |
| HPV56 | E2 | 8 | 152 |
| HPV56 | E2 | 8 | 301 |
| HPV56 | E2 | 11 | 19 |
| HPV56 | E2 | 11 | 6 |
| HPV56 | E2 | 8 | 73 |
| HPV56 | E2 | 9 | 73 |
| HPV56 | E2 | 10 | 73 |
| HPV56 | E2 | 8 | 253 |
| HPV56 | E2 | 9 | 253 |
| HPV56 | E2 | 9 | 246 |
| HPV56 | E2 | 10 | 251 |
| HPV56 | E2 | 11 | 251 |
| HPV56 | E2 | 8 | 293 |
| HPV56 | E2 | 9 | 272 |
| HPV56 | E2 | 10 | 272 |
| HPV56 | E2 | 10 | 26 |
| HPV56 | E2 | 8 | 141 |
| HPV56 | E2 | 8 | 28 |
| HPV56 | E2 | 10 | 28 |
| HPV56 | E2 | 10 | 259 |
| HPV56 | E2 | 9 | 36 |
| HPV56 | E2 | 10 | 36 |
| HPV56 | E2 | 11 | 36 |
| HPV56 | E2 | 9 | 27 |
| HPV56 | E2 | 11 | 27 |
| HPV56 | E2 | 11 | 237 |
| HPV56 | E2 | 11 | 62 |
| HPV56 | E2 | 10 | 63 |
| HPV56 | E2 | 9 | 45 |
| HPV56 | E2 | 10 | 35 |
| HPV56 | E2 | 11 | 35 |
| HPV56 | E2 | 9 | 270 |
| HPV56 | E2 | 11 | 270 |
| HPV56 | E2 | 10 | 79 |
| HPV56 | E2 | 11 | 111 |
| HPV56 | E2 | 8 | 74 |
| HPV56 | E2 | 9 | 74 |
| HPV56 | E2 | 9 | 102 |
| HPV56 | E2 | 10 | 102 |
| HPV56 | E2 | 8 | 81 |
| HPV56 | E2 | 10 | 101 |
| HPV56 | E2 | 11 | 101 |
| HPV56 | E6 | 11 | 89 |
| HPV56 | E6 | 8 | 64 |
| HPV56 | E6 | 9 | 64 |
| HPV56 | E6 | 10 | 64 |
| HPV56 | E6 | 11 | 69 |
| HPV56 | E6 | 8 | 50 |
| HPV56 | E6 | 8 | 33 |
| HPV56 | E6 | 8 | 106 |
| HPV56 | E6 | 11 | 60 |
| HPV56 | E6 | 8 | 28 |
| HPV56 | E6 | 9 | 83 |
| HPV56 | E6 | 9 | 23 |
| HPV56 | E6 | 10 | 52 |
| HPV56 | E6 | 8 | 39 |
| HPV56 | E6 | 10 | 39 |
| HPV56 | E6 | 8 | 20 |
| HPV56 | E6 | 10 | 20 |
| HPV56 | E6 | 10 | 44 |
| HPV56 | E6 | 8 | 72 |
| HPV56 | E6 | 10 | 72 |
| HPV56 | E6 | 11 | 72 |
| HPV56 | E6 | 10 | 134 |
| HPV56 | E6 | 8 | 17 |
| HPV56 | E6 | 10 | 17 |
| HPV56 | E6 | 11 | 17 |
| HPV56 | E6 | 9 | 94 |
| HPV56 | E6 | 10 | 94 |
| HPV56 | E6 | 11 | 94 |
| HPV56 | E6 | 8 | 54 |
| HPV56 | E6 | 10 | 54 |
| HPV56 | E6 | 8 | 75 |
| HPV56 | E6 | 10 | 75 |
| HPV56 | E6 | 10 | 78 |
| HPV56 | E6 | 9 | 71 |
| HPV56 | E6 | 11 | 71 |
| HPV56 | E6 | 11 | 130 |
| HPV56 | E6 | 10 | 26 |
| HPV56 | E6 | 11 | 103 |
| HPV56 | E6 | 10 | 70 |
| HPV56 | E6 | 8 | 113 |
| HPV56 | E6 | 9 | 40 |

TABLE X-continued

HLA A24 Supermotif Peptides

| 1 | 2 | 3 | 4 |
|---|---|---|---|
| HPV56 | E6 | 9 | 55 |
| HPV56 | E6 | 9 | 47 |
| HPV56 | E6 | 11 | 47 |
| HPV56 | E6 | 11 | 25 |
| HPV56 | E6 | 9 | 112 |
| HPV56 | E6 | 9 | 62 |
| HPV56 | E6 | 10 | 62 |
| HPV56 | E6 | 11 | 62 |
| HPV56 | E6 | 10 | 98 |
| HPV56 | E6 | 10 | 119 |
| HPV56 | E6 | 9 | 127 |
| HPV56 | E6 | 11 | 30 |
| HPV56 | E6 | 8 | 80 |
| HPV56 | E6 | 10 | 93 |
| HPV56 | E6 | 11 | 93 |
| HPV56 | E6 | 9 | 14 |
| HPV56 | E6 | 11 | 14 |
| HPV56 | E6 | 10 | 85 |
| HPV56 | E6 | 10 | 90 |
| HPV56 | E6 | 9 | 21 |
| HPV56 | E6 | 11 | 21 |
| HPV56 | E6 | 9 | 86 |
| HPV56 | E6 | 9 | 45 |
| HPV56 | E6 | 11 | 45 |
| HPV56 | E6 | 8 | 56 |
| HPV56 | E6 | 9 | 135 |
| HPV56 | E6 | 11 | 81 |
| HPV56 | E7 | 8 | 93 |
| HPV56 | E7 | 9 | 75 |
| HPV56 | E7 | 8 | 22 |
| HPV56 | E7 | 8 | 82 |
| HPV56 | E7 | 9 | 82 |
| HPV56 | E7 | 10 | 82 |
| HPV56 | E7 | 10 | 20 |
| HPV56 | E7 | 8 | 14 |
| HPV56 | E7 | 10 | 14 |
| HPV56 | E7 | 9 | 62 |
| HPV56 | E7 | 8 | 69 |
| HPV56 | E7 | 10 | 4 |
| HPV56 | E7 | 11 | 60 |
| HPV56 | E7 | 11 | 90 |
| HPV56 | E7 | 9 | 15 |
| HPV56 | E7 | 8 | 6 |
| HPV56 | E7 | 10 | 6 |
| HPV56 | E7 | 11 | 73 |
| HPV56 | E7 | 8 | 84 |
| HPV56 | E7 | 11 | 84 |
| HPV56 | E7 | 9 | 7 |
| HPV56 | E7 | 10 | 12 |
| HPV56 | E7 | 11 | 11 |
| HPV56 | E7 | 10 | 85 |
| HPV56 | L1 | 11 | 58 |
| HPV56 | L1 | 8 | 381 |
| HPV56 | L1 | 8 | 327 |
| HPV56 | L1 | 8 | 444 |
| HPV56 | L1 | 10 | 444 |
| HPV56 | L1 | 11 | 37 |
| HPV56 | L1 | 8 | 26 |
| HPV56 | L1 | 9 | 26 |
| HPV56 | L1 | 11 | 26 |
| HPV56 | L1 | 8 | 275 |
| HPV56 | L1 | 9 | 275 |
| HPV56 | L1 | 10 | 275 |
| HPV56 | L1 | 10 | 422 |
| HPV56 | L1 | 11 | 422 |
| HPV56 | L1 | 11 | 101 |
| HPV56 | L1 | 9 | 191 |
| HPV56 | L1 | 9 | 195 |
| HPV56 | L1 | 9 | 257 |
| HPV56 | L1 | 11 | 491 |
| HPV56 | L1 | 10 | 233 |
| HPV56 | L1 | 9 | 236 |
| HPV56 | L1 | 8 | 369 |
| HPV56 | L1 | 10 | 369 |
| HPV56 | L1 | 8 | 23 |
| HPV56 | L1 | 10 | 23 |
| HPV56 | L1 | 11 | 23 |
| HPV56 | L1 | 8 | 481 |
| HPV56 | L1 | 10 | 267 |
| HPV56 | L1 | 8 | 404 |
| HPV56 | L1 | 11 | 404 |
| HPV56 | L1 | 8 | 303 |
| HPV56 | L1 | 9 | 303 |
| HPV56 | L1 | 8 | 140 |
| HPV56 | L1 | 9 | 419 |
| HPV56 | L1 | 8 | 402 |
| HPV56 | L1 | 10 | 402 |
| HPV56 | L1 | 10 | 21 |
| HPV56 | L1 | 8 | 407 |
| HPV56 | L1 | 10 | 407 |
| HPV56 | L1 | 10 | 479 |
| HPV56 | L1 | 9 | 69 |
| HPV56 | L1 | 10 | 69 |
| HPV56 | L1 | 8 | 282 |
| HPV56 | L1 | 9 | 282 |
| HPV56 | L1 | 10 | 238 |
| HPV56 | L1 | 8 | 356 |
| HPV56 | L1 | 9 | 356 |
| HPV56 | L1 | 10 | 138 |
| HPV56 | L1 | 8 | 118 |
| HPV56 | L1 | 8 | 150 |
| HPV56 | L1 | 11 | 150 |
| HPV56 | L1 | 10 | 438 |
| HPV56 | L1 | 9 | 399 |
| HPV56 | L1 | 11 | 399 |
| HPV56 | L1 | 8 | 15 |
| HPV56 | L1 | 11 | 20 |
| HPV56 | L1 | 8 | 32 |
| HPV56 | L1 | 10 | 68 |
| HPV56 | L1 | 11 | 68 |
| HPV56 | L1 | 8 | 414 |
| HPV56 | L1 | 10 | 414 |
| HPV56 | L1 | 11 | 414 |
| HPV56 | L1 | 8 | 334 |
| HPV56 | L1 | 8 | 192 |
| HPV56 | L1 | 8 | 258 |
| HPV56 | L1 | 11 | 258 |
| HPV56 | L1 | 9 | 124 |
| HPV56 | L1 | 11 | 124 |
| HPV56 | L1 | 9 | 8 |
| HPV56 | L1 | 11 | 8 |
| HPV56 | L1 | 9 | 116 |
| HPV56 | L1 | 10 | 116 |
| HPV56 | L1 | 11 | 478 |
| HPV56 | L1 | 9 | 413 |
| HPV56 | L1 | 11 | 413 |
| HPV56 | L1 | 11 | 270 |
| HPV56 | L1 | 10 | 93 |
| HPV56 | L1 | 10 | 300 |
| HPV56 | L1 | 11 | 300 |
| HPV56 | L1 | 10 | 98 |
| HPV56 | L1 | 8 | 55 |
| HPV56 | L1 | 10 | 387 |
| HPV56 | L1 | 11 | 387 |
| HPV56 | L1 | 9 | 476 |
| HPV56 | L1 | 8 | 264 |
| HPV56 | L1 | 10 | 450 |
| HPV56 | L1 | 8 | 340 |
| HPV56 | L1 | 11 | 224 |
| HPV56 | L1 | 8 | 77 |
| HPV56 | L1 | 9 | 77 |
| HPV56 | L1 | 9 | 431 |
| HPV56 | L1 | 8 | 132 |
| HPV56 | L1 | 9 | 234 |
| HPV56 | L1 | 11 | 234 |
| HPV56 | L1 | 8 | 333 |
| HPV56 | L1 | 9 | 333 |
| HPV56 | L1 | 8 | 2 |
| HPV56 | L1 | 8 | 1 |
| HPV56 | L1 | 9 | 1 |

TABLE X-continued

HLA A24 Supermotif Peptides

| 1 | 2 | 3 | 4 |
|---|---|---|---|
| HPV56 | L1 | 10 | 5 |
| HPV56 | L1 | 10 | 376 |
| HPV56 | L1 | 10 | 280 |
| HPV56 | L1 | 11 | 280 |
| HPV56 | L1 | 9 | 6 |
| HPV56 | L1 | 11 | 6 |
| HPV56 | L1 | 8 | 95 |
| HPV56 | L1 | 10 | 95 |
| HPV56 | L1 | 11 | 180 |
| HPV56 | L1 | 10 | 123 |
| HPV56 | L1 | 8 | 167 |
| HPV56 | L1 | 8 | 430 |
| HPV56 | L1 | 10 | 430 |
| HPV56 | L1 | 10 | 483 |
| HPV56 | L1 | 10 | 426 |
| HPV56 | L1 | 11 | 375 |
| HPV56 | L1 | 9 | 226 |
| HPV56 | L1 | 10 | 226 |
| HPV56 | L1 | 9 | 28 |
| HPV56 | L1 | 10 | 172 |
| HPV56 | L1 | 8 | 228 |
| HPV56 | L1 | 9 | 31 |
| HPV56 | L1 | 8 | 473 |
| HPV56 | L1 | 9 | 221 |
| HPV56 | L1 | 11 | 255 |
| HPV56 | L1 | 11 | 146 |
| HPV56 | L1 | 8 | 496 |
| HPV56 | L1 | 10 | 496 |
| HPV56 | L1 | 8 | 13 |
| HPV56 | L1 | 9 | 13 |
| HPV56 | L1 | 10 | 13 |
| HPV56 | L1 | 11 | 4 |
| HPV56 | L1 | 8 | 467 |
| HPV56 | L1 | 11 | 467 |
| HPV56 | L1 | 10 | 442 |
| HPV56 | L1 | 11 | 52 |
| HPV56 | L1 | 8 | 494 |
| HPV56 | L1 | 9 | 494 |
| HPV56 | L1 | 10 | 494 |
| HPV56 | L1 | 9 | 406 |
| HPV56 | L1 | 11 | 406 |
| HPV56 | L1 | 11 | 189 |
| HPV56 | L1 | 8 | 288 |
| HPV56 | L1 | 8 | 339 |
| HPV56 | L1 | 9 | 339 |
| HPV56 | L1 | 10 | 384 |
| HPV56 | L1 | 10 | 213 |
| HPV56 | L1 | 9 | 395 |
| HPV56 | L1 | 11 | 395 |
| HPV56 | L1 | 9 | 103 |
| HPV56 | L1 | 10 | 159 |
| HPV56 | L1 | 9 | 76 |
| HPV56 | L1 | 10 | 76 |
| HPV56 | L1 | 8 | 110 |
| HPV56 | L1 | 10 | 110 |
| HPV56 | L1 | 9 | 131 |
| HPV56 | L1 | 10 | 108 |
| HPV56 | L1 | 8 | 452 |
| HPV56 | L1 | 9 | 487 |
| HPV56 | L1 | 11 | 487 |
| HPV56 | L1 | 11 | 67 |
| HPV56 | L1 | 8 | 446 |
| HPV56 | L1 | 9 | 332 |
| HPV56 | L1 | 10 | 332 |
| HPV56 | L1 | 11 | 279 |
| HPV56 | L1 | 10 | 379 |
| HPV56 | L1 | 8 | 261 |
| HPV56 | L1 | 9 | 261 |
| HPV56 | L1 | 11 | 261 |
| HPV56 | L1 | 9 | 489 |
| HPV56 | L1 | 9 | 182 |
| HPV56 | L1 | 11 | 182 |
| HPV56 | L1 | 11 | 86 |
| HPV56 | L1 | 11 | 323 |
| HPV56 | L1 | 8 | 61 |
| HPV56 | L1 | 9 | 61 |
| HPV56 | L1 | 10 | 61 |
| HPV56 | L1 | 8 | 304 |
| HPV56 | L1 | 9 | 377 |
| HPV56 | L1 | 9 | 415 |
| HPV56 | L1 | 10 | 415 |
| HPV56 | L1 | 8 | 215 |
| HPV56 | L1 | 10 | 215 |
| HPV56 | L1 | 11 | 215 |
| HPV56 | L1 | 9 | 370 |
| HPV56 | L1 | 11 | 366 |
| HPV56 | L1 | 10 | 38 |
| HPV56 | L1 | 11 | 38 |
| HPV56 | L1 | 8 | 29 |
| HPV56 | L1 | 11 | 29 |
| HPV56 | L1 | 9 | 408 |
| HPV56 | L1 | 9 | 173 |
| HPV56 | L1 | 11 | 246 |
| HPV56 | L1 | 8 | 420 |
| HPV56 | L1 | 10 | 87 |
| HPV56 | L1 | 9 | 214 |
| HPV56 | L1 | 11 | 214 |
| HPV56 | L1 | 10 | 367 |
| HPV56 | L1 | 10 | 324 |
| HPV56 | L1 | 11 | 324 |
| HPV56 | L1 | 9 | 281 |
| HPV56 | L1 | 10 | 281 |
| HPV56 | L1 | 8 | 7 |
| HPV56 | L1 | 10 | 7 |
| HPV56 | L1 | 9 | 423 |
| HPV56 | L1 | 10 | 423 |
| HPV56 | L1 | 9 | 268 |
| HPV56 | L1 | 8 | 396 |
| HPV56 | L1 | 10 | 396 |
| HPV56 | L1 | 8 | 283 |
| HPV56 | L1 | 9 | 325 |
| HPV56 | L1 | 10 | 325 |
| HPV56 | L1 | 8 | 62 |
| HPV56 | L1 | 9 | 62 |
| HPV56 | L2 | 9 | 240 |
| HPV56 | L2 | 11 | 286 |
| HPV56 | L2 | 8 | 438 |
| HPV56 | L2 | 11 | 303 |
| HPV56 | L2 | 10 | 246 |
| HPV56 | L2 | 11 | 246 |
| HPV56 | L2 | 9 | 367 |
| HPV56 | L2 | 10 | 14 |
| HPV56 | L2 | 10 | 201 |
| HPV56 | L2 | 8 | 275 |
| HPV56 | L2 | 11 | 322 |
| HPV56 | L2 | 11 | 406 |
| HPV56 | L2 | 8 | 425 |
| HPV56 | L2 | 9 | 83 |
| HPV56 | L2 | 11 | 30 |
| HPV56 | L2 | 9 | 429 |
| HPV56 | L2 | 11 | 429 |
| HPV56 | L2 | 8 | 331 |
| HPV56 | L2 | 10 | 398 |
| HPV56 | L2 | 8 | 175 |
| HPV56 | L2 | 10 | 444 |
| HPV56 | L2 | 8 | 241 |
| HPV56 | L2 | 9 | 122 |
| HPV56 | L2 | 10 | 287 |
| HPV56 | L2 | 9 | 51 |
| HPV56 | L2 | 9 | 401 |
| HPV56 | L2 | 10 | 217 |
| HPV56 | L2 | 11 | 217 |
| HPV56 | L2 | 8 | 188 |
| HPV56 | L2 | 10 | 188 |
| HPV56 | L2 | 11 | 118 |
| HPV56 | L2 | 9 | 346 |
| HPV56 | L2 | 11 | 25 |
| HPV56 | L2 | 8 | 258 |
| HPV56 | L2 | 10 | 206 |
| HPV56 | L2 | 10 | 62 |

TABLE X-continued

HLA A24 Supermotif Peptides

| 1 | 2 | 3 | 4 |
|---|---|---|---|
| HPV56 | L2 | 10 | 310 |
| HPV56 | L2 | 11 | 310 |
| HPV56 | L2 | 8 | 269 |
| HPV56 | L2 | 9 | 269 |
| HPV56 | L2 | 11 | 269 |
| HPV56 | L2 | 8 | 156 |
| HPV56 | L2 | 9 | 372 |
| HPV56 | L2 | 11 | 372 |
| HPV56 | L2 | 11 | 151 |
| HPV56 | L2 | 9 | 318 |
| HPV56 | L2 | 10 | 180 |
| HPV56 | L2 | 8 | 44 |
| HPV56 | L2 | 10 | 44 |
| HPV56 | L2 | 11 | 44 |
| HPV56 | L2 | 9 | 279 |
| HPV56 | L2 | 11 | 81 |
| HPV56 | L2 | 10 | 407 |
| HPV56 | L2 | 11 | 103 |
| HPV56 | L2 | 11 | 34 |
| HPV56 | L2 | 8 | 43 |
| HPV56 | L2 | 9 | 43 |
| HPV56 | L2 | 11 | 43 |
| HPV56 | L2 | 8 | 38 |
| HPV56 | L2 | 10 | 38 |
| HPV56 | L2 | 8 | 235 |
| HPV56 | L2 | 9 | 255 |
| HPV56 | L2 | 11 | 255 |
| HPV56 | L2 | 8 | 161 |
| HPV56 | L2 | 8 | 50 |
| HPV56 | L2 | 10 | 50 |
| HPV56 | L2 | 9 | 181 |
| HPV56 | L2 | 8 | 337 |
| HPV56 | L2 | 11 | 337 |
| HPV56 | L2 | 8 | 106 |
| HPV56 | L2 | 8 | 248 |
| HPV56 | L2 | 9 | 248 |
| HPV56 | L2 | 8 | 347 |
| HPV56 | L2 | 8 | 121 |
| HPV56 | L2 | 10 | 121 |
| HPV56 | L2 | 9 | 353 |
| HPV56 | L2 | 11 | 179 |
| HPV56 | L2 | 10 | 278 |
| HPV56 | L2 | 9 | 385 |
| HPV56 | L2 | 10 | 388 |
| HPV56 | L2 | 8 | 395 |
| HPV56 | L2 | 8 | 417 |
| HPV56 | L2 | 8 | 400 |
| HPV56 | L2 | 10 | 400 |
| HPV56 | L2 | 8 | 325 |
| HPV56 | L2 | 10 | 325 |
| HPV56 | L2 | 9 | 374 |
| HPV56 | L2 | 8 | 214 |
| HPV56 | L2 | 10 | 209 |
| HPV56 | L2 | 10 | 254 |
| HPV56 | L2 | 9 | 160 |
| HPV56 | L2 | 10 | 392 |
| HPV56 | L2 | 11 | 392 |
| HPV56 | L2 | 9 | 73 |
| HPV56 | L2 | 9 | 336 |
| HPV56 | L2 | 9 | 98 |
| HPV56 | L2 | 9 | 410 |
| HPV56 | L2 | 8 | 185 |
| HPV56 | L2 | 11 | 185 |
| HPV56 | L2 | 9 | 423 |
| HPV56 | L2 | 10 | 423 |
| HPV56 | L2 | 8 | 312 |
| HPV56 | L2 | 9 | 312 |
| HPV56 | L2 | 10 | 312 |
| HPV56 | L2 | 8 | 16 |
| HPV56 | L2 | 9 | 172 |
| HPV56 | L2 | 10 | 172 |
| HPV56 | L2 | 11 | 172 |
| HPV56 | L2 | 8 | 306 |
| HPV56 | L2 | 9 | 233 |
| HPV56 | L2 | 10 | 233 |
| HPV56 | L2 | 8 | 46 |
| HPV56 | L2 | 9 | 46 |
| HPV56 | L2 | 11 | 295 |
| HPV56 | L2 | 8 | 220 |
| HPV56 | L2 | 8 | 298 |
| HPV56 | L2 | 8 | 316 |
| HPV56 | L2 | 11 | 316 |
| HPV56 | L2 | 8 | 436 |
| HPV56 | L2 | 9 | 436 |
| HPV56 | L2 | 10 | 436 |
| HPV56 | L2 | 9 | 343 |
| HPV56 | L2 | 9 | 343 |
| HPV56 | L2 | 9 | 49 |
| HPV56 | L2 | 11 | 49 |
| HPV56 | L2 | 8 | 154 |
| HPV56 | L2 | 9 | 154 |
| HPV56 | L2 | 10 | 154 |
| HPV56 | L2 | 10 | 212 |
| HPV56 | L2 | 10 | 183 |
| HPV56 | L2 | 8 | 134 |
| HPV56 | L2 | 10 | 134 |
| HPV56 | L2 | 10 | 148 |
| HPV56 | L2 | 11 | 414 |
| HPV56 | L2 | 9 | 365 |
| HPV56 | L2 | 11 | 365 |
| HPV56 | L2 | 9 | 95 |
| HPV56 | L2 | 9 | 111 |
| HPV56 | L2 | 10 | 191 |
| HPV56 | L2 | 10 | 304 |
| HPV56 | L2 | 9 | 105 |
| HPV56 | L2 | 9 | 247 |
| HPV56 | L2 | 10 | 247 |
| HPV56 | L2 | 8 | 386 |
| HPV56 | L2 | 8 | 136 |
| HPV56 | L2 | 9 | 288 |
| HPV56 | L2 | 9 | 135 |
| HPV56 | L2 | 9 | 149 |
| HPV56 | L2 | 9 | 39 |
| HPV56 | L2 | 10 | 415 |
| HPV56 | L2 | 8 | 52 |
| HPV56 | L2 | 8 | 112 |
| HPV56 | L2 | 11 | 112 |
| HPV56 | L2 | 9 | 408 |
| HPV56 | L2 | 11 | 408 |
| HPV56 | L2 | 9 | 389 |
| HPV56 | L2 | 10 | 104 |
| HPV56 | L2 | 8 | 84 |
| HPV56 | L2 | 10 | 31 |
| HPV56 | L2 | 8 | 430 |
| HPV56 | L2 | 10 | 430 |
| HPV56 | L2 | 11 | 430 |
| HPV56 | L2 | 11 | 443 |
| HPV56 | L2 | 9 | 431 |
| HPV56 | L2 | 10 | 431 |
| HPV56 | L2 | 11 | 71 |
| HPV56 | L2 | 8 | 319 |

TABLE XA

HPV6A
HLA-A24 Supermotif Peptides

| 2 | 3 | 4 |
|---|---|---|
| E1 | 10 | 377 |
| E1 | 11 | 392 |
| L2 | 9 | 238 |
| L2 | 10 | 238 |
| L2 | 8 | 275 |
| E1 | 9 | 251 |
| E1 | 11 | 251 |
| E5 | 9 | 23 |

TABLE XA-continued

HPV6A
HLA-A24 Supermotif Peptides

| 2 | 3 | 4 |
|---|---|---|
| E5 | 10 | 23 |
| E5 | 11 | 23 |
| L2 | 8 | 286 |
| L2 | 11 | 286 |
| E2 | 8 | 72 |
| E2 | 11 | 72 |
| L2 | 10 | 112 |
| E1 | 11 | 22 |
| E4 | 8 | 14 |
| E4 | 9 | 14 |
| E4 | 11 | 14 |
| E1 | 11 | 520 |
| E1 | 10 | 207 |
| L1 | 8 | 81 |
| L2 | 8 | 421 |
| L2 | 9 | 421 |
| E1 | 10 | 554 |
| E1 | 11 | 554 |
| E6 | 8 | 37 |
| E6 | 10 | 37 |
| E5 | 8 | 79 |
| E1 | 9 | 319 |
| L1 | 11 | 22 |
| E1 | 11 | 296 |
| E4 | 9 | 61 |
| L2 | 10 | 14 |
| E1 | 8 | 525 |
| E1 | 9 | 525 |
| E6 | 11 | 10 |
| E1 | 10 | 77 |
| E1 | 11 | 77 |
| E1 | 10 | 101 |
| L1 | 9 | 43 |
| E1 | 10 | 601 |
| E1 | 9 | 271 |
| L1 | 11 | 384 |
| E6 | 8 | 47 |
| E6 | 9 | 47 |
| L1 | 8 | 25 |
| L1 | 9 | 25 |
| L1 | 10 | 25 |
| E1 | 10 | 612 |
| E1 | 9 | 215 |
| E1 | 10 | 215 |
| E5 | 8 | 27 |
| E5 | 10 | 27 |
| E5 | 11 | 27 |
| E6 | 8 | 67 |
| E6 | 11 | 67 |
| E6 | 9 | 137 |
| E2 | 9 | 296 |
| E2 | 8 | 35 |
| E2 | 9 | 35 |
| E2 | 10 | 35 |
| E1 | 8 | 488 |
| L1 | 9 | 153 |
| E1 | 10 | 14 |
| E6 | 8 | 131 |
| E6 | 11 | 131 |
| E6 | 8 | 31 |
| E1 | 10 | 640 |
| E4 | 9 | 64 |
| E1 | 8 | 529 |
| E1 | 9 | 529 |
| E6 | 9 | 140 |
| E6 | 10 | 140 |
| E5 | 8 | 75 |
| E5 | 11 | 75 |
| E6 | 8 | 104 |
| E1 | 9 | 385 |
| E1 | 10 | 385 |
| E1 | 8 | 49 |
| E5 | 9 | 39 |
| E5 | 11 | 39 |
| E1 | 8 | 369 |
| E1 | 10 | 369 |
| L1 | 9 | 219 |
| L2 | 10 | 278 |
| E6 | 10 | 96 |
| E6 | 11 | 96 |
| E7 | 8 | 75 |
| E7 | 9 | 75 |
| E7 | 10 | 75 |
| L2 | 9 | 404 |
| E1 | 8 | 570 |
| E1 | 10 | 570 |
| E1 | 11 | 570 |
| L2 | 11 | 347 |
| L2 | 10 | 396 |
| E2 | 9 | 313 |
| E1 | 11 | 81 |
| E2 | 9 | 25 |
| L1 | 8 | 366 |
| L1 | 11 | 366 |
| E7 | 10 | 14 |
| L1 | 11 | 208 |
| E1 | 10 | 203 |
| E1 | 11 | 46 |
| L1 | 10 | 195 |
| E2 | 11 | 141 |
| L2 | 10 | 344 |
| L1 | 9 | 198 |
| E1 | 9 | 481 |
| E1 | 11 | 481 |
| E1 | 10 | 73 |
| L1 | 8 | 331 |
| L1 | 10 | 331 |
| E1 | 8 | 534 |
| L1 | 11 | 411 |
| L2 | 11 | 30 |
| E6 | 8 | 99 |
| L2 | 11 | 258 |
| E2 | 10 | 136 |
| E1 | 9 | 236 |
| L1 | 9 | 146 |
| L1 | 10 | 229 |
| E2 | 9 | 130 |
| E6 | 9 | 69 |
| E1 | 9 | 453 |
| E1 | 11 | 453 |
| L2 | 9 | 192 |
| E1 | 9 | 105 |
| E1 | 11 | 105 |
| L2 | 10 | 120 |
| E6 | 10 | 42 |
| L1 | 11 | 453 |
| E1 | 8 | 197 |
| E1 | 10 | 604 |
| E1 | 11 | 604 |
| E1 | 9 | 131 |
| E2 | 10 | 17 |
| E2 | 9 | 74 |
| E2 | 10 | 74 |
| E1 | 10 | 417 |
| E1 | 11 | 417 |
| E1 | 11 | 360 |
| E2 | 11 | 100 |
| E7 | 10 | 73 |
| E7 | 11 | 73 |
| E6 | 10 | 92 |
| E6 | 11 | 92 |
| L2 | 8 | 135 |
| E4 | 9 | 75 |
| E2 | 9 | 185 |
| E7 | 10 | 39 |
| E1 | 9 | 39 |
| E6 | 8 | 113 |
| E6 | 9 | 113 |

TABLE XA-continued

HPV6A
HLA-A24 Supermotif Peptides

| 2 | 3 | 4 |
|---|---|---|
| L1 | 10 | 262 |
| L1 | 11 | 262 |
| L1 | 8 | 103 |
| L1 | 9 | 381 |
| L1 | 8 | 443 |
| E7 | 10 | 78 |
| E2 | 10 | 205 |
| E1 | 9 | 339 |
| E1 | 8 | 379 |
| L1 | 8 | 364 |
| L1 | 10 | 364 |
| L1 | 9 | 357 |
| L1 | 11 | 357 |
| E2 | 9 | 86 |
| E1 | 9 | 613 |
| E1 | 11 | 613 |
| L1 | 9 | 243 |
| L1 | 10 | 243 |
| E5 | 10 | 67 |
| L1 | 8 | 244 |
| L1 | 9 | 244 |
| E1 | 8 | 220 |
| L1 | 8 | 369 |
| L1 | 10 | 369 |
| E6 | 8 | 126 |
| E1 | 8 | 454 |
| E1 | 10 | 454 |
| E1 | 11 | 454 |
| L2 | 8 | 428 |
| L2 | 9 | 428 |
| E5 | 8 | 40 |
| E5 | 10 | 40 |
| E5 | 9 | 68 |
| E1 | 10 | 393 |
| E2 | 11 | 346 |
| L2 | 8 | 398 |
| L2 | 10 | 398 |
| E1 | 9 | 446 |
| E1 | 10 | 446 |
| L1 | 8 | 245 |
| E1 | 8 | 457 |
| E1 | 9 | 457 |
| L2 | 8 | 239 |
| L2 | 9 | 239 |
| L2 | 11 | 239 |
| E1 | 9 | 587 |
| E2 | 8 | 171 |
| E5 | 9 | 28 |
| E5 | 10 | 28 |
| E5 | 8 | 24 |
| E5 | 9 | 24 |
| E5 | 10 | 24 |
| E5 | 11 | 24 |
| L1 | 10 | 441 |
| L1 | 9 | 33 |
| L1 | 10 | 33 |
| L2 | 8 | 434 |
| L2 | 9 | 434 |
| L1 | 10 | 200 |
| E1 | 8 | 241 |
| E2 | 8 | 361 |
| L2 | 8 | 433 |
| L2 | 9 | 433 |
| L2 | 10 | 433 |
| L1 | 8 | 318 |
| L1 | 9 | 318 |
| E1 | 10 | 243 |
| E1 | 11 | 194 |
| E1 | 9 | 326 |
| E2 | 9 | 156 |
| E1 | 9 | 350 |
| L1 | 10 | 101 |
| E7 | 8 | 22 |
| E1 | 8 | 217 |

TABLE XA-continued

HPV6A
HLA-A24 Supermotif Peptides

| 2 | 3 | 4 |
|---|---|---|
| E1 | 11 | 217 |
| L1 | 10 | 400 |
| L2 | 8 | 292 |
| L1 | 9 | 144 |
| L1 | 11 | 144 |
| E2 | 8 | 55 |
| E1 | 10 | 273 |
| E1 | 8 | 191 |
| E1 | 9 | 191 |
| L2 | 10 | 215 |
| L2 | 11 | 215 |
| L2 | 8 | 25 |
| L2 | 8 | 64 |
| L2 | 11 | 64 |
| E1 | 8 | 436 |
| E1 | 11 | 436 |
| E7 | 9 | 85 |
| L1 | 9 | 407 |
| L2 | 10 | 413 |
| E1 | 8 | 467 |
| E1 | 10 | 467 |
| L2 | 8 | 75 |
| L1 | 9 | 222 |
| L1 | 10 | 222 |
| E5 | 8 | 11 |
| E5 | 11 | 11 |
| E4 | 8 | 90 |
| E4 | 10 | 90 |
| E1 | 8 | 316 |
| L2 | 9 | 51 |
| L1 | 9 | 111 |
| L1 | 10 | 111 |
| E2 | 10 | 242 |
| L1 | 8 | 113 |
| L1 | 11 | 113 |
| E1 | 8 | 16 |
| E1 | 8 | 44 |
| E6 | 11 | 58 |
| L1 | 11 | 64 |
| L1 | 8 | 468 |
| L2 | 8 | 312 |
| L2 | 9 | 312 |
| L2 | 10 | 312 |
| E2 | 10 | 53 |
| L2 | 9 | 177 |
| E6 | 8 | 119 |
| E6 | 9 | 119 |
| E6 | 11 | 119 |
| E1 | 9 | 264 |
| E1 | 11 | 264 |
| E4 | 8 | 59 |
| E4 | 11 | 59 |
| E2 | 10 | 78 |
| E2 | 10 | 310 |
| E4 | 10 | 10 |
| E6 | 9 | 25 |
| L1 | 8 | 387 |
| L1 | 11 | 387 |
| E4 | 10 | 26 |
| L2 | 8 | 306 |
| E1 | 9 | 581 |
| L1 | 9 | 361 |
| L1 | 10 | 361 |
| L1 | 11 | 361 |
| E2 | 8 | 29 |
| E1 | 8 | 502 |
| E1 | 9 | 502 |
| E1 | 10 | 502 |
| E7 | 9 | 5 |
| E7 | 11 | 5 |
| E2 | 11 | 32 |
| E1 | 8 | 75 |
| L2 | 9 | 318 |
| E1 | 10 | 412 |

TABLE XA-continued

HPV6A
HLA-A24 Supermotif Peptides

| 2 | 3 | 4 |
|---|---|---|
| L1 | 9 | 370 |
| L1 | 10 | 32 |
| L1 | 11 | 32 |
| E5 | 8 | 21 |
| E5 | 11 | 21 |
| E5 | 10 | 31 |
| E5 | 11 | 31 |
| L2 | 9 | 113 |
| L2 | 9 | 279 |
| E6 | 9 | 97 |
| E6 | 10 | 97 |
| E1 | 10 | 195 |
| L2 | 8 | 178 |
| E5 | 9 | 32 |
| E5 | 10 | 32 |
| L2 | 10 | 44 |
| L2 | 11 | 44 |
| E5 | 8 | 17 |
| E6 | 8 | 120 |
| E6 | 10 | 120 |
| L2 | 8 | 405 |
| L2 | 8 | 429 |
| E1 | 11 | 56 |
| E1 | 9 | 571 |
| E1 | 10 | 571 |
| L1 | 8 | 376 |
| L1 | 10 | 376 |
| L1 | 11 | 376 |
| E1 | 11 | 341 |
| L2 | 9 | 185 |
| L2 | 11 | 185 |
| L2 | 11 | 131 |
| L1 | 10 | 187 |
| L2 | 8 | 247 |
| E1 | 11 | 476 |
| L2 | 9 | 121 |
| L2 | 11 | 121 |
| E1 | 10 | 443 |
| E2 | 11 | 287 |
| E1 | 10 | 23 |
| L2 | 10 | 104 |
| L2 | 11 | 104 |
| E5 | 8 | 34 |
| E5 | 10 | 34 |
| E5 | 9 | 41 |
| E5 | 11 | 41 |
| L2 | 10 | 348 |
| E1 | 10 | 531 |
| E1 | 11 | 531 |
| E6 | 9 | 43 |
| L1 | 10 | 286 |
| E2 | 8 | 157 |
| E2 | 11 | 157 |
| L1 | 9 | 79 |
| L1 | 10 | 79 |
| E2 | 10 | 120 |
| E1 | 8 | 211 |
| E1 | 10 | 211 |
| E1 | 11 | 211 |
| L1 | 8 | 462 |
| L1 | 9 | 449 |
| L1 | 11 | 449 |
| E1 | 8 | 433 |
| E1 | 11 | 433 |
| E6 | 8 | 73 |
| E6 | 10 | 73 |
| E2 | 10 | 351 |
| E1 | 9 | 312 |
| E1 | 10 | 312 |
| E1 | 11 | 312 |
| E2 | 9 | 359 |
| E2 | 10 | 359 |
| E1 | 8 | 254 |
| E1 | 9 | 254 |
| E6 | 11 | 128 |
| E1 | 8 | 357 |
| E1 | 10 | 357 |
| L2 | 11 | 22 |
| E1 | 8 | 420 |
| E2 | 9 | 84 |
| E2 | 11 | 84 |
| E6 | 10 | 18 |
| E4 | 8 | 42 |
| L1 | 10 | 56 |
| L2 | 11 | 34 |
| E2 | 11 | 147 |
| E6 | 11 | 116 |
| E6 | 8 | 52 |
| E6 | 10 | 52 |
| E2 | 11 | 63 |
| L1 | 10 | 61 |
| L1 | 8 | 19 |
| L1 | 10 | 71 |
| L2 | 8 | 46 |
| L2 | 9 | 46 |
| E2 | 8 | 177 |
| E1 | 11 | 85 |
| E1 | 10 | 578 |
| L1 | 8 | 226 |
| E4 | 8 | 18 |
| E1 | 9 | 401 |
| E2 | 9 | 311 |
| E2 | 11 | 311 |
| L1 | 9 | 87 |
| L1 | 11 | 87 |
| L1 | 10 | 242 |
| L1 | 11 | 242 |
| L2 | 9 | 397 |
| L2 | 11 | 397 |
| L1 | 8 | 302 |
| E1 | 11 | 66 |
| E6 | 8 | 54 |
| L2 | 8 | 107 |
| E1 | 8 | 255 |
| E1 | 11 | 255 |
| E1 | 8 | 557 |
| E5 | 9 | 16 |
| E6 | 11 | 101 |
| E1 | 10 | 491 |
| E2 | 8 | 314 |
| L1 | 11 | 186 |
| L2 | 9 | 246 |
| E5 | 8 | 33 |
| E5 | 9 | 33 |
| E5 | 11 | 33 |
| L1 | 8 | 41 |
| L1 | 9 | 41 |
| L1 | 11 | 41 |
| E1 | 10 | 521 |
| E1 | 11 | 521 |
| E1 | 9 | 540 |
| E1 | 9 | 208 |
| E1 | 11 | 208 |
| E7 | 11 | 83 |
| E4 | 8 | 8 |
| E1 | 11 | 198 |
| E2 | 8 | 82 |
| E2 | 11 | 82 |
| E7 | 8 | 82 |
| E5 | 9 | 59 |
| E5 | 10 | 59 |
| E5 | 11 | 59 |
| E5 | 11 | 55 |
| E5 | 8 | 51 |
| E5 | 9 | 51 |
| E5 | 10 | 51 |
| E5 | 11 | 51 |
| E1 | 9 | 298 |

TABLE XA-continued

HPV6A
HLA-A24 Supermotif Peptides

| 2 | 3 | 4 |
|---|---|---|
| E1 | 10 | 298 |
| E1 | 11 | 298 |
| E5 | 8 | 69 |
| E5 | 8 | 60 |
| E5 | 9 | 60 |
| E5 | 10 | 60 |
| E5 | 11 | 60 |
| E5 | 9 | 72 |
| E5 | 10 | 72 |
| E5 | 11 | 72 |
| E1 | 9 | 563 |
| E5 | 10 | 56 |
| E2 | 8 | 42 |
| E2 | 10 | 42 |
| E5 | 8 | 52 |
| E5 | 9 | 52 |
| E5 | 10 | 52 |
| E1 | 8 | 132 |
| E1 | 9 | 358 |
| L2 | 10 | 23 |
| E6 | 9 | 121 |
| E1 | 9 | 555 |
| E1 | 10 | 555 |
| E5 | 8 | 49 |
| E5 | 9 | 49 |
| E5 | 10 | 49 |
| E5 | 11 | 49 |
| E5 | 11 | 70 |
| E1 | 9 | 268 |
| E1 | 10 | 268 |
| E6 | 9 | 38 |
| E6 | 11 | 38 |
| E5 | 8 | 61 |
| E5 | 9 | 61 |
| E5 | 10 | 61 |
| L2 | 9 | 338 |
| L2 | 11 | 338 |
| E5 | 8 | 73 |
| E5 | 9 | 73 |
| E5 | 10 | 73 |
| E1 | 8 | 514 |
| E1 | 9 | 514 |
| E5 | 8 | 47 |
| E5 | 9 | 47 |
| E5 | 10 | 47 |
| E5 | 11 | 47 |
| L1 | 8 | 295 |
| L1 | 9 | 295 |
| E1 | 8 | 564 |
| E7 | 10 | 67 |
| L1 | 8 | 95 |
| E5 | 9 | 57 |
| E5 | 11 | 57 |
| E1 | 8 | 261 |
| E2 | 9 | 18 |
| E2 | 9 | 43 |
| E4 | 9 | 11 |
| E4 | 11 | 11 |
| E5 | 8 | 53 |
| E5 | 9 | 53 |
| E4 | 8 | 5 |
| E4 | 9 | 5 |
| E4 | 11 | 5 |
| E1 | 8 | 320 |
| E1 | 8 | 306 |
| E2 | 8 | 151 |
| E2 | 9 | 151 |
| E1 | 10 | 47 |
| L1 | 9 | 196 |
| L1 | 11 | 196 |
| L1 | 8 | 154 |
| E1 | 9 | 274 |
| E1 | 10 | 361 |
| E2 | 10 | 101 |

TABLE XA-continued

HPV6A
HLA-A24 Supermotif Peptides

| 2 | 3 | 4 |
|---|---|---|
| L1 | 10 | 1 |
| E2 | 9 | 170 |
| E1 | 10 | 568 |
| E1 | 8 | 451 |
| E1 | 11 | 451 |
| L1 | 11 | 31 |
| E1 | 8 | 300 |
| E1 | 9 | 300 |
| L1 | 10 | 445 |
| E1 | 8 | 539 |
| E1 | 10 | 539 |
| L1 | 9 | 438 |
| E6 | 9 | 21 |
| L2 | 8 | 38 |
| L2 | 10 | 38 |
| E1 | 11 | 96 |
| E2 | 8 | 127 |
| L2 | 9 | 385 |
| L1 | 11 | 142 |
| E2 | 9 | 348 |
| E1 | 9 | 609 |
| E1 | 8 | 439 |
| E1 | 9 | 439 |
| E1 | 10 | 594 |
| E1 | 8 | 456 |
| E1 | 9 | 456 |
| E1 | 10 | 456 |
| L2 | 8 | 415 |
| L2 | 9 | 325 |
| L2 | 11 | 325 |
| L1 | 11 | 217 |
| L2 | 10 | 189 |
| E1 | 11 | 442 |
| E6 | 11 | 110 |
| L1 | 9 | 183 |
| L1 | 8 | 458 |
| L2 | 10 | 73 |
| L1 | 11 | 109 |
| E7 | 8 | 47 |
| E1 | 8 | 562 |
| E1 | 10 | 562 |
| E5 | 9 | 64 |
| E5 | 10 | 64 |
| E1 | 8 | 258 |
| E1 | 10 | 258 |
| E1 | 11 | 258 |
| L2 | 9 | 389 |
| L2 | 10 | 389 |
| L2 | 11 | 389 |
| L2 | 10 | 337 |
| E1 | 9 | 513 |
| E1 | 10 | 513 |
| E1 | 11 | 545 |
| L2 | 9 | 408 |
| E2 | 9 | 354 |
| E2 | 10 | 354 |
| L2 | 8 | 183 |
| L2 | 11 | 183 |
| L1 | 11 | 426 |
| L2 | 9 | 359 |
| L1 | 8 | 90 |
| L2 | 9 | 96 |
| E2 | 9 | 258 |
| E2 | 10 | 258 |
| L2 | 8 | 171 |
| L2 | 9 | 171 |
| L2 | 10 | 171 |
| L2 | 9 | 426 |
| L2 | 10 | 426 |
| L2 | 11 | 426 |
| E7 | 10 | 20 |
| E5 | 10 | 19 |
| L1 | 8 | 266 |
| L1 | 10 | 175 |

TABLE XA-continued

HPV6A
HLA-A24 Supermotif Peptides

| 2 | 3 | 4 |
|---|---|---|
| L1 | 11 | 16 |
| L2 | 11 | 418 |
| L2 | 9 | 363 |
| L2 | 10 | 363 |
| L2 | 9 | 382 |
| E2 | 9 | 91 |
| E2 | 11 | 91 |
| E4 | 11 | 71 |
| E6 | 9 | 60 |
| E6 | 11 | 60 |
| L1 | 8 | 237 |
| L1 | 9 | 237 |
| L1 | 10 | 237 |
| L1 | 8 | 435 |
| E1 | 9 | 90 |
| E5 | 8 | 66 |
| E5 | 11 | 66 |
| L1 | 9 | 368 |
| L1 | 11 | 368 |
| E1 | 10 | 355 |
| E2 | 9 | 163 |
| E2 | 8 | 345 |
| E1 | 8 | 445 |
| E1 | 10 | 445 |
| E1 | 11 | 445 |
| E2 | 9 | 289 |
| E6 | 10 | 7 |
| E5 | 11 | 7 |
| L2 | 8 | 43 |
| L2 | 11 | 43 |
| E6 | 11 | 28 |
| E6 | 8 | 15 |
| E6 | 10 | 15 |
| L1 | 11 | 151 |
| L1 | 8 | 301 |
| L1 | 9 | 301 |
| E6 | 10 | 50 |
| E7 | 9 | 81 |
| L2 | 8 | 16 |
| E4 | 8 | 4 |
| E4 | 9 | 4 |
| E4 | 10 | 4 |
| L1 | 11 | 232 |
| L1 | 8 | 250 |
| E2 | 9 | 48 |
| E2 | 8 | 76 |
| E1 | 9 | 305 |
| L1 | 9 | 210 |
| L1 | 11 | 210 |
| E2 | 8 | 103 |
| E1 | 10 | 128 |
| E1 | 8 | 344 |
| L2 | 9 | 231 |
| L2 | 10 | 231 |
| L2 | 8 | 233 |
| E1 | 8 | 363 |
| E2 | 11 | 183 |
| E1 | 10 | 425 |
| E1 | 9 | 266 |
| E1 | 11 | 266 |
| L1 | 8 | 456 |
| L1 | 9 | 456 |
| L1 | 10 | 456 |
| E6 | 10 | 76 |
| L1 | 9 | 66 |
| E6 | 9 | 125 |
| L2 | 8 | 298 |
| L2 | 8 | 316 |
| L2 | 11 | 316 |
| E2 | 9 | 7 |
| E2 | 10 | 7 |
| L1 | 11 | 241 |
| E1 | 8 | 125 |
| L2 | 10 | 245 |

TABLE XA-continued

HPV6A
HLA-A24 Supermotif Peptides

| 2 | 3 | 4 |
|---|---|---|
| L1 | 9 | 40 |
| L1 | 10 | 40 |
| E2 | 9 | 303 |
| E2 | 10 | 303 |
| E1 | 8 | 616 |
| E7 | 11 | 66 |
| L1 | 9 | 94 |
| E1 | 11 | 324 |
| E1 | 9 | 293 |
| L1 | 8 | 279 |
| L1 | 9 | 279 |
| L2 | 9 | 221 |
| L1 | 8 | 140 |
| E1 | 11 | 583 |
| E2 | 11 | 301 |
| L2 | 11 | 295 |
| L1 | 8 | 414 |
| E1 | 9 | 219 |
| E1 | 8 | 493 |
| L1 | 11 | 440 |
| E1 | 9 | 547 |
| E1 | 11 | 547 |
| L2 | 8 | 153 |
| L2 | 10 | 267 |
| L2 | 11 | 267 |
| E5 | 8 | 30 |
| E5 | 11 | 30 |
| E2 | 8 | 207 |
| L2 | 8 | 392 |
| E1 | 9 | 247 |
| E1 | 10 | 247 |
| L1 | 9 | 375 |
| L1 | 11 | 375 |
| L2 | 11 | 103 |
| L1 | 11 | 285 |
| E1 | 8 | 60 |
| L1 | 10 | 86 |
| L2 | 9 | 49 |
| L2 | 11 | 49 |
| L2 | 8 | 106 |
| L2 | 9 | 106 |
| E1 | 11 | 490 |
| E2 | 9 | 81 |
| L1 | 9 | 294 |
| L1 | 10 | 294 |
| E1 | 8 | 260 |
| E1 | 9 | 260 |
| E6 | 11 | 23 |
| L2 | 10 | 304 |
| E2 | 8 | 150 |
| E2 | 9 | 150 |
| E2 | 10 | 150 |
| E2 | 9 | 23 |
| E2 | 11 | 23 |
| E2 | 9 | 180 |
| E5 | 8 | 14 |
| E5 | 9 | 14 |
| E5 | 11 | 14 |
| L2 | 10 | 374 |
| L2 | 9 | 241 |
| E5 | 10 | 7 |
| E2 | 8 | 201 |
| E1 | 10 | 289 |
| E1 | 11 | 289 |
| E1 | 10 | 331 |
| E1 | 11 | 331 |
| L1 | 8 | 348 |
| L1 | 11 | 348 |
| L1 | 8 | 189 |
| L1 | 8 | 392 |
| L1 | 10 | 392 |
| E2 | 10 | 40 |
| E5 | 8 | 45 |
| E5 | 9 | 45 |

TABLE XA-continued

HPV6A
HLA-A24 Supermotif Peptides

| 2 | 3 | 4 |
|---|---|---|
| E5 | 10 | 45 |
| E5 | 11 | 45 |
| L2 | 9 | 260 |
| E1 | 11 | 185 |
| E2 | 11 | 198 |
| L2 | 10 | 145 |
| L2 | 11 | 145 |
| L1 | 8 | 343 |
| E2 | 8 | 144 |
| E6 | 10 | 45 |
| E6 | 11 | 45 |
| E1 | 8 | 485 |
| E1 | 10 | 485 |
| E1 | 11 | 485 |
| L2 | 9 | 345 |
| E6 | 9 | 19 |
| E6 | 11 | 19 |
| E1 | 8 | 588 |
| L2 | 11 | 406 |
| E1 | 8 | 586 |
| E1 | 10 | 586 |
| L2 | 9 | 39 |
| E1 | 10 | 97 |
| E6 | 9 | 12 |
| E6 | 11 | 12 |
| E2 | 8 | 355 |
| E2 | 9 | 355 |
| E2 | 11 | 355 |
| L2 | 10 | 184 |
| E1 | 8 | 294 |
| E7 | 8 | 86 |
| L1 | 8 | 408 |
| E1 | 8 | 556 |
| E1 | 9 | 556 |
| E5 | 8 | 15 |
| E5 | 10 | 15 |
| E7 | 9 | 7 |
| E5 | 8 | 50 |
| E5 | 9 | 50 |
| E5 | 10 | 50 |
| E5 | 11 | 50 |
| E1 | 10 | 297 |
| E1 | 11 | 297 |
| E5 | 10 | 71 |
| E5 | 11 | 71 |
| E2 | 9 | 93 |
| E2 | 10 | 93 |
| E6 | 8 | 26 |
| L1 | 9 | 377 |
| L1 | 10 | 377 |
| E1 | 11 | 408 |
| E2 | 11 | 128 |
| L1 | 10 | 388 |
| E6 | 8 | 39 |
| E6 | 10 | 39 |
| E1 | 11 | 232 |
| L1 | 8 | 223 |
| L1 | 9 | 223 |
| L1 | 11 | 223 |
| E6 | 8 | 142 |
| E1 | 9 | 585 |
| E1 | 11 | 585 |
| E6 | 10 | 11 |
| E5 | 8 | 62 |
| E5 | 9 | 62 |
| E5 | 11 | 62 |
| L1 | 9 | 332 |
| L2 | 10 | 151 |
| L1 | 11 | 345 |
| E5 | 10 | 12 |
| E5 | 11 | 12 |
| L2 | 11 | 150 |
| E4 | 8 | 76 |
| E6 | 11 | 87 |
| L2 | 8 | 386 |
| E4 | 9 | 91 |
| E1 | 9 | 290 |
| E1 | 10 | 290 |
| E6 | 10 | 88 |
| E6 | 11 | 88 |
| E4 | 9 | 73 |
| E4 | 11 | 73 |
| E1 | 9 | 332 |
| E1 | 10 | 332 |
| L2 | 11 | 387 |
| E1 | 9 | 78 |
| E1 | 10 | 78 |
| E4 | 8 | 92 |
| L1 | 11 | 328 |
| L1 | 9 | 57 |
| L1 | 11 | 57 |
| E6 | 10 | 132 |
| E2 | 11 | 336 |
| L1 | 10 | 412 |
| L1 | 10 | 349 |
| L1 | 11 | 349 |
| L2 | 8 | 52 |
| L2 | 8 | 427 |
| L2 | 9 | 427 |
| L2 | 10 | 427 |
| E1 | 11 | 346 |
| E1 | 8 | 333 |
| E1 | 9 | 333 |
| E5 | 9 | 20 |
| L2 | 10 | 31 |
| E1 | 11 | 499 |
| L1 | 9 | 393 |
| E6 | 9 | 53 |
| E4 | 9 | 7 |
| E1 | 8 | 275 |
| E2 | 9 | 41 |
| E2 | 11 | 41 |
| L1 | 8 | 73 |
| L1 | 10 | 73 |
| E5 | 8 | 48 |
| E5 | 9 | 48 |
| E5 | 10 | 48 |
| E5 | 11 | 48 |
| E5 | 8 | 46 |
| E5 | 9 | 46 |
| E5 | 10 | 46 |
| E5 | 11 | 46 |
| L1 | 8 | 382 |
| L2 | 10 | 419 |
| L2 | 11 | 419 |
| E7 | 8 | 6 |
| E7 | 10 | 6 |
| L2 | 8 | 364 |
| L2 | 9 | 364 |
| L1 | 8 | 27 |
| L2 | 9 | 146 |
| L2 | 10 | 146 |
| E1 | 10 | 584 |
| E1 | 11 | 238 |
| E5 | 8 | 25 |
| E5 | 9 | 25 |
| E5 | 10 | 25 |
| L1 | 10 | 329 |
| E2 | 8 | 349 |
| L1 | 9 | 72 |
| L1 | 11 | 72 |
| L1 | 8 | 58 |
| L1 | 10 | 58 |
| E7 | 9 | 68 |
| E5 | 9 | 35 |
| E4 | 8 | 65 |
| L2 | 11 | 253 |
| E1 | 9 | 602 |

TABLE XA-continued

HPV6A
HLA-A24 Supermotif Peptides

| 2 | 3 | 4 |
|---|---|---|
| E5 | 8 | 42 |
| E5 | 10 | 42 |
| E5 | 11 | 42 |
| E2 | 9 | 137 |
| E1 | 9 | 426 |
| E5 | 8 | 36 |
| E1 | 8 | 340 |
| E1 | 8 | 530 |
| E1 | 11 | 530 |
| E1 | 11 | 464 |
| E5 | 8 | 58 |
| E5 | 10 | 58 |
| E5 | 11 | 58 |
| E1 | 8 | 267 |
| E1 | 10 | 267 |
| E1 | 11 | 267 |
| E2 | 8 | 92 |
| E2 | 10 | 92 |
| E2 | 11 | 92 |
| E6 | 8 | 141 |
| E6 | 9 | 141 |
| E4 | 10 | 72 |
| E1 | 8 | 237 |
| L2 | 11 | 440 |
| L2 | 10 | 441 |
| E1 | 9 | 486 |
| E1 | 10 | 486 |
| L2 | 8 | 319 |
| L1 | 10 | 385 |
| E4 | 8 | 12 |
| E4 | 10 | 12 |
| E4 | 11 | 12 |
| E1 | 10 | 86 |
| L2 | 8 | 435 |
| E1 | 9 | 579 |
| E1 | 11 | 579 |
| E5 | 8 | 54 |
| L1 | 9 | 230 |
| E1 | 9 | 532 |
| E1 | 10 | 532 |
| L1 | 8 | 358 |
| L1 | 10 | 358 |
| E1 | 11 | 536 |
| E2 | 9 | 159 |
| E2 | 10 | 159 |
| L1 | 9 | 350 |
| L1 | 10 | 350 |
| E5 | 9 | 43 |
| E5 | 10 | 43 |
| E5 | 11 | 43 |
| E1 | 8 | 402 |
| E4 | 8 | 6 |
| E4 | 10 | 6 |
| E2 | 11 | 168 |
| L1 | 9 | 287 |
| E2 | 8 | 138 |
| E1 | 8 | 91 |
| L1 | 8 | 26 |
| L1 | 9 | 26 |
| E2 | 8 | 131 |
| E2 | 10 | 158 |
| E2 | 11 | 158 |

TABLE XB

HPV6B
HLA-A24 Supermotif Peptides

| 2 | 3 | 4 |
|---|---|---|
| E1 | 10 | 377 |
| E5B | 9 | 21 |
| E5B | 10 | 21 |
| E5B | 11 | 21 |
| E1 | 11 | 392 |
| L2 | 9 | 238 |
| L2 | 10 | 238 |
| L2 | 8 | 275 |
| E1 | 9 | 251 |
| E1 | 11 | 251 |
| E5A | 9 | 23 |
| E5A | 10 | 23 |
| E5A | 11 | 23 |
| L2 | 8 | 286 |
| L2 | 11 | 286 |
| E2 | 8 | 72 |
| E2 | 11 | 72 |
| L2 | 10 | 112 |
| E1 | 11 | 22 |
| E4 | 8 | 24 |
| E4 | 9 | 24 |
| E4 | 11 | 24 |
| E1 | 11 | 520 |
| E1 | 10 | 207 |
| L1 | 8 | 81 |
| L2 | 8 | 421 |
| L2 | 9 | 421 |
| E1 | 10 | 554 |
| E1 | 11 | 554 |
| E6 | 8 | 37 |
| E6 | 10 | 37 |
| E5A | 8 | 79 |
| E1 | 9 | 319 |
| L1 | 11 | 22 |
| E1 | 11 | 296 |
| E4 | 9 | 71 |
| L2 | 10 | 14 |
| E1 | 8 | 525 |
| E1 | 9 | 525 |
| E6 | 11 | 10 |
| E1 | 10 | 77 |
| E1 | 11 | 77 |
| E1 | 10 | 101 |
| L1 | 9 | 43 |
| E1 | 10 | 601 |
| E1 | 9 | 271 |
| E1 | 10 | 271 |
| L1 | 11 | 384 |
| E6 | 8 | 47 |
| E6 | 9 | 47 |
| L1 | 8 | 25 |
| L1 | 9 | 25 |
| L1 | 10 | 25 |
| E1 | 10 | 612 |
| E1 | 9 | 215 |
| E1 | 10 | 215 |
| E5A | 8 | 27 |
| E5A | 10 | 27 |
| E5A | 11 | 27 |
| E1 | 9 | 234 |
| E1 | 11 | 234 |
| E6 | 8 | 67 |
| E6 | 11 | 67 |
| E6 | 9 | 137 |
| E2 | 9 | 296 |
| E2 | 8 | 35 |
| E2 | 9 | 35 |
| E2 | 10 | 35 |
| E1 | 8 | 488 |
| L1 | 9 | 153 |
| E1 | 10 | 14 |
| E6 | 8 | 131 |
| E6 | 11 | 131 |
| E6 | 8 | 31 |

TABLE XB-continued

HPV6B
HLA-A24 Supermotif Peptides

| 2 | 3 | 4 |
|---|---|---|
| E1 | 10 | 640 |
| E4 | 9 | 74 |
| E1 | 8 | 529 |
| E1 | 9 | 529 |
| E6 | 9 | 140 |
| E6 | 10 | 140 |
| E5A | 8 | 75 |
| E5A | 10 | 75 |
| E5A | 11 | 75 |
| E6 | 8 | 104 |
| E1 | 9 | 385 |
| E1 | 10 | 385 |
| E1 | 8 | 49 |
| E1 | 8 | 369 |
| E1 | 10 | 369 |
| L1 | 9 | 219 |
| L2 | 10 | 278 |
| E6 | 10 | 96 |
| E6 | 11 | 96 |
| E7 | 8 | 75 |
| E7 | 9 | 75 |
| E7 | 10 | 75 |
| L2 | 9 | 403 |
| E1 | 8 | 570 |
| E1 | 10 | 570 |
| E1 | 11 | 570 |
| L2 | 11 | 347 |
| L2 | 10 | 395 |
| E2 | 9 | 25 |
| E2 | 9 | 313 |
| E1 | 11 | 81 |
| L1 | 8 | 366 |
| L1 | 11 | 366 |
| E7 | 10 | 14 |
| L1 | 11 | 208 |
| E1 | 10 | 203 |
| E1 | 11 | 46 |
| L1 | 10 | 195 |
| L2 | 10 | 344 |
| L1 | 9 | 198 |
| E1 | 9 | 481 |
| E1 | 11 | 481 |
| E1 | 10 | 73 |
| L1 | 8 | 331 |
| L1 | 10 | 331 |
| E5B | 8 | 11 |
| E5B | 9 | 11 |
| E2 | 9 | 143 |
| E1 | 8 | 534 |
| L1 | 11 | 411 |
| L2 | 11 | 30 |
| E6 | 8 | 99 |
| L2 | 11 | 258 |
| E2 | 9 | 348 |
| E2 | 10 | 136 |
| E1 | 9 | 236 |
| L1 | 9 | 146 |
| L1 | 10 | 229 |
| E2 | 9 | 130 |
| E6 | 9 | 69 |
| E1 | 9 | 453 |
| E1 | 11 | 453 |
| E5A | 9 | 39 |
| E5A | 11 | 39 |
| E1 | 9 | 105 |
| E1 | 11 | 105 |
| L2 | 10 | 120 |
| E6 | 10 | 42 |
| L1 | 11 | 453 |
| E1 | 8 | 197 |
| E1 | 10 | 604 |
| E1 | 11 | 604 |
| E1 | 9 | 131 |
| E2 | 10 | 17 |
| E2 | 9 | 74 |
| E2 | 10 | 74 |
| E1 | 10 | 417 |
| E1 | 11 | 417 |
| E1 | 11 | 360 |
| E2 | 11 | 100 |
| E7 | 10 | 73 |
| E7 | 11 | 73 |
| E6 | 10 | 92 |
| E6 | 11 | 92 |
| L2 | 8 | 135 |
| E4 | 9 | 85 |
| E2 | 9 | 185 |
| E7 | 10 | 39 |
| E1 | 9 | 39 |
| E6 | 8 | 113 |
| E6 | 9 | 113 |
| L1 | 10 | 262 |
| L1 | 11 | 262 |
| L1 | 8 | 103 |
| L1 | 9 | 381 |
| L1 | 8 | 443 |
| E7 | 10 | 78 |
| E2 | 10 | 205 |
| E1 | 9 | 339 |
| E1 | 8 | 379 |
| L1 | 8 | 364 |
| L1 | 10 | 364 |
| L1 | 9 | 357 |
| L1 | 11 | 357 |
| E2 | 9 | 86 |
| E1 | 9 | 613 |
| E1 | 11 | 613 |
| L1 | 9 | 243 |
| L1 | 10 | 243 |
| E5A | 10 | 67 |
| L1 | 8 | 244 |
| L1 | 9 | 244 |
| E1 | 8 | 220 |
| L1 | 8 | 369 |
| L1 | 10 | 369 |
| E6 | 8 | 126 |
| E5A | 9 | 16 |
| E1 | 8 | 454 |
| E1 | 10 | 454 |
| E1 | 11 | 454 |
| L2 | 8 | 428 |
| L2 | 9 | 428 |
| E5B | 8 | 22 |
| E5B | 9 | 22 |
| E5B | 10 | 22 |
| E5B | 11 | 22 |
| E5A | 8 | 40 |
| E5A | 10 | 40 |
| E2 | 11 | 346 |
| E5A | 9 | 68 |
| E1 | 10 | 393 |
| L2 | 8 | 397 |
| L2 | 10 | 397 |
| E1 | 9 | 446 |
| E1 | 10 | 446 |
| L1 | 8 | 245 |
| L2 | 8 | 239 |
| L2 | 9 | 239 |
| L2 | 11 | 239 |
| E1 | 8 | 457 |
| E1 | 9 | 457 |
| E1 | 9 | 587 |
| E2 | 8 | 171 |
| E5A | 9 | 28 |
| E5A | 10 | 28 |
| E5A | 8 | 24 |
| E5A | 9 | 24 |
| E5A | 10 | 24 |

TABLE XB-continued

HPV6B
HLA-A24 Supermotif Peptides

| 2 | 3 | 4 |
|---|---|---|
| E5A | 11 | 24 |
| L1 | 10 | 441 |
| L1 | 9 | 33 |
| L1 | 10 | 33 |
| L2 | 8 | 434 |
| L2 | 9 | 434 |
| L1 | 10 | 200 |
| E1 | 8 | 241 |
| E2 | 8 | 361 |
| L2 | 8 | 433 |
| L2 | 9 | 433 |
| L2 | 10 | 433 |
| L1 | 8 | 318 |
| L1 | 9 | 318 |
| E1 | 10 | 243 |
| E1 | 11 | 194 |
| E1 | 9 | 326 |
| E2 | 9 | 156 |
| E1 | 9 | 350 |
| L1 | 10 | 101 |
| E7 | 8 | 22 |
| E1 | 8 | 217 |
| E1 | 11 | 217 |
| L1 | 10 | 400 |
| L2 | 8 | 292 |
| E5B | 8 | 15 |
| E5B | 9 | 15 |
| L1 | 9 | 144 |
| L1 | 11 | 144 |
| E5B | 8 | 25 |
| E5B | 10 | 25 |
| E2 | 8 | 55 |
| E1 | 8 | 273 |
| E1 | 10 | 273 |
| E1 | 8 | 191 |
| E1 | 9 | 191 |
| L2 | 10 | 215 |
| L2 | 11 | 215 |
| L2 | 8 | 25 |
| L2 | 8 | 64 |
| L2 | 11 | 64 |
| E1 | 8 | 436 |
| E1 | 11 | 436 |
| L1 | 9 | 407 |
| E7 | 9 | 85 |
| L2 | 11 | 412 |
| E1 | 8 | 467 |
| E1 | 10 | 467 |
| L1 | 9 | 222 |
| L1 | 10 | 222 |
| E5A | 8 | 11 |
| E5A | 11 | 11 |
| E4 | 8 | 100 |
| E4 | 10 | 100 |
| E1 | 8 | 316 |
| L2 | 9 | 51 |
| L1 | 9 | 111 |
| L1 | 10 | 111 |
| E2 | 10 | 242 |
| L1 | 8 | 113 |
| L1 | 11 | 113 |
| E1 | 8 | 16 |
| E1 | 8 | 44 |
| E6 | 11 | 58 |
| L1 | 11 | 64 |
| L1 | 8 | 468 |
| L2 | 8 | 312 |
| L2 | 9 | 312 |
| L2 | 10 | 312 |
| E2 | 10 | 53 |
| E6 | 8 | 119 |
| E6 | 9 | 119 |
| E6 | 11 | 119 |
| E1 | 9 | 264 |
| E1 | 11 | 264 |
| E2 | 10 | 78 |
| E2 | 10 | 310 |
| E6 | 10 | 50 |
| E4 | 10 | 20 |
| E6 | 9 | 25 |
| L1 | 8 | 387 |
| L1 | 11 | 387 |
| E4 | 10 | 36 |
| L2 | 8 | 306 |
| E1 | 9 | 581 |
| L1 | 9 | 361 |
| L1 | 10 | 361 |
| L1 | 11 | 361 |
| E2 | 8 | 29 |
| E1 | 8 | 502 |
| E1 | 9 | 502 |
| E1 | 10 | 502 |
| E7 | 9 | 5 |
| E7 | 11 | 5 |
| E2 | 11 | 183 |
| E2 | 11 | 32 |
| E1 | 8 | 75 |
| L2 | 9 | 318 |
| E1 | 10 | 412 |
| E5B | 8 | 61 |
| E5B | 9 | 61 |
| E5B | 10 | 61 |
| E5B | 11 | 61 |
| L1 | 9 | 370 |
| L1 | 10 | 32 |
| L1 | 11 | 32 |
| E5A | 8 | 21 |
| E5A | 11 | 21 |
| E5A | 10 | 31 |
| E5A | 11 | 31 |
| L2 | 9 | 113 |
| L2 | 9 | 279 |
| E6 | 9 | 97 |
| E6 | 10 | 97 |
| E1 | 10 | 195 |
| E5A | 9 | 32 |
| E5A | 10 | 32 |
| L2 | 10 | 44 |
| L2 | 11 | 44 |
| E5A | 8 | 17 |
| E6 | 8 | 120 |
| E6 | 10 | 120 |
| L2 | 8 | 404 |
| L2 | 8 | 429 |
| E1 | 11 | 56 |
| E1 | 9 | 571 |
| E1 | 10 | 571 |
| L1 | 8 | 376 |
| L1 | 10 | 376 |
| L1 | 11 | 376 |
| E1 | 11 | 341 |
| L2 | 11 | 131 |
| L1 | 10 | 187 |
| L2 | 8 | 247 |
| E5B | 8 | 23 |
| E5B | 9 | 23 |
| E5B | 10 | 23 |
| E1 | 11 | 476 |
| L2 | 9 | 121 |
| L2 | 11 | 121 |
| E1 | 10 | 443 |
| E2 | 11 | 287 |
| E1 | 10 | 23 |
| L2 | 10 | 104 |
| L2 | 11 | 104 |
| E5A | 8 | 34 |
| E5A | 10 | 34 |
| E5A | 9 | 41 |

TABLE XB-continued

HPV6B
HLA-A24 Supermotif Peptides

| 2 | 3 | 4 |
|---|---|---|
| E5A | 11 | 41 |
| L2 | 10 | 348 |
| E1 | 10 | 531 |
| E1 | 11 | 531 |
| E6 | 9 | 43 |
| L1 | 10 | 286 |
| E2 | 8 | 157 |
| E2 | 11 | 157 |
| L1 | 9 | 79 |
| L1 | 10 | 79 |
| E2 | 10 | 120 |
| E1 | 8 | 211 |
| E1 | 10 | 211 |
| E1 | 11 | 211 |
| L1 | 8 | 462 |
| L1 | 9 | 449 |
| L1 | 11 | 449 |
| E1 | 8 | 433 |
| E1 | 11 | 433 |
| E6 | 8 | 73 |
| E6 | 10 | 73 |
| E2 | 10 | 351 |
| E1 | 9 | 312 |
| E1 | 10 | 312 |
| E1 | 11 | 312 |
| E2 | 9 | 359 |
| E2 | 10 | 359 |
| E1 | 8 | 254 |
| E1 | 9 | 254 |
| E6 | 11 | 128 |
| E1 | 8 | 357 |
| E1 | 10 | 357 |
| L2 | 11 | 22 |
| E1 | 8 | 420 |
| E6 | 10 | 18 |
| E4 | 8 | 52 |
| L1 | 10 | 56 |
| L2 | 11 | 34 |
| E2 | 11 | 147 |
| E6 | 11 | 116 |
| E6 | 8 | 52 |
| E6 | 10 | 52 |
| E2 | 11 | 63 |
| L1 | 10 | 61 |
| L1 | 8 | 19 |
| L1 | 10 | 71 |
| L2 | 8 | 46 |
| L2 | 9 | 46 |
| E2 | 8 | 177 |
| E1 | 11 | 85 |
| E1 | 10 | 578 |
| L1 | 8 | 226 |
| E4 | 8 | 28 |
| E1 | 9 | 401 |
| E4 | 8 | 8 |
| E4 | 9 | 8 |
| E4 | 11 | 8 |
| E2 | 9 | 311 |
| E2 | 11 | 311 |
| L1 | 9 | 87 |
| L1 | 11 | 87 |
| L1 | 10 | 242 |
| L1 | 11 | 242 |
| L2 | 9 | 396 |
| L2 | 11 | 396 |
| L1 | 8 | 302 |
| E1 | 11 | 66 |
| E6 | 8 | 54 |
| L2 | 8 | 107 |
| E1 | 8 | 255 |
| E1 | 11 | 255 |
| E1 | 8 | 557 |
| E6 | 11 | 101 |
| E1 | 10 | 491 |

TABLE XB-continued

HPV6B
HLA-A24 Supermotif Peptides

| 2 | 3 | 4 |
|---|---|---|
| E2 | 8 | 314 |
| L1 | 11 | 186 |
| L2 | 9 | 246 |
| E5A | 8 | 33 |
| E5A | 9 | 33 |
| E5A | 11 | 33 |
| L1 | 8 | 41 |
| L1 | 9 | 41 |
| L1 | 11 | 41 |
| E5B | 9 | 18 |
| E5B | 10 | 18 |
| E1 | 10 | 521 |
| E1 | 11 | 521 |
| E1 | 9 | 540 |
| E1 | 9 | 208 |
| E1 | 11 | 208 |
| E7 | 11 | 83 |
| E4 | 8 | 18 |
| E1 | 11 | 198 |
| E7 | 8 | 82 |
| E5A | 9 | 59 |
| E5A | 10 | 59 |
| E5A | 11 | 59 |
| E5A | 11 | 55 |
| E5A | 8 | 51 |
| E5A | 9 | 51 |
| E5A | 10 | 51 |
| E5A | 11 | 51 |
| E1 | 9 | 298 |
| E1 | 10 | 298 |
| E1 | 11 | 298 |
| E2 | 8 | 82 |
| E2 | 11 | 82 |
| E5A | 8 | 69 |
| E5A | 8 | 60 |
| E5A | 9 | 60 |
| E5A | 10 | 60 |
| E5A | 11 | 60 |
| E5A | 9 | 72 |
| E5A | 10 | 72 |
| E5A | 11 | 72 |
| E1 | 9 | 563 |
| E5A | 10 | 56 |
| E2 | 8 | 42 |
| E2 | 10 | 42 |
| E5A | 8 | 52 |
| E5A | 9 | 52 |
| E5A | 10 | 52 |
| E5B | 11 | 3 |
| E1 | 8 | 132 |
| E1 | 9 | 358 |
| L2 | 10 | 23 |
| E6 | 9 | 121 |
| E1 | 8 | 458 |
| E1 | 9 | 555 |
| E1 | 10 | 555 |
| E5A | 8 | 49 |
| E5A | 9 | 49 |
| E5A | 10 | 49 |
| E5A | 11 | 49 |
| E5A | 11 | 70 |
| E1 | 9 | 268 |
| E1 | 10 | 268 |
| E6 | 9 | 38 |
| E6 | 11 | 38 |
| E5A | 8 | 61 |
| E5A | 9 | 61 |
| E5A | 10 | 61 |
| L2 | 9 | 338 |
| L2 | 11 | 338 |
| E5A | 8 | 73 |
| E5A | 9 | 73 |
| E5A | 10 | 73 |
| E1 | 8 | 514 |

TABLE XB-continued

HPV6B
HLA-A24 Supermotif Peptides

| 2 | 3 | 4 |
|---|---|---|
| E1 | 9 | 514 |
| E5A | 8 | 47 |
| E5A | 9 | 47 |
| E5A | 10 | 47 |
| E5A | 11 | 47 |
| L1 | 8 | 295 |
| L1 | 9 | 295 |
| E1 | 8 | 564 |
| E7 | 10 | 67 |
| L1 | 8 | 95 |
| E5B | 8 | 16 |
| E5B | 11 | 16 |
| E5A | 9 | 57 |
| E5A | 11 | 57 |
| E1 | 8 | 261 |
| E2 | 9 | 18 |
| E2 | 9 | 43 |
| E4 | 9 | 21 |
| E4 | 11 | 21 |
| E5A | 8 | 53 |
| E5A | 9 | 53 |
| E4 | 8 | 15 |
| E4 | 9 | 15 |
| E4 | 11 | 15 |
| E1 | 8 | 320 |
| E5B | 9 | 26 |
| E1 | 8 | 306 |
| E2 | 8 | 151 |
| E2 | 9 | 151 |
| E1 | 10 | 47 |
| L1 | 9 | 196 |
| L1 | 11 | 196 |
| L1 | 8 | 154 |
| E1 | 9 | 274 |
| E1 | 10 | 361 |
| E2 | 10 | 101 |
| L1 | 10 | 1 |
| E2 | 9 | 170 |
| E1 | 10 | 568 |
| E1 | 8 | 451 |
| E1 | 11 | 451 |
| L1 | 11 | 31 |
| E4 | 11 | 5 |
| E1 | 8 | 300 |
| E1 | 9 | 300 |
| L1 | 10 | 445 |
| E1 | 8 | 539 |
| E1 | 10 | 539 |
| L1 | 9 | 438 |
| E6 | 9 | 21 |
| L2 | 8 | 38 |
| L2 | 10 | 38 |
| E1 | 11 | 96 |
| E2 | 8 | 127 |
| E1 | 8 | 607 |
| E1 | 11 | 607 |
| L2 | 8 | 385 |
| L1 | 11 | 142 |
| E1 | 9 | 609 |
| E1 | 8 | 439 |
| E1 | 9 | 439 |
| E1 | 10 | 594 |
| E1 | 10 | 226 |
| E1 | 8 | 456 |
| E1 | 9 | 456 |
| E1 | 10 | 456 |
| L2 | 9 | 414 |
| L2 | 9 | 325 |
| L2 | 11 | 325 |
| L1 | 11 | 217 |
| L2 | 10 | 189 |
| E1 | 11 | 442 |
| E4 | 8 | 69 |
| E4 | 11 | 69 |

TABLE XB-continued

HPV6B
HLA-A24 Supermotif Peptides

| 2 | 3 | 4 |
|---|---|---|
| E6 | 11 | 110 |
| L1 | 9 | 183 |
| L1 | 8 | 458 |
| L1 | 11 | 109 |
| E7 | 8 | 47 |
| E1 | 8 | 562 |
| E1 | 10 | 562 |
| E5A | 9 | 64 |
| E5A | 10 | 64 |
| L2 | 10 | 73 |
| L2 | 8 | 389 |
| L2 | 9 | 389 |
| L2 | 10 | 389 |
| E1 | 8 | 258 |
| E1 | 10 | 258 |
| E1 | 11 | 258 |
| L2 | 10 | 337 |
| E1 | 9 | 513 |
| E1 | 10 | 513 |
| E1 | 11 | 545 |
| L2 | 9 | 407 |
| E2 | 9 | 354 |
| E2 | 10 | 354 |
| L1 | 11 | 426 |
| L2 | 9 | 359 |
| L1 | 8 | 90 |
| L2 | 8 | 183 |
| L2 | 11 | 183 |
| L2 | 9 | 96 |
| E2 | 9 | 258 |
| E2 | 10 | 258 |
| L2 | 8 | 171 |
| L2 | 9 | 171 |
| L2 | 10 | 171 |
| L2 | 9 | 426 |
| L2 | 10 | 426 |
| L2 | 11 | 426 |
| E7 | 10 | 20 |
| E5A | 10 | 19 |
| L1 | 8 | 266 |
| L1 | 10 | 175 |
| L1 | 11 | 16 |
| L2 | 9 | 363 |
| L2 | 10 | 363 |
| L2 | 9 | 382 |
| L2 | 11 | 382 |
| E2 | 9 | 91 |
| E2 | 11 | 91 |
| E4 | 11 | 81 |
| E6 | 9 | 60 |
| E6 | 11 | 60 |
| L1 | 8 | 237 |
| L1 | 9 | 237 |
| L1 | 10 | 237 |
| L1 | 8 | 435 |
| E1 | 9 | 90 |
| E5A | 8 | 66 |
| E5A | 11 | 66 |
| L1 | 9 | 368 |
| L1 | 11 | 368 |
| E1 | 10 | 355 |
| E2 | 9 | 163 |
| E2 | 8 | 345 |
| E1 | 8 | 445 |
| E1 | 10 | 445 |
| E1 | 11 | 445 |
| E5B | 8 | 6 |
| E5B | 9 | 6 |
| E5B | 11 | 6 |
| E2 | 9 | 289 |
| E5A | 10 | 7 |
| E5A | 11 | 7 |
| L2 | 8 | 43 |
| L2 | 11 | 43 |

TABLE XB-continued

HPV6B
HLA-A24 Supermotif Peptides

| 2 | 3 | 4 |
|---|---|---|
| E6 | 11 | 28 |
| E6 | 8 | 15 |
| E6 | 10 | 15 |
| L1 | 11 | 151 |
| L1 | 8 | 301 |
| L1 | 9 | 301 |
| E7 | 9 | 81 |
| L2 | 8 | 16 |
| E4 | 8 | 14 |
| E4 | 9 | 14 |
| E4 | 10 | 14 |
| L1 | 11 | 232 |
| L1 | 8 | 250 |
| E2 | 9 | 48 |
| E2 | 8 | 76 |
| E1 | 9 | 305 |
| L1 | 9 | 210 |
| L1 | 11 | 210 |
| E2 | 8 | 103 |
| E1 | 10 | 128 |
| L2 | 8 | 75 |
| E1 | 8 | 344 |
| L2 | 9 | 231 |
| L2 | 10 | 231 |
| L2 | 8 | 233 |
| E1 | 8 | 363 |
| E1 | 10 | 425 |
| E1 | 9 | 266 |
| E1 | 11 | 266 |
| L1 | 8 | 456 |
| L1 | 9 | 456 |
| L1 | 10 | 456 |
| E6 | 10 | 76 |
| L1 | 9 | 66 |
| E6 | 9 | 125 |
| L2 | 8 | 298 |
| L2 | 8 | 316 |
| L2 | 11 | 316 |
| E2 | 9 | 7 |
| E2 | 10 | 7 |
| L1 | 11 | 241 |
| E1 | 8 | 125 |
| L2 | 10 | 245 |
| L1 | 9 | 40 |
| L1 | 10 | 40 |
| E2 | 9 | 303 |
| E2 | 10 | 303 |
| E1 | 8 | 616 |
| E7 | 11 | 66 |
| L1 | 9 | 94 |
| E2 | 9 | 84 |
| E2 | 11 | 84 |
| E1 | 11 | 324 |
| E1 | 9 | 293 |
| L1 | 8 | 279 |
| L1 | 9 | 279 |
| L2 | 9 | 221 |
| L1 | 8 | 140 |
| E1 | 11 | 583 |
| E2 | 11 | 301 |
| L2 | 11 | 295 |
| L1 | 8 | 414 |
| E1 | 9 | 219 |
| E1 | 8 | 493 |
| L1 | 11 | 440 |
| E1 | 9 | 547 |
| E1 | 11 | 547 |
| L2 | 8 | 153 |
| L2 | 10 | 267 |
| L2 | 11 | 267 |
| E5A | 8 | 30 |
| E5A | 11 | 30 |
| E2 | 8 | 207 |
| E1 | 9 | 247 |
| E1 | 10 | 247 |
| L1 | 9 | 375 |
| L1 | 11 | 375 |
| L2 | 11 | 103 |
| L1 | 11 | 285 |
| E1 | 8 | 60 |
| L1 | 10 | 86 |
| L2 | 9 | 49 |
| L2 | 11 | 49 |
| L2 | 8 | 106 |
| L2 | 9 | 106 |
| E1 | 11 | 490 |
| E2 | 9 | 81 |
| L2 | 8 | 391 |
| L1 | 9 | 294 |
| L1 | 10 | 294 |
| E1 | 8 | 260 |
| E1 | 9 | 260 |
| E6 | 11 | 23 |
| L2 | 10 | 304 |
| E2 | 8 | 150 |
| E2 | 9 | 150 |
| E2 | 10 | 150 |
| E2 | 9 | 23 |
| E2 | 11 | 23 |
| E5A | 8 | 14 |
| E5A | 9 | 14 |
| E5A | 11 | 14 |
| E2 | 9 | 180 |
| L2 | 10 | 374 |
| L2 | 9 | 241 |
| E6 | 10 | 7 |
| E2 | 8 | 201 |
| E1 | 10 | 289 |
| E1 | 11 | 289 |
| E1 | 10 | 331 |
| E1 | 11 | 331 |
| L1 | 8 | 348 |
| L1 | 11 | 348 |
| L1 | 8 | 189 |
| L1 | 8 | 392 |
| L1 | 10 | 392 |
| E2 | 10 | 40 |
| E5A | 8 | 45 |
| E5A | 9 | 45 |
| E5A | 10 | 45 |
| E5A | 11 | 45 |
| L2 | 9 | 260 |
| E1 | 11 | 185 |
| E2 | 11 | 198 |
| L2 | 10 | 145 |
| L2 | 11 | 145 |
| L1 | 8 | 343 |
| E6 | 10 | 45 |
| E5 | 11 | 45 |
| E1 | 8 | 485 |
| E1 | 10 | 485 |
| E1 | 11 | 485 |
| L2 | 9 | 345 |
| E5A | 8 | 15 |
| E5A | 10 | 15 |
| E6 | 9 | 19 |
| E6 | 11 | 19 |
| E1 | 8 | 588 |
| L2 | 11 | 405 |
| E1 | 8 | 586 |
| E1 | 10 | 586 |
| L2 | 9 | 39 |
| E1 | 10 | 97 |
| E6 | 9 | 12 |
| E6 | 11 | 12 |
| E2 | 8 | 355 |
| E2 | 9 | 355 |
| E2 | 11 | 355 |

TABLE XB-continued

HPV6B
HLA-A24 Supermotif Peptides

| 2 | 3 | 4 |
|---|---|---|
| E1 | 8 | 294 |
| L1 | 8 | 408 |
| E1 | 8 | 556 |
| E1 | 9 | 556 |
| E7 | 9 | 7 |
| E5A | 8 | 50 |
| E5A | 9 | 50 |
| E5A | 10 | 50 |
| E5A | 11 | 50 |
| E1 | 10 | 297 |
| E1 | 11 | 297 |
| E5A | 10 | 71 |
| E5A | 11 | 71 |
| E7 | 8 | 86 |
| E2 | 9 | 93 |
| E2 | 10 | 93 |
| E6 | 8 | 26 |
| L1 | 9 | 377 |
| L1 | 10 | 377 |
| E1 | 11 | 408 |
| E2 | 11 | 128 |
| E5B | 10 | 59 |
| E5B | 11 | 59 |
| L1 | 10 | 388 |
| E6 | 8 | 39 |
| E6 | 10 | 39 |
| L1 | 8 | 223 |
| L1 | 9 | 223 |
| L1 | 11 | 223 |
| E1 | 11 | 232 |
| E6 | 8 | 142 |
| E5B | 8 | 63 |
| E5B | 9 | 63 |
| E1 | 9 | 585 |
| E1 | 11 | 585 |
| E6 | 10 | 11 |
| E5A | 8 | 62 |
| E5A | 9 | 62 |
| E5A | 11 | 62 |
| L1 | 9 | 332 |
| L2 | 10 | 151 |
| L1 | 11 | 345 |
| E5A | 10 | 12 |
| E5A | 11 | 12 |
| L2 | 11 | 150 |
| E4 | 8 | 86 |
| E6 | 11 | 87 |
| L2 | 11 | 386 |
| E4 | 9 | 101 |
| E2 | 11 | 212 |
| E1 | 9 | 290 |
| E1 | 10 | 290 |
| E6 | 10 | 88 |
| E6 | 11 | 88 |
| E4 | 9 | 83 |
| E4 | 11 | 83 |
| E1 | 9 | 332 |
| E1 | 10 | 332 |
| L2 | 10 | 387 |
| L2 | 11 | 387 |
| E1 | 9 | 78 |
| E1 | 10 | 78 |
| L2 | 10 | 184 |
| E4 | 8 | 102 |
| L1 | 11 | 328 |
| L1 | 9 | 57 |
| L1 | 11 | 57 |
| E6 | 10 | 132 |
| E5B | 8 | 12 |
| E5B | 11 | 12 |
| E2 | 8 | 144 |
| E2 | 11 | 336 |
| L1 | 10 | 412 |
| L1 | 10 | 349 |
| L1 | 11 | 349 |
| E2 | 10 | 213 |
| L2 | 8 | 52 |
| L2 | 8 | 427 |
| L2 | 9 | 427 |
| L2 | 10 | 427 |
| E1 | 11 | 346 |
| E1 | 8 | 333 |
| E1 | 9 | 333 |
| E5A | 9 | 20 |
| L2 | 10 | 31 |
| E1 | 11 | 499 |
| L1 | 9 | 393 |
| E6 | 9 | 53 |
| E4 | 9 | 17 |
| E1 | 8 | 275 |
| E2 | 9 | 41 |
| E2 | 11 | 41 |
| L1 | 8 | 73 |
| L1 | 10 | 73 |
| E5A | 8 | 48 |
| E5A | 9 | 48 |
| E5A | 10 | 48 |
| E5A | 11 | 48 |
| E5A | 8 | 46 |
| E5A | 9 | 46 |
| E5A | 10 | 46 |
| E5A | 11 | 46 |
| E4 | 9 | 10 |
| E4 | 10 | 10 |
| L1 | 8 | 382 |
| E7 | 8 | 6 |
| E7 | 10 | 6 |
| E5B | 11 | 58 |
| L2 | 8 | 364 |
| L2 | 9 | 364 |
| L2 | 11 | 418 |
| L1 | 8 | 27 |
| L2 | 9 | 185 |
| L2 | 11 | 185 |
| L2 | 9 | 146 |
| L2 | 10 | 146 |
| E1 | 10 | 584 |
| E1 | 11 | 238 |
| E5A | 8 | 25 |
| E5A | 9 | 25 |
| E5A | 10 | 25 |
| L1 | 10 | 329 |
| E2 | 8 | 349 |
| L1 | 9 | 72 |
| L1 | 11 | 72 |
| L1 | 8 | 58 |
| L1 | 10 | 58 |
| E7 | 9 | 68 |
| E5A | 9 | 35 |
| E4 | 8 | 75 |
| L2 | 11 | 253 |
| E1 | 9 | 602 |
| E5A | 8 | 42 |
| E5A | 10 | 42 |
| E5A | 11 | 42 |
| E2 | 9 | 137 |
| E1 | 9 | 426 |
| E5A | 8 | 36 |
| E1 | 8 | 340 |
| E1 | 8 | 530 |
| E1 | 11 | 530 |
| E5B | 10 | 13 |
| E5B | 11 | 13 |
| E1 | 11 | 464 |
| E5B | 10 | 17 |
| E5B | 11 | 17 |
| E5A | 8 | 58 |
| E5A | 10 | 58 |

TABLE XB-continued

HPV6B
HLA-A24 Supermotif Peptides

| 2 | 3 | 4 |
|---|---|---|
| E5A | 11 | 58 |
| E1 | 8 | 267 |
| E1 | 10 | 267 |
| E1 | 11 | 267 |
| E2 | 8 | 92 |
| E2 | 10 | 92 |
| E2 | 11 | 92 |
| E6 | 8 | 141 |
| E6 | 9 | 141 |
| E4 | 10 | 82 |
| E1 | 8 | 237 |
| L2 | 11 | 440 |
| L2 | 10 | 441 |
| E1 | 9 | 486 |
| E1 | 10 | 486 |
| L2 | 8 | 319 |
| L1 | 10 | 385 |
| E4 | 8 | 22 |
| E4 | 10 | 22 |
| E4 | 11 | 22 |
| E1 | 10 | 86 |
| L2 | 8 | 435 |
| E1 | 9 | 579 |
| E1 | 11 | 579 |
| E5A | 8 | 54 |
| L1 | 9 | 230 |
| E1 | 9 | 532 |
| E1 | 10 | 532 |
| L1 | 8 | 358 |
| L1 | 10 | 358 |
| E1 | 11 | 536 |
| E2 | 9 | 159 |
| E2 | 10 | 159 |
| L1 | 9 | 350 |
| L1 | 10 | 350 |
| E2 | 9 | 214 |
| E5A | 9 | 43 |
| E5A | 10 | 43 |
| E5A | 11 | 43 |
| E5B | 8 | 62 |
| E5B | 9 | 62 |
| E5B | 10 | 62 |
| E1 | 8 | 402 |
| E4 | 8 | 16 |
| E4 | 10 | 16 |
| E4 | 8 | 9 |
| E4 | 10 | 9 |
| E4 | 11 | 9 |
| E2 | 11 | 168 |
| L1 | 9 | 287 |
| E2 | 8 | 138 |
| E1 | 8 | 91 |
| L1 | 8 | 26 |
| L1 | 9 | 26 |
| E2 | 8 | 131 |
| E2 | 10 | 158 |
| E2 | 11 | 158 |

TABLE X C

HPV11
HLA-A24 Supermotif Peptides

| 2 | 3 | 4 |
|---|---|---|
| E5 | 9 | 23 |
| E5 | 11 | 23 |
| E1 | 10 | 377 |
| E1 | 11 | 392 |
| L2 | 9 | 237 |
| L2 | 8 | 274 |

TABLE X C-continued

HPV11
HLA-A24 Supermotif Peptides

| 2 | 3 | 4 |
|---|---|---|
| L2 | 9 | 215 |
| L2 | 10 | 215 |
| E1 | 9 | 251 |
| E1 | 11 | 251 |
| E5 | 9 | 22 |
| E5 | 10 | 22 |
| E5 | 11 | 22 |
| E5 | 8 | 79 |
| E2 | 8 | 72 |
| E2 | 11 | 72 |
| L2 | 8 | 285 |
| L2 | 11 | 285 |
| E1 | 11 | 22 |
| E1 | 11 | 520 |
| L1 | 8 | 81 |
| L2 | 8 | 417 |
| L2 | 9 | 417 |
| E1 | 10 | 554 |
| E1 | 11 | 554 |
| E6 | 8 | 37 |
| E6 | 10 | 37 |
| E4 | 8 | 24 |
| E4 | 9 | 24 |
| E4 | 11 | 24 |
| E1 | 9 | 319 |
| L1 | 11 | 22 |
| L2 | 10 | 22 |
| E1 | 8 | 525 |
| E1 | 9 | 525 |
| E6 | 11 | 10 |
| E5 | 8 | 11 |
| E1 | 10 | 77 |
| E1 | 11 | 77 |
| L1 | 8 | 349 |
| L1 | 11 | 349 |
| E5 | 9 | 25 |
| E5 | 10 | 25 |
| E5 | 11 | 25 |
| E1 | 10 | 101 |
| L1 | 9 | 43 |
| E5 | 8 | 26 |
| E5 | 10 | 26 |
| E1 | 10 | 601 |
| E1 | 9 | 271 |
| E1 | 10 | 271 |
| E6 | 11 | 45 |
| L1 | 11 | 385 |
| E6 | 9 | 47 |
| L1 | 8 | 25 |
| L1 | 9 | 25 |
| L1 | 10 | 25 |
| E1 | 9 | 486 |
| E1 | 10 | 486 |
| E1 | 10 | 612 |
| E1 | 9 | 215 |
| E1 | 10 | 215 |
| E2 | 10 | 298 |
| E5 | 8 | 27 |
| E5 | 9 | 27 |
| E5 | 10 | 27 |
| E5 | 11 | 27 |
| E2 | 8 | 35 |
| E2 | 9 | 35 |
| E6 | 8 | 67 |
| E6 | 11 | 67 |
| E6 | 9 | 137 |
| E2 | 9 | 295 |
| E1 | 8 | 488 |
| L1 | 9 | 154 |
| E7 | 9 | 71 |
| E1 | 10 | 14 |
| E1 | 10 | 289 |
| E1 | 11 | 289 |
| E5 | 8 | 73 |

TABLE X C-continued

HPV11
HLA-A24 Supermotif Peptides

| 2 | 3 | 4 |
|---|---|---|
| E5 | 9 | 73 |
| E5 | 10 | 73 |
| E6 | 8 | 31 |
| E1 | 10 | 640 |
| E4 | 9 | 73 |
| E6 | 9 | 140 |
| E6 | 10 | 140 |
| E1 | 8 | 529 |
| E1 | 9 | 529 |
| E5 | 8 | 75 |
| E5 | 10 | 75 |
| E5 | 11 | 75 |
| E6 | 8 | 104 |
| E6 | 11 | 104 |
| E1 | 9 | 385 |
| E1 | 10 | 385 |
| E1 | 8 | 49 |
| E5 | 9 | 39 |
| E5 | 11 | 39 |
| L2 | 8 | 429 |
| L2 | 9 | 429 |
| L2 | 10 | 429 |
| E1 | 8 | 369 |
| E1 | 10 | 369 |
| L1 | 9 | 220 |
| E2 | 9 | 25 |
| L2 | 10 | 277 |
| E6 | 10 | 96 |
| E6 | 11 | 96 |
| E7 | 8 | 75 |
| E7 | 9 | 75 |
| E7 | 10 | 75 |
| E1 | 10 | 203 |
| E1 | 8 | 570 |
| E1 | 10 | 570 |
| E1 | 11 | 570 |
| L2 | 9 | 399 |
| L2 | 10 | 346 |
| E1 | 11 | 81 |
| E7 | 9 | 81 |
| L1 | 8 | 367 |
| L1 | 11 | 367 |
| E7 | 10 | 14 |
| L1 | 11 | 209 |
| L1 | 9 | 439 |
| E1 | 11 | 46 |
| L1 | 10 | 196 |
| L2 | 10 | 343 |
| L1 | 9 | 199 |
| E1 | 9 | 481 |
| E1 | 11 | 481 |
| E1 | 8 | 191 |
| E1 | 9 | 191 |
| E2 | 8 | 96 |
| L1 | 8 | 332 |
| L1 | 10 | 332 |
| E5 | 8 | 12 |
| E5 | 9 | 12 |
| E1 | 8 | 534 |
| L1 | 11 | 412 |
| L1 | 8 | 125 |
| L2 | 11 | 29 |
| L2 | 11 | 257 |
| L2 | 10 | 391 |
| E1 | 9 | 236 |
| L1 | 9 | 147 |
| L1 | 10 | 230 |
| L1 | 8 | 365 |
| L1 | 10 | 365 |
| E1 | 9 | 453 |
| E1 | 11 | 453 |
| E6 | 8 | 113 |
| E6 | 9 | 113 |
| E1 | 9 | 105 |
| E1 | 11 | 105 |
| E6 | 10 | 42 |
| E2 | 9 | 312 |
| L1 | 11 | 454 |
| E1 | 8 | 197 |
| E6 | 9 | 69 |
| E1 | 10 | 604 |
| E1 | 11 | 604 |
| E1 | 9 | 131 |
| E2 | 8 | 17 |
| E2 | 10 | 17 |
| E1 | 10 | 417 |
| E1 | 11 | 417 |
| E2 | 9 | 74 |
| E1 | 11 | 360 |
| E2 | 11 | 100 |
| E2 | 8 | 66 |
| E2 | 10 | 66 |
| E6 | 10 | 92 |
| E6 | 11 | 92 |
| E1 | 10 | 128 |
| E2 | 9 | 185 |
| E1 | 9 | 39 |
| L1 | 8 | 103 |
| L1 | 9 | 382 |
| L1 | 8 | 444 |
| E2 | 10 | 205 |
| L2 | 10 | 119 |
| E1 | 9 | 339 |
| E1 | 8 | 379 |
| L1 | 9 | 358 |
| L1 | 11 | 358 |
| E2 | 8 | 130 |
| E2 | 9 | 130 |
| E2 | 10 | 130 |
| E1 | 9 | 613 |
| E1 | 11 | 613 |
| E5 | 10 | 67 |
| E5 | 11 | 67 |
| L1 | 9 | 244 |
| L1 | 10 | 244 |
| L1 | 8 | 370 |
| L1 | 10 | 370 |
| E6 | 8 | 126 |
| E1 | 8 | 454 |
| E1 | 10 | 454 |
| E1 | 11 | 454 |
| L2 | 8 | 424 |
| L2 | 9 | 424 |
| E1 | 9 | 494 |
| E5 | 9 | 68 |
| E5 | 10 | 68 |
| E1 | 10 | 393 |
| E2 | 11 | 345 |
| E1 | 9 | 446 |
| E1 | 10 | 446 |
| E1 | 8 | 457 |
| E1 | 9 | 457 |
| L2 | 8 | 238 |
| L2 | 11 | 238 |
| E5 | 8 | 16 |
| E5 | 9 | 20 |
| E5 | 11 | 20 |
| E1 | 9 | 587 |
| E1 | 8 | 220 |
| L2 | 8 | 393 |
| L2 | 10 | 393 |
| E5 | 8 | 23 |
| E5 | 9 | 23 |
| E5 | 10 | 23 |
| E5 | 11 | 23 |
| E5 | 8 | 40 |
| E5 | 10 | 40 |
| L1 | 10 | 442 |

TABLE X C-continued

HPV11
HLA-A24 Supermotif Peptides

| 2 | 3 | 4 |
|---|---|---|
| L1 | 9 | 33 |
| L1 | 10 | 33 |
| L2 | 8 | 430 |
| L2 | 9 | 430 |
| L1 | 8 | 245 |
| L1 | 9 | 245 |
| L1 | 10 | 201 |
| E1 | 8 | 241 |
| E2 | 8 | 360 |
| L1 | 8 | 319 |
| L1 | 9 | 319 |
| E1 | 10 | 243 |
| E1 | 11 | 194 |
| E1 | 9 | 326 |
| E2 | 9 | 156 |
| L1 | 10 | 101 |
| E7 | 8 | 22 |
| E2 | 8 | 55 |
| E1 | 8 | 217 |
| E1 | 11 | 217 |
| L1 | 10 | 401 |
| L2 | 8 | 291 |
| L1 | 9 | 145 |
| L1 | 11 | 145 |
| E1 | 8 | 273 |
| E1 | 10 | 273 |
| L2 | 8 | 24 |
| E1 | 10 | 431 |
| L1 | 9 | 408 |
| E1 | 11 | 296 |
| E7 | 9 | 85 |
| L2 | 11 | 408 |
| E1 | 8 | 467 |
| E1 | 10 | 467 |
| E4 | 8 | 99 |
| E4 | 10 | 99 |
| L1 | 9 | 223 |
| L1 | 10 | 223 |
| L1 | 11 | 262 |
| L2 | 9 | 50 |
| L1 | 9 | 111 |
| L1 | 10 | 111 |
| E1 | 8 | 316 |
| L1 | 8 | 113 |
| L1 | 11 | 113 |
| E1 | 8 | 16 |
| E1 | 8 | 44 |
| L1 | 11 | 64 |
| L2 | 8 | 311 |
| L2 | 9 | 311 |
| E2 | 10 | 53 |
| E6 | 8 | 119 |
| E6 | 9 | 119 |
| E6 | 11 | 119 |
| L2 | 9 | 176 |
| E2 | 8 | 29 |
| E2 | 10 | 29 |
| E1 | 9 | 264 |
| E1 | 11 | 264 |
| E2 | 10 | 136 |
| E2 | 10 | 78 |
| E2 | 10 | 309 |
| E5 | 8 | 7 |
| E5 | 9 | 7 |
| E5 | 10 | 7 |
| E5 | 11 | 7 |
| E4 | 10 | 20 |
| E1 | 9 | 305 |
| E6 | 9 | 25 |
| L1 | 8 | 388 |
| L1 | 11 | 388 |
| E4 | 10 | 36 |
| L2 | 8 | 36 |
| L2 | 9 | 36 |
| L2 | 11 | 36 |
| L2 | 11 | 148 |
| L2 | 10 | 188 |
| L1 | 9 | 362 |
| L1 | 10 | 362 |
| L1 | 11 | 362 |
| E2 | 11 | 183 |
| E2 | 11 | 32 |
| E1 | 8 | 75 |
| E1 | 10 | 412 |
| L1 | 9 | 371 |
| L1 | 10 | 32 |
| L1 | 11 | 32 |
| E4 | 11 | 5 |
| E5 | 10 | 34 |
| L2 | 9 | 278 |
| E1 | 10 | 195 |
| E6 | 8 | 120 |
| E6 | 10 | 120 |
| L2 | 8 | 177 |
| E5 | 9 | 35 |
| E6 | 9 | 97 |
| E6 | 10 | 97 |
| L2 | 10 | 43 |
| L2 | 11 | 43 |
| E5 | 8 | 17 |
| E5 | 8 | 28 |
| E5 | 9 | 28 |
| E5 | 10 | 28 |
| E1 | 11 | 408 |
| E2 | 9 | 30 |
| L2 | 8 | 400 |
| L2 | 8 | 425 |
| L1 | 8 | 377 |
| L1 | 10 | 377 |
| L1 | 11 | 377 |
| E1 | 11 | 56 |
| E1 | 11 | 341 |
| L2 | 9 | 184 |
| L2 | 11 | 184 |
| L2 | 10 | 286 |
| L2 | 11 | 130 |
| L1 | 10 | 188 |
| E1 | 10 | 23 |
| E5 | 10 | 31 |
| E1 | 10 | 443 |
| E2 | 11 | 286 |
| L2 | 10 | 103 |
| L2 | 11 | 103 |
| L2 | 9 | 347 |
| E6 | 9 | 43 |
| E2 | 9 | 137 |
| L1 | 10 | 287 |
| E2 | 8 | 157 |
| E2 | 11 | 157 |
| L1 | 9 | 79 |
| L1 | 10 | 79 |
| E2 | 10 | 120 |
| E1 | 8 | 211 |
| E1 | 10 | 211 |
| E1 | 8 | 493 |
| E1 | 10 | 493 |
| L1 | 8 | 463 |
| L1 | 9 | 450 |
| L1 | 11 | 450 |
| E6 | 8 | 73 |
| E6 | 10 | 73 |
| E1 | 9 | 312 |
| E1 | 10 | 312 |
| E1 | 11 | 312 |
| E1 | 8 | 254 |
| E1 | 9 | 254 |
| E6 | 11 | 116 |
| E6 | 11 | 128 |

TABLE X C-continued

HPV11
HLA-A24 Supermotif Peptides

| 2 | 3 | 4 |
|---|---|---|
| E1 | 8 | 357 |
| E1 | 10 | 357 |
| E1 | 8 | 420 |
| E1 | 10 | 420 |
| E4 | 8 | 53 |
| E6 | 10 | 18 |
| E2 | 9 | 84 |
| E2 | 11 | 84 |
| L1 | 10 | 56 |
| E7 | 10 | 39 |
| E1 | 8 | 433 |
| E1 | 11 | 433 |
| L2 | 11 | 33 |
| E2 | 9 | 358 |
| E2 | 10 | 358 |
| E6 | 8 | 99 |
| L1 | 10 | 61 |
| E2 | 11 | 147 |
| L1 | 8 | 19 |
| L1 | 10 | 71 |
| E6 | 8 | 52 |
| E6 | 10 | 52 |
| L2 | 8 | 45 |
| L2 | 9 | 45 |
| L1 | 11 | 122 |
| E2 | 8 | 177 |
| E2 | 8 | 306 |
| E1 | 11 | 85 |
| E1 | 10 | 578 |
| L1 | 8 | 227 |
| E4 | 8 | 28 |
| E1 | 8 | 401 |
| E1 | 9 | 401 |
| E4 | 8 | 8 |
| E4 | 9 | 8 |
| E4 | 11 | 8 |
| L1 | 9 | 87 |
| L1 | 11 | 87 |
| E2 | 9 | 310 |
| E2 | 11 | 310 |
| L1 | 10 | 243 |
| L1 | 11 | 243 |
| E5 | 9 | 15 |
| L1 | 8 | 303 |
| E1 | 11 | 66 |
| E5 | 10 | 19 |
| L2 | 8 | 158 |
| L2 | 8 | 106 |
| E1 | 8 | 255 |
| E1 | 11 | 255 |
| E5 | 8 | 33 |
| E5 | 11 | 33 |
| E1 | 8 | 557 |
| E1 | 10 | 491 |
| E5 | 9 | 16 |
| E6 | 11 | 101 |
| E5 | 8 | 36 |
| L1 | 11 | 187 |
| L1 | 8 | 41 |
| L1 | 9 | 41 |
| L1 | 11 | 41 |
| E1 | 10 | 521 |
| E1 | 9 | 540 |
| E2 | 10 | 15 |
| E7 | 11 | 83 |
| E2 | 8 | 42 |
| E2 | 10 | 42 |
| E4 | 8 | 18 |
| E4 | 9 | 18 |
| E1 | 11 | 198 |
| E7 | 8 | 82 |
| E5 | 9 | 59 |
| E5 | 10 | 59 |
| E5 | 11 | 59 |

TABLE X C-continued

HPV11
HLA-A24 Supermotif Peptides

| 2 | 3 | 4 |
|---|---|---|
| E5 | 11 | 55 |
| E5 | 8 | 51 |
| E5 | 9 | 51 |
| E5 | 10 | 51 |
| E5 | 11 | 51 |
| E1 | 9 | 298 |
| E1 | 10 | 298 |
| E1 | 11 | 298 |
| E5 | 8 | 69 |
| E5 | 9 | 69 |
| E5 | 8 | 60 |
| E5 | 9 | 60 |
| E5 | 10 | 60 |
| E5 | 11 | 60 |
| E1 | 9 | 563 |
| E5 | 10 | 56 |
| E5 | 8 | 52 |
| E5 | 9 | 52 |
| E5 | 10 | 52 |
| E5 | 11 | 4 |
| E1 | 8 | 514 |
| E1 | 9 | 514 |
| E1 | 8 | 132 |
| E1 | 9 | 358 |
| E5 | 8 | 70 |
| E5 | 11 | 70 |
| E1 | 9 | 555 |
| E1 | 10 | 555 |
| E5 | 8 | 49 |
| E5 | 9 | 49 |
| E5 | 10 | 49 |
| E5 | 11 | 49 |
| E1 | 9 | 268 |
| E1 | 10 | 268 |
| E2 | 8 | 103 |
| E7 | 8 | 48 |
| L2 | 8 | 368 |
| E6 | 9 | 38 |
| E6 | 11 | 38 |
| E5 | 8 | 61 |
| E5 | 9 | 61 |
| E5 | 10 | 61 |
| L2 | 9 | 337 |
| L2 | 11 | 337 |
| E5 | 8 | 47 |
| E5 | 9 | 47 |
| E5 | 10 | 47 |
| E5 | 11 | 47 |
| L1 | 8 | 296 |
| L1 | 9 | 296 |
| E7 | 9 | 5 |
| E7 | 11 | 5 |
| E1 | 8 | 564 |
| L2 | 9 | 245 |
| E7 | 10 | 67 |
| L1 | 8 | 95 |
| E5 | 9 | 57 |
| E5 | 11 | 57 |
| E1 | 8 | 261 |
| E2 | 9 | 18 |
| E4 | 8 | 25 |
| E4 | 10 | 25 |
| E4 | 11 | 25 |
| E4 | 9 | 21 |
| E4 | 11 | 21 |
| E5 | 8 | 53 |
| E5 | 9 | 53 |
| E4 | 8 | 15 |
| E4 | 9 | 15 |
| E4 | 11 | 15 |
| E1 | 8 | 320 |
| E1 | 8 | 306 |
| E1 | 10 | 47 |
| L1 | 9 | 197 |

TABLE X C-continued

HPV11
HLA-A24 Supermotif Peptides

| 2 | 3 | 4 |
|---|---|---|
| L1 | 11 | 197 |
| L1 | 8 | 155 |
| E1 | 9 | 274 |
| E5 | 8 | 1 |
| E1 | 10 | 361 |
| E4 | 9 | 1 |
| E4 | 11 | 1 |
| E2 | 10 | 101 |
| L1 | 10 | 1 |
| L2 | 9 | 304 |
| E2 | 9 | 170 |
| E6 | 11 | 58 |
| E1 | 10 | 568 |
| E1 | 8 | 451 |
| E1 | 11 | 451 |
| L1 | 11 | 31 |
| E1 | 8 | 300 |
| E1 | 9 | 300 |
| E2 | 9 | 254 |
| L1 | 10 | 446 |
| E6 | 10 | 50 |
| E1 | 8 | 539 |
| E1 | 10 | 539 |
| E6 | 9 | 21 |
| E2 | 8 | 248 |
| E5 | 8 | 54 |
| E5 | 9 | 54 |
| L2 | 8 | 381 |
| E1 | 10 | 97 |
| L1 | 11 | 143 |
| E2 | 8 | 127 |
| E2 | 11 | 127 |
| E1 | 9 | 609 |
| E1 | 8 | 439 |
| E1 | 9 | 439 |
| E6 | 9 | 60 |
| E6 | 11 | 60 |
| E1 | 10 | 594 |
| E1 | 8 | 456 |
| E1 | 9 | 456 |
| E1 | 10 | 456 |
| L2 | 9 | 410 |
| E4 | 8 | 4 |
| E1 | 11 | 442 |
| E6 | 8 | 110 |
| E6 | 11 | 110 |
| L1 | 11 | 218 |
| L1 | 9 | 184 |
| L2 | 9 | 157 |
| L1 | 8 | 459 |
| L2 | 10 | 72 |
| L1 | 11 | 109 |
| E1 | 8 | 562 |
| E1 | 10 | 562 |
| E5 | 9 | 64 |
| L2 | 8 | 385 |
| L2 | 9 | 385 |
| E1 | 8 | 258 |
| E1 | 10 | 258 |
| E1 | 11 | 258 |
| E1 | 9 | 513 |
| E1 | 10 | 513 |
| E7 | 8 | 47 |
| E7 | 9 | 47 |
| E4 | 8 | 68 |
| L2 | 10 | 336 |
| E1 | 11 | 545 |
| L2 | 9 | 403 |
| E2 | 9 | 353 |
| E2 | 10 | 353 |
| L2 | 11 | 182 |
| L1 | 11 | 427 |
| L2 | 8 | 123 |
| L2 | 11 | 206 |
| L1 | 8 | 90 |
| E6 | 11 | 87 |
| L2 | 9 | 95 |
| L2 | 8 | 170 |
| L2 | 9 | 170 |
| L2 | 10 | 170 |
| L2 | 9 | 422 |
| L2 | 10 | 422 |
| L2 | 11 | 422 |
| E7 | 10 | 20 |
| L2 | 10 | 358 |
| L2 | 11 | 358 |
| L1 | 11 | 16 |
| L2 | 9 | 324 |
| L2 | 11 | 324 |
| E5 | 10 | 19 |
| E5 | 11 | 19 |
| L2 | 10 | 251 |
| E2 | 9 | 91 |
| E2 | 11 | 91 |
| E4 | 11 | 80 |
| L1 | 8 | 238 |
| L1 | 9 | 238 |
| L1 | 10 | 238 |
| L1 | 8 | 436 |
| E5 | 11 | 66 |
| L1 | 9 | 369 |
| L1 | 11 | 369 |
| E1 | 10 | 355 |
| E2 | 9 | 163 |
| E2 | 8 | 344 |
| E1 | 8 | 445 |
| E1 | 10 | 445 |
| E1 | 11 | 445 |
| L1 | 8 | 457 |
| L1 | 9 | 457 |
| L1 | 10 | 457 |
| E5 | 10 | 7 |
| E5 | 11 | 7 |
| L2 | 8 | 42 |
| L2 | 11 | 42 |
| E6 | 11 | 28 |
| E6 | 8 | 15 |
| E6 | 10 | 15 |
| L1 | 11 | 152 |
| L1 | 8 | 302 |
| L1 | 9 | 302 |
| E2 | 11 | 14 |
| E7 | 10 | 78 |
| E2 | 9 | 288 |
| E4 | 8 | 14 |
| E4 | 9 | 14 |
| E4 | 10 | 14 |
| L1 | 11 | 233 |
| L1 | 8 | 251 |
| E2 | 9 | 48 |
| L1 | 9 | 211 |
| L1 | 11 | 211 |
| E1 | 8 | 344 |
| L2 | 9 | 230 |
| L2 | 10 | 230 |
| L2 | 8 | 232 |
| E1 | 8 | 363 |
| E6 | 10 | 132 |
| E1 | 9 | 266 |
| E1 | 11 | 266 |
| E2 | 9 | 86 |
| E6 | 10 | 76 |
| L1 | 9 | 66 |
| E6 | 9 | 125 |
| L2 | 11 | 294 |
| L2 | 8 | 297 |
| L2 | 9 | 297 |
| L2 | 8 | 315 |

TABLE X C-continued

HPV11
HLA-A24 Supermotif Peptides

| 2 | 3 | 4 |
|---|---|---|
| E2 | 9 | 7 |
| E2 | 10 | 7 |
| E1 | 8 | 125 |
| L1 | 11 | 242 |
| E4 | 11 | 59 |
| L1 | 9 | 40 |
| L1 | 10 | 40 |
| E2 | 9 | 302 |
| E2 | 10 | 302 |
| E1 | 8 | 616 |
| E7 | 8 | 4 |
| E7 | 10 | 4 |
| L2 | 10 | 244 |
| E7 | 11 | 66 |
| L1 | 9 | 94 |
| E1 | 11 | 324 |
| E1 | 9 | 293 |
| L1 | 8 | 473 |
| L2 | 9 | 220 |
| L1 | 8 | 141 |
| E1 | 11 | 583 |
| E2 | 8 | 300 |
| E2 | 11 | 300 |
| L1 | 8 | 415 |
| E1 | 9 | 219 |
| L1 | 11 | 441 |
| E1 | 9 | 247 |
| E1 | 10 | 247 |
| E2 | 8 | 207 |
| E2 | 8 | 23 |
| E2 | 9 | 23 |
| E2 | 11 | 23 |
| E6 | 9 | 12 |
| E6 | 11 | 12 |
| E1 | 9 | 547 |
| E1 | 11 | 547 |
| L2 | 10 | 266 |
| L2 | 11 | 266 |
| E1 | 8 | 422 |
| L1 | 9 | 376 |
| L1 | 11 | 376 |
| E5 | 8 | 30 |
| E5 | 11 | 30 |
| L2 | 11 | 102 |
| L1 | 11 | 286 |
| E1 | 9 | 350 |
| L1 | 10 | 86 |
| L2 | 9 | 48 |
| L2 | 11 | 48 |
| E6 | 11 | 23 |
| L2 | 8 | 105 |
| L2 | 9 | 105 |
| E1 | 11 | 490 |
| L2 | 9 | 259 |
| L1 | 9 | 295 |
| L1 | 10 | 295 |
| E1 | 8 | 260 |
| E1 | 9 | 260 |
| L2 | 10 | 303 |
| E2 | 11 | 260 |
| E1 | 11 | 206 |
| E2 | 9 | 180 |
| E2 | 11 | 245 |
| L2 | 8 | 209 |
| L2 | 10 | 370 |
| L2 | 9 | 240 |
| E1 | 11 | 185 |
| E6 | 10 | 7 |
| E4 | 8 | 85 |
| E1 | 10 | 331 |
| E1 | 11 | 331 |
| E2 | 8 | 201 |
| E2 | 8 | 151 |
| E2 | 9 | 151 |

TABLE X C-continued

HPV11
HLA-A24 Supermotif Peptides

| 2 | 3 | 4 |
|---|---|---|
| E2 | 9 | 257 |
| E1 | 8 | 60 |
| L2 | 8 | 152 |
| E1 | 8 | 436 |
| E1 | 11 | 436 |
| L1 | 8 | 190 |
| E2 | 8 | 348 |
| L1 | 8 | 393 |
| L1 | 10 | 393 |
| E2 | 10 | 40 |
| E5 | 8 | 45 |
| E5 | 9 | 45 |
| E5 | 10 | 45 |
| E5 | 11 | 45 |
| L1 | 10 | 176 |
| L1 | 8 | 344 |
| E2 | 11 | 198 |
| L2 | 11 | 144 |
| L2 | 9 | 378 |
| L2 | 11 | 378 |
| L2 | 10 | 366 |
| E1 | 9 | 501 |
| E1 | 10 | 501 |
| E1 | 11 | 501 |
| L2 | 9 | 344 |
| E6 | 9 | 19 |
| E6 | 11 | 19 |
| E1 | 8 | 588 |
| L2 | 11 | 401 |
| E1 | 8 | 586 |
| E1 | 10 | 586 |
| L2 | 9 | 38 |
| E2 | 10 | 261 |
| E2 | 8 | 354 |
| E2 | 9 | 354 |
| E2 | 11 | 354 |
| L2 | 10 | 183 |
| E5 | 10 | 71 |
| E5 | 11 | 71 |
| L1 | 8 | 409 |
| E1 | 8 | 294 |
| E1 | 10 | 207 |
| E1 | 8 | 556 |
| E1 | 9 | 556 |
| E5 | 8 | 15 |
| E5 | 10 | 15 |
| E7 | 9 | 7 |
| E5 | 8 | 50 |
| E5 | 9 | 50 |
| E5 | 10 | 50 |
| E5 | 11 | 50 |
| E1 | 10 | 297 |
| E1 | 11 | 297 |
| E7 | 8 | 86 |
| E2 | 9 | 93 |
| E2 | 10 | 93 |
| E2 | 11 | 93 |
| E6 | 8 | 26 |
| L1 | 9 | 378 |
| L1 | 10 | 378 |
| L1 | 10 | 389 |
| E6 | 8 | 39 |
| E6 | 10 | 39 |
| E1 | 11 | 232 |
| E6 | 8 | 142 |
| E1 | 9 | 585 |
| E1 | 11 | 585 |
| L2 | 8 | 37 |
| L2 | 10 | 37 |
| E5 | 9 | 14 |
| E5 | 11 | 14 |
| E5 | 8 | 62 |
| E5 | 9 | 62 |
| E5 | 11 | 62 |

TABLE X C-continued

HPV11
HLA-A24 Supermotif Peptides

| 2 | 3 | 4 |
|---|---|---|
| E1 | 11 | 116 |
| L1 | 9 | 333 |
| L2 | 9 | 150 |
| L2 | 10 | 150 |
| E5 | 10 | 13 |
| L2 | 10 | 149 |
| L2 | 11 | 149 |
| E5 | 11 | 12 |
| L2 | 8 | 55 |
| L2 | 11 | 382 |
| E4 | 9 | 100 |
| E1 | 9 | 290 |
| E1 | 10 | 290 |
| L1 | 8 | 224 |
| L1 | 9 | 224 |
| L1 | 11 | 224 |
| E6 | 10 | 88 |
| E6 | 11 | 88 |
| L1 | 10 | 263 |
| L1 | 11 | 263 |
| E1 | 9 | 332 |
| E1 | 10 | 332 |
| L2 | 10 | 383 |
| L2 | 11 | 383 |
| E1 | 9 | 78 |
| E1 | 10 | 78 |
| E4 | 9 | 82 |
| E4 | 11 | 82 |
| E2 | 11 | 63 |
| E4 | 8 | 101 |
| L1 | 11 | 329 |
| L1 | 9 | 57 |
| L1 | 11 | 57 |
| E5 | 8 | 13 |
| E5 | 11 | 13 |
| E1 | 10 | 531 |
| E1 | 11 | 531 |
| L1 | 10 | 413 |
| E2 | 11 | 335 |
| L1 | 10 | 350 |
| L1 | 11 | 350 |
| L2 | 8 | 51 |
| L2 | 8 | 423 |
| L2 | 9 | 423 |
| L2 | 10 | 423 |
| E5 | 8 | 21 |
| E5 | 9 | 21 |
| E5 | 11 | 21 |
| E1 | 11 | 346 |
| E1 | 8 | 333 |
| E1 | 9 | 333 |
| L2 | 10 | 30 |
| E1 | 11 | 499 |
| L1 | 9 | 394 |
| E5 | 9 | 27 |
| E5 | 9 | 32 |
| E2 | 9 | 41 |
| E2 | 11 | 41 |
| E4 | 9 | 17 |
| E4 | 10 | 17 |
| E1 | 8 | 275 |
| L1 | 8 | 73 |
| L1 | 10 | 73 |
| E5 | 8 | 48 |
| E5 | 9 | 48 |
| E5 | 10 | 48 |
| E5 | 11 | 48 |
| E5 | 8 | 46 |
| E5 | 9 | 46 |
| E5 | 10 | 46 |
| E5 | 11 | 46 |
| E4 | 9 | 10 |
| E4 | 10 | 10 |
| L1 | 8 | 383 |
| E2 | 10 | 128 |
| E2 | 11 | 128 |
| E7 | 8 | 6 |
| E7 | 10 | 6 |
| L2 | 10 | 145 |
| L2 | 11 | 414 |
| L2 | 8 | 325 |
| L2 | 10 | 325 |
| E2 | 10 | 148 |
| E2 | 11 | 148 |
| E1 | 10 | 584 |
| L2 | 8 | 246 |
| E1 | 11 | 238 |
| E5 | 8 | 24 |
| E5 | 9 | 24 |
| E5 | 10 | 24 |
| L1 | 10 | 330 |
| E7 | 9 | 68 |
| E5 | 9 | 20 |
| E5 | 10 | 20 |
| L1 | 9 | 72 |
| L1 | 11 | 72 |
| E4 | 8 | 2 |
| E4 | 10 | 2 |
| L1 | 8 | 58 |
| L1 | 10 | 58 |
| L2 | 9 | 120 |
| L2 | 11 | 120 |
| E6 | 9 | 53 |
| E2 | 8 | 132 |
| E5 | 9 | 41 |
| E5 | 11 | 41 |
| E4 | 8 | 74 |
| E6 | 8 | 54 |
| L2 | 9 | 252 |
| L2 | 11 | 252 |
| E1 | 9 | 602 |
| E5 | 11 | 60 |
| E5 | 8 | 42 |
| E5 | 10 | 42 |
| E5 | 11 | 42 |
| L2 | 9 | 392 |
| L2 | 11 | 392 |
| E1 | 8 | 340 |
| E5 | 10 | 14 |
| E5 | 11 | 18 |
| E1 | 11 | 464 |
| E5 | 8 | 58 |
| E5 | 10 | 58 |
| E5 | 11 | 58 |
| E1 | 8 | 267 |
| E1 | 10 | 267 |
| E1 | 11 | 267 |
| E2 | 9 | 102 |
| E2 | 8 | 92 |
| E2 | 10 | 92 |
| E2 | 11 | 92 |
| E6 | 8 | 141 |
| E6 | 9 | 141 |
| E4 | 10 | 81 |
| E1 | 8 | 530 |
| E1 | 11 | 530 |
| E1 | 8 | 237 |
| L2 | 11 | 436 |
| L2 | 10 | 437 |
| E5 | 9 | 76 |
| E5 | 10 | 76 |
| E5 | 11 | 76 |
| L1 | 10 | 386 |
| E4 | 8 | 22 |
| E4 | 10 | 22 |
| E4 | 11 | 22 |
| E6 | 10 | 105 |
| E1 | 10 | 86 |

TABLE X C-continued

HPV11
HLA-A24 Supermotif Peptides

| 2 | 3 | 4 |
|---|---|---|
| L2 | 8 | 431 |
| E1 | 9 | 579 |
| E1 | 11 | 579 |
| E5 | 8 | 54 |
| E2 | 8 | 138 |
| L1 | 9 | 231 |
| L1 | 8 | 246 |
| L2 | 9 | 367 |
| E1 | 9 | 532 |
| E1 | 10 | 532 |
| L1 | 8 | 359 |
| L1 | 10 | 359 |
| E1 | 11 | 536 |
| E5 | 10 | 61 |
| E2 | 9 | 159 |
| E2 | 10 | 159 |
| L1 | 9 | 351 |
| L1 | 10 | 351 |
| L2 | 8 | 305 |
| E5 | 9 | 43 |
| E5 | 10 | 43 |
| E5 | 11 | 43 |
| L1 | 9 | 288 |
| E1 | 8 | 402 |
| L1 | 8 | 26 |
| L1 | 9 | 26 |
| E4 | 8 | 16 |
| E4 | 10 | 16 |
| E4 | 11 | 16 |
| E4 | 8 | 9 |
| E4 | 10 | 9 |
| E4 | 11 | 9 |
| E2 | 11 | 168 |
| E1 | 8 | 502 |
| E1 | 9 | 502 |
| E1 | 10 | 502 |
| E2 | 8 | 131 |
| E2 | 9 | 131 |
| E2 | 10 | 158 |
| E2 | 11 | 158 |

TABLE XI

HLA-B7 Supermotif Peptides

| 1 | 2 | 3 | 4 |
|---|---|---|---|
| HPV16 | E1 | 10 | 559 |
| HPV16 | E1 | 9 | 308 |
| HPV16 | E1 | 10 | 308 |
| HPV16 | E1 | 11 | 308 |
| HPV16 | E1 | 10 | 592 |
| HPV16 | E1 | 11 | 592 |
| HPV16 | E1 | 8 | 467 |
| HPV16 | E1 | 9 | 467 |
| HPV16 | E1 | 10 | 467 |
| HPV16 | E1 | 11 | 599 |
| HPV16 | E1 | 8 | 309 |
| HPV16 | E1 | 9 | 309 |
| HPV16 | E1 | 10 | 309 |
| HPV16 | E1 | 11 | 309 |
| HPV16 | E1 | 9 | 560 |
| HPV16 | E1 | 11 | 560 |
| HPV16 | E1 | 8 | 511 |
| HPV16 | E1 | 10 | 511 |
| HPV16 | E1 | 11 | 511 |
| HPV16 | E1 | 11 | 552 |
| HPV16 | E1 | 10 | 93 |
| HPV16 | E1 | 9 | 107 |
| HPV16 | E1 | 10 | 336 |
| HPV16 | E1 | 11 | 336 |

TABLE XI-continued

HLA-B7 Supermotif Peptides

| 1 | 2 | 3 | 4 |
|---|---|---|---|
| HPV16 | E1 | 9 | 189 |
| HPV16 | E1 | 10 | 189 |
| HPV16 | E1 | 8 | 244 |
| HPV16 | E1 | 11 | 244 |
| HPV16 | E1 | 11 | 526 |
| HPV16 | E1 | 8 | 576 |
| HPV16 | E1 | 9 | 576 |
| HPV16 | E1 | 10 | 576 |
| HPV16 | E1 | 11 | 576 |
| HPV16 | E2 | 11 | 105 |
| HPV16 | E2 | 11 | 195 |
| HPV16 | E2 | 9 | 218 |
| HPV16 | E2 | 10 | 218 |
| HPV16 | E2 | 11 | 218 |
| HPV16 | E2 | 11 | 352 |
| HPV16 | E2 | 8 | 249 |
| HPV16 | E2 | 9 | 249 |
| HPV16 | E2 | 9 | 207 |
| HPV16 | E2 | 10 | 207 |
| HPV16 | E2 | 10 | 286 |
| HPV16 | E2 | 11 | 59 |
| HPV16 | E5 | 10 | 69 |
| HPV16 | E5 | 10 | 30 |
| HPV16 | E6 | 9 | 118 |
| HPV16 | E6 | 9 | 11 |
| HPV16 | E6 | 8 | 101 |
| HPV16 | E6 | 11 | 101 |
| HPV16 | E6 | 8 | 19 |
| HPV16 | E6 | 10 | 65 |
| HPV16 | E6 | 8 | 15 |
| HPV16 | E7 | 9 | 46 |
| HPV16 | E7 | 10 | 46 |
| HPV16 | E7 | 11 | 40 |
| HPV16 | E7 | 8 | 16 |
| HPV16 | E7 | 10 | 16 |
| HPV16 | E7 | 8 | 5 |
| HPV16 | E7 | 9 | 5 |
| HPV16 | E7 | 11 | 5 |
| HPV16 | L1 | 10 | 461 |
| HPV16 | L1 | 10 | 211 |
| HPV16 | L1 | 11 | 211 |
| HPV16 | L1 | 8 | 465 |
| HPV16 | L1 | 9 | 465 |
| HPV16 | L1 | 11 | 465 |
| HPV16 | L1 | 8 | 266 |
| HPV16 | L1 | 9 | 266 |
| HPV16 | L1 | 10 | 266 |
| HPV16 | L1 | 11 | 266 |
| HPV16 | L1 | 11 | 76 |
| HPV16 | L1 | 8 | 488 |
| HPV16 | L1 | 9 | 488 |
| HPV16 | L1 | 11 | 488 |
| HPV16 | L1 | 8 | 318 |
| HPV16 | L1 | 9 | 318 |
| HPV16 | L1 | 11 | 503 |
| HPV16 | L1 | 8 | 80 |
| HPV16 | L1 | 9 | 80 |
| HPV16 | L1 | 8 | 188 |
| HPV16 | L1 | 8 | 335 |
| HPV16 | L1 | 9 | 103 |
| HPV16 | L1 | 9 | 39 |
| HPV16 | L1 | 10 | 39 |
| HPV16 | L1 | 8 | 31 |
| HPV16 | L1 | 9 | 31 |
| HPV16 | L1 | 8 | 118 |
| HPV16 | L1 | 9 | 118 |
| HPV16 | L1 | 10 | 118 |
| HPV16 | L1 | 8 | 207 |
| HPV16 | L1 | 10 | 207 |
| HPV16 | L1 | 11 | 207 |
| HPV16 | L1 | 9 | 459 |
| HPV16 | L1 | 10 | 435 |
| HPV16 | L1 | 9 | 212 |
| HPV16 | L1 | 10 | 212 |
| HPV16 | L1 | 11 | 434 |

TABLE XI-continued

HLA-B7 Supermotif Peptides

| 1 | 2 | 3 | 4 |
|---|---|---|---|
| HPV16 | L1 | 8 | 40 |
| HPV16 | L1 | 9 | 40 |
| HPV16 | L1 | 8 | 433 |
| HPV16 | L1 | 8 | 199 |
| HPV16 | L1 | 10 | 458 |
| HPV16 | L1 | 11 | 320 |
| HPV16 | L1 | 11 | 514 |
| HPV16 | L1 | 9 | 88 |
| HPV16 | L1 | 11 | 88 |
| HPV16 | L1 | 9 | 246 |
| HPV16 | L1 | 8 | 257 |
| HPV16 | L2 | 9 | 278 |
| HPV16 | L2 | 10 | 278 |
| HPV16 | L2 | 11 | 278 |
| HPV16 | L2 | 8 | 424 |
| HPV16 | L2 | 8 | 119 |
| HPV16 | L2 | 9 | 87 |
| HPV16 | L2 | 9 | 28 |
| HPV16 | L2 | 11 | 239 |
| HPV16 | L2 | 8 | 280 |
| HPV16 | L2 | 9 | 280 |
| HPV16 | L2 | 10 | 280 |
| HPV16 | L2 | 8 | 102 |
| HPV16 | L2 | 11 | 165 |
| HPV16 | L2 | 10 | 96 |
| HPV16 | L2 | 11 | 96 |
| HPV16 | L2 | 8 | 413 |
| HPV16 | L2 | 8 | 99 |
| HPV16 | L2 | 10 | 99 |
| HPV16 | L2 | 11 | 99 |
| HPV16 | L2 | 9 | 394 |
| HPV16 | L2 | 9 | 400 |
| HPV16 | L2 | 11 | 400 |
| HPV16 | L2 | 8 | 216 |
| HPV16 | L2 | 10 | 216 |
| HPV16 | L2 | 9 | 416 |
| HPV16 | L2 | 10 | 428 |
| HPV16 | L2 | 9 | 33 |
| HPV16 | L2 | 10 | 33 |
| HPV16 | L2 | 10 | 73 |
| HPV16 | L2 | 9 | 408 |
| HPV16 | L2 | 11 | 408 |
| HPV16 | L2 | 8 | 196 |
| HPV16 | L2 | 8 | 126 |
| HPV16 | L2 | 10 | 126 |
| HPV16 | L2 | 9 | 357 |
| HPV16 | L2 | 10 | 357 |
| HPV16 | L2 | 8 | 462 |
| HPV16 | L2 | 10 | 462 |
| HPV16 | L2 | 11 | 462 |
| HPV16 | L2 | 9 | 254 |
| HPV16 | L2 | 11 | 206 |
| HPV16 | L2 | 9 | 160 |
| HPV16 | L2 | 10 | 160 |
| HPV16 | L2 | 8 | 29 |
| HPV16 | L2 | 9 | 127 |
| HPV16 | L2 | 8 | 91 |
| HPV16 | L2 | 8 | 79 |
| HPV16 | L2 | 9 | 79 |
| HPV16 | L2 | 11 | 79 |
| HPV16 | L2 | 11 | 171 |
| HPV16 | L2 | 11 | 291 |
| HPV16 | L2 | 9 | 90 |
| HPV16 | L2 | 9 | 78 |
| HPV16 | L2 | 10 | 78 |
| HPV16 | L2 | 8 | 220 |
| HPV16 | L2 | 9 | 220 |
| HPV16 | L2 | 8 | 434 |
| HPV16 | L2 | 10 | 434 |
| HPV16 | L2 | 9 | 173 |
| HPV16 | L2 | 11 | 173 |
| HPV16 | L2 | 11 | 142 |
| HPV16 | L2 | 9 | 214 |
| HPV16 | L2 | 10 | 214 |
| HPV16 | L2 | 11 | 345 |
| HPV16 | L2 | 8 | 245 |
| HPV16 | L2 | 11 | 380 |
| HPV16 | L2 | 9 | 431 |
| HPV16 | L2 | 10 | 431 |
| HPV16 | L2 | 11 | 431 |
| HPV16 | L2 | 8 | 123 |
| HPV16 | L2 | 11 | 123 |
| HPV16 | L2 | 9 | 385 |
| HPV16 | L2 | 10 | 385 |
| HPV16 | L2 | 9 | 382 |
| HPV18 | E1 | 10 | 566 |
| HPV18 | E1 | 8 | 518 |
| HPV18 | E1 | 9 | 518 |
| HPV18 | E1 | 10 | 518 |
| HPV18 | E1 | 11 | 518 |
| HPV18 | E1 | 10 | 599 |
| HPV18 | E1 | 11 | 599 |
| HPV18 | E1 | 9 | 484 |
| HPV18 | E1 | 10 | 484 |
| HPV18 | E1 | 8 | 576 |
| HPV18 | E1 | 10 | 576 |
| HPV18 | E1 | 11 | 576 |
| HPV18 | E1 | 11 | 559 |
| HPV18 | E1 | 8 | 641 |
| HPV18 | E1 | 10 | 641 |
| HPV18 | E1 | 9 | 193 |
| HPV18 | E1 | 8 | 251 |
| HPV18 | E1 | 11 | 251 |
| HPV18 | E1 | 11 | 606 |
| HPV18 | E1 | 9 | 567 |
| HPV18 | E1 | 8 | 316 |
| HPV18 | E1 | 9 | 316 |
| HPV18 | E1 | 10 | 316 |
| HPV18 | E1 | 11 | 316 |
| HPV18 | E1 | 9 | 263 |
| HPV18 | E1 | 9 | 315 |
| HPV18 | E1 | 10 | 315 |
| HPV18 | E1 | 11 | 315 |
| HPV18 | E1 | 9 | 447 |
| HPV18 | E1 | 9 | 97 |
| HPV18 | E1 | 9 | 110 |
| HPV18 | E1 | 8 | 343 |
| HPV18 | E1 | 10 | 343 |
| HPV18 | E1 | 11 | 343 |
| HPV18 | E1 | 8 | 474 |
| HPV18 | E1 | 9 | 474 |
| HPV18 | E1 | 8 | 307 |
| HPV18 | E1 | 8 | 583 |
| HPV18 | E1 | 10 | 583 |
| HPV18 | E1 | 11 | 583 |
| HPV18 | E2 | 9 | 261 |
| HPV18 | E2 | 10 | 261 |
| HPV18 | E2 | 8 | 352 |
| HPV18 | E2 | 9 | 352 |
| HPV18 | E2 | 11 | 352 |
| HPV18 | E2 | 8 | 248 |
| HPV18 | E2 | 9 | 226 |
| HPV18 | E2 | 10 | 3 |
| HPV18 | E2 | 9 | 224 |
| HPV18 | E2 | 11 | 224 |
| HPV18 | E2 | 11 | 271 |
| HPV18 | E2 | 11 | 63 |
| HPV18 | E5 | 8 | 59 |
| HPV18 | E5 | 10 | 59 |
| HPV18 | E5 | 11 | 59 |
| HPV18 | E5 | 8 | 23 |
| HPV18 | E5 | 9 | 23 |
| HPV18 | E5 | 10 | 23 |
| HPV18 | E5 | 11 | 23 |
| HPV18 | E5 | 8 | 45 |
| HPV18 | E5 | 9 | 45 |
| HPV18 | E5 | 10 | 45 |
| HPV18 | E5 | 11 | 45 |
| HPV18 | E5 | 9 | 20 |
| HPV18 | E5 | 11 | 20 |

TABLE XI-continued

HLA-B7 Supermotif Peptides

| 1 | 2 | 3 | 4 |
|---|---|---|---|
| HPV18 | E6 | 9 | 6 |
| HPV18 | E6 | 10 | 60 |
| HPV18 | E6 | 9 | 110 |
| HPV18 | E6 | 8 | 14 |
| HPV18 | E6 | 9 | 113 |
| HPV18 | E6 | 8 | 10 |
| HPV18 | E7 | 8 | 16 |
| HPV18 | E7 | 10 | 16 |
| HPV18 | E7 | 11 | 16 |
| HPV18 | E7 | 8 | 55 |
| HPV18 | E7 | 10 | 55 |
| HPV18 | E7 | 9 | 3 |
| HPV18 | E7 | 10 | 3 |
| HPV18 | E7 | 11 | 3 |
| HPV18 | E7 | 11 | 21 |
| HPV18 | L1 | 9 | 495 |
| HPV18 | L1 | 8 | 223 |
| HPV18 | L1 | 9 | 223 |
| HPV18 | L1 | 11 | 549 |
| HPV18 | L1 | 10 | 246 |
| HPV18 | L1 | 11 | 246 |
| HPV18 | L1 | 8 | 501 |
| HPV18 | L1 | 9 | 501 |
| HPV18 | L1 | 11 | 501 |
| HPV18 | L1 | 8 | 301 |
| HPV18 | L1 | 9 | 301 |
| HPV18 | L1 | 11 | 301 |
| HPV18 | L1 | 8 | 56 |
| HPV18 | L1 | 9 | 56 |
| HPV18 | L1 | 10 | 56 |
| HPV18 | L1 | 9 | 19 |
| HPV18 | L1 | 11 | 19 |
| HPV18 | L1 | 10 | 543 |
| HPV18 | L1 | 10 | 23 |
| HPV18 | L1 | 11 | 23 |
| HPV18 | L1 | 9 | 123 |
| HPV18 | L1 | 11 | 123 |
| HPV18 | L1 | 8 | 557 |
| HPV18 | L1 | 10 | 557 |
| HPV18 | L1 | 11 | 539 |
| HPV18 | L1 | 8 | 370 |
| HPV18 | L1 | 9 | 138 |
| HPV18 | L1 | 8 | 27 |
| HPV18 | L1 | 9 | 27 |
| HPV18 | L1 | 10 | 27 |
| HPV18 | L1 | 11 | 27 |
| HPV18 | L1 | 8 | 15 |
| HPV18 | L1 | 9 | 74 |
| HPV18 | L1 | 10 | 74 |
| HPV18 | L1 | 9 | 343 |
| HPV18 | L1 | 10 | 343 |
| HPV18 | L1 | 8 | 153 |
| HPV18 | L1 | 9 | 153 |
| HPV18 | L1 | 10 | 153 |
| HPV18 | L1 | 8 | 108 |
| HPV18 | L1 | 9 | 247 |
| HPV18 | L1 | 10 | 247 |
| HPV18 | L1 | 8 | 469 |
| HPV18 | L1 | 9 | 469 |
| HPV18 | L1 | 8 | 75 |
| HPV18 | L1 | 9 | 75 |
| HPV18 | L1 | 8 | 470 |
| HPV18 | L1 | 11 | 470 |
| HPV18 | L1 | 8 | 76 |
| HPV18 | L1 | 10 | 471 |
| HPV18 | L1 | 8 | 25 |
| HPV18 | L1 | 9 | 25 |
| HPV18 | L1 | 10 | 25 |
| HPV18 | L1 | 11 | 25 |
| HPV18 | L1 | 11 | 239 |
| HPV18 | L1 | 8 | 66 |
| HPV18 | L1 | 9 | 66 |
| HPV18 | L1 | 8 | 353 |
| HPV18 | L1 | 9 | 353 |
| HPV18 | L1 | 9 | 411 |
| HPV18 | L1 | 8 | 398 |
| HPV18 | L1 | 10 | 398 |
| HPV18 | L1 | 9 | 90 |
| HPV18 | L1 | 11 | 113 |
| HPV18 | L1 | 10 | 413 |
| HPV18 | L1 | 9 | 281 |
| HPV18 | L1 | 9 | 468 |
| HPV18 | L1 | 10 | 468 |
| HPV18 | L1 | 9 | 292 |
| HPV18 | L1 | 8 | 524 |
| HPV18 | L1 | 9 | 524 |
| HPV18 | L1 | 11 | 524 |
| HPV18 | L2 | 8 | 421 |
| HPV18 | L2 | 10 | 421 |
| HPV18 | L2 | 9 | 327 |
| HPV18 | L2 | 9 | 27 |
| HPV18 | L2 | 11 | 266 |
| HPV18 | L2 | 8 | 100 |
| HPV18 | L2 | 8 | 208 |
| HPV18 | L2 | 11 | 208 |
| HPV18 | L2 | 9 | 257 |
| HPV18 | L2 | 10 | 94 |
| HPV18 | L2 | 11 | 94 |
| HPV18 | L2 | 8 | 223 |
| HPV18 | L2 | 9 | 223 |
| HPV18 | L2 | 8 | 97 |
| HPV18 | L2 | 10 | 97 |
| HPV18 | L2 | 11 | 97 |
| HPV18 | L2 | 8 | 85 |
| HPV18 | L2 | 9 | 85 |
| HPV18 | L2 | 8 | 444 |
| HPV18 | L2 | 10 | 444 |
| HPV18 | L2 | 11 | 444 |
| HPV18 | L2 | 10 | 72 |
| HPV18 | L2 | 11 | 72 |
| HPV18 | L2 | 8 | 407 |
| HPV18 | L2 | 10 | 407 |
| HPV18 | L2 | 11 | 407 |
| HPV18 | L2 | 8 | 215 |
| HPV18 | L2 | 11 | 253 |
| HPV18 | L2 | 9 | 159 |
| HPV18 | L2 | 10 | 159 |
| HPV18 | L2 | 11 | 238 |
| HPV18 | L2 | 8 | 28 |
| HPV18 | L2 | 8 | 89 |
| HPV18 | L2 | 11 | 284 |
| HPV18 | L2 | 9 | 88 |
| HPV18 | L2 | 8 | 244 |
| HPV18 | L2 | 10 | 119 |
| HPV18 | L2 | 10 | 329 |
| HPV18 | L2 | 11 | 329 |
| HPV18 | L2 | 9 | 324 |
| HPV18 | L2 | 10 | 324 |
| HPV18 | L2 | 10 | 418 |
| HPV18 | L2 | 11 | 418 |
| HPV18 | L2 | 10 | 375 |
| HPV18 | L2 | 9 | 213 |
| HPV18 | L2 | 10 | 213 |
| HPV18 | L2 | 9 | 144 |
| HPV18 | L2 | 9 | 184 |
| HPV18 | L2 | 9 | 271 |
| HPV18 | L2 | 10 | 271 |
| HPV18 | L2 | 9 | 32 |
| HPV18 | L2 | 10 | 32 |
| HPV18 | L2 | 9 | 389 |
| HPV18 | L2 | 11 | 389 |
| HPV18 | L2 | 8 | 170 |
| HPV18 | L2 | 11 | 170 |
| HPV18 | L2 | 9 | 361 |
| HPV18 | L2 | 10 | 361 |
| HPV18 | L2 | 11 | 361 |
| HPV18 | L2 | 11 | 359 |
| HPV18 | L2 | 9 | 397 |
| HPV18 | L2 | 11 | 397 |
| HPV18 | L2 | 9 | 451 |

TABLE XI-continued

HLA-B7 Supermotif Peptides

| 1 | 2 | 3 | 4 |
|---|---|---|---|
| HPV18 | L2 | 10 | 451 |
| HPV18 | L2 | 11 | 451 |
| HPV18 | L2 | 8 | 414 |
| HPV18 | L2 | 10 | 414 |
| HPV31 | E1 | 8 | 458 |
| HPV31 | E1 | 9 | 458 |
| HPV31 | E1 | 11 | 458 |
| HPV31 | E1 | 10 | 539 |
| HPV31 | E1 | 10 | 572 |
| HPV31 | E1 | 11 | 572 |
| HPV31 | E1 | 11 | 128 |
| HPV31 | E1 | 11 | 523 |
| HPV31 | E1 | 11 | 579 |
| HPV31 | E1 | 8 | 289 |
| HPV31 | E1 | 9 | 289 |
| HPV31 | E1 | 10 | 289 |
| HPV31 | E1 | 11 | 289 |
| HPV31 | E1 | 9 | 540 |
| HPV31 | E1 | 11 | 540 |
| HPV31 | E1 | 8 | 491 |
| HPV31 | E1 | 10 | 491 |
| HPV31 | E1 | 11 | 491 |
| HPV31 | E1 | 9 | 288 |
| HPV31 | E1 | 10 | 288 |
| HPV31 | E1 | 11 | 288 |
| HPV31 | E1 | 9 | 236 |
| HPV31 | E1 | 10 | 92 |
| HPV31 | E1 | 9 | 106 |
| HPV31 | E1 | 10 | 506 |
| HPV31 | E1 | 11 | 506 |
| HPV31 | E1 | 10 | 316 |
| HPV31 | E1 | 11 | 316 |
| HPV31 | E1 | 9 | 169 |
| HPV31 | E1 | 10 | 169 |
| HPV31 | E1 | 8 | 447 |
| HPV31 | E1 | 9 | 447 |
| HPV31 | E1 | 8 | 556 |
| HPV31 | E1 | 9 | 556 |
| HPV31 | E1 | 10 | 556 |
| HPV31 | E1 | 11 | 556 |
| HPV31 | E2 | 11 | 105 |
| HPV31 | E2 | 8 | 289 |
| HPV31 | E2 | 10 | 289 |
| HPV31 | E2 | 11 | 195 |
| HPV31 | E2 | 11 | 257 |
| HPV31 | E2 | 11 | 359 |
| HPV31 | E2 | 10 | 293 |
| HPV31 | E2 | 9 | 59 |
| HPV31 | E2 | 11 | 59 |
| HPV31 | E5 | 10 | 69 |
| HPV31 | E5 | 9 | 30 |
| HPV31 | E5 | 10 | 30 |
| HPV31 | E5 | 11 | 30 |
| HPV31 | E5 | 8 | 55 |
| HPV31 | E5 | 9 | 55 |
| HPV31 | E5 | 10 | 55 |
| HPV31 | E5 | 11 | 55 |
| HPV31 | E6 | 9 | 111 |
| HPV31 | E6 | 8 | 21 |
| HPV31 | E6 | 11 | 21 |
| HPV31 | E6 | 9 | 4 |
| HPV31 | E6 | 8 | 8 |
| HPV31 | E6 | 11 | 8 |
| HPV31 | E6 | 8 | 142 |
| HPV31 | E6 | 10 | 58 |
| HPV31 | E7 | 8 | 91 |
| HPV31 | E7 | 9 | 46 |
| HPV31 | E7 | 10 | 46 |
| HPV31 | E7 | 10 | 28 |
| HPV31 | E7 | 11 | 28 |
| HPV31 | E7 | 10 | 16 |
| HPV31 | E7 | 8 | 5 |
| HPV31 | E7 | 9 | 5 |
| HPV31 | E7 | 11 | 5 |
| HPV31 | L1 | 10 | 433 |
| HPV31 | L1 | 10 | 488 |
| HPV31 | L1 | 10 | 186 |
| HPV31 | L1 | 11 | 186 |
| HPV31 | L1 | 8 | 440 |
| HPV31 | L1 | 9 | 440 |
| HPV31 | L1 | 11 | 440 |
| HPV31 | L1 | 8 | 241 |
| HPV31 | L1 | 9 | 241 |
| HPV31 | L1 | 10 | 241 |
| HPV31 | L1 | 11 | 241 |
| HPV31 | L1 | 8 | 463 |
| HPV31 | L1 | 9 | 463 |
| HPV31 | L1 | 11 | 463 |
| HPV31 | L1 | 8 | 293 |
| HPV31 | L1 | 9 | 293 |
| HPV31 | L1 | 10 | 139 |
| HPV31 | L1 | 10 | 52 |
| HPV31 | L1 | 11 | 52 |
| HPV31 | L1 | 10 | 436 |
| HPV31 | L1 | 11 | 436 |
| HPV31 | L1 | 8 | 163 |
| HPV31 | L1 | 8 | 310 |
| HPV31 | L1 | 9 | 78 |
| HPV31 | L1 | 9 | 13 |
| HPV31 | L1 | 10 | 13 |
| HPV31 | L1 | 8 | 396 |
| HPV31 | L1 | 10 | 396 |
| HPV31 | L1 | 8 | 93 |
| HPV31 | L1 | 9 | 93 |
| HPV31 | L1 | 10 | 93 |
| HPV31 | L1 | 10 | 57 |
| HPV31 | L1 | 9 | 187 |
| HPV31 | L1 | 10 | 187 |
| HPV31 | L1 | 10 | 410 |
| HPV31 | L1 | 8 | 14 |
| HPV31 | L1 | 9 | 14 |
| HPV31 | L1 | 11 | 478 |
| HPV31 | L1 | 8 | 5 |
| HPV31 | L1 | 9 | 5 |
| HPV31 | L1 | 8 | 174 |
| HPV31 | L1 | 8 | 182 |
| HPV31 | L1 | 10 | 182 |
| HPV31 | L1 | 11 | 409 |
| HPV31 | L1 | 11 | 295 |
| HPV31 | L1 | 9 | 63 |
| HPV31 | L1 | 11 | 63 |
| HPV31 | L1 | 9 | 221 |
| HPV31 | L1 | 8 | 232 |
| HPV31 | L1 | 9 | 232 |
| HPV31 | L2 | 9 | 271 |
| HPV31 | L2 | 10 | 271 |
| HPV31 | L2 | 11 | 271 |
| HPV31 | L2 | 8 | 240 |
| HPV31 | L2 | 8 | 414 |
| HPV31 | L2 | 10 | 414 |
| HPV31 | L2 | 11 | 414 |
| HPV31 | L2 | 9 | 424 |
| HPV31 | L2 | 10 | 424 |
| HPV31 | L2 | 11 | 424 |
| HPV31 | L2 | 9 | 28 |
| HPV31 | L2 | 8 | 273 |
| HPV31 | L2 | 9 | 273 |
| HPV31 | L2 | 10 | 273 |
| HPV31 | L2 | 8 | 102 |
| HPV31 | L2 | 11 | 160 |
| HPV31 | L2 | 11 | 234 |
| HPV31 | L2 | 10 | 96 |
| HPV31 | L2 | 11 | 96 |
| HPV31 | L2 | 10 | 421 |
| HPV31 | L2 | 9 | 406 |
| HPV31 | L2 | 8 | 99 |
| HPV31 | L2 | 10 | 99 |
| HPV31 | L2 | 11 | 99 |
| HPV31 | L2 | 8 | 125 |
| HPV31 | L2 | 10 | 125 |

TABLE XI-continued

HLA-B7 Supermotif Peptides

| 1 | 2 | 3 | 4 |
|---|---|---|---|
| HPV31 | L2 | 11 | 125 |
| HPV31 | L2 | 8 | 211 |
| HPV31 | L2 | 10 | 211 |
| HPV31 | L2 | 10 | 123 |
| HPV31 | L2 | 9 | 401 |
| HPV31 | L2 | 11 | 401 |
| HPV31 | L2 | 9 | 87 |
| HPV31 | L2 | 9 | 33 |
| HPV31 | L2 | 10 | 33 |
| HPV31 | L2 | 8 | 191 |
| HPV31 | L2 | 9 | 327 |
| HPV31 | L2 | 9 | 249 |
| HPV31 | L2 | 9 | 155 |
| HPV31 | L2 | 10 | 155 |
| HPV31 | L2 | 11 | 166 |
| HPV31 | L2 | 9 | 126 |
| HPV31 | L2 | 10 | 126 |
| HPV31 | L2 | 8 | 91 |
| HPV31 | L2 | 11 | 91 |
| HPV31 | L2 | 11 | 284 |
| HPV31 | L2 | 8 | 216 |
| HPV31 | L2 | 11 | 216 |
| HPV31 | L2 | 9 | 90 |
| HPV31 | L2 | 8 | 78 |
| HPV31 | L2 | 10 | 78 |
| HPV31 | L2 | 11 | 372 |
| HPV31 | L2 | 9 | 168 |
| HPV31 | L2 | 10 | 168 |
| HPV31 | L2 | 11 | 168 |
| HPV31 | L2 | 10 | 141 |
| HPV31 | L2 | 10 | 209 |
| HPV31 | L2 | 8 | 427 |
| HPV31 | L2 | 10 | 409 |
| HPV31 | L2 | 11 | 409 |
| HPV31 | L2 | 9 | 393 |
| HPV31 | L2 | 11 | 393 |
| HPV31 | L2 | 10 | 73 |
| HPV31 | L2 | 9 | 387 |
| HPV33 | E1 | 8 | 3 |
| HPV33 | E1 | 10 | 3 |
| HPV33 | E1 | 11 | 301 |
| HPV33 | E1 | 10 | 585 |
| HPV33 | E1 | 11 | 585 |
| HPV33 | E1 | 9 | 470 |
| HPV33 | E1 | 10 | 470 |
| HPV33 | E1 | 8 | 293 |
| HPV33 | E1 | 8 | 460 |
| HPV33 | E1 | 9 | 460 |
| HPV33 | E1 | 11 | 592 |
| HPV33 | E1 | 10 | 302 |
| HPV33 | E1 | 11 | 302 |
| HPV33 | E1 | 11 | 553 |
| HPV33 | E1 | 8 | 504 |
| HPV33 | E1 | 10 | 504 |
| HPV33 | E1 | 11 | 504 |
| HPV33 | E1 | 9 | 433 |
| HPV33 | E1 | 8 | 237 |
| HPV33 | E1 | 10 | 237 |
| HPV33 | E1 | 11 | 237 |
| HPV33 | E1 | 8 | 329 |
| HPV33 | E1 | 10 | 329 |
| HPV33 | E1 | 11 | 329 |
| HPV33 | E1 | 8 | 518 |
| HPV33 | E1 | 11 | 518 |
| HPV33 | E1 | 8 | 569 |
| HPV33 | E1 | 10 | 569 |
| HPV33 | E1 | 11 | 569 |
| HPV33 | E2 | 10 | 195 |
| HPV33 | E2 | 9 | 247 |
| HPV33 | E2 | 11 | 340 |
| HPV33 | E2 | 10 | 294 |
| HPV33 | E2 | 8 | 26 |
| HPV33 | E2 | 10 | 26 |
| HPV33 | E2 | 11 | 26 |
| HPV33 | E2 | 10 | 341 |
| HPV33 | E2 | 11 | 341 |
| HPV33 | E2 | 9 | 238 |
| HPV33 | E2 | 9 | 229 |
| HPV33 | E2 | 11 | 59 |
| HPV33 | E5 | 8 | 59 |
| HPV33 | E5 | 10 | 59 |
| HPV33 | E5 | 10 | 20 |
| HPV33 | E5 | 11 | 20 |
| HPV33 | E5 | 9 | 45 |
| HPV33 | E5 | 10 | 45 |
| HPV33 | E5 | 11 | 45 |
| HPV33 | E6 | 9 | 111 |
| HPV33 | E6 | 11 | 111 |
| HPV33 | E6 | 8 | 94 |
| HPV33 | E6 | 11 | 94 |
| HPV33 | E6 | 8 | 35 |
| HPV33 | E6 | 9 | 35 |
| HPV33 | E6 | 11 | 35 |
| HPV33 | E6 | 8 | 8 |
| HPV33 | E6 | 11 | 8 |
| HPV33 | E6 | 8 | 58 |
| HPV33 | E6 | 10 | 58 |
| HPV33 | E7 | 8 | 18 |
| HPV33 | E7 | 11 | 18 |
| HPV33 | E7 | 8 | 5 |
| HPV33 | E7 | 9 | 5 |
| HPV33 | E7 | 11 | 5 |
| HPV33 | E7 | 8 | 46 |
| HPV33 | E7 | 9 | 46 |
| HPV33 | E7 | 10 | 46 |
| HPV33 | E7 | 9 | 40 |
| HPV33 | E7 | 11 | 40 |
| HPV33 | E7 | 8 | 16 |
| HPV33 | E7 | 10 | 16 |
| HPV33 | L1 | 9 | 180 |
| HPV33 | L1 | 11 | 180 |
| HPV33 | L1 | 10 | 483 |
| HPV33 | L1 | 10 | 185 |
| HPV33 | L1 | 11 | 185 |
| HPV33 | L1 | 8 | 438 |
| HPV33 | L1 | 9 | 438 |
| HPV33 | L1 | 11 | 438 |
| HPV33 | L1 | 8 | 240 |
| HPV33 | L1 | 9 | 240 |
| HPV33 | L1 | 10 | 240 |
| HPV33 | L1 | 11 | 240 |
| HPV33 | L1 | 8 | 461 |
| HPV33 | L1 | 9 | 461 |
| HPV33 | L1 | 11 | 461 |
| HPV33 | L1 | 8 | 292 |
| HPV33 | L1 | 9 | 292 |
| HPV33 | L1 | 8 | 476 |
| HPV33 | L1 | 8 | 163 |
| HPV33 | L1 | 8 | 309 |
| HPV33 | L1 | 9 | 78 |
| HPV33 | L1 | 9 | 13 |
| HPV33 | L1 | 10 | 13 |
| HPV33 | L1 | 8 | 394 |
| HPV33 | L1 | 10 | 394 |
| HPV33 | L1 | 8 | 93 |
| HPV33 | L1 | 9 | 93 |
| HPV33 | L1 | 10 | 93 |
| HPV33 | L1 | 8 | 54 |
| HPV33 | L1 | 9 | 54 |
| HPV33 | L1 | 10 | 54 |
| HPV33 | L1 | 9 | 432 |
| HPV33 | L1 | 9 | 186 |
| HPV33 | L1 | 10 | 186 |
| HPV33 | L1 | 11 | 407 |
| HPV33 | L1 | 10 | 408 |
| HPV33 | L1 | 11 | 164 |
| HPV33 | L1 | 8 | 14 |
| HPV33 | L1 | 9 | 14 |
| HPV33 | L1 | 10 | 139 |
| HPV33 | L1 | 8 | 5 |

TABLE XI-continued

HLA-B7 Supermotif Peptides

| 1 | 2 | 3 | 4 |
|---|---|---|---|
| HPV33 | L1 | 9 | 5 |
| HPV33 | L1 | 8 | 406 |
| HPV33 | L1 | 9 | 63 |
| HPV33 | L1 | 11 | 63 |
| HPV33 | L1 | 10 | 431 |
| HPV33 | L2 | 9 | 173 |
| HPV33 | L2 | 10 | 173 |
| HPV33 | L2 | 11 | 173 |
| HPV33 | L2 | 9 | 276 |
| HPV33 | L2 | 10 | 276 |
| HPV33 | L2 | 11 | 276 |
| HPV33 | L2 | 10 | 120 |
| HPV33 | L2 | 9 | 27 |
| HPV33 | L2 | 11 | 239 |
| HPV33 | L2 | 8 | 278 |
| HPV33 | L2 | 9 | 278 |
| HPV33 | L2 | 10 | 278 |
| HPV33 | L2 | 8 | 261 |
| HPV33 | L2 | 9 | 77 |
| HPV33 | L2 | 9 | 165 |
| HPV33 | L2 | 11 | 165 |
| HPV33 | L2 | 8 | 428 |
| HPV33 | L2 | 11 | 428 |
| HPV33 | L2 | 8 | 415 |
| HPV33 | L2 | 10 | 415 |
| HPV33 | L2 | 8 | 456 |
| HPV33 | L2 | 10 | 456 |
| HPV33 | L2 | 11 | 456 |
| HPV33 | L2 | 8 | 407 |
| HPV33 | L2 | 9 | 407 |
| HPV33 | L2 | 8 | 98 |
| HPV33 | L2 | 10 | 98 |
| HPV33 | L2 | 11 | 98 |
| HPV33 | L2 | 8 | 170 |
| HPV33 | L2 | 8 | 216 |
| HPV33 | L2 | 10 | 216 |
| HPV33 | L2 | 9 | 32 |
| HPV33 | L2 | 10 | 32 |
| HPV33 | L2 | 11 | 394 |
| HPV33 | L2 | 10 | 83 |
| HPV33 | L2 | 8 | 196 |
| HPV33 | L2 | 9 | 123 |
| HPV33 | L2 | 9 | 160 |
| HPV33 | L2 | 10 | 160 |
| HPV33 | L2 | 11 | 171 |
| HPV33 | L2 | 8 | 28 |
| HPV33 | L2 | 8 | 78 |
| HPV33 | L2 | 11 | 78 |
| HPV33 | L2 | 8 | 90 |
| HPV33 | L2 | 11 | 90 |
| HPV33 | L2 | 9 | 86 |
| HPV33 | L2 | 11 | 346 |
| HPV33 | L2 | 11 | 289 |
| HPV33 | L2 | 9 | 89 |
| HPV33 | L2 | 8 | 220 |
| HPV33 | L2 | 9 | 220 |
| HPV33 | L2 | 8 | 274 |
| HPV33 | L2 | 9 | 274 |
| HPV33 | L2 | 11 | 274 |
| HPV33 | L2 | 9 | 425 |
| HPV33 | L2 | 10 | 425 |
| HPV33 | L2 | 11 | 425 |
| HPV33 | L2 | 9 | 419 |
| HPV33 | L2 | 10 | 419 |
| HPV33 | L2 | 8 | 245 |
| HPV33 | L2 | 10 | 329 |
| HPV33 | L2 | 10 | 412 |
| HPV33 | L2 | 11 | 412 |
| HPV33 | L2 | 9 | 185 |
| HPV33 | L2 | 10 | 138 |
| HPV33 | L2 | 9 | 214 |
| HPV33 | L2 | 10 | 214 |
| HPV33 | L2 | 10 | 375 |
| HPV33 | L2 | 11 | 375 |
| HPV33 | L2 | 11 | 125 |
| HPV33 | L2 | 9 | 402 |
| HPV33 | L2 | 10 | 72 |
| HPV33 | L2 | 11 | 72 |
| HPV33 | L2 | 9 | 422 |
| HPV33 | L2 | 8 | 338 |
| HPV33 | L2 | 11 | 338 |
| HPV45 | E1 | 10 | 552 |
| HPV45 | E1 | 8 | 562 |
| HPV45 | E1 | 10 | 562 |
| HPV45 | E1 | 11 | 562 |
| HPV45 | E1 | 9 | 179 |
| HPV45 | E1 | 8 | 504 |
| HPV45 | E1 | 9 | 504 |
| HPV45 | E1 | 10 | 504 |
| HPV45 | E1 | 11 | 504 |
| HPV45 | E1 | 9 | 301 |
| HPV45 | E1 | 10 | 301 |
| HPV45 | E1 | 11 | 301 |
| HPV45 | E1 | 10 | 585 |
| HPV45 | E1 | 11 | 585 |
| HPV45 | E1 | 9 | 470 |
| HPV45 | E1 | 10 | 470 |
| HPV45 | E1 | 9 | 627 |
| HPV45 | E1 | 9 | 249 |
| HPV45 | E1 | 11 | 545 |
| HPV45 | E1 | 8 | 237 |
| HPV45 | E1 | 11 | 237 |
| HPV45 | E1 | 11 | 592 |
| HPV45 | E1 | 9 | 553 |
| HPV45 | E1 | 8 | 302 |
| HPV45 | E1 | 9 | 302 |
| HPV45 | E1 | 10 | 302 |
| HPV45 | E1 | 11 | 302 |
| HPV45 | E1 | 9 | 433 |
| HPV45 | E1 | 9 | 97 |
| HPV45 | E1 | 9 | 110 |
| HPV45 | E1 | 8 | 329 |
| HPV45 | E1 | 10 | 329 |
| HPV45 | E1 | 11 | 329 |
| HPV45 | E1 | 8 | 460 |
| HPV45 | E1 | 9 | 460 |
| HPV45 | E1 | 10 | 460 |
| HPV45 | E1 | 8 | 293 |
| HPV45 | E1 | 8 | 569 |
| HPV45 | E1 | 10 | 569 |
| HPV45 | E1 | 11 | 569 |
| HPV45 | E2 | 9 | 355 |
| HPV45 | E2 | 11 | 355 |
| HPV45 | E2 | 8 | 240 |
| HPV45 | E2 | 10 | 66 |
| HPV45 | E2 | 10 | 5 |
| HPV45 | E2 | 10 | 238 |
| HPV45 | E2 | 11 | 65 |
| HPV45 | E6 | 9 | 6 |
| HPV45 | E6 | 8 | 14 |
| HPV45 | E6 | 9 | 113 |
| HPV45 | E6 | 8 | 10 |
| HPV45 | E7 | 8 | 22 |
| HPV45 | E7 | 11 | 22 |
| HPV45 | E7 | 9 | 16 |
| HPV45 | E7 | 11 | 16 |
| HPV45 | E7 | 8 | 56 |
| HPV45 | E7 | 10 | 56 |
| HPV45 | E7 | 9 | 3 |
| HPV45 | E7 | 10 | 3 |
| HPV45 | E7 | 11 | 3 |
| HPV45 | L1 | 10 | 212 |
| HPV45 | L1 | 11 | 212 |
| HPV45 | L1 | 8 | 386 |
| HPV45 | L1 | 8 | 469 |
| HPV45 | L1 | 9 | 469 |
| HPV45 | L1 | 11 | 469 |
| HPV45 | L1 | 8 | 267 |
| HPV45 | L1 | 9 | 267 |
| HPV45 | L1 | 11 | 267 |

TABLE XI-continued

HLA-B7 Supermotif Peptides

| 1 | 2 | 3 | 4 |
|---|---|---|---|
| HPV45 | L1 | 8 | 21 |
| HPV45 | L1 | 9 | 21 |
| HPV45 | L1 | 10 | 21 |
| HPV45 | L1 | 8 | 511 |
| HPV45 | L1 | 8 | 338 |
| HPV45 | L1 | 9 | 104 |
| HPV45 | L1 | 9 | 39 |
| HPV45 | L1 | 10 | 39 |
| HPV45 | L1 | 8 | 119 |
| HPV45 | L1 | 9 | 119 |
| HPV45 | L1 | 10 | 119 |
| HPV45 | L1 | 11 | 73 |
| HPV45 | L1 | 8 | 464 |
| HPV45 | L1 | 11 | 464 |
| HPV45 | L1 | 9 | 213 |
| HPV45 | L1 | 10 | 213 |
| HPV45 | L1 | 8 | 437 |
| HPV45 | L1 | 9 | 437 |
| HPV45 | L1 | 8 | 40 |
| HPV45 | L1 | 9 | 40 |
| HPV45 | L1 | 8 | 438 |
| HPV45 | L1 | 11 | 438 |
| HPV45 | L1 | 8 | 41 |
| HPV45 | L1 | 10 | 439 |
| HPV45 | L1 | 8 | 208 |
| HPV45 | L1 | 10 | 208 |
| HPV45 | L1 | 9 | 515 |
| HPV45 | L1 | 8 | 525 |
| HPV45 | L1 | 8 | 31 |
| HPV45 | L1 | 9 | 31 |
| HPV45 | L1 | 11 | 507 |
| HPV45 | L1 | 8 | 321 |
| HPV45 | L1 | 9 | 463 |
| HPV45 | L1 | 8 | 189 |
| HPV45 | L1 | 9 | 189 |
| HPV45 | L1 | 9 | 89 |
| HPV45 | L1 | 11 | 89 |
| HPV45 | L1 | 9 | 247 |
| HPV45 | L1 | 10 | 381 |
| HPV45 | L1 | 9 | 436 |
| HPV45 | L1 | 10 | 436 |
| HPV45 | L1 | 10 | 79 |
| HPV45 | L1 | 11 | 79 |
| HPV45 | L1 | 9 | 258 |
| HPV45 | L1 | 8 | 492 |
| HPV45 | L1 | 9 | 492 |
| HPV45 | L1 | 11 | 492 |
| HPV45 | L2 | 9 | 27 |
| HPV45 | L2 | 8 | 100 |
| HPV45 | L2 | 8 | 208 |
| HPV45 | L2 | 11 | 208 |
| HPV45 | L2 | 9 | 257 |
| HPV45 | L2 | 11 | 266 |
| HPV45 | L2 | 10 | 94 |
| HPV45 | L2 | 11 | 94 |
| HPV45 | L2 | 8 | 445 |
| HPV45 | L2 | 10 | 445 |
| HPV45 | L2 | 11 | 445 |
| HPV45 | L2 | 8 | 223 |
| HPV45 | L2 | 8 | 97 |
| HPV45 | L2 | 10 | 97 |
| HPV45 | L2 | 11 | 97 |
| HPV45 | L2 | 8 | 85 |
| HPV45 | L2 | 9 | 85 |
| HPV45 | L2 | 8 | 244 |
| HPV45 | L2 | 9 | 452 |
| HPV45 | L2 | 10 | 452 |
| HPV45 | L2 | 11 | 452 |
| HPV45 | L2 | 8 | 408 |
| HPV45 | L2 | 9 | 377 |
| HPV45 | L2 | 9 | 159 |
| HPV45 | L2 | 10 | 159 |
| HPV45 | L2 | 11 | 253 |
| HPV45 | L2 | 10 | 355 |
| HPV45 | L2 | 8 | 28 |
| HPV45 | L2 | 11 | 354 |
| HPV45 | L2 | 8 | 89 |
| HPV45 | L2 | 11 | 284 |
| HPV45 | L2 | 9 | 88 |
| HPV45 | L2 | 9 | 324 |
| HPV45 | L2 | 11 | 324 |
| HPV45 | L2 | 10 | 419 |
| HPV45 | L2 | 11 | 419 |
| HPV45 | L2 | 11 | 137 |
| HPV45 | L2 | 9 | 213 |
| HPV45 | L2 | 9 | 360 |
| HPV45 | L2 | 11 | 360 |
| HPV45 | L2 | 9 | 184 |
| HPV45 | L2 | 9 | 144 |
| HPV45 | L2 | 9 | 271 |
| HPV45 | L2 | 10 | 271 |
| HPV45 | L2 | 9 | 398 |
| HPV45 | L2 | 10 | 398 |
| HPV45 | L2 | 11 | 398 |
| HPV45 | L2 | 10 | 72 |
| HPV45 | L2 | 11 | 72 |
| HPV45 | L2 | 9 | 390 |
| HPV45 | L2 | 11 | 390 |
| HPV45 | L2 | 11 | 170 |
| HPV45 | L2 | 10 | 119 |
| HPV45 | L2 | 9 | 415 |
| HPV45 | L2 | 8 | 370 |
| HPV56 | E2 | 11 | 138 |
| HPV56 | E2 | 10 | 243 |
| HPV56 | E2 | 9 | 229 |
| HPV56 | E2 | 10 | 229 |
| HPV56 | E2 | 8 | 300 |
| HPV56 | E2 | 9 | 300 |
| HPV56 | E2 | 8 | 182 |
| HPV56 | E2 | 9 | 186 |
| HPV56 | E2 | 9 | 151 |
| HPV56 | E2 | 9 | 2 |
| HPV56 | E2 | 11 | 2 |
| HPV56 | E6 | 8 | 61 |
| HPV56 | E6 | 10 | 61 |
| HPV56 | E6 | 11 | 61 |
| HPV56 | E6 | 8 | 24 |
| HPV56 | E6 | 11 | 24 |
| HPV56 | E6 | 9 | 7 |
| HPV56 | E6 | 8 | 11 |
| HPV56 | E6 | 11 | 11 |
| HPV56 | E6 | 10 | 111 |
| HPV56 | E7 | 8 | 46 |
| HPV56 | E7 | 8 | 16 |
| HPV56 | E7 | 8 | 63 |
| HPV56 | E7 | 9 | 63 |
| HPV56 | E7 | 10 | 63 |
| HPV56 | E7 | 8 | 5 |
| HPV56 | E7 | 9 | 5 |
| HPV56 | E7 | 11 | 5 |
| HPV56 | L1 | 9 | 521 |
| HPV56 | L1 | 11 | 219 |
| HPV56 | L1 | 8 | 472 |
| HPV56 | L1 | 9 | 472 |
| HPV56 | L1 | 11 | 472 |
| HPV56 | L1 | 8 | 11 |
| HPV56 | L1 | 10 | 11 |
| HPV56 | L1 | 11 | 11 |
| HPV56 | L1 | 8 | 318 |
| HPV56 | L1 | 9 | 318 |
| HPV56 | L1 | 10 | 318 |
| HPV56 | L1 | 8 | 30 |
| HPV56 | L1 | 10 | 30 |
| HPV56 | L1 | 8 | 495 |
| HPV56 | L1 | 9 | 495 |
| HPV56 | L1 | 11 | 495 |
| HPV56 | L1 | 9 | 96 |
| HPV56 | L1 | 11 | 96 |
| HPV56 | L1 | 8 | 343 |
| HPV56 | L1 | 9 | 111 |

TABLE XI-continued

HLA-B7 Supermotif Peptides

| 1 | 2 | 3 | 4 |
|---|---|---|---|
| HPV56 | L1 | 9 | 48 |
| HPV56 | L1 | 10 | 48 |
| HPV56 | L1 | 11 | 48 |
| HPV56 | L1 | 8 | 126 |
| HPV56 | L1 | 9 | 126 |
| HPV56 | L1 | 10 | 126 |
| HPV56 | L1 | 10 | 220 |
| HPV56 | L1 | 9 | 12 |
| HPV56 | L1 | 10 | 12 |
| HPV56 | L1 | 11 | 12 |
| HPV56 | L1 | 8 | 319 |
| HPV56 | L1 | 9 | 319 |
| HPV56 | L1 | 8 | 320 |
| HPV56 | L1 | 9 | 466 |
| HPV56 | L1 | 10 | 466 |
| HPV56 | L1 | 8 | 49 |
| HPV56 | L1 | 9 | 49 |
| HPV56 | L1 | 10 | 49 |
| HPV56 | L1 | 11 | 441 |
| HPV56 | L1 | 10 | 465 |
| HPV56 | L1 | 11 | 465 |
| HPV56 | L1 | 8 | 40 |
| HPV56 | L1 | 9 | 40 |
| HPV56 | L1 | 8 | 440 |
| HPV56 | L1 | 8 | 196 |
| HPV56 | L1 | 8 | 227 |
| HPV56 | L1 | 9 | 227 |
| HPV56 | L1 | 11 | 328 |
| HPV56 | L1 | 8 | 51 |
| HPV56 | L1 | 9 | 265 |
| HPV56 | L1 | 11 | 265 |
| HPV56 | L2 | 9 | 271 |
| HPV56 | L2 | 10 | 271 |
| HPV56 | L2 | 11 | 271 |
| HPV56 | L2 | 9 | 358 |
| HPV56 | L2 | 10 | 358 |
| HPV56 | L2 | 11 | 391 |
| HPV56 | L2 | 11 | 170 |
| HPV56 | L2 | 8 | 223 |
| HPV56 | L2 | 9 | 223 |
| HPV56 | L2 | 9 | 27 |
| HPV56 | L2 | 9 | 238 |
| HPV56 | L2 | 11 | 238 |
| HPV56 | L2 | 8 | 273 |
| HPV56 | L2 | 9 | 273 |
| HPV56 | L2 | 10 | 273 |
| HPV56 | L2 | 8 | 100 |
| HPV56 | L2 | 8 | 208 |
| HPV56 | L2 | 11 | 208 |
| HPV56 | L2 | 8 | 412 |
| HPV56 | L2 | 8 | 97 |
| HPV56 | L2 | 10 | 97 |
| HPV56 | L2 | 11 | 97 |
| HPV56 | L2 | 8 | 215 |
| HPV56 | L2 | 9 | 215 |
| HPV56 | L2 | 8 | 195 |
| HPV56 | L2 | 10 | 119 |
| HPV56 | L2 | 10 | 453 |
| HPV56 | L2 | 11 | 453 |
| HPV56 | L2 | 8 | 376 |
| HPV56 | L2 | 8 | 373 |
| HPV56 | L2 | 10 | 373 |
| HPV56 | L2 | 11 | 373 |
| HPV56 | L2 | 8 | 409 |
| HPV56 | L2 | 10 | 409 |
| HPV56 | L2 | 11 | 409 |
| HPV56 | L2 | 11 | 253 |
| HPV56 | L2 | 9 | 159 |
| HPV56 | L2 | 10 | 159 |
| HPV56 | L2 | 8 | 89 |
| HPV56 | L2 | 10 | 335 |
| HPV56 | L2 | 11 | 284 |
| HPV56 | L2 | 8 | 244 |
| HPV56 | L2 | 9 | 88 |
| HPV56 | L2 | 8 | 77 |
| HPV56 | L2 | 11 | 77 |
| HPV56 | L2 | 9 | 324 |
| HPV56 | L2 | 11 | 324 |
| HPV56 | L2 | 11 | 266 |
| HPV56 | L2 | 9 | 422 |
| HPV56 | L2 | 10 | 422 |
| HPV56 | L2 | 11 | 422 |
| HPV56 | L2 | 8 | 85 |
| HPV56 | L2 | 9 | 85 |
| HPV56 | L2 | 9 | 399 |
| HPV56 | L2 | 10 | 399 |
| HPV56 | L2 | 11 | 399 |
| HPV56 | L2 | 9 | 213 |
| HPV56 | L2 | 10 | 213 |
| HPV56 | L2 | 11 | 213 |
| HPV56 | L2 | 8 | 368 |
| HPV56 | L2 | 9 | 184 |
| HPV56 | L2 | 9 | 144 |
| HPV56 | L2 | 10 | 72 |
| HPV56 | L2 | 11 | 72 |
| HPV56 | L2 | 8 | 419 |
| HPV56 | L2 | 9 | 416 |
| HPV56 | L2 | 11 | 416 |

TABLE XI A

HPV 6A
HLA-B7 Supermotif Peptides

| 2 | 3 | 4 |
|---|---|---|
| L2 | 9 | 271 |
| L2 | 10 | 271 |
| L2 | 8 | 118 |
| E1 | 10 | 337 |
| E1 | 11 | 337 |
| E2 | 8 | 326 |
| E2 | 10 | 326 |
| L2 | 10 | 410 |
| L1 | 8 | 158 |
| E4 | 11 | 39 |
| L2 | 8 | 217 |
| L2 | 9 | 217 |
| L2 | 8 | 98 |
| L2 | 10 | 98 |
| L2 | 11 | 98 |
| L2 | 9 | 182 |
| E1 | 10 | 181 |
| E5 | 9 | 77 |
| E5 | 10 | 77 |
| E5 | 11 | 77 |
| L2 | 9 | 27 |
| L1 | 10 | 181 |
| L1 | 11 | 181 |
| E1 | 10 | 560 |
| L2 | 11 | 236 |
| L2 | 8 | 101 |
| L1 | 8 | 89 |
| L1 | 9 | 89 |
| L1 | 10 | 89 |
| E7 | 8 | 19 |
| E7 | 11 | 19 |
| L1 | 8 | 236 |
| L1 | 9 | 236 |
| L1 | 10 | 236 |
| L1 | 11 | 236 |
| L1 | 8 | 434 |
| L1 | 9 | 434 |
| L1 | 11 | 434 |
| L2 | 11 | 354 |
| E1 | 9 | 257 |
| E1 | 11 | 257 |

TABLE XI A-continued

HPV 6A
HLA-B7 Supermotif Peptides

| 2 | 3 | 4 |
|---|---|---|
| E1 | 9 | 309 |
| E1 | 10 | 309 |
| E1 | 11 | 309 |
| L2 | 11 | 162 |
| L2 | 10 | 95 |
| L2 | 11 | 95 |
| L1 | 8 | 265 |
| L1 | 9 | 265 |
| E2 | 10 | 90 |
| E1 | 9 | 593 |
| E1 | 10 | 593 |
| E1 | 11 | 593 |
| L2 | 10 | 407 |
| L2 | 9 | 402 |
| L2 | 11 | 402 |
| L2 | 8 | 85 |
| L2 | 9 | 85 |
| L2 | 10 | 85 |
| E1 | 9 | 478 |
| E1 | 10 | 478 |
| L2 | 8 | 206 |
| E2 | 10 | 257 |
| E2 | 11 | 257 |
| L2 | 10 | 425 |
| L2 | 11 | 425 |
| L1 | 10 | 117 |
| L2 | 8 | 188 |
| L2 | 11 | 188 |
| L2 | 11 | 336 |
| L2 | 10 | 362 |
| L2 | 11 | 362 |
| L1 | 9 | 46 |
| E1 | 8 | 301 |
| E2 | 10 | 208 |
| E1 | 9 | 455 |
| E1 | 10 | 455 |
| E1 | 11 | 455 |
| L2 | 9 | 32 |
| L2 | 10 | 32 |
| L2 | 8 | 193 |
| L2 | 8 | 450 |
| L2 | 9 | 450 |
| L2 | 10 | 450 |
| E2 | 9 | 352 |
| E2 | 11 | 352 |
| L1 | 8 | 432 |
| L1 | 10 | 432 |
| L1 | 11 | 432 |
| E6 | 9 | 109 |
| L2 | 9 | 79 |
| L2 | 10 | 79 |
| L1 | 8 | 305 |
| L1 | 8 | 74 |
| L1 | 9 | 74 |
| L2 | 8 | 422 |
| E5 | 8 | 18 |
| E5 | 9 | 18 |
| E5 | 11 | 18 |
| E1 | 11 | 591 |
| L1 | 8 | 134 |
| L1 | 10 | 134 |
| E1 | 11 | 544 |
| L1 | 8 | 390 |
| L1 | 10 | 390 |
| L2 | 10 | 358 |
| L2 | 9 | 157 |
| L1 | 8 | 15 |
| L1 | 11 | 15 |
| L2 | 9 | 251 |
| L2 | 11 | 251 |
| L2 | 9 | 123 |
| E7 | 10 | 17 |
| E1 | 8 | 479 |
| E1 | 9 | 479 |
| E1 | 11 | 479 |
| L2 | 8 | 28 |
| E4 | 8 | 28 |
| E1 | 8 | 310 |
| E1 | 9 | 310 |
| E1 | 10 | 310 |
| E1 | 11 | 310 |
| L1 | 9 | 182 |
| L1 | 10 | 182 |
| E2 | 8 | 60 |
| E1 | 9 | 561 |
| E1 | 11 | 561 |
| L1 | 10 | 404 |
| L1 | 8 | 13 |
| L1 | 9 | 13 |
| L1 | 10 | 13 |
| E4 | 8 | 32 |
| L1 | 11 | 403 |
| L1 | 9 | 12 |
| L1 | 10 | 12 |
| L1 | 11 | 12 |
| E2 | 9 | 235 |
| E2 | 8 | 353 |
| E2 | 10 | 353 |
| E2 | 11 | 353 |
| L2 | 9 | 170 |
| L2 | 10 | 170 |
| L2 | 11 | 170 |
| L2 | 8 | 90 |
| L2 | 9 | 90 |
| E1 | 10 | 527 |
| E1 | 11 | 527 |
| E1 | 9 | 118 |
| E1 | 10 | 118 |
| E7 | 9 | 46 |
| E7 | 10 | 46 |
| E1 | 8 | 512 |
| E1 | 9 | 512 |
| E1 | 10 | 512 |
| E1 | 11 | 512 |
| E7 | 8 | 16 |
| E7 | 11 | 16 |
| L2 | 10 | 169 |
| L2 | 11 | 169 |
| L2 | 8 | 167 |
| L2 | 8 | 381 |
| L2 | 10 | 381 |
| L2 | 10 | 284 |
| L2 | 11 | 284 |
| L1 | 9 | 481 |
| L1 | 10 | 481 |
| E1 | 11 | 225 |
| E4 | 9 | 31 |
| L2 | 9 | 89 |
| L2 | 10 | 89 |
| L2 | 10 | 219 |
| L2 | 11 | 219 |
| L1 | 8 | 3 |
| L1 | 9 | 3 |
| E2 | 8 | 246 |
| E2 | 9 | 246 |
| E2 | 11 | 246 |
| L2 | 10 | 324 |
| E1 | 9 | 93 |
| E1 | 10 | 93 |
| E2 | 9 | 323 |
| E2 | 10 | 323 |
| E2 | 11 | 323 |
| L1 | 8 | 402 |
| E1 | 9 | 107 |
| L2 | 11 | 417 |
| E1 | 10 | 89 |
| E1 | 11 | 89 |
| L2 | 9 | 138 |

TABLE XI A-continued

HPV 6A
HLA-B7 Supermotif Peptides

| 2 | 3 | 4 |
|---|---|---|
| E2 | 9 | 215 |
| E4 | 8 | 62 |
| E4 | 11 | 62 |
| L1 | 10 | 427 |
| L2 | 8 | 414 |
| L2 | 9 | 414 |
| E1 | 8 | 468 |
| E1 | 9 | 468 |
| E1 | 10 | 468 |
| E5 | 8 | 63 |
| E5 | 10 | 63 |
| E5 | 11 | 63 |
| L2 | 9 | 375 |
| E4 | 9 | 27 |
| E2 | 10 | 234 |
| L2 | 8 | 242 |
| L1 | 11 | 290 |
| L1 | 11 | 174 |
| E2 | 11 | 221 |
| L2 | 10 | 213 |
| E1 | 9 | 641 |
| L1 | 9 | 59 |
| L1 | 11 | 59 |
| L2 | 11 | 72 |
| L2 | 10 | 388 |
| L2 | 11 | 388 |
| L2 | 8 | 122 |
| L2 | 10 | 122 |
| E2 | 9 | 59 |
| L1 | 10 | 11 |
| L1 | 11 | 11 |
| E4 | 9 | 66 |
| L1 | 8 | 227 |
| L1 | 9 | 227 |
| L1 | 8 | 457 |
| L1 | 9 | 457 |
| E6 | 10 | 59 |

SF 1168107 vl

TABLE XI B

HPV 6B
HLA-B7 Supermotif Peptides

| 2 | 3 | 4 |
|---|---|---|
| L2 | 9 | 271 |
| L2 | 10 | 271 |
| L2 | 8 | 118 |
| E1 | 10 | 337 |
| E1 | 11 | 337 |
| E2 | 8 | 326 |
| E2 | 10 | 326 |
| L2 | 10 | 409 |
| E4 | 8 | 3 |
| E4 | 9 | 3 |
| E4 | 10 | 3 |
| E4 | 11 | 3 |
| L1 | 8 | 158 |
| E4 | 11 | 49 |
| L2 | 8 | 217 |
| L2 | 9 | 217 |
| L2 | 8 | 98 |
| L2 | 10 | 98 |
| L2 | 11 | 98 |
| E1 | 10 | 181 |
| L2 | 9 | 182 |
| E5A | 8 | 77 |
| E5A | 9 | 77 |
| E5A | 10 | 77 |
| E5A | 11 | 77 |

TABLE XI B-continued

HPV 6B
HLA-B7 Supermotif Peptides

| 2 | 3 | 4 |
|---|---|---|
| L2 | 9 | 27 |
| L1 | 10 | 181 |
| L1 | 11 | 181 |
| E1 | 10 | 560 |
| L2 | 11 | 236 |
| L2 | 8 | 101 |
| L1 | 8 | 89 |
| L1 | 9 | 89 |
| L1 | 10 | 89 |
| E7 | 8 | 19 |
| E7 | 11 | 19 |
| L1 | 8 | 236 |
| L1 | 9 | 236 |
| L1 | 10 | 236 |
| L1 | 11 | 236 |
| L1 | 8 | 434 |
| L1 | 9 | 434 |
| L1 | 11 | 434 |
| L2 | 11 | 354 |
| E1 | 9 | 257 |
| E1 | 11 | 257 |
| E1 | 9 | 309 |
| E1 | 10 | 309 |
| E1 | 11 | 309 |
| L2 | 11 | 162 |
| L2 | 10 | 95 |
| L2 | 11 | 95 |
| L1 | 8 | 265 |
| L1 | 9 | 265 |
| E2 | 10 | 90 |
| E1 | 9 | 593 |
| E1 | 10 | 593 |
| E1 | 11 | 593 |
| L2 | 10 | 406 |
| L2 | 9 | 401 |
| L2 | 11 | 401 |
| L2 | 8 | 85 |
| L2 | 9 | 85 |
| L2 | 10 | 85 |
| E1 | 9 | 478 |
| E1 | 10 | 478 |
| L2 | 8 | 206 |
| E2 | 10 | 257 |
| E2 | 11 | 257 |
| L2 | 10 | 425 |
| L2 | 11 | 425 |
| L1 | 10 | 117 |
| L2 | 8 | 188 |
| L2 | 11 | 188 |
| L2 | 11 | 336 |
| L2 | 10 | 362 |
| L2 | 11 | 362 |
| L1 | 9 | 46 |
| E1 | 8 | 301 |
| E2 | 10 | 208 |
| E1 | 9 | 455 |
| E1 | 10 | 455 |
| E1 | 11 | 455 |
| L2 | 9 | 32 |
| L2 | 10 | 32 |
| L2 | 8 | 193 |
| L2 | 8 | 450 |
| L2 | 9 | 450 |
| L2 | 10 | 450 |
| E2 | 9 | 352 |
| E2 | 11 | 352 |
| L1 | 8 | 432 |
| L1 | 10 | 432 |
| L1 | 11 | 432 |
| E6 | 9 | 109 |
| L2 | 9 | 79 |
| L2 | 10 | 79 |
| L1 | 8 | 305 |
| L1 | 8 | 74 |

TABLE XI B-continued

HPV 6B
HLA-B7 Supermotif Peptides

| 2 | 3 | 4 |
|---|---|---|
| L1 | 9 | 74 |
| L2 | 8 | 422 |
| E5A | 8 | 18 |
| E5A | 9 | 18 |
| E5A | 11 | 18 |
| E1 | 11 | 591 |
| L1 | 8 | 134 |
| L1 | 10 | 134 |
| E1 | 11 | 544 |
| L1 | 8 | 390 |
| L1 | 10 | 390 |
| L2 | 10 | 358 |
| L2 | 9 | 157 |
| L1 | 8 | 15 |
| L1 | 11 | 15 |
| L2 | 9 | 251 |
| L2 | 11 | 251 |
| L2 | 9 | 123 |
| E7 | 10 | 17 |
| E1 | 8 | 479 |
| E1 | 9 | 479 |
| E1 | 11 | 479 |
| L2 | 8 | 28 |
| E4 | 8 | 38 |
| E1 | 8 | 310 |
| E1 | 9 | 310 |
| E1 | 10 | 310 |
| E1 | 11 | 310 |
| L1 | 9 | 182 |
| L1 | 10 | 182 |
| E2 | 8 | 60 |
| E1 | 9 | 561 |
| E1 | 11 | 561 |
| L1 | 10 | 404 |
| L1 | 8 | 13 |
| L1 | 9 | 13 |
| L1 | 10 | 13 |
| E4 | 8 | 42 |
| L1 | 11 | 403 |
| L1 | 9 | 12 |
| L1 | 10 | 12 |
| L1 | 11 | 12 |
| E2 | 9 | 235 |
| E2 | 8 | 353 |
| E2 | 10 | 353 |
| E2 | 11 | 353 |
| L2 | 9 | 170 |
| L2 | 10 | 170 |
| L2 | 11 | 170 |
| L2 | 8 | 90 |
| L2 | 9 | 90 |
| E1 | 10 | 527 |
| E1 | 11 | 527 |
| E1 | 9 | 118 |
| E1 | 10 | 118 |
| E7 | 9 | 46 |
| E7 | 10 | 46 |
| E1 | 8 | 512 |
| E1 | 9 | 512 |
| E1 | 10 | 512 |
| E1 | 11 | 512 |
| E7 | 8 | 16 |
| E7 | 11 | 16 |
| L2 | 10 | 169 |
| L2 | 11 | 169 |
| L2 | 8 | 167 |
| L2 | 8 | 381 |
| L2 | 10 | 381 |
| L2 | 10 | 284 |
| L2 | 11 | 284 |
| L1 | 9 | 481 |
| L1 | 10 | 481 |
| E1 | 11 | 225 |
| E4 | 9 | 41 |
| L2 | 9 | 89 |
| L2 | 10 | 89 |
| L2 | 10 | 219 |
| L2 | 11 | 219 |
| L1 | 8 | 3 |
| L1 | 9 | 3 |
| E2 | 8 | 246 |
| E2 | 9 | 246 |
| E2 | 11 | 246 |
| L2 | 10 | 324 |
| E1 | 9 | 93 |
| E1 | 10 | 93 |
| E4 | 8 | 68 |
| E4 | 9 | 68 |
| L1 | 8 | 402 |
| E1 | 9 | 107 |
| E1 | 10 | 89 |
| E1 | 11 | 89 |
| L2 | 9 | 138 |
| L2 | 9 | 419 |
| L2 | 10 | 419 |
| L2 | 11 | 419 |
| E2 | 8 | 215 |
| E2 | 9 | 215 |
| E4 | 8 | 72 |
| E4 | 11 | 72 |
| L1 | 10 | 427 |
| L2 | 9 | 413 |
| L2 | 10 | 413 |
| E1 | 8 | 468 |
| E1 | 9 | 468 |
| E1 | 10 | 468 |
| E5A | 8 | 63 |
| E5A | 10 | 63 |
| E5A | 11 | 63 |
| L2 | 9 | 375 |
| E4 | 9 | 37 |
| E2 | 10 | 234 |
| L2 | 8 | 242 |
| L1 | 11 | 290 |
| L1 | 11 | 174 |
| L2 | 10 | 213 |
| E1 | 9 | 641 |
| L1 | 9 | 59 |
| L1 | 11 | 59 |
| L2 | 11 | 72 |
| L2 | 9 | 388 |
| L2 | 10 | 388 |
| L2 | 11 | 388 |
| L2 | 8 | 122 |
| L2 | 10 | 122 |
| E2 | 9 | 59 |
| L1 | 10 | 11 |
| L1 | 11 | 11 |
| E4 | 9 | 76 |
| L1 | 8 | 227 |
| L1 | 9 | 227 |
| L1 | 8 | 457 |
| L1 | 9 | 457 |
| E6 | 10 | 59 |

TABLE XI C

HPV11
HLA-B7 Supermotif Peptides

| 2 | 3 | 4 |
|---|---|---|
| L2 | 9 | 270 |
| L2 | 10 | 270 |
| E1 | 10 | 337 |

TABLE XI C-continued

HPV11
HLA-B7 Supermotif Peptides

| 2 | 3 | 4 |
|---|---|---|
| E1 | 11 | 337 |
| E2 | 8 | 325 |
| E2 | 10 | 325 |
| L1 | 8 | 159 |
| E4 | 11 | 50 |
| L2 | 8 | 97 |
| L2 | 10 | 97 |
| L2 | 11 | 97 |
| L2 | 9 | 181 |
| E4 | 9 | 47 |
| L2 | 9 | 26 |
| L1 | 10 | 182 |
| L1 | 11 | 182 |
| E1 | 10 | 560 |
| L2 | 11 | 235 |
| L2 | 11 | 353 |
| L2 | 8 | 100 |
| L1 | 8 | 89 |
| L1 | 9 | 89 |
| L1 | 10 | 89 |
| E7 | 8 | 19 |
| E7 | 11 | 19 |
| L2 | 11 | 357 |
| L1 | 8 | 237 |
| L1 | 9 | 237 |
| L1 | 10 | 237 |
| L1 | 11 | 237 |
| L1 | 8 | 435 |
| L1 | 9 | 435 |
| L1 | 11 | 435 |
| L2 | 10 | 350 |
| E1 | 9 | 257 |
| E1 | 11 | 257 |
| E1 | 9 | 309 |
| E1 | 11 | 309 |
| L2 | 11 | 161 |
| E2 | 8 | 210 |
| L2 | 10 | 94 |
| L2 | 11 | 94 |
| L1 | 8 | 266 |
| L1 | 9 | 266 |
| E2 | 10 | 90 |
| E5 | 8 | 77 |
| E5 | 9 | 77 |
| E5 | 10 | 77 |
| E5 | 11 | 77 |
| E6 | 10 | 59 |
| E1 | 9 | 593 |
| E1 | 10 | 593 |
| E1 | 11 | 593 |
| L1 | 8 | 458 |
| L1 | 9 | 458 |
| L2 | 8 | 216 |
| L2 | 9 | 216 |
| L2 | 10 | 402 |
| L2 | 8 | 84 |
| L2 | 9 | 84 |
| L2 | 10 | 84 |
| L2 | 9 | 397 |
| L2 | 11 | 397 |
| E1 | 10 | 478 |
| E2 | 8 | 243 |
| E2 | 10 | 243 |
| E2 | 11 | 243 |
| L2 | 8 | 205 |
| L2 | 11 | 205 |
| L2 | 10 | 421 |
| L2 | 11 | 421 |
| L1 | 10 | 117 |
| L2 | 11 | 335 |
| L1 | 9 | 46 |
| L2 | 9 | 355 |
| E1 | 8 | 301 |
| E1 | 9 | 455 |
| E1 | 10 | 455 |
| E1 | 11 | 455 |
| L2 | 9 | 31 |
| L2 | 10 | 31 |
| L2 | 8 | 192 |
| L2 | 8 | 446 |
| L2 | 9 | 446 |
| L2 | 10 | 446 |
| L2 | 10 | 71 |
| L2 | 11 | 71 |
| E2 | 9 | 351 |
| E2 | 11 | 351 |
| L2 | 9 | 78 |
| L2 | 10 | 78 |
| E6 | 9 | 109 |
| L2 | 10 | 2 |
| L1 | 8 | 306 |
| L1 | 8 | 74 |
| L1 | 9 | 74 |
| L2 | 10 | 212 |
| L2 | 8 | 418 |
| E5 | 8 | 18 |
| E5 | 9 | 18 |
| E5 | 11 | 18 |
| E1 | 11 | 591 |
| L1 | 8 | 135 |
| L1 | 10 | 135 |
| L2 | 9 | 156 |
| L2 | 10 | 156 |
| E1 | 11 | 544 |
| L1 | 8 | 391 |
| L1 | 10 | 391 |
| L1 | 8 | 15 |
| L1 | 11 | 15 |
| L2 | 9 | 250 |
| L2 | 11 | 250 |
| E4 | 8 | 48 |
| E7 | 10 | 17 |
| E1 | 9 | 479 |
| E1 | 11 | 479 |
| L2 | 8 | 27 |
| E4 | 8 | 38 |
| E1 | 8 | 310 |
| E1 | 10 | 310 |
| E1 | 11 | 310 |
| L1 | 9 | 183 |
| L1 | 10 | 183 |
| E1 | 9 | 561 |
| E1 | 11 | 561 |
| E4 | 8 | 43 |
| L1 | 10 | 405 |
| L1 | 8 | 13 |
| L1 | 9 | 13 |
| L1 | 10 | 13 |
| E4 | 9 | 42 |
| L1 | 11 | 404 |
| L1 | 9 | 12 |
| L1 | 10 | 12 |
| L1 | 11 | 12 |
| E2 | 8 | 352 |
| E2 | 10 | 352 |
| E2 | 11 | 352 |
| L2 | 9 | 122 |
| L2 | 9 | 169 |
| L2 | 10 | 169 |
| L2 | 11 | 169 |
| L2 | 8 | 89 |
| L2 | 9 | 89 |
| E1 | 10 | 527 |
| E1 | 11 | 527 |
| E1 | 9 | 118 |
| E1 | 10 | 118 |
| E1 | 8 | 512 |
| E1 | 9 | 512 |

TABLE XI C-continued

HPV11
HLA-B7 Supermotif Peptides

| 2 | 3 | 4 |
|---|---|---|
| E1 | 10 | 512 |
| E1 | 11 | 512 |
| E7 | 9 | 46 |
| E7 | 10 | 46 |
| E7 | 8 | 16 |
| E7 | 11 | 16 |
| L2 | 10 | 168 |
| L2 | 11 | 168 |
| L2 | 8 | 166 |
| L2 | 10 | 283 |
| L2 | 11 | 283 |
| L1 | 10 | 482 |
| E1 | 11 | 225 |
| E4 | 8 | 67 |
| E4 | 9 | 67 |
| E4 | 10 | 41 |
| L2 | 9 | 88 |
| L2 | 10 | 88 |
| L2 | 10 | 218 |
| L2 | 11 | 218 |
| L1 | 8 | 3 |
| L1 | 9 | 3 |
| E2 | 9 | 195 |
| E2 | 9 | 322 |
| E2 | 10 | 322 |
| E2 | 11 | 322 |
| E1 | 9 | 93 |
| E1 | 10 | 93 |
| L2 | 11 | 76 |
| L1 | 8 | 403 |
| E1 | 9 | 107 |
| L2 | 10 | 323 |
| E1 | 10 | 89 |
| E1 | 11 | 89 |
| L2 | 9 | 137 |
| L2 | 9 | 415 |
| L2 | 10 | 415 |
| L2 | 11 | 415 |
| E2 | 10 | 215 |
| E4 | 11 | 71 |
| L1 | 10 | 428 |
| L2 | 9 | 409 |
| L2 | 10 | 409 |
| E1 | 8 | 468 |
| E1 | 9 | 468 |
| E1 | 10 | 468 |
| E5 | 8 | 63 |
| E5 | 10 | 63 |
| L2 | 9 | 371 |
| E4 | 9 | 37 |
| L2 | 8 | 241 |
| L1 | 11 | 291 |
| E1 | 9 | 641 |
| E4 | 8 | 3 |
| E4 | 9 | 3 |
| E4 | 10 | 3 |
| E4 | 11 | 3 |
| L1 | 9 | 59 |
| L1 | 11 | 59 |
| L1 | 9 | 217 |
| L2 | 9 | 384 |
| L2 | 10 | 384 |
| L2 | 11 | 384 |
| L1 | 10 | 11 |
| L1 | 11 | 11 |
| L2 | 8 | 121 |
| L2 | 10 | 121 |
| E5 | 8 | 4 |
| E4 | 9 | 75 |
| L1 | 8 | 228 |
| L1 | 9 | 228 |

TABLE XII

HLA-B27 Supermotif Peptides

| 1 | 2 | 3 | 4 |
|---|---|---|---|
| HPV16 | E1 | 10 | 67 |
| HPV16 | E1 | 9 | 203 |
| HPV16 | E1 | 9 | 209 |
| HPV16 | E1 | 11 | 209 |
| HPV16 | E1 | 9 | 516 |
| HPV16 | E1 | 11 | 516 |
| HPV16 | E1 | 8 | 399 |
| HPV16 | E1 | 10 | 399 |
| HPV16 | E1 | 8 | 76 |
| HPV16 | E1 | 10 | 76 |
| HPV16 | E1 | 11 | 76 |
| HPV16 | E1 | 9 | 627 |
| HPV16 | E1 | 8 | 606 |
| HPV16 | E1 | 9 | 431 |
| HPV16 | E1 | 10 | 416 |
| HPV16 | E1 | 11 | 416 |
| HPV16 | E1 | 8 | 26 |
| HPV16 | E1 | 8 | 291 |
| HPV16 | E1 | 10 | 291 |
| HPV16 | E1 | 11 | 116 |
| HPV16 | E1 | 10 | 182 |
| HPV16 | E1 | 9 | 211 |
| HPV16 | E1 | 11 | 226 |
| HPV16 | E1 | 10 | 284 |
| HPV16 | E1 | 11 | 284 |
| HPV16 | E1 | 9 | 482 |
| HPV16 | E1 | 10 | 482 |
| HPV16 | E1 | 8 | 79 |
| HPV16 | E1 | 8 | 251 |
| HPV16 | E1 | 10 | 251 |
| HPV16 | E1 | 11 | 251 |
| HPV16 | E1 | 8 | 426 |
| HPV16 | E1 | 8 | 550 |
| HPV16 | E1 | 8 | 469 |
| HPV16 | E1 | 10 | 469 |
| HPV16 | E1 | 11 | 469 |
| HPV16 | E1 | 9 | 417 |
| HPV16 | E1 | 10 | 417 |
| HPV16 | E1 | 8 | 413 |
| HPV16 | E1 | 10 | 413 |
| HPV16 | E1 | 9 | 87 |
| HPV16 | E1 | 10 | 262 |
| HPV16 | E1 | 8 | 579 |
| HPV16 | E1 | 10 | 579 |
| HPV16 | E1 | 8 | 557 |
| HPV16 | E1 | 8 | 460 |
| HPV16 | E1 | 10 | 86 |
| HPV16 | E1 | 9 | 393 |
| HPV16 | E1 | 10 | 393 |
| HPV16 | E1 | 8 | 198 |
| HPV16 | E1 | 9 | 198 |
| HPV16 | E1 | 10 | 198 |
| HPV16 | E1 | 11 | 198 |
| HPV16 | E1 | 9 | 536 |
| HPV16 | E1 | 10 | 536 |
| HPV16 | E1 | 8 | 312 |
| HPV16 | E1 | 9 | 312 |
| HPV16 | E1 | 10 | 312 |
| HPV16 | E1 | 11 | 312 |
| HPV16 | E1 | 8 | 446 |
| HPV16 | E1 | 9 | 446 |
| HPV16 | E1 | 11 | 446 |
| HPV16 | E1 | 8 | 491 |
| HPV16 | E1 | 9 | 491 |
| HPV16 | E1 | 11 | 491 |
| HPV16 | E1 | 8 | 229 |
| HPV16 | E1 | 10 | 229 |
| HPV16 | E1 | 11 | 229 |
| HPV16 | E1 | 8 | 286 |
| HPV16 | E1 | 9 | 286 |
| HPV16 | E1 | 8 | 581 |
| HPV16 | E1 | 8 | 468 |
| HPV16 | E1 | 9 | 468 |
| HPV16 | E1 | 11 | 468 |
| HPV16 | E1 | 8 | 310 |

TABLE XII-continued

HLA-B27 Supermotif Peptides

| 1 | 2 | 3 | 4 |
|---|---|---|---|
| HPV16 | E1 | 9 | 310 |
| HPV16 | E1 | 10 | 310 |
| HPV16 | E1 | 11 | 310 |
| HPV16 | E1 | 8 | 108 |
| HPV16 | E1 | 8 | 78 |
| HPV16 | E1 | 9 | 78 |
| HPV16 | E1 | 9 | 347 |
| HPV16 | E1 | 11 | 347 |
| HPV16 | E1 | 10 | 341 |
| HPV16 | E1 | 11 | 150 |
| HPV16 | E1 | 9 | 183 |
| HPV16 | E1 | 11 | 410 |
| HPV16 | E1 | 8 | 88 |
| HPV16 | E1 | 11 | 88 |
| HPV16 | E1 | 11 | 124 |
| HPV16 | E1 | 8 | 506 |
| HPV16 | E1 | 9 | 506 |
| HPV16 | E1 | 11 | 506 |
| HPV16 | E1 | 9 | 295 |
| HPV16 | E1 | 11 | 295 |
| HPV16 | E1 | 10 | 504 |
| HPV16 | E1 | 11 | 504 |
| HPV16 | E1 | 8 | 119 |
| HPV16 | E1 | 9 | 119 |
| HPV16 | E1 | 9 | 614 |
| HPV16 | E1 | 10 | 574 |
| HPV16 | E1 | 11 | 574 |
| HPV16 | E1 | 11 | 402 |
| HPV16 | E1 | 9 | 549 |
| HPV16 | E1 | 8 | 439 |
| HPV16 | E1 | 10 | 439 |
| HPV16 | E1 | 9 | 609 |
| HPV16 | E1 | 10 | 281 |
| HPV16 | E1 | 9 | 412 |
| HPV16 | E1 | 11 | 412 |
| HPV16 | E1 | 8 | 322 |
| HPV16 | E1 | 11 | 322 |
| HPV16 | E2 | 9 | 46 |
| HPV16 | E2 | 9 | 28 |
| HPV16 | E2 | 11 | 28 |
| HPV16 | E2 | 8 | 90 |
| HPV16 | E2 | 10 | 90 |
| HPV16 | E2 | 8 | 176 |
| HPV16 | E2 | 9 | 176 |
| HPV16 | E2 | 11 | 176 |
| HPV16 | E2 | 8 | 171 |
| HPV16 | E2 | 8 | 51 |
| HPV16 | E2 | 9 | 51 |
| HPV16 | E2 | 8 | 305 |
| HPV16 | E2 | 10 | 305 |
| HPV16 | E2 | 11 | 305 |
| HPV16 | E2 | 9 | 323 |
| HPV16 | E2 | 10 | 323 |
| HPV16 | E2 | 11 | 323 |
| HPV16 | E2 | 8 | 328 |
| HPV16 | E2 | 10 | 328 |
| HPV16 | E2 | 8 | 258 |
| HPV16 | E2 | 10 | 258 |
| HPV16 | E2 | 11 | 258 |
| HPV16 | E2 | 8 | 110 |
| HPV16 | E2 | 10 | 110 |
| HPV16 | E2 | 10 | 211 |
| HPV16 | E2 | 11 | 211 |
| HPV16 | E2 | 8 | 164 |
| HPV16 | E2 | 8 | 307 |
| HPV16 | E2 | 9 | 307 |
| HPV16 | E2 | 8 | 112 |
| HPV16 | E2 | 10 | 112 |
| HPV16 | E2 | 8 | 52 |
| HPV16 | E2 | 11 | 52 |
| HPV16 | E2 | 9 | 327 |
| HPV16 | E2 | 11 | 327 |
| HPV16 | E2 | 8 | 34 |
| HPV16 | E2 | 9 | 34 |
| HPV16 | E2 | 10 | 34 |
| HPV16 | E2 | 11 | 34 |
| HPV16 | E2 | 9 | 306 |
| HPV16 | E2 | 10 | 306 |
| HPV16 | E2 | 9 | 111 |
| HPV16 | E2 | 11 | 111 |
| HPV16 | E2 | 9 | 257 |
| HPV16 | E2 | 11 | 257 |
| HPV16 | E2 | 8 | 298 |
| HPV16 | E2 | 8 | 291 |
| HPV16 | E2 | 11 | 291 |
| HPV16 | E2 | 8 | 26 |
| HPV16 | E2 | 11 | 26 |
| HPV16 | E2 | 11 | 301 |
| HPV16 | E2 | 9 | 129 |
| HPV16 | E2 | 10 | 129 |
| HPV16 | E2 | 11 | 129 |
| HPV16 | E2 | 8 | 36 |
| HPV16 | E2 | 9 | 36 |
| HPV16 | E2 | 11 | 36 |
| HPV16 | E2 | 10 | 217 |
| HPV16 | E2 | 11 | 217 |
| HPV16 | E2 | 8 | 55 |
| HPV16 | E2 | 9 | 55 |
| HPV16 | E2 | 10 | 55 |
| HPV16 | E2 | 9 | 67 |
| HPV16 | E2 | 11 | 67 |
| HPV16 | E2 | 8 | 181 |
| HPV16 | E2 | 10 | 353 |
| HPV16 | E2 | 11 | 353 |
| HPV16 | E2 | 8 | 213 |
| HPV16 | E2 | 9 | 213 |
| HPV16 | E2 | 9 | 342 |
| HPV16 | E2 | 11 | 342 |
| HPV16 | E2 | 10 | 6 |
| HPV16 | E2 | 11 | 6 |
| HPV16 | E2 | 8 | 65 |
| HPV16 | E2 | 9 | 65 |
| HPV16 | E2 | 11 | 65 |
| HPV16 | E2 | 8 | 179 |
| HPV16 | E2 | 10 | 179 |
| HPV16 | E2 | 9 | 135 |
| HPV16 | E2 | 11 | 135 |
| HPV16 | E2 | 8 | 222 |
| HPV16 | E2 | 10 | 17 |
| HPV16 | E2 | 9 | 254 |
| HPV16 | E2 | 8 | 186 |
| HPV16 | E2 | 9 | 186 |
| HPV16 | E2 | 8 | 160 |
| HPV16 | E2 | 9 | 160 |
| HPV16 | E2 | 10 | 160 |
| HPV16 | E2 | 10 | 289 |
| HPV16 | E2 | 8 | 326 |
| HPV16 | E2 | 10 | 326 |
| HPV16 | E2 | 9 | 350 |
| HPV16 | E2 | 8 | 319 |
| HPV16 | E2 | 9 | 33 |
| HPV16 | E2 | 10 | 33 |
| HPV16 | E2 | 11 | 33 |
| HPV16 | E2 | 8 | 44 |
| HPV16 | E2 | 11 | 44 |
| HPV16 | E2 | 9 | 303 |
| HPV16 | E2 | 10 | 303 |
| HPV16 | E5 | 8 | 57 |
| HPV16 | E5 | 9 | 57 |
| HPV16 | E5 | 10 | 57 |
| HPV16 | E5 | 11 | 57 |
| HPV16 | E5 | 8 | 74 |
| HPV16 | E5 | 9 | 74 |
| HPV16 | E5 | 8 | 29 |
| HPV16 | E5 | 11 | 29 |
| HPV16 | E6 | 10 | 40 |
| HPV16 | E6 | 11 | 40 |
| HPV16 | E6 | 10 | 71 |
| HPV16 | E6 | 9 | 127 |
| HPV16 | E6 | 9 | 14 |

TABLE XII-continued

HLA-B27 Supermotif Peptides

| 1 | 2 | 3 | 4 |
|---|---|---|---|
| HPV16 | E6 | 8 | 132 |
| HPV16 | E6 | 8 | 54 |
| HPV16 | E6 | 8 | 137 |
| HPV16 | E6 | 9 | 30 |
| HPV16 | E6 | 10 | 30 |
| HPV16 | E6 | 10 | 108 |
| HPV16 | E6 | 10 | 135 |
| HPV16 | E6 | 8 | 128 |
| HPV16 | E6 | 10 | 74 |
| HPV16 | E6 | 8 | 45 |
| HPV16 | E6 | 9 | 45 |
| HPV16 | E6 | 10 | 45 |
| HPV16 | E6 | 8 | 1 |
| HPV16 | E6 | 9 | 1 |
| HPV16 | E6 | 8 | 100 |
| HPV16 | E6 | 9 | 100 |
| HPV16 | E6 | 11 | 16 |
| HPV16 | E6 | 10 | 130 |
| HPV16 | E6 | 10 | 123 |
| HPV16 | E6 | 9 | 124 |
| HPV16 | E6 | 8 | 84 |
| HPV16 | E6 | 10 | 17 |
| HPV16 | E6 | 8 | 46 |
| HPV16 | E6 | 9 | 46 |
| HPV16 | E6 | 9 | 78 |
| HPV16 | E6 | 11 | 78 |
| HPV16 | E6 | 9 | 150 |
| HPV16 | E6 | 8 | 61 |
| HPV16 | E6 | 9 | 61 |
| HPV16 | E6 | 8 | 83 |
| HPV16 | E6 | 9 | 83 |
| HPV16 | E7 | 8 | 50 |
| HPV16 | E7 | 9 | 59 |
| HPV16 | E7 | 11 | 59 |
| HPV16 | E7 | 8 | 48 |
| HPV16 | E7 | 10 | 48 |
| HPV16 | E7 | 8 | 76 |
| HPV16 | E7 | 9 | 76 |
| HPV16 | E7 | 8 | 8 |
| HPV16 | E7 | 10 | 65 |
| HPV16 | E7 | 8 | 1 |
| HPV16 | E7 | 11 | 1 |
| HPV16 | E7 | 8 | 72 |
| HPV16 | E7 | 11 | 72 |
| HPV16 | L1 | 8 | 524 |
| HPV16 | L1 | 9 | 55 |
| HPV16 | L1 | 9 | 405 |
| HPV16 | L1 | 10 | 405 |
| HPV16 | L1 | 9 | 187 |
| HPV16 | L1 | 9 | 255 |
| HPV16 | L1 | 10 | 255 |
| HPV16 | L1 | 10 | 479 |
| HPV16 | L1 | 11 | 386 |
| HPV16 | L1 | 11 | 99 |
| HPV16 | L1 | 8 | 344 |
| HPV16 | L1 | 8 | 145 |
| HPV16 | L1 | 9 | 196 |
| HPV16 | L1 | 10 | 196 |
| HPV16 | L1 | 11 | 196 |
| HPV16 | L1 | 8 | 134 |
| HPV16 | L1 | 10 | 134 |
| HPV16 | L1 | 8 | 491 |
| HPV16 | L1 | 10 | 491 |
| HPV16 | L1 | 9 | 101 |
| HPV16 | L1 | 11 | 101 |
| HPV16 | L1 | 8 | 417 |
| HPV16 | L1 | 9 | 417 |
| HPV16 | L1 | 8 | 303 |
| HPV16 | L1 | 10 | 303 |
| HPV16 | L1 | 11 | 303 |
| HPV16 | L1 | 9 | 78 |
| HPV16 | L1 | 10 | 78 |
| HPV16 | L1 | 11 | 78 |
| HPV16 | L1 | 8 | 261 |
| HPV16 | L1 | 8 | 79 |
| HPV16 | L1 | 9 | 79 |
| HPV16 | L1 | 10 | 79 |
| HPV16 | L1 | 8 | 468 |
| HPV16 | L1 | 10 | 468 |
| HPV16 | L1 | 9 | 500 |
| HPV16 | L1 | 9 | 477 |
| HPV16 | L1 | 9 | 467 |
| HPV16 | L1 | 11 | 467 |
| HPV16 | L1 | 9 | 390 |
| HPV16 | L1 | 11 | 390 |
| HPV16 | L1 | 8 | 276 |
| HPV16 | L1 | 11 | 276 |
| HPV16 | L1 | 10 | 107 |
| HPV16 | L1 | 11 | 107 |
| HPV16 | L1 | 8 | 84 |
| HPV16 | L1 | 11 | 84 |
| HPV16 | L1 | 9 | 150 |
| HPV16 | L1 | 11 | 150 |
| HPV16 | L1 | 9 | 334 |
| HPV16 | L1 | 9 | 242 |
| HPV16 | L1 | 10 | 288 |
| HPV16 | L1 | 9 | 169 |
| HPV16 | L1 | 9 | 462 |
| HPV16 | L1 | 11 | 462 |
| HPV16 | L1 | 10 | 504 |
| HPV16 | L1 | 8 | 89 |
| HPV16 | L1 | 10 | 89 |
| HPV16 | L1 | 11 | 89 |
| HPV16 | L1 | 10 | 340 |
| HPV16 | L1 | 8 | 122 |
| HPV16 | L1 | 10 | 122 |
| HPV16 | L1 | 8 | 391 |
| HPV16 | L1 | 10 | 391 |
| HPV16 | L1 | 11 | 391 |
| HPV16 | L1 | 9 | 284 |
| HPV16 | L1 | 10 | 284 |
| HPV16 | L1 | 9 | 492 |
| HPV16 | L1 | 11 | 492 |
| HPV16 | L1 | 10 | 277 |
| HPV16 | L1 | 11 | 277 |
| HPV16 | L1 | 9 | 45 |
| HPV16 | L1 | 10 | 45 |
| HPV16 | L1 | 11 | 45 |
| HPV16 | L1 | 10 | 66 |
| HPV16 | L1 | 11 | 66 |
| HPV16 | L1 | 8 | 363 |
| HPV16 | L1 | 10 | 363 |
| HPV16 | L1 | 11 | 363 |
| HPV16 | L1 | 8 | 283 |
| HPV16 | L1 | 10 | 283 |
| HPV16 | L1 | 11 | 283 |
| HPV16 | L1 | 8 | 61 |
| HPV16 | L1 | 9 | 61 |
| HPV16 | L1 | 10 | 61 |
| HPV16 | L1 | 11 | 61 |
| HPV16 | L1 | 9 | 21 |
| HPV16 | L1 | 10 | 21 |
| HPV16 | L1 | 11 | 21 |
| HPV16 | L1 | 9 | 381 |
| HPV16 | L1 | 10 | 381 |
| HPV16 | L1 | 8 | 177 |
| HPV16 | L1 | 9 | 177 |
| HPV16 | L1 | 8 | 444 |
| HPV16 | L1 | 9 | 444 |
| HPV16 | L1 | 10 | 444 |
| HPV16 | L1 | 8 | 96 |
| HPV16 | L2 | 9 | 7 |
| HPV16 | L2 | 9 | 322 |
| HPV16 | L2 | 11 | 22 |
| HPV16 | L2 | 10 | 179 |
| HPV16 | L2 | 8 | 317 |
| HPV16 | L2 | 10 | 317 |
| HPV16 | L2 | 11 | 317 |
| HPV16 | L2 | 8 | 38 |
| HPV16 | L2 | 9 | 38 |

TABLE XII-continued

HLA-B27 Supermotif Peptides

| 1 | 2 | 3 | 4 |
|---|---|---|---|
| HPV16 | L2 | 11 | 38 |
| HPV16 | L2 | 8 | 68 |
| HPV16 | L2 | 11 | 3 |
| HPV16 | L2 | 8 | 11 |
| HPV16 | L2 | 9 | 11 |
| HPV16 | L2 | 10 | 460 |
| HPV16 | L2 | 8 | 457 |
| HPV16 | L2 | 9 | 457 |
| HPV16 | L2 | 10 | 457 |
| HPV16 | L2 | 10 | 4 |
| HPV16 | L2 | 8 | 8 |
| HPV16 | L2 | 11 | 8 |
| HPV16 | L2 | 8 | 448 |
| HPV16 | L2 | 8 | 455 |
| HPV16 | L2 | 10 | 455 |
| HPV16 | L2 | 11 | 455 |
| HPV16 | L2 | 9 | 312 |
| HPV16 | L2 | 11 | 312 |
| HPV16 | L2 | 8 | 34 |
| HPV16 | L2 | 9 | 34 |
| HPV16 | L2 | 8 | 459 |
| HPV16 | L2 | 11 | 459 |
| HPV16 | L2 | 9 | 456 |
| HPV16 | L2 | 10 | 456 |
| HPV16 | L2 | 11 | 456 |
| HPV16 | L2 | 8 | 458 |
| HPV16 | L2 | 9 | 458 |
| HPV16 | L2 | 10 | 297 |
| HPV16 | L2 | 9 | 353 |
| HPV16 | L2 | 9 | 304 |
| HPV16 | L2 | 9 | 219 |
| HPV16 | L2 | 10 | 219 |
| HPV16 | L2 | 8 | 296 |
| HPV16 | L2 | 11 | 296 |
| HPV16 | L2 | 9 | 229 |
| HPV16 | L2 | 10 | 229 |
| HPV16 | L2 | 9 | 190 |
| HPV16 | L2 | 10 | 247 |
| HPV16 | L2 | 11 | 247 |
| HPV16 | L2 | 9 | 10 |
| HPV16 | L2 | 10 | 10 |
| HPV16 | L2 | 10 | 77 |
| HPV16 | L2 | 11 | 77 |
| HPV16 | L2 | 9 | 314 |
| HPV16 | L2 | 11 | 314 |
| HPV16 | L2 | 10 | 324 |
| HPV16 | L2 | 8 | 235 |
| HPV16 | L2 | 9 | 235 |
| HPV16 | L2 | 10 | 89 |
| HPV18 | E1 | 10 | 269 |
| HPV18 | E1 | 8 | 578 |
| HPV18 | E1 | 9 | 578 |
| HPV18 | E1 | 8 | 298 |
| HPV18 | E1 | 10 | 298 |
| HPV18 | E1 | 8 | 125 |
| HPV18 | E1 | 8 | 406 |
| HPV18 | E1 | 10 | 406 |
| HPV18 | E1 | 8 | 276 |
| HPV18 | E1 | 9 | 276 |
| HPV18 | E1 | 10 | 276 |
| HPV18 | E1 | 11 | 276 |
| HPV18 | E1 | 8 | 25 |
| HPV18 | E1 | 8 | 602 |
| HPV18 | E1 | 10 | 602 |
| HPV18 | E1 | 8 | 613 |
| HPV18 | E1 | 8 | 236 |
| HPV18 | E1 | 9 | 236 |
| HPV18 | E1 | 11 | 236 |
| HPV18 | E1 | 8 | 555 |
| HPV18 | E1 | 10 | 555 |
| HPV18 | E1 | 9 | 101 |
| HPV18 | E1 | 9 | 621 |
| HPV18 | E1 | 10 | 70 |
| HPV18 | E1 | 9 | 218 |
| HPV18 | E1 | 11 | 233 |
| HPV18 | E1 | 8 | 258 |
| HPV18 | E1 | 9 | 258 |
| HPV18 | E1 | 10 | 258 |
| HPV18 | E1 | 11 | 258 |
| HPV18 | E1 | 8 | 291 |
| HPV18 | E1 | 11 | 291 |
| HPV18 | E1 | 9 | 489 |
| HPV18 | E1 | 10 | 489 |
| HPV18 | E1 | 8 | 498 |
| HPV18 | E1 | 9 | 498 |
| HPV18 | E1 | 11 | 498 |
| HPV18 | E1 | 9 | 575 |
| HPV18 | E1 | 11 | 575 |
| HPV18 | E1 | 8 | 433 |
| HPV18 | E1 | 8 | 557 |
| HPV18 | E1 | 11 | 417 |
| HPV18 | E1 | 8 | 123 |
| HPV18 | E1 | 10 | 123 |
| HPV18 | E1 | 11 | 476 |
| HPV18 | E1 | 9 | 424 |
| HPV18 | E1 | 10 | 424 |
| HPV18 | E1 | 8 | 629 |
| HPV18 | E1 | 8 | 82 |
| HPV18 | E1 | 9 | 82 |
| HPV18 | E1 | 8 | 305 |
| HPV18 | E1 | 9 | 305 |
| HPV18 | E1 | 10 | 305 |
| HPV18 | E1 | 8 | 564 |
| HPV18 | E1 | 11 | 409 |
| HPV18 | E1 | 10 | 471 |
| HPV18 | E1 | 11 | 471 |
| HPV18 | E1 | 9 | 400 |
| HPV18 | E1 | 10 | 400 |
| HPV18 | E1 | 9 | 205 |
| HPV18 | E1 | 10 | 205 |
| HPV18 | E1 | 11 | 205 |
| HPV18 | E1 | 10 | 648 |
| HPV18 | E1 | 8 | 319 |
| HPV18 | E1 | 9 | 319 |
| HPV18 | E1 | 10 | 319 |
| HPV18 | E1 | 11 | 319 |
| HPV18 | E1 | 10 | 286 |
| HPV18 | E1 | 8 | 453 |
| HPV18 | E1 | 9 | 453 |
| HPV18 | E1 | 11 | 453 |
| HPV18 | E1 | 10 | 543 |
| HPV18 | E1 | 8 | 209 |
| HPV18 | E1 | 9 | 209 |
| HPV18 | E1 | 10 | 209 |
| HPV18 | E1 | 10 | 581 |
| HPV18 | E1 | 8 | 475 |
| HPV18 | E1 | 8 | 317 |
| HPV18 | E1 | 9 | 317 |
| HPV18 | E1 | 10 | 317 |
| HPV18 | E1 | 11 | 317 |
| HPV18 | E1 | 8 | 111 |
| HPV18 | E1 | 9 | 354 |
| HPV18 | E1 | 11 | 354 |
| HPV18 | E1 | 8 | 122 |
| HPV18 | E1 | 9 | 122 |
| HPV18 | E1 | 11 | 122 |
| HPV18 | E1 | 10 | 423 |
| HPV18 | E1 | 11 | 423 |
| HPV18 | E1 | 10 | 348 |
| HPV18 | E1 | 9 | 556 |
| HPV18 | E1 | 8 | 420 |
| HPV18 | E1 | 10 | 420 |
| HPV18 | E1 | 11 | 127 |
| HPV18 | E1 | 8 | 513 |
| HPV18 | E1 | 9 | 438 |
| HPV18 | E1 | 8 | 588 |
| HPV18 | E1 | 11 | 588 |
| HPV18 | E1 | 9 | 293 |
| HPV18 | E1 | 9 | 523 |
| HPV18 | E1 | 8 | 75 |

TABLE XII-continued

HLA-B27 Supermotif Peptides

| 1 | 2 | 3 | 4 |
|---|---|---|---|
| HPV18 | E1 | 10 | 75 |
| HPV18 | E1 | 11 | 75 |
| HPV18 | E1 | 9 | 616 |
| HPV18 | E1 | 8 | 446 |
| HPV18 | E1 | 10 | 446 |
| HPV18 | E1 | 8 | 288 |
| HPV18 | E1 | 10 | 288 |
| HPV18 | E1 | 11 | 288 |
| HPV18 | E1 | 9 | 419 |
| HPV18 | E1 | 11 | 419 |
| HPV18 | E1 | 8 | 329 |
| HPV18 | E1 | 11 | 329 |
| HPV18 | E2 | 9 | 73 |
| HPV18 | E2 | 10 | 73 |
| HPV18 | E2 | 11 | 73 |
| HPV18 | E2 | 9 | 237 |
| HPV18 | E2 | 10 | 237 |
| HPV18 | E2 | 9 | 50 |
| HPV18 | E2 | 10 | 21 |
| HPV18 | E2 | 10 | 311 |
| HPV18 | E2 | 8 | 295 |
| HPV18 | E2 | 10 | 295 |
| HPV18 | E2 | 11 | 52 |
| HPV18 | E2 | 8 | 256 |
| HPV18 | E2 | 11 | 256 |
| HPV18 | E2 | 8 | 328 |
| HPV18 | E2 | 10 | 328 |
| HPV18 | E2 | 9 | 181 |
| HPV18 | E2 | 11 | 181 |
| HPV18 | E2 | 10 | 10 |
| HPV18 | E2 | 11 | 10 |
| HPV18 | E2 | 8 | 114 |
| HPV18 | E2 | 10 | 114 |
| HPV18 | E2 | 11 | 114 |
| HPV18 | E2 | 8 | 176 |
| HPV18 | E2 | 8 | 74 |
| HPV18 | E2 | 9 | 74 |
| HPV18 | E2 | 10 | 74 |
| HPV18 | E2 | 11 | 159 |
| HPV18 | E2 | 10 | 290 |
| HPV18 | E2 | 8 | 40 |
| HPV18 | E2 | 9 | 40 |
| HPV18 | E2 | 10 | 40 |
| HPV18 | E2 | 11 | 40 |
| HPV18 | E2 | 9 | 308 |
| HPV18 | E2 | 9 | 115 |
| HPV18 | E2 | 10 | 115 |
| HPV18 | E2 | 11 | 115 |
| HPV18 | E2 | 8 | 299 |
| HPV18 | E2 | 8 | 292 |
| HPV18 | E2 | 11 | 292 |
| HPV18 | E2 | 8 | 306 |
| HPV18 | E2 | 11 | 306 |
| HPV18 | E2 | 8 | 59 |
| HPV18 | E2 | 10 | 59 |
| HPV18 | E2 | 8 | 128 |
| HPV18 | E2 | 9 | 128 |
| HPV18 | E2 | 10 | 128 |
| HPV18 | E2 | 11 | 128 |
| HPV18 | E2 | 9 | 4 |
| HPV18 | E2 | 9 | 258 |
| HPV18 | E2 | 10 | 258 |
| HPV18 | E2 | 11 | 222 |
| HPV18 | E2 | 9 | 342 |
| HPV18 | E2 | 10 | 342 |
| HPV18 | E2 | 11 | 342 |
| HPV18 | E2 | 10 | 307 |
| HPV18 | E2 | 11 | 279 |
| HPV18 | E2 | 8 | 158 |
| HPV18 | E2 | 9 | 71 |
| HPV18 | E2 | 11 | 71 |
| HPV18 | E2 | 8 | 27 |
| HPV18 | E2 | 10 | 27 |
| HPV18 | E2 | 11 | 27 |
| HPV18 | E2 | 8 | 69 |
| HPV18 | E2 | 9 | 69 |
| HPV18 | E2 | 11 | 69 |
| HPV18 | E2 | 8 | 89 |
| HPV18 | E2 | 10 | 89 |
| HPV18 | E2 | 11 | 111 |
| HPV18 | E2 | 8 | 344 |
| HPV18 | E2 | 9 | 344 |
| HPV18 | E2 | 8 | 247 |
| HPV18 | E2 | 9 | 247 |
| HPV18 | E2 | 8 | 191 |
| HPV18 | E2 | 8 | 165 |
| HPV18 | E2 | 9 | 165 |
| HPV18 | E2 | 10 | 165 |
| HPV18 | E2 | 11 | 218 |
| HPV18 | E2 | 10 | 337 |
| HPV18 | E2 | 11 | 337 |
| HPV18 | E2 | 8 | 91 |
| HPV18 | E2 | 8 | 313 |
| HPV18 | E2 | 10 | 313 |
| HPV18 | E2 | 10 | 304 |
| HPV18 | E5 | 9 | 18 |
| HPV18 | E5 | 11 | 18 |
| HPV18 | E5 | 9 | 64 |
| HPV18 | E6 | 11 | 2 |
| HPV18 | E6 | 8 | 65 |
| HPV18 | E6 | 11 | 65 |
| HPV18 | E6 | 8 | 138 |
| HPV18 | E6 | 10 | 35 |
| HPV18 | E6 | 11 | 35 |
| HPV18 | E6 | 8 | 91 |
| HPV18 | E6 | 9 | 91 |
| HPV18 | E6 | 11 | 91 |
| HPV18 | E6 | 8 | 123 |
| HPV18 | E6 | 9 | 123 |
| HPV18 | E6 | 11 | 148 |
| HPV18 | E6 | 8 | 127 |
| HPV18 | E6 | 8 | 49 |
| HPV18 | E6 | 10 | 66 |
| HPV18 | E6 | 10 | 103 |
| HPV18 | E6 | 11 | 75 |
| HPV18 | E6 | 8 | 124 |
| HPV18 | E6 | 11 | 124 |
| HPV18 | E6 | 10 | 106 |
| HPV18 | E6 | 10 | 118 |
| HPV18 | E6 | 8 | 78 |
| HPV18 | E6 | 9 | 78 |
| HPV18 | E6 | 8 | 143 |
| HPV18 | E6 | 9 | 61 |
| HPV18 | E6 | 11 | 61 |
| HPV18 | E6 | 10 | 109 |
| HPV18 | E6 | 8 | 151 |
| HPV18 | E6 | 9 | 119 |
| HPV18 | E6 | 8 | 79 |
| HPV18 | E6 | 10 | 125 |
| HPV18 | E6 | 9 | 9 |
| HPV18 | E6 | 9 | 73 |
| HPV18 | E6 | 10 | 8 |
| HPV18 | E6 | 10 | 12 |
| HPV18 | E6 | 8 | 56 |
| HPV18 | E6 | 9 | 56 |
| HPV18 | E7 | 11 | 70 |
| HPV18 | E7 | 11 | 51 |
| HPV18 | E7 | 9 | 66 |
| HPV18 | E7 | 10 | 66 |
| HPV18 | E7 | 11 | 66 |
| HPV18 | E7 | 9 | 72 |
| HPV18 | E7 | 9 | 13 |
| HPV18 | E7 | 11 | 13 |
| HPV18 | E7 | 8 | 83 |
| HPV18 | E7 | 9 | 83 |
| HPV18 | E7 | 8 | 1 |
| HPV18 | E7 | 11 | 1 |
| HPV18 | E7 | 10 | 45 |
| HPV18 | E7 | 8 | 4 |
| HPV18 | E7 | 9 | 4 |

TABLE XII-continued

HLA-B27 Supermotif Peptides

| 1 | 2 | 3 | 4 |
|---|---|---|---|
| HPV18 | E7 | 10 | 4 |
| HPV18 | E7 | 8 | 47 |
| HPV18 | E7 | 8 | 57 |
| HPV18 | E7 | 10 | 52 |
| HPV18 | E7 | 11 | 52 |
| HPV18 | L1 | 11 | 231 |
| HPV18 | L1 | 8 | 559 |
| HPV18 | L1 | 8 | 318 |
| HPV18 | L1 | 11 | 318 |
| HPV18 | L1 | 9 | 80 |
| HPV18 | L1 | 10 | 80 |
| HPV18 | L1 | 9 | 290 |
| HPV18 | L1 | 11 | 290 |
| HPV18 | L1 | 8 | 504 |
| HPV18 | L1 | 10 | 504 |
| HPV18 | L1 | 8 | 228 |
| HPV18 | L1 | 10 | 515 |
| HPV18 | L1 | 8 | 422 |
| HPV18 | L1 | 11 | 422 |
| HPV18 | L1 | 11 | 134 |
| HPV18 | L1 | 8 | 379 |
| HPV18 | L1 | 8 | 180 |
| HPV18 | L1 | 8 | 43 |
| HPV18 | L1 | 11 | 43 |
| HPV18 | L1 | 8 | 169 |
| HPV18 | L1 | 10 | 169 |
| HPV18 | L1 | 8 | 527 |
| HPV18 | L1 | 10 | 527 |
| HPV18 | L1 | 10 | 375 |
| HPV18 | L1 | 8 | 453 |
| HPV18 | L1 | 9 | 453 |
| HPV18 | L1 | 8 | 338 |
| HPV18 | L1 | 11 | 374 |
| HPV18 | L1 | 8 | 29 |
| HPV18 | L1 | 9 | 29 |
| HPV18 | L1 | 11 | 29 |
| HPV18 | L1 | 8 | 10 |
| HPV18 | L1 | 9 | 10 |
| HPV18 | L1 | 9 | 513 |
| HPV18 | L1 | 8 | 506 |
| HPV18 | L1 | 11 | 251 |
| HPV18 | L1 | 9 | 50 |
| HPV18 | L1 | 10 | 50 |
| HPV18 | L1 | 11 | 50 |
| HPV18 | L1 | 8 | 311 |
| HPV18 | L1 | 11 | 311 |
| HPV18 | L1 | 8 | 499 |
| HPV18 | L1 | 10 | 499 |
| HPV18 | L1 | 11 | 499 |
| HPV18 | L1 | 10 | 142 |
| HPV18 | L1 | 11 | 142 |
| HPV18 | L1 | 11 | 185 |
| HPV18 | L1 | 9 | 369 |
| HPV18 | L1 | 8 | 119 |
| HPV18 | L1 | 10 | 119 |
| HPV18 | L1 | 11 | 119 |
| HPV18 | L1 | 10 | 323 |
| HPV18 | L1 | 8 | 124 |
| HPV18 | L1 | 10 | 124 |
| HPV18 | L1 | 11 | 124 |
| HPV18 | L1 | 9 | 544 |
| HPV18 | L1 | 9 | 24 |
| HPV18 | L1 | 10 | 24 |
| HPV18 | L1 | 11 | 24 |
| HPV18 | L1 | 8 | 157 |
| HPV18 | L1 | 10 | 157 |
| HPV18 | L1 | 10 | 319 |
| HPV18 | L1 | 8 | 427 |
| HPV18 | L1 | 10 | 427 |
| HPV18 | L1 | 11 | 427 |
| HPV18 | L1 | 9 | 528 |
| HPV18 | L1 | 8 | 545 |
| HPV18 | L1 | 10 | 312 |
| HPV18 | L1 | 11 | 312 |
| HPV18 | L1 | 8 | 193 |
| HPV18 | L1 | 9 | 556 |
| HPV18 | L1 | 11 | 556 |
| HPV18 | L1 | 9 | 426 |
| HPV18 | L1 | 11 | 426 |
| HPV18 | L1 | 10 | 101 |
| HPV18 | L1 | 11 | 101 |
| HPV18 | L1 | 9 | 277 |
| HPV18 | L1 | 10 | 420 |
| HPV18 | L1 | 8 | 5 |
| HPV18 | L1 | 10 | 5 |
| HPV18 | L1 | 11 | 5 |
| HPV18 | L1 | 9 | 37 |
| HPV18 | L1 | 10 | 37 |
| HPV18 | L1 | 11 | 37 |
| HPV18 | L1 | 9 | 204 |
| HPV18 | L1 | 9 | 386 |
| HPV18 | L1 | 10 | 386 |
| HPV18 | L1 | 8 | 65 |
| HPV18 | L1 | 9 | 65 |
| HPV18 | L1 | 10 | 65 |
| HPV18 | L1 | 8 | 96 |
| HPV18 | L1 | 9 | 96 |
| HPV18 | L1 | 11 | 96 |
| HPV18 | L1 | 10 | 12 |
| HPV18 | L1 | 11 | 12 |
| HPV18 | L1 | 8 | 22 |
| HPV18 | L1 | 11 | 22 |
| HPV18 | L1 | 8 | 212 |
| HPV18 | L1 | 9 | 212 |
| HPV18 | L1 | 8 | 480 |
| HPV18 | L1 | 9 | 480 |
| HPV18 | L1 | 8 | 131 |
| HPV18 | L2 | 8 | 7 |
| HPV18 | L2 | 11 | 7 |
| HPV18 | L2 | 9 | 315 |
| HPV18 | L2 | 11 | 21 |
| HPV18 | L2 | 9 | 42 |
| HPV18 | L2 | 11 | 42 |
| HPV18 | L2 | 10 | 372 |
| HPV18 | L2 | 9 | 76 |
| HPV18 | L2 | 8 | 67 |
| HPV18 | L2 | 9 | 4 |
| HPV18 | L2 | 11 | 4 |
| HPV18 | L2 | 8 | 430 |
| HPV18 | L2 | 9 | 430 |
| HPV18 | L2 | 11 | 430 |
| HPV18 | L2 | 8 | 280 |
| HPV18 | L2 | 8 | 446 |
| HPV18 | L2 | 9 | 446 |
| HPV18 | L2 | 10 | 446 |
| HPV18 | L2 | 11 | 446 |
| HPV18 | L2 | 8 | 10 |
| HPV18 | L2 | 9 | 10 |
| HPV18 | L2 | 8 | 447 |
| HPV18 | L2 | 9 | 447 |
| HPV18 | L2 | 10 | 447 |
| HPV18 | L2 | 8 | 449 |
| HPV18 | L2 | 11 | 449 |
| HPV18 | L2 | 9 | 445 |
| HPV18 | L2 | 10 | 445 |
| HPV18 | L2 | 11 | 445 |
| HPV18 | L2 | 8 | 33 |
| HPV18 | L2 | 9 | 33 |
| HPV18 | L2 | 8 | 224 |
| HPV18 | L2 | 11 | 224 |
| HPV18 | L2 | 11 | 118 |
| HPV18 | L2 | 10 | 267 |
| HPV18 | L2 | 11 | 267 |
| HPV18 | L2 | 9 | 9 |
| HPV18 | L2 | 10 | 9 |
| HPV18 | L2 | 8 | 448 |
| HPV18 | L2 | 9 | 448 |
| HPV18 | L2 | 10 | 290 |
| HPV18 | L2 | 10 | 8 |
| HPV18 | L2 | 11 | 8 |

TABLE XII-continued

HLA-B27 Supermotif Peptides

| 1 | 2 | 3 | 4 |
|---|---|---|---|
| HPV18 | L2 | 8 | 219 |
| HPV18 | L2 | 9 | 219 |
| HPV18 | L2 | 10 | 3 |
| HPV18 | L2 | 9 | 228 |
| HPV18 | L2 | 10 | 228 |
| HPV18 | L2 | 9 | 297 |
| HPV18 | L2 | 10 | 297 |
| HPV18 | L2 | 8 | 289 |
| HPV18 | L2 | 11 | 289 |
| HPV18 | L2 | 8 | 363 |
| HPV18 | L2 | 9 | 363 |
| HPV18 | L2 | 10 | 363 |
| HPV18 | L2 | 9 | 189 |
| HPV18 | L2 | 8 | 433 |
| HPV18 | L2 | 9 | 433 |
| HPV18 | L2 | 10 | 433 |
| HPV18 | L2 | 11 | 433 |
| HPV18 | L2 | 10 | 87 |
| HPV18 | L2 | 9 | 243 |
| HPV18 | L2 | 9 | 307 |
| HPV18 | L2 | 11 | 307 |
| HPV18 | L2 | 10 | 317 |
| HPV18 | L2 | 11 | 317 |
| HPV18 | L2 | 10 | 294 |
| HPV18 | L2 | 9 | 218 |
| HPV18 | L2 | 10 | 218 |
| HPV18 | L2 | 8 | 320 |
| HPV31 | E1 | 9 | 496 |
| HPV31 | E1 | 10 | 379 |
| HPV31 | E1 | 10 | 264 |
| HPV31 | E1 | 11 | 264 |
| HPV31 | E1 | 8 | 121 |
| HPV31 | E1 | 10 | 242 |
| HPV31 | E1 | 9 | 607 |
| HPV31 | E1 | 8 | 575 |
| HPV31 | E1 | 10 | 575 |
| HPV31 | E1 | 8 | 586 |
| HPV31 | E1 | 9 | 411 |
| HPV31 | E1 | 8 | 25 |
| HPV31 | E1 | 10 | 554 |
| HPV31 | E1 | 11 | 554 |
| HPV31 | E1 | 8 | 77 |
| HPV31 | E1 | 9 | 77 |
| HPV31 | E1 | 11 | 275 |
| HPV31 | E1 | 8 | 271 |
| HPV31 | E1 | 10 | 271 |
| HPV31 | E1 | 10 | 396 |
| HPV31 | E1 | 11 | 396 |
| HPV31 | E1 | 11 | 164 |
| HPV31 | E1 | 10 | 321 |
| HPV31 | E1 | 10 | 70 |
| HPV31 | E1 | 8 | 261 |
| HPV31 | E1 | 10 | 261 |
| HPV31 | E1 | 9 | 618 |
| HPV31 | E1 | 9 | 191 |
| HPV31 | E1 | 10 | 191 |
| HPV31 | E1 | 8 | 231 |
| HPV31 | E1 | 10 | 231 |
| HPV31 | E1 | 11 | 231 |
| HPV31 | E1 | 9 | 183 |
| HPV31 | E1 | 8 | 551 |
| HPV31 | E1 | 9 | 551 |
| HPV31 | E1 | 9 | 189 |
| HPV31 | E1 | 11 | 189 |
| HPV31 | E1 | 9 | 462 |
| HPV31 | E1 | 10 | 462 |
| HPV31 | E1 | 11 | 455 |
| HPV31 | E1 | 8 | 406 |
| HPV31 | E1 | 8 | 530 |
| HPV31 | E1 | 10 | 449 |
| HPV31 | E1 | 8 | 393 |
| HPV31 | E1 | 10 | 393 |
| HPV31 | E1 | 9 | 86 |
| HPV31 | E1 | 9 | 397 |
| HPV31 | E1 | 10 | 397 |
| HPV31 | E1 | 8 | 559 |
| HPV31 | E1 | 10 | 559 |
| HPV31 | E1 | 8 | 537 |
| HPV31 | E1 | 10 | 444 |
| HPV31 | E1 | 11 | 444 |
| HPV31 | E1 | 8 | 440 |
| HPV31 | E1 | 10 | 85 |
| HPV31 | E1 | 9 | 373 |
| HPV31 | E1 | 10 | 373 |
| HPV31 | E1 | 8 | 178 |
| HPV31 | E1 | 9 | 178 |
| HPV31 | E1 | 10 | 178 |
| HPV31 | E1 | 11 | 178 |
| HPV31 | E1 | 10 | 516 |
| HPV31 | E1 | 8 | 292 |
| HPV31 | E1 | 9 | 292 |
| HPV31 | E1 | 10 | 292 |
| HPV31 | E1 | 11 | 292 |
| HPV31 | E1 | 8 | 426 |
| HPV31 | E1 | 9 | 426 |
| HPV31 | E1 | 11 | 426 |
| HPV31 | E1 | 8 | 209 |
| HPV31 | E1 | 10 | 209 |
| HPV31 | E1 | 11 | 209 |
| HPV31 | E1 | 8 | 266 |
| HPV31 | E1 | 9 | 266 |
| HPV31 | E1 | 8 | 448 |
| HPV31 | E1 | 11 | 448 |
| HPV31 | E1 | 8 | 290 |
| HPV31 | E1 | 9 | 290 |
| HPV31 | E1 | 10 | 290 |
| HPV31 | E1 | 11 | 290 |
| HPV31 | E1 | 8 | 107 |
| HPV31 | E1 | 9 | 327 |
| HPV31 | E1 | 11 | 327 |
| HPV31 | E1 | 11 | 390 |
| HPV31 | E1 | 8 | 87 |
| HPV31 | E1 | 11 | 87 |
| HPV31 | E1 | 11 | 123 |
| HPV31 | E1 | 8 | 486 |
| HPV31 | E1 | 9 | 486 |
| HPV31 | E1 | 11 | 486 |
| HPV31 | E1 | 10 | 484 |
| HPV31 | E1 | 11 | 484 |
| HPV31 | E1 | 8 | 118 |
| HPV31 | E1 | 9 | 118 |
| HPV31 | E1 | 11 | 118 |
| HPV31 | E1 | 8 | 561 |
| HPV31 | E1 | 9 | 594 |
| HPV31 | E1 | 8 | 171 |
| HPV31 | E1 | 11 | 382 |
| HPV31 | E1 | 9 | 423 |
| HPV31 | E1 | 11 | 423 |
| HPV31 | E1 | 9 | 529 |
| HPV31 | E1 | 10 | 259 |
| HPV31 | E1 | 8 | 509 |
| HPV31 | E1 | 11 | 509 |
| HPV31 | E1 | 9 | 589 |
| HPV31 | E1 | 8 | 419 |
| HPV31 | E1 | 10 | 419 |
| HPV31 | E1 | 9 | 392 |
| HPV31 | E1 | 11 | 392 |
| HPV31 | E1 | 8 | 302 |
| HPV31 | E1 | 11 | 302 |
| HPV31 | E2 | 9 | 67 |
| HPV31 | E2 | 11 | 67 |
| HPV31 | E2 | 10 | 175 |
| HPV31 | E2 | 9 | 46 |
| HPV31 | E2 | 9 | 28 |
| HPV31 | E2 | 11 | 28 |
| HPV31 | E2 | 11 | 251 |
| HPV31 | E2 | 10 | 17 |
| HPV31 | E2 | 9 | 163 |
| HPV31 | E2 | 8 | 333 |
| HPV31 | E2 | 10 | 333 |

TABLE XII-continued

HLA-B27 Supermotif Peptides

| 1 | 2 | 3 | 4 |
|---|---|---|---|
| HPV31 | E2 | 8 | 181 |
| HPV31 | E2 | 8 | 335 |
| HPV31 | E2 | 10 | 335 |
| HPV31 | E2 | 11 | 335 |
| HPV31 | E2 | 10 | 252 |
| HPV31 | E2 | 11 | 252 |
| HPV31 | E2 | 9 | 296 |
| HPV31 | E2 | 10 | 296 |
| HPV31 | E2 | 8 | 51 |
| HPV31 | E2 | 9 | 51 |
| HPV31 | E2 | 11 | 51 |
| HPV31 | E2 | 8 | 36 |
| HPV31 | E2 | 9 | 36 |
| HPV31 | E2 | 11 | 36 |
| HPV31 | E2 | 8 | 112 |
| HPV31 | E2 | 10 | 112 |
| HPV31 | E2 | 8 | 34 |
| HPV31 | E2 | 9 | 34 |
| HPV31 | E2 | 10 | 34 |
| HPV31 | E2 | 11 | 34 |
| HPV31 | E2 | 9 | 334 |
| HPV31 | E2 | 11 | 334 |
| HPV31 | E2 | 9 | 111 |
| HPV31 | E2 | 11 | 111 |
| HPV31 | E2 | 11 | 182 |
| HPV31 | E2 | 9 | 176 |
| HPV31 | E2 | 11 | 176 |
| HPV31 | E2 | 9 | 24 |
| HPV31 | E2 | 10 | 24 |
| HPV31 | E2 | 8 | 305 |
| HPV31 | E2 | 11 | 305 |
| HPV31 | E2 | 8 | 298 |
| HPV31 | E2 | 11 | 298 |
| HPV31 | E2 | 8 | 110 |
| HPV31 | E2 | 10 | 110 |
| HPV31 | E2 | 9 | 262 |
| HPV31 | E2 | 8 | 308 |
| HPV31 | E2 | 11 | 308 |
| HPV31 | E2 | 8 | 129 |
| HPV31 | E2 | 9 | 129 |
| HPV31 | E2 | 10 | 129 |
| HPV31 | E2 | 11 | 129 |
| HPV31 | E2 | 8 | 55 |
| HPV31 | E2 | 10 | 55 |
| HPV31 | E2 | 9 | 259 |
| HPV31 | E2 | 9 | 349 |
| HPV31 | E2 | 11 | 349 |
| HPV31 | E2 | 10 | 6 |
| HPV31 | E2 | 11 | 6 |
| HPV31 | E2 | 8 | 65 |
| HPV31 | E2 | 9 | 65 |
| HPV31 | E2 | 11 | 65 |
| HPV31 | E2 | 8 | 23 |
| HPV31 | E2 | 10 | 23 |
| HPV31 | E2 | 11 | 23 |
| HPV31 | E2 | 10 | 313 |
| HPV31 | E2 | 8 | 255 |
| HPV31 | E2 | 8 | 284 |
| HPV31 | E2 | 8 | 186 |
| HPV31 | E2 | 9 | 186 |
| HPV31 | E2 | 10 | 186 |
| HPV31 | E2 | 8 | 160 |
| HPV31 | E2 | 9 | 160 |
| HPV31 | E2 | 10 | 160 |
| HPV31 | E2 | 10 | 125 |
| HPV31 | E2 | 9 | 357 |
| HPV31 | E2 | 8 | 134 |
| HPV31 | E2 | 9 | 33 |
| HPV31 | E2 | 10 | 33 |
| HPV31 | E2 | 11 | 33 |
| HPV31 | E2 | 8 | 44 |
| HPV31 | E2 | 11 | 44 |
| HPV31 | E2 | 8 | 87 |
| HPV31 | E2 | 8 | 315 |
| HPV31 | E2 | 9 | 310 |
| HPV31 | E2 | 10 | 310 |
| HPV31 | E5 | 8 | 74 |
| HPV31 | E5 | 8 | 29 |
| HPV31 | E5 | 10 | 29 |
| HPV31 | E5 | 11 | 29 |
| HPV31 | E5 | 8 | 57 |
| HPV31 | E5 | 9 | 57 |
| HPV31 | E5 | 10 | 57 |
| HPV31 | E5 | 11 | 57 |
| HPV31 | E6 | 10 | 33 |
| HPV31 | E6 | 11 | 33 |
| HPV31 | E6 | 9 | 120 |
| HPV31 | E6 | 8 | 89 |
| HPV31 | E6 | 11 | 89 |
| HPV31 | E6 | 9 | 7 |
| HPV31 | E6 | 8 | 125 |
| HPV31 | E6 | 11 | 2 |
| HPV31 | E6 | 8 | 76 |
| HPV31 | E6 | 9 | 76 |
| HPV31 | E6 | 8 | 130 |
| HPV31 | E6 | 9 | 130 |
| HPV31 | E6 | 11 | 130 |
| HPV31 | E6 | 10 | 101 |
| HPV31 | E6 | 8 | 121 |
| HPV31 | E6 | 11 | 122 |
| HPV31 | E6 | 10 | 123 |
| HPV31 | E6 | 8 | 12 |
| HPV31 | E6 | 10 | 12 |
| HPV31 | E6 | 10 | 67 |
| HPV31 | E6 | 8 | 93 |
| HPV31 | E6 | 9 | 93 |
| HPV31 | E6 | 9 | 59 |
| HPV31 | E6 | 11 | 59 |
| HPV31 | E6 | 10 | 9 |
| HPV31 | E6 | 11 | 9 |
| HPV31 | E6 | 10 | 115 |
| HPV31 | E6 | 9 | 117 |
| HPV31 | E6 | 9 | 10 |
| HPV31 | E6 | 10 | 10 |
| HPV31 | E6 | 9 | 141 |
| HPV31 | E6 | 8 | 71 |
| HPV31 | E6 | 9 | 71 |
| HPV31 | E6 | 11 | 71 |
| HPV31 | E6 | 10 | 64 |
| HPV31 | E6 | 10 | 140 |
| HPV31 | E6 | 9 | 54 |
| HPV31 | E6 | 10 | 79 |
| HPV31 | E7 | 9 | 61 |
| HPV31 | E7 | 8 | 76 |
| HPV31 | E7 | 9 | 76 |
| HPV31 | E7 | 10 | 65 |
| HPV31 | E7 | 8 | 1 |
| HPV31 | E7 | 11 | 1 |
| HPV31 | L1 | 10 | 40 |
| HPV31 | L1 | 11 | 40 |
| HPV31 | L1 | 9 | 380 |
| HPV31 | L1 | 10 | 380 |
| HPV31 | L1 | 9 | 162 |
| HPV31 | L1 | 9 | 230 |
| HPV31 | L1 | 10 | 230 |
| HPV31 | L1 | 11 | 230 |
| HPV31 | L1 | 10 | 454 |
| HPV31 | L1 | 8 | 481 |
| HPV31 | L1 | 11 | 481 |
| HPV31 | L1 | 9 | 442 |
| HPV31 | L1 | 11 | 442 |
| HPV31 | L1 | 11 | 361 |
| HPV31 | L1 | 9 | 356 |
| HPV31 | L1 | 10 | 356 |
| HPV31 | L1 | 11 | 356 |
| HPV31 | L1 | 11 | 74 |
| HPV31 | L1 | 8 | 319 |
| HPV31 | L1 | 8 | 120 |
| HPV31 | L1 | 10 | 171 |
| HPV31 | L1 | 11 | 171 |
| HPV31 | L1 | 8 | 484 |

TABLE XII-continued

HLA-B27 Supermotif Peptides

| 1 | 2 | 3 | 4 |
|---|---|---|---|
| HPV31 | L1 | 8 | 109 |
| HPV31 | L1 | 10 | 109 |
| HPV31 | L1 | 8 | 466 |
| HPV31 | L1 | 10 | 466 |
| HPV31 | L1 | 8 | 392 |
| HPV31 | L1 | 9 | 392 |
| HPV31 | L1 | 8 | 278 |
| HPV31 | L1 | 10 | 278 |
| HPV31 | L1 | 11 | 278 |
| HPV31 | L1 | 8 | 59 |
| HPV31 | L1 | 11 | 59 |
| HPV31 | L1 | 9 | 452 |
| HPV31 | L1 | 8 | 236 |
| HPV31 | L1 | 11 | 191 |
| HPV31 | L1 | 9 | 365 |
| HPV31 | L1 | 11 | 365 |
| HPV31 | L1 | 8 | 251 |
| HPV31 | L1 | 11 | 251 |
| HPV31 | L1 | 10 | 82 |
| HPV31 | L1 | 11 | 82 |
| HPV31 | L1 | 9 | 309 |
| HPV31 | L1 | 9 | 144 |
| HPV31 | L1 | 10 | 263 |
| HPV31 | L1 | 9 | 437 |
| HPV31 | L1 | 10 | 437 |
| HPV31 | L1 | 11 | 437 |
| HPV31 | L1 | 10 | 479 |
| HPV31 | L1 | 9 | 58 |
| HPV31 | L1 | 9 | 53 |
| HPV31 | L1 | 10 | 53 |
| HPV31 | L1 | 11 | 53 |
| HPV31 | L1 | 8 | 64 |
| HPV31 | L1 | 10 | 64 |
| HPV31 | L1 | 11 | 64 |
| HPV31 | L1 | 8 | 435 |
| HPV31 | L1 | 11 | 435 |
| HPV31 | L1 | 10 | 315 |
| HPV31 | L1 | 8 | 97 |
| HPV31 | L1 | 10 | 97 |
| HPV31 | L1 | 10 | 259 |
| HPV31 | L1 | 8 | 366 |
| HPV31 | L1 | 10 | 366 |
| HPV31 | L1 | 11 | 366 |
| HPV31 | L1 | 9 | 467 |
| HPV31 | L1 | 11 | 467 |
| HPV31 | L1 | 10 | 252 |
| HPV31 | L1 | 11 | 252 |
| HPV31 | L1 | 9 | 19 |
| HPV31 | L1 | 10 | 19 |
| HPV31 | L1 | 9 | 217 |
| HPV31 | L1 | 8 | 338 |
| HPV31 | L1 | 10 | 338 |
| HPV31 | L1 | 11 | 338 |
| HPV31 | L1 | 9 | 29 |
| HPV31 | L1 | 11 | 258 |
| HPV31 | L1 | 9 | 76 |
| HPV31 | L1 | 11 | 76 |
| HPV31 | L1 | 8 | 4 |
| HPV31 | L1 | 9 | 4 |
| HPV31 | L1 | 10 | 4 |
| HPV31 | L1 | 8 | 35 |
| HPV31 | L1 | 9 | 35 |
| HPV31 | L1 | 11 | 35 |
| HPV31 | L1 | 8 | 152 |
| HPV31 | L1 | 9 | 152 |
| HPV31 | L1 | 9 | 475 |
| HPV31 | L1 | 8 | 419 |
| HPV31 | L1 | 9 | 419 |
| HPV31 | L1 | 8 | 71 |
| HPV31 | L2 | 9 | 218 |
| HPV31 | L2 | 9 | 315 |
| HPV31 | L2 | 11 | 22 |
| HPV31 | L2 | 8 | 412 |
| HPV31 | L2 | 10 | 412 |
| HPV31 | L2 | 9 | 37 |
| HPV31 | L2 | 10 | 37 |
| HPV31 | L2 | 10 | 174 |
| HPV31 | L2 | 8 | 68 |
| HPV31 | L2 | 10 | 89 |
| HPV31 | L2 | 8 | 11 |
| HPV31 | L2 | 9 | 11 |
| HPV31 | L2 | 9 | 449 |
| HPV31 | L2 | 10 | 449 |
| HPV31 | L2 | 11 | 449 |
| HPV31 | L2 | 10 | 4 |
| HPV31 | L2 | 8 | 8 |
| HPV31 | L2 | 11 | 8 |
| HPV31 | L2 | 10 | 453 |
| HPV31 | L2 | 8 | 441 |
| HPV31 | L2 | 8 | 448 |
| HPV31 | L2 | 10 | 448 |
| HPV31 | L2 | 11 | 448 |
| HPV31 | L2 | 9 | 305 |
| HPV31 | L2 | 11 | 305 |
| HPV31 | L2 | 8 | 46 |
| HPV31 | L2 | 9 | 46 |
| HPV31 | L2 | 10 | 46 |
| HPV31 | L2 | 11 | 301 |
| HPV31 | L2 | 9 | 124 |
| HPV31 | L2 | 11 | 124 |
| HPV31 | L2 | 8 | 34 |
| HPV31 | L2 | 9 | 34 |
| HPV31 | L2 | 11 | 241 |
| HPV31 | L2 | 8 | 452 |
| HPV31 | L2 | 11 | 452 |
| HPV31 | L2 | 8 | 451 |
| HPV31 | L2 | 9 | 451 |
| HPV31 | L2 | 10 | 290 |
| HPV31 | L2 | 8 | 215 |
| HPV31 | L2 | 9 | 215 |
| HPV31 | L2 | 8 | 450 |
| HPV31 | L2 | 9 | 450 |
| HPV31 | L2 | 10 | 450 |
| HPV31 | L2 | 10 | 267 |
| HPV31 | L2 | 11 | 267 |
| HPV31 | L2 | 9 | 224 |
| HPV31 | L2 | 10 | 224 |
| HPV31 | L2 | 11 | 3 |
| HPV31 | L2 | 9 | 297 |
| HPV31 | L2 | 8 | 289 |
| HPV31 | L2 | 11 | 289 |
| HPV31 | L2 | 9 | 368 |
| HPV31 | L2 | 10 | 368 |
| HPV31 | L2 | 9 | 185 |
| HPV31 | L2 | 9 | 10 |
| HPV31 | L2 | 10 | 10 |
| HPV31 | L2 | 9 | 7 |
| HPV31 | L2 | 9 | 77 |
| HPV31 | L2 | 11 | 77 |
| HPV31 | L2 | 9 | 307 |
| HPV31 | L2 | 11 | 307 |
| HPV31 | L2 | 10 | 317 |
| HPV31 | L2 | 8 | 230 |
| HPV31 | L2 | 9 | 230 |
| HPV31 | L2 | 11 | 230 |
| HPV31 | L2 | 9 | 214 |
| HPV31 | L2 | 10 | 214 |
| HPV33 | E1 | 9 | 509 |
| HPV33 | E1 | 9 | 392 |
| HPV33 | E1 | 10 | 392 |
| HPV33 | E1 | 8 | 284 |
| HPV33 | E1 | 10 | 284 |
| HPV33 | E1 | 9 | 620 |
| HPV33 | E1 | 8 | 222 |
| HPV33 | E1 | 10 | 222 |
| HPV33 | E1 | 11 | 102 |
| HPV33 | E1 | 8 | 263 |
| HPV33 | E1 | 9 | 263 |
| HPV33 | E1 | 10 | 263 |
| HPV33 | E1 | 10 | 334 |

TABLE XII-continued

HLA-B27 Supermotif Peptides

| 1 | 2 | 3 | 4 |
|---|---|---|---|
| HPV33 | E1 | 10 | 409 |
| HPV33 | E1 | 11 | 409 |
| HPV33 | E1 | 9 | 424 |
| HPV33 | E1 | 8 | 25 |
| HPV33 | E1 | 9 | 204 |
| HPV33 | E1 | 10 | 204 |
| HPV33 | E1 | 8 | 453 |
| HPV33 | E1 | 11 | 219 |
| HPV33 | E1 | 8 | 274 |
| HPV33 | E1 | 10 | 274 |
| HPV33 | E1 | 11 | 274 |
| HPV33 | E1 | 8 | 315 |
| HPV33 | E1 | 11 | 315 |
| HPV33 | E1 | 9 | 475 |
| HPV33 | E1 | 10 | 475 |
| HPV33 | E1 | 10 | 248 |
| HPV33 | E1 | 10 | 272 |
| HPV33 | E1 | 8 | 543 |
| HPV33 | E1 | 8 | 406 |
| HPV33 | E1 | 10 | 406 |
| HPV33 | E1 | 11 | 462 |
| HPV33 | E1 | 11 | 86 |
| HPV33 | E1 | 9 | 410 |
| HPV33 | E1 | 10 | 410 |
| HPV33 | E1 | 8 | 572 |
| HPV33 | E1 | 10 | 572 |
| HPV33 | E1 | 8 | 191 |
| HPV33 | E1 | 10 | 191 |
| HPV33 | E1 | 11 | 191 |
| HPV33 | E1 | 8 | 550 |
| HPV33 | E1 | 9 | 487 |
| HPV33 | E1 | 10 | 457 |
| HPV33 | E1 | 11 | 457 |
| HPV33 | E1 | 9 | 386 |
| HPV33 | E1 | 10 | 386 |
| HPV33 | E1 | 10 | 244 |
| HPV33 | E1 | 11 | 244 |
| HPV33 | E1 | 8 | 305 |
| HPV33 | E1 | 9 | 305 |
| HPV33 | E1 | 10 | 305 |
| HPV33 | E1 | 11 | 305 |
| HPV33 | E1 | 8 | 439 |
| HPV33 | E1 | 10 | 439 |
| HPV33 | E1 | 11 | 439 |
| HPV33 | E1 | 10 | 529 |
| HPV33 | E1 | 9 | 623 |
| HPV33 | E1 | 11 | 115 |
| HPV33 | E1 | 8 | 113 |
| HPV33 | E1 | 8 | 279 |
| HPV33 | E1 | 9 | 279 |
| HPV33 | E1 | 8 | 461 |
| HPV33 | E1 | 9 | 303 |
| HPV33 | E1 | 10 | 303 |
| HPV33 | E1 | 11 | 303 |
| HPV33 | E1 | 8 | 340 |
| HPV33 | E1 | 9 | 340 |
| HPV33 | E1 | 11 | 340 |
| HPV33 | E1 | 8 | 250 |
| HPV33 | E1 | 11 | 250 |
| HPV33 | E1 | 11 | 403 |
| HPV33 | E1 | 10 | 87 |
| HPV33 | E1 | 11 | 87 |
| HPV33 | E1 | 11 | 123 |
| HPV33 | E1 | 8 | 411 |
| HPV33 | E1 | 9 | 411 |
| HPV33 | E1 | 8 | 121 |
| HPV33 | E1 | 8 | 499 |
| HPV33 | E1 | 11 | 499 |
| HPV33 | E1 | 8 | 277 |
| HPV33 | E1 | 10 | 277 |
| HPV33 | E1 | 11 | 277 |
| HPV33 | E1 | 10 | 497 |
| HPV33 | E1 | 8 | 574 |
| HPV33 | E1 | 9 | 607 |
| HPV33 | E1 | 10 | 607 |
| HPV33 | E1 | 10 | 567 |
| HPV33 | E1 | 9 | 196 |
| HPV33 | E1 | 11 | 395 |
| HPV33 | E1 | 9 | 542 |
| HPV33 | E1 | 9 | 602 |
| HPV33 | E1 | 8 | 432 |
| HPV33 | E1 | 10 | 432 |
| HPV33 | E1 | 9 | 202 |
| HPV33 | E1 | 11 | 202 |
| HPV33 | E1 | 9 | 405 |
| HPV33 | E1 | 11 | 405 |
| HPV33 | E1 | 9 | 120 |
| HPV33 | E2 | 9 | 46 |
| HPV33 | E2 | 8 | 176 |
| HPV33 | E2 | 9 | 176 |
| HPV33 | E2 | 11 | 176 |
| HPV33 | E2 | 10 | 6 |
| HPV33 | E2 | 11 | 6 |
| HPV33 | E2 | 8 | 55 |
| HPV33 | E2 | 9 | 55 |
| HPV33 | E2 | 10 | 55 |
| HPV33 | E2 | 8 | 124 |
| HPV33 | E2 | 11 | 124 |
| HPV33 | E2 | 9 | 22 |
| HPV33 | E2 | 8 | 31 |
| HPV33 | E2 | 11 | 31 |
| HPV33 | E2 | 9 | 13 |
| HPV33 | E2 | 8 | 164 |
| HPV33 | E2 | 8 | 171 |
| HPV33 | E2 | 8 | 110 |
| HPV33 | E2 | 10 | 110 |
| HPV33 | E2 | 8 | 168 |
| HPV33 | E2 | 9 | 168 |
| HPV33 | E2 | 11 | 168 |
| HPV33 | E2 | 8 | 150 |
| HPV33 | E2 | 9 | 150 |
| HPV33 | E2 | 10 | 150 |
| HPV33 | E2 | 11 | 150 |
| HPV33 | E2 | 8 | 160 |
| HPV33 | E2 | 9 | 160 |
| HPV33 | E2 | 11 | 160 |
| HPV33 | E2 | 8 | 36 |
| HPV33 | E2 | 9 | 36 |
| HPV33 | E2 | 11 | 36 |
| HPV33 | E2 | 10 | 125 |
| HPV33 | E2 | 9 | 111 |
| HPV33 | E2 | 11 | 111 |
| HPV33 | E2 | 8 | 286 |
| HPV33 | E2 | 11 | 286 |
| HPV33 | E2 | 8 | 279 |
| HPV33 | E2 | 11 | 279 |
| HPV33 | E2 | 8 | 293 |
| HPV33 | E2 | 11 | 293 |
| HPV33 | E2 | 8 | 289 |
| HPV33 | E2 | 11 | 289 |
| HPV33 | E2 | 8 | 313 |
| HPV33 | E2 | 9 | 313 |
| HPV33 | E2 | 11 | 313 |
| HPV33 | E2 | 11 | 263 |
| HPV33 | E2 | 8 | 218 |
| HPV33 | E2 | 11 | 107 |
| HPV33 | E2 | 9 | 265 |
| HPV33 | E2 | 10 | 265 |
| HPV33 | E2 | 10 | 228 |
| HPV33 | E2 | 11 | 227 |
| HPV33 | E2 | 8 | 52 |
| HPV33 | E2 | 11 | 52 |
| HPV33 | E2 | 8 | 316 |
| HPV33 | E2 | 10 | 316 |
| HPV33 | E2 | 11 | 316 |
| HPV33 | E2 | 10 | 83 |
| HPV33 | E2 | 8 | 65 |
| HPV33 | E2 | 9 | 65 |
| HPV33 | E2 | 11 | 65 |
| HPV33 | E2 | 8 | 179 |

TABLE XII-continued

HLA-B27 Supermotif Peptides

| 1 | 2 | 3 | 4 |
|---|---|---|---|
| HPV33 | E2 | 10 | 179 |
| HPV33 | E2 | 9 | 67 |
| HPV33 | E2 | 11 | 67 |
| HPV33 | E2 | 9 | 241 |
| HPV33 | E2 | 10 | 241 |
| HPV33 | E2 | 10 | 277 |
| HPV33 | E2 | 8 | 186 |
| HPV33 | E2 | 9 | 186 |
| HPV33 | E2 | 9 | 338 |
| HPV33 | E2 | 9 | 33 |
| HPV33 | E2 | 10 | 33 |
| HPV33 | E2 | 11 | 33 |
| HPV33 | E2 | 8 | 296 |
| HPV33 | E2 | 9 | 291 |
| HPV33 | E2 | 10 | 291 |
| HPV33 | E5 | 8 | 47 |
| HPV33 | E5 | 9 | 47 |
| HPV33 | E5 | 10 | 47 |
| HPV33 | E5 | 11 | 47 |
| HPV33 | E5 | 8 | 19 |
| HPV33 | E5 | 11 | 19 |
| HPV33 | E6 | 10 | 33 |
| HPV33 | E6 | 11 | 33 |
| HPV33 | E6 | 8 | 63 |
| HPV33 | E6 | 11 | 63 |
| HPV33 | E6 | 8 | 114 |
| HPV33 | E6 | 9 | 7 |
| HPV33 | E6 | 8 | 125 |
| HPV33 | E6 | 9 | 125 |
| HPV33 | E6 | 8 | 130 |
| HPV33 | E6 | 9 | 130 |
| HPV33 | E6 | 11 | 130 |
| HPV33 | E6 | 9 | 23 |
| HPV33 | E6 | 10 | 101 |
| HPV33 | E6 | 8 | 93 |
| HPV33 | E6 | 9 | 93 |
| HPV33 | E6 | 9 | 34 |
| HPV33 | E6 | 10 | 34 |
| HPV33 | E6 | 11 | 115 |
| HPV33 | E6 | 10 | 123 |
| HPV33 | E6 | 11 | 123 |
| HPV33 | E6 | 10 | 116 |
| HPV33 | E6 | 8 | 12 |
| HPV33 | E6 | 10 | 67 |
| HPV33 | E6 | 11 | 122 |
| HPV33 | E6 | 10 | 9 |
| HPV33 | E6 | 11 | 9 |
| HPV33 | E6 | 8 | 38 |
| HPV33 | E6 | 9 | 38 |
| HPV33 | E6 | 10 | 38 |
| HPV33 | E6 | 11 | 38 |
| HPV33 | E6 | 9 | 117 |
| HPV33 | E6 | 8 | 77 |
| HPV33 | E6 | 9 | 71 |
| HPV33 | E6 | 11 | 71 |
| HPV33 | E6 | 8 | 142 |
| HPV33 | E6 | 8 | 92 |
| HPV33 | E6 | 9 | 92 |
| HPV33 | E6 | 10 | 92 |
| HPV33 | E6 | 9 | 140 |
| HPV33 | E6 | 10 | 140 |
| HPV33 | E6 | 9 | 54 |
| HPV33 | E6 | 8 | 76 |
| HPV33 | E6 | 9 | 76 |
| HPV33 | E7 | 8 | 58 |
| HPV33 | E7 | 10 | 58 |
| HPV33 | E7 | 10 | 39 |
| HPV33 | E7 | 9 | 3 |
| HPV33 | E7 | 10 | 3 |
| HPV33 | E7 | 11 | 3 |
| HPV33 | E7 | 8 | 4 |
| HPV33 | E7 | 9 | 4 |
| HPV33 | E7 | 10 | 4 |
| HPV33 | E7 | 8 | 8 |
| HPV33 | E7 | 9 | 8 |
| HPV33 | E7 | 8 | 76 |
| HPV33 | E7 | 9 | 76 |
| HPV33 | E7 | 8 | 1 |
| HPV33 | E7 | 11 | 1 |
| HPV33 | E7 | 9 | 65 |
| HPV33 | L1 | 9 | 58 |
| HPV33 | L1 | 8 | 475 |
| HPV33 | L1 | 9 | 475 |
| HPV33 | L1 | 9 | 162 |
| HPV33 | L1 | 9 | 378 |
| HPV33 | L1 | 10 | 378 |
| HPV33 | L1 | 9 | 229 |
| HPV33 | L1 | 8 | 168 |
| HPV33 | L1 | 9 | 435 |
| HPV33 | L1 | 11 | 435 |
| HPV33 | L1 | 10 | 452 |
| HPV33 | L1 | 8 | 359 |
| HPV33 | L1 | 11 | 359 |
| HPV33 | L1 | 11 | 210 |
| HPV33 | L1 | 11 | 74 |
| HPV33 | L1 | 8 | 318 |
| HPV33 | L1 | 8 | 120 |
| HPV33 | L1 | 9 | 171 |
| HPV33 | L1 | 10 | 171 |
| HPV33 | L1 | 8 | 441 |
| HPV33 | L1 | 10 | 441 |
| HPV33 | L1 | 8 | 109 |
| HPV33 | L1 | 10 | 109 |
| HPV33 | L1 | 8 | 464 |
| HPV33 | L1 | 10 | 464 |
| HPV33 | L1 | 8 | 390 |
| HPV33 | L1 | 9 | 390 |
| HPV33 | L1 | 8 | 277 |
| HPV33 | L1 | 10 | 277 |
| HPV33 | L1 | 10 | 52 |
| HPV33 | L1 | 11 | 52 |
| HPV33 | L1 | 9 | 363 |
| HPV33 | L1 | 11 | 363 |
| HPV33 | L1 | 8 | 59 |
| HPV33 | L1 | 11 | 59 |
| HPV33 | L1 | 10 | 473 |
| HPV33 | L1 | 11 | 473 |
| HPV33 | L1 | 9 | 450 |
| HPV33 | L1 | 8 | 235 |
| HPV33 | L1 | 8 | 250 |
| HPV33 | L1 | 11 | 250 |
| HPV33 | L1 | 10 | 82 |
| HPV33 | L1 | 11 | 82 |
| HPV33 | L1 | 9 | 308 |
| HPV33 | L1 | 9 | 216 |
| HPV33 | L1 | 9 | 134 |
| HPV33 | L1 | 9 | 262 |
| HPV33 | L1 | 10 | 262 |
| HPV33 | L1 | 9 | 144 |
| HPV33 | L1 | 8 | 433 |
| HPV33 | L1 | 11 | 433 |
| HPV33 | L1 | 8 | 64 |
| HPV33 | L1 | 10 | 54 |
| HPV33 | L1 | 11 | 64 |
| HPV33 | L1 | 10 | 314 |
| HPV33 | L1 | 8 | 97 |
| HPV33 | L1 | 10 | 97 |
| HPV33 | L1 | 10 | 258 |
| HPV33 | L1 | 8 | 364 |
| HPV33 | L1 | 10 | 364 |
| HPV33 | L1 | 11 | 364 |
| HPV33 | L1 | 9 | 465 |
| HPV33 | L1 | 11 | 465 |
| HPV33 | L1 | 10 | 251 |
| HPV33 | L1 | 11 | 251 |
| HPV33 | L1 | 9 | 19 |
| HPV33 | L1 | 10 | 19 |
| HPV33 | L1 | 10 | 40 |
| HPV33 | L1 | 11 | 40 |
| HPV33 | L1 | 8 | 29 |

TABLE XII-continued

HLA-B27 Supermotif Peptides

| 1 | 2 | 3 | 4 |
|---|---|---|---|
| HPV33 | L1 | 9 | 29 |
| HPV33 | L1 | 8 | 337 |
| HPV33 | L1 | 11 | 487 |
| HPV33 | L1 | 8 | 257 |
| HPV33 | L1 | 11 | 257 |
| HPV33 | L1 | 9 | 76 |
| HPV33 | L1 | 11 | 76 |
| HPV33 | L1 | 8 | 4 |
| HPV33 | L1 | 9 | 4 |
| HPV33 | L1 | 10 | 4 |
| HPV33 | L1 | 9 | 354 |
| HPV33 | L1 | 10 | 354 |
| HPV33 | L1 | 8 | 152 |
| HPV33 | L1 | 9 | 152 |
| HPV33 | L1 | 8 | 417 |
| HPV33 | L1 | 9 | 417 |
| HPV33 | L1 | 8 | 71 |
| HPV33 | L2 | 9 | 320 |
| HPV33 | L2 | 11 | 21 |
| HPV33 | L2 | 9 | 335 |
| HPV33 | L2 | 11 | 335 |
| HPV33 | L2 | 10 | 179 |
| HPV33 | L2 | 8 | 315 |
| HPV33 | L2 | 10 | 315 |
| HPV33 | L2 | 11 | 315 |
| HPV33 | L2 | 8 | 67 |
| HPV33 | L2 | 10 | 247 |
| HPV33 | L2 | 11 | 247 |
| HPV33 | L2 | 10 | 3 |
| HPV33 | L2 | 10 | 322 |
| HPV33 | L2 | 11 | 322 |
| HPV33 | L2 | 10 | 88 |
| HPV33 | L2 | 8 | 10 |
| HPV33 | L2 | 9 | 10 |
| HPV33 | L2 | 10 | 454 |
| HPV33 | L2 | 9 | 4 |
| HPV33 | L2 | 11 | 4 |
| HPV33 | L2 | 9 | 348 |
| HPV33 | L2 | 11 | 348 |
| HPV33 | L2 | 9 | 169 |
| HPV33 | L2 | 8 | 442 |
| HPV33 | L2 | 9 | 310 |
| HPV33 | L2 | 11 | 310 |
| HPV33 | L2 | 8 | 45 |
| HPV33 | L2 | 9 | 45 |
| HPV33 | L2 | 10 | 45 |
| HPV33 | L2 | 8 | 449 |
| HPV33 | L2 | 10 | 449 |
| HPV33 | L2 | 11 | 449 |
| HPV33 | L2 | 11 | 246 |
| HPV33 | L2 | 8 | 33 |
| HPV33 | L2 | 9 | 33 |
| HPV33 | L2 | 8 | 269 |
| HPV33 | L2 | 8 | 378 |
| HPV33 | L2 | 11 | 2 |
| HPV33 | L2 | 9 | 296 |
| HPV33 | L2 | 9 | 9 |
| HPV33 | L2 | 10 | 9 |
| HPV33 | L2 | 8 | 453 |
| HPV33 | L2 | 11 | 453 |
| HPV33 | L2 | 10 | 295 |
| HPV33 | L2 | 10 | 8 |
| HPV33 | L2 | 11 | 8 |
| HPV33 | L2 | 8 | 452 |
| HPV33 | L2 | 9 | 452 |
| HPV33 | L2 | 8 | 451 |
| HPV33 | L2 | 9 | 451 |
| HPV33 | L2 | 10 | 451 |
| HPV33 | L2 | 9 | 450 |
| HPV33 | L2 | 10 | 450 |
| HPV33 | L2 | 11 | 450 |
| HPV33 | L2 | 9 | 229 |
| HPV33 | L2 | 10 | 229 |
| HPV33 | L2 | 9 | 219 |
| HPV33 | L2 | 10 | 219 |
| HPV33 | L2 | 8 | 294 |
| HPV33 | L2 | 11 | 294 |
| HPV33 | L2 | 9 | 302 |
| HPV33 | L2 | 8 | 7 |
| HPV33 | L2 | 11 | 7 |
| HPV33 | L2 | 9 | 312 |
| HPV33 | L2 | 11 | 312 |
| HPV33 | L2 | 8 | 387 |
| HPV33 | L2 | 10 | 387 |
| HPV33 | L2 | 9 | 373 |
| HPV33 | L2 | 8 | 235 |
| HPV33 | L2 | 9 | 235 |
| HPV33 | L2 | 10 | 299 |
| HPV45 | E1 | 10 | 255 |
| HPV45 | E1 | 8 | 564 |
| HPV45 | E1 | 9 | 564 |
| HPV45 | E1 | 8 | 284 |
| HPV45 | E1 | 10 | 284 |
| HPV45 | E1 | 8 | 125 |
| HPV45 | E1 | 8 | 392 |
| HPV45 | E1 | 9 | 392 |
| HPV45 | E1 | 10 | 392 |
| HPV45 | E1 | 8 | 262 |
| HPV45 | E1 | 9 | 262 |
| HPV45 | E1 | 10 | 262 |
| HPV45 | E1 | 11 | 262 |
| HPV45 | E1 | 8 | 588 |
| HPV45 | E1 | 10 | 588 |
| HPV45 | E1 | 8 | 599 |
| HPV45 | E1 | 8 | 222 |
| HPV45 | E1 | 9 | 222 |
| HPV45 | E1 | 10 | 222 |
| HPV45 | E1 | 11 | 222 |
| HPV45 | E1 | 8 | 541 |
| HPV45 | E1 | 10 | 541 |
| HPV45 | E1 | 8 | 25 |
| HPV45 | E1 | 9 | 607 |
| HPV45 | E1 | 10 | 70 |
| HPV45 | E1 | 9 | 204 |
| HPV45 | E1 | 11 | 219 |
| HPV45 | E1 | 8 | 244 |
| HPV45 | E1 | 10 | 244 |
| HPV45 | E1 | 11 | 244 |
| HPV45 | E1 | 9 | 121 |
| HPV45 | E1 | 10 | 121 |
| HPV45 | E1 | 8 | 277 |
| HPV45 | E1 | 11 | 277 |
| HPV45 | E1 | 9 | 475 |
| HPV45 | E1 | 10 | 475 |
| HPV45 | E1 | 8 | 122 |
| HPV45 | E1 | 9 | 122 |
| HPV45 | E1 | 11 | 122 |
| HPV45 | E1 | 8 | 484 |
| HPV45 | E1 | 9 | 484 |
| HPV45 | E1 | 11 | 484 |
| HPV45 | E1 | 8 | 248 |
| HPV45 | E1 | 10 | 248 |
| HPV45 | E1 | 8 | 419 |
| HPV45 | E1 | 8 | 543 |
| HPV45 | E1 | 8 | 196 |
| HPV45 | E1 | 9 | 196 |
| HPV45 | E1 | 8 | 123 |
| HPV45 | E1 | 10 | 123 |
| HPV45 | E1 | 8 | 462 |
| HPV45 | E1 | 11 | 462 |
| HPV45 | E1 | 8 | 406 |
| HPV45 | E1 | 10 | 406 |
| HPV45 | E1 | 9 | 410 |
| HPV45 | E1 | 10 | 410 |
| HPV45 | E1 | 8 | 615 |
| HPV45 | E1 | 8 | 82 |
| HPV45 | E1 | 9 | 82 |
| HPV45 | E1 | 8 | 291 |
| HPV45 | E1 | 9 | 291 |
| HPV45 | E1 | 10 | 291 |

TABLE XII-continued

HLA-B27 Supermotif Peptides

| 1 | 2 | 3 | 4 |
|---|---|---|---|
| HPV45 | E1 | 8 | 550 |
| HPV45 | E1 | 11 | 395 |
| HPV45 | E1 | 10 | 457 |
| HPV45 | E1 | 11 | 457 |
| HPV45 | E1 | 9 | 386 |
| HPV45 | E1 | 10 | 386 |
| HPV45 | E1 | 8 | 450 |
| HPV45 | E1 | 8 | 305 |
| HPV45 | E1 | 9 | 305 |
| HPV45 | E1 | 10 | 305 |
| HPV45 | E1 | 11 | 305 |
| HPV45 | E1 | 10 | 272 |
| HPV45 | E1 | 8 | 439 |
| HPV45 | E1 | 9 | 439 |
| HPV45 | E1 | 11 | 439 |
| HPV45 | E1 | 10 | 529 |
| HPV45 | E1 | 8 | 195 |
| HPV45 | E1 | 9 | 195 |
| HPV45 | E1 | 10 | 195 |
| HPV45 | E1 | 10 | 567 |
| HPV45 | E1 | 9 | 279 |
| HPV45 | E1 | 8 | 180 |
| HPV45 | E1 | 11 | 180 |
| HPV45 | E1 | 8 | 461 |
| HPV45 | E1 | 9 | 461 |
| HPV45 | E1 | 8 | 303 |
| HPV45 | E1 | 9 | 303 |
| HPV45 | E1 | 10 | 303 |
| HPV45 | E1 | 11 | 303 |
| HPV45 | E1 | 8 | 111 |
| HPV45 | E1 | 9 | 340 |
| HPV45 | E1 | 11 | 340 |
| HPV45 | E1 | 10 | 409 |
| HPV45 | E1 | 11 | 409 |
| HPV45 | E1 | 10 | 334 |
| HPV45 | E1 | 11 | 403 |
| HPV45 | E1 | 9 | 542 |
| HPV45 | E1 | 11 | 127 |
| HPV45 | E1 | 8 | 499 |
| HPV45 | E1 | 9 | 499 |
| HPV45 | E1 | 11 | 93 |
| HPV45 | E1 | 9 | 424 |
| HPV45 | E1 | 8 | 574 |
| HPV45 | E1 | 11 | 574 |
| HPV45 | E1 | 8 | 518 |
| HPV45 | E1 | 11 | 518 |
| HPV45 | E1 | 9 | 509 |
| HPV45 | E1 | 9 | 602 |
| HPV45 | E1 | 8 | 432 |
| HPV45 | E1 | 10 | 432 |
| HPV45 | E1 | 8 | 274 |
| HPV45 | E1 | 10 | 274 |
| HPV45 | E1 | 11 | 274 |
| HPV45 | E1 | 9 | 405 |
| HPV45 | E1 | 11 | 405 |
| HPV45 | E1 | 8 | 315 |
| HPV45 | E1 | 11 | 315 |
| HPV45 | E2 | 9 | 75 |
| HPV45 | E2 | 10 | 75 |
| HPV45 | E2 | 11 | 75 |
| HPV45 | E2 | 9 | 52 |
| HPV45 | E2 | 10 | 23 |
| HPV45 | E2 | 10 | 315 |
| HPV45 | E2 | 8 | 299 |
| HPV45 | E2 | 10 | 299 |
| HPV45 | E2 | 9 | 153 |
| HPV45 | E2 | 10 | 153 |
| HPV45 | E2 | 11 | 54 |
| HPV45 | E2 | 9 | 183 |
| HPV45 | E2 | 11 | 183 |
| HPV45 | E2 | 10 | 12 |
| HPV45 | E2 | 11 | 12 |
| HPV45 | E2 | 8 | 116 |
| HPV45 | E2 | 10 | 116 |
| HPV45 | E2 | 11 | 116 |
| HPV45 | E2 | 8 | 178 |
| HPV45 | E2 | 8 | 120 |
| HPV45 | E2 | 11 | 262 |
| HPV45 | E2 | 9 | 260 |
| HPV45 | E2 | 8 | 76 |
| HPV45 | E2 | 9 | 76 |
| HPV45 | E2 | 10 | 76 |
| HPV45 | E2 | 10 | 294 |
| HPV45 | E2 | 8 | 167 |
| HPV45 | E2 | 9 | 167 |
| HPV45 | E2 | 10 | 167 |
| HPV45 | E2 | 8 | 42 |
| HPV45 | E2 | 9 | 42 |
| HPV45 | E2 | 11 | 42 |
| HPV45 | E2 | 9 | 117 |
| HPV45 | E2 | 10 | 117 |
| HPV45 | E2 | 11 | 117 |
| HPV45 | E2 | 8 | 249 |
| HPV45 | E2 | 8 | 303 |
| HPV45 | E2 | 11 | 303 |
| HPV45 | E2 | 8 | 296 |
| HPV45 | E2 | 11 | 296 |
| HPV45 | E2 | 9 | 85 |
| HPV45 | E2 | 8 | 310 |
| HPV45 | E2 | 11 | 310 |
| HPV45 | E2 | 8 | 306 |
| HPV45 | E2 | 9 | 306 |
| HPV45 | E2 | 10 | 1 |
| HPV45 | E2 | 8 | 61 |
| HPV45 | E2 | 10 | 61 |
| HPV45 | E2 | 8 | 130 |
| HPV45 | E2 | 9 | 130 |
| HPV45 | E2 | 10 | 130 |
| HPV45 | E2 | 11 | 130 |
| HPV45 | E2 | 9 | 330 |
| HPV45 | E2 | 11 | 330 |
| HPV45 | E2 | 9 | 6 |
| HPV45 | E2 | 11 | 6 |
| HPV45 | E2 | 9 | 239 |
| HPV45 | E2 | 11 | 224 |
| HPV45 | E2 | 10 | 259 |
| HPV45 | E2 | 8 | 345 |
| HPV45 | E2 | 9 | 345 |
| HPV45 | E2 | 11 | 345 |
| HPV45 | E2 | 11 | 283 |
| HPV45 | E2 | 10 | 311 |
| HPV45 | E2 | 9 | 73 |
| HPV45 | E2 | 11 | 73 |
| HPV45 | E2 | 8 | 29 |
| HPV45 | E2 | 10 | 29 |
| HPV45 | E2 | 11 | 29 |
| HPV45 | E2 | 8 | 71 |
| HPV45 | E2 | 9 | 71 |
| HPV45 | E2 | 11 | 71 |
| HPV45 | E2 | 8 | 91 |
| HPV45 | E2 | 10 | 91 |
| HPV45 | E2 | 8 | 266 |
| HPV45 | E2 | 8 | 58 |
| HPV45 | E2 | 11 | 58 |
| HPV45 | E2 | 9 | 248 |
| HPV45 | E2 | 10 | 308 |
| HPV45 | E6 | 11 | 2 |
| HPV45 | E6 | 8 | 65 |
| HPV45 | E6 | 11 | 65 |
| HPV45 | E6 | 10 | 35 |
| HPV45 | E6 | 11 | 35 |
| HPV45 | E6 | 8 | 123 |
| HPV45 | E6 | 9 | 123 |
| HPV45 | E6 | 8 | 91 |
| HPV45 | E6 | 9 | 91 |
| HPV45 | E6 | 11 | 91 |
| HPV45 | E6 | 11 | 148 |
| HPV45 | E6 | 8 | 40 |
| HPV45 | E6 | 9 | 40 |
| HPV45 | E6 | 10 | 40 |

TABLE XII-continued

HLA-B27 Supermotif Peptides

| 1 | 2 | 3 | 4 |
|---|---|---|---|
| HPV45 | E6 | 8 | 127 |
| HPV45 | E6 | 8 | 49 |
| HPV45 | E6 | 10 | 66 |
| HPV45 | E6 | 10 | 103 |
| HPV45 | E6 | 11 | 75 |
| HPV45 | E6 | 8 | 124 |
| HPV45 | E6 | 11 | 124 |
| HPV45 | E6 | 11 | 117 |
| HPV45 | E6 | 10 | 121 |
| HPV45 | E6 | 11 | 121 |
| HPV45 | E6 | 10 | 106 |
| HPV45 | E6 | 9 | 150 |
| HPV45 | E6 | 8 | 78 |
| HPV45 | E6 | 9 | 78 |
| HPV45 | E6 | 9 | 9 |
| HPV45 | E6 | 9 | 119 |
| HPV45 | E6 | 10 | 125 |
| HPV45 | E6 | 10 | 118 |
| HPV45 | E6 | 8 | 151 |
| HPV45 | E6 | 8 | 73 |
| HPV45 | E6 | 9 | 73 |
| HPV45 | E6 | 10 | 12 |
| HPV45 | E6 | 8 | 56 |
| HPV45 | E6 | 9 | 56 |
| HPV45 | E7 | 11 | 52 |
| HPV45 | E7 | 9 | 67 |
| HPV45 | E7 | 11 | 67 |
| HPV45 | E7 | 11 | 71 |
| HPV45 | E7 | 9 | 13 |
| HPV45 | E7 | 8 | 84 |
| HPV45 | E7 | 9 | 84 |
| HPV45 | E7 | 8 | 1 |
| HPV45 | E7 | 11 | 1 |
| HPV45 | E7 | 8 | 4 |
| HPV45 | E7 | 9 | 4 |
| HPV45 | E7 | 10 | 4 |
| HPV45 | E7 | 8 | 58 |
| HPV45 | E7 | 10 | 53 |
| HPV45 | E7 | 11 | 53 |
| HPV45 | E7 | 10 | 46 |
| HPV45 | L1 | 8 | 159 |
| HPV45 | L1 | 10 | 2 |
| HPV45 | L1 | 11 | 2 |
| HPV45 | L1 | 9 | 197 |
| HPV45 | L1 | 11 | 197 |
| HPV45 | L1 | 8 | 284 |
| HPV45 | L1 | 10 | 284 |
| HPV45 | L1 | 11 | 284 |
| HPV45 | L1 | 9 | 45 |
| HPV45 | L1 | 10 | 45 |
| HPV45 | L1 | 9 | 256 |
| HPV45 | L1 | 11 | 256 |
| HPV45 | L1 | 8 | 472 |
| HPV45 | L1 | 10 | 472 |
| HPV45 | L1 | 8 | 194 |
| HPV45 | L1 | 10 | 483 |
| HPV45 | L1 | 9 | 466 |
| HPV45 | L1 | 11 | 466 |
| HPV45 | L1 | 8 | 390 |
| HPV45 | L1 | 11 | 390 |
| HPV45 | L1 | 11 | 100 |
| HPV45 | L1 | 8 | 76 |
| HPV45 | L1 | 8 | 8 |
| HPV45 | L1 | 11 | 8 |
| HPV45 | L1 | 8 | 347 |
| HPV45 | L1 | 8 | 146 |
| HPV45 | L1 | 8 | 135 |
| HPV45 | L1 | 10 | 135 |
| HPV45 | L1 | 8 | 495 |
| HPV45 | L1 | 10 | 495 |
| HPV45 | L1 | 10 | 343 |
| HPV45 | L1 | 8 | 421 |
| HPV45 | L1 | 9 | 421 |
| HPV45 | L1 | 8 | 304 |
| HPV45 | L1 | 10 | 391 |
| HPV45 | L1 | 10 | 514 |
| HPV45 | L1 | 11 | 342 |
| HPV45 | L1 | 9 | 481 |
| HPV45 | L1 | 8 | 474 |
| HPV45 | L1 | 11 | 217 |
| HPV45 | L1 | 9 | 15 |
| HPV45 | L1 | 10 | 15 |
| HPV45 | L1 | 11 | 15 |
| HPV45 | L1 | 8 | 277 |
| HPV45 | L1 | 11 | 277 |
| HPV45 | L1 | 9 | 311 |
| HPV45 | L1 | 10 | 311 |
| HPV45 | L1 | 10 | 108 |
| HPV45 | L1 | 11 | 108 |
| HPV45 | L1 | 9 | 151 |
| HPV45 | L1 | 11 | 151 |
| HPV45 | L1 | 9 | 337 |
| HPV45 | L1 | 8 | 85 |
| HPV45 | L1 | 10 | 85 |
| HPV45 | L1 | 11 | 85 |
| HPV45 | L1 | 10 | 289 |
| HPV45 | L1 | 8 | 90 |
| HPV45 | L1 | 10 | 90 |
| HPV45 | L1 | 11 | 90 |
| HPV45 | L1 | 8 | 123 |
| HPV45 | L1 | 10 | 123 |
| HPV45 | L1 | 9 | 285 |
| HPV45 | L1 | 10 | 285 |
| HPV45 | L1 | 8 | 395 |
| HPV45 | L1 | 10 | 395 |
| HPV45 | L1 | 11 | 395 |
| HPV45 | L1 | 9 | 496 |
| HPV45 | L1 | 11 | 513 |
| HPV45 | L1 | 10 | 278 |
| HPV45 | L1 | 11 | 278 |
| HPV45 | L1 | 9 | 394 |
| HPV45 | L1 | 11 | 394 |
| HPV45 | L1 | 10 | 66 |
| HPV45 | L1 | 11 | 66 |
| HPV45 | L1 | 9 | 524 |
| HPV45 | L1 | 9 | 55 |
| HPV45 | L1 | 9 | 243 |
| HPV45 | L1 | 10 | 388 |
| HPV45 | L1 | 8 | 366 |
| HPV45 | L1 | 10 | 366 |
| HPV45 | L1 | 9 | 170 |
| HPV45 | L1 | 9 | 354 |
| HPV45 | L1 | 10 | 354 |
| HPV45 | L1 | 8 | 30 |
| HPV45 | L1 | 9 | 30 |
| HPV45 | L1 | 10 | 30 |
| HPV45 | L1 | 8 | 61 |
| HPV45 | L1 | 9 | 61 |
| HPV45 | L1 | 11 | 61 |
| HPV45 | L1 | 8 | 178 |
| HPV45 | L1 | 9 | 178 |
| HPV45 | L1 | 8 | 448 |
| HPV45 | L1 | 9 | 448 |
| HPV45 | L1 | 8 | 97 |
| HPV45 | L2 | 8 | 7 |
| HPV45 | L2 | 11 | 7 |
| HPV45 | L2 | 11 | 21 |
| HPV45 | L2 | 9 | 42 |
| HPV45 | L2 | 11 | 42 |
| HPV45 | L2 | 8 | 310 |
| HPV45 | L2 | 10 | 310 |
| HPV45 | L2 | 11 | 310 |
| HPV45 | L2 | 9 | 76 |
| HPV45 | L2 | 8 | 67 |
| HPV45 | L2 | 9 | 315 |
| HPV45 | L2 | 9 | 365 |
| HPV45 | L2 | 11 | 365 |
| HPV45 | L2 | 9 | 4 |
| HPV45 | L2 | 11 | 4 |
| HPV45 | L2 | 8 | 431 |

TABLE XII-continued

HLA-B27 Supermotif Peptides

| 1 | 2 | 3 | 4 |
|---|---|---|---|
| HPV45 | L2 | 9 | 431 |
| HPV45 | L2 | 11 | 431 |
| HPV45 | L2 | 10 | 364 |
| HPV45 | L2 | 8 | 280 |
| HPV45 | L2 | 8 | 447 |
| HPV45 | L2 | 9 | 447 |
| HPV45 | L2 | 10 | 447 |
| HPV45 | L2 | 11 | 447 |
| HPV45 | L2 | 8 | 10 |
| HPV45 | L2 | 9 | 10 |
| HPV45 | L2 | 8 | 450 |
| HPV45 | L2 | 11 | 450 |
| HPV45 | L2 | 8 | 448 |
| HPV45 | L2 | 9 | 448 |
| HPV45 | L2 | 10 | 448 |
| HPV45 | L2 | 8 | 33 |
| HPV45 | L2 | 9 | 33 |
| HPV45 | L2 | 9 | 446 |
| HPV45 | L2 | 10 | 446 |
| HPV45 | L2 | 11 | 446 |
| HPV45 | L2 | 11 | 371 |
| HPV45 | L2 | 11 | 224 |
| HPV45 | L2 | 9 | 9 |
| HPV45 | L2 | 10 | 9 |
| HPV45 | L2 | 8 | 449 |
| HPV45 | L2 | 9 | 449 |
| HPV45 | L2 | 10 | 290 |
| HPV45 | L2 | 10 | 8 |
| HPV45 | L2 | 11 | 8 |
| HPV45 | L2 | 8 | 219 |
| HPV45 | L2 | 9 | 219 |
| HPV45 | L2 | 9 | 189 |
| HPV45 | L2 | 10 | 3 |
| HPV45 | L2 | 9 | 228 |
| HPV45 | L2 | 9 | 297 |
| HPV45 | L2 | 10 | 297 |
| HPV45 | L2 | 8 | 289 |
| HPV45 | L2 | 11 | 289 |
| HPV45 | L2 | 9 | 243 |
| HPV45 | L2 | 10 | 87 |
| HPV45 | L2 | 11 | 307 |
| HPV45 | L2 | 10 | 317 |
| HPV45 | L2 | 11 | 317 |
| HPV45 | L2 | 10 | 294 |
| HPV45 | L2 | 10 | 221 |
| HPV45 | L2 | 9 | 218 |
| HPV45 | L2 | 10 | 218 |
| HPV45 | L2 | 8 | 234 |
| HPV45 | L2 | 9 | 234 |
| HPV45 | L2 | 8 | 320 |
| HPV45 | L2 | 9 | 320 |
| HPV56 | E2 | 9 | 10 |
| HPV56 | E2 | 11 | 10 |
| HPV56 | E2 | 10 | 202 |
| HPV56 | E2 | 9 | 118 |
| HPV56 | E2 | 10 | 118 |
| HPV56 | E2 | 8 | 8 |
| HPV56 | E2 | 9 | 8 |
| HPV56 | E2 | 11 | 8 |
| HPV56 | E2 | 9 | 123 |
| HPV56 | E2 | 8 | 146 |
| HPV56 | E2 | 11 | 146 |
| HPV56 | E2 | 8 | 250 |
| HPV56 | E2 | 11 | 250 |
| HPV56 | E2 | 9 | 232 |
| HPV56 | E2 | 8 | 53 |
| HPV56 | E2 | 10 | 53 |
| HPV56 | E2 | 11 | 53 |
| HPV56 | E2 | 9 | 106 |
| HPV56 | E2 | 11 | 184 |
| HPV56 | E2 | 11 | 162 |
| HPV56 | E2 | 8 | 107 |
| HPV56 | E2 | 9 | 181 |
| HPV56 | E2 | 11 | 50 |
| HPV56 | E2 | 9 | 54 |
| HPV56 | E2 | 10 | 54 |
| HPV56 | E2 | 11 | 54 |
| HPV56 | E2 | 8 | 119 |
| HPV56 | E2 | 9 | 119 |
| HPV56 | E2 | 11 | 119 |
| HPV56 | E2 | 10 | 185 |
| HPV56 | E2 | 8 | 247 |
| HPV56 | E2 | 11 | 247 |
| HPV56 | E2 | 8 | 240 |
| HPV56 | E2 | 8 | 37 |
| HPV56 | E2 | 9 | 37 |
| HPV56 | E2 | 10 | 37 |
| HPV56 | E2 | 10 | 228 |
| HPV56 | E2 | 11 | 228 |
| HPV56 | E2 | 9 | 275 |
| HPV56 | E2 | 10 | 275 |
| HPV56 | E2 | 11 | 275 |
| HPV56 | E2 | 8 | 245 |
| HPV56 | E2 | 10 | 245 |
| HPV56 | E2 | 8 | 187 |
| HPV56 | E2 | 9 | 89 |
| HPV56 | E2 | 8 | 255 |
| HPV56 | E2 | 10 | 255 |
| HPV56 | E2 | 9 | 290 |
| HPV56 | E2 | 11 | 290 |
| HPV56 | E2 | 10 | 180 |
| HPV56 | E2 | 8 | 296 |
| HPV56 | E2 | 9 | 296 |
| HPV56 | E2 | 11 | 296 |
| HPV56 | E2 | 8 | 67 |
| HPV56 | E2 | 9 | 67 |
| HPV56 | E2 | 10 | 67 |
| HPV56 | E2 | 11 | 67 |
| HPV56 | E2 | 9 | 197 |
| HPV56 | E2 | 8 | 103 |
| HPV56 | E2 | 9 | 103 |
| HPV56 | E2 | 10 | 238 |
| HPV56 | E2 | 8 | 129 |
| HPV56 | E2 | 9 | 129 |
| HPV56 | E2 | 9 | 298 |
| HPV56 | E2 | 10 | 298 |
| HPV56 | E2 | 11 | 298 |
| HPV56 | E2 | 11 | 268 |
| HPV56 | E2 | 10 | 285 |
| HPV56 | E2 | 11 | 285 |
| HPV56 | E2 | 8 | 257 |
| HPV56 | E2 | 9 | 252 |
| HPV56 | E2 | 10 | 252 |
| HPV56 | E2 | 11 | 252 |
| HPV56 | E6 | 9 | 132 |
| HPV56 | E6 | 8 | 36 |
| HPV56 | E6 | 10 | 36 |
| HPV56 | E6 | 11 | 36 |
| HPV56 | E6 | 8 | 66 |
| HPV56 | E6 | 11 | 66 |
| HPV56 | E6 | 8 | 123 |
| HPV56 | E6 | 9 | 123 |
| HPV56 | E6 | 10 | 123 |
| HPV56 | E6 | 9 | 10 |
| HPV56 | E6 | 8 | 128 |
| HPV56 | E6 | 9 | 16 |
| HPV56 | E6 | 11 | 16 |
| HPV56 | E6 | 10 | 104 |
| HPV56 | E6 | 9 | 37 |
| HPV56 | E6 | 10 | 37 |
| HPV56 | E6 | 8 | 96 |
| HPV56 | E6 | 9 | 96 |
| HPV56 | E6 | 8 | 125 |
| HPV56 | E6 | 11 | 125 |
| HPV56 | E6 | 9 | 120 |
| HPV56 | E6 | 11 | 120 |
| HPV56 | E6 | 8 | 15 |
| HPV56 | E6 | 10 | 15 |
| HPV56 | E6 | 9 | 53 |
| HPV56 | E6 | 11 | 53 |

TABLE XII-continued

HLA-B27 Supermotif Peptides

| 1 | 2 | 3 | 4 |
|---|---|---|---|
| HPV56 | E6 | 10 | 12 |
| HPV56 | E6 | 11 | 12 |
| HPV56 | E6 | 8 | 124 |
| HPV56 | E6 | 9 | 124 |
| HPV56 | E6 | 8 | 77 |
| HPV56 | E6 | 10 | 77 |
| HPV56 | E6 | 11 | 77 |
| HPV56 | E6 | 10 | 126 |
| HPV56 | E6 | 8 | 74 |
| HPV56 | E6 | 9 | 74 |
| HPV56 | E6 | 11 | 74 |
| HPV56 | E6 | 9 | 147 |
| HPV56 | E6 | 8 | 95 |
| HPV56 | E6 | 9 | 95 |
| HPV56 | E6 | 10 | 95 |
| HPV56 | E6 | 8 | 41 |
| HPV56 | E6 | 9 | 41 |
| HPV56 | E6 | 9 | 76 |
| HPV56 | E6 | 11 | 76 |
| HPV56 | E6 | 8 | 57 |
| HPV56 | E6 | 9 | 57 |
| HPV56 | E6 | 8 | 79 |
| HPV56 | E6 | 9 | 79 |
| HPV56 | E6 | 11 | 79 |
| HPV56 | E7 | 8 | 53 |
| HPV56 | E7 | 9 | 53 |
| HPV56 | E7 | 11 | 53 |
| HPV56 | E7 | 10 | 50 |
| HPV56 | E7 | 11 | 50 |
| HPV56 | E7 | 9 | 68 |
| HPV56 | E7 | 10 | 41 |
| HPV56 | E7 | 9 | 45 |
| HPV56 | E7 | 9 | 3 |
| HPV56 | E7 | 10 | 3 |
| HPV56 | E7 | 11 | 3 |
| HPV56 | E7 | 10 | 61 |
| HPV56 | E7 | 11 | 61 |
| HPV56 | E7 | 8 | 83 |
| HPV56 | E7 | 9 | 83 |
| HPV56 | E7 | 11 | 83 |
| HPV56 | E7 | 8 | 1 |
| HPV56 | E7 | 11 | 1 |
| HPV56 | E7 | 9 | 55 |
| HPV56 | E7 | 8 | 79 |
| HPV56 | E7 | 11 | 79 |
| HPV56 | L1 | 8 | 475 |
| HPV56 | L1 | 10 | 475 |
| HPV56 | L1 | 8 | 291 |
| HPV56 | L1 | 11 | 291 |
| HPV56 | L1 | 8 | 390 |
| HPV56 | L1 | 11 | 390 |
| HPV56 | L1 | 9 | 412 |
| HPV56 | L1 | 10 | 412 |
| HPV56 | L1 | 11 | 412 |
| HPV56 | L1 | 9 | 263 |
| HPV56 | L1 | 11 | 263 |
| HPV56 | L1 | 10 | 449 |
| HPV56 | L1 | 11 | 449 |
| HPV56 | L1 | 8 | 201 |
| HPV56 | L1 | 9 | 469 |
| HPV56 | L1 | 11 | 469 |
| HPV56 | L1 | 8 | 130 |
| HPV56 | L1 | 10 | 130 |
| HPV56 | L1 | 9 | 244 |
| HPV56 | L1 | 11 | 244 |
| HPV56 | L1 | 11 | 107 |
| HPV56 | L1 | 8 | 352 |
| HPV56 | L1 | 8 | 153 |
| HPV56 | L1 | 8 | 185 |
| HPV56 | L1 | 9 | 185 |
| HPV56 | L1 | 9 | 299 |
| HPV56 | L1 | 11 | 299 |
| HPV56 | L1 | 9 | 316 |
| HPV56 | L1 | 10 | 316 |
| HPV56 | L1 | 11 | 316 |
| HPV56 | L1 | 8 | 142 |
| HPV56 | L1 | 10 | 142 |
| HPV56 | L1 | 8 | 498 |
| HPV56 | L1 | 9 | 64 |
| HPV56 | L1 | 8 | 424 |
| HPV56 | L1 | 9 | 424 |
| HPV56 | L1 | 8 | 14 |
| HPV56 | L1 | 9 | 14 |
| HPV56 | L1 | 11 | 14 |
| HPV56 | L1 | 8 | 269 |
| HPV56 | L1 | 9 | 397 |
| HPV56 | L1 | 11 | 397 |
| HPV56 | L1 | 8 | 284 |
| HPV56 | L1 | 11 | 284 |
| HPV56 | L1 | 10 | 115 |
| HPV56 | L1 | 11 | 115 |
| HPV56 | L1 | 9 | 342 |
| HPV56 | L1 | 10 | 44 |
| HPV56 | L1 | 10 | 296 |
| HPV56 | L1 | 11 | 158 |
| HPV56 | L1 | 8 | 97 |
| HPV56 | L1 | 10 | 97 |
| HPV56 | L1 | 11 | 97 |
| HPV56 | L1 | 10 | 348 |
| HPV56 | L1 | 8 | 398 |
| HPV56 | L1 | 10 | 398 |
| HPV56 | L1 | 11 | 398 |
| HPV56 | L1 | 10 | 292 |
| HPV56 | L1 | 10 | 391 |
| HPV56 | L1 | 10 | 285 |
| HPV56 | L1 | 11 | 285 |
| HPV56 | L1 | 9 | 250 |
| HPV56 | L1 | 10 | 250 |
| HPV56 | L1 | 9 | 54 |
| HPV56 | L1 | 10 | 54 |
| HPV56 | L1 | 8 | 386 |
| HPV56 | L1 | 11 | 386 |
| HPV56 | L1 | 10 | 75 |
| HPV56 | L1 | 11 | 75 |
| HPV56 | L1 | 9 | 88 |
| HPV56 | L1 | 11 | 204 |
| HPV56 | L1 | 8 | 92 |
| HPV56 | L1 | 10 | 92 |
| HPV56 | L1 | 11 | 92 |
| HPV56 | L1 | 8 | 507 |
| HPV56 | L1 | 8 | 371 |
| HPV56 | L1 | 11 | 371 |
| HPV56 | L1 | 8 | 63 |
| HPV56 | L1 | 10 | 63 |
| HPV56 | L1 | 9 | 109 |
| HPV56 | L1 | 11 | 109 |
| HPV56 | L1 | 8 | 39 |
| HPV56 | L1 | 9 | 39 |
| HPV56 | L1 | 10 | 39 |
| HPV56 | L1 | 8 | 70 |
| HPV56 | L1 | 9 | 70 |
| HPV56 | L1 | 10 | 70 |
| HPV56 | L1 | 11 | 70 |
| HPV56 | L1 | 8 | 477 |
| HPV56 | L1 | 8 | 9 |
| HPV56 | L1 | 10 | 9 |
| HPV56 | L1 | 8 | 104 |
| HPV56 | L1 | 8 | 451 |
| HPV56 | L1 | 9 | 451 |
| HPV56 | L2 | 10 | 371 |
| HPV56 | L2 | 10 | 3 |
| HPV56 | L2 | 10 | 87 |
| HPV56 | L2 | 9 | 315 |
| HPV56 | L2 | 11 | 21 |
| HPV56 | L2 | 9 | 42 |
| HPV56 | L2 | 10 | 42 |
| HPV56 | L2 | 9 | 243 |
| HPV56 | L2 | 9 | 218 |
| HPV56 | L2 | 10 | 218 |
| HPV56 | L2 | 9 | 445 |

TABLE XII-continued

HLA-B27 Supermotif Peptides

| 1 | 2 | 3 | 4 |
|---|---|---|---|
| HPV56 | L2 | 11 | 445 |
| HPV56 | L2 | 8 | 67 |
| HPV56 | L2 | 9 | 4 |
| HPV56 | L2 | 11 | 4 |
| HPV56 | L2 | 9 | 189 |
| HPV56 | L2 | 8 | 375 |
| HPV56 | L2 | 9 | 375 |
| HPV56 | L2 | 8 | 10 |
| HPV56 | L2 | 9 | 10 |
| HPV56 | L2 | 8 | 451 |
| HPV56 | L2 | 8 | 33 |
| HPV56 | L2 | 9 | 33 |
| HPV56 | L2 | 8 | 224 |
| HPV56 | L2 | 11 | 224 |
| HPV56 | L2 | 8 | 37 |
| HPV56 | L2 | 9 | 37 |
| HPV56 | L2 | 11 | 37 |
| HPV56 | L2 | 9 | 228 |
| HPV56 | L2 | 9 | 9 |
| HPV56 | L2 | 10 | 9 |
| HPV56 | L2 | 8 | 450 |
| HPV56 | L2 | 9 | 450 |
| HPV56 | L2 | 10 | 290 |
| HPV56 | L2 | 8 | 308 |
| HPV56 | L2 | 10 | 308 |
| HPV56 | L2 | 8 | 219 |
| HPV56 | L2 | 9 | 219 |
| HPV56 | L2 | 10 | 8 |
| HPV56 | L2 | 11 | 8 |
| HPV56 | L2 | 8 | 449 |
| HPV56 | L2 | 9 | 449 |
| HPV56 | L2 | 10 | 449 |
| HPV56 | L2 | 8 | 448 |
| HPV56 | L2 | 9 | 448 |
| HPV56 | L2 | 10 | 448 |
| HPV56 | L2 | 11 | 448 |
| HPV56 | L2 | 9 | 447 |
| HPV56 | L2 | 10 | 447 |
| HPV56 | L2 | 11 | 447 |
| HPV56 | L2 | 8 | 446 |
| HPV56 | L2 | 10 | 446 |
| HPV56 | L2 | 11 | 446 |
| HPV56 | L2 | 9 | 297 |
| HPV56 | L2 | 9 | 76 |
| HPV56 | L2 | 11 | 427 |
| HPV56 | L2 | 8 | 155 |
| HPV56 | L2 | 9 | 155 |
| HPV56 | L2 | 8 | 289 |
| HPV56 | L2 | 11 | 289 |
| HPV56 | L2 | 9 | 307 |
| HPV56 | L2 | 11 | 307 |
| HPV56 | L2 | 8 | 7 |
| HPV56 | L2 | 11 | 7 |
| HPV56 | L2 | 9 | 202 |
| HPV56 | L2 | 8 | 150 |
| HPV56 | L2 | 10 | 317 |
| HPV56 | L2 | 11 | 317 |
| HPV56 | L2 | 8 | 234 |
| HPV56 | L2 | 9 | 234 |
| HPV56 | L2 | 10 | 294 |
| HPV56 | L2 | 8 | 227 |
| HPV56 | L2 | 10 | 227 |

TABLE XII A

HPV6A
HLA-B27 Supermotif Peptides

| 2 | 3 | 4 |
|---|---|---|
| E1 | 10 | 263 |
| E2 | 9 | 67 |

TABLE XII A-continued

HPV6A
HLA-B27 Supermotif Peptides

| 2 | 3 | 4 |
|---|---|---|
| E2 | 11 | 67 |
| E2 | 11 | 154 |
| L2 | 10 | 78 |
| E2 | 9 | 46 |
| E2 | 11 | 46 |
| E2 | 11 | 5 |
| E1 | 10 | 400 |
| E1 | 9 | 390 |
| E6 | 10 | 124 |
| L2 | 9 | 315 |
| L2 | 8 | 443 |
| L2 | 10 | 443 |
| L2 | 11 | 443 |
| E1 | 8 | 292 |
| E1 | 10 | 292 |
| E1 | 8 | 201 |
| E1 | 9 | 201 |
| E6 | 10 | 34 |
| E6 | 11 | 34 |
| E6 | 8 | 17 |
| E6 | 11 | 17 |
| L1 | 9 | 225 |
| E1 | 9 | 410 |
| E2 | 9 | 306 |
| E2 | 10 | 306 |
| E1 | 8 | 230 |
| E1 | 9 | 549 |
| E1 | 10 | 549 |
| E1 | 8 | 596 |
| E1 | 10 | 596 |
| E1 | 8 | 188 |
| E1 | 9 | 188 |
| E1 | 11 | 188 |
| E4 | 9 | 52 |
| E1 | 9 | 348 |
| E1 | 11 | 348 |
| L2 | 9 | 36 |
| L2 | 10 | 36 |
| E1 | 8 | 164 |
| L1 | 8 | 429 |
| L1 | 11 | 429 |
| L1 | 10 | 448 |
| L1 | 9 | 431 |
| L1 | 11 | 431 |
| E2 | 9 | 176 |
| E1 | 9 | 615 |
| E6 | 8 | 70 |
| E6 | 11 | 70 |
| E1 | 9 | 212 |
| E1 | 10 | 212 |
| E1 | 9 | 356 |
| E1 | 11 | 356 |
| E1 | 11 | 227 |
| E2 | 8 | 164 |
| L1 | 11 | 70 |
| L2 | 10 | 176 |
| E2 | 9 | 69 |
| E2 | 11 | 69 |
| L1 | 8 | 314 |
| L1 | 8 | 116 |
| E1 | 9 | 210 |
| E1 | 11 | 210 |
| L2 | 8 | 310 |
| L2 | 10 | 310 |
| L2 | 11 | 310 |
| E6 | 9 | 72 |
| E6 | 11 | 72 |
| E1 | 9 | 483 |
| E1 | 10 | 483 |
| E2 | 8 | 114 |
| E6 | 11 | 135 |
| E7 | 9 | 3 |
| E7 | 11 | 3 |
| L1 | 10 | 460 |

TABLE XII A-continued

HPV6A
HLA-B27 Supermotif Peptides

| 2 | 3 | 4 |
|---|---|---|
| L2 | 8 | 67 |
| E1 | 8 | 245 |
| E1 | 11 | 245 |
| E2 | 10 | 328 |
| E4 | 9 | 16 |
| E4 | 10 | 16 |
| E2 | 8 | 358 |
| E2 | 10 | 358 |
| E2 | 11 | 358 |
| E2 | 8 | 308 |
| L2 | 11 | 283 |
| E1 | 9 | 244 |
| L2 | 9 | 268 |
| L2 | 10 | 268 |
| L1 | 9 | 386 |
| L2 | 10 | 317 |
| E1 | 8 | 427 |
| E6 | 10 | 102 |
| E7 | 8 | 76 |
| E7 | 9 | 76 |
| E2 | 8 | 356 |
| E2 | 10 | 356 |
| L2 | 8 | 280 |
| E1 | 8 | 414 |
| E1 | 10 | 414 |
| E2 | 9 | 329 |
| L2 | 9 | 311 |
| L2 | 10 | 311 |
| L2 | 11 | 311 |
| E6 | 9 | 118 |
| E6 | 10 | 118 |
| E1 | 8 | 551 |
| E2 | 8 | 307 |
| E2 | 9 | 307 |
| E2 | 9 | 28 |
| E2 | 11 | 111 |
| E1 | 8 | 120 |
| E4 | 8 | 17 |
| E4 | 9 | 17 |
| L2 | 8 | 10 |
| L2 | 9 | 10 |
| E2 | 10 | 112 |
| E1 | 9 | 83 |
| E2 | 10 | 6 |
| E2 | 11 | 6 |
| L2 | 8 | 445 |
| L2 | 9 | 445 |
| L2 | 10 | 445 |
| E1 | 10 | 123 |
| E6 | 8 | 138 |
| E6 | 11 | 138 |
| E1 | 10 | 465 |
| E4 | 8 | 15 |
| E4 | 10 | 15 |
| E4 | 11 | 15 |
| E4 | 11 | 9 |
| L2 | 11 | 229 |
| E4 | 11 | 25 |
| E1 | 8 | 580 |
| E1 | 10 | 580 |
| E2 | 8 | 297 |
| E1 | 10 | 199 |
| E1 | 11 | 199 |
| E7 | 8 | 8 |
| L1 | 9 | 446 |
| E1 | 10 | 82 |
| E2 | 10 | 83 |
| E6 | 9 | 51 |
| E6 | 11 | 51 |
| L2 | 9 | 45 |
| L2 | 10 | 45 |
| E1 | 9 | 204 |
| E1 | 8 | 447 |
| E1 | 9 | 447 |

TABLE XII A-continued

HPV6A
HLA-B27 Supermotif Peptides

| 2 | 3 | 4 |
|---|---|---|
| E1 | 11 | 447 |
| L1 | 11 | 246 |
| E7 | 8 | 1 |
| E7 | 11 | 1 |
| E2 | 11 | 77 |
| E6 | 10 | 24 |
| L2 | 9 | 305 |
| E2 | 8 | 36 |
| E2 | 9 | 36 |
| L1 | 9 | 359 |
| L1 | 11 | 359 |
| E1 | 9 | 418 |
| E1 | 10 | 418 |
| E1 | 10 | 537 |
| L1 | 10 | 78 |
| L1 | 11 | 78 |
| E2 | 10 | 27 |
| L1 | 9 | 212 |
| E1 | 11 | 285 |
| L1 | 11 | 55 |
| L1 | 9 | 68 |
| L1 | 9 | 278 |
| L1 | 10 | 278 |
| L1 | 9 | 139 |
| E2 | 11 | 327 |
| E2 | 9 | 324 |
| E1 | 10 | 311 |
| E1 | 11 | 311 |
| E1 | 8 | 469 |
| E1 | 8 | 119 |
| E1 | 9 | 119 |
| L2 | 8 | 33 |
| L1 | 8 | 60 |
| L1 | 11 | 60 |
| E4 | 10 | 40 |
| E1 | 8 | 108 |
| L2 | 8 | 218 |
| L2 | 10 | 220 |
| E1 | 8 | 25 |
| L2 | 11 | 361 |
| L1 | 10 | 310 |
| E1 | 9 | 253 |
| E1 | 10 | 253 |
| L2 | 11 | 244 |
| L1 | 10 | 93 |
| E2 | 11 | 342 |
| E2 | 8 | 37 |
| E6 | 8 | 78 |
| E2 | 9 | 357 |
| E2 | 11 | 357 |
| E2 | 11 | 309 |
| E1 | 8 | 448 |
| E1 | 10 | 448 |
| E1 | 11 | 448 |
| L1 | 8 | 360 |
| L1 | 10 | 360 |
| L1 | 11 | 360 |
| E7 | 8 | 4 |
| E7 | 10 | 4 |
| E1 | 8 | 411 |
| E1 | 11 | 411 |
| L1 | 10 | 247 |
| L1 | 11 | 247 |
| L1 | 9 | 461 |
| E1 | 8 | 550 |
| E1 | 9 | 550 |
| E1 | 8 | 419 |
| E1 | 9 | 419 |
| L2 | 9 | 9 |
| L2 | 10 | 9 |
| L2 | 8 | 447 |
| L2 | 9 | 444 |
| L2 | 10 | 444 |
| L2 | 11 | 444 |

TABLE XII A-continued

HPV6A
HLA-B27 Supermotif Peptides

| 2 | 3 | 4 |
|---|---|---|
| E4 | 9 | 41 |
| E1 | 8 | 84 |
| L2 | 10 | 290 |
| L2 | 10 | 8 |
| L2 | 11 | 8 |
| L2 | 8 | 446 |
| L2 | 9 | 446 |
| E1 | 9 | 124 |
| L2 | 11 | 7 |
| E1 | 8 | 507 |
| E2 | 11 | 52 |
| E4 | 9 | 58 |
| L2 | 9 | 187 |
| L2 | 8 | 148 |
| E1 | 9 | 501 |
| E1 | 10 | 501 |
| E1 | 11 | 501 |
| E1 | 9 | 432 |
| L1 | 9 | 18 |
| L2 | 9 | 297 |
| L1 | 10 | 39 |
| L1 | 11 | 39 |
| L2 | 8 | 289 |
| L2 | 11 | 289 |
| E1 | 9 | 287 |
| E1 | 10 | 57 |
| E1 | 11 | 57 |
| E1 | 9 | 74 |
| E6 | 8 | 122 |
| E1 | 8 | 572 |
| E1 | 9 | 572 |
| E4 | 11 | 87 |
| E6 | 9 | 93 |
| E6 | 10 | 93 |
| E2 | 8 | 181 |
| E1 | 9 | 129 |
| E1 | 11 | 129 |
| E1 | 11 | 116 |
| E1 | 10 | 342 |
| L2 | 11 | 307 |
| L1 | 8 | 333 |
| E1 | 8 | 582 |
| E2 | 10 | 148 |
| E2 | 11 | 148 |
| E1 | 11 | 403 |
| E2 | 11 | 119 |
| E6 | 10 | 117 |
| E6 | 11 | 117 |
| E2 | 11 | 350 |
| E1 | 11 | 122 |
| E1 | 10 | 186 |
| E1 | 11 | 186 |
| E1 | 8 | 610 |
| E2 | 10 | 33 |
| E2 | 11 | 33 |
| E6 | 9 | 133 |
| E1 | 8 | 440 |
| L1 | 9 | 2 |
| L1 | 8 | 34 |
| L1 | 9 | 34 |
| E2 | 10 | 337 |
| E2 | 11 | 337 |
| E2 | 8 | 44 |
| E2 | 11 | 44 |
| L1 | 11 | 355 |
| E1 | 9 | 413 |
| E1 | 11 | 413 |
| L1 | 11 | 436 |
| E6 | 8 | 48 |
| L1 | 8 | 147 |
| E1 | 11 | 577 |
| E6 | 9 | 77 |
| E2 | 10 | 302 |
| E2 | 11 | 302 |

TABLE XII A-continued

HPV6A
HLA-B27 Supermotif Peptides

| 2 | 3 | 4 |
|---|---|---|
| L1 | 8 | 67 |
| 2 | 9 | 413 |

TABLE XII B

HPV6B
HLA-B27 Supermotif Peptides

| 2 | 3 | 4 |
|---|---|---|
| E1 | 10 | 263 |
| E2 | 9 | 67 |
| E2 | 12 | 67 |
| E2 | 11 | 154 |
| L2 | 10 | 78 |
| E2 | 9 | 46 |
| E2 | 11 | 46 |
| E2 | 11 | 5 |
| E1 | 10 | 400 |
| E1 | 9 | 390 |
| E6 | 10 | 124 |
| L2 | 9 | 315 |
| L2 | 8 | 443 |
| L2 | 10 | 443 |
| L2 | 11 | 443 |
| E1 | 8 | 292 |
| E1 | 10 | 292 |
| E1 | 8 | 201 |
| E1 | 9 | 201 |
| E6 | 10 | 34 |
| E6 | 11 | 34 |
| E6 | 8 | 17 |
| E6 | 11 | 17 |
| L1 | 9 | 225 |
| E1 | 9 | 410 |
| E1 | 8 | 230 |
| E2 | 9 | 306 |
| E2 | 10 | 306 |
| E1 | 9 | 549 |
| E1 | 10 | 549 |
| E1 | 8 | 596 |
| E1 | 10 | 596 |
| E1 | 8 | 188 |
| E1 | 9 | 188 |
| E1 | 11 | 188 |
| E4 | 9 | 62 |
| E1 | 9 | 348 |
| E1 | 11 | 348 |
| L2 | 9 | 36 |
| L2 | 10 | 36 |
| E1 | 8 | 164 |
| L1 | 8 | 429 |
| L1 | 11 | 429 |
| L1 | 10 | 448 |
| L1 | 9 | 431 |
| L1 | 11 | 431 |
| E2 | 9 | 176 |
| E1 | 9 | 615 |
| E6 | 8 | 70 |
| E6 | 11 | 70 |
| E1 | 9 | 212 |
| E1 | 10 | 212 |
| E1 | 9 | 356 |
| E1 | 11 | 356 |
| E1 | 9 | 227 |
| E1 | 11 | 227 |
| E2 | 8 | 164 |
| L1 | 11 | 70 |
| E2 | 9 | 69 |
| E2 | 11 | 69 |
| L1 | 8 | 314 |

TABLE XII B-continued

HPV6B
HLA-B27 Supermotif Peptides

| 2 | 3 | 4 |
|---|---|---|
| L1 | 8 | 116 |
| E1 | 9 | 210 |
| E1 | 11 | 210 |
| L2 | 8 | 310 |
| L2 | 10 | 310 |
| L2 | 11 | 310 |
| E6 | 9 | 72 |
| E6 | 11 | 72 |
| E1 | 9 | 483 |
| E1 | 10 | 483 |
| E2 | 8 | 114 |
| E4 | 9 | 7 |
| E4 | 10 | 7 |
| E6 | 11 | 135 |
| E7 | 9 | 3 |
| E7 | 11 | 3 |
| L1 | 10 | 460 |
| L2 | 8 | 67 |
| E1 | 8 | 245 |
| E1 | 11 | 245 |
| E2 | 10 | 328 |
| E2 | 10 | 27 |
| E4 | 9 | 26 |
| E4 | 10 | 26 |
| E2 | 8 | 358 |
| E2 | 10 | 358 |
| E2 | 11 | 358 |
| E2 | 8 | 308 |
| L2 | 11 | 283 |
| E1 | 9 | 244 |
| L2 | 9 | 268 |
| L2 | 10 | 268 |
| L1 | 9 | 386 |
| L2 | 10 | 317 |
| E1 | 8 | 427 |
| E6 | 10 | 102 |
| E7 | 8 | 76 |
| E7 | 9 | 76 |
| L2 | 8 | 280 |
| E1 | 8 | 414 |
| E1 | 10 | 414 |
| E2 | 9 | 329 |
| L2 | 9 | 311 |
| L2 | 10 | 311 |
| L2 | 11 | 311 |
| E6 | 9 | 118 |
| E6 | 10 | 118 |
| E1 | 8 | 551 |
| E6 | 11 | 49 |
| E5B | 8 | 50 |
| E5B | 11 | 50 |
| E2 | 9 | 28 |
| E2 | 11 | 111 |
| E1 | 8 | 120 |
| E4 | 8 | 27 |
| E4 | 9 | 27 |
| L2 | 8 | 10 |
| L2 | 9 | 10 |
| E2 | 10 | 112 |
| E1 | 9 | 83 |
| E2 | 10 | 6 |
| E2 | 11 | 6 |
| L2 | 8 | 445 |
| L2 | 9 | 445 |
| L2 | 10 | 445 |
| E1 | 10 | 123 |
| E6 | 8 | 138 |
| E6 | 11 | 138 |
| E1 | 10 | 465 |
| E2 | 8 | 26 |
| E2 | 11 | 26 |
| E4 | 8 | 25 |
| E4 | 10 | 25 |
| E4 | 11 | 25 |
| E4 | 11 | 19 |
| L2 | 11 | 229 |
| E4 | 11 | 35 |
| E1 | 8 | 580 |
| E1 | 10 | 580 |
| E2 | 8 | 297 |
| E1 | 10 | 199 |
| E1 | 11 | 199 |
| E7 | 8 | 8 |
| L1 | 9 | 446 |
| E1 | 10 | 82 |
| E6 | 9 | 51 |
| E6 | 11 | 51 |
| L2 | 9 | 45 |
| L2 | 10 | 45 |
| E1 | 9 | 204 |
| E1 | 8 | 447 |
| E1 | 9 | 447 |
| E1 | 11 | 447 |
| L1 | 11 | 246 |
| E2 | 10 | 83 |
| E7 | 8 | 1 |
| E7 | 11 | 1 |
| E2 | 11 | 77 |
| E6 | 10 | 24 |
| L2 | 9 | 305 |
| E5B | 9 | 60 |
| E5B | 10 | 60 |
| E5B | 11 | 60 |
| E2 | 8 | 36 |
| E2 | 9 | 36 |
| L1 | 9 | 359 |
| L1 | 11 | 359 |
| E1 | 9 | 418 |
| E1 | 10 | 418 |
| E1 | 10 | 537 |
| L1 | 10 | 78 |
| L1 | 11 | 78 |
| E5B | 9 | 49 |
| L1 | 9 | 212 |
| E1 | 11 | 285 |
| L1 | 11 | 55 |
| E1 | 9 | 68 |
| L1 | 9 | 278 |
| L1 | 10 | 278 |
| L1 | 9 | 139 |
| E2 | 11 | 327 |
| E1 | 10 | 311 |
| E1 | 11 | 311 |
| E1 | 8 | 469 |
| E1 | 8 | 119 |
| E1 | 9 | 119 |
| L2 | 8 | 33 |
| L1 | 8 | 60 |
| L1 | 11 | 60 |
| E4 | 10 | 50 |
| E1 | 8 | 108 |
| L2 | 8 | 218 |
| L2 | 10 | 220 |
| E1 | 8 | 25 |
| L2 | 11 | 361 |
| L1 | 10 | 310 |
| E1 | 9 | 253 |
| E1 | 10 | 253 |
| L2 | 11 | 244 |
| L1 | 10 | 93 |
| E2 | 11 | 342 |
| E2 | 8 | 37 |
| E6 | 8 | 78 |
| E2 | 11 | 309 |
| E1 | 8 | 448 |
| E1 | 10 | 448 |
| E1 | 11 | 448 |
| E2 | 8 | 307 |

TABLE XII B-continued

HPV6B
HLA-B27 Supermotif Peptides

| 2 | 3 | 4 |
|---|---|---|
| E2 | 9 | 307 |
| L1 | 8 | 360 |
| L1 | 10 | 360 |
| L1 | 11 | 360 |
| E7 | 8 | 4 |
| E7 | 10 | 4 |
| E1 | 8 | 411 |
| E1 | 11 | 411 |
| L1 | 10 | 247 |
| L1 | 11 | 247 |
| L1 | 9 | 461 |
| E1 | 8 | 550 |
| E1 | 9 | 550 |
| E1 | 8 | 419 |
| E1 | 9 | 419 |
| L2 | 9 | 9 |
| L2 | 10 | 9 |
| L2 | 8 | 447 |
| L2 | 9 | 444 |
| L2 | 10 | 444 |
| L2 | 11 | 444 |
| E4 | 9 | 51 |
| E1 | 8 | 84 |
| L2 | 10 | 290 |
| L2 | 10 | 8 |
| L2 | 11 | 8 |
| L2 | 8 | 446 |
| L2 | 9 | 446 |
| E1 | 9 | 124 |
| L2 | 11 | 7 |
| E1 | 8 | 507 |
| E2 | 11 | 52 |
| E2 | 9 | 357 |
| E2 | 11 | 357 |
| L2 | 9 | 187 |
| L2 | 8 | 148 |
| E1 | 9 | 501 |
| E1 | 10 | 501 |
| E1 | 11 | 501 |
| E2 | 9 | 324 |
| E1 | 9 | 432 |
| L1 | 9 | 18 |
| L2 | 9 | 297 |
| L1 | 10 | 39 |
| L1 | 11 | 39 |
| L2 | 8 | 289 |
| L2 | 11 | 289 |
| E1 | 9 | 287 |
| E1 | 10 | 57 |
| E1 | 11 | 57 |
| E1 | 9 | 74 |
| E6 | 8 | 122 |
| E4 | 11 | 97 |
| E1 | 8 | 572 |
| E1 | 9 | 572 |
| E2 | 8 | 181 |
| E6 | 9 | 93 |
| E6 | 10 | 93 |
| E1 | 9 | 129 |
| E1 | 11 | 129 |
| E1 | 11 | 116 |
| E1 | 10 | 342 |
| L2 | 11 | 307 |
| L1 | 8 | 333 |
| E1 | 8 | 582 |
| E2 | 10 | 148 |
| E2 | 11 | 148 |
| E1 | 11 | 403 |
| E2 | 11 | 119 |
| E6 | 10 | 117 |
| E6 | 11 | 117 |
| E2 | 11 | 350 |
| E1 | 11 | 122 |
| E1 | 10 | 186 |

TABLE XII B-continued

HPV6B
HLA-B27 Supermotif Peptides

| 2 | 3 | 4 |
|---|---|---|
| E1 | 11 | 186 |
| E1 | 8 | 610 |
| E2 | 10 | 33 |
| E2 | 11 | 33 |
| E6 | 9 | 133 |
| E1 | 8 | 440 |
| L1 | 9 | 2 |
| L1 | 8 | 34 |
| L1 | 9 | 34 |
| E2 | 8 | 44 |
| E2 | 11 | 44 |
| L1 | 11 | 355 |
| E1 | 9 | 413 |
| E1 | 11 | 413 |
| E6 | 8 | 48 |
| L1 | 11 | 436 |
| L1 | 8 | 147 |
| E1 | 11 | 577 |
| E6 | 9 | 77 |
| E2 | 10 | 302 |
| E2 | 11 | 302 |
| L1 | 8 | 67 |
| L1 | 9 | 413 |

SF 1168114 v1

TABLE XII C

HPV11
HLA-B27 Supermotif Peptides

| 2 | 3 | 4 |
|---|---|---|
| E1 | 10 | 263 |
| E1 | 9 | 74 |
| E2 | 11 | 154 |
| E2 | 9 | 46 |
| E2 | 11 | 46 |
| E2 | 11 | 5 |
| E2 | 10 | 83 |
| E1 | 9 | 400 |
| E1 | 10 | 400 |
| E1 | 9 | 390 |
| E6 | 10 | 124 |
| E2 | 10 | 241 |
| L2 | 9 | 314 |
| L2 | 8 | 439 |
| L2 | 10 | 439 |
| L2 | 11 | 439 |
| E1 | 8 | 292 |
| E1 | 10 | 292 |
| E6 | 8 | 107 |
| E6 | 11 | 107 |
| E6 | 9 | 6 |
| E6 | 10 | 6 |
| E6 | 11 | 6 |
| E2 | 8 | 279 |
| E2 | 11 | 279 |
| E1 | 8 | 201 |
| E6 | 11 | 49 |
| E6 | 8 | 17 |
| E6 | 11 | 17 |
| L1 | 9 | 226 |
| E1 | 9 | 410 |
| E6 | 10 | 34 |
| E6 | 11 | 34 |
| E7 | 8 | 41 |
| E7 | 11 | 38 |
| E2 | 9 | 305 |
| E1 | 9 | 549 |
| E1 | 10 | 549 |
| E1 | 8 | 596 |

TABLE XII C-continued

HPV11
HLA-B27 Supermotif Peptides

| 2 | 3 | 4 |
|---|---|---|
| E1 | 10 | 596 |
| E4 | 10 | 66 |
| E1 | 8 | 230 |
| E1 | 8 | 188 |
| E1 | 9 | 188 |
| E1 | 11 | 188 |
| E1 | 9 | 348 |
| E1 | 11 | 348 |
| E1 | 8 | 25 |
| L2 | 9 | 35 |
| L2 | 10 | 35 |
| L1 | 8 | 430 |
| L1 | 11 | 430 |
| L1 | 10 | 449 |
| L1 | 9 | 432 |
| L1 | 11 | 432 |
| E4 | 8 | 27 |
| E4 | 9 | 27 |
| E1 | 8 | 162 |
| E1 | 9 | 615 |
| E1 | 9 | 212 |
| E1 | 9 | 356 |
| E1 | 11 | 356 |
| E1 | 11 | 227 |
| E2 | 8 | 164 |
| L1 | 11 | 70 |
| E2 | 9 | 299 |
| L2 | 10 | 175 |
| E2 | 9 | 69 |
| E2 | 11 | 69 |
| L1 | 8 | 315 |
| L1 | 8 | 116 |
| E6 | 8 | 122 |
| E1 | 9 | 210 |
| E1 | 11 | 210 |
| E6 | 9 | 72 |
| E6 | 11 | 72 |
| E1 | 9 | 483 |
| E1 | 10 | 483 |
| E4 | 9 | 7 |
| E4 | 10 | 7 |
| L2 | 8 | 66 |
| E6 | 11 | 135 |
| L1 | 10 | 461 |
| E7 | 9 | 3 |
| E7 | 11 | 3 |
| L1 | 9 | 472 |
| E1 | 8 | 245 |
| E1 | 11 | 245 |
| E2 | 8 | 44 |
| E2 | 11 | 44 |
| E2 | 10 | 27 |
| E2 | 8 | 327 |
| E2 | 10 | 327 |
| E6 | 10 | 108 |
| E2 | 8 | 357 |
| E2 | 10 | 357 |
| E2 | 11 | 357 |
| L2 | 11 | 282 |
| E1 | 9 | 244 |
| E2 | 8 | 26 |
| E2 | 11 | 26 |
| L2 | 9 | 267 |
| L2 | 10 | 267 |
| L1 | 9 | 387 |
| E1 | 9 | 492 |
| E1 | 11 | 492 |
| E6 | 10 | 102 |
| E2 | 8 | 355 |
| E2 | 10 | 355 |
| E2 | 8 | 36 |
| L2 | 8 | 279 |
| E7 | 8 | 76 |
| E7 | 9 | 76 |
| E1 | 9 | 204 |
| E2 | 8 | 255 |
| E2 | 11 | 255 |
| E1 | 8 | 414 |
| E1 | 10 | 414 |
| E6 | 9 | 118 |
| E6 | 10 | 118 |
| E2 | 9 | 28 |
| E2 | 11 | 28 |
| E2 | 11 | 308 |
| E1 | 8 | 551 |
| E1 | 8 | 419 |
| E1 | 9 | 419 |
| E1 | 11 | 419 |
| E2 | 11 | 111 |
| E1 | 8 | 120 |
| L2 | 8 | 9 |
| L2 | 9 | 9 |
| E1 | 9 | 83 |
| E2 | 10 | 6 |
| E2 | 11 | 6 |
| E1 | 10 | 123 |
| E6 | 8 | 138 |
| E6 | 11 | 138 |
| E1 | 9 | 208 |
| E1 | 11 | 208 |
| E1 | 10 | 465 |
| E2 | 9 | 43 |
| E4 | 8 | 19 |
| E4 | 11 | 19 |
| E1 | 8 | 580 |
| E1 | 10 | 580 |
| E6 | 10 | 24 |
| E4 | 11 | 35 |
| E2 | 8 | 296 |
| E1 | 10 | 199 |
| E7 | 8 | 8 |
| L1 | 9 | 447 |
| E6 | 10 | 117 |
| E6 | 11 | 117 |
| E1 | 10 | 82 |
| E6 | 8 | 98 |
| E6 | 9 | 98 |
| E6 | 9 | 51 |
| E6 | 11 | 51 |
| L2 | 9 | 44 |
| L2 | 10 | 44 |
| E1 | 8 | 447 |
| E1 | 9 | 447 |
| E1 | 11 | 447 |
| L1 | 11 | 247 |
| E7 | 8 | 1 |
| E7 | 11 | 1 |
| E2 | 11 | 77 |
| E2 | 8 | 31 |
| E1 | 9 | 418 |
| E1 | 10 | 418 |
| L1 | 9 | 360 |
| L1 | 11 | 360 |
| E1 | 10 | 537 |
| E1 | 10 | 304 |
| L2 | 8 | 147 |
| L1 | 10 | 78 |
| L1 | 11 | 78 |
| L1 | 9 | 213 |
| E1 | 11 | 285 |
| L1 | 11 | 55 |
| E6 | 8 | 52 |
| E6 | 10 | 52 |
| E6 | 11 | 52 |
| E1 | 9 | 68 |
| L1 | 9 | 279 |
| L1 | 10 | 279 |
| L1 | 9 | 140 |

TABLE XII C-continued

HPV11
HLA-B27 Supermotif Peptides

| 2 | 3 | 4 |
|---|---|---|
| E2 | 9 | 326 |
| E2 | 11 | 326 |
| E1 | 10 | 311 |
| E1 | 11 | 311 |
| E1 | 8 | 469 |
| E1 | 8 | 119 |
| E1 | 9 | 119 |
| L2 | 8 | 32 |
| L1 | 8 | 60 |
| L1 | 11 | 60 |
| L2 | 11 | 213 |
| E4 | 10 | 51 |
| E1 | 8 | 108 |
| L2 | 8 | 217 |
| L2 | 10 | 219 |
| L2 | 9 | 310 |
| L2 | 10 | 310 |
| L2 | 8 | 360 |
| L2 | 9 | 360 |
| L2 | 8 | 187 |
| L2 | 11 | 187 |
| L1 | 10 | 311 |
| E1 | 9 | 253 |
| E1 | 10 | 253 |
| E2 | 9 | 176 |
| L2 | 11 | 243 |
| L1 | 10 | 93 |
| E2 | 11 | 341 |
| E6 | 8 | 78 |
| E2 | 9 | 356 |
| E2 | 11 | 356 |
| E1 | 8 | 448 |
| E1 | 10 | 448 |
| E1 | 11 | 448 |
| L1 | 8 | 361 |
| L1 | 10 | 361 |
| L1 | 11 | 361 |
| E1 | 8 | 411 |
| E1 | 11 | 411 |
| L1 | 10 | 248 |
| L1 | 11 | 248 |
| L1 | 9 | 462 |
| E1 | 8 | 550 |
| E1 | 9 | 550 |
| L2 | 9 | 8 |
| L2 | 10 | 8 |
| L2 | 8 | 443 |
| E4 | 9 | 52 |
| E1 | 8 | 84 |
| L2 | 10 | 289 |
| L2 | 10 | 7 |
| L2 | 11 | 7 |
| L2 | 8 | 442 |
| L2 | 9 | 442 |
| E1 | 9 | 124 |
| L2 | 11 | 6 |
| L2 | 8 | 441 |
| L2 | 9 | 441 |
| L2 | 10 | 441 |
| L2 | 9 | 440 |
| L2 | 10 | 440 |
| L2 | 11 | 440 |
| E1 | 8 | 507 |
| E6 | 8 | 63 |
| E6 | 10 | 63 |
| E6 | 11 | 63 |
| E2 | 11 | 52 |
| E6 | 11 | 3 |
| E1 | 8 | 572 |
| E1 | 9 | 572 |
| L1 | 11 | 346 |
| L1 | 9 | 18 |
| E1 | 9 | 287 |
| L2 | 9 | 296 |

TABLE XII C-continued

HPV11
HLA-B27 Supermotif Peptides

| 2 | 3 | 4 |
|---|---|---|
| L2 | 10 | 296 |
| L1 | 10 | 39 |
| L1 | 11 | 39 |
| L2 | 8 | 288 |
| L2 | 11 | 288 |
| E1 | 8 | 582 |
| E2 | 11 | 135 |
| E4 | 11 | 96 |
| E2 | 9 | 67 |
| E2 | 11 | 67 |
| E1 | 9 | 432 |
| E1 | 40 | 186 |
| E1 | 11 | 186 |
| E1 | 9 | 129 |
| E1 | 11 | 129 |
| E1 | 10 | 342 |
| L2 | 11 | 306 |
| L1 | 8 | 334 |
| L1 | 8 | 289 |
| E1 | 11 | 403 |
| E2 | 11 | 119 |
| E1 | 11 | 122 |
| L1 | 8 | 27 |
| E1 | 11 | 317 |
| E1 | 8 | 610 |
| E2 | 10 | 33 |
| E2 | 11 | 33 |
| E6 | 9 | 133 |
| E1 | 8 | 440 |
| L1 | 9 | 2 |
| L1 | 8 | 34 |
| L1 | 9 | 34 |
| L1 | 11 | 437 |
| L1 | 11 | 356 |
| E1 | 9 | 413 |
| E1 | 11 | 413 |
| E6 | 8 | 48 |
| L1 | 8 | 148 |
| E1 | 11 | 577 |
| L1 | 11 | 470 |
| E6 | 9 | 77 |
| E2 | 10 | 301 |
| E2 | 11 | 301 |
| L1 | 8 | 67 |
| L1 | 9 | 414 |

SF 1168116 v1

TABLE XIII

HLA-B58 Supermotif Peptides

| 1 | 2 | 3 | 4 |
|---|---|---|---|
| HPV16 | E1 | 11 | 316 |
| HPV16 | E1 | 9 | 239 |
| HPV16 | E1 | 10 | 239 |
| HPV16 | E1 | 10 | 317 |
| HPV16 | E1 | 10 | 205 |
| HPV16 | E1 | 11 | 205 |
| HPV16 | E1 | 8 | 478 |
| HPV16 | E1 | 9 | 478 |
| HPV16 | E1 | 11 | 478 |
| HPV16 | E1 | 11 | 389 |
| HPV16 | E1 | 10 | 406 |
| HPV16 | E1 | 8 | 524 |
| HPV16 | E1 | 9 | 524 |
| HPV16 | E1 | 8 | 405 |
| HPV16 | E1 | 11 | 405 |
| HPV16 | E1 | 8 | 269 |
| HPV16 | E1 | 9 | 269 |
| HPV16 | E1 | 10 | 269 |

TABLE XIII-continued

HLA-B58 Supermotif Peptides

| 1 | 2 | 3 | 4 |
|---|---|---|---|
| HPV16 | E1 | 11 | 269 |
| HPV16 | E1 | 8 | 353 |
| HPV16 | E1 | 9 | 353 |
| HPV16 | E1 | 11 | 353 |
| HPV16 | E1 | 10 | 515 |
| HPV16 | E1 | 9 | 523 |
| HPV16 | E1 | 10 | 523 |
| HPV16 | E1 | 10 | 81 |
| HPV16 | E1 | 11 | 81 |
| HPV16 | E1 | 8 | 41 |
| HPV16 | E1 | 9 | 41 |
| HPV16 | E1 | 11 | 41 |
| HPV16 | E1 | 8 | 372 |
| HPV16 | E1 | 9 | 372 |
| HPV16 | E1 | 11 | 372 |
| HPV16 | E1 | 9 | 131 |
| HPV16 | E1 | 10 | 249 |
| HPV16 | E1 | 9 | 633 |
| HPV16 | E1 | 11 | 573 |
| HPV16 | E1 | 9 | 43 |
| HPV16 | E1 | 10 | 43 |
| HPV16 | E1 | 11 | 43 |
| HPV16 | E1 | 8 | 384 |
| HPV16 | E1 | 9 | 384 |
| HPV16 | E1 | 10 | 384 |
| HPV16 | E1 | 11 | 335 |
| HPV16 | E1 | 8 | 75 |
| HPV16 | E1 | 9 | 75 |
| HPV16 | E1 | 11 | 75 |
| HPV16 | E1 | 11 | 22 |
| HPV16 | E1 | 9 | 65 |
| HPV16 | E1 | 8 | 63 |
| HPV16 | E1 | 9 | 63 |
| HPV16 | E1 | 11 | 63 |
| HPV16 | E1 | 9 | 152 |
| HPV16 | E1 | 10 | 288 |
| HPV16 | E1 | 11 | 288 |
| HPV16 | E1 | 8 | 140 |
| HPV16 | E1 | 8 | 219 |
| HPV16 | E1 | 8 | 613 |
| HPV16 | E1 | 10 | 613 |
| HPV16 | E1 | 9 | 586 |
| HPV16 | E1 | 9 | 477 |
| HPV16 | E1 | 10 | 477 |
| HPV16 | E1 | 9 | 163 |
| HPV16 | E1 | 8 | 571 |
| HPV16 | E1 | 9 | 571 |
| HPV16 | E1 | 8 | 12 |
| HPV16 | E1 | 9 | 12 |
| HPV16 | E1 | 10 | 12 |
| HPV16 | E1 | 9 | 68 |
| HPV16 | E1 | 8 | 348 |
| HPV16 | E1 | 10 | 348 |
| HPV16 | E1 | 8 | 184 |
| HPV16 | E1 | 11 | 184 |
| HPV16 | E1 | 10 | 238 |
| HPV16 | E1 | 11 | 238 |
| HPV16 | E1 | 8 | 247 |
| HPV16 | E1 | 9 | 247 |
| HPV16 | E1 | 8 | 375 |
| HPV16 | E1 | 9 | 375 |
| HPV16 | E1 | 11 | 329 |
| HPV16 | E1 | 9 | 98 |
| HPV16 | E1 | 8 | 326 |
| HPV16 | E1 | 8 | 106 |
| HPV16 | E1 | 10 | 106 |
| HPV16 | E1 | 8 | 204 |
| HPV16 | E1 | 11 | 204 |
| HPV16 | E1 | 11 | 111 |
| HPV16 | E1 | 8 | 610 |
| HPV16 | E1 | 11 | 610 |
| HPV16 | E1 | 9 | 505 |
| HPV16 | E1 | 10 | 505 |
| HPV16 | E1 | 8 | 483 |
| HPV16 | E1 | 9 | 483 |
| HPV16 | E1 | 11 | 483 |
| HPV16 | E1 | 10 | 227 |
| HPV16 | E1 | 8 | 394 |
| HPV16 | E1 | 9 | 394 |
| HPV16 | E1 | 9 | 230 |
| HPV16 | E1 | 10 | 230 |
| HPV16 | E1 | 11 | 230 |
| HPV16 | E1 | 10 | 323 |
| HPV16 | E1 | 11 | 323 |
| HPV16 | E1 | 9 | 252 |
| HPV16 | E1 | 10 | 252 |
| HPV16 | E1 | 11 | 252 |
| HPV16 | E1 | 8 | 199 |
| HPV16 | E1 | 9 | 199 |
| HPV16 | E1 | 10 | 199 |
| HPV16 | E1 | 11 | 199 |
| HPV16 | E1 | 8 | 267 |
| HPV16 | E1 | 9 | 267 |
| HPV16 | E1 | 10 | 267 |
| HPV16 | E1 | 11 | 267 |
| HPV16 | E1 | 8 | 513 |
| HPV16 | E1 | 9 | 513 |
| HPV16 | E1 | 8 | 382 |
| HPV16 | E1 | 10 | 382 |
| HPV16 | E1 | 11 | 382 |
| HPV16 | E1 | 8 | 208 |
| HPV16 | E1 | 10 | 208 |
| HPV16 | E1 | 8 | 95 |
| HPV16 | E1 | 10 | 294 |
| HPV16 | E1 | 8 | 357 |
| HPV16 | E1 | 9 | 357 |
| HPV16 | E1 | 8 | 457 |
| HPV16 | E1 | 11 | 457 |
| HPV16 | E1 | 8 | 191 |
| HPV16 | E1 | 9 | 243 |
| HPV16 | E1 | 9 | 59 |
| HPV16 | E1 | 11 | 59 |
| HPV16 | E1 | 10 | 454 |
| HPV16 | E1 | 11 | 454 |
| HPV16 | E1 | 11 | 488 |
| HPV16 | E1 | 9 | 420 |
| HPV16 | E1 | 8 | 569 |
| HPV16 | E1 | 10 | 569 |
| HPV16 | E1 | 11 | 569 |
| HPV16 | E1 | 8 | 202 |
| HPV16 | E1 | 10 | 202 |
| HPV16 | E1 | 8 | 538 |
| HPV16 | E1 | 10 | 538 |
| HPV16 | E1 | 8 | 503 |
| HPV16 | E1 | 11 | 503 |
| HPV16 | E1 | 8 | 386 |
| HPV16 | E1 | 11 | 396 |
| HPV16 | E1 | 9 | 136 |
| HPV16 | E1 | 10 | 136 |
| HPV16 | E1 | 9 | 480 |
| HPV16 | E1 | 11 | 480 |
| HPV16 | E1 | 10 | 245 |
| HPV16 | E1 | 11 | 245 |
| HPV16 | E1 | 9 | 61 |
| HPV16 | E1 | 10 | 61 |
| HPV16 | E1 | 11 | 61 |
| HPV16 | E1 | 9 | 398 |
| HPV16 | E1 | 11 | 398 |
| HPV16 | E1 | 9 | 265 |
| HPV16 | E1 | 10 | 265 |
| HPV16 | E1 | 11 | 265 |
| HPV16 | E1 | 9 | 118 |
| HPV16 | E1 | 10 | 118 |
| HPV16 | E1 | 8 | 188 |
| HPV16 | E1 | 10 | 188 |
| HPV16 | E1 | 11 | 188 |
| HPV16 | E1 | 8 | 343 |
| HPV16 | E1 | 8 | 120 |
| HPV16 | E1 | 9 | 414 |
| HPV16 | E1 | 8 | 313 |

TABLE XIII-continued

HLA-B58 Supermotif Peptides

| 1 | 2 | 3 | 4 |
|---|---|---|---|
| HPV16 | E1 | 9 | 313 |
| HPV16 | E1 | 10 | 313 |
| HPV16 | E1 | 8 | 615 |
| HPV16 | E1 | 10 | 390 |
| HPV16 | E1 | 9 | 172 |
| HPV16 | E1 | 8 | 314 |
| HPV16 | E1 | 9 | 314 |
| HPV16 | E1 | 8 | 231 |
| HPV16 | E1 | 9 | 231 |
| HPV16 | E1 | 10 | 231 |
| HPV16 | E1 | 11 | 231 |
| HPV16 | E1 | 8 | 315 |
| HPV16 | E1 | 8 | 66 |
| HPV16 | E1 | 11 | 66 |
| HPV16 | E1 | 10 | 458 |
| HPV16 | E1 | 11 | 72 |
| HPV16 | E1 | 8 | 200 |
| HPV16 | E1 | 9 | 200 |
| HPV16 | E1 | 10 | 200 |
| HPV16 | E1 | 10 | 217 |
| HPV16 | E1 | 9 | 641 |
| HPV16 | E1 | 10 | 545 |
| HPV16 | E1 | 11 | 545 |
| HPV16 | E1 | 11 | 92 |
| HPV16 | E1 | 8 | 300 |
| HPV16 | E1 | 8 | 363 |
| HPV16 | E1 | 11 | 379 |
| HPV16 | E1 | 10 | 171 |
| HPV16 | E2 | 8 | 220 |
| HPV16 | E2 | 9 | 220 |
| HPV16 | E2 | 10 | 220 |
| HPV16 | E2 | 10 | 143 |
| HPV16 | E2 | 8 | 221 |
| HPV16 | E2 | 9 | 221 |
| HPV16 | E2 | 10 | 40 |
| HPV16 | E2 | 11 | 309 |
| HPV16 | E2 | 10 | 174 |
| HPV16 | E2 | 11 | 174 |
| HPV16 | E2 | 8 | 294 |
| HPV16 | E2 | 10 | 294 |
| HPV16 | E2 | 8 | 263 |
| HPV16 | E2 | 9 | 263 |
| HPV16 | E2 | 9 | 338 |
| HPV16 | E2 | 10 | 338 |
| HPV16 | E2 | 9 | 22 |
| HPV16 | E2 | 11 | 22 |
| HPV16 | E2 | 8 | 260 |
| HPV16 | E2 | 9 | 260 |
| HPV16 | E2 | 11 | 260 |
| HPV16 | E2 | 11 | 246 |
| HPV16 | E2 | 11 | 142 |
| HPV16 | E2 | 8 | 80 |
| HPV16 | E2 | 9 | 2 |
| HPV16 | E2 | 11 | 200 |
| HPV16 | E2 | 9 | 230 |
| HPV16 | E2 | 8 | 187 |
| HPV16 | E2 | 11 | 252 |
| HPV16 | E2 | 8 | 356 |
| HPV16 | E2 | 10 | 356 |
| HPV16 | E2 | 8 | 68 |
| HPV16 | E2 | 10 | 68 |
| HPV16 | E2 | 10 | 45 |
| HPV16 | E2 | 9 | 329 |
| HPV16 | E2 | 9 | 354 |
| HPV16 | E2 | 10 | 354 |
| HPV16 | E2 | 8 | 62 |
| HPV16 | E2 | 9 | 62 |
| HPV16 | E2 | 11 | 62 |
| HPV16 | E2 | 10 | 347 |
| HPV16 | E2 | 8 | 103 |
| HPV16 | E2 | 11 | 16 |
| HPV16 | E2 | 11 | 77 |
| HPV16 | E2 | 8 | 282 |
| HPV16 | E2 | 10 | 282 |
| HPV16 | E2 | 9 | 84 |
| HPV16 | E2 | 11 | 84 |
| HPV16 | E2 | 8 | 272 |
| HPV16 | E2 | 8 | 296 |
| HPV16 | E2 | 10 | 296 |
| HPV16 | E2 | 8 | 127 |
| HPV16 | E2 | 11 | 127 |
| HPV16 | E2 | 8 | 284 |
| HPV16 | E2 | 8 | 219 |
| HPV16 | E2 | 9 | 219 |
| HPV16 | E2 | 10 | 219 |
| HPV16 | E2 | 11 | 219 |
| HPV16 | E2 | 10 | 106 |
| HPV16 | E2 | 10 | 60 |
| HPV16 | E2 | 11 | 60 |
| HPV16 | E2 | 10 | 196 |
| HPV16 | E2 | 9 | 71 |
| HPV16 | E2 | 11 | 165 |
| HPV16 | E2 | 8 | 330 |
| HPV16 | E2 | 8 | 264 |
| HPV16 | E2 | 10 | 201 |
| HPV16 | E2 | 11 | 201 |
| HPV16 | E2 | 10 | 206 |
| HPV16 | E2 | 11 | 206 |
| HPV16 | E2 | 11 | 316 |
| HPV16 | E2 | 8 | 23 |
| HPV16 | E2 | 10 | 23 |
| HPV16 | E2 | 11 | 23 |
| HPV16 | E2 | 10 | 317 |
| HPV16 | E2 | 11 | 269 |
| HPV16 | E2 | 9 | 313 |
| HPV16 | E2 | 9 | 197 |
| HPV16 | E2 | 10 | 253 |
| HPV16 | E2 | 11 | 285 |
| HPV16 | E2 | 9 | 64 |
| HPV16 | E2 | 10 | 64 |
| HPV16 | E2 | 9 | 97 |
| HPV16 | E2 | 11 | 205 |
| HPV16 | E2 | 8 | 358 |
| HPV16 | E2 | 9 | 333 |
| HPV16 | E2 | 8 | 145 |
| HPV16 | E2 | 10 | 145 |
| HPV16 | E2 | 11 | 145 |
| HPV16 | E2 | 11 | 321 |
| HPV16 | E2 | 10 | 134 |
| HPV16 | E2 | 8 | 92 |
| HPV16 | E2 | 10 | 92 |
| HPV16 | E2 | 11 | 92 |
| RPV16 | E2 | 9 | 178 |
| HPV16 | E2 | 11 | 178 |
| HPV16 | E2 | 8 | 87 |
| HPV16 | E2 | 11 | 87 |
| HPV16 | E2 | 8 | 312 |
| HPV16 | E2 | 10 | 312 |
| HPV16 | E2 | 8 | 131 |
| HPV16 | E2 | 9 | 131 |
| HPV16 | E2 | 11 | 115 |
| HPV16 | E5 | 8 | 53 |
| HPV16 | E5 | 9 | 53 |
| HPV16 | E5 | 10 | 53 |
| HPV16 | E5 | 11 | 53 |
| HPV16 | E5 | 8 | 54 |
| HPV16 | E5 | 9 | 54 |
| HPV16 | E5 | 10 | 54 |
| HPV16 | E5 | 11 | 54 |
| HPV16 | E5 | 9 | 7 |
| HPV16 | E5 | 10 | 7 |
| HPV16 | E5 | 11 | 7 |
| HPV16 | E5 | 8 | 5 |
| HPV16 | E5 | 9 | 5 |
| HPV16 | E5 | 11 | 5 |
| HPV16 | E5 | 8 | 75 |
| HPV16 | E5 | 10 | 51 |
| HPV16 | E5 | 11 | 51 |
| HPV16 | E5 | 8 | 12 |
| HPV16 | E5 | 10 | 12 |

TABLE XIII-continued

HLA-B58 Supermotif Peptides

| 1 | 2 | 3 | 4 |
|---|---|---|---|
| HPV16 | E5 | 11 | 12 |
| HPV16 | E5 | 9 | 34 |
| HPV16 | E5 | 10 | 34 |
| HPV16 | E5 | 11 | 34 |
| HPV16 | E5 | 11 | 1 |
| HPV16 | E5 | 8 | 55 |
| HPV16 | E5 | 9 | 55 |
| HPV16 | E5 | 10 | 55 |
| HPV16 | E5 | 11 | 55 |
| HPV16 | E5 | 8 | 8 |
| HPV16 | E5 | 9 | 8 |
| HPV16 | E5 | 10 | 8 |
| HPV16 | E5 | 8 | 37 |
| HPV16 | E5 | 9 | 37 |
| HPV16 | E5 | 10 | 37 |
| HPV16 | E5 | 11 | 37 |
| HPV16 | E5 | 9 | 52 |
| HPV16 | E5 | 10 | 52 |
| HPV16 | E5 | 11 | 52 |
| HPV16 | E5 | 8 | 6 |
| HPV16 | E5 | 10 | 6 |
| HPV16 | E5 | 11 | 6 |
| HPV16 | E5 | 8 | 40 |
| HPV16 | E5 | 9 | 40 |
| HPV16 | E5 | 10 | 40 |
| HPV16 | E5 | 11 | 40 |
| HPV16 | E5 | 8 | 9 |
| HPV16 | E5 | 9 | 9 |
| HPV16 | E5 | 11 | 9 |
| HPV16 | E5 | 8 | 36 |
| HPV16 | E5 | 9 | 36 |
| HPV16 | E5 | 10 | 36 |
| HPV16 | E5 | 11 | 36 |
| HPV16 | E5 | 8 | 39 |
| HPV16 | E5 | 9 | 39 |
| HPV16 | E5 | 10 | 39 |
| HPV16 | E5 | 11 | 39 |
| HPV16 | E6 | 8 | 23 |
| HPV16 | E6 | 11 | 23 |
| HPV16 | E6 | 8 | 52 |
| HPV16 | E6 | 9 | 52 |
| HPV16 | E6 | 10 | 52 |
| HPV16 | E6 | 8 | 92 |
| HPV16 | E6 | 9 | 80 |
| HPV16 | E6 | 11 | 80 |
| HPV16 | E6 | 8 | 27 |
| HPV16 | E6 | 9 | 27 |
| HPV16 | E6 | 11 | 148 |
| HPV16 | E6 | 8 | 151 |
| HPV16 | E6 | 10 | 149 |
| HPV16 | E6 | 8 | 28 |
| HPV16 | E6 | 11 | 28 |
| HPV16 | E6 | 11 | 93 |
| HPV16 | E6 | 8 | 67 |
| HPV16 | E6 | 10 | 67 |
| HPV16 | E6 | 11 | 67 |
| HPV16 | E6 | 10 | 77 |
| HPV16 | E6 | 8 | 88 |
| HPV16 | E7 | 9 | 30 |
| HPV16 | E7 | 8 | 62 |
| HPV16 | E7 | 8 | 4 |
| HPV16 | E7 | 9 | 4 |
| HPV16 | E7 | 10 | 4 |
| HPV16 | E7 | 8 | 18 |
| HPV16 | E7 | 11 | 18 |
| HPV16 | E7 | 9 | 85 |
| HPV16 | E7 | 10 | 41 |
| HPV16 | E7 | 8 | 6 |
| HPV16 | E7 | 10 | 6 |
| HPV16 | E7 | 9 | 44 |
| HPV16 | E7 | 11 | 44 |
| HPV16 | E7 | 10 | 70 |
| HPV16 | E7 | 9 | 49 |
| HPV16 | E7 | 8 | 77 |
| HPV16 | E7 | 11 | 77 |
| HPV16 | E7 | 8 | 31 |
| HPV16 | E7 | 9 | 71 |
| HPV16 | E7 | 10 | 19 |
| HPV16 | E7 | 11 | 55 |
| HPV16 | L1 | 10 | 372 |
| HPV16 | L1 | 8 | 158 |
| HPV16 | L1 | 10 | 158 |
| HPV16 | L1 | 8 | 35 |
| HPV16 | L1 | 10 | 35 |
| HPV16 | L1 | 11 | 371 |
| HPV16 | L1 | 10 | 251 |
| HPV16 | L1 | 11 | 251 |
| HPV16 | L1 | 9 | 329 |
| HPV16 | L1 | 10 | 329 |
| HPV16 | L1 | 11 | 329 |
| HPV16 | L1 | 8 | 154 |
| HPV16 | L1 | 9 | 154 |
| HPV16 | L1 | 10 | 154 |
| HPV16 | L1 | 9 | 228 |
| HPV16 | L1 | 8 | 120 |
| HPV16 | L1 | 10 | 120 |
| HPV16 | L1 | 8 | 361 |
| HPV16 | L1 | 10 | 361 |
| HPV16 | L1 | 10 | 442 |
| HPV16 | L1 | 11 | 442 |
| HPV16 | L1 | 9 | 34 |
| HPV16 | L1 | 11 | 34 |
| HPV16 | L1 | 9 | 378 |
| HPV16 | L1 | 8 | 481 |
| HPV16 | L1 | 10 | 481 |
| HPV16 | L1 | 8 | 506 |
| HPV16 | L1 | 11 | 236 |
| HPV16 | L1 | 8 | 232 |
| HPV16 | L1 | 10 | 232 |
| HPV16 | L1 | 11 | 291 |
| HPV16 | L1 | 8 | 305 |
| HPV16 | L1 | 9 | 305 |
| HPV16 | L1 | 8 | 323 |
| HPV16 | L1 | 10 | 323 |
| HPV16 | L1 | 11 | 323 |
| HPV16 | L1 | 8 | 198 |
| HPV16 | L1 | 9 | 198 |
| HPV16 | L1 | 11 | 307 |
| HPV16 | L1 | 9 | 438 |
| HPV16 | L1 | 10 | 438 |
| HPV16 | L1 | 8 | 64 |
| HPV16 | L1 | 8 | 62 |
| HPV16 | L1 | 9 | 62 |
| HPV16 | L1 | 10 | 62 |
| HPV16 | L1 | 8 | 418 |
| HPV16 | L1 | 11 | 418 |
| HPV16 | L1 | 11 | 457 |
| HPV16 | L1 | 10 | 452 |
| HPV16 | L1 | 10 | 143 |
| HPV16 | L1 | 10 | 173 |
| HPV16 | L1 | 8 | 374 |
| HPV16 | L1 | 8 | 11 |
| HPV16 | L1 | 10 | 11 |
| HPV16 | L1 | 11 | 11 |
| HPV16 | L1 | 8 | 407 |
| HPV16 | L1 | 10 | 407 |
| HPV16 | L1 | 11 | 407 |
| HPV16 | L1 | 8 | 501 |
| HPV16 | L1 | 8 | 243 |
| HPV16 | L1 | 8 | 69 |
| HPV16 | L1 | 10 | 69 |
| HPV16 | L1 | 8 | 409 |
| HPV16 | L1 | 9 | 409 |
| HPV16 | L1 | 9 | 27 |
| HPV16 | L1 | 11 | 27 |
| HPV16 | L1 | 11 | 414 |
| HPV16 | L1 | 10 | 164 |
| HPV16 | L1 | 9 | 157 |
| HPV16 | L1 | 11 | 157 |
| HPV16 | L1 | 8 | 421 |

TABLE XIII-continued

HLA-B58 Supermotif Peptides

| 1 | 2 | 3 | 4 |
|---|---|---|---|
| HPV16 | L1 | 10 | 421 |
| HPV16 | L1 | 8 | 383 |
| HPV16 | L1 | 9 | 218 |
| HPV16 | L1 | 10 | 218 |
| HPV16 | L1 | 8 | 460 |
| HPV16 | L1 | 11 | 460 |
| HPV16 | L1 | 8 | 32 |
| HPV16 | L1 | 11 | 32 |
| HPV16 | L1 | 10 | 321 |
| HPV16 | L1 | 8 | 319 |
| HPV16 | L1 | 10 | 515 |
| HPV16 | L1 | 10 | 497 |
| HPV16 | L1 | 9 | 240 |
| HPV16 | L1 | 11 | 240 |
| HPV16 | L1 | 9 | 289 |
| HPV16 | L1 | 9 | 341 |
| HPV16 | L1 | 11 | 341 |
| HPV16 | L1 | 9 | 364 |
| HPV16 | L1 | 10 | 364 |
| HPV16 | L1 | 11 | 364 |
| HPV16 | L1 | 8 | 56 |
| HPV16 | L1 | 9 | 482 |
| HPV16 | L1 | 9 | 159 |
| HPV16 | L1 | 10 | 308 |
| HPV16 | L1 | 11 | 308 |
| HPV16 | L1 | 11 | 49 |
| HPV16 | L1 | 9 | 422 |
| HPV16 | L1 | 11 | 422 |
| HPV16 | L1 | 8 | 365 |
| HPV16 | L1 | 9 | 365 |
| HPV16 | L1 | 10 | 365 |
| HPV16 | L1 | 11 | 521 |
| HPV16 | L1 | 8 | 410 |
| HPV16 | L1 | 11 | 410 |
| HPV16 | L1 | 9 | 523 |
| HPV16 | L1 | 9 | 309 |
| HPV16 | L1 | 10 | 309 |
| HPV16 | L1 | 11 | 327 |
| HPV16 | L1 | 11 | 376 |
| HPV16 | L1 | 11 | 114 |
| HPV16 | L1 | 9 | 252 |
| HPV16 | L1 | 10 | 252 |
| HPV16 | L1 | 11 | 65 |
| HPV16 | L1 | 8 | 517 |
| HPV16 | L1 | 10 | 522 |
| HPV16 | L1 | 10 | 237 |
| HPV16 | L1 | 9 | 362 |
| HPV16 | L1 | 11 | 362 |
| HPV16 | L1 | 9 | 516 |
| HPV16 | L1 | 8 | 379 |
| HPV16 | L1 | 11 | 379 |
| HPV16 | L1 | 8 | 54 |
| HPV16 | L1 | 10 | 54 |
| HPV16 | L1 | 11 | 204 |
| HPV16 | L1 | 9 | 264 |
| HPV16 | L1 | 10 | 264 |
| HPV16 | L1 | 11 | 264 |
| HPV16 | L1 | 8 | 91 |
| HPV16 | L1 | 9 | 91 |
| HPV16 | L1 | 11 | 91 |
| HPV16 | L1 | 10 | 44 |
| HPV16 | L1 | 11 | 44 |
| HPV16 | L1 | 8 | 48 |
| HPV16 | L1 | 8 | 3 |
| HPV16 | L1 | 9 | 3 |
| HPV16 | L1 | 8 | 326 |
| HPV16 | L1 | 8 | 126 |
| HPV16 | L1 | 8 | 470 |
| HPV16 | L2 11 | 355 | |
| HPV16 | L2 | 8 | 82 |
| HPV16 | L2 | 11 | 15 |
| HPV16 | L2 | 8 | 116 |
| HPV16 | L2 | 11 | 116 |
| HPV16 | L2 | 11 | 442 |
| HPV16 | L2 | 8 | 33~ |
| HPV16 | L2 | 11 | 334 |
| HPV16 | L2 | 10 | 84 |
| HPV16 | L2 | 10 | 376 |
| HPV16 | L2 | 9 | 140 |
| HPV16 | L2 | 8 | 176 |
| HPV16 | L2 | 9 | 111 |
| HPV16 | L2 | 8 | 466 |
| HPV16 | L2 | 8 | 268 |
| HPV16 | L2 | 10 | 268 |
| HPV16 | L2 | 11 | 268 |
| HPV16 | L2 | 10 | 330 |
| HPV16 | L2 | 8 | 181 |
| HPV16 | L2 | 8 | 321 |
| HPV16 | L2 | 10 | 321 |
| HPV16 | L2 | 9 | 118 |
| HPV16 | L2 | 8 | 404 |
| HPV16 | L2 | 10 | 63 |
| HPV16 | L2 | 11 | 63 |
| HPV16 | L2 | 10 | 49 |
| HPV16 | L2 | 8 | 433 |
| HPV16 | L2 | 9 | 433 |
| HPV16 | L2 | 11 | 433 |
| HPV16 | L2 | 8 | 218 |
| HPV16 | L2 | 10 | 218 |
| HPV16 | L2 | 11 | 218 |
| HPV16 | L2 | 8 | 26 |
| HPV16 | L2 | 11 | 26 |
| HPV16 | L2 | 8 | 65 |
| HPV16 | L2 | 9 | 65 |
| HPV16 | L2 | 11 | 65 |
| HPV16 | L2 | 11 | 76 |
| HPV16 | L2 | 8 | 354 |
| HPV16 | L2 | 8 | 440 |
| HPV16 | L2 | 9 | 440 |
| HPV16 | L2 | 8 | 41 |
| HPV16 | L2 | 11 | 41 |
| HPV16 | L2 | 8 | 277 |
| HPV16 | L2 | 10 | 277 |
| HPV16 | L2 | 11 | 277 |
| HPV16 | L2 | 9 | 188 |
| HPV16 | L2 | 11 | 188 |
| HPV16 | L2 | 8 | 420 |
| HPV16 | L2 | 9 | 420 |
| HPV16 | L2 | 11 | 420 |
| HPV16 | L2 | 9 | 374 |
| HPV16 | L2 | 8 | 243 |
| HPV16 | L2 | 10 | 243 |
| HPV16 | L2 | 10 | 135 |
| HPV16 | L2 | 11 | 135 |
| HPV16 | L2 | 8 | 250 |
| HPV16 | L2 | 11 | 250 |
| HPV16 | L2 | 9 | 318 |
| HPV16 | L2 | 10 | 318 |
| HPV16 | L2 | 11 | 318 |
| HPV16 | L2 | 8 | 39 |
| HPV16 | L2 | 10 | 39 |
| HPV16 | L2 | 8 | 86 |
| HPV16 | L2 | 10 | 86 |
| HPV16 | L2 | 11 | 390 |
| HPV16 | L2 | 11 | 183 |
| HPV16 | L2 | 8 | 294 |
| HPV16 | L2 | 10 | 294 |
| HPV16 | L2 | 11 | 273 |
| HPV16 | L2 | 9 | 397 |
| HPV16 | L2 10 | 397 | |
| HPV16 | L2 | 9 | 208 |
| HPV16 | L2 | 8 | 174 |
| HPV16 | L2 | 10 | 174 |
| HPV16 | L2 | 10 | 240 |
| HPV16 | L2 | 11 | 240 |
| HPV16 | L2 | 10 | 143 |
| HPV16 | L2 | 10 | 292 |
| HPV16 | L2 | 8 | 395 |
| HPV16 | L2 | 11 | 395 |
| HPV16 | L2 | 8 | 255 |

TABLE XIII-continued

HLA-B58 Supermotif Peptides

| 1 | 2 | 3 | 4 |
|---|---|---|---|
| HPV16 | L2 | 9 | 100 |
| HPV16 | L2 | 10 | 100 |
| HPV16 | L2 | 10 | 124 |
| HPV16 | L2 | 8 | 386 |
| HPV16 | L2 | 9 | 386 |
| HPV16 | L2 | 11 | 386 |
| HPV16 | L2 | 10 | 346 |
| HPV16 | L2 | 11 | 346 |
| HPV16 | L2 | 10 | 166 |
| HPV16 | L2 | 8 | 383 |
| HPV16 | L2 | 11 | 383 |
| HPV16 | L2 | 8 | 80 |
| HPV16 | L2 | 10 | 80 |
| HPV16 | L2 | 8 | 161 |
| HPV16 | L2 | 9 | 161 |
| HPV16 | L2 | 11 | 246 |
| HPV16 | L2 | 10 | 172 |
| HPV16 | L2 | 8 | 358 |
| HPV16 | L2 | 9 | 358 |
| HPV16 | L2 | 11 | 358 |
| HPV16 | L2 | 11 | 120 |
| HPV16 | L2 | 9 | 24 |
| HPV16 | L2 | 10 | 24 |
| HPV16 | L2 | 8 | 423 |
| HPV16 | L2 | 9 | 423 |
| HPV16 | L2 | 8 | 342 |
| HPV16 | L2 | 11 | 310 |
| HPV16 | L2 | 8 | 12 |
| HPV16 | L2 | 9 | 5 |
| HPV16 | L2 | 11 | 5 |
| HPV16 | L2 | 8 | 315 |
| HPV16 | L2 | 10 | 315 |
| HPV16 | L2 | 9 | 298 |
| HPV16 | L2 | 10 | 9 |
| HPV16 | L2 | 11 | 9 |
| HPV16 | L2 | 8 | 313 |
| HPV16 | L2 | 10 | 313 |
| HPV16 | L2 | 8 | 230 |
| HPV16 | L2 | 9 | 230 |
| HPV16 | L2 | 10 | 335 |
| HPV16 | L2 | 8 | 6 |
| HPV16 | L2 | 10 | 6 |
| HPV16 | L2 | 9 | 269 |
| HPV16 | L2 | 10 | 269 |
| HPV16 | L2 | 10 | 184 |
| HPV16 | L2 | 9 | 185 |
| HPV16 | L2 | 11 | 212 |
| HPV16 | L2 | 8 | 138 |
| HPV16 | L2 | 9 | 138 |
| HPV16 | L2 | 11 | 138 |
| HPV16 | L2 | 8 | 189 |
| HPV16 | L2 | 10 | 189 |
| HPV16 | L2 | 9 | 331 |
| HPV16 | L2 | 11 | 331 |
| HPV16 | L2 | 8 | 186 |
| HPV16 | L2 | 11 | 186 |
| HPV16 | L2 | 10 | 213 |
| HPV16 | L2 | 11 | 213 |
| HPV16 | L2 | 8 | 387 |
| HPV16 | L2 | 10 | 387 |
| HPV16 | L2 | 8 | 378 |
| HPV16 | L2 | 9 | 347 |
| HPV16 | L2 | 10 | 347 |
| HPV16 | L2 | 11 | 347 |
| HPV16 | L2 | 9 | 81 |
| HPV16 | L2 | 8 | 112 |
| HPV16 | L2 | 10 | 352 |
| HPV16 | L2 | 8 | 359 |
| HPV16 | L2 | 10 | 359 |
| HPV16 | L2 | 11 | 359 |
| HPV16 | L2 | 9 | 388 |
| HPV16 | L2 | 9 | 295 |
| HPV16 | L2 | 8 | 137 |
| HPV16 | L2 | 9 | 137 |
| HPV16 | L2 | 10 | 137 |
| HPV16 | L2 | 9 | 377 |
| HPV16 | L2 | 10 | 121 |
| HPV16 | L2 | 8 | 156 |
| HPV16 | L2 | 8 | 398 |
| HPV16 | L2 | 9 | 398 |
| HPV16 | L2 | 11 | 398 |
| HPV16 | L2 | 8 | 141 |
| HPV16 | L2 | 9 | 244 |
| HPV16 | L2 | 8 | 231 |
| HPV16 | L2 | 11 | 231 |
| HPV16 | L2 | 11 | 351 |
| HPV16 | L2 | 9 | 136 |
| HPV16 | L2 | 10 | 136 |
| HPV16 | L2 | 11 | 136 |
| HPV16 | L2 | 8 | 350 |
| HPV16 | L2 | 11 | 153 |
| HPV16 | L2 | 8 | 287 |
| HPV16 | L2 | 8 | 411 |
| HPV16 | L2 | 10 | 411 |
| HPV16 | L2 | 9 | 106 |
| HPV16 | L2 | 10 | 106 |
| HPV16 | L2 | 8 | 203 |
| HPV16 | L2 | 9 | 155 |
| HPV16 | L2 | 10 | 303 |
| HPV16 | L2 | 8 | 228 |
| HPV16 | L2 | 10 | 228 |
| HPV16 | L2 | 11 | 228 |
| HPV16 | L2 | 10 | 437 |
| HPV16 | L2 | 11 | 437 |
| HPV16 | L2 | 8 | 349 |
| HPV16 | L2 | 9 | 349 |
| HPV18 | E1 | 11 | 396 |
| HPV18 | E1 | 10 | 397 |
| HPV18 | E1 | 10 | 324 |
| HPV18 | E1 | 8 | 40 |
| HPV18 | E1 | 9 | 40 |
| HPV18 | E1 | 11 | 40 |
| HPV18 | E1 | 10 | 413 |
| HPV18 | E1 | 8 | 531 |
| HPV18 | E1 | 9 | 531 |
| HPV18 | E1 | 8 | 412 |
| HPV18 | E1 | 11 | 412 |
| HPV18 | E1 | 9 | 139 |
| HPV18 | E1 | 11 | 139 |
| HPV18 | E1 | 8 | 160 |
| HPV18 | E1 | 9 | 160 |
| HPV18 | E1 | 10 | 437 |
| HPV18 | E1 | 8 | 240 |
| HPV18 | E1 | 9 | 240 |
| HPV18 | E1 | 11 | 240 |
| HPV18 | E1 | 9 | 196 |
| HPV18 | E1 | 10 | 196 |
| HPV18 | E1 | 9 | 635 |
| HPV18 | E1 | 8 | 78 |
| HPV18 | E1 | 9 | 530 |
| HPV18 | E1 | 10 | 530 |
| HPV18 | E1 | 9 | 134 |
| HPV18 | E1 | 11 | 134 |
| HPV18 | E1 | 9 | 359 |
| HPV18 | E1 | 10 | 359 |
| HPV18 | E1 | 8 | 391 |
| HPV18 | E1 | 9 | 391 |
| HPV18 | E1 | 10 | 391 |
| HPV18 | E1 | 10 | 637 |
| HPV18 | E1 | 8 | 106 |
| HPV18 | E1 | 11 | 106 |
| HPV18 | E1 | 9 | 42 |
| HPV18 | E1 | 10 | 42 |
| HPV18 | E1 | 10 | 522 |
| HPV18 | E1 | 9 | 342 |
| HPV18 | E1 | 11 | 342 |
| HPV18 | E1 | 10 | 52 |
| HPV18 | E1 | 10 | 220 |
| HPV18 | E1 | 11 | 220 |
| HPV18 | E1 | 8 | 540 |

TABLE XIII-continued

HLA-B58 Supermotif Peptides

| 1 | 2 | 3 | 4 |
|---|---|---|---|
| HPV18 | E1 | 8 | 379 |
| HPV18 | E1 | 9 | 379 |
| HPV18 | E1 | 10 | 379 |
| HPV18 | E1 | 11 | 379 |
| HPV18 | E1 | 9 | 587 |
| HPV18 | E1 | 9 | 64 |
| HPV18 | E1 | 11 | 309 |
| HPV18 | E1 | 11 | 89 |
| HPV18 | E1 | 8 | 226 |
| HPV18 | E1 | 8 | 130 |
| HPV18 | E1 | 11 | 212 |
| HPV18 | E1 | 8 | 44 |
| HPV18 | E1 | 8 | 92 |
| HPV18 | E1 | 9 | 172 |
| HPV18 | E1 | 9 | 55 |
| HPV18 | E1 | 8 | 11 |
| HPV18 | E1 | 9 | 11 |
| HPV18 | E1 | 10 | 11 |
| HPV18 | E1 | 8 | 473 |
| HPV18 | E1 | 9 | 473 |
| HPV18 | E1 | 10 | 473 |
| HPV18 | E1 | 8 | 182 |
| HPV18 | E1 | 11 | 182 |
| HPV18 | E1 | 9 | 71 |
| HPV18 | E1 | 11 | 71 |
| HPV18 | E1 | 8 | 254 |
| HPV18 | E1 | 9 | 254 |
| HPV18 | E1 | 8 | 198 |
| HPV18 | E1 | 10 | 198 |
| HPV18 | E1 | 9 | 32 |
| HPV18 | E1 | 11 | 132 |
| HPV18 | E1 | 11 | 336 |
| HPV18 | E1 | 10 | 506 |
| HPV18 | E1 | 11 | 506 |
| HPV18 | E1 | 10 | 552 |
| HPV18 | E1 | 11 | 552 |
| HPV18 | E1 | 10 | 116 |
| HPV18 | E1 | 8 | 333 |
| HPV18 | E1 | 10 | 461 |
| HPV18 | E1 | 11 | 461 |
| HPV18 | E1 | 9 | 590 |
| HPV18 | E1 | 10 | 590 |
| HPV18 | E1 | 9 | 124 |
| HPV18 | E1 | 10 | 234 |
| HPV18 | E1 | 11 | 234 |
| HPV18 | E1 | 8 | 401 |
| HPV18 | E1 | 9 | 401 |
| HPV18 | E1 | 10 | 292 |
| HPV18 | E1 | 8 | 490 |
| HPV18 | E1 | 9 | 490 |
| HPV18 | E1 | 11 | 490 |
| HPV18 | E1 | 8 | 259 |
| HPV18 | E1 | 9 | 259 |
| HPV18 | E1 | 10 | 259 |
| HPV18 | E1 | 11 | 259 |
| HPV18 | E1 | 8 | 237 |
| HPV18 | E1 | 10 | 237 |
| HPV18 | E1 | 11 | 237 |
| HPV18 | E1 | 8 | 389 |
| HPV18 | E1 | 9 | 389 |
| HPV18 | E1 | 10 | 389 |
| HPV18 | E1 | 11 | 389 |
| HPV18 | E1 | 8 | 215 |
| HPV18 | E1 | 10 | 215 |
| HPV18 | E1 | 8 | 364 |
| HPV18 | E1 | 9 | 364 |
| HPV18 | E1 | 10 | 224 |
| HPV18 | E1 | 8 | 109 |
| HPV18 | E1 | 10 | 109 |
| HPV18 | E1 | 8 | 376 |
| HPV18 | E1 | 9 | 376 |
| HPV18 | E1 | 11 | 376 |
| HPV18 | E1 | 8 | 520 |
| HPV18 | E1 | 9 | 520 |
| HPV18 | E1 | 8 | 350 |
| HPV18 | E1 | 8 | 571 |
| HPV18 | E1 | 10 | 295 |
| HPV18 | E1 | 11 | 295 |
| HPV18 | E1 | 8 | 382 |
| HPV18 | E1 | 9 | 382 |
| HPV18 | E1 | 10 | 495 |
| HPV18 | E1 | 11 | 495 |
| HPV18 | E1 | 8 | 545 |
| HPV18 | E1 | 10 | 545 |
| HPV18 | E1 | 9 | 39 |
| HPV18 | E1 | 10 | 39 |
| HPV18 | E1 | 11 | 119 |
| HPV18 | E1 | 8 | 393 |
| HPV18 | E1 | 8 | 96 |
| HPV18 | E1 | 10 | 96 |
| HPV18 | E1 | 8 | 510 |
| HPV18 | E1 | 11 | 510 |
| HPV18 | E1 | 9 | 487 |
| HPV18 | E1 | 11 | 487 |
| HPV18 | E1 | 9 | 577 |
| HPV18 | E1 | 10 | 577 |
| HPV18 | E1 | 8 | 485 |
| HPV18 | E1 | 9 | 485 |
| HPV18 | E1 | 11 | 485 |
| HPV18 | E1 | 10 | 252 |
| HPV18 | E1 | 11 | 252 |
| HPV18 | E1 | 9 | 60 |
| HPV18 | E1 | 10 | 60 |
| HPV18 | E1 | 11 | 60 |
| HPV18 | E1 | 11 | 21 |
| HPV18 | E1 | 9 | 405 |
| HPV18 | E1 | 11 | 405 |
| HPV18 | E1 | 9 | 67 |
| HPV18 | E1 | 9 | 649 |
| HPV18 | E1 | 9 | 421 |
| HPV18 | E1 | 8 | 320 |
| HPV18 | E1 | 9 | 320 |
| HPV18 | E1 | 10 | 320 |
| HPV18 | E1 | 10 | 330 |
| HPV18 | E1 | 11 | 330 |
| HPV18 | E1 | 8 | 622 |
| HPV18 | E1 | 8 | 321 |
| HPV18 | E1 | 9 | 321 |
| HPV18 | E1 | 11 | 93 |
| HPV18 | E1 | 11 | 302 |
| HPV18 | E1 | 10 | 511 |
| HPV18 | E1 | 10 | 245 |
| HPV18 | E1 | 11 | 245 |
| HPV18 | E1 | 8 | 65 |
| HPV18 | E1 | 11 | 65 |
| HPV18 | E1 | 10 | 183 |
| HPV18 | E1 | 9 | 512 |
| HPV18 | E1 | 9 | 238 |
| HPV18 | E1 | 10 | 238 |
| HPV18 | E1 | 11 | 238 |
| HPV18 | E1 | 10 | 533 |
| HPV18 | E1 | 11 | 533 |
| HPV18 | E1 | 10 | 150 |
| HPV18 | E1 | 8 | 532 |
| HPV18 | E1 | 11 | 532 |
| HPV18 | E1 | 11 | 323 |
| HPV18 | E1 | 8 | 297 |
| HPV18 | E1 | 9 | 297 |
| HPV18 | E1 | 11 | 297 |
| HPV18 | E1 | 11 | 244 |
| HPV18 | E1 | 11 | 149 |
| HPV18 | E1 | 8 | 536 |
| HPV18 | E1 | 11 | 536 |
| HPV18 | E1 | 11- | 268 |
| HPV18 | E1 | 11 | 386 |
| HPV18 | E2 | 10 | 49 |
| HPV18 | E2 | 10 | 245 |
| HPV18 | E2 | 11 | 245 |
| HPV18 | E2 | 9 | 154 |
| HPV18 | E2 | 10 | 154 |

TABLE XIII-continued

HLA-B58 Supermotif Peptides

| 1 | 2 | 3 | 4 |
|---|---|---|---|
| HPV18 | E2 | 11 | 154 |
| HPV18 | E2 | 8 | 214 |
| HPV18 | E2 | 9 | 246 |
| HPV18 | E2 | 10 | 246 |
| HPV18 | E2 | 8 | 282 |
| HPV18 | E2 | 9 | 282 |
| HPV18 | E2 | 11 | 282 |
| HPV18 | E2 | 8 | 205 |
| HPV18 | E2 | 10 | 205 |
| HPV18 | E2 | 9 | 146 |
| HPV18 | E2 | 9 | 26 |
| HPV18 | E2 | 11 | 26 |
| HPV18 | E2 | 11 | 202 |
| HPV18 | E2 | 9 | 31 |
| HPV18 | E2 | 10 | 31 |
| HPV18 | E2 | 9 | 354 |
| HPV18 | E2 | 10 | 354 |
| HPV18 | E2 | 9 | 139 |
| HPV18 | E2 | 8 | 210 |
| HPV18 | E2 | 9 | 210 |
| HPV18 | E2 | 10 | 6 |
| HPV18 | E2 | 8 | 340 |
| HPV18 | E2 | 11 | 340 |
| HPV18 | E2 | 8 | 48 |
| HPV18 | E2 | 11 | 48 |
| HPV18 | E2 | 9 | 324 |
| HPV18 | E2 | 10 | 324 |
| HPV18 | E2 | 11 | 235 |
| HPV18 | E2 | 10 | 148 |
| HPV18 | E2 | 11 | 187 |
| HPV18 | E2 | 8 | 309 |
| HPV18 | E2 | 9 | 338 |
| HPV18 | E2 | 10 | 338 |
| HPV18 | E2 | 10 | 223 |
| HPV18 | E2 | 9 | 68 |
| HPV18 | E2 | 10 | 68 |
| HPV18 | E2 | 10 | 316 |
| HPV18 | E2 | 8 | 72 |
| HPV18 | E2 | 10 | 72 |
| HPV18 | E2 | 11 | 72 |
| HPV18 | E2 | 8 | 75 |
| HPV18 | E2 | 9 | 75 |
| HPV18 | E2 | 8 | 70 |
| HPV18 | E210 | 70 | |
| HPV18 | E211 | 152 | |
| HPV18 | E2 | 9 | 329 |
| HPV18 | E2 | 8 | 238 |
| HPV18 | E2 | 9 | 238 |
| HPV18 | E210 | 254 | |
| HPV18 | E211 | 86 | |
| HPV18 | E2 | 8 | 12 |
| HPV18 | E2 | 9 | 12 |
| HPV18 | E2 | 8 | 8 |
| HPV18 | E2 | 11 | 81 |
| HPV18 | E2 | 11 | 144 |
| HPV18 | E2 | 9 | 133 |
| HPV18 | E2 | 10 | 133 |
| HPV18 | E2 | 11 | 133 |
| HPV18 | E2 | 8 | 297 |
| HPV18 | E2 | 10 | 297 |
| HPV18 | E2 | 8 | 107 |
| HPV18 | E2 | 9 | 185 |
| HPV18 | E2 | 8 | 285 |
| HPV18 | E2 | 9 | 348 |
| HPV18 | E2 | 11 | 348 |
| HPV18 | E2 | 10 | 64 |
| HPV18 | E2 | 8 | 225 |
| HPV18 | E2 | 10 | 225 |
| HPV18 | E2 | 10 | 272 |
| HPV18 | E2 | 9 | 88 |
| HPV18 | E2 | 11 | 88 |
| HPV18 | E2 | 8 | 56 |
| HPV18 | E2 | 10 | 56 |
| HPV18 | E2 | 11 | 56 |
| HPV18 | E2 | 11 | 2 |
| HPV18 | E2 | 8 | 343 |
| HPV18 | E2 | 9 | 343 |
| HPV18 | E2 | 10 | 343 |
| HPV18 | E2 | 11 | 244 |
| HPV18 | E2 | 9 | 213 |
| HPV18 | E2 | 9 | 229 |
| HPV18 | E2 | 9 | 317 |
| HPV18 | E2 | 9 | 206 |
| HPV18 | E2 | 8 | 230 |
| HPV18 | E2 | 11 | 230 |
| HPV18 | E2 | 8 | 318 |
| HPV18 | E2 | 10 | 236 |
| HPV18 | E2 | 11 | 236 |
| HPV18 | E2 | 10 | 153 |
| HPV18 | E2 | 11 | 153 |
| HPV18 | E2 | 8 | 207 |
| HPV18 | E2 | 11 | 207 |
| HPV18 | E2 | 9 | 350 |
| HPV18 | E2 | 10 | 350 |
| HPV18 | E2 | 11 | 350 |
| HPV18 | E2 | 8 | 136 |
| HPV18 | E2 | 9 | 136 |
| HPV18 | E2 | 10 | 212 |
| HPV18 | E2 | 8 | 157 |
| HPV18 | E2 | 9 | 157 |
| HPV18 | E2 | 9 | 232 |
| HPV18 | E2 | 11 | 322 |
| HPV18 | E2 | 10 | 96 |
| HPV18 | E2 | 11 | 96 |
| HPV18 | E2 | 10 | 228 |
| HPV18 | E5 | 8 | 47 |
| HPV18 | E5 | 9 | 47 |
| HPV18 | E5 | 11 | 47 |
| HPV18 | E5 | 8 | 29 |
| HPV18 | E5 | 9 | 29 |
| HPV18 | E5 | 10 | 29 |
| HPV18 | E5 | 11 | 29 |
| HPV18 | E5 | 8 | 50 |
| HPV18 | E5 | 9 | 50 |
| HPV18 | E5 | 10 | SO |
| HPV18 | E5 | 8 | 43 |
| HPV18 | E5 | 10 | 43 |
| HPV18 | E5 | 11 | 43 |
| HPV18 | E5 | 9 | 2 |
| HPV18 | E5 | 11 | 2 |
| HPV18 | E5 | 8 | 46 |
| HPV18 | E5 | 9 | 46 |
| HPV18 | E5 | 10 | 46 |
| HPV18 | E5 | 8 | 24 |
| HPV18 | E5 | 9 | 24 |
| HPV18 | E5 | 10 | 24 |
| HPV18 | E5 | 11 | 24 |
| HPV18 | E5 | 8 | 48 |
| HPV18 | E5 | 10 | 48 |
| HPV18 | E5 | 11 | 48 |
| HPV18 | E5 | 9 | 44 |
| HPV18 | E5 | 10 | 44 |
| HPV18 | E5 | 11 | 44 |
| HPV18 | E5 | 8 | 31 |
| HPV18 | E5 | 9 | 31 |
| HPV18 | E5 | 10 | 31 |
| HPV18 | E5 | 11 | 31 |
| HPV18 | E6 | 9 | 63 |
| HPV18 | E6 | 10 | 63 |
| HPV18 | E6 | 8 | 18 |
| HPV18 | E6 | 11 | 18 |
| HPV18 | E6 | 8 | 83 |
| HPV18 | E6 | 11 | 83 |
| HPV18 | E6 | 11 | 88 |
| HPV18 | E6 | 8 | 47 |
| HPV18 | E6 | 9 | 47 |
| HPV18 | E6 | 10 | 47 |
| HPV18 | E6 | 8 | 62 |
| HPV18 | E6 | 10 | 62 |
| HPV18 | E6 | 11 | 62 |

TABLE XIII-continued

HLA-B58 Supermotif Peptides

| 1 | 2 | 3 | 4 |
|---|---|---|---|
| HPV18 | E6 | 9 | 30 |
| HPV18 | E6 | 10 | 30 |
| HPV18 | E6 | 9 | 36 |
| HPV18 | E6 | 10 | 36 |
| HPV18 | E6 | 8 | 41 |
| HPV18 | E6 | 9 | 41 |
| HPV18 | E6 | 9 | 93 |
| HPV18 | E6 | 10 | 93 |
| HPV18 | E6 | 11 | 93 |
| HPV18 | E6 | 8 | 95 |
| HPV18 | E6 | 9 | 95 |
| HPV18 | E6 | 9 | 22 |
| HPV18 | E6 | 8 | 114 |
| HPV18 | E6 | 8 | 7 |
| HPV18 | E6 | 11 | 7 |
| HPV18 | E6 | 8 | 23 |
| HPV18 | E6 | 11 | 23 |
| HPV18 | E6 | 10 | 81 |
| HPV18 | E6 | 10 | 72 |
| HPV18 | E7 | 8 | 6 |
| HPV18 | E7 | 10 | 6 |
| HPV18 | E7 | 9 | 33 |
| HPV18 | E7 | 8 | 69 |
| HPV18 | E7 | 9 | 77 |
| HPV18 | E7 | 10 | 77 |
| HPV18 | E7 | 8 | 5 |
| HPV18 | E7 | 9 | 5 |
| HPV18 | E7 | 11 | 5 |
| HPV18 | E7 | 11 | 31 |
| HPV18 | E7 | 9 | 94 |
| HPV18 | E7 | 9 | 92 |
| HPV18 | E7 | 11 | 92 |
| HPV18 | E7 | 9 | 53 |
| HPV18 | E7 | 10 | 53 |
| HPV18 | E7 | 8 | 84 |
| HPV18 | E7 | 11 | 84 |
| HPV18 | E7 | 8 | 79 |
| HPV18 | E7 | 11 | 79 |
| HPV18 | E7 | 8 | 78 |
| HPV18 | E7 | 9 | 78 |
| HPV18 | L1 | 10 | 494 |
| HPV18 | L1 | 10 | 195 |
| HPV18 | L1 | 8 | 345 |
| HPV18 | L1 | 11 | 407 |
| HPV18 | L1 | 11 | 419 |
| HPV18 | L1 | 9 | 196 |
| HPV18 | L1 | 8 | 552 |
| HPV18 | L1 | 11 | 552 |
| HPV18 | L1 | 9 | 222 |
| HPV18 | L1 | 10 | 222 |
| HPV18 | L1 | 8 | 406 |
| HPV18 | L1 | 9 | 441 |
| HPV18 | L1 | 10 | 441 |
| HPV18 | L1 | 11 | 493 |
| HPV18 | L1 | 8 | 418 |
| HPV18 | L1 | 9 | 364 |
| HPV18 | L1 | 10 | 364 |
| HPV18 | L1 | 11 | 364 |
| HPV18 | L1 | 8 | 189 |
| HPV18 | L1 | 9 | 263 |
| HPV18 | L1 | 8 | 276 |
| HPV18 | L1 | 10 | 276 |
| HPV18 | L1 | 8 | 396 |
| HPV18 | L1 | 10 | 396 |
| HPV18 | L1 | 8 | 330 |
| HPV18 | L1 | 9 | 330 |
| HPV18 | L1 | 9 | 478 |
| HPV18 | L1 | 10 | 478 |
| HPV18 | L1 | 11 | 478 |
| HPV18 | L1 | 10 | 191 |
| HPV18 | L1 | 8 | 155 |
| HPV18 | L1 | 10 | 155 |
| HPV18 | L1 | 9 | 317 |
| HPV18 | L1 | 8 | 517 |
| HPV18 | L1 | 10 | 517 |
| HPV18 | L1 | 11 | 27 |
| HPV18 | L1 | 8 | 267 |
| HPV18 | L1 | 10 | 358 |
| HPV18 | L1 | 11 | 358 |
| HPV18 | L1 | 8 | 99 |
| HPV18 | L1 | 9 | 233 |
| HPV18 | L1 | 11 | 326 |
| HPV18 | L1 | 11 | 194 |
| HPV18 | L1 | 8 | 97 |
| HPV18 | L1 | 10 | 97 |
| HPV18 | L1 | 8 | 30 |
| HPV18 | L1 | 10 | 30 |
| HPV18 | L1 | 11 | 30 |
| HPV18 | L1 | 8 | 454 |
| HPV18 | L1 | 11 | 454 |
| HPV18 | L1 | 8 | 488 |
| HPV18 | L1 | 10 | 488 |
| HPV18 | L1 | 8 | 443 |
| HPV18 | L1 | 10 | 443 |
| HPV18 | L1 | 11 | 443 |
| HPV18 | L1 | 9 | 376 |
| HPV18 | L1 | 11 | 376 |
| HPV18 | L1 | 10 | 178 |
| HPV18 | L1 | 9 | 241 |
| HPV18 | L1 | 11 | 241 |
| HPV18 | L1 | 8 | 445 |
| HPV18 | L1 | 9 | 445 |
| HPV18 | L1 | 11 | 403 |
| HPV18 | L1 | 8 | 104 |
| HPV18 | L1 | 10 | 104 |
| HPV18 | L1 | 11 | 62 |
| HPV18 | L1 | 10 | 298 |
| HPV18 | L1 | 11 | 298 |
| HPV18 | L1 | 11 | 450 |
| HPV18 | L1 | 8 | 457 |
| HPV18 | L1 | 10 | 457 |
| HPV18 | L1 | 11 | 84 |
| HPV18 | L1 | 9 | 253 |
| HPV18 | L1 | 10 | 253 |
| HPV18 | L1 | 10 | 70 |
| HPV18 | L1 | 11 | 70 |
| HPV18 | L1 | 8 | 496 |
| HPV18 | L1 | 11 | 496 |
| HPV18 | L1 | 10 | 114 |
| HPV18 | L1 | 8 | 224 |
| HPV18 | L1 | 9 | 558 |
| HPV18 | L1 | 8 | 344 |
| HPV18 | L1 | 9 | 344 |
| HPV18 | L1 | 10 | 550 |
| HPV18 | L1 | 8 | 67 |
| HPV18 | L1 | 8 | 354 |
| HPV18 | L1 | 9 | 399 |
| HPV18 | L1 | 10 | 540 |
| HPV18 | L1 | 8 | 91 |
| HPV18 | L1 | 9 | 472 |
| HPV18 | L1 | 11 | 472 |
| HPV18 | L1 | 10 | 533 |
| HPV18 | L1 | 9 | 287 |
| HPV18 | L1 | 10 | 287 |
| HPV18 | L1 | 10 | 334 |
| HPV18 | L1 | 8 | 410 |
| HPV18 | L1 | 10 | 410 |
| HPV18 | L1 | 11 | 484 |
| HPV18 | L1 | 10 | 214 |
| HPV18 | L1 | 9 | 324 |
| HPV18 | L1 | 9 | 299 |
| HPV18 | L1 | 10 | 299 |
| HPV18 | L1 | 11 | 299 |
| HPV18 | L1 | 9 | 551 |
| HPV18 | L1 | 8 | 127 |
| HPV18 | L1 | 10 | 127 |
| HPV18 | L1 | 9 | 192 |
| HPV18 | L1 | 9 | 458 |
| HPV18 | L1 | 11 | 458 |
| HPV18 | L1 | 8 | 555 |

TABLE XIII-continued

HLA-B58 Supermotif Peptides

| 1 | 2 | 3 | 4 |
|---|---|---|---|
| HPV18 | L1 | 10 | 555 |
| HPV18 | L1 | 11 | 100 |
| HPV18 | L1 | 10 | 272 |
| HPV18 | L1 | 8 | 400 |
| HPV18 | L1 | 10 | 408 |
| HPV18 | L1 | 8 | 234 |
| HPV18 | L1 | 8 | 446 |
| HPV18 | L1 | 11 | 446 |
| HPV18 | L1 | 11 | 362 |
| HPV18 | L1 | 11 | 149 |
| HPV18 | L1 | 9 | 474 |
| HPV18 | L1 | 10 | 474 |
| HPV18 | L1 | 8 | 197 |
| HPV18 | L1 | 9 | 554 |
| HPV18 | L1 | 11 | 554 |
| HPV18 | L1 | 9 | 397 |
| HPV18 | L1 | 11 | 397 |
| HPV18 | L1 | 8 | 473 |
| HPV18 | L1 | 10 | 473 |
| HPV18 | L1 | 11 | 473 |
| HPV18 | L1 | 10 | 553 |
| HPV18 | L1 | 9 | 486 |
| HPV18 | L1 | 10 | 486 |
| HPV18 | L1 | 10 | 79 |
| HPV18 | L1 | 11 | 79 |
| HPV18 | L1 | 8 | 126 |
| HPV18 | L1 | 9 | 126 |
| HPV18 | L1 | 11 | 126 |
| HPV18 | L1 | 9 | 200 |
| HPV18 | L1 | 11 | 200 |
| HPV18 | L1 | 10 | 208 |
| HPV18 | L1 | 8 | 89 |
| HPV18 | L1 | 10 | 89 |
| HPV18 | L1 | 8 | 361 |
| HPV18 | L1 | 8 | 161 |
| HPV18 | L1 | 9 | 352 |
| HPV18 | L1 | 10 | 352 |
| HPV18 | L1 | 8 | 425 |
| HPV18 | L1 | 10 | 425 |
| HPV18 | L1 | 9 | 4 |
| HPV18 | L1 | 11 | 4 |
| HPV18 | L2 | 9 | 6 |
| HPV18 | L2 | 10 | 201 |
| HPV18 | L2 | 9 | 381 |
| HPV18 | L2 | 11 | 381 |
| HPV18 | L2 | 8 | 423 |
| HPV18 | L2 | 8 | 341 |
| HPV18 | L2 | 10 | 341 |
| HPV18 | L2 | 11 | 341 |
| HPV18 | L2 | 11 | 303 |
| HPV18 | L2 | 8 | 273 |
| HPV18 | L2 | 10 | 273 |
| HPV18 | L2 | 9 | 109 |
| HPV18 | L2 | 8 | 455 |
| HPV18 | L2 | 10 | 369 |
| HPV18 | L2 | 11 | 200 |
| HPV18 | L2 | 9 | 162 |
| HPV18 | L2 | 8 | 296 |
| HPV18 | L2 | 10 | 296 |
| HPV18 | L2 | 11 | 296 |
| HPV18 | L2 | 9 | 122 |
| HPV18 | L2 | 11 | 157 |
| HPV18 | L2 | 8 | 306 |
| HPV18 | L2 | 10 | 306 |
| HPV18 | L2 | 10 | 314 |
| HPV18 | L2 | 10 | 62 |
| HPV18 | L2 | 11 | 62 |
| HPV18 | L2 | 8 | 25 |
| HPV18 | L2 | 11 | 25 |
| HPV18 | L2 | 8 | 64 |
| HPV18 | L2 | 9 | 64 |
| HPV18 | L2 | 11 | 64 |
| HPV18 | L2 | 8 | 188 |
| HPV18 | L2 | 10 | 188 |
| HPV18 | L2 | 9 | 432 |
| HPV18 | L2 | 10 | 432 |
| HPV18 | L2 | 11 | 432 |
| HPV18 | L2 | 10 | 183 |
| HPV18 | L2 | 8 | 310 |
| HPV18 | L2 | 10 | 310 |
| HPV18 | L2 | 11 | 310 |
| HPV18 | L2 | 10 | 124 |
| HPV18 | L2 | 8 | 37 |
| HPV18 | L2 | 9 | 37 |
| HPV18 | L2 | 11 | 37 |
| HPV18 | L2 | 8 | 134 |
| HPV18 | L2 | 10 | 134 |
| HPV18 | L2 | 8 | 292 |
| HPV18 | L2 | 8 | 326 |
| HPV18 | L2 | 10 | 326 |
| HPV18 | L2 | 10 | 323 |
| HPV18 | L2 | 11 | 323 |
| HPV18 | L2 | 10 | 378 |
| HPV18 | L2 | 9 | 210 |
| HPV18 | L2 | 10 | 152 |
| HPV18 | L2 | 11 | 152 |
| HPV18 | L2 | 9 | 405 |
| HPV18 | L2 | 10 | 405 |
| HPV18 | L2 | 8 | 143 |
| HPV18 | L2 | 10 | 143 |
| HPV18 | L2 | 10 | 130 |
| HPV18 | L2 | 11 | 130 |
| HPV18 | L2 | 8 | 249 |
| HPV18 | L2 | 11 | 249 |
| HPV18 | L2 | 8 | 40 |
| HPV18 | L2 | 11 | 40 |
| HPV18 | L2 | 9 | 263 |
| HPV18 | L2 | 8 | 242 |
| HPV18 | L2 | 10 | 242 |
| HPV18 | L2 | 8 | 287 |
| HPV18 | L2 | 10 | 287 |
| HPV18 | L2 | 9 | 391 |
| HPV18 | L2 | 10 | 391 |
| HPV18 | L2 | 10 | 254 |
| HPV18 | L2 | 8 | 160 |
| HPV18 | L2 | 9 | 160 |
| HPV18 | L2 | 11 | 160 |
| HPV18 | L2 | 10 | 285 |
| HPV18 | L2 | 9 | 422 |
| HPV18 | L2 | 8 | 328 |
| HPV18 | L2 | 11 | 328 |
| HPV18 | L2 | 8 | 362 |
| HPV18 | L2 | 9 | 362 |
| HPV18 | L2 | 10 | 362 |
| HPV18 | L2 | 11 | 362 |
| HPV18 | L2 | 11 | 245 |
| HPV18 | L2 | 8 | 145 |
| HPV18 | L2 | 9 | 408 |
| HPV18 | L2 | 10 | 408 |
| HPV18 | L2 | 9 | 419 |
| HPV18 | L2 | 10 | 419 |
| HPV18 | L2 | 9 | 98 |
| HPV18 | L2 | 10 | 98 |
| HPV18 | L2 | 9 | 120 |
| HPV18 | L2 | 11 | 120 |
| HPV18 | L2 | 9 | 376 |
| HPV18 | L2 | 8 | 86 |
| HPV18 | L2 | 11 | 86 |
| HPV18 | L2 | 8 | 185 |
| HPV18 | L2 | 11 | 185 |
| HPV18 | L2 | 11 | 216 |
| HPV18 | L2 | 9 | 23 |
| HPV18 | L2 | 10 | 23 |
| HPV18 | L2 | 9 | 172 |
| HPV18 | L2 | 10 | 172 |
| HPV18 | L2 | 11 | 172 |
| HPV18 | L2 | 8 | 5 |
| HPV18 | L2 | 10 | 5 |
| HPV18 | L2 | 8 | 11 |
| HPV18 | L2 | 8 | 229 |

TABLE XIII-continued

HLA-B58 Supermotif Peptides

| 1 | 2 | 3 | 4 |
|---|---|---|---|
| HPV18 | L2 | 9 | 229 |
| HPV18 | L2 | 9 | 268 |
| HPV18 | L2 | 10 | 268 |
| HPV18 | L2 | 8 | 308 |
| HPV18 | L2 | 10 | 308 |
| HPV18 | L2 | 8 | 77 |
| HPV18 | L2 | 8 | 364 |
| HPV18 | L2 | 9 | 364 |
| HPV18 | L2 | 11 | 364 |
| HPV18 | L2 | 8 | 132 |
| HPV18 | L2 | 9 | 132 |
| HPV18 | L2 | 10 | 132 |
| HPV18 | L2 | 8 | 380 |
| HPV18 | L2 | 10 | 380 |
| HPV18 | L2 | 8 | 340 |
| HPV18 | L2 | 9 | 340 |
| HPV18 | L2 | 11 | 340 |
| HPV18 | L2 | 9 | 379 |
| HPV18 | L2 | 11 | 379 |
| HPV18 | L2 | 9 | 202 |
| HPV18 | L2 | 10 | 48 |
| HPV18 | L2 | 10 | 246 |
| HPV18 | L2 | 11 | 246 |
| HPV18 | L2 | 8 | 211 |
| HPV18 | L2 | 11 | 211 |
| HPV18 | L2 | 8 | 110 |
| HPV18 | L2 | 8 | 393 |
| HPV18 | L2 | 8 | 382 |
| HPV18 | L2 | 10 | 382 |
| HPV18 | L2 | 10 | 212 |
| HPV18 | L2 | 11 | 212 |
| HPV18 | L2 | 11 | 147 |
| HPV18 | L2 | 9 | 153 |
| HPV18 | L2 | 10 | 153 |
| HPV18 | L2 | 8 | 365 |
| HPV18 | L2 | 10 | 365 |
| HPV18 | L2 | 8 | 409 |
| HPV18 | L2 | 9 | 409 |
| HPV18 | L2 | 8 | 420 |
| HPV18 | L2 | 9 | 420 |
| HPV18 | L2 | 11 | 420 |
| HPV18 | L2 | 9 | 131 |
| HPV18 | L2 | 10 | 131 |
| HPV18 | L2 | 11 | 131 |
| HPV18 | L2 | 8 | 367 |
| HPV18 | L2 | 9 | 114 |
| HPV18 | L2 | 9 | 125 |
| HPV18 | L2 | 10 | 186 |
| HPV18 | L2 | 9 | 288 |
| HPV18 | L2 | 8 | 392 |
| HPV18 | L2 | 9 | 392 |
| HPV18 | L2 | 10 | 148 |
| HPV18 | L2 | 11 | 411 |
| HPV18 | L2 | 8 | 38 |
| HPV18 | L2 | 10 | 38 |
| HPV18 | L2 | 11 | 261 |
| HPV18 | L2 | 8 | 154 |
| HPV18 | L2 | 9 | 154 |
| HPV18 | L2 | 8 | 136 |
| HPV18 | L2 | 9 | 366 |
| HPV18 | L2 | 8 | 410 |
| HPV18 | L2 | 9 | 135 |
| HPV18 | L2 | 10 | 221 |
| HPV18 | L2 | 11 | 221 |
| HPV18 | L2 | 9 | 339 |
| HPV18 | L2 | 10 | 339 |
| HPV18 | L2 | 11 | 2 |
| HPV18 | L2 | 8 | 150 |
| HPV18 | L2 | 11 | 417 |
| HPV18 | L2 | 8 | 234 |
| HPV18 | L2 | 9 | 234 |
| HPV18 | L2 | 9 | 104 |
| HPV18 | L2 | 10 | 104 |
| HPV18 | L2 | 10 | 113 |
| HPV18 | L2 | 9 | 387 |
| HPV18 | L2 | 11 | 387 |
| HPV18 | L2 | 8 | 47 |
| HPV18 | L2 | 11 | 47 |
| HPV18 | L2 | 8 | 351 |
| HPV18 | L2 | 9 | 351 |
| HPV18 | L2 | 11 | 351 |
| HPV18 | L2 | 8 | 384 |
| HPV18 | L2 | 8 | 374 |
| HPV18 | L2 | 11 | 374 |
| HPV18 | L2 | 8 | 227 |
| HPV18 | L2 | 10 | 227 |
| HPV18 | L2 | 11 | 227 |
| HPV18 | L2 | 8 | 400 |
| HPV31 | E1 | 11 | 296 |
| HPV31 | E1 | 9 | 219 |
| HPV31 | E1 | 10 | 219 |
| HPV31 | E1 | 10 | 297 |
| HPV31 | E1 | 10 | 185 |
| HPV31 | E1 | 11 | 185 |
| HPV31 | E1 | 8 | 504 |
| HPV31 | E1 | 9 | 504 |
| HPV31 | E1 | 10 | 370 |
| HPV31 | E1 | 8 | 263 |
| HPV31 | E1 | 11 | 263 |
| HPV31 | E1 | 8 | 249 |
| HPV31 | E1 | 9 | 249 |
| HPV31 | E1 | 10 | 249 |
| HPV31 | E1 | 11 | 249 |
| HPV31 | E1 | 8 | 213 |
| HPV31 | E1 | 9 | 213 |
| HPV31 | E1 | 11 | 213 |
| HPV31 | E1 | 10 | 495 |
| HPV31 | E1 | 9 | 503 |
| HPV31 | E1 | 10 | 503 |
| HPV31 | E1 | 8 | 364 |
| HPV31 | E1 | 9 | 364 |
| HPV31 | E1 | 10 | 364 |
| HPV31 | E1 | 8 | 352 |
| HPV31 | E1 | 9 | 352 |
| HPV31 | E1 | 11 | 352 |
| HPV31 | E1 | 9 | 613 |
| HPV31 | E1 | 9 | 130 |
| HPV31 | E1 | 8 | 366 |
| HPV31 | E1 | 9 | 39 |
| HPV31 | E1 | 10 | 39 |
| HPV31 | E1 | 9 | 42 |
| HPV31 | E1 | 10 | 42 |
| HPV31 | E1 | 9 | 332 |
| HPV31 | E1 | 10 | 332 |
| HPV31 | E1 | 8 | 74 |
| HPV31 | E1 | 9 | 74 |
| HPV31 | E1 | 11 | 74 |
| HPV31 | E1 | 8 | 62 |
| HPV31 | E1 | 9 | 62 |
| HPV31 | E1 | 11 | 62 |
| HPV31 | E1 | 10 | 80 |
| HPV31 | E1 | 11 | 80 |
| HPV31 | E1 | 9 | 64 |
| HPV31 | E1 | 11 | 3i5 |
| HPV31 | E1 | 8 | 168 |
| HPV31 | E1 | 10 | 168 |
| HPV31 | E1 | 11 | 168 |
| HPV31 | E1 | 8 | 139 |
| HPV31 | E1 | 8 | 593 |
| HPV31 | E1 | 10 | 593 |
| HPV31 | E1 | 9 | 566 |
| HPV31 | E1 | 9 | 457 |
| HPV31 | E1 | 10 | 457 |
| HPV31 | E1 | 11 | 91 |
| HPV31 | E1 | 8 | 11 |
| HPV31 | E1 | 9 | 11 |
| HPV31 | E1 | 10 | 11 |
| HPV31 | E1 | 10 | 386 |
| HPV31 | E1 | 10 | 225 |
| HPV31 | E1 | 11 | 225 |

TABLE XIII-continued

HLA-B58 Supermotif Peptides

| 1 | 2 | 3 | 4 |
|---|---|---|---|
| HPV31 | E1 | 8 | 78 |
| HPV31 | E1 | 9 | 71 |
| HPV31 | E1 | 11 | 71 |
| HPV31 | E1 | 8 | 328 |
| HPV31 | E1 | 10 | 328 |
| HPV31 | E1 | 9 | 560 |
| HPV31 | E1 | 8 | 355 |
| HPV31 | E1 | 9 | 355 |
| HPV31 | E1 | 11 | 309 |
| HPV31 | E1 | 8 | 471 |
| HPV31 | E1 | 9 | 471 |
| HPV31 | E1 | 11 | 471 |
| HPV31 | E1 | 8 | 105 |
| HPV31 | E1 | 10 | 105 |
| HPV31 | E1 | 9 | 97 |
| HPV31 | E1 | 8 | 280 |
| HPV31 | E1 | 10 | 479 |
| HPV31 | E1 | 11 | 479 |
| HPV31 | E1 | 10 | 268 |
| HPV31 | E1 | 11 | 268 |
| HPV31 | E1 | 8 | 184 |
| HPV31 | E1 | 11 | 184 |
| HPV31 | E1 | 11 | 532 |
| HPV31 | E1 | 8 | 590 |
| HPV31 | E1 | 11 | 590 |
| HPV31 | E1 | 9 | 485 |
| HPV31 | E1 | 10 | 485 |
| HPV31 | E1 | 8 | 374 |
| HPV31 | E1 | 9 | 374 |
| HPV31 | E1 | 9 | 210 |
| HPV31 | E1 | 10 | 210 |
| HPV31 | E1 | 11 | 210 |
| HPV31 | E1 | 8 | 463 |
| HPV31 | E1 | 9 | 463 |
| HPV31 | E1 | 11 | 463 |
| HPV31 | E1 | 8 | 119 |
| HPV31 | E1 | 10 | 119 |
| HPV31 | E1 | 9 | 232 |
| HPV31 | E1 | 10 | 232 |
| HPV31 | E1 | 8 | 179 |
| HPV31 | E1 | 9 | 179 |
| HPV31 | E1 | 10 | 179 |
| HPV31 | E1 | 8 | 247 |
| HPV31 | E1 | 9 | 247 |
| HPV31 | E1 | 10 | 247 |
| HPV31 | E1 | 11 | 247 |
| HPV31 | E1 | 8 | 493 |
| HPV31 | E1 | 9 | 493 |
| HPV31 | E1 | 8 | 362 |
| HPV31 | E1 | 10 | 362 |
| HPV31 | E1 | 11 | 362 |
| HPV31 | E1 | 8 | 437 |
| HPV31 | E1 | 11 | 437 |
| HPV31 | E1 | 8 | 94 |
| HPV31 | E1 | 10 | 94 |
| HPV31 | E1 | 9 | 584 |
| HPV31 | E1 | 10 | 584 |
| HPV31 | E1 | 8 | 337 |
| HPV31 | E1 | 9 | 337 |
| HPV31 | E1 | 11 | 468 |
| HPV31 | E1 | 8 | 306 |
| HPV31 | E1 | 8 | 549 |
| HPV31 | E1 | 10 | 549 |
| HPV31 | E1 | 11 | 549 |
| HPV31 | E1 | 8 | 518 |
| HPV31 | E1 | 10 | 518 |
| HPV31 | E1 | 8 | 483 |
| HPV31 | E1 | 11 | 483 |
| HPV31 | E1 | 9 | 117 |
| HPV31 | E1 | 10 | 117 |
| HPV31 | E1 | 9 | 135 |
| HPV31 | E1 | 10 | 135 |
| HPV31 | E1 | 9 | 460 |
| HPV31 | E1 | 11 | 460 |
| HPV31 | E1 | 8 | 170 |
| HPV31 | E1 | 9 | 170 |
| HPV31 | E1 | 9 | 60 |
| HPV31 | E1 | 10 | 60 |
| HPV31 | E1 | 11 | 60 |
| HPV31 | E1 | 11 | 378 |
| HPV31 | E1 | 9 | 67 |
| HPV31 | E1 | 9 | 245 |
| HPV31 | E1 | 10 | 245 |
| HPV31 | E1 | 11 | 245 |
| HPV31 | E1 | 10 | 207 |
| HPV31 | E1 | 8 | 323 |
| HPV31 | E1 | 9 | 394 |
| HPV31 | E1 | 8 | 293 |
| HPV31 | E1 | 9 | 293 |
| HPV31 | E1 | 10 | 293 |
| HPV31 | E1 | 10 | 303 |
| HPV31 | E1 | 11 | 303 |
| HPV31 | E1 | 8 | 595 |
| HPV31 | E1 | 10 | 438 |
| HPV31 | E1 | 8 | 98 |
| HPV31 | E1 | 8 | 40 |
| HPV31 | E1 | 9 | 40 |
| HPV31 | E1 | 11 | 40 |
| HPV31 | E1 | 8 | 294 |
| HPV31 | E1 | 9 | 294 |
| HPV31 | E1 | 8 | 211 |
| HPV31 | E1 | 9 | 211 |
| HPV31 | E1 | 10 | 211 |
| HPV31 | E1 | 11 | 211 |
| HPV31 | E1 | 11 | 616 |
| HPV31 | E1 | 8 | 295 |
| HPV31 | E1 | 9 | 120 |
| HPV31 | E1 | 8 | 65 |
| HPV31 | E1 | 11 | 65 |
| HPV31 | E1 | 8 | 180 |
| HPV31 | E1 | 9 | 180 |
| HPV31 | E1 | 8 | 333 |
| HPV31 | E1 | 9 | 333 |
| HPV31 | E1 | 11 | 333 |
| HPV31 | E1 | 8 | 505 |
| HPV31 | E1 | 11 | 505 |
| HPV31 | E1 | 10 | 218 |
| HPV31 | E1 | 11 | 218 |
| HPV31 | E1 | 8 | 227 |
| HPV31 | E1 | 9 | 227 |
| HPV31 | E1 | 10 | 413 |
| HPV31 | E1 | 11 | 413 |
| HPV31 | E1 | 9 | 434 |
| HPV31 | E1 | 10 | 434 |
| HPV31 | E1 | 11 | 434 |
| HPV31 | E1 | 10 | 197 |
| HPV31 | E1 | 9 | 621 |
| HPV31 | E1 | 9 | 525 |
| HPV31 | E1 | 10 | 525 |
| HPV31 | E1 | 11 | 525 |
| HPV31 | E1 | 9 | 223 |
| HPV31 | E1 | 8 | 343 |
| HPV31 | E1 | 8 | 481 |
| HPV31 | E1 | 9 | 481 |
| HPV31 | E1 | 10 | 481 |
| HPV31 | E1 | 11 | 359 |
| HPV31 | E2 | 10 | 277 |
| HPV31 | E2 | 11 | 277 |
| HPV31 | E2 | 9 | 278 |
| HPV31 | E2 | 10 | 278 |
| HPV31 | E2 | 8 | 291 |
| HPV31 | E2 | 9 | 228 |
| HPV31 | E2 | 9 | 330 |
| HPV31 | E2 | 10 | 330 |
| HPV31 | E2 | 11 | 330 |
| HPV31 | E2 | 8 | 280 |
| HPV31 | E2 | 8 | 145 |
| HPV31 | E2 | 8 | 301 |
| HPV31 | E2 | 10 | 301 |
| HPV31 | E2 | 9 | 22 |

TABLE XIII-continued

HLA-B58 Supermotif Peptides

| 1 | 2 | 3 | 4 |
|---|---|---|---|
| HPV31 | E2 | 11 | 22 |
| HPV31 | E2 | 10 | 265 |
| HPV31 | E2 | 11 | 265 |
| HPV31 | E2 | 8 | 268 |
| HPV31 | E2 | 10 | 268 |
| HPV31 | E2 | 11 | 268 |
| HPV31 | E2 | 11 | 174 |
| HPV31 | E2 | 9 | 197 |
| HPV31 | E2 | 11 | 197 |
| HPV31 | E2 | 8 | 80 |
| HPV31 | E2 | 9 | 2 |
| HPV31 | E2 | 8 | 207 |
| HPV31 | E2 | 11 | 207 |
| HPV31 | E2 | 8 | 200 |
| HPV31 | E2 | 9 | 200 |
| HPV31 | E2 | 11 | 200 |
| HPV31 | E2 | 8 | 171 |
| HPV31 | E2 | 8 | 179 |
| HPV31 | E2 | 10 | 179 |
| HPV31 | E2 | 9 | 231 |
| HPV31 | E2 | 8 | 187 |
| HPV31 | E2 | 9 | 187 |
| HPV31 | E2 | 8 | 52 |
| HPV31 | E2 | 10 | 52 |
| HPV31 | E2 | 11 | 52 |
| HPV31 | E2 | 10 | 205 |
| HPV31 | E2 | 9 | 345 |
| HPV31 | E2 | 10 | 345 |
| HPV31 | E2 | 11 | 165 |
| HPV31 | E2 | 8 | 66 |
| HPV31 | E2 | 10 | 66 |
| HPV31 | E2 | 8 | 68 |
| HPV31 | E2 | 10 | 68 |
| HPV31 | E2 | 11 | 68 |
| HPV31 | E2 | 10 | 45 |
| HPV31 | E2 | 11 | 226 |
| HPV31 | E2 | 8 | 312 |
| HPV31 | E2 | 11 | 312 |
| HPV31 | E2 | 8 | 62 |
| HPV31 | E2 | 9 | 62 |
| HPV31 | E2 | 11 | 62 |
| HPV31 | E2 | 8 | 103 |
| HPV31 | E2 | 8 | 337 |
| HPV31 | E2 | 9 | 337 |
| HPV31 | E2 | 9 | 84 |
| HPV31 | E2 | 11 | 84 |
| HPV31 | E2 | 8 | 254 |
| HPV31 | E2 | 9 | 2S4 |
| HPV31 | E2 | 8 | 127 |
| HPV31 | E2 | 10 | 127 |
| HPV31 | E2 | 11 | 127 |
| HPV31 | E2 | 11 | 219 |
| HPV31 | E2 | 9 | 355 |
| HPV31 | E2 | 11 | 355 |
| HPV31 | E2 | 9 | 361 |
| HPV31 | E2 | 10 | 361 |
| HPV31 | E2 | 8 | 60 |
| HPV31 | E2 | 10 | 60 |
| HPV31 | E2 | 11 | 60 |
| HPV31 | E2 | 9 | 290 |
| HPV31 | E2 | 10 | 106 |
| HPV31 | E2 | 8 | 71 |
| HPV31 | E2 | 9 | 71 |
| HPV31 | E2 | 9 | 283 |
| HPV31 | E2 | 8 | 96 |
| HPV31 | E2 | 10 | 96 |
| HPV31 | E2 | 11 | 283 |
| HPV31 | E2 | 11 | 276 |
| HPV31 | E2 | 8 | 201 |
| HPV31 | E2 | 10 | 201 |
| HPV31 | E2 | 11 | 201 |
| HPV31 | E2 | 8 | 346 |
| HPV31 | E2 | 9 | 346 |
| HPV31 | E2 | 8 | 232 |
| HPV31 | E2 | 9 | 97 |
| HPV31 | E2 | 8 | 222 |
| HPV31 | E2 | 9 | 222 |
| HPV31 | E2 | 8 | 347 |
| HPV31 | E2 | 11 | 347 |
| HPV31 | E2 | 11 | 292 |
| HPV31 | E2 | 9 | 221 |
| HPV31 | E2 | 10 | 221 |
| HPV31 | E2 | 10 | 220 |
| HPV31 | E2 | 11 | 220 |
| HPV31 | E2 | 9 | 287 |
| HPV31 | E2 | 10 | 287 |
| HPV31 | E2 | 9 | 64 |
| HPV31 | E2 | 10 | 64 |
| HPV31 | E2 | 8 | 365 |
| HPV31 | E2 | 8 | 363 |
| HPV31 | E2 | 10 | 363 |
| HPV31 | E2 | 11 | 328 |
| HPV31 | E2 | 8 | 92 |
| HPV31 | E2 | 10 | 92 |
| HPV31 | E2 | 11 | 92 |
| HPV31 | E2 | 8 | 131 |
| HPV31 | E2 | 9 | 131 |
| HPV31 | E2 | 11 | 131 |
| HPV31 | E2 | 11 | 115 |
| HPV31 | E5 | 8 | 40 |
| HPV31 | ES | 9 | 40 |
| HPV31 | E5 | 10 | 40 |
| HPV31 | E5 | 11 | 40 |
| HPV31 | E5 | 8 | 53 |
| HPV31 | E5 | 10 | 53 |
| HPV31 | E5 | 11 | 53 |
| HPV31 | E5 | 9 | 52 |
| HPV31 | E5 | 11 | 52 |
| HPV31 | E5 | 8 | 6 |
| HPV31 | E5 | 10 | 6 |
| HPV31 | E5 | 11 | 6 |
| HPV31 | E5 | 9 | 34 |
| HPV31 | E5 | 10 | 34 |
| HPV31 | E5 | 11 | 34 |
| HPV31 | E5 | 9 | 7 |
| HPV31 | E5 | 10 | 7 |
| HPV31 | E5 | 11 | 7 |
| HPV31 | E5 | 9 | 54 |
| HPV31 | E5 | 10 | 54 |
| HPV31 | E5 | 11 | 54 |
| HPV31 | E5 | 8 | 9 |
| HPV31 | E5 | 9 | 9 |
| HPV31 | E5 | 11 | 9 |
| HPV31 | E5 | 8 | 36 |
| HPV31 | E5 | 9 | 36 |
| HPV31 | E5 | 10 | 36 |
| HPV31 | E5 | 11 | 36 |
| HPV31 | E5 | 8 | 39 |
| HPV31 | E5 | 9 | 39 |
| HPV31 | E5 | 10 | 39 |
| HPV31 | E5 | 11 | 39 |
| HPV31 | E6 | 8 | 63 |
| HPV31 | E6 | 41 | 63 |
| HPV31 | E6 | 11 | 57 |
| HPV31 | E6 | 8 | 39 |
| HPV31 | E6 | 9 | 39 |
| HPV31 | E6 | 8 | 45 |
| HPV31 | E6 | 9 | 45 |
| HPV31 | E6 | 10 | 45 |
| HPV31 | E6 | 8 | 47 |
| HPV31 | E6 | 9 | 15 |
| HPV31 | E6 | 9 | 37 |
| HPV31 | E6 | 10 | 37 |
| HPV31 | E6 | 11 | 37 |
| HPV31 | E6 | 9 | 91 |
| HPV31 | E6 | 10 | S1 |
| HPV31 | E6 | 11 | 91 |
| HPV31 | E6 | 8 | 5 |
| HPV31 | E6 | 11 | 5 |
| HPV31 | E6 | 10 | 17 |

TABLE XIII-continued

HLA-B58 Supermotif Peptides

| 1 | 2 | 3 | 4 |
|---|---|---|---|
| HPV31 | E6 | 8 | 16 |
| HPV31 | E6 | 11 | 16 |
| HPV31 | E6 | 11 | 86 |
| HPV31 | E6 | 9 | 73 |
| HPV31 | E6 | 11 | 73 |
| HPV31 | E6 | 9 | 132 |
| HPV31 | E6 | 9 | 70 |
| HPV31 | E6 | 10 | 70 |
| HPV31 | E6 | 8 | 81 |
| HPV31 | E6 | 11 | 81 |
| HPV31 | E7 | 10 | 19 |
| HPV31 | E7 | 8 | 30 |
| HPV31 | E7 | 9 | 30 |
| HPV31 | E7 | 8 | 48 |
| HPV31 | E7 | 10 | 48 |
| HPV31 | E7 | 8 | 18 |
| HPV31 | E7 | 11 | 18 |
| HPV31 | E7 | 8 | 4 |
| HPV31 | E7 | 9 | 4 |
| HPV31 | E7 | 10 | 4 |
| HPV31 | E7 | 8 | 62 |
| HPV31 | E7 | 8 | 5 |
| HPV31 | E7 | 10 | 5 |
| HPV31 | E7 | 9 | 44 |
| HPV31 | E7 | 11 | 44 |
| HPV31 | E7 | 9 | 70 |
| HPV31 | E7 | 10 | 70 |
| HPV31 | E7 | 8 | 31 |
| HPV31 | E7 | 8 | 71 |
| HPV31 | E7 | 9 | 71 |
| HPV31 | E7 | 9 | 49 |
| HPV31 | E7 | 11 | 55 |
| HPV31 | L1 | 10 | 347 |
| HPV31 | L1 | 8 | 285 |
| HPV31 | L1 | 9 | 285 |
| HPV31 | L1 | 8 | 9 |
| HPV31 | L1 | 10 | 9 |
| HPV31 | L1 | 11 | 346 |
| HPV31 | L1 | 9 | 304 |
| HPV31 | L1 | 10 | 304 |
| HPV31 | L1 | 11 | 304 |
| HPV31 | L1 | 8 | 129 |
| HPV31 | L1 | 9 | 129 |
| HPV31 | L1 | 9 | 203 |
| HPV31 | L1 | 11 | 203 |
| HPV31 | L1 | 8 | 216 |
| HPV31 | L1 | 10 | 216 |
| HPV31 | L1 | 9 | 353 |
| HPV31 | L1 | 8 | 336 |
| HPV31 | L1 | 10 | 336 |
| HPV31 | L1 | 10 | 417 |
| HPV31 | L1 | 11 | 417 |
| HPV31 | L1 | 9 | 8 |
| HPV31 | L1 | 11 | 8 |
| HPV31 | L1 | 8 | 270 |
| HPV31 | L1 | 9 | 270 |
| HPV31 | L1 | 8 | 95 |
| HPV31 | L1 | 10 | 95 |
| HPV31 | L1 | 8 | 456 |
| HPV31 | L1 | 10 | 456 |
| HPV31 | L1 | 11 | 211 |
| HPV31 | L1 | 8 | 207 |
| HPV31 | L1 | 8 | 38 |
| HPV31 | L1 | 8 | 280 |
| HPV31 | L1 | 9 | 280 |
| HPV31 | L1 | 9 | 413 |
| HPV31 | L1 | 10 | 413 |
| HPV31 | L1 | 8 | 298 |
| HPV31 | L1 | 10 | 298 |
| HPV31 | L1 | 11 | 298 |
| HPV31 | L1 | 8 | 173 |
| HPV31 | L1 | 9 | 173 |
| HPV31 | L1 | 11 | 282 |
| HPV31 | L1 | 8 | 141 |
| HPV31 | L1 | 10 | 141 |
| HPV31 | L1 | 11 | 266 |
| HPV31 | L1 | 8 | 36 |
| HPV31 | L1 | 10 | 36 |
| HPV31 | L1 | 8 | 393 |
| HPV31 | L1 | 11 | 393 |
| HPV31 | L1 | 8 | 349 |
| HPV31 | L1 | 10 | 118 |
| HPV31 | L1 | 10 | 148 |
| HPV31 | L1 | 8 | 382 |
| HPV31 | L1 | 10 | 382 |
| HPV31 | L1 | 11 | 382 |
| HPV31 | L1 | 9 | 181 |
| HPV31 | L1 | 11 | 181 |
| HPV31 | L1 | 10 | 482 |
| HPV31 | L1 | 8 | 54 |
| HPV31 | L1 | 9 | 54 |
| HPV31 | L1 | 10 | 54 |
| HPV31 | L1 | 8 | 218 |
| HPV31 | L1 | 8 | 357 |
| HPV31 | L1 | 9 | 357 |
| HPV31 | L1 | 8 | 384 |
| HPV31 | L1 | 9 | 384 |
| HPV31 | L1 | 9 | 407 |
| HPV31 | L1 | 8 | 43 |
| HPV31 | L1 | 10 | 43 |
| HPV31 | L1 | 9 | 1 |
| HPV31 | L1 | 11 | 1 |
| HPV31 | L1 | 8 | 343 |
| HPV31 | L1 | 10 | 389 |
| HPV31 | L1 | 11 | 389 |
| HPV31 | L1 | 11 | 179 |
| HPV31 | L1 | 11 | 351 |
| HPV31 | L1 | 9 | 227 |
| HPV31 | L1 | 10 | 227 |
| HPV31 | L1 | 9 | 193 |
| HPV31 | L1 | 10 | 193 |
| HPV31 | L1 | 9 | 397 |
| HPV31 | L1 | 11 | 397 |
| HPV31 | L1 | 9 | 489 |
| HPV31 | L1 | 8 | 6 |
| HPV31 | L1 | 11 | 6 |
| HPV31 | L1 | 9 | 411 |
| HPV31 | L1 | 11 | 411 |
| HPV31 | L1 | 10 | 296 |
| HPV31 | L1 | 8 | 294 |
| HPV31 | L1 | 10 | 472 |
| HPV31 | L1 | 9 | 425 |
| HPV31 | L1 | 9 | 316 |
| HPV31 | L1 | 11 | 316 |
| HPV31 | L1 | 8 | 476 |
| HPV31 | L1 | 9 | 264 |
| HPV31 | L1 | 9 | 339 |
| HPV31 | L1 | 10 | 339 |
| HPV31 | L1 | 11 | 339 |
| HPV31 | L1 | 8 | 30 |
| HPV31 | L1 | 11 | 30 |
| HPV31 | L1 | 8 | 385 |
| HPV31 | L1 | 11 | 385 |
| HPV31 | L1 | 9 | 457 |
| HPV31 | L1 | 11 | 487 |
| HPV31 | L1 | 11 | 39 |
| HPV31 | L1 | 8 | 490 |
| HPV31 | L1 | 8 | 358 |
| HPV31 | L1 | 10 | 283 |
| HPV31 | L1 | 11 | 283 |
| HPV31 | L1 | 11 | 23 |
| HPV31 | L1 | 8 | 340 |
| HPV31 | L1 | 9 | 340 |
| HPV31 | L1 | 10 | 340 |
| HPV31 | L1 | 11 | 340 |
| HPV31 | L1 | 11 | 290 |
| HPV31 | L1 | 10 | 2i2 |
| HPV31 | L1 | 11 | 432 |
| HPV31 | L1 | 9 | 284 |
| HPV31 | L1 | 10 | 284 |

TABLE XIII-continued

HLA-B58 Supermotif Peptides

| 1 | 2 | 3 | 4 |
|---|---|---|---|
| HPV31 | L1 | 11 | 302 |
| HPV31 | L1 | 11 | 89 |
| HPV31 | L1 | 11 | 423 |
| HPV31 | L1 | 8 | 354 |
| HPV31 | L1 | 11 | 354 |
| HPV31 | L1 | 8 | 408 |
| HPV31 | L1 | 9 | 337 |
| HPV31 | L1 | 11 | 337 |
| HPV31 | L1 | 9 | 239 |
| HPV31 | L1 | 10 | 239 |
| HPV31 | L1 | 11 | 239 |
| HPV31 | L1 | 8 | 66 |
| HPV31 | L1 | 9 | 66 |
| HPV31 | L1 | 11 | 66 |
| HPV31 | L1 | 10 | 18 |
| HPV31 | L1 | 11 | 18 |
| HPV31 | L1 | 8 | 28 |
| HPV31 | L1 | 10 | 28 |
| HPV31 | L1 | 8 | 301 |
| HPV31 | L1 | 8 | 101 |
| HPV31 | L2 | 9 | 24 |
| HPV31 | L2 | 10 | 24 |
| HPV31 | L2 | 9 | 340 |
| HPV31 | L2 | 9 | 85 |
| HPV31 | L2 | 11 | 85 |
| HPV31 | L2 | 10 | 367 |
| HPV31 | L2 | 11 | 367 |
| HPV31 | L2 | 9 | 311 |
| HPV31 | L2 | 10 | 311 |
| HPV31 | L2 | 11 | 311 |
| HPV31 | L2 | 10 | 15 |
| HPV31 | L2 | 11 | 15 |
| HPV31 | L2 | 8 | 226 |
| HPV31 | L2 | 9 | 135 |
| HPV31 | L2 | 10 | 135 |
| HPV31 | L2 | 11 | 135 |
| HPV31 | L2 | 11 | 342 |
| HPV31 | L2 | 10 | 358 |
| HPV31 | L2 | 8 | 364 |
| HPV31 | L2 | 9 | 139 |
| HPV31 | L2 | 10 | 84 |
| HPV31 | L2 | 9 | 111 |
| HPV31 | L2 | 11 | 111 |
| HPV31 | L2 | 8 | 331 |
| HPV31 | L2 | 10 | 331 |
| HPV31 | L2 | 8 | 171 |
| HPV31 | L2 | 9 | 253 |
| HPV31 | L2 | 10 | 253 |
| HPV31 | L2 | 11 | 253 |
| HPV31 | L2 | 8 | 404 |
| HPV31 | L2 | 11 | 404 |
| HPV31 | L2 | 8 | 263 |
| HPV31 | L2 | 9 | 263 |
| HPV31 | L2 | 8 | 459 |
| HPV31 | L2 | 11 | 361 |
| HPV31 | L2 | 8 | 314 |
| HPV31 | L2 | 10 | 314 |
| HPV31 | L2 | 10 | 339 |
| HPV31 | L2 | 8 | 310 |
| HPV31 | L2 | 10 | 310 |
| HPV31 | L2 | 11 | 310 |
| HPV31 | L2 | 10 | 63 |
| HPV31 | L2 | 11 | 63 |
| HPV31 | L2 | 10 | 49 |
| HPV31 | L2 | 8 | 26 |
| HPV31 | L2 | 11 | 26 |
| HPV31 | L2 | 8 | 65 |
| HPV31 | L2 | 9 | 65 |
| HPV31 | L2 | 11 | 65 |
| HPV31 | L2 | 9 | 413 |
| HPV31 | L2 | 11 | 413 |
| HPV31 | L2 | 8 | 38 |
| HPV31 | L2 | 9 | 38 |
| HPV31 | L2 | 11 | 38 |
| HPV31 | L2 | 8 | 41 |
| HPV31 | L2 | 11 | 41 |
| HPV31 | L2 | 8 | 280 |
| HPV31 | L2 | 8 | 270 |
| HPV31 | L2 | 10 | 270 |
| HPV31 | L2 | 11 | 270 |
| HPV31 | L2 | 10 | 134 |
| HPV31 | L2 | 11 | 134 |
| HPV31 | L2 | 11 | 323 |
| HPV31 | L2 | 9 | 183 |
| HPV31 | L2 | 11 | 183 |
| HPV31 | L2 | 10 | 205 |
| HPV31 | L2 | 8 | 245 |
| HPV31 | L2 | 11 | 245 |
| HPV31 | L2 | 10 | 23 |
| HPV31 | L2 | 11 | 23 |
| HPV31 | L2 | 8 | 225 |
| HPV31 | L2 | 9 | 225 |
| HPV31 | L2 | 8 | 423 |
| HPV31 | L2 | 10 | 423 |
| HPV31 | L2 | 11 | 423 |
| HPV31 | L2 | 8 | 238 |
| HPV31 | L2 | 10 | 238 |
| HPV31 | L2 | 11 | 178 |
| HPV31 | L2 | 9 | 395 |
| HPV31 | L2 | 10 | 395 |
| HPV31 | L2 | 8 | 75 |
| HPV31 | L2 | 11 | 75 |
| HPV31 | L2 | 8 | 287 |
| HPV31 | L2 | 10 | 287 |
| HPV31 | L2 | 8 | 256 |
| HPV31 | L2 | 10 | 390 |
| HPV31 | L2 | 8 | 292 |
| HPV31 | L2 | 8 | 169 |
| HPV31 | L2 | 9 | 169 |
| HPV31 | L2 | 10 | 169 |
| HPV31 | L2 | 8 | 328 |
| HPV31 | L2 | 11 | 328 |
| HPV31 | L2 | 9 | 142 |
| HPV31 | L2 | 10 | 285 |
| HPV31 | L2 | 10 | 217 |
| HPV31 | L2 | 11 | 366 |
| HPV31 | L2 | 8 | 250 |
| HPV31 | L2 | 8 | 29 |
| HPV31 | L2 | 10 | 373 |
| HPV31 | L2 | 11 | 373 |
| HPV31 | L2 | 9 | 79 |
| HPV31 | L2 | 11 | 79 |
| HPV31 | L2 | 10 | 161 |
| HPV31 | L2 | 10 | 235 |
| HPV31 | L2 | 11 | 235 |
| HPV31 | L2 | 8 | 156 |
| HPV31 | L2 | 9 | 156 |
| HPV31 | L2 | 8 | 388 |
| HPV31 | L2 | 10 | 167 |
| HPV31 | L2 | 11 | 167 |
| HPV31 | L2 | 9 | 415 |
| HPV31 | L2 | 10 | 415 |
| HPV31 | L2 | 8 | 425 |
| HPV31 | L2 | 9 | 425 |
| HPV31 | L2 | 10 | 425 |
| HPV31 | L2 | 8 | 127 |
| HPV31 | L2 | 9 | 127 |
| HPV31 | L2 | 8 | 378 |
| HPV31 | L2 | 9 | 378 |
| HPV31 | L2 | 10 | 378 |
| HPV31 | L2 | 9 | 303 |
| HPV31 | L2 | 11 | 303 |
| HPV31 | L2 | 8 | 12 |
| HPV31 | L2 | 8 | 308 |
| HPV31 | L2 | 10 | 308 |
| HPV31 | L2 | 9 | 5 |
| HPV31 | L2 | 11 | 5 |
| HPV31 | L2 | 10 | 9 |
| HPV31 | L2 | 11 | 9 |
| HPV31 | L2 | 8 | 306 |

TABLE XIII-continued

HLA-B58 Supermotif Peptides

| 1 | 2 | 3 | 4 |
|---|---|---|---|
| HPV31 | L2 | 10 | 306 |
| HPV31 | L2 | 9 | 239 |
| HPV31 | L2 | 11 | 14 |
| HPV31 | L2 | 8 | 341 |
| HPV31 | L2 | 10 | 384 |
| HPV31 | L2 | 10 | 324 |
| HPV31 | L2 | 8 | 181 |
| HPV31 | L2 | 11 | 181 |
| HPV31 | L2 | 9 | 180 |
| HPV31 | L2 | 10 | 179 |
| HPV31 | L2 | 8 | 207 |
| HPV31 | L2 | 9 | 374 |
| HPV31 | L2 | 10 | 374 |
| HPV31 | L2 | 8 | 396 |
| HPV31 | L2 | 9 | 396 |
| HPV31 | L2 | 8 | 151 |
| HPV31 | L2 | 8 | 184 |
| HPV31 | L2 | 10 | 184 |
| HPV31 | L2 | 8 | 6 |
| HPV31 | L2 | 10 | 6 |
| HPV31 | L2 | 8 | 346 |
| HPV31 | L2 | 10 | 346 |
| HPV31 | L2 | 11 | 346 |
| HPV31 | L2 | 11 | 208 |
| HPV31 | L2 | 10 | 76 |
| HPV31 | L2 | 8 | 379 |
| HPV31 | L2 | 9 | 379 |
| HPV31 | L2 | 8 | 80 |
| HPV31 | L2 | 10 | 80 |
| HPV31 | L2 | 8 | 137 |
| HPV31 | L2 | 9 | 137 |
| HPV31 | L2 | 11 | 137 |
| HPV31 | L2 | 8 | 375 |
| HPV31 | L2 | 9 | 375 |
| HPV31 | L2 | 11 | 375 |
| HPV31 | L2 | 8 | 380 |
| HPV31 | L2 | 10 | 129 |
| HPV31 | L2 | 11 | 266 |
| HPV31 | L2 | 9 | 288 |
| HPV31 | L2 | 9 | 206 |
| HPV31 | L2 | 8 | 345 |
| HPV31 | L2 | 9 | 345 |
| HPV31 | L2 | 11 | 345 |
| HPV31 | L2 | 11 | 148 |
| HPV31 | L2 | 8 | 136 |
| HPV31 | L2 | 9 | 136 |
| HPV31 | L2 | 10 | 136 |
| HPV31 | L2 | 8 | 39 |
| HPV31 | L2 | 10 | 39 |
| HPV31 | L2 | 8 | 140 |
| HPV31 | L2 | 11 | 140 |
| HPV31 | L2 | 8 | 426 |
| HPV31 | L2 | 9 | 426 |
| HPV31 | L2 | 8 | 128 |
| HPV31 | L2 | 11 | 128 |
| HPV31 | L2 | 9 | 344 |
| HPV31 | L2 | 10 | 344 |
| HPV31 | L2 | 10 | 343 |
| HPV31 | L2 | 11 | 343 |
| HPV31 | L2 | 9 | 391 |
| HPV31 | L2 | 11 | 391 |
| HPV31 | L2 | 11 | 383 |
| HPV31 | L2 | 8 | 82 |
| HPV31 | L2 | 9 | 93 |
| HPV31 | L2 | 10 | 430 |
| HPV31 | L2 | 11 | 430 |
| HPV31 | L2 | 9 | 106 |
| HPV31 | L2 | 10 | 106 |
| HPV31 | L2 | 9 | 150 |
| HPV31 | L2 | 8 | 198 |
| HPV31 | L2 | 8 | 455 |
| HPV31 | L2 | 10 | 455 |
| HPV31 | L2 | 11 | 455 |
| HPV31 | L2 | 8 | 356 |
| HPV31 | L2 | 8 | 223 |
| HPV31 | L2 | 10 | 223 |
| HPV31 | L2 | 11 | 223 |
| HPV31 | L2 | 10 | 296 |
| HPV33 | E1 | 11 | 382 |
| HPV33 | E1 | 8 | 90 |
| HPV33 | E1 | 11 | 90 |
| HPV33 | E1 | 9 | 96 |
| HPV33 | E1 | 10 | 96 |
| HPV33 | E1 | 10 | 383 |
| HPV33 | E1 | 9 | 104 |
| HPV33 | E1 | 8 | 65 |
| HPV33 | E1 | 8 | 83 |
| HPV33 | E1 | 9 | 83 |
| HPV33 | E1 | 9 | 310 |
| HPV33 | E1 | 10 | 310 |
| HPV33 | E1 | 10 | 633 |
| HPV33 | E1 | 8 | 276 |
| HPV33 | E1 | 9 | 276 |
| HPV33 | E1 | 11 | 276 |
| HPV33 | E1 | 9 | 92 |
| HPV33 | E1 | 10 | 92 |
| HPV33 | E1 | 9 | 226 |
| HPV33 | E1 | 11 | 226 |
| HPV33 | E1 | 9 | 14 |
| HPV33 | E1 | 10 | 14 |
| HPV33 | E1 | 11 | 14 |
| HPV33 | E1 | 8 | 118 |
| HPV33 | E1 | 11 | 118 |
| HPV33 | E1 | 10 | 508 |
| HPV33 | E1 | 8 | 177 |
| HPV33 | E1 | 11 | 177 |
| HPV33 | E1 | 8 | 365 |
| HPV33 | E1 | 9 | 365 |
| HPV33 | E1 | 11 | 365 |
| HPV33 | E1 | 10 | 167 |
| HPV33 | E1 | 9 | 42 |
| HPV33 | E1 | 10 | 42 |
| HPV33 | E1 | 9 | 130 |
| HPV33 | E1 | 9 | 53 |
| HPV33 | E1 | 8 | 377 |
| HPV33 | E1 | 9 | 377 |
| HPV33 | E1 | 10 | 377 |
| HPV33 | E1 | 11 | 566 |
| HPV33 | E1 | 8 | 62 |
| HPV33 | E1 | 9 | 62 |
| HPV33 | E1 | 11 | 62 |
| HPV33 | E1 | 9 | 64 |
| HPV33 | E1 | 8 | 206 |
| HPV33 | E1 | 10 | 206 |
| HPV33 | E1 | 11 | 206 |
| HPV33 | E1 | 9 | 148 |
| HPV33 | E1 | 11 | 160 |
| HPV33 | E1 | 10 | 38 |
| HPV33 | E1 | 11 | 38 |
| HPV33 | E1 | 11 | 295 |
| HPV33 | E1 | 10 | 173 |
| HPV33 | E1 | 9 | 139 |
| HPV33 | E1 | 8 | 89 |
| HPV33 | E1 | 9 | 89 |
| HPV33 | E1 | 8 | 606 |
| HPV33 | E1 | 10 | 606 |
| HPV33 | E1 | 11 | 606 |
| HPV33 | E1 | 8 | 446 |
| HPV33 | E1 | 11 | 446 |
| HPV33 | E1 | 10 | 451 |
| HPV33 | E1 | 9 | 9 |
| HPV33 | E1 | 10 | 9 |
| HPV33 | E1 | 8 | 44 |
| HPV33 | E1 | 8 | 564 |
| HPV33 | E1 | 9 | 564 |
| HPV33 | E1 | 10 | 327 |
| HPV33 | E1 | 8 | 341 |
| HPV33 | E1 | 10 | 341 |
| HPV33 | E1 | 10 | 251 |
| HPV33 | E1 | 9 | 573 |

TABLE XIII-continued

HLA-B58 Supermotif Peptides

| 1 | 2 | 3 | 4 |
|---|---|---|---|
| HPV33 | E1 | 9 | 192 |
| HPV33 | E1 | 10 | 192 |
| HPV33 | E1 | 11 | 192 |
| HPV33 | E1 | 8 | 368 |
| HPV33 | E1 | 9 | 368 |
| HPV33 | E1 | 10 | 492 |
| HPV33 | E1 | 11 | 492 |
| HPV33 | E1 | 11 | 322 |
| HPV33 | E1 | 9 | 32 |
| HPV33 | E1 | 10 | 210 |
| HPV33 | E1 | 9 | 538 |
| HPV33 | E1 | 10 | 538 |
| HPV33 | E1 | 11 | 538 |
| HPV33 | E1 | 9 | 236 |
| HPV33 | E1 | 11 | 236 |
| HPV33 | E1 | 8 | 628 |
| HPV33 | E1 | 9 | 520 |
| HPV33 | E1 | 10 | 520 |
| HPV33 | E1 | 10 | 231 |
| HPV33 | E1 | 11 | 231 |
| HPV33 | E1 | 9 | 407 |
| HPV33 | E1 | 8 | 197 |
| HPV33 | E1 | 11 | 197 |
| HPV33 | E1 | 10 | 463 |
| HPV33 | E1 | 10 | 220 |
| HPV33 | E1 | 8 | 603 |
| HPV33 | E1 | 11 | 603 |
| HPV33 | E1 | 9 | 498 |
| HPV33 | E1 | 8 | 387 |
| HPV33 | E1 | 9 | 387 |
| HPV33 | E1 | 8 | 476 |
| HPV33 | E1 | 9 | 476 |
| HPV33 | E1 | 11 | 476 |
| HPV33 | E1 | 8 | 425 |
| HPV33 | E1 | 11 | 425 |
| HPV33 | E1 | 9 | 223 |
| HPV33 | E1 | 8 | 375 |
| HPV33 | E1 | 9 | 375 |
| HPV33 | E1 | 10 | 375 |
| HPV33 | E1 | 11 | 375 |
| HPV33 | E1 | 8 | 506 |
| HPV33 | E1 | 9 | 506 |
| HPV33 | E1 | 8 | 350 |
| HPV33 | E1 | 9 | 350 |
| HPV33 | E1 | 8 | 291 |
| HPV33 | E1 | 9 | 291 |
| HPV33 | E1 | 10 | 291 |
| HPV33 | E1 | 8 | 260 |
| HPV33 | E1 | 9 | 260 |
| HPV33 | E1 | 10 | 260 |
| HPV33 | E1 | 11 | 260 |
| HPV33 | E1 | 8 | 362 |
| HPV33 | E1 | 9 | 362 |
| HPV33 | E1 | 10 | 362 |
| HPV33 | E1 | 11 | 362 |
| HPV33 | E1 | 10 | 281 |
| HPV33 | E1 | 11 | 281 |
| HPV33 | E1 | 10 | 576 |
| HPV33 | E1 | 8 | 336 |
| HPV33 | E1 | 10 | 1 |
| HPV33 | E1 | 11 | 481 |
| HPV33 | E1 | 8 | 562 |
| HPV33 | E1 | 10 | 562 |
| HPV33 | E1 | 11 | 562 |
| HPV33 | E1 | 8 | 531 |
| HPV33 | E1 | 10 | 531 |
| HPV33 | E1 | 10 | 80 |
| HPV33 | E1 | 11 | 80 |
| HPV33 | E1 | 9 | 57 |
| HPV33 | E1 | 10 | 57 |
| HPV33 | E1 | 8 | 496 |
| HPV33 | E1 | 11 | 496 |
| HPV33 | E1 | 8 | 379 |
| HPV33 | E1 | 9 | 135 |
| HPV33 | E1 | 10 | 135 |
| HPV33 | E1 | 9 | 473 |
| HPV33 | E1 | 11 | 473 |
| HPV33 | E1 | 8 | 195 |
| HPV33 | E1 | 10 | 195 |
| HPV33 | E1 | 10 | 560 |
| HPV33 | E1 | 8 | 471 |
| HPV33 | E1 | 9 | 471 |
| HPV33 | E1 | 11 | 471 |
| HPV33 | E1 | 9 | 238 |
| HPV33 | E1 | 10 | 238 |
| HPV33 | E1 | 11 | 238 |
| HPV33 | E1 | 9 | 60 |
| HPV33 | E1 | 10 | 60 |
| HPV33 | E1 | 11 | 60 |
| HPV33 | E1 | 10 | 391 |
| HPV33 | E1 | 11 | 391 |
| HPV33 | E1 | 8 | 94 |
| HPV33 | E1 | 11 | 94 |
| HPV33 | E1 | 8 | 308 |
| HPV33 | E1 | 11 | 308 |
| HPV33 | E1 | 10 | 103 |
| HPV33 | E1 | 11 | 545 |
| HPV33 | E1 | 8 | 306 |
| HPV33 | E1 | 9 | 306 |
| HPV33 | E1 | 10 | 306 |
| HPV33 | E1 | 10 | 316 |
| HPV33 | E1 | 8 | 608 |
| HPV33 | E1 | 9 | 608 |
| HPV33 | E1 | 10 | 95 |
| HPV33 | E1 | 11 | 95 |
| HPV33 | E1 | 9 | 634 |
| HPV33 | E1 | 10 | 161 |
| HPV33 | E1 | 8 | 193 |
| HPV33 | E1 | 9 | 193 |
| HPV33 | E1 | 10 | 193 |
| HPV33 | E1 | 9 | 39 |
| HPV33 | E1 | 10 | 39 |
| HPV33 | E1 | 10 | 447 |
| HPV33 | E1 | 11 | 447 |
| HPV33 | E1 | 9 | 317 |
| HPV33 | E1 | 8 | 224 |
| HPV33 | E1 | 11 | 224 |
| HPV33 | E1 | 11 | 110 |
| HPV33 | E1 | 9 | 328 |
| HPV33 | E1 | 11 | 328 |
| HPV33 | E1 | 8 | 240 |
| HPV33 | E1 | 9 | 240 |
| HPV33 | E1 | 8 | 283 |
| HPV33 | E1 | 9 | 283 |
| HPV33 | E1 | 11 | 283 |
| HPV33 | E1 | 9 | 182 |
| HPV33 | E1 | 10 | 182 |
| HPV33 | E1 | 8 | 517 |
| HPV33 | E1 | 9 | 517 |
| HPV33 | E1 | 8 | 522 |
| HPV33 | E1 | 11 | 522 |
| HPV33 | E1 | 8 | 595 |
| HPV33 | E1 | 11 | 595 |
| HPV33 | E1 | 11 | 372 |
| HPV33 | E2 | 9 | 223 |
| HPV33 | E2 | 8 | 224 |
| NPV33 | E2 | 9 | 175 |
| HPV33 | E2 | 10 | 175 |
| HPV33 | E2 | 9 | 64 |
| HPV33 | E2 | 10 | 64 |
| HPV33 | E2 | 11 | 258 |
| HPV33 | E2 | 11 | 245 |
| HPV33 | E2 | 10 | 40 |
| HPV33 | E2 | 8 | 269 |
| HPV33 | E2 | 9 | 269 |
| HPV33 | E2 | 11 | 269 |
| HPV33 | E2 | 8 | 145 |
| HPV33 | E2 | 10 | 145 |
| HPV33 | E2 | 11 | 145 |
| HPV33 | E2 | 8 | 261 |

TABLE XIII-continued

HLA-B58 Supermotif Peptides

| 1 | 2 | 3 | 4 |
|---|---|---|---|
| HPV33 | E2 | 10 | 174 |
| HPV33 | E2 | 11 | 174 |
| HPV33 | E2 | 9 | 235 |
| HPV33 | E2 | 10 | 235 |
| HPV33 | E2 | 10 | 143 |
| HPV33 | E2 | 9 | 232 |
| HPV33 | E2 | 11 | 20 |
| HPV33 | E2 | 8 | 282 |
| HPV33 | E2 | 10 | 282 |
| HPV33 | E2 | 8 | 80 |
| HPV33 | E2 | 8 | 51 |
| HPV33 | E2 | 9 | 51 |
| HPV33 | E2 | 9 | 336 |
| HPV33 | E2 | 11 | 336 |
| HPV33 | E2 | 8 | 4 |
| HPV33 | E2 | 8 | 346 |
| HPV33 | E2 | 9 | 204 |
| HPV33 | E2 | 8 | 68 |
| HPV33 | E2 | 10 | 68 |
| HPV33 | E2 | 11 | 68 |
| HPV33 | E2 | 9 | 84 |
| HPV33 | E2 | 11 | 84 |
| HPV33 | E2 | 8 | 23 |
| HPV33 | E2 | 11 | 23 |
| HPV33 | E2 | 8 | 66 |
| HPV33 | E2 | 10 | 66 |
| HPV33 | E2 | 9 | 180 |
| HPV33 | E2 | 8 | 63 |
| HPV33 | E2 | 10 | 63 |
| HPV33 | E2 | 11 | 63 |
| HPV33 | E2 | 11 | 82 |
| HPV33 | E2 | 10 | 240 |
| HPV33 | E2 | 11 | 240 |
| HPV33 | E2 | 11 | 77 |
| HPV33 | E2 | 8 | 9 |
| HPV33 | E2 | 10 | 9 |
| HPV33 | E2 | 11 | 9 |
| HPV33 | E2 | 9 | 315 |
| HPV33 | E2 | 11 | 315 |
| HPV33 | E2 | 8 | 284 |
| HPV33 | E2 | 10 | 284 |
| HPV33 | E2 | 8 | 127 |
| HPV33 | E2 | 11 | 127 |
| HPV33 | E2 | 8 | 230 |
| HPV33 | E2 | 11 | 230 |
| HPV33 | E2 | 8 | 248 |
| HPV33 | E2 | 11 | 248 |
| HPV33 | E2 | 10 | 60 |
| HPV33 | E2 | 13 | 60 |
| HPV33 | E2 | 9 | 27 |
| HPV33 | E2 | 10 | 27 |
| HPV33 | E2 | 9 | 196 |
| HPV33 | E2 | 9 | 342 |
| HPV33 | E2 | 10 | 342 |
| HPV33 | E2 | 10 | 222 |
| HPV33 | E2 | 11 | 213 |
| HPV33 | E2 | 8 | 96 |
| HPV33 | E2 | 8 | 266 |
| HPV33 | E2 | 9 | 266 |
| HPV33 | E2 | 11 | 266 |
| HPV33 | E2 | 11 | 5 |
| HPV33 | E2 | 9 | 301 |
| HPV33 | E2 | 11 | 200 |
| HPV33 | E2 | 8 | 270 |
| HPV33 | E2 | 10 | 270 |
| HPV33 | E2 | 8 | 205 |
| HPV33 | E2 | 10 | 45 |
| HPV33 | E2 | 8 | 236 |
| HPV33 | E2 | 9 | 236 |
| HPV33 | E2 | 11 | 236 |
| HPV33 | E2 | 11 | 310 |
| HPV33 | E2 | 8 | 197 |
| HPV33 | E2 | 11 | 89 |
| HPV33 | E2 | 8 | 233 |
| HPV33 | E2 | 11 | 233 |
| HPV33 | E2 | 8 | 326 |
| HPV33 | E2 | 9 | 326 |
| HPV33 | E2 | 10 | 326 |
| HPV33 | E2 | 11 | 323 |
| HPV33 | E2 | 8 | 148 |
| HPV33 | E2 | 10 | 148 |
| HPV33 | E2 | 11 | 148 |
| HPV33 | E2 | 8 | 92 |
| HPV33 | E2 | 10 | 92 |
| HPV33 | E2 | 11 | 92 |
| HPV33 | E2 | 9 | 178 |
| HPV33 | E2 | 11 | 178 |
| HPV33 | E2 | 8 | 300 |
| HPV33 | E2 | 10 | 300 |
| HPV33 | E2 | 8 | 87 |
| HPV33 | E2 | 8 | 44 |
| HPV33 | E2 | 11 | 44 |
| HPV33 | E2 | 8 | 131 |
| HPV33 | E2 | 9 | 131 |
| HPV33 | E2 | 10 | 131 |
| HPV33 | E5 | 8 | 44 |
| HPV33 | E5 | 10 | 44 |
| HPV33 | E5 | 11 | 44 |
| HPV33 | E5 | 8 | 26 |
| HPV33 | E5 | 9 | 26 |
| HPV33 | E5 | 10 | 26 |
| HPV33 | E5 | 11 | 26 |
| HPV33 | E5 | 8 | 24 |
| HPV33 | E5 | 9 | 24 |
| HPV33 | E5 | 10 | 24 |
| HPV33 | E5 | 11 | 24 |
| HPV33 | E5 | 8 | 15 |
| HPV33 | E5 | 9 | 15 |
| HPV33 | E5 | 10 | 15 |
| HPV33 | E5 | 8 | 27 |
| HPV33 | E5 | 9 | 27 |
| HPV33 | E5 | 10 | 27 |
| HPV33 | E5 | 11 | 27 |
| HPV33 | E5 | 8 | 29 |
| HPV33 | E5 | 9 | 29 |
| HPV33 | E5 | 10 | 29 |
| HPV33 | E5 | 11 | 29 |
| HPV33 | E5 | 9 | 4 |
| HPV33 | E6 | 9 | 20 |
| HPV33 | E6 | 8 | 47 |
| HPV33 | E6 | 8 | 45 |
| HPV33 | E6 | 9 | 45 |
| HPV33 | E6 | 10 | 45 |
| HPV33 | E6 | 9 | 73 |
| HPV33 | E6 | 11 | 73 |
| HPV33 | E6 | 10 | 128 |
| HPV33 | E6 | 11 | 128 |
| HPV33 | E6 | 10 | 70 |
| HPV33 | E6 | 11 | 50 |
| HPV23 | E6 | 11 | 86 |
| HPV33 | E6 | 10 | 17 |
| HPV33 | E6 | 10 | 90 |
| HPV33 | E6 | 11 | 90 |
| HPV33 | E6 | 8 | 39 |
| HPV33 | E6 | 9 | 39 |
| HPV33 | E6 | 10 | 39 |
| HPV33 | E6 | 8 | 141 |
| HPV33 | E6 | 9 | 141 |
| HPV33 | E6 | 9 | 10 |
| HPV33 | E6 | 10 | 10 |
| HPV33 | E6 | 8 | 21 |
| HPV33 | E6 | 11 | 21 |
| HPV33 | E6 | 9 | 132 |
| HPV33 | E6 | 8 | 81 |
| HPV33 | E7 | 10 | 73 |
| HPV33 | E7 | 11 | 73 |
| HPV33 | E7 | 8 | 48 |
| HPV33 | E7 | 9 | 30 |
| HPV33 | E7 | 11 | 85 |
| HPV33 | E7 | 9 | 59 |

TABLE XIII-continued

HLA-B58 Supermotif Peptides

| 1 | 2 | 3 | 4 |
|---|---|---|---|
| HPV33 | E7 | 11 | 59 |
| HPV33 | E7 | 11 | 28 |
| HPV33 | E7 | 10 | 70 |
| HPV33 | E7 | 8 | 62 |
| HPV33 | E7 | 8 | 47 |
| HPV33 | E7 | 9 | 47 |
| HPV33 | E7 | 10 | 19 |
| HPV33 | E7 | 8 | 6 |
| HPV33 | E7 | 10 | 6 |
| HPV33 | E7 | 11 | 6 |
| HPV33 | E7 | 9 | 44 |
| HPV33 | E7 | 10 | 44 |
| HPV33 | E7 | 11 | 44 |
| HPV33 | E7 | 8 | 77 |
| HPV33 | E7 | 11 | 77 |
| HPV33 | E7 | 8 | 31 |
| HPV33 | E7 | 9 | 71 |
| HPV33 | E7 | 8 | 72 |
| HPV33 | E7 | 11 | 72 |
| HPV33 | E7 | 11 | 63 |
| HPV33 | E7 | 11 | 55 |
| HPV33 | L1 | 10 | 179 |
| HPV33 | L1 | 11 | 482 |
| HPV33 | L1 | 8 | 284 |
| HPV33 | L1 | 9 | 284 |
| HPV33 | L1 | 9 | 411 |
| HPV33 | L1 | 10 | 411 |
| HPV33 | L1 | 8 | 9 |
| HPV33 | L1 | 10 | 9 |
| HPV33 | L1 | 10 | 345 |
| HPV33 | L1 | 9 | 351 |
| HPV33 | L1 | 8 | 129 |
| HPV33 | L1 | 9 | 202 |
| HPV33 | L1 | 8 | 95 |
| HPV33 | L1 | 10 | 95 |
| HPV33 | L1 | 8 | 335 |
| HPV33 | L1 | 10 | 335 |
| HPV33 | L1 | 10 | 415 |
| HPV33 | L1 | 11 | 415 |
| HPV33 | L1 | 9 | 8 |
| HPV33 | L1 | 11 | 8 |
| HPV33 | L1 | 8 | 269 |
| HPV33 | L1 | 9 | 269 |
| HPV33 | L1 | 9 | 303 |
| HPV33 | L1 | 10 | 303 |
| HPV33 | L1 | 11 | 303 |
| HPV33 | L1 | 8 | 454 |
| HPV33 | L1 | 10 | 454 |
| HPV33 | L1 | 9 | 50 |
| HPV33 | L1 | 8 | 141 |
| HPV33 | L1 | 10 | 141 |
| HPV33 | L1 | 8 | 279 |
| HPV33 | L1 | 10 | 297 |
| HPV33 | L1 | 11 | 297 |
| HPV33 | L1 | 8 | 38 |
| HPV33 | L1 | 9 | 226 |
| HPV33 | L1 | 10 | 226 |
| HPV33 | L1 | 11 | 265 |
| HPV33 | L1 | 10 | 281 |
| HPV33 | L1 | 11 | 281 |
| HPV33 | L1 | 8 | 391 |
| HPV33 | L1 | 11 | 391 |
| HPV33 | L1 | 10 | 118 |
| HPV33 | L1 | 9 | 474 |
| HPV33 | L1 | 10 | 474 |
| HPV33 | L1 | 8 | 217 |
| HPV33 | L1 | 10 | 211 |
| HPV33 | L1 | 8 | 43 |
| HPV33 | L1 | 10 | 43 |
| HPV33 | L1 | 10 | 148 |
| HPV33 | L1 | 8 | 382 |
| HPV33 | L1 | 9 | 382 |
| HPV33 | L1 | 11 | 382 |
| HPV33 | L1 | 9 | 405 |
| HPV33 | L1 | 9 | 1 |
| HPV33 | L1 | 11 | 1 |
| HPV33 | L1 | 10 | 237 |
| HPV33 | L1 | 11 | 237 |
| HPV33 | L1 | 11 | 387 |
| HPV33 | L1 | 11 | 178 |
| HPV33 | L1 | 10 | 57 |
| HPV33 | L1 | 9 | 192 |
| HPV33 | L1 | 10 | 192 |
| HPV33 | L1 | 8 | 181 |
| HPV33 | L1 | 10 | 181 |
| HPV33 | L1 | 11 | 181 |
| HPV33 | L1 | 9 | 409 |
| HPV33 | L1 | 11 | 409 |
| HPV33 | L1 | 8 | 6 |
| HPV33 | L1 | 11 | 6 |
| HPV33 | L1 | 10 | 165 |
| HPV33 | L1 | 11 | 165 |
| HPV33 | L1 | 8 | 55 |
| HPV33 | L1 | 9 | 55 |
| HPV33 | L1 | 8 | 293 |
| HPV33 | L1 | 9 | 484 |
| HPV33 | L1 | 10 | 470 |
| HPV33 | L1 | 9 | 423 |
| HPV33 | L1 | 9 | 214 |
| HPV33 | L1 | 11 | 214 |
| HPV33 | L1 | 8 | 263 |
| HPV33 | L1 | 9 | 263 |
| HPV33 | L1 | 9 | 315 |
| HPV33 | L1 | 11 | 315 |
| HPV33 | L1 | 11 | 338 |
| HPV33 | L1 | 8 | 30 |
| HPV33 | L1 | 10 | 488 |
| HPV33 | L1 | 9 | 455 |
| HPV33 | L1 | 11 | 289 |
| HPV33 | L1 | 8 | 410 |
| HPV33 | L1 | 10 | 410 |
| HPV33 | L1 | 11 | 410 |
| HPV33 | L1 | 8 | 490 |
| HPV33 | L1 | 11 | 39 |
| HPV33 | L1 | 8 | 227 |
| HPV33 | L1 | 9 | 227 |
| HPV33 | L1 | 11 | 227 |
| HPV33 | L1 | 11 | 23 |
| HPV33 | L1 | 10 | 339 |
| HPV33 | L1 | 8 | 352 |
| HPV33 | L1 | 11 | 352 |
| HPV33 | L1 | 8 | 383 |
| HPV33 | L1 | 10 | 383 |
| HPV33 | L1 | 11 | 383 |
| HPV33 | L1 | 8 | 283 |
| HPV33 | L1 | 9 | 283 |
| HPV33 | L1 | 10 | 283 |
| HPV33 | L1 | 11 | 349 |
| HPV33 | L1 | 9 | 238 |
| HPV33 | L1 | 10 | 238 |
| HPV33 | L1 | 11 | 238 |
| HPV33 | L1 | 11 | 301 |
| HPV33 | L1 | 11 | 89 |
| HPV33 | L1 | 11 | 42i |
| HPV33 | L1 | 9 | 489 |
| HPV33 | L1 | 8 | 485 |
| HPV33 | L1 | 9 | 282 |
| HPV33 | L1 | 10 | 282 |
| HPV33 | L1 | 11 | 282 |
| HPV33 | L1 | 9 | 336 |
| HPV33 | L1 | 9 | 174 |
| HPV33 | L1 | 8 | 66 |
| HPV33 | L1 | 9 | 66 |
| HPV33 | L1 | 11 | 66 |
| HPV33 | L1 | 10 | 18 |
| HPV33 | L1 | 11 | 18 |
| HPV33 | L1 | 8 | 28 |
| HPV33 | L1 | 9 | 28 |
| HPV33 | L1 | 10 | 28 |
| HPV33 | L1 | 8 | 380 |

TABLE XIII-continued

HLA-B58 Supermotif Peptides

| 1 | 2 | 3 | 4 |
|---|---|---|---|
| HPV33 | L1 | 10 | 380 |
| HPV33 | L1 | 11 | 380 |
| HPV33 | L1 | 8 | 300 |
| HPV33 | L1 | 8 | 101 |
| HPV33 | L1 | 8 | 36 |
| HPV33 | L1 | 9 | 36 |
| HPV33 | L1 | 10 | 36 |
| HPV33 | L1 | 8 | 443 |
| HPV33 | L2 | 8 | 81 |
| HPV33 | L2 | 9 | 23 |
| HPV33 | L2 | 10 | 23 |
| HPV33 | L2 | 11 | 308 |
| HPV33 | L2 | 10 | 14 |
| HPV33 | L2 | 8 | 385 |
| HPV33 | L2 | 10 | 385 |
| HPV33 | L2 | 8 | 101 |
| HPV33 | L2 | 11 | 206 |
| HPV33 | L2 | 8 | 431 |
| HPV33 | L2 | 10 | 431 |
| HPV33 | L2 | 11 | 431 |
| HPV33 | L2 | 10 | 264 |
| HPV33 | L2 | 10 | 401 |
| HPV33 | L2 | 9 | 350 |
| HPV33 | L2 | 9 | 136 |
| HPV33 | L2 | 10 | 95 |
| HPV33 | L2 | 11 | 95 |
| HPV33 | L2 | 9 | 115 |
| HPV33 | L2 | 8 | 176 |
| HPV33 | L2 | 9 | 258 |
| HPV33 | L2 | 11 | 258 |
| HPV33 | L2 | 11 | 149 |
| HPV33 | L2 | 9 | 110 |
| HPV33 | L2 | 11 | 110 |
| HPV33 | L2 | 9 | 384 |
| HPV33 | L2 | 11 | 384 |
| HPV33 | L2 | 8 | 301 |
| HPV33 | L2 | 10 | 301 |
| HPV33 | L2 | 11 | 183 |
| HPV33 | L2 | 8 | 460 |
| HPV33 | L2 | 11 | 163 |
| HPV33 | L2 | 10 | 437 |
| HPV33 | L2 | 11 | 437 |
| HPV33 | L2 | 10 | 319 |
| HPV33 | L2 | 8 | 64 |
| HPV33 | L2 | 9 | 64 |
| HPV33 | L2 | 11 | 64 |
| HPV33 | L2 | 10 | 62 |
| HPV33 | L2 | 11 | 62 |
| HPV33 | L2 | 10 | 48 |
| HPV33 | L2 | 8 | 218 |
| HPV33 | L2 | 10 | 218 |
| HPV33 | L2 | 11 | 218 |
| HPV33 | L2 | 8 | 37 |
| HPV33 | L2 | 9 | 37 |
| HPV33 | L2 | 11 | 37 |
| HPV33 | L2 | 8 | 25 |
| HPV33 | L2 | 11 | 25 |
| HPV33 | L2 | 8 | 75 |
| HPV33 | L2 | 9 | 75 |
| HPV33 | L2 | 11 | 75 |
| HPV33 | L2 | 8 | 374 |
| HPV33 | L2 | 11 | 374 |
| HPV33 | L2 | 8 | 336 |
| HPV33 | L2 | 10 | 336 |
| HPV33 | L2 | 8 | 297 |
| HPV33 | L2 | 8 | 40 |
| HPV33 | L2 | 11 | 40 |
| HPV33 | L2 | 8 | 285 |
| HPV33 | L2 | 9 | 273 |
| HPV33 | L2 | 10 | 273 |
| HPV33 | L2 | 10 | 424 |
| HPV33 | L2 | 11 | 424 |
| HPV33 | L2 | 9 | 155 |
| HPV33 | L2 | 8 | 292 |
| HPV33 | L2 | 10 | 292 |
| HPV33 | L2 | 8 | 250 |
| HPV33 | L2 | 11 | 250 |
| HPV33 | L2 | 10 | 22 |
| HPV33 | L211 | 22 | |
| HPV33 | L2 | 8 | 311 |
| HPV33 | L2 | 10 | 311 |
| HPV33 | L2 | 11 | 328 |
| HPV33 | L2 | 8 | 243 |
| HPV33 | L2 | 10 | 243 |
| HPV33 | L2 | 10 | 405 |
| HPV33 | L2 | 11 | 405 |
| HPV33 | L2 | 8 | 397 |
| HPV33 | L2 | 9 | 397 |
| HPV33 | L2 | 8 | 231 |
| HPV33 | L2 | 11 | 231 |
| HPV33 | L2 | 8 | 174 |
| HPV33 | L2 | 9 | 174 |
| HPV33 | L2 | 10 | 174 |
| HPV33 | L2 | 10 | 240 |
| HPV33 | L2 | 11 | 240 |
| HPV33 | L2 | 9 | 139 |
| HPV33 | L2 | 10 | 290 |
| HPV33 | L2 | 10 | 172 |
| HPV33 | L2 | 11 | 172 |
| HPV33 | L2 | 8 | 275 |
| HPV33 | L2 | 10 | 275 |
| HPV33 | L2 | 11 | 275 |
| HPV33 | L2 | 11 | 119 |
| HPV33 | L2 | 10 | 126 |
| HPV33 | L2 | 9 | 121 |
| HPV33 | L2 | 11 | 121 |
| HPV33 | L2 | 11 | 411 |
| HPV33 | L2 | 8 | 166 |
| HPV33 | L2 | 10 | 166 |
| HPV33 | L2 | 10 | 79 |
| HPV33 | L2 | 8 | 161 |
| HPV33 | L2 | 9 | 161 |
| HPV33 | L2 | 8 | 124 |
| HPV33 | L2 | 9 | 416 |
| HPV33 | L2 | 8 | 186 |
| HPV33 | L2 | 11 | 186 |
| HPV33 | L2 | 8 | 191 |
| HPV33 | L2 | 11 | 191 |
| HPV33 | L2 | 11 | 153 |
| HPV33 | L2 | 8 | 11 |
| HPV33 | L2 | 8 | 313 |
| HPV33 | L2 | 10 | 313 |
| HPV33 | L2 | 8 | 5 |
| HPV33 | L2 | 10 | 5 |
| HPV33 | L2 | 9 | 388 |
| HPV33 | L2 | 8 | 134 |
| HPV33 | L2 | 9 | 134 |
| HPV33 | L2 | 11 | 134 |
| HPV33 | L2 | 11 | 13 |
| HPV33 | L2 | 10 | 150 |
| HPV33 | L2 | 10 | 207 |
| HPV33 | L2 | 10 | 418 |
| HPV33 | L2 | 11 | 418 |
| HPV33 | L2 | 10 | 184 |
| HPV33 | L2 | 11 | 212 |
| HPV33 | L2 | 8 | 145 |
| HPV33 | L2 | 11 | 145 |
| HPV33 | L2 | 9 | 354 |
| HPV33 | L2 | 10 | 354 |
| HPV33 | L2 | 11 | 382 |
| HPV33 | L2 | 8 | 156 |
| HPV33 | L2 | 8 | 38 |
| HPV33 | L2 | 10 | 38 |
| HPV33 | L2 | 10 | 213 |
| HPV33 | L2 | 11 | 213 |
| HPV33 | L2 | 8 | 189 |
| HPV33 | L2 | 10 | 189 |
| HPV33 | L2 | 9 | 6 |
| HPV33 | L2 | 11 | 352 |
| HPV33 | L2 | 9 | 80 |

TABLE XIII-continued

HLA-B58 Supermotif Peptides

| 1 | 2 | 3 | 4 |
|---|---|---|---|
| HPV33 | L2 | 8 | 133 |
| HPV33 | L2 | 9 | 133 |
| HPV33 | L2 | 10 | 133 |
| HPV33 | L2 | 8 | 111 |
| HPV33 | L2 | 10 | 111 |
| HPV33 | L2 | 8 | 389 |
| HPV33 | L2 | 9 | 244 |
| HPV33 | L2 | 9 | 293 |
| HPV33 | L2 | 8 | 417 |
| HPV33 | L2 | 11 | 417 |
| HPV33 | L2 | 10 | 353 |
| HPV33 | L2 | 11 | 353 |
| HPV33 | L2 | 8 | 351 |
| HPV33 | L2 | 8 | 137 |
| HPV33 | L2 | 11 | 137 |
| HPV33 | L2 | 9 | 386 |
| HPV33 | L2 | 11 | 386 |
| HPV33 | L2 | 9 | 132 |
| HPV33 | L2 | 10 | 132 |
| HPV33 | L2 | 11 | 132 |
| HPV33 | L2 | 9 | 392 |
| HPV33 | L2 | 9 | 105 |
| HPV33 | L2 | 10 | 105 |
| HPV33 | L2 | 9 | 144 |
| HPV33 | L2 | 8 | 203 |
| HPV33 | L2 | 9 | 188 |
| HPV33 | L2 | 11 | 188 |
| HPV33 | L2 | 10 | 131 |
| HPV33 | L2 | 11 | 131 |
| HPV33 | L2 | 9 | 92 |
| HPV33 | L2 | 8 | 366 |
| HPV33 | L2 | 8 | 356 |
| HPV33 | L2 | 10 | 356 |
| HPV33 | L2 | 11 | 356 |
| HPV33 | L2 | 8 | 228 |
| HPV33 | L2 | 10 | 228 |
| HPV33 | L2 | 11 | 228 |
| HPV45 | E1 | 11 | 382 |
| HPV45 | E1 | 8 | 144 |
| HPV45 | E1 | 10 | 383 |
| HPV45 | E1 | 10 | 310 |
| HPV45 | E1 | 10 | 198 |
| HPV45 | E1 | 11 | 198 |
| HPV45 | E1 | 8 | 193 |
| HPV45 | E1 | 9 | 193 |
| HPV45 | E1 | 10 | 193 |
| HPV45 | E1 | 11 | 193 |
| HPV45 | E1 | 8 | 40 |
| HPV45 | E1 | 9 | 40 |
| HPV45 | E1 | 11 | 40 |
| HPV45 | E1 | 8 | 517 |
| HPV45 | E1 | 9 | 517 |
| HPV45 | E1 | 10 | 251 |
| HPV45 | E1 | 8 | 398 |
| HPV45 | E1 | 11 | 398 |
| HPV45 | E1 | 11 | 139 |
| HPV45 | E1 | 9 | 182 |
| HPV45 | E1 | 10 | 182 |
| HPV45 | E1 | 10 | 423 |
| HPV45 | E1 | 8 | 226 |
| HPV45 | E1 | 9 | 226 |
| HPV45 | E1 | 11 | 226 |
| HPV45 | E1 | 9 | 621 |
| HPV45 | E1 | 8 | 78 |
| HPV45 | E1 | 9 | 516 |
| HPV45 | E1 | 10 | 516 |
| HPV45 | E1 | 9 | 134 |
| HPV45 | E1 | 11 | 134 |
| HPV45 | E1 | 9 | 345 |
| HPV45 | E1 | 10 | 345 |
| HPV45 | E1 | 9 | 170 |
| HPV45 | E1 | 8 | 106 |
| HPV45 | E1 | 11 | 106 |
| HPV45 | E1 | 10 | 623 |
| HPV45 | E1 | 9 | 42 |
| HPV45 | E1 | 10 | 42 |
| HPV45 | E1 | 10 | 508 |
| HPV45 | E1 | 9 | 328 |
| HPV45 | E1 | 11 | 328 |
| HPV45 | E1 | 10 | 52 |
| HPV45 | E1 | 9 | 143 |
| HPV45 | E1 | 8 | 365 |
| HPV45 | E1 | 9 | 365 |
| HPV45 | E1 | 11 | 365 |
| HPV45 | E1 | 9 | 573 |
| HPV45 | E1 | 9 | 64 |
| HPV45 | E1 | 10 | 38 |
| HPV45 | E1 | 11 | 38 |
| HPV45 | E1 | 11 | 295 |
| HPV45 | E1 | 11 | 21 |
| HPV45 | E1 | 10 | 146 |
| HPV45 | E1 | 11 | 89 |
| HPV45 | E1 | 8 | 212 |
| HPV45 | E1 | 9 | 579 |
| HPV45 | E1 | 8 | 130 |
| HPV45 | E1 | 8 | 44 |
| HPV45 | E1 | 8 | 92 |
| HPV45 | E1 | 8 | 11 |
| HPV45 | E1 | 9 | 11 |
| HPV45 | E1 | 10 | 11 |
| HPV45 | E1 | 8 | 459 |
| HPV45 | E1 | 9 | 459 |
| HPV45 | E1 | 10 | 459 |
| HPV45 | E1 | 11 | 459 |
| HPV45 | E1 | 9 | 71 |
| HPV45 | E1 | 11 | 71 |
| HPV45 | E1 | 10 | 519 |
| HPV45 | E1 | 11 | 519 |
| HPV45 | E1 | 9 | 32 |
| HPV45 | E1 | 11 | 132 |
| HPV45 | E1 | 11 | 322 |
| HPV45 | E1 | 10 | 447 |
| HPV45 | E1 | 11 | 447 |
| HPV45 | E1 | 10 | 492 |
| HPV45 | E1 | 11 | 492 |
| HPV45 | E1 | 10 | 538 |
| HPV45 | E1 | 11 | 538 |
| HPV45 | E1 | 10 | 116 |
| HPV45 | E1 | 8 | 184 |
| HPV45 | E1 | 10 | 184 |
| HPV45 | E1 | 8 | 197 |
| HPV45 | E1 | 11 | 197 |
| HPV45 | E1 | 9 | 124 |
| HPV45 | E1 | 10 | 220 |
| HPV45 | E1 | 11 | 220 |
| HPV45 | E1 | 8 | 387 |
| HPV45 | E1 | 9 | 387 |
| HPV45 | E1 | 8 | 476 |
| HPV45 | E1 | 9 | 476 |
| HPV45 | E1 | 11 | 476 |
| HPV45 | E1 | 9 | 245 |
| HPV45 | E1 | 10 | 245 |
| HPV45 | E1 | 11 | 245 |
| HPV45 | E1 | 8 | 223 |
| HPV45 | E1 | 9 | 223 |
| HPV45 | E1 | 10 | 223 |
| HPV45 | E1 | 11 | 223 |
| HPV45 | E1 | 8 | 375 |
| HPV45 | E1 | 9 | 375 |
| HPV45 | E1 | 10 | 375 |
| HPV45 | E1 | 11 | 375 |
| HPV45 | E1 | 8 | 506 |
| HPV45 | E1 | 9 | 506 |
| HPV45 | E1 | 8 | 201 |
| HPV45 | E1 | 10 | 201 |
| HPV45 | E1 | 8 | 350 |
| HPV45 | E1 | 9 | 350 |
| HPV45 | E1 | 10 | 210 |
| HPV45 | E1 | 8 | 109 |
| HPV45 | E1 | 10 | 109 |

TABLE XIII-continued

HLA-B58 Supermotif Peptides

| 1 | 2 | 3 | 4 |
|---|---|---|---|
| HPV45 | E1 | 11 | 103 |
| HPV45 | E1 | 8 | 362 |
| HPV45 | E1 | 9 | 362 |
| HPV45 | E1 | 11 | 362 |
| HPV45 | E1 | 8 | 336 |
| HPV45 | E1 | 8 | 557 |
| HPV45 | E1 | 10 | 281 |
| HPV45 | E1 | 11 | 281 |
| HPV45 | E1 | 8 | 368 |
| HPV45 | E1 | 9 | 368 |
| HPV45 | E1 | 10 | 231 |
| HPV45 | E1 | 11 | 231 |
| HPV45 | E1 | 10 | 481 |
| HPV45 | E1 | 11 | 481 |
| HPV45 | E1 | 8 | 154 |
| HPV45 | E1 | 11 | 174 |
| HPV45 | E1 | 8 | 531 |
| HPV45 | E1 | 10 | 531 |
| HPV45 | E1 | 11 | 119 |
| HPV45 | E1 | 9 | 498 |
| HPV45 | E1 | 10 | 498 |
| HPV45 | E1 | 8 | 379 |
| HPV45 | E1 | 8 | 496 |
| HPV45 | E1 | 11 | 496 |
| HPV45 | E1 | 8 | 96 |
| HPV45 | E1 | 10 | 96 |
| HPV45 | E1 | 9 | 473 |
| HPV45 | E1 | 11 | 473 |
| HPV45 | E1 | 10 | 152 |
| HPV45 | E1 | 9 | 563 |
| HPV45 | E1 | 10 | 563 |
| HPV45 | E1 | 8 | 471 |
| HPV45 | E1 | 9 | 471 |
| HPV45 | E1 | 11 | 471 |
| HPV45 | E1 | 8 | 250 |
| HPV45 | E1 | 11 | 250 |
| HPV45 | E1 | 10 | 238 |
| HPV45 | E1 | 11 | 238 |
| HPV45 | E1 | 9 | 60 |
| HPV45 | E1 | 10 | 60 |
| HPV45 | E1 | 11 | 60 |
| HPV45 | E1 | 9 | 391 |
| HPV45 | E1 | 10 | 391 |
| HPV45 | E1 | 11 | 391 |
| HPV45 | E1 | 9 | 67 |
| HPV45 | E1 | 8 | 192 |
| HPV45 | E1 | 9 | 192 |
| HPV45 | E1 | 10 | 192 |
| HPV45 | E1 | 11 | 192 |
| HPV45 | E1 | 11 | 165 |
| HPV45 | E1 | 9 | 407 |
| HPV45 | E1 | 8 | 306 |
| HPV45 | E1 | 9 | 306 |
| HPV45 | E1 | 10 | 306 |
| HPV45 | E1 | 10 | 316 |
| HPV45 | E1 | 8 | 608 |
| HPV45 | E1 | 8 | 171 |
| HPV45 | E1 | 10 | 166 |
| HPV45 | E1 | 8 | 307 |
| HPV45 | E1 | 9 | 307 |
| HPV45 | E1 | 11 | 288 |
| HPV45 | E1 | 8 | 65 |
| HPV45 | E1 | 11 | 65 |
| HPV45 | E1 | 9 | 39 |
| HPV45 | E1 | 10 | 39 |
| HPV45 | E1 | 8 | 224 |
| HPV45 | E1 | 9 | 224 |
| HPV45 | E1 | 10 | 224 |
| HPV45 | E1 | 11 | 224 |
| HPV45 | E1 | 11 | 309 |
| HPV45 | E1 | 8 | 240 |
| HPV45 | E1 | 9 | 240 |
| HPV45 | E1 | 8 | 283 |
| HPV45 | E1 | 9 | 283 |
| HPV45 | E1 | 11 | 283 |
| HPV45 | E1 | 8 | 325 |
| HPV45 | E1 | 9 | 325 |
| HPV45 | E1 | 9 | 635 |
| HPV45 | E1 | 9 | 576 |
| HPV45 | E1 | 10 | 576 |
| HPV45 | E1 | 8 | 522 |
| HPV45 | E1 | 11 | 522 |
| HPV45 | E1 | 11 | 254 |
| HPV45 | E1 | 11 | 372 |
| HPV45 | E2 | 9 | 156 |
| HPV45 | E2 | 10 | 156 |
| HPV45 | E2 | 11 | 156 |
| HPV45 | E2 | 9 | 226 |
| HPV45 | E2 | 11 | 226 |
| HPV45 | E2 | 10 | 234 |
| HPV45 | E2 | 10 | 247 |
| HPV45 | E2 | 8 | 216 |
| HPV45 | E2 | 11 | 216 |
| HPV45 | E2 | 8 | 286 |
| HPV45 | E2 | 9 | 286 |
| HPV45 | E2 | 11 | 286 |
| HPV45 | E2 | 8 | 207 |
| HPV45 | E2 | 10 | 207 |
| HPV45 | E2 | 11 | 141 |
| HPV45 | E2 | 9 | 28 |
| HPV45 | E2 | 11 | 28 |
| HPV45 | E2 | 11 | 204 |
| HPV45 | E2 | 8 | 171 |
| HPV45 | E2 | 8 | 212 |
| HPV45 | E2 | 9 | 212 |
| HPV45 | E2 | 9 | 8 |
| HPV45 | E2 | 10 | 8 |
| HPV45 | E2 | 9 | 148 |
| HPV45 | E2 | 10 | 148 |
| HPV45 | E2 | 8 | 50 |
| HPV45 | E2 | 11 | 50 |
| HPV45 | E2 | 11 | 237 |
| HPV45 | E2 | 10 | 225 |
| HPV45 | E2 | 9 | 70 |
| HPV45 | E2 | 10 | 70 |
| HPV45 | E2 | 8 | 361 |
| HPV45 | E2 | 9 | 36 |
| HPV45 | E2 | 11 | 146 |
| HPV45 | E2 | 8 | 57 |
| HPV45 | E2 | 9 | 57 |
| HPV45 | E2 | 8 | 74 |
| HPV45 | E2 | 10 | 74 |
| HPV45 | E2 | 11 | 74 |
| HPV45 | E2 | 8 | 77 |
| HPV45 | E2 | 9 | 77 |
| HPV45 | E2 | 8 | 72 |
| HPV45 | E2 | 10 | 72 |
| HPV45 | E2 | 8 | 154 |
| HPV45 | E2 | 9 | 154 |
| HPV45 | E2 | 11 | 154 |
| HPV45 | E2 | 11 | 88 |
| HPV45 | E2 | 8 | 14 |
| HPV45 | E2 | 9 | 14 |
| HPV45 | E2 | 8 | 10 |
| HPV45 | E2 | 9 | 256 |
| HPV45 | E2 | 9 | 336 |
| HPV45 | E2 | 11 | 83 |
| HPV45 | E2 | 9 | 341 |
| HPV45 | E2 | 10 | 341 |
| HPV45 | E2 | 8 | 301 |
| HPV45 | E2 | 10 | 301 |
| HPV45 | E2 | 9 | 187 |
| HPV45 | E2 | 9 | 33 |
| HPV45 | E2 | 10 | 33 |
| HPV45 | E2 | 9 | 357 |
| HPV45 | E2 | 10 | 357 |
| HPV45 | E2 | 8 | 109 |
| HPV45 | E2 | 9 | 347 |
| HPV45 | E2 | 9 | 332 |
| HPV45 | E2 | 8 | 265 |

TABLE XIII-continued

HLA-B58 Supermotif Peptides

| 1 | 2 | 3 | 4 |
|---|---|---|---|
| HPV45 | E2 | 9 | 265 |
| HPV45 | E2 | 8 | 289 |
| HPV45 | E2 | 11 | 189 |
| HPV45 | E2 | 11 | 246 |
| HPV45 | E2 | 9 | 90 |
| HPV45 | E2 | 11 | 90 |
| HPV45 | E2 | 11 | 4 |
| HPV45 | E2 | 8 | 15 |
| HPV45 | E2 | 11 | 15 |
| HPV45 | E2 | 9 | 215 |
| HPV45 | E2 | 11 | 275 |
| HPV45 | E2 | 8 | 229 |
| HPV45 | E2 | 9 | 208 |
| HPV45 | E2 | 10 | 276 |
| HPV45 | E2 | 8 | 227 |
| HPV45 | E2 | 10 | 227 |
| HPV45 | E2 | 8 | 155. |
| HPV45 | E2 | 10 | 155 |
| HPV45 | E2 | 11 | 155 |
| HPV45 | E2 | 10 | 51 |
| HPV45 | E2 | 11 | 233 |
| HPV45 | E2 | 8 | 209 |
| HPV45 | E2 | 11 | 209 |
| HPV45 | E2 | 9 | 277 |
| HPV45 | E2 | 9 | 228 |
| HPV45 | E2 | 10 | 214 |
| HPV45 | E2 | 8 | 159 |
| HPV45 | E2 | 9 | 159 |
| HPV45 | E2 | 9 | 353 |
| HPV45 | E2 | 11 | 353 |
| HPV45 | E2 | 10 | 326 |
| HPV45 | E2 | 11 | 326 |
| HPV45 | E2 | 10 | 98 |
| HPV45 | E2 | 11 | 98 |
| HPV45 | E2 | 8 | 313 |
| HPV45 | E2 | 8 | 317 |
| HPV45 | E2 | 10 | 317 |
| HPV45 | E6 | 9 | 63 |
| HPV45 | E6 | 10 | 63 |
| HPV45 | E6 | 8 | 37 |
| HPV45 | E6 | 9 | 37 |
| HPV45 | E6 | 11 | 37 |
| HPV45 | E6 | 8 | 18 |
| HPV45 | E6 | 11 | 18 |
| HPV45 | E6 | 11 | 88 |
| HPV45 | E6 | 8 | 47 |
| HPV45 | E6 | 9 | 47 |
| HPV45 | E6 | 10 | 47 |
| HPV45 | E6 | 8 | 30 |
| HPV45 | E6 | 10 | 30 |
| HPV45 | E6 | 10 | 60 |
| HPV45 | E6 | 9 | 93 |
| HPV45 | E6 | 10 | 93 |
| HPV45 | E6 | 11 | 93 |
| HPV45 | E6 | 9 | 36 |
| HPV45 | E6 | 10 | 36 |
| HPV45 | E6 | 8 | 83 |
| HPV45 | E6 | 11 | 83 |
| HPV45 | E6 | 8 | 95 |
| HPV45 | E6 | 9 | 95 |
| HPV45 | E6 | 9 | 22 |
| HPV45 | E6 | 10 | 22 |
| HPV45 | E6 | 8 | 114 |
| HPV45 | E6 | 8 | 7 |
| HPV45 | E6 | 11 | 7 |
| HPV45 | E6 | 8 | 41 |
| HPV45 | E6 | 9 | 41 |
| HPV45 | E6 | 8 | 23 |
| HPV45 | E6 | 9 | 23 |
| HPV45 | E6 | 11 | 23 |
| HPV45 | E6 | 10 | 28 |
| HPV45 | E6 | 8 | 62 |
| HPV45 | E6 | 10 | 62 |
| HPV45 | E6 | 11 | 62 |
| HPV45 | E6 | 10 | 81 |
| HPV45 | E6 | 9 | 72 |
| HPV45 | E6 | 10 | 72 |
| HPV45 | E7 | 8 | 6 |
| HPV45 | E7 | 10 | 6 |
| HPV45 | E7 | 8 | 41 |
| HPV45 | E7 | 10 | 41 |
| HPV45 | E7 | 9 | 34 |
| HPV45 | E7 | 10 | 78 |
| HPV45 | E7 | 9 | 47 |
| HPV45 | E7 | 11 | 32 |
| HPV45 | E7 | 9 | 95 |
| HPV45 | E7 | 10 | 92 |
| HPV45 | E7 | 10 | 75 |
| HPV45 | E7 | 9 | 54 |
| HPV45 | E7 | 10 | 54 |
| HPV45 | E7 | 8 | S |
| HPV45 | E7 | 9 | 5 |
| HPV45 | E7 | 11 | 5 |
| HPV45 | E7 | 8 | 85 |
| HPV45 | E7 | 11 | 85 |
| HPV45 | E7 | 8 | 80 |
| HPV45 | E7 | 11 | 80 |
| HPV45 | E7 | 9 | 79 |
| HPV45 | E7 | 9 | 93 |
| HPV45 | E7 | 11 | 93 |
| HPV45 | E7 | 8 | 45 |
| HPV45 | E7 | 11 | 45 |
| HPV45 | L1 | 11 | 517 |
| HPV45 | L1 | 10 | 161 |
| HPV45 | L1 | 8 | 523 |
| HPV45 | L1 | 10 | 523 |
| HPV45 | L1 | 11 | 375 |
| HPV45 | L1 | 10 | 518 |
| HPV45 | L1 | 9 | 162 |
| HPV45 | L1 | 8 | 374 |
| HPV45 | L1 | 9 | 409 |
| HPV45 | L1 | 10 | 409 |
| HPV45 | L1 | 9 | 332 |
| HPV45 | L1 | 10 | 332 |
| HPV45 | L1 | 11 | 332 |
| HPV45 | L1 | 11 | 34 |
| HPV45 | L1 | 8 | 155 |
| HPV45 | L1 | 10 | 155 |
| HPV45 | L1 | 11 | 155 |
| HPV45 | L1 | 9 | 229 |
| HPV45 | L1 | 8 | 242 |
| HPV45 | L1 | 10 | 242 |
| HPV45 | L1 | 11 | 461 |
| HPV45 | L1 | 8 | 364 |
| HPV45 | L1 | 10 | 364 |
| HPV45 | L1 | 8 | 296 |
| HPV45 | L1 | 9 | 296 |
| HPV45 | L1 | 9 | 446 |
| HPV45 | L1 | 10 | 446 |
| HPV45 | L1 | 11 | 446 |
| HPV45 | L1 | 8 | 157 |
| HPV45 | L1 | 9 | 157 |
| HPV45 | L1 | 10 | 157 |
| HPV45 | L1 | 8 | 313 |
| HPV45 | L1 | 8 | 121 |
| HPV45 | L1 | 10 | 121 |
| HPV45 | L1 | 9 | 283 |
| HPV45 | L1 | 11 | 283 |
| HPV45 | L1 | 8 | 485 |
| HPV45 | L1 | 10 | 485 |
| HPV45 | L1 | 11 | 237 |
| HPV45 | L1 | 8 | 82 |
| HPV45 | L1 | 11 | 82 |
| HPV45 | L1 | 8 | 233 |
| HPV45 | L1 | 10 | 326 |
| HPV45 | L1 | 11 | 326 |
| HPV45 | L1 | 8 | 64 |
| HPV45 | L1 | 9 | 199 |
| HPV45 | L1 | 11 | 160 |
| HPV45 | L1 | 8 | 62 |

TABLE XIII-continued

HLA-B58 Supermotif Peptides

| 1 | 2 | 3 | 4 |
|---|---|---|---|
| HPV45 | L1 | 10 | 62 |
| HPV45 | L1 | 8 | 422 |
| HPV45 | L1 | 11 | 422 |
| HPV45 | L1 | 8 | 411 |
| HPV45 | L1 | 10 | 411 |
| HPV45 | L1 | 11 | 411 |
| HPV45 | L1 | 9 | 166 |
| HPV45 | L1 | 11 | 166 |
| HPV45 | L1 | 8 | 328 |
| HPV45 | L1 | 9 | 328 |
| HPV45 | L1 | 9 | 344 |
| HPV45 | L1 | 11 | 344 |
| HPV45 | L1 | 10 | 144 |
| HPV45 | L1 | 8 | 413 |
| HPV45 | L1 | 9 | 413 |
| HPV45 | L1 | 11 | 371 |
| HPV45 | L1 | 8 | 69 |
| HPV45 | L1 | 10 | 69 |
| HPV45 | L1 | 11 | 69 |
| HPV45 | L1 | 11 | 1 |
| HPV45 | L1 | 11 | 27 |
| HPV45 | L1 | 10 | 264 |
| HPV45 | L1 | 11 | 264 |
| HPV45 | L1 | 11 | 418 |
| HPV45 | L1 | 8 | 425 |
| HPV45 | L1 | 10 | 425 |
| HPV45 | L1 | 11 | 49 |
| HPV45 | L1 | 9 | 219 |
| HPV45 | L1 | 10 | 219 |
| HPV45 | L1 | 8 | 383 |
| HPV45 | L1 | 11 | 383 |
| HPV45 | L1 | 8 | 516 |
| HPV45 | L1 | 8 | 190 |
| HPV45 | L1 | 8 | 32 |
| HPV45 | L1 | 9 | 80 |
| HPV45 | L1 | 10 | 80 |
| HPV45 | L1 | 11 | 299 |
| HPV45 | L1 | 10 | 508 |
| HPV45 | L1 | 11 | 508 |
| HPV45 | L1 | 11 | 387 |
| HPV45 | L1 | 9 | 440 |
| HPV45 | L1 | 11 | 440 |
| HPV45 | L1 | 10 | 501 |
| HPV45 | L1 | 8 | 87 |
| HPV45 | L1 | 9 | 87 |
| HPV45 | L1 | 11 | 87 |
| HPV45 | L1 | 9 | 253 |
| HPV45 | L1 | 10 | 253 |
| HPV45 | L1 | 10 | 180 |
| HPV45 | L1 | 9 | 290 |
| HPV45 | L1 | 9 | 367 |
| HPV45 | L1 | 8 | 56 |
| HPV45 | L1 | 9 | 265 |
| HPV45 | L1 | 10 | 265 |
| HPV45 | L1 | 11 | 265 |
| HPV45 | L1 | 8 | 158 |
| HPV45 | L1 | 9 | 158 |
| HPV45 | L1 | 8 | 93 |
| HPV45 | L1 | 10 | 93 |
| HPV45 | L1 | 11 | 93 |
| HPV45 | L1 | 9 | 486 |
| HPV45 | L1 | 9 | 426 |
| HPV45 | L1 | 11 | 426 |
| HPV45 | L1 | 11 | 65 |
| HPV45 | L1 | 10 | 521 |
| HPV45 | L1 | 11 | 115 |
| HPV45 | L1 | 10 | 238 |
| HPV45 | L1 | 8 | 368 |
| HPV45 | L1 | 10 | 376 |
| HPV45 | L1 | 9 | 519 |
| HPV45 | L1 | 10 | 35 |
| HPV45 | L1 | 11 | 35 |
| HPV45 | L1 | 8 | 414 |
| HPV45 | L1 | 11 | 414 |
| HPV45 | L1 | 9 | 522 |
| HPV45 | L1 | 11 | 522 |
| HPV45 | L1 | 8 | 163 |
| HPV45 | L1 | 11 | 330 |
| HPV45 | L1 | 9 | 442 |
| HPV45 | L1 | 10 | 442 |
| HPV45 | L1 | 8 | 520 |
| HPV45 | L1 | 11 | 520 |
| HPV45 | L1 | 10 | 462 |
| HPV45 | L1 | 9 | 365 |
| HPV45 | L1 | 11 | 365 |
| HPV45 | L1 | 8 | 329 |
| HPV45 | L1 | 8 | 441 |
| HPV45 | L1 | 10 | 441 |
| HPV45 | L1 | 11 | 441 |
| HPV45 | L1 | 9 | 102 |
| HPV45 | L1 | 11 | 102 |
| HPV45 | L1 | 10 | 44 |
| HPV45 | L1 | 11 | 44 |
| HPV45 | L1 | 8 | 92 |
| HPV45 | L1 | 9 | 92 |
| HPV45 | L1 | 11 | 92 |
| HPV45 | L1 | 8 | 54 |
| HPV45 | L1 | 10 | 54 |
| HPV45 | L1 | 10 | 174 |
| HPV45 | L1 | 8 | 127 |
| HPV45 | L1 | 10 | 196 |
| HPV45 | L1 | 9 | 477 |
| HPV45 | L1 | 9 | 320 |
| HPV45 | L1 | 8 | 393 |
| HPV45 | L1 | 10 | 393 |
| HPV45 | L2 | 9 | 6 |
| HPV45 | L2 | 8 | 381 |
| HPV45 | L2 | 10 | 381 |
| HPV45 | L2 | 8 | 327 |
| HPV45 | L2 | 11 | 327 |
| HPV45 | L2 | 9 | 114 |
| HPV45 | L2 | 10 | 201 |
| HPV45 | L2 | 9 | 382 |
| HPV45 | L2 | 11 | 382 |
| HPV45 | L2 | 8 | 357 |
| HPV45 | L2 | 9 | 423 |
| HPV45 | L2 | 10 | 328 |
| HPV45 | L2 | 11 | 328 |
| HPV45 | L2 | 11 | 303 |
| HPV45 | L2 | 8 | 340 |
| HPV45 | L2 | 10 | 340 |
| HPV45 | L2 | 11 | 340 |
| HPV45 | L2 | 8 | 273 |
| HPV45 | L2 | 10 | 273 |
| HPV45 | L2 | 8 | 343 |
| HPV45 | L2 | 9 | 343 |
| HPV45 | L2 | 11 | 343 |
| HPV45 | L2 | 9 | 109 |
| HPV45 | L2 | 11 | 109 |
| HPV45 | L2 | 10 | 148 |
| HPV45 | L2 | 8 | 456 |
| HPV45 | L2 | 11 | 200 |
| HPV45 | L2 | 9 | 162 |
| HPV45 | L2 | 8 | 296 |
| HPV45 | L2 | 10 | 296 |
| HPV45 | L2 | 11 | 296 |
| HPV45 | L2 | 9 | 122 |
| HPV45 | L2 | 11 | 157 |
| HPV45 | L2 | 8 | 306 |
| HPV45 | L2 | 8 | 368 |
| HPV45 | L2 | 10 | 368 |
| HPV45 | L2 | 8 | 64 |
| HPV45 | L2 | 9 | 64 |
| HPV45 | L2 | 11 | 64 |
| HPV45 | L2 | 10 | 62 |
| HPV45 | L2 | 11 | 62 |
| HPV45 | L2 | 8 | 188 |
| HPV45 | L2 | 10 | 188 |
| HPV45 | L2 | 8 | 25 |
| HPV45 | L2 | 11 | 25 |

TABLE XIII-continued

HLA-B58 Supermotif Peptides

| 1 | 2 | 3 | 4 |
|---|---|---|---|
| HPV45 | L2 | 10 | 206 |
| HPV45 | L2 | 10 | 183 |
| HPV45 | L2 | 9 | 433 |
| HPV45 | L2 | 10 | 433 |
| HPV45 | L2 | 11 | 433 |
| HPV45 | L2 | 8 | 37 |
| HPV45 | L2 | 9 | 37 |
| HPV45 | L2 | 11 | 37 |
| HPV45 | L2 | 8 | 134 |
| HPV45 | L2 | 10 | 134 |
| HPV45 | L2 | 8 | 292 |
| HPV45 | L2 | 9 | 326 |
| HPV45 | L2 | 9 | 338 |
| HPV45 | L2 | 10 | 338 |
| HPV45 | L2 | 10 | 323 |
| HPV45 | L2 | 9 | 210 |
| HPV45 | L2 | 10 | 152 |
| HPV45 | L2 | 11 | 152 |
| HPV45 | L2 | 8 | 143 |
| HPV45 | L2 | 10 | 143 |
| HPV45 | L2 | 10 | 130 |
| HPV45 | L2 | 11 | 130 |
| HPV45 | L2 | 8 | 366 |
| HPV45 | L2 | 10 | 366 |
| HPV45 | L2 | 8 | 40 |
| HPV45 | L2 | 11 | 40 |
| HPV45 | L2 | 9 | 263 |
| HPV45 | L2 | 8 | 287 |
| HPV45 | L2 | 10 | 287 |
| HPV45 | L2 | 8 | 242 |
| HPV45 | L2 | 10 | 242 |
| HPV45 | L2 | 8 | 375 |
| HPV45 | L2 | 11 | 375 |
| HPV45 | L2 | 9 | 392 |
| HPV45 | L2 | 10 | 392 |
| HPV45 | L2 | 8 | 422 |
| HPV45 | L2 | 10 | 422 |
| HPV45 | L2 | 8 | 160 |
| HPV45 | L2 | 9 | 160 |
| HPV45 | L2 | 11 | 160 |
| HPV45 | L2 | 10 | 285 |
| HPV45 | L2 | 9 | 356 |
| HPV45 | L2 | 10 | 138 |
| HPV45 | L2 | 10 | 254 |
| HPV45 | L2 | 11 | 245 |
| HPV45 | L2 | 8 | 378 |
| HPV45 | L2 | 11 | 378 |
| HPV45 | L2 | 8 | 361 |
| HPV45 | L2 | 10 | 361 |
| HPV45 | L2 | 8 | 416 |
| HPV45 | L2 | 9 | 98 |
| HPV45 | L2 | 10 | 98 |
| HPV45 | L2 | 9 | 120 |
| HPV45 | L2 | 11 | 120 |
| HPV45 | L2 | 9 | 420 |
| HPV45 | L2 | 10 | 420 |
| HPV45 | L2 | 8 | 86 |
| HPV45 | L2 | 11 | 86 |
| HPV45 | L2 | 8 | 185 |
| HPV45 | L2 | 11 | 185 |
| HPV45 | L2 | 10 | 267 |
| HPV45 | L2 | 11 | 267 |
| HPV45 | L2 | 8 | 145 |
| HPV45 | L2 | 11 | 216 |
| HPV45 | L2 | 9 | 23 |
| HPV45 | L2 | 10 | 23 |
| HPV45 | L2 | 9 | 172 |
| HPV45 | L2 | 10 | 172 |
| HPV45 | L2 | 11 | 172 |
| HPV45 | L2 | 8 | 5 |
| HPV45 | L2 | 10 | 5 |
| HPV45 | L2 | 8 | 229 |
| HPV45 | L2 | 8 | 11 |
| HPV45 | L2 | 10 | 308 |
| HPV45 | L2 | 8 | 77 |
| HPV45 | L2 | 8 | 339 |
| HPV45 | L2 | 9 | 339 |
| HPV45 | L2 | 11 | 339 |
| HPV45 | L2 | 8 | 394 |
| HPV45 | L2 | 9 | 202 |
| HPV45 | L2 | 8 | 132 |
| HPV45 | L2 | 9 | 132 |
| HPV45 | L2 | 10 | 132 |
| HPV45 | L2 | 10 | 48 |
| HPV45 | L2 | 10 | 246 |
| HPV45 | L2 | 11 | 246 |
| HPV45 | L2 | 9 | 288 |
| HPV45 | L2 | 8 | 211 |
| HPV45 | L2 | 11 | 211 |
| HPV45 | L2 | 9 | 153 |
| HPV45 | L2 | 10 | 153 |
| HPV45 | L2 | 8 | 110 |
| HPV45 | L2 | 10 | 110 |
| HPV45 | L2 | 8 | 383 |
| HPV45 | L2 | 10 | 383 |
| HPV45 | L2 | 10 | 379 |
| HPV45 | L2 | 9 | 362 |
| HPV45 | L2 | 10 | 212 |
| HPV45 | L2 | 8 | 154 |
| HPV45 | L2 | 9 | 154 |
| HPV45 | L2 | 11 | 358 |
| HPV45 | L2 | 8 | 424 |
| HPV45 | L2 | 9 | 380 |
| HPV45 | L2 | 11 | 380 |
| HPV45 | L2 | 8 | 393 |
| HPV45 | L2 | 9 | 393 |
| HPV45 | L2 | 8 | 155 |
| HPV45 | L2 | 10 | 186 |
| HPV45 | L2 | 9 | 268 |
| HPV45 | L2 | 10 | 268 |
| HPV45 | L2 | 11 | 418 |
| HPV45 | L2 | 11 | 238 |
| HPV45 | L2 | 9 | 131 |
| HPV45 | L2 | 10 | 131 |
| HPV45 | L2 | 11 | 131 |
| HPV45 | L2 | 8 | 38 |
| HPV45 | L2 | 10 | 38 |
| HPV45 | L2 | 11 | 261 |
| HPV45 | L2 | 8 | 136 |
| HPV45 | L2 | 10 | 359 |
| HPV45 | L2 | 9 | 135 |
| HPV45 | L2 | 11 | 426 |
| HPV45 | L2 | 10 | 113 |
| HPV45 | L2 | 11 | 2 |
| HPV45 | L2 | 8 | 150 |
| HPV45 | L2 | 8 | 249 |
| HPV45 | L2 | 11 | 249 |
| HPV45 | L2 | 9 | 104 |
| HPV45 | L2 | 10 | 104 |
| HPV45 | L2 | 11 | 104 |
| HPV45 | L2 | 8 | 388 |
| HPV45 | L2 | 9 | 388 |
| HPV45 | L2 | 11 | 388 |
| HPV45 | L2 | 8 | 47 |
| HPV45 | L2 | 11 | 47 |
| HPV45 | L2 | 8 | 350 |
| HPV45 | L2 | 9 | 373 |
| HPV45 | L2 | 10 | 373 |
| HPV45 | L2 | 8 | 385 |
| HPV45 | L2 | 11 | 385 |
| HPV45 | L2 | 8 | 227 |
| HPV45 | L2 | 10 | 227 |
| HPV45 | L2 | 8 | 401 |
| HPV56 | E2 | 8 | 13 |
| HPV56 | E2 | 9 | 13 |
| HPV56 | E2 | 10 | 13 |
| HPV56 | E2 | 9 | 92 |
| HPV56 | E2 | 10 | 92 |
| HPV56 | E2 | 11 | 92 |
| HPV56 | E2 | 8 | 195 |

TABLE XIII-continued

HLA-B58 Supermotif Peptides

| 1 | 2 | 3 | 4 |
|---|---|---|---|
| HPV56 | E2 | 11 | 195 |
| HPV56 | E2 | 9 | 140 |
| HPV56 | E2 | 11 | 140 |
| HPV56 | E2 | 8 | 39 |
| HPV56 | E2 | 10 | 117 |
| HPV56 | E2 | 11 | 117 |
| HPV56 | E2 | 9 | 134 |
| HPV56 | E2 | 8 | 23 |
| HPV56 | E2 | 8 | 288 |
| HPV56 | E2 | 11 | 288 |
| HPV56 | E2 | 9 | 66 |
| HPV56 | E2 | 10 | 66 |
| HPV56 | E2 | 11 | 66 |
| HPV56 | E2 | 11 | 201 |
| HPV56 | E2 | 10 | 20 |
| HPV56 | E2 | 11 | 20 |
| HPV56 | E2 | 8 | 11 |
| HPV56 | E2 | 10 | 11 |
| HPV56 | E2 | 11 | 11 |
| HPV56 | E2 | 8 | 9 |
| HPV56 | E2 | 10 | 9 |
| HPV56 | E2 | 11 | 258 |
| HPV56 | E2 | 8 | 233 |
| HPV56 | E2 | 10 | 163 |
| HPV56 | E2 | 11 | 108 |
| HPV56 | E2 | 8 | 295 |
| HPV56 | E2 | 9 | 295 |
| HPV56 | E2 | 10 | 295 |
| HPV56 | E2 | 11 | 25 |
| HPV56 | E2 | 8 | 46 |
| HPV56 | E2 | 9 | 292 |
| HPV56 | E2 | 11 | 292 |
| HPV56 | E2 | 9 | 216 |
| HPV56 | E2 | a | 14 |
| HPV56 | E2 | 9 | 14 |
| HPV56 | E2 | 10 | 196 |
| HPV56 | E2 | 8 | 143 |
| HPV56 | E2 | 11 | 143 |
| HPV56 | E2 | 10 | 144 |
| HPV56 | E2 | 9 | 272 |
| HPV56 | E2 | 10 | 272 |
| HPV56 | E2 | 9 | 169 |
| HPV56 | E2 | 10 | 169 |
| HPV56 | E2 | 11 | 169 |
| HPV56 | E2 | 10 | 26 |
| HPV56 | E2 | 8 | 271 |
| HPV56 | E2 | 10 | 271 |
| HPV56 | E2 | 11 | 271 |
| HPV56 | E2 | 10 | 168 |
| HPV56 | E2 | 11 | 168 |
| HPV56 | E2 | 8 | 170 |
| HPV56 | E2 | 9 | 170 |
| HPV56 | E2 | 10 | 170 |
| HPV56 | E2 | 9 | 27 |
| HPV56 | E2 | 11 | 27 |
| HPV56 | E2 | 11 | 167 |
| HPV56 | E2 | 8 | 165 |
| HPV56 | E2 | 9 | 164 |
| HPV56 | E2 | 8 | 75 |
| HPV56 | E2 | 11 | 179 |
| HPV56 | E2 | 10 | 150 |
| HPV56 | E2 | 9 | 142 |
| HPV56 | E2 | 10 | 35 |
| HPV56 | E2 | 11 | 35 |
| HPV56 | E2 | 9 | 270 |
| HPV56 | E2 | 11 | 270 |
| HPV56 | E2 | 8 | 278 |
| HPV56 | E2 | 8 | 111 |
| HPV56 | E2 | 11 | 111 |
| HPV56 | E6 | 11 | 89 |
| HPV56 | E6 | 8 | 50 |
| HPV56 | E6 | 8 | 92 |
| HPV56 | E6 | 11 | 92 |
| HPV56 | E6 | 8 | 48 |
| HPV56 | E6 | 9 | 48 |
| HPV56 | E6 | 10 | 48 |
| HPV56 | E6 | 10 | 131 |
| HPV56 | E6 | 9 | 94 |
| HPV56 | E6 | 10 | 94 |
| HPV56 | E6 | 11 | 94 |
| HPV56 | E6 | 10 | 31 |
| HPV56 | E6 | 9 | 18 |
| HPV56 | E6 | 10 | 18 |
| HPV56 | E6 | 8 | 113 |
| HPV56 | E6 | 9 | 40 |
| HPV56 | E6 | 10 | 40 |
| HPV56 | E6 | 11 | 110 |
| HPV56 | E6 | 11 | 145 |
| HPV56 | E6 | 8 | 42 |
| HPV56 | E6 | 9 | 13 |
| HPV56 | E6 | 10 | 13 |
| HPV56 | E6 | 10 | 146 |
| HPV56 | E6 | 9 | 135 |
| HPV56 | E6 | 8 | 63 |
| HPV56 | E6 | 9 | 63 |
| HPV56 | E6 | 10 | 63 |
| HPV56 | E6 | 11 | 63 |
| HPV56 | E6 | 9 | 73 |
| HPV56 | E6 | 10 | 73 |
| HPV56 | E6 | 8 | 84 |
| HPV56 | E6 | 11 | 84 |
| HPV56 | E7 | 11 | 30 |
| HPV56 | E7 | 9 | 92 |
| HPV56 | E7 | 11 | 92 |
| HPV56 | E7 | 8 | 56 |
| HPV56 | E7 | 9 | 15 |
| HPV56 | E7 | 9 | 94 |
| HPV56 | E7 | 8 | 6 |
| HPV56 | E7 | 10 | 6 |
| HPV56 | E7 | 8 | 52 |
| HPV56 | E7 | 9 | 52 |
| HPV56 | E7 | 10 | 52 |
| HPV56 | E7 | 11 | 49 |
| HPV56 | E7 | 9 | 77 |
| HPV56 | E7 | 10 | 77 |
| HPV56 | E7 | 10 | 31 |
| HPV56 | E7 | 8 | 78 |
| HPV56 | E7 | 9 | 78 |
| HPV56 | L1 | 11 | 58 |
| HPV56 | L1 | 8 | 381 |
| HPV56 | L1 | 10 | 381 |
| HPV56 | L1 | 8 | 327 |
| HPV56 | L1 | 8 | 514 |
| HPV56 | L1 | 8 | 444 |
| HPV56 | L1 | 10 | 444 |
| HPV56 | L1 | 11 | 444 |
| HPV56 | L1 | 10 | 37 |
| HPV56 | L1 | 11 | 37 |
| HPV56 | L1 | 9 | 195 |
| HPV56 | L1 | 8 | 389 |
| HPV56 | L1 | 9 | 389 |
| HPV56 | L1 | 8 | 274 |
| HPV56 | L1 | 9 | 274 |
| HPV56 | L1 | 10 | 274 |
| HPV56 | L1 | 11 | 274 |
| HPV56 | L1 | 10 | 486 |
| HPV56 | L1 | 8 | 176 |
| HPV56 | L1 | 9 | 60 |
| HPV56 | L1 | 10 | 60 |
| HPV56 | L1 | 11 | 60 |
| HPV56 | L1 | 8 | 162 |
| HPV56 | L1 | 9 | 236 |
| HPV56 | L1 | 11 | 236 |
| HPV56 | L1 | 8 | 369 |
| HPV56 | L1 | 10 | 369 |
| HPV56 | L1 | 9 | 337 |
| HPV56 | L1 | 10 | 337 |
| HPV56 | L1 | 11 | 337 |
| HPV56 | L1 | 8 | 249 |
| HPV56 | L1 | 10 | 249 |

TABLE XIII-continued

HLA-B58 Supermotif Peptides

| 1 | 2 | 3 | 4 |
|---|---|---|---|
| HPV56 | L1 | 11 | 249 |
| HPV56 | L1 | 10 | 164 |
| HPV56 | L1 | 11 | 164 |
| HPV56 | L1 | 8 | 303 |
| HPV56 | L1 | 9 | 303 |
| HPV56 | L1 | 9 | 290 |
| HPV56 | L1 | 8 | 488 |
| HPV56 | L1 | 10 | 488 |
| HPV56 | L1 | 9 | 148 |
| HPV56 | L1 | 10 | 148 |
| HPV56 | L1 | 8 | 240 |
| HPV56 | L1 | 9 | 206 |
| HPV56 | L1 | 8 | 25 |
| HPV56 | L1 | 9 | 25 |
| HPV56 | L1 | 10 | 25 |
| HPV56 | L1 | 8 | 331 |
| HPV56 | L1 | 10 | 331 |
| HPV56 | L1 | 11 | 331 |
| HPV56 | L1 | 8 | 73 |
| HPV56 | L1 | 8 | 506 |
| HPV56 | L1 | 9 | 506 |
| HPV56 | L1 | 8 | 71 |
| HPV56 | L1 | 9 | 71 |
| HPV56 | L1 | 10 | 71 |
| HPV56 | L1 | 8 | 378 |
| HPV56 | L1 | 11 | 378 |
| HPV56 | L1 | 10 | 181 |
| HPV56 | L1 | 8 | 414 |
| HPV56 | L1 | 9 | 414 |
| HPV56 | L1 | 10 | 414 |
| HPV56 | L1 | 11 | 414 |
| HPV56 | L1 | 8 | 334 |
| HPV56 | L1 | 8 | 251 |
| HPV56 | L1 | 9 | 251 |
| HPV56 | L1 | 9 | 93 |
| HPV56 | L1 | 10 | 93 |
| HPV56 | L1 | 9 | 474 |
| HPV56 | L1 | 11 | 474 |
| HPV56 | L1 | 8 | 222 |
| HPV56 | L1 | 8 | 78 |
| HPV56 | L1 | 10 | 78 |
| HPV56 | L1 | 8 | 416 |
| HPV56 | L1 | 9 | 416 |
| HPV56 | L1 | 10 | 151 |
| HPV56 | L1 | 9 | 385 |
| HPV56 | L1 | 9 | 439 |
| HPV56 | L1 | 11 | 36 |
| HPV56 | L1 | 9 | 421 |
| HPV56 | L1 | 11 | 421 |
| HPV56 | L1 | 10 | 271 |
| HPV56 | L1 | 11 | 271 |
| HPV56 | L1 | 10 | 376 |
| HPV56 | L1 | 8 | 428 |
| HPV56 | L1 | 10 | 428 |
| HPV56 | L1 | 9 | 91 |
| HPV56 | L1 | 11 | 91 |
| HPV56 | L1 | 9 | 226 |
| HPV56 | L1 | 10 | 226 |
| HPV56 | L1 | 11 | 197 |
| HPV56 | L1 | 11 | 511 |
| HPV56 | L1 | 8 | 41 |
| HPV56 | L1 | 10 | 329 |
| HPV56 | L1 | 8 | 467 |
| HPV56 | L1 | 9 | 467 |
| HPV56 | L1 | 11 | 467 |
| HPV56 | L1 | 8 | 50 |
| HPV56 | L1 | 9 | 50 |
| HPV56 | L1 | 8 | 522 |
| HPV56 | L1 | 9 | 260 |
| HPV56 | L1 | 10 | 260 |
| HPV56 | L1 | 9 | 297 |
| HPV56 | L1 | 11 | 297 |
| HPV56 | L1 | 9 | 349 |
| HPV56 | L1 | 11 | 349 |
| HPV56 | L1 | 11 | 519 |
| HPV56 | L1 | 10 | 372 |
| HPV56 | L1 | 8 | 65 |
| HPV56 | L1 | 9 | 272 |
| HPV56 | L1 | 10 | 272 |
| HPV56 | L1 | 11 | 272 |
| HPV56 | L1 | 8 | 417 |
| HPV56 | L1 | 11 | 417 |
| HPV56 | L1 | 10 | 520 |
| HPV56 | L1 | 8 | 100 |
| HPV56 | L1 | 10 | 100 |
| HPV56 | L1 | 9 | 165 |
| HPV56 | L1 | 10 | 165 |
| HPV56 | L1 | 11 | 74 |
| HPV56 | L1 | 10 | 379 |
| HPV56 | L1 | 8 | 261 |
| HPV56 | L1 | 9 | 261 |
| HPV56 | L1 | 11 | 261 |
| HPV56 | L1 | 9 | 489 |
| HPV56 | L1 | 9 | 373 |
| HPV56 | L1 | 9 | 380 |
| HPV56 | L1 | 11 | 380 |
| HPV56 | L1 | 11 | 335 |
| HPV56 | L1 | 9 | 445 |
| HPV56 | L1 | 10 | 445 |
| HPV56 | L1 | 8 | 215 |
| HPV56 | L1 | 9 | 215 |
| HPV56 | L1 | 10 | 215 |
| HPV56 | L1 | 11 | 215 |
| HPV56 | L1 | 9 | 370 |
| HPV56 | L1 | 8 | 326 |
| HPV56 | L1 | 9 | 326 |
| HPV56 | L1 | 9 | 513 |
| HPV56 | L1 | 9 | 443 |
| HPV56 | L1 | 11 | 443 |
| HPV56 | L1 | 8 | 99 |
| HPV56 | L1 | 9 | 99 |
| HPV56 | L1 | 11 | 99 |
| HPV56 | L1 | 10 | 53 |
| HPV56 | L1 | 11 | 53 |
| HPV56 | L1 | 10 | 87 |
| HPV56 | L1 | 9 | 214 |
| HPV56 | L1 | 10 | 214 |
| HPV56 | L1 | 11 | 214 |
| HPV56 | L1 | 8 | 134 |
| HPV56 | L2 | 9 | 222 |
| HPV56 | L2 | 10 | 222 |
| HPV56 | L2 | 9 | 383 |
| HPV56 | L2 | 11 | 383 |
| HPV56 | L2 | 11 | 303 |
| HPV56 | L2 | 10 | 246 |
| HPV56 | L2 | 11 | 246 |
| HPV56 | L2 | 9 | 367 |
| HPV56 | L2 | 10 | 14 |
| HPV56 | L2 | 9 | 6 |
| HPV56 | L2 | 11 | 260 |
| HPV56 | L2 | 10 | 357 |
| HPV56 | L2 | 11 | 357 |
| HPV56 | L2 | 8 | 169 |
| HPV56 | L2 | 9 | 114 |
| HPV56 | L2 | 9 | 109 |
| HPV56 | L2 | 11 | 109 |
| HPV56 | L2 | 10 | 94 |
| HPV56 | L2 | 11 | 94 |
| HPV56 | L2 | 10 | 398 |
| HPV56 | L2 | 11 | 398 |
| HPV56 | L2 | 8 | 457 |
| HPV56 | L2 | 8 | 437 |
| HPV56 | L2 | 9 | 437 |
| HPV56 | L2 | 8 | 382 |
| HPV56 | L2 | 10 | 382 |
| HPV56 | L2 | 11 | 200 |
| HPV56 | L2 | 8 | 296 |
| HPV56 | L2 | 10 | 296 |
| HPV56 | L2 | 9 | 122 |
| HPV56 | L2 | 8 | 287 |

TABLE XIII-continued

HLA-B58 Supermotif Peptides

| 1 | 2 | 3 | 4 |
|---|---|---|---|
| HPV56 | L2 | 10 | 287 |
| HPV56 | L2 | 9 | 51 |
| HPV56 | L2 | 8 | 314 |
| HPV56 | L2 | 10 | 314 |
| HPV56 | L2 | 8 | 64 |
| HPV56 | L2 | 9 | 64 |
| HPV56 | L2 | 11 | 64 |
| HPV56 | L2 | 10 | 48 |
| HPV56 | L2 | 8 | 75 |
| HPV56 | L2 | 10 | 75 |
| HPV56 | L2 | 9 | 434 |
| HPV56 | L2 | 10 | 434 |
| HPV56 | L2 | 11 | 434 |
| HPV56 | L2 | 8 | 25 |
| HPV56 | L2 | 11 | 25 |
| HPV56 | L2 | 8 | 258 |
| HPV56 | L2 | 10 | 206 |
| HPV56 | L2 | 8 | 62 |
| HPV56 | L2 | 10 | 62 |
| HPV56 | L2 | 11 | 62 |
| HPV56 | L2 | 10 | 60 |
| HPV56 | L2 | 8 | 310 |
| HPV56 | L2 | 10 | 310 |
| HPV56 | L2 | 11 | 310 |
| HPV56 | L2 | 8 | 190 |
| HPV56 | L2 | 11 | 190 |
| HPV56 | L2 | 10 | 221 |
| HPV56 | L2 | 11 | 221 |
| HPV56 | L2 | 9 | 326 |
| HPV56 | L2 | 10 | 323 |
| HPV56 | L2 | 9 | 210 |
| HPV56 | L2 | 8 | 182 |
| HPV56 | L2 | 11 | 182 |
| HPV56 | L2 | 11 | 157 |
| HPV56 | L2 | 8 | 143 |
| HPV56 | L2 | 10 | 143 |
| HPV56 | L2 | 10 | 130 |
| HPV56 | L2 | 11 | 130 |
| HPV56 | L2 | 8 | 229 |
| HPV56 | L2 | 8 | 38 |
| HPV56 | L2 | 10 | 38 |
| HPV56 | L2 | 8 | 263 |
| HPV56 | L2 | 9 | 263 |
| HPV56 | L2 | 10 | 338 |
| HPV56 | L2 | 11 | 338 |
| HPV56 | L2 | 10 | 380 |
| HPV56 | L2 | 9 | 23 |
| HPV56 | L2 | 10 | 23 |
| HPV56 | L2 | 11 | 361 |
| HPV56 | L2 | 9 | 342 |
| HPV56 | L2 | 10 | 342 |
| HPV56 | L2 | 11 | 342 |
| HPV56 | L2 | 9 | 385 |
| HPV56 | L2 | 8 | 239 |
| HPV56 | L2 | 10 | 239 |
| HPV56 | L2 | 11 | 239 |
| HPV56 | L2 | 10 | 285 |
| HPV56 | L2 | 8 | 86 |
| HPV56 | L2 | 11 | 86 |
| HPV56 | L2 | 11 | 245 |
| HPV56 | L2 | 10 | 267 |
| HPV56 | L2 | 11 | 267 |
| HPV56 | L2 | 10 | 78 |
| HPV56 | L2 | 9 | 98 |
| HPV56 | L2 | 10 | 98 |
| HPV56 | L2 | 9 | 410 |
| HPV56 | L2 | 10 | 410 |
| HPV56 | L2 | 8 | 185 |
| HPV56 | L2 | 11 | 185 |
| HPV56 | L2 | 8 | 145 |
| HPV56 | L2 | 10 | 328 |
| HPV56 | L2 | 11 | 328 |
| HPV56 | L2 | 10 | 421 |
| HPV56 | L2 | 11 | 421 |
| HPV56 | L2 | 8 | 364 |
| HPV56 | L2 | 10 | 364 |
| HPV56 | L2 | 9 | 172 |
| HPV56 | L2 | 10 | 172 |
| HPV56 | L2 | 11 | 172 |
| HPV56 | L2 | 8 | 306 |
| HPV56 | L2 | 10 | 306 |
| HPV56 | L2 | 8 | 11 |
| HPV56 | L2 | 8 | 5 |
| HPV56 | L2 | 10 | 5 |
| HPV56 | L2 | 11 | 370 |
| HPV56 | L2 | 9 | 339 |
| HPV56 | L2 | 10 | 339 |
| HPV56 | L2 | 11 | 13 |
| HPV56 | L2 | 8 | 435 |
| HPV56 | L2 | 9 | 435 |
| HPV56 | L2 | 10 | 435 |
| HPV56 | L2 | 11 | 435 |
| HPV56 | L2 | 10 | 362 |
| HPV56 | L2 | 8 | 132 |
| HPV56 | L2 | 9 | 132 |
| HPV56 | L2 | 10 | 132 |
| HPV56 | L2 | 9 | 153 |
| HPV56 | L2 | 10 | 153 |
| HPV56 | L2 | 11 | 153 |
| HPV56 | L2 | 8 | 211 |
| HPV56 | L2 | 11 | 211 |
| HPV56 | L2 | 8 | 133 |
| HPV56 | L2 | 9 | 133 |
| HPV56 | L2 | 11 | 133 |
| HPV56 | L2 | 11 | 147 |
| HPV56 | L2 | 8 | 110 |
| HPV56 | L2 | 10 | 110 |
| HPV56 | L2 | 8 | 154 |
| HPV56 | L2 | 9 | 154 |
| HPV56 | L2 | 10 | 154 |
| HPV56 | L2 | 9 | 79 |
| HPV56 | L2 | 10 | 212 |
| HPV56 | L2 | 11 | 212 |
| HPV56 | L2 | 10 | 183 |
| HPV56 | L2 | 8 | 134 |
| HPV56 | L2 | 10 | 134 |
| HPV56 | L2 | 10 | 148 |
| HPV56 | L2 | 11 | 414 |
| HPV56 | L2 | 8 | 390 |
| HPV56 | L2 | 10 | 186 |
| HPV56 | L2 | 10 | 261 |
| HPV56 | L2 | 11 | 261 |
| HPV56 | L2 | 9 | 131 |
| HPV56 | L2 | 10 | 131 |
| HPV56 | L2 | 11 | 131 |
| HPV56 | L2 | 8 | 386 |
| HPV56 | L2 | 11 | 386 |
| HPV56 | L2 | 8 | 136 |
| HPV56 | L2 | 9 | 288 |
| HPV56 | L2 | 9 | 135 |
| HPV56 | L2 | 11 | 2 |
| HPV56 | L2 | 8 | 280 |
| HPV56 | L2 | 8 | 270 |
| HPV56 | L2 | 10 | 270 |
| HPV56 | L2 | 11 | 270 |
| HPV56 | L2 | 8 | 366 |
| HPV56 | L2 | 10 | 366 |
| HPV56 | L2 | 8 | 249 |
| HPV56 | L2 | 10 | 152 |
| HPV56 | L2 | 11 | 152 |
| HPV56 | L2 | 8 | 389 |
| HPV56 | L2 | 9 | 389 |
| HPV56 | L2 | 11 | 236 |
| HPV56 | L2 | 9 | 104 |
| HPV56 | L2 | 10 | 104 |
| HPV56 | L2 | 8 | 84 |
| HPV56 | L2 | 9 | 84 |
| HPV56 | L2 | 10 | 84 |
| HPV56 | L2 | 8 | 40 |
| HPV56 | L2 | 11 | 40 |

TABLE XIII-continued

HLA-B58 Supermotif Peptides

| 1 | 2 | 3 | 4 |
|---|---|---|---|
| HPV56 | L2 | 8 | 351 |
| HPV56 | L2 | 11 | 351 |
| HPV56 | L2 | 8 | 402 |
| SF 1168117 v1 | | | |

TABLE XIII A

HPV6A
HLA-B58 Supermotif Peptides

| 2 | 3 | 4 |
|---|---|---|
| E6 | 9 | 62 |
| L1 | 9 | 234 |
| L1 | 10 | 234 |
| L1 | 11 | 234 |
| L2 | 10 | 329 |
| L2 | 11 | 329 |
| E5 | 8 | 9 |
| E5 | 9 | 9 |
| E5 | 10 | 9 |
| E1 | 11 | 206 |
| E1 | 10 | 318 |
| L2 | 9 | 340 |
| L2 | 10 | 340 |
| E4 | 8 | 2 |
| E4 | 10 | 2 |
| E4 | 11 | 2 |
| E2 | 11 | 322 |
| L2 | 9 | 288 |
| L1 | 9 | 36 |
| E6 | 8 | 6 |
| E6 | 11 | 6 |
| E1 | 11 | 330 |
| E2 | 10 | 197 |
| L1 | 9 | 342 |
| L1 | 11 | 22 |
| E1 | 11 | 296 |
| E4 | 9 | 61 |
| L2 | 10 | 14 |
| E1 | 8 | 525 |
| E1 | 9 | 525 |
| E6 | 11 | 10 |
| E1 | 10 | 77 |
| E1 | 11 | 77 |
| E6 | 11 | 64 |
| E1 | 9 | 234 |
| E1 | 11 | 234 |
| E2 | 8 | 124 |
| E2 | 9 | 124 |
| E2 | 10 | 124 |
| E2 | 11 | 124 |
| L1 | 9 | 157 |
| L1 | 10 | 341 |
| E1 | 8 | 406 |
| L1 | 9 | 374 |
| L1 | 10 | 374 |
| E7 | 9 | 71 |
| E1 | 10 | 14 |
| E1 | 11 | 14 |
| E6 | 8 | 131 |
| E6 | 11 | 131 |
| E2 | 8 | 9 |
| E2 | 10 | 9 |
| E2 | 11 | 9 |
| E1 | 8 | 524 |
| E1 | 9 | 524 |
| E1 | 10 | 524 |
| L1 | 9 | 24 |
| L1 | 10 | 24 |
| L1 | 11 | 24 |
| E2 | 8 | 260 |
| L2 | 10 | 204 |
| E1 | 9 | 42 |
| E1 | 10 | 42 |
| E1 | 9 | 134 |
| L2 | 11 | 266 |
| E1 | 8 | 387 |
| E1 | 9 | 53 |
| E7 | 8 | 62 |
| E1 | 9 | 353 |
| E1 | 10 | 353 |
| E7 | 9 | 44 |
| E7 | 11 | 44 |
| E7 | 10 | 31 |
| E2 | 9 | 143 |
| E2 | 10 | 143 |
| E2 | 8 | 141 |
| E2 | 11 | 141 |
| L2 | 10 | 344 |
| L1 | 9 | 198 |
| E1 | 9 | 481 |
| E1 | 11 | 481 |
| E1 | 10 | 73 |
| L1 | 8 | 331 |
| L1 | 10 | 331 |
| L2 | 11 | 369 |
| E1 | 8 | 534 |
| L1 | 11 | 411 |
| E1 | 9 | 71 |
| E1 | 9 | 178 |
| E2 | 11 | 174 |
| L2 | 9 | 274 |
| E1 | 10 | 250 |
| E1 | 8 | 143 |
| E2 | 8 | 66 |
| E2 | 10 | 66 |
| L2 | 8 | 173 |
| E1 | 11 | 336 |
| L1 | 9 | 299 |
| L1 | 10 | 299 |
| L1 | 11 | 299 |
| E1 | 11 | 100 |
| E1 | 8 | 373 |
| E1 | 8 | 103 |
| E1 | 11 | 103 |
| E2 | 8 | 80 |
| E2 | 10 | 80 |
| E2 | 8 | 293 |
| E2 | 10 | 293 |
| E4 | 11 | 55 |
| E2 | 11 | 39 |
| E7 | 10 | 73 |
| E7 | 11 | 73 |
| E6 | 9 | 92 |
| E6 | 10 | 92 |
| E6 | 11 | 92 |
| L2 | 8 | 135 |
| L2 | 10 | 135 |
| E4 | 9 | 75 |
| L1 | 11 | 206 |
| L1 | 8 | 80 |
| L1 | 9 | 80 |
| L2 | 9 | 442 |
| L2 | 11 | 442 |
| L1 | 10 | 49 |
| L1 | 11 | 49 |
| L1 | 8 | 450 |
| L1 | 10 | 450 |
| E1 | 9 | 587 |
| L1 | 8 | 202 |
| L2 | 8 | 314 |
| L2 | 10 | 314 |
| E1 | 8 | 11 |
| E1 | 9 | 11 |
| E1 | 10 | 11 |

TABLE XIII A-continued

HPV6A
HLA-B58 Supermotif Peptides

| 2 | 3 | 4 |
|---|---|---|
| L2 | 10 | 431 |
| L2 | 11 | 431 |
| L1 | 8 | 275 |
| L2 | 10 | 62 |
| L2 | 11 | 62 |
| E1 | 10 | 431 |
| L2 | 10 | 48 |
| L1 | 10 | 293 |
| L1 | 11 | 293 |
| L2 | 11 | 303 |
| E1 | 10 | 632 |
| E1 | 8 | 88 |
| E1 | 11 | 88 |
| E2 | 8 | 179 |
| E2 | 10 | 179 |
| E2 | 11 | 189 |
| E1 | 8 | 191 |
| E1 | 9 | 191 |
| L2 | 8 | 215 |
| L2 | 10 | 215 |
| L2 | 11 | 215 |
| L2 | 8 | 25 |
| L2 | 11 | 25 |
| L2 | 8 | 64 |
| L2 | 9 | 64 |
| L2 | 11 | 64 |
| E1 | 8 | 436 |
| E1 | 9 | 436 |
| E1 | 11 | 436 |
| E1 | 11 | 145 |
| E7 | 9 | 85 |
| L1 | 9 | 407 |
| L1 | 10 | 407 |
| L2 | 10 | 413 |
| E1 | 8 | 467 |
| E1 | 10 | 467 |
| E1 | 11 | 467 |
| E1 | 9 | 147 |
| L2 | 8 | 75 |
| L1 | 9 | 222 |
| L1 | 10 | 222 |
| E5 | 8 | 11 |
| E5 | 10 | 11 |
| E5 | 11 | 11 |
| E4 | 8 | 90 |
| E4 | 10 | 90 |
| E1 | 9 | 415 |
| E1 | 8 | 189 |
| E1 | 10 | 189 |
| E1 | 11 | 189 |
| E2 | 8 | 330 |
| L1 | 8 | 35 |
| L1 | 10 | 35 |
| E2 | 9 | 338 |
| E2 | 10 | 338 |
| E1 | 10 | 246 |
| E1 | 11 | 246 |
| E2 | 9 | 149 |
| E2 | 10 | 149 |
| E2 | 11 | 149 |
| E1 | 11 | 176 |
| E6 | 8 | 25 |
| E6 | 9 | 25 |
| L1 | 8 | 387 |
| L1 | 11 | 387 |
| E4 | 10 | 26 |
| L2 | 8 | 306 |
| E1 | 9 | 581 |
| L2 | 11 | 149 |
| E5 | 9 | 8 |
| E5 | 10 | 8 |
| E5 | 11 | 8 |
| L2 | 8 | 40 |
| L2 | 11 | -40 |
| E1 | 9 | 98 |
| E1 | 11 | 376 |
| E5 | 8 | 22 |
| E5 | 10 | 22 |
| E5 | 11 | 22 |
| L2 | 8 | 326 |
| L2 | 10 | 326 |
| L2 | 8 | 287 |
| L2 | 10 | 287 |
| L2 | 11 | 180 |
| E1 | 9 | 32 |
| E5 | 10 | 37 |
| E5 | 11 | 37 |
| E1 | 8 | 248 |
| E1 | 9 | 248 |
| E1 | 8 | 492 |
| E1 | 9 | 492 |
| E1 | 10 | 500 |
| E1 | 11 | 500 |
| E1 | 8 | 327 |
| L2 | 11 | 323 |
| E1 | 8 | 106 |
| E1 | 10 | 106 |
| L2 | 8 | 405 |
| L2 | 8 | 429 |
| E1 | 11 | 56 |
| E1 | 9 | 571 |
| E1 | 10 | 571 |
| L1 | 8 | 376 |
| L1 | 10 | 376 |
| L1 | 11 | 376 |
| E1 | 11 | 341 |
| L2 | 11 | 82 |
| L2 | 9 | 185 |
| L2 | 11 | 185 |
| L2 | 11 | 131 |
| L1 | 10 | 187 |
| L1 | 11 | 187 |
| E4 | 11 | 83 |
| L2 | 8 | 247 |
| E2 | 10 | 45 |
| E1 | 11 | 553 |
| E2 | 8 | 325 |
| E2 | 9 | 325 |
| E2 | 11 | 325 |
| L1 | 9 | 311 |
| L1 | 11 | 311 |
| E6 | 11 | 123 |
| E1 | 10 | 228 |
| E1 | 11 | 228 |
| L1 | 8 | 213 |
| E1 | 10 | 286 |
| E1 | 8 | 484 |
| E1 | 9 | 484 |
| E1 | 11 | 484 |
| E2 | 9 | 84 |
| E2 | 11 | 84 |
| E6 | 10 | 18 |
| E4 | 8 | 42 |
| E1 | 8 | 231 |
| E1 | 9 | 231 |
| L1 | 10 | 56 |
| E2 | 8 | 165 |
| E1 | 8 | 351 |
| E1 | 11 | 351 |
| E4 | 9 | 13 |
| E4 | 10 | 13 |
| E4 | 10 | 60 |
| L1 | 8 | 42 |
| L1 | 10 | 42 |
| L1 | 8 | 378 |
| L1 | 9 | 378 |
| E1 | 10 | 218 |
| L1 | 8 | 439 |

TABLE XIII A-continued

HPV6A
HLA-B58 Supermotif Peptides

| 2 | 3 | 4 |
|---|---|---|
| E2 | 8 | 51 |
| E2 | 9 | 51 |
| E1 | 8 | 458 |
| E1 | 9 | 259 |
| E1 | 10 | 259 |
| E6 | 8 | 22 |
| E6 | 11 | 22 |
| E1 | 9 | 605 |
| E1 | 10 | 605 |
| L1 | 9 | 401 |
| L2 | 8 | 390 |
| L2 | 9 | 390 |
| L2 | 10 | 390 |
| L2 | 8 | 240 |
| L2 | 10 | 240 |
| E1 | 8 | 132 |
| E1 | 11 | 132 |
| E1 | 9 | 358 |
| L2 | 9 | 23 |
| L2 | 10 | 23 |
| E6 | 9 | 121 |
| E1 | 9 | 555 |
| E1 | 10 | 555 |
| E1 | 11 | 555 |
| E5 | 8 | 49 |
| E5 | 9 | 49 |
| E5 | 10 | 49 |
| E5 | 11 | 49 |
| E5 | 11 | 70 |
| E1 | 8 | 268 |
| E1 | 9 | 268 |
| E1 | 10 | 268 |
| E1 | 11 | 268 |
| E1 | 8 | 115 |
| L2 | 8 | 372 |
| E6 | 9 | 38 |
| E6 | 11 | 38 |
| E5 | 8 | 61 |
| E5 | 9 | 61 |
| E5 | 10 | 61 |
| L1 | 10 | 233 |
| L1 | 11 | 233 |
| E4 | 8 | 1 |
| E4 | 9 | 1 |
| E4 | 11 | 1 |
| L2 | 8 | 87 |
| L2 | 11 | 87 |
| L1 | 11 | 383 |
| E1 | 10 | 546 |
| E1 | 11 | 489 |
| L2 | 8 | 115 |
| E2 | 9 | 71 |
| E2 | 8 | 249 |
| E2 | 11 | 249 |
| E6 | 8 | 36 |
| E6 | 9 | 36 |
| E6 | 11 | 36 |
| E1 | 8 | 607 |
| E1 | 11 | 607 |
| L2 | 8 | 270 |
| L2 | 10 | 270 |
| L2 | 11 | 270 |
| E1 | 10 | 389 |
| E6 | 9 | 5 |
| E1 | 11 | 600 |
| E1 | 8 | 270 |
| E1 | 9 | 270 |
| E1 | 10 | 270 |
| E1 | 11 | 270 |
| L1 | 8 | 352 |
| L1 | 11 | 352 |
| E4 | 9 | 57 |
| E4 | 10 | 57 |
| E1 | 8 | 59 |
| E1 | 9 | 59 |
| E1 | 8 | 395 |
| E1 | 9 | 395 |
| E2 | 9 | 279 |
| E2 | 10 | 279 |
| E1 | 8 | 634 |
| E2 | 8 | 281 |
| E2 | 10 | 281 |
| E1 | 8 | 504 |
| E1 | 11 | 504 |
| E2 | 9 | 22 |
| E2 | 10 | 22 |
| L2 | 8 | 38 |
| L2 | 10 | 38 |
| E1 | 11 | 96 |
| E2 | 8 | 127 |
| E2 | 11 | 127 |
| L1 | 8 | 289 |
| L2 | 9 | 385 |
| L2 | 10 | 237 |
| L2 | 11 | 237 |
| L2 | 8 | 124 |
| L2 | 9 | 285 |
| L2 | 10 | 285 |
| L2 | 8 | 139 |
| E5 | 8 | 78 |
| E5 | 9 | 78 |
| E5 | 10 | 78 |
| E2 | 8 | 216 |
| E2 | 11 | 196 |
| L2 | 9 | 99 |
| L2 | 10 | 99 |
| L1 | 8 | 4 |
| L2 | 8 | 80 |
| L1 | 9 | 391 |
| L1 | 11 | 391 |
| L2 | 10 | 163 |
| L2 | 9 | 408 |
| E2 | 9 | 354 |
| E2 | 10 | 354 |
| L2 | 8 | 183 |
| L2 | 11 | 183 |
| E4 | 8 | 67 |
| L1 | 11 | 426 |
| L2 | 9 | 359 |
| L1 | 8 | 90 |
| L2 | 8 | 328 |
| L2 | 11 | 328 |
| E1 | 10 | 636 |
| E1 | 11 | 636 |
| L1 | 8 | 177 |
| L1 | 10 | 177 |
| L1 | 11 | 177 |
| E1 | 11 | 399 |
| L2 | 8 | 400 |
| E1 | 8 | 314 |
| E1 | 9 | 314 |
| E1 | 10 | 314 |
| L1 | 10 | 466 |
| E2 | 9 | 245 |
| L1 | 9 | 210 |
| L1 | 11 | 210 |
| E2 | 8 | 103 |
| E2 | 11 | 233 |
| E1 | 10 | 128 |
| E1 | 8 | 344 |
| E1 | 8 | 205 |
| E1 | 8 | 391 |
| L1 | 9 | 259 |
| L2 | 8 | 227 |
| L1 | 10 | 53 |
| L2 | 8 | 11 |
| L2 | 10 | 308 |
| L1 | 8 | 472 |

TABLE XIII A-continued

HPV6A
HLA-B58 Supermotif Peptides

| 2 | 3 | 4 |
|---|---|---|
| L1 | 11 | 334 |
| E1 | 8 | 288 |
| E1 | 11 | 288 |
| E1 | 10 | 324 |
| E1 | 11 | 324 |
| L1 | 9 | 476 |
| E1 | 9 | 293 |
| L1 | 8 | 279 |
| L1 | 9 | 279 |
| L1 | 10 | 279 |
| L1 | 8 | 379 |
| L1 | 11 | 379 |
| L2 | 11 | 111 |
| L2 | 11 | 77 |
| E6 | 11 | 3 |
| L2 | 10 | 181 |
| E2 | 8 | 283 |
| L2 | 11 | 13 |
| E6 | 8 | 9 |
| E2 | 9 | 282 |
| L1 | 11 | 297 |
| E7 | 9 | 32 |
| L1 | 9 | 451 |
| L2 | 9 | 133 |
| L2 | 10 | 133 |
| E1 | 9 | 506 |
| E1 | 10 | 506 |
| L2 | 8 | 391 |
| L2 | 9 | 391 |
| L1 | 11 | 85 |
| L1 | 11 | 38 |
| E1 | 10 | 505 |
| E1 | 11 | 505 |
| L1 | 8 | 37 |
| E2 | 9 | 224 |
| E2 | 8 | 225 |
| E2 | 9 | 200 |
| L1 | 9 | 347 |
| E2 | 8 | 23 |
| E2 | 9 | 23 |
| E2 | 11 | 23 |
| E4 | 8 | 86 |
| E4 | 10 | 86 |
| E2 | 9 | 180 |
| E5 | 8 | 14 |
| E5 | 9 | 14 |
| E5 | 11 | 14 |
| L1 | 10 | 335 |
| L2 | 10 | 374 |
| L2 | 9 | 241 |
| E6 | 10 | 7 |
| E2 | 8 | 201 |
| E1 | 10 | 289 |
| E1 | 11 | 289 |
| E2 | 10 | 190 |
| E1 | 10 | 331 |
| E1 | 11 | 331 |
| L1 | 11 | 7 |
| L1 | 8 | 348 |
| L1 | 11 | 348 |
| E6 | 9 | 40 |
| E1 | 8 | 192 |
| L2 | 8 | 420 |
| L2 | 9 | 420 |
| L2 | 10 | 420 |
| L2 | 8 | 409 |
| L2 | 11 | 409 |
| L2 | 9 | 216 |
| L2 | 10 | 216 |
| E6 | 9 | 8 |
| L2 | 10 | 83 |
| L2 | 11 | 83 |
| L2 | 8 | 186 |
| L2 | 10 | 186 |

TABLE XIII A-continued

HPV6A
HLA-B58 Supermotif Peptides

| 2 | 3 | 4 |
|---|---|---|
| L2 | 8 | 147 |
| L2 | 9 | 147 |
| L2 | 8 | 152 |
| L2 | 9 | 152 |
| L2 | 10 | 132 |
| L2 | 11 | 132 |
| L1 | 10 | 346 |
| E4 | 9 | 85 |
| E4 | 11 | 85 |
| E5 | 8 | 13 |
| E5 | 9 | 13 |
| E5 | 10 | 13 |
| L2 | 11 | 373 |
| L1 | 8 | 280 |
| L1 | 9 | 280 |
| L1 | 9 | 188 |
| L1 | 10 | 188 |
| E5 | 8 | 44 |
| E5 | 9 | 44 |
| E5 | 10 | 44 |
| E5 | 11 | 44 |
| E6 | 8 | 39 |
| E6 | 10 | 39 |
| E1 | 8 | 232 |
| E1 | 11 | 232 |
| L1 | 8 | 223 |
| L1 | 9 | 223 |
| L1 | 11 | 223 |
| E6 | 8 | 142 |
| E1 | 9 | 585 |
| E1 | 11 | 585 |
| E6 | 10 | 11 |
| L2 | 8 | 137 |
| L2 | 10 | 137 |
| E5 | 8 | 62 |
| E5 | 9 | 62 |
| E5 | 11 | 62 |
| L1 | 9 | 332 |
| L2 | 9 | 151 |
| L2 | 10 | 151 |
| L1 | 11 | 345 |
| E4 | 10 | 84 |
| E5 | 9 | 12 |
| E5 | 10 | 12 |
| E5 | 11 | 12 |
| L2 | 9 | 136 |
| L2 | 11 | 136 |
| L2 | 10 | 150 |
| L2 | 11 | 150 |
| E4 | 8 | 76 |
| E6 | 11 | 87 |
| L2 | 8 | 386 |
| E4 | 9 | 91 |
| E1 | 11 | 317 |
| L2 | 8 | 339 |
| L2 | 10 | 339 |
| L2 | 11 | 339 |
| E1 | 10 | 239 |
| L2 | 8 | 97 |
| L2 | 9 | 97 |
| L2 | 11 | 97 |
| E1 | 8 | 291 |
| E1 | 9 | 291 |
| E1 | 11 | 291 |
| E2 | 10 | 64 |
| L1 | 10 | 114 |
| L1 | 8 | 62 |
| L1 | 9 | 62 |
| L1 | 11 | 62 |
| E5 | 8 | 29 |
| E5 | 9 | 29 |
| E2 | 9 | 206 |
| L1 | 10 | 17 |
| L1 | 11 | 17 |

TABLE XIII A-continued

HPV6A
HLA-B58 Supermotif Peptides

| 2 | 3 | 4 |
|---|---|---|
| L2 | 9 | 105 |
| L2 | 10 | 105 |
| E1 | 11 | 92 |
| L1 | 8 | 296 |
| E2 | 10 | 223 |
| E2 | 8 | 199 |
| E2 | 10 | 199 |
| L2 | 10 | 259 |
| L2 | 11 | 144 |
| L2 | 9 | 419 |
| L2 | 10 | 419 |
| L2 | 11 | 419 |
| E7 | 11 | 55 |
| E7 | 8 | 6 |
| E7 | 10 | 6 |
| L2 | 8 | 364 |
| L2 | 9 | 364 |
| L2 | 8 | 165 |
| L2 | 10 | 379 |
| L1 | 8 | 27 |
| L2 | 9 | 146 |
| L2 | 10 | 146 |
| E1 | 10 | 584 |
| L1 | 8 | 97 |
| E2 | 8 | 92 |
| E2 | 10 | 92 |
| E2 | 11 | 92 |
| E6 | 8 | 141 |
| E6 | 9 | 141 |
| E4 | 10 | 72 |
| E6 | 8 | 61 |
| E6 | 10 | 61 |
| L2 | 9 | 349 |
| E6 | 8 | 82 |
| E1 | 11 | 262 |
| E1 | 11 | 76 |
| E6 | 8 | 46 |
| E6 | 9 | 46 |
| E6 | 10 | 46 |
| E2 | 8 | 87 |
| L2 | 8 | 225 |
| L2 | 10 | 225 |
| L2 | 10 | 296 |
| E6 | 8 | 44 |
| E6 | 10 | 44 |
| E6 | 11 | 44 |
| E2 | 9 | 159 |
| E2 | 10 | 159 |
| E2 | 11 | 159 |
| L1 | 9 | 350 |
| L1 | 10 | 350 |
| E2 | 10 | 214 |
| E5 | 9 | 43 |
| E5 | 10 | 43 |
| E5 | 11 | 43 |

TABLE XIII B

HPV6B
HLA-B58 Supermotif Peptides

| 2 | 3 | 4 |
|---|---|---|
| E6 | 9 | 62 |
| L1 | 9 | 234 |
| L1 | 10 | 234 |
| L1 | 11 | 234 |
| L2 | 10 | 329 |
| L2 | 11 | 329 |
| E5A | 8 | 9 |
| E5A | 9 | 9 |

TABLE XIII B-continued

HPV6B
HLA-B58 Supermotif Peptides

| 2 | 3 | 4 |
|---|---|---|
| E5A | 10 | 9 |
| E1 | 11 | 206 |
| E1 | 10 | 318 |
| L2 | 9 | 340 |
| L2 | 10 | 340 |
| E4 | 8 | 12 |
| E4 | 10 | 12 |
| E4 | 11 | 12 |
| L2 | 9 | 288 |
| E2 | 11 | 322 |
| L1 | 9 | 36 |
| E6 | 8 | 6 |
| E6 | 11 | 6 |
| E1 | 11 | 330 |
| E2 | 10 | 197 |
| L1 | 9 | 342 |
| L1 | 11 | 22 |
| E1 | 11 | 296 |
| E4 | 9 | 71 |
| L2 | 10 | 14 |
| E1 | 8 | 525 |
| E1 | 9 | 525 |
| E6 | 11 | 10 |
| E1 | 10 | 77 |
| E1 | 11 | 77 |
| E6 | 11 | 64 |
| E5B | 8 | 20 |
| E5B | 10 | 20 |
| E5B | 11 | 20 |
| E2 | 8 | 124 |
| E2 | 9 | 124 |
| E2 | 10 | 124 |
| E2 | 11 | 124 |
| L1 | 9 | 157 |
| L1 | 10 | 341 |
| E1 | 8 | 406 |
| L1 | 9 | 374 |
| L1 | 10 | 374 |
| E7 | 9 | 71 |
| E1 | 10 | 14 |
| E1 | 11 | 14 |
| E6 | 8 | 131 |
| E6 | 11 | 131 |
| E2 | 8 | 9 |
| E2 | 10 | 9 |
| E2 | 11 | 9 |
| E1 | 8 | 524 |
| E1 | 9 | 524 |
| E1 | 10 | 524 |
| L1 | 9 | 24 |
| L1 | 10 | 24 |
| L1 | 11 | 24 |
| E2 | 9 | 338 |
| E2 | 10 | 338 |
| E2 | 8 | 260 |
| L2 | 10 | 204 |
| E1 | 9 | 42 |
| E1 | 10 | 42 |
| E1 | 9 | 134 |
| L2 | 11 | 266 |
| E1 | 8 | 387 |
| E1 | 9 | 53 |
| E7 | 8 | 62 |
| E1 | 9 | 353 |
| E1 | 10 | 353 |
| E7 | 9 | 44 |
| E7 | 11 | 44 |
| E7 | 10 | 31 |
| L2 | 10 | 344 |
| L1 | 9 | 198 |
| E1 | 9 | 481 |
| E1 | 11 | 481 |
| E1 | 10 | 73 |
| L1 | 8 | 331 |

TABLE XIII B-continued

HPV6B
HLA-B58 Supermotif Peptides

| 2 | 3 | 4 |
|---|---|---|
| L1 | 10 | 331 |
| E5B | 8 | 11 |
| E5B | 9 | 11 |
| E2 | 9 | 143 |
| E2 | 10 | 143 |
| L2 | 11 | 369 |
| E1 | 8 | 534 |
| L1 | 11 | 411 |
| E1 | 9 | 71 |
| E1 | 9 | 178 |
| E2 | 11 | 174 |
| L2 | 9 | 274 |
| E1 | 10 | 250 |
| E1 | 8 | 143 |
| E2 | 8 | 66 |
| E2 | 10 | 66 |
| L2 | 8 | 173 |
| E1 | 11 | 336 |
| L1 | 9 | 299 |
| L1 | 10 | 299 |
| L1 | 11 | 299 |
| E1 | 11 | 100 |
| E1 | 8 | 373 |
| E1 | 8 | 103 |
| E1 | 11 | 103 |
| E2 | 8 | 80 |
| E2 | 10 | 80 |
| E2 | 8 | 293 |
| E2 | 10 | 293 |
| E4 | 11 | 65 |
| E2 | 11 | 39 |
| E7 | 10 | 73 |
| E7 | 11 | 73 |
| E6 | 9 | 92 |
| E6 | 10 | 92 |
| E6 | 11 | 92 |
| L2 | 8 | 135 |
| L2 | 10 | 135 |
| E4 | 9 | 85 |
| L1 | 11 | 206 |
| L1 | 8 | 80 |
| L1 | 9 | 80 |
| L2 | 9 | 442 |
| L2 | 11 | 442 |
| L1 | 10 | 49 |
| L1 | 11 | 49 |
| L2 | 8 | 415 |
| L1 | 8 | 450 |
| L1 | 10 | 450 |
| E1 | 9 | 587 |
| L1 | 8 | 202 |
| E4 | 8 | 2 |
| E4 | 9 | 2 |
| E4 | 10 | 2 |
| L2 | 8 | 314 |
| L2 | 10 | 314 |
| E1 | 8 | 11 |
| E1 | 9 | 11 |
| E1 | 10 | 11 |
| L2 | 10 | 431 |
| L2 | 11 | 431 |
| L1 | 8 | 275 |
| L2 | 10 | 62 |
| L2 | 11 | 62 |
| E1 | 10 | 431 |
| L2 | 10 | 48 |
| L1 | 10 | 293 |
| L1 | 11 | 293 |
| L2 | 11 | 303 |
| E1 | 10 | 632 |
| E1 | 8 | 88 |
| E1 | 11 | 88 |
| E2 | 8 | 179 |
| E2 | 10 | 179 |
| E2 | 11 | 189 |
| E1 | 8 | 191 |
| E1 | 9 | 191 |
| L2 | 8 | 215 |
| L2 | 10 | 215 |
| L2 | 11 | 215 |
| L2 | 8 | 25 |
| L2 | 11 | 25 |
| L2 | 8 | 64 |
| L2 | 9 | 64 |
| L2 | 11 | 64 |
| E1 | 8 | 436 |
| E1 | 9 | 436 |
| E1 | 11 | 436 |
| E1 | 11 | 145 |
| L1 | 9 | 407 |
| L1 | 10 | 407 |
| E7 | 9 | 85 |
| L2 | 11 | 412 |
| E1 | 8 | 467 |
| E1 | 10 | 467 |
| E1 | 11 | 467 |
| E1 | 9 | 147 |
| L1 | 9 | 222 |
| L1 | 10 | 222 |
| E5A | 8 | 11 |
| E5A | 10 | 11 |
| E5A | 11 | 11 |
| E4 | 8 | 100 |
| E4 | 10 | 100 |
| E1 | 9 | 415 |
| E1 | 8 | 189 |
| E1 | 10 | 189 |
| E1 | 11 | 189 |
| E2 | 8 | 330 |
| L1 | 8 | 35 |
| L1 | 10 | 35 |
| E1 | 10 | 246 |
| E1 | 11 | 246 |
| E2 | 9 | 149 |
| E2 | 10 | 149 |
| E2 | 11 | 149 |
| E1 | 11 | 176 |
| E6 | 8 | 25 |
| E6 | 9 | 25 |
| L1 | 8 | 387 |
| L1 | 11 | 387 |
| E4 | 10 | 36 |
| L2 | 8 | 306 |
| E1 | 9 | 581 |
| L2 | 11 | 149 |
| E5A | 9 | 8 |
| E5A | 10 | 8 |
| E5A | 11 | 8 |
| L2 | 8 | 40 |
| L2 | 11 | 40 |
| E1 | 9 | 98 |
| E1 | 11 | 376 |
| E5A | 8 | 22 |
| E5A | 10 | 22 |
| E5A | 11 | 22 |
| L2 | 8 | 326 |
| L2 | 10 | 326 |
| L2 | 8 | 287 |
| L2 | 10 | 287 |
| L2 | 11 | 180 |
| E1 | 9 | 32 |
| E1 | 8 | 248 |
| E1 | 9 | 248 |
| E5A | 10 | 37 |
| E5A | 11 | 37 |
| E1 | 8 | 492 |
| E1 | 9 | 492 |
| E2 | 8 | 356 |

TABLE XIII B-continued

HPV6B
HLA-B58 Supermotif Peptides

| 2 | 3 | 4 |
|---|---|---|
| E2 | 10 | 356 |
| E1 | 10 | 500 |
| E1 | 11 | 500 |
| E1 | 8 | 327 |
| L2 | 11 | 323 |
| E1 | 8 | 106 |
| E1 | 10 | 106 |
| L2 | 8 | 404 |
| L2 | 8 | 429 |
| E1 | 11 | 56 |
| E1 | 9 | 571 |
| E1 | 10 | 571 |
| L1 | 8 | 376 |
| L1 | 10 | 376 |
| L1 | 11 | 376 |
| E1 | 11 | 341 |
| L2 | 11 | 82 |
| L2 | 11 | 131 |
| L1 | 10 | 187 |
| L1 | 11 | 187 |
| E4 | 11 | 93 |
| L2 | 8 | 247 |
| E2 | 10 | 45 |
| E1 | 11 | 553 |
| E2 | 8 | 325 |
| E2 | 9 | 325 |
| E2 | 11 | 325 |
| L1 | 9 | 311 |
| L1 | 11 | 311 |
| E6 | 11 | 123 |
| E1 | 8 | 228 |
| E1 | 10 | 228 |
| E1 | 11 | 228 |
| L1 | 8 | 213 |
| E1 | 10 | 286 |
| E1 | 8 | 484 |
| E1 | 9 | 484 |
| E1 | 11 | 484 |
| E6 | 10 | 18 |
| E4 | 8 | 52 |
| E1 | 8 | 231 |
| E1 | 9 | 231 |
| L1 | 10 | 56 |
| E2 | 8 | 165 |
| E1 | 8 | 351 |
| E1 | 11 | 351 |
| E4 | 9 | 23 |
| E4 | 10 | 23 |
| E4 | 10 | 70 |
| L1 | 8 | 42 |
| L1 | 10 | 42 |
| L1 | 8 | 378 |
| L1 | 9 | 378 |
| E1 | 10 | 218 |
| L1 | 8 | 439 |
| E2 | 8 | 51 |
| E2 | 9 | 51 |
| L2 | 8 | 390 |
| L2 | 9 | 390 |
| E1 | 9 | 259 |
| E1 | 10 | 259 |
| E6 | 8 | 22 |
| E6 | 11 | 22 |
| E1 | 9 | 605 |
| E1 | 10 | 605 |
| L1 | 9 | 401 |
| L2 | 8 | 240 |
| L2 | 10 | 240 |
| E5B | 11 | 3 |
| E1 | 8 | 132 |
| E1 | 11 | 132 |
| E1 | 9 | 358 |
| L2 | 9 | 23 |
| L2 | 10 | 23 |
| E6 | 9 | 121 |
| E1 | 8 | 458 |
| E1 | 9 | 555 |
| E1 | 10 | 555 |
| E1 | 11 | 555 |
| E5A | 8 | 49 |
| E5A | 9 | 49 |
| E5A | 10 | 49 |
| E5A | 11 | 49 |
| E5A | 11 | 70 |
| E1 | 8 | 268 |
| E1 | 9 | 268 |
| E1 | 10 | 268 |
| E1 | 11 | 268 |
| E1 | 8 | 115 |
| L2 | 8 | 372 |
| E6 | 9 | 38 |
| E6 | 11 | 38 |
| E5A | 8 | 61 |
| E5A | 9 | 61 |
| E5A | 10 | 61 |
| L1 | 10 | 233 |
| L1 | 11 | 233 |
| E4 | 8 | 11 |
| E4 | 9 | 11 |
| E4 | 11 | 11 |
| L2 | 8 | 87 |
| L2 | 11 | 87 |
| L1 | 11 | 383 |
| E1 | 10 | 546 |
| E1 | 11 | 489 |
| L2 | 8 | 115 |
| E2 | 9 | 71 |
| E2 | 8 | 249 |
| E2 | 11 | 249 |
| E6 | 8 | 36 |
| E6 | 9 | 36 |
| E6 | 11 | 36 |
| L2 | 8 | 270 |
| L2 | 10 | 270 |
| L2 | 11 | 270 |
| E1 | 10 | 389 |
| E6 | 9 | 5 |
| E1 | 11 | 600 |
| E1 | 8 | 270 |
| E1 | 9 | 270 |
| E1 | 10 | 270 |
| E1 | 11 | 270 |
| L1 | 8 | 352 |
| L1 | 11 | 352 |
| E1 | 8 | 59 |
| E1 | 9 | 59 |
| E1 | 8 | 395 |
| E1 | 9 | 395 |
| E2 | 9 | 279 |
| E2 | 10 | 279 |
| E4 | 9 | 67 |
| E4 | 10 | 67 |
| E1 | 8 | 634 |
| E2 | 8 | 281 |
| E2 | 10 | 281 |
| E1 | 8 | 504 |
| E1 | 11 | 504 |
| E2 | 9 | 22 |
| E2 | 10 | 22 |
| L2 | 8 | 38 |
| L2 | 10 | 38 |
| E1 | 11 | 96 |
| E2 | 8 | 127 |
| E2 | 11 | 127 |
| E1 | 8 | 607 |
| E1 | 11 | 607 |
| L1 | 8 | 289 |
| L2 | 8 | 385 |

TABLE XIII B-continued

HPV6B
HLA-B58 Supermotif Peptides

| 2 | 3 | 4 |
|---|---|---|
| L2 | 10 | 237 |
| L2 | 11 | 237 |
| L2 | 8 | 124 |
| L2 | 9 | 285 |
| L2 | 10 | 285 |
| L2 | 8 | 139 |
| L2 | 8 | 420 |
| L2 | 9 | 420 |
| L2 | 10 | 420 |
| E5A | 8 | 78 |
| E5A | 9 | 78 |
| E5A | 10 | 78 |
| E2 | 8 | 216 |
| E2 | 11 | 196 |
| L2 | 9 | 99 |
| L2 | 10 | 99 |
| L1 | 8 | 4 |
| L2 | 8 | 80 |
| L1 | 9 | 391 |
| L1 | 11 | 391 |
| L2 | 10 | 163 |
| L2 | 9 | 407 |
| E2 | 9 | 354 |
| E2 | 10 | 354 |
| E4 | 8 | 77 |
| L1 | 11 | 426 |
| L2 | 9 | 359 |
| L1 | 8 | 90 |
| L2 | 8 | 183 |
| L2 | 11 | 183 |
| L2 | 8 | 328 |
| L2 | 11 | 328 |
| E1 | 10 | 636 |
| E1 | 11 | 636 |
| L1 | 8 | 177 |
| L1 | 10 | 177 |
| L1 | 11 | 177 |
| E1 | 11 | 399 |
| L2 | 8 | 399 |
| E1 | 8 | 314 |
| E1 | 9 | 314 |
| E1 | 10 | 314 |
| L1 | 10 | 466 |
| E2 | 9 | 245 |
| L1 | 9 | 210 |
| L1 | 11 | 210 |
| E2 | 8 | 103 |
| E2 | 11 | 233 |
| E1 | 10 | 128 |
| L2 | 8 | 75 |
| E1 | 8 | 344 |
| E1 | 8 | 205 |
| E1 | 8 | 391 |
| L1 | 9 | 259 |
| L2 | 8 | 227 |
| L1 | 10 | 53 |
| L2 | 8 | 11 |
| L2 | 10 | 308 |
| L1 | 8 | 472 |
| L1 | 11 | 334 |
| E1 | 8 | 288 |
| E1 | 11 | 288 |
| E2 | 9 | 84 |
| E2 | 11 | 84 |
| E1 | 10 | 324 |
| E1 | 11 | 324 |
| L1 | 9 | 476 |
| E1 | 9 | 293 |
| L1 | 8 | 279 |
| L1 | 9 | 279 |
| L1 | 10 | 279 |
| L1 | 8 | 379 |
| L1 | 11 | 379 |
| L2 | 11 | 111 |
| L2 | 11 | 77 |
| E6 | 11 | 3 |
| L2 | 10 | 181 |
| E2 | 8 | 283 |
| L2 | 11 | 13 |
| E6 | 8 | 9 |
| E2 | 9 | 282 |
| L1 | 11 | 297 |
| E7 | 9 | 32 |
| L1 | 9 | 451 |
| L2 | 9 | 133 |
| L2 | 10 | 133 |
| E1 | 9 | 506 |
| E1 | 10 | 506 |
| E2 | 10 | 323 |
| E2 | 11 | 323 |
| L1 | 11 | 85 |
| L1 | 11 | 38 |
| E1 | 10 | 505 |
| E1 | 11 | 505 |
| L1 | 8 | 37 |
| E2 | 9 | 224 |
| E2 | 8 | 225 |
| E2 | 9 | 200 |
| L1 | 9 | 347 |
| E2 | 8 | 23 |
| E2 | 9 | 23 |
| E2 | 11 | 23 |
| E5A | 8 | 14 |
| E5A | 9 | 14 |
| E5A | 11 | 14 |
| E4 | 8 | 96 |
| E4 | 10 | 96 |
| E2 | 9 | 180 |
| L1 | 10 | 335 |
| L2 | 10 | 374 |
| L2 | 9 | 241 |
| E6 | 10 | 7 |
| E2 | 8 | 201 |
| E1 | 10 | 289 |
| E1 | 11 | 289 |
| E2 | 10 | 190 |
| E1 | 10 | 331 |
| E1 | 11 | 331 |
| L1 | 11 | 7 |
| L1 | 8 | 348 |
| L1 | 11 | 348 |
| E6 | 9 | 40 |
| E1 | 8 | 192 |
| L2 | 8 | 408 |
| L2 | 11 | 408 |
| L2 | 9 | 216 |
| L2 | 10 | 216 |
| E6 | 9 | 8 |
| L2 | 10 | 83 |
| L2 | 11 | 83 |
| L2 | 8 | 186 |
| L2 | 10 | 186 |
| L2 | 8 | 147 |
| L2 | 9 | 147 |
| L2 | 8 | 152 |
| L2 | 9 | 152 |
| L2 | 10 | 132 |
| L2 | 11 | 132 |
| L1 | 10 | 346 |
| E5A | 8 | 13 |
| E5A | 9 | 13 |
| E5A | 10 | 13 |
| E4 | 9 | 95 |
| E4 | 11 | 95 |
| L2 | 11 | 373 |
| L1 | 8 | 280 |
| L1 | 9 | 280 |
| L1 | 9 | 188 |

TABLE XIII B-continued

HPV6B
HLA-B58 Supermotif Peptides

| 2 | 3 | 4 |
|---|---|---|
| L1 | 10 | 188 |
| E5A | 8 | 44 |
| E5A | 9 | 44 |
| E5A | 10 | 44 |
| E5A | 11 | 44 |
| E6 | 8 | 39 |
| E6 | 10 | 39 |
| L1 | 8 | 223 |
| L1 | 9 | 223 |
| L1 | 11 | 223 |
| E1 | 8 | 232 |
| E1 | 11 | 232 |
| E6 | 8 | 142 |
| E5B | 8 | 63 |
| E5B | 9 | 63 |
| E1 | 9 | 585 |
| E1 | 11 | 585 |
| E6 | 10 | 11 |
| L2 | 8 | 137 |
| L2 | 10 | 137 |
| E5A | 8 | 62 |
| E5A | 9 | 62 |
| E5A | 11 | 62 |
| L1 | 9 | 332 |
| L2 | 9 | 151 |
| L2 | 10 | 151 |
| L1 | 11 | 345 |
| E5A | 9 | 12 |
| E5A | 10 | 12 |
| E5A | 11 | 12 |
| E4 | 10 | 94 |
| L2 | 9 | 136 |
| L2 | 11 | 136 |
| L2 | 10 | 150 |
| L2 | 11 | 150 |
| E4 | 8 | 86 |
| E6 | 11 | 87 |
| L2 | 11 | 386 |
| E4 | 9 | 101 |
| E2 | 11 | 212 |
| E1 | 11 | 317 |
| L2 | 8 | 339 |
| L2 | 10 | 339 |
| L2 | 11 | 339 |
| E1 | 10 | 239 |
| L2 | 8 | 97 |
| L2 | 9 | 97 |
| L2 | 11 | 97 |
| E1 | 8 | 291 |
| E1 | 9 | 291 |
| E1 | 11 | 291 |
| E2 | 10 | 64 |
| L1 | 10 | 114 |
| L1 | 8 | 62 |
| L1 | 9 | 62 |
| L1 | 11 | 62 |
| E5A | 8 | 29 |
| E5A | 9 | 29 |
| E2 | 9 | 206 |
| L1 | 10 | 17 |
| L1 | 11 | 17 |
| L2 | 9 | 105 |
| L2 | 10 | 105 |
| E1 | 11 | 92 |
| L1 | 8 | 296 |
| E2 | 10 | 223 |
| E2 | 8 | 199 |
| E2 | 10 | 199 |
| L2 | 10 | 259 |
| L2 | 11 | 144 |
| E7 | 11 | 55 |
| E7 | 8 | 6 |
| E7 | 10 | 6 |
| E5B | 11 | 58 |
| L2 | 8 | 364 |
| L2 | 9 | 364 |
| L2 | 10 | 418 |
| L2 | 11 | 418 |
| L2 | 8 | 165 |
| L2 | 10 | 379 |
| L1 | 8 | 27 |
| L2 | 9 | 185 |
| L2 | 11 | 185 |
| L2 | 9 | 146 |
| L2 | 10 | 146 |
| E1 | 10 | 584 |
| L1 | 8 | 97 |
| E2 | 8 | 92 |
| E2 | 10 | 92 |
| E2 | 11 | 92 |
| E6 | 8 | 141 |
| E6 | 9 | 141 |
| E4 | 10 | 82 |
| E6 | 8 | 61 |
| E6 | 10 | 61 |
| L2 | 9 | 349 |
| E6 | 8 | 82 |
| E1 | 11 | 262 |
| E1 | 11 | 76 |
| E6 | 8 | 46 |
| E6 | 9 | 46 |
| E6 | 10 | 46 |
| E2 | 8 | 87 |
| L2 | 8 | 225 |
| L2 | 10 | 225 |
| L2 | 10 | 296 |
| E6 | 8 | 44 |
| E6 | 10 | 44 |
| E6 | 11 | 44 |
| E2 | 9 | 159 |
| E2 | 10 | 159 |
| E2 | 11 | 159 |
| L1 | 9 | 350 |
| L1 | 10 | 350 |
| E2 | 9 | 214 |
| E2 | 10 | 214 |
| E5A | 9 | 43 |
| E5A | 10 | 43 |
| E5A | 11 | 43 |
| E5B | 8 | 62 |
| E5B | 9 | 62 |
| E5B | 10 | 62 |

TABLE XIII C

HPV11
HLA-B58 Supermotif Peptides

| 2 | 3 | 4 |
|---|---|---|
| E5 | 8 | 9 |
| E5 | 9 | 9 |
| E5 | 10 | 9 |
| E6 | 9 | 62 |
| L1 | 9 | 235 |
| L1 | 10 | 235 |
| L1 | 11 | 235 |
| L2 | 10 | 328 |
| L2 | 11 | 328 |
| L2 | 9 | 339 |
| L2 | 10 | 339 |
| E4 | 8 | 12 |
| E4 | 10 | 12 |
| E4 | 11 | 12 |
| L2 | 8 | 86 |

TABLE XIII C-continued

HPV11
HLA-B58 Supermotif Peptides

| 2 | 3 | 4 |
|---|---|---|
| L2 | 11 | 86 |
| E2 | 8 | 282 |
| E5 | 8 | 10 |
| E5 | 9 | 10 |
| E5 | 11 | 10 |
| L2 | 10 | 405 |
| E2 | 11 | 321 |
| L1 | 9 | 36 |
| E6 | 8 | 6 |
| E6 | 11 | 6 |
| E1 | 11 | 330 |
| L1 | 9 | 343 |
| E2 | 10 | 197 |
| L1 | 11 | 22 |
| L2 | 9 | 22 |
| L2 | 10 | 22 |
| E1 | 8 | 525 |
| E1 | 9 | 525 |
| E6 | 11 | 10 |
| E5 | 8 | 11 |
| E5 | 10 | 11 |
| E5 | 11 | 11 |
| E1 | 10 | 77 |
| E1 | 11 | 77 |
| L1 | 8 | 349 |
| L1 | 11 | 349 |
| E6 | 11 | 64 |
| E1 | 9 | 234 |
| E1 | 11 | 234 |
| E1 | 8 | 406 |
| L1 | 9 | 158 |
| L1 | 10 | 342 |
| E1 | 9 | 506 |
| L1 | 9 | 375 |
| L1 | 10 | 375 |
| E2 | 10 | 194 |
| E7 | 9 | 71 |
| E1 | 10 | 14 |
| E1 | 11 | 14 |
| E1 | 10 | 289 |
| E1 | 11 | 289 |
| E2 | 8 | 9 |
| E2 | 10 | 9 |
| E2 | 11 | 9 |
| E1 | 10 | 250 |
| E1 | 10 | 73 |
| E1 | 8 | 607 |
| E1 | 11 | 607 |
| E7 | 9 | 44 |
| E7 | 11 | 44 |
| E6 | 9 | 5 |
| E1 | 9 | 524 |
| E1 | 10 | 524 |
| L1 | 9 | 24 |
| L1 | 10 | 24 |
| L1 | 11 | 24 |
| L2 | 10 | 203 |
| E1 | 9 | 42 |
| E1 | 10 | 42 |
| E1 | 9 | 134 |
| E1 | 8 | 387 |
| E2 | 8 | 292 |
| E2 | 10 | 292 |
| E7 | 8 | 62 |
| E1 | 9 | 353 |
| E1 | 10 | 353 |
| E7 | 10 | 31 |
| E2 | 8 | 259 |
| E1 | 9 | 435 |
| E1 | 10 | 435 |
| E2 | 10 | 143 |
| L2 | 10 | 343 |
| L1 | 9 | 199 |
| E1 | 9 | 481 |

TABLE XIII C-continued

HPV11
HLA-B58 Supermotif Peptides

| 2 | 3 | 4 |
|---|---|---|
| E1 | 11 | 481 |
| E1 | 11 | 164 |
| E1 | 8 | 191 |
| E1 | 9 | 191 |
| E2 | 8 | 96 |
| L1 | 8 | 332 |
| L1 | 10 | 332 |
| E5 | 8 | 12 |
| E5 | 9 | 12 |
| E1 | 8 | 534 |
| L1 | 11 | 412 |
| E1 | 9 | 71 |
| L2 | 9 | 273 |
| E1 | 11 | 336 |
| E2 | 8 | 324 |
| E2 | 9 | 324 |
| E2 | 11 | 324 |
| E2 | 11 | 174 |
| L1 | 9 | 300 |
| L1 | 10 | 300 |
| L1 | 11 | 300 |
| L2 | 8 | 172 |
| E1 | 8 | 373 |
| E1 | 8 | 103 |
| E1 | 11 | 103 |
| L2 | 11 | 265 |
| E2 | 8 | 80 |
| E2 | 10 | 80 |
| L2 | 8 | 134 |
| L2 | 10 | 134 |
| E2 | 11 | 39 |
| E2 | 8 | 66 |
| E2 | 10 | 66 |
| E6 | 9 | 92 |
| E6 | 10 | 92 |
| E6 | 11 | 92 |
| E1 | 10 | 128 |
| E6 | 8 | 61 |
| E6 | 10 | 61 |
| L1 | 11 | 207 |
| L1 | 8 | 80 |
| L1 | 9 | 80 |
| L2 | 9 | 438 |
| L2 | 11 | 438 |
| E5 | 8 | 24 |
| E5 | 9 | 24 |
| E5 | 10 | 24 |
| E5 | 11 | 24 |
| L2 | 8 | 411 |
| L2 | 10 | 295 |
| L2 | 11 | 295 |
| L1 | 8 | 451 |
| L1 | 10 | 451 |
| E5 | 8 | 20 |
| E5 | 9 | 20 |
| E5 | 11 | 20 |
| E1 | 9 | 587 |
| L2 | 10 | 61 |
| L2 | 11 | 61 |
| L1 | 8 | 203 |
| L2 | 10 | 313 |
| L2 | 10 | 427 |
| L2 | 11 | 427 |
| E4 | 9 | 61 |
| E1 | 8 | 11 |
| E1 | 9 | 11 |
| E1 | 10 | 11 |
| L2 | 8 | 63 |
| L2 | 9 | 63 |
| L2 | 11 | 63 |
| L2 | 10 | 47 |
| L1 | 10 | 294 |
| L1 | 11 | 294 |
| L2 | 11 | 302 |

TABLE XIII C-continued

HPV11
HLA-B58 Supermotif Peptides

| 2 | 3 | 4 |
|---|---|---|
| E1 | 10 | 632 |
| E1 | 8 | 88 |
| E1 | 11 | 88 |
| L2 | 8 | 74 |
| E2 | 8 | 179 |
| E2 | 10 | 179 |
| E2 | 11 | 189 |
| L2 | 8 | 24 |
| L2 | 11 | 24 |
| E1 | 10 | 431 |
| L1 | 9 | 408 |
| L1 | 10 | 408 |
| E1 | 11 | 296 |
| E7 | 9 | 85 |
| L2 | 11 | 408 |
| E1 | 8 | 467 |
| E1 | 10 | 467 |
| E1 | 11 | 467 |
| L1 | 9 | 169 |
| E4 | 8 | 99 |
| E4 | 10 | 99 |
| L1 | 9 | 223 |
| L1 | 10 | 223 |
| L1 | 11 | 262 |
| E1 | 8 | 189 |
| E1 | 10 | 189 |
| E1 | 11 | 189 |
| E1 | 9 | 415 |
| L1 | 8 | 35 |
| L1 | 10 | 35 |
| E2 | 8 | 280 |
| E2 | 10 | 280 |
| E1 | 10 | 246 |
| E1 | 11 | 246 |
| E1 | 8 | 349 |
| E1 | 10 | 349 |
| E1 | 9 | 581 |
| L2 | 8 | 361 |
| E6 | 8 | 25 |
| E6 | 9 | 25 |
| L1 | 8 | 388 |
| L1 | 11 | 388 |
| E4 | 10 | 36 |
| L1 | 8 | 290 |
| L2 | 8 | 36 |
| L2 | 9 | 36 |
| L2 | 11 | 36 |
| L2 | 11 | 148 |
| E5 | 9 | 8 |
| E5 | 10 | 8 |
| E5 | 11 | 8 |
| E1 | 8 | 248 |
| E1 | 9 | 248 |
| L2 | 8 | 39 |
| L2 | 11 | 39 |
| E5 | 8 | 22 |
| E5 | 10 | 22 |
| E5 | 11 | 22 |
| E1 | 11 | 376 |
| L2 | 11 | 179 |
| E5 | 10 | 37 |
| E5 | 11 | 37 |
| E1 | 9 | 32 |
| E1 | 9 | 571 |
| E1 | 10 | 571 |
| E1 | 8 | 327 |
| E1 | 8 | 95 |
| E1 | 8 | 106 |
| E1 | 10 | 106 |
| L2 | 11 | 322 |
| E1 | 10 | 500 |
| E1 | 11 | 500 |
| L2 | 8 | 400 |
| L2 | 11 | 81 |
| L2 | 8 | 425 |
| L1 | 8 | 377 |
| L1 | 10 | 377 |
| L1 | 11 | 377 |
| E1 | 11 | 56 |
| E1 | 11 | 341 |
| L2 | 9 | 184 |
| L2 | 11 | 184 |
| L2 | 8 | 286 |
| L2 | 10 | 286 |
| L2 | 11 | 130 |
| L1 | 10 | 188 |
| L1 | 11 | 188 |
| E4 | 11 | 92 |
| E2 | 10 | 45 |
| L1 | 9 | 312 |
| L1 | 11 | 312 |
| E6 | 11 | 123 |
| L2 | 10 | 21 |
| L2 | 11 | 21 |
| L1 | 10 | 347 |
| E1 | 8 | 484 |
| E1 | 9 | 484 |
| E1 | 11 | 484 |
| E1 | 10 | 228 |
| E1 | 11 | 228 |
| L1 | 8 | 214 |
| E5 | 8 | 50 |
| E5 | 10 | 50 |
| E5 | 11 | 50 |
| E1 | 10 | 286 |
| E4 | 8 | 53 |
| E6 | 10 | 18 |
| E2 | 9 | 84 |
| E2 | 11 | 84 |
| L1 | 10 | 56 |
| E1 | 8 | 351 |
| E1 | 11 | 351 |
| E2 | 8 | 82 |
| E2 | 11 | 82 |
| E4 | 9 | 23 |
| E4 | 10 | 23 |
| E2 | 8 | 313 |
| L1 | 8 | 42 |
| L1 | 10 | 42 |
| L1 | 8 | 379 |
| L1 | 9 | 379 |
| E1 | 9 | 605 |
| E1 | 10 | 605 |
| E1 | 10 | 218 |
| E2 | 8 | 51 |
| E2 | 9 | 51 |
| L2 | 8 | 386 |
| L2 | 9 | 386 |
| E5 | 8 | 29 |
| E5 | 9 | 29 |
| E1 | 8 | 458 |
| E6 | 8 | 22 |
| E6 | 11 | 22 |
| E1 | 9 | 259 |
| E1 | 10 | 259 |
| L1 | 9 | 402 |
| L2 | 10 | 375 |
| L2 | 8 | 239 |
| L2 | 10 | 239 |
| E7 | 11 | 55 |
| E5 | 11 | 4 |
| E1 | 8 | 514 |
| E1 | 9 | 514 |
| E1 | 8 | 132 |
| E1 | 11 | 132 |
| E1 | 9 | 358 |
| E5 | 8 | 70 |
| E5 | 11 | 70 |

TABLE XIII C-continued

HPV11
HLA-B58 Supermotif Peptides

| 2 | 3 | 4 |
|---|---|---|
| E1 | 9 | 555 |
| E1 | 10 | 555 |
| E1 | 11 | 555 |
| E5 | 8 | 49 |
| E5 | 9 | 49 |
| E5 | 10 | 49 |
| E5 | 11 | 49 |
| E1 | 8 | 268 |
| E1 | 9 | 268 |
| E1 | 10 | 268 |
| E1 | 11 | 268 |
| E2 | 8 | 103 |
| E7 | 8 | 48 |
| L2 | 8 | 368 |
| E6 | 9 | 38 |
| E6 | 11 | 38 |
| E5 | 8 | 61 |
| E5 | 9 | 61 |
| E5 | 10 | 61 |
| E1 | 8 | 115 |
| L1 | 10 | 234 |
| L1 | 11 | 234 |
| E4 | 8 | 11 |
| E4 | 9 | 11 |
| E4 | 11 | 11 |
| L1 | 11 | 384 |
| L1 | 8 | 440 |
| E5 | 9 | 62 |
| E5 | 10 | 62 |
| E5 | 11 | 62 |
| E1 | 10 | 546 |
| E1 | 9 | 421 |
| E1 | 11 | 489 |
| L2 | 8 | 114 |
| E2 | 9 | 71 |
| E2 | 8 | 329 |
| E6 | 8 | 36 |
| E6 | 9 | 36 |
| E6 | 11 | 36 |
| L2 | 8 | 269 |
| L2 | 10 | 269 |
| L2 | 11 | 269 |
| E1 | 10 | 389 |
| E1 | 11 | 100 |
| E1 | 11 | 600 |
| E1 | 8 | 270 |
| E1 | 9 | 270 |
| E1 | 10 | 270 |
| E1 | 11 | 270 |
| E1 | 8 | 504 |
| E1 | 11 | 504 |
| L1 | 8 | 353 |
| L1 | 11 | 353 |
| E2 | 9 | 22 |
| E2 | 10 | 22 |
| E1 | 8 | 395 |
| E1 | 9 | 395 |
| E1 | 8 | 634 |
| E1 | 8 | 59 |
| E1 | 9 | 59 |
| E2 | 9 | 347 |
| E2 | 8 | 248 |
| E2 | 11 | 248 |
| E5 | 8 | 54 |
| E5 | 9 | 54 |
| L2 | 8 | 381 |
| L2 | 8 | 85 |
| L2 | 9 | 85 |
| L2 | 10 | 236 |
| L2 | 11 | 236 |
| E5 | 8 | 78 |
| E5 | 9 | 78 |
| E5 | 10 | 78 |
| L2 | 8 | 138 |
| L2 | 9 | 284 |
| L2 | 10 | 284 |
| L2 | 8 | 416 |
| L2 | 9 | 416 |
| L2 | 10 | 416 |
| E2 | 9 | 216 |
| E2 | 8 | 196 |
| E2 | 11 | 196 |
| L2 | 9 | 98 |
| L2 | 10 | 98 |
| L1 | 8 | 4 |
| E2 | 9 | 244 |
| L2 | 10 | 162 |
| L1 | 9 | 392 |
| L1 | 11 | 392 |
| L2 | 9 | 403 |
| E2 | 9 | 353 |
| E2 | 10 | 353 |
| L2 | 8 | 182 |
| L2 | 11 | 182 |
| L1 | 11 | 427 |
| L2 | 8 | 123 |
| E4 | 8 | 76 |
| L2 | 11 | 206 |
| L1 | 8 | 90 |
| E6 | 11 | 87 |
| L2 | 8 | 327 |
| L2 | 11 | 327 |
| E1 | 10 | 636 |
| E1 | 11 | 636 |
| E1 | 10 | 399 |
| E1 | 11 | 399 |
| L2 | 8 | 395 |
| E1 | 8 | 314 |
| E1 | 9 | 314 |
| E1 | 10 | 314 |
| E4 | 9 | 84 |
| L2 | 8 | 377 |
| L2 | 10 | 377 |
| L2 | 11 | 365 |
| L1 | 9 | 211 |
| L1 | 11 | 211 |
| E1 | 8 | 344 |
| E1 | 8 | 391 |
| L2 | 8 | 214 |
| L2 | 10 | 214 |
| L2 | 11 | 214 |
| L1 | 9 | 260 |
| L2 | 8 | 226 |
| E1 | 11 | 553 |
| E1 | 10 | 318 |
| E2 | 11 | 240 |
| L2 | 8 | 10 |
| L2 | 10 | 307 |
| L1 | 8 | 280 |
| L1 | 9 | 280 |
| L1 | 10 | 280 |
| E1 | 8 | 205 |
| L1 | 11 | 335 |
| E2 | 10 | 256 |
| E2 | 11 | 256 |
| L1 | 9 | 477 |
| E1 | 10 | 324 |
| E1 | 11 | 324 |
| E1 | 9 | 293 |
| L1 | 8 | 473 |
| E1 | 8 | 231 |
| E1 | 9 | 231 |
| E2 | 9 | 281 |
| E2 | 9 | 225 |
| L1 | 8 | 380 |
| L1 | 11 | 380 |
| L2 | 11 | 110 |
| L2 | 10 | 180 |

TABLE XIII C-continued

HPV11
HLA-B58 Supermotif Peptides

| 2 | 3 | 4 |
|---|---|---|
| L1 | 11 | 475 |
| E6 | 8 | 9 |
| L1 | 9 | 348 |
| L1 | 11 | 298 |
| E7 | 9 | 32 |
| E2 | 9 | 337 |
| E2 | 10 | 337 |
| L1 | 9 | 452 |
| L2 | 9 | 132 |
| L2 | 10 | 132 |
| L1 | 11 | 85 |
| L1 | 11 | 38 |
| L1 | 8 | 37 |
| L2 | 9 | 208 |
| E2 | 9 | 200 |
| L1 | 8 | 281 |
| L1 | 9 | 281 |
| E2 | 8 | 150 |
| E2 | 9 | 150 |
| E2 | 10 | 150 |
| E2 | 11 | 260 |
| E4 | 8 | 95 |
| E4 | 10 | 95 |
| E1 | 11 | 206 |
| E2 | 9 | 180 |
| L1 | 10 | 336 |
| E2 | 8 | 245 |
| E2 | 11 | 245 |
| L2 | 8 | 209 |
| L2 | 10 | 370 |
| L2 | 9 | 240 |
| E1 | 11 | 185 |
| E6 | 10 | 7 |
| L2 | 9 | 135 |
| L2 | 11 | 135 |
| E4 | 8 | 85 |
| E2 | 10 | 190 |
| E1 | 10 | 331 |
| E1 | 11 | 331 |
| E2 | 8 | 201 |
| L1 | 11 | 7 |
| E6 | 9 | 40 |
| E5 | 8 | 21 |
| E5 | 10 | 21 |
| E5 | 11 | 21 |
| L2 | 8 | 404 |
| L2 | 11 | 404 |
| E6 | 9 | 8 |
| E1 | 8 | 192 |
| E6 | 10 | 11 |
| L2 | 8 | 185 |
| L2 | 10 | 185 |
| L2 | 9 | 287 |
| L2 | 10 | 131 |
| L2 | 11 | 131 |
| L2 | 10 | 207 |
| E2 | 9 | 149 |
| E2 | 10 | 149 |
| E2 | 11 | 149 |
| E4 | 9 | 94 |
| E4 | 11 | 94 |
| L2 | 11 | 369 |
| L2 | 8 | 151 |
| L2 | 9 | 151 |
| L1 | 9 | 189 |
| L1 | 10 | 189 |
| E5 | 8 | 44 |
| E5 | 9 | 44 |
| E5 | 10 | 44 |
| E5 | 11 | 44 |
| L1 | 11 | 175 |
| E6 | 8 | 39 |
| E6 | 10 | 39 |
| E1 | 8 | 232 |

TABLE XIII C-continued

HPV11
HLA-B58 Supermotif Peptides

| 2 | 3 | 4 |
|---|---|---|
| E1 | 11 | 232 |
| E6 | 8 | 142 |
| E1 | 9 | 585 |
| E1 | 11 | 585 |
| L2 | 8 | 37 |
| L2 | 10 | 37 |
| E5 | 8 | 14 |
| E5 | 9 | 14 |
| E5 | 11 | 14 |
| L2 | 8 | 136 |
| L2 | 10 | 136 |
| E5 | 8 | 62 |
| E5 | 9 | 62 |
| E5 | 11 | 62 |
| E1 | 11 | 116 |
| L1 | 9 | 333 |
| E4 | 10 | 93 |
| L2 | 9 | 150 |
| L2 | 10 | 150 |
| E5 | 8 | 13 |
| E5 | 9 | 13 |
| E5 | 10 | 13 |
| L2 | 10 | 149 |
| L2 | 11 | 149 |
| E5 | 9 | 12 |
| E5 | 10 | 12 |
| E5 | 11 | 12 |
| E5 | 8 | 55 |
| L2 | 11 | 382 |
| E4 | 9 | 100 |
| L2 | 8 | 338 |
| L2 | 10 | 338 |
| L2 | 11 | 338 |
| E1 | 10 | 239 |
| E1 | 9 | 98 |
| E2 | 11 | 252 |
| L2 | 8 | 96 |
| L2 | 9 | 96 |
| L2 | 11 | 96 |
| E1 | 8 | 291 |
| E1 | 9 | 291 |
| E1 | 11 | 291 |
| E5 | 8 | 25 |
| E5 | 9 | 25 |
| E5 | 11 | 25 |
| E2 | 10 | 224 |
| E2 | 10 | 64 |
| L1 | 10 | 114 |
| L1 | 8 | 62 |
| L1 | 9 | 62 |
| L1 | 11 | 62 |
| E2 | 9 | 206 |
| L1 | 10 | 17 |
| L1 | 11 | 17 |
| L2 | 9 | 104 |
| L2 | 10 | 104 |
| L2 | 10 | 258 |
| E1 | 11 | 92 |
| L1 | 8 | 297 |
| E2 | 8 | 199 |
| E2 | 10 | 199 |
| L2 | 11 | 143 |
| E7 | 8 | 6 |
| E7 | 10 | 6 |
| L2 | 9 | 145 |
| L2 | 10 | 145 |
| L2 | 10 | 414 |
| L2 | 11 | 414 |
| L2 | 8 | 325 |
| L2 | 10 | 325 |
| E2 | 10 | 148 |
| E2 | 11 | 148 |
| E1 | 10 | 584 |
| L2 | 8 | 246 |

TABLE XIII C-continued

HPV11
HLA-B58 Supermotif Peptides

| 2 | 3 | 4 |
|---|---|---|
| L1 | 8 | 97 |
| E2 | 8 | 92 |
| E2 | 10 | 92 |
| E2 | 11 | 92 |
| E6 | 8 | 141 |
| E6 | 9 | 141 |
| E4 | 10 | 81 |
| E1 | 8 | 530 |
| E1 | 11 | 530 |
| E6 | 8 | 82 |
| L2 | 8 | 348 |
| E1 | 11 | 262 |
| E1 | 11 | 76 |
| E6 | 8 | 44 |
| E6 | 10 | 44 |
| E6 | 11 | 44 |
| E6 | 8 | 46 |
| E6 | 9 | 46 |
| E6 | 10 | 46 |
| E1 | 10 | 139 |
| L1 | 10 | 49 |
| L1 | 11 | 49 |
| L2 | 8 | 224 |
| L2 | 10 | 224 |
| E2 | 10 | 336 |
| E2 | 11 | 336 |
| E2 | 9 | 159 |
| E2 | 10 | 159 |
| E2 | 11 | 159 |
| L1 | 9 | 351 |
| L1 | 10 | 351 |
| E2 | 11 | 214 |
| L2 | 8 | 305 |
| E5 | 9 | 43 |
| E5 | 10 | 43 |
| E5 | 11 | 43 |

TABLE XIV

HLA-B62 Supermotif Peptides

| 1 | 2 | 3 | 4 |
|---|---|---|---|
| HPV16 | E1 | 10 | 112 |
| HPV16 | E1 | 11 | 112 |
| HPV16 | E1 | 9 | 539 |
| HPV16 | E1 | 11 | 539 |
| HPV16 | E1 | 8 | 69 |
| HPV16 | E1 | 9 | 459 |
| HPV16 | E1 | 9 | 318 |
| HPV16 | E1 | 9 | 206 |
| HPV16 | E1 | 10 | 206 |
| HPV16 | E1 | 10 | 73 |
| HPV16 | E1 | 11 | 73 |
| HPV16 | E1 | 10 | 380 |
| HPV16 | E1 | 9 | 82 |
| HPV16 | E1 | 10 | 82 |
| HPV16 | E1 | 11 | 82 |
| HPV16 | E1 | 10 | 23 |
| HPV16 | E1 | 11 | 23 |
| HPV16 | E1 | 11 | 237 |
| HPV16 | E1 | 8 | 114 |
| HPV16 | E1 | 9 | 114 |
| HPV16 | E1 | 8 | 472 |
| HPV16 | E1 | 9 | 259 |
| HPV16 | E1 | 10 | 259 |
| HPV16 | E1 | 9 | 304 |
| HPV16 | E1 | 10 | 559 |
| HPV16 | E1 | 8 | 187 |
| HPV16 | E1 | 9 | 187 |
| HPV16 | E1 | 11 | 187 |

TABLE XIV-continued

HLA-B62 Supermotif Peptides

| 1 | 2 | 3 | 4 |
|---|---|---|---|
| HPV16 | E1 | 10 | 101 |
| HPV16 | E1 | 10 | 640 |
| HPV16 | E1 | 8 | 299 |
| HPV16 | E1 | 9 | 299 |
| HPV16 | E1 | 10 | 97 |
| HPV16 | E1 | 8 | 368 |
| HPV16 | E1 | 9 | 368 |
| HPV16 | E1 | 10 | 368 |
| HPV16 | E1 | 8 | 548 |
| HPV16 | E1 | 10 | 548 |
| HPV16 | E1 | 9 | 374 |
| HPV16 | E1 | 10 | 374 |
| HPV16 | E1 | 10 | 603 |
| HPV16 | E1 | 11 | 603 |
| HPV16 | E1 | 8 | 356 |
| HPV16 | E1 | 9 | 356 |
| HPV16 | E1 | 10 | 356 |
| HPV16 | E1 | 10 | 213 |
| HPV16 | E1 | 11 | 213 |
| HPV16 | E1 | 9 | 308 |
| HPV16 | E1 | 10 | 308 |
| HPV16 | E1 | 11 | 308 |
| HPV16 | E1 | 8 | 138 |
| HPV16 | E1 | 10 | 138 |
| HPV16 | E1 | 9 | 331 |
| HPV16 | E1 | 10 | 331 |
| HPV16 | E1 | 8 | 51 |
| HPV16 | E1 | 9 | 51 |
| HPV16 | E1 | 8 | 392 |
| HPV16 | E1 | 10 | 392 |
| HPV16 | E1 | 11 | 392 |
| HPV16 | E1 | 11 | 463 |
| HPV16 | E1 | 9 | 493 |
| HPV16 | E1 | 10 | 493 |
| HPV16 | E1 | 9 | 445 |
| HPV16 | E1 | 10 | 445 |
| HPV16 | E1 | 8 | 456 |
| HPV16 | E1 | 9 | 456 |
| HPV16 | E1 | 8 | 453 |
| HPV16 | E1 | 11 | 453 |
| HPV16 | E1 | 10 | 592 |
| HPV16 | E1 | 11 | 592 |
| HPV16 | E1 | 8 | 501 |
| HPV16 | E1 | 9 | 501 |
| HPV16 | E1 | 10 | 501 |
| HPV16 | E1 | 8 | 466 |
| HPV16 | E1 | 9 | 466 |
| HPV16 | E1 | 10 | 466 |
| HPV16 | E1 | 11 | 466 |
| HPV16 | E1 | 8 | 325 |
| HPV16 | E1 | 9 | 325 |
| HPV16 | E1 | 10 | 242 |
| HPV16 | E1 | 8 | 519 |
| HPV16 | E1 | 11 | 519 |
| HPV16 | E1 | 8 | 487 |
| HPV16 | E1 | 8 | 272 |
| HPV16 | E1 | 10 | 272 |
| HPV16 | E1 | 8 | 450 |
| HPV16 | E1 | 10 | 450 |
| HPV16 | E1 | 11 | 450 |
| HPV16 | E1 | 8 | 179 |
| HPV16 | E1 | 8 | 216 |
| HPV16 | E1 | 11 | 216 |
| HPV16 | E1 | 9 | 263 |
| HPV16 | E1 | 11 | 263 |
| HPV16 | E1 | 10 | 194 |
| HPV16 | E1 | 8 | 467 |
| HPV16 | E1 | 9 | 467 |
| HPV16 | E1 | 10 | 467 |
| HPV16 | E1 | 11 | 467 |
| HPV16 | E1 | 11 | 340 |
| HPV16 | E1 | 8 | 264 |
| HPV16 | E1 | 10 | 264 |
| HPV16 | E1 | 11 | 264 |
| HPV16 | E1 | 8 | 369 |
| HPV16 | E1 | 9 | 369 |

TABLE XIV-continued

HLA-B62 Supermotif Peptides

| 1 | 2 | 3 | 4 |
|---|---|---|---|
| HPV16 | E1 | 11 | 369 |
| HPV16 | E1 | 8 | 401 |
| HPV16 | E1 | 10 | 442 |
| HPV16 | E1 | 8 | 52 |
| HPV16 | E1 | 11 | 52 |
| HPV16 | E1 | 8 | 517 |
| HPV16 | E1 | 10 | 517 |
| HPV16 | E1 | 9 | 400 |
| HPV16 | E1 | 8 | 296 |
| HPV16 | E1 | 10 | 296 |
| HPV16 | E1 | 11 | 296 |
| HPV16 | E1 | 9 | 292 |
| HPV16 | E1 | 8 | 311 |
| HPV16 | E1 | 9 | 311 |
| HPV16 | E1 | 10 | 311 |
| HPV16 | E1 | 11 | 311 |
| HPV16 | E1 | 9 | 77 |
| HPV16 | E1 | 10 | 77 |
| HPV16 | E1 | 9 | 440 |
| HPV16 | E1 | 8 | 418 |
| HPV16 | E1 | 9 | 418 |
| HPV16 | E1 | 11 | 418 |
| HPV16 | E1 | 10 | 117 |
| HPV16 | E1 | 11 | 117 |
| HPV16 | E1 | 8 | 563 |
| HPV16 | E1 | 9 | 297 |
| HPV16 | E1 | 10 | 297 |
| HPV16 | E1 | 11 | 297 |
| HPV16 | E1 | 9 | 562 |
| HPV16 | E1 | 8 | 254 |
| HPV16 | E1 | 9 | 254 |
| HPV16 | E1 | 11 | 254 |
| HPV16 | E1 | 8 | 293 |
| HPV16 | E1 | 11 | 293 |
| HPV16 | E1 | 9 | 490 |
| HPV16 | E1 | 10 | 490 |
| HPV16 | E1 | 10 | 464 |
| HPV16 | E1 | 11 | 464 |
| HPV16 | E1 | 8 | 494 |
| HPV16 | E1 | 9 | 494 |
| HPV16 | E1 | 10 | 346 |
| HPV16 | E1 | 9 | 510 |
| HPV16 | E1 | 11 | 510 |
| HPV16 | E1 | 8 | 255 |
| HPV16 | E1 | 10 | 255 |
| HPV16 | E1 | 11 | 48 |
| HPV16 | E1 | 9 | 554 |
| HPV16 | E1 | 10 | 554 |
| HPV16 | E1 | 11 | 554 |
| HPV16 | E1 | 11 | 544 |
| HPV16 | E1 | 8 | 91 |
| HPV16 | E1 | 10 | 583 |
| HPV16 | E1 | 11 | 306 |
| HPV16 | E1 | 8 | 207 |
| HPV16 | E1 | 9 | 207 |
| HPV16 | E1 | 11 | 207 |
| HPV16 | E1 | 10 | 520 |
| HPV16 | E1 | 8 | 305 |
| HPV16 | E1 | 10 | 360 |
| HPV16 | E1 | 11 | 360 |
| HPV16 | E1 | 9 | 273 |
| HPV16 | E1 | 11 | 193 |
| HPV16 | E1 | 10 | 567 |
| HPV16 | E1 | 8 | 105 |
| HPV16 | E1 | 9 | 105 |
| HPV16 | E1 | 11 | 105 |
| HPV16 | E1 | 10 | 535 |
| HPV16 | E1 | 11 | 535 |
| HPV16 | E1 | 11 | 599 |
| HPV16 | E1 | 8 | 196 |
| HPV16 | E1 | 10 | 196 |
| HPV16 | E1 | 11 | 196 |
| HPV16 | E1 | 9 | 512 |
| HPV16 | E1 | 10 | 512 |
| HPV16 | E1 | 8 | 561 |
| HPV16 | E1 | 10 | 561 |
| HPV16 | E1 | 9 | 94 |
| HPV16 | E1 | 8 | 190 |
| HPV16 | E1 | 9 | 190 |
| HPV16 | E1 | 10 | 553 |
| HPV16 | E1 | 11 | 553 |
| HPV16 | E1 | 11 | 302 |
| HPV16 | E1 | 8 | 309 |
| HPV16 | E1 | 9 | 309 |
| HPV16 | E1 | 10 | 309 |
| HPV16 | E1 | 11 | 309 |
| HPV16 | E1 | 9 | 560 |
| HPV16 | E1 | 11 | 560 |
| HPV16 | E1 | 10 | 600 |
| HPV16 | E1 | 8 | 441 |
| HPV16 | E1 | 11 | 441 |
| HPV16 | E1 | 9 | 381 |
| HPV16 | E1 | 11 | 381 |
| HPV16 | E1 | 8 | 556 |
| HPV16 | E1 | 9 | 556 |
| HPV16 | E1 | 8 | 419 |
| HPV16 | E1 | 10 | 419 |
| HPV16 | E1 | 11 | 359 |
| HPV16 | E1 | 8 | 511 |
| HPV16 | E1 | 10 | 511 |
| HPV16 | E1 | 11 | 511 |
| HPV16 | E1 | 9 | 256 |
| HPV16 | E1 | 8 | 84 |
| HPV16 | E1 | 9 | 84 |
| HPV16 | E1 | 10 | 125 |
| HPV16 | E1 | 11 | 582 |
| HPV16 | E1 | 11 | 552 |
| HPV16 | E1 | 9 | 342 |
| HPV16 | E1 | 8 | 432 |
| HPV16 | E1 | 11 | 432 |
| HPV16 | E1 | 9 | 246 |
| HPV16 | E1 | 10 | 246 |
| HPV16 | E1 | 9 | 250 |
| HPV16 | E1 | 11 | 250 |
| HPV16 | E1 | 8 | 266 |
| HPV16 | E1 | 9 | 266 |
| HPV16 | E1 | 10 | 266 |
| HPV16 | E1 | 11 | 266 |
| HPV16 | E1 | 8 | 484 |
| HPV16 | E1 | 10 | 484 |
| HPV16 | E1 | 11 | 484 |
| HPV16 | E1 | 10 | 489 |
| HPV16 | E1 | 11 | 489 |
| HPV16 | E1 | 8 | 634 |
| HPV16 | E1 | 9 | 546 |
| HPV16 | E1 | 10 | 546 |
| HPV16 | E1 | 8 | 421 |
| HPV16 | E1 | 10 | 93 |
| HPV16 | E1 | 9 | 107 |
| HPV16 | E1 | 10 | 397 |
| HPV16 | E1 | 8 | 358 |
| HPV16 | E1 | 11 | 423 |
| HPV16 | E1 | 10 | 185 |
| HPV16 | E1 | 11 | 185 |
| HPV16 | E1 | 9 | 289 |
| HPV16 | E1 | 10 | 289 |
| HPV16 | E1 | 8 | 253 |
| HPV16 | E1 | 9 | 253 |
| HPV16 | E1 | 10 | 253 |
| HPV16 | E1 | 9 | 407 |
| HPV16 | E1 | 10 | 336 |
| HPV16 | E1 | 11 | 336 |
| HPV16 | E1 | 9 | 189 |
| HPV16 | E1 | 10 | 189 |
| HPV16 | E1 | 8 | 244 |
| HPV16 | E1 | 11 | 244 |
| HPV16 | E1 | 8 | 60 |
| HPV16 | E1 | 10 | 60 |
| HPV16 | E1 | 11 | 60 |
| HPV16 | E1 | 8 | 525 |

TABLE XIV-continued

HLA-B62 Supermotif Peptides

| 1 | 2 | 3 | 4 |
|---|---|---|---|
| HPV16 | E1 | 11 | 498 |
| HPV16 | E1 | 8 | 85 |
| HPV16 | E1 | 11 | 85 |
| HPV16 | E1 | 9 | 197 |
| HPV16 | E1 | 10 | 197 |
| HPV16 | E1 | 11 | 197 |
| HPV16 | E1 | 11 | 345 |
| HPV16 | E1 | 9 | 443 |
| HPV16 | E1 | 11 | 443 |
| HPV16 | E1 | 11 | 526 |
| HPV16 | E1 | 8 | 555 |
| HPV16 | E1 | 9 | 555 |
| HPV16 | E1 | 10 | 555 |
| HPV16 | E1 | 8 | 83 |
| HPV16 | E1 | 9 | 83 |
| HPV16 | E1 | 10 | 83 |
| HPV16 | E1 | 9 | 361 |
| HPV16 | E1 | 10 | 361 |
| HPV16 | E1 | 9 | 24 |
| HPV16 | E1 | 10 | 24 |
| HPV16 | E1 | 9 | 584 |
| HPV16 | E1 | 11 | 584 |
| HPV16 | E1 | 8 | 274 |
| HPV16 | E1 | 9 | 425 |
| HPV16 | E1 | 8 | 339 |
| HPV16 | E1 | 8 | 509 |
| HPV16 | E1 | 10 | 509 |
| HPV16 | E1 | 8 | 576 |
| HPV16 | E1 | 9 | 576 |
| HPV16 | E1 | 10 | 576 |
| HPV16 | E1 | 11 | 576 |
| HPV16 | E1 | 9 | 531 |
| HPV16 | E1 | 10 | 531 |
| HPV16 | E1 | 8 | 261 |
| HPV16 | E1 | 11 | 261 |
| HPV16 | E1 | 8 | 578 |
| HPV16 | E1 | 9 | 578 |
| HPV16 | E1 | 11 | 578 |
| HPV16 | E1 | 10 | 58 |
| HPV16 | E1 | 9 | 90 |
| HPV16 | E1 | 9 | 448 |
| HPV16 | E1 | 10 | 448 |
| HPV16 | E2 | 8 | 72 |
| HPV16 | E2 | 11 | 72 |
| HPV16 | E2 | 11 | 331 |
| HPV16 | E2 | 9 | 41 |
| HPV16 | E2 | 11 | 41 |
| HPV16 | E2 | 11 | 228 |
| HPV16 | E2 | 9 | 69 |
| HPV16 | E2 | 11 | 69 |
| HPV16 | E2 | 11 | 105 |
| HPV16 | E2 | 8 | 63 |
| HPV16 | E2 | 10 | 63 |
| HPV16 | E2 | 11 | 63 |
| HPV16 | E2 | 8 | 314 |
| HPV16 | E2 | 9 | 109 |
| HPV16 | E2 | 11 | 109 |
| HPV16 | E2 | 11 | 195 |
| HPV16 | E2 | 9 | 11 |
| HPV16 | E2 | 11 | 5 |
| HPV16 | E2 | 8 | 124 |
| HPV16 | E2 | 11 | 124 |
| HPV16 | E2 | 8 | 25 |
| HPV16 | E2 | 9 | 25 |
| HPV16 | E2 | 9 | 344 |
| HPV16 | E2 | 8 | 96 |
| HPV16 | E2 | 10 | 96 |
| HPV16 | E2 | 8 | 209 |
| HPV16 | E2 | 9 | 74 |
| HPV16 | E2 | 10 | 74 |
| HPV16 | E2 | 11 | 48 |
| HPV16 | E2 | 8 | 185 |
| HPV16 | E2 | 9 | 185 |
| HPV16 | E2 | 10 | 185 |
| HPV16 | E2 | 8 | 118 |
| HPV16 | E2 | 8 | 204 |
| HPV16 | E2 | 11 | 100 |
| HPV16 | E2 | 11 | 346 |
| HPV16 | E2 | 8 | 168 |
| HPV16 | E2 | 11 | 168 |
| HPV16 | E2 | 9 | 163 |
| HPV16 | E2 | 9 | 156 |
| HPV16 | E2 | 8 | 150 |
| HPV16 | E2 | 9 | 150 |
| HPV16 | E2 | 10 | 150 |
| HPV16 | E2 | 11 | 150 |
| HPV16 | E2 | 10 | 190 |
| HPV16 | E2 | 11 | 190 |
| HPV16 | E2 | 8 | 29 |
| HPV16 | E2 | 10 | 29 |
| HPV16 | E2 | 10 | 53 |
| HPV16 | E2 | 11 | 53 |
| HPV16 | E2 | 8 | 136 |
| HPV16 | E2 | 10 | 136 |
| HPV16 | E2 | 8 | 214 |
| HPV16 | E2 | 9 | 290 |
| HPV16 | E2 | 8 | 35 |
| HPV16 | E2 | 9 | 35 |
| HPV16 | E2 | 10 | 35 |
| HPV16 | E2 | 9 | 218 |
| HPV16 | E2 | 10 | 218 |
| HPV16 | E2 | 11 | 218 |
| HPV16 | E2 | 8 | 56 |
| HPV16 | E2 | 9 | 56 |
| HPV16 | E2 | 11 | 210 |
| HPV16 | E2 | 8 | 193 |
| HPV16 | E2 | 11 | 352 |
| HPV16 | E2 | 8 | 288 |
| HPV16 | E2 | 11 | 288 |
| HPV16 | E2 | 10 | 332 |
| HPV16 | E2 | 8 | 351 |
| HPV16 | E2 | 8 | 255 |
| HPV16 | E2 | 11 | 255 |
| HPV16 | E2 | 11 | 182 |
| HPV16 | E2 | 10 | 256 |
| HPV16 | E2 | 8 | 70 |
| HPV16 | E2 | 10 | 70 |
| HPV16 | E2 | 8 | 94 |
| HPV16 | E2 | 9 | 94 |
| HPV16 | E2 | 10 | 94 |
| HPV16 | E2 | 8 | 75 |
| HPV16 | E2 | 9 | 75 |
| HPV16 | E2 | 8 | 249 |
| HPV16 | E2 | 9 | 249 |
| HPV16 | E2 | 8 | 9 |
| HPV16 | E2 | 11 | 9 |
| HPV16 | E2 | 8 | 325 |
| HPV16 | E2 | 9 | 325 |
| HPV16 | E2 | 11 | 325 |
| HPV16 | E2 | 9 | 287 |
| HPV16 | E2 | 8 | 76 |
| HPV16 | E2 | 8 | 151 |
| HPV16 | E2 | 9 | 151 |
| HPV16 | E2 | 10 | 151 |
| HPV16 | E2 | 9 | 191 |
| HPV16 | E2 | 10 | 191 |
| HPV16 | E2 | 8 | 349 |
| HPV16 | E2 | 10 | 349 |
| HPV16 | E2 | 8 | 57 |
| HPV16 | E2 | 11 | 278 |
| HPV16 | E2 | 8 | 37 |
| HPV16 | E2 | 10 | 37 |
| HPV16 | E2 | 9 | 7 |
| HPV16 | E2 | 10 | 7 |
| HPV16 | E2 | 9 | 212 |
| HPV16 | E2 | 10 | 212 |
| HPV16 | E2 | 8 | 98 |
| HPV16 | E2 | 9 | 207 |
| HPV16 | E2 | 10 | 207 |
| HPV16 | E2 | 9 | 348 |

TABLE XIV-continued

HLA-B62 Supermotif Peptides

| 1 | 2 | 3 | 4 |
|---|---|---|---|
| HPV16 | E2 | 11 | 348 |
| HPV16 | E2 | 8 | 85 |
| HPV16 | E2 | 10 | 85 |
| HPV16 | E2 | 8 | 261 |
| HPV16 | E2 | 10 | 261 |
| HPV16 | E2 | 11 | 261 |
| HPV16 | E2 | 8 | 198 |
| HPV16 | E2 | 9 | 144 |
| HPV16 | E2 | 11 | 144 |
| HPV16 | E2 | 8 | 355 |
| HPV16 | E2 | 9 | 355 |
| HPV16 | E2 | 11 | 355 |
| HPV16 | E2 | 9 | 61 |
| HPV16 | E2 | 10 | 61 |
| HPV16 | E2 | 8 | 3 |
| HPV16 | E2 | 10 | 78 |
| HPV16 | E2 | 9 | 297 |
| HPV16 | E2 | 9 | 93 |
| HPV16 | E2 | 10 | 93 |
| HPV16 | E2 | 11 | 93 |
| HPV16 | E2 | 8 | 334 |
| HPV16 | E2 | 10 | 310 |
| HPV16 | E2 | 10 | 128 |
| HPV16 | E2 | 11 | 128 |
| HPV16 | E2 | 10 | 286 |
| HPV16 | E2 | 10 | 116 |
| HPV16 | E2 | 9 | 357 |
| HPV16 | E2 | 9 | 146 |
| HPV16 | E2 | 10 | 146 |
| HPV16 | E2 | 8 | 192 |
| HPV16 | E2 | 9 | 192 |
| HPV16 | E2 | 11 | 59 |
| HPV16 | E2 | 11 | 119 |
| HPV16 | E2 | 10 | 169 |
| HPV16 | E2 | 8 | 147 |
| HPV16 | E2 | 9 | 147 |
| HPV16 | E2 | 11 | 147 |
| HPV16 | E2 | 10 | 341 |
| HPV16 | E2 | 8 | 138 |
| HPV16 | E2 | 10 | 138 |
| HPV16 | E2 | 11 | 138 |
| HPV16 | E2 | 9 | 102 |
| HPV16 | E2 | 9 | 159 |
| HPV16 | E2 | 10 | 159 |
| HPV16 | E2 | 11 | 159 |
| HPV16 | E5 | 8 | 26 |
| HPV16 | E5 | 9 | 26 |
| HPV16 | E5 | 11 | 26 |
| HPV16 | E5 | 9 | 24 |
| HPV16 | E5 | 10 | 24 |
| HPV16 | E5 | 11 | 24 |
| HPV16 | E5 | 8 | 20 |
| HPV16 | E5 | 9 | 20 |
| HPV16 | E5 | 10 | 20 |
| HPV16 | E5 | 8 | 60 |
| HPV16 | E5 | 9 | 60 |
| HPV16 | E5 | 10 | 60 |
| HPV16 | E5 | 9 | 72 |
| HPV16 | E5 | 10 | 72 |
| HPV16 | E5 | 11 | 72 |
| HPV16 | E5 | 8 | 15 |
| HPV16 | E5 | 9 | 15 |
| HPV16 | E5 | 11 | 15 |
| HPV16 | E5 | 8 | 66 |
| HPV16 | E5 | 9 | 66 |
| HPV16 | E5 | 8 | 64 |
| HPV16 | E5 | 9 | 64 |
| HPV16 | E5 | 10 | 64 |
| HPV16 | E5 | 11 | 64 |
| HPV16 | E5 | 8 | 43 |
| HPV16 | E5 | 9 | 43 |
| HPV16 | E5 | 11 | 43 |
| HPV16 | E5 | 8 | 44 |
| HPV16 | E5 | 10 | 44 |
| HPV16 | E5 | 11 | 44 |
| HPV16 | E5 | 10 | 69 |
| HPV16 | E5 | 8 | 61 |
| HPV16 | E5 | 9 | 61 |
| HPV16 | E5 | 11 | 61 |
| HPV16 | E5 | 8 | 73 |
| HPV16 | E5 | 9 | 73 |
| HPV16 | E5 | 10 | 73 |
| HPV16 | E5 | 8 | 42 |
| HPV16 | E5 | 9 | 42 |
| HPV16 | E5 | 10 | 42 |
| HPV16 | E5 | 9 | 28 |
| HPV16 | E5 | 9 | 11 |
| HPV16 | E5 | 11 | 11 |
| HPV16 | E5 | 8 | 16 |
| HPV16 | E5 | 10 | 16 |
| HPV16 | E5 | 8 | 22 |
| HPV16 | E5 | 11 | 22 |
| HPV16 | E5 | 8 | 27 |
| HPV16 | E5 | 10 | 27 |
| HPV16 | E5 | 8 | 32 |
| HPV16 | E5 | 11 | 32 |
| HPV16 | E5 | 8 | 47 |
| HPV16 | E5 | 10 | 47 |
| HPV16 | E5 | 11 | 47 |
| HPV16 | E5 | 10 | 33 |
| HPV16 | E5 | 11 | 33 |
| HPV16 | E5 | 9 | 48 |
| HPV16 | E5 | 10 | 48 |
| HPV16 | E5 | 9 | 45 |
| HPV16 | E5 | 10 | 45 |
| HPV16 | E5 | 9 | 3 |
| HPV16 | E5 | 10 | 3 |
| HPV16 | E5 | 11 | 3 |
| HPV16 | E5 | 9 | 70 |
| HPV16 | E5 | 11 | 70 |
| HPV16 | E5 | 9 | 31 |
| HPV16 | E5 | 10 | 30 |
| HPV16 | E5 | 8 | 41 |
| HPV16 | E5 | 9 | 41 |
| HPV16 | E5 | 10 | 41 |
| HPV16 | E5 | 11 | 41 |
| HPV16 | E5 | 8 | 35 |
| HPV16 | E5 | 9 | 35 |
| HPV16 | E5 | 10 | 35 |
| HPV16 | E5 | 11 | 35 |
| HPV16 | E5 | 8 | 10 |
| HPV16 | E5 | 10 | 10 |
| HPV16 | E5 | 8 | 21 |
| HPV16 | E5 | 9 | 21 |
| HPV16 | E5 | 8 | 46 |
| HPV16 | E5 | 9 | 46 |
| HPV16 | E5 | 11 | 46 |
| HPV16 | E5 | 8 | 50 |
| HPV16 | E5 | 11 | 50 |
| HPV16 | E5 | 9 | 63 |
| HPV16 | E5 | 10 | 63 |
| HPV16 | E5 | 11 | 63 |
| HPV16 | E5 | 11 | 68 |
| HPV16 | E5 | 9 | 68 |
| HPV16 | E5 | 10 | 68 |
| HPV16 | E5 | 8 | 110 |
| HPV16 | E5 | 10 | 58 |
| HPV16 | E5 | 11 | 58 |
| HPV16 | E5 | 8 | 73 |
| HPV16 | E6 | 11 | 73 |
| HPV16 | E5 | 9 | 118 |
| HPV16 | E6 | 8 | 37 |
| HPV16 | E6 | 9 | 37 |
| HPV16 | E6 | 8 | 32 |
| HPV16 | E6 | 9 | 11 |
| HPV16 | E6 | 9 | 28 |
| HPV16 | E6 | 10 | 25 |
| HPV16 | E6 | 11 | 25 |
| HPV16 | E6 | 8 | 96 |
| HPV16 | E6 | 11 | 96 |

TABLE XIV-continued

HLA-B62 Supermotif Peptides

| 1 | 2 | 3 | 4 |
|---|---|---|---|
| HPV16 | E6 | 10 | 48 |
| HPV16 | E6 | 11 | 9 |
| HPV16 | E6 | 8 | 125 |
| HPV16 | E6 | 11 | 125 |
| HPV16 | E6 | 8 | 2 |
| HPV16 | E6 | 11 | 34 |
| HPV16 | E6 | 9 | 59 |
| HPV16 | E6 | 10 | 59 |
| HPV16 | E6 | 11 | 59 |
| HPV16 | E6 | 8 | 79 |
| HPV16 | E6 | 10 | 79 |
| HPV16 | E6 | 9 | 18 |
| HPV16 | E6 | 8 | 101 |
| HPV16 | E6 | 11 | 101 |
| HPV16 | E6 | 9 | 41 |
| HPV16 | E6 | 10 | 41 |
| HPV16 | E6 | 11 | 129 |
| HPV16 | E6 | 11 | 122 |
| HPV16 | E6 | 11 | 107 |
| HPV16 | E6 | 9 | 44 |
| HPV16 | E6 | 10 | 44 |
| HPV16 | E6 | 11 | 44 |
| HPV16 | E6 | 8 | 19 |
| HPV16 | E6 | 8 | 26 |
| HPV16 | E6 | 9 | 26 |
| HPV16 | E6 | 10 | 26 |
| HPV16 | E6 | 11 | 134 |
| HPV16 | E6 | 10 | 65 |
| HPV16 | E6 | 10 | 102 |
| HPV16 | E6 | 11 | 116 |
| HPV16 | E6 | 8 | 12 |
| HPV16 | E6 | 11 | 12 |
| HPV16 | E6 | 11 | 20 |
| HPV16 | E6 | 10 | 21 |
| HPV16 | E6 | 8 | 43 |
| HPV16 | E6 | 10 | 43 |
| HPV16 | E6 | 11 | 43 |
| HPV16 | E6 | 8 | 42 |
| HPV16 | E6 | 9 | 42 |
| HPV16 | E6 | 11 | 42 |
| HPV16 | E6 | 10 | 97 |
| HPV16 | E6 | 11 | 97 |
| HPV16 | E6 | 8 | 15 |
| HPV16 | E6 | 11 | 89 |
| HPV16 | E6 | 10 | 29 |
| HPV16 | E6 | 11 | 29 |
| HPV16 | E6 | 10 | 94 |
| HPV16 | E7 | 9 | 68 |
| HPV16 | E7 | 8 | 75 |
| HPV16 | E7 | 9 | 75 |
| HPV16 | E7 | 10 | 75 |
| HPV16 | E7 | 9 | 81 |
| HPV16 | E7 | 10 | 81 |
| HPV16 | E7 | 9 | 14 |
| HPV16 | E7 | 10 | 14 |
| HPV16 | E7 | 8 | 21 |
| HPV16 | E7 | 9 | 37 |
| HPV16 | E7 | 9 | 46 |
| HPV16 | E7 | 10 | 46 |
| HPV16 | E7 | 11 | 40 |
| HPV16 | E7 | 8 | 43 |
| HPV16 | E7 | 10 | 43 |
| HPV16 | E7 | 10 | 73 |
| HPV16 | E7 | 11 | 73 |
| HPV16 | E7 | 8 | 82 |
| HPV16 | E7 | 9 | 82 |
| HPV16 | E7 | 8 | 83 |
| HPV16 | E7 | 11 | 83 |
| HPV16 | E7 | 8 | 15 |
| HPV16 | E7 | 9 | 15 |
| HPV16 | E7 | 11 | 15 |
| HPV16 | E7 | 11 | 12 |
| HPV16 | E7 | 8 | 16 |
| HPV16 | E7 | 10 | 16 |
| HPV16 | E7 | 9 | 66 |
| HPV16 | E7 | 11 | 66 |
| HPV16 | E7 | 10 | 78 |
| HPV16 | E7 | 8 | 86 |
| HPV16 | E7 | 9 | 7 |
| HPV16 | E7 | 11 | 64 |
| HPV16 | E7 | 8 | 5 |
| HPV16 | E7 | 9 | 5 |
| HPV16 | E7 | 11 | 5 |
| HPV16 | E7 | 8 | 69 |
| HPV16 | E7 | 11 | 69 |
| HPV16 | L1 | 11 | 451 |
| HPV16 | L1 | 9 | 373 |
| HPV16 | L1 | 9 | 233 |
| HPV16 | L1 | 10 | 461 |
| HPV16 | L1 | 8 | 342 |
| HPV16 | L1 | 10 | 342 |
| HPV16 | L1 | 8 | 330 |
| HPV16 | L1 | 9 | 330 |
| HPV16 | L1 | 10 | 330 |
| HPV16 | L1 | 10 | 292 |
| HPV16 | L1 | 11 | 292 |
| HPV16 | L1 | 9 | 70 |
| HPV16 | L1 | 10 | 205 |
| HPV16 | L1 | 11 | 172 |
| HPV16 | L1 | 9 | 183 |
| HPV16 | L1 | 10 | 211 |
| HPV16 | L1 | 11 | 211 |
| HPV16 | L1 | 8 | 454 |
| HPV16 | L1 | 9 | 249 |
| HPV16 | L1 | 11 | 484 |
| HPV16 | L1 | 8 | 397 |
| HPV16 | L1 | 11 | 397 |
| HPV16 | L1 | 11 | 300 |
| HPV16 | L1 | 9 | 225 |
| HPV16 | L1 | 10 | 225 |
| HPV16 | L1 | 8 | 465 |
| HPV16 | L1 | 9 | 465 |
| HPV16 | L1 | 11 | 465 |
| HPV16 | L1 | 9 | 486 |
| HPV16 | L1 | 10 | 486 |
| HPV16 | L1 | 11 | 486 |
| HPV16 | L1 | 9 | 412 |
| HPV16 | L1 | 8 | 17 |
| HPV16 | L1 | 9 | 17 |
| HPV16 | L1 | 11 | 17 |
| HPV16 | L1 | 8 | 266 |
| HPV16 | L1 | 9 | 266 |
| HPV16 | L1 | 10 | 266 |
| HPV16 | L1 | 11 | 266 |
| HPV16 | L1 | 8 | 279 |
| HPV16 | L1 | 9 | 279 |
| HPV16 | L1 | 8 | 132 |
| HPV16 | L1 | 10 | 132 |
| HPV16 | L1 | 8 | 474 |
| HPV16 | L1 | 10 | 474 |
| HPV16 | L1 | 10 | 245 |
| HPV16 | L1 | 8 | 400 |
| HPV16 | L1 | 10 | 400 |
| HPV16 | L1 | 10 | 5 |
| HPV16 | L1 | 9 | 494 |
| HPV16 | L1 | 11 | 76 |
| HPV16 | L1 | 8 | 488 |
| HPV16 | L1 | 9 | 488 |
| HPV16 | L1 | 11 | 488 |
| HPV16 | L1 | 8 | 318 |
| HPV16 | L1 | 9 | 318 |
| HPV16 | L1 | 8 | 402 |
| HPV16 | L1 | 10 | 402 |
| HPV16 | L1 | 11 | 25 |
| HPV16 | L1 | 9 | 282 |
| HPV16 | L1 | 11 | 282 |
| HPV16 | L1 | 8 | 446 |
| HPV16 | L1 | 8 | 348 |
| HPV16 | L1 | 9 | 348 |
| HPV16 | L1 | 10 | 348 |

TABLE XIV-continued

HLA-B62 Supermotif Peptides

| 1 | 2 | 3 | 4 |
|---|---|---|---|
| HPV16 | L1 | 8 | 142 |
| HPV16 | L1 | 11 | 142 |
| HPV16 | L1 | 8 | 499 |
| HPV16 | L1 | 10 | 499 |
| HPV16 | L1 | 10 | 431 |
| HPV16 | L1 | 9 | 93 |
| HPV16 | L1 | 11 | 93 |
| HPV16 | L1 | 8 | 136 |
| HPV16 | L1 | 8 | 166 |
| HPV16 | L1 | 10 | 166 |
| HPV16 | L1 | 10 | 130 |
| HPV16 | L1 | 9 | 140 |
| HPV16 | L1 | 10 | 140 |
| HPV16 | L1 | 8 | 22 |
| HPV16 | L1 | 9 | 22 |
| HPV16 | L1 | 10 | 22 |
| HPV16 | L1 | 8 | 285 |
| HPV16 | L1 | 9 | 285 |
| HPV16 | L1 | 8 | 102 |
| HPV16 | L1 | 10 | 102 |
| HPV16 | L1 | 9 | 424 |
| HPV16 | L1 | 11 | 8 |
| HPV16 | L1 | 9 | 86 |
| HPV16 | L1 | 11 | 86 |
| HPV16 | L1 | 11 | 221 |
| HPV16 | L1 | 10 | 85 |
| HPV16 | L1 | 8 | 406 |
| HPV16 | L1 | 9 | 406 |
| HPV16 | L1 | 11 | 406 |
| HPV16 | L1 | 8 | 151 |
| HPV16 | L1 | 10 | 151 |
| HPV16 | L1 | 11 | 151 |
| HPV16 | L1 | 11 | 262 |
| HPV16 | L1 | 11 | 503 |
| HPV16 | L1 | 8 | 80 |
| HPV16 | L1 | 9 | 80 |
| HPV16 | L1 | 8 | 188 |
| HPV16 | L1 | 8 | 335 |
| HPV16 | L1 | 8 | 178 |
| HPV16 | L1 | 9 | 90 |
| HPV16 | L1 | 10 | 90 |
| HPV16 | L1 | 8 | 46 |
| HPV16 | L1 | 9 | 46 |
| HPV16 | L1 | 10 | 46 |
| HPV16 | L1 | 8 | 184 |
| HPV16 | L1 | 11 | 216 |
| HPV16 | L1 | 8 | 68 |
| HPV16 | L1 | 9 | 68 |
| HPV16 | L1 | 11 | 68 |
| HPV16 | L1 | 11 | 148 |
| HPV16 | L1 | 8 | 495 |
| HPV16 | L1 | 9 | 103 |
| HPV16 | L1 | 9 | 39 |
| HPV16 | L1 | 10 | 39 |
| HPV16 | L1 | 8 | 31 |
| HPV16 | L1 | 9 | 31 |
| HPV16 | L1 | 11 | 496 |
| HPV16 | L1 | 8 | 239 |
| HPV16 | L1 | 10 | 239 |
| HPV16 | L1 | 10 | 398 |
| HPV16 | L1 | 9 | 432 |
| HPV16 | L1 | 11 | 339 |
| HPV16 | L1 | 8 | 94 |
| HPV16 | L1 | 10 | 94 |
| HPV16 | L1 | 10 | 9 |
| HPV16 | L1 | 8 | 87 |
| HPV16 | L1 | 10 | 87 |
| HPV16 | L1 | 8 | 124 |
| HPV16 | L1 | 10 | 124 |
| HPV16 | L1 | 8 | 1 |
| HPV16 | L1 | 9 | 1 |
| HPV16 | L1 | 10 | 1 |
| HPV16 | L1 | 11 | 1 |
| HPV16 | L1 | 8 | 226 |
| HPV16 | L1 | 9 | 226 |
| HPV16 | L1 | 11 | 226 |
| HPV16 | L1 | 10 | 263 |
| HPV16 | L1 | 11 | 263 |
| HPV16 | L1 | 8 | 325 |
| HPV16 | L1 | 9 | 325 |
| HPV16 | L1 | 11 | 58 |
| HPV16 | L1 | 8 | 311 |
| HPV16 | L1 | 8 | 476 |
| HPV16 | L1 | 10 | 476 |
| HPV16 | L1 | 8 | 367 |
| HPV16 | L1 | 8 | 118 |
| HPV16 | L1 | 9 | 118 |
| HPV16 | L1 | 10 | 118 |
| HPV16 | L1 | 8 | 207 |
| HPV16 | L1 | 10 | 207 |
| HPV16 | L1 | 11 | 207 |
| HPV16 | L1 | 8 | 353 |
| HPV16 | L1 | 8 | 296 |
| HPV16 | L1 | 9 | 19 |
| HPV16 | L1 | 11 | 19 |
| HPV16 | L1 | 10 | 77 |
| HPV16 | L1 | 11 | 77 |
| HPV16 | L1 | 8 | 247 |
| HPV16 | L1 | 11 | 247 |
| HPV16 | L1 | 8 | 213 |
| HPV16 | L1 | 9 | 213 |
| HPV16 | L1 | 8 | 489 |
| HPV16 | L1 | 10 | 489 |
| HPV16 | L1 | 11 | 138 |
| HPV16 | L1 | 8 | 466 |
| HPV16 | L1 | 10 | 466 |
| HPV16 | L1 | 9 | 459 |
| HPV16 | L1 | 10 | 435 |
| HPV16 | L1 | 9 | 212 |
| HPV16 | L1 | 10 | 212 |
| HPV16 | L1 | 11 | 434 |
| HPV16 | L1 | 8 | 40 |
| HPV16 | L1 | 9 | 40 |
| HPV16 | L1 | 8 | 41 |
| HPV16 | L1 | 11 | 43 |
| HPV16 | L1 | 8 | 331 |
| HPV16 | L1 | 9 | 331 |
| HPV16 | L1 | 9 | 403 |
| HPV16 | L1 | 11 | 403 |
| HPV16 | L1 | 11 | 181 |
| HPV16 | L1 | 8 | 280 |
| HPV16 | L1 | 11 | 280 |
| HPV16 | L1 | 10 | 26 |
| HPV16 | L1 | 8 | 433 |
| HPV16 | L1 | 8 | 2 |
| HPV16 | L1 | 9 | 2 |
| HPV16 | L1 | 10 | 2 |
| HPV16 | L1 | 10 | 100 |
| HPV16 | L1 | 9 | 67 |
| HPV16 | L1 | 10 | 67 |
| HPV16 | L1 | 9 | 123 |
| HPV16 | L1 | 11 | 123 |
| HPV16 | L1 | 8 | 253 |
| HPV16 | L1 | 9 | 253 |
| HPV16 | L1 | 11 | 253 |
| HPV16 | L1 | 11 | 271 |
| HPV16 | L1 | 8 | 28 |
| HPV16 | L1 | 10 | 28 |
| HPV16 | L1 | 11 | 28 |
| HPV16 | L1 | 9 | 174 |
| HPV16 | L1 | 11 | 74 |
| HPV16 | L1 | 10 | 419 |
| HPV16 | L1 | 9 | 324 |
| HPV16 | L1 | 10 | 324 |
| HPV16 | L1 | 8 | 199 |
| HPV16 | L1 | 8 | 423 |
| HPV16 | L1 | 10 | 423 |
| HPV16 | L1 | 8 | 439 |
| HPV16 | L1 | 9 | 439 |
| HPV16 | L1 | 9 | 238 |

TABLE XIV-continued

HLA-B62 Supermotif Peptides

| 1 | 2 | 3 | 4 |
|---|---|---|---|
| HPV16 | L1 | 11 | 238 |
| HPV16 | L1 | 9 | 408 |
| HPV16 | L1 | 10 | 408 |
| HPV16 | L1 | 10 | 458 |
| HPV16 | L1 | 11 | 320 |
| HPV16 | L1 | 11 | 514 |
| HPV16 | L1 | 9 | 121 |
| HPV16 | L1 | 11 | 121 |
| HPV16 | L1 | 8 | 219 |
| HPV16 | L1 | 9 | 219 |
| HPV16 | L1 | 11 | 358 |
| HPV16 | L1 | 9 | 36 |
| HPV16 | L1 | 8 | 220 |
| HPV16 | L1 | 9 | 10 |
| HPV16 | L1 | 11 | 10 |
| HPV16 | L1 | 8 | 413 |
| HPV16 | L1 | 9 | 88 |
| HPV16 | L1 | 11 | 88 |
| HPV16 | L1 | 9 | 246 |
| HPV16 | L1 | 10 | 359 |
| HPV16 | L1 | 8 | 47 |
| HPV16 | L1 | 9 | 47 |
| HPV16 | L1 | 8 | 30 |
| HPV16 | L1 | 9 | 30 |
| HPV16 | L1 | 10 | 30 |
| HPV16 | L1 | 9 | 416 |
| HPV16 | L1 | 10 | 416 |
| HPV16 | L1 | 9 | 302 |
| HPV16 | L1 | 11 | 302 |
| HPV16 | L1 | 9 | 260 |
| HPV16 | L1 | 8 | 7 |
| HPV16 | L1 | 10 | 38 |
| HPV16 | L1 | 11 | 38 |
| HPV16 | L1 | 8 | 389 |
| HPV16 | L1 | 10 | 389 |
| HPV16 | L1 | 8 | 275 |
| HPV16 | L1 | 9 | 275 |
| HPV16 | L1 | 8 | 257 |
| HPV16 | L1 | 8 | 53 |
| HPV16 | L1 | 9 | 53 |
| HPV16 | L1 | 11 | 53 |
| HPV16 | L2 | 9 | 144 |
| HPV16 | L2 | 10 | 356 |
| HPV16 | L2 | 11 | 356 |
| HPV16 | L2 | 9 | 293 |
| HPV16 | L2 | 11 | 293 |
| HPV16 | L2 | 9 | 278 |
| HPV16 | L2 | 10 | 278 |
| HPV16 | L2 | 11 | 278 |
| HPV16 | L2 | 8 | 424 |
| HPV16 | L2 | 8 | 119 |
| HPV16 | L2 | 9 | 87 |
| HPV16 | L2 | 9 | 28 |
| HPV16 | L2 | 11 | 31 |
| HPV16 | L2 | 9 | 147 |
| HPV16 | L2 | 10 | 415 |
| HPV16 | L2 | 9 | 285 |
| HPV16 | L2 | 10 | 285 |
| HPV16 | L2 | 8 | 367 |
| HPV16 | L2 | 11 | 239 |
| HPV16 | L2 | 8 | 280 |
| HPV16 | L2 | 9 | 280 |
| HPV16 | L2 | 10 | 280 |
| HPV16 | L2 | 8 | 102 |
| HPV16 | L2 | 11 | 165 |
| HPV16 | L2 | 10 | 96 |
| HPV16 | L2 | 11 | 96 |
| HPV16 | L2 | 9 | 422 |
| HPV16 | L2 | 10 | 422 |
| HPV16 | L2 | 9 | 43 |
| HPV16 | L2 | 11 | 43 |
| HPV16 | L2 | 8 | 261 |
| HPV16 | L2 | 8 | 195 |
| HPV16 | L2 | 9 | 195 |
| HPV16 | L2 | 10 | 340 |
| HPV16 | L2 | 10 | 114 |
| HPV16 | L2 | 10 | 373 |
| HPV16 | L2 | 8 | 242 |
| HPV16 | L2 | 9 | 242 |
| HPV16 | L2 | 11 | 242 |
| HPV16 | L2 | 10 | 201 |
| HPV16 | L2 | 11 | 283 |
| HPV16 | L2 | 8 | 259 |
| HPV16 | L2 | 9 | 259 |
| HPV16 | L2 | 10 | 259 |
| HPV16 | L2 | 10 | 364 |
| HPV16 | L2 | 11 | 364 |
| HPV16 | L2 | 10 | 226 |
| HPV16 | L2 | 8 | 413 |
| HPV16 | L2 | 8 | 99 |
| HPV16 | L2 | 10 | 99 |
| HPV16 | L2 | 11 | 99 |
| HPV16 | L2 | 9 | 52 |
| HPV16 | L2 | 8 | 439 |
| HPV16 | L2 | 9 | 439 |
| HPV16 | L2 | 10 | 439 |
| HPV16 | L2 | 10 | 32 |
| HPV16 | L2 | 11 | 32 |
| HPV16 | L2 | 8 | 145 |
| HPV16 | L2 | 11 | 145 |
| HPV16 | L2 | 9 | 45 |
| HPV16 | L2 | 10 | 45 |
| HPV16 | L2 | 11 | 45 |
| HPV16 | L2 | 9 | 394 |
| HPV16 | L2 | 9 | 400 |
| HPV16 | L2 | 11 | 400 |
| HPV16 | L2 | 8 | 216 |
| HPV16 | L2 | 10 | 216 |
| HPV16 | L2 | 9 | 416 |
| HPV16 | L2 | 10 | 428 |
| HPV16 | L2 | 9 | 33 |
| HPV16 | L2 | 10 | 33 |
| HPV16 | L2 | 10 | 73 |
| HPV16 | L2 | 9 | 408 |
| HPV16 | L2 | 11 | 408 |
| HPV16 | L2 | 8 | 196 |
| HPV16 | L2 | 8 | 126 |
| HPV16 | L2 | 10 | 126 |
| HPV16 | L2 | 8 | 286 |
| HPV16 | L2 | 9 | 286 |
| HPV16 | L2 | 8 | 430 |
| HPV16 | L2 | 10 | 430 |
| HPV16 | L2 | 11 | 430 |
| HPV16 | L2 | 10 | 105 |
| HPV16 | L2 | 11 | 105 |
| HPV16 | L2 | 9 | 202 |
| HPV16 | L2 | 9 | 248 |
| HPV16 | L2 | 10 | 248 |
| HPV16 | L2 | 10 | 23 |
| HPV16 | L2 | 11 | 23 |
| HPV16 | L2 | 8 | 35 |
| HPV16 | L2 | 11 | 35 |
| HPV16 | L2 | 8 | 323 |
| HPV16 | L2 | 11 | 323 |
| HPV16 | L2 | 8 | 236 |
| HPV16 | L2 | 11 | 427 |
| HPV16 | L2 | 8 | 249 |
| HPV16 | L2 | 9 | 249 |
| HPV16 | L2 | 9 | 357 |
| HPV16 | L2 | 10 | 357 |
| HPV16 | L2 | 8 | 462 |
| HPV16 | L2 | 10 | 462 |
| HPV16 | L2 | 11 | 462 |
| HPV16 | L2 | 9 | 341 |
| HPV16 | L2 | 8 | 46 |
| HPV16 | L2 | 9 | 46 |
| HPV16 | L2 | 10 | 46 |
| HPV16 | L2 | 8 | 108 |
| HPV16 | L2 | 10 | 108 |
| HPV16 | L2 | 9 | 410 |

TABLE XIV-continued

HLA-B62 Supermotif Peptides

| 1 | 2 | 3 | 4 |
|---|---|---|---|
| HPV16 | L2 | 11 | 410 |
| HPV16 | L2 | 9 | 454 |
| HPV16 | L2 | 11 | 454 |
| HPV16 | L2 | 8 | 276 |
| HPV16 | L2 | 9 | 276 |
| HPV16 | L2 | 11 | 276 |
| HPV16 | L2 | 10 | 407 |
| HPV16 | L2 | 9 | 419 |
| HPV16 | L2 | 10 | 419 |
| HPV16 | L2 | 9 | 254 |
| HPV16 | L2 | 11 | 206 |
| HPV16 | L2 | 9 | 160 |
| HPV16 | L2 | 10 | 160 |
| HPV16 | L2 | 8 | 417 |
| HPV16 | L2 | 11 | 417 |
| HPV16 | L2 | 8 | 215 |
| HPV16 | L2 | 9 | 215 |
| HPV16 | L2 | 11 | 215 |
| HPV16 | L2 | 9 | 429 |
| HPV16 | L2 | 11 | 429 |
| HPV16 | L2 | 9 | 74 |
| HPV16 | L2 | 8 | 409 |
| HPV16 | L2 | 10 | 409 |
| HPV16 | L2 | 8 | 29 |
| HPV16 | L2 | 9 | 127 |
| HPV16 | L2 | 8 | 91 |
| HPV16 | L2 | 8 | 79 |
| HPV16 | L2 | 9 | 79 |
| HPV16 | L2 | 11 | 79 |
| HPV16 | L2 | 11 | 171 |
| HPV16 | L2 | 9 | 435 |
| HPV16 | L2 | 8 | 221 |
| HPV16 | L2 | 9 | 97 |
| HPV16 | L2 | 10 | 97 |
| HPV16 | L2 | 10 | 381 |
| HPV16 | L2 | 8 | 88 |
| HPV16 | L2 | 11 | 88 |
| HPV16 | L2 | 8 | 44 |
| HPV16 | L2 | 10 | 44 |
| HPV16 | L2 | 11 | 44 |
| HPV16 | L2 | 9 | 17 |
| HPV16 | L2 | 9 | 233 |
| HPV16 | L2 | 10 | 233 |
| HPV16 | L2 | 11 | 233 |
| HPV16 | L2 | 8 | 234 |
| HPV16 | L2 | 9 | 234 |
| HPV16 | L2 | 10 | 234 |
| HPV16 | L2 | 8 | 305 |
| HPV16 | L2 | 9 | 461 |
| HPV16 | L2 | 11 | 461 |
| HPV16 | L2 | 11 | 291 |
| HPV16 | L2 | 9 | 90 |
| HPV16 | L2 | 9 | 78 |
| HPV16 | L2 | 10 | 78 |
| HPV16 | L2 | 8 | 220 |
| HPV16 | L2 | 9 | 220 |
| HPV16 | L2 | 8 | 319 |
| HPV16 | L2 | 9 | 319 |
| HPV16 | L2 | 10 | 319 |
| HPV16 | L2 | 10 | 274 |
| HPV16 | L2 | 11 | 274 |
| HPV16 | L2 | 9 | 360 |
| HPV16 | L2 | 10 | 360 |
| HPV16 | L2 | 11 | 360 |
| HPV16 | L2 | 9 | 125 |
| HPV16 | L2 | 11 | 125 |
| HPV16 | L2 | 11 | 134 |
| HPV16 | L2 | 11 | 104 |
| HPV16 | L2 | 8 | 389 |
| HPV16 | L2 | 8 | 107 |
| HPV16 | L2 | 9 | 107 |
| HPV16 | L2 | 11 | 107 |
| HPV16 | L2 | 9 | 50 |
| HPV16 | L2 | 11 | 50 |
| HPV16 | L2 | 8 | 434 |
| HPV16 | L2 | 10 | 434 |
| HPV16 | L2 | 9 | 167 |
| HPV16 | L2 | 9 | 122 |
| HPV16 | L2 | 10 | 384 |
| HPV16 | L2 | 11 | 384 |
| HPV16 | L2 | 9 | 40 |
| HPV16 | L2 | 8 | 332 |
| HPV16 | L2 | 10 | 332 |
| HPV16 | L2 | 9 | 438 |
| HPV16 | L2 | 10 | 438 |
| HPV16 | L2 | 11 | 438 |
| HPV16 | L2 | 8 | 399 |
| HPV16 | L2 | 10 | 399 |
| HPV16 | L2 | 10 | 187 |
| HPV16 | L2 | 9 | 85 |
| HPV16 | L2 | 11 | 85 |
| HPV16 | L2 | 10 | 311 |
| HPV16 | L2 | 11 | 265 |
| HPV16 | L2 | 9 | 173 |
| HPV16 | L2 | 11 | 173 |
| HPV16 | L2 | 11 | 142 |
| HPV16 | L2 | 9 | 214 |
| HPV16 | L2 | 10 | 214 |
| HPV16 | L2 | 11 | 345 |
| HPV16 | L2 | 8 | 245 |
| HPV16 | L2 | 11 | 380 |
| HPV16 | L2 | 10 | 16 |
| HPV16 | L2 | 10 | 232 |
| HPV16 | L2 | 11 | 232 |
| HPV16 | L2 | 8 | 209 |
| HPV16 | L2 | 10 | 154 |
| HPV16 | L2 | 8 | 168 |
| HPV16 | L2 | 9 | 431 |
| HPV16 | L2 | 10 | 431 |
| HPV16 | L2 | 11 | 431 |
| HPV16 | L2 | 8 | 123 |
| HPV16 | L2 | 11 | 123 |
| HPV16 | L2 | 9 | 385 |
| HPV16 | L2 | 10 | 385 |
| HPV16 | L2 | 9 | 382 |
| HPV16 | L2 | 8 | 393 |
| HPV16 | L2 | 10 | 393 |
| HPV16 | L2 | 11 | 72 |
| HPV16 | L2 | 8 | 447 |
| HPV16 | L2 | 9 | 447 |
| HPV16 | L2 | 10 | 453 |
| HPV18 | E1 | 9 | 246 |
| HPV18 | E1 | 10 | 246 |
| HPV18 | E1 | 10 | 22 |
| HPV18 | E1 | 11 | 22 |
| HPV18 | E1 | 9 | 546 |
| HPV18 | E1 | 8 | 68 |
| HPV18 | E1 | 10 | 387 |
| HPV18 | E1 | 11 | 387 |
| HPV18 | E1 | 9 | 325 |
| HPV18 | E1 | 10 | 213 |
| HPV18 | E1 | 11 | 526 |
| HPV18 | E1 | 10 | 66 |
| HPV18 | E1 | 8 | 72 |
| HPV18 | E1 | 10 | 72 |
| HPV18 | E1 | 11 | 72 |
| HPV18 | E1 | 8 | 422 |
| HPV18 | E1 | 11 | 422 |
| HPV18 | E1 | 9 | 199 |
| HPV18 | E1 | 11 | 79 |
| HPV18 | E1 | 9 | 216 |
| HPV18 | E1 | 11 | 216 |
| HPV18 | E1 | 8 | 273 |
| HPV18 | E1 | 9 | 273 |
| HPV18 | E1 | 10 | 273 |
| HPV18 | E1 | 11 | 273 |
| HPV18 | E1 | 8 | 479 |
| HPV18 | E1 | 9 | 311 |
| HPV18 | E1 | 10 | 566 |
| HPV18 | E1 | 10 | 404 |

TABLE XIV-continued

HLA-B62 Supermotif Peptides

| 1 | 2 | 3 | 4 |
|---|---|---|---|
| HPV18 | E1 | 9 | 628 |
| HPV18 | E1 | 11 | 203 |
| HPV18 | E1 | 8 | 363 |
| HPV18 | E1 | 9 | 363 |
| HPV18 | E1 | 10 | 363 |
| HPV18 | E1 | 8 | 381 |
| HPV18 | E1 | 9 | 381 |
| HPV18 | E1 | 10 | 381 |
| HPV18 | E1 | 11 | 30 |
| HPV18 | E1 | 10 | 610 |
| HPV18 | E1 | 11 | 610 |
| HPV18 | E1 | 11 | 115 |
| HPV18 | E1 | 8 | 62 |
| HPV18 | E1 | 9 | 62 |
| HPV18 | E1 | 11 | 62 |
| HPV18 | E1 | 9 | 108 |
| HPV18 | E1 | 11 | 108 |
| HPV18 | E1 | 8 | 375 |
| HPV18 | E1 | 9 | 375 |
| HPV18 | E1 | 10 | 375 |
| HPV18 | E1 | 11 | 366 |
| HPV18 | E1 | 8 | 518 |
| HPV18 | E1 | 9 | 518 |
| HPV18 | E1 | 10 | 518 |
| HPV18 | E1 | 11 | 518 |
| HPV18 | E1 | 8 | 59 |
| HPV18 | E1 | 10 | 59 |
| HPV18 | E1 | 11 | 59 |
| HPV18 | E1 | 10 | 104 |
| HPV18 | E1 | 9 | 141 |
| HPV18 | E1 | 8 | 74 |
| HPV18 | E1 | 9 | 74 |
| HPV18 | E1 | 11 | 74 |
| HPV18 | E1 | 9 | 338 |
| HPV18 | E1 | 10 | 338 |
| HPV18 | E1 | 8 | 50 |
| HPV18 | E1 | 8 | 497 |
| HPV18 | E1 | 9 | 497 |
| HPV18 | E1 | 10 | 497 |
| HPV18 | E1 | 10 | 265 |
| HPV18 | E1 | 9 | 500 |
| HPV18 | E1 | 10 | 500 |
| HPV18 | E1 | 8 | 460 |
| HPV18 | E1 | 11 | 460 |
| HPV18 | E1 | 8 | 463 |
| HPV18 | E1 | 9 | 463 |
| HPV18 | E1 | 11 | 470 |
| HPV18 | E1 | 8 | 399 |
| HPV18 | E1 | 10 | 399 |
| HPV18 | E1 | 11 | 399 |
| HPV18 | E1 | 9 | 452 |
| HPV18 | E1 | 10 | 452 |
| HPV18 | E1 | 10 | 599 |
| HPV18 | E1 | 11 | 599 |
| HPV18 | E1 | 8 | 508 |
| HPV18 | E1 | 9 | 508 |
| HPV18 | E1 | 10 | 508 |
| HPV18 | E1 | 9 | 356 |
| HPV18 | E1 | 8 | 332 |
| HPV18 | E1 | 9 | 332 |
| HPV18 | E1 | 8 | 223 |
| HPV18 | E1 | 11 | 223 |
| HPV18 | E1 | 8 | 300 |
| HPV18 | E1 | 8 | 494 |
| HPV18 | E1 | 11 | 494 |
| HPV18 | E1 | 9 | 484 |
| HPV18 | E1 | 10 | 484 |
| HPV18 | E1 | 9 | 121 |
| HPV18 | E1 | 10 | 121 |
| HPV18 | E1 | 8 | 279 |
| HPV18 | E1 | 10 | 279 |
| HPV18 | E1 | 10 | 249 |
| HPV18 | E1 | 9 | 270 |
| HPV18 | E1 | 11 | 270 |
| HPV18 | E1 | 8 | 576 |
| HPV18 | E1 | 10 | 576 |
| HPV18 | E1 | 11 | 576 |
| HPV18 | E1 | 8 | 83 |
| HPV18 | E1 | 8 | 306 |
| HPV18 | E1 | 9 | 306 |
| HPV18 | E1 | 11 | 352 |
| HPV18 | E1 | 10 | 569 |
| HPV18 | E1 | 9 | 266 |
| HPV18 | E1 | 8 | 271 |
| HPV18 | E1 | 10 | 271 |
| HPV18 | E1 | 11 | 271 |
| HPV18 | E1 | 8 | 501 |
| HPV18 | E1 | 9 | 501 |
| HPV18 | E1 | 10 | 353 |
| HPV18 | E1 | 8 | 562 |
| HPV18 | E1 | 9 | 562 |
| HPV18 | E1 | 10 | 562 |
| HPV18 | E1 | 8 | 262 |
| HPV18 | E1 | 10 | 262 |
| HPV18 | E1 | 10 | 314 |
| HPV18 | E1 | 11 | 314 |
| HPV18 | E1 | 11 | 347 |
| HPV18 | E1 | 9 | 23 |
| HPV18 | E1 | 10 | 23 |
| HPV18 | E1 | 10 | 449 |
| HPV18 | E1 | 8 | 439 |
| HPV18 | E1 | 11 | 439 |
| HPV18 | E1 | 11 | 647 |
| HPV18 | E1 | 8 | 318 |
| HPV18 | E1 | 9 | 318 |
| HPV18 | E1 | 10 | 318 |
| HPV18 | E1 | 11 | 318 |
| HPV18 | E1 | 11 | 559 |
| HPV18 | E1 | 8 | 210 |
| HPV18 | E1 | 9 | 210 |
| HPV18 | E1 | 8 | 524 |
| HPV18 | E1 | 8 | 206 |
| HPV18 | E1 | 9 | 206 |
| HPV18 | E1 | 10 | 206 |
| HPV18 | E1 | 11 | 206 |
| HPV18 | E1 | 8 | 281 |
| HPV18 | E1 | 9 | 561 |
| HPV18 | E1 | 10 | 561 |
| HPV18 | E1 | 11 | 561 |
| HPV18 | E1 | 8 | 261 |
| HPV18 | E1 | 9 | 261 |
| HPV18 | E1 | 11 | 261 |
| HPV18 | E1 | 11 | 313 |
| HPV18 | E1 | 9 | 388 |
| HPV18 | E1 | 10 | 388 |
| HPV18 | E1 | 11 | 388 |
| HPV18 | E1 | 9 | 304 |
| HPV18 | E1 | 10 | 304 |
| HPV18 | E1 | 11 | 304 |
| HPV18 | E1 | 10 | 204 |
| HPV18 | E1 | 11 | 204 |
| HPV18 | E1 | 11 | 285 |
| HPV18 | E1 | 9 | 570 |
| HPV18 | E1 | 9 | 214 |
| HPV18 | E1 | 11 | 214 |
| HPV18 | E1 | 10 | 527 |
| HPV18 | E1 | 8 | 312 |
| HPV18 | E1 | 11 | 47 |
| HPV18 | E1 | 10 | 367 |
| HPV18 | E1 | 11 | 188 |
| HPV18 | E1 | 10 | 574 |
| HPV18 | E1 | 8 | 428 |
| HPV18 | E1 | 8 | 641 |
| HPV18 | E1 | 10 | 641 |
| HPV18 | E1 | 9 | 193 |
| HPV18 | E1 | 8 | 251 |
| HPV18 | E1 | 11 | 251 |
| HPV18 | E1 | 11 | 606 |
| HPV18 | E1 | 10 | 158 |
| HPV18 | E1 | 11 | 158 |

TABLE XIV-continued

HLA-B62 Supermotif Peptides

| 1 | 2 | 3 | 4 |
|---|---|---|---|
| HPV18 | E1 | 8 | 191 |
| HPV18 | E1 | 9 | 191 |
| HPV18 | E1 | 11 | 191 |
| HPV18 | E1 | 8 | 568 |
| HPV18 | E1 | 11 | 568 |
| HPV18 | E1 | 11 | 551 |
| HPV18 | E1 | 8 | 448 |
| HPV18 | E1 | 11 | 448 |
| HPV18 | E1 | 8 | 98 |
| HPV18 | E1 | 10 | 560 |
| HPV18 | E1 | 11 | 560 |
| HPV18 | E1 | 8 | 519 |
| HPV18 | E1 | 9 | 519 |
| HPV18 | E1 | 10 | 519 |
| HPV18 | E1 | 9 | 567 |
| HPV18 | E1 | 8 | 316 |
| HPV18 | E1 | 9 | 316 |
| HPV18 | E1 | 10 | 316 |
| HPV18 | E1 | 11 | 316 |
| HPV18 | E1 | 8 | 194 |
| HPV18 | E1 | 11 | 194 |
| HPV18 | E1 | 10 | 607 |
| HPV18 | E1 | 8 | 457 |
| HPV18 | E1 | 10 | 457 |
| HPV18 | E1 | 11 | 457 |
| HPV18 | E1 | 8 | 563 |
| HPV18 | E1 | 9 | 563 |
| HPV18 | E1 | 8 | 200 |
| HPV18 | E1 | 8 | 426 |
| HPV18 | E1 | 10 | 426 |
| HPV18 | E1 | 9 | 263 |
| HPV18 | E1 | 9 | 315 |
| HPV18 | E1 | 10 | 315 |
| HPV18 | E1 | 11 | 315 |
| HPV18 | E1 | 8 | 456 |
| HPV18 | E1 | 9 | 456 |
| HPV18 | E1 | 11 | 456 |
| HPV18 | E1 | 10 | 80 |
| HPV18 | E1 | 11 | 80 |
| HPV18 | E1 | 10 | 589 |
| HPV18 | E1 | 11 | 589 |
| HPV18 | E1 | 11 | 626 |
| HPV18 | E1 | 8 | 102 |
| HPV18 | E1 | 10 | 128 |
| HPV18 | E1 | 9 | 349 |
| HPV18 | E1 | 8 | 294 |
| HPV18 | E1 | 11 | 294 |
| HPV18 | E1 | 9 | 447 |
| HPV18 | E1 | 8 | 425 |
| HPV18 | E1 | 9 | 425 |
| HPV18 | E1 | 11 | 425 |
| HPV18 | E1 | 9 | 553 |
| HPV18 | E1 | 10 | 553 |
| HPV18 | E1 | 9 | 117 |
| HPV18 | E1 | 9 | 97 |
| HPV18 | E1 | 9 | 110 |
| HPV18 | E1 | 11 | 430 |
| HPV18 | E1 | 8 | 322 |
| HPV18 | E1 | 11 | 179 |
| HPV18 | E1 | 9 | 253 |
| HPV18 | E1 | 10 | 253 |
| HPV18 | E1 | 8 | 197 |
| HPV18 | E1 | 9 | 197 |
| HPV18 | E1 | 11 | 197 |
| HPV18 | E1 | 8 | 260 |
| HPV18 | E1 | 9 | 260 |
| HPV18 | E1 | 10 | 260 |
| HPV18 | E1 | 10 | 303 |
| HPV18 | E1 | 11 | 303 |
| HPV18 | E1 | 9 | 414 |
| HPV18 | E1 | 8 | 343 |
| HPV18 | E1 | 10 | 343 |
| HPV18 | E1 | 11 | 343 |
| HPV18 | E1 | 8 | 474 |
| HPV18 | E1 | 9 | 474 |
| HPV18 | E1 | 9 | 53 |
| HPV18 | E1 | 11 | 53 |
| HPV18 | E1 | 9 | 296 |
| HPV18 | E1 | 10 | 296 |
| HPV18 | E1 | 8 | 591 |
| HPV18 | E1 | 9 | 591 |
| HPV18 | E1 | 11 | 591 |
| HPV18 | E1 | 10 | 31 |
| HPV18 | E1 | 11 | 505 |
| HPV18 | E1 | 9 | 81 |
| HPV18 | E1 | 10 | 81 |
| HPV18 | E1 | 9 | 280 |
| HPV18 | E1 | 8 | 339 |
| HPV18 | E1 | 9 | 339 |
| HPV18 | E1 | 8 | 307 |
| HPV18 | E1 | 9 | 450 |
| HPV18 | E1 | 11 | 450 |
| HPV18 | E1 | 9 | 368 |
| HPV18 | E1 | 8 | 346 |
| HPV18 | E1 | 9 | 432 |
| HPV18 | E1 | 10 | 516 |
| HPV18 | E1 | 11 | 516 |
| HPV18 | E1 | 8 | 583 |
| HPV18 | E1 | 10 | 583 |
| HPV18 | E1 | 11 | 583 |
| HPV18 | E1 | 8 | 243 |
| HPV18 | E1 | 8 | 585 |
| HPV18 | E1 | 9 | 585 |
| HPV18 | E1 | 11 | 585 |
| HPV18 | E1 | 8 | 408 |
| HPV18 | E1 | 11 | 542 |
| HPV18 | E1 | 9 | 455 |
| HPV18 | E1 | 10 | 455 |
| HPV18 | E2 | 8 | 76 |
| HPV18 | E2 | 11 | 76 |
| HPV18 | E2 | 11 | 45 |
| HPV18 | E2 | 8 | 351 |
| HPV18 | E2 | 9 | 351 |
| HPV18 | E2 | 10 | 351 |
| HPV18 | E2 | 10 | 82 |
| HPV18 | E2 | 10 | 87 |
| HPV18 | E2 | 10 | 132 |
| HPV18 | E2 | 11 | 132 |
| HPV18 | E2 | 10 | 14 |
| HPV18 | E2 | 8 | 156 |
| HPV18 | E2 | 9 | 156 |
| HPV18 | E2 | 10 | 156 |
| HPV18 | E2 | 8 | 29 |
| HPV18 | E2 | 9 | 29 |
| HPV18 | E2 | 11 | 29 |
| HPV18 | E2 | 8 | 315 |
| HPV18 | E2 | 11 | 315 |
| HPV18 | E2 | 9 | 78 |
| HPV18 | E2 | 10 | 78 |
| HPV18 | E2 | 11 | 104 |
| HPV18 | E2 | 8 | 190 |
| HPV18 | E2 | 9 | 190 |
| HPV18 | E2 | 11 | 346 |
| HPV18 | E2 | 9 | 54 |
| HPV18 | E2 | 10 | 54 |
| HPV18 | E2 | 11 | 253 |
| HPV18 | E2 | 9 | 161 |
| HPV18 | E2 | 9 | 261 |
| HPV18 | E2 | 10 | 261 |
| HPV18 | E2 | 8 | 118 |
| HPV18 | E2 | 9 | 291 |
| HPV18 | E2 | 9 | 60 |
| HPV18 | E2 | 11 | 289 |
| HPV18 | E2 | 8 | 358 |
| HPV18 | E2 | 8 | 352 |
| HPV18 | E2 | 9 | 352 |
| HPV18 | E2 | 11 | 352 |
| HPV18 | E2 | 8 | 55 |
| HPV18 | E2 | 9 | 55 |
| HPV18 | E2 | 11 | 55 |

TABLE XIV-continued

HLA-B62 Supermotif Peptides

| 1 | 2 | 3 | 4 |
|---|---|---|---|
| HPV18 | E2 | 9 | 34 |
| HPV18 | E2 | 10 | 280 |
| HPV18 | E2 | 11 | 280 |
| HPV18 | E2 | 10 | 257 |
| HPV18 | E2 | 11 | 257 |
| HPV18 | E2 | 10 | 219 |
| HPV18 | E2 | 8 | 39 |
| HPV18 | E2 | 9 | 39 |
| HPV18 | E2 | 10 | 39 |
| HPV18 | E2 | 11 | 39 |
| HPV18 | E2 | 8 | 98 |
| HPV18 | E2 | 9 | 98 |
| HPV18 | E2 | 9 | 83 |
| HPV18 | E2 | 8 | 221 |
| HPV18 | E2 | 8 | 79 |
| HPV18 | E2 | 9 | 79 |
| HPV18 | E2 | 8 | 1 |
| HPV18 | E2 | 10 | 67 |
| HPV18 | E2 | 11 | 67 |
| HPV18 | E2 | 9 | 196 |
| HPV18 | E2 | 8 | 262 |
| HPV18 | E2 | 9 | 262 |
| HPV18 | E2 | 9 | 357 |
| HPV18 | E2 | 8 | 33 |
| HPV18 | E2 | 10 | 33 |
| HPV18 | E2 | 8 | 38 |
| HPV18 | E2 | 9 | 38 |
| HPV18 | E2 | 10 | 38 |
| HPV18 | E2 | 11 | 38 |
| HPV18 | E2 | 9 | 220 |
| HPV18 | E2 | 8 | 80 |
| HPV18 | E2 | 8 | 61 |
| HPV18 | E2 | 9 | 305 |
| HPV18 | E2 | 9 | 11 |
| HPV18 | E2 | 10 | 11 |
| HPV18 | E2 | 8 | 248 |
| HPV18 | E2 | 9 | 298 |
| HPV18 | E2 | 10 | 203 |
| HPV18 | E2 | 9 | 226 |
| HPV18 | E2 | 8 | 32 |
| HPV18 | E2 | 9 | 32 |
| HPV18 | E2 | 11 | 32 |
| HPV18 | E2 | 8 | 233 |
| HPV18 | E2 | 8 | 355 |
| HPV18 | E2 | 9 | 355 |
| HPV18 | E2 | 11 | 355 |
| HPV18 | E2 | 8 | 140 |
| HPV18 | E2 | 11 | 140 |
| HPV18 | E2 | 9 | 57 |
| HPV18 | E2 | 10 | 57 |
| HPV18 | E2 | 9 | 97 |
| HPV18 | E2 | 10 | 97 |
| HPV18 | E2 | 9 | 7 |
| HPV18 | E2 | 10 | 3 |
| HPV18 | E2 | 9 | 224 |
| HPV18 | E2 | 11 | 224 |
| HPV18 | E2 | 11 | 271 |
| HPV18 | E2 | 10 | 341 |
| HPV18 | E2 | 11 | 341 |
| HPV18 | E2 | 8 | 349 |
| HPV18 | E2 | 10 | 349 |
| HPV18 | E2 | 11 | 349 |
| HPV18 | E2 | 8 | 211 |
| HPV18 | E2 | 11 | 211 |
| HPV18 | E2 | 10 | 231 |
| HPV18 | E2 | 8 | 197 |
| HPV18 | E2 | 11 | 63 |
| HPV18 | E2 | 9 | 15 |
| HPV18 | E2 | 8 | 356 |
| HPV18 | E2 | 10 | 356 |
| HPV18 | E2 | 9 | 37 |
| HPV18 | E2 | 10 | 37 |
| HPV18 | E2 | 11 | 37 |
| HPV18 | E2 | 11 | 173 |
| HPV18 | E2 | 8 | 143 |
| HPV18 | E2 | 8 | 135 |
| HPV18 | E2 | 9 | 135 |
| HPV18 | E2 | 10 | 135 |
| HPV18 | E2 | 9 | 164 |
| HPV18 | E2 | 10 | 164 |
| HPV18 | E2 | 11 | 164 |
| HPV18 | E5 | 8 | 27 |
| HPV18 | E5 | 9 | 27 |
| HPV18 | E5 | 10 | 27 |
| HPV18 | E5 | 11 | 27 |
| HPV18 | E5 | 8 | 13 |
| HPV18 | E5 | 10 | 13 |
| HPV18 | E5 | 11 | 13 |
| HPV18 | E5 | 10 | 11 |
| HPV18 | E5 | 9 | 6 |
| HPV18 | E5 | 10 | 6 |
| HPV18 | E5 | 11 | 6 |
| HPV18 | E5 | 8 | 57 |
| HPV18 | E5 | 10 | 57 |
| HPV18 | E5 | 11 | 37 |
| HPV18 | E5 | 8 | 65 |
| HPV18 | E5 | 8 | 19 |
| HPV18 | E5 | 10 | 19 |
| HPV18 | E5 | 8 | 40 |
| HPV18 | E5 | 10 | 40 |
| HPV18 | E5 | 11 | 40 |
| HPV18 | E5 | 9 | 4 |
| HPV18 | E5 | 11 | 4 |
| HPV18 | E5 | 8 | 63 |
| HPV18 | E5 | 10 | 63 |
| HPV18 | E5 | 8 | 62 |
| HPV18 | E5 | 9 | 62 |
| HPV18 | E5 | 11 | 62 |
| HPV18 | E5 | 9 | 58 |
| HPV18 | E5 | 11 | 58 |
| HPV18 | E5 | 9 | 22 |
| HPV18 | E5 | 10 | 22 |
| HPV18 | E5 | 11 | 22 |
| HPV18 | E5 | 8 | 59 |
| HPV18 | E5 | 10 | 59 |
| HPV18 | E5 | 11 | 59 |
| HPV18 | E5 | 8 | 23 |
| HPV18 | E5 | 9 | 23 |
| HPV18 | E5 | 10 | 23 |
| HPV18 | E5 | 11 | 23 |
| HPV18 | E5 | 8 | 35 |
| HPV18 | E5 | 9 | 35 |
| HPV18 | E5 | 8 | 61 |
| HPV18 | E5 | 9 | 61 |
| HPV18 | E5 | 10 | 61 |
| HPV18 | E5 | 8 | 1 |
| HPV18 | E5 | 10 | 1 |
| HPV18 | E5 | 8 | 21 |
| HPV18 | E5 | 10 | 21 |
| HPV18 | E5 | 11 | 21 |
| HPV18 | E5 | 9 | 60 |
| HPV18 | E5 | 10 | 60 |
| HPV18 | E5 | 11 | 60 |
| HPV18 | E5 | 8 | 3 |
| HPV18 | E5 | 10 | 3 |
| HPV18 | E5 | 8 | 45 |
| HPV18 | E5 | 9 | 45 |
| HPV18 | E5 | 10 | 45 |
| HPV18 | E5 | 11 | 45 |
| HPV18 | E5 | 8 | 25 |
| HPV18 | E5 | 9 | 25 |
| HPV18 | E5 | 10 | 25 |
| HPV18 | E5 | 11 | 25 |
| HPV18 | E5 | 8 | 51 |
| HPV18 | E5 | 9 | 51 |
| HPV18 | E5 | 11 | 51 |
| HPV18 | E5 | 8 | 42 |
| HPV18 | E5 | 9 | 42 |
| HPV18 | E5 | 11 | 42 |
| HPV18 | E5 | 8 | 34 |

TABLE XIV-continued

HLA-B62 Supermotif Peptides

| 1 | 2 | 3 | 4 |
|---|---|---|---|
| HPV18 | E5 | 9 | 34 |
| HPV18 | E5 | 10 | 34 |
| HPV18 | E5 | 9 | 20 |
| HPV18 | E5 | 11 | 20 |
| HPV18 | E5 | 9 | 41 |
| HPV18 | E5 | 10 | 41 |
| HPV18 | E5 | 8 | 33 |
| HPV18 | E5 | 9 | 33 |
| HPV18 | E5 | 10 | 33 |
| HPV18 | E5 | 11 | 33 |
| HPV18 | E5 | 9 | 39 |
| HPV18 | E5 | 11 | 39 |
| HPV18 | E5 | 8 | 15 |
| HPV18 | E5 | 9 | 15 |
| HPV18 | E5 | 9 | 53 |
| HPV18 | E5 | 10 | 53 |
| HPV18 | E5 | 11 | 53 |
| HPV18 | E6 | 8 | 68 |
| HPV18 | E6 | 11 | 68 |
| HPV18 | E6 | 8 | 105 |
| HPV18 | E6 | 11 | 105 |
| HPV18 | E6 | 8 | 108 |
| HPV18 | E6 | 11 | 108 |
| HPV18 | E6 | 8 | 32 |
| HPV18 | E6 | 10 | 32 |
| HPV18 | E6 | 8 | 27 |
| HPV18 | E6 | 10 | 16 |
| HPV18 | E6 | 10 | 51 |
| HPV18 | E6 | 9 | 6 |
| HPV18 | E6 | 10 | 29 |
| HPV18 | E6 | 11 | 29 |
| HPV18 | E6 | 9 | 20 |
| HPV18 | E6 | 11 | 20 |
| HPV18 | E6 | 9 | 77 |
| HPV18 | E6 | 10 | 77 |
| HPV18 | E6 | 8 | 40 |
| HPV18 | E6 | 9 | 40 |
| HPV18 | E6 | 10 | 40 |
| HPV18 | E6 | 10 | 43 |
| HPV18 | E6 | 11 | 43 |
| HPV18 | E6 | 8 | 53 |
| HPV18 | E6 | 11 | 53 |
| HPV18 | E6 | 10 | 97 |
| HPV18 | E6 | 10 | 136 |
| HPV18 | E6 | 8 | 120 |
| HPV18 | E6 | 11 | 120 |
| HPV18 | E6 | 10 | 60 |
| HPV18 | E6 | 9 | 13 |
| HPV18 | E6 | 11 | 117 |
| HPV18 | E6 | 8 | 92 |
| HPV18 | E6 | 10 | 92 |
| HPV18 | E6 | 11 | 92 |
| HPV18 | E6 | 9 | 110 |
| HPV18 | E6 | 11 | 102 |
| HPV18 | E6 | 8 | 14 |
| HPV18 | E6 | 9 | 25 |
| HPV18 | E6 | 10 | 25 |
| HPV18 | E6 | 9 | 150 |
| HPV18 | E6 | 9 | 113 |
| HPV18 | E6 | 8 | 111 |
| HPV18 | E6 | 11 | 111 |
| HPV18 | E6 | 8 | 74 |
| HPV18 | E6 | 10 | 149 |
| HPV18 | E6 | 8 | 10 |
| HPV18 | E6 | 11 | 59 |
| HPV18 | E6 | 10 | 24 |
| HPV18 | E6 | 11 | 24 |
| HPV18 | E6 | 10 | 84 |
| HPV18 | E6 | 10 | 89 |
| HPV18 | E6 | 11 | 89 |
| HPV18 | E6 | 8 | 37 |
| HPV18 | E6 | 9 | 37 |
| HPV18 | E6 | 11 | 37 |
| HPV18 | E6 | 8 | 38 |
| HPV18 | E6 | 10 | 38 |
| HPV18 | E6 | 11 | 38 |
| HPV18 | E6 | 10 | 54 |
| HPV18 | E6 | 11 | 54 |
| HPV18 | E7 | 8 | 63 |
| HPV18 | E7 | 10 | 63 |
| HPV18 | E7 | 8 | 24 |
| HPV18 | E7 | 8 | 82 |
| HPV18 | E7 | 9 | 82 |
| HPV18 | E7 | 10 | 82 |
| HPV18 | E7 | 10 | 40 |
| HPV18 | E7 | 8 | 16 |
| HPV18 | E7 | 10 | 16 |
| HPV18 | E7 | 11 | 16 |
| HPV18 | E7 | 8 | 55 |
| HPV18 | E7 | 10 | 55 |
| HPV18 | E7 | 8 | 90 |
| HPV18 | E7 | 11 | 90 |
| HPV18 | E7 | 9 | 86 |
| HPV18 | E7 | 11 | 86 |
| HPV18 | E7 | 9 | 3 |
| HPV18 | E7 | 10 | 3 |
| HPV18 | E7 | 11 | 3 |
| HPV18 | E7 | 9 | 43 |
| HPV18 | E7 | 8 | 14 |
| HPV18 | E7 | 10 | 14 |
| HPV18 | E7 | 9 | 46 |
| HPV18 | E7 | 11 | 21 |
| HPV18 | E7 | 11 | 11 |
| HPV18 | E7 | 8 | 73 |
| HPV18 | E7 | 11 | 73 |
| HPV18 | E7 | 8 | 8 |
| HPV18 | E7 | 10 | 74 |
| HPV18 | E7 | 10 | 61 |
| HPV18 | E7 | 9 | 17 |
| HPV18 | E7 | 10 | 17 |
| HPV18 | E7 | 9 | 56 |
| HPV18 | E7 | 10 | 22 |
| HPV18 | E7 | 9 | 88 |
| HPV18 | E7 | 10 | 88 |
| HPV18 | E7 | 8 | 87 |
| HPV18 | E7 | 10 | 87 |
| HPV18 | E7 | 11 | 87 |
| HPV18 | E7 | 10 | 71 |
| HPV18 | E7 | 9 | 7 |
| HPV18 | E7 | 8 | 93 |
| HPV18 | E7 | 10 | 93 |
| HPV18 | E7 | 11 | 60 |
| HPV18 | E7 | 10 | 12 |
| HPV18 | E7 | 9 | 75 |
| HPV18 | E7 | 11 | 75 |
| HPV18 | L1 | 11 | 225 |
| HPV18 | L1 | 8 | 487 |
| HPV18 | L1 | 9 | 487 |
| HPV18 | L1 | 11 | 487 |
| HPV18 | L1 | 10 | 63 |
| HPV18 | L1 | 11 | 63 |
| HPV18 | L1 | 9 | 495 |
| HPV18 | L1 | 8 | 223 |
| HPV18 | L1 | 9 | 223 |
| HPV18 | L1 | 11 | 549 |
| HPV18 | L1 | 8 | 377 |
| HPV18 | L1 | 10 | 377 |
| HPV18 | L1 | 8 | 218 |
| HPV18 | L1 | 9 | 218 |
| HPV18 | L1 | 8 | 310 |
| HPV18 | L1 | 9 | 310 |
| HPV18 | L1 | 8 | 2 |
| HPV18 | L1 | 9 | 2 |
| HPV18 | L1 | 11 | 2 |
| HPV18 | L1 | 10 | 246 |
| HPV18 | L1 | 11 | 246 |
| HPV18 | L1 | 8 | 490 |
| HPV18 | L1 | 10 | 286 |
| HPV18 | L1 | 11 | 286 |
| HPV18 | L1 | 11 | 350 |

TABLE XIV-continued

HLA-B62 Supermotif Peptides

| 1 | 2 | 3 | 4 |
|---|---|---|---|
| HPV18 | L1 | 9 | 284 |
| HPV18 | L1 | 8 | 122 |
| HPV18 | L1 | 10 | 122 |
| HPV18 | L1 | 11 | 520 |
| HPV18 | L1 | 8 | 512 |
| HPV18 | L1 | 10 | 512 |
| HPV18 | L1 | 8 | 433 |
| HPV18 | L1 | 11 | 433 |
| HPV18 | L1 | 9 | 260 |
| HPV18 | L1 | 10 | 260 |
| HPV18 | L1 | 8 | 501 |
| HPV18 | L1 | 9 | 501 |
| HPV18 | L1 | 11 | 501 |
| HPV18 | L1 | 8 | 301 |
| HPV18 | L1 | 9 | 301 |
| HPV18 | L1 | 11 | 301 |
| HPV18 | L1 | 9 | 522 |
| HPV18 | L1 | 10 | 522 |
| HPV18 | L1 | 11 | 522 |
| HPV18 | L1 | 9 | 448 |
| HPV18 | L1 | 8 | 203 |
| HPV18 | L1 | 10 | 203 |
| HPV18 | L1 | 8 | 167 |
| HPV18 | L1 | 10 | 167 |
| HPV18 | L1 | 8 | 314 |
| HPV18 | L1 | 9 | 314 |
| HPV18 | L1 | 10 | 280 |
| HPV18 | L1 | 8 | 436 |
| HPV18 | L1 | 10 | 436 |
| HPV18 | L1 | 8 | 49 |
| HPV18 | L1 | 10 | 49 |
| HPV18 | L1 | 11 | 49 |
| HPV18 | L1 | 8 | 56 |
| HPV18 | L1 | 9 | 56 |
| HPV18 | L1 | 10 | 56 |
| HPV18 | L1 | 8 | 438 |
| HPV18 | L1 | 10 | 438 |
| HPV18 | L1 | 8 | 145 |
| HPV18 | L1 | 8 | 535 |
| HPV18 | L1 | 8 | 177 |
| HPV18 | L1 | 11 | 177 |
| HPV18 | L1 | 10 | 342 |
| HPV18 | L1 | 11 | 342 |
| HPV18 | L1 | 9 | 19 |
| HPV18 | L1 | 11 | 19 |
| HPV18 | L1 | 10 | 543 |
| HPV18 | L1 | 8 | 171 |
| HPV18 | L1 | 8 | 415 |
| HPV18 | L1 | 11 | 415 |
| HPV18 | L1 | 8 | 383 |
| HPV18 | L1 | 9 | 383 |
| HPV18 | L1 | 10 | 383 |
| HPV18 | L1 | 10 | 165 |
| HPV18 | L1 | 9 | 175 |
| HPV18 | L1 | 10 | 175 |
| HPV18 | L1 | 10 | 467 |
| HPV18 | L1 | 11 | 467 |
| HPV18 | L1 | 8 | 38 |
| HPV18 | L1 | 9 | 38 |
| HPV18 | L1 | 10 | 38 |
| HPV18 | L1 | 11 | 38 |
| HPV18 | L1 | 9 | 13 |
| HPV18 | L1 | 10 | 13 |
| HPV18 | L1 | 10 | 23 |
| HPV18 | L1 | 11 | 23 |
| HPV18 | L1 | 9 | 428 |
| HPV18 | L1 | 10 | 428 |
| HPV18 | L1 | 11 | 428 |
| HPV18 | L1 | 8 | 40 |
| HPV18 | L1 | 9 | 40 |
| HPV18 | L1 | 10 | 40 |
| HPV18 | L1 | 11 | 40 |
| HPV18 | L1 | 8 | 39 |
| HPV18 | L1 | 9 | 39 |
| HPV18 | L1 | 10 | 39 |
| HPV18 | L1 | 11 | 39 |
| HPV18 | L1 | 8 | 46 |
| HPV18 | L1 | 10 | 46 |
| HPV18 | L1 | 11 | 46 |
| HPV18 | L1 | 9 | 460 |
| HPV18 | L1 | 9 | 47 |
| HPV18 | L1 | 10 | 47 |
| HPV18 | L1 | 8 | 219 |
| HPV18 | L1 | 9 | 9 |
| HPV18 | L1 | 10 | 9 |
| HPV18 | L1 | 8 | 32 |
| HPV18 | L1 | 9 | 32 |
| HPV18 | L1 | 10 | 32 |
| HPV18 | L1 | 9 | 123 |
| HPV18 | L1 | 11 | 123 |
| HPV18 | L1 | 8 | 360 |
| HPV18 | L1 | 9 | 360 |
| HPV18 | L1 | 10 | 186 |
| HPV18 | L1 | 11 | 186 |
| HPV18 | L1 | 9 | 505 |
| HPV18 | L1 | 8 | 557 |
| HPV18 | L1 | 10 | 557 |
| HPV18 | L1 | 11 | 539 |
| HPV18 | L1 | 8 | 370 |
| HPV18 | L1 | 9 | 120 |
| HPV18 | L1 | 10 | 120 |
| HPV18 | L1 | 8 | 213 |
| HPV18 | L1 | 11 | 213 |
| HPV18 | L1 | 10 | 423 |
| HPV18 | L1 | 9 | 125 |
| HPV18 | L1 | 10 | 125 |
| HPV18 | L1 | 8 | 8 |
| HPV18 | L1 | 10 | 8 |
| HPV18 | L1 | 11 | 8 |
| HPV18 | L1 | 8 | 14 |
| HPV18 | L1 | 9 | 14 |
| HPV18 | L1 | 8 | 103 |
| HPV18 | L1 | 9 | 103 |
| HPV18 | L1 | 11 | 103 |
| HPV18 | L1 | 9 | 138 |
| HPV18 | L1 | 8 | 27 |
| HPV18 | L1 | 9 | 27 |
| HPV18 | L1 | 10 | 27 |
| HPV18 | L1 | 11 | 27 |
| HPV18 | L1 | 8 | 15 |
| HPV18 | L1 | 9 | 74 |
| HPV18 | L1 | 10 | 74 |
| HPV18 | L1 | 8 | 274 |
| HPV18 | L1 | 10 | 274 |
| HPV18 | L1 | 10 | 434 |
| HPV18 | L1 | 8 | 296 |
| HPV18 | L1 | 8 | 476 |
| HPV18 | L1 | 11 | 476 |
| HPV18 | L1 | 8 | 159 |
| HPV18 | L1 | 10 | 159 |
| HPV18 | L1 | 8 | 33 |
| HPV18 | L1 | 9 | 33 |
| HPV18 | L1 | 9 | 343 |
| HPV18 | L1 | 10 | 343 |
| HPV18 | L1 | 8 | 261 |
| HPV18 | L1 | 9 | 261 |
| HPV18 | L1 | 11 | 261 |
| HPV18 | L1 | 10 | 36 |
| HPV18 | L1 | 11 | 36 |
| HPV18 | L1 | 8 | 153 |
| HPV18 | L1 | 9 | 153 |
| HPV18 | L1 | 10 | 153 |
| HPV18 | L1 | 8 | 108 |
| HPV18 | L1 | 8 | 388 |
| HPV18 | L1 | 8 | 510 |
| HPV18 | L1 | 10 | 510 |
| HPV18 | L1 | 9 | 54 |
| HPV18 | L1 | 10 | 54 |
| HPV18 | L1 | 11 | 54 |
| HPV18 | L1 | 8 | 52 |

TABLE XIV-continued

HLA-B62 Supermotif Peptides

| 1 | 2 | 3 | 4 |
|---|---|---|---|
| HPV18 | L1 | 9 | 52 |
| HPV18 | L1 | 11 | 52 |
| HPV18 | L1 | 10 | 199 |
| HPV18 | L1 | 11 | 207 |
| HPV18 | L1 | 8 | 57 |
| HPV18 | L1 | 9 | 57 |
| HPV18 | L1 | 8 | 282 |
| HPV18 | L1 | 11 | 282 |
| HPV18 | L1 | 8 | 248 |
| HPV18 | L1 | 9 | 248 |
| HPV18 | L1 | 8 | 525 |
| HPV18 | L1 | 10 | 525 |
| HPV18 | L1 | 11 | 173 |
| HPV18 | L1 | 8 | 28 |
| HPV18 | L1 | 9 | 28 |
| HPV18 | L1 | 10 | 28 |
| HPV18 | L1 | 8 | 26 |
| HPV18 | L1 | 9 | 26 |
| HPV18 | L1 | 10 | 26 |
| HPV18 | L1 | 11 | 26 |
| HPV18 | L1 | 10 | 240 |
| HPV18 | L1 | 8 | 20 |
| HPV18 | L1 | 10 | 20 |
| HPV18 | L1 | 9 | 247 |
| HPV18 | L1 | 10 | 247 |
| HPV18 | L1 | 8 | 469 |
| HPV18 | L1 | 9 | 469 |
| HPV18 | L1 | 8 | 75 |
| HPV18 | L1 | 9 | 75 |
| HPV18 | L1 | 8 | 470 |
| HPV18 | L1 | 11 | 470 |
| HPV18 | L1 | 8 | 76 |
| HPV18 | L1 | 10 | 471 |
| HPV18 | L1 | 11 | 333 |
| HPV18 | L1 | 8 | 412 |
| HPV18 | L1 | 11 | 412 |
| HPV18 | L1 | 8 | 216 |
| HPV18 | L1 | 10 | 216 |
| HPV18 | L1 | 11 | 216 |
| HPV18 | L1 | 9 | 439 |
| HPV18 | L1 | 11 | 439 |
| HPV18 | L1 | 8 | 315 |
| HPV18 | L1 | 11 | 315 |
| HPV18 | L1 | 8 | 366 |
| HPV18 | L1 | 9 | 366 |
| HPV18 | L1 | 8 | 137 |
| HPV18 | L1 | 10 | 137 |
| HPV18 | L1 | 11 | 297 |
| HPV18 | L1 | 9 | 102 |
| HPV18 | L1 | 10 | 102 |
| HPV18 | L1 | 9 | 158 |
| HPV18 | L1 | 11 | 158 |
| HPV18 | L1 | 8 | 25 |
| HPV18 | L1 | 9 | 25 |
| HPV18 | L1 | 10 | 25 |
| HPV18 | L1 | 11 | 25 |
| HPV18 | L1 | 11 | 239 |
| HPV18 | L1 | 8 | 66 |
| HPV18 | L1 | 9 | 66 |
| HPV18 | L1 | 9 | 6 |
| HPV18 | L1 | 10 | 6 |
| HPV18 | L1 | 10 | 135 |
| HPV18 | L1 | 8 | 81 |
| HPV18 | L1 | 9 | 81 |
| HPV18 | L1 | 8 | 288 |
| HPV18 | L1 | 9 | 288 |
| HPV18 | L1 | 11 | 288 |
| HPV18 | L1 | 11 | 93 |
| HPV18 | L1 | 8 | 459 |
| HPV18 | L1 | 10 | 459 |
| HPV18 | L1 | 9 | 31 |
| HPV18 | L1 | 10 | 31 |
| HPV18 | L1 | 11 | 31 |
| HPV18 | L1 | 9 | 359 |
| HPV18 | L1 | 10 | 359 |
| HPV18 | L1 | 10 | 150 |
| HPV18 | L1 | 11 | 150 |
| HPV18 | L1 | 9 | 518 |
| HPV18 | L1 | 8 | 475 |
| HPV18 | L1 | 9 | 475 |
| HPV18 | L1 | 9 | 335 |
| HPV18 | L1 | 11 | 335 |
| HPV18 | L1 | 11 | 306 |
| HPV18 | L1 | 10 | 455 |
| HPV18 | L1 | 8 | 353 |
| HPV18 | L1 | 9 | 353 |
| HPV18 | L1 | 9 | 411 |
| HPV18 | L1 | 8 | 242 |
| HPV18 | L1 | 10 | 242 |
| HPV18 | L1 | 8 | 365 |
| HPV18 | L1 | 9 | 365 |
| HPV18 | L1 | 10 | 365 |
| HPV18 | L1 | 10 | 485 |
| HPV18 | L1 | 11 | 485 |
| HPV18 | L1 | 11 | 78 |
| HPV18 | L1 | 9 | 209 |
| HPV18 | L1 | 11 | 209 |
| HPV18 | L1 | 10 | 404 |
| HPV18 | L1 | 9 | 541 |
| HPV18 | L1 | 8 | 442 |
| HPV18 | L1 | 9 | 442 |
| HPV18 | L1 | 11 | 442 |
| HPV18 | L1 | 9 | 273 |
| HPV18 | L1 | 11 | 273 |
| HPV18 | L1 | 9 | 444 |
| HPV18 | L1 | 10 | 444 |
| HPV18 | L1 | 10 | 327 |
| HPV18 | L1 | 11 | 327 |
| HPV18 | L1 | 8 | 398 |
| HPV18 | L1 | 10 | 398 |
| HPV18 | L1 | 9 | 90 |
| HPV18 | L1 | 9 | 215 |
| HPV18 | L1 | 11 | 215 |
| HPV18 | L1 | 9 | 156 |
| HPV18 | L1 | 11 | 156 |
| HPV18 | L1 | 9 | 409 |
| HPV18 | L1 | 11 | 409 |
| HPV18 | L1 | 9 | 105 |
| HPV18 | L1 | 11 | 105 |
| HPV18 | L1 | 8 | 254 |
| HPV18 | L1 | 9 | 254 |
| HPV18 | L1 | 8 | 331 |
| HPV18 | L1 | 11 | 393 |
| HPV18 | L1 | 9 | 71 |
| HPV18 | L1 | 10 | 71 |
| HPV18 | L1 | 8 | 255 |
| HPV18 | L1 | 8 | 7 |
| HPV18 | L1 | 9 | 7 |
| HPV18 | L1 | 11 | 7 |
| HPV18 | L1 | 8 | 449 |
| HPV18 | L1 | 11 | 113 |
| HPV18 | L1 | 10 | 413 |
| HPV18 | L1 | 9 | 281 |
| HPV18 | L1 | 9 | 468 |
| HPV18 | L1 | 10 | 468 |
| HPV18 | L1 | 11 | 532 |
| HPV18 | L1 | 9 | 136 |
| HPV18 | L1 | 11 | 136 |
| HPV18 | L1 | 10 | 394 |
| HPV18 | L1 | 8 | 82 |
| HPV18 | L1 | 9 | 452 |
| HPV18 | L1 | 10 | 452 |
| HPV18 | L1 | 9 | 45 |
| HPV18 | L1 | 11 | 45 |
| HPV18 | L1 | 9 | 337 |
| HPV18 | L1 | 8 | 73 |
| HPV18 | L1 | 10 | 73 |
| HPV18 | L1 | 11 | 73 |
| HPV18 | L1 | 9 | 295 |
| HPV18 | L1 | 11 | 35 |

TABLE XIV-continued

HLA-B62 Supermotif Peptides

| 1 | 2 | 3 | 4 |
|---|---|---|---|
| HPV18 | L1 | 9 | 292 |
| HPV18 | L1 | 8 | 524 |
| HPV18 | L1 | 9 | 524 |
| HPV18 | L1 | 11 | 524 |
| HPV18 | L1 | 8 | 129 |
| HPV18 | L1 | 10 | 129 |
| HPV18 | L1 | 8 | 88 |
| HPV18 | L1 | 9 | 88 |
| HPV18 | L1 | 11 | 88 |
| HPV18 | L2 | 9 | 286 |
| HPV18 | L2 | 11 | 286 |
| HPV18 | L2 | 8 | 421 |
| HPV18 | L2 | 10 | 421 |
| HPV18 | L2 | 9 | 327 |
| HPV18 | L2 | 9 | 27 |
| HPV18 | L2 | 9 | 278 |
| HPV18 | L2 | 10 | 278 |
| HPV18 | L2 | 11 | 322 |
| HPV18 | L2 | 10 | 404 |
| HPV18 | L2 | 11 | 404 |
| HPV18 | L2 | 9 | 142 |
| HPV18 | L2 | 11 | 142 |
| HPV18 | L2 | 11 | 129 |
| HPV18 | L2 | 10 | 349 |
| HPV18 | L2 | 11 | 349 |
| HPV18 | L2 | 10 | 346 |
| HPV18 | L2 | 8 | 354 |
| HPV18 | L2 | 11 | 266 |
| HPV18 | L2 | 8 | 100 |
| HPV18 | L2 | 9 | 83 |
| HPV18 | L2 | 10 | 83 |
| HPV18 | L2 | 11 | 83 |
| HPV18 | L2 | 8 | 270 |
| HPV18 | L2 | 10 | 270 |
| HPV18 | L2 | 11 | 270 |
| HPV18 | L2 | 10 | 396 |
| HPV18 | L2 | 11 | 30 |
| HPV18 | L2 | 8 | 194 |
| HPV18 | L2 | 8 | 334 |
| HPV18 | L2 | 8 | 208 |
| HPV18 | L2 | 11 | 208 |
| HPV18 | L2 | 9 | 257 |
| HPV18 | L2 | 10 | 94 |
| HPV18 | L2 | 11 | 94 |
| HPV18 | L2 | 8 | 175 |
| HPV18 | L2 | 8 | 169 |
| HPV18 | L2 | 9 | 169 |
| HPV18 | L2 | 9 | 443 |
| HPV18 | L2 | 11 | 443 |
| HPV18 | L2 | 8 | 241 |
| HPV18 | L2 | 9 | 241 |
| HPV18 | L2 | 11 | 241 |
| HPV18 | L2 | 11 | 276 |
| HPV18 | L2 | 9 | 51 |
| HPV18 | L2 | 8 | 429 |
| HPV18 | L2 | 9 | 429 |
| HPV18 | L2 | 10 | 429 |
| HPV18 | L2 | 8 | 223 |
| HPV18 | L2 | 9 | 223 |
| HPV18 | L2 | 8 | 97 |
| HPV18 | L2 | 10 | 97 |
| HPV18 | L2 | 11 | 97 |
| HPV18 | L2 | 8 | 85 |
| HPV18 | L2 | 9 | 85 |
| HPV18 | L2 | 10 | 167 |
| HPV18 | L2 | 11 | 167 |
| HPV18 | L2 | 8 | 279 |
| HPV18 | L2 | 9 | 279 |
| HPV18 | L2 | 9 | 44 |
| HPV18 | L2 | 10 | 44 |
| HPV18 | L2 | 11 | 44 |
| HPV18 | L2 | 8 | 444 |
| HPV18 | L2 | 10 | 444 |
| HPV18 | L2 | 11 | 444 |
| HPV18 | L2 | 10 | 72 |
| HPV18 | L2 | 11 | 72 |
| HPV18 | L2 | 8 | 416 |
| HPV18 | L2 | 10 | 103 |
| HPV18 | L2 | 11 | 103 |
| HPV18 | L2 | 8 | 43 |
| HPV18 | L2 | 10 | 43 |
| HPV18 | L2 | 11 | 43 |
| HPV18 | L2 | 10 | 22 |
| HPV18 | L2 | 11 | 22 |
| HPV18 | L2 | 8 | 34 |
| HPV18 | L2 | 11 | 34 |
| HPV18 | L2 | 8 | 106 |
| HPV18 | L2 | 8 | 248 |
| HPV18 | L2 | 9 | 248 |
| HPV18 | L2 | 8 | 407 |
| HPV18 | L2 | 10 | 407 |
| HPV18 | L2 | 11 | 407 |
| HPV18 | L2 | 8 | 215 |
| HPV18 | L2 | 8 | 45 |
| HPV18 | L2 | 9 | 45 |
| HPV18 | L2 | 10 | 45 |
| HPV18 | L2 | 10 | 338 |
| HPV18 | L2 | 11 | 338 |
| HPV18 | L2 | 11 | 253 |
| HPV18 | L2 | 9 | 159 |
| HPV18 | L2 | 10 | 159 |
| HPV18 | L2 | 11 | 238 |
| HPV18 | L2 | 10 | 386 |
| HPV18 | L2 | 8 | 325 |
| HPV18 | L2 | 9 | 325 |
| HPV18 | L2 | 11 | 325 |
| HPV18 | L2 | 10 | 209 |
| HPV18 | L2 | 9 | 415 |
| HPV18 | L2 | 9 | 73 |
| HPV18 | L2 | 10 | 73 |
| HPV18 | L2 | 8 | 214 |
| HPV18 | L2 | 9 | 214 |
| HPV18 | L2 | 8 | 390 |
| HPV18 | L2 | 10 | 390 |
| HPV18 | L2 | 11 | 390 |
| HPV18 | L2 | 11 | 337 |
| HPV18 | L2 | 8 | 28 |
| HPV18 | L2 | 8 | 89 |
| HPV18 | L2 | 10 | 171 |
| HPV18 | L2 | 11 | 171 |
| HPV18 | L2 | 8 | 258 |
| HPV18 | L2 | 9 | 95 |
| HPV18 | L2 | 10 | 95 |
| HPV18 | L2 | 10 | 360 |
| HPV18 | L2 | 11 | 360 |
| HPV18 | L2 | 8 | 398 |
| HPV18 | L2 | 10 | 398 |
| HPV18 | L2 | 8 | 312 |
| HPV18 | L2 | 9 | 312 |
| HPV18 | L2 | 10 | 232 |
| HPV18 | L2 | 11 | 232 |
| HPV18 | L2 | 9 | 233 |
| HPV18 | L2 | 10 | 233 |
| HPV18 | L2 | 8 | 298 |
| HPV18 | L2 | 9 | 298 |
| HPV18 | L2 | 10 | 225 |
| HPV18 | L2 | 11 | 284 |
| HPV18 | L2 | 9 | 88 |
| HPV18 | L2 | 8 | 244 |
| HPV18 | L2 | 10 | 119 |
| HPV18 | L2 | 8 | 220 |
| HPV18 | L2 | 11 | 220 |
| HPV18 | L2 | 8 | 316 |
| HPV18 | L2 | 11 | 316 |
| HPV18 | L2 | 10 | 450 |
| HPV18 | L2 | 11 | 450 |
| HPV18 | L2 | 11 | 166 |
| HPV18 | L2 | 11 | 151 |
| HPV18 | L2 | 11 | 102 |
| HPV18 | L2 | 9 | 49 |

TABLE XIV-continued

HLA-B62 Supermotif Peptides

| 1 | 2 | 3 | 4 |
|---|---|---|---|
| HPV18 | L2 | 11 | 49 |
| HPV18 | L2 | 9 | 247 |
| HPV18 | L2 | 10 | 247 |
| HPV18 | L2 | 10 | 329 |
| HPV18 | L2 | 11 | 329 |
| HPV18 | L2 | 9 | 324 |
| HPV18 | L2 | 10 | 324 |
| HPV18 | L2 | 10 | 418 |
| HPV18 | L2 | 11 | 418 |
| HPV18 | L2 | 10 | 375 |
| HPV18 | L2 | 8 | 235 |
| HPV18 | L2 | 9 | 149 |
| HPV18 | L2 | 10 | 412 |
| HPV18 | L2 | 8 | 377 |
| HPV18 | L2 | 11 | 377 |
| HPV18 | L2 | 9 | 39 |
| HPV18 | L2 | 8 | 105 |
| HPV18 | L2 | 9 | 105 |
| HPV18 | L2 | 8 | 406 |
| HPV18 | L2 | 9 | 406 |
| HPV18 | L2 | 11 | 406 |
| HPV18 | L2 | 10 | 262 |
| HPV18 | L2 | 10 | 304 |
| HPV18 | L2 | 9 | 213 |
| HPV18 | L2 | 10 | 213 |
| HPV18 | L2 | 9 | 144 |
| HPV18 | L2 | 9 | 184 |
| HPV18 | L2 | 9 | 311 |
| HPV18 | L2 | 10 | 311 |
| HPV18 | L2 | 11 | 425 |
| HPV18 | L2 | 8 | 388 |
| HPV18 | L2 | 10 | 388 |
| HPV18 | L2 | 11 | 293 |
| HPV18 | L2 | 10 | 217 |
| HPV18 | L2 | 11 | 217 |
| HPV18 | L2 | 11 | 140 |
| HPV18 | L2 | 9 | 271 |
| HPV18 | L2 | 10 | 271 |
| HPV18 | L2 | 9 | 32 |
| HPV18 | L2 | 10 | 32 |
| HPV18 | L2 | 9 | 389 |
| HPV18 | L2 | 11 | 389 |
| HPV18 | L2 | 8 | 170 |
| HPV18 | L2 | 11 | 170 |
| HPV18 | L2 | 9 | 361 |
| HPV18 | L2 | 10 | 361 |
| HPV18 | L2 | 11 | 361 |
| HPV18 | L2 | 11 | 359 |
| HPV18 | L2 | 9 | 397 |
| HPV18 | L2 | 11 | 397 |
| HPV18 | L2 | 9 | 451 |
| HPV18 | L2 | 10 | 451 |
| HPV18 | L2 | 11 | 451 |
| HPV18 | L2 | 11 | 81 |
| HPV18 | L2 | 10 | 31 |
| HPV18 | L2 | 11 | 31 |
| HPV18 | L2 | 11 | 112 |
| HPV18 | L2 | 8 | 414 |
| HPV18 | L2 | 10 | 414 |
| HPV18 | L2 | 8 | 332 |
| HPV18 | L2 | 10 | 332 |
| HPV18 | L2 | 9 | 427 |
| HPV18 | L2 | 10 | 427 |
| HPV18 | L2 | 11 | 427 |
| HPV18 | L2 | 11 | 71 |
| HPV18 | L2 | 8 | 436 |
| HPV18 | L2 | 9 | 436 |
| HPV18 | L2 | 11 | 231 |
| HPV31 | E1 | 11 | 111 |
| HPV31 | E1 | 9 | 519 |
| HPV31 | E1 | 11 | 519 |
| HPV31 | E1 | 8 | 68 |
| HPV31 | E1 | 9 | 439 |
| HPV31 | E1 | 10 | 533 |
| HPV31 | E1 | 11 | 533 |
| HPV31 | E1 | 9 | 298 |
| HPV31 | E1 | 9 | 186 |
| HPV31 | E1 | 10 | 186 |
| HPV31 | E1 | 8 | 458 |
| HPV31 | E1 | 9 | 458 |
| HPV31 | E1 | 11 | 458 |
| HPV31 | E1 | 10 | 66 |
| HPV31 | E1 | 8 | 72 |
| HPV31 | E1 | 10 | 72 |
| HPV31 | E1 | 11 | 72 |
| HPV31 | E1 | 10 | 360 |
| HPV31 | E1 | 11 | 22 |
| HPV31 | E1 | 9 | 81 |
| HPV31 | E1 | 10 | 81 |
| HPV31 | E1 | 9 | 113 |
| HPV31 | E1 | 8 | 279 |
| HPV31 | E1 | 9 | 279 |
| HPV31 | E1 | 9 | 239 |
| HPV31 | E1 | 10 | 239 |
| HPV31 | E1 | 9 | 284 |
| HPV31 | E1 | 10 | 539 |
| HPV31 | E1 | 11 | 217 |
| HPV31 | E1 | 10 | 100 |
| HPV31 | E1 | 10 | 620 |
| HPV31 | E1 | 8 | 96 |
| HPV31 | E1 | 10 | 96 |
| HPV31 | E1 | 8 | 421 |
| HPV31 | E1 | 11 | 421 |
| HPV31 | E1 | 8 | 336 |
| HPV31 | E1 | 9 | 336 |
| HPV31 | E1 | 10 | 336 |
| HPV31 | E1 | 11 | 46 |
| HPV31 | E1 | 8 | 528 |
| HPV31 | E1 | 10 | 528 |
| HPV31 | E1 | 8 | 348 |
| HPV31 | E1 | 9 | 348 |
| HPV31 | E1 | 10 | 348 |
| HPV31 | E1 | 9 | 311 |
| HPV31 | E1 | 10 | 311 |
| HPV31 | E1 | 9 | 354 |
| HPV31 | E1 | 10 | 354 |
| HPV31 | E1 | 10 | 583 |
| HPV31 | E1 | 11 | 583 |
| HPV31 | E1 | 8 | 193 |
| HPV31 | E1 | 10 | 193 |
| HPV31 | E1 | 11 | 193 |
| HPV31 | E1 | 8 | 137 |
| HPV31 | E1 | 10 | 137 |
| HPV31 | E1 | 8 | 50 |
| HPV31 | E1 | 11 | 443 |
| HPV31 | E1 | 8 | 372 |
| HPV31 | E1 | 10 | 372 |
| HPV31 | E1 | 11 | 372 |
| HPV31 | E1 | 9 | 473 |
| HPV31 | E1 | 10 | 473 |
| HPV31 | E1 | 9 | 425 |
| HPV31 | E1 | 10 | 425 |
| HPV31 | E1 | 8 | 436 |
| HPV31 | E1 | 9 | 436 |
| HPV31 | E1 | 8 | 199 |
| HPV31 | E1 | 10 | 572 |
| HPV31 | E1 | 11 | 572 |
| HPV31 | E1 | 11 | 206 |
| HPV31 | E1 | 8 | 433 |
| HPV31 | E1 | 10 | 433 |
| HPV31 | E1 | 11 | 433 |
| HPV31 | E1 | 11 | 499 |
| HPV31 | E1 | 8 | 467 |
| HPV31 | E1 | 8 | 305 |
| HPV31 | E1 | 9 | 305 |
| HPV31 | E1 | 8 | 252 |
| HPV31 | E1 | 10 | 252 |
| HPV31 | E1 | 11 | 403 |
| HPV31 | E1 | 8 | 446 |
| HPV31 | E1 | 9 | 446 |

TABLE XIV-continued

HLA-B62 Supermotif Peptides

| 1 | 2 | 3 | 4 |
|---|---|---|---|
| HPV31 | E1 | 10 | 446 |
| HPV31 | E1 | 8 | 196 |
| HPV31 | E1 | 11 | 196 |
| HPV31 | E1 | 10 | 222 |
| HPV31 | E1 | 9 | 243 |
| HPV31 | E1 | 11 | 243 |
| HPV31 | E1 | 11 | 478 |
| HPV31 | E1 | 10 | 287 |
| HPV31 | E1 | 11 | 287 |
| HPV31 | E1 | 8 | 381 |
| HPV31 | E1 | 10 | 422 |
| HPV31 | E1 | 8 | 497 |
| HPV31 | E1 | 9 | 380 |
| HPV31 | E1 | 10 | 276 |
| HPV31 | E1 | 11 | 276 |
| HPV31 | E1 | 9 | 272 |
| HPV31 | E1 | 8 | 291 |
| HPV31 | E1 | 9 | 291 |
| HPV31 | E1 | 10 | 291 |
| HPV31 | E1 | 11 | 291 |
| HPV31 | E1 | 8 | 412 |
| HPV31 | E1 | 11 | 412 |
| HPV31 | E1 | 11 | 286 |
| HPV31 | E1 | 9 | 470 |
| HPV31 | E1 | 10 | 470 |
| HPV31 | E1 | 8 | 543 |
| HPV31 | E1 | 9 | 277 |
| HPV31 | E1 | 10 | 277 |
| HPV31 | E1 | 11 | 277 |
| HPV31 | E1 | 8 | 273 |
| HPV31 | E1 | 9 | 542 |
| HPV31 | E1 | 8 | 234 |
| HPV31 | E1 | 11 | 234 |
| HPV31 | E1 | 9 | 256 |
| HPV31 | E1 | 9 | 534 |
| HPV31 | E1 | 10 | 534 |
| HPV31 | E1 | 11 | 534 |
| HPV31 | E1 | 11 | 128 |
| HPV31 | E1 | 8 | 474 |
| HPV31 | E1 | 9 | 474 |
| HPV31 | E1 | 10 | 326 |
| HPV31 | E1 | 9 | 490 |
| HPV31 | E1 | 11 | 490 |
| HPV31 | E1 | 10 | 235 |
| HPV31 | E1 | 8 | 244 |
| HPV31 | E1 | 10 | 244 |
| HPV31 | E1 | 11 | 244 |
| HPV31 | E1 | 11 | 175 |
| HPV31 | E1 | 11 | 258 |
| HPV31 | E1 | 10 | 563 |
| HPV31 | E1 | 10 | 500 |
| HPV31 | E1 | 8 | 187 |
| HPV31 | E1 | 9 | 187 |
| HPV31 | E1 | 11 | 187 |
| HPV31 | E1 | 8 | 285 |
| HPV31 | E1 | 10 | 255 |
| HPV31 | E1 | 8 | 257 |
| HPV31 | E1 | 8 | 535 |
| HPV31 | E1 | 9 | 535 |
| HPV31 | E1 | 10 | 535 |
| HPV31 | E1 | 10 | 47 |
| HPV31 | E1 | 11 | 47 |
| HPV31 | E1 | 9 | 253 |
| HPV31 | E1 | 11 | 143 |
| HPV31 | E1 | 10 | 340 |
| HPV31 | E1 | 11 | 340 |
| HPV31 | E1 | 10 | 547 |
| HPV31 | E1 | 8 | 104 |
| HPV31 | E1 | 9 | 104 |
| HPV31 | E1 | 11 | 104 |
| HPV31 | E1 | 11 | 523 |
| HPV31 | E1 | 11 | 579 |
| HPV31 | E1 | 8 | 59 |
| HPV31 | E1 | 10 | 59 |
| HPV31 | E1 | 11 | 59 |
| HPV31 | E1 | 9 | 55 |
| HPV31 | E1 | 9 | 492 |
| HPV31 | E1 | 10 | 492 |
| HPV31 | E1 | 8 | 541 |
| HPV31 | E1 | 10 | 541 |
| HPV31 | E1 | 9 | 93 |
| HPV31 | E1 | 11 | 93 |
| HPV31 | E1 | 8 | 289 |
| HPV31 | E1 | 9 | 289 |
| HPV31 | E1 | 10 | 289 |
| HPV31 | E1 | 11 | 289 |
| HPV31 | E1 | 9 | 540 |
| HPV31 | E1 | 11 | 540 |
| HPV31 | E1 | 10 | 524 |
| HPV31 | E1 | 11 | 524 |
| HPV31 | E1 | 10 | 580 |
| HPV31 | E1 | 8 | 430 |
| HPV31 | E1 | 10 | 430 |
| HPV31 | E1 | 11 | 430 |
| HPV31 | E1 | 9 | 361 |
| HPV31 | E1 | 11 | 361 |
| HPV31 | E1 | 8 | 536 |
| HPV31 | E1 | 9 | 536 |
| HPV31 | E1 | 8 | 399 |
| HPV31 | E1 | 11 | 339 |
| HPV31 | E1 | 8 | 491 |
| HPV31 | E1 | 10 | 491 |
| HPV31 | E1 | 11 | 491 |
| HPV31 | E1 | 9 | 288 |
| HPV31 | E1 | 10 | 288 |
| HPV31 | E1 | 11 | 288 |
| HPV31 | E1 | 9 | 236 |
| HPV31 | E1 | 8 | 429 |
| HPV31 | E1 | 9 | 429 |
| HPV31 | E1 | 11 | 429 |
| HPV31 | E1 | 9 | 145 |
| HPV31 | E1 | 8 | 83 |
| HPV31 | E1 | 10 | 176 |
| HPV31 | E1 | 11 | 176 |
| HPV31 | E1 | 8 | 267 |
| HPV31 | E1 | 11 | 267 |
| HPV31 | E1 | 10 | 124 |
| HPV31 | E1 | 11 | 562 |
| HPV31 | E1 | 8 | 398 |
| HPV31 | E1 | 9 | 398 |
| HPV31 | E1 | 9 | 322 |
| HPV31 | E1 | 8 | 526 |
| HPV31 | E1 | 9 | 526 |
| HPV31 | E1 | 10 | 526 |
| HPV31 | E1 | 8 | 246 |
| HPV31 | E1 | 9 | 246 |
| HPV31 | E1 | 10 | 246 |
| HPV31 | E1 | 11 | 246 |
| HPV31 | E1 | 10 | 469 |
| HPV31 | E1 | 11 | 469 |
| HPV31 | E1 | 10 | 92 |
| HPV31 | E1 | 9 | 106 |
| HPV31 | E1 | 8 | 338 |
| HPV31 | E1 | 9 | 269 |
| HPV31 | E1 | 10 | 269 |
| HPV31 | E1 | 8 | 233 |
| HPV31 | E1 | 9 | 233 |
| HPV31 | E1 | 9 | 387 |
| HPV31 | E1 | 10 | 506 |
| HPV31 | E1 | 11 | 506 |
| HPV31 | E1 | 10 | 316 |
| HPV31 | E1 | 11 | 316 |
| HPV31 | E1 | 9 | 169 |
| HPV31 | E1 | 10 | 169 |
| HPV31 | E1 | 9 | 226 |
| HPV31 | E1 | 10 | 226 |
| HPV31 | E1 | 10 | 23 |
| HPV31 | E1 | 11 | 84 |
| HPV31 | E1 | 9 | 177 |
| HPV31 | E1 | 10 | 177 |

TABLE XIV-continued

HLA-B62 Supermotif Peptides

| 1 | 2 | 3 | 4 |
|---|---|---|---|
| HPV31 | E1 | 11 | 177 |
| HPV31 | E1 | 11 | 325 |
| HPV31 | E1 | 8 | 349 |
| HPV31 | E1 | 9 | 349 |
| HPV31 | E1 | 11 | 349 |
| HPV31 | E1 | 8 | 254 |
| HPV31 | E1 | 11 | 254 |
| HPV31 | E1 | 8 | 447 |
| HPV31 | E1 | 9 | 447 |
| HPV31 | E1 | 10 | 144 |
| HPV31 | E1 | 8 | 82 |
| HPV31 | E1 | 9 | 82 |
| HPV31 | E1 | 9 | 341 |
| HPV31 | E1 | 10 | 341 |
| HPV31 | E1 | 9 | 564 |
| HPV31 | E1 | 11 | 564 |
| HPV31 | E1 | 8 | 319 |
| HPV31 | E1 | 9 | 405 |
| HPV31 | E1 | 8 | 489 |
| HPV31 | E1 | 10 | 489 |
| HPV31 | E1 | 8 | 556 |
| HPV31 | E1 | 9 | 556 |
| HPV31 | E1 | 10 | 556 |
| HPV31 | E1 | 11 | 556 |
| HPV31 | E1 | 9 | 511 |
| HPV31 | E1 | 10 | 511 |
| HPV31 | E1 | 8 | 558 |
| HPV31 | E1 | 9 | 558 |
| HPV31 | E1 | 11 | 558 |
| HPV31 | E1 | 11 | 515 |
| HPV31 | E1 | 9 | 428 |
| HPV31 | E1 | 10 | 428 |
| HPV31 | E1 | 9 | 89 |
| HPV31 | E2 | 8 | 72 |
| HPV31 | E2 | 11 | 72 |
| HPV31 | E2 | 8 | 338 |
| HPV31 | E2 | 8 | 229 |
| HPV31 | E2 | 11 | 229 |
| HPV31 | E2 | 9 | 69 |
| HPV31 | E2 | 10 | 69 |
| HPV31 | E2 | 11 | 69 |
| HPV31 | E2 | 9 | 61 |
| HPV31 | E2 | 10 | 61 |
| HPV31 | E2 | 11 | 105 |
| HPV31 | E2 | 10 | 286 |
| HPV31 | E2 | 11 | 286 |
| HPV31 | E2 | 8 | 140 |
| HPV31 | E2 | 9 | 140 |
| HPV31 | E2 | 9 | 109 |
| HPV31 | E2 | 11 | 109 |
| HPV31 | E2 | 9 | 307 |
| HPV31 | E2 | 8 | 289 |
| HPV31 | E2 | 10 | 289 |
| HPV31 | E2 | 9 | 11 |
| HPV31 | E2 | 10 | 40 |
| HPV31 | E2 | 8 | 124 |
| HPV31 | E2 | 11 | 124 |
| HPV31 | E2 | 8 | 204 |
| HPV31 | E2 | 11 | 204 |
| HPV31 | E2 | 9 | 74 |
| HPV31 | E2 | 11 | 100 |
| HPV31 | E2 | 11 | 48 |
| HPV31 | E2 | 9 | 320 |
| HPV31 | E2 | 8 | 185 |
| HPV31 | E2 | 9 | 185 |
| HPV31 | E2 | 10 | 185 |
| HPV31 | E2 | 11 | 185 |
| HPV31 | E2 | 8 | 118 |
| HPV31 | E2 | 11 | 353 |
| HPV31 | E2 | 11 | 195 |
| HPV31 | E2 | 8 | 168 |
| HPV31 | E2 | 11 | 168 |
| HPV31 | E2 | 9 | 50 |
| HPV31 | E2 | 10 | 50 |
| HPV31 | E2 | 9 | 209 |
| HPV31 | E2 | 10 | 156 |
| HPV31 | E2 | 10 | 143 |
| HPV31 | E2 | 10 | 190 |
| HPV31 | E2 | 11 | 190 |
| HPV31 | E2 | 8 | 150 |
| HPV31 | E2 | 9 | 150 |
| HPV31 | E2 | 10 | 150 |
| HPV31 | E2 | 11 | 150 |
| HPV31 | E2 | 8 | 29 |
| HPV31 | E2 | 10 | 29 |
| HPV31 | E2 | 8 | 35 |
| HPV31 | E2 | 9 | 35 |
| HPV31 | E2 | 10 | 35 |
| HPV31 | E2 | 8 | 164 |
| HPV31 | E2 | 8 | 297 |
| HPV31 | E2 | 9 | 297 |
| HPV31 | E2 | 11 | 257 |
| HPV31 | E2 | 9 | 56 |
| HPV31 | E2 | 8 | 295 |
| HPV31 | E2 | 10 | 295 |
| HPV31 | E2 | 11 | 295 |
| HPV31 | E2 | 9 | 304 |
| HPV31 | E2 | 11 | 359 |
| HPV31 | E2 | 8 | 193 |
| HPV31 | E2 | 8 | 210 |
| HPV31 | E2 | 8 | 358 |
| HPV31 | E2 | 8 | 260 |
| HPV31 | E2 | 11 | 260 |
| HPV31 | E2 | 11 | 316 |
| HPV31 | E2 | 10 | 261 |
| HPV31 | E2 | 8 | 42 |
| HPV31 | E2 | 10 | 42 |
| HPV31 | E2 | 8 | 70 |
| HPV31 | E2 | 9 | 70 |
| HPV31 | E2 | 10 | 70 |
| HPV31 | E2 | 8 | 75 |
| HPV31 | E2 | 10 | 78 |
| HPV31 | E2 | 11 | 77 |
| HPV31 | E2 | 8 | 94 |
| HPV31 | E2 | 9 | 94 |
| HPV31 | E2 | 10 | 94 |
| HPV31 | E2 | 8 | 303 |
| HPV31 | E2 | 10 | 303 |
| HPV31 | E2 | 10 | 282 |
| HPV31 | E2 | 8 | 9 |
| HPV31 | E2 | 11 | 9 |
| HPV31 | E2 | 9 | 294 |
| HPV31 | E2 | 11 | 294 |
| HPV31 | E2 | 10 | 317 |
| HPV31 | E2 | 8 | 95 |
| HPV31 | E2 | 9 | 95 |
| HPV31 | E2 | 11 | 95 |
| HPV31 | E2 | 9 | 191 |
| HPV31 | E2 | 10 | 191 |
| HPV31 | E2 | 8 | 151 |
| HPV31 | E2 | 9 | 151 |
| HPV31 | E2 | 10 | 151 |
| HPV31 | E2 | 8 | 321 |
| HPV31 | E2 | 8 | 57 |
| HPV31 | E2 | 11 | 57 |
| HPV31 | E2 | 8 | 25 |
| HPV31 | E2 | 9 | 25 |
| HPV31 | E2 | 8 | 37 |
| HPV31 | E2 | 10 | 37 |
| HPV31 | E2 | 9 | 7 |
| HPV31 | E2 | 10 | 7 |
| HPV31 | E2 | 8 | 311 |
| HPV31 | E2 | 9 | 311 |
| HPV31 | E2 | 9 | 53 |
| HPV31 | E2 | 10 | 53 |
| HPV31 | E2 | 8 | 98 |
| HPV31 | E2 | 10 | 348 |
| HPV31 | E2 | 11 | 5 |
| HPV31 | E2 | 9 | 266 |
| HPV31 | E2 | 10 | 266 |

TABLE XIV-continued

HLA-B62 Supermotif Peptides

| 1 | 2 | 3 | 4 |
|---|---|---|---|
| HPV31 | E2 | 8 | 198 |
| HPV31 | E2 | 10 | 198 |
| HPV31 | E2 | 11 | 198 |
| HPV31 | E2 | 9 | 269 |
| HPV31 | E2 | 10 | 269 |
| HPV31 | E2 | 11 | 269 |
| HPV31 | E2 | 8 | 63 |
| HPV31 | E2 | 10 | 63 |
| HPV31 | E2 | 11 | 63 |
| HPV31 | E2 | 9 | 364 |
| HPV31 | E2 | 8 | 3 |
| HPV31 | E2 | 9 | 128 |
| HPV31 | E2 | 10 | 128 |
| HPV31 | E2 | 11 | 128 |
| HPV31 | E2 | 9 | 93 |
| HPV31 | E2 | 10 | 93 |
| HPV31 | E2 | 11 | 93 |
| HPV31 | E2 | 10 | 293 |
| HPV31 | E2 | 10 | 116 |
| HPV31 | E2 | 8 | 356 |
| HPV31 | E2 | 10 | 356 |
| HPV31 | E2 | 8 | 362 |
| HPV31 | E2 | 9 | 362 |
| HPV31 | E2 | 11 | 362 |
| HPV31 | E2 | 8 | 192 |
| HPV31 | E2 | 9 | 192 |
| HPV31 | E2 | 9 | 41 |
| HPV31 | E2 | 11 | 41 |
| HPV31 | E2 | 9 | 59 |
| HPV31 | E2 | 11 | 59 |
| HPV31 | E2 | 11 | 119 |
| HPV31 | E2 | 11 | 147 |
| HPV31 | E2 | 10 | 58 |
| HPV31 | E2 | 10 | 344 |
| HPV31 | E2 | 11 | 344 |
| HPV31 | E2 | 10 | 138 |
| HPV31 | E2 | 11 | 138 |
| HPV31 | E2 | 9 | 102 |
| HPV31 | E2 | 9 | 159 |
| HPV31 | E2 | 10 | 159 |
| HPV31 | E2 | 11 | 159 |
| HPV31 | E5 | 8 | 61 |
| HPV31 | E5 | 9 | 61 |
| HPV31 | E5 | 11 | 61 |
| HPV31 | E5 | 8 | 26 |
| HPV31 | E5 | 9 | 26 |
| HPV31 | E5 | 11 | 26 |
| HPV31 | E5 | 8 | 20 |
| HPV31 | E5 | 9 | 20 |
| HPV31 | E5 | 10 | 20 |
| HPV31 | E5 | 9 | 3 |
| HPV31 | E5 | 10 | 3 |
| HPV31 | E5 | 11 | 3 |
| HPV31 | E5 | 8 | 66 |
| HPV31 | E5 | 9 | 66 |
| HPV31 | E5 | 8 | 15 |
| HPV31 | E5 | 9 | 15 |
| HPV31 | E5 | 10 | 15 |
| HPV31 | E5 | 11 | 15 |
| HPV31 | E5 | 9 | 24 |
| HPV31 | E5 | 10 | 24 |
| HPV31 | E5 | 11 | 24 |
| HPV31 | E5 | 9 | 72 |
| HPV31 | E5 | 10 | 72 |
| HPV31 | E5 | 10 | 48 |
| HPV31 | E5 | 10 | 69 |
| HPV31 | E5 | 8 | 46 |
| HPV31 | E5 | 9 | 11 |
| HPV31 | E5 | 11 | 11 |
| HPV31 | E5 | 8 | 45 |
| HPV31 | E5 | 9 | 45 |
| HPV31 | E5 | 8 | 16 |
| HPV31 | E5 | 9 | 16 |
| HPV31 | E5 | 10 | 16 |
| HPV31 | E5 | 8 | 22 |
| HPV31 | E5 | 11 | 22 |
| HPV31 | E5 | 8 | 44 |
| HPV31 | E5 | 9 | 44 |
| HPV31 | E5 | 10 | 44 |
| HPV31 | E5 | 8 | 43 |
| HPV31 | E5 | 9 | 43 |
| HPV31 | E5 | 10 | 43 |
| HPV31 | E5 | 11 | 43 |
| HPV31 | E5 | 8 | 42 |
| HPV31 | E5 | 9 | 42 |
| HPV31 | E5 | 10 | 42 |
| HPV31 | E5 | 11 | 42 |
| HPV31 | E5 | 8 | 27 |
| HPV31 | E5 | 10 | 27 |
| HPV31 | E5 | 8 | 32 |
| HPV31 | E5 | 9 | 32 |
| HPV31 | E5 | 11 | 32 |
| HPV31 | E5 | 9 | 1 |
| HPV31 | E5 | 11 | 1 |
| HPV31 | E5 | 8 | 5 |
| HPV31 | E5 | 9 | 5 |
| HPV31 | E5 | 11 | 5 |
| HPV31 | E5 | 9 | 70 |
| HPV31 | E5 | 11 | 70 |
| HPV31 | E5 | 8 | 56 |
| HPV31 | E5 | 9 | 56 |
| HPV31 | E5 | 10 | 56 |
| HPV31 | E5 | 11 | 56 |
| HPV31 | E5 | 8 | 31 |
| HPV31 | E5 | 9 | 31 |
| HPV31 | E5 | 10 | 31 |
| HPV31 | E5 | 9 | 30 |
| HPV31 | E5 | 10 | 30 |
| HPV31 | E5 | 11 | 30 |
| HPV31 | E5 | 8 | 10 |
| HPV31 | E5 | 10 | 10 |
| HPV31 | E5 | 8 | 55 |
| HPV31 | E5 | 9 | 55 |
| HPV31 | E5 | 10 | 55 |
| HPV31 | E5 | 11 | 55 |
| HPV31 | E5 | 8 | 35 |
| HPV31 | E5 | 9 | 35 |
| HPV31 | E5 | 10 | 35 |
| HPV31 | E5 | 11 | 35 |
| HPV31 | E5 | 8 | 37 |
| HPV31 | E5 | 9 | 37 |
| HPV31 | E5 | 10 | 37 |
| HPV31 | E5 | 11 | 37 |
| HPV31 | E5 | 8 | 41 |
| HPV31 | E5 | 9 | 41 |
| HPV31 | E5 | 10 | 41 |
| HPV31 | E5 | 11 | 41 |
| HPV31 | E5 | 8 | 8 |
| HPV31 | E5 | 9 | 8 |
| HPV31 | E5 | 10 | 8 |
| HPV31 | E5 | 10 | 51 |
| HPV31 | E5 | 8 | 73 |
| HPV31 | E5 | 9 | 73 |
| HPV31 | E5 | 11 | 47 |
| HPV31 | E5 | 9 | 28 |
| HPV31 | E5 | 11 | 28 |
| HPV31 | E5 | 8 | 12 |
| HPV31 | E5 | 10 | 12 |
| HPV31 | E5 | 11 | 12 |
| HPV31 | E5 | 8 | 21 |
| HPV31 | E5 | 9 | 21 |
| HPV31 | E5 | 8 | 33 |
| HPV31 | E5 | 10 | 33 |
| HPV31 | E5 | 11 | 33 |
| HPV31 | E5 | 8 | 64 |
| HPV31 | E5 | 9 | 64 |
| HPV31 | E5 | 10 | 64 |
| HPV31 | E5 | 11 | 64 |
| HPV31 | E5 | 8 | 50 |
| HPV31 | E5 | 11 | 50 |

TABLE XIV-continued

HLA-B62 Supermotif Peptides

| 1 | 2 | 3 | 4 |
|---|---|---|---|
| HPV31 | E5 | 11 | 68 |
| HPV31 | E5 | 9 | 63 |
| HPV31 | E5 | 10 | 63 |
| HPV31 | E5 | 11 | 63 |
| HPV31 | E6 | 9 | 18 |
| HPV31 | E6 | 11 | 18 |
| HPV31 | E6 | 8 | 103 |
| HPV31 | E6 | 8 | 65 |
| HPV31 | E6 | 11 | 66 |
| HPV31 | E6 | 9 | 111 |
| HPV31 | E6 | 8 | 30 |
| HPV31 | E6 | 9 | 20 |
| HPV31 | E6 | 8 | 25 |
| HPV31 | E6 | 8 | 14 |
| HPV31 | E6 | 10 | 14 |
| HPV31 | E6 | 10 | 41 |
| HPV31 | E6 | 10 | 95 |
| HPV31 | E6 | 8 | 35 |
| HPV31 | E6 | 9 | 35 |
| HPV31 | E6 | 11 | 35 |
| HPV31 | E6 | 9 | 61 |
| HPV31 | E6 | 10 | 61 |
| HPV31 | E6 | 8 | 118 |
| HPV31 | E6 | 11 | 118 |
| HPV31 | E6 | 8 | 21 |
| HPV31 | E6 | 11 | 21 |
| HPV31 | E6 | 11 | 52 |
| HPV31 | E6 | 8 | 11 |
| HPV31 | E6 | 9 | 11 |
| HPV31 | E6 | 11 | 11 |
| HPV31 | E6 | 10 | 90 |
| HPV31 | E6 | 11 | 90 |
| HPV31 | E6 | 11 | 115 |
| HPV31 | E6 | 8 | 72 |
| HPV31 | E6 | 10 | 72 |
| HPV31 | E6 | 11 | 100 |
| HPV31 | E6 | 11 | 127 |
| HPV31 | E6 | 9 | 4 |
| HPV31 | E6 | 11 | 109 |
| HPV31 | E6 | 8 | 36 |
| HPV31 | E6 | 10 | 36 |
| HPV31 | E6 | 11 | 36 |
| HPV31 | E6 | 11 | 27 |
| HPV31 | E6 | 8 | 8 |
| HPV31 | E6 | 11 | 8 |
| HPV31 | E6 | 8 | 142 |
| HPV31 | E6 | 10 | 82 |
| HPV31 | E6 | 10 | 87 |
| HPV31 | E6 | 10 | 58 |
| HPV31 | E6 | 9 | 42 |
| HPV31 | E6 | 11 | 42 |
| HPV31 | E7 | 8 | 91 |
| HPV31 | E7 | 9 | 59 |
| HPV31 | E7 | 11 | 59 |
| HPV31 | E7 | 9 | 68 |
| HPV31 | E7 | 11 | 68 |
| HPV31 | E7 | 8 | 75 |
| HPV31 | E7 | 9 | 75 |
| HPV31 | E7 | 10 | 75 |
| HPV31 | E7 | 8 | 21 |
| HPV31 | E7 | 9 | 14 |
| HPV31 | E7 | 10 | 36 |
| HPV31 | E7 | 9 | 81 |
| HPV31 | E7 | 10 | 81 |
| HPV31 | E7 | 9 | 46 |
| HPV31 | E7 | 10 | 46 |
| HPV31 | E7 | 11 | 88 |
| HPV31 | E7 | 10 | 43 |
| HPV31 | E7 | 10 | 78 |
| HPV31 | E7 | 10 | 89 |
| HPV31 | E7 | 8 | 82 |
| HPV31 | E7 | 9 | 82 |
| HPV31 | E7 | 8 | 83 |
| HPV31 | E7 | 10 | 28 |
| HPV31 | E7 | 11 | 28 |
| HPV31 | E7 | 8 | 8 |
| HPV31 | E7 | 9 | 79 |
| HPV31 | E7 | 11 | 79 |
| HPV31 | E7 | 8 | 15 |
| HPV31 | E7 | 11 | 15 |
| HPV31 | E7 | 11 | 27 |
| HPV31 | E7 | 10 | 16 |
| HPV31 | E7 | 10 | 73 |
| HPV31 | E7 | 11 | 73 |
| HPV31 | E7 | 8 | 77 |
| HPV31 | E7 | 11 | 77 |
| HPV31 | E7 | 9 | 66 |
| HPV31 | E7 | 11 | 66 |
| HPV31 | E7 | 9 | 7 |
| HPV31 | E7 | 11 | 64 |
| HPV31 | E7 | 8 | 5 |
| HPV31 | E7 | 9 | 5 |
| HPV31 | E7 | 11 | 5 |
| HPV31 | E7 | 8 | 72 |
| HPV31 | E7 | 11 | 72 |
| HPV31 | E7 | 9 | 37 |
| HPV31 | E7 | 8 | 12 |
| HPV31 | E7 | 11 | 12 |
| HPV31 | E7 | 8 | 69 |
| HPV31 | E7 | 10 | 69 |
| HPV31 | E7 | 11 | 69 |
| HPV31 | E7 | 9 | 11 |
| HPV31 | L1 | 9 | 348 |
| HPV31 | L1 | 8 | 398 |
| HPV31 | L1 | 10 | 398 |
| HPV31 | L1 | 8 | 426 |
| HPV31 | L1 | 10 | 180 |
| HPV31 | L1 | 9 | 213 |
| HPV31 | L1 | 11 | 213 |
| HPV31 | L1 | 10 | 433 |
| HPV31 | L1 | 10 | 488 |
| HPV31 | L1 | 8 | 317 |
| HPV31 | L1 | 10 | 317 |
| HPV31 | L1 | 8 | 305 |
| HPV31 | L1 | 9 | 305 |
| HPV31 | L1 | 10 | 305 |
| HPV31 | L1 | 11 | 147 |
| HPV31 | L1 | 9 | 158 |
| HPV31 | L1 | 10 | 186 |
| HPV31 | L1 | 11 | 186 |
| HPV31 | L1 | 9 | 224 |
| HPV31 | L1 | 9 | 387 |
| HPV31 | L1 | 11 | 459 |
| HPV31 | L1 | 8 | 372 |
| HPV31 | L1 | 11 | 372 |
| HPV31 | L1 | 11 | 275 |
| HPV31 | L1 | 9 | 200 |
| HPV31 | L1 | 10 | 200 |
| HPV31 | L1 | 8 | 440 |
| HPV31 | L1 | 9 | 440 |
| HPV31 | L1 | 11 | 440 |
| HPV31 | L1 | 9 | 461 |
| HPV31 | L1 | 10 | 461 |
| HPV31 | L1 | 11 | 461 |
| HPV31 | L1 | 8 | 241 |
| HPV31 | L1 | 9 | 241 |
| HPV31 | L1 | 10 | 241 |
| HPV31 | L1 | 11 | 241 |
| HPV31 | L1 | 8 | 254 |
| HPV31 | L1 | 9 | 254 |
| HPV31 | L1 | 8 | 107 |
| HPV31 | L1 | 10 | 107 |
| HPV31 | L1 | 8 | 449 |
| HPV31 | L1 | 10 | 449 |
| HPV31 | L1 | 8 | 375 |
| HPV31 | L1 | 10 | 375 |
| HPV31 | L1 | 9 | 469 |
| HPV31 | L1 | 8 | 463 |
| HPV31 | L1 | 9 | 463 |
| HPV31 | L1 | 11 | 463 |

TABLE XIV-continued

HLA-B62 Supermotif Peptides

| 1 | 2 | 3 | 4 |
|---|---|---|---|
| HPV31 | L1 | 8 | 293 |
| HPV31 | L1 | 9 | 293 |
| HPV31 | L1 | 8 | 377 |
| HPV31 | L1 | 10 | 377 |
| HPV31 | L1 | 8 | 323 |
| HPV31 | L1 | 9 | 323 |
| HPV31 | L1 | 10 | 323 |
| HPV31 | L1 | 8 | 117 |
| HPV31 | L1 | 11 | 117 |
| HPV31 | L1 | 10 | 105 |
| HPV31 | L1 | 9 | 68 |
| HPV31 | L1 | 11 | 68 |
| HPV31 | L1 | 10 | 406 |
| HPV31 | L1 | 10 | 139 |
| HPV31 | L1 | 8 | 111 |
| HPV31 | L1 | 9 | 115 |
| HPV31 | L1 | 10 | 115 |
| HPV31 | L1 | 9 | 399 |
| HPV31 | L1 | 8 | 388 |
| HPV31 | L1 | 11 | 388 |
| HPV31 | L1 | 10 | 52 |
| HPV31 | L1 | 11 | 52 |
| HPV31 | L1 | 11 | 196 |
| HPV31 | L1 | 9 | 61 |
| HPV31 | L1 | 11 | 61 |
| HPV31 | L1 | 8 | 381 |
| HPV31 | L1 | 9 | 381 |
| HPV31 | L1 | 11 | 381 |
| HPV31 | L1 | 10 | 60 |
| HPV31 | L1 | 11 | 237 |
| HPV31 | L1 | 10 | 436 |
| HPV31 | L1 | 11 | 436 |
| HPV31 | L1 | 8 | 163 |
| HPV31 | L1 | 8 | 310 |
| HPV31 | L1 | 8 | 153 |
| HPV31 | L1 | 9 | 65 |
| HPV31 | L1 | 10 | 65 |
| HPV31 | L1 | 8 | 20 |
| HPV31 | L1 | 9 | 20 |
| HPV31 | L1 | 8 | 159 |
| HPV31 | L1 | 8 | 470 |
| HPV31 | L1 | 8 | 42 |
| HPV31 | L1 | 9 | 42 |
| HPV31 | L1 | 11 | 42 |
| HPV31 | L1 | 9 | 78 |
| HPV31 | L1 | 9 | 13 |
| HPV31 | L1 | 10 | 13 |
| HPV31 | L1 | 11 | 471 |
| HPV31 | L1 | 8 | 214 |
| HPV31 | L1 | 10 | 214 |
| HPV31 | L1 | 10 | 373 |
| HPV31 | L1 | 8 | 69 |
| HPV31 | L1 | 10 | 69 |
| HPV31 | L1 | 8 | 99 |
| HPV31 | L1 | 10 | 99 |
| HPV31 | L1 | 11 | 314 |
| HPV31 | L1 | 10 | 238 |
| HPV31 | L1 | 11 | 238 |
| HPV31 | L1 | 8 | 201 |
| HPV31 | L1 | 9 | 201 |
| HPV31 | L1 | 11 | 201 |
| HPV31 | L1 | 8 | 300 |
| HPV31 | L1 | 9 | 300 |
| HPV31 | L1 | 9 | 32 |
| HPV31 | L1 | 11 | 32 |
| HPV31 | L1 | 8 | 451 |
| HPV31 | L1 | 10 | 451 |
| HPV31 | L1 | 8 | 342 |
| HPV31 | L1 | 9 | 342 |
| HPV31 | L1 | 8 | 396 |
| HPV31 | L1 | 10 | 396 |
| HPV31 | L1 | 8 | 93 |
| HPV31 | L1 | 9 | 93 |
| HPV31 | L1 | 10 | 93 |
| HPV31 | L1 | 10 | 57 |
| HPV31 | L1 | 8 | 328 |
| HPV31 | L1 | 10 | 220 |
| HPV31 | L1 | 8 | 222 |
| HPV31 | L1 | 11 | 222 |
| HPV31 | L1 | 8 | 188 |
| HPV31 | L1 | 9 | 188 |
| HPV31 | L1 | 8 | 464 |
| HPV31 | L1 | 10 | 464 |
| HPV31 | L1 | 11 | 113 |
| HPV31 | L1 | 9 | 187 |
| HPV31 | L1 | 10 | 187 |
| HPV31 | L1 | 10 | 410 |
| HPV31 | L1 | 8 | 14 |
| HPV31 | L1 | 9 | 14 |
| HPV31 | L1 | 9 | 434 |
| HPV31 | L1 | 8 | 15 |
| HPV31 | L1 | 11 | 17 |
| HPV31 | L1 | 8 | 306 |
| HPV31 | L1 | 9 | 306 |
| HPV31 | L1 | 9 | 378 |
| HPV31 | L1 | 11 | 378 |
| HPV31 | L1 | 11 | 156 |
| HPV31 | L1 | 8 | 255 |
| HPV31 | L1 | 9 | 41 |
| HPV31 | L1 | 10 | 41 |
| HPV31 | L1 | 8 | 77 |
| HPV31 | L1 | 10 | 77 |
| HPV31 | L1 | 9 | 98 |
| HPV31 | L1 | 11 | 98 |
| HPV31 | L1 | 11 | 478 |
| HPV31 | L1 | 8 | 5 |
| HPV31 | L1 | 9 | 5 |
| HPV31 | L1 | 10 | 75 |
| HPV31 | L1 | 8 | 228 |
| HPV31 | L1 | 9 | 228 |
| HPV31 | L1 | 11 | 228 |
| HPV31 | L1 | 11 | 51 |
| HPV31 | L1 | 8 | 414 |
| HPV31 | L1 | 9 | 414 |
| HPV31 | L1 | 8 | 2 |
| HPV31 | L1 | 10 | 2 |
| HPV31 | L1 | 11 | 2 |
| HPV31 | L1 | 9 | 149 |
| HPV31 | L1 | 11 | 149 |
| HPV31 | L1 | 10 | 394 |
| HPV31 | L1 | 9 | 299 |
| HPV31 | L1 | 10 | 299 |
| HPV31 | L1 | 8 | 174 |
| HPV31 | L1 | 10 | 424 |
| HPV31 | L1 | 8 | 194 |
| HPV31 | L1 | 9 | 194 |
| HPV31 | L1 | 8 | 271 |
| HPV31 | L1 | 8 | 286 |
| HPV31 | L1 | 11 | 246 |
| HPV31 | L1 | 9 | 383 |
| HPV31 | L1 | 10 | 383 |
| HPV31 | L1 | 8 | 182 |
| HPV31 | L1 | 10 | 182 |
| HPV31 | L1 | 11 | 409 |
| HPV31 | L1 | 11 | 295 |
| HPV31 | L1 | 9 | 96 |
| HPV31 | L1 | 11 | 96 |
| HPV31 | L1 | 10 | 267 |
| HPV31 | L1 | 11 | 267 |
| HPV31 | L1 | 9 | 44 |
| HPV31 | L1 | 11 | 333 |
| HPV31 | L1 | 9 | 10 |
| HPV31 | L1 | 8 | 195 |
| HPV31 | L1 | 9 | 63 |
| HPV31 | L1 | 11 | 63 |
| HPV31 | L1 | 9 | 221 |
| HPV31 | L1 | 10 | 334 |
| HPV31 | L1 | 8 | 62 |
| HPV31 | L1 | 10 | 62 |
| HPV31 | L1 | 8 | 21 |

TABLE XIV-continued

HLA-B62 Supermotif Peptides

| 1 | 2 | 3 | 4 |
|---|---|---|---|
| HPV31 | L1 | 8 | 391 |
| HPV31 | L1 | 9 | 391 |
| HPV31 | L1 | 10 | 391 |
| HPV31 | L1 | 9 | 277 |
| HPV31 | L1 | 11 | 277 |
| HPV31 | L1 | 9 | 235 |
| HPV31 | L1 | 10 | 12 |
| HPV31 | L1 | 11 | 12 |
| HPV31 | L1 | 8 | 364 |
| HPV31 | L1 | 10 | 364 |
| HPV31 | L1 | 8 | 250 |
| HPV31 | L1 | 9 | 250 |
| HPV31 | L1 | 8 | 232 |
| HPV31 | L1 | 9 | 232 |
| HPV31 | L1 | 8 | 445 |
| HPV31 | L1 | 8 | 27 |
| HPV31 | L1 | 9 | 27 |
| HPV31 | L1 | 11 | 27 |
| HPV31 | L2 | 8 | 143 |
| HPV31 | L2 | 9 | 286 |
| HPV31 | L2 | 11 | 286 |
| HPV31 | L2 | 9 | 271 |
| HPV31 | L2 | 10 | 271 |
| HPV31 | L2 | 11 | 271 |
| HPV31 | L2 | 8 | 240 |
| HPV31 | L2 | 8 | 414 |
| HPV31 | L2 | 10 | 414 |
| HPV31 | L2 | 11 | 414 |
| HPV31 | L2 | 9 | 424 |
| HPV31 | L2 | 10 | 424 |
| HPV31 | L2 | 11 | 424 |
| HPV31 | L2 | 8 | 376 |
| HPV31 | L2 | 10 | 376 |
| HPV31 | L2 | 11 | 376 |
| HPV31 | L2 | 9 | 28 |
| HPV31 | L2 | 11 | 133 |
| HPV31 | L2 | 9 | 278 |
| HPV31 | L2 | 10 | 278 |
| HPV31 | L2 | 10 | 400 |
| HPV31 | L2 | 8 | 322 |
| HPV31 | L2 | 8 | 354 |
| HPV31 | L2 | 10 | 354 |
| HPV31 | L2 | 8 | 273 |
| HPV31 | L2 | 9 | 273 |
| HPV31 | L2 | 10 | 273 |
| HPV31 | L2 | 8 | 102 |
| HPV31 | L2 | 11 | 160 |
| HPV31 | L2 | 11 | 234 |
| HPV31 | L2 | 10 | 96 |
| HPV31 | L2 | 11 | 96 |
| HPV31 | L2 | 9 | 43 |
| HPV31 | L2 | 11 | 43 |
| HPV31 | L2 | 8 | 116 |
| HPV31 | L2 | 11 | 31 |
| HPV31 | L2 | 11 | 408 |
| HPV31 | L2 | 8 | 190 |
| HPV31 | L2 | 9 | 190 |
| HPV31 | L2 | 9 | 334 |
| HPV31 | L2 | 10 | 196 |
| HPV31 | L2 | 11 | 276 |
| HPV31 | L2 | 8 | 237 |
| HPV31 | L2 | 9 | 237 |
| HPV31 | L2 | 11 | 237 |
| HPV31 | L2 | 10 | 421 |
| HPV31 | L2 | 8 | 433 |
| HPV31 | L2 | 9 | 433 |
| HPV31 | L2 | 9 | 113 |
| HPV31 | L2 | 11 | 113 |
| HPV31 | L2 | 11 | 351 |
| HPV31 | L2 | 10 | 221 |
| HPV31 | L2 | 9 | 406 |
| HPV31 | L2 | 8 | 99 |
| HPV31 | L2 | 10 | 99 |
| HPV31 | L2 | 11 | 99 |
| HPV31 | L2 | 9 | 52 |
| HPV31 | L2 | 8 | 213 |
| HPV31 | L2 | 10 | 213 |
| HPV31 | L2 | 11 | 213 |
| HPV31 | L2 | 9 | 175 |
| HPV31 | L2 | 8 | 125 |
| HPV31 | L2 | 10 | 125 |
| HPV31 | L2 | 11 | 125 |
| HPV31 | L2 | 8 | 279 |
| HPV31 | L2 | 9 | 279 |
| HPV31 | L2 | 9 | 45 |
| HPV31 | L2 | 10 | 45 |
| HPV31 | L2 | 11 | 45 |
| HPV31 | L2 | 8 | 211 |
| HPV31 | L2 | 10 | 211 |
| HPV31 | L2 | 10 | 123 |
| HPV31 | L2 | 9 | 401 |
| HPV31 | L2 | 11 | 401 |
| HPV31 | L2 | 9 | 87 |
| HPV31 | L2 | 9 | 33 |
| HPV31 | L2 | 10 | 33 |
| HPV31 | L2 | 8 | 191 |
| HPV31 | L2 | 8 | 114 |
| HPV31 | L2 | 10 | 114 |
| HPV31 | L2 | 10 | 105 |
| HPV31 | L2 | 11 | 105 |
| HPV31 | L2 | 9 | 197 |
| HPV31 | L2 | 8 | 35 |
| HPV31 | L2 | 11 | 35 |
| HPV31 | L2 | 10 | 242 |
| HPV31 | L2 | 11 | 242 |
| HPV31 | L2 | 10 | 302 |
| HPV31 | L2 | 8 | 231 |
| HPV31 | L2 | 10 | 231 |
| HPV31 | L2 | 8 | 244 |
| HPV31 | L2 | 9 | 244 |
| HPV31 | L2 | 8 | 176 |
| HPV31 | L2 | 8 | 108 |
| HPV31 | L2 | 10 | 108 |
| HPV31 | L2 | 9 | 447 |
| HPV31 | L2 | 11 | 447 |
| HPV31 | L2 | 8 | 335 |
| HPV31 | L2 | 8 | 269 |
| HPV31 | L2 | 9 | 269 |
| HPV31 | L2 | 11 | 269 |
| HPV31 | L2 | 8 | 204 |
| HPV31 | L2 | 11 | 204 |
| HPV31 | L2 | 9 | 327 |
| HPV31 | L2 | 9 | 249 |
| HPV31 | L2 | 9 | 155 |
| HPV31 | L2 | 10 | 155 |
| HPV31 | L2 | 8 | 370 |
| HPV31 | L2 | 9 | 410 |
| HPV31 | L2 | 10 | 410 |
| HPV31 | L2 | 8 | 402 |
| HPV31 | L2 | 10 | 402 |
| HPV31 | L2 | 9 | 210 |
| HPV31 | L2 | 11 | 210 |
| HPV31 | L2 | 11 | 122 |
| HPV31 | L2 | 8 | 88 |
| HPV31 | L2 | 11 | 88 |
| HPV31 | L2 | 9 | 422 |
| HPV31 | L2 | 11 | 422 |
| HPV31 | L2 | 9 | 100 |
| HPV31 | L2 | 10 | 100 |
| HPV31 | L2 | 8 | 394 |
| HPV31 | L2 | 10 | 394 |
| HPV31 | L2 | 11 | 394 |
| HPV31 | L2 | 9 | 74 |
| HPV31 | L2 | 11 | 166 |
| HPV31 | L2 | 9 | 126 |
| HPV31 | L2 | 10 | 126 |
| HPV31 | L2 | 8 | 91 |
| HPV31 | L2 | 11 | 91 |
| HPV31 | L2 | 9 | 97 |
| HPV31 | L2 | 10 | 97 |

TABLE XIV-continued

HLA-B62 Supermotif Peptides

| 1 | 2 | 3 | 4 |
|---|---|---|---|
| HPV31 | L2 | 10 | 92 |
| HPV31 | L2 | 8 | 44 |
| HPV31 | L2 | 10 | 44 |
| HPV31 | L2 | 11 | 44 |
| HPV31 | L2 | 9 | 243 |
| HPV31 | L2 | 10 | 243 |
| HPV31 | L2 | 8 | 17 |
| HPV31 | L2 | 9 | 17 |
| HPV31 | L2 | 10 | 228 |
| HPV31 | L2 | 11 | 228 |
| HPV31 | L2 | 8 | 417 |
| HPV31 | L2 | 9 | 229 |
| HPV31 | L2 | 10 | 229 |
| HPV31 | L2 | 11 | 429 |
| HPV31 | L2 | 8 | 219 |
| HPV31 | L2 | 8 | 298 |
| HPV31 | L2 | 11 | 284 |
| HPV31 | L2 | 8 | 216 |
| HPV31 | L2 | 11 | 216 |
| HPV31 | L2 | 9 | 90 |
| HPV31 | L2 | 8 | 78 |
| HPV31 | L2 | 10 | 78 |
| HPV31 | L2 | 8 | 316 |
| HPV31 | L2 | 11 | 316 |
| HPV31 | L2 | 9 | 454 |
| HPV31 | L2 | 11 | 454 |
| HPV31 | L2 | 8 | 94 |
| HPV31 | L2 | 9 | 332 |
| HPV31 | L2 | 11 | 332 |
| HPV31 | L2 | 9 | 431 |
| HPV31 | L2 | 10 | 431 |
| HPV31 | L2 | 11 | 431 |
| HPV31 | L2 | 9 | 325 |
| HPV31 | L2 | 11 | 325 |
| HPV31 | L2 | 8 | 86 |
| HPV31 | L2 | 10 | 86 |
| HPV31 | L2 | 10 | 182 |
| HPV31 | L2 | 11 | 104 |
| HPV31 | L2 | 8 | 107 |
| HPV31 | L2 | 9 | 107 |
| HPV31 | L2 | 11 | 107 |
| HPV31 | L2 | 11 | 260 |
| HPV31 | L2 | 9 | 50 |
| HPV31 | L2 | 11 | 50 |
| HPV31 | L2 | 11 | 372 |
| HPV31 | L2 | 9 | 162 |
| HPV31 | L2 | 10 | 149 |
| HPV31 | L2 | 9 | 40 |
| HPV31 | L2 | 8 | 312 |
| HPV31 | L2 | 9 | 312 |
| HPV31 | L2 | 10 | 312 |
| HPV31 | L2 | 9 | 347 |
| HPV31 | L2 | 10 | 347 |
| HPV31 | L2 | 11 | 347 |
| HPV31 | L2 | 8 | 304 |
| HPV31 | L2 | 10 | 304 |
| HPV31 | L2 | 9 | 168 |
| HPV31 | L2 | 10 | 168 |
| HPV31 | L2 | 11 | 168 |
| HPV31 | L2 | 10 | 141 |
| HPV31 | L2 | 10 | 209 |
| HPV31 | L2 | 8 | 427 |
| HPV31 | L2 | 9 | 16 |
| HPV31 | L2 | 10 | 16 |
| HPV31 | L2 | 11 | 227 |
| HPV31 | L2 | 8 | 416 |
| HPV31 | L2 | 9 | 416 |
| HPV31 | L2 | 10 | 362 |
| HPV31 | L2 | 8 | 254 |
| HPV31 | L2 | 9 | 254 |
| HPV31 | L2 | 10 | 254 |
| HPV31 | L2 | 8 | 392 |
| HPV31 | L2 | 10 | 392 |
| HPV31 | L2 | 9 | 81 |
| HPV31 | L2 | 9 | 232 |
| HPV31 | L2 | 10 | 32 |
| HPV31 | L2 | 11 | 32 |
| HPV31 | L2 | 8 | 163 |
| HPV31 | L2 | 10 | 409 |
| HPV31 | L2 | 11 | 409 |
| HPV31 | L2 | 9 | 393 |
| HPV31 | L2 | 11 | 393 |
| HPV31 | L2 | 10 | 73 |
| HPV31 | L2 | 9 | 387 |
| HPV31 | L2 | 9 | 377 |
| HPV31 | L2 | 10 | 377 |
| HPV31 | L2 | 11 | 377 |
| HPV31 | L2 | 8 | 440 |
| HPV31 | L2 | 9 | 440 |
| HPV31 | L2 | 10 | 446 |
| HPV31 | L2 | 11 | 72 |
| HPV31 | L2 | 8 | 386 |
| HPV31 | L2 | 10 | 386 |
| HPV33 | E1 | 10 | 596 |
| HPV33 | E1 | 11 | 596 |
| HPV33 | E1 | 9 | 532 |
| HPV33 | E1 | 11 | 532 |
| HPV33 | E1 | 8 | 84 |
| HPV33 | E1 | 10 | 546 |
| HPV33 | E1 | 11 | 546 |
| HPV33 | E1 | 8 | 311 |
| HPV33 | E1 | 9 | 311 |
| HPV33 | E1 | 8 | 318 |
| HPV33 | E1 | 10 | 373 |
| HPV33 | E1 | 11 | 373 |
| HPV33 | E1 | 9 | 81 |
| HPV33 | E1 | 10 | 81 |
| HPV33 | E1 | 11 | 81 |
| HPV33 | E1 | 11 | 22 |
| HPV33 | E1 | 11 | 230 |
| HPV33 | E1 | 8 | 259 |
| HPV33 | E1 | 9 | 259 |
| HPV33 | E1 | 10 | 259 |
| HPV33 | E1 | 11 | 259 |
| HPV33 | E1 | 8 | 465 |
| HPV33 | E1 | 9 | 297 |
| HPV33 | E1 | 8 | 494 |
| HPV33 | E1 | 9 | 494 |
| HPV33 | E1 | 10 | 494 |
| HPV33 | E1 | 9 | 367 |
| HPV33 | E1 | 10 | 367 |
| HPV33 | E1 | 10 | 46 |
| HPV33 | E1 | 8 | 78 |
| HPV33 | E1 | 8 | 349 |
| HPV33 | E1 | 9 | 349 |
| HPV33 | E1 | 10 | 349 |
| HPV33 | E1 | 8 | 3 |
| HPV33 | E1 | 10 | 3 |
| HPV33 | E1 | 8 | 541 |
| HPV33 | E1 | 10 | 541 |
| HPV33 | E1 | 9 | 324 |
| HPV33 | E1 | 10 | 324 |
| HPV33 | E1 | 9 | 516 |
| HPV33 | E1 | 10 | 516 |
| HPV33 | E1 | 10 | 537 |
| HPV33 | E1 | 11 | 537 |
| HPV33 | E1 | 8 | 361 |
| HPV33 | E1 | 9 | 361 |
| HPV33 | E1 | 10 | 361 |
| HPV33 | E1 | 11 | 361 |
| HPV33 | E1 | 11 | 352 |
| HPV33 | E1 | 11 | 301 |
| HPV33 | E1 | 8 | 137 |
| HPV33 | E1 | 11 | 137 |
| HPV33 | E1 | 8 | 169 |
| HPV33 | E1 | 10 | 50 |
| HPV33 | E1 | 8 | 449 |
| HPV33 | E1 | 9 | 449 |
| HPV33 | E1 | 10 | 486 |
| HPV33 | E1 | 11 | 456 |

TABLE XIV-continued

HLA-B62 Supermotif Peptides

| 1 | 2 | 3 | 4 |
|---|---|---|---|
| HPV33 | E1 | 8 | 385 |
| HPV33 | E1 | 10 | 385 |
| HPV33 | E1 | 11 | 385 |
| HPV33 | E1 | 8 | 212 |
| HPV33 | E1 | 10 | 585 |
| HPV33 | E1 | 11 | 585 |
| HPV33 | E1 | 8 | 265 |
| HPV33 | E1 | 10 | 265 |
| HPV33 | E1 | 10 | 399 |
| HPV33 | E1 | 8 | 459 |
| HPV33 | E1 | 9 | 459 |
| HPV33 | E1 | 10 | 459 |
| HPV33 | E1 | 8 | 209 |
| HPV33 | E1 | 11 | 209 |
| HPV33 | E1 | 10 | 235 |
| HPV33 | E1 | 8 | 11 |
| HPV33 | E1 | 10 | 11 |
| HPV33 | E1 | 9 | 512 |
| HPV33 | E1 | 11 | 512 |
| HPV33 | E1 | 8 | 480 |
| HPV33 | E1 | 9 | 470 |
| HPV33 | E1 | 10 | 470 |
| HPV33 | E1 | 8 | 163 |
| HPV33 | E1 | 11 | 256 |
| HPV33 | E1 | 9 | 266 |
| HPV33 | E1 | 8 | 267 |
| HPV33 | E1 | 8 | 200 |
| HPV33 | E1 | 9 | 200 |
| HPV33 | E1 | 11 | 200 |
| HPV33 | E1 | 9 | 400 |
| HPV33 | E1 | 8 | 293 |
| HPV33 | E1 | 8 | 460 |
| HPV33 | E1 | 9 | 460 |
| HPV33 | E1 | 8 | 59 |
| HPV33 | E1 | 10 | 59 |
| HPV33 | E1 | 11 | 59 |
| HPV33 | E1 | 8 | 72 |
| HPV33 | E1 | 10 | 72 |
| HPV33 | E1 | 11 | 72 |
| HPV33 | E1 | 8 | 484 |
| HPV33 | E1 | 9 | 484 |
| HPV33 | E1 | 8 | 394 |
| HPV33 | E1 | 10 | 435 |
| HPV33 | E1 | 10 | 124 |
| HPV33 | E1 | 8 | 510 |
| HPV33 | E1 | 11 | 510 |
| HPV33 | E1 | 8 | 393 |
| HPV33 | E1 | 9 | 393 |
| HPV33 | E1 | 9 | 285 |
| HPV33 | E1 | 8 | 304 |
| HPV33 | E1 | 9 | 304 |
| HPV33 | E1 | 10 | 304 |
| HPV33 | E1 | 11 | 304 |
| HPV33 | E1 | 8 | 412 |
| HPV33 | E1 | 9 | 249 |
| HPV33 | E1 | 9 | 245 |
| HPV33 | E1 | 10 | 245 |
| HPV33 | E1 | 8 | 247 |
| HPV33 | E1 | 11 | 247 |
| HPV33 | E1 | 9 | 483 |
| HPV33 | E1 | 10 | 483 |
| HPV33 | E1 | 11 | 271 |
| HPV33 | E1 | 9 | 47 |
| HPV33 | E1 | 9 | 555 |
| HPV33 | E1 | 9 | 438 |
| HPV33 | E1 | 11 | 438 |
| HPV33 | E1 | 9 | 290 |
| HPV33 | E1 | 10 | 290 |
| HPV33 | E1 | 11 | 290 |
| HPV33 | E1 | 8 | 556 |
| HPV33 | E1 | 8 | 286 |
| HPV33 | E1 | 10 | 257 |
| HPV33 | E1 | 11 | 257 |
| HPV33 | E1 | 8 | 184 |
| HPV33 | E1 | 9 | 339 |
| HPV33 | E1 | 10 | 339 |
| HPV33 | E1 | 9 | 503 |
| HPV33 | E1 | 11 | 503 |
| HPV33 | E1 | 9 | 547 |
| HPV33 | E1 | 10 | 547 |
| HPV33 | E1 | 11 | 547 |
| HPV33 | E1 | 8 | 513 |
| HPV33 | E1 | 10 | 513 |
| HPV33 | E1 | 8 | 298 |
| HPV33 | E1 | 10 | 353 |
| HPV33 | E1 | 8 | 443 |
| HPV33 | E1 | 10 | 443 |
| HPV33 | E1 | 11 | 443 |
| HPV33 | E1 | 8 | 346 |
| HPV33 | E1 | 9 | 346 |
| HPV33 | E1 | 11 | 346 |
| HPV33 | E1 | 9 | 199 |
| HPV33 | E1 | 10 | 199 |
| HPV33 | E1 | 9 | 71 |
| HPV33 | E1 | 11 | 71 |
| HPV33 | E1 | 10 | 31 |
| HPV33 | E1 | 9 | 627 |
| HPV33 | E1 | 10 | 289 |
| HPV33 | E1 | 11 | 289 |
| HPV33 | E1 | 10 | 155 |
| HPV33 | E1 | 11 | 592 |
| HPV33 | E1 | 8 | 175 |
| HPV33 | E1 | 10 | 175 |
| HPV33 | E1 | 10 | 189 |
| HPV33 | E1 | 10 | 181 |
| HPV33 | E1 | 11 | 181 |
| HPV33 | E1 | 10 | 519 |
| HPV33 | E1 | 11 | 519 |
| HPV33 | E1 | 8 | 434 |
| HPV33 | E1 | 11 | 434 |
| HPV33 | E1 | 10 | 554 |
| HPV33 | E1 | 9 | 505 |
| HPV33 | E1 | 10 | 505 |
| HPV33 | E1 | 10 | 302 |
| HPV33 | E1 | 11 | 302 |
| HPV33 | E1 | 11 | 553 |
| HPV33 | E1 | 10 | 593 |
| HPV33 | E1 | 9 | 374 |
| HPV33 | E1 | 10 | 374 |
| HPV33 | E1 | 11 | 374 |
| HPV33 | E1 | 8 | 549 |
| HPV33 | E1 | 9 | 549 |
| HPV33 | E1 | 8 | 437 |
| HPV33 | E1 | 10 | 437 |
| HPV33 | E1 | 8 | 504 |
| HPV33 | E1 | 10 | 504 |
| HPV33 | E1 | 11 | 504 |
| HPV33 | E1 | 11 | 146 |
| HPV33 | E1 | 8 | 280 |
| HPV33 | E1 | 11 | 280 |
| HPV33 | E1 | 11 | 575 |
| HPV33 | E1 | 9 | 335 |
| HPV33 | E1 | 9 | 433 |
| HPV33 | E1 | 8 | 539 |
| HPV33 | E1 | 9 | 539 |
| HPV33 | E1 | 10 | 539 |
| HPV33 | E1 | 10 | 111 |
| HPV33 | E1 | 8 | 292 |
| HPV33 | E1 | 9 | 292 |
| HPV33 | E1 | 8 | 58 |
| HPV33 | E1 | 9 | 58 |
| HPV33 | E1 | 11 | 58 |
| HPV33 | E1 | 10 | 482 |
| HPV33 | E1 | 11 | 482 |
| HPV33 | E1 | 11 | 243 |
| HPV33 | E1 | 9 | 252 |
| HPV33 | E1 | 8 | 54 |
| HPV33 | E1 | 8 | 237 |
| HPV33 | E1 | 10 | 237 |
| HPV33 | E1 | 11 | 237 |

TABLE XIV-continued

HLA-B62 Supermotif Peptides

| 1 | 2 | 3 | 4 |
|---|---|---|---|
| HPV33 | E1 | 11 | 390 |
| HPV33 | E1 | 8 | 149 |
| HPV33 | E1 | 11 | 149 |
| HPV33 | E1 | 8 | 93 |
| HPV33 | E1 | 9 | 93 |
| HPV33 | E1 | 8 | 307 |
| HPV33 | E1 | 9 | 307 |
| HPV33 | E1 | 8 | 239 |
| HPV33 | E1 | 9 | 239 |
| HPV33 | E1 | 10 | 239 |
| HPV33 | E1 | 8 | 183 |
| HPV33 | E1 | 9 | 183 |
| HPV33 | E1 | 8 | 329 |
| HPV33 | E1 | 10 | 329 |
| HPV33 | E1 | 11 | 329 |
| HPV33 | E1 | 8 | 518 |
| HPV33 | E1 | 11 | 518 |
| HPV33 | E1 | 8 | 140 |
| HPV33 | E1 | 9 | 282 |
| HPV33 | E1 | 10 | 282 |
| HPV33 | E1 | 9 | 577 |
| HPV33 | E1 | 11 | 577 |
| HPV33 | E1 | 11 | 337 |
| HPV33 | E1 | 10 | 23 |
| HPV33 | E1 | 11 | 491 |
| HPV33 | E1 | 9 | 190 |
| HPV33 | E1 | 11 | 190 |
| HPV33 | E1 | 8 | 246 |
| HPV33 | E1 | 9 | 246 |
| HPV33 | E1 | 10 | 338 |
| HPV33 | E1 | 11 | 338 |
| HPV33 | E1 | 8 | 325 |
| HPV33 | E1 | 9 | 325 |
| HPV33 | E1 | 8 | 548 |
| HPV33 | E1 | 9 | 548 |
| HPV33 | E1 | 10 | 548 |
| HPV33 | E1 | 9 | 436 |
| HPV33 | E1 | 11 | 436 |
| HPV33 | E1 | 9 | 354 |
| HPV33 | E1 | 8 | 332 |
| HPV33 | E1 | 8 | 502 |
| HPV33 | E1 | 10 | 502 |
| HPV33 | E1 | 8 | 569 |
| HPV33 | E1 | 10 | 569 |
| HPV33 | E1 | 11 | 569 |
| HPV33 | E1 | 9 | 524 |
| HPV33 | E1 | 10 | 524 |
| HPV33 | E1 | 8 | 571 |
| HPV33 | E1 | 9 | 571 |
| HPV33 | E1 | 11 | 571 |
| HPV33 | E1 | 11 | 528 |
| HPV33 | E1 | 8 | 441 |
| HPV33 | E1 | 9 | 441 |
| HPV33 | E1 | 10 | 441 |
| HPV33 | E2 | 10 | 249 |
| HPV33 | E2 | 10 | 78 |
| HPV33 | E2 | 9 | 41 |
| HPV33 | E2 | 11 | 41 |
| HPV33 | E2 | 8 | 237 |
| HPV33 | E2 | 10 | 237 |
| HPV33 | E2 | 9 | 10 |
| HPV33 | E2 | 10 | 10 |
| HPV33 | E2 | 9 | 288 |
| HPV33 | E2 | 10 | 195 |
| HPV33 | E2 | 9 | 25 |
| HPV33 | E2 | 11 | 25 |
| HPV33 | E2 | 10 | 17 |
| HPV33 | E2 | 9 | 247 |
| HPV33 | E2 | 8 | 3 |
| HPV33 | E2 | 9 | 3 |
| HPV33 | E2 | 9 | 74 |
| HPV33 | E2 | 10 | 298 |
| HPV33 | E2 | 8 | 328 |
| HPV33 | E2 | 11 | 328 |
| HPV33 | E2 | 8 | 185 |
| HPV33 | E2 | 9 | 185 |
| HPV33 | E2 | 10 | 185 |
| HPV33 | E2 | 11 | 100 |
| HPV33 | E2 | 11 | 334 |
| HPV33 | E2 | 8 | 70 |
| HPV33 | E2 | 9 | 70 |
| HPV33 | E2 | 10 | 70 |
| HPV33 | E2 | 9 | 325 |
| HPV33 | E2 | 10 | 325 |
| HPV33 | E2 | 11 | 325 |
| HPV33 | E2 | 8 | 319 |
| HPV33 | E2 | 11 | 156 |
| HPV33 | E2 | 10 | 190 |
| HPV33 | E2 | 10 | 53 |
| HPV33 | E2 | 11 | 53 |
| HPV33 | E2 | 9 | 278 |
| HPV33 | E2 | 8 | 56 |
| HPV33 | E2 | 9 | 56 |
| HPV33 | E2 | 8 | 187 |
| HPV33 | E2 | 9 | 139 |
| HPV33 | E2 | 10 | 139 |
| HPV33 | E2 | 11 | 340 |
| HPV33 | E2 | 11 | 276 |
| HPV33 | E2 | 8 | 14 |
| HPV33 | E2 | 8 | 339 |
| HPV33 | E2 | 8 | 242 |
| HPV33 | E2 | 9 | 242 |
| HPV33 | E2 | 8 | 34 |
| HPV33 | E2 | 9 | 34 |
| HPV33 | E2 | 10 | 34 |
| HPV33 | E2 | 11 | 34 |
| HPV33 | E2 | 10 | 294 |
| HPV33 | E2 | 8 | 112 |
| HPV33 | E2 | 10 | 112 |
| HPV33 | E2 | 8 | 47 |
| HPV33 | E2 | 10 | 264 |
| HPV33 | E2 | 11 | 264 |
| HPV33 | E2 | 8 | 151 |
| HPV33 | E2 | 9 | 151 |
| HPV33 | E2 | 10 | 151 |
| HPV33 | E2 | 11 | 165 |
| HPV33 | E2 | 8 | 35 |
| HPV33 | E2 | 9 | 35 |
| HPV33 | E2 | 10 | 35 |
| HPV33 | E2 | 8 | 62 |
| HPV33 | E2 | 9 | 62 |
| HPV33 | E2 | 11 | 62 |
| HPV33 | E2 | 8 | 42 |
| HPV33 | E2 | 10 | 42 |
| HPV33 | E2 | 8 | 26 |
| HPV33 | E2 | 10 | 26 |
| HPV33 | E2 | 11 | 26 |
| HPV33 | E2 | 8 | 75 |
| HPV33 | E2 | 8 | 94 |
| HPV33 | E2 | 9 | 94 |
| HPV33 | E2 | 10 | 94 |
| HPV33 | E2 | 8 | 147 |
| HPV33 | E2 | 9 | 147 |
| HPV33 | E2 | 11 | 147 |
| HPV33 | E2 | 9 | 202 |
| HPV33 | E2 | 11 | 202 |
| HPV33 | E2 | 8 | 272 |
| HPV33 | E2 | 8 | 239 |
| HPV33 | E2 | 11 | 239 |
| HPV33 | E2 | 10 | 341 |
| HPV33 | E2 | 11 | 341 |
| HPV33 | E2 | 11 | 221 |
| HPV33 | E2 | 8 | 29 |
| HPV33 | E2 | 10 | 29 |
| HPV33 | E2 | 9 | 345 |
| HPV33 | E2 | 8 | 203 |
| HPV33 | E2 | 10 | 203 |
| HPV33 | E2 | 9 | 332 |
| HPV33 | E2 | 11 | 48 |
| HPV33 | E2 | 11 | 182 |

TABLE XIV-continued

HLA-B62 Supermotif Peptides

| 1 | 2 | 3 | 4 |
|---|---|---|---|
| HPV33 | E2 | 9 | 238 |
| HPV33 | E2 | 8 | 331 |
| HPV33 | E2 | 10 | 331 |
| HPV33 | E2 | 9 | 330 |
| HPV33 | E2 | 11 | 330 |
| HPV33 | E2 | 10 | 329 |
| HPV33 | E2 | 8 | 95 |
| HPV33 | E2 | 9 | 95 |
| HPV33 | E2 | 8 | 71 |
| HPV33 | E2 | 9 | 71 |
| HPV33 | E2 | 9 | 191 |
| HPV33 | E2 | 8 | 57 |
| HPV33 | E2 | 8 | 292 |
| HPV33 | E2 | 9 | 292 |
| HPV33 | E2 | 9 | 7 |
| HPV33 | E2 | 10 | 7 |
| HPV33 | E2 | 8 | 37 |
| HPV33 | E2 | 10 | 37 |
| HPV33 | E2 | 9 | 229 |
| HPV33 | E2 | 9 | 285 |
| HPV33 | E2 | 9 | 61 |
| HPV33 | E2 | 10 | 61 |
| HPV33 | E2 | 8 | 302 |
| HPV33 | E2 | 8 | 28 |
| HPV33 | E2 | 9 | 28 |
| HPV33 | E2 | 11 | 28 |
| HPV33 | E2 | 10 | 90 |
| HPV33 | E2 | 8 | 85 |
| HPV33 | E2 | 10 | 85 |
| HPV33 | E2 | 9 | 93 |
| HPV33 | E2 | 10 | 93 |
| HPV33 | E2 | 11 | 93 |
| HPV33 | E2 | 10 | 128 |
| HPV33 | E2 | 11 | 128 |
| HPV33 | E2 | 9 | 146 |
| HPV33 | E2 | 10 | 146 |
| HPV33 | E2 | 8 | 181 |
| HPV33 | E2 | 8 | 267 |
| HPV33 | E2 | 10 | 267 |
| HPV33 | E2 | 11 | 267 |
| HPV33 | E2 | 8 | 337 |
| HPV33 | E2 | 10 | 337 |
| HPV33 | E2 | 8 | 343 |
| HPV33 | E2 | 9 | 343 |
| HPV33 | E2 | 11 | 343 |
| HPV33 | E2 | 8 | 72 |
| HPV33 | E2 | 11 | 72 |
| HPV33 | E2 | 8 | 192 |
| HPV33 | E2 | 11 | 59 |
| HPV33 | E2 | 8 | 11 |
| HPV33 | E2 | 9 | 11 |
| HPV33 | E2 | 11 | 11 |
| HPV33 | E2 | 8 | 344 |
| HPV33 | E2 | 10 | 344 |
| HPV33 | E2 | 11 | 119 |
| HPV33 | E2 | 9 | 102 |
| HPV33 | E2 | 8 | 159 |
| HPV33 | E2 | 9 | 159 |
| HPV33 | E2 | 10 | 159 |
| HPV33 | E2 | 10 | 138 |
| HPV33 | E2 | 11 | 138 |
| HPV33 | E5 | 9 | 63 |
| HPV33 | E5 | 9 | 14 |
| HPV33 | E5 | 10 | 14 |
| HPV33 | E5 | 11 | 14 |
| HPV33 | E5 | 9 | 9 |
| HPV33 | E5 | 10 | 9 |
| HPV33 | E5 | 11 | 9 |
| HPV33 | E5 | 8 | 12 |
| HPV33 | E5 | 11 | 12 |
| HPV33 | E5 | 9 | 56 |
| HPV33 | E5 | 11 | 56 |
| HPV33 | E5 | 8 | 3 |
| HPV33 | E5 | 9 | 3 |
| HPV33 | E5 | 10 | 3 |
| HPV33 | E5 | 11 | 3 |
| HPV33 | E5 | 8 | 42 |
| HPV33 | E5 | 9 | 42 |
| HPV33 | E5 | 10 | 42 |
| HPV33 | E5 | 8 | 5 |
| HPV33 | E5 | 9 | 5 |
| HPV33 | E5 | 11 | 5 |
| HPV33 | E5 | 8 | 10 |
| HPV33 | E5 | 9 | 10 |
| HPV33 | E5 | 10 | 10 |
| HPV33 | E5 | 8 | 23 |
| HPV33 | E5 | 9 | 23 |
| HPV33 | E5 | 10 | 23 |
| HPV33 | E5 | 11 | 23 |
| HPV33 | E5 | 8 | 48 |
| HPV33 | E5 | 9 | 48 |
| HPV33 | E5 | 10 | 48 |
| HPV33 | E5 | 11 | 48 |
| HPV33 | E5 | 8 | 22 |
| HPV33 | E5 | 9 | 22 |
| HPV33 | E5 | 10 | 22 |
| HPV33 | E5 | 11 | 22 |
| HPV33 | E5 | 8 | 54 |
| HPV33 | E5 | 9 | 54 |
| HPV33 | E5 | 11 | 54 |
| HPV33 | E5 | 8 | 17 |
| HPV33 | E5 | 10 | 17 |
| HPV33 | E5 | 11 | 37 |
| HPV33 | E5 | 9 | 18 |
| HPV33 | E5 | 8 | 32 |
| HPV33 | E5 | 9 | 32 |
| HPV33 | E5 | 10 | 32 |
| HPV33 | E5 | 11 | 32 |
| HPV33 | E5 | 10 | 38 |
| HPV33 | E5 | 8 | 59 |
| HPV33 | E5 | 10 | 59 |
| HPV33 | E5 | 8 | 35 |
| HPV33 | E5 | 9 | 35 |
| HPV33 | E5 | 8 | 33 |
| HPV33 | E5 | 9 | 33 |
| HPV33 | E5 | 10 | 33 |
| HPV33 | E5 | 11 | 33 |
| HPV33 | E5 | 9 | 1 |
| HPV33 | E5 | 10 | 1 |
| HPV33 | E5 | 11 | 1 |
| HPV33 | E5 | 8 | 61 |
| HPV33 | E5 | 11 | 61 |
| HPV33 | E5 | 9 | 21 |
| HPV33 | E5 | 10 | 21 |
| HPV33 | E5 | 11 | 21 |
| HPV33 | E5 | 8 | 46 |
| HPV33 | E5 | 9 | 46 |
| HPV33 | E5 | 10 | 46 |
| HPV33 | E5 | 11 | 46 |
| HPV33 | E5 | 9 | 60 |
| HPV33 | E5 | 10 | 20 |
| HPV33 | E5 | 11 | 20 |
| HPV33 | E5 | 8 | 25 |
| HPV33 | E5 | 9 | 25 |
| HPV33 | E5 | 10 | 25 |
| HPV33 | E5 | 11 | 25 |
| HPV33 | E5 | 8 | 16 |
| HPV33 | E5 | 9 | 16 |
| HPV33 | E5 | 11 | 16 |
| HPV33 | E5 | 9 | 45 |
| HPV33 | E5 | 10 | 45 |
| HPV33 | E5 | 11 | 45 |
| HPV33 | E5 | 8 | 6 |
| HPV33 | E5 | 10 | 6 |
| HPV33 | E5 | 8 | 36 |
| HPV33 | E5 | 8 | 34 |
| HPV33 | E5 | 9 | 34 |
| HPV33 | E5 | 10 | 34 |
| HPV33 | E5 | 8 | 31 |
| HPV33 | E5 | 9 | 31 |

TABLE XIV-continued

HLA-B62 Supermotif Peptides

| 1 | 2 | 3 | 4 |
|---|---|---|---|
| HPV33 | E5 | 10 | 31 |
| HPV33 | E5 | 11 | 31 |
| HPV33 | E5 | 8 | 40 |
| HPV33 | E5 | 10 | 40 |
| HPV33 | E5 | 11 | 40 |
| HPV33 | E5 | 9 | 53 |
| HPV33 | E5 | 10 | 53 |
| HPV33 | E5 | 9 | 58 |
| HPV33 | E5 | 11 | 58 |
| HPV33 | E6 | 9 | 18 |
| HPV33 | E6 | 11 | 18 |
| HPV33 | E6 | 8 | 103 |
| HPV33 | E6 | 8 | 66 |
| HPV33 | E6 | 11 | 66 |
| HPV33 | E6 | 9 | 111 |
| HPV33 | E6 | 11 | 111 |
| HPV33 | E6 | 8 | 16 |
| HPV33 | E6 | 11 | 16 |
| HPV33 | E6 | 8 | 30 |
| HPV33 | E6 | 10 | 14 |
| HPV33 | E6 | 9 | 120 |
| HPV33 | E6 | 8 | 98 |
| HPV33 | E6 | 11 | 27 |
| HPV33 | E6 | 8 | 89 |
| HPV33 | E6 | 11 | 89 |
| HPV33 | E6 | 8 | 41 |
| HPV33 | E6 | 10 | 41 |
| HPV33 | E6 | 8 | 69 |
| HPV33 | E6 | 11 | 69 |
| HPV33 | E6 | 11 | 2 |
| HPV33 | E6 | 9 | 61 |
| HPV33 | E6 | 10 | 61 |
| HPV33 | E6 | 8 | 118 |
| HPV33 | E6 | 11 | 118 |
| HPV33 | E6 | 8 | 72 |
| HPV33 | E6 | 10 | 72 |
| HPV33 | E6 | 10 | 64 |
| HPV33 | E6 | 8 | 94 |
| HPV33 | E6 | 11 | 94 |
| HPV33 | E6 | 8 | 35 |
| HPV33 | E6 | 9 | 35 |
| HPV33 | E6 | 11 | 35 |
| HPV33 | E6 | 8 | 8 |
| HPV33 | E6 | 11 | 8 |
| HPV33 | E6 | 11 | 100 |
| HPV33 | E6 | 10 | 28 |
| HPV33 | E6 | 9 | 37 |
| HPV33 | E6 | 10 | 37 |
| HPV33 | E6 | 11 | 37 |
| HPV33 | E6 | 11 | 127 |
| HPV33 | E6 | 8 | 58 |
| HPV33 | E6 | 10 | 58 |
| HPV33 | E6 | 11 | 109 |
| HPV33 | E6 | 10 | 95 |
| HPV33 | E6 | 11 | 95 |
| HPV33 | E6 | 8 | 36 |
| HPV33 | E6 | 10 | 36 |
| HPV33 | E6 | 11 | 36 |
| HPV33 | E6 | 8 | 112 |
| HPV33 | E6 | 10 | 112 |
| HPV33 | E6 | 11 | 82 |
| HPV33 | E6 | 10 | 22 |
| HPV33 | E6 | 10 | 87 |
| HPV33 | E6 | 8 | 11 |
| HPV33 | E6 | 9 | 11 |
| HPV33 | E6 | 9 | 91 |
| HPV33 | E6 | 10 | 91 |
| HPV33 | E6 | 11 | 91 |
| HPV33 | E6 | 10 | 51 |
| HPV33 | E6 | 9 | 52 |
| HPV33 | E6 | 11 | 52 |
| HPV33 | E7 | 8 | 45 |
| HPV33 | E7 | 9 | 45 |
| HPV33 | E7 | 10 | 45 |
| HPV33 | E7 | 11 | 45 |
| HPV33 | E7 | 9 | 68 |
| HPV33 | E7 | 8 | 75 |
| HPV33 | E7 | 9 | 75 |
| HPV33 | E7 | 10 | 75 |
| HPV33 | E7 | 8 | 21 |
| HPV33 | E7 | 9 | 14 |
| HPV33 | E7 | 10 | 14 |
| HPV33 | E7 | 8 | 18 |
| HPV33 | E7 | 11 | 18 |
| HPV33 | E7 | 9 | 37 |
| HPV33 | E7 | 8 | 43 |
| HPV33 | E7 | 10 | 43 |
| HPV33 | E7 | 11 | 43 |
| HPV33 | E7 | 9 | 79 |
| HPV33 | E7 | 11 | 79 |
| HPV33 | E7 | 8 | 5 |
| HPV33 | E7 | 9 | 5 |
| HPV33 | E7 | 11 | 5 |
| HPV33 | E7 | 8 | 82 |
| HPV33 | E7 | 9 | 82 |
| HPV33 | E7 | 8 | 83 |
| HPV33 | E7 | 8 | 88 |
| HPV33 | E7 | 9 | 81 |
| HPV33 | E7 | 10 | 81 |
| HPV33 | E7 | 8 | 46 |
| HPV33 | E7 | 9 | 46 |
| HPV33 | E7 | 10 | 46 |
| HPV33 | E7 | 8 | 80 |
| HPV33 | E7 | 10 | 80 |
| HPV33 | E7 | 11 | 80 |
| HPV33 | E7 | 8 | 66 |
| HPV33 | E7 | 11 | 66 |
| HPV33 | E7 | 9 | 40 |
| HPV33 | E7 | 11 | 40 |
| HPV33 | E7 | 10 | 78 |
| HPV33 | E7 | 9 | 7 |
| HPV33 | E7 | 10 | 7 |
| HPV33 | E7 | 10 | 86 |
| HPV33 | E7 | 10 | 64 |
| HPV33 | E7 | 11 | 12 |
| HPV33 | E7 | 8 | 16 |
| HPV33 | E7 | 10 | 16 |
| HPV33 | L1 | 8 | 424 |
| HPV33 | L1 | 10 | 392 |
| HPV33 | L1 | 9 | 180 |
| HPV33 | L1 | 11 | 180 |
| HPV33 | L1 | 10 | 483 |
| HPV33 | L1 | 8 | 316 |
| HPV33 | L1 | 10 | 316 |
| HPV33 | L1 | 9 | 44 |
| HPV33 | L1 | 8 | 270 |
| HPV33 | L1 | 11 | 147 |
| HPV33 | L1 | 9 | 207 |
| HPV33 | L1 | 10 | 185 |
| HPV33 | L1 | 11 | 185 |
| HPV33 | L1 | 9 | 223 |
| HPV33 | L1 | 8 | 396 |
| HPV33 | L1 | 10 | 396 |
| HPV33 | L1 | 11 | 457 |
| HPV33 | L1 | 8 | 449 |
| HPV33 | L1 | 10 | 449 |
| HPV33 | L1 | 8 | 370 |
| HPV33 | L1 | 11 | 370 |
| HPV33 | L1 | 11 | 274 |
| HPV33 | L1 | 10 | 199 |
| HPV33 | L1 | 8 | 438 |
| HPV33 | L1 | 9 | 438 |
| HPV33 | L1 | 11 | 438 |
| HPV33 | L1 | 9 | 459 |
| HPV33 | L1 | 10 | 459 |
| HPV33 | L1 | 11 | 459 |
| HPV33 | L1 | 8 | 107 |
| HPV33 | L1 | 10 | 107 |
| HPV33 | L1 | 8 | 240 |
| HPV33 | L1 | 9 | 240 |

TABLE XIV-continued

HLA-B62 Supermotif Peptides

| 1 | 2 | 3 | 4 |
|---|---|---|---|
| HPV33 | L1 | 10 | 240 |
| HPV33 | L1 | 11 | 240 |
| HPV33 | L1 | 8 | 253 |
| HPV33 | L1 | 9 | 253 |
| HPV33 | L1 | 8 | 447 |
| HPV33 | L1 | 10 | 447 |
| HPV33 | L1 | 8 | 385 |
| HPV33 | L1 | 9 | 385 |
| HPV33 | L1 | 9 | 467 |
| HPV33 | L1 | 8 | 249 |
| HPV33 | L1 | 9 | 249 |
| HPV33 | L1 | 8 | 461 |
| HPV33 | L1 | 9 | 461 |
| HPV33 | L1 | 11 | 461 |
| HPV33 | L1 | 8 | 292 |
| HPV33 | L1 | 9 | 292 |
| HPV33 | L1 | 8 | 375 |
| HPV33 | L1 | 10 | 375 |
| HPV33 | L1 | 8 | 373 |
| HPV33 | L1 | 10 | 373 |
| HPV33 | L1 | 9 | 256 |
| HPV33 | L1 | 8 | 322 |
| HPV33 | L1 | 9 | 322 |
| HPV33 | L1 | 10 | 322 |
| HPV33 | L1 | 8 | 117 |
| HPV33 | L1 | 11 | 117 |
| HPV33 | L1 | 10 | 105 |
| HPV33 | L1 | 8 | 472 |
| HPV33 | L1 | 11 | 472 |
| HPV33 | L1 | 9 | 68 |
| HPV33 | L1 | 11 | 68 |
| HPV33 | L1 | 8 | 404 |
| HPV33 | L1 | 10 | 404 |
| HPV33 | L1 | 11 | 138 |
| HPV33 | L1 | 8 | 111 |
| HPV33 | L1 | 8 | 173 |
| HPV33 | L1 | 10 | 173 |
| HPV33 | L1 | 9 | 115 |
| HPV33 | L1 | 10 | 115 |
| HPV33 | L1 | 9 | 365 |
| HPV33 | L1 | 10 | 365 |
| HPV33 | L1 | 11 | 365 |
| HPV33 | L1 | 8 | 194 |
| HPV33 | L1 | 9 | 397 |
| HPV33 | L1 | 10 | 60 |
| HPV33 | L1 | 11 | 236 |
| HPV33 | L1 | 8 | 476 |
| HPV33 | L1 | 8 | 163 |
| HPV33 | L1 | 8 | 309 |
| HPV33 | L1 | 8 | 153 |
| HPV33 | L1 | 9 | 65 |
| MPV33 | L1 | 10 | 65 |
| HPV33 | L1 | 8 | 379 |
| HPV33 | L1 | 9 | 379 |
| HPV33 | L1 | 11 | 379 |
| HPV33 | L1 | 8 | 20 |
| HPV33 | L1 | 9 | 20 |
| HPV33 | L1 | 11 | 190 |
| HPV33 | L1 | 8 | 42 |
| HPV33 | L1 | 9 | 42 |
| HPV33 | L1 | 11 | 42 |
| HPV33 | L1 | 8 | 468 |
| HPV33 | L1 | 9 | 61 |
| HPV33 | L1 | 11 | 61 |
| HPV33 | L1 | 9 | 78 |
| HPV33 | L1 | 9 | 13 |
| HPV33 | L1 | 10 | 13 |
| HPV33 | L1 | 11 | 469 |
| HPV33 | L1 | 8 | 213 |
| HPV33 | L1 | 10 | 213 |
| HPV33 | L1 | 8 | 413 |
| HPV33 | L1 | 10 | 371 |
| HPV33 | L1 | 11 | 313 |
| HPV33 | L1 | 8 | 69 |
| HPV33 | L1 | 10 | 69 |
| HPV33 | L1 | 8 | 62 |
| HPV33 | L1 | 10 | 62 |
| HPV33 | L1 | 8 | 99 |
| HPV33 | L1 | 10 | 99 |
| HPV33 | L1 | 9 | 200 |
| HPV33 | L1 | 11 | 200 |
| HPV33 | L1 | 8 | 299 |
| HPV33 | L1 | 9 | 299 |
| HPV33 | L1 | 8 | 341 |
| HPV33 | L1 | 8 | 394 |
| HPV33 | L1 | 10 | 394 |
| HPV33 | L1 | 8 | 93 |
| HPV33 | L1 | 9 | 93 |
| HPV33 | L1 | 10 | 93 |
| HPV33 | L1 | 8 | 54 |
| HPV33 | L1 | 9 | 54 |
| HPV33 | L1 | 10 | 54 |
| HPV33 | L1 | 8 | 327 |
| HPV33 | L1 | 11 | 221 |
| HPV33 | L1 | 8 | 187 |
| HPV33 | L1 | 9 | 187 |
| HPV33 | L1 | 8 | 439 |
| HPV33 | L1 | 10 | 439 |
| HPV33 | L1 | 8 | 462 |
| HPV33 | L1 | 10 | 462 |
| HPV33 | L1 | 11 | 113 |
| HPV33 | L1 | 9 | 432 |
| HPV33 | L1 | 9 | 186 |
| HPV33 | L1 | 10 | 186 |
| HPV33 | L1 | 11 | 407 |
| HPV33 | L1 | 10 | 408 |
| HPV33 | L1 | 11 | 164 |
| HPV33 | L1 | 8 | 14 |
| HPV33 | L1 | 9 | 14 |
| HPV33 | L1 | 8 | 15 |
| HPV33 | L1 | 11 | 17 |
| HPV33 | L1 | 9 | 376 |
| HPV33 | L1 | 11 | 376 |
| HPV33 | L1 | 8 | 305 |
| HPV33 | L1 | 9 | 305 |
| HPV33 | L1 | 8 | 254 |
| HPV33 | L1 | 11 | 254 |
| HPV33 | L1 | 10 | 139 |
| HPV33 | L1 | 8 | 347 |
| HPV33 | L1 | 9 | 41 |
| HPV33 | L1 | 10 | 41 |
| HPV33 | L1 | 8 | 77 |
| HPV33 | L1 | 10 | 77 |
| HPV33 | L1 | 9 | 98 |
| HPV33 | L1 | 11 | 98 |
| HPV33 | L1 | 8 | 5 |
| HPV33 | L1 | 9 | 5 |
| HPV33 | L1 | 10 | 75 |
| HPV33 | L1 | 8 | 51 |
| HPV33 | L1 | 11 | 51 |
| HPV33 | L1 | 8 | 285 |
| HPV33 | L1 | 11 | 32 |
| HPV33 | L1 | 11 | 245 |
| HPV33 | L1 | 8 | 412 |
| HPV33 | L1 | 9 | 412 |
| HPV33 | L1 | 9 | 149 |
| HPV33 | L1 | 11 | 149 |
| HPV33 | L1 | 9 | 298 |
| HPV33 | L1 | 10 | 298 |
| HPV33 | L1 | 10 | 422 |
| HPV33 | L1 | 8 | 304 |
| HPV33 | L1 | 9 | 304 |
| HPV33 | L1 | 10 | 304 |
| HPV33 | L1 | 8 | 2 |
| HPV33 | L1 | 10 | 2 |
| HPV33 | L1 | 11 | 2 |
| HPV33 | L1 | 8 | 193 |
| HPV33 | L1 | 9 | 193 |
| HPV33 | L1 | 10 | 266 |
| HPV33 | L1 | 11 | 266 |

TABLE XIV-continued

HLA-B62 Supermotif Peptides

| 1 | 2 | 3 | 4 |
|---|---|---|---|
| HPV33 | L1 | 9 | 212 |
| HPV33 | L1 | 11 | 212 |
| HPV33 | L1 | 9 | 381 |
| HPV33 | L1 | 10 | 381 |
| HPV33 | L1 | 8 | 406 |
| HPV33 | L1 | 9 | 96 |
| HPV33 | L1 | 11 | 96 |
| HPV33 | L1 | 9 | 346 |
| HPV33 | L1 | 11 | 430 |
| HPV33 | L1 | 11 | 332 |
| HPV33 | L1 | 9 | 10 |
| HPV33 | L1 | 8 | 386 |
| HPV33 | L1 | 9 | 63 |
| HPV33 | L1 | 11 | 63 |
| HPV33 | L1 | 10 | 431 |
| HPV33 | L1 | 10 | 333 |
| HPV33 | L1 | 8 | 21 |
| HPV33 | L1 | 11 | 401 |
| HPV33 | L1 | 9 | 389 |
| HPV33 | L1 | 10 | 389 |
| HPV33 | L1 | 9 | 276 |
| HPV33 | L1 | 11 | 276 |
| HPV33 | L1 | 8 | 362 |
| HPV33 | L1 | 10 | 362 |
| HPV33 | L1 | 9 | 234 |
| HPV33 | L1 | 10 | 12 |
| HPV33 | L1 | 11 | 12 |
| HPV33 | L1 | 8 | 27 |
| HPV33 | L1 | 9 | 27 |
| HPV33 | L1 | 10 | 27 |
| HPV33 | L1 | 11 | 27 |
| HPV33 | L2 | 8 | 140 |
| HPV33 | L2 | 11 | 82 |
| HPV33 | L2 | 9 | 291 |
| HPV33 | L2 | 11 | 291 |
| HPV33 | L2 | 9 | 173 |
| HPV33 | L2 | 10 | 173 |
| HPV33 | L2 | 11 | 173 |
| HPV33 | L2 | 9 | 276 |
| HPV33 | L2 | 10 | 276 |
| HPV33 | L2 | 11 | 276 |
| HPV33 | L2 | 10 | 120 |
| HPV33 | L2 | 9 | 27 |
| HPV33 | L2 | 9 | 283 |
| HPV33 | L2 | 10 | 283 |
| HPV33 | L2 | 10 | 272 |
| HPV33 | L2 | 11 | 272 |
| HPV33 | L2 | 8 | 327 |
| HPV33 | L2 | 11 | 239 |
| HPV33 | L2 | 8 | 278 |
| HPV33 | L2 | 9 | 278 |
| HPV33 | L2 | 10 | 278 |
| HPV33 | L2 | 8 | 261 |
| HPV33 | L2 | 9 | 77 |
| HPV33 | L2 | 9 | 42 |
| HPV33 | L2 | 11 | 42 |
| HPV33 | L2 | 9 | 369 |
| HPV33 | L2 | 11 | 30 |
| HPV33 | L2 | 11 | 130 |
| HPV33 | L2 | 10 | 364 |
| HPV33 | L2 | 9 | 165 |
| HPV33 | L2 | 11 | 165 |
| HPV33 | L2 | 8 | 341 |
| HPV33 | L2 | 8 | 113 |
| HPV33 | L2 | 11 | 113 |
| HPV33 | L2 | 8 | 181 |
| HPV33 | L2 | 10 | 447 |
| HPV33 | L2 | 11 | 281 |
| HPV33 | L2 | 8 | 242 |
| HPV33 | L2 | 9 | 242 |
| HPV33 | L2 | 11 | 242 |
| HPV33 | L2 | 8 | 428 |
| HPV33 | L2 | 11 | 428 |
| HPV33 | L2 | 8 | 415 |
| HPV33 | L2 | 10 | 415 |
| HPV33 | L2 | 8 | 456 |
| HPV33 | L2 | 10 | 456 |
| HPV33 | L2 | 11 | 456 |
| HPV33 | L2 | 9 | 268 |
| HPV33 | L2 | 8 | 440 |
| HPV33 | L2 | 9 | 440 |
| HPV33 | L2 | 10 | 440 |
| HPV33 | L2 | 8 | 421 |
| HPV33 | L2 | 10 | 421 |
| HPV33 | L2 | 10 | 201 |
| HPV33 | L2 | 10 | 361 |
| HPV33 | L2 | 10 | 226 |
| HPV33 | L2 | 8 | 407 |
| HPV33 | L2 | 9 | 407 |
| HPV33 | L2 | 8 | 98 |
| HPV33 | L2 | 10 | 98 |
| HPV33 | L2 | 11 | 98 |
| HPV33 | L2 | 9 | 51 |
| HPV33 | L2 | 11 | 158 |
| HPV33 | L2 | 8 | 170 |
| HPV33 | L2 | 8 | 284 |
| HPV33 | L2 | 9 | 284 |
| HPV33 | L2 | 9 | 44 |
| HPV33 | L2 | 10 | 44 |
| HPV33 | L2 | 11 | 44 |
| HPV33 | L2 | 9 | 448 |
| HPV33 | L2 | 11 | 448 |
| HPV33 | L2 | 8 | 216 |
| HPV33 | L2 | 10 | 216 |
| HPV33 | L2 | 9 | 32 |
| HPV33 | L2 | 10 | 32 |
| HPV33 | L2 | 11 | 394 |
| HPV33 | L2 | 10 | 83 |
| HPV33 | L2 | 8 | 196 |
| HPV33 | L2 | 9 | 123 |
| HPV33 | L2 | 8 | 152 |
| HPV33 | L2 | 8 | 331 |
| HPV33 | L2 | 10 | 104 |
| HPV33 | L2 | 11 | 104 |
| HPV33 | L2 | 8 | 433 |
| HPV33 | L2 | 9 | 433 |
| HPV33 | L2 | 10 | 433 |
| HPV33 | L2 | 9 | 248 |
| HPV33 | L2 | 10 | 248 |
| HPV33 | L2 | 9 | 316 |
| HPV33 | L2 | 10 | 316 |
| HPV33 | L2 | 8 | 34 |
| HPV33 | L2 | 11 | 34 |
| HPV33 | L2 | 8 | 236 |
| HPV33 | L2 | 8 | 107 |
| HPV33 | L2 | 10 | 107 |
| HPV33 | L2 | 8 | 249 |
| HPV33 | L2 | 9 | 249 |
| HPV33 | L2 | 8 | 266 |
| HPV33 | L2 | 11 | 266 |
| HPV33 | L2 | 8 | 85 |
| HPV33 | L2 | 10 | 85 |
| HPV33 | L2 | 8 | 377 |
| HPV33 | L2 | 9 | 377 |
| HPV33 | L2 | 8 | 195 |
| HPV33 | L2 | 9 | 195 |
| HPV33 | L2 | 9 | 160 |
| HPV33 | L2 | 10 | 160 |
| HPV33 | L2 | 10 | 372 |
| HPV33 | L2 | 10 | 391 |
| HPV33 | L2 | 10 | 143 |
| HPV33 | L2 | 8 | 209 |
| HPV33 | L2 | 9 | 73 |
| HPV33 | L2 | 10 | 73 |
| HPV33 | L2 | 11 | 73 |
| HPV33 | L2 | 8 | 215 |
| HPV33 | L2 | 9 | 215 |
| HPV33 | L2 | 11 | 215 |
| HPV33 | L2 | 8 | 87 |
| HPV33 | L2 | 11 | 87 |

TABLE XIV-continued

HLA-B62 Supermotif Peptides

| 1 | 2 | 3 | 4 |
|---|---|---|---|
| HPV33 | L2 | 8 | 423 |
| HPV33 | L2 | 11 | 423 |
| HPV33 | L2 | 9 | 330 |
| HPV33 | L2 | 11 | 333 |
| HPV33 | L2 | 9 | 99 |
| HPV33 | L2 | 10 | 99 |
| HPV33 | L2 | 9 | 413 |
| HPV33 | L2 | 10 | 413 |
| HPV33 | L2 | 10 | 347 |
| HPV33 | L2 | 10 | 395 |
| HPV33 | L2 | 11 | 395 |
| HPV33 | L2 | 9 | 84 |
| HPV33 | L2 | 11 | 84 |
| HPV33 | L2 | 9 | 376 |
| HPV33 | L2 | 10 | 376 |
| HPV33 | L2 | 11 | 171 |
| HPV33 | L2 | 8 | 28 |
| HPV33 | L2 | 8 | 78 |
| HPV33 | L2 | 11 | 78 |
| HPV33 | L2 | 8 | 90 |
| HPV33 | L2 | 11 | 90 |
| HPV33 | L2 | 8 | 221 |
| HPV33 | L2 | 8 | 403 |
| HPV33 | L2 | 10 | 91 |
| HPV33 | L2 | 8 | 317 |
| HPV33 | L2 | 9 | 317 |
| HPV33 | L2 | 8 | 43 |
| HPV33 | L2 | 10 | 43 |
| HPV33 | L2 | 11 | 43 |
| HPV33 | L2 | 8 | 16 |
| HPV33 | L2 | 9 | 86 |
| HPV33 | L2 | 11 | 346 |
| HPV33 | L2 | 9 | 233 |
| HPV33 | L2 | 10 | 233 |
| HPV33 | L2 | 11 | 233 |
| HPV33 | L2 | 8 | 234 |
| HPV33 | L2 | 9 | 234 |
| HPV33 | L2 | 10 | 234 |
| HPV33 | L2 | 8 | 321 |
| HPV33 | L2 | 11 | 321 |
| HPV33 | L2 | 11 | 289 |
| HPV33 | L2 | 9 | 89 |
| HPV33 | L2 | 8 | 220 |
| HPV33 | L2 | 9 | 220 |
| HPV33 | L2 | 8 | 303 |
| HPV33 | L2 | 9 | 357 |
| HPV33 | L2 | 10 | 357 |
| HPV33 | L2 | 11 | 357 |
| HPV33 | L2 | 8 | 393 |
| HPV33 | L2 | 8 | 122 |
| HPV33 | L2 | 10 | 122 |
| HPV33 | L2 | 9. | 151 |
| HPV33 | L2 | 11 | 103 |
| HPV33 | L2 | 9 | 49 |
| HPV33 | L2 | 11 | 49 |
| HPV33 | L2 | 8 | 106 |
| HPV33 | L2 | 9 | 106 |
| HPV33 | L2 | 11 | 106 |
| HPV33 | L2 | 8 | 274 |
| HPV33 | L2 | 9 | 274 |
| HPV33 | L2 | 11 | 274 |
| HPV33 | L2 | 9 | 425 |
| HPV33 | L2 | 10 | 425 |
| HPV33 | L2 | 11 | 425 |
| HPV33 | L2 | 9 | 419 |
| HPV33 | L2 | 10 | 419 |
| HPV33 | L2 | 8 | 245 |
| HPV33 | L2 | 10 | 329 |
| HPV33 | L2 | 10 | 412 |
| HPV33 | L2 | 11 | 412 |
| HPV33 | L2 | 9 | 185 |
| HPV33 | L2 | 10 | 146 |
| HPV33 | L2 | 9 | 167 |
| HPV33 | L2 | 11 | 167 |
| HPV33 | L2 | 9 | 39 |
| HPV33 | L2 | 10 | 154 |
| HPV33 | L2 | 9 | 432 |
| HPV33 | L2 | 10 | 432 |
| HPV33 | L2 | 11 | 432 |
| HPV33 | L2 | 10 | 309 |
| HPV33 | L2 | 9 | 265 |
| HPV33 | L2 | 10 | 138 |
| HPV33 | L2 | 9 | 214 |
| HPV33 | L2 | 10 | 214 |
| HPV33 | L2 | 10 | 375 |
| HPV33 | L2 | 11 | 375 |
| HPV33 | L2 | 11 | 125 |
| HPV33 | L2 | 9 | 402 |
| HPV33 | L2 | 9 | 15 |
| HPV33 | L2 | 10 | 232 |
| HPV33 | L2 | 11 | 232 |
| HPV33 | L2 | 9 | 190 |
| HPV33 | L2 | 8 | 93 |
| HPV33 | L2 | 9 | 96 |
| HPV33 | L2 | 10 | 96 |
| HPV33 | L2 | 9 | 337 |
| HPV33 | L2 | 11 | 298 |
| HPV33 | L2 | 10 | 187 |
| HPV33 | L2 | 10 | 31 |
| HPV33 | L2 | 11 | 31 |
| HPV33 | L2 | 8 | 168 |
| HPV33 | L2 | 10 | 168 |
| HPV33 | L2 | 8 | 441 |
| HPV33 | L2 | 9 | 441 |
| HPV33 | L2 | 11 | 404 |
| HPV33 | L2 | 10 | 72 |
| HPV33 | L2 | 11 | 72 |
| HPV33 | L2 | 9 | 422 |
| HPV33 | L2 | 8 | 338 |
| HPV33 | L2 | 11 | 338 |
| HPV33 | L2 | 8 | 434 |
| HPV33 | L2 | 9 | 434 |
| HPV33 | L2 | 9 | 202 |
| HPV33 | L2 | 8 | 325 |
| HPV33 | L2 | 10 | 325 |
| HPV33 | L2 | 11 | 71 |
| HPV45 | E1 | 9 | 232 |
| HPV45 | E1 | 10 | 232 |
| HPV45 | E1 | 9 | 532 |
| HPV45 | E1 | 8 | 68 |
| HPV45 | E1 | 9 | 311 |
| HPV45 | E1 | 9 | 199 |
| HPV45 | E1 | 10 | 199 |
| HPV45 | E1 | 11 | 512 |
| HPV45 | E1 | 10 | 66 |
| HPV45 | E1 | 8 | 72 |
| HPV45 | E1 | 10 | 72 |
| HPV45 | E1 | 11 | 72 |
| HPV45 | E1 | 8 | 408 |
| HPV45 | E1 | 11 | 408 |
| HPV45 | E1 | 10 | 373 |
| HPV45 | E1 | 11 | 373 |
| HPV45 | E1 | 11 | 79 |
| HPV45 | E1 | 9 | 202 |
| HPV45 | E1 | 11 | 202 |
| HPV45 | E1 | 10 | 399 |
| HPV45 | E1 | 8 | 465 |
| HPV45 | E1 | 8 | 259 |
| HPV45 | E1 | 9 | 259 |
| HPV45 | E1 | 10 | 259 |
| HPV45 | E1 | 11 | 259 |
| HPV45 | E1 | 9 | 297 |
| HPV45 | E1 | 10 | 552 |
| HPV45 | E1 | 10 | 390 |
| HPV45 | E1 | 11 | 390 |
| HPV45 | E1 | 10 | 634 |
| HPV45 | E1 | 10 | 206 |
| HPV45 | E1 | 11 | 206 |
| HPV45 | E1 | 9 | 614 |
| HPV45 | E1 | 8 | 349 |

TABLE XIV-continued

HLA-B62 Supermotif Peptides

| 1 | 2 | 3 | 4 |
|---|---|---|---|
| HPV45 | E1 | 9 | 349 |
| HPV45 | E1 | 10 | 349 |
| HPV45 | E1 | 9 | 108 |
| HPV45 | E1 | 11 | 108 |
| HPV45 | E1 | 8 | 361 |
| HPV45 | E1 | 9 | 361 |
| HPV45 | E1 | 10 | 361 |
| HPV45 | E1 | 9 | 367 |
| HPV45 | E1 | 10 | 367 |
| HPV45 | E1 | 10 | 46 |
| HPV45 | E1 | 11 | 352 |
| HPV45 | E1 | 8 | 562 |
| HPV45 | E1 | 10 | 562 |
| HPV45 | E1 | 11 | 562 |
| HPV45 | E1 | 9 | 179 |
| HPV45 | E1 | 11 | 30 |
| HPV45 | E1 | 10 | 596 |
| HPV45 | E1 | 11 | 596 |
| HPV45 | E1 | 11 | 115 |
| HPV45 | E1 | 8 | 186 |
| HPV45 | E1 | 10 | 189 |
| HPV45 | E1 | 11 | 189 |
| HPV45 | E1 | 8 | 504 |
| HPV45 | E1 | 9 | 504 |
| HPV45 | E1 | 10 | 504 |
| HPV45 | E1 | 11 | 504 |
| HPV45 | E1 | 9 | 301 |
| HPV45 | E1 | 10 | 301 |
| HPV45 | E1 | 11 | 301 |
| HPV45 | E1 | 8 | 59 |
| HPV45 | E1 | 10 | 59 |
| HPV45 | E1 | 11 | 59 |
| HPV45 | E1 | 8 | 62 |
| HPV45 | E1 | 9 | 62 |
| HPV45 | E1 | 11 | 62 |
| HPV45 | E1 | 9 | 101 |
| HPV45 | E1 | 9 | 141 |
| HPV45 | E1 | 11 | 141 |
| HPV45 | E1 | 8 | 74 |
| HPV45 | E1 | 9 | 74 |
| HPV45 | E1 | 11 | 74 |
| HPV45 | E1 | 9 | 324 |
| HPV45 | E1 | 10 | 324 |
| HPV45 | E1 | 8 | 50 |
| HPV45 | E1 | 8 | 483 |
| HPV45 | E1 | 9 | 483 |
| HPV45 | E1 | 10 | 483 |
| HPV45 | E1 | 8 | 446 |
| HPV45 | E1 | 11 | 446 |
| HPV45 | E1 | 11 | 456 |
| HPV45 | E1 | 8 | 385 |
| HPV45 | E1 | 10 | 385 |
| HPV45 | E1 | 11 | 385 |
| HPV45 | E1 | 9 | 486 |
| HPV45 | E1 | 10 | 486 |
| HPV45 | E1 | 8 | 449 |
| HPV45 | E1 | 9 | 449 |
| HPV45 | E1 | 9 | 438 |
| HPV45 | E1 | 10 | 438 |
| HPV45 | E1 | 10 | 585 |
| HPV45 | E1 | 11 | 585 |
| HPV45 | E1 | 8 | 494 |
| HPV45 | E1 | 9 | 494 |
| HPV45 | E1 | 10 | 494 |
| HPV45 | E1 | 9 | 342 |
| HPV45 | E1 | 10 | 626 |
| HPV45 | E1 | 8 | 318 |
| HPV45 | E1 | 8 | 209 |
| HPV45 | E1 | 11 | 209 |
| HPV45 | E1 | 8 | 286 |
| HPV45 | E1 | 8 | 480 |
| HPV45 | E1 | 11 | 480 |
| HPV45 | E1 | 9 | 470 |
| HPV45 | E1 | 10 | 470 |
| HPV45 | E1 | 8 | 443 |
| HPV45 | E1 | 10 | 443 |
| HPV45 | E1 | 11 | 443 |
| HPV45 | E1 | 8 | 265 |
| HPV45 | E1 | 10 | 265 |
| HPV45 | E1 | 10 | 235 |
| HPV45 | E1 | 9 | 256 |
| HPV45 | E1 | 11 | 256 |
| HPV45 | E1 | 8 | 83 |
| HPV45 | E1 | 8 | 292 |
| HPV45 | E1 | 9 | 292 |
| HPV45 | E1 | 11 | 338 |
| HPV45 | E1 | 11 | 491 |
| HPV45 | E1 | 10 | 555 |
| HPV45 | E1 | 9 | 627 |
| HPV45 | E1 | 8 | 257 |
| HPV45 | E1 | 10 | 257 |
| HPV45 | E1 | 11 | 257 |
| HPV45 | E1 | 10 | 339 |
| HPV45 | E1 | 11 | 333 |
| HPV45 | E1 | 9 | 23 |
| HPV45 | E1 | 10 | 23 |
| HPV45 | E1 | 10 | 435 |
| HPV45 | E1 | 8 | 425 |
| HPV45 | E1 | 11 | 425 |
| HPV45 | E1 | 8 | 304 |
| HPV45 | E1 | 9 | 304 |
| HPV45 | E1 | 10 | 304 |
| HPV45 | E1 | 11 | 304 |
| HPV45 | E1 | 9 | 249 |
| HPV45 | E1 | 11 | 545 |
| HPV45 | E1 | 8 | 510 |
| HPV45 | E1 | 11 | 299 |
| HPV45 | E1 | 8 | 247 |
| HPV45 | E1 | 9 | 247 |
| HPV45 | E1 | 11 | 247 |
| HPV45 | E1 | 8 | 267 |
| HPV45 | E1 | 9 | 290 |
| HPV45 | E1 | 10 | 290 |
| HPV45 | E1 | 11 | 290 |
| HPV45 | E1 | 9 | 190 |
| HPV45 | E1 | 10 | 190 |
| HPV45 | E1 | 11 | 190 |
| HPV45 | E1 | 9 | 547 |
| HPV45 | E1 | 10 | 547 |
| HPV45 | E1 | 11 | 547 |
| HPV45 | E1 | 11 | 271 |
| HPV45 | E1 | 9 | 556 |
| HPV45 | E1 | 8 | 191 |
| HPV45 | E1 | 9 | 191 |
| HPV45 | E1 | 10 | 191 |
| HPV45 | E1 | 11 | 191 |
| HPV45 | E1 | 8 | 487 |
| HPV45 | E1 | 9 | 487 |
| HPV45 | E1 | 8 | 548 |
| HPV45 | E1 | 9 | 548 |
| HPV45 | E1 | 10 | 548 |
| HPV45 | E1 | 8 | 200 |
| HPV45 | E1 | 9 | 200 |
| HPV45 | E1 | 11 | 200 |
| HPV45 | E1 | 10 | 513 |
| HPV45 | E1 | 8 | 298 |
| HPV45 | E1 | 9 | 47 |
| HPV45 | E1 | 11 | 47 |
| HPV45 | E1 | 10 | 353 |
| HPV45 | E1 | 10 | 560 |
| HPV45 | E1 | 8 | 414 |
| HPV45 | E1 | 8 | 237 |
| HPV45 | E1 | 11 | 237 |
| HPV45 | E1 | 11 | 592 |
| HPV45 | E1 | 8 | 177 |
| HPV45 | E1 | 11 | 177 |
| HPV45 | E1 | 8 | 554 |
| HPV45 | E1 | 11 | 554 |
| HPV45 | E1 | 11 | 537 |
| HPV45 | E1 | 8 | 434 |

TABLE XIV-continued

HLA-B62 Supermotif Peptides

| 1 | 2 | 3 | 4 |
|---|---|---|---|
| HPV45 | E1 | 11 | 434 |
| HPV45 | E1 | 8 | 505 |
| HPV45 | E1 | 9 | 505 |
| HPV45 | E1 | 10 | 505 |
| HPV45 | E1 | 8 | 98 |
| HPV45 | E1 | 10 | 546 |
| HPV45 | E1 | 11 | 546 |
| HPV45 | E1 | 9 | 553 |
| HPV45 | E1 | 8 | 302 |
| HPV45 | E1 | 9 | 302 |
| HPV45 | E1 | 10 | 302 |
| HPV45 | E1 | 11 | 302 |
| HPV45 | E1 | 10 | 593 |
| HPV45 | E1 | 9 | 374 |
| HPV45 | E1 | 10 | 374 |
| HPV45 | E1 | 11 | 374 |
| HPV45 | E1 | 8 | 549 |
| HPV45 | E1 | 9 | 549 |
| HPV45 | E1 | 8 | 54 |
| HPV45 | E1 | 8 | 102 |
| HPV45 | E1 | 8 | 412 |
| HPV45 | E1 | 10 | 412 |
| HPV45 | E1 | 10 | 80 |
| HPV45 | E1 | 11 | 80 |
| HPV45 | E1 | 8 | 148 |
| HPV45 | E1 | 11 | 612 |
| HPV45 | E1 | 10 | 128 |
| HPV45 | E1 | 9 | 335 |
| HPV45 | E1 | 8 | 280 |
| HPV45 | E1 | 11 | 280 |
| HPV45 | E1 | 9 | 433 |
| HPV45 | E1 | 8 | 411 |
| HPV45 | E1 | 9 | 411 |
| HPV45 | E1 | 11 | 411 |
| HPV45 | E1 | 10 | 575 |
| HPV45 | E1 | 11 | 575 |
| HPV45 | E1 | 11 | 56 |
| HPV45 | E1 | 9 | 539 |
| HPV45 | E1 | 10 | 539 |
| HPV45 | E1 | 8 | 183 |
| HPV45 | E1 | 9 | 183 |
| HPV45 | E1 | 11 | 183 |
| HPV45 | E1 | 9 | 117 |
| HPV45 | E1 | 9 | 97 |
| HPV45 | E1 | 9 | 110 |
| HPV45 | E1 | 11 | 416 |
| HPV45 | E1 | 8 | 308 |
| HPV45 | E1 | 10 | 104 |
| HPV45 | E1 | 10 | 22 |
| HPV45 | E1 | 11 | 22 |
| HPV45 | E1 | 8 | 246 |
| HPV45 | E1 | 9 | 246 |
| HPV45 | E1 | 10 | 246 |
| HPV45 | E1 | 10 | 289 |
| HPV45 | E1 | 11 | 289 |
| HPV45 | E1 | 9 | 252 |
| HPV45 | E1 | 8 | 329 |
| HPV45 | E1 | 10 | 329 |
| HPV45 | E1 | 11 | 329 |
| HPV45 | E1 | 8 | 460 |
| HPV45 | E1 | 9 | 460 |
| HPV45 | E1 | 10 | 460 |
| HPV45 | E1 | 9 | 53 |
| HPV45 | E1 | 9 | 147 |
| HPV45 | E1 | 9 | 239 |
| HPV45 | E1 | 10 | 239 |
| HPV45 | E1 | 9 | 282 |
| HPV45 | E1 | 10 | 282 |
| HPV45 | E1 | 8 | 577 |
| HPV45 | E1 | 9 | 577 |
| HPV45 | E1 | 11 | 577 |
| HPV45 | E1 | 10 | 31 |
| HPV45 | E1 | 9 | 81 |
| HPV45 | E1 | 10 | 81 |
| HPV45 | E1 | 9 | 266 |
| HPV45 | E1 | 11 | 230 |
| HPV45 | E1 | 9 | 400 |
| HPV45 | E1 | 8 | 293 |
| HPV45 | E1 | 9 | 436 |
| HPV45 | E1 | 11 | 436 |
| HPV45 | E1 | 8 | 75 |
| HPV45 | E1 | 10 | 75 |
| HPV45 | E1 | 11 | 75 |
| HPV45 | E1 | 9 | 354 |
| HPV45 | E1 | 9 | 418 |
| HPV45 | E1 | 8 | 332 |
| HPV45 | E1 | 10 | 502 |
| HPV45 | E1 | 11 | 502 |
| HPV45 | E1 | 8 | 569 |
| HPV45 | E1 | 10 | 569 |
| HPV45 | E1 | 11 | 569 |
| HPV45 | E1 | 8 | 229 |
| HPV45 | E1 | 8 | 571 |
| HPV45 | E1 | 9 | 571 |
| HPV45 | E1 | 11 | 571 |
| HPV45 | E1 | 8 | 394 |
| HPV45 | E1 | 11 | 528 |
| HPV45 | E1 | 9 | 441 |
| HPV45 | E1 | 10 | 441 |
| HPV45 | E2 | 8 | 78 |
| HPV45 | E2 | 11 | 78 |
| HPV45 | E2 | 11 | 47 |
| HPV45 | E2 | 10 | 84 |
| HPV45 | E2 | 10 | 16 |
| HPV45 | E2 | 10 | 89 |
| HPV45 | E2 | 9 | 305 |
| HPV45 | E2 | 10 | 305 |
| HPV45 | E2 | 10 | 134 |
| HPV45 | E2 | 11 | 134 |
| HPV45 | E2 | 8 | 158 |
| HPV45 | E2 | 9 | 158 |
| HPV45 | E2 | 10 | 158 |
| HPV45 | E2 | 8 | 31 |
| HPV45 | E2 | 9 | 31 |
| HPV45 | E2 | 11 | 31 |
| HPV45 | E2 | 9 | 351 |
| HPV45 | E2 | 11 | 351 |
| HPV45 | E2 | 8 | 319 |
| HPV45 | E2 | 9 | 80 |
| HPV45 | E2 | 10 | 80 |
| HPV45 | E2 | 11 | 106 |
| HPV45 | E2 | 11 | 258 |
| HPV45 | E2 | 8 | 343 |
| HPV45 | E2 | 10 | 343 |
| HPV45 | E2 | 11 | 343 |
| HPV45 | E2 | 8 | 192 |
| HPV45 | E2 | 9 | 192 |
| HPV45 | E2 | 11 | 349 |
| HPV45 | E2 | 11 | 334 |
| HPV45 | E2 | 9 | 56 |
| HPV45 | E2 | 10 | 56 |
| HPV45 | E2 | 8 | 150 |
| HPV45 | E2 | 10 | 150 |
| HPV45 | E2 | 10 | 255 |
| HPV45 | E2 | 9 | 295 |
| HPV45 | E2 | 9 | 62 |
| HPV45 | E2 | 11 | 293 |
| HPV45 | E2 | 10 | 48 |
| HPV45 | E2 | 10 | 335 |
| HPV45 | E2 | 9 | 355 |
| HPV45 | E2 | 11 | 355 |
| HPV45 | E2 | 8 | 219 |
| HPV45 | E2 | 10 | 59 |
| HPV45 | E2 | 9 | 2 |
| HPV45 | E2 | 8 | 240 |
| HPV45 | E2 | 10 | 284 |
| HPV45 | E2 | 11 | 284 |
| HPV45 | E2 | 8 | 41 |
| HPV45 | E2 | 9 | 41 |
| HPV45 | E2 | 10 | 41 |

TABLE XIV-continued

HLA-B62 Supermotif Peptides

| 1 | 2 | 3 | 4 |
|---|---|---|---|
| HPV45 | E2 | 9 | 17 |
| HPV45 | E2 | 8 | 100 |
| HPV45 | E2 | 9 | 100 |
| HPV45 | E2 | 8 | 81 |
| HPV45 | E2 | 9 | 81 |
| HPV45 | E2 | 8 | 3 |
| HPV45 | E2 | 10 | 69 |
| HPV45 | E2 | 11 | 69 |
| HPV45 | E2 | 9 | 198 |
| HPV45 | E2 | 9 | 67 |
| HPV45 | E2 | 10 | 66 |
| HPV45 | E2 | 9 | 360 |
| HPV45 | E2 | 8 | 35 |
| HPV45 | E2 | 10 | 35 |
| HPV45 | E2 | 9 | 218 |
| HPV45 | E2 | 8 | 40 |
| HPV45 | E2 | 9 | 40 |
| HPV45 | E2 | 10 | 40 |
| HPV45 | E2 | 11 | 40 |
| HPV45 | E2 | 8 | 82 |
| HPV45 | E2 | 8 | 63 |
| HPV45 | E2 | 8 | 43 |
| HPV45 | E2 | 10 | 43 |
| HPV45 | E2 | 9 | 309 |
| HPV45 | E2 | 9 | 13 |
| HPV45 | E2 | 10 | 13 |
| HPV45 | E2 | 10 | 263 |
| HPV45 | E2 | 11 | 263 |
| HPV45 | E2 | 10 | 142 |
| HPV45 | E2 | 11 | 142 |
| HPV45 | E2 | 9 | 302 |
| HPV45 | E2 | 8 | 9 |
| HPV45 | E2 | 9 | 9 |
| HPV45 | E2 | 10 | 205 |
| HPV45 | E2 | 11 | 113 |
| HPV45 | E2 | 8 | 34 |
| HPV45 | E2 | 9 | 34 |
| HPV45 | E2 | 11 | 34 |
| HPV45 | E2 | 9 | 235 |
| HPV45 | E2 | 8 | 358 |
| HPV45 | E2 | 9 | 358 |
| HPV45 | E2 | 11 | 358 |
| HPV45 | E2 | 8 | 354 |
| HPV45 | E2 | 10 | 354 |
| HPV45 | E2 | 9 | 99 |
| HPV45 | E2 | 10 | 99 |
| HPV45 | E2 | 10 | 5 |
| HPV45 | E2 | 10 | 238 |
| HPV45 | E2 | 10 | 217 |
| HPV45 | E2 | 8 | 213 |
| HPV45 | E2 | 11 | 213 |
| HPV45 | E2 | 8 | 337 |
| HPV45 | E2 | 8 | 199 |
| HPV45 | E2 | 11 | 65 |
| HPV45 | E2 | 10 | 176 |
| HPV45 | E2 | 8 | 359 |
| HPV45 | E2 | 10 | 359 |
| HPV45 | E2 | 9 | 344 |
| HPV45 | E2 | 10 | 344 |
| HPV45 | E2 | 8 | 193 |
| HPV45 | E2 | 8 | 352 |
| HPV45 | E2 | 10 | 352 |
| HPV45 | E2 | 8 | 138 |
| HPV45 | E2 | 9 | 138 |
| HPV45 | E2 | 9 | 39 |
| HPV45 | E2 | 10 | 39 |
| HPV45 | E2 | 11 | 39 |
| HPV45 | E2 | 9 | 166 |
| HPV45 | E2 | 10 | 166 |
| HPV45 | E2 | 11 | 166 |
| HPV45 | E2 | 8 | 145 |
| HPV45 | E2 | 11 | 175 |
| HPV45 | E2 | 8 | 137 |
| HPV45 | E2 | 9 | 137 |
| HPV45 | E2 | 10 | 137 |
| HPV45 | E6 | 11 | 59 |
| HPV45 | E6 | 8 | 68 |
| HPV45 | E6 | 11 | 68 |
| HPV45 | E6 | 8 | 105 |
| HPV45 | E6 | 11 | 105 |
| HPV45 | E6 | 8 | 108 |
| HPV45 | E6 | 8 | 32 |
| HPV45 | E6 | 10 | 16 |
| HPV45 | E6 | 10 | 51 |
| HPV45 | E6 | 11 | 51 |
| HPV45 | E6 | 9 | 6 |
| HPV45 | E6 | 8 | 143 |
| HPV45 | E6 | 8 | 27 |
| HPV45 | E6 | 11 | 27 |
| HPV45 | E6 | 9 | 20 |
| HPV45 | E6 | 11 | 20 |
| HPV45 | E6 | 9 | 77 |
| HPV45 | E6 | 10 | 77 |
| HPV45 | E6 | 10 | 97 |
| HPV45 | E6 | 10 | 43 |
| HPV45 | E6 | 11 | 43 |
| HPV45 | E6 | 8 | 53 |
| HPV45 | E6 | 9 | 53 |
| HPV45 | E6 | 10 | 53 |
| HPV45 | E6 | 11 | 53 |
| HPV45 | E6 | 10 | 136 |
| HPV45 | E6 | 8 | 120 |
| HPV45 | E6 | 11 | 120 |
| HPV45 | E6 | 8 | 54 |
| HPV45 | E6 | 9 | 54 |
| HPV45 | E6 | 10 | 54 |
| HPV45 | E6 | 11 | 54 |
| HPV45 | E6 | 8 | 92 |
| HPV45 | E6 | 10 | 92 |
| HPV45 | E6 | 11 | 92 |
| HPV45 | E6 | 9 | 13 |
| HPV45 | E6 | 11 | 102 |
| HPV45 | E6 | 8 | 14 |
| HPV45 | E6 | 9 | 25 |
| HPV45 | E6 | 10 | 25 |
| HPV45 | E6 | 9 | 113 |
| HPV45 | E6 | 11 | 111 |
| HPV45 | E6 | 8 | 74 |
| HPV45 | E6 | 10 | 149 |
| HPV45 | E6 | 8 | 10 |
| HPV45 | E6 | 9 | 29 |
| HPV45 | E6 | 11 | 29 |
| HPV45 | E6 | 8 | 24 |
| HPV45 | E6 | 10 | 24 |
| HPV45 | E6 | 11 | 24 |
| HPV45 | E6 | 10 | 84 |
| HPV45 | E6 | 10 | 89 |
| HPV45 | E6 | 11 | 89 |
| HPV45 | E6 | 8 | 38 |
| HPV45 | E6 | 10 | 38 |
| HPV45 | E6 | 11 | 38 |
| HPV45 | E6 | 10 | 8 |
| HPV45 | E6 | 8 | 45 |
| HPV45 | E6 | 9 | 45 |
| HPV45 | E6 | 10 | 45 |
| HPV45 | E6 | 11 | 45 |
| HPV45 | E7 | 8 | 48 |
| HPV45 | E7 | 10 | 64 |
| HPV45 | E7 | 8 | 25 |
| HPV45 | E7 | 8 | 83 |
| HPV45 | E7 | 9 | 83 |
| HPV45 | E7 | 10 | 83 |
| HPV45 | E7 | 8 | 22 |
| HPV45 | E7 | 11 | 22 |
| HPV45 | E7 | 8 | 20 |
| HPV45 | E7 | 10 | 20 |
| HPV45 | E7 | 8 | 74 |
| HPV45 | E7 | 11 | 74 |
| HPV45 | E7 | 9 | 16 |
| HPV45 | E7 | 11 | 16 |

TABLE XIV-continued

HLA-B62 Supermotif Peptides

| 1 | 2 | 3 | 4 |
|---|---|---|---|
| HPV45 | E7 | 8 | 56 |
| HPV45 | E7 | 10 | 56 |
| HPV45 | E7 | 8 | 91 |
| HPV45 | E7 | 11 | 91 |
| HPV45 | E7 | 9 | 3 |
| HPV45 | E7 | 10 | 3 |
| HPV45 | E7 | 11 | 3 |
| HPV45 | E7 | 9 | 44 |
| HPV45 | E7 | 8 | 14 |
| HPV45 | E7 | 11 | 14 |
| HPV45 | E7 | 11 | 11 |
| HPV45 | E7 | 8 | 8 |
| HPV45 | E7 | 9 | 87 |
| HPV45 | E7 | 11 | 87 |
| HPV45 | E7 | 8 | 17 |
| HPV45 | E7 | 10 | 17 |
| HPV45 | E7 | 11 | 17 |
| HPV45 | E7 | 9 | 57 |
| HPV45 | E7 | 10 | 23 |
| HPV45 | E7 | 9 | 89 |
| HPV45 | E7 | 10 | 89 |
| HPV45 | E7 | 8 | 88 |
| HPV45 | E7 | 10 | 88 |
| HPV45 | E7 | 11 | 88 |
| HPV45 | E7 | 10 | 72 |
| HPV45 | E7 | 9 | 7 |
| HPV45 | E7 | 10 | 86 |
| HPV45 | E7 | 8 | 94 |
| HPV45 | E7 | 10 | 94 |
| HPV45 | E7 | 9 | 76 |
| HPV45 | E7 | 10 | 12 |
| HPV45 | L1 | 11 | 191 |
| HPV45 | L1 | 8 | 103 |
| HPV45 | L1 | 10 | 103 |
| HPV45 | L1 | 10 | 28 |
| HPV45 | L1 | 11 | 28 |
| HPV45 | L1 | 8 | 345 |
| HPV45 | L1 | 10 | 345 |
| HPV45 | L1 | 11 | 205 |
| HPV45 | L1 | 11 | 164 |
| HPV45 | L1 | 8 | 88 |
| HPV45 | L1 | 10 | 88 |
| HPV45 | L1 | 8 | 184 |
| HPV45 | L1 | 9 | 184 |
| HPV45 | L1 | 8 | 276 |
| HPV45 | L1 | 9 | 276 |
| HPV45 | L1 | 10 | 212 |
| HPV45 | L1 | 11 | 212 |
| HPV45 | L1 | 10 | 252 |
| HPV45 | L1 | 11 | 252 |
| HPV45 | L1 | 9 | 188 |
| HPV45 | L1 | 10 | 188 |
| HPV45 | L1 | 11 | 318 |
| HPV45 | L1 | 9 | 250 |
| HPV45 | L1 | 11 | 488 |
| HPV45 | L1 | 10 | 480 |
| HPV45 | L1 | 8 | 401 |
| HPV45 | L1 | 11 | 401 |
| HPV45 | L1 | 9 | 301 |
| HPV45 | L1 | 11 | 301 |
| HPV45 | L1 | 9 | 226 |
| HPV45 | L1 | 10 | 226 |
| HPV45 | L1 | 8 | 386 |
| HPV45 | L1 | 8 | 469 |
| HPV45 | L1 | 9 | 469 |
| HPV45 | L1 | 11 | 469 |
| HPV45 | L1 | 8 | 267 |
| HPV45 | L1 | 9 | 267 |
| HPV45 | L1 | 11 | 267 |
| HPV45 | L1 | 9 | 490 |
| HPV45 | L1 | 10 | 490 |
| HPV45 | L1 | 11 | 490 |
| HPV45 | L1 | 8 | 169 |
| HPV45 | L1 | 10 | 169 |
| HPV45 | L1 | 8 | 133 |
| HPV45 | L1 | 10 | 133 |
| HPV45 | L1 | 8 | 280 |
| HPV45 | L1 | 9 | 280 |
| HPV45 | L1 | 9 | 416 |
| HPV45 | L1 | 10 | 246 |
| HPV45 | L1 | 8 | 404 |
| HPV45 | L1 | 10 | 404 |
| HPV45 | L1 | 8 | 14 |
| HPV45 | L1 | 10 | 14 |
| HPV45 | L1 | 11 | 14 |
| HPV45 | L1 | 8 | 21 |
| HPV45 | L1 | 9 | 21 |
| HPV45 | L1 | 10 | 21 |
| HPV45 | L1 | 8 | 406 |
| HPV45 | L1 | 10 | 406 |
| HPV45 | L1 | 8 | 351 |
| HPV45 | L1 | 9 | 351 |
| HPV45 | L1 | 10 | 351 |
| HPV45 | L1 | 9 | 141 |
| HPV45 | L1 | 10 | 141 |
| HPV45 | L1 | 9 | 10 |
| HPV45 | L1 | 11 | 10 |
| HPV45 | L1 | 8 | 111 |
| HPV45 | L1 | 8 | 503 |
| HPV45 | L1 | 8 | 143 |
| HPV45 | L1 | 11 | 143 |
| HPV45 | L1 | 10 | 131 |
| HPV45 | L1 | 8 | 511 |
| HPV45 | L1 | 8 | 137 |
| HPV45 | L1 | 11 | 292 |
| HPV45 | L1 | 10 | 435 |
| HPV45 | L1 | 11 | 435 |
| HPV45 | L1 | 9 | 396 |
| HPV45 | L1 | 10 | 396 |
| HPV45 | L1 | 11 | 396 |
| HPV45 | L1 | 8 | 221 |
| HPV45 | L1 | 9 | 12 |
| HPV45 | L1 | 10 | 12 |
| HPV45 | L1 | 8 | 11 |
| HPV45 | L1 | 10 | 11 |
| HPV45 | L1 | 11 | 11 |
| HPV45 | L1 | 8 | 5 |
| HPV45 | L1 | 9 | 5 |
| HPV45 | L1 | 10 | 5 |
| HPV45 | L1 | 11 | 5 |
| HPV45 | L1 | 9 | 428 |
| HPV45 | L1 | 8 | 185 |
| HPV45 | L1 | 8 | 152 |
| HPV45 | L1 | 10 | 152 |
| HPV45 | L1 | 11 | 152 |
| HPV45 | L1 | 9 | 473 |
| HPV45 | L1 | 8 | 338 |
| HPV45 | L1 | 9 | 86 |
| HPV45 | L1 | 10 | 86 |
| HPV45 | L1 | 8 | 467 |
| HPV45 | L1 | 10 | 467 |
| HPV45 | L1 | 11 | 467 |
| HPV45 | L1 | 8 | 179 |
| HPV45 | L1 | 11 | 179 |
| HPV45 | L1 | 9 | 91 |
| HPV45 | L1 | 10 | 91 |
| HPV45 | L1 | 8 | 68 |
| HPV45 | L1 | 9 | 68 |
| HPV45 | L1 | 11 | 68 |
| HPV45 | L1 | 9 | 104 |
| HPV45 | L1 | 9 | 39 |
| HPV45 | L1 | 10 | 39 |
| HPV45 | L1 | 8 | 240 |
| HPV45 | L1 | 10 | 240 |
| HPV45 | L1 | 10 | 402 |
| HPV45 | L1 | 8 | 262 |
| HPV45 | L1 | 9 | 207 |
| HPV45 | L1 | 11 | 207 |
| HPV45 | L1 | 8 | 444 |
| HPV45 | L1 | 11 | 444 |

TABLE XIV-continued

HLA-B62 Supermotif Peptides

| 1 | 2 | 3 | 4 |
|---|---|---|---|
| HPV45 | L1 | 8 | 125 |
| HPV45 | L1 | 10 | 125 |
| HPV45 | L1 | 8 | 227 |
| HPV45 | L1 | 9 | 227 |
| HPV45 | L1 | 11 | 227 |
| HPV45 | L1 | 8 | 4 |
| HPV45 | L1 | 9 | 4 |
| HPV45 | L1 | 10 | 4 |
| HPV45 | L1 | 11 | 4 |
| HPV45 | L1 | 10 | 310 |
| HPV45 | L1 | 11 | 310 |
| HPV45 | L1 | 8 | 119 |
| HPV45 | L1 | 9 | 119 |
| HPV45 | L1 | 10 | 119 |
| HPV45 | L1 | 11 | 73 |
| HPV45 | L1 | 8 | 356 |
| HPV45 | L1 | 9 | 19 |
| HPV45 | L1 | 10 | 19 |
| HPV45 | L1 | 11 | 19 |
| HPV45 | L1 | 8 | 17 |
| HPV45 | L1 | 9 | 17 |
| HPV45 | L1 | 11 | 17 |
| HPV45 | L1 | 11 | 173 |
| HPV45 | L1 | 8 | 22 |
| HPV45 | L1 | 9 | 22 |
| HPV45 | L1 | 8 | 248 |
| HPV45 | L1 | 11 | 248 |
| HPV45 | L1 | 8 | 214 |
| HPV45 | L1 | 9 | 214 |
| HPV45 | L1 | 11 | 139 |
| HPV45 | L1 | 8 | 493 |
| HPV45 | L1 | 10 | 493 |
| HPV45 | L1 | 8 | 464 |
| HPV45 | L1 | 11 | 464 |
| HPV45 | L1 | 9 | 213 |
| HPV45 | L1 | 10 | 213 |
| HPV45 | L1 | 8 | 437 |
| HPV45 | L1 | 9 | 437 |
| HPV45 | L1 | 8 | 40 |
| HPV45 | L1 | 9 | 40 |
| HPV45 | L1 | 8 | 438 |
| HPV45 | L1 | 11 | 438 |
| HPV45 | L1 | 8 | 41 |
| HPV45 | L1 | 10 | 439 |
| HPV45 | L1 | 11 | 380 |
| HPV45 | L1 | 8 | 182 |
| HPV45 | L1 | 10 | 182 |
| HPV45 | L1 | 11 | 182 |
| HPV45 | L1 | 9 | 407 |
| HPV45 | L1 | 11 | 407 |
| HPV45 | L1 | 8 | 281 |
| HPV45 | L1 | 11 | 281 |
| HPV45 | L1 | 8 | 334 |
| HPV45 | L1 | 9 | 334 |
| HPV45 | L1 | 10 | 206 |
| HPV45 | L1 | 11 | 263 |
| HPV45 | L1 | 8 | 208 |
| HPV45 | L1 | 10 | 208 |
| HPV45 | L1 | 9 | 67 |
| HPV45 | L1 | 10 | 67 |
| HPV45 | L1 | 9 | 124 |
| HPV45 | L1 | 11 | 124 |
| HPV45 | L1 | 9 | 515 |
| HPV45 | L1 | 8 | 525 |
| FIPV45 | L1 | 8 | 31 |
| HPV45 | L1 | 9 | 31 |
| HPV45 | L1 | 11 | 507 |
| HPV45 | L1 | 10 | 101 |
| HPV45 | L1 | 8 | 46 |
| HPV45 | L1 | 9 | 46 |
| HPV45 | L1 | 8 | 254 |
| HPV45 | L1 | 9 | 254 |
| HPV45 | L1 | 11 | 254 |
| HPV45 | L1 | 11 | 58 |
| HPV45 | L1 | 8 | 427 |
| HPV45 | L1 | 10 | 427 |
| HPV45 | L1 | 9 | 327 |
| HPV45 | L1 | 10 | 327 |
| HPV45 | L1 | 8 | 443 |
| HPV45 | L1 | 9 | 443 |
| HPV45 | L1 | 11 | 272 |
| HPV45 | L1 | 10 | 423 |
| HPV45 | L1 | 8 | 321 |
| HPV45 | L1 | 8 | 333 |
| HPV45 | L1 | 9 | 333 |
| HPV45 | L1 | 10 | 333 |
| HPV45 | L1 | 11 | 43 |
| HPV45 | L1 | 9 | 175 |
| HPV45 | L1 | 11 | 175 |
| HPV45 | L1 | 9 | 509 |
| HPV45 | L1 | 10 | 509 |
| HPV45 | L1 | 8 | 220 |
| HPV45 | L1 | 9 | 220 |
| HPV45 | L1 | 8 | 410 |
| HPV45 | L1 | 9 | 410 |
| HPV45 | L1 | 11 | 410 |
| HPV45 | L1 | 10 | 116 |
| HPV45 | L1 | 11 | 116 |
| HPV45 | L1 | 10 | 372 |
| HPV45 | L1 | 8 | 200 |
| HPV45 | L1 | 9 | 239 |
| HPV45 | L1 | 11 | 239 |
| HPV45 | L1 | 9 | 412 |
| HPV45 | L1 | 10 | 412 |
| HPV45 | L1 | 9 | 463 |
| HPV45 | L1 | 8 | 167 |
| HPV45 | L1 | 10 | 167 |
| H9V45 | L1 | 9 | 181 |
| HPV45 | L1 | 11 | 181 |
| HPV45 | L1 | 9 | 377 |
| HPV45 | L1 | 9 | 122 |
| HPV45 | L1 | 11 | 122 |
| HPV45 | L1 | 8 | 478 |
| HPV45 | L1 | 9 | 70 |
| HPV45 | L1 | 10 | 70 |
| HPV45 | L1 | 8 | 297 |
| HPV45 | L1 | 11 | 361 |
| HPV45 | L1 | 9 | 36 |
| HPV45 | L1 | 10 | 36 |
| HPV45 | L1 | 10 | 165 |
| HPV45 | L1 | 10 | 293 |
| HPV45 | L1 | 11 | 293 |
| HPV45 | L1 | 8 | 417 |
| HPV45 | L1 | 8 | 189 |
| HPV45 | L1 | 9 | 189 |
| HPV45 | L1 | 9 | 89 |
| HPV45 | L1 | 11 | 89 |
| HPV45 | L1 | 9 | 247 |
| HPV45 | L1 | 10 | 381 |
| HPV45 | L1 | 9 | 436 |
| HPV45 | L1 | 10 | 436 |
| HPV45 | L1 | 10 | 79 |
| HPV45 | L1 | 11 | 79 |
| HPV45 | L1 | 11 | 500 |
| HPV45 | L1 | 10 | 362 |
| HPV45 | L1 | 8 | 47 |
| HPV45 | L1 | 11 | 78 |
| HPV45 | L1 | 9 | 420 |
| HPV45 | L1 | 10 | 420 |
| HPV45 | L1 | 9 | 303 |
| HPV45 | L1 | 8 | 38 |
| HPV45 | L1 | 10 | 38 |
| HPV45 | L1 | 11 | 38 |
| HPV45 | L1 | 9 | 261 |
| HPV45 | L1 | 9 | 258 |
| HPV45 | L1 | 8 | 492 |
| HPV45 | L1 | 9 | 492 |
| HPV45 | L1 | 11 | 492 |
| HPV45 | L1 | 8 | 95 |
| HPV45 | L1 | 9 | 95 |

TABLE XIV-continued

HLA-B62 Supermotif Peptides

| 1 | 2 | 3 | 4 |
|---|---|---|---|
| HPV45 | L1 | 10 | 95 |
| HPV45 | L1 | 8 | 53 |
| HPV45 | L1 | 9 | 53 |
| HPV45 | L1 | 11 | 53 |
| HPV45 | L2 | 9 | 286 |
| HPV45 | L2 | 11 | 286 |
| HPV45 | L2 | 9 | 139 |
| HPV45 | L2 | 9 | 27 |
| HPV45 | L2 | 10 | 405 |
| HPV45 | L2 | 11 | 405 |
| HPV45 | L2 | 9 | 278 |
| HPV45 | L2 | 10 | 278 |
| HPV45 | L2 | 11 | 322 |
| HPV45 | L2 | 9 | 142 |
| HPV45 | L2 | 11 | 142 |
| HPV45 | L2 | 9 | 345 |
| HPV45 | L2 | 8 | 100 |
| HPV45 | L2 | 9 | 83 |
| HPV45 | L2 | 10 | 83 |
| HPV45 | L2 | 11 | 83 |
| HPV45 | L2 | 11 | 30 |
| HPV45 | L2 | 10 | 397 |
| HPV45 | L2 | 11 | 397 |
| HPV45 | L2 | 10 | 348 |
| HPV45 | L2 | 8 | 331 |
| HPV45 | L2 | 10 | 331 |
| HPV45 | L2 | 8 | 194 |
| HPV45 | L2 | 11 | 129 |
| HPV45 | L2 | 8 | 333 |
| HPV45 | L2 | 8 | 208 |
| HPV45 | L2 | 11 | 208 |
| HPV45 | L2 | 9 | 257 |
| HPV45 | L2 | 11 | 266 |
| HPV45 | L2 | 10 | 94 |
| HPV45 | L2 | 11 | 94 |
| HPV45 | L2 | 8 | 169 |
| HPV45 | L2 | 8 | 175 |
| HPV45 | L2 | 8 | 241 |
| HPV45 | L2 | 9 | 241 |
| HPV45 | L2 | 11 | 241 |
| HPV45 | L2 | 11 | 276 |
| HPV45 | L2 | 8 | 445 |
| HPV45 | L2 | 10 | 445 |
| HPV45 | L2 | 11 | 445 |
| HPV45 | L2 | 9 | 51 |
| HPV45 | L2 | 8 | 430 |
| HPV45 | L2 | 9 | 430 |
| HPV45 | L2 | 10 | 430 |
| HPV45 | L2 | 8 | 223 |
| HPV45 | L2 | 8 | 97 |
| HPV45 | L2 | 10 | 97 |
| HPV45 | L2 | 11 | 97 |
| HPV45 | L2 | 8 | 85 |
| HPV45 | L2 | 9 | 85 |
| HPV45 | L2 | 8 | 244 |
| HPV45 | L2 | 10 | 167 |
| HPV45 | L2 | 9 | 406 |
| HPV45 | L2 | 10 | 406 |
| HPV45 | L2 | 8 | 279 |
| HPV45 | L2 | 9 | 279 |
| HPV45 | L2 | 8 | 407 |
| HPV45 | L2 | 9 | 407 |
| HPV45 | L2 | 9 | 44 |
| HPV45 | L2 | 10 | 44 |
| HPV45 | L2 | 11 | 44 |
| HPV45 | L2 | 9 | 452 |
| HPV45 | L2 | 10 | 452 |
| HPV45 | L2 | 11 | 452 |
| HPV45 | L2 | 10 | 103 |
| HPV45 | L2 | 11 | 103 |
| HPV45 | L2 | 8 | 43 |
| HPV45 | L2 | 10 | 43 |
| HPV45 | L2 | 11 | 43 |
| HPV45 | L2 | 9 | 311 |
| HPV45 | L2 | 10 | 311 |
| HPV45 | L2 | 10 | 22 |
| HPV45 | L2 | 11 | 22 |
| HPV45 | L2 | 8 | 34 |
| HPV45 | L2 | 11 | 34 |
| HPV45 | L2 | 10 | 337 |
| HPV45 | L2 | 11 | 337 |
| HPV45 | L2 | 8 | 408 |
| HPV45 | L2 | 8 | 45 |
| HPV45 | L2 | 9 | 45 |
| HPV45 | L2 | 10 | 45 |
| HPV45 | L2 | 8 | 106 |
| HPV45 | L2 | 9 | 106 |
| HPV45 | L2 | 8 | 248 |
| HPV45 | L2 | 9 | 248 |
| HPV45 | L2 | 9 | 377 |
| HPV45 | L2 | 9 | 159 |
| HPV45 | L2 | 10 | 159 |
| HPV45 | L2 | 11 | 253 |
| HPV45 | L2 | 11 | 231 |
| HPV45 | L2 | 8 | 270 |
| HPV45 | L2 | 10 | 270 |
| HPV45 | L2 | 11 | 270 |
| HPV45 | L2 | 9 | 387 |
| HPV45 | L2 | 10 | 387 |
| HPV45 | L2 | 8 | 325 |
| HPV45 | L2 | 10 | 325 |
| HPV45 | L2 | 10 | 209 |
| HPV45 | L2 | 8 | 399 |
| HPV45 | L2 | 9 | 399 |
| HPV45 | L2 | 10 | 399 |
| HPV45 | L2 | 8 | 258 |
| HPV45 | L2 | 9 | 73 |
| HPV45 | L2 | 10 | 73 |
| HPV45 | L2 | 11 | 336 |
| HPV45 | L2 | 8 | 214 |
| HPV45 | L2 | 8 | 391 |
| HPV45 | L2 | 10 | 391 |
| HPV45 | L2 | 11 | 391 |
| HPV45 | L2 | 11 | 413 |
| HPV45 | L2 | 10 | 355 |
| HPV45 | L2 | 8 | 28 |
| HPV45 | L2 | 11 | 354 |
| HPV45 | L2 | 8 | 89 |
| HPV45 | L2 | 10 | 171 |
| HPV45 | L2 | 11 | 171 |
| HPV45 | L2 | 9 | 95 |
| HPV45 | L2 | 10 | 95 |
| HPV45 | L2 | 11 | 118 |
| HPV45 | L2 | 8 | 312 |
| HPV45 | L2 | 9 | 312 |
| HPV45 | L2 | 10 | 232 |
| HPV45 | L2 | 11 | 232 |
| HPV45 | L2 | 9 | 233 |
| HPV45 | L2 | 10 | 233 |
| HPV45 | L2 | 10 | 451 |
| HPV45 | L2 | 11 | 451 |
| HPV45 | L2 | 8 | 298 |
| HPV45 | L2 | 9 | 298 |
| HPV45 | L2 | 10 | 225 |
| HPV45 | 1,2 | 11 | 284 |
| HPV45 | L2 | 9 | 88 |
| HPV45 | L2 | 8 | 316 |
| HPV45 | L2 | 11 | 316 |
| HPV45 | L2 | 8 | 220 |
| HPV45 | L2 | 11 | 220 |
| HPV45 | L2 | 8 | 235 |
| HPV45 | L2 | 11 | 166 |
| HPV45 | L2 | 11 | 151 |
| HPV45 | L2 | 11 | 102 |
| HPV45 | L2 | 9 | 49 |
| HPV45 | L2 | 11 | 49 |
| HPV45 | L2 | 8 | 374 |
| HPV45 | L2 | 9 | 374 |
| HPV45 | L2 | 9 | 247 |
| HPV45 | L2 | 10 | 247 |

TABLE XIV-continued

HLA-B62 Supermotif Peptides

| 1 | 2 | 3 | 4 |
|---|---|---|---|
| HPV45 | L2 | 9 | 324 |
| HPV45 | L2 | 11 | 324 |
| HPV45 | L2 | 10 | 419 |
| HPV45 | L2 | 11 | 419 |
| HPV45 | L2 | 10 | 239 |
| HPV45 | L2 | 11 | 239 |
| HPV45 | L2 | 9 | 149 |
| HPV45 | L2 | 9 | 111 |
| HPV45 | L2 | 8 | 363 |
| HPV45 | L2 | 11 | 363 |
| HPV45 | L2 | 9 | 39 |
| HPV45 | L2 | 10 | 262 |
| HPV45 | L2 | 8 | 105 |
| HPV45 | L2 | 9 | 105 |
| HPV45 | L2 | 10 | 105 |
| HPV45 | L2 | 10 | 304 |
| HPV45 | L2 | 10 | 376 |
| HPV45 | L2 | 11 | 137 |
| HPV45 | L2 | 9 | 213 |
| HPV45 | L2 | 9 | 360 |
| HPV45 | L2 | 11 | 360 |
| HPV45 | L2 | 9 | 184 |
| HPV45 | L2 | 9 | 144 |
| HPV45 | L2 | 8 | 434 |
| HPV45 | L2 | 9 | 434 |
| HPV45 | L2 | 10 | 434 |
| HPV45 | L2 | 11 | 434 |
| HPV45 | L2 | 8 | 389 |
| HPV45 | L2 | 10 | 389 |
| HPV45 | L2 | 11 | 293 |
| HPV45 | L2 | 10 | 217 |
| HPV45 | L2 | 11 | 217 |
| HPV45 | L2 | 10 | 31 |
| HPV45 | L2 | 11 | 31 |
| HPV45 | L2 | 8 | 140 |
| HPV45 | L2 | 11 | 140 |
| HPV45 | L2 | 9 | 271 |
| HPV45 | L2 | 10 | 271 |
| HPV45 | L2 | 9 | 398 |
| HPV45 | L2 | 10 | 398 |
| HPV45 | L2 | 11 | 398 |
| HPV45 | L2 | 10 | 72 |
| HPV45 | L2 | 11 | 72 |
| HPV45 | L2 | 9 | 390 |
| HPV45 | L2 | 11 | 390 |
| HPV45 | L2 | 11 | 170 |
| HPV45 | L2 | 10 | 119 |
| HPV45 | L2 | 8 | 112 |
| HPV45 | L2 | 11 | 112 |
| HPV45 | L2 | 11 | 81 |
| HPV45 | L2 | 9 | 415 |
| HPV45 | L2 | 9 | 428 |
| HPV45 | L2 | 10 | 428 |
| HPV45 | L2 | 11 | 428 |
| HPV45 | L2 | 8 | 437 |
| HPV45 | L2 | 9 | 437 |
| HPV45 | L2 | 8 | 370 |
| HPV45 | L2 | 11 | 71 |
| HPV56 | E2 | 8 | 15 |
| HPV56 | E2 | 11 | 15 |
| HPV56 | E2 | 9 | 21 |
| HPV56 | E2 | 10 | 21 |
| HPV56 | E2 | 9 | 4 |
| HPV56 | E2 | 9 | 71 |
| HPV56 | E2 | 10 | 71 |
| HPV56 | E2 | 11 | 71 |
| HPV56 | E2 | 11 | 138 |
| HPV56 | E2 | 8 | 204 |
| HPV56 | E2 | 8 | 263 |
| HPV56 | E2 | 11 | 43 |
| HPV56 | E2 | 10 | 243 |
| HPV56 | E2 | 9 | 128 |
| HPV56 | E2 | 10 | 128 |
| HPV56 | E2 | 9 | 17 |
| HPV56 | E2 | 9 | 294 |
| HPV56 | E2 | 10 | 294 |
| HPV56 | E2 | 11 | 294 |
| HPV56 | E2 | 8 | 254 |
| HPV56 | E2 | 9 | 254 |
| HPV56 | E2 | 11 | 254 |
| HPV56 | E2 | 8 | 261 |
| HPV56 | E2 | 10 | 261 |
| HPV56 | E2 | 8 | 57 |
| HPV56 | E2 | 8 | 94 |
| HPV56 | E2 | 9 | 94 |
| HPV56 | E2 | 10 | 94 |
| HPV56 | E2 | 9 | 239 |
| HPV56 | E2 | 8 | 130 |
| HPV56 | E2 | 9 | 229 |
| HPV56 | E2 | 10 | 229 |
| HPV56 | E2 | 8 | 297 |
| HPV56 | E2 | 10 | 297 |
| HPV56 | E2 | 11 | 297 |
| HPV56 | E2 | 8 | 300 |
| HPV56 | E2 | 9 | 300 |
| HPV56 | E2 | 8 | 299 |
| HPV56 | E2 | 9 | 299 |
| HPV56 | E2 | 10 | 299 |
| HPV56 | E2 | 8 | 90 |
| HPV56 | E2 | 11 | 90 |
| HPV56 | E2 | 8 | 5 |
| HPV56 | E2 | 11 | 5 |
| HPV56 | E2 | 8 | 72 |
| HPV56 | E2 | 9 | 72 |
| HPV56 | E2 | 10 | 72 |
| HPV56 | E2 | 11 | 72 |
| HPV56 | E2 | 10 | 1 |
| HPV56 | E2 | 8 | 149 |
| HPV56 | E2 | 11 | 149 |
| HPV56 | E2 | 8 | 152 |
| HPV56 | E2 | 8 | 301 |
| HPV56 | E2 | 11 | 19 |
| HPV56 | E2 | 10 | 6 |
| HPV56 | E2 | 11 | 6 |
| HPV56 | E2 | 9 | 246 |
| HPV56 | E2 | 8 | 182 |
| HPV56 | E2 | 9 | 186 |
| HPV56 | E2 | 8 | 135 |
| HPV56 | E2 | 9 | 151 |
| HPV56 | E2 | 8 | 171 |
| HPV56 | E2 | 9 | 171 |
| HPV56 | E2 | 8 | 141 |
| HPV56 | E2 | 10 | 141 |
| HPV56 | E2 | 8 | 28 |
| HPV56 | E2 | 10 | 28 |
| HPV56 | E2 | 10 | 259 |
| HPV56 | E2 | 9 | 36 |
| HPV56 | E2 | 10 | 36 |
| HPV56 | E2 | 11 | 36 |
| HPV56 | E2 | 10 | 289 |
| HPV56 | E2 | 9 | 2 |
| HPV56 | E2 | 11 | 2 |
| HPV56 | E2 | 8 | 18 |
| HPV56 | E2 | 11 | 237 |
| HPV56 | E2 | 9 | 45 |
| HPV56 | E2 | 8 | 88 |
| HPV56 | E2 | 10 | 88 |
| HPV56 | E2 | 10 | 79 |
| HPV56 | E2 | 8 | 74 |
| HPV56 | E2 | 9 | 74 |
| HPV56 | E2 | 9 | 102 |
| HPV56 | E2 | 10 | 102 |
| HPV56 | E6 | 8 | 64 |
| HPV56 | E6 | 9 | 64 |
| HPV56 | E6 | 10 | 64 |
| HPV56 | E6 | 8 | 69 |
| HPV56 | E6 | 11 | 69 |
| HPV56 | E6 | 8 | 33 |
| HPV56 | E6 | 11 | 33 |
| HPV56 | E6 | 8 | 28 |

TABLE XIV-continued

HLA-B62 Supermotif Peptides

| 1 | 2 | 3 | 4 |
|---|---|---|---|
| HPV56 | E6 | 9 | 23 |
| HPV56 | E6 | 10 | 52 |
| HPV56 | E6 | 8 | 39 |
| HPV56 | E6 | 10 | 39 |
| HPV56 | E6 | 11 | 39 |
| HPV56 | E6 | 8 | 20 |
| HPV56 | E6 | 10 | 20 |
| HPV56 | E6 | 10 | 44 |
| HPV56 | E6 | 8 | 61 |
| HPV56 | E6 | 10 | 61 |
| HPV56 | E6 | 11 | 61 |
| HPV56 | E6 | 8 | 17 |
| HPV56 | E6 | 10 | 17 |
| HPV56 | E6 | 11 | 17 |
| HPV56 | E6 | 8 | 24 |
| HPV56 | E6 | 11 | 24 |
| HPV56 | E6 | 8 | 54 |
| HPV56 | E6 | 10 | 54 |
| HPV56 | E6 | 11 | 54 |
| HPV56 | E6 | 8 | 97 |
| HPV56 | E6 | 11 | 97 |
| HPV56 | E6 | 11 | 118 |
| HPV56 | E6 | 8 | 75 |
| HPV56 | E6 | 10 | 75 |
| HPV56 | E6 | 11 | 130 |
| HPV56 | E6 | 9 | 26 |
| HPV56 | E6 | 10 | 26 |
| HPV56 | E6 | 11 | 103 |
| HPV56 | E6 | 10 | 70 |
| HPV56 | E6 | 9 | 55 |
| HPV56 | E6 | 10 | 55 |
| HPV56 | E6 | 11 | 55 |
| HPV56 | E6 | 9 | 7 |
| HPV56 | E6 | 10 | 25 |
| HPV56 | E6 | 11 | 25 |
| HPV56 | E6 | 9 | 112 |
| HPV56 | E6 | 8 | 8 |
| HPV56 | E6 | 11 | 8 |
| HPV56 | E6 | 10 | 98 |
| HPV56 | E6 | 10 | 119 |
| HPV56 | E6 | 11 | 30 |
| HPV56 | E6 | 8 | 11 |
| HPV56 | E6 | 11 | 11 |
| HPV56 | E6 | 10 | 67 |
| HPV56 | E6 | 10 | 93 |
| HPV56 | E6 | 11 | 93 |
| HPV56 | E6 | 8 | 14 |
| HPV56 | E6 | 9 | 14 |
| HPV56 | E6 | 11 | 14 |
| HPV56 | E6 | 10 | 111 |
| HPV56 | E6 | 10 | 85 |
| HPV56 | E6 | 10 | 90 |
| HPV56 | E6 | 9 | 21 |
| HPV56 | E6 | 11 | 21 |
| HPV56 | E7 | 8 | 93 |
| HPV56 | E7 | 10 | 93 |
| HPV56 | E7 | 9 | 75 |
| HPV56 | E7 | 11 | 75 |
| HPV56 | E7 | 8 | 22 |
| HPV56 | E7 | 8 | 82 |
| HPV56 | E7 | 9 | 82 |
| HPV56 | E7 | 10 | 82 |
| HPV56 | E7 | 10 | 20 |
| HPV56 | E7 | 8 | 14 |
| HPV56 | E7 | 10 | 14 |
| HPV56 | E7 | 9 | 42 |
| HPV56 | E7 | 9 | 62 |
| HPV56 | E7 | 10 | 62 |
| HPV56 | E7 | 11 | 62 |
| HPV56 | E7 | 8 | 76 |
| HPV56 | E7 | 10 | 76 |
| HPV56 | E7 | 11 | 76 |
| HPV56 | E7 | 8 | 54 |
| HPV56 | E7 | 10 | 54 |
| HPV56 | E7 | 8 | 4 |
| HPV56 | E7 | 9 | 4 |
| HPV56 | E7 | 10 | 4 |
| HPV56 | E7 | 11 | 60 |
| HPV56 | E7 | 8 | 89 |
| HPV56 | E7 | 11 | 90 |
| HPV56 | E7 | 8 | 8 |
| HPV56 | E7 | 8 | 43 |
| HPV56 | E7 | 11 | 43 |
| HPV56 | E7 | 11 | 73 |
| HPV56 | E7 | 9 | 88 |
| HPV56 | E7 | 8 | 87 |
| HPV56 | E7 | 10 | 87 |
| HPV56 | E7 | 8 | 46 |
| HPV56 | E7 | 9 | 51 |
| HPV56 | E7 | 10 | 51 |
| HPV56 | E7 | 11 | 51 |
| HPV56 | E7 | 8 | 84 |
| HPV56 | E7 | 10 | 84 |
| HPV56 | E7 | 11 | 84 |
| HPV56 | E7 | 9 | 7 |
| HPV56 | E7 | 8 | 16 |
| HFV56 | E7 | 8 | 95 |
| HPV56 | E7 | 10 | 12 |
| HPV56 | E7 | 8 | 63 |
| HPV56 | E7 | 9 | 63 |
| HPV56 | E7 | 10 | 63 |
| HPV56 | E7 | 8 | 5 |
| HPV56 | E7 | 9 | 5 |
| HPV56 | E7 | 11 | 5 |
| HPV56 | E7 | 8 | 86 |
| HPV56 | E7 | 9 | 86 |
| HPV56 | E7 | 11 | 86 |
| HPV56 | E7 | 11 | 11 |
| HPV56 | E7 | 9 | 85 |
| HPV56 | E7 | 10 | 85 |
| HPV56 | L1 | 10 | 198 |
| HPV56 | L1 | 11 | 198 |
| HPV56 | L1 | 9 | 521 |
| HPV56 | L1 | 8 | 350 |
| HPV56 | L1 | 10 | 350 |
| HPV56 | L1 | 8 | 338 |
| HPV56 | L1 | 9 | 338 |
| HPV56 | L1 | 10 | 338 |
| HPV56 | L1 | 10 | 512 |
| HPV56 | L1 | 8 | 207 |
| HPV56 | L1 | 9 | 79 |
| HPV56 | L1 | 8 | 26 |
| HPV56 | L1 | 9 | 26 |
| HPV56 | L1 | 11 | 26 |
| HPV56 | L1 | 8 | 19 |
| HPV56 | L1 | 9 | 19 |
| HPV56 | L1 | 11 | 19 |
| HPV56 | L1 | 8 | 191 |
| HPV56 | L1 | 9 | 191 |
| HPV56 | L1 | 11 | 219 |
| HPV56 | L1 | 9 | 257 |
| HPV56 | L1 | 11 | 491 |
| HPV56 | L1 | 9 | 233 |
| HPV56 | L1 | 10 | 233 |
| HPV56 | L1 | 8 | 472 |
| HPV56 | L1 | 9 | 472 |
| HPV56 | L1 | 11 | 472 |
| HPV56 | L1 | 8 | 11 |
| HPV56 | L1 | 10 | 11 |
| HPV56 | L1 | 11 | 11 |
| HPV56 | L1 | 8 | 128 |
| HPV56 | L1 | 10 | 128 |
| HPV56 | L1 | 9 | 493 |
| HPV56 | L1 | 10 | 493 |
| HPV56 | L1 | 11 | 493 |
| HPV56 | L1 | 8 | 23 |
| HPV56 | L1 | 10 | 23 |
| HPV56 | L1 | 11 | 23 |
| HPV56 | L1 | 8 | 481 |
| HPV56 | L1 | 8 | 404 |

TABLE XIV-continued

HLA-B62 Supermotif Peptides

| 1 | 2 | 3 | 4 |
|---|---|---|---|
| HPV56 | L1 | 11 | 404 |
| HPV56 | L1 | 8 | 318 |
| HPV56 | L1 | 9 | 318 |
| HPV56 | L1 | 10 | 318 |
| HPV56 | L1 | 8 | 287 |
| HPV56 | L1 | 9 | 287 |
| HPV56 | L1 | 8 | 383 |
| HPV56 | L1 | 11 | 383 |
| HPV56 | L1 | 11 | 464 |
| HPV56 | L1 | 8 | 140 |
| HPV56 | L1 | 10 | 140 |
| HPV56 | L1 | 9 | 419 |
| HPV56 | L1 | 11 | 419 |
| HPV56 | L1 | 9 | 21 |
| HPV56 | L1 | 10 | 21 |
| HPV56 | L1 | 8 | 30 |
| HPV56 | L1 | 10 | 30 |
| HPV56 | L1 | 8 | 495 |
| HPV56 | L1 | 9 | 495 |
| HPV56 | L1 | 11 | 495 |
| HPV56 | L1 | 8 | 409 |
| HPV56 | L1 | 10 | 409 |
| HPV56 | L1 | 8 | 407 |
| HPV56 | L1 | 10 | 407 |
| HPV56 | L1 | 8 | 356 |
| HPV56 | L1 | 9 | 356 |
| HPV56 | L1 | 10 | 356 |
| HPV56 | L1 | 8 | 17 |
| HPV56 | L1 | 10 | 17 |
| HPV56 | L1 | 11 | 17 |
| HPV56 | L1 | 10 | 138 |
| HPV56 | L1 | 8 | 118 |
| HPV56 | L1 | 8 | 150 |
| HPV56 | L1 | 11 | 150 |
| HPV56 | L1 | 10 | 438 |
| HPV56 | L1 | 8 | 144 |
| HPV56 | L1 | 9 | 399 |
| HPV56 | L1 | 10 | 399 |
| HPV56 | L1 | 11 | 399 |
| HPV56 | L1 | 9 | 96 |
| HPV56 | L1 | 11 | 96 |
| HPV56 | L1 | 8 | 192 |
| HPV56 | L1 | 8 | 258 |
| HPV56 | L1 | 11 | 258 |
| HPV56 | L1 | 9 | 392 |
| HPV56 | L1 | 8 | 413 |
| HPV56 | L1 | 9 | 413 |
| HPV56 | L1 | 10 | 413 |
| HPV56 | L1 | 11 | 413 |
| HPV56 | L1 | 11 | 270 |
| HPV56 | L1 | 8 | 343 |
| HPV56 | L1 | 8 | 470 |
| HPV56 | L1 | 10 | 470 |
| HPV56 | L1 | 11 | 470 |
| HPV56 | L1 | 8 | 186 |
| HPV56 | L1 | 8 | 300 |
| HPV56 | L1 | 10 | 300 |
| HPV56 | L1 | 11 | 300 |
| HPV56 | L1 | 8 | 245 |
| HPV56 | L1 | 10 | 245 |
| HPV56 | L1 | 9 | 98 |
| HPV56 | L1 | 10 | 98 |
| HPV56 | L1 | 8 | 55 |
| HPV56 | L1 | 9 | 55 |
| HPV56 | L1 | 9 | 45 |
| HPV56 | L1 | 11 | 224 |
| HPV56 | L1 | 8 | 77 |
| HPV56 | L1 | 9 | 77 |
| HPV56 | L1 | 11 | 77 |
| HPV56 | L1 | 9 | 431 |
| HPV56 | L1 | 11 | 502 |
| HPV56 | L1 | 9 | 111 |
| HPV56 | L1 | 9 | 48 |
| HPV56 | L1 | 10 | 48 |
| HPV56 | L1 | 11 | 48 |
| HPV56 | L1 | 9 | 484 |
| HPV56 | L1 | 8 | 247 |
| HPV56 | L1 | 10 | 247 |
| HPV56 | L1 | 10 | 405 |
| HPV56 | L1 | 11 | 347 |
| HPV56 | L1 | 8 | 132 |
| HPV56 | L1 | 10 | 132 |
| HPV56 | L1 | 8 | 234 |
| HPV56 | L1 | 9 | 234 |
| HPV56 | L1 | 11 | 234 |
| HPV56 | L1 | 8 | 333 |
| HPV56 | L1 | 9 | 333 |
| HPV56 | L1 | 8 | 2 |
| HPV56 | L1 | 8 | 1 |
| HPV56 | L1 | 9 | 1 |
| HPV56 | L1 | 10 | 5 |
| HPV56 | L1 | 10 | 503 |
| HPV56 | L1 | 11 | 503 |
| HPV56 | L1 | 8 | 436 |
| HPV56 | L1 | 9 | 436 |
| HPV56 | L1 | 8 | 95 |
| HPV56 | L1 | 10 | 95 |
| HPV56 | L1 | 11 | 180 |
| HPV56 | L1 | 10 | 123 |
| HPV56 | L1 | 11 | 123 |
| HPV56 | L1 | 8 | 167 |
| HPV56 | L1 | 8 | 430 |
| HPV56 | L1 | 10 | 430 |
| HPV56 | L1 | 10 | 483 |
| HPV56 | L1 | 10 | 426 |
| HPV56 | L1 | 11 | 375 |
| HPV56 | L1 | 8 | 126 |
| HPV56 | L1 | 9 | 126 |
| HPV56 | L1 | 10 | 126 |
| HPV56 | L1 | 8 | 361 |
| HPV56 | L1 | 10 | 394 |
| HPV56 | L1 | 9 | 28 |
| HPV56 | L1 | 10 | 28 |
| HPV56 | L1 | 10 | 172 |
| HPV56 | L1 | 8 | 228 |
| HPV56 | L1 | 9 | 31 |
| HPV56 | L1 | 8 | 473 |
| HPV56 | L1 | 10 | 473 |
| HPV56 | L1 | 9 | 221 |
| HPV56 | L1 | 11 | 255 |
| HPV56 | L1 | 11 | 146 |
| HPV56 | L1 | 8 | 496 |
| HPV56 | L1 | 10 | 496 |
| HPV56 | L1 | 8 | 13 |
| HPV56 | L1 | 9 | 13 |
| HPV56 | L1 | 10 | 13 |
| HPV56 | L1 | 11 | 4 |
| HPV56 | L1 | 10 | 220 |
| HPV56 | L1 | 9 | 12 |
| HPV56 | L1 | 10 | 12 |
| HPV56 | L1 | 11 | 12 |
| HPV56 | L1 | 8 | 319 |
| HPV56 | L1 | 9 | 319 |
| HPV56 | L1 | 8 | 320 |
| HPV56 | L1 | 9 | 466 |
| HPV56 | L1 | 10 | 466 |
| HPV56 | L1 | 8 | 49 |
| HPV56 | L1 | 9 | 49 |
| HPV56 | L1 | 10 | 49 |
| HPV56 | L1 | 11 | 441 |
| HPV56 | L1 | 10 | 442 |
| HPV56 | L1 | 11 | 52 |
| HPV56 | L1 | 10 | 189 |
| HPV56 | L1 | 11 | 189 |
| HPV56 | L1 | 9 | 410 |
| HPV56 | L1 | 11 | 410 |
| HPV56 | L1 | 8 | 288 |
| HPV56 | L1 | 11 | 288 |
| HPV56 | L1 | 8 | 339 |
| HPV56 | L1 | 9 | 339 |

TABLE XIV-continued

HLA-B62 Supermotif Peptides

| 1 | 2 | 3 | 4 |
|---|---|---|---|
| HPV56 | L1 | 9 | 504 |
| HPV56 | L1 | 10 | 504 |
| HPV56 | L1 | 11 | 504 |
| HPV56 | L1 | 10 | 384 |
| HPV56 | L1 | 10 | 465 |
| HPV56 | L1 | 11 | 465 |
| HPV56 | L1 | 10 | 213 |
| HPV56 | L1 | 11 | 213 |
| HPV56 | L1 | 10 | 159 |
| HPV56 | L1 | 11 | 159 |
| HPV56 | L1 | 9 | 76 |
| HPV56 | L1 | 10 | 76 |
| HPV56 | L1 | 8 | 110 |
| HPV56 | L1 | 10 | 110 |
| HPV56 | L1 | 9 | 131 |
| HPV56 | L1 | 11 | 131 |
| HPV56 | L1 | 8 | 40 |
| HPV56 | L1 | 9 | 40 |
| HPV56 | L1 | 10 | 108 |
| HPV56 | L1 | 11 | 67 |
| HPV56 | L1 | 8 | 446 |
| HPV56 | L1 | 9 | 446 |
| HPV56 | L1 | 9 | 332 |
| HPV56 | L1 | 10 | 332 |
| HPV56 | L1 | 11 | 279 |
| HPV56 | L1 | 8 | 440 |
| HPV56 | L1 | 9 | 182 |
| HPV56 | L1 | 11 | 182 |
| HPV56 | L1 | 11 | 86 |
| HPV56 | L1 | 11 | 323 |
| HPV56 | L1 | 8 | 304 |
| HPV56 | L1 | 9 | 377 |
| HPV56 | L1 | 8 | 415 |
| HPV56 | L1 | 9 | 415 |
| HPV56 | L1 | 10 | 415 |
| HPV56 | L1 | 8 | 196 |
| HPV56 | L1 | 8 | 227 |
| HPV56 | L1 | 9 | 227 |
| HPV56 | L1 | 11 | 328 |
| HPV56 | L1 | 8 | 51 |
| HPV56 | L1 | 11 | 188 |
| HPV56 | L1 | 11 | 212 |
| HPV56 | L1 | 11 | 366 |
| HPV56 | L1 | 9 | 173 |
| HPV56 | L1 | 11 | 173 |
| HPV56 | L1 | 9 | 246 |
| HPV56 | L1 | 11 | 246 |
| HPV56 | L1 | 8 | 420 |
| HPV56 | L1 | 10 | 420 |
| HPV56 | L1 | 10 | 259 |
| HPV56 | L1 | 11 | 259 |
| HPV56 | L1 | 8 | 56 |
| HPV56 | L1 | 10 | 367 |
| HPV56 | L1 | 8 | 7 |
| HPV56 | L1 | 10 | 7 |
| HPV56 | L1 | 9 | 423 |
| HPV56 | L1 | 10 | 423 |
| HPV56 | L1 | 8 | 268 |
| HPV56 | L1 | 9 | 268 |
| HPV56 | L1 | 10 | 47 |
| HPV56 | L1 | 11 | 47 |
| HPV56 | L1 | 8 | 396 |
| HPV56 | L1 | 10 | 396 |
| HPV56 | L1 | 8 | 283 |
| HPV56 | L1 | 9 | 283 |
| HPV56 | L1 | 9 | 265 |
| HPV56 | L1 | 11 | 265 |
| HPV56 | L1 | 8 | 102 |
| HPV56 | L1 | 10 | 102 |
| HPV56 | L1 | 9 | 325 |
| HPV56 | L1 | 10 | 325 |
| HPV56 | L1 | 8 | 62 |
| HPV56 | L1 | 9 | 62 |
| HPV56 | L1 | 11 | 62 |
| HPV56 | L2 | 8 | 438 |
| HPV56 | L2 | 9 | 271 |
| HPV56 | L2 | 10 | 271 |
| HPV56 | L2 | 11 | 271 |
| HPV56 | L2 | 9 | 358 |
| HPV56 | L2 | 10 | 358 |
| HPV56 | L2 | 11 | 391 |
| HPV56 | L2 | 11 | 170 |
| HPV56 | L2 | 8 | 223 |
| HPV56 | L2 | 9 | 223 |
| HPV56 | L2 | 8 | 327 |
| HPV56 | L2 | 11 | 327 |
| HPV56 | L2 | 10 | 201 |
| HPV56 | L2 | 9 | 27 |
| HPV56 | L2 | 8 | 322 |
| HPV56 | L2 | 11 | 322 |
| HPV56 | L2 | 9 | 142 |
| HPV56 | L2 | 11 | 142 |
| HPV56 | L2 | 11 | 406 |
| HPV56 | L2 | 10 | 349 |
| HPV56 | L2 | 9 | 238 |
| HPV56 | L2 | 11 | 238 |
| HPV56 | L2 | 8 | 273 |
| HPV56 | L2 | 9 | 273 |
| HPV56 | L2 | 10 | 273 |
| HPV56 | L2 | 8 | 100 |
| HPV56 | L2 | 8 | 425 |
| HPV56 | L2 | 9 | 83 |
| HPV56 | L2 | 10 | 83 |
| HPV56 | L2 | 11 | 83 |
| HPV56 | L2 | 11 | 30 |
| HPV56 | L2 | 9 | 429 |
| HPV56 | L2 | 10 | 429 |
| HPV56 | L2 | 11 | 429 |
| HPV56 | L2 | 8 | 331 |
| HPV56 | L2 | 10 | 331 |
| HPV56 | L2 | 8 | 194 |
| HPV56 | L2 | 9 | 194 |
| HPV56 | L2 | 11 | 129 |
| HPV56 | L2 | 8 | 333 |
| HPV56 | L2 | 8 | 208 |
| HPV56 | L2 | 11 | 208 |
| HPV56 | L2 | 9 | 36 |
| HPV56 | L2 | 10 | 36 |
| HPV56 | L2 | 8 | 175 |
| HPV56 | L2 | 9 | 162 |
| HPV56 | L2 | 8 | 241 |
| HPV56 | L2 | 9 | 241 |
| HPV56 | L2 | 11 | 241 |
| HPV56 | L2 | 11 | 276 |
| HPV56 | L2 | 10 | 231 |
| HPV56 | L2 | 11 | 231 |
| HPV56 | L2 | 9 | 418 |
| HPV56 | L2 | 8 | 188 |
| HPV56 | L2 | 10 | 188 |
| HPV56 | L2 | 11 | 118 |
| HPV56 | L2 | 8 | 360 |
| HPV56 | L2 | 9 | 346 |
| HPV56 | L2 | 8 | 412 |
| HPV56 | L2 | 8 | 97 |
| HPV56 | L2 | 10 | 97 |
| HPV56 | L2 | 11 | 97 |
| HPV56 | L2 | 8 | 269 |
| HPV56 | L2 | 9 | 269 |
| HPV56 | L2 | 11 | 269 |
| HPV56 | L2 | 11 | 293 |
| HPV56 | L2 | 8 | 156 |
| HPV56 | L2 | 9 | 372 |
| HPV56 | L2 | 11 | 372 |
| HPV56 | L2 | 11 | 151 |
| HPV56 | L2 | 10 | 180 |
| HPV56 | L2 | 8 | 44 |
| HPV56 | L2 | 10 | 44 |
| HPV56 | L2 | 11 | 44 |
| HPV56 | L2 | 8 | 215 |
| HPV56 | L2 | 9 | 215 |

TABLE XIV-continued

HLA-B62 Supermotif Peptides

| 1 | 2 | 3 | 4 |
|---|---|---|---|
| HPV56 | L2 | 8 | 195 |
| HPV56 | L2 | 10 | 119 |
| HPV56 | L2 | 10 | 453 |
| HPV56 | L2 | 11 | 453 |
| HPV56 | L2 | 8 | 432 |
| HPV56 | L2 | 9 | 432 |
| HPV56 | L2 | 11 | 432 |
| HPV56 | L2 | 9 | 305 |
| HPV56 | L2 | 11 | 305 |
| HPV56 | L2 | 8 | 279 |
| HPV56 | L2 | 9 | 279 |
| HPV56 | L2 | 11 | 81 |
| HPV56 | L2 | 10 | 407 |
| HPV56 | L2 | 10 | 103 |
| HPV56 | L2 | 11 | 103 |
| HPV56 | L2 | 8 | 34 |
| HPV56 | L2 | 11 | 34 |
| HPV56 | L2 | 8 | 43 |
| HPV56 | L2 | 9 | 43 |
| HPV56 | L2 | 11 | 43 |
| HPV56 | L2 | 10 | 22 |
| HPV56 | L2 | 11 | 22 |
| HPV56 | L2 | 8 | 376 |
| HPV56 | L2 | 8 | 235 |
| HPV56 | L2 | 9 | 181 |
| HPV56 | L2 | 8 | 337 |
| HPV56 | L2 | 11 | 337 |
| HPV56 | L2 | 8 | 373 |
| HPV56 | L2 | 10 | 373 |
| HPV56 | L2 | 11 | 373 |
| HPV56 | L2 | 8 | 409 |
| HPV56 | L2 | 10 | 409 |
| HPV56 | L2 | 11 | 409 |
| HPV56 | L2 | 9 | 45 |
| HPV56 | L2 | 10 | 45 |
| HPV56 | L2 | 8 | 106 |
| HPV56 | L2 | 8 | 248 |
| HPV56 | L2 | 9 | 248 |
| HPV56 | L2 | 11 | 334 |
| HPV56 | L2 | 9 | 353 |
| HPV56 | L2 | 11 | 179 |
| HPV56 | L2 | 9 | 278 |
| HPV56 | L2 | 10 | 278 |
| HPV56 | L2 | 11 | 253 |
| HPV56 | L2 | 9 | 159 |
| HPV56 | L2 | 10 | 159 |
| HPV56 | L2 | 9 | 388 |
| HPV56 | L2 | 10 | 388 |
| HPV56 | L2 | 8 | 395 |
| HPV56 | L2 | 8 | 325 |
| HPV56 | L2 | 10 | 325 |
| HPV56 | L2 | 9 | 374 |
| HPV56 | L2 | 10 | 374 |
| HPV56 | L2 | 8 | 214 |
| HPV56 | L2 | 9 | 214 |
| HPV56 | L2 | 10 | 214 |
| HPV56 | L2 | 10 | 209 |
| HPV56 | L2 | 10 | 254 |
| HPV56 | L2 | 11 | 254 |
| HPV56 | L2 | 8 | 160 |
| HPV56 | L2 | 9 | 160 |
| HPV56 | L2 | 11 | 160 |
| HPV56 | L2 | 10 | 392 |
| HPV56 | L2 | 11 | 392 |
| HPV56 | L2 | 9 | 73 |
| HPV56 | L2 | 10 | 73 |
| HPV56 | L2 | 9 | 336 |
| HPV56 | L2 | 8 | 89 |
| HPV56 | L2 | 11 | 420 |
| HPV56 | L2 | 10 | 171 |
| HPV56 | L2 | 11 | 171 |
| HPV56 | L2 | 11 | 166 |
| HPV56 | L2 | 8 | 312 |
| HPV56 | L2 | 9 | 312 |
| HPV56 | L2 | 10 | 312 |
| HPV56 | L2 | 8 | 16 |
| HPV56 | L2 | 10 | 335 |
| HPV56 | L2 | 9 | 232 |
| HPV56 | L2 | 10 | 232 |
| HPV56 | L2 | 11 | 232 |
| HPV56 | L2 | 8 | 233 |
| HPV56 | L2 | 9 | 233 |
| HPV56 | L2 | 10 | 233 |
| HPV56 | L2 | 8 | 220 |
| HPV56 | L2 | 11 | 220 |
| HPV56 | L2 | 11 | 452 |
| HPV56 | L2 | 8 | 298 |
| HPV56 | L2 | 10 | 225 |
| HPV56 | L2 | 11 | 284 |
| HPV56 | L2 | 8 | 244 |
| HPV56 | L2 | 9 | 88 |
| HPV56 | L2 | 8 | 77 |
| HPV56 | L2 | 11 | 77 |
| HPV56 | L2 | 8 | 316 |
| HPV56 | L2 | 11 | 316 |
| HPV56 | L2 | 11 | 102 |
| HPV56 | L2 | 9 | 262 |
| HPV56 | L2 | 10 | 262 |
| HPV56 | L2 | 9 | 49 |
| HPV56 | L2 | 11 | 49 |
| HPV56 | L2 | 9 | 324 |
| HPV56 | L2 | 11 | 324 |
| HPV56 | L2 | 11 | 266 |
| HPV56 | L2 | 9 | 422 |
| HPV56 | L2 | 10 | 422 |
| HPV56 | L2 | 11 | 422 |
| HPV56 | L2 | 9 | 363 |
| HPV56 | L2 | 11 | 363 |
| HPV56 | L2 | 9 | 365 |
| HPV56 | L2 | 11 | 365 |
| HPV56 | L2 | 9 | 95 |
| HPV56 | L2 | 10 | 95 |
| HPV56 | L2 | 9 | 111 |
| HPV56 | L2 | 10 | 304 |
| HPV56 | L2 | 8 | 80 |
| HPV56 | L2 | 11 | 379 |
| HPV56 | L2 | 8 | 105 |
| HPV56 | L2 | 9 | 105 |
| HPV56 | L2 | 9 | 247 |
| HPV56 | L2 | 10 | 247 |
| HPV56 | L2 | 8 | 85 |
| HPV56 | L2 | 9 | 85 |
| HPV56 | L2 | 9 | 399 |
| HPV56 | L2 | 10 | 399 |
| HPV56 | L2 | 11 | 399 |
| HPV56 | L2 | 9 | 213 |
| HPV56 | L2 | 10 | 213 |
| HPV56 | L2 | 11 | 213 |
| HPV56 | L2 | 8 | 368 |
| HPV56 | L2 | 9 | 184 |
| HPV56 | L2 | 9 | 144 |
| HPV56 | L2 | 9 | 311 |
| HPV56 | L2 | 10 | 311 |
| HPV56 | L2 | 11 | 311 |
| HPV56 | L2 | 9 | 15 |
| HPV56 | L2 | 9 | 149 |
| HPV56 | L2 | 10 | 167 |
| HPV56 | L2 | 8 | 112 |
| HPV56 | L2 | 11 | 112 |
| HPV56 | L2 | 11 | 140 |
| HPV56 | L2 | 9 | 408 |
| HPV56 | L2 | 11 | 408 |
| HPV56 | L2 | 10 | 72 |
| HPV56 | L2 | 11 | 72 |
| HPV56 | L2 | 8 | 419 |
| HPV56 | L2 | 10 | 31 |
| HPV56 | L2 | 11 | 31 |
| HPV56 | L2 | 9 | 416 |
| HPV56 | L2 | 11 | 416 |
| HPV56 | L2 | 8 | 431 |

TABLE XIV-continued

HLA-B62 Supermotif Peptides

| 1 | 2 | 3 | 4 |
|---|---|---|---|
| HPV56 | L2 | 9 | 431 |
| HPV56 | L2 | 10 | 431 |
| HPV56 | L2 | 11 | 71 |
| SF 1168123 v1 | | | |

TABLE XIV A

HPV6A
HLA-B62 Supermotif Peptides

| 2 | 3 | 4 |
|---|---|---|
| L2 | 9 | 286 |
| L2 | 11 | 286 |
| L2 | 10 | 112 |
| L2 | 11 | 112 |
| E1 | 11 | 112 |
| E1 | 11 | 22 |
| E2 | 10 | 250 |
| E4 | 8 | 14 |
| E1 | 11 | 520 |
| E1 | 10 | 207 |
| L1 | 8 | 81 |
| L2 | 8 | 421 |
| L2 | 9 | 421 |
| E6 | 8 | 37 |
| E6 | 10 | 37 |
| E5 | 8 | 79 |
| E5 | 9 | 79 |
| E1 | 9 | 319 |
| L2 | 9 | 271 |
| L2 | 10 | 271 |
| E1 | 10 | 337 |
| E1 | 11 | 337 |
| E2 | 8 | 326 |
| E2 | 10 | 326 |
| L2 | 10 | 410 |
| L1 | 8 | 158 |
| L2 | 9 | 217 |
| L2 | 8 | 98 |
| L2 | 11 | 98 |
| L2 | 9 | 182 |
| L2 | 9 | 327 |
| L2 | 8 | 341 |
| L2 | 9 | 341 |
| L1 | 8 | 312 |
| L1 | 10 | 312 |
| L1 | 8 | 300 |
| L1 | 9 | 300 |
| E4 | 10 | 3 |
| L1 | 9 | 43 |
| E1 | 10 | 601 |
| E6 | 8 | 67 |
| E6 | 11 | 67 |
| E6 | 9 | 137 |
| E2 | 10 | 35 |
| E5 | 9 | 77 |
| E5 | 10 | 77 |
| E5 | 11 | 77 |
| L2 | 9 | 27 |
| L1 | 10 | 181 |
| L1 | 11 | 181 |
| E1 | 10 | 560 |
| E2 | 9 | 11 |
| E2 | 8 | 252 |
| E4 | 9 | 64 |
| E4 | 11 | 64 |
| E1 | 8 | 369 |
| E1 | 10 | 369 |
| L1 | 9 | 219 |
| L2 | 10 | 278 |
| E6 | 10 | 96 |
| L2 | 9 | 356 |
| L2 | 9 | 404 |
| E1 | 8 | 570 |
| E1 | 10 | 570 |
| L2 | 11 | 347 |
| L2 | 10 | 396 |
| E2 | 9 | 313 |
| E1 | 11 | 81 |
| E2 | 9 | 25 |
| L1 | 11 | 366 |
| E7 | 8 | 14 |
| L1 | 9 | 208 |
| L1 | 11 | 208 |
| E1 | 10 | 203 |
| E1 | 11 | 46 |
| L1 | 10 | 195 |
| L2 | 8 | 101 |
| L1 | 8 | 89 |
| L1 | 9 | 89 |
| E7 | 8 | 19 |
| L1 | 8 | 236 |
| L1 | 9 | 236 |
| L1 | 10 | 236 |
| L1 | 8 | 434 |
| L1 | 9 | 434 |
| L1 | 11 | 434 |
| L2 | 11 | 42 |
| E6 | 11 | 14 |
| L1 | 9 | 455 |
| L2 | 11 | 30 |
| L2 | 11 | 258 |
| E2 | 10 | 136 |
| E2 | 11 | 136 |
| L2 | 8 | 332 |
| L2 | 8 | 192 |
| L2 | 9 | 192 |
| E1 | 9 | 105 |
| L2 | 10 | 120 |
| L1 | 11 | 453 |
| E1 | 10 | 604 |
| E1 | 11 | 604 |
| E1 | 9 | 131 |
| E1 | 10 | 417 |
| E1 | 11 | 417 |
| E1 | 11 | 360 |
| E2 | 11 | 100 |
| L2 | 11 | 354 |
| E1 | 9 | 257 |
| E1 | 11 | 257 |
| E1 | 9 | 309 |
| L2 | 11 | 162 |
| L2 | 10 | 95 |
| L2 | 11 | 95 |
| L1 | 8 | 265 |
| L1 | 9 | 265 |
| E2 | 10 | 90 |
| E7 | 11 | 27 |
| L1 | 8 | 249 |
| L1 | 9 | 249 |
| E2 | 9 | 341 |
| E2 | 10 | 341 |
| E2 | 8 | 185 |
| E2 | 9 | 185 |
| E1 | 10 | 141 |
| E1 | 9 | 39 |
| E1 | 10 | 39 |
| E6 | 8 | 113 |
| L1 | 11 | 262 |
| L1 | 10 | 103 |
| L1 | 9 | 381 |
| L1 | 8 | 443 |
| E2 | 10 | 205 |
| E1 | 8 | 220 |
| L1 | 8 | 369 |

TABLE XIV A-continued

HPV6A
HLA-B62 Supermotif Peptides

| 2 | 3 | 4 |
|---|---|---|
| E6 | 8 | 126 |
| E1 | 8 | 454 |
| E1 | 11 | 454 |
| L2 | 8 | 428 |
| E5 | 9 | 40 |
| E1 | 10 | 494 |
| E5 | 9 | 68 |
| L1 | 8 | 119 |
| E1 | 10 | 393 |
| E1 | 11 | 393 |
| E2 | 11 | 346 |
| L2 | 8 | 398 |
| L2 | 10 | 398 |
| E1 | 9 | 446 |
| E1 | 10 | 446 |
| L1 | 8 | 245 |
| E1 | 8 | 457 |
| L2 | 9 | 239 |
| L2 | 11 | 239 |
| E1 | 10 | 593 |
| E1 | 11 | 593 |
| L2 | 10 | 407 |
| E2 | 11 | 290 |
| E1 | 11 | 252 |
| E1 | 11 | 127 |
| E2 | 8 | 171 |
| E5 | 8 | 28 |
| E5 | 9 | 28 |
| E5 | 10 | 28 |
| E5 | 8 | 24 |
| E5 | 9 | 24 |
| E5 | 11 | 24 |
| L1 | 9 | 318 |
| L1 | 10 | 318 |
| E1 | 10 | 243 |
| E1 | 8 | 326 |
| E1 | 9 | 326 |
| E2 | 9 | 156 |
| E7 | 9 | 22 |
| E1 | 8 | 217 |
| E1 | 11 | 217 |
| E2 | 9 | 50 |
| E2 | 10 | 50 |
| L2 | 8 | 292 |
| L2 | 10 | 223 |
| L1 | 11 | 144 |
| E2 | 10 | 55 |
| E1 | 8 | 273 |
| E1 | 10 | 273 |
| L2 | 11 | 402 |
| L2 | 8 | 85 |
| L2 | 9 | 85 |
| L2 | 10 | 85 |
| E1 | 9 | 478 |
| E1 | 10 | 478 |
| L2 | 8 | 206 |
| E2 | 11 | 257 |
| L2 | 10 | 425 |
| L2 | 11 | 425 |
| L1 | 8 | 136 |
| L1 | 10 | 136 |
| E7 | 11 | 42 |
| E1 | 10 | 162 |
| E2 | 8 | 162 |
| E2 | 10 | 162 |
| E2 | 11 | 162 |
| L1 | 8 | 107 |
| E1 | 8 | 316 |
| L2 | 9 | 51 |
| L1 | 9 | 111 |
| L1 | 11 | 113 |
| L2 | 8 | 312 |
| L2 | 9 | 312 |
| L2 | 10 | 312 |
| L2 | 9 | 177 |
| E6 | 8 | 119 |
| E6 | 9 | 119 |
| E1 | 9 | 264 |
| E1 | 11 | 264 |
| E4 | 8 | 59 |
| E2 | 10 | 78 |
| E2 | 10 | 310 |
| E4 | 10 | 10 |
| L1 | 10 | 117 |
| L2 | 11 | 188 |
| L2 | 11 | 336 |
| L2 | 10 | 362 |
| E1 | 9 | 449 |
| L2 | 10 | 230 |
| L1 | 9 | 361 |
| L1 | 10 | 361 |
| L1 | 11 | 361 |
| E2 | 8 | 29 |
| E1 | 8 | 502 |
| E1 | 9 | 502 |
| E7 | 8 | 5 |
| E5 | 8 | 21 |
| E5 | 9 | 21 |
| E5 | 11 | 21 |
| L1 | 11 | 272 |
| E5 | 10 | 31 |
| E5 | 11 | 31 |
| L2 | 9 | 113 |
| L2 | 10 | 113 |
| L2 | 9 | 279 |
| E6 | 9 | 97 |
| L2 | 8 | 178 |
| E5 | 9 | 32 |
| E5 | 10 | 32 |
| E5 | 11 | 32 |
| L2 | 9 | 44 |
| L2 | 10 | 44 |
| L2 | 11 | 44 |
| E5 | 8 | 17 |
| E5 | 9 | 17 |
| E5 | 10 | 17 |
| E6 | 8 | 120 |
| E1 | 8 | 301 |
| E1 | 10 | 455 |
| L2 | 9 | 32 |
| L2 | 8 | 193 |
| L2 | 8 | 450 |
| E2 | 11 | 352 |
| L1 | 11 | 191 |
| E1 | 9 | 313 |
| E1 | 10 | 313 |
| E1 | 11 | 313 |
| E1 | 8 | 265 |
| E1 | 10 | 265 |
| E1 | 11 | 265 |
| E1 | 11 | 476 |
| E7 | 11 | 11 |
| L2 | 9 | 121 |
| L2 | 11 | 121 |
| E1 | 10 | 443 |
| E1 | 10 | 23 |
| L2 | 10 | 104 |
| L2 | 11 | 104 |
| E5 | 8 | 34 |
| E5 | 9 | 34 |
| E5 | 10 | 34 |
| E5 | 8 | 41 |
| E1 | 8 | 433 |
| E1 | 11 | 433 |
| E6 | 8 | 73 |
| E6 | 10 | 73 |
| E1 | 10 | 312 |
| E1 | 11 | 312 |

TABLE XIV A-continued

HPV6A
HLA-B62 Supermotif Peptides

| 2 | 3 | 4 |
|---|---|---|
| E1 | 9 | 254 |
| E1 | 8 | 357 |
| E1 | 10 | 357 |
| L2 | 10 | 22 |
| L2 | 11 | 22 |
| E1 | 9 | 114 |
| E1 | 8 | 420 |
| L1 | 10 | 432 |
| L1 | 11 | 432 |
| E6 | 9 | 109 |
| L2 | 9 | 79 |
| L1 | 8 | 169 |
| E6 | 9 | 94 |
| E6 | 11 | 49 |
| E2 | 8 | 47 |
| E2 | 10 | 47 |
| L1 | 8 | 148 |
| E2 | 11 | 182 |
| E1 | 11 | 424 |
| L2 | 11 | 34 |
| E2 | 11 | 147 |
| E6 | 11 | 116 |
| E6 | 8 | 52 |
| E6 | 10 | 52 |
| E1 | 9 | 283 |
| E2 | 11 | 63 |
| L1 | 9 | 61 |
| L1 | 10 | 61 |
| L1 | 8 | 19 |
| L1 | 9 | 19 |
| L1 | 10 | 71 |
| L2 | 8 | 107 |
| E1 | 8 | 255 |
| E1 | 11 | 255 |
| E1 | 11 | 307 |
| E1 | 9 | 557 |
| E5 | 9 | 16 |
| E5 | 10 | 16 |
| E5 | 11 | 16 |
| E1 | 9 | 491 |
| E1 | 10 | 491 |
| E2 | 8 | 314 |
| L1 | 11 | 186 |
| L2 | 8 | 246 |
| L2 | 9 | 246 |
| E5 | 8 | 33 |
| E5 | 9 | 33 |
| E5 | 10 | 33 |
| E5 | 11 | 33 |
| L1 | 8 | 41 |
| L1 | 9 | 41 |
| L1 | 11 | 41 |
| E1 | 10 | 521 |
| E1 | 11 | 521 |
| E1 | 9 | 540 |
| E1 | 9 | 208 |
| E7 | 8 | 83 |
| E7 | 11 | 83 |
| E2 | 8 | 82 |
| E2 | 11 | 82 |
| E7 | 8 | 82 |
| E7 | 9 | 82 |
| E5 | 9 | 59 |
| E5 | 10 | 59 |
| E5 | 8 | 51 |
| E1 | 9 | 298 |
| E1 | 11 | 298 |
| E5 | 8 | 69 |
| E5 | 8 | 60 |
| E5 | 9 | 60 |
| E5 | 10 | 72 |
| E5 | 11 | 72 |
| E1 | 9 | 276 |
| E1 | 9 | 563 |

TABLE XIV A-continued

HPV6A
HLA-B62 Supermotif Peptides

| 2 | 3 | 4 |
|---|---|---|
| E2 | 8 | 42 |
| L2 | 8 | 422 |
| E5 | 8 | 18 |
| E5 | 9 | 18 |
| E5 | 11 | 18 |
| E2 | 8 | 94 |
| E2 | 9 | 94 |
| E5 | 10 | 65 |
| L1 | 10 | 367 |
| L1 | 11 | 309 |
| L1 | 8 | 231 |
| E1 | 9 | 511 |
| L2 | 9 | 399 |
| L1 | 11 | 465 |
| L1 | 8 | 209 |
| L1 | 10 | 209 |
| L2 | 9 | 338 |
| L2 | 11 | 338 |
| E5 | 9 | 73 |
| E5 | 10 | 73 |
| E7 | 9 | 29 |
| E5 | 8 | 47 |
| E1 | 8 | 277 |
| L1 | 9 | 295 |
| E1 | 8 | 564 |
| E7 | 10 | 67 |
| L1 | 10 | 95 |
| E1 | 8 | 306 |
| E2 | 9 | 56 |
| E2 | 8 | 151 |
| E2 | 9 | 151 |
| E1 | 10 | 47 |
| L1 | 9 | 196 |
| L1 | 11 | 196 |
| E1 | 9 | 274 |
| E1 | 11 | 274 |
| E1 | 10 | 361 |
| E1 | 10 | 568 |
| E1 | 11 | 451 |
| E1 | 9 | 300 |
| E1 | 8 | 539 |
| E1 | 10 | 539 |
| E6 | 9 | 21 |
| L1 | 8 | 337 |
| L1 | 8 | 134 |
| L1 | 10 | 134 |
| L1 | 8 | 390 |
| L1 | 10 | 390 |
| L2 | 10 | 358 |
| L2 | 9 | 157 |
| L2 | 9 | 251 |
| L2 | 11 | 251 |
| L1 | 8 | 323 |
| E1 | 10 | 304 |
| E6 | 8 | 75 |
| E6 | 11 | 75 |
| E2 | 9 | 348 |
| L2 | 9 | 325 |
| L2 | 11 | 325 |
| L1 | 11 | 217 |
| L2 | 10 | 189 |
| L2 | 11 | 189 |
| E1 | 9 | 94 |
| E1 | 11 | 442 |
| E6 | 8 | 110 |
| E6 | 11 | 110 |
| L1 | 8 | 183 |
| L1 | 9 | 183 |
| L2 | 10 | 73 |
| L1 | 11 | 109 |
| E7 | 8 | 47 |
| E7 | 9 | 47 |
| E1 | 8 | 562 |
| E1 | 10 | 562 |

TABLE XIV A-continued

HPV6A
HLA-B62 Supermotif Peptides

| 2 | 3 | 4 |
|---|---|---|
| E5 | 11 | 64 |
| E1 | 8 | 258 |
| E1 | 10 | 258 |
| L2 | 10 | 389 |
| L2 | 10 | 337 |
| L2 | 8 | 86 |
| L2 | 9 | 86 |
| L2 | 9 | 411 |
| L2 | 9 | 123 |
| E7 | 10 | 17 |
| E1 | 8 | 479 |
| E1 | 9 | 479 |
| E1 | 11 | 479 |
| L2 | 8 | 28 |
| E1 | 8 | 310 |
| L1 | 9 | 182 |
| L1 | 10 | 182 |
| E1 | 9 | 561 |
| E1 | 11 | 561 |
| L1 | 10 | 404 |
| L1 | 8 | 13 |
| L1 | 9 | 13 |
| L1 | 11 | 403 |
| L1 | 9 | 12 |
| L1 | 10 | 12 |
| E2 | 9 | 235 |
| E2 | 10 | 353 |
| E2 | 11 | 353 |
| L2 | 9 | 170 |
| L2 | 11 | 170 |
| L2 | 8 | 90 |
| L2 | 11 | 168 |
| L2 | 11 | 243 |
| L2 | 9 | 96 |
| L2 | 10 | 96 |
| E2 | 10 | 258 |
| L2 | 8 | 171 |
| L2 | 10 | 171 |
| L2 | 9 | 426 |
| L2 | 10 | 426 |
| L2 | 8 | 158 |
| E7 | 11 | 20 |
| E5 | 8 | 19 |
| E5 | 10 | 19 |
| E5 | 11 | 19 |
| L1 | 8 | 266 |
| L2 | 11 | 212 |
| L1 | 11 | 16 |
| E2 | 11 | 222 |
| L2 | 10 | 418 |
| L2 | 11 | 418 |
| L2 | 9 | 363 |
| L2 | 8 | 252 |
| L2 | 10 | 252 |
| E5 | 11 | 7 |
| L2 | 10 | 43 |
| L2 | 11 | 43 |
| E1 | 10 | 31 |
| E6 | 10 | 15 |
| L1 | 11 | 372 |
| L1 | 8 | 301 |
| E6 | 10 | 50 |
| E7 | 9 | 81 |
| E7 | 10 | 81 |
| E7 | 10 | 28 |
| E4 | 9 | 4 |
| L1 | 8 | 250 |
| E2 | 9 | 48 |
| E2 | 11 | 48 |
| E1 | 9 | 305 |
| E1 | 10 | 527 |
| E1 | 11 | 527 |
| E1 | 10 | 118 |
| E7 | 9 | 46 |

TABLE XIV A-continued

HPV6A
HLA-B62 Supermotif Peptides

| 2 | 3 | 4 |
|---|---|---|
| E7 | 10 | 46 |
| E1 | 8 | 512 |
| E7 | 11 | 16 |
| L2 | 10 | 169 |
| L2 | 8 | 381 |
| E2 | 9 | 344 |
| E7 | 10 | 80 |
| E7 | 11 | 80 |
| E2 | 10 | 244 |
| L2 | 9 | 231 |
| E2 | 8 | 57 |
| L2 | 8 | 298 |
| L2 | 8 | 316 |
| L2 | 11 | 316 |
| L2 | 9 | 449 |
| L1 | 11 | 241 |
| L2 | 9 | 245 |
| L2 | 10 | 245 |
| L1 | 9 | 40 |
| L1 | 10 | 40 |
| E2 | 10 | 303 |
| E1 | 8 | 616 |
| E7 | 11 | 66 |
| L1 | 11 | 94 |
| L2 | 11 | 284 |
| L2 | 9 | 89 |
| L1 | 8 | 3 |
| L1 | 9 | 3 |
| E1 | 8 | 69 |
| E1 | 11 | 69 |
| E1 | 11 | 117 |
| E2 | 8 | 343 |
| E2 | 10 | 343 |
| L1 | 8 | 140 |
| E1 | 11 | 583 |
| L2 | 8 | 153 |
| L2 | 10 | 267 |
| L2 | 11 | 267 |
| E5 | 8 | 30 |
| E5 | 11 | 30 |
| L1 | 9 | 50 |
| L1 | 10 | 50 |
| E2 | 8 | 207 |
| L1 | 11 | 474 |
| E1 | 10 | 247 |
| L1 | 8 | 375 |
| L1 | 9 | 375 |
| L1 | 11 | 375 |
| L2 | 11 | 103 |
| E1 | 8 | 60 |
| L1 | 11 | 86 |
| L2 | 11 | 49 |
| L2 | 8 | 106 |
| L2 | 9 | 106 |
| E1 | 10 | 490 |
| E1 | 11 | 490 |
| E2 | 9 | 81 |
| L1 | 10 | 294 |
| E1 | 8 | 260 |
| E6 | 10 | 23 |
| E6 | 11 | 23 |
| L2 | 10 | 304 |
| E2 | 8 | 150 |
| E2 | 9 | 150 |
| E2 | 10 | 150 |
| E2 | 8 | 246 |
| E2 | 11 | 246 |
| L2 | 10 | 324 |
| E1 | 10 | 93 |
| E2 | 10 | 323 |
| E2 | 11 | 323 |
| L2 | 11 | 417 |
| E1 | 10 | 89 |
| E1 | 11 | 635 |

TABLE XIV A-continued

HPV6A
HLA-B62 Supermotif Peptides

| 2 | 3 | 4 |
|---|---|---|
| E1 | 8 | 354 |
| E1 | 9 | 354 |
| E1 | 11 | 354 |
| E7 | 8 | 45 |
| E7 | 10 | 45 |
| E7 | 11 | 45 |
| L1 | 8 | 281 |
| L1 | 8 | 189 |
| L1 | 9 | 189 |
| L1 | 8 | 392 |
| E2 | 10 | 40 |
| E5 | 10 | 45 |
| L2 | 9 | 260 |
| E1 | 11 | 185 |
| E2 | 9 | 198 |
| E2 | 11 | 198 |
| L2 | 9 | 164 |
| L2 | 10 | 145 |
| L2 | 11 | 145 |
| L1 | 8 | 343 |
| L2 | 9 | 39 |
| E1 | 10 | 97 |
| E6 | 9 | 12 |
| E2 | 8 | 355 |
| E2 | 9 | 355 |
| L2 | 10 | 184 |
| E1 | 8 | 294 |
| E7 | 8 | 86 |
| L1 | 8 | 408 |
| L1 | 9 | 408 |
| E1 | 10 | 556 |
| E5 | 8 | 15 |
| E5 | 10 | 15 |
| E5 | 11 | 15 |
| E5 | 9 | 50 |
| E1 | 10 | 297 |
| E5 | 11 | 71 |
| E2 | 9 | 93 |
| E2 | 10 | 93 |
| E6 | 8 | 26 |
| L1 | 9 | 377 |
| L1 | 10 | 377 |
| E1 | 11 | 408 |
| E2 | 10 | 128 |
| E2 | 11 | 128 |
| L1 | 10 | 388 |
| L2 | 9 | 138 |
| E2 | 9 | 215 |
| E4 | 11 | 62 |
| L1 | 10 | 427 |
| E1 | 9 | 468 |
| E1 | 10 | 468 |
| L2 | 9 | 375 |
| E2 | 10 | 234 |
| L2 | 8 | 242 |
| L2 | 8 | 360 |
| E1 | 11 | 30 |
| E1 | 8 | 526 |
| E1 | 11 | 526 |
| L2 | 9 | 380 |
| E1 | 8 | 148 |
| E6 | 10 | 88 |
| E4 | 11 | 73 |
| E2 | 9 | 191 |
| E1 | 9 | 332 |
| E1 | 10 | 332 |
| E1 | 9 | 78 |
| L2 | 11 | 378 |
| L1 | 11 | 328 |
| L1 | 9 | 57 |
| L1 | 11 | 57 |
| L1 | 10 | 8 |
| E2 | 8 | 192 |
| E1 | 11 | 346 |

TABLE XIV A-continued

HPV6A
HLA-B62 Supermotif Peptides

| 2 | 3 | 4 |
|---|---|---|
| E1 | 8 | 333 |
| E1 | 9 | 333 |
| E5 | 9 | 20 |
| E5 | 10 | 20 |
| L2 | 10 | 31 |
| L1 | 8 | 190 |
| E1 | 11 | 499 |
| E7 | 10 | 12 |
| E6 | 9 | 53 |
| E1 | 8 | 275 |
| E1 | 10 | 275 |
| E2 | 9 | 41 |
| L1 | 8 | 73 |
| E5 | 11 | 48 |
| E5 | 9 | 46 |
| L1 | 8 | 382 |
| L2 | 10 | 213 |
| L1 | 9 | 59 |
| L1 | 11 | 59 |
| L2 | 11 | 72 |
| L2 | 11 | 388 |
| L2 | 8 | 122 |
| L2 | 10 | 122 |
| L1 | 10 | 11 |
| L1 | 11 | 11 |
| E7 | 8 | 69 |
| E7 | 11 | 69 |
| E1 | 8 | 79 |
| E2 | 8 | 139 |
| E2 | 10 | 139 |
| E1 | 9 | 444 |
| E1 | 11 | 444 |
| L2 | 8 | 261 |
| E1 | 9 | 24 |
| E7 | 11 | 79 |
| E2 | 11 | 243 |
| L2 | 8 | 232 |
| E1 | 9 | 362 |
| E1 | 11 | 238 |
| L1 | 8 | 20 |
| E5 | 8 | 25 |
| E5 | 10 | 25 |
| E5 | 11 | 25 |
| L1 | 10 | 329 |
| E2 | 8 | 349 |
| L1 | 9 | 72 |
| L1 | 8 | 58 |
| L1 | 10 | 58 |
| E7 | 9 | 68 |
| E2 | 8 | 132 |
| E1 | 9 | 426 |
| E5 | 8 | 36 |
| E5 | 11 | 36 |
| E1 | 8 | 340 |
| E1 | 8 | 530 |
| E1 | 11 | 464 |
| E5 | 10 | 58 |
| E5 | 11 | 58 |
| E1 | 10 | 510 |
| E1 | 8 | 267 |
| E1 | 9 | 267 |
| E4 | 9 | 66 |
| E2 | 9 | 102 |
| E2 | 8 | 145 |
| E1 | 8 | 237 |
| L1 | 9 | 385 |
| E4 | 8 | 12 |
| E4 | 10 | 12 |
| E6 | 10 | 105 |
| E1 | 10 | 86 |
| L2 | 8 | 435 |
| E1 | 9 | 579 |
| E1 | 11 | 579 |
| L1 | 9 | 230 |

TABLE XIV A-continued

HPV6A
HLA-B62 Supermotif Peptides

| 2 | 3 | 4 |
|---|---|---|
| L2 | 9 | 371 |
| L1 | 8 | 358 |
| E1 | 11 | 536 |
| L1 | 8 | 65 |
| L1 | 9 | 65 |
| E1 | 8 | 402 |
| E2 | 11 | 168 |
| L1 | 10 | 287 |
| L1 | 8 | 10 |
| L1 | 11 | 10 |
| E2 | 8 | 138 |
| E2 | 9 | 138 |
| E2 | 11 | 138 |
| E1 | 8 | 91 |
| L1 | 8 | 26 |
| L1 | 9 | 26 |
| E2 | 8 | 131 |
| E2 | 9 | 131 |

TABLE XIV B

HPV6B
HLA-B62 Supermotif Peptides

| 2 | 3 | 4 |
|---|---|---|
| L2 | 9 | 286 |
| L2 | 11 | 286 |
| L2 | 10 | 112 |
| L2 | 11 | 112 |
| E1 | 11 | 112 |
| E1 | 11 | 22 |
| E2 | 10 | 250 |
| E4 | 8 | 24 |
| E1 | 11 | 520 |
| E1 | 10 | 207 |
| L1 | 8 | 81 |
| L2 | 8 | 421 |
| L2 | 9 | 421 |
| E6 | 8 | 37 |
| E6 | 10 | 37 |
| E5A | 8 | 79 |
| E5A | 9 | 79 |
| E1 | 9 | 319 |
| L2 | 9 | 271 |
| L2 | 10 | 271 |
| E1 | 10 | 337 |
| E1 | 11 | 337 |
| E2 | 8 | 326 |
| E2 | 10 | 326 |
| L2 | 10 | 409 |
| E4 | 8 | 3 |
| E4 | 9 | 3 |
| L1 | 8 | 158 |
| L2 | 9 | 217 |
| L2 | 8 | 98 |
| L2 | 11 | 98 |
| L2 | 9 | 182 |
| L2 | 9 | 327 |
| L2 | 8 | 341 |
| L2 | 9 | 341 |
| L1 | 8 | 312 |
| L1 | 10 | 312 |
| L1 | 8 | 300 |
| L1 | 9 | 300 |
| E4 | 10 | 13 |
| L1 | 9 | 43 |
| E1 | 10 | 601 |
| E1 | 9 | 234 |
| E1 | 11 | 234 |
| E6 | 8 | 67 |

TABLE XIV B-continued

HPV6B
HLA-B62 Supermotif Peptides

| 2 | 3 | 4 |
|---|---|---|
| E6 | 11 | 67 |
| E6 | 9 | 137 |
| E2 | 10 | 35 |
| E5A | 8 | 77 |
| E5A | 9 | 77 |
| E5A | 10 | 77 |
| E5A | 11 | 77 |
| L2 | 9 | 27 |
| L1 | 10 | 181 |
| L1 | 11 | 181 |
| E1 | 10 | 560 |
| E2 | 9 | 11 |
| E5B | 9 | 5 |
| E2 | 8 | 252 |
| E4 | 9 | 74 |
| E4 | 11 | 74 |
| E1 | 8 | 369 |
| E1 | 10 | 369 |
| L1 | 9 | 219 |
| L2 | 10 | 278 |
| E6 | 10 | 96 |
| L2 | 9 | 403 |
| E1 | 8 | 570 |
| E1 | 10 | 570 |
| L2 | 11 | 347 |
| L2 | 10 | 395 |
| E2 | 9 | 25 |
| E2 | 9 | 313 |
| E1 | 11 | 81 |
| L1 | 11 | 366 |
| E7 | 8 | 14 |
| L1 | 9 | 208 |
| L1 | 11 | 208 |
| E1 | 10 | 203 |
| E1 | 11 | 46 |
| L1 | 10 | 195 |
| L2 | 8 | 101 |
| L1 | 8 | 89 |
| L1 | 9 | 89 |
| E7 | 8 | 19 |
| L1 | 8 | 236 |
| L1 | 9 | 236 |
| L1 | 10 | 236 |
| L1 | 8 | 434 |
| L1 | 9 | 434 |
| L1 | 11 | 434 |
| L2 | 11 | 42 |
| E6 | 11 | 14 |
| L1 | 9 | 455 |
| L2 | 11 | 30 |
| L2 | 11 | 258 |
| E2 | 9 | 348 |
| E2 | 10 | 136 |
| E2 | 11 | 136 |
| L2 | 8 | 332 |
| L2 | 8 | 192 |
| L2 | 9 | 192 |
| E1 | 9 | 105 |
| L2 | 10 | 120 |
| L1 | 11 | 453 |
| E1 | 10 | 604 |
| E1 | 11 | 604 |
| E1 | 9 | 131 |
| E1 | 10 | 417 |
| E1 | 11 | 417 |
| E1 | 11 | 360 |
| E2 | 11 | 100 |
| L2 | 11 | 354 |
| E1 | 9 | 257 |
| E1 | 11 | 257 |
| E1 | 9 | 309 |
| L2 | 11 | 162 |
| L2 | 10 | 95 |
| L2 | 11 | 95 |

TABLE XIV B-continued

HPV6B
HLA-B62 Supermotif Peptides

| 2 | 3 | 4 |
|---|---|---|
| L1 | 8 | 265 |
| L1 | 9 | 265 |
| E2 | 10 | 90 |
| E7 | 11 | 27 |
| L1 | 8 | 249 |
| L1 | 9 | 249 |
| E2 | 9 | 341 |
| E2 | 10 | 341 |
| E2 | 8 | 185 |
| E2 | 9 | 185 |
| E1 | 10 | 141 |
| E1 | 9 | 39 |
| E1 | 10 | 39 |
| E6 | 8 | 113 |
| L1 | 11 | 262 |
| L1 | 10 | 103 |
| L1 | 9 | 381 |
| L1 | 8 | 443 |
| E2 | 10 | 205 |
| E1 | 8 | 220 |
| L1 | 8 | 369 |
| E6 | 8 | 126 |
| E5A | 9 | 16 |
| E5A | 10 | 16 |
| E5A | 11 | 16 |
| E1 | 8 | 454 |
| E1 | 11 | 454 |
| L2 | 8 | 428 |
| E5B | 11 | 22 |
| E5A | 9 | 40 |
| E2 | 11 | 346 |
| E1 | 10 | 494 |
| E5A | 9 | 68 |
| L1 | 8 | 119 |
| E1 | 10 | 393 |
| E1 | 11 | 393 |
| L2 | 8 | 397 |
| L2 | 10 | 397 |
| E1 | 9 | 446 |
| E1 | 10 | 446 |
| L1 | 8 | 245 |
| L2 | 9 | 239 |
| L2 | 11 | 239 |
| E1 | 8 | 457 |
| E1 | 10 | 593 |
| E1 | 11 | 593 |
| L2 | 10 | 406 |
| E2 | 11 | 290 |
| E1 | 11 | 252 |
| E1 | 11 | 127 |
| E2 | 8 | 171 |
| E5A | 8 | 28 |
| E5A | 9 | 28 |
| E5A | 10 | 28 |
| E5A | 8 | 24 |
| E5A | 9 | 24 |
| E5A | 11 | 24 |
| L1 | 9 | 318 |
| L1 | 10 | 318 |
| E1 | 10 | 243 |
| L2 | 9 | 356 |
| E1 | 8 | 326 |
| E1 | 9 | 326 |
| E2 | 9 | 156 |
| E7 | 9 | 22 |
| E5B | 10 | 28 |
| E1 | 8 | 217 |
| E1 | 11 | 217 |
| E2 | 9 | 50 |
| E2 | 10 | 50 |
| L2 | 8 | 292 |
| E5B | 8 | 15 |
| E5B | 9 | 15 |
| E5B | 10 | 15 |

TABLE XIV B-continued

HPV6B
HLA-B62 Supermotif Peptides

| 2 | 3 | 4 |
|---|---|---|
| L2 | 10 | 223 |
| L1 | 11 | 144 |
| E5B | 8 | 25 |
| E5B | 10 | 25 |
| E2 | 10 | 55 |
| E1 | 10 | 273 |
| L2 | 11 | 401 |
| L2 | 8 | 85 |
| L2 | 9 | 85 |
| L2 | 10 | 85 |
| E1 | 9 | 478 |
| E1 | 10 | 478 |
| L2 | 8 | 206 |
| E2 | 11 | 257 |
| L2 | 10 | 425 |
| L2 | 11 | 425 |
| L1 | 8 | 136 |
| L1 | 10 | 136 |
| E7 | 11 | 42 |
| E1 | 10 | 162 |
| E2 | 8 | 162 |
| E2 | 10 | 162 |
| E2 | 11 | 162 |
| L1 | 8 | 107 |
| E1 | 8 | 316 |
| L2 | 9 | 51 |
| L1 | 9 | 111 |
| L1 | 11 | 113 |
| L2 | 8 | 312 |
| L2 | 9 | 312 |
| L2 | 10 | 312 |
| L2 | 9 | 177 |
| E6 | 8 | 119 |
| E6 | 9 | 119 |
| E1 | 9 | 264 |
| E1 | 11 | 264 |
| E2 | 10 | 78 |
| E2 | 10 | 310 |
| E6 | 10 | 50 |
| E4 | 10 | 20 |
| L1 | 10 | 117 |
| L2 | 11 | 188 |
| L2 | 11 | 336 |
| L2 | 10 | 362 |
| E1 | 9 | 449 |
| L2 | 10 | 230 |
| L1 | 9 | 361 |
| L1 | 10 | 361 |
| L1 | 11 | 361 |
| E2 | 8 | 29 |
| E1 | 8 | 502 |
| E1 | 9 | 502 |
| E7 | 8 | 5 |
| E5A | 8 | 21 |
| E5A | 9 | 21 |
| E5A | 11 | 21 |
| L1 | 11 | 272 |
| E5A | 10 | 31 |
| E5A | 11 | 31 |
| L2 | 9 | 113 |
| L2 | 10 | 113 |
| L2 | 9 | 279 |
| E6 | 9 | 97 |
| L2 | 8 | 178 |
| E5A | 9 | 32 |
| E5A | 10 | 32 |
| E5A | 11 | 32 |
| L2 | 9 | 44 |
| L2 | 10 | 44 |
| L2 | 11 | 44 |
| E5A | 8 | 17 |
| E5A | 9 | 17 |
| E5A | 10 | 17 |
| E6 | 8 | 120 |

TABLE XIV B-continued

HPV6B
HLA-B62 Supermotif Peptides

| 2 | 3 | 4 |
|---|---|---|
| E1 | 8 | 301 |
| E1 | 10 | 455 |
| L2 | 9 | 32 |
| L2 | 8 | 193 |
| L2 | 8 | 450 |
| E2 | 11 | 352 |
| L1 | 11 | 191 |
| E1 | 9 | 313 |
| E1 | 10 | 313 |
| E1 | 11 | 313 |
| E1 | 8 | 265 |
| E1 | 10 | 265 |
| E1 | 11 | 265 |
| E5B | 10 | 23 |
| E1 | 11 | 476 |
| E7 | 11 | 11 |
| L2 | 9 | 121 |
| L2 | 11 | 121 |
| E1 | 10 | 443 |
| E1 | 10 | 23 |
| L2 | 10 | 104 |
| L2 | 11 | 104 |
| E5A | 8 | 34 |
| E5A | 9 | 34 |
| E5A | 10 | 34 |
| E5A | 8 | 41 |
| E1 | 8 | 433 |
| E1 | 11 | 433 |
| E6 | 8 | 73 |
| E6 | 10 | 73 |
| E1 | 10 | 312 |
| E1 | 11 | 312 |
| E1 | 9 | 254 |
| E1 | 8 | 357 |
| E1 | 10 | 357 |
| L2 | 10 | 22 |
| L2 | 11 | 22 |
| E1 | 9 | 114 |
| E1 | 8 | 420 |
| L1 | 10 | 432 |
| L1 | 11 | 432 |
| E6 | 9 | 109 |
| L2 | 9 | 79 |
| L1 | 8 | 169 |
| E6 | 9 | 94 |
| E2 | 8 | 47 |
| E2 | 10 | 47 |
| L1 | 8 | 148 |
| E1 | 11 | 424 |
| L2 | 11 | 34 |
| E2 | 11 | 147 |
| E6 | 11 | 116 |
| E6 | 8 | 52 |
| E6 | 10 | 52 |
| E1 | 9 | 283 |
| E2 | 11 | 63 |
| L1 | 9 | 61 |
| L1 | 10 | 61 |
| L1 | 8 | 19 |
| L1 | 9 | 19 |
| L1 | 10 | 71 |
| L2 | 8 | 107 |
| E1 | 8 | 255 |
| E1 | 11 | 255 |
| E1 | 11 | 307 |
| E1 | 9 | 557 |
| E1 | 9 | 491 |
| E1 | 10 | 491 |
| E2 | 8 | 314 |
| L1 | 11 | 186 |
| L2 | 8 | 246 |
| L2 | 9 | 246 |
| E5A | 8 | 33 |
| E5A | 9 | 33 |
| E5A | 10 | 33 |
| E5A | 11 | 33 |
| L1 | 8 | 41 |
| L1 | 9 | 41 |
| L1 | 11 | 41 |
| E5B | 9 | 18 |
| E1 | 10 | 521 |
| E1 | 11 | 521 |
| E1 | 9 | 540 |
| E1 | 9 | 208 |
| E7 | 8 | 83 |
| E7 | 11 | 83 |
| E7 | 8 | 82 |
| E7 | 9 | 82 |
| E5B | 9 | 29 |
| E5A | 9 | 59 |
| E5A | 10 | 59 |
| E5A | 8 | 51 |
| E5B | 8 | 30 |
| E1 | 9 | 298 |
| E1 | 11 | 298 |
| E2 | 8 | 82 |
| E2 | 11 | 82 |
| E5A | 8 | 69 |
| E5A | 8 | 60 |
| E5A | 9 | 60 |
| E5A | 10 | 72 |
| E5A | 11 | 72 |
| E1 | 9 | 276 |
| E1 | 9 | 563 |
| E2 | 8 | 42 |
| L2 | 8 | 422 |
| E5A | 8 | 18 |
| E5A | 9 | 18 |
| E5A | 11 | 18 |
| E2 | 8 | 94 |
| E2 | 9 | 94 |
| E5A | 10 | 65 |
| L1 | 10 | 367 |
| L1 | 11 | 309 |
| L1 | 8 | 231 |
| E1 | 9 | 511 |
| L2 | 9 | 398 |
| L1 | 11 | 465 |
| L1 | 8 | 209 |
| L1 | 10 | 209 |
| L2 | 9 | 74 |
| L2 | 9 | 338 |
| L2 | 11 | 338 |
| E5A | 9 | 73 |
| E5A | 10 | 73 |
| E7 | 9 | 29 |
| E1 | 8 | 277 |
| E5A | 8 | 47 |
| L1 | 9 | 295 |
| E2 | 11 | 222 |
| E1 | 8 | 564 |
| E7 | 10 | 67 |
| L1 | 10 | 95 |
| E5B | 9 | 26 |
| E1 | 8 | 306 |
| E2 | 9 | 56 |
| E2 | 8 | 151 |
| E2 | 9 | 151 |
| E1 | 10 | 47 |
| L1 | 9 | 196 |
| L1 | 11 | 196 |
| E1 | 9 | 274 |
| E1 | 11 | 274 |
| E1 | 10 | 361 |
| E1 | 10 | 568 |
| E1 | 11 | 451 |
| E1 | 9 | 300 |
| E1 | 8 | 539 |

TABLE XIV B-continued

HPV6B
HLA-B62 Supermotif Peptides

| 2 | 3 | 4 |
|---|---|---|
| E1 | 10 | 539 |
| E6 | 9 | 21 |
| L1 | 8 | 337 |
| L1 | 8 | 134 |
| L1 | 10 | 134 |
| L1 | 8 | 390 |
| L1 | 10 | 390 |
| L2 | 10 | 358 |
| L2 | 9 | 157 |
| L2 | 9 | 251 |
| L2 | 11 | 251 |
| L1 | 8 | 323 |
| E1 | 10 | 304 |
| E6 | 8 | 75 |
| E6 | 11 | 75 |
| L2 | 9 | 325 |
| L2 | 11 | 325 |
| L1 | 11 | 217 |
| L2 | 10 | 189 |
| L2 | 11 | 189 |
| E1 | 9 | 94 |
| E1 | 11 | 442 |
| E4 | 8 | 69 |
| E6 | 8 | 110 |
| E6 | 11 | 110 |
| L1 | 8 | 183 |
| L1 | 9 | 183 |
| L1 | 11 | 109 |
| E7 | 8 | 47 |
| E7 | 9 | 47 |
| E1 | 8 | 562 |
| E1 | 10 | 562 |
| E5A | 11 | 64 |
| L2 | 10 | 73 |
| L2 | 9 | 389 |
| E1 | 8 | 258 |
| E1 | 10 | 258 |
| L2 | 10 | 337 |
| L2 | 8 | 86 |
| L2 | 9 | 86 |
| L2 | 9 | 410 |
| L2 | 9 | 123 |
| E7 | 10 | 17 |
| E1 | 8 | 479 |
| E1 | 9 | 479 |
| E1 | 11 | 479 |
| L2 | 8 | 28 |
| E1 | 8 | 310 |
| L1 | 9 | 182 |
| L1 | 10 | 182 |
| E1 | 9 | 561 |
| E1 | 11 | 561 |
| L1 | 10 | 404 |
| L1 | 8 | 13 |
| L1 | 9 | 13 |
| L1 | 11 | 403 |
| L1 | 9 | 12 |
| L1 | 10 | 12 |
| E2 | 9 | 235 |
| E2 | 10 | 353 |
| E2 | 11 | 353 |
| L2 | 9 | 170 |
| L2 | 11 | 170 |
| L2 | 8 | 90 |
| L2 | 11 | 168 |
| L2 | 11 | 243 |
| L2 | 9 | 96 |
| L2 | 10 | 96 |
| E2 | 10 | 258 |
| L2 | 8 | 171 |
| L2 | 10 | 171 |
| L2 | 9 | 426 |
| L2 | 10 | 426 |
| L2 | 8 | 158 |

TABLE XIV B-continued

HPV6B
HLA-B62 Supermotif Peptides

| 2 | 3 | 4 |
|---|---|---|
| E7 | 11 | 20 |
| E5A | 8 | 19 |
| E5A | 10 | 19 |
| E5A | 11 | 19 |
| L1 | 8 | 266 |
| L2 | 11 | 212 |
| L1 | 11 | 16 |
| L2 | 9 | 363 |
| L2 | 11 | 417 |
| L2 | 8 | 252 |
| L2 | 10 | 252 |
| E5A | 10 | 7 |
| E5A | 11 | 7 |
| L2 | 10 | 43 |
| L2 | 11 | 43 |
| E1 | 10 | 31 |
| E6 | 10 | 15 |
| L1 | 11 | 372 |
| L1 | 8 | 301 |
| E7 | 9 | 81 |
| E7 | 10 | 81 |
| E7 | 10 | 28 |
| E4 | 9 | 14 |
| L1 | 8 | 250 |
| E2 | 9 | 48 |
| E2 | 11 | 48 |
| E1 | 9 | 305 |
| E1 | 10 | 527 |
| E1 | 11 | 527 |
| E1 | 10 | 118 |
| E7 | 9 | 46 |
| E7 | 10 | 46 |
| E1 | 8 | 512 |
| E7 | 11 | 16 |
| L2 | 10 | 169 |
| L2 | 8 | 381 |
| E2 | 9 | 344 |
| E7 | 10 | 80 |
| E7 | 11 | 80 |
| E2 | 10 | 244 |
| L2 | 9 | 231 |
| E2 | 8 | 57 |
| L2 | 8 | 298 |
| L2 | 8 | 316 |
| L2 | 11 | 316 |
| L2 | 9 | 449 |
| L1 | 11 | 241 |
| L2 | 9 | 245 |
| L2 | 10 | 245 |
| L1 | 9 | 40 |
| L1 | 10 | 40 |
| E2 | 10 | 303 |
| E1 | 8 | 616 |
| E7 | 11 | 66 |
| L1 | 11 | 94 |
| L2 | 11 | 284 |
| L2 | 9 | 89 |
| L1 | 8 | 3 |
| L1 | 9 | 3 |
| E1 | 8 | 69 |
| E1 | 11 | 69 |
| E1 | 11 | 117 |
| E2 | 8 | 343 |
| E2 | 10 | 343 |
| L1 | 8 | 140 |
| E1 | 11 | 583 |
| L2 | 8 | 153 |
| L2 | 10 | 267 |
| L2 | 11 | 267 |
| E5A | 8 | 30 |
| E5A | 11 | 30 |
| L1 | 9 | 50 |
| L1 | 10 | 50 |
| E2 | 8 | 207 |

TABLE XIV B-continued

HPV6B
HLA-B62 Supermotif Peptides

| 2 | 3 | 4 |
|---|---|---|
| L1 | 11 | 474 |
| E1 | 10 | 247 |
| L1 | 8 | 375 |
| L1 | 9 | 375 |
| L1 | 11 | 375 |
| L2 | 11 | 103 |
| E1 | 8 | 60 |
| L1 | 11 | 86 |
| L2 | 11 | 49 |
| L2 | 8 | 106 |
| L2 | 9 | 106 |
| E1 | 10 | 490 |
| E1 | 11 | 490 |
| E2 | 9 | 81 |
| L1 | 10 | 294 |
| E1 | 8 | 260 |
| E6 | 10 | 23 |
| E6 | 11 | 23 |
| L2 | 10 | 304 |
| E2 | 8 | 150 |
| E2 | 9 | 150 |
| E2 | 10 | 150 |
| E2 | 8 | 246 |
| E2 | 11 | 246 |
| L2 | 10 | 324 |
| E1 | 10 | 93 |
| E4 | 8 | 68 |
| E4 | 9 | 68 |
| E1 | 10 | 89 |
| E1 | 11 | 635 |
| E1 | 8 | 354 |
| E1 | 9 | 354 |
| E1 | 11 | 354 |
| E7 | 8 | 45 |
| E7 | 10 | 45 |
| E7 | 11 | 45 |
| L1 | 8 | 281 |
| L1 | 8 | 189 |
| L1 | 9 | 189 |
| L1 | 8 | 392 |
| E2 | 10 | 40 |
| E5A | 10 | 45 |
| L2 | 9 | 260 |
| E1 | 11 | 185 |
| E2 | 9 | 198 |
| E2 | 11 | 198 |
| L2 | 9 | 164 |
| L2 | 10 | 145 |
| L2 | 11 | 145 |
| L1 | 8 | 343 |
| L2 | 9 | 39 |
| E1 | 10 | 97 |
| E6 | 9 | 12 |
| E2 | 8 | 355 |
| E2 | 9 | 355 |
| E1 | 8 | 294 |
| L1 | 8 | 408 |
| L1 | 9 | 408 |
| E1 | 10 | 556 |
| E5A | 9 | 50 |
| E1 | 10 | 297 |
| E5A | 11 | 71 |
| E7 | 8 | 86 |
| E2 | 9 | 93 |
| E2 | 10 | 93 |
| E6 | 8 | 26 |
| L1 | 9 | 377 |
| L1 | 10 | 377 |
| E1 | 11 | 408 |
| E2 | 10 | 128 |
| E2 | 11 | 128 |
| E5B | 10 | 59 |
| E5B | 11 | 59 |
| L1 | 10 | 388 |
| L2 | 9 | 138 |
| L2 | 9 | 419 |
| L2 | 10 | 419 |
| L2 | 11 | 419 |
| E2 | 9 | 215 |
| E4 | 11 | 72 |
| L1 | 10 | 427 |
| E1 | 9 | 468 |
| E1 | 10 | 468 |
| L2 | 9 | 375 |
| E2 | 10 | 234 |
| L2 | 8 | 242 |
| L2 | 8 | 360 |
| E1 | 11 | 30 |
| E1 | 8 | 526 |
| E1 | 11 | 526 |
| L2 | 9 | 380 |
| E1 | 8 | 148 |
| E6 | 10 | 88 |
| E4 | 11 | 83 |
| E2 | 9 | 191 |
| E1 | 9 | 332 |
| E1 | 10 | 332 |
| L2 | 11 | 387 |
| E1 | 9 | 78 |
| L2 | 11 | 378 |
| L2 | 10 | 184 |
| L1 | 11 | 328 |
| L1 | 9 | 57 |
| L1 | 11 | 57 |
| L1 | 10 | 8 |
| E2 | 8 | 192 |
| E1 | 11 | 346 |
| E1 | 8 | 333 |
| E1 | 9 | 333 |
| E5A | 9 | 20 |
| E5A | 10 | 20 |
| L2 | 10 | 31 |
| L1 | 8 | 190 |
| E1 | 11 | 499 |
| E7 | 10 | 12 |
| E6 | 9 | 53 |
| E1 | 8 | 275 |
| E1 | 10 | 275 |
| E2 | 9 | 41 |
| L1 | 8 | 73 |
| E5A | 11 | 48 |
| E5A | 9 | 46 |
| E4 | 8 | 10 |
| L1 | 8 | 382 |
| L2 | 10 | 213 |
| L1 | 9 | 59 |
| L1 | 11 | 59 |
| L2 | 11 | 72 |
| L2 | 10 | 388 |
| L2 | 8 | 122 |
| L2 | 10 | 122 |
| L1 | 10 | 11 |
| L1 | 11 | 11 |
| E7 | 8 | 69 |
| E7 | 11 | 69 |
| E1 | 8 | 79 |
| E2 | 8 | 139 |
| E2 | 10 | 139 |
| E1 | 9 | 444 |
| E1 | 11 | 444 |
| L2 | 8 | 261 |
| E1 | 9 | 24 |
| E5A | 11 | 6 |
| E7 | 11 | 79 |
| E2 | 11 | 243 |
| L2 | 8 | 232 |
| E1 | 9 | 362 |
| E1 | 11 | 238 |

TABLE XIV B-continued

HPV6B
HLA-B62 Supermotif Peptides

| 2 | 3 | 4 |
|---|---|---|
| L1 | 8 | 20 |
| E5A | 8 | 25 |
| E5A | 10 | 25 |
| E5A | 11 | 25 |
| L1 | 10 | 329 |
| E2 | 8 | 349 |
| L1 | 9 | 72 |
| L1 | 8 | 58 |
| L1 | 10 | 58 |
| E7 | 9 | 68 |
| E2 | 8 | 132 |
| E1 | 9 | 426 |
| E5A | 8 | 36 |
| E5A | 11 | 36 |
| E1 | 8 | 340 |
| E1 | 8 | 530 |
| E5B | 10 | 13 |
| E5B | 11 | 13 |
| E1 | 11 | 464 |
| E5B | 8 | 17 |
| E5B | 10 | 17 |
| E5A | 10 | 58 |
| E5A | 11 | 58 |
| E1 | 10 | 510 |
| E1 | 8 | 267 |
| E1 | 9 | 267 |
| E4 | 9 | 76 |
| E2 | 9 | 102 |
| E2 | 8 | 145 |
| E1 | 8 | 237 |
| L1 | 9 | 385 |
| E4 | 8 | 22 |
| E4 | 10 | 22 |
| E6 | 10 | 105 |
| E1 | 10 | 86 |
| L2 | 8 | 435 |
| E1 | 9 | 579 |
| E1 | 11 | 579 |
| L1 | 9 | 230 |
| L2 | 9 | 371 |
| L1 | 8 | 358 |
| E1 | 11 | 536 |
| L1 | 8 | 65 |
| L1 | 9 | 65 |
| E1 | 8 | 402 |
| E4 | 8 | 9 |
| E4 | 9 | 9 |
| E2 | 11 | 168 |
| L1 | 10 | 287 |
| L1 | 8 | 10 |
| L1 | 11 | 10 |
| E2 | 8 | 138 |
| E2 | 9 | 138 |
| E2 | 11 | 138 |
| E1 | 8 | 91 |
| L1 | 8 | 26 |
| L1 | 9 | 26 |
| E2 | 8 | 131 |
| E2 | 9 | 131 |

TABLE XIV

C. HPVI 1
HLA B62 Supermotif Peptides

| 2 | 3 | 4 |
|---|---|---|
| L2 | 10 | 111 |
| L2 | 11 | 111 |
| E1 | 11 | 112 |
| L2 | 9 | 285 |

TABLE XIV-continued

C. HPVI 1
HLA B62 Supermotif Peptides

| 2 | 3 | 4 |
|---|---|---|
| L2 | 11 | 285 |
| E1 | 11 | 22 |
| E1 | 11 | 520 |
| L1 | 8 | 81 |
| L2 | 8 | 417 |
| L2 | 9 | 417 |
| E6 | 8 | 37 |
| E6 | 10 | 37 |
| E1 | 9 | 319 |
| L2 | 9 | 270 |
| L2 | 10 | 270 |
| E1 | 10 | 337 |
| E1 | 11 | 337 |
| E2 | 8 | 325 |
| L1 | 8 | 159 |
| L2 | 8 | 97 |
| L2 | 11 | 97 |
| L2 | 9 | 181 |
| L1 | 8 | 313 |
| L1 | 10 | 313 |
| E2 | 10 | 175 |
| L1 | 8 | 301 |
| L1 | 9 | 301 |
| E4 | 10 | 13 |
| E7 | 8 | 45 |
| E7 | 10 | 45 |
| E2 | 8 | 217 |
| E5 | 8 | 25 |
| E5 | 10 | 25 |
| E5 | 11 | 25 |
| L1 | 9 | 43 |
| E5 | 10 | 26 |
| E1 | 10 | 601 |
| E5 | 8 | 27 |
| E5 | 9 | 27 |
| E5 | 11 | 27 |
| E6 | 8 | 67 |
| E6 | 11 | 67 |
| E6 | 9 | 137 |
| L2 | 9 | 26 |
| L1 | 10 | 182 |
| L1 | 11 | 182 |
| E1 | 10 | 560 |
| E2 | 9 | 11 |
| E2 | 8 | 251 |
| E5 | 8 | 73 |
| E5 | 9 | 73 |
| E5 | 10 | 73 |
| E4 | 9 | 73 |
| E4 | 11 | 73 |
| E1 | 8 | 369 |
| E1 | 10 | 369 |
| L1 | 9 | 220 |
| E2 | 9 | 25 |
| L2 | 10 | 277 |
| E6 | 10 | 96 |
| L2 | 8 | 191 |
| L2 | 9 | 191 |
| E1 | 10 | 203 |
| E1 | 8 | 570 |
| E1 | 10 | 570 |
| L2 | 9 | 399 |
| L2 | 10 | 346 |
| E1 | 11 | 81 |
| E7 | 9 | 81 |
| E7 | 10 | 81 |
| L1 | 11 | 367 |
| E7 | 8 | 14 |
| L1 | 9 | 209 |
| E1 | 11 | 46 |
| L1 | 10 | 196 |
| L2 | 11 | 353 |
| L2 | 8 | 100 |
| L1 | 8 | 89 |

TABLE XIV-continued

C. HPVI 1
HLA B62 Supermotif Peptides

| 2 | 3 | 4 |
|---|---|---|
| L1 | 9 | 89 |
| E7 | 8 | 19 |
| L2 | 11 | 357 |
| L1 | 8 | 237 |
| L1 | 9 | 237 |
| L1 | 10 | 237 |
| L1 | 8 | 435 |
| L1 | 9 | 435 |
| L1 | 11 | 435 |
| L1 | 9 | 456 |
| L2 | 11 | 41 |
| L1 | 8 | 125 |
| L2 | 11 | 29 |
| L1 | 10 | 216 |
| L2 | 11 | 257 |
| E6 | 8 | 113 |
| L2 | 8 | 331 |
| E1 | 9 | 105 |
| E2 | 9 | 312 |
| L1 | 11 | 454 |
| E1 | 8 | 197 |
| E6 | 9 | 69 |
| E1 | 10 | 604 |
| E1 | 11 | 604 |
| E1 | 9 | 131 |
| E2 | 8 | 17 |
| E2 | 10 | 17 |
| E1 | 10 | 417 |
| E1 | 11 | 417 |
| E1 | 11 | 360 |
| E2 | 11 | 100 |
| L2 | 10 | 350 |
| E1 | 9 | 257 |
| E1 | 11 | 257 |
| E1 | 9 | 309 |
| L2 | 11 | 161 |
| L2 | 10 | 94 |
| L2 | 11 | 94 |
| L1 | 9 | 266 |
| E2 | 10 | 90 |
| E7 | 11 | 27 |
| L1 | 8 | 250 |
| L1 | 9 | 250 |
| E2 | 10 | 340 |
| E2 | 8 | 185 |
| E2 | 9 | 185 |
| E1 | 8 | 141 |
| E1 | 9 | 39 |
| E1 | 10 | 39 |
| L1 | 10 | 103 |
| E2 | 11 | 118 |
| L1 | 9 | 382 |
| L1 | 8 | 444 |
| E2 | 10 | 205 |
| L2 | 10 | 119 |
| L1 | 8 | 370 |
| E6 | 8 | 126 |
| E1 | 11 | 454 |
| L2 | 8 | 424 |
| E1 | 9 | 494 |
| E1 | 10 | 494 |
| E5 | 9 | 68 |
| E5 | 10 | 68 |
| E1 | 10 | 393 |
| E1 | 11 | 393 |
| E2 | 11 | 345 |
| E1 | 9 | 446 |
| E1 | 10 | 446 |
| E1 | 8 | 457 |
| L2 | 9 | 238 |
| L2 | 11 | 238 |
| E5 | 8 | 16 |
| E5 | 9 | 16 |
| E5 | 10 | 16 |

TABLE XIV-continued

C. HPVI 1
HLA B62 Supermotif Peptides

| 2 | 3 | 4 |
|---|---|---|
| E5 | 8 | 77 |
| E5 | 9 | 77 |
| E5 | 10 | 77 |
| E5 | 11 | 77 |
| E1 | 10 | 593 |
| E1 | 11 | 593 |
| L2 | 9 | 216 |
| L2 | 10 | 402 |
| E1 | 11 | 252 |
| L2 | 11 | 154 |
| E1 | 8 | 220 |
| L2 | 8 | 393 |
| L2 | 10 | 393 |
| E5 | 9 | 40 |
| L1 | 9 | 319 |
| L1 | 10 | 319 |
| E1 | 10 | 243 |
| E1 | 11 | 194 |
| E1 | 8 | 326 |
| E1 | 9 | 326 |
| E2 | 9 | 156 |
| E5 | 10 | 29 |
| E2 | 10 | 55 |
| E1 | 8 | 217 |
| E1 | 11 | 217 |
| E2 | 9 | 50 |
| E2 | 10 | 50 |
| L2 | 8 | 291 |
| L2 | 10 | 222 |
| L1 | 11 | 145 |
| E1 | 8 | 273 |
| E1 | 10 | 273 |
| L2 | 8 | 84 |
| L2 | 10 | 84 |
| L2 | 11 | 397 |
| E1 | 10 | 478 |
| E2 | 10 | 243 |
| L2 | 10 | 421 |
| L2 | 11 | 421 |
| L1 | 8 | 137 |
| L1 | 10 | 137 |
| E1 | 10 | 160 |
| E2 | 8 | 162 |
| E2 | 10 | 162 |
| L2 | 8 | 309 |
| L2 | 10 | 309 |
| L2 | 11 | 309 |
| L1 | 8 | 107 |
| E1 | 10 | 173 |
| L2 | 9 | 50 |
| E1 | 8 | 316 |
| L1 | 11 | 113 |
| L2 | 8 | 311 |
| L2 | 9 | 311 |
| E6 | 8 | 119 |
| E6 | 9 | 119 |
| L2 | 9 | 176 |
| E2 | 8 | 29 |
| E1 | 9 | 264 |
| E1 | 11 | 264 |
| E2 | 10 | 136 |
| E2 | 11 | 136 |
| E2 | 10 | 78 |
| E2 | 10 | 309 |
| E5 | 8 | 7 |
| E5 | 10 | 7 |
| E4 | 10 | 20 |
| E1 | 9 | 305 |
| L1 | 10 | 117 |
| L2 | 11 | 335 |
| L1 | 9 | 46 |
| E1 | 9 | 449 |
| E4 | 11 | 64 |
| L2 | 10 | 188 |

TABLE XIV-continued

C. HPVI 1
HLA B62 Supermotif Peptides

| 2 | 3 | 4 |
|---|---|---|
| L2 | 11 | 188 |
| L1 | 9 | 362 |
| L1 | 10 | 362 |
| L1 | 11 | 362 |
| E5 | 8 | 34 |
| E5 | 9 | 34 |
| E5 | 10 | 34 |
| L2 | 9 | 112 |
| L2 | 10 | 112 |
| L2 | 9 | 278 |
| E1 | 10 | 195 |
| E6 | 8 | 120 |
| L2 | 8 | 177 |
| E5 | 8 | 35 |
| E5 | 9 | 35 |
| E6 | 9 | 97 |
| L2 | 9 | 43 |
| L2 | 10 | 43 |
| L2 | 11 | 43 |
| E5 | 8 | 17 |
| E5 | 10 | 17 |
| E5 | 8 | 28 |
| E5 | 10 | 28 |
| E1 | 11 | 408 |
| L2 | 9 | 355 |
| E1 | 8 | 301 |
| E1 | 10 | 455 |
| L2 | 9 | 31 |
| L2 | 8 | 192 |
| L2 | 8 | 446 |
| L2 | 11 | 71 |
| E2 | 9 | 351 |
| E2 | 11 | 351 |
| L1 | 11 | 192 |
| E1 | 9 | 313 |
| E1 | 10 | 313 |
| E1 | 11 | 313 |
| E1 | 8 | 265 |
| E1 | 10 | 265 |
| E1 | 11 | 265 |
| E1 | 10 | 23 |
| E7 | 11 | 11 |
| E5 | 10 | 31 |
| E5 | 11 | 31 |
| E1 | 10 | 443 |
| L2 | 10 | 103 |
| L2 | 11 | 103 |
| E6 | 8 | 73 |
| E6 | 10 | 73 |
| E2 | 10 | 350 |
| E1 | 10 | 312 |
| E1 | 11 | 312 |
| E1 | 9 | 254 |
| E6 | 11 | 116 |
| E1 | 8 | 357 |
| E1 | 10 | 357 |
| E1 | 9 | 114 |
| E1 | 8 | 420 |
| E1 | 10 | 420 |
| E7 | 11 | 42 |
| L1 | 8 | 433 |
| L1 | 10 | 433 |
| L1 | 11 | 433 |
| E2 | 8 | 112 |
| E2 | 10 | 112 |
| E2 | 8 | 47 |
| L1 | 8 | 149 |
| E1 | 11 | 424 |
| E1 | 8 | 433 |
| E1 | 11 | 433 |
| L2 | 11 | 33 |
| E1 | 9 | 283 |
| L1 | 10 | 53 |
| L1 | 9 | 61 |
| L1 | 10 | 61 |
| E2 | 11 | 147 |
| L1 | 8 | 19 |
| L1 | 9 | 19 |
| L1 | 10 | 71 |
| E6 | 8 | 52 |
| E6 | 10 | 52 |
| L2 | 8 | 106 |
| E1 | 8 | 255 |
| E1 | 11 | 255 |
| E1 | 11 | 307 |
| E5 | 8 | 33 |
| E5 | 9 | 33 |
| E5 | 10 | 33 |
| E5 | 11 | 33 |
| E1 | 9 | 557 |
| E1 | 9 | 491 |
| E1 | 10 | 491 |
| E5 | 9 | 16 |
| E5 | 11 | 16 |
| E5 | 8 | 36 |
| E5 | 11 | 36 |
| L1 | 11 | 187 |
| L1 | 8 | 41 |
| L1 | 9 | 41 |
| L1 | 11 | 41 |
| E1 | 10 | 521 |
| E1 | 9 | 540 |
| E2 | 10 | 15 |
| E7 | 8 | 83 |
| E7 | 11 | 83 |
| E2 | 8 | 42 |
| E4 | 9 | 18 |
| E7 | 8 | 82 |
| E7 | 9 | 82 |
| E5 | 8 | 31 |
| E5 | 9 | 30 |
| E5 | 9 | 59 |
| E5 | 10 | 59 |
| E5 | 8 | 51 |
| E1 | 9 | 298 |
| E1 | 11 | 298 |
| L1 | 8 | 119 |
| E5 | 8 | 69 |
| E5 | 9 | 69 |
| E5 | 8 | 60 |
| E5 | 9 | 60 |
| E1 | 9 | 276 |
| E1 | 9 | 563 |
| L2 | 10 | 212 |
| L2 | 8 | 418 |
| E5 | 9 | 18 |
| E5 | 11 | 18 |
| E7 | 11 | 79 |
| E2 | B | 139 |
| E2 | 10 | 139 |
| E2 | 8 | 94 |
| E2 | 9 | 94 |
| E5 | 10 | 65 |
| L1 | 10 | 368 |
| L2 | 8 | 260 |
| E2 | 11 | 289 |
| E6 | 8 | 70 |
| E6 | 11 | 70 |
| L1 | 11 | 310 |
| L1 | 8 | 232 |
| E1 | 9 | 511 |
| L2 | 11 | 228 |
| L1 | 8 | 210 |
| E2 | 9 | 56 |
| L2 | 9 | 337 |
| L2 | 11 | 337 |
| L1 | 11 | 273 |
| E1 | 8 | 277 |

TABLE XIV-continued

C. HPVI 1
HLA B62 Supermotif Peptides

| 2 | 3 | 4 |
|---|---|---|
| E5 | 8 | 47 |
| L1 | 9 | 296 |
| E7 | 8 | 5 |
| E1 | 8 | 564 |
| L2 | 8 | 245 |
| L2 | 9 | 245 |
| E7 | 10 | 67 |
| L1 | 10 | 95 |
| E1 | 8 | 306 |
| E1 | 11 | 398 |
| E1 | 10 | 47 |
| L1 | 9 | 197 |
| L1 | 11 | 197 |
| E1 | 9 | 274 |
| E1 | 11 | 274 |
| E1 | 10 | 361 |
| E4 | 9 | 1 |
| E4 | 10 | 1 |
| E4 | 11 | 1 |
| E1 | 10 | 568 |
| E1 | 9 | 300 |
| E2 | 9 | 254 |
| E6 | 10 | 50 |
| E1 | 8 | 539 |
| E1 | 10 | 539 |
| E6 | 9 | 21 |
| L1 | 8 | 338 |
| L1 | 8 | 135 |
| L1 | 10 | 135 |
| L2 | 9 | 156 |
| L2 | 10 | 156 |
| L1 | 8 | 391 |
| L1 | 10 | 391 |
| L2 | 9 | 250 |
| E6 | 11 | 131 |
| E6 | 8 | 75 |
| E6 | 11 | 75 |
| E1 | 10 | 97 |
| E2 | 8 | 127 |
| E2 | 11 | 127 |
| E4 | 8 | 4 |
| L2 | 10 | 354 |
| E1 | 9 | 94 |
| E1 | 11 | 442 |
| E6 | 11 | 110 |
| L1 | 8 | 218 |
| L1 | 11 | 218 |
| L1 | 8 | 184 |
| L1 | 9 | 184 |
| L2 | 8 | 157 |
| L2 | 9 | 157 |
| L2 | 10 | 72 |
| L1 | 9 | 118 |
| E1 | 8 | 562 |
| E1 | 10 | 562 |
| L2 | 11 | 211 |
| E5 | 11 | 64 |
| L2 | 8 | 385 |
| L2 | 9 | 385 |
| L2 | 10 | 385 |
| E1 | 8 | 258 |
| E1 | 10 | 258 |
| E7 | 8 | 47 |
| E4 | 8 | 68 |
| L2 | 10 | 336 |
| E7 | 10 | 17 |
| E1 | 9 | 479 |
| E1 | 11 | 479 |
| L2 | 8 | 27 |
| E1 | 8 | 310 |
| L1 | 9 | 183 |
| L1 | 10 | 183 |
| E1 | 9 | 561 |
| E1 | 11 | 561 |
| L1 | 10 | 405 |
| L1 | 8 | 13 |
| L1 | 9 | 13 |
| L1 | 11 | 404 |
| L1 | 9 | 12 |
| L1 | 10 | 12 |
| E2 | 8 | 352 |
| E2 | 10 | 352 |
| E2 | 11 | 352 |
| L2 | 9 | 122 |
| L2 | 9 | 169 |
| L2 | 11 | 169 |
| L2 | 8 | 89 |
| L2 | 11 | 167 |
| L2 | 11 | 242 |
| L2 | 9 | 95 |
| L2 | 10 | 95 |
| L2 | 8 | 170 |
| L2 | 10 | 170 |
| L2 | 9 | 422 |
| L2 | 10 | 422 |
| L1 | 8 | 267 |
| L2 | 10 | 358 |
| L1 | 11 | 16 |
| L2 | 11 | 413 |
| L2 | 9 | 324 |
| E5 | 8 | 19 |
| E5 | 10 | 19 |
| L2 | 8 | 251 |
| E5 | 11 | 7 |
| L2 | 10 | 42 |
| L2 | 11 | 42 |
| E1 | 10 | 31 |
| L1 | 11 | 373 |
| E7 | 10 | 28 |
| L1 | 8 | 302 |
| E2 | 11 | 14 |
| E4 | 9 | 14 |
| L1 | 8 | 251 |
| E2 | 11 | 48 |
| E1 | 10 | 527 |
| E1 | 11 | 527 |
| E1 | 10 | 118 |
| E1 | 8 | 512 |
| E7 | 9 | 46 |
| E7 | 11 | 16 |
| L2 | 10 | 168 |
| E2 | 9 | 343 |
| L2 | 10 | 229 |
| L2 | 9 | 230 |
| E2 | 8 | 57 |
| L2 | 8 | 297 |
| L2 | 9 | 297 |
| L2 | 8 | 315 |
| L2 | 11 | 315 |
| L2 | 9 | 445 |
| L1 | 11 | 242 |
| L1 | 9 | 40 |
| L1 | 10 | 40 |
| E2 | 10 | 302 |
| E1 | 8 | 616 |
| E7 | 8 | 4 |
| E7 | 9 | 4 |
| L2 | 9 | 244 |
| L2 | 10 | 244 |
| E7 | 11 | 66 |
| L1 | 11 | 94 |
| L2 | 11 | 283 |
| E4 | 8 | 67 |
| E4 | 9 | 67 |
| L2 | 9 | 88 |
| L1 | 8 | 3 |
| L1 | 9 | 3 |
| E1 | 8 | 69 |

TABLE XIV-continued

C. HPVI 1
HLA B62 Supermotif Peptides

| 2 | 3 | 4 |
|---|---|---|
| E1 | 11 | 69 |
| E2 | 8 | 342 |
| E2 | 10 | 342 |
| L1 | 8 | 141 |
| E1 | 11 | 583 |
| E1 | 10 | 247 |
| E2 | 8 | 207 |
| E2 | 8 | 23 |
| E2 | 9 | 23 |
| E2 | 11 | 23 |
| E6 | 9 | 12 |
| L2 | 10 | 266 |
| L2 | 11 | 266 |
| L1 | 9 | 50 |
| L1 | 10 | 50 |
| E1 | 8 | 422 |
| L2 | 8 | 387 |
| L1 | 8 | 376 |
| L1 | 9 | 376 |
| L1 | 11 | 376 |
| E5 | 8 | 30 |
| E5 | 11 | 30 |
| L2 | 11 | 102 |
| E2 | 9 | 81 |
| L1 | 11 | 86 |
| L2 | 11 | 48 |
| E6 | 10 | 23 |
| E6 | 11 | 23 |
| L2 | 8 | 105 |
| L2 | 9 | 105 |
| E1 | 10 | 490 |
| E1 | 11 | 490 |
| L2 | 9 | 259 |
| L1 | 10 | 295 |
| E1 | 8 | 260 |
| L2 | 9 | 406 |
| L2 | 10 | 303 |
| E2 | 9 | 195 |
| E2 | 10 | 322 |
| E2 | 11 | 322 |
| E1 | 10 | 93 |
| L2 | 10 | 323 |
| E1 | 10 | 89 |
| E1 | 11 | 635 |
| E1 | 8 | 354 |
| E1 | 9 | 354 |
| E1 | 11 | 354 |
| L2 | 9 | 376 |
| L1 | 8 | 282 |
| E2 | 8 | 151 |
| E2 | 9 | 151 |
| E2 | 9 | 257 |
| E2 | 10 | 257 |
| E1 | 8 | 60 |
| L2 | 8 | 152 |
| E1 | 8 | 436 |
| E1 | 9 | 436 |
| E1 | 11 | 436 |
| L1 | 8 | 190 |
| L1 | 9 | 190 |
| L2 | 9 | 163 |
| E2 | 8 | 348 |
| L1 | 8 | 393 |
| E2 | 10 | 40 |
| E5 | 10 | 45 |
| L1 | 8 | 344 |
| E2 | 9 | 198 |
| E2 | 11 | 198 |
| L2 | 10 | 144 |
| L2 | 11 | 144 |
| L2 | 9 | 38 |
| E2 | 10 | 261 |
| E2 | 8 | 354 |
| E2 | 9 | 354 |
| L2 | 10 | 183 |
| E2 | 10 | 249 |
| E5 | 10 | 71 |
| E5 | 11 | 71 |
| L1 | 8 | 409 |
| L1 | 9 | 409 |
| E1 | 8 | 294 |
| E1 | 10 | 207 |
| E1 | 10 | 556 |
| E5 | 8 | 15 |
| E5 | 10 | 15 |
| E5 | 9 | 50 |
| E1 | 10 | 297 |
| E7 | 8 | 86 |
| E2 | 9 | 93 |
| E2 | 10 | 93 |
| E5 | 8 | 26 |
| L1 | 9 | 378 |
| L1 | 10 | 378 |
| L2 | 11 | 374 |
| L1 | 10 | 389 |
| L2 | 9 | 137 |
| L2 | 9 | 415 |
| L2 | 10 | 415 |
| L2 | 11 | 415 |
| E2 | 10 | 215 |
| E4 | 11 | 71 |
| L1 | 10 | 428 |
| E1 | 9 | 468 |
| E1 | 10 | 468 |
| L2 | 9 | 371 |
| L2 | 8 | 241 |
| L1 | 8 | 170 |
| E1 | 11 | 30 |
| E1 | 11 | 57 |
| E1 | 8 | 526 |
| E1 | 11 | 526 |
| E1 | 11 | 117 |
| E2 | 8 | 85 |
| L1 | 8 | 224 |
| L1 | 11 | 224 |
| E5 | 10 | 88 |
| E2 | 9 | 191 |
| E1 | 9 | 332 |
| E1 | 10 | 332 |
| L2 | 10 | 383 |
| L2 | 11 | 383 |
| E1 | 9 | 78 |
| E4 | 11 | 82 |
| E2 | 11 | 223 |
| E2 | 11 | 63 |
| L1 | 11 | 329 |
| L1 | 9 | 57 |
| L1 | 11 | 57 |
| L1 | 10 | 8 |
| E5 | 8 | 21 |
| E5 | 11 | 21 |
| E2 | 8 | 192 |
| E1 | 11 | 346 |
| E1 | 8 | 333 |
| E1 | 9 | 333 |
| L2 | 10 | 30 |
| L1 | 8 | 191 |
| L2 | 8 | 164 |
| E1 | 11 | 499 |
| E7 | 10 | 12 |
| E5 | 9 | 27 |
| E5 | 9 | 32 |
| E5 | 10 | 32 |
| E5 | 11 | 32 |
| E2 | 9 | 41 |
| E4 | 10 | 17 |
| E1 | 8 | 275 |
| E1 | 10 | 275 |

TABLE XIV-continued

C. HPVI 1
HLA B62 Supermotif Peptides

| 2 | 3 | 4 |
|---|---|---|
| L1 | 8 | 73 |
| E5 | 11 | 48 |
| E5 | 9 | 46 |
| E4 | 8 | 10 |
| L1 | 8 | 383 |
| E2 | 10 | 128 |
| E2 | 11 | 128 |
| E4 | 8 | 3 |
| E4 | 9 | 3 |
| L1 | 9 | 59 |
| L1 | 11 | 59 |
| L1 | 9 | 217 |
| L2 | 9 | 384 |
| L2 | 10 | 384 |
| L2 | 11 | 384 |
| L1 | 10 | 11 |
| L1 | 11 | 11 |
| L2 | 8 | 121 |
| L2 | 10 | 121 |
| E1 | 8 | 79 |
| E1 | 9 | 444 |
| E1 | 11 | 444 |
| L2 | 9 | 359 |
| L2 | 9 | 394 |
| E4 | 10 | 83 |
| L2 | 8 | 231 |
| E1 | 9 | 362 |
| E1 | 11 | 238 |
| L1 | 8 | 20 |
| L1 | 10 | 330 |
| E7 | 9 | 68 |
| E5 | 9 | 20 |
| L1 | 9 | 72 |
| E4 | 8 | 2 |
| E4 | 9 | 2 |
| E4 | 10 | 2 |
| L1 | 8 | 58 |
| L1 | 10 | 58 |
| L2 | 9 | 120 |
| L2 | 11 | 120 |
| E5 | 9 | 53 |
| E5 | 8 | 41 |
| E1 | 9 | 426 |
| E1 | 8 | 340 |
| E5 | 10 | 14 |
| E5 | 11 | 14 |
| E5 | 8 | 18 |
| E5 | 10 | 18 |
| E1 | 11 | 464 |
| E5 | 10 | 58 |
| E5 | 11 | 58 |
| E1 | 10 | 510 |
| E1 | 8 | 267 |
| E1 | 9 | 267 |
| E2 | 9 | 102 |
| E4 | 9 | 75 |
| E2 | 8 | 145 |
| E1 | 8 | 237 |
| L1 | 9 | 386 |
| E4 | 8 | 22 |
| E6 | 10 | 105 |
| E1 | 10 | 86 |
| L2 | 8 | 431 |
| E1 | 9 | 579 |
| E1 | 11 | 579 |
| E2 | 8 | 138 |
| E2 | 9 | 138 |
| E2 | 11 | 138 |
| L1 | 9 | 231 |
| L1 | 8 | 246 |
| L1 | 8 | 359 |
| E1 | 11 | 536 |
| E2 | 10 | 61 |
| E2 | 11 | 61 |
| L1 | 8 | 65 |
| L1 | 9 | 65 |
| L1 | 10 | 288 |
| E1 | 8 | 402 |
| L1 | 8 | 26 |
| L1 | 9 | 26 |
| E4 | 11 | 16 |
| E4 | 8 | 9 |
| E4 | 9 | 9 |
| E2 | 11 | 168 |
| E1 | 8 | 502 |
| E1 | 9 | 502 |
| L1 | 8 | 10 |
| L1 | 11 | 10 |
| E1 | 8 | 91 |
| E2 | 8 | 131 |

TABLE XV

HLA-A1 Motif Peptides

| 1 | 2 | 3 | 4 |
|---|---|---|---|
| HPV16 | E1 | 11 | 248 |
| HPV16 | E1 | 10 | 206 |
| HPV16 | E1 | 8 | 524 |
| HPV16 | E1 | 9 | 404 |
| HPV16 | E1 | 10 | 522 |
| HPV16 | E1 | 9 | 371 |
| HPV16 | E1 | 8 | 372 |
| HPV16 | E1 | 10 | 249 |
| HPV16 | E1 | 10 | 356 |
| HPV16 | E1 | 9 | 152 |
| HPV16 | E1 | 9 | 594 |
| HPV16 | E1 | 8 | 127 |
| HPV16 | E1 | 10 | 162 |
| HPV16 | E1 | 9 | 325 |
| HPV16 | E1 | 10 | 272 |
| HPV16 | E1 | 9 | 163 |
| HPV16 | E1 | 8 | 571 |
| HPV16 | E1 | 9 | 12 |
| HPV16 | E1 | 11 | 568 |
| HPV16 | E1 | 8 | 326 |
| HPV16 | E1 | 9 | 369 |
| HPV16 | E1 | 11 | 369 |
| HPV16 | E1 | 11 | 323 |
| HPV16 | E1 | 10 | 252 |
| HPV16 | E1 | 11 | 521 |
| HPV16 | E1 | 9 | 126 |
| HPV16 | E1 | 9 | 312 |
| HPV16 | E1 | 11 | 312 |
| HPV16 | E1 | 9 | 357 |
| HPV16 | E1 | 11 | 48 |
| HPV16 | E1 | 9 | 207 |
| HPV16 | E1 | 9 | 420 |
| HPV16 | E1 | 10 | 593 |
| HPV16 | E1 | 10 | 419 |
| HPV16 | E1 | 11 | 80 |
| HPV16 | E1 | 11 | 150 |
| HPV16 | E1 | 8 | 313 |
| HPV16 | E1 | 10 | 313 |
| HPV16 | E1 | 8 | 421 |
| HPV16 | E1 | 9 | 314 |
| HPV16 | E1 | 8 | 315 |
| HPV16 | E1 | 8 | 370 |
| HPV16 | E1 | 10 | 370 |
| HPV16 | E1 | 11 | 402 |
| HPV16 | E2 | 9 | 11 |
| HPV16 | E2 | 10 | 122 |
| HPV16 | E2 | 11 | 22 |
| HPV16 | E2 | 8 | 80 |

TABLE XV-continued

HLA-A1 Motif Peptides

| 1 | 2 | 3 | 4 |
|---|---|---|---|
| HPV16 | E2 | 8 | 171 |
| HPV16 | E2 | 11 | 293 |
| HPV16 | E2 | 10 | 328 |
| HPV16 | E2 | 9 | 35 |
| HPV16 | E2 | 10 | 35 |
| HPV16 | E2 | 9 | 329 |
| HPV16 | E2 | 9 | 94 |
| HPV16 | E2 | 11 | 77 |
| HPV16 | E2 | 8 | 296 |
| HPV16 | E2 | 10 | 106 |
| HPV16 | E2 | 8 | 151 |
| HPV16 | E2 | 9 | 151 |
| HPV16 | E2 | 8 | 37 |
| HPV16 | E2 | 10 | 23 |
| HPV16 | E2 | 10 | 78 |
| HPV16 | E2 | 11 | 128 |
| HPV16 | E2 | 8 | 160 |
| HPV16 | E2 | 10 | 145 |
| HPV16 | E2 | 11 | 145 |
| HPV16 | E2 | 8 | 147 |
| HPV16 | E2 | 9 | 147 |
| HPV16 | E2 | 11 | 92 |
| HPV16 | E2 | 8 | 131 |
| HPV16 | E5 | 11 | 53 |
| HPV16 | E5 | 10 | 54 |
| HPV16 | E6 | 11 | 51 |
| HPV16 | E6 | 8 | 54 |
| HPV16 | E6 | 8 | 76 |
| HPV16 | E6 | 11 | 76 |
| HPV16 | E6 | 8 | 92 |
| HPV16 | E6 | 10 | 30 |
| HPV16 | E6 | 9 | 80 |
| HPV16 | E6 | 8 | 79 |
| HPV16 | E6 | 10 | 79 |
| HPV16 | E6 | 9 | 69 |
| HPV16 | E6 | 10 | 77 |
| HPV16 | E7 | 8 | 4 |
| HPV16 | E7 | 8 | 18 |
| HPV16 | E7 | 10 | 43 |
| HPV16 | E7 | 10 | 2 |
| HPV16 | E7 | 9 | 44 |
| HPV16 | E7 | 8 | 16 |
| HPV16 | E7 | 10 | 16 |
| HPV16 | L1 | 9 | 373 |
| HPV16 | L1 | 11 | 371 |
| HPV16 | L1 | 10 | 251 |
| HPV16 | L1 | 9 | 13 |
| HPV16 | L1 | 8 | 154 |
| HPV16 | L1 | 11 | 386 |
| HPV16 | L1 | 11 | 307 |
| HPV16 | L1 | 8 | 374 |
| HPV16 | L1 | 11 | 11 |
| HPV16 | L1 | 10 | 407 |
| HPV16 | L1 | 8 | 463 |
| HPV16 | L1 | 11 | 151 |
| HPV16 | L1 | 10 | 152 |
| HPV16 | L1 | 8 | 68 |
| HPV16 | L1 | 8 | 31 |
| HPV16 | L1 | 8 | 409 |
| HPV16 | L1 | 9 | 169 |
| HPV16 | L1 | 9 | 462 |
| HPV16 | L1 | 11 | 247 |
| HPV16 | L1 | 11 | 43 |
| HPV16 | L1 | 10 | 328 |
| HPV16 | L1 | 10 | 308 |
| HPV16 | L1 | 11 | 50 |
| HPV16 | L1 | 11 | 327 |
| HPV16 | L1 | 9 | 252 |
| HPV16 | L1 | 11 | 65 |
| HPV16 | L1 | 11 | 379 |
| HPV16 | L1 | 10 | 293 |
| HPV16 | L1 | 10 | 44 |
| HPV16 | L1 | 8 | 268 |
| HPV16 | L1 | 8 | 53 |
| HPV16 | L1 | 9 | 53 |
| HPV16 | L2 | 10 | 443 |
| HPV16 | L2 | 11 | 443 |
| HPV16 | L2 | 9 | 259 |
| HPV16 | L2 | 10 | 317 |
| HPV16 | L2 | 11 | 317 |
| HPV16 | L2 | 10 | 63 |
| HPV16 | L2 | 11 | 218 |
| HPV16 | L2 | 8 | 65 |
| HPV16 | L2 | 8 | 440 |
| HPV16 | L2 | 8 | 41 |
| HPV16 | L2 | 8 | 320 |
| HPV16 | L2 | 9 | 320 |
| HPV16 | L2 | 9 | 439 |
| HPV16 | L2 | 10 | 243 |
| HPV16 | L2 | 8 | 250 |
| HPV16 | L2 | 9 | 11 |
| HPV16 | L2 | 9 | 318 |
| HPV16 | L2 | 10 | 318 |
| HPV16 | L2 | 11 | 318 |
| HPV16 | L2 | 10 | 39 |
| HPV16 | L2 | 11 | 183 |
| HPV16 | L2 | 10 | 294 |
| HPV16 | L2 | 10 | 397 |
| HPV16 | L2 | 8 | 386 |
| HPV16 | L2 | 11 | 383 |
| HPV16 | L2 | 9 | 358 |
| HPV16 | L2 | 8 | 221 |
| HPV16 | L2 | 8 | 342 |
| HPV16 | L2 | 8 | 12 |
| HPV16 | L2 | 11 | 9 |
| HPV16 | L2 | 10 | 184 |
| HPV16 | L2 | 9 | 185 |
| HPV16 | L2 | 8 | 186 |
| HPV16 | L2 | 11 | 62 |
| HPV16 | L2 | 9 | 40 |
| HPV16 | L2 | 11 | 359 |
| HPV16 | L2 | 11 | 359 |
| HPV16 | L2 | 9 | 295 |
| HPV16 | L2 | 9 | 398 |
| HPV16 | L2 | 9 | 244 |
| HPV16 | L2 | 9 | 385 |
| HPV16 | L2 | 11 | 437 |
| HPV18 | E1 | 8 | 578 |
| HPV18 | E1 | 10 | 213 |
| HPV18 | E1 | 8 | 531 |
| HPV18 | E1 | 9 | 411 |
| HPV18 | E1 | 10 | 529 |
| HPV18 | E1 | 9 | 378 |
| HPV18 | E1 | 8 | 379 |
| HPV18 | E1 | 8 | 130 |
| HPV18 | E1 | 9 | 484 |
| HPV18 | E1 | 9 | 11 |
| HPV18 | E1 | 10 | 576 |
| HPV18 | E1 | 8 | 401 |
| HPV18 | E1 | 10 | 259 |
| HPV18 | E1 | 11 | 528 |
| HPV18 | E1 | 11 | 409 |
| HPV18 | E1 | 9 | 400 |
| HPV18 | E1 | 9 | 319 |
| HPV18 | E1 | 11 | 319 |
| HPV18 | E1 | 11 | 376 |
| HPV18 | E1 | 9 | 214 |
| HPV18 | E1 | 10 | 600 |
| HPV18 | E1 | 8 | 320 |
| HPV18 | E1 | 10 | 320 |
| HPV18 | E1 | 9 | 321 |
| HPV18 | E1 | 8 | 322 |
| HPV18 | E1 | 10 | 377 |
| HPV18 | E1 | 10 | 533 |
| HPV18 | E1 | 11 | 532 |
| HPV18 | E2 | 10 | 154 |
| HPV18 | E2 | 11 | 154 |
| HPV18 | E2 | 11 | 132 |
| HPV18 | E2 | 8 | 156 |
| HPV18 | E2 | 9 | 156 |

TABLE XV-continued

HLA-A1 Motif Peptides

| 1 | 2 | 3 | 4 |
|---|---|---|---|
| HPV18 | E2 | 8 | 29 |
| HPV18 | E2 | 11 | 26 |
| HPV18 | E2 | 9 | 354 |
| HPV18 | E2 | 8 | 176 |
| HPV18 | E2 | 11 | 352 |
| HPV18 | E2 | 9 | 329 |
| HPV18 | E2 | 10 | 133 |
| HPV18 | E2 | 11 | 133 |
| HPV18 | E2 | 8 | 128 |
| HPV18 | E2 | 8 | 297 |
| HPV18 | E2 | 10 | 353 |
| HPV18 | E2 | 11 | 56 |
| HPV18 | E2 | 9 | 296 |
| HPV18 | E2 | 10 | 27 |
| HPV18 | E2 | 11 | 230 |
| HPV18 | E2 | 10 | 231 |
| HPV18 | E2 | 9 | 165 |
| HPV18 | E2 | 9 | 15 |
| HPV18 | E2 | 8 | 157 |
| HPV18 | E2 | 9 | 232 |
| HPV18 | E2 | 11 | 173 |
| HPV18 | E2 | 8 | 135 |
| HPV18 | E2 | 9 | 135 |
| HPV18 | E5 | 10 | 30 |
| HPV18 | E5 | 11 | 43 |
| HPV18 | E5 | 9 | 23 |
| HPV18 | E5 | 8 | 24 |
| HPV18 | E5 | 9 | 45 |
| HPV18 | E5 | 10 | 44 |
| HPV18 | E6 | 8 | 27 |
| HPV18 | E6 | 11 | 46 |
| HPV18 | E6 | 9 | 4 |
| HPV18 | E6 | 8 | 49 |
| HPV18 | E6 | 11 | 71 |
| HPV18 | E6 | 11 | 62 |
| HPV18 | E6 | 10 | 25 |
| HPV18 | E6 | 10 | 3 |
| HPV18 | E6 | 11 | 89 |
| HPV18 | E6 | 10 | 72 |
| HPV18 | L1 | 9 | 495 |
| HPV18 | L1 | 8 | 345 |
| HPV18 | L1 | 11 | 407 |
| HPV18 | L1 | 10 | 286 |
| HPV18 | L1 | 11 | 493 |
| HPV18 | L1 | 9 | 258 |
| HPV18 | L1 | 9 | 364 |
| HPV18 | L1 | 8 | 330 |
| HPV18 | L1 | 8 | 517 |
| HPV18 | L1 | 8 | 177 |
| HPV18 | L1 | 11 | 342 |
| HPV18 | L1 | 10 | 443 |
| HPV18 | L1 | 9 | 516 |
| HPV18 | L1 | 10 | 120 |
| HPV18 | L1 | 11 | 256 |
| HPV18 | L1 | 8 | 445 |
| HPV18 | L1 | 10 | 328 |
| HPV18 | L1 | 10 | 343 |
| HPV18 | L1 | 8 | 496 |
| HPV18 | L1 | 9 | 344 |
| HPV18 | L1 | 11 | 282 |
| HPV18 | L1 | 9 | 472 |
| HPV18 | L1 | 9 | 287 |
| HPV18 | L1 | 8 | 410 |
| HPV18 | L1 | 10 | 416 |
| HPV18 | L1 | 9 | 424 |
| HPV18 | L1 | 8 | 66 |
| HPV18 | L1 | 10 | 363 |
| HPV18 | L1 | 11 | 100 |
| HPV18 | L1 | 10 | 408 |
| HPV18 | L1 | 11 | 78 |
| HPV18 | L1 | 11 | 327 |
| HPV18 | L1 | 9 | 409 |
| HPV18 | L1 | 11 | 362 |
| HPV18 | L1 | 8 | 473 |
| HPV18 | L1 | 9 | 204 |
| HPV18 | L1 | 8 | 89 |
| HPV18 | L1 | 9 | 417 |
| HPV18 | L1 | 11 | 35 |
| HPV18 | L1 | 8 | 425 |
| HPV18 | L1 | 9 | 4 |
| HPV18 | L2 | 11 | 341 |
| HPV18 | L2 | 11 | 322 |
| HPV18 | L2 | 8 | 344 |
| HPV18 | L2 | 10 | 62 |
| HPV18 | L2 | 8 | 64 |
| HPV18 | L2 | 10 | 432 |
| HPV18 | L2 | 11 | 432 |
| HPV18 | L2 | 10 | 183 |
| HPV18 | L2 | 11 | 310 |
| HPV18 | L2 | 8 | 313 |
| HPV18 | L2 | 10 | 323 |
| HPV18 | L2 | 9 | 10 |
| HPV18 | L2 | 10 | 242 |
| HPV18 | L2 | 10 | 391 |
| HPV18 | L2 | 8 | 325 |
| HPV18 | L2 | 9 | 419 |
| HPV18 | L2 | 9 | 376 |
| HPV18 | L2 | 8 | 185 |
| HPV18 | L2 | 8 | 11 |
| HPV18 | L2 | 8 | 244 |
| HPV18 | L2 | 11 | 364 |
| HPV18 | L2 | 8 | 220 |
| HPV18 | L2 | 8 | 393 |
| HPV18 | L2 | 10 | 365 |
| HPV18 | L2 | 10 | 342 |
| HPV18 | L2 | 11 | 61 |
| HPV18 | L2 | 8 | 377 |
| HPV18 | L2 | 8 | 367 |
| HPV18 | L2 | 9 | 392 |
| HPV18 | L2 | 9 | 366 |
| HPV18 | L2 | 11 | 417 |
| HPV18 | L2 | 11 | 374 |
| HPV31 | E1 | 11 | 79 |
| HPV31 | E1 | 10 | 186 |
| HPV31 | E1 | 8 | 504 |
| HPV31 | E1 | 10 | 502 |
| HPV31 | E1 | 9 | 351 |
| HPV31 | E1 | 8 | 96 |
| HPV31 | E1 | 10 | 336 |
| HPV31 | E1 | 8 | 352 |
| HPV31 | E1 | 8 | 50 |
| HPV31 | E1 | 8 | 551 |
| HPV31 | E1 | 9 | 305 |
| HPV31 | E1 | 9 | 11 |
| HPV31 | E1 | 10 | 456 |
| HPV31 | E1 | 11 | 548 |
| HPV31 | E1 | 11 | 471 |
| HPV31 | E1 | 10 | 232 |
| HPV31 | E1 | 11 | 501 |
| HPV31 | E1 | 9 | 125 |
| HPV31 | E1 | 9 | 292 |
| HPV31 | E1 | 11 | 292 |
| HPV31 | E1 | 10 | 94 |
| HPV31 | E1 | 9 | 337 |
| HPV31 | E1 | 8 | 350 |
| HPV31 | E1 | 10 | 350 |
| HPV31 | E1 | 8 | 306 |
| HPV31 | E1 | 11 | 47 |
| HPV31 | E1 | 10 | 573 |
| HPV31 | E1 | 11 | 93 |
| HPV31 | E1 | 8 | 293 |
| HPV31 | E1 | 10 | 293 |
| HPV31 | E1 | 11 | 303 |
| HPV31 | E1 | 9 | 294 |
| HPV31 | E1 | 8 | 295 |
| HPV31 | E1 | 11 | 505 |
| HPV31 | E1 | 11 | 382 |
| HPV31 | E1 | 9 | 349 |
| HPV31 | E1 | 11 | 349 |
| HPV31 | E1 | 10 | 419 |

TABLE XV-continued

HLA-A1 Motif Peptides

| 1 | 2 | 3 | 4 |
|---|---|---|---|
| HPV31 | E2 | 9 | 11 |
| HPV31 | E2 | 10 | 122 |
| HPV31 | E2 | 11 | 22 |
| HPV31 | E2 | 8 | 80 |
| HPV31 | E2 | 8 | 171 |
| HPV31 | E2 | 11 | 300 |
| HPV31 | E2 | 9 | 336 |
| HPV31 | E2 | 8 | 312 |
| HPV31 | E2 | 10 | 78 |
| HPV31 | E2 | 11 | 77 |
| HPV31 | E2 | 9 | 361 |
| HPV31 | E2 | 10 | 106 |
| HPV31 | E2 | 8 | 37 |
| HPV31 | E2 | 9 | 311 |
| HPV31 | E2 | 11 | 128 |
| HPV31 | E2 | 10 | 93 |
| HPV31 | E2 | 8 | 362 |
| HPV31 | E2 | 8 | 160 |
| HPV31 | E2 | 11 | 92 |
| HPV31 | E2 | 8 | 131 |
| HPV31 | E5 | 11 | 53 |
| HPV31 | E5 | 10 | 54 |
| HPV31 | E6 | 8 | 63 |
| HPV31 | E6 | 11 | 44 |
| HPV31 | E6 | 10 | 14 |
| HPV31 | E6 | 8 | 47 |
| HPV31 | E6 | 11 | 69 |
| HPV31 | E6 | 8 | 72 |
| HPV31 | E6 | 10 | 72 |
| HPV31 | E6 | 9 | 15 |
| HPV31 | E6 | 11 | 22 |
| HPV31 | E6 | 8 | 16 |
| HPV31 | E6 | 9 | 73 |
| HPV31 | E6 | 10 | 23 |
| HPV31 | E6 | 10 | 70 |
| HPV31 | E7 | 8 | 4 |
| HPV31 | E7 | 10 | 43 |
| HPV31 | E7 | 9 | 17 |
| HPV31 | E7 | 9 | 44 |
| HPV31 | E7 | 10 | 16 |
| HPV31 | E7 | 10 | 2 |
| HPV31 | L1 | 8 | 285 |
| HPV31 | L1 | 10 | 226 |
| HPV31 | L1 | 8 | 129 |
| HPV31 | L1 | 8 | 270 |
| HPV31 | L1 | 10 | 127 |
| HPV31 | L1 | 9 | 356 |
| HPV31 | L1 | 9 | 269 |
| HPV31 | L1 | 11 | 282 |
| HPV31 | L1 | 10 | 382 |
| HPV31 | L1 | 8 | 438 |
| HPV31 | L1 | 11 | 126 |
| HPV31 | L1 | 8 | 357 |
| HPV31 | L1 | 8 | 384 |
| HPV31 | L1 | 8 | 43 |
| HPV31 | L1 | 9 | 144 |
| HPV31 | L1 | 9 | 227 |
| HPV31 | L1 | 9 | 437 |
| HPV31 | L1 | 11 | 222 |
| HPV31 | L1 | 10 | 410 |
| HPV31 | L1 | 9 | 411 |
| HPV31 | L1 | 11 | 17 |
| HPV31 | L1 | 8 | 5 |
| HPV31 | L1 | 10 | 303 |
| HPV31 | L1 | 8 | 412 |
| HPV31 | L1 | 10 | 283 |
| HPV31 | L1 | 11 | 24 |
| HPV31 | L1 | 9 | 383 |
| HPV31 | L1 | 11 | 302 |
| HPV31 | L1 | 11 | 354 |
| HPV31 | L1 | 10 | 268 |
| HPV31 | L1 | 10 | 18 |
| HPV31 | L1 | 8 | 28 |
| HPV31 | L1 | 8 | 243 |
| HPV31 | L2 | 9 | 311 |
| HPV31 | L2 | 10 | 311 |
| HPV31 | L2 | 11 | 311 |
| HPV31 | L2 | 10 | 253 |
| HPV31 | L2 | 11 | 237 |
| HPV31 | L2 | 8 | 433 |
| HPV31 | L2 | 10 | 436 |
| HPV31 | L2 | 11 | 436 |
| HPV31 | L2 | 10 | 63 |
| HPV31 | L2 | 8 | 65 |
| HPV31 | L2 | 11 | 38 |
| HPV31 | L2 | 8 | 41 |
| HPV31 | L2 | 8 | 313 |
| HPV31 | L2 | 9 | 313 |
| HPV31 | L2 | 8 | 245 |
| HPV31 | L2 | 9 | 11 |
| HPV31 | L2 | 9 | 348 |
| HPV31 | L2 | 10 | 238 |
| HPV31 | L2 | 11 | 178 |
| HPV31 | L2 | 10 | 287 |
| HPV31 | L2 | 9 | 378 |
| HPV31 | L2 | 8 | 12 |
| HPV31 | L2 | 8 | 216 |
| HPV31 | L2 | 11 | 9 |
| HPV31 | L2 | 11 | 309 |
| HPV31 | L2 | 11 | 62 |
| HPV31 | L2 | 8 | 181 |
| HPV31 | L2 | 9 | 180 |
| HPV31 | L2 | 10 | 179 |
| HPV31 | L2 | 8 | 346 |
| HPV31 | L2 | 11 | 346 |
| HPV31 | L2 | 8 | 379 |
| HPV31 | L2 | 9 | 40 |
| HPV31 | L2 | 9 | 288 |
| HPV31 | L2 | 9 | 345 |
| HPV31 | L2 | 10 | 39 |
| HPV31 | L2 | 10 | 344 |
| HPV31 | L2 | 11 | 343 |
| HPV31 | L2 | 8 | 255 |
| HPV31 | L2 | 10 | 377 |
| HPV31 | L2 | 11 | 430 |
| HPV33 | E1 | 9 | 226 |
| HPV33 | E1 | 8 | 364 |
| HPV33 | E1 | 9 | 364 |
| HPV33 | E1 | 10 | 349 |
| HPV33 | E1 | 8 | 365 |
| HPV33 | E1 | 9 | 587 |
| HPV33 | E1 | 9 | 470 |
| HPV33 | E1 | 8 | 564 |
| HPV33 | E1 | 11 | 192 |
| HPV33 | E1 | 11 | 514 |
| HPV33 | E1 | 9 | 125 |
| HPV33 | E1 | 9 | 520 |
| HPV33 | E1 | 10 | 124 |
| HPV33 | E1 | 9 | 305 |
| HPV33 | E1 | 9 | 350 |
| HPV33 | E1 | 9 | 362 |
| HPV33 | E1 | 10 | 362 |
| HPV33 | E1 | 11 | 362 |
| HPV33 | E1 | 8 | 195 |
| HPV33 | E1 | 10 | 586 |
| HPV33 | E1 | 10 | 519 |
| HPV33 | E1 | 8 | 306 |
| HPV33 | E1 | 10 | 193 |
| HPV33 | E1 | 8 | 363 |
| HPV33 | E1 | 9 | 363 |
| HPV33 | E1 | 10 | 363 |
| HPV33 | E1 | 11 | 561 |
| HPV33 | E1 | 11 | 224 |
| HPV33 | E1 | 11 | 110 |
| HPV33 | E1 | 11 | 395 |
| HPV33 | E1 | 8 | 517 |
| HPV33 | E2 | 10 | 78 |
| HPV33 | E2 | 10 | 145 |
| HPV33 | E2 | 10 | 122 |
| HPV33 | E2 | 10 | 282 |

TABLE XV-continued

HLA-A1 Motif Peptides

| 1 | 2 | 3 | 4 |
|---|---|---|---|
| HPV33 | E2 | 8 | 80 |
| HPV33 | E2 | 8 | 171 |
| HPV33 | E2 | 11 | 281 |
| HPV33 | E2 | 8 | 151 |
| HPV33 | E2 | 9 | 151 |
| HPV33 | E2 | 9 | 162 |
| HPV33 | E2 | 8 | 284 |
| HPV33 | E2 | 9 | 113 |
| HPV33 | E2 | 8 | 37 |
| HPV33 | E2 | 9 | 283 |
| HPV33 | E2 | 11 | 128 |
| HPV33 | E2 | 9 | 146 |
| HPV33 | E2 | 9 | 11 |
| HPV33 | E2 | 11 | 148 |
| HPV33 | E2 | 8 | 131 |
| HPV33 | E5 | 10 | 44 |
| HPV33 | E5 | 11 | 43 |
| HPV33 | E6 | 9 | 46 |
| HPV33 | E6 | 11 | 44 |
| HPV33 | E6 | 8 | 47 |
| HPV33 | E6 | 8 | 69 |
| HPV33 | E6 | 11 | 69 |
| HPV33 | E6 | 9 | 73 |
| HPV33 | E6 | 8 | 72 |
| HPV33 | E6 | 10 | 72 |
| HPV33 | E6 | 10 | 70 |
| HPV33 | E7 | 10 | 43 |
| HPV33 | E7 | 11 | 43 |
| HPV33 | E7 | 9 | 8 |
| HPV33 | E7 | 11 | 6 |
| HPV33 | E7 | 8 | 46 |
| HPV33 | E7 | 8 | 16 |
| HPV33 | E7 | 10 | 16 |
| HPV33 | L1 | 10 | 225 |
| HPV33 | L1 | 10 | 345 |
| HPV33 | L1 | 8 | 129 |
| HPV33 | L1 | 9 | 435 |
| HPV33 | L1 | 9 | 303 |
| HPV33 | L1 | 10 | 127 |
| HPV33 | L1 | 11 | 359 |
| HPV33 | L1 | 9 | 268 |
| HPV33 | L1 | 9 | 226 |
| HPV33 | L1 | 8 | 436 |
| HPV33 | L1 | 11 | 126 |
| HPV33 | L1 | 8 | 355 |
| HPV33 | L1 | 10 | 267 |
| HPV33 | L1 | 8 | 42 |
| HPV33 | L1 | 8 | 382 |
| HPV33 | L1 | 9 | 144 |
| HPV33 | L1 | 11 | 221 |
| HPV33 | L1 | 11 | 433 |
| HPV33 | L1 | 10 | 408 |
| HPV33 | L1 | 9 | 409 |
| HPV33 | L1 | 11 | 17 |
| HPV33 | L1 | 8 | 5 |
| HPV33 | L1 | 8 | 410 |
| HPV33 | L1 | 10 | 302 |
| HPV33 | L1 | 11 | 39 |
| HPV33 | L1 | 8 | 227 |
| HPV33 | L1 | 11 | 352 |
| HPV33 | L1 | 11 | 24 |
| HPV33 | L1 | 11 | 301 |
| HPV33 | L1 | 10 | 18 |
| HPV33 | L1 | 8 | 28 |
| HPV33 | L1 | 9 | 28 |
| HPV33 | L1 | 10 | 380 |
| HPV33 | L1 | 8 | 27 |
| HPV33 | L1 | 9 | 27 |
| HPV33 | L1 | 10 | 27 |
| HPV33 | L2 | 11 | 436 |
| HPV33 | L2 | 11 | 183 |
| HPV33 | L2 | 10 | 437 |
| HPV33 | L2 | 8 | 64 |
| HPV33 | L2 | 10 | 62 |
| HPV33 | L2 | 11 | 218 |
| HPV33 | L2 | 11 | 37 |
| HPV33 | L2 | 8 | 374 |
| HPV33 | L2 | 8 | 336 |
| HPV33 | L2 | 8 | 40 |
| HPV33 | L2 | 8 | 318 |
| HPV33 | L2 | 9 | 358 |
| HPV33 | L2 | 9 | 10 |
| HPV33 | L2 | 9 | 348 |
| HPV33 | L2 | 10 | 243 |
| HPV33 | L2 | 11 | 333 |
| HPV33 | L2 | 8 | 186 |
| HPV33 | L2 | 8 | 221 |
| HPV33 | L2 | 8 | 11 |
| HPV33 | L2 | 9 | 63 |
| HPV33 | L2 | 10 | 184 |
| HPV33 | L2 | 10 | 354 |
| HPV33 | L2 | 10 | 38 |
| HPV33 | L2 | 9 | 355 |
| HPV33 | L2 | 11 | 61 |
| HPV33 | L2 | 9 | 39 |
| HPV33 | L2 | 9 | 244 |
| HPV33 | L2 | 11 | 353 |
| HPV33 | L2 | 8 | 356 |
| HPV33 | L2 | 11 | 356 |
| HPV45 | E1 | 8 | 564 |
| HPV45 | E1 | 10 | 199 |
| HPV45 | E1 | 8 | 517 |
| HPV45 | E1 | 9 | 397 |
| HPV45 | E1 | 10 | 515 |
| HPV45 | E1 | 9 | 364 |
| HPV45 | E1 | 10 | 562 |
| HPV45 | E1 | 8 | 365 |
| HPV45 | E1 | 8 | 130 |
| HPV45 | E1 | 9 | 470 |
| HPV45 | E1 | 11 | 459 |
| HPV45 | E1 | 10 | 519 |
| HPV45 | E1 | 8 | 387 |
| HPV45 | E1 | 10 | 245 |
| HPV45 | E1 | 11 | 514 |
| HPV45 | E1 | 11 | 395 |
| HPV45 | E1 | 9 | 386 |
| HPV45 | E1 | 9 | 305 |
| HPV45 | E1 | 11 | 305 |
| HPV45 | E1 | 11 | 362 |
| HPV45 | E1 | 9 | 200 |
| HPV45 | E1 | 8 | 414 |
| HPV45 | E1 | 10 | 586 |
| HPV45 | E1 | 10 | 412 |
| HPV45 | E1 | 8 | 306 |
| HPV45 | E1 | 10 | 306 |
| HPV45 | E1 | 9 | 307 |
| HPV45 | E1 | 8 | 308 |
| HPV45 | E1 | 10 | 363 |
| HPV45 | E2 | 11 | 134 |
| HPV45 | E2 | 8 | 158 |
| HPV45 | E2 | 9 | 158 |
| HPV45 | E2 | 11 | 28 |
| HPV45 | E2 | 8 | 178 |
| HPV45 | E2 | 10 | 186 |
| HPV45 | E2 | 8 | 167 |
| HPV45 | E2 | 9 | 167 |
| HPV45 | E2 | 11 | 151 |
| HPV45 | E2 | 9 | 300 |
| HPV45 | E2 | 8 | 154 |
| HPV45 | E2 | 9 | 17 |
| HPV45 | E2 | 8 | 130 |
| HPV45 | E2 | 8 | 301 |
| HPV45 | E2 | 9 | 187 |
| HPV45 | E2 | 9 | 357 |
| HPV45 | E2 | 9 | 332 |
| HPV45 | E2 | 10 | 356 |
| HPV45 | E2 | 10 | 29 |
| HPV45 | E2 | 11 | 155 |
| HPV45 | E2 | 8 | 159 |
| HPV45 | E6 | 9 | 37 |

TABLE XV-continued

HLA-A1 Motif Peptides

| 1 | 2 | 3 | 4 |
|---|---|---|---|
| HPV45 | E6 | 11 | 35 |
| HPV45 | E6 | 8 | 27 |
| HPV45 | E6 | 9 | 4 |
| HPV45 | E6 | 8 | 127 |
| HPV45 | E6 | 8 | 49 |
| HPV45 | E6 | 10 | 71 |
| HPV45 | E6 | 11 | 71 |
| HPV45 | E6 | 10 | 25 |
| HPV45 | E6 | 11 | 46 |
| HPV45 | E6 | 10 | 3 |
| HPV45 | E6 | 11 | 89 |
| HPV45 | E6 | 8 | 38 |
| HPV45 | E6 | 11 | 62 |
| HPV45 | E6 | 9 | 72 |
| HPV45 | E6 | 10 | 72 |
| HPV45 | E7 | 10 | 20 |
| HPV45 | L1 | 11 | 375 |
| HPV45 | L1 | 10 | 252 |
| HPV45 | L1 | 9 | 224 |
| HPV45 | L1 | 9 | 332 |
| HPV45 | L1 | 11 | 461 |
| HPV45 | L1 | 8 | 296 |
| HPV45 | L1 | 8 | 313 |
| HPV45 | L1 | 8 | 485 |
| HPV45 | L1 | 8 | 143 |
| HPV45 | L1 | 9 | 392 |
| HPV45 | L1 | 11 | 222 |
| HPV45 | L1 | 10 | 411 |
| HPV45 | L1 | 9 | 484 |
| HPV45 | L1 | 10 | 86 |
| HPV45 | L1 | 8 | 413 |
| HPV45 | L1 | 10 | 294 |
| HPV45 | L1 | 10 | 311 |
| HPV45 | L1 | 11 | 310 |
| HPV45 | L1 | 11 | 383 |
| HPV45 | L1 | 11 | 248 |
| HPV45 | L1 | 8 | 464 |
| HPV45 | L1 | 9 | 440 |
| HPV45 | L1 | 9 | 253 |
| HPV45 | L1 | 8 | 31 |
| HPV45 | L1 | 10 | 331 |
| HPV45 | L1 | 11 | 65 |
| HPV45 | L1 | 10 | 376 |
| HPV45 | L1 | 11 | 43 |
| HPV45 | L1 | 11 | 330 |
| HPV45 | L1 | 10 | 462 |
| HPV45 | L1 | 8 | 441 |
| HPV45 | L1 | 10 | 384 |
| HPV45 | L1 | 11 | 293 |
| HPV45 | L1 | 9 | 170 |
| HPV45 | L1 | 8 | 54 |
| HPV45 | L1 | 8 | 393 |
| HPV45 | L1 | 9 | 53 |
| HPV45 | L2 | 11 | 340 |
| HPV45 | L2 | 8 | 343 |
| HPV45 | L2 | 8 | 64 |
| HPV45 | L2 | 10 | 62 |
| HPV45 | L2 | 10 | 183 |
| HPV45 | L2 | 10 | 433 |
| HPV45 | L2 | 11 | 433 |
| HPV45 | L2 | 9 | 365 |
| HPV45 | L2 | 9 | 10 |
| HPV45 | L2 | 8 | 366 |
| HPV45 | L2 | 11 | 375 |
| HPV45 | L2 | 10 | 392 |
| HPV45 | L2 | 9 | 377 |
| HPV45 | L2 | 9 | 342 |
| HPV45 | L2 | 8 | 378 |
| HPV45 | L2 | 10 | 361 |
| HPV45 | L2 | 9 | 420 |
| HPV45 | L2 | 8 | 185 |
| HPV45 | L2 | 8 | 11 |
| HPV45 | L2 | 9 | 63 |
| HPV45 | L2 | 11 | 246 |
| HPV45 | L2 | 9 | 362 |
| HPV45 | L2 | 11 | 61 |
| HPV45 | L2 | 10 | 376 |
| HPV45 | L2 | 8 | 421 |
| HPV45 | L2 | 10 | 341 |
| HPV45 | L2 | 11 | 360 |
| HPV45 | L2 | 9 | 393 |
| HPV45 | L2 | 11 | 418 |
| HPV45 | L2 | 11 | 426 |
| HPV45 | L2 | 8 | 249 |
| HPV56 | E2 | 10 | 21 |
| HPV56 | E2 | 9 | 71 |
| HPV56 | E2 | 11 | 71 |
| HPV56 | E2 | 11 | 138 |
| HPV56 | E2 | 10 | 92 |
| HPV56 | E2 | 11 | 92 |
| HPV56 | E2 | 10 | 65 |
| HPV56 | E2 | 9 | 140 |
| HPV56 | E2 | 8 | 23 |
| HPV56 | E2 | 11 | 294 |
| HPV56 | E2 | 8 | 261 |
| HPV56 | E2 | 9 | 66 |
| HPV56 | E2 | 8 | 94 |
| HPV56 | E2 | 9 | 94 |
| HPV56 | E2 | 8 | 130 |
| HPV56 | E2 | 11 | 258 |
| HPV56 | E2 | 9 | 22 |
| HPV56 | E2 | 10 | 295 |
| HPV56 | E2 | 11 | 149 |
| HPV56 | E2 | 9 | 277 |
| HPV56 | E2 | 10 | 139 |
| HPV56 | E2 | 8 | 152 |
| HPV56 | E2 | 8 | 141 |
| HPV56 | E2 | 8 | 271 |
| HPV56 | E2 | 11 | 91 |
| HPV56 | E2 | 8 | 103 |
| HPV56 | E2 | 9 | 103 |
| HPV56 | E2 | 10 | 150 |
| HPV56 | E2 | 9 | 270 |
| HPV56 | E2 | 8 | 278 |
| HPV56 | E2 | 8 | 74 |
| HPV56 | E2 | 9 | 74 |
| HPV56 | E6 | 8 | 50 |
| HPV56 | E6 | 8 | 72 |
| HPV56 | E6 | 10 | 72 |
| HPV56 | E6 | 11 | 72 |
| HPV56 | E6 | 10 | 37 |
| HPV56 | E6 | 9 | 99 |
| HPV56 | E6 | 10 | 26 |
| HPV56 | E6 | 11 | 47 |
| HPV56 | E6 | 9 | 73 |
| HPV56 | E6 | 10 | 73 |
| HPV56 | E7 | 9 | 51 |
| HPV56 | L1 | 11 | 273 |
| HPV56 | L1 | 8 | 381 |
| HPV56 | L1 | 8 | 444 |
| HPV56 | L1 | 10 | 444 |
| HPV56 | L1 | 11 | 37 |
| HPV56 | L1 | 11 | 60 |
| HPV56 | L1 | 8 | 303 |
| HPV56 | L1 | 10 | 316 |
| HPV56 | L1 | 11 | 378 |
| HPV56 | L1 | 10 | 414 |
| HPV56 | L1 | 8 | 470 |
| HPV56 | L1 | 10 | 93 |
| HPV56 | L1 | 10 | 387 |
| HPV56 | L1 | 8 | 77 |
| HPV56 | L1 | 9 | 77 |
| HPV56 | L1 | 8 | 416 |
| HPV56 | L1 | 9 | 1 |
| HPV56 | L1 | 11 | 255 |
| HPV56 | L1 | 11 | 467 |
| HPV56 | L1 | 10 | 442 |
| HPV56 | L1 | 11 | 52 |
| HPV56 | L1 | 9 | 260 |
| HPV56 | L1 | 8 | 40 |

TABLE XV-continued

HLA-A1 Motif Peptides

| 1 | 2 | 3 | 4 |
|---|---|---|---|
| HPV56 | L1 | 10 | 285 |
| HPV56 | L1 | 10 | 336 |
| HPV56 | L1 | 8 | 446 |
| HPV56 | L1 | 11 | 74 |
| HPV56 | L1 | 10 | 379 |
| HPV56 | L1 | 8 | 261 |
| HPV56 | L1 | 9 | 415 |
| HPV56 | L1 | 11 | 335 |
| HPV56 | L1 | 9 | 445 |
| HPV56 | L1 | 10 | 301 |
| HPV56 | L1 | 10 | 259 |
| HPV56 | L1 | 10 | 53 |
| HPV56 | L1 | 9 | 388 |
| HPV56 | L1 | 8 | 276 |
| HPV56 | L1 | 8 | 9 |
| HPV56 | L2 | 8 | 64 |
| HPV56 | L2 | 10 | 434 |
| HPV56 | L2 | 10 | 62 |
| HPV56 | L2 | 10 | 310 |
| HPV56 | L2 | 11 | 310 |
| HPV56 | L2 | 8 | 313 |
| HPV56 | L2 | 9 | 313 |
| HPV56 | L2 | 11 | 182 |
| HPV56 | L2 | 9 | 10 |
| HPV56 | L2 | 11 | 338 |
| HPV56 | L2 | 8 | 341 |
| HPV56 | L2 | 11 | 341 |
| HPV56 | L2 | 10 | 342 |
| HPV56 | L2 | 8 | 185 |
| HPV56 | L2 | 9 | 423 |
| HPV56 | L2 | 11 | 433 |
| HPV56 | L2 | 11 | 421 |
| HPV56 | L2 | 8 | 11 |
| HPV56 | L2 | 8 | 220 |
| HPV56 | L2 | 8 | 436 |
| HPV56 | L2 | 9 | 343 |
| HPV56 | L2 | 9 | 435 |
| HPV56 | L2 | 10 | 183 |
| HPV56 | L2 | 11 | 414 |
| HPV56 | L2 | 9 | 63 |

TABLE XV

A. HPV6A
HLA-A 1 Motif Peptides

| 2 | 3 | 4 |
|---|---|---|
| L2 | 11 | 286 |
| L2 | 9 | 341 |
| L2 | 9 | 288 |
| L1 | 9 | 342 |
| E1 | 8 | 525 |
| E1 | 10 | 77 |
| L1 | 10 | 341 |
| E1 | 10 | 371 |
| E6 | 11 | 67 |
| E2 | 10 | 35 |
| E5 | 9 | 77 |
| E2 | 9 | 11 |
| E1 | 9 | 405 |
| E1 | 10 | 523 |
| E1 | 11 | 35 |
| E1 | 9 | 37 |
| E1 | 10 | 36 |
| E1 | 9 | 372 |
| L1 | 8 | 429 |
| E1 | 8 | 373 |
| E2 | 8 | 80 |
| E2 | 10 | 293 |
| E2 | 10 | 205 |
| L2 | 11 | 239 |

TABLE XV-continued

A. HPV6A
HLA-A 1 Motif Peptides

| 2 | 3 | 4 |
|---|---|---|
| L1 | 8 | 450 |
| E2 | 9 | 123 |
| E2 | 11 | 292 |
| L2 | 11 | 431 |
| L2 | 10 | 62 |
| E2 | 10 | 179 |
| L2 | 11 | 215 |
| L2 | 8 | 64 |
| L1 | 9 | 407 |
| L1 | 9 | 222 |
| L1 | 11 | 113 |
| E2 | 10 | 78 |
| E2 | 10 | 149 |
| E2 | 11 | 149 |
| L2 | 10 | 287 |
| E1 | 11 | 370 |
| L2 | 9 | 313 |
| E6 | 9 | 97 |
| E1 | 9 | 313 |
| E1 | 9 | 571 |
| L1 | 10 | 376 |
| L2 | 8 | 247 |
| L1 | 9 | 449 |
| E2 | 9 | 329 |
| E6 | 10 | 35 |
| L2 | 9 | 10 |
| L1 | 10 | 56 |
| L1 | 11 | 340 |
| E1 | 11 | 522 |
| E2 | 9 | 79 |
| E1 | 8 | 255 |
| L1 | 8 | 41 |
| E1 | 9 | 394 |
| L1 | 8 | 378 |
| L2 | 10 | 240 |
| E1 | 8 | 132 |
| E1 | 9 | 358 |
| E6 | 9 | 38 |
| E6 | 11 | 38 |
| E2 | 8 | 151 |
| E2 | 9 | 151 |
| E1 | 10 | 568 |
| E1 | 8 | 395 |
| E1 | 10 | 594 |
| L1 | 11 | 217 |
| E7 | 10 | 17 |
| E1 | 8 | 479 |
| L1 | 11 | 426 |
| L1 | 11 | 16 |
| L2 | 8 | 342 |
| E1 | 8 | 314 |
| E1 | 10 | 128 |
| L2 | 8 | 11 |
| E2 | 8 | 37 |
| L1 | 8 | 3 |
| E1 | 8 | 69 |
| L1 | 9 | 279 |
| L1 | 10 | 298 |
| E2 | 9 | 150 |
| E2 | 10 | 150 |
| L1 | 11 | 297 |
| L1 | 11 | 38 |
| L1 | 9 | 347 |
| E2 | 9 | 180 |
| L2 | 9 | 241 |
| L1 | 8 | 348 |
| L1 | 11 | 348 |
| E6 | 9 | 40 |
| L2 | 11 | 61 |
| E1 | 8 | 572 |
| L1 | 8 | 408 |
| L1 | 9 | 377 |
| E2 | 11 | 128 |
| L1 | 8 | 351 |

TABLE XV-continued

A. HPV6A
HLA-A 1 Motif Peptides

| 2 | 3 | 4 |
|---|---|---|
| L1 | 10 | 427 |
| E1 | 9 | 129 |
| E1 | 11 | 129 |
| L1 | 10 | 346 |
| L1 | 5 | 280 |
| E5 | 11 | 44 |
| E6 | 8 | 39 |
| E6 | 10 | 39 |
| L1 | 8 | 223 |
| L1 | 11 | 345 |
| L2 | 11 | 339 |
| E2 | 8 | 152 |
| E2 | 11 | 148 |
| E1 | 11 | 403 |
| E1 | 8 | 79 |
| L1 | 10 | 114 |
| E2 | 9 | 206 |
| L1 | 10 | 17 |
| L2 | 8 | 364 |
| L1 | 8 | 27 |
| E5 | 8 | 36 |
| E2 | 8 | 92 |
| E2 | 11 | 178 |
| L1 | 11 | 355 |
| E4 | 8 | 12 |
| L1 | 8 | 358 |
| E2 | 9 | 159 |
| E2 | 10 | 159 |
| L1 | 9 | 350 |

TABLE XV

B. HPV6B
HLA-A1 Motif Peptides

| 2 | 3 | 4 |
|---|---|---|
| L2 | 11 | 286 |
| L2 | 9 | 341 |
| L2 | 9 | 288 |
| L1 | 9 | 342 |
| E1 | 8 | 525 |
| E1 | 10 | 77 |
| L1 | 10 | 341 |
| E1 | 10 | 371 |
| E6 | 11 | 67 |
| E2 | 10 | 35 |
| E5B | 10 | 53 |
| E5A | 8 | 77 |
| E5A | 9 | 77 |
| E2 | 9 | 11 |
| E1 | 9 | 405 |
| E1 | 10 | 523 |
| E1 | 11 | 35 |
| E1 | 9 | 37 |
| E1 | 10 | 36 |
| E1 | 9 | 372 |
| L1 | 8 | 429 |
| E1 | 8 | 373 |
| E2 | 8 | 80 |
| E2 | 10 | 293 |
| E2 | 10 | 205 |
| L2 | 11 | 239 |
| L1 | 8 | 450 |
| E2 | 9 | 123 |
| E2 | 11 | 292 |
| E5B | 10 | 25 |
| L2 | 11 | 431 |
| L2 | 10 | 62 |
| E2 | 10 | 179 |
| L2 | 11 | 215 |

TABLE XV-continued

B. HPV6B
HLA-A1 Motif Peptides

| 2 | 3 | 4 |
|---|---|---|
| L2 | 8 | 64 |
| L1 | 9 | 407 |
| L1 | 9 | 222 |
| L1 | 11 | 113 |
| E2 | 10 | 78 |
| E2 | 10 | 149 |
| E2 | 11 | 149 |
| L2 | 10 | 287 |
| E1 | 11 | 370 |
| L2 | 9 | 313 |
| E6 | 9 | 97 |
| E1 | 9 | 313 |
| E1 | 9 | 571 |
| L1 | 10 | 376 |
| L2 | 8 | 247 |
| L1 | 9 | 449 |
| E2 | 9 | 329 |
| E6 | 10 | 35 |
| L2 | 9 | 10 |
| L1 | 10 | 56 |
| L1 | 11 | 340 |
| E1 | 11 | 522 |
| E2 | 9 | 79 |
| E1 | 8 | 255 |
| L1 | 8 | 41 |
| E1 | 9 | 394 |
| L1 | 8 | 378 |
| L2 | 10 | 240 |
| E1 | 8 | 132 |
| E1 | 9 | 358 |
| E6 | 9 | 38 |
| E6 | 11 | 38 |
| E4 | 9 | 1 |
| E2 | 8 | 151 |
| E2 | 9 | 151 |
| E5B | 9 | 54 |
| E1 | 10 | 568 |
| E1 | 8 | 395 |
| E1 | 10 | 594 |
| L1 | 11 | 217 |
| E7 | 10 | 17 |
| E1 | 8 | 479 |
| L1 | 11 | 426 |
| L1 | 11 | 16 |
| L2 | 8 | 342 |
| E1 | 8 | 314 |
| E1 | 10 | 128 |
| L2 | 8 | 11 |
| E2 | 8 | 37 |
| L1 | 8 | 3 |
| E1 | 8 | 69 |
| L1 | 9 | 279 |
| L1 | 10 | 298 |
| E2 | 9 | 150 |
| E2 | 10 | 150 |
| L1 | 11 | 297 |
| L1 | 11 | 38 |
| L1 | 9 | 347 |
| E2 | 9 | 180 |
| L2 | 9 | 241 |
| L1 | 8 | 348 |
| L1 | 11 | 348 |
| E6 | 9 | 40 |
| L2 | 11 | 61 |
| E1 | 8 | 572 |
| L1 | 8 | 408 |
| L1 | 9 | 377 |
| E2 | 11 | 128 |
| E5B | 10 | 59 |
| L1 | 8 | 351 |
| L1 | 10 | 427 |
| E1 | 9 | 129 |
| E1 | 11 | 129 |
| L1 | 10 | 346 |

TABLE XV-continued

B. HPV6B
HLA-A1 Motif Peptides

| 2 | 3 | 4 |
|---|---|---|
| L1 | 8 | 280 |
| E5A | 11 | 44 |
| E6 | 8 | 39 |
| E6 | 10 | 39 |
| L1 | 8 | 223 |
| E5B | 8 | 63 |
| L1 | 11 | 345 |
| L2 | 11 | 339 |
| E2 | 8 | 152 |
| E2 | 11 | 148 |
| E1 | 11 | 403 |
| E1 | 8 | 79 |
| L1 | 10 | 114 |
| E2 | 9 | 206 |
| L1 | 10 | 17 |
| E5B | 11 | 58 |
| L2 | 8 | 364 |
| L1 | 8 | 27 |
| E5A | 8 | 36 |
| E2 | 8 | 92 |
| E2 | 11 | 178 |
| L1 | 11 | 355 |
| E4 | 8 | 22 |
| L1 | 8 | 358 |
| E2 | 9 | 159 |
| E2 | 10 | 159 |
| L1 | 9 | 350 |
| E5B | 9 | 62 |

TABLE XV

C. HPV11
HLA-A1 Motif Peptides

| 2 | 3 | 4 |
|---|---|---|
| L2 | 10 | 339 |
| L2 | 9 | 62 |
| L1 | 9 | 343 |
| E1 | 8 | 525 |
| E1 | 10 | 77 |
| L1 | 8 | 349 |
| L1 | 11 | 349 |
| L1 | 10 | 342 |
| E2 | 8 | 124 |
| E1 | 10 | 371 |
| E5 | 11 | 49 |
| E6 | 11 | 67 |
| E2 | 9 | 11 |
| E1 | 9 | 405 |
| E1 | 10 | 523 |
| E1 | 11 | 35 |
| E1 | 8 | 570 |
| E1 | 10 | 570 |
| E2 | 10 | 292 |
| L1 | 8 | 125 |
| E1 | 10 | 36 |
| E1 | 9 | 37 |
| E1 | 9 | 372 |
| L1 | 8 | 430 |
| L2 | 8 | 341 |
| E1 | 8 | 373 |
| E2 | 8 | 80 |
| E1 | 10 | 128 |
| E2 | 10 | 205 |
| L2 | 11 | 238 |
| E5 | 9 | 77 |
| L2 | 11 | 295 |
| E2 | 9 | 123 |
| E2 | 11 | 291 |
| L2 | 11 | 427 |
| L2 | 8 | 63 |
| E2 | 10 | 179 |
| L1 | 9 | 408 |
| L1 | 9 | 223 |
| L1 | 11 | 113 |
| E5 | 9 | 64 |
| E2 | 10 | 78 |
| E1 | 11 | 370 |
| E1 | 9 | 313 |
| E1 | 9 | 571 |
| L1 | 10 | 377 |
| E1 | 10 | 420 |
| E2 | 9 | 328 |
| E7 | 11 | 42 |
| L2 | 9 | 9 |
| L1 | 10 | 347 |
| E5 | 10 | 50 |
| L1 | 10 | 56 |
| L1 | 11 | 122 |
| L1 | 11 | 341 |
| E1 | 11 | 522 |
| E2 | 9 | 79 |
| E1 | 8 | 255 |
| E5 | 8 | 36 |
| L1 | 8 | 41 |
| L1 | 9 | 41 |
| E1 | 9 | 394 |
| L1 | 8 | 379 |
| L2 | 10 | 239 |
| E1 | 8 | 132 |
| E1 | 9 | 358 |
| E6 | 9 | 38 |
| E6 | 11 | 38 |
| E5 | 9 | 62 |
| E5 | 11 | 62 |
| E1 | 9 | 421 |
| E1 | 10 | 568 |
| L1 | 10 | 279 |
| E1 | 8 | 395 |
| E5 | 8 | 54 |
| E1 | 10 | 594 |
| L1 | 11 | 218 |
| E7 | 10 | 17 |
| L1 | 11 | 427 |
| L1 | 11 | 16 |
| E7 | 10 | 43 |
| L2 | 8 | 360 |
| E1 | 8 | 314 |
| L2 | 8 | 10 |
| E6 | 10 | 35 |
| L1 | 8 | 3 |
| E1 | 8 | 69 |
| L1 | 9 | 280 |
| L1 | 10 | 299 |
| E2 | 8 | 207 |
| E1 | 8 | 572 |
| L1 | 11 | 346 |
| L1 | 11 | 298 |
| L1 | 11 | 38 |
| L1 | 8 | 281 |
| E2 | 9 | 150 |
| E2 | 10 | 150 |
| E2 | 11 | 260 |
| E2 | 9 | 180 |
| L2 | 9 | 240 |
| E2 | 8 | 151 |
| E2 | 9 | 151 |
| L1 | 8 | 344 |
| E6 | 9 | 40 |
| L2 | 11 | 60 |
| L1 | 8 | 409 |
| L1 | 9 | 378 |
| L1 | 8 | 352 |
| L1 | 10 | 428 |

TABLE XV-continued

C. HPV11
HLA-A 1 Motif Peptides

| 2 | 3 | 4 |
|---|---|---|
| E1 | 9 | 129 |
| E1 | 11 | 129 |
| E2 | 10 | 149 |
| E2 | 11 | 149 |
| E5 | 11 | 44 |
| E6 | 8 | 39 |
| E6 | 10 | 39 |
| L2 | 11 | 338 |
| E2 | 8 | 152 |
| E1 | 11 | 403 |
| E2 | 11 | 128 |
| E1 | 8 | 79 |
| L1 | 10 | 114 |
| E2 | 9 | 206 |
| L1 | 10 | 17 |
| E2 | 11 | 148 |
| L2 | 8 | 246 |
| E2 | 8 | 92 |
| L1 | 10 | 123 |
| L1 | 8 | 239 |
| E2 | 11 | 178 |
| E4 | 8 | 22 |
| E5 | 10 | 61 |
| E2 | 9 | 159 |
| E2 | 10 | 159 |
| L1 | 9 | 351 |

TABLE XVI

HLA-A3 Motif Peptides

| 1 | 2 | 3 | 4 |
|---|---|---|---|
| HPV16 | E1 | 8 | 316 |
| HPV16 | E1 | 10 | 239 |
| HPV16 | E1 | 8 | 205 |
| HPV16 | E1 | 11 | 205 |
| HPV16 | E1 | 9 | 478 |
| HPV16 | E1 | 11 | 514 |
| HPV16 | E1 | 11 | 248 |
| HPV16 | E1 | 9 | 383 |
| HPV16 | E1 | 10 | 383 |
| HPV16 | E1 | 9 | 240 |
| HPV16 | E1 | 9 | 391 |
| HPV16 | E1 | 10 | 391 |
| HPV16 | E1 | 9 | 570 |
| HPV16 | E1 | 11 | 570 |
| HPV16 | E1 | 9 | 112 |
| HPV16 | E1 | 10 | 112 |
| HPV16 | E1 | 11 | 112 |
| HPV16 | E1 | 8 | 69 |
| HPV16 | E1 | 9 | 69 |
| HPV16 | E1 | 11 | 69 |
| HPV16 | E1 | 11 | 459 |
| HPV16 | E1 | 10 | 206 |
| HPV16 | E1 | 11 | 389 |
| HPV16 | E1 | 8 | 406 |
| HPV16 | E1 | 9 | 406 |
| HPV16 | E1 | 10 | 406 |
| HPV16 | E1 | 8 | 524 |
| HPV16 | E1 | 8 | 82 |
| HPV16 | E1 | 9 | 82 |
| HPV16 | E1 | 10 | 23 |
| HPV16 | E1 | 8 | 405 |
| HPV16 | E1 | 9 | 405 |
| HPV16 | E1 | 10 | 405 |
| HPV16 | E1 | 11 | 405 |
| HPV16 | E1 | 8 | 233 |
| HPV16 | E1 | 9 | 233 |
| HPV16 | E1 | 11 | 430 |
| HPV16 | E1 | 8 | 234 |

TABLE XVI-continued

HLA-A3 Motif Peptides

| 1 | 2 | 3 | 4 |
|---|---|---|---|
| HPV16 | E1 | 8 | 500 |
| HPV16 | E1 | 9 | 500 |
| HPV16 | E1 | 10 | 283 |
| HPV16 | E1 | 8 | 114 |
| HPV16 | E1 | 9 | 114 |
| HPV16 | E1 | 10 | 114 |
| HPV16 | E1 | 11 | 114 |
| HPV16 | E1 | 8 | 472 |
| HPV16 | E1 | 10 | 259 |
| HPV16 | E1 | 8 | 304 |
| HPV16 | E1 | 10 | 304 |
| HPV16 | E1 | 9 | 101 |
| HPV16 | E1 | 11 | 101 |
| HPV16 | E1 | 10 | 515 |
| HPV16 | E1 | 9 | 523 |
| HPV16 | E1 | 8 | 81 |
| HPV16 | E1 | 9 | 81 |
| HPV16 | E1 | 10 | 81 |
| HPV16 | E1 | 8 | 404 |
| HPV16 | E1 | 9 | 404 |
| HPV16 | E1 | 10 | 404 |
| HPV16 | E1 | 11 | 404 |
| HPV16 | E1 | 10 | 522 |
| HPV16 | E1 | 8 | 371 |
| HPV16 | E1 | 9 | 371 |
| HPV16 | E1 | 10 | 371 |
| HPV16 | E1 | 9 | 50 |
| HPV16 | E1 | 8 | 631 |
| HPV16 | E1 | 9 | 631 |
| HPV16 | E1 | 11 | 435 |
| HPV16 | E1 | 10 | 541 |
| HPV16 | E1 | 11 | 541 |
| HPV16 | E1 | 9 | 368 |
| HPV16 | E1 | 10 | 368 |
| HPV16 | E1 | 11 | 368 |
| HPV16 | E1 | 11 | 41 |
| HPV16 | E1 | 8 | 372 |
| HPV16 | E1 | 9 | 372 |
| HPV16 | E1 | 10 | 249 |
| HPV16 | E1 | 8 | 573 |
| HPV16 | E1 | 10 | 573 |
| HPV16 | E1 | 9 | 43 |
| HPV16 | E1 | 8 | 384 |
| HPV16 | E1 | 9 | 384 |
| HPV16 | E1 | 11 | 384 |
| HPV16 | E1 | 8 | 335 |
| HPV16 | E1 | 11 | 548 |
| HPV16 | E1 | 8 | 75 |
| HPV16 | E1 | 11 | 22 |
| HPV16 | E1 | 8 | 452 |
| HPV16 | E1 | 10 | 452 |
| HPV16 | E1 | 11 | 452 |
| HPV16 | E1 | 9 | 11 |
| HPV16 | E1 | 10 | 11 |
| HPV16 | E1 | 10 | 374 |
| HPV16 | E1 | 8 | 603 |
| HPV16 | E1 | 10 | 603 |
| HPV16 | E1 | 11 | 603 |
| HPV16 | E1 | 9 | 356 |
| HPV16 | E1 | 10 | 356 |
| HPV16 | E1 | 10 | 221 |
| HPV16 | E1 | 9 | 65 |
| HPV16 | E1 | 9 | 63 |
| HPV16 | E1 | 11 | 63 |
| HPV16 | E1 | 9 | 152 |
| HPV16 | E1 | 9 | 288 |
| HPV16 | E1 | 11 | 140 |
| HPV16 | E1 | 9 | 594 |
| HPV16 | E1 | 8 | 612 |
| HPV16 | E1 | 8 | 241 |
| HPV16 | E1 | 8 | 486 |
| HPV16 | E1 | 8 | 51 |
| HPV16 | E1 | 8 | 392 |
| HPV16 | E1 | 9 | 392 |
| HPV16 | E1 | 8 | 463 |

TABLE XVI-continued

HLA-A3 Motif Peptides

| 1 | 2 | 3 | 4 |
|---|---|---|---|
| HPV16 | E1 | 9 | 493 |
| HPV16 | E1 | 9 | 445 |
| HPV16 | E1 | 8 | 456 |
| HPV16 | E1 | 9 | 453 |
| HPV16 | E1 | 10 | 453 |
| HPV16 | E1 | 11 | 453 |
| HPV16 | E1 | 8 | 219 |
| HPV16 | E1 | 9 | 219 |
| HPV16 | E1 | 11 | 613 |
| HPV16 | E1 | 9 | 71 |
| HPV16 | E1 | 10 | 71 |
| HPV16 | E1 | 9 | 586 |
| HPV16 | E1 | 8 | 501 |
| HPV16 | E1 | 10 | 477 |
| HPV16 | E1 | 10 | 14 |
| HPV16 | E1 | 10 | 100 |
| HPV16 | E1 | 8 | 632 |
| HPV16 | E1 | 9 | 334 |
| HPV16 | E1 | 9 | 437 |
| HPV16 | E1 | 11 | 437 |
| HPV16 | E1 | 10 | 436 |
| HPV16 | E1 | 8 | 176 |
| HPV16 | E1 | 9 | 176 |
| HPV16 | E1 | 10 | 162 |
| HPV16 | E1 | 11 | 466 |
| HPV16 | E1 | 9 | 325 |
| HPV16 | E1 | 11 | 242 |
| HPV16 | E1 | 9 | 272 |
| HPV16 | E1 | 10 | 272 |
| HPV16 | E1 | 11 | 272 |
| HPV16 | E1 | 10 | 174 |
| HPV16 | E1 | 11 | 174 |
| HPV16 | E1 | 9 | 163 |
| HPV16 | E1 | 10 | 496 |
| HPV16 | E1 | 8 | 571 |
| HPV16 | E1 | 10 | 571 |
| HPV16 | E1 | 8 | 12 |
| HPV16 | E1 | 9 | 12 |
| HPV16 | E1 | 10 | 450 |
| HPV16 | E1 | 9 | 216 |
| HPV16 | E1 | 11 | 216 |
| HPV16 | E1 | 9 | 68 |
| HPV16 | E1 | 10 | 68 |
| HPV16 | E1 | 8 | 507 |
| HPV16 | E1 | 10 | 507 |
| HPV16 | E1 | 11 | 507 |
| HPV16 | E1 | 8 | 348 |
| HPV16 | E1 | 11 | 238 |
| HPV16 | E1 | 9 | 375 |
| HPV16 | E1 | 9 | 499 |
| HPV16 | E1 | 10 | 499 |
| HPV16 | E1 | 8 | 113 |
| HPV16 | E1 | 9 | 113 |
| HPV16 | E1 | 10 | 113 |
| HPV16 | E1 | 11 | 113 |
| HPV16 | E1 | 8 | 532 |
| HPV16 | E1 | 11 | 473 |
| HPV16 | E1 | 10 | 194 |
| HPV16 | E1 | 11 | 194 |
| HPV16 | E1 | 8 | 326 |
| HPV16 | E1 | 8 | 369 |
| HPV16 | E1 | 9 | 369 |
| HPV16 | E1 | 10 | 369 |
| HPV16 | E1 | 11 | 369 |
| HPV16 | E1 | 10 | 401 |
| HPV16 | E1 | 11 | 401 |
| HPV16 | E1 | 11 | 52 |
| HPV16 | E1 | 8 | 204 |
| HPV16 | E1 | 9 | 204 |
| HPV16 | E1 | 10 | 111 |
| HPV16 | E1 | 11 | 111 |
| HPV16 | E1 | 11 | 282 |
| HPV16 | E1 | 8 | 403 |
| HPV16 | E1 | 9 | 403 |
| HPV16 | E1 | 10 | 403 |
| HPV16 | E1 | 11 | 403 |
| HPV16 | E1 | 10 | 210 |
| HPV16 | E1 | 10 | 492 |
| HPV16 | E1 | 8 | 517 |
| HPV16 | E1 | 11 | 400 |
| HPV16 | E1 | 8 | 311 |
| HPV16 | E1 | 10 | 311 |
| HPV16 | E1 | 10 | 610 |
| HPV16 | E1 | 10 | 505 |
| HPV16 | E1 | 10 | 483 |
| HPV16 | E1 | 11 | 483 |
| HPV16 | E1 | 10 | 394 |
| HPV16 | E1 | 10 | 230 |
| HPV16 | E1 | 11 | 230 |
| HPV16 | E1 | 11 | 323 |
| HPV16 | E1 | 10 | 252 |
| HPV16 | E1 | 8 | 199 |
| HPV16 | E1 | 11 | 199 |
| HPV16 | E1 | 8 | 382 |
| HPV16 | E1 | 10 | 382 |
| HPV16 | E1 | 11 | 382 |
| HPV16 | E1 | 8 | 208 |
| HPV16 | E1 | 11 | 521 |
| HPV16 | E1 | 11 | 540 |
| HPV16 | E1 | 9 | 126 |
| HPV16 | E1 | 8 | 485 |
| HPV16 | E1 | 9 | 485 |
| HPV16 | E1 | 8 | 70 |
| HPV16 | E1 | 10 | 70 |
| HPV16 | E1 | 11 | 70 |
| HPV16 | E1 | 8 | 563 |
| HPV16 | E1 | 9 | 562 |
| HPV16 | E1 | 10 | 276 |
| HPV16 | E1 | 8 | 254 |
| HPV16 | E1 | 10 | 254 |
| HPV16 | E1 | 9 | 277 |
| HPV16 | E1 | 11 | 277 |
| HPV16 | E1 | 10 | 474 |
| HPV16 | E1 | 9 | 620 |
| HPV16 | E1 | 8 | 357 |
| HPV16 | E1 | 9 | 357 |
| HPV16 | E1 | 9 | 191 |
| HPV16 | E1 | 10 | 243 |
| HPV16 | E1 | 9 | 59 |
| HPV16 | E1 | 10 | 59 |
| HPV16 | E1 | 11 | 59 |
| HPV16 | E1 | 11 | 48 |
| HPV16 | E1 | 9 | 222 |
| HPV16 | E1 | 8 | 278 |
| HPV16 | E1 | 10 | 278 |
| HPV16 | E1 | 8 | 544 |
| HPV16 | E1 | 9 | 544 |
| HPV16 | E1 | 10 | 583 |
| HPV16 | E1 | 9 | 303 |
| HPV16 | E1 | 11 | 303 |
| HPV16 | E1 | 8 | 408 |
| HPV16 | E1 | 10 | 408 |
| HPV16 | E1 | 11 | 408 |
| HPV16 | E1 | 10 | 444 |
| HPV16 | E1 | 8 | 306 |
| HPV16 | E1 | 11 | 306 |
| HPV16 | E1 | 9 | 207 |
| HPV16 | E1 | 8 | 144 |
| HPV16 | E1 | 9 | 305 |
| HPV16 | E1 | 8 | 454 |
| HPV16 | E1 | 9 | 454 |
| HPV16 | E1 | 10 | 454 |
| HPV16 | E1 | 8 | 420 |
| HPV16 | E1 | 9 | 420 |
| HPV16 | E1 | 10 | 420 |
| HPV16 | E1 | 8 | 422 |
| HPV16 | E1 | 11 | 422 |
| HPV16 | E1 | 8 | 273 |
| HPV16 | E1 | 9 | 273 |
| HPV16 | E1 | 10 | 273 |

TABLE XVI-continued

HLA-A3 Motif Peptides

| 1 | 2 | 3 | 4 |
|---|---|---|---|
| HPV16 | E1 | 10 | 569 |
| HPV16 | E1 | 8 | 202 |
| HPV16 | E1 | 9 | 202 |
| HPV16 | E1 | 10 | 202 |
| HPV16 | E1 | 11 | 202 |
| HPV16 | E1 | 8 | 471 |
| HPV16 | E1 | 9 | 471 |
| HPV16 | E1 | 9 | 630 |
| HPV16 | E1 | 10 | 630 |
| HPV16 | E1 | 10 | 367 |
| HPV16 | E1 | 11 | 367 |
| HPV16 | E1 | 8 | 605 |
| HPV16 | E1 | 9 | 605 |
| HPV16 | E1 | 11 | 605 |
| HPV16 | E1 | 9 | 54 |
| HPV16 | E1 | 11 | 597 |
| HPV16 | E1 | 8 | 16 |
| HPV16 | E1 | 11 | 193 |
| HPV16 | E1 | 9 | 567 |
| HPV16 | E1 | 8 | 105 |
| HPV16 | E1 | 8 | 543 |
| HPV16 | E1 | 9 | 543 |
| HPV16 | E1 | 10 | 543 |
| HPV16 | E1 | 9 | 386 |
| HPV16 | E1 | 8 | 396 |
| HPV16 | E1 | 11 | 396 |
| HPV16 | E1 | 8 | 196 |
| HPV16 | E1 | 9 | 196 |
| HPV16 | E1 | 10 | 196 |
| HPV16 | E1 | 11 | 196 |
| HPV16 | E1 | 11 | 527 |
| HPV16 | E1 | 10 | 593 |
| HPV16 | E1 | 10 | 561 |
| HPV16 | E1 | 10 | 190 |
| HPV16 | E1 | 10 | 302 |
| HPV16 | E1 | 8 | 245 |
| HPV16 | E1 | 8 | 600 |
| HPV16 | E1 | 11 | 600 |
| HPV16 | E1 | 8 | 61 |
| HPV16 | E1 | 9 | 61 |
| HPV16 | E1 | 11 | 61 |
| HPV16 | E1 | 9 | 398 |
| HPV16 | E1 | 11 | 495 |
| HPV16 | E1 | 8 | 449 |
| HPV16 | E1 | 11 | 449 |
| HPV16 | E1 | 8 | 441 |
| HPV16 | E1 | 9 | 381 |
| HPV16 | E1 | 11 | 381 |
| HPV16 | E1 | 8 | 143 |
| HPV16 | E1 | 9 | 143 |
| HPV16 | E1 | 9 | 419 |
| HPV16 | E1 | 10 | 419 |
| HPV16 | E1 | 11 | 419 |
| HPV16 | E1 | 8 | 118 |
| HPV16 | E1 | 10 | 118 |
| HPV16 | E1 | 8 | 343 |
| HPV16 | E1 | 8 | 120 |
| HPV16 | E1 | 8 | 80 |
| HPV16 | E1 | 9 | 80 |
| HPV16 | E1 | 10 | 80 |
| HPV16 | E1 | 11 | 80 |
| HPV16 | E1 | 8 | 462 |
| HPV16 | E1 | 9 | 462 |
| HPV16 | E1 | 10 | 125 |
| HPV16 | E1 | 9 | 109 |
| HPV16 | E1 | 10 | 619 |
| HPV16 | E1 | 11 | 582 |
| HPV16 | E1 | 8 | 313 |
| HPV16 | E1 | 10 | 313 |
| HPV16 | E1 | 11 | 313 |
| HPV16 | E1 | 9 | 615 |
| HPV16 | E1 | 9 | 432 |
| HPV16 | E1 | 10 | 390 |
| HPV16 | E1 | 11 | 390 |
| HPV16 | E1 | 10 | 42 |
| HPV16 | E1 | 9 | 611 |
| HPV16 | E1 | 8 | 455 |
| HPV16 | E1 | 9 | 455 |
| HPV16 | E1 | 9 | 218 |
| HPV16 | E1 | 10 | 218 |
| HPV16 | E1 | 11 | 99 |
| HPV16 | E1 | 9 | 175 |
| HPV16 | E1 | 10 | 175 |
| HPV16 | E1 | 8 | 164 |
| HPV16 | E1 | 11 | 161 |
| HPV16 | E1 | 11 | 173 |
| HPV16 | E1 | 9 | 250 |
| HPV16 | E1 | 9 | 484 |
| HPV16 | E1 | 10 | 484 |
| HPV16 | E1 | 8 | 621 |
| HPV16 | E1 | 8 | 421 |
| HPV16 | E1 | 9 | 421 |
| HPV16 | E1 | 9 | 314 |
| HPV16 | E1 | 10 | 314 |
| HPV16 | E1 | 9 | 231 |
| HPV16 | E1 | 10 | 231 |
| HPV16 | E1 | 11 | 231 |
| HPV16 | E1 | 9 | 497 |
| HPV16 | E1 | 11 | 497 |
| HPV16 | E1 | 8 | 315 |
| HPV16 | E1 | 9 | 315 |
| HPV16 | E1 | 8 | 66 |
| HPV16 | E1 | 11 | 66 |
| HPV16 | E1 | 8 | 72 |
| HPV16 | E1 | 9 | 72 |
| HPV16 | E1 | 11 | 72 |
| HPV16 | E1 | 8 | 232 |
| HPV16 | E1 | 9 | 232 |
| HPV16 | E1 | 10 | 232 |
| HPV16 | E1 | 9 | 572 |
| HPV16 | E1 | 11 | 572 |
| HPV16 | E1 | 11 | 354 |
| HPV16 | E1 | 8 | 587 |
| HPV16 | E1 | 8 | 13 |
| HPV16 | E1 | 11 | 13 |
| HPV16 | E1 | 8 | 44 |
| HPV16 | E1 | 10 | 324 |
| HPV16 | E1 | 8 | 289 |
| HPV16 | E1 | 9 | 253 |
| HPV16 | E1 | 11 | 253 |
| HPV16 | E1 | 8 | 407 |
| HPV16 | E1 | 9 | 407 |
| HPV16 | E1 | 11 | 407 |
| HPV16 | E1 | 10 | 200 |
| HPV16 | E1 | 11 | 200 |
| HPV16 | E1 | 11 | 565 |
| HPV16 | E1 | 8 | 433 |
| HPV16 | E1 | 8 | 370 |
| HPV16 | E1 | 9 | 370 |
| HPV16 | E1 | 10 | 370 |
| HPV16 | E1 | 11 | 370 |
| HPV16 | E1 | 10 | 49 |
| HPV16 | E1 | 8 | 102 |
| HPV16 | E1 | 10 | 102 |
| HPV16 | E1 | 11 | 102 |
| HPV16 | E1 | 8 | 585 |
| HPV16 | E1 | 10 | 585 |
| HPV16 | E1 | 8 | 498 |
| HPV16 | E1 | 10 | 498 |
| HPV16 | E1 | 11 | 498 |
| HPV16 | E1 | 8 | 197 |
| HPV16 | E1 | 9 | 197 |
| HPV16 | E1 | 10 | 197 |
| HPV16 | E1 | 8 | 275 |
| HPV16 | E1 | 11 | 275 |
| HPV16 | E1 | 11 | 345 |
| HPV16 | E1 | 11 | 443 |
| HPV16 | E1 | 8 | 217 |
| HPV16 | E1 | 10 | 217 |
| HPV16 | E1 | 11 | 217 |

TABLE XVI-continued

HLA-A3 Motif Peptides

| 1 | 2 | 3 | 4 |
|---|---|---|---|
| HPV16 | E1 | 8 | 545 |
| HPV16 | E1 | 9 | 24 |
| HPV16 | E1 | 9 | 584 |
| HPV16 | E1 | 11 | 584 |
| HPV16 | E1 | 8 | 274 |
| HPV16 | E1 | 9 | 274 |
| HPV16 | E1 | 10 | 18 |
| HPV16 | E1 | 11 | 18 |
| HPV16 | E1 | 10 | 271 |
| HPV16 | E1 | 11 | 271 |
| HPV16 | E1 | 8 | 425 |
| HPV16 | E1 | 10 | 339 |
| HPV16 | E1 | 8 | 509 |
| HPV16 | E1 | 9 | 509 |
| HPV16 | E1 | 11 | 379 |
| HPV16 | E1 | 11 | 258 |
| HPV16 | E1 | 8 | 476 |
| HPV16 | E1 | 11 | 476 |
| HPV16 | E1 | 10 | 333 |
| HPV16 | E1 | 10 | 215 |
| HPV16 | E1 | 9 | 531 |
| HPV16 | E1 | 8 | 261 |
| HPV16 | E1 | 9 | 578 |
| HPV16 | E1 | 11 | 578 |
| HPV16 | E1 | 10 | 58 |
| HPV16 | E1 | 11 | 58 |
| HPV16 | E1 | 8 | 20 |
| HPV16 | E1 | 9 | 20 |
| HPV16 | E2 | 9 | 220 |
| HPV16 | E2 | 9 | 270 |
| HPV16 | E2 | 11 | 41 |
| HPV16 | E2 | 8 | 221 |
| HPV16 | E2 | 10 | 63 |
| HPV16 | E2 | 11 | 314 |
| HPV16 | E2 | 8 | 40 |
| HPV16 | E2 | 8 | 300 |
| HPV16 | E2 | 9 | 300 |
| HPV16 | E2 | 9 | 174 |
| HPV16 | E2 | 9 | 294 |
| HPV16 | E2 | 10 | 294 |
| HPV16 | E2 | 11 | 294 |
| HPV16 | E2 | 8 | 173 |
| HPV16 | E2 | 10 | 173 |
| HPV16 | E2 | 9 | 122 |
| HPV16 | E2 | 10 | 122 |
| HPV16 | E2 | 8 | 124 |
| HPV16 | E2 | 8 | 25 |
| HPV16 | E2 | 10 | 25 |
| HPV16 | E2 | 11 | 25 |
| HPV16 | E2 | 8 | 263 |
| HPV16 | E2 | 9 | 263 |
| HPV16 | E2 | 9 | 338 |
| HPV16 | E2 | 8 | 22 |
| HPV16 | E2 | 11 | 22 |
| HPV16 | E2 | 11 | 260 |
| HPV16 | E2 | 10 | 246 |
| HPV16 | E2 | 10 | 96 |
| HPV16 | E2 | 8 | 39 |
| HPV16 | E2 | 9 | 39 |
| HPV16 | E2 | 10 | 162 |
| HPV16 | E2 | 11 | 162 |
| HPV16 | E2 | 10 | 149 |
| HPV16 | E2 | 11 | 149 |
| HPV16 | E2 | 8 | 209 |
| HPV16 | E2 | 10 | 209 |
| HPV16 | E2 | 10 | 74 |
| HPV16 | E2 | 9 | 48 |
| HPV16 | E2 | 8 | 80 |
| HPV16 | E2 | 8 | 233 |
| HPV16 | E2 | 10 | 233 |
| HPV16 | E2 | 9 | 204 |
| HPV16 | E2 | 11 | 204 |
| HPV16 | E2 | 10 | 121 |
| HPV16 | E2 | 11 | 121 |
| HPV16 | E2 | 9 | 346 |
| HPV16 | E2 | 8 | 168 |
| HPV16 | E2 | 10 | 168 |
| HPV16 | E2 | 11 | 168 |
| HPV16 | E2 | 8 | 108 |
| HPV16 | E2 | 10 | 293 |
| HPV16 | E2 | 11 | 293 |
| HPV16 | E2 | 8 | 123 |
| HPV16 | E2 | 9 | 123 |
| HPV16 | E2 | 9 | 163 |
| HPV16 | E2 | 10 | 163 |
| HPV16 | E2 | 10 | 156 |
| HPV16 | E2 | 11 | 230 |
| HPV16 | E2 | 9 | 113 |
| HPV16 | E2 | 9 | 29 |
| HPV16 | E2 | 11 | 53 |
| HPV16 | E2 | 8 | 136 |
| HPV16 | E2 | 8 | 214 |
| HPV16 | E2 | 10 | 214 |
| HPV16 | E2 | 10 | 290 |
| HPV16 | E2 | 9 | 35 |
| HPV16 | E2 | 10 | 35 |
| HPV16 | E2 | 11 | 35 |
| HPV16 | E2 | 8 | 252 |
| HPV16 | E2 | 8 | 30 |
| HPV16 | E2 | 9 | 210 |
| HPV16 | E2 | 11 | 210 |
| HPV16 | E2 | 8 | 193 |
| HPV16 | E2 | 9 | 267 |
| HPV16 | E2 | 10 | 267 |
| HPV16 | E2 | 8 | 288 |
| HPV16 | E2 | 8 | 45 |
| HPV16 | E2 | 9 | 45 |
| HPV16 | E2 | 8 | 299 |
| HPV16 | E2 | 9 | 299 |
| HPV16 | E2 | 10 | 299 |
| HPV16 | E2 | 9 | 172 |
| HPV16 | E2 | 11 | 172 |
| HPV16 | E2 | 8 | 292 |
| HPV16 | E2 | 11 | 292 |
| HPV16 | E2 | 11 | 255 |
| HPV16 | E2 | 9 | 329 |
| HPV16 | E2 | 9 | 354 |
| HPV16 | E2 | 9 | 215 |
| HPV16 | E2 | 11 | 215 |
| HPV16 | E2 | 8 | 62 |
| HPV16 | E2 | 11 | 62 |
| HPV16 | E2 | 11 | 4 |
| HPV16 | E2 | 10 | 256 |
| HPV16 | E2 | 8 | 347 |
| HPV16 | E2 | 8 | 268 |
| HPV16 | E2 | 9 | 268 |
| HPV16 | E2 | 11 | 268 |
| HPV16 | E2 | 9 | 103 |
| HPV16 | E2 | 10 | 103 |
| HPV16 | E2 | 11 | 103 |
| HPV16 | E2 | 11 | 77 |
| HPV16 | E2 | 9 | 335 |
| HPV16 | E2 | 8 | 49 |
| HPV16 | E2 | 11 | 280 |
| HPV16 | E2 | 9 | 21 |
| HPV16 | E2 | 9 | 282 |
| HPV16 | E2 | 11 | 282 |
| HPV16 | E2 | 8 | 84 |
| HPV16 | E2 | 8 | 296 |
| HPV16 | E2 | 9 | 296 |
| HPV16 | E2 | 10 | 296 |
| HPV16 | E2 | 11 | 296 |
| HPV16 | E2 | 10 | 127 |
| HPV16 | E2 | 9 | 284 |
| HPV16 | E2 | 10 | 9 |
| HPV16 | E2 | 11 | 9 |
| HPV16 | E2 | 8 | 219 |
| HPV16 | E2 | 10 | 219 |
| HPV16 | E2 | 9 | 250 |
| HPV16 | E2 | 10 | 250 |

TABLE XVI-continued

HLA-A3 Motif Peptides

| 1 | 2 | 3 | 4 |
|---|---|---|---|
| HPV16 | E2 | 8 | 245 |
| HPV16 | E2 | 11 | 245 |
| HPV16 | E2 | 10 | 266 |
| HPV16 | E2 | 11 | 266 |
| HPV16 | E2 | 9 | 287 |
| HPV16 | E2 | 8 | 106 |
| HPV16 | E2 | 10 | 106 |
| HPV16 | E2 | 9 | 60 |
| HPV16 | E2 | 10 | 60 |
| HPV16 | E2 | 8 | 12 |
| HPV16 | E2 | 8 | 95 |
| HPV16 | E2 | 11 | 95 |
| HPV16 | E2 | 11 | 120 |
| HPV16 | E2 | 8 | 170 |
| HPV16 | E2 | 9 | 170 |
| HPV16 | E2 | 11 | 170 |
| HPV16 | E2 | 10 | 345 |
| HPV16 | E2 | 8 | 76 |
| HPV16 | E2 | 8 | 235 |
| HPV16 | E2 | 8 | 151 |
| HPV16 | E2 | 9 | 151 |
| HPV16 | E2 | 11 | 151 |
| HPV16 | E2 | 10 | 191 |
| HPV16 | E2 | 10 | 57 |
| HPV16 | E2 | 8 | 27 |
| HPV16 | E2 | 9 | 27 |
| HPV16 | E2 | 11 | 27 |
| HPV16 | E2 | 9 | 343 |
| HPV16 | E2 | 9 | 304 |
| HPV16 | E2 | 11 | 304 |
| HPV16 | E2 | 8 | 37 |
| HPV16 | E2 | 9 | 37 |
| HPV16 | E2 | 10 | 37 |
| HPV16 | E2 | 11 | 37 |
| HPV16 | E2 | 8 | 7 |
| HPV16 | E2 | 11 | 242 |
| HPV16 | E2 | 8 | 165 |
| HPV16 | E2 | 11 | 165 |
| HPV16 | E2 | 8 | 330 |
| HPV16 | E2 | 8 | 264 |
| HPV16 | E2 | 8 | 98 |
| HPV16 | E2 | 9 | 206 |
| HPV16 | E2 | 11 | 206 |
| HPV16 | E2 | 9 | 316 |
| HPV16 | E2 | 10 | 23 |
| HPV16 | E2 | 8 | 317 |
| HPV16 | E2 | 11 | 317 |
| HPV16 | E2 | 10 | 261 |
| HPV16 | E2 | 11 | 261 |
| HPV16 | E2 | 11 | 144 |
| HPV16 | E2 | 8 | 269 |
| HPV16 | E2 | 10 | 269 |
| HPV16 | E2 | 8 | 104 |
| HPV16 | E2 | 9 | 104 |
| HPV16 | E2 | 10 | 104 |
| HPV16 | E2 | 8 | 313 |
| HPV16 | E2 | 9 | 24 |
| HPV16 | E2 | 11 | 24 |
| HPV16 | E2 | 9 | 107 |
| HPV16 | E2 | 8 | 322 |
| HPV16 | E2 | 10 | 322 |
| HPV16 | E2 | 9 | 247 |
| HPV16 | E2 | 8 | 355 |
| HPV16 | E2 | 11 | 81 |
| HPV16 | E2 | 8 | 61 |
| HPV16 | E2 | 9 | 61 |
| HPV16 | E2 | 10 | 78 |
| HPV16 | E2 | 8 | 297 |
| HPV16 | E2 | 9 | 297 |
| HPV16 | E2 | 10 | 297 |
| HPV16 | E2 | 11 | 297 |
| HPV16 | E2 | 10 | 93 |
| HPV16 | E2 | 10 | 334 |
| HPV16 | E2 | 11 | 310 |
| HPV16 | E2 | 9 | 128 |
| HPV16 | E2 | 11 | 128 |
| HPV16 | E2 | 8 | 285 |
| HPV16 | E2 | 11 | 285 |
| HPV16 | E2 | 9 | 146 |
| HPV16 | E2 | 10 | 146 |
| HPV16 | E2 | 9 | 10 |
| HPV16 | E2 | 10 | 10 |
| HPV16 | E2 | 9 | 262 |
| HPV16 | E2 | 10 | 262 |
| HPV16 | E2 | 8 | 152 |
| HPV16 | E2 | 10 | 152 |
| HPV16 | E2 | 9 | 192 |
| HPV16 | E2 | 9 | 64 |
| HPV16 | E2 | 9 | 97 |
| HPV16 | E2 | 8 | 205 |
| HPV16 | E2 | 10 | 205 |
| HPV16 | E2 | 10 | 315 |
| HPV16 | E2 | 11 | 333 |
| HPV16 | E2 | 10 | 145 |
| HPV16 | E2 | 11 | 145 |
| HPV16 | E2 | 8 | 147 |
| HPV16 | E2 | 9 | 147 |
| HPV16 | E2 | 9 | 58 |
| HPV16 | E2 | 11 | 58 |
| HPV16 | E2 | 8 | 321 |
| HPV16 | E2 | 9 | 321 |
| HPV16 | E2 | 11 | 321 |
| HPV16 | E2 | 10 | 134 |
| HPV16 | E2 | 11 | 92 |
| HPV16 | E2 | 10 | 337 |
| HPV16 | E2 | 9 | 167 |
| HPV16 | E2 | 11 | 167 |
| HPV16 | E2 | 11 | 155 |
| HPV16 | E2 | 10 | 102 |
| HPV16 | E2 | 11 | 102 |
| HPV16 | E2 | 10 | 178 |
| HPV16 | E2 | 11 | 178 |
| HPV16 | E2 | 9 | 312 |
| HPV16 | E2 | 8 | 131 |
| HPV16 | E2 | 9 | 159 |
| HPV16 | E2 | 10 | 159 |
| HPV16 | E5 | 8 | 53 |
| HPV16 | E5 | 11 | 53 |
| HPV16 | E5 | 8 | 56 |
| HPV16 | E5 | 11 | 56 |
| HPV16 | E5 | 10 | 54 |
| HPV16 | E5 | 9 | 7 |
| HPV16 | E5 | 8 | 59 |
| HPV16 | E5 | 10 | 59 |
| HPV16 | E5 | 11 | 20 |
| HPV16 | E5 | 9 | 5 |
| HPV16 | E5 | 11 | 5 |
| HPV16 | E5 | 9 | 60 |
| HPV16 | E5 | 8 | 72 |
| HPV16 | E5 | 9 | 72 |
| HPV16 | E5 | 10 | 66 |
| HPV16 | E5 | 8 | 65 |
| HPV16 | E5 | 11 | 65 |
| HPV16 | E5 | 9 | 64 |
| HPV16 | E5 | 11 | 43 |
| HPV16 | E5 | 10 | 44 |
| HPV16 | E5 | 11 | 44 |
| HPV16 | E5 | 8 | 51 |
| HPV16 | E5 | 10 | 51 |
| HPV16 | E5 | 8 | 61 |
| HPV16 | E5 | 8 | 12 |
| HPV16 | E5 | 8 | 23 |
| HPV16 | E5 | 10 | 4 |
| HPV16 | E5 | 8 | 71 |
| HPV16 | E5 | 9 | 71 |
| HPV16 | E5 | 10 | 71 |
| HPV16 | E5 | 8 | 73 |
| HPV16 | E5 | 9 | 11 |
| HPV16 | E5 | 9 | 22 |
| HPV16 | E5 | 8 | 32 |

TABLE XVI-continued

HLA-A3 Motif Peptides

| 1 | 2 | 3 | 4 |
|---|---|---|---|
| HPV16 | E5 | 8 | 47 |
| HPV16 | E5 | 10 | 47 |
| HPV16 | E5 | 11 | 47 |
| HPV16 | E5 | 9 | 48 |
| HPV16 | E5 | 10 | 48 |
| HPV16 | E5 | 11 | 48 |
| HPV16 | E5 | 9 | 45 |
| HPV16 | E5 | 10 | 45 |
| HPV16 | E5 | 11 | 3 |
| HPV16 | E5 | 8 | 70 |
| HPV16 | E5 | 9 | 70 |
| HPV16 | E5 | 10 | 70 |
| HPV16 | E5 | 11 | 70 |
| HPV16 | E5 | 9 | 31 |
| HPV16 | E5 | 9 | 58 |
| HPV16 | E5 | 11 | 58 |
| HPV16 | E5 | 9 | 55 |
| HPV16 | E5 | 8 | 8 |
| HPV16 | E5 | 9 | 52 |
| HPV16 | E5 | 8 | 6 |
| HPV16 | E5 | 10 | 5 |
| HPV16 | E5 | 10 | 10 |
| HPV16 | E5 | 11 | 9 |
| HPV16 | E5 | 10 | 21 |
| HPV16 | E5 | 8 | 45 |
| HPV16 | E5 | 9 | 46 |
| HPV16 | E5 | 11 | 45 |
| HPV16 | E5 | 8 | 50 |
| HPV16 | E5 | 9 | 50 |
| HPV16 | E5 | 11 | 50 |
| HPV16 | E5 | 10 | 63 |
| HPV16 | E5 | 8 | 68 |
| HPV16 | E5 | 10 | 68 |
| HPV16 | E5 | 11 | 68 |
| HPV16 | E6 | 9 | 53 |
| HPV16 | E6 | 10 | 53 |
| HPV16 | E6 | 9 | 7 |
| HPV16 | E6 | 11 | 7 |
| HPV16 | E6 | 8 | 68 |
| HPV16 | E6 | 9 | 68 |
| HPV16 | E6 | 10 | 68 |
| HPV16 | E6 | 8 | 146 |
| HPV16 | E6 | 9 | 146 |
| HPV16 | E6 | 8 | 70 |
| HPV16 | E6 | 10 | 70 |
| HPV16 | E6 | 10 | 58 |
| HPV16 | E6 | 11 | 58 |
| HPV16 | E6 | 11 | 73 |
| HPV16 | E6 | 9 | 143 |
| HPV16 | E6 | 11 | 143 |
| HPV16 | E6 | 9 | 23 |
| HPV16 | E6 | 10 | 37 |
| HPV16 | E6 | 11 | 37 |
| HPV16 | E6 | 11 | 51 |
| HPV16 | E6 | 10 | 63 |
| HPV16 | E6 | 8 | 32 |
| HPV16 | E6 | 10 | 32 |
| HPV16 | E6 | 11 | 105 |
| HPV16 | E6 | 11 | 36 |
| HPV16 | E6 | 8 | 48 |
| HPV16 | E6 | 10 | 52 |
| HPV16 | E6 | 11 | 52 |
| HPV16 | E6 | 8 | 92 |
| HPV16 | E6 | 10 | 92 |
| HPV16 | E6 | 9 | 31 |
| HPV16 | E6 | 11 | 31 |
| HPV16 | E6 | 8 | 125 |
| HPV16 | E6 | 9 | 125 |
| HPV16 | E6 | 9 | 33 |
| HPV16 | E6 | 8 | 34 |
| HPV16 | E6 | 9 | 80 |
| HPV16 | E6 | 9 | 59 |
| HPV16 | E6 | 10 | 59 |
| HPV16 | E6 | 8 | 72 |
| HPV16 | E6 | 9 | 75 |
| HPV16 | E6 | 10 | 75 |
| HPV16 | E6 | 11 | 75 |
| HPV16 | E6 | 8 | 79 |
| HPV16 | E6 | 10 | 79 |
| HPV16 | E6 | 11 | 57 |
| HPV16 | E6 | 8 | 117 |
| HPV16 | E6 | 9 | 117 |
| HPV16 | E6 | 10 | 22 |
| HPV16 | E6 | 8 | 126 |
| HPV16 | E6 | 11 | 126 |
| HPV16 | E6 | 9 | 107 |
| HPV16 | E6 | 10 | 105 |
| HPV16 | E6 | 9 | 44 |
| HPV16 | E6 | 10 | 44 |
| HPV16 | E6 | 11 | 44 |
| HPV16 | E6 | 8 | 8 |
| HPV16 | E6 | 10 | 8 |
| HPV16 | E6 | 11 | 8 |
| HPV16 | E6 | 8 | 144 |
| HPV16 | E6 | 10 | 144 |
| HPV16 | E6 | 11 | 144 |
| HPV16 | E6 | 11 | 112 |
| HPV16 | E6 | 9 | 134 |
| HPV16 | E6 | 8 | 102 |
| HPV16 | E6 | 9 | 116 |
| HPV16 | E6 | 10 | 116 |
| HPV16 | E6 | 8 | 10 |
| HPV16 | E6 | 9 | 10 |
| HPV16 | E6 | 11 | 21 |
| HPV16 | E6 | 8 | 43 |
| HPV16 | E6 | 10 | 43 |
| HPV16 | E6 | 11 | 43 |
| HPV16 | E6 | 10 | 142 |
| HPV16 | E6 | 11 | 62 |
| HPV16 | E6 | 8 | 55 |
| HPV16 | E6 | 8 | 131 |
| HPV16 | E6 | 11 | 5 |
| HPV16 | E6 | 9 | 145 |
| HPV16 | E6 | 10 | 145 |
| HPV16 | E6 | 11 | 89 |
| HPV16 | E6 | 10 | 5 |
| HPV16 | E6 | 9 | 140 |
| HPV16 | E6 | 11 | 29 |
| HPV16 | E6 | 8 | 94 |
| HPV16 | E6 | 9 | 93 |
| HPV16 | E6 | 8 | 69 |
| HPV16 | E6 | 9 | 69 |
| HPV16 | E6 | 11 | 69 |
| HPV16 | E6 | 10 | 139 |
| HPV16 | E6 | 9 | 67 |
| HPV16 | E6 | 10 | 67 |
| HPV16 | E6 | 11 | 67 |
| HPV16 | E6 | 8 | 39 |
| HPV16 | E6 | 9 | 39 |
| HPV16 | E6 | 9 | 91 |
| HPV16 | E6 | 11 | 91 |
| HPV16 | E6 | 8 | 77 |
| HPV16 | E6 | 9 | 77 |
| HPV16 | E6 | 10 | 77 |
| HPV16 | E7 | 8 | 42 |
| HPV16 | E7 | 9 | 42 |
| HPV16 | E7 | 10 | 42 |
| HPV16 | E7 | 11 | 42 |
| HPV16 | E7 | 9 | 58 |
| HPV16 | E7 | 10 | 68 |
| HPV16 | E7 | 11 | 39 |
| HPV16 | E7 | 10 | 14 |
| HPV16 | E7 | 8 | 4 |
| HPV16 | E7 | 8 | 35 |
| HPV16 | E7 | 11 | 35 |
| HPV16 | E7 | 9 | 37 |
| HPV16 | E7 | 8 | 18 |
| HPV16 | E7 | 10 | 57 |
| HPV16 | E7 | 9 | 3 |
| HPV16 | E7 | 10 | 88 |

TABLE XVI-continued

HLA-A3 Motif Peptides

| 1 | 2 | 3 | 4 |
|---|---|---|---|
| HPV16 | E7 | 8 | 2 |
| HPV16 | E7 | 10 | 2 |
| HPV16 | E7 | 8 | 38 |
| HPV16 | E7 | 9 | 89 |
| HPV16 | E7 | 11 | 67 |
| HPV16 | E7 | 11 | 13 |
| HPV16 | E7 | 11 | 87 |
| HPV16 | E7 | 8 | 53 |
| HPV16 | E7 | 9 | 41 |
| HPV16 | E7 | 10 | 41 |
| HPV16 | E7 | 11 | 41 |
| HPV16 | E7 | 11 | 47 |
| HPV16 | E7 | 8 | 44 |
| HPV16 | E7 | 9 | 44 |
| HPV16 | E7 | 8 | 70 |
| HPV16 | E7 | 9 | 49 |
| HPV16 | E7 | 8 | 66 |
| HPV16 | E7 | 11 | 63 |
| HPV16 | E7 | 11 | 56 |
| HPV16 | E7 | 10 | 64 |
| HPV16 | E7 | 8 | 90 |
| HPV16 | L1 | 10 | 372 |
| HPV16 | L1 | 11 | 372 |
| HPV16 | L1 | 9 | 162 |
| HPV16 | L1 | 9 | 453 |
| HPV16 | L1 | 11 | 453 |
| HPV16 | L1 | 9 | 127 |
| HPV16 | L1 | 10 | 483 |
| HPV16 | L1 | 11 | 483 |
| HPV16 | L1 | 8 | 411 |
| HPV16 | L1 | 8 | 498 |
| HPV16 | L1 | 9 | 498 |
| HPV16 | L1 | 8 | 63 |
| HPV16 | L1 | 11 | 63 |
| HPV16 | L1 | 11 | 451 |
| HPV16 | L1 | 9 | 373 |
| HPV16 | L1 | 10 | 373 |
| HPV16 | L1 | 9 | 233 |
| HPV16 | L1 | 11 | 233 |
| HPV16 | L1 | 8 | 158 |
| HPV16 | L1 | 11 | 292 |
| HPV16 | L1 | 10 | 70 |
| HPV16 | L1 | 11 | 70 |
| HPV16 | L1 | 11 | 371 |
| HPV16 | L1 | 10 | 251 |
| HPV16 | L1 | 8 | 128 |
| HPV16 | L1 | 9 | 329 |
| HPV16 | L1 | 8 | 153 |
| HPV16 | L1 | 9 | 153 |
| HPV16 | L1 | 10 | 153 |
| HPV16 | L1 | 11 | 153 |
| HPV16 | L1 | 9 | 235 |
| HPV16 | L1 | 9 | 223 |
| HPV16 | L1 | 11 | 223 |
| HPV16 | L1 | 8 | 249 |
| HPV16 | L1 | 9 | 249 |
| HPV16 | L1 | 9 | 484 |
| HPV16 | L1 | 10 | 484 |
| HPV16 | L1 | 11 | 484 |
| HPV16 | L1 | 10 | 397 |
| HPV16 | L1 | 11 | 300 |
| HPV16 | L1 | 9 | 225 |
| HPV16 | L1 | 8 | 270 |
| HPV16 | L1 | 9 | 270 |
| HPV16 | L1 | 8 | 154 |
| HPV16 | L1 | 9 | 154 |
| HPV16 | L1 | 10 | 154 |
| HPV16 | L1 | 9 | 228 |
| HPV16 | L1 | 8 | 120 |
| HPV16 | L1 | 11 | 113 |
| HPV16 | L1 | 10 | 442 |
| HPV16 | L1 | 8 | 17 |
| HPV16 | L1 | 9 | 17 |
| HPV16 | L1 | 8 | 171 |
| HPV16 | L1 | 9 | 464 |
| HPV16 | L1 | 11 | 441 |
| HPV16 | L1 | 9 | 378 |
| HPV16 | L1 | 10 | 378 |
| HPV16 | L1 | 8 | 474 |
| HPV16 | L1 | 10 | 474 |
| HPV16 | L1 | 10 | 273 |
| HPV16 | L1 | 11 | 231 |
| HPV16 | L1 | 8 | 109 |
| HPV16 | L1 | 9 | 109 |
| HPV16 | L1 | 10 | 109 |
| HPV16 | L1 | 10 | 5 |
| HPV16 | L1 | 8 | 494 |
| HPV16 | L1 | 9 | 494 |
| HPV16 | L1 | 10 | 494 |
| HPV16 | L1 | 8 | 481 |
| HPV16 | L1 | 8 | 506 |
| HPV16 | L1 | 8 | 236 |
| HPV16 | L1 | 8 | 282 |
| HPV16 | L1 | 9 | 282 |
| HPV16 | L1 | 11 | 282 |
| HPV16 | L1 | 8 | 446 |
| HPV16 | L1 | 11 | 446 |
| HPV16 | L1 | 9 | 356 |
| HPV16 | L1 | 10 | 232 |
| HPV16 | L1 | 9 | 186 |
| HPV16 | L1 | 8 | 224 |
| HPV16 | L1 | 16 | 224 |
| HPV16 | L1 | 9 | 269 |
| HPV16 | L1 | 10 | 269 |
| HPV16 | L1 | 8 | 110 |
| HPV16 | L1 | 8 | 437 |
| HPV16 | L1 | 9 | 437 |
| HPV16 | L1 | 10 | 437 |
| HPV16 | L1 | 9 | 348 |
| HPV16 | L1 | 10 | 142 |
| HPV16 | L1 | 8 | 499 |
| HPV16 | L1 | 8 | 93 |
| HPV16 | L1 | 10 | 93 |
| HPV16 | L1 | 9 | 305 |
| HPV16 | L1 | 8 | 323 |
| HPV16 | L1 | 11 | 323 |
| HPV16 | L1 | 8 | 198 |
| HPV16 | L1 | 11 | 307 |
| HPV16 | L1 | 8 | 438 |
| HPV16 | L1 | 9 | 438 |
| HPV16 | L1 | 10 | 64 |
| HPV16 | L1 | 9 | 62 |
| HPV16 | L1 | 9 | 392 |
| HPV16 | L1 | 11 | 392 |
| HPV16 | L1 | 8 | 285 |
| HPV16 | L1 | 8 | 102 |
| HPV16 | L1 | 10 | 102 |
| HPV16 | L1 | 10 | 452 |
| HPV16 | L1 | 9 | 254 |
| HPV16 | L1 | 8 | 250 |
| HPV16 | L1 | 11 | 250 |
| HPV16 | L1 | 8 | 349 |
| HPV16 | L1 | 10 | 332 |
| HPV16 | L1 | 11 | 332 |
| HPV16 | L1 | 11 | 401 |
| HPV16 | L1 | 10 | 185 |
| HPV16 | L1 | 11 | 86 |
| HPV16 | L1 | 9 | 143 |
| HPV16 | L1 | 8 | 374 |
| HPV16 | L1 | 9 | 374 |
| HPV16 | L1 | 11 | 11 |
| HPV16 | L1 | 10 | 407 |
| HPV16 | L1 | 10 | 501 |
| HPV16 | L1 | 11 | 501 |
| HPV16 | L1 | 9 | 108 |
| HPV16 | L1 | 10 | 108 |
| HPV16 | L1 | 9 | 493 |
| HPV16 | L1 | 10 | 493 |
| HPV16 | L1 | 11 | 493 |
| HPV16 | L1 | 9 | 480 |
| HPV16 | L1 | 8 | 505 |

TABLE XVI-continued

HLA-A3 Motif Peptides

| 1 | 2 | 3 | 4 |
|---|---|---|---|
| HPV16 | L1 | 9 | 505 |
| HPV16 | L1 | 10 | 304 |
| HPV16 | L1 | 9 | 197 |
| HPV16 | L1 | 11 | 406 |
| HPV16 | L1 | 8 | 151 |
| HPV16 | L1 | 10 | 151 |
| HPV16 | L1 | 11 | 151 |
| HPV16 | L1 | 8 | 90 |
| HPV16 | L1 | 10 | 90 |
| HPV16 | L1 | 11 | 90 |
| HPV16 | L1 | 8 | 46 |
| HPV16 | L1 | 10 | 46 |
| HPV16 | L1 | 11 | 46 |
| HPV16 | L1 | 8 | 69 |
| HPV16 | L1 | 11 | 69 |
| HPV16 | L1 | 8 | 404 |
| HPV16 | L1 | 9 | 152 |
| HPV16 | L1 | 10 | 152 |
| HPV16 | L1 | 11 | 152 |
| HPV16 | L1 | 9 | 248 |
| HPV16 | L1 | 10 | 248 |
| HPV16 | L1 | 8 | 485 |
| HPV16 | L1 | 9 | 485 |
| HPV16 | L1 | 10 | 485 |
| HPV16 | L1 | 11 | 272 |
| HPV16 | L1 | 10 | 355 |
| HPV16 | L1 | 9 | 490 |
| HPV16 | L1 | 8 | 139 |
| HPV16 | L1 | 11 | 184 |
| HPV16 | L1 | 8 | 68 |
| HPV16 | L1 | 9 | 68 |
| HPV16 | L1 | 11 | 148 |
| HPV16 | L1 | 8 | 495 |
| HPV16 | L1 | 9 | 495 |
| HPV16 | L1 | 11 | 495 |
| HPV16 | L1 | 8 | 409 |
| HPV16 | L1 | 10 | 409 |
| HPV16 | L1 | 10 | 87 |
| HPV16 | L1 | 11 | 87 |
| HPV16 | L1 | 8 | 234 |
| HPV16 | L1 | 10 | 234 |
| HPV16 | L1 | 9 | 281 |
| HPV16 | L1 | 10 | 281 |
| HPV16 | L1 | 9 | 27 |
| HPV16 | L1 | 8 | 226 |
| HPV16 | L1 | 11 | 226 |
| HPV16 | L1 | 11 | 263 |
| HPV16 | L1 | 9 | 325 |
| HPV16 | L1 | 11 | 325 |
| HPV16 | L1 | 9 | 157 |
| HPV16 | L1 | 9 | 16 |
| HPV16 | L1 | 10 | 16 |
| HPV16 | L1 | 8 | 385 |
| HPV16 | L1 | 10 | 347 |
| HPV16 | L1 | 10 | 58 |
| HPV16 | L1 | 8 | 311 |
| HPV16 | L1 | 8 | 476 |
| HPV16 | L1 | 10 | 421 |
| HPV16 | L1 | 9 | 383 |
| HPV16 | L1 | 10 | 383 |
| HPV16 | L1 | 9 | 296 |
| HPV16 | L1 | 9 | 460 |
| HPV16 | L1 | 10 | 460 |
| HPV16 | L1 | 11 | 460 |
| HPV16 | L1 | 8 | 104 |
| HPV16 | L1 | 9 | 119 |
| HPV16 | L1 | 11 | 258 |
| HPV16 | L1 | 9 | 436 |
| HPV16 | L1 | 10 | 436 |
| HPV16 | L1 | 11 | 436 |
| HPV16 | L1 | 8 | 190 |
| HPV16 | L1 | 9 | 77 |
| HPV16 | L1 | 10 | 247 |
| HPV16 | L1 | 11 | 247 |
| HPV16 | L1 | 10 | 489 |
| HPV16 | L1 | 9 | 138 |
| HPV16 | L1 | 10 | 321 |
| HPV16 | L1 | 10 | 515 |
| HPV16 | L1 | 11 | 515 |
| HPV16 | L1 | 11 | 43 |
| HPV16 | L1 | 9 | 497 |
| HPV16 | L1 | 10 | 497 |
| HPV16 | L1 | 8 | 450 |
| HPV16 | L1 | 10 | 222 |
| HPV16 | L1 | 8 | 399 |
| HPV16 | L1 | 8 | 487 |
| HPV16 | L1 | 11 | 331 |
| HPV16 | L1 | 9 | 403 |
| HPV16 | L1 | 8 | 181 |
| HPV16 | L1 | 11 | 354 |
| HPV16 | L1 | 8 | 280 |
| HPV16 | L1 | 10 | 280 |
| HPV16 | L1 | 11 | 280 |
| HPV16 | L1 | 10 | 26 |
| HPV16 | L1 | 10 | 179 |
| HPV16 | L1 | 9 | 445 |
| HPV16 | L1 | 9 | 100 |
| HPV16 | L1 | 10 | 100 |
| HPV16 | L1 | 9 | 67 |
| HPV16 | L1 | 10 | 67 |
| HPV16 | L1 | 9 | 364 |
| HPV16 | L1 | 10 | 364 |
| HPV16 | L1 | 8 | 56 |
| HPV16 | L1 | 11 | 482 |
| HPV16 | L1 | 8 | 328 |
| HPV16 | L1 | 10 | 328 |
| HPV16 | L1 | 9 | 115 |
| HPV16 | L1 | 8 | 144 |
| HPV16 | L1 | 8 | 92 |
| HPV16 | L1 | 9 | 92 |
| HPV16 | L1 | 11 | 92 |
| HPV16 | L1 | 9 | 322 |
| HPV16 | L1 | 8 | 306 |
| HPV16 | L1 | 8 | 253 |
| HPV16 | L1 | 10 | 253 |
| HPV16 | L1 | 8 | 271 |
| HPV16 | L1 | 8 | 28 |
| HPV16 | L1 | 11 | 28 |
| HPV16 | L1 | 10 | 324 |
| HPV16 | L1 | 8 | 518 |
| HPV16 | L1 | 9 | 518 |
| HPV16 | L1 | 10 | 518 |
| HPV16 | L1 | 11 | 518 |
| HPV16 | L1 | 10 | 308 |
| HPV16 | L1 | 11 | 308 |
| HPV16 | L1 | 8 | 49 |
| HPV16 | L1 | 9 | 422 |
| HPV16 | L1 | 8 | 365 |
| HPV16 | L1 | 9 | 365 |
| HPV16 | L1 | 8 | 375 |
| HPV16 | L1 | 8 | 519 |
| HPV16 | L1 | 9 | 519 |
| HPV16 | L1 | 10 | 519 |
| HPV16 | L1 | 11 | 519 |
| HPV16 | L1 | 8 | 521 |
| HPV16 | L1 | 9 | 521 |
| HPV16 | L1 | 10 | 521 |
| HPV16 | L1 | 9 | 410 |
| HPV16 | L1 | 8 | 523 |
| HPV16 | L1 | 9 | 309 |
| HPV16 | L1 | 10 | 309 |
| HPV16 | L1 | 10 | 12 |
| HPV16 | L1 | 11 | 12 |
| HPV16 | L1 | 11 | 50 |
| HPV16 | L1 | 11 | 4 |
| HPV16 | L1 | 8 | 471 |
| HPV16 | L1 | 10 | 471 |
| HPV16 | L1 | 11 | 471 |
| HPV16 | L1 | 8 | 229 |
| HPV16 | L1 | 8 | 423 |

TABLE XVI-continued

HLA-A3 Motif Peptides

| 1 | 2 | 3 | 4 |
|---|---|---|---|
| HPV16 | L1 | 8 | 439 |
| HPV16 | L1 | 9 | 408 |
| HPV16 | L1 | 11 | 408 |
| HPV16 | L1 | 9 | 327 |
| HPV16 | L1 | 11 | 327 |
| HPV16 | L1 | 11 | 376 |
| HPV16 | L1 | 10 | 114 |
| HPV16 | L1 | 9 | 252 |
| HPV16 | L1 | 11 | 252 |
| HPV16 | L1 | 9 | 448 |
| HPV16 | L1 | 10 | 448 |
| HPV16 | L1 | 9 | 65 |
| HPV16 | L1 | 11 | 65 |
| HPV16 | L1 | 8 | 517 |
| HPV16 | L1 | 9 | 517 |
| HPV16 | L1 | 10 | 517 |
| HPV16 | L1 | 11 | 517 |
| HPV16 | L1 | 8 | 520 |
| HPV16 | L1 | 9 | 520 |
| HPV16 | L1 | 10 | 520 |
| HPV16 | L1 | 11 | 520 |
| HPV16 | L1 | 8 | 522 |
| HPV16 | L1 | 9 | 522 |
| HPV16 | L1 | 11 | 362 |
| HPV16 | L1 | 9 | 516 |
| UPV16 | L1 | 10 | 516 |
| HPV16 | L1 | 11 | 516 |
| HPV16 | L1 | 8 | 379 |
| HPV16 | L1 | 9 | 379 |
| HPV16 | L1 | 11 | 379 |
| HPV16 | L1 | 11 | 36 |
| HPV16 | L1 | 8 | 54 |
| HPV16 | L1 | 9 | 54 |
| HPV16 | L1 | 10 | 54 |
| HPV16 | L1 | 11 | 167 |
| HPV16 | L1 | 10 | 227 |
| HPV16 | L1 | 11 | 98 |
| HPV16 | L1 | 10 | 293 |
| HPV16 | L1 | 9 | 71 |
| HPV16 | L1 | 10 | 71 |
| HPV16 | L1 | 11 | 141 |
| HPV16 | L1 | 10 | 264 |
| HPV16 | L1 | 11 | 264 |
| HPV16 | L1 | 9 | 91 |
| HPV16 | L1 | 10 | 91 |
| HPV16 | L1 | 10 | 44 |
| HPV16 | L1 | 8 | 48 |
| HPV16 | L1 | 9 | 48 |
| HPV16 | L1 | 8 | 326 |
| HPV16 | L1 | 10 | 326 |
| HPV16 | L1 | 10 | 447 |
| HPV16 | L1 | 11 | 447 |
| HPV16 | L1 | 8 | 357 |
| HPV16 | L1 | 9 | 47 |
| HPV16 | L1 | 10 | 47 |
| HPV16 | L1 | 10 | 126 |
| HPV16 | L1 | 11 | 195 |
| HPV16 | L1 | 9 | 30 |
| HPV16 | L1 | 8 | 338 |
| HPV16 | L1 | 10 | 161 |
| HPV16 | L1 | 11 | 396 |
| HPV16 | L1 | 11 | 75 |
| HPV16 | L1 | 8 | 268 |
| HPV16 | L1 | 10 | 268 |
| HPV16 | L1 | 11 | 268 |
| HPV16 | L1 | 9 | 302 |
| HPV16 | L1 | 9 | 260 |
| HPV16 | L1 | 8 | 7 |
| HPV16 | L1 | 9 | 38 |
| HPV16 | L1 | 8 | 389 |
| HPV16 | L1 | 8 | 275 |
| HPV16 | L1 | 10 | 275 |
| HPV16 | L1 | 11 | 275 |
| HPV16 | L1 | 9 | 470 |
| HPV16 | L1 | 11 | 470 |
| HPV16 | L1 | 8 | 53 |
| HPV16 | L1 | 9 | 53 |
| HPV16 | L1 | 10 | 53 |
| HPV16 | L1 | 11 | 53 |
| HPV16 | L2 | 9 | 441 |
| HPV16 | L2 | 8 | 241 |
| HPV16 | L2 | 10 | 443 |
| HPV16 | L2 | 11 | 443 |
| HPV16 | L2 | 11 | 25 |
| HPV16 | L2 | 10 | 288 |
| HPV16 | L2 | 11 | 288 |
| HPV16 | L2 | 11 | 356 |
| HPV16 | L2 | 10 | 293 |
| HPV16 | L2 | 11 | 293 |
| HPV16 | L2 | 8 | 13 |
| HPV16 | L2 | 11 | 13 |
| HPV16 | L2 | 9 | 82 |
| HPV16 | L2 | 9 | 15 |
| HPV16 | L2 | 11 | 15 |
| HPV16 | L2 | 8 | 442 |
| HPV16 | L2 | 11 | 442 |
| HPV16 | L2 | 9 | 282 |
| HPV16 | L2 | 10 | 282 |
| HPV16 | L2 | 8 | 329 |
| HPV16 | L2 | 8 | 445 |
| HPV16 | L2 | 9 | 445 |
| HPV16 | L2 | 9 | 31 |
| HPV16 | L2 | 10 | 415 |
| HPV16 | L2 | 9 | 285 |
| HPV16 | L2 | 8 | 261 |
| HPV16 | L2 | 10 | 258 |
| HPV16 | L2 | 11 | 258 |
| HPV16 | L2 | 10 | 340 |
| HPV16 | L2 | 9 | 111 |
| HPV16 | L2 | 8 | 465 |
| HPV16 | L2 | 9 | 465 |
| HPV16 | L2 | 11 | 242 |
| HPV16 | L2 | 8 | 283 |
| HPV16 | L2 | 9 | 283 |
| HPV16 | L2 | 11 | 283 |
| HPV16 | L2 | 8 | 466 |
| HPV16 | L2 | 11 | 268 |
| HPV16 | L2 | 11 | 181 |
| HPV16 | L2 | 8 | 321 |
| HPV16 | L2 | 10 | 321 |
| HPV16 | L2 | 9 | 444 |
| HPV16 | L2 | 10 | 444 |
| HPV16 | L2 | 9 | 259 |
| HPV16 | L2 | 10 | 259 |
| HPV16 | L2 | 11 | 59 |
| HPV16 | L2 | 10 | 300 |
| HPV16 | L2 | 10 | 364 |
| HPV16 | L2 | 11 | 226 |
| HPV16 | L2 | 10 | 63 |
| HPV16 | L2 | 9 | 433 |
| HPV16 | L2 | 11 | 433 |
| HPV16 | L2 | 11 | 218 |
| HPV16 | L2 | 10 | 26 |
| HPV16 | L2 | 8 | 65 |
| HPV16 | L2 | 9 | 61 |
| HPV16 | L2 | 8 | 440 |
| HPV16 | L2 | 10 | 440 |
| HPV16 | L2 | 8 | 41 |
| HPV16 | L2 | 8 | 260 |
| HPV16 | L2 | 9 | 260 |
| HPV16 | L2 | 8 | 320 |
| HPV16 | L2 | 9 | 320 |
| HPV16 | L2 | 11 | 320 |
| HPV16 | L2 | 8 | 306 |
| HPV16 | L2 | 10 | 306 |
| HPV16 | L2 | 10 | 60 |
| HPV16 | L2 | 8 | 439 |
| HPV16 | L2 | 9 | 439 |
| HPV16 | L2 | 11 | 439 |
| HPV16 | L2 | 8 | 32 |

TABLE XVI-continued

HLA-A3 Motif Peptides

| 1 | 2 | 3 | 4 |
|---|---|---|---|
| HPV16 | L2 | 11 | 32 |
| HPV16 | L2 | 10 | 45 |
| HPV16 | L2 | 11 | 45 |
| HPV16 | L2 | 11 | 344 |
| HPV16 | L2 | 10 | 243 |
| HPV16 | L2 | 10 | 135 |
| HPV16 | L2 | 8 | 250 |
| HPV16 | L2 | 8 | 286 |
| HPV16 | L2 | 8 | 430 |
| HPV16 | L2 | 10 | 105 |
| HPV16 | L2 | 9 | 248 |
| HPV16 | L2 | 10 | 248 |
| HPV16 | L2 | 8 | 318 |
| HPV16 | L2 | 9 | 318 |
| HPV16 | L2 | 10 | 318 |
| HPV16 | L2 | 11 | 318 |
| HPV16 | L2 | 10 | 39 |
| HPV16 | L2 | 8 | 35 |
| HPV16 | L2 | 8 | 323 |
| HPV16 | L2 | 8 | 284 |
| HPV16 | L2 | 10 | 284 |
| HPV16 | L2 | 8 | 75 |
| HPV16 | L2 | 11 | 427 |
| HPV16 | L2 | 8 | 249 |
| HPV16 | L2 | 9 | 249 |
| HPV16 | L2 | 9 | 183 |
| HPV16 | L2 | 11 | 183 |
| HPV16 | L2 | 9 | 294 |
| HPV16 | L2 | 10 | 294 |
| HPV16 | L2 | 10 | 108 |
| HPV16 | L2 | 8 | 454 |
| HPV16 | L2 | 11 | 454 |
| HPV16 | L2 | 8 | 271 |
| HPV16 | L2 | 8 | 363 |
| HPV16 | L2 | 11 | 363 |
| HPV16 | L2 | 8 | 276 |
| HPV16 | L2 | 11 | 273 |
| HPV16 | L2 | 9 | 397 |
| HPV16 | L2 | 10 | 397 |
| HPV16 | L2 | 9 | 150 |
| HPV16 | L2 | 8 | 174 |
| HPV16 | L2 | 9 | 240 |
| HPV16 | L2 | 11 | 292 |
| HPV16 | L2 | 8 | 395 |
| HPV16 | L2 | 11 | 395 |
| HPV16 | L2 | 8 | 281 |
| HPV16 | L2 | 10 | 281 |
| HPV16 | L2 | 11 | 281 |
| HPV16 | L2 | 10 | 30 |
| HPV16 | L2 | 11 | 414 |
| HPV16 | L2 | 10 | 279 |
| HPV16 | L2 | 10 | 432 |
| HPV16 | L2 | 8 | 217 |
| HPV16 | L2 | 8 | 417 |
| HPV16 | L2 | 9 | 215 |
| HPV16 | L2 | 10 | 215 |
| HPV16 | L2 | 9 | 429 |
| HPV16 | L2 | 9 | 74 |
| HPV16 | L2 | 10 | 124 |
| HPV16 | L2 | 8 | 386 |
| HPV16 | L2 | 11 | 386 |
| HPV16 | L2 | 9 | 346 |
| HPV16 | L2 | 10 | 346 |
| HPV16 | L2 | 11 | 346 |
| HPV16 | L2 | 10 | 166 |
| HPV16 | L2 | 11 | 383 |
| HPV16 | L2 | 8 | 450 |
| HPV16 | L2 | 9 | 450 |
| HPV16 | L2 | 10 | 450 |
| HPV16 | L2 | 11 | 450 |
| HPV16 | L2 | 8 | 80 |
| HPV16 | L2 | 11 | 80 |
| HPV16 | L2 | 11 | 246 |
| HPV16 | L2 | 9 | 172 |
| HPV16 | L2 | 10 | 172 |
| HPV16 | L2 | 9 | 358 |
| HPV16 | L2 | 8 | 221 |
| HPV16 | L2 | 10 | 221 |
| HPV16 | L2 | 11 | 44 |
| HPV16 | L2 | 9 | 17 |
| HPV16 | L2 | 8 | 342 |
| HPV16 | L2 | 9 | 310 |
| HPV16 | L2 | 8 | 234 |
| HPV16 | L2 | 9 | 234 |
| HPV16 | L2 | 8 | 12 |
| HPV16 | L2 | 9 | 12 |
| HPV16 | L2 | 9 | 305 |
| HPV16 | L2 | 11 | 305 |
| HPV16 | L2 | 8 | 5 |
| HPV16 | L2 | 9 | 5 |
| HPV16 | L2 | 11 | 5 |
| HPV16 | L2 | 8 | 315 |
| HPV16 | L2 | 9 | 315 |
| HPV16 | L2 | 11 | 315 |
| HPV16 | L2 | 8 | 298 |
| HPV16 | L2 | 10 | 69 |
| HPV16 | L2 | 11 | 9 |
| HPV16 | L2 | 10 | 313 |
| HPV16 | L2 | 11 | 313 |
| HPV16 | L2 | 8 | 6 |
| HPV16 | L2 | 10 | 6 |
| HPV16 | L2 | 10 | 14 |
| HPV16 | L2 | 8 | 316 |
| HPV16 | L2 | 10 | 316 |
| HPV16 | L2 | 11 | 316 |
| HPV16 | L2 | 9 | 64 |
| HPV16 | L2 | 8 | 319 |
| HPV16 | L2 | 9 | 319 |
| HPV16 | L2 | 10 | 319 |
| HPV16 | L2 | 10 | 274 |
| HPV16 | L2 | 10 | 360 |
| HPV16 | L2 | 11 | 360 |
| HPV16 | L2 | 9 | 125 |
| HPV16 | L2 | 11 | 134 |
| HPV16 | L2 | 11 | 104 |
| HPV16 | L2 | 8 | 389 |
| HPV16 | L2 | 8 | 107 |
| HPV16 | L2 | 11 | 107 |
| HPV16 | L2 | 10 | 269 |
| HPV16 | L2 | 8 | 184 |
| HPV16 | L2 | 10 | 184 |
| HPV16 | L2 | 9 | 185 |
| HPV16 | L2 | 9 | 212 |
| HPV16 | L2 | 8 | 186 |
| HPV16 | L2 | 8 | 213 |
| HPV16 | L2 | 11 | 213 |
| HPV16 | L2 | 10 | 387 |
| HPV16 | L2 | 8 | 347 |
| HPV16 | L2 | 9 | 347 |
| HPV16 | L2 | 10 | 347 |
| HPV16 | L2 | 9 | 167 |
| HPV16 | L2 | 10 | 384 |
| HPV16 | L2 | 10 | 81 |
| HPV16 | L2 | 9 | 27 |
| HPV16 | L2 | 8 | 83 |
| HPV16 | L2 | 11 | 299 |
| HPV16 | L2 | 8 | 62 |
| HPV16 | L2 | 11 | 62 |
| HPV16 | L2 | 9 | 70 |
| HPV16 | L2 | 9 | 40 |
| HPV16 | L2 | 9 | 438 |
| HPV16 | L2 | 10 | 438 |
| HPV16 | L2 | 8 | 399 |
| HPV16 | L2 | 8 | 311 |
| HPV16 | L2 | 10 | 182 |
| HPV16 | L2 | 8 | 112 |
| HPV16 | L2 | 8 | 359 |
| HPV16 | L2 | 11 | 359 |
| HPV16 | L2 | 9 | 388 |
| HPV16 | L2 | 8 | 295 |

TABLE XVI-continued

HLA-A3 Motif Peptides

| 1 | 2 | 3 | 4 |
|---|---|---|---|
| HPV16 | L2 | 9 | 295 |
| HPV16 | L2 | 11 | 295 |
| HPV16 | L2 | 10 | 211 |
| HPV16 | L2 | 8 | 137 |
| HPV16 | L2 | 8 | 156 |
| HPV16 | L2 | 8 | 398 |
| HPV16 | L2 | 9 | 398 |
| HPV16 | L2 | 9 | 244 |
| HPV16 | L2 | 11 | 231 |
| HPV16 | L2 | 9 | 136 |
| HPV16 | L2 | 11 | 153 |
| HPV16 | L2 | 10 | 154 |
| HPV16 | L2 | 8 | 151 |
| HPV16 | L2 | 11 | 287 |
| HPV16 | L2 | 9 | 222 |
| HPV16 | L2 | 11 | 238 |
| HPV16 | L2 | 8 | 168 |
| HPV16 | L2 | 9 | 106 |
| HPV16 | L2 | 11 | 210 |
| HPV16 | L2 | 9 | 155 |
| HPV16 | L2 | 9 | 328 |
| HPV16 | L2 | 8 | 366 |
| HPV16 | L2 | 9 | 464 |
| HPV16 | L2 | 10 | 464 |
| HPV16 | L2 | 8 | 48 |
| HPV16 | L2 | 10 | 393 |
| HPV16 | L2 | 11 | 72 |
| HPV16 | L2 | 10 | 447 |
| HPV16 | L2 | 11 | 447 |
| HPV16 | L2 | 8 | 453 |
| HPV16 | L2 | 9 | 453 |
| HPV16 | L2 | 11 | 303 |
| HPV16 | L2 | 9 | 228 |
| HPV16 | L2 | 10 | 437 |
| HPV16 | L2 | 11 | 437 |
| HPV16 | L2 | 8 | 349 |
| HPV18 | E1 | 11 | 396 |
| HPV18 | E1 | 10 | 397 |
| HPV18 | E1 | 11 | 397 |
| HPV18 | E1 | 8 | 390 |
| HPV18 | E1 | 9 | 390 |
| HPV18 | E1 | 10 | 390 |
| HPV18 | E1 | 8 | 636 |
| HPV18 | E1 | 11 | 636 |
| HPV18 | E1 | 8 | 383 |
| HPV18 | E1 | 9 | 398 |
| HPV18 | E1 | 10 | 398 |
| HPV18 | E1 | 11 | 398 |
| HPV18 | E1 | 10 | 246 |
| HPV18 | E1 | 11 | 546 |
| HPV18 | E1 | 9 | 68 |
| HPV18 | E1 | 11 | 466 |
| HPV18 | E1 | 10 | 387 |
| HPV18 | E1 | 11 | 387 |
| HPV18 | E1 | 9 | 284 |
| HPV18 | E1 | 11 | 284 |
| HPV18 | E1 | 10 | 213 |
| HPV18 | E1 | 11 | 40 |
| HPV18 | E1 | 8 | 413 |
| HPV18 | E1 | 9 | 413 |
| HPV18 | E1 | 10 | 413 |
| HPV18 | E1 | 8 | 531 |
| HPV18 | E1 | 9 | 531 |
| HPV18 | E1 | 11 | 216 |
| HPV18 | E1 | 11 | 504 |
| HPV18 | E1 | 8 | 412 |
| HPV18 | E1 | 9 | 412 |
| HPV18 | E1 | 10 | 412 |
| HPV18 | E1 | 11 | 412 |
| HPV18 | E1 | 9 | 618 |
| HPV18 | E1 | 9 | 290 |
| HPV18 | E1 | 10 | 290 |
| HPV18 | E1 | 8 | 483 |
| HPV18 | E1 | 10 | 483 |
| HPV18 | E1 | 11 | 483 |
| HPV18 | E1 | 8 | 479 |
| HPV18 | E1 | 8 | 311 |
| HPV18 | E1 | 10 | 311 |
| HPV18 | E1 | 8 | 160 |
| HPV18 | E1 | 11 | 437 |
| HPV18 | E1 | 9 | 240 |
| HPV18 | E1 | 11 | 196 |
| HPV18 | E1 | 9 | 635 |
| HPV18 | E1 | 9 | 78 |
| HPV18 | E1 | 10 | 78 |
| HPV18 | E1 | 11 | 78 |
| HPV18 | E1 | 9 | 530 |
| HPV18 | E1 | 10 | 530 |
| HPV18 | E1 | 8 | 411 |
| HPV18 | E1 | 9 | 411 |
| HPV18 | E1 | 10 | 411 |
| HPV18 | E1 | 11 | 411 |
| HPV18 | E1 | 10 | 275 |
| HPV18 | E1 | 10 | 529 |
| HPV18 | E1 | 11 | 529 |
| HPV18 | E1 | 9 | 49 |
| HPV18 | E1 | 11 | 8 |
| HPV18 | E1 | 9 | 548 |
| HPV18 | E1 | 10 | 548 |
| HPV18 | E1 | 11 | 548 |
| HPV18 | E1 | 9 | 628 |
| HPV18 | E1 | 8 | 203 |
| HPV18 | E1 | 11 | 203 |
| HPV18 | E1 | 9 | 363 |
| HPV18 | E1 | 10 | 363 |
| HPV18 | E1 | 10 | 228 |
| HPV18 | E1 | 10 | 381 |
| HPV18 | E1 | 11 | 134 |
| HPV18 | E1 | 8 | 391 |
| HPV18 | E1 | 9 | 391 |
| HPV18 | E1 | 11 | 391 |
| HPV18 | E1 | 10 | 637 |
| HPV18 | E1 | 11 | 637 |
| HPV18 | E1 | 9 | 42 |
| HPV18 | E1 | 10 | 522 |
| HPV18 | E1 | 8 | 342 |
| HPV18 | E1 | 10 | 52 |
| HPV18 | E1 | 11 | 30 |
| HPV18 | E1 | 10 | 634 |
| HPV18 | E1 | 8 | 459 |
| HPV18 | E1 | 10 | 459 |
| HPV18 | E1 | 8 | 594 |
| HPV18 | E1 | 10 | 594 |
| HPV18 | E1 | 10 | 256 |
| HPV18 | E1 | 11 | 442 |
| HPV18 | E1 | 8 | 639 |
| HPV18 | E1 | 9 | 639 |
| HPV18 | E1 | 11 | 639 |
| HPV18 | E1 | 9 | 10 |
| HPV18 | E1 | 10 | 10 |
| HPV18 | E1 | 8 | 610 |
| HPV18 | E1 | 10 | 610 |
| HPV18 | E1 | 11 | 610 |
| HPV18 | E1 | 9 | 115 |
| HPV18 | E1 | 10 | 115 |
| HPV18 | E1 | 11 | 115 |
| HPV18 | E1 | 9 | 62 |
| HPV18 | E1 | 10 | 62 |
| HPV18 | E1 | 11 | 62 |
| HPV18 | E1 | 9 | 375 |
| HPV18 | E1 | 10 | 375 |
| HPV18 | E1 | 8 | 379 |
| HPV18 | E1 | 9 | 379 |
| HPV18 | E1 | 9 | 587 |
| HPV18 | E1 | 8 | 64 |
| HPV18 | E1 | 9 | 64 |
| HPV18 | E1 | 10 | 309 |
| HPV18 | E1 | 9 | 104 |
| HPV18 | E1 | 10 | 74 |
| HPV18 | E1 | 10 | 57 |

TABLE XVI-continued

HLA-A3 Motif Peptides

| 1 | 2 | 3 | 4 |
|---|---|---|---|
| HPV18 | E1 | 9 | 482 |
| HPV18 | E1 | 11 | 482 |
| HPV18 | E1 | 9 | 601 |
| HPV18 | E1 | 10 | 362 |
| HPV18 | E1 | 11 | 362 |
| HPV18 | E1 | 8 | 539 |
| HPV18 | E1 | 8 | 619 |
| HPV18 | E1 | 8 | 493 |
| HPV18 | E1 | 8 | 643 |
| HPV18 | E1 | 8 | 248 |
| HPV18 | E1 | 11 | 248 |
| HPV18 | E1 | 8 | 50 |
| HPV18 | E1 | 8 | 497 |
| HPV18 | E1 | 9 | 500 |
| HPV18 | E1 | 9 | 460 |
| HPV18 | E1 | 11 | 460 |
| HPV18 | E1 | 8 | 463 |
| HPV18 | E1 | 10 | 463 |
| HPV18 | E1 | 8 | 470 |
| HPV18 | E1 | 8 | 399 |
| HPV18 | E1 | 9 | 399 |
| HPV18 | E1 | 10 | 399 |
| HPV18 | E1 | 9 | 452 |
| HPV18 | E1 | 8 | 226 |
| HPV18 | E1 | 9 | 226 |
| HPV18 | E1 | 8 | 130 |
| HPV18 | E1 | 8 | 508 |
| HPV18 | E1 | 8 | 465 |
| HPV18 | E1 | 8 | 212 |
| HPV18 | E1 | 11 | 212 |
| HPV18 | E1 | 10 | 13 |
| HPV18 | E1 | 9 | 341 |
| HPV18 | E1 | 9 | 444 |
| HPV18 | E1 | 11 | 444 |
| HPV18 | E1 | 9 | 257 |
| HPV18 | E1 | 10 | 443 |
| HPV18 | E1 | 9 | 223 |
| HPV18 | E1 | 11 | 223 |
| HPV18 | E1 | 11 | 494 |
| HPV18 | E1 | 11 | 92 |
| HPV18 | E1 | 11 | 644 |
| HPV18 | E1 | 8 | 11 |
| HPV18 | E1 | 9 | 11 |
| HPV18 | E1 | 10 | 473 |
| HPV18 | E1 | 9 | 279 |
| HPV18 | E1 | 10 | 279 |
| HPV18 | E1 | 11 | 279 |
| HPV18 | E1 | 10 | 249 |
| HPV18 | E1 | 11 | 249 |
| HPV18 | E1 | 9 | 71 |
| HPV18 | E1 | 10 | 499 |
| HPV18 | E1 | 11 | 514 |
| HPV18 | E1 | 8 | 355 |
| HPV18 | E1 | 8 | 270 |
| HPV18 | E1 | 8 | 83 |
| HPV18 | E1 | 9 | 198 |
| HPV18 | E1 | 8 | 440 |
| HPV18 | E1 | 11 | 51 |
| HPV18 | E1 | 9 | 247 |
| HPV18 | E1 | 11 | 352 |
| HPV18 | E1 | 8 | 282 |
| HPV18 | E1 | 11 | 282 |
| HPV18 | E1 | 8 | 569 |
| HPV18 | E1 | 10 | 569 |
| HPV18 | E1 | 11 | 569 |
| HPV18 | E1 | 9 | 32 |
| HPV18 | E1 | 9 | 506 |
| HPV18 | E1 | 10 | 506 |
| HPV18 | E1 | 8 | 552 |
| HPV18 | E1 | 8 | 116 |
| HPV18 | E1 | 9 | 116 |
| HPV18 | E1 | 10 | 116 |
| HPV18 | E1 | 11 | 116 |
| HPV18 | E1 | 8 | 461 |
| HPV18 | E1 | 10 | 461 |

TABLE XVI-continued

HLA-A3 Motif Peptides

| 1 | 2 | 3 | 4 |
|---|---|---|---|
| HPV18 | E1 | 9 | 590 |
| HPV18 | E1 | 10 | 590 |
| HPV18 | E1 | 10 | 617 |
| HPV18 | E1 | 10 | 289 |
| HPV18 | E1 | 11 | 289 |
| HPV18 | E1 | 8 | 410 |
| HPV18 | E1 | 9 | 410 |
| HPV18 | E1 | 10 | 410 |
| HPV18 | E1 | 11 | 410 |
| HPV18 | E1 | 9 | 202 |
| HPV18 | E1 | 11 | 579 |
| HPV18 | E1 | 8 | 219 |
| HPV18 | E1 | 8 | 299 |
| HPV18 | E1 | 11 | 472 |
| HPV18 | E1 | 9 | 439 |
| HPV18 | E1 | 8 | 647 |
| HPV18 | E1 | 9 | 647 |
| HPV18 | E1 | 8 | 318 |
| HPV18 | E1 | 10 | 318 |
| HPV18 | E1 | 9 | 468 |
| HPV18 | E1 | 10 | 468 |
| HPV18 | E1 | 8 | 401 |
| HPV18 | E1 | 10 | 401 |
| HPV18 | E1 | 8 | 292 |
| HPV18 | E1 | 8 | 490 |
| HPV18 | E1 | 10 | 490 |
| HPV18 | E1 | 11 | 490 |
| HPV18 | E1 | 10 | 259 |
| HPV18 | E1 | 11 | 259 |
| HPV18 | E1 | 10 | 237 |
| HPV18 | E1 | 8 | 524 |
| HPV18 | E1 | 8 | 206 |
| HPV18 | E1 | 11 | 206 |
| HPV18 | E1 | 8 | 389 |
| HPV18 | E1 | 9 | 389 |
| HPV18 | E1 | 10 | 389 |
| HPV18 | E1 | 11 | 389 |
| HPV18 | E1 | 10 | 283 |
| HPV18 | E1 | 8 | 215 |
| HPV18 | E1 | 11 | 274 |
| HPV18 | E1 | 11 | 528 |
| HPV18 | E1 | 10 | 547 |
| HPV18 | E1 | 11 | 547 |
| HPV18 | E1 | 10 | 627 |
| HPV18 | E1 | 8 | 69 |
| HPV18 | E1 | 11 | 69 |
| HPV18 | E1 | 9 | 129 |
| HPV18 | E1 | 9 | 464 |
| HPV18 | E1 | 8 | 281 |
| HPV18 | E1 | 9 | 281 |
| HPV18 | E1 | 8 | 261 |
| HPV18 | E1 | 9 | 261 |
| HPV18 | E1 | 10 | 261 |
| HPV18 | E1 | 8 | 313 |
| HPV18 | E1 | 9 | 388 |
| HPV18 | E1 | 10 | 388 |
| HPV18 | E1 | 11 | 388 |
| HPV18 | E1 | 10 | 204 |
| HPV18 | E1 | 8 | 285 |
| HPV18 | E1 | 10 | 285 |
| HPV18 | E1 | 9 | 570 |
| HPV18 | E1 | 10 | 570 |
| HPV18 | E1 | 8 | 364 |
| HPV18 | E1 | 9 | 364 |
| HPV18 | E1 | 8 | 224 |
| HPV18 | E1 | 10 | 224 |
| HPV18 | E1 | 11 | 224 |
| HPV18 | E1 | 8 | 376 |
| HPV18 | E1 | 9 | 376 |
| HPV18 | E1 | 11 | 376 |
| HPV18 | E1 | 8 | 571 |
| HPV18 | E1 | 9 | 571 |
| HPV18 | E1 | 11 | 480 |
| HPV18 | E1 | 9 | 229 |
| HPV18 | E1 | 9 | 382 |

TABLE XVI-continued

HLA-A3 Motif Peptides

| 1 | 2 | 3 | 4 |
|---|---|---|---|
| HPV18 | E1 | 8 | 415 |
| HPV18 | E1 | 10 | 415 |
| HPV18 | E1 | 11 | 415 |
| HPV18 | E1 | 10 | 340 |
| HPV18 | E1 | 9 | 214 |
| HPV18 | E1 | 9 | 312 |
| HPV18 | E1 | 10 | 495 |
| HPV18 | E1 | 8 | 429 |
| HPV18 | E1 | 11 | 429 |
| HPV18 | E1 | 11 | 47 |
| HPV18 | E1 | 9 | 478 |
| HPV18 | E1 | 8 | 403 |
| HPV18 | E1 | 11 | 403 |
| HPV18 | E1 | 10 | 77 |
| HPV18 | E1 | 11 | 77 |
| HPV18 | E1 | 8 | 612 |
| HPV18 | E1 | 9 | 612 |
| HPV18 | E1 | 11 | 612 |
| HPV18 | E1 | 11 | 361 |
| HPV18 | E1 | 11 | 604 |
| HPV18 | E1 | 8 | 15 |
| HPV18 | E1 | 9 | 574 |
| HPV18 | E1 | 8 | 428 |
| HPV18 | E1 | 9 | 428 |
| HPV18 | E1 | 8 | 119 |
| HPV18 | E1 | 9 | 119 |
| HPV18 | E1 | 10 | 119 |
| HPV18 | E1 | 9 | 393 |
| HPV18 | E1 | 11 | 487 |
| HPV18 | E1 | 10 | 158 |
| HPV18 | E1 | 9 | 191 |
| HPV18 | E1 | 9 | 577 |
| HPV18 | E1 | 8 | 485 |
| HPV18 | E1 | 9 | 485 |
| HPV18 | E1 | 10 | 600 |
| HPV18 | E1 | 8 | 642 |
| HPV18 | E1 | 9 | 642 |
| HPV18 | E1 | 9 | 568 |
| HPV18 | E1 | 11 | 568 |
| HPV18 | E1 | 8 | 551 |
| HPV18 | E1 | 9 | 551 |
| HPV18 | E1 | 8 | 448 |
| HPV18 | E1 | 8 | 519 |
| HPV18 | E1 | 8 | 252 |
| HPV18 | E1 | 8 | 607 |
| HPV18 | E1 | 11 | 607 |
| HPV18 | E1 | 9 | 60 |
| HPV18 | E1 | 11 | 60 |
| HPV18 | E1 | 9 | 405 |
| HPV18 | E1 | 10 | 67 |
| HPV18 | E1 | 8 | 195 |
| HPV18 | E1 | 10 | 451 |
| HPV18 | E1 | 8 | 211 |
| HPV18 | E1 | 9 | 211 |
| HPV18 | E1 | 8 | 54 |
| HPV18 | E1 | 10 | 457 |
| HPV18 | E1 | 10 | 146 |
| HPV18 | E1 | 11 | 200 |
| HPV18 | E1 | 9 | 426 |
| HPV18 | E1 | 10 | 426 |
| HPV18 | E1 | 11 | 426 |
| HPV18 | E1 | 8 | 80 |
| HPV18 | E1 | 9 | 80 |
| HPV18 | E1 | 10 | 80 |
| HPV18 | E1 | 11 | 80 |
| HPV18 | E1 | 8 | 148 |
| HPV18 | E1 | 10 | 589 |
| HPV18 | E1 | 11 | 589 |
| HPV18 | E1 | 11 | 626 |
| HPV18 | E1 | 11 | 102 |
| HPV18 | E1 | 10 | 128 |
| HPV18 | E1 | 8 | 320 |
| HPV18 | E1 | 10 | 320 |
| HPV18 | E1 | 11 | 320 |
| HPV18 | E1 | 9 | 622 |
| HPV18 | E1 | 8 | 33 |
| HPV18 | E1 | 8 | 380 |
| HPV18 | E1 | 11 | 380 |
| HPV18 | E1 | 9 | 496 |
| HPV18 | E1 | 8 | 469 |
| HPV18 | E1 | 9 | 469 |
| HPV18 | E1 | 9 | 225 |
| HPV18 | E1 | 10 | 225 |
| HPV18 | E1 | 8 | 507 |
| HPV18 | E1 | 9 | 507 |
| HPV18 | E1 | 8 | 120 |
| HPV18 | E1 | 9 | 120 |
| HPV18 | E1 | 11 | 120 |
| HPV18 | E1 | 10 | 135 |
| HPV18 | E1 | 8 | 117 |
| HPV18 | E1 | 9 | 117 |
| HPV18 | E1 | 10 | 117 |
| HPV18 | E1 | 11 | 117 |
| HPV18 | E1 | 9 | 321 |
| HPV18 | E1 | 10 | 321 |
| HPV18 | E1 | 10 | 93 |
| HPV18 | E1 | 8 | 322 |
| HPV18 | E1 | 9 | 322 |
| HPV18 | E1 | 11 | 245 |
| HPV18 | E1 | 8 | 65 |
| HPV18 | E1 | 9 | 310 |
| HPV18 | E1 | 11 | 310 |
| HPV18 | E1 | 8 | 239 |
| HPV18 | E1 | 10 | 239 |
| HPV18 | E1 | 9 | 534 |
| HPV18 | E1 | 11 | 534 |
| HPV18 | E1 | 8 | 377 |
| HPV18 | E1 | 10 | 377 |
| HPV18 | E1 | 11 | 377 |
| HPV18 | E1 | 8 | 227 |
| HPV18 | E1 | 11 | 227 |
| HPV18 | E1 | 10 | 41 |
| HPV18 | E1 | 11 | 521 |
| HPV18 | E1 | 8 | 241 |
| HPV18 | E1 | 11 | 56 |
| HPV18 | E1 | 10 | 645 |
| HPV18 | E1 | 11 | 645 |
| HPV18 | E1 | 9 | 462 |
| HPV18 | E1 | 11 | 462 |
| HPV18 | E1 | 8 | 12 |
| HPV18 | E1 | 11 | 12 |
| HPV18 | E1 | 10 | 488 |
| HPV18 | E1 | 8 | 43 |
| HPV18 | E1 | 10 | 197 |
| HPV18 | E1 | 9 | 260 |
| HPV18 | E1 | 10 | 260 |
| HPV18 | E1 | 11 | 260 |
| HPV18 | E1 | 8 | 414 |
| HPV18 | E1 | 9 | 414 |
| HPV18 | E1 | 11 | 414 |
| HPV18 | E1 | 9 | 238 |
| HPV18 | E1 | 11 | 238 |
| HPV18 | E1 | 10 | 533 |
| HPV18 | E1 | 8 | 572 |
| HPV18 | E1 | 11 | 572 |
| HPV18 | E1 | 8 | 532 |
| HPV18 | E1 | 11 | 532 |
| HPV18 | E1 | 11 | 296 |
| HPV18 | E1 | 8 | 591 |
| HPV18 | E1 | 9 | 591 |
| HPV18 | E1 | 11 | 591 |
| HPV18 | E1 | 8 | 323 |
| HPV18 | E1 | 10 | 297 |
| HPV18 | E1 | 9 | 159 |
| HPV18 | E1 | 10 | 48 |
| HPV18 | E1 | 8 | 105 |
| HPV18 | E1 | 10 | 481 |
| HPV18 | E1 | 8 | 592 |
| HPV18 | E1 | 10 | 592 |
| HPV18 | E1 | 10 | 217 |

TABLE XVI-continued

HLA-A3 Motif Peptides

| 1 | 2 | 3 | 4 |
|---|---|---|---|
| HPV18 | E1 | 10 | 31 |
| HPV18 | E1 | 10 | 505 |
| HPV18 | E1 | 11 | 505 |
| HPV18 | E1 | 8 | 81 |
| HPV18 | E1 | 9 | 81 |
| HPV18 | E1 | 10 | 81 |
| HPV18 | E1 | 8 | 280 |
| HPV18 | E1 | 9 | 280 |
| HPV18 | E1 | 10 | 280 |
| HPV18 | E1 | 11 | 339 |
| HPV18 | E1 | 10 | 17 |
| HPV18 | E1 | 11 | 17 |
| HPV18 | E1 | 10 | 278 |
| HPV18 | E1 | 11 | 278 |
| HPV18 | E1 | 10 | 346 |
| HPV18 | E1 | 8 | 432 |
| HPV18 | E1 | 9 | 516 |
| HPV18 | E1 | 11 | 516 |
| HPV18 | E1 | 9 | 536 |
| HPV18 | E1 | 11 | 536 |
| HPV18 | E1 | 10 | 268 |
| HPV18 | E1 | 11 | 386 |
| HPV18 | E1 | 9 | 538 |
| HPV18 | E1 | 8 | 492 |
| HPV18 | E1 | 9 | 492 |
| HPV18 | E1 | 8 | 137 |
| HPV18 | E1 | 10 | 222 |
| HPV18 | E1 | 9 | 585 |
| HPV18 | E1 | 11 | 585 |
| HPV18 | E1 | 10 | 408 |
| HPV18 | E1 | 11 | 408 |
| HPV18 | E1 | 8 | 19 |
| HPV18 | E1 | 9 | 19 |
| HPV18 | E2 | 9 | 269 |
| HPV18 | E2 | 10 | 269 |
| HPV18 | E2 | 11 | 269 |
| HPV18 | E2 | 11 | 245 |
| HPV18 | E2 | 8 | 147 |
| HPV18 | E2 | 9 | 45 |
| HPV18 | E2 | 9 | 82 |
| HPV18 | E2 | 10 | 82 |
| HPV18 | E2 | 11 | 82 |
| HPV18 | E2 | 10 | 154 |
| HPV18 | E2 | 11 | 154 |
| HPV18 | E2 | 8 | 270 |
| HPV18 | E2 | 9 | 270 |
| HPV18 | E2 | 10 | 270 |
| HPV18 | E2 | 11 | 270 |
| HPV18 | E2 | 10 | 214 |
| HPV18 | E2 | 10 | 246 |
| HPV18 | E2 | 8 | 252 |
| HPV18 | E2 | 10 | 260 |
| HPV18 | E2 | 11 | 260 |
| HPV18 | E2 | 8 | 301 |
| HPV18 | E2 | 9 | 301 |
| HPV18 | E2 | 11 | 132 |
| HPV18 | E2 | 10 | 282 |
| HPV18 | E2 | 10 | 205 |
| HPV18 | E2 | 9 | 14 |
| HPV18 | E2 | 10 | 14 |
| HPV18 | E2 | 8 | 156 |
| HPV18 | E2 | 9 | 156 |
| HPV18 | E2 | 11 | 156 |
| HPV18 | E2 | 9 | 146 |
| HPV18 | E2 | 11 | 209 |
| HPV18 | E2 | 10 | 126 |
| HPV18 | E2 | 8 | 29 |
| HPV18 | E2 | 11 | 315 |
| HPV18 | E2 | 11 | 26 |
| HPV18 | E2 | 11 | 31 |
| HPV18 | E2 | 9 | 354 |
| HPV18 | E2 | 9 | 139 |
| HPV18 | E2 | 10 | 210 |
| HPV18 | E2 | 8 | 175 |
| HPV18 | E2 | 9 | 175 |
| HPV18 | E2 | 10 | 167 |
| HPV18 | E2 | 11 | 167 |
| HPV18 | E2 | 10 | 78 |
| HPV18 | E2 | 9 | 104 |
| HPV18 | E2 | 11 | 104 |
| HPV18 | E2 | 11 | 12 |
| HPV18 | E2 | 10 | 268 |
| HPV18 | E2 | 11 | 268 |
| HPV18 | E2 | 10 | 294 |
| HPV18 | E2 | 11 | 294 |
| HPV18 | E2 | 8 | 117 |
| HPV18 | E2 | 9 | 117 |
| HPV18 | E2 | 8 | 331 |
| HPV18 | E2 | 8 | 85 |
| HPV18 | E2 | 9 | 161 |
| HPV18 | E2 | 11 | 235 |
| HPV18 | E2 | 9 | 251 |
| HPV18 | E2 | 11 | 259 |
| HPV18 | E2 | 8 | 53 |
| HPV18 | E2 | 10 | 291 |
| HPV18 | E2 | 8 | 338 |
| HPV18 | E2 | 9 | 338 |
| HPV18 | E2 | 9 | 20 |
| HPV18 | E2 | 8 | 46 |
| HPV18 | E2 | 10 | 19 |
| HPV18 | E2 | 8 | 289 |
| HPV18 | E2 | 8 | 68 |
| HPV18 | E2 | 9 | 68 |
| HPV18 | E2 | 10 | 316 |
| HPV18 | E2 | 11 | 72 |
| HPV18 | E2 | 8 | 75 |
| HPV18 | E2 | 8 | 300 |
| HPV18 | E2 | 9 | 300 |
| HPV18 | E2 | 10 | 300 |
| HPV18 | E2 | 9 | 28 |
| HPV18 | E2 | 9 | 129 |
| HPV18 | E2 | 8 | 293 |
| HPV18 | E2 | 11 | 293 |
| HPV18 | E2 | 9 | 116 |
| HPV18 | E2 | 10 | 116 |
| HPV18 | E2 | 11 | 18 |
| HPV18 | E2 | 8 | 152 |
| HPV18 | E2 | 9 | 152 |
| HPV18 | E2 | 9 | 329 |
| HPV18 | E2 | 10 | 329 |
| HPV18 | E2 | 8 | 238 |
| HPV18 | E2 | 9 | 238 |
| HPV18 | E2 | 11 | 238 |
| HPV18 | E2 | 11 | 281 |
| HPV18 | E2 | 11 | 267 |
| HPV18 | E2 | 9 | 39 |
| HPV18 | E2 | 10 | 39 |
| HPV18 | E2 | 11 | 39 |
| HPV18 | E2 | 11 | 12 |
| HPV18 | E2 | 11 | 8 |
| HPV18 | E2 | 11 | 333 |
| HPV18 | E2 | 10 | 81 |
| HPV18 | E2 | 11 | 81 |
| HPV18 | E2 | 11 | 204 |
| HPV18 | E2 | 9 | 144 |
| HPV18 | E2 | 11 | 144 |
| HPV18 | E2 | 10 | 133 |
| HPV18 | E2 | 11 | 133 |
| HPV18 | E2 | 8 | 44 |
| HPV18 | E2 | 10 | 44 |
| HPV18 | E2 | 8 | 67 |
| HPV18 | E2 | 9 | 67 |
| HPV18 | E2 | 10 | 67 |
| HPV18 | E2 | 8 | 297 |
| HPV18 | E2 | 9 | 297 |
| HPV18 | E2 | 11 | 297 |
| HPV18 | E2 | 8 | 107 |
| HPV18 | E2 | 9 | 107 |
| HPV18 | E2 | 10 | 107 |
| HPV18 | E2 | 8 | 170 |

TABLE XVI-continued

HLA-A3 Motif Peptides

| 1 | 2 | 3 | 4 |
|---|---|---|---|
| HPV18 | E2 | 8 | 185 |
| HPV18 | E2 | 9 | 185 |
| HPV18 | E2 | 9 | 285 |
| HPV18 | E2 | 9 | 64 |
| HPV18 | E2 | 10 | 64 |
| HPV18 | E2 | 11 | 64 |
| HPV18 | E2 | 10 | 353 |
| HPV18 | E2 | 9 | 249 |
| HPV18 | E2 | 11 | 249 |
| HPV18 | E2 | 9 | 288 |
| HPV18 | E2 | 8 | 272 |
| HPV18 | E2 | 9 | 272 |
| HPV18 | E2 | 8 | 262 |
| HPV18 | E2 | 9 | 262 |
| HPV18 | E2 | 8 | 16 |
| HPV18 | E2 | 8 | 84 |
| HPV18 | E2 | 9 | 84 |
| HPV18 | E2 | 9 | 33 |
| HPV18 | E2 | 8 | 38 |
| HPV18 | E2 | 10 | 38 |
| HPV18 | E2 | 11 | 38 |
| HPV18 | E2 | 9 | 220 |
| HPV18 | E2 | 8 | 216 |
| HPV18 | E2 | 8 | 80 |
| HPV18 | E2 | 11 | 80 |
| HPV18 | E2 | 10 | 56 |
| HPV18 | E2 | 11 | 56 |
| HPV18 | E2 | 10 | 2 |
| HPV18 | E2 | 10 | 242 |
| HPV18 | E2 | 11 | 119 |
| HPV18 | E2 | 10 | 61 |
| HPV18 | E2 | 8 | 122 |
| HPV1B | E2 | 8 | 314 |
| HPV18 | E2 | 10 | 160 |
| HPV18 | E2 | 8 | 305 |
| HPV18 | E2 | 9 | 305 |
| HPV18 | E2 | 10 | 305 |
| HPV18 | E2 | 8 | 11 |
| HPV18 | E2 | 9 | 343 |
| HPV18 | E2 | 8 | 244 |
| HPV18 | E2 | 11 | 213 |
| HPV18 | E2 | 10 | 13 |
| HPV18 | E2 | 11 | 13 |
| HPV18 | E2 | 9 | 283 |
| HPV18 | E2 | 11 | 283 |
| HPV18 | E2 | 8 | 298 |
| HPV18 | E2 | 10 | 298 |
| HPV18 | E2 | 11 | 298 |
| HPV18 | E2 | 9 | 229 |
| HPV18 | E2 | 10 | 229 |
| HPV18 | E2 | 9 | 317 |
| HPV18 | E2 | 9 | 206 |
| HPV18 | E2 | 8 | 230 |
| HPV18 | E2 | 9 | 230 |
| HPV18 | E2 | 11 | 230 |
| HPV18 | E2 | 8 | 318 |
| HPV18 | E2 | 8 | 233 |
| HPV18 | E2 | 8 | 355 |
| HPV18 | E2 | 8 | 140 |
| HPV18 | E2 | 10 | 236 |
| HPV18 | E2 | 11 | 236 |
| HPV18 | E2 | 8 | 153 |
| HPV18 | E2 | 11 | 153 |
| HPV18 | E2 | 9 | 155 |
| HPV18 | E2 | 10 | 155 |
| HPV18 | E2 | 8 | 145 |
| HPV18 | E2 | 10 | 145 |
| HPV18 | E2 | 8 | 330 |
| HPV18 | E2 | 9 | 330 |
| HPV18 | E2 | 8 | 273 |
| HPV18 | E2 | 8 | 186 |
| HPV18 | E2 | 9 | 57 |
| HPV18 | E2 | 10 | 57 |
| HPV18 | E2 | 9 | 243 |
| HPV18 | E2 | 8 | 207 |
| HPV18 | E2 | 8 | 286 |
| HPV18 | E2 | 11 | 286 |
| HPV18 | E2 | 10 | 120 |
| HPV18 | E2 | 9 | 211 |
| HPV18 | E2 | 8 | 231 |
| HPV18 | E2 | 10 | 231 |
| HPV18 | E2 | 10 | 334 |
| HPV18 | E2 | 8 | 136 |
| HPV18 | E2 | 8 | 212 |
| HPV18 | E2 | 8 | 157 |
| HPV18 | E2 | 10 | 157 |
| HPV18 | E2 | 9 | 232 |
| HPV18 | E2 | 9 | 335 |
| HPV18 | E2 | 11 | 335 |
| HPV18 | E2 | 9 | 62 |
| HPV18 | E2 | 11 | 62 |
| HPV18 | E2 | 10 | 150 |
| HPV18 | E2 | 11 | 150 |
| HPV18 | E2 | 10 | 138 |
| HPV18 | E2 | 8 | 322 |
| HPV18 | E2 | 10 | 183 |
| HPV18 | E2 | 11 | 183 |
| HPV18 | E2 | 9 | 240 |
| HPV18 | E2 | 10 | 173 |
| HPV18 | E2 | 11 | 173 |
| HPV18 | E2 | 10 | 143 |
| HPV18 | E2 | 10 | 228 |
| HPV18 | E2 | 11 | 228 |
| HPV18 | E2 | 8 | 135 |
| HPV18 | E2 | 9 | 135 |
| HPV18 | E2 | 9 | 164 |
| HPV18 | E2 | 10 | 164 |
| HPV18 | E5 | 9 | 49 |
| HPV18 | E5 | 9 | 47 |
| HPV18 | E5 | 11 | 47 |
| HPV18 | E5 | 9 | 29 |
| HPV18 | E5 | 11 | 29 |
| HPV18 | E5 | 11 | 9 |
| HPV18 | E5 | 10 | 56 |
| HPV18 | E5 | 11 | 27 |
| HPV18 | E5 | 9 | 11 |
| HPV18 | E5 | 8 | 8 |
| HPV18 | E5 | 11 | 55 |
| HPV18 | E5 | 10 | 10 |
| HPV18 | E5 | 10 | 6 |
| HPV18 | E5 | 9 | 57 |
| HPV18 | E5 | 11 | 57 |
| HPV18 | E5 | 8 | 50 |
| HPV18 | E5 | 11 | 37 |
| HPV18 | E5 | 11 | 5 |
| HPV18 | E5 | 8 | 43 |
| HPV18 | E5 | 11 | 43 |
| HPV18 | E5 | 8 | 40 |
| HPV18 | E5 | 10 | 40 |
| HPV18 | E5 | 11 | 40 |
| HPV18 | E5 | 9 | 7 |
| HPV18 | E5 | 8 | 58 |
| HPV18 | E5 | 10 | 58 |
| HPV18 | E5 | 11 | 58 |
| HPV18 | E5 | 9 | 22 |
| HPV18 | E5 | 10 | 22 |
| HPV18 | E5 | 11 | 22 |
| HPV18 | E5 | 9 | 2 |
| HPV18 | E5 | 10 | 28 |
| HPV18 | E5 | 8 | 51 |
| HPV18 | E5 | 8 | 1 |
| HPV18 | E5 | 10 | 1 |
| HPV18 | E5 | 8 | 46 |
| HPV18 | E5 | 10 | 46 |
| HPV18 | E5 | 10 | 21 |
| HPV18 | E5 | 11 | 21 |
| HPV18 | E5 | 8 | 50 |
| HPV18 | E5 | 9 | 50 |
| HPV18 | E5 | 8 | 24 |
| HPV18 | E5 | 9 | 24 |

TABLE XVI-continued

HLA-A3 Motif Peptides

| 1 | 2 | 3 | 4 |
|---|---|---|---|
| HPV18 | E5 | 8 | 3 |
| HPV18 | E5 | 8 | 25 |
| HPV18 | E5 | 8 | 48 |
| HPV18 | E5 | 10 | 48 |
| HPV18 | E5 | 10 | 44 |
| HPV18 | E5 | 8 | 12 |
| HPV18 | E5 | 8 | 42 |
| HPV18 | E5 | 9 | 42 |
| HPV18 | E5 | 9 | 41 |
| HPV18 | E5 | 10 | 41 |
| HPV18 | E5 | 9 | 31 |
| HPV18 | E5 | 9 | 39 |
| HPV18 | E5 | 11 | 39 |
| HPV18 | E6 | 9 | 53 |
| HPV18 | E6 | 10 | 63 |
| HPV18 | E6 | 8 | 64 |
| HPV18 | E6 | 9 | 64 |
| HPV18 | E6 | 11 | 64 |
| HPV18 | E6 | 9 | 48 |
| HPV18 | E6 | 10 | 48 |
| HPV18 | E6 | 9 | 131 |
| HPV18 | E6 | 9 | 141 |
| HPV18 | E6 | 9 | 68 |
| HPV18 | E6 | 11 | 105 |
| HPV18 | E6 | 10 | 70 |
| HPV18 | E6 | 11 | 70 |
| HPV18 | E6 | 8 | 27 |
| HPV18 | E6 | 10 | 27 |
| HPV18 | E6 | 9 | 58 |
| HPV18 | E6 | 10 | 58 |
| HPV18 | E6 | 10 | 83 |
| HPV18 | E6 | 8 | 5 |
| HPV18 | E6 | 9 | 5 |
| HPV18 | E6 | 8 | 46 |
| HPV18 | E6 | 11 | 46 |
| HPV18 | E6 | 8 | 29 |
| HPV18 | E6 | 10 | 77 |
| HPV18 | E6 | 8 | 40 |
| HPV18 | E6 | 9 | 40 |
| HPV18 | E6 | 10 | 40 |
| HPV18 | E6 | 11 | 40 |
| HPV18 | E6 | 8 | 43 |
| HPV18 | E6 | 11 | 43 |
| HPV18 | E6 | 10 | 47 |
| HPV18 | E6 | 11 | 47 |
| HPV18 | E6 | 10 | 53 |
| HPV18 | E6 | 11 | 53 |
| HPV18 | E6 | 8 | 97 |
| HPV18 | E6 | 11 | 97 |
| HPV18 | E6 | 10 | 62 |
| HPV18 | E6 | 11 | 62 |
| HPV18 | E6 | 8 | 120 |
| HPV18 | E6 | 9 | 120 |
| HPV18 | E6 | 8 | 139 |
| HPV18 | E6 | 11 | 139 |
| HPV18 | E6 | 10 | 130 |
| HPV18 | E6 | 8 | 69 |
| HPV18 | E6 | 11 | 69 |
| HPV18 | E6 | 8 | 67 |
| HPV18 | E6 | 10 | 57 |
| HPV18 | E6 | 8 | 50 |
| HPV18 | E6 | 8 | 117 |
| HPV18 | E6 | 9 | 117 |
| HPV18 | E6 | 10 | 117 |
| HPV18 | E6 | 11 | 117 |
| HPV18 | E6 | 8 | 92 |
| HPV18 | E6 | 10 | 36 |
| HPV18 | E6 | 11 | 52 |
| HPV18 | E6 | 9 | 102 |
| HPV18 | E6 | 10 | 101 |
| HPV18 | E6 | 8 | 41 |
| HPV18 | E6 | 9 | 41 |
| HPV18 | E6 | 10 | 41 |
| HPV18 | E6 | 9 | 1 |
| HPV18 | E6 | 10 | 1 |
| HPV18 | E6 | 11 | 129 |
| HPV18 | E6 | 8 | 100 |
| HPV18 | E6 | 11 | 100 |
| HPV18 | E6 | 10 | 95. |
| HPV18 | E6 | 11 | 114 |
| HPV18 | E6 | 9 | 111 |
| HPV18 | E6 | 10 | 111 |
| HPV18 | E6 | 8 | 137 |
| HPV18 | E6 | 9 | 137 |
| HPV18 | E6 | 10 | 137 |
| HPV18 | E6 | 9 | 26 |
| HPV18 | E6 | 11 | 26 |
| HPV18 | E6 | 9 | 144 |
| HPV18 | E6 | 10 | 144 |
| HPV18 | E6 | 11 | 144 |
| HPV18 | E6 | 9 | 107 |
| HPV18 | E6 | 11 | 107 |
| HPV18 | E6 | 8 | 57 |
| HPV18 | E6 | 10 | 57 |
| HPV18 | E6 | 11 | 57 |
| HPV18 | E6 | 8 | 3 |
| HPV18 | E6 | 10 | 3 |
| HPV18 | E6 | 11 | 3 |
| HPV18 | E6 | 8 | 126 |
| HPV18 | E6 | 9 | 126 |
| HPV18 | E6 | 10 | 125 |
| HPV18 | E6 | 10 | 135 |
| HPV18 | E6 | 11 | 135 |
| HPV18 | E6 | 8 | 74 |
| HPV18 | E6 | 10 | 140 |
| HPV18 | E6 | 11 | 82 |
| HPV18 | E6 | 8 | 59 |
| HPV18 | E6 | 9 | 59 |
| HPV18 | E6 | 11 | 24 |
| HPV18 | E6 | 9 | 84 |
| HPV18 | E6 | 9 | 95 |
| HPV18 | E6 | 11 | 89 |
| HPV18 | E6 | 9 | 37 |
| HPV18 | E6 | 11 | 37 |
| HPV18 | E6 | 10 | 44 |
| HPV18 | E6 | 8 | 38 |
| HPV18 | E6 | 10 | 38 |
| HPV18 | E6 | 11 | 38 |
| HPV18 | E6 | 9 | 54 |
| HPV18 | E6 | 10 | 54 |
| HPV18 | E6 | 11 | 54 |
| HPV18 | E6 | 8 | 72 |
| HPV18 | E6 | 9 | 72 |
| HPV18 | E6 | 10 | 72 |
| HPV18 | E7 | 11 | 80 |
| HPV18 | E7 | 9 | 6 |
| HPV18 | E7 | 9 | 55 |
| HPV18 | E7 | 8 | 63 |
| HPV18 | E7 | 9 | 63 |
| HPV18 | E7 | 11 | 63 |
| HPV18 | E7 | 10 | 81 |
| HPV18 | E7 | 10 | 42 |
| HPV18 | E7 | 11 | 42 |
| HPV18 | E7 | 9 | 82 |
| HPV18 | E7 | 9 | 40 |
| HPV18 | E7 | 9 | 20 |
| HPV18 | E7 | 8 | 77 |
| HPV18 | E7 | 9 | 77 |
| HPV18 | E7 | 10 | 77 |
| HPV18 | E7 | 9 | 43 |
| HPV18 | E7 | 10 | 43 |
| HPV18 | E7 | 11 | 43 |
| HPV18 | E7 | 11 | 48 |
| HPV18 | E7 | 9 | 59 |
| HPV18 | E7 | 8 | 41 |
| HPV18 | E7 | 11 | 41 |
| HPV18 | E7 | 10 | 5 |
| HPV18 | E7 | 8 | 73 |
| HPV18 | E7 | 9 | 62 |
| HPV18 | E7 | 10 | 62 |

TABLE XVI-continued

HLA-A3 Motif Peptides

| 1 | 2 | 3 | 4 |
|---|---|---|---|
| HPV18 | E7 | 8 | 89 |
| HPV18 | E7 | 9 | 94 |
| HPV18 | E7 | 11 | 74 |
| HPV18 | E7 | 8 | 64 |
| HPV18 | E7 | 10 | 54 |
| HPV18 | E7 | 10 | 51 |
| HPV18 | E7 | 11 | 51 |
| HPV18 | E7 | 9 | 38 |
| HPV18 | E7 | 11 | 38 |
| HPV18 | E7 | 11 | 92 |
| HPV18 | E7 | 9 | 50 |
| HPV18 | E7 | 10 | 50 |
| HPV18 | E7 | 9 | 88 |
| HPV18 | E7 | 10 | 71 |
| HPV18 | E7 | 8 | 79 |
| HPV18 | E7 | 8 | 95 |
| HPV18 | E7 | 8 | 78 |
| HPV18 | E7 | 9. | 78 |
| HPV18 | E7 | 8 | 7 |
| HPV18 | E7 | 10 | 93 |
| HPV18 | E7 | 8 | 50 |
| HPV18 | E7 | 11 | 50 |
| HPV18 | E7 | 10 | 75 |
| HPV18 | E7 | 11 | 75 |
| HPV18 | L1 | 10 | 494 |
| HPV18 | L1 | 11 | 195 |
| HPV18 | L1 | 9 | 162 |
| HPV18 | L1 | 9 | 300 |
| HPV18 | L1 | 10 | 300 |
| HPV18 | L1 | 8 | 447 |
| HPV18 | L1 | 11 | 115 |
| HPV18 | L1 | 8 | 225 |
| HPV18 | L1 | 11 | 225 |
| HPV18 | L1 | 8 | 487 |
| HPV18 | L1 | 9 | 487 |
| HPV18 | L1 | 11 | 487 |
| HPV18 | L1 | 11 | 63 |
| HPV18 | L1 | 11 | 268 |
| HPV18 | L1 | 8 | 345 |
| HPV18 | L1 | 11 | 407 |
| HPV18 | L1 | 9 | 419 |
| HPV18 | L1 | 10 | 419 |
| HPV18 | L1 | 10 | 196 |
| HPV18 | L1 | 8 | 552 |
| HPV18 | L1 | 9 | 552 |
| HPV18 | L1 | 10 | 552 |
| HPV18 | L1 | 8 | 163 |
| HPV18 | L1 | 8 | 222 |
| HPV18 | L1 | 10 | 222 |
| HPV18 | L1 | 11 | 222 |
| HPV18 | L1 | 8 | 42 |
| HPV18 | L1 | 10 | 42 |
| HPV18 | L1 | 8 | 218 |
| HPV18 | L1 | 8 | 310 |
| HPV18 | L1 | 9 | 310 |
| HPV18 | L1 | 10 | 310 |
| HPV18 | L1 | 11 | 310 |
| HPV18 | L1 | 10 | 2 |
| HPV18 | L1 | 11 | 2 |
| HPV18 | L1 | 8 | 493 |
| HPV18 | L1 | 11 | 493 |
| HPV18 | L1 | 8 | 418 |
| HPV18 | L1 | 10 | 418 |
| HPV18 | L1 | 11 | 418 |
| HPV18 | L1 | 8 | 245 |
| HPV18 | L1 | 8 | 188 |
| HPV18 | L1 | 9 | 188 |
| HPV18 | L1 | 10 | 86 |
| HPV18 | L1 | 11 | 86 |
| HPV18 | L1 | 9 | 270 |
| HPV18 | L1 | 9 | 258 |
| HPV18 | L1 | 11 | 258 |
| HPV18 | L1 | 8 | 284 |
| HPV18 | L1 | 9 | 284 |
| HPV18 | L1 | 8 | 122 |
| HPV18 | L1 | 10 | 122 |
| HPV18 | L1 | 11 | 122 |
| HPV18 | L1 | 9 | 520 |
| HPV18 | L1 | 10 | 520 |
| HPV18 | L1 | 11 | 520 |
| HPV18 | L1 | 9 | 260 |
| HPV18 | L1 | 8 | 305 |
| HPV18 | L1 | 9 | 305 |
| HPV18 | L1 | 9 | 364 |
| HPV18 | L1 | 8 | 189 |
| HPV18 | L1 | 9 | 263 |
| HPV18 | L1 | 11 | 148 |
| HPV18 | L1 | 8 | 330 |
| HPV18 | L1 | 10 | 330 |
| HPV18 | L1 | 10 | 478 |
| HPV18 | L1 | 10 | 203 |
| HPV18 | L1 | 11 | 203 |
| HPV18 | L1 | 10 | 257 |
| HPV18 | L1 | 11 | 202 |
| HPV18 | L1 | 8 | 155 |
| HPV18 | L1 | 10 | 155 |
| HPV18 | L1 | 8 | 317 |
| HPV18 | L1 | 9 | 317 |
| HPV18 | L1 | 9 | 309 |
| HPV18 | L1 | 10 | 309 |
| HPV18 | L1 | 11 | 309 |
| HPV18 | L1 | 10 | 308 |
| HPV18 | L1 | 11 | 308 |
| HPV18 | L1 | 9 | 144 |
| HPV18 | L1 | 8 | 59 |
| HPV18 | L1 | 8 | 49 |
| HPV18 | L1 | 11 | 49 |
| HPV18 | L1 | 8 | 530 |
| HPV18 | L1 | 9 | 530 |
| HPV18 | L1 | 10 | 530 |
| HPV18 | L1 | 8 | 517 |
| HPV18 | L1 | 8 | 271 |
| HPV18 | L1 | 11 | 482 |
| HPV18 | L1 | 9 | 221 |
| HPV18 | L1 | 11 | 221 |
| HPV18 | L1 | 9 | 244 |
| HPV18 | L1 | 8 | 259 |
| HPV18 | L1 | 10 | 259 |
| HPV18 | L1 | 9 | 304 |
| HPV18 | L1 | 10 | 304 |
| HPV18 | L1 | 9 | 329 |
| HPV18 | L1 | 11 | 329 |
| HPV18 | L1 | 10 | 116 |
| HPV18 | L1 | 9 | 117 |
| HPV18 | L1 | 8 | 145 |
| HPV18 | L1 | 11 | 535 |
| HPV18 | L1 | 8 | 177 |
| HPV18 | L1 | 10 | 177 |
| HPV18 | L1 | 11 | 342 |
| HPV18 | L1 | 11 | 358 |
| HPV18 | L1 | 9 | 383 |
| HPV18 | L1 | 9 | 175 |
| HPV18 | L1 | 10 | 175 |
| HPV18 | L1 | 8 | 38 |
| HPV18 | L1 | 10 | 13 |
| HPV18 | L1 | 11 | 13 |
| HPV18 | L1 | 9 | 30 |
| HPV18 | L1 | 9 | 428 |
| HPV18 | L1 | 11 | 428 |
| HPV18 | L1 | 9 | 41 |
| HPV18 | L1 | 11 | 41 |
| HPV18 | L1 | 8 | 285 |
| HPV18 | L1 | 11 | 285 |
| HPV18 | L1 | 9 | 58 |
| HPV18 | L1 | 11 | 437 |
| HPV18 | L1 | 9 | 94 |
| HPV18 | L1 | 10 | 226 |
| HPV18 | L1 | 8 | 542 |
| HPV18 | L1 | 11 | 542 |
| HPV18 | L1 | 10 | 40 |

TABLE XVI-continued

HLA-A3 Motif Peptides

| 1 | 2 | 3 | 4 |
|---|---|---|---|
| HPV18 | L1 | 11 | 39 |
| HPV18 | L1 | 11 | 46 |
| HPV18 | L1 | 10 | 47 |
| HPV18 | L1 | 11 | 219 |
| HPV18 | L1 | 10 | 9 |
| HPV18 | L1 | 8 | 488 |
| HPV18 | L1 | 10 | 488 |
| HPV18 | L1 | 10 | 443 |
| HPV18 | L1 | 9 | 360 |
| HPV18 | L1 | 11 | 360 |
| HPV18 | L1 | 9 | 492 |
| HPV18 | L1 | 8 | 500 |
| HPV18 | L1 | 9 | 500 |
| HPV18 | L1 | 10 | 143 |
| HPV18 | L1 | 8 | 421 |
| HPV18 | L1 | 9 | 529 |
| HPV18 | L1 | 10 | 529 |
| HPV18 | L1 | 11 | 529 |
| HPV18 | L1 | 9 | 516 |
| HPV18 | L1 | 8 | 507 |
| HPV18 | L1 | 10 | 507 |
| HPV18 | L1 | 11 | 507 |
| HPV18 | L1 | 8 | 232 |
| HPV18 | L1 | 9 | 186 |
| HPV18 | L1 | 10 | 186 |
| HPV18 | L1 | 11 | 186 |
| HPV18 | L1 | 10 | 505 |
| HPV18 | L1 | 8 | 125 |
| HPV18 | L1 | 10 | 125 |
| HPV18 | L1 | 11 | 125 |
| HPV18 | L1 | 9 | 217 |
| HPV18 | L1 | 8 | 440 |
| HPV18 | L1 | 8 | 187 |
| HPV18 | L1 | 9 | 187 |
| HPV18 | L1 | 10 | 187 |
| HPV18 | L1 | 9 | 283 |
| HPV18 | L1 | 10 | 283 |
| HPV18 | L1 | 10 | 519 |
| HPV18 | L1 | 11 | 519 |
| HPV18 | L1 | 8 | 521 |
| HPV18 | L1 | 9 | 521 |
| HPV18 | L1 | 10 | 521 |
| HPV18 | L1 | 9 | 316 |
| HPV18 | L1 | 10 | 316 |
| HPV18 | L1 | 9 | 48 |
| HPV18 | L1 | 9 | 367 |
| HPV18 | L1 | 10 | 367 |
| HPV18 | L1 | 11 | 367 |
| HPV18 | L1 | 10 | 220 |
| HPV18 | L1 | 9 | 526 |
| HPV18 | L1 | 8 | 174 |
| HPV18 | L1 | 10 | 174 |
| HPV18 | L1 | 11 | 174 |
| HPV18 | L1 | 11 | 8 |
| HPV18 | L1 | 9 | 14 |
| HPV18 | L1 | 10 | 14 |
| HPV18 | L1 | 8 | 103 |
| HPV18 | L1 | 9 | 103 |
| HPV18 | L1 | 10 | 103 |
| HPV18 | L1 | 9 | 178 |
| HPV18 | L1 | 8 | 445 |
| HPV18 | L1 | 10 | 445 |
| HPV18 | L1 | 8 | 104 |
| HPV18 | L1 | 9 | 104 |
| HPV18 | L1 | 8 | 531 |
| HPV18 | L1 | 9 | 531 |
| HPV18 | L1 | 11 | 1 |
| HPV18 | L1 | 10 | 269 |
| HPV18 | L1 | 11 | 307 |
| HPV18 | L1 | 10 | 328 |
| HPV18 | L1 | 11 | 298 |
| HPV18 | L1 | 8 | 261 |
| HPV18 | L1 | 11 | 261 |
| HPV18 | L1 | 9 | 36 |
| HPV18 | L1 | 10 | 36 |
| HPV18 | L1 | 10 | 382 |
| HPV18 | L1 | 10 | 457 |
| HPV18 | L1 | 11 | 70 |
| HPV18 | L1 | 8 | 510 |
| HPV18 | L1 | 10 | 54 |
| HPV18 | L1 | 8 | 52 |
| HPV18 | L1 | 8 | 496 |
| HPV18 | L1 | 10 | 496 |
| HPV18 | L1 | 8 | 224 |
| HPV18 | L1 | 9 | 224 |
| HPV18 | L1 | 8 | 558 |
| HPV18 | L1 | 9 | 558 |
| HPV18 | L1 | 10 | 558 |
| HPV18 | L1 | 11 | 558 |
| HPV18 | L1 | 9 | 344 |
| HPV18 | L1 | 8 | 293 |
| HPV18 | L1 | 11 | 293 |
| HPV18 | L1 | 8 | 414 |
| HPV18 | L1 | 9 | 414 |
| HPV18 | L1 | 10 | 414 |
| HPV18 | L1 | 10 | 57 |
| HPV18 | L1 | 10 | 282 |
| HPV18 | L1 | 11 | 282 |
| HPV18 | L1 | 10 | 525 |
| HPV18 | L1 | 9 | 173 |
| HPV18 | L1 | 11 | 173 |
| HPV18 | L1 | 8 | 28 |
| HPV18 | L1 | 11 | 28 |
| HPV18 | L1 | 10 | 26 |
| HPV18 | L1 | 8 | 16 |
| HPV18 | L1 | 10 | 16 |
| HPV18 | L1 | 11 | 20 |
| HPV18 | L1 | 8 | 550 |
| HPV18 | L1 | 10 | 550 |
| HPV18 | L1 | 11 | 550 |
| HPV18 | L1 | 9 | 399 |
| HPV18 | L1 | 8 | 540 |
| HPV18 | L1 | 10 | 540 |
| HPV18 | L1 | 8 | 91 |
| HPV18 | L1 | 9 | 472 |
| HPV18 | L1 | 10 | 472 |
| HPV18 | L1 | 11 | 472 |
| HPV18 | L1 | 8 | 412 |
| HPV18 | L1 | 10 | 412 |
| HPV18 | L1 | 11 | 412 |
| HPV18 | L1 | 8 | 121 |
| HPV18 | L1 | 9 | 121 |
| HPV18 | L1 | 11 | 121 |
| HPV18 | L1 | 10 | 243 |
| HPV18 | L1 | 10 | 378 |
| HPV18 | L1 | 8 | 216 |
| HPV18 | L1 | 10 | 216 |
| HPV18 | L1 | 9 | 439 |
| HPV18 | L1 | 10 | 315 |
| HPV18 | L1 | 11 | 315 |
| HPV18 | L1 | 10 | 366 |
| HPV18 | L1 | 11 | 366 |
| HPV18 | L1 | 8 | 137 |
| HPV18 | L1 | 9 | 287 |
| HPV18 | L1 | 8 | 410 |
| HPV18 | L1 | 10 | 410 |
| HPV18 | L1 | 9 | 484 |
| HPV18 | L1 | 11 | 484 |
| HPV18 | L1 | 10 | 214 |
| HPV18 | L1 | 8 | 205 |
| HPV18 | L1 | 9 | 205 |
| HPV18 | L1 | 9 | 102 |
| HPV18 | L1 | 10 | 102 |
| HPV18 | L1 | 11 | 102 |
| HPV18 | L1 | 11 | 547 |
| HPV18 | L1 | 8 | 6 |
| HPV18 | L1 | 9 | 112 |
| HPV18 | L1 | 9 | 135 |
| HPV18 | L1 | 10 | 135 |
| HPV18 | L1 | 8 | 561 |

TABLE XVI-continued

HLA-A3 Motif Peptides

| 1 | 2 | 3 | 4 |
|---|---|---|---|
| HPV18 | L1 | 8 | 81 |
| HPV18 | L1 | 10 | 299 |
| HPV18 | L1 | 11 | 299 |
| HPV18 | L1 | 10 | 548 |
| HPV18 | L1 | 9 | 551 |
| HPV18 | L1 | 10 | 551 |
| HPV18 | L1 | 11 | 551 |
| HPV18 | L1 | 8 | 127 |
| HPV18 | L1 | 9 | 127 |
| HPV18 | L1 | 8 | 363 |
| HPV18 | L1 | 10 | 363 |
| HPV18 | L1 | 8 | 179 |
| HPV18 | L1 | 8 | 288 |
| HPV18 | L1 | 10 | 93 |
| HPV18 | L1 | 8 | 459 |
| HPV18 | L1 | 8 | 31 |
| HPV18 | L1 | 10 | 359 |
| HPV18 | L1 | 9 | 150 |
| HPV18 | L1 | 11 | 518 |
| HPV18 | L1 | 8 | 475 |
| HPV18 | L1 | 11 | 335 |
| HPV18 | L1 | 8 | 306 |
| HPV18 | L1 | 9 | 458 |
| HPV18 | L1 | 9 | 555 |
| HPV18 | L1 | 11 | 555 |
| HPV18 | L1 | 11 | 100 |
| HPV18 | L1 | 8 | 400 |
| HPV18 | L1 | 10 | 408 |
| HPV18 | L1 | 8 | 485 |
| HPV18 | L1 | 10 | 485 |
| HPV18 | L1 | 11 | 485 |
| HPV18 | L1 | 11 | 78 |
| HPV18 | L1 | 9 | 446 |
| HPV18 | L1 | 9 | 489 |
| HPV18 | L1 | 11 | 85 |
| HPV18 | L1 | 8 | 264 |
| HPV18 | L1 | 9 | 541 |
| HPV18 | L1 | 11 | 442 |
| HPV18 | L1 | 9 | 444 |
| HPV18 | L1 | 11 | 444 |
| HPV18 | L1 | 11 | 327 |
| HPV18 | L1 | 9 | 362 |
| HPV18 | L1 | 11 | 362 |
| HPV18 | L1 | 11 | 92 |
| HPV18 | L1 | 10 | 149 |
| HPV18 | L1 | 8 | 474 |
| HPV18 | L1 | 9 | 474 |
| HPV18 | L1 | 9 | 197 |
| HPV18 | L1 | 8 | 554 |
| HPV18 | L1 | 10 | 554 |
| HPV18 | L1 | 11 | 397 |
| HPV18 | L1 | 8 | 473 |
| HPV18 | L1 | 9 | 473 |
| HPV18 | L1 | 10 | 473 |
| HPV18 | L1 | 8 | 553 |
| HPV18 | L1 | 9 | 553 |
| HPV18 | L1 | 11 | 553 |
| HPV18 | L1 | 8 | 105 |
| HPV18 | L1 | 11 | 105 |
| HPV18 | L1 | 9 | 331 |
| HPV18 | L1 | 10 | 71 |
| HPV18 | L1 | 11 | 71 |
| HPV18 | L1 | 9 | 486 |
| HPV18 | L1 | 10 | 486 |
| HPV18 | L1 | 10 | 79 |
| HPV18 | L1 | 8 | 384 |
| HPV18 | L1 | 10 | 262 |
| HPV18 | L1 | 11 | 477 |
| HPV18 | L1 | 9 | 55 |
| HPV18 | L1 | 11 | 133 |
| HPV18 | L1 | 8 | 176 |
| HPV18 | L1 | 9 | 176 |
| HPV18 | L1 | 11 | 176 |
| HPV18 | L1 | 10 | 106 |
| HPV18 | L1 | 9 | 126 |
| HPV18 | L1 | 10 | 126 |
| HPV18 | L1 | 8 | 89 |
| HPV18 | L1 | 9 | 89 |
| HPV18 | L1 | 10 | 89 |
| HPV18 | L1 | 8 | 361 |
| HPV18 | L1 | 10 | 361 |
| HPV18 | L1 | 10 | 161 |
| HPV18 | L1 | 8 | 230 |
| HPV18 | L1 | 10 | 230 |
| HPV18 | L1 | 8 | 373 |
| HPV18 | L1 | 9 | 417 |
| HPV18 | L1 | 11 | 417 |
| HPV18 | L1 | 11 | 110 |
| HPV18 | L1 | 10 | 303 |
| HPV18 | L1 | 11 | 303 |
| HPV18 | L1 | 8 | 18 |
| HPV18 | L1 | 9 | 337 |
| HPV18 | L1 | 8 | 73 |
| HPV18 | L1 | 9 | 73 |
| HPV18 | L1 | 9 | 295 |
| HPV18 | L1 | 10 | 35 |
| HPV18 | L1 | 11 | 35 |
| HPV18 | L1 | 8 | 425 |
| HPV18 | L1 | 8 | 4 |
| HPV18 | L1 | 9 | 4 |
| HPV18 | L1 | 10 | 183 |
| HPV18 | L1 | 8 | 88 |
| HPV18 | L1 | 9 | 88 |
| HPV18 | L1 | 10 | 88 |
| HPV18 | L1 | 11 | 88 |
| HPV18 | L2 | 11 | 255 |
| HPV18 | L2 | 8 | 222 |
| HPV18 | L2 | 9 | 222 |
| HPV18 | L2 | 10 | 222 |
| HPV18 | L2 | 10 | 286 |
| HPV18 | L2 | 11 | 286 |
| HPV18 | L2 | 9 | 423 |
| HPV18 | L2 | 8 | 12 |
| HPV18 | L2 | 11 | 12 |
| HPV18 | L2 | 8 | 341 |
| HPV18 | L2 | 11 | 341 |
| HPV18 | L2 | 9 | 275 |
| HPV18 | L2 | 10 | 275 |
| HPV18 | L2 | 9 | 278 |
| HPV18 | L2 | 11 | 322 |
| HPV18 | L2 | 11 | 129 |
| HPV18 | L2 | 10 | 349 |
| HPV18 | L2 | 11 | 354 |
| HPV18 | L2 | 9 | 273 |
| HPV18 | L2 | 11 | 273 |
| HPV18 | L2 | 9 | 109 |
| HPV18 | L2 | 11 | 109 |
| HPV18 | L2 | 9 | 260 |
| HPV18 | L2 | 9 | 343 |
| HPV18 | L2 | 10 | 343 |
| HPV18 | L2 | 10 | 108 |
| HPV18 | L2 | 8 | 36 |
| HPV18 | L2 | 8 | 194 |
| HPV18 | L2 | 8 | 334 |
| HPV18 | L2 | 9 | 169 |
| HPV18 | L2 | 8 | 455 |
| HPV18 | L2 | 11 | 348 |
| HPV18 | L2 | 8 | 454 |
| HPV18 | L2 | 9 | 454 |
| HPV18 | L2 | 11 | 371 |
| HPV18 | L2 | 8 | 443 |
| HPV18 | L2 | 11 | 443 |
| HPV18 | L2 | 11 | 241 |
| HPV18 | L2 | 8 | 276 |
| HPV18 | L2 | 9 | 276 |
| HPV18 | L2 | 11 | 276 |
| HPV18 | L2 | 8 | 296 |
| HPV18 | L2 | 11 | 296 |
| HPV18 | L2 | 10 | 306 |
| HPV18 | L2 | 11 | 306 |

TABLE XVI-continued

HLA-A3 Motif Peptides

| 1 | 2 | 3 | 4 |
|---|---|---|---|
| HPV18 | L2 | 10 | 181 |
| HPV18 | L2 | 8 | 314 |
| HPV18 | L2 | 11 | 58 |
| HPV18 | L2 | 8 | 429 |
| HPV18 | L2 | 10 | 62 |
| HPV18 | L2 | 10 | 25 |
| HPV18 | L2 | 8 | 64 |
| HPV18 | L2 | 9 | 60 |
| HPV18 | L2 | 10 | 432 |
| HPV18 | L2 | 11 | 432 |
| HPV18 | L2 | 8 | 183 |
| HPV18 | L2 | 10 | 183 |
| HPV18 | L2 | 9 | 310 |
| HPV18 | L2 | 10 | 310 |
| HPV18 | L2 | 11 | 310 |
| HPV18 | L2 | 10 | 124 |
| HPV18 | L2 | 11 | 292 |
| HPV18 | L2 | 10 | 318 |
| HPV18 | L2 | 11 | 431 |
| HPV18 | L2 | 11 | 190 |
| HPV18 | L2 | 8 | 313 |
| HPV18 | L2 | 9 | 313 |
| HPV18 | L2 | 8 | 428 |
| HPV18 | L2 | 9 | 428 |
| HPV18 | L2 | 10 | 59 |
| HPV18 | L2 | 11 | 167 |
| HPV18 | L2 | 8 | 279 |
| HPV18 | L2 | 10 | 44 |
| HPV18 | L2 | 10 | 323 |
| HPV18 | L2 | 10 | 210 |
| HPV18 | L2 | 11 | 210 |
| HPV18 | L2 | 10 | 152 |
| HPV18 | L2 | 11 | 152 |
| HPV18 | L2 | 10 | 130 |
| HPV18 | L2 | 8 | 249 |
| HPV18 | L2 | 8 | 416 |
| HPV18 | L2 | 11 | 43 |
| HPV18 | L2 | 8 | 34 |
| HPV18 | L2 | 10 | 34 |
| HPV18 | L2 | 8 | 299 |
| HPV18 | L2 | 10 | 299 |
| HPV18 | L2 | 8 | 248 |
| HPV18 | L2 | 9 | 248 |
| HPV18 | L2 | 10 | 242 |
| HPV18 | L2 | 9 | 287 |
| HPV18 | L2 | 10 | 287 |
| HPV18 | L2 | 10 | 391 |
| HPV18 | L2 | 11 | 338 |
| HPV18 | L2 | 8 | 277 |
| HPV18 | L2 | 10 | 277 |
| HPV18 | L2 | 10 | 355 |
| HPV18 | L2 | 11 | 305 |
| HPV18 | L2 | 8 | 1 |
| HPV18 | L2 | 9 | 1 |
| HPV18 | L2 | 10 | 1 |
| HPV18 | L2 | 11 | 1 |
| HPV18 | L2 | 8 | 345 |
| HPV18 | L2 | 10 | 79 |
| HPV18 | L2 | 11 | 285 |
| HPV18 | L2 | 10 | 422 |
| HPV18 | L2 | 8 | 357 |
| HPV18 | L2 | 10 | 272 |
| HPV18 | L2 | 8 | 325 |
| HPV18 | L2 | 11 | 209 |
| HPV18 | L2 | 9 | 415 |
| HPV18 | L2 | 9 | 214 |
| HPV18 | L2 | 11 | 390 |
| HPV18 | L2 | 8 | 439 |
| HPV18 | L2 | 9 | 439 |
| HPV18 | L2 | 10 | 439 |
| HPV18 | L2 | 11 | 439 |
| HPV18 | L2 | 8 | 362 |
| HPV18 | L2 | 9 | 362 |
| HPV18 | L2 | 10 | 362 |
| HPV18 | L2 | 11 | 362 |
| HPV18 | L2 | 11 | 245 |
| HPV18 | L2 | 9 | 419 |
| HPV18 | L2 | 9 | 120 |
| HPV18 | L2 | 9 | 376 |
| HPV18 | L2 | 8 | 185 |
| HPV18 | L2 | 10 | 216 |
| HPV18 | L2 | 8 | 258 |
| HPV18 | L2 | 11 | 258 |
| HPV18 | L2 | 10 | 360 |
| HPV18 | L2 | 11 | 360 |
| HPV18 | L2 | 8 | 312 |
| HPV18 | L2 | 9 | 312 |
| HPV18 | L2 | 10 | 312 |
| HPV18 | L2 | 10 | 172 |
| HPV18 | L2 | 9 | 233 |
| HPV18 | L2 | 8 | 5 |
| HPV18 | L2 | 8 | 11 |
| HPV18 | L2 | 9 | 11 |
| HPV18 | L2 | 9 | 229 |
| HPV18 | L2 | 8 | 295 |
| HPV18 | L2 | 9 | 295 |
| HPV18 | L2 | 8 | 291 |
| HPV18 | L2 | 9 | 298 |
| HPV18 | L2 | 11 | 298 |
| HPV18 | L2 | 10 | 281 |
| HPV18 | L2 | 11 | 281 |
| HPV18 | L2 | 9 | 268 |
| HPV18 | L2 | 8 | 308 |
| HPV18 | L2 | 9 | 308 |
| HPV18 | L2 | 11 | 308 |
| HPV18 | L2 | 8 | 364 |
| HPV18 | L2 | 9 | 364 |
| HPV18 | L2 | 10 | 364 |
| HPV18 | L2 | 11 | 364 |
| HPV18 | L2 | 10 | 68 |
| HPV18 | L2 | 8 | 220 |
| HPV18 | L2 | 10 | 220 |
| HPV18 | L2 | 11 | 220 |
| HPV18 | L2 | 10 | 450 |
| HPV18 | L2 | 8 | 132 |
| HPV18 | L2 | 9 | 340 |
| HPV18 | L2 | 8 | 274 |
| HPV18 | L2 | 10 | 274 |
| HPV18 | L2 | 11 | 274 |
| HPV18 | L2 | 8 | 269 |
| HPV18 | L2 | 8 | 115 |
| HPV18 | L2 | 8 | 126 |
| HPV18 | L2 | 11 | 24 |
| HPV18 | L2 | 9 | 63 |
| HPV18 | L2 | 8 | 309 |
| HPV18 | L2 | 10 | 309 |
| HPV18 | L2 | 11 | 309 |
| HPV18 | L2 | 11 | 151 |
| HPV18 | L2 | 9 | 247 |
| HPV18 | L2 | 10 | 247 |
| HPV18 | L2 | 10 | 246 |
| HPV18 | L2 | 11 | 246 |
| HPV18 | L2 | 9 | 211 |
| HPV18 | L2 | 10 | 211 |
| HPV18 | L2 | 8 | 110 |
| HPV18 | L2 | 10 | 110 |
| HPV18 | L2 | 8 | 393 |
| HPV18 | L2 | 8 | 212 |
| HPV18 | L2 | 9 | 212 |
| HPV18 | L2 | 11 | 212 |
| HPV18 | L2 | 8 | 424 |
| HPV18 | L2 | 11 | 424 |
| HPV18 | L2 | 11 | 147 |
| HPV18 | L2 | 9 | 153 |
| HPV18 | L2 | 10 | 153 |
| HPV18 | L2 | 8 | 365 |
| HPV18 | L2 | 9 | 365 |
| HPV18 | L2 | 10 | 365 |
| HPV18 | L2 | 10 | 235 |
| HPV18 | L2 | 9 | 149 |

TABLE XVI-continued

HLA-A3 Motif Peptides

| 1 | 2 | 3 | 4 |
|---|---|---|---|
| HPV18 | L2 | 10 | 13 |
| HPV18 | L2 | 9 | 111 |
| HPV18 | L2 | 10 | 412 |
| HPV18 | L2 | 8 | 420 |
| HPV18 | L2 | 9 | 26 |
| HPV18 | L2 | 8 | 15 |
| HPV18 | L2 | 8 | 121 |
| HPV18 | L2 | 9 | 173 |
| HPV18 | L2 | 8 | 61 |
| HPV18 | L2 | 11 | 61 |
| HPV18 | L2 | 11 | 123 |
| HPV18 | L2 | 9 | 69 |
| HPV18 | L2 | 8 | 377 |
| HPV18 | L2 | 9 | 131 |
| HPV18 | L2 | 8 | 367 |
| HPV18 | L2 | 9 | 114 |
| HPV18 | L2 | 9 | 125 |
| HPV18 | L2 | 8 | 288 |
| HPV18 | L2 | 9 | 288 |
| HPV18 | L2 | 11 | 288 |
| HPV18 | L2 | 9 | 392 |
| HPV18 | L2 | 10 | 148 |
| HPV18 | L2 | 11 | 411 |
| HPV18 | L2 | 8 | 261 |
| HPV18 | L2 | 8 | 154 |
| HPV18 | L2 | 9 | 154 |
| HPV18 | L2 | 8 | 366 |
| HPV18 | L2 | 9 | 366 |
| HPV18 | L2 | 10 | 293 |
| HPV18 | L2 | 11 | 293 |
| HPV18 | L2 | 9 | 217 |
| HPV18 | L2 | 11 | 217 |
| HPV18 | L2 | 9 | 80 |
| HPV18 | L2 | 9 | 221 |
| HPV18 | L2 | 10 | 221 |
| HPV18 | L2 | 11 | 221 |
| HPV18 | L2 | 9 | 236 |
| HPV18 | L2 | 10 | 259 |
| HPV18 | L2 | 11 | 180 |
| HPV18 | L2 | 9 | 182 |
| HPV18 | L2 | 11 | 182 |
| HPV18 | L2 | 10 | 339 |
| HPV18 | L2 | 8 | 2 |
| HPV18 | L2 | 9 | 2 |
| HPV18 | L2 | 10 | 2 |
| HPV18 | L2 | 11 | 2 |
| HPV18 | L2 | 8 | 150 |
| HPV18 | L2 | 11 | 417 |
| HPV18 | L2 | 8 | 234 |
| HPV18 | L2 | 11 | 234 |
| HPV18 | L2 | 9 | 14 |
| HPV18 | L2 | 10 | 113 |
| HPV18 | L2 | 8 | 81 |
| HPV18 | L2 | 11 | 31 |
| HPV18 | L2 | 8 | 112 |
| HPV18 | L2 | 11 | 112 |
| HPV18 | L2 | 8 | 351 |
| HPV18 | L2 | 9 | 453 |
| HPV18 | L2 | 10 | 453 |
| HPV18 | L2 | 8 | 442 |
| HPV18 | L2 | 9 | 442 |
| HPV18 | L2 | 10 | 332 |
| HPV18 | L2 | 8 | 427 |
| HPV18 | L2 | 9 | 427 |
| HPV18 | L2 | 10 | 427 |
| HPV18 | L2 | 8 | 436 |
| HPV18 | L2 | 11 | 436 |
| HPV18 | L2 | 8 | 374 |
| HPV18 | L2 | 11 | 374 |
| HPV18 | L2 | 11 | 227 |
| HPV31 | E1 | 8 | 296 |
| HPV31 | E1 | 10 | 219 |
| HPV31 | E1 | 8 | 185 |
| HPV31 | E1 | 11 | 185 |
| HPV31 | E1 | 11 | 369 |
| HPV31 | E1 | 11 | 494 |
| HPV31 | E1 | 9 | 363 |
| HPV31 | E1 | 10 | 363 |
| HPV31 | E1 | 9 | 220 |
| HPV31 | E1 | 9 | 371 |
| HPV31 | E1 | 10 | 371 |
| HPV31 | E1 | 9 | 550 |
| NPV31 | E1 | 11 | 550 |
| HPV31 | E1 | 9 | 111 |
| HPV31 | E1 | 11 | 111 |
| HPV31 | E1 | 8 | 68 |
| HPV31 | E1 | 11 | 68 |
| HPV31 | E1 | 11 | 439 |
| HPV31 | E1 | 10 | 186 |
| HPV31 | E1 | 8 | 504 |
| HPV31 | E1 | 8 | 81 |
| HPV31 | E1 | 9 | 81 |
| HPV31 | E1 | 10 | 370 |
| HPV31 | E1 | 11 | 370 |
| HPV31 | E1 | 10 | 263 |
| HPV31 | E1 | 11 | 410 |
| HPV31 | E1 | 8 | 385 |
| HPV31 | E1 | 9 | 385 |
| HPV31 | E1 | 10 | 385 |
| HPV31 | E1 | 11 | 385 |
| HPV31 | E1 | 9 | 113 |
| HPV31 | E1 | 10 | 113 |
| HPV31 | E1 | 11 | 113 |
| HPV31 | E1 | 9 | 477 |
| HPV31 | E1 | 11 | 477 |
| HPV31 | E1 | 10 | 239 |
| HPV31 | E1 | 8 | 284 |
| HPV31 | E1 | 10 | 284 |
| HPV31 | E1 | 8 | 213 |
| HPV31 | E1 | 9 | 213 |
| HPV31 | E1 | 9 | 100 |
| HPV31 | E1 | 11 | 100 |
| HPV31 | E1 | 8 | 620 |
| HPV31 | E1 | 10 | 495 |
| HPV31 | E1 | 8 | 503 |
| HPV31 | E1 | 9 | 503 |
| HPV31 | E1 | 8 | 384 |
| HPV31 | E1 | 9 | 384 |
| HPV31 | E1 | 10 | 384 |
| HPV31 | E1 | 11 | 384 |
| HPV31 | E1 | 9 | 502 |
| HPV31 | E1 | 10 | 502 |
| HPV31 | E1 | 8 | 553 |
| HPV31 | E1 | 10 | 553 |
| HPV31 | E1 | 8 | 351 |
| HPV31 | E1 | 9 | 351 |
| HPV31 | E1 | 10 | 351 |
| HPV31 | E1 | 9 | 49 |
| HPV31 | E1 | 8 | 611 |
| HPV31 | E1 | 9 | 611 |
| HPV31 | E1 | 11 | 8 |
| HPV31 | E1 | 10 | 521 |
| HPV31 | E1 | 11 | 521 |
| HPV31 | E1 | 8 | 96 |
| HPV31 | E1 | 8 | 421 |
| HPV31 | E1 | 9 | 336 |
| HPV31 | E1 | 10 | 336 |
| HPV31 | E1 | 8 | 364 |
| HPV31 | E1 | 9 | 364 |
| HPV31 | E1 | 11 | 364 |
| HPV31 | E1 | 8 | 352 |
| HPV31 | E1 | 9 | 352 |
| HPV31 | E1 | 9 | 366 |
| HPV31 | E1 | 9 | 42 |
| HPV31 | E1 | 11 | 528 |
| HPV31 | E1 | 9 | 348 |
| HPV31 | E1 | 10 | 348 |
| HPV31 | E1 | 11 | 348 |
| HPV31 | E1 | 8 | 74 |
| HPV31 | E1 | 9 | 62 |

TABLE XVI-continued

HLA-A3 Motif Peptides

| 1 | 2 | 3 | 4 |
|---|---|---|---|
| HPV31 | E1 | 10 | 62 |
| HPV31 | E1 | 11 | 62 |
| HPV31 | E1 | 8 | 80 |
| HPV31 | E1 | 9 | 80 |
| HPV31 | E1 | 10 | 80 |
| HPV31 | E1 | 10 | 606 |
| HPV31 | E1 | 8 | 432 |
| HPV31 | E1 | 10 | 432 |
| HPV31 | E1 | 9 | 416 |
| HPV31 | E1 | 10 | 416 |
| HPV31 | E1 | 10 | 229 |
| HPV31 | E1 | 9 | 10 |
| HPV31 | E1 | 10 | 10 |
| HPV31 | E1 | 10 | 354 |
| HPV31 | E1 | 10 | 201 |
| HPV31 | E1 | 8 | 583 |
| HPV31 | E1 | 10 | 583 |
| HPV31 | E1 | 11 | 583 |
| HPV31 | E1 | 8 | 64 |
| HPV31 | E1 | 9 | 64 |
| HPV31 | E1 | 8 | 315 |
| HPV31 | E1 | 9 | 574 |
| HPV31 | E1 | 10 | 335 |
| HPV31 | E1 | 11 | 335 |
| HPV31 | E1 | 8 | 592 |
| HPV31 | E1 | 8 | 466 |
| HPV31 | E1 | 8 | 221 |
| HPV31 | E1 | 11 | 221 |
| HPV31 | E1 | 8 | 50 |
| HPV31 | E1 | 8 | 443 |
| HPV31 | E1 | 8 | 372 |
| HPV31 | E1 | 9 | 372 |
| HPV31 | E1 | 9 | 473 |
| HPV31 | E1 | 10 | 473 |
| HPV31 | E1 | 9 | 425 |
| HPV31 | E1 | 8 | 436 |
| HPV31 | E1 | 10 | 436 |
| HPV31 | E1 | 8 | 199 |
| HPV31 | E1 | 11 | 593 |
| HPV31 | E1 | 9 | 566 |
| HPV31 | E1 | 11 | 566 |
| HPV31 | E1 | 9 | 433 |
| HPV31 | E1 | 11 | 433 |
| HPV31 | E1 | 9 | 457 |
| HPV31 | E1 | 10 | 457 |
| HPV31 | E1 | 10 | 476 |
| HPV31 | E1 | 10 | 13 |
| HPV31 | E1 | 8 | 612 |
| HPV31 | E1 | 8 | 417 |
| HPV31 | E1 | 9 | 417 |
| HPV31 | E1 | 11 | 417 |
| HPV31 | E1 | 9 | 230 |
| HPV31 | E1 | 9 | 305 |
| HPV31 | E1 | 9 | 252 |
| HPV31 | E1 | 10 | 252 |
| HPV31 | E1 | 11 | 252 |
| HPV31 | E1 | 9 | 157 |
| HPV31 | E1 | 8 | 11 |
| HPV31 | E1 | 9 | 11 |
| HPV31 | E1 | 8 | 386 |
| HPV31 | E1 | 9 | 386 |
| HPV31 | E1 | 10 | 386 |
| HPV31 | E1 | 8 | 225 |
| HPV31 | E1 | 11 | 446 |
| HPV31 | E1 | 9 | 196 |
| HPV31 | E1 | 11 | 196 |
| HPV31 | E1 | 10 | 222 |
| HPV31 | E1 | 11 | 222 |
| HPV31 | E1 | 9 | 78 |
| HPV31 | E1 | 10 | 78 |
| HPV31 | E1 | 11 | 78 |
| HPV31 | E1 | 8 | 71 |
| HPV31 | E1 | 9 | 71 |
| HPV31 | E1 | 11 | 71 |
| HPV31 | E1 | 8 | 487 |
| HPV31 | E1 | 10 | 487 |
| HPV31 | E1 | 11 | 487 |
| HPV31 | E1 | 8 | 456 |
| HPV31 | E1 | 10 | 456 |
| HPV31 | E1 | 11 | 456 |
| HPV31 | E1 | 11 | 162 |
| HPV31 | E1 | 8 | 328 |
| HPV31 | E1 | 9 | 560 |
| HPV31 | E1 | 9 | 355 |
| HPV31 | E1 | 8 | 112 |
| HPV31 | E1 | 10 | 112 |
| HPV31 | E1 | 11 | 112 |
| HPV31 | E1 | 11 | 51 |
| HPV31 | E1 | 8 | 512 |
| HPV31 | E1 | 8 | 478 |
| HPV31 | E1 | 10 | 478 |
| HPV31 | E1 | 11 | 478 |
| HPV31 | E1 | 11 | 453 |
| HPV31 | E1 | 11 | 174 |
| HPV31 | E1 | 11 | 471 |
| HPV31 | E1 | 9 | 479 |
| HPV31 | E1 | 10 | 479 |
| HPV31 | E1 | 9 | 268 |
| HPV31 | E1 | 9 | 544 |
| HPV31 | E1 | 10 | 381 |
| HPV31 | E1 | 11 | 381 |
| HPV31 | E1 | 8 | 184 |
| HPV31 | E1 | 9 | 184 |
| HPV31 | E1 | 10 | 110 |
| HPV31 | E1 | 11 | 262 |
| HPV31 | E1 | 9 | 619 |
| HPV31 | E1 | 8 | 383 |
| HPV31 | E1 | 9 | 383 |
| HPV31 | E1 | 10 | 383 |
| HPV31 | E1 | 11 | 383 |
| HPV31 | E1 | 9 | 552 |
| HPV31 | E1 | 11 | 552 |
| HPV31 | E1 | 10 | 190 |
| HPV31 | E1 | 10 | 424 |
| HPV31 | E1 | 8 | 497 |
| HPV31 | E1 | 11 | 380 |
| HPV31 | E1 | 9 | 441 |
| HPV31 | E1 | 10 | 441 |
| HPV31 | E1 | 8 | 291 |
| HPV31 | E1 | 10 | 291 |
| HPV31 | E1 | 10 | 590 |
| HPV31 | E1 | 10 | 485 |
| HPV31 | E1 | 10 | 374 |
| HPV31 | E1 | 10 | 210 |
| HPV31 | E1 | 11 | 210 |
| HPV31 | E1 | 11 | 463 |
| HPV31 | E1 | 8 | 119 |
| HPV31 | E1 | 10 | 232 |
| HPV31 | E1 | 8 | 179 |
| HPV31 | E1 | 9 | 412 |
| HPV31 | E1 | 8 | 362 |
| HPV31 | E1 | 10 | 362 |
| HPV31 | E1 | 11 | 362 |
| HPV31 | E1 | 10 | 501 |
| HPV31 | E1 | 11 | 501 |
| HPV31 | E1 | 11 | 520 |
| HPV31 | E1 | 9 | 125 |
| HPV31 | E1 | 10 | 69 |
| HPV31 | E1 | 11 | 69 |
| HPV31 | E1 | 8 | 442 |
| HPV31 | E1 | 9 | 442 |
| HPV31 | E1 | 8 | 188 |
| HPV31 | E1 | 10 | 454 |
| HPV31 | E1 | 8 | 286 |
| HPV31 | E1 | 11 | 286 |
| HPV31 | E1 | 9 | 202 |
| HPV31 | E1 | 8 | 543 |
| HPV31 | E1 | 10 | 543 |
| HPV31 | E1 | 9 | 542 |
| HPV31 | E1 | 11 | 542 |

TABLE XVI-continued

HLA-A3 Motif Peptides

| 1 | 2 | 3 | 4 |
|---|---|---|---|
| HPV31 | E1 | 8 | 234 |
| HPV31 | E1 | 10 | 234 |
| HPV31 | E1 | 9 | 256 |
| HPV31 | E1 | 10 | 256 |
| HPV31 | E1 | 9 | 437 |
| HPV31 | E1 | 10 | 153 |
| HPV31 | E1 | 10 | 94 |
| HPV31 | E1 | 9 | 584 |
| HPV31 | E1 | 10 | 584 |
| HPV31 | E1 | 8 | 337 |
| HPV31 | E1 | 9 | 337 |
| HPV31 | E1 | 8 | 258 |
| HPV31 | E1 | 10 | 258 |
| HPV31 | E1 | 10 | 563 |
| HPV31 | E1 | 8 | 388 |
| HPV31 | E1 | 10 | 388 |
| HPV31 | E1 | 11 | 388 |
| HPV31 | E1 | 8 | 350 |
| HPV31 | E1 | 9 | 350 |
| HPV31 | E1 | 10 | 350 |
| HPV31 | E1 | 11 | 350 |
| HPV31 | E1 | 8 | 402 |
| HPV31 | E1 | 11 | 402 |
| HPV31 | E1 | 11 | 500 |
| HPV31 | E1 | 9 | 187 |
| HPV31 | E1 | 9 | 285 |
| HPV31 | E1 | 8 | 255 |
| HPV31 | E1 | 10 | 255 |
| HPV31 | E1 | 11 | 255 |
| HPV31 | E1 | 8 | 257 |
| HPV31 | E1 | 9 | 257 |
| HPV31 | E1 | 11 | 257 |
| HPV31 | E1 | 8 | 400 |
| HPV31 | E1 | 10 | 400 |
| HPV31 | E1 | 8 | 306 |
| HPV31 | E1 | 11 | 47 |
| HPV31 | E1 | 8 | 253 |
| HPV31 | E1 | 9 | 253 |
| HPV31 | E1 | 10 | 253 |
| HPV31 | E1 | 10 | 549 |
| HPV31 | E1 | 8 | 451 |
| HPV31 | E1 | 9 | 283 |
| HPV31 | E1 | 11 | 283 |
| HPV31 | E1 | 9 | 53 |
| HPV31 | E1 | 11 | 53 |
| HPV31 | E1 | 9 | 610 |
| HPV31 | E1 | 10 | 610 |
| HPV31 | E1 | 10 | 347 |
| HPV31 | E1 | 11 | 347 |
| HPV31 | E1 | 9 | 182 |
| HPV31 | E1 | 10 | 182 |
| HPV31 | E1 | 11 | 182 |
| HPV31 | E1 | 11 | 577 |
| HPV31 | E1 | 10 | 156 |
| HPV31 | E1 | 8 | 15 |
| HPV31 | E1 | 9 | 547 |
| HPV31 | E1 | 8 | 104 |
| HPV31 | E1 | 8 | 601 |
| HPV31 | E1 | 8 | 117 |
| HPV31 | E1 | 10 | 117 |
| HPV31 | E1 | 8 | 376 |
| HPV31 | E1 | 9 | 55 |
| HPV31 | E1 | 9 | 507 |
| HPV31 | E1 | 11 | 507 |
| HPV31 | E1 | 10 | 573 |
| HPV31 | E1 | 10 | 541 |
| HPV31 | E1 | 11 | 93 |
| HPV31 | E1 | 10 | 170 |
| HPV31 | E1 | 8 | 524 |
| HPV31 | E1 | 9 | 524 |
| HPV31 | E1 | 10 | 524 |
| HPV31 | E1 | 8 | 580 |
| HPV31 | E1 | 11 | 580 |
| HPV31 | E1 | 9 | 60 |
| HPV31 | E1 | 11 | 60 |
| HPV31 | E1 | 9 | 67 |
| HPV31 | E1 | 8 | 475 |
| HPV31 | E1 | 11 | 475 |
| HPV31 | E1 | 10 | 430 |
| HPV31 | E1 | 9 | 361 |
| HPV31 | E1 | 11 | 361 |
| HPV31 | E1 | 9 | 399 |
| HPV31 | E1 | 11 | 399 |
| HPV31 | E1 | 8 | 323 |
| HPV31 | E1 | 9 | 176 |
| HPV31 | E1 | 10 | 176 |
| HPV31 | E1 | 11 | 176 |
| HPV31 | E1 | 8 | 420 |
| HPV31 | E1 | 9 | 420 |
| HPV31 | E1 | 8 | 260 |
| HPV31 | E1 | 10 | 267 |
| HPV31 | E1 | 10 | 124 |
| HPV31 | E1 | 10 | 599 |
| HPV31 | E1 | 11 | 562 |
| HPV31 | E1 | 8 | 293 |
| HPV31 | E1 | 10 | 293 |
| HPV31 | E1 | 11 | 293 |
| HPV31 | E1 | 11 | 303 |
| HPV31 | E1 | 9 | 595 |
| HPV31 | E1 | 8 | 438 |
| HPV31 | E1 | 9 | 154 |
| HPV31 | E1 | 10 | 99 |
| HPV31 | E1 | 11 | 414 |
| HPV31 | E1 | 8 | 158 |
| HPV31 | E1 | 9 | 95 |
| HPV31 | E1 | 8 | 585 |
| HPV31 | E1 | 9 | 585 |
| HPV31 | E1 | 11 | 585 |
| HPV31 | E1 | 8 | 365 |
| HPV31 | E1 | 10 | 365 |
| HPV31 | E1 | 10 | 41 |
| HPV31 | E1 | 9 | 591 |
| HPV31 | E1 | 10 | 472 |
| HPV31 | E1 | 11 | 472 |
| HPV31 | E1 | 9 | 435 |
| HPV31 | E1 | 11 | 435 |
| HPV31 | E1 | 9 | 198 |
| HPV31 | E1 | 8 | 526 |
| HPV31 | E1 | 9 | 401 |
| HPV31 | E1 | 11 | 98 |
| HPV31 | E1 | 11 | 40 |
| HPV31 | E1 | 9 | 294 |
| HPV31 | E1 | 10 | 294 |
| HPV31 | E1 | 9 | 211 |
| HPV31 | E1 | 10 | 211 |
| HPV31 | E1 | 11 | 211 |
| HPV31 | E1 | 11 | 281 |
| HPV31 | E1 | 8 | 295 |
| HPV31 | E1 | 9 | 295 |
| HPV31 | E1 | 8 | 65 |
| HPV31 | E1 | 11 | 65 |
| HPV31 | E1 | 8 | 212 |
| HPV31 | E1 | 9 | 212 |
| HPV31 | E1 | 10 | 212 |
| HPV31 | E1 | 8 | 214 |
| HPV31 | E1 | 11 | 334 |
| HPV31 | E1 | 11 | 617 |
| HPV31 | E1 | 8 | 567 |
| HPV31 | E1 | 10 | 567 |
| HPV31 | E1 | 8 | 12 |
| HPV31 | E1 | 11 | 12 |
| HPV31 | E1 | 8 | 43 |
| HPV31 | E1 | 10 | 304 |
| HPV31 | E1 | 8 | 224 |
| HPV31 | E1 | 9 | 224 |
| HPV31 | E1 | 8 | 269 |
| HPV31 | E1 | 9 | 233 |
| HPV31 | E1 | 11 | 233 |
| HPV31 | E1 | 11 | 152 |
| HPV31 | E1 | 8 | 387 |

TABLE XVI-continued

HLA-A3 Motif Peptides

| 1 | 2 | 3 | 4 |
|---|---|---|---|
| HPV31 | E1 | 9 | 387 |
| HPV31 | E1 | 11 | 387 |
| HPV31 | E1 | 11 | 180 |
| HPV31 | E1 | 8 | 545 |
| HPV31 | E1 | 11 | 545 |
| HPV31 | E1 | 11 | 505 |
| HPV31 | E1 | 11 | 218 |
| HPV31 | E1 | 10 | 48 |
| HPV31 | E1 | 8 | 101 |
| HPV31 | E1 | 10 | 101 |
| HPV31 | E1 | 11 | 101 |
| HPV31 | E1 | 8 | 565 |
| HPV31 | E1 | 10 | 565 |
| HPV31 | E1 | 8 | 177 |
| HPV31 | E1 | 9 | 177 |
| HPV31 | E1 | 10 | 177 |
| HPV31 | E1 | 11 | 325 |
| HPV31 | E1 | 8 | 349 |
| HPV31 | E1 | 9 | 349 |
| HPV31 | E1 | 10 | 349 |
| HPV31 | E1 | 11 | 349 |
| HPV31 | E1 | 8 | 254 |
| HPV31 | E1 | 9 | 254 |
| HPV31 | E1 | 11 | 254 |
| HPV31 | E1 | 8 | 413 |
| HPV31 | E1 | 8 | 434 |
| HPV31 | E1 | 10 | 434 |
| HPV31 | E1 | 8 | 197 |
| HPV31 | E1 | 10 | 197 |
| HPV31 | E1 | 8 | 525 |
| HPV31 | E1 | 9 | 525 |
| HPV31 | E1 | 9 | 223 |
| HPV31 | E1 | 10 | 223 |
| HPV31 | E1 | 9 | 564 |
| HPV31 | E1 | 11 | 564 |
| HPV31 | E1 | 10 | 17 |
| HPV31 | E1 | 10 | 251 |
| HPV31 | E1 | 11 | 251 |
| HPV31 | E1 | 10 | 319 |
| HPV31 | E1 | 8 | 405 |
| HPV31 | E1 | 8 | 489 |
| HPV31 | E1 | 9 | 489 |
| HPV31 | E1 | 8 | 481 |
| HPV31 | E1 | 11 | 359 |
| HPV31 | E1 | 8 | 241 |
| HPV31 | E1 | 11 | 238 |
| HPV31 | E1 | 9 | 465 |
| HPV31 | E1 | 10 | 313 |
| HPV31 | E1 | 10 | 195 |
| HPV31 | E1 | 9 | 511 |
| HPV31 | E1 | 9 | 558 |
| HPV31 | E1 | 11 | 558 |
| HPV31 | E1 | 8 | 19 |
| HPV31 | E2 | 9 | 277 |
| HPV31 | E2 | 10 | 277 |
| HPV31 | E2 | 8 | 278 |
| HPV31 | E2 | 9 | 278 |
| HPV31 | E2 | 8 | 279 |
| HPV31 | E2 | 8 | 188 |
| HPV31 | E2 | 10 | 208 |
| HPV31 | E2 | 9 | 229 |
| HPV31 | E2 | 10 | 229 |
| HPV31 | E2 | 11 | 229 |
| HPV31 | E2 | 8 | 61 |
| HPV31 | E2 | 9 | 61 |
| HPV31 | E2 | 9 | 291 |
| HPV31 | E2 | 9 | 239 |
| HPV31 | E2 | 10 | 228 |
| HPV31 | E2 | 11 | 228 |
| HPV31 | E2 | 8 | 27 |
| HPV31 | E2 | 9 | 27 |
| HPV31 | E2 | 11 | 27 |
| HPV31 | E2 | 8 | 272 |
| HPV31 | E2 | 8 | 307 |
| HPV31 | E2 | 9 | 307 |
| HPV31 | E2 | 10 | 307 |
| HPV31 | E2 | 9 | 330 |
| HPV31 | E2 | 11 | 145 |
| HPV31 | E2 | 8 | 40 |
| HPV31 | E2 | 9 | 301 |
| HPV31 | E2 | 10 | 301 |
| HPV31 | E2 | 11 | 301 |
| HPV31 | E2 | 8 | 351 |
| HPV31 | E2 | 9 | 122 |
| HPV31 | E2 | 10 | 122 |
| HPV31 | E2 | 8 | 22 |
| HPV31 | E2 | 11 | 22 |
| HPV31 | E2 | 10 | 268 |
| HPV31 | E2 | 11 | 268 |
| HPV31 | E2 | 8 | 124 |
| HPV31 | E2 | 9 | 174 |
| HPV31 | E2 | 10 | 174 |
| HPV31 | E2 | 8 | 39 |
| HPV31 | E2 | 9 | 39 |
| HPV31 | E2 | 10 | 162 |
| HPV31 | E2 | 10 | 149 |
| HPV31 | E2 | 11 | 149 |
| HPV31 | E2 | 11 | 234 |
| HPV31 | E2 | 10 | 204 |
| HPV31 | E2 | 9 | 48 |
| HPV31 | E2 | 11 | 197 |
| HPV31 | E2 | 8 | 80 |
| HPV31 | E2 | 9 | 80 |
| HPV31 | E2 | 11 | 185 |
| HPV31 | E2 | 9 | 118 |
| HPV31 | E2 | 11 | 207 |
| HPV31 | E2 | 10 | 121 |
| HPV31 | E2 | 11 | 121 |
| HPV31 | E2 | 8 | 200 |
| HPV31 | E2 | 9 | 200 |
| HPV31 | E2 | 8 | 171 |
| HPV31 | E2 | 8 | 168 |
| HPV31 | E2 | 9 | 168 |
| HPV31 | E2 | 10 | 168 |
| HPV31 | E2 | 11 | 168 |
| HPV31 | E2 | 8 | 108 |
| HPV31 | E2 | 10 | 300 |
| HPV31 | E2 | 11 | 300 |
| HPV31 | E2 | 8 | 123 |
| HPV31 | E2 | 9 | 123 |
| HPV31 | E2 | 9 | 209 |
| HPV31 | E2 | 9 | 156 |
| HPV31 | E2 | 9 | 179 |
| HPV31 | E2 | 10 | 179 |
| HPV31 | E2 | 8 | 231 |
| HPV31 | E2 | 9 | 231 |
| HPV31 | E2 | 10 | 235 |
| HPV31 | E2 | 11 | 235 |
| HPV31 | E2 | 9 | 187 |
| HPV31 | E2 | 9 | 113 |
| HPV31 | E2 | 9 | 29 |
| HPV31 | E2 | 10 | 35 |
| HPV31 | E2 | 11 | 35 |
| HPV31 | E2 | 8 | 164 |
| HPV31 | E2 | 10 | 297 |
| HPV31 | E2 | 10 | 52 |
| HPV31 | E2 | 8 | 30 |
| HPV31 | E2 | 8 | 295 |
| HPV31 | E2 | 10 | 15 |
| HPV31 | E2 | 11 | 15 |
| HPV31 | E2 | 8 | 304 |
| HPV31 | E2 | 11 | 304 |
| HPV31 | E2 | 11 | 275 |
| HPV31 | E2 | 9 | 205 |
| HPV31 | E2 | 9 | 345 |
| HPV31 | E2 | 11 | 165 |
| HPV31 | E2 | 8 | 193 |
| HPV31 | E2 | 8 | 210 |
| HPV31 | E2 | 8 | 45 |
| HPV31 | E2 | 9 | 306 |

TABLE XVI-continued

HLA-A3 Motif Peptides

| 1 | 2 | 3 | 4 |
|---|---|---|---|
| HPV31 | E2 | 10 | 306 |
| HPV31 | E2 | 11 | 306 |
| HPV31 | E2 | 8 | 299 |
| HPV31 | E2 | 11 | 299 |
| HPV31 | E2 | 10 | 155 |
| HPV31 | E2 | 11 | 14 |
| HPV31 | E2 | 9 | 26 |
| HPV31 | E2 | 10 | 26 |
| HPV31 | E2 | 8 | 230 |
| HPV31 | E2 | 9 | 230 |
| HPV31 | E2 | 10 | 230 |
| HPV31 | E2 | 11 | 42 |
| HPV31 | E2 | 8 | 312 |
| HPV31 | E2 | 11 | 4 |
| HPV31 | E2 | 8 | 62 |
| HPV31 | E2 | 11 | 62 |
| HPV31 | E2 | 9 | 103 |
| HPV31 | E2 | 10 | 103 |
| HPV31 | E2 | 11 | 103 |
| HPV31 | E2 | 9 | 342 |
| HPV31 | E2 | 8 | 49 |
| HPV31 | E2 | 10 | 78 |
| HPV31 | E2 | 11 | 78 |
| HPV31 | E2 | 11 | 77 |
| HPV31 | E2 | 8 | 337 |
| HPV31 | E2 | 8 | 271 |
| HPV31 | E2 | 9 | 271 |
| HPV31 | E2 | 9 | 153 |
| HPV31 | E2 | 9 | 21 |
| HPV31 | E2 | 8 | 170 |
| HPV31 | E2 | 9 | 170 |
| HPV31 | E2 | 8 | 303 |
| HPV31 | E2 | 9 | 303 |
| HPV31 | E2 | 10 | 254 |
| HPV31 | E2 | 9 | 127 |
| HPV31 | E2 | 10 | 127 |
| HPV31 | E2 | 8 | 219 |
| HPV31 | E2 | 11 | 219 |
| HPV31 | E2 | 9 | 361 |
| HPV31 | E2 | 10 | 9 |
| HPV31 | E2 | 11 | 9 |
| HPV31 | E2 | 8 | 60 |
| HPV31 | E2 | 9 | 60 |
| HPV31 | E2 | 10 | 60 |
| HPV31 | E2 | 8 | 290 |
| HPV31 | E2 | 10 | 290 |
| HPV31 | E2 | 9 | 294 |
| HPV31 | E2 | 8 | 106 |
| HPV31 | E2 | 10 | 106 |
| HPV31 | E2 | 8 | 12 |
| HPV31 | E2 | 11 | 120 |
| HPV31 | E2 | 11 | 317 |
| HPV31 | E2 | 9 | 283 |
| HPV31 | E2 | 10 | 96 |
| HPV31 | E2 | 10 | 191 |
| HPV31 | E2 | 8 | 151 |
| HPV31 | E2 | 9 | 151 |
| HPV31 | E2 | 11 | 151 |
| HPV31 | E2 | 10 | 57 |
| HPV31 | E2 | 11 | 57 |
| HPV31 | E2 | 8 | 238 |
| HPV31 | E2 | 10 | 238 |
| HPV31 | E2 | 9 | 350 |
| HPV31 | E2 | 8 | 25 |
| HPV31 | E2 | 10 | 25 |
| HPV31 | E2 | 11 | 25 |
| HPV31 | E2 | 8 | 37 |
| HPV31 | E2 | 9 | 37 |
| HPV31 | E2 | 10 | 37 |
| HPV31 | E2 | 11 | 37 |
| HPV31 | E2 | 8 | 7 |
| HPV31 | E2 | 9 | 311 |
| HPV31 | E2 | 10 | 247 |
| HPV31 | E2 | 11 | 247 |
| HPV31 | E2 | 10 | 276 |
| HPV31 | E2 | 11 | 276 |
| HPV31 | E2 | 10 | 288 |
| HPV31 | E2 | 8 | 206 |
| HPV31 | E2 | 9 | 53 |
| HPV31 | E2 | 8 | 98 |
| HPV31 | E2 | 8 | 201 |
| HPV31 | E2 | 11 | 242 |
| HPV31 | E2 | 8 | 346 |
| HPV31 | E2 | 11 | 324 |
| HPV31 | E2 | 10 | 198 |
| HPV31 | E2 | 11 | 198 |
| HPV31 | E2 | 9 | 269 |
| HPV31 | E2 | 10 | 269 |
| HPV31 | E2 | 11 | 269 |
| HPV31 | E2 | 10 | 63 |
| HPV31 | E2 | 11 | 216 |
| HPV31 | E2 | 8 | 104 |
| HPV31 | E2 | 9 | 104 |
| HPV31 | E2 | 10 | 104 |
| HPV31 | E2 | 11 | 227 |
| HPV31 | E2 | 8 | 329 |
| HPV31 | E2 | 10 | 329 |
| HPV31 | E2 | 8 | 331 |
| HPV31 | E2 | 9 | 107 |
| HPV31 | E2 | 8 | 180 |
| HPV31 | E2 | 9 | 180 |
| HPV31 | E2 | 8 | 81 |
| HPV31 | E2 | 10 | 341 |
| HPV31 | E2 | 8 | 128 |
| HPV31 | E2 | 9 | 128 |
| HPV31 | E2 | 11 | 128 |
| HPV31 | E2 | 10 | 93 |
| HPV31 | E2 | 8 | 232 |
| HPV31 | E2 | 9 | 97 |
| HPV31 | E2 | 8 | 222 |
| HPV31 | E2 | 8 | 292 |
| HPV31 | E2 | 11 | 292 |
| HPV31 | E2 | 9 | 221 |
| HPV31 | E2 | 8 | 240 |
| HPV31 | E2 | 10 | 220 |
| HPV31 | E2 | 11 | 116 |
| HPV31 | E2 | 8 | 362 |
| HPV31 | E2 | 10 | 146 |
| HPV31 | E2 | 9 | 10 |
| HPV31 | E2 | 10 | 10 |
| HPV31 | E2 | 11 | 267 |
| HPV31 | E2 | 9 | 199 |
| HPV31 | E2 | 10 | 199 |
| HPV31 | E2 | 9 | 192 |
| HPV31 | E2 | 11 | 287 |
| HPV31 | E2 | 9 | 64 |
| HPV31 | E2 | 11 | 340 |
| HPV31 | E2 | 9 | 147 |
| HPV31 | E2 | 9 | 58 |
| HPV31 | E2 | 10 | 58 |
| HPV31 | E2 | 11 | 58 |
| HPV31 | E2 | 8 | 328 |
| HPV31 | E2 | 9 | 328 |
| HPV31 | E2 | 11 | 328 |
| HPV31 | E2 | 11 | 92 |
| HPV31 | E2 | 9 | 167 |
| HPV31 | E2 | 10 | 167 |
| HPV31 | E2 | 11 | 167 |
| HPV31 | E2 | 10 | 178 |
| HPV31 | E2 | 11 | 178 |
| HPV31 | E2 | 10 | 344 |
| HPV31 | E2 | 10 | 102 |
| HPV31 | E2 | 11 | 102 |
| HPV31 | E2 | 8 | 131 |
| HPV31 | E2 | 9 | 159 |
| HPV31 | E2 | 10 | 159 |
| HPV31 | E5 | 8 | 53 |
| HPV31 | E5 | 11 | 53 |
| HPV31 | E5 | 8 | 59 |
| HPV31 | E5 | 10 | 59 |

TABLE XVI-continued

HLA-A3 Motif Peptides

| 1 | 2 | 3 | 4 |
|---|---|---|---|
| HPV31 | E5 | 11 | 14 |
| HPV31 | E5 | 8 | 61 |
| HPV31 | E5 | 11 | 20 |
| HPV31 | E5 | 9 | 60 |
| HPV31 | E5 | 10 | 66 |
| HPV31 | E5 | 10 | 15 |
| HPV31 | E5 | 9 | 72 |
| HPV31 | E5 | 9 | 52 |
| HPV31 | E5 | 11 | 48 |
| HPV31 | E5 | 10 | 6 |
| HPV31 | E5 | 8 | 46 |
| HPV31 | E5 | 9 | 11 |
| HPV31 | E5 | 8 | 17 |
| HPV31 | E5 | 8 | 23 |
| HPV31 | E5 | 8 | 71 |
| HPV31 | E5 | 10 | 71 |
| HPV31 | E5 | 9 | 45 |
| HPV31 | E5 | 9 | 15 |
| HPV31 | E5 | 9 | 22 |
| HPV31 | E5 | 10 | 44 |
| HPV31 | E5 | 11 | 43 |
| HPV31 | E5 | 8 | 32 |
| HPV31 | E5 | 9 | 32 |
| HPV31 | E5 | 11 | 5 |
| HPV31 | E5 | 8 | 70 |
| HPV31 | E5 | 9 | 70 |
| HPV31 | E5 | 11 | 70 |
| HPV31 | E5 | 8 | 56 |
| HPV31 | E5 | 11 | 56 |
| HPV31 | E5 | 9 | 31 |
| HPV31 | E5 | 10 | 31 |
| HPV31 | E5 | 9 | 58 |
| HPV31 | E5 | 11 | 58 |
| HPV31 | E5 | 10 | 10 |
| HPV31 | E5 | 9 | 7 |
| HPV31 | E5 | 10 | 54 |
| HPV31 | E5 | 8 | 8 |
| HPV31 | E5 | 8 | 65 |
| HPV31 | E5 | 11 | 65 |
| HPV31 | E5 | 8 | 51 |
| HPV31 | E5 | 10 | 51 |
| HPV31 | E5 | 8 | 73 |
| HPV31 | E5 | 8 | 12 |
| HPV31 | E5 | 10 | 21 |
| HPV31 | E5 | 8 | 33 |
| HPV31 | E5 | 11 | 9 |
| HPV31 | E5 | 9 | 64 |
| HPV31 | E5 | 9 | 50 |
| HPV31 | E5 | 11 | 50 |
| HPV31 | E5 | 8 | 68 |
| HPV31 | E5 | 10 | 58 |
| HPV31 | E5 | 11 | 68 |
| HPV31 | E5 | 10 | 63 |
| HPV31 | E6 | 9 | 46 |
| HPV31 | E6 | 10 | 46 |
| HPV31 | E6 | 10 | 18 |
| HPV31 | E6 | 9 | 136 |
| HPV31 | E6 | 11 | 56 |
| HPV31 | E6 | 8 | 63 |
| HPV31 | E6 | 10 | 63 |
| HPV31 | E6 | 10 | 5 |
| HPV31 | E6 | 11 | 44 |
| HPV31 | E6 | 11 | 98 |
| HPV31 | E6 | 9 | 57 |
| HPV31 | E6 | 10 | 75 |
| HPV31 | E6 | 8 | 20 |
| HPV31 | E6 | 8 | 25 |
| HPV31 | E6 | 10 | 25 |
| HPV31 | E6 | 10 | 14 |
| HPV31 | E6 | 8 | 39 |
| HPV31 | E6 | 9 | 39 |
| HPV31 | E6 | 10 | 45 |
| HPV31 | E6 | 11 | 45 |
| HPV31 | E6 | 8 | 47 |
| HPV31 | E6 | 9 | 47 |
| HPV31 | E6 | 10 | 129 |
| HPV31 | E6 | 8 | 95 |
| HPV31 | E6 | 10 | 85 |
| HPV31 | E6 | 8 | 61 |
| HPV31 | E6 | 9 | 61 |
| HPV31 | E6 | 10 | 61 |
| HPV31 | E6 | 9 | 60 |
| HPV31 | E6 | 10 | 60 |
| HPV31 | E6 | 11 | 60 |
| HPV31 | E6 | 8 | 118 |
| HPV31 | E6 | 9 | 118 |
| HPV31 | E6 | 8 | 137 |
| HPV31 | E6 | 8 | 128 |
| HPV31 | E6 | 11 | 128 |
| HPV31 | E6 | 9 | 52 |
| HPV31 | E6 | 8 | 55 |
| HPV31 | E6 | 9 | 94 |
| HPV31 | E6 | 8 | 11 |
| HPV31 | E6 | 8 | 72 |
| HPV31 | E6 | 9 | 72 |
| HPV31 | E6 | 10 | 72 |
| HPV31 | E6 | 8 | 110 |
| HPV31 | E6 | 9 | 110 |
| HPV31 | E6 | 8 | 119 |
| HPV31 | E6 | 9 | 100 |
| HPV31 | E6 | 10 | 99 |
| HPV31 | E6 | 9 | 15 |
| HPV31 | E6 | 9 | 37 |
| HPV31 | E6 | 10 | 37 |
| HPV31 | E6 | 11 | 37 |
| HPV31 | E6 | 11 | 50 |
| HPV31 | E6 | 8 | 1 |
| HPV31 | E6 | 10 | 1 |
| HPV31 | E6 | 11 | 1 |
| HPV31 | E6 | 9 | 127 |
| HPV31 | E6 | 9 | 5 |
| HPV31 | E6 | 9 | 109 |
| HPV31 | E6 | 10 | 109 |
| HPV31 | E6 | 10 | 36 |
| HPV31 | E6 | 11 | 36 |
| HPV31 | E6 | 8 | 135 |
| HPV31 | E6 | 10 | 135 |
| HPV31 | E6 | 11 | 55 |
| HPV31 | E6 | 8 | 124 |
| HPV31 | E6 | 9 | 68 |
| HPV31 | E6 | 10 | 58 |
| HPV31 | E6 | 8 | 27 |
| HPV31 | E6 | 11 | 17 |
| HPV31 | E6 | 8 | 15 |
| HPV31 | E6 | 9 | 82 |
| HPV31 | E6 | 11 | 105 |
| HPV31 | E6 | 8 | 48 |
| HPV31 | E6 | 9 | 133 |
| HPV31 | E6 | 10 | 133 |
| HPV31 | E6 | 10 | 51 |
| HPV31 | E6 | 8 | 87 |
| HPV31 | E6 | 9 | 86 |
| HPV31 | E6 | 8 | 62 |
| HPV31 | E6 | 9 | 62 |
| HPV31 | E6 | 11 | 62 |
| HPV31 | E6 | 8 | 73 |
| HPV31 | E6 | 9 | 73 |
| HPV31 | E6 | 10 | 132 |
| HPV31 | E6 | 11 | 132 |
| HPV31 | E6 | 10 | 23 |
| HPV31 | E6 | 11 | 84 |
| HPV31 | E5 | 8 | 70 |
| HPV31 | E6 | 10 | 70 |
| HPV31 | E6 | 11 | 70 |
| HPV31 | E6 | 10 | 81 |
| HPV31 | E7 | 11 | 42 |
| HPV31 | E7 | 9 | 58 |
| HPV31 | E7 | 10 | 68 |
| HPV31 | E7 | 10 | 14 |
| HPV31 | E7 | 10 | 48 |

TABLE XVI-continued

HLA-A3 Motif Peptides

| 1 | 2 | 3 | 4 |
|---|---|---|---|
| HPV31 | E7 | 10 | 36 |
| HPV31 | E7 | 8 | 18 |
| HPV31 | E7 | 8 | 35 |
| HPV31 | E7 | 11 | 35 |
| HPV31 | E7 | 8 | 4 |
| HPV31 | E7 | 10 | 57 |
| HPV31 | E7 | 11 | 87 |
| HPV31 | E7 | 10 | 88 |
| HPV31 | E7 | 8 | 38 |
| HPV31 | E7 | 10 | 78 |
| HPV31 | E7 | 9 | 89 |
| HPV31 | E7 | 9 | 54 |
| HPV31 | E7 | 11 | 67 |
| HPV31 | E7 | 11 | 13 |
| HPV31 | E7 | 10 | 53 |
| HPV31 | E7 | 11 | 47 |
| HPV31 | E7 | 9 | 44 |
| HPV31 | E7 | 11 | 9 |
| HPV31 | E7 | 8 | 70 |
| HPV31 | E7 | 10 | 2 |
| HPV31 | E7 | 11 | 77 |
| HPV31 | E7 | 11 | 32 |
| HPV31 | E7 | 11 | 56 |
| HPV31 | E7 | 9 | 49 |
| HPV31 | E7 | 8 | 90 |
| HPV31 | E7 | 9 | 37 |
| HPV31 | E7 | 8 | 12 |
| HPV31 | E7 | 8 | 55 |
| HPV31 | E7 | 9 | 11 |
| HPV31 | L1 | 10 | 347 |
| HPV31 | L1 | 11 | 347 |
| HPV31 | L1 | 9 | 102 |
| HPV31 | L1 | 8 | 386 |
| HPV31 | L1 | 10 | 458 |
| HPV31 | L1 | 11 | 458 |
| HPV31 | L1 | 9 | 137 |
| HPV31 | L1 | 9 | 483 |
| HPV31 | L1 | 11 | 37 |
| HPV31 | L1 | 8 | 473 |
| HPV31 | L1 | 9 | 473 |
| HPV31 | L1 | 10 | 473 |
| HPV31 | L1 | 11 | 473 |
| HPV31 | L1 | 9 | 348 |
| HPV31 | L1 | 10 | 348 |
| HPV31 | L1 | 8 | 398 |
| HPV31 | L1 | 8 | 426 |
| HPV31 | L1 | 11 | 426 |
| HPV31 | L1 | 11 | 208 |
| HPV31 | L1 | 8 | 491 |
| HPV31 | L1 | 9 | 491 |
| HPV31 | L1 | 10 | 491 |
| HPV31 | L1 | 11 | 491 |
| HPV31 | L1 | 8 | 285 |
| HPV31 | L1 | 9 | 285 |
| HPV31 | L1 | 11 | 346 |
| HPV31 | L1 | 8 | 103 |
| HPV31 | L1 | 9 | 304 |
| HPV31 | L1 | 8 | 185 |
| HPV31 | L1 | 8 | 128 |
| HPV31 | L1 | 9 | 128 |
| HPV31 | L1 | 10 | 128 |
| HPV31 | L1 | 9 | 210 |
| HPV31 | L1 | 9 | 198 |
| HPV31 | L1 | 11 | 198 |
| HPV31 | L1 | 8 | 224 |
| HPV31 | L1 | 9 | 224 |
| HPV31 | L1 | 9 | 459 |
| HPV31 | L1 | 10 | 459 |
| HPV31 | L1 | 11 | 459 |
| HPV31 | L1 | 10 | 372 |
| HPV31 | L1 | 11 | 275 |
| HPV31 | L1 | 9 | 200 |
| HPV31 | L1 | 8 | 129 |
| HPV31 | L1 | 9 | 129 |
| HPV31 | L1 | 9 | 203 |
| HPV31 | L1 | 11 | 203 |
| HPV31 | L1 | 8 | 245 |
| HPV31 | L1 | 9 | 245 |
| HPV31 | L1 | 11 | 88 |
| HPV31 | L1 | 9 | 353 |
| HPV31 | L1 | 10 | 353 |
| HPV31 | L1 | 10 | 417 |
| HPV31 | L1 | 8 | 146 |
| HPV31 | L1 | 9 | 439 |
| HPV31 | L1 | 11 | 416 |
| HPV31 | L1 | 8 | 370 |
| HPV31 | L1 | 8 | 270 |
| HPV31 | L1 | 10 | 270 |
| HPV31 | L1 | 8 | 95 |
| HPV31 | L1 | 8 | 449 |
| HPV31 | L1 | 10 | 449 |
| HPV31 | L1 | 9 | 127 |
| HPV31 | L1 | 10 | 127 |
| HPV31 | L1 | 11 | 127 |
| HPV31 | L1 | 11 | 371 |
| HPV31 | L1 | 10 | 248 |
| HPV31 | L1 | 8 | 206 |
| HPV31 | L1 | 8 | 84 |
| HPV31 | L1 | 9 | 84 |
| HPV31 | L1 | 8 | 469 |
| HPV31 | L1 | 9 | 469 |
| HPV31 | L1 | 10 | 469 |
| HPV31 | L1 | 8 | 456 |
| HPV31 | L1 | 8 | 211 |
| HPV31 | L1 | 8 | 257 |
| HPV31 | L1 | 11 | 421 |
| HPV31 | L1 | 9 | 331 |
| HPV31 | L1 | 9 | 161 |
| HPV31 | L1 | 9 | 184 |
| HPV31 | L1 | 8 | 199 |
| HPV31 | L1 | 10 | 199 |
| HPV31 | L1 | 9 | 244 |
| HPV31 | L1 | 10 | 244 |
| HPV31 | L1 | 9 | 205 |
| HPV31 | L1 | 8 | 85 |
| HPV31 | L1 | 8 | 138 |
| HPV31 | L1 | 9 | 323 |
| HPV31 | L1 | 10 | 117 |
| HPV31 | L1 | 11 | 117 |
| HPV31 | L1 | 8 | 68 |
| HPV31 | L1 | 10 | 68 |
| HPV31 | L1 | 10 | 38 |
| HPV31 | L1 | 9 | 280 |
| HPV31 | L1 | 8 | 413 |
| HPV31 | L1 | 9 | 413 |
| HPV31 | L1 | 8 | 298 |
| HPV31 | L1 | 11 | 298 |
| HPV31 | L1 | 8 | 173 |
| HPV31 | L1 | 11 | 282 |
| HPV31 | L1 | 9 | 367 |
| HPV31 | L1 | 11 | 367 |
| HPV31 | L1 | 8 | 349 |
| HPV31 | L1 | 9 | 349 |
| HPV31 | L1 | 9 | 229 |
| HPV31 | L1 | 8 | 225 |
| HPV31 | L1 | 11 | 225 |
| HPV31 | L1 | 8 | 324 |
| HPV31 | L1 | 10 | 307 |
| HPV31 | L1 | 11 | 307 |
| HPV31 | L1 | 11 | 376 |
| HPV31 | L1 | 11 | 388 |
| HPV31 | L1 | 9 | 118 |
| HPV31 | L1 | 10 | 118 |
| HPV31 | L1 | 10 | 427 |
| HPV31 | L1 | 10 | 382 |
| HPV31 | L1 | 11 | 61 |
| HPV31 | L1 | 10 | 482 |
| HPV31 | L1 | 11 | 443 |
| HPV31 | L1 | 10 | 126 |
| HPV31 | L1 | 11 | 126 |

TABLE XVI-continued

HLA-A3 Motif Peptides

| 1 | 2 | 3 | 4 |
|---|---|---|---|
| HPV31 | L1 | 9 | 83 |
| HPV31 | L1 | 10 | 83 |
| HPV31 | L1 | 9 | 480 |
| HPV31 | L1 | 8 | 468 |
| HPV31 | L1 | 9 | 468 |
| HPV31 | L1 | 10 | 468 |
| HPV31 | L1 | 11 | 468 |
| HPV31 | L1 | 9 | 455 |
| HPV31 | L1 | 10 | 279 |
| HPV31 | L1 | 9 | 172 |
| HPV31 | L1 | 11 | 381 |
| HPV31 | L1 | 8 | 357 |
| HPV31 | L1 | 10 | 357 |
| HPV31 | L1 | 11 | 357 |
| HPV31 | L1 | 8 | 431 |
| HPV31 | L1 | 8 | 65 |
| HPV31 | L1 | 10 | 65 |
| HPV31 | L1 | 11 | 65 |
| HPV31 | L1 | 8 | 20 |
| HPV31 | L1 | 11 | 20 |
| HPV31 | L1 | 8 | 379 |
| HPV31 | L1 | 9 | 223 |
| HPV31 | L1 | 10 | 223 |
| HPV31 | L1 | 8 | 460 |
| HPV31 | L1 | 9 | 460 |
| HPV31 | L1 | 10 | 460 |
| HPV31 | L1 | 11 | 247 |
| HPV31 | L1 | 10 | 330 |
| HPV31 | L1 | 10 | 160 |
| HPV31 | L1 | 9 | 465 |
| HPV31 | L1 | 11 | 465 |
| HPV31 | L1 | 8 | 114 |
| HPV31 | L1 | 11 | 159 |
| HPV31 | L1 | 8 | 470 |
| HPV31 | L1 | 9 | 470 |
| HPV31 | L1 | 11 | 470 |
| HPV31 | L1 | 8 | 42 |
| HPV31 | L1 | 9 | 42 |
| HPV31 | L1 | 8 | 384 |
| HPV31 | L1 | 10 | 384 |
| HPV31 | L1 | 8 | 43 |
| HPV31 | L1 | 10 | 209 |
| HPV31 | L1 | 9 | 256 |
| HPV31 | L1 | 9 | 1 |
| HPV31 | L1 | 8 | 343 |
| HPV31 | L1 | 10 | 389 |
| HPV31 | L1 | 11 | 238 |
| HPV31 | L1 | 8 | 201 |
| HPV31 | L1 | 11 | 201 |
| HPV31 | L1 | 9 | 300 |
| HPV31 | L1 | 11 | 300 |
| HPV31 | L1 | 8 | 360 |
| HPV31 | L1 | 10 | 322 |
| HPV31 | L1 | 9 | 32 |
| HPV31 | L1 | 10 | 32 |
| HPV31 | L1 | 8 | 451 |
| HPV31 | L1 | 9 | 342 |
| HPV31 | L1 | 11 | 351 |
| HPV31 | L1 | 9 | 227 |
| HPV31 | L1 | 11 | 227 |
| HPV31 | L1 | 9 | 397 |
| HPV31 | L1 | 8 | 496 |
| HPV31 | L1 | 9 | 496 |
| HPV31 | L1 | 8 | 79 |
| HPV31 | L1 | 8 | 233 |
| HPV31 | L1 | 11 | 233 |
| HPV31 | L1 | 10 | 183 |
| HPV31 | L1 | 8 | 165 |
| HPV31 | L1 | 10 | 222 |
| HPV31 | L1 | 11 | 222 |
| HPV31 | L1 | 10 | 464 |
| HPV31 | L1 | 9 | 11 |
| HPV31 | L1 | 9 | 489 |
| HPV31 | L1 | 10 | 489 |
| HPV31 | L1 | 11 | 489 |
| HPV31 | L1 | 9 | 411 |
| HPV31 | L1 | 10 | 411 |
| HPV31 | L1 | 11 | 411 |
| HPV31 | L1 | 10 | 296 |
| HPV31 | L1 | 11 | 17 |
| HPV31 | L1 | 9 | 472 |
| HPV31 | L1 | 10 | 472 |
| HPV31 | L1 | 11 | 472 |
| HPV31 | L1 | 9 | 425 |
| HPV31 | L1 | 10 | 197 |
| HPV31 | L1 | 8 | 374 |
| HPV31 | L1 | 8 | 462 |
| HPV31 | L1 | 11 | 306 |
| HPV31 | L1 | 9 | 378 |
| HPV31 | L1 | 8 | 156 |
| HPV31 | L1 | 11 | 329 |
| HPV31 | L1 | 8 | 255 |
| HPV31 | L1 | 10 | 255 |
| HPV31 | L1 | 10 | 154 |
| HPV31 | L1 | 8 | 476 |
| HPV31 | L1 | 10 | 476 |
| HPV31 | L1 | 11 | 476 |
| HPV31 | L1 | 9 | 41 |
| HPV31 | L1 | 10 | 41 |
| HPV31 | L1 | 8 | 77 |
| HPV31 | L1 | 10 | 77 |
| HPV31 | L1 | 9 | 339 |
| HPV31 | L1 | 10 | 339 |
| HPV31 | L1 | 8 | 30 |
| HPV31 | L1 | 11 | 30 |
| HPV31 | L1 | 9 | 75 |
| HPV31 | L1 | 10 | 75 |
| HPV31 | L1 | 9 | 385 |
| HPV31 | L1 | 11 | 457 |
| HPV31 | L1 | 11 | 487 |
| HPV31 | L1 | 9 | 39 |
| HPV31 | L1 | 11 | 39 |
| HPV31 | L1 | 8 | 490 |
| HPV31 | L1 | 9 | 490 |
| HPV31 | L1 | 10 | 490 |
| HPV31 | L1 | 11 | 490 |
| HPV31 | L1 | 8 | 303 |
| HPV31 | L1 | 10 | 303 |
| HPV31 | L1 | 11 | 55 |
| HPV31 | L1 | 10 | 352 |
| HPV31 | L1 | 11 | 352 |
| HPV31 | L1 | 9 | 90 |
| HPV31 | L1 | 8 | 119 |
| HPV31 | L1 | 9 | 119 |
| HPV31 | L1 | 8 | 67 |
| HPV31 | L1 | 9 | 67 |
| HPV31 | L1 | 11 | 67 |
| HPV31 | L1 | 8 | 412 |
| HPV31 | L1 | 9 | 412 |
| HPV31 | L1 | 10 | 412 |
| HPV31 | L1 | 9 | 297 |
| HPV31 | L1 | 8 | 281 |
| HPV31 | L1 | 8 | 228 |
| HPV31 | L1 | 10 | 228 |
| HPV31 | L1 | 9 | 51 |
| HPV31 | L1 | 10 | 51 |
| HPV31 | L1 | 8 | 414 |
| HPV31 | L1 | 8 | 2 |
| HPV31 | L1 | 11 | 2 |
| HPV31 | L1 | 10 | 299 |
| HPV31 | L1 | 9 | 358 |
| HPV31 | L1 | 10 | 358 |
| HPV31 | L1 | 10 | 283 |
| HPV31 | L1 | 11 | 283 |
| HPV31 | L1 | 8 | 23 |
| HPV31 | L1 | 8 | 340 |
| HPV31 | L1 | 9 | 340 |
| HPV31 | L1 | 11 | 340 |
| HPV31 | L1 | 8 | 492 |
| HPV31 | L1 | 9 | 492 |

TABLE XVI-continued

HLA-A3 Motif Peptides

| 1 | 2 | 3 | 4 |
|---|---|---|---|
| HPV31 | L1 | 10 | 492 |
| HPV31 | L1 | 9 | 271 |
| HPV31 | L1 | 11 | 432 |
| HPV31 | L1 | 9 | 284 |
| HPV31 | L1 | 10 | 284 |
| HPV31 | L1 | 9 | 428 |
| HPV31 | L1 | 11 | 428 |
| HPV31 | L1 | 11 | 24 |
| HPV31 | L1 | 11 | 142 |
| HPV31 | L1 | 8 | 355 |
| HPV31 | L1 | 10 | 355 |
| HPV31 | L1 | 8 | 204 |
| HPV31 | L1 | 10 | 204 |
| HPV31 | L1 | 8 | 286 |
| HPV31 | L1 | 8 | 246 |
| HPV31 | L1 | 9 | 383 |
| HPV31 | L1 | 11 | 383 |
| HPV31 | L1 | 9 | 302 |
| HPV31 | L1 | 11 | 302 |
| HPV31 | L1 | 10 | 89 |
| HPV31 | L1 | 9 | 423 |
| HPV31 | L1 | 11 | 423 |
| HPV31 | L1 | 8 | 354 |
| HPV31 | L1 | 9 | 354 |
| HPV31 | L1 | 11 | 354 |
| HPV31 | L1 | 8 | 494 |
| HPV31 | L1 | 10 | 494 |
| HPV31 | L1 | 11 | 494 |
| HPV31 | L1 | 11 | 337 |
| HPV31 | L1 | 8 | 493 |
| HPV31 | L1 | 9 | 493 |
| HPV31 | L1 | 11 | 493 |
| HPV31 | L1 | 11 | 267 |
| HPV31 | L1 | 11 | 44 |
| HPV31 | L1 | 11 | 10 |
| HPV31 | L1 | 10 | 239 |
| HPV31 | L1 | 11 | 239 |
| HPV31 | L1 | 10 | 202 |
| HPV31 | L1 | 11 | 73 |
| HPV31 | L1 | 8 | 446 |
| HPV31 | L1 | 10 | 446 |
| HPV31 | L1 | 11 | 446 |
| HPV31 | L1 | 10 | 268 |
| HPV31 | L1 | 10 | 45 |
| HPV31 | L1 | 11 | 116 |
| HPV31 | L1 | 9 | 66 |
| HPV31 | L1 | 10 | 66 |
| HPV31 | L1 | 10 | 18 |
| HPV31 | L1 | 9 | 22 |
| HPV31 | L1 | 8 | 28 |
| HPV31 | L1 | 9 | 28 |
| HPV31 | L1 | 10 | 28 |
| HPV31 | L1 | 8 | 301 |
| HPV31 | L1 | 10 | 301 |
| HPV31 | L1 | 10 | 422 |
| HPV31 | L1 | 8 | 332 |
| HPV31 | L1 | 10 | 62 |
| HPV31 | L1 | 11 | 62 |
| HPV31 | L1 | 10 | 21 |
| HPV31 | L1 | 10 | 101 |
| HPV31 | L1 | 11 | 170 |
| HPV31 | L1 | 8 | 313 |
| HPV31 | L1 | 10 | 136 |
| HPV31 | L1 | 8 | 243 |
| HPV31 | L1 | 10 | 243 |
| HPV31 | L1 | 11 | 243 |
| HPV31 | L1 | 8 | 391 |
| HPV31 | L1 | 9 | 277 |
| HPV31 | L1 | 9 | 235 |
| HPV31 | L1 | 9 | 12 |
| HPV31 | L1 | 8 | 364 |
| HPV31 | L1 | 8 | 250 |
| HPV31 | L1 | 10 | 250 |
| HPV31 | L1 | 11 | 250 |
| HPV31 | L1 | 10 | 50 |
| HPV31 | L1 | 11 | 50 |
| HPV31 | L1 | 9 | 445 |
| HPV31 | L1 | 11 | 445 |
| HPV31 | L1 | 8 | 27 |
| HPV31 | L1 | 9 | 27 |
| HPV31 | L1 | 10 | 27 |
| HPV31 | L1 | 11 | 27 |
| HPV31 | L2 | 11 | 357 |
| HPV31 | L2 | 11 | 25 |
| HPV31 | L2 | 11 | 143 |
| HPV31 | L2 | 10 | 281 |
| HPV31 | L2 | 11 | 281 |
| HPV31 | L2 | 10 | 286 |
| HPV31 | L2 | 11 | 286 |
| HPV31 | L2 | 11 | 13 |
| HPV31 | L2 | 10 | 367 |
| HPV31 | L2 | 8 | 311 |
| HPV31 | L2 | 9 | 311 |
| HPV31 | L2 | 10 | 311 |
| HPV31 | L2 | 11 | 311 |
| HPV31 | L2 | 9 | 15 |
| HPV31 | L2 | 10 | 15 |
| HPV31 | L2 | 11 | 15 |
| HPV31 | L2 | 9 | 135 |
| HPV31 | L2 | 10 | 376 |
| HPV31 | L2 | 11 | 376 |
| HPV31 | L2 | 9 | 275 |
| HPV31 | L2 | 10 | 275 |
| HPV31 | L2 | 8 | 360 |
| HPV31 | L2 | 10 | 360 |
| HPV31 | L2 | 8 | 438 |
| HPV31 | L2 | 9 | 438 |
| HPV31 | L2 | 8 | 435 |
| HPV31 | L2 | 11 | 435 |
| HPV31 | L2 | 8 | 350 |
| HPV31 | L2 | 11 | 133 |
| HPV31 | L2 | 9 | 278 |
| HPV31 | L2 | 8 | 322 |
| HPV31 | L2 | 8 | 354 |
| HPV31 | L2 | 10 | 358 |
| HPV31 | L2 | 10 | 116 |
| HPV31 | L2 | 8 | 31 |
| HPV31 | L2 | 8 | 146 |
| HPV31 | L2 | 9 | 334 |
| HPV31 | L2 | 9 | 111 |
| HPV31 | L2 | 11 | 111 |
| HPV31 | L2 | 10 | 331 |
| HPV31 | L2 | 10 | 259 |
| HPV31 | L2 | 10 | 253 |
| HPV31 | L2 | 11 | 253 |
| HPV31 | L2 | 8 | 458 |
| HPV31 | L2 | 9 | 458 |
| HPV31 | L2 | 8 | 276 |
| HPV31 | L2 | 9 | 276 |
| HPV31 | L2 | 11 | 276 |
| HPV31 | L2 | 11 | 237 |
| HPV31 | L2 | 10 | 404 |
| HPV31 | L2 | 11 | 404 |
| HPV31 | L2 | 9 | 263 |
| HPV31 | L2 | 8 | 459 |
| HPV31 | L2 | 9 | 361 |
| HPV31 | L2 | 8 | 433 |
| HPV31 | L2 | 10 | 433 |
| HPV31 | L2 | 8 | 118 |
| HPV31 | L2 | 8 | 314 |
| HPV31 | L2 | 9 | 310 |
| HPV31 | L2 | 10 | 310 |
| HPV31 | L2 | 11 | 310 |
| HPV31 | L2 | 9 | 437 |
| HPV31 | L2 | 10 | 437 |
| HPV31 | L2 | 8 | 131 |
| HPV31 | L2 | 10 | 436 |
| HPV31 | L2 | 11 | 436 |
| HPV31 | L2 | 11 | 59 |
| HPV31 | L2 | 9 | 113 |

TABLE XVI-continued

HLA-A3 Motif Peptides

| 1 | 2 | 3 | 4 |
|---|---|---|---|
| HPV31 | L2 | 11 | 351 |
| HPV31 | L2 | 11 | 221 |
| HPV31 | L2 | 9 | 61 |
| HPV31 | L2 | 10 | 63 |
| HPV31 | L2 | 10 | 26 |
| HPV31 | L2 | 8 | 65 |
| HPV31 | L2 | 11 | 213 |
| HPV31 | L2 | 9 | 413 |
| HPV31 | L2 | 10 | 38 |
| HPV31 | L2 | 11 | 38 |
| HPV31 | L2 | 8 | 41 |
| HPV31 | L2 | 11 | 280 |
| HPV31 | L2 | 10 | 134 |
| HPV31 | L2 | 8 | 233 |
| HPV31 | L2 | 10 | 233 |
| HPV31 | L2 | 11 | 403 |
| HPV31 | L2 | 8 | 432 |
| HPV31 | L2 | 9 | 432 |
| HPV31 | L2 | 11 | 432 |
| HPV31 | L2 | 8 | 313 |
| HPV31 | L2 | 9 | 313 |
| HPV31 | L2 | 10 | 60 |
| HPV31 | L2 | 8 | 279 |
| HPV31 | L2 | 10 | 144 |
| HPV31 | L2 | 10 | 45 |
| HPV31 | L2 | 11 | 45 |
| HPV31 | L2 | 11 | 205 |
| HPV31 | L2 | 8 | 245 |
| HPV31 | L2 | 8 | 114 |
| HPV31 | L2 | 8 | 35 |
| HPV31 | L2 | 10 | 231 |
| HPV31 | L2 | 11 | 423 |
| HPV31 | L2 | 8 | 277 |
| HPV31 | L2 | 10 | 277 |
| HPV31 | L2 | 9 | 145 |
| HPV31 | L2 | 8 | 299 |
| HPV31 | L2 | 10 | 299 |
| HPV31 | L2 | 8 | 244 |
| HPV31 | L2 | 9 | 244 |
| HPV31 | L2 | 11 | 176 |
| HPV31 | L2 | 10 | 177 |
| HPV31 | L2 | 10 | 238 |
| HPV31 | L2 | 9 | 178 |
| HPV31 | L2 | 11 | 178 |
| HPV31 | L2 | 10 | 395 |
| HPV31 | L2 | 11 | 75 |
| HPV31 | L2 | 9 | 287 |
| HPV31 | L2 | 10 | 287 |
| HPV31 | L2 | 8 | 447 |
| HPV31 | L2 | 11 | 447 |
| HPV31 | L2 | 8 | 256 |
| HPV31 | L2 | 8 | 349 |
| HPV31 | L2 | 9 | 349 |
| HPV31 | L2 | 8 | 269 |
| HPV31 | L2 | 10 | 390 |
| HPV31 | L2 | 11 | 292 |
| HPV31 | L2 | 11 | 285 |
| HPV31 | L2 | 9 | 217 |
| HPV31 | L2 | 10 | 217 |
| HPV31 | L2 | 11 | 366 |
| HPV31 | L2 | 8 | 250 |
| HPV31 | L2 | 8 | 274 |
| HPV31 | L2 | 10 | 274 |
| HPV31 | L2 | 11 | 274 |
| HPV31 | L2 | 10 | 272 |
| HPV31 | L2 | 8 | 407 |
| HPV31 | L2 | 8 | 212 |
| HPV31 | L2 | 10 | 410 |
| HPV31 | L2 | 9 | 210 |
| HPV31 | L2 | 10 | 210 |
| HPV31 | L2 | 11 | 122 |
| HPV31 | L2 | 11 | 394 |
| HPV31 | L2 | 10 | 29 |
| HPV31 | L2 | 10 | 373 |
| HPV31 | L2 | 10 | 161 |
| HPV31 | L2 | 8 | 443 |
| HPV31 | L2 | 9 | 443 |
| HPV31 | L2 | 10 | 443 |
| HPV31 | L2 | 11 | 443 |
| HPV31 | L2 | 8 | 235 |
| HPV31 | L2 | 9 | 167 |
| HPV31 | L2 | 10 | 415 |
| HPV31 | L2 | 9 | 425 |
| HPV31 | L2 | 9 | 127 |
| HPV31 | L2 | 11 | 44 |
| HPV31 | L2 | 9 | 243 |
| HPV31 | L2 | 10 | 243 |
| HPV31 | L2 | 8 | 17 |
| HPV31 | L2 | 9 | 17 |
| HPV31 | L2 | 8 | 378 |
| HPV31 | L2 | 9 | 378 |
| HPV31 | L2 | 9 | 303 |
| HPV31 | L2 | 8 | 417 |
| HPV31 | L2 | 9 | 229 |
| HPV31 | L2 | 11 | 429 |
| HPV31 | L2 | 8 | 12 |
| HPV31 | L2 | 8 | 219 |
| HPV31 | L2 | 9 | 298 |
| HPV31 | L2 | 11 | 298 |
| HPV31 | L2 | 8 | 308 |
| HPV31 | L2 | 9 | 308 |
| HPV31 | L2 | 11 | 308 |
| HPV31 | L2 | 8 | 2 |
| HPV31 | L2 | 10 | 2 |
| HPV31 | L2 | 11 | 2 |
| HPV31 | L2 | 8 | 5 |
| HPV31 | L2 | 9 | 5 |
| HPV31 | L2 | 11 | 5 |
| HPV31 | L2 | 10 | 69 |
| HPV31 | L2 | 11 | 9 |
| HPV31 | L2 | 10 | 306 |
| HPV31 | L2 | 11 | 306 |
| HPV31 | L2 | 9 | 239 |
| HPV31 | L2 | 10 | 14 |
| HPV31 | L2 | 11 | 14 |
| HPV31 | L2 | 9 | 30 |
| HPV31 | L2 | 8 | 309 |
| HPV31 | L2 | 10 | 309 |
| HPV31 | L2 | 11 | 309 |
| HPV31 | L2 | 9 | 130 |
| HPV31 | L2 | 8 | 112 |
| HPV31 | L2 | 10 | 112 |
| HPV31 | L2 | 9 | 405 |
| HPV31 | L2 | 10 | 405 |
| HPV31 | L2 | 8 | 62 |
| HPV31 | L2 | 11 | 62 |
| HPV31 | L2 | 9 | 64 |
| HPV31 | L2 | 9 | 332 |
| HPV31 | L2 | 11 | 332 |
| HPV31 | L2 | 9 | 431 |
| HPV31 | L2 | 10 | 431 |
| HPV31 | L2 | 9 | 260 |
| HPV31 | L2 | 8 | 181 |
| HPV31 | L2 | 9 | 180 |
| HPV31 | L2 | 8 | 179 |
| HPV31 | L2 | 10 | 179 |
| HPV31 | L2 | 9 | 207 |
| HPV31 | L2 | 10 | 207 |
| HPV31 | L2 | 9 | 374 |
| HPV31 | L2 | 9 | 396 |
| HPV31 | L2 | 8 | 151 |
| HPV31 | L2 | 8 | 6 |
| HPV31 | L2 | 10 | 6 |
| HPV31 | L2 | 8 | 346 |
| HPV31 | L2 | 11 | 346 |
| HPV31 | L2 | 8 | 208 |
| HPV31 | L2 | 9 | 208 |
| HPV31 | L2 | 11 | 208 |
| HPV31 | L2 | 10 | 76 |
| HPV31 | L2 | 8 | 379 |

TABLE XVI-continued

HLA-A3 Motif Peptides

| 1 | 2 | 3 | 4 |
|---|---|---|---|
| HPV31 | L2 | 11 | 80 |
| HPV31 | L2 | 9 | 162 |
| HPV31 | L2 | 10 | 149 |
| HPV31 | L2 | 8 | 375 |
| HPV31 | L2 | 11 | 375 |
| HPV31 | L2 | 9 | 27 |
| HPV31 | L2 | 9 | 359 |
| HPV31 | L2 | 11 | 359 |
| HPV31 | L2 | 8 | 397 |
| HPV31 | L2 | 9 | 70 |
| HPV31 | L2 | 8 | 40 |
| HPV31 | L2 | 9 | 40 |
| HPV31 | L2 | 8 | 312 |
| HPV31 | L2 | 9 | 312 |
| HPV31 | L2 | 10 | 312 |
| HPV31 | L2 | 10 | 347 |
| HPV31 | L2 | 11 | 347 |
| HPV31 | L2 | 8 | 304 |
| HPV31 | L2 | 10 | 129 |
| HPV31 | L2 | 11 | 266 |
| HPV31 | L2 | 8 | 288 |
| HPV31 | L2 | 9 | 288 |
| HPV31 | L2 | 11 | 288 |
| HPV31 | L2 | 10 | 206 |
| HPV31 | L2 | 11 | 206 |
| HPV31 | L2 | 9 | 345 |
| HPV31 | L2 | 11 | 148 |
| HPV31 | L2 | 8 | 136 |
| HPV31 | L2 | 9 | 39 |
| HPV31 | L2 | 10 | 39 |
| HPV31 | L2 | 8 | 426 |
| HPV31 | L2 | 8 | 128 |
| HPV31 | L2 | 11 | 128 |
| HPV31 | L2 | 10 | 344 |
| HPV31 | L2 | 11 | 343 |
| HPV31 | L2 | 9 | 391 |
| HPV31 | L2 | 8 | 362 |
| HPV31 | L2 | 9 | 254 |
| HPV31 | L2 | 10 | 254 |
| HPV31 | L2 | 8 | 392 |
| HPV31 | L2 | 10 | 293 |
| HPV31 | L2 | 10 | 81 |
| HPV31 | L2 | 9 | 434 |
| HPV31 | L2 | 11 | 115 |
| HPV31 | L2 | 9 | 117 |
| HPV31 | L2 | 9 | 232 |
| HPV31 | L2 | 11 | 232 |
| HPV31 | L2 | 11 | 32 |
| HPV31 | L2 | 8 | 163 |
| HPV31 | L2 | 9 | 82 |
| HPV31 | L2 | 10 | 430 |
| HPV31 | L2 | 11 | 430 |
| HPV31 | L2 | 9 | 150 |
| HPV31 | L2 | 11 | 455 |
| HPV31 | L2 | 9 | 321 |
| HPV31 | L2 | 9 | 353 |
| HPV31 | L2 | 9 | 457 |
| HPV31 | L2 | 10 | 457 |
| HPV31 | L2 | 10 | 262 |
| HPV31 | L2 | 8 | 48 |
| HPV31 | L2 | 10 | 440 |
| HPV31 | L2 | 11 | 440 |
| HPV31 | L2 | 8 | 446 |
| HPV31 | L2 | 9 | 446 |
| HPV31 | L2 | 9 | 223 |
| HPV31 | L2 | 11 | 296 |
| HPV33 | E1 | 11 | 382 |
| HPV33 | E1 | 8 | 90 |
| HPV33 | E1 | 8 | 96 |
| HPV33 | E1 | 9 | 96 |
| HPV33 | E1 | 10 | 96 |
| HPV33 | E1 | 10 | 383 |
| HPV33 | E1 | 11 | 383 |
| HPV33 | E1 | 11 | 104 |
| HPV33 | E1 | 11 | 40 |
| HPV33 | E1 | 9 | 2 |
| HPV33 | E1 | 8 | 376 |
| HPV33 | E1 | 9 | 376 |
| HPV33 | E1 | 10 | 376 |
| HPV33 | E1 | 8 | 61 |
| HPV33 | E1 | 10 | 61 |
| HPV33 | E1 | 11 | 452 |
| HPV33 | E1 | 8 | 448 |
| HPV33 | E1 | 9 | 448 |
| HPV33 | E1 | 11 | 448 |
| HPV33 | E1 | 9 | 384 |
| HPV33 | E1 | 10 | 384 |
| HPV33 | E1 | 9 | 635 |
| HPV33 | E1 | 9 | 10 |
| HPV33 | E1 | 9 | 563 |
| HPV33 | E1 | 11 | 563 |
| HPV33 | E1 | 8 | 596 |
| HPV33 | E1 | 10 | 596 |
| HPV33 | E1 | 11 | 596 |
| HPV33 | E1 | 8 | 84 |
| HPV33 | E1 | 8 | 311 |
| HPV33 | E1 | 8 | 81 |
| HPV33 | E1 | 9 | 81 |
| HPV33 | E1 | 10 | 81 |
| HPV33 | E1 | 11 | 81 |
| HPV33 | E1 | 8 | 83 |
| HPV33 | E1 | 9 | 83 |
| HPV33 | E1 | 9 | 310 |
| HPV33 | E1 | 8 | 398 |
| HPV33 | E1 | 9 | 398 |
| HPV33 | E1 | 10 | 398 |
| HPV33 | E1 | 11 | 398 |
| HPV33 | E1 | 8 | 469 |
| HPV33 | E1 | 10 | 469 |
| HPV33 | E1 | 11 | 469 |
| HPV33 | E1 | 8 | 465 |
| HPV33 | E1 | 8 | 297 |
| HPV33 | E1 | 10 | 297 |
| HPV33 | E1 | 8 | 633 |
| HPV33 | E1 | 11 | 633 |
| HPV33 | E1 | 9 | 276 |
| HPV33 | E1 | 10 | 276 |
| HPV33 | E1 | 9 | 226 |
| HPV33 | E1 | 9 | 14 |
| HPV33 | E1 | 9 | 490 |
| HPV33 | E1 | 11 | 490 |
| HPV33 | E1 | 8 | 494 |
| HPV33 | E1 | 8 | 397 |
| HPV33 | E1 | 9 | 397 |
| HPV33 | E1 | 10 | 397 |
| HPV33 | E1 | 11 | 397 |
| HPV33 | E1 | 8 | 77 |
| HPV33 | E1 | 10 | 77 |
| HPV33 | E1 | 11 | 77 |
| HPV33 | E1 | 8 | 364 |
| HPV33 | E1 | 9 | 364 |
| HPV33 | E1 | 10 | 364 |
| HPV33 | E1 | 10 | 41 |
| HPV33 | E1 | 10 | 52 |
| HPV33 | E1 | 10 | 515 |
| HPV33 | E1 | 10 | 534 |
| HPV33 | E1 | 11 | 534 |
| HPV33 | E1 | 10 | 367 |
| HPV33 | E1 | 8 | 614 |
| HPV33 | E1 | 11 | 614 |
| HPV33 | E1 | 9 | 78 |
| HPV33 | E1 | 10 | 78 |
| HPV33 | E1 | 11 | 78 |
| HPV33 | E1 | 9 | 349 |
| HPV33 | E1 | 10 | 349 |
| HPV33 | E1 | 8 | 365 |
| HPV33 | E1 | 9 | 365 |
| HPV33 | E1 | 9 | 42 |
| HPV33 | E1 | 9 | 53 |
| HPV33 | E1 | 8 | 377 |

TABLE XVI-continued

HLA-A3 Motif Peptides

| 1 | 2 | 3 | 4 |
|---|---|---|---|
| HPV33 | E1 | 9 | 377 |
| HPV33 | E1 | 11 | 377 |
| HPV33 | E1 | 8 | 566 |
| HPV33 | E1 | 10 | 566 |
| HPV33 | E1 | 9 | 62 |
| HPV33 | E1 | 11 | 541 |
| HPV33 | E1 | 9 | 516 |
| HPV33 | E1 | 11 | 99 |
| HPV33 | E1 | 8 | 117 |
| HPV33 | E1 | 9 | 76 |
| HPV33 | E1 | 11 | 76 |
| HPV33 | E1 | 8 | 98 |
| HPV33 | E1 | 8 | 580 |
| HPV33 | E1 | 8 | 445 |
| HPV33 | E1 | 9 | 445 |
| HPV33 | E1 | 10 | 445 |
| HPV33 | E1 | 11 | 445 |
| HPV33 | E1 | 8 | 74 |
| HPV33 | E1 | 11 | 74 |
| HPV33 | E1 | 8 | 537 |
| HPV33 | E1 | 9 | 537 |
| HPV33 | E1 | 10 | 537 |
| HPV33 | E1 | 9 | 361 |
| HPV33 | E1 | 10 | 361 |
| HPV33 | E1 | 11 | 361 |
| HPV33 | E1 | 10 | 214 |
| HPV33 | E1 | 8 | 242 |
| HPV33 | E1 | 10 | 242 |
| HPV33 | E1 | 10 | 295 |
| HPV33 | E1 | 8 | 19 |
| HPV33 | E1 | 9 | 19 |
| HPV33 | E1 | 8 | 89 |
| HPV33 | E1 | 9 | 89 |
| HPV33 | E1 | 9 | 587 |
| HPV33 | E1 | 10 | 587 |
| HPV33 | E1 | 10 | 348 |
| HPV33 | E1 | 11 | 348 |
| HPV33 | E1 | 8 | 605 |
| HPV33 | E1 | 8 | 479 |
| HPV33 | E1 | 10 | 479 |
| HPV33 | E1 | 8 | 449 |
| HPV33 | E1 | 10 | 449 |
| HPV33 | E1 | 8 | 456 |
| HPV33 | E1 | 8 | 385 |
| HPV33 | E1 | 9 | 385 |
| HPV33 | E1 | 8 | 212 |
| HPV33 | E1 | 9 | 212 |
| HPV33 | E1 | 8 | 446 |
| HPV33 | E1 | 9 | 446 |
| HPV33 | E1 | 10 | 446 |
| HPV33 | E1 | 11 | 446 |
| HPV33 | E1 | 8 | 451 |
| HPV33 | E1 | 10 | 9 |
| HPV33 | E1 | 10 | 13 |
| HPV33 | E1 | 10 | 489 |
| HPV33 | E1 | 8 | 625 |
| HPV33 | E1 | 11 | 625 |
| HPV33 | E1 | 9 | 265 |
| HPV33 | E1 | 10 | 265 |
| HPV33 | E1 | 11 | 265 |
| HPV33 | E1 | 8 | 399 |
| HPV33 | E1 | 9 | 399 |
| HPV33 | E1 | 10 | 399 |
| HPV33 | E1 | 9 | 209 |
| HPV33 | E1 | 11 | 209 |
| HPV33 | E1 | 11 | 235 |
| HPV33 | E1 | 8 | 11 |
| HPV33 | E1 | 9 | 480 |
| HPV33 | E1 | 8 | 564 |
| HPV33 | E1 | 10 | 564 |
| HPV33 | E1 | 9 | 327 |
| HPV33 | E1 | 10 | 500 |
| HPV33 | E1 | 11 | 500 |
| HPV33 | E1 | 8 | 624 |
| HPV33 | E1 | 9 | 624 |
| HPV33 | E1 | 9 | 256 |
| HPV33 | E1 | 8 | 341 |
| HPV33 | E1 | 9 | 573 |
| HPV33 | E1 | 10 | 573 |
| HPV33 | E1 | 11 | 192 |
| HPV33 | E1 | 9 | 368 |
| HPV33 | E1 | 9 | 468 |
| HPV33 | E1 | 11 | 468 |
| HPV33 | E1 | 11 | 51 |
| HPV33 | E1 | 11 | 514 |
| HPV33 | E1 | 8 | 525 |
| HPV33 | E1 | 9 | 125 |
| HPV33 | E1 | 9 | 333 |
| HPV33 | E1 | 11 | 333 |
| HPV33 | E1 | 11 | 347 |
| HPV33 | E1 | 8 | 415 |
| HPV33 | E1 | 11 | 415 |
| HPV33 | E1 | 8 | 266 |
| HPV33 | E1 | 9 | 266 |
| HPV33 | E1 | 10 | 266 |
| HPV33 | E1 | 8 | 267 |
| HPV33 | E1 | 9 | 267 |
| HPV33 | E1 | 8 | 268 |
| HPV33 | E1 | 11 | 268 |
| HPV33 | E1 | 8 | 200 |
| HPV33 | E1 | 9 | 200 |
| HPV33 | E1 | 8 | 400 |
| HPV33 | E1 | 9 | 400 |
| HPV33 | E1 | 11 | 400 |
| HPV33 | E1 | 9 | 492 |
| HPV33 | E1 | 10 | 492 |
| HPV33 | E1 | 9 | 32 |
| HPV33 | E1 | 8 | 210 |
| HPV33 | E1 | 10 | 210 |
| HPV33 | E1 | 11 | 210 |
| HPV33 | E1 | 8 | 538 |
| HPV33 | E1 | 9 | 538 |
| HPV33 | E1 | 11 | 187 |
| HPV33 | E1 | 10 | 236 |
| HPV33 | E1 | 8 | 628 |
| HPV33 | E1 | 9 | 520 |
| HPV33 | E1 | 11 | 520 |
| HPV33 | E1 | 11 | 231 |
| HPV33 | E1 | 10 | 394 |
| HPV33 | E1 | 11 | 394 |
| HPV33 | E1 | 8 | 197 |
| HPV33 | E1 | 9 | 197 |
| HPV33 | E1 | 11 | 197 |
| HPV33 | E1 | 9 | 632 |
| HPV33 | E1 | 8 | 396 |
| HPV33 | E1 | 9 | 396 |
| HPV33 | E1 | 10 | 396 |
| HPV33 | E1 | 11 | 396 |
| HPV33 | E1 | 9 | 88 |
| HPV33 | E1 | 10 | 88 |
| HPV33 | E1 | 10 | 203 |
| HPV33 | E1 | 8 | 455 |
| HPV33 | E1 | 9 | 455 |
| HPV33 | E1 | 11 | 488 |
| HPV33 | E1 | 10 | 124 |
| HPV33 | E1 | 11 | 393 |
| HPV33 | E1 | 10 | 612 |
| HPV33 | E1 | 8 | 304 |
| HPV33 | E1 | 10 | 304 |
| HPV33 | E1 | 11 | 412 |
| HPV33 | E1 | 10 | 463 |
| HPV33 | E1 | 10 | 603 |
| HPV33 | E1 | 10 | 387 |
| HPV33 | E1 | 11 | 476 |
| HPV33 | E1 | 9 | 425 |
| HPV33 | E1 | 10 | 245 |
| HPV33 | E1 | 8 | 375 |
| HPV33 | E1 | 9 | 375 |
| HPV33 | E1 | 10 | 375 |
| HPV33 | E1 | 11 | 375 |

TABLE XVI-continued

HLA-A3 Motif Peptides

| 1 | 2 | 3 | 4 |
|---|---|---|---|
| HPV33 | E1 | 11 | 533 |
| HPV33 | E1 | 9 | 613 |
| HPV33 | E1 | 9 | 450 |
| HPV33 | E1 | 10 | 467 |
| HPV33 | E1 | 10 | 615 |
| HPV33 | E1 | 8 | 247 |
| HPV33 | E1 | 10 | 247 |
| HPV33 | E1 | 8 | 271 |
| HPV33 | E1 | 10 | 271 |
| HPV33 | E1 | 9 | 270 |
| HPV33 | E1 | 11 | 270 |
| HPV33 | E1 | 10 | 269 |
| HPV33 | E1 | 9 | 555 |
| HPV33 | E1 | 9 | 438 |
| HPV33 | E1 | 11 | 438 |
| HPV33 | E1 | 8 | 556 |
| HPV33 | E1 | 8 | 350 |
| HPV33 | E1 | 9 | 350 |
| HPV33 | E1 | 8 | 362 |
| HPV33 | E1 | 9 | 362 |
| HPV33 | E1 | 10 | 362 |
| HPV33 | E1 | 11 | 362 |
| HPV33 | E1 | 10 | 576 |
| HPV33 | E1 | 8 | 336 |
| HPV33 | E1 | 9 | 215 |
| HPV33 | E1 | 10 | 1 |
| HPV33 | E1 | 8 | 401 |
| HPV33 | E1 | 10 | 401 |
| HPV33 | E1 | 11 | 401 |
| HPV33 | E1 | 11 | 12 |
| HPV33 | E1 | 11 | 466 |
| HPV33 | E1 | 10 | 413 |
| HPV33 | E1 | 8 | 481 |
| HPV33 | E1 | 9 | 298 |
| HPV33 | E1 | 10 | 562 |
| HPV33 | E1 | 8 | 80 |
| HPV33 | E1 | 9 | 80 |
| HPV33 | E1 | 10 | 80 |
| HPV33 | E1 | 11 | 80 |
| HPV33 | E1 | 8 | 598 |
| HPV33 | E1 | 9 | 598 |
| HPV33 | E1 | 11 | 598 |
| HPV33 | E1 | 11 | 8 |
| HPV33 | E1 | 10 | 443 |
| HPV33 | E1 | 11 | 443 |
| HPV33 | E1 | 9 | 199 |
| HPV33 | E1 | 10 | 199 |
| HPV33 | E1 | 11 | 71 |
| HPV33 | E1 | 10 | 31 |
| HPV33 | E1 | 9 | 627 |
| HPV33 | E1 | 10 | 57 |
| HPV33 | E1 | 11 | 57 |
| HPV33 | E1 | 9 | 379 |
| HPV33 | E1 | 8 | 389 |
| HPV33 | E1 | 8 | 195 |
| HPV33 | E1 | 9 | 195 |
| HPV33 | E1 | 10 | 195 |
| HPV33 | E1 | 11 | 195 |
| HPV33 | E1 | 9 | 560 |
| HPV33 | E1 | 9 | 189 |
| HPV33 | E1 | 10 | 189 |
| HPV33 | E1 | 8 | 471 |
| HPV33 | E1 | 9 | 471 |
| HPV33 | E1 | 8 | 107 |
| HPV33 | E1 | 10 | 107 |
| HPV33 | E1 | 10 | 586 |
| HPV33 | E1 | 11 | 586 |
| HPV33 | E1 | 10 | 519 |
| HPV33 | E1 | 8 | 434 |
| HPV33 | E1 | 10 | 554 |
| HPV33 | E1 | 8 | 238 |
| HPV33 | E1 | 11 | 593 |
| HPV33 | E1 | 8 | 60 |
| HPV33 | E1 | 9 | 60 |
| HPV33 | E1 | 11 | 60 |
| HPV33 | E1 | 10 | 326 |
| HPV33 | E1 | 9 | 374 |
| HPV33 | E1 | 10 | 374 |
| HPV33 | E1 | 11 | 374 |
| HPV33 | E1 | 10 | 437 |
| HPV33 | E1 | 10 | 94 |
| HPV33 | E1 | 11 | 94 |
| HPV33 | E1 | 8 | 308 |
| HPV33 | E1 | 9 | 308 |
| HPV33 | E1 | 11 | 308 |
| HPV33 | E1 | 10 | 275 |
| HPV33 | E1 | 11 | 275 |
| HPV33 | E1 | 8 | 273 |
| HPV33 | E1 | 10 | 264 |
| HPV33 | E1 | 11 | 264 |
| HPV33 | E1 | 8 | 575 |
| HPV33 | E1 | 11 | 575 |
| HPV33 | E1 | 9 | 335 |
| HPV33 | E1 | 8 | 306 |
| HPV33 | E1 | 10 | 306 |
| HPV33 | E1 | 11 | 306 |
| HPV33 | E1 | 8 | 109 |
| HPV33 | E1 | 9 | 95 |
| HPV33 | E1 | 10 | 95 |
| HPV33 | E1 | 11 | 95 |
| HPV33 | E1 | 10 | 634 |
| HPV33 | E1 | 9 | 464 |
| HPV33 | E1 | 10 | 225 |
| HPV33 | E1 | 8 | 493 |
| HPV33 | E1 | 9 | 493 |
| HPV33 | E1 | 8 | 366 |
| HPV33 | E1 | 11 | 366 |
| HPV33 | E1 | 9 | 604 |
| HPV33 | E1 | 9 | 211 |
| HPV33 | E1 | 10 | 211 |
| HPV33 | E1 | 8 | 43 |
| HPV33 | E1 | 8 | 539 |
| HPV33 | E1 | 9 | 414 |
| HPV33 | E1 | 10 | 111 |
| HPV33 | E1 | 11 | 111 |
| HPV33 | E1 | 8 | 58 |
| HPV33 | E1 | 9 | 58 |
| HPV33 | E1 | 10 | 58 |
| HPV33 | E1 | 11 | 58 |
| HPV33 | E1 | 9 | 243 |
| HPV33 | E1 | 8 | 54 |
| HPV33 | E1 | 10 | 193 |
| HPV33 | E1 | 11 | 193 |
| HPV33 | E1 | 11 | 239 |
| HPV33 | E1 | 8 | 447 |
| HPV33 | E1 | 9 | 447 |
| HPV33 | E1 | 10 | 447 |
| HPV33 | E1 | 8 | 309 |
| HPV33 | E1 | 10 | 309 |
| HPV33 | E1 | 9 | 296 |
| HPV33 | E1 | 11 | 296 |
| HPV33 | E1 | 8 | 363 |
| HPV33 | E1 | 9 | 363 |
| HPV33 | E1 | 10 | 363 |
| HPV33 | E1 | 11 | 363 |
| HPV33 | E1 | 9 | 565 |
| HPV33 | E1 | 11 | 565 |
| HPV33 | E1 | 8 | 227 |
| HPV33 | E1 | 11 | 630 |
| HPV33 | E1 | 8 | 15 |
| HPV33 | E1 | 10 | 232 |
| HPV33 | E1 | 10 | 183 |
| HPV33 | E1 | 11 | 224 |
| HPV33 | E1 | 11 | 110 |
| HPV33 | E1 | 11 | 558 |
| HPV33 | E1 | 8 | 328 |
| HPV33 | E1 | 9 | 577 |
| HPV33 | E1 | 11 | 577 |
| HPV33 | E1 | 10 | 240 |

TABLE XVI-continued

HLA-A3 Motif Peptides

| 1 | 2 | 3 | 4 |
|---|---|---|---|
| HPV33 | E1 | 8 | 82 |
| HPV33 | E1 | 9 | 82 |
| HPV33 | E1 | 10 | 82 |
| HPV33 | E1 | 9 | 101 |
| HPV33 | E1 | 8 | 578 |
| HPV33 | E1 | 10 | 578 |
| HPV33 | E1 | 8 | 299 |
| HPV33 | E1 | 8 | 491 |
| HPV33 | E1 | 10 | 491 |
| HPV33 | E1 | 11 | 491 |
| HPV33 | E1 | 8 | 190 |
| HPV33 | E1 | 9 | 190 |
| HPV33 | E1 | 9 | 246 |
| HPV33 | E1 | 11 | 246 |
| HPV33 | E1 | 11 | 338 |
| HPV33 | E1 | 11 | 182 |
| HPV33 | E1 | 8 | 517 |
| HPV33 | E1 | 10 | 100 |
| HPV33 | E1 | 10 | 17 |
| HPV33 | E1 | 11 | 17 |
| HPV33 | E1 | 10 | 332 |
| HPV33 | E1 | 8 | 418 |
| HPV33 | E1 | 8 | 502 |
| HPV33 | E1 | 9 | 502 |
| HPV33 | E1 | 9 | 522 |
| HPV33 | E1 | 11 | 522 |
| HPV33 | E1 | 9 | 595 |
| HPV33 | E1 | 11 | 595 |
| HPV33 | E1 | 11 | 372 |
| HPV33 | E1 | 9 | 478 |
| HPV33 | E1 | 11 | 478 |
| HPV33 | E1 | 10 | 208 |
| HPV33 | E1 | 8 | 234 |
| HPV33 | E1 | 9 | 524 |
| HPV33 | E1 | 9 | 571 |
| HPV33 | E1 | 11 | 571 |
| HPV33 | E1 | 11 | 254 |
| HPV33 | E2 | 9 | 223 |
| HPV33 | E2 | 8 | 224 |
| HPV33 | E2 | 10 | 210 |
| HPV33 | E2 | 8 | 246 |
| HPV33 | E2 | 10 | 246 |
| HPV33 | E2 | 11 | 246 |
| HPV33 | E2 | 10 | 69 |
| HPV33 | E2 | 8 | 249 |
| HPV33 | E2 | 10 | 249 |
| HPV33 | E2 | 10 | 78 |
| HPV33 | E2 | 11 | 41 |
| HPV33 | E2 | 9 | 258 |
| HPV33 | E2 | 10 | 10 |
| HPV33 | E2 | 9 | 245 |
| HPV33 | E2 | 11 | 245 |
| HPV33 | E2 | 8 | 40 |
| HPV33 | E2 | 9 | 288 |
| HPV33 | E2 | 10 | 288 |
| HPV33 | E2 | 10 | 269 |
| HPV33 | E2 | 10 | 145 |
| HPV33 | E2 | 9 | 211 |
| HPV33 | E2 | 8 | 25 |
| HPV33 | E2 | 10 | 25 |
| HPV33 | E2 | 8 | 235 |
| HPV33 | E2 | 10 | 235 |
| HPV33 | E2 | 9 | 143 |
| HPV33 | E2 | 11 | 232 |
| HPV33 | E2 | 8 | 39 |
| HPV33 | E2 | 9 | 39 |
| HPV33 | E2 | 8 | 173 |
| HPV33 | E2 | 10 | 142 |
| HPV33 | E2 | 8 | 3 |
| HPV33 | E2 | 11 | 74 |
| HPV33 | E2 | 11 | 298 |
| HPV33 | E2 | 9 | 282 |
| HPV33 | E2 | 10 | 282 |
| HPV33 | E2 | 11 | 282 |
| HPV33 | E2 | 8 | 80 |
| HPV33 | E2 | 11 | 115 |
| HPV33 | E2 | 9 | 100 |
| HPV33 | E2 | 11 | 100 |
| HPV33 | E2 | 10 | 244 |
| HPV33 | E2 | 10 | 325 |
| HPV33 | E2 | 10 | 156 |
| HPV33 | E2 | 10 | 278 |
| HPV33 | E2 | 11 | 155 |
| HPV33 | E2 | 9 | 15 |
| HPV33 | E2 | 11 | 4 |
| HPV33 | E2 | 11 | 68 |
| HPV33 | E2 | 8 | 287 |
| HPV33 | E2 | 10 | 287 |
| HPV33 | E2 | 11 | 287 |
| HPV33 | E2 | 8 | 280 |
| HPV33 | E2 | 11 | 280 |
| HPV33 | E2 | 8 | 14 |
| HPV33 | E2 | 10 | 14 |
| HPV33 | E2 | 8 | 242 |
| HPV33 | E2 | 8 | 34 |
| HPV33 | E2 | 11 | 34 |
| HPV33 | E2 | 10 | 23 |
| HPV33 | E2 | 8 | 180 |
| HPV33 | E2 | 8 | 151 |
| HPV33 | E2 | 9 | 151 |
| HPV33 | E2 | 11 | 151 |
| HPV33 | E2 | 8 | 165 |
| HPV33 | E2 | 11 | 165 |
| HPV33 | E2 | 8 | 63 |
| HPV33 | E2 | 8 | 103 |
| HPV33 | E2 | 9 | 103 |
| HPV33 | E2 | 10 | 103 |
| HPV33 | E2 | 11 | 54 |
| HPV33 | E2 | 8 | 16 |
| HPV33 | E2 | 9 | 250 |
| HPV33 | E2 | 11 | 243 |
| HPV33 | E2 | 10 | 35 |
| HPV33 | E2 | 8 | 62 |
| HPV33 | E2 | 9 | 62 |
| HPV33 | E2 | 10 | 42 |
| HPV33 | E2 | 10 | 240 |
| HPV33 | E2 | 8 | 77 |
| HPV33 | E2 | 11 | 77 |
| HPV33 | E2 | 10 | 129 |
| HPV33 | E2 | 8 | 49 |
| HPV33 | E2 | 8 | 147 |
| HPV33 | E2 | 11 | 9 |
| HPV33 | E2 | 8 | 162 |
| HPV33 | E2 | 9 | 162 |
| HPV33 | E2 | 10 | 162 |
| HPV33 | E2 | 11 | 162 |
| HPV33 | E2 | 9 | 123 |
| HPV33 | E2 | 8 | 216 |
| HPV33 | E2 | 9 | 216 |
| HPV33 | E2 | 10 | 216 |
| HPV33 | E2 | 11 | 216 |
| HPV33 | E2 | 8 | 318 |
| HPV33 | E2 | 11 | 315 |
| HPV33 | E2 | 8 | 284 |
| HPV33 | E2 | 9 | 284 |
| HPV33 | E2 | 11 | 284 |
| HPV33 | E2 | 9 | 272 |
| HPV33 | E2 | 8 | 230 |
| HPV33 | E2 | 8 | 248 |
| HPV33 | E2 | 9 | 248 |
| HPV33 | E2 | 11 | 248 |
| HPV33 | E2 | 8 | 239 |
| HPV33 | E2 | 11 | 239 |
| HPV33 | E2 | 9 | 60 |
| HPV33 | E2 | 10 | 60 |
| HPV33 | E2 | 11 | 60 |
| HPV33 | E2 | 8 | 27 |
| HPV33 | E2 | 11 | 27 |
| HPV33 | E2 | 9 | 342 |
| HPV33 | E2 | 8 | 222 |

TABLE XVI-continued

HLA-A3 Motif Peptides

| 1 | 2 | 3 | 4 |
|---|---|---|---|
| HPV33 | E2 | 10 | 222 |
| HPV33 | E2 | 9 | 113 |
| HPV33 | E2 | 9 | 29 |
| HPV33 | E2 | 8 | 203 |
| HPV33 | E2 | 9 | 76 |
| HPV33 | E2 | 8 | 332 |
| HPV33 | E2 | 9 | 48 |
| HPV33 | E2 | 11 | 213 |
| HPV33 | E2 | 8 | 71 |
| HPV33 | E2 | 8 | 57 |
| HPV33 | E2 | 10 | 57 |
| HPV33 | E2 | 9 | 292 |
| HPV33 | E2 | 8 | 7 |
| HPV33 | E2 | 8 | 37 |
| HPV33 | E2 | 10 | 37 |
| HPV33 | E2 | 11 | 37 |
| HPV33 | E2 | 9 | 256 |
| HPV33 | E2 | 11 | 256 |
| HPV33 | E2 | 9 | 266 |
| HPV33 | E2 | 10 | 5 |
| HPV33 | E2 | 11 | 98 |
| HPV33 | E2 | 8 | 285 |
| HPV33 | E2 | 10 | 285 |
| HPV33 | E2 | 8 | 61 |
| HPV33 | E2 | 9 | 61 |
| HPV33 | E2 | 10 | 61 |
| HPV33 | E2 | 8 | 301 |
| HPV33 | E2 | 11 | 200 |
| HPV33 | E2 | 9 | 270 |
| HPV33 | E2 | 11 | 270 |
| HPV33 | E2 | 11 | 304 |
| HPV33 | E2 | 10 | 305 |
| HPV33 | E2 | 11 | 209 |
| HPV33 | E2 | 9 | 45 |
| HPV33 | E2 | 9 | 236 |
| HPV33 | E2 | 11 | 236 |
| HPV33 | E2 | 11 | 254 |
| HPV33 | E2 | 8 | 257 |
| HPV33 | E2 | 10 | 257 |
| HPV33 | E2 | 8 | 144 |
| HPV33 | E2 | 11 | 144 |
| HPV33 | E2 | 9 | 24 |
| HPV33 | E2 | 11 | 24 |
| HPV33 | E2 | 10 | 214 |
| HPV33 | E2 | 11 | 214 |
| HPV33 | E2 | 9 | 234 |
| HPV33 | E2 | 11 | 234 |
| HPV33 | E2 | 11 | 324 |
| HPV33 | E2 | 10 | 149 |
| HPV33 | E2 | 11 | 149 |
| HPV33 | E2 | 11 | 128 |
| HPV33 | E2 | 9 | 146 |
| HPV33 | E2 | 8 | 310 |
| HPV33 | E2 | 10 | 233 |
| HPV33 | E2 | 8 | 267 |
| HPV33 | E2 | 8 | 343 |
| HPV33 | E2 | 8 | 118 |
| HPV33 | E2 | 9 | 118 |
| HPV33 | E2 | 10 | 116 |
| HPV33 | E2 | 11 | 116 |
| HPV33 | E2 | 8 | 273 |
| HPV33 | E2 | 11 | 268 |
| HPV33 | E2 | 8 | 152 |
| HPV33 | E2 | 10 | 152 |
| HPV33 | E2 | 9 | 326 |
| HPV33 | E2 | 11 | 148 |
| HPV33 | E2 | 9 | 117 |
| HPV33 | E2 | 10 | 117 |
| HPV33 | E2 | 9 | 58 |
| HPV33 | E2 | 11 | 58 |
| HPV33 | E2 | 9 | 102 |
| HPV33 | E2 | 10 | 102 |
| HPV33 | E2 | 11 | 102 |
| HPV33 | E2 | 9 | 309 |
| HPV33 | E2 | 11 | 121 |
| HPV33 | E2 | 8 | 170 |
| HPV33 | E2 | 9 | 170 |
| HPV33 | E2 | 11 | 170 |
| HPV33 | E2 | 9 | 167 |
| HPV33 | E2 | 10 | 167 |
| HPV33 | E2 | 11 | 167 |
| HPV33 | E2 | 8 | 154 |
| HPV33 | E2 | 9 | 159 |
| HPV33 | E2 | 10 | 159 |
| HPV33 | E2 | 11 | 159 |
| HPV33 | E2 | 10 | 178 |
| HPV33 | E2 | 9 | 300 |
| HPV33 | E2 | 8 | 44 |
| HPV33 | E2 | 10 | 44 |
| HPV33 | E2 | 8 | 131 |
| HPV33 | E5 | 8 | 63 |
| HPV33 | E5 | 8 | 51 |
| HPV33 | E5 | 9 | 50 |
| HPV33 | E5 | 9 | 12 |
| HPV33 | E5 | 11 | 56 |
| HPV33 | E5 | 10 | 3 |
| HPV33 | E5 | 9 | 42 |
| HPV33 | E5 | 10 | 42 |
| HPV33 | E5 | 8 | 5 |
| HPV33 | E5 | 8 | 44 |
| HPV33 | E5 | 10 | 44 |
| HPV33 | E5 | 8 | 49 |
| HPV33 | E5 | 10 | 49 |
| HPV33 | E5 | 8 | 2 |
| HPV33 | E5 | 11 | 2 |
| HPV33 | E5 | 11 | 10 |
| HPV33 | E5 | 8 | 23 |
| HPV33 | E5 | 9 | 48 |
| HPV33 | E5 | 11 | 48 |
| HPV33 | E5 | 8 | 13 |
| HPV33 | E5 | 10 | 11 |
| HPV33 | E5 | 8 | 22 |
| HPV33 | E5 | 9 | 22 |
| HPV33 | E5 | 11 | 32 |
| HPV33 | E5 | 11 | 38 |
| HPV33 | E5 | 8 | 35 |
| HPV33 | E5 | 10 | 33 |
| HPV33 | E5 | 9 | 52 |
| HPV33 | E5 | 9 | 1 |
| HPV33 | E5 | 8 | 51 |
| HPV33 | E5 | 10 | 51 |
| HPV33 | E5 | 9 | 21 |
| HPV33 | E5 | 10 | 21 |
| HPV33 | E5 | 8 | 45 |
| HPV33 | E5 | 11 | 46 |
| HPV33 | E5 | 8 | 50 |
| HPV33 | E5 | 9 | 50 |
| HPV33 | E5 | 11 | 60 |
| HPV33 | E5 | 8 | 41 |
| HPV33 | E5 | 10 | 41 |
| HPV33 | E5 | 11 | 41 |
| HPV33 | E5 | 9 | 4 |
| HPV33 | E5 | 8 | 43 |
| HPV33 | E5 | 9 | 43 |
| HPV33 | E5 | 11 | 43 |
| HPV33 | E5 | 9 | 34 |
| HPV33 | E5 | 9 | 40 |
| HPV33 | E5 | 11 | 40 |
| HPV33 | E5 | 9 | 58 |
| HPV33 | E5 | 10 | 58 |
| HPV33 | E5 | 11 | 58 |
| HPV33 | E6 | 8 | 137 |
| HPV33 | E6 | 9 | 137 |
| HPV33 | E6 | 8 | 138 |
| HPV33 | E6 | 11 | 138 |
| HPV33 | E6 | 8 | 48 |
| HPV33 | E6 | 9 | 46 |
| HPV33 | E6 | 10 | 45 |
| HPV33 | E6 | 9 | 133 |
| HPV33 | E6 | 11 | 133 |

TABLE XVI-continued

HLA-A3 Motif Peptides

| 1 | 2 | 3 | 4 |
|---|---|---|---|
| HPV33 | E6 | 8 | 136 |
| HPV33 | E6 | 9 | 136 |
| HPV33 | E6 | 10 | 136 |
| HPV33 | E6 | 11 | 66 |
| HPV33 | E6 | 10 | 30 |
| HPV33 | E6 | 11 | 44 |
| HPV33 | E6 | 11 | 14 |
| HPV33 | E6 | 10 | 4 |
| HPV33 | E6 | 8 | 32 |
| HPV33 | E6 | 9 | 56 |
| HPV33 | E6 | 11 | 98 |
| HPV33 | E6 | 8 | 27 |
| HPV33 | E6 | 9 | 27 |
| HPV33 | E6 | 8 | 41 |
| HPV33 | E6 | 8 | 47 |
| HPV33 | E6 | 9 | 47 |
| HPV33 | E6 | 10 | 45 |
| HPV33 | E6 | 11 | 45 |
| HPV33 | E6 | 9 | 60 |
| HPV33 | E6 | 10 | 60 |
| HPV33 | E6 | 8 | 69 |
| HPV33 | E6 | 9 | 69 |
| HPV33 | E6 | 10 | 69 |
| HPV33 | E6 | 11 | 69 |
| HPV33 | E6 | 8 | 61 |
| HPV33 | E6 | 9 | 51 |
| HPV33 | E6 | 8 | 118 |
| HPV33 | E6 | 9 | 118 |
| HPV33 | E6 | 8 | 62 |
| HPV33 | E6 | 11 | 62 |
| HPV33 | E6 | 11 | 105 |
| HPV33 | E6 | 10 | 99 |
| HPV33 | E6 | 9 | 73 |
| HPV33 | E6 | 8 | 128 |
| HPV33 | E6 | 10 | 128 |
| HPV33 | E6 | 11 | 128 |
| HPV33 | E6 | 8 | 72 |
| HPV33 | E6 | 10 | 72 |
| HPV33 | E6 | 9 | 64 |
| HPV33 | E6 | 8 | 65 |
| HPV33 | E6 | 8 | 110 |
| HPV33 | E6 | 9 | 110 |
| HPV33 | E6 | 10 | 15 |
| HPV33 | E6 | 9 | 100 |
| HPV33 | E6 | 8 | 70 |
| HPV33 | E6 | 9 | 70 |
| HPV33 | E6 | 10 | 70 |
| HPV33 | E6 | 11 | 50 |
| HPV33 | E6 | 8 | 1 |
| HPV33 | E6 | 10 | 1 |
| HPV33 | E6 | 10 | 25 |
| HPV33 | E6 | 11 | 25 |
| HPV33 | E6 | 9 | 127 |
| HPV33 | E6 | 11 | 127 |
| HPV33 | E6 | 8 | 86 |
| HPV33 | E6 | 9 | 85 |
| HPV33 | E6 | 10 | 59 |
| HPV33 | E6 | 11 | 59 |
| HPV33 | E6 | 8 | 109 |
| HPV33 | E6 | 9 | 109 |
| HPV33 | E6 | 10 | 109 |
| HPV33 | E6 | 8 | 95 |
| HPV33 | E6 | 8 | 36 |
| HPV33 | E6 | 10 | 36 |
| HPV33 | E6 | 11 | 36 |
| HPV33 | E6 | 8 | 17 |
| HPV33 | E6 | 11 | 29 |
| HPV33 | E6 | 8 | 3 |
| HPV33 | E6 | 11 | 3 |
| HPV33 | E6 | 9 | 135 |
| HPV33 | E6 | 10 | 135 |
| HPV33 | E6 | 11 | 135 |
| HPV33 | E6 | 8 | 124 |
| HPV33 | E6 | 10 | 124 |
| HPV33 | E6 | 9 | 68 |
| HPV33 | E6 | 10 | 68 |
| HPV33 | E6 | 11 | 68 |
| HPV33 | E6 | 8 | 39 |
| HPV33 | E6 | 9 | 39 |
| HPV33 | E6 | 10 | 39 |
| HPV33 | E6 | 8 | 141 |
| HPV33 | E6 | 9 | 10 |
| HPV33 | E6 | 9 | 129 |
| HPV33 | E6 | 10 | 129 |
| HPV33 | E6 | 8 | 87 |
| HPV33 | E6 | 8 | 11 |
| HPV33 | E6 | 10 | 51 |
| HPV33 | E6 | 8 | 119 |
| HPV33 | E6 | 9 | 52 |
| HPV33 | E6 | 10 | 132 |
| HPV33 | E6 | 10 | 84 |
| HPV33 | E6 | 11 | 84 |
| HPV33 | E7 | 10 | 50 |
| HPV33 | E7 | 10 | 57 |
| HPV33 | E7 | 10 | 68 |
| HPV33 | E7 | 9 | 42 |
| HPV33 | E7 | 11 | 42 |
| HPV33 | E7 | 10 | 14 |
| HPV33 | E7 | 11 | 30 |
| HPV33 | E7 | 10 | 36 |
| HPV33 | E7 | 9 | 37 |
| HPV33 | E7 | 11 | 85 |
| HPV33 | E7 | 8 | 59 |
| HPV33 | E7 | 11 | 67 |
| HPV33 | E7 | 11 | 13 |
| HPV33 | E7 | 8 | 38 |
| HPV33 | E7 | 11 | 38 |
| HPV33 | E7 | 8 | 88 |
| HPV33 | E7 | 8 | 70 |
| HPV33 | E7 | 8 | 41 |
| HPV33 | E7 | 10 | 41 |
| HPV33 | E7 | 11 | 6 |
| HPV33 | E7 | 9 | 44 |
| HPV33 | E7 | 10 | 44 |
| HPV33 | E7 | 8 | 2 |
| HPV33 | E7 | 10 | 2 |
| HPV33 | E7 | 8 | 66 |
| HPV33 | E7 | 9 | 32 |
| HPV33 | E7 | 10 | 31 |
| HPV33 | E7 | 11 | 49 |
| HPV33 | E7 | 11 | 56 |
| HPV33 | E7 | 10 | 7 |
| HPV33 | E7 | 11 | 63 |
| HPV33 | E7 | 10 | 86 |
| HPV33 | E7 | 10 | 64 |
| HPV33 | L1 | 11 | 482 |
| HPV33 | L1 | 8 | 175 |
| HPV33 | L1 | 9 | 102 |
| HPV33 | L1 | 10 | 456 |
| HPV33 | L1 | 11 | 456 |
| HPV33 | L1 | 11 | 142 |
| HPV33 | L1 | 8 | 471 |
| HPV33 | L1 | 10 | 471 |
| HPV33 | L1 | 11 | 471 |
| HPV33 | L1 | 8 | 37 |
| HPV33 | L1 | 11 | 37 |
| HPV33 | L1 | 11 | 424 |
| HPV33 | L1 | 8 | 284 |
| HPV33 | L1 | 9 | 284 |
| HPV33 | L1 | 8 | 411 |
| HPV33 | L1 | 9 | 411 |
| HPV33 | L1 | 10 | 44 |
| HPV33 | L1 | 9 | 270 |
| HPV33 | L1 | 10 | 225 |
| HPV33 | L1 | 9 | 207 |
| HPV33 | L1 | 11 | 207 |
| HPV33 | L1 | 10 | 345 |
| HPV33 | L1 | 11 | 345 |
| HPV33 | L1 | 8 | 103 |
| HPV33 | L1 | 8 | 128 |

TABLE XVI-continued

HLA-A3 Motif Peptides

| 1 | 2 | 3 | 4 |
|---|---|---|---|
| HPV33 | L1 | 9 | 128 |
| HPV33 | L1 | 9 | 209 |
| HPV33 | L1 | 9 | 197 |
| HPV33 | L1 | 8 | 223 |
| HPV33 | L1 | 9 | 223 |
| HPV33 | L1 | 8 | 396 |
| HPV33 | L1 | 9 | 457 |
| HPV33 | L1 | 10 | 457 |
| HPV33 | L1 | 11 | 457 |
| HPV33 | L1 | 8 | 449 |
| HPV33 | L1 | 10 | 370 |
| HPV33 | L1 | 11 | 274 |
| HPV33 | L1 | 8 | 244 |
| HPV33 | L1 | 9 | 244 |
| HPV33 | L1 | 9 | 351 |
| HPV33 | L1 | 10 | 351 |
| HPV33 | L1 | 8 | 129 |
| HPV33 | L1 | 9 | 202 |
| HPV33 | L1 | 10 | 202 |
| HPV33 | L1 | 8 | 95 |
| HPV33 | L1 | 11 | 88 |
| HPV33 | L1 | 10 | 415 |
| HPV33 | L1 | 8 | 269 |
| HPV33 | L1 | 10 | 269 |
| HPV33 | L1 | 8 | 146 |
| HPV33 | L1 | 10 | 196 |
| HPV33 | L1 | 9 | 437 |
| HPV33 | L1 | 9 | 303 |
| HPV33 | L1 | 8 | 447 |
| HPV33 | L1 | 10 | 447 |
| HPV33 | L1 | 8 | 385 |
| HPV33 | L1 | 9 | 127 |
| HPV33 | L1 | 10 | 127 |
| HPV33 | L1 | 10 | 247 |
| HPV33 | L1 | 9 | 248 |
| HPV33 | L1 | 11 | 248 |
| HPV33 | L1 | 11 | 260 |
| HPV33 | L1 | 11 | 205 |
| HPV33 | L1 | 8 | 84 |
| HPV33 | L1 | 9 | 84 |
| HPV33 | L1 | 9 | 403 |
| HPV33 | L1 | 8 | 467 |
| HPV33 | L1 | 9 | 467 |
| HPV33 | L1 | 10 | 467 |
| HPV33 | L1 | 8 | 249 |
| HPV33 | L1 | 10 | 249 |
| HPV33 | L1 | 11 | 249 |
| HPV33 | L1 | 8 | 454 |
| HPV33 | L1 | 9 | 50 |
| HPV33 | L1 | 10 | 50 |
| HPV33 | L1 | 11 | 50 |
| HPV33 | L1 | 8 | 256 |
| HPV33 | L1 | 9 | 256 |
| HPV33 | L1 | 11 | 419 |
| HPV33 | L1 | 9 | 330 |
| HPV33 | L1 | 9 | 161 |
| HPV33 | L1 | 10 | 206 |
| HPV33 | L1 | 8 | 198 |
| HPV33 | L1 | 9 | 243 |
| HPV33 | L1 | 10 | 243 |
| HPV33 | L1 | 8 | 204 |
| HPV33 | L1 | 8 | 85 |
| HPV33 | L1 | 9 | 322 |
| HPV33 | L1 | 10 | 117 |
| HPV33 | L1 | 11 | 117 |
| HPV33 | L1 | 9 | 472 |
| HPV33 | L1 | 10 | 472 |
| HPV33 | L1 | 11 | 472 |
| HPV33 | L1 | 8 | 68 |
| HPV33 | L1 | 10 | 68 |
| HPV33 | L1 | 8 | 404 |
| HPV33 | L1 | 11 | 297 |
| HPV33 | L1 | 10 | 38 |
| HPV33 | L1 | 9 | 226 |
| HPV33 | L1 | 11 | 226 |
| HPV33 | L1 | 10 | 281 |
| HPV33 | L1 | 11 | 281 |
| HPV33 | L1 | 8 | 173 |
| HPV33 | L1 | 10 | 173 |
| HPV33 | L1 | 9 | 365 |
| HPV33 | L1 | 11 | 365 |
| HPV33 | L1 | 8 | 224 |
| HPV33 | L1 | 11 | 224 |
| HPV33 | L1 | 8 | 323 |
| HPV33 | L1 | 9 | 222 |
| HPV33 | L1 | 10 | 222 |
| HPV33 | L1 | 9 | 118 |
| HPV33 | L1 | 10 | 118 |
| HPV33 | L1 | 10 | 425 |
| HPV33 | L1 | 8 | 474 |
| HPV33 | L1 | 9 | 474 |
| HPV33 | L1 | 10 | 474 |
| HPV33 | L1 | 10 | 126 |
| HPV33 | L1 | 11 | 126 |
| HPV33 | L1 | 9 | 83 |
| HPV33 | L1 | 10 | 83 |
| HPV33 | L1 | 9 | 466 |
| HPV33 | L1 | 10 | 466 |
| HPV33 | L1 | 11 | 466 |
| HPV33 | L1 | 9 | 453 |
| HPV33 | L1 | 8 | 172 |
| HPV33 | L1 | 9 | 172 |
| HPV33 | L1 | 11 | 172 |
| HPV33 | L1 | 11 | 478 |
| HPV33 | L1 | 8 | 429 |
| HPV33 | L1 | 8 | 65 |
| HPV33 | L1 | 10 | 65 |
| HPV33 | L1 | 11 | 65 |
| HPV33 | L1 | 11 | 379 |
| HPV33 | L1 | 8 | 20 |
| HPV33 | L1 | 11 | 20 |
| HPV33 | L1 | 8 | 43 |
| HPV33 | L1 | 11 | 43 |
| HPV33 | L1 | 8 | 377 |
| HPV33 | L1 | 11 | 344 |
| HPV33 | L1 | 8 | 458 |
| HPV33 | L1 | 9 | 458 |
| HPV33 | L1 | 10 | 458 |
| HPV33 | L1 | 11 | 246 |
| HPV33 | L1 | 10 | 306 |
| HPV33 | L1 | 11 | 306 |
| HPV33 | L1 | 10 | 160 |
| HPV33 | L1 | 10 | 267 |
| HPV33 | L1 | 9 | 463 |
| HPV33 | L1 | 8 | 114 |
| HPV33 | L1 | 8 | 42 |
| HPV33 | L1 | 9 | 42 |
| HPV33 | L1 | 11 | 159 |
| HPV33 | L1 | 8 | 468 |
| HPV33 | L1 | 9 | 468 |
| HPV33 | L1 | 11 | 468 |
| HPV33 | L1 | 11 | 61 |
| HPV33 | L1 | 8 | 382 |
| HPV33 | L1 | 10 | 382 |
| HPV33 | L1 | 11 | 382 |
| HPV33 | L1 | 10 | 62 |
| HPV33 | L1 | 11 | 62 |
| HPV33 | L1 | 8 | 208 |
| HPV33 | L1 | 10 | 208 |
| HPV33 | L1 | 9 | 255 |
| HPV33 | L1 | 10 | 255 |
| HPV33 | L1 | 9 | 1 |
| HPV33 | L1 | 11 | 237 |
| HPV33 | L1 | 11 | 200 |
| HPV33 | L1 | 9 | 299 |
| HPV33 | L1 | 11 | 299 |
| HPV33 | L1 | 9 | 57 |
| HPV33 | L1 | 8 | 358 |
| HPV33 | L1 | 10 | 321 |
| HPV33 | L1 | 9 | 395 |

TABLE XVI-continued

HLA-A3 Motif Peptides

| 1 | 2 | 3 | 4 |
|---|---|---|---|
| HPV33 | L1 | 8 | 79 |
| HPV33 | L1 | 9 | 94 |
| HPV33 | L1 | 11 | 232 |
| HPV33 | L1 | 9 | 137 |
| HPV33 | L1 | 10 | 221 |
| HPV33 | L1 | 11 | 221 |
| HPV33 | L1 | 10 | 462 |
| HPV33 | L1 | 9 | 113 |
| HPV33 | L1 | 9 | 409 |
| HPV33 | L1 | 10 | 409 |
| HPV33 | L1 | 11 | 409 |
| HPV33 | L1 | 8 | 165 |
| HPV33 | L1 | 11 | 165 |
| HPV33 | L1 | 11 | 55 |
| HPV33 | L1 | 9 | 484 |
| HPV33 | L1 | 10 | 484 |
| HPV33 | L1 | 11 | 484 |
| HPV33 | L1 | 11 | 17 |
| HPV33 | L1 | 9 | 470 |
| HPV33 | L1 | 11 | 470 |
| HPV33 | L1 | 11 | 414 |
| HPV33 | L1 | 10 | 402 |
| HPV33 | L1 | 8 | 460 |
| HPV33 | L1 | 8 | 372 |
| HPV33 | L1 | 9 | 376 |
| HPV33 | L1 | 8 | 156 |
| HPV33 | L1 | 11 | 305 |
| HPV33 | L1 | 8 | 254 |
| HPV33 | L1 | 10 | 254 |
| HPV33 | L1 | 11 | 254 |
| HPV33 | L1 | 10 | 154 |
| HPV33 | L1 | 11 | 328 |
| HPV33 | L1 | 8 | 347 |
| HPV33 | L1 | 9 | 347 |
| HPV33 | L1 | 8 | 481 |
| HPV33 | L1 | 8 | 263 |
| HPV33 | L1 | 9 | 41 |
| HPV33 | L1 | 10 | 41 |
| HPV33 | L1 | 8 | 77 |
| HPV33 | L1 | 10 | 77 |
| HPV33 | L1 | 8 | 30 |
| HPV33 | L1 | 8 | 488 |
| HPV33 | L1 | 9 | 488 |
| HPV33 | L1 | 11 | 488 |
| HPV33 | L1 | 9 | 75 |
| HPV33 | L1 | 10 | 75 |
| HPV33 | L1 | 11 | 455 |
| HPV33 | L1 | 8 | 491 |
| HPV33 | L1 | 9 | 491 |
| HPV33 | L1 | 8 | 410 |
| HPV33 | L1 | 9 | 410 |
| HPV33 | L1 | 10 | 410 |
| HPV33 | L1 | 10 | 350 |
| HPV33 | L1 | 11 | 350 |
| HPV33 | L1 | 9 | 90 |
| HPV33 | L1 | 8 | 119 |
| HPV33 | L1 | 9 | 119 |
| HPV33 | L1 | 8 | 67 |
| HPV33 | L1 | 9 | 67 |
| HPV33 | L1 | 11 | 67 |
| HPV33 | L1 | 11 | 280 |
| HPV33 | L1 | 8 | 51 |
| HPV33 | L1 | 9 | 51 |
| HPV33 | L1 | 10 | 51 |
| HPV33 | L1 | 8 | 285 |
| HPV33 | L1 | 10 | 32 |
| HPV33 | L1 | 8 | 245 |
| HPV33 | L1 | 8 | 412 |
| HPV33 | L1 | 10 | 298 |
| HPV33 | L1 | 9 | 490 |
| HPV33 | L1 | 10 | 490 |
| HPV33 | L1 | 9 | 39 |
| HPV33 | L1 | 11 | 39 |
| HPV33 | L1 | 8 | 227 |
| HPV33 | L1 | 10 | 227 |
| HPV33 | L1 | 8 | 23 |
| HPV33 | L1 | 8 | 486 |
| HPV33 | L1 | 9 | 486 |
| HPV33 | L1 | 10 | 486 |
| HPV33 | L1 | 11 | 486 |
| HPV33 | L1 | 8 | 352 |
| HPV33 | L1 | 9 | 352 |
| HPV33 | L1 | 11 | 352 |
| HPV33 | L1 | 8 | 2 |
| HPV33 | L1 | 11 | 2 |
| HPV33 | L1 | 9 | 383 |
| HPV33 | L1 | 10 | 383 |
| HPV33 | L1 | 8 | 283 |
| HPV33 | L1 | 9 | 283 |
| HPV33 | L1 | 10 | 283 |
| HPV33 | L1 | 9 | 228 |
| HPV33 | L1 | 9 | 426 |
| HPV33 | L1 | 11 | 426 |
| HPV33 | L1 | 11 | 24 |
| HPV33 | L1 | 8 | 444 |
| HPV33 | L1 | 10 | 444 |
| HPV33 | L1 | 11 | 444 |
| HPV33 | L1 | 10 | 166 |
| HPV33 | L1 | 8 | 203 |
| HPV33 | L1 | 9 | 203 |
| HPV33 | L1 | 11 | 132 |
| HPV33 | L1 | 11 | 266 |
| HPV33 | L1 | 9 | 381 |
| HPV33 | L1 | 11 | 381 |
| HPV33 | L1 | 11 | 349 |
| HPV33 | L1 | 10 | 238 |
| HPV33 | L1 | 11 | 238 |
| HPV33 | L1 | 9 | 301 |
| HPV33 | L1 | 11 | 301 |
| HPV33 | L1 | 10 | 89 |
| HPV33 | L1 | 11 | 31 |
| HPV33 | L1 | 9 | 421 |
| HPV33 | L1 | 8 | 489 |
| HPV33 | L1 | 10 | 489 |
| HPV33 | L1 | 11 | 489 |
| HPV33 | L1 | 8 | 485 |
| HPV33 | L1 | 9 | 485 |
| HPV33 | L1 | 10 | 485 |
| HPV33 | L1 | 11 | 485 |
| HPV33 | L1 | 9 | 282 |
| HPV33 | L1 | 10 | 282 |
| HPV33 | L1 | 11 | 282 |
| HPV33 | L1 | 11 | 10 |
| HPV33 | L1 | 9 | 174 |
| HPV33 | L1 | 9 | 448 |
| HPV33 | L1 | 10 | 201 |
| HPV33 | L1 | 11 | 201 |
| HPV33 | L1 | 11 | 374 |
| HPV33 | L1 | 11 | 73 |
| HPV33 | L1 | 10 | 329 |
| HPV33 | L1 | 9 | 45 |
| HPV33 | L1 | 11 | 116 |
| HPV33 | L1 | 9 | 66 |
| HPV33 | L1 | 10 | 66 |
| HPV33 | L1 | 10 | 18 |
| HPV33 | L1 | 8 | 28 |
| HPV33 | L1 | 9 | 28 |
| HPV33 | L1 | 10 | 28 |
| HPV33 | L1 | 9 | 22 |
| HPV33 | L1 | 10 | 380 |
| HPV33 | L1 | 8 | 348 |
| HPV33 | L1 | 8 | 300 |
| HPV33 | L1 | 10 | 300 |
| HPV33 | L1 | 10 | 420 |
| HPV33 | L1 | 8 | 331 |
| HPV33 | L1 | 10 | 21 |
| HPV33 | L1 | 10 | 101 |
| HPV33 | L1 | 10 | 170 |
| HPV33 | L1 | 11 | 170 |
| HPV33 | L1 | 8 | 312 |

TABLE XVI-continued

HLA-A3 Motif Peptides

| 1 | 2 | 3 | 4 |
|---|---|---|---|
| HPV33 | L1 | 9 | 36 |
| HPV33 | L1 | 11 | 369 |
| HPV33 | L1 | 10 | 49 |
| HPV33 | L1 | 11 | 49 |
| HPV33 | L1 | 8 | 242 |
| HPV33 | L1 | 10 | 242 |
| HPV33 | L1 | 11 | 242 |
| HPV33 | L1 | 9 | 276 |
| HPV33 | L1 | 8 | 362 |
| HPV33 | L1 | 9 | 234 |
| HPV33 | L1 | 9 | 12 |
| HPV33 | L1 | 9 | 443 |
| HPV33 | L1 | 11 | 443 |
| HPV33 | L1 | 8 | 27 |
| HPV33 | L1 | 9 | 27 |
| HPV33 | L1 | 10 | 27 |
| HPV33 | L1 | 11 | 27 |
| HPV33 | L2 | 9 | 81 |
| HPV33 | L2 | 8 | 367 |
| HPV33 | L2 | 9 | 438 |
| HPV33 | L2 | 10 | 438 |
| HPV33 | L2 | 8 | 241 |
| HPV33 | L2 | 8 | 82 |
| HPV33 | L2 | 10 | 291 |
| HPV33 | L2 | 11 | 291 |
| HPV33 | L2 | 10 | 286 |
| HPV33 | L2 | 11 | 286 |
| HPV33 | L2 | 11 | 12 |
| HPV33 | L2 | 9 | 308 |
| HPV33 | L2 | 9 | 14 |
| HPV33 | L2 | 10 | 14 |
| HPV33 | L2 | 9 | 280 |
| HPV33 | L2 | 10 | 280 |
| HPV33 | L2 | 8 | 439 |
| HPV33 | L2 | 9 | 439 |
| HPV33 | L2 | 8 | 436 |
| HPV33 | L2 | 11 | 436 |
| HPV33 | L2 | 8 | 360 |
| HPV33 | L2 | 9 | 283 |
| HPV33 | L2 | 10 | 272 |
| HPV33 | L2 | 10 | 327 |
| HPV33 | L2 | 8 | 431 |
| HPV33 | L2 | 10 | 431 |
| HPV33 | L2 | 11 | 369 |
| HPV33 | L2 | 11 | 130 |
| HPV33 | L2 | 11 | 364 |
| HPV33 | L2 | 8 | 176 |
| HPV33 | L2 | 8 | 263 |
| HPV33 | L2 | 11 | 36 |
| HPV33 | L2 | 11 | 258 |
| HPV33 | L2 | 10 | 149 |
| HPV33 | L2 | 9 | 110 |
| HPV33 | L2 | 11 | 110 |
| HPV33 | L2 | 9 | 260 |
| HPV33 | L2 | 11 | 260 |
| HPV33 | L2 | 9 | 430 |
| HPV33 | L2 | 11 | 430 |
| HPV33 | L2 | 8 | 459 |
| HPV33 | L2 | 9 | 459 |
| HPV33 | L2 | 8 | 113 |
| HPV33 | L2 | 8 | 447 |
| HPV33 | L2 | 9 | 447 |
| HPV33 | L2 | 10 | 447 |
| HPV33 | L2 | 8 | 281 |
| HPV33 | L2 | 9 | 281 |
| HPV33 | L2 | 11 | 281 |
| HPV33 | L2 | 11 | 242 |
| HPV33 | L2 | 8 | 301 |
| HPV33 | L2 | 11 | 301 |
| HPV33 | L2 | 11 | 183 |
| HPV33 | L2 | 8 | 460 |
| HPV33 | L2 | 8 | 163 |
| HPV33 | L2 | 11 | 163 |
| HPV33 | L2 | 8 | 440 |
| HPV33 | L2 | 11 | 440 |
| HPV33 | L2 | 8 | 421 |
| HPV33 | L2 | 10 | 421 |
| HPV33 | L2 | 10 | 437 |
| HPV33 | L2 | 11 | 437 |
| HPV33 | L2 | 8 | 128 |
| HPV33 | L2 | 11 | 58 |
| HPV33 | L2 | 11 | 226 |
| HPV33 | L2 | 8 | 64 |
| HPV33 | L2 | 10 | 62 |
| HPV33 | L2 | 11 | 218 |
| HPV33 | L2 | 10 | 37 |
| HPV33 | L2 | 11 | 37 |
| HPV33 | L2 | 10 | 25 |
| HPV33 | L2 | 8 | 75 |
| HPV33 | L2 | 9 | 60 |
| HPV33 | L2 | 8 | 349 |
| HPV33 | L2 | 10 | 379 |
| HPV33 | L2 | 8 | 374 |
| HPV33 | L2 | 11 | 374 |
| HPV33 | L2 | 8 | 336 |
| HPV33 | L2 | 11 | 297 |
| HPV33 | L2 | 8 | 40 |
| HPV33 | L2 | 11 | 285 |
| HPV33 | L2 | 8 | 318 |
| HPV33 | L2 | 8 | 74 |
| HPV33 | L2 | 9 | 74 |
| HPV33 | L2 | 10 | 59 |
| HPV33 | L2 | 8 | 284 |
| HPV33 | L2 | 10 | 44 |
| HPV33 | L2 | 11 | 44 |
| HPV33 | L2 | 8 | 448 |
| HPV33 | L2 | 9 | 448 |
| HPV33 | L2 | 11 | 448 |
| HPV33 | L2 | 9 | 273 |
| HPV33 | L2 | 9 | 155 |
| HPV33 | L2 | 9 | 292 |
| HPV33 | L2 | 10 | 292 |
| HPV33 | L2 | 8 | 250 |
| HPV33 | L2 | 11 | 250 |
| HPV33 | L2 | 10 | 104 |
| HPV33 | L2 | 8 | 433 |
| HPV33 | L2 | 11 | 433 |
| HPV33 | L2 | 10 | 307 |
| HPV33 | L2 | 9 | 248 |
| HPV33 | L2 | 10 | 248 |
| HPV33 | L2 | 10 | 311 |
| HPV33 | L2 | 11 | 311 |
| HPV33 | L2 | 8 | 34 |
| HPV33 | L2 | 10 | 334 |
| HPV33 | L2 | 8 | 282 |
| HPV33 | L2 | 10 | 282 |
| HPV33 | L2 | 8 | 414 |
| HPV33 | L2 | 10 | 107 |
| HPV33 | L2 | 8 | 249 |
| HPV33 | L2 | 9 | 249 |
| HPV33 | L2 | 9 | 328 |
| HPV33 | L2 | 10 | 243 |
| HPV33 | L2 | 11 | 405 |
| HPV33 | L2 | 8 | 359 |
| HPV33 | L2 | 9 | 359 |
| HPV33 | L2 | 11 | 231 |
| HPV33 | L2 | 8 | 372 |
| HPV33 | L2 | 10 | 372 |
| HPV33 | L2 | 10 | 391 |
| HPV33 | L2 | 8 | 174 |
| HPV33 | L2 | 10 | 174 |
| HPV33 | L2 | 8 | 240 |
| HPV33 | L2 | 9 | 240 |
| HPV33 | L2 | 8 | 290 |
| HPV33 | L2 | 11 | 290 |
| HPV33 | L2 | 9 | 172 |
| HPV33 | L2 | 10 | 172 |
| HPV33 | L2 | 11 | 119 |
| HPV33 | L2 | 8 | 279 |
| HPV33 | L2 | 10 | 279 |

TABLE XVI-continued

HLA-A3 Motif Peptides

| 1 | 2 | 3 | 4 |
|---|---|---|---|
| HPV33 | L2 | 11 | 279 |
| HPV33 | L2 | 8 | 408 |
| HPV33 | L2 | 10 | 277 |
| HPV33 | L2 | 10 | 429 |
| HPV33 | L2 | 8 | 420 |
| HPV33 | L2 | 9 | 420 |
| HPV33 | L2 | 11 | 420 |
| HPV33 | L2 | 8 | 217 |
| HPV33 | L2 | 9 | 73 |
| HPV33 | L2 | 10 | 73 |
| HPV33 | L2 | 9 | 215 |
| HPV33 | L2 | 10 | 215 |
| HPV33 | L2 | 8 | 423 |
| HPV33 | L2 | 11 | 333 |
| HPV33 | L2 | 9 | 413 |
| HPV33 | L2 | 10 | 347 |
| HPV33 | L2 | 9 | 376 |
| HPV33 | L2 | 10 | 376 |
| HPV33 | L2 | 10 | 126 |
| HPV33 | L2 | 9 | 121 |
| HPV33 | L2 | 11 | 411 |
| HPV33 | L2 | 8 | 166 |
| HPV33 | L2 | 10 | 166 |
| HPV33 | L2 | 8 | 444 |
| HPV33 | L2 | 9 | 444 |
| HPV33 | L2 | 10 | 444 |
| HPV33 | L2 | 11 | 444 |
| HPV33 | L2 | 11 | 79 |
| HPV33 | L2 | 10 | 161 |
| HPV33 | L2 | 8 | 186 |
| HPV33 | L2 | 8 | 221 |
| HPV33 | L2 | 10 | 221 |
| HPV33 | L2 | 11 | 326 |
| HPV33 | L2 | 10 | 267 |
| HPV33 | L2 | 8 | 317 |
| HPV33 | L2 | 9 | 317 |
| HPV33 | L2 | 11 | 43 |
| HPV33 | L2 | 8 | 16 |
| HPV33 | L2 | 11 | 191 |
| HPV33 | L2 | 11 | 153 |
| HPV33 | L2 | 8 | 234 |
| HPV33 | L2 | 9 | 234 |
| HPV33 | L2 | 8 | 11 |
| HPV33 | L2 | 10 | 455 |
| HPV33 | L2 | 8 | 300 |
| HPV33 | L2 | 9 | 300 |
| HPV33 | L2 | 8 | 313 |
| HPV33 | L2 | 9 | 313 |
| HPV33 | L2 | 11 | 313 |
| HPV33 | L2 | 8 | 5 |
| HPV33 | L2 | 10 | 5 |
| HPV33 | L2 | 9 | 303 |
| HPV33 | L2 | 11 | 303 |
| HPV33 | L2 | 10 | 13 |
| HPV33 | L2 | 11 | 13 |
| HPV33 | L2 | 11 | 271 |
| HPV33 | L2 | 10 | 259 |
| HPV33 | L2 | 9 | 112 |
| HPV33 | L2 | 9 | 127 |
| HPV33 | L2 | 8 | 314 |
| HPV33 | L2 | 10 | 314 |
| HPV33 | L2 | 11 | 314 |
| HPV33 | L2 | 10 | 406 |
| HPV33 | L2 | 9 | 63 |
| HPV33 | L2 | 10 | 357 |
| HPV33 | L2 | 11 | 357 |
| HPV33 | L2 | 8 | 393 |
| HPV33 | L2 | 8 | 122 |
| HPV33 | L2 | 8 | 151 |
| HPV33 | L2 | 11 | 103 |
| HPV33 | L2 | 8 | 106 |
| HPV33 | L2 | 11 | 106 |
| HPV33 | L2 | 9 | 150 |
| HPV33 | L2 | 10 | 418 |
| HPV33 | L2 | 11 | 418 |

| 1 | 2 | 3 | 4 |
|---|---|---|---|
| HPV33 | L2 | 10 | 184 |
| HPV33 | L2 | 9 | 212 |
| HPV33 | L2 | 10 | 354 |
| HPV33 | L2 | 8 | 156 |
| HPV33 | L2 | 9 | 38 |
| HPV33 | L2 | 10 | 38 |
| HPV33 | L2 | 8 | 213 |
| HPV33 | L2 | 11 | 213 |
| HPV33 | L2 | 9 | 6 |
| HPV33 | L2 | 9 | 167 |
| HPV33 | L2 | 11 | 167 |
| HPV33 | L2 | 10 | 80 |
| HPV33 | L2 | 9 | 26 |
| HPV33 | L2 | 9 | 162 |
| HPV33 | L2 | 8 | 61 |
| HPV33 | L2 | 11 | 61 |
| HPV33 | L2 | 11 | 24 |
| HPV33 | L2 | 8 | 39 |
| HPV33 | L2 | 9 | 39 |
| HPV33 | L2 | 10 | 154 |
| HPV33 | L2 | 9 | 432 |
| HPV33 | L2 | 8 | 309 |
| HPV33 | L2 | 8 | 133 |
| HPV33 | L2 | 8 | 111 |
| HPV33 | L2 | 10 | 111 |
| HPV33 | L2 | 9 | 244 |
| HPV33 | L2 | 8 | 293 |
| HPV33 | L2 | 9 | 293 |
| HPV33 | L2 | 11 | 293 |
| HPV33 | L2 | 11 | 417 |
| HPV33 | L2 | 10 | 211 |
| HPV33 | L2 | 11 | 353 |
| HPV33 | L2 | 9 | 132 |
| HPV33 | L2 | 10 | 298 |
| HPV33 | L2 | 11 | 298 |
| HPV33 | L2 | 9 | 222 |
| HPV33 | L2 | 9 | 435 |
| HPV33 | L2 | 10 | 370 |
| HPV33 | L2 | 10 | 238 |
| HPV33 | L2 | 11 | 238 |
| HPV33 | L2 | 8 | 304 |
| HPV33 | L2 | 10 | 304 |
| HPV33 | L2 | 11 | 31 |
| HPV33 | L2 | 8 | 168 |
| HPV33 | L2 | 10 | 168 |
| HPV33 | L2 | 10 | 441 |
| HPV33 | L2 | 11 | 441 |
| HPV33 | L2 | 9 | 392 |
| HPV33 | L2 | 9 | 105 |
| HPV33 | L2 | 11 | 210 |
| HPV33 | L2 | 10 | 131 |
| HPV33 | L2 | 10 | 434 |
| HPV33 | L2 | 11 | 237 |
| HPV33 | L2 | 9 | |
| HPV33 | L2 | 9 | 252 |
| HPV33 | L2 | 9 | 458 |
| HPV33 | L2 | 10 | 458 |
| HPV33 | L2 | 8 | 446 |
| HPV33 | L2 | 9 | 446 |
| HPV33 | L2 | 10 | 446 |
| HPV33 | L2 | 11 | 446 |
| HPV33 | L2 | 8 | 47 |
| HPV33 | L2 | 8 | 356 |
| HPV33 | L2 | 11 | 356 |
| HPV33 | L2 | 9 | 228 |
| HPV33 | L2 | 8 | 381 |
| HPV33 | L2 | 11 | 71 |
| HPV45 | E1 | 11 | 382 |
| HPV45 | E1 | 10 | 383 |
| HPV45 | E1 | 11 | 383 |
| HPV45 | E1 | 8 | 198 |
| HPV45 | E1 | 11 | 198 |
| HPV45 | E1 | 8 | 376 |
| HPV45 | E1 | 9 | 376 |
| HPV45 | E1 | 10 | 376 |

TABLE XVI-continued

HLA-A3 Motif Peptides

| 1 | 2 | 3 | 4 |
|---|---|---|---|
| HPV45 | E1 | 8 | 622 |
| HPV45 | E1 | 11 | 622 |
| HPV45 | E1 | 11 | 507 |
| HPV45 | E1 | 9 | 384 |
| HPV45 | E1 | 10 | 384 |
| HPV45 | E1 | 11 | 384 |
| HPV45 | E1 | 8 | 369 |
| HPV45 | E1 | 10 | 232 |
| HPV45 | E1 | 11 | 490 |
| HPV45 | E1 | 11 | 532 |
| HPV45 | E1 | 11 | 452 |
| HPV45 | E1 | 9 | 270 |
| HPV45 | E1 | 11 | 270 |
| HPV45 | E1 | 10 | 199 |
| HPV45 | E1 | 8 | 512 |
| HPV45 | E1 | 10 | 193 |
| HPV45 | E1 | 11 | 40 |
| HPV45 | E1 | 8 | 517 |
| HPV45 | E1 | 9 | 517 |
| HPV45 | E1 | 11 | 202 |
| HPV45 | E1 | 8 | 399 |
| HPV45 | E1 | 9 | 399 |
| HPV45 | E1 | 10 | 399 |
| HPV45 | E1 | 8 | 398 |
| HPV45 | E1 | 9 | 398 |
| HPV45 | E1 | 10 | 398 |
| HPV45 | E1 | 11 | 398 |
| HPV45 | E1 | 9 | 604 |
| HPV45 | E1 | 9 | 276 |
| HPV45 | E1 | 10 | 276 |
| HPV45 | E1 | 8 | 465 |
| HPV45 | E1 | 8 | 297 |
| HPV45 | E1 | 10 | 297 |
| HPV45 | E1 | 11 | 423 |
| HPV45 | E1 | 9 | 226 |
| HPV45 | E1 | 8 | 634 |
| HPV45 | E1 | 9 | 621 |
| HPV45 | E1 | 9 | 78 |
| HPV45 | E1 | 10 | 78 |
| HPV45 | E1 | 11 | 78 |
| HPV45 | E1 | 9 | 516 |
| HPV45 | E1 | 10 | 516 |
| HPV45 | E1 | 8 | 397 |
| HPV45 | E1 | 9 | 397 |
| HPV45 | E1 | 10 | 397 |
| HPV45 | E1 | 11 | 397 |
| HPV45 | E1 | 10 | 261 |
| HPV45 | E1 | 8 | 377 |
| HPV45 | E1 | 9 | 377 |
| HPV45 | E1 | 11 | 377 |
| HPV45 | E1 | 10 | 515 |
| HPV45 | E1 | 11 | 515 |
| HPV45 | E1 | 11 | 8 |
| HPV45 | E1 | 9 | 534 |
| HPV45 | E1 | 10 | 534 |
| HPV45 | E1 | 11 | 534 |
| HPV45 | E1 | 9 | 614 |
| HPV45 | E1 | 9 | 349 |
| HPV45 | E1 | 10 | 349 |
| HPV45 | E1 | 9 | 361 |
| HPV45 | E1 | 10 | 361 |
| HPV45 | E1 | 10 | 214 |
| HPV45 | E1 | 10 | 367 |
| HPV45 | E1 | 11 | 134 |
| HPV45 | E1 | 10 | 623 |
| HPV45 | E1 | 11 | 623 |
| HPV45 | E1 | 9 | 42 |
| HPV45 | E1 | 10 | 508 |
| HPV45 | E1 | 8 | 328 |
| HPV45 | E1 | 10 | 52 |
| HPV45 | E1 | 11 | 30 |
| HPV45 | E1 | 10 | 620 |
| HPV45 | E1 | 8 | 445 |
| HPV45 | E1 | 10 | 445 |
| HPV45 | E1 | 8 | 455 |
| HPV45 | E1 | 9 | 455 |
| HPV45 | E1 | 8 | 242 |
| HPV45 | E1 | 10 | 242 |
| HPV45 | E1 | 11 | 428 |
| HPV45 | E1 | 8 | 625 |
| HPV45 | E1 | 9 | 625 |
| HPV45 | E1 | 9 | 10 |
| HPV45 | E1 | 10 | 10 |
| HPV45 | E1 | 8 | 596 |
| HPV45 | E1 | 10 | 596 |
| HPV45 | E1 | 11 | 596 |
| HPV45 | E1 | 8 | 115 |
| HPV45 | E1 | 9 | 115 |
| HPV45 | E1 | 10 | 115 |
| HPV45 | E1 | 11 | 115 |
| HPV45 | E1 | 8 | 186 |
| HPV45 | E1 | 11 | 186 |
| HPV45 | E1 | 8 | 189 |
| HPV45 | E1 | 9 | 189 |
| HPV45 | E1 | 10 | 189 |
| HPV45 | E1 | 11 | 189 |
| HPV45 | E1 | 8 | 365 |
| HPV45 | E1 | 9 | 365 |
| HPV45 | E1 | 9 | 573 |
| HPV45 | E1 | 11 | 573 |
| HPV45 | E1 | 8 | 64 |
| HPV45 | E1 | 9 | 64 |
| HPV45 | E1 | 10 | 295 |
| HPV45 | E1 | 10 | 146 |
| HPV45 | E1 | 10 | 74 |
| HPV45 | E1 | 9 | 587 |
| HPV45 | E1 | 10 | 348 |
| HPV45 | E1 | 11 | 348 |
| HPV45 | E1 | 8 | 525 |
| HPV45 | E1 | 8 | 605 |
| HPV45 | E1 | 9 | 18 |
| HPV45 | E1 | 10 | 18 |
| HPV45 | E1 | 8 | 479 |
| HPV45 | E1 | 8 | 234 |
| HPV45 | E1 | 11 | 234 |
| HPV45 | E1 | 8 | 483 |
| HPV45 | E1 | 9 | 446 |
| HPV45 | E1 | 11 | 446 |
| HPV45 | E1 | 8 | 456 |
| HPV45 | E1 | 8 | 385 |
| HPV45 | E1 | 9 | 385 |
| HPV45 | E1 | 10 | 385 |
| HPV45 | E1 | 9 | 486 |
| HPV45 | E1 | 8 | 449 |
| HPV45 | E1 | 10 | 449 |
| HPV45 | E1 | 9 | 438 |
| HPV45 | E1 | 8 | 212 |
| HPV45 | E1 | 9 | 212 |
| HPV45 | E1 | 9 | 579 |
| HPV45 | E1 | 11 | 579 |
| HPV45 | E1 | 8 | 130 |
| HPV45 | E1 | 8 | 19 |
| HPV45 | E1 | 9 | 19 |
| HPV45 | E1 | 8 | 494 |
| HPV45 | E1 | 8 | 138 |
| HPV45 | E1 | 9 | 327 |
| HPV45 | E1 | 9 | 430 |
| HPV45 | E1 | 11 | 430 |
| HPV45 | E1 | 9 | 243 |
| HPV45 | E1 | 8 | 168 |
| HPV45 | E1 | 10 | 429 |
| HPV45 | E1 | 8 | 626 |
| HPV45 | E1 | 9 | 209 |
| HPV45 | E1 | 11 | 209 |
| HPV45 | E1 | 11 | 480 |
| HPV45 | E1 | 8 | 11 |
| HPV45 | E1 | 9 | 11 |
| HPV45 | E1 | 11 | 459 |
| HPV45 | E1 | 9 | 443 |
| HPV45 | E1 | 10 | 443 |

TABLE XVI-continued

HLA-A3 Motif Peptides

| 1 | 2 | 3 | 4 |
|---|---|---|---|
| HPV45 | E1 | 9 | 265 |
| HPV45 | E1 | 10 | 265 |
| HPV45 | E1 | 11 | 265 |
| HPV45 | E1 | 10 | 235 |
| HPV45 | E1 | 11 | 235 |
| HPV45 | E1 | 9 | 71 |
| HPV45 | E1 | 8 | 181 |
| HPV45 | E1 | 10 | 485 |
| HPV45 | E1 | 8 | 500 |
| HPV45 | E1 | 11 | 500 |
| HPV45 | E1 | 8 | 341 |
| HPV45 | E1 | 8 | 256 |
| HPV45 | E1 | 8 | 83 |
| HPV45 | E1 | 10 | 519 |
| HPV45 | E1 | 10 | 57 |
| HPV45 | E1 | 8 | 426 |
| HPV45 | E1 | 8 | 561 |
| HPV45 | E1 | 11 | 561 |
| HPV45 | E1 | 11 | 51 |
| HPV45 | E1 | 9 | 233 |
| HPV45 | E1 | 11 | 338 |
| HPV45 | E1 | 10 | 491 |
| HPV45 | E1 | 11 | 491 |
| HPV45 | E1 | 8 | 268 |
| HPV45 | E1 | 11 | 268 |
| HPV45 | E1 | 10 | 555 |
| HPV45 | E1 | 11 | 555 |
| HPV45 | E1 | 11 | 466 |
| HPV45 | E1 | 9 | 32 |
| HPV45 | E1 | 8 | 447 |
| HPV45 | E1 | 10 | 447 |
| HPV45 | E1 | 9 | 492 |
| HPV45 | E1 | 10 | 492 |
| HPV45 | E1 | 8 | 538 |
| HPV45 | E1 | 8 | 116 |
| HPV45 | E1 | 9 | 116 |
| HPV45 | E1 | 10 | 116 |
| HPV45 | E1 | 11 | 116 |
| HPV45 | E1 | 10 | 184 |
| HPV45 | E1 | 8 | 197 |
| HPV45 | E1 | 9 | 197 |
| HPV45 | E1 | 10 | 603 |
| HPV45 | E1 | 10 | 275 |
| HPV45 | E1 | 11 | 275 |
| HPV45 | E1 | 9 | 633 |
| HPV45 | E1 | 8 | 396 |
| HPV45 | E1 | 9 | 396 |
| HPV45 | E1 | 10 | 396 |
| HPV45 | E1 | 11 | 396 |
| HPV45 | E1 | 8 | 205 |
| HPV45 | E1 | 11 | 565 |
| HPV45 | E1 | 8 | 285 |
| HPV45 | E1 | 9 | 425 |
| HPV45 | E1 | 8 | 304 |
| HPV45 | E1 | 10 | 304 |
| HPV45 | E1 | 8 | 387 |
| HPV45 | E1 | 10 | 387 |
| HPV45 | E1 | 8 | 476 |
| HPV45 | E1 | 10 | 476 |
| HPV45 | E1 | 11 | 476 |
| HPV45 | E1 | 10 | 245 |
| HPV45 | E1 | 11 | 245 |
| HPV45 | E1 | 10 | 223 |
| HPV45 | E1 | 8 | 510 |
| HPV45 | E1 | 10 | 510 |
| HPV45 | E1 | 8 | 375 |
| HPV45 | E1 | 9 | 375 |
| HPV45 | E1 | 10 | 375 |
| HPV45 | E1 | 11 | 375 |
| HPV45 | E1 | 10 | 269 |
| HPV45 | E1 | 8 | 201 |
| HPV45 | E1 | 11 | 260 |
| HPV45 | E1 | 11 | 514 |
| HPV45 | E1 | 10 | 533 |
| HPV45 | E1 | 11 | 533 |
| HPV45 | E1 | 10 | 613 |
| HPV45 | E1 | 11 | 69 |
| NPV45 | E1 | 9 | 129 |
| HPV45 | E1 | 8 | 299 |
| HPV45 | E1 | 8 | 247 |
| HPV45 | E1 | 9 | 247 |
| HPV45 | E1 | 10 | 247 |
| HPV45 | E1 | 8 | 267 |
| HPV45 | E1 | 9 | 267 |
| HPV45 | E1 | 11 | 84 |
| HPV45 | E1 | 8 | 190 |
| HPV45 | E1 | 9 | 190 |
| HPV45 | E1 | 10 | 190 |
| HPV45 | E1 | 8 | 271 |
| HPV45 | E1 | 10 | 271 |
| HPV45 | E1 | 9 | 556 |
| HPV45 | E1 | 10 | 556 |
| HPV45 | E1 | 10 | 467 |
| HPV45 | E1 | 8 | 350 |
| HPV45 | E1 | 9 | 350 |
| HPV45 | E1 | 8 | 210 |
| HPV45 | E1 | 10 | 210 |
| HPV45 | E1 | 11 | 210 |
| HPV45 | E1 | 10 | 103 |
| HPV45 | E1 | 8 | 362 |
| HPV45 | E1 | 9 | 362 |
| HPV45 | E1 | 11 | 362 |
| HPV45 | E1 | 8 | 557 |
| HPV45 | E1 | 9 | 557 |
| HPV45 | E1 | 9 | 215 |
| HPV45 | E1 | 9 | 368 |
| HPV45 | E1 | 11 | 231 |
| HPV45 | E1 | 8 | 401 |
| HPV45 | E1 | 10 | 401 |
| HPV45 | E1 | 11 | 401 |
| HPV45 | E1 | 9 | 200 |
| HPV45 | E1 | 9 | 298 |
| HPV45 | E1 | 10 | 481 |
| HPV45 | E1 | 8 | 415 |
| HPV45 | E1 | 11 | 415 |
| HPV45 | E1 | 9 | 154 |
| HPV45 | E1 | 8 | 174 |
| HPV45 | E1 | 9 | 464 |
| HPV45 | E1 | 8 | 389 |
| HPV45 | E1 | 11 | 389 |
| HPV45 | E1 | 10 | 77 |
| HPV45 | E1 | 11 | 77 |
| HPV45 | E1 | 8 | 598 |
| HPV45 | E1 | 9 | 598 |
| HPV45 | E1 | 11 | 598 |
| HPV45 | E1 | 10 | 360 |
| HPV45 | E1 | 11 | 360 |
| HPV45 | E1 | 11 | 347 |
| HPV45 | E1 | 11 | 590 |
| HPV45 | E1 | 9 | 560 |
| HPV45 | E1 | 8 | 414 |
| HPV45 | E1 | 9 | 414 |
| HPV45 | E1 | 8 | 119 |
| HPV45 | E1 | 9 | 119 |
| HPV45 | E1 | 10 | 119 |
| HPV45 | E1 | 10 | 498 |
| HPV45 | E1 | 9 | 379 |
| HPV45 | E1 | 11 | 473 |
| HPV45 | E1 | 11 | 152 |
| HPV45 | E1 | 9 | 563 |
| HPV45 | E1 | 8 | 471 |
| HPV45 | E1 | 9 | 471 |
| HPV45 | E1 | 10 | 586 |
| HPV45 | E1 | 11 | 554 |
| HPV45 | E1 | 8 | 537 |
| HPV45 | E1 | 9 | 537 |
| HPV45 | E1 | 8 | 434 |
| HPV45 | E1 | 8 | 505 |
| HPV45 | E1 | 8 | 238 |
| HPV45 | E1 | 8 | 593 |

TABLE XVI-continued

HLA-A3 Motif Peptides

| 1 | 2 | 3 | 4 |
|---|---|---|---|
| HPV45 | E1 | 11 | 593 |
| HPV45 | E1 | 9 | 60 |
| HPV45 | E1 | 11 | 60 |
| HPV45 | E1 | 9 | 391 |
| HPV45 | E1 | 8 | 192 |
| HPV45 | E1 | 11 | 192 |
| HPV45 | E1 | 10 | 437 |
| HPV45 | E1 | 8 | 442 |
| HPV45 | E1 | 10 | 442 |
| HPV45 | E1 | 11 | 442 |
| HPV45 | E1 | 9 | 374 |
| HPV45 | E1 | 10 | 374 |
| HPV45 | E1 | 11 | 374 |
| HPV45 | E1 | 8 | 54 |
| HPV45 | E1 | 11 | 102 |
| HPV45 | E1 | 9 | 412 |
| HPV45 | E1 | 10 | 412 |
| HPV45 | E1 | 11 | 412 |
| HPV45 | E1 | 11 | 165 |
| HPV45 | E1 | 8 | 80 |
| HPV45 | E1 | 9 | 80 |
| HPV45 | E1 | 10 | 80 |
| HPV45 | E1 | 11 | 80 |
| HPV45 | E1 | 8 | 148 |
| HPV45 | E1 | 8 | 451 |
| HPV45 | E1 | 11 | 612 |
| HPV45 | E1 | 10 | 128 |
| HPV45 | E1 | 11 | 112 |
| HPV45 | E1 | 8 | 306 |
| HPV45 | E1 | 10 | 306 |
| HPV45 | E1 | 11 | 306 |
| HPV45 | E1 | 9 | 608 |
| HPV45 | E1 | 9 | 575 |
| HPV45 | E1 | 10 | 575 |
| HPV45 | E1 | 11 | 575 |
| HPV45 | E1 | 8 | 33 |
| HPV45 | E1 | 8 | 366 |
| HPV45 | E1 | 11 | 366 |
| HPV45 | E1 | 8 | 351 |
| HPV45 | E1 | 10 | 172 |
| HPV45 | E1 | 9 | 482 |
| HPV45 | E1 | 9 | 448 |
| HPV45 | E1 | 11 | 448 |
| HPV45 | E1 | 9 | 211 |
| HPV45 | E1 | 10 | 211 |
| HPV45 | E1 | 8 | 493 |
| HPV45 | E1 | 9 | 493 |
| HPV45 | E1 | 10 | 326 |
| HPV45 | E1 | 9 | 167 |
| HPV45 | E1 | 8 | 120 |
| HPV45 | E1 | 9 | 120 |
| HPV45 | E1 | 11 | 120 |
| HPV45 | E1 | 10 | 135 |
| HPV45 | E1 | 11 | 135 |
| HPV45 | E1 | 11 | 56 |
| HPV45 | E1 | 11 | 183 |
| HPV45 | E1 | 8 | 117 |
| HPV45 | E1 | 9 | 117 |
| HPV45 | E1 | 10 | 117 |
| HPV45 | E1 | 11 | 117 |
| HPV45 | E1 | 11 | 171 |
| HPV45 | E1 | 10 | 166 |
| HPV45 | E1 | 9 | 307 |
| HPV45 | E1 | 10 | 307 |
| HPV45 | E1 | 8 | 308 |
| HPV45 | E1 | 9 | 308 |
| HPV45 | E1 | 9 | 104 |
| HPV45 | E1 | 8 | 65 |
| HPV45 | E1 | 9 | 296 |
| HPV45 | E1 | 11 | 296 |
| HPV45 | E1 | 8 | 225 |
| HPV45 | E1 | 10 | 225 |
| HPV45 | E1 | 9 | 520 |
| HPV45 | E1 | 11 | 520 |
| HPV45 | E1 | 8 | 363 |
| HPV45 | E1 | 10 | 363 |
| HPV45 | E1 | 11 | 363 |
| HPV45 | E1 | 8 | 213 |
| HPV45 | E1 | 11 | 213 |
| HPV45 | E1 | 10 | 41 |
| HPV45 | E1 | 8 | 227 |
| HPV45 | E1 | 11 | 631 |
| HPV45 | E1 | 8 | 580 |
| HPV45 | E1 | 10 | 580 |
| HPV45 | E1 | 8 | 12 |
| HPV45 | E1 | 10 | 474 |
| HPV45 | E1 | 8 | 43 |
| HPV45 | E1 | 9 | 246 |
| HPV45 | E1 | 10 | 246 |
| HPV45 | E1 | 11 | 246 |
| HPV45 | E1 | 8 | 558 |
| HPV45 | E1 | 11 | 558 |
| HPV45 | E1 | 9 | 224 |
| HPV45 | E1 | 11 | 224 |
| HPV45 | E1 | 11 | 239 |
| HPV45 | E1 | 11 | 282 |
| HPV45 | E1 | 8 | 577 |
| HPV45 | E1 | 9 | 577 |
| HPV45 | E1 | 11 | 577 |
| HPV45 | E1 | 8 | 309 |
| HPV45 | E1 | 10 | 240 |
| HPV45 | E1 | 10 | 283 |
| HPV45 | E1 | 9 | 511 |
| HPV45 | E1 | 11 | 178 |
| HPV45 | E1 | 8 | 105 |
| HPV45 | E1 | 10 | 203 |
| HPV45 | E1 | 8 | 578 |
| HPV45 | E1 | 10 | 578 |
| HPV45 | E1 | 10 | 31 |
| HPV45 | E1 | 8 | 81 |
| HPV45 | E1 | 9 | 81 |
| HPV45 | E1 | 10 | 81 |
| HPV45 | E1 | 8 | 266 |
| HPV45 | E1 | 9 | 266 |
| HPV45 | E1 | 10 | 266 |
| HPV45 | E1 | 8 | 400 |
| HPV45 | E1 | 9 | 400 |
| HPV45 | E1 | 11 | 400 |
| HPV45 | E1 | 11 | 325 |
| HPV45 | E1 | 8 | 576 |
| HPV45 | E1 | 9 | 576 |
| HPV45 | E1 | 10 | 576 |
| HPV45 | E1 | 10 | 17 |
| HPV45 | E1 | 11 | 17 |
| HPV45 | E1 | 10 | 264 |
| HPV45 | E1 | 11 | 264 |
| HPV45 | E1 | 8 | 418 |
| HPV45 | E1 | 10 | 332 |
| HPV45 | E1 | 9 | 502 |
| HPV45 | E1 | 11 | 502 |
| HPV45 | E1 | 9 | 522 |
| HPV45 | E1 | 11 | 522 |
| HPV45 | E1 | 10 | 254 |
| HPV45 | E1 | 11 | 372 |
| HPV45 | E1 | 9 | 524 |
| HPV45 | E1 | 8 | 478 |
| HPV45 | E1 | 9 | 478 |
| HPV45 | E1 | 8 | 137 |
| HPV45 | E1 | 9 | 137 |
| HPV45 | E1 | 10 | 208 |
| HPV45 | E1 | 8 | 469 |
| HPV45 | E1 | 10 | 469 |
| HPV45 | E1 | 11 | 469 |
| HPV45 | E1 | 9 | 571 |
| HPV45 | E1 | 11 | 571 |
| HPV45 | E1 | 10 | 394 |
| HPV45 | E1 | 11 | 394 |
| HPV45 | E2 | 10 | 156 |
| HPV45 | E2 | 11 | 156 |
| HPV45 | E2 | 9 | 157 |

TABLE XVI-continued

HLA-A3 Motif Peptides

| 1 | 2 | 3 | 4 |
|---|---|---|---|
| HPV45 | E2 | 10 | 157 |
| HPV45 | E2 | 9 | 78 |
| HPV45 | E2 | 9 | 47 |
| HPV45 | E2 | 9 | 84 |
| HPV45 | E2 | 10 | 84 |
| HPV45 | E2 | 9 | 16 |
| HPV45 | E2 | 10 | 16 |
| HPV45 | E2 | 9 | 226 |
| HPV45 | E2 | 9 | 234 |
| HPV45 | E2 | 10 | 216 |
| HPV45 | E2 | 11 | 216 |
| HPV45 | E2 | 10 | 115 |
| HPV45 | E2 | 8 | 254 |
| HPV45 | E2 | 10 | 254 |
| HPV45 | E2 | 8 | 305 |
| HPV45 | E2 | 9 | 305 |
| HPV45 | E2 | 10 | 305 |
| HPV45 | E2 | 11 | 134 |
| HPV45 | E2 | 10 | 286 |
| HPV45 | E2 | 8 | 274 |
| HPV45 | E2 | 9 | 274 |
| HPV45 | E2 | 10 | 274 |
| HPV45 | E2 | 11 | 274 |
| HPV45 | E2 | 10 | 207 |
| HPV45 | E2 | 8 | 158 |
| HPV45 | E2 | 9 | 158 |
| HPV45 | E2 | 11 | 158 |
| HPV45 | E2 | 11 | 211 |
| HPV45 | E2 | 10 | 169 |
| HPV45 | E2 | 11 | 169 |
| HPV45 | E2 | 10 | 128 |
| HPV45 | E2 | 8 | 31 |
| HPV45 | E2 | 11 | 28 |
| HPV45 | E2 | 8 | 171 |
| HPV45 | E2 | 9 | 171 |
| HPV45 | E2 | 10 | 212 |
| HPV45 | E2 | 10 | 80 |
| HPV45 | E2 | 11 | 106 |
| HPV45 | E2 | 9 | 8 |
| HPV45 | E2 | 9 | 148 |
| HPV45 | E2 | 10 | 148 |
| HPV45 | E2 | 11 | 127 |
| HPV45 | E2 | 10 | 50 |
| HPV45 | E2 | 10 | 298 |
| HPV45 | E2 | 11 | 298 |
| HPV45 | E2 | 9 | 170 |
| HPV45 | E2 | 10 | 170 |
| HPV45 | E2 | 8 | 119 |
| HPV45 | E2 | 9 | 119 |
| HPV45 | E2 | 8 | 150 |
| HPV45 | E2 | 9 | 255 |
| HPV45 | E2 | 11 | 237 |
| HPV45 | E2 | 8 | 225 |
| HPV45 | E2 | 10 | 225 |
| HPV45 | E2 | 8 | 55 |
| HPV45 | E2 | 9 | 261 |
| HPV45 | E2 | 8 | 242 |
| HPV45 | E2 | 9 | 242 |
| HPV45 | E2 | 11 | 242 |
| HPV45 | E2 | 10 | 295 |
| HPV45 | E2 | 8 | 124 |
| HPV45 | E2 | 8 | 293 |
| HPV45 | E2 | 10 | 21 |
| HPV45 | E2 | 8 | 48 |
| HPV45 | E2 | 8 | 70 |
| HPV45 | E2 | 9 | 70 |
| HPV45 | E2 | 8 | 36 |
| HPV45 | E2 | 9 | 146 |
| HPV45 | E2 | 11 | 146 |
| HPV45 | E2 | 8 | 219 |
| HPV45 | E2 | 11 | 74 |
| HPV45 | E2 | 8 | 77 |
| HPV45 | E2 | 10 | 77 |
| HPV45 | E2 | 8 | 304 |
| HPV45 | E2 | 9 | 304 |
| HPV45 | E2 | 10 | 304 |
| HPV45 | E2 | 11 | 177 |
| HPV45 | E2 | 8 | 168 |
| HPV45 | E2 | 11 | 168 |
| HPV45 | E2 | 9 | 30 |
| HPV45 | E2 | 8 | 297 |
| HPV45 | E2 | 11 | 297 |
| HPV45 | E2 | 9 | 118 |
| HPV45 | E2 | 10 | 118 |
| HPV45 | E2 | 8 | 86 |
| HPV45 | E2 | 11 | 20 |
| HPV45 | E2 | 8 | 154 |
| HPV45 | E2 | 9 | 232 |
| HPV45 | E2 | 11 | 232 |
| HPV45 | E2 | 11 | 121 |
| HPV45 | E2 | 9 | 273 |
| HPV45 | E2 | 10 | 273 |
| HPV45 | E2 | 11 | 273 |
| HPV45 | E2 | 9 | 22 |
| HPV45 | E2 | 11 | 49 |
| HPV45 | E2 | 10 | 41 |
| HPV45 | E2 | 10 | 272 |
| HPV45 | E2 | 11 | 272 |
| HPV45 | E2 | 11 | 14 |
| HPV45 | E2 | 11 | 10 |
| HPV45 | E2 | 8 | 256 |
| HPV45 | E2 | 11 | 336 |
| HPV45 | E2 | 10 | 83 |
| HPV45 | E2 | 11 | 83 |
| HPV45 | E2 | 11 | 206 |
| HPV45 | E2 | 8 | 46 |
| HPV45 | E2 | 10 | 46 |
| HPV45 | E2 | 8 | 69 |
| HPV45 | E2 | 9 | 69 |
| HPV45 | E2 | 10 | 69 |
| HPV45 | E2 | 9 | 341 |
| HPV45 | E2 | 8 | 301 |
| HPV45 | E2 | 9 | 301 |
| HPV45 | E2 | 11 | 301 |
| HPV45 | E2 | 9 | 187 |
| HPV45 | E2 | 11 | 33 |
| HPV45 | E2 | 9 | 357 |
| HPV45 | E2 | 8 | 109 |
| HPV45 | E2 | 9 | 109 |
| HPV45 | E2 | 10 | 109 |
| HPV45 | E2 | 9 | 332 |
| HPV45 | E2 | 9 | 289 |
| HPV45 | E2 | 9 | 292 |
| HPV45 | E2 | 8 | 67 |
| HPV45 | E2 | 9 | 67 |
| HPV45 | E2 | 10 | 67 |
| HPV45 | E2 | 11 | 67 |
| HPV45 | E2 | 11 | 271 |
| HPV45 | E2 | 10 | 112 |
| HPV45 | E2 | 8 | 114 |
| HPV45 | E2 | 11 | 114 |
| HPV45 | E2 | 8 | 253 |
| HPV45 | E2 | 9 | 253 |
| HPV45 | E2 | 11 | 253 |
| HPV45 | E2 | 8 | 18 |
| HPV45 | E2 | 8 | 177 |
| HPV45 | E2 | 9 | 177 |
| HPV45 | E2 | 9 | 35 |
| HPV45 | E2 | 8 | 218 |
| HPV45 | E2 | 9 | 218 |
| HPV45 | E2 | 8 | 40 |
| HPV45 | E2 | 11 | 40 |
| HPV45 | E2 | 11 | 222 |
| HPV45 | E2 | 8 | 82 |
| HPV45 | E2 | 11 | 82 |
| HPV45 | E2 | 9 | 244 |
| HPV45 | E2 | 10 | 4 |
| HPV45 | E2 | 10 | 63 |
| HPV45 | E2 | 8 | 43 |
| HPV45 | E2 | 10 | 43 |

TABLE XVI-continued

HLA-A3 Motif Peptides

| 1 | 2 | 3 | 4 |
|---|---|---|---|
| HPV45 | E2 | 11 | 43 |
| HPV45 | E2 | 8 | 309 |
| HPV45 | E2 | 9 | 309 |
| HPV45 | E2 | 8 | 13 |
| HPV45 | E2 | 10 | 15 |
| HPV45 | E2 | 11 | 15 |
| HPV45 | E2 | 11 | 215 |
| HPV45 | E2 | 9 | 287 |
| HPV45 | E2 | 11 | 287 |
| HPV45 | E2 | 8 | 302 |
| HPV45 | E2 | 10 | 302 |
| HPV45 | E2 | 11 | 302 |
| HPV45 | E2 | 8 | 9 |
| HPV45 | E2 | 8 | 275 |
| HPV45 | E2 | 9 | 275 |
| HPV45 | E2 | 10 | 275 |
| HPV45 | E2 | 11 | 321 |
| HPV45 | E2 | 9 | 208 |
| HPV45 | E2 | 8 | 276 |
| HPV45 | E2 | 9 | 276 |
| HPV45 | E2 | 8 | 227 |
| HPV45 | E2 | 10 | 322 |
| HPV45 | E2 | 8 | 235 |
| HPV45 | E2 | 8 | 358 |
| HPV45 | E2 | 11 | 155 |
| HPV45 | E2 | 9 | 51 |
| HPV45 | E2 | 8 | 233 |
| HPV45 | E2 | 10 | 233 |
| HPV45 | E2 | 8 | 333 |
| HPV45 | E2 | 8 | 149 |
| HPV45 | E2 | 9 | 149 |
| HPV45 | E2 | 8 | 209 |
| MPV45 | E2 | 8 | 277 |
| HPV45 | E2 | 8 | 290 |
| HPV45 | E2 | 11 | 290 |
| HPV45 | E2 | 8 | 172 |
| HPV45 | E2 | 10 | 122 |
| HPV45 | E2 | 9 | 213 |
| HPV45 | E2 | 10 | 337 |
| HPV45 | E2 | 11 | 285 |
| HPV45 | E2 | 8 | 214 |
| HPV45 | E2 | 8 | 159 |
| HPV45 | E2 | 10 | 159 |
| HPV45 | E2 | 9 | 338 |
| HPV45 | E2 | 9 | 54 |
| HPV45 | E2 | 11 | 54 |
| HPV45 | E2 | 8 | 138 |
| HPV45 | E2 | 10 | 152 |
| HPV45 | E2 | 11 | 185 |
| HPV45 | E2 | 9 | 166 |
| HPV45 | E2 | 10 | 166 |
| HPV45 | E2 | 10 | 145 |
| HPV45 | E2 | 9 | 317 |
| HPV45 | E2 | 10 | 175 |
| HPV45 | E2 | 11 | 175 |
| HPV45 | E2 | 8 | 137 |
| HPV45 | E2 | 9 | 137 |
| HPV45 | E6 | 9 | 63 |
| HPV45 | E6 | 10 | 63 |
| HPV45 | E6 | 8 | 64 |
| HPV45 | E6 | 9 | 64 |
| HPV45 | E6 | 11 | 54 |
| HPV45 | E6 | 11 | 31 |
| HPV45 | E6 | 9 | 48 |
| HPV45 | E6 | 10 | 48 |
| HPV45 | E6 | 9 | 37 |
| HPV45 | E6 | 11 | 37 |
| HPV45 | E6 | 9 | 141 |
| HPV45 | E6 | 11 | 141 |
| HPV45 | E6 | 8 | 142 |
| HPV45 | E6 | 10 | 142 |
| HPV45 | E6 | 11 | 142 |
| HPV45 | E6 | 8 | 59 |
| HPV45 | E6 | 9 | 59 |
| HPV45 | E6 | 9 | 58 |
| HPV45 | E6 | 11 | 105 |
| HPV45 | E6 | 10 | 32 |
| HPV45 | E6 | 9 | 58 |
| HPV45 | E6 | 10 | 58 |
| HPV45 | E6 | 8 | 5 |
| HPV45 | E6 | 9 | 5 |
| HPV45 | E6 | 10 | 70 |
| HPV45 | E6 | 11 | 70 |
| HPV45 | E6 | 11 | 51 |
| HPV45 | E6 | 8 | 27 |
| HPV45 | E6 | 10 | 27 |
| HPV45 | E6 | 11 | 27 |
| HPV45 | E6 | 10 | 77 |
| HPV45 | E6 | 8 | 97 |
| HPV45 | E6 | 11 | 97 |
| HPV45 | E6 | 8 | 43 |
| HPV45 | E6 | 11 | 43 |
| HPV45 | E6 | 10 | 47 |
| HPV45 | E6 | 11 | 47 |
| HPV45 | E6 | 9 | 4 |
| HPV45 | E6 | 10 | 4 |
| HPV45 | E6 | 9 | 53 |
| HPV45 | E6 | 10 | 53 |
| HPV45 | E6 | 11 | 53 |
| HPV45 | E6 | 8 | 120 |
| HPV45 | E6 | 9 | 120 |
| HPV45 | E6 | 8 | 128 |
| HPV45 | E6 | 8 | 30 |
| HPV45 | E6 | 8 | 50 |
| HPV45 | E6 | 8 | 59 |
| HPV45 | E6 | 11 | 69 |
| HPV45 | E6 | 8 | 54 |
| HPV45 | E6 | 9 | 54 |
| HPV45 | E6 | 10 | 54 |
| HPV45 | E6 | 11 | 54 |
| HPV45 | E6 | 10 | 36 |
| HPV45 | E6 | 8 | 67 |
| HPV45 | E6 | 10 | 67 |
| HPV45 | E6 | 10 | 122 |
| HPV45 | E6 | 8 | 50 |
| HPV45 | E6 | 8 | 92 |
| HPV45 | E6 | 10 | 52 |
| HPV45 | E6 | 11 | 52 |
| HPV45 | E6 | 9 | 102 |
| HPV45 | E6 | 10 | 101 |
| HPV45 | E6 | 10 | 1 |
| HPV45 | E6 | 8 | 100 |
| HPV45 | E6 | 11 | 100 |
| HPV45 | E6 | 10 | 83 |
| HPV45 | E6 | 8 | 139 |
| HPV45 | E6 | 11 | 139 |
| HPV45 | E6 | 10 | 95 |
| HPV45 | E6 | 10 | 22 |
| HPV45 | E6 | 9 | 114 |
| HPV45 | E6 | 11 | 114 |
| HPV45 | E6 | 8 | 111 |
| HPV45 | E6 | 9 | 111 |
| HPV45 | E6 | 10 | 111 |
| HPV45 | E6 | 8 | 144 |
| HPV45 | E6 | 9 | 144 |
| HPV45 | E6 | 10 | 144 |
| HPV45 | E6 | 11 | 144 |
| HPV45 | E6 | 9 | 137 |
| HPV45 | E6 | 10 | 137 |
| HPV45 | E6 | 9 | 26 |
| HPV45 | E6 | 11 | 25 |
| HPV45 | E6 | 8 | 46 |
| HPV45 | E6 | 11 | 46 |
| HPV45 | E6 | 9 | 107 |
| HPV45 | E6 | 11 | 107 |
| HPV45 | E6 | 8 | 57 |
| HPV45 | E6 | 10 | 57 |
| HPV45 | E6 | 11 | 57 |
| HPV45 | E6 | 8 | 3 |
| HPV45 | E6 | 10 | 3 |

TABLE XVI-continued

HLA-A3 Motif Peptides

| 1 | 2 | 3 | 4 |
|---|---|---|---|
| HPV45 | E6 | 11 | 3 |
| HPV45 | E6 | 9 | 126 |
| HPV45 | E6 | 10 | 126 |
| HPV45 | E6 | 11 | 135 |
| HPV45 | E6 | 8 | 74 |
| HPV45 | E6 | 8 | 41 |
| HPV45 | E6 | 9 | 41 |
| HPV45 | E6 | 10 | 41 |
| HPV45 | E6 | 8 | 29 |
| HPV45 | E6 | 9 | 29 |
| HPV45 | E6 | 8 | 24 |
| HPV45 | E6 | 11 | 24 |
| HPV45 | E6 | 9 | 84 |
| HPV45 | E6 | 10 | 140 |
| HPV45 | E6 | 11 | 89 |
| HPV45 | E6 | 8 | 38 |
| HPV45 | E6 | 10 | 38 |
| HPV45 | E6 | 11 | 38 |
| HPV45 | E6 | 9 | 23 |
| HPV45 | E6 | 9 | 28 |
| HPV45 | E6 | 10 | 28 |
| HPV45 | E6 | 10 | 62 |
| HPV45 | E6 | 11 | 62 |
| HPV45 | E6 | 8 | 34 |
| HPV45 | E6 | 8 | 72 |
| HPV45 | E6 | 9 | 72 |
| HPV45 | E6 | 10 | 72 |
| HPV45 | E7 | 11 | 81 |
| HPV45 | E7 | 11 | 42 |
| HPV45 | E7 | 9 | 5 |
| HPV45 | E7 | 9 | 64 |
| HPV45 | E7 | 10 | 82 |
| HPV45 | E7 | 10 | 43 |
| HPV45 | E7 | 11 | 43 |
| HPV45 | E7 | 9 | 83 |
| HPV45 | E7 | 8 | 41 |
| HPV45 | E7 | 10 | 20 |
| HPV45 | E7 | 8 | 74 |
| HPV45 | E7 | 9 | 34 |
| HPV45 | E7 | 8 | 78 |
| HPV45 | E7 | 9 | 44 |
| HPV45 | E7 | 10 | 44 |
| HPV45 | E7 | 11 | 44 |
| HPV45 | E7 | 8 | 47 |
| HPV45 | E7 | 9 | 47 |
| HPV45 | E7 | 11 | 62 |
| HPV45 | E7 | 8 | 61 |
| HPV45 | E7 | 10 | 63 |
| HPV45 | E7 | 9 | 21 |
| HPV45 | E7 | 8 | 90 |
| HPV45 | E7 | 11 | 32 |
| HPV45 | E7 | 9 | 95 |
| HPV45 | E7 | 11 | 75 |
| HPV45 | E7 | 9 | 39 |
| HPV45 | E7 | 10 | 39 |
| HPV45 | E7 | 9 | 51 |
| HPV45 | E7 | 10 | 51 |
| HPV45 | E7 | 11 | 51 |
| HPV45 | E7 | 9 | 89 |
| HPV45 | E7 | 11 | 49 |
| HPV45 | E7 | 8 | 54 |
| HPV45 | E7 | 10 | 5 |
| HPV45 | E7 | 10 | 72 |
| HPV45 | E7 | 8 | 96 |
| HPV45 | E7 | 11 | 93 |
| HPV45 | E7 | 8 | 7 |
| HPV45 | E7 | 10 | 94 |
| HPV45 | E7 | 10 | 76 |
| HPV45 | E7 | 8 | 65 |
| HPV45 | E7 | 8 | 45 |
| HPV45 | E7 | 9 | 45 |
| HPV45 | E7 | 10 | 45 |
| HPV45 | E7 | 11 | 45 |
| HPV45 | L1 | 9 | 517 |
| HPV45 | L1 | 11 | 517 |
| HPV45 | L1 | 11 | 161 |
| HPV45 | L1 | 9 | 128 |
| HPV45 | L1 | 9 | 266 |
| HPV45 | L1 | 10 | 266 |
| HPV45 | L1 | 9 | 83 |
| HPV45 | L1 | 8 | 191 |
| HPV45 | L1 | 8 | 103 |
| HPV45 | L1 | 11 | 28 |
| HPV45 | L1 | 11 | 234 |
| HPV45 | L1 | 9 | 523 |
| HPV45 | L1 | 11 | 523 |
| HPV45 | L1 | 11 | 375 |
| HPV45 | L1 | 8 | 518 |
| HPV45 | L1 | 10 | 518 |
| HPV45 | L1 | 11 | 518 |
| HPV45 | L1 | 10 | 162 |
| HPV45 | L1 | 8 | 164 |
| HPV45 | L1 | 8 | 88 |
| HPV45 | L1 | 10 | 88 |
| HPV45 | L1 | 11 | 88 |
| HPV45 | L1 | 8 | 184 |
| HPV45 | L1 | 8 | 276 |
| HPV45 | L1 | 9 | 276 |
| HPV45 | L1 | 10 | 276 |
| HPV45 | L1 | 11 | 276 |
| HPV45 | L1 | 8 | 129 |
| HPV45 | L1 | 8 | 188 |
| HPV45 | L1 | 10 | 188 |
| HPV45 | L1 | 11 | 188 |
| HPV45 | L1 | 8 | 211 |
| HPV45 | L1 | 8 | 154 |
| HPV45 | L1 | 9 | 154 |
| HPV45 | L1 | 11 | 154 |
| HPV45 | L1 | 10 | 51 |
| HPV45 | L1 | 11 | 51 |
| HPV45 | L1 | 9 | 236 |
| HPV45 | L1 | 9 | 224 |
| HPV45 | L1 | 11 | 224 |
| HPV45 | L1 | 8 | 250 |
| HPV45 | L1 | 9 | 250 |
| HPV45 | L1 | 9 | 488 |
| HPV45 | L1 | 10 | 488 |
| HPV45 | L1 | 11 | 488 |
| HPV45 | L1 | 9 | 301 |
| HPV45 | L1 | 9 | 226 |
| HPV45 | L1 | 8 | 271 |
| HPV45 | L1 | 9 | 271 |
| HPV45 | L1 | 9 | 332 |
| HPV45 | L1 | 11 | 114 |
| HPV45 | L1 | 8 | 155 |
| HPV45 | L1 | 10 | 155 |
| HPV45 | L1 | 9 | 229 |
| HPV45 | L1 | 11 | 461 |
| HPV45 | L1 | 8 | 296 |
| HPV45 | L1 | 10 | 296 |
| HPV45 | L1 | 10 | 446 |
| HPV45 | L1 | 10 | 169 |
| HPV45 | L1 | 11 | 169 |
| HPV45 | L1 | 10 | 223 |
| HPV45 | L1 | 8 | 157 |
| HPV45 | L1 | 8 | 313 |
| HPV45 | L1 | 8 | 121 |
| HPV45 | L1 | 8 | 283 |
| HPV45 | L1 | 9 | 283 |
| HPV45 | L1 | 9 | 275 |
| HPV45 | L1 | 10 | 275 |
| HPV45 | L1 | 11 | 275 |
| HPV45 | L1 | 10 | 274 |
| HPV45 | L1 | 11 | 274 |
| HPV45 | L1 | 9 | 110 |
| HPV45 | L1 | 8 | 14 |
| HPV45 | L1 | 11 | 14 |
| HPV45 | L1 | 8 | 24 |
| HPV45 | L1 | 8 | 498 |
| HPV45 | L1 | 9 | 498 |

TABLE XVI-continued

HLA-A3 Motif Peptides

| 1 | 2 | 3 | 4 |
|---|---|---|---|
| HPV45 | L1 | 10 | 498 |
| HPV45 | L1 | 8 | 485 |
| HPV45 | L1 | 8 | 237 |
| HPV45 | L1 | 11 | 450 |
| HPV45 | L1 | 9 | 359 |
| HPV45 | L1 | 10 | 82 |
| HPV45 | L1 | 9 | 187 |
| HPV45 | L1 | 11 | 187 |
| HPV45 | L1 | 9 | 210 |
| HPV45 | L1 | 8 | 225 |
| HPV45 | L1 | 10 | 225 |
| HPV45 | L1 | 9 | 270 |
| HPV45 | L1 | 10 | 270 |
| HPV45 | L1 | 9 | 295 |
| HPV45 | L1 | 11 | 295 |
| HPV45 | L1 | 9 | 351 |
| HPV45 | L1 | 9 | 141 |
| HPV45 | L1 | 10 | 141 |
| HPV45 | L1 | 8 | 11 |
| HPV45 | L1 | 11 | 503 |
| HPV45 | L1 | 8 | 143 |
| HPV45 | L1 | 10 | 143 |
| HPV45 | L1 | 11 | 326 |
| HPV45 | L1 | 8 | 9 |
| HPV45 | L1 | 9 | 396 |
| HPV45 | L1 | 11 | 396 |
| HPV45 | L1 | 8 | 251 |
| HPV45 | L1 | 11 | 251 |
| HPV45 | L1 | 8 | 352 |
| HPV45 | L1 | 9 | 13 |
| HPV45 | L1 | 9 | 23 |
| HPV45 | L1 | 11 | 405 |
| HPV45 | L1 | 9 | 59 |
| HPV45 | L1 | 8 | 142 |
| HPV45 | L1 | 9 | 142 |
| HPV45 | L1 | 11 | 142 |
| HPV45 | L1 | 8 | 510 |
| HPV45 | L1 | 9 | 510 |
| HPV45 | L1 | 10 | 12 |
| HPV45 | L1 | 11 | 11 |
| HPV45 | L1 | 10 | 5 |
| HPV45 | L1 | 11 | 185 |
| HPV45 | L1 | 10 | 411 |
| HPV45 | L1 | 9 | 328 |
| HPV45 | L1 | 11 | 328 |
| HPV45 | L1 | 8 | 460 |
| HPV45 | L1 | 10 | 109 |
| HPV45 | L1 | 8 | 389 |
| HPV45 | L1 | 9 | 497 |
| HPV45 | L1 | 10 | 497 |
| HPV45 | L1 | 11 | 497 |
| HPV45 | L1 | 9 | 484 |
| HPV45 | L1 | 8 | 475 |
| HPV45 | L1 | 10 | 475 |
| HPV45 | L1 | 11 | 475 |
| HPV45 | L1 | 8 | 198 |
| HPV45 | L1 | 8 | 305 |
| HPV45 | L1 | 8 | 152 |
| HPV45 | L1 | 9 | 152 |
| HPV45 | L1 | 10 | 152 |
| HPV45 | L1 | 11 | 152 |
| HPV45 | L1 | 10 | 473 |
| HPV45 | L1 | 8 | 91 |
| HPV45 | L1 | 10 | 91 |
| HPV45 | L1 | 11 | 91 |
| HPV45 | L1 | 9 | 183 |
| HPV45 | L1 | 8 | 408 |
| HPV45 | L1 | 8 | 153 |
| HPV45 | L1 | 9 | 153 |
| HPV45 | L1 | 10 | 153 |
| HPV45 | L1 | 9 | 249 |
| HPV45 | L1 | 10 | 249 |
| HPV45 | L1 | 8 | 489 |
| HPV45 | L1 | 9 | 489 |
| HPV45 | L1 | 10 | 489 |
| HPV45 | L1 | 9 | 282 |
| HPV45 | L1 | 10 | 282 |
| HPV45 | L1 | 9 | 335 |
| HPV45 | L1 | 10 | 335 |
| HPV45 | L1 | 11 | 335 |
| HPV45 | L1 | 10 | 358 |
| HPV45 | L1 | 10 | 186 |
| HPV45 | L1 | 8 | 140 |
| HPV45 | L1 | 10 | 140 |
| HPV45 | L1 | 11 | 140 |
| HPV45 | L1 | 9 | 494 |
| HPV45 | L1 | 8 | 68 |
| HPV45 | L1 | 9 | 68 |
| HPV45 | L1 | 10 | 68 |
| HPV45 | L1 | 9 | 144 |
| HPV45 | L1 | 8 | 413 |
| HPV45 | L1 | 10 | 413 |
| HPV45 | L1 | 8 | 69 |
| HPV45 | L1 | 9 | 69 |
| HPV45 | L1 | 8 | 499 |
| HPV45 | L1 | 9 | 499 |
| HPV45 | L1 | 9 | 111 |
| HPV45 | L1 | 10 | 235 |
| HPV45 | L1 | 11 | 273 |
| HPV45 | L1 | 10 | 294 |
| HPV45 | L1 | 11 | 264 |
| HPV45 | L1 | 8 | 227 |
| HPV45 | L1 | 11 | 227 |
| HPV45 | L1 | 10 | 350 |
| HPV45 | L1 | 11 | 4 |
| HPV45 | L1 | 11 | 310 |
| HPV45 | L1 | 10 | 425 |
| HPV45 | L1 | 8 | 49 |
| HPV45 | L1 | 8 | 383 |
| HPV45 | L1 | 9 | 383 |
| HPV45 | L1 | 10 | 383 |
| HPV45 | L1 | 11 | 383 |
| HPV45 | L1 | 10 | 19 |
| HPV45 | L1 | 8 | 17 |
| HPV45 | L1 | 8 | 516 |
| HPV45 | L1 | 10 | 516 |
| HPV45 | L1 | 8 | 190 |
| HPV45 | L1 | 9 | 190 |
| HPV45 | L1 | 8 | 526 |
| HPV45 | L1 | 10 | 526 |
| HPV45 | L1 | 11 | 526 |
| HPV45 | L1 | 8 | 259 |
| HPV45 | L1 | 11 | 259 |
| HPV45 | L1 | 10 | 209 |
| HPV45 | L1 | 10 | 22 |
| HPV45 | L1 | 10 | 248 |
| HPV45 | L1 | 11 | 248 |
| HPV45 | L1 | 9 | 139 |
| HPV45 | L1 | 11 | 139 |
| HPV45 | L1 | 10 | 493 |
| HPV45 | L1 | 9 | 80 |
| HPV45 | L1 | 11 | 299 |
| HPV45 | L1 | 8 | 508 |
| HPV45 | L1 | 10 | 508 |
| HPV45 | L1 | 11 | 508 |
| HPV45 | L1 | 9 | 387 |
| HPV45 | L1 | 10 | 387 |
| HPV45 | L1 | 9 | 440 |
| HPV45 | L1 | 10 | 440 |
| HPV45 | L1 | 11 | 440 |
| HPV45 | L1 | 10 | 380 |
| HPV45 | L1 | 11 | 380 |
| HPV45 | L1 | 8 | 87 |
| HPV45 | L1 | 9 | 87 |
| HPV45 | L1 | 11 | 87 |
| HPV45 | L1 | 8 | 468 |
| HPV45 | L1 | 9 | 468 |
| HPV45 | L1 | 11 | 168 |
| HPV45 | L1 | 10 | 346 |
| HPV45 | L1 | 10 | 182 |

TABLE XVI-continued

HLA-A3 Motif Peptides

| 1 | 2 | 3 | 4 |
|---|---|---|---|
| HPV45 | L1 | 9 | 407 |
| HPV45 | L1 | 10 | 281 |
| HPV45 | L1 | 11 | 281 |
| HPV45 | L1 | 10 | 334 |
| HPV45 | L1 | 11 | 334 |
| HPV45 | L1 | 11 | 357 |
| HPV45 | L1 | 9 | 253 |
| HPV45 | L1 | 9 | 452 |
| HPV45 | L1 | 8 | 171 |
| HPV45 | L1 | 9 | 171 |
| HPV45 | L1 | 9 | 67 |
| HPV45 | L1 | 10 | 67 |
| HPV45 | L1 | 11 | 67 |
| HPV45 | L1 | 9 | 367 |
| HPV45 | L1 | 8 | 56 |
| HPV45 | L1 | 9 | 101 |
| HPV45 | L1 | 10 | 101 |
| HPV45 | L1 | 8 | 529 |
| HPV45 | L1 | 8 | 46 |
| HPV45 | L1 | 11 | 46 |
| HPV45 | L1 | 10 | 77 |
| HPV45 | L1 | 10 | 265 |
| HPV45 | L1 | 11 | 265 |
| HPV45 | L1 | 8 | 93 |
| HPV45 | L1 | 9 | 93 |
| HPV45 | L1 | 11 | 93 |
| HPV45 | L1 | 10 | 487 |
| HPV45 | L1 | 11 | 487 |
| HPV45 | L1 | B | 331 |
| HPV45 | L1 | 10 | 331 |
| HPV45 | L1 | 8 | 81 |
| HPV45 | L1 | 11 | 81 |
| HPV45 | L1 | 8 | 145 |
| HPV45 | L1 | 8 | 254 |
| HPV45 | L1 | 10 | 58 |
| HPV45 | L1 | 8 | 427 |
| HPV45 | L1 | 10 | 327 |
| HPV45 | L1 | 8 | 443 |
| HPV45 | L1 | 8 | 272 |
| HPV45 | L1 | 11 | 486 |
| HPV45 | L1 | 9 | 426 |
| HPV45 | L1 | 11 | 65 |
| HPV45 | L1 | 8 | 521 |
| HPV45 | L1 | 9 | 521 |
| HPV45 | L1 | 11 | 521 |
| HPV45 | L1 | 10 | 115 |
| HPV45 | L1 | 8 | 368 |
| HPV45 | L1 | 10 | 376 |
| HPV45 | L1 | 9 | 519 |
| HPV45 | L1 | 10 | 519 |
| HPV45 | L1 | 11 | 519 |
| HPV45 | L1 | 11 | 35 |
| HPV45 | L1 | 11 | 43 |
| HPV45 | L1 | 8 | 453 |
| HPV45 | L1 | 9 | 414 |
| HPV45 | L1 | 8 | 522 |
| HPV45 | L1 | 10 | 522 |
| HPV45 | L1 | 9 | 163 |
| HPV45 | L1 | 11 | 457 |
| HPV45 | L1 | 11 | 50 |
| HPV45 | L1 | 10 | 300 |
| HPV45 | L1 | 8 | 230 |
| HPV45 | L1 | 9 | 509 |
| HPV45 | L1 | 10 | 509 |
| HPV45 | L1 | 11 | 410 |
| HPV45 | L1 | 9 | 116 |
| HPV45 | L1 | 9 | 412 |
| HPV45 | L1 | 11 | 412 |
| HPV45 | L1 | 9 | 330 |
| HPV45 | L1 | 11 | 330 |
| HPV45 | L1 | 11 | 57 |
| HPV45 | L1 | 8 | 442 |
| HPV45 | L1 | 9 | 442 |
| HPV45 | L1 | 8 | 520 |
| HPV45 | L1 | 9 | 520 |
| HPV45 | L1 | 10 | 520 |
| HPV45 | L1 | 10 | 462 |
| HPV45 | L1 | 11 | 365 |
| HPV45 | L1 | 8 | 329 |
| HPV45 | L1 | 10 | 329 |
| HPV45 | L1 | 8 | 441 |
| HPV45 | L1 | 9 | 441 |
| HPV45 | L1 | 10 | 441 |
| HPV45 | L1 | 8 | 478 |
| HPV45 | L1 | 8 | 70 |
| HPV45 | L1 | 9 | 297 |
| HPV45 | L1 | 10 | 36 |
| HPV45 | L1 | 11 | 36 |
| HPV45 | L1 | 8 | 102 |
| HPV45 | L1 | 9 | 102 |
| HPV45 | L1 | 10 | 44 |
| HPV45 | L1 | 10 | 228 |
| HPV45 | L1 | 11 | 445 |
| HPV45 | L1 | 9 | 20 |
| HPV45 | L1 | 11 | 99 |
| HPV45 | L1 | 11 | 293 |
| HPV45 | L1 | 9 | 92 |
| HPV45 | L1 | 10 | 92 |
| HPV45 | L1 | 8 | 54 |
| HPV45 | L1 | 9 | 54 |
| HPV45 | L1 | 10 | 54 |
| HPV45 | L1 | 8 | 360 |
| HPV45 | L1 | 10 | 47 |
| HPV45 | L1 | 9 | 78 |
| HPV45 | L1 | 11 | 78 |
| HPV45 | L1 | 10 | 127 |
| HPV45 | L1 | 8 | 196 |
| HPV45 | L1 | 10 | 196 |
| HPV45 | L1 | 8 | 341 |
| HPV45 | L1 | 8 | 477 |
| HPV45 | L1 | 9 | 477 |
| HPV45 | L1 | 8 | 385 |
| HPV45 | L1 | 9 | 385 |
| HPV45 | L1 | 11 | 385 |
| HPV45 | L1 | 9 | 75 |
| HPV45 | L1 | 10 | 269 |
| HPV45 | L1 | 11 | 269 |
| HPV45 | L1 | 8 | 7 |
| HPV45 | L1 | 10 | 7 |
| HPV45 | L1 | 10 | 303 |
| HPV45 | L1 | 8 | 38 |
| HPV45 | L1 | 9 | 38 |
| HPV45 | L1 | 9 | 261 |
| HPV45 | L1 | 8 | 393 |
| HPV45 | L1 | 8 | 53 |
| HPV45 | L1 | 9 | 53 |
| HPV45 | L1 | 10 | 53 |
| HPV45 | L1 | 11 | 53 |
| HPV45 | L2 | 9 | 6 |
| HPV45 | L2 | 10 | 286 |
| HPV45 | L2 | 11 | 286 |
| HPV45 | L2 | 8 | 12 |
| HPV45 | L2 | 11 | 12 |
| HPV45 | L2 | 9 | 114 |
| HPV45 | L2 | 9 | 357 |
| HPV45 | L2 | 10 | 357 |
| HPV45 | L2 | 10 | 423 |
| HPV45 | L2 | 9 | 14 |
| HPV45 | L2 | 9 | 303 |
| HPV45 | L2 | 8 | 340 |
| HPV45 | L2 | 11 | 340 |
| HPV45 | L2 | 9 | 275 |
| HPV45 | L2 | 10 | 275 |
| HPV45 | L2 | 9 | 278 |
| HPV45 | L2 | 9 | 345 |
| HPV45 | L2 | 9 | 273 |
| HPV45 | L2 | 11 | 273 |
| HPV45 | L2 | 8 | 343 |
| HPV45 | L2 | 9 | 343 |
| HPV45 | L2 | 11 | 343 |

TABLE XVI-continued

HLA-A3 Motif Peptides

| 1 | 2 | 3 | 4 |
|---|---|---|---|
| HPV45 | L2 | 9 | 109 |
| HPV45 | L2 | 10 | 148 |
| HPV45 | L2 | 10 | 348 |
| HPV45 | L2 | 10 | 108 |
| HPV45 | L2 | 8 | 36 |
| HPV45 | L2 | 10 | 331 |
| HPV45 | L2 | 8 | 194 |
| HPV45 | L2 | 11 | 129 |
| HPV45 | L2 | 8 | 333 |
| HPV45 | L2 | 8 | 456 |
| HPV45 | L2 | 11 | 347 |
| HPV45 | L2 | 8 | 455 |
| HPV45 | L2 | 9 | 455 |
| HPV45 | L2 | 11 | 241 |
| HPV45 | L2 | 8 | 276 |
| HPV45 | L2 | 9 | 276 |
| HPV45 | L2 | 11 | 276 |
| HPV45 | L2 | 8 | 296 |
| HPV45 | L2 | 11 | 296 |
| HPV45 | L2 | 11 | 306 |
| HPV45 | L2 | 10 | 181 |
| HPV45 | L2 | 8 | 314 |
| HPV45 | L2 | 11 | 58 |
| HPV45 | L2 | 8 | 430 |
| HPV45 | L2 | 8 | 64 |
| HPV45 | L2 | 10 | 62 |
| HPV45 | L2 | 10 | 25 |
| HPV45 | L2 | 9 | 60 |
| HPV45 | L2 | 8 | 183 |
| HPV45 | L2 | 10 | 183 |
| HPV45 | L2 | 10 | 433 |
| HPV45 | L2 | 11 | 433 |
| HPV45 | L2 | 11 | 292 |
| HPV45 | L2 | 8 | 321 |
| HPV45 | L2 | 10 | 318 |
| HPV45 | L2 | 11 | 318 |
| HPV45 | L2 | 11 | 432 |
| HPV45 | L2 | 11 | 190 |
| HPV45 | L2 | 11 | 180 |
| HPV45 | L2 | 8 | 313 |
| HPV45 | L2 | 9 | 313 |
| HPV45 | L2 | 8 | 429 |
| HPV45 | L2 | 9 | 429 |
| HPV45 | L2 | 10 | 59 |
| HPV45 | L2 | 8 | 279 |
| HPV45 | L2 | 10 | 44 |
| HPV45 | L2 | 10 | 338 |
| HPV45 | L2 | 10 | 210 |
| HPV45 | L2 | 11 | 210 |
| HPV45 | L2 | 10 | 152 |
| HPV45 | L2 | 11 | 152 |
| HPV45 | L2 | 10 | 130 |
| HPV45 | L2 | 11 | 43 |
| HPV45 | L2 | 8 | 366 |
| HPV45 | L2 | 8 | 34 |
| HPV45 | L2 | 10 | 34 |
| HPV45 | L2 | 8 | 346 |
| HPV45 | L2 | 8 | 299 |
| HPV45 | L2 | 10 | 299 |
| HPV45 | L2 | 11 | 337 |
| HPV45 | L2 | 9 | 287 |
| HPV45 | L2 | 10 | 287 |
| HPV45 | L2 | 10 | 242 |
| HPV45 | L2 | 8 | 375 |
| HPV45 | L2 | 11 | 375 |
| HPV45 | L2 | 10 | 392 |
| HPV45 | L2 | 9 | 106 |
| HPV45 | L2 | 8 | 248 |
| HPV45 | L2 | 9 | 248 |
| HPV45 | L2 | 8 | 277 |
| HPV45 | L2 | 10 | 277 |
| HPV45 | L2 | 8 | 1 |
| HPV45 | L2 | 9 | 1 |
| HPV45 | L2 | 10 | 1 |
| HPV45 | L2 | 11 | 1 |
| HPV45 | L2 | 11 | 422 |
| HPV45 | L2 | 9 | 342 |
| HPV45 | L2 | 10 | 342 |
| HPV45 | L2 | 10 | 79 |
| HPV45 | L2 | 9 | 387 |
| HPV45 | L2 | 11 | 285 |
| HPV45 | L2 | 10 | 356 |
| HPV45 | L2 | 11 | 356 |
| HPV45 | L2 | 8 | 404 |
| HPV45 | L2 | 10 | 272 |
| HPV45 | L2 | 11 | 209 |
| HPV45 | L2 | 8 | 258 |
| HPV45 | L2 | 9 | 214 |
| HPV45 | L2 | 11 | 391 |
| HPV45 | L2 | 11 | 413 |
| HPV45 | L2 | 11 | 245 |
| HPV45 | L2 | 8 | 378 |
| HPV45 | L2 | 8 | 361 |
| HPV45 | L2 | 10 | 361 |
| HPV45 | L2 | 8 | 416 |
| HPV45 | L2 | 9 | 120 |
| HPV45 | L2 | 9 | 420 |
| HPV45 | L2 | 8 | 185 |
| HPV45 | L2 | 10 | 267 |
| HPV45 | L2 | 10 | 216 |
| HPV45 | L2 | 11 | 118 |
| HPV45 | L2 | 8 | 312 |
| HPV45 | L2 | 9 | 312 |
| HPV45 | L2 | 10 | 312 |
| HPV45 | L2 | 10 | 172 |
| HPV45 | L2 | 9 | 233 |
| HPV45 | L2 | 8 | 5 |
| HPV45 | L2 | 10 | 5 |
| HPV45 | L2 | 8 | 11 |
| HPV45 | L2 | 9 | 11 |
| HPV45 | L2 | 10 | 302 |
| HPV45 | L2 | 8 | 295 |
| HPV45 | L2 | 9 | 295 |
| HPV45 | L2 | 8 | 222 |
| HPV45 | L2 | 9 | 222 |
| HPV45 | L2 | 8 | 291 |
| HPV45 | L2 | 10 | 451 |
| HPV45 | L2 | 9 | 298 |
| HPV45 | L2 | 11 | 298 |
| HPV45 | L2 | 10 | 281 |
| HPV45 | L2 | 11 | 281 |
| HPV45 | L2 | 11 | 225 |
| HPV45 | L2 | 9 | 308 |
| HPV45 | L2 | 11 | 308 |
| HPV45 | L2 | 10 | 68 |
| HPV45 | L2 | 8 | 220 |
| HPV45 | L2 | 10 | 220 |
| HPV45 | L2 | 11 | 220 |
| HPV45 | L2 | 10 | 235 |
| HPV45 | L2 | 10 | 13 |
| HPV45 | L2 | 9 | 339 |
| HPV45 | L2 | 8 | 394 |
| HPV45 | L2 | 8 | 274 |
| HPV45 | L2 | 10 | 274 |
| HPV45 | L2 | 11 | 274 |
| HPV45 | L2 | 8 | 344 |
| HPV45 | L2 | 10 | 344 |
| HPV45 | L2 | 8 | 115 |
| HPV45 | L2 | 8 | 309 |
| HPV45 | L2 | 10 | 309 |
| HPV45 | L2 | 11 | 309 |
| HPV45 | L2 | 9 | 63 |
| HPV45 | L2 | 11 | 24 |
| HPV45 | L2 | 11 | 151 |
| HPV45 | L2 | 8 | 374 |
| HPV45 | L2 | 9 | 374 |
| HPV45 | L2 | 9 | 247 |
| HPV45 | L2 | 10 | 247 |
| HPV45 | L2 | 8 | 132 |
| HPV45 | L2 | 10 | 246 |

TABLE XVI-continued

HLA-A3 Motif Peptides

| 1 | 2 | 3 | 4 |
|---|---|---|---|
| HPV45 | L2 | 11 | 246 |
| HPV45 | L2 | 8 | 288 |
| HPV45 | L2 | 9 | 288 |
| HPV45 | L2 | 11 | 288 |
| HPV45 | L2 | 9 | 211 |
| HPV45 | L2 | 10 | 211 |
| HPV45 | L2 | 9 | 153 |
| HPV45 | L2 | 10 | 153 |
| HPV45 | L2 | 8 | 110 |
| HPV45 | L2 | 9 | 362 |
| HPV45 | L2 | 11 | 362 |
| HPV45 | L2 | 8 | 212 |
| HPV45 | L2 | 9 | 212 |
| HPV45 | L2 | 11 | 212 |
| HPV45 | L2 | 8 | 154 |
| HPV45 | L2 | 9 | 154 |
| HPV45 | L2 | 8 | 237 |
| HPV45 | L2 | 8 | 358 |
| HPV45 | L2 | 9 | 358 |
| HPV45 | L2 | 11 | 358 |
| HPV45 | L2 | 9 | 424 |
| HPV45 | L2 | 9 | 149 |
| HPV45 | L2 | 9 | 26 |
| HPV45 | L2 | 8 | 15 |
| HPV45 | L2 | 8 | 121 |
| HPV45 | L2 | 9 | 173 |
| HPV45 | L2 | 10 | 402 |
| HPV45 | L2 | 8 | 61 |
| HPV45 | L2 | 11 | 61 |
| HPV45 | L2 | 9 | 69 |
| HPV45 | L2 | 8 | 363 |
| HPV45 | L2 | 10 | 363 |
| HPV45 | L2 | 11 | 363 |
| HPV45 | L2 | 10 | 105 |
| HPV45 | L2 | 8 | 304 |
| HPV45 | L2 | 10 | 376 |
| HPV45 | L2 | 9 | 393 |
| HPV45 | L2 | 8 | 155 |
| HPV45 | L2 | 9 | 268 |
| HPV45 | L2 | 11 | 418 |
| HPV45 | L2 | 9 | 131 |
| HPV45 | L2 | 8 | 359 |
| HPV45 | L2 | 10 | 359 |
| HPV45 | L2 | 8 | 425 |
| HPV45 | L2 | 11 | 426 |
| HPV45 | L2 | 10 | 293 |
| HPV45 | L2 | 11 | 293 |
| HPV45 | L2 | 9 | 217 |
| HPV45 | L2 | 11 | 217 |
| HPV45 | L2 | 9 | 80 |
| HPV45 | L2 | 10 | 113 |
| HPV45 | L2 | 11 | 147 |
| HPV45 | L2 | 9 | 182 |
| HPV45 | L2 | 11 | 182 |
| HPV45 | L2 | 11 | 31 |
| HPV45 | L2 | 8 | 2 |
| HPV45 | L2 | 9 | 2 |
| HPV45 | L2 | 10 | 2 |
| HPV45 | L2 | 11 | 2 |
| HPV45 | L2 | 8 | 150 |
| HPV45 | L2 | 9 | 236 |
| HPV45 | L2 | 8 | 249 |
| HPV45 | L2 | 11 | 104 |
| HPV45 | L2 | 8 | 388 |
| HPV45 | L2 | 11 | 112 |
| HPV45 | L2 | 8 | 81 |
| HPV45 | L2 | 8 | 350 |
| HPV45 | L2 | 9 | 454 |
| HPV45 | L2 | 10 | 454 |
| HPV45 | L2 | 8 | 444 |
| HPV45 | L2 | 11 | 444 |
| HPV45 | L2 | 9 | 428 |
| HPV45 | L2 | 10 | 428 |
| HPV45 | L2 | 8 | 437 |
| HPV45 | L2 | 9 | 437 |
| HPV45 | L2 | 11 | 437 |
| HPV45 | L2 | 9 | 373 |
| HPV45 | L2 | 10 | 373 |
| HPV45 | L2 | 11 | 385 |
| HPV45 | L2 | 9 | 227 |
| HPV45 | L2 | 11 | 401 |
| HPV56 | E2 | 9 | 177 |
| HPV56 | E2 | 10 | 177 |
| HPV56 | E2 | 10 | 12 |
| HPV56 | E2 | 10 | 21 |
| HPV56 | E2 | 8 | 178 |
| HPV56 | E2 | 9 | 178 |
| HPV56 | E2 | 11 | 178 |
| HPV56 | E2 | 8 | 249 |
| HPV56 | E2 | 9 | 249 |
| HPV56 | E2 | 10 | 249 |
| HPV56 | E2 | 8 | 52 |
| HPV5G | E2 | 8 | 4 |
| HPV56 | E2 | 9 | 4 |
| HPV56 | E2 | 8 | 71 |
| HPV56 | E2 | 9 | 71 |
| HPV56 | E2 | 11 | 71 |
| HPV56 | E2 | 9 | 13 |
| HPV56 | E2 | 10 | 92 |
| HPV56 | E2 | 11 | 92 |
| HPV56 | E2 | 10 | 176 |
| HPV56 | E2 | 11 | 176 |
| HPV56 | E2 | 8 | 113 |
| HPV56 | E2 | 9 | 113 |
| HPV56 | E2 | 10 | 105 |
| HPV56 | E2 | 10 | 65 |
| HPV56 | E2 | 8 | 195 |
| HPV56 | E2 | 9 | 195 |
| HPV56 | E2 | 8 | 140 |
| HPV56 | E2 | 9 | 140 |
| HPV56 | E2 | 8 | 213 |
| HPV56 | E2 | 10 | 213 |
| HPV56 | E2 | 8 | 117 |
| HPV56 | E2 | 9 | 193 |
| HPV56 | E2 | 10 | 193 |
| HPV56 | E2 | 11 | 193 |
| HPV56 | E2 | 9 | 56 |
| HPV56 | E2 | 8 | 43 |
| HPV56 | E2 | 9 | 43 |
| HPV56 | E2 | 11 | 43 |
| HPV56 | E2 | 8 | 191 |
| HPV56 | E2 | 11 | 191 |
| HPV56 | E2 | 10 | 199 |
| HPV56 | E2 | 8 | 23 |
| HPV56 | E2 | 10 | 288 |
| HPV56 | E2 | 9 | 154 |
| HPV56 | E2 | 10 | 154 |
| HPV56 | E2 | 10 | 128 |
| HPV56 | E2 | 8 | 61 |
| HPV56 | E2 | 11 | 64 |
| HPV56 | E2 | 8 | 194 |
| HPV56 | E2 | 9 | 194 |
| HPV56 | E2 | 10 | 194 |
| HPV56 | E2 | 10 | 121 |
| HPV56 | E2 | 11 | 294 |
| HPV56 | E2 | 8 | 261 |
| HPV56 | E2 | 9 | 261 |
| HPV56 | E2 | 9 | 122 |
| HPV56 | E2 | 9 | 231 |
| HPV56 | E2 | 11 | 231 |
| HPV56 | E2 | 9 | 99 |
| HPV56 | E2 | 10 | 99 |
| HPV56 | E2 | 9 | 66 |
| HPV56 | E2 | 11 | 66 |
| HPV56 | E2 | 8 | 94 |
| HPV56 | E2 | 9 | 94 |
| HPV56 | E2 | 11 | 94 |
| HPV56 | E2 | 8 | 201 |
| HPV56 | E2 | 10 | 201 |
| HPV56 | E2 | 8 | 104 |

TABLE XVI-continued

HLA-A3 Motif Peptides

| 1 | 2 | 3 | 4 |
|---|---|---|---|
| HPV56 | E2 | 11 | 104 |
| HPV56 | E2 | 10 | 59 |
| HPV56 | E2 | 11 | 210 |
| HPV56 | E2 | 8 | 239 |
| HPV56 | E2 | 10 | 239 |
| HPV56 | E2 | 8 | 130 |
| HPV56 | E2 | 8 | 297 |
| HPV56 | E2 | 9 | 297 |
| HPV56 | E2 | 11 | 20 |
| HPV56 | E2 | 9 | 283 |
| HPV56 | E2 | 10 | 211 |
| HPV56 | E2 | 11 | 281 |
| HPV56 | E2 | 11 | 11 |
| HPV56 | E2 | 9 | 248 |
| HPV56 | E2 | 10 | 248 |
| HPV56 | E2 | 11 | 248 |
| HPV56 | E2 | 9 | 51 |
| HPV56 | E2 | 8 | 203 |
| HPV56 | E2 | 9 | 286 |
| HPV56 | E2 | 11 | 120 |
| HPV56 | E2 | 8 | 241 |
| HPV56 | E2 | 11 | 241 |
| HPV56 | E2 | 11 | 258 |
| HPV56 | E2 | 9 | 233 |
| HPV56 | E2 | 11 | 108 |
| HPV56 | E2 | 8 | 90 |
| HPV56 | E2 | 9 | 90 |
| HPV56 | E2 | 9 | 260 |
| HPV56 | E2 | 10 | 260 |
| HPV56 | E2 | 10 | 295 |
| HPV56 | E2 | 11 | 295 |
| HPV56 | E2 | 8 | 46 |
| HPV56 | E2 | 9 | 46 |
| HPV56 | E2 | 10 | 46 |
| HPV56 | E2 | 9 | 1 |
| HPV56 | E2 | 10 | 1 |
| HPV56 | E2 | 11 | 1 |
| HPV56 | E2 | 9 | 70 |
| HPV56 | E2 | 10 | 70 |
| HPV56 | E2 | 8 | 83 |
| HPV56 | E2 | 8 | 292 |
| HPV56 | E2 | 11 | 149 |
| HPV56 | E2 | 8 | 3 |
| HPV56 | E2 | 9 | 3 |
| HPV56 | E2 | 10 | 3 |
| HPV56 | E2 | 9 | 139 |
| HPV56 | E2 | 10 | 139 |
| HPV56 | E2 | 10 | 230 |
| HPV56 | E2 | 8 | 183 |
| HPV56 | E2 | 8 | 152 |
| HPV56 | E2 | 11 | 152 |
| HPV56 | E2 | 11 | 236 |
| HPV56 | E2 | 10 | 301 |
| HPV56 | E2 | 8 | 175 |
| HPV56 | E2 | 11 | 175 |
| HPV56 | E2 | 10 | 6 |
| HPV56 | E2 | 9 | 253 |
| HPV56 | E2 | 10 | 98 |
| HPV56 | E2 | 11 | 98 |
| HPV56 | E2 | 8 | 246 |
| HPV56 | E2 | 9 | 246 |
| HPV56 | E2 | 11 | 246 |
| HPV56 | E2 | 11 | 188 |
| HPV56 | E2 | 8 | 222 |
| HPV56 | E2 | 10 | 220 |
| HPV56 | E2 | 8 | 14 |
| HPV56 | E2 | 9 | 212 |
| HPV56 | E2 | 11 | 212 |
| HPV56 | E2 | 9 | 93 |
| HPV56 | E2 | 10 | 93 |
| HPV56 | E2 | 8 | 279 |
| HPV56 | E2 | 11 | 223 |
| HPV56 | E2 | 8 | 196 |
| HPV56 | E2 | 9 | 169 |
| HPV56 | E2 | 10 | 169 |
| HPV56 | E2 | 11 | 266 |
| HPV56 | E2 | 8 | 171 |
| HPV56 | E2 | 11 | 171 |
| HPV56 | E2 | 8 | 141 |
| HPV56 | E2 | 11 | 40 |
| HPV56 | E2 | 8 | 112 |
| HPV56 | E2 | 9 | 112 |
| HPV56 | E2 | 10 | 112 |
| HPV56 | E2 | 9 | 214 |
| HPV56 | E2 | 10 | 282 |
| HPV56 | E2 | 11 | 28 |
| HPV56 | E2 | 10 | 259 |
| HPV56 | E2 | 11 | 259 |
| HPV56 | E2 | 8 | 271 |
| HPV56 | E2 | 10 | 168 |
| HPV56 | E2 | 11 | 168 |
| HPV56 | E2 | 8 | 170 |
| HPV56 | E2 | 9 | 170 |
| HPV56 | E2 | 8 | 234 |
| HPV56 | E2 | 11 | 167 |
| HPV56 | E2 | 8 | 155 |
| HPV56 | E2 | 9 | 155 |
| HPV56 | E2 | 8 | 75 |
| HPV56 | E2 | 9 | 7 |
| HPV56 | E2 | 8 | 91 |
| HPV56 | E2 | 11 | 91 |
| HPV56 | E2 | B | 252 |
| HPV56 | E2 | 8 | 95 |
| HPV56 | E2 | 10 | 95 |
| HPV56 | E2 | 10 | 172 |
| HPV56 | E2 | 11 | 172 |
| HPV56 | E2 | 8 | 179 |
| HPV56 | E2 | 10 | 179 |
| HPV56 | E2 | 10 | 150 |
| HPV56 | E2 | 10 | 237 |
| HPV56 | E2 | 9 | 302 |
| HPV56 | E2 | 9 | 45 |
| HPV56 | E2 | 10 | 45 |
| HPV56 | E2 | 11 | 45 |
| HPV56 | E2 | 9 | 270 |
| HPV56 | E2 | 11 | 137 |
| HPV56 | E2 | 8 | 278 |
| HPV56 | E2 | 9 | 278 |
| HPV56 | E2 | 8 | 111 |
| HPV56 | E2 | 9 | 111 |
| HPV56 | E2 | 10 | 111 |
| HPV56 | E2 | 11 | 111 |
| HPV56 | E2 | 8 | 74 |
| HPV56 | E2 | 9 | 74 |
| HPV56 | E2 | 9 | 102 |
| HPV56 | E2 | 10 | 102 |
| HPV56 | E6 | 9 | 49 |
| HPV56 | E6 | 10 | 49 |
| HPV56 | E6 | 8 | 89 |
| HPV56 | E6 | 9 | 89 |
| HPV56 | E6 | 9 | 64 |
| HPV56 | E6 | 10 | 64 |
| HPV56 | E6 | 8 | 100 |
| HPV56 | E6 | 9 | 100 |
| HPV56 | E6 | 8 | 122 |
| HPV56 | E6 | 11 | 122 |
| HPV56 | E6 | 10 | 139 |
| HPV56 | E6 | 9 | 69 |
| HPV56 | E6 | 10 | 59 |
| HPV56 | E6 | 11 | 59 |
| HPV56 | E6 | 8 | 50 |
| HPV56 | E6 | 9 | 50 |
| HPV56 | E6 | 10 | 33 |
| HPV56 | E6 | 11 | 33 |
| HPV56 | E6 | 9 | 59 |
| HPV56 | E6 | 8 | 50 |
| HPV56 | E6 | 8 | 101 |
| HPV56 | E6 | 8 | 28 |
| HPV56 | E6 | 10 | 28 |
| HPV56 | E6 | 11 | 28 |

TABLE XVI-continued

HLA-A3 Motif Peptides

| 1 | 2 | 3 | 4 |
|---|---|---|---|
| HPV56 | E6 | 8 | 23 |
| HPV56 | E6 | 10 | 52 |
| HPV56 | E6 | 8 | 39 |
| HPV56 | E6 | 10 | 39 |
| HPV56 | E6 | 11 | 39 |
| HPV56 | E6 | 11 | 20 |
| HPV56 | E6 | 11 | 44 |
| HPV56 | E6 | 10 | 48 |
| HPV56 | E6 | 11 | 48 |
| HPV56 | E6 | 9 | 88 |
| HPV56 | E6 | 10 | 88 |
| HPV56 | E6 | 8 | 141 |
| HPV56 | E6 | 11 | 141 |
| HPV56 | E6 | 8 | 137 |
| HPV56 | E6 | 8 | 121 |
| HPV56 | E6 | 9 | 121 |
| HPV56 | E6 | 9 | 27 |
| HPV56 | E6 | 11 | 27 |
| HPV56 | E6 | 8 | 54 |
| HPV56 | E6 | 10 | 54 |
| HPV56 | E6 | 11 | 54 |
| HPV56 | E6 | 8 | 75 |
| HPV56 | E6 | 10 | 75 |
| HPV56 | E6 | 9 | 99 |
| HPV56 | E6 | 10 | 99 |
| HPV56 | E6 | 8 | 71 |
| HPV56 | E6 | 9 | 71 |
| HPV56 | E6 | 10 | 71 |
| HPV56 | E6 | 11 | 71 |
| HPV56 | E6 | 9 | 140 |
| HPV56 | E6 | 10 | 26 |
| HPV56 | E6 | 8 | 70 |
| HPV56 | E6 | 9 | 70 |
| HPV56 | E6 | 10 | 70 |
| HPV56 | E6 | 11 | 70 |
| HPV56 | E6 | 8 | 31 |
| HPV56 | E6 | 9 | 113 |
| HPV56 | E6 | 9 | 40 |
| HPV56 | E6 | 10 | 40 |
| HPV56 | E6 | 9 | 55 |
| HPV56 | E6 | 10 | 55 |
| HPV56 | E6 | 8 | 47 |
| HPV56 | E6 | 11 | 47 |
| HPV56 | E6 | 11 | 25 |
| HPV56 | E6 | 10 | 112 |
| HPV56 | E6 | 8 | 4 |
| HPV56 | E6 | 10 | 4 |
| HPV56 | E6 | 8 | 98 |
| HPV56 | E6 | 10 | 98 |
| HPV56 | E6 | 11 | 98 |
| HPV56 | E6 | 8 | 119 |
| HPV56 | E6 | 9 | 119 |
| HPV56 | E6 | 10 | 119 |
| HPV56 | E6 | 11 | 119 |
| HPV56 | E6 | 9 | 110 |
| HPV56 | E6 | 8 | 42 |
| HPV56 | E6 | 11 | 108 |
| HPV56 | E6 | 10 | 58 |
| HPV56 | E6 | 8 | 30 |
| HPV56 | E6 | 9 | 30 |
| HPV56 | E6 | 9 | 67 |
| HPV56 | E6 | 11 | 67 |
| HPV56 | E6 | 11 | 138 |
| HPV56 | E6 | 11 | 32 |
| HPV56 | E6 | 9 | 136 |
| HPV56 | E6 | 8 | 90 |
| HPV56 | E6 | 8 | 68 |
| HPV56 | E6 | 10 | 68 |
| HPV56 | E6 | 11 | 68 |
| HPV56 | E6 | 8 | 65 |
| HPV56 | E6 | 9 | 65 |
| HPV56 | E6 | 11 | 65 |
| HPV56 | E6 | 10 | 21 |
| HPV56 | E6 | 10 | 135 |
| HPV56 | E6 | 10 | 63 |
| HPV56 | E6 | 11 | 63 |
| HPV56 | E6 | 8 | 35 |
| HPV56 | E6 | 9 | 35 |
| HPV56 | E6 | 8 | 82 |
| HPV56 | E6 | 10 | 87 |
| HPV56 | E6 | 11 | 87 |
| HPV56 | E6 | 8 | 73 |
| HPV56 | E6 | 9 | 73 |
| HPV56 | E6 | 10 | 73 |
| HPV56 | E7 | 10 | 93 |
| HPV56 | E7 | 10 | 75 |
| HPV56 | E7 | 10 | 33 |
| HPV56 | E7 | 8 | 35 |
| HPV56 | E7 | 10 | 37 |
| HPV56 | E7 | 8 | 39 |
| HPV56 | E7 | 11 | 70 |
| HPV56 | E7 | 11 | 92 |
| HPV56 | E7 | 9 | 42 |
| HPV56 | E7 | 10 | 42 |
| HPV56 | E7 | 8 | 62 |
| HPV56 | E7 | 9 | 62 |
| HPV56 | E7 | 11 | 74 |
| HPV56 | E7 | 10 | 50 |
| HPV56 | E7 | 11 | 60 |
| HPV56 | E7 | 9 | 94 |
| HPV56 | E7 | 8 | 52 |
| HPV56 | E7 | 11 | 52 |
| HPV56 | E7 | 8 | 49 |
| HPV56 | E7 | 11 | 49 |
| HPV56 | E7 | 8 | 73 |
| HPV56 | E7 | 8 | 77 |
| HPV56 | E7 | 10 | 84 |
| HPV56 | E7 | 8 | 95 |
| HPV56 | E7 | 11 | 40 |
| HPV56 | E7 | 10 | 71 |
| HPV56 | E7 | 9 | 85 |
| HPV56 | E7 | 11 | 59 |
| HPV56 | L1 | 9 | 135 |
| HPV56 | L1 | 10 | 273 |
| HPV56 | L1 | 11 | 273 |
| HPV56 | L1 | 10 | 298 |
| HPV56 | L1 | 9 | 149 |
| HPV56 | L1 | 11 | 149 |
| HPV56 | L1 | 8 | 72 |
| HPV56 | L1 | 11 | 72 |
| HPV56 | L1 | 11 | 241 |
| HPV56 | L1 | 8 | 198 |
| HPV56 | L1 | 10 | 198 |
| HPV56 | L1 | 8 | 58 |
| HPV56 | L1 | 8 | 381 |
| HPV56 | L1 | 10 | 381 |
| HPV56 | L1 | 11 | 381 |
| HPV56 | L1 | 8 | 514 |
| HPV56 | L1 | 8 | 444 |
| HPV56 | L1 | 9 | 444 |
| HPV56 | L1 | 10 | 444 |
| HPV56 | L1 | 9 | 37 |
| HPV56 | L1 | 11 | 37 |
| HPV56 | L1 | 8 | 512 |
| HPV56 | L1 | 10 | 512 |
| HPV56 | L1 | 11 | 79 |
| HPV56 | L1 | 8 | 26 |
| HPV56 | L1 | 8 | 19 |
| HPV56 | L1 | 8 | 191 |
| HPV56 | L1 | 8 | 195 |
| HPV56 | L1 | 11 | 195 |
| HPV56 | L1 | 8 | 136 |
| HPV56 | L1 | 8 | 389 |
| HPV56 | L1 | 10 | 389 |
| HPV56 | L1 | 11 | 389 |
| HPV56 | L1 | 9 | 274 |
| HPV56 | L1 | 10 | 274 |
| HPV56 | L1 | 9 | 161 |
| HPV56 | L1 | 9 | 243 |
| HPV56 | L1 | 10 | 243 |

TABLE XVI-continued

HLA-A3 Motif Peptides

| 1 | 2 | 3 | 4 |
|---|---|---|---|
| HPV56 | L1 | 9 | 231 |
| HPV56 | L1 | 11 | 231 |
| HPV56 | L1 | 8 | 257 |
| HPV56 | L1 | 9 | 257 |
| HPV56 | L1 | 9 | 491 |
| HPV56 | L1 | 10 | 491 |
| HPV56 | L1 | 11 | 491 |
| HPV56 | L1 | 9 | 233 |
| HPV56 | L1 | 10 | 486 |
| HPV56 | L1 | 8 | 278 |
| HPV56 | L1 | 9 | 278 |
| HPV56 | L1 | 11 | 176 |
| HPV56 | L1 | 10 | 50 |
| HPV56 | L1 | 11 | 60 |
| HPV56 | L1 | 8 | 162 |
| HPV56 | L1 | 9 | 236 |
| HPV56 | L1 | 10 | 236 |
| HPV56 | L1 | 11 | 121 |
| HPV56 | L1 | 8 | 23 |
| HPV56 | L1 | 11 | 23 |
| HPV56 | L1 | 8 | 481 |
| HPV56 | L1 | 9 | 337 |
| HPV56 | L1 | 10 | 230 |
| HPV56 | L1 | 8 | 448 |
| HPV56 | L1 | 11 | 448 |
| HPV56 | L1 | 10 | 404 |
| HPV56 | L1 | 10 | 308 |
| HPV56 | L1 | 8 | 303 |
| HPV56 | L1 | 10 | 303 |
| HPV56 | L1 | 10 | 140 |
| HPV56 | L1 | 11 | 419 |
| HPV56 | L1 | 8 | 290 |
| HPV56 | L1 | 9 | 290 |
| HPV56 | L1 | 11 | 290 |
| HPV56 | L1 | 9 | 117 |
| HPV56 | L1 | 10 | 21 |
| HPV56 | L1 | 8 | 501 |
| HPV56 | L1 | 10 | 5Q1 |
| HPV56 | L1 | 8 | 33 |
| HPV56 | L1 | 8 | 488 |
| HPV56 | L1 | 9 | 364 |
| HPV56 | L1 | 10 | 148 |
| HPV56 | L1 | 9 | 25 |
| HPV56 | L1 | 9 | 194 |
| HPV56 | L1 | 8 | 232 |
| HPV56 | L1 | 10 | 232 |
| HPV56 | L1 | 9 | 277 |
| HPV56 | L1 | 10 | 277 |
| HPV56 | L1 | 8 | 238 |
| HPV56 | L1 | 9 | 356 |
| HPV56 | L1 | 10 | 17 |
| HPV56 | L1 | 8 | 118 |
| HPV56 | L1 | 8 | 15O |
| HPV56 | L1 | 10 | 150 |
| HPV56 | L1 | 8 | 331 |
| HPV56 | L1 | 11 | 331 |
| HPV56 | L1 | 10 | 73 |
| HPV56 | L1 | 9 | 506 |
| HPV56 | L1 | 9 | 71 |
| HPV56 | L1 | 9 | 399 |
| HPV56 | L1 | 11 | 399 |
| HPV56 | L1 | 8 | 357 |
| HPV56 | L1 | 10 | 235 |
| HPV56 | L1 | 11 | 235 |
| HPV56 | L1 | 11 | 20 |
| HPV56 | L1 | 9 | 32 |
| HPV56 | L1 | 9 | 68 |
| HPV56 | L1 | 8 | 437 |
| HPV56 | L1 | 10 | 378 |
| HPV56 | L1 | 11 | 378 |
| HPV56 | L1 | 9 | 414 |
| HPV56 | L1 | 10 | 414 |
| HPV56 | L1 | 8 | 334 |
| HPV56 | L1 | 10 | 334 |
| HPV56 | L1 | 11 | 192 |
| HPV56 | L1 | 8 | 258 |
| HPV56 | L1 | 11 | 258 |
| HPV56 | L1 | 10 | 89 |
| HPV56 | L1 | 10 | 116 |
| HPV56 | L1 | 9 | 500 |
| HPV56 | L1 | 11 | 500 |
| HPV56 | L1 | 11 | 478 |
| HPV56 | L1 | 8 | 392 |
| HPV56 | L1 | 10 | 413 |
| HPV56 | L1 | 11 | 413 |
| HPV56 | L1 | 9 | 93 |
| HPV56 | L1 | 10 | 93 |
| HPV56 | L1 | 8 | 300 |
| HPV56 | L1 | 11 | 300 |
| HPV56 | L1 | 8 | 245 |
| HPV56 | L1 | 8 | 98 |
| HPV56 | L1 | 10 | 98 |
| HPV56 | L1 | 11 | 98 |
| HPV56 | L1 | 8 | 55 |
| HPV56 | L1 | 10 | 55 |
| HPV56 | L1 | 11 | 55 |
| HPV56 | L1 | 11 | 45 |
| HPV56 | L1 | 11 | 168 |
| HPV56 | L1 | 8 | 78 |
| HPV56 | L1 | 9 | 18 |
| HPV56 | L1 | 9 | 190 |
| HPV56 | L1 | 8 | 411 |
| HPV56 | L1 | 10 | 160 |
| HPV56 | L1 | 9 | 256 |
| HPV56 | L1 | 10 | 256 |
| HPV56 | L1 | 8 | 492 |
| HPV56 | L1 | 9 | 492 |
| HPV56 | L1 | 10 | 492 |
| HPV56 | L1 | 9 | 22 |
| HPV56 | L1 | 9 | 289 |
| HPV56 | L1 | 10 | 289 |
| HPV56 | L1 | 10 | 340 |
| HPV56 | L1 | 11 | 340 |
| HPV56 | L1 | 10 | 363 |
| HPV56 | L1 | 8 | 147 |
| HPV56 | L1 | 11 | 147 |
| HPV56 | L1 | 8 | 505 |
| HPV56 | L1 | 10 | 505 |
| HPV56 | L1 | 8 | 77 |
| HPV56 | L1 | 9 | 77 |
| HPV56 | L1 | 9 | 502 |
| HPV56 | L1 | 11 | 502 |
| HPV56 | L1 | 8 | 416 |
| HPV56 | L1 | 10 | 416 |
| HPV56 | L1 | 9 | 151 |
| HPV56 | L1 | 8 | 385 |
| HPV56 | L1 | 10 | 36 |
| HPV56 | L1 | 9 | 421 |
| HPV56 | L1 | 10 | 242 |
| HPV56 | L1 | 11 | 242 |
| HPV56 | L1 | 9 | 199 |
| HPV56 | L1 | 8 | 234 |
| HPV56 | L1 | 11 | 234 |
| HPV56 | L1 | 9 | 333 |
| HPV56 | L1 | 11 | 333 |
| HPV56 | L1 | 8 | 2 |
| HPV56 | L1 | 9 | 2 |
| HPV56 | L1 | 9 | 1 |
| HPV56 | L1 | 10 | 1 |
| HPV56 | L1 | 11 | 5 |
| HPV56 | L1 | 10 | 355 |
| HPV56 | L1 | 11 | 315 |
| HPV56 | L1 | 9 | 436 |
| HPV56 | L1 | 8 | 95 |
| HPV56 | L1 | 10 | 95 |
| HPV56 | L1 | 11 | 95 |
| HPV56 | L1 | 9 | 123 |
| HPV56 | L1 | 8 | 91 |
| HPV56 | L1 | 11 | 91 |
| HPV56 | L1 | 10 | 28 |

TABLE XVI-continued

HLA-A3 Motif Peptides

| 1 | 2 | 3 | 4 |
|---|---|---|---|
| HPV56 | L1 | 9 | 197 |
| HPV56 | L1 | 11 | 197 |
| HPV56 | L1 | 8 | 511 |
| HPV56 | L1 | 9 | 511 |
| HPV56 | L1 | 11 | 511 |
| HPV56 | L1 | 9 | 127 |
| HPV56 | L1 | 8 | 266 |
| HPV56 | L1 | 10 | 266 |
| HPV56 | L1 | 11 | 266 |
| HPV56 | L1 | 10 | 31 |
| HPV56 | L1 | 10 | 255 |
| HPV56 | L1 | 11 | 255 |
| HPV56 | L1 | 9 | 146 |
| HPV56 | L1 | 9 | 13 |
| HPV56 | L1 | 10 | 329 |
| HPV56 | L1 | 9 | 467 |
| HPV56 | L1 | 10 | 467 |
| HPV56 | L1 | 11 | 467 |
| HPV56 | L1 | 9 | 50 |
| HPV56 | L1 | 8 | 522 |
| HPV56 | L1 | 9 | 522 |
| HPV56 | L1 | 10 | 522 |
| HPV56 | L1 | 11 | 522 |
| HPV56 | L1 | 9 | 442 |
| HPV56 | L1 | 10 | 442 |
| HPV56 | L1 | 11 | 442 |
| HPV56 | L1 | 11 | 52 |
| HPV56 | L1 | 8 | 471 |
| HPV56 | L1 | 9 | 471 |
| HPV56 | L1 | 11 | 485 |
| HPV56 | L1 | 8 | 494 |
| HPV56 | L1 | 8 | 406 |
| HPV56 | L1 | 10 | 189 |
| HPV56 | L1 | 9 | 410 |
| HPV56 | L1 | 8 | 288 |
| HPV56 | L1 | 10 | 288 |
| HPV56 | L1 | 11 | 288 |
| HPV56 | L1 | 11 | 339 |
| HPV56 | L1 | 11 | 362 |
| HPV56 | L1 | 9 | 504 |
| HPV56 | L1 | 11 | 504 |
| HPV56 | L1 | 8 | 384 |
| HPV56 | L1 | 9 | 384 |
| HPV56 | L1 | 11 | 35 |
| HPV56 | L1 | 9 | 260 |
| HPV56 | L1 | 11 | 260 |
| HPV56 | L1 | 11 | 213 |
| HPV56 | L1 | 11 | 297 |
| HPV56 | L1 | 9 | 178 |
| HPV56 | L1 | 11 | 159 |
| HPV56 | L1 | 9 | 76 |
| HPV56 | L1 | 10 | 76 |
| HPV56 | L1 | 8 | 110 |
| HPV56 | L1 | 11 | 519 |
| HPV56 | L1 | 10 | 508 |
| HPV56 | L1 | 11 | 508 |
| HPV56 | L1 | 9 | 455 |
| HPV56 | L1 | 10 | 372 |
| HPV56 | L1 | 8 | 65 |
| HPV56 | L1 | 9 | 108 |
| HPV56 | L1 | 10 | 108 |
| HPV56 | L1 | 11 | 272 |
| HPV56 | L1 | 9 | 417 |
| HPV56 | L1 | 10 | 520 |
| HPV56 | L1 | 11 | 520 |
| HPV56 | L1 | 8 | 100 |
| HPV56 | L1 | 9 | 100 |
| HPV56 | L1 | 11 | 100 |
| HPV56 | L1 | 9 | 487 |
| HPV56 | L1 | 8 | 152 |
| HPV56 | L1 | 9 | 330 |
| HPV56 | L1 | 10 | 67 |
| HPV56 | L1 | 8 | 446 |
| HPV56 | L1 | 10 | 446 |
| HPV56 | L1 | 10 | 332 |
| HPV56 | L1 | 8 | 279 |
| HPV56 | L1 | 9 | 74 |
| HPV56 | L1 | 11 | 74 |
| HPV56 | L1 | 8 | 456 |
| HPV56 | L1 | 9 | 379 |
| HPV56 | L1 | 10 | 379 |
| HPV56 | L1 | 8 | 261 |
| HPV56 | L1 | 10 | 261 |
| HPV56 | L1 | 11 | 489 |
| HPV56 | L1 | 9 | 373 |
| HPV56 | L1 | 8 | 526 |
| HPV56 | L1 | 9 | 526 |
| HPV56 | L1 | 8 | 524 |
| HPV56 | L1 | 9 | 524 |
| HPV56 | L1 | 10 | 524 |
| HPV56 | L1 | 11 | 524 |
| HPV56 | L1 | 8 | 86 |
| HPV56 | L1 | 8 | 380 |
| HPV56 | L1 | 9 | 380 |
| HPV56 | L1 | 11 | 380 |
| HPV56 | L1 | 9 | 262 |
| HPV56 | L1 | 11 | 460 |
| HPV56 | L1 | 10 | 490 |
| HPV56 | L1 | 11 | 490 |
| HPV56 | L1 | 11 | 59 |
| HPV56 | L1 | 8 | 216 |
| HPV56 | L1 | 8 | 237 |
| HPV56 | L1 | 9 | 237 |
| HPV56 | L1 | 9 | 304 |
| HPV56 | L1 | 11 | 377 |
| HPV56 | L1 | 8 | 415 |
| HPV56 | L1 | 9 | 415 |
| HPV56 | L1 | 11 | 415 |
| HPV56 | L1 | 9 | 335 |
| HPV56 | L1 | 11 | 335 |
| HPV56 | L1 | 11 | 66 |
| HPV56 | L1 | 8 | 445 |
| HPV56 | L1 | 9 | 445 |
| HPV56 | L1 | 11 | 445 |
| HPV56 | L1 | 8 | 525 |
| HPV56 | L1 | 9 | 525 |
| HPV56 | L1 | 10 | 525 |
| HPV56 | L1 | 8 | 523 |
| HPV56 | L1 | 9 | 523 |
| HPV56 | L1 | 10 | 523 |
| HPV56 | L1 | 11 | 523 |
| HPV56 | L1 | 9 | 215 |
| HPV56 | L1 | 8 | 57 |
| HPV56 | L1 | 9 | 57 |
| HPV56 | L1 | 9 | 513 |
| HPV56 | L1 | 8 | 443 |
| HPV56 | L1 | 9 | 443 |
| HPV56 | L1 | 10 | 443 |
| HPV56 | L1 | 11 | 443 |
| HPV56 | L1 | 9 | 29 |
| HPV56 | L1 | 11 | 408 |
| HPV56 | L1 | 11 | 106 |
| HPV56 | L1 | 10 | 24 |
| HPV56 | L1 | 10 | 193 |
| HPV56 | L1 | 10 | 301 |
| HPV56 | L1 | 10 | 80 |
| HPV56 | L1 | 9 | 141 |
| HPV56 | L1 | 10 | 420 |
| HPV56 | L1 | 9 | 99 |
| HPV56 | L1 | 10 | 99 |
| HPV56 | L1 | 10 | 53 |
| HPV56 | L1 | 10 | 214 |
| HPV56 | L1 | 8 | 365 |
| HPV56 | L1 | 9 | 56 |
| HPV56 | L1 | 10 | 56 |
| HPV56 | L1 | 10 | 134 |
| HPV56 | L1 | 9 | 480 |
| HPV56 | L1 | 10 | 281 |
| HPV56 | L1 | 11 | 281 |
| HPV56 | L1 | 8 | 346 |

TABLE XVI-continued

HLA-A3 Motif Peptides

| 1 | 2 | 3 | 4 |
|---|---|---|---|
| HPV56 | L1 | 8 | 203 |
| HPV56 | L1 | 9 | 388 |
| HPV56 | L1 | 11 | 388 |
| HPV56 | L1 | 8 | 276 |
| HPV56 | L1 | 10 | 276 |
| HPV56 | L1 | 11 | 276 |
| HPV56 | L1 | 11 | 16 |
| HPV56 | L1 | 9 | 7 |
| HPV56 | L1 | 10 | 7 |
| HPV56 | L1 | 8 | 310 |
| HPV56 | L1 | 8 | 268 |
| HPV56 | L1 | 9 | 268 |
| HPV56 | L1 | 9 | 47 |
| HPV56 | L1 | 8 | 396 |
| HPV56 | L1 | 8 | 283 |
| HPV56 | L1 | 9 | 283 |
| HPV56 | L1 | 10 | 283 |
| HPV56 | L1 | 11 | 283 |
| HPV56 | L1 | 9 | 85 |
| HPV56 | L1 | 8 | 62 |
| HPV56 | L1 | 9 | 62 |
| HPV56 | L1 | 10 | 62 |
| HPV56 | L1 | 11 | 62 |
| HPV56 | L1 | 11 | 453 |
| HPV56 | L2 | 8 | 222 |
| HPV56 | L2 | 9 | 222 |
| HPV56 | L2 | 10 | 222 |
| HPV56 | L2 | 11 | 41 |
| HPV56 | L2 | 11 | 230 |
| HPV56 | L2 | 8 | 264 |
| HPV56 | L2 | 10 | 286 |
| HPV56 | L2 | 11 | 286 |
| HPV56 | L2 | 9 | 69 |
| HPV56 | L2 | 10 | 281 |
| HPV56 | L2 | 11 | 281 |
| HPV56 | L2 | 8 | 438 |
| HPV56 | L2 | 9 | 438 |
| HPV56 | L2 | 10 | 438 |
| HPV56 | L2 | 11 | 438 |
| HPV56 | L2 | 8 | 12 |
| HPV56 | L2 | 11 | 12 |
| HPV56 | L2 | 9 | 383 |
| HPV56 | L2 | 11 | 246 |
| HPV56 | L2 | 10 | 367 |
| HPV56 | L2 | 9 | 14 |
| HPV56 | L2 | 9 | 6 |
| HPV56 | L2 | 9 | 275 |
| HPV56 | L2 | 10 | 275 |
| HPV56 | L2 | 8 | 345 |
| HPV56 | L2 | 8 | 322 |
| HPV56 | L2 | 10 | 142 |
| HPV56 | L2 | 10 | 349 |
| HPV56 | L2 | 9 | 30 |
| HPV56 | L2 | 9 | 429 |
| HPV56 | L2 | 10 | 429 |
| HPV56 | L2 | 11 | 357 |
| HPV56 | L2 | 10 | 29 |
| HPV56 | L2 | 8 | 257 |
| HPV56 | L2 | 9 | 257 |
| HPV56 | L2 | 10 | 331 |
| HPV56 | L2 | 8 | 194 |
| HPV56 | L2 | 10 | 194 |
| HPV56 | L2 | 11 | 129 |
| HPV56 | L2 | 8 | 333 |
| HPV56 | L2 | 9 | 114 |
| HPV56 | L2 | 9 | 109 |
| HPV56 | L2 | 8 | 457 |
| HPV56 | L2 | 8 | 437 |
| HPV56 | L2 | 9 | 437 |
| HPV56 | L2 | 10 | 437 |
| HPV56 | L2 | 11 | 437 |
| HPV56 | L2 | 10 | 382 |
| HPV56 | L2 | 8 | 344 |
| HPV56 | L2 | 9 | 344 |
| HPV56 | L2 | 8 | 456 |
| HPV56 | L2 | 9 | 456 |
| HPV56 | L2 | 8 | 444 |
| HPV56 | L2 | 9 | 444 |
| HPV56 | L2 | 9 | 162 |
| HPV56 | L2 | 11 | 241 |
| HPV56 | L2 | 8 | 276 |
| HPV56 | L2 | 9 | 276 |
| HPV56 | L2 | 11 | 276 |
| HPV56 | L2 | 8 | 296 |
| HPV56 | L2 | 9 | 287 |
| HPV56 | L2 | 10 | 287 |
| HPV56 | L2 | 11 | 418 |
| HPV56 | L2 | 8 | 314 |
| HPV56 | L2 | 9 | 217 |
| HPV56 | L2 | 11 | 217 |
| HPV56 | L2 | 10 | 292 |
| HPV56 | L2 | 11 | 292 |
| HPV56 | L2 | 11 | 58 |
| HPV56 | L2 | 11 | 118 |
| HPV56 | L2 | 8 | 360 |
| HPV56 | L2 | 8 | 64 |
| HPV56 | L2 | 10 | 434 |
| HPV56 | L2 | 11 | 434 |
| HPV56 | L2 | 10 | 25 |
| HPV56 | L2 | 8 | 258 |
| HPV56 | L2 | 8 | 62 |
| HPV56 | L2 | 10 | 62 |
| HPV56 | L2 | 9 | 60 |
| HPV56 | L2 | 10 | 60 |
| HPV56 | L2 | 9 | 310 |
| HPV56 | L2 | 10 | 310 |
| HPV56 | L2 | 11 | 310 |
| HPV56 | L2 | 8 | 269 |
| HPV56 | L2 | 9 | 293 |
| HPV56 | L2 | 10 | 293 |
| HPV56 | L2 | 11 | 293 |
| HPV56 | L2 | 10 | 428 |
| HPV56 | L2 | 11 | 428 |
| HPV56 | L2 | 11 | 372 |
| HPV56 | L2 | 11 | 190 |
| HPV56 | L2 | 8 | 221 |
| HPV56 | L2 | 9 | 221 |
| HPV56 | L2 | 10 | 221 |
| HPV56 | L2 | 11 | 221 |
| HPV56 | L2 | 8 | 163 |
| HPV56 | L2 | 8 | 313 |
| HPV56 | L2 | 9 | 313 |
| HPV56 | L2 | 10 | 59 |
| HPV56 | L2 | 11 | 59 |
| HPV56 | L2 | 11 | 180 |
| HPV56 | L2 | 8 | 44 |
| HPV56 | L2 | 10 | 44 |
| HPV56 | L2 | 11 | 44 |
| HPV56 | L2 | 9 | 210 |
| HPV56 | L2 | 10 | 210 |
| HPV56 | L2 | 11 | 210 |
| HPV56 | L2 | 9 | 182 |
| HPV56 | L2 | 11 | 182 |
| HPV56 | L2 | 9 | 143 |
| HPV56 | L2 | 10 | 130 |
| HPV56 | L2 | 8 | 279 |
| HPV56 | L2 | 9 | 279 |
| HPV56 | L2 | 8 | 81 |
| HPV56 | L2 | 8 | 302 |
| HPV56 | L2 | 8 | 34 |
| HPV56 | L2 | 10 | 34 |
| HPV56 | L2 | 9 | 43 |
| HPV56 | L2 | 11 | 43 |
| HPV56 | L2 | 10 | 235 |
| HPV56 | L2 | 9 | 263 |
| HPV56 | L2 | 11 | 141 |
| HPV56 | L2 | 10 | 242 |
| HPV56 | L2 | 10 | 255 |
| HPV56 | L2 | 11 | 255 |
| HPV56 | L2 | 10 | 161 |

TABLE XVI-continued

HLA-A3 Motif Peptides

| 1 | 2 | 3 | 4 |
|---|---|---|---|
| HPV56 | L2 | 9 | 393 |
| HPV56 | L2 | 10 | 393 |
| HPV56 | L2 | 10 | 299 |
| HPV56 | L2 | 11 | 299 |
| HPV56 | L2 | 10 | 181 |
| HPV56 | L2 | 8 | 337 |
| HPV56 | L2 | 11 | 338 |
| HPV56 | L2 | 11 | 361 |
| HPV56 | L2 | 9 | 248 |
| HPV56 | L2 | 8 | 1 |
| HPV56 | L2 | 9 | 1 |
| HPV56 | L2 | 10 | 1 |
| HPV56 | L2 | 11 | 1 |
| HPV56 | L2 | 8 | 121 |
| HPV56 | L2 | 9 | 278 |
| HPV56 | L2 | 10 | 278 |
| HPV56 | L2 | 10 | 342 |
| HPV56 | L2 | 11 | 342 |
| HPV56 | L2 | 8 | 395 |
| HPV56 | L2 | 8 | 239 |
| HPV56 | L2 | 11 | 285 |
| HPV56 | L2 | 8 | 274 |
| HPV56 | L2 | 10 | 274 |
| HPV56 | L2 | 11 | 274 |
| HPV56 | L2 | 10 | 272 |
| HPV56 | L2 | 8 | 417 |
| HPV56 | L2 | 8 | 216 |
| HPV56 | L2 | 10 | 216 |
| HPV56 | L2 | 9 | 359 |
| HPV56 | L2 | 9 | 374 |
| HPV56 | L2 | 10 | 374 |
| HPV56 | L2 | 9 | 214 |
| HPV56 | L2 | 10 | 214 |
| HPV56 | L2 | 10 | 209 |
| HPV56 | L2 | 11 | 209 |
| HPV56 | L2 | 11 | 254 |
| HPV56 | L2 | 11 | 160 |
| HPV56 | L2 | 10 | 392 |
| HPV56 | L2 | 11 | 392 |
| HPV56 | L2 | 9 | 336 |
| HPV56 | L2 | 8 | 196 |
| HPV56 | L2 | 8 | 369 |
| HPV56 | L2 | 10 | 267 |
| HPV56 | L2 | 10 | 78 |
| HPV56 | L2 | 11 | 78 |
| HPV56 | L2 | 9 | 410 |
| HPV56 | L2 | 8 | 185 |
| HPV56 | L2 | 8 | 441 |
| HPV56 | L2 | 9 | 441 |
| HPV56 | L2 | 10 | 441 |
| HPV56 | L2 | 11 | 441 |
| HPV56 | L2 | 11 | 433 |
| HPV56 | L2 | 8 | 312 |
| HPV56 | L2 | 9 | 312 |
| HPV56 | L2 | 10 | 312 |
| HPV56 | L2 | 8 | 421 |
| HPV56 | L2 | 11 | 421 |
| HPV56 | L2 | 8 | 364 |
| HPV56 | L2 | 9 | 364 |
| HPV56 | L2 | 10 | 306 |
| HPV56 | L2 | 11 | 306 |
| HPV56 | L2 | 8 | 233 |
| HPV56 | L2 | 9 | 233 |
| HPV56 | L2 | 10 | 68 |
| HPV56 | L2 | 8 | 11 |
| HPV56 | L2 | 9 | 11 |
| HPV56 | L2 | 8 | 5 |
| HPV56 | L2 | 10 | 5 |
| HPV56 | L2 | 8 | 295 |
| HPV56 | L2 | 9 | 295 |
| HPV56 | L2 | 8 | 291 |
| HPV56 | L2 | 11 | 291 |
| HPV56 | L2 | 8 | 309 |
| HPV56 | L2 | 10 | 309 |
| HPV56 | L2 | 11 | 309 |
| HPV56 | L2 | 8 | 220 |
| HPV56 | L2 | 9 | 220 |
| HPV56 | L2 | 10 | 220 |
| HPV56 | L2 | 12 | 220 |
| HPV56 | L2 | 11 | 298 |
| HPV56 | L2 | 11 | 225 |
| HPV56 | L2 | 10 | 339 |
| HPV56 | L2 | 10 | 13 |
| HPV56 | L2 | 8 | 436 |
| HPV56 | L2 | 9 | 436 |
| HPV56 | L2 | 10 | 436 |
| HPV56 | L2 | 11 | 436 |
| HPV56 | L2 | 12 | 381 |
| HPV56 | L2 | 9 | 343 |
| HPV56 | L2 | 10 | 343 |
| HPV56 | L2 | 8 | u5 |
| HPV56 | L2 | 11 | 24 |
| HPV56 | L2 | 9 | 268 |
| HPV56 | L2 | 10 | 262 |
| HPV56 | L2 | 9 | 435 |
| HPV56 | L2 | 10 | 435 |
| HPV56 | L2 | 11 | 435 |
| HPV56 | L2 | 10 | 362 |
| HPV56 | L2 | 11 | 362 |
| HPV56 | L2 | 8 | 132 |
| HPV56 | L2 | 10 | 153 |
| HPV56 | L2 | 8 | 211 |
| HPV56 | L2 | 9 | 211 |
| HPV56 | L2 | 10 | 211 |
| HPV56 | L2 | 10 | 147 |
| HPV56 | L2 | 8 | 110 |
| HPV56 | L2 | 9 | 154 |
| HPV56 | L2 | 9 | 79 |
| HPV56 | L2 | 10 | 79 |
| HPV56 | L2 | 8 | 212 |
| HPV56 | L2 | 9 | 212 |
| HPV56 | L2 | 11 | 212 |
| HPV56 | L2 | 8 | 183 |
| HPV56 | L2 | 10 | 183 |
| HPV56 | L2 | 9 | 148 |
| HPV56 | L2 | 11 | 414 |
| HPV56 | L2 | 8 | 365 |
| HPV56 | L2 | 9 | 26 |
| HPV56 | L2 | 8 | 237 |
| HPV56 | L2 | 10 | 237 |
| HPV56 | L2 | 8 | 411 |
| HPV56 | L2 | 9 | 63 |
| HPV56 | L2 | 8 | 61 |
| HPV56 | L2 | 9 | 61 |
| HPV56 | L2 | 11 | 61 |
| HPV56 | L2 | 8 | 80 |
| HPV56 | L2 | 9 | 80 |
| HPV56 | L2 | 10 | 247 |
| HPV56 | L2 | 11 | 261 |
| HPV56 | L2 | 9 | 131 |
| HPV56 | L2 | 11 | 146 |
| HPV56 | L2 | 8 | 288 |
| HPV56 | L2 | 9 | 288 |
| HPV56 | L2 | 11 | 288 |
| HPV56 | L2 | 8 | 149 |
| HPV56 | L2 | 8 | 2 |
| HPV56 | L2 | 9 | 2 |
| HPV56 | L2 | 10 | 2 |
| HPV56 | L2 | 11 | 2 |
| HPV56 | L2 | 8 | 280 |
| HPV56 | L2 | 11 | 280 |
| HPV56 | L2 | 11 | 366 |
| HPV56 | L2 | 11 | 112 |
| HPV56 | L2 | 11 | 408 |
| HPV56 | L2 | 8 | 249 |
| HPV56 | L2 | 11 | 152 |
| HPV56 | L2 | 9 | 236 |
| HPV56 | L2 | 11 | 236 |
| HPV56 | L2 | 8 | 31 |
| HPV56 | L2 | 11 | 31 |

TABLE XVI-continued

HLA-A3 Motif Peptides

| 1 | 2 | 3 | 4 |
|---|---|---|---|
| HPV56 | L2 | 8 | 47 |
| HPV56 | L2 | 8 | 351 |
| HPV56 | L2 | 9 | 321 |
| HPV56 | L2 | 11 | 348 |
| HPV56 | L2 | 8 | 424 |
| HPV56 | L2 | 9 | 455 |
| HPV56 | L2 | 10 | 455 |
| HPV56 | L2 | 8 | 443 |
| HPV56 | L2 | 9 | 443 |
| HPV56 | L2 | 10 | 443 |
| HPV56 | L2 | 8 | 431 |

TABLE XVI

A. HPV6A
HLA-A3 Motif Peptides

| 2 | 3 | 4 |
|---|---|---|
| E6 | 9 | 62 |
| E6 | 10 | 62 |
| L1 | 8 | 234 |
| L1 | 10 | 234 |
| L1 | 11 | 234 |
| L2 | 8 | 329 |
| E1 | 8 | 206 |
| E1 | 11 | 206 |
| L1 | 8 | 489 |
| L1 | 9 | 489 |
| L1 | 11 | 489 |
| L2 | 10 | 340 |
| L2 | 11 | 340 |
| E4 | 9 | 2 |
| E4 | 11 | 2 |
| E6 | 8 | 63 |
| E6 | 9 | 63 |
| E6 | 11 | 63 |
| E6 | 9 | 65 |
| E2 | 10 | 10 |
| L1 | 9 | 98 |
| L1 | 9 | 235 |
| L1 | 10 | 235 |
| L1 | 11 | 235 |
| E1 | 8 | 235 |
| E1 | 11 | 235 |
| E1 | 10 | 377 |
| E1 | 9 | 392 |
| E1 | 10 | 392 |
| E1 | 11 | 392 |
| L2 | 8 | 238 |
| L2 | 9 | 275 |
| L2 | 10 | 275 |
| E1 | 11 | 637 |
| L2 | 10 | 116 |
| L2 | 11 | 116 |
| E1 | 8 | 193 |
| E1 | 10 | 193 |
| E1 | 11 | 190 |
| E1 | 9 | 144 |
| E1 | 10 | 144 |
| E2 | 8 | 3 |
| L2 | 10 | 286 |
| L2 | 11 | 286 |
| E1 | 9 | 112 |
| E1 | 10 | 112 |
| L2 | 10 | 140 |
| L1 | 11 | 420 |
| E1 | 10 | 475 |
| E2 | 8 | 331 |
| E1 | 8 | 65 |
| E1 | 11 | 65 |
| E4 | 8 | 14 |

TABLE XVI-continued

A. HPV6A
HLA-A3 Motif Peptides

| 2 | 3 | 4 |
|---|---|---|
| L2 | 11 | 228 |
| E1 | 10 | 207 |
| L1 | 8 | 81 |
| L2 | 8 | 421 |
| E6 | 8 | 37 |
| E6 | 10 | 37 |
| E6 | 11 | 37 |
| L1 | 11 | 203 |
| L1 | 8 | 487 |
| L1 | 9 | 487 |
| L1 | 10 | 487 |
| L1 | 11 | 487 |
| L2 | 11 | 12 |
| E2 | 8 | 322 |
| E2 | 9 | 322 |
| E2 | 10 | 322 |
| L2 | 8 | 288 |
| L2 | 9 | 288 |
| L2 | 11 | 288 |
| L1 | 8 | 36 |
| L1 | 11 | 36 |
| E1 | 8 | 330 |
| L1 | 9 | 342 |
| L1 | 8 | 22 |
| E1 | 8 | 407 |
| E1 | 9 | 407 |
| E1 | 10 | 407 |
| L2 | 9 | 14 |
| E1 | 8 | 525 |
| E6 | 9 | 10 |
| E6 | 11 | 10 |
| E6 | 9 | 86 |
| E1 | 8 | 77 |
| E1 | 9 | 77 |
| E1 | 10 | 77 |
| E1 | 9 | 101 |
| L1 | 10 | 43 |
| L1 | 11 | 43 |
| E2 | 8 | 231 |
| E2 | 9 | 231 |
| E2 | 10 | 231 |
| E2 | 11 | 231 |
| L1 | 8 | 483 |
| L1 | 10 | 483 |
| L1 | 11 | 483 |
| E1 | 8 | 601 |
| E1 | 11 | 601 |
| E6 | 8 | 64 |
| E6 | 10 | 64 |
| E1 | 9 | 234 |
| E2 | 8 | 124 |
| L1 | 8 | 157 |
| L1 | 11 | 157 |
| L1 | 10 | 341 |
| E1 | 8 | 406 |
| E1 | 9 | 406 |
| E1 | 10 | 406 |
| E1 | 11 | 406 |
| E7 | 10 | 57 |
| E7 | 9 | 58 |
| E6 | 8 | 66 |
| E1 | 11 | 215 |
| E2 | 9 | 299 |
| E2 | 10 | 299 |
| E2 | 11 | 299 |
| E7 | 8 | 59 |
| E2 | 8 | 161 |
| E2 | 11 | 161 |
| L1 | 10 | 221 |
| E6 | 11 | 67 |
| E2 | 8 | 296 |
| E2 | 10 | 35 |
| E2 | 11 | 35 |
| L1 | 11 | 374 |

TABLE XVI-continued

A. HPV6A
HLA-A3 Motif Peptides

| 2 | 3 | 4 |
|---|---|---|
| L1 | 8 | 99 |
| E1 | 9 | 14 |
| L1 | 8 | 171 |
| E5 | 9 | 131 |
| E6 | 11 | 31 |
| E1 | 8 | 640 |
| E2 | 11 | 9 |
| E1 | 10 | 111 |
| E1 | 11 | 111 |
| E1 | 10 | 516 |
| E1 | 9 | 524 |
| E2 | 8 | 230 |
| E2 | 9 | 230 |
| E2 | 10 | 230 |
| E2 | 11 | 230 |
| L1 | 10 | 24 |
| L1 | 11 | 24 |
| E1 | 8 | 405 |
| E1 | 9 | 405 |
| E1 | 10 | 405 |
| E1 | 11 | 405 |
| E1 | 10 | 523 |
| L2 | 8 | 343 |
| L2 | 11 | 343 |
| E1 | 8 | 385 |
| E1 | 9 | 385 |
| E1 | 10 | 49 |
| E2 | 10 | 122 |
| 'L1 | 9 | 193 |
| L1 | 11 | 193 |
| E1 | 9 | 542 |
| E1 | 10 | 542 |
| E1 | 11 | 542 |
| E7 | 9 | 41 |
| E7 | 11 | 41 |
| E1 | 9 | 161 |
| E1 | 8 | 631 |
| E1 | 9 | 631 |
| E1 | 9 | 369 |
| E1 | 10 | 369 |
| L1 | 8 | 219 |
| L1 | 9 | 219 |
| E1 | 10 | 170 |
| L2 | 9 | 278 |
| L2 | 11 | 278 |
| E6 | 8 | 96 |
| E6 | 10 | 96 |
| L2 | 8 | 322 |
| L2 | 9 | 322 |
| E1 | 8 | 570 |
| E1 | 9 | 570 |
| E1 | 10 | 570 |
| E7 | 8 | 88 |
| E7 | 10 | 88 |
| E1 | 10 | 222 |
| E2 | 8 | 313 |
| E2 | 10 | 313 |
| E1 | 11 | 81 |
| E2 | 8 | 25 |
| E2 | 10 | 25 |
| E7 | 11 | 14 |
| E1 | 9 | 203 |
| E1 | 10 | 203 |
| E1 | 11 | 203 |
| L1 | 9 | 195 |
| E1 | 9 | 42 |
| E1 | 11 | 134 |
| L2 | 10 | 266 |
| L2 | 11 | 266 |
| E1 | 11 | 53 |
| E7 | 8 | 44 |
| E7 | 9 | 44 |
| L1 | 11 | 84 |
| E2 | 9 | 141 |
| L2 | 10 | 344 |
| L1 | 9 | 198 |
| L1 | 10 | 198 |
| E1 | 11 | 166 |
| E1 | 11 | 73 |
| L1 | 11 | 269 |
| L1 | 10 | 411 |
| L2 | 8 | 30 |
| E5 | 10 | 99 |
| E6 | 11 | 99 |
| L2 | 8 | 258 |
| E1 | 10 | 178 |
| E2 | 9 | 174 |
| L2 | 8 | 274 |
| L2 | 10 | 274 |
| L2 | 11 | 274 |
| E1 | 10 | 143 |
| E1 | 11 | 143 |
| E2 | 9 | 2 |
| L2 | 10 | 173 |
| E1 | 8 | 336 |
| E1 | 8 | 180 |
| E1 | 10 | 180 |
| E1 | 11 | 180 |
| E1 | 8 | 62 |
| E1 | 11 | 62 |
| L1 | 9 | 299 |
| E1 | 10 | 100 |
| E2 | 9 | 229 |
| E2 | 10 | 229 |
| E2 | 11 | 229 |
| E1 | 11 | 627 |
| E1 | 10 | 36 |
| E1 | 8 | 630 |
| E1 | 9 | 630 |
| E1 | 10 | 630 |
| E1 | 10 | 41 |
| L1 | 11 | 410 |
| L2 | 9 | 257 |
| E6 | 9 | 69 |
| E6 | 10 | 69 |
| E6 | 11 | 69 |
| E1 | 8 | 453 |
| E1 | 9 | 453 |
| E1 | 10 | 453 |
| L2 | 9 | 255 |
| L2 | 11 | 255 |
| E1 | 8 | 172 |
| E1 | 10 | 172 |
| E1 | 9 | 10 |
| E4 | 10 | 89 |
| E1 | 9 | 375 |
| L2 | 9 | 332 |
| L2 | 10 | 332 |
| E1 | 8 | 105 |
| E1 | 10 | 105 |
| L2 | 10 | 120 |
| E6 | 8 | 42 |
| E6 | 11 | 42 |
| L1 | 9 | 453 |
| L1 | 10 | 453 |
| L1 | 11 | 453 |
| E1 | 9 | 197 |
| E1 | 10 | 197 |
| E1 | 11 | 197 |
| E1 | 8 | 604 |
| E1 | 10 | 604 |
| E1 | 11 | 604 |
| E1 | 9 | 131 |
| L2 | 8 | 334 |
| E2 | 11 | 74 |
| E1 | 8 | 417 |
| E2 | 8 | 100 |
| E2 | 9 | 100 |

TABLE XVI-continued

A. HPV6A
HLA-A3 Motif Peptides

| 2 | 3 | 4 |
|---|---|---|
| E2 | 11 | 100 |
| L2 | 9 | 110 |
| E6 | 9 | 2 |
| E1 | 8 | 373 |
| E1 | 9 | 373 |
| E1 | 11 | 373 |
| E1 | 10 | 103 |
| E2 | 8 | 80 |
| E2 | 8 | 293 |
| E2 | 9 | 293 |
| E2 | 10 | 293 |
| E2 | 11 | 293 |
| E2 | 8 | 210 |
| E2 | 8 | 39 |
| E2 | 9 | 39 |
| E7 | 11 | 39 |
| E6 | 11 | 113 |
| E2 | 8 | 118 |
| L1 | 8 | 443 |
| E2 | 10 | 205 |
| E5 | 8 | 2 |
| E5 | 9 | 2 |
| L1 | 8 | 206 |
| L1 | 9 | 80 |
| L1 | 8 | 252 |
| L1 | 9 | 252 |
| L2 | 8 | 442 |
| E6 | 9 | 33 |
| E1 | 8 | 487 |
| E2 | 11 | 121 |
| L2 | 8 | 346 |
| E2 | 9 | 312 |
| E2 | 11 | 312 |
| L1 | 11 | 88 |
| E1 | 9 | 595 |
| E1 | 8 | 386 |
| L1 | 10 | 243 |
| L1 | 11 | 243 |
| E5 | 10 | 67 |
| L1 | 9 | 244 |
| L1 | 10 | 244 |
| L1 | 11 | 244 |
| E1 | 10 | 242 |
| E1 | 11 | 242 |
| E1 | 10 | 216 |
| E1 | 9 | 50 |
| E1 | 8 | 220 |
| E1 | 9 | 220 |
| E6 | 9 | 126 |
| E6 | 11 | 126 |
| E1 | 8 | 454 |
| E1 | 9 | 454 |
| L2 | 8 | 428 |
| L2 | 10 | 428 |
| E1 | 9 | 494 |
| L1 | 8 | 463 |
| L1 | 10 | 463 |
| E5 | 9 | 68 |
| E4 | 10 | 21 |
| E4 | 11 | 21 |
| E1 | 8 | 393 |
| E1 | 9 | 393 |
| E1 | 10 | 393 |
| L2 | 10 | 398 |
| E1 | 9 | 446 |
| L1 | 8 | 245 |
| L1 | 9 | 245 |
| L1 | 10 | 245 |
| L1 | 11 | 245 |
| E1 | 10 | 4S7 |
| L2 | 11 | 239 |
| L2 | 8 | 276 |
| L2 | 9 | 276 |
| L2 | 11 | 276 |
| E1 | 9 | 18 |
| L2 | 9 | 263 |
| L1 | 8 | 49 |
| L1 | 8 | 450 |
| E1 | 9 | 587 |
| E1 | 11 | 587 |
| E2 | 8 | 171 |
| L1 | 9 | 326 |
| L2 | 9 | 117 |
| L2 | 10 | 117 |
| L2 | 8 | 314 |
| E2 | 9 | 123 |
| L1 | 9 | 156 |
| E1 | 10 | 13 |
| E1 | 8 | 384 |
| E1 | 9 | 384 |
| E1 | 10 | 384 |
| E1 | 10 | 160 |
| L1 | 8 | 194 |
| L1 | 10 | 194 |
| L1 | 9 | 239 |
| L1 | 10 | 239 |
| L1 | 8 | 200 |
| E1 | 11 | 241 |
| L2 | 9 | 433 |
| L2 | 10 | 433 |
| L2 | 11 | 433 |
| E1 | 11 | 159 |
| L1 | 9 | 132 |
| E6 | 9 | 57 |
| L1 | 9 | 318 |
| L2 | 11 | 58 |
| E1 | 9 | 243 |
| E1 | 10 | 243 |
| E1 | 9 | 194 |
| E2 | 9 | 156 |
| E2 | 10 | 156 |
| E1 | 8 | 350 |
| E1 | 9 | 217 |
| E1 | 11 | 217 |
| L2 | 11 | 292 |
| L2 | 8 | 223 |
| E2 | 9 | 55 |
| E1 | 9 | 273 |
| E1 | 10 | 273 |
| E1 | 11 | 273 |
| E1 | 8 | 11 |
| L2 | 9 | 431 |
| L2 | 11 | 431 |
| L1 | 11 | 130 |
| L2 | 10 | 62 |
| E1 | 11 | 431 |
| L1 | 8 | 293 |
| L1 | 11 | 293 |
| L2 | 9 | 303 |
| L2 | 10 | 303 |
| E1 | 8 | 632 |
| E2 | 10 | 179 |
| E2 | 9 | 189 |
| E1 | 10 | 191 |
| L2 | 11 | 215 |
| L2 | 10 | 25 |
| L2 | 8 | 64 |
| E1 | 11 | 436 |
| L2 | 9 | 60 |
| E1 | 8 | 145 |
| E1 | 9 | 145 |
| E7 | 11 | 85 |
| L1 | 8 | 407 |
| L1 | 9 | 407 |
| L2 | 9 | 413 |
| E1 | 9 | 467 |
| L1 | 9 | 222 |
| E4 | 9 | 90 |

TABLE XVI-continued

A. HPV6A
HLA-A3 Motif Peptides

| 2 | 3 | 4 |
|---|---|---|
| E1 | 8 | 316 |
| E1 | 9 | 316 |
| L1 | 9 | 111 |
| L1 | 9 | 478 |
| L1 | 10 | 478 |
| E2 | 9 | 242 |
| L1 | 10 | 113 |
| L1 | 11 | 113 |
| E1 | 10 | 415 |
| E2 | 8 | 330 |
| E2 | 9 | 330 |
| L1 | 9 | 35 |
| L2 | 11 | 265 |
| E6 | 8 | 79 |
| E1 | 10 | 508 |
| E1 | 11 | 508 |
| E6 | 8 | 71 |
| E6 | 9 | 71 |
| E6 | 10 | 71 |
| E1 | 8 | 349 |
| E1 | 9 | 349 |
| E7 | 8 | 2 |
| E1 | 10 | 466 |
| L2 | 8 | 312 |
| L2 | 9 | 312 |
| L2 | 10 | 312 |
| E2 | 11 | 53 |
| E2 | 10 | 255 |
| E6 | 8 | 119 |
| E6 | 10 | 119 |
| E1 | 8 | 264 |
| E2 | 10 | 78 |
| E2 | 11 | 310 |
| E4 | 8 | 10 |
| E4 | 9 | 10 |
| E4 | 10 | 10 |
| E2 | 9 | 338 |
| E1 | 9 | 246 |
| E2 | 10 | 149 |
| E2 | 11 | 149 |
| L2 | 8 | 3 |
| L2 | 9 | 3 |
| L2 | 10 | 3 |
| E6 | 9 | 25 |
| E6 | 11 | 25 |
| L2 | 10 | 306 |
| L2 | 11 | 306 |
| E1 | 9 | 581 |
| L2 | 8 | 149 |
| L1 | 9 | 361 |
| L1 | 11 | 361 |
| E2 | 9 | 29 |
| E2 | 10 | 29 |
| E1 | 8 | 502 |
| E1 | 8 | 376 |
| E1 | 11 | 376 |
| E1 | 11 | 474 |
| L2 | 11 | 326 |
| L2 | 9 | 287 |
| L2 | 10 | 287 |
| E1 | 8 | 370 |
| E1 | 9 | 370 |
| E1 | 11 | 370 |
| L1 | 8 | 220 |
| L1 | 11 | 220 |
| L1 | 8 | 319 |
| E1 | 8 | 51 |
| L1 | 9 | 218 |
| L1 | 10 | 218 |
| E1 | 8 | 569 |
| E1 | 9 | 569 |
| E1 | 10 | 569 |
| E1 | 11 | 569 |
| E1 | 8 | 221 |
| E1 | 11 | 221 |
| E6 | 8 | 13 |
| L1 | 11 | 370 |
| L1 | 9 | 32 |
| L2 | 8 | 313 |
| L2 | 9 | 313 |
| E1 | 10 | 334 |
| E2 | 10 | 54 |
| E2 | 9 | 256 |
| L2 | 8 | 299 |
| L2 | 10 | 299 |
| L2 | 10 | 59 |
| E5 | 8 | 21 |
| L1 | 8 | 272 |
| E5 | 10 | 31 |
| L2 | 8 | 279 |
| L2 | 10 | 279 |
| E6 | 9 | 97 |
| L2 | 9 | 141 |
| E1 | 8 | 195 |
| E1 | 11 | 195 |
| L2 | 11 | 178 |
| E5 | 9 | 32 |
| L2 | 10 | 44 |
| L2 | 11 | 44 |
| E5 | 8 | 17 |
| E6 | 9 | 120 |
| L2 | 9 | 180 |
| E1 | 11 | 492 |
| E1 | 9 | 500 |
| E1 | 10 | 500 |
| E1 | 11 | 327 |
| L2 | 8 | 323 |
| E1 | 9 | 106 |
| E2 | 8 | 315 |
| E2 | 11 | 315 |
| L1 | 10 | 421 |
| L2 | 9 | 429 |
| L2 | 11 | 429 |
| E1 | 8 | 56 |
| E1 | 10 | 56 |
| E1 | 8 | 571 |
| E1 | 9 | 571 |
| E1 | 11 | 571 |
| L1 | 9 | 376 |
| L1 | 10 | 376 |
| E2 | 8 | 267 |
| E2 | 10 | 267 |
| E2 | 11 | 267 |
| E1 | 9 | 341 |
| L2 | 8 | 82 |
| L2 | 10 | 131 |
| L2 | 8 | 247 |
| E7 | 9 | 89 |
| E1 | 9 | 476 |
| E1 | 11 | 476 |
| L2 | 9 | 121 |
| L2 | 9 | 104 |
| E5 | 10 | 34 |
| E2 | 9 | 45 |
| L1 | 8 | 486 |
| L1 | 9 | 486 |
| L1 | 10 | 486 |
| L1 | 11 | 486 |
| E2 | 10 | 298 |
| E2 | 11 | 298 |
| E1 | 8 | 200 |
| E2 | 11 | 34 |
| E1 | 8 | 404 |
| E1 | 9 | 404 |
| E1 | 10 | 404 |
| E1 | 11 | 404 |
| E1 | 10 | 202 |
| E1 | 11 | 202 |

TABLE XVI-continued

A. HPV6A
HLA-A3 Motif Peptides

| 2 | 3 | 4 |
|---|---|---|
| L1 | 10 | 79 |
| E1 | 10 | 211 |
| E1 | 11 | 460 |
| L1 | 8 | 462 |
| L1 | 9 | 462 |
| L1 | 11 | 462 |
| L1 | 9 | 449 |
| E2 | 11 | 68 |
| E2 | 10 | 155 |
| E2 | 11 | 155 |
| E1 | 9 | 433 |
| E6 | 8 | 73 |
| E6 | 10 | 73 |
| E6 | 11 | 73 |
| E2 | 8 | 351 |
| E2 | 9 | 351 |
| E1 | 8 | 312 |
| E1 | 10 | 312 |
| E2 | 8 | 359 |
| E1 | 9 | 254 |
| E1 | 10 | 254 |
| E1 | 11 | 254 |
| E6 | 9 | 128 |
| E1 | 9 | 357 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| E1 | 8 | 228 |
| E1 | 8 | 286 |
| E1 | 11 | 286 |
| E1 | 11 | 484 |
| E6 | 8 | 18 |
| E1 | 10 | 231 |
| E2 | 11 | 115 |
| L1 | 10 | 56 |
| E2 | 9 | 165 |
| E2 | 11 | 165 |
| E1 | 8 | 518 |
| L2 | 8 | 34 |
| E2 | 8 | 147 |
| E2 | 9 | 147 |
| E6 | 8 | 116 |
| E6 | 9 | 116 |
| E6 | 10 | 116 |
| E6 | 11 | 116 |
| E1 | 10 | 121 |
| E6 | 8 | 52 |
| E6 | 10 | 52 |
| E6 | 11 | 52 |
| E1 | 10 | 283 |
| E1 | 11 | 283 |
| E2 | 8 | 63 |
| E2 | 10 | 63 |
| L1 | 8 | 61 |
| L1 | 10 | 61 |
| L1 | 11 | 61 |
| L1 | 8 | 19 |
| L1 | 11 | 19 |
| L1 | 9 | 71 |
| L1 | 10 | 71 |
| L1 | 11 | 71 |
| E4 | 9 | 13 |
| L1 | 8 | 42 |
| L1 | 11 | 42 |
| L1 | 11 | 340 |
| E6 | 8 | 111 |
| E6 | 9 | 111 |
| E6 | 11 | 106 |
| E6 | 10 | 16 |
| E4 | 8 | 35 |
| L1 | 8 | 373 |
| E1 | 8 | 110 |
| E1 | 11 | 110 |
| E1 | 11 | 522 |
| E1 | 10 | 541 |
| E1 | 11 | 541 |
| E7 | 9 | 87 |
| E7 | 11 | 87 |
| L1 | 8 | 454 |
| L1 | 9 | 454 |
| L1 | 10 | 454 |
| E6 | 8 | 98 |
| E6 | 11 | 98 |
| L2 | 8 | 142 |
| E2 | 10 | 311 |
| L1 | 8 | 87 |
| L1 | 11 | 242 |
| L2 | 8 | 452 |
| L2 | 11 | 397 |
| L1 | 10 | 302 |
| L1 | 11 | 302 |
| E1 | 10 | 66 |
| E1 | 11 | 66 |
| E6 | 8 | 54 |
| E6 | 9 | 54 |
| E6 | 10 | 54 |
| L1 | 10 | 325 |
| L1 | 9 | 161 |
| E1 | 8 | 495 |
| E1 | 8 | 209 |
| L1 | 11 | 459 |
| L1 | 8 | 110 |
| L1 | 10 | 110 |
| L2 | 10 | 107 |
| E1 | 8 | 255 |
| E1 | 9 | 255 |
| E1 | 10 | 255 |
| L1 | 9 | 271 |
| E5 | 8 | 16 |
| E5 | 9 | 16 |
| E6 | 8 | 101 |
| E6 | 9 | 101 |
| E1 | 9 | 223 |
| L2 | 10 | 179 |
| E2 | 9 | 314 |
| E2 | 9 | 266 |
| E2 | 11 | 266 |
| L2 | 9 | 246 |
| E5 | 8 | 33 |
| E5 | 11 | 33 |
| L1 | 8 | 41 |
| L1 | 9 | 41 |
| E1 | 11 | 540 |
| E1 | 9 | 208 |
| E4 | 9 | 8 |
| E4 | 10 | 8 |
| E4 | 11 | 8 |
| E4 | 8 | 24 |
| E1 | 8 | 198 |
| E1 | 9 | 198 |
| E1 | 10 | 198 |
| E5 | 9 | 59 |
| E5 | 10 | 59 |
| L1 | 9 | 464 |
| E5 | 8 | 69 |
| E5 | 11 | 69 |
| E5 | 8 | 60 |
| E5 | 9 | 60 |
| E5 | 8 | 72 |
| E5 | 10 | 72 |
| E1 | 8 | 276 |
| E1 | 11 | 276 |

TABLE XVI-continued

A. HPV6A
HLA-A3 Motif Peptides

| 2 | 3 | 4 |
|---|---|---|
| E1 | 11 | 563 |
| L1 | 8 | 378 |
| L1 | 10 | 378 |
| E1 | 8 | 218 |
| E1 | 10 | 218 |
| E1 | 11 | 218 |
| L1 | 9 | 439 |
| L1 | 11 | 439 |
| E1 | 9 | 458 |
| E1 | 9 | 605 |
| E1 | 10 | 605 |
| L2 | 9 | 390 |
| L2 | 10 | 240 |
| E1 | 8 | 132 |
| E1 | 8 | 358 |
| E1 | 9 | 358 |
| E4 | 8 | 81 |
| E6 | 8 | 121 |
| E5 | 10 | 70 |
| E1 | 9 | 115 |
| E1 | 10 | 115 |
| E1 | 11 | 115 |
| E6 | 9 | 38 |
| E6 | 10 | 38 |
| E6 | 11 | 38 |
| E5 | 8 | 61 |
| L2 | 9 | 338 |
| E5 | 9 | 73 |
| E5 | 11 | 73 |
| E5 | 8 | 47 |
| E1 | 10 | 277 |
| E1 | 8 | 279 |
| E1 | 10 | 279 |
| L2 | 10 | 293 |
| L1 | 9 | 295 |
| L1 | 11 | 295 |
| E1 | 10 | 564 |
| E7 | 11 | 67 |
| L1 | 9 | 233 |
| L1 | 11 | 233 |
| E4 | 10 | 1 |
| L2 | 8 | 1 |
| L2 | 9 | 1 |
| L2 | 10 | 1 |
| L2 | 11 | 1 |
| E1 | 8 | 409 |
| E1 | 11 | 409 |
| L2 | 8 | 277 |
| L2 | 10 | 277 |
| E2 | 10 | 129 |
| L1 | 9 | 251 |
| L1 | 10 | 251 |
| L2 | 10 | 412 |
| E1 | 8 | 546 |
| E1 | 9 | 546 |
| E1 | 8 | 421 |
| E1 | 9 | 421 |
| E1 | 10 | 421 |
| E2 | 8 | 151 |
| E2 | 9 | 151 |
| L1 | 8 | 196 |
| L1 | 11 | 196 |
| E1 | 8 | 19 |
| L1 | 11 | 154 |
| E1 | 8 | 274 |
| E1 | 9 | 274 |
| E1 | 10 | 274 |
| L2 | 11 | 115 |
| E2 | 8 | 71 |
| E6 | 9 | 36 |
| E6 | 11 | 36 |
| E1 | 8 | 607 |
| E1 | 10 | 607 |
| E1 | 9 | 329 |
| E1 | 9 | 600 |
| E2 | 8 | 295 |
| E2 | 9 | 295 |
| E6 | 10 | 130 |
| E6 | 8 | 30 |
| E1 | 10 | 368 |
| E1 | 11 | 368 |
| E2 | 8 | 305 |
| L1 | 9 | 205 |
| E2 | 8 | 170 |
| E2 | 9 | 170 |
| E1 | 8 | 158 |
| L2 | 8 | 175 |
| L1 | 10 | 317 |
| E1 | 11 | 598 |
| L1 | 8 | 406 |
| L1 | 9 | 406 |
| L1 | 10 | 406 |
| E1 | 9 | 568 |
| E1 | 10 | 568 |
| E1 | 11 | 568 |
| E1 | 10 | 451 |
| E1 | 11 | 451 |
| L1 | 10 | 31 |
| E1 | 9 | 55 |
| E1 | 11 | 55 |
| E2 | 10 | 265 |
| E4 | 8 | 23 |
| E4 | 9 | 23 |
| L1 | 10 | 438 |
| E1 | 8 | 397 |
| E1 | 11 | 397 |
| L1 | 9 | 352 |
| L1 | 10 | 352 |
| E1 | 9 | 59 |
| E1 | 11 | 59 |
| E1 | 8 | 395 |
| E1 | 10 | 395 |
| E2 | 10 | 281 |
| E2 | 8 | 22 |
| E2 | 11 | 22 |
| E1 | 10 | 184 |
| L2 | 9 | 38 |
| E2 | 10 | 348 |
| E2 | 11 | 348 |
| L2 | 9 | 237 |
| L2 | 11 | 285 |
| L2 | 11 | 139 |
| E5 | 8 | 78 |
| L1 | 8 | 482 |
| L1 | 9 | 482 |
| L1 | 11 | 482 |
| L2 | 8 | 438 |
| L2 | 9 | 438 |
| L2 | 10 | 438 |
| L2 | 11 | 438 |
| E2 | 8 | 247 |
| E2 | 9 | 247 |
| E1 | 9 | 528 |
| E1 | 11 | 528 |
| L2 | 10 | 272 |
| L2 | 8 | 355 |
| L2 | 8 | 403 |
| E1 | 11 | 302 |
| E7 | 9 | 18 |
| L1 | 9 | 433 |
| E1 | 8 | 480 |
| L2 | 9 | 29 |
| L1 | 8 | 228 |
| L1 | 11 | 228 |
| E1 | 8 | 594 |
| E1 | 10 | 594 |
| E1 | 10 | 226 |
| E4 | 11 | 20 |

TABLE XVI-continued

A. HPV6A
HLA-A3 Motif Peptides

| 2 | 3 | 4 |
|---|---|---|
| E1 | 11 | 456 |
| E1 | 10 | 592 |
| L2 | 8 | 214 |
| L1 | 10 | 217 |
| L1 | 11 | 217 |
| L2 | 10 | 189 |
| E1 | 8 | 94 |
| E1 | 8 | 442 |
| E6 | 9 | 110 |
| E6 | 10 | 110 |
| E4 | 8 | 34 |
| E4 | 9 | 34 |
| L2 | 8 | 451 |
| L2 | 9 | 451 |
| L1 | 8 | 160 |
| L1 | 10 | 160 |
| L1 | 9 | 109 |
| L1 | 11 | 109 |
| E2 | 8 | 61 |
| E2 | 10 | 61 |
| L2 | 10 | 389 |
| L2 | 10 | 337 |
| E1 | 8 | 513 |
| L2 | 11 | 411 |
| E1 | 8 | 545 |
| E1 | 9 | 545 |
| E1 | 10 | 545 |
| L1 | 10 | 291 |
| L2 | 9 | 80 |
| L2 | 10 | 80 |
| L2 | 11 | 102 |
| L1 | 9 | 391 |
| L2 | 9 | 408 |
| E2 | 9 | 354 |
| E1 | 8 | 182 |
| E1 | 9 | 182 |
| L1 | 11 | 426 |
| L2 | 11 | 207 |
| L1 | 9 | 90 |
| L2 | 9 | 426 |
| L2 | 10 | 426 |
| E5 | 10 | 19 |
| L1 | 9 | 266 |
| L2 | 8 | 212 |
| L2 | 10 | 212 |
| L1 | 10 | 16 |
| L1 | 11 | 16 |
| E2 | 10 | 222 |
| L2 | 11 | 418 |
| L2 | 9 | 363 |
| L2 | 8 | 91 |
| L2 | 9 | 328 |
| E1 | 9 | 399 |
| E1 | 9 | 64 |
| E4 | 9 | 38 |
| E4 | 10 | 38 |
| E4 | 11 | 38 |
| E4 | 10 | 44 |
| E7 | 8 | 70 |
| L1 | 9 | 170 |
| L2 | 8 | 342 |
| L2 | 9 | 342 |
| L1 | 10 | 192 |
| E6 | 9 | 95 |
| E6 | 11 | 95 |
| L1 | 11 | 137 |
| E7 | 9 | 43 |
| E7 | 10 | 43 |
| E2 | 8 | 140 |
| E2 | 10 | 140 |
| E5 | 11 | 66 |
| E1 | 11 | 355 |
| E2 | 9 | 163 |
| E2 | 11 | 163 |
| E1 | 10 | 445 |
| E2 | 10 | 289 |
| L2 | 8 | 262 |
| L2 | 10 | 262 |
| E2 | 8 | 291 |
| E2 | 10 | 291 |
| E2 | 11 | 291 |
| L2 | 11 | 43 |
| E6 | 8 | 28 |
| E6 | 10 | 28 |
| E6 | 11 | 15 |
| L1 | 8 | 151 |
| L1 | 9 | 372 |
| L1 | 11 | 301 |
| L1 | 11 | 324 |
| E6 | 10 | 50 |
| E4 | 9 | 4 |
| E4 | 11 | 4 |
| L1 | 10 | 232 |
| L1 | 8 | 250 |
| L1 | 10 | 250 |
| L1 | 11 | 250 |
| E2 | 9 | 76 |
| E1 | 8 | 305 |
| L2 | 8 | 400 |
| L2 | 11 | 400 |
| E1 | 8 | 314 |
| E1 | 10 | 314 |
| E1 | 11 | 314 |
| L1 | 11 | 466 |
| E2 | 10 | 245 |
| E2 | 11 | 245 |
| L1 | 9 | 417 |
| E2 | 8 | 103 |
| E2 | 9 | 103 |
| E2 | 10 | 103 |
| E2 | 11 | 103 |
| E2 | 8 | 233 |
| E2 | 9 | 233 |
| L1 | 10 | 149 |
| E1 | 10 | 128 |
| E1 | 9 | 344 |
| L2 | 8 | 231 |
| L2 | 9 | 231 |
| E2 | 11 | 57 |
| E1 | 8 | 205 |
| E1 | 9 | 205 |
| E1 | 10 | 391 |
| E1 | 11 | 391 |
| L1 | 9 | 53 |
| L2 | 8 | 5 |
| L2 | 10 | 5 |
| L2 | 8 | 11 |
| E2 | 8 | 108 |
| E1 | 9 | 639 |
| E1 | 8 | 169 |
| E1 | 11 | 169 |
| E6 | 10 | 125 |
| E1 | 8 | 281 |
| E1 | 8 | 383 |
| E1 | 9 | 383 |
| E1 | 10 | 383 |
| E1 | 11 | 383 |
| E6 | 8 | 56 |
| E6 | 10 | 56 |
| E2 | 8 | 113 |
| E2 | 9 | 113 |
| L2 | 8 | 291 |
| L1 | 11 | 470 |
| L2 | 10 | 302 |
| L2 | 11 | 302 |
| E2 | 10 | 241 |
| L2 | 9 | 298 |
| L2 | 11 | 298 |

TABLE XVI-continued

A. HPV6A
HLA-A3 Motif Peptides

| 2 | 3 | 4 |
|---|---|---|
| L2 | 10 | 449 |
| L2 | 11 | 449 |
| E1 | 9 | 109 |
| L1 | 8 | 241 |
| L2 | 8 | 281 |
| L2 | 10 | 281 |
| L2 | 11 | 281 |
| L2 | 10 | 245 |
| L1 | 9 | 40 |
| L1 | 10 | 40 |
| E2 | 8 | 303 |
| E2 | 10 | 303 |
| L2 | 8 | 308 |
| L2 | 9 | 308 |
| L2 | 11 | 308 |
| L1 | 9 | 472 |
| L1 | 10 | 472 |
| L1 | 9 | 334 |
| E1 | 9 | 288 |
| L1 | 8 | 476 |
| L1 | 11 | 476 |
| L2 | 11 | 68 |
| L1 | 8 | 29 |
| L1 | 9 | 279 |
| L2 | 8 | 221 |
| L2 | 10 | 221 |
| L1 | 8 | 140 |
| L1 | 9 | 140 |
| E1 | 11 | 583 |
| L1 | 8 | 488 |
| L1 | 9 | 488 |
| L1 | 10 | 488 |
| L1 | 9 | 379 |
| L2 | 8 | 111 |
| E6 | 8 | 3 |
| L2 | 8 | 181 |
| E2 | 8 | 283 |
| L2 | 10 | 13 |
| E6 | 10 | 9 |
| L1 | 8 | 353 |
| L1 | 9 | 353 |
| L2 | 11 | 352 |
| E1 | 9 | 219 |
| E1 | 10 | 219 |
| E1 | 10 | 493 |
| L1 | 8 | 440 |
| L1 | 10 | 440 |
| L1 | 11 | 440 |
| E1 | 11 | 12 |
| L2 | 8 | 432 |
| L2 | 10 | 432 |
| L2 | 11 | 432 |
| L1 | 10 | 131 |
| L1 | 8 | 115 |
| L1 | 9 | 115 |
| L2 | 8 | 309 |
| L2 | 10 | 309 |
| L2 | 11 | 309 |
| E2 | 11 | 261 |
| L2 | 10 | 401 |
| L1 | 9 | 292 |
| L2 | 9 | 63 |
| E1 | 9 | 315 |
| E1 | 10 | 315 |
| E1 | 8 | 43 |
| E1 | 10 | 135 |
| L1 | 8 | 63 |
| L1 | 9 | 63 |
| L1 | 10 | 467 |
| E1 | 8 | 547 |
| L2 | 8 | 153 |
| L2 | 9 | 267 |
| L2 | 10 | 267 |
| E5 | 11 | 30 |
| E1 | 8 | 422 |
| E1 | 9 | 422 |
| E2 | 8 | 207 |
| E2 | 11 | 207 |
| L1 | 8 | 474 |
| L1 | 10 | 474 |
| E1 | 8 | 247 |
| L1 | 10 | 375 |
| L1 | 11 | 375 |
| L2 | 8 | 81 |
| L2 | 9 | 81 |
| L2 | 10 | 103 |
| E1 | 8 | 60 |
| E1 | 10 | 60 |
| L1 | 9 | 86 |
| L2 | 11 | 106 |
| E4 | 9 | 80 |
| L1 | 10 | 294 |
| E6 | 11 | 23 |
| L2 | 8 | 304 |
| L2 | 9 | 304 |
| E2 | 9 | 150 |
| E2 | 10 | 150 |
| E2 | 9 | 282 |
| L1 | 9 | 297 |
| L1 | 11 | 297 |
| L1 | 11 | 451 |
| L2 | 8 | 133 |
| L2 | 8 | 391 |
| L1 | 8 | 473 |
| L1 | 9 | 473 |
| L1 | 11 | 473 |
| L1 | 10 | 85 |
| E4 | 10 | 79 |
| L1 | 9 | 38 |
| L1 | 11 | 38 |
| L1 | 10 | 37 |
| E2 | 8 | 224 |
| L2 | 9 | 209 |
| L2 | 11 | 209 |
| E2 | 10 | 316 |
| E2 | 11 | 316 |
| L1 | 9 | 347 |
| L1 | 10 | 347 |
| E2 | 10 | 23 |
| E2 | 9 | 180 |
| E5 | 10 | 14 |
| E5 | 11 | 14 |
| L1 | 8 | 335 |
| L2 | 9 | 241 |
| L2 | 8 | 210 |
| L2 | 10 | 210 |
| E1 | 8 | 289 |
| E2 | 8 | 190 |
| E2 | 9 | 317 |
| E2 | 10 | 317 |
| L1 | 8 | 348 |
| L1 | 9 | 348 |
| L1 | 11 | 348 |
| L1 | 8 | 392 |
| E2 | 8 | 40 |
| E5 | 10 | 45 |
| L2 | 10 | 260 |
| E1 | 9 | 185 |
| L2 | 11 | 164 |
| L2 | 11 | 145 |
| L1 | 8 | 343 |
| E6 | 8 | 40 |
| E6 | 9 | 40 |
| E6 | 10 | 40 |
| E1 | 9 | 192 |
| E1 | 11 | 192 |
| L2 | 9 | 420 |
| L2 | 8 | 409 |

TABLE XVI-continued

A. HPV6A
HLA-A3 Motif Peptides

| 2 | 3 | 4 |
|---|---|---|
| L2 | 10 | 216 |
| E1 | 8 | 233 |
| E1 | 10 | 233 |
| E7 | 11 | 56 |
| E2 | 8 | 160 |
| E2 | 9 | 160 |
| L1 | 11 | 224 |
| L2 | 9 | 26 |
| L1 | 9 | 422 |
| L1 | 11 | 422 |
| L1 | 11 | 23 |
| E2 | 9 | 24 |
| E2 | 11 | 24 |
| L2 | 11 | 235 |
| E2 | 8 | 142 |
| L2 | 9 | 345 |
| E1 | 8 | 588 |
| E1 | 10 | 588 |
| L2 | 11 | 406 |
| E1 | 8 | 586 |
| E1 | 10 | 586 |
| L1 | 8 | 199 |
| L1 | 9 | 199 |
| E1 | 10 | 437 |
| L2 | 11 | 424 |
| E1 | 10 | 167 |
| L2 | 8 | 430 |
| L2 | 10 | 430 |
| L2 | 8 | 61 |
| L2 | 11 | 61 |
| L2 | 11 | 24 |
| E1 | 8 | 146 |
| L1 | 10 | 477 |
| L1 | 11 | 477 |
| E1 | 8 | 15 |
| L2 | 10 | 69 |
| L2 | 11 | 69 |
| L2 | 8 | 39 |
| E6 | 9 | 12 |
| E2 | 8 | 355 |
| L2 | 11 | 130 |
| E7 | 10 | 86 |
| L1 | 8 | 408 |
| L1 | 10 | 270 |
| E5 | 9 | 15 |
| E5 | 10 | 15 |
| E5 | 9 | 71 |
| E5 | 11 | 71 |
| E6 | 8 | 26 |
| E6 | 10 | 26 |
| L1 | 8 | 377 |
| L1 | 9 | 377 |
| L1 | 11 | 377 |
| E1 | 8 | 408 |
| E1 | 9 | 408 |
| E2 | 11 | 128 |
| EE | 11 | 8 |
| L2 | 9 | 147 |
| L2 | 10 | 147 |
| L2 | 9 | 152 |
| E1 | 8 | 566 |
| E1 | 11 | 566 |
| L2 | 9 | 132 |
| E4 | 11 | 78 |
| L2 | 10 | 208 |
| L1 | 10 | 346 |
| L1 | 11 | 346 |
| E5 | 11 | 13 |
| L1 | 8 | 280 |
| E5 | 11 | 44 |
| E2 | 11 | 97 |
| E6 | 8 | 39 |
| E6 | 9 | 39 |
| E6 | 10 | 39 |
| E6 | 11 | 39 |
| E1 | 9 | 232 |
| E1 | 11 | 232 |
| L1 | 8 | 223 |
| E1 | 9 | 585 |
| E1 | 11 | 585 |
| E6 | 8 | 11 |
| E6 | 10 | 11 |
| L1 | 8 | 91 |
| L1 | 11 | 332 |
| L2 | 10 | 151 |
| L1 | 11 | 345 |
| L2 | 11 | 150 |
| E6 | 8 | 87 |
| E4 | 8 | 91 |
| E2 | 10 | 116 |
| E1 | 8 | 345 |
| E1 | 11 | 498 |
| E1 | 8 | 78 |
| E1 | 9 | 78 |
| E2 | 10 | 334 |
| L1 | 9 | 57 |
| L1 | 11 | 57 |
| E1 | 8 | 317 |
| L2 | 8 | 339 |
| L2 | 11 | 339 |
| E1 | 8 | 239 |
| L1 | 9 | 21 |
| E7 | 8 | 90 |
| E5 | 8 | 74 |
| E5 | 10 | 74 |
| E5 | 11 | 74 |
| E2 | 8 | 152 |
| E1 | 11 | 515 |
| E1 | 11 | 48 |
| E7 | 10 | 40 |
| L1 | 10 | 197 |
| L1 | 11 | 197 |
| E6 | 10 | 32 |
| L2 | 8 | 427 |
| L2 | 9 | 427 |
| L2 | 11 | 427 |
| L1 | 11 | 69 |
| L1 | 10 | 155 |
| L1 | 9 | 44 |
| L1 | 10 | 44 |
| L1 | 11 | 44 |
| L2 | 9 | 222 |
| E1 | 8 | 477 |
| E1 | 10 | 477 |
| E1 | 11 | 477 |
| L1 | 8 | 112 |
| L1 | 11 | 112 |
| E1 | 11 | 346 |
| E1 | 11 | 333 |
| E5 | 9 | 20 |
| L2 | 11 | 31 |
| E1 | 10 | 499 |
| E1 | 11 | 499 |
| E6 | 9 | 53 |
| E6 | 10 | 53 |
| E6 | 11 | 53 |
| E2 | 8 | 30 |
| E2 | 9 | 30 |
| E6 | 9 | 100 |
| E6 | 10 | 100 |
| E4 | 8 | 7 |
| E4 | 10 | 7 |
| E4 | 11 | 7 |
| E1 | 8 | 275 |
| E1 | 9 | 275 |
| L1 | 8 | 73 |
| L1 | 9 | 73 |
| E5 | 9 | 46 |

TABLE XVI-continued

A. HPV6A
HLA-A3 Motif Peptides

| 2 | 3 | 4 |
|---|---|---|
| E1 | 9 | 278 |
| E1 | 11 | 278 |
| E2 | 9 | 64 |
| L1 | 9 | 114 |
| L1 | 10 | 114 |
| L1 | 9 | 62 |
| L1 | 10 | 62 |
| E2 | 9 | 206 |
| L1 | 9 | 484 |
| L1 | 10 | 484 |
| L1 | 11 | 484 |
| L1 | 9 | 17 |
| L1 | 10 | 17 |
| L2 | 8 | 105 |
| E1 | 8 | 92 |
| E1 | 10 | 92 |
| L1 | 8 | 296 |
| L1 | 10 | 296 |
| E2 | 9 | 223 |
| L2 | 11 | 259 |
| L2 | 10 | 419 |
| L2 | 8 | 364 |
| L2 | 10 | 165 |
| L1 | 8 | 27 |
| L1 | 9 | 27 |
| L1 | 10 | 27 |
| L2 | 10 | 146 |
| L2 | 11 | 146 |
| E1 | 9 | 565 |
| E1 | 10 | 584 |
| E2 | 11 | 333 |
| L1 | 8 | 327 |
| E2 | 9 | 335 |
| E1 | 8 | 238 |
| E1 | 9 | 238 |
| L1 | 10 | 20 |
| E2 | 9 | 349 |
| E2 | 10 | 349 |
| E2 | 11 | 349 |
| L1 | 8 | 72 |
| L1 | 9 | 72 |
| L1 | 10 | 72 |
| L1 | 8 | 58 |
| L1 | 10 | 58 |
| L1 | 11 | 58 |
| E2 | 10 | 58 |
| E2 | 11 | 58 |
| E5 | 8 | 3 |
| E7 | 10 | 68 |
| L1 | 10 | 97 |
| E2 | 8 | 321 |
| E2 | 9 | 321 |
| E2 | 10 | 321 |
| E2 | 11 | 321 |
| E1 | 10 | 17 |
| E1 | 9 | 322 |
| E1 | 10 | 272 |
| E1 | 11 | 272 |
| L2 | 8 | 47 |
| E1 | 8 | 426 |
| E5 | 8 | 36 |
| E1 | 10 | 340 |
| E1 | 9 | 530 |
| E1 | 8 | 464 |
| E5 | 10 | 58 |
| E5 | 11 | 58 |
| L1 | 8 | 308 |
| E1 | 8 | 510 |
| E1 | 9 | 510 |
| E1 | 11 | 510 |
| E2 | 8 | 92 |
| E2 | 10 | 145 |
| E2 | 11 | 145 |
| E1 | 9 | 237 |
| E1 | 10 | 237 |
| E6 | 10 | 61 |
| E6 | 11 | 61 |
| E1 | 10 | 262 |
| E1 | 11 | 380 |
| E6 | 10 | 85 |
| E1 | 8 | 76 |
| E1 | 9 | 76 |
| E1 | 10 | 76 |
| E1 | 11 | 76 |
| E6 | 10 | 46 |
| E6 | 11 | 46 |
| E5 | 8 | 76 |
| E5 | 9 | 76 |
| E5 | 10 | 76 |
| L2 | 9 | 321 |
| L2 | 10 | 321 |
| L2 | 8 | 441 |
| L2 | 9 | 441 |
| E1 | 9 | 486 |
| L1 | 9 | 48 |
| L2 | 9 | 319 |
| L2 | 11 | 319 |
| L1 | 8 | 238 |
| L1 | 10 | 238 |
| L1 | 11 | 238 |
| E2 | 11 | 178 |
| E2 | 10 | 188 |
| E1 | 8 | 137 |
| E4 | 8 | 12 |
| E4 | 10 | 12 |
| L2 | 8 | 435 |
| L2 | 9 | 435 |
| L2 | 10 | 435 |
| L2 | 11 | 435 |
| E1 | 9 | 579 |
| E1 | 11 | 579 |
| L1 | 9 | 230 |
| L1 | 8 | 358 |
| L2 | 11 | 296 |
| E5 | 9 | 44 |
| E2 | 9 | 159 |
| E2 | 10 | 159 |
| L1 | 9 | 350 |
| L1 | 11 | 350 |
| E1 | 10 | 402 |
| E1 | 11 | 402 |
| E4 | 9 | 6 |
| E4 | 11 | 6 |
| E2 | 8 | 168 |
| E2 | 10 | 168 |
| E2 | 11 | 168 |
| L2 | 8 | 71 |
| L2 | 9 | 71 |
| L1 | 10 | 10 |
| E2 | 10 | 138 |
| L1 | 11 | 415 |
| E1 | 9 | 91 |
| E1 | 11 | 91 |
| L1 | 8 | 26 |
| L1 | 9 | 26 |
| L1 | 10 | 26 |
| L1 | 11 | 26 |
| E2 | 8 | 131 |

TABLE XVI

B. HPV6B
HLA-A3 Motif Peptides

| 2 | 3 | 4 |
|---|---|---|
| E6 | 9 | 62 |
| E6 | 10 | 62 |
| L1 | 8 | 234 |
| L1 | 10 | 234 |
| L1 | 11 | 234 |
| L2 | 8 | 329 |
| E5A | 8 | 9 |
| E1 | 8 | 206 |
| E1 | 11 | 206 |
| L1 | 8 | 489 |
| L1 | 9 | 489 |
| L1 | 11 | 489 |
| L2 | 10 | 340 |
| L2 | 11 | 340 |
| E4 | 9 | 12 |
| E4 | 11 | 12 |
| E6 | 8 | 63 |
| E6 | 9 | 63 |
| E6 | 11 | 63 |
| E6 | 9 | 65 |
| E2 | 10 | 10 |
| L1 | 9 | 98 |
| L1 | 9 | 235 |
| L1 | 10 | 235 |
| L1 | 11 | 235 |
| E1 | 10 | 377 |
| E1 | 9 | 392 |
| E1 | 10 | 392 |
| E1 | 11 | 392 |
| L2 | 8 | 238 |
| L2 | 9 | 275 |
| L2 | 10 | 275 |
| E1 | 11 | 637 |
| L2 | 10 | 116 |
| L2 | 11 | 116 |
| E1 | 8 | 193 |
| E1 | 10 | 193 |
| E1 | 11 | 190 |
| E1 | 9 | 144 |
| E1 | 10 | 144 |
| E2 | 8 | 3 |
| L2 | 10 | 286 |
| L2 | 11 | 286 |
| E1 | 9 | 112 |
| E1 | 10 | 112 |
| L2 | 10 | 140 |
| L1 | 11 | 420 |
| E1 | 10 | 475 |
| E1 | 8 | 65 |
| E1 | 11 | 65 |
| E4 | 8 | 24 |
| L2 | 11 | 228 |
| E1 | 10 | 207 |
| L1 | 8 | 81 |
| L2 | 8 | 421 |
| E6 | 8 | 37 |
| E6 | 10 | 37 |
| E6 | 11 | 37 |
| L1 | 11 | 203 |
| L1 | 8 | 487 |
| L1 | 9 | 487 |
| L1 | 10 | 487 |
| L1 | 11 | 487 |
| L2 | 11 | 12 |
| L2 | 8 | 288 |
| L2 | 9 | 288 |
| L2 | 11 | 288 |
| E2 | 8 | 322 |
| E2 | 9 | 322 |
| E2 | 10 | 322 |
| L1 | 8 | 36 |
| L1 | 11 | 36 |
| E1 | 8 | 330 |
| L1 | 9 | 342 |
| L1 | 8 | 22 |
| E1 | 8 | 407 |
| E1 | 9 | 407 |
| E1 | 10 | 407 |
| L2 | 9 | 14 |
| E1 | 8 | 525 |
| E6 | 9 | 10 |
| E6 | 11 | 10 |
| E6 | 9 | 86 |
| E1 | 8 | 77 |
| E1 | 9 | 77 |
| E1 | 10 | 77 |
| E1 | 9 | 101 |
| L1 | 10 | 43 |
| L1 | 11 | 43 |
| E5B | 9 | 36 |
| E5B | 11 | 36 |
| E2 | 8 | 231 |
| E2 | 9 | 231 |
| E2 | 10 | 231 |
| E2 | 11 | 231 |
| L1 | 8 | 483 |
| L1 | 10 | 483 |
| L1 | 11 | 483 |
| E1 | 11 | 601 |
| E6 | 8 | 64 |
| E6 | 10 | 64 |
| E2 | 8 | 124 |
| L1 | 8 | 157 |
| L1 | 11 | 157 |
| L1 | 10 | 341 |
| E1 | 8 | 406 |
| E1 | 9 | 406 |
| E1 | 10 | 406 |
| E1 | 11 | 406 |
| E7 | 10 | 57 |
| E7 | 9 | 58 |
| E6 | 8 | 66 |
| E1 | 11 | 215 |
| E2 | 9 | 299 |
| E2 | 10 | 299 |
| E2 | 11 | 299 |
| E7 | 8 | 59 |
| E2 | 8 | 161 |
| E2 | 11 | 161 |
| L1 | 10 | 221 |
| E1 | 9 | 234 |
| E6 | 11 | 67 |
| E2 | 8 | 296 |
| E2 | 10 | 35 |
| E2 | 11 | 35 |
| L1 | 11 | 374 |
| L1 | 8 | 99 |
| E1 | 9 | 14 |
| L1 | 8 | 171 |
| E6 | 9 | 131 |
| E6 | 11 | 31 |
| E1 | 8 | 640 |
| E2 | 11 | 9 |
| E1 | 10 | 111 |
| E1 | 11 | 111 |
| E1 | 10 | 516 |
| E1 | 9 | 524 |
| E2 | 8 | 230 |
| E2 | 9 | 230 |
| E2 | 10 | 230 |
| E2 | 11 | 230 |
| L1 | 10 | 24 |
| L1 | 11 | 24 |
| E1 | 8 | 405 |
| E1 | 9 | 405 |
| E1 | 10 | 405 |
| E1 | 11 | 405 |
| E1 | 10 | 523 |

TABLE XVI-continued

B. HPV6B
HLA-A3 Motif Peptides

| 2 | 3 | 4 |
|---|---|---|
| L2 | 8 | 343 |
| L2 | 11 | 343 |
| E5B | 8 | 55 |
| E1 | 8 | 385 |
| E1 | 9 | 385 |
| E1 | 10 | 49 |
| E2 | 10 | 122 |
| L1 | 9 | 193 |
| L1 | 11 | 193 |
| E1 | 9 | 542 |
| E1 | 10 | 542 |
| E1 | 11 | 542 |
| E7 | 9 | 41 |
| E7 | 11 | 41 |
| E1 | 9 | 161 |
| E1 | 8 | 631 |
| E1 | 9 | 631 |
| E4 | 10 | 99 |
| E1 | 9 | 369 |
| E1 | 10 | 369 |
| L1 | 8 | 219 |
| L1 | 9 | 219 |
| E1 | 10 | 170 |
| L2 | 9 | 278 |
| L2 | 11 | 278 |
| E6 | 8 | 96 |
| E6 | 10 | 96 |
| L2 | 8 | 322 |
| L2 | 9 | 322 |
| E1 | 8 | 570 |
| E1 | 9 | 570 |
| E1 | 10 | 570 |
| E2 | 8 | 25 |
| E2 | 10 | 25 |
| E1 | 10 | 222 |
| E2 | 8 | 313 |
| E2 | 10 | 313 |
| E1 | 11 | 81 |
| E7 | 11 | 14 |
| E1 | 9 | 203 |
| E1 | 10 | 203 |
| E1 | 11 | 203 |
| L1 | 9 | 195 |
| E2 | 9 | 338 |
| E1 | 9 | 42 |
| E1 | 11 | 134 |
| L2 | 10 | 266 |
| L2 | 11 | 266 |
| E1 | 11 | 53 |
| E7 | 8 | 44 |
| E7 | 9 | 44 |
| L1 | 11 | 84 |
| L2 | 10 | 344 |
| L1 | 9 | 198 |
| L1 | 10 | 198 |
| E1 | 11 | 166 |
| E1 | 11 | 73 |
| L1 | 11 | 269 |
| E5B | 11 | 11 |
| L1 | 10 | 411 |
| L2 | 8 | 30 |
| E6 | 10 | 99 |
| E6 | 11 | 99 |
| L2 | 8 | 258 |
| E2 | 11 | 348 |
| E1 | 10 | 178 |
| E2 | 9 | 174 |
| E2 | 10 | 174 |
| L2 | 8 | 274 |
| L2 | 10 | 274 |
| L2 | 11 | 274 |
| E1 | 10 | 143 |
| E1 | 11 | 143 |
| E2 | 9 | 2 |

TABLE XVI-continued

B. HPV6B
HLA-A3 Motif Peptides

| 2 | 3 | 4 |
|---|---|---|
| L2 | 10 | 173 |
| E1 | 8 | 336 |
| E1 | 8 | 180 |
| E1 | 10 | 180 |
| E1 | 11 | 180 |
| E1 | 8 | 62 |
| E1 | 11 | 62 |
| L1 | 9 | 299 |
| E1 | 10 | 100 |
| E2 | 9 | 229 |
| E2 | 10 | 229 |
| E2 | 11 | 229 |
| E1 | 11 | 627 |
| E1 | 10 | 36 |
| E1 | 8 | 630 |
| E1 | 9 | 630 |
| E1 | 10 | 630 |
| E1 | 8 | 574 |
| E1 | 10 | 574 |
| E1 | 10 | 41 |
| L1 | 11 | 410 |
| L2 | 9 | 257 |
| E6 | 9 | 69 |
| E6 | 10 | 69 |
| E6 | 11 | 69 |
| E1 | 8 | 453 |
| E1 | 9 | 453 |
| E1 | 10 | 453 |
| L2 | 9 | 255 |
| L2 | 11 | 255 |
| E1 | 8 | 172 |
| E1 | 10 | 172 |
| E1 | 9 | 10 |
| E1 | 9 | 375 |
| L2 | 9 | 332 |
| L2 | 10 | 332 |
| E1 | 8 | 105 |
| E1 | 10 | 105 |
| L2 | 10 | 120 |
| E6 | 8 | 42 |
| E6 | 9 | 42 |
| E6 | 11 | 42 |
| L1 | 9 | 453 |
| L1 | 10 | 453 |
| L1 | 11 | 453 |
| E1 | 9 | 197 |
| E1 | 10 | 197 |
| E1 | 11 | 197 |
| E1 | 8 | 604 |
| E1 | 10 | 604 |
| E1 | 11 | 604 |
| E1 | 9 | 131 |
| E2 | 11 | 17 |
| L2 | 8 | 334 |
| E2 | 11 | 74 |
| E1 | 8 | 417 |
| E2 | 8 | 100 |
| E2 | 9 | 100 |
| E2 | 11 | 100 |
| L2 | 9 | 110 |
| E6 | 9 | 2 |
| E1 | 8 | 373 |
| E1 | 9 | 373 |
| E1 | 11 | 373 |
| E1 | 10 | 103 |
| E2 | 8 | 80 |
| E2 | 8 | 293 |
| E2 | 9 | 293 |
| E2 | 10 | 293 |
| E2 | 11 | 293 |
| E2 | 8 | 210 |
| E2 | 8 | 39 |
| E2 | 9 | 39 |
| E7 | 11 | 39 |

TABLE XVI-continued

B. HPV6B
HLA-A3 Motif Peptides

| 2 | 3 | 4 |
|---|---|---|
| E6 | 11 | 113 |
| E2 | 8 | 118 |
| L1 | 8 | 443 |
| E2 | 10 | 205 |
| E5A | 8 | 2 |
| E5A | 9 | 2 |
| L1 | 8 | 206 |
| L1 | 9 | 80 |
| L1 | 8 | 252 |
| L1 | 9 | 252 |
| L2 | 8 | 442 |
| E6 | 9 | 33 |
| E1 | 8 | 487 |
| E2 | 11 | 121 |
| L2 | 8 | 346 |
| E2 | 9 | 312 |
| E2 | 11 | 312 |
| L1 | 11 | 88 |
| E1 | 9 | 595 |
| E1 | 8 | 386 |
| L1 | 10 | 243 |
| L1 | 11 | 243 |
| E5A | 10 | 67 |
| L1 | 9 | 244 |
| L1 | 10 | 244 |
| L1 | 11 | 244 |
| E1 | 10 | 242 |
| E1 | 11 | 242 |
| E1 | 10 | 216 |
| E1 | 9 | 50 |
| E1 | 8 | 220 |
| E1 | 9 | 220 |
| E6 | 9 | 126 |
| E6 | 11 | 126 |
| E5A | 8 | 16 |
| E5A | 9 | 16 |
| E1 | 8 | 454 |
| E1 | 9 | 454 |
| L2 | 8 | 428 |
| L2 | 10 | 428 |
| E1 | 9 | 494 |
| L1 | 8 | 463 |
| L1 | 10 | 463 |
| E5A | 9 | 68 |
| E4 | 10 | 31 |
| E4 | 11 | 31 |
| E1 | 8 | 393 |
| E1 | 9 | 393 |
| E1 | 10 | 393 |
| L2 | 10 | 397 |
| E1 | 9 | 446 |
| L1 | 8 | 245 |
| L1 | 9 | 245 |
| L1 | 10 | 245 |
| L1 | 11 | 245 |
| L2 | 11 | 239 |
| E1 | 10 | 457 |
| L2 | 8 | 276 |
| L2 | 9 | 276 |
| L2 | 11 | 276 |
| E1 | 9 | 18 |
| L2 | 9 | 263 |
| L1 | 8 | 49 |
| L1 | 8 | 450 |
| E1 | 9 | 587 |
| E1 | 11 | 587 |
| E2 | 8 | 171 |
| L1 | 9 | 326 |
| L2 | 9 | 117 |
| L2 | 10 | 117 |
| E4 | 8 | 2 |
| E4 | 11 | 2 |
| L2 | 8 | 314 |
| E2 | 9 | 123 |
| L1 | 9 | 156 |
| E1 | 10 | 13 |
| E1 | 8 | 384 |
| E1 | 9 | 384 |
| E1 | 10 | 384 |
| E1 | 10 | 160 |
| E5B | 8 | 39 |
| E5B | 9 | 39 |
| L1 | 8 | 194 |
| L1 | 10 | 194 |
| L1 | 9 | 239 |
| L1 | 10 | 239 |
| L1 | 8 | 200 |
| E1 | 11 | 241 |
| L2 | 9 | 433 |
| L2 | 10 | 433 |
| L2 | 11 | 433 |
| E1 | 11 | 159 |
| L1 | 9 | 132 |
| E6 | 9 | 57 |
| L1 | 9 | 318 |
| L2 | 11 | 58 |
| E1 | 9 | 243 |
| E1 | 10 | 243 |
| E1 | 9 | 194 |
| E2 | 9 | 156 |
| E2 | 10 | 156 |
| E1 | 8 | 350 |
| E5B | 8 | 28 |
| E5B | 9 | 28 |
| E1 | 9 | 217 |
| E1 | 11 | 217 |
| L2 | 11 | 292 |
| E5B | 8 | 15 |
| L2 | 8 | 223 |
| E5B | 9 | 25 |
| E5B | 10 | 25 |
| E5B | 11 | 25 |
| E2 | 9 | 55 |
| E1 | 9 | 273 |
| E1 | 10 | 273 |
| E1 | 11 | 273 |
| E1 | 8 | 11 |
| L2 | 9 | 431 |
| L2 | 11 | 431 |
| L1 | 11 | 130 |
| L2 | 10 | 62 |
| E1 | 11 | 431 |
| L1 | 8 | 293 |
| L1 | 11 | 293 |
| L2 | 9 | 303 |
| L2 | 10 | 303 |
| E1 | 8 | 632 |
| E2 | 10 | 179 |
| E2 | 9 | 189 |
| E1 | 10 | 191 |
| L2 | 11 | 215 |
| L2 | 10 | 25 |
| L2 | 8 | 64 |
| E1 | 11 | 436 |
| L2 | 9 | 60 |
| E1 | 8 | 145 |
| E1 | 9 | 145 |
| L1 | 8 | 407 |
| L1 | 9 | 407 |
| E7 | 11 | 85 |
| L2 | 10 | 412 |
| E1 | 9 | 467 |
| L1 | 9 | 222 |
| E4 | 9 | 100 |
| E1 | 8 | 316 |
| E1 | 9 | 316 |
| L1 | 9 | 111 |
| L1 | 9 | 478 |

TABLE XVI-continued

B. HPV6B
HLA-A3 Motif Peptides

| 2 | 3 | 4 |
|---|---|---|
| L1 | 10 | 478 |
| E2 | 9 | 242 |
| L1 | 10 | 113 |
| L1 | 11 | 113 |
| E1 | 10 | 415 |
| E2 | 8 | 330 |
| L1 | 9 | 35 |
| L2 | 11 | 265 |
| E6 | 8 | 79 |
| E1 | 10 | 508 |
| E1 | 11 | 508 |
| E6 | 8 | 71 |
| E6 | 9 | 71 |
| E6 | 10 | 71 |
| E1 | 8 | 349 |
| E1 | 9 | 349 |
| E7 | 8 | 2 |
| E1 | 10 | 466 |
| L2 | 8 | 312 |
| L2 | 9 | 312 |
| L2 | 10 | 312 |
| E2 | 11 | 53 |
| E2 | 10 | 255 |
| E6 | 8 | 119 |
| E6 | 10 | 119 |
| E1 | 8 | 264 |
| E2 | 10 | 78 |
| E2 | 11 | 310 |
| E6 | 10 | 50 |
| E4 | 8 | 20 |
| E4 | 9 | 20 |
| E4 | 10 | 20 |
| E1 | 9 | 246 |
| E2 | 10 | 149 |
| E2 | 11 | 149 |
| L2 | 8 | 3 |
| L2 | 9 | 3 |
| L2 | 10 | 3 |
| E5B | 9 | 42 |
| E5B | 10 | 42 |
| E6 | 9 | 25 |
| E5 | 11 | 25 |
| L2 | 10 | 306 |
| L2 | 11 | 306 |
| E1 | 9 | 581 |
| L2 | 8 | 149 |
| L1 | 9 | 361 |
| L1 | 11 | 361 |
| E2 | 9 | 29 |
| E2 | 10 | 29 |
| E1 | 8 | 502 |
| E5A | 9 | 8 |
| E1 | 8 | 376 |
| E1 | 11 | 376 |
| E1 | 11 | 474 |
| L2 | 11 | 326 |
| L2 | 9 | 287 |
| L2 | 10 | 287 |
| E1 | 8 | 370 |
| E1 | 9 | 370 |
| E1 | 11 | 370 |
| L1 | 8 | 220 |
| L1 | 11 | 220 |
| L1 | 8 | 319 |
| E1 | 8 | 51 |
| L1 | 9 | 218 |
| L1 | 10 | 218 |
| E1 | 8 | 569 |
| E1 | 9 | 569 |
| E1 | 10 | 569 |
| E1 | 11 | 569 |
| E1 | 8 | 221 |
| E1 | 11 | 221 |
| E6 | 8 | 13 |
| L1 | 11 | 370 |
| L1 | 9 | 32 |
| L2 | 8 | 313 |
| L2 | 9 | 313 |
| E1 | 10 | 334 |
| E4 | 8 | 6 |
| E4 | 11 | 6 |
| E2 | 10 | 54 |
| E2 | 9 | 256 |
| L2 | 8 | 299 |
| L2 | 10 | 299 |
| L2 | 10 | 59 |
| E5A | 8 | 21 |
| L1 | 8 | 272 |
| E5A | 10 | 31 |
| L2 | 8 | 279 |
| L2 | 10 | 279 |
| E6 | 9 | 97 |
| L2 | 9 | 141 |
| E1 | 8 | 195 |
| E1 | 11 | 195 |
| L2 | 11 | 178 |
| E5A | 9 | 32 |
| L2 | 10 | 44 |
| L2 | 11 | 44 |
| E5A | 8 | 17 |
| E5 | 9 | 120 |
| L2 | 9 | 180 |
| E1 | 11 | 492 |
| E2 | 11 | 356 |
| E1 | 9 | 500 |
| E1 | 10 | 500 |
| E1 | 11 | 327 |
| L2 | 8 | 323 |
| E1 | 9 | 106 |
| E2 | 8 | 315 |
| E2 | 11 | 315 |
| L1 | 10 | 421 |
| L2 | 9 | 429 |
| L2 | 11 | 429 |
| E1 | 8 | 56 |
| E1 | 10 | 56 |
| E1 | 8 | 571 |
| E1 | 9 | 571 |
| E1 | 11 | 571 |
| L1 | 9 | 376 |
| L1 | 10 | 376 |
| E2 | 8 | 267 |
| E2 | 10 | 267 |
| E2 | 11 | 267 |
| E1 | 9 | 341 |
| L2 | 8 | 82 |
| L2 | 10 | 131 |
| L2 | 8 | 247 |
| E7 | 9 | 89 |
| E5B | 11 | 23 |
| E1 | 9 | 476 |
| E1 | 11 | 476 |
| L2 | 9 | 121 |
| L2 | 9 | 104 |
| E5A | 10 | 34 |
| E2 | 9 | 45 |
| L1 | 8 | 486 |
| L1 | 9 | 486 |
| L1 | 10 | 486 |
| L1 | 11 | 486 |
| E2 | 10 | 298 |
| E2 | 11 | 298 |
| E1 | 8 | 200 |
| E5B | 8 | 44 |
| E2 | 11 | 34 |
| E5B | 11 | 47 |
| E1 | 8 | 404 |
| E1 | 9 | 404 |

TABLE XVI-continued

B. HPV6B
HLA-A3 Motif Peptides

| 2 | 3 | 4 |
|---|---|---|
| E1 | 10 | 404 |
| E1 | 11 | 404 |
| E4 | 11 | 98 |
| E1 | 10 | 202 |
| E1 | 11 | 202 |
| L1 | 10 | 79 |
| E1 | 10 | 211 |
| E1 | 11 | 460 |
| L1 | 8 | 462 |
| L1 | 9 | 462 |
| L1 | 11 | 462 |
| L1 | 9 | 449 |
| E2 | 11 | 68 |
| E2 | 10 | 155 |
| E2 | 11 | 155 |
| E1 | 9 | 433 |
| E6 | 8 | 73 |
| E6 | 10 | 73 |
| E6 | 11 | 73 |
| E2 | 8 | 351 |
| E2 | 9 | 351 |
| E1 | 8 | 312 |
| E1 | 10 | 312 |
| E2 | 8 | 359 |
| E1 | 9 | 254 |
| E1 | 10 | 254 |
| E1 | 11 | 254 |
| E6 | 9 | 128 |
| E1 | 9 | 357 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| E1 | 8 | 286 |
| E1 | 11 | 286 |
| E1 | 11 | 484 |
| E6 | 8 | 18 |
| E1 | 10 | 231 |
| E2 | 11 | 115 |
| L1 | 10 | 55 |
| E2 | 9 | 165 |
| E2 | 11 | 165 |
| E1 | 8 | 518 |
| L2 | 8 | 34 |
| E2 | 8 | 147 |
| E2 | 9 | 147 |
| E6 | 8 | 116 |
| E6 | 9 | 116 |
| E6 | 10 | 116 |
| E6 | 11 | 116 |
| E1 | 10 | 121 |
| E6 | 8 | 52 |
| E6 | 10 | 52 |
| E6 | 11 | 52 |
| E1 | 10 | 283 |
| E1 | 11 | 283 |
| E2 | 8 | 63 |
| E2 | 10 | 63 |
| L1 | 8 | 61 |
| L1 | 10 | 61 |
| L1 | 11 | 61 |
| L1 | 8 | 19 |
| L1 | 11 | 19 |
| L1 | 9 | 71 |
| L1 | 10 | 71 |
| L1 | 11 | 71 |
| E4 | 9 | 23 |
| L1 | 8 | 42 |
| L1 | 11 | 42 |
| L1 | 11 | 340 |
| E6 | 8 | 111 |
| E6 | 9 | 111 |
| E6 | 11 | 106 |
| E6 | 10 | 16 |
| E4 | 8 | 45 |
| L1 | 8 | 373 |
| E1 | 8 | 110 |
| E1 | 11 | 110 |
| E1 | 11 | 522 |
| E1 | 10 | 541 |
| E1 | 11 | 541 |
| L1 | 8 | 454 |
| L1 | 9 | 454 |
| L1 | 10 | 454 |
| E6 | 8 | 98 |
| E6 | 11 | 98 |
| L2 | 8 | 142 |
| E1 | 8 | 235 |
| E1 | 11 | 235 |
| E2 | 10 | 311 |
| L1 | 8 | 87 |
| L1 | 11 | 242 |
| L2 | 8 | 452 |
| L2 | 11 | 396 |
| L1 | 10 | 302 |
| L1 | 11 | 302 |
| E1 | 10 | 66 |
| E1 | 11 | 66 |
| E6 | 8 | 54 |
| E6 | 9 | 54 |
| E6 | 10 | 54 |
| L1 | 10 | 325 |
| L1 | 9 | 161 |
| E1 | 8 | 495 |
| E1 | 8 | 209 |
| E5B | 8 | 27 |
| E5B | 9 | 27 |
| E5B | 10 | 27 |
| E5B | 8 | 14 |
| E5B | 9 | 14 |
| L1 | 11 | 459 |
| L1 | 8 | 110 |
| L1 | 10 | 110 |
| L2 | 10 | 107 |
| E1 | 8 | 255 |
| E1 | 9 | 255 |
| E1 | 10 | 255 |
| L1 | 9 | 271 |
| E6 | 8 | 101 |
| E6 | 9 | 101 |
| E1 | 9 | 223 |
| L2 | 10 | 179 |
| E2 | 9 | 314 |
| E2 | 9 | 266 |
| E2 | 11 | 266 |
| L2 | 9 | 246 |
| E5A | 8 | 33 |
| E5A | 11 | 33 |
| L1 | 8 | 41 |
| L1 | 9 | 41 |
| E1 | 11 | 540 |
| E1 | 9 | 208 |
| E4 | 9 | 18 |
| E4 | 10 | 18 |
| E4 | 11 | 18 |
| E4 | 8 | 34 |
| E1 | 8 | 198 |
| E1 | 9 | 198 |
| E1 | 10 | 198 |
| E5B | 8 | 29 |
| E5A | 9 | 59 |
| E5A | 10 | 59 |
| L1 | 9 | 464 |

TABLE XVI-continued

B. HPV6B
HLA-A3 Motif Peptides

| 2 | 3 | 4 |
|---|---|---|
| E1 | 8 | 279 |
| E1 | 10 | 279 |
| E5A | 8 | 69 |
| E5A 11 | 69 | |
| E5A | 8 | 60 |
| E5A | 9 | 60 |
| E5A | 8 | 72 |
| E5A | 10 | 72 |
| E1 | 8 | 276 |
| E1 | 11 | 276 |
| E1 | 11 | 563 |
| E5B | 11 | 31 |
| L1 | 8 | 378 |
| L1 | 10 | 378 |
| E1 | 8 | 218 |
| E1 | 10 | 218 |
| E1 | 11 | 218 |
| L1 | 9 | 439 |
| L1 | 11 | 439 |
| L2 | 8 | 390 |
| E1 | 9 | 605 |
| E1 | 10 | 605 |
| L2 | 10 | 240 |
| E1 | 8 | 132 |
| E1 | 8 | 358 |
| E1 | 9 | 358 |
| E4 | 8 | 91 |
| E6 | 8 | 121 |
| E1 | 9 | 458 |
| E5A | 10 | 70 |
| E1 | 9 | 115 |
| E1 | 10 | 115 |
| E1 | 11 | 115 |
| E6 | 9 | 38 |
| E6 | 10 | 38 |
| E6 | 11 | 38 |
| E5A | 8 | 61 |
| L2 | 9 | 338 |
| E5A | 9 | 73 |
| E5A | 11 | 73 |
| E1 | 10 | 277 |
| E5A | 8 | 47 |
| L2 | 10 | 293 |
| L1 | 9 | 295 |
| L1 | 11 | 295 |
| E2 | 10 | 222 |
| E1 | 10 | 564 |
| E7 | 11 | 67 |
| L1 | 9 | 233 |
| L1 | 11 | 233 |
| E4 | 10 | 11 |
| L2 | 8 | 1 |
| L2 | 9 | 1 |
| L2 | 10 | 1 |
| L2 | 11 | 1 |
| E1 | 8 | 409 |
| E1 | 11 | 409 |
| L2 | 8 | 277 |
| L2 | 10 | 277 |
| E2 | 10 | 129 |
| L1 | 9 | 251 |
| L1 | 10 | 251 |
| E4 | 8 | 1 |
| E4 | 9 | 1 |
| L2 | 11 | 411 |
| E5B | 8 | 26 |
| E5B | 9 | 26 |
| E5B | 10 | 26 |
| E5B | 11 | 26 |
| E1 | 8 | 546 |
| E1 | 9 | 546 |
| E1 | 8 | 421 |
| E1 | 9 | 421 |
| E1 | 10 | 421 |
| E2 | 8 | 151 |
| E2 | 9 | 151 |
| L1 | 8 | 196 |
| L1 | 11 | 196 |
| E1 | 8 | 19 |
| L1 | 11 | 154 |
| E1 | 8 | 274 |
| E1 | 9 | 274 |
| E1 | 10 | 274 |
| L2 | 11 | 115 |
| E2 | 8 | 71 |
| E6 | 9 | 36 |
| E6 | 11 | 36 |
| E1 | 9 | 329 |
| E2 | 8 | 295 |
| E2 | 9 | 295 |
| E5B | 10 | 52 |
| E5B | 11 | 52 |
| E6 | 10 | 130 |
| E6 | 8 | 30 |
| E5B | 8 | 54 |
| E5B | 9 | 54 |
| E1 | 10 | 368 |
| E1 | 11 | 368 |
| E2 | 8 | 305 |
| E2 | 8 | 142 |
| L1 | 9 | 205 |
| E2 | 8 | 170 |
| E2 | 9 | 170 |
| E1 | 8 | 158 |
| L2 | 8 | 175 |
| L1 | 10 | 317 |
| L1 | 8 | 406 |
| L1 | 9 | 406 |
| L1 | 10 | 406 |
| E1 | 9 | 568 |
| E1 | 10 | 568 |
| E1 | 11 | 568 |
| E1 | 10 | 451 |
| E1 | 11 | 451 |
| L1 | 10 | 31 |
| E4 | 8 | 5 |
| E4 | 9 | 5 |
| E1 | 9 | 55 |
| E1 | 11 | 55 |
| E7 | 8 | 88 |
| E7 | 10 | 88 |
| E2 | 10 | 265 |
| E4 | 8 | 33 |
| E4 | 9 | 33 |
| L1 | 10 | 438 |
| E1 | 8 | 397 |
| E1 | 11 | 397 |
| L1 | 9 | 352 |
| L1 | 10 | 352 |
| E1 | 9 | 59 |
| E1 | 11 | 59 |
| E1 | 8 | 395 |
| E1 | 10 | 395 |
| E2 | 10 | 281 |
| E2 | 8 | 22 |
| E2 | 11 | 22 |
| E1 | 10 | 184 |
| L2 | 9 | 38 |
| E1 | 8 | 607 |
| E1 | 10 | 607 |
| L2 | 9 | 237 |
| L2 | 11 | 285 |
| L2 | 11 | 139 |
| L2 | 9 | 420 |
| E5A | 8 | 78 |
| L1 | 8 | 482 |
| L1 | 9 | 482 |
| L1 | 11 | 482 |

TABLE XVI-continued

B. HPV6B
HLA-A3 Motif Peptides

| 2 | 3 | 4 |
|---|---|---|
| L2 | 8 | 438 |
| L2 | 9 | 438 |
| L2 | 10 | 438 |
| L2 | 11 | 438 |
| E2 | 8 | 247 |
| E2 | 9 | 247 |
| E1 | 9 | 528 |
| E1 | 11 | 528 |
| L2 | 10 | 272 |
| L2 | 8 | 402 |
| E7 | 9 | 18 |
| L1 | 9 | 433 |
| E1 | 8 | 480 |
| L2 | 9 | 29 |
| L1 | 8 | 228 |
| L1 | 11 | 228 |
| E1 | 8 | 594 |
| E1 | 10 | 594 |
| E4 | 11 | 30 |
| E1 | 11 | 456 |
| E1 | 10 | 592 |
| L2 | 8 | 414 |
| L2 | 8 | 355 |
| L2 | 8 | 214 |
| L1 | 10 | 217 |
| L1 | 11 | 217 |
| L2 | 10 | 189 |
| E1 | 8 | 94 |
| E1 | 8 | 442 |
| E6 | 9 | 110 |
| E5 | 10 | 110 |
| E4 | 8 | 44 |
| E4 | 9 | 44 |
| L2 | 8 | 451 |
| L2 | 9 | 451 |
| L1 | 8 | 160 |
| L1 | 10 | 160 |
| L1 | 9 | 109 |
| L1 | 11 | 109 |
| E2 | 8 | 61 |
| E2 | 10 | 61 |
| L2 | 9 | 389 |
| L2 | 10 | 337 |
| E1 | 8 | 513 |
| E1 | 8 | 545 |
| E1 | 9 | 545 |
| E1 | 10 | 545 |
| L1 | 10 | 291 |
| L2 | 9 | 80 |
| L2 | 10 | 80 |
| L2 | 11 | 102 |
| L1 | 9 | 391 |
| L2 | 9 | 407 |
| E2 | 9 | 354 |
| E1 | 8 | 182 |
| E1 | 9 | 182 |
| L1 | 11 | 426 |
| L2 | 11 | 207 |
| L1 | 9 | 90 |
| L2 | 9 | 426 |
| L2 | 10 | 426 |
| E5A | 10 | 19 |
| L1 | 9 | 266 |
| L2 | 8 | 212 |
| L2 | 10 | 212 |
| L1 | 10 | 16 |
| L1 | 11 | 16 |
| L2 | 9 | 363 |
| L2 | 8 | 91 |
| L2 | 9 | 328 |
| E1 | 9 | 399 |
| E1 | 9 | 64 |
| E4 | 9 | 48 |
| E4 | 10 | 48 |
| E4 | 11 | 48 |
| E4 | 10 | 54 |
| E7 | 8 | 70 |
| L1 | 9 | 170 |
| L2 | 8 | 342 |
| L2 | 9 | 342 |
| L1 | 10 | 192 |
| E6 | 9 | 95 |
| E6 | 11 | 95 |
| E2 | 8 | 140 |
| E2 | 10 | 140 |
| L1 | 11 | 137 |
| E7 | 9 | 43 |
| E7 | 10 | 43 |
| E5A | 11 | 66 |
| E1 | 11 | 355 |
| E2 | 9 | 163 |
| E2 | 11 | 163 |
| E1 | 10 | 445 |
| E2 | 10 | 289 |
| L2 | 8 | 262 |
| L2 | 10 | 262 |
| E5B | 9 | 38 |
| E5B | 10 | 38 |
| E2 | 8 | 291 |
| E2 | 10 | 291 |
| E2 | 11 | 291 |
| E5A | 10 | 7 |
| L2 | 11 | 43 |
| E6 | 8 | 28 |
| E6 | 10 | 28 |
| E6 | 11 | 15 |
| L1 | 8 | 151 |
| L1 | 9 | 372 |
| L1 | 11 | 301 |
| L1 | 11 | 324 |
| E4 | 9 | 14 |
| E4 | 11 | 14 |
| L1 | 10 | 232 |
| L1 | 8 | 250 |
| L1 | 10 | 250 |
| L1 | 11 | 250 |
| E2 | 9 | 76 |
| E1 | 8 | 305 |
| L2 | 8 | 399 |
| L2 | 11 | 399 |
| E1 | 8 | 314 |
| E1 | 10 | 314 |
| E1 | 11 | 314 |
| L1 | 11 | 466 |
| E2 | 10 | 245 |
| E2 | 11 | 245 |
| L1 | 9 | 417 |
| E2 | 8 | 103 |
| E2 | 9 | 103 |
| E2 | 10 | 103 |
| E2 | 11 | 103 |
| E2 | 8 | 233 |
| E2 | 9 | 233 |
| L1 | 10 | 149 |
| E1 | 10 | 128 |
| E2 | 11 | 218 |
| E1 | 9 | 344 |
| L2 | 8 | 231 |
| L2 | 9 | 231 |
| E2 | 11 | 57 |
| E1 | 8 | 205 |
| E1 | 9 | 205 |
| E1 | 10 | 391 |
| E1 | 11 | 391 |
| L1 | 9 | 53 |
| L2 | 8 | 5 |
| L2 | 10 | 5 |
| L2 | 8 | 11 |

TABLE XVI-continued

B. HPV6B
HLA-A3 Motif Peptides

| 2 | 3 | 4 |
|---|---|---|
| E5B | 8 | 35 |
| E5B | 10 | 35 |
| E2 | 8 | 108 |
| E1 | 9 | 639 |
| E1 | 8 | 169 |
| E1 | 11 | 169 |
| E6 | 10 | 125 |
| E1 | 8 | 281 |
| E1 | 8 | 383 |
| E1 | 9 | 383 |
| E1 | 10 | 383 |
| E1 | 11 | 383 |
| E6 | 8 | 56 |
| E6 | 10 | 56 |
| E2 | 8 | 113 |
| E2 | 9 | 113 |
| L2 | 8 | 291 |
| L1 | 11 | 470 |
| L2 | 10 | 302 |
| L2 | 11 | 302 |
| E2 | 10 | 241 |
| L2 | 9 | 298 |
| L2 | 11 | 298 |
| L2 | 10 | 449 |
| L2 | 11 | 449 |
| E1 | 9 | 109 |
| L1 | 8 | 241 |
| L2 | 8 | 281 |
| L2 | 10 | 281 |
| L2 | 11 | 281 |
| L2 | 10 | 245 |
| L1 | 9 | 40 |
| L1 | 10 | 40 |
| E2 | 8 | 303 |
| E2 | 10 | 303 |
| L2 | 8 | 308 |
| L2 | 9 | 308 |
| L2 | 11 | 308 |
| L1 | 9 | 472 |
| L1 | 10 | 472 |
| L1 | 9 | 334 |
| E1 | 9 | 288 |
| L1 | 8 | 476 |
| L1 | 11 | 476 |
| L2 | 11 | 68 |
| L1 | 8 | 29 |
| L1 | 9 | 279 |
| L2 | 8 | 221 |
| L2 | 10 | 221 |
| L1 | 8 | 140 |
| L1 | 9 | 140 |
| E1 | 11 | 583 |
| L1 | 8 | 488 |
| L1 | 9 | 488 |
| L1 | 10 | 488 |
| L1 | 9 | 379 |
| L2 | 8 | 111 |
| E6 | 8 | 3 |
| L2 | 8 | 181 |
| E2 | 8 | 283 |
| L2 | 10 | 13 |
| E6 | 10 | 9 |
| L1 | 8 | 353 |
| L1 | 9 | 353 |
| L2 | 11 | 352 |
| E1 | 9 | 219 |
| E1 | 10 | 219 |
| E1 | 10 | 493 |
| L1 | 8 | 440 |
| L1 | 10 | 440 |
| L1 | 11 | 440 |
| E1 | 11 | 12 |
| L2 | 8 | 432 |
| L2 | 10 | 432 |
| L2 | 11 | 432 |
| L1 | 10 | 131 |
| L1 | 8 | 115 |
| L1 | 9 | 115 |
| L2 | 8 | 309 |
| L2 | 10 | 309 |
| L2 | 11 | 309 |
| E2 | 11 | 261 |
| L2 | 10 | 400 |
| L1 | 9 | 292 |
| L2 | 9 | 63 |
| E1 | 9 | 315 |
| E1 | 10 | 315 |
| E1 | 8 | 43 |
| E1 | 10 | 135 |
| L1 | 8 | 63 |
| L1 | 9 | 63 |
| L1 | 10 | 467 |
| E1 | 8 | 547 |
| L2 | 8 | 153 |
| L2 | 9 | 267 |
| L2 | 10 | 267 |
| E5A | 11 | 30 |
| E1 | 8 | 422 |
| E1 | 9 | 422 |
| E2 | 8 | 207 |
| E2 | 11 | 207 |
| L1 | 8 | 474 |
| L1 | 10 | 474 |
| E1 | 8 | 247 |
| L1 | 10 | 375 |
| L1 | 11 | 375 |
| L2 | 8 | 81 |
| L2 | 9 | 81 |
| L2 | 10 | 103 |
| E1 | 8 | 60 |
| E1 | 10 | 60 |
| L1 | 9 | 86 |
| L2 | 11 | 106 |
| E4 | 9 | 90 |
| L1 | 10 | 294 |
| E6 | 11 | 23 |
| L2 | 8 | 304 |
| L2 | 9 | 304 |
| E2 | 9 | 150 |
| E2 | 10 | 150 |
| E2 | 9 | 282 |
| L1 | 9 | 297 |
| L1 | 11 | 297 |
| L2 | 8 | 133 |
| L1 | 8 | 473 |
| L1 | 9 | 473 |
| L1 | 11 | 473 |
| E2 | 8 | 323 |
| E2 | 9 | 323 |
| L1 | 10 | 85 |
| E4 | 10 | 89 |
| L1 | 9 | 38 |
| L1 | 11 | 38 |
| L1 | 10 | 37 |
| E2 | 8 | 224 |
| L2 | 9 | 209 |
| L2 | 11 | 209 |
| E2 | 10 | 316 |
| E2 | 11 | 316 |
| L1 | 9 | 347 |
| L1 | 10 | 347 |
| E2 | 10 | 23 |
| E5A | 10 | 14 |
| E5A | 11 | 14 |
| E2 | 9 | 180 |
| E2 | 9 | 220 |
| L1 | 8 | 335 |

TABLE XVI-continued

B. HPV6B
HLA-A3 Motif Peptides

| 2 | 3 | 4 |
|---|---|---|
| L2 | 9 | 241 |
| L2 | 8 | 210 |
| L2 | 10 | 210 |
| E1 | 8 | 289 |
| E2 | 8 | 190 |
| E2 | 9 | 317 |
| E2 | 10 | 317 |
| L1 | 8 | 348 |
| L1 | 9 | 348 |
| L1 | 11 | 348 |
| L1 | 8 | 392 |
| E2 | 8 | 40 |
| E5A | 10 | 45 |
| L2 | 10 | 260 |
| E1 | 9 | 185 |
| L2 | 11 | 164 |
| L2 | 11 | 145 |
| L1 | 8 | 343 |
| E6 | 8 | 40 |
| E6 | 9 | 40 |
| E6 | 10 | 40 |
| E6 | 11 | 40 |
| E1 | 9 | 192 |
| E1 | 11 | 192 |
| L2 | 8 | 408 |
| L2 | 10 | 216 |
| E7 | 11 | 56 |
| E2 | 8 | 160 |
| E2 | 9 | 160 |
| L1 | 11 | 224 |
| E1 | 8 | 233 |
| E1 | 10 | 233 |
| L2 | 9 | 26 |
| L1 | 9 | 422 |
| L1 | 11 | 422 |
| L1 | 11 | 23 |
| E2 | 9 | 24 |
| E2 | 11 | 24 |
| L2 | 11 | 235 |
| L2 | 9 | 345 |
| E5A | 9 | 15 |
| E5A | 10 | 15 |
| E1 | 8 | 588 |
| E1 | 10 | 588 |
| L2 | 11 | 405 |
| E1 | 8 | 586 |
| E1 | 10 | 586 |
| L1 | 8 | 199 |
| L1 | 9 | 199 |
| E1 | 10 | 437 |
| L2 | 11 | 424 |
| E1 | 10 | 167 |
| L2 | 8 | 430 |
| L2 | 10 | 430 |
| L2 | 8 | 61 |
| L2 | 11 | 61 |
| L2 | 11 | 24 |
| E1 | 8 | 146 |
| L1 | 10 | 477 |
| L1 | 11 | 477 |
| E1 | 8 | 15 |
| L2 | 10 | 69 |
| L2 | 11 | 69 |
| L2 | 8 | 39 |
| E6 | 9 | 12 |
| E2 | 8 | 355 |
| L2 | 11 | 130 |
| L1 | 8 | 408 |
| L1 | 10 | 270 |
| E5A | 9 | 71 |
| E5A | 11 | 71 |
| E7 | 10 | 86 |
| E5 | 8 | 26 |
| E5 | 10 | 26 |
| L1 | 8 | 377 |
| L1 | 9 | 377 |
| L1 | 11 | 377 |
| E2 | 8 | 221 |
| E2 | 11 | 221 |
| E1 | 8 | 408 |
| E1 | 9 | 408 |
| E2 | 11 | 128 |
| E5B | 10 | 59 |
| E5 | 11 | 8 |
| L2 | 9 | 147 |
| L2 | 10 | 147 |
| L2 | 9 | 152 |
| E1 | 8 | 566 |
| E1 | 11 | 566 |
| L2 | 9 | 132 |
| E4 | 11 | 88 |
| L2 | 10 | 208 |
| L1 | 10 | 346 |
| L1 | 11 | 346 |
| E5A | 11 | 13 |
| E2 | 10 | 219 |
| L1 | 8 | 280 |
| E5A | 11 | 44 |
| E2 | 11 | 97 |
| E6 | 8 | 39 |
| E6 | 9 | 39 |
| E6 | 10 | 39 |
| E6 | 11 | 39 |
| L1 | 8 | 223 |
| E1 | 9 | 232 |
| E1 | 11 | 232 |
| E5B | 8 | 63 |
| E1 | 9 | 585 |
| E1 | 11 | 585 |
| E6 | 8 | 11 |
| E6 | 10 | 11 |
| L1 | 8 | 91 |
| L1 | 11 | 332 |
| L2 | 10 | 151 |
| L1 | 11 | 345 |
| L2 | 11 | 150 |
| E6 | 8 | 87 |
| E4 | 8 | 101 |
| E2 | 10 | 116 |
| E1 | 8 | 345 |
| E1 | 11 | 498 |
| L2 | 11 | 387 |
| E1 | 8 | 78 |
| E1 | 9 | 78 |
| E2 | 10 | 334 |
| L1 | 9 | 57 |
| L1 | 11 | 57 |
| E1 | 8 | 317 |
| L2 | 8 | 339 |
| L2 | 11 | 339 |
| E1 | 8 | 239 |
| L1 | 9 | 21 |
| E7 | 8 | 90 |
| E5A | 8 | 74 |
| E5A | 10 | 74 |
| E5A | 11 | 74 |
| E2 | 8 | 152 |
| E1 | 11 | 515 |
| E1 | 11 | 48 |
| E7 | 10 | 40 |
| L1 | 10 | 197 |
| L1 | 11 | 197 |
| E6 | 10 | 32 |
| L2 | 8 | 427 |
| L2 | 9 | 427 |
| L2 | 11 | 427 |
| L1 | 11 | 69 |
| L1 | 10 | 155 |

TABLE XVI-continued

B. HPV6B
HLA-A3 Motif Peptides

| 2 | 3 | 4 |
|---|---|---|
| L1 | 9 | 44 |
| L1 | 10 | 44 |
| L1 | 11 | 44 |
| L2 | 9 | 222 |
| E5B | 10 | 24 |
| E5B | 11 | 24 |
| E1 | 8 | 477 |
| E1 | 10 | 477 |
| E1 | 11 | 477 |
| L1 | 8 | 112 |
| L1 | 11 | 112 |
| E1 | 11 | 346 |
| E1 | 11 | 333 |
| E5A | 9 | 20 |
| L2 | 11 | 31 |
| E1 | 10 | 499 |
| E1 | 11 | 499 |
| E6 | 9 | 53 |
| E6 | 10 | 53 |
| E6 | 11 | 53 |
| E2 | 8 | 30 |
| E2 | 9 | 30 |
| E6 | 9 | 100 |
| E6 | 10 | 100 |
| E4 | 8 | 17 |
| E4 | 10 | 17 |
| E4 | 11 | 17 |
| E1 | 9 | 278 |
| E1 | 11 | 278 |
| E1 | 8 | 275 |
| E1 | 9 | 275 |
| L1 | 8 | 73 |
| L1 | 9 | 73 |
| E5A | 9 | 46 |
| E4 | 11 | 10 |
| E2 | 9 | 64 |
| L1 | 9 | 114 |
| L1 | 10 | 114 |
| L1 | 9 | 62 |
| L1 | 10 | 62 |
| E2 | 9 | 206 |
| L1 | 9 | 484 |
| L1 | 10 | 484 |
| L1 | 11 | 484 |
| L1 | 9 | 17 |
| L1 | 10 | 17 |
| L2 | 8 | 105 |
| E1 | 8 | 92 |
| E1 | 10 | 92 |
| L1 | 8 | 296 |
| L1 | 10 | 296 |
| E2 | 9 | 223 |
| L2 | 11 | 259 |
| E5B | 11 | 58 |
| L2 | 8 | 364 |
| L2 | 11 | 418 |
| L2 | 10 | 165 |
| L1 | 8 | 27 |
| L1 | 9 | 27 |
| L1 | 10 | 27 |
| L2 | 10 | 146 |
| L2 | 11 | 146 |
| E1 | 9 | 565 |
| E1 | 10 | 584 |
| E2 | 11 | 333 |
| L1 | 8 | 327 |
| E2 | 9 | 335 |
| E1 | 8 | 238 |
| E1 | 9 | 238 |
| L1 | 10 | 20 |
| E2 | 10 | 349 |
| E2 | 11 | 349 |
| L1 | 8 | 72 |
| L1 | 9 | 72 |

TABLE XVI-continued

B. HPV6B
HLA-A3 Motif Peptides

| 2 | 3 | 4 |
|---|---|---|
| L1 | 10 | 72 |
| L1 | 8 | 58 |
| L1 | 10 | 58 |
| L1 | 11 | 58 |
| E2 | 10 | 58 |
| E2 | 11 | 58 |
| E5A | 8 | 3 |
| E7 | 10 | 68 |
| L1 | 10 | 97 |
| E2 | 8 | 321 |
| E2 | 9 | 321 |
| E2 | 10 | 321 |
| E2 | 11 | 321 |
| E1 | 10 | 17 |
| E1 | 9 | 322 |
| E1 | 10 | 272 |
| E1 | 11 | 272 |
| L2 | 8 | 47 |
| E1 | 8 | 426 |
| E5A | 8 | 36 |
| E1 | 10 | 340 |
| E1 | 9 | 530 |
| E5B | 9 | 13 |
| E5B | 10 | 13 |
| E1 | 8 | 464 |
| E5A | 10 | 58 |
| E5A | 11 | 58 |
| L1 | 8 | 308 |
| E1 | 8 | 510 |
| E1 | 9 | 510 |
| E1 | 11 | 510 |
| E2 | 8 | 92 |
| E2 | 10 | 145 |
| E2 | 11 | 145 |
| E1 | 9 | 237 |
| E1 | 10 | 237 |
| E6 | 10 | 61 |
| E6 | 11 | 61 |
| E1 | 10 | 262 |
| E1 | 11 | 380 |
| E6 | 10 | 85 |
| E1 | 8 | 76 |
| E1 | 9 | 76 |
| E1 | 10 | 76 |
| E1 | 11 | 76 |
| E6 | 10 | 46 |
| E6 | 11 | 46 |
| E5A | 8 | 76 |
| E5A | 9 | 76 |
| E5A | 10 | 76 |
| L2 | 9 | 321 |
| L2 | 10 | 321 |
| E2 | 10 | 337 |
| L2 | 8 | 441 |
| L2 | 9 | 441 |
| E1 | 9 | 486 |
| L1 | 9 | 48 |
| L2 | 9 | 319 |
| L2 | 11 | 319 |
| L1 | 8 | 238 |
| L1 | 10 | 238 |
| L1 | 11 | 238 |
| E2 | 11 | 178 |
| E2 | 10 | 188 |
| E1 | 8 | 137 |
| E4 | 8 | 22 |
| E4 | 10 | 22 |
| L2 | 8 | 435 |
| L2 | 9 | 435 |
| L2 | 10 | 435 |
| L2 | 11 | 435 |
| E1 | 9 | 579 |
| E1 | 11 | 579 |
| L1 | 9 | 230 |

TABLE XVI-continued

B. HPV6B
HLA-A3 Motif Peptides

| 2 | 3 | 4 |
|---|---|---|
| L1 | 8 | 358 |
| L2 | 11 | 296 |
| E6 | 9 | 44 |
| E2 | 9 | 159 |
| E2 | 10 | 159 |
| L1 | 9 | 350 |
| L1 | 11 | 350 |
| E5B | 9 | 62 |
| E1 | 10 | 402 |
| E1 | 11 | 402 |
| E4 | 9 | 16 |
| E4 | 11 | 16 |
| E4 | 8 | 9 |
| E2 | 8 | 168 |
| E2 | 10 | 168 |
| E2 | 11 | 168 |
| L2 | 8 | 71 |
| L2 | 9 | 71 |
| L1 | 10 | 10 |
| E2 | 10 | 138 |
| L1 | 11 | 415 |
| E1 | 9 | 91 |
| E1 | 11 | 91 |
| L1 | 8 | 26 |
| L1 | 9 | 26 |
| L1 | 10 | 26 |
| L1 | 11 | 26 |
| E2 | 8 | 131 |

TABLE XVI

C. HPVI1
HLA-A3 Motif Peptides

| 2 | 3 | 4 |
|---|---|---|
| L1 | 8 | 235 |
| L1 | 10 | 235 |
| L1 | 11 | 235 |
| L2 | 8 | 328 |
| L2 | 10 | 339 |
| L2 | 11 | 339 |
| E4 | 9 | 12 |
| E4 | 11 | 12 |
| E1 | 8 | 144 |
| E6 | 11 | 63 |
| E6 | 9 | 65 |
| E2 | 10 | 10 |
| E4 | 10 | 55 |
| L1 | 9 | 98 |
| E2 | 10 | 226 |
| L1 | 9 | 236 |
| L1 | 10 | 236 |
| L1 | 11 | 236 |
| E1 | 11 | 190 |
| E1 | 8 | 235 |
| E1 | 11 | 235 |
| E1 | 10 | 377 |
| E1 | 9 | 392 |
| E1 | 10 | 392 |
| E1 | 11 | 392 |
| L2 | 8 | 237 |
| L2 | 9 | 274 |
| L2 | 10 | 274 |
| L2 | 10 | 215 |
| E1 | 11 | 637 |
| E1 | 10 | 240 |
| L2 | 9 | 62 |
| L2 | 11 | 68 |
| E2 | 8 | 3 |
| E1 | 9 | 112 |

TABLE XVI-continued

C. HPVI1
HLA-A3 Motif Peptides

| 2 | 3 | 4 |
|---|---|---|
| E1 | 10 | 112 |
| L2 | 10 | 139 |
| E1 | 8 | 407 |
| E1 | 9 | 407 |
| E1 | 10 | 407 |
| L1 | 11 | 421 |
| L2 | 8 | 80 |
| L2 | 9 | 80 |
| L2 | 10 | 285 |
| L2 | 11 | 285 |
| E1 | 10 | 475 |
| E1 | 8 | 65 |
| E1 | 10 | 65 |
| E1 | 11 | 65 |
| L1 | 8 | 81 |
| L2 | 8 | 417 |
| L2 | 11 | 227 |
| E6 | 8 | 37 |
| E6 | 9 | 37 |
| E6 | 10 | 37 |
| E6 | 11 | 37 |
| L1 | 11 | 204 |
| L2 | 11 | 11 |
| L2 | 9 | 173 |
| E2 | 8 | 321 |
| E2 | 10 | 321 |
| L1 | 8 | 36 |
| L1 | 11 | 36 |
| E2 | 8 | 314 |
| E1 | 8 | 330 |
| L1 | 9 | 343 |
| E2 | 8 | 197 |
| L1 | 8 | 22 |
| L2 | 9 | 13 |
| L2 | 10 | 13 |
| E1 | 8 | 525 |
| E6 | 9 | 10 |
| E6 | 11 | 10 |
| E1 | 8 | 77 |
| E1 | 9 | 77 |
| E1 | 10 | 77 |
| L1 | 8 | 349 |
| L1 | 9 | 349 |
| L1 | 11 | 349 |
| E1 | 9 | 181 |
| E1 | 10 | 181 |
| E1 | 9 | 101 |
| L1 | 10 | 43 |
| L1 | 11 | 43 |
| E5 | 9 | 37 |
| E5 | 11 | 37 |
| E5 | 9 | 26 |
| E5 | 10 | 26 |
| E5 | 11 | 26 |
| L1 | 8 | 484 |
| L1 | 10 | 484 |
| L1 | 11 | 484 |
| E1 | 8 | 601 |
| E1 | 11 | 601 |
| E6 | 10 | 64 |
| E1 | 9 | 234 |
| E1 | 8 | 406 |
| E1 | 9 | 406 |
| E1 | 10 | 406 |
| E1 | 11 | 406 |
| E5 | 8 | 46 |
| L1 | 8 | 158 |
| L1 | 11 | 158 |
| L1 | 8 | 342 |
| L1 | 10 | 342 |
| E7 | 10 | 57 |
| E7 | 9 | 58 |
| E6 | 8 | 66 |
| E1 | 8 | 486 |

TABLE XVI-continued

C. HPVI1
HLA-A3 Motif Peptides

| 2 | 3 | 4 |
|---|---|---|
| E1 | 9 | 486 |
| E1 | 11 | 215 |
| E2 | 9 | 298 |
| E2 | 10 | 298 |
| E2 | 11 | 298 |
| E7 | 8 | 59 |
| E2 | 8 | 161 |
| E2 | 11 | 161 |
| L1 | 10 | 222 |
| E2 | 10 | 35 |
| E2 | 11 | 35 |
| E6 | 11 | 67 |
| E2 | 8 | 295 |
| L1 | 11 | 375 |
| E2 | 11 | 194 |
| L1 | 8 | 99 |
| E1 | 9 | 14 |
| E2 | 9 | 227 |
| E5 | 8 | 73 |
| E5 | 9 | 73 |
| E5 | 11 | 73 |
| E6 | 11 | 31 |
| E1 | 8 | 640 |
| E2 | 11 | 9 |
| E1 | 11 | 73 |
| E1 | 10 | 111 |
| E1 | 11 | 111 |
| E1 | 10 | 516 |
| E1 | 8 | 607 |
| E1 | 10 | 607 |
| E7 | 8 | 44 |
| E7 | 9 | 44 |
| E1 | 9 | 524 |
| L1 | 10 | 24 |
| L1 | 11 | 24 |
| E1 | 8 | 405 |
| E1 | 9 | 405 |
| E1 | 10 | 405 |
| E1 | 11 | 405 |
| E1 | 10 | 523 |
| L1 | 11 | 270 |
| E1 | 8 | 183 |
| L1 | 9 | 124 |
| E1 | 8 | 385 |
| E1 | 9 | 385 |
| L2 | 9 | 429 |
| L2 | 10 | 429 |
| L2 | 11 | 429 |
| E2 | 10 | 122 |
| L1 | 9 | 194 |
| L1 | 11 | 194 |
| E5 | 11 | 10 |
| E1 | 9 | 542 |
| E1 | 10 | 542 |
| E1 | 11 | 542 |
| E1 | 9 | 159 |
| E1 | 8 | 631 |
| E1 | 9 | 631 |
| E2 | 8 | 231 |
| E2 | 9 | 231 |
| E2 | 10 | 231 |
| E2 | 11 | 231 |
| E1 | 9 | 369 |
| E1 | 10 | 369 |
| L1 | 8 | 220 |
| L1 | 9 | 220 |
| E1 | 9 | 168 |
| E1 | 10 | 168 |
| E2 | 8 | 25 |
| E2 | 10 | 25 |
| L2 | 9 | 277 |
| E6 | 8 | 96 |
| E6 | 10 | 96 |
| E1 | 9 | 203 |
| E1 | 10 | 203 |
| E1 | 11 | 203 |
| E1 | 8 | 570 |
| E1 | 9 | 570 |
| E1 | 10 | 570 |
| L2 | 8 | 321 |
| L2 | 9 | 321 |
| E1 | 10 | 222 |
| E1 | 11 | 81 |
| L1 | 10 | 271 |
| E7 | 11 | 14 |
| L1 | 10 | 439 |
| E1 | 9 | 46 |
| E1 | 10 | 46 |
| L1 | 9 | 196 |
| E1 | 9 | 42 |
| E1 | 11 | 134 |
| E2 | 8 | 292 |
| E2 | 9 | 292 |
| E2 | 10 | 292 |
| E2 | 11 | 292 |
| E7 | 9 | 31 |
| L1 | 11 | 84 |
| L2 | 10 | 343 |
| L1 | 9 | 199 |
| L1 | 10 | 199 |
| E1 | 10 | 191 |
| E5 | 9 | 12 |
| E5 | 11 | 12 |
| L1 | 10 | 412 |
| L1 | 8 | 125 |
| L2 | 8 | 29 |
| L2 | 8 | 257 |
| E1 | 8 | 143 |
| E1 | 9 | 143 |
| E1 | 10 | 178 |
| L2 | 8 | 273 |
| L2 | 10 | 273 |
| L2 | 11 | 273 |
| E2 | 9 | 2 |
| E1 | 8 | 336 |
| E1 | 8 | 62 |
| E1 | 11 | 62 |
| E2 | 10 | 174 |
| L1 | 9 | 300 |
| L2 | 10 | 172 |
| E1 | 8 | 180 |
| E1 | 10 | 180 |
| E1 | 11 | 180 |
| E7 | 8 | 70 |
| E1 | 11 | 627 |
| E7 | 9 | 34 |
| E1 | 8 | 630 |
| E1 | 9 | 630 |
| E1 | 10 | 630 |
| E2 | 9 | 230 |
| E2 | 10 | 230 |
| E2 | 11 | 230 |
| E6 | 9 | 95 |
| E6 | 11 | 95 |
| L2 | 8 | 190 |
| E1 | 10 | 41 |
| E7 | 10 | 30 |
| L1 | 11 | 411 |
| L2 | 9 | 256 |
| L1 | 8 | 365 |
| E1 | 8 | 453 |
| E1 | 10 | 453 |
| L2 | 9 | 254 |
| L2 | 11 | 254 |
| E1 | 8 | 170 |
| E1 | 10 | 170 |
| E1 | 9 | 10 |
| E4 | 10 | 98 |

TABLE XVI-continued

C. HPVI1
HLA-A3 Motif Peptides

| 2 | 3 | 4 |
|---|---|---|
| E1 | 8 | 172 |
| E1 | 10 | 172 |
| E1 | 9 | 375 |
| E6 | 11 | 113 |
| L2 | 9 | 331 |
| L2 | 10 | 331 |
| E1 | 8 | 105 |
| E1 | 10 | 105 |
| E6 | 8 | 42 |
| E6 | 11 | 42 |
| E2 | 8 | 312 |
| E2 | 10 | 312 |
| L1 | 9 | 454 |
| L1 | 10 | 454 |
| L1 | 11 | 454 |
| L2 | 8 | 333 |
| E1 | 9 | 197 |
| E6 | 9 | 69 |
| E6 | 10 | 69 |
| E6 | 11 | 69 |
| E1 | 8 | 604 |
| E1 | 10 | 604 |
| E1 | 11 | 604 |
| E1 | 9 | 131 |
| E2 | 11 | 17 |
| E1 | 8 | 417 |
| E2 | 10 | 74 |
| E2 | 11 | 74 |
| E2 | 8 | 100 |
| E2 | 9 | 100 |
| E2 | 11 | 100 |
| L2 | 9 | 109 |
| E1 | 8 | 373 |
| E1 | 9 | 373 |
| E1 | 11 | 373 |
| E1 | 10 | 103 |
| L2 | 10 | 265 |
| L2 | 11 | 265 |
| E6 | 9 | 2 |
| E2 | 8 | 80 |
| E2 | 8 | 39 |
| E2 | 9 | 39 |
| E6 | 8 | 92 |
| E1 | 10 | 128 |
| E7 | 10 | 36 |
| E1 | 10 | 141 |
| E1 | 11 | 141 |
| L1 | 8 | 444 |
| E2 | 10 | 205 |
| L2 | 10 | 119 |
| E5 | 8 | 2 |
| E5 | 9 | 2 |
| E5 | 10 | 2 |
| L1 | 8 | 207 |
| L1 | 9 | 80 |
| L1 | 8 | 253 |
| L1 | 9 | 253 |
| L2 | 8 | 438 |
| E1 | 8 | 487 |
| E6 | 9 | 33 |
| E2 | 11 | 121 |
| L2 | 8 | 345 |
| L2 | 10 | 352 |
| L1 | 11 | 88 |
| E1 | 9 | 595 |
| E1 | 8 | 386 |
| L2 | 11 | 52 |
| E5 | 10 | 67 |
| E5 | 11 | 67 |
| L1 | 10 | 244 |
| L1 | 11 | 244 |
| L2 | 10 | 53 |
| E1 | 8 | 242 |
| E1 | 10 | 242 |

TABLE XVI-continued

C. HPVI1
HLA-A3 Motif Peptides

| 2 | 3 | 4 |
|---|---|---|
| E1 | 11 | 242 |
| E1 | 10 | 216 |
| E6 | 9 | 126 |
| E6 | 11 | 126 |
| E1 | 9 | 454 |
| L2 | 8 | 424 |
| L2 | 10 | 424 |
| E1 | 9 | 494 |
| L1 | 8 | 464 |
| L1 | 10 | 464 |
| E5 | 9 | 68 |
| E5 | 10 | 68 |
| E1 | 8 | 393 |
| E1 | 9 | 393 |
| E1 | 10 | 393 |
| E1 | 9 | 446 |
| E1 | 10 | 457 |
| L2 | 11 | 238 |
| E5 | 8 | 16 |
| E5 | 11 | 16 |
| L2 | 8 | 275 |
| L2 | 9 | 275 |
| L2 | 11 | 275 |
| E1 | 9 | 18 |
| L2 | 11 | 295 |
| L1 | 8 | 451 |
| E1 | 9 | 587 |
| E1 | 11 | 587 |
| L2 | 9 | 262 |
| E1 | 8 | 220 |
| E1 | 9 | 220 |
| L2 | 10 | 393 |
| L1 | 9 | 327 |
| L2 | 8 | 61 |
| L2 | 10 | 61 |
| L1 | 9 | 157 |
| E2 | 9 | 123 |
| E1 | 10 | 13 |
| E1 | 8 | 384 |
| E1 | 9 | 384 |
| E1 | 10 | 384 |
| E1 | 10 | 158 |
| L1 | 8 | 195 |
| L1 | 10 | 195 |
| E5 | 8 | 65 |
| L1 | 9 | 240 |
| L1 | 10 | 240 |
| E2 | 9 | 291 |
| E2 | 10 | 291 |
| E2 | 11 | 291 |
| E5 | 10 | 11 |
| L1 | 8 | 201 |
| E1 | 9 | 241 |
| E1 | 11 | 241 |
| E1 | 11 | 157 |
| L2 | 9 | 54 |
| L1 | 9 | 276 |
| L1 | 9 | 133 |
| L1 | 9 | 319 |
| L2 | 11 | 57 |
| E1 | 9 | 243 |
| E1 | 10 | 243 |
| L1 | 9 | 479 |
| E1 | 9 | 194 |
| E2 | 9 | 156 |
| E2 | 10 | 156 |
| L2 | 8 | 55 |
| E5 | 8 | 29 |
| E5 | 9 | 29 |
| E5 | 11 | 29 |
| E1 | 9 | 217 |
| E1 | 11 | 217 |
| L2 | 11 | 291 |
| E1 | 9 | 273 |

TABLE XVI-continued

C. HPVI1
HLA-A3 Motif Peptides

| 2 | 3 | 4 |
|---|---|---|
| E1 | 10 | 273 |
| E1 | 11 | 273 |
| L2 | 11 | 427 |
| E1 | 8 | 11 |
| L2 | 8 | 63 |
| L1 | 8 | 294 |
| L1 | 11 | 294 |
| L2 | 10 | 302 |
| E1 | 8 | 632 |
| E2 | 10 | 179 |
| E2 | 9 | 189 |
| L2 | 10 | 24 |
| E5 | 8 | 40 |
| E5 | 9 | 40 |
| E5 | 11 | 40 |
| L2 | 9 | 59 |
| L2 | 10 | 59 |
| E1 | 11 | 431 |
| L1 | 8 | 408 |
| L1 | 9 | 408 |
| E1 | 10 | 296 |
| E7 | 11 | 85 |
| L2 | 10 | 408 |
| E1 | 9 | 467 |
| E4 | 9 | 99 |
| L1 | 9 | 223 |
| E1 | 9 | 173 |
| E1 | 8 | 316 |
| E1 | 9 | 316 |
| E2 | 8 | 232 |
| E2 | 9 | 232 |
| E2 | 10 | 232 |
| E2 | 11 | 232 |
| L1 | 10 | 113 |
| L1 | 11 | 113 |
| E1 | 10 | 415 |
| L1 | 9 | 35 |
| E6 | 8 | 79 |
| E1 | 10 | 508 |
| E1 | 11 | 508 |
| E5 | 9 | 54 |
| E1 | 8 | 209 |
| E7 | 8 | 2 |
| E5 | 9 | 39 |
| E5 | 10 | 39 |
| E1 | 10 | 466 |
| L2 | 8 | 311 |
| L2 | 9 | 311 |
| E6 | 8 | 119 |
| E6 | 10 | 119 |
| E2 | 9 | 29 |
| E1 | 8 | 264 |
| E1 | 9 | 55 |
| E1 | 11 | 55 |
| E2 | 10 | 78 |
| E2 | 11 | 309 |
| L1 | 11 | 325 |
| E5 | 10 | 7 |
| E4 | 9 | 20 |
| E4 | 10 | 20 |
| E1 | 8 | 305 |
| E1 | 9 | 246 |
| E1 | 8 | 349 |
| E1 | 9 | 349 |
| E1 | 9 | 581 |
| E6 | 9 | 25 |
| E6 | 11 | 25 |
| L2 | 10 | 36 |
| L2 | 10 | 188 |
| L1 | 9 | 362 |
| L1 | 11 | 362 |
| E2 | 10 | 208 |
| E1 | 8 | 376 |
| E1 | 11 | 376 |

TABLE XVI-continued

C. HPVI1
HLA-A3 Motif Peptides

| 2 | 3 | 4 |
|---|---|---|
| E1 | 11 | 474 |
| E1 | 8 | 370 |
| E1 | 9 | 370 |
| E1 | 11 | 370 |
| L1 | 8 | 221 |
| L1 | 11 | 221 |
| L1 | 8 | 320 |
| E2 | 9 | 24 |
| E2 | 11 | 24 |
| E1 | 8 | 569 |
| E1 | 9 | 569 |
| E1 | 10 | 569 |
| E1 | 11 | 569 |
| E6 | 8 | 13 |
| L1 | 11 | 371 |
| L1 | 9 | 32 |
| L2 | 8 | 312 |
| E1 | 10 | 334 |
| E4 | 8 | 6 |
| E4 | 11 | 6 |
| L2 | 8 | 298 |
| L2 | 10 | 298 |
| L2 | 10 | 58 |
| L2 | 11 | 58 |
| E4 | 8 | 5 |
| E4 | 9 | 5 |
| E5 | 10 | 34 |
| L2 | 8 | 278 |
| L2 | 9 | 140 |
| E1 | 8 | 195 |
| E1 | 11 | 195 |
| E6 | 9 | 120 |
| E5 | 9 | 35 |
| E6 | 9 | 97 |
| L2 | 10 | 43 |
| L2 | 11 | 43 |
| E5 | 8 | 17 |
| E5 | 9 | 17 |
| E1 | 8 | 408 |
| E1 | 9 | 408 |
| E2 | 8 | 30 |
| L2 | 10 | 179 |
| E1 | 8 | 571 |
| E1 | 9 | 571 |
| E1 | 11 | 571 |
| E1 | 11 | 327 |
| E1 | 9 | 106 |
| L2 | 8 | 322 |
| E1 | 9 | 500 |
| E1 | 10 | 500 |
| L1 | 10 | 422 |
| L2 | 8 | 81 |
| L2 | 9 | 425 |
| L1 | 9 | 377 |
| L1 | 10 | 377 |
| E1 | 8 | 56 |
| E1 | 10 | 56 |
| E1 | 9 | 341 |
| L2 | 9 | 286 |
| L2 | 10 | 286 |
| L2 | 10 | 130 |
| E7 | 9 | 89 |
| E1 | 9 | 476 |
| E5 | 10 | 31 |
| L2 | 9 | 103 |
| E2 | 8 | 265 |
| E2 | 9 | 265 |
| E2 | 11 | 265 |
| E2 | 9 | 45 |
| E5 | 9 | 45 |
| E2 | 10 | 297 |
| E2 | 11 | 297 |
| E2 | 11 | 34 |
| E1 | 10 | 200 |

TABLE XVI-continued

C. HPVI1
HLA-A3 Motif Peptides

| 2 | 3 | 4 |
|---|---|---|
| E1 | 8 | 404 |
| E1 | 9 | 404 |
| E1 | 10 | 404 |
| E1 | 11 | 404 |
| E1 | 8 | 213 |
| E1 | 8 | 202 |
| E1 | 10 | 202 |
| E1 | 11 | 202 |
| L1 | 11 | 438 |
| L1 | 10 | 79 |
| E1 | 10 | 211 |
| E1 | 10 | 493 |
| L1 | 8 | 463 |
| L1 | 9 | 463 |
| L1 | 11 | 463 |
| L1 | 9 | 450 |
| L1 | 10 | 275 |
| E2 | 11 | 68 |
| E2 | 10 | 155 |
| E2 | 11 | 155 |
| E6 | 8 | 73 |
| E6 | 10 | 73 |
| E6 | 11 | 73 |
| E2 | 8 | 350 |
| E2 | 9 | 350 |
| E1 | 8 | 312 |
| E1 | 10 | 312 |
| E1 | 9 | 254 |
| E1 | 10 | 254 |
| E1 | 11 | 254 |
| E6 | 8 | 116 |
| E6 | 9 | 116 |
| E6 | 10 | 116 |
| E6 | 11 | 116 |
| E1 | 11 | 460 |
| E6 | 9 | 128 |
| E1 | 9 | 357 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| L1 | 10 | 347 |
| L1 | 11 | 347 |
| E1 | 10 | 484 |
| E1 | 11 | 484 |
| E1 | 8 | 228 |
| E5 | 10 | 50 |
| E1 | 8 | 286 |
| E6 | 8 | 18 |
| E5 | 8 | 43 |
| E5 | 11 | 43 |
| L1 | 10 | 56 |
| E2 | 9 | 165 |
| E2 | 11 | 165 |
| E1 | 8 | 518 |
| E1 | 9 | 433 |
| L2 | 8 | 33 |
| E2 | 8 | 358 |
| E1 | 10 | 121 |
| E6 | 10 | 99 |
| E6 | 11 | 99 |
| E1 | 10 | 283 |
| E1 | 11 | 283 |
| L1 | 9 | 53 |
| L1 | 8 | 61 |
| L1 | 10 | 61 |
| L1 | 11 | 61 |
| E2 | 8 | 147 |
| E2 | 9 | 147 |
| L1 | 8 | 19 |
| L1 | 10 | 19 |
| L1 | 11 | 19 |
| L1 | 9 | 71 |
| L1 | 10 | 71 |
| L1 | 11 | 71 |
| E6 | 8 | 52 |
| E6 | 10 | 52 |
| E6 | 11 | 52 |
| E2 | 9 | 313 |
| L1 | 8 | 42 |
| L1 | 11 | 42 |
| L1 | 9 | 341 |
| L1 | 11 | 341 |
| E6 | 8 | 111 |
| E6 | 9 | 111 |
| E6 | 11 | 106 |
| E6 | 10 | 16 |
| L1 | 8 | 374 |
| E5 | 8 | 72 |
| E5 | 9 | 72 |
| E5 | 10 | 72 |
| E1 | 11 | 110 |
| E1 | 11 | 522 |
| E1 | 10 | 541 |
| E1 | 11 | 541 |
| L1 | 9 | 219 |
| L1 | 10 | 219 |
| L1 | 8 | 455 |
| L1 | 9 | 455 |
| L1 | 10 | 455 |
| L2 | 8 | 141 |
| L1 | 8 | 87 |
| E2 | 10 | 310 |
| L2 | 8 | 448 |
| L1 | 11 | 243 |
| E5 | 8 | 15 |
| E5 | 9 | 15 |
| L1 | 10 | 303 |
| L1 | 11 | 303 |
| E1 | 9 | 66 |
| E1 | 10 | 66 |
| E1 | 11 | 66 |
| E5 | 8 | 19 |
| L1 | 10 | 326 |
| E1 | 8 | 495 |
| E6 | 8 | 121 |
| E5 | 8 | 28 |
| E5 | 9 | 28 |
| E5 | 10 | 28 |
| L1 | 11 | 460 |
| E4 | 8 | 60 |
| L2 | 8 | 73 |
| E1 | 11 | 295 |
| L1 | 8 | 110 |
| L2 | 10 | 106 |
| E1 | 8 | 255 |
| E1 | 9 | 255 |
| E1 | 10 | 255 |
| E5 | 8 | 33 |
| E5 | 11 | 33 |
| E5 | 8 | 16 |
| E5 | 9 | 16 |
| E5 | 10 | 16 |
| E6 | 8 | 101 |
| E5 | 9 | 101 |
| E1 | 8 | 279 |
| E1 | 10 | 279 |
| E1 | 9 | 223 |
| L2 | 11 | 178 |
| E5 | 8 | 36 |
| L1 | 8 | 41 |
| L1 | 9 | 41 |
| E1 | 11 | 540 |

TABLE XVI-continued

C. HPVI1
HLA-A3 Motif Peptides

| 2 | 3 | 4 |
|---|---|---|
| E4 | 9 | 18 |
| E4 | 11 | 18 |
| E4 | 8 | 34 |
| E5 | 8 | 32 |
| E1 | 8 | 198 |
| E5 | 9 | 31 |
| E5 | 8 | 30 |
| E5 | 10 | 30 |
| E5 | 9 | 59 |
| E5 | 10 | 59 |
| E1 | 8 | 298 |
| E4 | 10 | 31 |
| E4 | 11 | 31 |
| L1 | 9 | 465 |
| E5 | 8 | 69 |
| E5 | 9 | 69 |
| E5 | 11 | 69 |
| E5 | 8 | 60 |
| E5 | 9 | 60 |
| L1 | 9 | 272 |
| E1 | 8 | 276 |
| E1 | 11 | 276 |
| E1 | 11 | 563 |
| L1 | 8 | 379 |
| L1 | 10 | 379 |
| E1 | 9 | 605 |
| E1 | 10 | 605 |
| E1 | 8 | 218 |
| E1 | 10 | 218 |
| E1 | 11 | 218 |
| L2 | 8 | 386 |
| E1 | 9 | 458 |
| L2 | 10 | 239 |
| E1 | 8 | 132 |
| E1 | 8 | 358 |
| E1 | 9 | 358 |
| E4 | 8 | 90 |
| E5 | 8 | 70 |
| E5 | 10 | 70 |
| E5 | 11 | 70 |
| E2 | 8 | 103 |
| E2 | 9 | 103 |
| E2 | 10 | 103 |
| E6 | 8 | 38 |
| E6 | 9 | 38 |
| E6 | 10 | 38 |
| E6 | 11 | 38 |
| E5 | 8 | 61 |
| E1 | 9 | 115 |
| E1 | 10 | 115 |
| E1 | 11 | 115 |
| E2 | 9 | 62 |
| E2 | 11 | 62 |
| E2 | 9 | 334 |
| L2 | 9 | 337 |
| L1 | 8 | 273 |
| E1 | 10 | 277 |
| E5 | 8 | 47 |
| L2 | 10 | 292 |
| L1 | 9 | 296 |
| L1 | 11 | 296 |
| E1 | 10 | 564 |
| L2 | 9 | 245 |
| E7 | 11 | 67 |
| L1 | 9 | 234 |
| L1 | 11 | 234 |
| E4 | 10 | 11 |
| E1 | 8 | 409 |
| E1 | 11 | 409 |
| L2 | 8 | 276 |
| L2 | 10 | 276 |
| L1 | 9 | 252 |
| L1 | 10 | 252 |
| L2 | 11 | 407 |
| L1 | 9 | 440 |
| L1 | 11 | 440 |
| E5 | 9 | 62 |
| E5 | 11 | 62 |
| E1 | 8 | 546 |
| E1 | 9 | 546 |
| E1 | 8 | 421 |
| E1 | 9 | 421 |
| E1 | 10 | 421 |
| L1 | 9 | 339 |
| L1 | 11 | 339 |
| E1 | 8 | 47 |
| E1 | 9 | 47 |
| L1 | 8 | 197 |
| L1 | 11 | 197 |
| E1 | 8 | 19 |
| L1 | 11 | 155 |
| E1 | 8 | 274 |
| E1 | 9 | 274 |
| E1 | 10 | 274 |
| E4 | 8 | 1 |
| E4 | 9 | 1 |
| E2 | 8 | 71 |
| E2 | 8 | 329 |
| E6 | 9 | 36 |
| E6 | 10 | 36 |
| E6 | 11 | 36 |
| E1 | 9 | 329 |
| E1 | 10 | 100 |
| E1 | 9 | 600 |
| E2 | 8 | 294 |
| E2 | 9 | 294 |
| E5 | 8 | 9 |
| E1 | 10 | 368 |
| E1 | 11 | 368 |
| E2 | 8 | 304 |
| E2 | 11 | 304 |
| L2 | 8 | 342 |
| L2 | 11 | 342 |
| L1 | 9 | 206 |
| E2 | 8 | 170 |
| E2 | 9 | 170 |
| E6 | 8 | 58 |
| E1 | 8 | 156 |
| L1 | 8 | 318 |
| L1 | 10 | 318 |
| E1 | 11 | 598 |
| L1 | 8 | 407 |
| L1 | 9 | 407 |
| L1 | 10 | 407 |
| E1 | 9 | 568 |
| E1 | 10 | 568 |
| E1 | 11 | 568 |
| E1 | 10 | 451 |
| L1 | 10 | 31 |
| E7 | 8 | 88 |
| E7 | 10 | 88 |
| E2 | 9 | 264 |
| E2 | 10 | 264 |
| E6 | 10 | 50 |
| E4 | 8 | 33 |
| E4 | 9 | 33 |
| E1 | 8 | 397 |
| E1 | 11 | 397 |
| L1 | 10 | 338 |
| L1 | 9 | 353 |
| L1 | 10 | 353 |
| E2 | 8 | 22 |
| E2 | 11 | 22 |
| E1 | 8 | 395 |
| E1 | 10 | 395 |
| E1 | 9 | 59 |
| E1 | 11 | 59 |
| E2 | 10 | 347 |

TABLE XVI-continued

C. HPVI1
HLA-A3 Motif Peptides

| 2 | 3 | 4 |
|---|---|---|
| E2 | 11 | 347 |
| E2 | 9 | 248 |
| E5 | 8 | 54 |
| E5 | 11 | 54 |
| E2 | 10 | 127 |
| L2 | 9 | 236 |
| E5 | 8 | 78 |
| L2 | 11 | 138 |
| L2 | 8 | 79 |
| L2 | 9 | 79 |
| L2 | 10 | 79 |
| L2 | 11 | 284 |
| L2 | 9 | 416 |
| E4 | 9 | 49 |
| E4 | 10 | 49 |
| E4 | 11 | 49 |
| E2 | 11 | 216 |
| E2 | 9 | 196 |
| L1 | 9 | 483 |
| L1 | 11 | 483 |
| E1 | 9 | 528 |
| E1 | 11 | 528 |
| L2 | 10 | 271 |
| L2 | 8 | 398 |
| E7 | 9 | 18 |
| E1 | 8 | 480 |
| L2 | 9 | 28 |
| L1 | 8 | 229 |
| L1 | 11 | 229 |
| L2 | 11 | 351 |
| E1 | 8 | 594 |
| E1 | 10 | 594 |
| E1 | 10 | 226 |
| E1 | 11 | 456 |
| E1 | 10 | 592 |
| L2 | 8 | 410 |
| E4 | 9 | 4 |
| E4 | 10 | 4 |
| L2 | 8 | 354 |
| E1 | 8 | 94 |
| E1 | 8 | 442 |
| E6 | 9 | 110 |
| E6 | 10 | 110 |
| L1 | 10 | 218 |
| L1 | 11 | 218 |
| L2 | 8 | 447 |
| L2 | 9 | 447 |
| L1 | 8 | 161 |
| L2 | 9 | 72 |
| L1 | 9 | 109 |
| E4 | 11 | 30 |
| L2 | 8 | 211 |
| L2 | 10 | 211 |
| E4 | 9 | 44 |
| E4 | 10 | 44 |
| L2 | 9 | 385 |
| E1 | 8 | 513 |
| E2 | 8 | 61 |
| E2 | 10 | 61 |
| L2 | 10 | 336 |
| E1 | 8 | 545 |
| E1 | 9 | 545 |
| E1 | 10 | 545 |
| L1 | 10 | 292 |
| L2 | 11 | 101 |
| L1 | 8 | 488 |
| L1 | 9 | 488 |
| L1 | 11 | 488 |
| E2 | 10 | 244 |
| L1 | 9 | 392 |
| L2 | 9 | 403 |
| E2 | 9 | 353 |
| L1 | 11 | 427 |
| L2 | 9 | 206 |
| L2 | 10 | 206 |
| L2 | 11 | 206 |
| L1 | 9 | 90 |
| E2 | 11 | 211 |
| L2 | 8 | 434 |
| L2 | 9 | 434 |
| L2 | 10 | 434 |
| L2 | 11 | 434 |
| L2 | 9 | 422 |
| L2 | 10 | 422 |
| L2 | 8 | 90 |
| L1 | 9 | 267 |
| L2 | 10 | 358 |
| L1 | 10 | 16 |
| L1 | 11 | 16 |
| L2 | 9 | 327 |
| E1 | 9 | 399 |
| E1 | 9 | 64 |
| E1 | 11 | 64 |
| E4 | 8 | 46 |
| E4 | 10 | 46 |
| E6 | 8 | 30 |
| E7 | 9 | 43 |
| E7 | 10 | 43 |
| L1 | 10 | 193 |
| L2 | 9 | 320 |
| L2 | 10 | 320 |
| E2 | 8 | 140 |
| L1 | 11 | 138 |
| L1 | 9 | 434 |
| E2 | 8 | 12 |
| E5 | 11 | 66 |
| E1 | 11 | 355 |
| E2 | 9 | 163 |
| E2 | 11 | 163 |
| E1 | 10 | 445 |
| L1 | 8 | 457 |
| L2 | 8 | 261 |
| L2 | 10 | 261 |
| E2 | 8 | 290 |
| E2 | 10 | 290 |
| E2 | 11 | 290 |
| E6 | 8 | 71 |
| E6 | 9 | 71 |
| E6 | 10 | 71 |
| E2 | 8 | 113 |
| E2 | 9 | 113 |
| L2 | 11 | 42 |
| E6 | 8 | 28 |
| E6 | 10 | 28 |
| E6 | 11 | 15 |
| L1 | 8 | 152 |
| L1 | 9 | 373 |
| L1 | 11 | 302 |
| E2 | 10 | 288 |
| L2 | 8 | 15 |
| E4 | 9 | 14 |
| E4 | 11 | 14 |
| L1 | 10 | 233 |
| L1 | 8 | 251 |
| L1 | 10 | 251 |
| L1 | 11 | 251 |
| E2 | 8 | 76 |
| E2 | 9 | 76 |
| L2 | 8 | 395 |
| L2 | 11 | 395 |
| E1 | 8 | 314 |
| E1 | 10 | 314 |
| E1 | 11 | 314 |
| L1 | 10 | 467 |
| L1 | 11 | 467 |
| L1 | 9 | 418 |
| L1 | 10 | 150 |
| E2 | 9 | 218 |

TABLE XVI-continued

C. HPVI1
HLA-A3 Motif Peptides

| 2 | 3 | 4 |
|---|---|---|
| E1 | 9 | 344 |
| L2 | 8 | 230 |
| L2 | 9 | 230 |
| E1 | 10 | 391 |
| E1 | 11 | 391 |
| L2 | 11 | 214 |
| L2 | 8 | 4 |
| L2 | 10 | 4 |
| L2 | 8 | 10 |
| E5 | 8 | 36 |
| E5 | 10 | 36 |
| E1 | 9 | 639 |
| E1 | 10 | 167 |
| E1 | 11 | 167 |
| E6 | 8 | 56 |
| E6 | 10 | 56 |
| E6 | 10 | 125 |
| E1 | 8 | 281 |
| L2 | 8 | 294 |
| E1 | 8 | 383 |
| E1 | 9 | 383 |
| E1 | 10 | 383 |
| E1 | 11 | 383 |
| L2 | 8 | 290 |
| L1 | 11 | 471 |
| L2 | 11 | 301 |
| L2 | 9 | 297 |
| L2 | 11 | 297 |
| L2 | 10 | 445 |
| L2 | 11 | 445 |
| E2 | 8 | 37 |
| E2 | 9 | 37 |
| E2 | 10 | 37 |
| E2 | 11 | 37 |
| L1 | 8 | 242 |
| E4 | 9 | 59 |
| L2 | 10 | 280 |
| L2 | 11 | 280 |
| L1 | 9 | 40 |
| L1 | 10 | 40 |
| E2 | 8 | 302 |
| E2 | 10 | 302 |
| L2 | 10 | 244 |
| L2 | 8 | 307 |
| L2 | 9 | 307 |
| L2 | 11 | 307 |
| L1 | 9 | 280 |
| L1 | 11 | 280 |
| E1 | 8 | 205 |
| E1 | 9 | 205 |
| L1 | 9 | 335 |
| L1 | 8 | 477 |
| L1 | 11 | 477 |
| L1 | 8 | 29 |
| L1 | 9 | 473 |
| L1 | 10 | 473 |
| E1 | 10 | 231 |
| L2 | 8 | 220 |
| L1 | 8 | 141 |
| L1 | 9 | 141 |
| E1 | 11 | 583 |
| E2 | 11 | 225 |
| L1 | 9 | 380 |
| L2 | 8 | 110 |
| E2 | 8 | 234 |
| E2 | 9 | 234 |
| L2 | 9 | 180 |
| L1 | 8 | 475 |
| L1 | 10 | 475 |
| L2 | 10 | 12 |
| L2 | 11 | 12 |
| E6 | 10 | 9 |
| L1 | 9 | 348 |
| L1 | 10 | 348 |

TABLE XVI-continued

C. HPVI1
HLA-A3 Motif Peptides

| 2 | 3 | 4 |
|---|---|---|
| E1 | 9 | 485 |
| E1 | 10 | 485 |
| E1 | 8 | 606 |
| E1 | 9 | 606 |
| E1 | 11 | 606 |
| L2 | 10 | 428 |
| L2 | 11 | 428 |
| L1 | 8 | 354 |
| L1 | 9 | 354 |
| E1 | 9 | 219 |
| E1 | 10 | 219 |
| L1 | 8 | 441 |
| L1 | 10 | 441 |
| L1 | 11 | 441 |
| E1 | 11 | 12 |
| L2 | 8 | 174 |
| L1 | 8 | 115 |
| L1 | 9 | 115 |
| E1 | 8 | 193 |
| E1 | 10 | 193 |
| L2 | 10 | 396 |
| L2 | 11 | 204 |
| L2 | 8 | 308 |
| L2 | 10 | 308 |
| L2 | 11 | 308 |
| L1 | 9 | 293 |
| E1 | 9 | 315 |
| E1 | 10 | 315 |
| E1 | 8 | 43 |
| E1 | 10 | 135 |
| E1 | 11 | 135 |
| L1 | 8 | 63 |
| L1 | 9 | 63 |
| L1 | 9 | 468 |
| L1 | 10 | 468 |
| E1 | 8 | 247 |
| E2 | 8 | 207 |
| E2 | 11 | 207 |
| E2 | 10 | 23 |
| E6 | 9 | 12 |
| E1 | 8 | 547 |
| L2 | 9 | 266 |
| L2 | 10 | 266 |
| E1 | 8 | 422 |
| E1 | 9 | 422 |
| L1 | 10 | 376 |
| L1 | 11 | 376 |
| E5 | 11 | 30 |
| L2 | 10 | 102 |
| E1 | 8 | 350 |
| L1 | 9 | 86 |
| E6 | 11 | 23 |
| L2 | 11 | 105 |
| L2 | 10 | 259 |
| E4 | 9 | 89 |
| L1 | 10 | 295 |
| L2 | 9 | 303 |
| L1 | 9 | 298 |
| L1 | 11 | 298 |
| E7 | 8 | 32 |
| E7 | 11 | 32 |
| E2 | 9 | 337 |
| L1 | 11 | 452 |
| L2 | 8 | 132 |
| L1 | 10 | 85 |
| E4 | 10 | 88 |
| L1 | 9 | 38 |
| L1 | 11 | 38 |
| L1 | 10 | 37 |
| L2 | 8 | 208 |
| L2 | 9 | 208 |
| L2 | 11 | 208 |
| E2 | 10 | 200 |
| E2 | 11 | 315 |

TABLE XVI-continued

C. HPVI1
HLA-A3 Motif Peptides

| 2 | 3 | 4 |
|---|---|---|
| L1 | 8 | 281 |
| L1 | 10 | 281 |
| E2 | 9 | 150 |
| E2 | 10 | 150 |
| L1 | 8 | 489 |
| L1 | 10 | 489 |
| E2 | 11 | 260 |
| E1 | 8 | 206 |
| E1 | 11 | 206 |
| E2 | 9 | 180 |
| L1 | 8 | 336 |
| E2 | 9 | 245 |
| L2 | 8 | 209 |
| L2 | 10 | 209 |
| L2 | 9 | 240 |
| E2 | 8 | 190 |
| E2 | 9 | 201 |
| E2 | 10 | 316 |
| L1 | 9 | 282 |
| E2 | 8 | 151 |
| E2 | 9 | 151 |
| E1 | 8 | 60 |
| E1 | 10 | 60 |
| L2 | 8 | 152 |
| E1 | 11 | 436 |
| L2 | 11 | 163 |
| E2 | 9 | 348 |
| E2 | 10 | 348 |
| E2 | 11 | 348 |
| L1 | 8 | 393 |
| E2 | 8 | 40 |
| E5 | 10 | 45 |
| L1 | 8 | 344 |
| L2 | 11 | 144 |
| E4 | 11 | 54 |
| E6 | 8 | 40 |
| E6 | 9 | 40 |
| E6 | 10 | 40 |
| L1 | 9 | 490 |
| L1 | 11 | 490 |
| L2 | 8 | 404 |
| E1 | 8 | 233 |
| E1 | 10 | 233 |
| E7 | 11 | 56 |
| E2 | 8 | 160 |
| E2 | 9 | 160 |
| L2 | 9 | 25 |
| L1 | 9 | 423 |
| L1 | 11 | 423 |
| E1 | 11 | 515 |
| L1 | 11 | 23 |
| E2 | 9 | 267 |
| E2 | 10 | 267 |
| L2 | 11 | 234 |
| L2 | 9 | 344 |
| E1 | 8 | 588 |
| E1 | 10 | 588 |
| L2 | 11 | 401 |
| E1 | 8 | 586 |
| E1 | 10 | 586 |
| L2 | 8 | 60 |
| L2 | 9 | 60 |
| L2 | 11 | 60 |
| L1 | 8 | 200 |
| L1 | 9 | 200 |
| L1 | 10 | 478 |
| L2 | 11 | 420 |
| L2 | 8 | 426 |
| L2 | 11 | 23 |
| E1 | 8 | 15 |
| L2 | 8 | 38 |
| E2 | 10 | 261 |
| E2 | 8 | 354 |
| L2 | 11 | 129 |

TABLE XVI-continued

C. HPVI1
HLA-A3 Motif Peptides

| 2 | 3 | 4 |
|---|---|---|
| L1 | 8 | 340 |
| L1 | 10 | 340 |
| E2 | 8 | 249 |
| E5 | 9 | 71 |
| E5 | 10 | 71 |
| E5 | 11 | 71 |
| L1 | 8 | 409 |
| E1 | 10 | 207 |
| E5 | 9 | 15 |
| E5 | 10 | 15 |
| E5 | 11 | 15 |
| E1 | 9 | 297 |
| E7 | 10 | 86 |
| E6 | 8 | 26 |
| E6 | 10 | 26 |
| L1 | 8 | 378 |
| L1 | 9 | 378 |
| L1 | 11 | 378 |
| E2 | 10 | 333 |
| L1 | 8 | 474 |
| L1 | 9 | 474 |
| L1 | 11 | 474 |
| E6 | 11 | 8 |
| E1 | 9 | 192 |
| E1 | 11 | 192 |
| E6 | 8 | 11 |
| E6 | 10 | 11 |
| E1 | 8 | 566 |
| E1 | 11 | 566 |
| L2 | 8 | 287 |
| L2 | 9 | 287 |
| L2 | 11 | 287 |
| L2 | 9 | 131 |
| E4 | 11 | 87 |
| L2 | 8 | 207 |
| L2 | 9 | 207 |
| L2 | 10 | 207 |
| E2 | 10 | 149 |
| E2 | 11 | 149 |
| L2 | 9 | 151 |
| E5 | 11 | 44 |
| E2 | 11 | 97 |
| E6 | 8 | 39 |
| E6 | 9 | 39 |
| E6 | 10 | 39 |
| E6 | 11 | 39 |
| E2 | 8 | 219 |
| E1 | 9 | 232 |
| E1 | 11 | 232 |
| E2 | 8 | 228 |
| E2 | 11 | 228 |
| E1 | 9 | 585 |
| E1 | 11 | 585 |
| L2 | 9 | 37 |
| E5 | 10 | 14 |
| E5 | 11 | 14 |
| E1 | 8 | 116 |
| E1 | 9 | 116 |
| E1 | 10 | 116 |
| L1 | 8 | 91 |
| L1 | 11 | 333 |
| L2 | 10 | 150 |
| E5 | 11 | 13 |
| L2 | 11 | 149 |
| E5 | 10 | 55 |
| E4 | 8 | 100 |
| E2 | 10 | 212 |
| L1 | 8 | 224 |
| E5 | 9 | 56 |
| E1 | 8 | 345 |
| E1 | 11 | 498 |
| L2 | 11 | 383 |
| E1 | 8 | 78 |
| E1 | 9 | 78 |

TABLE XVI-continued

C. HPVI1
HLA-A3 Motif Peptides

| 2 | 3 | 4 |
|---|---|---|
| E2 | 8 | 202 |
| E2 | 8 | 63 |
| E2 | 10 | 63 |
| L1 | 9 | 57 |
| L1 | 11 | 57 |
| L2 | 8 | 338 |
| L2 | 11 | 338 |
| E1 | 8 | 239 |
| E1 | 11 | 239 |
| L1 | 8 | 283 |
| L1 | 8 | 21 |
| L1 | 9 | 21 |
| E5 | 10 | 25 |
| E5 | 11 | 25 |
| L1 | 11 | 225 |
| E7 | 8 | 90 |
| E5 | 8 | 74 |
| E5 | 10 | 74 |
| E2 | 8 | 152 |
| E1 | 8 | 182 |
| E1 | 9 | 182 |
| E1 | 8 | 48 |
| E7 | 9 | 37 |
| E1 | 8 | 221 |
| E1 | 11 | 221 |
| E1 | 8 | 434 |
| L1 | 10 | 198 |
| L1 | 11 | 198 |
| E5 | 8 | 57 |
| E6 | 10 | 32 |
| L2 | 8 | 423 |
| L2 | 9 | 423 |
| L2 | 11 | 423 |
| L1 | 11 | 69 |
| L1 | 10 | 156 |
| L1 | 9 | 44 |
| L1 | 10 | 44 |
| E1 | 10 | 437 |
| E1 | 8 | 477 |
| E1 | 11 | 477 |
| L1 | 11 | 112 |
| E1 | 11 | 346 |
| E1 | 11 | 333 |
| L2 | 11 | 30 |
| L2 | 10 | 164 |
| E1 | 10 | 499 |
| E1 | 11 | 499 |
| E5 | 8 | 27 |
| E5 | 9 | 27 |
| E5 | 10 | 27 |
| E5 | 11 | 27 |
| E5 | 9 | 32 |
| E6 | 9 | 100 |
| E6 | 10 | 100 |
| E1 | 9 | 278 |
| E1 | 11 | 278 |
| E4 | 8 | 17 |
| E4 | 10 | 17 |
| E1 | 8 | 275 |
| E1 | 9 | 275 |
| L1 | 8 | 73 |
| L1 | 9 | 73 |
| E5 | 9 | 46 |
| E4 | 11 | 10 |
| E2 | 9 | 128 |
| E2 | 11 | 128 |
| E2 | 8 | 233 |
| E2 | 9 | 233 |
| E2 | 10 | 233 |
| E2 | 9 | 64 |
| L1 | 9 | 114 |
| L1 | 10 | 114 |
| L1 | 9 | 62 |
| L1 | 10 | 62 |

TABLE XVI-continued

C. HPVI1
HLA-A3 Motif Peptides

| 2 | 3 | 4 |
|---|---|---|
| E2 | 9 | 206 |
| L1 | 9 | 485 |
| L1 | 10 | 485 |
| L1 | 11 | 485 |
| L1 | 9 | 17 |
| L1 | 10 | 17 |
| L2 | 8 | 104 |
| L2 | 11 | 258 |
| E1 | 8 | 92 |
| E1 | 10 | 92 |
| L1 | 8 | 297 |
| L1 | 10 | 297 |
| E2 | 11 | 199 |
| E2 | 8 | 266 |
| E2 | 10 | 266 |
| E2 | 11 | 266 |
| E2 | 11 | 332 |
| L2 | 10 | 145 |
| L2 | 11 | 414 |
| L2 | 11 | 325 |
| E1 | 9 | 565 |
| E2 | 8 | 148 |
| E2 | 11 | 148 |
| E1 | 10 | 584 |
| L1 | 8 | 328 |
| L2 | 8 | 246 |
| E1 | 8 | 238 |
| E1 | 9 | 238 |
| L1 | 9 | 20 |
| L1 | 10 | 20 |
| E5 | 11 | 24 |
| E7 | 10 | 68 |
| L1 | 8 | 72 |
| L1 | 9 | 72 |
| L1 | 10 | 72 |
| E4 | 8 | 2 |
| E4 | 11 | 2 |
| L1 | 8 | 58 |
| L1 | 10 | 58 |
| L1 | 11 | 58 |
| E2 | 11 | 58 |
| L2 | 9 | 120 |
| E5 | 8 | 3 |
| E5 | 9 | 3 |
| E6 | 9 | 53 |
| E6 | 10 | 53 |
| E6 | 11 | 53 |
| L1 | 10 | 97 |
| E2 | 8 | 320 |
| E2 | 9 | 320 |
| E2 | 11 | 320 |
| E1 | 10 | 17 |
| E1 | 9 | 322 |
| L2 | 11 | 392 |
| E1 | 10 | 272 |
| E1 | 11 | 272 |
| L2 | 8 | 46 |
| E1 | 8 | 426 |
| E1 | 10 | 340 |
| E5 | 9 | 14 |
| E5 | 10 | 14 |
| E5 | 9 | 18 |
| E1 | 8 | 464 |
| E5 | 10 | 58 |
| E5 | 11 | 58 |
| L1 | 8 | 309 |
| E1 | 8 | 510 |
| E1 | 9 | 510 |
| E1 | 11 | 510 |
| E2 | 9 | 102 |
| E2 | 10 | 102 |
| E2 | 11 | 102 |
| E2 | 8 | 92 |
| E1 | 9 | 530 |

TABLE XVI-continued

C. HPVI1
HLA-A3 Motif Peptides

| 2 | 3 | 4 |
|---|---|---|
| E2 | 10 | 145 |
| E2 | 11 | 145 |
| E1 | 9 | 237 |
| E1 | 10 | 237 |
| E1 | 10 | 262 |
| E1 | 11 | 380 |
| E1 | 8 | 76 |
| E1 | 9 | 76 |
| E1 | 10 | 76 |
| E1 | 11 | 76 |
| E6 | 9 | 44 |
| E6 | 11 | 46 |
| L1 | 10 | 123 |
| E1 | 10 | 45 |
| E1 | 11 | 45 |
| L2 | 8 | 437 |
| L2 | 9 | 437 |
| E5 | 8 | 76 |
| E5 | 10 | 76 |
| L2 | 11 | 318 |
| L1 | 8 | 239 |
| L1 | 10 | 239 |
| L1 | 11 | 239 |
| L1 | 10 | 132 |
| E2 | 11 | 178 |
| E2 | 10 | 188 |
| E1 | 8 | 137 |
| E1 | 9 | 137 |
| L2 | 9 | 70 |
| L2 | 11 | 70 |
| E4 | 8 | 22 |
| L2 | 8 | 431 |
| L2 | 9 | 431 |
| L2 | 10 | 431 |
| L2 | 11 | 431 |
| E1 | 9 | 579 |
| E1 | 11 | 579 |
| E2 | 10 | 138 |
| L1 | 9 | 231 |
| L1 | 8 | 246 |
| L1 | 9 | 246 |
| L1 | 10 | 246 |
| L1 | 11 | 246 |
| E5 | 10 | 61 |
| L1 | 8 | 49 |
| E2 | 10 | 336 |
| E2 | 9 | 159 |
| E2 | 10 | 159 |
| L1 | 9 | 351 |
| L1 | 11 | 351 |
| E2 | 8 | 214 |
| L2 | 10 | 305 |
| L2 | 11 | 305 |
| E1 | 10 | 402 |
| E1 | 11 | 402 |
| L1 | 8 | 26 |
| L1 | 9 | 26 |
| L1 | 10 | 26 |
| L1 | 11 | 26 |
| E4 | 9 | 16 |
| E4 | 11 | 16 |
| E4 | 8 | 9 |
| E2 | 8 | 168 |
| E2 | 10 | 168 |
| E2 | 11 | 168 |
| E1 | 8 | 502 |
| L1 | 10 | 10 |
| L1 | 11 | 416 |
| E1 | 9 | 91 |
| E1 | 11 | 91 |
| E2 | 8 | 131 |

SF 1168134 v1

TABLE XVII

HLA-AI1 Motif Peptides

| 1 | 2 | 3 | 4 |
|---|---|---|---|
| HPV16 | E1 | 8 | 316 |
| HPV16 | E1 | 8 | 205 |
| HPV16 | E1 | 11 | 205 |
| HPV16 | E1 | 11 | 248 |
| HPV16 | E1 | 10 | 391 |
| HPV16 | E1 | 9 | 570 |
| HPV16 | E1 | 11 | 570 |
| HPV16 | E1 | 9 | 112 |
| HPV16 | E1 | 9 | 69 |
| HPV16 | E1 | 11 | 69 |
| HPV16 | E1 | 11 | 459 |
| HPV16 | E1 | 10 | 206 |
| HPV16 | E1 | 8 | 406 |
| HPV16 | E1 | 9 | 406 |
| HPV16 | E1 | 8 | 524 |
| HPV16 | E1 | 8 | 82 |
| HPV16 | E1 | 9 | 82 |
| HPV16 | E1 | 8 | 405 |
| HPV16 | E1 | 9 | 405 |
| HPV16 | E1 | 10 | 405 |
| HPV16 | E1 | 11 | 430 |
| HPV16 | E1 | 8 | 500 |
| HPV16 | E1 | 10 | 283 |
| HPV16 | E1 | 10 | 114 |
| HPV16 | E1 | 11 | 114 |
| HPV16 | E1 | 8 | 304 |
| HPV16 | E1 | 10 | 304 |
| HPV16 | E1 | 9 | 101 |
| HPV16 | E1 | 11 | 101 |
| HPV16 | E1 | 9 | 523 |
| HPV16 | E1 | 8 | 81 |
| HPV16 | E1 | 9 | 81 |
| HPV16 | E1 | 10 | 81 |
| HPV16 | E1 | 8 | 404 |
| HPV16 | E1 | 9 | 404 |
| HPV16 | E1 | 10 | 404 |
| HPV16 | E1 | 11 | 404 |
| HPV16 | E1 | 10 | 522 |
| HPV16 | E1 | 8 | 371 |
| HPV16 | E1 | 9 | 371 |
| HPV16 | E1 | 9 | 50 |
| HPV16 | E1 | 9 | 631 |
| HPV16 | E1 | 10 | 541 |
| HPV16 | E1 | 11 | 541 |
| HPV16 | E1 | 10 | 368 |
| HPV16 | E1 | 11 | 368 |
| HPV16 | E1 | 9 | 103 |
| HPV16 | E1 | 8 | 372 |
| HPV16 | E1 | 10 | 249 |
| HPV16 | E1 | 8 | 573 |
| HPV16 | E1 | 10 | 573 |
| HPV16 | E1 | 11 | 384 |
| HPV16 | E1 | 8 | 335 |
| HPV16 | E1 | 11 | 548 |
| HPV16 | E1 | 10 | 452 |
| HPV16 | E1 | 11 | 452 |
| HPV16 | E1 | 10 | 11 |
| HPV16 | E1 | 8 | 603 |
| HPV16 | E1 | 10 | 356 |
| HPV16 | E1 | 10 | 221 |
| HPV16 | E1 | 11 | 629 |
| HPV16 | E1 | 9 | 152 |
| HPV16 | E1 | 9 | 288 |
| HPV16 | E1 | 11 | 140 |
| HPV16 | E1 | 9 | 594 |
| HPV16 | E1 | 8 | 612 |
| HPV16 | E1 | 8 | 51 |
| HPV16 | E1 | 9 | 392 |
| HPV16 | E1 | 8 | 463 |
| HPV16 | E1 | 9 | 453 |
| HPV16 | E1 | 10 | 453 |
| HPV16 | E1 | 9 | 219 |
| HPV16 | E1 | 11 | 613 |
| HPV16 | E1 | 9 | 71 |
| HPV16 | E1 | 10 | 71 |

TABLE XVII-continued

HLA-AI1 Motif Peptides

| 1 | 2 | 3 | 4 |
|---|---|---|---|
| HPV16 | E1 | 10 | 100 |
| HPV16 | E1 | 8 | 632 |
| HPV16 | E1 | 9 | 334 |
| HPV16 | E1 | 11 | 437 |
| HPV16 | E1 | 8 | 176 |
| HPV16 | E1 | 9 | 176 |
| HPV16 | E1 | 10 | 162 |
| HPV16 | E1 | 11 | 466 |
| HPV16 | E1 | 9 | 325 |
| HPV16 | E1 | 11 | 242 |
| HPV16 | E1 | 9 | 272 |
| HPV16 | E1 | 10 | 272 |
| HPV16 | E1 | 11 | 272 |
| HPV16 | E1 | 9 | 542 |
| HPV16 | E1 | 10 | 542 |
| HPV16 | E1 | 11 | 542 |
| HPV16 | E1 | 10 | 598 |
| HPV16 | E1 | 10 | 174 |
| HPV16 | E1 | 11 | 174 |
| HPV16 | E1 | 9 | 163 |
| HPV16 | E1 | 10 | 496 |
| HPV16 | E1 | 8 | 571 |
| HPV16 | E1 | 10 | 571 |
| HPV16 | E1 | 9 | 12 |
| HPV16 | E1 | 9 | 216 |
| HPV16 | E1 | 10 | 68 |
| HPV16 | E1 | 11 | 507 |
| HPV16 | E1 | 9 | 499 |
| HPV16 | E1 | 8 | 113 |
| HPV16 | E1 | 11 | 113 |
| HPV16 | E1 | 11 | 473 |
| HPV16 | E1 | 11 | 194 |
| HPV16 | E1 | 8 | 568 |
| HPV16 | E1 | 11 | 568 |
| HPV16 | E1 | 8 | 326 |
| HPV16 | E1 | 9 | 369 |
| HPV16 | E1 | 10 | 369 |
| HPV16 | E1 | 11 | 369 |
| HPV16 | E1 | 10 | 401 |
| HPV16 | E1 | 11 | 401 |
| HPV16 | E1 | 9 | 204 |
| HPV16 | E1 | 10 | 111 |
| HPV16 | E1 | 11 | 282 |
| HPV16 | E1 | 8 | 403 |
| HPV16 | E1 | 9 | 403 |
| HPV16 | E1 | 10 | 403 |
| HPV16 | E1 | 11 | 403 |
| HPV16 | E1 | 11 | 400 |
| HPV16 | E1 | 10 | 311 |
| HPV16 | E1 | 8 | 285 |
| HPV16 | E1 | 9 | 607 |
| HPV16 | E1 | 10 | 610 |
| HPV16 | E1 | 10 | 483 |
| HPV16 | E1 | 10 | 394 |
| HPV16 | E1 | 11 | 323 |
| HPV16 | E1 | 10 | 252 |
| HPV16 | E1 | 8 | 208 |
| HPV16 | E1 | 11 | 521 |
| HPV16 | E1 | 11 | 540 |
| HPV16 | E1 | 9 | 126 |
| HPV16 | E1 | 8 | 485 |
| HPV16 | E1 | 8 | 70 |
| HPV16 | E1 | 10 | 70 |
| HPV16 | E1 | 11 | 70 |
| HPV16 | E1 | 10 | 276 |
| HPV16 | E1 | 8 | 254 |
| HPV16 | E1 | 10 | 254 |
| HPV16 | E1 | 9 | 277 |
| HPV16 | E1 | 11 | 277 |
| HPV16 | E1 | 10 | 474 |
| HPV16 | E1 | 10 | 195 |
| HPV16 | E1 | 9 | 620 |
| HPV16 | E1 | 9 | 357 |
| HPV16 | E1 | 9 | 191 |
| HPV16 | E1 | 10 | 243 |
| HPV16 | E1 | 10 | 59 |
| HPV16 | E1 | 11 | 48 |
| HPV16 | E1 | 9 | 222 |
| HPV16 | E1 | 8 | 278 |
| HPV16 | E1 | 10 | 278 |
| HPV16 | E1 | 8 | 544 |
| HPV16 | E1 | 9 | 544 |
| HPV16 | E1 | 9 | 303 |
| HPV16 | E1 | 11 | 303 |
| HPV16 | E1 | 10 | 408 |
| HPV16 | E1 | 11 | 408 |
| HPV16 | E1 | 8 | 306 |
| HPV16 | E1 | 9 | 207 |
| HPV16 | E1 | 8 | 144 |
| HPV16 | E1 | 9 | 305 |
| HPV16 | E1 | 8 | 454 |
| HPV16 | E1 | 9 | 454 |
| HPV16 | E1 | 8 | 420 |
| HPV16 | E1 | 9 | 420 |
| HPV16 | E1 | 10 | 420 |
| HPV16 | E1 | 8 | 422 |
| HPV16 | E1 | 11 | 422 |
| HPV16 | E1 | 8 | 273 |
| HPV16 | E1 | 9 | 273 |
| HPV16 | E1 | 10 | 273 |
| HPV16 | E1 | 10 | 569 |
| HPV16 | E1 | 9 | 202 |
| HPV16 | E1 | 11 | 202 |
| HPV16 | E1 | 10 | 630 |
| HPV16 | E1 | 11 | 367 |
| HPV16 | E1 | 11 | 605 |
| HPV16 | E1 | 11 | 597 |
| HPV16 | E1 | 9 | 567 |
| HPV16 | E1 | 8 | 543 |
| HPV16 | E1 | 9 | 543 |
| HPV16 | E1 | 10 | 543 |
| HPV16 | E1 | 8 | 104 |
| HPV16 | E1 | 9 | 386 |
| HPV16 | E1 | 8 | 396 |
| HPV16 | E1 | 9 | 196 |
| HPV16 | E1 | 11 | 527 |
| HPV16 | E1 | 10 | 593 |
| HPV16 | E1 | 10 | 190 |
| HPV16 | E1 | 10 | 302 |
| HPV16 | E1 | 8 | 245 |
| HPV16 | E1 | 8 | 600 |
| HPV16 | E1 | 11 | 600 |
| HPV16 | E1 | 8 | 61 |
| HPV16 | E1 | 11 | 495 |
| HPV16 | E1 | 8 | 441 |
| HPV16 | E1 | 8 | 143 |
| HPV16 | E1 | 9 | 143 |
| HPV16 | E1 | 9 | 419 |
| HPV16 | E1 | 10 | 419 |
| HPV16 | E1 | 11 | 419 |
| HPV16 | E1 | 8 | 118 |
| HPV16 | E1 | 8 | 80 |
| HPV16 | E1 | 9 | 80 |
| HPV16 | E1 | 10 | 80 |
| HPV16 | E1 | 11 | 80 |
| HPV16 | E1 | 8 | 462 |
| HPV16 | E1 | 9 | 462 |
| HPV16 | E1 | 10 | 125 |
| HPV16 | E1 | 9 | 109 |
| HPV16 | E1 | 10 | 619 |
| HPV16 | E1 | 8 | 313 |
| HPV16 | E1 | 10 | 313 |
| HPV16 | E1 | 11 | 313 |
| HPV16 | E1 | 9 | 615 |
| HPV16 | E1 | 9 | 432 |
| HPV16 | E1 | 11 | 390 |
| HPV16 | E1 | 9 | 611 |
| HPV16 | E1 | 8 | 455 |
| HPV16 | E1 | 10 | 218 |
| HPV16 | E1 | 11 | 99 |

TABLE XVII-continued

HLA-AI1 Motif Peptides

| 1 | 2 | 3 | 4 |
|---|---|---|---|
| HPV16 | E1 | 9 | 175 |
| HPV16 | E1 | 10 | 175 |
| HPV16 | E1 | 8 | 164 |
| HPV16 | E1 | 11 | 161 |
| HPV16 | E1 | 11 | 173 |
| HPV16 | E1 | 9 | 250 |
| HPV16 | E1 | 9 | 484 |
| HPV16 | E1 | 8 | 621 |
| HPV16 | E1 | 8 | 421 |
| HPV16 | E1 | 9 | 421 |
| HPV16 | E1 | 10 | 201 |
| HPV16 | E1 | 8 | 387 |
| HPV16 | E1 | 10 | 566 |
| HPV16 | E1 | 9 | 395 |
| HPV16 | E1 | 9 | 314 |
| HPV16 | E1 | 10 | 314 |
| HPV16 | E1 | 9 | 497 |
| HPV16 | E1 | 11 | 497 |
| HPV16 | E1 | 8 | 315 |
| HPV16 | E1 | 9 | 315 |
| HPV16 | E1 | 8 | 72 |
| HPV16 | E1 | 9 | 72 |
| HPV16 | E1 | 9 | 572 |
| HPV16 | E1 | 11 | 572 |
| HPV16 | E1 | 8 | 13 |
| HPV16 | E1 | 10 | 324 |
| HPV16 | E1 | 8 | 289 |
| HPV16 | E1 | 9 | 253 |
| HPV16 | E1 | 11 | 253 |
| HPV16 | E1 | 8 | 407 |
| HPV16 | E1 | 11 | 407 |
| HPV16 | E1 | 8 | 192 |
| HPV16 | E1 | 10 | 385 |
| HPV16 | E1 | 11 | 200 |
| HPV16 | E1 | 11 | 565 |
| HPV16 | E1 | 8 | 433 |
| HPV16 | E1 | 8 | 370 |
| HPV16 | E1 | 9 | 370 |
| HPV16 | E1 | 10 | 370 |
| HPV16 | E1 | 10 | 49 |
| HPV16 | E1 | 8 | 102 |
| HPV16 | E1 | 10 | 102 |
| HPV16 | E1 | 8 | 498 |
| HPV16 | E1 | 10 | 498 |
| HPV16 | E1 | 8 | 197 |
| HPV16 | E1 | 8 | 275 |
| HPV16 | E1 | 11 | 275 |
| HPV16 | E1 | 8 | 217 |
| HPV16 | E1 | 11 | 217 |
| HPV16 | E1 | 8 | 545 |
| HPV16 | E1 | 8 | 274 |
| HPV16 | E1 | 9 | 274 |
| HPV16 | E1 | 10 | 18 |
| HPV16 | E1 | 11 | 18 |
| HPV16 | E1 | 10 | 271 |
| HPV16 | E1 | 11 | 271 |
| HPV16 | E1 | 8 | 425 |
| HPV16 | E1 | 10 | 339 |
| HPV16 | E1 | 9 | 509 |
| HPV16 | E1 | 9 | 529 |
| HPV16 | E1 | 8 | 476 |
| HPV16 | E1 | 10 | 333 |
| HPV16 | E1 | 10 | 215 |
| HPV16 | E1 | 11 | 58 |
| HPV16 | E1 | 8 | 20 |
| HPV16 | E1 | 9 | 20 |
| HPV16 | E2 | 9 | 270 |
| HPV16 | E2 | 8 | 216 |
| HPV16 | E2 | 10 | 216 |
| HPV16 | E2 | 8 | 295 |
| HPV16 | E2 | 9 | 295 |
| HPV16 | E2 | 10 | 295 |
| HPV16 | E2 | 11 | 314 |
| HPV16 | E2 | 8 | 40 |
| HPV16 | E2 | 8 | 300 |
| HPV16 | E2 | 9 | 300 |
| HPV16 | E2 | 10 | 281 |
| HPV16 | E2 | 11 | 126 |
| HPV16 | E2 | 9 | 174 |
| HPV16 | E2 | 9 | 294 |
| HPV16 | E2 | 10 | 294 |
| HPV16 | E2 | 11 | 294 |
| HPV16 | E2 | 8 | 173 |
| HPV16 | E2 | 10 | 173 |
| HPV16 | E2 | 9 | 122 |
| HPV16 | E2 | 10 | 122 |
| HPV16 | E2 | 8 | 124 |
| HPV16 | E2 | 8 | 25 |
| HPV16 | E2 | 10 | 25 |
| HPV16 | E2 | 11 | 25 |
| HPV16 | E2 | 8 | 22 |
| HPV16 | E2 | 11 | 22 |
| HPV16 | E2 | 10 | 246 |
| HPV16 | E2 | 9 | 39 |
| HPV16 | E2 | 11 | 162 |
| HPV16 | E2 | 10 | 149 |
| HPV16 | E2 | 11 | 149 |
| HPV16 | E2 | 10 | 209 |
| HPV16 | E2 | 10 | 74 |
| HPV16 | E2 | 9 | 48 |
| HPV16 | E2 | 8 | 20 |
| HPV16 | E2 | 10 | 20 |
| HPV16 | E2 | 8 | 80 |
| HPV16 | E2 | 8 | 233 |
| HPV16 | E2 | 10 | 233 |
| HPV16 | E2 | 9 | 204 |
| HPV16 | E2 | 11 | 204 |
| HPV16 | E2 | 10 | 121 |
| HPV16 | E2 | 11 | 121 |
| HPV16 | E2 | 9 | 346 |
| HPV16 | E2 | 8 | 271 |
| HPV16 | E2 | 10 | 168 |
| HPV16 | E2 | 11 | 168 |
| HPV16 | E2 | 8 | 108 |
| HPV16 | E2 | 10 | 293 |
| HPV16 | E2 | 11 | 293 |
| HPV16 | E2 | 8 | 123 |
| HPV16 | E2 | 9 | 123 |
| HPV16 | E2 | 10 | 163 |
| HPV16 | E2 | 10 | 156 |
| HPV16 | E2 | 8 | 248 |
| HPV16 | E2 | 11 | 248 |
| HPV16 | E2 | 11 | 230 |
| HPV16 | E2 | 9 | 29 |
| HPV16 | E2 | 10 | 214 |
| HPV16 | E2 | 10 | 290 |
| HPV16 | E2 | 9 | 35 |
| HPV16 | E2 | 10 | 35 |
| HPV16 | E2 | 11 | 35 |
| HPV16 | E2 | 8 | 252 |
| HPV16 | E2 | 8 | 30 |
| HPV16 | E2 | 9 | 210 |
| HPV16 | E2 | 9 | 267 |
| HPV16 | E2 | 10 | 267 |
| HPV16 | E2 | 8 | 45 |
| HPV16 | E2 | 9 | 45 |
| HPV16 | E2 | 8 | 299 |
| HPV16 | E2 | 9 | 299 |
| HPV16 | E2 | 10 | 299 |
| HPV16 | E2 | 9 | 172 |
| HPV16 | E2 | 11 | 172 |
| HPV16 | E2 | 8 | 292 |
| HPV16 | E2 | 11 | 292 |
| HPV16 | E2 | 8 | 180 |
| HPV16 | E2 | 9 | 329 |
| HPV16 | E2 | 9 | 215 |
| HPV16 | E2 | 11 | 215 |
| HPV16 | E2 | 11 | 4 |
| HPV16 | E2 | 11 | 8 |
| HPV16 | E2 | 8 | 347 |

TABLE XVII-continued

HLA-AI1 Motif Peptides

| 1 | 2 | 3 | 4 |
|---|---|---|---|
| HPV16 | E2 | 8 | 268 |
| HPV16 | E2 | 9 | 268 |
| HPV16 | E2 | 11 | 268 |
| HPV16 | E2 | 9 | 103 |
| HPV16 | E2 | 10 | 103 |
| HPV16 | E2 | 11 | 103 |
| HPV16 | E2 | 11 | 77 |
| HPV16 | E2 | 9 | 335 |
| HPV16 | E2 | 8 | 49 |
| HPV16 | E2 | 11 | 280 |
| HPV16 | E2 | 9 | 21 |
| HPV16 | E2 | 9 | 282 |
| HPV16 | E2 | 11 | 282 |
| HPV16 | E2 | 8 | 84 |
| HPV16 | E2 | 8 | 296 |
| HPV16 | E2 | 9 | 296 |
| HPV16 | E2 | 11 | 296 |
| HPV16 | E2 | 10 | 127 |
| HPV16 | E2 | 9 | 284 |
| HPV16 | E2 | 10 | 9 |
| HPV16 | E2 | 11 | 9 |
| HPV16 | E2 | 9 | 250 |
| HPV16 | E2 | 10 | 250 |
| HPV16 | E2 | 8 | 245 |
| HPV16 | E2 | 11 | 245 |
| HPV16 | E2 | 10 | 266 |
| HPV16 | E2 | 11 | 266 |
| HPV16 | E2 | 8 | 106 |
| HPV16 | E2 | 10 | 106 |
| HPV16 | E2 | 9 | 60 |
| HPV16 | E2 | 8 | 12 |
| HPV16 | E2 | 8 | 95 |
| HPV16 | E2 | 11 | 120 |
| HPV16 | E2 | 8 | 170 |
| HPV16 | E2 | 9 | 170 |
| HPV16 | E2 | 11 | 170 |
| HPV16 | E2 | 10 | 345 |
| HPV16 | E2 | 8 | 76 |
| HPV16 | E2 | 8 | 235 |
| HPV16 | E2 | 8 | 151 |
| HPV16 | E2 | 9 | 151 |
| HPV16 | E2 | 11 | 151 |
| HPV16 | E2 | 10 | 57 |
| HPV16 | E2 | 8 | 27 |
| HPV16 | E2 | 9 | 27 |
| HPV16 | E2 | 11 | 27 |
| HPV16 | E2 | 9 | 343 |
| HPV16 | E2 | 9 | 304 |
| HPV16 | E2 | 8 | 37 |
| HPV16 | E2 | 9 | 37 |
| HPV16 | E2 | 11 | 37 |
| HPV16 | E2 | 8 | 7 |
| HPV16 | E2 | 11 | 242 |
| HPV16 | E2 | 8 | 165 |
| HPV16 | E2 | 8 | 330 |
| HPV16 | E2 | 11 | 202 |
| HPV16 | E2 | 8 | 283 |
| HPV16 | E2 | 10 | 283 |
| HPV16 | E2 | 9 | 206 |
| HPV16 | E2 | 9 | 316 |
| HPV16 | E2 | 10 | 23 |
| HPV16 | E2 | 8 | 317 |
| HPV16 | E2 | 11 | 317 |
| HPV16 | E2 | 11 | 144 |
| HPV16 | E2 | 8 | 269 |
| HPV16 | E2 | 10 | 269 |
| HPV16 | E2 | 8 | 104 |
| HPV16 | E2 | 9 | 104 |
| HPV16 | E2 | 10 | 104 |
| HPV16 | E2 | 8 | 313 |
| HPV16 | E2 | 8 | 24 |
| HPV16 | E2 | 11 | 24 |
| HPV16 | E2 | 9 | 107 |
| HPV16 | E2 | 8 | 322 |
| HPV16 | E2 | 9 | 247 |

TABLE XVII-continued

HLA-AI1 Motif Peptides

| 1 | 2 | 3 | 4 |
|---|---|---|---|
| HPV16 | E2 | 11 | 81 |
| HPV16 | E2 | 8 | 61 |
| HPV16 | E2 | 10 | 78 |
| HPV16 | E2 | 8 | 297 |
| HPV16 | E2 | 10 | 297 |
| HPV16 | E2 | 11 | 297 |
| HPV16 | E2 | 10 | 93 |
| HPV16 | E2 | 10 | 334 |
| HPV16 | E2 | 11 | 310 |
| HPV16 | E2 | 9 | 128 |
| HPV16 | E2 | 11 | 128 |
| HPV16 | E2 | 8 | 285 |
| HPV16 | E2 | 9 | 146 |
| HPV16 | E2 | 10 | 146 |
| HPV16 | E2 | 9 | 10 |
| HPV16 | E2 | 10 | 10 |
| HPV16 | E2 | 8 | 152 |
| HPV16 | E2 | 10 | 152 |
| HPV16 | E2 | 8 | 205 |
| HPV16 | E2 | 10 | 205 |
| HPV16 | E2 | 10 | 315 |
| HPV16 | E2 | 11 | 333 |
| HPV16 | E2 | 10 | 145 |
| HPV16 | E2 | 11 | 145 |
| HPV16 | E2 | 8 | 147 |
| HPV16 | E2 | 9 | 147 |
| HPV16 | E2 | 9 | 58 |
| HPV16 | E2 | 11 | 58 |
| HPV16 | E2 | 8 | 321 |
| HPV16 | E2 | 9 | 321 |
| HPV16 | E2 | 11 | 92 |
| HPV16 | E2 | 11 | 167 |
| HPV16 | E2 | 11 | 155 |
| HPV16 | E2 | 10 | 102 |
| HPV16 | E2 | 11 | 102 |
| HPV16 | E2 | 9 | 83 |
| HPV16 | E2 | 10 | 178 |
| HPV16 | E2 | 9 | 312 |
| HPV16 | E2 | 8 | 131 |
| HPV16 | E2 | 9 | 159 |
| HPV16 | E5 | 11 | 53 |
| HPV16 | E5 | 8 | 56 |
| HPV16 | E5 | 10 | 54 |
| HPV16 | E5 | 10 | 59 |
| HPV16 | E5 | 11 | 20 |
| HPV16 | E5 | 9 | 60 |
| HPV16 | E5 | 8 | 72 |
| HPV16 | E5 | 10 | 66 |
| HPV16 | E5 | 11 | 65 |
| HPV16 | E5 | 8 | 51 |
| HPV16 | E5 | 8 | 61 |
| HPV16 | E5 | 8 | 23 |
| HPV16 | E5 | 9 | 71 |
| HPV16 | E5 | 9 | 22 |
| HPV16 | E5 | 8 | 32 |
| HPV16 | E5 | 11 | 48 |
| HPV16 | E5 | 8 | 70 |
| HPV16 | E5 | 10 | 70 |
| HPV16 | E5 | 9 | 31 |
| HPV16 | E5 | 11 | 58 |
| HPV16 | E5 | 9 | 55 |
| HPV16 | E5 | 10 | 21 |
| HPV16 | E5 | 9 | 50 |
| HPV16 | E5 | 8 | 68 |
| HPV16 | E5 | 10 | 68 |
| HPV16 | E6 | 9 | 53 |
| HPV16 | E6 | 10 | 53 |
| HPV16 | E6 | 9 | 7 |
| HPV16 | E6 | 11 | 7 |
| HPV16 | E6 | 8 | 68 |
| HPV16 | E6 | 10 | 68 |
| HPV16 | E6 | 8 | 146 |
| HPV16 | E6 | 9 | 146 |
| HPV16 | E6 | 8 | 70 |
| HPV16 | E6 | 10 | 70 |

TABLE XVII-continued

HLA-AI1 Motif Peptides

| 1 | 2 | 3 | 4 |
|---|---|---|---|
| HPV16 | E6 | 10 | 58 |
| HPV16 | E6 | 11 | 73 |
| HPV16 | E6 | 9 | 143 |
| HPV16 | E6 | 11 | 143 |
| HPV16 | E6 | 9 | 23 |
| HPV16 | E6 | 10 | 37 |
| HPV16 | E6 | 11 | 37 |
| HPV16 | E6 | 11 | 51 |
| HPV16 | E6 | 10 | 63 |
| HPV16 | E6 | 8 | 32 |
| HPV16 | E6 | 10 | 32 |
| HPV16 | E6 | 11 | 105 |
| HPV16 | E6 | 11 | 36 |
| HPV16 | E6 | 8 | 48 |
| HPV16 | E6 | 10 | 52 |
| HPV16 | E6 | 11 | 52 |
| HPV16 | E6 | 9 | 64 |
| HPV16 | E6 | 8 | 92 |
| HPV16 | E6 | 10 | 92 |
| HPV16 | E6 | 9 | 31 |
| HPV16 | E6 | 11 | 31 |
| HPV16 | E6 | 9 | 125 |
| HPV16 | E6 | 10 | 133 |
| HPV16 | E6 | 9 | 33 |
| HPV16 | E6 | 8 | 34 |
| HPV16 | E6 | 9 | 80 |
| HPV16 | E6 | 9 | 59 |
| HPV16 | E6 | 8 | 72 |
| HPV16 | E6 | 9 | 75 |
| HPV16 | E6 | 10 | 75 |
| HPV16 | E6 | 11 | 75 |
| HPV16 | E6 | 8 | 79 |
| HPV16 | E6 | 10 | 79 |
| HPV16 | E6 | 11 | 57 |
| HPV16 | E6 | 8 | 117 |
| HPV16 | E6 | 9 | 117 |
| HPV16 | E6 | 10 | 22 |
| HPV16 | E6 | 8 | 126 |
| HPV16 | E6 | 11 | 126 |
| HPV16 | E6 | 9 | 107 |
| HPV16 | E6 | 10 | 106 |
| HPV16 | E6 | 8 | 8 |
| HPV16 | E6 | 10 | 8 |
| HPV16 | E6 | 11 | 8 |
| HPV16 | E6 | 8 | 144 |
| HPV16 | E6 | 10 | 144 |
| HPV16 | E6 | 11 | 144 |
| HPV16 | E6 | 11 | 112 |
| HPV16 | E6 | 9 | 134 |
| HPV16 | E6 | 8 | 102 |
| HPV16 | E6 | 9 | 116 |
| HPV16 | E6 | 10 | 116 |
| HPV16 | E6 | 8 | 10 |
| HPV16 | E6 | 9 | 10 |
| HPV16 | E6 | 11 | 21 |
| HPV16 | E6 | 8 | 43 |
| HPV16 | E6 | 10 | 142 |
| HPV16 | E6 | 11 | 62 |
| HPV16 | E6 | 8 | 55 |
| HPV16 | E6 | 8 | 131 |
| HPV16 | E6 | 11 | 5 |
| HPV16 | E6 | 9 | 145 |
| HPV16 | E6 | 10 | 145 |
| HPV16 | E6 | 11 | 89 |
| HPV16 | E6 | 10 | 6 |
| HPV16 | E6 | 9 | 140 |
| HPV16 | E6 | 11 | 29 |
| HPV16 | E6 | 8 | 94 |
| HPV16 | E6 | 9 | 93 |
| HPV16 | E6 | 9 | 69 |
| HPV16 | E6 | 11 | 69 |
| HPV16 | E6 | 10 | 139 |
| HPV16 | E6 | 9 | 67 |
| HPV16 | E6 | 11 | 67 |
| HPV16 | E6 | 8 | 39 |
| HPV16 | E6 | 9 | 39 |
| HPV16 | E6 | 9 | 91 |
| HPV16 | E6 | 11 | 91 |
| HPV16 | E6 | 11 | 99 |
| HPV16 | E6 | 8 | 77 |
| HPV16 | E6 | 9 | 77 |
| HPV16 | E6 | 10 | 77 |
| HPV16 | E7 | 8 | 42 |
| HPV16 | E7 | 10 | 42 |
| HPV16 | E7 | 11 | 42 |
| HPV16 | E7 | 9 | 58 |
| HPV16 | E7 | 10 | 68 |
| HPV16 | E7 | 11 | 39 |
| HPV16 | E7 | 10 | 14 |
| HPV16 | E7 | 8 | 4 |
| HPV16 | E7 | 8 | 18 |
| HPV16 | E7 | 10 | 57 |
| HPV16 | E7 | 9 | 3 |
| HPV16 | E7 | 10 | 88 |
| HPV16 | E7 | 8 | 2 |
| HPV16 | E7 | 10 | 2 |
| HPV16 | E7 | 9 | 89 |
| HPV16 | E7 | 11 | 67 |
| HPV16 | E7 | 11 | 13 |
| HPV16 | E7 | 11 | 87 |
| HPV16 | E7 | 8 | 53 |
| HPV16 | E7 | 9 | 41 |
| HPV16 | E7 | 11 | 41 |
| HPV16 | E7 | 8 | 44 |
| HPV16 | E7 | 9 | 44 |
| HPV16 | E7 | 8 | 70 |
| HPV16 | E7 | 8 | 66 |
| HPV16 | E7 | 11 | 63 |
| HPV16 | E7 | 11 | 56 |
| HPV16 | E7 | 10 | 64 |
| HPV16 | E7 | 8 | 90 |
| HPV16 | E7 | 9 | 52 |
| HPV16 | L1 | 10 | 372 |
| HPV16 | L1 | 11 | 372 |
| HPV16 | L1 | 9 | 162 |
| HPV16 | L1 | 11 | 453 |
| HPV16 | L1 | 9 | 127 |
| HPV16 | L1 | 10 | 483 |
| HPV16 | L1 | 11 | 483 |
| HPV16 | L1 | 8 | 411 |
| HPV16 | L1 | 8 | 498 |
| HPV16 | L1 | 11 | 63 |
| HPV16 | L1 | 9 | 373 |
| HPV16 | L1 | 10 | 373 |
| HPV16 | L1 | 11 | 233 |
| HPV16 | L1 | 8 | 163 |
| HPV16 | L1 | 8 | 310 |
| HPV16 | L1 | 11 | 292 |
| HPV16 | L1 | 10 | 70 |
| HPV16 | L1 | 11 | 70 |
| HPV16 | L1 | 11 | 371 |
| HPV16 | L1 | 10 | 251 |
| HPV16 | L1 | 8 | 128 |
| HPV16 | L1 | 9 | 329 |
| HPV16 | L1 | 9 | 153 |
| HPV16 | L1 | 9 | 235 |
| HPV16 | L1 | 8 | 249 |
| HPV16 | L1 | 9 | 249 |
| HPV16 | L1 | 9 | 484 |
| HPV16 | L1 | 10 | 484 |
| HPV16 | L1 | 10 | 397 |
| HPV16 | L1 | 10 | 168 |
| HPV16 | L1 | 11 | 168 |
| HPV16 | L1 | 8 | 270 |
| HPV16 | L1 | 9 | 270 |
| HPV16 | L1 | 8 | 154 |
| HPV16 | L1 | 11 | 113 |
| HPV16 | L1 | 8 | 171 |
| HPV16 | L1 | 8 | 15 |
| HPV16 | L1 | 8 | 295 |

TABLE XVII-continued

HLA-AI1 Motif Peptides

| 1 | 2 | 3 | 4 |
|---|---|---|---|
| HPV16 | L1 | 10 | 295 |
| HPV16 | L1 | 10 | 378 |
| HPV16 | L1 | 9 | 109 |
| HPV16 | L1 | 10 | 5 |
| HPV16 | L1 | 8 | 494 |
| HPV16 | L1 | 10 | 494 |
| HPV16 | L1 | 9 | 333 |
| HPV16 | L1 | 8 | 236 |
| HPV16 | L1 | 8 | 282 |
| HPV16 | L1 | 11 | 446 |
| HPV16 | L1 | 9 | 356 |
| HPV16 | L1 | 9 | 186 |
| HPV16 | L1 | 9 | 269 |
| HPV16 | L1 | 10 | 269 |
| HPV16 | L1 | 8 | 110 |
| HPV16 | L1 | 8 | 437 |
| HPV16 | L1 | 9 | 437 |
| HPV16 | L1 | 10 | 142 |
| HPV16 | L1 | 8 | 93 |
| HPV16 | L1 | 10 | 93 |
| HPV16 | L1 | 11 | 307 |
| HPV16 | L1 | 8 | 438 |
| HPV16 | L1 | 10 | 64 |
| HPV16 | L1 | 9 | 254 |
| HPV16 | L1 | 8 | 250 |
| HPV16 | L1 | 11 | 250 |
| HPV16 | L1 | 10 | 332 |
| HPV16 | L1 | 10 | 185 |
| HPV16 | L1 | 11 | 86 |
| HPV16 | L1 | 9 | 143 |
| HPV16 | L1 | 8 | 374 |
| HPV16 | L1 | 9 | 374 |
| HPV16 | L1 | 11 | 11 |
| HPV16 | L1 | 10 | 407 |
| HPV16 | L1 | 10 | 501 |
| HPV16 | L1 | 11 | 501 |
| HPV16 | L1 | 10 | 108 |
| HPV16 | L1 | 9 | 493 |
| HPV16 | L1 | 11 | 493 |
| HPV16 | L1 | 8 | 505 |
| HPV16 | L1 | 11 | 406 |
| HPV16 | L1 | 11 | 151 |
| HPV16 | L1 | 8 | 382 |
| HPV16 | L1 | 10 | 382 |
| HPV16 | L1 | 11 | 382 |
| HPV16 | L1 | 8 | 90 |
| HPV16 | L1 | 11 | 90 |
| HPV16 | L1 | 8 | 46 |
| HPV16 | L1 | 11 | 46 |
| HPV16 | L1 | 11 | 69 |
| HPV16 | L1 | 10 | 152 |
| HPV16 | L1 | 9 | 248 |
| HPV16 | L1 | 10 | 248 |
| HPV16 | L1 | 8 | 485 |
| HPV16 | L1 | 9 | 485 |
| HPV16 | L1 | 10 | 355 |
| HPV16 | L1 | 8 | 139 |
| HPV16 | L1 | 11 | 184 |
| HPV16 | L1 | 8 | 68 |
| HPV16 | L1 | 9 | 495 |
| HPV16 | L1 | 11 | 495 |
| HPV16 | L1 | 8 | 409 |
| HPV16 | L1 | 10 | 409 |
| HPV16 | L1 | 10 | 87 |
| HPV16 | L1 | 11 | 87 |
| HPV16 | L1 | 10 | 234 |
| HPV16 | L1 | 9 | 281 |
| HPV16 | L1 | 11 | 325 |
| HPV16 | L1 | 8 | 385 |
| HPV16 | L1 | 10 | 58 |
| HPV16 | L1 | 8 | 83 |
| HPV16 | L1 | 9 | 82 |
| HPV16 | L1 | 9 | 383 |
| HPV16 | L1 | 10 | 383 |
| HPV16 | L1 | 9 | 296 |
| HPV16 | L1 | 9 | 460 |
| HPV16 | L1 | 10 | 460 |
| HPV16 | L1 | 11 | 460 |
| HPV16 | L1 | 11 | 258 |
| HPV16 | L1 | 9 | 436 |
| HPV16 | L1 | 10 | 436 |
| HPV16 | L1 | 8 | 190 |
| HPV16 | L1 | 9 | 77 |
| HPV16 | L1 | 10 | 247 |
| HPV16 | L1 | 11 | 247 |
| HPV16 | L1 | 9 | 138 |
| HPV16 | L1 | 10 | 81 |
| HPV16 | L1 | 11 | 515 |
| HPV16 | L1 | 11 | 43 |
| HPV16 | L1 | 9 | 497 |
| HPV16 | L1 | 8 | 450 |
| HPV16 | L1 | 8 | 399 |
| HPV16 | L1 | 11 | 331 |
| HPV16 | L1 | 8 | 181 |
| HPV16 | L1 | 11 | 354 |
| HPV16 | L1 | 10 | 280 |
| HPV16 | L1 | 10 | 179 |
| HPV16 | L1 | 9 | 100 |
| HPV16 | L1 | 9 | 67 |
| HPV16 | L1 | 11 | 482 |
| HPV16 | L1 | 8 | 328 |
| HPV16 | L1 | 10 | 328 |
| HPV16 | L1 | 9 | 115 |
| HPV16 | L1 | 8 | 144 |
| HPV16 | L1 | 9 | 92 |
| HPV16 | L1 | 11 | 92 |
| HPV16 | L1 | 8 | 253 |
| HPV16 | L1 | 10 | 253 |
| HPV16 | L1 | 8 | 271 |
| HPV16 | L1 | 11 | 28 |
| HPV16 | L1 | 8 | 518 |
| HPV16 | L1 | 9 | 518 |
| HPV16 | L1 | 10 | 518 |
| HPV16 | L1 | 11 | 518 |
| HPV16 | L1 | 10 | 308 |
| HPV16 | L1 | 8 | 49 |
| HPV16 | L1 | 8 | 375 |
| HPV16 | L1 | 8 | 519 |
| HPV16 | L1 | 9 | 519 |
| HPV16 | L1 | 10 | 519 |
| HPV16 | L1 | 11 | 519 |
| HPV16 | L1 | 8 | 521 |
| HPV16 | L1 | 9 | 521 |
| HPV16 | L1 | 10 | 521 |
| HPV16 | L1 | 9 | 410 |
| HPV16 | L1 | 8 | 523 |
| HPV16 | L1 | 9 | 309 |
| HPV16 | L1 | 10 | 12 |
| HPV16 | L1 | 11 | 12 |
| HPV16 | L1 | 11 | 50 |
| HPV16 | L1 | 11 | 4 |
| HPV16 | L1 | 8 | 471 |
| HPV16 | L1 | 10 | 471 |
| HPV16 | L1 | 9 | 408 |
| HPV16 | L1 | 11 | 408 |
| HPV16 | L1 | 8 | 384 |
| HPV16 | L1 | 9 | 384 |
| HPV16 | L1 | 11 | 57 |
| HPV16 | L1 | 9 | 327 |
| HPV16 | L1 | 11 | 327 |
| HPV16 | L1 | 10 | 114 |
| HPV16 | L1 | 9 | 252 |
| HPV16 | L1 | 11 | 252 |
| HPV16 | L1 | 9 | 448 |
| HPV16 | L1 | 10 | 448 |
| HPV16 | L1 | 9 | 65 |
| HPV16 | L1 | 11 | 65 |
| HPV16 | L1 | 9 | 517 |
| HPV16 | L1 | 10 | 517 |
| HPV16 | L1 | 11 | 517 |

TABLE XVII-continued

HLA-AI1 Motif Peptides

| 1 | 2 | 3 | 4 |
|---|---|---|---|
| HPV16 | L1 | 8 | 520 |
| HPV16 | L1 | 9 | 520 |
| HPV16 | L1 | 10 | 520 |
| HPV16 | L1 | 11 | 520 |
| HPV16 | L1 | 8 | 522 |
| HPV16 | L1 | 9 | 522 |
| HPV16 | L1 | 10 | 516 |
| HPV16 | L1 | 11 | 516 |
| HPV16 | L1 | 9 | 379 |
| HPV16 | L1 | 11 | 379 |
| HPV16 | L1 | 11 | 36 |
| HPV16 | L1 | 8 | 54 |
| HPV16 | L1 | 9 | 54 |
| HPV16 | L1 | 11 | 167 |
| HPV16 | L1 | 11 | 98 |
| HPV16 | L1 | 10 | 293 |
| HPV16 | L1 | 9 | 71 |
| HPV16 | L1 | 10 | 71 |
| HPV16 | L1 | 11 | 141 |
| HPV16 | L1 | 10 | 91 |
| HPV16 | L1 | 10 | 44 |
| HPV16 | L1 | 9 | 48 |
| HPV16 | L1 | 10 | 326 |
| HPV16 | L1 | 10 | 447 |
| HPV16 | L1 | 11 | 447 |
| HPV16 | L1 | 8 | 357 |
| HPV16 | L1 | 10 | 47 |
| HPV16 | L1 | 10 | 126 |
| HPV16 | L1 | 9 | 30 |
| HPV16 | L1 | 8 | 338 |
| HPV16 | L1 | 10 | 161 |
| HPV16 | L1 | 11 | 396 |
| HPV16 | L1 | 11 | 75 |
| HPV16 | L1 | 8 | 268 |
| HPV16 | L1 | 10 | 268 |
| HPV16 | L1 | 11 | 268 |
| HPV16 | L1 | 9 | 260 |
| HPV16 | L1 | 8 | 7 |
| HPV16 | L1 | 9 | 38 |
| HPV16 | L1 | 8 | 389 |
| HPV16 | L1 | 10 | 275 |
| HPV16 | L1 | 11 | 275 |
| HPV16 | L1 | 9 | 470 |
| HPV16 | L1 | 11 | 470 |
| HPV16 | L1 | 8 | 53 |
| HPV16 | L1 | 9 | 53 |
| HPV16 | L1 | 10 | 53 |
| HPV16 | L2 | 9 | 441 |
| HPV16 | L2 | 8 | 241 |
| HPV16 | L2 | 10 | 443 |
| HPV16 | L2 | 11 | 443 |
| HPV16 | L2 | 11 | 25 |
| HPV16 | L2 | 10 | 288 |
| HPV16 | L2 | 11 | 288 |
| HPV16 | L2 | 11 | 356 |
| HPV16 | L2 | 10 | 293 |
| HPV16 | L2 | 11 | 293 |
| HPV16 | L2 | 11 | 396 |
| HPV16 | L2 | 8 | 13 |
| HPV16 | L2 | 11 | 13 |
| HPV16 | L2 | 9 | 82 |
| HPV16 | L2 | 9 | 15 |
| HPV16 | L2 | 8 | 442 |
| HPV16 | L2 | 11 | 442 |
| HPV16 | L2 | 9 | 282 |
| HPV16 | L2 | 10 | 282 |
| HPV16 | L2 | 8 | 445 |
| HPV16 | L2 | 9 | 445 |
| HPV16 | L2 | 9 | 31 |
| HPV16 | L2 | 10 | 258 |
| HPV16 | L2 | 10 | 340 |
| HPV16 | L2 | 11 | 242 |
| HPV16 | L2 | 8 | 283 |
| HPV16 | L2 | 9 | 283 |
| HPV16 | L2 | 11 | 181 |
| HPV16 | L2 | 8 | 321 |
| HPV16 | L2 | 9 | 444 |
| HPV16 | L2 | 10 | 444 |
| HPV16 | L2 | 9 | 259 |
| HPV16 | L2 | 11 | 59 |
| HPV16 | L2 | 10 | 300 |
| HPV16 | L2 | 11 | 226 |
| HPV16 | L2 | 9 | 307 |
| HPV16 | L2 | 10 | 63 |
| HPV16 | L2 | 11 | 218 |
| HPV16 | L2 | 10 | 26 |
| HPV16 | L2 | 8 | 65 |
| HPV16 | L2 | 9 | 61 |
| HPV16 | L2 | 8 | 440 |
| HPV16 | L2 | 10 | 440 |
| HPV16 | L2 | 8 | 41 |
| HPV16 | L2 | 8 | 260 |
| HPV16 | L2 | 8 | 320 |
| HPV16 | L2 | 9 | 320 |
| HPV16 | L2 | 8 | 306 |
| HPV16 | L2 | 10 | 306 |
| HPV16 | L2 | 10 | 60 |
| HPV16 | L2 | 9 | 439 |
| HPV16 | L2 | 11 | 439 |
| HPV16 | L2 | 8 | 32 |
| HPV16 | L2 | 9 | 361 |
| HPV16 | L2 | 11 | 148 |
| HPV16 | L2 | 11 | 344 |
| HPV16 | L2 | 10 | 243 |
| HPV16 | L2 | 8 | 250 |
| HPV16 | L2 | 8 | 430 |
| HPV16 | L2 | 10 | 248 |
| HPV16 | L2 | 8 | 318 |
| HPV16 | L2 | 9 | 318 |
| HPV16 | L2 | 10 | 318 |
| HPV16 | L2 | 11 | 318 |
| HPV16 | L2 | 10 | 39 |
| HPV16 | L2 | 8 | 284 |
| HPV16 | L2 | 11 | 427 |
| HPV16 | L2 | 9 | 249 |
| HPV16 | L2 | 9 | 183 |
| HPV16 | L2 | 11 | 183 |
| HPV16 | L2 | 9 | 294 |
| HPV16 | L2 | 10 | 294 |
| HPV16 | L2 | 8 | 454 |
| HPV16 | L2 | 11 | 454 |
| HPV16 | L2 | 8 | 362 |
| HPV16 | L2 | 10 | 149 |
| HPV16 | L2 | 10 | 397 |
| HPV16 | L2 | 9 | 150 |
| HPV16 | L2 | 9 | 240 |
| HPV16 | L2 | 11 | 292 |
| HPV16 | L2 | 10 | 281 |
| HPV16 | L2 | 11 | 281 |
| HPV16 | L2 | 10 | 30 |
| HPV16 | L2 | 8 | 217 |
| HPV16 | L2 | 10 | 215 |
| HPV16 | L2 | 9 | 429 |
| HPV16 | L2 | 8 | 386 |
| HPV16 | L2 | 9 | 346 |
| HPV16 | L2 | 11 | 383 |
| HPV16 | L2 | 8 | 450 |
| HPV16 | L2 | 9 | 450 |
| HPV16 | L2 | 10 | 450 |
| HPV16 | L2 | 11 | 450 |
| HPV16 | L2 | 11 | 80 |
| HPV16 | L2 | 9 | 172 |
| HPV16 | L2 | 9 | 358 |
| HPV16 | L2 | 8 | 221 |
| HPV16 | L2 | 10 | 221 |
| HPV16 | L2 | 8 | 342 |
| HPV16 | L2 | 9 | 310 |
| HPV16 | L2 | 8 | 12 |
| HPV16 | L2 | 9 | 12 |
| HPV16 | L2 | 9 | 305 |

TABLE XVII-continued

HLA-AI1 Motif Peptides

| 1 | 2 | 3 | 4 |
|---|---|---|---|
| HPV16 | L2 | 11 | 305 |
| HPV16 | L2 | 8 | 5 |
| HPV16 | L2 | 9 | 315 |
| HPV16 | L2 | 11 | 315 |
| HPV16 | L2 | 8 | 298 |
| HPV16 | L2 | 10 | 69 |
| HPV16 | L2 | 11 | 9 |
| HPV16 | L2 | 11 | 313 |
| HPV16 | L2 | 10 | 14 |
| HPV16 | L2 | 8 | 316 |
| HPV16 | L2 | 10 | 316 |
| HPV16 | L2 | 11 | 316 |
| HPV16 | L2 | 9 | 64 |
| HPV16 | L2 | 8 | 319 |
| HPV16 | L2 | 9 | 319 |
| HPV16 | L2 | 10 | 319 |
| HPV16 | L2 | 10 | 360 |
| HPV16 | L2 | 8 | 184 |
| HPV16 | L2 | 10 | 184 |
| HPV16 | L2 | 9 | 185 |
| HPV16 | L2 | 9 | 212 |
| HPV16 | L2 | 8 | 186 |
| HPV16 | L2 | 8 | 213 |
| HPV16 | L2 | 8 | 347 |
| HPV16 | L2 | 10 | 384 |
| HPV16 | L2 | 10 | 81 |
| HPV16 | L2 | 9 | 27 |
| HPV16 | L2 | 8 | 83 |
| HPV16 | L2 | 11 | 299 |
| HPV16 | L2 | 8 | 62 |
| HPV16 | L2 | 11 | 62 |
| HPV16 | L2 | 9 | 70 |
| HPV16 | L2 | 9 | 40 |
| HPV16 | L2 | 10 | 438 |
| HPV16 | L2 | 8 | 399 |
| HPV16 | L2 | 8 | 311 |
| HPV16 | L2 | 10 | 182 |
| HPV16 | L2 | 8 | 359 |
| HPV16 | L2 | 11 | 359 |
| HPV16 | L2 | 8 | 295 |
| HPV16 | L2 | 9 | 295 |
| HPV16 | L2 | 11 | 295 |
| HPV16 | L2 | 10 | 211 |
| HPV16 | L2 | 9 | 398 |
| HPV16 | L2 | 9 | 244 |
| HPV16 | L2 | 8 | 151 |
| HPV16 | L2 | 11 | 287 |
| HPV16 | L2 | 9 | 222 |
| HPV16 | L2 | 11 | 238 |
| HPV16 | L2 | 11 | 210 |
| HPV16 | L2 | 10 | 447 |
| HPV16 | L2 | 11 | 447 |
| HPV16 | L2 | 8 | 453 |
| HPV16 | L2 | 9 | 453 |
| HPV16 | L2 | 11 | 303 |
| HPV16 | L2 | 9 | 228 |
| HPV16 | L2 | 11 | 437 |
| HPV18 | E1 | 11 | 397 |
| HPV18 | E1 | 10 | 398 |
| HPV18 | E1 | 11 | 398 |
| HPV18 | E1 | 11 | 546 |
| HPV18 | E1 | 9 | 68 |
| HPV18 | E1 | 11 | 466 |
| HPV18 | E1 | 9 | 284 |
| HPV18 | E1 | 11 | 284 |
| HPV18 | E1 | 10 | 213 |
| HPV18 | E1 | 8 | 413 |
| HPV18 | E1 | 9 | 413 |
| HPV18 | E1 | 8 | 531 |
| HPV18 | E1 | 11 | 504 |
| HPV18 | E1 | 8 | 412 |
| HPV18 | E1 | 9 | 412 |
| HPV18 | E1 | 10 | 412 |
| HPV18 | E1 | 9 | 618 |
| HPV18 | E1 | 10 | 290 |
| HPV18 | E1 | 8 | 483 |
| HPV18 | E1 | 10 | 483 |
| HPV18 | E1 | 8 | 311 |
| HPV18 | E1 | 10 | 311 |
| HPV18 | E1 | 11 | 437 |
| HPV18 | E1 | 11 | 196 |
| HPV18 | E1 | 9 | 78 |
| HPV18 | E1 | 10 | 78 |
| HPV18 | E1 | 11 | 78 |
| HPV18 | E1 | 9 | 530 |
| HPV18 | E1 | 8 | 411 |
| HPV18 | E1 | 9 | 411 |
| HPV18 | E1 | 10 | 411 |
| HPV18 | E1 | 11 | 411 |
| HPV18 | E1 | 10 | 529 |
| HPV18 | E1 | 9 | 548 |
| HPV18 | E1 | 10 | 548 |
| HPV18 | E1 | 11 | 548 |
| HPV18 | E1 | 8 | 203 |
| HPV18 | E1 | 10 | 228 |
| HPV18 | E1 | 10 | 580 |
| HPV18 | E1 | 11 | 391 |
| HPV18 | E1 | 11 | 637 |
| HPV18 | E1 | 8 | 342 |
| HPV18 | E1 | 10 | 459 |
| HPV18 | E1 | 10 | 594 |
| HPV18 | E1 | 9 | 639 |
| HPV18 | E1 | 11 | 639 |
| HPV18 | E1 | 10 | 10 |
| HPV18 | E1 | 8 | 610 |
| HPV18 | E1 | 9 | 115 |
| HPV18 | E1 | 10 | 115 |
| HPV18 | E1 | 10 | 62 |
| HPV18 | E1 | 8 | 95 |
| HPV18 | E1 | 8 | 379 |
| HPV18 | E1 | 8 | 64 |
| HPV18 | E1 | 10 | 309 |
| HPV18 | E1 | 9 | 104 |
| HPV18 | E1 | 10 | 74 |
| HPV18 | E1 | 9 | 482 |
| HPV18 | E1 | 11 | 482 |
| HPV18 | E1 | 9 | 601 |
| HPV18 | E1 | 8 | 619 |
| HPV18 | E1 | 9 | 460 |
| HPV18 | E1 | 10 | 463 |
| HPV18 | E1 | 8 | 470 |
| HPV18 | E1 | 9 | 399 |
| HPV18 | E1 | 10 | 399 |
| HPV18 | E1 | 9 | 226 |
| HPV18 | E1 | 8 | 130 |
| HPV18 | E1 | 8 | 465 |
| HPV18 | E1 | 8 | 212 |
| HPV18 | E1 | 11 | 212 |
| HPV18 | E1 | 9 | 341 |
| HPV18 | E1 | 11 | 444 |
| HPV18 | E1 | 9 | 223 |
| HPV18 | E1 | 8 | 640 |
| HPV18 | E1 | 10 | 640 |
| HPV18 | E1 | 8 | 549 |
| HPV18 | E1 | 9 | 549 |
| HPV18 | E1 | 10 | 549 |
| HPV18 | E1 | 11 | 549 |
| HPV18 | E1 | 10 | 605 |
| HPV18 | E1 | 11 | 92 |
| HPV18 | E1 | 11 | 644 |
| HPV18 | E1 | 9 | 11 |
| HPV18 | E1 | 9 | 279 |
| HPV18 | E1 | 10 | 279 |
| HPV18 | E1 | 11 | 279 |
| HPV18 | E1 | 11 | 249 |
| HPV18 | E1 | 11 | 514 |
| HPV18 | E1 | 8 | 270 |
| HPV18 | E1 | 8 | 76 |
| HPV18 | E1 | 11 | 76 |
| HPV18 | E1 | 9 | 198 |

TABLE XVII-continued

HLA-AI1 Motif Peptides

| 1 | 2 | 3 | 4 |
|---|---|---|---|
| HPV18 | E1 | 8 | 440 |
| HPV18 | E1 | 8 | 282 |
| HPV18 | E1 | 11 | 282 |
| HPV18 | E1 | 8 | 569 |
| HPV18 | E1 | 11 | 569 |
| HPV18 | E1 | 9 | 506 |
| HPV18 | E1 | 8 | 552 |
| HPV18 | E1 | 8 | 116 |
| HPV18 | E1 | 9 | 116 |
| HPV18 | E1 | 11 | 116 |
| HPV18 | E1 | 8 | 461 |
| HPV18 | E1 | 10 | 617 |
| HPV18 | E1 | 11 | 289 |
| HPV18 | E1 | 8 | 410 |
| HPV18 | E1 | 9 | 410 |
| HPV18 | E1 | 10 | 410 |
| HPV18 | E1 | 11 | 410 |
| HPV18 | E1 | 9 | 202 |
| HPV18 | E1 | 11 | 579 |
| HPV18 | E1 | 8 | 299 |
| HPV18 | E1 | 9 | 439 |
| HPV18 | E1 | 8 | 647 |
| HPV18 | E1 | 9 | 647 |
| HPV18 | E1 | 10 | 318 |
| HPV18 | E1 | 9 | 614 |
| HPV18 | E1 | 9 | 468 |
| HPV18 | E1 | 10 | 468 |
| HPV18 | E1 | 8 | 401 |
| HPV18 | E1 | 10 | 401 |
| HPV18 | E1 | 8 | 292 |
| HPV18 | E1 | 10 | 490 |
| HPV18 | E1 | 10 | 259 |
| HPV18 | E1 | 10 | 283 |
| HPV18 | E1 | 8 | 215 |
| HPV18 | E1 | 11 | 528 |
| HPV18 | E1 | 10 | 547 |
| HPV18 | E1 | 11 | 547 |
| HPV18 | E1 | 8 | 69 |
| HPV18 | E1 | 9 | 129 |
| HPV18 | E1 | 9 | 464 |
| HPV18 | E1 | 8 | 281 |
| HPV18 | E1 | 9 | 281 |
| HPV18 | E1 | 8 | 261 |
| HPV18 | E1 | 10 | 261 |
| HPV18 | E1 | 8 | 313 |
| HPV18 | E1 | 8 | 285 |
| HPV18 | E1 | 10 | 285 |
| HPV18 | E1 | 10 | 570 |
| HPV18 | E1 | 9 | 118 |
| HPV18 | E1 | 10 | 118 |
| HPV18 | E1 | 11 | 118 |
| HPV18 | E1 | 8 | 224 |
| HPV18 | E1 | 11 | 224 |
| HPV18 | E1 | 11 | 376 |
| HPV18 | E1 | 9 | 571 |
| HPV18 | E1 | 11 | 480 |
| HPV18 | E1 | 9 | 229 |
| HPV18 | E1 | 10 | 415 |
| HPV18 | E1 | 11 | 415 |
| HPV18 | E1 | 10 | 340 |
| HPV18 | E1 | 9 | 214 |
| HPV18 | E1 | 9 | 312 |
| HPV18 | E1 | 8 | 427 |
| HPV18 | E1 | 10 | 427 |
| HPV18 | E1 | 8 | 429 |
| HPV18 | E1 | 11 | 429 |
| HPV18 | E1 | 8 | 403 |
| HPV18 | E1 | 10 | 77 |
| HPV18 | E1 | 11 | 77 |
| HPV18 | E1 | 11 | 612 |
| HPV18 | E1 | 11 | 604 |
| HPV18 | E1 | 9 | 574 |
| HPV18 | E1 | 9 | 428 |
| HPV18 | E1 | 8 | 119 |
| HPV18 | E1 | 9 | 119 |
| HPV18 | E1 | 10 | 119 |
| HPV18 | E1 | 9 | 393 |
| HPV18 | E1 | 9 | 577 |
| HPV18 | E1 | 8 | 485 |
| HPV18 | E1 | 10 | 600 |
| HPV18 | E1 | 8 | 642 |
| HPV18 | E1 | 9 | 568 |
| HPV18 | E1 | 8 | 551 |
| HPV18 | E1 | 9 | 551 |
| HPV18 | E1 | 8 | 448 |
| HPV18 | E1 | 8 | 596 |
| HPV18 | E1 | 8 | 252 |
| HPV18 | E1 | 8 | 607 |
| HPV18 | E1 | 11 | 607 |
| HPV18 | E1 | 10 | 67 |
| HPV18 | E1 | 8 | 195 |
| HPV18 | E1 | 9 | 211 |
| HPV18 | E1 | 10 | 146 |
| HPV18 | E1 | 11 | 200 |
| HPV18 | E1 | 9 | 426 |
| HPV18 | E1 | 11 | 426 |
| HPV18 | E1 | 8 | 80 |
| HPV18 | E1 | 9 | 80 |
| HPV18 | E1 | 8 | 148 |
| HPV18 | E1 | 11 | 102 |
| HPV18 | E1 | 10 | 128 |
| HPV18 | E1 | 8 | 320 |
| HPV18 | E1 | 10 | 320 |
| HPV18 | E1 | 11 | 320 |
| HPV18 | E1 | 9 | 622 |
| HPV18 | E1 | 8 | 469 |
| HPV18 | E1 | 9 | 469 |
| HPV18 | E1 | 10 | 225 |
| HPV18 | E1 | 8 | 507 |
| HPV18 | E1 | 8 | 120 |
| HPV18 | E1 | 9 | 120 |
| HPV18 | E1 | 8 | 117 |
| HPV18 | E1 | 10 | 117 |
| HPV18 | E1 | 11 | 117 |
| HPV18 | E1 | 8 | 394 |
| HPV18 | E1 | 9 | 402 |
| HPV18 | E1 | 10 | 392 |
| HPV18 | E1 | 9 | 321 |
| HPV18 | E1 | 10 | 321 |
| HPV18 | E1 | 10 | 93 |
| HPV18 | E1 | 8 | 322 |
| HPV18 | E1 | 9 | 322 |
| HPV18 | E1 | 9 | 310 |
| HPV18 | E1 | 11 | 310 |
| HPV18 | E1 | 9 | 534 |
| HPV18 | E1 | 11 | 534 |
| HPV18 | E1 | 10 | 377 |
| HPV18 | E1 | 8 | 227 |
| HPV18 | E1 | 11 | 227 |
| HPV18 | E1 | 10 | 645 |
| HPV18 | E1 | 11 | 645 |
| HPV18 | E1 | 11 | 462 |
| HPV18 | E1 | 8 | 12 |
| HPV18 | E1 | 10 | 197 |
| HPV18 | E1 | 9 | 260 |
| HPV18 | E1 | 11 | 260 |
| HPV18 | E1 | 8 | 414 |
| HPV18 | E1 | 11 | 414 |
| HPV18 | E1 | 10 | 573 |
| HPV18 | E1 | 10 | 533 |
| HPV18 | E1 | 8 | 572 |
| HPV18 | E1 | 11 | 572 |
| HPV18 | E1 | 11 | 532 |
| HPV18 | E1 | 11 | 296 |
| HPV18 | E1 | 8 | 323 |
| HPV18 | E1 | 10 | 297 |
| HPV18 | E1 | 8 | 105 |
| HPV18 | E1 | 10 | 481 |
| HPV18 | E1 | 10 | 505 |
| HPV18 | E1 | 8 | 81 |

TABLE XVII-continued

HLA-A11 Motif Peptides

| 1 | 2 | 3 | 4 |
|---|---|---|---|
| HPV18 | E1 | 8 | 280 |
| HPV18 | E1 | 9 | 280 |
| HPV18 | E1 | 10 | 280 |
| HPV18 | E1 | 11 | 339 |
| HPV18 | E1 | 11 | 192 |
| HPV18 | E1 | 10 | 250 |
| HPV18 | E1 | 10 | 17 |
| HPV18 | E1 | 11 | 17 |
| HPV18 | E1 | 10 | 278 |
| HPV18 | E1 | 11 | 278 |
| HPV18 | E1 | 10 | 346 |
| HPV18 | E1 | 8 | 432 |
| HPV18 | E1 | 9 | 516 |
| HPV18 | E1 | 9 | 536 |
| HPV18 | E1 | 10 | 268 |
| HPV18 | E1 | 8 | 492 |
| HPV18 | E1 | 10 | 222 |
| HPV18 | E1 | 10 | 408 |
| HPV18 | E1 | 11 | 408 |
| HPV18 | E1 | 8 | 19 |
| HPV18 | E1 | 9 | 19 |
| HPV18 | E2 | 9 | 269 |
| HPV18 | E2 | 10 | 269 |
| HPV18 | E2 | 11 | 269 |
| HPV18 | E2 | 9 | 45 |
| HPV18 | E2 | 9 | 82 |
| HPV18 | E2 | 10 | 82 |
| HPV18 | E2 | 11 | 82 |
| HPV18 | E2 | 10 | 154 |
| HPV18 | E2 | 11 | 154 |
| HPV18 | E2 | 8 | 270 |
| HPV18 | E2 | 9 | 270 |
| HPV18 | E2 | 10 | 270 |
| HPV18 | E2 | 11 | 270 |
| HPV18 | E2 | 10 | 214 |
| HPV18 | E2 | 8 | 252 |
| HPV18 | E2 | 8 | 301 |
| HPV18 | E2 | 9 | 301 |
| HPV18 | E2 | 11 | 132 |
| HPV18 | E2 | 10 | 282 |
| HPV18 | E2 | 9 | 14 |
| HPV18 | E2 | 10 | 14 |
| HPV18 | E2 | 8 | 156 |
| HPV18 | E2 | 9 | 156 |
| HPV18 | E2 | 11 | 156 |
| HPV18 | E2 | 11 | 209 |
| HPV18 | E2 | 10 | 126 |
| HPV18 | E2 | 8 | 29 |
| HPV18 | E2 | 11 | 26 |
| HPV18 | E2 | 11 | 31 |
| HPV18 | E2 | 9 | 354 |
| HPV18 | E2 | 10 | 210 |
| HPV18 | E2 | 8 | 175 |
| HPV18 | E2 | 9 | 175 |
| HPV18 | E2 | 11 | 167 |
| HPV18 | E2 | 9 | 104 |
| HPV18 | E2 | 9 | 43 |
| HPV18 | E2 | 11 | 43 |
| HPV18 | E2 | 11 | 125 |
| HPV18 | E2 | 10 | 268 |
| HPV18 | E2 | 11 | 268 |
| HPV18 | E2 | 10 | 294 |
| HPV18 | E2 | 11 | 294 |
| HPV18 | E2 | 8 | 117 |
| HPV18 | E2 | 8 | 331 |
| HPV18 | E2 | 8 | 85 |
| HPV18 | E2 | 9 | 161 |
| HPV18 | E2 | 9 | 127 |
| HPV18 | E2 | 9 | 184 |
| HPV18 | E2 | 8 | 284 |
| HPV18 | E2 | 10 | 284 |
| HPV18 | E2 | 9 | 251 |
| HPV18 | E2 | 8 | 53 |
| HPV18 | E2 | 10 | 291 |
| HPV18 | E2 | 8 | 338 |
| HPV18 | E2 | 9 | 20 |
| HPV18 | E2 | 8 | 46 |
| HPV18 | E2 | 10 | 19 |
| HPV18 | E2 | 8 | 289 |
| HPV18 | E2 | 8 | 68 |
| HPV18 | E2 | 8 | 300 |
| HPV18 | E2 | 9 | 300 |
| HPV18 | E2 | 10 | 300 |
| HPV18 | E2 | 9 | 28 |
| HPV18 | E2 | 8 | 293 |
| HPV18 | E2 | 11 | 293 |
| HPV18 | E2 | 9 | 116 |
| HPV18 | E2 | 11 | 18 |
| HPV18 | E2 | 8 | 152 |
| HPV18 | E2 | 9 | 152 |
| HPV18 | E2 | 9 | 329 |
| HPV18 | E2 | 10 | 329 |
| HPV18 | E2 | 11 | 238 |
| HPV18 | E2 | 11 | 281 |
| HPV18 | E2 | 11 | 267 |
| HPV18 | E2 | 9 | 58 |
| HPV18 | E2 | 11 | 12 |
| HPV18 | E2 | 11 | 8 |
| HPV18 | E2 | 11 | 333 |
| HPV18 | E2 | 10 | 81 |
| HPV18 | E2 | 11 | 81 |
| HPV18 | E2 | 9 | 144 |
| HPV18 | E2 | 10 | 133 |
| HPV18 | E2 | 11 | 133 |
| HPV18 | E2 | 8 | 44 |
| HPV18 | E2 | 10 | 44 |
| HPV18 | E2 | 8 | 67 |
| HPV18 | E2 | 9 | 67 |
| HPV18 | E2 | 8 | 297 |
| HPV18 | E2 | 9 | 297 |
| HPV18 | E2 | 11 | 297 |
| HPV18 | E2 | 9 | 107 |
| HPV18 | E2 | 10 | 107 |
| HPV18 | E2 | 8 | 170 |
| HPV18 | E2 | 8 | 185 |
| HPV18 | E2 | 9 | 285 |
| HPV18 | E2 | 9 | 64 |
| HPV18 | E2 | 11 | 64 |
| HPV18 | E2 | 10 | 353 |
| HPV18 | E2 | 9 | 249 |
| HPV18 | E2 | 11 | 249 |
| HPV18 | E2 | 9 | 288 |
| HPV18 | E2 | 8 | 272 |
| HPV18 | E2 | 9 | 272 |
| HPV18 | E2 | 8 | 16 |
| HPV18 | E2 | 8 | 84 |
| HPV18 | E2 | 9 | 84 |
| HPV18 | E2 | 9 | 33 |
| HPV18 | E2 | 9 | 220 |
| HPV18 | E2 | 8 | 216 |
| HPV18 | E2 | 11 | 80 |
| HPV18 | E2 | 11 | 56 |
| HPV18 | E2 | 10 | 2 |
| HPV18 | E2 | 10 | 242 |
| HPV18 | E2 | 11 | 119 |
| HPV18 | E2 | 10 | 61 |
| HPV18 | E2 | 8 | 122 |
| HPV18 | E2 | 8 | 314 |
| HPV18 | E2 | 10 | 160 |
| HPV18 | E2 | 8 | 305 |
| HPV18 | E2 | 9 | 305 |
| HPV18 | E2 | 10 | 305 |
| HPV18 | E2 | 8 | 11 |
| HPV18 | E2 | 8 | 296 |
| HPV18 | E2 | 9 | 296 |
| HPV18 | E2 | 10 | 296 |
| HPV18 | E2 | 8 | 244 |
| HPV18 | E2 | 11 | 213 |
| HPV18 | E2 | 10 | 13 |
| HPV18 | E2 | 11 | 13 |

TABLE XVII-continued

HLA-AI1 Motif Peptides

| 1 | 2 | 3 | 4 |
|---|---|---|---|
| HPV18 | E2 | 9 | 283 |
| HPV18 | E2 | 11 | 283 |
| HPV18 | E2 | 8 | 298 |
| HPV18 | E2 | 10 | 298 |
| HPV18 | E2 | 11 | 298 |
| HPV18 | E2 | 10 | 229 |
| HPV18 | E2 | 9 | 230 |
| HPV18 | E2 | 11 | 230 |
| HPV18 | E2 | 8 | 233 |
| HPV18 | E2 | 8 | 355 |
| HPV18 | E2 | 8 | 153 |
| HPV18 | E2 | 11 | 153 |
| HPV18 | E2 | 9 | 155 |
| HPV18 | E2 | 10 | 155 |
| HPV18 | E2 | 8 | 145 |
| HPV18 | E2 | 8 | 330 |
| HPV18 | E2 | 9 | 330 |
| HPV18 | E2 | 8 | 273 |
| HPV18 | E2 | 10 | 57 |
| HPV18 | E2 | 9 | 243 |
| HPV18 | E2 | 8 | 286 |
| HPV18 | E2 | 11 | 286 |
| HPV18 | E2 | 10 | 120 |
| HPV18 | E2 | 9 | 211 |
| HPV18 | E2 | 8 | 231 |
| HPV18 | E2 | 10 | 231 |
| HPV18 | E2 | 10 | 334 |
| HPV18 | E2 | 8 | 136 |
| HPV18 | E2 | 8 | 212 |
| HPV18 | E2 | 8 | 157 |
| HPV18 | E2 | 10 | 157 |
| HPV18 | E2 | 9 | 232 |
| HPV18 | E2 | 9 | 335 |
| HPV18 | E2 | 11 | 335 |
| HPV18 | E2 | 9 | 62 |
| HPV18 | E2 | 11 | 62 |
| HPV18 | E2 | 10 | 150 |
| HPV18 | E2 | 11 | 150 |
| HPV18 | E2 | 10 | 106 |
| HPV18 | E2 | 11 | 105 |
| HPV18 | E2 | 8 | 322 |
| HPV18 | E2 | 10 | 183 |
| HPV18 | E2 | 9 | 240 |
| HPV18 | E2 | 10 | 173 |
| HPV18 | E2 | 11 | 173 |
| HPV18 | E2 | 10 | 143 |
| HPV18 | E2 | 9 | 66 |
| HPV18 | E2 | 10 | 66 |
| HPV18 | E2 | 9 | 169 |
| HPV18 | E2 | 11 | 228 |
| HPV18 | E2 | 8 | 135 |
| HPV18 | E2 | 9 | 135 |
| HPV18 | E2 | 10 | 164 |
| HPV18 | E5 | 11 | 29 |
| HPV18 | E5 | 11 | 9 |
| HPV18 | E5 | 10 | 56 |
| HPV18 | E5 | 9 | 11 |
| HPV18 | E5 | 8 | 8 |
| HPV18 | E5 | 11 | 55 |
| HPV18 | E5 | 10 | 10 |
| HPV18 | E5 | 10 | 5 |
| HPV18 | E5 | 9 | 57 |
| HPV18 | E5 | 11 | 57 |
| HPV18 | E5 | 11 | 5 |
| HPV18 | E5 | 11 | 43 |
| HPV18 | E5 | 9 | 7 |
| HPV18 | E5 | 8 | 58 |
| HPV18 | E5 | 10 | 58 |
| HPV18 | E5 | 10 | 22 |
| HPV18 | E5 | 8 | 46 |
| HPV18 | E5 | 11 | 21 |
| HPV18 | E5 | 8 | 50 |
| HPV18 | E5 | 8 | 24 |
| HPV18 | E5 | 10 | 44 |
| HPV18 | E5 | 8 | 12 |
| HPV18 | E5 | 9 | 31 |
| HPV18 | E6 | 10 | 63 |
| HPV18 | E6 | 9 | 64 |
| HPV18 | E6 | 11 | 64 |
| HPV18 | E6 | 9 | 48 |
| HPV18 | E6 | 10 | 48 |
| HPV18 | E6 | 9 | 131 |
| HPV18 | E6 | 9 | 141 |
| HPV18 | E6 | 9 | 68 |
| HPV18 | E6 | 8 | 142 |
| HPV18 | E6 | 11 | 142 |
| HPV18 | E6 | 10 | 70 |
| HPV18 | E6 | 11 | 70 |
| HPV18 | E6 | 8 | 27 |
| HPV18 | E6 | 10 | 27 |
| HPV18 | E6 | 9 | 58 |
| HPV18 | E6 | 10 | 58 |
| HPV18 | E6 | 10 | 83 |
| HPV18 | E6 | 8 | 5 |
| HPV18 | E6 | 9 | 5 |
| HPV18 | E6 | 11 | 46 |
| HPV18 | E6 | 8 | 29 |
| HPV18 | E6 | 10 | 77 |
| HPV18 | E6 | 11 | 40 |
| HPV18 | E6 | 8 | 43 |
| HPV18 | E6 | 10 | 47 |
| HPV18 | E6 | 11 | 47 |
| HPV18 | E6 | 10 | 53 |
| HPV18 | E6 | 8 | 97 |
| HPV18 | E6 | 11 | 97 |
| HPV18 | E6 | 11 | 62 |
| HPV18 | E6 | 9 | 120 |
| HPV18 | E6 | 8 | 128 |
| HPV18 | E6 | 8 | 139 |
| HPV18 | E6 | 11 | 139 |
| HPV18 | E6 | 10 | 130 |
| HPV18 | E6 | 8 | 69 |
| HPV18 | E6 | 11 | 69 |
| HPV18 | E6 | 8 | 67 |
| HPV18 | E6 | 10 | 67 |
| HPV18 | E6 | 8 | 50 |
| HPV18 | E6 | 8 | 117 |
| HPV18 | E6 | 9 | 117 |
| HPV18 | E6 | 10 | 117 |
| HPV18 | E6 | 8 | 92 |
| HPV18 | E6 | 11 | 52 |
| HPV18 | E6 | 9 | 102 |
| HPV18 | E6 | 10 | 101 |
| HPV18 | E6 | 8 | 121 |
| HPV18 | E6 | 8 | 112 |
| HPV18 | E6 | 9 | 112 |
| HPV18 | E6 | 10 | 41 |
| HPV18 | E6 | 9 | 1 |
| HPV18 | E6 | 10 | 1 |
| HPV18 | E6 | 11 | 129 |
| HPV18 | E6 | 8 | 100 |
| HPV18 | E6 | 11 | 100 |
| HPV18 | E6 | 10 | 95 |
| HPV18 | E6 | 11 | 114 |
| HPV18 | E6 | 9 | 111 |
| HPV18 | E6 | 10 | 111 |
| HPV18 | E6 | 8 | 137 |
| HPV18 | E6 | 10 | 137 |
| HPV18 | E6 | 9 | 26 |
| HPV18 | E6 | 11 | 26 |
| HPV18 | E6 | 9 | 144 |
| HPV18 | E6 | 10 | 144 |
| HPV18 | E6 | 11 | 144 |
| HPV18 | E6 | 11 | 107 |
| HPV18 | E6 | 10 | 57 |
| HPV18 | E6 | 11 | 57 |
| HPV18 | E6 | 8 | 3 |
| HPV18 | E6 | 10 | 3 |
| HPV18 | E6 | 11 | 3 |
| HPV18 | E6 | 8 | 126 |

TABLE XVII-continued

HLA-AI1 Motif Peptides

| 1 | 2 | 3 | 4 |
|---|---|---|---|
| HPV18 | E6 | 9 | 126 |
| HPV18 | E6 | 10 | 126 |
| HPV18 | E6 | 10 | 135 |
| HPV18 | E6 | 8 | 74 |
| HPV18 | E6 | 10 | 140 |
| HPV18 | E6 | 11 | 82 |
| HPV18 | E6 | 8 | 59 |
| HPV18 | E6 | 9 | 59 |
| HPV18 | E6 | 11 | 24 |
| HPV18 | E6 | 9 | 84 |
| HPV18 | E6 | 9 | 96 |
| HPV18 | E6 | 11 | 89 |
| HPV18 | E6 | 11 | 94 |
| HPV18 | E6 | 9 | 54 |
| HPV18 | E6 | 9 | 99 |
| HPV18 | E6 | 8 | 72 |
| HPV18 | E6 | 9 | 72 |
| HPV18 | E6 | 10 | 72 |
| HPV18 | E7 | 9 | 6 |
| HPV18 | E7 | 9 | 65 |
| HPV18 | E7 | 9 | 63 |
| HPV18 | E7 | 11 | 63 |
| HPV18 | E7 | 11 | 42 |
| HPV18 | E7 | 9 | 40 |
| HPV18 | E7 | 9 | 20 |
| HPV18 | E7 | 10 | 37 |
| HPV18 | E7 | 8 | 77 |
| HPV18 | E7 | 10 | 43 |
| HPV18 | E7 | 11 | 43 |
| HPV18 | E7 | 11 | 48 |
| HPV18 | E7 | 9 | 59 |
| HPV18 | E7 | 8 | 41 |
| HPV18 | E7 | 10 | 5 |
| HPV18 | E7 | 10 | 62 |
| HPV18 | E7 | 11 | 74 |
| HPV18 | E7 | 8 | 64 |
| HPV18 | E7 | 10 | 64 |
| HPV18 | E7 | 11 | 61 |
| HPV18 | E7 | 9 | 38 |
| HPV18 | E7 | 11 | 38 |
| HPV18 | E7 | 9 | 50 |
| HPV18 | E7 | 10 | 50 |
| HPV18 | E7 | 11 | 18 |
| HPV18 | E7 | 8 | 7 |
| HPV18 | E7 | 8 | 60 |
| HPV18 | E7 | 9 | 44 |
| HPV18 | E7 | 10 | 44 |
| HPV18 | E7 | 10 | 75 |
| HPV18 | L1 | 10 | 494 |
| HPV18 | L1 | 11 | 195 |
| HPV18 | L1 | 9 | 162 |
| HPV18 | L1 | 8 | 447 |
| HPV18 | L1 | 11 | 115 |
| HPV18 | L1 | 8 | 225 |
| HPV18 | L1 | 11 | 63 |
| HPV18 | L1 | 11 | 268 |
| HPV18 | L1 | 8 | 345 |
| HPV18 | L1 | 11 | 407 |
| HPV18 | L1 | 9 | 419 |
| HPV18 | L1 | 10 | 419 |
| HPV18 | L1 | 10 | 196 |
| HPV18 | L1 | 9 | 552 |
| HPV18 | L1 | 10 | 552 |
| HPV18 | L1 | 8 | 163 |
| HPV18 | L1 | 8 | 222 |
| HPV18 | L1 | 11 | 222 |
| HPV18 | L1 | 10 | 42 |
| HPV18 | L1 | 10 | 310 |
| HPV18 | L1 | 11 | 310 |
| HPV18 | L1 | 10 | 2 |
| HPV18 | L1 | 11 | 2 |
| HPV18 | L1 | 8 | 493 |
| HPV18 | L1 | 11 | 493 |
| HPV18 | L1 | 8 | 418 |
| HPV18 | L1 | 10 | 418 |
| HPV18 | L1 | 11 | 418 |
| HPV18 | L1 | 8 | 245 |
| HPV18 | L1 | 11 | 86 |
| HPV18 | L1 | 9 | 270 |
| HPV18 | L1 | 9 | 258 |
| HPV18 | L1 | 8 | 284 |
| HPV18 | L1 | 9 | 284 |
| HPV18 | L1 | 8 | 122 |
| HPV18 | L1 | 10 | 122 |
| HPV18 | L1 | 11 | 122 |
| HPV18 | L1 | 9 | 520 |
| HPV18 | L1 | 10 | 520 |
| HPV18 | L1 | 8 | 205 |
| HPV18 | L1 | 8 | 305 |
| HPV18 | L1 | 9 | 305 |
| HPV18 | L1 | 9 | 364 |
| HPV18 | L1 | 11 | 148 |
| HPV18 | L1 | 8 | 330 |
| HPV18 | L1 | 10 | 330 |
| HPV18 | L1 | 10 | 203 |
| HPV18 | L1 | 11 | 203 |
| HPV18 | L1 | 10 | 257 |
| HPV18 | L1 | 11 | 202 |
| HPV18 | L1 | 8 | 498 |
| HPV18 | L1 | 10 | 498 |
| HPV18 | L1 | 8 | 317 |
| HPV18 | L1 | 11 | 309 |
| HPV18 | L1 | 9 | 144 |
| HPV18 | L1 | 8 | 59 |
| HPV18 | L1 | 8 | 530 |
| HPV18 | L1 | 9 | 530 |
| HPV18 | L1 | 10 | 530 |
| HPV18 | L1 | 8 | 368 |
| HPV18 | L1 | 9 | 368 |
| HPV18 | L1 | 8 | 517 |
| HPV18 | L1 | 8 | 271 |
| HPV18 | L1 | 11 | 482 |
| HPV18 | L1 | 9 | 221 |
| HPV18 | L1 | 9 | 244 |
| HPV18 | L1 | 8 | 259 |
| HPV18 | L1 | 9 | 304 |
| HPV18 | L1 | 10 | 304 |
| HPV18 | L1 | 9 | 329 |
| HPV18 | L1 | 11 | 329 |
| HPV18 | L1 | 10 | 116 |
| HPV18 | L1 | 9 | 117 |
| HPV18 | L1 | 8 | 145 |
| HPV18 | L1 | 11 | 535 |
| HPV18 | L1 | 8 | 177 |
| HPV18 | L1 | 10 | 177 |
| HPV18 | L1 | 11 | 342 |
| HPV18 | L1 | 8 | 118 |
| HPV18 | L1 | 10 | 175 |
| HPV18 | L1 | 8 | 38 |
| HPV18 | L1 | 10 | 13 |
| HPV18 | L1 | 11 | 13 |
| HPV18 | L1 | 8 | 380 |
| HPV18 | L1 | 9 | 30 |
| HPV18 | L1 | 11 | 41 |
| HPV18 | L1 | 8 | 285 |
| HPV18 | L1 | 11 | 285 |
| HPV18 | L1 | 9 | 58 |
| HPV18 | L1 | 9 | 94 |
| HPV18 | L1 | 11 | 219 |
| HPV18 | L1 | 10 | 9 |
| HPV18 | L1 | 10 | 443 |
| HPV18 | L1 | 11 | 360 |
| HPV18 | L1 | 9 | 492 |
| HPV18 | L1 | 8 | 500 |
| HPV18 | L1 | 10 | 143 |
| HPV18 | L1 | 8 | 421 |
| HPV18 | L1 | 9 | 529 |
| HPV18 | L1 | 10 | 529 |
| HPV18 | L1 | 11 | 529 |
| HPV18 | L1 | 9 | 516 |

TABLE XVII-continued

HLA-A11 Motif Peptides

| 1 | 2 | 3 | 4 |
|---|---|---|---|
| HPV18 | L1 | 8 | 507 |
| HPV18 | L1 | 10 | 507 |
| HPV18 | L1 | 8 | 232 |
| HPV18 | L1 | 9 | 186 |
| HPV18 | L1 | 10 | 505 |
| HPV18 | L1 | 8 | 125 |
| HPV18 | L1 | 11 | 125 |
| HPV18 | L1 | 8 | 187 |
| HPV18 | L1 | 9 | 283 |
| HPV18 | L1 | 10 | 283 |
| HPV18 | L1 | 10 | 519 |
| HPV18 | L1 | 11 | 519 |
| HPV18 | L1 | 8 | 521 |
| HPV18 | L1 | 9 | 521 |
| HPV18 | L1 | 9 | 316 |
| HPV18 | L1 | 9 | 367 |
| HPV18 | L1 | 10 | 367 |
| HPV18 | L1 | 10 | 220 |
| HPV18 | L1 | 8 | 174 |
| HPV18 | L1 | 11 | 174 |
| HPV18 | L1 | 11 | 8 |
| HPV18 | L1 | 9 | 14 |
| HPV18 | L1 | 10 | 14 |
| HPV18 | L1 | 8 | 103 |
| HPV18 | L1 | 10 | 103 |
| HPV18 | L1 | 9 | 178 |
| HPV18 | L1 | 8 | 445 |
| HPV18 | L1 | 10 | 445 |
| HPV18 | L1 | 9 | 104 |
| HPV18 | L1 | 8 | 531 |
| HPV18 | L1 | 9 | 531 |
| HPV18 | L1 | 11 | 1 |
| HPV18 | L1 | 10 | 269 |
| HPV18 | L1 | 10 | 328 |
| HPV18 | L1 | 9 | 36 |
| HPV18 | L1 | 10 | 36 |
| HPV18 | L1 | 8 | 496 |
| HPV18 | L1 | 10 | 496 |
| HPV18 | L1 | 9 | 224 |
| HPV18 | L1 | 8 | 558 |
| HPV18 | L1 | 10 | 558 |
| HPV18 | L1 | 11 | 558 |
| HPV18 | L1 | 9 | 344 |
| HPV18 | L1 | 11 | 293 |
| HPV18 | L1 | 8 | 414 |
| HPV18 | L1 | 10 | 414 |
| HPV18 | L1 | 10 | 57 |
| HPV18 | L1 | 10 | 282 |
| HPV18 | L1 | 11 | 282 |
| HPV18 | L1 | 9 | 173 |
| HPV18 | L1 | 8 | 28 |
| HPV18 | L1 | 11 | 28 |
| HPV18 | L1 | 10 | 26 |
| HPV18 | L1 | 8 | 16 |
| HPV18 | L1 | 10 | 16 |
| HPV18 | L1 | 11 | 20 |
| HPV18 | L1 | 8 | 550 |
| HPV18 | L1 | 11 | 550 |
| HPV18 | L1 | 8 | 540 |
| HPV18 | L1 | 9 | 472 |
| HPV18 | L1 | 10 | 472 |
| HPV18 | L1 | 10 | 412 |
| HPV18 | L1 | 9 | 121 |
| HPV18 | L1 | 11 | 121 |
| HPV18 | L1 | 10 | 243 |
| HPV18 | L1 | 10 | 378 |
| HPV18 | L1 | 10 | 315 |
| HPV18 | L1 | 10 | 366 |
| HPV18 | L1 | 11 | 366 |
| HPV18 | L1 | 9 | 287 |
| HPV18 | L1 | 8 | 410 |
| HPV18 | L1 | 9 | 484 |
| HPV18 | L1 | 8 | 205 |
| HPV18 | L1 | 9 | 205 |
| HPV18 | L1 | 9 | 102 |

TABLE XVII-continued

HLA-A11 Motif Peptides

| 1 | 2 | 3 | 4 |
|---|---|---|---|
| HPV18 | L1 | 11 | 102 |
| HPV18 | L1 | 11 | 547 |
| HPV18 | L1 | 8 | 6 |
| HPV18 | L1 | 9 | 112 |
| HPV18 | L1 | 9 | 135 |
| HPV18 | L1 | 8 | 561 |
| HPV18 | L1 | 8 | 81 |
| HPV18 | L1 | 10 | 548 |
| HPV18 | L1 | 10 | 551 |
| HPV18 | L1 | 11 | 551 |
| HPV18 | L1 | 9 | 127 |
| HPV18 | L1 | 8 | 363 |
| HPV18 | L1 | 10 | 363 |
| HPV18 | L1 | 8 | 179 |
| HPV18 | L1 | 8 | 288 |
| HPV18 | L1 | 10 | 93 |
| HPV18 | L1 | 8 | 31 |
| HPV18 | L1 | 9 | 150 |
| HPV18 | L1 | 11 | 518 |
| HPV18 | L1 | 8 | 306 |
| HPV18 | L1 | 8 | 198 |
| HPV18 | L1 | 9 | 555 |
| HPV18 | L1 | 11 | 555 |
| HPV18 | L1 | 11 | 100 |
| HPV18 | L1 | 10 | 408 |
| HPV18 | L1 | 8 | 485 |
| HPV18 | L1 | 11 | 78 |
| HPV18 | L1 | 9 | 446 |
| HPV18 | L1 | 11 | 442 |
| HPV18 | L1 | 9 | 444 |
| HPV18 | L1 | 11 | 444 |
| HPV18 | L1 | 11 | 327 |
| HPV18 | L1 | 9 | 362 |
| HPV18 | L1 | 11 | 362 |
| HPV18 | L1 | 11 | 92 |
| HPV18 | L1 | 10 | 149 |
| HPV18 | L1 | 8 | 474 |
| HPV18 | L1 | 9 | 197 |
| HPV18 | L1 | 8 | 554 |
| HPV18 | L1 | 10 | 554 |
| HPV18 | L1 | 8 | 473 |
| HPV18 | L1 | 9 | 473 |
| HPV18 | L1 | 8 | 553 |
| HPV18 | L1 | 9 | 553 |
| HPV18 | L1 | 11 | 553 |
| HPV18 | L1 | 8 | 105 |
| HPV18 | L1 | 9 | 331 |
| HPV18 | L1 | 11 | 71 |
| HPV18 | L1 | 10 | 79 |
| HPV18 | L1 | 11 | 133 |
| HPV18 | L1 | 9 | 176 |
| HPV18 | L1 | 11 | 176 |
| HPV18 | L1 | 10 | 126 |
| HPV18 | L1 | 8 | 89 |
| HPV18 | L1 | 9 | 89 |
| HPV18 | L1 | 10 | 361 |
| HPV18 | L1 | 10 | 161 |
| HPV18 | L1 | 8 | 230 |
| HPV18 | L1 | 10 | 230 |
| HPV18 | L1 | 8 | 373 |
| HPV18 | L1 | 8 | 509 |
| HPV18 | L1 | 9 | 417 |
| HPV18 | L1 | 11 | 417 |
| HPV18 | L1 | 11 | 110 |
| HPV18 | L1 | 10 | 303 |
| HPV18 | L1 | 11 | 303 |
| HPV18 | L1 | 8 | 18 |
| HPV18 | L1 | 9 | 73 |
| HPV18 | L1 | 9 | 295 |
| HPV18 | L1 | 10 | 35 |
| HPV18 | L1 | 11 | 35 |
| HPV18 | L1 | 11 | 184 |
| HPV18 | L1 | 8 | 425 |
| HPV18 | L1 | 8 | 4 |
| HPV18 | L1 | 9 | 4 |

TABLE XVII-continued

HLA-AI1 Motif Peptides

| 1 | 2 | 3 | 4 |
|---|---|---|---|
| HPV18 | L1 | 10 | 4 |
| HPV18 | L1 | 9 | 88 |
| HPV18 | L1 | 10 | 88 |
| HPV18 | L2 | 8 | 222 |
| HPV18 | L2 | 10 | 222 |
| HPV18 | L2 | 10 | 286 |
| HPV18 | L2 | 8 | 237 |
| HPV18 | L2 | 9 | 423 |
| HPV18 | L2 | 8 | 12 |
| HPV18 | L2 | 11 | 12 |
| HPV18 | L2 | 11 | 341 |
| HPV18 | L2 | 9 | 275 |
| HPV18 | L2 | 10 | 275 |
| HPV18 | L2 | 11 | 322 |
| HPV18 | L2 | 11 | 354 |
| HPV18 | L2 | 8 | 344 |
| HPV18 | L2 | 9 | 273 |
| HPV18 | L2 | 11 | 273 |
| HPV18 | L2 | 11 | 109 |
| HPV18 | L2 | 9 | 260 |
| HPV18 | L2 | 9 | 343 |
| HPV18 | L2 | 8 | 36 |
| HPV18 | L2 | 8 | 443 |
| HPV18 | L2 | 11 | 443 |
| HPV18 | L2 | 11 | 241 |
| HPV18 | L2 | 8 | 276 |
| HPV18 | L2 | 9 | 276 |
| HPV18 | L2 | 11 | 306 |
| HPV18 | L2 | 10 | 181 |
| HPV18 | L2 | 8 | 314 |
| HPV18 | L2 | 11 | 58 |
| HPV18 | L2 | 8 | 429 |
| HPV18 | L2 | 10 | 62 |
| HPV18 | L2 | 10 | 25 |
| HPV18 | L2 | 8 | 64 |
| HPV18 | L2 | 9 | 60 |
| HPV18 | L2 | 10 | 432 |
| HPV18 | L2 | 11 | 432 |
| HPV18 | L2 | 8 | 183 |
| HPV18 | L2 | 10 | 183 |
| HPV18 | L2 | 9 | 310 |
| HPV18 | L2 | 11 | 310 |
| HPV18 | L2 | 11 | 292 |
| HPV18 | L2 | 11 | 431 |
| HPV18 | L2 | 8 | 313 |
| HPV18 | L2 | 9 | 313 |
| HPV18 | L2 | 8 | 428 |
| HPV18 | L2 | 9 | 428 |
| HPV18 | L2 | 10 | 59 |
| HPV18 | L2 | 10 | 323 |
| HPV18 | L2 | 10 | 210 |
| HPV18 | L2 | 11 | 210 |
| HPV18 | L2 | 10 | 34 |
| HPV18 | L2 | 10 | 299 |
| HPV18 | L2 | 10 | 242 |
| HPV18 | L2 | 9 | 287 |
| HPV18 | L2 | 10 | 391 |
| HPV18 | L2 | 8 | 277 |
| HPV18 | L2 | 10 | 355 |
| HPV18 | L2 | 8 | 1 |
| HPV18 | L2 | 9 | 1 |
| HPV18 | L2 | 10 | 1 |
| HPV18 | L2 | 11 | 1 |
| HPV18 | L2 | 10 | 79 |
| HPV18 | L2 | 11 | 285 |
| HPV18 | L2 | 10 | 422 |
| HPV18 | L2 | 8 | 357 |
| HPV18 | L2 | 10 | 272 |
| HPV18 | L2 | 8 | 325 |
| HPV18 | L2 | 11 | 209 |
| HPV18 | L2 | 11 | 390 |
| HPV18 | L2 | 8 | 439 |
| HPV18 | L2 | 9 | 439 |
| HPV18 | L2 | 10 | 439 |
| HPV18 | L2 | 11 | 439 |
| HPV18 | L2 | 9 | 419 |
| HPV18 | L2 | 9 | 376 |
| HPV18 | L2 | 8 | 185 |
| HPV18 | L2 | 10 | 216 |
| HPV18 | L2 | 11 | 258 |
| HPV18 | L2 | 9 | 312 |
| HPV18 | L2 | 10 | 312 |
| HPV18 | L2 | 8 | 11 |
| HPV18 | L2 | 9 | 11 |
| HPV18 | L2 | 8 | 295 |
| HPV18 | L2 | 8 | 291 |
| HPV18 | L2 | 11 | 298 |
| HPV18 | L2 | 10 | 281 |
| HPV18 | L2 | 11 | 281 |
| HPV18 | L2 | 9 | 308 |
| HPV18 | L2 | 11 | 308 |
| HPV18 | L2 | 10 | 364 |
| HPV18 | L2 | 11 | 364 |
| HPV18 | L2 | 10 | 68 |
| HPV18 | L2 | 8 | 220 |
| HPV18 | L2 | 10 | 220 |
| HPV18 | L2 | 8 | 274 |
| HPV18 | L2 | 10 | 274 |
| HPV18 | L2 | 11 | 274 |
| HPV18 | L2 | 11 | 24 |
| HPV18 | L2 | 9 | 63 |
| HPV18 | L2 | 8 | 309 |
| HPV18 | L2 | 10 | 309 |
| HPV18 | L2 | 11 | 78 |
| HPV18 | L2 | 9 | 211 |
| HPV18 | L2 | 10 | 211 |
| HPV18 | L2 | 10 | 110 |
| HPV18 | L2 | 8 | 393 |
| HPV18 | L2 | 8 | 212 |
| HPV18 | L2 | 9 | 212 |
| HPV18 | L2 | 8 | 424 |
| HPV18 | L2 | 11 | 424 |
| HPV18 | L2 | 9 | 365 |
| HPV18 | L2 | 10 | 365 |
| HPV18 | L2 | 10 | 235 |
| HPV18 | L2 | 10 | 13 |
| HPV18 | L2 | 9 | 111 |
| HPV18 | L2 | 8 | 420 |
| HPV18 | L2 | 9 | 26 |
| HPV18 | L2 | 8 | 15 |
| HPV18 | L2 | 8 | 61 |
| HPV18 | L2 | 11 | 61 |
| HPV18 | L2 | 9 | 69 |
| HPV18 | L2 | 8 | 377 |
| HPV18 | L2 | 8 | 367 |
| HPV18 | L2 | 8 | 288 |
| HPV18 | L2 | 11 | 288 |
| HPV18 | L2 | 9 | 392 |
| HPV18 | L2 | 8 | 261 |
| HPV18 | L2 | 8 | 366 |
| HPV18 | L2 | 9 | 366 |
| HPV18 | L2 | 10 | 293 |
| HPV18 | L2 | 9 | 217 |
| HPV18 | L2 | 11 | 217 |
| HPV18 | L2 | 9 | 80 |
| HPV18 | L2 | 9 | 221 |
| HPV18 | L2 | 11 | 221 |
| HPV18 | L2 | 9 | 236 |
| HPV18 | L2 | 10 | 259 |
| HPV18 | L2 | 11 | 180 |
| HPV18 | L2 | 9 | 182 |
| HPV18 | L2 | 11 | 182 |
| HPV18 | L2 | 8 | 2 |
| HPV18 | L2 | 9 | 2 |
| HPV18 | L2 | 10 | 2 |
| HPV18 | L2 | 11 | 417 |
| HPV18 | L2 | 11 | 234 |
| HPV18 | L2 | 9 | 14 |
| HPV18 | L2 | 8 | 81 |
| HPV18 | L2 | 8 | 112 |

TABLE XVII-continued

HLA-AI1 Motif Peptides

| 1 | 2 | 3 | 4 |
|---|---|---|---|
| HPV18 | L2 | 8 | 442 |
| HPV18 | L2 | 9 | 442 |
| HPV18 | L2 | 8 | 427 |
| HPV18 | L2 | 9 | 427 |
| HPV18 | L2 | 10 | 427 |
| HPV18 | L2 | 11 | 436 |
| HPV18 | L2 | 11 | 374 |
| HPV31 | E1 | 8 | 296 |
| HPV31 | E1 | 8 | 185 |
| HPV31 | E1 | 11 | 185 |
| HPV31 | E1 | 10 | 371 |
| HPV31 | E1 | 9 | 550 |
| HPV31 | E1 | 11 | 550 |
| HPV31 | E1 | 9 | 111 |
| HPV31 | E1 | 11 | 68 |
| HPV31 | E1 | 11 | 439 |
| HPV31 | E1 | 10 | 186 |
| HPV31 | E1 | 8 | 504 |
| HPV31 | E1 | 8 | 81 |
| HPV31 | E1 | 9 | 81 |
| HPV31 | E1 | 11 | 370 |
| HPV31 | E1 | 10 | 263 |
| HPV31 | E1 | 11 | 410 |
| HPV31 | E1 | 8 | 385 |
| HPV31 | E1 | 9 | 385 |
| HPV31 | E1 | 10 | 385 |
| HPV31 | E1 | 10 | 113 |
| HPV31 | E1 | 11 | 113 |
| HPV31 | E1 | 9 | 477 |
| HPV31 | E1 | 11 | 477 |
| HPV31 | E1 | 8 | 284 |
| HPV31 | E1 | 10 | 284 |
| HPV31 | E1 | 8 | 155 |
| HPV31 | E1 | 11 | 155 |
| HPV31 | E1 | 9 | 100 |
| HPV31 | E1 | 11 | 100 |
| HPV31 | E1 | 8 | 620 |
| HPV31 | E1 | 8 | 503 |
| HPV31 | E1 | 9 | 503 |
| HPV31 | E1 | 8 | 384 |
| HPV31 | E1 | 9 | 384 |
| HPV31 | E1 | 10 | 384 |
| HPV31 | E1 | 11 | 384 |
| HPV31 | E1 | 9 | 502 |
| HPV31 | E1 | 10 | 502 |
| HPV31 | E1 | 8 | 553 |
| HPV31 | E1 | 10 | 553 |
| HPV31 | E1 | 8 | 351 |
| HPV31 | E1 | 9 | 351 |
| HPV31 | E1 | 9 | 49 |
| HPV31 | E1 | 9 | 611 |
| HPV31 | E1 | 10 | 521 |
| HPV31 | E1 | 11 | 521 |
| HPV31 | E1 | 8 | 96 |
| HPV31 | E1 | 8 | 421 |
| HPV31 | E1 | 10 | 336 |
| HPV31 | E1 | 11 | 364 |
| HPV31 | E1 | 8 | 352 |
| HPV31 | E1 | 9 | 366 |
| HPV31 | E1 | 11 | 528 |
| HPV31 | E1 | 10 | 348 |
| HPV31 | E1 | 11 | 348 |
| HPV31 | E1 | 10 | 62 |
| HPV31 | E1 | 8 | 80 |
| HPV31 | E1 | 9 | 80 |
| HPV31 | E1 | 10 | 80 |
| HPV31 | E1 | 10 | 432 |
| HPV31 | E1 | 9 | 416 |
| HPV31 | E1 | 10 | 229 |
| HPV31 | E1 | 10 | 10 |
| HPV31 | E1 | 10 | 201 |
| HPV31 | E1 | 8 | 583 |
| HPV31 | E1 | 11 | 609 |
| HPV31 | E1 | 8 | 115 |
| HPV31 | E1 | 9 | 115 |
| HPV31 | E1 | 10 | 115 |
| HPV31 | E1 | 8 | 64 |
| HPV31 | E1 | 8 | 315 |
| HPV31 | E1 | 9 | 574 |
| HPV31 | E1 | 11 | 335 |
| HPV31 | E1 | 8 | 592 |
| HPV31 | E1 | 8 | 50 |
| HPV31 | E1 | 8 | 443 |
| HPV31 | E1 | 9 | 372 |
| HPV31 | E1 | 9 | 473 |
| HPV31 | E1 | 10 | 436 |
| HPV31 | E1 | 11 | 593 |
| HPV31 | E1 | 11 | 566 |
| HPV31 | E1 | 9 | 433 |
| HPV31 | E1 | 9 | 457 |
| HPV31 | E1 | 10 | 476 |
| HPV31 | E1 | 8 | 612 |
| HPV31 | E1 | 8 | 417 |
| HPV31 | E1 | 11 | 417 |
| HPV31 | E1 | 9 | 230 |
| HPV31 | E1 | 9 | 305 |
| HPV31 | E1 | 9 | 252 |
| HPV31 | E1 | 11 | 252 |
| HPV31 | E1 | 9 | 522 |
| HPV31 | E1 | 10 | 522 |
| HPV31 | E1 | 11 | 522 |
| HPV31 | E1 | 10 | 578 |
| HPV31 | E1 | 9 | 157 |
| HPV31 | E1 | 9 | 11 |
| HPV31 | E1 | 8 | 386 |
| HPV31 | E1 | 9 | 386 |
| HPV31 | E1 | 8 | 225 |
| HPV31 | E1 | 11 | 446 |
| HPV31 | E1 | 9 | 196 |
| HPV31 | E1 | 11 | 222 |
| HPV31 | E1 | 9 | 78 |
| HPV31 | E1 | 10 | 78 |
| HPV31 | E1 | 11 | 78 |
| HPV31 | E1 | 8 | 71 |
| HPV31 | E1 | 11 | 487 |
| HPV31 | E1 | 8 | 456 |
| HPV31 | E1 | 10 | 456 |
| HPV31 | E1 | 11 | 162 |
| HPV31 | E1 | 8 | 112 |
| HPV31 | E1 | 11 | 112 |
| HPV31 | E1 | 8 | 478 |
| HPV31 | E1 | 10 | 478 |
| HPV31 | E1 | 11 | 453 |
| HPV31 | E1 | 11 | 174 |
| HPV31 | E1 | 8 | 548 |
| HPV31 | E1 | 11 | 548 |
| HPV31 | E1 | 11 | 471 |
| HPV31 | E1 | 9 | 479 |
| HPV31 | E1 | 9 | 268 |
| HPV31 | E1 | 9 | 544 |
| HPV31 | E1 | 10 | 381 |
| HPV31 | E1 | 11 | 381 |
| HPV31 | E1 | 9 | 184 |
| HPV31 | E1 | 10 | 110 |
| HPV31 | E1 | 11 | 262 |
| HPV31 | E1 | 9 | 619 |
| HPV31 | E1 | 8 | 383 |
| HPV31 | E1 | 9 | 383 |
| HPV31 | E1 | 10 | 383 |
| HPV31 | E1 | 11 | 383 |
| HPV31 | E1 | 9 | 552 |
| HPV31 | E1 | 11 | 552 |
| HPV31 | E1 | 11 | 380 |
| HPV31 | E1 | 9 | 441 |
| HPV31 | E1 | 10 | 441 |
| HPV31 | E1 | 10 | 291 |
| HPV31 | E1 | 8 | 265 |
| HPV31 | E1 | 9 | 587 |
| HPV31 | E1 | 10 | 590 |
| HPV31 | E1 | 10 | 374 |

TABLE XVII-continued

HLA-AI1 Motif Peptides

| 1 | 2 | 3 | 4 |
|---|---|---|---|
| HPV31 | E1 | 10 | 232 |
| HPV31 | E1 | 9 | 412 |
| HPV31 | E1 | 10 | 501 |
| HPV31 | E1 | 11 | 501 |
| HPV31 | E1 | 11 | 520 |
| HPV31 | E1 | 9 | 125 |
| HPV31 | E1 | 10 | 69 |
| HPV31 | E1 | 8 | 442 |
| HPV31 | E1 | 9 | 442 |
| HPV31 | E1 | 8 | 188 |
| HPV31 | E1 | 10 | 454 |
| HPV31 | E1 | 8 | 286 |
| HPV31 | E1 | 9 | 202 |
| HPV31 | E1 | 10 | 543 |
| HPV31 | E1 | 11 | 542 |
| HPV31 | E1 | 8 | 234 |
| HPV31 | E1 | 10 | 234 |
| HPV31 | E1 | 10 | 256 |
| HPV31 | E1 | 9 | 600 |
| HPV31 | E1 | 9 | 437 |
| HPV31 | E1 | 10 | 153 |
| HPV31 | E1 | 10 | 94 |
| HPV31 | E1 | 9 | 337 |
| HPV31 | E1 | 8 | 258 |
| HPV31 | E1 | 10 | 258 |
| HPV31 | E1 | 10 | 388 |
| HPV31 | E1 | 11 | 388 |
| HPV31 | E1 | 8 | 350 |
| HPV31 | E1 | 9 | 350 |
| HPV31 | E1 | 10 | 350 |
| HPV31 | E1 | 8 | 402 |
| HPV31 | E1 | 11 | 402 |
| HPV31 | E1 | 11 | 500 |
| HPV31 | E1 | 9 | 187 |
| HPV31 | E1 | 9 | 285 |
| HPV31 | E1 | 8 | 255 |
| HPV31 | E1 | 11 | 255 |
| HPV31 | E1 | 9 | 257 |
| HPV31 | E1 | 11 | 257 |
| HPV31 | E1 | 8 | 400 |
| HPV31 | E1 | 10 | 400 |
| HPV31 | E1 | 8 | 306 |
| HPV31 | E1 | 11 | 47 |
| HPV31 | E1 | 8 | 253 |
| HPV31 | E1 | 10 | 253 |
| HPV31 | E1 | 10 | 549 |
| HPV31 | E1 | 9 | 283 |
| HPV31 | E1 | 11 | 283 |
| HPV31 | E1 | 10 | 610 |
| HPV31 | E1 | 11 | 347 |
| HPV31 | E1 | 9 | 182 |
| HPV31 | E1 | 11 | 182 |
| HPV31 | E1 | 11 | 577 |
| HPV31 | E1 | 10 | 156 |
| HPV31 | E1 | 9 | 547 |
| HPV31 | E1 | 8 | 601 |
| HPV31 | E1 | 8 | 116 |
| HPV31 | E1 | 9 | 116 |
| HPV31 | E1 | 8 | 117 |
| HPV31 | E1 | 8 | 376 |
| HPV31 | E1 | 9 | 507 |
| HPV31 | E1 | 11 | 507 |
| HPV31 | E1 | 10 | 573 |
| HPV31 | E1 | 11 | 93 |
| HPV31 | E1 | 8 | 569 |
| HPV31 | E1 | 10 | 170 |
| HPV31 | E1 | 8 | 524 |
| HPV31 | E1 | 9 | 524 |
| HPV31 | E1 | 8 | 580 |
| HPV31 | E1 | 11 | 580 |
| HPV31 | E1 | 11 | 475 |
| HPV31 | E1 | 9 | 399 |
| HPV31 | E1 | 11 | 399 |
| HPV31 | E1 | 9 | 176 |
| HPV31 | E1 | 8 | 420 |
| HPV31 | E1 | 9 | 420 |
| HPV31 | E1 | 8 | 260 |
| HPV31 | E1 | 10 | 267 |
| HPV31 | E1 | 10 | 124 |
| HPV31 | E1 | 10 | 599 |
| HPV31 | E1 | 8 | 172 |
| HPV31 | E1 | 8 | 293 |
| HPV31 | E1 | 10 | 293 |
| HPV31 | E1 | 11 | 293 |
| HPV31 | E1 | 11 | 303 |
| HPV31 | E1 | 9 | 595 |
| HPV31 | E1 | 8 | 438 |
| HPV31 | E1 | 9 | 154 |
| HPV31 | E1 | 10 | 99 |
| HPV31 | E1 | 11 | 414 |
| HPV31 | E1 | 8 | 158 |
| HPV31 | E1 | 9 | 95 |
| HPV31 | E1 | 11 | 585 |
| HPV31 | E1 | 10 | 365 |
| HPV31 | E1 | 9 | 591 |
| HPV31 | E1 | 10 | 472 |
| HPV31 | E1 | 11 | 435 |
| HPV31 | E1 | 9 | 401 |
| HPV31 | E1 | 8 | 367 |
| HPV31 | E1 | 10 | 181 |
| HPV31 | E1 | 10 | 546 |
| HPV31 | E1 | 9 | 375 |
| HPV31 | E1 | 11 | 98 |
| HPV31 | E1 | 9 | 294 |
| HPV31 | E1 | 10 | 294 |
| HPV31 | E1 | 11 | 281 |
| HPV31 | E1 | 8 | 295 |
| HPV31 | E1 | 9 | 295 |
| HPV31 | E1 | 11 | 617 |
| HPV31 | E1 | 10 | 567 |
| HPV31 | E1 | 8 | 12 |
| HPV31 | E1 | 10 | 304 |
| HPV31 | E1 | 9 | 224 |
| HPV31 | E1 | 8 | 269 |
| HPV31 | E1 | 9 | 233 |
| HPV31 | E1 | 11 | 233 |
| HPV31 | E1 | 11 | 152 |
| HPV31 | E1 | 8 | 387 |
| HPV31 | E1 | 11 | 387 |
| HPV31 | E1 | 10 | 282 |
| HPV31 | E1 | 11 | 180 |
| HPV31 | E1 | 8 | 545 |
| HPV31 | E1 | 11 | 545 |
| HPV31 | E1 | 11 | 505 |
| HPV31 | E1 | 10 | 48 |
| HPV31 | E1 | 8 | 101 |
| HPV31 | E1 | 10 | 101 |
| HPV31 | E1 | 8 | 177 |
| HPV31 | E1 | 9 | 349 |
| HPV31 | E1 | 10 | 349 |
| HPV31 | E1 | 11 | 349 |
| HPV31 | E1 | 9 | 254 |
| HPV31 | E1 | 8 | 413 |
| HPV31 | E1 | 8 | 434 |
| HPV31 | E1 | 8 | 197 |
| HPV31 | E1 | 8 | 525 |
| HPV31 | E1 | 10 | 223 |
| HPV31 | E1 | 10 | 17 |
| HPV31 | E1 | 10 | 251 |
| HPV31 | E1 | 10 | 319 |
| HPV31 | E1 | 8 | 405 |
| HPV31 | E1 | 9 | 489 |
| HPV31 | E1 | 10 | 313 |
| HPV31 | E1 | 10 | 195 |
| HPV31 | E1 | 8 | 103 |
| HPV31 | E1 | 8 | 19 |
| HPV31 | E2 | 9 | 277 |
| HPV31 | E2 | 8 | 278 |
| HPV31 | E2 | 9 | 229 |
| HPV31 | E2 | 10 | 229 |

TABLE XVII-continued

HLA-AI1 Motif Peptides

| 1 | 2 | 3 | 4 |
|---|---|---|---|
| HPV31 | E2 | 8 | 61 |
| HPV31 | E2 | 8 | 302 |
| HPV31 | E2 | 9 | 302 |
| HPV31 | E2 | 10 | 302 |
| HPV31 | E2 | 10 | 217 |
| HPV31 | E2 | 9 | 291 |
| HPV31 | E2 | 9 | 239 |
| HPV31 | E2 | 10 | 228 |
| HPV31 | E2 | 11 | 228 |
| HPV31 | E2 | 8 | 27 |
| HPV31 | E2 | 9 | 27 |
| HPV31 | E2 | 11 | 27 |
| HPV31 | E2 | 8 | 307 |
| HPV31 | E2 | 9 | 307 |
| HPV31 | E2 | 10 | 307 |
| HPV31 | E2 | 11 | 145 |
| HPV31 | E2 | 8 | 40 |
| HPV31 | E2 | 9 | 301 |
| HPV31 | E2 | 10 | 301 |
| HPV31 | E2 | 11 | 301 |
| HPV31 | E2 | 8 | 351 |
| HPV31 | E2 | 9 | 122 |
| HPV31 | E2 | 10 | 122 |
| HPV31 | E2 | 8 | 22 |
| HPV31 | E2 | 11 | 22 |
| HPV31 | E2 | 8 | 124 |
| HPV31 | E2 | 9 | 174 |
| HPV31 | E2 | 10 | 174 |
| HPV31 | E2 | 9 | 39 |
| HPV31 | E2 | 10 | 149 |
| HPV31 | E2 | 11 | 149 |
| HPV31 | E2 | 11 | 234 |
| HPV31 | E2 | 10 | 204 |
| HPV31 | E2 | 9 | 48 |
| HPV31 | E2 | 10 | 20 |
| HPV31 | E2 | 8 | 80 |
| HPV31 | E2 | 9 | 80 |
| HPV31 | E2 | 9 | 118 |
| HPV31 | E2 | 10 | 121 |
| HPV31 | E2 | 11 | 121 |
| HPV31 | E2 | 8 | 171 |
| HPV31 | E2 | 9 | 168 |
| HPV31 | E2 | 10 | 168 |
| HPV31 | E2 | 11 | 168 |
| HPV31 | E2 | 8 | 108 |
| HPV31 | E2 | 10 | 300 |
| HPV31 | E2 | 11 | 300 |
| HPV31 | E2 | 8 | 123 |
| HPV31 | E2 | 9 | 123 |
| HPV31 | E2 | 9 | 156 |
| HPV31 | E2 | 9 | 179 |
| HPV31 | E2 | 8 | 231 |
| HPV31 | E2 | 10 | 235 |
| HPV31 | E2 | 11 | 235 |
| HPV31 | E2 | 9 | 29 |
| HPV31 | E2 | 10 | 35 |
| HPV31 | E2 | 11 | 35 |
| HPV31 | E2 | 10 | 297 |
| HPV31 | E2 | 10 | 126 |
| HPV31 | E2 | 8 | 30 |
| HPV31 | E2 | 10 | 15 |
| HPV31 | E2 | 11 | 15 |
| HPV31 | E2 | 8 | 304 |
| HPV31 | E2 | 11 | 304 |
| HPV31 | E2 | 11 | 275 |
| HPV31 | E2 | 9 | 205 |
| HPV31 | E2 | 8 | 45 |
| HPV31 | E2 | 9 | 306 |
| HPV31 | E2 | 10 | 306 |
| HPV31 | E2 | 11 | 306 |
| HPV31 | E2 | 8 | 299 |
| HPV31 | E2 | 11 | 299 |
| HPV31 | E2 | 10 | 155 |
| HPV31 | E2 | 11 | 14 |
| HPV31 | E2 | 9 | 336 |
| HPV31 | E2 | 9 | 26 |
| HPV31 | E2 | 10 | 26 |
| HPV31 | E2 | 8 | 230 |
| HPV31 | E2 | 9 | 230 |
| HPV31 | E2 | 11 | 42 |
| HPV31 | E2 | 11 | 8 |
| HPV31 | E2 | 8 | 312 |
| HPV31 | E2 | 11 | 4 |
| HPV31 | E2 | 9 | 103 |
| HPV31 | E2 | 10 | 103 |
| HPV31 | E2 | 11 | 103 |
| HPV31 | E2 | 9 | 342 |
| HPV31 | E2 | 8 | 49 |
| HPV31 | E2 | 10 | 78 |
| HPV31 | E2 | 11 | 78 |
| HPV31 | E2 | 11 | 77 |
| HPV31 | E2 | 8 | 337 |
| HPV31 | E2 | 9 | 153 |
| HPV31 | E2 | 9 | 21 |
| HPV31 | E2 | 8 | 170 |
| HPV31 | E2 | 9 | 170 |
| HPV31 | E2 | 8 | 303 |
| HPV31 | E2 | 9 | 303 |
| HPV31 | E2 | 9 | 218 |
| HPV31 | E2 | 10 | 254 |
| HPV31 | E2 | 9 | 127 |
| HPV31 | E2 | 8 | 219 |
| HPV31 | E2 | 9 | 361 |
| HPV31 | E2 | 10 | 9 |
| HPV31 | E2 | 11 | 9 |
| HPV31 | E2 | 9 | 60 |
| HPV31 | E2 | 8 | 290 |
| HPV31 | E2 | 10 | 290 |
| HPV31 | E2 | 10 | 360 |
| HPV31 | E2 | 8 | 106 |
| HPV31 | E2 | 10 | 106 |
| HPV3L | E2 | 8 | 12 |
| HPV31 | E2 | 11 | 120 |
| HPV31 | E2 | 11 | 317 |
| HPV31 | E2 | 8 | 151 |
| HPV31 | E2 | 9 | 151 |
| HPV31 | E2 | 11 | 151 |
| HPV31 | E2 | 10 | 57 |
| HPV31 | E2 | 8 | 238 |
| HPV31 | E2 | 10 | 238 |
| HPV31 | E2 | 9 | 350 |
| HPV31 | E2 | 8 | 25 |
| HPV31 | E2 | 10 | 25 |
| HPV31 | E2 | 11 | 25 |
| HPV31 | E2 | 8 | 37 |
| HPV31 | E2 | 9 | 37 |
| HPV31 | E2 | 11 | 37 |
| HPV31 | E2 | 8 | 7 |
| HPV31 | E2 | 9 | 311 |
| HPV31 | E2 | 8 | 253 |
| HPV31 | E2 | 11 | 253 |
| HPV31 | E2 | 10 | 247 |
| HPV31 | E2 | 11 | 247 |
| HPV31 | E2 | 10 | 276 |
| HPV31 | E2 | 10 | 288 |
| HPV31 | E2 | 8 | 206 |
| HPV31 | E2 | 11 | 242 |
| HPV31 | E2 | 11 | 324 |
| HPV31 | E2 | 11 | 216 |
| HPV31 | E2 | 8 | 104 |
| HPV31 | E2 | 9 | 104 |
| HPV31 | E2 | 10 | 104 |
| HPV31 | E2 | 11 | 227 |
| HPV31 | E2 | 8 | 329 |
| HPV31 | E2 | 9 | 107 |
| HPV31 | E2 | 8 | 180 |
| HPV31 | E2 | 8 | 81 |
| HPV31 | E2 | 10 | 341 |
| HPV31 | E2 | 8 | 128 |
| HPV31 | E2 | 11 | 128 |

TABLE XVII-continued

HLA-AI1 Motif Peptides

| 1 | 2 | 3 | 4 |
|---|---|---|---|
| HPV31 | E2 | 10 | 93 |
| HPV31 | E2 | 8 | 292 |
| HPV31 | E2 | 8 | 240 |
| HPV31 | E2 | 11 | 116 |
| HPV31 | E2 | 8 | 362 |
| HPV31 | E2 | 10 | 146 |
| HPV31 | E2 | 9 | 10 |
| HPV31 | E2 | 10 | 10 |
| HPV31 | E2 | 8 | 152 |
| HPV31 | E2 | 10 | 152 |
| HPV31 | E2 | 8 | 169 |
| HPV31 | E2 | 9 | 169 |
| HPV31 | E2 | 10 | 169 |
| HPV31 | E2 | 11 | 287 |
| HPV31 | E2 | 11 | 340 |
| HPV31 | E2 | 9 | 147 |
| HPV31 | E2 | 9 | 58 |
| HPV31 | E2 | 11 | 58 |
| HPV31 | E2 | 8 | 328 |
| HPV31 | E2 | 9 | 328 |
| HPV31 | E2 | 11 | 92 |
| HPV31 | E2 | 10 | 167 |
| HPV31 | E2 | 11 | 167 |
| HPV31 | E2 | 10 | 178 |
| HPV31 | E2 | 10 | 102 |
| HPV31 | E2 | 11 | 102 |
| HPV31 | E2 | 8 | 131 |
| HPV31 | E2 | 9 | 159 |
| HPV31 | E5 | 11 | 53 |
| HPV31 | E5 | 10 | 59 |
| HPV31 | E5 | 8 | 61 |
| HPV31 | E5 | 11 | 20 |
| HPV31 | E5 | 9 | 60 |
| HPV31 | E5 | 10 | 66 |
| HPV31 | E5 | 11 | 48 |
| HPV31 | E5 | 8 | 23 |
| HPV31 | E5 | 9 | 22 |
| HPV31 | E5 | 8 | 32 |
| HPV31 | E5 | 8 | 70 |
| HPV31 | E5 | 8 | 56 |
| HPV31 | E5 | 9 | 31 |
| HPV31 | E5 | 11 | 58 |
| HPV31 | E5 | 10 | 54 |
| HPV31 | E5 | 11 | 65 |
| HPV31 | E5 | 8 | 51 |
| HPV31 | E5 | 10 | 21 |
| HPV31 | E5 | 9 | 50 |
| HPV31 | E5 | 8 | 68 |
| HPV31 | E5 | 10 | 68 |
| HPV31 | E6 | 9 | 46 |
| HPV31 | E6 | 10 | 46 |
| HPV31 | E6 | 10 | 18 |
| HPV31 | E6 | 9 | 136 |
| HPV31 | E6 | 8 | 63 |
| HPV31 | E6 | 10 | 63 |
| HPV31 | E6 | 10 | 56 |
| HPV31 | E6 | 11 | 44 |
| HPV31 | E6 | 11 | 98 |
| HPV31 | E6 | 9 | 57 |
| HPV31 | E6 | 10 | 75 |
| HPV31 | E6 | 8 | 20 |
| HPV31 | E6 | 8 | 25 |
| HPV31 | E6 | 10 | 25 |
| HPV31 | E6 | 10 | 14 |
| HPV31 | E6 | 10 | 45 |
| HPV31 | E6 | 11 | 45 |
| HPV31 | E6 | 8 | 47 |
| HPV31 | E6 | 9 | 47 |
| HPV31 | E6 | 8 | 95 |
| HPV31 | E6 | 10 | 85 |
| HPV31 | E6 | 8 | 61 |
| HPV31 | E6 | 10 | 61 |
| HPV31 | E6 | 9 | 60 |
| HPV31 | E6 | 11 | 60 |
| HPV31 | E6 | 9 | 118 |
| HPV31 | E6 | 10 | 126 |
| HPV31 | E6 | 8 | 137 |
| HPV31 | E6 | 8 | 128 |
| HPV31 | E6 | 9 | 52 |
| HPV31 | E6 | 8 | 65 |
| HPV31 | E6 | 9 | 94 |
| HPV31 | E6 | 8 | 3 |
| HPV31 | E6 | 9 | 3 |
| HPV31 | E6 | 11 | 3 |
| HPV31 | E6 | 8 | 72 |
| HPV31 | E6 | 9 | 72 |
| HPV31 | E6 | 10 | 72 |
| HPV31 | E6 | 8 | 110 |
| HPV31 | E6 | 9 | 110 |
| HPV31 | E6 | 8 | 119 |
| HPV31 | E6 | 9 | 100 |
| HPV31 | E6 | 10 | 99 |
| HPV31 | E6 | 9 | 15 |
| HPV31 | E6 | 11 | 50 |
| HPV31 | E6 | 8 | 1 |
| HPV31 | E6 | 10 | 1 |
| HPV31 | E6 | 11 | 1 |
| HPV31 | E6 | 9 | 127 |
| HPV31 | E6 | 9 | 5 |
| HPV31 | E6 | 9 | 109 |
| HPV31 | E6 | 10 | 109 |
| HPV31 | E6 | 8 | 135 |
| HPV31 | E6 | 10 | 135 |
| HPV31 | E6 | 11 | 55 |
| HPV31 | E6 | 8 | 124 |
| HPV31 | E6 | 10 | 58 |
| HPV31 | E6 | 8 | 27 |
| HPV31 | E6 | 11 | 17 |
| HPV31 | E6 | 8 | 16 |
| HPV31 | E6 | 9 | 82 |
| HPV31 | E6 | 11 | 105 |
| HPV31 | E6 | 8 | 48 |
| HPV31 | E6 | 9 | 133 |
| HPV31 | E6 | 10 | 133 |
| HPV31 | E6 | 10 | 51 |
| HPV31 | E6 | 8 | 87 |
| HPV31 | E6 | 11 | 92 |
| HPV31 | E6 | 9 | 86 |
| HPV31 | E6 | 9 | 62 |
| HPV31 | E6 | 11 | 62 |
| HPV31 | E6 | 8 | 73 |
| HPV31 | E6 | 9 | 73 |
| HPV31 | E6 | 10 | 132 |
| HPV31 | E6 | 11 | 132 |
| HPV31 | E6 | 10 | 23 |
| HPV31 | E6 | 11 | 84 |
| HPV31 | E6 | 8 | 70 |
| HPV31 | E6 | 10 | 70 |
| HPV31 | E6 | 11 | 70 |
| HPV31 | E6 | 10 | 81 |
| HPV31 | E7 | 11 | 42 |
| HPV31 | E7 | 9 | 58 |
| HPV31 | E7 | 10 | 68 |
| HPV31 | E7 | 10 | 14 |
| HPV31 | E7 | 8 | 18 |
| HPV31 | E7 | 8 | 4 |
| HPV31 | E7 | 10 | 57 |
| HPV31 | E7 | 11 | 87 |
| HPV31 | E7 | 10 | 88 |
| HPV31 | E7 | 9 | 89 |
| HPV31 | E7 | 9 | 54 |
| HPV31 | E7 | 11 | 67 |
| HPV31 | E7 | 11 | 13 |
| HPV31 | E7 | 10 | 53 |
| HPV31 | E7 | 9 | 44 |
| HPV31 | E7 | 8 | 70 |
| HPV31 | E7 | 10 | 2 |
| HPV31 | E7 | 11 | 56 |
| HPV31 | E7 | 8 | 90 |
| HPV31 | E7 | 8 | 55 |

TABLE XVII-continued

HLA-AI1 Motif Peptides

| 1 | 2 | 3 | 4 |
|---|---|---|---|
| HPV31 | E7 | 11 | 52 |
| HPV31 | L1 | 11 | 347 |
| HPV31 | L1 | 9 | 102 |
| HPV31 | L1 | 8 | 386 |
| HPV31 | L1 | 10 | 458 |
| HPV31 | L1 | 11 | 458 |
| HPV31 | L1 | 9 | 137 |
| HPV31 | L1 | 11 | 37 |
| HPV31 | L1 | 8 | 473 |
| HPV31 | L1 | 10 | 473 |
| HPV31 | L1 | 10 | 348 |
| HPV31 | L1 | 11 | 426 |
| HPV31 | L1 | 11 | 208 |
| HPV31 | L1 | 8 | 350 |
| HPV31 | L1 | 8 | 491 |
| HPV31 | L1 | 9 | 491 |
| HPV31 | L1 | 10 | 491 |
| HPV31 | L1 | 11 | 491 |
| HPV31 | L1 | 8 | 285 |
| HPV31 | L1 | 10 | 226 |
| HPV31 | L1 | 8 | 103 |
| HPV31 | L1 | 9 | 304 |
| HPV31 | L1 | 8 | 185 |
| HPV31 | L1 | 8 | 128 |
| HPV31 | L1 | 9 | 128 |
| HPV31 | L1 | 9 | 210 |
| HPV31 | L1 | 8 | 224 |
| HPV31 | L1 | 9 | 224 |
| HPV31 | L1 | 9 | 459 |
| HPV31 | L1 | 10 | 459 |
| HPV31 | L1 | 10 | 372 |
| HPV31 | L1 | 10 | 56 |
| HPV31 | L1 | 10 | 143 |
| HPV31 | L1 | 11 | 143 |
| HPV31 | L1 | 8 | 129 |
| HPV31 | L1 | 8 | 245 |
| HPV31 | L1 | 9 | 245 |
| HPV31 | L1 | 11 | 88 |
| HPV31 | L1 | 10 | 353 |
| HPV31 | L1 | 8 | 146 |
| HPV31 | L1 | 8 | 270 |
| HPV31 | L1 | 10 | 270 |
| HPV31 | L1 | 9 | 127 |
| HPV31 | L1 | 10 | 127 |
| HPV31 | L1 | 11 | 371 |
| HPV31 | L1 | 9 | 84 |
| HPV31 | L1 | 8 | 469 |
| HPV31 | L1 | 10 | 469 |
| HPV31 | L1 | 9 | 308 |
| HPV31 | L1 | 8 | 211 |
| HPV31 | L1 | 8 | 257 |
| HPV31 | L1 | 11 | 421 |
| HPV31 | L1 | 9 | 331 |
| HPV31 | L1 | 9 | 161 |
| HPV31 | L1 | 9 | 184 |
| HPV31 | L1 | 9 | 244 |
| HPV31 | L1 | 10 | 244 |
| HPV31 | L1 | 8 | 85 |
| HPV31 | L1 | 8 | 138 |
| HPV31 | L1 | 10 | 117 |
| HPV31 | L1 | 8 | 68 |
| HPV31 | L1 | 10 | 68 |
| HPV31 | L1 | 10 | 38 |
| HPV31 | L1 | 8 | 413 |
| HPV31 | L1 | 11 | 282 |
| HPV31 | L1 | 9 | 349 |
| HPV31 | L1 | 9 | 229 |
| HPV31 | L1 | 8 | 225 |
| HPV31 | L1 | 11 | 225 |
| HPV31 | L1 | 10 | 307 |
| HPV31 | L1 | 9 | 118 |
| HPV31 | L1 | 10 | 427 |
| HPV31 | L1 | 10 | 382 |
| HPV31 | L1 | 11 | 61 |
| HPV31 | L1 | 11 | 443 |
| HPV31 | L1 | 10 | 126 |
| HPV31 | L1 | 11 | 126 |
| HPV31 | L1 | 10 | 83 |
| HPV31 | L1 | 8 | 468 |
| HPV31 | L1 | 9 | 468 |
| HPV31 | L1 | 11 | 468 |
| HPV31 | L1 | 11 | 381 |
| HPV31 | L1 | 8 | 357 |
| HPV31 | L1 | 10 | 357 |
| HPV31 | L1 | 11 | 357 |
| HPV31 | L1 | 8 | 431 |
| HPV31 | L1 | 8 | 65 |
| HPV31 | L1 | 11 | 65 |
| HPV31 | L1 | 8 | 20 |
| HPV31 | L1 | 11 | 20 |
| HPV31 | L1 | 9 | 223 |
| HPV31 | L1 | 10 | 223 |
| HPV31 | L1 | 8 | 460 |
| HPV31 | L1 | 9 | 460 |
| HPV31 | L1 | 10 | 330 |
| HPV31 | L1 | 10 | 160 |
| HPV31 | L1 | 11 | 465 |
| HPV31 | L1 | 8 | 114 |
| HPV31 | L1 | 11 | 159 |
| HPV31 | L1 | 9 | 470 |
| HPV31 | L1 | 11 | 470 |
| HPV31 | L1 | 8 | 42 |
| HPV31 | L1 | 9 | 42 |
| HPV31 | L1 | 8 | 384 |
| HPV31 | L1 | 10 | 384 |
| HPV31 | L1 | 8 | 43 |
| HPV31 | L1 | 10 | 209 |
| HPV31 | L1 | 9 | 256 |
| HPV31 | L1 | 11 | 300 |
| HPV31 | L1 | 8 | 360 |
| HPV31 | L1 | 10 | 32 |
| HPV31 | L1 | 9 | 227 |
| HPV31 | L1 | 11 | 227 |
| HPV31 | L1 | 8 | 496 |
| HPV31 | L1 | 9 | 496 |
| HPV31 | L1 | 11 | 233 |
| HPV31 | L1 | 10 | 183 |
| HPV31 | L1 | 8 | 165 |
| HPV31 | L1 | 10 | 222 |
| HPV31 | L1 | 11 | 222 |
| HPV31 | L1 | 9 | 113 |
| HPV31 | L1 | 10 | 489 |
| HPV31 | L1 | 11 | 489 |
| HPV31 | L1 | 9 | 411 |
| HPV31 | L1 | 10 | 411 |
| HPV31 | L1 | 11 | 17 |
| HPV31 | L1 | 9 | 472 |
| HPV31 | L1 | 11 | 472 |
| HPV31 | L1 | 8 | 374 |
| HPV31 | L1 | 11 | 306 |
| HPV31 | L1 | 8 | 156 |
| HPV31 | L1 | 11 | 329 |
| HPV31 | L1 | 10 | 255 |
| HPV31 | L1 | 10 | 154 |
| HPV31 | L1 | 10 | 476 |
| HPV31 | L1 | 11 | 476 |
| HPV31 | L1 | 9 | 41 |
| HPV31 | L1 | 10 | 41 |
| HPV31 | L1 | 9 | 75 |
| HPV31 | L1 | 9 | 385 |
| HPV31 | L1 | 11 | 457 |
| HPV31 | L1 | 9 | 39 |
| HPV31 | L1 | 11 | 39 |
| HPV31 | L1 | 9 | 490 |
| HPV31 | L1 | 10 | 490 |
| HPV31 | L1 | 11 | 490 |
| HPV31 | L1 | 8 | 303 |
| HPV31 | L1 | 10 | 303 |
| HPV31 | L1 | 11 | 55 |
| HPV31 | L1 | 11 | 352 |

TABLE XVII-continued

HLA-AI1 Motif Peptides

| 1 | 2 | 3 | 4 |
|---|---|---|---|
| HPV31 | L1 | 9 | 90 |
| HPV31 | L1 | 8 | 119 |
| HPV31 | L1 | 9 | 67 |
| HPV31 | L1 | 11 | 67 |
| HPV31 | L1 | 8 | 412 |
| HPV31 | L1 | 9 | 412 |
| HPV31 | L1 | 8 | 228 |
| HPV31 | L1 | 10 | 228 |
| HPV31 | L1 | 9 | 51 |
| HPV31 | L1 | 10 | 51 |
| HPV31 | L1 | 11 | 2 |
| HPV31 | L1 | 8 | 359 |
| HPV31 | L1 | 9 | 359 |
| HPV31 | L1 | 9 | 358 |
| HPV31 | L1 | 10 | 358 |
| HPV31 | L1 | 10 | 283 |
| HPV31 | L1 | 8 | 23 |
| HPV31 | L1 | 8 | 492 |
| HPV31 | L1 | 9 | 492 |
| HPV31 | L1 | 10 | 492 |
| HPV31 | L1 | 9 | 271 |
| HPV31 | L1 | 9 | 284 |
| HPV31 | L1 | 9 | 428 |
| HPV31 | L1 | 11 | 428 |
| HPV31 | L1 | 11 | 24 |
| HPV31 | L1 | 11 | 142 |
| HPV31 | L1 | 8 | 355 |
| HPV31 | L1 | 10 | 355 |
| HPV31 | L1 | 8 | 246 |
| HPV31 | L1 | 9 | 383 |
| HPV31 | L1 | 11 | 383 |
| HPV31 | L1 | 11 | 31 |
| HPV31 | L1 | 9 | 302 |
| HPV31 | L1 | 11 | 302 |
| HPV31 | L1 | 10 | 89 |
| HPV31 | L1 | 9 | 423 |
| HPV31 | L1 | 9 | 354 |
| HPV31 | L1 | 11 | 354 |
| HPV31 | L1 | 8 | 494 |
| HPV31 | L1 | 10 | 494 |
| HPV31 | L1 | 11 | 494 |
| HPV31 | L1 | 8 | 493 |
| HPV31 | L1 | 9 | 493 |
| HPV31 | L1 | 11 | 493 |
| HPV31 | L1 | 11 | 267 |
| HPV31 | L1 | 11 | 44 |
| HPV31 | L1 | 11 | 10 |
| HPV31 | L1 | 11 | 73 |
| HPV31 | L1 | 8 | 446 |
| HPV31 | L1 | 10 | 446 |
| HPV31 | L1 | 10 | 268 |
| HPV31 | L1 | 10 | 45 |
| HPV31 | L1 | 11 | 116 |
| HPV31 | L1 | 10 | 66 |
| HPV31 | L1 | 10 | 18 |
| HPV31 | L1 | 9 | 22 |
| HPV31 | L1 | 8 | 28 |
| HPV31 | L1 | 9 | 28 |
| HPV31 | L1 | 10 | 301 |
| HPV31 | L1 | 10 | 422 |
| HPV31 | L1 | 8 | 332 |
| HPV31 | L1 | 10 | 62 |
| HPV31 | L1 | 11 | 62 |
| HPV31 | L1 | 10 | 21 |
| HPV31 | L1 | 10 | 101 |
| HPV31 | L1 | 8 | 313 |
| HPV31 | L1 | 10 | 136 |
| HPV31 | L1 | 8 | 243 |
| HPV31 | L1 | 10 | 243 |
| HPV31 | L1 | 11 | 243 |
| HPV31 | L1 | 9 | 235 |
| HPV31 | L1 | 9 | 12 |
| HPV31 | L1 | 10 | 250 |
| HPV31 | L1 | 11 | 250 |
| HPV31 | L1 | 10 | 50 |
| HPV31 | L1 | 11 | 50 |
| HPV31 | L1 | 9 | 445 |
| HPV31 | L1 | 11 | 445 |
| HPV31 | L1 | 8 | 27 |
| HPV31 | L1 | 9 | 27 |
| HPV31 | L1 | 10 | 27 |
| HPV31 | L2 | 11 | 25 |
| HPV31 | L2 | 11 | 143 |
| HPV31 | L2 | 10 | 281 |
| HPV31 | L2 | 11 | 281 |
| HPV31 | L2 | 10 | 286 |
| HPV31 | L2 | 11 | 286 |
| HPV31 | L2 | 11 | 13 |
| HPV31 | L2 | 8 | 311 |
| HPV31 | L2 | 9 | 311 |
| HPV31 | L2 | 10 | 311 |
| HPV31 | L2 | 11 | 311 |
| HPV31 | L2 | 9 | 15 |
| HPV31 | L2 | 11 | 376 |
| HPV31 | L2 | 9 | 275 |
| HPV31 | L2 | 10 | 275 |
| HPV31 | L2 | 10 | 360 |
| HPV31 | L2 | 8 | 438 |
| HPV31 | L2 | 9 | 438 |
| HPV31 | L2 | 8 | 435 |
| HPV31 | L2 | 11 | 435 |
| HPV31 | L2 | 10 | 116 |
| HPV31 | L2 | 8 | 31 |
| HPV31 | L2 | 8 | 146 |
| HPV31 | L2 | 10 | 259 |
| HPV31 | L2 | 10 | 253 |
| HPV31 | L2 | 8 | 276 |
| HPV31 | L2 | 9 | 276 |
| HPV31 | L2 | 11 | 237 |
| HPV31 | L2 | 10 | 404 |
| HPV31 | L2 | 9 | 361 |
| HPV31 | L2 | 8 | 433 |
| HPV31 | L2 | 10 | 433 |
| HPV31 | L2 | 8 | 118 |
| HPV31 | L2 | 8 | 314 |
| HPV31 | L2 | 9 | 310 |
| HPV31 | L2 | 10 | 310 |
| HPV31 | L2 | 11 | 310 |
| HPV31 | L2 | 9 | 437 |
| HPV31 | L2 | 10 | 437 |
| HPV31 | L2 | 10 | 436 |
| HPV31 | L2 | 11 | 436 |
| HPV31 | L2 | 11 | 59 |
| HPV31 | L2 | 11 | 221 |
| HPV31 | L2 | 9 | 300 |
| HPV31 | L2 | 9 | 61 |
| HPV31 | L2 | 10 | 63 |
| HPV31 | L2 | 10 | 26 |
| HPV31 | L2 | 8 | 65 |
| HPV31 | L2 | 11 | 213 |
| HPV31 | L2 | 10 | 38 |
| HPV31 | L2 | 11 | 38 |
| HPV31 | L2 | 8 | 41 |
| HPV31 | L2 | 11 | 280 |
| HPV31 | L2 | 10 | 233 |
| HPV31 | L2 | 11 | 403 |
| HPV31 | L2 | 9 | 432 |
| HPV31 | L2 | 11 | 432 |
| HPV31 | L2 | 8 | 313 |
| HPV31 | L2 | 9 | 313 |
| HPV31 | L2 | 10 | 60 |
| HPV31 | L2 | 10 | 144 |
| HPV31 | L2 | 11 | 205 |
| HPV31 | L2 | 8 | 245 |
| HPV31 | L2 | 8 | 277 |
| HPV31 | L2 | 9 | 145 |
| HPV31 | L2 | 8 | 299 |
| HPV31 | L2 | 10 | 299 |
| HPV31 | L2 | 9 | 244 |
| HPV31 | L2 | 11 | 176 |

TABLE XVII-continued

HLA-AI1 Motif Peptides

| 1 | 2 | 3 | 4 |
|---|---|---|---|
| HPV31 | L2 | 10 | 177 |
| HPV31 | L2 | 9 | 348 |
| HPV31 | L2 | 10 | 238 |
| HPV31 | L2 | 9 | 178 |
| HPV31 | L2 | 11 | 178 |
| HPV31 | L2 | 9 | 287 |
| HPV31 | L2 | 10 | 287 |
| HPV31 | L2 | 8 | 447 |
| HPV31 | L2 | 11 | 447 |
| HPV31 | L2 | 8 | 349 |
| HPV31 | L2 | 11 | 292 |
| HPV31 | L2 | 11 | 285 |
| HPV31 | L2 | 9 | 217 |
| HPV31 | L2 | 10 | 274 |
| HPV31 | L2 | 11 | 274 |
| HPV31 | L2 | 8 | 212 |
| HPV31 | L2 | 10 | 210 |
| HPV31 | L2 | 10 | 29 |
| HPV31 | L2 | 8 | 443 |
| HPV31 | L2 | 9 | 443 |
| HPV31 | L2 | 10 | 443 |
| HPV31 | L2 | 11 | 443 |
| HPV31 | L2 | 8 | 235 |
| HPV31 | L2 | 9 | 167 |
| HPV31 | L2 | 10 | 243 |
| HPV31 | L2 | 9 | 378 |
| HPV31 | L2 | 8 | 12 |
| HPV31 | L2 | 9 | 298 |
| HPV31 | L2 | 11 | 298 |
| HPV31 | L2 | 8 | 291 |
| HPV31 | L2 | 9 | 308 |
| HPV31 | L2 | 11 | 308 |
| HPV31 | L2 | 8 | 2 |
| HPV31 | L2 | 10 | 2 |
| HPV31 | L2 | 11 | 2 |
| HPV31 | L2 | 8 | 5 |
| HPV31 | L2 | 10 | 69 |
| HPV31 | L2 | 11 | 9 |
| HPV31 | L2 | 11 | 306 |
| HPV31 | L2 | 9 | 239 |
| HPV31 | L2 | 10 | 14 |
| HPV31 | L2 | 9 | 30 |
| HPV31 | L2 | 8 | 309 |
| HPV31 | L2 | 10 | 309 |
| HPV31 | L2 | 11 | 309 |
| HPV31 | L2 | 9 | 405 |
| HPV31 | L2 | 8 | 62 |
| HPV31 | L2 | 11 | 62 |
| HPV31 | L2 | 9 | 64 |
| HPV31 | L2 | 10 | 431 |
| HPV31 | L2 | 9 | 260 |
| HPV31 | L2 | 8 | 181 |
| HPV31 | L2 | 9 | 180 |
| HPV31 | L2 | 8 | 179 |
| HPV31 | L2 | 10 | 179 |
| HPV31 | L2 | 9 | 207 |
| HPV31 | L2 | 10 | 207 |
| HPV31 | L2 | 8 | 346 |
| HPV31 | L2 | 11 | 346 |
| HPV31 | L2 | 8 | 208 |
| HPV31 | L2 | 9 | 208 |
| HPV31 | L2 | 8 | 379 |
| HPV31 | L2 | 11 | 80 |
| HPV31 | L2 | 9 | 27 |
| HPV31 | L2 | 11 | 359 |
| HPV31 | L2 | 9 | 70 |
| HPV31 | L2 | 8 | 40 |
| HPV31 | L2 | 9 | 40 |
| HPV31 | L2 | 8 | 312 |
| HPV31 | L2 | 9 | 312 |
| HPV31 | L2 | 10 | 312 |
| HPV31 | L2 | 10 | 347 |
| HPV31 | L2 | 8 | 288 |
| HPV31 | L2 | 9 | 288 |
| HPV31 | L2 | 11 | 288 |
| HPV31 | L2 | 10 | 206 |
| HPV31 | L2 | 11 | 206 |
| HPV31 | L2 | 9 | 345 |
| HPV31 | L2 | 9 | 39 |
| HPV31 | L2 | 10 | 39 |
| HPV31 | L2 | 10 | 344 |
| HPV31 | L2 | 11 | 343 |
| HPV31 | L2 | 8 | 362 |
| HPV31 | L2 | 9 | 254 |
| HPV31 | L2 | 10 | 293 |
| HPV31 | L2 | 10 | 81 |
| HPV31 | L2 | 9 | 434 |
| HPV31 | L2 | 11 | 115 |
| HPV31 | L2 | 9 | 117 |
| HPV31 | L2 | 11 | 232 |
| HPV31 | L2 | 8 | 255 |
| HPV31 | L2 | 9 | 82 |
| HPV31 | L2 | 11 | 430 |
| HPV31 | L2 | 10 | 440 |
| HPV31 | L2 | 11 | 440 |
| HPV31 | L2 | 8 | 446 |
| HPV31 | L2 | 9 | 446 |
| HPV31 | L2 | 9 | 223 |
| HPV31 | L2 | 11 | 296 |
| HPV33 | E1 | 8 | 96 |
| HPV33 | E1 | 11 | 383 |
| HPV33 | E1 | 11 | 104 |
| HPV33 | E1 | 11 | 452 |
| HPV33 | E1 | 8 | 448 |
| HPV33 | E1 | 11 | 448 |
| HPV33 | E1 | 10 | 384 |
| HPV33 | E1 | 9 | 635 |
| HPV33 | E1 | 9 | 563 |
| HPV33 | E1 | 11 | 563 |
| HPV33 | E1 | 8 | 596 |
| HPV33 | E1 | 8 | 198 |
| HPV33 | E1 | 11 | 198 |
| HPV33 | E1 | 10 | 105 |
| HPV33 | E1 | 8 | 81 |
| HPV33 | E1 | 8 | 398 |
| HPV33 | E1 | 9 | 398 |
| HPV33 | E1 | 10 | 398 |
| HPV33 | E1 | 8 | 469 |
| HPV33 | E1 | 10 | 469 |
| HPV33 | E1 | 8 | 297 |
| HPV33 | E1 | 10 | 297 |
| HPV33 | E1 | 8 | 633 |
| HPV33 | E1 | 11 | 633 |
| HPV33 | E1 | 10 | 276 |
| HPV33 | E1 | 9 | 226 |
| HPV33 | E1 | 9 | 490 |
| HPV33 | E1 | 11 | 490 |
| HPV33 | E1 | 8 | 397 |
| HPV33 | E1 | 9 | 397 |
| HPV33 | E1 | 10 | 397 |
| HPV33 | E1 | 11 | 397 |
| HPV33 | E1 | 10 | 77 |
| HPV33 | E1 | 11 | 77 |
| HPV33 | E1 | 8 | 364 |
| HPV33 | E1 | 9 | 364 |
| HPV33 | E1 | 10 | 515 |
| HPV33 | E1 | 10 | 534 |
| HPV33 | E1 | 11 | 534 |
| HPV33 | E1 | 8 | 614 |
| HPV33 | E1 | 11 | 614 |
| HPV33 | E1 | 9 | 78 |
| HPV33 | E1 | 10 | 78 |
| HPV33 | E1 | 11 | 78 |
| HPV33 | E1 | 10 | 349 |
| HPV33 | E1 | 8 | 365 |
| HPV33 | E1 | 11 | 377 |
| HPV33 | E1 | 8 | 566 |
| HPV33 | E1 | 10 | 566 |
| HPV33 | E1 | 11 | 541 |
| HPV33 | E1 | 9 | 516 |

TABLE XVII-continued

HLA-AI1 Motif Peptides

| 1 | 2 | 3 | 4 |
|---|---|---|---|
| HPV33 | E1 | 11 | 99 |
| HPV33 | E1 | 8 | 117 |
| HPV33 | E1 | 11 | 76 |
| HPV33 | E1 | 10 | 445 |
| HPV33 | E1 | 11 | 445 |
| HPV33 | E1 | 8 | 537 |
| HPV33 | E1 | 9 | 537 |
| HPV33 | E1 | 10 | 361 |
| HPV33 | E1 | 11 | 361 |
| HPV33 | E1 | 10 | 214 |
| HPV33 | E1 | 11 | 622 |
| HPV33 | E1 | 9 | 600 |
| HPV33 | E1 | 8 | 242 |
| HPV33 | E1 | 10 | 242 |
| HPV33 | E1 | 10 | 295 |
| HPV33 | E1 | 8 | 19 |
| HPV33 | E1 | 9 | 19 |
| HPV33 | E1 | 9 | 587 |
| HPV33 | E1 | 11 | 348 |
| HPV33 | E1 | 8 | 605 |
| HPV33 | E1 | 10 | 479 |
| HPV33 | E1 | 10 | 449 |
| HPV33 | E1 | 8 | 456 |
| HPV33 | E1 | 9 | 385 |
| HPV33 | E1 | 9 | 212 |
| HPV33 | E1 | 9 | 446 |
| HPV33 | E1 | 10 | 446 |
| HPV33 | E1 | 8 | 451 |
| HPV33 | E1 | 10 | 489 |
| HPV33 | E1 | 8 | 625 |
| HPV33 | E1 | 9 | 265 |
| HPV33 | E1 | 11 | 265 |
| HPV33 | E1 | 8 | 399 |
| HPV33 | E1 | 9 | 399 |
| HPV33 | E1 | 9 | 209 |
| HPV33 | E1 | 11 | 235 |
| HPV33 | E1 | 9 | 480 |
| HPV33 | E1 | 9 | 535 |
| HPV33 | E1 | 10 | 535 |
| HPV33 | E1 | 11 | 535 |
| HPV33 | E1 | 11 | 430 |
| HPV33 | E1 | 8 | 564 |
| HPV33 | E1 | 10 | 564 |
| HPV33 | E1 | 9 | 327 |
| HPV33 | E1 | 11 | 500 |
| HPV33 | E1 | 9 | 624 |
| HPV33 | E1 | 9 | 256 |
| HPV33 | E1 | 10 | 573 |
| HPV33 | E1 | 11 | 192 |
| HPV33 | E1 | 9 | 468 |
| HPV33 | E1 | 11 | 468 |
| HPV33 | E1 | 11 | 514 |
| HPV33 | E1 | 9 | 125 |
| HPV33 | E1 | 9 | 333 |
| HPV33 | E1 | 8 | 415 |
| HPV33 | E1 | 11 | 415 |
| HPV33 | E1 | 8 | 266 |
| HPV33 | E1 | 10 | 266 |
| HPV33 | E1 | 9 | 267 |
| HPV33 | E1 | 8 | 268 |
| HPV33 | E1 | 11 | 268 |
| HPV33 | E1 | 9 | 200 |
| HPV33 | E1 | 8 | 400 |
| HPV33 | E1 | 11 | 400 |
| HPV33 | E1 | 9 | 112 |
| HPV33 | E1 | 10 | 112 |
| HPV33 | E1 | 11 | 112 |
| HPV33 | E1 | 9 | 492 |
| HPV33 | E1 | 8 | 210 |
| HPV33 | E1 | 11 | 210 |
| HPV33 | E1 | 8 | 538 |
| HPV33 | E1 | 11 | 187 |
| HPV33 | E1 | 10 | 236 |
| HPV33 | E1 | 9 | 520 |
| HPV33 | E1 | 11 | 520 |
| HPV33 | E1 | 10 | 394 |
| HPV33 | E1 | 11 | 394 |
| HPV33 | E1 | 9 | 197 |
| HPV33 | E1 | 9 | 632 |
| HPV33 | E1 | 8 | 396 |
| HPV33 | E1 | 9 | 396 |
| HPV33 | E1 | 10 | 396 |
| HPV33 | E1 | 11 | 396 |
| HPV33 | E1 | 8 | 455 |
| HPV33 | E1 | 9 | 455 |
| HPV33 | E1 | 11 | 488 |
| HPV33 | E1 | 10 | 124 |
| HPV33 | E1 | 11 | 393 |
| HPV33 | E1 | 10 | 612 |
| HPV33 | E1 | 10 | 304 |
| HPV33 | E1 | 11 | 412 |
| HPV33 | E1 | 8 | 114 |
| HPV33 | E1 | 9 | 114 |
| HPV33 | E1 | 10 | 114 |
| HPV33 | E1 | 11 | 114 |
| HPV33 | E1 | 8 | 278 |
| HPV33 | E1 | 10 | 603 |
| HPV33 | E1 | 10 | 387 |
| HPV33 | E1 | 9 | 425 |
| HPV33 | E1 | 10 | 245 |
| HPV33 | E1 | 11 | 533 |
| HPV33 | E1 | 9 | 613 |
| HPV33 | E1 | 9 | 450 |
| HPV33 | E1 | 10 | 467 |
| HPV33 | E1 | 10 | 615 |
| HPV33 | E1 | 8 | 247 |
| HPV33 | E1 | 10 | 247 |
| HPV33 | E1 | 8 | 271 |
| HPV33 | E1 | 10 | 271 |
| HPV33 | E1 | 9 | 270 |
| HPV33 | E1 | 11 | 270 |
| HPV33 | E1 | 10 | 269 |
| HPV33 | E1 | 8 | 79 |
| HPV33 | E1 | 9 | 79 |
| HPV33 | E1 | 10 | 79 |
| HPV33 | E1 | 9 | 350 |
| HPV33 | E1 | 9 | 362 |
| HPV33 | E1 | 10 | 362 |
| HPV33 | E1 | 11 | 362 |
| HPV33 | E1 | 9 | 215 |
| HPV33 | E1 | 10 | 401 |
| HPV33 | E1 | 11 | 402 |
| HPV33 | E1 | 11 | 466 |
| HPV33 | E1 | 10 | 413 |
| HPV33 | E1 | 8 | 481 |
| HPV33 | E1 | 9 | 298 |
| HPV33 | E1 | 10 | 562 |
| HPV33 | E1 | 8 | 80 |
| HPV33 | E1 | 9 | 80 |
| HPV33 | E1 | 11 | 598 |
| HPV33 | E1 | 10 | 199 |
| HPV33 | E1 | 11 | 57 |
| HPV33 | E1 | 9 | 379 |
| HPV33 | E1 | 8 | 389 |
| HPV33 | E1 | 8 | 195 |
| HPV33 | E1 | 9 | 195 |
| HPV33 | E1 | 11 | 195 |
| HPV33 | E1 | 9 | 560 |
| HPV33 | E1 | 9 | 189 |
| HPV33 | E1 | 8 | 471 |
| HPV33 | E1 | 8 | 107 |
| HPV33 | E1 | 10 | 107 |
| HPV33 | E1 | 10 | 586 |
| HPV33 | E1 | 10 | 519 |
| HPV33 | E1 | 8 | 434 |
| HPV33 | E1 | 8 | 238 |
| HPV33 | E1 | 11 | 593 |
| HPV33 | E1 | 8 | 60 |
| HPV33 | E1 | 10 | 326 |
| HPV33 | E1 | 10 | 94 |

TABLE XVII-continued

HLA-AI1 Motif Peptides

| 1 | 2 | 3 | 4 |
|---|---|---|---|
| HPV33 | E1 | 9 | 308 |
| HPV33 | E1 | 11 | 275 |
| HPV33 | E1 | 8 | 273 |
| HPV33 | E1 | 10 | 264 |
| HPV33 | E1 | 8 | 575 |
| HPV33 | E1 | 8 | 306 |
| HPV33 | E1 | 11 | 306 |
| HPV33 | E1 | 8 | 109 |
| HPV33 | E1 | 9 | 95 |
| HPV33 | E1 | 10 | 634 |
| HPV33 | E1 | 10 | 225 |
| HPV33 | E1 | 8 | 493 |
| HPV33 | E1 | 9 | 604 |
| HPV33 | E1 | 10 | 211 |
| HPV33 | E1 | 9 | 414 |
| HPV33 | E1 | 10 | 111 |
| HPV33 | E1 | 11 | 111 |
| HPV33 | E1 | 10 | 58 |
| HPV33 | E1 | 9 | 243 |
| HPV33 | E1 | 8 | 380 |
| HPV33 | E1 | 10 | 378 |
| HPV33 | E1 | 9 | 368 |
| HPV33 | E1 | 9 | 194 |
| HPV33 | E1 | 10 | 194 |
| HPV33 | E1 | 10 | 559 |
| HPV33 | E1 | 10 | 188 |
| HPV33 | E1 | 10 | 193 |
| HPV33 | E1 | 11 | 193 |
| HPV33 | E1 | 11 | 239 |
| HPV33 | E1 | 8 | 447 |
| HPV33 | E1 | 9 | 447 |
| HPV33 | E1 | 8 | 309 |
| HPV33 | E1 | 9 | 296 |
| HPV33 | E1 | 11 | 296 |
| HPV33 | E1 | 8 | 363 |
| HPV33 | E1 | 9 | 363 |
| HPV33 | E1 | 10 | 363 |
| HPV33 | E1 | 9 | 565 |
| HPV33 | E1 | 11 | 565 |
| HPV33 | E1 | 8 | 227 |
| HPV33 | E1 | 11 | 630 |
| HPV33 | E1 | 10 | 183 |
| HPV33 | E1 | 8 | 561 |
| HPV33 | E1 | 11 | 561 |
| HPV33 | E1 | 8 | 426 |
| HPV33 | E1 | 11 | 224 |
| HPV33 | E1 | 11 | 110 |
| HPV33 | E1 | 11 | 558 |
| HPV33 | E1 | 8 | 328 |
| HPV33 | E1 | 10 | 240 |
| HPV33 | E1 | 9 | 101 |
| HPV33 | E1 | 8 | 299 |
| HPV33 | E1 | 8 | 491 |
| HPV33 | E1 | 10 | 491 |
| HPV33 | E1 | 8 | 190 |
| HPV33 | E1 | 9 | 246 |
| HPV33 | E1 | 11 | 246 |
| HPV33 | E1 | 11 | 182 |
| HPV33 | E1 | 8 | 517 |
| HPV33 | E1 | 10 | 100 |
| HPV33 | E1 | 10 | 17 |
| HPV33 | E1 | 11 | 17 |
| HPV33 | E1 | 10 | 332 |
| HPV33 | E1 | 8 | 418 |
| HPV33 | E1 | 9 | 502 |
| HPV33 | E1 | 9 | 522 |
| HPV33 | E1 | 9 | 595 |
| HPV33 | E1 | 11 | 478 |
| HPV33 | E1 | 10 | 208 |
| HPV33 | E1 | 11 | 254 |
| HPV33 | E2 | 10 | 210 |
| HPV33 | E2 | 8 | 246 |
| HPV33 | E2 | 11 | 246 |
| HPV33 | E2 | 8 | 249 |
| HPV33 | E2 | 10 | 78 |
| HPV33 | E2 | 9 | 258 |
| HPV33 | E2 | 10 | 10 |
| HPV33 | E2 | 9 | 245 |
| HPV33 | E2 | 8 | 40 |
| HPV33 | E2 | 9 | 288 |
| HPV33 | E2 | 10 | 288 |
| HPV33 | E2 | 10 | 269 |
| HPV33 | E2 | 10 | 145 |
| HPV33 | E2 | 9 | 211 |
| HPV33 | E2 | 8 | 25 |
| HPV33 | E2 | 10 | 25 |
| HPV33 | E2 | 10 | 122 |
| HPV33 | E2 | 10 | 217 |
| HPV33 | E2 | 11 | 217 |
| HPV33 | E2 | 8 | 235 |
| HPV33 | E2 | 9 | 143 |
| HPV33 | E2 | 11 | 232 |
| HPV33 | E2 | 9 | 39 |
| HPV33 | E2 | 8 | 173 |
| HPV33 | E2 | 10 | 142 |
| HPV33 | E2 | 11 | 74 |
| HPV33 | E2 | 11 | 298 |
| HPV33 | E2 | 9 | 282 |
| HPV33 | E2 | 10 | 282 |
| HPV33 | E2 | 11 | 282 |
| HPV33 | E2 | 8 | 80 |
| HPV33 | E2 | 11 | 115 |
| HPV33 | E2 | 9 | 100 |
| HPV33 | E2 | 10 | 244 |
| HPV33 | E2 | 10 | 156 |
| HPV33 | E2 | 10 | 278 |
| HPV33 | E2 | 9 | 161 |
| HPV33 | E2 | 10 | 161 |
| HPV33 | E2 | 11 | 155 |
| HPV33 | E2 | 9 | 15 |
| HPV33 | E2 | 11 | 4 |
| HPV33 | E2 | 8 | 287 |
| HPV33 | E2 | 10 | 287 |
| HPV33 | E2 | 11 | 287 |
| HPV33 | E2 | 8 | 280 |
| HPV33 | E2 | 11 | 280 |
| HPV33 | E2 | 10 | 14 |
| HPV33 | E2 | 11 | 34 |
| HPV33 | E2 | 10 | 23 |
| HPV33 | E2 | 8 | 180 |
| HPV33 | E2 | 8 | 151 |
| HPV33 | E2 | 9 | 151 |
| HPV33 | E2 | 11 | 151 |
| HPV33 | E2 | 8 | 165 |
| HPV33 | E2 | 9 | 103 |
| HPV33 | E2 | 10 | 103 |
| HPV33 | E2 | 8 | 16 |
| HPV33 | E2 | 11 | 243 |
| HPV33 | E2 | 10 | 35 |
| HPV33 | E2 | 8 | 77 |
| HPV33 | E2 | 11 | 77 |
| HPV33 | E2 | 10 | 129 |
| HPV33 | E2 | 8 | 49 |
| HPV33 | E2 | 8 | 147 |
| HPV33 | E2 | 11 | 9 |
| HPV33 | E2 | 8 | 162 |
| HPV33 | E2 | 9 | 162 |
| HPV33 | E2 | 11 | 162 |
| HPV33 | E2 | 9 | 123 |
| HPV33 | E2 | 11 | 216 |
| HPV33 | E2 | 8 | 284 |
| HPV33 | E2 | 9 | 284 |
| HPV33 | E2 | 11 | 284 |
| HPV33 | E2 | 9 | 272 |
| HPV33 | E2 | 9 | 248 |
| HPV33 | E2 | 9 | 60 |
| HPV33 | E2 | 8 | 27 |
| HPV33 | E2 | 11 | 27 |
| HPV33 | E2 | 8 | 222 |
| HPV33 | E2 | 9 | 113 |

TABLE XVII-continued

HLA-AI1 Motif Peptides

| 1 | 2 | 3 | 4 |
|---|---|---|---|
| HPV33 | E2 | 9 | 29 |
| HPV33 | E2 | 9 | 76 |
| HPV33 | E2 | 8 | 332 |
| HPV33 | E2 | 9 | 48 |
| HPV33 | E2 | 10 | 57 |
| HPV33 | E2 | 9 | 292 |
| HPV33 | E2 | 8 | 7 |
| HPV33 | E2 | 8 | 37 |
| HPV33 | E2 | 11 | 37 |
| HPV33 | E2 | 9 | 256 |
| HPV33 | E2 | 11 | 256 |
| HPV33 | E2 | 10 | 5 |
| HPV33 | E2 | 11 | 98 |
| HPV33 | E2 | 8 | 285 |
| HPV33 | E2 | 10 | 285 |
| HPV33 | E2 | 8 | 61 |
| HPV33 | E2 | 8 | 283 |
| HPV33 | E2 | 9 | 283 |
| HPV33 | E2 | 10 | 283 |
| HPV33 | E2 | 8 | 271 |
| HPV33 | E2 | 10 | 271 |
| HPV33 | E2 | 8 | 301 |
| HPV33 | E2 | 9 | 270 |
| HPV33 | E2 | 11 | 270 |
| HPV33 | E2 | 11 | 304 |
| HPV33 | E2 | 10 | 305 |
| HPV33 | E2 | 11 | 209 |
| HPV33 | E2 | 9 | 45 |
| HPV33 | E2 | 11 | 254 |
| HPV33 | E2 | 8 | 257 |
| HPV33 | E2 | 10 | 257 |
| HPV33 | E2 | 8 | 144 |
| HPV33 | E2 | 11 | 144 |
| HPV33 | E2 | 9 | 24 |
| HPV33 | E2 | 11 | 24 |
| HPV33 | E2 | 9 | 234 |
| HPV33 | E2 | 10 | 149 |
| HPV33 | E2 | 11 | 149 |
| HPV33 | E2 | 11 | 128 |
| HPV33 | E2 | 9 | 146 |
| HPV33 | E2 | 8 | 259 |
| HPV33 | E2 | 8 | 310 |
| HPV33 | E2 | 10 | 233 |
| HPV33 | E2 | 8 | 118 |
| HPV33 | E2 | 9 | 118 |
| HPV33 | E2 | 10 | 116 |
| HPV33 | E2 | 11 | 116 |
| HPV33 | E2 | 8 | 273 |
| HPV33 | E2 | 11 | 268 |
| HPV33 | E2 | 8 | 152 |
| HPV33 | E2 | 10 | 152 |
| HPV33 | E2 | 11 | 148 |
| HPV33 | E2 | 9 | 117 |
| HPV33 | E2 | 10 | 117 |
| HPV33 | E2 | 9 | 58 |
| HPV33 | E2 | 11 | 58 |
| HPV33 | E2 | 10 | 102 |
| HPV33 | E2 | 11 | 102 |
| HPV33 | E2 | 9 | 309 |
| HPV33 | E2 | 11 | 121 |
| HPV33 | E2 | 8 | 170 |
| HPV33 | E2 | 9 | 170 |
| HPV33 | E2 | 11 | 170 |
| HPV33 | E2 | 11 | 167 |
| HPV33 | E2 | 8 | 154 |
| HPV33 | E2 | 9 | 159 |
| HPV33 | E2 | 11 | 159 |
| HPV33 | E2 | 10 | 178 |
| HPV33 | E2 | 9 | 300 |
| HPV33 | E2 | 10 | 44 |
| HPV33 | E2 | 8 | 131 |
| HPV33 | E5 | 8 | 63 |
| HPV33 | E5 | 8 | 51 |
| HPV33 | E5 | 9 | 50 |
| HPV33 | E5 | 9 | 12 |
| HPV33 | E5 | 10 | 44 |
| HPV33 | E5 | 10 | 49 |
| HPV33 | E5 | 11 | 10 |
| HPV33 | E5 | 11 | 48 |
| HPV33 | E5 | 8 | 13 |
| HPV33 | E5 | 10 | 11 |
| HPV33 | E5 | 8 | 22 |
| HPV33 | E5 | 11 | 38 |
| HPV33 | E5 | 9 | 62 |
| HPV33 | E5 | 10 | 61 |
| HPV33 | E5 | 9 | 21 |
| HPV33 | E5 | 8 | 46 |
| HPV33 | E5 | 8 | 60 |
| HPV33 | E5 | 11 | 60 |
| HPV33 | E5 | 8 | 41 |
| HPV33 | E5 | 11 | 43 |
| HPV33 | E5 | 9 | 40 |
| HPV33 | E5 | 10 | 58 |
| HPV33 | E6 | 8 | 137 |
| HPV33 | E6 | 9 | 137 |
| HPV33 | E6 | 8 | 138 |
| HPV33 | E6 | 8 | 48 |
| HPV33 | E6 | 9 | 46 |
| HPV33 | E6 | 10 | 46 |
| HPV33 | E6 | 9 | 133 |
| HPV33 | E6 | 11 | 133 |
| HPV33 | E6 | 8 | 136 |
| HPV33 | E6 | 9 | 136 |
| HPV33 | E6 | 10 | 136 |
| HPV33 | E6 | 11 | 66 |
| HPV33 | E6 | 10 | 30 |
| HPV33 | E6 | 11 | 44 |
| HPV33 | E6 | 11 | 14 |
| HPV33 | E6 | 10 | 4 |
| HPV33 | E6 | 8 | 32 |
| HPV33 | E6 | 9 | 56 |
| HPV33 | E6 | 11 | 98 |
| HPV33 | E6 | 8 | 27 |
| HPV33 | E6 | 9 | 27 |
| HPV33 | E6 | 8 | 47 |
| HPV33 | E6 | 9 | 47 |
| HPV33 | E6 | 10 | 45 |
| HPV33 | E6 | 11 | 45 |
| HPV33 | E6 | 9 | 60 |
| HPV33 | E6 | 8 | 69 |
| HPV33 | E6 | 9 | 69 |
| HPV33 | E6 | 10 | 69 |
| HPV33 | E6 | 11 | 69 |
| HPV33 | E6 | 8 | 51 |
| HPV33 | E6 | 8 | 57 |
| HPV33 | E6 | 9 | 85 |
| HPV33 | E6 | 10 | 85 |
| HPV33 | E6 | 11 | 24 |
| HPV33 | E6 | 10 | 126 |
| HPV33 | E6 | 9 | 118 |
| HPV33 | E6 | 11 | 62 |
| HPV33 | E6 | 11 | 105 |
| HPV33 | E6 | 10 | 99 |
| HPV33 | E6 | 9 | 73 |
| HPV33 | E6 | 8 | 128 |
| HPV33 | E6 | 8 | 72 |
| HPV33 | E6 | 10 | 72 |
| HPV33 | E6 | 9 | 64 |
| HPV33 | E6 | 8 | 65 |
| HPV33 | E6 | 8 | 110 |
| HPV33 | E6 | 9 | 110 |
| HPV33 | E6 | 10 | 15 |
| HPV33 | E6 | 9 | 100 |
| HPV33 | E6 | 11 | 121 |
| HPV33 | E6 | 8 | 70 |
| HPV33 | E6 | 9 | 70 |
| HPV33 | E6 | 10 | 70 |
| HPV33 | E6 | 8 | 1 |
| HPV33 | E6 | 10 | 1 |
| HPV33 | E6 | 10 | 25 |

TABLE XVII-continued

HLA-AI1 Motif Peptides

| 1 | 2 | 3 | 4 |
|---|---|---|---|
| HPV33 | E6 | 11 | 25 |
| HPV33 | E6 | 9 | 127 |
| HPV33 | E6 | 8 | 86 |
| HPV33 | E6 | 9 | 86 |
| HPV33 | E6 | 10 | 59 |
| HPV33 | E6 | 8 | 109 |
| HPV33 | E6 | 9 | 109 |
| HPV33 | E6 | 10 | 109 |
| HPV33 | E6 | 8 | 95 |
| HPV33 | E6 | 8 | 36 |
| HPV33 | E6 | 8 | 17 |
| HPV33 | E6 | 11 | 29 |
| HPV33 | E6 | 8 | 3 |
| HPV33 | E6 | 11 | 3 |
| HPV33 | E6 | 9 | 135 |
| HPV33 | E6 | 10 | 135 |
| HPV33 | E6 | 11 | 135 |
| HPV33 | E6 | 8 | 124 |
| HPV33 | E6 | 9 | 68 |
| HPV33 | E6 | 10 | 68 |
| HPV33 | E6 | 11 | 68 |
| HPV33 | E6 | 8 | 87 |
| HPV33 | E6 | 8 | 119 |
| HPV33 | E6 | 10 | 132 |
| HPV33 | E6 | 10 | 84 |
| HPV33 | E6 | 11 | 84 |
| HPV33 | E7 | 10 | 50 |
| HPV33 | E7 | 10 | 57 |
| HPV33 | E7 | 10 | 68 |
| HPV33 | E7 | 11 | 42 |
| HPV33 | E7 | 10 | 14 |
| HPV33 | E7 | 11 | 30 |
| HPV33 | E7 | 8 | 59 |
| HPV33 | E7 | 11 | 67 |
| HPV33 | E7 | 11 | 13 |
| HPV33 | E7 | 8 | 70 |
| HPV33 | E7 | 11 | 6 |
| HPV33 | E7 | 9 | 44 |
| HPV33 | E7 | 10 | 44 |
| HPV33 | E7 | 8 | 2 |
| HPV33 | E7 | 10 | 2 |
| HPV33 | E7 | 9 | 32 |
| HPV33 | E7 | 10 | 31 |
| HPV33 | E7 | 11 | 49 |
| HPV33 | E7 | 11 | 55 |
| HPV33 | E7 | 10 | 7 |
| HPV33 | E7 | 9 | 69 |
| HPV33 | L1 | 9 | 102 |
| HPV33 | L1 | 10 | 456 |
| HPV33 | L1 | 11 | 456 |
| HPV33 | L1 | 11 | 142 |
| HPV33 | L1 | 8 | 471 |
| HPV33 | L1 | 10 | 471 |
| HPV33 | L1 | 11 | 471 |
| HPV33 | L1 | 11 | 37 |
| HPV33 | L1 | 11 | 424 |
| HPV33 | L1 | 8 | 411 |
| HPV33 | L1 | 10 | 44 |
| HPV33 | L1 | 9 | 270 |
| HPV33 | L1 | 10 | 225 |
| HPV33 | L1 | 11 | 207 |
| HPV33 | L1 | 10 | 345 |
| HPV33 | L1 | 11 | 345 |
| HPV33 | L1 | 8 | 103 |
| HPV33 | L1 | 8 | 128 |
| HPV33 | L1 | 9 | 128 |
| HPV33 | L1 | 9 | 209 |
| HPV33 | L1 | 8 | 223 |
| HPV33 | L1 | 9 | 223 |
| HPV33 | L1 | 9 | 457 |
| HPV33 | L1 | 10 | 457 |
| HPV33 | L1 | 10 | 370 |
| HPV33 | L1 | 10 | 143 |
| HPV33 | L1 | 11 | 143 |
| HPV33 | L1 | 8 | 244 |
| HPV33 | L1 | 9 | 244 |
| HPV33 | L1 | 10 | 351 |
| HPV33 | L1 | 8 | 129 |
| HPV33 | L1 | 10 | 202 |
| HPV33 | L1 | 11 | 88 |
| HPV33 | L1 | 8 | 269 |
| HPV33 | L1 | 10 | 269 |
| HPV33 | L1 | 8 | 146 |
| HPV33 | L1 | 8 | 357 |
| HPV33 | L1 | 9 | 357 |
| HPV33 | L1 | 9 | 303 |
| HPV33 | L1 | 9 | 127 |
| HPV33 | L1 | 10 | 127 |
| HPV33 | L1 | 11 | 248 |
| HPV33 | L1 | 9 | 84 |
| HPV33 | L1 | 8 | 467 |
| HPV33 | L1 | 10 | 467 |
| HPV33 | L1 | 10 | 249 |
| HPV33 | L1 | 11 | 249 |
| HPV33 | L1 | 9 | 307 |
| HPV33 | L1 | 10 | 50 |
| HPV33 | L1 | 11 | 50 |
| HPV33 | L1 | 8 | 256 |
| HPV33 | L1 | 11 | 419 |
| HPV33 | L1 | 9 | 330 |
| HPV33 | L1 | 9 | 161 |
| HPV33 | L1 | 9 | 243 |
| HPV33 | L1 | 10 | 243 |
| HPV33 | L1 | 8 | 204 |
| HPV33 | L1 | 8 | 85 |
| HPV33 | L1 | 10 | 117 |
| HPV33 | L1 | 9 | 472 |
| HPV33 | L1 | 10 | 472 |
| HPV33 | L1 | 8 | 68 |
| HPV33 | L1 | 10 | 68 |
| HPV33 | L1 | 10 | 38 |
| HPV33 | L1 | 9 | 226 |
| HPV33 | L1 | 11 | 226 |
| HPV33 | L1 | 8 | 224 |
| HPV33 | L1 | 11 | 224 |
| HPV33 | L1 | 9 | 222 |
| HPV33 | L1 | 10 | 222 |
| HPV33 | L1 | 9 | 118 |
| HPV33 | L1 | 10 | 425 |
| HPV33 | L1 | 8 | 474 |
| HPV33 | L1 | 10 | 126 |
| HPV33 | L1 | 11 | 126 |
| HPV33 | L1 | 10 | 83 |
| HPV33 | L1 | 9 | 466 |
| HPV33 | L1 | 11 | 466 |
| HPV33 | L1 | 11 | 478 |
| HPV33 | L1 | 8 | 355 |
| HPV33 | L1 | 10 | 355 |
| HPV33 | L1 | 11 | 355 |
| HPV33 | L1 | 8 | 53 |
| HPV33 | L1 | 8 | 429 |
| HPV33 | L1 | 8 | 65 |
| HPV33 | L1 | 11 | 65 |
| HPV33 | L1 | 11 | 379 |
| HPV33 | L1 | 8 | 20 |
| HPV33 | L1 | 11 | 20 |
| HPV33 | L1 | 11 | 43 |
| HPV33 | L1 | 11 | 344 |
| HPV33 | L1 | 8 | 458 |
| HPV33 | L1 | 9 | 458 |
| HPV33 | L1 | 10 | 306 |
| HPV33 | L1 | 10 | 160 |
| HPV33 | L1 | 10 | 267 |
| HPV33 | L1 | 8 | 114 |
| HPV33 | L1 | 8 | 42 |
| HPV33 | L1 | 11 | 159 |
| HPV33 | L1 | 9 | 468 |
| HPV33 | L1 | 11 | 468 |
| HPV33 | L1 | 11 | 61 |
| HPV33 | L1 | 8 | 382 |

TABLE XVII-continued

HLA-AI1 Motif Peptides

| 1 | 2 | 3 | 4 |
|---|---|---|---|
| HPV33 | L1 | 10 | 382 |
| HPV33 | L1 | 10 | 62 |
| HPV33 | L1 | 11 | 62 |
| HPV33 | L1 | 10 | 208 |
| HPV33 | L1 | 9 | 255 |
| HPV33 | L1 | 11 | 299 |
| HPV33 | L1 | 9 | 57 |
| HPV33 | L1 | 8 | 358 |
| HPV33 | L1 | 11 | 232 |
| HPV33 | L1 | 9 | 137 |
| HPV33 | L1 | 10 | 221 |
| HPV33 | L1 | 11 | 221 |
| HPV33 | L1 | 9 | 113 |
| HPV33 | L1 | 9 | 409 |
| HPV33 | L1 | 10 | 409 |
| HPV33 | L1 | 8 | 165 |
| HPV33 | L1 | 11 | 55 |
| HPV33 | L1 | 10 | 484 |
| HPV33 | L1 | 11 | 484 |
| HPV33 | L1 | 11 | 17 |
| HPV33 | L1 | 9 | 470 |
| HPV33 | L1 | 11 | 470 |
| HPV33 | L1 | 8 | 372 |
| HPV33 | L1 | 8 | 156 |
| HPV33 | L1 | 11 | 305 |
| HPV33 | L1 | 10 | 254 |
| HPV33 | L1 | 10 | 154 |
| HPV33 | L1 | 11 | 328 |
| HPV33 | L1 | 8 | 347 |
| HPV33 | L1 | 9 | 347 |
| HPV33 | L1 | 8 | 481 |
| HPV33 | L1 | 9 | 41 |
| HPV33 | L1 | 8 | 488 |
| HPV33 | L1 | 9 | 488 |
| HPV33 | L1 | 11 | 488 |
| HPV33 | L1 | 9 | 75 |
| HPV33 | L1 | 11 | 455 |
| HPV33 | L1 | 8 | 491 |
| HPV33 | L1 | 9 | 491 |
| HPV33 | L1 | 8 | 410 |
| HPV33 | L1 | 9 | 410 |
| HPV33 | L1 | 11 | 350 |
| HPV33 | L1 | 9 | 90 |
| HPV33 | L1 | 8 | 119 |
| HPV33 | L1 | 9 | 67 |
| HPV33 | L1 | 11 | 67 |
| HPV33 | L1 | 9 | 51 |
| HPV33 | L1 | 10 | 51 |
| HPV33 | L1 | 10 | 32 |
| HPV33 | L1 | 8 | 245 |
| HPV33 | L1 | 9 | 490 |
| HPV33 | L1 | 10 | 490 |
| HPV33 | L1 | 9 | 39 |
| HPV33 | L1 | 11 | 39 |
| HPV33 | L1 | 8 | 227 |
| HPV33 | L1 | 10 | 227 |
| HPV33 | L1 | 8 | 23 |
| HPV33 | L1 | 8 | 486 |
| HPV33 | L1 | 9 | 486 |
| HPV33 | L1 | 10 | 486 |
| HPV33 | L1 | 11 | 486 |
| HPV33 | L1 | 9 | 352 |
| HPV33 | L1 | 11 | 352 |
| HPV33 | L1 | 11 | 2 |
| HPV33 | L1 | 9 | 383 |
| HPV33 | L1 | 9 | 228 |
| HPV33 | L1 | 9 | 426 |
| HPV33 | L1 | 11 | 426 |
| HPV33 | L1 | 11 | 24 |
| HPV33 | L1 | 8 | 444 |
| HPV33 | L1 | 10 | 444 |
| HPV33 | L1 | 9 | 203 |
| HPV33 | L1 | 11 | 266 |
| HPV33 | L1 | 9 | 381 |
| HPV33 | L1 | 11 | 381 |
| HPV33 | L1 | 10 | 56 |
| HPV33 | L1 | 9 | 301 |
| HPV33 | L1 | 11 | 301 |
| HPV33 | L1 | 10 | 89 |
| HPV33 | L1 | 11 | 31 |
| HPV33 | L1 | 9 | 421 |
| HPV33 | L1 | 8 | 489 |
| HPV33 | L1 | 10 | 489 |
| HPV33 | L1 | 11 | 489 |
| HPV33 | L1 | 9 | 485 |
| HPV33 | L1 | 10 | 485 |
| HPV33 | L1 | 11 | 485 |
| HPV33 | L1 | 11 | 10 |
| HPV33 | L1 | 11 | 201 |
| HPV33 | L1 | 11 | 73 |
| HPV33 | L1 | 10 | 329 |
| HPV33 | L1 | 9 | 45 |
| HPV33 | L1 | 11 | 116 |
| HPV33 | L1 | 10 | 66 |
| HPV33 | L1 | 10 | 18 |
| HPV33 | L1 | 8 | 28 |
| HPV33 | L1 | 9 | 28 |
| HPV33 | L1 | 9 | 22 |
| HPV33 | L1 | 10 | 380 |
| HPV33 | L1 | 8 | 348 |
| HPV33 | L1 | 10 | 300 |
| HPV33 | L1 | 10 | 420 |
| HPV33 | L1 | 8 | 331 |
| HPV33 | L1 | 10 | 21 |
| HPV33 | L1 | 10 | 101 |
| HPV33 | L1 | 8 | 312 |
| HPV33 | L1 | 11 | 369 |
| HPV33 | L1 | 11 | 49 |
| HPV33 | L1 | 10 | 242 |
| HPV33 | L1 | 11 | 242 |
| HPV33 | L1 | 8 | 362 |
| HPV33 | L1 | 9 | 234 |
| HPV33 | L1 | 9 | 12 |
| HPV33 | L1 | 9 | 443 |
| HPV33 | L1 | 11 | 443 |
| HPV33 | L1 | 8 | 27 |
| HPV33 | L1 | 9 | 27 |
| HPV33 | L1 | 10 | 27 |
| HPV33 | L2 | 9 | 81 |
| HPV33 | L2 | 8 | 367 |
| HPV33 | L2 | 9 | 438 |
| HPV33 | L2 | 8 | 241 |
| HPV33 | L2 | 8 | 82 |
| HPV33 | L2 | 10 | 291 |
| HPV33 | L2 | 10 | 286 |
| HPV33 | L2 | 11 | 286 |
| HPV33 | L2 | 11 | 12 |
| HPV33 | L2 | 9 | 308 |
| HPV33 | L2 | 9 | 14 |
| HPV33 | L2 | 9 | 280 |
| HPV33 | L2 | 10 | 280 |
| HPV33 | L2 | 8 | 439 |
| HPV33 | L2 | 8 | 436 |
| HPV33 | L2 | 11 | 436 |
| HPV33 | L2 | 10 | 327 |
| HPV33 | L2 | 9 | 371 |
| HPV33 | L2 | 11 | 371 |
| HPV33 | L2 | 11 | 369 |
| HPV33 | L2 | 11 | 364 |
| HPV33 | L2 | 8 | 263 |
| HPV33 | L2 | 11 | 36 |
| HPV33 | L2 | 10 | 149 |
| HPV33 | L2 | 11 | 260 |
| HPV33 | L2 | 8 | 447 |
| HPV33 | L2 | 9 | 447 |
| HPV33 | L2 | 8 | 281 |
| HPV33 | L2 | 9 | 281 |
| HPV33 | L2 | 11 | 242 |
| HPV33 | L2 | 11 | 301 |
| HPV33 | L2 | 11 | 183 |

TABLE XVII-continued

HLA-AI1 Motif Peptides

| 1 | 2 | 3 | 4 |
|---|---|---|---|
| HPV33 | L2 | 8 | 163 |
| HPV33 | L2 | 11 | 440 |
| HPV33 | L2 | 10 | 437 |
| HPV33 | L2 | 11 | 58 |
| HPV33 | L2 | 11 | 226 |
| HPV33 | L2 | 8 | 64 |
| HPV33 | L2 | 10 | 62 |
| HPV33 | L2 | 11 | 218 |
| HPV33 | L2 | 10 | 37 |
| HPV33 | L2 | 11 | 37 |
| HPV33 | L2 | 10 | 25 |
| HPV33 | L2 | 9 | 60 |
| HPV33 | L2 | 8 | 349 |
| HPV33 | L2 | 10 | 379 |
| HPV33 | L2 | 8 | 374 |
| HPV33 | L2 | 8 | 336 |
| HPV33 | L2 | 11 | 297 |
| HPV33 | L2 | 8 | 40 |
| HPV33 | L2 | 11 | 285 |
| HPV33 | L2 | 8 | 318 |
| HPV33 | L2 | 10 | 59 |
| HPV33 | L2 | 8 | 448 |
| HPV33 | L2 | 11 | 448 |
| HPV33 | L2 | 9 | 358 |
| HPV33 | L2 | 9 | 292 |
| HPV33 | L2 | 11 | 433 |
| HPV33 | L2 | 10 | 307 |
| HPV33 | L2 | 11 | 311 |
| HPV33 | L2 | 10 | 334 |
| HPV33 | L2 | 8 | 282 |
| HPV33 | L2 | 9 | 328 |
| HPV33 | L2 | 10 | 243 |
| HPV33 | L2 | 8 | 359 |
| HPV33 | L2 | 8 | 372 |
| HPV33 | L2 | 10 | 372 |
| HPV33 | L2 | 8 | 240 |
| HPV33 | L2 | 9 | 240 |
| HPV33 | L2 | 8 | 290 |
| HPV33 | L2 | 11 | 290 |
| HPV33 | L2 | 9 | 172 |
| HPV33 | L2 | 10 | 279 |
| HPV33 | L2 | 11 | 279 |
| HPV33 | L2 | 8 | 217 |
| HPV33 | L2 | 10 | 215 |
| HPV33 | L2 | 11 | 333 |
| HPV33 | L2 | 10 | 347 |
| HPV33 | L2 | 11 | 339 |
| HPV33 | L2 | 8 | 444 |
| HPV33 | L2 | 9 | 444 |
| HPV33 | L2 | 10 | 444 |
| HPV33 | L2 | 11 | 444 |
| HPV33 | L2 | 11 | 79 |
| HPV33 | L2 | 10 | 161 |
| HPV33 | L2 | 8 | 186 |
| HPV33 | L2 | 8 | 221 |
| HPV33 | L2 | 10 | 221 |
| HPV33 | L2 | 11 | 326 |
| HPV33 | L2 | 8 | 317 |
| HPV33 | L2 | 9 | 317 |
| HPV33 | L2 | 8 | 11 |
| HPV33 | L2 | 10 | 455 |
| HPV33 | L2 | 8 | 300 |
| HPV33 | L2 | 9 | 313 |
| HPV33 | L2 | 11 | 313 |
| HPV33 | L2 | 9 | 303 |
| HPV33 | L2 | 11 | 303 |
| HPV33 | L2 | 10 | 13 |
| HPV33 | L2 | 8 | 314 |
| HPV33 | L2 | 10 | 314 |
| HPV33 | L2 | 11 | 314 |
| HPV33 | L2 | 9 | 63 |
| HPV33 | L2 | 10 | 357 |
| HPV33 | L2 | 8 | 151 |
| HPV33 | L2 | 9 | 150 |
| HPV33 | L2 | 10 | 184 |
| HPV33 | L2 | 9 | 212 |
| HPV33 | L2 | 10 | 354 |
| HPV33 | L2 | 9 | 38 |
| HPV33 | L2 | 10 | 38 |
| HPV33 | L2 | 8 | 213 |
| HPV33 | L2 | 10 | 80 |
| HPV33 | L2 | 9 | 26 |
| HPV33 | L2 | 9 | 162 |
| HPV33 | L2 | 8 | 61 |
| HPV33 | L2 | 11 | 61 |
| HPV33 | L2 | 11 | 24 |
| HPV33 | L2 | 8 | 39 |
| HPV33 | L2 | 9 | 39 |
| HPV33 | L2 | 8 | 309 |
| HPV33 | L2 | 9 | 244 |
| HPV33 | L2 | 8 | 293 |
| HPV33 | L2 | 11 | 293 |
| HPV33 | L2 | 10 | 211 |
| HPV33 | L2 | 11 | 353 |
| HPV33 | L2 | 10 | 298 |
| HPV33 | L2 | 9 | 222 |
| HPV33 | L2 | 9 | 435 |
| HPV33 | L2 | 10 | 370 |
| HPV33 | L2 | 10 | 238 |
| HPV33 | L2 | 11 | 238 |
| HPV33 | L2 | 8 | 304 |
| HPV33 | L2 | 10 | 304 |
| HPV33 | L2 | 10 | 441 |
| HPV33 | L2 | 11 | 441 |
| HPV33 | L2 | 11 | 210 |
| HPV33 | L2 | 10 | 434 |
| HPV33 | L2 | 11 | 237 |
| HPV33 | L2 | 9 | 366 |
| HPV33 | L2 | 8 | 446 |
| HPV33 | L2 | 9 | 446 |
| HPV33 | L2 | 10 | 446 |
| HPV33 | L2 | 8 | 356 |
| HPV33 | L2 | 11 | 356 |
| HPV33 | L2 | 9 | 228 |
| HPV33 | L2 | 8 | 381 |
| HPV45 | E1 | 11 | 383 |
| HPV45 | E1 | 8 | 198 |
| HPV45 | E1 | 11 | 198 |
| HPV45 | E1 | 10 | 384 |
| HPV45 | E1 | 11 | 384 |
| HPV45 | E1 | 11 | 490 |
| HPV45 | E1 | 11 | 532 |
| HPV45 | E1 | 11 | 452 |
| HPV45 | E1 | 9 | 270 |
| HPV45 | E1 | 11 | 270 |
| HPV45 | E1 | 10 | 199 |
| HPV45 | E1 | 8 | 512 |
| HPV45 | E1 | 8 | 517 |
| HPV45 | E1 | 8 | 399 |
| HPV45 | E1 | 9 | 399 |
| HPV45 | E1 | 8 | 398 |
| HPV45 | E1 | 9 | 398 |
| HPV45 | E1 | 10 | 398 |
| HPV45 | E1 | 9 | 604 |
| HPV45 | E1 | 10 | 276 |
| HPV45 | E1 | 8 | 297 |
| HPV45 | E1 | 10 | 297 |
| HPV45 | E1 | 10 | 378 |
| HPV45 | E1 | 11 | 423 |
| HPV45 | E1 | 8 | 634 |
| HPV45 | E1 | 9 | 78 |
| HPV45 | E1 | 10 | 78 |
| HPV45 | E1 | 11 | 78 |
| HPV45 | E1 | 9 | 516 |
| HPV45 | E1 | 8 | 397 |
| HPV45 | E1 | 9 | 397 |
| HPV45 | E1 | 10 | 397 |
| HPV45 | E1 | 11 | 397 |
| HPV45 | E1 | 11 | 377 |
| HPV45 | E1 | 10 | 515 |

TABLE XVII-continued

HLA-AI1 Motif Peptides

| 1 | 2 | 3 | 4 |
|---|---|---|---|
| HPV45 | E1 | 9 | 534 |
| HPV45 | E1 | 10 | 534 |
| HPV45 | E1 | 11 | 534 |
| HPV45 | E1 | 10 | 214 |
| HPV45 | E1 | 9 | 173 |
| HPV45 | E1 | 10 | 566 |
| HPV45 | E1 | 11 | 623 |
| HPV45 | E1 | 8 | 328 |
| HPV45 | E1 | 10 | 445 |
| HPV45 | E1 | 8 | 455 |
| HPV45 | E1 | 9 | 455 |
| HPV45 | E1 | 8 | 242 |
| HPV45 | E1 | 9 | 625 |
| HPV45 | E1 | 8 | 596 |
| HPV45 | E1 | 8 | 115 |
| HPV45 | E1 | 9 | 115 |
| HPV45 | E1 | 10 | 115 |
| HPV45 | E1 | 11 | 186 |
| HPV45 | E1 | 8 | 189 |
| HPV45 | E1 | 9 | 189 |
| HPV45 | E1 | 8 | 365 |
| HPV45 | E1 | 11 | 573 |
| HPV45 | E1 | 8 | 64 |
| HPV45 | E1 | 10 | 295 |
| HPV45 | E1 | 10 | 74 |
| HPV45 | E1 | 9 | 587 |
| HPV45 | E1 | 8 | 605 |
| HPV45 | E1 | 9 | 18 |
| HPV45 | E1 | 10 | 18 |
| HPV45 | E1 | 9 | 446 |
| HPV45 | E1 | 8 | 456 |
| HPV45 | E1 | 9 | 385 |
| HPV45 | E1 | 10 | 385 |
| HPV45 | E1 | 10 | 449 |
| HPV45 | E1 | 9 | 212 |
| HPV45 | E1 | 11 | 579 |
| HPV45 | E1 | 8 | 130 |
| HPV45 | E1 | 8 | 19 |
| HPV45 | E1 | 9 | 19 |
| HPV45 | E1 | 9 | 327 |
| HPV45 | E1 | 11 | 430 |
| HPV45 | E1 | 8 | 626 |
| HPV45 | E1 | 9 | 209 |
| HPV45 | E1 | 8 | 535 |
| HPV45 | E1 | 9 | 535 |
| HPV45 | E1 | 10 | 535 |
| HPV45 | E1 | 11 | 535 |
| HPV45 | E1 | 10 | 591 |
| HPV45 | E1 | 11 | 459 |
| HPV45 | E1 | 9 | 443 |
| HPV45 | E1 | 9 | 265 |
| HPV45 | E1 | 10 | 265 |
| HPV45 | E1 | 11 | 265 |
| HPV45 | E1 | 11 | 235 |
| HPV45 | E1 | 8 | 181 |
| HPV45 | E1 | 11 | 500 |
| HPV45 | E1 | 8 | 256 |
| HPV45 | E1 | 10 | 519 |
| HPV45 | E1 | 8 | 426 |
| HPV45 | E1 | 8 | 561 |
| HPV45 | E1 | 11 | 561 |
| HPV45 | E1 | 10 | 491 |
| HPV45 | E1 | 8 | 268 |
| HPV45 | E1 | 11 | 268 |
| HPV45 | E1 | 11 | 555 |
| HPV45 | E1 | 11 | 466 |
| HPV45 | E1 | 8 | 447 |
| HPV45 | E1 | 9 | 492 |
| HPV45 | E1 | 8 | 538 |
| HPV45 | E1 | 8 | 116 |
| HPV45 | E1 | 9 | 116 |
| HPV45 | E1 | 11 | 116 |
| HPV45 | E1 | 9 | 197 |
| HPV45 | E1 | 10 | 603 |
| HPV45 | E1 | 11 | 275 |
| HPV45 | E1 | 9 | 633 |
| HPV45 | E1 | 8 | 396 |
| HPV45 | E1 | 9 | 396 |
| HPV45 | E1 | 10 | 396 |
| HPV45 | E1 | 11 | 396 |
| HPV45 | E1 | 11 | 565 |
| HPV45 | E1 | 8 | 285 |
| HPV45 | E1 | 9 | 425 |
| HPV45 | E1 | 10 | 304 |
| HPV45 | E1 | 8 | 278 |
| HPV45 | E1 | 9 | 600 |
| HPV45 | E1 | 8 | 387 |
| HPV45 | E1 | 10 | 387 |
| HPV45 | E1 | 10 | 476 |
| HPV45 | E1 | 10 | 245 |
| HPV45 | E1 | 10 | 510 |
| HPV45 | E1 | 10 | 269 |
| HPV45 | E1 | 8 | 201 |
| HPV45 | E1 | 11 | 514 |
| HPV45 | E1 | 10 | 533 |
| HPV45 | E1 | 11 | 533 |
| HPV45 | E1 | 9 | 129 |
| HPV45 | E1 | 8 | 299 |
| HPV45 | E1 | 8 | 247 |
| HPV45 | E1 | 10 | 247 |
| HPV45 | E1 | 8 | 267 |
| HPV45 | E1 | 9 | 267 |
| HPV45 | E1 | 11 | 84 |
| HPV45 | E1 | 8 | 190 |
| HPV45 | E1 | 8 | 271 |
| HPV45 | E1 | 10 | 271 |
| HPV45 | E1 | 10 | 556 |
| HPV45 | E1 | 10 | 467 |
| HPV45 | E1 | 9 | 118 |
| HPV45 | E1 | 10 | 118 |
| HPV45 | E1 | 11 | 118 |
| HPV45 | E1 | 8 | 210 |
| HPV45 | E1 | 11 | 210 |
| HPV45 | E1 | 10 | 103 |
| HPV45 | E1 | 11 | 362 |
| HPV45 | E1 | 9 | 557 |
| HPV45 | E1 | 9 | 215 |
| HPV45 | E1 | 10 | 401 |
| HPV45 | E1 | 11 | 401 |
| HPV45 | E1 | 9 | 200 |
| HPV45 | E1 | 9 | 298 |
| HPV45 | E1 | 8 | 413 |
| HPV45 | E1 | 9 | 413 |
| HPV45 | E1 | 10 | 413 |
| HPV45 | E1 | 8 | 415 |
| HPV45 | E1 | 11 | 415 |
| HPV45 | E1 | 9 | 154 |
| HPV45 | E1 | 8 | 174 |
| HPV45 | E1 | 8 | 389 |
| HPV45 | E1 | 10 | 77 |
| HPV45 | E1 | 11 | 77 |
| HPV45 | E1 | 11 | 598 |
| HPV45 | E1 | 11 | 590 |
| HPV45 | E1 | 9 | 560 |
| HPV45 | E1 | 8 | 414 |
| HPV45 | E1 | 9 | 414 |
| HPV45 | E1 | 8 | 119 |
| HPV45 | E1 | 9 | 119 |
| HPV45 | E1 | 10 | 119 |
| HPV45 | E1 | 9 | 379 |
| HPV45 | E1 | 11 | 152 |
| HPV45 | E1 | 9 | 563 |
| HPV45 | E1 | 8 | 471 |
| HPV45 | E1 | 10 | 586 |
| HPV45 | E1 | 8 | 537 |
| HPV45 | E1 | 9 | 537 |
| HPV45 | E1 | 8 | 434 |
| HPV45 | E1 | 8 | 238 |
| HPV45 | E1 | 8 | 593 |
| HPV45 | E1 | 11 | 593 |

TABLE XVII-continued

HLA-AI1 Motif Peptides

| 1 | 2 | 3 | 4 |
|---|---|---|---|
| HPV45 | E1 | 10 | 442 |
| HPV45 | E1 | 11 | 102 |
| HPV45 | E1 | 9 | 412 |
| HPV45 | E1 | 10 | 412 |
| HPV45 | E1 | 11 | 412 |
| HPV45 | E1 | 8 | 76 |
| HPV45 | E1 | 11 | 76 |
| HPV45 | E1 | 8 | 80 |
| HPV45 | E1 | 9 | 80 |
| HPV45 | E1 | 8 | 451 |
| HPV45 | E1 | 10 | 128 |
| HPV45 | E1 | 11 | 112 |
| HPV45 | E1 | 8 | 306 |
| HPV45 | E1 | 10 | 306 |
| HPV45 | E1 | 11 | 306 |
| HPV45 | E1 | 9 | 608 |
| HPV45 | E1 | 9 | 575 |
| HPV45 | E1 | 10 | 172 |
| HPV45 | E1 | 11 | 448 |
| HPV45 | E1 | 10 | 211 |
| HPV45 | E1 | 8 | 493 |
| HPV45 | E1 | 10 | 326 |
| HPV45 | E1 | 8 | 120 |
| HPV45 | E1 | 9 | 120 |
| HPV45 | E1 | 8 | 117 |
| HPV45 | E1 | 10 | 117 |
| HPV45 | E1 | 11 | 117 |
| HPV45 | E1 | 8 | 380 |
| HPV45 | E1 | 9 | 388 |
| HPV45 | E1 | 10 | 559 |
| HPV45 | E1 | 11 | 171 |
| HPV45 | E1 | 9 | 307 |
| HPV45 | E1 | 10 | 307 |
| HPV45 | E1 | 8 | 308 |
| HPV45 | E1 | 9 | 308 |
| HPV45 | E1 | 9 | 104 |
| HPV45 | E1 | 9 | 296 |
| HPV45 | E1 | 11 | 296 |
| HPV45 | E1 | 9 | 520 |
| HPV45 | E1 | 11 | 520 |
| HPV45 | E1 | 10 | 363 |
| HPV45 | E1 | 8 | 213 |
| HPV45 | E1 | 11 | 213 |
| HPV45 | E1 | 11 | 631 |
| HPV45 | E1 | 10 | 580 |
| HPV45 | E1 | 9 | 246 |
| HPV45 | E1 | 11 | 246 |
| HPV45 | E1 | 10 | 153 |
| HPV45 | E1 | 8 | 558 |
| HPV45 | E1 | 11 | 558 |
| HPV45 | E1 | 11 | 239 |
| HPV45 | E1 | 11 | 282 |
| HPV45 | E1 | 8 | 309 |
| HPV45 | E1 | 10 | 240 |
| HPV45 | E1 | 10 | 283 |
| HPV45 | E1 | 9 | 511 |
| HPV45 | E1 | 11 | 178 |
| HPV45 | E1 | 8 | 105 |
| HPV45 | E1 | 8 | 81 |
| HPV45 | E1 | 8 | 266 |
| HPV45 | E1 | 9 | 266 |
| HPV45 | E1 | 10 | 266 |
| HPV45 | E1 | 8 | 400 |
| HPV45 | E1 | 11 | 400 |
| HPV45 | E1 | 10 | 236 |
| HPV45 | E1 | 11 | 325 |
| HPV45 | E1 | 8 | 576 |
| HPV45 | E1 | 10 | 17 |
| HPV45 | E1 | 11 | 17 |
| HPV45 | E1 | 10 | 264 |
| HPV45 | E1 | 11 | 264 |
| HPV45 | E1 | 8 | 418 |
| HPV45 | E1 | 10 | 332 |
| HPV45 | E1 | 9 | 502 |
| HPV45 | E1 | 9 | 522 |
| HPV45 | E1 | 10 | 254 |
| HPV45 | E1 | 8 | 478 |
| HPV45 | E1 | 10 | 208 |
| HPV45 | E1 | 8 | 469 |
| HPV45 | E1 | 10 | 469 |
| HPV45 | E1 | 10 | 394 |
| HPV45 | E1 | 11 | 394 |
| HPV45 | E2 | 10 | 156 |
| HPV45 | E2 | 11 | 156 |
| HPV45 | E2 | 9 | 157 |
| HPV45 | E2 | 10 | 157 |
| HPV45 | E2 | 9 | 78 |
| HPV45 | E2 | 9 | 47 |
| HPV45 | E2 | 9 | 84 |
| HPV45 | E2 | 10 | 84 |
| HPV45 | E2 | 9 | 16 |
| HPV45 | E2 | 10 | 16 |
| HPV45 | E2 | 9 | 234 |
| HPV45 | E2 | 10 | 216 |
| HPV45 | E2 | 10 | 115 |
| HPV45 | E2 | 8 | 254 |
| HPV45 | E2 | 10 | 254 |
| HPV45 | E2 | 8 | 305 |
| HPV45 | E2 | 9 | 305 |
| HPV45 | E2 | 11 | 134 |
| HPV45 | E2 | 10 | 286 |
| HPV45 | E2 | 8 | 274 |
| HPV45 | E2 | 9 | 274 |
| HPV45 | E2 | 10 | 274 |
| HPV45 | E2 | 11 | 274 |
| HPV45 | E2 | 8 | 158 |
| HPV45 | E2 | 9 | 158 |
| HPV45 | E2 | 11 | 158 |
| HPV45 | E2 | 11 | 211 |
| HPV45 | E2 | 11 | 169 |
| HPV45 | E2 | 10 | 128 |
| HPV45 | E2 | 8 | 31 |
| HPV45 | E2 | 11 | 28 |
| HPV45 | E2 | 9 | 171 |
| HPV45 | E2 | 10 | 212 |
| HPV45 | E2 | 9 | 45 |
| HPV45 | E2 | 11 | 45 |
| HPV45 | E2 | 11 | 127 |
| HPV45 | E2 | 10 | 50 |
| HPV45 | E2 | 10 | 298 |
| HPV45 | E2 | 11 | 298 |
| HPV45 | E2 | 10 | 170 |
| HPV45 | E2 | 8 | 119 |
| HPV45 | E2 | 9 | 255 |
| HPV45 | E2 | 9 | 129 |
| HPV45 | E2 | 10 | 186 |
| HPV45 | E2 | 8 | 288 |
| HPV45 | E2 | 10 | 288 |
| HPV45 | E2 | 8 | 225 |
| HPV45 | E2 | 8 | 55 |
| HPV45 | E2 | 9 | 261 |
| HPV45 | E2 | 8 | 242 |
| HPV45 | E2 | 9 | 242 |
| HPV45 | E2 | 11 | 242 |
| HPV45 | E2 | 10 | 295 |
| HPV45 | E2 | 8 | 124 |
| HPV45 | E2 | 8 | 293 |
| HPV45 | E2 | 10 | 21 |
| HPV45 | E2 | 8 | 48 |
| HPV45 | E2 | 9 | 68 |
| HPV45 | E2 | 10 | 68 |
| HPV45 | E2 | 8 | 70 |
| HPV45 | E2 | 8 | 36 |
| HPV45 | E2 | 9 | 146 |
| HPV45 | E2 | 10 | 77 |
| HPV45 | E2 | 8 | 304 |
| HPV45 | E2 | 9 | 304 |
| HPV45 | E2 | 10 | 304 |
| HPV45 | E2 | 8 | 168 |
| HPV45 | E2 | 9 | 30 |

TABLE XVII-continued

HLA-AI1 Motif Peptides

| 1 | 2 | 3 | 4 |
|---|---|---|---|
| HPV45 | E2 | 8 | 297 |
| HPV45 | E2 | 11 | 297 |
| HPV45 | E2 | 9 | 118 |
| HPV45 | E2 | 8 | 86 |
| HPV45 | E2 | 11 | 20 |
| HPV45 | E2 | 8 | 300 |
| HPV45 | E2 | 9 | 300 |
| HPV45 | E2 | 10 | 300 |
| HPV45 | E2 | 10 | 331 |
| HPV45 | E2 | 8 | 154 |
| HPV45 | E2 | 9 | 232 |
| HPV45 | E2 | 11 | 232 |
| HPV45 | E2 | 11 | 121 |
| HPV45 | E2 | 9 | 273 |
| HPV45 | E2 | 10 | 273 |
| HPV45 | E2 | 11 | 273 |
| HPV45 | E2 | 9 | 22 |
| HPV45 | E2 | 11 | 49 |
| HPV45 | E2 | 10 | 272 |
| HPV45 | E2 | 11 | 272 |
| HPV45 | E2 | 11 | 14 |
| HPV45 | E2 | 11 | 10 |
| HPV45 | E2 | 8 | 256 |
| HPV45 | E2 | 11 | 336 |
| HPV45 | E2 | 10 | 83 |
| HPV45 | E2 | 11 | 83 |
| HPV45 | E2 | 10 | 135 |
| HPV45 | E2 | 11 | 135 |
| HPV45 | E2 | 8 | 46 |
| HPV45 | E2 | 10 | 46 |
| HPV45 | E2 | 8 | 69 |
| HPV45 | E2 | 9 | 69 |
| HPV45 | E2 | 8 | 301 |
| HPV45 | E2 | 9 | 301 |
| HPV45 | E2 | 11 | 301 |
| HPV45 | E2 | 9 | 187 |
| HPV45 | E2 | 11 | 33 |
| HPV45 | E2 | 9 | 357 |
| HPV45 | E2 | 9 | 109 |
| HPV45 | E2 | 10 | 109 |
| HPV45 | E2 | 9 | 332 |
| HPV45 | E2 | 9 | 289 |
| HPV45 | E2 | 9 | 292 |
| HPV45 | E2 | 8 | 67 |
| HPV45 | E2 | 10 | 67 |
| HPV45 | E2 | 11 | 67 |
| HPV45 | E2 | 11 | 271 |
| HPV45 | E2 | 10 | 356 |
| HPV45 | E2 | 10 | 112 |
| HPV45 | E2 | 8 | 114 |
| HPV45 | E2 | 11 | 114 |
| HPV45 | E2 | 8 | 253 |
| HPV45 | E2 | 9 | 253 |
| HPV45 | E2 | 11 | 253 |
| HPV45 | E2 | 8 | 18 |
| HPV45 | E2 | 8 | 177 |
| HPV45 | E2 | 9 | 177 |
| HPV45 | E2 | 9 | 35 |
| HPV45 | E2 | 8 | 218 |
| HPV45 | E2 | 11 | 222 |
| HPV45 | E2 | 11 | 82 |
| HPV45 | E2 | 9 | 244 |
| HPV45 | E2 | 10 | 4 |
| HPV45 | E2 | 10 | 63 |
| HPV45 | E2 | 11 | 43 |
| HPV45 | E2 | 8 | 309 |
| HPV45 | E2 | 9 | 309 |
| HPV45 | E2 | 8 | 13 |
| HPV45 | E2 | 10 | 15 |
| HPV45 | E2 | 11 | 15 |
| HPV45 | E2 | 11 | 215 |
| HPV45 | E2 | 9 | 287 |
| HPV45 | E2 | 11 | 287 |
| HPV45 | E2 | 8 | 302 |
| HPV45 | E2 | 10 | 302 |
| HPV45 | E2 | 11 | 302 |
| HPV45 | E2 | 8 | 188 |
| HPV45 | E2 | 8 | 275 |
| HPV45 | E2 | 9 | 275 |
| HPV45 | E2 | 10 | 275 |
| HPV45 | E2 | 11 | 321 |
| HPV45 | E2 | 8 | 276 |
| HPV45 | E2 | 9 | 276 |
| HPV45 | E2 | 10 | 322 |
| HPV45 | E2 | 8 | 235 |
| HPV45 | E2 | 8 | 358 |
| HPV45 | E2 | 11 | 155 |
| HPV45 | E2 | 9 | 51 |
| HPV45 | E2 | 8 | 233 |
| HPV45 | E2 | 10 | 233 |
| HPV45 | E2 | 8 | 333 |
| HPV45 | E2 | 8 | 277 |
| HPV45 | E2 | 8 | 290 |
| HPV45 | E2 | 11 | 290 |
| HPV45 | E2 | 8 | 172 |
| HPV45 | E2 | 10 | 122 |
| HPV45 | E2 | 9 | 213 |
| HPV45 | E2 | 10 | 337 |
| HPV45 | E2 | 11 | 285 |
| HPV45 | E2 | 8 | 214 |
| HPV45 | E2 | 8 | 159 |
| HPV45 | E2 | 10 | 159 |
| HPV45 | E2 | 9 | 338 |
| HPV45 | E2 | 9 | 64 |
| HPV45 | E2 | 11 | 64 |
| HPV45 | E2 | 8 | 138 |
| HPV45 | E2 | 10 | 152 |
| HPV45 | E2 | 10 | 108 |
| HPV45 | E2 | 11 | 108 |
| HPV45 | E2 | 11 | 185 |
| HPV45 | E2 | 9 | 166 |
| HPV45 | E2 | 10 | 166 |
| HPV45 | E2 | 10 | 145 |
| HPV45 | E2 | 9 | 317 |
| HPV45 | E2 | 10 | 175 |
| HPV45 | E2 | 11 | 175 |
| HPV45 | E2 | 8 | 137 |
| HPV45 | E2 | 9 | 137 |
| HPV45 | E6 | 10 | 63 |
| HPV45 | E6 | 9 | 64 |
| HPV45 | E6 | 11 | 64 |
| HPV45 | E6 | 11 | 31 |
| HPV45 | E6 | 9 | 48 |
| HPV45 | E6 | 10 | 48 |
| HPV45 | E6 | 9 | 37 |
| HPV45 | E6 | 9 | 141 |
| HPV45 | E6 | 11 | 141 |
| HPV45 | E6 | 8 | 142 |
| HPV45 | E6 | 10 | 142 |
| HPV45 | E6 | 11 | 142 |
| HPV45 | E6 | 8 | 59 |
| HPV45 | E6 | 9 | 59 |
| HPV45 | E6 | 9 | 68 |
| HPV45 | E6 | 9 | 138 |
| HPV45 | E6 | 10 | 32 |
| HPV45 | E6 | 9 | 58 |
| HPV45 | E6 | 10 | 58 |
| HPV45 | E6 | 8 | 5 |
| HPV45 | E6 | 9 | 5 |
| HPV45 | E6 | 10 | 70 |
| HPV45 | E6 | 11 | 70 |
| HPV45 | E6 | 8 | 27 |
| HPV45 | E6 | 10 | 27 |
| HPV45 | E6 | 10 | 77 |
| HPV45 | E6 | 8 | 97 |
| HPV45 | E6 | 11 | 97 |
| HPV45 | E6 | 8 | 43 |
| HPV45 | E6 | 10 | 47 |
| HPV45 | E6 | 11 | 47 |
| HPV45 | E6 | 9 | 4 |

TABLE XVII-continued

HLA-AI1 Motif Peptides

| 1 | 2 | 3 | 4 |
|---|---|---|---|
| HPV45 | E6 | 10 | 4 |
| HPV45 | E6 | 10 | 53 |
| HPV45 | E6 | 9 | 120 |
| HPV45 | E6 | 8 | 128 |
| HPV45 | E6 | 8 | 60 |
| HPV45 | E6 | 8 | 69 |
| HPV45 | E6 | 11 | 69 |
| HPV45 | E6 | 9 | 54 |
| HPV45 | E6 | 10 | 36 |
| HPV45 | E6 | 8 | 67 |
| HPV45 | E6 | 10 | 67 |
| HPV45 | E6 | 8 | 50 |
| HPV45 | E6 | 8 | 92 |
| HPV45 | E6 | 11 | 52 |
| HPV45 | E6 | 9 | 102 |
| HPV45 | E6 | 10 | 101 |
| HPV45 | E6 | 8 | 112 |
| HPV45 | E6 | 9 | 112 |
| HPV45 | E6 | 11 | 112 |
| HPV45 | E6 | 10 | 1 |
| HPV45 | E6 | 8 | 100 |
| HPV45 | E6 | 11 | 100 |
| HPV45 | E6 | 10 | 83 |
| HPV45 | E6 | 8 | 139 |
| HPV45 | E6 | 11 | 139 |
| HPV45 | E6 | 10 | 95 |
| HPV45 | E6 | 9 | 114 |
| HPV45 | E6 | 11 | 114 |
| HPV45 | E6 | 8 | 111 |
| HPV45 | E6 | 9 | 111 |
| HPV45 | E6 | 10 | 111 |
| HPV45 | E6 | 8 | 144 |
| HPV45 | E6 | 9 | 144 |
| HPV45 | E6 | 10 | 144 |
| HPV45 | E6 | 11 | 144 |
| HPV45 | E6 | 10 | 137 |
| HPV45 | E6 | 9 | 26 |
| HPV45 | E6 | 11 | 26 |
| HPV45 | E6 | 11 | 46 |
| HPV45 | E6 | 11 | 107 |
| HPV45 | E6 | 10 | 57 |
| HPV45 | E6 | 11 | 57 |
| HPV45 | E6 | 8 | 3 |
| HPV45 | E6 | 10 | 3 |
| HPV45 | E6 | 11 | 3 |
| HPV45 | E6 | 9 | 126 |
| HPV45 | E6 | 10 | 126 |
| HPV45 | E6 | 8 | 74 |
| HPV45 | E6 | 10 | 41 |
| HPV45 | E6 | 8 | 29 |
| HPV45 | E6 | 11 | 24 |
| HPV45 | E6 | 11 | 82 |
| HPV45 | E6 | 9 | 84 |
| HPV45 | E6 | 10 | 140 |
| HPV45 | E6 | 11 | 89 |
| HPV45 | E6 | 8 | 38 |
| HPV45 | E6 | 11 | 94 |
| HPV45 | E6 | 9 | 28 |
| HPV45 | E6 | 11 | 62 |
| HPV45 | E6 | 8 | 34 |
| HPV45 | E6 | 9 | 99 |
| HPV45 | E6 | 8 | 72 |
| HPV45 | E6 | 9 | 72 |
| HPV45 | E6 | 10 | 72 |
| HPV45 | E7 | 9 | 6 |
| HPV45 | E7 | 9 | 64 |
| HPV45 | E7 | 11 | 43 |
| HPV45 | E7 | 10 | 20 |
| HPV45 | E7 | 10 | 38 |
| HPV45 | E7 | 8 | 78 |
| HPV45 | E7 | 10 | 44 |
| HPV45 | E7 | 11 | 44 |
| HPV45 | E7 | 8 | 47 |
| HPV45 | E7 | 11 | 62 |
| HPV45 | E7 | 8 | 61 |
| HPV45 | E7 | 10 | 63 |
| HPV45 | E7 | 9 | 21 |
| HPV45 | E7 | 11 | 75 |
| HPV45 | E7 | 9 | 39 |
| HPV45 | E7 | 9 | 51 |
| HPV45 | E7 | 10 | 51 |
| HPV45 | E7 | 11 | 51 |
| HPV45 | E7 | 11 | 49 |
| HPV45 | E7 | 8 | 54 |
| HPV45 | E7 | 10 | 5 |
| HPV45 | E7 | 8 | 7 |
| HPV45 | E7 | 10 | 76 |
| HPV45 | E7 | 8 | 65 |
| HPV45 | E7 | 9 | 45 |
| HPV45 | E7 | 10 | 45 |
| HPV45 | L1 | 9 | 517 |
| HPV45 | L1 | 11 | 161 |
| HPV45 | L1 | 9 | 128 |
| HPV45 | L1 | 9 | 83 |
| HPV45 | L1 | 8 | 191 |
| HPV45 | L1 | 11 | 28 |
| HPV45 | L1 | 11 | 234 |
| HPV45 | L1 | 9 | 523 |
| HPV45 | L1 | 11 | 523 |
| HPV45 | L1 | 11 | 375 |
| HPV45 | L1 | 8 | 518 |
| HPV45 | L1 | 11 | 518 |
| HPV45 | L1 | 10 | 162 |
| HPV45 | L1 | 8 | 164 |
| HPV45 | L1 | 8 | 88 |
| HPV45 | L1 | 10 | 88 |
| HPV45 | L1 | 11 | 88 |
| HPV45 | L1 | 10 | 276 |
| HPV45 | L1 | 11 | 276 |
| HPV45 | L1 | 8 | 129 |
| HPV45 | L1 | 8 | 188 |
| HPV45 | L1 | 11 | 188 |
| HPV45 | L1 | 8 | 211 |
| HPV45 | L1 | 11 | 51 |
| HPV45 | L1 | 9 | 236 |
| HPV45 | L1 | 9 | 224 |
| HPV45 | L1 | 8 | 250 |
| HPV45 | L1 | 9 | 250 |
| HPV45 | L1 | 9 | 488 |
| HPV45 | L1 | 10 | 488 |
| HPV45 | L1 | 8 | 172 |
| HPV45 | L1 | 8 | 271 |
| HPV45 | L1 | 9 | 271 |
| HPV45 | L1 | 9 | 332 |
| HPV45 | L1 | 11 | 114 |
| HPV45 | L1 | 11 | 461 |
| HPV45 | L1 | 8 | 296 |
| HPV45 | L1 | 10 | 296 |
| HPV45 | L1 | 10 | 169 |
| HPV45 | L1 | 11 | 169 |
| HPV45 | L1 | 10 | 223 |
| HPV45 | L1 | 8 | 313 |
| HPV45 | L1 | 8 | 283 |
| HPV45 | L1 | 11 | 275 |
| HPV45 | L1 | 9 | 110 |
| HPV45 | L1 | 8 | 24 |
| HPV45 | L1 | 8 | 498 |
| HPV45 | L1 | 9 | 498 |
| HPV45 | L1 | 10 | 498 |
| HPV45 | L1 | 8 | 336 |
| HPV45 | L1 | 9 | 336 |
| HPV45 | L1 | 8 | 485 |
| HPV45 | L1 | 8 | 237 |
| HPV45 | L1 | 11 | 450 |
| HPV45 | L1 | 9 | 359 |
| HPV45 | L1 | 10 | 82 |
| HPV45 | L1 | 9 | 187 |
| HPV45 | L1 | 9 | 210 |
| HPV45 | L1 | 8 | 225 |
| HPV45 | L1 | 9 | 270 |

TABLE XVII-continued

HLA-AI1 Motif Peptides

| 1 | 2 | 3 | 4 |
|---|---|---|---|
| HPV45 | L1 | 10 | 270 |
| HPV45 | L1 | 9 | 295 |
| HPV45 | L1 | 11 | 295 |
| HPV45 | L1 | 10 | 141 |
| HPV45 | L1 | 8 | 111 |
| HPV45 | L1 | 11 | 503 |
| HPV45 | L1 | 8 | 143 |
| HPV45 | L1 | 10 | 143 |
| HPV45 | L1 | 8 | 84 |
| HPV45 | L1 | 8 | 9 |
| HPV45 | L1 | 8 | 348 |
| HPV45 | L1 | 8 | 251 |
| HPV45 | L1 | 11 | 251 |
| HPV45 | L1 | 9 | 23 |
| HPV45 | L1 | 9 | 59 |
| HPV45 | L1 | 9 | 142 |
| HPV45 | L1 | 11 | 142 |
| HPV45 | L1 | 11 | 185 |
| HPV45 | L1 | 10 | 411 |
| HPV45 | L1 | 11 | 328 |
| HPV45 | L1 | 8 | 460 |
| HPV45 | L1 | 10 | 109 |
| HPV45 | L1 | 8 | 389 |
| HPV45 | L1 | 9 | 497 |
| HPV45 | L1 | 10 | 497 |
| HPV45 | L1 | 11 | 497 |
| HPV45 | L1 | 9 | 484 |
| HPV45 | L1 | 8 | 475 |
| HPV45 | L1 | 10 | 475 |
| HPV45 | L1 | 8 | 305 |
| HPV45 | L1 | 9 | 152 |
| HPV45 | L1 | 10 | 473 |
| HPV45 | L1 | 8 | 91 |
| HPV45 | L1 | 11 | 91 |
| HPV45 | L1 | 8 | 153 |
| HPV45 | L1 | 9 | 249 |
| HPV45 | L1 | 10 | 249 |
| HPV45 | L1 | 8 | 489 |
| HPV45 | L1 | 9 | 489 |
| HPV45 | L1 | 9 | 282 |
| HPV45 | L1 | 9 | 335 |
| HPV45 | L1 | 10 | 335 |
| HPV45 | L1 | 10 | 358 |
| HPV45 | L1 | 10 | 186 |
| HPV45 | L1 | 8 | 140 |
| HPV45 | L1 | 11 | 140 |
| HPV45 | L1 | 8 | 68 |
| HPV45 | L1 | 10 | 68 |
| HPV45 | L1 | 9 | 144 |
| HPV45 | L1 | 8 | 413 |
| HPV45 | L1 | 10 | 413 |
| HPV45 | L1 | 9 | 69 |
| HPV45 | L1 | 8 | 499 |
| HPV45 | L1 | 9 | 499 |
| HPV45 | L1 | 9 | 1 |
| HPV45 | L1 | 10 | 235 |
| HPV45 | L1 | 10 | 294 |
| HPV45 | L1 | 11 | 310 |
| HPV45 | L1 | 8 | 49 |
| HPV45 | L1 | 9 | 383 |
| HPV45 | L1 | 10 | 383 |
| HPV45 | L1 | 11 | 383 |
| HPV45 | L1 | 10 | 516 |
| HPV45 | L1 | 9 | 190 |
| HPV45 | L1 | 8 | 526 |
| HPV45 | L1 | 10 | 526 |
| HPV45 | L1 | 11 | 526 |
| HPV45 | L1 | 11 | 259 |
| HPV45 | L1 | 10 | 209 |
| HPV45 | L1 | 10 | 22 |
| HPV45 | L1 | 10 | 248 |
| HPV45 | L1 | 11 | 248 |
| HPV45 | L1 | 9 | 139 |
| HPV45 | L1 | 8 | 382 |
| HPV45 | L1 | 10 | 382 |
| HPV45 | L1 | 11 | 382 |
| HPV45 | L1 | 8 | 508 |
| HPV45 | L1 | 9 | 387 |
| HPV45 | L1 | 10 | 387 |
| HPV45 | L1 | 9 | 440 |
| HPV45 | L1 | 10 | 440 |
| HPV45 | L1 | 10 | 380 |
| HPV45 | L1 | 9 | 87 |
| HPV45 | L1 | 11 | 87 |
| HPV45 | L1 | 8 | 468 |
| HPV45 | L1 | 11 | 168 |
| HPV45 | L1 | 10 | 346 |
| HPV45 | L1 | 10 | 281 |
| HPV45 | L1 | 10 | 334 |
| HPV45 | L1 | 11 | 334 |
| HPV45 | L1 | 11 | 357 |
| HPV45 | L1 | 8 | 378 |
| HPV45 | L1 | 9 | 253 |
| HPV45 | L1 | 9 | 452 |
| HPV45 | L1 | 8 | 171 |
| HPV45 | L1 | 9 | 171 |
| HPV45 | L1 | 9 | 67 |
| HPV45 | L1 | 11 | 67 |
| HPV45 | L1 | 9 | 101 |
| HPV45 | L1 | 8 | 529 |
| HPV45 | L1 | 8 | 46 |
| HPV45 | L1 | 11 | 46 |
| HPV45 | L1 | 10 | 77 |
| HPV45 | L1 | 9 | 93 |
| HPV45 | L1 | 10 | 487 |
| HPV45 | L1 | 11 | 487 |
| HPV45 | L1 | 8 | 331 |
| HPV45 | L1 | 10 | 331 |
| HPV45 | L1 | 11 | 81 |
| HPV45 | L1 | 8 | 145 |
| HPV45 | L1 | 8 | 254 |
| HPV45 | L1 | 10 | 58 |
| HPV45 | L1 | 8 | 272 |
| HPV45 | L1 | 11 | 486 |
| HPV45 | L1 | 11 | 65 |
| HPV45 | L1 | 8 | 521 |
| HPV45 | L1 | 9 | 521 |
| HPV45 | L1 | 11 | 521 |
| HPV45 | L1 | 10 | 115 |
| HPV45 | L1 | 10 | 376 |
| HPV45 | L1 | 10 | 519 |
| HPV45 | L1 | 11 | 519 |
| HPV45 | L1 | 11 | 43 |
| HPV45 | L1 | 8 | 453 |
| HPV45 | L1 | 9 | 414 |
| HPV45 | L1 | 8 | 522 |
| HPV45 | L1 | 10 | 522 |
| HPV45 | L1 | 9 | 163 |
| HPV45 | L1 | 11 | 457 |
| HPV45 | L1 | 11 | 410 |
| HPV45 | L1 | 9 | 116 |
| HPV45 | L1 | 9 | 412 |
| HPV45 | L1 | 11 | 412 |
| HPV45 | L1 | 9 | 330 |
| HPV45 | L1 | 11 | 330 |
| HPV45 | L1 | 11 | 57 |
| HPV45 | L1 | 8 | 442 |
| HPV45 | L1 | 9 | 520 |
| HPV45 | L1 | 10 | 520 |
| HPV45 | L1 | 10 | 462 |
| HPV45 | L1 | 10 | 329 |
| HPV45 | L1 | 8 | 441 |
| HPV45 | L1 | 9 | 441 |
| HPV45 | L1 | 8 | 70 |
| HPV45 | L1 | 9 | 297 |
| HPV45 | L1 | 11 | 36 |
| HPV45 | L1 | 8 | 102 |
| HPV45 | L1 | 10 | 44 |
| HPV45 | L1 | 11 | 99 |
| HPV45 | L1 | 11 | 293 |

TABLE XVII-continued

HLA-AI1 Motif Peptides

| 1 | 2 | 3 | 4 |
|---|---|---|---|
| HPV45 | L1 | 9 | 48 |
| HPV45 | L1 | 10 | 92 |
| HPV45 | L1 | 8 | 54 |
| HPV45 | L1 | 9 | 54 |
| HPV45 | L1 | 8 | 360 |
| HPV45 | L1 | 10 | 47 |
| HPV45 | L1 | 9 | 78 |
| HPV45 | L1 | 10 | 127 |
| HPV45 | L1 | 8 | 196 |
| HPV45 | L1 | 8 | 341 |
| HPV45 | L1 | 8 | 477 |
| HPV45 | L1 | 8 | 385 |
| HPV45 | L1 | 9 | 385 |
| HPV45 | L1 | 11 | 385 |
| HPV45 | L1 | 10 | 269 |
| HPV45 | L1 | 11 | 269 |
| HPV45 | L1 | 10 | 7 |
| HPV45 | L1 | 10 | 303 |
| HPV45 | L1 | 9 | 38 |
| HPV45 | L1 | 9 | 261 |
| HPV45 | L1 | 11 | 150 |
| HPV45 | L1 | 8 | 393 |
| HPV45 | L1 | 9 | 53 |
| HPV45 | L1 | 10 | 53 |
| HPV45 | L2 | 10 | 286 |
| HPV45 | L2 | 8 | 12 |
| HPV45 | L2 | 11 | 12 |
| HPV45 | L2 | 9 | 357 |
| HPV45 | L2 | 10 | 357 |
| HPV45 | L2 | 10 | 423 |
| HPV45 | L2 | 9 | 14 |
| HPV45 | L2 | 9 | 303 |
| HPV45 | L2 | 11 | 340 |
| HPV45 | L2 | 9 | 275 |
| HPV45 | L2 | 10 | 275 |
| HPV45 | L2 | 9 | 273 |
| HPV45 | L2 | 11 | 273 |
| HPV45 | L2 | 8 | 343 |
| HPV45 | L2 | 8 | 36 |
| HPV45 | L2 | 8 | 276 |
| HPV45 | L2 | 9 | 276 |
| HPV45 | L2 | 11 | 306 |
| HPV45 | L2 | 10 | 181 |
| HPV45 | L2 | 8 | 314 |
| HPV45 | L2 | 11 | 58 |
| HPV45 | L2 | 8 | 430 |
| HPV45 | L2 | 8 | 64 |
| HPV45 | L2 | 10 | 62 |
| HPV45 | L2 | 10 | 25 |
| HPV45 | L2 | 9 | 60 |
| HPV45 | L2 | 8 | 183 |
| HPV45 | L2 | 10 | 183 |
| HPV45 | L2 | 10 | 433 |
| HPV45 | L2 | 11 | 433 |
| HPV45 | L2 | 11 | 292 |
| HPV45 | L2 | 11 | 432 |
| HPV45 | L2 | 11 | 180 |
| HPV45 | L2 | 8 | 313 |
| HPV45 | L2 | 9 | 313 |
| HPV45 | L2 | 8 | 429 |
| HPV45 | L2 | 9 | 429 |
| HPV45 | L2 | 10 | 59 |
| HPV45 | L2 | 10 | 210 |
| HPV45 | L2 | 11 | 210 |
| HPV45 | L2 | 8 | 366 |
| HPV45 | L2 | 10 | 34 |
| HPV45 | L2 | 10 | 299 |
| HPV45 | L2 | 9 | 287 |
| HPV45 | L2 | 11 | 375 |
| HPV45 | L2 | 10 | 392 |
| HPV45 | L2 | 9 | 248 |
| HPV45 | L2 | 8 | 277 |
| HPV45 | L2 | 8 | 1 |
| HPV45 | L2 | 9 | 1 |
| HPV45 | L2 | 10 | 1 |
| HPV45 | L2 | 11 | 1 |
| HPV45 | L2 | 11 | 422 |
| HPV45 | L2 | 9 | 342 |
| HPV45 | L2 | 10 | 79 |
| HPV45 | L2 | 11 | 285 |
| HPV45 | L2 | 10 | 356 |
| HPV45 | L2 | 11 | 356 |
| HPV45 | L2 | 8 | 404 |
| HPV45 | L2 | 10 | 272 |
| HPV45 | L2 | 11 | 209 |
| HPV45 | L2 | 9 | 214 |
| HPV45 | L2 | 11 | 391 |
| HPV45 | L2 | 8 | 378 |
| HPV45 | L2 | 10 | 361 |
| HPV45 | L2 | 9 | 420 |
| HPV45 | L2 | 8 | 185 |
| HPV45 | L2 | 10 | 216 |
| HPV45 | L2 | 9 | 312 |
| HPV45 | L2 | 10 | 312 |
| HPV45 | L2 | 8 | 11 |
| HPV45 | L2 | 9 | 11 |
| HPV45 | L2 | 10 | 302 |
| HPV45 | L2 | 8 | 295 |
| HPV45 | L2 | 8 | 222 |
| HPV45 | L2 | 8 | 291 |
| HPV45 | L2 | 11 | 298 |
| HPV45 | L2 | 10 | 281 |
| HPV45 | L2 | 11 | 281 |
| HPV45 | L2 | 11 | 225 |
| HPV45 | L2 | 9 | 308 |
| HPV45 | L2 | 11 | 308 |
| HPV45 | L2 | 10 | 68 |
| HPV45 | L2 | 8 | 220 |
| HPV45 | L2 | 10 | 220 |
| HPV45 | L2 | 10 | 235 |
| HPV45 | L2 | 10 | 13 |
| HPV45 | L2 | 8 | 394 |
| HPV45 | L2 | 8 | 274 |
| HPV45 | L2 | 10 | 274 |
| HPV45 | L2 | 11 | 274 |
| HPV45 | L2 | 8 | 309 |
| HPV45 | L2 | 10 | 309 |
| HPV45 | L2 | 9 | 63 |
| HPV45 | L2 | 11 | 24 |
| HPV45 | L2 | 10 | 247 |
| HPV45 | L2 | 11 | 78 |
| HPV45 | L2 | 11 | 246 |
| HPV45 | L2 | 8 | 288 |
| HPV45 | L2 | 11 | 288 |
| HPV45 | L2 | 9 | 211 |
| HPV45 | L2 | 10 | 211 |
| HPV45 | L2 | 9 | 362 |
| HPV45 | L2 | 11 | 362 |
| HPV45 | L2 | 8 | 212 |
| HPV45 | L2 | 9 | 212 |
| HPV45 | L2 | 11 | 212 |
| HPV45 | L2 | 8 | 237 |
| HPV45 | L2 | 8 | 358 |
| HPV45 | L2 | 9 | 358 |
| HPV45 | L2 | 9 | 424 |
| HPV45 | L2 | 9 | 26 |
| HPV45 | L2 | 8 | 15 |
| HPV45 | L2 | 10 | 402 |
| HPV45 | L2 | 8 | 61 |
| HPV45 | L2 | 11 | 61 |
| HPV45 | L2 | 9 | 69 |
| HPV45 | L2 | 8 | 363 |
| HPV45 | L2 | 10 | 363 |
| HPV45 | L2 | 11 | 363 |
| HPV45 | L2 | 8 | 304 |
| HPV45 | L2 | 10 | 376 |
| HPV45 | L2 | 8 | 421 |
| HPV45 | L2 | 10 | 341 |
| HPV45 | L2 | 9 | 393 |
| HPV45 | L2 | 11 | 418 |

TABLE XVII-continued

HLA-AI1 Motif Peptides

| 1 | 2 | 3 | 4 |
|---|---|---|---|
| HPV45 | L2 | 8 | 359 |
| HPV45 | L2 | 8 | 425 |
| HPV45 | L2 | 11 | 426 |
| HPV45 | L2 | 10 | 293 |
| HPV45 | L2 | 9 | 217 |
| HPV45 | L2 | 11 | 217 |
| HPV45 | L2 | 9 | 80 |
| HPV45 | L2 | 9 | 182 |
| HPV45 | L2 | 11 | 182 |
| HPV45 | L2 | 8 | 2 |
| HPV45 | L2 | 9 | 2 |
| HPV45 | L2 | 10 | 2 |
| HPV45 | L2 | 9 | 236 |
| HPV45 | L2 | 8 | 249 |
| HPV45 | L2 | 8 | 81 |
| HPV45 | L2 | 8 | 444 |
| HPV45 | L2 | 11 | 444 |
| HPV45 | L2 | 9 | 428 |
| HPV45 | L2 | 10 | 428 |
| HPV45 | L2 | 8 | 437 |
| HPV45 | L2 | 11 | 437 |
| HPV45 | L2 | 9 | 227 |
| HPV45 | L2 | 11 | 401 |
| HPV56 | E2 | 9 | 177 |
| HPV56 | E2 | 10 | 177 |
| HPV56 | E2 | 10 | 21 |
| HPV56 | E2 | 8 | 178 |
| HPV56 | E2 | 9 | 178 |
| HPV56 | E2 | 11 | 178 |
| HPV56 | E2 | 8 | 249 |
| HPV56 | E2 | 9 | 249 |
| HPV56 | E2 | 10 | 249 |
| HPV56 | E2 | 8 | 52 |
| HPV56 | E2 | 8 | 4 |
| HPV56 | E2 | 8 | 71 |
| HPV56 | E2 | 9 | 71 |
| HPV56 | E2 | 11 | 71 |
| HPV56 | E2 | 10 | 92 |
| HPV56 | E2 | 11 | 92 |
| HPV56 | E2 | 10 | 176 |
| HPV56 | E2 | 11 | 176 |
| HPV56 | E2 | 8 | 113 |
| HPV56 | E2 | 10 | 65 |
| HPV56 | E2 | 8 | 215 |
| HPV56 | E2 | 9 | 195 |
| HPV56 | E2 | 8 | 140 |
| HPV56 | E2 | 9 | 140 |
| HPV56 | E2 | 8 | 213 |
| HPV56 | E2 | 10 | 213 |
| HPV56 | E2 | 8 | 117 |
| HPV56 | E2 | 9 | 193 |
| HPV56 | E2 | 11 | 193 |
| HPV56 | E2 | 8 | 43 |
| HPV56 | E2 | 9 | 43 |
| HPV56 | E2 | 8 | 191 |
| HPV56 | E2 | 11 | 191 |
| HPV56 | E2 | 10 | 199 |
| HPV56 | E2 | 8 | 23 |
| HPV56 | E2 | 10 | 288 |
| HPV56 | E2 | 9 | 154 |
| HPV56 | E2 | 10 | 154 |
| HPV56 | E2 | 10 | 128 |
| HPV56 | E2 | 8 | 61 |
| HPV56 | E2 | 11 | 64 |
| HPV56 | E2 | 8 | 194 |
| HPV56 | E2 | 10 | 194 |
| HPV56 | E2 | 10 | 121 |
| HPV56 | E2 | 11 | 294 |
| HPV56 | E2 | 8 | 261 |
| HPV56 | E2 | 9 | 261 |
| HPV56 | E2 | 9 | 122 |
| HPV56 | E2 | 9 | 231 |
| HPV56 | E2 | 11 | 231 |
| HPV56 | E2 | 9 | 99 |
| HPV56 | E2 | 10 | 99 |
| HPV56 | E2 | 9 | 173 |
| HPV56 | E2 | 10 | 173 |
| HPV56 | E2 | 9 | 66 |
| HPV56 | E2 | 8 | 94 |
| HPV56 | E2 | 9 | 94 |
| HPV56 | E2 | 11 | 94 |
| HPV56 | E2 | 8 | 201 |
| HPV56 | E2 | 10 | 201 |
| HPV56 | E2 | 8 | 104 |
| HPV56 | E2 | 10 | 59 |
| HPV56 | E2 | 11 | 210 |
| HPV56 | E2 | 8 | 239 |
| HPV56 | E2 | 10 | 239 |
| HPV56 | E2 | 8 | 130 |
| HPV56 | E2 | 8 | 297 |
| HPV56 | E2 | 9 | 297 |
| HPV56 | E2 | 11 | 20 |
| HPV56 | E2 | 9 | 283 |
| HPV56 | E2 | 10 | 224 |
| HPV56 | E2 | 10 | 211 |
| HPV56 | E2 | 11 | 281 |
| HPV56 | E2 | 9 | 248 |
| HPV56 | E2 | 10 | 248 |
| HPV56 | E2 | 11 | 248 |
| HPV56 | E2 | 9 | 51 |
| HPV56 | E2 | 8 | 203 |
| HPV56 | E2 | 11 | 120 |
| HPV56 | E2 | 8 | 241 |
| HPV56 | E2 | 11 | 241 |
| HPV56 | E2 | 11 | 68 |
| HPV56 | E2 | 10 | 276 |
| HPV56 | E2 | 11 | 276 |
| HPV56 | E2 | 11 | 258 |
| HPV56 | E2 | 9 | 233 |
| HPV56 | E2 | 8 | 90 |
| HPV56 | E2 | 9 | 90 |
| HPV56 | E2 | 9 | 260 |
| HPV56 | E2 | 10 | 260 |
| HPV56 | E2 | 10 | 295 |
| HPV56 | E2 | 11 | 295 |
| HPV56 | E2 | 9 | 46 |
| HPV56 | E2 | 10 | 46 |
| HPV56 | E2 | 9 | 1 |
| HPV56 | E2 | 11 | 1 |
| HPV56 | E2 | 9 | 70 |
| HPV56 | E2 | 10 | 70 |
| HPV56 | E2 | 8 | 83 |
| HPV56 | E2 | 10 | 69 |
| HPV56 | E2 | 11 | 69 |
| HPV56 | E2 | 8 | 31 |
| HPV56 | E2 | 8 | 226 |
| HPV56 | E2 | 9 | 225 |
| HPV56 | E2 | 8 | 292 |
| HPV56 | E2 | 11 | 149 |
| HPV56 | E2 | 9 | 3 |
| HPV56 | E2 | 9 | 139 |
| HPV56 | E2 | 10 | 139 |
| HPV56 | E2 | 10 | 230 |
| HPV56 | E2 | 8 | 183 |
| HPV56 | E2 | 8 | 244 |
| HPV56 | E2 | 9 | 244 |
| HPV56 | E2 | 10 | 244 |
| HPV56 | E2 | 8 | 152 |
| HPV56 | E2 | 11 | 152 |
| HPV56 | E2 | 11 | 236 |
| HPV56 | E2 | 10 | 301 |
| HPV56 | E2 | 8 | 175 |
| HPV56 | E2 | 11 | 175 |
| HPV56 | E2 | 10 | 98 |
| HPV56 | E2 | 11 | 98 |
| HPV56 | E2 | 8 | 246 |
| HPV56 | E2 | 11 | 246 |
| HPV56 | E2 | 11 | 188 |
| HPV56 | E2 | 9 | 291 |
| HPV56 | E2 | 8 | 222 |

TABLE XVII-continued

HLA-AI1 Motif Peptides

| 1 | 2 | 3 | 4 |
|---|---|---|---|
| HPV56 | E2 | 10 | 220 |
| HPV56 | E2 | 9 | 212 |
| HPV56 | E2 | 11 | 212 |
| HPV56 | E2 | 9 | 93 |
| HPV56 | E2 | 10 | 93 |
| HPV56 | E2 | 8 | 279 |
| HPV56 | E2 | 11 | 223 |
| HPV56 | E2 | 8 | 196 |
| HPV56 | E2 | 11 | 266 |
| HPV56 | E2 | 11 | 171 |
| HPV56 | E2 | 8 | 141 |
| HPV56 | E2 | 11 | 40 |
| HPV56 | E2 | 8 | 112 |
| HPV56 | E2 | 9 | 112 |
| HPV56 | E2 | 9 | 214 |
| HPV56 | E2 | 10 | 282 |
| HPV56 | E2 | 11 | 28 |
| HPV56 | E2 | 10 | 259 |
| HPV56 | E2 | 11 | 259 |
| HPV56 | E2 | 8 | 271 |
| HPV56 | E2 | 8 | 234 |
| HPV56 | E2 | 8 | 155 |
| HPV56 | E2 | 9 | 155 |
| HPV56 | E2 | 8 | 75 |
| HPV56 | E2 | 8 | 91 |
| HPV56 | E2 | 11 | 91 |
| HPV56 | E2 | 8 | 262 |
| HPV56 | E2 | 8 | 95 |
| HPV56 | E2 | 10 | 95 |
| HPV56 | E2 | 10 | 172 |
| HPV56 | E2 | 11 | 172 |
| HPV56 | E2 | 8 | 156 |
| HPV56 | E2 | 8 | 179 |
| HPV56 | E2 | 10 | 179 |
| HPV56 | E2 | 10 | 150 |
| HPV56 | E2 | 10 | 237 |
| HPV56 | E2 | 9 | 302 |
| HPV56 | E2 | 10 | 45 |
| HPV56 | E2 | 11 | 45 |
| HPV56 | E2 | 9 | 270 |
| HPV56 | E2 | 11 | 137 |
| HPV56 | E2 | 9 | 82 |
| HPV56 | E2 | 9 | 30 |
| HPV56 | E2 | 8 | 278 |
| HPV56 | E2 | 9 | 278 |
| HPV56 | E2 | 9 | 111 |
| HPV56 | E2 | 10 | 111 |
| HPV56 | E2 | 8 | 74 |
| HPV56 | E2 | 9 | 74 |
| HPV56 | E2 | 9 | 102 |
| HPV56 | E2 | 10 | 102 |
| HPV56 | E6 | 9 | 49 |
| HPV56 | E6 | 10 | 49 |
| HPV56 | E6 | 8 | 89 |
| HPV56 | E6 | 9 | 89 |
| HPV56 | E6 | 10 | 64 |
| HPV56 | E6 | 8 | 100 |
| HPV56 | E6 | 9 | 100 |
| HPV56 | E6 | 8 | 122 |
| HPV56 | E6 | 10 | 139 |
| HPV56 | E6 | 9 | 69 |
| HPV56 | E6 | 10 | 69 |
| HPV56 | E6 | 11 | 69 |
| HPV56 | E6 | 8 | 50 |
| HPV56 | E6 | 9 | 50 |
| HPV56 | E6 | 10 | 33 |
| HPV56 | E6 | 9 | 59 |
| HPV56 | E6 | 8 | 60 |
| HPV56 | E6 | 8 | 101 |
| HPV56 | E6 | 8 | 28 |
| HPV56 | E6 | 10 | 28 |
| HPV56 | E6 | 11 | 28 |
| HPV56 | E6 | 8 | 23 |
| HPV56 | E6 | 8 | 39 |
| HPV56 | E6 | 11 | 20 |
| HPV56 | E6 | 11 | 44 |
| HPV56 | E6 | 10 | 48 |
| HPV56 | E6 | 11 | 48 |
| HPV56 | E6 | 9 | 5 |
| HPV56 | E6 | 9 | 88 |
| HPV56 | E6 | 10 | 88 |
| HPV56 | E6 | 8 | 141 |
| HPV56 | E6 | 11 | 141 |
| HPV56 | E6 | 8 | 137 |
| HPV56 | E6 | 9 | 121 |
| HPV56 | E6 | 9 | 27 |
| HPV56 | E6 | 11 | 27 |
| HPV56 | E6 | 10 | 54 |
| HPV56 | E6 | 8 | 75 |
| HPV56 | E6 | 10 | 75 |
| HPV56 | E6 | 9 | 99 |
| HPV56 | E6 | 10 | 99 |
| HPV56 | E6 | 8 | 71 |
| HPV56 | E6 | 9 | 71 |
| HPV56 | E6 | 10 | 71 |
| HPV56 | E6 | 11 | 71 |
| HPV56 | E6 | 9 | 140 |
| HPV56 | E6 | 10 | 26 |
| HPV56 | E6 | 8 | 70 |
| HPV56 | E6 | 9 | 70 |
| HPV56 | E6 | 10 | 70 |
| HPV56 | E6 | 11 | 70 |
| HPV56 | E6 | 8 | 31 |
| HPV56 | E6 | 9 | 113 |
| HPV56 | E6 | 9 | 55 |
| HPV56 | E6 | 8 | 47 |
| HPV56 | E6 | 11 | 47 |
| HPV56 | E6 | 8 | 5 |
| HPV56 | E6 | 11 | 5 |
| HPV56 | E6 | 11 | 25 |
| HPV56 | E6 | 10 | 112 |
| HPV56 | E6 | 8 | 4 |
| HPV56 | E6 | 10 | 4 |
| HPV56 | E6 | 8 | 98 |
| HPV56 | E6 | 10 | 98 |
| HPV56 | E6 | 11 | 98 |
| HPV56 | E6 | 8 | 119 |
| HPV56 | E6 | 9 | 119 |
| HPV56 | E6 | 11 | 119 |
| HPV56 | E6 | 9 | 110 |
| HPV56 | E6 | 11 | 108 |
| HPV56 | E6 | 10 | 58 |
| HPV56 | E6 | 8 | 30 |
| HPV56 | E6 | 9 | 30 |
| HPV56 | E6 | 9 | 67 |
| HPV56 | E6 | 11 | 67 |
| HPV56 | E6 | 11 | 138 |
| HPV56 | E6 | 11 | 32 |
| HPV56 | E6 | 9 | 136 |
| HPV56 | E6 | 8 | 90 |
| HPV56 | E6 | 8 | 68 |
| HPV56 | E6 | 10 | 68 |
| HPV56 | E6 | 11 | 68 |
| HPV56 | E6 | 9 | 65 |
| HPV56 | E6 | 11 | 65 |
| HPV56 | E6 | 10 | 21 |
| HPV56 | E6 | 10 | 135 |
| HPV56 | E6 | 11 | 63 |
| HPV56 | E6 | 8 | 35 |
| HPV56 | E6 | 10 | 87 |
| HPV56 | E6 | 11 | 87 |
| HPV56 | E6 | 9 | 46 |
| HPV56 | E6 | 8 | 73 |
| HPV56 | E6 | 9 | 73 |
| HPV56 | E6 | 10 | 73 |
| HPV56 | E7 | 10 | 75 |
| HPV56 | E7 | 10 | 33 |
| HPV56 | E7 | 8 | 35 |
| HPV56 | E7 | 10 | 37 |
| HPV56 | E7 | 8 | 39 |

TABLE XVII-continued

HLA-AI1 Motif Peptides

| 1 | 2 | 3 | 4 |
|---|---|---|---|
| HPV56 | E7 | 11 | 70 |
| HPV56 | E7 | 10 | 42 |
| HPV56 | E7 | 8 | 62 |
| HPV56 | E7 | 11 | 74 |
| HPV56 | E7 | 10 | 60 |
| HPV56 | E7 | 8 | 52 |
| HPV56 | E7 | 11 | 52 |
| HPV56 | E7 | 8 | 49 |
| HPV56 | E7 | 11 | 49 |
| HPV56 | E7 | 8 | 73 |
| HPV56 | E7 | 8 | 77 |
| HPV56 | E7 | 10 | 71 |
| HPV56 | E7 | 11 | 59 |
| HPV56 | L1 | 9 | 135 |
| HPV56 | L1 | 11 | 273 |
| HPV56 | L1 | 11 | 149 |
| HPV56 | L1 | 11 | 72 |
| HPV56 | L1 | 11 | 241 |
| HPV56 | L1 | 8 | 198 |
| HPV56 | L1 | 10 | 169 |
| HPV56 | L1 | 8 | 58 |
| HPV56 | L1 | 8 | 381 |
| HPV56 | L1 | 11 | 381 |
| HPV56 | L1 | 8 | 444 |
| HPV56 | L1 | 9 | 444 |
| HPV56 | L1 | 10 | 444 |
| HPV56 | L1 | 9 | 37 |
| HPV56 | L1 | 11 | 37 |
| HPV56 | L1 | 8 | 512 |
| HPV56 | L1 | 11 | 79 |
| HPV56 | L1 | 8 | 195 |
| HPV56 | L1 | 11 | 195 |
| HPV56 | L1 | 8 | 136 |
| HPV56 | L1 | 8 | 389 |
| HPV56 | L1 | 10 | 389 |
| HPV56 | L1 | 11 | 389 |
| HPV56 | L1 | 10 | 274 |
| HPV56 | L1 | 9 | 243 |
| HPV56 | L1 | 8 | 257 |
| HPV56 | L1 | 9 | 257 |
| HPV56 | L1 | 9 | 491 |
| HPV56 | L1 | 10 | 491 |
| HPV56 | L1 | 8 | 179 |
| HPV56 | L1 | 9 | 90 |
| HPV56 | L1 | 8 | 278 |
| HPV56 | L1 | 9 | 278 |
| HPV56 | L1 | 11 | 176 |
| HPV56 | L1 | 11 | 60 |
| HPV56 | L1 | 10 | 236 |
| HPV56 | L1 | 11 | 121 |
| HPV56 | L1 | 9 | 337 |
| HPV56 | L1 | 8 | 448 |
| HPV56 | L1 | 10 | 404 |
| HPV56 | L1 | 10 | 308 |
| HPV56 | L1 | 8 | 303 |
| HPV56 | L1 | 10 | 303 |
| HPV56 | L1 | 8 | 290 |
| HPV56 | L1 | 11 | 290 |
| HPV56 | L1 | 9 | 117 |
| HPV56 | L1 | 8 | 501 |
| HPV56 | L1 | 10 | 501 |
| HPV56 | L1 | 8 | 33 |
| HPV56 | L1 | 9 | 341 |
| HPV56 | L1 | 9 | 364 |
| HPV56 | L1 | 9 | 194 |
| HPV56 | L1 | 9 | 277 |
| HPV56 | L1 | 10 | 277 |
| HPV56 | L1 | 8 | 238 |
| HPV56 | L1 | 8 | 118 |
| HPV56 | L1 | 10 | 150 |
| HPV56 | L1 | 10 | 73 |
| HPV56 | L1 | 11 | 235 |
| HPV56 | L1 | 9 | 32 |
| HPV56 | L1 | 9 | 68 |
| HPV56 | L1 | 11 | 393 |
| HPV56 | L1 | 10 | 378 |
| HPV56 | L1 | 11 | 378 |
| HPV56 | L1 | 10 | 414 |
| HPV56 | L1 | 10 | 334 |
| HPV56 | L1 | 11 | 192 |
| HPV56 | L1 | 8 | 258 |
| HPV56 | L1 | 11 | 258 |
| HPV56 | L1 | 10 | 89 |
| HPV56 | L1 | 10 | 116 |
| HPV56 | L1 | 9 | 500 |
| HPV56 | L1 | 11 | 500 |
| HPV56 | L1 | 8 | 392 |
| HPV56 | L1 | 11 | 413 |
| HPV56 | L1 | 10 | 93 |
| HPV56 | L1 | 11 | 300 |
| HPV56 | L1 | 8 | 98 |
| HPV56 | L1 | 11 | 98 |
| HPV56 | L1 | 8 | 55 |
| HPV56 | L1 | 10 | 55 |
| HPV56 | L1 | 11 | 55 |
| HPV56 | L1 | 11 | 45 |
| HPV56 | L1 | 11 | 168 |
| HPV56 | L1 | 8 | 78 |
| HPV56 | L1 | 9 | 256 |
| HPV56 | L1 | 10 | 256 |
| HPV56 | L1 | 8 | 492 |
| HPV56 | L1 | 9 | 492 |
| HPV56 | L1 | 9 | 289 |
| HPV56 | L1 | 10 | 340 |
| HPV56 | L1 | 10 | 363 |
| HPV56 | L1 | 8 | 147 |
| HPV56 | L1 | 8 | 77 |
| HPV56 | L1 | 9 | 77 |
| HPV56 | L1 | 9 | 502 |
| HPV56 | L1 | 8 | 416 |
| HPV56 | L1 | 10 | 416 |
| HPV56 | L1 | 9 | 151 |
| HPV56 | L1 | 8 | 385 |
| HPV56 | L1 | 10 | 36 |
| HPV56 | L1 | 10 | 242 |
| HPV56 | L1 | 11 | 333 |
| HPV56 | L1 | 8 | 2 |
| HPV56 | L1 | 9 | 2 |
| HPV56 | L1 | 9 | 1 |
| HPV56 | L1 | 10 | 1 |
| HPV56 | L1 | 11 | 5 |
| HPV56 | L1 | 11 | 315 |
| HPV56 | L1 | 8 | 95 |
| HPV56 | L1 | 10 | 95 |
| HPV56 | L1 | 11 | 95 |
| HPV56 | L1 | 9 | 123 |
| HPV56 | L1 | 9 | 170 |
| HPV56 | L1 | 8 | 171 |
| HPV56 | L1 | 8 | 91 |
| HPV56 | L1 | 9 | 197 |
| HPV56 | L1 | 8 | 511 |
| HPV56 | L1 | 9 | 511 |
| HPV56 | L1 | 11 | 266 |
| HPV56 | L1 | 10 | 31 |
| HPV56 | L1 | 10 | 255 |
| HPV56 | L1 | 11 | 255 |
| HPV56 | L1 | 9 | 146 |
| HPV56 | L1 | 10 | 467 |
| HPV56 | L1 | 11 | 467 |
| HPV56 | L1 | 9 | 522 |
| HPV56 | L1 | 10 | 522 |
| HPV56 | L1 | 11 | 522 |
| HPV56 | L1 | 9 | 442 |
| HPV56 | L1 | 10 | 442 |
| HPV56 | L1 | 11 | 442 |
| HPV56 | L1 | 11 | 52 |
| HPV56 | L1 | 8 | 471 |
| HPV56 | L1 | 8 | 406 |
| HPV56 | L1 | 10 | 288 |
| HPV56 | L1 | 11 | 339 |

TABLE XVII-continued

HLA-AI1 Motif Peptides

| 1 | 2 | 3 | 4 |
|---|---|---|---|
| HPV56 | L1 | 11 | 362 |
| HPV56 | L1 | 8 | 384 |
| HPV56 | L1 | 9 | 384 |
| HPV56 | L1 | 11 | 35 |
| HPV56 | L1 | 9 | 260 |
| HPV56 | L1 | 11 | 260 |
| HPV56 | L1 | 9 | 178 |
| HPV56 | L1 | 9 | 76 |
| HPV56 | L1 | 10 | 76 |
| HPV56 | L1 | 10 | 508 |
| HPV56 | L1 | 11 | 508 |
| HPV56 | L1 | 9 | 455 |
| HPV56 | L1 | 9 | 108 |
| HPV56 | L1 | 9 | 417 |
| HPV56 | L1 | 11 | 520 |
| HPV56 | L1 | 9 | 100 |
| HPV56 | L1 | 11 | 100 |
| HPV56 | L1 | 8 | 152 |
| HPV56 | L1 | 10 | 67 |
| HPV56 | L1 | 8 | 446 |
| HPV56 | L1 | 10 | 446 |
| HPV56 | L1 | 8 | 279 |
| HPV56 | L1 | 9 | 74 |
| HPV56 | L1 | 11 | 74 |
| HPV56 | L1 | 8 | 456 |
| HPV56 | L1 | 9 | 379 |
| HPV56 | L1 | 10 | 379 |
| HPV56 | L1 | 8 | 261 |
| HPV56 | L1 | 10 | 261 |
| HPV56 | L1 | 11 | 489 |
| HPV56 | L1 | 8 | 526 |
| HPV56 | L1 | 9 | 526 |
| HPV56 | L1 | 8 | 524 |
| HPV56 | L1 | 9 | 524 |
| HPV56 | L1 | 10 | 524 |
| HPV56 | L1 | 11 | 524 |
| HPV56 | L1 | 8 | 86 |
| HPV56 | L1 | 8 | 380 |
| HPV56 | L1 | 9 | 380 |
| HPV56 | L1 | 9 | 262 |
| HPV56 | L1 | 11 | 460 |
| HPV56 | L1 | 10 | 490 |
| HPV56 | L1 | 11 | 490 |
| HPV56 | L1 | 9 | 237 |
| HPV56 | L1 | 9 | 304 |
| HPV56 | L1 | 11 | 377 |
| HPV56 | L1 | 9 | 415 |
| HPV56 | L1 | 11 | 415 |
| HPV56 | L1 | 9 | 94 |
| HPV56 | L1 | 11 | 94 |
| HPV56 | L1 | 10 | 122 |
| HPV56 | L1 | 9 | 335 |
| HPV56 | L1 | 11 | 335 |
| HPV56 | L1 | 11 | 66 |
| HPV56 | L1 | 8 | 445 |
| HPV56 | L1 | 9 | 445 |
| HPV56 | L1 | 11 | 445 |
| HPV56 | L1 | 8 | 525 |
| HPV56 | L1 | 9 | 525 |
| HPV56 | L1 | 10 | 525 |
| HPV56 | L1 | 8 | 523 |
| HPV56 | L1 | 9 | 523 |
| HPV56 | L1 | 10 | 523 |
| HPV56 | L1 | 11 | 523 |
| HPV56 | L1 | 8 | 57 |
| HPV56 | L1 | 9 | 57 |
| HPV56 | L1 | 8 | 443 |
| HPV56 | L1 | 9 | 443 |
| HPV56 | L1 | 10 | 443 |
| HPV56 | L1 | 11 | 443 |
| HPV56 | L1 | 11 | 106 |
| HPV56 | L1 | 10 | 193 |
| HPV56 | L1 | 10 | 301 |
| HPV56 | L1 | 10 | 80 |
| HPV56 | L1 | 10 | 99 |
| HPV56 | L1 | 10 | 53 |
| HPV56 | L1 | 8 | 365 |
| HPV56 | L1 | 9 | 56 |
| HPV56 | L1 | 10 | 56 |
| HPV56 | L1 | 10 | 134 |
| HPV56 | L1 | 8 | 346 |
| HPV56 | L1 | 8 | 203 |
| HPV56 | L1 | 9 | 388 |
| HPV56 | L1 | 11 | 388 |
| HPV56 | L1 | 8 | 276 |
| HPV56 | L1 | 10 | 276 |
| HPV56 | L1 | 11 | 276 |
| HPV56 | L1 | 9 | 7 |
| HPV56 | L1 | 10 | 7 |
| HPV56 | L1 | 8 | 310 |
| HPV56 | L1 | 9 | 268 |
| HPV56 | L1 | 9 | 47 |
| HPV56 | L1 | 8 | 396 |
| HPV56 | L1 | 10 | 283 |
| HPV56 | L1 | 11 | 283 |
| HPV56 | L1 | 9 | 85 |
| HPV56 | L1 | 9 | 62 |
| HPV56 | L1 | 10 | 62 |
| HPV56 | L1 | 11 | 453 |
| HPV56 | L2 | 8 | 222 |
| HPV56 | L2 | 10 | 286 |
| HPV56 | L2 | 9 | 69 |
| HPV56 | L2 | 10 | 281 |
| HPV56 | L2 | 11 | 281 |
| HPV56 | L2 | 9 | 438 |
| HPV56 | L2 | 10 | 438 |
| HPV56 | L2 | 11 | 438 |
| HPV56 | L2 | 9 | 340 |
| HPV56 | L2 | 8 | 12 |
| HPV56 | L2 | 11 | 12 |
| HPV56 | L2 | 10 | 367 |
| HPV56 | L2 | 9 | 14 |
| HPV56 | L2 | 9 | 275 |
| HPV56 | L2 | 10 | 275 |
| HPV56 | L2 | 10 | 142 |
| HPV56 | L2 | 9 | 30 |
| HPV56 | L2 | 10 | 29 |
| HPV56 | L2 | 10 | 194 |
| HPV56 | L2 | 10 | 437 |
| HPV56 | L2 | 11 | 437 |
| HPV56 | L2 | 8 | 344 |
| HPV56 | L2 | 8 | 444 |
| HPV56 | L2 | 9 | 444 |
| HPV56 | L2 | 8 | 276 |
| HPV56 | L2 | 9 | 276 |
| HPV56 | L2 | 9 | 287 |
| HPV56 | L2 | 11 | 418 |
| HPV56 | L2 | 8 | 314 |
| HPV56 | L2 | 9 | 217 |
| HPV56 | L2 | 11 | 217 |
| HPV56 | L2 | 10 | 292 |
| HPV56 | L2 | 11 | 292 |
| HPV56 | L2 | 11 | 58 |
| HPV56 | L2 | 9 | 394 |
| HPV56 | L2 | 8 | 64 |
| HPV56 | L2 | 10 | 434 |
| HPV56 | L2 | 10 | 25 |
| HPV56 | L2 | 10 | 62 |
| HPV56 | L2 | 9 | 60 |
| HPV56 | L2 | 9 | 310 |
| HPV56 | L2 | 10 | 310 |
| HPV56 | L2 | 11 | 310 |
| HPV56 | L2 | 9 | 293 |
| HPV56 | L2 | 10 | 293 |
| HPV56 | L2 | 8 | 221 |
| HPV56 | L2 | 9 | 221 |
| HPV56 | L2 | 8 | 313 |
| HPV56 | L2 | 9 | 313 |
| HPV56 | L2 | 10 | 59 |
| HPV56 | L2 | 11 | 180 |

TABLE XVII-continued

HLA-AI1 Motif Peptides

| 1 | 2 | 3 | 4 |
|---|---|---|---|
| HPV56 | L2 | 10 | 44 |
| HPV56 | L2 | 10 | 210 |
| HPV56 | L2 | 11 | 210 |
| HPV56 | L2 | 9 | 182 |
| HPV56 | L2 | 11 | 182 |
| HPV56 | L2 | 9 | 143 |
| HPV56 | L2 | 8 | 81 |
| HPV56 | L2 | 8 | 302 |
| HPV56 | L2 | 10 | 34 |
| HPV56 | L2 | 11 | 43 |
| HPV56 | L2 | 10 | 235 |
| HPV56 | L2 | 11 | 141 |
| HPV56 | L2 | 10 | 393 |
| HPV56 | L2 | 10 | 299 |
| HPV56 | L2 | 11 | 299 |
| HPV56 | L2 | 10 | 181 |
| HPV56 | L2 | 11 | 338 |
| HPV56 | L2 | 8 | 277 |
| HPV56 | L2 | 8 | 1 |
| HPV56 | L2 | 9 | 1 |
| HPV56 | L2 | 10 | 1 |
| HPV56 | L2 | 11 | 1 |
| HPV56 | L2 | 8 | 341 |
| HPV56 | L2 | 11 | 341 |
| HPV56 | L2 | 10 | 342 |
| HPV56 | L2 | 8 | 395 |
| HPV56 | L2 | 11 | 285 |
| HPV56 | L2 | 10 | 274 |
| HPV56 | L2 | 11 | 274 |
| HPV56 | L2 | 8 | 417 |
| HPV56 | L2 | 10 | 216 |
| HPV56 | L2 | 11 | 209 |
| HPV56 | L2 | 11 | 392 |
| HPV56 | L2 | 8 | 196 |
| HPV56 | L2 | 8 | 369 |
| HPV56 | L2 | 11 | 78 |
| HPV56 | L2 | 8 | 185 |
| HPV56 | L2 | 8 | 441 |
| HPV56 | L2 | 9 | 441 |
| HPV56 | L2 | 10 | 441 |
| HPV56 | L2 | 11 | 441 |
| HPV56 | L2 | 11 | 433 |
| HPV56 | L2 | 8 | 312 |
| HPV56 | L2 | 9 | 312 |
| HPV56 | L2 | 10 | 312 |
| HPV56 | L2 | 8 | 421 |
| HPV56 | L2 | 11 | 421 |
| HPV56 | L2 | 9 | 364 |
| HPV56 | L2 | 11 | 306 |
| HPV56 | L2 | 10 | 68 |
| HPV56 | L2 | 8 | 11 |
| HPV56 | L2 | 9 | 11 |
| HPV56 | L2 | 8 | 295 |
| HPV56 | L2 | 8 | 291 |
| HPV56 | L2 | 11 | 291 |
| HPV56 | L2 | 8 | 309 |
| HPV56 | L2 | 10 | 309 |
| HPV56 | L2 | 11 | 309 |
| HPV56 | L2 | 8 | 220 |
| HPV56 | L2 | 9 | 220 |
| HPV56 | L2 | 10 | 220 |
| HPV56 | L2 | 11 | 298 |
| HPV56 | L2 | 11 | 225 |
| HPV56 | L2 | 10 | 339 |
| HPV56 | L2 | 10 | 13 |
| HPV56 | L2 | 8 | 436 |
| HPV56 | L2 | 11 | 436 |
| HPV56 | L2 | 9 | 343 |
| HPV56 | L2 | 11 | 24 |
| HPV56 | L2 | 9 | 435 |
| HPV56 | L2 | 11 | 362 |
| HPV56 | L2 | 9 | 211 |
| HPV56 | L2 | 10 | 211 |
| HPV56 | L2 | 10 | 147 |
| HPV56 | L2 | 10 | 79 |
| HPV56 | L2 | 8 | 212 |
| HPV56 | L2 | 9 | 212 |
| HPV56 | L2 | 8 | 183 |
| HPV56 | L2 | 10 | 183 |
| HPV56 | L2 | 9 | 148 |
| HPV56 | L2 | 11 | 414 |
| HPV56 | L2 | 8 | 365 |
| HPV56 | L2 | 9 | 26 |
| HPV56 | L2 | 8 | 237 |
| HPV56 | L2 | 9 | 63 |
| HPV56 | L2 | 8 | 61 |
| HPV56 | L2 | 11 | 61 |
| HPV56 | L2 | 9 | 80 |
| HPV56 | L2 | 11 | 146 |
| HPV56 | L2 | 8 | 288 |
| HPV56 | L2 | 11 | 288 |
| HPV56 | L2 | 8 | 149 |
| HPV56 | L2 | 8 | 2 |
| HPV56 | L2 | 9 | 2 |
| HPV56 | L2 | 10 | 2 |
| HPV56 | L2 | 11 | 280 |
| HPV56 | L2 | 11 | 366 |
| HPV56 | L2 | 9 | 236 |
| HPV56 | L2 | 8 | 31 |
| HPV56 | L2 | 8 | 424 |
| HPV56 | L2 | 8 | 443 |
| HPV56 | L2 | 9 | 443 |
| HPV56 | L2 | 10 | 443 |

SF 1168136 v1

TABLE XVII A

HPV6A
HLA-A11 Motif Peptides

| 2 | 3 | 4 |
|---|---|---|
| E6 | 10 | 62 |
| L1 | 8 | 234 |
| L2 | 8 | 329 |
| E1 | 8 | 206 |
| L1 | 9 | 489 |
| L1 | 11 | 489 |
| L2 | 10 | 340 |
| E4 | 9 | 2 |
| E4 | 11 | 2 |
| E6 | 9 | 63 |
| E6 | 11 | 63 |
| E6 | 9 | 65 |
| E2 | 10 | 10 |
| L1 | 9 | 98 |
| E1 | 11 | 235 |
| E1 | 10 | 392 |
| E1 | 11 | 392 |
| L2 | 8 | 238 |
| L2 | 9 | 275 |
| L2 | 10 | 275 |
| E1 | 11 | 637 |
| L2 | 11 | 116 |
| E1 | 8 | 193 |
| E1 | 10 | 193 |
| E1 | 11 | 190 |
| E1 | 9 | 144 |
| E1 | 10 | 144 |
| L2 | 10 | 286 |
| L2 | 11 | 286 |
| E1 | 9 | 112 |
| E1 | 10 | 112 |
| L2 | 10 | 140 |
| L1 | 11 | 420 |
| E1 | 10 | 475 |
| E2 | 8 | 331 |

TABLE XVII A-continued

HPV6A
HLA-A11 Motif Peptides

| 2 | 3 | 4 |
|---|---|---|
| E1 | 11 | 65 |
| E6 | 8 | 37 |
| E6 | 10 | 37 |
| L1 | 11 | 203 |
| L1 | 8 | 54 |
| E1 | 9 | 608 |
| L1 | 8 | 487 |
| L1 | 9 | 487 |
| L1 | 11 | 487 |
| L2 | 11 | 12 |
| E2 | 8 | 322 |
| E2 | 9 | 322 |
| L2 | 8 | 288 |
| L2 | 9 | 288 |
| L2 | 11 | 288 |
| L1 | 11 | 36 |
| L1 | 9 | 342 |
| L1 | 8 | 22 |
| E1 | 8 | 407 |
| E1 | 9 | 407 |
| L2 | 9 | 14 |
| E1 | 8 | 525 |
| E6 | 9 | 10 |
| E6 | 9 | 86 |
| E1 | 8 | 77 |
| E1 | 9 | 77 |
| E1 | 10 | 77 |
| E1 | 9 | 101 |
| L1 | 10 | 43 |
| L1 | 11 | 43 |
| E2 | 8 | 231 |
| E2 | 9 | 231 |
| E2 | 11 | 231 |
| L1 | 10 | 483 |
| L1 | 11 | 483 |
| E1 | 11 | 601 |
| E6 | 8 | 64 |
| E6 | 10 | 64 |
| E2 | 8 | 124 |
| L1 | 8 | 157 |
| L1 | 11 | 157 |
| L1 | 10 | 341 |
| E1 | 8 | 406 |
| E1 | 9 | 406 |
| E1 | 10 | 406 |
| E7 | 10 | 57 |
| E7 | 9 | 58 |
| E6 | 8 | 66 |
| E1 | 11 | 215 |
| E2 | 9 | 299 |
| E2 | 10 | 299 |
| E2 | 11 | 299 |
| E7 | 8 | 59 |
| E2 | 8 | 161 |
| L1 | 10 | 221 |
| E6 | 11 | 67 |
| E2 | 8 | 296 |
| E2 | 10 | 35 |
| E2 | 11 | 35 |
| E2 | 8 | 248 |
| L1 | 8 | 99 |
| E6 | 9 | 131 |
| E1 | 8 | 640 |
| E2 | 11 | 9 |
| E1 | 10 | 111 |
| E1 | 11 | 111 |
| E1 | 9 | 524 |
| E2 | 8 | 230 |
| E2 | 9 | 230 |
| E2 | 10 | 230 |
| L1 | 11 | 24 |
| E1 | 8 | 405 |
| E1 | 9 | 405 |
| E1 | 10 | 405 |

TABLE XVII A-continued

HPV6A
HLA-A11 Motif Peptides

| 2 | 3 | 4 |
|---|---|---|
| E1 | 11 | 405 |
| E1 | 10 | 523 |
| E1 | 10 | 49 |
| E2 | 10 | 122 |
| E1 | 9 | 542 |
| E1 | 10 | 542 |
| E1 | 11 | 542 |
| E7 | 9 | 41 |
| E7 | 11 | 41 |
| E1 | 9 | 161 |
| E1 | 9 | 631 |
| L1 | 8 | 219 |
| L1 | 9 | 219 |
| E6 | 8 | 96 |
| E6 | 10 | 96 |
| E1 | 8 | 570 |
| E1 | 9 | 570 |
| E1 | 10 | 570 |
| E7 | 10 | 88 |
| E1 | 10 | 222 |
| E2 | 8 | 313 |
| E1 | 11 | 81 |
| E2 | 8 | 25 |
| E2 | 10 | 25 |
| E7 | 11 | 14 |
| E1 | 9 | 203 |
| E1 | 11 | 203 |
| E1 | 10 | 303 |
| L1 | 10 | 138 |
| L1 | 11 | 138 |
| E7 | 8 | 44 |
| L1 | 11 | 84 |
| E2 | 9 | 141 |
| E1 | 11 | 166 |
| E1 | 11 | 73 |
| L1 | 11 | 269 |
| L2 | 8 | 30 |
| E6 | 10 | 99 |
| E6 | 11 | 99 |
| L2 | 8 | 258 |
| E1 | 10 | 178 |
| E2 | 9 | 174 |
| L2 | 8 | 274 |
| L2 | 10 | 274 |
| L2 | 11 | 274 |
| E1 | 10 | 143 |
| E1 | 11 | 143 |
| E1 | 8 | 336 |
| E1 | 8 | 180 |
| E1 | 10 | 180 |
| E1 | 8 | 62 |
| L1 | 9 | 299 |
| E1 | 10 | 100 |
| E2 | 9 | 229 |
| E2 | 10 | 229 |
| E2 | 11 | 229 |
| E1 | 10 | 36 |
| E1 | 10 | 630 |
| L2 | 9 | 257 |
| E6 | 9 | 69 |
| E6 | 10 | 69 |
| E6 | 11 | 69 |
| E1 | 8 | 453 |
| E1 | 10 | 453 |
| L2 | 11 | 255 |
| E4 | 10 | 89 |
| E1 | 9 | 375 |
| E1 | 10 | 105 |
| E6 | 8 | 42 |
| E6 | 11 | 42 |
| L1 | 9 | 453 |
| L1 | 10 | 453 |
| E1 | 9 | 197 |
| E1 | 8 | 604 |

TABLE XVII A-continued

HPV6A
HLA-A11 Motif Peptides

| 2 | 3 | 4 |
|---|---|---|
| E1 | 9 | 131 |
| E2 | 11 | 74 |
| E1 | 8 | 417 |
| E2 | 8 | 100 |
| E2 | 9 | 100 |
| E4 | 10 | 50 |
| E1 | 9 | 157 |
| E2 | 8 | 21 |
| E2 | 9 | 21 |
| E1 | 8 | 373 |
| E1 | 11 | 373 |
| E2 | 8 | 80 |
| E2 | 9 | 293 |
| E2 | 10 | 293 |
| E2 | 11 | 293 |
| E2 | 9 | 39 |
| E7 | 11 | 39 |
| E6 | 11 | 113 |
| E2 | 10 | 205 |
| L1 | 8 | 206 |
| L1 | 8 | 252 |
| L2 | 8 | 442 |
| E2 | 11 | 121 |
| E2 | 9 | 312 |
| E1 | 9 | 595 |
| E5 | 10 | 67 |
| L1 | 11 | 244 |
| E1 | 10 | 216 |
| E1 | 9 | 50 |
| E1 | 9 | 220 |
| E6 | 9 | 126 |
| E6 | 11 | 126 |
| E1 | 9 | 454 |
| L2 | 8 | 428 |
| L2 | 10 | 428 |
| E1 | 9 | 494 |
| L1 | 8 | 463 |
| L1 | 10 | 463 |
| E5 | 9 | 68 |
| E4 | 10 | 21 |
| E4 | 11 | 21 |
| E1 | 9 | 393 |
| E1 | 10 | 393 |
| L1 | 10 | 245 |
| L1 | 11 | 245 |
| E1 | 10 | 457 |
| L2 | 11 | 239 |
| L2 | 8 | 276 |
| L2 | 9 | 276 |
| E1 | 9 | 18 |
| L1 | 9 | 303 |
| E1 | 9 | 67 |
| E1 | 10 | 67 |
| L1 | 8 | 49 |
| L1 | 8 | 450 |
| E1 | 11 | 587 |
| E2 | 8 | 171 |
| L1 | 9 | 326 |
| L2 | 10 | 117 |
| L2 | 8 | 314 |
| E2 | 9 | 123 |
| L1 | 9 | 156 |
| E1 | 8 | 384 |
| E1 | 10 | 160 |
| L1 | 9 | 239 |
| L1 | 10 | 239 |
| L2 | 9 | 433 |
| E1 | 11 | 159 |
| L1 | 9 | 132 |
| L2 | 11 | 58 |
| E1 | 9 | 194 |
| E2 | 10 | 156 |
| E1 | 8 | 350 |
| E1 | 9 | 217 |
| L2 | 11 | 292 |
| L2 | 8 | 223 |
| E2 | 9 | 55 |
| E1 | 9 | 273 |
| E1 | 11 | 273 |
| E2 | 10 | 262 |
| L1 | 8 | 133 |
| E1 | 8 | 543 |
| E1 | 9 | 543 |
| E1 | 10 | 543 |
| E1 | 11 | 543 |
| L1 | 11 | 277 |
| E1 | 11 | 438 |
| L2 | 11 | 431 |
| L1 | 11 | 130 |
| L2 | 10 | 62 |
| E1 | 11 | 431 |
| L2 | 9 | 303 |
| L2 | 10 | 303 |
| E1 | 8 | 632 |
| E2 | 10 | 179 |
| E1 | 10 | 191 |
| L2 | 11 | 215 |
| L2 | 10 | 25 |
| L2 | 8 | 64 |
| L2 | 9 | 60 |
| E1 | 8 | 145 |
| E1 | 9 | 145 |
| L1 | 8 | 407 |
| L1 | 9 | 407 |
| L1 | 9 | 222 |
| E4 | 9 | 90 |
| E1 | 9 | 316 |
| L1 | 9 | 478 |
| L1 | 10 | 113 |
| L1 | 11 | 113 |
| E1 | 10 | 415 |
| E2 | 8 | 330 |
| E2 | 9 | 330 |
| E1 | 11 | 508 |
| E6 | 8 | 71 |
| E6 | 9 | 71 |
| E1 | 9 | 349 |
| E7 | 8 | 2 |
| L2 | 8 | 312 |
| L2 | 10 | 312 |
| E2 | 11 | 53 |
| E2 | 10 | 255 |
| E6 | 10 | 119 |
| E2 | 10 | 78 |
| E2 | 11 | 310 |
| E4 | 8 | 10 |
| E4 | 9 | 10 |
| E4 | 10 | 10 |
| E2 | 9 | 70 |
| E2 | 8 | 264 |
| E2 | 11 | 264 |
| L2 | 10 | 37 |
| E1 | 9 | 246 |
| E2 | 10 | 149 |
| E2 | 11 | 149 |
| L2 | 8 | 3 |
| L2 | 9 | 3 |
| E6 | 11 | 25 |
| L2 | 11 | 306 |
| L2 | 8 | 149 |
| E2 | 9 | 29 |
| E2 | 10 | 29 |
| E1 | 8 | 376 |
| E1 | 11 | 474 |
| L2 | 11 | 326 |
| L2 | 9 | 287 |
| L2 | 10 | 287 |
| E1 | 11 | 370 |

TABLE XVII A-continued

HPV6A
HLA-A11 Motif Peptides

| 2 | 3 | 4 |
|---|---|---|
| L1 | 8 | 220 |
| L1 | 11 | 220 |
| E1 | 8 | 51 |
| L1 | 9 | 218 |
| L1 | 10 | 218 |
| E1 | 8 | 569 |
| E1 | 9 | 569 |
| E1 | 10 | 569 |
| E1 | 11 | 569 |
| E1 | 8 | 221 |
| E1 | 11 | 221 |
| L1 | 9 | 32 |
| L2 | 9 | 313 |
| E1 | 10 | 334 |
| E2 | 10 | 54 |
| E2 | 9 | 256 |
| L2 | 8 | 299 |
| L2 | 10 | 299 |
| L2 | 10 | 59 |
| L1 | 8 | 272 |
| E6 | 9 | 97 |
| L2 | 9 | 141 |
| E1 | 8 | 195 |
| E1 | 11 | 195 |
| L2 | 11 | 178 |
| E6 | 9 | 120 |
| E6 | 9 | 74 |
| L2 | 9 | 180 |
| E1 | 11 | 492 |
| E1 | 9 | 500 |
| E1 | 9 | 106 |
| E2 | 11 | 315 |
| L1 | 10 | 421 |
| L2 | 9 | 429 |
| E1 | 8 | 571 |
| E1 | 9 | 571 |
| E1 | 11 | 571 |
| L1 | 10 | 376 |
| E2 | 8 | 267 |
| E2 | 10 | 267 |
| E2 | 11 | 267 |
| E1 | 9 | 341 |
| L2 | 8 | 82 |
| L2 | 8 | 247 |
| E7 | 9 | 89 |
| E1 | 9 | 476 |
| E1 | 11 | 476 |
| E5 | 10 | 34 |
| E2 | 9 | 45 |
| L1 | 8 | 486 |
| L1 | 9 | 486 |
| L1 | 10 | 486 |
| E2 | 10 | 298 |
| E2 | 11 | 298 |
| E2 | 11 | 34 |
| E1 | 8 | 404 |
| E1 | 9 | 404 |
| E1 | 10 | 404 |
| E1 | 11 | 404 |
| E1 | 10 | 202 |
| E1 | 11 | 460 |
| L1 | 8 | 462 |
| L1 | 9 | 462 |
| L1 | 11 | 462 |
| L1 | 9 | 449 |
| E2 | 11 | 68 |
| E2 | 11 | 155 |
| E1 | 9 | 433 |
| E6 | 10 | 73 |
| E2 | 8 | 351 |
| E2 | 9 | 351 |
| E1 | 10 | 312 |
| E2 | 8 | 359 |
| E1 | 9 | 254 |

TABLE XVII A-continued

HPV6A
HLA-A11 Motif Peptides

| 2 | 3 | 4 |
|---|---|---|
| E1 | 11 | 254 |
| E6 | 9 | 128 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| E6 | 10 | 35 |
| L1 | 11 | 437 |
| E1 | 8 | 286 |
| E6 | 8 | 18 |
| L1 | 10 | 56 |
| E2 | 9 | 165 |
| E2 | 9 | 147 |
| E6 | 8 | 116 |
| E6 | 10 | 116 |
| E1 | 10 | 121 |
| E6 | 8 | 52 |
| E6 | 10 | 52 |
| E1 | 11 | 283 |
| E2 | 8 | 63 |
| L1 | 8 | 61 |
| L1 | 11 | 61 |
| L1 | 8 | 19 |
| L1 | 11 | 19 |
| L1 | 9 | 71 |
| L1 | 11 | 42 |
| L1 | 11 | 340 |
| E6 | 8 | 111 |
| E6 | 9 | 111 |
| E6 | 11 | 106 |
| E6 | 10 | 16 |
| E4 | 8 | 35 |
| E1 | 8 | 110 |
| E1 | 11 | 110 |
| E1 | 11 | 522 |
| E1 | 10 | 541 |
| E1 | 11 | 541 |
| E7 | 11 | 87 |
| L1 | 8 | 454 |
| L1 | 9 | 454 |
| E6 | 8 | 98 |
| E6 | 11 | 98 |
| L2 | 8 | 142 |
| E2 | 10 | 311 |
| L1 | 8 | 87 |
| L1 | 10 | 302 |
| E1 | 10 | 66 |
| E1 | 11 | 66 |
| E6 | 8 | 54 |
| L1 | 10 | 325 |
| L1 | 9 | 161 |
| E1 | 8 | 495 |
| L1 | 11 | 459 |
| L1 | 8 | 110 |
| E1 | 8 | 255 |
| E1 | 10 | 255 |
| L1 | 9 | 271 |
| E6 | 8 | 101 |
| E6 | 9 | 101 |
| E1 | 9 | 223 |
| L2 | 10 | 179 |
| E2 | 9 | 266 |
| E2 | 11 | 266 |
| L2 | 9 | 246 |
| E5 | 11 | 33 |
| L1 | 8 | 41 |
| E1 | 11 | 540 |
| E4 | 9 | 8 |
| E4 | 10 | 8 |

TABLE XVII A-continued

HPV6A
HLA-A11 Motif Peptides

| 2 | 3 | 4 |
|---|---|---|
| E4 | 11 | 8 |
| E4 | 8 | 24 |
| E1 | 8 | 198 |
| L1 | 9 | 464 |
| E5 | 8 | 69 |
| E5 | 10 | 72 |
| E1 | 8 | 276 |
| E1 | 11 | 276 |
| E1 | 11 | 563 |
| E6 | 8 | 129 |
| E6 | 11 | 129 |
| E2 | 9 | 26 |
| E4 | 9 | 22 |
| E4 | 10 | 22 |
| E1 | 8 | 394 |
| E1 | 9 | 394 |
| E1 | 11 | 394 |
| E2 | 11 | 347 |
| L1 | 8 | 378 |
| L1 | 10 | 378 |
| E1 | 8 | 218 |
| E1 | 11 | 218 |
| L1 | 9 | 439 |
| L1 | 11 | 439 |
| E1 | 9 | 458 |
| L2 | 10 | 240 |
| E1 | 8 | 132 |
| E1 | 9 | 358 |
| E4 | 8 | 81 |
| E6 | 8 | 121 |
| E1 | 9 | 115 |
| E1 | 10 | 115 |
| E1 | 11 | 115 |
| E6 | 9 | 38 |
| E6 | 11 | 38 |
| E5 | 9 | 73 |
| E5 | 11 | 73 |
| E5 | 8 | 47 |
| E1 | 10 | 277 |
| E1 | 8 | 279 |
| E1 | 10 | 279 |
| L2 | 10 | 293 |
| L1 | 11 | 295 |
| E1 | 10 | 564 |
| E7 | 11 | 67 |
| L1 | 9 | 233 |
| E4 | 10 | 1 |
| L2 | 8 | 1 |
| L2 | 9 | 1 |
| L2 | 10 | 1 |
| L2 | 11 | 1 |
| E1 | 11 | 409 |
| L2 | 8 | 277 |
| E2 | 10 | 129 |
| L1 | 9 | 251 |
| L1 | 10 | 204 |
| E1 | 8 | 546 |
| E1 | 8 | 421 |
| E1 | 9 | 421 |
| E1 | 10 | 421 |
| E2 | 8 | 151 |
| E2 | 9 | 151 |
| E1 | 8 | 19 |
| L1 | 11 | 154 |
| E1 | 8 | 274 |
| E1 | 10 | 274 |
| E2 | 8 | 71 |
| E6 | 9 | 36 |
| E6 | 11 | 36 |
| E1 | 10 | 607 |
| E2 | 8 | 295 |
| E2 | 9 | 295 |
| E6 | 10 | 130 |
| L1 | 9 | 205 |
| E2 | 8 | 170 |
| E2 | 9 | 170 |
| E1 | 8 | 158 |
| L1 | 8 | 406 |
| L1 | 9 | 406 |
| L1 | 10 | 406 |
| E1 | 9 | 568 |
| E1 | 10 | 568 |
| E1 | 11 | 568 |
| E1 | 10 | 451 |
| L1 | 10 | 31 |
| E2 | 10 | 265 |
| E4 | 8 | 23 |
| E4 | 9 | 23 |
| L1 | 10 | 438 |
| E1 | 8 | 397 |
| E2 | 8 | 269 |
| E2 | 9 | 269 |
| L1 | 9 | 352 |
| L1 | 10 | 352 |
| E1 | 11 | 59 |
| E1 | 8 | 395 |
| E1 | 10 | 395 |
| E2 | 8 | 22 |
| E2 | 11 | 22 |
| L2 | 9 | 38 |
| E2 | 10 | 348 |
| E2 | 11 | 348 |
| L2 | 9 | 237 |
| L2 | 11 | 285 |
| L2 | 11 | 139 |
| E5 | 8 | 78 |
| L1 | 11 | 482 |
| L2 | 8 | 438 |
| L2 | 9 | 438 |
| L2 | 10 | 438 |
| L2 | 11 | 438 |
| E2 | 9 | 247 |
| E1 | 9 | 528 |
| E1 | 11 | 528 |
| L2 | 10 | 272 |
| L2 | 8 | 355 |
| E1 | 11 | 302 |
| E7 | 9 | 18 |
| L2 | 9 | 29 |
| L1 | 11 | 228 |
| E1 | 10 | 594 |
| E4 | 11 | 20 |
| E1 | 11 | 456 |
| L2 | 8 | 214 |
| L1 | 10 | 217 |
| L1 | 11 | 217 |
| E1 | 8 | 442 |
| E6 | 9 | 110 |
| E6 | 10 | 110 |
| E4 | 8 | 34 |
| E4 | 9 | 34 |
| L1 | 8 | 160 |
| L1 | 10 | 160 |
| L1 | 9 | 109 |
| E2 | 8 | 61 |
| E2 | 10 | 61 |
| E1 | 8 | 545 |
| E1 | 9 | 545 |
| L1 | 9 | 405 |
| L1 | 10 | 405 |
| L1 | 11 | 405 |
| E1 | 8 | 590 |
| L2 | 10 | 80 |
| E1 | 8 | 182 |
| L1 | 11 | 426 |
| L2 | 10 | 426 |
| L1 | 9 | 266 |
| L2 | 8 | 212 |

TABLE XVII A-continued

HPV6A
HLA-A11 Motif Peptides

| 2 | 3 | 4 |
|---|---|---|
| L2 | 10 | 212 |
| L1 | 11 | 16 |
| L2 | 9 | 363 |
| L2 | 9 | 328 |
| E4 | 9 | 38 |
| E4 | 10 | 38 |
| E4 | 11 | 38 |
| E4 | 10 | 44 |
| E7 | 8 | 70 |
| L2 | 8 | 342 |
| E6 | 9 | 95 |
| E6 | 11 | 95 |
| L1 | 11 | 137 |
| E7 | 9 | 43 |
| E2 | 8 | 140 |
| E2 | 10 | 140 |
| E6 | 11 | 66 |
| E2 | 11 | 163 |
| E2 | 10 | 289 |
| L2 | 8 | 262 |
| E2 | 8 | 291 |
| E2 | 11 | 291 |
| E6 | 8 | 28 |
| E6 | 11 | 15 |
| L1 | 11 | 301 |
| L1 | 11 | 324 |
| E6 | 10 | 50 |
| E4 | 9 | 4 |
| L1 | 10 | 232 |
| L1 | 10 | 250 |
| E2 | 9 | 76 |
| E1 | 8 | 305 |
| E1 | 11 | 450 |
| E1 | 8 | 314 |
| E1 | 11 | 314 |
| L1 | 11 | 466 |
| E2 | 11 | 245 |
| L1 | 9 | 417 |
| E2 | 9 | 103 |
| E2 | 10 | 103 |
| E2 | 11 | 103 |
| E2 | 9 | 233 |
| E1 | 10 | 128 |
| E1 | 9 | 205 |
| E1 | 11 | 391 |
| L1 | 9 | 53 |
| L2 | 8 | 11 |
| E2 | 8 | 108 |
| E1 | 9 | 639 |
| E1 | 8 | 169 |
| E6 | 10 | 125 |
| E1 | 8 | 281 |
| E1 | 9 | 383 |
| E2 | 8 | 113 |
| L2 | 8 | 291 |
| L1 | 11 | 470 |
| L2 | 10 | 302 |
| L2 | 11 | 302 |
| L2 | 9 | 298 |
| L2 | 11 | 298 |
| E1 | 9 | 109 |
| L1 | 8 | 241 |
| L2 | 10 | 281 |
| L2 | 11 | 281 |
| L2 | 10 | 245 |
| L1 | 9 | 40 |
| E2 | 8 | 303 |
| L2 | 9 | 308 |
| L2 | 11 | 308 |
| L1 | 9 | 472 |
| L1 | 10 | 472 |
| L1 | 11 | 476 |
| L1 | 9 | 279 |
| L2 | 10 | 221 |

TABLE XVII A-continued

HPV6A
HLA-A11 Motif Peptides

| 2 | 3 | 4 |
|---|---|---|
| L1 | 8 | 140 |
| L1 | 9 | 140 |
| L1 | 8 | 488 |
| L1 | 10 | 488 |
| L1 | 9 | 379 |
| L2 | 8 | 181 |
| L2 | 10 | 13 |
| E6 | 10 | 9 |
| L1 | 8 | 353 |
| L1 | 9 | 353 |
| L2 | 11 | 352 |
| E1 | 10 | 219 |
| E1 | 10 | 493 |
| L1 | 8 | 440 |
| L1 | 10 | 440 |
| L2 | 10 | 432 |
| L1 | 10 | 131 |
| L1 | 8 | 115 |
| L1 | 9 | 115 |
| L2 | 8 | 309 |
| L2 | 10 | 309 |
| L2 | 11 | 309 |
| E2 | 11 | 261 |
| L2 | 9 | 63 |
| E1 | 10 | 315 |
| L1 | 9 | 63 |
| L1 | 10 | 467 |
| E1 | 8 | 422 |
| E1 | 9 | 422 |
| E2 | 8 | 207 |
| L1 | 8 | 474 |
| E1 | 8 | 247 |
| L1 | 11 | 375 |
| L2 | 9 | 81 |
| E1 | 10 | 60 |
| L1 | 9 | 86 |
| E4 | 9 | 80 |
| L2 | 8 | 304 |
| L2 | 9 | 304 |
| E2 | 9 | 150 |
| E2 | 10 | 150 |
| E1 | 11 | 606 |
| E2 | 8 | 294 |
| E2 | 9 | 294 |
| E2 | 10 | 294 |
| E1 | 10 | 567 |
| E1 | 11 | 567 |
| E1 | 9 | 396 |
| L1 | 9 | 297 |
| L1 | 11 | 297 |
| L1 | 11 | 451 |
| L1 | 8 | 473 |
| L1 | 9 | 473 |
| L1 | 10 | 85 |
| E4 | 10 | 79 |
| L1 | 9 | 38 |
| L1 | 11 | 38 |
| L1 | 10 | 37 |
| L2 | 11 | 209 |
| E2 | 10 | 316 |
| L1 | 9 | 347 |
| L1 | 10 | 347 |
| E2 | 10 | 23 |
| E2 | 9 | 180 |
| L2 | 9 | 241 |
| L2 | 10 | 210 |
| E2 | 9 | 317 |
| L1 | 8 | 348 |
| L1 | 9 | 348 |
| L1 | 11 | 348 |
| E2 | 8 | 40 |
| E5 | 10 | 45 |
| L2 | 10 | 260 |
| L1 | 8 | 343 |

TABLE XVII A-continued

HPV6A
HLA-A11 Motif Peptides

| 2 | 3 | 4 |
|---|---|---|
| E6 | 9 | 40 |
| E6 | 10 | 40 |
| E1 | 9 | 192 |
| E1 | 11 | 192 |
| L2 | 10 | 216 |
| E7 | 11 | 56 |
| E2 | 8 | 160 |
| E2 | 9 | 160 |
| L2 | 9 | 26 |
| L1 | 9 | 422 |
| L1 | 11 | 422 |
| E2 | 9 | 24 |
| E2 | 11 | 24 |
| L2 | 11 | 235 |
| E2 | 8 | 142 |
| E1 | 10 | 588 |
| E1 | 10 | 167 |
| L2 | 8 | 430 |
| L2 | 8 | 61 |
| L2 | 11 | 61 |
| L2 | 11 | 24 |
| E1 | 8 | 146 |
| L1 | 10 | 477 |
| L2 | 11 | 69 |
| L2 | 8 | 39 |
| L1 | 8 | 408 |
| L1 | 10 | 270 |
| E5 | 11 | 71 |
| E6 | 10 | 26 |
| L1 | 9 | 377 |
| L1 | 11 | 377 |
| E1 | 8 | 408 |
| E2 | 11 | 128 |
| L1 | 11 | 30 |
| E2 | 9 | 268 |
| E2 | 10 | 268 |
| L1 | 8 | 351 |
| L1 | 10 | 351 |
| L1 | 11 | 351 |
| E6 | 11 | 8 |
| L2 | 10 | 147 |
| E1 | 8 | 566 |
| E1 | 11 | 566 |
| E4 | 11 | 78 |
| L1 | 10 | 346 |
| L1 | 11 | 346 |
| L1 | 8 | 280 |
| E5 | 11 | 44 |
| E2 | 11 | 97 |
| E6 | 8 | 39 |
| E6 | 10 | 39 |
| E6 | 11 | 39 |
| L1 | 8 | 223 |
| E6 | 8 | 11 |
| L1 | 11 | 345 |
| E6 | 8 | 87 |
| E4 | 8 | 91 |
| E1 | 11 | 498 |
| E1 | 8 | 78 |
| E1 | 9 | 78 |
| E2 | 10 | 334 |
| L1 | 9 | 57 |
| L1 | 11 | 57 |
| E1 | 8 | 317 |
| L2 | 11 | 339 |
| E1 | 8 | 239 |
| L1 | 9 | 21 |
| E7 | 8 | 90 |
| E5 | 8 | 74 |
| E5 | 10 | 74 |
| E5 | 11 | 74 |
| E2 | 8 | 152 |
| E1 | 11 | 48 |
| E7 | 10 | 40 |

TABLE XVII A-continued

HPV6A
HLA-A11 Motif Peptides

| 2 | 3 | 4 |
|---|---|---|
| L2 | 9 | 427 |
| L2 | 11 | 427 |
| L1 | 11 | 69 |
| L1 | 10 | 155 |
| L1 | 9 | 44 |
| L1 | 10 | 44 |
| L2 | 9 | 222 |
| E1 | 8 | 477 |
| E1 | 10 | 477 |
| L1 | 11 | 112 |
| E1 | 11 | 333 |
| E1 | 10 | 499 |
| E6 | 9 | 53 |
| E2 | 8 | 30 |
| E2 | 9 | 30 |
| E6 | 9 | 100 |
| E6 | 10 | 100 |
| E4 | 10 | 7 |
| E4 | 11 | 7 |
| E1 | 9 | 275 |
| E5 | 9 | 46 |
| E1 | 9 | 278 |
| E1 | 11 | 278 |
| E2 | 9 | 169 |
| E2 | 10 | 169 |
| E1 | 10 | 284 |
| L1 | 8 | 141 |
| L1 | 9 | 114 |
| L1 | 10 | 114 |
| L1 | 10 | 62 |
| E2 | 9 | 206 |
| L1 | 9 | 484 |
| L1 | 10 | 484 |
| L1 | 11 | 484 |
| L1 | 10 | 17 |
| L1 | 10 | 296 |
| L2 | 11 | 259 |
| L2 | 8 | 364 |
| L1 | 8 | 27 |
| L1 | 9 | 27 |
| L2 | 11 | 146 |
| E1 | 9 | 565 |
| E2 | 11 | 333 |
| L1 | 8 | 327 |
| E2 | 9 | 335 |
| E1 | 8 | 238 |
| E1 | 9 | 238 |
| L1 | 10 | 20 |
| E2 | 9 | 349 |
| E2 | 10 | 349 |
| E2 | 11 | 349 |
| L1 | 8 | 72 |
| L1 | 8 | 58 |
| L1 | 10 | 58 |
| L1 | 11 | 58 |
| E2 | 11 | 58 |
| E7 | 10 | 68 |
| L1 | 10 | 97 |
| E2 | 8 | 321 |
| E2 | 9 | 321 |
| E2 | 10 | 321 |
| E1 | 10 | 17 |
| E1 | 10 | 272 |
| E1 | 8 | 426 |
| E5 | 8 | 36 |
| E1 | 10 | 340 |
| E1 | 9 | 530 |
| E1 | 8 | 464 |
| L1 | 8 | 308 |
| E1 | 9 | 510 |
| E2 | 8 | 92 |
| E2 | 11 | 145 |
| E1 | 9 | 237 |
| E1 | 10 | 237 |

TABLE XVII A-continued

HPV6A
HLA-A11 Motif Peptides

| 2 | 3 | 4 |
|---|---|---|
| E6 | 11 | 61 |
| E6 | 10 | 85 |
| E1 | 8 | 76 |
| E1 | 9 | 76 |
| E1 | 10 | 76 |
| E1 | 11 | 76 |
| E6 | 11 | 46 |
| E5 | 8 | 76 |
| E5 | 9 | 76 |
| E5 | 10 | 76 |
| L2 | 8 | 441 |
| L2 | 9 | 441 |
| L1 | 9 | 48 |
| L1 | 10 | 238 |
| L1 | 11 | 238 |
| E2 | 11 | 178 |
| E4 | 8 | 12 |
| L2 | 10 | 435 |
| L2 | 11 | 435 |
| L1 | 9 | 230 |
| L1 | 8 | 358 |
| L2 | 11 | 296 |
| E6 | 9 | 44 |
| E2 | 9 | 159 |
| E2 | 10 | 159 |
| L1 | 9 | 350 |
| L1 | 11 | 350 |
| E1 | 10 | 402 |
| E1 | 11 | 402 |
| E4 | 11 | 6 |
| E2 | 10 | 168 |
| E2 | 11 | 168 |
| L2 | 9 | 71 |
| L1 | 10 | 10 |
| E2 | 10 | 138 |
| L1 | 11 | 415 |
| L1 | 9 | 26 |
| L1 | 10 | 26 |
| E2 | 8 | 131 |

TABLE XVII B

HPV6B
HLA-A11 Motif Peptides

| 2 | 3 | 4 |
|---|---|---|
| E6 | 10 | 62 |
| L1 | 8 | 234 |
| L2 | 8 | 329 |
| E1 | 8 | 206 |
| L1 | 9 | 489 |
| L1 | 11 | 489 |
| L2 | 10 | 340 |
| E4 | 9 | 12 |
| E4 | 11 | 12 |
| E6 | 9 | 63 |
| E6 | 11 | 63 |
| E6 | 9 | 65 |
| E2 | 10 | 10 |
| L1 | 9 | 98 |
| E1 | 10 | 392 |
| E1 | 11 | 392 |
| L2 | 8 | 238 |
| L2 | 9 | 275 |
| L2 | 10 | 275 |
| E1 | 11 | 637 |
| L2 | 11 | 116 |
| E1 | 8 | 193 |
| E1 | 10 | 193 |
| E1 | 11 | 190 |

TABLE XVII B-continued

HPV6B
HLA-A11 Motif Peptides

| 2 | 3 | 4 |
|---|---|---|
| E1 | 9 | 144 |
| E1 | 10 | 144 |
| L2 | 10 | 286 |
| L2 | 11 | 286 |
| E1 | 9 | 112 |
| E1 | 10 | 112 |
| L2 | 10 | 140 |
| L1 | 11 | 420 |
| E1 | 10 | 475 |
| E1 | 11 | 65 |
| E6 | 8 | 37 |
| E6 | 10 | 37 |
| L1 | 11 | 203 |
| L1 | 8 | 54 |
| L1 | 8 | 487 |
| L1 | 9 | 487 |
| L1 | 11 | 487 |
| L2 | 11 | 12 |
| L2 | 8 | 288 |
| L2 | 9 | 288 |
| L2 | 11 | 288 |
| E2 | 8 | 322 |
| E2 | 9 | 322 |
| L1 | 11 | 36 |
| L1 | 9 | 342 |
| L1 | 8 | 22 |
| E1 | 8 | 407 |
| E1 | 9 | 407 |
| L2 | 9 | 14 |
| E1 | 8 | 525 |
| E6 | 9 | 10 |
| E6 | 9 | 86 |
| E1 | 8 | 77 |
| E1 | 9 | 77 |
| E1 | 10 | 77 |
| E1 | 9 | 101 |
| L1 | 10 | 43 |
| L1 | 11 | 43 |
| E5B | 9 | 36 |
| E5B | 11 | 36 |
| E2 | 8 | 231 |
| E2 | 9 | 231 |
| E2 | 11 | 231 |
| L1 | 10 | 483 |
| L1 | 11 | 483 |
| E1 | 11 | 601 |
| E6 | 8 | 64 |
| E6 | 10 | 64 |
| E2 | 8 | 124 |
| L1 | 8 | 157 |
| L1 | 11 | 157 |
| L1 | 10 | 341 |
| E1 | 8 | 406 |
| E1 | 9 | 406 |
| E1 | 10 | 406 |
| E7 | 10 | 57 |
| E7 | 9 | 58 |
| E6 | 8 | 66 |
| E1 | 11 | 215 |
| E2 | 9 | 299 |
| E2 | 10 | 299 |
| E2 | 11 | 299 |
| E7 | 8 | 59 |
| E2 | 8 | 161 |
| L1 | 10 | 221 |
| E6 | 11 | 67 |
| E2 | 8 | 296 |
| E2 | 10 | 35 |
| E2 | 11 | 35 |
| E2 | 8 | 248 |
| E5B | 9 | 53 |
| E5B | 10 | 53 |
| E5B | 10 | 48 |
| L1 | 8 | 99 |

TABLE XVII B-continued

HPV6B
HLA-A11 Motif Peptides

| 2 | 3 | 4 |
|---|---|---|
| E6 | 9 | 131 |
| E1 | 8 | 640 |
| E2 | 11 | 9 |
| E1 | 10 | 111 |
| E1 | 11 | 111 |
| E1 | 9 | 524 |
| E2 | 8 | 230 |
| E2 | 9 | 230 |
| E2 | 10 | 230 |
| L1 | 11 | 24 |
| E1 | 8 | 405 |
| E1 | 9 | 405 |
| E1 | 10 | 405 |
| E1 | 11 | 405 |
| E1 | 10 | 523 |
| E5B | 8 | 55 |
| E1 | 10 | 49 |
| E2 | 10 | 122 |
| E1 | 9 | 542 |
| E1 | 10 | 542 |
| E1 | 11 | 542 |
| E7 | 9 | 41 |
| E7 | 11 | 41 |
| E1 | 9 | 161 |
| E1 | 9 | 631 |
| E4 | 10 | 99 |
| L1 | 8 | 219 |
| L1 | 9 | 219 |
| E6 | 8 | 96 |
| E6 | 10 | 96 |
| E1 | 8 | 570 |
| E1 | 9 | 570 |
| E1 | 10 | 570 |
| E2 | 8 | 25 |
| E2 | 10 | 25 |
| E1 | 10 | 222 |
| E2 | 8 | 313 |
| E1 | 11 | 81 |
| E7 | 11 | 14 |
| E1 | 9 | 203 |
| E1 | 11 | 203 |
| E2 | 9 | 141 |
| L1 | 10 | 138 |
| L1 | 11 | 138 |
| E7 | 8 | 44 |
| L1 | 11 | 84 |
| E1 | 11 | 166 |
| E1 | 11 | 73 |
| L1 | 11 | 269 |
| L2 | 8 | 30 |
| E6 | 10 | 99 |
| E6 | 11 | 99 |
| L2 | 8 | 258 |
| E2 | 11 | 348 |
| E1 | 10 | 178 |
| E2 | 9 | 174 |
| E2 | 10 | 174 |
| L2 | 8 | 274 |
| L2 | 10 | 274 |
| L2 | 11 | 274 |
| E1 | 10 | 143 |
| E1 | 11 | 143 |
| E1 | 8 | 336 |
| E1 | 8 | 180 |
| E1 | 10 | 180 |
| E1 | 8 | 62 |
| L1 | 9 | 299 |
| E1 | 10 | 100 |
| E2 | 9 | 229 |
| E2 | 10 | 229 |
| E2 | 11 | 229 |
| E1 | 10 | 36 |
| E1 | 10 | 630 |
| E1 | 8 | 574 |

TABLE XVII B-continued

HPV6B
HLA-A11 Motif Peptides

| 2 | 3 | 4 |
|---|---|---|
| E1 | 10 | 574 |
| L2 | 9 | 257 |
| E6 | 9 | 69 |
| E6 | 10 | 69 |
| E6 | 11 | 69 |
| E1 | 8 | 453 |
| E1 | 10 | 453 |
| L2 | 11 | 255 |
| E1 | 9 | 375 |
| E1 | 10 | 105 |
| E6 | 8 | 42 |
| E6 | 9 | 42 |
| E6 | 11 | 42 |
| L1 | 9 | 453 |
| L1 | 10 | 453 |
| E1 | 9 | 197 |
| E1 | 8 | 604 |
| E1 | 9 | 131 |
| E2 | 11 | 17 |
| E2 | 11 | 74 |
| E1 | 8 | 417 |
| E2 | 8 | 100 |
| E2 | 9 | 100 |
| E1 | 9 | 157 |
| E1 | 10 | 303 |
| E2 | 8 | 21 |
| E2 | 9 | 21 |
| E1 | 8 | 373 |
| E1 | 11 | 373 |
| E2 | 8 | 80 |
| E2 | 9 | 293 |
| E2 | 10 | 293 |
| E2 | 11 | 293 |
| E2 | 9 | 39 |
| E7 | 11 | 39 |
| E6 | 11 | 113 |
| E2 | 10 | 205 |
| L1 | 8 | 206 |
| L1 | 8 | 252 |
| L2 | 8 | 442 |
| E2 | 11 | 121 |
| E2 | 9 | 312 |
| E1 | 9 | 595 |
| E5A | 10 | 67 |
| L1 | 11 | 244 |
| E1 | 10 | 216 |
| E1 | 9 | 50 |
| E1 | 9 | 220 |
| E6 | 9 | 126 |
| E6 | 11 | 126 |
| E1 | 9 | 454 |
| L2 | 8 | 428 |
| L2 | 10 | 428 |
| E1 | 9 | 494 |
| L1 | 8 | 463 |
| L1 | 10 | 463 |
| E5A | 9 | 68 |
| E4 | 10 | 31 |
| E4 | 11 | 31 |
| E1 | 9 | 393 |
| E1 | 10 | 393 |
| L1 | 10 | 245 |
| L1 | 11 | 245 |
| L2 | 11 | 239 |
| E1 | 10 | 457 |
| L2 | 8 | 276 |
| L2 | 9 | 276 |
| E1 | 9 | 18 |
| L1 | 9 | 303 |
| E1 | 9 | 67 |
| E1 | 10 | 67 |
| L1 | 8 | 49 |
| L1 | 8 | 450 |
| E1 | 11 | 587 |

TABLE XVII B-continued

HPV6B
HLA-A11 Motif Peptides

| 2 | 3 | 4 |
|---|---|---|
| E2 | 8 | 171 |
| L1 | 9 | 326 |
| L2 | 10 | 117 |
| E4 | 8 | 2 |
| L2 | 8 | 314 |
| E2 | 9 | 123 |
| L1 | 9 | 156 |
| E1 | 8 | 384 |
| E1 | 10 | 160 |
| E5B | 8 | 39 |
| E5B | 9 | 39 |
| L1 | 9 | 239 |
| L1 | 10 | 239 |
| L2 | 9 | 433 |
| E1 | 11 | 159 |
| L1 | 9 | 132 |
| L2 | 11 | 58 |
| E1 | 9 | 194 |
| E2 | 10 | 156 |
| E1 | 8 | 350 |
| E5B | 8 | 28 |
| E1 | 9 | 217 |
| L2 | 11 | 292 |
| L2 | 8 | 223 |
| E5B | 9 | 25 |
| E5B | 10 | 25 |
| E5B | 11 | 25 |
| E2 | 9 | 55 |
| E1 | 9 | 273 |
| E1 | 11 | 273 |
| E2 | 10 | 262 |
| L1 | 8 | 133 |
| E1 | 8 | 543 |
| E1 | 9 | 543 |
| E1 | 10 | 543 |
| E1 | 11 | 543 |
| L1 | 11 | 277 |
| E1 | 11 | 438 |
| L2 | 11 | 431 |
| L1 | 11 | 130 |
| L2 | 10 | 62 |
| E1 | 11 | 431 |
| L2 | 9 | 303 |
| L2 | 10 | 303 |
| E1 | 8 | 632 |
| E2 | 10 | 179 |
| E1 | 10 | 191 |
| L2 | 11 | 215 |
| L2 | 10 | 25 |
| L2 | 8 | 64 |
| L2 | 9 | 60 |
| E1 | 8 | 145 |
| E1 | 9 | 145 |
| L1 | 8 | 407 |
| L1 | 9 | 407 |
| L1 | 9 | 222 |
| E4 | 9 | 100 |
| E1 | 9 | 316 |
| L1 | 9 | 478 |
| L1 | 10 | 113 |
| L1 | 11 | 113 |
| E1 | 10 | 415 |
| E2 | 8 | 330 |
| E1 | 11 | 508 |
| E6 | 8 | 71 |
| E6 | 9 | 71 |
| E1 | 9 | 349 |
| E7 | 8 | 2 |
| L2 | 8 | 312 |
| L2 | 10 | 312 |
| E2 | 11 | 53 |
| E2 | 10 | 255 |
| E6 | 10 | 119 |
| E2 | 10 | 78 |
| E2 | 11 | 310 |
| E6 | 10 | 50 |
| E4 | 8 | 20 |
| E4 | 9 | 20 |
| E4 | 10 | 20 |
| E2 | 9 | 70 |
| E5B | 11 | 51 |
| E2 | 8 | 264 |
| E2 | 11 | 264 |
| L2 | 10 | 37 |
| E1 | 9 | 246 |
| E2 | 10 | 149 |
| E2 | 11 | 149 |
| L2 | 8 | 3 |
| L2 | 9 | 3 |
| E5B | 9 | 42 |
| E5B | 10 | 42 |
| E6 | 11 | 25 |
| L2 | 11 | 306 |
| L2 | 8 | 149 |
| E2 | 9 | 29 |
| E2 | 10 | 29 |
| E1 | 8 | 376 |
| E1 | 11 | 474 |
| L2 | 11 | 326 |
| L2 | 9 | 287 |
| L2 | 10 | 287 |
| E1 | 11 | 370 |
| L1 | 8 | 220 |
| L1 | 11 | 220 |
| E1 | 8 | 51 |
| L1 | 9 | 218 |
| L1 | 10 | 218 |
| E1 | 8 | 569 |
| E1 | 9 | 569 |
| E1 | 10 | 569 |
| E1 | 11 | 569 |
| E1 | 8 | 221 |
| E1 | 11 | 221 |
| L1 | 9 | 32 |
| L2 | 9 | 313 |
| E1 | 10 | 334 |
| E4 | 11 | 6 |
| E2 | 10 | 54 |
| E2 | 9 | 256 |
| L2 | 8 | 299 |
| L2 | 10 | 299 |
| L2 | 10 | 59 |
| L1 | 8 | 272 |
| E6 | 9 | 97 |
| L2 | 9 | 141 |
| E1 | 8 | 195 |
| E1 | 11 | 195 |
| L2 | 11 | 178 |
| E6 | 9 | 120 |
| E6 | 9 | 74 |
| L2 | 9 | 180 |
| E1 | 11 | 492 |
| E2 | 11 | 356 |
| E1 | 9 | 500 |
| E1 | 9 | 106 |
| E2 | 11 | 315 |
| L1 | 10 | 421 |
| L2 | 9 | 429 |
| E1 | 8 | 571 |
| E1 | 9 | 571 |
| E1 | 11 | 571 |
| L1 | 10 | 376 |
| E2 | 8 | 267 |
| E2 | 10 | 267 |
| E2 | 11 | 267 |
| E1 | 9 | 341 |
| L2 | 8 | 82 |
| L2 | 8 | 247 |

TABLE XVII B-continued

HPV6B
HLA-A11 Motif Peptides

| 2 | 3 | 4 |
|---|---|---|
| E7 | 9 | 89 |
| E5B | 11 | 23 |
| E1 | 9 | 476 |
| E1 | 11 | 476 |
| E5A | 10 | 34 |
| E2 | 9 | 45 |
| L1 | 8 | 486 |
| L1 | 9 | 486 |
| L1 | 10 | 486 |
| E2 | 10 | 298 |
| E2 | 11 | 298 |
| E5B | 8 | 44 |
| E2 | 11 | 34 |
| E5B | 11 | 47 |
| E1 | 8 | 404 |
| E1 | 9 | 404 |
| E1 | 10 | 404 |
| E1 | 11 | 404 |
| E4 | 11 | 98 |
| E1 | 10 | 202 |
| E1 | 11 | 460 |
| L1 | 8 | 462 |
| L1 | 9 | 462 |
| L1 | 11 | 462 |
| L1 | 9 | 449 |
| E2 | 11 | 68 |
| E2 | 11 | 155 |
| E1 | 9 | 433 |
| E6 | 10 | 73 |
| E2 | 8 | 351 |
| E2 | 9 | 351 |
| E1 | 10 | 312 |
| E2 | 8 | 359 |
| E1 | 9 | 254 |
| E1 | 11 | 254 |
| E6 | 9 | 128 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| E6 | 10 | 35 |
| L1 | 11 | 437 |
| E1 | 8 | 286 |
| E6 | 8 | 18 |
| L1 | 10 | 56 |
| E2 | 9 | 165 |
| E2 | 9 | 147 |
| E6 | 8 | 116 |
| E6 | 10 | 116 |
| E1 | 10 | 121 |
| E6 | 8 | 52 |
| E6 | 10 | 52 |
| E1 | 11 | 283 |
| E2 | 8 | 63 |
| L1 | 8 | 61 |
| L1 | 11 | 61 |
| L1 | 8 | 19 |
| L1 | 11 | 19 |
| L1 | 9 | 71 |
| L1 | 11 | 42 |
| L1 | 11 | 340 |
| E6 | 8 | 111 |
| E6 | 9 | 111 |
| E6 | 11 | 106 |
| E6 | 10 | 16 |
| E4 | 8 | 45 |
| E1 | 8 | 110 |
| E1 | 11 | 110 |
| E1 | 11 | 522 |

TABLE XVII B-continued

HPV6B
HLA-A11 Motif Peptides

| 2 | 3 | 4 |
|---|---|---|
| E1 | 10 | 541 |
| E1 | 11 | 541 |
| L1 | 8 | 454 |
| L1 | 9 | 454 |
| E6 | 8 | 98 |
| E6 | 11 | 98 |
| L2 | 8 | 142 |
| E1 | 11 | 235 |
| E2 | 10 | 311 |
| L1 | 8 | 87 |
| L1 | 10 | 302 |
| E1 | 10 | 66 |
| E1 | 11 | 66 |
| E6 | 8 | 54 |
| L1 | 10 | 325 |
| L1 | 9 | 161 |
| E1 | 8 | 495 |
| E5B | 8 | 27 |
| E5B | 9 | 27 |
| L1 | 11 | 459 |
| L1 | 8 | 110 |
| E1 | 8 | 255 |
| E1 | 10 | 255 |
| L1 | 9 | 271 |
| E6 | 8 | 101 |
| E6 | 9 | 101 |
| E1 | 9 | 223 |
| L2 | 10 | 179 |
| E2 | 9 | 266 |
| E2 | 11 | 266 |
| L2 | 9 | 246 |
| E5A | 11 | 33 |
| L1 | 8 | 41 |
| E1 | 11 | 540 |
| E4 | 9 | 18 |
| E4 | 10 | 18 |
| E4 | 11 | 18 |
| E4 | 8 | 34 |
| E1 | 8 | 198 |
| L1 | 9 | 464 |
| E1 | 8 | 279 |
| E1 | 10 | 279 |
| E5A | 8 | 69 |
| E5A | 10 | 72 |
| E1 | 8 | 276 |
| E1 | 11 | 276 |
| E1 | 11 | 563 |
| E5B | 11 | 31 |
| E6 | 8 | 129 |
| E6 | 11 | 129 |
| E7 | 11 | 87 |
| E4 | 9 | 32 |
| E4 | 10 | 32 |
| E1 | 8 | 394 |
| E1 | 9 | 394 |
| E1 | 11 | 394 |
| L1 | 8 | 378 |
| L1 | 10 | 378 |
| E1 | 8 | 218 |
| E1 | 11 | 218 |
| L1 | 9 | 439 |
| L1 | 11 | 439 |
| L2 | 10 | 240 |
| E1 | 8 | 132 |
| E1 | 9 | 358 |
| E4 | 8 | 91 |
| E6 | 8 | 121 |
| E1 | 9 | 458 |
| E1 | 9 | 115 |
| E1 | 10 | 115 |
| E1 | 11 | 115 |
| E6 | 9 | 38 |
| E6 | 11 | 38 |
| E5A | 9 | 73 |

TABLE XVII B-continued

HPV6B
HLA-A11 Motif Peptides

| 2 | 3 | 4 |
|---|---|---|
| E5A | 11 | 73 |
| E1 | 10 | 277 |
| E5A | 8 | 47 |
| L2 | 10 | 293 |
| L1 | 11 | 295 |
| E1 | 10 | 564 |
| E7 | 11 | 67 |
| L1 | 9 | 233 |
| E4 | 10 | 11 |
| L2 | 8 | 1 |
| L2 | 9 | 1 |
| L2 | 10 | 1 |
| L2 | 11 | 1 |
| E1 | 11 | 409 |
| L2 | 8 | 277 |
| E2 | 10 | 129 |
| L1 | 9 | 251 |
| E4 | 8 | 1 |
| E4 | 9 | 1 |
| E5B | 8 | 26 |
| E5B | 9 | 26 |
| E5B | 10 | 26 |
| L1 | 10 | 204 |
| E1 | 8 | 546 |
| E1 | 8 | 421 |
| E1 | 9 | 421 |
| E1 | 10 | 421 |
| E2 | 8 | 151 |
| E2 | 9 | 151 |
| E1 | 8 | 19 |
| L1 | 11 | 154 |
| E1 | 8 | 274 |
| E1 | 10 | 274 |
| E2 | 8 | 71 |
| E6 | 9 | 36 |
| E6 | 11 | 36 |
| E2 | 8 | 295 |
| E2 | 9 | 295 |
| E5B | 10 | 52 |
| E5B | 11 | 52 |
| E6 | 10 | 130 |
| E5B | 8 | 54 |
| E5B | 9 | 54 |
| E2 | 8 | 142 |
| L1 | 9 | 205 |
| E2 | 8 | 170 |
| E2 | 9 | 170 |
| E1 | 8 | 158 |
| L1 | 8 | 406 |
| L1 | 9 | 406 |
| L1 | 10 | 406 |
| E1 | 9 | 568 |
| E1 | 10 | 568 |
| E1 | 11 | 568 |
| E1 | 10 | 451 |
| L1 | 10 | 31 |
| E7 | 10 | 88 |
| E2 | 10 | 265 |
| E4 | 8 | 33 |
| E4 | 9 | 33 |
| L1 | 10 | 438 |
| E1 | 8 | 397 |
| E2 | 8 | 269 |
| E2 | 9 | 269 |
| L1 | 9 | 352 |
| L1 | 10 | 352 |
| E1 | 11 | 59 |
| E1 | 8 | 395 |
| E1 | 10 | 395 |
| E2 | 8 | 22 |
| E2 | 11 | 22 |
| L2 | 9 | 38 |
| E1 | 10 | 607 |
| L2 | 9 | 237 |

TABLE XVII B-continued

HPV6B
HLA-A11 Motif Peptides

| 2 | 3 | 4 |
|---|---|---|
| L2 | 11 | 285 |
| L2 | 11 | 139 |
| E5A | 8 | 78 |
| L1 | 11 | 482 |
| L2 | 8 | 438 |
| L2 | 9 | 438 |
| L2 | 10 | 438 |
| L2 | 11 | 438 |
| E2 | 9 | 247 |
| E1 | 9 | 528 |
| E1 | 11 | 528 |
| L2 | 10 | 272 |
| E7 | 9 | 18 |
| L2 | 9 | 29 |
| L1 | 11 | 228 |
| E1 | 10 | 594 |
| E4 | 11 | 30 |
| E1 | 11 | 456 |
| L2 | 8 | 355 |
| L2 | 8 | 214 |
| L1 | 10 | 217 |
| L1 | 11 | 217 |
| E1 | 8 | 442 |
| E6 | 9 | 110 |
| E6 | 10 | 110 |
| E4 | 8 | 44 |
| E4 | 9 | 44 |
| L1 | 8 | 160 |
| L1 | 10 | 160 |
| L1 | 9 | 109 |
| E2 | 8 | 61 |
| E2 | 10 | 61 |
| E1 | 8 | 545 |
| E1 | 9 | 545 |
| L1 | 9 | 405 |
| L1 | 10 | 405 |
| L1 | 11 | 405 |
| E1 | 8 | 590 |
| L2 | 10 | 80 |
| E1 | 8 | 182 |
| L1 | 11 | 426 |
| L2 | 10 | 426 |
| L1 | 9 | 266 |
| L2 | 8 | 212 |
| L2 | 10 | 212 |
| L1 | 11 | 16 |
| L2 | 9 | 363 |
| L2 | 9 | 328 |
| E4 | 9 | 48 |
| E4 | 10 | 48 |
| E4 | 11 | 48 |
| E4 | 10 | 54 |
| E7 | 8 | 70 |
| L2 | 8 | 342 |
| E6 | 9 | 95 |
| E6 | 11 | 95 |
| E2 | 8 | 140 |
| E2 | 10 | 140 |
| L1 | 11 | 137 |
| E7 | 9 | 43 |
| E5A | 11 | 66 |
| E2 | 11 | 163 |
| E2 | 10 | 289 |
| L2 | 8 | 262 |
| E5B | 9 | 38 |
| E5B | 10 | 38 |
| E2 | 8 | 291 |
| E2 | 11 | 291 |
| E6 | 8 | 28 |
| E6 | 11 | 15 |
| L1 | 11 | 301 |
| L1 | 11 | 324 |
| E4 | 9 | 14 |
| L1 | 10 | 232 |

TABLE XVII B-continued

HPV6B
HLA-A11 Motif Peptides

| 2 | 3 | 4 |
|---|---|---|
| L1 | 10 | 250 |
| E2 | 9 | 76 |
| E1 | 8 | 305 |
| E1 | 11 | 450 |
| E1 | 8 | 314 |
| E1 | 11 | 314 |
| L1 | 11 | 466 |
| E2 | 11 | 245 |
| L1 | 9 | 417 |
| E2 | 9 | 103 |
| E2 | 10 | 103 |
| E2 | 11 | 103 |
| E2 | 9 | 233 |
| E1 | 10 | 128 |
| E2 | 11 | 218 |
| E1 | 9 | 205 |
| E1 | 11 | 391 |
| L1 | 9 | 53 |
| L2 | 8 | 11 |
| E5B | 8 | 35 |
| E5B | 10 | 35 |
| E2 | 8 | 108 |
| E1 | 9 | 639 |
| E1 | 8 | 169 |
| E6 | 10 | 125 |
| E1 | 8 | 281 |
| E1 | 9 | 383 |
| E2 | 8 | 113 |
| L2 | 8 | 291 |
| L1 | 11 | 470 |
| L2 | 10 | 302 |
| L2 | 11 | 302 |
| L2 | 9 | 298 |
| L2 | 11 | 298 |
| E1 | 9 | 109 |
| L1 | 8 | 241 |
| L2 | 10 | 281 |
| L2 | 11 | 281 |
| L2 | 10 | 245 |
| L1 | 9 | 40 |
| E2 | 8 | 303 |
| L2 | 9 | 308 |
| L2 | 11 | 308 |
| L1 | 9 | 472 |
| L1 | 10 | 472 |
| L1 | 11 | 476 |
| L1 | 9 | 279 |
| L2 | 10 | 221 |
| L1 | 8 | 140 |
| L1 | 9 | 140 |
| L1 | 8 | 488 |
| L1 | 10 | 488 |
| L1 | 9 | 379 |
| L2 | 8 | 181 |
| L2 | 10 | 13 |
| E6 | 10 | 9 |
| L1 | 8 | 353 |
| L1 | 9 | 353 |
| L2 | 11 | 352 |
| E1 | 10 | 219 |
| E1 | 10 | 493 |
| L1 | 8 | 440 |
| L1 | 10 | 440 |
| L2 | 10 | 432 |
| L1 | 10 | 131 |
| L1 | 8 | 115 |
| L1 | 9 | 115 |
| L2 | 8 | 309 |
| L2 | 10 | 309 |
| L2 | 11 | 309 |
| E2 | 11 | 261 |
| L2 | 9 | 63 |
| E1 | 10 | 315 |
| L1 | 9 | 63 |
| L1 | 10 | 467 |
| E1 | 8 | 422 |
| E1 | 9 | 422 |
| E2 | 8 | 207 |
| L1 | 8 | 474 |
| E1 | 8 | 247 |
| L1 | 11 | 375 |
| L2 | 9 | 81 |
| E1 | 10 | 60 |
| L1 | 9 | 86 |
| E4 | 9 | 90 |
| L2 | 8 | 304 |
| L2 | 9 | 304 |
| E2 | 9 | 150 |
| E2 | 10 | 150 |
| E2 | 8 | 294 |
| E2 | 9 | 294 |
| E2 | 10 | 294 |
| E1 | 10 | 567 |
| E1 | 11 | 567 |
| E1 | 9 | 396 |
| E1 | 11 | 606 |
| L1 | 9 | 297 |
| L1 | 11 | 297 |
| L1 | 11 | 451 |
| L1 | 8 | 473 |
| L1 | 9 | 473 |
| E2 | 8 | 323 |
| L1 | 10 | 85 |
| E4 | 10 | 89 |
| L1 | 9 | 38 |
| L1 | 11 | 38 |
| L1 | 10 | 37 |
| L2 | 11 | 209 |
| E2 | 10 | 316 |
| L1 | 9 | 347 |
| L1 | 10 | 347 |
| E2 | 10 | 23 |
| E2 | 9 | 180 |
| E2 | 9 | 220 |
| L2 | 9 | 241 |
| L2 | 10 | 210 |
| E2 | 9 | 317 |
| L1 | 8 | 348 |
| L1 | 9 | 348 |
| L1 | 11 | 348 |
| E2 | 8 | 40 |
| E5A | 10 | 45 |
| L2 | 10 | 260 |
| L1 | 8 | 343 |
| E6 | 9 | 40 |
| E6 | 10 | 40 |
| E6 | 11 | 40 |
| E1 | 9 | 192 |
| E1 | 11 | 192 |
| L2 | 10 | 216 |
| E7 | 11 | 56 |
| E2 | 8 | 160 |
| E2 | 9 | 160 |
| L2 | 9 | 26 |
| L1 | 9 | 422 |
| L1 | 11 | 422 |
| E2 | 9 | 24 |
| E2 | 11 | 24 |
| L2 | 11 | 235 |
| E1 | 10 | 588 |
| E1 | 10 | 167 |
| L2 | 8 | 430 |
| L2 | 8 | 61 |
| L2 | 11 | 61 |
| L2 | 11 | 24 |
| E1 | 8 | 146 |
| L1 | 10 | 477 |
| L2 | 11 | 69 |

TABLE XVII B-continued

HPV6B
HLA-A11 Motif Peptides

| 2 | 3 | 4 |
|---|---|---|
| L2 | 8 | 39 |
| L1 | 8 | 408 |
| L1 | 10 | 270 |
| E5A | 11 | 71 |
| E6 | 10 | 26 |
| L1 | 9 | 377 |
| L1 | 11 | 377 |
| E2 | 8 | 221 |
| E1 | 8 | 408 |
| E2 | 11 | 128 |
| E5B | 10 | 59 |
| L1 | 11 | 30 |
| E2 | 9 | 268 |
| E2 | 10 | 268 |
| L1 | 8 | 351 |
| L1 | 10 | 351 |
| L1 | 11 | 351 |
| E1 | 9 | 608 |
| E6 | 11 | 8 |
| L2 | 10 | 147 |
| E1 | 8 | 566 |
| E1 | 11 | 566 |
| E4 | 11 | 88 |
| L1 | 10 | 346 |
| L1 | 11 | 346 |
| E2 | 10 | 219 |
| L1 | 8 | 280 |
| E5A | 11 | 44 |
| E2 | 11 | 97 |
| E6 | 8 | 39 |
| E6 | 10 | 39 |
| E6 | 11 | 39 |
| L1 | 8 | 223 |
| E5B | 8 | 63 |
| E6 | 8 | 11 |
| L1 | 11 | 345 |
| E6 | 8 | 87 |
| E4 | 8 | 101 |
| E1 | 11 | 498 |
| E1 | 8 | 78 |
| E1 | 9 | 78 |
| E2 | 10 | 334 |
| L1 | 9 | 57 |
| L1 | 11 | 57 |
| E1 | 8 | 317 |
| L2 | 11 | 339 |
| E1 | 8 | 239 |
| L1 | 9 | 21 |
| E7 | 8 | 90 |
| E5A | 8 | 74 |
| E5A | 10 | 74 |
| E5A | 11 | 74 |
| E2 | 8 | 152 |
| E1 | 11 | 48 |
| E7 | 10 | 40 |
| L2 | 9 | 427 |
| L2 | 11 | 427 |
| L1 | 11 | 69 |
| L1 | 10 | 155 |
| L1 | 9 | 44 |
| L1 | 10 | 44 |
| L2 | 9 | 222 |
| E5B | 10 | 24 |
| E5B | 11 | 24 |
| E1 | 8 | 477 |
| E1 | 10 | 477 |
| L1 | 11 | 112 |
| E1 | 11 | 333 |
| E1 | 10 | 499 |
| E6 | 9 | 53 |
| E2 | 8 | 30 |
| E2 | 9 | 30 |
| E6 | 9 | 100 |
| E6 | 10 | 100 |
| E4 | 10 | 17 |
| E4 | 11 | 17 |
| E1 | 9 | 278 |
| E1 | 11 | 278 |
| E1 | 9 | 275 |
| E5A | 9 | 46 |
| E4 | 11 | 10 |
| E2 | 9 | 169 |
| E2 | 10 | 169 |
| E1 | 10 | 284 |
| L1 | 8 | 141 |
| L1 | 9 | 114 |
| L1 | 10 | 114 |
| L1 | 10 | 62 |
| E2 | 9 | 206 |
| L1 | 9 | 484 |
| L1 | 10 | 484 |
| L1 | 11 | 484 |
| L1 | 10 | 17 |
| L1 | 10 | 296 |
| L2 | 11 | 259 |
| E5B | 11 | 58 |
| L2 | 8 | 364 |
| L1 | 8 | 27 |
| L1 | 9 | 27 |
| L2 | 11 | 146 |
| E1 | 9 | 565 |
| E2 | 11 | 333 |
| L1 | 8 | 327 |
| E2 | 9 | 335 |
| E1 | 8 | 238 |
| E1 | 9 | 238 |
| L1 | 10 | 20 |
| E2 | 10 | 349 |
| E2 | 11 | 349 |
| L1 | 8 | 72 |
| L1 | 8 | 58 |
| L1 | 10 | 58 |
| L1 | 11 | 58 |
| E2 | 11 | 58 |
| E7 | 10 | 68 |
| L1 | 10 | 97 |
| E2 | 8 | 321 |
| E2 | 9 | 321 |
| E2 | 10 | 321 |
| E1 | 10 | 17 |
| E1 | 10 | 272 |
| E1 | 8 | 426 |
| E5A | 8 | 36 |
| E1 | 10 | 340 |
| E1 | 9 | 530 |
| E1 | 8 | 464 |
| L1 | 8 | 308 |
| E1 | 9 | 510 |
| E2 | 8 | 92 |
| E2 | 11 | 145 |
| E1 | 9 | 237 |
| E1 | 10 | 237 |
| E6 | 11 | 61 |
| E6 | 10 | 85 |
| E1 | 8 | 76 |
| E1 | 9 | 76 |
| E1 | 10 | 76 |
| E1 | 11 | 76 |
| E6 | 11 | 46 |
| E5A | 8 | 76 |
| E5A | 9 | 76 |
| E5A | 10 | 76 |
| L2 | 8 | 441 |
| L2 | 9 | 441 |
| L1 | 9 | 48 |
| L1 | 10 | 238 |
| L1 | 11 | 238 |
| E2 | 11 | 178 |

TABLE XVII B-continued

HPV6B
HLA-A11 Motif Peptides

| 2 | 3 | 4 |
|---|---|---|
| E4 | 8 | 22 |
| L2 | 10 | 435 |
| L2 | 11 | 435 |
| L1 | 9 | 230 |
| L1 | 8 | 358 |
| L2 | 11 | 296 |
| E6 | 9 | 44 |
| E2 | 9 | 159 |
| E2 | 10 | 159 |
| L1 | 9 | 350 |
| L1 | 11 | 350 |
| E5B | 9 | 62 |
| E1 | 10 | 402 |
| E1 | 11 | 402 |
| E4 | 11 | 16 |
| E4 | 8 | 9 |
| E2 | 10 | 168 |
| E2 | 11 | 168 |
| L2 | 9 | 71 |
| L1 | 10 | 10 |
| E2 | 10 | 138 |
| L1 | 11 | 415 |
| L1 | 9 | 26 |
| L1 | 10 | 26 |
| E2 | 8 | 131 |

TABLE XVII C

HPV11
HLA-A11 Motif Peptides

| 2 | 3 | 4 |
|---|---|---|
| L1 | 8 | 235 |
| L2 | 8 | 328 |
| L2 | 10 | 339 |
| E4 | 9 | 12 |
| E4 | 11 | 12 |
| E1 | 8 | 144 |
| E6 | 11 | 63 |
| E6 | 9 | 65 |
| E2 | 10 | 10 |
| E4 | 10 | 55 |
| L1 | 9 | 98 |
| L1 | 11 | 236 |
| E1 | 11 | 190 |
| E1 | 11 | 235 |
| E1 | 10 | 392 |
| E1 | 11 | 392 |
| L2 | 8 | 237 |
| L2 | 9 | 274 |
| L2 | 10 | 274 |
| L2 | 10 | 215 |
| E1 | 11 | 637 |
| L2 | 9 | 62 |
| L2 | 11 | 68 |
| E1 | 9 | 112 |
| E1 | 10 | 112 |
| L2 | 10 | 139 |
| E1 | 8 | 407 |
| E1 | 9 | 407 |
| L1 | 11 | 421 |
| L2 | 9 | 80 |
| L2 | 10 | 285 |
| E1 | 10 | 475 |
| E1 | 11 | 65 |
| E6 | 8 | 37 |
| E6 | 10 | 37 |
| L1 | 11 | 204 |
| E1 | 11 | 99 |
| E1 | 9 | 608 |

TABLE XVII C-continued

HPV11
HLA-A11 Motif Peptides

| 2 | 3 | 4 |
|---|---|---|
| L2 | 11 | 11 |
| E2 | 8 | 321 |
| L1 | 11 | 36 |
| L1 | 9 | 343 |
| E2 | 8 | 197 |
| L1 | 8 | 22 |
| L2 | 9 | 13 |
| E1 | 8 | 525 |
| E6 | 9 | 10 |
| E1 | 8 | 77 |
| E1 | 9 | 77 |
| E1 | 10 | 77 |
| L1 | 8 | 349 |
| L1 | 9 | 349 |
| L1 | 11 | 349 |
| E1 | 9 | 181 |
| E1 | 9 | 101 |
| L1 | 10 | 43 |
| L1 | 11 | 43 |
| E5 | 9 | 37 |
| E5 | 9 | 26 |
| E5 | 10 | 26 |
| E5 | 11 | 26 |
| L1 | 10 | 484 |
| L1 | 11 | 484 |
| E1 | 11 | 601 |
| E6 | 10 | 64 |
| E1 | 8 | 406 |
| E1 | 9 | 406 |
| E1 | 10 | 406 |
| E5 | 8 | 46 |
| L1 | 8 | 158 |
| L1 | 11 | 158 |
| L1 | 10 | 342 |
| E7 | 10 | 57 |
| E7 | 9 | 58 |
| E6 | 8 | 66 |
| E1 | 8 | 486 |
| E1 | 11 | 215 |
| E2 | 9 | 298 |
| E2 | 10 | 298 |
| E2 | 11 | 298 |
| E7 | 8 | 59 |
| E2 | 8 | 161 |
| L1 | 10 | 222 |
| E2 | 10 | 35 |
| E2 | 11 | 35 |
| E6 | 11 | 67 |
| E2 | 8 | 295 |
| E2 | 11 | 194 |
| L1 | 8 | 99 |
| E5 | 9 | 73 |
| E5 | 11 | 73 |
| E1 | 8 | 640 |
| E2 | 11 | 9 |
| E1 | 11 | 73 |
| E1 | 10 | 111 |
| E1 | 11 | 111 |
| E1 | 10 | 607 |
| E7 | 8 | 44 |
| E7 | 9 | 44 |
| E1 | 9 | 524 |
| L1 | 11 | 24 |
| E1 | 8 | 405 |
| E1 | 9 | 405 |
| E1 | 10 | 405 |
| E1 | 11 | 405 |
| E1 | 10 | 523 |
| L1 | 11 | 270 |
| L1 | 9 | 124 |
| L2 | 9 | 429 |
| E2 | 10 | 122 |
| E1 | 9 | 542 |
| E1 | 10 | 542 |

TABLE XVII C-continued

HPV11
HLA-A11 Motif Peptides

| 2 | 3 | 4 |
|---|---|---|
| E1 | 11 | 542 |
| E1 | 9 | 159 |
| E1 | 9 | 631 |
| E2 | 8 | 231 |
| E2 | 9 | 231 |
| E2 | 10 | 231 |
| L1 | 8 | 220 |
| L1 | 9 | 220 |
| E1 | 9 | 168 |
| E1 | 10 | 168 |
| E2 | 8 | 25 |
| E2 | 10 | 25 |
| E6 | 8 | 96 |
| E6 | 10 | 96 |
| E1 | 9 | 203 |
| E1 | 11 | 203 |
| E1 | 8 | 570 |
| E1 | 9 | 570 |
| E1 | 10 | 570 |
| E1 | 10 | 222 |
| E1 | 11 | 81 |
| L1 | 10 | 271 |
| E7 | 11 | 14 |
| L1 | 10 | 439 |
| E1 | 9 | 46 |
| E1 | 10 | 46 |
| L1 | 10 | 139 |
| L1 | 11 | 139 |
| E2 | 11 | 126 |
| E2 | 8 | 268 |
| E2 | 9 | 268 |
| E2 | 9 | 292 |
| E2 | 10 | 292 |
| E2 | 11 | 292 |
| E7 | 9 | 31 |
| L1 | 11 | 84 |
| E1 | 10 | 191 |
| L1 | 8 | 125 |
| L2 | 8 | 29 |
| L2 | 8 | 257 |
| E1 | 8 | 143 |
| E1 | 9 | 143 |
| E1 | 10 | 178 |
| L2 | 8 | 273 |
| L2 | 10 | 273 |
| L2 | 11 | 273 |
| E1 | 8 | 336 |
| E1 | 8 | 62 |
| E2 | 10 | 174 |
| L1 | 9 | 300 |
| E1 | 8 | 180 |
| E1 | 10 | 180 |
| E7 | 8 | 70 |
| E7 | 9 | 34 |
| E1 | 10 | 630 |
| E2 | 9 | 230 |
| E2 | 10 | 230 |
| E2 | 11 | 230 |
| E6 | 9 | 95 |
| E6 | 11 | 95 |
| E7 | 10 | 30 |
| L2 | 9 | 256 |
| E1 | 8 | 453 |
| E1 | 10 | 453 |
| L2 | 11 | 254 |
| E1 | 8 | 170 |
| E4 | 10 | 98 |
| E1 | 9 | 375 |
| E6 | 11 | 113 |
| E1 | 10 | 105 |
| E6 | 8 | 42 |
| E6 | 11 | 42 |
| E2 | 8 | 312 |
| L1 | 9 | 454 |

TABLE XVII C-continued

HPV11
HLA-A11 Motif Peptides

| 2 | 3 | 4 |
|---|---|---|
| L1 | 10 | 454 |
| E1 | 9 | 197 |
| E6 | 9 | 69 |
| E6 | 10 | 69 |
| E6 | 11 | 69 |
| E1 | 8 | 604 |
| E1 | 9 | 131 |
| E2 | 11 | 17 |
| E1 | 8 | 417 |
| E2 | 11 | 74 |
| E2 | 8 | 100 |
| E2 | 9 | 100 |
| L2 | 8 | 341 |
| E1 | 9 | 155 |
| E1 | 10 | 303 |
| E2 | 8 | 21 |
| E2 | 9 | 21 |
| E1 | 8 | 373 |
| E1 | 11 | 373 |
| E2 | 8 | 80 |
| E2 | 9 | 39 |
| E6 | 8 | 92 |
| E1 | 10 | 128 |
| E1 | 10 | 141 |
| E1 | 11 | 141 |
| E2 | 10 | 205 |
| L1 | 8 | 207 |
| L1 | 8 | 253 |
| L2 | 8 | 438 |
| E2 | 11 | 121 |
| L2 | 10 | 352 |
| E1 | 9 | 595 |
| E5 | 10 | 67 |
| E1 | 10 | 216 |
| E6 | 9 | 126 |
| E6 | 11 | 126 |
| E1 | 9 | 454 |
| L2 | 8 | 424 |
| L2 | 10 | 424 |
| E1 | 9 | 494 |
| L1 | 8 | 464 |
| L1 | 10 | 464 |
| E5 | 9 | 68 |
| E1 | 9 | 393 |
| E1 | 10 | 393 |
| E1 | 10 | 457 |
| L2 | 11 | 238 |
| L2 | 8 | 275 |
| L2 | 9 | 275 |
| E1 | 9 | 18 |
| E2 | 8 | 171 |
| L1 | 9 | 304 |
| E1 | 9 | 67 |
| E1 | 10 | 67 |
| L2 | 11 | 295 |
| E1 | 11 | 587 |
| E1 | 9 | 220 |
| L1 | 9 | 327 |
| L2 | 10 | 61 |
| L1 | 9 | 157 |
| E2 | 9 | 123 |
| E1 | 8 | 384 |
| E1 | 10 | 158 |
| E5 | 8 | 65 |
| L1 | 9 | 240 |
| L1 | 10 | 240 |
| E2 | 10 | 291 |
| E2 | 11 | 291 |
| E1 | 11 | 157 |
| L1 | 9 | 133 |
| L2 | 11 | 57 |
| L1 | 9 | 479 |
| E1 | 9 | 194 |
| E2 | 10 | 156 |

TABLE XVII C-continued

HPV11
HLA-A11 Motif Peptides

| 2 | 3 | 4 |
|---|---|---|
| E5 | 8 | 29 |
| E5 | 11 | 29 |
| E1 | 9 | 217 |
| L2 | 11 | 291 |
| E1 | 9 | 273 |
| E1 | 11 | 273 |
| L1 | 8 | 134 |
| E1 | 8 | 543 |
| E1 | 9 | 543 |
| E1 | 10 | 543 |
| E1 | 11 | 543 |
| E1 | 11 | 438 |
| L2 | 11 | 427 |
| L2 | 8 | 63 |
| L2 | 10 | 302 |
| E1 | 8 | 632 |
| E2 | 10 | 179 |
| L2 | 10 | 24 |
| E5 | 9 | 40 |
| E5 | 11 | 40 |
| L2 | 9 | 59 |
| E1 | 11 | 431 |
| L1 | 8 | 408 |
| L1 | 9 | 408 |
| E1 | 10 | 296 |
| E4 | 9 | 99 |
| L1 | 9 | 223 |
| E1 | 9 | 316 |
| E2 | 8 | 232 |
| E2 | 9 | 232 |
| E2 | 11 | 232 |
| L1 | 10 | 113 |
| L1 | 11 | 113 |
| E1 | 10 | 415 |
| E1 | 11 | 508 |
| E5 | 9 | 64 |
| E7 | 8 | 2 |
| E5 | 10 | 39 |
| L2 | 8 | 311 |
| E6 | 10 | 119 |
| E2 | 9 | 29 |
| E2 | 10 | 78 |
| E2 | 11 | 309 |
| L1 | 11 | 325 |
| E4 | 9 | 20 |
| E4 | 10 | 20 |
| E1 | 8 | 305 |
| E2 | 9 | 70 |
| L1 | 10 | 316 |
| E1 | 9 | 246 |
| E1 | 9 | 349 |
| E6 | 11 | 25 |
| L2 | 10 | 36 |
| E1 | 8 | 376 |
| E1 | 11 | 474 |
| E1 | 11 | 370 |
| L1 | 8 | 221 |
| L1 | 11 | 221 |
| E2 | 9 | 24 |
| E2 | 11 | 24 |
| E1 | 8 | 569 |
| E1 | 9 | 569 |
| E1 | 10 | 569 |
| E1 | 11 | 569 |
| L1 | 9 | 32 |
| E1 | 10 | 334 |
| E4 | 11 | 6 |
| L2 | 8 | 298 |
| L2 | 10 | 298 |
| L2 | 10 | 58 |
| E5 | 10 | 34 |
| L2 | 9 | 140 |
| E1 | 8 | 195 |
| E1 | 11 | 195 |

TABLE XVII C-continued

HPV11
HLA-A11 Motif Peptides

| 2 | 3 | 4 |
|---|---|---|
| E6 | 9 | 120 |
| E5 | 9 | 35 |
| E6 | 9 | 97 |
| E1 | 8 | 408 |
| E2 | 8 | 30 |
| E2 | 9 | 262 |
| E2 | 11 | 262 |
| E6 | 9 | 74 |
| L2 | 10 | 179 |
| E1 | 8 | 571 |
| E1 | 9 | 571 |
| E1 | 11 | 571 |
| E1 | 9 | 106 |
| E1 | 9 | 500 |
| L1 | 10 | 422 |
| L2 | 8 | 81 |
| L2 | 9 | 425 |
| L1 | 10 | 377 |
| E1 | 9 | 341 |
| L2 | 9 | 286 |
| E7 | 9 | 89 |
| E1 | 9 | 476 |
| E2 | 8 | 265 |
| E2 | 9 | 265 |
| E2 | 11 | 265 |
| E2 | 9 | 45 |
| E5 | 9 | 45 |
| E2 | 10 | 297 |
| E2 | 11 | 297 |
| E2 | 11 | 34 |
| E1 | 10 | 200 |
| E1 | 8 | 404 |
| E1 | 9 | 404 |
| E1 | 10 | 404 |
| E1 | 11 | 404 |
| E1 | 8 | 202 |
| E1 | 10 | 202 |
| L1 | 11 | 438 |
| E1 | 10 | 493 |
| L1 | 8 | 463 |
| L1 | 9 | 463 |
| L1 | 11 | 463 |
| E2 | 11 | 58 |
| E2 | 11 | 155 |
| E6 | 10 | 73 |
| E2 | 8 | 350 |
| E2 | 9 | 350 |
| E1 | 10 | 312 |
| E1 | 9 | 254 |
| E1 | 11 | 254 |
| E6 | 8 | 116 |
| E6 | 10 | 116 |
| E1 | 11 | 460 |
| E6 | 9 | 128 |
| E1 | 10 | 357 |
| E1 | 8 | 114 |
| E1 | 10 | 114 |
| E1 | 11 | 114 |
| E1 | 9 | 462 |
| E1 | 10 | 462 |
| E1 | 9 | 420 |
| E1 | 10 | 420 |
| E1 | 11 | 420 |
| E2 | 9 | 328 |
| E6 | 8 | 49 |
| L1 | 10 | 347 |
| L1 | 11 | 347 |
| E1 | 10 | 484 |
| E5 | 10 | 50 |
| E1 | 8 | 286 |
| E6 | 8 | 18 |
| E5 | 8 | 43 |
| E5 | 11 | 43 |
| L1 | 10 | 56 |

TABLE XVII C-continued

HPV11
HLA-A11 Motif Peptides

| 2 | 3 | 4 |
|---|---|---|
| E2 | 9 | 165 |
| E1 | 9 | 433 |
| E2 | 8 | 358 |
| E1 | 10 | 121 |
| E6 | 10 | 99 |
| E6 | 11 | 99 |
| E1 | 11 | 283 |
| L1 | 9 | 53 |
| L1 | 8 | 61 |
| L1 | 11 | 61 |
| E2 | 9 | 147 |
| L1 | 8 | 19 |
| L1 | 10 | 19 |
| L1 | 11 | 19 |
| L1 | 9 | 71 |
| L1 | 8 | 42 |
| L1 | 11 | 42 |
| L1 | 11 | 341 |
| E6 | 8 | 111 |
| E6 | 9 | 111 |
| E6 | 11 | 106 |
| E6 | 10 | 15 |
| E5 | 10 | 72 |
| E1 | 11 | 110 |
| E1 | 11 | 522 |
| E1 | 10 | 541 |
| E1 | 11 | 541 |
| L1 | 9 | 219 |
| L1 | 10 | 219 |
| L1 | 8 | 455 |
| L1 | 9 | 455 |
| L2 | 8 | 141 |
| L1 | 8 | 87 |
| E2 | 10 | 310 |
| L1 | 10 | 303 |
| E1 | 10 | 66 |
| E1 | 11 | 66 |
| L1 | 10 | 326 |
| E1 | 8 | 495 |
| E6 | 8 | 121 |
| E5 | 8 | 28 |
| E5 | 9 | 28 |
| L1 | 11 | 460 |
| E4 | 8 | 60 |
| E1 | 11 | 295 |
| L1 | 8 | 110 |
| E1 | 8 | 255 |
| E1 | 10 | 255 |
| E5 | 11 | 33 |
| E6 | 8 | 101 |
| E6 | 9 | 101 |
| E1 | 8 | 279 |
| E1 | 10 | 279 |
| E1 | 9 | 223 |
| L2 | 11 | 178 |
| E5 | 8 | 36 |
| L1 | 8 | 41 |
| L1 | 9 | 41 |
| E1 | 11 | 540 |
| E4 | 9 | 18 |
| E4 | 11 | 18 |
| E4 | 8 | 34 |
| E5 | 8 | 32 |
| E1 | 8 | 198 |
| E5 | 9 | 31 |
| E5 | 10 | 30 |
| E1 | 8 | 298 |
| E4 | 10 | 31 |
| E4 | 11 | 31 |
| L1 | 9 | 465 |
| E5 | 8 | 69 |
| L1 | 9 | 272 |
| E1 | 8 | 276 |
| E1 | 11 | 276 |
| E1 | 11 | 563 |
| E7 | 11 | 87 |
| E4 | 9 | 32 |
| E4 | 10 | 32 |
| E6 | 8 | 129 |
| E6 | 11 | 129 |
| E1 | 8 | 394 |
| E1 | 9 | 394 |
| E1 | 11 | 394 |
| E2 | 11 | 346 |
| L1 | 8 | 379 |
| L1 | 10 | 379 |
| E1 | 8 | 218 |
| E1 | 11 | 218 |
| E1 | 9 | 458 |
| L2 | 10 | 239 |
| E1 | 8 | 132 |
| E1 | 9 | 358 |
| E4 | 8 | 90 |
| E2 | 9 | 103 |
| E2 | 10 | 103 |
| E6 | 9 | 38 |
| E6 | 11 | 38 |
| E1 | 9 | 115 |
| E1 | 10 | 115 |
| E1 | 11 | 115 |
| E2 | 9 | 62 |
| E2 | 9 | 334 |
| L1 | 8 | 273 |
| E1 | 10 | 277 |
| E5 | 8 | 47 |
| L2 | 10 | 292 |
| L1 | 11 | 296 |
| E1 | 10 | 564 |
| L2 | 9 | 245 |
| E7 | 11 | 67 |
| L1 | 9 | 234 |
| E4 | 10 | 11 |
| E1 | 11 | 409 |
| L2 | 8 | 276 |
| L1 | 9 | 252 |
| L1 | 10 | 205 |
| L1 | 9 | 440 |
| L1 | 11 | 440 |
| E5 | 9 | 62 |
| E5 | 11 | 62 |
| E1 | 8 | 546 |
| E1 | 8 | 421 |
| E1 | 9 | 421 |
| E1 | 10 | 421 |
| L1 | 9 | 339 |
| E1 | 8 | 47 |
| E1 | 9 | 47 |
| E1 | 8 | 19 |
| L1 | 11 | 155 |
| E1 | 8 | 274 |
| E1 | 10 | 274 |
| E4 | 8 | 1 |
| E4 | 9 | 1 |
| E2 | 8 | 71 |
| E2 | 8 | 329 |
| E6 | 9 | 36 |
| E6 | 11 | 36 |
| E1 | 10 | 100 |
| E2 | 8 | 294 |
| E2 | 9 | 294 |
| L1 | 9 | 206 |
| E2 | 8 | 170 |
| E2 | 9 | 170 |
| E1 | 8 | 156 |
| L1 | 8 | 318 |
| L1 | 8 | 407 |
| L1 | 9 | 407 |
| L1 | 10 | 407 |

TABLE XVII C-continued

HPV11
HLA-A11 Motif Peptides

| 2 | 3 | 4 |
|---|---|---|
| E1 | 9 | 568 |
| E1 | 10 | 568 |
| E1 | 11 | 568 |
| E1 | 10 | 451 |
| L1 | 10 | 31 |
| E7 | 10 | 88 |
| E2 | 9 | 264 |
| E2 | 10 | 264 |
| E4 | 8 | 33 |
| E4 | 9 | 33 |
| E1 | 8 | 397 |
| L1 | 10 | 338 |
| L1 | 9 | 317 |
| E2 | 8 | 263 |
| E2 | 10 | 263 |
| E2 | 11 | 263 |
| E6 | 10 | 130 |
| L1 | 11 | 278 |
| E2 | 10 | 247 |
| L1 | 9 | 353 |
| L1 | 10 | 353 |
| E2 | 8 | 22 |
| E2 | 11 | 22 |
| E1 | 8 | 395 |
| E1 | 10 | 395 |
| E1 | 11 | 59 |
| E2 | 10 | 347 |
| E2 | 11 | 347 |
| E2 | 9 | 248 |
| E5 | 8 | 54 |
| E5 | 11 | 54 |
| E2 | 10 | 127 |
| L2 | 9 | 236 |
| E6 | 8 | 78 |
| L2 | 11 | 138 |
| L2 | 10 | 79 |
| L2 | 11 | 284 |
| E4 | 9 | 49 |
| E4 | 10 | 49 |
| E4 | 11 | 49 |
| E2 | 9 | 196 |
| L1 | 11 | 483 |
| E1 | 9 | 528 |
| E1 | 11 | 528 |
| L2 | 10 | 271 |
| E7 | 9 | 18 |
| L2 | 9 | 28 |
| L1 | 11 | 229 |
| L2 | 11 | 351 |
| E1 | 10 | 594 |
| E1 | 11 | 456 |
| L2 | 8 | 354 |
| E1 | 8 | 442 |
| E6 | 9 | 110 |
| E6 | 10 | 110 |
| L1 | 10 | 218 |
| L1 | 11 | 218 |
| L1 | 8 | 161 |
| L1 | 9 | 109 |
| E4 | 11 | 30 |
| L2 | 8 | 211 |
| L2 | 10 | 211 |
| E4 | 9 | 44 |
| E4 | 10 | 44 |
| E2 | 8 | 61 |
| E2 | 10 | 61 |
| E1 | 8 | 545 |
| E1 | 9 | 545 |
| L1 | 9 | 406 |
| L1 | 10 | 406 |
| L1 | 11 | 406 |
| E1 | 8 | 590 |
| L1 | 8 | 488 |
| L1 | 9 | 488 |
| L1 | 11 | 488 |
| L1 | 11 | 427 |
| L2 | 9 | 206 |
| L2 | 8 | 434 |
| L2 | 9 | 434 |
| L2 | 10 | 434 |
| L2 | 11 | 434 |
| L2 | 10 | 422 |
| L1 | 9 | 267 |
| L2 | 10 | 358 |
| L1 | 11 | 16 |
| L2 | 9 | 327 |
| E4 | 8 | 46 |
| E7 | 9 | 43 |
| E7 | 10 | 43 |
| E2 | 8 | 140 |
| L1 | 11 | 138 |
| E2 | 8 | 12 |
| E5 | 11 | 66 |
| E2 | 11 | 163 |
| L2 | 8 | 261 |
| E2 | 8 | 290 |
| E2 | 11 | 290 |
| E6 | 8 | 71 |
| E6 | 9 | 71 |
| E2 | 8 | 113 |
| E6 | 8 | 28 |
| E6 | 11 | 15 |
| L1 | 11 | 302 |
| E2 | 10 | 288 |
| E4 | 9 | 14 |
| L1 | 10 | 233 |
| L1 | 10 | 251 |
| E2 | 9 | 76 |
| E1 | 11 | 450 |
| E1 | 8 | 314 |
| E1 | 11 | 314 |
| L1 | 11 | 467 |
| L1 | 9 | 418 |
| E1 | 11 | 391 |
| L2 | 11 | 214 |
| L2 | 8 | 10 |
| E5 | 8 | 36 |
| E5 | 10 | 36 |
| E1 | 9 | 639 |
| E1 | 10 | 167 |
| E1 | 11 | 167 |
| E6 | 10 | 125 |
| E1 | 8 | 281 |
| L2 | 8 | 294 |
| E1 | 9 | 383 |
| L2 | 8 | 290 |
| L1 | 11 | 471 |
| L2 | 11 | 301 |
| L2 | 9 | 297 |
| L2 | 11 | 297 |
| E2 | 8 | 37 |
| E2 | 9 | 37 |
| E2 | 11 | 37 |
| L1 | 8 | 242 |
| E4 | 9 | 59 |
| L2 | 10 | 280 |
| L2 | 11 | 280 |
| L1 | 9 | 40 |
| L1 | 10 | 40 |
| E2 | 8 | 302 |
| L2 | 10 | 244 |
| E6 | 10 | 35 |
| E5 | 9 | 53 |
| L2 | 9 | 307 |
| L2 | 11 | 307 |
| L1 | 9 | 280 |
| L1 | 11 | 280 |
| E1 | 9 | 205 |

TABLE XVII C-continued

HPV11
HLA-A11 Motif Peptides

| 2 | 3 | 4 |
|---|---|---|
| L1 | 11 | 477 |
| L1 | 9 | 473 |
| L1 | 10 | 473 |
| L1 | 8 | 141 |
| L1 | 9 | 141 |
| L1 | 9 | 380 |
| E2 | 9 | 234 |
| L2 | 9 | 180 |
| L1 | 8 | 475 |
| L2 | 10 | 12 |
| E6 | 10 | 9 |
| L1 | 9 | 348 |
| L1 | 10 | 348 |
| E1 | 9 | 485 |
| E1 | 11 | 606 |
| L2 | 10 | 428 |
| L1 | 8 | 354 |
| L1 | 9 | 354 |
| E1 | 10 | 219 |
| L1 | 8 | 441 |
| L1 | 10 | 441 |
| L1 | 8 | 115 |
| L1 | 9 | 115 |
| E1 | 8 | 193 |
| E1 | 10 | 193 |
| L2 | 11 | 204 |
| L2 | 8 | 308 |
| L2 | 10 | 308 |
| L2 | 11 | 308 |
| E1 | 10 | 315 |
| L1 | 9 | 63 |
| L1 | 10 | 468 |
| E1 | 8 | 247 |
| E2 | 8 | 207 |
| E2 | 10 | 23 |
| E1 | 8 | 422 |
| E1 | 9 | 422 |
| L1 | 11 | 376 |
| E1 | 8 | 350 |
| L1 | 9 | 86 |
| L2 | 10 | 259 |
| E4 | 9 | 89 |
| L2 | 9 | 303 |
| E2 | 8 | 293 |
| E2 | 9 | 293 |
| E2 | 10 | 293 |
| E1 | 10 | 567 |
| E1 | 11 | 567 |
| E1 | 9 | 396 |
| E5 | 9 | 51 |
| E5 | 11 | 51 |
| L1 | 9 | 298 |
| L1 | 11 | 298 |
| E7 | 8 | 32 |
| E7 | 11 | 32 |
| L1 | 11 | 452 |
| L1 | 10 | 85 |
| E4 | 10 | 88 |
| L1 | 9 | 38 |
| L1 | 11 | 38 |
| L1 | 10 | 37 |
| L2 | 11 | 208 |
| L1 | 8 | 281 |
| L1 | 10 | 281 |
| E2 | 9 | 150 |
| E2 | 10 | 150 |
| L1 | 8 | 489 |
| L1 | 10 | 489 |
| E2 | 11 | 260 |
| E1 | 8 | 206 |
| E2 | 9 | 180 |
| L2 | 10 | 209 |
| L2 | 9 | 240 |
| L1 | 9 | 282 |

TABLE XVII C-continued

HPV11
HLA-A11 Motif Peptides

| 2 | 3 | 4 |
|---|---|---|
| E2 | 8 | 151 |
| E2 | 9 | 151 |
| E1 | 10 | 60 |
| E2 | 9 | 348 |
| E2 | 10 | 348 |
| E2 | 11 | 348 |
| E2 | 8 | 40 |
| E5 | 10 | 45 |
| L1 | 8 | 344 |
| E4 | 11 | 54 |
| E6 | 9 | 40 |
| E6 | 10 | 40 |
| L1 | 9 | 490 |
| L1 | 11 | 490 |
| E7 | 11 | 56 |
| E2 | 8 | 160 |
| E2 | 9 | 160 |
| L2 | 9 | 25 |
| L1 | 9 | 423 |
| L1 | 11 | 423 |
| E2 | 9 | 267 |
| E2 | 10 | 267 |
| L2 | 11 | 234 |
| E1 | 10 | 588 |
| L2 | 8 | 60 |
| L2 | 11 | 60 |
| L1 | 10 | 478 |
| L2 | 8 | 426 |
| L2 | 11 | 23 |
| L2 | 8 | 38 |
| E2 | 10 | 261 |
| L1 | 8 | 340 |
| E2 | 8 | 249 |
| E5 | 11 | 71 |
| L1 | 8 | 409 |
| E1 | 9 | 297 |
| E6 | 10 | 26 |
| L1 | 9 | 378 |
| L1 | 11 | 378 |
| E2 | 10 | 333 |
| E6 | 11 | 93 |
| E2 | 8 | 181 |
| L1 | 11 | 30 |
| L1 | 11 | 337 |
| E2 | 11 | 246 |
| L1 | 8 | 352 |
| L1 | 10 | 352 |
| L1 | 11 | 352 |
| L1 | 8 | 474 |
| L1 | 9 | 474 |
| E6 | 11 | 8 |
| E1 | 9 | 192 |
| E1 | 11 | 192 |
| E6 | 8 | 11 |
| E1 | 8 | 566 |
| E1 | 11 | 566 |
| L2 | 8 | 287 |
| L2 | 11 | 287 |
| E4 | 11 | 87 |
| L2 | 8 | 207 |
| E2 | 10 | 149 |
| E2 | 11 | 149 |
| E5 | 11 | 44 |
| E2 | 11 | 97 |
| E6 | 8 | 39 |
| E6 | 10 | 39 |
| E6 | 11 | 39 |
| E2 | 11 | 228 |
| L2 | 9 | 37 |
| E1 | 8 | 116 |
| E1 | 9 | 116 |
| E1 | 10 | 116 |
| E5 | 10 | 55 |
| E4 | 8 | 100 |

TABLE XVII C-continued

HPV11
HLA-A11 Motif Peptides

| 2 | 3 | 4 |
|---|---|---|
| L1 | 8 | 224 |
| E5 | 9 | 56 |
| E1 | 11 | 498 |
| E1 | 8 | 78 |
| E1 | 9 | 78 |
| E2 | 8 | 63 |
| L1 | 9 | 57 |
| L1 | 11 | 57 |
| L2 | 11 | 338 |
| E1 | 8 | 239 |
| L1 | 8 | 283 |
| L1 | 8 | 21 |
| L1 | 9 | 21 |
| E5 | 10 | 25 |
| E5 | 11 | 25 |
| E7 | 8 | 90 |
| E5 | 8 | 74 |
| E5 | 10 | 74 |
| E2 | 8 | 152 |
| E1 | 8 | 182 |
| E1 | 8 | 48 |
| E1 | 8 | 221 |
| E1 | 11 | 221 |
| E1 | 8 | 434 |
| E5 | 8 | 57 |
| L2 | 9 | 423 |
| L2 | 11 | 423 |
| L1 | 11 | 69 |
| L1 | 10 | 156 |
| L1 | 9 | 44 |
| L1 | 10 | 44 |
| E1 | 8 | 477 |
| L1 | 11 | 112 |
| E1 | 11 | 333 |
| E1 | 10 | 499 |
| E5 | 8 | 27 |
| E5 | 9 | 27 |
| E5 | 10 | 27 |
| E6 | 9 | 100 |
| E6 | 10 | 100 |
| E1 | 9 | 278 |
| E1 | 11 | 278 |
| E4 | 10 | 17 |
| E1 | 9 | 275 |
| E5 | 9 | 46 |
| E4 | 11 | 10 |
| E2 | 9 | 128 |
| E2 | 11 | 128 |
| E2 | 9 | 169 |
| E2 | 10 | 169 |
| E1 | 10 | 284 |
| L1 | 8 | 54 |
| L1 | 8 | 142 |
| E2 | 8 | 233 |
| E2 | 10 | 233 |
| L1 | 9 | 114 |
| L1 | 10 | 114 |
| L1 | 10 | 62 |
| E2 | 9 | 206 |
| L1 | 9 | 485 |
| L1 | 10 | 485 |
| L1 | 11 | 485 |
| L1 | 10 | 17 |
| L2 | 11 | 258 |
| L1 | 10 | 297 |
| E2 | 8 | 266 |
| E2 | 10 | 266 |
| E2 | 11 | 266 |
| E2 | 11 | 332 |
| L2 | 11 | 325 |
| E1 | 9 | 565 |
| E2 | 8 | 148 |
| E2 | 11 | 148 |
| L1 | 8 | 328 |
| L2 | 8 | 246 |
| E1 | 8 | 238 |
| E1 | 9 | 238 |
| L1 | 9 | 20 |
| L1 | 10 | 20 |
| E5 | 11 | 24 |
| E7 | 10 | 68 |
| L1 | 8 | 72 |
| E4 | 8 | 2 |
| L1 | 8 | 58 |
| L1 | 10 | 58 |
| L1 | 11 | 58 |
| E2 | 11 | 58 |
| L1 | 10 | 97 |
| E2 | 8 | 320 |
| E2 | 9 | 320 |
| E1 | 10 | 17 |
| E1 | 10 | 272 |
| E1 | 8 | 426 |
| E1 | 10 | 340 |
| E1 | 8 | 464 |
| L1 | 8 | 309 |
| E1 | 9 | 510 |
| E2 | 10 | 102 |
| E2 | 11 | 102 |
| E2 | 8 | 92 |
| E1 | 9 | 530 |
| E2 | 11 | 145 |
| E1 | 9 | 237 |
| E1 | 10 | 237 |
| E1 | 8 | 76 |
| E1 | 9 | 76 |
| E1 | 10 | 76 |
| E1 | 11 | 76 |
| E6 | 9 | 44 |
| E6 | 11 | 46 |
| L1 | 10 | 123 |
| E1 | 10 | 45 |
| E1 | 11 | 45 |
| L2 | 8 | 437 |
| L2 | 9 | 437 |
| E5 | 8 | 76 |
| E5 | 10 | 76 |
| L1 | 8 | 239 |
| L1 | 10 | 239 |
| L1 | 11 | 239 |
| L1 | 10 | 132 |
| E2 | 11 | 178 |
| L2 | 9 | 70 |
| E4 | 8 | 22 |
| L2 | 10 | 431 |
| L2 | 11 | 431 |
| E2 | 10 | 138 |
| L1 | 9 | 231 |
| L1 | 10 | 246 |
| L1 | 11 | 246 |
| E5 | 10 | 61 |
| E2 | 11 | 270 |
| L1 | 8 | 49 |
| E2 | 9 | 159 |
| E2 | 10 | 159 |
| L1 | 9 | 351 |
| L1 | 11 | 351 |
| L2 | 11 | 305 |
| E1 | 10 | 402 |
| E1 | 11 | 402 |
| L1 | 9 | 26 |
| L1 | 10 | 26 |
| E4 | 11 | 16 |
| E4 | 8 | 9 |
| E2 | 10 | 168 |
| E2 | 11 | 168 |
| L1 | 10 | 10 |

TABLE XVII C-continued

HPV11
HLA-A11 Motif Peptides

| 1 | 2 | 3 | 4 |
|---|---|---|---|
| | L1 | 11 | 416 |
| | E2 | 8 | 131 |

TABLE XVIII

HLA.A24 Motif Peptides

| 1 | 2 | 3 | 4 |
|---|---|---|---|
| HPV16 | E1 | 8 | 240 |
| HPV16 | E1 | 11 | 391 |
| HPV16 | E1 | 9 | 206 |
| HPV16 | E1 | 9 | 500 |
| HPV16 | E1 | 10 | 500 |
| HPV16 | E1 | 11 | 500 |
| HPV16 | E1 | 9 | 304 |
| HPV16 | E1 | 9 | 528 |
| HPV16 | E1 | 10 | 50 |
| HPV16 | E1 | 9 | 235 |
| HPV16 | E1 | 8 | 438 |
| HPV16 | E1 | 9 | 438 |
| HPV16 | E1 | 9 | 452 |
| HPV16 | E1 | 9 | 338 |
| HPV16 | E1 | 9 | 612 |
| HPV16 | E1 | 11 | 612 |
| HPV16 | E1 | 8 | 453 |
| HPV16 | E1 | 11 | 453 |
| HPV16 | E1 | 11 | 508 |
| HPV16 | E1 | 11 | 519 |
| HPV16 | E1 | 8 | 487 |
| HPV16 | E1 | 10 | 210 |
| HPV16 | E1 | 8 | 492 |
| HPV16 | E1 | 10 | 492 |
| HPV16 | E1 | 10 | 89 |
| HPV16 | E1 | 9 | 485 |
| HPV16 | E1 | 10 | 485 |
| HPV16 | E1 | 10 | 490 |
| HPV16 | E1 | 11 | 475 |
| HPV16 | E1 | 9 | 214 |
| HPV16 | E1 | 8 | 260 |
| HPV16 | E1 | 8 | 319 |
| HPV16 | E1 | 11 | 319 |
| HPV16 | E1 | 10 | 444 |
| HPV16 | E1 | 8 | 305 |
| HPV16 | E1 | 10 | 608 |
| HPV16 | E1 | 11 | 530 |
| HPV16 | E1 | 11 | 302 |
| HPV16 | E1 | 10 | 577 |
| HPV16 | E1 | 8 | 419 |
| HPV16 | E1 | 11 | 359 |
| HPV16 | E1 | 8 | 362 |
| HPV16 | E1 | 8 | 257 |
| HPV16 | E1 | 11 | 257 |
| HPV16 | E1 | 9 | 575 |
| HPV16 | E1 | 11 | 280 |
| HPV16 | E1 | 10 | 447 |
| HPV16 | E1 | 11 | 447 |
| HPV16 | E1 | 10 | 611 |
| HPV16 | E1 | 9 | 455 |
| HPV16 | E1 | 10 | 455 |
| HPV16 | E1 | 9 | 349 |
| HPV16 | E1 | 9 | 218 |
| HPV16 | E1 | 9 | 546 |
| HPV16 | E1 | 8 | 270 |
| HPV16 | E1 | 9 | 270 |
| HPV16 | E1 | 10 | 354 |
| HPV16 | E1 | 8 | 587 |
| HPV16 | E1 | 8 | 585 |
| HPV16 | E1 | 10 | 585 |
| HPV16 | E1 | 11 | 443 |
| HPV16 | E1 | 9 | 601 |

TABLE XVIII-continued

HLA.A24 Motif Peptides

| 1 | 2 | 3 | 4 |
|---|---|---|---|
| HPV16 | E1 | 8 | 332 |
| HPV16 | E1 | 9 | 332 |
| HPV16 | E1 | 9 | 321 |
| HPV16 | E1 | 10 | 320 |
| HPV16 | E2 | 10 | 270 |
| HPV16 | E2 | 8 | 31 |
| HPV16 | E2 | 8 | 340 |
| HPV16 | E2 | 8 | 114 |
| HPV16 | E2 | 8 | 35 |
| HPV16 | E2 | 9 | 18 |
| HPV16 | E2 | 8 | 130 |
| HPV16 | E2 | 10 | 130 |
| HPV16 | E2 | 11 | 82 |
| HPV16 | E2 | 10 | 42 |
| HPV16 | E2 | 9 | 91 |
| HPV16 | E2 | 8 | 177 |
| HPV16 | E2 | 9 | 311 |
| HPV16 | E2 | 11 | 311 |
| HPV16 | E2 | 8 | 157 |
| HPV16 | E2 | 8 | 345 |
| HPV16 | E2 | 9 | 86 |
| HPV16 | E2 | 8 | 304 |
| HPV16 | E2 | 10 | 302 |
| HPV16 | E2 | 10 | 128 |
| HPV16 | E2 | 11 | 336 |
| HPV16 | E2 | 11 | 183 |
| HPV16 | E2 | 10 | 101 |
| HPV16 | E2 | 11 | 32 |
| HPV16 | E2 | 11 | 154 |
| HPV16 | E2 | 9 | 43 |
| HPV16 | E2 | 11 | 158 |
| HPV16 | E5 | 9 | 56 |
| HPV16 | E5 | 10 | 56 |
| HPV16 | E5 | 11 | 56 |
| HPV16 | E5 | 10 | 18 |
| HPV16 | E5 | 11 | 18 |
| HPV16 | E5 | 8 | 59 |
| HPV16 | E5 | 11 | 59 |
| HPV16 | E5 | 9 | 14 |
| HPV16 | E5 | 10 | 14 |
| HPV16 | E5 | 8 | 65 |
| HPV16 | E5 | 9 | 65 |
| HPV16 | E5 | 10 | 65 |
| HPV16 | E5 | 10 | 71 |
| HPV16 | E5 | 11 | 71 |
| HPV16 | E5 | 9 | 49 |
| HPV16 | E5 | 8 | 38 |
| HPV16 | E5 | 10 | 38 |
| HPV16 | E5 | 11 | 38 |
| HPV16 | E5 | 8 | 62 |
| HPV16 | E5 | 10 | 62 |
| HPV16 | E5 | 11 | 62 |
| HPV16 | E5 | 8 | 67 |
| HPV16 | E6 | 9 | 87 |
| HPV16 | E6 | 9 | 51 |
| HPV16 | E6 | 9 | 82 |
| HPV16 | E6 | 11 | 85 |
| HPV16 | E6 | 9 | 66 |
| HPV16 | E6 | 11 | 66 |
| HPV16 | E6 | 9 | 98 |
| HPV16 | E6 | 10 | 98 |
| HPV16 | E6 | 11 | 98 |
| HPV16 | E6 | 9 | 131 |
| HPV16 | E6 | 8 | 38 |
| HPV16 | E6 | 9 | 49 |
| HPV16 | E6 | 11 | 49 |
| HPV16 | E7 | 11 | 83 |
| HPV16 | E7 | 10 | 56 |
| HPV16 | L1 | 11 | 13 |
| HPV16 | L1 | 9 | 176 |
| HPV16 | L1 | 10 | 176 |
| HPV16 | L1 | 8 | 395 |
| HPV16 | L1 | 10 | 395 |
| HPV16 | L1 | 11 | 388 |
| HPV16 | L1 | 8 | 52 |

TABLE XVIII-continued

HLA.A24 Motif Peptides

| 1 | 2 | 3 | 4 |
|---|---|---|---|
| HPV16 | L1 | 8 | 24 |
| HPV16 | L1 | 10 | 273 |
| HPV16 | L1 | 10 | 472 |
| HPV16 | L1 | 9 | 274 |
| HPV16 | L1 | 9 | 116 |
| HPV16 | L1 | 11 | 116 |
| HPV16 | L1 | 10 | 230 |
| HPV16 | L1 | 8 | 23 |
| HPV16 | L1 | 9 | 23 |
| HPV16 | L1 | 8 | 332 |
| HPV16 | L1 | 9 | 401 |
| HPV16 | L1 | 10 | 59 |
| HPV16 | L1 | 11 | 59 |
| HPV16 | L1 | 9 | 108 |
| HPV16 | L1 | 8 | 493 |
| HPV16 | L1 | 9 | 480 |
| HPV16 | L1 | 11 | 480 |
| HPV16 | L1 | 11 | 262 |
| HPV16 | L1 | 9 | 469 |
| HPV16 | L1 | 11 | 272 |
| HPV16 | L1 | 11 | 29 |
| HPV16 | L1 | 8 | 367 |
| HPV16 | L1 | 8 | 267 |
| HPV16 | L1 | 10 | 267 |
| HPV16 | L1 | 9 | 399 |
| HPV16 | L1 | 11 | 399 |
| HPV16 | L1 | 8 | 487 |
| HPV16 | L1 | 9 | 487 |
| HPV16 | L1 | 10 | 487 |
| HPV16 | L1 | 8 | 280 |
| HPV16 | L1 | 9 | 95 |
| HPV16 | L1 | 8 | 445 |
| HPV16 | L1 | 10 | 115 |
| HPV16 | L1 | 9 | 174 |
| HPV16 | L1 | 11 | 174 |
| HPV16 | L1 | 10 | 419 |
| HPV16 | L1 | 9 | 324 |
| HPV16 | L1 | 10 | 324 |
| HPV16 | L1 | 8 | 4 |
| HPV16 | L1 | 11 | 471 |
| HPV16 | L1 | 10 | 415 |
| HPV16 | L1 | 11 | 415 |
| HPV16 | L1 | 11 | 380 |
| HPV16 | L1 | 10 | 443 |
| HPV16 | L1 | 10 | 20 |
| HPV16 | L1 | 11 | 20 |
| HPV16 | L1 | 9 | 60 |
| HPV16 | L1 | 10 | 60 |
| HPV16 | L2 | 9 | 241 |
| HPV16 | L2 | 10 | 241 |
| HPV16 | L2 | 11 | 256 |
| HPV16 | L2 | 8 | 282 |
| HPV16 | L2 | 11 | 329 |
| HPV16 | L2 | 11 | 445 |
| HPV16 | L2 | 10 | 446 |
| HPV16 | L2 | 9 | 392 |
| HPV16 | L2 | 11 | 392 |
| HPV16 | L2 | 9 | 180 |
| HPV16 | L2 | 9 | 325 |
| HPV16 | L2 | 9 | 365 |
| HPV16 | L2 | 10 | 365 |
| HPV16 | L2 | 10 | 266 |
| HPV16 | L2 | 10 | 192 |
| HPV16 | L2 | 11 | 192 |
| HPV16 | L2 | 8 | 401 |
| HPV16 | L2 | 10 | 401 |
| HPV16 | L2 | 9 | 463 |
| HPV16 | L2 | 8 | 47 |
| HPV16 | L2 | 9 | 47 |
| HPV16 | L2 | 11 | 436 |
| HPV16 | L2 | 11 | 302 |
| HPV16 | L2 | 9 | 50 |
| HPV16 | L2 | 11 | 50 |
| HPV16 | L2 | 8 | 162 |
| HPV16 | L2 | 10 | 251 |
| HPV16 | L2 | 10 | 348 |
| HPV16 | L2 | 8 | 53 |
| HPV16 | L2 | 8 | 464 |
| HPV16 | L2 | 9 | 267 |
| HPV16 | L2 | 11 | 267 |
| HPV16 | L2 | 10 | 453 |
| HPV16 | L2 | 11 | 452 |
| HPV16 | L2 | 8 | 326 |
| HPV18 | E1 | 11 | 526 |
| HPV18 | E1 | 10 | 618 |
| HPV18 | E1 | 9 | 311 |
| HPV18 | E1 | 9 | 49 |
| HPV18 | E1 | 8 | 381 |
| HPV18 | E1 | 9 | 381 |
| HPV18 | E1 | 8 | 445 |
| HPV18 | E1 | 9 | 445 |
| HPV18 | E1 | 9 | 459 |
| HPV18 | E1 | 8 | 594 |
| HPV18 | E1 | 11 | 366 |
| HPV18 | E1 | 8 | 345 |
| HPV18 | E1 | 9 | 345 |
| HPV18 | E1 | 9 | 619 |
| HPV18 | E1 | 11 | 619 |
| HPV18 | E1 | 9 | 257 |
| HPV18 | E1 | 10 | 257 |
| HPV18 | E1 | 11 | 257 |
| HPV18 | E1 | 8 | 494 |
| HPV18 | E1 | 8 | 16 |
| HPV18 | E1 | 8 | 499 |
| HPV18 | E1 | 10 | 499 |
| HPV18 | E1 | 8 | 247 |
| HPV18 | E1 | 9 | 277 |
| HPV18 | E1 | 10 | 277 |
| HPV18 | E1 | 8 | 267 |
| HPV18 | E1 | 8 | 326 |
| HPV18 | E1 | 11 | 326 |
| HPV18 | E1 | 10 | 361 |
| HPV18 | E1 | 8 | 428 |
| HPV18 | E1 | 10 | 615 |
| HPV18 | E1 | 8 | 264 |
| HPV18 | E1 | 11 | 264 |
| HPV18 | E1 | 10 | 584 |
| HPV18 | E1 | 8 | 451 |
| HPV18 | E1 | 10 | 451 |
| HPV18 | E1 | 11 | 451 |
| HPV18 | E1 | 8 | 426 |
| HPV18 | E1 | 10 | 426 |
| HPV18 | E1 | 8 | 369 |
| HPV18 | E1 | 10 | 431 |
| HPV18 | E1 | 9 | 582 |
| HPV18 | E1 | 9 | 287 |
| HPV18 | E1 | 8 | 454 |
| HPV18 | E1 | 10 | 454 |
| HPV18 | E1 | 11 | 454 |
| HPV18 | E1 | 11 | 496 |
| HPV18 | E1 | 9 | 225 |
| HPV18 | E1 | 9 | 507 |
| HPV18 | E1 | 10 | 507 |
| HPV18 | E1 | 11 | 507 |
| HPV18 | E1 | 8 | 491 |
| HPV18 | E1 | 10 | 491 |
| HPV18 | E1 | 11 | 491 |
| HPV18 | E1 | 8 | 56 |
| HPV18 | E1 | 9 | 462 |
| HPV18 | E1 | 10 | 462 |
| HPV18 | E1 | 11 | 537 |
| HPV18 | E1 | 9 | 221 |
| HPV18 | E1 | 8 | 592 |
| HPV18 | E1 | 10 | 592 |
| HPV18 | E1 | 8 | 217 |
| HPV18 | E1 | 10 | 217 |
| HPV18 | E1 | 8 | 339 |
| HPV18 | E1 | 9 | 339 |
| HPV18 | E1 | 9 | 608 |
| HPV18 | E1 | 9 | 328 |

TABLE XVIII-continued

HLA.A24 Motif Peptides

| 1 | 2 | 3 | 4 |
|---|---|---|---|
| HPV18 | E1 | 10 | 538 |
| HPV18 | E1 | 9 | 492 |
| HPV18 | E1 | 10 | 492 |
| HPV18 | E1 | 11 | 542 |
| HPV18 | E1 | 10 | 327 |
| HPV18 | E2 | 11 | 95 |
| HPV18 | E2 | 9 | 47 |
| HPV18 | E2 | 9 | 168 |
| HPV18 | E2 | 9 | 22 |
| HPV18 | E2 | 9 | 312 |
| HPV18 | E2 | 11 | 312 |
| HPV18 | E2 | 10 | 46 |
| HPV18 | E2 | 8 | 345 |
| HPV18 | E2 | 8 | 182 |
| HPV18 | E2 | 10 | 105 |
| HPV18 | E2 | 11 | 162 |
| HPV18 | E2 | 8 | 35 |
| HPV18 | E2 | 8 | 41 |
| HPV18 | E2 | 9 | 90 |
| HPV18 | E2 | 11 | 188 |
| HPV18 | E2 | 11 | 336 |
| HPV18 | E2 | 10 | 141 |
| HPV18 | E2 | 8 | 143 |
| HPV18 | E2 | 11 | 36 |
| HPV18 | E2 | 9 | 142 |
| HPV18 | E2 | 10 | 163 |
| HPV18 | E5 | 9 | 49 |
| HPV18 | E5 | 10 | 49 |
| HPV18 | E5 | 11 | 49 |
| HPV18 | E5 | 9 | 32 |
| HPV18 | E5 | 8 | 30 |
| HPV18 | E5 | 11 | 30 |
| HPV18 | E5 | 8 | 56 |
| HPV18 | E5 | 9 | 56 |
| HPV18 | E5 | 11 | 56 |
| HPV18 | E5 | 9 | 27 |
| HPV18 | E5 | 11 | 27 |
| HPV18 | E5 | 10 | 13 |
| HPV18 | E5 | 11 | 13 |
| HPV18 | E5 | 9 | 14 |
| HPV18 | E5 | 10 | 14 |
| HPV18 | E5 | 10 | 60 |
| HPV18 | E5 | 11 | 60 |
| HPV18 | E5 | 9 | 54 |
| HPV18 | E5 | 10 | 54 |
| HPV18 | E5 | 11 | 54 |
| HPV18 | E5 | 8 | 36 |
| HPV18 | E5 | 8 | 52 |
| HPV18 | E5 | 11 | 52 |
| HPV18 | E6 | 9 | 70 |
| HPV18 | E6 | 8 | 46 |
| HPV18 | E6 | 8 | 71 |
| HPV18 | E6 | 11 | 80 |
| HPV18 | E6 | 9 | 52 |
| HPV18 | E6 | 9 | 98 |
| HPV18 | E6 | 11 | 11 |
| HPV18 | E6 | 9 | 44 |
| HPV18 | E6 | 10 | 44 |
| HPV18 | E6 | 9 | 33 |
| HPV18 | E6 | 9 | 85 |
| HPV18 | E7 | 10 | 85 |
| HPV18 | E7 | 10 | 63 |
| HPV18 | E7 | 8 | 89 |
| HPV18 | L1 | 11 | 128 |
| HPV18 | L1 | 9 | 211 |
| HPV18 | L1 | 10 | 211 |
| HPV18 | L1 | 8 | 87 |
| HPV18 | L1 | 9 | 87 |
| HPV18 | L1 | 8 | 431 |
| HPV18 | L1 | 10 | 431 |
| HPV18 | L1 | 9 | 308 |
| HPV18 | L1 | 10 | 308 |
| HPV18 | L1 | 10 | 508 |
| HPV18 | L1 | 9 | 95 |
| HPV18 | L1 | 10 | 95 |

TABLE XVIII-continued

HLA.A24 Motif Peptides

| 1 | 2 | 3 | 4 |
|---|---|---|---|
| HPV18 | L1 | 10 | 265 |
| HPV18 | L1 | 11 | 11 |
| HPV18 | L1 | 8 | 58 |
| HPV18 | L1 | 9 | 437 |
| HPV18 | L1 | 10 | 94 |
| HPV18 | L1 | 11 | 94 |
| HPV18 | L1 | 9 | 151 |
| HPV18 | L1 | 11 | 151 |
| HPV18 | L1 | 9 | 143 |
| HPV18 | L1 | 8 | 529 |
| HPV18 | L1 | 11 | 516 |
| HPV18 | L1 | 11 | 507 |
| HPV18 | L1 | 9 | 48 |
| HPV18 | L1 | 11 | 48 |
| HPV18 | L1 | 8 | 367 |
| HPV18 | L1 | 11 | 64 |
| HPV18 | L1 | 11 | 17 |
| HPV18 | L1 | 9 | 21 |
| HPV18 | L1 | 8 | 3 |
| HPV18 | L1 | 10 | 307 |
| HPV18 | L1 | 11 | 307 |
| HPV18 | L1 | 8 | 502 |
| HPV18 | L1 | 8 | 302 |
| HPV18 | L1 | 10 | 302 |
| HPV18 | L1 | 9 | 435 |
| HPV18 | L1 | 11 | 435 |
| HPV18 | L1 | 8 | 523 |
| HPV18 | L1 | 9 | 523 |
| HPV18 | L1 | 9 | 130 |
| HPV18 | L1 | 11 | 424 |
| HPV18 | L1 | 8 | 481 |
| HPV18 | L1 | 11 | 306 |
| HPV18 | L1 | 10 | 455 |
| HPV18 | L1 | 10 | 451 |
| HPV18 | L1 | 11 | 451 |
| HPV18 | L1 | 10 | 327 |
| HPV18 | L1 | 10 | 479 |
| HPV18 | L1 | 10 | 55 |
| HPV18 | L1 | 11 | 55 |
| HPV18 | L1 | 9 | 160 |
| HPV18 | L1 | 8 | 34 |
| HPV18 | L1 | 10 | 351 |
| HPV18 | L2 | 9 | 255 |
| HPV18 | L2 | 11 | 255 |
| HPV18 | L2 | 9 | 370 |
| HPV18 | L2 | 8 | 161 |
| HPV18 | L2 | 8 | 275 |
| HPV18 | L2 | 9 | 240 |
| HPV18 | L2 | 10 | 240 |
| HPV18 | L2 | 8 | 331 |
| HPV18 | L2 | 8 | 371 |
| HPV18 | L2 | 8 | 319 |
| HPV18 | L2 | 10 | 191 |
| HPV18 | L2 | 9 | 318 |
| HPV18 | L2 | 10 | 434 |
| HPV18 | L2 | 11 | 434 |
| HPV18 | L2 | 8 | 52 |
| HPV18 | L2 | 8 | 437 |
| HPV18 | L2 | 9 | 305 |
| HPV18 | L2 | 8 | 452 |
| HPV18 | L2 | 8 | 46 |
| HPV18 | L2 | 9 | 46 |
| HPV18 | L2 | 11 | 368 |
| HPV18 | L2 | 9 | 383 |
| HPV18 | L2 | 8 | 121 |
| HPV18 | L2 | 10 | 121 |
| HPV18 | L2 | 10 | 304 |
| HPV18 | L2 | 9 | 399 |
| HPV18 | L2 | 9 | 435 |
| HPV18 | L2 | 10 | 435 |
| HPV31 | E1 | 11 | 371 |
| HPV31 | E1 | 9 | 186 |
| HPV31 | E1 | 9 | 284 |
| HPV31 | E1 | 9 | 508 |
| HPV31 | E1 | 8 | 418 |

TABLE XVIII-continued

HLA.A24 Motif Peptides

| 1 | 2 | 3 | 4 |
|---|---|---|---|
| HPV31 | E1 | 9 | 418 |
| HPV31 | E1 | 8 | 102 |
| HPV31 | E1 | 11 | 102 |
| HPV31 | E1 | 9 | 432 |
| HPV31 | E1 | 11 | 432 |
| HPV31 | E1 | 9 | 318 |
| HPV31 | E1 | 9 | 592 |
| HPV31 | E1 | 11 | 592 |
| HPV31 | E1 | 8 | 199 |
| HPV31 | E1 | 11 | 488 |
| HPV31 | E1 | 11 | 230 |
| HPV31 | E1 | 11 | 499 |
| HPV31 | E1 | 8 | 467 |
| HPV31 | E1 | 10 | 252 |
| HPV31 | E1 | 9 | 16 |
| HPV31 | E1 | 11 | 510 |
| HPV31 | E1 | 10 | 190 |
| HPV31 | E1 | 8 | 424 |
| HPV31 | E1 | 10 | 424 |
| HPV31 | E1 | 10 | 88 |
| HPV31 | E1 | 9 | 534 |
| HPV31 | E1 | 10 | 534 |
| HPV31 | E1 | 11 | 534 |
| HPV31 | E1 | 8 | 240 |
| HPV31 | E1 | 9 | 194 |
| HPV31 | E1 | 10 | 194 |
| HPV31 | E1 | 11 | 299 |
| HPV31 | E1 | 10 | 588 |
| HPV31 | E1 | 8 | 237 |
| HPV31 | E1 | 11 | 237 |
| HPV31 | E1 | 10 | 557 |
| HPV31 | E1 | 8 | 399 |
| HPV31 | E1 | 9 | 260 |
| HPV31 | E1 | 11 | 260 |
| HPV31 | E1 | 9 | 555 |
| HPV31 | E1 | 10 | 427 |
| HPV31 | E1 | 11 | 427 |
| HPV31 | E1 | 10 | 591 |
| HPV31 | E1 | 8 | 472 |
| HPV31 | E1 | 8 | 435 |
| HPV31 | E1 | 9 | 435 |
| HPV31 | E1 | 10 | 435 |
| HPV31 | E1 | 9 | 198 |
| HPV31 | E1 | 9 | 329 |
| HPV31 | E1 | 9 | 250 |
| HPV31 | E1 | 9 | 480 |
| HPV31 | E1 | 10 | 480 |
| HPV31 | E1 | 11 | 480 |
| HPV31 | E1 | 8 | 464 |
| HPV31 | E1 | 10 | 464 |
| HPV31 | E1 | 11 | 464 |
| HPV31 | E1 | 10 | 334 |
| HPV31 | E1 | 10 | 617 |
| HPV31 | E1 | 8 | 567 |
| HPV31 | E1 | 8 | 565 |
| HPV31 | E1 | 10 | 565 |
| HPV31 | E1 | 8 | 254 |
| HPV31 | E1 | 9 | 581 |
| HPV31 | E1 | 8 | 312 |
| HPV31 | E1 | 9 | 312 |
| HPV31 | E1 | 8 | 17 |
| HPV31 | E1 | 9 | 301 |
| HPV31 | E1 | 9 | 465 |
| HPV31 | E1 | 10 | 465 |
| HPV31 | E1 | 10 | 300 |
| HPV31 | E2 | 8 | 352 |
| HPV31 | E2 | 9 | 91 |
| HPV31 | E2 | 11 | 91 |
| HPV31 | E2 | 8 | 31 |
| HPV31 | E2 | 8 | 114 |
| HPV31 | E2 | 9 | 18 |
| HPV31 | E2 | 8 | 130 |
| HPV31 | E2 | 10 | 130 |
| HPV31 | E2 | 9 | 157 |
| HPV31 | E2 | 11 | 183 |
| HPV31 | E2 | 8 | 177 |
| HPV31 | E2 | 10 | 42 |
| HPV31 | E2 | 9 | 318 |
| HPV31 | E2 | 11 | 318 |
| HPV31 | E2 | 10 | 101 |
| HPV31 | E2 | 9 | 43 |
| HPV31 | E2 | 9 | 133 |
| HPV31 | E2 | 10 | 309 |
| HPV31 | E2 | 9 | 206 |
| HPV31 | E2 | 9 | 128 |
| HPV31 | E2 | 10 | 128 |
| HPV31 | E2 | 9 | 93 |
| HPV31 | E2 | 11 | 93 |
| HPV31 | E2 | 11 | 343 |
| HPV31 | E2 | 9 | 199 |
| HPV31 | E2 | 11 | 32 |
| HPV31 | E2 | 8 | 158 |
| HPV31 | E2 | 11 | 158 |
| HPV31 | E5 | 8 | 59 |
| HPV31 | E5 | 9 | 59 |
| HPV31 | E5 | 11 | 59 |
| HPV31 | E5 | 10 | 18 |
| HPV31 | E5 | 9 | 14 |
| HPV31 | E5 | 10 | 14 |
| HPV31 | E5 | 11 | 14 |
| HPV31 | E5 | 8 | 67 |
| HPV31 | E5 | 8 | 62 |
| HPV31 | E5 | 10 | 62 |
| HPV31 | E5 | 11 | 62 |
| HPV31 | E5 | 10 | 23 |
| HPV31 | E5 | 10 | 71 |
| HPV31 | E5 | 11 | 71 |
| HPV31 | E5 | 9 | 49 |
| HPV31 | E5 | 8 | 65 |
| HPV31 | E5 | 10 | 65 |
| HPV31 | E5 | 8 | 38 |
| HPV31 | E5 | 9 | 38 |
| HPV31 | E5 | 11 | 38 |
| HPV31 | E6 | 9 | 44 |
| HPV31 | E6 | 8 | 69 |
| HPV31 | E6 | 10 | 69 |
| HPV31 | E6 | 9 | 124 |
| HPV31 | E6 | 9 | 68 |
| HPV31 | E6 | 11 | 68 |
| HPV31 | E6 | 10 | 131 |
| HPV31 | E6 | 9 | 80 |
| HPV31 | E6 | 9 | 83 |
| HPV31 | E6 | 11 | 78 |
| HPV31 | E7 | 10 | 56 |
| HPV31 | L1 | 9 | 151 |
| HPV31 | L1 | 10 | 151 |
| HPV31 | L1 | 9 | 444 |
| HPV31 | L1 | 8 | 370 |
| HPV31 | L1 | 10 | 370 |
| HPV31 | L1 | 9 | 363 |
| HPV31 | L1 | 11 | 363 |
| HPV31 | L1 | 8 | 26 |
| HPV31 | L1 | 10 | 248 |
| HPV31 | L1 | 10 | 447 |
| HPV31 | L1 | 9 | 249 |
| HPV31 | L1 | 9 | 91 |
| HPV31 | L1 | 11 | 91 |
| HPV31 | L1 | 10 | 205 |
| HPV31 | L1 | 8 | 474 |
| HPV31 | L1 | 9 | 376 |
| HPV31 | L1 | 10 | 33 |
| HPV31 | L1 | 11 | 33 |
| HPV31 | L1 | 9 | 83 |
| HPV31 | L1 | 9 | 455 |
| HPV31 | L1 | 11 | 455 |
| HPV31 | L1 | 11 | 237 |
| HPV31 | L1 | 11 | 247 |
| HPV31 | L1 | 11 | 3 |
| HPV31 | L1 | 8 | 342 |
| HPV31 | L1 | 8 | 441 |

TABLE XVIII-continued

HLA.A24 Motif Peptides

| 1 | 2 | 3 | 4 |
|---|---|---|---|
| HPV31 | L1 | 8 | 242 |
| HPV31 | L1 | 10 | 242 |
| HPV31 | L1 | 9 | 374 |
| HPV31 | L1 | 11 | 374 |
| HPV31 | L1 | 8 | 462 |
| HPV31 | L1 | 9 | 462 |
| HPV31 | L1 | 10 | 462 |
| HPV31 | L1 | 8 | 255 |
| HPV31 | L1 | 9 | 70 |
| HPV31 | L1 | 8 | 420 |
| HPV31 | L1 | 10 | 90 |
| HPV31 | L1 | 9 | 149 |
| HPV31 | L1 | 11 | 149 |
| HPV31 | L1 | 10 | 394 |
| HPV31 | L1 | 9 | 299 |
| HPV31 | L1 | 10 | 299 |
| HPV31 | L1 | 11 | 355 |
| HPV31 | L1 | 10 | 390 |
| HPV31 | L1 | 11 | 390 |
| HPV31 | L1 | 10 | 418 |
| HPV31 | L1 | 11 | 446 |
| HPV31 | L1 | 9 | 34 |
| HPV31 | L1 | 10 | 34 |
| HPV31 | L2 | 11 | 251 |
| HPV31 | L2 | 11 | 385 |
| HPV31 | L2 | 8 | 275 |
| HPV31 | L2 | 11 | 438 |
| HPV31 | L2 | 10 | 439 |
| HPV31 | L2 | 9 | 318 |
| HPV31 | L2 | 9 | 403 |
| HPV31 | L2 | 8 | 432 |
| HPV31 | L2 | 10 | 432 |
| HPV31 | L2 | 10 | 352 |
| HPV31 | L2 | 10 | 261 |
| HPV31 | L2 | 10 | 187 |
| HPV31 | L2 | 11 | 187 |
| HPV31 | L2 | 8 | 47 |
| HPV31 | L2 | 9 | 47 |
| HPV31 | L2 | 11 | 295 |
| HPV31 | L2 | 9 | 50 |
| HPV31 | L2 | 11 | 50 |
| HPV31 | L2 | 11 | 195 |
| HPV31 | L2 | 9 | 236 |
| HPV31 | L2 | 10 | 236 |
| HPV31 | L2 | 8 | 157 |
| HPV31 | L2 | 8 | 53 |
| HPV31 | L2 | 9 | 262 |
| HPV31 | L2 | 8 | 319 |
| HPV33 | E1 | 9 | 452 |
| HPV33 | E1 | 9 | 448 |
| HPV33 | E1 | 10 | 448 |
| HPV33 | E1 | 11 | 384 |
| HPV33 | E1 | 9 | 207 |
| HPV33 | E1 | 9 | 297 |
| HPV33 | E1 | 9 | 228 |
| HPV33 | E1 | 11 | 49 |
| HPV33 | E1 | 8 | 580 |
| HPV33 | E1 | 9 | 445 |
| HPV33 | E1 | 11 | 352 |
| HPV33 | E1 | 9 | 331 |
| HPV33 | E1 | 9 | 605 |
| HPV33 | E1 | 11 | 605 |
| HPV33 | E1 | 8 | 212 |
| HPV33 | E1 | 11 | 501 |
| HPV33 | E1 | 8 | 11 |
| HPV33 | E1 | 9 | 512 |
| HPV33 | E1 | 11 | 512 |
| HPV33 | E1 | 8 | 480 |
| HPV33 | E1 | 9 | 16 |
| HPV33 | E1 | 10 | 347 |
| HPV33 | E1 | 8 | 203 |
| HPV33 | E1 | 10 | 203 |
| HPV33 | E1 | 8 | 412 |
| HPV33 | E1 | 11 | 69 |
| HPV33 | E1 | 8 | 286 |
| HPV33 | E1 | 10 | 201 |
| HPV33 | E1 | 8 | 253 |
| HPV33 | E1 | 11 | 312 |
| HPV33 | E1 | 10 | 601 |
| HPV33 | E1 | 8 | 431 |
| HPV33 | E1 | 9 | 431 |
| HPV33 | E1 | 10 | 570 |
| HPV33 | E1 | 8 | 485 |
| HPV33 | E1 | 8 | 355 |
| HPV33 | E1 | 9 | 273 |
| HPV33 | E1 | 9 | 568 |
| HPV33 | E1 | 10 | 440 |
| HPV33 | E1 | 11 | 440 |
| HPV33 | E1 | 10 | 604 |
| HPV33 | E1 | 9 | 211 |
| HPV33 | E1 | 9 | 342 |
| HPV33 | E1 | 8 | 477 |
| HPV33 | E1 | 10 | 477 |
| HPV33 | E1 | 11 | 477 |
| HPV33 | E1 | 8 | 609 |
| HPV33 | E1 | 11 | 523 |
| HPV33 | E1 | 10 | 119 |
| HPV33 | E1 | 8 | 578 |
| HPV33 | E1 | 10 | 578 |
| HPV33 | E1 | 9 | 594 |
| HPV33 | E1 | 8 | 17 |
| HPV33 | E1 | 9 | 314 |
| HPV33 | E1 | 9 | 478 |
| HPV33 | E1 | 10 | 478 |
| HPV33 | E1 | 11 | 528 |
| HPV33 | E1 | 10 | 313 |
| HPV33 | E2 | 11 | 69 |
| HPV33 | E2 | 8 | 153 |
| HPV33 | E2 | 8 | 130 |
| HPV33 | E2 | 10 | 130 |
| HPV33 | E2 | 11 | 130 |
| HPV33 | E2 | 11 | 32 |
| HPV33 | E2 | 8 | 177 |
| HPV33 | E2 | 8 | 243 |
| HPV33 | E2 | 9 | 18 |
| HPV33 | E2 | 9 | 299 |
| HPV33 | E2 | 11 | 299 |
| HPV33 | E2 | 9 | 43 |
| HPV33 | E2 | 8 | 333 |
| HPV33 | E2 | 11 | 183 |
| HPV33 | E2 | 8 | 133 |
| HPV33 | E2 | 9 | 332 |
| HPV33 | E2 | 9 | 91 |
| HPV33 | E2 | 9 | 86 |
| HPV33 | E2 | 10 | 290 |
| HPV33 | E2 | 8 | 302 |
| HPV33 | E2 | 11 | 324 |
| HPV33 | E2 | 10 | 128 |
| HPV33 | E2 | 10 | 146 |
| HPV33 | E2 | 10 | 101 |
| HPV33 | E2 | 11 | 158 |
| HPV33 | E5 | 8 | 30 |
| HPV33 | E5 | 9 | 30 |
| HPV33 | E5 | 10 | 30 |
| HPV33 | E5 | 11 | 30 |
| HPV33 | E5 | 8 | 8 |
| HPV33 | E5 | 10 | 8 |
| HPV33 | E5 | 11 | 8 |
| HPV33 | E5 | 8 | 52 |
| HPV33 | E5 | 8 | 50 |
| HPV33 | E5 | 10 | 50 |
| HPV33 | E5 | 8 | 49 |
| HPV33 | E5 | 9 | 49 |
| HPV33 | E5 | 11 | 49 |
| HPV33 | E5 | 8 | 2 |
| HPV33 | E5 | 9 | 2 |
| HPV33 | E5 | 10 | 2 |
| HPV33 | E5 | 11 | 2 |
| HPV33 | E5 | 8 | 11 |
| HPV33 | E5 | 9 | 11 |

TABLE XVIII-continued

HLA.A24 Motif Peptides

| 1 | 2 | 3 | 4 |
|---|---|---|---|
| HPV33 | E5 | 10 | 55 |
| HPV33 | E5 | 9 | 39 |
| HPV33 | E5 | 11 | 39 |
| HPV33 | E5 | 8 | 57 |
| HPV33 | E5 | 10 | 57 |
| HPV33 | E5 | 8 | 28 |
| HPV33 | E5 | 10 | 28 |
| HPV33 | E5 | 11 | 28 |
| HPV33 | E5 | 9 | 41 |
| HPV33 | E5 | 10 | 41 |
| HPV33 | E5 | 11 | 41 |
| HPV33 | E5 | 8 | 4 |
| HPV33 | E5 | 9 | 4 |
| HPV33 | E5 | 10 | 4 |
| HPV33 | E6 | 11 | 139 |
| HPV33 | E6 | 11 | 78 |
| HPV33 | E6 | 9 | 80 |
| HPV33 | E6 | 9 | 59 |
| HPV33 | E6 | 11 | 59 |
| HPV33 | E6 | 9 | 124 |
| HPV33 | E6 | 10 | 131 |
| HPV33 | E6 | 9 | 42 |
| HPV33 | E6 | 8 | 53 |
| HPV33 | E6 | 10 | 53 |
| HPV33 | E7 | 8 | 15 |
| HPV33 | L1 | 10 | 392 |
| HPV33 | L1 | 9 | 151 |
| HPV33 | L1 | 10 | 151 |
| HPV33 | L1 | 8 | 368 |
| HPV33 | L1 | 10 | 368 |
| HPV33 | L1 | 11 | 361 |
| HPV33 | L1 | 8 | 26 |
| HPV33 | L1 | 10 | 247 |
| HPV33 | L1 | 9 | 248 |
| HPV33 | L1 | 8 | 260 |
| HPV33 | L1 | 10 | 445 |
| HPV33 | L1 | 9 | 91 |
| HPV33 | L1 | 11 | 91 |
| HPV33 | L1 | 10 | 204 |
| HPV33 | L1 | 9 | 259 |
| HPV33 | L1 | 10 | 33 |
| HPV33 | L1 | 11 | 33 |
| HPV33 | L1 | 9 | 83 |
| HPV33 | L1 | 8 | 466 |
| HPV33 | L1 | 9 | 453 |
| HPV33 | L1 | 11 | 453 |
| HPV33 | L1 | 11 | 236 |
| HPV33 | L1 | 9 | 442 |
| HPV33 | L1 | 11 | 246 |
| HPV33 | L1 | 8 | 306 |
| HPV33 | L1 | 8 | 241 |
| HPV33 | L1 | 9 | 241 |
| HPV33 | L1 | 10 | 241 |
| HPV33 | L1 | 8 | 460 |
| HPV33 | L1 | 9 | 460 |
| HPV33 | L1 | 10 | 460 |
| HPV33 | L1 | 11 | 372 |
| HPV33 | L1 | 8 | 254 |
| HPV33 | L1 | 9 | 70 |
| HPV33 | L1 | 8 | 418 |
| HPV33 | L1 | 10 | 90 |
| HPV33 | L1 | 9 | 149 |
| HPV33 | L1 | 11 | 149 |
| HPV33 | L1 | 9 | 298 |
| HPV33 | L1 | 10 | 298 |
| HPV33 | L1 | 11 | 444 |
| HPV33 | L1 | 10 | 388 |
| HPV33 | L1 | 11 | 388 |
| HPV33 | L1 | 11 | 353 |
| HPV33 | L1 | 10 | 416 |
| HPV33 | L1 | 9 | 374 |
| HPV33 | L1 | 9 | 100 |
| HPV33 | L1 | 11 | 3 |
| HPV33 | L1 | 8 | 35 |
| HPV33 | L1 | 9 | 35 |
| HPV33 | L1 | 9 | 34 |
| HPV33 | L1 | 10 | 34 |
| HPV33 | L2 | 11 | 256 |
| HPV33 | L2 | 9 | 241 |
| HPV33 | L2 | 10 | 241 |
| HPV33 | L2 | 8 | 280 |
| HPV33 | L2 | 9 | 439 |
| HPV33 | L2 | 10 | 439 |
| HPV33 | L2 | 11 | 439 |
| HPV33 | L2 | 9 | 323 |
| HPV33 | L2 | 8 | 46 |
| HPV33 | L2 | 9 | 46 |
| HPV33 | L2 | 8 | 414 |
| HPV33 | L2 | 11 | 414 |
| HPV33 | L2 | 8 | 426 |
| HPV33 | L2 | 8 | 420 |
| HPV33 | L2 | 9 | 420 |
| HPV33 | L2 | 11 | 420 |
| HPV33 | L2 | 9 | 376 |
| HPV33 | L2 | 11 | 300 |
| HPV33 | L2 | 8 | 259 |
| HPV33 | L2 | 10 | 259 |
| HPV33 | L2 | 10 | 192 |
| HPV33 | L2 | 8 | 355 |
| HPV33 | L2 | 8 | 162 |
| HPV33 | L2 | 10 | 251 |
| HPV33 | L2 | 8 | 52 |
| HPV33 | L2 | 11 | 404 |
| HPV33 | L2 | 11 | 446 |
| HPV33 | L2 | 8 | 324 |
| HPV33 | L2 | 11 | 324 |
| HPV45 | E1 | 9 | 199 |
| HPV45 | E1 | 11 | 512 |
| HPV45 | E1 | 10 | 604 |
| HPV45 | E1 | 9 | 297 |
| HPV45 | E1 | 9 | 49 |
| HPV45 | E1 | 9 | 367 |
| HPV45 | E1 | 10 | 46 |
| HPV45 | E1 | 11 | 352 |
| HPV45 | E1 | 8 | 431 |
| HPV45 | E1 | 9 | 431 |
| HPV45 | E1 | 9 | 445 |
| HPV45 | E1 | 8 | 331 |
| HPV45 | E1 | 9 | 331 |
| HPV45 | E1 | 9 | 605 |
| HPV45 | E1 | 11 | 605 |
| HPV45 | E1 | 11 | 243 |
| HPV45 | E1 | 8 | 480 |
| HPV45 | E1 | 8 | 16 |
| HPV45 | E1 | 8 | 485 |
| HPV45 | E1 | 10 | 485 |
| HPV45 | E1 | 9 | 207 |
| HPV45 | E1 | 9 | 263 |
| HPV45 | E1 | 10 | 263 |
| HPV45 | E1 | 8 | 253 |
| HPV45 | E1 | 8 | 312 |
| HPV45 | E1 | 11 | 312 |
| HPV45 | E1 | 10 | 347 |
| HPV45 | E1 | 10 | 601 |
| HPV45 | E1 | 10 | 570 |
| HPV45 | E1 | 10 | 437 |
| HPV45 | E1 | 11 | 437 |
| HPV45 | E1 | 8 | 412 |
| HPV45 | E1 | 8 | 355 |
| HPV45 | E1 | 10 | 417 |
| HPV45 | E1 | 9 | 273 |
| HPV45 | E1 | 8 | 440 |
| HPV45 | E1 | 10 | 440 |
| HPV45 | E1 | 11 | 440 |
| HPV45 | E1 | 10 | 482 |
| HPV45 | E1 | 11 | 482 |
| HPV45 | E1 | 9 | 448 |
| HPV45 | E1 | 10 | 448 |
| HPV45 | E1 | 9 | 211 |
| HPV45 | E1 | 9 | 493 |

TABLE XVIII-continued

HLA.A24 Motif Peptides

| 1 | 2 | 3 | 4 |
|---|---|---|---|
| HPV45 | E1 | 10 | 493 |
| HPV45 | E1 | 11 | 493 |
| HPV45 | E1 | 8 | 477 |
| HPV45 | E1 | 10 | 477 |
| HPV45 | E1 | 11 | 477 |
| HPV45 | E1 | 8 | 580 |
| HPV45 | E1 | 11 | 523 |
| HPV45 | E1 | 8 | 203 |
| HPV45 | E1 | 10 | 203 |
| HPV45 | E1 | 8 | 578 |
| HPV45 | E1 | 10 | 578 |
| HPV45 | E1 | 9 | 594 |
| HPV45 | E1 | 9 | 314 |
| HPV45 | E1 | 10 | 524 |
| HPV45 | E1 | 9 | 478 |
| HPV45 | E1 | 10 | 478 |
| HPV45 | E1 | 11 | 528 |
| HPV45 | E1 | 10 | 313 |
| HPV45 | E2 | 10 | 134 |
| HPV45 | E2 | 11 | 97 |
| HPV45 | E2 | 11 | 325 |
| HPV45 | E2 | 9 | 24 |
| HPV45 | E2 | 9 | 316 |
| HPV45 | E2 | 11 | 316 |
| HPV45 | E2 | 9 | 143 |
| HPV45 | E2 | 10 | 143 |
| HPV45 | E2 | 9 | 2 |
| HPV45 | E2 | 9 | 312 |
| HPV45 | E2 | 8 | 184 |
| HPV45 | E2 | 9 | 92 |
| HPV45 | E2 | 9 | 49 |
| HPV45 | E2 | 10 | 107 |
| HPV45 | E2 | 8 | 136 |
| HPV45 | E2 | 11 | 136 |
| HPV45 | E2 | 8 | 160 |
| HPV45 | E2 | 8 | 37 |
| HPV45 | E2 | 8 | 348 |
| HPV45 | E2 | 11 | 190 |
| HPV45 | E2 | 11 | 339 |
| HPV45 | E2 | 8 | 139 |
| HPV45 | E2 | 11 | 38 |
| HPV45 | E2 | 8 | 144 |
| HPV45 | E2 | 9 | 144 |
| HPV45 | E6 | 9 | 61 |
| HPV45 | E6 | 11 | 61 |
| HPV45 | E6 | 9 | 70 |
| HPV45 | E6 | 8 | 71 |
| HPV45 | E6 | 9 | 52 |
| HPV45 | E6 | 9 | 98 |
| HPV45 | E6 | 11 | 11 |
| HPV45 | E6 | 8 | 46 |
| HPV45 | E6 | 9 | 46 |
| HPV45 | E6 | 9 | 85 |
| HPV45 | E6 | 9 | 44 |
| HPV45 | E6 | 10 | 44 |
| HPV45 | E6 | 11 | 44 |
| HPV45 | E6 | 11 | 80 |
| HPV45 | E7 | 8 | 90 |
| HPV45 | L1 | 11 | 94 |
| HPV45 | L1 | 9 | 177 |
| HPV45 | L1 | 10 | 177 |
| HPV45 | L1 | 8 | 52 |
| HPV45 | L1 | 9 | 52 |
| HPV45 | L1 | 8 | 399 |
| HPV45 | L1 | 10 | 399 |
| HPV45 | L1 | 9 | 274 |
| HPV45 | L1 | 10 | 274 |
| HPV45 | L1 | 10 | 476 |
| HPV45 | L1 | 9 | 60 |
| HPV45 | L1 | 10 | 60 |
| HPV45 | L1 | 10 | 131 |
| HPV45 | L1 | 10 | 231 |
| HPV45 | L1 | 11 | 392 |
| HPV45 | L1 | 9 | 13 |
| HPV45 | L1 | 11 | 13 |
| HPV45 | L1 | 8 | 23 |
| HPV45 | L1 | 9 | 405 |
| HPV45 | L1 | 10 | 59 |
| HPV45 | L1 | 11 | 59 |
| HPV45 | L1 | 8 | 6 |
| HPV45 | L1 | 9 | 6 |
| HPV45 | L1 | 10 | 6 |
| HPV45 | L1 | 9 | 117 |
| HPV45 | L1 | 11 | 117 |
| HPV45 | L1 | 9 | 109 |
| HPV45 | L1 | 8 | 497 |
| HPV45 | L1 | 11 | 484 |
| HPV45 | L1 | 11 | 475 |
| HPV45 | L1 | 8 | 335 |
| HPV45 | L1 | 11 | 29 |
| HPV45 | L1 | 10 | 273 |
| HPV45 | L1 | 11 | 273 |
| HPV45 | L1 | 8 | 470 |
| HPV45 | L1 | 8 | 268 |
| HPV45 | L1 | 10 | 268 |
| HPV45 | L1 | 9 | 403 |
| HPV45 | L1 | 11 | 403 |
| HPV45 | L1 | 8 | 491 |
| HPV45 | L1 | 9 | 491 |
| HPV45 | L1 | 9 | 96 |
| HPV45 | L1 | 11 | 272 |
| HPV45 | L1 | 10 | 423 |
| HPV45 | L1 | 10 | 419 |
| HPV45 | L1 | 11 | 419 |
| HPV45 | L1 | 10 | 20 |
| HPV45 | L1 | 11 | 20 |
| HPV45 | L1 | 10 | 293 |
| HPV45 | L1 | 9 | 126 |
| HPV45 | L1 | 10 | 319 |
| HPV45 | L2 | 8 | 161 |
| HPV45 | L2 | 9 | 255 |
| HPV45 | L2 | 11 | 255 |
| HPV45 | L2 | 8 | 275 |
| HPV45 | L2 | 8 | 319 |
| HPV45 | L2 | 10 | 191 |
| HPV45 | L2 | 9 | 318 |
| HPV45 | L2 | 8 | 52 |
| HPV45 | L2 | 8 | 400 |
| HPV45 | L2 | 9 | 400 |
| HPV45 | L2 | 8 | 346 |
| HPV45 | L2 | 8 | 438 |
| HPV45 | L2 | 9 | 305 |
| HPV45 | L2 | 8 | 453 |
| HPV45 | L2 | 9 | 240 |
| HPV45 | L2 | 8 | 46 |
| HPV45 | L2 | 9 | 46 |
| HPV45 | L2 | 11 | 435 |
| HPV45 | L2 | 9 | 367 |
| HPV45 | L2 | 9 | 384 |
| HPV45 | L2 | 10 | 250 |
| HPV45 | L2 | 8 | 121 |
| HPV45 | L2 | 10 | 121 |
| HPV45 | L2 | 10 | 304 |
| HPV45 | L2 | 9 | 444 |
| HPV45 | L2 | 10 | 443 |
| HPV45 | L2 | 10 | 436 |
| HPV45 | L2 | 11 | 442 |
| HPV56 | E2 | 9 | 52 |
| HPV56 | E2 | 10 | 71 |
| HPV56 | E2 | 9 | 113 |
| HPV56 | E2 | 11 | 34 |
| HPV56 | E2 | 11 | 126 |
| HPV56 | E2 | 11 | 284 |
| HPV56 | E2 | 9 | 29 |
| HPV56 | E2 | 9 | 80 |
| HPV56 | E2 | 8 | 120 |
| HPV56 | E2 | 11 | 78 |
| HPV56 | E2 | 11 | 260 |
| HPV56 | E2 | 10 | 44 |
| HPV56 | E2 | 8 | 277 |

TABLE XVIII-continued

HLA.A24 Motif Peptides

| 1 | 2 | 3 | 4 |
|---|---|---|---|
| HPV56 | E2 | 8 | 73 |
| HPV56 | E2 | 8 | 253 |
| HPV56 | E2 | 9 | 253 |
| HPV56 | E2 | 10 | 251 |
| HPV56 | E2 | 11 | 251 |
| HPV56 | E2 | 8 | 293 |
| HPV56 | E2 | 8 | 81 |
| HPV56 | E6 | 8 | 106 |
| HPV56 | E6 | 11 | 60 |
| HPV56 | E6 | 9 | 83 |
| HPV56 | E6 | 10 | 134 |
| HPV56 | E6 | 9 | 47 |
| HPV56 | E6 | 9 | 62 |
| HPV56 | E6 | 10 | 62 |
| HPV56 | E6 | 11 | 62 |
| HPV56 | E6 | 9 | 127 |
| HPV56 | E6 | 9 | 86 |
| HPV56 | E6 | 9 | 45 |
| HPV56 | E6 | 11 | 45 |
| HPV56 | E6 | 11 | 81 |
| HPV56 | E7 | 8 | 69 |
| HPV56 | E7 | 11 | 90 |
| HPV56 | L1 | 8 | 275 |
| HPV56 | L1 | 10 | 275 |
| HPV56 | L1 | 10 | 422 |
| HPV56 | L1 | 11 | 422 |
| HPV56 | L1 | 11 | 101 |
| HPV56 | L1 | 8 | 402 |
| HPV56 | L1 | 10 | 402 |
| HPV56 | L1 | 10 | 479 |
| HPV56 | L1 | 9 | 69 |
| HPV56 | L1 | 10 | 69 |
| HPV56 | L1 | 8 | 282 |
| HPV56 | L1 | 9 | 282 |
| HPV56 | L1 | 10 | 238 |
| HPV56 | L1 | 8 | 15 |
| HPV56 | L1 | 11 | 20 |
| HPV56 | L1 | 8 | 32 |
| HPV56 | L1 | 10 | 68 |
| HPV56 | L1 | 11 | 68 |
| HPV56 | L1 | 9 | 124 |
| HPV56 | L1 | 11 | 124 |
| HPV56 | L1 | 11 | 8 |
| HPV56 | L1 | 9 | 116 |
| HPV56 | L1 | 11 | 478 |
| HPV56 | L1 | 11 | 387 |
| HPV56 | L1 | 9 | 476 |
| HPV56 | L1 | 10 | 450 |
| HPV56 | L1 | 8 | 340 |
| HPV56 | L1 | 8 | 1 |
| HPV56 | L1 | 10 | 5 |
| HPV56 | L1 | 10 | 280 |
| HPV56 | L1 | 11 | 280 |
| HPV56 | L1 | 9 | 6 |
| HPV56 | L1 | 10 | 426 |
| HPV56 | L1 | 11 | 375 |
| HPV56 | L1 | 11 | 4 |
| HPV56 | L1 | 8 | 494 |
| HPV56 | L1 | 9 | 494 |
| HPV56 | L1 | 9 | 406 |
| HPV56 | L1 | 11 | 406 |
| HPV56 | L1 | 11 | 395 |
| HPV56 | L1 | 9 | 103 |
| HPV56 | L1 | 8 | 452 |
| HPV56 | L1 | 9 | 487 |
| HPV56 | L1 | 11 | 487 |
| HPV56 | L1 | 9 | 332 |
| HPV56 | L1 | 10 | 332 |
| HPV56 | L1 | 11 | 279 |
| HPV56 | L1 | 8 | 61 |
| HPV56 | L1 | 9 | 61 |
| HPV56 | L1 | 11 | 38 |
| HPV56 | L1 | 11 | 29 |
| HPV56 | L1 | 9 | 408 |
| HPV56 | L1 | 11 | 324 |
| HPV56 | L1 | 9 | 281 |
| HPV56 | L1 | 10 | 281 |
| HPV56 | L2 | 9 | 240 |
| HPV56 | L2 | 11 | 286 |
| HPV56 | L2 | 8 | 275 |
| HPV56 | L2 | 10 | 444 |
| HPV56 | L2 | 9 | 401 |
| HPV56 | L2 | 10 | 217 |
| HPV56 | L2 | 9 | 318 |
| HPV56 | L2 | 9 | 255 |
| HPV56 | L2 | 11 | 255 |
| HPV56 | L2 | 8 | 161 |
| HPV56 | L2 | 8 | 50 |
| HPV56 | L2 | 10 | 50 |
| HPV56 | L2 | 8 | 347 |
| HPV56 | L2 | 8 | 121 |
| HPV56 | L2 | 10 | 121 |
| HPV56 | L2 | 8 | 400 |
| HPV56 | L2 | 10 | 400 |
| HPV56 | L2 | 10 | 423 |
| HPV56 | L2 | 9 | 46 |
| HPV56 | L2 | 11 | 295 |
| HPV56 | L2 | 9 | 436 |
| HPV56 | L2 | 10 | 436 |
| HPV56 | L2 | 8 | 343 |
| HPV56 | L2 | 10 | 191 |
| HPV56 | L2 | 9 | 39 |
| HPV56 | L2 | 8 | 52 |
| HPV56 | L2 | 8 | 430 |
| HPV56 | L2 | 10 | 430 |
| HPV56 | L2 | 11 | 430 |
| HPV56 | L2 | 11 | 443 |
| HPV56 | L2 | 8 | 319 |

TABLE XVIII A

HPV6A
HLA-A24 Motif Peptides

| 2 | 3 | 4 |
|---|---|---|
| E1 | 10 | 377 |
| L2 | 9 | 238 |
| L2 | 10 | 238 |
| L2 | 8 | 275 |
| E1 | 9 | 251 |
| E1 | 11 | 251 |
| E5 | 9 | 23 |
| E5 | 10 | 23 |
| E5 | 11 | 23 |
| E1 | 9 | 271 |
| L1 | 11 | 384 |
| E6 | 8 | 47 |
| E6 | 9 | 47 |
| L1 | 8 | 25 |
| L1 | 9 | 25 |
| E1 | 10 | 612 |
| E1 | 9 | 215 |
| E1 | 10 | 215 |
| E5 | 8 | 27 |
| E5 | 10 | 27 |
| E5 | 11 | 27 |
| E2 | 8 | 35 |
| E2 | 9 | 35 |
| E1 | 8 | 488 |
| L1 | 9 | 153 |
| E6 | 10 | 140 |
| E5 | 8 | 75 |
| E6 | 8 | 104 |
| E1 | 9 | 385 |
| E1 | 10 | 385 |
| E1 | 8 | 49 |

TABLE XVIII A-continued

HPV6A
HLA-A24 Motif Peptides

| 2 | 3 | 4 |
|---|---|---|
| E5 | 9 | 39 |
| E5 | 11 | 39 |
| E1 | 11 | 46 |
| E1 | 9 | 236 |
| E1 | 9 | 453 |
| E1 | 11 | 453 |
| E2 | 9 | 74 |
| E2 | 10 | 74 |
| E1 | 10 | 417 |
| E1 | 11 | 417 |
| E1 | 11 | 360 |
| E2 | 11 | 100 |
| E1 | 9 | 339 |
| E1 | 8 | 379 |
| L1 | 8 | 364 |
| L1 | 10 | 364 |
| L1 | 11 | 357 |
| E2 | 9 | 86 |
| E1 | 9 | 613 |
| E1 | 11 | 613 |
| L1 | 10 | 243 |
| L1 | 9 | 244 |
| L1 | 10 | 441 |
| L1 | 9 | 33 |
| L1 | 10 | 33 |
| L2 | 9 | 434 |
| L1 | 10 | 200 |
| E1 | 8 | 241 |
| E2 | 8 | 361 |
| L2 | 8 | 433 |
| L2 | 10 | 433 |
| L1 | 9 | 144 |
| E2 | 8 | 55 |
| E1 | 10 | 273 |
| E1 | 8 | 16 |
| E1 | 8 | 44 |
| E6 | 11 | 58 |
| L1 | 11 | 64 |
| L1 | 8 | 468 |
| E2 | 11 | 32 |
| E1 | 8 | 75 |
| L2 | 9 | 318 |
| L1 | 9 | 370 |
| L1 | 10 | 32 |
| L1 | 11 | 32 |
| L2 | 10 | 348 |
| E1 | 10 | 531 |
| E1 | 11 | 531 |
| E6 | 9 | 43 |
| L1 | 10 | 286 |
| E2 | 8 | 157 |
| L1 | 9 | 79 |
| L1 | 10 | 79 |
| E1 | 8 | 211 |
| E1 | 10 | 211 |
| E1 | 11 | 211 |
| L1 | 11 | 449 |
| E1 | 8 | 420 |
| L2 | 8 | 46 |
| L2 | 9 | 46 |
| E2 | 8 | 177 |
| E1 | 11 | 85 |
| E1 | 10 | 578 |
| E4 | 8 | 18 |
| E2 | 9 | 311 |
| E2 | 11 | 311 |
| L1 | 9 | 87 |
| L1 | 11 | 87 |
| L1 | 11 | 242 |
| L2 | 9 | 397 |
| L2 | 11 | 397 |
| L1 | 8 | 302 |
| E5 | 9 | 57 |
| E5 | 11 | 57 |
| E1 | 8 | 261 |
| E2 | 9 | 18 |
| E2 | 9 | 43 |
| E4 | 11 | 11 |
| E5 | 8 | 53 |
| E5 | 9 | 53 |
| E4 | 9 | 5 |
| E4 | 11 | 5 |
| E1 | 8 | 320 |
| E2 | 10 | 101 |
| E1 | 9 | 609 |
| E1 | 8 | 439 |
| E1 | 9 | 439 |
| E1 | 8 | 456 |
| E1 | 9 | 456 |
| E1 | 10 | 456 |
| L2 | 8 | 415 |
| E1 | 11 | 545 |
| L2 | 9 | 382 |
| E4 | 11 | 71 |
| E6 | 9 | 60 |
| E6 | 11 | 60 |
| L1 | 8 | 237 |
| L1 | 9 | 237 |
| L1 | 10 | 237 |
| L1 | 8 | 435 |
| E1 | 9 | 90 |
| E5 | 8 | 66 |
| L1 | 9 | 368 |
| L1 | 11 | 368 |
| E1 | 10 | 355 |
| E2 | 9 | 163 |
| E2 | 8 | 345 |
| E1 | 8 | 445 |
| E1 | 10 | 445 |
| E1 | 11 | 445 |
| E2 | 9 | 289 |
| L1 | 11 | 232 |
| L1 | 8 | 250 |
| E2 | 8 | 76 |
| E1 | 9 | 305 |
| E1 | 8 | 363 |
| E2 | 11 | 183 |
| E1 | 10 | 425 |
| E1 | 11 | 266 |
| L1 | 8 | 456 |
| L1 | 9 | 456 |
| L1 | 10 | 456 |
| L1 | 9 | 66 |
| E6 | 9 | 125 |
| E2 | 11 | 301 |
| L1 | 8 | 414 |
| E1 | 9 | 219 |
| E1 | 8 | 493 |
| L1 | 11 | 440 |
| E6 | 11 | 23 |
| L2 | 10 | 304 |
| E2 | 8 | 150 |
| E6 | 10 | 45 |
| E6 | 11 | 45 |
| E1 | 8 | 485 |
| E1 | 10 | 485 |
| E1 | 11 | 485 |
| L2 | 9 | 345 |
| E6 | 9 | 19 |
| E6 | 11 | 19 |
| E1 | 8 | 588 |
| L2 | 11 | 406 |
| E1 | 8 | 586 |
| E1 | 10 | 586 |
| L1 | 10 | 388 |
| E6 | 10 | 132 |
| E2 | 11 | 336 |
| L1 | 10 | 412 |

TABLE XVIII A-continued

HPV6A
HLA-A24 Motif Peptides

| 2 | 3 | 4 |
|---|---|---|
| L2 | 8 | 52 |
| L2 | 8 | 427 |
| L2 | 10 | 427 |
| E4 | 8 | 65 |
| L2 | 11 | 253 |
| E1 | 9 | 602 |
| E5 | 8 | 42 |
| E5 | 10 | 42 |
| E5 | 11 | 42 |
| E2 | 9 | 137 |
| L2 | 11 | 440 |
| L2 | 10 | 441 |
| E1 | 9 | 486 |
| E1 | 10 | 486 |
| L2 | 8 | 319 |
| E1 | 9 | 532 |
| E1 | 10 | 532 |
| L1 | 10 | 358 |

TABLE XVIII B

HPV6B
HLA-A24 Motif Peptides

| 2 | 3 | 4 |
|---|---|---|
| E1 | 10 | 377 |
| E5B | 9 | 21 |
| E5B | 10 | 21 |
| E5B | 11 | 21 |
| L2 | 9 | 238 |
| L2 | 10 | 238 |
| L2 | 8 | 275 |
| E1 | 9 | 251 |
| E1 | 11 | 251 |
| E5A | 9 | 23 |
| E5A | 10 | 23 |
| E5A | 11 | 23 |
| E1 | 9 | 271 |
| E1 | 10 | 271 |
| L1 | 11 | 384 |
| E6 | 8 | 47 |
| E6 | 9 | 47 |
| L1 | 8 | 25 |
| L1 | 9 | 25 |
| E1 | 10 | 612 |
| E1 | 9 | 215 |
| E1 | 10 | 215 |
| E5A | 8 | 27 |
| E5A | 10 | 27 |
| E5A | 11 | 27 |
| E2 | 8 | 35 |
| E2 | 9 | 35 |
| E1 | 8 | 488 |
| L1 | 9 | 153 |
| E6 | 10 | 140 |
| E5A | 8 | 75 |
| E6 | 8 | 104 |
| E1 | 9 | 385 |
| E1 | 10 | 385 |
| E1 | 8 | 49 |
| E1 | 11 | 46 |
| E1 | 9 | 236 |
| E1 | 9 | 453 |
| E1 | 11 | 453 |
| E5A | 9 | 39 |
| E5A | 11 | 39 |
| E2 | 9 | 74 |
| E2 | 10 | 74 |
| E1 | 10 | 417 |
| E1 | 11 | 417 |

TABLE XVIII B-continued

HPV6B
HLA-A24 Motif Peptides

| 2 | 3 | 4 |
|---|---|---|
| E1 | 11 | 360 |
| E2 | 11 | 100 |
| E1 | 9 | 339 |
| E1 | 8 | 379 |
| L1 | 8 | 364 |
| L1 | 10 | 364 |
| L1 | 11 | 357 |
| E2 | 9 | 86 |
| E1 | 9 | 613 |
| E1 | 11 | 613 |
| L1 | 10 | 243 |
| L1 | 9 | 244 |
| L1 | 10 | 441 |
| L1 | 9 | 33 |
| L1 | 10 | 33 |
| L2 | 9 | 434 |
| L1 | 10 | 200 |
| E1 | 8 | 241 |
| E2 | 8 | 361 |
| L2 | 8 | 433 |
| L2 | 10 | 433 |
| L1 | 9 | 144 |
| E2 | 8 | 55 |
| E1 | 8 | 273 |
| E1 | 10 | 273 |
| E1 | 8 | 16 |
| E1 | 8 | 44 |
| E6 | 11 | 58 |
| L1 | 11 | 64 |
| L1 | 8 | 468 |
| E2 | 11 | 183 |
| E2 | 11 | 32 |
| E1 | 8 | 75 |
| L2 | 9 | 318 |
| E5B | 9 | 61 |
| L1 | 9 | 370 |
| L1 | 10 | 32 |
| L1 | 11 | 32 |
| L2 | 10 | 348 |
| E1 | 10 | 531 |
| E1 | 11 | 531 |
| E6 | 9 | 43 |
| L1 | 10 | 286 |
| E2 | 8 | 157 |
| L1 | 9 | 79 |
| L1 | 10 | 79 |
| E1 | 8 | 211 |
| E1 | 10 | 211 |
| E1 | 11 | 211 |
| L1 | 11 | 449 |
| E1 | 8 | 420 |
| L2 | 8 | 46 |
| L2 | 9 | 46 |
| E2 | 8 | 177 |
| E1 | 11 | 85 |
| E1 | 10 | 578 |
| E4 | 8 | 28 |
| E4 | 8 | 8 |
| E4 | 11 | 8 |
| E2 | 9 | 311 |
| E2 | 11 | 311 |
| L1 | 9 | 87 |
| L1 | 11 | 87 |
| L1 | 11 | 242 |
| L2 | 9 | 396 |
| L2 | 11 | 396 |
| L1 | 8 | 302 |
| E5B | 8 | 16 |
| E5A | 9 | 57 |
| E5A | 11 | 57 |
| E1 | 8 | 261 |
| E2 | 9 | 18 |
| E2 | 9 | 43 |
| E4 | 11 | 21 |

TABLE XVIII B-continued

HPV6B
HLA-A24 Motif Peptides

| 2 | 3 | 4 |
|---|---|---|
| E5A | 8 | 53 |
| E5A | 9 | 53 |
| E4 | 9 | 15 |
| E4 | 11 | 15 |
| E1 | 8 | 320 |
| E2 | 10 | 101 |
| E1 | 9 | 609 |
| E1 | 8 | 439 |
| E1 | 9 | 439 |
| E1 | 10 | 226 |
| E1 | 8 | 456 |
| E1 | 9 | 456 |
| E1 | 10 | 456 |
| L2 | 9 | 414 |
| E1 | 11 | 545 |
| L2 | 9 | 382 |
| L2 | 11 | 382 |
| E4 | 11 | 81 |
| E6 | 9 | 60 |
| E6 | 11 | 60 |
| L1 | 8 | 237 |
| L1 | 9 | 237 |
| L1 | 10 | 237 |
| L1 | 8 | 435 |
| E1 | 9 | 90 |
| E5A | 8 | 66 |
| L1 | 9 | 368 |
| L1 | 11 | 368 |
| E1 | 10 | 355 |
| E2 | 9 | 163 |
| E2 | 8 | 345 |
| E1 | 8 | 445 |
| E1 | 10 | 445 |
| E1 | 11 | 445 |
| E5B | 8 | 6 |
| E5B | 9 | 6 |
| E5B | 11 | 6 |
| E2 | 9 | 289 |
| L1 | 11 | 232 |
| L1 | 8 | 250 |
| E2 | 8 | 76 |
| E1 | 9 | 305 |
| E1 | 8 | 363 |
| E1 | 10 | 425 |
| E1 | 11 | 266 |
| L1 | 8 | 456 |
| L1 | 9 | 456 |
| L1 | 10 | 456 |
| L1 | 9 | 66 |
| E6 | 9 | 125 |
| E2 | 11 | 301 |
| L1 | 8 | 414 |
| E1 | 9 | 219 |
| E1 | 8 | 493 |
| L1 | 11 | 440 |
| E6 | 11 | 23 |
| L2 | 10 | 304 |
| E2 | 8 | 150 |
| E6 | 10 | 45 |
| E6 | 11 | 45 |
| E1 | 8 | 485 |
| E1 | 10 | 485 |
| E1 | 11 | 485 |
| L2 | 9 | 345 |
| E5A | 8 | 15 |
| E5A | 10 | 15 |
| E6 | 9 | 19 |
| E6 | 11 | 19 |
| E1 | 8 | 588 |
| L2 | 11 | 405 |
| E1 | 8 | 586 |
| E1 | 10 | 586 |
| E5B | 11 | 59 |
| L1 | 10 | 388 |

TABLE XVIII B-continued

HPV6B
HLA-A24 Motif Peptides

| 2 | 3 | 4 |
|---|---|---|
| E6 | 10 | 132 |
| E5B | 8 | 12 |
| E5B | 11 | 12 |
| E2 | 11 | 336 |
| L1 | 10 | 412 |
| E2 | 10 | 213 |
| L2 | 8 | 52 |
| L2 | 8 | 427 |
| L2 | 10 | 427 |
| E4 | 9 | 10 |
| E4 | 10 | 10 |
| E4 | 8 | 75 |
| L2 | 11 | 253 |
| E1 | 9 | 602 |
| E5A | 8 | 42 |
| E5A | 10 | 42 |
| E5A | 11 | 42 |
| E2 | 9 | 137 |
| L2 | 11 | 440 |
| L2 | 10 | 441 |
| E1 | 9 | 486 |
| E1 | 10 | 486 |
| L2 | 8 | 319 |
| E1 | 9 | 532 |
| E1 | 10 | 532 |
| L1 | 10 | 358 |

TABLE XVIII C

HPV1I
HLA-A24 Motif Peptides

| 2 | 3 | 4 |
|---|---|---|
| E5 | 9 | 23 |
| E5 | 11 | 23 |
| E1 | 10 | 377 |
| L2 | 9 | 237 |
| L2 | 8 | 274 |
| L2 | 9 | 215 |
| E1 | 9 | 251 |
| E1 | 11 | 251 |
| E5 | 9 | 22 |
| E5 | 10 | 22 |
| E5 | 11 | 22 |
| E5 | 8 | 79 |
| E1 | 9 | 271 |
| E1 | 10 | 271 |
| E6 | 11 | 45 |
| L1 | 11 | 385 |
| E6 | 9 | 47 |
| L1 | 8 | 25 |
| L1 | 9 | 25 |
| E1 | 9 | 486 |
| E1 | 10 | 486 |
| E1 | 10 | 612 |
| E1 | 9 | 215 |
| E1 | 10 | 215 |
| E1 | 8 | 488 |
| L1 | 9 | 154 |
| E6 | 9 | 140 |
| E6 | 10 | 140 |
| E5 | 8 | 75 |
| E5 | 10 | 75 |
| E6 | 8 | 104 |
| E6 | 11 | 104 |
| E1 | 9 | 385 |
| E1 | 10 | 385 |
| E1 | 8 | 49 |
| E5 | 9 | 39 |
| E5 | 11 | 39 |

TABLE XVIII C-continued

HPV1I
HLA-A24 Motif Peptides

| 2 | 3 | 4 |
|---|---|---|
| L2 | 8 | 429 |
| L2 | 10 | 429 |
| L1 | 9 | 439 |
| E1 | 11 | 46 |
| L2 | 10 | 391 |
| E1 | 9 | 236 |
| L1 | 8 | 365 |
| L1 | 10 | 365 |
| E1 | 9 | 453 |
| E1 | 11 | 453 |
| E1 | 10 | 417 |
| E1 | 11 | 417 |
| E2 | 9 | 74 |
| E1 | 11 | 360 |
| E2 | 11 | 100 |
| E1 | 9 | 339 |
| E1 | 8 | 379 |
| L1 | 9 | 358 |
| L1 | 11 | 358 |
| E2 | 8 | 130 |
| E2 | 10 | 130 |
| E1 | 9 | 613 |
| E1 | 11 | 613 |
| E5 | 11 | 67 |
| L1 | 10 | 244 |
| L1 | 10 | 442 |
| L1 | 9 | 33 |
| L1 | 10 | 33 |
| L2 | 9 | 430 |
| L1 | 9 | 245 |
| L1 | 10 | 201 |
| E1 | 8 | 241 |
| E2 | 8 | 360 |
| L1 | 9 | 145 |
| E1 | 8 | 273 |
| E1 | 10 | 273 |
| E1 | 8 | 16 |
| E1 | 8 | 44 |
| L1 | 11 | 64 |
| E1 | 9 | 305 |
| E2 | 11 | 183 |
| E2 | 11 | 32 |
| E1 | 8 | 75 |
| L1 | 9 | 371 |
| L1 | 10 | 32 |
| L1 | 11 | 32 |
| E2 | 9 | 30 |
| L2 | 9 | 347 |
| E6 | 9 | 43 |
| E2 | 9 | 137 |
| L1 | 10 | 287 |
| E2 | 8 | 157 |
| L1 | 9 | 79 |
| L1 | 10 | 79 |
| E1 | 8 | 211 |
| E1 | 10 | 211 |
| E1 | 8 | 493 |
| L1 | 9 | 450 |
| L1 | 11 | 450 |
| E1 | 8 | 420 |
| L2 | 8 | 45 |
| L2 | 9 | 45 |
| E2 | 8 | 177 |
| E2 | 8 | 306 |
| E1 | 11 | 85 |
| E1 | 10 | 578 |
| E4 | 8 | 28 |
| E1 | 8 | 401 |
| E4 | 8 | 8 |
| E4 | 11 | 8 |
| L1 | 9 | 87 |
| L1 | 11 | 87 |
| E2 | 9 | 310 |
| E2 | 11 | 310 |
| L1 | 11 | 243 |
| E5 | 9 | 15 |
| L1 | 8 | 303 |
| E5 | 10 | 19 |
| L2 | 8 | 158 |
| E5 | 9 | 57 |
| E5 | 11 | 57 |
| E1 | 8 | 261 |
| E2 | 9 | 18 |
| E4 | 8 | 25 |
| E4 | 10 | 25 |
| E4 | 11 | 25 |
| E4 | 11 | 21 |
| E5 | 8 | 53 |
| E5 | 9 | 53 |
| E4 | 9 | 15 |
| E4 | 11 | 15 |
| E1 | 8 | 320 |
| E2 | 10 | 101 |
| L2 | 9 | 304 |
| E6 | 11 | 58 |
| E1 | 9 | 609 |
| E1 | 8 | 439 |
| E1 | 9 | 439 |
| E6 | 9 | 60 |
| E6 | 11 | 60 |
| E1 | 8 | 456 |
| E1 | 9 | 456 |
| E1 | 10 | 456 |
| L2 | 9 | 410 |
| E1 | 11 | 545 |
| E4 | 11 | 80 |
| L1 | 8 | 238 |
| L1 | 10 | 238 |
| L1 | 8 | 436 |
| L1 | 9 | 369 |
| L1 | 11 | 369 |
| E1 | 10 | 355 |
| E2 | 9 | 163 |
| E2 | 8 | 344 |
| E1 | 8 | 445 |
| E1 | 10 | 445 |
| E1 | 11 | 445 |
| L1 | 8 | 457 |
| L1 | 9 | 457 |
| L1 | 10 | 457 |
| L1 | 11 | 233 |
| L1 | 8 | 251 |
| E2 | 9 | 48 |
| E1 | 8 | 363 |
| E6 | 10 | 132 |
| E1 | 11 | 266 |
| E2 | 9 | 86 |
| L1 | 9 | 66 |
| E6 | 9 | 125 |
| E2 | 11 | 300 |
| L1 | 8 | 415 |
| E1 | 9 | 219 |
| L1 | 11 | 441 |
| L2 | 10 | 303 |
| L2 | 9 | 378 |
| L2 | 11 | 378 |
| L2 | 10 | 366 |
| E1 | 9 | 501 |
| E1 | 10 | 501 |
| E1 | 11 | 501 |
| L2 | 9 | 344 |
| E6 | 9 | 19 |
| E6 | 11 | 19 |
| E1 | 8 | 588 |
| L2 | 11 | 401 |
| E1 | 8 | 586 |
| E1 | 10 | 586 |
| L1 | 10 | 389 |

TABLE XVIII C-continued

HPV1I
HLA-A24 Motif Peptides

| 2 | 3 | 4 |
|---|---|---|
| E5 | 8 | 13 |
| E5 | 11 | 13 |
| E1 | 10 | 531 |
| E1 | 11 | 531 |
| L1 | 10 | 413 |
| E2 | 11 | 335 |
| L2 | 8 | 51 |
| L2 | 8 | 423 |
| L2 | 10 | 423 |
| E4 | 9 | 10 |
| E4 | 10 | 10 |
| E2 | 10 | 128 |
| E4 | 8 | 74 |
| E6 | 8 | 54 |
| L2 | 9 | 252 |
| L2 | 11 | 252 |
| E1 | 9 | 602 |
| E5 | 8 | 42 |
| E5 | 10 | 42 |
| E5 | 11 | 42 |
| L2 | 9 | 392 |
| L2 | 11 | 392 |
| L2 | 11 | 436 |
| L2 | 10 | 437 |
| E5 | 9 | 76 |
| E5 | 11 | 76 |
| E1 | 9 | 532 |
| E1 | 10 | 532 |
| L1 | 8 | 359 |
| L1 | 10 | 359 |

TABLE XIX

DR Supermotif Peptides

| 1 | 2 | 3 | 4 |
|---|---|---|---|
| HPV16 | E1 | 9 | 319 |
| HPV16 | E1 | 9 | 271 |
| HPV16 | E1 | 9 | 243 |
| HPV16 | E1 | 9 | 402 |
| HPV16 | E1 | 9 | 321 |
| HPV16 | E1 | 9 | 392 |
| HPV16 | E1 | 9 | 262 |
| HPV16 | E1 | 9 | 307 |
| HPV16 | E1 | 9 | 18 |
| HPV16 | E1 | 9 | 531 |
| HPV16 | E1 | 9 | 355 |
| HPV16 | E1 | 9 | 544 |
| HPV16 | E1 | 9 | 609 |
| HPV16 | E1 | 9 | 375 |
| HPV16 | E1 | 9 | 134 |
| HPV16 | E1 | 9 | 238 |
| HPV16 | E1 | 9 | 377 |
| HPV16 | E1 | 9 | 294 |
| HPV16 | E1 | 9 | 641 |
| HPV16 | E1 | 9 | 635 |
| HPV16 | E1 | 9 | 48 |
| HPV16 | E1 | 9 | 180 |
| HPV16 | E1 | 9 | 439 |
| HPV16 | E1 | 9 | 485 |
| HPV16 | E1 | 9 | 499 |
| HPV16 | E1 | 9 | 453 |
| HPV16 | E1 | 9 | 20 |
| HPV16 | E1 | 9 | 71 |
| HPV16 | E1 | 9 | 554 |
| HPV16 | E1 | 9 | 241 |
| HPV16 | E1 | 9 | 293 |
| HPV16 | E1 | 9 | 521 |
| HPV16 | E1 | 9 | 254 |
| HPV16 | E1 | 9 | 476 |

TABLE XIX-continued

DR Supermotif Peptides

| 1 | 2 | 3 | 4 |
|---|---|---|---|
| HPV16 | E1 | 9 | 332 |
| HPV16 | E1 | 9 | 215 |
| HPV16 | E1 | 9 | 520 |
| HPV16 | E1 | 9 | 473 |
| HPV16 | E1 | 9 | 90 |
| HPV16 | E1 | 9 | 613 |
| HPV16 | E1 | 9 | 508 |
| HPV16 | E1 | 9 | 486 |
| HPV16 | E1 | 9 | 255 |
| HPV16 | E1 | 9 | 463 |
| HPV16 | E1 | 9 | 300 |
| HPV16 | E1 | 9 | 493 |
| HPV16 | E1 | 9 | 198 |
| HPV16 | E1 | 9 | 467 |
| HPV16 | E1 | 9 | 513 |
| HPV16 | E1 | 9 | 297 |
| HPV16 | E1 | 9 | 557 |
| HPV16 | E1 | 9 | 217 |
| HPV16 | E1 | 9 | 322 |
| HPV16 | E1 | 9 | 494 |
| HPV16 | E1 | 9 | 425 |
| HPV16 | E1 | 9 | 474 |
| HPV16 | E1 | 9 | 370 |
| HPV16 | E1 | 9 | 59 |
| HPV16 | E1 | 9 | 19 |
| HPV16 | E1 | 9 | 584 |
| HPV16 | E1 | 9 | 139 |
| HPV16 | E1 | 9 | 340 |
| HPV16 | E1 | 9 | 305 |
| HPV16 | E1 | 9 | 312 |
| HPV16 | E1 | 9 | 563 |
| HPV16 | E1 | 9 | 401 |
| HPV16 | E1 | 9 | 365 |
| HPV16 | E1 | 9 | 290 |
| HPV16 | E1 | 9 | 186 |
| HPV16 | E1 | 9 | 91 |
| HPV16 | E1 | 9 | 540 |
| HPV16 | E1 | 9 | 555 |
| HPV16 | E1 | 9 | 127 |
| HPV16 | E1 | 9 | 578 |
| HPV16 | E1 | 9 | 223 |
| HPV16 | E1 | 9 | 102 |
| HPV16 | E1 | 9 | 509 |
| HPV16 | E1 | 9 | 298 |
| HPV16 | E1 | 9 | 549 |
| HPV16 | E1 | 9 | 110 |
| HPV16 | E1 | 9 | 617 |
| HPV16 | E1 | 9 | 273 |
| HPV16 | E1 | 9 | 195 |
| HPV16 | E1 | 9 | 339 |
| HPV16 | E1 | 9 | 24 |
| HPV16 | E1 | 9 | 454 |
| HPV16 | E1 | 9 | 588 |
| HPV16 | E1 | 9 | 501 |
| HPV16 | E1 | 9 | 278 |
| HPV16 | E1 | 9 | 446 |
| HPV16 | E1 | 9 | 86 |
| HPV16 | E1 | 9 | 226 |
| HPV16 | E1 | 9 | 274 |
| HPV16 | E1 | 9 | 428 |
| HPV16 | E1 | 9 | 579 |
| HPV16 | E1 | 9 | 382 |
| HPV16 | E1 | 9 | 261 |
| HPV16 | E1 | 9 | 264 |
| HPV16 | E2 | 9 | 178 |
| HPV16 | E2 | 9 | 44 |
| HPV16 | E2 | 9 | 268 |
| HPV16 | E2 | 9 | 49 |
| HPV16 | E2 | 9 | 229 |
| HPV16 | E2 | 9 | 312 |
| HPV16 | E2 | 9 | 347 |
| HPV16 | E2 | 9 | 99 |
| HPV16 | E2 | 9 | 152 |
| HPV16 | E2 | 9 | 77 |
| HPV16 | E2 | 9 | 83 |

TABLE XIX-continued

DR Supermotif Peptides

| 1 | 2 | 3 | 4 |
|---|---|---|---|
| HPV16 | E2 | 9 | 121 |
| HPV16 | E2 | 9 | 54 |
| HPV16 | E2 | 9 | 192 |
| HPV16 | E2 | 9 | 326 |
| HPV16 | E2 | 9 | 159 |
| HPV16 | E2 | 9 | 193 |
| HPV16 | E2 | 9 | 311 |
| HPV16 | E2 | 9 | 164 |
| HPV16 | E2 | 9 | 139 |
| HPV16 | E2 | 9 | 59 |
| HPV16 | E2 | 9 | 33 |
| HPV16 | E2 | 9 | 183 |
| HPV16 | E2 | 9 | 94 |
| HPV16 | E2 | 9 | 102 |
| HPV16 | E2 | 9 | 73 |
| HPV16 | E2 | 9 | 350 |
| HPV16 | E2 | 9 | 19 |
| HPV16 | E2 | 9 | 92 |
| HPV16 | E2 | 9 | 58 |
| HPV16 | E2 | 9 | 70 |
| HPV16 | E2 | 9 | 211 |
| HPV16 | E2 | 9 | 238 |
| HPV16 | E2 | 9 | 194 |
| HPV16 | E2 | 9 | 352 |
| HPV16 | E2 | 9 | 262 |
| HPV16 | E2 | 9 | 10 |
| HPV16 | E2 | 9 | 215 |
| HPV16 | E2 | 9 | 305 |
| HPV16 | E2 | 9 | 101 |
| HPV16 | E2 | 9 | 205 |
| HPV16 | E2 | 9 | 210 |
| HPV16 | E2 | 9 | 147 |
| HPV16 | E2 | 9 | 138 |
| HPV16 | E2 | 9 | 257 |
| HPV16 | E2 | 9 | 64 |
| HPV16 | E2 | 9 | 200 |
| HPV16 | E2 | 9 | 256 |
| HPV16 | E2 | 9 | 321 |
| HPV16 | E2 | 9 | 155 |
| HPV16 | E2 | 9 | 36 |
| HPV16 | E2 | 9 | 134 |
| HPV16 | E5 | 9 | 1 |
| HPV16 | E5 | 9 | 16 |
| HPV16 | E5 | 9 | 57 |
| HPV16 | E5 | 9 | 21 |
| HPV16 | E5 | 9 | 62 |
| HPV16 | E5 | 9 | 17 |
| HPV16 | E5 | 9 | 29 |
| HPV16 | E5 | 9 | 27 |
| HPV16 | E5 | 9 | 23 |
| HPV16 | E5 | 9 | 22 |
| HPV16 | E5 | 9 | 60 |
| HPV16 | E5 | 9 | 69 |
| HPV16 | E5 | 9 | 68 |
| HPV16 | E5 | 9 | 46 |
| HPV16 | E5 | 9 | 47 |
| HPV16 | E5 | 9 | 32 |
| HPV16 | E5 | 9 | 64 |
| HPV16 | E5 | 9 | 15 |
| HPV16 | E5 | 9 | 19 |
| HPV16 | E5 | 9 | 50 |
| HPV16 | E5 | 9 | 36 |
| HPV16 | E5 | 9 | 51 |
| HPV16 | E5 | 9 | 48 |
| HPV16 | E5 | 9 | 4 |
| HPV16 | E5 | 9 | 73 |
| HPV16 | E5 | 9 | 33 |
| HPV16 | E5 | 9 | 44 |
| HPV16 | E5 | 9 | 11 |
| HPV16 | E5 | 9 | 43 |
| HPV16 | E5 | 9 | 12 |
| HPV16 | E5 | 9 | 28 |
| HPV16 | E5 | 9 | 49 |
| HPV16 | E5 | 9 | 39 |
| HPV16 | E5 | 9 | 65 |
| HPV16 | E5 | 9 | 66 |
| HPV16 | E5 | 9 | 71 |
| HPV16 | E5 | 9 | 42 |
| HPV16 | E6 | 9 | 1 |
| HPV16 | E6 | 9 | 61 |
| HPV16 | E6 | 9 | 76 |
| HPV16 | E6 | 9 | 90 |
| HPV16 | E6 | 9 | 54 |
| HPV16 | E6 | 9 | 35 |
| HPV16 | E6 | 9 | 108 |
| HPV16 | E6 | 9 | 39 |
| HPV16 | E6 | 9 | 99 |
| HPV16 | E6 | 9 | 135 |
| HPV16 | E6 | 9 | 144 |
| HPV16 | E6 | 9 | 88 |
| HPV16 | E6 | 9 | 33 |
| HPV16 | E6 | 9 | 111 |
| HPV16 | E6 | 9 | 44 |
| HPV16 | E6 | 9 | 106 |
| HPV16 | E6 | 9 | 103 |
| HPV16 | E6 | 9 | 19 |
| HPV16 | E6 | 9 | 69 |
| HPV16 | E6 | 9 | 30 |
| HPV16 | E6 | 9 | 139 |
| HPV16 | E6 | 9 | 52 |
| HPV16 | E7 | 9 | 1 |
| HPV16 | E7 | 9 | 84 |
| HPV16 | E7 | 9 | 12 |
| HPV16 | E7 | 9 | 54 |
| HPV16 | E7 | 9 | 79 |
| HPV16 | E7 | 9 | 82 |
| HPV16 | E7 | 9 | 90 |
| HPV16 | E7 | 9 | 87 |
| HPV16 | E7 | 9 | 15 |
| HPV16 | E7 | 9 | 69 |
| HPV16 | E7 | 9 | 74 |
| HPV16 | E7 | 9 | 23 |
| HPV16 | E7 | 9 | 89 |
| HPV16 | E7 | 9 | 67 |
| HPV16 | E7 | 9 | 8 |
| HPV16 | L1 | 9 | 1 |
| HPV16 | L1 | 9 | 3 |
| HPV16 | L1 | 9 | 414 |
| HPV16 | L1 | 9 | 293 |
| HPV16 | L1 | 9 | 236 |
| HPV16 | L1 | 9 | 38 |
| HPV16 | L1 | 9 | 374 |
| HPV16 | L1 | 9 | 175 |
| HPV16 | L1 | 9 | 214 |
| HPV16 | L1 | 9 | 54 |
| HPV16 | L1 | 9 | 400 |
| HPV16 | L1 | 9 | 303 |
| HPV16 | L1 | 9 | 116 |
| HPV16 | L1 | 9 | 430 |
| HPV16 | L1 | 9 | 37 |
| HPV16 | L1 | 9 | 444 |
| HPV16 | L1 | 9 | 18 |
| HPV16 | L1 | 9 | 477 |
| HPV16 | L1 | 9 | 248 |
| HPV16 | L1 | 9 | 27 |
| HPV16 | L1 | 9 | 276 |
| HPV16 | L1 | 9 | 234 |
| HPV16 | L1 | 9 | 8 |
| HPV16 | L1 | 9 | 239 |
| HPV16 | L1 | 9 | 396 |
| HPV16 | L1 | 9 | 195 |
| HPV16 | L1 | 9 | 96 |
| HPV16 | L1 | 9 | 355 |
| HPV16 | L1 | 9 | 139 |
| HPV16 | L1 | 9 | 133 |
| HPV16 | L1 | 9 | 143 |
| HPV16 | L1 | 9 | 76 |
| HPV16 | L1 | 9 | 404 |
| HPV16 | L1 | 9 | 420 |
| HPV16 | L1 | 9 | 508 |

TABLE XIX-continued

DR Supermotif Peptides

| 1 | 2 | 3 | 4 |
|---|---|---|---|
| HPV16 | L1 | 9 | 409 |
| HPV16 | L1 | 9 | 246 |
| HPV16 | L1 | 9 | 472 |
| HPV16 | L1 | 9 | 185 |
| HPV16 | L1 | 9 | 470 |
| HPV16 | L1 | 9 | 42 |
| HPV16 | L1 | 9 | 30 |
| HPV16 | L1 | 9 | 417 |
| HPV16 | L1 | 9 | 167 |
| HPV16 | L1 | 9 | 61 |
| HPV16 | L1 | 9 | 87 |
| HPV16 | L1 | 9 | 337 |
| HPV16 | L1 | 9 | 370 |
| HPV16 | L1 | 9 | 86 |
| HPV16 | L1 | 9 | 221 |
| HPV16 | L1 | 9 | 206 |
| HPV16 | L1 | 9 | 301 |
| HPV16 | L1 | 9 | 250 |
| HPV16 | L1 | 9 | 216 |
| HPV16 | L1 | 9 | 109 |
| HPV16 | L1 | 9 | 44 |
| HPV16 | L1 | 9 | 402 |
| HPV16 | L1 | 9 | 490 |
| HPV16 | L1 | 9 | 184 |
| HPV16 | L1 | 9 | 357 |
| HPV16 | L1 | 9 | 182 |
| HPV16 | L1 | 9 | 5 |
| HPV16 | L1 | 9 | 98 |
| HPV16 | L1 | 9 | 281 |
| HPV16 | L1 | 9 | 287 |
| HPV16 | L1 | 9 | 495 |
| HPV16 | L1 | 9 | 126 |
| HPV16 | L1 | 9 | 485 |
| HPV16 | L1 | 9 | 325 |
| HPV16 | L1 | 9 | 31 |
| HPV16 | L1 | 9 | 177 |
| HPV16 | L1 | 9 | 69 |
| HPV16 | L1 | 9 | 317 |
| HPV16 | L1 | 9 | 368 |
| HPV16 | L1 | 9 | 7 |
| HPV16 | L1 | 9 | 60 |
| HPV16 | L1 | 9 | 124 |
| HPV16 | L1 | 9 | 39 |
| HPV16 | L1 | 9 | 446 |
| HPV16 | L1 | 9 | 101 |
| HPV16 | L1 | 9 | 6 |
| HPV16 | L1 | 9 | 360 |
| HPV16 | L1 | 9 | 23 |
| HPV16 | L1 | 9 | 24 |
| HPV16 | L1 | 9 | 260 |
| HPV16 | L1 | 9 | 447 |
| HPV16 | L1 | 9 | 99 |
| HPV16 | L2 | 9 | 1 |
| HPV16 | L2 | 9 | 373 |
| HPV16 | L2 | 9 | 45 |
| HPV16 | L2 | 9 | 339 |
| HPV16 | L2 | 9 | 446 |
| HPV16 | L2 | 9 | 427 |
| HPV16 | L2 | 9 | 374 |
| HPV16 | L2 | 9 | 242 |
| HPV16 | L2 | 9 | 283 |
| HPV16 | L2 | 9 | 168 |
| HPV16 | L2 | 9 | 46 |
| HPV16 | L2 | 9 | 202 |
| HPV16 | L2 | 9 | 341 |
| HPV16 | L2 | 9 | 198 |
| HPV16 | L2 | 9 | 114 |
| HPV16 | L2 | 9 | 406 |
| HPV16 | L2 | 9 | 181 |
| HPV16 | L2 | 9 | 41 |
| HPV16 | L2 | 9 | 416 |
| HPV16 | L2 | 9 | 55 |
| HPV16 | L2 | 9 | 183 |
| HPV16 | L2 | 9 | 328 |
| HPV16 | L2 | 9 | 148 |
| HPV16 | L2 | 9 | 48 |
| HPV16 | L2 | 9 | 36 |
| HPV16 | L2 | 9 | 411 |
| HPV16 | L2 | 9 | 289 |
| HPV16 | L2 | 9 | 108 |
| HPV16 | L2 | 9 | 326 |
| HPV16 | L2 | 9 | 89 |
| HPV16 | L2 | 9 | 287 |
| HPV16 | L2 | 9 | 430 |
| HPV16 | L2 | 9 | 465 |
| HPV16 | L2 | 9 | 393 |
| HPV16 | L2 | 9 | 365 |
| HPV16 | L2 | 9 | 152 |
| HPV16 | L2 | 9 | 257 |
| HPV16 | L2 | 9 | 163 |
| HPV16 | L2 | 9 | 400 |
| HPV16 | L2 | 9 | 146 |
| HPV16 | L2 | 9 | 284 |
| HPV16 | L2 | 9 | 420 |
| HPV16 | L2 | 9 | 95 |
| HPV16 | L2 | 9 | 210 |
| HPV16 | L2 | 9 | 130 |
| HPV16 | L2 | 9 | 169 |
| HPV16 | L2 | 9 | 123 |
| HPV16 | L2 | 9 | 462 |
| HPV16 | L2 | 9 | 227 |
| HPV16 | L2 | 9 | 464 |
| HPV16 | L2 | 9 | 294 |
| HPV16 | L2 | 9 | 93 |
| HPV16 | L2 | 9 | 301 |
| HPV16 | L2 | 9 | 72 |
| HPV16 | L2 | 9 | 394 |
| HPV16 | L2 | 9 | 53 |
| HPV16 | L2 | 9 | 222 |
| HPV16 | L2 | 9 | 216 |
| HPV16 | L2 | 9 | 390 |
| HPV16 | L2 | 9 | 86 |
| HPV16 | L2 | 9 | 193 |
| HPV16 | L2 | 9 | 250 |
| HPV16 | L2 | 9 | 235 |
| HPV16 | L2 | 9 | 115 |
| HPV16 | L2 | 9 | 382 |
| HPV16 | L2 | 9 | 98 |
| HPV16 | L2 | 9 | 327 |
| HPV16 | L2 | 9 | 238 |
| HPV16 | L2 | 9 | 126 |
| HPV16 | L2 | 9 | 385 |
| HPV16 | L2 | 9 | 133 |
| HPV16 | L2 | 9 | 369 |
| HPV16 | L2 | 9 | 260 |
| HPV16 | L2 | 9 | 75 |
| HPV16 | L2 | 9 | 306 |
| HPV16 | L2 | 9 | 330 |
| HPV18 | E1 | 9 | 399 |
| HPV18 | E1 | 9 | 409 |
| HPV18 | E1 | 9 | 328 |
| HPV18 | E1 | 9 | 314 |
| HPV18 | E1 | 9 | 17 |
| HPV18 | E1 | 9 | 142 |
| HPV18 | E1 | 9 | 538 |
| HPV18 | E1 | 9 | 278 |
| HPV18 | E1 | 9 | 384 |
| HPV18 | E1 | 9 | 583 |
| HPV18 | E1 | 9 | 137 |
| HPV18 | E1 | 9 | 362 |
| HPV18 | E1 | 9 | 624 |
| HPV18 | E1 | 9 | 382 |
| HPV18 | E1 | 9 | 312 |
| HPV18 | E1 | 9 | 542 |
| HPV18 | E1 | 9 | 500 |
| HPV18 | E1 | 9 | 268 |
| HPV18 | E1 | 9 | 261 |
| HPV18 | E1 | 9 | 506 |
| HPV18 | E1 | 9 | 159 |
| HPV18 | E1 | 9 | 643 |

TABLE XIX-continued

DR Supermotif Peptides

| 1 | 2 | 3 | 4 |
|---|---|---|---|
| HPV18 | E1 | 9 | 19 |
| HPV18 | E1 | 9 | 561 |
| HPV18 | E1 | 9 | 461 |
| HPV18 | E1 | 9 | 192 |
| HPV18 | E1 | 9 | 250 |
| HPV18 | E1 | 9 | 501 |
| HPV18 | E1 | 9 | 285 |
| HPV18 | E1 | 9 | 339 |
| HPV18 | E1 | 9 | 464 |
| HPV18 | E1 | 9 | 593 |
| HPV18 | E1 | 9 | 620 |
| HPV18 | E1 | 9 | 222 |
| HPV18 | E1 | 9 | 480 |
| HPV18 | E1 | 9 | 562 |
| HPV18 | E1 | 9 | 89 |
| HPV18 | E1 | 9 | 493 |
| HPV18 | E1 | 9 | 262 |
| HPV18 | E1 | 9 | 527 |
| HPV18 | E1 | 9 | 280 |
| HPV18 | E1 | 9 | 520 |
| HPV18 | E1 | 9 | 85 |
| HPV18 | E1 | 9 | 564 |
| HPV18 | E1 | 9 | 470 |
| HPV18 | E1 | 9 | 307 |
| HPV18 | E1 | 9 | 288 |
| HPV18 | E1 | 9 | 329 |
| HPV18 | E1 | 9 | 432 |
| HPV18 | E1 | 9 | 481 |
| HPV18 | E1 | 9 | 18 |
| HPV18 | E1 | 9 | 189 |
| HPV18 | E1 | 9 | 347 |
| HPV18 | E1 | 9 | 570 |
| HPV18 | E1 | 9 | 319 |
| HPV18 | E1 | 9 | 63 |
| HPV18 | E1 | 9 | 408 |
| HPV18 | E1 | 9 | 70 |
| HPV18 | E1 | 9 | 266 |
| HPV18 | E1 | 9 | 372 |
| HPV18 | E1 | 9 | 105 |
| HPV18 | E1 | 9 | 352 |
| HPV18 | E1 | 9 | 297 |
| HPV18 | E1 | 9 | 547 |
| HPV18 | E1 | 9 | 130 |
| HPV18 | E1 | 9 | 585 |
| HPV18 | E1 | 9 | 48 |
| HPV18 | E1 | 9 | 516 |
| HPV18 | E1 | 9 | 113 |
| HPV18 | E1 | 9 | 433 |
| HPV18 | E1 | 9 | 305 |
| HPV18 | E1 | 9 | 248 |
| HPV18 | E1 | 9 | 230 |
| HPV18 | E1 | 9 | 168 |
| HPV18 | E1 | 9 | 346 |
| HPV18 | E1 | 9 | 515 |
| HPV18 | E1 | 9 | 536 |
| HPV18 | E1 | 9 | 224 |
| HPV18 | E1 | 9 | 326 |
| HPV18 | E1 | 9 | 528 |
| HPV18 | E1 | 9 | 51 |
| HPV18 | E1 | 9 | 595 |
| HPV18 | E1 | 9 | 508 |
| HPV18 | E1 | 9 | 23 |
| HPV18 | E1 | 9 | 453 |
| HPV18 | E1 | 9 | 233 |
| HPV18 | E1 | 9 | 247 |
| HPV18 | E1 | 9 | 281 |
| HPV18 | E1 | 9 | 435 |
| HPV18 | E1 | 9 | 586 |
| HPV18 | E1 | 9 | 271 |
| HPV18 | E1 | 9 | 389 |
| HPV18 | E2 | 9 | 150 |
| HPV18 | E2 | 9 | 240 |
| HPV18 | E2 | 9 | 157 |
| HPV18 | E2 | 9 | 68 |
| HPV18 | E2 | 9 | 105 |

TABLE XIX-continued

DR Supermotif Peptides

| 1 | 2 | 3 | 4 |
|---|---|---|---|
| HPV18 | E2 | 9 | 183 |
| HPV18 | E2 | 9 | 135 |
| HPV18 | E2 | 9 | 212 |
| HPV18 | E2 | 9 | 34 |
| HPV18 | E2 | 9 | 142 |
| HPV18 | E2 | 9 | 106 |
| HPV18 | E2 | 9 | 81 |
| HPV18 | E2 | 9 | 193 |
| HPV18 | E2 | 9 | 77 |
| HPV18 | E2 | 9 | 63 |
| HPV18 | E2 | 9 | 58 |
| HPV18 | E2 | 9 | 169 |
| HPV18 | E2 | 9 | 8 |
| HPV18 | E2 | 9 | 350 |
| HPV18 | E2 | 9 | 15 |
| HPV18 | E2 | 9 | 136 |
| HPV18 | E2 | 9 | 198 |
| HPV18 | E2 | 9 | 267 |
| HPV18 | E2 | 9 | 173 |
| HPV18 | E2 | 9 | 228 |
| HPV18 | E2 | 9 | 281 |
| HPV18 | E2 | 9 | 346 |
| HPV18 | E2 | 9 | 313 |
| HPV18 | E2 | 9 | 232 |
| HPV18 | E2 | 9 | 320 |
| HPV18 | E2 | 9 | 96 |
| HPV18 | E2 | 9 | 347 |
| HPV18 | E2 | 9 | 234 |
| HPV18 | E2 | 9 | 221 |
| HPV18 | E2 | 9 | 266 |
| HPV18 | E2 | 9 | 66 |
| HPV18 | E2 | 9 | 144 |
| HPV18 | E2 | 9 | 40 |
| HPV18 | E5 | 9 | 2 |
| HPV18 | E5 | 9 | 35 |
| HPV18 | E5 | 9 | 33 |
| HPV18 | E5 | 9 | 20 |
| HPV18 | E5 | 9 | 12 |
| HPV18 | E5 | 9 | 59 |
| HPV18 | E5 | 9 | 16 |
| HPV18 | E5 | 9 | 58 |
| HPV18 | E5 | 9 | 53 |
| HPV18 | E5 | 9 | 40 |
| HPV18 | E5 | 9 | 22 |
| HPV18 | E5 | 9 | 8 |
| HPV18 | E5 | 9 | 43 |
| HPV18 | E5 | 9 | 7 |
| HPV18 | E5 | 9 | 61 |
| HPV18 | E5 | 9 | 38 |
| HPV18 | E5 | 9 | 31 |
| HPV18 | E5 | 9 | 64 |
| HPV18 | E5 | 9 | 4 |
| HPV18 | E5 | 9 | 63 |
| HPV18 | E5 | 9 | 6 |
| HPV18 | E5 | 9 | 54 |
| HPV18 | E5 | 9 | 15 |
| HPV18 | E5 | 9 | 57 |
| HPV18 | E5 | 9 | 39 |
| HPV18 | E5 | 9 | 37 |
| HPV18 | E5 | 9 | 23 |
| HPV18 | E5 | 9 | 41 |
| HPV18 | E5 | 9 | 55 |
| HPV18 | E5 | 9 | 36 |
| HPV18 | E5 | 9 | 42 |
| HPV18 | E6 | 9 | 30 |
| HPV18 | E6 | 9 | 54 |
| HPV18 | E6 | 9 | 49 |
| HPV18 | E6 | 9 | 56 |
| HPV18 | E6 | 9 | 106 |
| HPV18 | E6 | 9 | 33 |
| HPV18 | E6 | 9 | 39 |
| HPV18 | E6 | 9 | 93 |
| HPV18 | E6 | 9 | 55 |
| HPV18 | E6 | 9 | 28 |
| HPV18 | E6 | 9 | 101 |

TABLE XIX-continued

DR Supermotif Peptides

| 1 | 2 | 3 | 4 |
|---|---|---|---|
| HPV18 | E6 | 9 | 103 |
| HPV18 | E6 | 9 | 98 |
| HPV18 | E6 | 9 | 25 |
| HPV18 | E6 | 9 | 14 |
| HPV18 | E6 | 9 | 60 |
| HPV18 | E6 | 9 | 12 |
| HPV18 | E6 | 9 | 85 |
| HPV18 | E6 | 9 | 34 |
| HPV18 | E6 | 9 | 47 |
| HPV18 | E7 | 9 | 1 |
| HPV18 | E7 | 9 | 89 |
| HPV18 | E7 | 9 | 49 |
| HPV18 | E7 | 9 | 44 |
| HPV18 | E7 | 9 | 75 |
| HPV18 | E7 | 9 | 8 |
| HPV18 | E7 | 9 | 94 |
| HPV18 | E7 | 9 | 86 |
| HPV18 | E7 | 9 | 97 |
| HPV18 | E7 | 9 | 12 |
| HPV18 | E7 | 9 | 21 |
| HPV18 | E7 | 9 | 90 |
| HPV18 | E7 | 9 | 61 |
| HPV18 | E7 | 9 | 74 |
| HPV18 | E7 | 9 | 96 |
| HPV18 | E7 | 9 | 26 |
| HPV18 | L1 | 9 | 3 |
| HPV18 | L1 | 9 | 450 |
| HPV18 | L1 | 9 | 328 |
| HPV18 | L1 | 9 | 226 |
| HPV18 | L1 | 9 | 131 |
| HPV18 | L1 | 9 | 45 |
| HPV18 | L1 | 9 | 249 |
| HPV18 | L1 | 9 | 89 |
| HPV18 | L1 | 9 | 436 |
| HPV18 | L1 | 9 | 72 |
| HPV18 | L1 | 9 | 151 |
| HPV18 | L1 | 9 | 466 |
| HPV18 | L1 | 9 | 283 |
| HPV18 | L1 | 9 | 311 |
| HPV18 | L1 | 9 | 62 |
| HPV18 | L1 | 9 | 59 |
| HPV18 | L1 | 9 | 274 |
| HPV18 | L1 | 9 | 394 |
| HPV18 | L1 | 9 | 230 |
| HPV18 | L1 | 9 | 110 |
| HPV18 | L1 | 9 | 22 |
| HPV18 | L1 | 9 | i74 |
| HPV18 | L1 | 9 | 351 |
| HPV18 | L1 | 9 | 168 |
| HPV18 | L1 | 9 | 41 |
| HPV18 | L1 | 9 | 390 |
| HPV18 | L1 | 9 | 440 |
| HPV18 | L1 | 9 | 456 |
| HPV18 | L1 | 9 | 50 |
| HPV18 | L1 | 9 | 12 |
| HPV18 | L1 | 9 | 35 |
| HPV18 | L1 | 9 | 281 |
| HPV18 | L1 | 9 | 146 |
| HPV18 | L1 | 9 | 508 |
| HPV18 | L1 | 9 | 123 |
| HPV18 | L1 | 9 | 220 |
| HPV18 | L1 | 9 | 464 |
| HPV18 | L1 | 9 | 32 |
| HPV18 | L1 | 9 | 437 |
| HPV18 | L1 | 9 | 53 |
| HPV18 | L1 | 9 | 36 |
| HPV18 | L1 | 9 | 4 |
| HPV18 | L1 | 9 | 453 |
| HPV18 | L1 | 9 | 468 |
| HPV18 | L1 | 9 | 372 |
| HPV18 | L1 | 9 | 256 |
| HPV18 | L1 | 9 | 73 |
| HPV18 | L1 | 9 | 513 |
| HPV18 | L1 | 9 | 55 |
| HPV18 | L1 | 9 | 210 |
| HPV18 | L1 | 9 | 285 |
| HPV18 | L1 | 9 | 251 |
| HPV18 | L1 | 9 | 29 |
| HPV18 | L1 | 9 | 144 |
| HPV18 | L1 | 9 | 336 |
| HPV18 | L1 | 9 | 27 |
| HPV18 | L1 | 9 | 536 |
| HPV18 | L1 | 9 | 438 |
| HPV18 | L1 | 9 | 219 |
| HPV18 | L1 | 9 | 392 |
| HPV18 | L1 | 9 | 217 |
| HPV18 | L1 | 9 | 526 |
| HPV18 | L1 | 9 | 133 |
| HPV18 | L1 | 9 | 322 |
| HPV18 | L1 | 9 | 531 |
| HPV18 | L1 | 9 | 161 |
| HPV18 | L1 | 9 | 9 |
| HPV18 | L1 | 9 | 352 |
| HPV18 | L1 | 9 | 204 |
| HPV18 | L1 | 9 | 360 |
| HPV18 | L1 | 9 | 96 |
| HPV18 | L1 | 9 | 34 |
| HPV18 | L1 | 9 | 521 |
| HPV18 | L1 | 9 | 338 |
| HPV18 | L1 | 9 | 429 |
| HPV18 | L1 | 9 | 104 |
| HPV18 | L1 | 9 | 241 |
| HPV18 | L1 | 9 | 403 |
| HPV18 | L1 | 9 | 212 |
| HPV18 | L1 | 9 | 88 |
| HPV18 | L1 | 9 | 445 |
| HPV18 | L1 | 9 | 159 |
| HPV18 | L1 | 9 | 95 |
| HPV18 | L1 | 9 | 74 |
| HPV18 | L1 | 9 | 482 |
| HPV18 | L1 | 9 | 480 |
| HPV18 | L1 | 9 | 432 |
| HPV18 | L1 | 9 | 58 |
| HPV18 | L1 | 9 | 136 |
| HPV18 | L1 | 9 | 10 |
| HPV18 | L1 | 9 | 395 |
| HPV18 | L1 | 9 | 37 |
| HPV18 | L1 | 9 | 506 |
| HPV18 | L1 | 9 | 269 |
| HPV18 | L1 | 9 | 21 |
| HPV18 | L1 | 9 | 15 |
| HPV18 | L1 | 9 | 48 |
| HPV18 | L1 | 9 | 187 |
| HPV18 | L1 | 9 | 295 |
| HPV18 | L1 | 9 | 483 |
| HPV18 | L1 | 9 | 134 |
| HPV18 | L2 | 9 | 1 |
| HPV18 | L2 | 9 | 2 |
| HPV18 | L2 | 9 | 355 |
| HPV18 | L2 | 9 | 44 |
| HPV18 | L2 | 9 | 180 |
| HPV18 | L2 | 9 | 384 |
| HPV18 | L2 | 9 | 306 |
| HPV18 | L2 | 9 | 361 |
| HPV18 | L2 | 9 | 407 |
| HPV18 | L2 | 9 | 45 |
| HPV18 | L2 | 9 | 347 |
| HPV18 | L2 | 9 | 112 |
| HPV18 | L2 | 9 | 210 |
| HPV18 | L2 | 9 | 197 |
| HPV18 | L2 | 9 | 372 |
| HPV18 | L2 | 9 | 259 |
| HPV18 | L2 | 9 | 374 |
| HPV18 | L2 | 9 | 299 |
| HPV18 | L2 | 9 | 130 |
| HPV18 | L2 | 9 | 54 |
| HPV18 | L2 | 9 | 181 |
| HPV18 | L2 | 9 | 405 |
| HPV18 | L2 | 9 | 435 |
| HPV18 | L2 | 9 | 40 |

TABLE XIX-continued

DR Supermotif Peptides

| 1 | 2 | 3 | 4 |
|---|---|---|---|
| HPV18 | L2 | 9 | 96 |
| HPV18 | L2 | 9 | 282 |
| HPV18 | L2 | 9 | 47 |
| HPV18 | L2 | 9 | 106 |
| HPV18 | L2 | 9 | 350 |
| HPV18 | L2 | 9 | 200 |
| HPV18 | L2 | 9 | 440 |
| HPV18 | L2 | 9 | 280 |
| HPV18 | L2 | 9 | 256 |
| HPV18 | L2 | 9 | 162 |
| HPV18 | L2 | 9 | 241 |
| HPV18 | L2 | 9 | 82 |
| HPV18 | L2 | 9 | 182 |
| HPV18 | L2 | 9 | 389 |
| HPV18 | L2 | 9 | 141 |
| HPV18 | L2 | 9 | 242 |
| HPV18 | L2 | 9 | 333 |
| HPV18 | L2 | 9 | 168 |
| HPV18 | L2 | 9 | 93 |
| HPV18 | L2 | 9 | 294 |
| HPV18 | L2 | 9 | 451 |
| HPV18 | L2 | 9 | 91 |
| HPV18 | L2 | 9 | 319 |
| HPV18 | L2 | 9 | 277 |
| HPV18 | L2 | 9 | 371 |
| HPV18 | L2 | 9 | 52 |
| HPV18 | L2 | 9 | 81 |
| HPV18 | L2 | 9 | 332 |
| HPV18 | L2 | 9 | 378 |
| HPV18 | L2 | 9 | 231 |
| HPV18 | L2 | 9 | 249 |
| HPV18 | L2 | 9 | 113 |
| HPV18 | L2 | 9 | 150 |
| HPV18 | L2 | 9 | 192 |
| HPV18 | L2 | 9 | 140 |
| HPV18 | L2 | 9 | 428 |
| HPV18 | L2 | 9 | 128 |
| HPV18 | L2 | 9 | 414 |
| HPV18 | L2 | 9 | 413 |
| HPV18 | L2 | 9 | 320 |
| HPV18 | L2 | 9 | 143 |
| HPV18 | L2 | 9 | 35 |
| HPV18 | L2 | 9 | 400 |
| HPV18 | L2 | 9 | 221 |
| HPV18 | L2 | 9 | 107 |
| HPV18 | L2 | 9 | 84 |
| HPV18 | L2 | 9 | 416 |
| HPV18 | L2 | 9 | 417 |
| HPV18 | L2 | 9 | 323 |
| HPV18 | L2 | 9 | 335 |
| HPV18 | L2 | 9 | 234 |
| HPV18 | L2 | 9 | 387 |
| HPV31 | E1 | 9 | 299 |
| HPV31 | E1 | 9 | 372 |
| HPV31 | E1 | 9 | 251 |
| HPV31 | E1 | 9 | 223 |
| HPV31 | E1 | 9 | 382 |
| HPV31 | E1 | 9 | 442 |
| HPV31 | E1 | 9 | 301 |
| HPV31 | E1 | 9 | 287 |
| HPV31 | E1 | 9 | 17 |
| HPV31 | E1 | 9 | 511 |
| HPV31 | E1 | 9 | 556 |
| HPV31 | E1 | 9 | 589 |
| HPV31 | E1 | 9 | 355 |
| HPV31 | E1 | 9 | 133 |
| HPV31 | E1 | 9 | 335 |
| HPV31 | E1 | 9 | 218 |
| HPV31 | E1 | 9 | 357 |
| HPV31 | E1 | 9 | 274 |
| HPV31 | E1 | 9 | 621 |
| HPV31 | E1 | 9 | 234 |
| HPV31 | E1 | 9 | 479 |
| HPV31 | E1 | 9 | 615 |
| HPV31 | E1 | 9 | 465 |
| HPV31 | E1 | 9 | 94 |
| HPV31 | E1 | 9 | 19 |
| HPV31 | E1 | 9 | 534 |
| HPV31 | E1 | 9 | 515 |
| HPV31 | E1 | 9 | 434 |
| HPV31 | E1 | 9 | 273 |
| HPV31 | E1 | 9 | 501 |
| HPV31 | E1 | 9 | 481 |
| HPV31 | E1 | 9 | 206 |
| HPV31 | E1 | 9 | 312 |
| HPV31 | E1 | 9 | 474 |
| HPV31 | E1 | 9 | 535 |
| HPV31 | E1 | 9 | 195 |
| HPV31 | E1 | 9 | 500 |
| HPV31 | E1 | 9 | 453 |
| HPV31 | E1 | 9 | 268 |
| HPV31 | E1 | 9 | 89 |
| HPV31 | E1 | 9 | 593 |
| HPV31 | E1 | 9 | 488 |
| HPV31 | E1 | 9 | 466 |
| HPV31 | E1 | 9 | 235 |
| HPV31 | E1 | 9 | 277 |
| HPV31 | E1 | 9 | 473 |
| HPV31 | E1 | 9 | 447 |
| HPV31 | E1 | 9 | 443 |
| HPV31 | E1 | 9 | 280 |
| HPV31 | E1 | 9 | 259 |
| HPV31 | E1 | 9 | 537 |
| HPV31 | E1 | 9 | 493 |
| HPV31 | E1 | 9 | 566 |
| HPV31 | E1 | 9 | 197 |
| HPV31 | E1 | 9 | 302 |
| HPV31 | E1 | 9 | 203 |
| HPV31 | E1 | 9 | 405 |
| HPV31 | E1 | 9 | 258 |
| HPV31 | E1 | 9 | 146 |
| HPV31 | E1 | 9 | 454 |
| HPV31 | E1 | 9 | 56 |
| HPV31 | E1 | 9 | 350 |
| HPV31 | E1 | 9 | 18 |
| HPV31 | E1 | 9 | 138 |
| HPV31 | E1 | 9 | 320 |
| HPV31 | E1 | 9 | 292 |
| HPV31 | E1 | 9 | 543 |
| HPV31 | E1 | 9 | 70 |
| HPV31 | E1 | 9 | 433 |
| HPV31 | E1 | 9 | 153 |
| HPV31 | E1 | 9 | 345 |
| HPV31 | E1 | 9 | 90 |
| HPV31 | E1 | 9 | 520 |
| HPV31 | E1 | 9 | 175 |
| HPV31 | E1 | 9 | 126 |
| HPV31 | E1 | 9 | 558 |
| HPV31 | E1 | 9 | 489 |
| HPV31 | E1 | 9 | 529 |
| HPV31 | E1 | 9 | 109 |
| HPV31 | E1 | 9 | 564 |
| HPV31 | E1 | 9 | 597 |
| HPV31 | E1 | 9 | 101 |
| HPV31 | E1 | 9 | 253 |
| HPV31 | E1 | 9 | 285 |
| HPV31 | E1 | 9 | 319 |
| HPV31 | E1 | 9 | 221 |
| HPV31 | E1 | 9 | 51 |
| HPV31 | E1 | 9 | 23 |
| HPV31 | E1 | 9 | 568 |
| HPV31 | E1 | 9 | 426 |
| HPV31 | E1 | 9 | 85 |
| HPV31 | E1 | 9 | 437 |
| HPV31 | E1 | 9 | 200 |
| HPV31 | E1 | 9 | 254 |
| HPV31 | E1 | 9 | 559 |
| HPV31 | E1 | 9 | 362 |
| HPV31 | E1 | 9 | 244 |
| HPV31 | E1 | 9 | 241 |

TABLE XIX-continued

DR Supermotif Peptides

| 1 | 2 | 3 | 4 |
|---|---|---|---|
| HPV31 | E2 | 9 | 211 |
| HPV31 | E2 | 9 | 70 |
| HPV31 | E2 | 9 | 64 |
| HPV31 | E2 | 9 | 49 |
| HPV31 | E2 | 9 | 275 |
| HPV31 | E2 | 9 | 354 |
| HPV31 | E2 | 9 | 94 |
| HPV31 | E2 | 9 | 152 |
| HPV31 | E2 | 9 | 207 |
| HPV31 | E2 | 9 | 77 |
| HPV31 | E2 | 9 | 200 |
| HPV31 | E2 | 9 | 210 |
| HPV31 | E2 | 9 | 267 |
| HPV31 | E2 | 9 | 193 |
| HPV31 | E2 | 9 | 38 |
| HPV31 | E2 | 9 | 167 |
| HPV31 | E2 | 9 | 59 |
| HPV31 | E2 | 9 | 33 |
| HPV31 | E2 | 9 | 54 |
| HPV31 | E2 | 9 | 342 |
| HPV31 | E2 | 9 | 160 |
| HPV31 | E2 | 9 | 319 |
| HPV31 | E2 | 9 | 41 |
| HPV31 | E2 | 9 | 102 |
| HPV31 | E2 | 9 | 308 |
| HPV31 | E2 | 9 | 357 |
| HPV31 | E2 | 9 | 73 |
| HPV31 | E2 | 9 | 340 |
| HPV31 | E2 | 9 | 274 |
| HPV31 | E2 | 9 | 92 |
| HPV31 | E2 | 9 | 58 |
| HPV31 | E2 | 9 | 262 |
| HPV31 | E2 | 9 | 136 |
| HPV31 | E2 | 9 | 261 |
| HPV31 | E2 | 9 | 147 |
| HPV31 | E2 | 9 | 99 |
| HPV31 | E2 | 9 | 194 |
| HPV31 | E2 | 9 | 10 |
| HPV31 | E2 | 9 | 205 |
| HPV31 | E2 | 9 | 236 |
| HPV31 | E2 | 9 | 101 |
| HPV31 | E2 | 9 | 326 |
| HPV31 | E2 | 9 | 287 |
| HPV31 | E2 | 9 | 359 |
| HPV31 | E2 | 9 | 270 |
| HPV31 | E2 | 9 | 44 |
| HPV31 | E2 | 9 | 62 |
| HPV31 | E2 | 9 | 36 |
| HPV31 | E2 | 9 | 318 |
| HPV31 | E2 | 9 | 141 |
| HPV31 | E2 | 9 | 134 |
| HPV31 | E5 | 9 | 1 |
| HPV31 | E5 | 9 | 2 |
| HPV31 | E5 | 9 | 43 |
| HPV31 | E5 | 9 | 62 |
| HPV31 | E5 | 9 | 21 |
| HPV31 | E5 | 9 | 17 |
| HPV31 | E5 | 9 | 64 |
| HPV31 | E5 | 9 | 29 |
| HPV31 | E5 | 9 | 23 |
| HPV31 | E5 | 9 | 6 |
| HPV31 | E5 | 9 | 22 |
| HPV31 | E5 | 9 | 69 |
| HPV31 | E5 | 9 | 27 |
| HPV31 | E5 | 9 | 51 |
| HPV31 | E5 | 9 | 32 |
| HPV31 | E5 | 9 | 9 |
| HPV31 | E5 | 9 | 49 |
| HPV31 | E5 | 9 | 65 |
| HPV31 | E5 | 9 | 16 |
| HPV31 | E5 | 9 | 74 |
| HPV31 | E5 | 9 | 48 |
| HPV31 | E5 | 9 | 47 |
| HPV31 | E5 | 9 | 46 |
| HPV31 | E5 | 9 | 60 |
| HPV31 | E5 | 9 | 52 |
| HPV31 | E5 | 9 | 4 |
| HPV31 | E5 | 9 | 73 |
| HPV31 | E5 | 9 | 33 |
| HPV31 | E5 | 9 | 13 |
| HPV31 | E5 | 9 | 38 |
| HPV31 | E5 | 9 | 44 |
| HPV31 | E5 | 9 | 57 |
| HPV31 | E5 | 9 | 11 |
| HPV31 | E5 | 9 | 28 |
| HPV31 | E5 | 9 | 68 |
| HPV31 | E5 | 9 | 50 |
| HPV31 | E5 | 9 | 15 |
| HPV31 | E5 | 9 | 24 |
| HPV31 | E5 | 9 | 36 |
| HPV31 | E5 | 9 | 12 |
| HPV31 | E5 | 9 | 39 |
| HPV31 | E5 | 9 | 42 |
| HPV31 | E5 | 9 | 71 |
| HPV31 | E5 | 9 | 66 |
| HPV31 | E6 | 9 | 1 |
| HPV31 | E6 | 9 | 21 |
| HPV31 | E6 | 9 | 100 |
| HPV31 | E6 | 9 | 69 |
| HPV31 | E6 | 9 | 47 |
| HPV31 | E6 | 9 | 101 |
| HPV31 | E6 | 9 | 78 |
| HPV31 | E6 | 9 | 23 |
| HPV31 | E6 | 9 | 28 |
| HPV31 | E6 | 9 | 128 |
| HPV31 | E6 | 9 | 132 |
| HPV31 | E6 | 9 | 140 |
| HPV31 | E6 | 9 | 99 |
| HPV31 | E6 | 9 | 104 |
| HPV31 | E6 | 9 | 37 |
| HPV31 | E6 | 9 | 91 |
| HPV31 | E6 | 9 | 53 |
| HPV31 | E6 | 9 | 32 |
| HPV31 | E6 | 9 | 96 |
| HPV31 | E6 | 9 | 62 |
| HPV31 | E6 | 9 | 12 |
| HPV31 | E6 | 9 | 83 |
| HPV31 | E6 | 9 | 43 |
| HPV31 | E6 | 9 | 54 |
| HPV31 | E6 | 9 | 45 |
| HPV31 | E6 | 9 | 81 |
| HPV31 | E6 | 9 | 26 |
| HPV31 | E7 | 9 | 1 |
| HPV31 | E7 | 9 | 78 |
| HPV31 | E7 | 9 | 37 |
| HPV31 | E7 | 9 | 84 |
| HPV31 | E7 | 9 | 90 |
| HPV31 | E7 | 9 | 79 |
| HPV31 | E7 | 9 | 87 |
| HPV31 | E7 | 9 | 54 |
| HPV31 | E7 | 9 | 12 |
| HPV31 | E7 | 9 | 69 |
| HPV31 | E7 | 9 | 89 |
| HPV31 | E7 | 9 | 74 |
| HPV31 | E7 | 9 | 67 |
| HPV31 | E7 | 9 | 8 |
| HPV31 | E7 | 9 | 15 |
| HPV31 | L1 | 9 | 1 |
| HPV31 | L1 | 9 | 389 |
| HPV31 | L1 | 9 | 43 |
| HPV31 | L1 | 9 | 12 |
| HPV31 | L1 | 9 | 349 |
| HPV31 | L1 | 9 | 150 |
| HPV31 | L1 | 9 | 189 |
| HPV31 | L1 | 9 | 28 |
| HPV31 | L1 | 9 | 375 |
| HPV31 | L1 | 9 | 278 |
| HPV31 | L1 | 9 | 91 |
| HPV31 | L1 | 9 | 405 |
| HPV31 | L1 | 9 | 447 |

TABLE XIX-continued

DR Supermotif Peptides

| 1 | 2 | 3 | 4 |
|---|---|---|---|
| HPV31 | L1 | 9 | 11 |
| HPV31 | L1 | 9 | 419 |
| HPV31 | L1 | 9 | 452 |
| HPV31 | L1 | 9 | 251 |
| HPV31 | L1 | 9 | 209 |
| HPV31 | L1 | 9 | 445 |
| HPV31 | L1 | 9 | 214 |
| HPV31 | L1 | 9 | 371 |
| HPV31 | L1 | 9 | 170 |
| HPV31 | L1 | 9 | 108 |
| HPV31 | L1 | 9 | 71 |
| HPV31 | L1 | 9 | 330 |
| HPV31 | L1 | 9 | 114 |
| HPV31 | L1 | 9 | 118 |
| HPV31 | L1 | 9 | 50 |
| HPV31 | L1 | 9 | 379 |
| HPV31 | L1 | 9 | 395 |
| HPV31 | L1 | 9 | 384 |
| HPV31 | L1 | 9 | 62 |
| HPV31 | L1 | 9 | 221 |
| HPV31 | L1 | 9 | 160 |
| HPV31 | L1 | 9 | 403 |
| HPV31 | L1 | 9 | 16 |
| HPV31 | L1 | 9 | 4 |
| HPV31 | L1 | 9 | 392 |
| HPV31 | L1 | 9 | 407 |
| HPV31 | L1 | 9 | 35 |
| HPV31 | L1 | 9 | 312 |
| HPV31 | L1 | 9 | 345 |
| HPV31 | L1 | 9 | 181 |
| HPV31 | L1 | 9 | 292 |
| HPV31 | L1 | 9 | 196 |
| HPV31 | L1 | 9 | 223 |
| HPV31 | L1 | 9 | 61 |
| HPV31 | L1 | 9 | 225 |
| HPV31 | L1 | 9 | 191 |
| HPV31 | L1 | 9 | 84 |
| HPV31 | L1 | 9 | 276 |
| HPV31 | L1 | 9 | 18 |
| HPV31 | L1 | 9 | 377 |
| HPV31 | L1 | 9 | 465 |
| HPV31 | L1 | 9 | 159 |
| HPV31 | L1 | 9 | 332 |
| HPV31 | L1 | 9 | 157 |
| HPV31 | L1 | 9 | 73 |
| HPV31 | L1 | 9 | 262 |
| HPV31 | L1 | 9 | 101 |
| HPV31 | L1 | 9 | 460 |
| HPV31 | L1 | 9 | 300 |
| HPV31 | L1 | 9 | 268 |
| HPV31 | L1 | 9 | 152 |
| HPV31 | L1 | 9 | 427 |
| HPV31 | L1 | 9 | 343 |
| HPV31 | L1 | 9 | 34 |
| HPV31 | L1 | 9 | 99 |
| HPV31 | L1 | 9 | 13 |
| HPV31 | L1 | 9 | 421 |
| HPV31 | L1 | 9 | 76 |
| HPV31 | L1 | 9 | 335 |
| HPV31 | L1 | 9 | 235 |
| HPV31 | L1 | 9 | 422 |
| HPV31 | L1 | 9 | 74 |
| HPV31 | L2 | 9 | 1 |
| HPV31 | L2 | 9 | 45 |
| HPV31 | L2 | 9 | 363 |
| HPV31 | L2 | 9 | 276 |
| HPV31 | L2 | 9 | 163 |
| HPV31 | L2 | 9 | 46 |
| HPV31 | L2 | 9 | 361 |
| HPV31 | L2 | 9 | 411 |
| HPV31 | L2 | 9 | 87 |
| HPV31 | L2 | 9 | 261 |
| HPV31 | L2 | 9 | 193 |
| HPV31 | L2 | 9 | 114 |
| HPV31 | L2 | 9 | 262 |
| HPV31 | L2 | 9 | 333 |
| HPV31 | L2 | 9 | 439 |
| HPV31 | L2 | 9 | 177 |
| HPV31 | L2 | 9 | 409 |
| HPV31 | L2 | 9 | 55 |
| HPV31 | L2 | 9 | 178 |
| HPV31 | L2 | 9 | 41 |
| HPV31 | L2 | 9 | 321 |
| HPV31 | L2 | 9 | 98 |
| HPV31 | L2 | 9 | 282 |
| HPV31 | L2 | 9 | 147 |
| HPV31 | L2 | 9 | 48 |
| HPV31 | L2 | 9 | 404 |
| HPV31 | L2 | 9 | 36 |
| HPV31 | L2 | 9 | 117 |
| HPV31 | L2 | 9 | 245 |
| HPV31 | L2 | 9 | 280 |
| HPV31 | L2 | 9 | 338 |
| HPV31 | L2 | 9 | 352 |
| HPV31 | L2 | 9 | 205 |
| HPV31 | L2 | 9 | 252 |
| HPV31 | L2 | 9 | 158 |
| HPV31 | L2 | 9 | 145 |
| HPV31 | L2 | 9 | 123 |
| HPV31 | L2 | 9 | 277 |
| HPV31 | L2 | 9 | 423 |
| HPV31 | L2 | 9 | 82 |
| HPV31 | L2 | 9 | 164 |
| HPV31 | L2 | 9 | 418 |
| HPV31 | L2 | 9 | 95 |
| HPV31 | L2 | 9 | 455 |
| HPV31 | L2 | 9 | 222 |
| HPV31 | L2 | 9 | 294 |
| HPV31 | L2 | 9 | 93 |
| HPV31 | L2 | 9 | 72 |
| HPV31 | L2 | 9 | 319 |
| HPV31 | L2 | 9 | 457 |
| HPV31 | L2 | 9 | 387 |
| HPV31 | L2 | 9 | 176 |
| HPV31 | L2 | 9 | 115 |
| HPV31 | L2 | 9 | 335 |
| HPV31 | L2 | 9 | 89 |
| HPV31 | L2 | 9 | 53 |
| HPV31 | L2 | 9 | 377 |
| HPV31 | L2 | 9 | 371 |
| HPV31 | L2 | 9 | 188 |
| HPV31 | L2 | 9 | 144 |
| HPV31 | L2 | 9 | 19 |
| HPV31 | L2 | 9 | 230 |
| HPV31 | L2 | 9 | 419 |
| HPV31 | L2 | 9 | 383 |
| HPV31 | L2 | 9 | 132 |
| HPV31 | L2 | 9 | 421 |
| HPV31 | L2 | 9 | 101 |
| HPV31 | L2 | 9 | 320 |
| HPV31 | L2 | 9 | 233 |
| HPV31 | L2 | 9 | 386 |
| HPV31 | L2 | 9 | 109 |
| HPV31 | L2 | 9 | 458 |
| HPV31 | L2 | 9 | 255 |
| HPV31 | L2 | 9 | 299 |
| HPV31 | L2 | 9 | 75 |
| HPV31 | L2 | 9 | 323 |
| HPV33 | E1 | 9 | 385 |
| HPV33 | E1 | 9 | 100 |
| HPV33 | E1 | 9 | 395 |
| HPV33 | E1 | 9 | 287 |
| HPV33 | E1 | 9 | 314 |
| HPV33 | E1 | 9 | 210 |
| HPV33 | E1 | 9 | 313 |
| HPV33 | E1 | 9 | 182 |
| HPV33 | E1 | 9 | 300 |
| HPV33 | E1 | 9 | 17 |
| HPV33 | E1 | 9 | 602 |
| HPV33 | E1 | 9 | 370 |

TABLE XIX-continued

DR Supermotif Peptides

| 1 | 2 | 3 | 4 |
|---|---|---|---|
| HPV33 | E1 | 9 | 348 |
| HPV33 | E1 | 9 | 266 |
| HPV33 | E1 | 9 | 368 |
| HPV33 | E1 | 9 | 133 |
| HPV33 | E1 | 9 | 569 |
| HPV33 | E1 | 9 | 156 |
| HPV33 | E1 | 9 | 231 |
| HPV33 | E1 | 9 | 120 |
| HPV33 | E1 | 9 | 79 |
| HPV33 | E1 | 9 | 298 |
| HPV33 | E1 | 9 | 456 |
| HPV33 | E1 | 9 | 492 |
| HPV33 | E1 | 9 | 628 |
| HPV33 | E1 | 9 | 478 |
| HPV33 | E1 | 9 | 236 |
| HPV33 | E1 | 9 | 547 |
| HPV33 | E1 | 9 | 254 |
| HPV33 | E1 | 9 | 371 |
| HPV33 | E1 | 9 | 528 |
| HPV33 | E1 | 9 | 514 |
| HPV33 | E1 | 9 | 418 |
| HPV33 | E1 | 9 | 271 |
| HPV33 | E1 | 9 | 487 |
| HPV33 | E1 | 9 | 325 |
| HPV33 | E1 | 9 | 213 |
| HPV33 | E1 | 9 | 234 |
| HPV33 | E1 | 9 | 208 |
| HPV33 | E1 | 9 | 513 |
| HPV33 | E1 | 9 | 281 |
| HPV33 | E1 | 9 | 466 |
| HPV33 | E1 | 9 | 606 |
| HPV33 | E1 | 9 | 501 |
| HPV33 | E1 | 9 | 479 |
| HPV33 | E1 | 9 | 248 |
| HPV33 | E1 | 9 | 486 |
| HPV33 | E1 | 9 | 460 |
| HPV33 | E1 | 9 | 247 |
| HPV33 | E1 | 9 | 50 |
| HPV33 | E1 | 9 | 272 |
| HPV33 | E1 | 9 | 293 |
| HPV33 | E1 | 9 | 159 |
| HPV33 | E1 | 9 | 506 |
| HPV33 | E1 | 9 | 579 |
| HPV33 | E1 | 9 | 550 |
| HPV33 | E1 | 9 | 315 |
| HPV33 | E1 | 9 | 216 |
| HPV33 | E1 | 9 | 202 |
| HPV33 | E1 | 9 | 138 |
| HPV33 | E1 | 9 | 333 |
| HPV33 | E1 | 9 | 305 |
| HPV33 | E1 | 9 | 556 |
| HPV33 | E1 | 9 | 144 |
| HPV33 | E1 | 9 | 358 |
| HPV33 | E1 | 9 | 548 |
| HPV33 | E1 | 9 | 267 |
| HPV33 | E1 | 9 | 283 |
| HPV33 | E1 | 9 | 533 |
| HPV33 | E1 | 9 | 571 |
| HPV33 | E1 | 9 | 467 |
| HPV33 | E1 | 9 | 502 |
| HPV33 | E1 | 9 | 542 |
| HPV33 | E1 | 9 | 291 |
| HPV33 | E1 | 9 | 191 |
| HPV33 | E1 | 9 | 610 |
| HPV33 | E1 | 9 | 524 |
| HPV33 | E1 | 9 | 312 |
| HPV33 | E1 | 9 | 18 |
| HPV33 | E1 | 9 | 332 |
| HPV33 | E1 | 9 | 286 |
| HPV33 | E1 | 9 | 85 |
| HPV33 | E1 | 9 | 23 |
| HPV33 | E1 | 9 | 581 |
| HPV33 | E1 | 9 | 439 |
| HPV33 | E1 | 9 | 219 |
| HPV33 | E1 | 9 | 520 |
| HPV33 | E1 | 9 | 572 |
| HPV33 | E1 | 9 | 375 |
| HPV33 | E1 | 9 | 257 |
| HPV33 | E2 | 9 | 1 |
| HPV33 | E2 | 9 | 178 |
| HPV33 | E2 | 9 | 72 |
| HPV33 | E2 | 9 | 49 |
| HPV33 | E2 | 9 | 44 |
| HPV33 | E2 | 9 | 240 |
| HPV33 | E2 | 9 | 58 |
| HPV33 | E2 | 9 | 250 |
| HPV33 | E2 | 9 | 139 |
| HPV33 | E2 | 9 | 16 |
| HPV33 | E2 | 9 | 77 |
| HPV33 | E2 | 9 | 188 |
| HPV33 | E2 | 9 | 171 |
| HPV33 | E2 | 9 | 73 |
| HPV33 | E2 | 9 | 54 |
| HPV33 | E2 | 9 | 192 |
| HPV33 | E2 | 9 | 193 |
| HPV33 | E2 | 9 | 59 |
| HPV33 | E2 | 9 | 35 |
| HPV33 | E2 | 9 | 33 |
| HPV33 | E2 | 9 | 158 |
| HPV33 | E2 | 9 | 140 |
| HPV33 | E2 | 9 | 300 |
| HPV33 | E2 | 9 | 183 |
| HPV33 | E2 | 9 | 19 |
| HPV33 | E2 | 9 | 102 |
| HPV33 | E2 | 9 | 338 |
| HPV33 | E2 | 9 | 38 |
| HPV33 | E2 | 9 | 296 |
| HPV33 | E2 | 9 | 11 |
| HPV33 | E2 | 9 | 243 |
| HPV33 | E2 | 9 | 321 |
| HPV33 | E2 | 9 | 30 |
| HPV33 | E2 | 9 | 199 |
| HPV33 | E2 | 9 | 335 |
| HPV33 | E2 | 9 | 333 |
| HPV33 | E2 | 9 | 268 |
| HPV33 | E2 | 9 | 99 |
| HPV33 | E2 | 9 | 194 |
| HPV33 | E2 | 9 | 94 |
| HPV33 | E2 | 9 | 101 |
| HPV33 | E2 | 9 | 204 |
| HPV33 | E2 | 9 | 147 |
| HPV33 | E2 | 9 | 152 |
| HPV33 | E2 | 9 | 70 |
| HPV33 | E2 | 9 | 244 |
| HPV33 | E2 | 9 | 92 |
| HPV33 | E2 | 9 | 155 |
| HPV33 | E2 | 9 | 62 |
| HPV33 | E2 | 9 | 36 |
| HPV33 | E2 | 9 | 170 |
| HPV33 | E2 | 9 | 299 |
| HPV33 | E2 | 9 | 134 |
| HPV33 | E5 | 9 | 1 |
| HPV33 | E5 | 9 | 2 |
| HPV33 | E5 | 9 | 3 |
| HPV33 | E5 | 9 | 33 |
| HPV33 | E5 | 9 | 11 |
| HPV33 | E5 | 9 | 66 |
| HPV33 | E5 | 9 | 17 |
| HPV33 | E5 | 9 | 55 |
| HPV33 | E5 | 9 | 54 |
| HPV33 | E5 | 9 | 12 |
| HPV33 | E5 | 9 | 59 |
| HPV33 | E5 | 9 | 6 |
| HPV33 | E5 | 9 | 47 |
| HPV33 | E5 | 9 | 5 |
| HPV33 | E5 | 9 | 13 |
| HPV33 | E5 | 9 | 29 |
| HPV33 | E5 | 9 | 10 |
| HPV33 | E5 | 9 | 58 |
| HPV33 | E5 | 9 | 50 |

TABLE XIX-continued

DR Supermotif Peptides

| 1 | 2 | 3 | 4 |
|---|---|---|---|
| HPV33 | E5 | 9 | 57 |
| HPV33 | E5 | 9 | 40 |
| HPV33 | E5 | 9 | 41 |
| HPV33 | E5 | 9 | 22 |
| HPV33 | E5 | 9 | 18 |
| HPV33 | E5 | 9 | 38 |
| HPV33 | E5 | 9 | 36 |
| HPV33 | E5 | 9 | 42 |
| HPV33 | E5 | 9 | 49 |
| HPV33 | E5 | 9 | 23 |
| HPV33 | E5 | 9 | 19 |
| HPV33 | E5 | 9 | 31 |
| HPV33 | E5 | 9 | 9 |
| HPV33 | E5 | 9 | 34 |
| HPV33 | E5 | 9 | 32 |
| HPV33 | E5 | 9 | 56 |
| HPV33 | E6 | 9 | 69 |
| HPV33 | E6 | 9 | 47 |
| HPV33 | E6 | 9 | 101 |
| HPV33 | E6 | 9 | 23 |
| HPV33 | E6 | 9 | 128 |
| HPV33 | E6 | 9 | 60 |
| HPV33 | E6 | 9 | 65 |
| HPV33 | E6 | 9 | 26 |
| HPV33 | E6 | 9 | 104 |
| HPV33 | E6 | 9 | 96 |
| HPV33 | E6 | 9 | 37 |
| HPV33 | E6 | 9 | 99 |
| HPV33 | E6 | 9 | 31 |
| HPV33 | E6 | 9 | 100 |
| HPV33 | E6 | 9 | 28 |
| HPV33 | E6 | 9 | 83 |
| HPV33 | E6 | 9 | 62 |
| HPV33 | E6 | 9 | 105 |
| HPV33 | E6 | 9 | 43 |
| HPV33 | E6 | 9 | 132 |
| HPV33 | E6 | 9 | 54 |
| HPV33 | E6 | 9 | 45 |
| HPV33 | E7 | 9 | 1 |
| HPV33 | E7 | 9 | 53 |
| HPV33 | E7 | 9 | 82 |
| HPV33 | E7 | 9 | 12 |
| HPV33 | E7 | 9 | 8 |
| HPV33 | E7 | 9 | 79 |
| HPV33 | E7 | 9 | 87 |
| HPV33 | E7 | 9 | 84 |
| HPV33 | E7 | 9 | 69 |
| HPV33 | E7 | 9 | 52 |
| HPV33 | E7 | 9 | 23 |
| HPV33 | E7 | 9 | 89 |
| HPV33 | E7 | 9 | 67 |
| HPV33 | E7 | 9 | 15 |
| HPV33 | E7 | 9 | 55 |
| HPV33 | L1 | 9 | 1 |
| HPV33 | L1 | 9 | 387 |
| HPV33 | L1 | 9 | 267 |
| HPV33 | L1 | 9 | 61 |
| HPV33 | L1 | 9 | 12 |
| HPV33 | L1 | 9 | 150 |
| HPV33 | L1 | 9 | 210 |
| HPV33 | L1 | 9 | 188 |
| HPV33 | L1 | 9 | 348 |
| HPV33 | L1 | 9 | 28 |
| HPV33 | L1 | 9 | 373 |
| HPV33 | L1 | 9 | 277 |
| HPV33 | L1 | 9 | 91 |
| HPV33 | L1 | 9 | 222 |
| HPV33 | L1 | 9 | 403 |
| HPV33 | L1 | 9 | 11 |
| HPV33 | L1 | 9 | 450 |
| HPV33 | L1 | 9 | 250 |
| HPV33 | L1 | 9 | 208 |
| HPV33 | L1 | 9 | 213 |
| HPV33 | L1 | 9 | 170 |
| HPV33 | L1 | 9 | 174 |
| HPV33 | L1 | 9 | 108 |
| HPV33 | L1 | 9 | 71 |
| HPV33 | L1 | 9 | 329 |
| HPV33 | L1 | 9 | 114 |
| HPV33 | L1 | 9 | 118 |
| HPV33 | L1 | 9 | 50 |
| HPV33 | L1 | 9 | 393 |
| HPV33 | L1 | 9 | 366 |
| HPV33 | L1 | 9 | 62 |
| HPV33 | L1 | 9 | 479 |
| HPV33 | L1 | 9 | 220 |
| HPV33 | L1 | 9 | 382 |
| HPV33 | L1 | 9 | 445 |
| HPV33 | L1 | 9 | 160 |
| HPV33 | L1 | 9 | 401 |
| HPV33 | L1 | 9 | 443 |
| HPV33 | L1 | 9 | 127 |
| HPV33 | L1 | 9 | 16 |
| HPV33 | L1 | 9 | 4 |
| HPV33 | L1 | 9 | 390 |
| HPV33 | L1 | 9 | 311 |
| HPV33 | L1 | 9 | 344 |
| HPV33 | L1 | 9 | 195 |
| HPV33 | L1 | 9 | 275 |
| HPV33 | L1 | 9 | 224 |
| HPV33 | L1 | 9 | 190 |
| HPV33 | L1 | 9 | 84 |
| HPV33 | L1 | 9 | 18 |
| HPV33 | L1 | 9 | 417 |
| HPV33 | L1 | 9 | 405 |
| HPV33 | L1 | 9 | 463 |
| HPV33 | L1 | 9 | 375 |
| HPV33 | L1 | 9 | 159 |
| HPV33 | L1 | 9 | 157 |
| HPV33 | L1 | 9 | 331 |
| HPV33 | L1 | 9 | 73 |
| HPV33 | L1 | 9 | 261 |
| HPV33 | L1 | 9 | 468 |
| HPV33 | L1 | 9 | 101 |
| HPV33 | L1 | 9 | 458 |
| HPV33 | L1 | 9 | 299 |
| HPV33 | L1 | 9 | 35 |
| HPV33 | L1 | 9 | 152 |
| HPV33 | L1 | 9 | 425 |
| HPV33 | L1 | 9 | 43 |
| HPV33 | L1 | 9 | 291 |
| HPV33 | L1 | 9 | 27 |
| HPV33 | L1 | 9 | 99 |
| HPV33 | L1 | 9 | 34 |
| HPV33 | L1 | 9 | 13 |
| HPV33 | L1 | 9 | 419 |
| HPV33 | L1 | 9 | 369 |
| HPV33 | L1 | 9 | 377 |
| HPV33 | L1 | 9 | 76 |
| HPV33 | L1 | 9 | 334 |
| HPV33 | L1 | 9 | 234 |
| HPV33 | L1 | 9 | 420 |
| HPV33 | L1 | 9 | 74 |
| HPV33 | L2 | 9 | 1 |
| HPV33 | L2 | 9 | 370 |
| HPV33 | L2 | 9 | 44 |
| HPV33 | L2 | 9 | 85 |
| HPV33 | L2 | 9 | 281 |
| HPV33 | L2 | 9 | 45 |
| HPV33 | L2 | 9 | 202 |
| HPV33 | L2 | 9 | 266 |
| HPV33 | L2 | 9 | 168 |
| HPV33 | L2 | 9 | 152 |
| HPV33 | L2 | 9 | 113 |
| HPV33 | L2 | 9 | 433 |
| HPV33 | L2 | 9 | 260 |
| HPV33 | L2 | 9 | 430 |
| HPV33 | L2 | 9 | 304 |
| HPV33 | L2 | 9 | 424 |
| HPV33 | L2 | 9 | 440 |

TABLE XIX-continued

DR Supermotif Peptides

| 1 | 2 | 3 | 4 |
|---|---|---|---|
| HPV33 | L2 | 9 | 182 |
| HPV33 | L2 | 9 | 40 |
| HPV33 | L2 | 9 | 54 |
| HPV33 | L2 | 9 | 183 |
| HPV33 | L2 | 9 | 250 |
| HPV33 | L2 | 9 | 377 |
| HPV33 | L2 | 9 | 325 |
| HPV33 | L2 | 9 | 287 |
| HPV33 | L2 | 9 | 47 |
| HPV33 | L2 | 9 | 35 |
| HPV33 | L2 | 9 | 427 |
| HPV33 | L2 | 9 | 334 |
| HPV33 | L2 | 9 | 107 |
| HPV33 | L2 | 9 | 285 |
| HPV33 | L2 | 9 | 88 |
| HPV33 | L2 | 9 | 348 |
| HPV33 | L2 | 9 | 365 |
| HPV33 | L2 | 9 | 362 |
| HPV33 | L2 | 9 | 343 |
| HPV33 | L2 | 9 | 198 |
| HPV33 | L2 | 9 | 257 |
| HPV33 | L2 | 9 | 163 |
| HPV33 | L2 | 9 | 400 |
| HPV33 | L2 | 9 | 142 |
| HPV33 | L2 | 9 | 282 |
| HPV33 | L2 | 9 | 129 |
| HPV33 | L2 | 9 | 414 |
| HPV33 | L2 | 9 | 169 |
| HPV33 | L2 | 9 | 94 |
| HPV33 | L2 | 9 | 381 |
| HPV33 | L2 | 9 | 458 |
| HPV33 | L2 | 9 | 299 |
| HPV33 | L2 | 9 | 324 |
| HPV33 | L2 | 9 | 456 |
| HPV33 | L2 | 9 | 227 |
| HPV33 | L2 | 9 | 92 |
| HPV33 | L2 | 9 | 71 |
| HPV33 | L2 | 9 | 181 |
| HPV33 | L2 | 9 | 52 |
| HPV33 | L2 | 9 | 428 |
| HPV33 | L2 | 9 | 332 |
| HPV33 | L2 | 9 | 415 |
| HPV33 | L2 | 9 | 222 |
| HPV33 | L2 | 9 | 210 |
| HPV33 | L2 | 9 | 421 |
| HPV33 | L2 | 9 | 159 |
| HPV33 | L2 | 9 | 216 |
| HPV33 | L2 | 9 | 83 |
| HPV33 | L2 | 9 | 203 |
| HPV33 | L2 | 9 | 268 |
| HPV33 | L2 | 9 | 141 |
| HPV33 | L2 | 9 | 405 |
| HPV33 | L2 | 9 | 18 |
| HPV33 | L2 | 9 | 235 |
| HPV33 | L2 | 9 | 193 |
| HPV33 | L2 | 9 | 114 |
| HPV33 | L2 | 9 | 97 |
| HPV33 | L2 | 9 | 100 |
| HPV33 | L2 | 9 | 238 |
| HPV33 | L2 | 9 | 147 |
| HPV33 | L2 | 9 | 328 |
| HPV33 | L2 | 9 | 384 |
| HPV33 | L2 | 9 | 74 |
| HPV45 | E1 | 9 | 385 |
| HPV45 | E1 | 9 | 178 |
| HPV45 | E1 | 9 | 395 |
| HPV45 | E1 | 9 | 314 |
| HPV45 | E1 | 9 | 254 |
| HPV45 | E1 | 9 | 300 |
| HPV45 | E1 | 9 | 17 |
| HPV45 | E1 | 9 | 142 |
| HPV45 | E1 | 9 | 524 |
| HPV45 | E1 | 9 | 264 |
| HPV45 | E1 | 9 | 370 |
| HPV45 | E1 | 9 | 569 |
| HPV45 | E1 | 9 | 137 |
| HPV45 | E1 | 9 | 348 |
| HPV45 | E1 | 9 | 231 |
| HPV45 | E1 | 9 | 610 |
| HPV45 | E1 | 9 | 368 |
| HPV45 | E1 | 9 | 298 |
| HPV45 | E1 | 9 | 528 |
| HPV45 | E1 | 9 | 486 |
| HPV45 | E1 | 9 | 635 |
| HPV45 | E1 | 9 | 247 |
| HPV45 | E1 | 9 | 492 |
| HPV45 | E1 | 9 | 161 |
| HPV45 | E1 | 9 | 629 |
| HPV45 | E1 | 9 | 19 |
| HPV45 | E1 | 9 | 547 |
| HPV45 | E1 | 9 | 236 |
| HPV45 | E1 | 9 | 487 |
| HPV45 | E1 | 9 | 494 |
| HPV45 | E1 | 9 | 271 |
| HPV45 | E1 | 9 | 469 |
| HPV45 | E1 | 9 | 325 |
| HPV45 | E1 | 9 | 210 |
| HPV45 | E1 | 9 | 606 |
| HPV45 | E1 | 9 | 208 |
| HPV45 | E1 | 9 | 466 |
| HPV45 | E1 | 9 | 548 |
| HPV45 | E1 | 9 | 479 |
| HPV45 | E1 | 9 | 248 |
| HPV45 | E1 | 9 | 513 |
| HPV45 | E1 | 9 | 266 |
| HPV45 | E1 | 9 | 571 |
| HPV45 | E1 | 9 | 506 |
| HPV45 | E1 | 9 | 85 |
| HPV45 | E1 | 9 | 456 |
| HPV45 | E1 | 9 | 293 |
| HPV45 | E1 | 9 | 550 |
| HPV45 | E1 | 9 | 315 |
| HPV45 | E1 | 9 | 234 |
| HPV45 | E1 | 9 | 418 |
| HPV45 | E1 | 9 | 50 |
| HPV45 | E1 | 9 | 467 |
| HPV45 | E1 | 9 | 18 |
| HPV45 | E1 | 9 | 501 |
| HPV45 | E1 | 9 | 99 |
| HPV45 | E1 | 9 | 333 |
| HPV45 | E1 | 9 | 556 |
| HPV45 | E1 | 9 | 305 |
| HPV45 | E1 | 9 | 394 |
| HPV45 | E1 | 9 | 70 |
| HPV45 | E1 | 9 | 105 |
| HPV45 | E1 | 9 | 358 |
| HPV45 | E1 | 9 | 338 |
| HPV45 | E1 | 9 | 283 |
| HPV45 | E1 | 9 | 533 |
| HPV45 | E1 | 9 | 130 |
| HPV45 | E1 | 9 | 48 |
| HPV45 | E1 | 9 | 502 |
| HPV45 | E1 | 9 | 113 |
| HPV45 | E1 | 9 | 419 |
| HPV45 | E1 | 9 | 291 |
| HPV45 | E1 | 9 | 216 |
| HPV45 | E1 | 9 | 332 |
| HPV45 | E1 | 9 | 312 |
| HPV45 | E1 | 9 | 51 |
| HPV45 | E1 | 9 | 447 |
| HPV45 | E1 | 9 | 23 |
| HPV45 | E1 | 9 | 581 |
| HPV45 | E1 | 9 | 233 |
| HPV45 | E1 | 9 | 439 |
| HPV45 | E1 | 9 | 219 |
| HPV45 | E1 | 9 | 579 |
| HPV45 | E1 | 9 | 267 |
| HPV45 | E1 | 9 | 421 |
| HPV45 | E1 | 9 | 572 |
| HPV45 | E1 | 9 | 257 |

TABLE XIX-continued

DR Supermotif Peptides

| 1 | 2 | 3 | 4 |
|---|---|---|---|
| HPV45 | E1 | 9 | 375 |
| HPV45 | E2 | 9 | 1 |
| HPV45 | E2 | 9 | 159 |
| HPV45 | E2 | 9 | 317 |
| HPV45 | E2 | 9 | 107 |
| HPV45 | E2 | 9 | 185 |
| HPV45 | E2 | 9 | 137 |
| HPV45 | E2 | 9 | 214 |
| HPV45 | E2 | 9 | 144 |
| HPV45 | E2 | 9 | 108 |
| HPV45 | E2 | 9 | 83 |
| HPV45 | E2 | 9 | 151 |
| HPV45 | E2 | 9 | 195 |
| HPV45 | E2 | 9 | 200 |
| HPV45 | E2 | 9 | 79 |
| HPV45 | E2 | 9 | 272 |
| HPV45 | E2 | 9 | 65 |
| HPV45 | E2 | 9 | 39 |
| HPV45 | E2 | 9 | 60 |
| HPV45 | E2 | 9 | 146 |
| HPV45 | E2 | 9 | 10 |
| HPV45 | E2 | 9 | 243 |
| HPV45 | E2 | 9 | 353 |
| HPV45 | E2 | 9 | 44 |
| HPV45 | E2 | 9 | 313 |
| HPV45 | E2 | 9 | 17 |
| HPV45 | E2 | 9 | 138 |
| HPV45 | E2 | 9 | 98 |
| HPV45 | E2 | 9 | 273 |
| HPV45 | E2 | 9 | 36 |
| HPV45 | E2 | 9 | 350 |
| HPV45 | E2 | 9 | 268 |
| HPV45 | E2 | 9 | 70 |
| HPV45 | E2 | 9 | 349 |
| HPV45 | E2 | 9 | 285 |
| HPV45 | E2 | 9 | 32 |
| HPV45 | E2 | 9 | 324 |
| HPV45 | E2 | 9 | 236 |
| HPV45 | E2 | 9 | 152 |
| HPV45 | E2 | 9 | 175 |
| HPV45 | E2 | 9 | 68 |
| HPV45 | E2 | 9 | 223 |
| HPV45 | E2 | 9 | 162 |
| HPV45 | E2 | 9 | 167 |
| HPV45 | E2 | 9 | 42 |
| HPV45 | E6 | 9 | 34 |
| HPV45 | E6 | 9 | 54 |
| HPV45 | E6 | 9 | 30 |
| HPV45 | E6 | 9 | 80 |
| HPV45 | E6 | 9 | 56 |
| HPV45 | E6 | 9 | 33 |
| HPV45 | E6 | 9 | 106 |
| HPV45 | E6 | 9 | 39 |
| HPV45 | E6 | 9 | 93 |
| HPV45 | E6 | 9 | 55 |
| HPV45 | E6 | 9 | 28 |
| HPV45 | E6 | 9 | 101 |
| HPV45 | E6 | 9 | 103 |
| HPV45 | E6 | 9 | 98 |
| HPV45 | E6 | 9 | 25 |
| HPV45 | E6 | 9 | 14 |
| HPV45 | E6 | 9 | 49 |
| HPV45 | E6 | 9 | 12 |
| HPV45 | E6 | 9 | 60 |
| HPV45 | E6 | 9 | 85 |
| HPV45 | E6 | 9 | 47 |
| HPV45 | E7 | 9 | 1 |
| HPV45 | E7 | 9 | 45 |
| HPV45 | E7 | 9 | 50 |
| HPV45 | E7 | 9 | 90 |
| HPV45 | E7 | 9 | 87 |
| HPV45 | E7 | 9 | 98 |
| HPV45 | E7 | 9 | 95 |
| HPV45 | E7 | 9 | 12 |
| HPV45 | E7 | 9 | 21 |
| HPV45 | E7 | 9 | 91 |
| HPV45 | E7 | 9 | 8 |
| HPV45 | E7 | 9 | 62 |
| HPV45 | E7 | 9 | 75 |
| HPV45 | E7 | 9 | 97 |
| HPV45 | E7 | 9 | 27 |
| HPV45 | L1 | 9 | 1 |
| HPV45 | L1 | 9 | 418 |
| HPV45 | L1 | 9 | 294 |
| HPV45 | L1 | 9 | 165 |
| HPV45 | L1 | 9 | 97 |
| HPV45 | L1 | 9 | 215 |
| HPV45 | L1 | 9 | 54 |
| HPV45 | L1 | 9 | 404 |
| HPV45 | L1 | 9 | 304 |
| HPV45 | L1 | 9 | 117 |
| HPV45 | L1 | 9 | 37 |
| HPV45 | L1 | 9 | 249 |
| HPV45 | L1 | 9 | 277 |
| HPV45 | L1 | 9 | 27 |
| HPV45 | L1 | 9 | 24 |
| HPV45 | L1 | 9 | 240 |
| HPV45 | L1 | 9 | 196 |
| HPV45 | L1 | 9 | 13 |
| HPV45 | L1 | 9 | 134 |
| HPV45 | L1 | 9 | 75 |
| HPV45 | L1 | 9 | 140 |
| HPV45 | L1 | 9 | 319 |
| HPV45 | L1 | 9 | 6 |
| HPV45 | L1 | 9 | 358 |
| HPV45 | L1 | 9 | 408 |
| HPV45 | L1 | 9 | 424 |
| HPV45 | L1 | 9 | 15 |
| HPV45 | L1 | 9 | 247 |
| HPV45 | L1 | 9 | 112 |
| HPV45 | L1 | 9 | 476 |
| HPV45 | L1 | 9 | 89 |
| HPV45 | L1 | 9 | 186 |
| HPV45 | L1 | 9 | 432 |
| HPV45 | L1 | 9 | 18 |
| HPV45 | L1 | 9 | 405 |
| HPV45 | L1 | 9 | 30 |
| HPV45 | L1 | 9 | 421 |
| HPV45 | L1 | 9 | 436 |
| HPV45 | L1 | 9 | 7 |
| HPV45 | L1 | 9 | 340 |
| HPV45 | L1 | 9 | 76 |
| HPV45 | L1 | 9 | 222 |
| HPV45 | L1 | 9 | 20 |
| HPV45 | L1 | 9 | 176 |
| HPV45 | L1 | 9 | 434 |
| HPV45 | L1 | 9 | 207 |
| HPV45 | L1 | 9 | 251 |
| HPV45 | L1 | 9 | 217 |
| HPV45 | L1 | 9 | 110 |
| HPV45 | L1 | 9 | 302 |
| HPV45 | L1 | 9 | 504 |
| HPV45 | L1 | 9 | 406 |
| HPV45 | L1 | 9 | 185 |
| HPV45 | L1 | 9 | 360 |
| HPV45 | L1 | 9 | 183 |
| HPV45 | L1 | 9 | 494 |
| HPV45 | L1 | 9 | 99 |
| HPV45 | L1 | 9 | 293 |
| HPV45 | L1 | 9 | 288 |
| HPV45 | L1 | 9 | 499 |
| HPV45 | L1 | 9 | 127 |
| HPV45 | L1 | 9 | 320 |
| HPV45 | L1 | 9 | 328 |
| HPV45 | L1 | 9 | 61 |
| HPV45 | L1 | 9 | 397 |
| HPV45 | L1 | 9 | 69 |
| HPV45 | L1 | 9 | 489 |
| HPV45 | L1 | 9 | 371 |
| HPV45 | L1 | 9 | 38 |

TABLE XIX-continued

DR Supermotif Peptides

| 1 | 2 | 3 | 4 |
|---|---|---|---|
| HPV45 | L1 | 9 | 178 |
| HPV45 | L1 | 9 | 53 |
| HPV45 | L1 | 9 | 303 |
| HPV45 | L1 | 9 | 413 |
| HPV45 | L1 | 9 | 170 |
| HPV45 | L1 | 9 | 125 |
| HPV45 | L1 | 9 | 60 |
| HPV45 | L1 | 9 | 481 |
| HPV45 | L1 | 9 | 39 |
| HPV45 | L1 | 9 | 450 |
| HPV45 | L1 | 9 | 448 |
| HPV45 | L1 | 9 | 400 |
| HPV45 | L1 | 9 | 23 |
| HPV45 | L1 | 9 | 102 |
| HPV45 | L1 | 9 | 192 |
| HPV45 | L1 | 9 | 363 |
| HPV45 | L1 | 9 | 474 |
| HPV45 | L1 | 9 | 78 |
| HPV45 | L1 | 9 | 235 |
| HPV45 | L1 | 9 | 153 |
| HPV45 | L1 | 9 | 261 |
| HPV45 | L1 | 9 | 451 |
| HPV45 | L1 | 9 | 100 |
| HPV45 | L2 | 9 | 1 |
| HPV45 | L2 | 9 | 2 |
| HPV45 | L2 | 9 | 44 |
| HPV45 | L2 | 9 | 385 |
| HPV45 | L2 | 9 | 408 |
| HPV45 | L2 | 9 | 45 |
| HPV45 | L2 | 9 | 346 |
| HPV45 | L2 | 9 | 112 |
| HPV45 | L2 | 9 | 263 |
| HPV45 | L2 | 9 | 334 |
| HPV45 | L2 | 9 | 197 |
| HPV45 | L2 | 9 | 350 |
| HPV45 | L2 | 9 | 299 |
| HPV45 | L2 | 9 | 130 |
| HPV45 | L2 | 9 | 54 |
| HPV45 | L2 | 9 | 181 |
| HPV45 | L2 | 9 | 40 |
| HPV45 | L2 | 9 | 414 |
| HPV45 | L2 | 9 | 96 |
| HPV45 | L2 | 9 | 282 |
| HPV45 | L2 | 9 | 47 |
| HPV45 | L2 | 9 | 35 |
| HPV45 | L2 | 9 | 106 |
| HPV45 | L2 | 9 | 375 |
| HPV45 | L2 | 9 | 349 |
| HPV45 | L2 | 9 | 200 |
| HPV45 | L2 | 9 | 441 |
| HPV45 | L2 | 9 | 280 |
| HPV45 | L2 | 9 | 182 |
| HPV45 | L2 | 9 | 162 |
| HPV45 | L2 | 9 | 256 |
| HPV45 | L2 | 9 | 234 |
| HPV45 | L2 | 9 | 82 |
| HPV45 | L2 | 9 | 390 |
| HPV45 | L2 | 9 | 141 |
| HPV45 | L2 | 9 | 407 |
| HPV45 | L2 | 9 | 168 |
| HPV45 | L2 | 9 | 364 |
| HPV45 | L2 | 9 | 93 |
| HPV45 | L2 | 9 | 294 |
| HPV45 | L2 | 9 | 452 |
| HPV45 | L2 | 9 | 91 |
| HPV45 | L2 | 9 | 319 |
| HPV45 | L2 | 9 | 277 |
| HPV45 | L2 | 9 | 370 |
| HPV45 | L2 | 9 | 180 |
| HPV45 | L2 | 9 | 192 |
| HPV45 | L2 | 9 | 52 |
| HPV45 | L2 | 9 | 377 |
| HPV45 | L2 | 9 | 81 |
| HPV45 | L2 | 9 | 242 |
| HPV45 | L2 | 9 | 249 |
| HPV45 | L2 | 9 | 113 |
| HPV45 | L2 | 9 | 332 |
| HPV45 | L2 | 9 | 210 |
| HPV45 | L2 | 9 | 140 |
| HPV45 | L2 | 9 | 415 |
| HPV45 | L2 | 9 | 147 |
| HPV45 | L2 | 9 | 128 |
| HPV45 | L2 | 9 | 241 |
| HPV45 | L2 | 9 | 429 |
| HPV45 | L2 | 9 | 150 |
| HPV45 | L2 | 9 | 320 |
| HPV45 | L2 | 9 | 401 |
| HPV45 | L2 | 9 | 221 |
| HPV45 | L2 | 9 | 107 |
| HPV45 | L2 | 9 | 84 |
| HPV45 | L2 | 9 | 353 |
| HPV45 | L2 | 9 | 259 |
| HPV45 | L2 | 9 | 323 |
| HPV45 | L2 | 9 | 373 |
| HPV45 | L2 | 9 | 388 |
| HPV56 | E2 | 9 | 2 |
| HPV56 | E2 | 9 | 121 |
| HPV56 | E2 | 9 | 44 |
| HPV56 | E2 | 9 | 126 |
| HPV56 | E2 | 9 | 7 |
| HPV56 | E2 | 9 | 16 |
| HPV56 | E2 | 9 | 95 |
| HPV56 | E2 | 9 | 88 |
| HPV56 | E2 | 9 | 137 |
| HPV56 | E2 | 9 | 131 |
| HPV56 | E2 | 9 | 20 |
| HPV56 | E2 | 9 | 257 |
| HPV56 | E2 | 9 | 62 |
| HPV56 | E2 | 9 | 284 |
| HPV56 | E2 | 9 | 302 |
| HPV56 | E2 | 9 | 261 |
| HPV56 | E2 | 9 | 81 |
| HPV56 | E2 | 9 | 298 |
| HPV56 | E2 | 9 | 75 |
| HPV56 | E2 | 9 | 35 |
| HPV56 | E2 | 9 | 136 |
| HPV56 | E2 | 9 | 278 |
| HPV56 | E2 | 9 | 295 |
| HPV56 | E2 | 9 | 22 |
| HPV56 | E2 | 9 | 150 |
| HPV56 | E2 | 9 | 254 |
| HPV56 | E2 | 9 | 172 |
| HPV56 | E2 | 9 | 148 |
| HPV56 | E2 | 9 | 262 |
| HPV56 | E2 | 9 | 268 |
| HPV56 | E2 | 9 | 156 |
| HPV56 | E2 | 9 | 159 |
| HPV56 | E2 | 9 | 5 |
| HPV56 | E2 | 9 | 260 |
| HPV56 | E6 | 9 | 46 |
| HPV56 | E6 | 9 | 135 |
| HPV56 | E6 | 9 | 63 |
| HPV56 | E6 | 9 | 104 |
| HPV56 | E6 | 9 | 31 |
| HPV56 | E6 | 9 | 86 |
| HPV56 | E6 | 9 | 26 |
| HPV56 | E6 | 9 | 131 |
| HPV56 | E6 | 9 | 27 |
| HPV56 | E6 | 9 | 107 |
| HPV56 | E6 | 9 | 40 |
| HPV56 | E6 | 9 | 99 |
| HPV56 | E6 | 9 | 57 |
| HPV56 | E6 | 9 | 81 |
| HPV56 | E6 | 9 | 94 |
| HPV56 | E6 | 9 | 29 |
| HPV56 | E6 | 9 | 21 |
| HPV56 | E6 | 9 | 65 |
| HPV56 | E6 | 9 | 45 |
| HPV56 | E6 | 9 | 61 |
| HPV56 | E6 | 9 | 35 |

TABLE XIX-continued

DR Supermotif Peptides

| 1 | 2 | 3 | 4 |
|---|---|---|---|
| HPV56 | E6 | 9 | 22 |
| HPV56 | E6 | 9 | 71 |
| HPV56 | E6 | 9 | 24 |
| HPV56 | E6 | 9 | 48 |
| HPV56 | E6 | 9 | 84 |
| HPV56 | E7 | 9 | 1 |
| HPV56 | E7 | 9 | 96 |
| HPV56 | E7 | 9 | 71 |
| HPV56 | E7 | 9 | 61 |
| HPV56 | E7 | 9 | 85 |
| HPV56 | E7 | 9 | 59 |
| HPV56 | E7 | 9 | 63 |
| HPV56 | E7 | 9 | 11 |
| HPV56 | E7 | 9 | 86 |
| HPV56 | E7 | 9 | 94 |
| HPV56 | E7 | 9 | 12 |
| HPV56 | E7 | 9 | 91 |
| HPV56 | E7 | 9 | 90 |
| HPV56 | E7 | 9 | 60 |
| HPV56 | E7 | 9 | 8 |
| HPV56 | E7 | 9 | 89 |
| HPV56 | E7 | 9 | 74 |
| HPV56 | L1 | 9 | 1 |
| HPV56 | L1 | 9 | 3 |
| HPV56 | L1 | 9 | 301 |
| HPV56 | L1 | 9 | 432 |
| HPV56 | L1 | 9 | 29 |
| HPV56 | L1 | 9 | 104 |
| HPV56 | L1 | 9 | 22 |
| HPV56 | L1 | 9 | 222 |
| HPV56 | L1 | 9 | 14 |
| HPV56 | L1 | 9 | 63 |
| HPV56 | L1 | 9 | 484 |
| HPV56 | L1 | 9 | 437 |
| HPV56 | L1 | 9 | 451 |
| HPV56 | L1 | 9 | 407 |
| HPV56 | L1 | 9 | 46 |
| HPV56 | L1 | 9 | 256 |
| HPV56 | L1 | 9 | 242 |
| HPV56 | L1 | 9 | 247 |
| HPV56 | L1 | 9 | 24 |
| HPV56 | L1 | 9 | 36 |
| HPV56 | L1 | 9 | 160 |
| HPV56 | L1 | 9 | 33 |
| HPV56 | L1 | 9 | 482 |
| HPV56 | L1 | 9 | 151 |
| HPV56 | L1 | 9 | 203 |
| HPV56 | L1 | 9 | 141 |
| HPV56 | L1 | 9 | 363 |
| HPV56 | L1 | 9 | 147 |
| HPV56 | L1 | 9 | 254 |
| HPV56 | L1 | 9 | 119 |
| HPV56 | L1 | 9 | 416 |
| HPV56 | L1 | 9 | 96 |
| HPV56 | L1 | 9 | 48 |
| HPV56 | L1 | 9 | 479 |
| HPV56 | L1 | 9 | 453 |
| HPV56 | L1 | 9 | 477 |
| HPV56 | L1 | 9 | 21 |
| HPV56 | L1 | 9 | 193 |
| HPV56 | L1 | 9 | 435 |
| HPV56 | L1 | 9 | 427 |
| HPV56 | L1 | 9 | 400 |
| HPV56 | L1 | 9 | 388 |
| HPV56 | L1 | 9 | 424 |
| HPV56 | L1 | 9 | 8 |
| HPV56 | L1 | 9 | 9 |
| HPV56 | L1 | 9 | 439 |
| HPV56 | L1 | 9 | 183 |
| HPV56 | L1 | 9 | 345 |
| HPV56 | L1 | 9 | 47 |
| HPV56 | L1 | 9 | 229 |
| HPV56 | L1 | 9 | 309 |
| HPV56 | L1 | 9 | 224 |
| HPV56 | L1 | 9 | 258 |
| HPV56 | L1 | 9 | 7 |
| HPV56 | L1 | 9 | 117 |
| HPV56 | L1 | 9 | 324 |
| HPV56 | L1 | 9 | 53 |
| HPV56 | L1 | 9 | 132 |
| HPV56 | L1 | 9 | 497 |
| HPV56 | L1 | 9 | 409 |
| HPV56 | L1 | 9 | 192 |
| HPV56 | L1 | 9 | 365 |
| HPV56 | L1 | 9 | 190 |
| HPV56 | L1 | 9 | 106 |
| HPV56 | L1 | 9 | 502 |
| HPV56 | L1 | 9 | 134 |
| HPV56 | L1 | 9 | 333 |
| HPV56 | L1 | 9 | 70 |
| HPV56 | L1 | 9 | 78 |
| HPV56 | L1 | 9 | 168 |
| HPV56 | L1 | 9 | 325 |
| HPV56 | L1 | 9 | 492 |
| HPV56 | L1 | 9 | 376 |
| HPV56 | L1 | 9 | 214 |
| HPV56 | L1 | 9 | 62 |
| HPV56 | L1 | 9 | 385 |
| HPV56 | L1 | 9 | 199 |
| HPV56 | L1 | 9 | 69 |
| HPV56 | L1 | 9 | 403 |
| HPV56 | L1 | 9 | 32 |
| HPV56 | L1 | 9 | 411 |
| HPV56 | L1 | 9 | 109 |
| HPV56 | L1 | 9 | 27 |
| HPV56 | L1 | 9 | 56 |
| HPV56 | L1 | 9 | 368 |
| HPV56 | L1 | 9 | 284 |
| HPV56 | L1 | 9 | 268 |
| HPV56 | L1 | 9 | 107 |
| HPV56 | L1 | 9 | 454 |
| HPV56 | L1 | 9 | 87 |
| HPV56 | L2 | 9 | 1 |
| HPV56 | L2 | 9 | 2 |
| HPV56 | L2 | 9 | 44 |
| HPV56 | L2 | 9 | 332 |
| HPV56 | L2 | 9 | 361 |
| HPV56 | L2 | 9 | 249 |
| HPV56 | L2 | 9 | 409 |
| HPV56 | L2 | 9 | 45 |
| HPV56 | L2 | 9 | 241 |
| HPV56 | L2 | 9 | 276 |
| HPV56 | L2 | 9 | 263 |
| HPV56 | L2 | 9 | 334 |
| HPV56 | L2 | 9 | 197 |
| HPV56 | L2 | 9 | 112 |
| HPV56 | L2 | 9 | 347 |
| HPV56 | L2 | 9 | 234 |
| HPV56 | L2 | 9 | 221 |
| HPV56 | L2 | 9 | 299 |
| HPV56 | L2 | 9 | 54 |
| HPV56 | L2 | 9 | 130 |
| HPV56 | L2 | 9 | 181 |
| HPV56 | L2 | 9 | 437 |
| HPV56 | L2 | 9 | 431 |
| HPV56 | L2 | 9 | 375 |
| HPV56 | L2 | 9 | 321 |
| HPV56 | L2 | 9 | 192 |
| HPV56 | L2 | 9 | 47 |
| HPV56 | L2 | 9 | 218 |
| HPV56 | L2 | 9 | 84 |
| HPV56 | L2 | 9 | 106 |
| HPV56 | L2 | 9 | 280 |
| HPV56 | L2 | 9 | 200 |
| HPV56 | L2 | 9 | 182 |
| HPV56 | L2 | 9 | 256 |
| HPV56 | L2 | 9 | 162 |
| HPV56 | L2 | 9 | 242 |
| HPV56 | L2 | 9 | 141 |
| HPV56 | L2 | 9 | 277 |

TABLE XIX-continued

DR Supermotif Peptides

| 1 | 2 | 3 | 4 |
|---|---|---|---|
| HPV56 | L2 | 9 | 408 |
| HPV56 | L2 | 9 | 93 |
| HPV56 | L2 | 9 | 163 |
| HPV56 | L2 | 9 | 168 |
| HPV56 | L2 | 9 | 81 |
| HPV56 | L2 | 9 | 40 |
| HPV56 | L2 | 9 | 338 |
| HPV56 | L2 | 9 | 71 |
| HPV56 | L2 | 9 | 294 |
| HPV56 | L2 | 9 | 231 |
| HPV56 | L2 | 9 | 453 |
| HPV56 | L2 | 9 | 91 |
| HPV56 | L2 | 9 | 319 |
| HPV56 | L2 | 9 | 373 |
| HPV56 | L2 | 9 | 128 |
| HPV56 | L2 | 9 | 180 |
| HPV56 | L2 | 9 | 265 |
| HPV56 | L2 | 9 | 366 |
| HPV56 | L2 | 9 | 150 |
| HPV56 | L2 | 9 | 82 |
| HPV56 | L2 | 9 | 23 |
| HPV56 | L2 | 9 | 210 |
| HPV56 | L2 | 9 | 202 |
| HPV56 | L2 | 9 | 176 |
| HPV56 | L2 | 9 | 430 |
| HPV56 | L2 | 9 | 382 |
| HPV56 | L2 | 9 | 161 |
| HPV56 | L2 | 9 | 140 |
| HPV56 | L2 | 9 | 402 |
| HPV56 | L2 | 9 | 18 |
| HPV56 | L2 | 9 | 152 |
| HPV56 | L2 | 9 | 418 |
| HPV56 | L2 | 9 | 96 |
| HPV56 | L2 | 9 | 320 |
| HPV56 | L2 | 9 | 143 |
| HPV56 | L2 | 9 | 107 |
| HPV56 | L2 | 9 | 354 |
| HPV56 | L2 | 9 | 74 |

TABLE XIX A

HPV6A
DR Supermotif Peptides

| 2 | 3 | 4 |
|---|---|---|
| L2 | 9 | 44 |
| E1 | 9 | 102 |
| L2 | 9 | 333 |
| L1 | 9 | 383 |
| E5 | 9 | 26 |
| L1 | 9 | 263 |
| E1 | 9 | 196 |
| E2 | 9 | 49 |
| E1 | 9 | 403 |
| E2 | 9 | 253 |
| E1 | 9 | 557 |
| E5 | 9 | 82 |
| E1 | 9 | 322 |
| L1 | 9 | 206 |
| E1 | 9 | 340 |
| L2 | 9 | 185 |
| E4 | 9 | 6 |
| E1 | 9 | 393 |
| E6 | 9 | 127 |
| E2 | 9 | 243 |
| E1 | 9 | 333 |
| E1 | 9 | 274 |
| L1 | 9 | 344 |
| E1 | 9 | 218 |
| E2 | 9 | 164 |
| E1 | 9 | 204 |
| E2 | 9 | 251 |
| L1 | 9 | 184 |
| E1 | 9 | 413 |
| E1 | 9 | 17 |
| E1 | 9 | 532 |
| L1 | 9 | 27 |
| E5 | 9 | 42 |
| L2 | 9 | 407 |
| E7 | 9 | 13 |
| L1 | 9 | 369 |
| E1 | 9 | 306 |
| L2 | 9 | 45 |
| E1 | 9 | 137 |
| E1 | 9 | 56 |
| E1 | 9 | 356 |
| L1 | 9 | 87 |
| L1 | 9 | 9 |
| E2 | 9 | 146 |
| E6 | 9 | 102 |
| L1 | 9 | 218 |
| L2 | 9 | 146 |
| E2 | 9 | 139 |
| L1 | 9 | 399 |
| E1 | 9 | 239 |
| L2 | 9 | 277 |
| L1 | 9 | 413 |
| E1 | 9 | 577 |
| L2 | 9 | 335 |
| L2 | 9 | 195 |
| E2 | 9 | 77 |
| L2 | 9 | 165 |
| L2 | 9 | 113 |
| E1 | 9 | 376 |
| E2 | 9 | 83 |
| E2 | 9 | 99 |
| E2 | 9 | 188 |
| L1 | 9 | 446 |
| E2 | 9 | 208 |
| E2 | 9 | 89 |
| L1 | 9 | 209 |
| L1 | 9 | 246 |
| E5 | 9 | 70 |
| L1 | 9 | 204 |
| E5 | 9 | 43 |
| E1 | 9 | 464 |
| E2 | 9 | 167 |
| E4 | 9 | 24 |
| E2 | 9 | 349 |
| E1 | 9 | 255 |
| E1 | 9 | 641 |
| L2 | 9 | 419 |
| L2 | 9 | 259 |
| L1 | 9 | 267 |
| E1 | 9 | 244 |
| L2 | 9 | 131 |
| L2 | 9 | 179 |
| E1 | 9 | 486 |
| L1 | 9 | 104 |
| L1 | 9 | 147 |
| L1 | 9 | 325 |
| L2 | 9 | 405 |
| L1 | 9 | 110 |
| E6 | 9 | 138 |
| E7 | 9 | 6 |
| L2 | 9 | 434 |
| L1 | 9 | 286 |
| E2 | 9 | 192 |
| L2 | 9 | 416 |
| E1 | 9 | 150 |
| E1 | 9 | 500 |
| L2 | 9 | 54 |
| E1 | 9 | 19 |
| E1 | 9 | 139 |
| E6 | 9 | 61 |

TABLE XIX A-continued

HPV6A DR Supermotif Peptides

| 2 | 3 | 4 |
|---|---|---|
| L1 | 9 | 67 |
| E1 | 9 | 418 |
| E2 | 9 | 41 |
| E6 | 9 | 82 |
| E7 | 9 | 54 |
| L2 | 9 | 129 |
| E2 | 9 | 56 |
| L2 | 9 | 180 |
| E1 | 9 | 555 |
| E4 | 9 | 19 |
| E1 | 9 | 61 |
| L2 | 9 | 40 |
| L1 | 9 | 49 |
| E2 | 9 | 311 |
| E2 | 9 | 152 |
| E7 | 9 | 8 |
| L2 | 9 | 321 |
| E5 | 9 | 25 |
| E1 | 9 | 477 |
| E1 | 9 | 224 |
| L1 | 9 | 373 |
| L1 | 9 | 389 |
| L2 | 9 | 320 |
| E5 | 9 | 24 |
| L2 | 9 | 282 |
| L2 | 9 | 47 |
| E5 | 9 | 20 |
| E6 | 9 | 32 |
| E1 | 9 | 458 |
| L2 | 9 | 35 |
| E6 | 9 | 105 |
| E7 | 9 | 79 |
| E1 | 9 | 227 |
| E5 | 9 | 40 |
| E1 | 9 | 495 |
| L2 | 9 | 107 |
| E5 | 9 | 37 |
| E6 | 9 | 46 |
| E6 | 9 | 126 |
| E1 | 9 | 614 |
| E7 | 9 | 12 |
| E1 | 9 | 216 |
| L1 | 9 | 82 |
| E1 | 9 | 463 |
| E2 | 9 | 31 |
| E6 | 9 | 38 |
| E1 | 9 | 474 |
| L2 | 9 | 82 |
| E6 | 9 | 97 |
| E7 | 9 | 52 |
| E1 | 9 | 427 |
| L1 | 9 | 216 |
| E1 | 9 | 487 |
| E1 | 9 | 521 |
| E6 | 9 | 55 |
| E1 | 9 | 579 |
| L1 | 9 | 155 |
| E7 | 9 | 90 |
| E4 | 9 | 72 |
| L2 | 9 | 198 |
| E6 | 9 | 101 |
| L1 | 9 | 397 |
| E1 | 9 | 199 |
| E2 | 9 | 19 |
| E7 | 9 | 87 |
| L2 | 9 | 232 |
| E1 | 9 | 494 |
| E5 | 9 | 36 |
| E2 | 9 | 18 |
| E5 | 9 | 58 |
| E5 | 9 | 54 |
| E1 | 9 | 301 |
| E5 | 9 | 72 |
| E1 | 9 | 279 |
| E5 | 9 | 59 |
| E5 | 9 | 55 |
| E2 | 9 | 350 |
| E5 | 9 | 21 |
| E5 | 9 | 68 |
| L1 | 9 | 370 |
| E1 | 9 | 514 |
| E1 | 9 | 221 |
| E2 | 9 | 54 |
| E1 | 9 | 558 |
| E5 | 9 | 52 |
| E5 | 9 | 73 |
| E1 | 9 | 282 |
| E2 | 9 | 60 |
| E5 | 9 | 56 |
| E4 | 9 | 8 |
| E1 | 9 | 323 |
| L2 | 9 | 1 |
| L1 | 9 | 386 |
| L2 | 9 | 280 |
| E1 | 9 | 536 |
| E2 | 9 | 132 |
| E2 | 9 | 92 |
| E6 | 9 | 1 |
| E5 | 9 | 1 |
| E5 | 9 | 3 |
| E5 | 9 | 4 |
| E7 | 9 | 1 |
| E6 | 9 | 27 |
| E2 | 9 | 59 |
| L1 | 9 | 362 |
| E1 | 9 | 540 |
| L1 | 9 | 2 |
| E1 | 9 | 603 |
| E6 | 9 | 133 |
| E6 | 9 | 33 |
| L2 | 9 | 398 |
| L2 | 9 | 178 |
| E1 | 9 | 454 |
| L1 | 9 | 34 |
| E2 | 9 | 30 |
| L1 | 9 | 307 |
| L1 | 9 | 58 |
| L1 | 9 | 441 |
| E6 | 9 | 24 |
| L1 | 9 | 340 |
| L2 | 9 | 160 |
| L2 | 9 | 254 |
| E4 | 9 | 60 |
| E1 | 9 | 398 |
| L1 | 9 | 176 |
| L2 | 9 | 388 |
| L1 | 9 | 145 |
| E7 | 9 | 67 |
| L2 | 9 | 142 |
| E5 | 9 | 81 |
| E4 | 9 | 66 |
| L1 | 9 | 271 |
| E1 | 9 | 341 |
| L1 | 9 | 220 |
| L1 | 9 | 186 |
| E5 | 9 | 67 |
| L1 | 9 | 80 |
| L1 | 9 | 17 |
| E1 | 9 | 313 |
| E1 | 9 | 564 |
| E4 | 9 | 35 |
| L2 | 9 | 93 |
| E5 | 9 | 22 |
| E5 | 9 | 8 |
| L2 | 9 | 94 |
| E4 | 9 | 74 |
| E1 | 9 | 402 |
| E1 | 9 | 67 |

TABLE XIX A-continued

HPV6A
DR Supermotif Peptides

| 2 | 3 | 4 |
|---|---|---|
| E5 | 9 | 69 |
| L1 | 9 | 371 |
| E1 | 9 | 256 |
| L1 | 9 | 154 |
| L1 | 9 | 327 |
| E7 | 9 | 84 |
| E2 | 9 | 51 |
| E1 | 9 | 308 |
| E1 | 9 | 530 |
| E1 | 9 | 515 |
| E2 | 9 | 347 |
| L2 | 9 | 247 |
| L1 | 9 | 469 |
| L1 | 9 | 152 |
| E1 | 9 | 347 |
| E1 | 9 | 366 |
| E2 | 9 | 186 |
| L1 | 9 | 459 |
| L1 | 9 | 69 |
| E6 | 9 | 106 |
| E1 | 9 | 284 |
| E6 | 9 | 59 |
| L2 | 9 | 294 |
| E2 | 9 | 360 |
| E2 | 9 | 312 |
| L2 | 9 | 319 |
| L2 | 9 | 450 |
| E1 | 9 | 87 |
| E7 | 9 | 69 |
| L1 | 9 | 97 |
| E1 | 9 | 541 |
| L2 | 9 | 159 |
| L1 | 9 | 484 |
| L2 | 9 | 92 |
| E1 | 9 | 346 |
| E1 | 9 | 127 |
| E1 | 9 | 291 |
| E1 | 9 | 327 |
| L1 | 9 | 479 |
| L2 | 9 | 71 |
| L1 | 9 | 32 |
| L2 | 9 | 224 |
| L2 | 9 | 114 |
| E5 | 9 | 41 |
| L2 | 9 | 371 |
| L2 | 9 | 87 |
| L1 | 9 | 295 |
| E1 | 9 | 510 |
| L2 | 9 | 190 |
| E5 | 9 | 33 |
| L1 | 9 | 378 |
| L2 | 9 | 52 |
| E1 | 9 | 110 |
| E1 | 9 | 92 |
| L1 | 9 | 421 |
| L2 | 9 | 229 |
| L1 | 9 | 42 |
| L1 | 9 | 454 |
| E1 | 9 | 509 |
| L1 | 9 | 287 |
| E1 | 9 | 621 |
| E2 | 9 | 319 |
| E2 | 9 | 26 |
| E5 | 9 | 17 |
| L1 | 9 | 338 |
| L2 | 9 | 213 |
| E2 | 9 | 214 |
| E2 | 9 | 193 |
| E5 | 9 | 48 |
| L2 | 9 | 263 |
| E6 | 9 | 48 |
| E2 | 9 | 101 |
| L2 | 9 | 412 |
| L2 | 9 | 23 |

TABLE XIX A-continued

HPV6A
DR Supermotif Peptides

| 2 | 3 | 4 |
|---|---|---|
| E2 | 9 | 145 |
| E6 | 9 | 22 |
| E1 | 9 | 589 |
| L2 | 9 | 200 |
| L2 | 9 | 427 |
| E1 | 9 | 18 |
| L2 | 9 | 72 |
| E7 | 9 | 89 |
| E5 | 9 | 18 |
| E5 | 9 | 74 |
| E6 | 9 | 29 |
| E1 | 9 | 272 |
| L1 | 9 | 33 |
| L2 | 9 | 141 |
| E2 | 9 | 206 |
| L2 | 9 | 18 |
| L2 | 9 | 383 |
| L1 | 9 | 95 |
| E4 | 9 | 81 |
| E5 | 9 | 16 |
| L1 | 9 | 191 |
| E5 | 9 | 47 |
| E5 | 9 | 65 |
| L2 | 9 | 154 |
| E2 | 9 | 119 |
| L1 | 9 | 11 |
| E2 | 9 | 321 |
| L1 | 9 | 415 |
| E1 | 9 | 320 |
| E1 | 9 | 242 |
| E2 | 9 | 256 |
| E5 | 9 | 29 |
| E7 | 9 | 40 |
| E1 | 9 | 51 |
| E1 | 9 | 23 |
| L1 | 9 | 365 |
| E6 | 9 | 117 |
| L2 | 9 | 97 |
| L1 | 9 | 72 |
| E7 | 9 | 15 |
| E2 | 9 | 44 |
| E5 | 9 | 51 |
| E2 | 9 | 62 |
| E1 | 9 | 82 |
| E1 | 9 | 447 |
| E7 | 9 | 82 |
| E5 | 9 | 32 |
| L1 | 9 | 20 |
| L2 | 9 | 108 |
| L2 | 9 | 422 |
| L2 | 9 | 367 |
| E1 | 9 | 587 |
| L1 | 9 | 330 |
| E5 | 9 | 28 |
| E1 | 9 | 275 |
| E1 | 9 | 613 |
| E2 | 9 | 36 |
| E4 | 9 | 69 |
| E2 | 9 | 137 |
| L1 | 9 | 126 |
| L1 | 9 | 439 |
| E1 | 9 | 580 |
| E4 | 9 | 15 |
| E5 | 9 | 57 |
| L1 | 9 | 230 |
| E4 | 9 | 22 |
| L1 | 9 | 70 |
| L1 | 9 | 416 |
| L2 | 9 | 299 |
| E5 | 9 | 46 |
| E4 | 9 | 9 |
| E2 | 9 | 134 |

TABLE XIX B

HPV6B DR Supermotif Peptides

| 2 | 3 | 4 |
|---|---|---|
| L2 | 9 | 44 |
| E1 | 9 | 102 |
| L2 | 9 | 333 |
| L1 | 9 | 383 |
| E5B | 9 | 24 |
| E5A | 9 | 26 |
| L1 | 9 | 263 |
| E1 | 9 | 196 |
| E2 | 9 | 49 |
| E1 | 9 | 403 |
| E2 | 9 | 253 |
| E1 | 9 | 557 |
| E5A | 9 | 82 |
| E1 | 9 | 322 |
| L1 | 9 | 206 |
| E1 | 9 | 340 |
| E4 | 9 | 6 |
| L2 | 9 | 185 |
| E4 | 9 | 16 |
| E1 | 9 | 393 |
| E6 | 9 | 127 |
| E2 | 9 | 243 |
| E1 | 9 | 333 |
| E1 | 9 | 274 |
| L1 | 9 | 344 |
| E1 | 9 | 218 |
| E2 | 9 | 164 |
| E1 | 9 | 204 |
| E2 | 9 | 251 |
| L1 | 9 | 184 |
| E1 | 9 | 413 |
| E1 | 9 | 17 |
| E1 | 9 | 532 |
| L1 | 9 | 27 |
| E5B | 9 | 58 |
| L2 | 9 | 406 |
| E7 | 9 | 13 |
| L1 | 9 | 369 |
| L2 | 9 | 45 |
| E1 | 9 | 137 |
| E1 | 9 | 56 |
| E1 | 9 | 356 |
| L1 | 9 | 87 |
| L1 | 9 | 9 |
| E5B | 9 | 14 |
| E2 | 9 | 146 |
| E6 | 9 | 102 |
| L1 | 9 | 218 |
| L2 | 9 | 146 |
| E2 | 9 | 139 |
| L1 | 9 | 399 |
| E1 | 9 | 239 |
| L2 | 9 | 277 |
| E1 | 9 | 577 |
| L1 | 9 | 413 |
| E5A | 9 | 42 |
| L2 | 9 | 335 |
| L2 | 9 | 195 |
| E2 | 9 | 77 |
| E1 | 9 | 306 |
| L2 | 9 | 165 |
| L2 | 9 | 113 |
| E1 | 9 | 376 |
| E2 | 9 | 83 |
| E2 | 9 | 99 |
| E2 | 9 | 188 |
| L1 | 9 | 446 |
| E2 | 9 | 208 |
| E2 | 9 | 89 |
| L1 | 9 | 209 |
| L1 | 9 | 246 |
| E5A | 9 | 70 |
| L1 | 9 | 204 |
| E5A | 9 | 43 |
| E1 | 9 | 464 |
| E2 | 9 | 167 |
| E2 | 9 | 349 |
| E4 | 9 | 34 |
| E1 | 9 | 255 |
| E1 | 9 | 641 |
| L2 | 9 | 418 |
| E5B | 9 | 13 |
| L2 | 9 | 259 |
| L1 | 9 | 267 |
| E1 | 9 | 244 |
| L2 | 9 | 131 |
| L2 | 9 | 179 |
| E1 | 9 | 486 |
| E4 | 9 | 10 |
| L1 | 9 | 104 |
| E5B | 9 | 31 |
| E5B | 9 | 18 |
| L1 | 9 | 147 |
| L1 | 9 | 325 |
| L2 | 9 | 404 |
| L1 | 9 | 110 |
| E6 | 9 | 138 |
| E7 | 9 | 6 |
| L2 | 9 | 434 |
| L1 | 9 | 286 |
| E2 | 9 | 192 |
| L2 | 9 | 415 |
| E1 | 9 | 150 |
| E1 | 9 | 500 |
| L2 | 9 | 54 |
| E1 | 9 | 19 |
| E1 | 9 | 139 |
| E6 | 9 | 61 |
| L1 | 9 | 67 |
| E1 | 9 | 418 |
| E2 | 9 | 41 |
| E6 | 9 | 82 |
| E7 | 9 | 54 |
| L2 | 9 | 129 |
| E2 | 9 | 56 |
| L2 | 9 | 180 |
| E1 | 9 | 555 |
| E2 | 9 | 30 |
| E4 | 9 | 29 |
| E1 | 9 | 61 |
| L2 | 9 | 40 |
| L1 | 9 | 49 |
| E2 | 9 | 311 |
| E2 | 9 | 152 |
| E7 | 9 | 8 |
| E2 | 9 | 186 |
| L2 | 9 | 321 |
| E5A | 9 | 25 |
| E1 | 9 | 477 |
| E1 | 9 | 224 |
| L1 | 9 | 373 |
| L1 | 9 | 389 |
| L2 | 9 | 320 |
| E5A | 9 | 24 |
| L2 | 9 | 282 |
| L2 | 9 | 47 |
| E5A | 9 | 20 |
| E6 | 9 | 32 |
| E1 | 9 | 458 |
| L2 | 9 | 35 |
| E6 | 9 | 105 |
| E7 | 9 | 79 |
| E1 | 9 | 227 |
| E5A | 9 | 40 |
| E1 | 9 | 495 |
| E5B | 9 | 26 |
| L2 | 9 | 107 |
| E5A | 9 | 37 |

TABLE XIX B-continued

HPV6B
DR Supermotif Peptides

| 2 | 3 | 4 |
|---|---|---|
| E6 | 9 | 46 |
| E6 | 9 | 126 |
| E1 | 9 | 614 |
| E7 | 9 | 12 |
| E1 | 9 | 216 |
| L1 | 9 | 82 |
| E1 | 9 | 463 |
| E2 | 9 | 31 |
| E6 | 9 | 38 |
| E1 | 9 | 474 |
| L2 | 9 | 82 |
| E6 | 9 | 97 |
| E7 | 9 | 52 |
| E1 | 9 | 427 |
| L1 | 9 | 216 |
| E1 | 9 | 487 |
| E1 | 9 | 521 |
| E6 | 9 | 55 |
| E1 | 9 | 579 |
| E5B | 9 | 22 |
| L1 | 9 | 155 |
| E4 | 9 | 82 |
| L2 | 9 | 198 |
| E6 | 9 | 101 |
| E2 | 9 | 350 |
| L1 | 9 | 397 |
| E1 | 9 | 199 |
| E2 | 9 | 19 |
| E7 | 9 | 87 |
| L2 | 9 | 232 |
| E1 | 9 | 494 |
| E5A | 9 | 36 |
| E2 | 9 | 18 |
| E5B | 9 | 32 |
| E5A | 9 | 58 |
| E5A | 9 | 54 |
| E1 | 9 | 301 |
| E1 | 9 | 282 |
| E5A | 9 | 72 |
| E1 | 9 | 279 |
| E5A | 9 | 59 |
| E5A | 9 | 55 |
| E7 | 9 | 90 |
| E5A | 9 | 21 |
| E5A | 9 | 68 |
| L1 | 9 | 370 |
| E1 | 9 | 514 |
| E1 | 9 | 221 |
| E2 | 9 | 54 |
| E1 | 9 | 558 |
| E5A | 9 | 52 |
| E5A | 9 | 73 |
| E5B | 9 | 19 |
| E5A | 9 | 60 |
| E5A | 9 | 56 |
| E4 | 9 | 18 |
| E1 | 9 | 323 |
| L2 | 9 | 1 |
| L1 | 9 | 386 |
| L2 | 9 | 280 |
| E1 | 9 | 536 |
| E2 | 9 | 132 |
| E2 | 9 | 92 |
| E6 | 9 | 1 |
| E5A | 9 | 1 |
| E5A | 9 | 3 |
| E5A | 9 | 4 |
| E4 | 9 | 1 |
| E7 | 9 | 1 |
| E6 | 9 | 27 |
| E2 | 9 | 59 |
| L1 | 9 | 362 |
| E1 | 9 | 540 |
| L1 | 9 | 2 |
| E1 | 9 | 603 |
| E6 | 9 | 133 |
| E6 | 9 | 33 |
| L2 | 9 | 397 |
| E2 | 9 | 145 |
| L2 | 9 | 178 |
| E1 | 9 | 454 |
| L1 | 9 | 34 |
| L1 | 9 | 307 |
| L1 | 9 | 58 |
| L1 | 9 | 441 |
| E6 | 9 | 24 |
| L1 | 9 | 340 |
| L2 | 9 | 160 |
| L2 | 9 | 254 |
| E1 | 9 | 398 |
| E4 | 9 | 70 |
| L1 | 9 | 176 |
| L2 | 9 | 388 |
| L1 | 9 | 145 |
| E7 | 9 | 67 |
| L2 | 9 | 142 |
| E5A | 9 | 81 |
| E4 | 9 | 76 |
| L1 | 9 | 271 |
| E1 | 9 | 341 |
| L1 | 9 | 220 |
| L1 | 9 | 186 |
| E5A | 9 | 67 |
| L1 | 9 | 80 |
| L1 | 9 | 17 |
| E1 | 9 | 313 |
| E1 | 9 | 564 |
| E4 | 9 | 45 |
| L2 | 9 | 93 |
| E5A | 9 | 22 |
| E5A | 9 | 8 |
| L2 | 9 | 94 |
| E4 | 9 | 84 |
| E1 | 9 | 402 |
| E1 | 9 | 67 |
| E5A | 9 | 69 |
| L1 | 9 | 371 |
| E1 | 9 | 256 |
| L1 | 9 | 154 |
| L1 | 9 | 327 |
| E7 | 9 | 84 |
| E2 | 9 | 51 |
| E1 | 9 | 308 |
| E1 | 9 | 530 |
| E1 | 9 | 515 |
| E2 | 9 | 347 |
| L2 | 9 | 247 |
| L1 | 9 | 469 |
| L1 | 9 | 152 |
| E1 | 9 | 347 |
| E1 | 9 | 366 |
| L1 | 9 | 459 |
| L1 | 9 | 69 |
| E6 | 9 | 106 |
| E1 | 9 | 284 |
| E6 | 9 | 59 |
| L2 | 9 | 294 |
| E2 | 9 | 312 |
| L2 | 9 | 319 |
| L2 | 9 | 450 |
| E1 | 9 | 87 |
| E7 | 9 | 69 |
| L1 | 9 | 97 |
| E1 | 9 | 541 |
| L2 | 9 | 159 |
| L1 | 9 | 484 |
| L2 | 9 | 92 |
| E1 | 9 | 346 |

TABLE XIX B-continued

HPV6B
DR Supermotif Peptides

| 2 | 3 | 4 |
|---|---|---|
| E1 | 9 | 127 |
| E1 | 9 | 291 |
| E1 | 9 | 327 |
| L1 | 9 | 479 |
| L2 | 9 | 71 |
| L1 | 9 | 32 |
| L2 | 9 | 224 |
| L2 | 9 | 114 |
| L2 | 9 | 371 |
| E5A | 9 | 41 |
| L2 | 9 | 87 |
| L1 | 9 | 295 |
| E1 | 9 | 510 |
| E2 | 9 | 360 |
| L2 | 9 | 190 |
| E5A | 9 | 33 |
| L1 | 9 | 378 |
| L2 | 9 | 52 |
| E1 | 9 | 110 |
| E1 | 9 | 92 |
| L1 | 9 | 421 |
| L2 | 9 | 229 |
| L1 | 9 | 42 |
| L1 | 9 | 454 |
| E1 | 9 | 509 |
| L1 | 9 | 287 |
| E1 | 9 | 621 |
| E2 | 9 | 319 |
| E2 | 9 | 26 |
| E5A | 9 | 17 |
| L1 | 9 | 338 |
| L2 | 9 | 213 |
| E2 | 9 | 214 |
| E2 | 9 | 193 |
| E5A | 9 | 48 |
| L2 | 9 | 263 |
| E6 | 9 | 48 |
| E2 | 9 | 101 |
| L2 | 9 | 411 |
| L2 | 9 | 23 |
| E5B | 9 | 7 |
| E5A | 9 | 18 |
| E6 | 9 | 22 |
| E1 | 9 | 589 |
| L2 | 9 | 200 |
| L2 | 9 | 427 |
| E1 | 9 | 18 |
| L2 | 9 | 72 |
| E5A | 9 | 74 |
| E7 | 9 | 89 |
| E6 | 9 | 29 |
| E1 | 9 | 272 |
| L1 | 9 | 33 |
| L2 | 9 | 141 |
| L2 | 9 | 422 |
| E2 | 9 | 206 |
| L2 | 9 | 18 |
| L2 | 9 | 383 |
| L1 | 9 | 95 |
| E4 | 9 | 91 |
| E5A | 9 | 16 |
| E2 | 9 | 222 |
| L1 | 9 | 191 |
| E5A | 9 | 47 |
| E1 | 9 | 235 |
| E5A | 9 | 65 |
| L2 | 9 | 154 |
| E2 | 9 | 119 |
| L1 | 9 | 11 |
| E2 | 9 | 321 |
| L1 | 9 | 415 |
| E1 | 9 | 320 |
| E1 | 9 | 242 |
| E2 | 9 | 256 |

TABLE XIX B-continued

HPV6B
DR Supermotif Peptides

| 2 | 3 | 4 |
|---|---|---|
| E5A | 9 | 29 |
| E7 | 9 | 40 |
| E1 | 9 | 51 |
| E1 | 9 | 23 |
| L1 | 9 | 365 |
| E6 | 9 | 117 |
| L2 | 9 | 97 |
| L1 | 9 | 72 |
| E5B | 9 | 27 |
| E7 | 9 | 15 |
| E2 | 9 | 44 |
| E5A | 9 | 51 |
| E2 | 9 | 62 |
| E1 | 9 | 82 |
| E1 | 9 | 447 |
| E7 | 9 | 82 |
| E5A | 9 | 32 |
| L1 | 9 | 20 |
| L2 | 9 | 108 |
| L2 | 9 | 367 |
| E1 | 9 | 587 |
| L1 | 9 | 330 |
| E5A | 9 | 28 |
| E2 | 9 | 352 |
| E1 | 9 | 275 |
| E1 | 9 | 613 |
| E2 | 9 | 36 |
| E5B | 9 | 16 |
| E4 | 9 | 79 |
| L1 | 9 | 126 |
| L1 | 9 | 439 |
| E1 | 9 | 580 |
| E4 | 9 | 25 |
| E5A | 9 | 57 |
| L1 | 9 | 230 |
| E4 | 9 | 32 |
| L1 | 9 | 70 |
| L1 | 9 | 416 |
| L2 | 9 | 299 |
| E5A | 9 | 46 |
| E4 | 9 | 19 |
| E2 | 9 | 134 |

TABLE XIX C

HPV11
DR Supermotif Peptides

| 2 | 3 | 4 |
|---|---|---|
| L2 | 9 | 43 |
| L2 | 9 | 332 |
| L1 | 9 | 384 |
| E5A | 9 | 26 |
| E5B | 9 | 25 |
| E5A | 9 | 82 |
| L1 | 9 | 264 |
| L2 | 9 | 71 |
| E2 | 9 | 49 |
| E1 | 9 | 403 |
| E1 | 9 | 557 |
| E1 | 9 | 322 |
| L1 | 9 | 207 |
| E1 | 9 | 102 |
| E1 | 9 | 340 |
| L2 | 9 | 184 |
| E2 | 9 | 224 |
| E4 | 9 | 16 |
| E1 | 9 | 393 |
| L1 | 9 | 287 |
| E1 | 9 | 333 |

TABLE XIX C-continued

HPV11 DR Supermotif Peptides

| 2 | 3 | 4 |
|---|---|---|
| E5A | 9 | 28 |
| E1 | 9 | 274 |
| E6 | 9 | 48 |
| L1 | 9 | 345 |
| E1 | 9 | 218 |
| E2 | 9 | 164 |
| E2 | 9 | 38 |
| L1 | 9 | 185 |
| E1 | 9 | 413 |
| E1 | 9 | 509 |
| E1 | 9 | 17 |
| E1 | 9 | 532 |
| L1 | 9 | 27 |
| E5A | 9 | 42 |
| L2 | 9 | 194 |
| L2 | 9 | 402 |
| E7 | 9 | 13 |
| E7 | 9 | 84 |
| L1 | 9 | 370 |
| L1 | 9 | 442 |
| L2 | 9 | 44 |
| E1 | 9 | 56 |
| E4 | 9 | 69 |
| E1 | 9 | 137 |
| E1 | 9 | 356 |
| L1 | 9 | 87 |
| E2 | 9 | 262 |
| L1 | 9 | 9 |
| E2 | 9 | 146 |
| E2 | 9 | 99 |
| L1 | 9 | 219 |
| L2 | 9 | 145 |
| L1 | 9 | 400 |
| E1 | 9 | 239 |
| L2 | 9 | 276 |
| E2 | 9 | 128 |
| L1 | 9 | 414 |
| E1 | 9 | 577 |
| L2 | 9 | 334 |
| E2 | 9 | 77 |
| E1 | 9 | 306 |
| L2 | 9 | 164 |
| L2 | 9 | 112 |
| E1 | 9 | 376 |
| E2 | 9 | 188 |
| L1 | 9 | 447 |
| E2 | 9 | 208 |
| L1 | 9 | 210 |
| E5A | 9 | 70 |
| L1 | 9 | 247 |
| L1 | 9 | 205 |
| E5B | 9 | 19 |
| E1 | 9 | 255 |
| E1 | 9 | 641 |
| L2 | 9 | 414 |
| L2 | 9 | 298 |
| E5B | 9 | 23 |
| E5A | 9 | 43 |
| E5B | 9 | 14 |
| L2 | 9 | 258 |
| E1 | 9 | 174 |
| L1 | 9 | 268 |
| E1 | 9 | 244 |
| L2 | 9 | 130 |
| L2 | 9 | 178 |
| E4 | 9 | 10 |
| L1 | 9 | 104 |
| E5B | 9 | 32 |
| E2 | 9 | 58 |
| L1 | 9 | 148 |
| L1 | 9 | 326 |
| L2 | 9 | 400 |
| L1 | 9 | 110 |
| E6 | 9 | 138 |
| E1 | 9 | 169 |
| E7 | 9 | 6 |
| L2 | 9 | 430 |
| E1 | 9 | 91 |
| E2 | 9 | 192 |
| L2 | 9 | 411 |
| E1 | 9 | 500 |
| L2 | 9 | 53 |
| L1 | 9 | 114 |
| E1 | 9 | 19 |
| E1 | 9 | 139 |
| L1 | 9 | 67 |
| E1 | 9 | 418 |
| E6 | 9 | 82 |
| E2 | 9 | 56 |
| L2 | 9 | 179 |
| E2 | 9 | 139 |
| E2 | 9 | 30 |
| L1 | 9 | 328 |
| E1 | 9 | 308 |
| L1 | 9 | 49 |
| E1 | 9 | 555 |
| L2 | 9 | 39 |
| E2 | 9 | 186 |
| E7 | 9 | 54 |
| E1 | 9 | 477 |
| L1 | 9 | 374 |
| L1 | 9 | 390 |
| L2 | 9 | 319 |
| E5A | 9 | 37 |
| L2 | 9 | 281 |
| E1 | 9 | 495 |
| L1 | 9 | 54 |
| L2 | 9 | 46 |
| E5A | 9 | 20 |
| E5A | 9 | 31 |
| E2 | 9 | 33 |
| E1 | 9 | 458 |
| L2 | 9 | 34 |
| E6 | 9 | 32 |
| E6 | 9 | 105 |
| E1 | 9 | 227 |
| E7 | 9 | 79 |
| E5A | 9 | 40 |
| L2 | 9 | 106 |
| E6 | 9 | 46 |
| E1 | 9 | 614 |
| E1 | 9 | 216 |
| E7 | 9 | 12 |
| L1 | 9 | 82 |
| E2 | 9 | 31 |
| E2 | 9 | 311 |
| E1 | 9 | 463 |
| E1 | 9 | 474 |
| L2 | 9 | 81 |
| E1 | 9 | 427 |
| E1 | 9 | 487 |
| L1 | 9 | 217 |
| E1 | 9 | 521 |
| E6 | 9 | 102 |
| E6 | 9 | 55 |
| E1 | 9 | 579 |
| E4 | 9 | 26 |
| L1 | 9 | 156 |
| L2 | 9 | 197 |
| L1 | 9 | 398 |
| E1 | 9 | 199 |
| E2 | 9 | 19 |
| E2 | 9 | 41 |
| E7 | 9 | 87 |
| E6 | 9 | 27 |
| E5A | 9 | 36 |
| E1 | 9 | 494 |
| E1 | 9 | 282 |

TABLE XIX C-continued

HPV11 DR Supermotif Peptides

| 2 | 3 | 4 |
|---|---|---|
| E1 | 9 | 464 |
| E6 | 9 | 101 |
| E2 | 9 | 18 |
| E5B | 9 | 33 |
| E5A | 9 | 58 |
| E5A | 9 | 54 |
| E1 | 9 | 301 |
| E4 | 9 | 34 |
| E1 | 9 | 279 |
| E5A | 9 | 59 |
| E5A | 9 | 55 |
| E7 | 9 | 90 |
| E2 | 9 | 349 |
| E5A | 9 | 21 |
| E7 | 9 | 82 |
| E5A | 9 | 68 |
| L1 | 9 | 371 |
| E1 | 9 | 514 |
| L2 | 9 | 231 |
| E2 | 9 | 59 |
| E1 | 9 | 221 |
| E2 | 9 | 54 |
| E5A | 9 | 32 |
| E1 | 9 | 558 |
| E5A | 9 | 52 |
| E7 | 9 | 8 |
| E5B | 9 | 20 |
| E5A | 9 | 60 |
| E5A | 9 | 56 |
| E4 | 9 | 18 |
| E1 | 9 | 323 |
| L1 | 9 | 387 |
| L2 | 9 | 279 |
| E1 | 9 | 536 |
| E6 | 9 | 1 |
| E5A | 9 | 1 |
| E5A | 9 | 3 |
| E5A | 9 | 4 |
| E2 | 9 | 132 |
| E7 | 9 | 1 |
| L1 | 9 | 363 |
| E1 | 9 | 540 |
| E5B | 9 | 1 |
| E5B | 9 | 3 |
| E4 | 9 | 1 |
| L1 | 9 | 2 |
| E2 | 9 | 332 |
| E1 | 9 | 603 |
| E2 | 9 | 145 |
| E6 | 9 | 97 |
| E6 | 9 | 61 |
| E1 | 9 | 454 |
| L1 | 9 | 34 |
| L1 | 9 | 308 |
| L1 | 9 | 58 |
| E6 | 9 | 24 |
| L1 | 9 | 341 |
| E6 | 9 | 133 |
| E2 | 9 | 250 |
| L2 | 9 | 159 |
| L2 | 9 | 253 |
| E1 | 9 | 398 |
| L1 | 9 | 177 |
| E5B | 9 | 57 |
| L2 | 9 | 384 |
| L1 | 9 | 146 |
| E7 | 9 | 67 |
| E5A | 9 | 81 |
| L2 | 9 | 141 |
| E4 | 9 | 75 |
| L2 | 9 | 359 |
| E1 | 9 | 341 |
| L1 | 9 | 221 |
| L1 | 9 | 187 |
| E5A | 9 | 67 |
| L1 | 9 | 80 |
| L1 | 9 | 17 |
| E1 | 9 | 564 |
| E4 | 9 | 45 |
| L2 | 9 | 92 |
| L2 | 9 | 216 |
| L2 | 9 | 165 |
| E2 | 9 | 214 |
| L2 | 9 | 93 |
| E5A | 9 | 8 |
| E5A | 9 | 22 |
| E4 | 9 | 83 |
| E1 | 9 | 402 |
| E1 | 9 | 67 |
| E6 | 9 | 33 |
| E5A | 9 | 69 |
| L1 | 9 | 372 |
| L1 | 9 | 460 |
| L2 | 9 | 128 |
| L2 | 9 | 363 |
| E1 | 9 | 256 |
| L1 | 9 | 155 |
| E2 | 9 | 51 |
| L2 | 9 | 158 |
| E1 | 9 | 61 |
| E1 | 9 | 530 |
| E2 | 9 | 346 |
| L2 | 9 | 246 |
| L1 | 9 | 470 |
| L1 | 9 | 153 |
| E1 | 9 | 347 |
| E1 | 9 | 366 |
| E2 | 9 | 89 |
| L1 | 9 | 69 |
| L2 | 9 | 70 |
| E6 | 9 | 106 |
| E6 | 9 | 59 |
| E1 | 9 | 284 |
| L2 | 9 | 293 |
| L1 | 9 | 258 |
| E2 | 9 | 359 |
| L2 | 9 | 318 |
| L2 | 9 | 446 |
| E1 | 9 | 87 |
| L1 | 9 | 97 |
| E6 | 9 | 38 |
| E1 | 9 | 541 |
| L1 | 9 | 485 |
| L2 | 9 | 91 |
| E1 | 9 | 346 |
| E1 | 9 | 127 |
| E4 | 9 | 60 |
| L1 | 9 | 480 |
| E1 | 9 | 327 |
| L1 | 9 | 32 |
| L2 | 9 | 223 |
| L2 | 9 | 113 |
| E5A | 9 | 41 |
| E4 | 9 | 81 |
| L2 | 9 | 393 |
| E4 | 9 | 65 |
| L2 | 9 | 177 |
| E1 | 9 | 196 |
| L1 | 9 | 296 |
| E1 | 9 | 510 |
| E2 | 9 | 26 |
| L1 | 9 | 379 |
| E5A | 9 | 33 |
| L2 | 9 | 51 |
| L2 | 9 | 262 |
| E1 | 9 | 110 |
| L1 | 9 | 422 |
| L2 | 9 | 189 |

TABLE XIX C-continued

HPV11
DR Supermotif Peptides

| 2 | 3 | 4 |
|---|---|---|
| L2 | 9 | 379 |
| L2 | 9 | 228 |
| L1 | 9 | 42 |
| L1 | 9 | 455 |
| L1 | 9 | 288 |
| E1 | 9 | 621 |
| E2 | 9 | 203 |
| E2 | 9 | 318 |
| L1 | 9 | 339 |
| L2 | 9 | 212 |
| E2 | 9 | 193 |
| E5A | 9 | 48 |
| E2 | 9 | 101 |
| L2 | 9 | 407 |
| E5B | 9 | 8 |
| E6 | 9 | 22 |
| E1 | 9 | 589 |
| L2 | 9 | 199 |
| L2 | 9 | 423 |
| E1 | 9 | 18 |
| E2 | 9 | 252 |
| E5A | 9 | 74 |
| E5A | 9 | 18 |
| E7 | 9 | 89 |
| E6 | 9 | 29 |
| E1 | 9 | 272 |
| L1 | 9 | 33 |
| L2 | 9 | 140 |
| L2 | 9 | 418 |
| E7 | 9 | 52 |
| L2 | 9 | 17 |
| L1 | 9 | 95 |
| L2 | 9 | 367 |
| E4 | 9 | 90 |
| E2 | 9 | 152 |
| L1 | 9 | 152 |
| E5A | 9 | 47 |
| E5A | 9 | 17 |
| E5A | 9 | 65 |
| L2 | 9 | 153 |
| E5A | 9 | 16 |
| E2 | 9 | 119 |
| L1 | 9 | 11 |
| E2 | 9 | 320 |
| E5B | 9 | 16 |
| L1 | 9 | 416 |
| E1 | 9 | 242 |
| E2 | 9 | 255 |
| E5B | 9 | 28 |
| E5A | 9 | 29 |
| E5A | 9 | 77 |
| E1 | 9 | 51 |
| E7 | 9 | 40 |
| E1 | 9 | 224 |
| E1 | 9 | 437 |
| E1 | 9 | 23 |
| L1 | 9 | 366 |
| L2 | 9 | 96 |
| E2 | 9 | 92 |
| L1 | 9 | 72 |
| E5A | 9 | 24 |
| E1 | 9 | 502 |
| E7 | 9 | 15 |
| E5A | 9 | 51 |
| E4 | 9 | 6 |
| E2 | 9 | 62 |
| E1 | 9 | 82 |
| E1 | 9 | 447 |
| E1 | 9 | 320 |
| E2 | 9 | 206 |
| L1 | 9 | 20 |
| L2 | 9 | 107 |
| E1 | 9 | 587 |
| L1 | 9 | 331 |

TABLE XIX C-continued

HPV11
DR Supermotif Peptides

| 2 | 3 | 4 |
|---|---|---|
| E5B | 9 | 27 |
| E4 | 9 | 5 |
| E5A | 9 | 6 |
| E1 | 9 | 275 |
| E1 | 9 | 429 |
| E1 | 9 | 613 |
| E2 | 9 | 36 |
| E5B | 9 | 17 |
| E4 | 9 | 29 |
| L1 | 9 | 440 |
| E2 | 9 | 310 |
| E1 | 9 | 580 |
| E4 | 9 | 25 |
| E5A | 9 | 57 |
| L1 | 9 | 231 |
| E4 | 9 | 32 |
| L1 | 9 | 70 |
| L1 | 9 | 417 |
| E5A | 9 | 46 |
| E4 | 9 | 19 |
| E2 | 9 | 134 |

TABLE XXa

DR3a Motif Peptides

| 1 | 2 | 3 | 4 |
|---|---|---|---|
| HPV16 | E1 | 9 | 531 |
| HPV16 | E1 | 9 | 369 |
| HPV16 | E1 | 9 | 33 |
| HPV16 | E1 | 9 | 332 |
| HPV16 | E1 | 9 | 520 |
| HPV16 | E1 | 9 | 113 |
| HPV16 | E1 | 9 | 19 |
| HPV16 | E1 | 9 | 305 |
| HPV16 | E1 | 9 | 592 |
| HPV16 | E1 | 9 | 401 |
| HPV16 | E1 | 9 | 365 |
| HPV16 | E1 | 9 | 622 |
| HPV16 | E1 | 9 | 127 |
| HPV16 | E1 | 9 | 52 |
| HPV16 | E1 | 9 | 588 |
| HPV16 | E1 | 9 | 428 |
| HPV16 | E2 | 9 | 229 |
| HPV16 | E2 | 9 | 77 |
| HPV16 | E2 | 9 | 121 |
| HPV16 | E2 | 9 | 171 |
| HPV16 | E2 | 9 | 159 |
| HPV16 | E2 | 9 | 139 |
| HPV16 | E2 | 9 | 291 |
| HPV16 | E2 | 9 | 335 |
| HPV16 | E2 | 9 | 115 |
| HPV16 | E2 | 9 | 97 |
| HPV16 | E2 | 9 | 19 |
| HPV16 | E2 | 9 | 87 |
| HPV16 | E2 | 9 | 10 |
| HPV16 | E2 | 9 | 138 |
| HPV16 | E2 | 9 | 257 |
| HPV16 | E2 | 9 | 337 |
| HPV16 | E2 | 9 | 119 |
| HPV16 | E2 | 9 | 36 |
| HPV16 | E6 | 9 | 33 |
| HPV16 | E6 | 9 | 60 |
| HPV16 | E6 | 9 | 22 |
| HPV16 | E6 | 9 | 45 |
| HPV16 | E6 | 9 | 8 |
| HPV16 | E7 | 9 | 1 |
| HPV16 | E7 | 9 | 11 |
| HPV16 | E7 | 9 | 15 |
| HPV16 | E7 | 9 | 23 |

TABLE XXa-continued

DR3a Motif Peptides

| | | | |
|---|---|---|---|
| HPV16 | L1 | 9 | 276 |
| HPV16 | L1 | 9 | 297 |
| HPV16 | L1 | 9 | 326 |
| HPV16 | L1 | 9 | 220 |
| HPV16 | L1 | 9 | 14 |
| HPV16 | L1 | 9 | 481 |
| HPV16 | L1 | 9 | 409 |
| HPV16 | L1 | 9 | 246 |
| HPV16 | L1 | 9 | 424 |
| HPV16 | L1 | 9 | 48 |
| HPV16 | L1 | 9 | 31 |
| HPV16 | L1 | 9 | 117 |
| HPV16 | L1 | 9 | 129 |
| HPV16 | L1 | 9 | 263 |
| HPV16 | L2 | 9 | 373 |
| HPV16 | L2 | 9 | 108 |
| HPV16 | L2 | 9 | 326 |
| HPV16 | L2 | 9 | 465 |
| HPV16 | L2 | 9 | 368 |
| HPV16 | L2 | 9 | 439 |
| HPV16 | L2 | 9 | 93 |
| HPV16 | L2 | 9 | 277 |
| HPV16 | L2 | 9 | 250 |
| HPV16 | L2 | 9 | 126 |
| HPV16 | L2 | 9 | 369 |
| HPV16 | L2 | 9 | 196 |
| HPV16 | L2 | 9 | 260 |
| HPV18 | E1 | 9 | 75 |
| HPV18 | E1 | 9 | 376 |
| HPV18 | E1 | 9 | 382 |
| HPV18 | E1 | 9 | 388 |
| HPV18 | E1 | 9 | 32 |
| HPV18 | E1 | 9 | 103 |
| HPV18 | E1 | 9 | 339 |
| HPV18 | E1 | 9 | 527 |
| HPV18 | E1 | 9 | 217 |
| HPV18 | E1 | 9 | 599 |
| HPV18 | E1 | 9 | 408 |
| HPV18 | E1 | 9 | 372 |
| HPV18 | E1 | 9 | 629 |
| HPV18 | E1 | 9 | 105 |
| HPV18 | E1 | 9 | 31 |
| HPV18 | E1 | 9 | 515 |
| HPV18 | E1 | 9 | 233 |
| HPV18 | E2 | 9 | 164 |
| HPV18 | E2 | 9 | 292 |
| HPV18 | E2 | 9 | 136 |
| HPV18 | 32 | 9 | 91 |
| HPV18 | E2 | 9 | 143 |
| HPV18 | E2 | 9 | 123 |
| HPV18 | E2 | 9 | 337 |
| HPV18 | E2 | 9 | 40 |
| HPV18 | E2 | 9 | 176 |
| HPV18 | E6 | 9 | 55 |
| HPV18 | E6 | 9 | 17 |
| HPV18 | E6 | 9 | 85 |
| HPV18 | E7 | 9 | 13 |
| HPV18 | E7 | 9 | 21 |
| HPV18 | E7 | 9 | 74 |
| HPV18 | E7 | 9 | 26 |
| HPV18 | L1 | 9 | 83 |
| HPV18 | L1 | 9 | 311 |
| HPV18 | L1 | 9 | 361 |
| HPV18 | L1 | 9 | 281 |
| HPV18 | L1 | 9 | 517 |
| HPV18 | L1 | 9 | 519 |
| HPV18 | L1 | 9 | 255 |
| HPV18 | L1 | 9 | 460 |
| HPV18 | L1 | 9 | 445 |
| HPV18 | L1 | 9 | 152 |
| HPV18 | L1 | 9 | 298 |
| HPV18 | L2 | 9 | 351 |
| HPV18 | L2 | 9 | 106 |
| HPV18 | L2 | 9 | 350 |
| HPV18 | L2 | 9 | 91 |
| HPV18 | L2 | 9 | 319 |
| HPV18 | L2 | 9 | 249 |

TABLE XXa-continued

DR3a Motif Peptides

| | | | |
|---|---|---|---|
| HPV18 | L2 | 9 | 454 |
| HPV31 | E1 | 9 | 413 |
| HPV31 | E1 | 9 | 349 |
| HPV31 | E1 | 9 | 32 |
| HPV31 | E1 | 9 | 312 |
| HPV31 | E1 | 9 | 500 |
| HPV31 | E1 | 9 | 268 |
| HPV31 | E1 | 9 | 112 |
| HPV31 | E1 | 9 | 18 |
| HPV31 | E1 | 9 | 572 |
| HPV31 | E1 | 9 | 381 |
| HPV31 | E1 | 9 | 144 |
| HPV31 | E1 | 9 | 345 |
| HPV31 | E1 | 9 | 602 |
| HPV31 | E2 | 9 | 77 |
| HPV31 | E2 | 9 | 200 |
| HPV31 | E2 | 9 | 139 |
| HPV31 | E2 | 9 | 298 |
| HPV31 | E2 | 9 | 115 |
| HPV31 | E2 | 9 | 262 |
| HPV31 | E2 | 9 | 87 |
| HPV31 | E2 | 9 | 194 |
| HPV31 | E2 | 9 | 10 |
| HPV31 | E2 | 9 | 119 |
| HPV31 | E2 | 9 | 36 |
| HPV31 | E6 | 9 | 21 |
| HPV31 | E6 | 9 | 53 |
| EPV31 | E6 | 9 | 54 |
| HPV31 | E7 | 9 | 1 |
| HPV31 | E7 | 9 | 78 |
| HPV31 | E7 | 9 | 11 |
| HPV31 | E7 | 9 | 15 |
| HPV31 | L1 | 9 | 251 |
| HPV31 | L1 | 9 | 272 |
| HPV31 | L1 | 9 | 301 |
| HPV31 | L1 | 9 | 446 |
| HPV31 | L1 | 9 | 456 |
| HPV31 | L1 | 9 | 384 |
| HPV31 | L1 | 9 | 195 |
| HPV31 | L1 | 9 | 221 |
| HPV31 | L1 | 9 | 399 |
| HPV31 | L1 | 9 | 22 |
| HPV31 | L1 | 9 | 92 |
| HPV31 | L1 | 9 | 104 |
| HPV31 | L1 | 9 | 238 |
| HPV31 | L2 | 9 | 361 |
| HPV31 | L2 | 9 | 409 |
| HPV31 | L2 | 9 | 108 |
| HPV31 | L2 | 9 | 245 |
| HPV31 | L2 | 9 | 355 |
| HPV31 | L2 | 9 | 432 |
| HPV31 | L2 | 9 | 93 |
| HPV31 | L2 | 9 | 319 |
| HPV31 | L2 | 9 | 270 |
| HPV31 | L2 | 9 | 458 |
| HPV31 | L2 | 9 | 191 |
| HPV31 | L2 | 9 | 255 |
| HPV33 | E1 | 9 | 362 |
| HPV33 | E1 | 9 | 170 |
| HPV33 | E1 | 9 | 59 |
| HPV33 | E1 | 9 | 298 |
| HPV33 | E1 | 9 | 32 |
| HPV33 | E1 | 9 | 513 |
| HPV33 | E1 | 9 | 615 |
| HPV33 | E1 | 9 | 585 |
| HPV33 | E1 | 9 | 50 |
| HPV33 | E1 | 9 | 260 |
| HPV33 | E1 | 9 | 394 |
| HPV33 | E1 | 9 | 358 |
| HPV33 | E1 | 9 | 164 |
| HPV33 | E1 | 9 | 524 |
| HPV33 | E1 | 9 | 18 |
| HPV33 | E1 | 9 | 219 |
| HPV33 | E1 | 9 | 597 |
| HPV33 | E2 | 9 | 139 |
| HPV33 | E2 | 9 | 77 |
| HPV33 | E2 | 9 | 171 |

TABLE XXa-continued

DR3a Motif Peptides

| | | | |
|---|---|---|---|
| HPV33 | E2 | 9 | 138 |
| HPV33 | E2 | 9 | 279 |
| HPV33 | E2 | 9 | 140 |
| HPV33 | E2 | 9 | 19 |
| HPV33 | E2 | 9 | 212 |
| HPV33 | E2 | 9 | 244 |
| HPV33 | E2 | 9 | 325 |
| HPV33 | E2 | 9 | 119 |
| HPV33 | E2 | 9 | 36 |
| HPV33 | E2 | 9 | 170 |
| HPV33 | E6 | 9 | 1 |
| HPV33 | E6 | 9 | 53 |
| HPV33 | E7 | 9 | 11 |
| HPV33 | E7 | 9 | 23 |
| HPV33 | E7 | 9 | 15 |
| HPV33 | L1 | 9 | 348 |
| HPV33 | L1 | 9 | 354 |
| HPV33 | L1 | 9 | 250 |
| HPV33 | L1 | 9 | 271 |
| HPV33 | L1 | 9 | 300 |
| HPV33 | L1 | 9 | 393 |
| HPV33 | L1 | 9 | 194 |
| HPV33 | L1 | 9 | 454 |
| HPV33 | L1 | 9 | 220 |
| HPV33 | L1 | 9 | 382 |
| HPV33 | L1 | 9 | 397 |
| HPV33 | L1 | 9 | 22 |
| HPV33 | L1 | 9 | 92 |
| HPV33 | L1 | 9 | 104 |
| HPV33 | L1 | 9 | 237 |
| HPV33 | L2 | 9 | 338 |
| HPV33 | L2 | 9 | 433 |
| HPV33 | L2 | 9 | 260 |
| HPV33 | L2 | 9 | 250 |
| HPV33 | L2 | 9 | 107 |
| HPV33 | L2 | 9 | 365 |
| HPV33 | L2 | 9 | 324 |
| HPV33 | L2 | 9 | 92 |
| HPV33 | L2 | 9 | 428 |
| HPV33 | L2 | 9 | 332 |
| HPV33 | L2 | 9 | 203 |
| HPV33 | L2 | 9 | 366 |
| HPV33 | L2 | 9 | 196 |
| HPV33 | L2 | 9 | 74 |
| HPV45 | E1 | 9 | 75 |
| HPV45 | E1 | 9 | 362 |
| HPV45 | E1 | 9 | 298 |
| HPV45 | E1 | 9 | 32 |
| HPV45 | E1 | 9 | 103 |
| HPV45 | E1 | 9 | 325 |
| HPV45 | E1 | 9 | 513 |
| HPV45 | E1 | 9 | 203 |
| HPV45 | E1 | 9 | 18 |
| HPV45 | E1 | 9 | 501 |
| HPV45 | E1 | 9 | 585 |
| HPV45 | E1 | 9 | 394 |
| HPV45 | E1 | 9 | 105 |
| HPV45 | E1 | 9 | 358 |
| HPV45 | E1 | 9 | 615 |
| HPV45 | E1 | 9 | 31 |
| HPV45 | E1 | 9 | 219 |
| HPV45 | E2 | 9 | 166 |
| HPV45 | E2 | 9 | 296 |
| HPV45 | E2 | 9 | 138 |
| HPV45 | E2 | 9 | 93 |
| HPV45 | E2 | 9 | 145 |
| HPV45 | E2 | 9 | 125 |
| HPV45 | E2 | 9 | 340 |
| HPV45 | E2 | 9 | 42 |
| HPV45 | E2 | 9 | 178 |
| HPV45 | E6 | 9 | 55 |
| HPV45 | E6 | 9 | 17 |
| HPV45 | E6 | 9 | 85 |
| HPV45 | E7 | 9 | 13 |
| HPV45 | E7 | 9 | 75 |
| HPV45 | E7 | 9 | 27 |
| HPV45 | L1 | 9 | 48 |
| HPV45 | L1 | 9 | 277 |
| HPV45 | L1 | 9 | 298 |
| HPV45 | L1 | 9 | 247 |
| HPV45 | L1 | 9 | 485 |
| HPV45 | L1 | 9 | 221 |
| HPV45 | L1 | 9 | 293 |
| HPV45 | L1 | 9 | 118 |
| HPV45 | L1 | 9 | 413 |
| HPV45 | L1 | 9 | 130 |
| HPV45 | L1 | 9 | 264 |
| HPV45 | L2 | 9 | 263 |
| HPV45 | L2 | 9 | 455 |
| HPV45 | L2 | 9 | 106 |
| HPV45 | L2 | 9 | 349 |
| HPV45 | L2 | 9 | 91 |
| HPV45 | L2 | 9 | 319 |
| HPV45 | L2 | 9 | 249 |
| HPV56 | E2 | 9 | 137 |
| HPV56 | E2 | 9 | 131 |
| HPV56 | E2 | 9 | 20 |
| HPV56 | E2 | 9 | 62 |
| HPV56 | E2 | 9 | 110 |
| HPV56 | E2 | 9 | 284 |
| HPV56 | E2 | 9 | 129 |
| HPV56 | E2 | 9 | 53 |
| HPV56 | E2 | 9 | 285 |
| HPV56 | E2 | 9 | 30 |
| HPV56 | E2 | 9 | 240 |
| HPV56 | E2 | 9 | 82 |
| HPV56 | E2 | 9 | 260 |
| HPV56 | E6 | 9 | 57 |
| HPV56 | E6 | 9 | 56 |
| HPV56 | E7 | 9 | 72 |
| HPV56 | E7 | 9 | 11 |
| HPV56 | L1 | 9 | 305 |
| HPV56 | L1 | 9 | 20 |
| HPV56 | L1 | 9 | 334 |
| HPV56 | L1 | 9 | 254 |
| HPV56 | L1 | 9 | 416 |
| HPV56 | L1 | 9 | 8 |
| HPV56 | L1 | 9 | 431 |
| HPV56 | L1 | 9 | 488 |
| HPV56 | L1 | 9 | 57 |
| HPV56 | L1 | 9 | 125 |
| HPV56 | L1 | 9 | 137 |
| HPV56 | L1 | 9 | 284 |
| HPV56 | L1 | 9 | 271 |
| HPV56 | L1 | 9 | 87 |
| HPV56 | L2 | 9 | 249 |
| HPV56 | L2 | 9 | 456 |
| HPV56 | L2 | 9 | 106 |
| HPV56 | L2 | 9 | 270 |
| HPV56 | L2 | 9 | 426 |
| HPV56 | L2 | 9 | 91 |
| HPV56 | L2 | 9 | 319 |
| HPV56 | L2 | 9 | 161 |
| HPV56 | L2 | 9 | 354 |

HPV6A

| 2 | 3 | 4 |
|---|---|---|
| E1 | 9 | 102 |
| L2 | 9 | 353 |
| E1 | 9 | 333 |
| E1 | 9 | 370 |
| E1 | 9 | 306 |
| E2 | 9 | 133 |
| E2 | 9 | 77 |
| E1 | 9 | 376 |
| E2 | 9 | 83 |
| L1 | 9 | 246 |
| L1 | 9 | 73 |
| L1 | 9 | 296 |
| E1 | 9 | 32 |
| L2 | 9 | 193 |
| E1 | 9 | 227 |

TABLE XXa-continued

DR3a Motif Peptides

| | | |
|---|---|---|
| L1 | 9 | 190 |
| E2 | 9 | 290 |
| L2 | 9 | 107 |
| L1 | 9 | 450 |
| E4 | 9 | 49 |
| L1 | 9 | 216 |
| E2 | 9 | 87 |
| E1 | 9 | 521 |
| E7 | 9 | 11 |
| E2 | 9 | 18 |
| L2 | 9 | 393 |
| E1 | 9 | 1 |
| E1 | 9 | 50 |
| L1 | 9 | 393 |
| L2 | 9 | 254 |
| E1 | 9 | 531 |
| E1 | 9 | 593 |
| E1 | 9 | 402 |
| L2 | 9 | 247 |
| E1 | 9 | 366 |
| L2 | 9 | 319 |
| L2 | 9 | 159 |
| L2 | 9 | 92 |
| L1 | 9 | 378 |
| L1 | 9 | 21 |
| L2 | 9 | 263 |
| E2 | 9 | 138 |
| L2 | 9 | 348 |
| E1 | 9 | 18 |
| E2 | 9 | 119 |
| E2 | 9 | 337 |
| E2 | 9 | 36 |
| L1 | 9 | 233 |
| E2 | 9 | 171 |
| SF 1168148 v1 | | |
| E1 | 9 | 102 |
| E1 | 9 | 333 |
| E1 | 9 | 370 |
| E2 | 9 | 133 |
| E2 | 9 | 77 |
| E1 | 9 | 306 |
| E1 | 9 | 376 |
| E2 | 9 | 83 |
| L1 | 9 | 246 |
| L1 | 9 | 73 |
| L1 | 9 | 296 |
| E1 | 9 | 32 |
| L2 | 9 | 193 |
| E1 | 9 | 227 |
| L1 | 9 | 190 |
| E2 | 9 | 290 |
| L2 | 9 | 107 |
| E2 | 9 | 335 |
| L1 | 9 | 450 |
| E4 | 9 | 59 |
| L1 | 9 | 216 |
| E1 | 9 | 521 |
| E7 | 9 | 11 |
| E2 | 9 | 18 |
| E1 | 9 | 1 |
| E1 | 9 | 50 |
| L1 | 9 | 393 |
| L2 | 9 | 254 |
| E1 | 9 | 531 |
| L2 | 9 | 392 |
| E1 | 9 | 593 |
| E1 | 9 | 402 |
| L2 | 9 | 247 |
| E1 | 9 | 366 |
| L2 | 9 | 319 |
| L2 | 9 | 159 |
| L2 | 9 | 92 |
| E2 | 9 | 87 |
| L1 | 9 | 378 |
| L1 | 9 | 21 |
| L2 | 9 | 263 |
| E2 | 9 | 138 |

TABLE XXa-continued

DR3a Motif Peptides

| | | |
|---|---|---|
| L2 | 9 | 348 |
| E1 | 9 | 18 |
| E5B | 9 | 62 |
| E2 | 9 | 119 |
| E2 | 9 | 337 |
| E2 | 9 | 36 |
| L1 | 9 | 233 |
| E2 | 9 | 171 |
| E1 | 9 | 102 |
| E6 | 9 | 89 |
| E1 | 9 | 333 |
| E1 | 9 | 370 |
| E2 | 9 | 77 |
| E1 | 9 | 306 |
| E1 | 9 | 376 |
| L1 | 9 | 247 |
| L1 | 9 | 73 |
| L1 | 9 | 268 |
| E1 | 9 | 169 |
| L1 | 9 | 297 |
| E1 | 9 | 32 |
| L2 | 9 | 338 |
| E2 | 9 | 265 |
| E1 | 9 | 227 |
| L1 | 9 | 191 |
| E2 | 9 | 289 |
| L2 | 9 | 106 |
| L1 | 9 | 451 |
| L1 | 9 | 217 |
| E2 | 9 | 87 |
| E1 | 9 | 521 |
| E5A | 9 | 36 |
| E7 | 9 | 11 |
| E6 | 9 | 54 |
| E2 | 9 | 18 |
| E1 | 9 | 1 |
| L1 | 9 | 394 |
| L2 | 9 | 253 |
| E7 | 9 | 67 |
| L2 | 9 | 388 |
| E1 | 9 | 593 |
| E1 | 9 | 402 |
| L2 | 9 | 158 |
| L2 | 9 | 246 |
| E1 | 9 | 366 |
| L2 | 9 | 318 |
| L2 | 9 | 91 |
| E4 | 9 | 60 |
| L1 | 9 | 379 |
| L1 | 9 | 21 |
| L2 | 9 | 262 |
| E1 | 9 | 621 |
| L2 | 9 | 347 |
| E1 | 9 | 18 |
| E2 | 9 | 138 |
| E2 | 9 | 336 |
| E2 | 9 | 119 |
| L2 | 9 | 192 |
| E2 | 9 | 36 |
| L1 | 9 | 234 |
| E2 | 9 | 171 |

TABLE XXb

DR3b Motif Peptides

| 1 | 2 | 3 | 4 |
|---|---|---|---|
| HPV16 | E1 | 9 | 115 |
| HPV16 | E1 | 9 | 545 |
| HPV16 | E1 | 9 | 478 |
| HPV16 | E1 | 9 | 570 |
| HPV16 | E1 | 9 | 602 |
| HPV16 | E1 | 9 | 145 |

TABLE XXb-continued

DR3b Motif Peptides

| | | | |
|---|---|---|---|
| HPV16 | E1 | 9 | 247 |
| HPV16 | E1 | 9 | 532 |
| HPV16 | E1 | 9 | 23 |
| HPV16 | E2 | 9 | 125 |
| HPV16 | E2 | 9 | 270 |
| HPV16 | E2 | 9 | 167 |
| HPV16 | E2 | 9 | 271 |
| HPV16 | E2 | 9 | 346 |
| HPV16 | E2 | 9 | 315 |
| HPV16 | E6 | 9 | 26 |
| HPV16 | E6 | 9 | 117 |
| HPV16 | L1 | 9 | 165 |
| HPV16 | L1 | 9 | 359 |
| HPV16 | L1 | 9 | 440 |
| HPV16 | L1 | 9 | 141 |
| HPV16 | L1 | 9 | 173 |
| HPV16 | L1 | 9 | 452 |
| HPV16 | L2 | 9 | 18 |
| HPV16 | L2 | 9 | 293 |
| HPV16 | L2 | 9 | 7 |
| HPV16 | L2 | 9 | 349 |
| HPV18 | E1 | 9 | 229 |
| HPV18 | E1 | 9 | 552 |
| HPV18 | E1 | 9 | 509 |
| HPV18 | E1 | 9 | 205 |
| HPV18 | E1 | 9 | 471 |
| HPV18 | E1 | 9 | 609 |
| HPV18 | E1 | 9 | 571 |
| HPV18 | E1 | 9 | 22 |
| HPV18 | E2 | 9 | 23 |
| HPV18 | E2 | 9 | 333 |
| HPV18 | E2 | 9 | 172 |
| HPV18 | E2 | 9 | 316 |
| HPV18 | E6 | 9 | 134 |
| HPV18 | E7 | 9 | 54 |
| HPV18 | L1 | 9 | 552 |
| HPV18 | L1 | 9 | 495 |
| HPV18 | L1 | 9 | 176 |
| HPV18 | L1 | 9 | 208 |
| HPV18 | L1 | 9 | 200 |
| HPV18 | L1 | 9 | 476 |
| HPV18 | L2 | 9 | 263 |
| HPV18 | L2 | 9 | 286 |
| HPV18 | L2 | 9 | 17 |
| HPV31 | E1 | 9 | 114 |
| HPV31 | E1 | 9 | 103 |
| HPV31 | E1 | 9 | 525 |
| HPV31 | E1 | 9 | 458 |
| HPV31 | E1 | 9 | 533 |
| HPV31 | E1 | 9 | 550 |
| HPV31 | E1 | 9 | 582 |
| HPV31 | E2 | 9 | 125 |
| HPV31 | E2 | 9 | 121 |
| HPV31 | E2 | 9 | 171 |
| HPV31 | E2 | 9 | 159 |
| HPV31 | E2 | 9 | 19 |
| HPV31 | E2 | 9 | 345 |
| HPV31 | E2 | 9 | 353 |
| HPV31 | E2 | 9 | 239 |
| HPV31 | E2 | 9 | 322 |
| HPV31 | E6 | 9 | 110 |
| HPV31 | E7 | 9 | 57 |
| HPV31 | L1 | 9 | 213 |
| HPV31 | L1 | 9 | 334 |
| HPV31 | L1 | 9 | 116 |
| HPV31 | L1 | 9 | 148 |
| HPV31 | L1 | 9 | 415 |
| HPV31 | L2 | 9 | 18 |
| HPV31 | L2 | 9 | 286 |
| HPV31 | L2 | 9 | 170 |
| HPV31 | L2 | 9 | 263 |
| HPV31 | L2 | 9 | 73 |
| HPV31 | L2 | 9 | 226 |
| HPV33 | E1 | 9 | 22 |
| HPV33 | E1 | 9 | 538 |
| HPV33 | E1 | 9 | 635 |
| HPV33 | E1 | 9 | 546 |
| HPV33 | E1 | 9 | 616 |
| HPV33 | E1 | 9 | 563 |
| HPV33 | E1 | 9 | 240 |
| HPV33 | E2 | 9 | 42 |
| HPV33 | E2 | 9 | 334 |
| HPV33 | E2 | 9 | 121 |
| HPV33 | E2 | 9 | 303 |
| HPV33 | E5 | 9 | 62 |
| HPV33 | E6 | 9 | 19 |
| HPV33 | E6 | 9 | 88 |
| HPV33 | E6 | 9 | 119 |
| HPV33 | E6 | 9 | 110 |
| HPV33 | L1 | 9 | 333 |
| HPV33 | L1 | 9 | 36 |
| HPV33 | L1 | 9 | 483 |
| HPV33 | L1 | 9 | 116 |
| HPV33 | L1 | 9 | 148 |
| HPV33 | L1 | 9 | 413 |
| HPV33 | L2 | 9 | 17 |
| HPV33 | L2 | 9 | 242 |
| HPV33 | L2 | 9 | 459 |
| HPV33 | L2 | 9 | 291 |
| HPV33 | L2 | 9 | 175 |
| HPV45 | E1 | 9 | 215 |
| HPV45 | E1 | 9 | 538 |
| HPV45 | E1 | 9 | 495 |
| HPV45 | E1 | 9 | 457 |
| HPV45 | E1 | 9 | 191 |
| HPV45 | E1 | 9 | 595 |
| HPV45 | E2 | 9 | 174 |
| HPV45 | E2 | 9 | 48 |
| HPV45 | E2 | 9 | 25 |
| HPV45 | E2 | 9 | 256 |
| HPV45 | E2 | 9 | 320 |
| HPV45 | E6 | 9 | 130 |
| HPV45 | E7 | 9 | 55 |
| HPV45 | L1 | 9 | 362 |
| HPV45 | L1 | 9 | 142 |
| HPV45 | L1 | 9 | 174 |
| HPV45 | L1 | 9 | 166 |
| HPV45 | L1 | 9 | 444 |
| HPV45 | L2 | 9 | 17 |
| HPV45 | L2 | 9 | 306 |
| HPV45 | L2 | 9 | 286 |
| HPV45 | L2 | 9 | 230 |
| HPV56 | E2 | 9 | 264 |
| HPV56 | E2 | 9 | 102 |
| HPV56 | E2 | 9 | 177 |
| HPV56 | E2 | 9 | 142 |
| HPVS6 | E2 | 9 | 224 |
| HPV56 | E2 | 9 | 114 |
| HPV56 | E6 | 9 | 120 |
| HPV56 | E6 | 9 | 113 |
| HPV56 | E6 | 9 | 49 |
| HPV56 | L1 | 9 | 246 |
| HPV56 | L1 | 9 | 367 |
| HPV56 | L1 | 9 | 513 |
| HPV56 | L1 | 9 | 259 |
| HPV56 | L1 | 9 | 173 |
| HPV56 | L1 | 9 | 149 |
| HPV56 | L1 | 9 | 181 |
| HPV56 | L1 | 9 | 512 |
| HPV56 | L2 | 9 | 17 |
| HPV56 | L2 | 9 | 303 |
| HPV56 | L2 | 9 | 286 |
| HPV56 | L2 | 9 | 367 |
| HPV56 | L2 | 9 | 230 |

HPV6A

| 2 | 3 | 4 |
|---|---|---|
| E1 | 9 | 171 |
| E1 | 9 | 546 |
| E1 | 9 | 571 |
| E1 | 9 | 115 |
| E1 | 9 | 352 |

TABLE XXb-continued

DR3b Motif Peptides

| | | |
|---|---|---|
| E1 | 9 | 386 |
| E1 | 9 | 465 |
| E1 | 9 | 503 |
| E2 | 9 | 73 |
| E2 | 9 | 266 |
| E2 | 9 | 302 |
| E2 | 9 | 315 |
| E2 | 9 | 333 |
| E2 | 9 | 352 |
| E4 | 9 | 83 |
| E6 | 9 | 89 |
| E6 | 9 | 47 |
| E6 | 9 | 20 |
| E6 | 9 | 129 |
| L1 | 9 | 143 |
| L1 | 9 | 112 |
| L1 | 9 | 329 |
| L1 | 9 | 409 |
| L2 | 9 | 172 |
| L2 | 9 | 17 |
| L2 | 9 | 74 |
| L2 | 9 | 144 |
| L2 | 9 | 286 |
| L2 | 9 | 357 |

HPV6B

| 2 | 3 | 4n |
|---|---|---|
| E2 | 9 | 178 |
| E1 | 9 | 115 |
| L2 | 9 | 17 |
| E6 | 9 | 89 |
| E2 | 9 | 302 |
| E6 | 9 | 20 |
| L2 | 9 | 357 |
| E2 | 9 | 315 |
| E6 | 9 | 129 |
| L1 | 9 | 329 |
| E1 | 9 | 546 |
| E1 | 9 | 171 |
| E1 | 9 | 352 |
| E2 | 9 | 73 |
| L2 | 9 | 286 |
| L2 | 9 | 144 |
| E1 | 9 | 503 |
| E1 | 9 | 465 |
| L1 | 9 | 409 |

TABLE XXb-continued

DR3b Motif Peptides

| | | |
|---|---|---|
| E2 | 9 | 266 |
| E1 | 9 | 571 |
| L1 | 9 | 112 |
| L2 | 9 | 172 |
| E1 | 9 | 386 |
| L1 | 9 | 143 |
| E4 | 9 | 93 |
| E2 | 9 | 223 |
| E5B | 9 | 37 |
| L2 | 9 | 74 |

HPV11

| 2 | 3 | 4 |
|---|---|---|
| E6 | 9 | 68 |
| E1 | 9 | 182 |
| E1 | 9 | 115 |
| E2 | 9 | 178 |
| L2 | 9 | 16 |
| E2 | 9 | 301 |
| E1 | 9 | 204 |
| E6 | 9 | 20 |
| E2 | 9 | 314 |
| E6 | 9 | 129 |
| L1 | 9 | 330 |
| E1 | 9 | 546 |
| E2 | 9 | 73 |
| L2 | 9 | 285 |
| E1 | 9 | 352 |
| L2 | 9 | 143 |
| E1 | 9 | 465 |
| E1 | 9 | 50 |
| E5B | 9 | 2 |
| L1 | 9 | 410 |
| E1 | 9 | 571 |
| E2 | 9 | 199 |
| L1 | 9 | 112 |
| L2 | 9 | 171 |
| E1 | 9 | 386 |
| E2 | 9 | 345 |
| L1 | 9 | 144 |
| E4 | 9 | 92 |
| E2 | 9 | 351 |
| E6 | 9 | 47 |
| L2 | 9 | 73 |
| E5B | 9 | 38 |

---

What is claimed is:

1. An isolated peptide having 13 residues or less in length and comprising a human papilloma virus (HPV) epitope consisting of the sequence YVVWDSIYYI (SEQ ID NO. 50).

2. A composition comprising the peptide of claim 1, wherein the peptide is admixed with at least one other peptide comprising a cytotoxic T lymphocyte (CTL) epitope.

3. A composition according to claim 2, wherein the at least one other peptide comprises a CTL epitope selected from the group consisting of the sequences set out in Tables VII-XVIII.

4. A composition comprising the peptide of claim 1, wherein the peptide is admixed with at least one other peptide comprising a helper T lymphocyte (HTL) epitope.

5. A composition according to claim 4, wherein the at least one other peptide comprises an HTL epitope selected from the group consisting of the sequences set out in Tables XIX-XX.

6. A composition according to claim 4, wherein the at least one other peptide comprises an HTL epitope which is a pan-DR binding molecule.

7. A composition comprising the peptide of claim 1, further comprising at least two other peptides each comprising an epitope selected from the group consisting of the sequences set out in Tables VII-XX.

8. A composition comprising the peptide of claim 1, further comprising a liposome, wherein the peptide is on or within the liposome.

9. A composition comprising the peptide of claim 1, wherein the peptide is joined to a lipid.

10. A composition comprising the peptide of claim 1, wherein the peptide is joined to a linker, wherein said linker is between one and six amino acids in length.

11. A composition comprising the peptide of claim 1, wherein the peptide is bound to a human leukocyte antigen (HLA) heavy chain, β2-microglobulin, and strepavidin complex, whereby a tetramer is formed.

12. A composition comprising the peptide of claim 1, further comprising an antigen presenting cell, wherein the peptide is on or within the antigen presenting cell.

13. A composition according to claim 12, wherein the peptide is bound to an HLA molecule on an antigen presenting cell, whereby when a cytotoxic lymphocyte (CTL) is present that is restricted to the HLA molecule, a receptor of the CTL binds to a complex of the HLA molecule and the peptide.

* * * * *

UNITED STATES PATENT AND TRADEMARK OFFICE
CERTIFICATE OF CORRECTION

PATENT NO. : 7,572,882 B2  
APPLICATION NO. : 10/149136  
DATED : August 11, 2009  
INVENTOR(S) : Sette et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,222 days.

Signed and Sealed this

Twenty-sixth Day of October, 2010

David J. Kappos  
*Director of the United States Patent and Trademark Office*